(12) United States Patent
Schlessinger et al.

(10) Patent No.: US 7,129,072 B1
(45) Date of Patent: Oct. 31, 2006

(54) CRYSTAL OF FIBROBLAST GROWTH FACTOR RECEPTOR 1 IN COMPLEX WITH FIBROBLAST GROWTH FACTOR

(75) Inventors: Joseph Schlessinger, New York, NY (US); Stevan R. Hubbard, Riverside, NY (US); Moosa Mohammadi, Scarsdale, NY (US); Alexander Plotnikov, Emeryville, CA (US); Zhongtao Zhang, Haworth, NJ (US); Xiang-Peng Kong, New York, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 10/049,429

(22) PCT Filed: Aug. 30, 2000

(86) PCT No.: PCT/US00/23744

§ 371 (c)(1),
(2), (4) Date: Sep. 8, 2003

(87) PCT Pub. No.: WO01/16181

PCT Pub. Date: Mar. 8, 2001

Related U.S. Application Data

(60) Provisional application No. 60/151,810, filed on Aug. 30, 1999.

(51) Int. Cl.
*C12N 9/12* (2006.01)
(52) U.S. Cl. .................................................. 435/194
(58) Field of Classification Search .................. None
See application file for complete search history.

(56) References Cited

U.S. PATENT DOCUMENTS

2004/0005686 A1 * 1/2004 Kurumbail et al. ......... 435/194

FOREIGN PATENT DOCUMENTS

WO 98/07835 2/1998

OTHER PUBLICATIONS

Betzel et al. (1994) Microgravity Sci Technol 7(3):242-245; abstract only.*
Branden et al. "Introduction to Protein Structure Second Edition", Garland Publishing Inc., New York, 1999, pp. 374-375.*
Wiesmann et al. (1997) Cell 91:695-704.*
Panek et al. (1998) J Pharmacol Exp Therap 286:569-577.*
"Encyclopedia of Molecular Biology," Creighton, T., John Wiley and Sons, Inc. New York, 1999, pp. 586 and 2725.*
Pellegrini et al., "The Role of Heparin in the Complex Formation Between Fibroblast Growth Factor 2 and Its High Affinity Receptor: Comparative Modeling and Biochemical Studies", Biochemical Society Transactions, 1998, pp. 545-549, vol. 26, No. 3.
Huhtala et al., "A Dimeric Ternary Complex of FGFR1, Heparin and FGF-1 Leads to an 'Electrostatic Sandwich' Model for Heparin Binding", Structure London, 1999, pp. 699-709, vol. 7, No. 6.
Givol et al., "Complexity of FGF receptors: Genetic Basis for Structural Diversity and Functional Specificity", FASEB, 1992, pp. 3362-3369, vol. 6, No. 15.
Liekens et al., "Modulcation of Fibroblast Growth Factor-2 Receptor Binding, Signaling, and Mitogenic Activity by Heparin-Mimicking Polysulfonated Compounds", Molecular Pharmacology, 1999, pp. 204-213 vol. 56, No. 1.
Plotnikov et al., "Structural Basis for FGF Receptor Dimerization and Activation", Cell, 1999, pp. 641-650, vol. 98, No. 5.
Plotnikov et al., "Crystal Structures of Two FGF-FGFR Complexes Reveal the Determinants of Ligand-Receptor Specificity", Cell, 2000, pp. 413-424, vol. 101, No. 4.
Pellegrini et al., "Crystal Structure of Fibroblast Growth Factor Receptor Ectodomain Bound to Ligand and Heparin", Nature, 2000, pp. 1029-1034, vol. 407, No. 6807.
Stauber et al., "Structural Interactions of Fibroblast Growth Factor Receptor with its Ligands", Proceedings Of the National Academy of Sciences of the United States, 2000, pp. 49-54, vol. 97, No. 1.

* cited by examiner

*Primary Examiner*—David J. Steadman
(74) *Attorney, Agent, or Firm*—Foley & Lardner

(57) ABSTRACT

The determination and use of three dimensional structures of receptor protein tyrosine kinases and/or their ligands are described. One particular group of such structures includes three dimensional structures of the extracellular domain of RPTKs. The three dimensional structures of RPTKs can faciliate the design and identification of modulators of RPTK function. Other such structures can include of RPTK ligands, such as stem cell factor or a fragment thereof. Modulators of RPTK function can be used to treat diseases that are mediated by inappropriate RPTK activity.

1 Claim, 26 Drawing Sheets

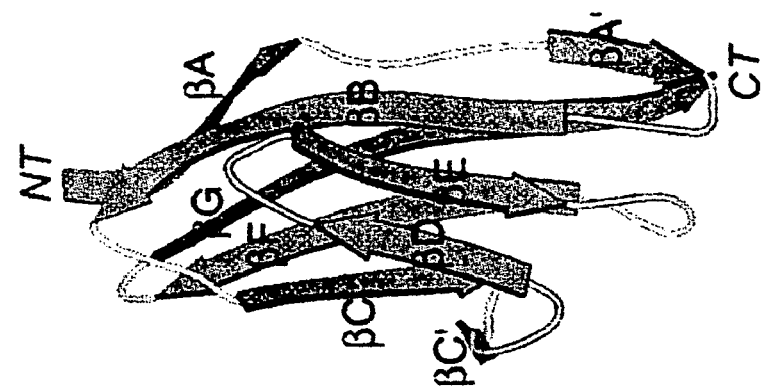
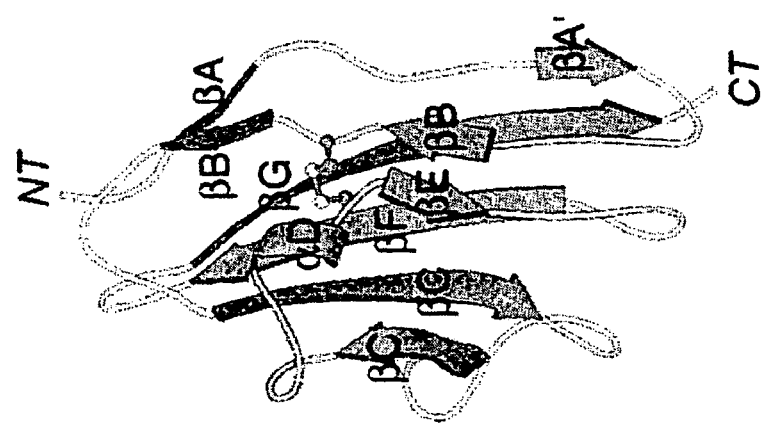
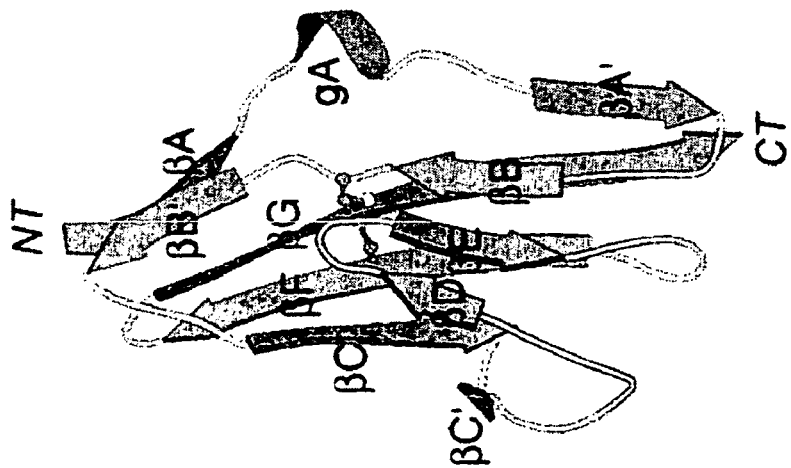
Figure 3

```
            bbbbA    gggA   bbbbbA'    bbbB   bbbB'   bbbbbC   bc'
            150      160    170        180    190             200
FGFR1   MPVAPYWTSPEKMEKKLHAVPA..F..VKFKCPSSGTPNPTLRWLKNGKEFKPDH
FGFR2   NKR.....NT......R........N....R..AG.N.M..M...........QE.
FGFR3   DTG.....R..R.D...L.......N..R.R..AA.N.T.SIS.....R..RGE.
FGFR4   PQQ.....H.QR............CN....R..AA.N.T..I....D.QA.HGEN bbD      bbbE          bbbbbbbbF   bbbbbbbbbbbbG
            210      220    230        240            250
FGFR1   RIGGYKVRYATWSIIMDSVVPSDKGNYTCIVENEYGSINHTYQLDVVERS
FGFR2   ........NQH..L..E............V...........H..]....
FGFR3   ....I.L.HQQ..LV.E......R.....V...KP...RQ..T...L...
FGFR4   ....IRL.HQH..LV.E......R.T...L...AV...RYN.L...L...

bA       bbA'     bbbB    bB'    bbbbbbbC
            260      270      280     290
FGFR1   PHRPILQAGLPANKTVALGSNVEFMCKVYSDPQPHIQWLKHIEVNGS
FGFR2   ..............ASTVV.GD...V......A.......I..V.K...
FGFR3   ..............Q.AV...D...H......A..........V....
FGFR4   ..............T.AVV..D..LL......A..........VI...

bbbbbbC'     hhhD   bbbE       bbbbbbbF   bbbbbbbbbbG
            300      310     320    330        340          350
FGFR1   KIGPDNLPYVQILKTAGVNTTDKEMEVLHLRNVSFEDAGEYTCLAGNSIGLSHHSAWLTVL
FGFR2   .Y...G...LKV..A..........I...YI...T.................I.P........
FGFR3   .V...GT...TV.....A......L...S.H..T..................F......V..
FGFR4   SP.AVGT....V....DI.SS--.V...Y.....A..................YQ........
```

Figure 4

```
          bbbbA    gggA   bbbbbA'    bbbB   bbbB'   bbbbbC   bC'
          150      160    170        180    190     200
R1        MPV.....SP.....K.......K...K..SS.T.N..L..........P
R2        NKRAPYWTNTEKMEKRLHAVPAANTVKFRCPAGGNPMPTMRWLKNGKEFKQ
R3        DTG.....RP.R.D.K.L........R.....A...T.SIS.....R..RG
R4        PQQ.....HPQR...K......G.........A...T..I....D.QA.HG bbD      bbbE        bbbbbbbbF   bbbbbbbbbbbG
          210      220         230    240          250
R1        D.........YAT..I...D..............I............Q.......
R2        EHRIGGYKVRNQHWSLIMESVVPSDKGNYTCVVENEYGSINHTYHLDVVERS
R3        ......I.L.H.Q...V........R........KF...RQ..T...L...
R4        .N....IRL.H.....V........R.T...L...AV...RYN.L...L...
```

Figure 15

```
             bA      bbA'     bbbB    bB'    bbbbbbbC
             260     270      280     290    300
R1 (IIIc)    ............KTVAL.SN...M......P......L..I.V....I...N.
R2 (IIIc)    PHRPILQAGLPANASTVVGGDVEFVCKVYSDAQPHIQWIKHVEKNGSKYGPDGL
R3 (IIIc)    ............QTA.L.S....H.............L....V....V....T
R4           ............TTA...S...LL............L..IVI...SF.AV.F
R1 (IIIb)    ............KTVAL.SN...M......P......L..I.V....I...N.
R2 (IIIb)    ......................................................
R3 (IIIb)    ............QTA.L.S....H.............L....V....V....T
R1 (IIIa)    ............KTVAL.SN...M......P......L..I.V....I...N.

bbbbbbC'    bbbE       bbbbbbbF   bbbbbbbbbbG
             310    320         330        340         350       360
R1 (IIIc)    ..VQI..T....... ..M...HL...S................L.H........
R2 (IIIc)    PYLKVLKA GVNT  KEIEVLYIRNVTFEDAGEYTCLAGNSIGISFHSAWLTVL
R3 (IIIc)    ..VT...T A .....L...SLH................F.H.....V..
R4           ..VQ...T DI SSE--V....L...SA................L.YQ.......
R1 (IIIb)    ..VQI..HS I SS --A...TLF...EAQS...V.KVS.Y..EANQ......T
R2 (IIIb)    .......HS I SSN--A...ALF...EA.....I.KVS.Y..QANQ.......
R3 (IIIb)    ..VT...TSWISESVEADVR.RLA..SER.G...L.R.T.F..VAEKAF...S.H
R1 (IIIa)    ..VQI..VIMAPVFVGQSTGKETTVSGAQVPVGRLSCPRMGSFLTLQAHTLHLS
```

```
                        A              1
SCF     EGICRNRVTN▓▓▓▓▓▓NLPKDYM--ITLK YVPGMDVL-
M-CSF   SE▓▓▓▓IG▓▓▓▓▓▓SQMETSCQ ITFEFV DQEQLKD
IL-5    IP▓▓▓▓▓▓▓▓▓▓▓▓NETL--RIPV PVHKN-----

B                        C
SCF     PSHC▓▓▓▓▓▓▓▓▓▓DKFSNISEGLS▓▓▓▓▓▓▓▓▓▓▓NSSKDL
M-CSF   -▓▓▓▓▓▓▓▓▓▓▓NT▓▓▓▓▓▓▓▓▓▓GCFTKDY--------
IL-5    ▓▓▓▓▓▓▓▓TVQ----GG▓▓▓▓▓▓▓▓▓▓▓▓GE-------

2          D
SCF     KKSFKSPE PRLF T---▓▓▓▓▓▓▓▓▓DAFKDF---VVASETSDCVVS
M-CSF   SEHDKAC  VRTFYET-▓▓▓▓▓▓▓▓▓▓DWNIFSKNCNNSFAECSSQGH
IL-5    -------- ERRR----▓▓▓▓▓▓▓▓▓▓----EWI
```

Figure 20

```
human  EGIC N VTNNVKDVTKLVANLPKDYMITLKYVPGMDVLPSHCWISEMVVQLSDSLTDLL
rat    QEIC N VTDNVKDITKLVANLPKDYMITLNYVAGMDVLPSHCWLRDMVTHLSVSLTTLL
mouse  KEIC N VTDNVKDITKLVANLPNDYMITLNYVAGMDVLPSHCWLRDMVIQLSLSTTLL
dog    KGIC K VTDDVKDVTKLVANLPKDYKIALKYVPGMDVLPSHCWISVMVEQLSVSLTDLL
pig    QGIC N VTDDVKDVTKLVANLPKDYKITLKYVPGMDVLPSHCWISEMVEQLSVSLTDLL
ss            EEEE.................................HHHHHHHHHHHHH
                                HHHHHHHH human  DKFSNISEGLSNYSIIDKLVNIV DD LV CV L NSSKDL  SF  SPEPRLFTPEEFFRIFN
rat    DKFSNISEGLSNYSIIDKLGKIV DD LV L L NAPKNV     SL  KPETRNFTPEEFFSIFN
mouse  DKFSNISEGLSNYSIIDKLGKIV EN LV CM L NAPKNI     SP  RPETRSFTPEEFFSIFN
dog    DKFSNISEGLSNYSIIDKLVKIV DD LV CT Y YSFENV    AP  SPELRLFTPEEFFRIFN
pig    DKFSNISEGLSNYSIIDKLVKIV DD LV CM H HSFENV    SS  SPEFRLFTPEKFFGIFN
ss     HHHHHHHHHHHHHHHHHHH                         EEEE...HHHHHHHH human  RSIDAF DF-VVASETSDCVVS
rat    RSIDAF DF-MVASDTSDCVLS
mouse  RSIDAF DF-MVASDTSDCVLS
dog    RSIDAF DLETVASKSSECVVS
pig    RSIDAF DLEMVAPKTSECVIS
ss     HHH..................
```

Figure 25

SEQUENCE LISTING

<160> NUMBER OF SEQ ID NOS: 202

<210> SEQ ID NO 1
<211> LENGTH: 211
<212> TYPE: PRT
<213> ORGANISM: Homo sapiens

<400> SEQUENCE: 1

Met Pro Val Ala Pro Tyr Trp Thr Ser Pro Glu Lys Met Glu Lys Lys
1               5                   10                  15

Leu His Ala Val Pro Ala Ala Lys Thr Val Lys Phe Lys Cys Pro Ser
            20                  25                  30

Ser Gly Thr Pro Asn Pro Thr Leu Arg Trp Leu Lys Asn Gly Lys Glu
        35                  40                  45

Phe Lys Pro Asp His Arg Ile Gly Gly Tyr Lys Val Arg Tyr Ala Thr
    50                  55                  60

Trp Ser Ile Ile Met Asp Ser Val Val Pro Ser Asp Lys Gly Asn Tyr
65                  70                  75                  80

Thr Cys Ile Val Glu Asn Glu Tyr Gly Ser Ile Asn His Thr Tyr Gln
                85                  90                  95

Leu Asp Val Val Glu Arg Ser Pro His Arg Pro Ile Leu Gln Ala Gly

-continued

```
            100                 105                 110
Leu Pro Ala Asn Lys Thr Val Ala Leu Gly Ser Asn Val Glu Phe Met
            115                 120                 125
Cys Lys Val Tyr Ser Asp Pro Gln Pro His Ile Gln Trp Leu Lys His
            130                 135                 140
Ile Glu Val Asn Gly Ser Lys Ile Gly Pro Asp Asn Leu Pro Tyr Val
145                 150                 155                 160
Gln Ile Leu Lys Thr Ala Gly Val Asn Thr Thr Asp Lys Glu Met Glu
                165                 170                 175
Val Leu His Leu Arg Asn Val Ser Phe Glu Asp Ala Gly Glu Tyr Thr
            180                 185                 190
Cys Leu Ala Gly Asn Ser Ile Gly Leu Ser His His Ser Ala Trp Leu
            195                 200                 205
Thr Val Leu
    210

<210> SEQ ID NO 2
<211> LENGTH: 211
<212> TYPE: PRT
<213> ORGANISM: Homo sapiens

<400> SEQUENCE: 2

Asn Lys Arg Ala Pro Tyr Trp Thr Asn Thr Glu Lys Met Glu Lys Arg
1               5                   10                  15
Leu His Ala Val Pro Ala Ala Asn Thr Val Lys Phe Arg Cys Pro Ala
            20                  25                  30
Gly Gly Asn Pro Met Pro Thr Met Arg Trp Leu Lys Asn Gly Lys Glu
        35                  40                  45
Phe Lys Gln Glu His Arg Ile Gly Gly Tyr Lys Val Arg Asn Gln His
    50                  55                  60
Trp Ser Leu Ile Met Glu Ser Val Val Pro Ser Asp Lys Gly Asn Tyr
65                  70                  75                  80
Thr Cys Val Val Glu Asn Glu Tyr Gly Ser Ile Asn His Thr Tyr His
                85                  90                  95
Leu Asp Val Val Glu Arg Ser Pro His Arg Pro Ile Leu Gln Ala Gly
                100                 105                 110
Leu Pro Ala Asn Ala Ser Thr Val Val Gly Gly Asp Val Glu Phe Val
            115                 120                 125
Cys Lys Val Tyr Ser Asp Ala Gln Pro His Ile Gln Trp Ile Lys His
            130                 135                 140
Val Glu Lys Asn Gly Ser Lys Tyr Gly Pro Asp Gly Leu Pro Tyr Leu
145                 150                 155                 160
Lys Val Leu Lys Ala Ala Gly Val Asn Thr Thr Asp Lys Glu Ile Glu
                165                 170                 175
Val Leu Tyr Ile Arg Asn Val Thr Phe Glu Asp Ala Gly Glu Tyr Thr
            180                 185                 190
Cys Leu Ala Gly Asn Ser Ile Gly Ile Ser Phe His Ser Ala Trp Leu
            195                 200                 205
Thr Val Leu
    210

<210> SEQ ID NO 3
<211> LENGTH: 211
<212> TYPE: PRT
<213> ORGANISM: Homo sapiens
```

```
<400> SEQUENCE: 3

Asp Thr Gly Ala Pro Tyr Trp Thr Arg Pro Glu Arg Met Asp Lys Lys
  1               5                  10                  15

Leu Leu Ala Val Pro Ala Ala Asn Thr Val Arg Phe Arg Cys Pro Ala
             20                  25                  30

Ala Gly Thr Pro Thr Pro Ser Ile Ser Trp Leu Lys Asn Gly Arg Glu
         35                  40                  45

Phe Arg Gly Glu His Arg Ile Gly Gly Ile Lys Leu Arg His Gln Gln
     50                  55                  60

Trp Ser Leu Val Met Glu Ser Val Val Pro Ser Asp Arg Gly Asn Tyr
 65                  70                  75                  80

Thr Cys Val Val Glu Asn Lys Phe Gly Ser Ile Arg Gln Thr Tyr Thr
                 85                  90                  95

Leu Asp Val Leu Glu Arg Ser Pro His Arg Pro Ile Leu Gln Ala Gly
             100                 105                 110

Leu Pro Ala Asn Gln Thr Ala Val Leu Gly Ser Asp Val Glu Phe His
         115                 120                 125

Cys Lys Val Tyr Ser Asp Ala Gln Pro His Ile Gln Trp Leu Lys His
    130                 135                 140

Val Glu Val Asn Gly Ser Lys Val Gly Pro Asp Gly Thr Pro Tyr Val
145                 150                 155                 160

Thr Val Leu Lys Thr Ala Gly Ala Asn Thr Thr Asp Lys Glu Leu Glu
                165                 170                 175

Val Leu Ser Leu His Asn Val Thr Phe Glu Asp Ala Gly Glu Tyr Thr
            180                 185                 190

Cys Leu Ala Gly Asn Ser Ile Gly Phe Ser His His Ser Ala Trp Leu
        195                 200                 205

Val Val Leu
    210

<210> SEQ ID NO 4
<211> LENGTH: 209
<212> TYPE: PRT
<213> ORGANISM: Homo sapiens

<400> SEQUENCE: 4

Pro Gln Gln Ala Pro Tyr Trp Thr His Pro Gln Arg Met Glu Lys Lys
  1               5                  10                  15

Leu His Ala Val Pro Ala Cys Asn Thr Val Lys Phe Arg Cys Pro Ala
             20                  25                  30

Ala Gly Asn Pro Thr Pro Thr Ile Arg Trp Leu Lys Asp Gly Gln Ala
         35                  40                  45

Phe His Gly Glu Asn Arg Ile Gly Gly Ile Arg Leu Arg Tyr His Gln
     50                  55                  60

His Ser Leu Val Met Glu Ser Val Val Pro Ser Asp Arg Gly Thr Tyr
 65                  70                  75                  80

Thr Cys Leu Val Glu Asn Ala Val Gly Ser Ile Arg Tyr Asn Tyr Leu
                 85                  90                  95

Leu Asp Val Leu Glu Arg Ser Pro His Arg Pro Ile Leu Gln Ala Gly
             100                 105                 110

Leu Pro Ala Asn Thr Thr Ala Val Val Gly Ser Asn Asp Glu Leu Leu
         115                 120                 125

Cys Lys Val Tyr Ser Asp Ala Gln Pro His Ile Gln Trp Leu Lys His
    130                 135                 140
```

-continued

```
Ile Val Ile Asn Gly Ser Ser Phe Gly Ala Val Gly Thr Pro Tyr Val
145                 150                 155                 160

Gln Val Leu Lys Thr Ala Asp Ile Asn Ser Ser Glu Val Glu Val Leu
            165                 170                 175

Tyr Leu Arg Asn Val Ser Ala Glu Asp Ala Gly Glu Tyr Thr Cys Leu
        180                 185                 190

Ala Gly Asn Ser Ile Gly Leu Ser Tyr Gln Ser Ala Trp Leu Thr Val
    195                 200                 205

Leu

<210> SEQ ID NO 5
<211> LENGTH: 103
<212> TYPE: PRT
<213> ORGANISM: Homo sapiens

<400> SEQUENCE: 5

Met Pro Val Ala Pro Tyr Trp Thr Ser Pro Glu Lys Met Glu Lys Lys
1               5                   10                  15

Leu His Ala Val Pro Ala Ala Lys Thr Val Lys Phe Arg Cys Pro Ser
            20                  25                  30

Ser Gly Thr Pro Asn Pro Thr Leu Arg Trp Leu Lys Asn Gly Lys Glu
        35                  40                  45

Phe Lys Pro Asp His Arg Ile Gly Gly Tyr Lys Val Arg Tyr Ala Thr
    50                  55                  60

Trp Ile Leu Ile Met Asp Ser Val Val Pro Ser Asp Lys Gly Asn Tyr
65                  70                  75                  80

Thr Cys Ile Val Glu Asn Glu Tyr Gly Ser Ile Asn Gln Thr Tyr Gln
                85                  90                  95

Leu Asp Val Val Glu Arg Ser
            100

<210> SEQ ID NO 6
<211> LENGTH: 103
<212> TYPE: PRT
<213> ORGANISM: Homo sapiens

<400> SEQUENCE: 6

Asn Lys Arg Ala Pro Tyr Trp Thr Asn Thr Glu Lys Met Glu Lys Arg
1               5                   10                  15

Leu His Ala Val Pro Ala Ala Asn Thr Val Lys Phe Arg Cys Pro Ala
            20                  25                  30

Gly Gly Asn Pro Met Pro Thr Met Arg Trp Leu Lys Asn Gly Lys Glu
        35                  40                  45

Phe Lys Gln Glu His Arg Ile Gly Gly Tyr Lys Val Arg Asn Gln His
    50                  55                  60

Trp Ser Leu Ile Met Glu Ser Val Val Pro Ser Asp Lys Gly Asn Tyr
65                  70                  75                  80

Thr Cys Val Val Glu Asn Glu Tyr Gly Ser Ile Asn His Thr Tyr His
                85                  90                  95

Leu Asp Val Val Glu Arg Ser
            100

<210> SEQ ID NO 7
<211> LENGTH: 103
<212> TYPE: PRT
<213> ORGANISM: Homo sapiens

<400> SEQUENCE: 7
```

```
Asp Thr Gly Ala Pro Tyr Trp Thr Arg Pro Glu Arg Met Asp Lys Lys
  1               5                  10                  15

Leu Leu Ala Val Pro Ala Ala Asn Thr Val Arg Phe Arg Cys Pro Ala
             20                  25                  30

Ala Gly Asn Pro Thr Pro Ser Ile Ser Trp Leu Lys Asn Gly Arg Glu
             35                  40                  45

Phe Arg Gly Glu His Arg Ile Gly Gly Ile Lys Leu Arg His Gln Gln
         50                  55                  60

Trp Ser Leu Val Met Glu Ser Val Val Pro Ser Asp Arg Gly Asn Tyr
 65                  70                  75                  80

Thr Cys Val Val Glu Asn Lys Phe Gly Ser Ile Arg Gln Thr Tyr Thr
                 85                  90                  95

Leu Asp Val Leu Glu Arg Ser
             100
```

```
<210> SEQ ID NO 8
<211> LENGTH: 103
<212> TYPE: PRT
<213> ORGANISM: Homo sapiens

<400> SEQUENCE: 8

Pro Gln Gln Ala Pro Tyr Trp Thr His Pro Gln Arg Met Glu Lys Lys
  1               5                  10                  15

Leu His Ala Val Pro Ala Gly Asn Thr Val Lys Phe Arg Cys Pro Ala
             20                  25                  30

Ala Gly Asn Pro Thr Pro Thr Ile Arg Trp Leu Lys Asp Gly Gln Ala
             35                  40                  45

Phe His Gly Glu Asn Arg Ile Gly Gly Ile Arg Leu Arg His Gln His
         50                  55                  60

Trp Ser Leu Val Met Glu Ser Val Val Pro Ser Asp Arg Gly Thr Tyr
 65                  70                  75                  80

Thr Cys Leu Val Glu Asn Ala Val Gly Ser Ile Arg Tyr Asn Tyr Leu
                 85                  90                  95

Leu Asp Val Leu Glu Arg Ser
             100
```

```
<210> SEQ ID NO 9
<211> LENGTH: 108
<212> TYPE: PRT
<213> ORGANISM: Homo sapiens

<400> SEQUENCE: 9

Pro His Arg Pro Ile Leu Gln Ala Gly Leu Pro Ala Asn Lys Thr Val
  1               5                  10                  15

Ala Leu Gly Ser Asn Val Glu Phe Met Cys Lys Val Tyr Ser Asp Pro
             20                  25                  30

Gln Pro His Ile Gln Trp Leu Lys His Ile Glu Val Asn Gly Ser Lys
             35                  40                  45

Ile Gly Pro Asp Asn Leu Pro Tyr Val Gln Ile Leu Lys Thr Ala Gly
         50                  55                  60

Val Asn Thr Thr Asp Lys Glu Met Glu Val Leu His Leu Arg Asn Val
 65                  70                  75                  80

Ser Phe Glu Asp Ala Gly Glu Tyr Thr Cys Leu Ala Gly Asn Ser Ile
                 85                  90                  95

Gly Leu Ser His His Ser Ala Trp Leu Thr Val Leu
             100                 105
```

<210> SEQ ID NO 10
<211> LENGTH: 108
<212> TYPE: PRT
<213> ORGANISM: Homo sapiens

<400> SEQUENCE: 10

Pro His Arg Pro Ile Leu Gln Ala Gly Leu Pro Ala Asn Ala Ser Thr
1               5                   10                  15

Val Val Gly Gly Asp Val Glu Phe Val Cys Lys Val Tyr Ser Asp Ala
            20                  25                  30

Gln Pro His Ile Gln Trp Ile Lys His Val Glu Lys Asn Gly Ser Lys
        35                  40                  45

Tyr Gly Pro Asp Gly Leu Pro Tyr Leu Lys Val Leu Lys Ala Ala Gly
    50                  55                  60

Val Asn Thr Thr Asp Lys Glu Ile Glu Val Leu Tyr Ile Arg Asn Val
65                  70                  75                  80

Thr Phe Glu Asp Ala Gly Glu Tyr Thr Cys Leu Ala Gly Asn Ser Ile
                85                  90                  95

Gly Ile Ser Phe His Ser Ala Trp Leu Thr Val Leu
            100                 105

<210> SEQ ID NO 11
<211> LENGTH: 108
<212> TYPE: PRT
<213> ORGANISM: Homo sapiens

<400> SEQUENCE: 11

Pro His Arg Pro Ile Leu Gln Ala Gly Leu Pro Ala Asn Gln Thr Ala
1               5                   10                  15

Val Leu Gly Ser Asp Val Glu Phe His Cys Lys Val Tyr Ser Asp Ala
            20                  25                  30

Gln Pro His Ile Gln Trp Leu Lys His Val Glu Val Asn Gly Ser Lys
        35                  40                  45

Val Gly Pro Asp Gly Thr Pro Tyr Val Thr Val Leu Lys Thr Ala Gly
    50                  55                  60

Ala Asn Thr Thr Asp Lys Glu Leu Glu Val Leu Ser Leu His Asn Val
65                  70                  75                  80

Thr Phe Glu Asp Ala Gly Glu Tyr Thr Cys Leu Ala Gly Asn Ser Ile
                85                  90                  95

Gly Phe Ser His His Ser Ala Trp Leu Val Val Leu
            100                 105

<210> SEQ ID NO 12
<211> LENGTH: 106
<212> TYPE: PRT
<213> ORGANISM: Homo sapiens

<400> SEQUENCE: 12

Pro His Arg Pro Ile Leu Gln Ala Gly Leu Pro Ala Asn Thr Thr Ala
1               5                   10                  15

Val Val Gly Ser Asp Val Glu Leu Leu Cys Lys Val Tyr Ser Asp Ala
            20                  25                  30

Gln Pro His Ile Gln Trp Leu Lys His Ile Val Ile Asn Gly Ser Ser
        35                  40                  45

Phe Gly Ala Val Gly Phe Pro Tyr Leu Lys Val Val Gln Thr Ala Asp
    50                  55                  60

```
Ile Asn Ser Ser Glu Val Glu Val Leu Tyr Leu Arg Asn Val Ser Ala
 65                  70                  75                  80

Glu Asp Ala Gly Glu Tyr Thr Cys Leu Ala Gly Asn Ser Ile Gly Leu
                 85                  90                  95

Ser Tyr Gln Ser Ala Trp Leu Thr Val Leu
            100                 105
```

<210> SEQ ID NO 13
<211> LENGTH: 106
<212> TYPE: PRT
<213> ORGANISM: Homo sapiens

<400> SEQUENCE: 13

```
Pro His Arg Pro Ile Leu Gln Ala Gly Leu Pro Ala Asn Lys Thr Val
  1               5                  10                  15

Ala Leu Gly Ser Asn Val Glu Phe Met Cys Lys Val Tyr Ser Asp Pro
                 20                  25                  30

Gln Pro His Ile Gln Trp Leu Lys His Ile Glu Val Asn Gly Ser Lys
             35                  40                  45

Ile Gly Pro Asp Asn Leu Pro Tyr Val Gln Ile Leu Lys His Ser Gly
 50                  55                  60

Ile Asn Ser Ser Asp Ala Glu Val Leu Thr Leu Phe Asn Val Thr Glu
 65                  70                  75                  80

Ala Gln Ser Gly Glu Tyr Val Cys Lys Val Ser Asn Tyr Ile Gly Glu
                 85                  90                  95

Ala Asn Gln Ser Ala Trp Leu Thr Val Thr
            100                 105
```

<210> SEQ ID NO 14
<211> LENGTH: 106
<212> TYPE: PRT
<213> ORGANISM: Homo sapiens

<400> SEQUENCE: 14

```
Pro His Arg Pro Ile Leu Gln Ala Gly Leu Pro Ala Asn Ala Ser Thr
  1               5                  10                  15

Val Val Gly Gly Asp Val Glu Phe Val Cys Lys Val Tyr Ser Asp Ala
                 20                  25                  30

Gln Pro His Ile Gln Trp Ile Lys His Val Glu Lys Asn Gly Ser Lys
             35                  40                  45

Tyr Gly Pro Asp Gly Leu Pro Tyr Leu Lys Val Leu Lys His Ser Gly
 50                  55                  60

Ile Asn Ser Ser Asn Ala Glu Val Leu Ala Leu Phe Asn Val Thr Glu
 65                  70                  75                  80

Ala Asp Ala Gly Glu Tyr Ile Cys Lys Val Ser Asn Tyr Ile Gly Gln
                 85                  90                  95

Ala Asn Gln Ser Ala Trp Leu Thr Val Leu
            100                 105
```

<210> SEQ ID NO 15
<211> LENGTH: 108
<212> TYPE: PRT
<213> ORGANISM: Homo sapiens

<400> SEQUENCE: 15

```
Pro His Arg Pro Ile Leu Gln Ala Gly Leu Pro Ala Asn Gln Thr Ala
  1               5                  10                  15

Val Leu Gly Ser Asp Val Glu Phe His Cys Lys Val Tyr Ser Asp Ala
```

```
            20                  25                  30

Gln Pro His Ile Gln Trp Leu Lys His Val Glu Val Asn Gly Ser Lys
        35                  40                  45

Val Gly Pro Asp Gly Thr Pro Tyr Val Thr Val Leu Lys Thr Ser Trp
    50                  55                  60

Ile Ser Glu Ser Val Glu Ala Asp Val Arg Leu Arg Leu Ala Asn Val
65                  70                  75                  80

Ser Glu Arg Asp Gly Glu Tyr Thr Leu Cys Arg Ala Thr Asn Phe Ile
                85                  90                  95

Gly Val Ala Glu Lys Ala Phe Ala Trp Ser Val His
            100                 105

<210> SEQ ID NO 16
<211> LENGTH: 108
<212> TYPE: PRT
<213> ORGANISM: Homo sapiens

<400> SEQUENCE: 16

Pro His Arg Pro Ile Leu Gln Ala Gly Leu Pro Ala Asn Lys Thr Val
1               5                   10                  15

Ala Leu Gly Ser Asn Val Glu Phe Met Cys Lys Val Tyr Ser Asp Pro
            20                  25                  30

Gln Pro His Ile Gln Trp Leu Lys His Ile Glu Val Asn Gly Ser Lys
        35                  40                  45

Ile Gly Pro Asp Asn Leu Pro Tyr Val Gln Ile Leu Lys Val Ile Met
    50                  55                  60

Ala Pro Val Phe Val Gly Gln Ser Thr Gly Lys Glu Thr Thr Val Ser
65                  70                  75                  80

Gly Ala Gln Val Pro Val Gly Arg Leu Ser Cys Pro Arg Met Gly Ser
                85                  90                  95

Phe Leu Thr Leu Gln Ala His Thr Leu His Leu Ser
            100                 105

<210> SEQ ID NO 17
<211> LENGTH: 132
<212> TYPE: PRT
<213> ORGANISM: Homo sapiens

<400> SEQUENCE: 17

Pro Gly Asn Tyr Lys Lys Pro Lys Leu Leu Tyr Cys Ser Asn Gly His
1               5                   10                  15

Phe Leu Arg Ile Leu Pro Asp Gly Thr Val Asp Gly Asp Arg Ser Asp
            20                  25                  30

Gln His Ile Gln Leu Gln Leu Ser Ala Glu Ser Val Glu Val Tyr Ile
        35                  40                  45

Lys Ser Thr Glu Thr Gly Gln Tyr Leu Ala Met Asp Thr Asp Gly Leu
    50                  55                  60

Leu Tyr Gly Ser Gln Thr Pro Asn Glu Glu Cys Leu Phe Leu Glu Arg
65                  70                  75                  80

Leu Glu Glu Asn His Tyr Asn Thr Tyr Ile Ser Lys Lys His Ala Glu
                85                  90                  95

Lys Asn Trp Phe Val Gly Leu Lys Lys Asn Gly Ser Cys Lys Arg Gly
            100                 105                 110

Pro Arg Thr His Tyr Gly Gln Lys Ala Ile Leu Phe Leu Pro Leu Pro
        115                 120                 125

Val Ser Ser Asp
```

```
                130

<210> SEQ ID NO 18
<211> LENGTH: 133
<212> TYPE: PRT
<213> ORGANISM: Homo sapiens

<400> SEQUENCE: 18

Pro Gly His Phe Lys Asp Pro Lys Arg Leu Tyr Cys Lys Asn Gly Gly
  1               5                  10                  15

Phe Phe Leu Arg Ile His Pro Asp Gly Arg Val Asp Gly Val Arg Glu
             20                  25                  30

Lys Ser Asp Pro His Ile Lys Leu Gln Leu Gln Ala Glu Glu Arg Gly
         35                  40                  45

Val Val Ser Ile Lys Gly Val Cys Ala Asn Arg Tyr Leu Ala Met Lys
     50                  55                  60

Glu Asp Gly Arg Leu Leu Ala Ser Lys Cys Val Thr Asp Glu Cys Phe
 65                  70                  75                  80

Phe Phe Glu Arg Leu Glu Ser Asn Asn Tyr Asn Thr Tyr Arg Ser Arg
                 85                  90                  95

Lys Tyr Thr Ser Trp Tyr Val Ala Leu Lys Arg Thr Gly Gln Tyr Lys
            100                 105                 110

Leu Gly Ser Lys Thr Gly Pro Gly Gln Lys Ala Ile Leu Phe Leu Pro
        115                 120                 125

Met Ser Ala Lys Ser
        130

<210> SEQ ID NO 19
<211> LENGTH: 150
<212> TYPE: PRT
<213> ORGANISM: Homo sapiens

<400> SEQUENCE: 19

Leu Gly Gly Ala Pro Arg Arg Lys Leu Tyr Cys Ala Thr Lys Tyr
  1               5                  10                  15

His Leu Gln Leu His Pro Ser Gly Arg Val Asn Gly Ser Leu Glu Asn
             20                  25                  30

Ser Ala Tyr Ser Ile Leu Glu Ile Thr Ala Val Glu Val Gly Ile Val
         35                  40                  45

Ala Ile Arg Gly Leu Phe Ser Gly Arg Tyr Leu Ala Met Asn Lys Arg
     50                  55                  60

Gly Arg Leu Tyr Ala Ser Glu His Tyr Ser Ala Glu Cys Glu Phe Val
 65                  70                  75                  80

Glu Arg Ile His Glu Leu Gly Tyr Asn Thr Tyr Ala Ser Arg Leu Tyr
                 85                  90                  95

Arg Thr Val Ser Ser Thr Pro Gly Ala Arg Arg Gln Pro Ser Ala Glu
            100                 105                 110

Arg Leu Trp Tyr Val Ser Val Asn Gly Lys Gly Arg Pro Arg Arg Gly
        115                 120                 125

Phe Lys Thr Arg Arg Thr Gln Lys Ser Ser Leu Phe Leu Pro Arg Val
    130                 135                 140

Leu Asp His Arg Asp His
145                 150

<210> SEQ ID NO 20
<211> LENGTH: 132
<212> TYPE: PRT
```

-continued

<213> ORGANISM: Homo sapiens

<400> SEQUENCE: 20

Leu Leu Gly Ile Pro Arg Leu Arg Leu Tyr Cys Asn Val Gly Ile
1               5                   10                  15

Gly Phe His Leu Gln Ala Leu Pro Asp Gly Arg Ile Gly Gly Ala His
            20                  25                  30

Ala Asp Thr Arg Asp Ser Leu Leu Glu Glu Leu Ser Pro Val Glu Arg
        35                  40                  45

Gly Val Val Ser Ile Phe Gly Val Ala Ser Arg Phe Phe Val Ala Met
    50                  55                  60

Ser Ser Lys Gly Lys Leu Tyr Tyr Gly Ser Pro Phe Phe Thr Asp Glu
65                  70                  75                  80

Cys Thr Phe Lys Glu Ile Leu Leu Pro Asn Asn Tyr Asn Ala Tyr Glu
                85                  90                  95

Ser Tyr Lys Tyr Pro Gly Met Phe Ile Ala Leu Ser Lys Asn Gly Lys
            100                 105                 110

Thr Lys Lys Gly Asn Arg Val Ser Pro Thr Met Lys Val Thr His Phe
        115                 120                 125

Leu Pro Arg Leu
    130

<210> SEQ ID NO 21
<211> LENGTH: 143
<212> TYPE: PRT
<213> ORGANISM: Homo sapiens

<400> SEQUENCE: 21

Ser Pro Ser Gly Arg Arg Thr Gly Ser Leu Tyr Cys Arg Val Gly Ile
1               5                   10                  15

Gly Phe His Leu Gln Ile Tyr Pro Asp Gly Lys Val Asn Gly Ser His
            20                  25                  30

Glu Ala Asn Met Leu Ser Val Leu Glu Ile Phe Ala Val Ser Gln Gly
        35                  40                  45

Ile Val Gly Ile Arg Gly Val Phe Ser Asn Lys Phe Leu Ala Met Ser
    50                  55                  60

Lys Lys Gly Lys Leu His Ala Ser Ala Lys Phe Thr Asp Asp Cys Lys
65                  70                  75                  80

Phe Arg Glu Arg Phe Gln Glu Asn Ser Asn Tyr Thr Tyr Ala Ser Ala
                85                  90                  95

Ala Ile His Arg Thr Glu Lys Thr Gly Arg Glu Trp Tyr Val Ala Leu
            100                 105                 110

Asn Lys Arg Gly Lys Ala Lys Arg Gly Cys Ala Pro Arg Val Lys Gln
        115                 120                 125

His Ile Ser Thr Phe Leu Pro Arg Phe Lys Gln Ser Glu Gln Pro
    130                 135                 140

<210> SEQ ID NO 22
<211> LENGTH: 130
<212> TYPE: PRT
<213> ORGANISM: Homo sapiens

<400> SEQUENCE: 22

Leu Val Gly Ile Lys Arg Gln Arg Arg Leu Tyr Cys Asn Val Gly Ile
1               5                   10                  15

Gly Phe His Leu Gln Val Leu Pro Asp Gly Arg Ile Ser Gly Thr His
            20                  25                  30

-continued

```
Glu Glu Asn Pro Tyr Ser Leu Leu Glu Ile Ser Thr Val Glu Arg Gly
         35                  40                  45

Val Val Ser Leu Phe Gly Val Arg Ser Ala Leu Phe Val Ala Met Asn
 50                  55                  60

Ser Lys Gly Arg Leu Tyr Ala Thr Pro Ser Gln Phe Glu Glu Cys Lys
 65                  70                  75                  80

Phe Arg Glu Thr Leu Leu Pro Asn Asn Tyr Asn Ala Tyr Glu Ser Asp
                 85                  90                  95

Leu Tyr Gln Gly Thr Tyr Ile Ala Leu Ser Lys Tyr Gly Arg Val Lys
                100                 105                 110

Arg Gly Ser Lys Val Ser Pro Ile Met Thr Val Thr His Phe Leu Pro
        115                 120                 125

Arg Ile
    130
```

<210> SEQ ID NO 23
<211> LENGTH: 135
<212> TYPE: PRT
<213> ORGANISM: Homo sapiens

<400> SEQUENCE: 23

```
Glu Gly Gly Asp Ile Arg Val Arg Arg Leu Phe Cys Arg Thr Gln Trp
 1               5                  10                  15

Tyr Leu Arg Ile Asp Lys Arg Gly Lys Val Lys Gly Thr Gln Glu Met
                20                  25                  30

Lys Asn Asn Tyr Asn Ile Met Glu Ile Arg Thr Val Ala Val Gly Ile
         35                  40                  45

Val Ala Ile Lys Gly Val Glu Ser Glu Phe Tyr Leu Ala Met Asn Lys
 50                  55                  60

Glu Gly Lys Leu Tyr Ala Lys Lys Glu Cys Asn Glu Asp Cys Asn Phe
 65                  70                  75                  80

Lys Glu Leu Ile Leu Glu Asn His Tyr Asn Thr Tyr Ala Ser Ala Lys
                 85                  90                  95

Trp Thr His Asn Gly Gly Glu Met Phe Val Ala Leu Asn Gln Lys Gly
                100                 105                 110

Ile Pro Val Arg Gly Lys Lys Thr Lys Lys Glu Gln Lys Thr Ala His
        115                 120                 125

Phe Leu Pro Met Ala Ile Thr
    130                 135
```

<210> SEQ ID NO 24
<211> LENGTH: 138
<212> TYPE: PRT
<213> ORGANISM: Homo sapiens

<400> SEQUENCE: 24

```
Ser Arg Arg Leu Ile Arg Thr Tyr Gln Leu Tyr Ser Arg Thr Ser Gly
 1               5                  10                  15

Lys His Val Gln Val Leu Ala Asn Lys Arg Ile Asn Ala Met Ala Glu
                20                  25                  30

Asp Gly Asp Pro Phe Ala Lys Leu Ile Val Glu Thr Asp Thr Phe Gly
         35                  40                  45

Ser Arg Val Arg Val Arg Gly Ala Glu Thr Gly Leu Tyr Ile Cys Met
 50                  55                  60

Asn Lys Lys Gly Lys Leu Ile Ala Lys Ser Asn Gly Lys Gly Lys Asp
 65                  70                  75                  80
```

-continued

```
Cys Val Phe Thr Glu Ile Val Leu Glu Asn Asn Tyr Thr Ala Leu Gln
             85                  90                  95

Asn Ala Lys Tyr Glu Gly Trp Tyr Met Ala Phe Thr Arg Lys Gly Arg
            100                 105                 110

Pro Arg Lys Gly Ser Lys Thr Arg Gln His Gln Arg Glu Val His Phe
            115                 120                 125

Met Lys Arg Leu Pro Arg Gly His His Thr
130                 135

<210> SEQ ID NO 25
<211> LENGTH: 141
<212> TYPE: PRT
<213> ORGANISM: Homo sapiens

<400> SEQUENCE: 25

Leu Lys Gly Ile Leu Arg Arg Gln Leu Tyr Cys Arg Thr Gly Phe
 1               5                  10                  15

His Leu Glu Ile Phe Pro Asn Gly Thr Ile Gln Gly Thr Arg Lys Asp
             20                  25                  30

His Ser Arg Phe Gly Ile Leu Glu Phe Ile Ser Ile Ala Val Gly Leu
         35                  40                  45

Val Ser Ile Arg Gly Val Asp Ser Gly Leu Tyr Leu Gly Met Asn Glu
 50                  55                  60

Lys Gly Glu Leu Tyr Gly Ser Glu Lys Leu Thr Gln Glu Cys Val Phe
65                   70                  75                  80

Arg Glu Gln Phe Glu Glu Asn Trp Tyr Asn Thr Tyr Ser Ser Asn Leu
             85                  90                  95

Tyr Lys His Val Asp Thr Gly Arg Arg Tyr Tyr Val Ala Leu Asn Lys
            100                 105                 110

Asp Gly Thr Pro Arg Glu Gly Thr Arg Thr Lys Arg His Gln Lys Phe
            115                 120                 125

Thr His Phe Leu Pro Arg Pro Ala Asp Pro Asp Lys Val
130                 135                 140

<210> SEQ ID NO 26
<211> LENGTH: 137
<212> TYPE: PRT
<213> ORGANISM: Homo sapiens

<400> SEQUENCE: 26

Leu Gln Gly Asp Gly Val Arg Trp Lys Lys Leu Phe Ser Phe Thr Lys
 1               5                  10                  15

Tyr Phe Leu Lys Ile Glu Lys Asn Gly Lys Val Ser Gly Thr Lys Lys
             20                  25                  30

Glu Asn Cys Pro Tyr Ser Ile Leu Glu Ile Thr Ser Val Glu Ile Gly
         35                  40                  45

Val Val Ala Val Lys Ala Ile Asn Ser Asn Tyr Tyr Leu Ala Met Asn
 50                  55                  60

Lys Lys Gly Lys Leu Tyr Gly Ser Lys Glu Phe Asn Asn Asp Cys Lys
65                   70                  75                  80

Leu Lys Glu Arg Ile Glu Glu Asn Gly Tyr Asn Thr Tyr Ala Ser Phe
             85                  90                  95

Asn Trp Gln His Asn Gly Arg Gln Met Tyr Val Ala Leu Asn Gly Lys
            100                 105                 110

Gly Ala Pro Arg Arg Gly Gln Lys Thr Arg Arg Lys Asn Thr Ser Ala
            115                 120                 125
```

His Phe Leu Pro Met Val Ala His Ser
    130                 135

<210> SEQ ID NO 27
<211> LENGTH: 140
<212> TYPE: PRT
<213> ORGANISM: Homo sapiens

<400> SEQUENCE: 27

Pro Gln Leu Lys Gly Ile Val Thr Lys Leu Phe Cys Arg Gln Gly Phe
  1               5                  10                  15

Tyr Leu Gln Ala Asn Pro Asp Gly Ser Ile Gln Gly Thr Pro Glu Asp
                 20                  25                  30

Thr Ser Ser Phe Thr His Phe Asn Leu Ile Pro Val Gly Leu Arg Val
             35                  40                  45

Val Thr Ile Gln Ser Ala Lys Leu Gly His Tyr Met Ala Met Asn Ala
         50                  55                  60

Glu Gly Leu Leu Tyr Ser Ser Pro His Phe Thr Ala Glu Cys Arg Phe
 65                  70                  75                  80

Lys Glu Cys Val Phe Glu Asn Tyr Tyr Val Leu Tyr Ala Ser Ala Leu
                 85                  90                  95

Tyr Arg Gln Arg Arg Ser Gly Arg Ala Trp Tyr Leu Gly Leu Asp Lys
                100                 105                 110

Glu Gly Gln Val Met Lys Gly Asn Arg Val Lys Thr Lys Ala Ala
            115                 120                 125

His Phe Leu Pro Lys Leu Leu Glu Val Ala Met Tyr
    130                 135                 140

<210> SEQ ID NO 28
<211> LENGTH: 141
<212> TYPE: PRT
<213> ORGANISM: Homo sapiens

<400> SEQUENCE: 28

Pro Gln Leu Lys Gly Ile Val Thr Arg Leu Phe Ser Gln Gln Gly Tyr
  1               5                  10                  15

Phe Leu Gln Met His Pro Asp Gly Thr Ile Gly Val Thr Lys Asp Glu
                 20                  25                  30

Asn Ser Asp Tyr Thr Leu Phe Asn Leu Ile Pro Val Gly Leu Arg Val
             35                  40                  45

Val Ala Ile Gln Gly Val Lys Ala Ser Leu Tyr Val Ala Met Asn Gly
         50                  55                  60

Glu Gly Tyr Leu Tyr Ser Ser Asp Val Phe Thr Pro Glu Cys Lys Phe
 65                  70                  75                  80

Lys Glu Ser Val Phe Glu Asn Tyr Tyr Val Ile Tyr Ser Ser Thr Leu
                 85                  90                  95

Tyr Arg Gln Gln Glu Ser Gly Arg Ala Trp Phe Leu Gly Leu Asn Lys
                100                 105                 110

Glu Gly Gln Ile Met Lys Gly Asn Arg Val Lys Lys Thr Lys Pro Ser
            115                 120                 125

Ser His Phe Val Pro Lys Pro Ile Glu Val Cys Met Tyr
    130                 135                 140

<210> SEQ ID NO 29
<211> LENGTH: 141
<212> TYPE: PRT
<213> ORGANISM: Homo sapiens

```
<400> SEQUENCE: 29

Pro Gln Leu Lys Gly Ile Val Thr Lys Leu Tyr Ser Arg Gln Gly Tyr
 1               5                  10                  15

His Leu Gln Leu Gln Ala Asp Gly Thr Ile Asp Gly Thr Lys Asp Glu
            20                  25                  30

Asp Ser Thr Tyr Thr Leu Phe Asn Leu Ile Pro Val Gly Leu Arg Val
        35                  40                  45

Val Ala Ile Gln Gly Val Gln Thr Lys Leu Tyr Leu Ala Met Asn Ser
 50                  55                  60

Glu Gly Tyr Leu Tyr Thr Glu Ser Glu Leu Phe Thr Pro Glu Cys Lys
 65                  70                  75                  80

Phe Lys Glu Ser Val Phe Glu Asn Tyr Tyr Val Thr Tyr Ser Met Ile
                85                  90                  95

Tyr Arg Gln Gln Gln Ser Gly Arg Gly Trp Tyr Leu Gly Leu Asn Lys
            100                 105                 110

Glu Gly Glu Ile Met Lys Gly Asn His Val Lys Lys Asn Lys Pro Ala
        115                 120                 125

Ala His Phe Leu Pro Lys Pro Leu Lys Val Ala Met Tyr
    130                 135                 140

<210> SEQ ID NO 30
<211> LENGTH: 142
<212> TYPE: PRT
<213> ORGANISM: Homo sapiens

<400> SEQUENCE: 30

Leu Gln Leu Lys Gly Ile Val Thr Arg Leu Tyr Cys Arg Gln Gly Tyr
 1               5                  10                  15

Tyr Leu Gln Met His Pro Asp Gly Ala Leu Asp Gly Thr Lys Asp Asp
            20                  25                  30

Ser Thr Asn Ser Thr Leu Phe Asn Leu Ile Pro Val Gly Leu Arg Val
        35                  40                  45

Val Ala Ile Gln Gly Val Lys Thr Gly Leu Tyr Ile Ala Met Asn Gly
 50                  55                  60

Glu Gly Tyr Leu Tyr Pro Ser Glu Leu Phe Pro Thr Pro Glu Cys Lys
 65                  70                  75                  80

Phe Lys Glu Ser Val Phe Glu Asn Tyr Tyr Val Ile Tyr Ser Ser Met
                85                  90                  95

Leu Tyr Arg Gln Gln Glu Ser Gly Arg Ala Tyr Phe Leu Gly Val Asn
            100                 105                 110

Lys Glu Gly Gln Ala Met Lys Gly Asn Arg Val Lys Lys Thr Lys Pro
        115                 120                 125

Ala Ala His Phe Leu Pro Lys Pro Leu Glu Val Ala Met Tyr
130                 135                 140

<210> SEQ ID NO 31
<211> LENGTH: 134
<212> TYPE: PRT
<213> ORGANISM: Gallus sp.

<400> SEQUENCE: 31

Trp Gly Lys Ile Thr Arg Leu Gln Tyr Leu Tyr Ser Ala Gly Pro Tyr
 1               5                  10                  15

Val Ser Asn Cys Phe Leu Arg Ile Arg Ser Asp Gly Ser Asp Gly Cys
            20                  25                  30
```

-continued

Glu Glu Asp Gln Asn Glu Arg Asn Leu Leu Glu Phe Arg Ala Val Ala
         35                  40                  45

Leu Lys Thr Ile Ala Ile Lys Asp Val Ser Ser Val Arg Tyr Leu Cys
     50                  55                  60

Met Ser Ala Asp Gly Lys Ile Tyr Gly Leu Ile Arg Tyr Ser Glu Glu
 65                  70                  75                  80

Asp Cys Thr Phe Arg Glu Glu Met Asp Cys Leu Gly Tyr Asn Gln Tyr
                 85                  90                  95

Arg Ser Met Lys His His Leu His Ile Ile Phe Ile Gln Ala Lys Pro
             100                 105                 110

Arg Glu Gln Leu Gln Asp Gln Lys Pro Ser Asn Phe Ile Pro Val Phe
         115                 120                 125

His Arg Ser Phe Phe Glu
         130

<210> SEQ ID NO 32
<211> LENGTH: 141
<212> TYPE: PRT
<213> ORGANISM: Homo sapiens

<400> SEQUENCE: 32

Leu Lys Gly Ile Leu Arg Arg Gln Leu Tyr Cys Arg Thr Gly Phe
 1               5                  10                  15

His Leu Glu Ile Phe Pro Asn Gly Thr Asp His Gly Thr Arg His Asp
             20                  25                  30

His Ser Arg Phe Gly Ile Leu Glu Phe Ile Ser Leu Ala Val Gly Leu
         35                  40                  45

Ile Ser Ile Arg Gly Val Asp Ser Gly Leu Tyr Leu Gly Met Asn Glu
     50                  55                  60

Arg Gly Glu Leu Tyr Gly Ser Lys Lys Leu Thr Arg Glu Cys Val Phe
 65                  70                  75                  80

Arg Glu Gln Phe Glu Glu Asn Trp Tyr Asn Thr Tyr Ala Ser Thr Leu
                 85                  90                  95

Tyr Lys His Ser Asp Ser Glu Arg Gln Tyr Tyr Val Ala Leu Asn Lys
             100                 105                 110

Asp Gly Ser Pro Arg Glu Gly Tyr Arg Thr Lys Arg His Gln Lys Phe
         115                 120                 125

Thr His Phe Leu Pro Arg Pro Ala Asp Pro Ser Lys Leu
     130                 135                 140

<210> SEQ ID NO 33
<211> LENGTH: 136
<212> TYPE: PRT
<213> ORGANISM: Homo sapiens

<400> SEQUENCE: 33

Ser Arg Arg Gln Ile Arg Glu Tyr Gln Leu Tyr Ser Arg Thr Ser Gly
 1               5                  10                  15

Lys His Val Gln Val Thr Gly Arg Arg Ile Ser Ala Thr Ala Glu Asp
             20                  25                  30

Gly Asn Lys Phe Ala Lys Leu Ile Val Glu Thr Asp Thr Phe Gly Ser
         35                  40                  45

Arg Val Arg Lys Gly Val Ala Glu Ser Lys Tyr Ile Cys Met Asn Lys
     50                  55                  60

Arg Gly Lys Leu Ile Gly Lys Pro Ser Gly Lys Ser Lys Asp Cys Val
 65                  70                  75                  80

-continued

```
Phe Thr Glu Ile Val Leu Glu Asn Asn Tyr Thr Ala Phe Gln Asn Ala
                 85                  90                  95

Arg His Glu Gly Trp Phe Met Ala Phe Thr Arg Gln Gly Arg Pro Arg
            100                 105                 110

Gln Ala Ser Arg Ser Arg Gln Asn Gln Arg Glu Ala His Phe Ile Lys
        115                 120                 125

Arg Leu Tyr Gln Gly Gln Leu Pro
    130                 135

<210> SEQ ID NO 34
<211> LENGTH: 137
<212> TYPE: PRT
<213> ORGANISM: Homo sapiens

<400> SEQUENCE: 34

Ser Arg Lys Gln Leu Arg Leu Tyr Gln Leu Tyr Ser Arg Thr Ser Gly
  1               5                  10                  15

Lys His Ile Gln Val Leu Gly Arg Arg Ile Ser Ala Arg Gly Glu Asp
                 20                  25                  30

Gly Pro Lys Tyr Ala Gln Leu Leu Val Glu Thr Asp Thr Phe Gly Ser
             35                  40                  45

Gln Val Arg Ile Lys Gly Lys Glu Thr Glu Phe Tyr Leu Cys Met Asn
 50                  55                  60

Arg Lys Gly Lys Leu Val Gly Lys Pro Asp Gly Thr Ser Lys Glu Cys
 65                  70                  75                  80

Val Phe Ile Glu Lys Val Leu Glu Asn Asn Tyr Thr Ala Leu Met Ser
                 85                  90                  95

Ala Lys Tyr Ser Gly Trp Tyr Val Gly Phe Thr Lys Lys Gly Arg Pro
            100                 105                 110

Arg Lys Gly Pro Lys Thr Arg Glu Asn Gln Gln Asp Val His Phe Met
        115                 120                 125

Lys Arg Tyr Pro Lys Gly Gln Pro Glu
    130                 135

<210> SEQ ID NO 35
<211> LENGTH: 137
<212> TYPE: PRT
<213> ORGANISM: Homo sapiens

<400> SEQUENCE: 35

Trp Gly Pro Ile Arg Leu Arg His Leu Tyr Thr Ser Gly Pro His Gly
  1               5                  10                  15

Leu Ser Ser Cys Phe Leu Arg Ile Arg Ala Asp Gly Val Asp Gly Cys
                 20                  25                  30

Ala Arg Gly Gln Ser Ala Ile Ser Leu Leu Glu Ile Lys Ala Val Ala
             35                  40                  45

Leu Arg Thr Val Ala Ile Lys Gly Val His Ser Val Arg Tyr Leu Cys
 50                  55                  60

Met Gly Ala Asp Gly Lys Met Gln Gly Leu Leu Gln Tyr Ser Glu Glu
 65                  70                  75                  80

Asp Cys Ala Phe Glu Glu Ile Arg Pro Asp Gly Tyr Asn Val Tyr
                 85                  90                  95

Arg Ser Glu Lys His Arg Leu Pro Val Ser Leu Ser Ser Ala Lys Gln
            100                 105                 110

Arg Gln Leu Tyr Lys Asn Arg Gly Phe Leu Pro Leu Ser His Phe Leu
        115                 120                 125
```

```
Pro Met Leu Pro Met Val Pro Glu Glu
    130                 135
```

<210> SEQ ID NO 36
<211> LENGTH: 39
<212> TYPE: PRT
<213> ORGANISM: Unknown Organism
<220> FEATURE:
<223> OTHER INFORMATION: Description of Unknown Organism: SCF peptide

<400> SEQUENCE: 36

```
Glu Gly Ile Cys Arg Asn Arg Val Thr Asn Asn Val Lys Asp Val Thr
  1               5                  10                  15

Lys Leu Val Ala Asn Leu Pro Lys Asp Tyr Met Ile Thr Leu Lys Tyr
             20                  25                  30

Val Pro Gly Met Asp Val Leu
             35
```

<210> SEQ ID NO 37
<211> LENGTH: 42
<212> TYPE: PRT
<213> ORGANISM: Unknown Organism
<220> FEATURE:
<223> OTHER INFORMATION: Description of Unknown Organism: M-SCF peptide

<400> SEQUENCE: 37

```
Ser Glu Tyr Cys Ser His Met Ile Gly Ser Gly His Leu Gln Ser Leu
  1               5                  10                  15

Gln Arg Leu Ile Asp Ser Gln Met Glu Thr Ser Cys Gln Ile Thr Phe
             20                  25                  30

Glu Phe Val Asp Gln Glu Gln Leu Lys Asp
         35                  40
```

<210> SEQ ID NO 38
<211> LENGTH: 36
<212> TYPE: PRT
<213> ORGANISM: Unknown Organism
<220> FEATURE:
<223> OTHER INFORMATION: Description of Unknown Organism: IL-5 peptide

<400> SEQUENCE: 38

```
Ile Pro Thr Ser Ala Leu Val Lys Glu Thr Leu Ala Leu Leu Ser Thr
  1               5                  10                  15

His Arg Thr Leu Leu Ile Ala Asn Glu Thr Leu Arg Ile Pro Val Pro
             20                  25                  30

Val His Lys Asn
         35
```

<210> SEQ ID NO 39
<211> LENGTH: 59
<212> TYPE: PRT
<213> ORGANISM: Unknown Organism
<220> FEATURE:
<223> OTHER INFORMATION: Description of Unknown Organism: SCF peptide

<400> SEQUENCE: 39

```
Pro Ser His Cys Trp Ile Ser Glu Met Val Val Gln Leu Ser Asp Ser
  1               5                  10                  15

Leu Thr Asp Leu Leu Asp Lys Phe Ser Asn Ile Ser Glu Gly Leu Ser
             20                  25                  30

Asn Tyr Ser Leu Ile Asp Lys Ile Val Asn Ile Val Asp Asp Leu Val
             35                  40                  45
```

```
Glu Cys Val Lys Glu Asn Ser Ser Lys Asp Leu
    50                  55
```

<210> SEQ ID NO 40
<211> LENGTH: 50
<212> TYPE: PRT
<213> ORGANISM: Unknown Organism
<220> FEATURE:
<223> OTHER INFORMATION: Description of Unknown Organism: M-SCF peptide

<400> SEQUENCE: 40

```
Pro Val Cys Tyr Leu Lys Lys Ala Phe Leu Leu Val Gln Asp Ile Met
 1               5                  10                  15

Glu Asp Thr Met Arg Phe Arg Asp Asn Thr Pro Asn Ala Ile Ala Ile
                20                  25                  30

Val Gln Leu Gln Glu Leu Ser Ile Arg Leu Lys Ser Cys Phe Thr Lys
            35                  40                  45

Asp Tyr
    50
```

<210> SEQ ID NO 41
<211> LENGTH: 48
<212> TYPE: PRT
<213> ORGANISM: Unknown Organism
<220> FEATURE:
<223> OTHER INFORMATION: Description of Unknown Organism: IL-5 peptide

<400> SEQUENCE: 41

```
His Gln Leu Cys Thr Glu Glu Ile Phe Gln Gly Ile Gly Thr Leu Glu
 1               5                  10                  15

Ser Gln Thr Val Gln Gly Gly Thr Val Glu Arg Leu Phe Lys Asn Leu
                20                  25                  30

Ser Leu Ile Lys Lys Tyr Ile Asp Gly Gln Lys Lys Lys Cys Gly Glu
            35                  40                  45
```

<210> SEQ ID NO 42
<211> LENGTH: 43
<212> TYPE: PRT
<213> ORGANISM: Unknown Organism
<220> FEATURE:
<223> OTHER INFORMATION: Description of Unknown Organism: SCF peptide

<400> SEQUENCE: 42

```
Lys Lys Ser Phe Lys Ser Pro Glu Pro Arg Leu Phe Thr Pro Glu Glu
 1               5                  10                  15

Phe Phe Arg Ile Phe Asn Arg Ser Ile Asp Ala Phe Lys Asp Phe Val
                20                  25                  30

Val Ala Ser Glu Thr Ser Asp Cys Val Val Ser
            35                  40
```

<210> SEQ ID NO 43
<211> LENGTH: 56
<212> TYPE: PRT
<213> ORGANISM: Unknown Organism
<220> FEATURE:
<223> OTHER INFORMATION: Description of Unknown Organism: M-SCF peptide

<400> SEQUENCE: 43

```
Glu Glu His Asp Lys Ala Cys Val Arg Thr Phe Tyr Glu Thr Pro Leu
 1               5                  10                  15

Gln Leu Leu Glu Lys Val Lys Asn Val Phe Asn Glu Thr Lys Asn Leu
                20                  25                  30
```

```
Leu Asp Lys Asp Trp Asn Ile Phe Ser Lys Asn Cys Asn Asn Ser Phe
         35                  40                  45

Ala Glu Cys Ser Ser Gln Gly His
    50                  55

<210> SEQ ID NO 44
<211> LENGTH: 24
<212> TYPE: PRT
<213> ORGANISM: Unknown Organism
<220> FEATURE:
<223> OTHER INFORMATION: Description of Unknown Organism: IL-5 peptide

<400> SEQUENCE: 44

Glu Arg Arg Arg Val Asn Gln Phe Leu Asp Tyr Leu Gln Glu Phe Leu
  1               5                  10                  15

Gly Val Met Asn Thr Glu Trp Ile
             20

<210> SEQ ID NO 45
<211> LENGTH: 141
<212> TYPE: PRT
<213> ORGANISM: Homo sapiens

<400> SEQUENCE: 45

Glu Gly Ile Cys Arg Asn Arg Val Thr Asn Asn Val Lys Asp Val Thr
  1               5                  10                  15

Lys Leu Val Ala Asn Leu Pro Lys Asp Tyr Met Ile Thr Leu Lys Tyr
             20                  25                  30

Val Pro Gly Met Asp Val Leu Pro Ser His Cys Trp Ile Ser Glu Met
         35                  40                  45

Val Val Gln Leu Ser Asp Ser Leu Thr Asp Leu Leu Asp Lys Phe Ser
    50                  55                  60

Asn Ile Ser Glu Gly Leu Ser Asn Tyr Ser Ile Ile Asp Lys Leu Val
 65                  70                  75                  80

Asn Ile Val Asp Asp Leu Val Glu Cys Val Lys Glu Asn Ser Ser Lys
                 85                  90                  95

Asp Leu Lys Lys Ser Phe Lys Ser Pro Glu Pro Arg Leu Phe Thr Pro
            100                 105                 110

Glu Glu Phe Phe Arg Ile Phe Asn Arg Ser Ile Asp Ala Phe Lys Asp
        115                 120                 125

Phe Val Val Ala Ser Glu Thr Ser Asp Cys Val Val Ser
    130                 135                 140

<210> SEQ ID NO 46
<211> LENGTH: 141
<212> TYPE: PRT
<213> ORGANISM: Rattus sp.

<400> SEQUENCE: 46

Gln Glu Ile Cys Arg Asn Pro Val Thr Asp Asn Val Lys Asp Ile Thr
  1               5                  10                  15

Lys Leu Val Ala Asn Leu Pro Asn Asp Tyr Met Ile Thr Leu Asn Tyr
             20                  25                  30

Val Ala Gly Met Asp Val Leu Pro Ser His Cys Trp Leu Arg Asp Met
         35                  40                  45

Val Thr His Ser Leu Val Ser Leu Thr Thr Leu Leu Asp Lys Phe Ser
    50                  55                  60

Asn Ile Ser Glu Gly Leu Ser Asn Tyr Ser Ile Ile Asp Lys Leu Gly
 65                  70                  75                  80
```

```
Asn Ile Val Asp Asp Leu Val Ala Cys Met Glu Glu Asn Ala Pro Lys
                85                  90                  95

Asn Val Lys Glu Ser Leu Lys Lys Pro Glu Thr Arg Asn Phe Thr Pro
            100                 105                 110

Glu Glu Phe Phe Arg Ile Phe Asn Arg Ser Ile Asp Ala Phe Lys Asp
        115                 120                 125

Phe Met Val Ala Ser Asp Thr Ser Asp Cys Val Leu Ser
    130                 135                 140

<210> SEQ ID NO 47
<211> LENGTH: 141
<212> TYPE: PRT
<213> ORGANISM: Mus sp.

<400> SEQUENCE: 47

Lys Glu Ile Cys Gly Asn Pro Val Thr Asp Asn Val Lys Asp Ile Thr
  1               5                  10                  15

Lys Leu Val Ala Asn Leu Pro Asn Asp Tyr Met Ile Thr Leu Asn Tyr
             20                  25                  30

Val Ala Gly Met Asp Val Leu Pro Ser His Cys Trp Leu Arg Asp Met
         35                  40                  45

Val Ile Gln Leu Ser Leu Ser Leu Thr Thr Leu Leu Asp Lys Phe Ser
 50                  55                  60

Asn Ile Ser Glu Gly Leu Ser Asn Tyr Ser Ile Ile Asp Lys Leu Gly
 65                  70                  75                  80

Lys Ile Val Asp Asp Leu Val Leu Cys Met Glu Glu Asn Ala Pro Lys
                85                  90                  95

Asn Ile Lys Glu Ser Pro Lys Arg Pro Glu Thr Arg Ser Phe Thr Pro
            100                 105                 110

Glu Glu Phe Phe Ser Ile Phe Asn Arg Ser Ile Ala Asp Phe Lys Asp
        115                 120                 125

Phe Met Val Ala Ser Asp Thr Ser Asp Cys Val Leu Ser
    130                 135                 140

<210> SEQ ID NO 48
<211> LENGTH: 142
<212> TYPE: PRT
<213> ORGANISM: Canis familiaris

<400> SEQUENCE: 48

Lys Gly Ile Cys Gly Lys Arg Val Thr Asp Asp Val Lys Asp Val Thr
  1               5                  10                  15

Lys Leu Val Ala Asn Leu Pro Lys Asp Tyr Lys Ile Ala Leu Lys Tyr
             20                  25                  30

Val Pro Gly Met Asp Val Leu Pro Ser His Cys Trp Ile Ser Val Met
         35                  40                  45

Val Glu Gln Leu Ser Val Ser Leu Thr Asp Leu Leu Asp Lys Phe Ser
 50                  55                  60

Asn Ile Ser Glu Gly Leu Ser Asn Tyr Ser Ile Ile Asp Lys Leu Val
 65                  70                  75                  80

Lys Ile Val Asp Asp Leu Val Glu Cys Thr Glu Gly Tyr Ser Phe Glu
                85                  90                  95

Asn Val Lys Lys Ala Pro Lys Ser Pro Glu Leu Arg Leu Phe Thr Pro
            100                 105                 110

Glu Glu Phe Phe Arg Ile Phe Asn Arg Ser Ile Asp Ala Phe Lys Asp
        115                 120                 125
```

```
Leu Glu Thr Val Ala Ser Lys Ser Ser Glu Cys Val Val Ser
        130                 135                 140
```

<210> SEQ ID NO 49
<211> LENGTH: 142
<212> TYPE: PRT
<213> ORGANISM: Sus scrofa

<400> SEQUENCE: 49

```
Gln Gly Ile Cys Arg Asn Arg Val Thr Asp Asp Val Lys Asp Val Thr
 1               5                  10                  15

Lys Leu Val Ala Asn Leu Pro Lys Asp Tyr Lys Ile Thr Leu Lys Tyr
            20                  25                  30

Val Pro Gly Met Asp Val Leu Pro Ser His Cys Trp Ile Ser Glu Met
        35                  40                  45

Val Glu Gln Leu Ser Val Ser Leu Thr Asp Leu Leu Asp Lys Phe Ser
    50                  55                  60

Asn Ile Ser Glu Gly Leu Ser Asn Tyr Ser Ile Ile Asp Lys Leu Gly
 65                  70                  75                  80

Lys Ile Val Asp Asp Leu Val Glu Cys Met Glu Glu His Ser Phe Glu
                85                  90                  95

Asn Val Lys Lys Ser Ser Lys Ser Pro Glu Pro Arg Leu Phe Thr Pro
            100                 105                 110

Glu Lys Phe Phe Gly Ile Phe Asn Arg Ser Ile Asp Ala Phe Lys Asp
        115                 120                 125

Leu Glu Met Val Ala Pro Lys Thr Ser Glu Cys Val Ile Ser
    130                 135                 140
```

<210> SEQ ID NO 50
<211> LENGTH: 13
<212> TYPE: PRT
<213> ORGANISM: Homo sapiens

<400> SEQUENCE: 50

```
Gly His Phe Lys Asp Pro Lys Arg Leu Tyr Cys Lys Asn
 1               5                  10
```

<210> SEQ ID NO 51
<211> LENGTH: 13
<212> TYPE: PRT
<213> ORGANISM: Homo sapiens

<400> SEQUENCE: 51

```
Gly Gly Phe Phe Leu Arg Ile His Pro Asp Gly Arg Val
 1               5                  10
```

<210> SEQ ID NO 52
<211> LENGTH: 13
<212> TYPE: PRT
<213> ORGANISM: Homo sapiens

<400> SEQUENCE: 52

```
Asp Gly Val Arg Glu Lys Ser Asp Pro His Ile Lys Leu
 1               5                  10
```

<210> SEQ ID NO 53
<211> LENGTH: 13
<212> TYPE: PRT
<213> ORGANISM: Homo sapiens

<400> SEQUENCE: 53

Gln Leu Gln Ala Glu Glu Arg Gly Val Val Ser Ile Lys
1               5                   10

<210> SEQ ID NO 54
<211> LENGTH: 13
<212> TYPE: PRT
<213> ORGANISM: Homo sapiens

<400> SEQUENCE: 54

Gly Val Ser Ala Asn Arg Tyr Leu Ala Met Lys Glu Asp
1               5                   10

<210> SEQ ID NO 55
<211> LENGTH: 13
<212> TYPE: PRT
<213> ORGANISM: Homo sapiens

<400> SEQUENCE: 55

Gly Arg Leu Leu Ala Ser Lys Ser Val Thr Asp Glu Cys
1               5                   10

<210> SEQ ID NO 56
<211> LENGTH: 13
<212> TYPE: PRT
<213> ORGANISM: Homo sapiens

<400> SEQUENCE: 56

Phe Phe Phe Glu Arg Leu Glu Ser Asn Tyr Asn Thr
1               5                   10

<210> SEQ ID NO 57
<211> LENGTH: 13
<212> TYPE: PRT
<213> ORGANISM: Homo sapiens

<400> SEQUENCE: 57

Tyr Arg Ser Arg Lys Tyr Thr Ser Trp Tyr Val Ala Leu
1               5                   10

<210> SEQ ID NO 58
<211> LENGTH: 13
<212> TYPE: PRT
<213> ORGANISM: Homo sapiens

<400> SEQUENCE: 58

Lys Arg Thr Gly Gln Tyr Lys Leu Gly Ser Lys Thr Gly
1               5                   10

<210> SEQ ID NO 59
<211> LENGTH: 13
<212> TYPE: PRT
<213> ORGANISM: Homo sapiens

<400> SEQUENCE: 59

Pro Gly Gln Lys Ala Ile Leu Phe Leu Pro Met Ser Ala
1               5                   10

<210> SEQ ID NO 60
<211> LENGTH: 13
<212> TYPE: PRT
<213> ORGANISM: Homo sapiens

<400> SEQUENCE: 60

Gly His Phe Lys Asp Pro Lys Arg Leu Tyr Cys Lys Asn

<210> SEQ ID NO 61
<211> LENGTH: 13
<212> TYPE: PRT
<213> ORGANISM: Homo sapiens

<400> SEQUENCE: 61

Gly Gly Phe Phe Leu Arg Ile His Pro Asp Gly Arg Val
 1               5                  10

<210> SEQ ID NO 62
<211> LENGTH: 13
<212> TYPE: PRT
<213> ORGANISM: Homo sapiens

<400> SEQUENCE: 62

Asp Gly Val Arg Glu Lys Ser Asp Pro His Ile Lys Leu
 1               5                  10

<210> SEQ ID NO 63
<211> LENGTH: 13
<212> TYPE: PRT
<213> ORGANISM: Homo sapiens

<400> SEQUENCE: 63

Gln Leu Gln Ala Glu Glu Arg Gly Val Val Ser Ile Lys
 1               5                  10

<210> SEQ ID NO 64
<211> LENGTH: 13
<212> TYPE: PRT
<213> ORGANISM: Homo sapiens

<400> SEQUENCE: 64

Gly Val Ser Ala Asn Arg Tyr Leu Ala Met Lys Glu Asp
 1               5                  10

<210> SEQ ID NO 65
<211> LENGTH: 13
<212> TYPE: PRT
<213> ORGANISM: Homo sapiens

<400> SEQUENCE: 65

Gly Arg Leu Leu Ala Ser Lys Ser Val Thr Asp Glu Cys
 1               5                  10

<210> SEQ ID NO 66
<211> LENGTH: 13
<212> TYPE: PRT
<213> ORGANISM: Homo sapiens

<400> SEQUENCE: 66

Phe Phe Phe Glu Arg Leu Glu Ser Asn Asn Tyr Asn Thr
 1               5                  10

<210> SEQ ID NO 67
<211> LENGTH: 13
<212> TYPE: PRT
<213> ORGANISM: Homo sapiens

<400> SEQUENCE: 67

Tyr Arg Ser Arg Lys Tyr Thr Ser Trp Tyr Val Ala Leu
 1               5                  10

```
<210> SEQ ID NO 68
<211> LENGTH: 13
<212> TYPE: PRT
<213> ORGANISM: Homo sapiens

<400> SEQUENCE: 68

Lys Arg Thr Gly Gln Tyr Lys Leu Gly Ser Lys Thr Gly
 1               5                  10

<210> SEQ ID NO 69
<211> LENGTH: 13
<212> TYPE: PRT
<213> ORGANISM: Homo sapiens

<400> SEQUENCE: 69

Pro Gly Gln Lys Ala Ile Leu Phe Leu Pro Met Ser Ala
 1               5                  10

<210> SEQ ID NO 70
<211> LENGTH: 13
<212> TYPE: PRT
<213> ORGANISM: Homo sapiens

<400> SEQUENCE: 70

Gly His Phe Lys Asp Pro Lys Arg Leu Tyr Cys Lys Asn
 1               5                  10

<210> SEQ ID NO 71
<211> LENGTH: 13
<212> TYPE: PRT
<213> ORGANISM: Homo sapiens

<400> SEQUENCE: 71

Gly Gly Phe Phe Leu Arg Ile His Pro Asp Gly Arg Val
 1               5                  10

<210> SEQ ID NO 72
<211> LENGTH: 13
<212> TYPE: PRT
<213> ORGANISM: Homo sapiens

<400> SEQUENCE: 72

Asp Gly Val Arg Glu Lys Ser Asp Pro His Ile Lys Leu
 1               5                  10

<210> SEQ ID NO 73
<211> LENGTH: 13
<212> TYPE: PRT
<213> ORGANISM: Homo sapiens

<400> SEQUENCE: 73

Gln Leu Gln Ala Glu Glu Arg Gly Val Val Ser Ile Lys
 1               5                  10

<210> SEQ ID NO 74
<211> LENGTH: 13
<212> TYPE: PRT
<213> ORGANISM: Homo sapiens

<400> SEQUENCE: 74

Gly Val Ser Ala Asn Arg Tyr Leu Ala Met Lys Glu Asp
 1               5                  10

<210> SEQ ID NO 75
```

```
<211> LENGTH: 13
<212> TYPE: PRT
<213> ORGANISM: Homo sapiens

<400> SEQUENCE: 75

Gly Arg Leu Leu Ala Ser Lys Ser Val Thr Asp Glu Cys
 1               5                  10

<210> SEQ ID NO 76
<211> LENGTH: 13
<212> TYPE: PRT
<213> ORGANISM: Homo sapiens

<400> SEQUENCE: 76

Phe Phe Phe Glu Arg Leu Glu Ser Asn Tyr Asn Thr
 1               5                  10

<210> SEQ ID NO 77
<211> LENGTH: 13
<212> TYPE: PRT
<213> ORGANISM: Homo sapiens

<400> SEQUENCE: 77

Tyr Arg Ser Arg Lys Tyr Thr Ser Trp Tyr Val Ala Leu
 1               5                  10

<210> SEQ ID NO 78
<211> LENGTH: 13
<212> TYPE: PRT
<213> ORGANISM: Homo sapiens

<400> SEQUENCE: 78

Lys Arg Thr Gly Gln Tyr Lys Leu Gly Ser Lys Thr Gly
 1               5                  10

<210> SEQ ID NO 79
<211> LENGTH: 13
<212> TYPE: PRT
<213> ORGANISM: Homo sapiens

<400> SEQUENCE: 79

Pro Gly Gln Lys Ala Ile Leu Phe Leu Pro Met Ser Ala
 1               5                  10

<210> SEQ ID NO 80
<211> LENGTH: 13
<212> TYPE: PRT
<213> ORGANISM: Homo sapiens

<400> SEQUENCE: 80

Gly His Phe Lys Asp Pro Lys Arg Leu Tyr Cys Lys Asn
 1               5                  10

<210> SEQ ID NO 81
<211> LENGTH: 13
<212> TYPE: PRT
<213> ORGANISM: Homo sapiens

<400> SEQUENCE: 81

Gly Gly Phe Phe Leu Arg Ile His Pro Asp Gly Arg Val
 1               5                  10

<210> SEQ ID NO 82
<211> LENGTH: 13
<212> TYPE: PRT
```

<213> ORGANISM: Homo sapiens

<400> SEQUENCE: 82

Asp Gly Val Arg Glu Lys Ser Asp Pro His Ile Lys Leu
1               5                   10

<210> SEQ ID NO 83
<211> LENGTH: 13
<212> TYPE: PRT
<213> ORGANISM: Homo sapiens

<400> SEQUENCE: 83

Gln Leu Gln Ala Glu Glu Arg Gly Val Val Ser Ile Lys
1               5                   10

<210> SEQ ID NO 84
<211> LENGTH: 13
<212> TYPE: PRT
<213> ORGANISM: Homo sapiens

<400> SEQUENCE: 84

Gly Val Ser Ala Asn Arg Tyr Leu Ala Met Lys Glu Asp
1               5                   10

<210> SEQ ID NO 85
<211> LENGTH: 13
<212> TYPE: PRT
<213> ORGANISM: Homo sapiens

<400> SEQUENCE: 85

Gly Arg Leu Leu Ala Ser Lys Ser Val Thr Asp Glu Cys
1               5                   10

<210> SEQ ID NO 86
<211> LENGTH: 13
<212> TYPE: PRT
<213> ORGANISM: Homo sapiens

<400> SEQUENCE: 86

Tyr Arg Ser Arg Lys Tyr Thr Ser Trp Tyr Val Ala Leu
1               5                   10

<210> SEQ ID NO 87
<211> LENGTH: 13
<212> TYPE: PRT
<213> ORGANISM: Homo sapiens

<400> SEQUENCE: 87

Tyr Arg Ser Arg Lys Tyr Thr Ser Trp Tyr Val Ala Leu
1               5                   10

<210> SEQ ID NO 88
<211> LENGTH: 13
<212> TYPE: PRT
<213> ORGANISM: Homo sapiens

<400> SEQUENCE: 88

Lys Arg Thr Gly Gln Tyr Lys Leu Gly Ser Lys Thr Gly
1               5                   10

<210> SEQ ID NO 89
<211> LENGTH: 13
<212> TYPE: PRT
<213> ORGANISM: Homo sapiens

```
<400> SEQUENCE: 89

Pro Gly Gln Lys Ala Ile Leu Phe Leu Pro Met Ser Ala
 1               5                  10

<210> SEQ ID NO 90
<211> LENGTH: 13
<212> TYPE: PRT
<213> ORGANISM: Homo sapiens

<400> SEQUENCE: 90

Asn Ser Asn Asn Lys Arg Ala Pro Tyr Trp Thr Asn Thr
 1               5                  10

<210> SEQ ID NO 91
<211> LENGTH: 13
<212> TYPE: PRT
<213> ORGANISM: Homo sapiens

<400> SEQUENCE: 91

Glu Lys Met Glu Lys Arg Leu His Ala Val Pro Ala Ala
 1               5                  10

<210> SEQ ID NO 92
<211> LENGTH: 13
<212> TYPE: PRT
<213> ORGANISM: Homo sapiens

<400> SEQUENCE: 92

Asn Thr Val Lys Phe Arg Cys Pro Ala Gly Gly Asn Pro
 1               5                  10

<210> SEQ ID NO 93
<211> LENGTH: 13
<212> TYPE: PRT
<213> ORGANISM: Homo sapiens

<400> SEQUENCE: 93

Met Pro Thr Met Arg Trp Leu Lys Asn Gly Lys Glu Phe
 1               5                  10

<210> SEQ ID NO 94
<211> LENGTH: 13
<212> TYPE: PRT
<213> ORGANISM: Homo sapiens

<400> SEQUENCE: 94

Lys Gln Glu His Arg Ile Gly Gly Tyr Lys Val Arg Asn
 1               5                  10

<210> SEQ ID NO 95
<211> LENGTH: 13
<212> TYPE: PRT
<213> ORGANISM: Homo sapiens

<400> SEQUENCE: 95

Gln His Trp Ser Leu Ile Met Glu Ser Val Val Pro Ser
 1               5                  10

<210> SEQ ID NO 96
<211> LENGTH: 13
<212> TYPE: PRT
<213> ORGANISM: Homo sapiens

<400> SEQUENCE: 96
```

Asp Lys Gly Asn Tyr Thr Cys Val Val Glu Asn Glu Tyr
1               5                   10

<210> SEQ ID NO 97
<211> LENGTH: 13
<212> TYPE: PRT
<213> ORGANISM: Homo sapiens

<400> SEQUENCE: 97

Gly Ser Ile Asn His Thr Tyr His Leu Asp Val Val Glu
1               5                   10

<210> SEQ ID NO 98
<211> LENGTH: 13
<212> TYPE: PRT
<213> ORGANISM: Homo sapiens

<400> SEQUENCE: 98

Arg Ser Pro His Arg Pro Ile Leu Gln Ala Gly Leu Pro
1               5                   10

<210> SEQ ID NO 99
<211> LENGTH: 13
<212> TYPE: PRT
<213> ORGANISM: Homo sapiens

<400> SEQUENCE: 99

Ala Asn Ala Ser Thr Val Val Gly Gly Asp Val Glu Phe
1               5                   10

<210> SEQ ID NO 100
<211> LENGTH: 13
<212> TYPE: PRT
<213> ORGANISM: Homo sapiens

<400> SEQUENCE: 100

Val Cys Lys Val Tyr Ser Asp Ala Gln Pro His Ile Gln
1               5                   10

<210> SEQ ID NO 101
<211> LENGTH: 13
<212> TYPE: PRT
<213> ORGANISM: Homo sapiens

<400> SEQUENCE: 101

Trp Ile Lys His Val Glu Lys Asn Gly Ser Lys Tyr Gly
1               5                   10

<210> SEQ ID NO 102
<211> LENGTH: 13
<212> TYPE: PRT
<213> ORGANISM: Homo sapiens

<400> SEQUENCE: 102

Pro Asp Gly Leu Pro Tyr Leu Lys Val Leu Lys Ala Ala
1               5                   10

<210> SEQ ID NO 103
<211> LENGTH: 13
<212> TYPE: PRT
<213> ORGANISM: Homo sapiens

<400> SEQUENCE: 103

Gly Val Asn Thr Thr Asp Lys Glu Ile Glu Val Leu Tyr
1               5                   10

<210> SEQ ID NO 104
<211> LENGTH: 13
<212> TYPE: PRT
<213> ORGANISM: Homo sapiens

<400> SEQUENCE: 104

Ile Arg Asn Val Thr Phe Glu Asp Ala Gly Glu Tyr Thr
1               5                   10

<210> SEQ ID NO 105
<211> LENGTH: 13
<212> TYPE: PRT
<213> ORGANISM: Homo sapiens

<400> SEQUENCE: 105

Cys Leu Ala Gly Asn Ser Ile Gly Ile Ser Phe His Ser
1               5                   10

<210> SEQ ID NO 106
<211> LENGTH: 12
<212> TYPE: PRT
<213> ORGANISM: Homo sapiens

<400> SEQUENCE: 106

Ala Trp Leu Thr Val Leu Pro Ala Pro Gly Arg Glu
1               5                   10

<210> SEQ ID NO 107
<211> LENGTH: 13
<212> TYPE: PRT
<213> ORGANISM: Homo sapiens

<400> SEQUENCE: 107

Asn Ser Asn Asn Lys Arg Ala Pro Tyr Trp Thr Asn Thr
1               5                   10

<210> SEQ ID NO 108
<211> LENGTH: 13
<212> TYPE: PRT
<213> ORGANISM: Homo sapiens

<400> SEQUENCE: 108

Glu Lys Met Glu Lys Arg Leu His Ala Val Pro Ala Ala
1               5                   10

<210> SEQ ID NO 109
<211> LENGTH: 13
<212> TYPE: PRT
<213> ORGANISM: Homo sapiens

<400> SEQUENCE: 109

Asn Thr Val Lys Phe Arg Cys Pro Ala Gly Gly Asn Pro
1               5                   10

<210> SEQ ID NO 110
<211> LENGTH: 13
<212> TYPE: PRT
<213> ORGANISM: Homo sapiens

<400> SEQUENCE: 110

Met Pro Thr Met Arg Thr Leu Lys Asn Gly Lys Glu Phe
1               5                   10

```
<210> SEQ ID NO 111
<211> LENGTH: 13
<212> TYPE: PRT
<213> ORGANISM: Homo sapiens

<400> SEQUENCE: 111

Lys Gln Glu His Arg Ile Gly Gly Tyr Lys Val Arg Asn
 1               5                  10

<210> SEQ ID NO 112
<211> LENGTH: 13
<212> TYPE: PRT
<213> ORGANISM: Homo sapiens

<400> SEQUENCE: 112

Gln His Trp Ser Leu Ile Met Glu Ser Val Val Pro Ser
 1               5                  10

<210> SEQ ID NO 113
<211> LENGTH: 13
<212> TYPE: PRT
<213> ORGANISM: Homo sapiens

<400> SEQUENCE: 113

Asp Lys Gly Asn Tyr Thr Cys Val Val Glu Asn Glu Tyr
 1               5                  10

<210> SEQ ID NO 114
<211> LENGTH: 13
<212> TYPE: PRT
<213> ORGANISM: Homo sapiens

<400> SEQUENCE: 114

Gly Ser Ile Asn His Thr Tyr His Leu Asp Val Val Glu
 1               5                  10

<210> SEQ ID NO 115
<211> LENGTH: 13
<212> TYPE: PRT
<213> ORGANISM: Homo sapiens

<400> SEQUENCE: 115

Arg Ser Pro His Arg Pro Ile Leu Gln Ala Gly Leu Pro
 1               5                  10

<210> SEQ ID NO 116
<211> LENGTH: 13
<212> TYPE: PRT
<213> ORGANISM: Homo sapiens

<400> SEQUENCE: 116

Ala Asn Ala Ser Thr Val Val Gly Gly Asp Val Glu Phe
 1               5                  10

<210> SEQ ID NO 117
<211> LENGTH: 13
<212> TYPE: PRT
<213> ORGANISM: Homo sapiens

<400> SEQUENCE: 117

Val Cys Lys Val Tyr Ser Asp Ala Gln Pro His Ile Gln
 1               5                  10

<210> SEQ ID NO 118
<211> LENGTH: 13
```

<212> TYPE: PRT
<213> ORGANISM: Homo sapiens

<400> SEQUENCE: 118

Trp Ile Lys His Val Glu Lys Asn Gly Ser Lys Tyr Gly
 1               5                  10

<210> SEQ ID NO 119
<211> LENGTH: 13
<212> TYPE: PRT
<213> ORGANISM: Homo sapiens

<400> SEQUENCE: 119

Pro Asp Gly Leu Pro Tyr Leu Lys Val Leu Lys Ala Ala
 1               5                  10

<210> SEQ ID NO 120
<211> LENGTH: 13
<212> TYPE: PRT
<213> ORGANISM: Homo sapiens

<400> SEQUENCE: 120

Gly Val Asn Thr Thr Asp Lys Glu Ile Glu Val Leu Tyr
 1               5                  10

<210> SEQ ID NO 121
<211> LENGTH: 13
<212> TYPE: PRT
<213> ORGANISM: Homo sapiens

<400> SEQUENCE: 121

Ile Arg Asn Val Thr Phe Glu Asp Ala Gly Glu Tyr Thr
 1               5                  10

<210> SEQ ID NO 122
<211> LENGTH: 13
<212> TYPE: PRT
<213> ORGANISM: Homo sapiens

<400> SEQUENCE: 122

Cys Leu Ala Gly Asn Ser Ile Gly Ile Ser Phe His Ser
 1               5                  10

<210> SEQ ID NO 123
<211> LENGTH: 12
<212> TYPE: PRT
<213> ORGANISM: Homo sapiens

<400> SEQUENCE: 123

Ala Trp Leu Thr Val Leu Pro Ala Pro Gly Arg Glu
 1               5                  10

<210> SEQ ID NO 124
<211> LENGTH: 13
<212> TYPE: PRT
<213> ORGANISM: Homo sapiens

<400> SEQUENCE: 124

Asn Ser Asn Asn Lys Arg Ala Pro Tyr Trp Thr Asn Thr
 1               5                  10

<210> SEQ ID NO 125
<211> LENGTH: 13
<212> TYPE: PRT
<213> ORGANISM: Homo sapiens

<400> SEQUENCE: 125

Glu Lys Met Glu Lys Arg Leu His Ala Val Pro Ala Ala
1               5                   10

<210> SEQ ID NO 126
<211> LENGTH: 13
<212> TYPE: PRT
<213> ORGANISM: Homo sapiens

<400> SEQUENCE: 126

Asn Thr Val Lys Phe Arg Cys Pro Ala Gly Gly Asn Pro
1               5                   10

<210> SEQ ID NO 127
<211> LENGTH: 13
<212> TYPE: PRT
<213> ORGANISM: Homo sapiens

<400> SEQUENCE: 127

Met Pro Thr Met Arg Thr Leu Lys Asn Gly Lys Glu Phe
1               5                   10

<210> SEQ ID NO 128
<211> LENGTH: 13
<212> TYPE: PRT
<213> ORGANISM: Homo sapiens

<400> SEQUENCE: 128

Lys Gln Glu His Arg Ile Gly Gly Tyr Lys Val Arg Asn
1               5                   10

<210> SEQ ID NO 129
<211> LENGTH: 13
<212> TYPE: PRT
<213> ORGANISM: Homo sapiens

<400> SEQUENCE: 129

Gln His Trp Ser Leu Ile Met Glu Ser Val Val Pro Ser
1               5                   10

<210> SEQ ID NO 130
<211> LENGTH: 13
<212> TYPE: PRT
<213> ORGANISM: Homo sapiens

<400> SEQUENCE: 130

Asp Lys Gly Asn Tyr Thr Cys Val Val Glu Asn Glu Tyr
1               5                   10

<210> SEQ ID NO 131
<211> LENGTH: 13
<212> TYPE: PRT
<213> ORGANISM: Homo sapiens

<400> SEQUENCE: 131

Gly Ser Ile Asn His Thr Tyr His Leu Asp Val Val Glu
1               5                   10

<210> SEQ ID NO 132
<211> LENGTH: 13
<212> TYPE: PRT
<213> ORGANISM: Homo sapiens

<400> SEQUENCE: 132

Arg Ser Pro His Arg Pro Ile Leu Gln Ala Gly Leu Pro
1               5                   10

<210> SEQ ID NO 133
<211> LENGTH: 13
<212> TYPE: PRT
<213> ORGANISM: Homo sapiens

<400> SEQUENCE: 133

Ala Asn Ala Ser Thr Val Val Gly Gly Asp Val Glu Phe
1               5                   10

<210> SEQ ID NO 134
<211> LENGTH: 13
<212> TYPE: PRT
<213> ORGANISM: Homo sapiens

<400> SEQUENCE: 134

Val Cys Lys Val Tyr Ser Asp Ala Gln Pro His Ile Gln
1               5                   10

<210> SEQ ID NO 135
<211> LENGTH: 13
<212> TYPE: PRT
<213> ORGANISM: Homo sapiens

<400> SEQUENCE: 135

Trp Ile Lys His Val Glu Lys Asn Gly Ser Lys Tyr Gly
1               5                   10

<210> SEQ ID NO 136
<211> LENGTH: 13
<212> TYPE: PRT
<213> ORGANISM: Homo sapiens

<400> SEQUENCE: 136

Pro Asp Gly Leu Pro Tyr Leu Lys Val Leu Lys Ala Ala
1               5                   10

<210> SEQ ID NO 137
<211> LENGTH: 13
<212> TYPE: PRT
<213> ORGANISM: Homo sapiens

<400> SEQUENCE: 137

Gly Val Asn Thr Thr Asp Lys Glu Ile Glu Val Leu Tyr
1               5                   10

<210> SEQ ID NO 138
<211> LENGTH: 13
<212> TYPE: PRT
<213> ORGANISM: Homo sapiens

<400> SEQUENCE: 138

Ile Arg Asn Val Thr Phe Glu Asp Ala Gly Glu Tyr Thr
1               5                   10

<210> SEQ ID NO 139
<211> LENGTH: 13
<212> TYPE: PRT
<213> ORGANISM: Homo sapiens

<400> SEQUENCE: 139

Cys Leu Ala Gly Asn Ser Ile Gly Ile Ser Phe His Ser

<210> SEQ ID NO 140
<211> LENGTH: 12
<212> TYPE: PRT
<213> ORGANISM: Homo sapiens

<400> SEQUENCE: 140

Ala Trp Leu Thr Val Leu Pro Ala Pro Gly Arg Glu
 1               5                  10

<210> SEQ ID NO 141
<211> LENGTH: 13
<212> TYPE: PRT
<213> ORGANISM: Homo sapiens

<400> SEQUENCE: 141

Asn Ser Asn Asn Lys Arg Ala Pro Tyr Trp Thr Asn Thr
 1               5                  10

<210> SEQ ID NO 142
<211> LENGTH: 13
<212> TYPE: PRT
<213> ORGANISM: Homo sapiens

<400> SEQUENCE: 142

Glu Lys Met Glu Lys Arg Leu His Ala Val Pro Ala Ala
 1               5                  10

<210> SEQ ID NO 143
<211> LENGTH: 13
<212> TYPE: PRT
<213> ORGANISM: Homo sapiens

<400> SEQUENCE: 143

Asn Thr Val Lys Phe Arg Cys Pro Ala Gly Gly Asn Pro
 1               5                  10

<210> SEQ ID NO 144
<211> LENGTH: 13
<212> TYPE: PRT
<213> ORGANISM: Homo sapiens

<400> SEQUENCE: 144

Met Pro Thr Met Arg Thr Leu Lys Asn Gly Lys Glu Phe
 1               5                  10

<210> SEQ ID NO 145
<211> LENGTH: 13
<212> TYPE: PRT
<213> ORGANISM: Homo sapiens

<400> SEQUENCE: 145

Lys Gln Glu His Arg Ile Gly Gly Tyr Lys Val Arg Asn
 1               5                  10

<210> SEQ ID NO 146
<211> LENGTH: 13
<212> TYPE: PRT
<213> ORGANISM: Homo sapiens

<400> SEQUENCE: 146

Gln His Trp Ser Leu Ile Met Glu Ser Val Val Pro Ser
 1               5                  10

```
<210> SEQ ID NO 147
<211> LENGTH: 13
<212> TYPE: PRT
<213> ORGANISM: Homo sapiens

<400> SEQUENCE: 147

Asp Lys Gly Asn Tyr Thr Cys Val Val Glu Asn Glu Tyr
 1               5                  10

<210> SEQ ID NO 148
<211> LENGTH: 13
<212> TYPE: PRT
<213> ORGANISM: Homo sapiens

<400> SEQUENCE: 148

Gly Ser Ile Asn His Thr Tyr His Leu Asp Val Val Glu
 1               5                  10

<210> SEQ ID NO 149
<211> LENGTH: 13
<212> TYPE: PRT
<213> ORGANISM: Homo sapiens

<400> SEQUENCE: 149

Arg Ser Pro His Arg Pro Ile Leu Gln Ala Gly Leu Pro
 1               5                  10

<210> SEQ ID NO 150
<211> LENGTH: 13
<212> TYPE: PRT
<213> ORGANISM: Homo sapiens

<400> SEQUENCE: 150

Ala Asn Ala Ser Thr Val Val Gly Gly Asp Val Glu Phe
 1               5                  10

<210> SEQ ID NO 151
<211> LENGTH: 13
<212> TYPE: PRT
<213> ORGANISM: Homo sapiens

<400> SEQUENCE: 151

Val Cys Lys Val Tyr Ser Asp Ala Gln Pro His Ile Gln
 1               5                  10

<210> SEQ ID NO 152
<211> LENGTH: 13
<212> TYPE: PRT
<213> ORGANISM: Homo sapiens

<400> SEQUENCE: 152

Trp Ile Lys His Val Glu Lys Asn Gly Ser Lys Tyr Gly
 1               5                  10

<210> SEQ ID NO 153
<211> LENGTH: 13
<212> TYPE: PRT
<213> ORGANISM: Homo sapiens

<400> SEQUENCE: 153

Pro Asp Gly Leu Pro Tyr Leu Lys Val Leu Lys Ala Ala
 1               5                  10

<210> SEQ ID NO 154
```

-continued

<211> LENGTH: 13
<212> TYPE: PRT
<213> ORGANISM: Homo sapiens

<400> SEQUENCE: 154

Gly Val Asn Thr Thr Asp Lys Glu Ile Glu Val Leu Tyr
 1               5                  10

<210> SEQ ID NO 155
<211> LENGTH: 13
<212> TYPE: PRT
<213> ORGANISM: Homo sapiens

<400> SEQUENCE: 155

Ile Arg Asn Val Thr Phe Glu Asp Ala Gly Glu Tyr Thr
 1               5                  10

<210> SEQ ID NO 156
<211> LENGTH: 13
<212> TYPE: PRT
<213> ORGANISM: Homo sapiens

<400> SEQUENCE: 156

Cys Leu Ala Gly Asn Ser Ile Gly Ile Ser Phe His Ser
 1               5                  10

<210> SEQ ID NO 157
<211> LENGTH: 12
<212> TYPE: PRT
<213> ORGANISM: Homo sapiens

<400> SEQUENCE: 157

Ala Trp Leu Thr Val Leu Pro Ala Pro Gly Arg Glu
 1               5                  10

<210> SEQ ID NO 158
<211> LENGTH: 13
<212> TYPE: PRT
<213> ORGANISM: Homo sapiens

<400> SEQUENCE: 158

Glu Gly Ile Cys Arg Asn Arg Val Thr Asn Asn Val Lys
 1               5                  10

<210> SEQ ID NO 159
<211> LENGTH: 13
<212> TYPE: PRT
<213> ORGANISM: Homo sapiens

<400> SEQUENCE: 159

Asp Val Thr Lys Leu Val Ala Asn Leu Pro Lys Asp Tyr
 1               5                  10

<210> SEQ ID NO 160
<211> LENGTH: 13
<212> TYPE: PRT
<213> ORGANISM: Homo sapiens

<400> SEQUENCE: 160

Met Ile Thr Leu Lys Tyr Val Pro Gly Met Asp Val Leu
 1               5                  10

<210> SEQ ID NO 161
<211> LENGTH: 13
<212> TYPE: PRT

-continued

<213> ORGANISM: Homo sapiens

<400> SEQUENCE: 161

Pro Ser His Cys Trp Ile Ser Glu Met Val Val Gln Leu
1               5                   10

<210> SEQ ID NO 162
<211> LENGTH: 13
<212> TYPE: PRT
<213> ORGANISM: Homo sapiens

<400> SEQUENCE: 162

Ser Asp Ser Leu Thr Asp Leu Leu Asp Lys Phe Ser Asn
1               5                   10

<210> SEQ ID NO 163
<211> LENGTH: 13
<212> TYPE: PRT
<213> ORGANISM: Homo sapiens

<400> SEQUENCE: 163

Ile Ser Glu Gly Leu Ser Asn Tyr Ser Ile Ile Asp Lys
1               5                   10

<210> SEQ ID NO 164
<211> LENGTH: 13
<212> TYPE: PRT
<213> ORGANISM: Homo sapiens

<400> SEQUENCE: 164

Leu Val Asn Ile Val Asp Asp Leu Val Glu Cys Val Lys
1               5                   10

<210> SEQ ID NO 165
<211> LENGTH: 13
<212> TYPE: PRT
<213> ORGANISM: Homo sapiens

<400> SEQUENCE: 165

Glu Asn Ser Ser Lys Asp Leu Lys Lys Ser Phe Lys Ser
1               5                   10

<210> SEQ ID NO 166
<211> LENGTH: 13
<212> TYPE: PRT
<213> ORGANISM: Homo sapiens

<400> SEQUENCE: 166

Pro Glu Pro Arg Leu Phe Thr Pro Glu Glu Phe Phe Arg
1               5                   10

<210> SEQ ID NO 167
<211> LENGTH: 13
<212> TYPE: PRT
<213> ORGANISM: Homo sapiens

<400> SEQUENCE: 167

Ile Phe Asn Arg Ser Ile Asp Ala Phe Lys Asp Phe Val
1               5                   10

<210> SEQ ID NO 168
<211> LENGTH: 11
<212> TYPE: PRT
<213> ORGANISM: Homo sapiens

```
<400> SEQUENCE: 168

Val Ala Ser Glu Thr Ser Asp Cys Val Val Ser
 1               5                  10

<210> SEQ ID NO 169
<211> LENGTH: 13
<212> TYPE: PRT
<213> ORGANISM: Homo sapiens

<400> SEQUENCE: 169

Glu Gly Ile Cys Arg Asn Arg Val Thr Asn Asn Val Lys
 1               5                  10

<210> SEQ ID NO 170
<211> LENGTH: 13
<212> TYPE: PRT
<213> ORGANISM: Homo sapiens

<400> SEQUENCE: 170

Asp Val Thr Lys Leu Val Ala Asn Leu Pro Lys Asp Tyr
 1               5                  10

<210> SEQ ID NO 171
<211> LENGTH: 13
<212> TYPE: PRT
<213> ORGANISM: Homo sapiens

<400> SEQUENCE: 171

Met Ile Thr Leu Lys Tyr Val Pro Gly Met Asp Val Leu
 1               5                  10

<210> SEQ ID NO 172
<211> LENGTH: 13
<212> TYPE: PRT
<213> ORGANISM: Homo sapiens

<400> SEQUENCE: 172

Pro Ser His Cys Trp Ile Ser Glu Met Val Val Gln Leu
 1               5                  10

<210> SEQ ID NO 173
<211> LENGTH: 13
<212> TYPE: PRT
<213> ORGANISM: Homo sapiens

<400> SEQUENCE: 173

Ser Asp Ser Leu Thr Asp Leu Leu Asp Lys Phe Ser Asn
 1               5                  10

<210> SEQ ID NO 174
<211> LENGTH: 13
<212> TYPE: PRT
<213> ORGANISM: Homo sapiens

<400> SEQUENCE: 174

Ile Ser Glu Gly Leu Ser Asn Tyr Ser Ile Ile Asp Lys
 1               5                  10

<210> SEQ ID NO 175
<211> LENGTH: 13
<212> TYPE: PRT
<213> ORGANISM: Homo sapiens

<400> SEQUENCE: 175
```

Leu Val Asn Ile Val Asp Asp Leu Val Glu Cys Val Lys
1               5                   10

<210> SEQ ID NO 176
<211> LENGTH: 13
<212> TYPE: PRT
<213> ORGANISM: Homo sapiens

<400> SEQUENCE: 176

Glu Asn Ser Ser Lys Asp Leu Lys Lys Ser Phe Lys Ser
1               5                   10

<210> SEQ ID NO 177
<211> LENGTH: 13
<212> TYPE: PRT
<213> ORGANISM: Homo sapiens

<400> SEQUENCE: 177

Pro Glu Pro Arg Leu Phe Thr Pro Glu Glu Phe Phe Arg
1               5                   10

<210> SEQ ID NO 178
<211> LENGTH: 13
<212> TYPE: PRT
<213> ORGANISM: Homo sapiens

<400> SEQUENCE: 178

Ile Phe Asn Arg Ser Ile Asp Ala Phe Lys Asp Phe Val
1               5                   10

<210> SEQ ID NO 179
<211> LENGTH: 11
<212> TYPE: PRT
<213> ORGANISM: Homo sapiens

<400> SEQUENCE: 179

Val Ala Ser Glu Thr Ser Asp Cys Val Val Ser
1               5                   10

<210> SEQ ID NO 180
<211> LENGTH: 13
<212> TYPE: PRT
<213> ORGANISM: Homo sapiens

<400> SEQUENCE: 180

Glu Gly Ile Cys Arg Asn Arg Val Thr Asn Asn Val Lys
1               5                   10

<210> SEQ ID NO 181
<211> LENGTH: 13
<212> TYPE: PRT
<213> ORGANISM: Homo sapiens

<400> SEQUENCE: 181

Asp Val Thr Lys Leu Val Ala Asn Leu Pro Lys Asp Tyr
1               5                   10

<210> SEQ ID NO 182
<211> LENGTH: 13
<212> TYPE: PRT
<213> ORGANISM: Homo sapiens

<400> SEQUENCE: 182

Met Ile Thr Leu Lys Tyr Val Pro Gly Met Asp Val Leu
1               5                   10

<210> SEQ ID NO 183
<211> LENGTH: 13
<212> TYPE: PRT
<213> ORGANISM: Homo sapiens

<400> SEQUENCE: 183

Pro Ser His Cys Trp Ile Ser Glu Met Val Val Gln Leu
1               5                   10

<210> SEQ ID NO 184
<211> LENGTH: 13
<212> TYPE: PRT
<213> ORGANISM: Homo sapiens

<400> SEQUENCE: 184

Ser Asp Ser Leu Thr Asp Leu Leu Asp Lys Phe Ser Asn
1               5                   10

<210> SEQ ID NO 185
<211> LENGTH: 13
<212> TYPE: PRT
<213> ORGANISM: Homo sapiens

<400> SEQUENCE: 185

Ile Ser Glu Gly Leu Ser Asn Tyr Ser Ile Ile Asp Lys
1               5                   10

<210> SEQ ID NO 186
<211> LENGTH: 13
<212> TYPE: PRT
<213> ORGANISM: Homo sapiens

<400> SEQUENCE: 186

Leu Val Asn Ile Val Asp Asp Leu Val Glu Cys Val Lys
1               5                   10

<210> SEQ ID NO 187
<211> LENGTH: 13
<212> TYPE: PRT
<213> ORGANISM: Homo sapiens

<400> SEQUENCE: 187

Glu Asn Ser Ser Lys Asp Leu Lys Lys Ser Phe Lys Ser
1               5                   10

<210> SEQ ID NO 188
<211> LENGTH: 13
<212> TYPE: PRT
<213> ORGANISM: Homo sapiens

<400> SEQUENCE: 188

Pro Glu Pro Arg Leu Phe Thr Pro Glu Glu Phe Phe Arg
1               5                   10

<210> SEQ ID NO 189
<211> LENGTH: 13
<212> TYPE: PRT
<213> ORGANISM: Homo sapiens

<400> SEQUENCE: 189

Ile Phe Asn Arg Ser Ile Asp Ala Phe Lys Asp Phe Val
1               5                   10

```
<210> SEQ ID NO 190
<211> LENGTH: 11
<212> TYPE: PRT
<213> ORGANISM: Homo sapiens

<400> SEQUENCE: 190

Val Ala Ser Glu Thr Ser Asp Cys Val Val Ser
 1               5                  10

<210> SEQ ID NO 191
<211> LENGTH: 13
<212> TYPE: PRT
<213> ORGANISM: Homo sapiens

<400> SEQUENCE: 191

Glu Gly Ile Cys Arg Asn Arg Val Thr Asn Asn Val Lys
 1               5                  10

<210> SEQ ID NO 192
<211> LENGTH: 13
<212> TYPE: PRT
<213> ORGANISM: Homo sapiens

<400> SEQUENCE: 192

Asp Val Thr Lys Leu Val Ala Asn Leu Pro Lys Asp Tyr
 1               5                  10

<210> SEQ ID NO 193
<211> LENGTH: 13
<212> TYPE: PRT
<213> ORGANISM: Homo sapiens

<400> SEQUENCE: 193

Met Ile Thr Leu Lys Tyr Val Pro Gly Met Asp Val Leu
 1               5                  10

<210> SEQ ID NO 194
<211> LENGTH: 13
<212> TYPE: PRT
<213> ORGANISM: Homo sapiens

<400> SEQUENCE: 194

Pro Ser His Cys Trp Ile Ser Glu Met Val Val Gln Leu
 1               5                  10

<210> SEQ ID NO 195
<211> LENGTH: 13
<212> TYPE: PRT
<213> ORGANISM: Homo sapiens

<400> SEQUENCE: 195

Ser Asp Ser Leu Thr Asp Leu Leu Asp Lys Phe Ser Asn
 1               5                  10

<210> SEQ ID NO 196
<211> LENGTH: 13
<212> TYPE: PRT
<213> ORGANISM: Homo sapiens

<400> SEQUENCE: 196

Ile Ser Glu Gly Leu Ser Asn Tyr Ser Ile Ile Asp Lys
 1               5                  10

<210> SEQ ID NO 197
<211> LENGTH: 13
```

```
<212> TYPE: PRT
<213> ORGANISM: Homo sapiens

<400> SEQUENCE: 197

Leu Val Asn Ile Val Asp Asp Leu Val Glu Cys Val Lys
 1               5                  10

<210> SEQ ID NO 198
<211> LENGTH: 13
<212> TYPE: PRT
<213> ORGANISM: Homo sapiens

<400> SEQUENCE: 198

Glu Asn Ser Ser Lys Asp Leu Lys Lys Ser Phe Lys Ser
 1               5                  10

<210> SEQ ID NO 199
<211> LENGTH: 13
<212> TYPE: PRT
<213> ORGANISM: Homo sapiens

<400> SEQUENCE: 199

Pro Glu Pro Arg Leu Phe Thr Pro Glu Glu Phe Phe Arg
 1               5                  10

<210> SEQ ID NO 200
<211> LENGTH: 13
<212> TYPE: PRT
<213> ORGANISM: Homo sapiens

<400> SEQUENCE: 200

Ile Phe Asn Arg Ser Ile Asp Ala Phe Lys Asp Phe Val
 1               5                  10

<210> SEQ ID NO 201
<211> LENGTH: 11
<212> TYPE: PRT
<213> ORGANISM: Homo sapiens

<400> SEQUENCE: 201

Val Ala Ser Glu Thr Ser Asp Cys Val Val Ser
 1               5                  10

<210> SEQ ID NO 202
<211> LENGTH: 7
<212> TYPE: PRT
<213> ORGANISM: Homo sapiens

<400> SEQUENCE: 202

Asn Tyr Lys Lys Pro Lys Leu
 1               5
```

CRYSTAL OF FIBROBLAST GROWTH FACTOR RECEPTOR 1 IN COMPLEX WITH FIBROBLAST GROWTH FACTOR

This application is a 371 of PCT/US00/23744 filed Aug. 30, 2000, which claims priority to Ser. No. 60/151,810, filed Aug. 30, 1999.

CROSS REFERENCE TO RELATED APPLICATIONS

This application claims priority under 35 U.S.C. § 119(e) of U.S. Provisional Application Ser. No. 60/151,810, filed Aug. 30, 1999, the disclosure of which is herein incorporated by reference in its entirety.

BACKGROUND

The following description of the background of the invention is provided simply as an aid in understanding the invention and is not admitted to describe or constitute prior art to the invention.

Receptor protein tyrosine kinases ("RPTKs") include a large and diverse family of enzymes. The RPTK family contains multiple subfamilies, one of which is the fibroblast growth factor receptor (FGFR) subfamily. Another subfamily is the type III receptor tyrosine kinase (RTK) subfamily whose members include platelet-derived growth factor receptors a and β ("PDGFR α" and "PDGFR β"), macrophage colony-stimulating factor receptor (M-CSFR), c-kit (also referred to as SCF receptor ("SCFR")) and the flt3 receptor. The members of this RTK subfamily contain five immunoglobulin-like (Ig) domains in their extracellular ligand binding domains followed by a single transmembrane domain and a cytoplasmic tyrosine kinase domain interrupted by a large kinase-insert. For a review of RPTKs, see Schlessinger and Ullrich, 1992, Neuron 9: 383–391; for a review describing the FGFR subfamily, see Givol and Yayon, 1992, FASEB J. 6 (15): 3362–3369.

All RPTKs enzymatically transfer a high energy phosphate from adenosine triphosphate to a tyrosine residue in a target protein. These phosphorylation events regulate certain cellular phenomena in signal transduction processes. Cellular signal transduction processes contain multiple steps that convert an extracellular signal into an intracellular signal. The intracellular signal is then converted into a cellular response. RPTKs are components in many signal transduction processes. Typically, an RPTK regulates the flow of a signal in a particular step in the process by phosphorylating a downstream molecule. This phosphorylation modulates the downstream molecule's activity by turning it either "on" or "off," causing excessive or deficient signalling by the downstream molecule. Excessive signalling can lead to such abnormalities as uncontrolled cell proliferation, which is characteristic of such disorders as cancer, angiogenesis induced by various tumors, atherosclerosis, and arthritis. Alternatively, cellular proliferation can be induced therapeutically, for example angiogenesis may be used to ameliorate coronary artery disease by inducing collateral vascularization.

Ligand-induced dimerization of RPTKs is an important step in the RPTK-mediated signal transduction process. For review of the importance of dimerization of RPTKs, see Lemmon and Schlessinger, 1994, Trends in Biochem. Sci. 19: 459463; and Ullrich and Schlessinger, 1990, Cell 61:203–212. Some growth factors, for example platelet-derived growth factor ("PDGF") and stem cell factor ("SCF"), are dimeric molecules that, by themselves, induce dimerization of their specific receptors. In contrast, other growth factors, such as fibroblast growth factors (FGFs), are monomeric molecules that must act in concert with other molecules to induce dimerization of their specific receptors. See Schlessenger et al., 1995, Cell 83: 357–360; Spivak-Kroizman et al., 1994, Cell 79: 1015–1024; Ornitz et al., 1992, Mol. Cell. Biol. 12: 240–247. In particular, FGFs typically function in concert with soluble or cell surface-bound heparin sulfate-containing proteoglycans (HSPGs).

The FGFR subfamily consists of at least 21 structurally related polypeptides, designated FGFR1 through FGFR21, that are expressed in embryonic, fetal, and adult vertebrates. FGFR1 through FGFR4, are known as "high affinity FGFRs," due to their ability to bind appropriate fibroblast growth factors with a high affinity. These high affinity FGFRs are characterized by an extracellular ligand-binding domain which comprises three immunoglobulin (IG)-like domains (known as D1, D2, and D3), a single transmembrane helix, and a cytoplasmic domain containing tyrosine kinase activity. See Lee et al., 1989, Science 245: 57–60; Jaye et al., 1992, J. Mol. Biol. 227: 840–851; Johnson & Williams, 1993, Adv. Cancer. Res. 60: 1–41. Each of the four high affinity FGFRs binds to a specific subset of FGFs. Ornitz et al., 1996, J. Biol. Chem. 271: 15292–15297.

Naturally occuring variants of the high affinity FGFRs-lacking D1, or D1 and the linker region between D1 and D2 known as the "acid box," have been identified. These varient FGFRs retain the ability to bind appropriate FGFs with high affinity, suggesting that the D2 and D3 regions are sufficient to confer FGF binding ability and specificity. See Crumley et al., 1991, Oncogene 6: 2255–2262; Dionne et al., 1990, EMBO J. 9: 2685–2692; Johnson and Williams, 1993, Adv. Cancer. Res. 60: 141. In particular, D3 has been shown to play a critical role in the binding specificity of FGFRs. See Bottaro, et al., 1990, J. Biol. Chem. 265: 12767–12770; Miki et al., 1992, Proc. Natl. Acad. Sci. 89: 246–250; Dell et al., 1992, J. Biol. Chem. 267: 21225–21229; Yayon et al., 1992 EMBO J. 11: 1885–1890.

Recently, three dimensional structures of the intracellular catalytic domains of various PTKs have been described in International Publication No. WO 98/07835, U.S. patent application Ser. No. 60/034,168, filed Dec. 19, 1996, and U.S. Pat. No. 5,942,428, issued on Aug. 24, 1999, each of which is hereby incorporated herein by reference in its entirety including all claims, drawings, tables, and figures.

Despite recent advances in the understanding of signal transduction and function of the receptor PTKs and their ligands, there remains a need in the art for the atomic-level characterization and analysis of such molecules, particularly with respect to the design and synthesis of novel and improved therapeutic molecules.

SUMMARY

The present invention relates to the three dimensional structures of receptor protein tyrosine kinases and/or their ligands. These molecular structures may include an RPTK or ligand thereof, alone or as a complex including one or more ligands. In particular, this application relates to molecular structures comprising a polypeptide which includes the extracellular domain of a receptor protein tyrosine kinase, alone and in complexes comprising one or more ligands. In another aspect, the application describes molecular structures comprising a polypeptide which includes the receptor binding core of a growth factor, such as stem cell facter, alone or in a complex with one or more ligands such as a receptor protein tyrosine kinase.

The present application concerns solving and using the three dimensional structures of receptor protein tyrosine kinases, and more particularly to structures including the extracellular domain of receptor protein tyrosine kinases, alone and in complexes comprising one or more ligands. As an example, X-ray crystallograpic techniques are used herein to determine the three dimensional structure of certain RPTK extracellular domains bound to certain ligands, such as FGF molecules or SCF molecules, at atomic resolution. The application also concerns solving and using the three dimensional structures of stem cell factor, and more particularly to structures including the receptor binding core of stem cell factor, alone and in complexes comprising one or more ligands.

The three dimensional structures described herein elucidate specific interactions between receptor protein tyrosine kinases and/or ligands bound to them. The coordinates that define the three dimensional structures of receptor protein tyrosine kinases are useful for determining three dimensional structures of receptor RPTKs with unknown structure. In addition, the coordinates are also useful for designing and identifying modulators of receptor protein tyrosine kinase function. These modulators are potentially useful as therapeutics for treating or preventing disease, including (but not limited to) cell proliferative diseases, such as cancer, tumorigenic angiogenesis, atherosclerosis, and arthritis. Alternatively, cellular proliferation can be induced therapeutically, for example angiogenesis may be used to ameliorate coronary artery disease by inducing collateral vascularization. Thus in a first aspect, the invention features a crystalline form of a polypeptide corresponding to all or a portion of the extracellular domain of an RPTK. In certain embodiments, the invention features a crystalline form of an RPTK bound to a ligand or ligand analog. In typical embodiments, the RPTK is an FGFR, such as FGFR1 or FGFR2, and the ligand is an FGF, such as FGF1 or FGF2. In particularly suitable embodiments, the polypeptide comprises residues 150–360 of FGFR1 or residues 150–360 of FGFR2, the sequences of which are shown in FIG. 4. The ligand can be a fibroblast growth factor, such as an FGF1 including the amino acid sequence as shown in FIG. 17 or an FGF2 including the amino acid sequence as shown in FIG. 17.

The term "crystalline form," in the context of the invention, refers to a crystal formed from an aqueous solution comprising a purified polypeptide. In certain embodiments, a crystal is formed from an aqueous solution comprising all or part of the extracellular domain of an RPTK. A crystalline form of a polypeptide is characterized as being capable of diffracting x-rays in a pattern defined by one of the crystal forms depicted in Blundel et al., 1976, *Protein Crystallography*, Academic Press, and in Hahn, 1996, *The International Tables for Crystallography, Volume A*, Fourth Edition, Kluwer Academic Publishers. In preferred embodiments, a crystalline form may also be formed from a purified polypeptide corresponding to all or part of the extracellular domain of an RPTK in a complex with one or more ligands or ligand analogs, as defined herein.

A crystalline form of an RPTK may also comprise a crystal formed from an aqueous solution comprising a purified polypeptide corresponding to all or part of the extracellular domain of an RPTK, with or without a complexed ligand or ligand analogue, into which one or more heavy atoms are introduced. Preferably, introduction of a heavy atom results in as minimal a change to the original crystalline structure as possible. A heavy atom can be introduced into the protein crystal by well known techniques. Preferred reagents for introduction of heavy atoms are platinum tetrachloride, mercuric acetate, ethyl mercury thiosalicylate, iridium hexachloride, gadolinium sulfate, samarium acetate, gold chloride, uranyl acetate, mercury chloride, and ethyl mercury chloride.

The term "receptor protein tyrosine kinase," or "RPTK," as used herein refers to an enzyme comprising an intracellular catalytic domain capable of transferring the high energy phosphate of adenosine triphosphate to a tyrosine residue located on a protein target, an extracellular domain that serves as a receptor for a specific ligand or set of ligands, and a membrane-spanning domain linking the intracellular and extracellular domains. In vivo, the binding of a ligand to its receptor results in receptor dimerization and activation of the intracellular catalytic domain. Preferred RPTKs of the invention are PDGFR, SCFR, EGFR, VEGFR, HGFR, neurotrophinR, HER2, HER3, HER4, InsulinR, IGFR, CSFIR, FLK, KDR, VEGFR2, CCK4, MET, TRKA, AXL, TIE, EPH, RYK, DDR, ROS, RET, LTK, ROR1, or MUSK. More preferably, a receptor PTK of the invention is a member of the FGFR family, such as FGFR1, FGFR2, FGFR3, and FGFR4. Certain receptor PTKs have no known ligand, and are referred to as "orphan receptor PTKs."

The term "FGFR1" refers to one member of multiple receptor PTKs that are homologous to one another, and which bind FGF. In this context, the term "homologous" preferably refers to about 70% or greater amino acid identity between two members of the FGFR family, more preferably at least about 80% amino acid identity, and most preferably at least about 90% amino acid identity. The term "FGFR1" includes human FGFR1 which comprises or consists of the amino acid sequence of residues 150–360 of FGFR1 as shown in FIG. 4. "Homologous" in this and other contexts also includes molecules of similarity sufficient to indicate relation by a common origin or archetype.

As used herein, the term "extracellular domain" refers to all or a portion of the region of an RPTK that exists outside the plasma membrane of a cell. Preferably, an extracellular domain is anchored to the plasma membrane by a polypeptide region that associates with the plasma membrane, and most preferably by a polypeptide region that is embedded within or crosses the plasma membrane. An extracellular domain can also be a soluble domain that is not anchored to the plasma membrane of a cell. Most preferably, an extracellular domain comprises one or more binding sites for one or more ligands.

RPTK extracellular domains can comprise one or more known structural motifs. Preferably, these structural motifs can be one or more of the following: cysteine-rich regions, fibronectin III-like domains, Ig-like domains, EGF-like domains, factor VIII-like domains, and Kringle domains. Most preferred are RPTKs comprising one or more IG-like domains. For example, FGFR1, FGFR2, FGFR3, and FGFR4 each contain three IG-like domains, labeled D1, D2, and D3. Other preferred RPTKs comprising IG-like domains include, but are not limited to, PDGFR, c-Kit, Flk1, Flk2, Flk4, KLG, TrkA, TrkB, TrkC, Axl, Tie, c-Eyk, and Elk.

The term "ligand" as used herein refers to a molecule that specifically binds to a receptor. In various embodiments, ligands are growth factors, cytokines, lymphokines, or hormones. Preferred ligands include, but are not limited to, epidermal growth factors, insulin, platelet-derived growth factors, stem cell factors, vascular endothelial growth factors, hepatocyte growth factors, and neurotrophins. Particularly preferred ligands are fibroblast growth factors.

The term "fibroblast growth factor" as used herein refers to a family of polypeptide growth factors that share extensive sequence homologies and a common structural fold. At the time of the invention, the FGF family contains about 21 known members, named FGF1 through FGF21. Those skilled in the art will understand that other members of the FGF family may be later identified and used in practicing the present invention. FGFs bind to FGFRs, and to HSPGs. Preferred FGFs are FGF1, FGF2, FGF3, and FGF4.

The term "ligand analog" as used herein refers to a molecule that is structurally or functionally similar to a ligand and that binds to the ligand binding site on a polypeptide. A ligand analog may be structurally similar to a ligand if the analog results from the substitution, addition, or deletion of one or more atoms, functional groups, or amino acid residues of a ligand. A ligand analog is functionally similar to a ligand if the ligand analog binds to the ligand binding site of the ligand receptor, or if binding of the ligand analog to the ligand receptor results in a similar biochemical event(s) to those resulting from ligand binding. Such a ligand analog may also be referred to as a ligand "mimic."

Binding of a ligand analog may also result in an inhibition of one or more biochemical events which result from ligand binding, or may act as a competitor of ligand binding. Such a ligand analog may also be referred to as an "inhibitor." A ligand analog may also bind to the putative ligand binding site of an orphan receptor PTK.

A ligand analog may preferably bind to its ligand receptor with lower, equal, or greater affinity than does the corresponding ligand. In certain embodiments, a ligand analog may be a mutant ligand. The term "mutant" is defined herein.

The term "bind" as used herein refers to a specific interaction of two or more molecules. Binding preferably refers to noncovalent binding. Such binding is typically mediated by one or more of hydrogen-bonding, van der Waals interactions, aromatic interactions, electrostatic interactions, and hydrophobic interactions. In certain embodiments, binding can refer to covalent binding of two or more molecules.

The term "catalytic domain" refers to a region of a protein that can exist as a separate entity from the protein, but that retains complete or partial catalytic function. The catalytic domain of a protein tyrosine kinase is characterized as having considerable amino acid identity to the catalytic domain of other protein tyrosine kinases. The catalytic domain of a protein tyrosine kinase is also characterized as being a polypeptide that is soluble in solution.

The term "considerable amino acid identity" preferably refers to at least about 30°/identity, more preferably at least about 35% identity, and most preferably at least about 40°/identity. These degrees of amino acid identity refer to the identity between different protein tyrosine kinase families. Amino acid identity for members of a given protein tyrosine kinase family range from about 55% to about 90%.

The term "identity" as used herein refers to a property of sequences that measures their similarity or relationship. Identity is measured by dividing the number of identical residues in the two sequences by the total number of residues and multiplying the product by 100. Thus, two copies of exactly the same sequence have 100% identity, but sequences that are less highly conserved and have deletions, additions, or replacements have a lower degree of identity. Two sequences may also be homologous to one another. The term "homologous" is defined herein, and can include, but is not limited to molecules (e.g., proteins) of similarity sufficient to indicate relation by a common origin or archetype.

Those skilled in the art will recognize that several computer programs are available for determining sequence identity and homology, including BLAST (Altschul, et al., 1990, *J. Mol. Biol.* 215:403410) and FASTA (Pearson and Lipman, 1988, *Proc. Natl. Acad. Sci. USA* 85:2444–2448).

The term "functional" refers to the ability of a portion of a protein to retain all or partial function of the intact protein. For example, a functional RPTK catalytic domain may retain the ability to convert a substrate into a product by phosphorylating the substrate, while a functional RPTK extracellular domain may retain the ability to bind to its ligand.

In certain embodiments, a polypeptide can exist as an extracellular domain, even though it is not functional. For example, a polypeptide corresponding to an extracellular domain may not comprise all of the structures necessary for binding a ligand or ligand analog. In these embodiments, a measure of an RPTK extracellular domain can be a polypeptide that is homologous to other RPTK extracellular domains.

In another embodiment, the crystal comprises a polypeptide, which includes an extracellular domain of a receptor protein tyrosine kinase, and a ligand bound to the extracellular domain. For example, the receptor protein tyrosine kinase can be a fibroblast growth factor receptor, such as FGFR1 or FGFR2, and the ligand can be a fibroblast growth factor, such as FGF1 or FGF2. The crystal may also include a sulfated oligosaccharide bound to the receptor protein tyrosine kinase and/or a ligand bound thereto. The size (and thus molecular weight) of the sulfated oligosaccharide may vary. Examples of suitable sulfated oligosaccharide which may be contained in the crystal include a sulfated disaccharides, hexasaccharides, octasaccharides, decasaccharides, dodecasaccharides. Preferably, the sulfated oligosaccharide is sulfated mucooligosaccharide, such as heparin. In a particular aspect of this embodiment, the crystal includes a FGF:FGFR:heparin ternary complex. For example, the crystal can include a FGF:FGFR:heparin ternary complex such as an FGF1:FGFR1:heparin ternary complex, an FGF2:FGFR:heparin ternary complex, an FGF1:FGFR2:heparin ternary complex, or an FGF2:FGFR2:heparin ternary complex.

In certain other aspects, a crystal may comprise a polypeptide which includes the receptor binding core of a stem cell factor. The receptor binding core generally has a three dimensional structure which includes a four-helix bundle and two strands. Stem cell factors and fragments containing the receptor binding core typically crystallize in a form which includes a homodimer of the polypeptide. While the monomers which make up the homodimer may be covalently linked, e.g., by one or more intermolecular disulfide bonds, the SCF crystals described herein include a noncovalent homodimer. The SCF homodimer forms orthorhombic crystal which has unit cell dimensions: a=72.47 Å, b=83.45 Å and c=89.15 Å. The SCF homodimer may also be crystallized (e.g., in the presence of to form monoclinic crystals. Monoclinic crystals of a noncovalent SCF homodimer were used to obtain the atomic structural coordinates shown in Table 4. These atomic coordinates are for crystals formed from a homodimer of a polypeptide which contains amino acid residues 1–141 of stem cell factor. These crystals have C2 symmetry. Crystals of this type may also include an RPTK, such as c-kit (SCFR) bound to a stem cell factor or fragment thereof. Preferably, the crystal includes c-kit bound to the receptor binding core of a stem cell factor.

The term "polypeptide" refers to an amino acid chain representing a portion of, or the entire sequence of, amino acid residues comprising a protein.

The term "association" refers to a condition of proximity between a chemical entity or compound, or portions or fragments thereof, and RPTK, or portions or fragments thereof. The association may be non-covalent, i.e., where the juxtaposition is energetically favored by, e.g., hydrogen-bonding, van der Waals, electrostatic or hydrophobic interactions, or it may be covalent.

The terms "heavy atom" and "heavy metal atom" refer to an atom that is a transition element, a lanthanide metal, or an actinide metal. Lanthanide metals include elements with atomic numbers between 57 and 71, inclusive. Actinide metals include elements with atomic numbers between 89 and 103, inclusive. In preferred embodiments, a crystal of the invention can comprise one or more heavy metal atoms. Such a crystal is referred to herein as a "derivative crystal."

In another aspect, the invention features a crystalline form of a polypeptide corresponding to the D2-D3 region of an RPTK extracellular domain. In preferred embodiments, the invention features a crystalline form of the D2-D3 region of a receptor PTK extracellular domain bound to a ligand or ligand analog. In preferred embodiments, the RPTK is an FGFR, such as FGFR1 or FGFR2, and the ligand is an FGF, preferably FGF1 or FGF2. In particularly preferred embodiments, the polypeptide comprises residues 150–360 of FGFR1 or residues 150–360 of FGFR2 the sequences of which are shown in FIG. 4. The ligand may counterpart protein or a mimic thereof. For example, where the RPTK includes the extracellular binding domain of FGFR1 or FGFR2, the ligand can be a fibroblast growth factor, such as an FGF1 including the amino acid sequence as shown in FIG. 17 or an FGF2 including the amino acid sequence as shown in FIG. 17.

The term "D2-D3 region" as used herein refers to the second and third Ig-like domains of an FGFR1 The term "Ig-like domain" is well known to those of skill in the art. In certain embodiments, the D2-D3 region of the invention may not comprise the entire second and third Ig-like domains, but contain sufficient residues to provide a binding site for the ligand of the FGFR. Most preferably, the term "D2-D3 region" refers to proteins which include residues 150–360 of human FGFR1.

The term "mutant" refers to a polypeptide which is obtained by replacing at least one amino acid residue in a native RPTK or polypeptide ligand with a different amino acid residue. Mutation can also be accomplished by adding and/or deleting amino acid residues within the native polypeptide or at the N- and/or C-terminus of a polypeptide. Preferably, a mutant polypeptide has substantially the same three-dimensional structure as the native polypeptide.

The term "having substantially the same three-dimensional structure" as used herein refers to a set of atomic structure coordinates that have a root mean square deviation (r.m.s.d.) of less than or equal to about 2 Å when superimposed with the atomic structure coordinates of the native polypeptide from which the mutant is derived, when at least about 50% to 100% of the Cα atoms of the native tyrosine kinase are included in the superposition.

In another aspect, the invention relates to a crystalline form of an RPTK extracellular domain bound to a ligand defined by the structural coordinates set forth in Table 1 or Table 2.

The term "atomic structural coordinates" as used herein refers to a data set that defines the three dimensional structure of a molecule or molecules. Structural coordinates can be slightly modified and still render nearly identical three dimensional structures. A measure of a unique set of structural coordinates is the root-mean-square deviation of the resulting structure. Structural coordinates that render three dimensional structures that deviate from one another by a root-mean-square deviation of less than about 1.5 Å may be viewed by a person of ordinary skill in the art as identical. Hence, the structural coordinates set forth in Tables 1–4 and 6 are not limited to the values defined therein.

The use of X-ray crystallography can elucidate the three dimensional structure of crystalline forms of the invention. Typically, the first characterization of crystalline forms by X-ray crystallography can determine the unit cell shape and its orientation in the crystal. The term "unit cell" refers to the smallest and simplest volume element of a crystal that is completely representative of the unit of pattern of the crystal. The dimensions of the unit cell are defined by six numbers: dimensions a, b and c and angles α, β and γ. A crystal can be viewed as an efficiently packed array of multiple unit cells. Detailed descriptions of crystallographic terms are described in Hahn, 1996, *The International Tables for Crystallography, Volume A*, Fourth Edition, Kluwer Academic Publishers; and Shmueli, *The International Tables for Crystallography, Volume B*, First Edition, Kluwer Academic Publishers.

In another aspect, the invention features a crystalline form of a polypeptide corresponding to the D2-D3 region of a receptor PTK extracellular domain bound to a ligand or ligand analog, where the crystal is characterized by having tetragonal unit cells and space group symmetry $P4_12_12$. In preferred embodiments, the RPTK is an FGFR, preferably FGFR1, and the ligand is an FGF, preferably FGF2. In particularly preferred embodiments, the polypeptide includes residues 150–360 of FGFR1 or residues 150–360 of FGFR2, the sequences of which are shown in FIG. 4. Most preferably, the invention features a crystalline form of FGFR1 D2-D3 bound to FGF2, where the tetragonal unit cells of the crystal have dimensions of about a=98.5 Å, b=98.5 Å, c=197.0 Å and β=90°.

In yet another aspect, the invention features a crystalline form of a polypeptide corresponding to the D2-D3 region of a receptor PTK extracellular domain bound to a ligand or ligand analog, where the crystal is characterized by having tetragonal unit cells and space group symmetry β1. In preferred embodiments, the RPTK is an FGFR, preferably FGFR1, and the ligand is an FGF, preferably FGF1. In particularly preferred embodiments, the polypeptide comprises residues 150–360 of FGFR1 or residues 150–360 of FGFR2, the sequences of which are shown in FIG. 4. Most preferably, the invention features a crystalline form of FGFR1 D2-D3 bound to FGF1, where the tetragonal unit cells of the crystal have dimensions of about a=62.55 Å, b=64.06 Å, c=64.14 Å, α=93.40°, β=111.17°, and γ=97.18°.

In yet another aspect, the invention features a crystalline form of a polypeptide corresponding to the D2-D3 region of a receptor PTK extracellular domain bound to a ligand or ligand analog, where the crystal is characterized by having triclinic unit cells and space group symmetry β1. In preferred embodiments, the RPTK is an FGFR, such as FGFR2, and the ligand is an FGF, such as FGF2. In particularly preferred embodiments, the polypeptide comprises residues 150–360 of FGFR2, the sequences of which are shown in FIG. 4, and FGF2 has the sequence set forth in FIG. 17. For example, there is a crystalline form of FGFR2 D2-D3 bound to FGF2 having triclinic unit cells with dimensions of about a=72.20 Å, b=71.68 Å, c=90.92 Å, α=90.53°, β89.98°, and γ89.99°.

The term "space group" refers to the symmetry of a unit cell. In a space group designation (e.g., P4$_1$2$_1$2, or P1) the capital letter indicates the lattice type and the other symbols represent symmetry operations that can be carried out on the unit cell without changing its appearance.

The term "lattice" in reference to crystal structures refers to the array of points defined by the vertices of packed unit cells.

The term "symmetry operations" refers to geometrically defined ways of exchanging equivalent parts of a unit cell, or exchanging equivalent molecules between two different unit cells. Examples of symmetry operations are screw axes, centers of inversion, and mirror planes.

By "isolated" in reference to a polypeptide is meant a polymer of, for example, 6, 12, 18 or more amino acids linked to each other by chemical (e.g., peptide) bonds, including polypeptides that are isolated from natural or recombinant sources or that are chemically synthesized. The isolated polypeptides of the present invention are unique in the sense that they are not found in a pure or separated state in nature. Use of the term "isolated" indicates that a naturally occurring sequence, or an analog thereof, has been removed from its normal cellular environment. Thus, the sequence may be in a cell-free solution or placed in a different cellular environment. The term does not imply that the sequence is the only amino acid chain present, but that it is essentially free (about 90–95% pure at least) of other material.

The term "enriched" as used herein in reference to a polypeptide refers to a specific amino acid sequence constituting a significantly higher fraction of the total of polypeptides present in the cells or solution of interest than in the cells or solution from which the sequence was taken. Preferably, a polypeptide is enriched about 2-fold, about 3-fold, about 5-fold, about 10-fold, about 20-fold, about 50-fold, or about 100-fold. Enrichment may be effected by preferential reduction in the amount of other polypeptides, or by a preferential increase in the amount of the specific polypeptide of interest, or by a combination of the two. However, it should be noted that "enriched" does not imply that there are no other polypeptides present, just that the relative amount of the polypeptide of interest has been significantly increased. The term "significant" here is used to indicate that the level of increase is useful to the person making such an increase, and generally means an increase relative to other amino acids of about at least 2 fold, more preferably about 2-fold, about 3-fold, about 5-fold, about 10-fold, about 20-fold, about 50-fold, about 100-fold, or more.

It is also advantageous for some purposes that an amino acid sequence be in purified form. The term "purified" as used herein in reference to a polypeptide does not refer to absolute purity (such as a homogeneous preparation); instead, it refers to a polypeptide that is relatively purer than in the natural environment. Preferably, a polypeptide is purified about 2-fold, about 3-fold, about 5-fold, about 10-fold, about 20-fold, about 50-fold, or about 100-fold. Most preferably, purification of at least one order of magnitude, preferably two or three orders, and more preferably four or five orders of magnitude is expressly contemplated. In preferred embodiments, the substance is free of contamination at a functionally significant level.

In another aspect, the invention features a method for creating crystalline forms described herein. The method may utilize the polypeptides described herein to form a crystal.

The method comprises the steps of:

(a) mixing a volume of polypeptide solution with a reservoir solution; and (b) incubating the mixture obtained in step (a) over the reservoir solution in a closed container, under conditions suitable for crystallization.

Preferably, the polypeptide solution comprises about 1 mg/ml to about 50 mg/ml of the polypeptide to be crystallized, and most preferably about 1 mg/ml, 2 mg/ml, 5 mg/ml, about 10 mg/ml, about 15 mg/ml, about 20 mg/ml, about 25 mg/ml, about 30 mg/ml, about 35 mg/ml, about 40 mg/ml, about 45 mg/ml, and about 50 mg/ml. The polypeptide solution is preferably buffered to between about pH 6.5 and about pH 9.5, most preferably about pH 8.5. In preferred embodiments, the solution also comprises salt, preferably in the form of KCl or NaCl, between about 1 mM and about 500 mM, most preferably about 150 mM. In certain embodiments, the reservoir solution preferably comprises between about 0.5 and about 3 M ammonium sulfate, most preferably about 1.6 M ammonium sulfate, and between about 5% and about 50% glycerol, most preferably 20% glycerol. In other embodiments, the reservoir solution preferably comprises between about 5% and about 50% polyethylene glycol, and most preferably about 20%, and between 0.05 M and 0.5 M Li$_2$SO$_4$, most preferably about 0.2 M. The reservoir solution is preferably buffered to between about pH 6.5 and about pH 9.5, and most preferably about pH 8.5. These processes are described in detail in the section entitled "Detailed Description of the Invention."

In another aspect, the invention features a three dimensional representation of a structure of an RPTK extracellular domain, alone or in complex with a ligand or ligand analog. In preferred embodiments, the invention features a three dimensional representation of a structure of the D2-D3 region of a receptor PTK extracellular domain bound to a ligand or ligand analog. In preferred embodiments, the RPTK is an FGFR, such as FGFR1 or FGFR2, and the ligand is an FGF, preferably FGF1 or FGF2. In one group of preferred embodiments, the polypeptide comprises residues 150–360 of FGFR1 or residues 150–360 of FGFR2, the sequences of which are shown in FIG. 4. The ligand can be a fibroblast growth factor, such as an FGF1 including the amino acid sequence as shown in FIG. 17 or an FGF2 including the amino acid sequence as shown in FIG. 17.

The term "three dimensional representation" as used herein refers to any non-natural representation of one or more molecules which utilize a three dimensional coordinate space. The skilled artisan will recognize that the atomic structural coordinates in Tables 1–4 and 6, for example, use a three dimensional coordinate space, and thus are three dimensional representations. In preferred embodiments, a three dimensional representation can be a model prepared from the atomic coordinates of one or more molecules. In particularly preferred embodiments, a three dimensional representation can be a model prepared from the atomic coordinates of one or more molecules that exists in a computer's memory and/or that is displayed on a computer's screen. The coordinates disclosed herein provide the skilled person with the information needed to study molecular structures and interactions. Comparable data can be obtained by crystallizing the molecules in view of the teachings contained herein and conducting x-ray analysis in accordance with the teachings contained herein. Such data so obtained are within the scope of the present invention. Moreover, variations made to the data contained herein are within the scope of the present invention.

In another aspect, the invention features a recombinant DNA encoding an RPTK extracellular domain. For example, the recombinant DNA can include a coding strand which includes a nucleotide sequence coding for amino acid residues 150–360 of FGFR1 or residues 150–360 of FGFR2, the sequences of which are shown in FIG. 4.

In yet another aspect, the invention relates to methods of determining three dimensional structures of RPTK extracellular domains with unknown structure by utilizing known atomic structural coordinates of an RPTK extracellular domain. These methods can relate to homology modeling, molecular replacement, and nuclear magnetic resonance methods.

In preferred embodiments, the invention relates to a method of determining three dimensional structures of RPTK extracellular domains with unknown structures by homology modelling. These methods use the known atomic structural coordinates of an RPTK extracellular domain in conjunction with the amino acid sequences of receptor PTKs having unknown three dimensional structures. The methods comprise the steps of: (a) aligning an amino acid sequence of an RPTK with unknown structure with that of an RPTK with known atomic structural coordinates, where alignment is achieved by matching homologous regions of the amino acid sequences; (b) transferring the atomic structural coordinates of each of the homologous amino acids from the known atomic structural coordinates to a computer representation of a structure of the corresponding amino acids in the RPTK sequence with unknown structure; and (c) determining low energy conformations of the resulting RPTK structure.

Preferably, the known atomic structural coordinates are of an RPTK extracellular domain bound to a ligand or ligand analog. More preferably, the known atomic structural coordinates are of an FGFR extracelluar domain, preferably FGFR1, bound to an FGF, preferably FGF1 or FGF2. Most preferably, the known atomic structural coordinates are the coordinates set forth in Table 1 or Table 2.

The term "amino acid sequence" describes the order of amino acids in the amino acid chain comprising a polypeptide corresponding to all or a portion of an RPTK. In preferred embodiments, the amino acid sequence describes the order of amino acids in all or a portion of the extracellular domain of an RPTK.

The term "aligning" describes matching the beginning and the end of two or more amino acid sequences. Homologous amino acid sequences are placed on top of one another during the alignment process.

The term "homologous" as used herein in reference to protein sequences describes amino acids in two sequences that are identical or have similar side-chain chemical groups (e.g., aliphatic, aromatic, polar, negatively charged, or positively charged). Thus, protein sequences of similarity sufficient to indicate relation by a common origin or archetype are considered to possess homology, for instance. Examples of homologous amino acids are provided below.

The term "corresponding" refers to an amino acid that is aligned with another in the sequence alignment mentioned above.

The term "determining the low energy conformation" describes a process of changing the conformation of the RPTK structure such that the structure is of low free energy. The RPTK structure may or may not have a molecule(s), such as a ligand or ligand analog, bound to it.

The term "low free energy" describes a state where the molecules are in a stable state as measured by the process. A stable state is achieved when favorable interactions are formed within the complex.

The term "favorable interactions" refers to, among other things, hydrophobic, aromatic, and ionic forces, and hydrogen bonds.

The term "compound" refers to an organic molecule. The term "organic molecule" refers to a molecule which has at least one carbon atom in its structure. The compound can have a molecular weight of less than 6 kDa. Both the geometry of the compound and the interactions formed between the compound and the polypeptide preferably govern high affinity binding between the two molecules. High affinity binding is preferably governed by a dissociation equilibrium constant on the order of $10^{-6}$ M or less The term "binding site" refers to a location on an enzyme or polypeptide chain to which one or more molecules may bind. In preferred embodiments, a binding site can be a ligand binding site, a HSPG binding site, or an interaction surface between two receptors which form a dimer upon ligand binding.

The term "interactions" refers to hydrophobic, aromatic, and ionic forces and hydrogen bonds formed between atoms. Such interactions can be "intramolecular," or within the same molecule, or "intermolecular," or between separate molecules.

The term "cofactor" refers to a compound that may, in addition to the substrate, bind to a protein and undergo a chemical reaction. Multiple co-factors are nucleotides or nucleotide derivatives, such as phosphate and nicotinamide derivatives of adenosine.

The term "substrate" refers to a compound that reacts with an enzyme. Enzymes can catalyze a specific reaction on a specific substrate. For example, RPTKs can phosphorylate specific protein and peptide substrates on tyrosine moieties. In addition, nucleotides can act as substrates for protein kinases.

The term "substrate analog" refers to a compound that is structurally similar, but not identical, to a substrate. The substrate analog may be a nucleotide analog. Examples of nucleotide analogs are described below.

The term "allosteric effector" refers to a compound that causes allosteric interactions in a protein. The term "allosteric interactions" refers to interactions between separate sites on a protein. The sites can be different from the active site. The allosteric effector can enhance or inhibit catalytic activity by binding to a site that may be different than the active site.

The term "co-crystal" refers to a crystal where the polypeptide is in association with one or more compounds.

The term "ATP" refers to the chemical compound adenosine triphosphate.

The term "non-hydrolyzable" refers to a compound having a covalent bond that does not readily react with water. Examples of non-hydrolyzable analogs of ATP are AMP-PNP and AMP-PCP, whose structures are well known to those skilled in the art.

The term "AMP-PNP" refers to adenylyl imidodiphosphate, a non-hydrolyzable analog of ATP.

The term "AMP-PCP" refers to adenylyl diphosphonate, a non-hydrolyzable analogue of ATP.

"Alkyl" refers to a straight-chain, branched or cyclic saturated aliphatic hydrocarbon. Preferably, the alkyl group has 1 to 12 carbons. More preferably, it is a lower alkyl of from 1 to 7 carbons, more preferably 1 to 4 carbons. Typical alkyl groups include methyl, ethyl, propyl, isopropyl, butyl, isobutyl, tertiary butyl, pentyl, hexyl and the like. The alkyl group may preferably be optionally substituted with one or more substituents selected from the group consisting of hydroxyl, cyano, alkoxy, =O, =S, $NO_2$, halogen, $N(CH_3)_2$ amino, and SH.

"Alkenyl" refers to a straight-chain, branched or cyclic unsaturated hydrocarbon group containing at least one carbon—carbon double bond. Preferably, the alkenyl group has 2 to 12 carbons. More preferably it is a lower alkenyl of from 2 to 7 carbons, more preferably 2 to 4 carbons. The alkenyl group may preferably be optionally substituted with one or more substituents selected from the group consisting of hydroxyl, cyano, alkoxy, =O, =S, $NO_2$, halogen, $N(CH_3)_2$ amino, and SH.

"Alkynyl" refers to a straight-chain, branched or cyclic unsaturated hydrocarbon containing at least one carbon—carbon triple bond. Preferably, the alkynyl group has 2 to 12 carbons. More preferably it is a lower alkynyl of from 2 to 7 carbons, more preferably 2 to 4 carbons. The alkynyl group may preferably be optionally substituted with one or more substituents selected from the group consisting of hydroxyl, cyano, alkoxy, =O, =S, $NO_2$, halogen, $N(CH_3)_2$ amino, and SH.

"Alkoxy" refers to an "O-alkyl" group.

"Aryl" refers to an aromatic group which has at least one ring having a conjugated pi-electron system and includes carbocyclic aryl, heterocyclic aryl and biaryl groups. The aryl group may preferably be optionally substituted with one or more substituents selected from the group consisting of halogen, trihalomethyl, hydroxyl, SH, OH, $NO_2$, amine, thioether, cyano, alkoxy, alkyl, and amino.

"Alkaryl" refers to an alkyl that is covalently joined to an aryl group. Preferably, the alkyl is a lower alkyl.

"Carbocyclic aryl" refers to an aryl group wherein the ring atoms are carbon.

"Heterocyclic aryl" refers to an aryl group having from 1 to 3 heteroatoms as ring atoms, the remainder of the ring atoms being carbon. Heteroatoms include oxygen, sulfur, and nitrogen. Thus, heterocyclic aryl groups include furanyl, thienyl, pyridyl, pyrrolyl, N-lower alkyl pyrrolo, pyrimidyl, pyrazinyl, imidazolyl and the like.

"Amide" refers to —C(O)—NH—R, where R is alkyl, aryl, alkylaryl or hydrogen.

"Thioamide" refers to —C(S)NH—R, where R is alkyl, aryl, alkylaryl or hydrogen.

"Amine" refers to a —N(R')R'' group, where R' and R'' are independently selected from the group consisting of alkyl, aryl, and alkylaryl.

"Thioether" refers to —S—R, where R is alkyl, aryl, or alkylaryl.

"Sulfonyl" refers to —S(O)—R, where R is aryl, C(CN)=C-aryl, $CH_2CN$, alkylaryl, sulfonamide, NH-alkyl, NH-alkylaryl, or NH-aryl.

The term "acyl" denotes groups —C(O)R, where R is alkyl as defined above, such as formyl, acetyl, propionyl, or butyryl.

In other preferred embodiments, the invention relates to methods of determining three dimensional structures of RPTK extracellular domains with unknown structures by applying the known atomic structural coordinates of an RPTK extracellular domain to incomplete X-ray crystallographic data sets for RPTK extracellular domains having unknown three dimensional structures. The methods comprise the steps of: (a) determining the positions of atoms in the unit cell by matching diffraction data from two crystals, where one data set is from a crystal comprising an RPTK of unknown structure and the other is from a crystal comprising an RPTK having known atomic structural coordinates; and (b) determining a low energy conformation of the resulting RPTK structure.

Preferably, the complete diffraction data is from a crystal of an RPTK extracellular domain bound to a ligand or ligand analog. More preferably, the complete diffraction data is from a crystal of an FGFR extracelluar domain, preferably FGFR1, bound to an FGF, preferably FGF1 or FGF2.

The diffraction data set from the crystal comprising an RPTK of unknown structure may be a complete data set or an incomplete data set. The term "incomplete data set" as used herein relates to a X-ray crystallographic data set that does not have enough information to give rise to a three dimensional structure.

In other preferred embodiments, the invention relates to methods of determining three dimensional structures of receptor PTK extracellular domains with unknown structure by applying the known atomic structural coordinates of an RPTK extracellular domain to nuclear magnetic resonance (NMR) data of RPTK extracellular domains having unknown three dimensional structures. The methods comprise the steps of: (a) determining the secondary structure of an RPTK extracellular domain of unknown three dimensional structure using NMR data; and (b) simplifying the assignment of through-space interactions of amino acids using the known atomic structural coordinates of an RPTK. The RPTK extracellular domain of unknown three dimensional structure may or may not be complexed with compounds, ligands or modulators.

Preferably, the known atomic structural coordinates are of an RPTK extracellular domain bound to a ligand or ligand analog. More preferably, the known atomic structural coordinates are of an FGFR extracelluar domain, preferably FGFR1, bound to an FGF, preferably FGF1 or FGF2. Most preferably, the known atomic structural coordinates are the coordinates set forth in Table 1 or Table 2.

The term "secondary structure" describes the arrangement of amino acids in a three dimensional structure, such as in α-helix or β-sheet elements.

The term "through-space interactions" defines the orientation of the secondary structural elements in the three dimensional structure and the distances between amino acids from different portions of the amino acid sequence.

The term "assignment" defines a method of analyzing NMR data and identifying which amino acids give rise to signals in the NMR spectrum.

In another aspect, the invention features methods of identifying potential modulators of PTK function. By identifying one or more potential modulators from a larger group of molecules, it is possible to reduce the number of molecules that must be tested using costly and time-consuming biological assays. Thus, the methods described herein for identifying potential modulators of PTK function can provide increased efficiencies in identifying actual modulators of PTK function.

These potential modulators are preferably identified by docking a three dimensional representation of a structure of a compound with a three dimensional representation of the RPTK extracellular domain. The computer representation of the RPTK extracellular domain can be defined by atomic structural coordinates. In certain embodiments, one or more modulators are docked into the ligand binding site of the RPTK extracellular domain, and/or into the binding site for heparin sulfate-containing proteoglycans (HSPGs) of the RPTK extracellular domain.

In preferred embodiments, the method of identifying potential modulators of RPTK function comprises the steps of: (a) providing a three dimensional representation of the atomic structural coordinates of an RPTK and docking a three dimensional representation of a compound from a computer data base with the three dimensional representation of the RPTK; (b) determining a conformation of the resulting complex having a favorable geometric fit and favorable complementary interactions; and (c) identifying compounds that best fit the RPTK as potential modulators of RPTK function. The initial RPTK structure may or may not have one or more compounds, ligands, or modulators bound to it.

Preferably, the atomic structural coordinates are of an RPTK extracellular domain bound to a ligand or ligand analog. More preferably, the atomic structural coordinates are of an FGFR extracelluar domain, preferably FGFR1, bound to an FGF, preferably FGF1 or FGF2. Most preferably, the atomic structural coordinates are the coordinates set forth in Table 1 or Table 2.

The term "modulator of RPTK function" as used herein refers to a compound or ligand analog which alters the catalytic activity of an RPTK. A modulator of RPTK function can either stimulate or inhibit RPTK catalytic activity. For example, inhibitory modulators may be one or more compounds or ligand analogs that disrupt dimerization of an RPTK, prevent dimerization of an RPTK, or prevent binding of an RPTK to its ligand or to HSPGs. Alternatively, a stimulatory modulator may be one or more compounds or ligand analogs that stabilize dimer formation, or mimic the activity of the ligand of an RPTK, or mimic the activity of HSPGs.

The term "chemical group" refers to moieties that can form hydrogen bonds, hydrophobic, aromatic, or ionic interactions.

The term "docking" refers to a process of placing a compound, ligand or ligand analog in close proximity with an RPTK. In certain embodiments, docking can refer to placing a three dimensional representation of the compound, ligand, or ligand analog in close proximity with a three dimensional representation of the RPTK. The term can also refer to a process of finding low energy conformations of the resulting compound/RPTK, ligand/RPTK, or ligand analog/RPTK complex.

The term "favorable geometric fit" refers to a conformation of the compound/RPTK, ligand/RPTK, or ligand analog/RPTK complex where the surface area of the compound, ligand, or ligand analog is in close proximity with a surface of the RPTK-site without forming unfavorable interactions. Unfavorable interactions can be steric hindrances between atoms in the bound molecule and atoms in the RPTK.

The term "favorable complementary interactions" relates to hydrophobic, aromatic, ionic, and hydrogen bond donating, and hydrogen bond accepting forces formed between the compound, ligand, or ligand analog and the RPTK.

The term "potential" qualifies the term "modulator of RPTK function" because the potential modulator of RPTK function may not yet have been tested for activity in vitro or in vivo.

The term "best fit" describes compounds, ligands, or ligand analogs that complexed the most surface area and/or form the most favorable complementary interactions with the receptor PTK in a given experiment. The term "best fit" can also refer to a subset of compounds, ligands, or ligand analogs from amongst a larger group of compounds, ligands, or ligand analogs which complex the most surface area and/or form the most favorable complementary interactions with the receptor PTK. In preferred embodiments, a molecule which exhibits a best fit is in the $70^{th}$ percentile or better of molecules tested in terms of complexing the most surface area and/or forming the most favorable complementary interactions, more preferably a molecule which exhibits a best fit is in the $80^{th}$ percentile or better of molecules tested, and most preferably, a molecule which exhibits a best fit is in the $90^{th}$ percentile or better of molecules tested.

Other preferred embodiments of the invention are methods of identifying potential modulators of receptor PTK function. The method involves utilizing a three dimensional structure of a receptor PTK. The method comprises the steps of: (a) modifying a three dimensional representation of a receptor PTK having one or more compounds, ligands, or ligand analogs bound to it, where the three dimensional representations of the compounds, ligands, or ligand analogs and the receptor PTK are defined by atomic structural coordinates; (b) determining a conformation of the resulting complex having a favorable geometric fit and favorable complementary interactions; and (c) identifying the compounds, ligands, or ligand analogs that best fit the receptor PTK active-site as potential modulators of receptor PTK function.

Preferably, the atomic structural coordinates are of an RPTK extracellular domain bound to a ligand or ligand analog. More preferably, the atomic structural coordinates are of an FGFR extracelluar domain, preferably FGFR1, bound to an FGF, preferably FGF1 or FGF2. Most preferably, the atomic structural coordinates are the coordinates set forth in Table 1 or Table 2.

The term "modifying" refers to replacing, deleting, or adding one or more chemical groups. Computer representations of the chemical groups can be selected from a computer data base.

Yet another preferred embodiment of the invention is a method of identifying potential modulators of RPTK function by operating modulator construction or modulator searching computer programs on the compounds, ligands, or ligand analogs complexed with the RPTK. The method comprises the steps of: (a) providing a three-dimensional representation of one or more compounds, ligands, or ligand analogs complexed with an RPTK, where the computer representations of the compounds, ligands, or ligand analogs and the receptor PTK are defined by atomic structural coordinates; and (b) searching a data base for compounds, ligands, or ligand analogs similar to the compounds, ligands, or ligand analogs using a compound searching computer program, or replacing portions of the compounds, ligands, or ligand analogs complexed with the RPTK with similar chemical structures from a data base using a compound construction computer program, where the representations of the compounds are defined by structural coordinates. The skilled artisan will recognize that a number of suitable computer programs are available for compound searching and construction, including UNITY™ (Tripos, Inc.) and CATALYST® (MSI, Inc.)

Preferably, the atomic structural coordinates are of an RPTK extracellular domain bound to a ligand or ligand analog. More preferably, the atomic structural coordinates are of an FGFR extracelluar domain, preferably FGFR1, bound to an FGF, preferably FGF1 or FGF2. Most preferably, the known atomic structural coordinates are the coordinates set forth in Table 1 or Table 2.

The term "operating" as used herein refers to utilizing the three-dimensional conformation of molecules defined by the processes described herein in various computer programs.

The terms "similar compound," "similar ligand," and "similar ligand analog" refer to a compound, ligand, or ligand analog that has a similar geometric structure as compounds, ligands, or ligand analogs that can bind to a receptor PTK. The similar molecule can also have similar chemical groups as a molecule that is either bound to an RPTK or once bound to an RPTK. The similar chemical groups can form complementary interactions with the RPTK.

The term "compound searching computer program" describes a computer program that searches computer representations of compounds, ligands, or ligand analogs from a computer data base that have similar three dimensional structures and similar chemical groups as a compound of interest.

The term "similar chemical structures" as used herein refers to one or more chemical groups that share similar a similar geometry with one or more portions of another molecule. In preferred embodiments, a similar chemical structure shares a similar geometry with a molecule that is in a complex with an RPTK, or shares a similar geometry with a molecule that has been removed from an RPTK structure. Similar chemical structures can also refer to chemical groups that can form one or more complementary interactions with an RPTK that are similar to those formed between and an RPTK and a complexed molecule.

The term "replacing structures" refers to removing one or more portions of a molecule that is in a complex with an RPTK, or removing one or more portions of a molecule that has been removed from an RPTK, and connecting the broken bonds to produce a similar molecule.

The term "compound construction computer program" describes a computer program that replaces computer representations of chemical groups in a compound, ligand, or ligand analog with groups from a computer data base.

The term "similar three dimensional structure" describes two molecules with nearly identical shape and volume.

The methods for using the crystalline forms and three dimensional structures of the invention can relate to a broad range of protein kinases. Thus, in preferred embodiments, the invention relates to an RPTK. The RPTK is preferably PDGFR, EGFR, SCFR, VEGFR, HGFR, neurotrophinR, HER2, HER3, HER4, InsulinR, IGFR, CSFIR, FLK, KDR, VEGFR2, CCK4, MET, TRKA, AXL, TIE, EPH, RYK, DDR, ROS, RET, LTK, ROR1, MUSK, members of the FGFR family, such as FGFR1, FGFR2, FGFR3, and FGFR4, or an orphan receptor PTK.

In another aspect, the invention features a potential modulator of RPTK function identified by methods disclosed in the invention.

Another aspect of the invention is a method for synthesizing a potential modulator of RPTK function or its pharmaceutically acceptable salts, isomers, metabolites, esters, amides, or prodrugs by a standard synthetic method known in the art. Synthetic procedures are discussed below.

In another aspect, the invention features methods for identifying a modulator of RPTK function. The method comprises the steps of: (a) administering a potential modulator of RPTK function, ligand, ligand analog, or compound to cells; (b) comparing the level of RPTK phosphorylation between cells not administered the potential modulator, ligand, ligand analog, or compound and cells administered the potential modulator; and (c) identifying the potential modulator, ligand, ligand analog, or compound as a modulator of RPTK function based on the difference in the level of receptor PTK phosphorylation. The skilled artisan will recognize that the difference in PTK phosphorylation required for a potential modulator, ligand, ligand analog, or compound to be identified as a modulator of RPTK function will depend on the particular RPTK, the specificity of the modulator, the nature of the disorder associated with the RPTK function, etc.

The term "cells" refers to any type of cells either primary or cultured. Primary cells can be extracted directly from an organism while cultured cells rapidly divide and can be cultured in many successive rounds. Cells can be grown in a variety of containers including, but not limited to flasks, dishes, and well plates.

The term "administer," as used in reference to cells, refers to a method of delivering a potential modulator, ligand, ligand analog, or compound to cells. The compound can be prepared using a carrier such as dimethyl sulfoxide (DMSO) in an aqueous solution. The aqueous solution comprising the compound, also termed an "aqueous preparation", can be simply mixed into the medium bathing the layer of cells or microinjected into the cells themselves. The compounds may be administered to the cells using a suitable buffered solution.

The term "suitable buffered solution" refers to an aqueous preparation of the compound that comprises a salt that can control the pH of the solution at low concentrations. Because the salt exists at low concentrations, the salt preferably does not alter the function of the cells.

The term "RPTK phosphorylation" refers to the presence of phosphate on the RPTK. Phosphates on RPTKs can be identified by antibodies that bind them specifically with high affinity.

In another aspect, the invention features a method of identifying a potential modulator of RPTK function as a modulator of RPTK function. The method comprises the steps of: (a) administering a potential modulator of RPTK function to cells; (b) comparing the level of cell growth between cells not administered the potential modulator and cells administered the potential modulator; and (c) identifying the potential modulator as a modulator of RPTK function based on the difference in cell growth.

The term "cell growth" refers to the rate at which a group of cells divides. Cell division rates can be readily measured by methods utilized by those skilled in the art.

Another aspect of the invention features a method of diagnosing a disease by identifying cells harboring a RPTK with inappropriate activity. The method comprises the steps of: (a) administering a modulator of RPTK function to cells; (b) comparing the rate of cell growth between cells not administered the modulator and cells administered the modulator; and (c) diagnosing a disease by characterizing cells harboring a RPTK with inappropriate activity from the effect of the modulator on the difference in the rate of cell growth. The modulator can be identified by the methods of the invention.

The term "inappropriate activity" refers to an RPTK that regulates a step in a signal transduction process at a higher or lower rate than normal cells. Aberrations in the rate of signal transduction can be caused by alterations in the stimulation of an RPTK by a growth factor, alterations in the activity of RPTK-specific phosphatase, over-expression of a RPTK in a cell, or mutations in the catalytic region of the RPTK itself.

The term "signal transduction process" describes the steps in a cascade of events where an extracellular signal is transmitted into an intracellular signal.

The term "RPTK-specific phosphatase" describes an enzyme that dephosphorylates a particular RPTK and thereby regulates that RPTK's activity.

Another aspect of the invention is a method of treating a disease associated with a RPTK with inappropriate activity in a cellular organism, where the method comprises the steps of: (a) administering the modulator of RPTK function to the organism, where the modulator is in an acceptable pharmaceutical preparation; and (b) activating or inhibiting the RPTK function to treat the disease.

The term "organism" relates to any living being comprised of at least one cell. An organism can be as simple as one eukaryotic cell or as complex as a mammal.

The term "administering", in reference to an organism, refers to a method of introducing the compound to the organism. The compound can be administered when the cells or tissues of the organism exist within the organism or outside of the organism. Cells existing outside the organism can be maintained or grown in cell culture dishes. For cells harbored within the organism, many techniques exist in the art to administer compounds, including (but not limited to) oral, parenteral, dermal, ocular, subcutaneous, and rectal applications. For cells outside of the patient, multiple techniques exist in the art to administer the compounds, including (but not limited to) cell microinjection techniques, transformation techniques, and carrier techniques.

The term "pharmaceutically acceptable composition" refers to a preparation comprising the modulator of RPTK activity. The composition is acceptable if it does not appreciably cause irritations to the organism administered the compound.

In preferred embodiments of the of the invention, the receptor PTK is selected from the group consisting of PDGFR, SCFR, EGFR, VEGFR, HGFR, neurotrophinR, HER2, HER3, HER4, InsulinR, IGFR, CSFIR, FLK, KDR, VEGFR2, CCK4, MET, TRKA, AXL, TIE, EPH, RYK, DDR, ROS, RET, LTK, ROR1, MUSK, members of the FGFR family, such as FGFR1, FGFR2, FGFR3, and FGFR4, and orphan receptor PTKs.

The summary of the invention described above is non-limiting and other features and advantages of the invention will be apparent from the following detailed description, and from the claims.

BRIEF DESCRIPTION OF THE FIGURES

FIG. 3 provides a topology diagram of the Ig folds of FGFR1 D2 and D3 in comparison to the Ig fold of telokin.

FIG. 4 provides a sequence alignment of the D2-D3 region of human FGFR1, FGFR2, FGFR3, and FGFR4.

FIG. 15 shows Structure-based sequence alignment of the ligand binding domains of D2 and D2-D3 linker of human FGF receptors (SEQ ID NOS 5–8, respectively).

FIG. 16 shows Structure-based sequence alignment of the ligand binding domains of D3 of human FGF receptors (SEQ ID NOS 9–16, respectively).

FIG. 17 shows structure-based sequence alignment of FGFs (SEQ ID NOS 17–35, respectively, in order of appearance) performed using the CLUSTALW program (Thompson et al., *Nucleic Acids Res.* 22, 4673–4680 (1994)). All of the FGFs used in this alignment are from human, with the exception of FGF15, for which only the chicken sequence is available. The secondary structure assignment is according to the published nomenclature, with the beta strands labeled from 1 through 12 (Faham et al., Curr. Opin. Struct. Biol. 8, 578–586 (1998)). The location and the length of the beta strands are shown on the top of the sequence alignment. FGF residues are colored with respect to the region on FGFR with which they interact: FGF residues that interact with D2 are colored green, residues that interact with the linker region are colored gray, and residues that interact with D3 are colored cyan. FGF residues that interact with the betaC'-betaE segment in D3 are colored red. A period indicates sequence identity to FGF2. A dash represents a gap introduced to optimize the alignment. A tilde at the C-terminus of FGF indicates that there are additional sequences down stream to the last amino acid shown. A star indicates that numbering does not start at the initiation methionine. Residue numbering for FGF2 is according to Springer et al., J. Biol. Chem. 269, 26879–26884 (1994). Residue numbering for FGF1 is according to Zhu et al., Science 251, 90–93 (1991). A checkmark indicates FGF residues that have been shown by mutagenesis to be important for receptor binding.

FIG. 20 depicts the sequence alignment based on secondary structures of SCF, M-CSF and IL-5 (SEQ ID NOS 36–44, respectively, in order of appearance). Secondary structure assignments for M-CSF and IL-5 are from PDB databank. beta-Strands are yellow and helices are marked bright green.

FIG. 25 shows sequence alignments of human, rat, mouse, dog and pig SCFs (SEQ ID NOS 45–49, respectively). Residues of the acidic patch are colored red and residues of the two basic patches are colored blue. Stars mark amino acid residues that are altered in rodents. The secondary structures are marked below the sequences with 'H' representing helices and 'E' representing beta strands.

BRIEF DESCRIPTION OF THE CRYSTALLOGRAPHIC ATOMIC STRUCTURAL COORDINATES

Figure 1:
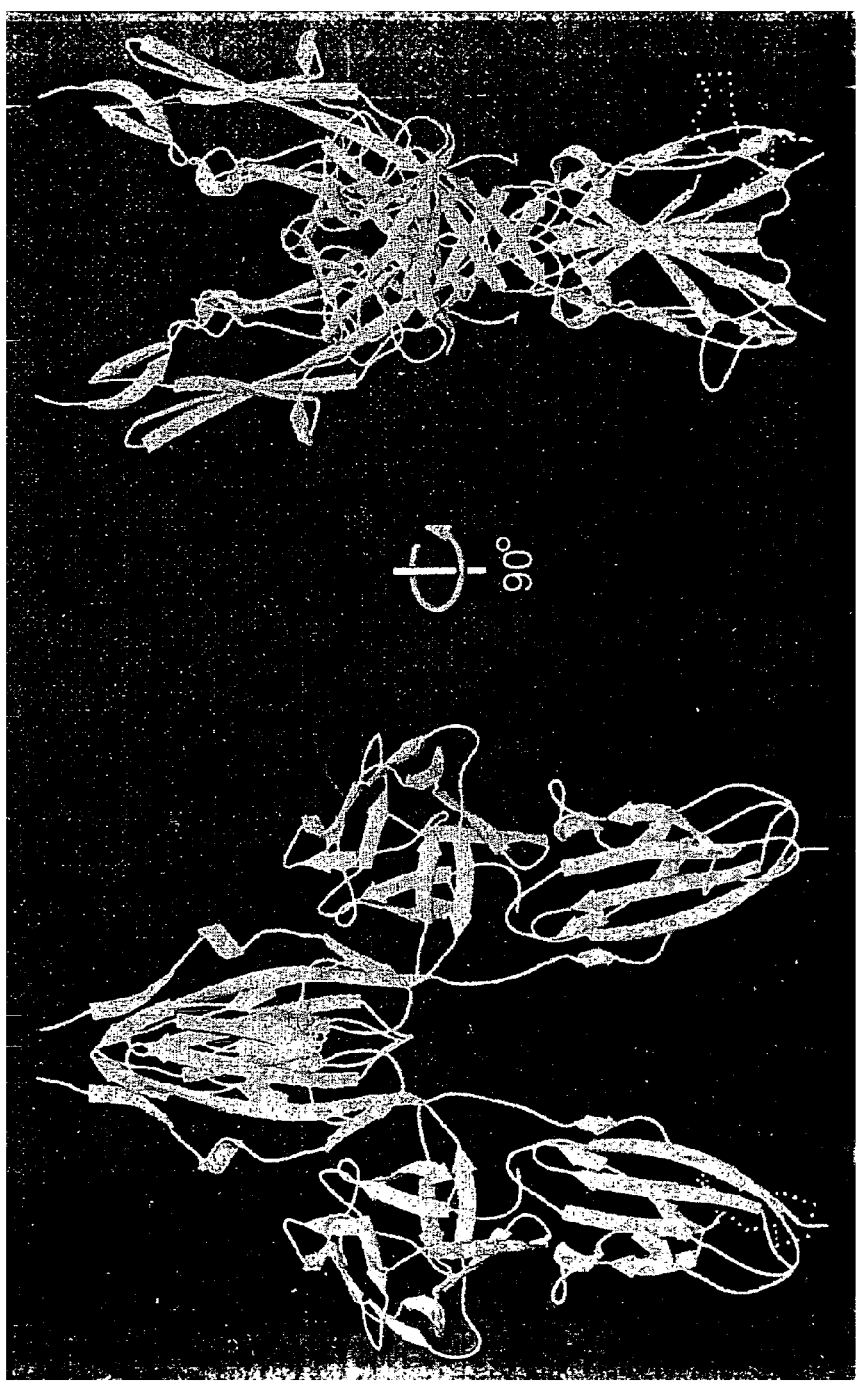
FIG. 1 provides a ribbon diagram of the structure of a dimer of FGFR1 D2-D3 complexed with FGF2. Two views are related by a rotation of about 90° about the vertical axis. The D2 and D3 domains are shown in green and blue, respectively, the short linker connecting D2 and D3 is shown in gray, and the FGF2 molecules are shown in orange.
Figure 2:
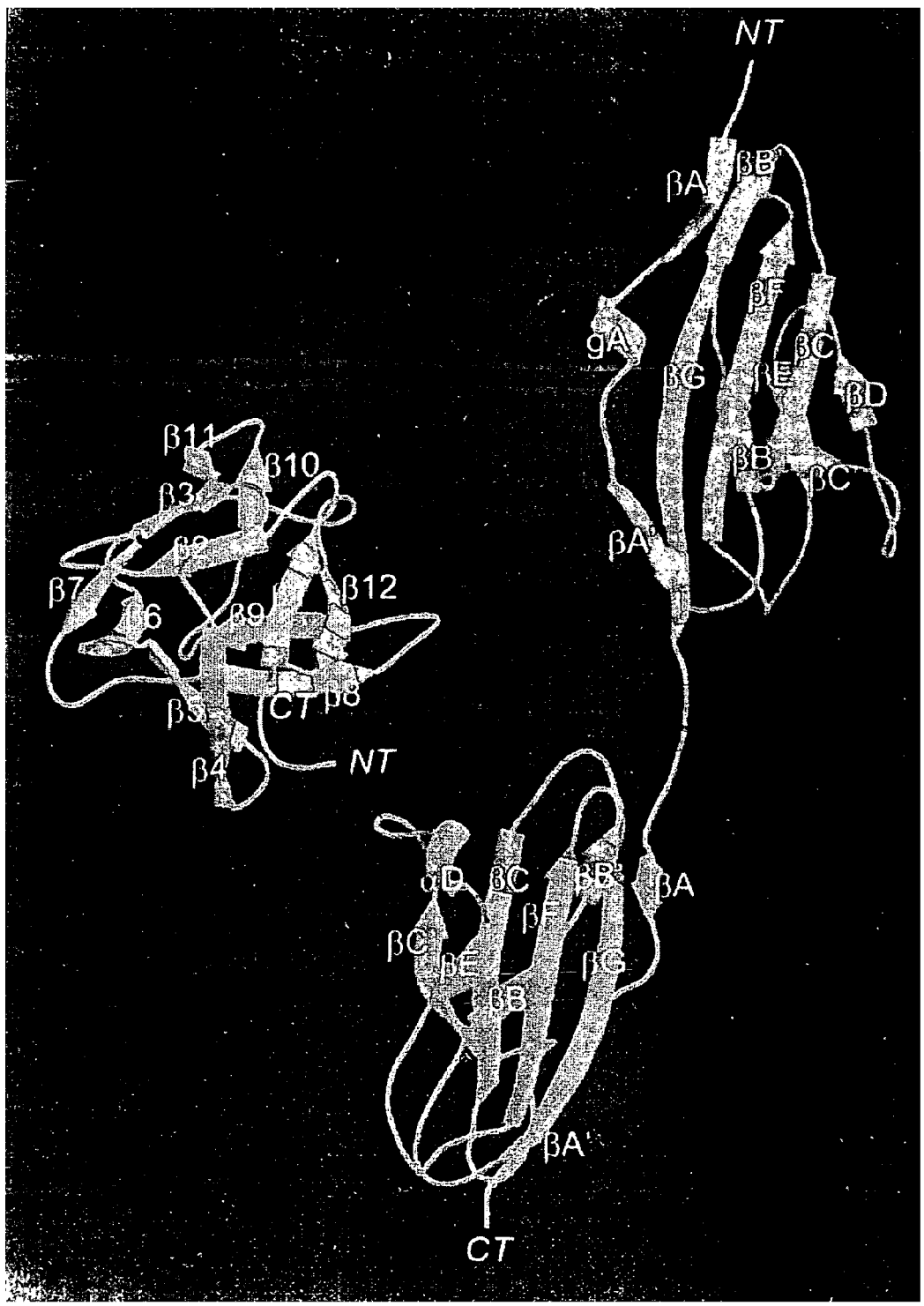
FIG. 2 provides a ribbon diagram of the structure of FGFR1 D2-D3 complexed with FGF1. The D2 and D3 domains are shown in green and blue, respectively, the short linker connecting D2 and D3 is shown in gray, and FGF1 is shown in orange.

The crystallographic structural coordinates are located at the end of the section entitled "Examples" and before the claims. Table 1 provides the atomic structure coordinates of crystals of FGFR1-D2-D3 complexed with FGF2 of the invention as determined by X-ray crystallography. Table 2 provides the atomic structure coordinates of crystals of FGFR1-D2-D3 complexed with FGF1 of the invention as determined by X-ray crystallography. Table 4 provides the atomic structure coordinates of crystals of an SCF (1–141) non-covalent homodimer. Table 6 provides the atomic structure coordinates of crystals of a dimeric 2:2:2 FGF2:FGFR1: heparin ternary complex.

The columns (from left to right) in these tables are descriptions of the atoms by number and type, amino acid and number containing the atom, the x coordinate, y coordinate, z coordinate, bond connectivity, and temperature factor. All of these parameters are well defined in the art.

DETAILED DESCRIPTION OF THE INVENTION

The present invention is directed to the determination and use of three dimensional structures of receptor protein tyrosine kinases. The three dimensional structures of receptor PTKs can facilitate the design and identification of modulators of receptor PTK function.

Protein tyrosine kinases (PTKs) comprise a large and diverse class of enzymes. Schlessinger and Ullrich, 1992, *Neuron* 9: 383–391. The PTK family is subdivided into members that are receptors and those that are non-receptors. The receptor PTK (RPTK) family contains multiple subfamilies, one of which is the fibroblast growth factor receptor (FGFR) PTK which is a molecule implicated in regulating angiogenesis a well as cellular proliferation and differentiation. Givol and Yayon, 1992, *FASEB J.* 6 (15): 3362–3369.

FGFR1 through FGFR4, are known as "high affinity FGFRs," due to the ability to bind fibroblast growth factors with a high affinity. These high affinity FGFRs are characterized by an extracellular ligand-binding domain which comprises three immunoglobulin (IG)-like domains (known as D1 through D3), a single transmembrane helix, and a cytoplasmic domain containing tyrosine kinase activity. See Lee et al., 1989, *Science* 245: 57–60; Jaye et al., 1992, *J. Mol. Biol.* 227: 840–851; Johnson & Williams, 1993, *Adv. Cancer. Res.* 60: 1–41. FGFRs can mediate cellular functions by their role in one or more cellular signal transduction processes. Cellular signal transduction processes comprise a cascade of multiple steps that convert an extracellular signal into an intracellular signal.

RPTK-mediated signal transduction is initiated by binding of a specific extracellular ligand to the extracellular domain, followed by receptor dimerization, and subsequent autophosphorylation of the RPTK. Preferred ligands are epidermal growth factors, insulin, platelet-derived growth factors, vascular endothelial growth factors, fibroblast growth factors, hepatocyte growth factors, and neurotrophins. The FGF subfamily presently contains about 18 members, named FGF1 through FGF18, which bind to FGFRs, and to HSPGs. Those skilled in the art can identify presently unknown members of the FGF subfamily by sequence homology to known subfamily members, and/or by the presence of a common protein fold. Each of the four high affinity FGFRs binds to a specific subset of FGFs. Ornitz et al., 1996, *J. Biol. Chem.* 271: 15292–15297.

Once an RPTK is autophosphorylated, the phosphate groups are binding sites for intracellular signal transduction molecules which leads to the formation of protein complexes at the cell membrane. These complexes facilitate an appropriate cellular effect (e.g., cell division, metabolic effects to the extracellular microenvironment) in response to the ligand that began the cascade of events.

RPTKs function as binding sites for several intracellular proteins. Intracellular RPTK binding proteins are divided into two principal groups: (1) those which harbor a catalytic domain; and (2) those which lack such a domain but serve as adapters and associate with catalytically active molecules. Songyang et al., 1993, *Cell* 72:767–778. SH2 (src homology) domains are common adaptors found in proteins which directly bind to the RPTK. SH2 domains are harbored by RPTK binding proteins of both groups mentioned above. Fantl et al., 1992, *Cell* 69:413423; Songyang et al., 1994, *Mol. Cell. Biol.* 14:2777–2785); Songyang et al., 1993, *Cell* 72:767–778; and Koch et al., 1991, *Science* 252:668–678.

The specificity of the interactions between RPTKs and the SH2 domains of their binding proteins is determined by the amino acid residues immediately surrounding the phosphorylated tyrosine residue. Differences in the binding affinities of SH2 domains is correlated with the observed differences in substrate phosphorylation profiles of downstream molecules in the signal transduction process. Songyang et al., 1993, *Cell* 72:767–778. These observations suggest that the function of each RPTK is determined not only by its pattern of expression and ligand availability but also by the array of downstream signal transduction pathways that are activated by a particular receptor. Thus, RPTKs provide a controlling regulatory role in signal transduction processes as a consequence of autophosphorylation.

RPTK-mediated signal transduction regulates cell proliferative, differentiation, and metabolic responses in cells. Therefore, inappropriate RPTK activity can result in a wide array of disorders and diseases. These disorders, which are described below, may be treated by the modulators of RPTK function designed or identified by the methods disclosed herein.

The present invention also relates to crystalline polypeptides corresponding to the extracellular domain of receptor tyrosine kinases. Such receptor protein tyrosine kinases are not covalently cross-linked, but are understood to undergo ligand-induced dimerization. Preferably, the crystalline extracellular domains are of sufficient quality to allow for the determination of a three-dimensional X-ray diffraction structure to a resolution of about 1.5 Å to about 3 Å, and most preferably about 2.8 Å. The invention also relates to methods for preparing and crystallizing the polypeptides. The polypeptides themselves, as well as information derived from their crystal structures can be used to analyze and modify tyrosine kinase activity as well as to identify compounds that interact with the extracellular domain.

The polypeptides of the invention are most preferably designed on the basis of the structure of a region in the extracellular domain of the RPTKs that contains the ligand binding domain. By way of illustration, FIG. 4 shows the amino acid sequence alignment of the ligand binding D2-D3 domains of human FGFR1, FGFR2, FGFR3, and FGFR4. The applicants have discovered and determined the boundaries of the extracellular domain required for crystallization of the resulting polypeptide. Surprisingly, these boundaries are very similar to a naturally occurring variant of FGFR1 which retains approximatly full ligand binding capacity and specificity. See Johnson et al., *Mol Cell. Biol.*, 1990 10: 4728–4736.

The resulting crystal structures consists of a unit cell comprising a dimer of two FGFR1 D2-D3 domains, each bound to an FGF molecule. The dimeric structure is stabilized by interactions between the two D2 domains, and by interactions between the FGF molecule in one member of the dimer and the D2 domain of the other member of the dimer. These contacts which stabilize the dimeric structure within the crystal are believed to be similar or identical to contacts which result in dimerization and activation of FGFR1 in vivo. Thus, the crystal structures of the invention provides for the first time a detailed view of the events leading to ligand-induced dimerization and activation of RPTKs.

The crystal structures also disclose a possible role for the acid box region of the extracellular domain of RPTKs in dimerization and activation. The acid box is a continuous stretch of acidic residues in the linker between D1 and D2. Models inferred from the crystal structures of the invention imply that the acid box may interact with the heparin binding region of D2, competing with heparin for binding. Surprisingly, these models imply that loss of the of the acid box/D2 interaction may permit heparin-induced dimerization and activation of FGFR1 in the absence of FGF.

The understanding of dimerization and activation at the atomic level can allow the design of modulators of RPTK function, for example molecules which contribute to or disrupt receptor/ligand binding or intradimer contacts. Such modulators may provide useful treatments for various RPTK diseases.

I. PTK Associated Diseases

PTK-associated diseases and disorders include, but are not limited to, blood vessel proliferative disorders, fibrotic disorders, and mesangial cell proliferative disorders. Blood vessel proliferative disorders refer to angiogenic and vasculogenic disorders generally resulting in abnormal proliferation of blood vessels. The formation and spreading of blood vessels play important roles in a variety of physiological processes such as embryonic development, corpus luteum formation, wound healing and organ regeneration. They also play a pivotal role in cancer development, for example in Kaposi's sarcoma. Other examples of blood vessel proliferation disorders include arthritis, where new capillary blood vessels invade the joint and destroy cartilage, ocular diseases, like diabetic retinopathy, where new capillaries in the retina invade the vitreous, bleed and cause blindness, and von Hippel-Lindau disease (VHL), which is characterized by a predisposition for retinal angiomas, hemangioblastomas in the central nervous system, renal cell carcinomas, pheochromocytomas, and islet cell tumors of the pancreas. Conversely, disorders related to the shrinkage, contraction or closing of blood vessels are implicated in such diseases as restenosis.

Fibrotic disorders refer to the abnormal formation of extracellular matrix. Examples of fibrotic disorders include hepatic cirrhosis and mesangial cell proliferative disorders. Hepatic cirrhosis is characterized by the increase in extracellular matrix constituents resulting in the formation of a hepatic scar. Hepatic cirrhosis can cause diseases such as cirrhosis of the liver. An increased extracellular matrix resulting in a hepatic scar can also be caused by viral infection such as hepatitis.

Mesangial cell proliferative disorders refer to disorders brought about by abnormal proliferation of mesangial cells. Mesangial proliferative disorders include various human renal diseases, such as glomerulonephritis, diabetic nephropathy, malignant nephrosclerosis, thrombotic microangiopathy syndromes, transplant rejection, and glomerulopathies. The PDGF-R has been implicated in the maintenance of mesangial cell proliferation. Floege et al., 1993, *Kidney International* 43:47S–54S.

RPTKs are directly associated with the cell proliferative disorders described above. For example, some members of the RPTK family have been associated with the development of cancer. Some of these receptors, like EGFR (Tuzi et al., 1991, *Br. J. Cancer* 63:227–233; Torp et al., 1992, *APMIS* 100:713–719) HER2/neu (Slamon et al., 1989, *Science* 244:707–712) and PDGF-R (Kumabe et al., 1992, *Oncogene* 7:627–633) are over-expressed in many tumors and/or persistently activated by autocrine loops. In fact, RPTK over-expression (Akbasak and Suner-Akbasak et al., 1992, *J. Neurol. Sci.* 111:119–133; Dickson et al., 1992, *Cancer Treatment Res.* 61:249–273; Korc et al., 1992, *J. Clin. Invest.* 90:1352–1360) and autocrine loop stimulation (Lee and Donoghue, 1992, *J. Cell. Biol.* 118:1057–1070; Korc et al., supra; Akbasak and Suner-Akbasak et al., supra) account for the most common and severe cancers. For example, EGFR is associated with squamous cell carcinoma, astrocytoma, glioblastoma, head and neck cancer, lung cancer and bladder cancer. HER2 is associated with breast, ovarian, gastric, lung, pancreas and bladder cancer. PDGFR is associated with glioblastoma, lung, ovarian, and prostate cancer. The RPTK c-met is generally associated with hepatocarcinogenesis and thus hepatocellular carcinoma. Additionally, c-met is linked to malignant tumor formation. More specifically, c-met has been associated with, among other cancers, colorectal, thyroid, pancreatic and gastric carcinoma, leukemia and lymphoma. Additionally, over-expression of the c-met gene has been detected in patients with Hodgkin's disease, Burkitt's disease, and the lymphoma cell line.

The IGF-I RPTK, in addition to being implicated in nutritional support and in type-II diabetes, is also associated with several types of cancers. For example, IGF-I has been implicated as an autocrine growth stimulator for several tumor types, e.g. human breast cancer carcinoma cells (Arteaga et al., 1989, *J. Clin. Invest.* 84:1418–1423) and small lung tumor cells (Macauley et al., 1990, *Cancer Res.* 50:2511–2517). In addition, IGF-I, integrally involved in the normal growth and differentiation of the nervous system, appears to be an autocrine stimulator of human gliomas. Sandberg-Nordqvist et al., 1993, *Cancer Res.* 53:2475–2478. The importance of the IGF-R and its modulators in cell proliferation is further supported by the fact that many cell types in culture (fibroblasts, epithelial cells, smooth muscle cells, T-lymphocytes, myeloid cells, chondrocytes, osteoblasts, the stem cells of the bone marrow) are stimulated to grow by IGF-I. Goldring and Goldring, 1991, *Eukaryotic Gene Expression* 1:301–326. A series of recent publications suggest that IGF-R plays a central role in the mechanisms of transformation and, as such, could be a preferred target for therapeutic interventions for a broad spectrum of human malignancies. Baserga, 1995, *Cancer Res.* 55:249–252; Baserga, 1994, *Cell* 79:927–930; Coppola et al., 1994, *Mol. Cell. Biol.* 14:45884595.

The association between abnormalities in RPTKs and disease are not restricted to cancer, however. For example, RPTKs are associated with metabolic diseases like psoriasis, diabetes mellitus, wound healing, inflammation, and neuro-degenerative diseases. EGFR is indicated in corneal and dermal wound healing. Defects in InsulinR and IGFR are indicated in type-II diabetes mellitus. A more complete correlation between specific RPTKs and their therapeutic indications is set forth in Plowman et al., 1994, *DN&P* 7:334–339.

The instant invention is directed in part towards designing modulators of RPTK function that could indirectly kill tumors by cutting off their source of sustenance. Normal vasculogenesis and angiogenesis play important roles in a variety of physiological processes such as embryonic development, wound healing, organ regeneration and female reproductive processes such as follicle development in the corpus luteum during ovulation and placental growth after pregnancy. Folkman and Shing, 1992, *J. Biological Chem.* 267:10931–34. However, many diseases are driven by persistent unregulated or inappropriate angiogenesis. For example, in arthritis, new capillary blood vessels invade the joint and destroy the cartilage. In diabetes, new capillaries in the retina invade the vitreous, bleed and cause blindness. Folkman, 1987, in: *Congress of Thrombosis and Haemostasis* (Verstraete, et. al, eds.), Leuven University Press, Leuven, pp. 583–596. Ocular neovascularization is the most common cause of blindness and dominates approximately twenty (20) eye diseases.

Moreover, vasculogenesis and/or angiogenesis can be associated with the growth of malignant solid tumors and metastasis. A tumor must continuously stimulate the growth of new capillary blood vessels for the tumor itself to grow. Furthermore, the new blood vessels embedded in a tumor provide a gateway for tumor cells to enter the circulation and to metastasize to distant sites in the body. Folkman, 1990, *J. Natl. Cancer Inst.* 82:4–6; Klagsbrunn and Soker, 1993, *Current Biology* 3:699–702; Folkman, 1991, *J. Natl., Cancer Inst.* 82:4–6; Weidner et al., 1991, *New Engl. J. Med.* 324:1–5.

Several polypeptides with in vitro endothelial cell growth promoting activity have been identified. Examples include acidic and basic fibroblastic growth factor (αFGF, βFGF), vascular endothelial growth factor (VEGF) and placental growth factor. Unlike αFGF and βFGF, VEGF has recently been reported to be an endothelial cell specific mitogen. Ferrara and Henzel, 1989, *Biochem. Biophys. Res. Comm.* 161:851–858; Vaisman et al., 1990, *J. Biol. Chem.* 265:19461–19566.

Thus, identifying the specific receptors that bind FGF or VEGF is important for understanding endothelial cell proliferation regulation. Two structurally related receptor PTKs that bind VEGF with high affinity are identified: the flt-1 receptor (Shibuya et al, 1990, *Oncogene* 5:519–524; De Vries et al., 1992, *Science* 255:989–991) and the KDR/FLK-1 receptor (VEGFR2), discussed in the U.S. patent application Ser. No. 08/193,829. In addition, a receptor that binds FGF is identified. Jaye et al., 1992, *Biochem. Biophys. Acta* 1135:185–199). Consequently, these RPTKs most likely regulate endothelial cell proliferation.

FGFRs play important roles in angiogenesis, wound healing, embryonic development, and malignant transformation. Basilico and Moscatelli, 1992, *Adv. Cancer Res.* 59:115–165. Four high affinity mammalian FGFRs (FGFR14) have been described and additional diversity is generated by alternative RNA splicing within the extracellular domains. Jaye et al., 1992, *Biochem. Biophys. Acta* 1135:185–199. Like other RPTKs, dimerization of FGF receptors is essential for their activation. Soluble or cell surface-bound heparin sulfate proteoglycans act in concert with FGF to induce dimerization (Schlessinger et al., 1995, *Cell* 83:357–360), which leads to autophosphorylation of specific tyrosine residues in the cytoplasmic domain. Mohammadi et al., 1996, *Mol. Cell Biol.* 16:977–989.

Mutations in three human FGF receptor genes, FGFR1, FGFR2, and FGFR3, have been implicated in a variety of human genetic skeletal disorders. Mutations in FGFR1 and FGFR2 result in the premature fusion of the flat bones of the skull and cause the craniosynostosis syndromes, such as Apert (FGFR2) (Wilkie et al., 1994, Nat. Genet. 8:269–274), Pfeiffer (FGFR1 and FGFR2) (Muenke et al., 1994, Nat. Genet. 8:269–274), Jackson-Weiss (FGFR2) (Jabs et al., 1994, *Nat. Genet.* 8:275–279) and Crouzon (FGFR2) (Jabs et al., 1994, *Nat. Genet.* 8:275–279) syndromes. In contrast, mutations in FGFR3 are implicated in long bone disorders and cause several clinically related forms of dwarfism including achondroplasia (Shiang et al., 1994, *Cell* 78:335–342), hypochondroplasia (Bellus et al., 1995, *Nat. Genet.* 10:357–359) and the neonatal lethal thanatophoric dysplasia (Tavormina et al., 1995, *Nat. Genet.* 9:321–328). It has been shown that these mutations lead to constitutive activation of the tyrosine kinase activity of FGFR3 (Webster et al., 1996, *EMBO J.* 15:520–527). Furthermore gene-targeting experiments in mice have revealed an essential role for FGFR3 in developmental bone formation (Deng et al., 1996, *Cell* 84:911–921).

Another major role proposed for FGFs in vivo is the induction of angiogenesis (Folkman and Klagsbrun, 1987, *Science* 236:442). Therefore, inappropriate expression of FGFs or of their receptors or aberrant function of the tyrosine kinase activity could contribute to several human angiogenic pathologies such as diabetic retinopathy, rheumatoid arthritis, atherosclerosis and tumor neovascularization (Klagsbrun and Edelman, 1989, *Arteriosclerosis* 9:269). Moreover, FGFs are thought to be involved in malignant transformation. Indeed, the genes coding for the three FGF homologues int-2, FGF-5 and hst-1/K-fgf were originally isolated as oncogenes. Furthermore, the cDNA encoding FGFR1 and FGFR2 are amplified in a population of breast cancers (Adnane et al., 1991, *Oncogene* 6:659–663). Overexpression of FGF receptors has been also detected in human pancreatic cancers, astrocytomas, salivary gland adenosarcomas, Kaposi's sarcomas, ovarian cancers and prostate cancers.

Evidence, such as the disclosure set forth in copending U.S. application Ser. No. 08/193,829, strongly suggests that VEGF is not only responsible for endothelial cell proliferation, but also is a prime regulator of normal and pathological angiogenesis. See generally, Klagsburn and Soker, 1993, *Current Biology* 3:699–702; Houck et al., 1992, *J. Biol. Chem.* 267:26031–26037. Moreover, it has been shown that KDR/FLK-1 and flt-I are abundantly expressed in the proliferating endothelial cells of a growing tumor, but not in the surrounding quiescent endothelial cells. Plate et al., 1992, *Nature* 359:845–848; Shweiki et al., 1992, *Nature* 359: 843–845.

The invention is directed to designing and identifying modulators of RPTK functions that could modify the inappropriate activity of a RPTK involved with a clinical disorder. The rational design and identification of modulators of RPTK functions can be accomplished by utilizing the structural coordinates that define a RPTK three dimensional structure.

II. Modulators of PTK functions as Therapeutics for Disease

As a consequence of the disorders discussed above, scientists in the biomedical community are searching for modulators of RPTK functions that down-regulate signal transduction pathways associated with inappropriate RPTK activity.

Several small molecule modulators of RPTK functions have been identified which can traverse the cell membrane and do not hydrolyze in acidic environments. For example, bis monocyclic, bicyclic or heterocyclic aryl compounds (PCT WO 92/20642), vinylene-azaindole derivatives (PCT WO 94/14808) 1-cyclopropyl-4-pyridyl-quinolones (U.S. Pat. No. 5,330,992), styryl compounds (U.S. Pat. No. 5,217,999), styryl-substituted pyridyl compounds (U.S. Pat. No. 5,302,606), certain quinazoline derivatives (EP Application No. 0 566 266 A1), seleoindoles and selenides (PCT WO 94/03427), tricyclic polyhydroxylic compounds (PCT WO 92/21660), and benzylphosphonic acid compounds (PCT WO 91/15495) are described as RPTK inhibitors.

Although some modulators of RPTK function are known, many of these are not specific for RPTK subfamilies and will therefore cause multiple side-effects as therapeutics. Certain compounds of the oxindolinone/thiolindolinone family, however, are believed to be specific for the FGF receptor subfamily (U.S. patent application Ser. No. 08/702,232, filed Aug. 23, 1996, invented by Tang et al., entitled "Indolinone Combinatorial Libraries and Related Products and Methods for the Treatment of Disease"). In addition, compounds of the oxindolinone/thiolindolinone family are non-hydrolyzable in acidic conditions and can be highly bioavailable. These modulators of RPTK function, however, target the catalytic domain of the FGFR subfamily, and thus are not directed towards affecting receptor RPTK dimerization and activation via inteactions in the extracellular domain.

III. Crystalline Tyrosine Kinases

Crystalline RPTKs of the invention include native crystals, derivative crystals and co-crystals. The native crystals of the invention generally comprise substantially pure polypeptides corresponding to the extracellular domain of an RPTK in crystalline form. In preferred embodiments, the crystals of the invention comprise polypeptides corresponding to the extracellular domain of an RPTK in a complex with a ligand.

It is to be understood that the crystalline extracellular domains of the invention are not limited to naturally occurring or native extracellular domains. Indeed, the crystals of the invention include mutants of native extracellular domains. Mutants of native extracellular domains are obtained by replacing at least one amino acid residue in a native extracellular domain with a different amino acid residue, or by adding or deleting amino acid residues within the native polypeptide or at the N- or C-terminus of the native polypeptide, and have substantially the same three-dimensional structure as the native extracellular domain from which the mutant is derived.

Similarly, in certain embodiments in which the extracellular domain is bound to a ligand, the crystals of the invention include mutants of native extracellular domains and mutant ligands. As discussed above, mutant ligands can be obtained by replacing at least one amino acid residue in a polypeptide ligand with a different amino acid residue, or by adding or deleting amino acid residues within the native polypeptide or at the N- or C-terminus of the native polypeptide, and have substantially the same three-dimensional structure as the native ligand from which the mutant is derived.

By having substantially the same three-dimensional structure is meant having a set of atomic structure coordinates that have a root-mean-square deviation (rmsd) of less than or equal to about 2Å when superimposed with the atomic structure coordinates of the native extracellular domain and/or ligand from which the mutant is derived when at least about 50% to 100% of the C$\alpha$ atoms of the polypeptide are included in the superposition. For example, FIG. 3 shows that 68 common C$\alpha$ atoms in the D2 and D3 regions of FGFR1 and telokin, a canonical IG-fold polypeptide, can be superimposed with a rms deviation of 0.8 Å.

Amino acid substitutions, deletions and additions which do not significantly interfere with the three-dimensional structure of a polypeptide will depend, in part, on the region of the polypeptide where the substitution, addition or deletion occurs. In highly variable regions of the molecule, non-conservative substitutions as well as conservative substitutions may be tolerated without significantly disrupting the three-dimensional structure of the molecule. In highly conserved regions, or regions containing significant secondary structure, conservative amino acid substitutions may be preferred.

Conservative amino acid substitutions are well-known in the art, and include substitutions made on the basis of similarity in polarity, charge, solubility, hydrophobicity, hydrophilicity and/or the amphipathic nature of the amino acid residues involved. For example, negatively charged amino acids include aspartic acid and glutamic acid; positively charged amino acids include lysine and arginine; amino acids with uncharged polar head groups having similar hydrophilicity values include the following: leucine, isoleucine, valine; glycine, alanine; asparagine, glutamine; serine, threonine; phenylalanine, tyrosine. Other conservative amino acid substitutions are well known in the art.

For RPTK extracellular domains obtained in whole or in part by chemical synthesis, the selection of amino acids available for substitution or addition is not limited to the genetically encoded amino acids. Indeed, the mutants described herein may contain non-genetically encoded amino acids. Conservative amino acid substitutions for many of the commonly known non-genetically encoded amino acids are well known in the art. Conservative substitutions for other amino acids can be determined based on their physical properties as compared to the properties of the genetically encoded amino acids.

In some instances, it may be particularly advantageous or convenient to substitute, delete and/or add amino acid residues to a native extracellular domain in order to provide convenient cloning sites in a DNA, such as a cDNA, encoding the polypeptide, to aid in purification of the polypeptide, and for crystallization of the polypeptide. Such substitutions, deletions and/or additions which do not substantially alter the three dimensional structure of the native tyrosine kinase domain will be apparent to those of ordinary skill in the art.

It should be noted that the mutants contemplated herein need not exhibit ligand binding activity. Indeed, amino acid substitutions, additions or deletions that interfere with the ligand binding activity of the RPTK extracellular domain but which do not significantly alter the three-dimensional structure of the domain are specifically contemplated by the invention. Such crystalline polypeptides, or the atomic structure coordinates obtained therefrom, can be used to identify compounds or molecules that bind to the native domain. These compounds or molecules may affect the activity of the native domain.

The derivative crystals of the invention generally comprise a crystalline RPTK extracellular domain polypeptide in covalent association with one or more heavy metal atoms. The polypeptide may correspond to a native or a mutated tyrosine kinase domain. Heavy metal atoms useful for providing derivative crystals include, by way of example and not limitation, gold, mercury, etc.

The co-crystals of the invention generally comprise a crystalline RPTK extracellular domain polypeptide in association with one or more compounds or other molecules. The association may be covalent or non-covalent. Such molecules include, but are not limited to, ligands, ligand analogs, cofactors, substrates, substrate analogues, inhibitors, activators, allosteric effectors, polypeptides, etc.

IV. Three Dimensional Structure Determination Using X-ray Crystallography

X-ray crystallography is a method of solving the three dimensional structures of molecules. The structure of a molecule is calculated from X-ray diffraction patterns using a crystal as a diffraction grating. Three dimensional structures of protein molecules arise from crystals grown from a concentrated aqueous solution of that protein. The process of X-ray crystallography can include the following steps:

(a) synthesizing and isolating a polypeptide;

(b) growing a crystal from an appropriate solution comprising the polypeptide with or without a compound, modulator, ligand, or ligand analog; and (c) collecting X-ray diffraction patterns from the crystals, determining unit cell dimensions and symmetry, determining electron density, fitting the amino acid sequence of the polypeptide to the electron density, and refining the structure.

Production of Polypeptides

The native and mutated tyrosine kinase domain polypeptides described herein may be chemically synthesized in whole or part using techniques that are well-known in the art (see, e.g., Creighton, 1983). Alternatively, methods which are well known to those skilled in the art can be used to construct expression vectors containing the native or mutated tyrosine kinase domain polypeptide coding sequence and appropriate transcriptional/translational control signals. These methods include in vitro recombinant DNA techniques, synthetic techniques and in vivo recombination/genetic recombination. See, for example, the techniques described in Maniatis et al., 1989 and Ausubel et al., 1989.

A variety of host-expression vector systems may be utilized to express the RPTK extracellular domain coding sequence. These include but are not limited to microorganisms such as bacteria transformed with recombinant bacteriophage DNA, plasmid DNA or cosmid DNA expression vectors containing the RPTK extracellular domain coding sequence; yeast transformed with recombinant yeast expression vectors containing the RPTK extracellular domain coding sequence; insect cell systems infected with recombinant virus expression vectors (e.g., baculovirus) containing the RPTK extracellular domain coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the RPTK extracellular domain coding sequence; or animal cell systems. The expression elements of these systems vary in their strength and specificities.

Depending on the host/vector system utilized, any of a number of suitable transcription and translation elements, including constitutive and inducible promoters, may be used in the expression vector. For example, when cloning in bacterial systems, inducible promoters such as pL of bacteriophage λ, plac, ptrp, ptac (ptrp-lac hybrid promoter) and the like may be used; when cloning in insect cell systems, promoters such as the baculovirus polyhedrin promoter may be used; when cloning in plant cell systems, promoters derived from the genome of plant cells (e.g., heat shock promoters; the promoter for the small subunit of RUBISCO; the promoter for the chlorophyll a/b binding protein) or from plant viruses (e.g., the 35S RNA promoter of CaMV; the coat protein promoter of TMV) may be used; when cloning in mammalian cell systems, promoters derived from the genome of mammalian cells (e.g., metallothionein promoter) or from mammalian viruses (e.g., the adenovirus late promoter; the vaccinia virus 7.5K promoter) may be used; when generating cell lines that contain multiple copies of the receptor PTK extracellular domain DNA, SV40-, BPV- and EBV-based vectors may be used with an appropriate selectable marker.

Methods describing methods of DNA manipulation, vectors, various types of cells used, methods of incorporating the vectors into the cells, expression techniques, protein purification and isolation methods, and protein concentration methods are disclosed in detail with respect to the protein PYK-2 in U.S. Pat. Nos. 5,837,524, 5,837,815, and PCT publication WO 96/18738, each of which is incorporated herein by reference in its entirety, including all claims, figures, and drawings. Those skilled in the art will appreciate that such descriptions are applicable to the present invention and can be easily adapted to it.

Crystal Growth

Crystals are grown from solutions containing the purified and concentrated polypeptide by a variety of techniques. These techniques include batch, liquid, bridge, dialysis, vapor diffusion, and hanging drop methods. McPherson, 1982, John Wiley, New York; McPherson, 1990, Eur. J. Biochem. 189:1–23; Webber, 1991, Adv. Protein Chem. 41:1–36, incorporated by reference herein in its entirety, including all figures, tables, and drawings.

Generally, the crystals of the invention are grown by adding precipitants to the concentrated solution of the polypeptide corresponding to the RPTK extracellular domain, with or without bound compound, modulator, ligand, or ligand analog. The precipitants are added at a concentration just below that necessary to precipitate the protein. Water is removed by controlled evaporation to produce precipitating conditions, which are maintained until crystal growth ceases.

For one of the exemplary crystals of the invention, it has been found that hanging drops containing about 2.0 µL of RPTK extracellular domain polypeptide with a bound ligand provide crystals suitable for high resolution X-ray structure determination. Preferably, crystals are grown by mixing equal volumes of protein solution (10 mg/mL in 25 mM Tris-HCl, pH 8.5, and 150 mM NaCl) and reservoir buffer (1.6 M $(NH_4)_2SO_4$, 20% v/v glycerol and 100 mM Tris-HCl, pH 8.5), and suspending a hanging drop of the resulting solution over 0.5 mL reservoir buffer at 20° C. In preferred embodiments, the protein solution comprises 10 mg/mL FGFR1 D2-D3 domain bound to an FGF2 molecule.

In another exemplary crystal of the invention, crystals are grown by mixing one volume of protein solution (1 mg/mL in 25 mM Tris-HCl, pH 8.5, and 150 mM NaCl) with four volumes of reservoir buffer (20% PEG 4000, 0.2 M Li2SO4, and 0.1 M Tris-HCl, pH 8.5), and suspending a hanging drop of the resulting solution over 0.5 mL reservoir buffer at 20° C. In preferred embodiments, the protein solution comprises 1 mg/mL FGFR1 D2-D3 domain bound to an FGF 1 molecule.

Those of ordinary skill in the art will recognize that the above-described crystallization conditions can be varied. Such variations may be used alone or in combination, and include polypeptide solutions containing polypeptide concentrations between about 1 mg/ml and about 50 mg/ml, Tris-HCl concentrations between about 10 mM and about 200 mM, dithiothreitol concentrations between about 0 mM and about 20 mM, pH ranges between about 5.5 and about 9.5; and reservoir solutions containing polyethylene glycol concentrations between about 10% and about 50% (w/v), polyethylene glycol molecular weights between about 1000 and about 20,000, $(NH_4)_2SO_4$ concentrations between about 0.1 M and about 2.5 M, ethylene glycol or glycerol concentrations between about 0% and about 20% (v/v), bis-Tris concentrations between about 10 mM and about 200 mM, pH ranges between about 5.5 and about 9.5 and temperature ranges between about 0° C. and about 25° C. Other buffer solutions may be used such as HEPES buffer, so long as the desired pH range is maintained.

Derivative crystals of the invention can be obtained by soaking native crystals in mother liquor containing salts of heavy metal atoms. It has been found that soaking a native crystal in a solution containing about 0.1 mM to about 5 mM thimerosal, 4-chloromeruribenzoic acid or $KAu(CN)_2$ for about 2 hr to about 72 hr provides derivative crystals suitable for use as isomorphous replacements in determining the X-ray crystal structure of the RPTK extracellular domain polypeptide.

Co-crystals of the invention can be obtained by soaking a native crystal in mother liquor containing one or more compounds, ligands, or ligand analogs that bind the receptor PTK extracellular domain, as described above, or can be obtained by co-crystallizing the RPTK extracellular domain polypeptide in the presence of one or more binding compounds, ligands, or ligand analogs.

Crystals comprising a polypeptide corresponding to a RPTK extracellular domain complexed with a compound, ligand, or ligand analog can be grown by one of two methods. In the first method, the compound, ligand, or ligand analog is added to the aqueous solution containing the polypeptide corresponding to the RPTK extracellular domain before the crystal is grown. In the second method, the compound, ligand, or ligand analog is soaked into an already existing crystal of a polypeptide corresponding to a RPTK extracellular domain.

Crystalline FGFR Extracellular Domain/FGF Complexes

The overall structures of the FGF1-FGFR1 and FGF2-FGFR2 complexes are similar to the previously determined FGF2-FGFR1 structure (FIG. 5) (Plotnikov et al., 1999). The FGFR ligand-binding domain consists of two Ig-like domains connected by a short linker. The three-dimensional folds of D2 and D3 in both the FGF1-FGFR1 and FGF2-FGFR2 structures resemble that of the I-set prototype member telokin, in which a β sandwich is formed by two layers of β sheets (Holden et al., 1992). A highly conserved disulfide bond is buried in the hydrophobic core of D2 and D3 and bridges the two β sheets. In both structures, the βC–βC' loop in D3 is disordered (FIG. 5).

Figure 5:
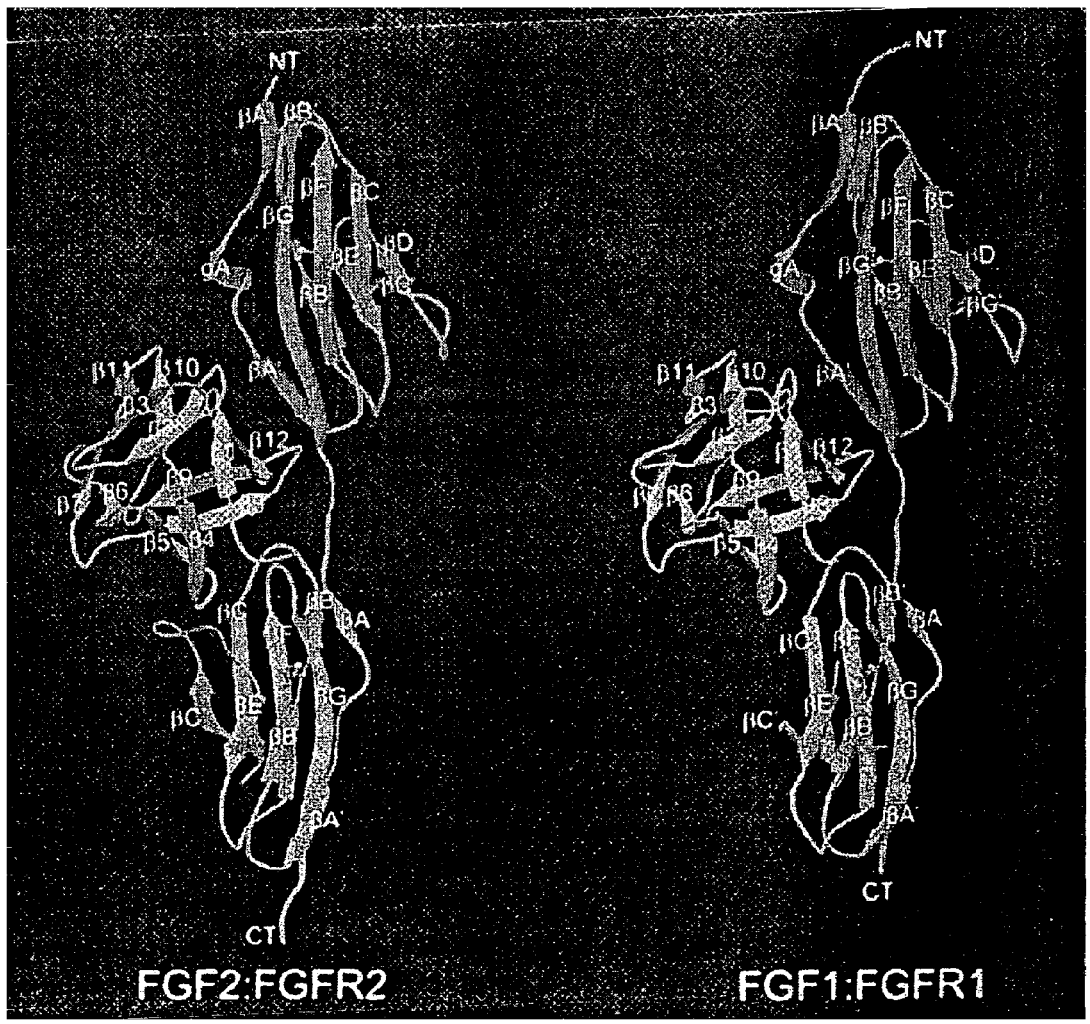
FIG. 5 shows ribbon diagrams of the FGF1-FGFR1 and FGF2-FGFR2 complexes with the Ig-like domains 2 (D2) and 3 (D3) are shown in green and cyan, respectively. The short linker that connects D2 and D3 is colored gray. FGF 1 and FGF2 are shown in orange. The secondary structure assignments for FGFR1 and FGFR2 were obtained with the program PROCHECK (Laskowski et al., J. Appl. Cryst., 26,283–291 (1993)). The beta strands for D2 and D3 are labeled according to the strand nomenclature for the canonical I-set member telokin. The helix between betaA and betaA', gA, is a $3_{10}$ helix. In both FGF1-FGFR1 and FGF2-FGFR2 structures, the betaC-betaC' loops in D3 are disordered. In addition, most of the segment between betaC' and betaE in D3 of FGF1-FGFR1 is disordered as well. In the FGF2-FGFR2 structure, this segment is well ordered and is colored purple. The amino- and carboxy-termini are denoted by NT and CT. The disulfide bonds in D2 and D3 are shown in ball-and-stick rendering with sulfur atoms colored yellow. The beta strands of FGF1 are labeled from 1 to 12 according to published nomenclature (Faham et al., Curr. Opin. Struct. Biol. 8, 578–586 (1998)). This figure was created using the programs Molscript (Kraulis, J. Appl. Crystallogr. 24,946–950(1991)) and Raster3D (Merrit et al., *Methods Enzymol.* 277, 505–524 (1997)).

The main difference between the structures of FGF1-FGFR1 and FGF2-FGFR2 is the conformation of the segment connecting βC' and βE in D3 (FIG. 5). In the FGF2-FGFR2 structure, this segment is well ordered and interacts with FGF2, while in the FGF1-FGFR1 structure, this segment is disordered and is not included in the atomic model. In the previously determined structure of FGF2-FGFR1, this segment is also well ordered and interacts with the ligand (Plotnikov et al., 1999). At the C-terminal end of this segment in the FGF2-FGFR1 structure, a short α helix (αD) has been assigned by PROCHECK (Laskowski et al., 1993). In the present FGF2-FGFR2 structure, the polypeptide chain at the C-terminal end adopts a very similar conformation, but is not assigned as a α helix.

Figure 6:
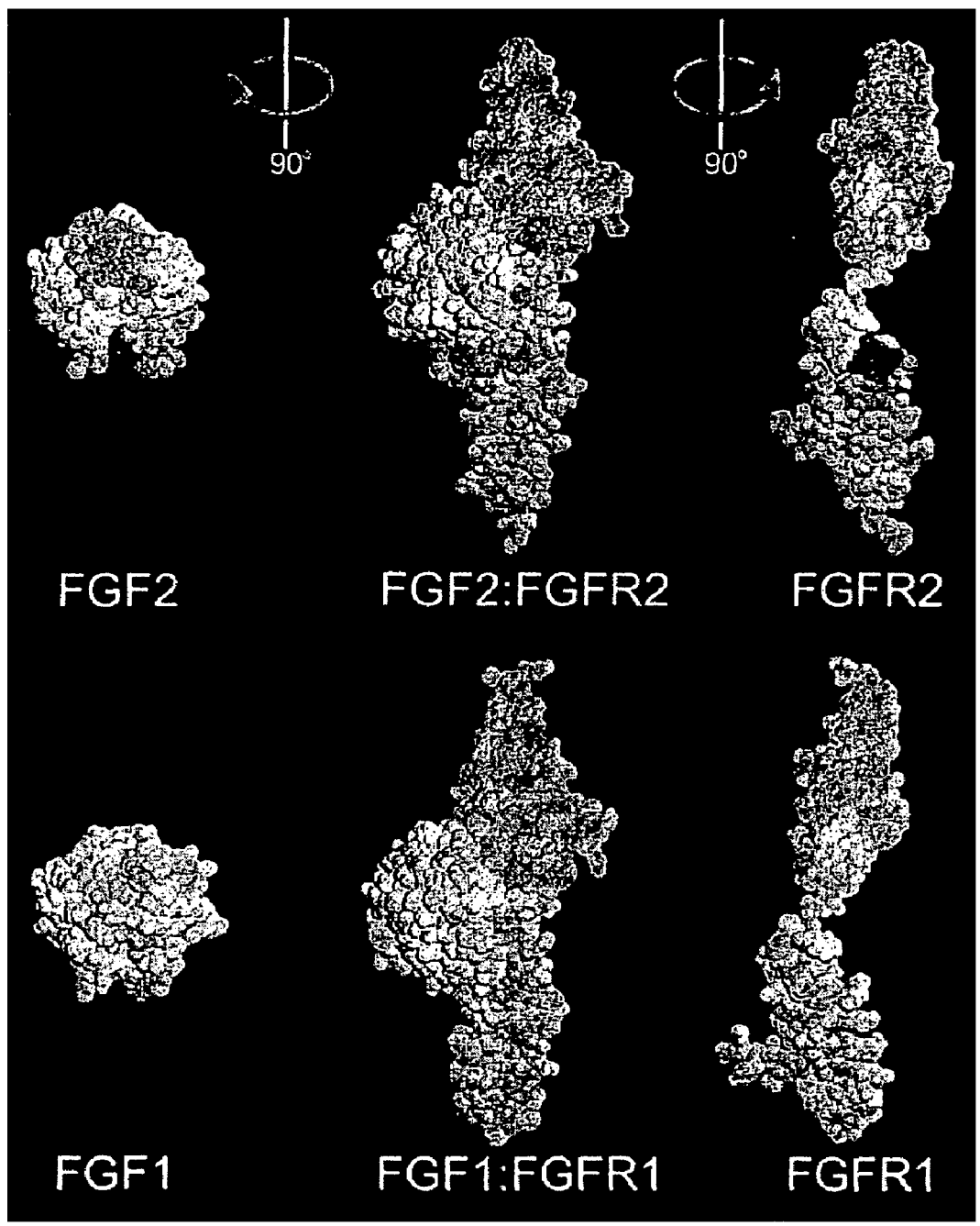
FIG. 6 shows Space-filling models of the FGF1-FGFR1 and FGF2-FGFR2 complexes. The view and the coloring for D2, D3, the linker and FGFs are the same as in FIG. 5. To better visualize the binding interfaces on FGFs and on FGFRs, the molecules are pulled away from each other and rotated 90° about the vertical axis as indicated (left and right panels). Residues in FGF1 and FGF2 are colored with respect to the FGFR regions with which they interact. FGF1 and FGF2 residues that interact with D2 are colored green, residues that interact with the linker region are colored gray, and residues that interact with D3 are colored cyan. FGF2 residues that interact with the betaC'-betaE segment (shown in purple) of FGFR2 are colored red. The residues in FGFR1 and FGFR2 that interact with FGF1 and FGF2, respectively, are colored orange. In addition, in the FGF2-FGFR2 structure, receptor residues in the betaC'-betaE segment that contact FGF2 are in red. Ligand and receptor residues are considered to be in the FGF-FGFR interface if at least one pair of atoms (side chain or main chain) has an inter-atomic distance of 3.8 Å or less. This figure was created using the programs Molscript and Raster3D.

It has previously been reported that both FGF1 and FGF2 adopt a β-trefoil fold which consists of three copies of a four-stranded antiparallel β sheet (FIG. 5). Superposition of receptor-bound FGF1 and FGF2 with the free FGF1 and FGF2 indicates that no significant conformational changes occur in FGF1 and FGF2 upon receptor binding. In addition, as with the crystal structures of free FGF1 and FGF2, ordered sulfate ions are found in the heparin-binding sites of both FGF1 and FGF2. As in the determined crystal structure of FGF2-FGFR1, the ligands in both the FGF1-FGFR1 and FGF2-FGFR2 structures interact with residues of the receptors in D2, in D3 and in the linker that connects D2 and D3 (FIG. 6).

In one illustrative embodiment, the invention provides crystals of FGFR1 D2-D3 domain bound to an FGF2 molecule. The D2-D3 domain of this embodiment consists of residues 142–365, and thus is missing the D1 domain, the acid box, and the linker between D3 and the transmembrane helix. Each D2-D3 domain is bound to a single FGF2 molecule. The crystals were obtained by the methods provided in the Examples. The FGFR1 D2-D3/FGF2 crystals, which may be native crystals, derivative crystals or co-crystals, have tetragonal unit cells (i.e., unit cells wherein a=b≠c) and space group symmetry $P4_12_12$. There are two FGFR1 D2-D3/FGF2 complexes in the asymmetric unit, related by an approximate two-fold axis. The unit cell has dimensions of a=b=98.5 Å, c=197.0 Å and β=90°.

The FGF-D2 Interface

Figure 7:
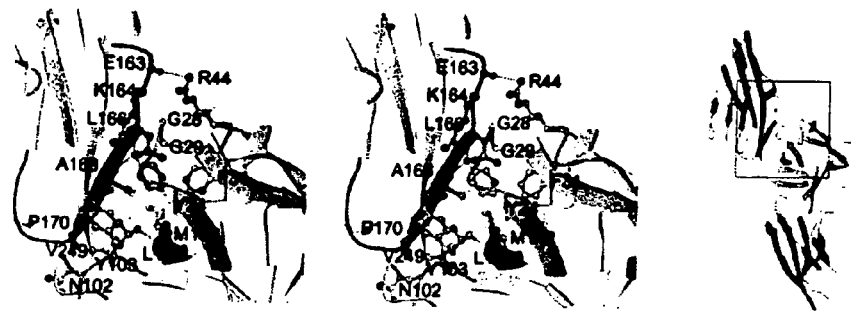
FIG. 7 shows a stereo view of detailed interactions in the hydrophobic interface between FGF2 and D2 of FGFR2
Figure 8:
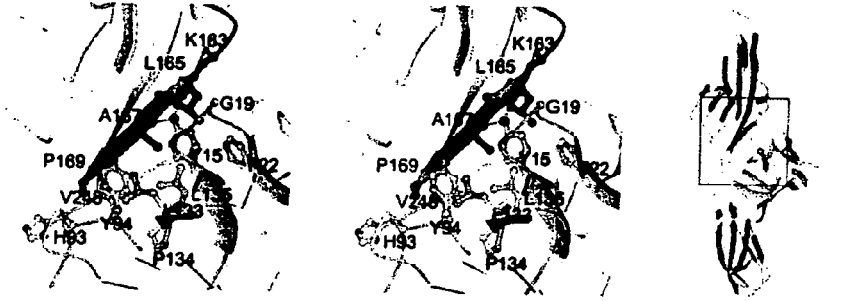
FIG. 8 shows a stereo view of detailed interactions in the hydrophobic interface between between FGF1 and D2 of FGFR1.

The interface between FGF and D2 in both complexes is mainly hydrophobic (FIGS. 7 and 8). A solvent-exposed hydrophobic surface in FGF packs against a highly conserved hydrophobic surface at the bottom of D2 in FGFR. In the FGF2-FGFR2 structure, Tyr24, Leu140, and Met142 in FGF2 make hydrophobic contacts with Ala168 in FGFR2.

Leu140, Tyr103 and the aliphatic portion of the Asn102 side chain in FGF2 make hydrophobic contacts with Pro 170 in FGFR2. Phe31 of FGF2 is engaged in hydrophobic interactions with Leu166 of FGFR2. Leu166, Ala168 and Pro170 of FGFR2 are located in βA' at the bottom of D2. Val249, located in the C-terminal end of βG in D2, is also in the FGF2-D2 interface and interacts with Leu140 and Met142 in FGF2. Several hydrogen bonds further fortify the mainly hydrophobic FGF2-D2 interface: the hydroxyl group of Tyr24 in FGF2 forms two hydrogen bonds with backbone atoms of Leu166 and Ala168 in FGFR2, and Tyr103 makes a hydrogen bond via a water molecule with the backbone of Ala168.

The observed interactions between FGF2 and FGFR2 in the FGF2-D2 interface are entirely consistent with mutagenesis studies on FGF2. It is demonstrated that individual replacements with alanine of Tyr24, Tyr103, Leu140 and Met140, all of which located in the FGF2-D2 interface (FIG. 7), results in a large decrease in FGFR1 binding affinity (Springer et al., 1994).

Within each D2-D3/FGF2 complex of the illustrative embodiment, FGF2 interacts extensively with D2, D3, and the linker between the two domains. While a single hydrogen bond is noted between Tyr-24 in FGF2 and Leu-165 in FGFR1, the majority of interactions between D2 and FGF2 are hydrophobic. For example, hydrophobic contacts can be seen between Tyr-24 and Met-142 of FGF2 and Ala 167 of D2, between Asn-102, Tyr-103, and Leu-140 of FGF2 and Pro-169 of D2, and between Leu-140 of FGF2 and Val-248 of FGFR1. It is noteworthy that Ala 167, Pro-169, and Val-248 are conserved amongst FGFRs 1–4, and thus may represent a therapeutically important site in members of the FGFR subfamily.

Comparison of the FGF-D2 interfaces in the structures of FGF2-FGFR2 and FGF1-FGFR1 reveals a close similarity (FIGS. 7 and 8). FGF2 and FGF1 differ in only two positions in the FGF-D2 interface: Met142 in FGF2 is replaced by a homologous hydrophobic residue Leu135 in FGF1, and Asn102 in FGF2 is substituted by His93 in FGF1. However, this latter substitution may not affect the binding of FGF1 to D2, since only the aliphatic portion of this residue interacts with FGFR and not the actual functional group.

The FGF-Linker Interface

Figure 9:
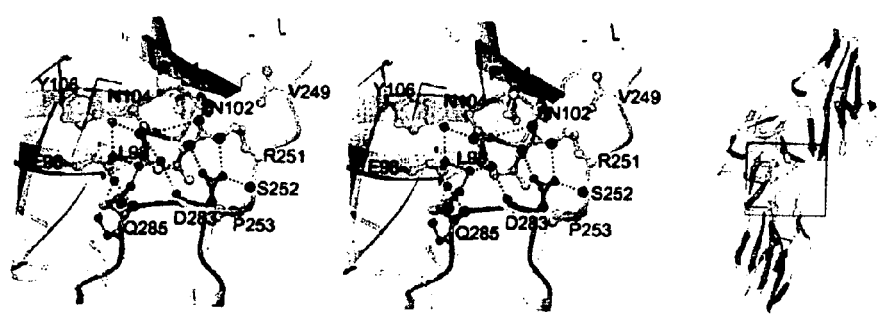
FIG. 9 shows a stereo view of detailed interactions of the conserved network of hydrogen bonds between FGF2 and FGFR2 in the vicinity of Arg251 in the D2-D3 linker.
Figure 10:
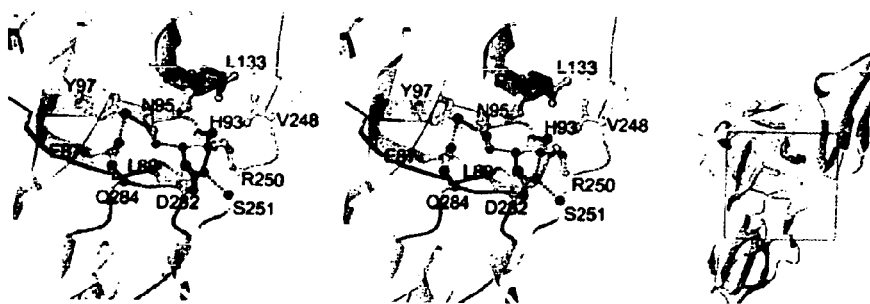
FIG. 10 shows a stereo view of detailed interactions the network of hydrogen bonds between FGF1 and FGFR1 in the vicinity of Arg250 in the D2-D3 linker.

The D2-D3 linker is highly conserved among FGFRs (FIG. 15). The hydrogen bonds between FGFs and the linker region play a critical role in binding of FGFs to FGFRs (FIGS. 9 and 10). In the FGF2-FGFR2 structure, an invariant arginine located in the D2-D3 linker, Arg251 (in FGFR2), forms hydrogen bonds with the side chain of Asn104 and the backbone carbonyl oxygen of Asn102 (FIG. 9). Indeed, replacement of Asn104 in FGF2 with an alanine causes a 400-fold reduction in the binding affinity of FGF2 for FGFR1 (Zhu et al., 1997), revealing the importance of the interaction between Asn104 and FGFR.

Figure 17:
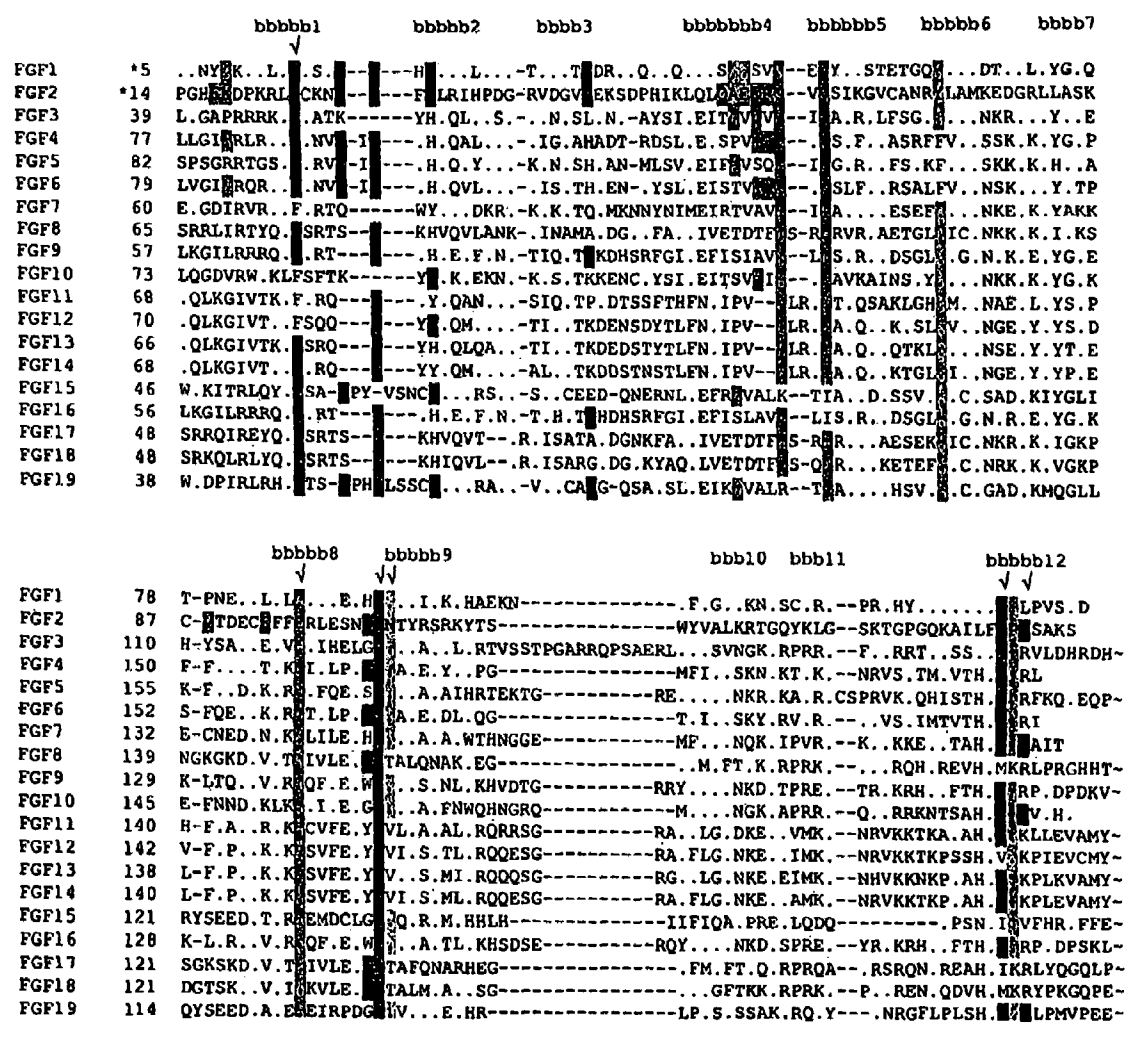

A sequence alignment of the 19 available FGFs shows that the majority of FGFs have an asparagine in the position corresponding to Asn104 of FGF2 (FIG. 17). However, FGF8, FGF 17 and FGF 18 have a threonine residue at this position, whose side chain is shorter than asparagine. It is predicted that these FGFs will not form a direct hydrogen bond with the key linker arginine residue, and therefore will exhibit lower binding affinity towards FGFRs. Interestingly, FGF11, FGF 12, FGF13, and FGF14 have a valine in place of Asn104 of FGF2 (FIG. 17). This substitution is expected to cause a strong decrease in FGFR binding.

The hydrogen bond between Arg251 and FGF2 takes place in a hydrophobic pocket composed of the aliphatic side chains of highly conserved Val249 and Pro253 in FGFR2 and Leu98 and Pro141 in FGF2 (FIG. 9). The proximity to this hydrophobic environment will most likely stabilize this hydrogen bond. Moreover, the intramolecular hydrogen bonds between Arg251 and the invariant Asp283 in FGFR2 and Asn104 and Tyr106 in FGF2 serve to restrict the rotational freedom of the guanidium group of Arg251 and amide group of Asn104 (FIG. 9). These interactions may increase the ligand-binding affinity by lowering the entropy of FGF-FGFR complex formation. Indeed, substitution of Tyr106 with a phenylalanine in FGF2 caused a 5-fold reduction in receptor binding (Zhu et al., 1995).

The FGF-linker interfaces in both FGF1-FGFR1 and FGF2-FGFR2 structures are highly conserved (FIGS. 9 and 10). Moreover, the hydrophobic environment surrounding the critical hydrogen bond between FGFR-invariant linker arginine and FGF is nearly identical in both structures (FIGS. 9 and 10). A sequence alignment of all known members of the FGF and FGFR families, reveals that residues in FGF and FGFR that constitute the FGF-D2 and FGF-linker interfaces are conserved among the 4 mammalian FGFRs (FIG. 15) and the 19 available FGFs (FIG. 17). Based on our structures and the sequence alignment, we propose that the FGF-D2 and FGF-linker interfaces described above represents a general conserved binding interface for all FGF-FGFR complexes.

Interactions between FGF2 and the linker between D2 and D3 in the illustrative embodiment include hydrogen bonds between Asn-102 and Asn-104 of FGF2 with Arg-250 of FGFR1, and a hydrophobic interaction between Leu-98 of FGF2 and Val-248 of FGFR1. Arg-250 is invariant in the FGFR subfamily, and thus may also represent a therapeutically important site.

The FGF-D3 Interface

While the FGF-D2 and the FGF-linker interfaces are conserved in FGF-FGFR complexes, a large part of the FGF-D3 interface is highly divergent, thus revealing the determinants of FGF-binding specificity. FIGS. 11–14 depict the interactions between FGF and the upper part of the D3 module. These interactions are mediated mainly by the βB'-βC, βC'-βE, and βF-βG loops of FGFRs. While residues in the βB'-βC are highly conserved, the amino acid sequences of the βC'-βE and βF-βG loops are significantly divergent among FGFRs (FIG. 16). Notably, alternative splicing occurs at the junction between βC' and the βC'-βE loop. Thus, the βC'-βE and βF-βG loops are located in the second half of D3, which is subject to alternative splicing. Interactions of D3 with FGF involve several regions of FGF including the most divergent regions at the N-terminal segment outside of the 1-trefoil core (prior to 1) and at the central segment consisting of β4 and the β4-β5 loop. In contrast to the FGF-D2 interface which is dominated by hydrophobic interactions, most of the interactions in the FGF-D3 interface are mediated by hydrogen bonds. Moreover, many of the hydrogen bonds between FGF and D3 are made via water molecules. The polar nature of this FGF-D3 interface is consistent with the notion that this interface plays a critical role in FGF-FGFR binding specificity.

Figure 11:
FIG. 11 shows a stereo view of detailed interactions in the interface between FGF2 and the betaF-betaG loop of D3 in the FGF2-FGFR2 structure. At the right side of each stereo pair, a view of the whole structure in the exact orientation as in stereo views is shown and the region of interest is highlighted. Only side chains of interacting residues are shown. Color coding is the same as in FIG. 7. Dotted lines represent hydrogen bonds.

The conserved interactions between FGF2 and the βB'–βC loop in D3 are mediated by four hydrogen bonds (one direct, three water-mediated) between an FGF-invariant glutamic acid residue, Glu96 in FGF2, and FGFR-invariant Gln285 in the βB'-βC loop of D3 (FIGS. 9 and 11). A water-mediated hydrogen bond between the side chain of Asn104 and the backbone carbonyl oxygen of Asp283 is also made in this interface (FIG. 9). The significance of Glu96 in FGF2 for FGFR binding was confirmed by a 1000-fold reduced receptor binding affinity of an FGF2 mutant containing an alanine in place of Glu96 (Zhu et al., 1995).

Figure 13:
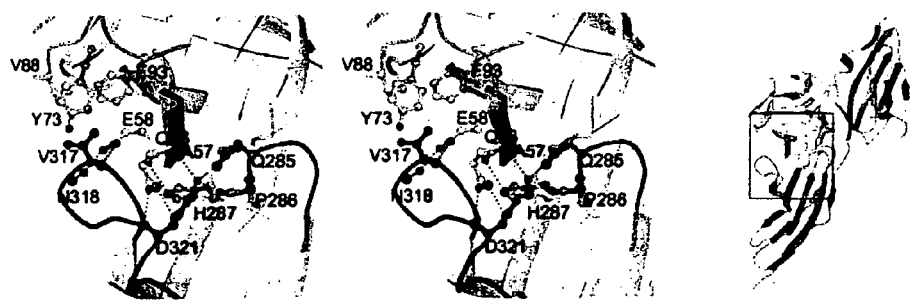
FIG. 13 shows a stereo view of detailed interactions in the interface between FGF2 and the betaC'-betaE segment (shown in purple) of D3 in the FGF2-FGFR2 structure. Views and coding are the same as in FIG. 11.

In contrast to the interface between FGF and the βB'-βC loop, the interactions between FGF and the βC'-βE loop in D3 are highly variable. A major difference between the crystal structures of FGF2-FGFR2 and FGF1-FGFR1 is the conformation of the βC'-βE segment (FIG. 5). In the FGF2-FGFR2 structure, the βC'-βE loop is well ordered and forms several specific contacts with residues in β4 of FGF2 (FIG. 13). This loop, on the other hand, is disordered in the crystal structure of FGF1-FGFR1 (FIG. 5). This difference reflects the lack of interaction between this loop and FGF1 and is not the result of crystal packing; this segment is ordered in all the four FGF2-FGFR2 complexes in the unit cell and disordered in both FGF1-FGFR1 complexes in the unit cell. As a result of this difference, the total accessible surface area buried in the FGF1-FGFR1 complex is 2200 Å$^2$ as compared to 2700 Å$^2$ in the FGF2-FGFR2 complex.

A total of five hydrogen bonds are formed at the interface between FGF2 and the βC'-βE segment in the FGF2-FGFR2 structure (FIG. 13). Two hydrogen bonds are formed between the side chain of Gln56 of FGF2 and Asp321 of FGFR2, and two hydrogen bonds are made between the side chain of Glu58 of FGF2 and backbone atoms of Val317 and Asn318 in FGFR2. A fifth hydrogen bond is made between the backbone of Ala57 in FGF2 and the side chain of Asp321 via an ordered water molecule. Hydrophobic contacts between the side chain of Val317 in FGFR2 and the side chains of Tyr73, Val88, and Phe93 in FGF2 fortify this interface (FIG. 13). Mutagenesis experiments support the involvement of both Val88 and Phe93 in receptor binding. Replacement of Val88 and Phe93 with alanine in FGF2 cause a 10-fold and 80-fold reduction in receptor binding affinity, respectively (Zhu et al., 1998).

It is possible that the βC'-βE loop exists in several different conformations and that interactions with different FGFs will modulate its secondary structure. In the crystal structures of FGF2-FGFR2 and FGF2-FGFR1, the βC'-βE segment forms a small hydrophobic plug by means of interactions between three residues in this region (Ala315, Thr319 and Ile324) along with Ile288 located in βC in D3. It is conceivable that in the unoccupied receptors, the side chains of these residues are not sufficiently hydrophobic to form a stable core. In the occupied receptors, on the contrary, interactions with FGF2 may facilitate the positioning of these hydrophobic residues leading to formation of a more stable structure. In FGF1, the residue corresponding to Gln56 of FGF2 is a serine (FIG. 17), whose side chain is not long enough to form hydrogen bonds with Asp320 in FGFR1. A loss of these hydrogen bonds may increase the flexibility of the βC'-βE segment. This region is disordered in the FGF1-FGFR1 structure (FIG. 5 and FIG. 10).

On the basis of the structural analysis described above, it is proposed that FGF1 does not engage in any specific contacts with the βC'-βE loop, providing a potential explanation for why FGF1 binds indiscriminately to most FGFRs including the various alternatively-spliced forms, thus functioning as a universal ligand for all known FGFRs.

The crystal structure of an FGF1-FGFR2 complex was recently reported (Stauber et al., 2000). In contrast to the FGF1-FGFR1 structure described here, in the FGF1-FGFR2 structure the βC'-βE loop is ordered and makes several contacts with FGF1. Based on this structure changes in the primary sequence of the βC'-βE loop (as a result of alternative splicing) would clearly affect FGF1 binding. This structural feature, however, does not agree with the well-documented universal binding characteristics of FGF1.

The βC'-βE loop of all known FGFRs, irrespective of exon IIIb or IIIc, contains a highly conserved potential N-glycosylation site (Asn318 in FGFR2). The results described herein confirm that Asn318 is glycosylated in the extracellular domain of FGFR2 when expressed in insect cells. In the crystal structure of FGF1-FGFR2 (Stauber et al., 2000), the side chain of Asn318 makes two hydrogen bonds with FGF1. This peculiarity along with the specificity conundrum led us to consider whether the interactions between the βC'-βE loop and FGF1, observed in this structure, could be due to crystal packing and thus not reflect the situation in vivo.

Analysis of the relative disposition of D2 and D3 in all the FGF-FGFR structures revealed that the linkage between D2 and D3 is flexible, and the angle between the two domains is not dictated solely by the contacts between the two domains and the ligand. That is, crystal packing also affects the relative disposition of the two domains. Although the FGF1-FGFR1 (reported in this manuscript) and FGF1-FGFR2 (Stauber et al., 2000) structures feature a common ligand, superimposition of the Cα atoms of D2 between the two structures reveals a 7.8° difference in the relative orientation of D3 and D2. As a consequence, the βC'-βE loop in the FGF1-FGFR2 structure is closer to the ligand, and it is conceivable that the interactions between the βC'-βE loop and FGF1 in this structure are the result of crystal packing. In the FGF1-FGFR1 structure, the βC'-βE loop is disordered in both complexes in the asymmetric unit, providing two independent instances in which the βC'-βE loop does not engage FGF1.

Analysis of the lattice contacts in FGF1-FGFR2 structure provides a plausible mechanism by which crystal packing might have contributed to the observed interactions between the βC'-βE loop and FGF1. In this structure, the D2s of two symmetry mates insert into the space between the two D3s of the primary dimer, and appear to push the D3s closer to the FGF1 molecules.

Interactions Between FGFR and FGF which Stabilize Dimerization

The D2-D3/FGF2 dimer observed in the crystal structure of one illustrative embodiment is stabilized by interactions between each FGFR in the dimer, and by interactions between the FGF bound to one FGFR and the other receptor in the dimer. The ligand-receptor contacts which stabilize dimerization are largely weak van der Waals interactions between residues Asp-99, Ser-100, Asn-101, Pro-132, Gly-133, and Leu-138 of FGF2 and Pro-199, Asp-200, Ile-203, Gly-204, Gly-205, Ser-219, and Val-221 of FGFR1. Also noted are hydrogen bonds between Pro-132 of FGF2 and Gly-204 of FGFR1, and Lys-26 of FGF2 and Asp-218 of FGFR1.

In contrast, the receptor—receptor contacts which stabilize dimerization include a hydrophobic contact between Ala-171 residues of each receptor, hydrogen bonds between Lys 172, Thr-173, and Asp-218 of each receptor, and van der Waals interactions between Ala-171 and Lys-172 of each receptor. The present invention describes a receptor—receptor interface which was not postulated previously, involving residues conserved in the FGFR subfamily.

Disruption of the contacts which stabilize dimerization, for example by a molecule(s) which prevents the formation of one or more contacts, may provide a means of inhibiting RPTK function. Alternatively, a molecule(s) which further stabilize dimer formation may provide a means of stimulating RPTK function.

Structural Basis for the Role of Alternative Splicing in FGF-Binding Specificity Role of the βC'-βE Segment A comparison of the amino acid sequences of FGFs and FGFRs in the interface between βC'-βE loop and FGFs shows significant diversity (FIG. 16 and FIG. 17). Moreover, alternative splicing occurs at the end of βC', resulting in major changes in the primary sequence and length of the βC'-βE loop. For example, the amino acid sequence of the βC'-βE loop in KGFR/FGFR2(IIIb) has seven substitutions and is two amino acids shorter than the corresponding region in FGFR2(IIIc) (FIG. 16). Significantly, the three residues (Ala3 15, Thr319, and Ile324) in FGFR2(IIIc) that participate in formation of the βC'-βE hydrophobic plug are replaced by residues (Ser315, Ser319, and Ala322) in KGFR/FGFR2(IIIb) that are less likely to form a hydrophobic plug (FIG. 16). The result of these changes, the βC'-βE loop in KGFR will not be able to interact efficiently with FGF2. This proposal is supported by binding experiments of FGF2 to a mutant FGFR2, in which its βC'-βE loop is replaced with the corresponding region from KGFR. The affinity of FGF2 towards this mutant is reduced by an order of magnitude (Gray et al., 1995). Conversely, insertion of the two residues and/or amino acid substitutions in the βC'-βE loop of KGFR did not affect FGF 1 binding but abolished KGF/FGF7 binding (Wang et al., 1995b). Moreover, replacement of the corresponding region in FGFR1(IIIc) conferred upon the mutant receptor the ability to bind KGF (Wang et al., 1999), while wild type FGFR1(IIIc) does not bind KGF/FGF7. These data indicate that there may be steric clashes between KGF/FGF7 and the βC'-βE segment in FGFR2(IIIc) resulting in the reduced affinity of KGF/FGF7 to FGFR2(IIIc). On the contrary, the βC'-βE segment of KGFR/FGFR2(IIIb) may interact more efficiently with KGF/FGF7. The latter hypothesis is supported by the finding that a synthetic peptide derived from KGFR/FGFR2(IIIb) encompassing the βC'-βE segment competes specifically with the binding of KGF/FGF7 to KGFR/FGFR2(IIIb) (Bottaro et al., 1993). Final validation of these proposals, however, awaits a crystal structure of KGF/FGF7 in complex with KGFR/FGFR2(IIIb).

The structural findings described herein are also consistent with the identification of a central segment in KGF/FGF7 (residues 91–110) necessary for specific recognition and activation of KGFR (Reich-Slotsky et al., 1995). This region mainly corresponds to β4 and the β4-β5 loop in FGF2 (FIG. 6), which in the crystal structure of FGF2-FGFR2 make specific contacts with βC'-βE and βF-βG loop in D3, respectively (FIGS. 13 and 11, respectively). Taken together, the structural data provide a molecular explanation as to how alternative splicing switches specificity in FGFR2/KGFR system.

Although alternative splicing plays a major role in specificity, similarly spliced variants of FGFRs also exhibit differential binding specificity (Ornitz et al., 1996). It was shown that FGF2 binds strongly to FGFR1(IIIc) and FGFR2(IIIc) but poorly to FGFR3(IIIc) and FGFR4 (Chellaiah et al., 1999; Vainikka et al., 1992). A survey of amino acid sequences of the βC'-βE loop of these receptors shows that the βC'-βE loop of FGFR4 as with KGFR/FGFR2(IIIb) is two amino acids shorter than the corresponding loop in FGFR1-3 (FIG. 16). Based on the results described herein, it is predicted that this loop in FGFR4 can not efficiently interact with FGF2. This will result in reduced FGF2 binding affinity to FGFR4 as compared to FGFR1. The βC'-βE loop of FGFR3 differs from that of FGFR1 by two amino acid substitutions (FIG. 16). Significantly, in FGFR3 the residue corresponding to Val317 of FGFR2 is an alanine, an amino acid with a smaller side chain than valine (FIG. 16). This will result in a weaker hydrophobic interaction with FGF2, affecting the affinity of FGF2 towards FGFR3. Indeed, when these residues in FGFR3 were replaced with the corresponding residues in FGFR1, the resultant FGFR3 mutant exhibited comparable binding affinity towards FGF2 (Chellaiah et al., 1999). The interactions between FGF and the βC'-βE loop in the crystal structure (FIG. 13) provide a molecular explanation for how specificity is regulated by the primary sequence composition of the βC'-βE loop.

Role of the βF-βG Loop

The βF-βG loop in D3 also plays an important role in the modulation of FGF binding specificity. In the FGF2-FGFR2 structure, Ser347 of FGFR2, located in OF-OG loop, makes two water mediated-hydrogen bonds with Glu96 and Leu98 of FGF2 (FIG. 11). A water-mediated hydrogen bond between Gly345 in FGFR2 and Gly61 in FGF2 and a direct hydrogen bond between the backbone of Asn346 in FGFR2 and the side chain of Arg60 in FGF2 provide additional contacts in this region (FIG. 11). Residues Arg60 and Gly61 are located in the β4-β5 loop in FGF2 (FIG. 17). Comparison of amino acid sequences shows that FGFs display considerable sequence variation at the position of Arg60 of FGF2. Residue Gly61, on the other hand, is highly conserved in FGFs (FIG. 17). The βF-βG loop is invariant in the IIIb and IIIc forms of FGFRs (FIG. 16). However, Gly345 and Ser347 of FGFR2(IIIc) are replaced by Ser342 and Tyr345 in KGFR/FGFR2(IIIb). Replacement of Ser347 in FGFR2 by a tyrosine in KGFR/FGFR2(IIIb) may result in steric clashes with FGF2 leading to reduced binding affinity of FGF2 to KGFR/FGFR2(IIIb). This proposal is consistent with ligand binding properties of a double mutant KGFR, in which Tyr345 and Gln348 in KGFR were replaced by serine and isoleucine as in FGFR2. This mutant receptor acquired significant binding affinity towards FGF2 as compared to the parent molecule (Gray et al., 1995). Interestingly, mutation of an invariant asparagine located in the βF-βG (Asn344 in KGFR) to an alanine abolished binding ability of KGFR/FGFR2(IIIb) towards all FGFs tested (Gray et al., 1996). These results are expected based on our FGF-FGFR strcutures: in FGF2-FGFR2 structure the corresponding asparagine (Asn346) makes two intramolecular hydrogen bonds with backbone atoms of Ile348 and Gly349 in FGFR2. These hydrogen bonds play an important role in maintaining the local fold of the βF-βG loop. Substitution of Asn346 with an Ala residue will interfere with the folding of this loop resulting in possible steric clashes with all FGFs. Taken together, the structural data provide a plausible molecular explanation for how alternative splicing in D3 regulates FGF binding specificity towards different receptor isoforms.

The Role of the N-Terminal Segment of FGF

Figure 12:
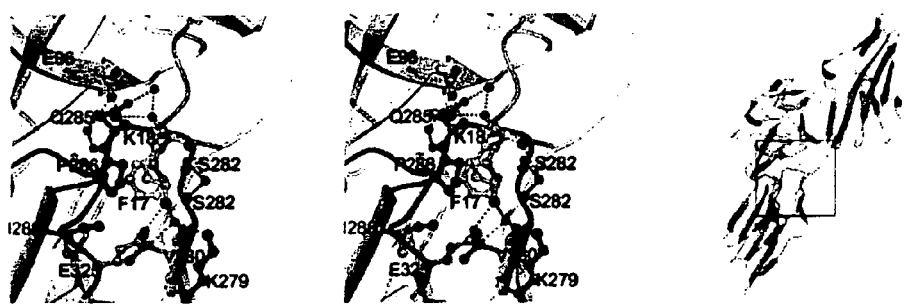
FIG. 12 shows a stereo view of detailed interactions in the interface between N-terminal sequences (prior to beta1) of FGF2 and D3 in the FGF2-FGFR2 structure. Views and coding are the same as in FIG. 11.
Figure 14:
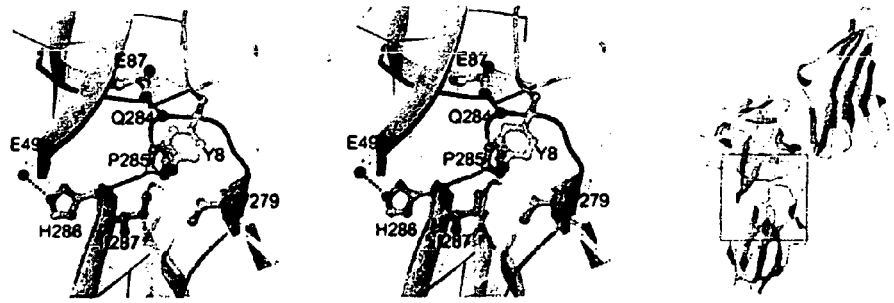
FIG. 14 shows a stereo view of detailed interactions in the interface between FGF1 and D3 in the FGF1-FGFR1 structure. Views and coding are the same as in FIG. 11.

In the crystal structures of the receptor-bound FGF1 and FGF2, residues upstream of β1 are found to be disordered (Eriksson et al., 1991; Blaber et al., 1996; Zhu et al., 1991). However, in the crystal structures of the receptor-bound FGF1 and FGF2 these residues are ordered and in proximity to D3 of FGFRs (FIGS. 12 and 14). In the FGF2-FGFR2 structure, the side chain of Phe17 is located in a shallow hydrophobic pocket in D3 that is formed by Pro286, Ile288 and Val280 (FIG. 12). Moreover, Phe17 forms several hydrogen bonds via backbone atoms with Ser282 and Gln285 in D3. Lys18 in FGF2 also makes several hydrogen bonds with the side chains of Lys279 and Glu325 and with the backbone of Val280 in D3 (FIG. 12). In agreement with these structural observations, it has been shown that a synthetic peptide consisting of residues 13–18 of FGF2 (prior to β1) competes with the binding of FGF2 to FGFR (Yayon et al., 1993). The amino acids $^7$NYKKPKL$^{13}$ (SEQ ID NO: 202) located at the junction between the N-terminal segment and β1 in FGF1 have been proposed to signal the nuclear accumulation of FGF1 that occurs during sustained exposure of cells to FGF1 (Imamura et al., 1990). In the FGF1-FGFR1 structure, Tyr8 located in this amino acid stretch inserts into a shallow hydrophobic pocket formed by the side chains of Val279, Pro285 and Ile287. The structural data described herein provide a direct role for this region in receptor binding. Deletion mutagenesis experiments support our structural finding. FGFR1 molecules lacking this amino acid stretch have a 250-fold reduced ability to bind FGFR (Imamura et al., 1990). A structure-based sequence alignment of FGFs reveals significant sequence diversity in the segment upstream of β1 in FGFs, suggesting that this region may also play a role in determining FGF binding specificity (FIG. 17).

In view of the interactions between residues prior to PI of FGFs and residues in D3 of FGFRs, it is possible that additional N-terminal residues that are not included in the currently analyzed FGF1 or FGF2 may also play a role in the determining specificity. To test this hypothesis, the crystal structure of full length FGF2 in complex with FGFR2 was determined (data not shown). In this crystal structure, however, all the residues N-terminal to Phe17 are disordered, suggesting that this region does not play a major role in FGFR binding. The significance of the N-terminal residues of FGF2 remains unclear.

FGFR Mutations Responsible for Human Skeletal Disorders

Mutations in the extracellular domains of FGFR1 and FGFR2 have been identified in patients with birth defects involving craniosynostosis (premature fusion of the cranial sutures) such as Pfeifer, Crouzon, Jackson-Weiss, and Apert syndromes (reviewed by Naski and Ornitz, 1998; Burke et al., 1998). These mutations cluster in three regions: in the D2-D3 linker, in D3 and in the linker connecting D3 to the transmembrane helix. These mutations can be classified into two groups: (1) Most of these mutations are substitutions of a cysteine with another amino acid or vice versa, resulting in the creation of unpaired cysteines. This leads to ligand-independent dimerization and activation via formation of an intermolecular disulfide bond between receptor molecules. (2) There are mutations that do not involve cysteine substitutions. Nevertheless, it is thought that these mutations must also result in constitutive activation (ligand-independent) of the affected receptors because they cause similar disease phenotypes as those mutations that create free cysteines. The precise molecular mechanisms by which these mutations lead to receptor activation are less clear.

Figure 18:
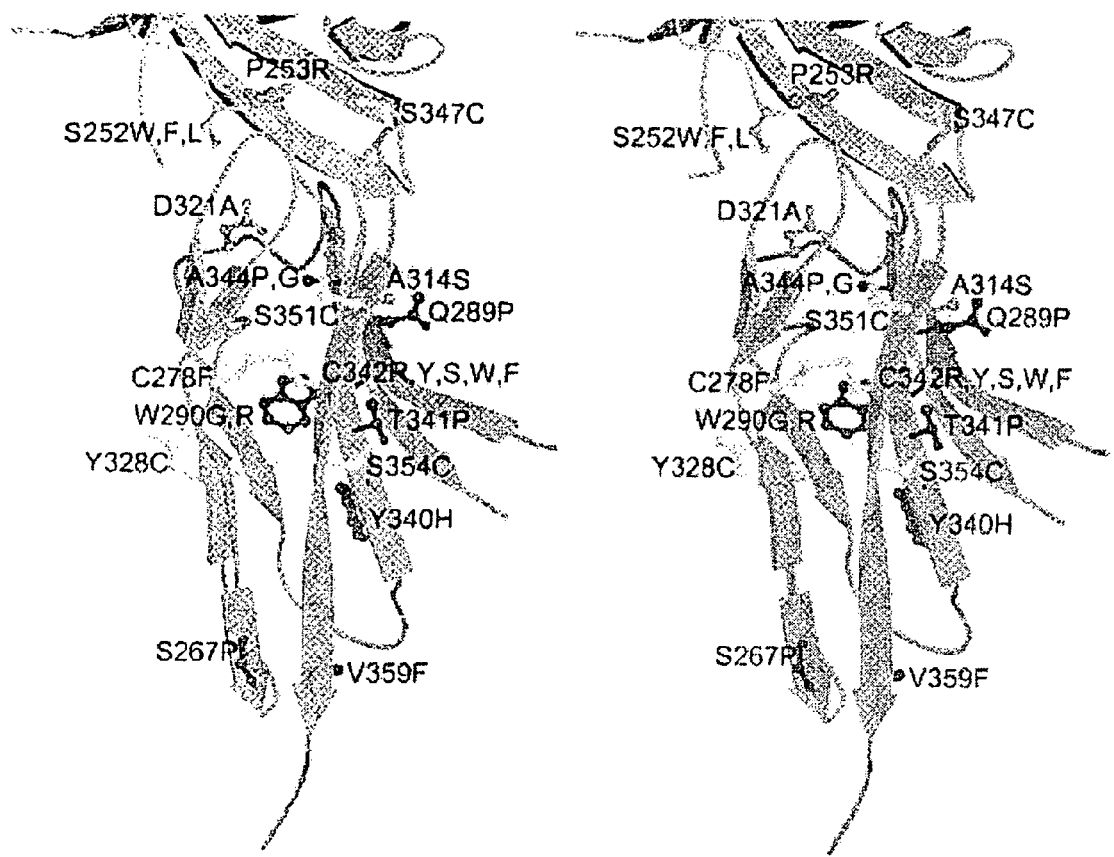
FIG. 18 depicts the locations of the mutations in the human FGFR2 gene that lead to skeletal disorders are mapped onto a ribbon representation the FGF2-FGFR2 structure. Side chains of the residues are colored with respect to the type of substitution. In yellow are mutations that substitute a cysteine with another amino acid or vice versa, resulting in the creation of unpaired cysteines. In red are mutations that are expected to destabilize the tertiary structure of D3 and thus disfavor the formation of the correct intra-domain disulfide bridge. In green are mutations that are predicted to affect ligand-binding affinity or specificity.
Figure 19:
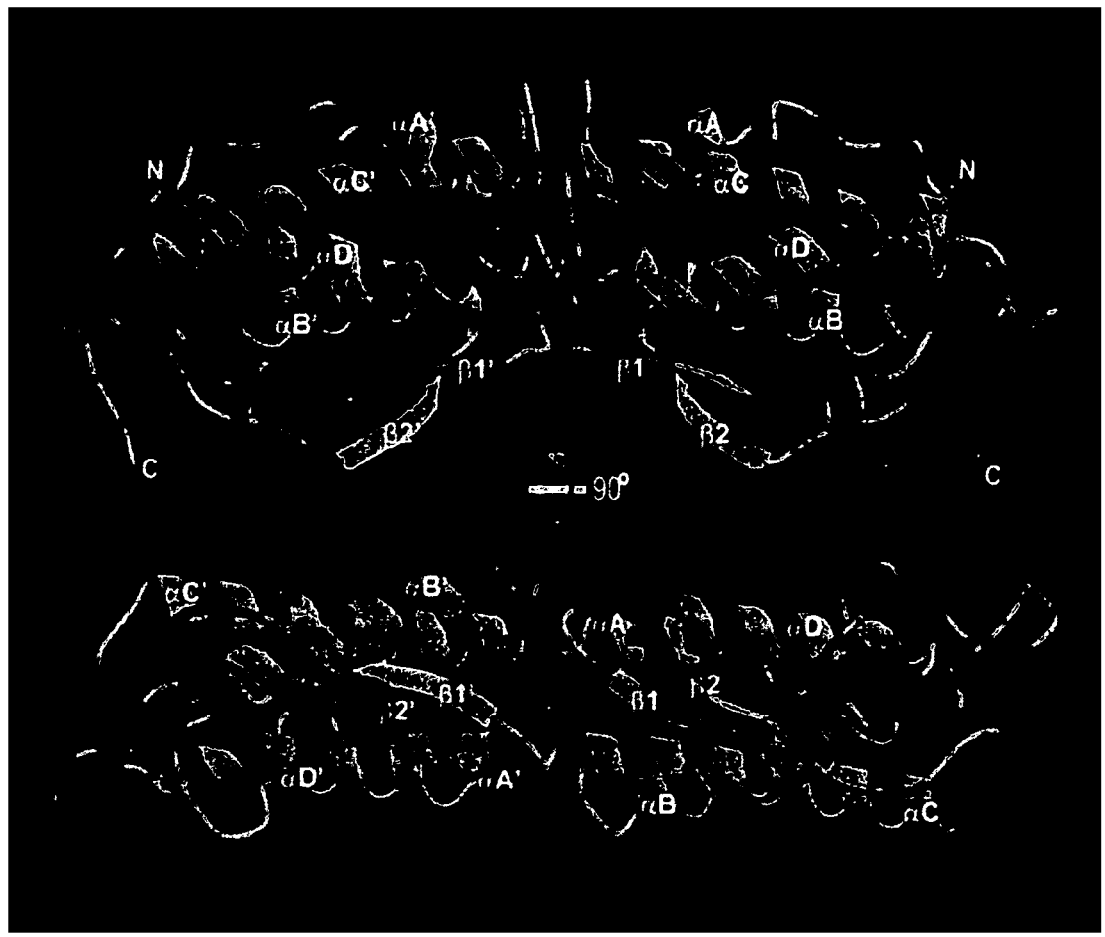
FIG. 19 depicts the overall structure of SCF (constructed by Molscript and Raster3D (Kraulis, J. Appl. Crystallogr. 24, 946–950 (1991); Merrit et al., *Methods Enzymol.* 277, 505–524 (1991))) and its relation with other cytokines by showing a ribbon representation of the SCF structure, in two views related by a rotation of approximately 90°. The termini and secondary structures are labeled; the strands are rendered as arrows, the helices as ribbons, and the loop regions as tubes. The two-fold axis is marked with a diamond.

To understand the molecular bases for the effects of these mutations on FGFR function, we have mapped these mutations onto the three-dimensional structure of FGF2FGFR2 (FIG. 18). Based on our structural data we predict that many mutations in D3, although not directly involving cysteines, could destabilize the tertiary structure of D3 and disfavor the formation of the intra-domain disulfide bridge, thus increasing the likelihood of disulfide bridging between receptor molecules (FIG. 18). Perhaps this notion is best exemplified by the substitution of Trp290 with glycine or arginine. Residue Trp290 is located in the core of D3, adjacent to the disulfide bridge, and replacement of this residue with either of the two amino acids will likely reduce the stability of D3 (FIG. 18).

Mutations of two highly conserved residues Ser252 and Pro253 in the D2-D3 linker of FGFR2 are responsible for all the known cases of Apert syndrome. Mutation of the equivalent proline in FGFR1 (Pro252) has been reported in some cases of Pfeifer syndrome. Based on our structural data we predict that these mutations introduce specific interactions between FGFR and FGF. Indeed, Anderson et al. (1998) have shown that, compared with wild type FGFR2, mutant FGFR2 molecules bearing the Apert mutations exhibit a selective increase in affinity towards FGF2, leading to enhanced signaling where availability of ligand is limiting (Anderson et al., 1998).

As described above, the amino acid stretch between βC' and βE plays a critical role in determining specificity. Residue Asp321 makes three hydrogen bonds with FGF2 (FIG. 13). Replacement of Asp321 with alanine, which is detected in some cases of Pfeifer syndrome, will therefore reduce the affinity of FGF2 towards FGFR2. It is conceivable, that this amino acid substitution will increase the affinity of FGFR2 for other members of the FGF family. Substitution of Ala35, also located in the βC'-βE loop, with a serine is also associated with Pfeifer syndrome. Residue Ala315 participates in the formation of the hydrophobic βC'-βE plug. This substitution can destabilize the hydrophobic plug and may affect ligand binding specificity.

Heparin-Binding Canyon

In the crystal structure of the illustrative embodiment, a highly positively charged "canyon" that continues onto the top side of both ligands is formed by the interaction of the two D2 regions in the dimer. The canyon receives its positive potential from lysines 160, 163, 172, 175, and 177 of FGFR1. This canyon may represent the site of heparin binding. FGF2 also contains a high affinity heparin binding site, consisting of Asn-27, Lys-125, Gln-134, and Arg-120, and heparin increases the apparent affinity of FGF2 for FGFR1. Thus, these residues may represent a useful therapeutic target, for example using a molecule(s) which affects the affinity of a receptor PTK for its ligand.

It has been postulated that heparin traverses this canyon and bridges the two 1:1 FGF:FGFR complexes. A recently reported crystal structure of another dimeric assemblage of two FGF1:FGFR2 complexes lends additional support to this model (Stauber et al., Proc. Natl. Acad. Sci. USA 97,49–54 (2000)).

Based on the dimeric structure, manual docking experiments have shown that a maximally active dodecasaccharide perfectly traverses the canyon and engages both the high- and low-affinity heparin binding sites of the ligands. In contrast, an octasaccharide placed centrally into the canyon can only interact with the low-affinity heparin binding sites of the ligands. A canyon-docked hexasaccharide is unable to interact with any heparin binding sites of the ligands, implying that oligosaccharides smaller than an octasaccharide do not possess biological activity. There has been some controversy, however, in determining the minimal length of heparin necessary for FGF signaling. It has been proposed that the shortest biologically active heparin oligosaccharide is an octasaccharide and that an increase in heparin length parallels an increase in biological activity up to a dodecasaccharide. However, other studies report that hexasaccharides are biologically active and that even disaccharides possess biological activity.

The inability of this model to fully reconcile all of the previous literature led us to further characterize the role of heparin in FGF signaling. The determination of the crystal structure of a ternary FGF2-FGFR1-heparin complex is described herein. Interactions between heparin, FGF and FGFR provide a molecular basis for the dual role of heparin in augmenting 1:1 FGF:FGFR affinity and promoting dimerization of two FGF-FGFR complexes. Moreover, the unexpected 2:2:2 stoichiometry of FGF:FGFR:heparin observed in the structure led us to propose an new model that also accounts for FGF-dependent FGFR activation by short heparin analogs.

While the heparin binding residues in D2 of FGFRs are highly conserved, the heparin binding residues of the FGF family are known to display considerable diversity (Faham et al., Curr. Opin. Struct. Biol. 8, 578–586 (1998); Venkataraman et al., Proc. Natl. Acad. Sci. USA 96, 3658–3663 (1999)). Moreover, the $\beta 1$-$\beta 2$ heparin binding loop is of variable length in different FGFs. As a result of this heterogeneity, it is likely that different FGFs require heparan sulfates of distinct sulfation and/or length to exert their optimal biological activity. In fact, it has been demonstrated that FGF2 requires 2-O-sulfate for heparin binding but not 6-O-sulfate. In contrast, FGF1 requires both sulfate groups to bind to heparin (Ishihara, 1994). Pericellular HSPGs from different cells exhibit significant heterogeneity in sulfation patterns, carbohydrate content and length. These variations could have a profound effect on FGF-FGFR interactions. Moreover, remodeling of the extracellular matrix during development may be a means to regulate the biological activities of FGFs.

Figure 31:
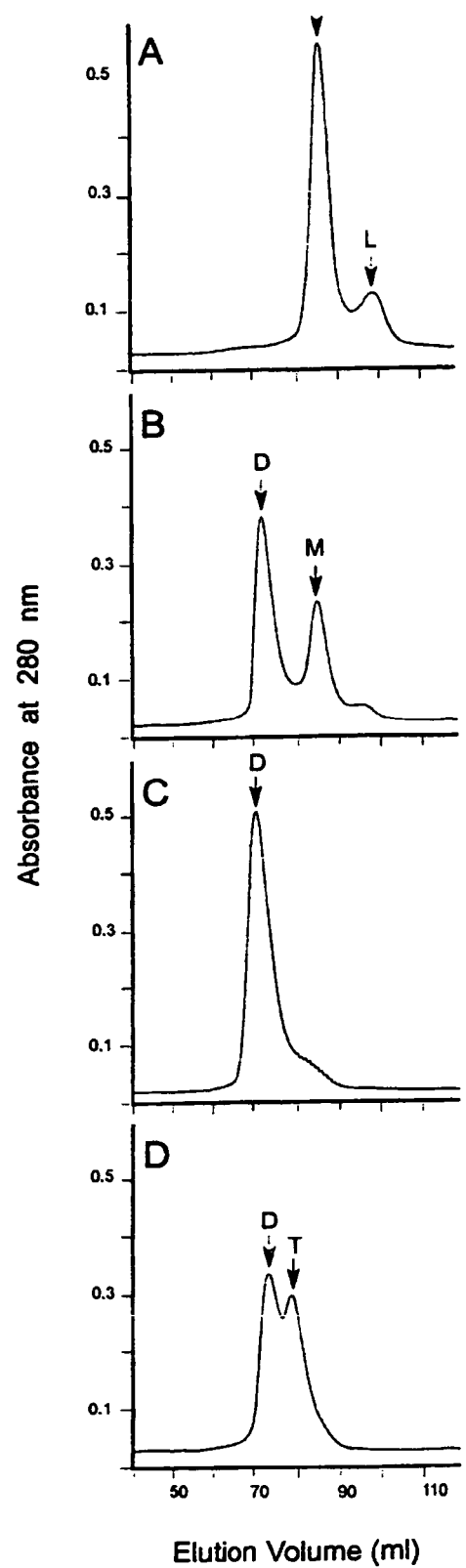
FIG. 31 shows the results of a separation on a Superdex 200 column (Pharmacia) of dimer formation for a set of mixtures of various ratios of homogeneously-sulfated hexasaccharide with purified 1:1 FGF1-FGFR2 complex. The following reaction mixture were used: A, control (no hexasaccharide added); B, hexasaccharide:FGF1-FGFR2 complex molar ratio of 0.5:1; C, hexasaccharide:FGF1-FGFR2 complex molar ratio of 1:1; D, and hexasaccharide:FGF1-FGFR2 complex molar ratio of 2.85:1. The positions of monomers and dimers are indicated by the letters "M" and "D" respectively. The letter "T" shows the position of the tight monomeric ternary 1:1:1 hexasaccharide: FGF1: FGFR2 complex. The letter "L" shows the position of free FGF1.

The heparin binding mode in the present structure disputes the previous findings regarding the minimal length requirement for heparin to promote FGF-FGFR dimerization as well as the stoichiometry of FGF:FGFR:heparin interactions. The tripartite interactions between FGF, FGFR and heparin observed in the crystal structure suggest that heparin hexasaccharides are sufficient to promote receptor dimerization. Therefore, we decided to test the ability of a hexasaccharide to promote dimerization of FGF-FGFR complexes in vitro. Homogeneously-sulfated hexasaccharide was mixed at various molar ratios with a purified 1:1 FGF1:FGFR2 complex and the reaction mixtures were analyzed by size exclusion chromatography to quantitate dimerization (FIG. 31). Addition of hexasaccharide at a molar ratio of 0.5:1 hexasaccharide:complex dimerized half of the FGF1-FGFR2 complexes (FIG. 31, Panel B). Hexasaccharide at a molar ratio of 1:1 hexasaccharide:complex led to the quantitative dimerization of all the FGF1-FGFR2 complexes (FIG. 31, Panel C). Excess hexasaccharide reduced dimerization and resulted in the appearance of a peak which elutes slightly earlier than the control (FIG. 31, Panel D). This peak corresponds to the ternary 1:1:1 hexasaccharide:FGF1:FGFR2 complex. It is noteworthy that in the absence of heparin, FGF-FGFR complexes tend to dissociate under size exclusion chromatography conditions, indicating that heparin increases the affinity of FGF for FGFR and stabilizes dimer formation. Hence, the biochemical experiments presented in FIG. 31 support the observed mode of heparin binding in the crystals.

Figure 32:
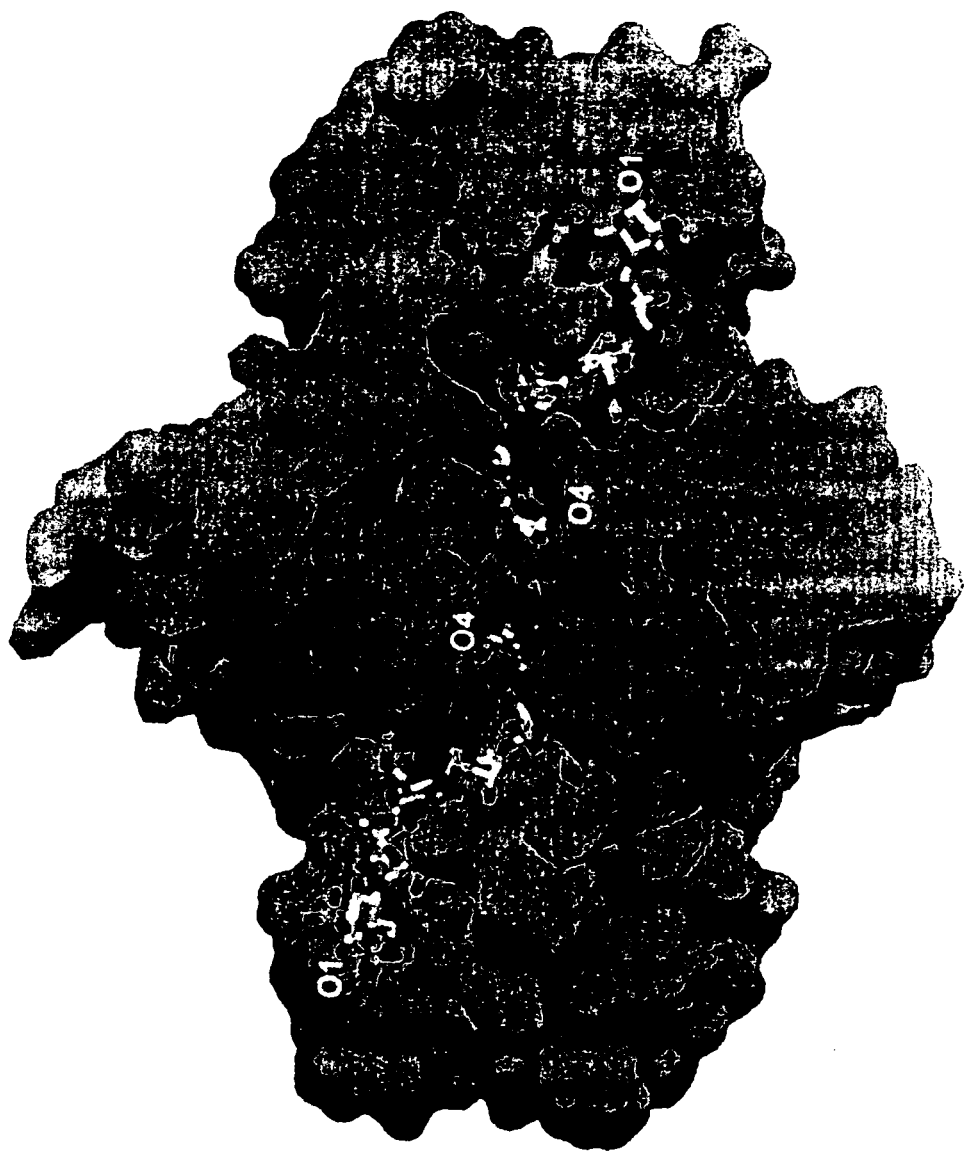
FIG. 32 depicts a molecular surface representation of the "two end" model of the dimeric 2:2:2 FGF2-FGFR1-heparin ternary complex. The view is from the top (same view as FIG. 27) looking down into the heparin-binding canyon. The FGF2 surface is shown in orange and D2 in green. Only the first 6 sugar rings of the decasaccharides are rendered in ball-and-stick and the non-reducing and reducing ends are labeled.

Based upon the crystal structure and supporting biochemical experiments described herein, a new "two end" model by which heparin induces FGF-dependent FGFR dimerization (see FIG. 32) is proposed. According to this model, heparin interacts via its non-reducing ends with both FGF and FGFR and promotes the formation of a stable 1:1:1 FGF:FGFR: heparin ternary complex. A second 1:1:1 FGF:FGFR:heparin ternary complex is then recruited to the first complex via direct FGFR:FGFR contacts, secondary interactions between FGF in one ternary complex and FGFR in the other ternary complex, and indirect heparin-mediated FGFR—FGFR contacts. In the absence of heparin the direct receptor—receptor contacts and secondary ligand-receptor interactions are not sufficient for appreciable dimerization. Clearly, heparin augments direct FGFR—FGFR and secondary FGF-FGFR interactions.

The proposed "two end" model presented in this report is consistent with the chemical architecture of heparan sulfate chains, which are linked by the reduced end (O1) to the protein core of HSPG. Furthermore, heparan sulfate can be roughly divided into low and high sulfate regions (Gambarini et al., Mol. Cell Biochem. 124, 121–129 (1993)). The low sulfate region is proximal to the protein core. The high sulfate region is located towards the non-reducing end (O4) that corresponds to the non-reducing ends of the decasaccharides bound in the center of the canyon in our structure. Moreover, the chemical nature of the highly sulfated non-reducing ends resemble heparin and are made up of tri-sulfated disaccharide units (IdoA,2S-GlcNS,6S) considered to be the building block of HSPG (Gambarini et al., Mol. Cell Biochem. 124, 121–129 (1993)). In fact, these highly sulfated regions of heparan sulfate have been shown to be the major determinants of the potentiating effect of heparan sulfate on FGF1 mitogenic activity (Gambarini et al., Mol. Cell Biochem. 124,121–129 (1993)).

A survey of the nature of the tripartite interactions between FGF, FGFR and heparin shows that about half of these interactions are mediated through carboxylate, linker and ring oxygens of heparin. Therefore, the results presented here afford a structural basis for the reported ability of certain synthetic non-sulfated heparan-derived di- and tri-saccharides to promote FGF-dependent FGFR activation in vivo (Ornitz et al., 1995). Synthesis of heparin molecules with a homogeneous sulfation pattern is difficult. On the basis of the structure presented here, it is possible to design small molecule heparin analogs in which the sulfate groups are replaced with similar functional groups. Thus, our structural studies establish a framework for the rational design of heparin mimetics capable of modulating FGF activity. Given the important roles FGF play in angiogenesis and their biological processes, synthetic heparin agonists and antagonists may have potential therapeutic value.

Crystalline FGFR Extracellular Domain/FGF1 complexes

In a second illustrative embodiment, the invention provides crystals of FGFR1 D2-D3 domain bound to an FGF1 molecule. The D2-D3 domain of this embodiment again consists of residues 142–365, and each D2-D3 domain is bound to a single FGF1 molecule. The crystals were obtained by the methods provided in the Examples. The FGFR1 D2-D3/FGF1 crystals, which may be native crystals, derivative crystals or co-crystals, have triclinic unit cells, and space group symmetry $\beta 1$. There are two FGFR1 D2-D3/FGF1 complexes in the asymmetric unit, related by an approximate two-fold axis. The unit cell has dimensions of about a=62.55 Å, b=64.06 Å, c=64.14 Å, $\alpha$=93.40°, $\beta$=111.17°, and $\gamma$97.18°.

Binding Interactions Between FGFR and FGF1

Within each D2-D3/FGF1 complex of the illustrative embodiment, FGF1 interacts extensively with D2, D3, and the linker between the two domains. A single hydrogen bond is noted between Tyr-15 in FGF 1 and Leu-165 in FGFR1, but the majority of interactions between D2 and FGF 1 are hydrophobic. For example, hydrophobic contacts can be seen between Tyr-15 and Leu-133, and Leu-135 of FGF1 and Ala 167 of D2, between Tyr-94, Leu-133, and His-93 of FGF1 and Pro-169 of D2, and between Phe-22 of FGF1 and Val-248 of FGFR1. These contacts are similar to the contacts described herein for the D2-D3/FGF2 crystal.

Interactions between FGF1 and the linker between D2 and D3 in the illustrative embodiment include hydrogen bonds between His-93 and Asn-95 of FGF 1 with Arg-250 of FGFR1. Again, these contacts are similar to the contacts described herein for the D2-D3/FGF2 crystal.

Additionally, several regions of FGF1 interact with D3, including Tyr-8, which inserts into a hydrophobic pocket in D3 formed by Val 279, Pro-285, and Ile-287. Additionally, Tyr-8 participates in a hydrogen bond with Gln-284 of FGFR1. In a region which is diverse amongst the members of the FGF family, residues 46,48–51, and 54 of FGF1 form van der Waals contacts with Gln-284, Pro-285, His-286, Gly-344, and Asn-345 of FGFR1 Ala-57 of FGF2, and Glu-49 in FGF1 forms a hydrogen bond with His-286 of FGFR1. As was described herein for the D2-D3/FGF2 crystals, this latter region may be important in defining the binding specificity of FGFRs, and thus may be a therapeutically important site.

Determining Unit Cell Dimensions and the Three Dimensional Structure of a Polypeptide or Polypeptide Complex Once the crystal is grown, it can be placed in a glass capillary tube and mounted onto a holding device connected to an X-ray generator and an X-ray detection device. Collection of X-ray diffraction patterns are well documented by those in the art. Ducruix and Geige, 1992, IRL Press, Oxford, England, and references cited therein. A beam of X-rays enter the crystal and then diffract from the crystal. An X-ray detection device can be utilized to record the diffraction patterns emanating from the crystal. Although the X-ray detection device on older models of these instruments is a piece of film, modern instruments digitally record X-ray diffraction scattering.

Methods for obtaining the three dimensional structure of the crystalline form of a peptide molecule or molecule complex are well known in the art. Ducruix and Geige, 1992, IRL Press, Oxford, England, and references cited therein. The following are steps in the process of determining the three dimensional structure of a molecule or complex from X-ray diffraction data.

After the X-ray diffraction patterns are collected from the crystal, the unit cell dimensions and orientation in the crystal can be determined. They can be determined from the spacing between the diffraction emissions as well as the patterns made from these emissions. The unit cell dimensions are characterized in three dimensions in units of Angstroms (one Å=$10^{-10}$ meters) and by angles at each vertices. The symmetry of the unit cell in the crystals is also characterized at this stage. The symmetry of the unit cell in the crystal simplifies the complexity of the collected data by identifying repeating patterns. Application of the symmetry and dimensions of the unit cell is described below.

Each diffraction pattern emission is characterized as a vector and the data collected at this stage of the method determines the amplitude of each vector. The phases of the vectors can be determined using multiple techniques. In one method, heavy atoms can be soaked into a crystal, a method called isomorphous replacement, and the phases of the vectors can be determined by using these heavy atoms as reference points in the X-ray analysis. Otwinowski, 1991, Daresbury, United Kingdom, 80–86. The isomorphous replacement method usually requires more than one heavy atom derivative. In another method, the amplitudes and phases of vectors from a crystalline polypeptide with an already determined structure can be applied to the amplitudes of the vectors from a crystalline polypeptide of unknown structure and consequently determine the phases of these vectors. This second method is known as molecular replacement and the protein structure which is used as a reference must have a closely related structure to the protein of interest. Naraza, 1994, *Proteins* 11:281–296. Thus, the vector information from a receptor PTK of known structure, such as those reported herein, are useful for the molecular replacement analysis of another receptor PTK with unknown structure.

Once the phases of the vectors describing the unit cell of a crystal are determined, the vector amplitudes and phases, unit cell dimensions, and unit cell symmetry can be used as terms in a Fourier transform function. The Fourier transform function calculates the electron density in the unit cell from these measurements. The electron density that describes one of the molecules or one of the molecule complexes in the unit cell can be referred to as an electron density map. The amino acid structures of the sequence or the molecular structures of compounds complexed with the crystalline polypeptide may then be fit to the electron density using a variety of computer programs. This step of the process is sometimes referred to as model building and can be accomplished by using computer programs such as TOM/FRODO. Jones, 1985, *Methods in Enzymology* 115:157–171.

A theoretical electron density map can then be calculated from the amino acid structures fit to the experimentally determined electron density. The theoretical and experimental electron density maps can be compared to one another and the agreement between these two maps can be described by a parameter called an R-factor. A low value for an R-factor describes a high degree of overlapping electron density between a theoretical and experimental electron density map.

The R-factor is then minimized by using computer programs that refine the theoretical electron density map. A computer program such as X-PLOR can be used for model refinement by those skilled in the art. Brunger, 1992, *Nature* 355:472475. Refinement may be achieved in an iterative process. A first step can entail altering the conformation of atoms defined in an electron density map. The conformations of the atoms can be altered by simulating a rise in temperature which will increase the vibrational frequency of the bonds and modify positions of atoms in the structure. At a particular point in the atomic perturbation process, a force field, which typically defines interactions between atoms in terms of allowed bond angles and bond lengths, Van der Waals interactions, hydrogen bonds, ionic interactions, and hydrophobic interactions, can be applied to the system of atoms. Favorable interactions may be described in terms of free energy and the atoms can be moved over many iterations until a free energy minimum is achieved. The refinement process can be iterated until the R-factor reaches a minimum value.

The three dimensional structure of the molecule or molecule complex is described by atoms that fit the theoretical electron density characterized by a minimum R-value. A file can then be created for the three dimensional structure that defines each atom by coordinates in three dimensions. Examples of such structural coordinate files are defined in Tables 1–4 and 6.

V. Stem Cell Factor

Stem cell factor ("SCF") is a growth factor implicated in the stimulation of the survival, proliferation, and differentiation of hematopoietic cells. SCF is also known as mast cell growth factor ("MCGF"), steel (Sl) factor ("SLF") or kit ligand ("KL"). SCF is believed to be critical for mast cell production and function and to play an important role in the development of melanocytes, germ cells, and intestinal pacemaker cells. SCF is believed to mediate its biological effects by binding to and activating a receptor protein tyrosine kinase designated c-kit (also referred to as SCF receptor ("SCFR"). Like other RPTK ligands, SCF induces dimerization of c-kit followed by trans-autophosphorylation of the cytoplasmic protein tyrosine kinase domain leading to subsequent recruitment of signaling proteins, tyrosine phosphorylation of substrates and activation of multiple signaling pathways.

It is believed that stem cell factor ("SCF") can play an important role in hematopoeisis by stimulating the survival, proliferation and differentiation of mast cells, melanocytes and germ cells. SCF has been tested extensively in both animals and human because of its ability to promote hematopoietic recovery. It has been demonstrated that SCF treatments produce an increase in the number of peripheral blood neutrophiles and hematopoietic progenitor cells and modest rises in the numbers of platelets and lymphocytes. SCF, alone or in combination with other cytokines, is used to reduce the hematological damage of chemotherapy. In a separate clinical trial, SCF has also been proven to be effective in enhancing the ability of G-CSF to mobilize peripheral blood hematopoietic progenitor and stem cells. It is believed that these cells can be transplanted to reconstitute the hematopoietic system in patients receiving bone marrow ablative therapy (Nicola et al., Protein Chem. 52, 1–65 (1998)).

SCF exist naturally as membrane anchored and soluble isoforms as a result of alternative RNA splicing and proteolytic processing. The soluble form of SCF has 165 amino acids, but its receptor binding core has been mapped to the first 141 residues (Langley et al., Arch. Biochem. Biophys. 311, 55–61 (1994)). SCF functions as a non-covalent homodimer, but under physiological conditions, the majority of SCF is reported to exist as a monomer. Dimerization of SCF is a dynamic process and it may play a regulatory role in the control of SCFR binding affinity and receptor activation.

Comparison of SCF with Other Growth Factors

SCF belongs to the short-chain helical cytokine family (Bazan, 1991; Rozwarski et al., 1994), but its resemblance to the other cytokines is limited only to the overall fold. The primary structures exhibit very weak similarity and sequences can be aligned only by comparison of the secondary structures (FIG. 20). The structure of SCF is most similar to the structure of M-CSF (Pandit et al., Science 258, 1358–1362 (1992)). The core four helix bundles of the two proteins superimpose relatively well, with r.m.s. deviation of 1.98 Å for the alpha-C atoms. However, upon superimposition of the helices, the two beta-strands deviate significantly. Two loops in SCF, residues 29 to 41 and residues 90 to 98, extrude more than those of M-CSF. At the dimer interface, the SCF loop from residue 61 to 72 also extrudes further away from the core and packs against the same loop from the second protomer. The x-ray crystallography work described herein suggests that there is more contact between the two protomers of SCF as compared to the contact between the two M-CSF protomers. Furthermore, M-CSF is a covalent homodimer linked by an intermolecular disulfide bond whereas SCF is a noncovalent homodimer. Flt3 ligand is also a noncovalent homodimer, but it has an extra intramolecular disulfide bond as does M-CSF. Nevertheless, the structure of flt3 ligand (Hannum et al., Nature 368, 643–648 (1994)) can be predicted with reasonable confidence based upon the crystal structures of SCF described herein together with the previously described crystal structure of M-CSF (Pandit et al., Science 258, 1358–1362 (1992)).

In contrast to the disulfide linked PDGF and M-CSF homodimers, two other ligands of the same family of receptor tyrosine kinases, SCF functions as a non-covalent homodimer (Pandit et al., Science 258, 1358–1362 (1992)). It has been shown that the bivalency of SCF is the sole driving force responsible for dimerization of the extracellular ligand binding domain of c-kit. Hence analysis of the molecular interactions that control SCF-dimer formation are critical for understanding the mechanism of activation of c-kit.

It is known that dimerization of SCF is sensitive to pH and salt concentration changes. This property is likely due to the fact that the interface is formed in part by polar interactions via salt bridges at the periphery and by a water molecule-mediated hydrogen bonds among buried polar residues at the core of the interface. In an attempt to identify residues that play a role in SCF dimerization, a Phe63Cys mutant was generated and characterized for receptor binding activity (Hsu et al., J. Biol. Chem. 272, 6406–6415 (1997)). It was demonstrated that this mutation led to the formation of a covalent SCF dimer. However, the mutant SCF dimer was biologically inactive. The structure of the SCF interface described herein provides a plausible explanation for the lack of activity of this mutant. (see FIG. 21). In the structure, the shortest distance between the side chains of the two symmetry related Phe63 is about 8 Å with the well-coordinated water molecule between them. It is impossible to create a disulfide bond between these two residues without disrupting the secondary and tertiary structures of the SCF dimer.

Domain Swapping and the Covalent Dimer of SCF

Figure 23:
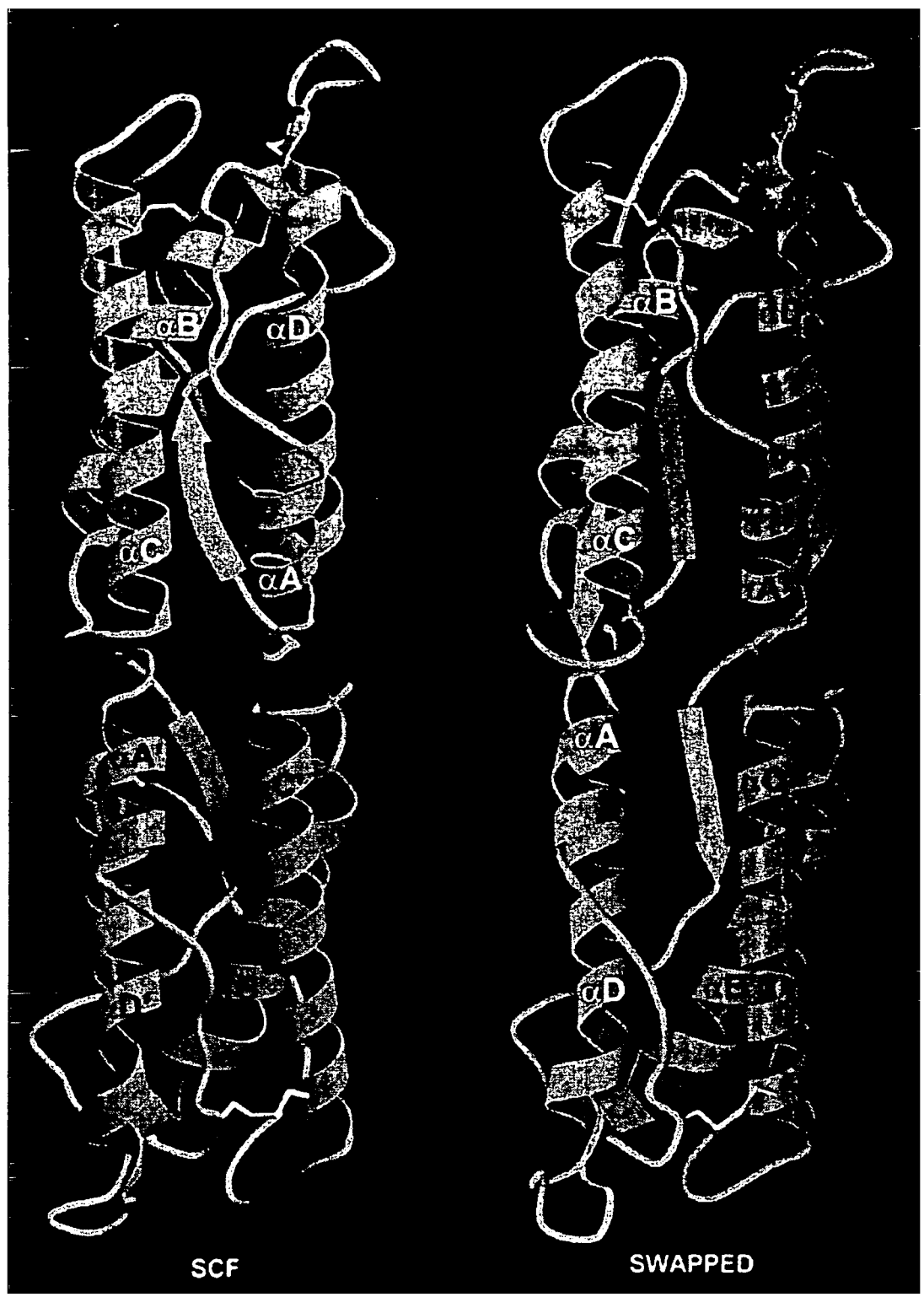
FIG. 23 depicts a model of covalent SCF dimer constructed by Molscript and Raster3D (Kraulis, J. Appl. Crystallogr. 24, 946–950 (1991); Merrit et al., Methods Enzymol. 277, 505–524 (1991)). The non-covalent (native) dimer is on the left and a model for the covalent SCF dimer is on the right. Each protomer is colored either orange or green. The disulfide bonds are shown in ball-and-stick with sulfur atoms colored in yellow.

Recombinant SCF is expressed in *E. coli* as inclusion bodies in a denatured form and an active SCF protein is produced by a procedure involving refolding and oxidation. It has previously been reported that a small fraction of the refolded-oxidized protein is a covalent disulfide linked form of SCF. Interestingly, the covalent SCF dimer has bben reported to bind to c-kit with slightly reduced affinity but was more potent in stimulation of hematopoietic cells. Comparison of the secondary and tertiary structures by spectroscopic methods demonstrated that the covalent dimer is indistinguishable from the non-covalent dimer (Lu et al., J. Biol. Chem. 271, 11309–11316 (1996)). Surprisingly, the disulfide linkages of the covalent dimer were found to be identical to those in the non-covalent dimer except that the disulfide linkages in the variant protein were intermolecular. That is, Cys4 and Cys43 from one protomer form disulfide bonds with Cys89 and Cys138, respectively, of the second protomer. It was thus proposed that the covalent dimer could be formed by a three-dimensional domain swapping of helices alphaA and alphaD between the two monomers (Lu et al., J. Biol. Chem. 271, 11309–11316 (1996)). A close examination of the three-dimension structure of SCF reported herein shows that the C2 symmetry of the dimer may allow these helices to be swapped between the protomers while preserving the overall structure and identical surface at the tails of each protomer. FIG. 23 shows a model generated by swapping helices alphaA and alphaD between the two protomers. Interestingly, the interactions at the core between the helices from the original dimer are preserved in the swapped model while the loops around the C2 axis and the orientation of the strands have to be adjusted. The disulfide pairs are identical in both forms except that they are intramolecular in the non-covalent dimer and intermolecular in the covalent dimer. It is worth noting that other four helix bundle cytokines such as L-5, IL-10 and IFN- are reported to form similar covalent interdigitated dimers naturally. In IL-5, helix alphaD and strand 2 of one protomer, together with helices alphaA, alphaB, alphaC and strand 1 from the other protomer, form one domain of the two-domain dimer. Indeed, because of the symmetric nature of the structure, it was possible to generate monomeric IL-5 mutants (Dickason et al., Nature 379, 652–655 (1996); Dickason et al., J Mol Med 74, 535–546 (1996); Edgerton et al., J. Biol. Chem. 272, 20611–20618 (1997)). By the same token, new type interdigitated covalent SCF dimers could be formed by introducing mutations in the loops between helix αA and strand 1 and between 2 and helix αD that favor the covalent dimer structure. These similarities in fold and dimeric symmetry among the helical cytokines probably reflect their common evolutionary origin.

Three-dimensional domain swapping is considered to be a general mechanism for the regulation of oligomer assembly, that is oligomers are formed from stable monomers by exchanging domains during evolution or under controlled laboratory conditions (Bennett et al., 1995). It has been suggested that under normal physiological conditions, the majority of soluble SCF exists as monomers. The balance between SCF monomers and dimers may be linked to the physiological requirement for activation of c-kit expressed on target cells in vivo. For therapeutic purpose, however, the more potent disulfide-linked dimer is generally preferred because it can be administered at low doses to avoid significant mast cell activation while stimulating hematopoietic recovery (Nocka et al., Blood 90, 3874–3883 (1997)).

Receptor Binding Region on SCF

SCF dimer are known to bind soluble or membrane forms of c-kit with high affinity and specificity. The binding of SCF to c-kit was analyzed by biochemical methods, by employing site-directed mutagenesis and by epitope mapping with site-specific anti-c-kit antibodies. It was reported that deletions of residues 1 to 3 from the N-terminus reduced the binding of SCF to c-kit by approximately 50%. Deletion of Cys4 inactivated SCF, whereas deletion of Cys138 and additional residues form the C-terminus only compromised SCF activity. Moreover, an SCF double mutant at Cys43Ala and Cys138Ala, which eliminate one pair of disulfide bonds, resulted in a partially active SCF as well. These experiments demonstrated that the N-terminus of SCF and the integrity of the Cys4–Cys89 disulfide bond are crucial for full CSF activity.

Figure 24:
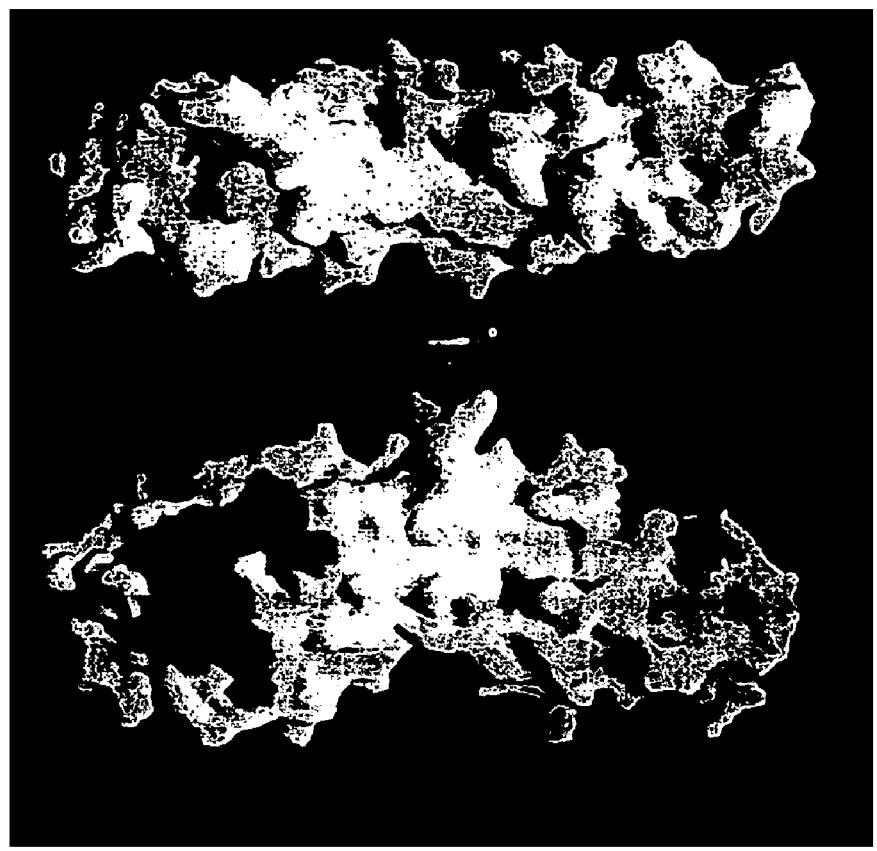
FIG. 24 depicts a potential binding site on SCF for c-kit and a model of SCF:SCFR complex created by GRASP Nicolls et al., Proteins 11, 281–296 (1991)). The molecular surface of SCF and proposed c-kit binding regions, in two views related by a rotation of approximately 90° are shown. A hydrophobic crevice at both tails is colored yellow. Two basic patches are colored blue and the acidic patch is colored red.

By analyzing the activities of a variety of SCF/M-CSF chimeric proteins, it has been shown that Arg121, Asp124, Lys127 and Asp128 are essential for SCF activity (Matous et al., Blood 88,437–444(1996)). Moreover, by using antibodies that neutralize different epitopes on SCF, it has been demonstrated that the regions flanked by amino acids 61 to 65 and 91 to 95 are also essential for SCF activity (Mendiaz et al., Eur. J. Biochem. 239, 842–849 (1996)). In general the regions mapped by biochemical methods are located in close proximity at the tail region of each SCF protomer. This region contains a deep crevice at the end of alphaC formed by side chains of the hydrophobic residues Phe102, Leu98, Pro34, Tyr32, and by the Cys43–Cys138 disulfide bridge (see FIG. 24). Next to the crevice, there are three charged patches; a positively charged patch (Arg5, Arg7, and Lys127) followed by a negatively charged patch (Asp84, Asp85, Glu88, and Glu92) and then by an additional positively charged patch (Lys91, Lys99, Lys100 and Lys103). FIG. 24 shows the locations of the positively charged and negative charged patches as well as the hydrophobic crevice. This surface may function as a receptor binding site with the charged interactions providing anchor and specificity for ligand/receptor interactions and the hydrophobic interactions providing enthalpy to complex formation.

While human and rodent SCF are highly conserved, the charged patches that may function as part of receptor binding regions are quite divergent (see FIG. 25). Residues Arg5 and Arg7 in the first positively charged patch of the human SCF are replaced by glycine and proline residues in rodents, respectively. In the second positively charged patch, residues Lys100 and Lys91 are substituted by glutamate residues in both mouse and rat. These changes could account for the difference in the binding affinity of human and murine SCF to the human c-kit that has been reported.

Natural and CHO-cell derived recombinant SCF are glycosylated on multiple asparagine, serine and threonine residues. The receptor binding properties of glycosylated SCF are consistent with the assignment of SCFR binding region shown in FIG. 24. There are four putative asparagine glycosylation sites in the functional core of SCF: Asn65, Asn72, Asn93 and Asn120. Asn72 is not glycosylated probably because its side chain is buried in the dimer interface. However, the side chains of Asn120, Asn65, and Asn93 remain accessible to the solvent in the structure and are indeed glycosylated to different extent. Asn120 is always glycosylated but this does not affect the binding of SCF to c-kit. In contrast, Asn65 and Asn93 are glycosylated in some, but not all, SCF molecules. Importantly, glycosylation of these asparagine residues has been reported to have an adverse effect on SCF binding to SCFR The structure described herein provides possible explanations for the adverse effect of glycosylation of these residues on the activity of SCF. The glycosylation of Asn93 may hinder SCF binding to c-kit as this residue is located very close to the acidic patch and to the hydrophobic crevice. On the other hand, Asn65 is located close to the dimer interface and glycosylation of this residue may interfere with SCF dimerization.

Model for SCF:SCFR Complex

The extracellular ligand binding domains of several receptor tyrosine kinases contain multiple Ig-like domains. For instance, the extracellular domains of FGF receptors contain three Ig-like domains while the extracellular domain of PDGF-receptor family to which c-kit belongs is composed of five Ig-like domains. Similarly, the extracellular domain of the VEGF-receptor has been reported to contain seven Ig-like domains. Although the ligands of these receptors are very diverse, the ligand binding regions in these three families of receptors have been mapped to Ig-like domains two and three (see, e.g., Plotnikov et al., Cell 98, 641–650 (1999)). The determination of the structures of the ligand binding domains of FGF and VEGF receptors demonstrated that FGF and VEGF bind differently to their respective receptors. In the FGF:FGFR complex the two receptors are packed side by side to one face and the ligands occupy the second face. On the other hand, the two VEGFR bind to the far ends of the VEGF-dimer creating an inverted "A" shaped complex with the ligand representing the cross bar in the "capital A". Since SCF functions as a dimer, SCF binding to c-kit would be expected to resemble the structure which has been reported for the VEGF:VEGFR complex.

Figure 26:
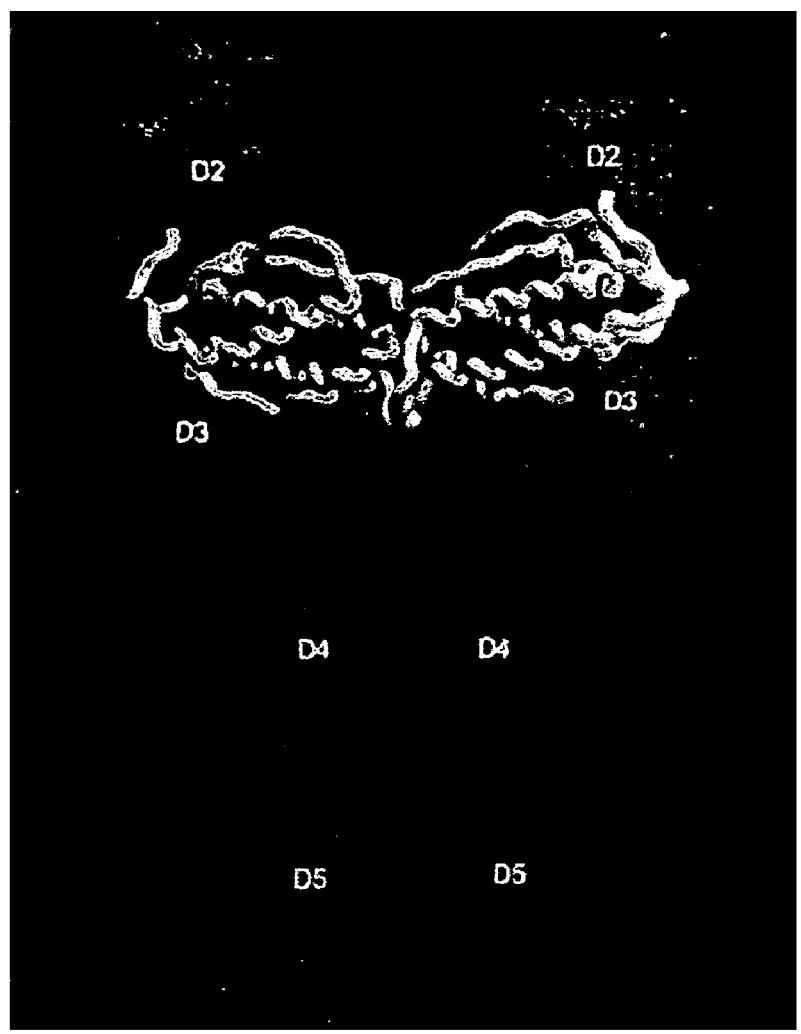
FIG. 26 shows a proposed model of the SCF in complex with Ig-like domains 2–5 of the extracellular domain of c-kit (labeled D2 to D5) created by GRASP (Nicolls et al., *Proteins* 11, 281–296 (1991)). The SCF dimer is represented in a worm model and the c-kit model by a molecular surface.
Figure 27:
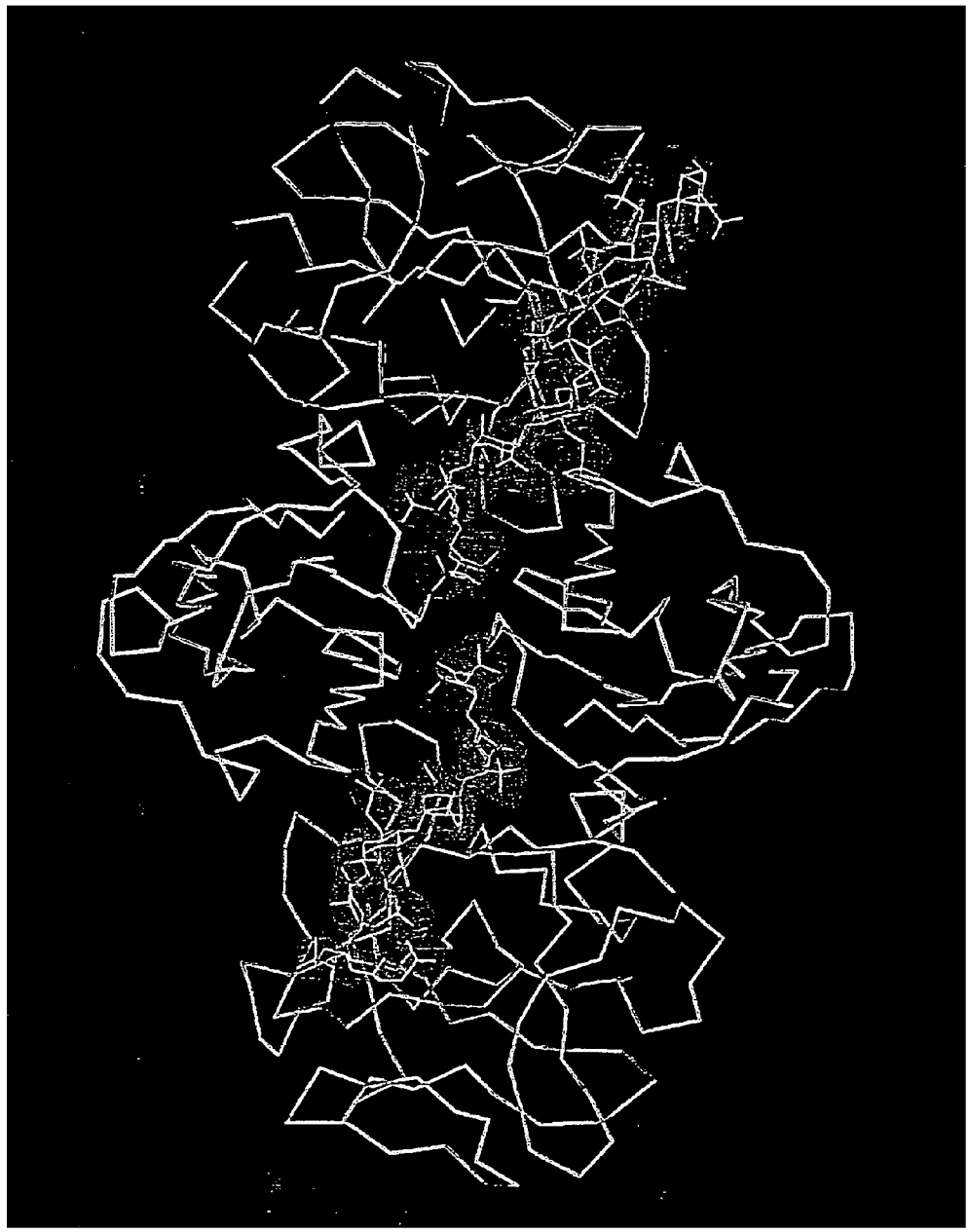
FIG. 27 depicts an electron density map of decasaccharides soaked into preformed crystals of an FGF2-FGFR1 complex showing the location of decasaccharides in the dimeric assemblage. Only the Cα traces of D2s (cyan) and FGFs (orange) are shown. The decasaccharides are rendered in white sticks.

The x-ray crystal structure of the SCF dimer was used to build a model of SCF:c-kit complex formation and dimerization. Using the structure of FGFR as a template, a model for Ig-like domains 2–3 as well as 4–5 of c-kit was developed. Ig-like domains 2 and 3 were then docked to the proposed SCF binding surface adopting the mode of FGFR binding to FGF2 (Plotnikov et al., Cell 98, 641–650 (1999)). In addition, the orientation of Ig-like domains 4 and 5 was adjusted to allow for interactions between domain 4 in the complex as suggested by previous biochemical studies (Blechman et al., Cell 80, 103–113 (1995)); see FIG. 26).

c-kit belongs to the same family of RTKs that also includes M-CSFR, PDGFR alpha, PDGFR alpha and flt3. Comparison of their primary structures shows that these RTKs are much more conserved than their ligands. Indeed, the structures of PDGF-A and PDGF-B are dramatically different from the structures of M-CSF and SCF and probably also flt3 ligand. The similarity of the RTKs is also reflected in the chromosomal localizations of their human and murine genes (Kondo et al., *Gene.* 208, 297–305 (1998)). It is thought that this family of RTKs has evolved from a common ancestral gene that undergone several gene-duplication events. It is worth noting that RTKs that bind to and are activated by ligands with structures of four-bundle helix (i.e., M-CSF, SCF) are primarily involved in the control of hematopoeisis, whereas other members of this family of RTKs exhibit broader expression pattern and are involved in the regulation of growth and development of several tissues and organs.

Determination of the three dimensional structure of SCF would facilitate the determination of the structure of SCF in complex with the extracellular domain of c-kit, and enable the design and production of more potent forms of therapeutic SCF analogues. With the detailed structural information described herein, it may now be possible to design novel SCF variants with increased therapeutic potency.

VI. Uses of the Crystals and Atomic Structure Coordinates

The crystals of the invention, and particularly the atomic structure coordinates obtained therefrom, have a wide variety of uses. For example, the crystals described herein can be used as a starting material in any of the art-known methods of use for RPTKs. Such methods of use include, for example, identifying molecules that bind to the native or mutated extracellular domain of RPTKs. The crystals and structure coordinates are particularly useful for identifying compounds which are modulators of RPTK function as an approach towards developing new therapeutic agents (see, e.g., Levitzki and Gazit, 1995, *Science* 267:1782–8).

The structure coordinates described herein can also be used as phasing models for determining the crystal structures of additional native or mutated receptor PTK extracellular domains, as well as the structures of co-crystals of such domains complexed with molecules such as ligands, ligand analogs, inhibitors, activators, agonists, antagonists, polypeptides, and other molecules. The structure coordinates, as well as models of the three-dimensional structures obtained therefrom, can also be used to aid the elucidation of solution-based structures of native or mutated receptor PTK extracellular domains, such as those obtained via NMR. Thus, the crystals and atomic structure coordinates of the invention provide a convenient means for elucidating the structures and functions of receptor tyrosine kinases.

For purposes of clarity and discussion, the crystals of the invention will be described by reference to specific FGFR1 D2-D3/FGF2 and FGFR1 D2-D3/FGF1 exemplary crystals. Those skilled in the art will appreciate that the principles described herein are generally applicable to crystals of the extracellular domain of any receptor tyrosine kinase, including but not limited to receptor PTKs such as are PDGFR, EGFR, VEGFR, HGFR, neurotrophinR, HER2, HER3, HER4, InsulinR, IGFR, CSFIR, FLK, KDR, VEGFR2, CCK4, MET, TRKA, AXL, TIE, EPH, RYK, DDR, ROS, RET, LTK, ROR1, MUSK, members of the FGFR family, such as FGFR1, FGFR2, FGFR3, and FGFR4, and orphan receptor PTKs.

VII. Structure Determination for PTKs with Unknown Structure Using Structural Coordinates Structural coordinates, such as those set forth in Tables 1–4 and 6 can be used to determine the three dimensional structures of RPTKs with unknown structure. The methods described below can apply structural coordinates of a polypeptide with known structure to another data set, such as an amino acid sequence, X-ray crystallographic diffraction data, or nuclear magnetic resonance (NMR) data. Preferred embodiments of the invention relate to determining the three dimensional structures of receptor PTKs and related polypeptides. These include receptor PTKs such as are PDGFR, EGFR, VEGFR, HGFR, neurotrophinR, HER2, HER3, HER4, InsulinR, IGFR, CSFIR, FLK, KDR, VEGFR2, CCK4, MET, TRKA, AXL, TIE, EPH, RYK, DDR, ROS, RET, LTK, ROR1, MUSK, members of the FGFR family, such as FGFR1, FGFR2, FGFR3, and FGFR4, and orphan receptor PTKs.

Structures Using Amino Acid Homology

Homology modeling is a method of applying structural coordinates of a polypeptide of known structure to the amino acid sequence of a polypeptide of unknown structure. This method is accomplished using a computer representation of the three dimensional structure of a polypeptide or polypeptide complex, the computer representation of amino acid sequences of the polypeptides with known and unknown structures, and standard computer representations of the structures of amino acids. Homology modeling comprises the steps of (a) aligning the amino acid sequences of the polypeptides with and without known structure; (b) transferring the coordinates of the conserved amino acids in the known structure to the corresponding amino acids of the polypeptide of unknown structure; (c) constructing structures of the rest of the polypeptide; and (d) refining the subsequent three dimensional structure. One skilled in the art recognizes that conserved amino acids between two proteins can be determined from the sequence alignment step in step (a).

The above method is well known to those skilled in the art. Greer, 1985, *Science* 228, 1055. Blundell et al., 1988, *Eur. J. Biochem.* 172, 513. A computer program currently utilized for homology modeling by those skilled in the art is the Homology module in the Insight II modeling package distributed by Molecular Simulations Inc.

Alignment of the amino acid sequence is accomplished by first placing the computer representation of the amino acid sequence of a polypeptide with known structure above the amino acid sequence of the polypeptide of unknown structure. Amino acids in the sequences are then compared and groups of amino acids that are homologous (e.g., amino acid side chains that are similar in chemical nature—aliphatic, aromatic, polar, or charged) are grouped together. This method will detect conserved regions of the polypeptides and account for amino acid insertions or deletions.

Once the amino acid sequences of the polypeptides with known and unknown structures are aligned, the structures of the conserved amino acids in the computer representation of the polypeptide with known structure are transferred to the corresponding amino acids of the polypeptide whose structure is unknown. For example, a tyrosine in the amino acid sequence of known structure may be replaced by a phenylalanine, the corresponding homologous amino acid in the amino acid sequence of unknown structure.

The structures of amino acids located in non-conserved regions are to be assigned by either using standard peptide geometries or molecular simulation techniques, such as molecular dynamics. The final step in the process is accomplished by refining the entire structure using molecular dynamics and/or energy minimization.

The homology modeling method is well known to those skilled in the art and has been practiced using different protein molecules. For example, the three dimensional structure of the polypeptide corresponding to the catalytic domain of a serine/threonine protein kinase, myosin light chain protein kinase, was homology modeled from the cAMP-dependent protein kinase catalytic subunit. Knighton et al., 1992, *Science* 258:130–135.

Structures Using Molecular Replacement

Molecular replacement is a method of applying the X-ray diffraction data of a polypeptide of known structure to the X-ray diffraction data of a polypeptide of unknown sequence. This method can be utilized to define the phases describing the X-ray diffraction data of a polypeptide of unknown structure when only the amplitudes are known. X-PLOR is a commonly utilized computer software package used for molecular replacement. Brunger, 1992, *Nature* 355:472–475. AMORE is another program used for molecular replacement. Navaza, 1994, *Acta Crystallogr.* A50:157–163. Preferably, the resulting structure does not exhibit a root-mean-square deviation of more than 3 Å.

A goal of molecular replacement is to align the positions of atoms in the unit cell by matching electron diffraction data from two crystals. A program such as X-PLOR can involve four steps. A first step can be to determine the number of molecules in the unit cell and define the angles between them. A second step can involve rotating the diffraction data to define the orientation of the molecules in the unit cell. A third step can be to translate the electron density in three dimensions to correctly position the molecules in the unit cell. Once the amplitudes and phases of the X-ray diffraction data are determined, an R-factor can be calculated by comparing electron diffraction maps calculated experimentally from the reference data set and calculated from the new data set. An R-factor between 30–50% indicates that the orientations of the atoms in the unit cell are reasonably determined by this method. A fourth step in the process can be to decrease the R-factor to roughly 20% by refining the new electron density map using iterative refinement techniques described herein and known to those or ordinary skill in the art.

Structures Using NMR Data

Structural coordinates of a polypeptide or polypeptide complex derived from X-ray crystallographic techniques can be applied towards the elucidation of three dimensional structures of polypeptides from nuclear magnetic resonance (NMR) data. This method is used by those skilled in the art. Wuthrich, 1986, John Wiley and Sons, New York: 176–199; Pflugrath et al., 1986, *J. Molecular Biology* 189:383–386; Kline et al., 1986, *J. Molecular Biology* 189:377–382. While the secondary structure of a polypeptide is often readily determined by utilizing two-dimensional NMR data, the spatial connections between individual pieces of secondary structure are not as readily determinable. The coordinates defining a three-dimensional structure of a polypeptide derived from X-ray crystallographic techniques can guide the NMR spectroscopist to an understanding of these spatial interactions between secondary structural elements in a polypeptide of related structure.

The knowledge of spatial interactions between secondary structural elements can greatly simplify Nuclear Overhauser Effect (NOE) data from two-dimensional NMR experiments. Additionally, applying the crystallographic coordinates after the determination of secondary structure by NMR techniques only simplifies the assignment of NOEs relating to particular amino acids in the polypeptide sequence and does not greatly bias the NMR analysis of polypeptide structure. Conversely, using the crystallographic coordinates to simplify NOE data while determining secondary structure of the polypeptide would bias the NMR analysis of protein structure.

As the analysis of polypeptide structure by NMR methods is a relatively new technique, the use of structural coordinates defining an RPTK structure will most likely be utilized more frequently in the near future. As the method progresses, the three dimensional structure analysis of polypeptides of the same size as an RPTK extracellular domain will become more frequent.

VIII. Structure-Based Design of Modulators of PTK Function Utilizing Structural Coordinates Structure-based modulator design and identification methods are powerful techniques that can involve searches of computer data bases containing a wide variety of potential modulators and chemical functional groups. The computerized design and identification of modulators is useful as the computer data bases contain more compounds than the chemical libraries, often by an order of magnitude. For reviews of structure-based drug design and identification see Kuntz et al., 1994, *Acc. Chem. Res.* 27:117; Guida, 1994, *Current Opinion in Struc. Biol.* 4: 777; Colman, 1994, *Current Opinion in Struc. Biol.* 4: 868.

The three dimensional structure of a polypeptide defined by structural coordinates can be utilized by these design methods. Preferably, the structural coordinates of Table 1 or Table 2 can be utilized by this method. In addition, the three dimensional structures of RPTKs determined by the homology, molecular replacement, and NMR techniques described herein can also be applied to modulator design and identification methods. Thus, the structures of receptor PTKs, such as are PDGFR, EGFR, VEGFR, HGFR, neurotrophinR, HER2, HER3, HER4, InsulinR, IGFR, CSFIR, FLK, KDR, VEGFR2, CCK4, MET, TRKA, AXL, TIE, EPH, RYK, DDR, ROS, RET, LTK, ROR1, MUSK, members of the FGFR family, such as FGFR1, FGFR2, FGFR3, and FGFR4, and orphan receptor PTKs, can be utilized by the methods described herein.

Design by Searching Molecular Data Bases

One method of rational modulator design searches for modulators by docking the computer representation of compounds from a data base of molecules. Publicly available data bases include:
    a) ACD from Molecular Designs Limited
    b) NCI from National Cancer Institute
    c) CCDC from Cambridge Crystallographic Data Center
    d) CAST from Chemical Abstract Service e) Derwent from Derwent Information Limited
f) Maybridge from Maybridge Chemical Company LTD
g) Aldrich from Aldrich Chemical Company
h) Directory of Natural Products from Chapman & Hall One such data base (ACD distributed by Molecular Designs Limited Information Systems) contains, for example, 200,000 compounds that are synthetically derived or are natural products. Methods available to those skilled in the art can convert a data set represented in two dimensions to one represented in three dimensions. These methods are enabled by such computer programs as CONCORD from Tripos Associates or DB-Converter from Molecular Simulations Limited.

Multiple methods of structure-based modulator design are known to those in the art. Kuntz et al., 1982, *J. Mol. Biol.* 162: 269; Kuntz et al., 1994, *Acc. Chem. Res.* 27: 117; Meng et al., 1992, *J. Compt. Chem.* 13: 505; Bohm, 1994, *J. Comp. Aided Molec. Design* 8: 623.

A computer program widely utilized by those skilled in the art of rational modulator design is DOCK from the University of California in San Francisco. The general methods utilized by this computer program and programs like it are described in three applications below. More detailed information regarding some of these techniques can be found in the Molecular Simulations User Guide, 1995.

A typical computer program used for this purpose can comprise the following steps:

(a) remove an existing compound, ligand, or ligand analog from the protein;

(b) dock the structure of another compound, ligand, or ligand analog into the compound binding site using the computer program (such as DOCK) or by interactively moving the compound into the active-site;

(c) characterize the space between the compound and the binding site atoms;

(d) search libraries for molecular fragments which (i) can fit into the empty space between the compound and the active-site, and (ii) can be linked to the compound; and (e) link the fragments found above to the compound and evaluate the new modified compound.

Part (c) refers to characterizing the geometry and the complementary interactions formed between the atoms of the RPTK and the compound, ligand, or ligand analog. A favorable geometric fit is attained when a significant surface area is shared between the compound and RPTK atoms without forming unfavorable steric interactions.

One skilled in the art would note that the method can be performed by skipping parts (d) and (e) and screening a data base of many compounds.

Structure-based design and identification of modulators of RPTK function can be used in conjunction with assay screening. As large computer data base of compounds (around 10,000 compounds) can be searched in a matter of hours, the computer based method can narrow the compounds tested as potential modulators of RPTK function in cellular assays.

The above descriptions of structure-based modulator design are not all encompassing and other methods are reported in the literature:

(1) CAVEAT: Bartlett et al., 1989, in "Chemical and Biological Problems in Molecular Recognition", Roberts, S. M.; Ley, S. V.; Campbell, M. M. eds.; Royal Society of Chemistry: Cambridge, pp182–196.

(2) FLOG: Miller et al., 1994, *J. Comp. Aided Molec. Design* 8:153.

(3) PRO Modulator: Clark et al., 1995, *J. Comp. Aided Molec. Design* 9:13.

(4) MCSS: Miranker and Karplus, 1991, *Proteins: Structure, Function, and Genetics* 11:29.

(5) AUTODOCK: Goodsell and Olson, 1990, *Proteins: Structure, Function, and Genetics* 8:195.

(6) GRID: Goodford, 1985, *J. Med. Chem.* 28:849.

Design by Modifying Compounds in Complex with RPTKs

Another way of identifying compounds, ligands, or ligand analogs as potential modulators is to modify an existing modulator in the polypeptide active-site. For example, the computer representation of modulators can be modified within the computer representation of a RPTK ligand binding site. Detailed instructions for this technique can be found in the Molecular Simulations User Manual, 1995 in LUDI. The computer representation of the modulator is modified by changing, deleting, or adding one or chemical groups.

Upon each modification to the compound, ligand, or ligand analog, the atoms of the modified compound, ligand, or ligand analog and the RPTK can be shifted in conformation, and the distance between the compound, ligand, or ligand analog and the RPTK atoms may be scored along with any complimentary interactions formed between the two molecules. Scoring can be complete when a favorable geometric fit and favorable complementary interactions are attained. Compounds that have favorable scores are potential modulators of RPTK function.

Design by Modifying the Structure of Compounds that Bind Receptor PTKs

A third method of structure-based modulator design is to screen compounds designed by a modulator building or modulator searching computer program. Examples of these types of programs can be found in the Molecular Simulations Package, Catalyst. Descriptions for using this program are documented in the Molecular Simulations User Guide (1995). Other computer programs used in this application are ISIS/HOST, ISIS/BASE, ISIS/DRAW) from Molecular Designs Limited and UNITY from Tripos Associates.

These programs can be operated on the structure of a compound, ligand, or ligand analog that has been removed from the active-site of the three dimensional structure of a compound, ligand, or ligand analog-completed RPTK complex. Operating the program on such a compound, ligand, or ligand analog is preferable since it is in a biologically active conformation.

A modulator construction computer program is a computer program that may be used to replace computer representations of chemical groups in a compound, ligand, or ligand analog complexed with a RPTK with groups from a computer data base. A modulator searching computer program is a computer program that may be used to search computer representations of compounds from a computer data base that have similar three dimensional structures and similar chemical groups as compounds bound to a receptor PTK.

A typical program can operate by using the following general steps:

(a) map the compounds, ligands, or ligand analogs by chemical features such as by hydrogen bond donors or acceptors, hydrophobic/lipophilic sites, positively ionizable sites, or negatively ionizable sites;

(b) add geometric constraints to the mapped features; and (c) search data bases with the model generated in (b).

Those skilled in the art recognize that important chemical features include, but are not limited to, a hydrogen bond donor, a hydrogen bond acceptor, and/or two hydrophobic points of contact. Those skilled in the art also recognize that not all of the possible chemical features of the compound

IX. Organic Synthetic Techniques

The versatility of computer-based modulator design and identification lies in the diversity of structures screened by the computer programs. The computer programs can search data bases that contain 200,000 molecules and can modify modulators already complexed with a polypeptide, using a wide variety of chemical functional groups. A consequence of this chemical diversity is that a potential modulator of RPTK function may take a chemical form that is not predictable. A wide array of organic synthetic techniques exist in the art to meet the challenge of constructing these potential modulators of RPTK function. Many of these organic synthetic methods are described in detail in standard reference sources utilized by those skilled in the art. One example of such a reference is March, 1994, *Advanced Organic Chemistry, Reactions, Mechanisms, and Structure*, New York, McGraw Hill. Thus, the techniques required to synthesize a potential modulator of RPTK function identified by computer-based methods are readily available to those skilled in the art of organic chemical synthesis.

X. Cellular Assays Measuring the Effect of a Receptor PTK Modulator in Signal Transduction Pathways Cellular assays can be used to test the activity of a potential modulator of RPTK function as well as diagnose a disease associated with inappropriate RPTK activity. A potential modulator of RPTK function can be tested for activity in vitro by assays that measure the effect of a potential modulator on the autophosphorylation of a particular RPTK over-expressed in a cell line. Thus, a modulator that acts as a potent inhibitor of ligand binding to the extracellular domain corresponding to a RPTK would decrease the amount of autophosphorylation catalyzed by that RPTK. Potential modulators could also be tested for activity in cell growth assays in vitro as well as in animal model assays in vivo.

In vivo assays are also useful for testing the bioactivity of a potential modulator designed by the methods of the invention.

Materials, methods, and experimental data for these assays are fully described in U.S. Pat. No. 5,792,783, and WO 96/40116 published on Dec. 19, 1996, entitled "Indolinone Compounds for the Treatment of Disease," each of which is incorporated herein by reference in its entirety, including all drawings, figures, and tables.

XI. Administration of Modulators of Receptor PTK Function as Therapeutics for Disease Methods of administering compounds to organisms as therapeutics for disease are fully described in U.S. Pat. No. 5,792,783, and WO 96/40116 published on Dec. 19, 1996, entitled "Indolinone Compounds for the Treatment of Disease," each of which is incorporated herein by reference in its entirety, including all drawings, figures, and tables.

Figure 33:
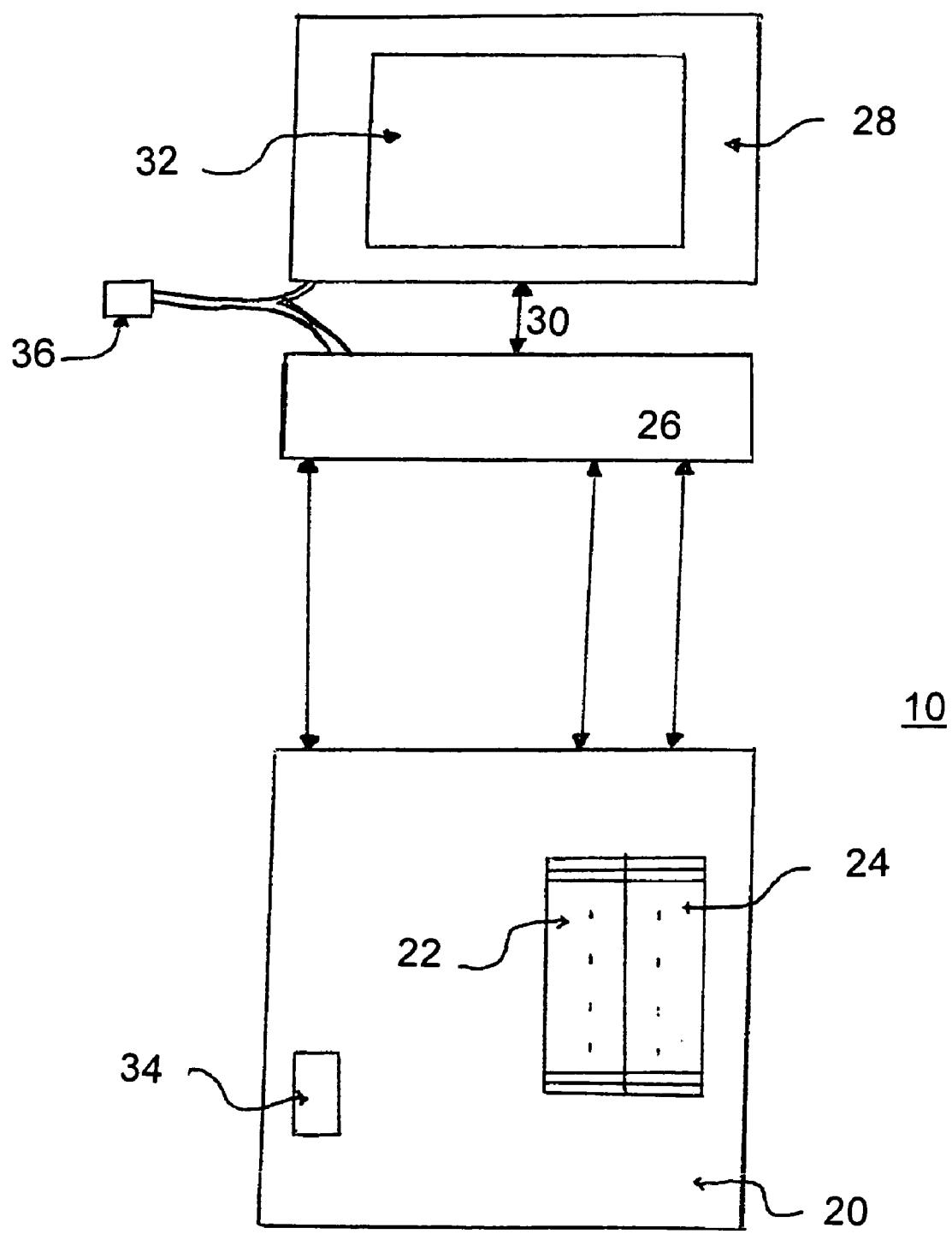
FIG. 33 shows a schematic illustration of a computer based system which can be used for displaying, studying, comparing, manipulating, interpreting and/or extrapolating data from the crystallographic analysis of molecular structures, such as the molecular structures of RPTKs, their ligands and related complexes.

XII. Computer-Based Systems for Determining, Designing, Modeling and/or Modifying Molecular Structures An illustrative computer based system 10 is depicted in FIG. 33 for displaying, studying, comparing, manipulating, interpreting and/or extrapolating data from the crystallographic analysis of molecular structures which include molecules, portion(s) of molecules and/or molecular interactions, such as the molecular structures of RPTKs, their ligands and related complexes depicted in FIGS. 1, 2, 5, 19, 26 and 27. Exemplary molecules are proteins and/or complexes of proteins with ligands. Exemplary molecular portions are catalytic domains of proteins, ligand/receptor binding sites of proteins, signaling regions of proteins and transport regions of proteins. Exemplary molecular interactions include binding between an enzyme and its substrate, factor/co-factor relationships, antibody/antigen binding, and protein/receptor recognition and binding, such as that occurring in signal transduction. One or more of the above types of studies are useful for elucidating and understanding natural biochemical processes and to design and screen mimetics, agonists, inhibitors, and antagonists. Thus, this aspect of the invention, among other things, permits the skilled person to understand and practice molecular modeling processes and provides the skilled person with the necessary hardware and software to create and display images that represent the multi-dimensional structure of a molecule, molecular portion or molecular interaction, as desired. Thus, these undertakings are greatly facilitated by employing computer technology.

The system 10 includes data storage entity(ies) 20, such as a memory (e.g., as archival memory and/or video memory and computer-readable medias), that retrievably stores information representing molecule, molecule portions and/or molecular interactions. The memory typically has a first-type storage region or capability 22, having recorded thereon or contained therein structural data, like a set of spatial (atomic) coordinates, specifying a location in a three dimensional space, as disclosed herein or obtained in accordance with the teachings contained herein. The memory also can have a second-type storage region or capability 24, which contains information. This information typically represents a property, characteristic or attribute of one of a plurality of amino acids, or other chemical moiety, for example. A second-type storage region or capability can be associated with the first-type storage regions in the storage entity 20 to represent a geometric and/or spatial arrangement of at least one characteristic, property or attribute of a molecule, molecule portion or molecular interaction, preferably one that represents three dimensional space. The memory can take the form of any type recognizable by the skilled person such as RAM and ROM, and other computer-readable mediums like magnetic media, optical media, magnetic-optical media, floppy disks, hard disks, mini-disks, servers, web-based systems, CD, DVD, tape, etc. Memory 22 (a type of storage region or capability) can include or contain, for example, the coordinate data shown in Tables 1, 2, 3, 4 or 6, or other coordinates obtained in accordance with the present teachings, and memory 24 (a type of storage region or capability) can include or contain associated charge or electron density data, for example. Quite commonly, the system includes a plurality of the first-type and second-type storage regions. The storage entities 20, namely the first-type storage regions or capabilities 22, said second-type storage regions or capabilities 24, and the storage devices or capabilities 34 can be regions of, for example, a shared semiconductor memory, cache, RAM, ROM, regions of a shared optical disk, regions of a shared magnetic memory, and/or be server based to be accessible by intranet and the internet, including the world wide web. Thus, the systems of the present invention include unitary systems, network-based systems, satellite communications, and internet-based systems, which can be interactively connected regardless of geography.

The system 10 also includes a processor and/or is interactively associated with a processor, interactively coupled to the data storage entity(ies) to access the first-type storage regions 22 and optionally the second-type storage regions 24, to generate image signals for depicting a visual three dimensional image of at least one characteristic of the molecule, molecule portion or molecular interaction in the three dimensional space based on data from the storage entity 20. The processor can be a general or special purpose processor with a CPU, register, memory and the like. Software, and logic architecture and circuitry, can be employed as desired. According to one embodiment, processor 26 and storage entity 20, among other things, can be in the form of a UNIX or VAX computer, such those available from Silicon Graphics, Sun Microsystems, and IBM. However, the invention is not limited to use of these types of hardware and software systems.

A display 28 is commonly interactively coupled to the processor 26 via lines or a wireless connection 30 to receive the image signals in order to depict a visual three dimensional image of at least one characteristic of a molecule, molecule portion or molecular interaction in the three dimensional space based on the data. Suitable displays for use in the system include a computer screen 32 (e.g., CRT, LCD, active and passive matrix, etc.), printer, plotter or film.

In one embodiment of the invention, the image data includes data for depicting a visual three dimensional image of a structure of molecule, molecule portion or molecular interaction in three dimensional space, such as shown in FIGS. 1, 2, 5, 19, 26 and 27. In another embodiment, the image data includes data for depicting a visual three dimensional image of a solid model representation of molecule, molecule portion or molecular interaction in three dimensional space. In still another embodiment, the image data includes data for depicting a visual three dimensional image of electrostatic surface potential of molecule, molecule portion or molecular interaction in three dimensional space. In yet another embodiment, the image data includes data for depicting a visual three dimensional stereo image of molecule, molecule portion or molecular interaction in three dimensional space.

The system 10 of the present invention may further comprise a storage device, structure, region or capability 34 that stores data representing a geometric and/or spatial arrangement of a characteristic of a composition in addition to the molecule, molecule portion or molecular interaction, such as shown in FIGS. 9, 10, 22 and 24. Storage devices or capabilities 34 can include or contain, for example, the three-dimensional X-ray coordinate data for other chemical entities, including other proteins for comparison purposes. The storage devices and capabilities 34 can take the form of any type recognizable by the skilled person such as RAM and ROM, and other computer-readable mediums like magnetic media, optical media, magnetic-optical media, floppy disks, hard disks, mini-disks, servers, CD, DVD, tape, etc. The processor 26 can be interactively coupled to the storage device or capability 34 and the display 28, and generates additional image data for depicting the geometric arrangement of the characteristic of the composition relative to said visual three dimensional image of said at least one characteristic of the molecule, molecule portion or molecular interaction on the screen 32 based on instructions. In the FIG. 33 embodiment, the storage device or capability 34 is shown as part of the storage entity 20, although other arrangements are available to the skilled person.

The computer system includes or employs instructions, which can be software or hardware based. The instructions, such as those in logic circuits and software program(s), permit the computer system to, among other things, input, handle, analyze and output data. Exemplary programs are identified herein, although the skilled person is not limited to such programs in the practice of the invention.

Typically, the system 10 also includes an operator interface 36, such as a mouse, tracker ball, touch pad, projector (including multi-dimensional projector systems), touch screen, joy stick, pointer, keyboard, modem, card and/or voice recognition system, or docking system for receiving instructions from a operator, which is interactively connected with the display 28, processor 26 and storage entity (ies) 20. Other aspects of computers and computer components are well-known, and are readily obtained.

The computer systems according to the invention, including storage entity 20 (including 22, 24, 34, and others as well) can be programmed and contain data to undertake the analyses discussed in Sections VI–IX above, for example, including the use of x-ray crystallographic data in conjunction with other analytical techniques, such as NMR.

The invention also includes computer-readable media containing various data structures and the information disclosed herein. For example, magnetic media, optical media, magnetic-optical media, floppy disks, hard disks, mini-disks, servers, CD, DVD, tape, etc. containing the coordinate data set forth in the accompanying tables and figures, when computer analyzed according to set(s) of instructions and rules provided by hardware and/or software, are useful for ascertaining the three-dimensional structures of molecules, molecular portions and molecular interactions.

EXAMPLES

The examples below are non-limiting and are merely representative of various aspects and features of the present invention. The examples provide illustrative methods for obtaining crystalline forms of protein kinase polypeptides, methods for determining three dimensional structures of these protein kinase polypeptides, and methods for identifying modulators of protein kinases using the three dimensional structures of the protein kinases.

Atomic Structural Coordinates

Tables 1–3 provide the atomic structural coordinates for a number of ligand/FGFR complex dimers. Table 5 provides the atomic structural coordinates for a SCF dimer. Table 6 provides the atomic structural coordinates for a the ternary FGF2-FGFR1-heparin complex. The following abbreviations are used in the Tables:

"Atom Type" refers to the element whose coordinates are provided. The first letter in the column defines the element.

"A.A." refers to amino acid.

"X, Y and Z" provide the Cartesian coordinates of the element.

"B" is a thermal factor that measures movement of the atom around its atomic center.

"OCC" refers to occupancy, and represents the percentage of time the atom type occupies the particular coordinate. OCC values range from 0 to 1, with 1 being 100%.

"PRT1" or "PRT2" relate to occupancy, with PRT1 designating the coordinates of the atom when in the first conformation and PRT2 designating the coordinates of the atom when in the second or alternate conformation.

The structural coordinates for the dimers may be modified by mathematical manipulation. Such manipulations include, but are not limited to, crystallographic permutations of the raw structure coordinates, fractionalization of the raw structure coordinates, integer additions or subtractions to sets of the raw structure coordinates, inversion of the raw structure coordinates and any combination of the above.

In addition, the structural coordinates can be slightly modified and still render nearly identical three dimensional structures. Therefore, a measure of a unique set of structural coordinates is the root-mean-square deviation of the resulting structure. Structural coordinates that render three dimensional structures that deviate from one another by a root-mean-square deviation of less than 1.5 Å may be viewed as identical.

Example 1

X-ray Crystallographic Structure Determination of FGFR1 D2-D3/FGF2 Complexes

Polypeptide Synthesis and Isolation

A DNA fragment encoding residues 142–365 of human FGFR1 ("D2-D3") was subcloned into bacterial expression vector pET-23a using NcoI and HindIII restriction sites using techniques well known to the skilled artisan. Bacterial strain BL21 (DE3) was used for expression of D2-D3, and was induced with IPTG for 5 hours. Following induction of expression, the cells were collected by centrifugation, and lysed using a French press in a buffer containing 25 mM potassium phosphate, 150 mM NaCl, 2 mM EDTA, and 10% glycerol.

A pellet containing D2-D3 was collected by centrifugation, and dissolved in 6M guanidium hydrochloride, 100 mM Tris-HCl, pH 8.0. D2-D3 was allowed to refold by dialyzing for 48 hours against a buffer containing 50 mM Tris-HCl, pH 8.0, 150 mM NaCl, 10% glycerol, and 1 mM L-cysteine. The refolded D2-D3 was chromatographed on a heparin sepharose column on which FGF2 had been previously immobilized. The resulting D2-D3/FGF2 complex was eluted from the heparin sepharose column with a buffer containing 25 mM Tris-HCl, pH 7.5, and 1.5 M NaCl.

The D2-D3/FGF2 complex was concentrated by ultrafiltration using a Centricon 10™ (Amicon) centrifugal concentrator, and further purified by size exclusion chromatography on a Superdex™ 200 column (Pharmacia) using a buffer containing 25 mM Tris-HCl, pH 7.5, and 1.5 M NaCl. Prior to crystallization, the D2-D3/FGF2 complex was concentrated to 10 mg/mL in a buffer containing 25 mM Tris-HCl, pH 7.5, and 150 mM NaCl.

Crystal Growth

Crystals of purified D2-D3/FGF2 complex were grown at 20° C. by vapor diffusion in hanging drops by mixing equal volumes of protein solution (10 mg/mL D2-D3/FGF2 complex in 25 mM Tris-HCl, pH 8.5, and 150 mM NaCl) and reservoir buffer (1.6 M $(NH_4)_2SO_4$, 20% v/v glycerol and 100 mM Tris-HCl, pH 8.5), and suspending a 2.0 µl hanging drop of the resulting solution over 0.5 mL reservoir buffer at 20° C.

Data Collection and Structure Determination

Diffraction data were collected from a crystalline specimen, which had been flash frozen in a dry nitrogen stream, at beamline X-4A at the National Synchrotron Light Source, Brookhaven National Laboratory. Synchrotron data were collected on a CCD detector. All data were processed using DENZO and SCALEPACK. Otwinowski, 1993, "Oscillation data reduction program," Proceedings of the CCP4 Study Weekend, Sawyer et al., eds. (Daresbury, United Kingdom: SERC Daresbury Laboratory), 56–62.

The structure of the D2-D3/FGF2 complex was determined by molecular replacement using the program AmoRe (Navaza, 1994, Acta Cryst. A 50: 157–163) using the structures of FGF2 (2FGF, Zhang et al., 1991, Proc. Natl. Acad. Sci. 88: 3446–3450) and telokin (1TLK, Holden et al., 1992, J. Mol. Biol. 227: 840–851) as search models. Homology models were constructed from the telokin structure for the FGFR1 D2 and D3 domains. A molecular replacement solution was determined for both FGF2 molecules and one copy of D2 and D3 in the dimer, and the second copy of D2 and D3 was determined by rigid body rotation and translation of the first copy of D2 and D3 onto the second FGF2 molecule. The placement of the second copy of D2 and D3 was confirmed by rigid body refinement techniques using CNS (Brunnger et al., 1998, Acta Cryst. D 54: 905–921).

Simulated annealing and positional B-factor refinement were performed using CNS, and bulk solvent and anisotropic B-factor corrections were applied. Additionally, tight noncrystallographic symmetry constraints were imposed during refinement of the backbone atoms of FGF2, D2, and D3. RMS deviation for Cα atoms between the two copies of FGF2, D2, or D3 in the dimer was 0.04 Å.

Model building into the electon density maps was performed using the program O (Jones et al., 1991, Acta Cryst. A 47: 110–119). The atomic model of the D2-D3/FGF2 complex includes FGF2 residues 16–144 and FGFR1 residues 149–359, except in one of the FGFR1 receptors in the dimer, where residues 293–307 are disordered. The average B-factor for all atoms is 38.7 Å$^2$ for all atoms, 37.6/38.9 Å$^2$ for FGF2, and 38.3/39.1 Å$^2$ for FGFR1.

Atomic Structural Coordinates

Table 1 provides the atomic structural coordinates of the FGFR1(D2-D3)/FGF2 complex dimer complex dimer. The structure of the FGFR1(D2-D3)/FGF2 complex has been described in Plotnikov et al., Cell 98, 641–650 (1999) and the coordinates for the FGFR1(D2-D3)/FGF2 complex are available on the internet through the Protein Data Bank (assigned Protein Data Bank ID code 1CVS), the disclosures of which are herein incorporated by reference.

Example 2

X-ray Crystallographic Structure Determination of FGFR1 D2-D3/FGF1 Complexes

Polypeptide Synthesis and Isolation

A DNA fragment encoding residues 142–365 of human FGFR1 ("D2-D3") was subcloned into bacterial expression vector pET-23a using NcoI and HindIII restriction sites using techniques well known to the skilled artisan. Bacterial strain BL21(DE3) war used for expression of D2-D3, and was induced with IPTG for 5 hours. Following induction of expression, the cells were collected by centrifugation, and lysed using a French press in a buffer containing 25 mM potassium phosphate, 150 mM NaCl, 2 mM EDTA, and 10% glycerol.

A pellet containing D2-D3 was collected by centrifugation, and dissolved in 6M guanidium hydrochloride, 100 mM Tris-HCl, pH 8.0. D2-D3 was allowed to refold by dialyzing for 48 hours against a buffer containing 50 mM Tris-HCl, pH 8.0, 150 mM NaCl, 10% glycerol, and 1 mM L-cysteine. The refolded D2-D3 was chromatographed on a heparin sepharose column on which FGF1 had been previously immobilized. The resulting D2-D3/FGF1 complex was eluted from the heparin sepharose column with a buffer containing 25 mM Tris-HCl, pH 7.5, and 1.5 M NaCl.

The D2-D3/FGF1 complex was concentrated by ultrafiltration using a CENTRICON 10™ (Amicon) centrifugal concentrator, and further purified by size exclusion chromatography on a SUPERDEX™ 200 column (Pharmacia) using a buffer containing 25 mM Tris-HCl, pH 7.5, and 1.5 M NaCl. Prior to crystallization, the D2-D3/FGF1 complex was concentrated to 1 mg/mL in a buffer containing 25 mM Tris-HCl, pH 7.5, and 10 mM NaCl.

Crystal Growth

Crystals of purified D2-D3/FGF1 complex were grown at 20° C. by vapor diffusion in hanging drops by mixing one volume of protein solution (1 mg/mL in 25 mM Tris-HCl, pH 8.5, and 150 mM NaCl) with four volumes of reservoir buffer (20% PEG 4000, 0.2 M Li2SO$_4$, and 0.1 M Tris-HCl, pH 8.5), and suspending a 2.0 µl hanging drop of the resulting solution over 0.5 mL reservoir buffer at 20° C.

Data Collection and Structure Determination

Diffraction data were collected from a crystalline specimen, which had been flash frozen in mother liquor containing 10% glycerol using a dry nitrogen stream, at beamline X-4A at the National Synchrotron Light Source, Brookhaven National Laboratory. Synchrotron data were collected on a CCD detector. All data were processed using DENZO and SCALEPACK. Otwinowski, 1993, "Oscillation data reduction program," Proceedings of the CCP4 Study Weekend, Sawyer et al., eds. (Daresbury, United Kingdom: SERC Daresbury Laboratory), 56–62.

The structure of the D2-D3/FGF1 complex was determined by molecular replacement using the program AmoRe (Navaza, 1994, *Acta Cryst. A* 50: 157–163) using the structures of FGF1 (2AFG, Blaber et al., 1996, *Biochemistry* 35: 2086–2094) and telokin (1 TLK, Holden et al., 1992, *J. Mol. Biol.* 227: 840–851) as search models. Homology models were constructed from the telokin structure for the FGFR1 D2 and D3 domains. A molecular replacement solution was determined for two copies each of FGF1, D2, and D3 in the dimer.

Simulated annealing and positional B-factor refinement were performed using CNS, and bulk solvent and anisotropic B-factor corrections were applied. Additionall, tight noncrystallographic symmetry constraints were imposed during refinement of the backbone atoms of FGF1, D2, and D3. RMS deviation for Cα atoms between the two copies of FGF1, D2, or D3 in the dimer was 0.01 Å.

Model building into the electon density maps was performed using the program 0 (Jones et al., 1991, *Acta Cryst. A* 47: 110–119). The atomic model of the D2-D3/FGF1 complex includes FGF1 residues 8–138 and FGFR1 residues 147–359 except residues 294–305 and 315–323, which are disordered. The average B-factor for all atoms is 30.4 Å$^2$ for all atoms, 31.2/33.0 Å$^2$ for FGF1, and 29.1/28.7 Å$^2$ for FGFR1.

Atomic Structural Coordinates

Table 2 provides the atomic structural coordinates of the FGFR1(D2-D3)/FGF1 complex dimer. In the first FGFR1 molecule of the dimer the residue number is preceded by a 1, i.e., residue number 464 of the first FGFR1 molecule of the dimer is denoted by "1464". The structure of the FGFR1(D2-D3)/FGF1 complex has been described in Plotnikov et al., *Cell* 101, 413–424 (2000) and the coordinates for the FGFR1(D2-D3)/FGF1 complex are available on the internet through the Protein Data Bank (assigned Protein Data Bank ID code 1EVT), the disclosures of which are herein incorporated by reference.

Example 3

Determination of the FGF2-FGFR2 Structure

Crystallization and Data Collection

DNA fragments encoding residues 147 to 366 of FGFR2 were amplified by polymerase chain reaction (PCR) and subcloned into the bacterial expression vector pET-28a using NcoI and HindIII cloning sites and transfected into the bacterial strain BL21(DE3). Cells were induced with IPTG for 5 hours, centrifuged and the bacterial pellet was lysed in 25 mM K—Na phosphate buffer pH 7.5 containing 150 mM NaCl, 2 mM EDTA and 10% glycerol using a French press. Following centrifugation, the pellet containing primarily FGFR2 was dissolved in 6M guanidium hydrochloride and 10 mM DTT in 100 mM Tris-HCl buffer (pH 8.0). The solubilized FGFR2 protein was refolded by dialysis against 25 mM HEPES buffer pH 7.5 containing 150 mM NaCl, 10% Glycerol, and 1 mM L-Cysteine. The refolded FGFR2 protein was loaded onto heparin sepharose columns on which FGF2 (basic FGF) had previously been immobilized. The FGF2-FGFR2 complex was then eluted from the heparin sepharose column with a buffer containing 25 mM Tris-HCl (pH 7.5) and 1.5M NaCl. The FGF2-FGFR2 complex was concentrated using Centricon 10 (Amicon) filters and further purified by size exclusion chromatography (Pharmacia, Superdex 200) with a buffer containing 25 mM Tris-HCl (pH 7.5) and 1.5M NaCl. The complex migrated at a position consistent with the formation of a 1:1 FGF:FGFR complex.

Crystals were grown by vapor diffusion at 20° C. using the hanging drop method. For crystallization of the FGF2-FGFR2 complex, 2 microliters of protein solution 10 mg/ml, 25 mM Tris-HCl (pH 7.5), 150 mM NaCl) were mixed with 2 microliters of the crystallization buffer containing 10–15% PEG 4000, 10% isopropanol, and 0.1M HEPES—NaOH (pH 7.5). The FGF2-FGFR2 crystals belong to the triclinic space group P1 with unit cell dimensions a=72.20 Å, b=71.68 Å, c=90.92 Å, α=90.53°, β=89.98° and γ89.99°. There are four molecules of FGF2 and four molecules of FGFR2 in the unit cell with a solvent content of ~58%. Diffraction data were collected from flash-frozen (in a dry nitrogen stream using mother liquor containing 10% glycerol as cryo-protectant) crystals on a CCD detector (FGF2-FGFR2) at beamline X4A at the National Synchrotron Light Source, Brookhaven National Laboratory. All data were processed using DENZO and SCALEPACK (Otwinowski et al., Methods Enzymol. 276, 307–326 (1997)).

Structure Determination and Refinement of the FGF2-FGFR2 structure

The structure of the FGF2-FGFR2 complex was determined by molecular replacement using the program AmoRe (Navaza, Acta Cryst. A 50, 157–163 (1994)) and the structure of FGF2-FGFR1 (1CVS; Plotnikov et al., *Cell* 98, 641–650 (1999)) as the search model. A molecular replacement solution was found for four copies of FGF2-FGFR2 complexes. Model building and refinement were performed with the programs O (Jones et al., *Acta Crystallogr. A* 47, 110–119 (1991)) and CNS (Brünger et al., Acta Crystallogr. D 54, 905–921 (1998)), respectively. Tight non-crystallographic symmetry restraints were imposed throughout the refinement for the backbone atoms of FGF2, D2 and D3. The structures of the FGF2-FGFR2 complex and the related FGF1-FGFR1 complex are reported together with the corresponding X-ray coordinates in Plotnikov et al., *Cell* 101: 413–24 (2000), the disclosure of which is herein incorporated by reference.

The atomic model for FGF2-FGFR2 consists of four FGF2 molecules, four FGFR2 molecules, four sulfate ions, and 263 water molecules. The structure of FGF2-FGFR2 was refined at 2.2 Å with an R value of 24.8% (free R value of 27.3%). Data collection and refinement statistics are given in Table 7. The atomic model includes FGF2 residues 16–145 and FGFR2 residues 148–365, 4 sulfate ions, and 263 water molecules. In all four FGFR2 molecules residues 295–306 (βC-βC' loop in D3) are disordered. The average B-factor is 40.5 Å$^2$ for FGF2 molecules, 37.7 Å$^2$ for FGFR2 molecules, 73 Å$^2$ for sulfate ions, and 32.6 Å$^2$ for water molecules.

Atomic Structural Coordinates

Table 3 provides the atomic structural coordinates of the FGF2/FGFR2 complex dimer. The structure of the FGFR2/FGF2 complex has been described in Plotnikov et al., *Cell* 101, 413–424 (2000) and the coordinates for the FGFR2/FGF2 complex are available on the internet through the Protein Data Bank (assigned Protein Data Bank ID code 1 EV2), the disclosures of which are herein incorporated by reference. Table 3 contains sequence data that meets the requirements for inclusion into a Sequence Listing. Sequences SEQRES1A (p. 292) through SEQRES17H (p. 294) have been assigned SEQ ID NOS 50–157, respectively, in order of appearance, with the exceptions of nonqualifying sequences SEQRES11A, SEQRES11B, SEQRES11C, and SEQRES11D.

TABLE 7

Summary of Crystallographic Analysis

Data Collection Statistics

| Structure | Resolution (Å) | Reflections (total/unique) | Completeness (%) | $R_{sym}$[a] (%) | Signal (<I/δI>) |
|---|---|---|---|---|---|
| FGF1-FGFR1 | 25.0–2.8 | 49288/22330 | 97.9(90.5)[b] | 8.3(22.6)[b] | 8.6 |
| FGF2-FGFR2 | 25.0–2.2 | 206913/93440 | 96.3(87.8)[b] | 4.2(24.1)[b] | 16.3 |

Refinement Statistics[c]

| | | | | Root-mean-square Deviations | | |
|---|---|---|---|---|---|---|
| Structure | Resolution (Å) | Reflections | $R_{cryst}/R_{free}$[d] (%) | Bonds (Å) | Angles (°) | B-factors[e] (Å$^2$) |
| FGF1-FGFR1 | 25.0–2.8 | 21539 | 24.9/30.0 | 0.009 | 1.5 | 2.3 |
| FGF2-FGFR2 | 25.0–2.2 | 84816 | 24.8/27.3 | 0.007 | 1.3 | 1.0 |

[a] $R_{sym} = 100 \times \Sigma_{hkl}\Sigma_i |I_i(hkl) - <I(hkl)>|/\Sigma_{hkl}\Sigma_i I_i(hkl)$.
[b] Value in parentheses is for the highest resolution shell: 2.90–2.80 Å (FGF1-FGFR1), 2.28–2.20 Å (FGF2-FGFR2).
[c] Atomic model: 4963 protein atoms and 4 SO$_4$ ions (FGF1-FGFR1) and 9818 protein atoms, 4 SO$_4$ ions, and 263 water molecules (FGF2-FGFR2).
[d] $R_{cryst/free} = 100 \times \Sigma_{hkl}||F_o(hkl)| - |F_c(hkl)||/\Sigma_{hkl}|F_o(hkl)|$, where $F_o$ (>0δ) and $F_c$ are the observed and calculated structure factors, respectively. 5% of the reflections were used for calculation of $R_{free}$.
[e] For bonded protein atoms.

Example 4

SCF Production and Structure Determination

Protein Expression, Refolding and Purification

Residue 1–141 of human stem cell factor ("SCF") were expressed in *E. coli* as inclusion bodies as described previously (Langley et al., *Arch. Biochem. Biophys.* 295, 21–28 (1992)). Inclusion bodies from 1 liter of bacterial culture were dissolved in 25 to 30 ml of 6M guanidine hydrochloride solution. After the solution became clear, DTT was added to a final concentration of 40 mM and incubated at 37° C. for 30 minutes. The resulting solution was diluted into 4 liters of buffered solution (10 mM Tris, pH 8.5) and allowed to stand overnight. Refolded protein was purified by ion-exchange chromatography. Protein purity, electrophoretic mobility, and biological activity were compared to SCF that had been prepared with an established procedure (Langley et al., *Arch. Biochem. Biophys.* 295, 21–28 (1992)) and to a commercially available sample of SCF. Disulfide linked SCF dimers were not detected in this preparation as revealed by non-reducing gel electrophoresis (Langley et al., *Arch. Biochem. Biophys.* 295, 21–28 (1992)).

Crystallization and Data Collection

Crystals of SCF were grown by vapor diffusion at 20° C. using the hanging drop method. Two crystal forms are produced. Orthorhombic crystals with unit cell dimensions a =72.47 Å, b=83.45 Å and c=89.15 Å were grown by mixing 2 microliters of protein sample (15~20 mg/ml) with 2 microliters of reservoir consisting of 25~30% PEG 400, 0.25 M CaCl$_2$, and 0.1 M HEPES (pH 7.0). The addition of 1 mM SmCl$_3$ to the protein solution produced the monoclinic crystals that were used in the structure determination (see Table 4). Monoclinic crystals appeared within hours of set up.

Crystals for data collections were flash-frozen in liquid propane directly from the crystallization drops. Initial characterization of the SCF crystals was done at synchrotron beamlines X26C and X4A of the National Synchrotron Light Source, Brookhaven National Laboratory and the final data collection was done at Argonne National Laboratory Structural Biology Center beamline 19-ID at the Advanced Photon Source. All data were processed using DENZO and the intensities were reduced and scaled using SCALEPACK (Otwinowski et al., Methods Enzymol. 276,307–326 (1997)).

Structure Determination

A molecular replacement attempt with the data collected from the orthorhombic crystals using a model built from the alpha C atom positions of the human colony stimulating factor was not successful. Data used for the structure determination were collected from the monoclinic crystals at wavelengths 1.01 Å and 1.5 Å that are not at the absorption edge of Sm. The anomalous signal was clear from Patterson difference maps. The heavy metal position refinement and phasing was done with PHAESE (Furey et al., Methods Enzymol. 277, 590–620 (1997)). A total of three Sm sites were used for phasing while four Sm atoms were placed in the final model. Only short pieces of helices were visible from the initial solvent flattened electron density map and they were built into the density with program 0 (Jones et al., Acta Crystallogr. A 47, 110–119 (1991)). Repeated cycles of model building and solvent flattening combined with partial structures were performed until most of all four molecules in the asymmetric unit were built. Subsequent refinements were carried out against the lower energy (wavelength of 1.01 Å) diffraction data with Crystallography and NMR System (CNS) (Brunger et al., Acta. Crystallogr. D 54, 905–921 (1998)). Refinement progress was monitored with the $R_{free}$ value using a 10% randomly selected test data set, and residue positions adjusted against 2Fo-Fc electron density maps.

The structure was determined by using anomalous scattering differences of samarium ions in the crystal at two wavelengths and refined to 2.3 Å (Table 4). There are four molecules in each asymmetric unit and the initial experimental electron density clearly showed the four-helix bundle and two beta strands in the molecules. The connecting loops, as well as the N-terminal and C-terminal regions, were built from 2Fo-Fc maps. Table 4 gives the statistics of the final model, which contains 120 solvent molecules, four samarium ions, two calcium ions and one Tris molecule. The structure of the human stem cell factor homodimer has been described in Zhang et al., Proc. Nat. Acad. Sci. 97(14), 7732–7737 (2000) and the coordinates for the human SCF dimer are available on the internet through the Protein Data Bank (Protein Data Bank ID code IEXZ), the disclosures of which are herein incorporated by reference.

General Features of the Structure

Although there are four SCF protomers in the crystallographic asymmetric unit, the biological dimer is unmistakably recognizable. The four protomers are superimposable except for the N-terminal and C-terminal loop regions. These loops are flexible and adopt multiple conformations in the four molecules in the asymmetric unit. The protomers in the biological dimer are packed head-to-head in a manner of almost perfect C2 symmetry (see FIG. 19). The dimer bends approximately 30° toward the side of the beta strands, resulting in an elongated shape with approximate dimensions of 87 Å×32 Å×25 Å.

SCF is a non-covalent homodimer composed of two slightly wedged protomers. The overall topology of a SCF protomer displays an antiparallel four-helix bundle fold (see FIG. 19), in a manner similar to other short-chain helix cytokines (Roswarski et al., Structure 2, 159–173 (1994)). The helices run up-up-down-down, with two crossing beta strands wrapped on one side. The structure of the dimer interface shows that dimerization is mediated by extensive polar and non-polar interactions between the two protomers with a large buried surface area The structure includes a hydrophobic crevice and a charged region at the tail of each protomer that functions as a potential receptor binding site. The X-ray structure of SCF shows that there are extensive interactions between the two SCF protomers, with approximately 1700 Å$^2$ surface area buried upon dimerization (calculated with a probe of radius 1.4 Å). This buried surface area accounts for about 20% of the total surface of each individual protomer, and is twice that reported for the 850 Å$^2$ buried surface area of the disulfide linked M-CSF dimer.

The side chains of the hydrophobic residues of the four helices pack the core of each monomer. Cys4 and Cys89 as well as Cys43 and Cys138 form two intramolecular disulfide pairs. Both disulfide bonds are located at one end (tail) of each protomer away from the dimer interface. The Cys4–Cys89 disulfide bond is more exposed than Cys43–Cys138, a disulfide bond wrapped by the side chains of Val39, Leu98, Pro40 and His42. This probably explains why the Cys4–Cys89 bond is more susceptible to chemical reduction than the Cys43–Cys138 disulfide bond (Lu et al., J. Biol. Chem. 271, 11309–1131 (1996)).

Figure 21:
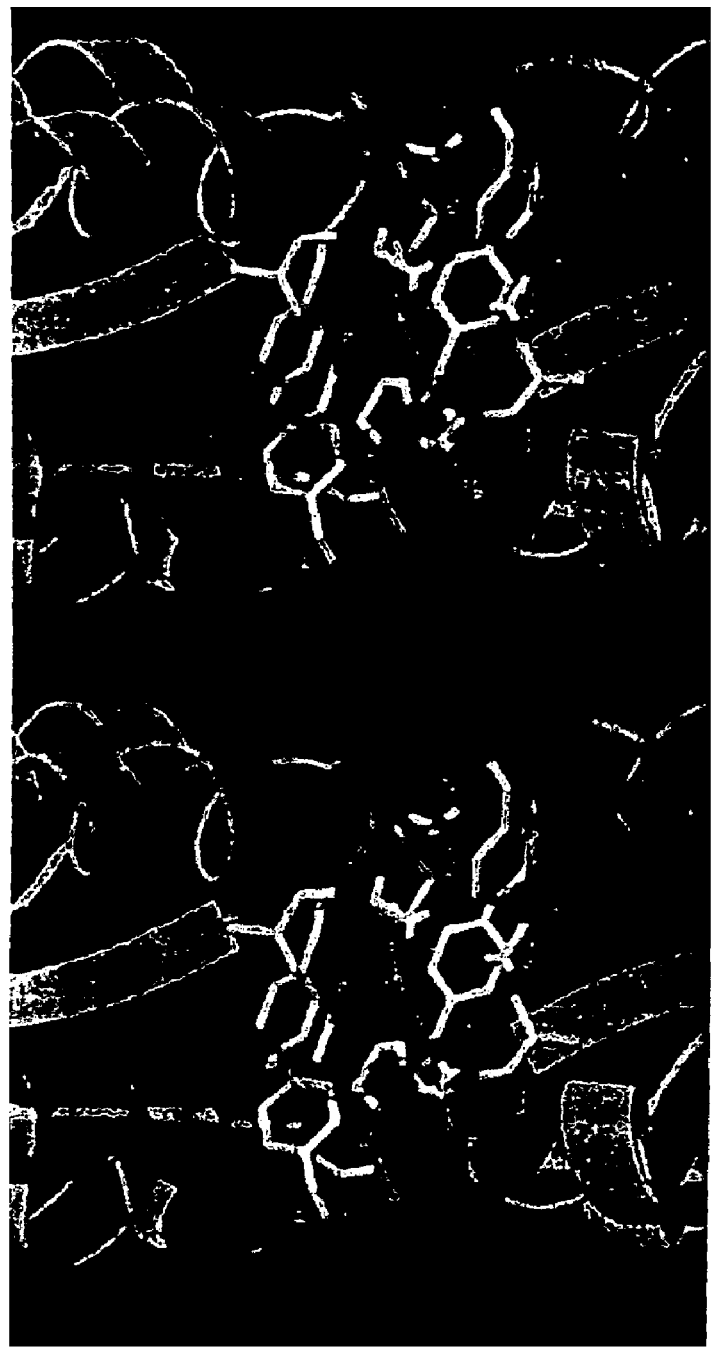
FIG. 21 shows a stereo view of the dimeric interface of SCF constructed by Molscript and Raster3D (Kraulis, J. Appl. Crystallogr. 24, 946–950 (1991); Merrit et al., Methods Enzymol. 277, 505–524(1991)). For clarity, only sidechains of residues at the core of the interface are shown. The coding of the secondary structures is the same as used in FIG. 19, the strands are rendered as arrows, the helices as ribbons, and the loop regions as tubes.
Figure 22:
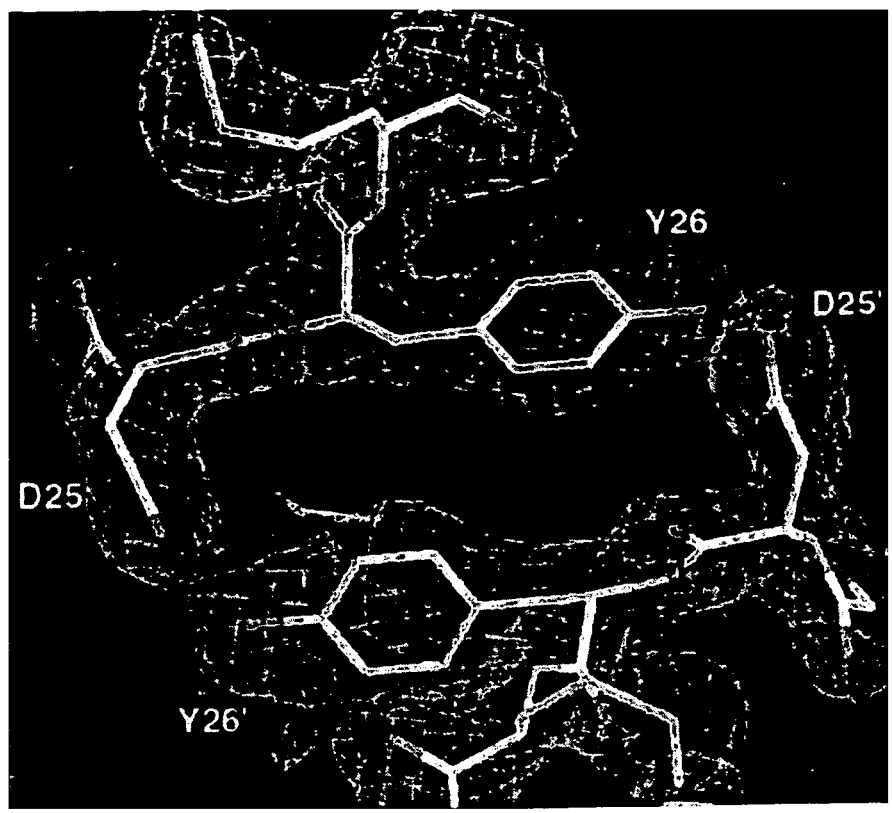
FIG. 22 shows 2Fo-Fc electron density created by O (Jones et al., *Acta Crystallogr. A* 47, 110–119 (1991)), contoured at 1.2, for the hydrogen bond circle of Tyr26 and Asp25' at the dimeric interface.

The SCF dimer interface is composed of loops between alphaA and beta1, alphaB and alphaC, and can also be divided into three layers (see FIG. 21). The bottom layer at the side of the beta strands is composed of hydrophobic interactions. Side chains from Tyr26, Pro23, Phe63 and Leu22 from one protomer pack against corresponding side chains from the other protomer, with Tyr26-Asp25' and Tyr26'-Asp25 forming a hydrogen bond circle as the carpet (see FIG. 2B). These intermolecular hydrogen bond pair replace the intermolecular disulfide bond between the two M-CSF protomers (Bazan, Cell 65, 9–10 (1991); Broudy, Blood 90, 1345–1364 (1997)). Sequence alignment shows that this Tyr-Asp pair is preserved in flt3 ligand, the third member of this family of cytokines that also forms dimers by non-covalent interactions (Hannum et al., Nature 368, 643–648 (1994)). At the core of the interface, the side chains of four asparagine residues (Asn72 and Asn21 from both protomers) form hydrogen bonds among themselves as well as via a water molecule (see FIG. 21). This well coordinated water molecule forms hydrogen bonds with an average bond length of 2.7 Å with the two carbonyl oxygen atoms of the two symmetry related Asn21 residues. The top layer involves interactions between loop alphaB-alphaC of one protomer against that of the other protomer. In addition to a dozen hydrogen bonds formed between the two protomers, there are four possible salt bridges between Lys17-Glu68', Lys24-Asp61', and their symmetry related counterparts.

Example 5

Structure Determination Ternary
FGF2-FGFR1-Heparin complex

The expression, purification and crystallization of FGF2-FGFR1 complexes were carried out as described previously (Plotnikov et al., Cell 98, 641–650 (1999)). Crystals of the native FGF2-FGFR1 complex were incubated in 10 μl of stabilizing solution (40% PEG 8000, 0.25M ammonium sulfate, 0.1M Tris-HCl (pH 8.5)) containing 1 mM decasaccharide for one week at 20° C. Data were collected on a flash-frozen crystal (in a dry nitrogen stream using mother liquor containing 10% glycerol as cryo-protectant) on a CCD detector at beamline X4A at the National Synchrotron Light Source, Brookhaven National Laboratory. Data were processed using DENZO and SCALEPACK (Otwinowski, "Oscillation data reduction program," in *Proceedings of the CCP4 Study Weekend*, Sawyer et al., (eds). (SERC Daresbury Laboratory, Daresbury, United Kingdom) (1993)). Difference Fourier electron density maps were computated using the FGF2-FGFR1 structure (Plotnikov et al., 1999). Initial model for the oligosaccharide was taken from the crystal structure of FGF2 in complex with hexasaccharide (1BFC) (Faham et al., Science 271, 1116–1120 (1996)). The parameters for the oligosaccharide were generated using the HIC-Up server (Kleywegt et al., Acta Crystallogr. D54, 1119–1131 (1998)). Simulated annealing and positional/B-factor refinement were performed using CNS (Bruenger et al., Acta. Crystallogr. D 54, 905–921 (1998)). Model building into $2F_o$-$F_c$ and $F_o$-$F_c$ electron density maps was performed with the program O (Jones et al., *Acta Crystallogr. A* 47, 110–119 (1991)). The average B-factor is 36.9 Å$^2$ for all atoms, 35.0 Å$^2$ for FGF2, 35.3 Å$^2$ for FGFR1, and 72.4 Å$^2$ for decasaccharide molecules.

Structure Determination

Figure 28:
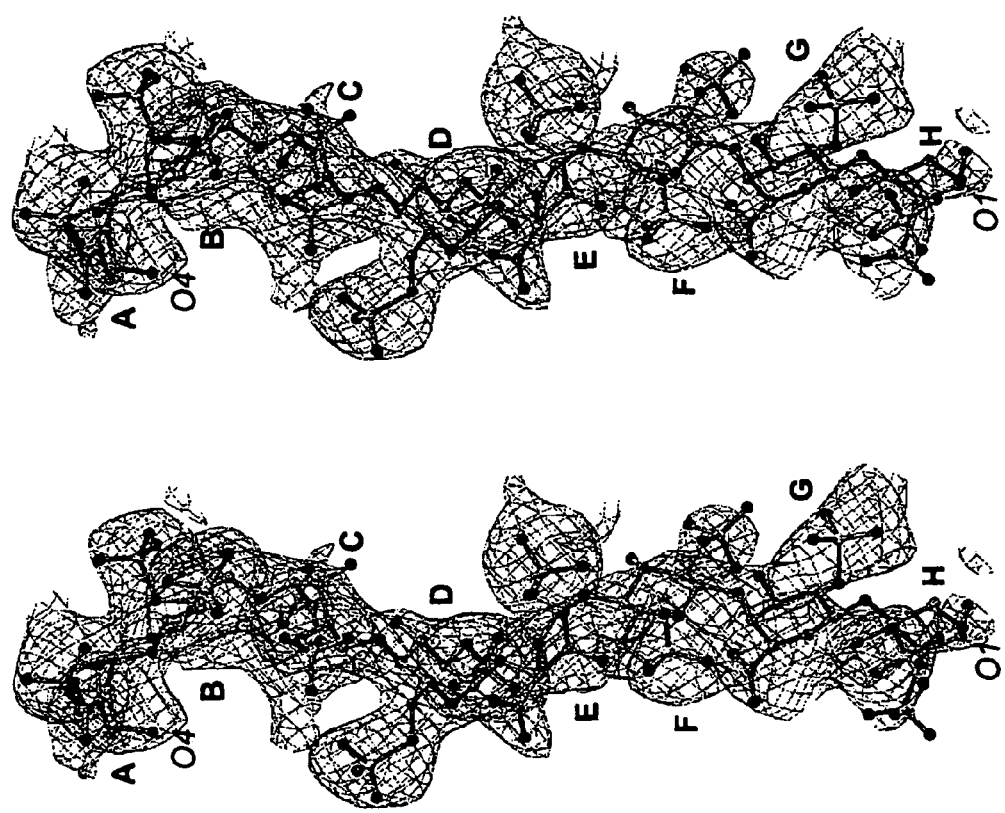
FIG. 28 depicts a stereoview of an FoFc electron density map of an FGF2-FGFR1 complex shown in FIG. 27 computed after simulated annealing with decasaccharide omitted from the atomic model. The map is computed at 3.0 Å resolution and contoured at 1.8 σ. Sugar rings are labeled A through H starting at the non-reducing end of the decasaccharide. Atom coloring is as follows: oxygens in red, sulfurs in yellow, nitrogens in blue, and carbons in gray. This figure was constructed using Bobscript (Esnouf, J. Mol. Graph. Model 15, 132–134 (1997).

Since a heparin binding canyon is present in the FGF2-FGFR1 crystals, incubation of these crystals with decasaccharide facilitated obtaining a ternary FGF-FGFR-heparin complex. The crystal structure of the ternary FGF2-FGFR1-heparin complex was solved using the phases obtained from the FGF2-FGFR1 structure. Data collection and refinement statistics are given in Table 5. It was anticipated to find a single decasaccharide molecule (heparin) traversing the canyon and bridging the ligands. However, the difference Fourier electron density map clearly shows two decasaccharide molecules in the canyon (see FIGS. 27 and 28). Only the first 6 sugar rings (A to F) are observed to interact with protein. Consequently, the electron density is well defined for these rings. In addition, due to favorable lattice contacts, two additional sugars (rings G and H) could be modeled for one of the decasaccharides.

Atomic Structural Coordinates

Table 6 provides the atomic structural coordinates of the the ternary FGF2-FGFR1-heparin complex.

Heparin Structure

The heparin can be approximated as a helix generated by repeating disaccharide units of D-glucosamine (GlcN) and L-iduronic acid (IdoA) joined by α-1–4 linkages. Each disaccharide unit is sulfated at three positions; one at the 2-hydroxyl group of IdoA and two at the 2-amino and 6-hydroxyl groups of GlcN. Sulfate and carboxylate groups form the negatively-charged edges of the heparin helix and appear on a given side of the helix every 17–19 Å on average. These helical parameters are in agreement with the X-ray fiber diffraction values of 8.7 Å and 180° for a heparin polymer (Nieduszynski et al., Am. Chem. Soc. Symp. Ser. 48, 73 (1977)). Heparin polysaccharides are polar entities with a non-reducing end (O4) and a reducing end (O1). In the crystal structure, the decasaccharides bind with their non-reducing ends in the center of canyon and run out onto the high-affinity heparin binding sites of the ligands. Consequently, the symmetry of the dimeric assembly is maintained. Traversing of the canyon by one polar heparin molecule disrupts the two-fold symmetry of the system.

Several intramolecular hydrogen bonds stabilize the helical conformation of the decasaccharide (data not shown). The GlcN rings are all found in a chair conformation. The IdoA rings are in either a chair or a skewed boat conformation as previously observed in the solution structure of a dodecasaccharide (Mulloy et al., Biochem. J. 293, 849–858 (1993)), suggesting that IdoA can adopt multiple conformations depending on the contacts it makes with FGF or FGFR. It is likely that the conformational flexibility of IdoA plays a role in specific recognition of various FGFs or FGFRs.

Heparin-FGF and Heparin-FGFR Interactions

Figure 29:
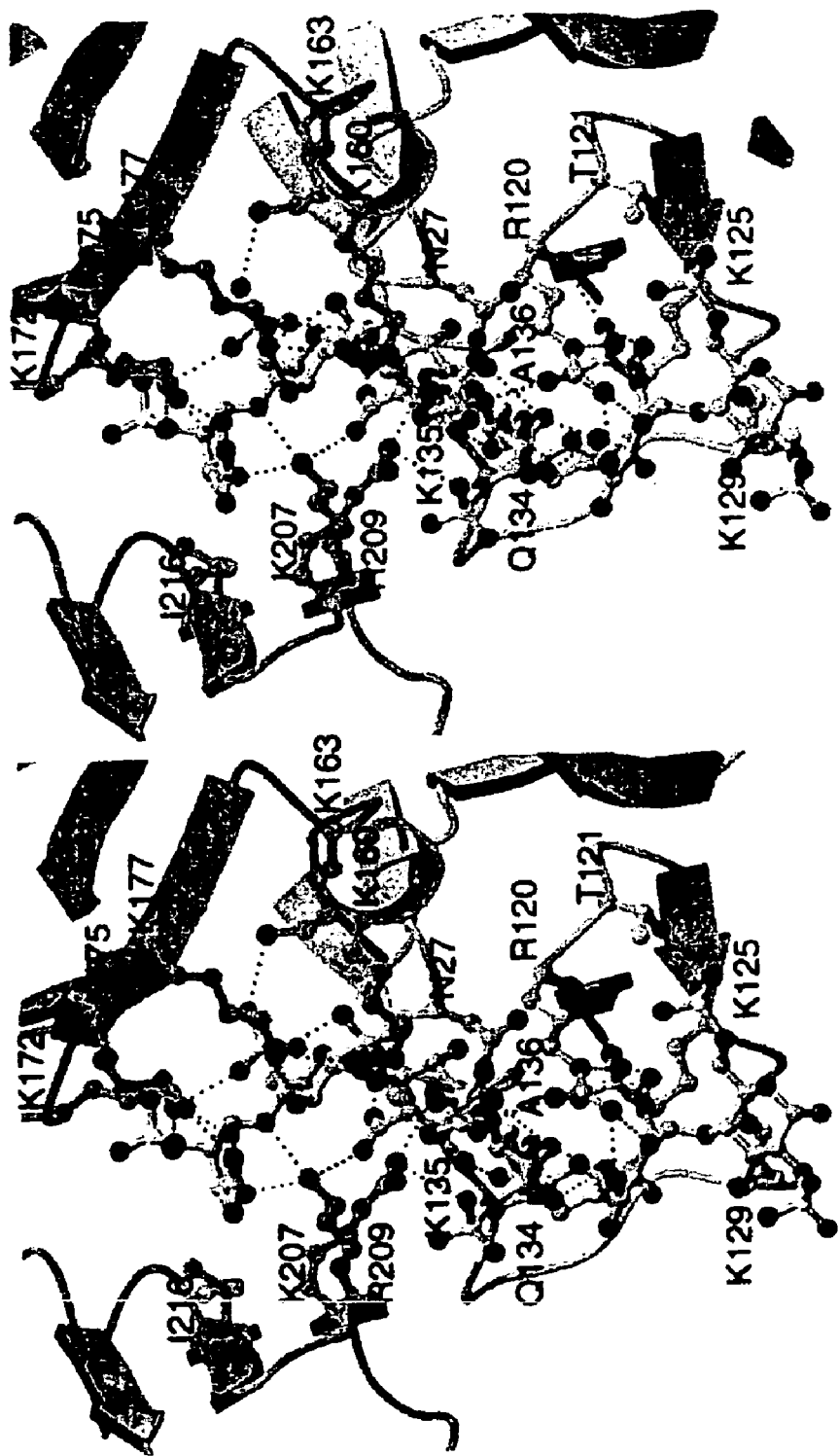
FIG. 29 shows a stereoview of the detailed interactions between ordered decasaccharide rings (A–F), FGF and FGFR. Only the side chains of interacting residues are shown. The two D2s of the adjoining FGFRs are colored cyan and green respectively. Atom coloring is the same as in FIG. 27. The carbon atoms in FGFRs have the same coloring as the D2 to which they belong. Dotted lines represent hydrogen bonds.
Figure 30:
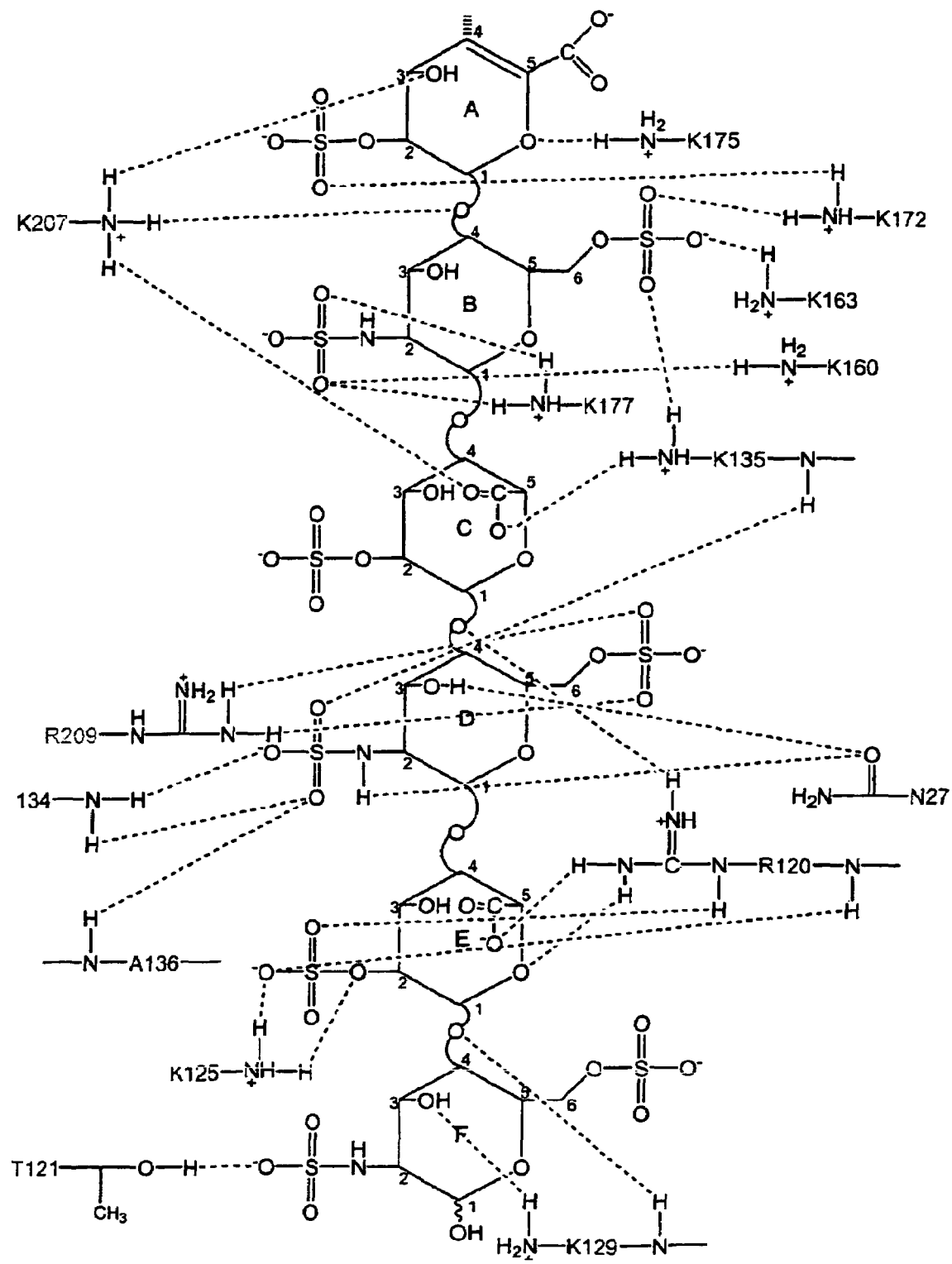
FIG. 30 shows a schematic diagram of interactions between decasaccharide (heparrin), FGF and FGFR in the ternary complex. Only the relevant functional groups and backbone atoms of the interacting amino acids are shown. Dashed lines represent hydrogen bonds. Hashed lines represent hydrophobic interactions. The sugar rings of heparin are labeled A through F starting at the non-reducing end. The backbone carbon atoms of heparin are numbered according to IUPAC nomenclature. The type and the number of interacting residues are colored based on the molecule to which they belong.

Each decasaccharide makes a total of 30 hydrogen bonds with FGF and both FGFRs (see FIGS. 29 and 30). Within one 1:1 FGF:FGFR complex, 25 hydrogen bonds are made with heparin. The remaining 5 hydrogen bonds with heparin originate from the FGFR of the adjoining 1:1 FGF:FGFR complex. Lysines 160,163, 172,175 and 177, located on the heparin-binding surface of D2, form 7 hydrogen bonds between FGFR and heparin in the context of a 1:1 FGF:FGFR complex. With the exception of a single hydrogen bond between Lys-175 and heparin, which is mediated by a ring oxygen of heparin (ring A), the remainder of these hydrogen bonds are sulfate-mediated. All three types of heparin sulfate groups (N-sulfate, 2-O-sulfate and 6-O-sulfate) are employed in these interactions (FIGS. 29 and 30).

At the FGF-heparin interface, a total of 18 hydrogen bonds are made, of which half are sulfate-mediated (FIGS. 29 and 30). The other half is mediated by carboxylate, linker or ring oxygens of heparin. Surface residues Asn-27 (located in the β1-β2 loop), Arg-120, and Thr-121 (located in the β9-β10 loop), Lys-125, Lys-129, Gln-134, Lys-135, and Ala-136 (located in β11-β12 loop) form the heparin-binding site on FGF. These residues are the same ones that interact with heparin in the FGF2-hexasaccharide structure (Faham et al., Science 271, 1116–1120 (1996)). However, since the orientation of the heparin helix with respect to FGF is flipped between these two structures, the hydrogen binding pairs are not identical.

Aside from a single hydrogen bond between Lys-135 of FGF2 and a 6-O-sulfate (ring B) of heparin, the remainder of the sulfate-mediated interactions involve N-sulfate and 2-O-sulfate groups. This provides an explanation for why FGF2 has been reported to retain binding ability to 6-O-desulfated heparin. Nevertheless, 6-O-desulfated heparin oligosaccharides are still ineffective in promoting FGF2-FGFR interaction. In the present crystal structure, the 6-O-sulfate of ring B (FIGS. 29 and 30) makes hydrogen bonds with heparin-binding residues of both FGF and FGFR. Concurrent binding of both FGF and FGFR to the same sulfate group of heparin clearly serves to increase the apparent affinity of FGF for FGFR. Hence, the present structure also provides a molecular basis for the well-documented heparin-dependent 1:1 FGF:FGFR interaction.

In addition to promoting FGF-FGFR interaction within the 1:1 FGF:FGFR complex, heparin also interacts with the adjoining receptor across the two-fold dimer. A total of 5 hydrogen bonds are made at this interface between FGFR residues Lys-207 and Arg-209 and sugar rings A–D of heparin (FIGS. 29 and 30). Hydrophobic contacts between Ile-216 and the non-reduced ring A of heparin further fortify this interface. The hydrogen bonds between Lys-207 and heparin are mediated via carboxylate, linker and ring oxygens of heparin. In contrast, Arg-209 makes hydrogen bonds with the 6-O-sulfate group of ring D, thereby emphasizing the critical dual role of 6-O-sulfate in promoting 1:1 FGF2:FGFR interaction and inducing 2:2 FGF:FGFR dimer formation. The crystal structure provides a plausible explanation for the well-documented inability of 6-O-desulfated heparin oligosaccharides to promote mitogenic activities by failing to induce receptor dimerization.

TABLE 5

Summary of Crystallographic Analysis

Data Collection Statistics

| Resolution (Å) | Reflections (total/unique) | Completeness (%) | $R_{sym}^a$ (%) | Signal (<I/δI>) |
|---|---|---|---|---|
| 30.0–3.0 | 97669/19774 | 97.2 (92.6)$^b$ | 7.0 (30.3)$^b$ | 12.3 |

Refinement Statistics$^c$

| | | | | Root-mean-square Deviations | |
|---|---|---|---|---|---|
| Resolution (Å) | Reflections | $R_{cryst}/R_{free}^d$ (%) | Bonds (Å) | Angles (°) | B-factors$^e$ (Å$^2$) |
| 25.0–3.0 | 18305 | 23.1/28.9 | 0.011 | 1.6 | 1.28 |

$^a R_{sym} = 100 \times \Sigma_{hkl}\Sigma_i |I_i(hkl) - <I(hkl)>|/\Sigma_{hkl}\Sigma_i I_i(hkl)$.
$^b$Value in parentheses is for the highest resolution shell: 3.11–3.00 Å.
$^c$Atomic model: 5245 protein atoms and 245 decasaccharide atoms.
$^d R_{cryst/free} = 100 \times \Sigma_{hkl}||F_o(hkl)| - |F_c(hkl)||/\Sigma_{hkl}|F_o(hkl)|$, where $F_o$ (>2δ) and $F_c$ are the observed and calculated structure factors, respectively. 5% of the reflections were used for calculation of $R_{free}$.
$^e$For bonded atoms.

The invention illustratively described herein may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other documents.

The terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The structure of the FGFR1(D2-D3)/FGF2 complex has been described in Plotnikov et al., Cell 98, 641–650 (1999). The structures of the FGFR1(D2-D3)/FGF1 complex and the FGFR2/FGF2 complex are described in Plotnikov et al., Cell 101, 413424 (2000). The structure of the human stem cell factor homodimer is described in Zhang et al., Proc. Nat. Acad. Sci. 97(14), 7732–7737 (2000). The disclosures of these three references are herein incorporated by reference.

The following bibliography includes general references relating to RPTKs as well as citations relating more specifically to the structure of the FGF-FGFR-heparin ternary complexes described herein.

Basilico, C., and Moscatelli, D. (1992). The FGF family of growth factors and oncogenes. Adv. Cancer Res. 59, 115–165.

Bruenger, A. T., Adams, P. D., Clore, G. M., DeLano, W. L., Gros, P., Grosse-Kunstleve, R. W., Jiang, J. S., Kuszewski, J., Nigles, M., Pannu, N. S., Read, R. J., Rice, L. M., Simonson, T., and Warren, G. L. (1998). Crystallography and NMR system: A new software suite for macromolecular structure determination. Acta. Crystallogr. D 54, 905–921.

Burgess, W. H., and Maciag, T. (1989). The heparin-binding (fibroblast) growth factor family of proteins. Annu. Rev. Biochem. 58, 575–606.

Esnouf, R. M. (1997). An extensively modified version of MolScript that includes greatly enhanced coloring capabilities. J. Mol. Graph. Model 15, 132–134.

Faham, S., Hileman, R. E., Fromm, J. R., Linhardt, R. J., and Rees, D.C. (1996). Heparin structure and interactions with basic fibroblast growth factor. Science 271, 1116–1120.

Faham, S., Linhardt, R. J., and Rees, D.C. (1998). Diversity does make a difference: fibroblast growth factor-heparin interactions. Curr. Opin. Struct. Biol. 8, 578–586.

Gambarini, A. G., Miyamoto, C. A., Lima, G. A., Nader, H. B., and Dietrich, C. P. (1993). Mitogenic activity of acidic fibroblast growth factor is enhanced by highly sulfated oligosaccharides derived from heparin and heparan sulfate. Mol. Cell Biochem. 124, 121–129.

Galzie, Z., Kinsella, A. R., and Smith, J. A. (1997). Fibroblast growth factors and their receptors. Biochem. Cell. Biol. 75, 669–685.

Guimond, S., Maccarana, M., Olwin, B. B., Lindahl, U., and Rapraeger, A. C. (1993). Activating and inhibitory heparin sequences for FGF-2 (basic FGF). Distinct requirements for FGF-1, FGF-2 and FGF4. J. Biol. Chem. 268, 23906–23914.

Ishihara, M. (1994). Structural requirements in heparin for binding and activation of FGF-1 and FGF4 are different from that for FGF-2. Glycobiology 4, 817–824.

Jaye, M., (1992). Fibroblast growth factor receptor tyrosine kinases: molecular analysis and signal transduction. Biochim. Biophys. Acta 1135, 185–199.

Johnson, D. E., and Williams, L. T. (1993). Structural and functional diversity in the FGF receptor multigene family. Adv. Cancer Res. 60, 1–41.

Jones, T. A. (1991). Improved methods for binding protein models in electron density maps and the location of errors in these models. Acta Crystallogr,. A 47, 110–119.

Kleywegt, (1998). Databases in protein crystallography. Acta Crystallogr. D54, 1119–1131.

Kraulis, P. J. (1991). MOLSCRIPT: a program to produce both detailed and schematic plots of protein structures. J. Appl. Crystallogr. 24, 946–950.

Merrit, E. A. and Bacon, D. J. (1997). Raster3D: photorealistic molecular graphics. Meth. Enzymol. 277, 505–524.

Mulloy, B, Forster, M. J., Jones, C., and Davies, D. B. (1993). N.M.R. and molecular-modelling studies of the solution conformation of heparin. Biochem. J. 293, 849–858.

Naski, M. C. (1998). FGF signaling in skeletal development. Front Biosci. 3, D781–794.

Nicholls, A., Sharp, K. A., and Honig, B. (1991). Protein folding and association: insights from interfacial and thermodynamic properties of hydrocarbons. Proteins 11, 281–296.

Nieduszynski, (1977). Am. Chem. Soc. Symp. Ser. 48,73.

Nishimura, T., Nakatake, Y., Konishi, M., and Itoh, N. (2000). Identification of a novel FGF, FGF-21, preferentially expressed in the liver. Biochim. Biophys. Acta, 1492, 203–206.

Ornitz, D. M., Xu, J., Colvin, J. S., McEwen, D. G., MacArthur, C. A., Coulier, F., Gao, G., and Goldfarb, M. (1996). Receptor specificity of the fibroblast growth factor family. J. Biol. Chem. 271, 15292–15297.

Ornitz, D. M., Yayon, A., Flanagan, J. G., Svahn, C. M., Levi, E., and Leder, P. (1992). Heparin is required for cell-free binding of bFGF to a soluble receptor and for mitogenesis in whole cells. Mol. Cell. Biol. 12,240–247.

Ornitz, D. M., Herr, A. B., Nilsson, M., Westman, J., Svahn, C. M., and Waksman, G. (1995). FGF binding and FGF receptor activation by synthetic heparan-derived di- and trisaccharides. Science 268, 432–436

Otwinowski, Z. (1993). Oscillation data reduction program. In Proceedings of the CCP4 Study Weekend. (SERC Daresbury Laboratory, Daresbury, United Kingdom).

Plotnikov, A. N., Schlessinger, J., Hubbard, S. R., and Mohammadi, M. (1999). Structural basis for FGF receptor dimerization and activation. Cell 98, 641–650.

Plotnikov, A. N., Hubbard, S. R., Schlessinger, J., and Mohammadi, M. (2000). Structural basis for FGF receptor dimerization and activation. Cell 101, 413–424.

Pye, D. A., Vives, R. R., Turnbull, J. E., Hyde, P., and Gallagher, J. T. (1998). Heparan sulfate oligosaccharides require 6-O-sulfation for promotion of basic fibroblast growth factor mitogenic activity. J. Biol. Chem. 273, 22936–22942.

Rapraeger, A. C., Krufka, A., and Olwin, B. B. (1991). Requirement of heparan sulfate for bFGF-mediated fibroblast growth and myoblast differentiation. Science 252, 1708–1708.

Rusnati, M., Coltrini, D., Caccia, P., Dell'Era, P., Zoppetti, G., Oreste, P., Valsasina, B., and Presta, M. (1994). Distinct role of 2-O—, N—, and 6-O-sulfate groups of heparin in the formation of the ternary complex with basic fibroblast growth factor and soluble FGF receptor-1. Biochem. Biophys. Res. Commun. 203, 450–458.

Stauber, et al. (2000). *Proc. Natl. Acad. Sci. USA* 97, 49–54.

Venkataraman, G (1999). Proc. Natl. Acad. Sci. USA 96, 3658–3663.

Yayon,. (1991). Cell 64, 841–848.

Spivak-Kroizman. (1994). Heparin-induced oligomerization of FGF molecules is responsible for FGF receptor dimerization, activation, and cell proliferation. Cell 79, 1015–1024.

Zhou, F. Y. et al. *Eur. J. Cell Biol.* 73, 71–80.

TABLE 1

FGFR1 D2–D3 Complexed with FGF2

| | | | | | | | | | |
|---|---|---|---|---|---|---|---|---|---|
| ATOM | 1 | CB | HIS | A | 16 | 69.016 | 29.963 | 137.171 | 1.00 41.99 |
| ATOM | 2 | CG | HIS | A | 16 | 67.950 | 29.424 | 138.074 | 1.00 44.70 |
| ATOM | 3 | CD2 | HIS | A | 16 | 67.435 | 29.899 | 139.233 | 1.00 44.60 |
| ATOM | 4 | ND1 | HIS | A | 16 | 67.286 | 28.242 | 137.817 | 1.00 45.58 |
| ATOM | 5 | CE1 | HIS | A | 16 | 66.412 | 28.011 | 138.781 | 1.00 45.34 |
| ATOM | 6 | NE2 | HIS | A | 16 | 66.481 | 29.002 | 139.652 | 1.00 45.97 |
| ATOM | 7 | C | HIS | A | 16 | 68.950 | 28.141 | 135.513 | 1.00 42.15 |
| ATOM | 8 | O | HIS | A | 16 | 68.419 | 28.749 | 134.583 | 1.00 44.62 |
| ATOM | 9 | N | HIS | A | 16 | 71.039 | 29.455 | 135.830 | 1.00 40.32 |
| ATOM | 10 | CA | HIS | A | 16 | 69.840 | 28.875 | 136.502 | 1.00 41.81 |
| ATOM | 11 | N | PHE | A | 17 | 68.761 | 26.844 | 135.742 | 1.00 41.35 |
| ATOM | 12 | CA | PHE | A | 17 | 67.965 | 25.985 | 134.864 | 1.00 40.26 |
| ATOM | 13 | CB | PHE | A | 17 | 68.024 | 24.543 | 135.383 | 1.00 37.06 |
| ATOM | 14 | CG | PHE | A | 17 | 67.253 | 24.321 | 136.661 | 1.00 36.58 |
| ATOM | 15 | CD1 | PHE | A | 17 | 65.951 | 23.823 | 136.632 | 1.00 35.88 |
| ATOM | 16 | CD2 | PHE | A | 17 | 67.796 | 24.674 | 137.891 | 1.00 35.10 |
| ATOM | 17 | CE1 | PHE | A | 17 | 65.210 | 23.686 | 137.809 | 1.00 32.72 |
| ATOM | 18 | CE2 | PHE | A | 17 | 67.052 | 24.539 | 139.064 | 1.00 31.85 |
| ATOM | 19 | CZ | PHE | A | 17 | 65.761 | 24.047 | 139.018 | 1.00 30.46 |
| ATOM | 20 | C | PHE | A | 17 | 66.501 | 26.413 | 134.643 | 1.00 41.70 |
| ATOM | 21 | O | PHE | A | 17 | 65.914 | 26.068 | 133.623 | 1.00 42.96 |
| ATOM | 22 | N | LYS | A | 18 | 65.942 | 27.163 | 135.587 | 1.00 42.87 |
| ATOM | 23 | CA | LYS | A | 18 | 64.556 | 27.622 | 135.488 | 1.00 42.89 |
| ATOM | 24 | CB | LYS | A | 18 | 64.083 | 28.161 | 136.843 | 1.00 40.05 |
| ATOM | 25 | C | LYS | A | 18 | 64.348 | 28.702 | 134.420 | 1.00 43.25 |
| ATOM | 26 | O | LYS | A | 18 | 63.273 | 28.783 | 133.818 | 1.00 43.36 |
| ATOM | 27 | N | ASP | A | 19 | 65.377 | 29.522 | 134.190 | 1.00 42.81 |
| ATOM | 28 | CA | ASP | A | 19 | 65.312 | 30.618 | 133.216 | 1.00 40.93 |
| ATOM | 29 | CB | ASP | A | 19 | 66.335 | 31.686 | 133.579 | 1.00 41.73 |
| ATOM | 30 | CG | ASP | A | 19 | 66.025 | 32.348 | 134.896 | 1.00 43.73 |
| ATOM | 31 | OD1 | ASP | A | 19 | 65.882 | 31.624 | 135.903 | 1.00 46.50 |
| ATOM | 32 | OD2 | ASP | A | 19 | 65.919 | 33.591 | 134.931 | 1.00 43.92 |
| ATOM | 33 | C | ASP | A | 19 | 65.520 | 30.193 | 131.765 | 1.00 38.86 |
| ATOM | 34 | O | ASP | A | 19 | 66.038 | 29.108 | 131.492 | 1.00 38.38 |
| ATOM | 35 | N | PRO | A | 20 | 65.097 | 31.044 | 130.809 | 1.00 36.59 |
| ATOM | 36 | CD | PRO | A | 20 | 64.245 | 32.233 | 130.938 | 1.00 36.39 |
| ATOM | 37 | CA | PRO | A | 20 | 65.263 | 30.712 | 129.396 | 1.00 34.39 |
| ATOM | 38 | CB | PRO | A | 20 | 64.474 | 31.799 | 128.673 | 1.00 31.04 |
| ATOM | 39 | CG | PRO | A | 20 | 63.467 | 32.189 | 129.638 | 1.00 33.58 |
| ATOM | 40 | C | PRO | A | 20 | 66.726 | 30.773 | 129.038 | 1.00 34.58 |
| ATOM | 41 | O | PRO | A | 20 | 67.507 | 31.506 | 129.657 | 1.00 35.62 |
| ATOM | 42 | N | LYS | A | 21 | 67.089 | 30.000 | 128.027 | 1.00 32.92 |
| ATOM | 43 | CA | LYS | A | 21 | 68.449 | 29.959 | 127.556 | 1.00 32.11 |
| ATOM | 44 | CB | LYS | A | 21 | 69.042 | 28.572 | 127.773 | 1.00 31.65 |
| ATOM | 45 | CG | LYS | A | 21 | 69.408 | 28.268 | 129.214 | 1.00 33.27 |
| ATOM | 46 | CD | LYS | A | 21 | 70.054 | 26.901 | 129.323 | 1.00 32.63 |
| ATOM | 47 | CE | LYS | A | 21 | 70.056 | 26.396 | 130.757 | 1.00 34.58 |
| ATOM | 48 | NZ | LYS | A | 21 | 70.472 | 24.961 | 130.814 | 1.00 35.96 |
| ATOM | 49 | C | LYS | A | 21 | 68.481 | 30.296 | 126.078 | 1.00 32.97 |
| ATOM | 50 | O | LYS | A | 21 | 67.484 | 30.154 | 125.377 | 1.00 32.04 |
| ATOM | 51 | N | ARG | A | 22 | 69.626 | 30.779 | 125.613 | 1.00 33.48 |
| ATOM | 52 | CA | ARG | A | 22 | 69.784 | 31.097 | 124.209 | 1.00 32.66 |
| ATOM | 53 | CB | ARG | A | 22 | 70.360 | 32.501 | 124.032 | 1.00 32.91 |
| ATOM | 54 | CG | ARG | A | 22 | 69.297 | 33.575 | 123.837 | 1.00 34.86 |
| ATOM | 55 | CD | ARG | A | 22 | 69.895 | 34.819 | 123.216 | 1.00 36.56 |
| ATOM | 56 | NE | ARG | A | 22 | 70.410 | 35.730 | 124.227 | 1.00 41.57 |
| ATOM | 57 | CZ | ARG | A | 22 | 69.640 | 36.525 | 124.961 | 1.00 44.42 |
| ATOM | 58 | NH1 | ARG | A | 22 | 68.326 | 36.510 | 124.781 | 1.00 47.29 |
| ATOM | 59 | NH2 | ARG | A | 22 | 70.174 | 37.330 | 125.873 | 1.00 46.76 |
| ATOM | 60 | C | ARG | A | 22 | 70.743 | 30.050 | 123.680 | 1.00 31.65 |
| ATOM | 61 | O | ARG | A | 22 | 71.782 | 29.812 | 124.285 | 1.00 32.89 |
| ATOM | 62 | N | LEU | A | 23 | 70.392 | 29.389 | 122.585 | 1.00 29.77 |
| ATOM | 63 | CA | LEU | A | 23 | 71.296 | 28.386 | 122.050 | 1.00 28.94 |
| ATOM | 64 | CB | LEU | A | 23 | 70.528 | 27.131 | 121.626 | 1.00 26.35 |
| ATOM | 65 | CG | LEU | A | 23 | 69.825 | 26.375 | 122.758 | 1.00 24.87 |
| ATOM | 66 | CD1 | LEU | A | 23 | 69.641 | 24.951 | 122.332 | 1.00 21.75 |
| ATOM | 67 | CD2 | LEU | A | 23 | 70.656 | 26.393 | 124.034 | 1.00 26.45 |
| ATOM | 68 | C | LEU | A | 23 | 72.160 | 28.911 | 120.897 | 1.00 30.13 |

TABLE 1-continued

FGFR1 D2–D3 Complexed with FGF2

| ATOM | 69 | O | LEU | A | 23 | 71.690 | 29.114 | 119.774 | 1.00 | 29.81 |
|---|---|---|---|---|---|---|---|---|---|---|
| ATOM | 70 | N | TYR | A | 24 | 73.436 | 29.136 | 121.199 | 1.00 | 29.52 |
| ATOM | 71 | CA | TYR | A | 24 | 74.399 | 29.633 | 120.224 | 1.00 | 27.79 |
| ATOM | 72 | CB | TYR | A | 24 | 75.404 | 30.516 | 120.962 | 1.00 | 25.04 |
| ATOM | 73 | CG | TYR | A | 24 | 76.606 | 30.962 | 120.168 | 1.00 | 27.06 |
| ATOM | 74 | CD1 | TYR | A | 24 | 77.653 | 30.079 | 119.899 | 1.00 | 26.87 |
| ATOM | 75 | CE1 | TYR | A | 24 | 78.785 | 30.489 | 119.219 | 1.00 | 24.47 |
| ATOM | 76 | CD2 | TYR | A | 24 | 76.727 | 32.283 | 119.722 | 1.00 | 26.32 |
| ATOM | 77 | CE2 | TYR | A | 24 | 77.865 | 32.705 | 119.039 | 1.00 | 24.37 |
| ATOM | 78 | CZ | TYR | A | 24 | 78.888 | 31.796 | 118.795 | 1.00 | 23.72 |
| ATOM | 79 | OH | TYR | A | 24 | 80.023 | 32.183 | 118.134 | 1.00 | 22.17 |
| ATOM | 80 | C | TYR | A | 24 | 75.077 | 28.448 | 119.509 | 1.00 | 28.20 |
| ATOM | 81 | O | TYR | A | 24 | 75.748 | 27.635 | 120.132 | 1.00 | 27.40 |
| ATOM | 82 | N | CYS | A | 25 | 74.887 | 28.342 | 118.199 | 1.00 | 29.93 |
| ATOM | 83 | CA | CYS | A | 25 | 75.471 | 27.239 | 117.437 | 1.00 | 30.80 |
| ATOM | 84 | CB | CYS | A | 25 | 74.690 | 27.015 | 116.141 | 1.00 | 29.39 |
| ATOM | 85 | SG | CYS | A | 25 | 75.266 | 25.611 | 115.174 | 1.00 | 27.95 |
| ATOM | 86 | C | CYS | A | 25 | 76.926 | 27.506 | 117.111 | 1.00 | 32.90 |
| ATOM | 87 | O | CYS | A | 25 | 77.279 | 28.585 | 116.633 | 1.00 | 35.05 |
| ATOM | 88 | N | LYS | A | 26 | 77.774 | 26.519 | 117.370 | 1.00 | 34.20 |
| ATOM | 89 | CA | LYS | A | 26 | 79.205 | 26.646 | 117.103 | 1.00 | 33.90 |
| ATOM | 90 | CB | LYS | A | 26 | 79.917 | 25.362 | 117.540 | 1.00 | 33.25 |
| ATOM | 91 | CG | LYS | A | 26 | 81.420 | 25.379 | 117.382 | 1.00 | 33.15 |
| ATOM | 92 | CD | LYS | A | 26 | 82.028 | 24.156 | 118.038 | 1.00 | 33.12 |
| ATOM | 93 | CE | LYS | A | 26 | 83.540 | 24.186 | 117.966 | 1.00 | 33.97 |
| ATOM | 94 | NZ | LYS | A | 26 | 84.056 | 23.910 | 116.590 | 1.00 | 38.44 |
| ATOM | 95 | C | LYS | A | 26 | 79.466 | 26.903 | 115.621 | 1.00 | 34.79 |
| ATOM | 96 | O | LYS | A | 26 | 80.472 | 27.520 | 115.253 | 1.00 | 35.31 |
| ATOM | 97 | N | ASN | A | 27 | 78.548 | 26.439 | 114.775 | 1.00 | 34.52 |
| ATOM | 98 | CA | ASN | A | 27 | 78.696 | 26.588 | 113.340 | 1.00 | 33.29 |
| ATOM | 99 | CB | ASN | A | 27 | 78.043 | 25.408 | 112.637 | 1.00 | 35.53 |
| ATOM | 100 | CG | ASN | A | 27 | 78.423 | 25.320 | 111.176 | 1.00 | 37.03 |
| ATOM | 101 | OD1 | ASN | A | 27 | 79.601 | 25.349 | 110.829 | 1.00 | 39.05 |
| ATOM | 102 | ND2 | ASN | A | 27 | 77.427 | 25.200 | 110.311 | 1.00 | 38.14 |
| ATOM | 103 | C | ASN | A | 27 | 78.129 | 27.886 | 112.794 | 1.00 | 33.64 |
| ATOM | 104 | O | ASN | A | 27 | 77.013 | 27.917 | 112.271 | 1.00 | 32.60 |
| ATOM | 105 | N | GLY | A | 28 | 78.909 | 28.958 | 112.922 | 1.00 | 33.42 |
| ATOM | 106 | CA | GLY | A | 28 | 78.489 | 30.247 | 112.408 | 1.00 | 32.48 |
| ATOM | 107 | C | GLY | A | 28 | 78.101 | 31.273 | 113.447 | 1.00 | 31.65 |
| ATOM | 108 | O | GLY | A | 28 | 77.968 | 32.458 | 113.146 | 1.00 | 30.93 |
| ATOM | 109 | N | GLY | A | 29 | 77.904 | 30.821 | 114.673 | 1.00 | 30.89 |
| ATOM | 110 | CA | GLY | A | 29 | 77.527 | 31.745 | 115.716 | 1.00 | 32.62 |
| ATOM | 111 | C | GLY | A | 29 | 76.065 | 32.109 | 115.616 | 1.00 | 33.06 |
| ATOM | 112 | O | GLY | A | 29 | 75.639 | 33.179 | 116.061 | 1.00 | 33.90 |
| ATOM | 113 | N | PHE | A | 30 | 75.293 | 31.214 | 115.013 | 1.00 | 33.36 |
| ATOM | 114 | CA | PHE | A | 30 | 73.863 | 31.425 | 114.869 | 1.00 | 33.15 |
| ATOM | 115 | CB | PHE | A | 30 | 73.339 | 30.732 | 113.604 | 1.00 | 32.93 |
| ATOM | 116 | CG | PHE | A | 30 | 73.802 | 31.366 | 112.320 | 1.00 | 34.10 |
| ATOM | 117 | CD1 | PHE | A | 30 | 74.945 | 30.912 | 111.674 | 1.00 | 33.99 |
| ATOM | 118 | CD2 | PHE | A | 30 | 73.101 | 32.438 | 111.763 | 1.00 | 33.52 |
| ATOM | 119 | CE1 | PHE | A | 30 | 75.381 | 31.511 | 110.494 | 1.00 | 32.91 |
| ATOM | 120 | CE2 | PHE | A | 30 | 73.533 | 33.042 | 110.585 | 1.00 | 31.25 |
| ATOM | 121 | CZ | PHE | A | 30 | 74.674 | 32.578 | 109.951 | 1.00 | 31.88 |
| ATOM | 122 | C | PHE | A | 30 | 73.091 | 30.900 | 116.083 | 1.00 | 32.68 |
| ATOM | 123 | O | PHE | A | 30 | 73.306 | 29.778 | 116.531 | 1.00 | 31.40 |
| ATOM | 124 | N | PHE | A | 31 | 72.206 | 31.737 | 116.611 | 1.00 | 33.00 |
| ATOM | 125 | CA | PHE | A | 31 | 71.341 | 31.386 | 117.732 | 1.00 | 34.02 |
| ATOM | 126 | CB | PHE | A | 31 | 70.856 | 32.643 | 118.445 | 1.00 | 34.25 |
| ATOM | 127 | CG | PHE | A | 31 | 71.883 | 33.283 | 119.306 | 1.00 | 35.90 |
| ATOM | 128 | CD1 | PHE | A | 31 | 72.290 | 32.670 | 120.488 | 1.00 | 36.24 |
| ATOM | 129 | CD2 | PHE | A | 31 | 72.438 | 34.503 | 118.952 | 1.00 | 34.85 |
| ATOM | 130 | CE1 | PHE | A | 31 | 73.237 | 33.266 | 121.306 | 1.00 | 35.63 |
| ATOM | 131 | CE2 | PHE | A | 31 | 73.385 | 35.105 | 119.763 | 1.00 | 35.21 |
| ATOM | 132 | CZ | PHE | A | 31 | 73.786 | 34.484 | 120.946 | 1.00 | 35.42 |
| ATOM | 133 | C | PHE | A | 31 | 70.110 | 30.681 | 117.163 | 1.00 | 33.76 |
| ATOM | 134 | O | PHE | A | 31 | 69.507 | 31.172 | 116.216 | 1.00 | 34.00 |
| ATOM | 135 | N | LEU | A | 32 | 69.727 | 29.544 | 117.735 | 1.00 | 33.72 |
| ATOM | 136 | CA | LEU | A | 32 | 68.546 | 28.843 | 117.246 | 1.00 | 32.35 |
| ATOM | 137 | CB | LEU | A | 32 | 68.324 | 27.520 | 117.978 | 1.00 | 33.20 |
| ATOM | 138 | CG | LEU | A | 32 | 67.212 | 26.674 | 117.337 | 1.00 | 35.02 |
| ATOM | 139 | CD1 | LEU | A | 32 | 67.743 | 26.012 | 116.074 | 1.00 | 34.56 |
| ATOM | 140 | CD2 | LEU | A | 32 | 66.724 | 25.611 | 118.301 | 1.00 | 34.97 |
| ATOM | 141 | C | LEU | A | 32 | 67.333 | 29.739 | 117.448 | 1.00 | 30.84 |
| ATOM | 142 | O | LEU | A | 32 | 67.113 | 30.288 | 118.533 | 1.00 | 31.20 |
| ATOM | 143 | N | ARG | A | 33 | 66.550 | 29.887 | 116.390 | 1.00 | 29.27 |
| ATOM | 144 | CA | ARG | A | 33 | 65.374 | 30.734 | 116.445 | 1.00 | 30.54 |
| ATOM | 145 | CB | ARG | A | 33 | 65.548 | 31.920 | 115.508 | 1.00 | 28.32 |

TABLE 1-continued

FGFR1 D2–D3 Complexed with FGF2

| ATOM | 146 | CG | ARG | A | 33 | 64.365 | 32.834 | 115.547 | 1.00 | 26.41 |
|---|---|---|---|---|---|---|---|---|---|---|
| ATOM | 147 | CD | ARG | A | 33 | 64.640 | 34.102 | 114.822 | 1.00 | 23.29 |
| ATOM | 148 | NE | ARG | A | 33 | 65.039 | 33.869 | 113.445 | 1.00 | 18.71 |
| ATOM | 149 | CZ | ARG | A | 33 | 65.222 | 34.854 | 112.574 | 1.00 | 18.55 |
| ATOM | 150 | NH1 | ARG | A | 33 | 65.037 | 36.113 | 112.957 | 1.00 | 13.11 |
| ATOM | 151 | NH2 | ARG | A | 33 | 65.602 | 34.585 | 111.334 | 1.00 | 18.20 |
| ATOM | 152 | C | ARG | A | 33 | 64.062 | 30.030 | 116.100 | 1.00 | 32.27 |
| ATOM | 153 | O | ARG | A | 33 | 63.993 | 29.229 | 115.149 | 1.00 | 33.66 |
| ATOM | 154 | N | ILE | A | 34 | 63.022 | 30.330 | 116.876 | 1.00 | 30.42 |
| ATOM | 155 | CA | ILE | A | 34 | 61.718 | 29.750 | 116.625 | 1.00 | 29.36 |
| ATOM | 156 | CB | ILE | A | 34 | 61.230 | 28.904 | 117.788 | 1.00 | 27.41 |
| ATOM | 157 | CG2 | ILE | A | 34 | 59.744 | 28.626 | 117.631 | 1.00 | 25.89 |
| ATOM | 158 | CG1 | ILE | A | 34 | 62.001 | 27.587 | 117.822 | 1.00 | 26.27 |
| ATOM | 159 | CD1 | ILE | A | 34 | 61.727 | 26.757 | 119.052 | 1.00 | 25.37 |
| ATOM | 160 | C | ILE | A | 34 | 60.710 | 30.847 | 116.370 | 1.00 | 30.63 |
| ATOM | 161 | O | ILE | A | 34 | 60.280 | 31.534 | 117.293 | 1.00 | 30.14 |
| ATOM | 162 | N | HIS | A | 35 | 60.350 | 31.001 | 115.099 | 1.00 | 31.46 |
| ATOM | 163 | CA | HIS | A | 35 | 59.383 | 32.002 | 114.665 | 1.00 | 33.03 |
| ATOM | 164 | CB | HIS | A | 35 | 59.334 | 32.064 | 113.136 | 1.00 | 32.91 |
| ATOM | 165 | CG | HIS | A | 35 | 60.620 | 32.472 | 112.498 | 1.00 | 32.44 |
| ATOM | 166 | CD2 | HIS | A | 35 | 61.634 | 31.734 | 111.985 | 1.00 | 33.64 |
| ATOM | 167 | ND1 | HIS | A | 35 | 60.975 | 33.790 | 112.321 | 1.00 | 32.36 |
| ATOM | 168 | CE1 | HIS | A | 35 | 62.151 | 33.849 | 111.722 | 1.00 | 33.74 |
| ATOM | 169 | NE2 | HIS | A | 35 | 62.573 | 32.615 | 111.506 | 1.00 | 33.60 |
| ATOM | 170 | C | HIS | A | 35 | 57.981 | 31.667 | 115.155 | 1.00 | 32.67 |
| ATOM | 171 | O | HIS | A | 35 | 57.588 | 30.500 | 115.213 | 1.00 | 32.12 |
| ATOM | 172 | N | PRO | A | 36 | 57.205 | 32.691 | 115.508 | 1.00 | 33.10 |
| ATOM | 173 | CD | PRO | A | 36 | 57.659 | 34.079 | 115.691 | 1.00 | 32.12 |
| ATOM | 174 | CA | PRO | A | 36 | 55.829 | 32.511 | 115.988 | 1.00 | 34.09 |
| ATOM | 175 | CB | PRO | A | 36 | 55.339 | 33.942 | 116.136 | 1.00 | 32.69 |
| ATOM | 176 | CG | PRO | A | 36 | 56.588 | 34.657 | 116.587 | 1.00 | 33.71 |
| ATOM | 177 | C | PRO | A | 36 | 54.968 | 31.705 | 115.009 | 1.00 | 34.10 |
| ATOM | 178 | O | PRO | A | 36 | 53.993 | 31.080 | 115.393 | 1.00 | 34.65 |
| ATOM | 179 | N | ASP | A | 37 | 55.347 | 31.720 | 113.742 | 1.00 | 34.54 |
| ATOM | 180 | CA | ASP | A | 37 | 54.610 | 31.009 | 112.719 | 1.00 | 34.85 |
| ATOM | 181 | CB | ASP | A | 37 | 54.831 | 31.717 | 111.378 | 1.00 | 35.76 |
| ATOM | 182 | CG | ASP | A | 37 | 56.219 | 31.444 | 110.778 | 1.00 | 39.05 |
| ATOM | 183 | OD1 | ASP | A | 37 | 57.142 | 30.974 | 111.495 | 1.00 | 37.89 |
| ATOM | 184 | OD2 | ASP | A | 37 | 56.387 | 31.709 | 109.566 | 1.00 | 41.38 |
| ATOM | 185 | C | ASP | A | 37 | 55.021 | 29.532 | 112.623 | 1.00 | 35.51 |
| ATOM | 186 | O | ASP | A | 37 | 54.530 | 28.801 | 111.755 | 1.00 | 35.50 |
| ATOM | 187 | N | GLY | A | 38 | 55.927 | 29.098 | 113.500 | 1.00 | 34.87 |
| ATOM | 188 | CA | GLY | A | 38 | 56.371 | 27.715 | 113.471 | 1.00 | 32.57 |
| ATOM | 189 | C | GLY | A | 38 | 57.635 | 27.428 | 112.676 | 1.00 | 32.56 |
| ATOM | 190 | O | GLY | A | 38 | 58.130 | 26.300 | 112.696 | 1.00 | 31.39 |
| ATOM | 191 | N | ARG | A | 39 | 58.170 | 28.421 | 111.974 | 1.00 | 32.64 |
| ATOM | 192 | CA | ARG | A | 39 | 59.387 | 28.197 | 111.200 | 1.00 | 34.59 |
| ATOM | 193 | CB | ARG | A | 39 | 59.576 | 29.307 | 110.170 | 1.00 | 35.46 |
| ATOM | 194 | CG | ARG | A | 39 | 58.676 | 29.184 | 108.946 | 1.00 | 37.20 |
| ATOM | 195 | CD | ARG | A | 39 | 58.918 | 30.321 | 107.970 | 1.00 | 37.24 |
| ATOM | 196 | NE | ARG | A | 39 | 58.727 | 31.623 | 108.606 | 1.00 | 36.10 |
| ATOM | 197 | CZ | ARG | A | 39 | 59.006 | 32.785 | 108.025 | 1.00 | 36.28 |
| ATOM | 198 | NH1 | ARG | A | 39 | 58.800 | 33.917 | 108.681 | 1.00 | 38.00 |
| ATOM | 199 | NH2 | ARG | A | 39 | 59.493 | 32.816 | 106.791 | 1.00 | 35.62 |
| ATOM | 200 | C | ARG | A | 39 | 60.585 | 28.157 | 112.135 | 1.00 | 35.64 |
| ATOM | 201 | O | ARG | A | 39 | 60.576 | 28.812 | 113.177 | 1.00 | 37.00 |
| ATOM | 202 | N | VAL | A | 40 | 61.610 | 27.390 | 111.763 | 1.00 | 35.00 |
| ATOM | 203 | CA | VAL | A | 40 | 62.829 | 27.257 | 112.565 | 1.00 | 33.88 |
| ATOM | 204 | CB | VAL | A | 40 | 62.989 | 25.787 | 113.115 | 1.00 | 33.74 |
| ATOM | 205 | CG1 | VAL | A | 40 | 64.364 | 25.590 | 113.742 | 1.00 | 31.93 |
| ATOM | 206 | CG2 | VAL | A | 40 | 61.918 | 25.487 | 114.146 | 1.00 | 30.42 |
| ATOM | 207 | C | VAL | A | 40 | 64.070 | 27.611 | 111.735 | 1.00 | 34.33 |
| ATOM | 208 | O | VAL | A | 40 | 64.236 | 27.126 | 110.617 | 1.00 | 33.67 |
| ATOM | 209 | N | ASP | A | 41 | 64.939 | 28.457 | 112.285 | 1.00 | 34.88 |
| ATOM | 210 | CA | ASP | A | 41 | 66.172 | 28.851 | 111.603 | 1.00 | 33.77 |
| ATOM | 211 | CE | ASP | A | 41 | 65.871 | 29.850 | 110.483 | 1.00 | 33.17 |
| ATOM | 212 | CG | ASP | A | 41 | 65.184 | 31.111 | 110.984 | 1.00 | 34.75 |
| ATOM | 213 | OD1 | ASP | A | 41 | 65.026 | 32.052 | 110.177 | 1.00 | 34.83 |
| ATOM | 214 | OD2 | ASP | A | 41 | 64.794 | 31.167 | 112.173 | 1.00 | 36.12 |
| ATOM | 215 | C | ASP | A | 41 | 67.148 | 29.462 | 112.600 | 1.00 | 33.16 |
| ATOM | 216 | O | ASP | A | 41 | 66.972 | 29.327 | 113.809 | 1.00 | 32.95 |
| ATOM | 217 | N | GLY | A | 42 | 68.170 | 30.144 | 112.093 | 1.00 | 32.65 |
| ATOM | 218 | CA | GLY | A | 42 | 69.154 | 30.761 | 112.966 | 1.00 | 32.74 |
| ATOM | 219 | C | GLY | A | 42 | 69.387 | 32.246 | 112.721 | 1.00 | 33.27 |
| ATOM | 220 | O | GLY | A | 42 | 69.042 | 32.781 | 111.663 | 1.00 | 34.04 |
| ATOM | 221 | N | VAL | A | 43 | 69.979 | 32.913 | 113.707 | 1.00 | 31.48 |
| ATOM | 222 | CA | VAL | A | 43 | 70.277 | 34.334 | 113.626 | 1.00 | 31.31 |

TABLE 1-continued

FGFR1 D2–D3 Complexed with FGF2

| ATOM | 223 | CB | VAL | A | 43 | 69.081 | 35.211 | 114.037 | 1.00 | 31.65 |
|---|---|---|---|---|---|---|---|---|---|---|
| ATOM | 224 | CG1 | VAL | A | 43 | 68.090 | 35.255 | 112.932 | 1.00 | 32.00 |
| ATOM | 225 | CG2 | VAL | A | 43 | 68.446 | 34.680 | 115.327 | 1.00 | 29.54 |
| ATOM | 226 | C | VAL | A | 43 | 71.391 | 34.689 | 114.578 | 1.00 | 31.62 |
| ATOM | 227 | O | VAL | A | 43 | 71.384 | 34.269 | 115.725 | 1.00 | 32.45 |
| ATOM | 228 | N | ARG | A | 44 | 72.330 | 35.501 | 114.120 | 1.00 | 32.59 |
| ATOM | 229 | CA | ARG | A | 44 | 73.430 | 35.900 | 114.978 | 1.00 | 32.23 |
| ATOM | 230 | CB | ARG | A | 44 | 74.634 | 36.305 | 114.133 | 1.00 | 30.10 |
| ATOM | 231 | CG | ARG | A | 44 | 75.173 | 35.165 | 113.321 | 1.00 | 28.38 |
| ATOM | 232 | CD | ARG | A | 44 | 76.442 | 35.549 | 112.600 | 1.00 | 29.66 |
| ATOM | 233 | NE | ARG | A | 44 | 76.916 | 34.448 | 111.762 | 1.00 | 32.18 |
| ATOM | 234 | CZ | ARG | A | 44 | 77.421 | 34.607 | 110.543 | 1.00 | 30.72 |
| ATOM | 235 | NH1 | ARG | A | 44 | 77.521 | 35.821 | 110.020 | 1.00 | 31.62 |
| ATOM | 236 | NH2 | ARG | A | 44 | 77.809 | 33.556 | 109.842 | 1.00 | 29.64 |
| ATOM | 237 | C | ARG | A | 44 | 73.047 | 37.025 | 115.928 | 1.00 | 32.13 |
| ATOM | 238 | O | ARG | A | 44 | 73.689 | 37.207 | 116.960 | 1.00 | 31.61 |
| ATOM | 239 | N | GLU | A | 45 | 71.990 | 37.762 | 115.598 | 1.00 | 32.69 |
| ATOM | 240 | CA | GLU | A | 45 | 71.573 | 38.873 | 116.445 | 1.00 | 34.53 |
| ATOM | 241 | CB | GLU | A | 45 | 70.578 | 39.769 | 115.694 | 1.00 | 36.59 |
| ATOM | 242 | CG | GLU | A | 45 | 70.223 | 41.025 | 116.479 | 1.00 | 41.80 |
| ATOM | 243 | CD | GLU | A | 45 | 71.440 | 41.594 | 117.213 | 1.00 | 44.59 |
| ATOM | 244 | OE1 | GLU | A | 45 | 72.466 | 41.834 | 116.522 | 1.00 | 46.33 |
| ATOM | 245 | OE2 | GLU | A | 45 | 71.371 | 41.786 | 118.460 | 1.00 | 41.23 |
| ATOM | 246 | CG | GLU | A | 45 | 71.00 | 338.474 | 117.814 | 1.00 | 32.72 |
| ATOM | 247 | O | GLU | A | 45 | 69.852 | 38.092 | 117.935 | 1.00 | 33.26 |
| ATOM | 248 | N | LYS | A | 46 | 71.829 | 38.604 | 118.842 | 1.00 | 31.74 |
| ATOM | 249 | CA | LYS | A | 46 | 71.461 | 38.254 | 120.193 | 1.00 | 31.44 |
| ATOM | 250 | CB | LYS | A | 46 | 72.650 | 38.548 | 121.111 | 1.00 | 33.55 |
| ATOM | 251 | CG | LYS | A | 46 | 72.550 | 37.959 | 122.516 | 1.00 | 37.58 |
| ATOM | 252 | CD | LYS | A | 46 | 73.931 | 37.596 | 123.067 | 1.00 | 37.72 |
| ATOM | 253 | CE | LYS | A | 46 | 73.862 | 37.059 | 124.488 | 1.00 | 36.84 |
| ATOM | 254 | NZ | LYS | A | 46 | 73.418 | 38.106 | 125.450 | 1.00 | 39.04 |
| ATOM | 255 | C | LYS | A | 46 | 70.200 | 38.959 | 120.691 | 1.00 | 32.17 |
| ATOM | 256 | O | LYS | A | 46 | 69.531 | 38.468 | 121.609 | 1.00 | 33.32 |
| ATOM | 257 | N | SER | A | 47 | 69.848 | 40.096 | 120.095 | 1.00 | 31.91 |
| ATOM | 258 | CA | SER | A | 47 | 68.649 | 40.804 | 120.550 | 1.00 | 30.89 |
| ATOM | 259 | CB | SER | A | 47 | 68.814 | 42.333 | 120.404 | 1.00 | 29.98 |
| ATOM | 260 | OG | SER | A | 47 | 68.697 | 42.795 | 119.066 | 1.00 | 28.59 |
| ATOM | 261 | C | SER | A | 47 | 67.374 | 40.335 | 119.853 | 1.00 | 29.76 |
| ATOM | 262 | O | SER | A | 47 | 66.293 | 40.863 | 120.108 | 1.00 | 28.86 |
| ATOM | 263 | N | ASP | A | 48 | 67.504 | 39.338 | 118.978 | 1.00 | 29.77 |
| ATOM | 264 | CA | ASP | A | 48 | 66.350 | 38.781 | 118.262 | 1.00 | 30.47 |
| ATOM | 265 | CB | ASP | A | 48 | 66.751 | 37.543 | 117.459 | 1.00 | 28.93 |
| ATOM | 266 | CG | ASP | A | 48 | 65.691 | 37.127 | 116.459 | 1.00 | 30.60 |
| ATOM | 267 | OD1 | ASP | A | 48 | 65.627 | 37.727 | 115.366 | 1.00 | 32.23 |
| ATOM | 268 | OD2 | ASP | A | 48 | 64.913 | 36.202 | 116.759 | 1.00 | 30.50 |
| ATOM | 269 | C | ASP | A | 48 | 65.287 | 38.383 | 119.277 | 1.00 | 31.67 |
| ATOM | 270 | O | ASP | A | 48 | 65.582 | 37.714 | 120.279 | 1.00 | 33.65 |
| ATOM | 271 | N | PRO | A | 49 | 64.032 | 38.779 | 119.028 | 1.00 | 30.74 |
| ATOM | 272 | CD | PRO | A | 49 | 63.576 | 39.618 | 117.907 | 1.00 | 28.94 |
| ATOM | 273 | CA | PRO | A | 49 | 62.923 | 38.467 | 119.933 | 1.00 | 30.97 |
| ATOM | 274 | CB | PRO | A | 49 | 61.787 | 39.340 | 119.387 | 1.00 | 28.99 |
| ATOM | 275 | CG | PRO | A | 49 | 62.086 | 39.416 | 117.952 | 1.00 | 28.31 |
| ATOM | 276 | C | PRO | A | 49 | 62.530 | 36.990 | 120.069 | 1.00 | 30.63 |
| ATOM | 277 | O | PRO | A | 49 | 62.015 | 36.565 | 121.106 | 1.00 | 30.71 |
| ATOM | 278 | N | HIS | A | 50 | 62.815 | 36.208 | 119.043 | 1.00 | 30.61 |
| ATOM | 279 | CA | HIS | A | 50 | 62.433 | 34.811 | 119.044 | 1.00 | 31.64 |
| ATOM | 280 | CB | HIS | A | 50 | 61.790 | 34.502 | 117.704 | 1.00 | 32.65 |
| ATOM | 281 | CG | HIS | A | 50 | 60.935 | 35.616 | 117.201 | 1.00 | 35.28 |
| ATOM | 282 | CD2 | HIS | A | 50 | 61.070 | 36.428 | 116.126 | 1.00 | 34.75 |
| ATOM | 283 | ND1 | HIS | A | 50 | 59.822 | 36.060 | 117.883 | 1.00 | 36.16 |
| ATOM | 284 | CE1 | HIS | A | 50 | 59.311 | 37.101 | 117.251 | 1.00 | 36.04 |
| ATOM | 285 | NE2 | HIS | A | 50 | 60.050 | 37.345 | 116.182 | 1.00 | 35.40 |
| ATOM | 286 | C | HIS | A | 50 | 63.527 | 33.800 | 119.330 | 1.00 | 32.15 |
| ATOM | 287 | O | HIS | A | 50 | 63.411 | 32.636 | 118.922 | 1.00 | 33.26 |
| ATOM | 288 | N | ILE | A | 51 | 64.593 | 34.209 | 120.008 | 1.00 | 30.57 |
| ATOM | 289 | CA | ILE | A | 51 | 65.611 | 33.217 | 120.283 | 1.00 | 30.02 |
| ATOM | 290 | CB | ILE | A | 51 | 66.984 | 33.631 | 119.775 | 1.00 | 26.66 |
| ATOM | 291 | CG2 | ILE | A | 51 | 67.006 | 33.469 | 118.276 | 1.00 | 22.82 |
| ATOM | 292 | CG1 | ILE | A | 51 | 67.340 | 35.032 | 120.263 | 1.00 | 26.24 |
| ATOM | 293 | CD1 | ILE | A | 51 | 68.817 | 35.345 | 120.095 | 1.00 | 24.74 |
| ATOM | 294 | C | ILE | A | 51 | 65.698 | 32.758 | 121.729 | 1.00 | 31.15 |
| ATOM | 295 | O | ILE | A | 51 | 66.518 | 31.894 | 122.050 | 1.00 | 33.30 |
| ATOM | 296 | N | LYS | A | 52 | 64.846 | 33.303 | 122.594 | 1.00 | 29.85 |
| ATOM | 297 | CA | LYS | A | 52 | 64.839 | 32.860 | 123.979 | 1.00 | 30.59 |
| ATOM | 298 | CB | LYS | A | 52 | 64.263 | 33.937 | 124.893 | 1.00 | 30.72 |
| ATOM | 299 | CG | LYS | A | 52 | 65.254 | 35.054 | 125.151 | 1.00 | 30.18 |

TABLE 1-continued

FGFR1 D2–D3 Complexed with FGF2

| ATOM | 300 | CD | LYS | A | 52 | 64.722 | 36.068 | 126.127 | 1.00 | 31.56 |
|---|---|---|---|---|---|---|---|---|---|---|
| ATOM | 301 | CE | LYS | A | 52 | 65.679 | 37.234 | 126.251 | 1.00 | 32.74 |
| ATOM | 302 | NZ | LYS | A | 52 | 65.133 | 38.319 | 127.108 | 1.00 | 35.64 |
| ATOM | 303 | C | LYS | A | 52 | 64.040 | 31.558 | 124.074 | 1.00 | 30.27 |
| ATOM | 304 | O | LYS | A | 52 | 62.833 | 31.522 | 123.817 | 1.00 | 30.12 |
| ATOM | 305 | N | LEU | A | 53 | 64.748 | 30.490 | 124.433 | 1.00 | 29.82 |
| ATOM | 306 | CA | LEU | A | 53 | 64.178 | 29.153 | 124.547 | 1.00 | 28.57 |
| ATOM | 307 | CB | LEU | A | 53 | 65.069 | 28.163 | 123.810 | 1.00 | 26.87 |
| ATOM | 308 | CG | LEU | A | 53 | 65.440 | 28.616 | 122.403 | 1.00 | 25.04 |
| ATOM | 309 | CD1 | LEU | A | 53 | 66.496 | 27.717 | 121.801 | 1.00 | 26.29 |
| ATOM | 310 | CD2 | LEU | A | 53 | 64.198 | 28.609 | 121.561 | 1.00 | 28.71 |
| ATOM | 311 | C | LEU | A | 53 | 64.026 | 28.696 | 125.987 | 1.00 | 28.76 |
| ATOM | 312 | O | LEU | A | 53 | 64.776 | 29.105 | 126.870 | 1.00 | 29.48 |
| ATOM | 313 | N | GLN | A | 54 | 63.028 | 27.856 | 126.221 | 1.00 | 30.22 |
| ATOM | 314 | CA | GLN | A | 54 | 62.786 | 27.314 | 127.558 | 1.00 | 29.52 |
| ATOM | 315 | CB | GLN | A | 54 | 61.370 | 27.617 | 128.041 | 1.00 | 28.20 |
| ATOM | 316 | CG | GLN | A | 54 | 61.152 | 27.291 | 129.505 | 1.00 | 30.47 |
| ATOM | 317 | CD | GLN | A | 54 | 61.887 | 28.243 | 130.440 | 1.00 | 30.27 |
| ATOM | 318 | OE1 | GLN | A | 54 | 61.775 | 29.461 | 130.312 | 1.00 | 31.93 |
| ATOM | 319 | NE2 | GLN | A | 54 | 62.627 | 27.690 | 131.392 | 1.00 | 29.64 |
| ATOM | 320 | C | GLN | A | 54 | 62.974 | 25.814 | 127.444 | 1.00 | 28.34 |
| ATOM | 321 | O | GLN | A | 54 | 62.132 | 25.106 | 126.884 | 1.00 | 28.87 |
| ATOM | 322 | N | LEU | A | 55 | 64.111 | 25.352 | 127.940 | 1.00 | 26.92 |
| ATOM | 323 | CA | LEU | A | 55 | 64.449 | 23.948 | 127.910 | 1.00 | 26.23 |
| ATOM | 324 | CB | LEU | A | 55 | 65.972 | 23.784 | 127.983 | 1.00 | 24.83 |
| ATOM | 325 | CG | LEU | A | 55 | 66.905 | 24.355 | 126.903 | 1.00 | 24.23 |
| ATOM | 326 | CD1 | LEU | A | 55 | 66.962 | 23.433 | 125.713 | 1.00 | 24.55 |
| ATOM | 327 | CD2 | LEU | A | 55 | 66.438 | 25.731 | 126.480 | 1.00 | 26.63 |
| ATOM | 328 | C | LEU | A | 55 | 63.796 | 23.322 | 129.136 | 1.00 | 27.06 |
| ATOM | 329 | O | LEU | A | 55 | 64.004 | 23.768 | 130.272 | 1.00 | 26.61 |
| ATOM | 330 | N | GLN | A | 56 | 62.984 | 22.304 | 128.898 | 1.00 | 27.30 |
| ATOM | 331 | CA | GLN | A | 56 | 62.312 | 21.606 | 129.981 | 1.00 | 28.34 |
| ATOM | 332 | CB | GLN | A | 56 | 60.798 | 21.788 | 129.867 | 1.00 | 26.66 |
| ATOM | 333 | CG | GLN | A | 56 | 60.030 | 21.033 | 130.907 | 1.00 | 23.34 |
| ATOM | 334 | CD | GLN | A | 56 | 60.538 | 21.321 | 132.299 | 1.00 | 28.68 |
| ATOM | 335 | OE1 | GLN | A | 56 | 60.418 | 22.451 | 132.802 | 1.00 | 29.89 |
| ATOM | 336 | NE2 | GLN | A | 56 | 61.115 | 20.302 | 132.941 | 1.00 | 26.31 |
| ATOM | 337 | CG | LN | A | 56 | 62.678 | 20.126 | 129.906 | 1.00 | 28.99 |
| ATOM | 338 | O | GLN | A | 56 | 62.699 | 19.535 | 128.825 | 1.00 | 29.17 |
| ATOM | 339 | N | ALA | A | 57 | 62.994 | 19.533 | 131.050 | 1.00 | 30.52 |
| ATOM | 340 | CA | ALA | A | 57 | 63.354 | 18.118 | 131.072 | 1.00 | 31.59 |
| ATOM | 341 | CB | ALA | A | 57 | 64.322 | 17.828 | 132.237 | 1.00 | 31.98 |
| ATOM | 342 | C | ALA | A | 57 | 62.085 | 17.299 | 131.228 | 1.00 | 30.88 |
| ATOM | 343 | O | ALA | A | 57 | 61.226 | 17.638 | 132.045 | 1.00 | 30.25 |
| ATOM | 344 | N | GLU | A | 58 | 61.956 | 16.241 | 130.436 | 1.00 | 31.07 |
| ATOM | 345 | CA | GLU | A | 58 | 60.786 | 15.385 | 130.543 | 1.00 | 34.30 |
| ATOM | 346 | CB | GLU | A | 58 | 60.338 | 14.907 | 129.160 | 1.00 | 35.65 |
| ATOM | 347 | CG | GLU | A | 58 | 58.793 | 14.838 | 128.986 | 1.00 | 36.64 |
| ATOM | 348 | CD | GLU | A | 58 | 58.041 | 16.071 | 129.527 | 1.00 | 36.53 |
| ATOM | 349 | OE1 | GLU | A | 58 | 58.538 | 17.214 | 129.363 | 1.00 | 38.32 |
| ATOM | 350 | OE2 | GLU | A | 58 | 56.941 | 15.894 | 130.104 | 1.00 | 33.99 |
| ATOM | 351 | C | GLU | A | 58 | 61.201 | 14.213 | 131.425 | 1.00 | 35.52 |
| ATOM | 352 | O | GLU | A | 58 | 60.381 | 13.576 | 132.082 | 1.00 | 35.87 |
| ATOM | 353 | N | GLU | A | 59 | 62.506 | 13.977 | 131.456 | 1.00 | 36.68 |
| ATOM | 354 | CA | GLU | A | 59 | 63.106 | 12.922 | 132.246 | 1.00 | 36.67 |
| ATOM | 355 | CB | GLU | A | 59 | 62.691 | 11.558 | 131.694 | 1.00 | 38.47 |
| ATOM | 356 | CG | GLU | A | 59 | 63.287 | 11.241 | 130.343 | 1.00 | 42.93 |
| ATOM | 357 | CD | GLU | A | 59 | 63.214 | 9.760 | 130.001 | 1.00 | 46.79 |
| ATOM | 358 | OE1 | GLU | A | 59 | 62.144 | 9.292 | 129.544 | 1.00 | 47.48 |
| ATOM | 359 | OE2 | GLU | A | 59 | 64.239 | 9.063 | 130.198 | 1.00 | 47.84 |
| ATOM | 360 | C | GLU | A | 59 | 64.619 | 13.108 | 132.116 | 1.00 | 35.99 |
| ATOM | 361 | O | GLU | A | 59 | 65.068 | 13.938 | 131.332 | 1.00 | 35.86 |
| ATOM | 362 | N | ARG | A | 60 | 65.402 | 12.338 | 132.866 | 1.00 | 35.25 |
| ATOM | 363 | CA | ARG | A | 60 | 66.855 | 12.454 | 132.801 | 1.00 | 34.39 |
| ATOM | 364 | CB | ARG | A | 60 | 67.536 | 11.325 | 133.589 | 1.00 | 35.43 |
| ATOM | 365 | CG | ARG | A | 60 | 67.711 | 11.638 | 135.064 | 1.00 | 38.14 |
| ATOM | 366 | CD | ARG | A | 60 | 68.487 | 10.568 | 135.787 | 1.00 | 40.57 |
| ATOM | 367 | NE | ARG | A | 60 | 69.811 | 10.376 | 135.207 | 1.00 | 44.90 |
| ATOM | 368 | CZ | ARG | A | 60 | 70.789 | 9.688 | 135.790 | 1.00 | 45.49 |
| ATOM | 369 | NH1 | ARG | A | 60 | 70.583 | 9.129 | 136.973 | 1.00 | 46.54 |
| ATOM | 370 | NH2 | ARG | A | 60 | 71.971 | 9.562 | 135.195 | 1.00 | 46.25 |
| ATOM | 371 | C | ARG | A | 60 | 67.392 | 12.459 | 131.380 | 1.00 | 32.51 |
| ATOM | 372 | O | ARG | A | 60 | 67.131 | 11.541 | 130.600 | 1.00 | 29.35 |
| ATOM | 373 | N | GLY | A | 61 | 68.132 | 13.516 | 131.058 | 1.00 | 30.50 |
| ATOM | 374 | CA | GLY | A | 61 | 68.734 | 13.635 | 129.744 | 1.00 | 30.56 |
| ATOM | 375 | C | GLY | A | 61 | 67.821 | 13.868 | 128.554 | 1.00 | 30.06 |
| ATOM | 376 | O | GLY | A | 61 | 68.264 | 13.731 | 127.406 | 1.00 | 30.72 |

TABLE 1-continued

FGFR1 D2–D3 Complexed with FGF2

| | | | | | | | | | | |
|---|---|---|---|---|---|---|---|---|---|---|
| ATOM | 377 | N | VAL | A | 62 | 66.564 | 14.223 | 128.810 | 1.00 | 28.30 |
| ATOM | 378 | CA | VAL | A | 62 | 65.613 | 14.470 | 127.734 | 1.00 | 27.79 |
| ATOM | 379 | CB | VAL | A | 62 | 64.547 | 13.347 | 127.641 | 1.00 | 28.76 |
| ATOM | 380 | CG1 | VAL | A | 62 | 63.525 | 13.703 | 126.571 | 1.00 | 28.93 |
| ATOM | 381 | CG2 | VAL | A | 62 | 65.208 | 12.008 | 127.327 | 1.00 | 25.92 |
| ATOM | 382 | C | VAL | A | 62 | 64.897 | 15.799 | 127.937 | 1.00 | 28.19 |
| ATOM | 383 | O | VAL | A | 62 | 64.305 | 16.045 | 128.995 | 1.00 | 27.55 |
| ATOM | 384 | N | VAL | A | 63 | 64.941 | 16.651 | 126.915 | 1.00 | 27.67 |
| ATOM | 385 | CA | VAL | A | 63 | 64.292 | 17.952 | 127.006 | 1.00 | 27.32 |
| ATOM | 386 | CB | VAL | A | 63 | 65.318 | 19.109 | 127.120 | 1.00 | 26.53 |
| ATOM | 387 | CG1 | VAL | A | 63 | 66.211 | 18.918 | 128.330 | 1.00 | 25.20 |
| ATOM | 388 | CG2 | VAL | A | 63 | 66.127 | 19.201 | 125.840 | 1.00 | 23.28 |
| ATOM | 389 | C | VAL | A | 63 | 63.417 | 18.284 | 125.803 | 1.00 | 29.19 |
| ATOM | 390 | O | VAL | A | 63 | 63.595 | 17.740 | 124.698 | 1.00 | 30.04 |
| ATOM | 391 | N | SER | A | 64 | 62.469 | 19.184 | 126.043 | 1.00 | 27.23 |
| ATOM | 392 | CA | SER | A | 64 | 61.593 | 19.690 | 125.008 | 1.00 | 28.22 |
| ATOM | 393 | CB | SER | A | 64 | 60.119 | 19.691 | 125.449 | 1.00 | 30.07 |
| ATOM | 394 | OG | SER | A | 64 | 59.827 | 20.752 | 126.355 | 1.00 | 32.47 |
| ATOM | 395 | C | SER | A | 64 | 62.116 | 21.116 | 124.934 | 1.00 | 28.93 |
| ATOM | 396 | O | SER | A | 64 | 62.448 | 21.714 | 125.968 | 1.00 | 29.38 |
| ATOM | 397 | N | ILE | A | 65 | 62.221 | 21.650 | 123.722 | 1.00 | 28.04 |
| ATOM | 398 | CA | ILE | A | 65 | 62.718 | 22.999 | 123.529 | 1.00 | 27.05 |
| ATOM | 399 | CB | ILE | A | 65 | 63.789 | 23.005 | 122.422 | 1.00 | 26.59 |
| ATOM | 400 | CG2 | ILE | A | 65 | 64.172 | 24.434 | 122.035 | 1.00 | 24.34 |
| ATOM | 401 | CG1 | ILE | A | 65 | 64.998 | 22.213 | 122.910 | 1.00 | 24.17 |
| ATOM | 402 | CD1 | ILE | A | 65 | 65.874 | 21.698 | 121.799 | 1.00 | 26.19 |
| ATOM | 403 | C | ILE | A | 65 | 61.540 | 23.872 | 123.144 | 1.00 | 27.68 |
| ATOM | 404 | O | ILE | A | 65 | 60.977 | 23.715 | 122.066 | 1.00 | 28.09 |
| ATOM | 405 | N | LYS | A | 66 | 61.153 | 24.778 | 124.032 | 1.00 | 27.82 |
| ATOM | 406 | CA | LYS | A | 66 | 60.020 | 25.648 | 123.742 | 1.00 | 27.41 |
| ATOM | 407 | CB | LYS | A | 66 | 59.025 | 25.629 | 124.905 | 1.00 | 29.28 |
| ATOM | 408 | CG | LYS | A | 66 | 57.662 | 26.227 | 124.565 | 1.00 | 30.44 |
| ATOM | 409 | CD | LYS | A | 66 | 56.898 | 26.687 | 125.814 | 1.00 | 30.89 |
| ATOM | 410 | CE | LYS | A | 66 | 55.535 | 27.276 | 125.439 | 1.00 | 33.17 |
| ATOM | 411 | NZ | LYS | A | 66 | 54.860 | 28.001 | 126.561 | 1.00 | 34.75 |
| ATOM | 412 | C | LYS | A | 66 | 60.415 | 27.086 | 123.450 | 1.00 | 26.21 |
| ATOM | 413 | O | LYS | A | 66 | 61.122 | 27.723 | 124.234 | 1.00 | 25.68 |
| ATOM | 414 | N | GLY | A | 67 | 59.962 | 27.591 | 122.309 | 1.00 | 27.07 |
| ATOM | 415 | CA | GLY | A | 67 | 60.246 | 28.970 | 121.953 | 1.00 | 27.99 |
| ATOM | 416 | C | GLY | A | 67 | 59.338 | 29.858 | 122.792 | 1.00 | 26.28 |
| ATOM | 417 | O | GLY | A | 67 | 58.128 | 29.844 | 122.622 | 1.00 | 24.02 |
| ATOM | 418 | N | VAL | A | 68 | 59.918 | 30.622 | 123.706 | 1.00 | 26.60 |
| ATOM | 419 | CA | VAL | A | 68 | 59.129 | 31.475 | 124.574 | 1.00 | 27.61 |
| ATOM | 420 | CB | VAL | A | 68 | 60.010 | 32.232 | 125.527 | 1.00 | 25.66 |
| ATOM | 421 | CG1 | VAL | A | 68 | 59.169 | 33.214 | 126.326 | 1.00 | 22.69 |
| ATOM | 422 | CG2 | VAL | A | 68 | 60.733 | 31.253 | 126.420 | 1.00 | 24.49 |
| ATOM | 423 | C | VAL | A | 68 | 58.259 | 32.491 | 123.856 | 1.00 | 31.12 |
| ATOM | 424 | O | VAL | A | 68 | 57.100 | 32.682 | 124.210 | 1.00 | 32.65 |
| ATOM | 425 | N | SER | A | 69 | 58.821 | 33.164 | 122.861 | 1.00 | 34.30 |
| ATOM | 426 | CA | SER | A | 69 | 58.068 | 34.159 | 122.111 | 1.00 | 34.47 |
| ATOM | 427 | CB | SER | A | 69 | 59.011 | 34.932 | 121.190 | 1.00 | 33.89 |
| ATOM | 428 | OG | SER | A | 69 | 58.374 | 36.059 | 120.617 | 1.00 | 31.52 |
| ATOM | 429 | C | SER | A | 69 | 56.989 | 33.475 | 121.282 | 1.00 | 34.11 |
| ATOM | 430 | O | SER | A | 69 | 55.817 | 33.794 | 121.388 | 1.00 | 34.65 |
| ATOM | 431 | N | ALA | A | 70 | 57.397 | 32.520 | 120.463 | 1.00 | 34.71 |
| ATOM | 432 | CA | ALA | A | 70 | 56.459 | 31.809 | 119.603 | 1.00 | 38.14 |
| ATOM | 433 | CB | ALA | A | 70 | 57.228 | 31.060 | 118.527 | 1.00 | 37.34 |
| ATOM | 434 | C | ALA | A | 70 | 55.508 | 30.844 | 120.322 | 1.00 | 39.12 |
| ATOM | 435 | O | ALA | A | 70 | 54.511 | 30.405 | 119.747 | 1.00 | 39.71 |
| ATOM | 436 | N | ASN | A | 71 | 55.811 | 30.520 | 121.573 | 1.00 | 39.27 |
| ATOM | 437 | CA | ASN | A | 71 | 54.986 | 29.584 | 122.320 | 1.00 | 39.70 |
| ATOM | 438 | CB | ASN | A | 71 | 53.626 | 30.212 | 122.640 | 1.00 | 40.65 |
| ATOM | 439 | CG | ASN | A | 71 | 52.815 | 29.386 | 123.638 | 1.00 | 41.06 |
| ATOM | 440 | OD1 | ASN | A | 71 | 52.788 | 29.684 | 124.835 | 1.00 | 41.08 |
| ATOM | 441 | ND2 | ASN | A | 71 | 52.158 | 28.334 | 123.145 | 1.00 | 41.61 |
| ATOM | 442 | C | ASN | A | 71 | 54.786 | 28.295 | 121.497 | 1.00 | 39.74 |
| ATOM | 443 | O | ASN | A | 71 | 53.667 | 27.806 | 121.356 | 1.00 | 40.01 |
| ATOM | 444 | N | ARG | A | 72 | 55.874 | 27.766 | 120.940 | 1.00 | 38.92 |
| ATOM | 445 | CA | ARG | A | 72 | 55.837 | 26.534 | 120.155 | 1.00 | 37.82 |
| ATOM | 446 | CB | ARG | A | 72 | 55.961 | 26.813 | 118.652 | 1.00 | 38.60 |
| ATOM | 447 | CG | ARG | A | 72 | 54.771 | 27.458 | 117.997 | 1.00 | 40.39 |
| ATOM | 448 | CD | ARG | A | 72 | 55.025 | 27.683 | 116.503 | 1.00 | 41.15 |
| ATOW | 449 | NE | ARG | A | 72 | 53.873 | 28.320 | 115.866 | 1.00 | 43.72 |
| ATOM | 450 | CZ | ARG | A | 72 | 52.870 | 27.668 | 115.279 | 1.00 | 43.26 |
| ATOM | 451 | NH1 | ARG | A | 72 | 52.865 | 26.342 | 115.221 | 1.00 | 43.91 |
| ATOM | 452 | NH2 | ARG | A | 72 | 51.844 | 28.349 | 114.782 | 1.00 | 42.43 |
| ATOM | 453 | C | ARG | A | 72 | 57.008 | 25.655 | 120.576 | 1.00 | 36.80 |

TABLE 1-continued

FGFR1 D2–D3 Complexed with FGF2

| ATOM | 454 | O | ARG | A | 72 | 58.002 | 26.149 | 121.096 | 1.00 | 35.83 |
|---|---|---|---|---|---|---|---|---|---|---|
| ATOM | 455 | N | TYR | A | 73 | 56.888 | 24.358 | 120.310 | 1.00 | 36.24 |
| ATOM | 456 | CA | TYR | A | 73 | 57.904 | 23.383 | 120.666 | 1.00 | 34.68 |
| ATOM | 457 | CB | TYR | A | 73 | 57.241 | 22.193 | 121.365 | 1.00 | 34.67 |
| ATOM | 458 | CG | TYR | A | 73 | 56.510 | 22.600 | 122.634 | 1.00 | 37.17 |
| ATOM | 459 | CD1 | TYR | A | 73 | 55.248 | 23.208 | 122.586 | 1.00 | 35.65 |
| ATOM | 460 | CE1 | TYR | A | 73 | 54.625 | 23.675 | 123.752 | 1.00 | 33.81 |
| ATOM | 461 | CD2 | TYR | A | 73 | 57.123 | 22.463 | 123.888 | 1.00 | 37.73 |
| ATOM | 462 | CE2 | TYR | A | 73 | 56.505 | 22.928 | 125.054 | 1.00 | 34.97 |
| ATOM | 463 | CZ | TYR | A | 73 | 55.264 | 23.530 | 124.974 | 1.00 | 33.93 |
| ATOM | 464 | OH | TYR | A | 73 | 54.684 | 23.988 | 126.125 | 1.00 | 31.81 |
| ATOM | 465 | C | TYR | A | 73 | 58.680 | 22.904 | 119.460 | 1.00 | 35.98 |
| ATOM | 466 | O | TYR | A | 73 | 58.093 | 22.516 | 118.453 | 1.00 | 36.90 |
| ATOM | 467 | N | LEU | A | 74 | 60.006 | 22.941 | 119.558 | 1.00 | 36.36 |
| ATOM | 468 | CA | LEU | A | 74 | 60.869 | 22.495 | 118.471 | 1.00 | 36.15 |
| ATOM | 469 | CB | LEU | A | 74 | 62.340 | 22.635 | 118.868 | 1.00 | 35.84 |
| ATOM | 470 | CG | LEU | A | 74 | 63.337 | 21.933 | 117.941 | 1.00 | 35.61 |
| ATOM | 471 | CD1 | LEU | A | 74 | 63.478 | 22.738 | 116.675 | 1.00 | 37.88 |
| ATOM | 472 | CD2 | LEU | A | 74 | 64.689 | 21.791 | 118.601 | 1.00 | 35.93 |
| ATOM | 473 | C | LEU | A | 74 | 60.571 | 21.029 | 118.192 | 1.00 | 37.21 |
| ATOM | 474 | O | LEU | A | 74 | 60.536 | 20.219 | 119.119 | 1.00 | 38.28 |
| ATOM | 475 | N | ALA | A | 75 | 60.361 | 20.685 | 116.926 | 1.00 | 37.24 |
| ATOM | 476 | CA | ALA | A | 75 | 60.076 | 19.310 | 116.572 | 1.00 | 36.32 |
| ATOM | 477 | CB | ALA | A | 75 | 58.599 | 19.140 | 116.354 | 1.00 | 34.38 |
| ATOM | 478 | C | ALA | A | 75 | 60.849 | 18.841 | 115.347 | 1.00 | 38.35 |
| ATOM | 479 | O | ALA | A | 75 | 61.073 | 19.591 | 114.398 | 1.00 | 39.59 |
| ATOM | 480 | N | MET | A | 76 | 61.262 | 17.583 | 115.398 | 1.00 | 41.23 |
| ATOM | 481 | CA | MET | A | 76 | 62.005 | 16.928 | 114.337 | 1.00 | 43.91 |
| ATOM | 482 | CB | MET | A | 76 | 63.081 | 16.043 | 114.955 | 1.00 | 43.17 |
| ATOM | 483 | CG | MET | A | 76 | 63.893 | 15.252 | 113.964 | 1.00 | 42.26 |
| ATOM | 484 | SD | MET | A | 76 | 65.172 | 16.245 | 113.248 | 1.00 | 44.57 |
| ATOM | 485 | CE | MET | A | 76 | 66.636 | 15.543 | 113.985 | 1.00 | 40.99 |
| ATOM | 486 | C | MET | A | 76 | 60.983 | 16.058 | 113.614 | 1.00 | 47.78 |
| ATOM | 487 | O | MET | A | 76 | 60.247 | 15.306 | 114.256 | 1.00 | 47.85 |
| ATOM | 488 | N | LYS | A | 77 | 60.941 | 16.151 | 112.289 | 1.00 | 51.17 |
| ATOM | 489 | CA | LYS | A | 77 | 59.989 | 15.376 | 111.506 | 1.00 | 53.40 |
| ATOM | 490 | CB | LYS | A | 77 | 59.462 | 16.230 | 110.359 | 1.00 | 55.29 |
| ATOM | 491 | CG | LYS | A | 77 | 59.035 | 17.633 | 110.791 | 1.00 | 57.32 |
| ATOM | 492 | CD | LYS | A | 77 | 57.874 | 17.601 | 111.772 | 1.00 | 59.11 |
| ATOM | 493 | CE | LYS | A | 77 | 56.622 | 17.010 | 111.129 | 1.00 | 60.34 |
| ATOM | 494 | NZ | LYS | A | 77 | 55.421 | 17.122 | 112.010 | 1.00 | 60.76 |
| ATOM | 495 | C | LYS | A | 77 | 60.644 | 14.114 | 110.975 | 1.00 | 54.55 |
| ATOM | 496 | O | LYS | A | 77 | 61.869 | 14.008 | 110.949 | 1.00 | 54.47 |
| ATOM | 497 | N | GLU | A | 78 | 59.818 | 13.165 | 110.548 | 1.00 | 56.34 |
| ATOM | 498 | CA | GLU | A | 78 | 60.299 | 11.888 | 110.038 | 1.00 | 58.33 |
| ATOM | 499 | CB | GLU | A | 78 | 59.135 | 11.094 | 109.470 | 1.00 | 60.98 |
| ATOM | 500 | CG | GLU | A | 78 | 58.563 | 11.682 | 108.209 | 1.00 | 65.49 |
| ATOM | 501 | CD | GLU | A | 78 | 57.240 | 11.052 | 107.846 | 1.00 | 69.33 |
| ATOM | 502 | OE1 | GLU | A | 78 | 57.134 | 9.804 | 107.922 | 1.00 | 70.62 |
| ATOM | 503 | OE2 | GLU | A | 78 | 56.308 | 11.805 | 107.484 | 1.00 | 71.91 |
| ATOM | 504 | C | GLU | A | 78 | 61.397 | 12.002 | 108.987 | 1.00 | 57.93 |
| ATOM | 505 | O | GLU | A | 78 | 62.294 | 11.163 | 108.933 | 1.00 | 57.53 |
| ATOM | 506 | N | ASP | A | 79 | 61.328 | 13.036 | 108.154 | 1.00 | 57.03 |
| ATOM | 507 | CA | ASP | A | 79 | 62.324 | 13.234 | 107.102 | 1.00 | 56.19 |
| ATOM | 508 | CB | ASP | A | 79 | 61.695 | 13.958 | 105.914 | 1.00 | 54.79 |
| ATOM | 509 | CG | ASP | A | 79 | 61.251 | 15.353 | 106.264 | 1.00 | 54.84 |
| ATOM | 510 | OD1 | ASP | A | 79 | 60.626 | 16.013 | 105.406 | 1.00 | 55.03 |
| ATOM | 511 | OD2 | ASP | A | 79 | 61.531 | 15.788 | 107.400 | 1.00 | 54.33 |
| ATOM | 512 | C | ASP | A | 79 | 63.527 | 14.032 | 107.599 | 1.00 | 55.83 |
| ATOM | 513 | O | ASP | A | 79 | 64.516 | 14.210 | 106.876 | 1.00 | 56.39 |
| ATOM | 514 | N | GLY | A | 80 | 63.430 | 14.528 | 108.827 | 1.00 | 53.82 |
| ATOM | 515 | CA | GLY | A | 80 | 64.532 | 15.283 | 109.388 | 1.00 | 51.60 |
| ATOM | 516 | C | GLY | A | 80 | 64.448 | 16.794 | 109.282 | 1.00 | 49.35 |
| ATOM | 517 | O | GLY | A | 80 | 65.457 | 17.483 | 109.428 | 1.00 | 48.60 |
| ATOM | 518 | N | ARG | A | 81 | 63.263 | 17.328 | 109.023 | 1.00 | 47.11 |
| ATOM | 519 | CA | ARG | A | 81 | 63.142 | 18.772 | 108.942 | 1.00 | 45.50 |
| ATOM | 520 | CB | ARG | A | 81 | 62.191 | 19.185 | 107.814 | 1.00 | 46.15 |
| ATOM | 521 | CG | ARG | A | 81 | 60.754 | 18.770 | 108.012 | 1.00 | 47.86 |
| ATOM | 522 | CD | ARG | A | 81 | 59.879 | 19.203 | 106.845 | 1.00 | 48.98 |
| ATOM | 523 | NE | ARG | A | 81 | 58.461 | 18.940 | 107.100 | 1.00 | 50.64 |
| ATOM | 524 | CZ | ARG | A | 81 | 57.931 | 17.726 | 107.253 | 1.00 | 51.67 |
| ATOM | 525 | NH1 | ARG | A | 81 | 58.696 | 16.635 | 107.176 | 1.00 | 50.89 |
| ATOM | 526 | NH2 | ARG | A | 81 | 56.631 | 17.597 | 107.492 | 1.00 | 51.50 |
| ATOM | 527 | C | ARG | A | 81 | 62.649 | 19.296 | 110.283 | 1.00 | 44.44 |
| ATOM | 528 | O | ARG | A | 81 | 61.926 | 18.614 | 111.001 | 1.00 | 43.89 |
| ATOM | 529 | N | LEU | A | 82 | 63.052 | 20.510 | 110.629 | 1.00 | 43.77 |
| ATOM | 530 | CA | LEU | A | 82 | 62.641 | 21.096 | 111.897 | 1.00 | 42.44 |

TABLE 1-continued

FGFR1 D2–D3 Complexed with FGF2

| ATOM | 531 | CB | LEU | A | 82 | 63.772 | 21.908 | 112.533 | 1.00 | 43.49 |
|---|---|---|---|---|---|---|---|---|---|---|
| ATOM | 532 | CG | LEU | A | 82 | 65.163 | 21.304 | 112.660 | 1.00 | 44.62 |
| ATOM | 533 | CD1 | LEU | A | 82 | 66.064 | 22.291 | 113.388 | 1.00 | 44.86 |
| ATOM | 534 | CD2 | LEU | A | 82 | 65.080 | 19.985 | 113.408 | 1.00 | 46.49 |
| ATOM | 535 | C | LEU | A | 82 | 61.466 | 22.025 | 111.717 | 1.00 | 41.65 |
| ATOM | 536 | O | LEU | A | 82 | 61.255 | 22.585 | 110.643 | 1.00 | 42.91 |
| ATOM | 537 | N | LEU | A | 83 | 60.709 | 22.189 | 112.791 | 1.00 | 40.18 |
| ATOM | 538 | CA | LEU | A | 83 | 59.565 | 23.083 | 112.812 | 1.00 | 39.02 |
| ATOM | 539 | CB | LEU | A | 83 | 58.405 | 22.518 | 111.987 | 1.00 | 36.36 |
| ATOM | 540 | CG | LEU | A | 83 | 57.635 | 21.274 | 112.448 | 1.00 | 34.63 |
| ATOM | 541 | CD1 | LEU | A | 83 | 56.792 | 21.559 | 113.671 | 1.00 | 31.47 |
| ATOM | 542 | CD2 | LEU | A | 83 | 56.746 | 20.832 | 111.313 | 1.00 | 34.37 |
| ATOM | 543 | C | LEU | A | 83 | 59.177 | 23.194 | 114.273 | 1.00 | 40.14 |
| ATOM | 544 | O | LEU | A | 83 | 59.630 | 22.403 | 115.095 | 1.00 | 38.27 |
| ATOM | 545 | N | ALA | A | 84 | 58.351 | 24.176 | 114.604 | 1.00 | 41.60 |
| ATOM | 546 | CA | ALA | A | 64 | 57.934 | 24.344 | 115.986 | 1.00 | 43.32 |
| ATOM | 547 | CB | ALA | A | 84 | 58.311 | 25.730 | 116.490 | 1.00 | 41.67 |
| ATOM | 548 | C | ALA | A | 84 | 56.438 | 24.112 | 116.114 | 1.00 | 45.19 |
| ATOM | 549 | O | ALA | A | 84 | 55.623 | 24.927 | 115.677 | 1.00 | 46.57 |
| ATOM | 550 | N | SER | A | 85 | 56.096 | 22.981 | 116.721 | 1.00 | 46.92 |
| ATOM | 551 | CA | SER | A | 85 | 54.714 | 22.561 | 116.938 | 1.00 | 47.45 |
| ATOM | 552 | CB | SER | A | 85 | 54.703 | 21.115 | 117.450 | 1.00 | 47.39 |
| ATOM | 553 | OG | SER | A | 85 | 53.386 | 20.674 | 117.709 | 1.00 | 49.88 |
| ATOM | 554 | C | SER | A | 85 | 53.983 | 23.465 | 117.928 | 1.00 | 48.14 |
| ATOM | 555 | O | SER | A | 85 | 54.601 | 24.078 | 118.799 | 1.00 | 49.09 |
| ATOM | 556 | N | LYS | A | 86 | 52.664 | 23.547 | 117.793 | 1.00 | 47.71 |
| ATOM | 557 | CA | LYS | A | 86 | 51.878 | 24.385 | 118.684 | 1.00 | 47.45 |
| ATOM | 558 | CB | LYS | A | 86 | 50.490 | 24.614 | 118.095 | 1.00 | 49.56 |
| ATOM | 559 | CG | LYS | A | 86 | 49.813 | 25.891 | 118.567 | 1.00 | 51.27 |
| ATOM | 560 | CD | LYS | A | 86 | 50.287 | 27.073 | 117.740 | 1.00 | 53.09 |
| ATOM | 561 | CE | LYS | A | 86 | 49.472 | 28.321 | 118.005 | 1.00 | 53.92 |
| ATOM | 562 | NZ | LYS | A | 86 | 49.716 | 29.341 | 116.934 | 1.00 | 57.90 |
| ATOM | 563 | C | LYS | A | 86 | 51.752 | 23.692 | 120.033 | 1.00 | 46.65 |
| ATOM | 564 | O | LYS | A | 86 | 51.873 | 24.319 | 121.086 | 1.00 | 46.47 |
| ATOM | 565 | N | SER | A | 87 | 51.496 | 22.389 | 119.986 | 1.00 | 45.59 |
| ATOM | 566 | CA | SER | A | 87 | 51.351 | 21.587 | 121.194 | 1.00 | 44.66 |
| ATOM | 567 | CB | SER | A | 87 | 49.939 | 20.992 | 121.282 | 1.00 | 43.08 |
| ATOM | 568 | OG | SER | A | 87 | 49.701 | 20.091 | 120.221 | 1.00 | 40.33 |
| ATOM | 569 | C | SER | A | 87 | 52.391 | 20.474 | 121.144 | 1.00 | 44.59 |
| ATOM | 570 | O | SER | A | 87 | 52.881 | 20.111 | 120.074 | 1.00 | 43.61 |
| ATOM | 571 | N | VAL | A | 88 | 52.718 | 19.926 | 122.306 | 1.00 | 44.63 |
| ATOM | 572 | CA | VAL | A | 88 | 53.729 | 18.883 | 122.374 | 1.00 | 43.82 |
| ATOM | 573 | CB | VAL | A | 88 | 54.187 | 18.656 | 123.824 | 1.00 | 43.24 |
| ATOM | 574 | CG1 | VAL | A | 88 | 55.408 | 17.749 | 123.837 | 1.00 | 42.87 |
| ATOM | 575 | CG2 | VAL | A | 88 | 54.495 | 19.995 | 124.490 | 1.00 | 41.50 |
| ATOM | 576 | C | VAL | A | 88 | 53.314 | 17.542 | 121.782 | 1.00 | 43.66 |
| ATOM | 577 | O | VAL | A | 88 | 52.230 | 17.028 | 122.066 | 1.00 | 44.12 |
| ATOM | 578 | N | THR | A | 89 | 54.182 | 16.991 | 120.938 | 1.00 | 43.04 |
| ATOM | 579 | CA | THR | A | 89 | 53.950 | 15.683 | 120.337 | 1.00 | 42.15 |
| ATOM | 580 | CB | THR | A | 89 | 53.761 | 15.750 | 118.798 | 1.00 | 43.10 |
| ATOM | 581 | OG1 | THR | A | 89 | 55.033 | 15.794 | 118.144 | 1.00 | 46.42 |
| ATOM | 582 | CG2 | THR | A | 89 | 52.976 | 16.988 | 118.422 | 1.00 | 43.70 |
| ATOM | 583 | C | THR | A | 89 | 55.183 | 14.862 | 120.706 | 1.00 | 41.22 |
| ATOM | 584 | O | THR | A | 89 | 56.020 | 15.320 | 121.480 | 1.00 | 40.52 |
| ATOM | 585 | N | ASP | A | 90 | 55.311 | 13.657 | 120.172 | 1.00 | 41.76 |
| ATOM | 586 | CA | ASP | A | 90 | 56.447 | 12.821 | 120.545 | 1.00 | 42.49 |
| ATOM | 587 | CB | ASP | A | 90 | 56.095 | 11.340 | 120.379 | 1.00 | 43.14 |
| ATOM | 588 | CG | ASP | A | 90 | 56.112 | 10.893 | 118.925 | 1.00 | 45.82 |
| ATOM | 589 | OD1 | ASP | A | 90 | 55.470 | 11.559 | 118.084 | 1.00 | 45.52 |
| ATOM | 590 | OD2 | ASP | A | 90 | 56.769 | 9.869 | 118.625 | 1.00 | 47.64 |
| ATOM | 591 | C | ASP | A | 90 | 57.727 | 13.143 | 119.785 | 1.00 | 42.84 |
| ATOM | 592 | O | ASP | A | 90 | 58.759 | 12.495 | 119.989 | 1.00 | 43.34 |
| ATOM | 593 | N | GLU | A | 91 | 57.664 | 14.148 | 118.915 | 1.00 | 42.08 |
| ATOM | 594 | CA | GLU | A | 91 | 58.825 | 14.557 | 118.127 | 1.00 | 39.76 |
| ATOM | 595 | CB | GLU | A | 91 | 58.409 | 14.855 | 116.681 | 1.00 | 39.16 |
| ATOM | 596 | CG | GLU | A | 91 | 58.045 | 13.608 | 115.869 | 1.00 | 39.61 |
| ATOM | 597 | CD | GLU | A | 91 | 57.290 | 13.940 | 114.595 | 1.00 | 39.92 |
| ATOM | 598 | OE1 | GLU | A | 91 | 56.277 | 14.666 | 114.694 | 1.00 | 40.67 |
| ATOM | 599 | OE2 | GLU | A | 91 | 57.696 | 13.475 | 113.505 | 1.00 | 37.43 |
| ATOM | 600 | C | GLU | A | 91 | 59.435 | 15.794 | 118.756 | 1.00 | 37.44 |
| ATOM | 601 | O | GLU | A | 91 | 60.395 | 16.354 | 118.241 | 1.00 | 35.98 |
| ATOM | 602 | N | CYS | A | 92 | 58.878 | 16.201 | 119.887 | 1.00 | 35.82 |
| ATOM | 603 | CA | CYS | A | 92 | 59.355 | 17.386 | 120.581 | 1.00 | 36.58 |
| ATOM | 604 | CB | CYS | A | 92 | 58.161 | 18.157 | 121.138 | 1.00 | 38.16 |
| ATOM | 605 | SG | CYS | A | 92 | 57.052 | 18.772 | 119.863 | 1.00 | 43.78 |
| ATOM | 606 | C | CYS | A | 92 | 60.363 | 17.110 | 121.703 | 1.00 | 35.32 |
| ATOM | 607 | O | CYS | A | 92 | 60.642 | 17.990 | 122.530 | 1.00 | 33.99 |

TABLE 1-continued

FGFR1 D2–D3 Complexed with FGF2

| ATOM | 608 | N | PHE | A | 93 | 60.926 | 15.902 | 121.716 | 1.00 | 33.77 |
|---|---|---|---|---|---|---|---|---|---|---|
| ATOM | 609 | CA | PHE | A | 93 | 61.886 | 15.526 | 122.750 | 1.00 | 31.34 |
| ATOM | 610 | CB | PHE | A | 93 | 61.323 | 14.349 | 123.541 | 1.00 | 27.27 |
| ATOM | 611 | CG | PHE | A | 93 | 60.019 | 14.670 | 124.211 | 1.00 | 24.63 |
| ATOM | 612 | CD1 | PHE | A | 93 | 59.981 | 15.537 | 125.297 | 1.00 | 23.64 |
| ATOM | 613 | CD2 | PHE | A | 93 | 58.819 | 14.185 | 123.703 | 1.00 | 24.13 |
| ATOM | 614 | CE1 | PHE | A | 93 | 58.766 | 15.924 | 125.864 | 1.00 | 22.52 |
| ATOM | 615 | CE2 | PHE | A | 93 | 57.598 | 14.571 | 124.268 | 1.00 | 23.86 |
| ATOM | 616 | CZ | PHE | A | 93 | 57.576 | 15.442 | 125.351 | 1.00 | 21.53 |
| ATOM | 617 | C | PHE | A | 93 | 63.261 | 15.218 | 122.184 | 1.00 | 31.25 |
| ATOM | 618 | O | PHE | A | 93 | 63.389 | 14.592 | 121.132 | 1.00 | 31.43 |
| ATOM | 619 | N | PHE | A | 94 | 64.290 | 15.679 | 122.889 | 1.00 | 31.24 |
| ATOM | 620 | CA | PHE | A | 94 | 65.663 | 15.489 | 122.445 | 1.00 | 30.43 |
| ATOM | 621 | CB | PHE | A | 94 | 66.181 | 16.789 | 121.821 | 1.00 | 30.29 |
| ATOM | 622 | CG | PHE | A | 94 | 65.320 | 17.309 | 120.701 | 1.00 | 29.49 |
| ATOM | 623 | CD1 | PHE | A | 94 | 65.534 | 16.892 | 119.386 | 1.00 | 28.03 |
| ATOM | 624 | CD2 | PHE | A | 94 | 64.265 | 18.182 | 120.967 | 1.00 | 27.75 |
| ATOM | 625 | CE1 | PHE | A | 94 | 64.707 | 17.333 | 118.363 | 1.00 | 26.35 |
| ATOM | 626 | CE2 | PHE | A | 94 | 63.434 | 18.625 | 119.947 | 1.00 | 25.73 |
| ATOM | 627 | CZ | PHE | A | 94 | 63.653 | 18.204 | 118.649 | 1.00 | 25.48 |
| ATOM | 628 | C | PHE | A | 94 | 66.584 | 15.089 | 123.582 | 1.00 | 30.16 |
| ATOM | 629 | O | PHE | A | 94 | 66.328 | 15.407 | 124.748 | 1.00 | 30.02 |
| ATOM | 630 | N | PHE | A | 95 | 67.657 | 14.393 | 123.225 | 1.00 | 29.48 |
| ATOM | 631 | CA | PHE | A | 95 | 68.658 | 13.968 | 124.186 | 1.00 | 29.03 |
| ATOM | 632 | CB | PHE | A | 95 | 69.362 | 12.721 | 123.668 | 1.00 | 31.70 |
| ATOM | 633 | CG | PHE | A | 95 | 68.469 | 11.523 | 123.582 | 1.00 | 34.61 |
| ATOM | 634 | CD1 | PHE | A | 95 | 68.600 | 10.618 | 122.533 | 1.00 | 36.23 |
| ATOM | 635 | CD2 | PHE | A | 95 | 67.497 | 11.291 | 124.553 | 1.00 | 36.09 |
| ATOM | 636 | CE1 | PHE | A | 95 | 67.776 | 9.492 | 122.447 | 1.00 | 35.87 |
| ATOM | 637 | CE2 | PHE | A | 95 | 66.665 | 10.170 | 124.480 | 1.00 | 36.33 |
| ATOM | 638 | CZ | PHE | A | 95 | 66.807 | 9.269 | 123.421 | 1.00 | 36.80 |
| ATOM | 639 | C | PHE | A | 95 | 69.659 | 15.099 | 124.365 | 1.00 | 28.52 |
| ATOM | 640 | O | PHE | A | 95 | 70.512 | 15.339 | 123.502 | 1.00 | 27.18 |
| ATOM | 641 | N | GLU | A | 96 | 69.533 | 15.819 | 125.474 | 1.00 | 28.65 |
| ATOM | 642 | CA | GLU | A | 96 | 70.448 | 16.910 | 125.744 | 1.00 | 29.50 |
| ATOM | 643 | CB | GLU | A | 96 | 69.858 | 17.889 | 126.756 | 1.00 | 27.99 |
| ATOM | 644 | CG | GLU | A | 96 | 70.801 | 19.042 | 127.058 | 1.00 | 29.21 |
| ATOM | 645 | CD | GLU | A | 96 | 70.265 | 20.005 | 128.098 | 1.00 | 31.55 |
| ATOM | 646 | OE1 | GLU | A | 96 | 70.020 | 19.575 | 129.250 | 1.00 | 31.32 |
| ATOM | 647 | OE2 | GLU | A | 96 | 70.097 | 21.198 | 127.767 | 1.00 | 33.49 |
| ATOM | 648 | C | GLU | A | 96 | 71.707 | 16.280 | 126.311 | 1.00 | 31.72 |
| ATOM | 649 | O | GLU | A | 96 | 71.683 | 15.666 | 127.384 | 1.00 | 34.11 |
| ATOM | 650 | N | ARG | A | 97 | 72.803 | 16.404 | 125.578 | 1.00 | 31.74 |
| ATOM | 651 | CA | ARG | A | 97 | 74.056 | 15.835 | 126.034 | 1.00 | 31.84 |
| ATOM | 652 | CB | ARG | A | 97 | 74.425 | 14.637 | 125.176 | 1.00 | 34.27 |
| ATOM | 653 | CG | ARG | A | 97 | 75.761 | 14.043 | 125.540 | 1.00 | 38.54 |
| ATOM | 654 | CD | ARG | A | 97 | 76.319 | 13.201 | 124.417 | 1.00 | 42.56 |
| ATOM | 655 | NE | ARG | A | 97 | 77.711 | 12.881 | 124.699 | 1.00 | 49.50 |
| ATOM | 656 | CZ | ARG | A | 97 | 78.102 | 11.907 | 125.513 | 1.00 | 52.72 |
| ATOM | 657 | NH1 | ARG | A | 97 | 77.191 | 11.143 | 126.114 | 1.00 | 52.62 |
| ATOM | 658 | NH2 | ARG | A | 97 | 79.400 | 11.722 | 125.756 | 1.00 | 51.89 |
| ATOM | 659 | C | ARG | A | 97 | 75.198 | 16.838 | 125.995 | 1.00 | 30.59 |
| ATOM | 660 | O | ARG | A | 97 | 75.453 | 17.463 | 124.969 | 1.00 | 32.34 |
| ATOM | 661 | N | LEU | A | 98 | 75.872 | 16.999 | 127.126 | 1.00 | 28.50 |
| ATOM | 662 | C | ALEU | A | 98 | 77.019 | 17.884 | 127.221 | 1.00 | 27.17 |
| ATOM | 663 | CB | LEU | A | 98 | 77.184 | 18.371 | 128.661 | 1.00 | 21.92 |
| ATOM | 664 | CG | LEU | A | 98 | 78.523 | 18.977 | 129.071 | 1.00 | 20.39 |
| ATOM | 665 | CD1 | LEU | A | 98 | 78.988 | 19.998 | 128.063 | 1.00 | 21.52 |
| ATOM | 666 | CD2 | LEU | A | 98 | 78.376 | 19.607 | 130.430 | 1.00 | 21.24 |
| ATOM | 667 | C | LEU | A | 98 | 78.242 | 17.063 | 126.777 | 1.00 | 28.93 |
| ATOM | 668 | O | LEU | A | 98 | 78.787 | 16.276 | 127.546 | 1.00 | 31.40 |
| ATOM | 669 | N | GLU | A | 99 | 78.652 | 17.240 | 125.524 | 1.00 | 30.17 |
| ATOM | 670 | CA | GLU | A | 99 | 79.785 | 16.515 | 124.951 | 1.00 | 31.19 |
| ATOM | 671 | CB | GLU | A | 99 | 79.948 | 16.876 | 123.476 | 1.00 | 29.56 |
| ATOM | 672 | CG | GLU | A | 99 | 78.693 | 16.717 | 122.678 | 1.00 | 31.83 |
| ATOM | 673 | CD | GLU | A | 99 | 78.207 | 15.291 | 122.655 | 1.00 | 33.86 |
| ATOM | 674 | OE1 | GLU | A | 99 | 77.101 | 15.036 | 122.129 | 1.00 | 32.15 |
| ATOM | 675 | OE2 | GLU | A | 99 | 78.943 | 14.422 | 123.161 | 1.00 | 37.73 |
| ATOM | 676 | C | GLU | A | 99 | 81.098 | 16.808 | 125.661 | 1.00 | 33.20 |
| ATOM | 677 | O | GLU | A | 99 | 81.194 | 17.747 | 126.467 | 1.00 | 32.11 |
| ATOM | 678 | N | SER | A | 100 | 82.119 | 16.020 | 125.323 | 1.00 | 34.00 |
| ATOM | 679 | CA | SER | A | 100 | 83.432 | 16.186 | 125.930 | 1.00 | 36.02 |
| ATOM | 680 | CB | SER | A | 100 | 84.331 | 14.982 | 125.628 | 1.00 | 37.15 |
| ATOM | 681 | OG | SER | A | 100 | 84.846 | 15.048 | 124.312 | 1.00 | 42.19 |
| ATOM | 682 | C | SER | A | 100 | 84.142 | 17.468 | 125.502 | 1.00 | 35.51 |
| ATOM | 683 | O | SER | A | 100 | 85.099 | 17.882 | 126.151 | 1.00 | 36.82 |
| ATOM | 684 | N | ASN | A | 101 | 83.690 | 18.104 | 124.425 | 1.00 | 35.15 |

TABLE 1-continued

FGFR1 D2–D3 Complexed with FGF2

| ATOM | 685 | CA | ASN | A | 101 | 84.338 | 19.343 | 123.984 | 1.00 | 33.34 |
|---|---|---|---|---|---|---|---|---|---|---|
| ATOM | 686 | CB | ASN | A | 101 | 84.212 | 19.521 | 122.475 | 1.00 | 35.00 |
| ATOM | 687 | CG | ASN | A | 101 | 82.782 | 19.684 | 122.040 | 1.00 | 37.73 |
| ATOM | 688 | OD1 | ASN | A | 101 | 81.895 | 19.882 | 122.873 | 1.00 | 39.82 |
| ATOM | 689 | ND2 | ASN | A | 101 | 82.541 | 19.609 | 120.736 | 1.00 | 39.52 |
| ATOM | 690 | C | ASN | A | 101 | 83.721 | 20.546 | 124.677 | 1.00 | 30.87 |
| ATOM | 691 | O | ASN | A | 101 | 84.142 | 21.669 | 124.448 | 1.00 | 29.80 |
| ATOM | 692 | N | ASN | A | 102 | 82.722 | 20.287 | 125.521 | 1.00 | 30.67 |
| ATOM | 693 | CA | ASN | A | 102 | 81.991 | 21.309 | 126.286 | 1.00 | 29.39 |
| ATOM | 694 | CB | ASN | A | 102 | 82.929 | 22.348 | 126.914 | 1.00 | 31.37 |
| ATOM | 695 | CG | ASN | A | 102 | 83.496 | 21.900 | 128.257 | 1.00 | 33.09 |
| ATOM | 696 | OD1 | ASN | A | 102 | 83.095 | 20.871 | 128.810 | 1.00 | 33.67 |
| ATOM | 697 | ND2 | ASN | A | 102 | 84.429 | 22.683 | 128.789 | 1.00 | 32.79 |
| ATOM | 698 | C | ASN | A | 102 | 80.911 | 22.031 | 125.508 | 1.00 | 27.39 |
| ATOM | 699 | O | ASN | A | 102 | 80.558 | 23.164 | 125.818 | 1.00 | 26.13 |
| ATOM | 700 | N | TYR | A | 103 | 80.389 | 21.354 | 124.500 | 1.00 | 26.24 |
| ATOM | 701 | CA | TYR | A | 103 | 79.314 | 21.879 | 123.697 | 1.00 | 26.55 |
| ATOM | 702 | CB | TYR | A | 103 | 79.766 | 21.964 | 122.244 | 1.00 | 29.17 |
| ATOM | 703 | CG | TYR | A | 103 | 80.580 | 23.210 | 121.940 | 1.00 | 30.57 |
| ATOM | 704 | CD1 | TYR | A | 103 | 79.959 | 24.456 | 121.824 | 1.00 | 30.73 |
| ATOM | 705 | CE1 | TYR | A | 103 | 80.692 | 25.600 | 121.576 | 1.00 | 30.98 |
| ATOM | 706 | CD2 | TYR | A | 103 | 81.968 | 23.151 | 121.797 | 1.00 | 29.10 |
| ATOM | 707 | CE2 | TYR | A | 103 | 82.713 | 24.300 | 121.551 | 1.00 | 28.71 |
| ATOM | 708 | CZ | TYR | A | 103 | 82.068 | 25.518 | 121.441 | 1.00 | 31.03 |
| ATOM | 709 | OH | TYR | A | 103 | 82.785 | 26.665 | 121.192 | 1.00 | 33.17 |
| ATOM | 710 | C | TYR | A | 103 | 78.150 | 20.904 | 123.883 | 1.00 | 26.39 |
| ATOM | 711 | O | TYR | A | 103 | 78.359 | 19.738 | 124.203 | 1.00 | 25.31 |
| ATOM | 712 | N | ASN | A | 104 | 76.926 | 21.394 | 123.729 | 1.00 | 26.69 |
| ATOM | 713 | CA | ASN | A | 104 | 75.738 | 20.565 | 123.893 | 1.00 | 25.29 |
| ATOM | 714 | CB | ASN | A | 104 | 74.596 | 21.367 | 124.536 | 1.00 | 25.30 |
| ATOM | 715 | CG | ASN | A | 104 | 74.775 | 21.582 | 126.038 | 1.00 | 25.81 |
| ATOM | 716 | OD1 | ASN | A | 104 | 75.896 | 21.637 | 126.545 | 1.00 | 26.52 |
| ATOM | 717 | ND2 | ASN | A | 104 | 73.658 | 21.728 | 126.750 | 1.00 | 24.06 |
| ATOM | 718 | C | ASN | A | 104 | 75.267 | 20.094 | 122.534 | 1.00 | 25.53 |
| ATOM | 719 | O | ASN | A | 104 | 75.528 | 20.734 | 121.521 | 1.00 | 24.70 |
| ATOM | 720 | N | THR | A | 105 | 74.580 | 18.960 | 122.523 | 1.00 | 26.46 |
| ATOM | 721 | CA | THR | A | 105 | 74.005 | 18.429 | 121.299 | 1.00 | 27.72 |
| ATOM | 722 | CB | THR | A | 105 | 74.758 | 17.240 | 120.765 | 1.00 | 28.31 |
| ATOM | 723 | OG1 | THR | A | 105 | 74.707 | 16.185 | 121.730 | 1.00 | 30.41 |
| ATOM | 724 | CG2 | THR | A | 105 | 76.187 | 17.630 | 120.464 | 1.00 | 29.27 |
| ATOM | 725 | C | THR | A | 105 | 72.597 | 17.975 | 121.621 | 1.00 | 27.86 |
| ATOM | 726 | O | THR | A | 105 | 72.337 | 17.441 | 122.703 | 1.00 | 26.82 |
| ATOM | 727 | N | TYR | A | 106 | 71.691 | 18.189 | 120.675 | 1.00 | 27.97 |
| ATOM | 728 | CA | TYR | A | 106 | 70.309 | 17.808 | 120.869 | 1.00 | 28.05 |
| ATOM | 729 | CB | TYR | A | 106 | 69.443 | 19.054 | 120.819 | 1.00 | 25.08 |
| ATOM | 730 | CG | TYR | A | 106 | 69.764 | 19.973 | 121.966 | 1.00 | 23.18 |
| ATOM | 731 | CD1 | TYR | A | 106 | 68.973 | 19.987 | 123.118 | 1.00 | 21.13 |
| ATOM | 732 | CE1 | TYR | A | 106 | 69.297 | 20.791 | 124.205 | 1.00 | 20.58 |
| ATOM | 733 | CD2 | TYR | A | 106 | 70.894 | 20.790 | 121.928 | 1.00 | 20.43 |
| ATOM | 734 | CE2 | TYR | A | 106 | 71.229 | 21.591 | 123.004 | 1.00 | 21.60 |
| ATOM | 735 | CZ | TYR | A | 106 | 70.431 | 21.591 | 124.147 | 1.00 | 21.86 |
| ATOM | 736 | OH | TYR | A | 106 | 70.798 | 22.368 | 125.234 | 1.00 | 22.45 |
| ATOM | 737 | C | TYR | A | 106 | 69.893 | 16.784 | 119.838 | 1.00 | 30.08 |
| ATOM | 738 | O | TYR | A | 106 | 69.630 | 17.105 | 118.676 | 1.00 | 30.82 |
| ATOM | 739 | N | ARG | A | 107 | 69.841 | 15.538 | 120.292 | 1.00 | 31.66 |
| ATOM | 740 | CA | ARG | A | 107 | 69.503 | 14.405 | 119.447 | 1.00 | 32.61 |
| ATOM | 741 | CB | ARG | A | 107 | 70.392 | 13.220 | 119.842 | 1.00 | 32.36 |
| ATOM | 742 | CG | ARG | A | 107 | 70.434 | 12.064 | 118.872 | 1.00 | 32.70 |
| ATOM | 743 | CD | ARG | A | 107 | 71.697 | 11.253 | 119.117 | 1.00 | 34.85 |
| ATOM | 744 | NE | ARG | A | 107 | 71.800 | 10.744 | 120.491 | 1.00 | 36.65 |
| ATOM | 745 | CZ | ARG | A | 107 | 71.106 | 9.708 | 120.963 | 1.00 | 35.72 |
| ATOM | 746 | NH1 | ARG | A | 107 | 70.258 | 9.071 | 120.169 | 1.00 | 36.28 |
| ATOM | 747 | NH2 | ARG | A | 107 | 71.259 | 9.301 | 122.218 | 1.00 | 32.47 |
| ATOM | 748 | C | ARG | A | 107 | 68.039 | 14.040 | 119.589 | 1.00 | 33.19 |
| ATOM | 749 | O | ARG | A | 107 | 67.524 | 13.930 | 120.700 | 1.00 | 34.18 |
| ATOM | 750 | N | SER | A | 108 | 67.375 | 13.858 | 118.453 | 1.00 | 34.58 |
| ATOM | 751 | CA | SER | A | 108 | 65.966 | 13.477 | 118.416 | 1.00 | 36.35 |
| ATOM | 752 | CB | SER | A | 108 | 65.511 | 13.306 | 116.960 | 1.00 | 37.24 |
| ATOM | 753 | OG | SER | A | 108 | 64.124 | 13.019 | 116.878 | 1.00 | 39.38 |
| ATOM | 754 | C | SER | A | 108 | 65.735 | 12.162 | 119.160 | 1.00 | 37.63 |
| ATOM | 755 | O | SER | A | 108 | 66.339 | 11.134 | 118.837 | 1.00 | 35.70 |
| ATOM | 756 | N | ARG | A | 109 | 64.851 | 12.189 | 120.148 | 1.00 | 40.12 |
| ATOM | 757 | CA | ARG | A | 109 | 64.557 | 10.984 | 120.905 | 1.00 | 42.97 |
| ATOM | 758 | CB | ARG | A | 109 | 63.705 | 11.321 | 122.139 | 1.00 | 46.15 |
| ATOM | 759 | CG | ARG | A | 109 | 63.406 | 10.117 | 123.032 | 1.00 | 49.94 |
| ATOM | 760 | CD | ARG | A | 109 | 62.781 | 10.490 | 124.386 | 1.00 | 53.41 |
| ATOM | 761 | NE | ARG | A | 109 | 61.383 | 10.928 | 124.305 | 1.00 | 56.68 |

TABLE 1-continued

FGFR1 D2–D3 Complexed with FGF2

| | | | | | | | | | | |
|---|---|---|---|---|---|---|---|---|---|---|
| ATOM | 762 | CZ | ARG | A | 109 | 60.598 | 11.121 | 125.367 | 1.00 | 57.49 |
| ATOM | 763 | NH1 | ARG | A | 109 | 61.066 | 10.914 | 126.594 | 1.00 | 58.10 |
| ATOM | 764 | NH2 | ARG | A | 109 | 59.345 | 11.526 | 125.210 | 1.00 | 57.66 |
| ATOM | 765 | C | ARG | A | 109 | 63.810 | 10.009 | 120.006 | 1.00 | 43.50 |
| ATOM | 766 | O | ARG | A | 109 | 63.879 | 8.800 | 120.204 | 1.00 | 43.69 |
| ATOM | 767 | N | LYS | A | 110 | 63.112 | 10.541 | 119.007 | 1.00 | 44.03 |
| ATOM | 768 | CA | LYS | A | 110 | 62.349 | 9.706 | 118.097 | 1.00 | 44.44 |
| ATOM | 769 | CB | LYS | A | 110 | 61.105 | 10.457 | 117.627 | 1.00 | 45.66 |
| ATOM | 770 | CG | LYS | A | 110 | 60.215 | 9.607 | 116.755 | 1.00 | 47.20 |
| ATOM | 771 | CD | LYS | A | 110 | 58.823 | 10.168 | 116.618 | 1.00 | 49.29 |
| ATOM | 772 | CE | LYS | A | 110 | 57.912 | 9.130 | 115.962 | 1.00 | 50.25 |
| ATOM | 773 | NZ | LYS | A | 110 | 56.508 | 9.603 | 115.819 | 1.00 | 51.01 |
| ATOM | 774 | C | LYS | A | 110 | 63.150 | 9.222 | 116.893 | 1.00 | 46.02 |
| ATOM | 775 | O | LYS | A | 110 | 63.013 | 8.068 | 116.477 | 1.00 | 47.58 |
| ATOM | 776 | N | TYR | A | 111 | 63.974 | 10.099 | 116.324 | 1.00 | 46.38 |
| ATOM | 777 | CA | TYR | A | 111 | 64.807 | 9.743 | 115.172 | 1.00 | 46.60 |
| ATOM | 778 | CB | TYR | A | 111 | 64.630 | 10.778 | 114.061 | 1.00 | 46.06 |
| ATOM | 779 | CG | TYR | A | 111 | 63.177 | 11.000 | 113.702 | 1.00 | 45.65 |
| ATOM | 780 | CD1 | TYR | A | 111 | 62.432 | 9.998 | 113.081 | 1.00 | 46.57 |
| ATOM | 781 | CE1 | TYR | A | 111 | 61.069 | 10.160 | 112.823 | 1.00 | 44.89 |
| ATOM | 782 | CD2 | TYR | A | 111 | 62.523 | 12.183 | 114.052 | 1.00 | 45.29 |
| ATOM | 783 | CE2 | TYR | A | 111 | 61.164 | 12.357 | 113.801 | 1.00 | 45.59 |
| ATOM | 784 | CZ | TYR | A | 111 | 60.444 | 11.338 | 113.188 | 1.00 | 45.93 |
| ATOM | 785 | OH | TYR | A | 111 | 59.100 | 11.493 | 112.952 | 1.00 | 45.61 |
| ATOM | 786 | C | TYR | A | 111 | 66.248 | 9.721 | 115.666 | 1.00 | 47.88 |
| ATOM | 787 | O | TYR | A | 111 | 67.111 | 10.437 | 115.162 | 1.00 | 49.06 |
| ATOM | 788 | N | THR | A | 112 | 66.462 | 8.879 | 116.674 | 1.00 | 48.36 |
| ATOM | 789 | CA | THR | A | 112 | 67.730 | 8.672 | 117.373 | 1.00 | 48.90 |
| ATOM | 790 | CB | THR | A | 112 | 67.812 | 7.236 | 117.871 | 1.00 | 49.47 |
| ATOM | 791 | OG1 | THR | A | 112 | 67.705 | 6.338 | 116.757 | 1.00 | 51.22 |
| ATOM | 792 | CG2 | THR | A | 112 | 66.698 | 6.968 | 118.851 | 1.00 | 49.93 |
| ATOM | 793 | C | THR | A | 112 | 69.081 | 8.987 | 116.732 | 1.00 | 48.64 |
| ATOM | 794 | O | THR | A | 112 | 70.041 | 9.265 | 117.452 | 1.00 | 48.37 |
| ATOM | 795 | N | SER | A | 113 | 69.183 | 8.932 | 115.408 | 1.00 | 47.78 |
| ATOM | 796 | CA | SER | A | 113 | 70.465 | 9.207 | 114.759 | 1.00 | 47.11 |
| ATOM | 797 | CB | SER | A | 113 | 70.764 | 8.116 | 113.710 | 1.00 | 48.27 |
| ATOM | 798 | OG | SER | A | 113 | 69.752 | 8.012 | 112.716 | 1.00 | 49.10 |
| ATOM | 799 | C | SER | A | 113 | 70.606 | 10.606 | 114.122 | 1.00 | 46.61 |
| ATOM | 800 | O | SER | A | 113 | 71.570 | 10.866 | 113.388 | 1.00 | 46.29 |
| ATOM | 801 | N | TRP | A | 114 | 69.666 | 11.505 | 114.418 | 1.00 | 44.06 |
| ATOM | 802 | CA | TRP | A | 114 | 69.687 | 12.849 | 113.856 | 1.00 | 41.41 |
| ATOM | 803 | CB | TRP | A | 114 | 68.442 | 13.091 | 113.015 | 1.00 | 41.01 |
| ATOM | 804 | CG | TRP | A | 114 | 68.258 | 12.140 | 111.889 | 1.00 | 40.42 |
| ATOM | 805 | CD2 | TRP | A | 114 | 67.052 | 11.918 | 111.155 | 1.00 | 38.46 |
| ATOM | 806 | CE2 | TRP | A | 114 | 67.359 | 11.016 | 110.108 | 1.00 | 38.51 |
| ATOM | 807 | CE3 | TRP | A | 114 | 65.744 | 12.398 | 111.276 | 1.00 | 37.09 |
| ATOM | 808 | CD1 | TRP | A | 114 | 69.221 | 11.380 | 111.284 | 1.00 | 41.23 |
| ATOM | 809 | NE1 | TRP | A | 114 | 68.689 | 10.704 | 110.212 | 1.00 | 40.74 |
| ATOM | 810 | CZ2 | TRP | A | 114 | 66.405 | 10.586 | 109.184 | 1.00 | 35.23 |
| ATOM | 811 | CZ3 | TRP | A | 114 | 64.793 | 11.972 | 110.357 | 1.00 | 37.18 |
| ATOM | 812 | CH2 | TRP | A | 114 | 65.133 | 11.074 | 109.322 | 1.00 | 37.14 |
| ATOM | 813 | C | TRP | A | 114 | 69.732 | 13.918 | 114.923 | 1.00 | 41.41 |
| ATOM | 814 | O | TRP | A | 114 | 69.090 | 13.778 | 115.963 | 1.00 | 41.05 |
| ATOM | 815 | N | TYR | A | 115 | 70.462 | 14.999 | 114.635 | 1.00 | 41.08 |
| ATOM | 816 | CA | TYR | A | 115 | 70.618 | 16.136 | 115.548 | 1.00 | 39.88 |
| ATOM | 817 | CB | TYR | A | 115 | 72.096 | 16.472 | 115.766 | 1.00 | 41.04 |
| ATOM | 818 | CG | TYR | A | 115 | 72.945 | 15.383 | 116.345 | 1.00 | 43.89 |
| ATOM | 819 | CD1 | TYR | A | 115 | 73.605 | 14.478 | 115.523 | 1.00 | 43.91 |
| ATOM | 820 | CE1 | TYR | A | 115 | 74.394 | 13.474 | 116.058 | 1.00 | 45.80 |
| ATOM | 821 | CD2 | TYR | A | 115 | 73.092 | 15.258 | 117.726 | 1.00 | 45.48 |
| ATOM | 822 | CE2 | TYR | A | 115 | 73.870 | 14.258 | 118.273 | 1.00 | 45.73 |
| ATOM | 823 | CZ | TYR | A | 115 | 74.519 | 13.367 | 117.438 | 1.00 | 46.36 |
| ATOM | 824 | OH | TYR | A | 115 | 75.277 | 12.356 | 117.992 | 1.00 | 47.60 |
| ATOM | 825 | C | TYR | A | 115 | 69.989 | 17.445 | 115.073 | 1.00 | 38.37 |
| ATOM | 826 | O | TYR | A | 115 | 69.880 | 17.706 | 113.876 | 1.00 | 37.51 |
| ATOM | 827 | N | VAL | A | 116 | 69.598 | 18.276 | 116.031 | 1.00 | 36.40 |
| ATOM | 828 | CA | VAL | A | 116 | 69.099 | 19.603 | 115.730 | 1.00 | 35.41 |
| ATOM | 829 | CB | VAL | A | 116 | 68.590 | 20.297 | 117.010 | 1.00 | 32.19 |
| ATOM | 830 | CG1 | VAL | A | 116 | 68.369 | 21.759 | 116.754 | 1.00 | 32.30 |
| ATOM | 831 | CG2 | VAL | A | 116 | 67.313 | 19.662 | 117.480 | 1.00 | 32.27 |
| ATOM | 832 | C | VAL | A | 116 | 70.416 | 20.279 | 115.297 | 1.00 | 37.32 |
| ATOM | 833 | O | VAL | A | 116 | 71.411 | 20.209 | 116.024 | 1.00 | 39.26 |
| ATOM | 834 | N | ALA | A | 117 | 70.453 | 20.912 | 114.129 | 1.00 | 37.44 |
| ATOM | 835 | CA | ALA | A | 117 | 71.697 | 21.547 | 113.677 | 1.00 | 37.22 |
| ATOM | 836 | CB | ALA | A | 117 | 72.604 | 20.510 | 113.015 | 1.00 | 34.89 |
| ATOM | 837 | C | ALA | A | 117 | 71.454 | 22.702 | 112.717 | 1.00 | 37.59 |
| ATOM | 838 | O | ALA | A | 117 | 70.430 | 22.747 | 112.042 | 1.00 | 41.05 |

TABLE 1-continued

FGFR1 D2–D3 Complexed with FGF2

| ATOM | 839 | N | LEU | A | 118 | 72.398 | 23.636 | 112.652 | 1.00 | 35.93 |
|---|---|---|---|---|---|---|---|---|---|---|
| ATOM | 840 | CA | LEU | A | 118 | 72.264 | 24.780 | 111.760 | 1.00 | 33.55 |
| ATOM | 841 | CB | LEU | A | 118 | 72.152 | 26.065 | 112.587 | 1.00 | 29.51 |
| ATOM | 842 | CG | LEU | A | 118 | 70.944 | 26.105 | 113.531 | 1.00 | 27.36 |
| ATOM | 843 | CD1 | LEU | A | 118 | 70.899 | 27.395 | 114.344 | 1.00 | 25.77 |
| ATOM | 844 | CD2 | LEU | A | 118 | 69.692 | 25.969 | 112.710 | 1.00 | 25.54 |
| ATOM | 845 | C | LEU | A | 118 | 73.436 | 24.869 | 110.772 | 1.00 | 35.22 |
| ATOM | 846 | O | LEU | A | 118 | 74.592 | 24.611 | 111.125 | 1.00 | 33.57 |
| ATOM | 847 | N | LYS | A | 119 | 73.130 | 25.217 | 109.523 | 1.00 | 37.24 |
| ATOM | 848 | CA | LYS | A | 119 | 74.162 | 25.347 | 108.493 | 1.00 | 36.59 |
| ATOM | 849 | CB | LYS | A | 119 | 73.560 | 25.312 | 107.092 | 1.00 | 33.96 |
| ATOM | 850 | CG | LYS | A | 119 | 72.815 | 24.064 | 106.692 | 1.00 | 29.96 |
| ATOM | 851 | CD | LYS | A | 119 | 71.942 | 24.425 | 105.511 | 1.00 | 29.66 |
| ATOM | 852 | CE | LYS | A | 119 | 71.331 | 23.224 | 104.833 | 1.00 | 33.54 |
| ATOM | 853 | NZ | LYS | A | 119 | 71.921 | 22.954 | 103.486 | 1.00 | 35.42 |
| ATOM | 854 | C | LYS | A | 119 | 74.902 | 26.677 | 108.653 | 1.00 | 39.10 |
| ATOM | 855 | O | LYS | A | 119 | 74.431 | 27.604 | 109.332 | 1.00 | 36.63 |
| ATOM | 856 | N | ARG | A | 120 | 76.061 | 26.758 | 108.001 | 1.00 | 42.69 |
| ATOM | 857 | CA | ARG | A | 120 | 76.912 | 27.947 | 108.038 | 1.00 | 44.11 |
| ATOM | 858 | CB | ARG | A | 120 | 78.206 | 27.696 | 107.225 | 1.00 | 47.39 |
| ATOM | 859 | CG | ARG | A | 120 | 78.957 | 26.401 | 107.626 | 1.00 | 53.28 |
| ATOM | 860 | CD | ARG | A | 120 | 80.288 | 26.112 | 106.862 | 1.00 | 56.82 |
| ATOM | 861 | NE | ARG | A | 120 | 81.424 | 26.933 | 107.312 | 1.00 | 60.63 |
| ATOM | 862 | CZ | ARG | A | 120 | 82.712 | 26.621 | 107.140 | 1.00 | 60.35 |
| ATOM | 863 | NH1 | ARG | A | 120 | 83.051 | 25.494 | 106.528 | 1.00 | 60.36 |
| ATOM | 864 | NH2 | ARG | A | 120 | 83.668 | 27.439 | 107.578 | 1.00 | 60.20 |
| ATOM | 865 | C | ARG | A | 120 | 76.141 | 29.148 | 107.471 | 1.00 | 43.14 |
| ATOM | 866 | O | ARG | A | 120 | 76.507 | 30.300 | 107.708 | 1.00 | 41.07 |
| ATOM | 867 | N | THR | A | 121 | 75.059 | 28.858 | 106.746 | 1.00 | 42.80 |
| ATOM | 868 | CA | THR | A | 121 | 74.216 | 29.876 | 106.117 | 1.00 | 41.17 |
| ATOM | 869 | CB | THR | A | 121 | 73.562 | 29.337 | 104.811 | 1.00 | 40.10 |
| ATOM | 870 | OG1 | THR | A | 121 | 72.603 | 28.317 | 105.123 | 1.00 | 38.39 |
| ATOM | 871 | CG2 | THR | A | 121 | 74.617 | 28.758 | 103.894 | 1.00 | 38.65 |
| ATOM | 872 | C | THR | A | 121 | 73.100 | 30.417 | 107.012 | 1.00 | 41.97 |
| ATOM | 873 | O | THR | A | 121 | 72.415 | 31.370 | 106.648 | 1.00 | 42.59 |
| ATOM | 874 | N | GLY | A | 122 | 72.906 | 29.809 | 108.175 | 1.00 | 42.85 |
| ATOM | 875 | CA | GLY | A | 122 | 71.861 | 30.279 | 109.063 | 1.00 | 43.14 |
| ATOM | 876 | C | GLY | A | 122 | 70.534 | 29.559 | 108.903 | 1.00 | 42.89 |
| ATOM | 877 | O | GLY | A | 122 | 69.504 | 30.038 | 109.370 | 1.00 | 42.66 |
| ATOM | 878 | N | GLN | A | 123 | 70.541 | 28.411 | 108.240 | 1.00 | 43.13 |
| ATOM | 879 | CA | GLN | A | 123 | 69.310 | 27.651 | 108.068 | 1.00 | 44.40 |
| ATOM | 880 | CB | GLN | A | 123 | 68.999 | 27.460 | 106.593 | 1.00 | 43.97 |
| ATOM | 881 | CG | GLN | A | 123 | 68.606 | 28.738 | 105.924 | 1.00 | 45.73 |
| ATOM | 882 | CD | GLN | A | 123 | 68.358 | 28.550 | 104.461 | 1.00 | 47.36 |
| ATOM | 883 | OE1 | GLN | A | 123 | 69.230 | 28.059 | 103.730 | 1.00 | 49.61 |
| ATOM | 884 | NE2 | GLN | A | 123 | 67.171 | 28.939 | 104.008 | 1.00 | 45.86 |
| ATOM | 885 | C | GLN | A | 123 | 69.459 | 26.304 | 108.736 | 1.00 | 43.81 |
| ATOM | 886 | O | GLN | A | 123 | 70.562 | 25.758 | 108.791 | 1.00 | 43.65 |
| ATOM | 887 | N | TYR | A | 124 | 68.360 | 25.759 | 109.249 | 1.00 | 42.36 |
| ATOM | 888 | CA | TYR | A | 124 | 68.477 | 24.473 | 109.905 | 1.00 | 42.34 |
| ATOM | 889 | CB | TYR | A | 124 | 67.150 | 24.034 | 110.549 | 1.00 | 42.89 |
| ATOM | 890 | CG | TYR | A | 124 | 66.061 | 23.552 | 109.619 | 1.00 | 43.69 |
| ATOM | 891 | CD | TYR | A | 124 | 66.216 | 22.388 | 108.869 | 1.00 | 45.57 |
| ATOM | 892 | CE1 | TYR | A | 124 | 65.180 | 21.905 | 108.060 | 1.00 | 46.18 |
| ATOM | 893 | CD2 | TYR | A | 124 | 64.845 | 24.230 | 109.538 | 1.00 | 44.59 |
| ATOM | 894 | CE2 | TYR | A | 124 | 63.805 | 23.759 | 108.741 | 1.00 | 45.52 |
| ATOM | 895 | CZ | TYR | A | 124 | 63.977 | 22.596 | 108.005 | 1.00 | 46.26 |
| ATOM | 896 | OH | TYR | A | 124 | 62.943 | 22.123 | 107.231 | 1.00 | 46.93 |
| ATOM | 897 | C | TYR | A | 124 | 68.973 | 23.433 | 108.917 | 1.00 | 41.35 |
| ATOM | 898 | O | TYR | A | 124 | 68.729 | 23.530 | 107.718 | 1.00 | 41.57 |
| ATOM | 899 | N | LYS | A | 125 | 69.701 | 22.455 | 109.436 | 1.00 | 40.46 |
| ATOM | 900 | CA | LYS | A | 125 | 70.243 | 21.372 | 108.637 | 1.00 | 39.14 |
| ATOM | 901 | CB | LYS | A | 125 | 71.682 | 21.087 | 109.051 | 1.00 | 39.11 |
| ATOM | 902 | CG | LYS | A | 125 | 72.407 | 20.091 | 108.190 | 1.00 | 37.48 |
| ATOM | 903 | CD | LYS | A | 125 | 73.887 | 20.151 | 108.518 | 1.00 | 37.19 |
| ATOM | 904 | CE | LYS | A | 125 | 74.688 | 19.209 | 107.642 | 1.00 | 38.30 |
| ATOM | 905 | NZ | LYS | A | 125 | 76.163 | 19.376 | 107.821 | 1.00 | 40.09 |
| ATOM | 906 | C | LYS | A | 125 | 69.377 | 20.149 | 108.884 | 1.00 | 38.94 |
| ATOM | 907 | O | LYS | A | 125 | 69.009 | 19.841 | 110.028 | 1.00 | 37.71 |
| ATOM | 908 | N | LEU | A | 126 | 69.046 | 19.463 | 107.799 | 1.00 | 38.64 |
| ATOM | 909 | CA | LEU | A | 126 | 68.210 | 18.281 | 107.871 | 1.00 | 38.50 |
| ATOM | 910 | CE | LEU | A | 126 | 67.949 | 17.740 | 106.470 | 1.00 | 38.60 |
| ATOM | 911 | CG | LEU | A | 126 | 66.789 | 18.378 | 105.716 | 1.00 | 38.62 |
| ATOM | 912 | CD1 | LEU | A | 126 | 66.711 | 17.759 | 104.329 | 1.00 | 38.87 |
| ATOM | 913 | CD2 | LEU | A | 126 | 65.484 | 18.156 | 106.484 | 1.00 | 37.99 |
| ATOM | 914 | C | LEU | A | 126 | 68.817 | 17.191 | 108.723 | 1.00 | 38.32 |
| ATOM | 915 | O | LEU | A | 126 | 70.006 | 16.895 | 108.603 | 1.00 | 37.82 |

TABLE 1-continued

FGFR1 D2–D3 Complexed with FGF2

| ATOM | 916 | N | GLY | A | 127 | 67.989 | 16.599 | 109.581 | 1.00 | 38.45 |
|---|---|---|---|---|---|---|---|---|---|---|
| ATOM | 917 | CA | GLY | A | 127 | 68.449 | 15.530 | 110.445 | 1.00 | 39.64 |
| ATOM | 918 | C | GLY | A | 127 | 69.158 | 14.482 | 109.616 | 1.00 | 40.85 |
| ATOM | 919 | O | GLY | A | 127 | 70.275 | 14.067 | 109.930 | 1.00 | 42.00 |
| ATOM | 920 | N | SER | A | 128 | 68.513 | 14.063 | 108.535 | 1.00 | 41.54 |
| ATOM | 921 | CA | SER | A | 128 | 69.084 | 13.064 | 107.641 | 1.00 | 42.63 |
| ATOM | 922 | CB | SER | A | 128 | 68.188 | 12.916 | 106.404 | 1.00 | 43.01 |
| ATOM | 923 | OG | SER | A | 128 | 67.359 | 14.059 | 106.223 | 1.00 | 43.58 |
| ATOM | 924 | C | SER | A | 128 | 70.524 | 13.379 | 107.203 | 1.00 | 44.28 |
| ATOM | 925 | O | SER | A | 128 | 71.232 | 12.515 | 106.685 | 1.00 | 44.87 |
| ATOM | 926 | N | LYS | A | 129 | 70.966 | 14.612 | 107.423 | 1.00 | 45.93 |
| ATOM | 927 | CA | LYS | A | 129 | 72.307 | 15.013 | 107.017 | 1.00 | 45.44 |
| ATOM | 928 | CB | LYS | A | 129 | 72.228 | 16.234 | 106.083 | 1.00 | 46.85 |
| ATOM | 929 | CG | LYS | A | 129 | 71.242 | 16.098 | 104.909 | 1.00 | 51.95 |
| ATOM | 930 | CD | LYS | A | 129 | 71.502 | 17.129 | 103.783 | 1.00 | 55.26 |
| ATOM | 931 | CE | LYS | A | 129 | 71.325 | 18.594 | 104.254 | 1.00 | 60.79 |
| ATOM | 932 | NZ | LYS | A | 129 | 71.878 | 19.660 | 103.325 | 1.00 | 61.01 |
| ATOM | 933 | C | LYS | A | 129 | 73.250 | 15.336 | 108.175 | 1.00 | 44.17 |
| ATOM | 934 | O | LYS | A | 129 | 74.367 | 15.774 | 107.945 | 1.00 | 43.85 |
| ATOM | 935 | N | THR | A | 130 | 72.828 | 15.123 | 109.414 | 1.00 | 42.92 |
| ATOM | 936 | CA | THR | A | 130 | 73.709 | 15.457 | 110.525 | 1.00 | 42.43 |
| ATOM | 937 | CB | THR | A | 130 | 72.934 | 16.133 | 111.682 | 1.00 | 41.22 |
| ATOM | 938 | OG1 | THR | A | 130 | 71.931 | 15.243 | 112.194 | 1.00 | 39.15 |
| ATOM | 939 | CG2 | THR | A | 130 | 72.282 | 17.408 | 111.197 | 1.00 | 38.70 |
| ATOM | 940 | C | THR | A | 130 | 74.506 | 14.280 | 111.073 | 1.00 | 44.22 |
| ATOM | 941 | O | THR | A | 130 | 74.024 | 13.147 | 111.127 | 1.00 | 44.98 |
| ATOM | 942 | N | GLY | A | 131 | 75.739 | 14.567 | 111.474 | 1.00 | 44.70 |
| ATOM | 943 | CA | GLY | A | 131 | 76.608 | 13.541 | 112.018 | 1.00 | 45.33 |
| ATOM | 944 | C | GLY | A | 131 | 77.376 | 14.055 | 113.222 | 1.00 | 46.80 |
| ATOM | 945 | O | GLY | A | 131 | 77.409 | 15.265 | 113.471 | 1.00 | 47.55 |
| ATOM | 946 | N | PRO | A | 132 | 78.016 | 13.159 | 113.985 | 1.00 | 46.38 |
| ATOM | 947 | CD | PRO | A | 132 | 78.213 | 11.755 | 113.589 | 1.00 | 47.25 |
| ATOM | 948 | CA | PRO | A | 132 | 78.808 | 13.457 | 115.182 | 1.00 | 45.69 |
| ATOM | 949 | CB | PRO | A | 132 | 79.259 | 12.079 | 115.622 | 1.00 | 47.47 |
| ATOM | 950 | CG | PRO | A | 132 | 79.497 | 11.407 | 114.305 | 1.00 | 46.80 |
| ATOM | 951 | C | PRO | A | 132 | 80.013 | 14.370 | 114.926 | 1.00 | 44.62 |
| ATOM | 952 | O | PRO | A | 132 | 80.330 | 15.253 | 115.731 | 1.00 | 45.57 |
| ATOM | 953 | N | GLY | A | 133 | 80.698 | 14.140 | 113.815 | 1.00 | 42.56 |
| ATOM | 954 | CA | GLY | A | 133 | 81.850 | 14.960 | 113.508 | 1.00 | 41.60 |
| ATOM | 955 | C | GLY | A | 133 | 81.486 | 16.319 | 112.938 | 1.00 | 41.19 |
| ATOM | 956 | O | GLY | A | 133 | 82.339 | 17.023 | 112.411 | 1.00 | 40.45 |
| ATOM | 957 | N | GLN | A | 134 | 80.223 | 16.707 | 113.053 | 1.00 | 41.05 |
| ATOM | 958 | CA | GLN | A | 134 | 79.784 | 17.986 | 112.507 | 1.00 | 41.03 |
| ATOM | 959 | CB | GLN | A | 134 | 78.422 | 17.820 | 111.858 | 1.00 | 42.60 |
| ATOM | 960 | CG | GLN | A | 134 | 78.439 | 17.045 | 110.575 | 1.00 | 42.17 |
| ATOM | 961 | CD | GLN | A | 134 | 77.077 | 17.019 | 109.953 | 1.00 | 41.64 |
| ATOM | 962 | OE1 | GLN | A | 134 | 76.335 | 18.001 | 110.035 | 1.00 | 42.15 |
| ATOM | 963 | NE2 | GLN | A | 134 | 76.733 | 15.905 | 109.319 | 1.00 | 41.49 |
| ATOM | 964 | C | GLN | A | 134 | 79.726 | 19.180 | 113.460 | 1.00 | 40.14 |
| ATOM | 965 | O | GLN | A | 134 | 79.214 | 19.090 | 114.577 | 1.00 | 39.81 |
| ATOM | 966 | N | LYS | A | 135 | 80.233 | 20.308 | 112.972 | 1.00 | 38.91 |
| ATOM | 967 | CA | LYS | A | 135 | 80.278 | 21.562 | 113.715 | 1.00 | 36.79 |
| ATOM | 968 | CB | LYS | A | 135 | 81.217 | 22.521 | 112.985 | 1.00 | 36.65 |
| ATOM | 969 | CG | LYS | A | 135 | 81.505 | 23.848 | 113.651 | 1.00 | 38.80 |
| ATOM | 970 | CD | LYS | A | 135 | 82.711 | 24.479 | 112.939 | 1.00 | 41.93 |
| ATOM | 971 | CE | LYS | A | 135 | 82.735 | 26.008 | 113.003 | 1.00 | 44.55 |
| ATOM | 972 | NZ | LYS | A | 135 | 83.581 | 26.607 | 111.908 | 1.00 | 44.29 |
| ATOM | 973 | C | LYS | A | 135 | 78.876 | 22.155 | 113.831 | 1.00 | 35.29 |
| ATOM | 974 | O | LYS | A | 135 | 78.604 | 22.978 | 114.705 | 1.00 | 34.18 |
| ATOM | 975 | N | ALA | A | 136 | 77.981 | 21.705 | 112.958 | 1.00 | 34.66 |
| ATOM | 976 | CA | ALA | A | 136 | 76.610 | 22.191 | 112.942 | 1.00 | 33.50 |
| ATOM | 977 | CB | ALA | A | 136 | 75.951 | 21.816 | 111.623 | 1.00 | 32.41 |
| ATOM | 978 | C | ALA | A | 136 | 75.763 | 21.687 | 114.109 | 1.00 | 33.64 |
| ATOM | 979 | O | ALA | A | 136 | 74.823 | 22.366 | 114.533 | 1.00 | 33.54 |
| ATOM | 980 | N | ILE | A | 137 | 76.091 | 20.510 | 114.637 | 1.00 | 32.69 |
| ATOM | 981 | CA | ILE | A | 137 | 75.317 | 19.942 | 115.739 | 1.00 | 32.18 |
| ATOM | 982 | CB | ILE | A | 137 | 75.445 | 18.405 | 115.815 | 1.00 | 32.98 |
| ATOM | 983 | CG2 | ILE | A | 137 | 74.871 | 17.773 | 114.554 | 1.00 | 33.96 |
| ATOM | 984 | CG1 | ILE | A | 137 | 76.908 | 18.011 | 116.079 | 1.00 | 32.14 |
| ATOM | 985 | CD1 | ILE | A | 137 | 77.141 | 16.506 | 116.268 | 1.00 | 29.78 |
| ATOM | 986 | C | ILE | A | 137 | 75.693 | 20.448 | 117.111 | 1.00 | 32.80 |
| ATOM | 987 | O | ILE | A | 137 | 75.029 | 20.112 | 118.098 | 1.00 | 34.26 |
| ATOM | 988 | N | LEU | A | 138 | 76.753 | 21.244 | 117.186 | 1.00 | 32.26 |
| ATOM | 989 | CA | LEU | A | 138 | 77.213 | 21.743 | 118.476 | 1.00 | 31.34 |
| ATOM | 990 | CB | LEU | A | 138 | 78.746 | 21.780 | 118.491 | 1.00 | 30.49 |
| ATOM | 991 | CG | LEU | A | 138 | 79.371 | 20.440 | 118.088 | 1.00 | 30.42 |
| ATOM | 992 | CD1 | LEU | A | 138 | 80.876 | 20.550 | 118.071 | 1.00 | 31.69 |

TABLE 1-continued

FGFR1 D2–D3 Complexed with FGF2

| ATOM | 993 | CD2 | LEU | A | 138 | 78.944 | 19.352 | 119.061 | 1.00 | 32.51 |
|---|---|---|---|---|---|---|---|---|---|---|
| ATOM | 994 | C | LEU | A | 138 | 76.640 | 23.104 | 118.862 | 1.00 | 30.99 |
| ATOM | 995 | O | LEU | A | 138 | 76.717 | 24.068 | 118.099 | 1.00 | 30.94 |
| ATOM | 996 | N | PHE | A | 139 | 76.061 | 23.166 | 120.058 | 1.00 | 30.10 |
| ATOM | 997 | CA | PHE | A | 139 | 75.479 | 24.397 | 120.573 | 1.00 | 29.61 |
| ATOM | 998 | CB | PHE | A | 139 | 73.959 | 24.294 | 120.685 | 1.00 | 29.86 |
| ATOM | 999 | CG | PHE | A | 139 | 73.291 | 23.992 | 119.402 | 1.00 | 30.42 |
| ATOM | 1000 | CD1 | PHE | A | 139 | 73.283 | 22.695 | 118.905 | 1.00 | 31.20 |
| ATOM | 1001 | CD2 | PHE | A | 139 | 72.712 | 25.009 | 118.659 | 1.00 | 31.75 |
| ATOM | 1002 | CE1 | PHE | A | 139 | 72.709 | 22.407 | 117.681 | 1.00 | 32.46 |
| ATOM | 1003 | CE2 | PHE | A | 139 | 72.133 | 24.739 | 117.427 | 1.00 | 33.50 |
| ATOM | 1004 | CZ | PHE | A | 139 | 72.132 | 23.430 | 116.934 | 1.00 | 33.41 |
| ATOM | 1005 | C | PHE | A | 139 | 76.021 | 24.709 | 121.946 | 1.00 | 29.99 |
| ATOM | 1006 | O | PHE | A | 139 | 76.456 | 23.822 | 122.678 | 1.00 | 29.92 |
| ATOM | 1007 | N | LEU | A | 140 | 75.978 | 25.987 | 122.293 | 1.00 | 29.55 |
| ATOM | 1008 | CA | LEU | A | 140 | 76.443 | 26.436 | 123.580 | 1.00 | 28.07 |
| ATOM | 1009 | CB | LEU | A | 140 | 77.649 | 27.357 | 123.415 | 1.00 | 25.38 |
| ATOM | 1010 | CG | LEU | A | 140 | 78.343 | 27.762 | 124.719 | 1.00 | 26.90 |
| ATOM | 1011 | CD1 | LEU | A | 140 | 79.389 | 26.707 | 125.117 | 1.00 | 23.01 |
| ATOM | 1012 | CD2 | LEU | A | 140 | 78.991 | 29.120 | 124.523 | 1.00 | 26.49 |
| ATOM | 1013 | C | LEU | A | 140 | 75.280 | 27.175 | 124.244 | 1.00 | 30.30 |
| ATOM | 1014 | O | LEU | A | 140 | 74.763 | 28.169 | 123.714 | 1.00 | 30.33 |
| ATOM | 1015 | N | PRO | A | 141 | 74.830 | 26.678 | 125.407 | 1.00 | 30.93 |
| ATOM | 1016 | CD | PRO | A | 141 | 75.130 | 25.361 | 125.992 | 1.00 | 29.93 |
| ATOM | 1017 | CA | PRO | A | 141 | 73.720 | 27.320 | 126.116 | 1.00 | 30.37 |
| ATOM | 1018 | CB | PRO | A | 141 | 73.354 | 26.292 | 127.188 | 1.00 | 29.43 |
| ATOM | 1019 | CG | PRO | A | 141 | 73.803 | 24.997 | 126.597 | 1.00 | 30.39 |
| ATOM | 1020 | C | PRO | A | 141 | 74.160 | 28.644 | 126.720 | 1.00 | 29.99 |
| ATOM | 1021 | O | PRO | A | 141 | 75.263 | 28.755 | 127.230 | 1.00 | 29.80 |
| ATOM | 1022 | N | MET | A | 142 | 73.296 | 29.645 | 126.654 | 1.00 | 31.55 |
| ATOM | 1023 | CA | MET | A | 142 | 73.605 | 30.949 | 127.215 | 1.00 | 33.42 |
| ATOM | 1024 | CB | MET | A | 142 | 74.054 | 31.913 | 126.121 | 1.00 | 34.28 |
| ATOM | 1025 | CG | MET | A | 142 | 75.418 | 31.603 | 125.534 | 1.00 | 35.59 |
| ATOM | 1026 | SD | MET | A | 142 | 75.795 | 32.644 | 124.108 | 1.00 | 36.91 |
| ATOM | 1027 | CE | MET | A | 142 | 76.070 | 34.233 | 124.865 | 1.00 | 37.00 |
| ATOM | 1028 | C | MET | A | 142 | 72.380 | 31.496 | 127.933 | 1.00 | 35.30 |
| ATOM | 1029 | O | MET | A | 142 | 71.343 | 31.769 | 127.325 | 1.00 | 33.50 |
| ATOM | 1030 | N | SER | A | 143 | 72.518 | 31.639 | 129.244 | 1.00 | 38.45 |
| ATOM | 1031 | CA | SER | A | 143 | 71.449 | 32.134 | 130.092 | 1.00 | 41.94 |
| ATOM | 1032 | CB | SER | A | 143 | 71.935 | 32.262 | 131.545 | 1.00 | 43.82 |
| ATOM | 1033 | OG | SER | A | 143 | 73.020 | 33.175 | 131.668 | 1.00 | 46.24 |
| ATOM | 1034 | C | SER | A | 143 | 70.892 | 33.462 | 129.605 | 1.00 | 43.77 |
| ATOM | 1035 | O | SER | A | 143 | 71.627 | 34.330 | 129.133 | 1.00 | 44.56 |
| ATOM | 1036 | N | ALA | A | 144 | 69.578 | 33.601 | 129.731 | 1.00 | 45.87 |
| ATOM | 1037 | CA | ALA | A | 144 | 68.872 | 34.797 | 129.304 | 1.00 | 47.92 |
| ATOM | 1038 | CB | ALA | A | 144 | 68.241 | 34.556 | 127.941 | 1.00 | 46.91 |
| ATOM | 1039 | C | ALA | A | 144 | 67.796 | 35.151 | 130.327 | 1.00 | 49.42 |
| ATOM | 1040 | O | ALA | A | 144 | 67.606 | 36.366 | 130.560 | 1.00 | 50.94 |
| ATOM | 1041 | CB | HIS | B | 16 | 101.445 | 8.523 | 141.693 | 1.00 | 53.58 |
| ATOM | 1042 | CG | HIS | B | 16 | 101.728 | 8.165 | 143.119 | 1.00 | 58.45 |
| ATOM | 1043 | CD2 | HIS | B | 16 | 101.794 | 6.964 | 143.742 | 1.00 | 60.61 |
| ATOM | 1044 | ND1 | HIS | B | 16 | 101.993 | 9.112 | 144.087 | 1.00 | 60.79 |
| ATOM | 1045 | CE1 | HIS | B | 16 | 102.207 | 8.509 | 145.243 | 1.00 | 61.84 |
| ATOM | 1046 | NE2 | HIS | B | 16 | 102.093 | 7.205 | 145.061 | 1.00 | 62.31 |
| ATOM | 1047 | C | HIS | B | 16 | 102.083 | 10.901 | 141.902 | 1.00 | 48.11 |
| ATOM | 1048 | O | HIS | B | 16 | 103.177 | 10.845 | 141.327 | 1.00 | 47.34 |
| ATOM | 1049 | N | HIS | B | 16 | 100.509 | 10.188 | 140.098 | 1.00 | 46.31 |
| ATOM | 1050 | CA | HIS | B | 16 | 100.953 | 9.958 | 141.508 | 1.00 | 49.06 |
| ATOM | 1051 | N | PHE | B | 17 | 101.816 | 11.731 | 142.910 | 1.00 | 47.00 |
| ATOM | 1052 | CA | PHE | B | 17 | 102.763 | 12.726 | 143.423 | 1.00 | 45.92 |
| ATOM | 1053 | CB | PHE | B | 17 | 102.107 | 13.493 | 144.587 | 1.00 | 45.44 |
| ATOM | 1054 | CG | PHE | B | 17 | 101.954 | 12.679 | 145.857 | 1.00 | 44.25 |
| ATOM | 1055 | CD1 | PHE | B | 17 | 102.968 | 12.657 | 146.815 | 1.00 | 43.19 |
| ATOM | 1056 | CD2 | PHE | B | 17 | 100.799 | 11.928 | 146.093 | 1.00 | 42.90 |
| ATOM | 1057 | CE1 | PHE | B | 17 | 102.833 | 11.898 | 147.985 | 1.00 | 41.41 |
| ATOM | 1058 | CE2 | PHE | B | 17 | 100.657 | 11.164 | 147.263 | 1.00 | 40.06 |
| ATOM | 1059 | CZ | PHE | B | 17 | 101.670 | 11.150 | 148.204 | 1.00 | 40.32 |
| ATOM | 1060 | C | PHE | B | 17 | 104.133 | 12.181 | 143.869 | 1.00 | 45.68 |
| ATOM | 1061 | O | PHE | B | 17 | 105.147 | 12.890 | 143.818 | 1.00 | 43.64 |
| ATOM | 1062 | N | LYS | B | 18 | 104.166 | 10.927 | 144.307 | 1.00 | 46.37 |
| ATOM | 1063 | CA | LYS | B | 18 | 105.415 | 10.325 | 144.772 | 1.00 | 47.59 |
| ATOM | 1064 | CB | LYS | B | 18 | 105.142 | 9.028 | 145.550 | 1.00 | 46.13 |
| ATOM | 1065 | C | LYS | B | 18 | 106.421 | 10.030 | 143.658 | 1.00 | 47.69 |
| ATOM | 1066 | O | LYS | B | 18 | 107.636 | 10.060 | 143.895 | 1.00 | 47.25 |
| ATOM | 1067 | N | ASP | B | 19 | 105.918 | 9.752 | 142.453 | 1.00 | 47.51 |
| ATOM | 1068 | CA | ASP | B | 19 | 106.774 | 9.416 | 141.311 | 1.00 | 46.25 |
| ATOM | 1069 | CB | ASP | B | 19 | 105.996 | 8.597 | 140.278 | 1.00 | 48.23 |

TABLE 1-continued

FGFR1 D2–D3 Complexed with FGF2

| ATOM | 1070 | CG | ASP | B | 19 | 105.414 | 7.315 | 140.862 | 1.00 | 51.06 |
|---|---|---|---|---|---|---|---|---|---|---|
| ATOM | 1071 | OD1 | ASP | B | 19 | 106.151 | 6.591 | 141.580 | 1.00 | 49.53 |
| ATOM | 1072 | OD2 | ASP | B | 19 | 104.220 | 7.034 | 140.592 | 1.00 | 50.69 |
| ATOM | 1073 | C | ASP | B | 19 | 107.375 | 10.622 | 140.624 | 1.00 | 44.83 |
| ATOM | 1074 | O | ASP | B | 19 | 106.895 | 11.745 | 140.781 | 1.00 | 47.81 |
| ATOM | 1075 | N | PRO | B | 20 | 108.439 | 10.407 | 139.838 | 1.00 | 42.28 |
| ATOM | 1076 | CD | PRO | B | 20 | 109.144 | 9.140 | 139.612 | 1.00 | 41.29 |
| ATOM | 1077 | CA | PRO | B | 20 | 109.106 | 11.496 | 139.124 | 1.00 | 39.23 |
| ATOM | 1078 | CB | PRO | B | 20 | 110.348 | 10.825 | 138.540 | 1.00 | 40.15 |
| ATOM | 1079 | CG | PRO | B | 20 | 110.550 | 9.624 | 139.424 | 1.00 | 41.97 |
| ATOM | 1080 | C | PRO | B | 20 | 108.204 | 12.019 | 138.037 | 1.00 | 35.93 |
| ATOM | 1081 | O | PRO | B | 20 | 107.371 | 11.291 | 137.511 | 1.00 | 35.62 |
| ATOM | 1082 | N | LYS | B | 21 | 108.381 | 13.281 | 137.695 | 1.00 | 34.38 |
| ATOM | 1083 | C | ALYS | B | 21 | 107.581 | 13.877 | 136.656 | 1.00 | 33.82 |
| ATOM | 1084 | CB | LYS | B | 21 | 106.633 | 14.890 | 137.290 | 1.00 | 32.42 |
| ATOM | 1085 | CG | LYS | B | 21 | 105.802 | 14.240 | 138.382 | 1.00 | 35.36 |
| ATOM | 1086 | CD | LYS | B | 21 | 104.698 | 15.135 | 138.905 | 1.00 | 38.67 |
| ATOM | 1087 | CE | LYS | B | 21 | 103.854 | 14.410 | 139.947 | 1.00 | 39.11 |
| ATOM | 1088 | NZ | LYS | B | 21 | 102.725 | 15.254 | 140.441 | 1.00 | 39.48 |
| ATOM | 1089 | C | LYS | B | 21 | 108.494 | 14.501 | 135.607 | 1.00 | 33.46 |
| ATOM | 1090 | O | LYS | B | 21 | 109.656 | 14.795 | 135.879 | 1.00 | 33.20 |
| ATOM | 1091 | N | ARG | B | 22 | 107.983 | 14.645 | 134.392 | 1.00 | 32.18 |
| ATOM | 1092 | CA | ARG | B | 22 | 108.751 | 15.249 | 133.318 | 1.00 | 32.62 |
| ATOM | 1093 | CB | ARG | B | 22 | 108.623 | 14.423 | 132.021 | 1.00 | 35.35 |
| ATOM | 1094 | CG | ARG | B | 22 | 109.685 | 13.336 | 131.798 | 1.00 | 39.07 |
| ATOM | 1095 | CD | ARG | B | 22 | 109.521 | 12.639 | 130.429 | 1.00 | 43.42 |
| ATOM | 1096 | NE | ARG | B | 22 | 108.763 | 11.383 | 130.484 | 1.00 | 48.74 |
| ATOM | 1097 | CZ | ARG | B | 22 | 109.266 | 10.207 | 130.871 | 1.00 | 51.40 |
| ATOM | 1098 | NH1 | ARG | B | 22 | 110.541 | 10.111 | 131.240 | 1.00 | 53.26 |
| ATOM | 1099 | NH2 | ARG | B | 22 | 108.494 | 9.121 | 130.895 | 1.00 | 51.66 |
| ATOM | 1100 | C | ARG | B | 22 | 108.111 | 16.606 | 133.117 | 1.00 | 31.88 |
| ATOM | 1101 | O | ARG | B | 22 | 106.899 | 16.699 | 133.019 | 1.00 | 32.34 |
| ATOM | 1102 | N | LEU | B | 23 | 108.901 | 17.666 | 133.068 | 1.00 | 31.50 |
| ATOM | 1103 | CA | LEU | B | 23 | 108.316 | 18.984 | 132.849 | 1.00 | 30.85 |
| ATOM | 1104 | CB | LEU | B | 23 | 108.953 | 19.997 | 133.809 | 1.00 | 29.80 |
| ATOM | 1105 | CG | LEU | B | 23 | 108.568 | 19.805 | 135.282 | 1.00 | 30.02 |
| ATOM | 1106 | CD1 | LEU | B | 23 | 109.288 | 20.822 | 136.157 | 1.00 | 29.71 |
| ATOM | 1107 | CD2 | LEU | B | 23 | 107.062 | 19.962 | 135.441 | 1.00 | 29.76 |
| ATOM | 1108 | C | LEU | B | 23 | 108.437 | 19.441 | 131.377 | 1.00 | 31.55 |
| ATOM | 1109 | O | LEU | B | 23 | 109.509 | 19.818 | 130.898 | 1.00 | 31.98 |
| ATOM | 1110 | N | TYR | B | 24 | 107.318 | 19.391 | 130.665 | 1.00 | 31.38 |
| ATOM | 1111 | CA | TYR | B | 24 | 107.257 | 19.768 | 129.258 | 1.00 | 30.32 |
| ATOM | 1112 | CB | TYR | B | 24 | 106.202 | 18.885 | 128.593 | 1.00 | 31.90 |
| ATOM | 1113 | CG | TYR | B | 24 | 105.930 | 19.160 | 127.140 | 1.00 | 34.51 |
| ATOM | 1114 | CD1 | TYR | B | 24 | 105.203 | 20.282 | 126.741 | 1.00 | 33.58 |
| ATOM | 1115 | CE1 | TYR | B | 24 | 104.898 | 20.489 | 125.402 | 1.00 | 33.99 |
| ATOM | 1116 | CD2 | TYR | B | 24 | 106.351 | 18.264 | 126.161 | 1.00 | 33.10 |
| ATOM | 1117 | CE2 | TYR | B | 24 | 106.054 | 18.469 | 124.828 | 1.00 | 31.74 |
| ATOM | 1118 | CZ | TYR | B | 24 | 105.327 | 19.572 | 124.454 | 1.00 | 32.06 |
| ATOM | 1119 | OH | TYR | B | 24 | 105.001 | 19.738 | 123.131 | 1.00 | 33.37 |
| ATOM | 1120 | C | TYR | B | 24 | 106.908 | 21.257 | 129.135 | 1.00 | 29.21 |
| ATOM | 1121 | O | TYR | B | 24 | 105.830 | 21.674 | 129.545 | 1.00 | 28.83 |
| ATOM | 1122 | N | CYS | B | 25 | 107.822 | 22.053 | 128.578 | 1.00 | 28.00 |
| ATOM | 1123 | CA | CYS | B | 25 | 107.592 | 23.492 | 128.430 | 1.00 | 28.66 |
| ATOM | 1124 | CB | CYS | B | 25 | 108.920 | 24.246 | 128.273 | 1.00 | 28.41 |
| ATOM | 1125 | SG | CYS | B | 25 | 108.778 | 26.080 | 128.299 | 1.00 | 24.31 |
| ATOM | 1126 | C | CYS | B | 25 | 106.703 | 23.807 | 127.238 | 1.00 | 30.84 |
| ATOM | 1127 | O | CYS | B | 25 | 106.941 | 23.303 | 126.136 | 1.00 | 33.28 |
| ATOM | 1128 | N | LYS | B | 26 | 105.685 | 24.644 | 127.449 | 1.00 | 30.59 |
| ATOM | 1129 | CA | LYS | B | 26 | 104.772 | 24.993 | 126.363 | 1.00 | 30.75 |
| ATOM | 1130 | CB | LYS | B | 26 | 103.642 | 25.911 | 126.833 | 1.00 | 30.15 |
| ATOM | 1131 | CG | LYS | B | 26 | 102.644 | 26.241 | 125.718 | 1.00 | 26.13 |
| ATOM | 1132 | CD | LYS | B | 26 | 101.597 | 27.212 | 126.165 | 1.00 | 23.86 |
| ATOM | 1133 | CE | LYS | B | 26 | 100.711 | 27.617 | 125.007 | 1.00 | 25.53 |
| ATOM | 1134 | NZ | LYS | B | 26 | 99.854 | 28.790 | 125.357 | 1.00 | 23.37 |
| ATOM | 1135 | C | LYS | B | 26 | 105.504 | 25.696 | 125.249 | 1.00 | 31.19 |
| ATOM | 1136 | O | LYS | B | 26 | 105.090 | 25.658 | 124.099 | 1.00 | 32.72 |
| ATOM | 1137 | N | ASN | B | 27 | 106.605 | 26.336 | 125.595 | 1.00 | 33.18 |
| ATOM | 1138 | CA | ASN | B | 27 | 107.368 | 27.073 | 124.618 | 1.00 | 34.32 |
| ATOM | 1139 | CB | ASN | B | 27 | 108.038 | 28.254 | 125.289 | 1.00 | 35.05 |
| ATOM | 1140 | CG | ASN | B | 27 | 108.694 | 29.154 | 124.301 | 1.00 | 37.69 |
| ATOM | 1141 | OD1 | ASN | B | 27 | 108.213 | 29.294 | 123.179 | 1.00 | 40.64 |
| ATOM | 1142 | ND2 | ASN | B | 27 | 109.791 | 29.789 | 124.702 | 1.00 | 39.91 |
| ATOM | 1143 | C | ASN | B | 27 | 108.413 | 26.258 | 123.871 | 1.00 | 36.01 |
| ATOM | 1144 | O | ASN | B | 27 | 109.604 | 26.318 | 124.188 | 1.00 | 36.60 |
| ATOM | 1145 | N | GLY | B | 28 | 107.960 | 25.497 | 122.876 | 1.00 | 36.54 |
| ATOM | 1146 | CA | GLY | B | 28 | 108.868 | 24.701 | 122.072 | 1.00 | 34.89 |

TABLE 1-continued

FGFR1 D2–D3 Complexed with FGF2

| ATOM | 1147 | C | GLY | B | 28 | 108.758 | 23.214 | 122.278 | 1.00 | 35.90 |
|---|---|---|---|---|---|---|---|---|---|---|
| ATOM | 1148 | O | GLY | B | 28 | 109.283 | 22.439 | 121.482 | 1.00 | 35.86 |
| ATOM | 1149 | N | GLY | B | 29 | 108.082 | 22.809 | 123.348 | 1.00 | 37.35 |
| ATOM | 1150 | CA | GLY | B | 29 | 107.933 | 21.392 | 123.627 | 1.00 | 37.23 |
| ATOM | 1151 | C | GLY | B | 29 | 109.202 | 20.823 | 124.223 | 1.00 | 37.28 |
| ATOM | 1152 | O | GLY | B | 29 | 109.479 | 19.625 | 124.094 | 1.00 | 38.96 |
| ATOM | 1153 | N | PHE | B | 30 | 109.982 | 21.694 | 124.860 | 1.00 | 36.18 |
| ATOM | 1154 | CA | PHE | B | 30 | 111.228 | 21.291 | 125.499 | 1.00 | 36.03 |
| ATOM | 1155 | CB | PHE | B | 30 | 112.224 | 22.458 | 125.569 | 1.00 | 35.91 |
| ATOM | 1156 | CG | PHE | B | 30 | 112.801 | 22.859 | 124.243 | 1.00 | 36.45 |
| ATOM | 1157 | CD1 | PHE | B | 30 | 112.337 | 23.996 | 123.583 | 1.00 | 34.88 |
| ATOM | 1158 | CD2 | PHE | B | 30 | 113.799 | 22.090 | 123.647 | 1.00 | 36.18 |
| ATOM | 1159 | CE1 | PHE | B | 30 | 112.846 | 24.363 | 122.353 | 1.00 | 34.85 |
| ATOM | 1160 | CE2 | PHE | B | 30 | 114.316 | 22.447 | 122.416 | 1.00 | 35.27 |
| ATOM | 1161 | CZ | PHE | B | 30 | 113.837 | 23.590 | 121.764 | 1.00 | 36.19 |
| ATOM | 1162 | C | PHE | B | 30 | 110.983 | 20.811 | 126.925 | 1.00 | 36.21 |
| ATOM | 1163 | O | PHE | B | 30 | 110.292 | 21.473 | 127.707 | 1.00 | 36.14 |
| ATOM | 1164 | N | PHE | B | 31 | 111.555 | 19.659 | 127.249 | 1.00 | 35.85 |
| ATOM | 1165 | CA | PHE | B | 31 | 111.469 | 19.097 | 128.589 | 1.00 | 37.40 |
| ATOM | 1166 | CB | PHE | B | 31 | 111.618 | 17.580 | 128.526 | 1.00 | 37.92 |
| ATOM | 1167 | CG | PHE | B | 31 | 110.402 | 16.878 | 128.027 | 1.00 | 40.04 |
| ATOM | 1168 | CD1 | PHE | B | 31 | 109.385 | 16.526 | 128.901 | 1.00 | 41.04 |
| ATOM | 1169 | CD2 | PHE | B | 31 | 110.281 | 16.543 | 126.684 | 1.00 | 41.32 |
| ATOM | 117O | CE1 | PHE | B | 31 | 108.260 | 15.838 | 128.446 | 1.00 | 42.85 |
| ATOM | 1171 | CE2 | PHE | B | 31 | 109.162 | 15.855 | 126.212 | 1.00 | 42.54 |
| ATOM | 1172 | CZ | PHE | B | 31 | 108.148 | 15.500 | 127.097 | 1.00 | 43.55 |
| ATOM | 1173 | C | PHE | B | 31 | 112.622 | 19.682 | 129.420 | 1.00 | 37.60 |
| ATOM | 1174 | O | PHE | B | 31 | 113.771 | 19.700 | 128.963 | 1.00 | 38.92 |
| ATOM | 1175 | N | LEU | B | 32 | 112.323 | 20.163 | 130.625 | 1.00 | 35.55 |
| ATOM | 1176 | CA | LEU | B | 32 | 113.355 | 20.716 | 131.488 | 1.00 | 34.17 |
| ATOM | 1177 | CB | LEU | B | 32 | 112.728 | 21.197 | 132.795 | 1.00 | 35.16 |
| ATOM | 1178 | CG | LEU | B | 32 | 113.638 | 21.861 | 133.832 | 1.00 | 36.30 |
| ATOM | 1179 | CD1 | LEU | B | 32 | 114.192 | 23.176 | 133.306 | 1.00 | 33.58 |
| ATOM | 1180 | CD2 | LEU | B | 32 | 112.832 | 22.093 | 135.097 | 1.00 | 36.73 |
| ATOM | 1181 | C | LEU | B | 32 | 114.384 | 19.619 | 131.774 | 1.00 | 33.55 |
| ATOM | 1182 | O | LEU | B | 32 | 114.026 | 18.501 | 132.172 | 1.00 | 30.47 |
| ATOM | 1183 | N | ARG | B | 33 | 115.658 | 19.936 | 131.556 | 1.00 | 32.82 |
| ATOM | 1184 | CA | ARG | B | 33 | 116.722 | 18.975 | 131.792 | 1.00 | 32.99 |
| ATOM | 1185 | CB | ARG | B | 33 | 117.387 | 18.584 | 130.483 | 1.00 | 32.91 |
| ATOM | 1186 | CG | ARG | B | 33 | 118.606 | 17.695 | 130.699 | 1.00 | 34.53 |
| ATOM | 1187 | CD | ARG | B | 33 | 119.161 | 17.186 | 129.381 | 1.00 | 34.21 |
| ATOM | 1188 | NE | ARG | B | 33 | 119.641 | 18.270 | 128.530 | 1.00 | 32.09 |
| ATOM | 1189 | CZ | ARG | B | 33 | 120.035 | 18.101 | 127.275 | 1.00 | 29.40 |
| ATOM | 1190 | NH1 | ARG | B | 33 | 120.002 | 16.894 | 126.734 | 1.00 | 26.60 |
| ATOM | 1191 | NH2 | ARG | B | 33 | 120.456 | 19.135 | 126.563 | 1.00 | 26.93 |
| ATOM | 1192 | C | ARG | B | 33 | 117.802 | 19.445 | 132.760 | 1.00 | 33.81 |
| ATOM | 1193 | O | ARG | B | 33 | 118.268 | 20.589 | 132.702 | 1.00 | 34.83 |
| ATOM | 1194 | N | ILE | B | 34 | 118.207 | 18.541 | 133.645 | 1.00 | 33.61 |
| ATOM | 1195 | CA | ILE | B | 34 | 119.243 | 18.835 | 134.624 | 1.00 | 34.06 |
| ATOM | 1196 | CB | ILE | B | 34 | 118.743 | 18.638 | 136.050 | 1.00 | 31.91 |
| ATOM | 1197 | CG2 | ILE | B | 34 | 119.898 | 18.733 | 137.023 | 1.00 | 31.52 |
| ATOM | 1198 | CG1 | ILE | B | 34 | 117.676 | 19.672 | 136.371 | 1.00 | 28.95 |
| ATOM | 1199 | CD1 | ILE | B | 34 | 117.027 | 19.425 | 137.693 | 1.00 | 28.65 |
| ATOM | 1200 | C | ILE | B | 34 | 120.408 | 17.884 | 134.412 | 1.00 | 36.60 |
| ATOM | 1201 | O | ILE | B | 34 | 120.322 | 16.702 | 134.770 | 1.00 | 36.08 |
| ATOM | 1202 | N | HIS | B | 35 | 121.485 | 18.413 | 133.828 | 1.00 | 38.97 |
| ATOM | 1203 | CA | HIS | B | 35 | 122.704 | 17.653 | 133.548 | 1.00 | 40.24 |
| ATOM | 1204 | CB | HIS | B | 35 | 123.634 | 18.480 | 132.656 | 1.00 | 42.94 |
| ATOM | 1205 | CG | HIS | B | 35 | 123.049 | 18.814 | 131.322 | 1.00 | 47.19 |
| ATOM | 1206 | CD2 | HIS | B | 35 | 122.371 | 19.906 | 130.892 | 1.00 | 48.47 |
| ATOM | 1207 | ND1 | HIS | B | 35 | 123.109 | 17.951 | 130.247 | 1.00 | 49.89 |
| ATOM | 1208 | CE1 | HIS | B | 35 | 122.495 | 18.499 | 129.212 | 1.00 | 50.03 |
| ATOM | 1209 | NE2 | HIS | B | 35 | 122.037 | 19.684 | 129.576 | 1.00 | 48.17 |
| ATOM | 1210 | C | HIS | B | 35 | 123.436 | 17.302 | 134.848 | 1.00 | 39.62 |
| ATOM | 1211 | O | HIS | B | 35 | 123.449 | 18.093 | 135.796 | 1.00 | 38.77 |
| ATOM | 1212 | N | PRO | B | 36 | 124.045 | 16.104 | 134.912 | 1.00 | 39.09 |
| ATOM | 1213 | CD | PRO | B | 36 | 123.867 | 14.947 | 134.014 | 1.00 | 39.98 |
| ATOM | 1214 | CA | PRO | B | 36 | 124.769 | 15.698 | 136.117 | 1.00 | 38.70 |
| ATOM | 1215 | CB | PRO | B | 36 | 125.303 | 14.324 | 135.746 | 1.00 | 37.90 |
| ATOM | 1216 | CG | PRO | B | 36 | 124.187 | 13.773 | 134.938 | 1.00 | 38.98 |
| ATOM | 1217 | C | PRO | B | 36 | 125.870 | 16.673 | 136.521 | 1.00 | 38.41 |
| ATOM | 1218 | O | PRO | B | 36 | 126.284 | 16.687 | 137.678 | 1.00 | 37.55 |
| ATOM | 1219 | N | ASP | B | 37 | 126.327 | 17.494 | 135.575 | 1.00 | 38.67 |
| ATOM | 1220 | CA | ASP | B | 37 | 127.367 | 18.476 | 135.866 | 1.00 | 39.47 |
| ATOM | 1221 | CB | ASP | B | 37 | 128.194 | 18.804 | 134.620 | 1.00 | 41.64 |
| ATOM | 1222 | CG | ASP | B | 37 | 127.404 | 19.576 | 133.574 | 1.00 | 44.39 |
| ATOM | 1223 | OD1 | ASP | B | 37 | 126.465 | 20.313 | 133.950 | 1.00 | 44.40 |

TABLE 1-continued

FGFR1 D2–D3 Complexed with FGF2

| ATOM | 1224 | OD2 | ASP | B | 37 | 127.734 | 19.458 | 132.370 | 1.00 | 45.65 |
|---|---|---|---|---|---|---|---|---|---|---|
| ATOM | 1225 | C | ASP | B | 37 | 126.796 | 19.783 | 136.409 | 1.00 | 40.37 |
| ATOM | 1226 | O | ASP | B | 37 | 127.542 | 20.745 | 136.601 | 1.00 | 41.14 |
| ATOM | 1227 | N | GLY | B | 38 | 125.482 | 19.836 | 136.629 | 1.00 | 40.30 |
| ATOM | 1228 | CA | GLY | B | 38 | 124.875 | 21.055 | 137.152 | 1.00 | 38.99 |
| ATOM | 1229 | C | GLY | B | 38 | 124.299 | 22.029 | 136.125 | 1.00 | 38.03 |
| ATOM | 1230 | O | GLY | B | 38 | 123.657 | 23.009 | 136.501 | 1.00 | 36.64 |
| ATOM | 1231 | N | ARG | B | 39 | 124.525 | 21.787 | 134.837 | 1.00 | 37.93 |
| ATOM | 1232 | CA | ARG | B | 39 | 123.969 | 22.666 | 133.809 | 1.00 | 39.37 |
| ATOM | 1233 | CB | ARG | B | 39 | 124.578 | 22.392 | 132.436 | 1.00 | 42.00 |
| ATOM | 1234 | CG | ARG | B | 39 | 126.018 | 22.802 | 132.223 | 1.00 | 46.71 |
| ATOM | 1235 | CD | ARG | B | 39 | 126.459 | 22.370 | 130.817 | 1.00 | 51.06 |
| ATOM | 1236 | NE | ARG | B | 39 | 126.320 | 20.921 | 130.634 | 1.00 | 54.86 |
| ATOM | 1237 | CZ | ARG | B | 39 | 125.992 | 20.323 | 129.487 | 1.00 | 56.96 |
| ATOM | 1238 | NH1 | ARG | B | 39 | 125.893 | 18.996 | 129.436 | 1.00 | 57.35 |
| ATOM | 1239 | NH2 | ARG | B | 39 | 125.751 | 21.044 | 128.395 | 1.00 | 56.77 |
| ATOM | 1240 | C | ARG | B | 39 | 122.470 | 22.413 | 133.680 | 1.00 | 39.42 |
| ATOM | 1241 | O | ARG | B | 39 | 121.997 | 21.295 | 133.899 | 1.00 | 38.02 |
| ATOM | 1242 | N | VAL | B | 40 | 121.733 | 23.452 | 133.298 | 1.00 | 40.07 |
| ATOM | 1243 | CA | VAL | B | 40 | 120.284 | 23.353 | 133.107 | 1.00 | 40.65 |
| ATOM | 1244 | CB | VAL | B | 40 | 119.526 | 24.162 | 134.182 | 1.00 | 41.39 |
| ATOM | 1245 | CG1 | VAL | B | 40 | 118.045 | 24.203 | 133.862 | 1.00 | 41.97 |
| ATOM | 1246 | CG2 | VAL | B | 40 | 119.738 | 23.525 | 135.545 | 1.00 | 42.94 |
| ATOM | 1247 | C | VAL | B | 40 | 119.876 | 23.848 | 131.713 | 1.00 | 40.44 |
| ATOM | 1248 | O | VAL | B | 40 | 120.300 | 24.921 | 131.274 | 1.00 | 41.16 |
| ATOM | 1249 | N | ASP | B | 41 | 119.056 | 23.064 | 131.018 | 1.00 | 39.94 |
| ATOM | 1250 | CA | ASP | B | 41 | 118.607 | 23.430 | 129.669 | 1.00 | 39.12 |
| ATOM | 1251 | CB | ASP | B | 41 | 119.706 | 23.118 | 128.659 | 1.00 | 39.83 |
| ATOM | 1252 | CG | ASP | B | 41 | 119.986 | 21.622 | 128.554 | 1.00 | 43.38 |
| ATOM | 1253 | OD1 | ASP | B | 41 | 120.942 | 21.243 | 127.844 | 1.00 | 45.53 |
| ATOM | 1254 | OD2 | ASP | B | 41 | 119.251 | 20.820 | 129.180 | 1.00 | 42.00 |
| ATOM | 1255 | C | ASP | B | 41 | 117.365 | 22.622 | 129.312 | 1.00 | 37.83 |
| ATOM | 1256 | O | ASP | B | 41 | 116.745 | 22.011 | 130.184 | 1.00 | 38.38 |
| ATOM | 1257 | N | GLY | B | 42 | 117.021 | 22.603 | 128.028 | 1.00 | 35.97 |
| ATOM | 1258 | CA | GLY | B | 42 | 115.860 | 21.849 | 127.590 | 1.00 | 35.38 |
| ATOM | 1259 | C | GLY | B | 42 | 116.124 | 20.881 | 126.446 | 1.00 | 35.25 |
| ATOM | 1260 | O | GLY | B | 42 | 117.119 | 21.001 | 125.742 | 1.00 | 37.44 |
| ATOM | 1261 | N | VAL | B | 43 | 115.233 | 19.912 | 126.268 | 1.00 | 33.57 |
| ATOM | 1262 | CA | VAL | B | 43 | 115.352 | 18.928 | 125.203 | 1.00 | 32.47 |
| ATOM | 1263 | CB | VAL | B | 43 | 116.279 | 17.752 | 125.573 | 1.00 | 30.78 |
| ATOM | 1264 | CG1 | VAL | B | 43 | 117.687 | 18.146 | 125.372 | 1.00 | 30.16 |
| ATOM | 1265 | CG2 | VAL | B | 43 | 116.049 | 17.324 | 127.008 | 1.00 | 30.59 |
| ATOM | 1266 | C | VAL | B | 43 | 113.997 | 18.340 | 124.899 | 1.00 | 33.51 |
| ATOM | 1267 | O | VAL | B | 43 | 113.227 | 18.032 | 125.810 | 1.00 | 34.09 |
| ATOM | 1268 | N | ARG | B | 44 | 113.720 | 18.162 | 123.615 | 1.00 | 33.46 |
| ATOM | 1269 | CA | ARG | B | 44 | 112.456 | 17.600 | 123.178 | 1.00 | 33.32 |
| ATOM | 1270 | CB | ARG | B | 44 | 112.217 | 17.925 | 121.711 | 1.00 | 32.91 |
| ATOM | 1271 | CG | ARG | B | 44 | 112.222 | 19.390 | 121.366 | 1.00 | 33.07 |
| ATOM | 1272 | CD | ARG | B | 44 | 111.099 | 19.639 | 120.384 | 1.00 | 34.99 |
| ATOM | 1273 | NE | ARG | B | 44 | 111.156 | 20.953 | 119.760 | 1.00 | 35.14 |
| ATOM | 1274 | CZ | ARG | B | 44 | 112.144 | 21.349 | 118.969 | 1.00 | 36.05 |
| ATOM | 1275 | NH1 | ARG | B | 44 | 113.166 | 20.523 | 118.714 | 1.00 | 36.18 |
| ATOM | 1276 | NH2 | ARG | B | 44 | 112.097 | 22.556 | 118.420 | 1.00 | 33.20 |
| ATOM | 1277 | C | ARG | B | 44 | 112.416 | 16.087 | 123.338 | 1.00 | 33.08 |
| ATOM | 1278 | O | ARG | B | 44 | 111.340 | 15.502 | 123.471 | 1.00 | 32.18 |
| ATOM | 1279 | N | GLU | B | 45 | 113.579 | 15.450 | 123.322 | 1.00 | 33.83 |
| ATOM | 1280 | CA | GLU | B | 45 | 113.611 | 13.994 | 123.424 | 1.00 | 36.58 |
| ATOM | 1281 | CB | GLU | B | 45 | 114.997 | 13.433 | 123.108 | 1.00 | 38.67 |
| ATOM | 1282 | CG | GLU | B | 45 | 115.037 | 11.900 | 123.234 | 1.00 | 41.88 |
| ATOM | 1283 | CD | GLU | B | 45 | 113.997 | 11.189 | 122.343 | 1.00 | 44.31 |
| ATOM | 1284 | OE1 | GLU | B | 45 | 114.080 | 11.341 | 121.102 | 1.00 | 42.64 |
| ATOM | 1285 | OE2 | GLU | B | 45 | 113.104 | 10.476 | 122.878 | 1.00 | 43.97 |
| ATOM | 1286 | C | GLU | B | 45 | 113.161 | 13.415 | 124.748 | 1.00 | 36.47 |
| ATOM | 1287 | O | GLU | B | 45 | 113.914 | 13.398 | 125.724 | 1.00 | 37.20 |
| ATOM | 1288 | N | LYS | B | 46 | 111.939 | 12.899 | 124.752 | 1.00 | 36.81 |
| ATOM | 1289 | CA | LYS | B | 46 | 111.332 | 12.304 | 125.935 | 1.00 | 37.99 |
| ATOM | 1290 | CB | LYS | B | 46 | 109.933 | 11.794 | 125.581 | 1.00 | 39.90 |
| ATOM | 1291 | CG | LYS | B | 46 | 109.087 | 11.317 | 126.752 | 1.00 | 43.95 |
| ATOM | 1292 | CD | LYS | B | 46 | 107.666 | 10.993 | 126.262 | 1.00 | 47.36 |
| ATOM | 1293 | CE | LYS | B | 46 | 106.787 | 10.333 | 127.338 | 1.00 | 48.53 |
| ATOM | 1294 | NZ | LYS | B | 46 | 106.393 | 8.920 | 126.999 | 1.00 | 47.10 |
| ATOM | 1295 | C | LYS | B | 46 | 112.159 | 11.175 | 126.553 | 1.00 | 37.61 |
| ATOM | 1296 | O | LYS | B | 46 | 112.018 | 10.874 | 127.736 | 1.00 | 38.77 |
| ATOM | 1297 | N | SER | B | 47 | 113.032 | 10.554 | 125.773 | 1.00 | 37.27 |
| ATOM | 1298 | CA | SER | B | 47 | 113.843 | 9.464 | 126.314 | 1.00 | 37.83 |
| ATOM | 1299 | CB | SER | B | 47 | 114.182 | 8.465 | 125.209 | 1.00 | 40.05 |
| ATOM | 1300 | OG | SER | B | 47 | 114.903 | 9.101 | 124.168 | 1.00 | 41.43 |

TABLE 1-continued

FGFR1 D2–D3 Complexed with FGF2

| ATOM | 1301 | C | SER | B | 47 | 115.137 | 9.953 | 126.971 | 1.00 | 37.29 |
|---|---|---|---|---|---|---|---|---|---|---|
| ATOM | 1302 | O | SER | B | 47 | 115.942 | 9.151 | 127.461 | 1.00 | 36.39 |
| ATOM | 1303 | N | ASP | B | 48 | 115.337 | 11.267 | 126.984 | 1.00 | 35.33 |
| ATOM | 1304 | CA | ASP | B | 48 | 116.536 | 11.807 | 127.588 | 1.00 | 34.88 |
| ATOM | 1305 | CB | ASP | B | 48 | 116.502 | 13.319 | 127.628 | 1.00 | 35.85 |
| ATOM | 1306 | CG | ASP | B | 48 | 117.822 | 13.882 | 128.042 | 1.00 | 37.14 |
| ATOM | 1307 | OD1 | ASP | B | 48 | 118.492 | 14.504 | 127.195 | 1.00 | 38.97 |
| ATOM | 1308 | OD2 | ASP | B | 48 | 118.203 | 13.669 | 129.212 | 1.00 | 38.89 |
| ATOM | 1309 | C | ASP | B | 48 | 116.675 | 11.275 | 129.005 | 1.00 | 34.83 |
| ATOM | 1310 | O | ASP | B | 48 | 115.711 | 11.244 | 129.771 | 1.00 | 34.62 |
| ATOM | 1311 | N | PRO | B | 49 | 117.890 | 10.875 | 129.388 | 1.00 | 34.68 |
| ATOM | 1312 | CD | PRO | B | 49 | 119.175 | 11.093 | 128.695 | 1.00 | 35.21 |
| ATOM | 1313 | CA | PRO | B | 49 | 118.114 | 10.336 | 130.730 | 1.00 | 34.34 |
| ATOM | 1314 | CB | PRO | B | 49 | 119.507 | 9.758 | 130.624 | 1.00 | 34.29 |
| ATOM | 1315 | CG | PRO | B | 49 | 120.194 | 10.836 | 129.798 | 1.00 | 35.75 |
| ATOM | 1316 | C | PRO | B | 49 | 118.026 | 11.340 | 131.869 | 1.00 | 34.60 |
| ATOM | 1317 | O | PRO | B | 49 | 117.728 | 10.969 | 133.004 | 1.00 | 34.68 |
| ATOM | 1318 | N | HIS | B | 50 | 118.274 | 12.611 | 131.569 | 1.00 | 34.99 |
| ATOM | 1319 | CA | HIS | B | 50 | 118.281 | 13.640 | 132.605 | 1.00 | 35.11 |
| ATOM | 1320 | CB | HIS | B | 50 | 119.514 | 14.516 | 132.433 | 1.00 | 38.33 |
| ATOM | 1321 | CG | HIS | B | 50 | 120.771 | 13.732 | 132.248 | 1.00 | 39.99 |
| ATOM | 1322 | CD2 | HIS | B | 50 | 121.628 | 13.656 | 131.205 | 1.00 | 40.25 |
| ATOM | 1323 | ND1 | HIS | B | 50 | 121.224 | 12.830 | 133.186 | 1.00 | 40.36 |
| ATOM | 1324 | CE1 | HIS | B | 50 | 122.304 | 12.228 | 132.725 | 1.00 | 41.16 |
| ATOM | 1325 | NE2 | HIS | B | 50 | 122.569 | 12.711 | 131.525 | 1.00 | 41.80 |
| ATOM | 1326 | C | HIS | B | 50 | 117.064 | 14.529 | 132.695 | 1.00 | 33.22 |
| ATOM | 1327 | O | HIS | B | 50 | 117.154 | 15.649 | 133.191 | 1.00 | 32.87 |
| ATOM | 1328 | N | ILE | B | 51 | 115.921 | 14.046 | 132.237 | 1.00 | 31.67 |
| ATOM | 1329 | CA | ILE | B | 51 | 114.726 | 14.867 | 132.302 | 1.00 | 29.82 |
| ATOM | 1330 | CB | ILE | B | 51 | 113.988 | 14.899 | 130.938 | 1.00 | 27.56 |
| ATOM | 1331 | CG2 | ILE | B | 51 | 114.947 | 15.389 | 129.861 | 1.00 | 27.80 |
| ATOM | 1332 | CG1 | ILE | B | 51 | 113.427 | 13.520 | 130.591 | 1.00 | 23.56 |
| ATOM | 1333 | CD1 | ILE | B | 51 | 112.630 | 13.498 | 129.324 | 1.00 | 19.14 |
| ATOM | 1334 | C | ILE | B | 51 | 113.744 | 14.454 | 133.387 | 1.00 | 29.57 |
| ATOM | 1335 | O | ILE | B | 51 | 112.771 | 15.156 | 133.625 | 1.00 | 29.45 |
| ATOM | 1336 | N | LYS | B | 52 | 113.998 | 13.324 | 134.043 | 1.00 | 30.99 |
| ATOM | 1337 | CA | LYS | B | 52 | 113.119 | 12.857 | 135.114 | 1.00 | 32.77 |
| ATOM | 1338 | CB | LYS | B | 52 | 113.319 | 11.364 | 135.377 | 1.00 | 35.63 |
| ATOM | 1339 | CG | LYS | B | 52 | 112.769 | 10.497 | 134.265 | 1.00 | 40.57 |
| ATOM | 1340 | CD | LYS | B | 52 | 112.534 | 9.059 | 134.718 | 1.00 | 43.44 |
| ATOM | 1341 | CE | LYS | B | 52 | 111.798 | 8.274 | 133.625 | 1.00 | 44.57 |
| ATOM | 1342 | NZ | LYS | B | 52 | 111.173 | 7.015 | 134.138 | 1.00 | 46.19 |
| ATOM | 1343 | C | LYS | B | 52 | 113.387 | 13.651 | 136.386 | 1.00 | 31.74 |
| ATOM | 1344 | O | LYS | B | 52 | 114.458 | 13.540 | 136.990 | 1.00 | 30.75 |
| ATOM | 1345 | N | LEU | B | 53 | 112.389 | 14.443 | 136.776 | 1.00 | 30.81 |
| ATOM | 1346 | CA | LEU | B | 53 | 112.450 | 15.321 | 137.941 | 1.00 | 28.75 |
| ATOM | 1347 | CB | LEU | B | 53 | 111.893 | 16.689 | 137.561 | 1.00 | 26.09 |
| ATOM | 1348 | CG | LEU | B | 53 | 112.283 | 17.154 | 136.159 | 1.00 | 23.54 |
| ATOM | 1349 | CD1 | LEU | B | 53 | 111.568 | 18.436 | 135.788 | 1.00 | 21.62 |
| ATOM | 1350 | CD2 | LEU | B | 53 | 113.780 | 17.343 | 136.124 | 1.00 | 22.95 |
| ATOM | 1351 | C | LEU | B | 53 | 111.656 | 14.791 | 139.123 | 1.00 | 28.90 |
| ATOM | 1352 | O | LEU | B | 53 | 110.652 | 14.108 | 138.960 | 1.00 | 29.34 |
| ATOM | 1353 | N | GLN | B | 54 | 112.116 | 15.114 | 140.323 | 1.00 | 29.74 |
| ATOM | 1354 | CA | GLN | B | 54 | 111.426 | 14.695 | 141.530 | 1.00 | 28.75 |
| ATOM | 1355 | CB | GLN | B | 54 | 112.362 | 13.864 | 142.403 | 1.00 | 26.78 |
| ATOM | 1356 | CG | GLN | B | 54 | 111.667 | 13.080 | 143.490 | 1.00 | 28.67 |
| ATOM | 1357 | CD | GLN | B | 54 | 110.638 | 12.088 | 142.956 | 1.00 | 30.79 |
| ATOM | 1358 | OE1 | GLN | B | 54 | 110.960 | 11.197 | 142.163 | 1.00 | 33.61 |
| ATOM | 1359 | NE2 | GLN | B | 54 | 109.396 | 12.235 | 143.398 | 1.00 | 30.23 |
| ATOM | 1360 | C | GLN | B | 54 | 111.025 | 15.986 | 142.234 | 1.00 | 28.64 |
| ATOM | 1361 | O | GLN | B | 54 | 111.854 | 16.671 | 142.816 | 1.00 | 29.72 |
| ATOM | 1362 | N | LEU | B | 55 | 109.752 | 16.340 | 142.132 | 1.00 | 28.94 |
| ATOM | 1363 | CA | LEU | B | 55 | 109.270 | 17.554 | 142.759 | 1.00 | 27.80 |
| ATOM | 1364 | CB | LEU | B | 55 | 108.072 | 18.148 | 142.006 | 1.00 | 27.78 |
| ATOM | 1365 | CG | LEU | B | 55 | 108.160 | 18.507 | 140.514 | 1.00 | 26.52 |
| ATOM | 1366 | CD1 | LEU | B | 55 | 109.194 | 19.576 | 140.274 | 1.00 | 27.66 |
| ATOM | 1367 | CD2 | LEU | B | 55 | 108.480 | 17.267 | 139.724 | 1.00 | 27.39 |
| ATOM | 1368 | C | LEU | B | 55 | 108.863 | 17.173 | 144.167 | 1.00 | 27.87 |
| ATOM | 1369 | O | LEU | B | 55 | 108.118 | 16.210 | 144.389 | 1.00 | 27.58 |
| ATOM | 1370 | N | GLN | B | 56 | 109.394 | 17.925 | 145.119 | 1.00 | 27.07 |
| ATOM | 1371 | CA | GLN | B | 56 | 109.115 | 17.699 | 146.519 | 1.00 | 26.11 |
| ATOM | 1372 | CB | GLN | B | 56 | 110.390 | 17.269 | 147.244 | 1.00 | 25.15 |
| ATOM | 1373 | CG | GLN | B | 56 | 110.220 | 17.014 | 148.719 | 1.00 | 20.80 |
| ATOM | 1374 | CD | GLN | B | 56 | 109.326 | 15.828 | 149.010 | 1.00 | 23.03 |
| ATOM | 1375 | OE1 | GLN | B | 56 | 109.585 | 14.707 | 148.564 | 1.00 | 21.86 |
| ATOM | 1376 | NE2 | GLN | B | 56 | 108.265 | 16.067 | 149.771 | 1.00 | 24.69 |
| ATOM | 1377 | C | GLN | B | 56 | 108.601 | 18.997 | 147.114 | 1.00 | 27.37 |

TABLE 1-continued

FGFR1 D2–D3 Complexed with FGF2

| | | | | | | | | | |
|---|---|---|---|---|---|---|---|---|---|
| ATOM | 1378 | O | GLN | B | 56 | 109.140 | 20.076 | 146.863 | 1.00 | 26.42 |
| ATOM | 1379 | N | ALA | B | 57 | 107.545 | 18.891 | 147.902 | 1.00 | 27.79 |
| ATOM | 1380 | CA | ALA | B | 57 | 106.985 | 20.068 | 148.521 | 1.00 | 27.74 |
| ATOM | 1381 | CB | ALA | B | 57 | 105.495 | 19.869 | 148.763 | 1.00 | 27.74 |
| ATOM | 1382 | C | ALA | B | 57 | 107.705 | 20.310 | 149.833 | 1.00 | 28.44 |
| ATOM | 1383 | O | ALA | B | 57 | 107.961 | 19.372 | 150.593 | 1.00 | 26.26 |
| ATOM | 1384 | N | GLU | B | 58 | 108.042 | 21.572 | 150.087 | 1.00 | 30.24 |
| ATOM | 1385 | CA | GLU | B | 58 | 108.710 | 21.951 | 151.328 | 1.00 | 31.94 |
| ATOM | 1386 | CB | GLU | B | 58 | 109.725 | 23.073 | 151.089 | 1.00 | 32.06 |
| ATOM | 1387 | CG | GLU | B | 58 | 110.875 | 23.099 | 152.094 | 1.00 | 32.70 |
| ATOM | 1388 | CD | GLU | B | 58 | 111.582 | 21.747 | 152.219 | 1.00 | 35.13 |
| ATOM | 1389 | OE1 | GLU | B | 58 | 111.629 | 20.999 | 151.210 | 1.00 | 37.39 |
| ATOM | 1390 | OE2 | GLU | B | 58 | 112.104 | 21.436 | 153.319 | 1.00 | 34.15 |
| ATOM | 1391 | C | GLU | B | 58 | 107.614 | 22.433 | 152.255 | 1.00 | 32.23 |
| ATOM | 1392 | O | GLU | B | 58 | 107.745 | 22.371 | 153.471 | 1.00 | 33.09 |
| ATOM | 1393 | N | GLU | B | 59 | 106.531 | 22.903 | 151.643 | 1.00 | 32.83 |
| ATOM | 1394 | CA | GLU | B | 59 | 105.347 | 23.391 | 152.336 | 1.00 | 32.73 |
| ATOM | 1395 | CB | GLU | B | 59 | 105.676 | 24.642 | 153.137 | 1.00 | 34.19 |
| ATOM | 1396 | CG | GLU | B | 59 | 106.362 | 25.734 | 152.354 | 1.00 | 37.42 |
| ATOM | 1397 | CD | GLU | B | 59 | 106.419 | 27.017 | 153.160 | 1.00 | 41.98 |
| ATOM | 1398 | OE1 | GLU | B | 59 | 106.713 | 26.920 | 154.376 | 1.00 | 43.49 |
| ATOM | 1399 | OE2 | GLU | B | 59 | 106.175 | 28.109 | 152.594 | 1.00 | 42.36 |
| ATOM | 1400 | C | GLU | B | 59 | 104.294 | 23.697 | 151.275 | 1.00 | 31.75 |
| ATOM | 1401 | O | GLU | B | 59 | 104.594 | 23.657 | 150.086 | 1.00 | 30.10 |
| ATOM | 1402 | N | ARG | B | 60 | 103.070 | 24.007 | 151.689 | 1.00 | 31.28 |
| ATOM | 1403 | CA | ARG | B | 60 | 102.009 | 24.291 | 150.722 | 1.00 | 32.14 |
| ATOM | 1404 | CB | ARG | B | 60 | 100.765 | 24.866 | 151.402 | 1.00 | 31.64 |
| ATOM | 1405 | CG | ARG | B | 60 | 99.878 | 23.830 | 152.044 | 1.00 | 36.28 |
| ATOM | 1406 | CD | ARG | B | 60 | 98.689 | 24.483 | 152.722 | 1.00 | 39.82 |
| ATOM | 1407 | NE | ARG | B | 60 | 97.848 | 25.183 | 151.756 | 1.00 | 44.52 |
| ATOM | 1408 | CZ | ARG | B | 60 | 96.775 | 25.901 | 152.076 | 1.00 | 44.93 |
| ATOM | 1409 | NH1 | ARG | B | 60 | 96.409 | 26.017 | 153.349 | 1.00 | 44.87 |
| ATOM | 1410 | NH2 | ARG | B | 60 | 96.066 | 26.499 | 151.121 | 1.00 | 44.99 |
| ATOM | 1411 | C | ARG | B | 60 | 102.426 | 25.228 | 149.604 | 1.00 | 30.88 |
| ATOM | 1412 | O | ARG | B | 60 | 102.863 | 26.347 | 149.856 | 1.00 | 30.20 |
| ATOM | 1413 | N | GLY | B | 61 | 102.279 | 24.754 | 148.368 | 1.00 | 29.53 |
| ATOM | 1414 | CA | GLY | B | 61 | 102.623 | 25.558 | 147.209 | 1.00 | 28.37 |
| ATOM | 1415 | C | GLY | B | 61 | 104.097 | 25.855 | 146.951 | 1.00 | 26.54 |
| ATOM | 1416 | O | GLY | B | 61 | 104.413 | 26.716 | 146.125 | 1.00 | 25.85 |
| ATOM | 1417 | N | VAL | B | 62 | 104.994 | 25.154 | 147.642 | 1.00 | 23.72 |
| ATOM | 1418 | CA | VAL | B | 62 | 106.428 | 25.364 | 147.463 | 1.00 | 21.76 |
| ATOM | 1419 | CB | VAL | B | 62 | 107.067 | 26.030 | 148.710 | 1.00 | 18.92 |
| ATOM | 1420 | CG1 | VAL | B | 62 | 108.589 | 25.949 | 148.630 | 1.00 | 18.20 |
| ATOM | 1421 | CG2 | VAL | B | 62 | 106.637 | 27.468 | 148.811 | 1.00 | 14.47 |
| ATOM | 1422 | C | VAL | B | 62 | 107.132 | 24.036 | 147.206 | 1.00 | 22.30 |
| ATOM | 1423 | O | VAL | B | 62 | 106.994 | 23.093 | 147.982 | 1.00 | 22.35 |
| ATOM | 1424 | N | VAL | B | 63 | 107.899 | 23.972 | 146.125 | 1.00 | 21.78 |
| ATOM | 1425 | CA | VAL | B | 63 | 108.599 | 22.750 | 145.787 | 1.00 | 23.21 |
| ATOM | 1426 | CB | VAL | B | 63 | 107.937 | 22.058 | 144.578 | 1.00 | 21.42 |
| ATOM | 1427 | CG1 | VAL | B | 63 | 106.487 | 21.831 | 144.850 | 1.00 | 20.97 |
| ATOM | 1428 | CG2 | VAL | B | 63 | 108.106 | 22.900 | 143.338 | 1.00 | 19.19 |
| ATOM | 1429 | C | VAL | B | 63 | 110.067 | 22.963 | 145.440 | 1.00 | 25.78 |
| ATOM | 1430 | O | VAL | B | 63 | 110.484 | 24.060 | 145.071 | 1.00 | 28.04 |
| ATOM | 1431 | N | SER | B | 64 | 110.842 | 21.894 | 145.577 | 1.00 | 26.96 |
| ATOM | 1432 | CA | SER | B | 64 | 112.253 | 21.905 | 145.214 | 1.00 | 27.58 |
| ATOM | 1433 | CB | SER | B | 64 | 113.153 | 21.333 | 146.323 | 1.00 | 26.89 |
| ATOM | 1434 | OG | SER | B | 64 | 113.006 | 19.927 | 146.434 | 1.00 | 27.20 |
| ATOM | 1435 | C | SER | B | 64 | 112.197 | 20.941 | 144.048 | 1.00 | 27.27 |
| ATOM | 1436 | O | SER | B | 64 | 111.467 | 19.956 | 144.090 | 1.00 | 27.77 |
| ATOM | 1437 | N | ILE | B | 65 | 112.943 | 21.239 | 143.000 | 1.00 | 27.86 |
| ATOM | 1438 | CA | ILE | B | 65 | 112.954 | 20.399 | 141.820 | 1.00 | 26.92 |
| ATOM | 1439 | CB | ILE | B | 65 | 112.755 | 21.274 | 140.552 | 1.00 | 26.65 |
| ATOM | 1440 | CG2 | ILE | B | 65 | 112.860 | 20.409 | 139.280 | 1.00 | 26.91 |
| ATOM | 1441 | CG1 | ILE | B | 65 | 111.390 | 21.982 | 140.646 | 1.00 | 24.20 |
| ATOM | 1442 | CD1 | ILE | B | 65 | 111.158 | 23.103 | 139.653 | 1.00 | 21.27 |
| ATOM | 1443 | C | ILE | B | 65 | 114.284 | 19.663 | 141.781 | 1.00 | 27.92 |
| ATOM | 1444 | O | ILE | B | 65 | 115.338 | 20.279 | 141.604 | 1.00 | 29.68 |
| ATOM | 1445 | N | LYS | B | 66 | 114.235 | 18.349 | 141.975 | 1.00 | 27.70 |
| ATOM | 1446 | CA | LYS | B | 66 | 115.443 | 17.536 | 141.974 | 1.00 | 27.93 |
| ATOM | 1447 | CB | LYS | B | 66 | 115.433 | 16.571 | 143.141 | 1.00 | 28.47 |
| ATOM | 1448 | CG | LYS | B | 66 | 116.602 | 15.613 | 143.107 | 1.00 | 28.99 |
| ATOM | 1449 | CD | LYS | B | 66 | 116.637 | 14.760 | 144.353 | 1.00 | 31.91 |
| ATOM | 1450 | CE | LYS | B | 66 | 118.065 | 14.652 | 144.880 | 1.00 | 34.91 |
| ATOM | 1451 | NZ | LYS | B | 66 | 118.119 | 13.913 | 146.175 | 1.00 | 37.70 |
| ATOM | 1452 | C | LYS | B | 66 | 115.621 | 16.709 | 140.717 | 1.00 | 29.46 |
| ATOM | 1453 | O | LYS | B | 66 | 114.724 | 15.950 | 140.354 | 1.00 | 29.47 |
| ATOM | 1454 | N | GLY | B | 67 | 116.777 | 16.847 | 140.064 | 1.00 | 29.55 |

TABLE 1-continued

FGFR1 D2–D3 Complexed with FGF2

| ATOM | 1455 | CA | GLY | B | 67 | 117.058 | 16.059 | 138.877 | 1.00 | 29.40 |
|---|---|---|---|---|---|---|---|---|---|---|
| ATOM | 1456 | C | GLY | B | 67 | 117.436 | 14.674 | 139.374 | 1.00 | 30.54 |
| ATOM | 1457 | O | GLY | B | 67 | 118.471 | 14.506 | 140.019 | 1.00 | 31.69 |
| ATOM | 1458 | N | VAL | B | 68 | 116.600 | 13.680 | 139.097 | 1.00 | 30.20 |
| ATOM | 1459 | CA | VAL | B | 68 | 116.861 | 12.328 | 139.577 | 1.00 | 31.28 |
| ATOM | 1460 | CB | VAL | B | 68 | 115.708 | 11.363 | 139.188 | 1.00 | 29.45 |
| ATOM | 1461 | CG1 | VAL | B | 68 | 116.075 | 9.937 | 139.551 | 1.00 | 24.11 |
| ATOM | 1462 | CG2 | VAL | B | 68 | 114.424 | 11.768 | 139.911 | 1.00 | 26.34 |
| ATOM | 1463 | C | VAL | B | 68 | 118.184 | 11.744 | 139.110 | 1.00 | 33.38 |
| ATOM | 1464 | O | VAL | B | 68 | 118.915 | 11.157 | 139.899 | 1.00 | 33.82 |
| ATOM | 1465 | N | SER | B | 69 | 118.494 | 11.893 | 137.830 | 1.00 | 36.86 |
| ATOM | 1466 | CA | SER | B | 69 | 119.744 | 11.352 | 137.317 | 1.00 | 38.82 |
| ATOM | 1467 | CB | SER | B | 69 | 119.751 | 11.387 | 135.792 | 1.00 | 40.75 |
| ATOM | 1468 | OG | SER | B | 69 | 120.967 | 10.861 | 135.293 | 1.00 | 42.57 |
| ATOM | 1469 | C | SER | B | 69 | 120.941 | 12.137 | 137.867 | 1.00 | 39.71 |
| ATOM | 1470 | O | SER | B | 69 | 121.865 | 11.550 | 138.434 | 1.00 | 40.03 |
| ATOM | 1471 | N | ALA | B | 70 | 120.911 | 13.459 | 137.717 | 1.00 | 39.07 |
| ATOM | 1472 | CA | ALA | B | 70 | 121.998 | 14.316 | 138.187 | 1.00 | 38.97 |
| ATOM | 1473 | CB | ALA | B | 70 | 121.841 | 15.714 | 137.608 | 1.00 | 37.82 |
| ATOM | 1474 | C | ALA | B | 70 | 122.102 | 14.422 | 139.702 | 1.00 | 39.68 |
| ATOM | 1475 | O | ALA | B | 70 | 123.134 | 14.840 | 140.231 | 1.00 | 40.63 |
| ATOM | 1476 | N | ASN | B | 71 | 121.041 | 14.044 | 140.401 | 1.00 | 40.19 |
| ATOM | 1477 | CA | ASN | B | 71 | 121.007 | 14.161 | 141.854 | 1.00 | 40.46 |
| ATOM | 1478 | CB | ASN | B | 71 | 121.953 | 13.170 | 142.516 | 1.00 | 40.79 |
| ATOM | 1479 | CG | ASN | B | 71 | 121.742 | 13.090 | 144.016 | 1.00 | 40.60 |
| ATOM | 1480 | OD1 | ASN | B | 71 | 120.735 | 12.562 | 144.486 | 1.00 | 41.57 |
| ATOM | 1481 | ND2 | ASN | B | 71 | 122.683 | 13.630 | 144.775 | 1.00 | 41.54 |
| ATOM | 1482 | C | ASN | B | 71 | 121.398 | 15.584 | 142.270 | 1.00 | 40.88 |
| ATOM | 1483 | O | ASN | B | 71 | 122.240 | 15.780 | 143.154 | 1.00 | 41.28 |
| ATOM | 1484 | N | ARG | B | 72 | 120.788 | 16.567 | 141.611 | 1.00 | 40.64 |
| ATOM | 1485 | CA | ARG | B | 72 | 121.036 | 17.980 | 141.891 | 1.00 | 40.55 |
| ATOM | 1486 | CB | ARG | B | 72 | 121.898 | 18.600 | 140.793 | 1.00 | 41.41 |
| ATOM | 1487 | CG | ARG | B | 72 | 123.366 | 18.189 | 140.786 | 1.00 | 42.06 |
| ATOM | 1488 | CD | ARG | B | 72 | 124.021 | 18.715 | 139.515 | 1.00 | 43.85 |
| ATOM | 1489 | NE | ARG | B | 72 | 125.474 | 18.584 | 139.511 | 1.00 | 44.83 |
| ATOM | 1490 | CZ | ARG | B | 72 | 126.299 | 19.341 | 140.226 | 1.00 | 42.83 |
| ATOM | 1491 | NH1 | ARG | B | 72 | 125.819 | 20.294 | 141.013 | 1.00 | 42.08 |
| ATOM | 1492 | NH2 | ARG | B | 72 | 127.606 | 19.137 | 140.154 | 1.00 | 41.81 |
| ATOM | 1493 | C | ARG | B | 72 | 119.704 | 18.716 | 141.946 | 1.00 | 40.00 |
| ATOM | 1494 | O | ARG | B | 72 | 118.725 | 18.279 | 141.350 | 1.00 | 40.69 |
| ATOM | 1495 | N | TYR | B | 73 | 119.678 | 19.841 | 142.650 | 1.00 | 39.69 |
| ATOM | 1496 | CA | TYR | B | 73 | 118.462 | 20.629 | 142.784 | 1.00 | 38.01 |
| ATOM | 1497 | CB | TYR | B | 73 | 118.266 | 21.040 | 144.239 | 1.00 | 37.74 |
| ATOM | 1498 | CG | TYR | B | 73 | 118.162 | 19.861 | 145.156 | 1.00 | 38.72 |
| ATOM | 1499 | CD1 | TYR | B | 73 | 119.296 | 19.134 | 145.518 | 1.00 | 38.86 |
| ATOM | 1500 | CE1 | TYR | B | 73 | 119.198 | 18.006 | 146.319 | 1.00 | 39.71 |
| ATOM | 1501 | CD2 | TYR | B | 73 | 116.923 | 19.433 | 145.624 | 1.00 | 39.11 |
| ATOM | 1502 | CE2 | TYR | B | 73 | 116.810 | 18.306 | 146.430 | 1.00 | 39.71 |
| ATOM | 1503 | CZ | TYR | B | 73 | 117.948 | 17.596 | 146.771 | 1.00 | 40.56 |
| ATOM | 1504 | OH | TYR | B | 73 | 117.831 | 16.467 | 147.548 | 1.00 | 42.94 |
| ATOM | 1505 | C | TYR | B | 73 | 118.489 | 21.872 | 141.920 | 1.00 | 37.16 |
| ATOM | 1506 | O | TYR | B | 73 | 119.464 | 22.620 | 141.928 | 1.00 | 36.61 |
| ATOM | 1507 | N | LEU | B | 74 | 117.411 | 22.098 | 141.177 | 1.00 | 35.71 |
| ATOM | 1508 | CA | LEU | B | 74 | 117.324 | 23.283 | 140.332 | 1.00 | 35.01 |
| ATOM | 1509 | CB | LEU | B | 74 | 116.031 | 23.268 | 139.519 | 1.00 | 35.05 |
| ATOM | 1510 | CG | LEU | B | 74 | 115.822 | 24.514 | 138.649 | 1.00 | 37.90 |
| ATOM | 1511 | CD1 | LEU | B | 74 | 116.901 | 24.617 | 137.565 | 1.00 | 37.05 |
| ATOM | 1512 | CD2 | LEU | B | 74 | 114.441 | 24.456 | 138.020 | 1.00 | 37.87 |
| ATOM | 1513 | C | LEU | B | 74 | 117.368 | 24.537 | 141.203 | 1.00 | 34.61 |
| ATOM | 1514 | O | LEU | B | 74 | 116.637 | 24.650 | 142.188 | 1.00 | 33.92 |
| ATOM | 1515 | N | ALA | B | 75 | 118.240 | 25.472 | 140.847 | 1.00 | 34.97 |
| ATOM | 1516 | CA | ALA | B | 75 | 118.367 | 26.704 | 141.610 | 1.00 | 36.06 |
| ATOM | 1517 | CB | ALA | B | 75 | 119.599 | 26.647 | 142.493 | 1.00 | 33.12 |
| ATOM | 1518 | C | ALA | B | 75 | 118.410 | 27.955 | 140.741 | 1.00 | 36.98 |
| ATOM | 1519 | O | ALA | B | 75 | 118.963 | 27.959 | 139.643 | 1.00 | 36.77 |
| ATOM | 1520 | N | MET | B | 76 | 117.800 | 29.014 | 141.252 | 1.00 | 39.19 |
| ATOM | 1521 | CA | MET | B | 76 | 117.756 | 30.296 | 140.576 | 1.00 | 42.08 |
| ATOM | 1522 | CB | MET | B | 76 | 116.372 | 30.928 | 140.715 | 1.00 | 42.36 |
| ATOM | 1523 | CG | MET | B | 76 | 116.301 | 32.378 | 140.264 | 1.00 | 41.46 |
| ATOM | 1524 | SD | MET | B | 76 | 115.478 | 32.588 | 138.680 | 1.00 | 43.04 |
| ATOM | 1525 | CE | MET | B | 76 | 113.881 | 33.019 | 139.188 | 1.00 | 40.48 |
| ATOM | 1526 | C | MET | B | 76 | 118.771 | 31.160 | 141.291 | 1.00 | 45.25 |
| ATOM | 1527 | O | MET | B | 76 | 118.787 | 31.217 | 142.523 | 1.00 | 44.89 |
| ATOM | 1528 | N | LYS | B | 77 | 119.619 | 31.831 | 140.521 | 1.00 | 48.52 |
| ATOM | 1529 | CA | LYS | B | 77 | 120.639 | 32.695 | 141.097 | 1.00 | 52.31 |
| ATOM | 1530 | CB | LYS | B | 77 | 121.934 | 32.641 | 140.280 | 1.00 | 53.30 |
| ATOM | 1531 | CG | LYS | B | 77 | 122.496 | 31.239 | 140.049 | 1.00 | 56.11 |

TABLE 1-continued

FGFR1 D2–D3 Complexed with FGF2

| ATOM | 1532 | CD | LYS | B | 77 | 122.588 | 30.435 | 141.334 | 1.00 | 58.28 |
|---|---|---|---|---|---|---|---|---|---|---|
| ATOM | 1533 | CE | LYS | B | 77 | 123.405 | 31.153 | 142.391 | 1.00 | 59.93 |
| ATOM | 1534 | NZ | LYS | B | 77 | 123.562 | 30.287 | 143.589 | 1.00 | 62.93 |
| ATOM | 1535 | C | LYS | B | 77 | 120.158 | 34.135 | 141.161 | 1.00 | 54.00 |
| ATOM | 1536 | O | LYS | B | 77 | 119.186 | 34.510 | 140.505 | 1.00 | 53.67 |
| ATOM | 1537 | N | GLU | B | 78 | 120.865 | 34.937 | 141.950 | 1.00 | 56.33 |
| ATOM | 1538 | CA | GLU | B | 78 | 120.542 | 36.344 | 142.137 | 1.00 | 58.25 |
| ATOM | 1539 | CB | GLU | B | 78 | 121.662 | 37.045 | 142.912 | 1.00 | 61.62 |
| ATOM | 1540 | CG | GLU | B | 78 | 122.843 | 37.464 | 142.034 | 1.00 | 67.26 |
| ATOM | 1541 | CD | GLU | B | 78 | 123.925 | 38.221 | 142.798 | 1.00 | 70.03 |
| ATOM | 1542 | OE1 | GLU | B | 78 | 123.568 | 39.077 | 143.639 | 1.00 | 69.74 |
| ATOM | 1543 | OE2 | GLU | B | 78 | 125.132 | 37.969 | 142.546 | 1.00 | 71.37 |
| ATOM | 1544 | C | GLU | B | 78 | 120.319 | 37.093 | 140.827 | 1.00 | 57.71 |
| ATOM | 1545 | O | GLU | B | 78 | 119.465 | 37.974 | 140.757 | 1.00 | 58.26 |
| ATOM | 1546 | N | ASP | B | 79 | 121.092 | 36.757 | 139.797 | 1.00 | 56.53 |
| ATOM | 1547 | CA | ASP | B | 79 | 120.966 | 37.431 | 138.510 | 1.00 | 54.63 |
| ATOM | 1548 | CB | ASP | B | 79 | 122.319 | 37.464 | 137.798 | 1.00 | 52.84 |
| ATOM | 1549 | CG | ASP | B | 79 | 122.815 | 36.092 | 137.430 | 1.00 | 51.45 |
| ATOM | 1550 | OD1 | ASP | B | 79 | 123.915 | 35.997 | 136.854 | 1.00 | 51.83 |
| ATOM | 1551 | OD2 | ASP | B | 79 | 122.107 | 35.105 | 137.714 | 1.00 | 51.29 |
| ATOM | 1552 | C | ASP | B | 79 | 119.916 | 36.780 | 137.611 | 1.00 | 54.78 |
| ATOM | 1553 | O | ASP | B | 79 | 119.636 | 37.264 | 136.506 | 1.00 | 55.45 |
| ATOM | 1554 | N | GLY | B | 80 | 119.344 | 35.677 | 138.084 | 1.00 | 53.84 |
| ATOM | 1555 | CA | GLY | B | 80 | 118.320 | 34.996 | 137.315 | 1.00 | 51.77 |
| ATOM | 1556 | C | GLY | B | 80 | 118.778 | 33.857 | 136.426 | 1.00 | 50.03 |
| ATOM | 1557 | O | GLY | B | 80 | 118.055 | 33.464 | 135.515 | 1.00 | 49.68 |
| ATOM | 1558 | N | ARG | B | 81 | 119.966 | 33.320 | 136.669 | 1.00 | 48.16 |
| ATOM | 1559 | CA | ARG | B | 81 | 120.433 | 32.214 | 135.850 | 1.00 | 48.37 |
| ATOM | 1560 | CB | ARG | B | 81 | 121.935 | 32.331 | 135.589 | 1.00 | 51.00 |
| ATOM | 1561 | CG | ARG | B | 81 | 122.780 | 32.353 | 136.833 | 1.00 | 56.56 |
| ATOM | 1562 | CD | ARG | B | 81 | 124.245 | 32.646 | 136.531 | 1.00 | 60.32 |
| ATOM | 1563 | NE | ARG | B | 81 | 125.073 | 32.401 | 137.714 | 1.00 | 66.82 |
| ATOM | 1564 | CZ | ARG | B | 81 | 125.085 | 33.162 | 138.811 | 1.00 | 68.79 |
| ATOM | 1565 | NH1 | ARG | B | 81 | 124.320 | 34.243 | 138.895 | 1.00 | 69.57 |
| ATOM | 1566 | NH2 | ARG | B | 81 | 125.848 | 32.822 | 139.846 | 1.00 | 69.73 |
| ATOM | 1567 | C | ARG | B | 81 | 120.113 | 30.917 | 136.563 | 1.00 | 46.60 |
| ATOM | 1568 | O | ARG | B | 81 | 120.075 | 30.867 | 137.786 | 1.00 | 47.16 |
| ATOM | 1569 | N | LEU | B | 82 | 119.866 | 29.870 | 135.793 | 1.00 | 45.60 |
| ATOM | 1570 | CA | LEU | B | 82 | 119.536 | 28.572 | 136.361 | 1.00 | 45.32 |
| ATOM | 1571 | CB | LEU | B | 82 | 118.471 | 27.885 | 135.504 | 1.00 | 44.81 |
| ATOM | 1572 | CG | LEU | B | 82 | 117.161 | 28.639 | 135.289 | 1.00 | 43.76 |
| ATOM | 1573 | CD1 | LEU | B | 82 | 116.270 | 27.844 | 134.357 | 1.00 | 43.35 |
| ATOM | 1574 | CD2 | LEU | B | 82 | 116.475 | 28.865 | 136.623 | 1.00 | 42.51 |
| ATOM | 1575 | C | LEU | B | 82 | 120.747 | 27.659 | 136.432 | 1.00 | 44.48 |
| ATOM | 1576 | O | LEU | B | 82 | 121.666 | 27.784 | 135.638 | 1.00 | 44.80 |
| ATOM | 1577 | N | LEU | B | 83 | 120.732 | 26.747 | 137.394 | 1.00 | 44.12 |
| ATOM | 1578 | CA | LEU | B | 83 | 121.787 | 25.759 | 137.555 | 1.00 | 43.94 |
| ATOM | 1579 | CB | LEU | B | 83 | 123.105 | 26.406 | 137.989 | 1.00 | 44.49 |
| ATOM | 1580 | CG | LEU | B | 83 | 123.219 | 27.253 | 139.250 | 1.00 | 47.44 |
| ATOM | 1581 | CD1 | LEU | B | 83 | 123.023 | 26.367 | 140.485 | 1.00 | 47.58 |
| ATOM | 1582 | CD2 | LEU | B | 83 | 124.606 | 27.928 | 139.272 | 1.00 | 45.96 |
| ATOM | 1583 | C | LEU | B | 83 | 121.276 | 24.759 | 138.572 | 1.00 | 43.94 |
| ATOM | 1584 | O | LEU | B | 83 | 120.284 | 25.024 | 139.252 | 1.00 | 43.82 |
| ATOM | 1585 | N | ALA | B | 84 | 121.919 | 23.603 | 138.658 | 1.00 | 44.85 |
| ATOM | 1586 | CA | ALA | B | 84 | 121.466 | 22.577 | 139.589 | 1.00 | 46.61 |
| ATOM | 1587 | CB | ALA | B | 84 | 121.174 | 21.274 | 138.841 | 1.00 | 46.16 |
| ATOM | 1588 | C | ALA | B | 84 | 122.495 | 22.346 | 140.674 | 1.00 | 46.94 |
| ATOM | 1589 | O | ALA | B | 84 | 123.552 | 21.774 | 140.424 | 1.00 | 48.51 |
| ATOM | 1590 | N | SER | B | 85 | 122.166 | 22.806 | 141.878 | 1.00 | 47.21 |
| ATOM | 1591 | CA | SER | B | 85 | 123.029 | 22.689 | 143.040 | 1.00 | 46.19 |
| ATOM | 1592 | CB | SER | B | 85 | 122.485 | 23.579 | 144.153 | 1.00 | 45.16 |
| ATOM | 1593 | OG | SER | B | 85 | 123.154 | 23.322 | 145.364 | 1.00 | 48.28 |
| ATOM | 1594 | C | SER | B | 85 | 123.172 | 21.246 | 143.525 | 1.00 | 46.62 |
| ATOM | 1595 | O | SER | B | 85 | 122.293 | 20.411 | 143.310 | 1.00 | 46.65 |
| ATOM | 1596 | N | LYS | B | 86 | 124.295 | 20.952 | 144.171 | 1.00 | 47.71 |
| ATOM | 1597 | CA | LYS | B | 86 | 124.548 | 19.605 | 144.675 | 1.00 | 47.68 |
| ATOM | 1598 | CB | LYS | B | 86 | 126.028 | 19.438 | 145.025 | 1.00 | 49.80 |
| ATOM | 1599 | CG | LYS | B | 86 | 126.566 | 18.033 | 144.786 | 1.00 | 53.25 |
| ATOM | 1600 | CD | LYS | B | 86 | 126.384 | 17.633 | 143.330 | 1.00 | 56.56 |
| ATOM | 1601 | CE | LYS | B | 86 | 127.312 | 16.493 | 142.943 | 1.00 | 60.15 |
| ATOM | 1602 | NZ | LYS | B | 86 | 127.290 | 16.233 | 141.465 | 1.00 | 62.57 |
| ATOM | 1603 | C | LYS | B | 86 | 123.695 | 19.359 | 145.908 | 1.00 | 45.92 |
| ATOM | 1604 | O | LYS | B | 86 | 123.088 | 18.302 | 146.060 | 1.00 | 45.78 |
| ATOM | 1605 | N | SER | B | 87 | 123.663 | 20.345 | 146.794 | 1.00 | 44.95 |
| ATOM | 1606 | CA | SER | B | 87 | 122.859 | 20.251 | 148.004 | 1.00 | 44.18 |
| ATOM | 1607 | CB | SER | B | 87 | 123.744 | 20.317 | 149.253 | 1.00 | 44.78 |
| ATOM | 1608 | OG | SER | B | 87 | 124.591 | 21.449 | 149.210 | 1.00 | 45.74 |

TABLE 1-continued

| | | | FGFR1 D2–D3 Complexed with FGF2 | | | | | | |
|---|---|---|---|---|---|---|---|---|---|
| ATOM | 1609 | C | SER | B | 87 | 121.847 | 21.394 | 148.010 | 1.00 | 42.91 |
| ATOM | 1610 | O | SER | B | 87 | 122.017 | 22.403 | 147.324 | 1.00 | 41.78 |
| ATOM | 1611 | N | VAL | B | 88 | 120.789 | 21.220 | 148.785 | 1.00 | 40.56 |
| ATOM | 1612 | CA | VAL | B | 88 | 119.733 | 22.207 | 148.881 | 1.00 | 38.85 |
| ATOM | 1613 | CB | VAL | B | 88 | 118.567 | 21.602 | 149.674 | 1.00 | 37.72 |
| ATOM | 1614 | CG1 | VAL | B | 88 | 117.461 | 22.626 | 149.871 | 1.00 | 38.20 |
| ATOM | 1615 | CG2 | VAL | B | 88 | 118.059 | 20.377 | 148.960 | 1.00 | 35.37 |
| ATOM | 1616 | C | VAL | B | 88 | 120.150 | 23.536 | 149.534 | 1.00 | 39.23 |
| ATOM | 1617 | O | VAL | B | 88 | 120.736 | 23.553 | 150.620 | 1.00 | 39.42 |
| ATOM | 1618 | N | THR | B | 89 | 119.845 | 24.642 | 148.857 | 1.00 | 38.16 |
| ATOM | 1619 | CA | THR | B | 89 | 120.125 | 25.980 | 149.365 | 1.00 | 38.00 |
| ATOM | 1620 | CB | THR | B | 89 | 121.119 | 26.779 | 148.452 | 1.00 | 38.35 |
| ATOM | 1621 | OG1 | THR | B | 89 | 120.462 | 27.238 | 147.262 | 1.00 | 36.90 |
| ATOM | 1622 | CG2 | THR | B | 89 | 122.278 | 25.903 | 148.059 | 1.00 | 37.82 |
| ATOM | 1623 | C | THR | B | 89 | 118.776 | 26.685 | 149.378 | 1.00 | 38.23 |
| ATOM | 1624 | O | THR | B | 89 | 117.757 | 26.067 | 149.092 | 1.00 | 38.55 |
| ATOM | 1625 | N | ASP | B | 90 | 118.767 | 27.974 | 149.689 | 1.00 | 39.48 |
| ATOM | 1626 | CA | ASP | B | 90 | 117.531 | 28.747 | 149.751 | 1.00 | 40.53 |
| ATOM | 1627 | CB | ASP | B | 90 | 117.766 | 29.980 | 150.619 | 1.00 | 45.07 |
| ATOM | 1628 | CG | ASP | B | 90 | 118.708 | 30.983 | 149.963 | 1.00 | 49.28 |
| ATOM | 1629 | OD1 | ASP | B | 90 | 119.724 | 30.564 | 149.352 | 1.00 | 51.36 |
| ATOM | 1630 | OD2 | ASP | B | 90 | 118.432 | 32.198 | 150.066 | 1.00 | 50.64 |
| ATOM | 1631 | C | ASP | B | 90 | 117.020 | 29.184 | 148.378 | 1.00 | 39.14 |
| ATOM | 1632 | O | ASP | B | 90 | 115.947 | 29.777 | 148.263 | 1.00 | 39.83 |
| ATOM | 1633 | N | GLU | B | 91 | 117.794 | 28.908 | 147.339 | 1.00 | 37.50 |
| ATOM | 1634 | CA | GLU | B | 91 | 117.396 | 29.283 | 145.989 | 1.00 | 36.18 |
| ATOM | 1635 | CB | GLU | B | 91 | 118.600 | 29.828 | 145.214 | 1.00 | 34.46 |
| ATOM | 1636 | CG | GLU | B | 91 | 119.385 | 30.900 | 145.952 | 1.00 | 35.83 |
| ATOM | 1637 | CD | GLU | B | 91 | 120.581 | 31.430 | 145.146 | 1.00 | 37.27 |
| ATOM | 1638 | OE1 | GLU | B | 91 | 121.449 | 30.619 | 144.757 | 1.00 | 37.05 |
| ATOM | 1639 | OE2 | GLU | B | 91 | 120.655 | 32.657 | 144.902 | 1.00 | 36.08 |
| ATOM | 1640 | C | GLU | B | 91 | 116.815 | 28.066 | 145.263 | 1.00 | 34.93 |
| ATOM | 1641 | O | GLU | B | 91 | 116.515 | 28.121 | 144.070 | 1.00 | 32.42 |
| ATOM | 1642 | N | CYS | B | 92 | 116.648 | 26.973 | 145.998 | 1.00 | 33.43 |
| ATOM | 1643 | CA | CYS | B | 92 | 116.133 | 25.753 | 145.410 | 1.00 | 33.96 |
| ATOM | 1644 | CB | CYS | B | 92 | 116.918 | 24.558 | 145.956 | 1.00 | 33.84 |
| ATOM | 1645 | SG | CYS | B | 92 | 118.642 | 24.511 | 145.386 | 1.00 | 31.04 |
| ATOM | 1646 | C | CYS | B | 92 | 114.634 | 25.545 | 145.604 | 1.00 | 33.90 |
| ATOM | 1647 | O | CYS | B | 92 | 114.114 | 24.447 | 145.378 | 1.00 | 34.76 |
| ATOM | 1648 | N | PHE | B | 93 | 113.934 | 26.604 | 145.993 | 1.00 | 32.95 |
| ATOM | 1649 | CA | PHE | B | 93 | 112.495 | 26.513 | 146.204 | 1.00 | 31.87 |
| ATOM | 1650 | CB | PHE | B | 93 | 112.182 | 26.819 | 147.659 | 1.00 | 31.02 |
| ATOM | 1651 | CG | PHE | B | 93 | 112.813 | 25.853 | 148.604 | 1.00 | 31.34 |
| ATOM | 1652 | CD1 | PHE | B | 93 | 112.373 | 24.532 | 148.660 | 1.00 | 32.18 |
| ATOM | 1653 | CD2 | PHE | B | 93 | 113.882 | 26.235 | 149.401 | 1.00 | 30.66 |
| ATOM | 1654 | CE1 | PHE | B | 93 | 112.996 | 23.606 | 149.502 | 1.00 | 29.81 |
| ATOM | 1655 | CE2 | PHE | B | 93 | 114.508 | 25.318 | 150.242 | 1.00 | 29.19 |
| ATOM | 1656 | CZ | PHE | B | 93 | 114.061 | 24.001 | 150.289 | 1.00 | 29.42 |
| ATOM | 1657 | C | PHE | B | 93 | 111.692 | 27.409 | 145.266 | 1.00 | 31.34 |
| ATOM | 1658 | O | PHE | B | 93 | 112.080 | 28.542 | 144.967 | 1.00 | 31.56 |
| ATOM | 1659 | N | PHE | B | 94 | 110.564 | 26.886 | 144.798 | 1.00 | 29.36 |
| ATOM | 1660 | CA | PHE | B | 94 | 109.731 | 27.621 | 143.860 | 1.00 | 26.56 |
| ATOM | 1661 | CB | PHE | B | 94 | 109.992 | 27.093 | 142.452 | 1.00 | 25.63 |
| ATOM | 1662 | CG | PHE | B | 94 | 111.426 | 27.126 | 142.071 | 1.00 | 24.51 |
| ATOM | 1663 | CD1 | PHE | B | 94 | 112.004 | 28.299 | 141.607 | 1.00 | 25.06 |
| ATOM | 1664 | CD2 | PHE | B | 94 | 112.220 | 26.000 | 142.243 | 1.00 | 25.56 |
| ATOM | 1665 | CE1 | PHE | B | 94 | 113.356 | 28.356 | 141.321 | 1.00 | 25.77 |
| ATOM | 1666 | CE2 | PHE | B | 94 | 113.574 | 26.039 | 141.962 | 1.00 | 25.63 |
| ATOM | 1667 | CZ | PHE | B | 94 | 114.148 | 27.219 | 141.499 | 1.00 | 25.73 |
| ATOM | 1668 | C | PHE | B | 94 | 108.255 | 27.503 | 144.175 | 1.00 | 25.19 |
| ATOM | 1669 | O | PHE | B | 94 | 107.820 | 26.531 | 144.803 | 1.00 | 23.94 |
| ATOM | 1670 | N | PHE | B | 95 | 107.493 | 28.502 | 143.742 | 1.00 | 22.53 |
| ATOM | 1671 | CA | PHE | B | 95 | 106.055 | 28.485 | 143.944 | 1.00 | 23.75 |
| ATOM | 1672 | CB | PHE | B | 95 | 105.469 | 29.894 | 143.954 | 1.00 | 21.99 |
| ATOM | 1673 | CG | PHE | B | 95 | 105.775 | 30.663 | 145.196 | 1.00 | 22.80 |
| ATOM | 1674 | CD1 | PHE | B | 95 | 106.414 | 31.901 | 145.120 | 1.00 | 22.56 |
| ATOM | 1675 | CD2 | PHE | B | 95 | 105.441 | 30.144 | 146.448 | 1.00 | 21.37 |
| ATOM | 1676 | CE1 | PHE | B | 95 | 106.723 | 32.608 | 146.274 | 1.00 | 24.07 |
| ATOM | 1677 | CE2 | PHE | B | 95 | 105.743 | 30.836 | 147.610 | 1.00 | 20.75 |
| ATOM | 1678 | CZ | PHE | B | 95 | 106.386 | 32.072 | 147.530 | 1.00 | 23.23 |
| ATOM | 1679 | C | PHE | B | 95 | 105.425 | 27.707 | 142.804 | 1.00 | 25.56 |
| ATOM | 1680 | O | PHE | B | 95 | 105.349 | 28.188 | 141.670 | 1.00 | 27.02 |
| ATOM | 1681 | N | GLU | B | 96 | 104.991 | 26.489 | 143.089 | 1.00 | 26.35 |
| ATOM | 1682 | CA | GLU | B | 96 | 104.359 | 25.706 | 142.056 | 1.00 | 27.18 |
| ATOM | 1683 | CB | GLU | B | 96 | 104.443 | 24.212 | 142.361 | 1.00 | 26.72 |
| ATOM | 1684 | CG | GLU | B | 96 | 103.867 | 23.337 | 141.254 | 1.00 | 26.24 |
| ATOM | 1685 | CD | GLU | B | 96 | 103.691 | 21.901 | 141.685 | 1.00 | 28.35 |

TABLE 1-continued

FGFR1 D2–D3 Complexed with FGF2

| | | | | | | | | | | |
|---|---|---|---|---|---|---|---|---|---|---|
| ATOM | 1686 | OE1 | GLU | B | 96 | 103.162 | 21.678 | 142.795 | 1.00 | 30.76 |
| ATOM | 1687 | OE2 | GLU | B | 96 | 104.064 | 20.988 | 140.920 | 1.00 | 31.23 |
| ATOM | 1688 | C | GLU | B | 96 | 102.909 | 26.158 | 142.020 | 1.00 | 28.96 |
| ATOM | 1689 | O | GLU | B | 96 | 102.167 | 26.018 | 142.993 | 1.00 | 31.23 |
| ATOM | 1690 | N | ARG | B | 97 | 102.509 | 26.726 | 140.897 | 1.00 | 29.93 |
| ATOM | 1691 | CA | ARG | B | 97 | 101.148 | 27.187 | 140.751 | 1.00 | 29.36 |
| ATOM | 1692 | CB | ARG | B | 97 | 101.105 | 28.718 | 140.754 | 1.00 | 32.52 |
| ATOM | 1693 | CG | ARG | B | 97 | 99.740 | 29.288 | 140.426 | 1.00 | 35.07 |
| ATOM | 1694 | CD | ARG | B | 97 | 99.770 | 30.797 | 140.343 | 1.00 | 41.18 |
| ATOM | 1695 | NE | ARG | B | 97 | 98.453 | 31.329 | 139.994 | 1.00 | 47.09 |
| ATOM | 1696 | CZ | ARG | B | 97 | 97.402 | 31.326 | 140.812 | 1.00 | 48.95 |
| ATOM | 1697 | NH1 | ARG | B | 97 | 97.520 | 30.823 | 142.036 | 1.00 | 50.33 |
| ATOM | 1698 | NH2 | ARG | B | 97 | 96.231 | 31.812 | 140.405 | 1.00 | 48.08 |
| ATOM | 1699 | C | ARG | B | 97 | 100.526 | 26.663 | 139.471 | 1.00 | 27.73 |
| ATOM | 1700 | O | ARG | B | 97 | 101.104 | 26.783 | 138.392 | 1.00 | 26.45 |
| ATOM | 1701 | N | LEU | B | 98 | 99.350 | 26.059 | 139.611 | 1.00 | 27.65 |
| ATOM | 1702 | CA | LEU | B | 98 | 98.585 | 25.555 | 138.473 | 1.00 | 27.40 |
| ATOM | 1703 | CB | LEU | B | 98 | 97.707 | 24.376 | 138.909 | 1.00 | 23.68 |
| ATOM | 1704 | CG | LEU | B | 98 | 96.669 | 23.882 | 137.894 | 1.00 | 21.58 |
| ATOM | 1705 | CD1 | LEU | B | 98 | 97.341 | 23.545 | 136.586 | 1.00 | 20.86 |
| ATOM | 1706 | CD2 | LEU | B | 98 | 95.952 | 22.658 | 138.444 | 1.00 | 20.79 |
| ATOM | 1707 | C | LEU | B | 98 | 97.720 | 26.737 | 137.990 | 1.00 | 27.81 |
| ATOM | 1708 | O | LEU | B | 98 | 96.682 | 27.043 | 138.571 | 1.00 | 29.38 |
| ATOM | 1709 | N | GLU | B | 99 | 98.177 | 27.409 | 136.940 | 1.00 | 28.61 |
| ATOM | 1710 | CA | GLU | B | 99 | 97.493 | 28.572 | 136.394 | 1.00 | 28.93 |
| ATOM | 1711 | CB | GLU | B | 99 | 98.395 | 29.219 | 135.349 | 1.00 | 28.89 |
| ATOM | 1712 | CG | GLU | B | 99 | 99.753 | 29.616 | 135.912 | 1.00 | 28.08 |
| ATOM | 1713 | CD | GLU | B | 99 | 99.671 | 30.824 | 136.832 | 1.00 | 31.83 |
| ATOM | 1714 | OE1 | GLU | B | 99 | 100.684 | 31.141 | 137.499 | 1.00 | 30.76 |
| ATOM | 1715 | OE2 | GLU | B | 99 | 98.589 | 31.463 | 136.878 | 1.00 | 33.87 |
| ATOM | 1716 | C | GLU | B | 99 | 96.128 | 28.243 | 135.810 | 1.00 | 29.29 |
| ATOM | 1717 | O | GLU | B | 99 | 95.766 | 27.069 | 135.659 | 1.00 | 28.75 |
| ATOM | 1718 | N | SER | B | 100 | 95.374 | 29.289 | 135.483 | 1.00 | 29.92 |
| ATOM | 1719 | CA | SER | B | 100 | 94.028 | 29.126 | 134.939 | 1.00 | 30.61 |
| ATOM | 1720 | CB | SER | B | 100 | 93.283 | 30.467 | 134.926 | 1.00 | 28.25 |
| ATOM | 1721 | OG | SER | B | 100 | 93.858 | 31.384 | 134.009 | 1.00 | 24.98 |
| ATOM | 1722 | C | SER | B | 100 | 94.002 | 28.527 | 133.538 | 1.00 | 32.21 |
| ATOM | 1723 | O | SER | B | 100 | 92.957 | 28.065 | 133.087 | 1.00 | 34.96 |
| ATOM | 1724 | N | ASN | B | 101 | 95.141 | 28.527 | 132.853 | 1.00 | 32.04 |
| ATOM | 1725 | CA | ASN | B | 101 | 95.221 | 27.972 | 131.503 | 1.00 | 30.78 |
| ATOM | 1726 | CB | ASN | B | 101 | 96.303 | 28.694 | 130.704 | 1.00 | 29.70 |
| ATOM | 1727 | CG | ASN | B | 101 | 97.627 | 28.688 | 131.416 | 1.00 | 28.96 |
| ATOM | 1728 | OD1 | ASN | B | 101 | 97.688 | 28.381 | 132.603 | 1.00 | 29.57 |
| ATOM | 1729 | ND2 | ASN | B | 101 | 98.695 | 29.036 | 130.708 | 1.00 | 28.13 |
| ATOM | 1730 | C | ASN | B | 101 | 95.541 | 26.490 | 131.559 | 1.00 | 29.90 |
| ATOM | 1731 | O | ASN | B | 101 | 95.611 | 25.823 | 130.528 | 1.00 | 31.66 |
| ATOM | 1732 | N | ASN | B | 102 | 95.740 | 25.988 | 132.772 | 1.00 | 28.75 |
| ATOM | 1733 | CA | ASN | B | 102 | 96.054 | 24.580 | 133.010 | 1.00 | 27.81 |
| ATOM | 1734 | CB | ASN | B | 102 | 95.143 | 23.695 | 132.193 | 1.00 | 25.64 |
| ATOM | 1735 | CG | ASN | B | 102 | 93.733 | 23.887 | 132.576 | 1.00 | 25.66 |
| ATOM | 1736 | OD1 | ASN | B | 102 | 93.384 | 23.686 | 133.737 | 1.00 | 27.29 |
| ATOM | 1737 | ND2 | ASN | B | 102 | 92.901 | 24.313 | 131.627 | 1.00 | 27.10 |
| ATOM | 1738 | C | ASN | B | 102 | 97.494 | 24.199 | 132.779 | 1.00 | 26.40 |
| ATOM | 1739 | O | ASN | B | 102 | 97.812 | 23.049 | 132.472 | 1.00 | 24.65 |
| ATOM | 1740 | N | TYR | B | 103 | 98.358 | 25.192 | 132.937 | 1.00 | 26.13 |
| ATOM | 1741 | CA | TYR | B | 103 | 99.795 | 25.017 | 132.810 | 1.00 | 26.46 |
| ATOM | 1742 | CB | TYR | B | 103 | 100.380 | 25.977 | 131.781 | 1.00 | 26.68 |
| ATOM | 1743 | CG | TYR | B | 103 | 100.227 | 25.513 | 130.360 | 1.00 | 28.89 |
| ATOM | 1744 | CD1 | TYR | B | 103 | 101.046 | 24.506 | 129.852 | 1.00 | 29.01 |
| ATOM | 1745 | CE1 | TYR | B | 103 | 100.901 | 24.047 | 128.551 | 1.00 | 31.54 |
| ATOM | 1746 | CD2 | TYR | B | 103 | 99.246 | 26.059 | 129.528 | 1.00 | 27.75 |
| ATOM | 1747 | CE2 | TYR | B | 103 | 99.084 | 25.604 | 128.214 | 1.00 | 30.75 |
| ATOM | 1748 | CZ | TYR | B | 103 | 99.918 | 24.596 | 127.728 | 1.00 | 32.28 |
| ATOM | 1749 | OH | TYR | B | 103 | 99.787 | 24.135 | 126.429 | 1.00 | 32.13 |
| ATOM | 1750 | C | TYR | B | 103 | 100.355 | 25.382 | 134.163 | 1.00 | 26.02 |
| ATOM | 1751 | O | TYR | B | 103 | 99.770 | 26.184 | 134.880 | 1.00 | 27.29 |
| ATOM | 1752 | N | ASN | B | 104 | 101.485 | 24.793 | 134.511 | 1.00 | 24.28 |
| ATOM | 1753 | CA | ASN | B | 104 | 102.130 | 25.083 | 135.773 | 1.00 | 22.21 |
| ATOM | 1754 | CB | ASN | B | 104 | 102.798 | 23.831 | 136.329 | 1.00 | 23.81 |
| ATOM | 1755 | CG | ASN | B | 104 | 101.841 | 22.940 | 137.065 | 1.00 | 22.38 |
| ATOM | 1756 | OD1 | ASN | B | 104 | 100.634 | 23.190 | 137.090 | 1.00 | 24.27 |
| ATOM | 1757 | ND2 | ASN | B | 104 | 102.372 | 21.887 | 137.674 | 1.00 | 19.93 |
| ATOM | 1758 | C | ASN | B | 104 | 103.200 | 26.123 | 135.559 | 1.00 | 21.77 |
| ATOM | 1759 | O | ASN | B | 104 | 103.741 | 26.258 | 134.466 | 1.00 | 18.48 |
| ATOM | 1760 | N | THR | B | 105 | 103.505 | 26.856 | 136.620 | 1.00 | 23.55 |
| ATOM | 1761 | CA | THR | B | 105 | 104.555 | 27.862 | 136.580 | 1.00 | 25.40 |
| ATOM | 1762 | CB | THR | B | 105 | 103.987 | 29.298 | 136.497 | 1.00 | 23.35 |

TABLE 1-continued

FGFR1 D2–D3 Complexed with FGF2

| ATOM | 1763 | OG1 | THR | B | 105 | 103.069 | 29.521 | 137.576 | 1.00 | 24.27 |
|---|---|---|---|---|---|---|---|---|---|---|
| ATOM | 1764 | CG2 | THR | B | 105 | 103.293 | 29.509 | 135.178 | 1.00 | 19.24 |
| ATOM | 1765 | C | THR | B | 105 | 105.380 | 27.713 | 137.851 | 1.00 | 26.45 |
| ATOM | 1766 | O | THR | B | 105 | 104.847 | 27.446 | 138.924 | 1.00 | 27.70 |
| ATOM | 1767 | N | TYR | B | 106 | 106.685 | 27.882 | 137.727 | 1.00 | 27.80 |
| ATOM | 1768 | CA | TYR | B | 106 | 107.554 | 27.755 | 138.881 | 1.00 | 28.15 |
| ATOM | 1769 | CB | TYR | B | 106 | 108.503 | 26.592 | 138.646 | 1.00 | 24.96 |
| ATOM | 1770 | CG | TYR | B | 106 | 107.735 | 25.288 | 138.599 | 1.00 | 23.60 |
| ATOM | 1771 | CD1 | TYR | B | 106 | 107.488 | 24.566 | 139.769 | 1.00 | 21.27 |
| ATOM | 1772 | CE1 | TYR | B | 106 | 106.742 | 23.395 | 139.750 | 1.00 | 21.89 |
| ATOM | 1773 | CD2 | TYR | B | 106 | 107.208 | 24.800 | 137.394 | 1.00 | 21.41 |
| ATOM | 1774 | CE2 | TYR | B | 106 | 106.456 | 23.626 | 137.360 | 1.00 | 21.03 |
| ATOM | 1775 | CZ | TYR | B | 106 | 106.229 | 22.925 | 138.548 | 1.00 | 24.06 |
| ATOM | 1776 | OH | TYR | B | 106 | 105.515 | 21.741 | 138.546 | 1.00 | 23.62 |
| ATOM | 1777 | C | TYR | B | 106 | 108.280 | 29.061 | 139.145 | 1.00 | 30.41 |
| ATOM | 1778 | O | TYR | B | 106 | 109.245 | 29.426 | 138.469 | 1.00 | 31.45 |
| ATOM | 1779 | N | ARG | B | 107 | 107.780 | 29.768 | 140.149 | 1.00 | 31.96 |
| ATOM | 1780 | CA | ARG | B | 107 | 108.312 | 31.061 | 140.535 | 1.00 | 32.79 |
| ATOM | 1781 | CE | ARG | B | 107 | 107.152 | 31.979 | 140.912 | 1.00 | 32.00 |
| ATOM | 1782 | CG | ARG | B | 107 | 107.533 | 33.406 | 141.148 | 1.00 | 33.23 |
| ATOM | 1783 | CD | ARG | B | 107 | 106.334 | 34.300 | 140.910 | 1.00 | 35.90 |
| ATOM | 1784 | NE | ARG | B | 107 | 105.191 | 33.986 | 141.771 | 1.00 | 40.00 |
| ATOM | 1785 | CZ | ARG | B | 107 | 105.077 | 34.354 | 143.045 | 1.00 | 39.85 |
| ATOM | 1786 | NH1 | ARG | B | 107 | 106.034 | 35.054 | 143.638 | 1.00 | 38.97 |
| ATOM | 1787 | NH2 | ARG | B | 107 | 103.996 | 34.019 | 143.729 | 1.00 | 41.38 |
| ATOM | 1788 | C | ARG | B | 107 | 109.274 | 30.938 | 141.696 | 1.00 | 33.01 |
| ATOM | 1789 | O | ARG | B | 107 | 108.957 | 30.282 | 142.690 | 1.00 | 32.53 |
| ATOM | 1790 | N | SER | B | 108 | 110.441 | 31.571 | 141.558 | 1.00 | 34.47 |
| ATOM | 1791 | CA | SER | B | 108 | 111.481 | 31.557 | 142.595 | 1.00 | 36.46 |
| ATOM | 1792 | CB | SER | B | 108 | 112.690 | 32.402 | 142.178 | 1.00 | 37.32 |
| ATOM | 1793 | OG | SER | B | 108 | 113.657 | 32.459 | 143.215 | 1.00 | 36.67 |
| ATOM | 1794 | C | SER | B | 108 | 110.947 | 32.111 | 143.898 | 1.00 | 36.91 |
| ATOM | 1795 | O | SER | B | 108 | 110.438 | 33.233 | 143.932 | 1.00 | 37.00 |
| ATOM | 1796 | N | ARG | B | 109 | 111.059 | 31.335 | 144.970 | 1.00 | 37.99 |
| ATOM | 1797 | CA | ARG | B | 109 | 110.564 | 31.808 | 146.249 | 1.00 | 40.27 |
| ATOM | 1798 | CE | ARG | B | 109 | 110.465 | 30.672 | 147.263 | 1.00 | 40.19 |
| ATOM | 1799 | CG | ARG | B | 109 | 109.690 | 31.068 | 148.511 | 1.00 | 41.08 |
| ATOM | 1800 | CD | ARG | B | 109 | 109.061 | 29.853 | 149.173 | 1.00 | 42.63 |
| ATOM | 1801 | NE | ARG | B | 109 | 110.060 | 28.944 | 149.723 | 1.00 | 44.24 |
| ATOM | 1802 | CZ | ARG | B | 109 | 110.484 | 28.960 | 150.984 | 1.00 | 45.28 |
| ATOM | 1803 | NH1 | ARG | B | 109 | 109.993 | 29.843 | 151.848 | 1.00 | 46.59 |
| ATOM | 1804 | NH2 | ARG | B | 109 | 111.402 | 28.084 | 151.379 | 1.00 | 45.30 |
| ATOM | 1805 | C | ARG | B | 109 | 111.485 | 32.895 | 146.769 | 1.00 | 42.63 |
| ATOM | 1806 | O | ARG | B | 109 | 111.067 | 33.741 | 147.570 | 1.00 | 43.11 |
| ATOM | 1807 | N | LYS | B | 110 | 112.736 | 32.890 | 146.308 | 1.00 | 43.86 |
| ATOM | 1808 | CA | LYS | B | 110 | 113.673 | 33.913 | 146.748 | 1.00 | 44.94 |
| ATOM | 1809 | CB | LYS | B | 110 | 115.098 | 33.364 | 146.858 | 1.00 | 46.17 |
| ATOM | 1810 | CG | LYS | B | 110 | 116.062 | 34.455 | 147.292 | 1.00 | 47.98 |
| ATOM | 1811 | CD | LYS | B | 110 | 117.294 | 33.939 | 147.986 | 1.00 | 50.45 |
| ATOM | 1812 | CE | LYS | B | 110 | 117.932 | 35.064 | 148.805 | 1.00 | 51.51 |
| ATOM | 1813 | NZ | LYS | B | 110 | 119.185 | 34.665 | 149.515 | 1.00 | 52.68 |
| ATOM | 1814 | C | LYS | B | 110 | 113.666 | 35.166 | 145.865 | 1.00 | 45.12 |
| ATOM | 1815 | O | LYS | B | 110 | 113.757 | 36.278 | 146.375 | 1.00 | 45.84 |
| ATOM | 1816 | N | TYR | B | 111 | 113.559 | 34.992 | 144.553 | 1.00 | 45.15 |
| ATOM | 1817 | CA | TYR | B | 111 | 113.520 | 36.128 | 143.636 | 1.00 | 45.47 |
| ATOM | 1818 | CB | TYR | B | 111 | 114.595 | 35.945 | 142.570 | 1.00 | 44.77 |
| ATOM | 1819 | CG | TYR | B | 111 | 115.949 | 35.789 | 143.216 | 1.00 | 45.41 |
| ATOM | 1820 | CD1 | TYR | B | 111 | 116.546 | 36.858 | 143.883 | 1.00 | 46.17 |
| ATOM | 1821 | CE1 | TYR | B | 111 | 117.744 | 36.700 | 144.573 | 1.00 | 44.71 |
| ATOM | 1822 | CD2 | TYR | B | 111 | 116.595 | 34.553 | 143.249 | 1.00 | 45.96 |
| ATOM | 1823 | CE2 | TYR | B | 111 | 117.794 | 34.388 | 143.936 | 1.00 | 45.72 |
| ATOM | 1824 | CZ | TYR | B | 111 | 118.357 | 35.467 | 144.596 | 1.00 | 44.93 |
| ATOM | 1825 | OH | TYR | B | 111 | 119.524 | 35.317 | 145.296 | 1.00 | 45.11 |
| ATOM | 1826 | C | TYR | B | 111 | 112.114 | 36.172 | 143.056 | 1.00 | 46.44 |
| ATOM | 1827 | O | TYR | B | 111 | 111.892 | 36.091 | 141.848 | 1.00 | 48.14 |
| ATOM | 1828 | N | THR | B | 112 | 111.174 | 36.301 | 143.983 | 1.00 | 47.26 |
| ATOM | 1829 | CA | THR | B | 112 | 109.738 | 36.320 | 143.740 | 1.00 | 48.53 |
| ATOM | 1830 | CB | THR | B | 112 | 109.021 | 37.059 | 144.878 | 1.00 | 49.29 |
| ATOM | 1831 | OG1 | THR | B | 112 | 109.774 | 38.227 | 145.246 | 1.00 | 49.98 |
| ATOM | 1832 | CG2 | THR | B | 112 | 108.870 | 36.133 | 146.086 | 1.00 | 49.24 |
| ATOM | 1833 | C | THR | B | 112 | 109.133 | 36.786 | 142.422 | 1.00 | 48.60 |
| ATOM | 1834 | O | THR | B | 112 | 108.006 | 36.406 | 142.115 | 1.00 | 48.90 |
| ATOM | 1835 | N | SER | B | 113 | 109.839 | 37.594 | 141.638 | 1.00 | 48.32 |
| ATOM | 1836 | CA | SER | B | 113 | 109.263 | 38.035 | 140.369 | 1.00 | 46.93 |
| ATOM | 1837 | CB | SER | B | 113 | 109.375 | 39.548 | 140.241 | 1.00 | 45.36 |
| ATOM | 1838 | OG | SER | B | 113 | 110.696 | 39.952 | 140.511 | 1.00 | 48.70 |
| ATOM | 1839 | C | SER | B | 113 | 109.842 | 37.360 | 139.120 | 1.00 | 45.91 |

TABLE 1-continued

FGFR1 D2–D3 Complexed with FGF2

| ATOM | 1840 | O | SER | B | 113 | 109.622 | 37.831 | 138.005 | 1.00 | 46.93 |
|---|---|---|---|---|---|---|---|---|---|---|
| ATOM | 1841 | N | TRP | B | 114 | 110.570 | 36.260 | 139.295 | 1.00 | 43.86 |
| ATOM | 1842 | CA | TRP | B | 114 | 111.122 | 35.566 | 138.143 | 1.00 | 43.51 |
| ATOM | 1843 | CB | TRP | B | 114 | 112.641 | 35.650 | 138.130 | 1.00 | 47.61 |
| ATOM | 1844 | CG | TRP | B | 114 | 113.203 | 37.028 | 138.254 | 1.00 | 50.02 |
| ATOM | 1845 | CD2 | TRP | B | 114 | 114.484 | 37.368 | 138.779 | 1.00 | 51.18 |
| ATOM | 1846 | CE2 | TRP | B | 114 | 114.627 | 38.765 | 138.660 | 1.00 | 51.19 |
| ATOM | 1847 | CE3 | TRP | B | 114 | 115.531 | 36.624 | 139.340 | 1.00 | 52.31 |
| ATOM | 1848 | CD1 | TRP | B | 114 | 112.631 | 38.199 | 137.845 | 1.00 | 50.13 |
| ATOM | 1849 | NE1 | TRP | B | 114 | 113.481 | 39.247 | 138.085 | 1.00 | 50.60 |
| ATOM | 1850 | CZ2 | TRP | B | 114 | 115.772 | 39.434 | 139.081 | 1.00 | 51.87 |
| ATOM | 1851 | CZ3 | TRP | B | 114 | 116.670 | 37.288 | 139.759 | 1.00 | 52.13 |
| ATOM | 1852 | CH2 | TRP | B | 114 | 116.782 | 38.680 | 139.628 | 1.00 | 52.79 |
| ATOM | 1853 | C | TRP | B | 114 | 110.702 | 34.109 | 138.121 | 1.00 | 42.54 |
| ATOM | 1854 | O | TRP | B | 114 | 110.521 | 33.493 | 139.173 | 1.00 | 42.95 |
| ATOM | 1855 | N | TYR | B | 115 | 110.561 | 33.559 | 136.917 | 1.00 | 40.61 |
| ATOM | 1856 | CA | TYR | B | 115 | 110.139 | 32.170 | 136.740 | 1.00 | 39.09 |
| ATOM | 1857 | CB | TYR | B | 115 | 108.873 | 32.068 | 135.879 | 1.00 | 40.31 |
| ATOM | 1858 | CG | TYR | B | 115 | 107.669 | 32.872 | 136.301 | 1.00 | 39.72 |
| ATOM | 1859 | CD1 | TYR | B | 115 | 107.651 | 34.250 | 136.156 | 1.00 | 39.96 |
| ATOM | 1860 | CE1 | TYR | B | 115 | 106.527 | 34.992 | 136.490 | 1.00 | 40.25 |
| ATOM | 1861 | CD2 | TYR | B | 115 | 106.522 | 32.242 | 136.799 | 1.00 | 39.15 |
| ATOM | 1862 | CE2 | TYR | B | 115 | 105.393 | 32.975 | 137.135 | 1.00 | 37.77 |
| ATOM | 1863 | CZ | TYR | B | 115 | 105.402 | 34.353 | 136.979 | 1.00 | 39.46 |
| ATOM | 1864 | OH | TYR | B | 115 | 104.299 | 35.113 | 137.315 | 1.00 | 40.52 |
| ATOM | 1865 | C | TYR | B | 115 | 111.161 | 31.286 | 136.050 | 1.00 | 37.81 |
| ATOM | 1866 | O | TYR | B | 115 | 111.996 | 31.755 | 135.276 | 1.00 | 38.99 |
| ATOM | 1867 | N | VAL | B | 116 | 111.069 | 29.990 | 136.317 | 1.00 | 36.36 |
| ATOM | 1868 | CA | VAL | B | 116 | 111.929 | 29.032 | 135.645 | 1.00 | 36.77 |
| ATOM | 1869 | CB | VAL | B | 116 | 111.813 | 27.616 | 136.261 | 1.00 | 35.73 |
| ATOM | 1870 | CG1 | VAL | B | 116 | 112.514 | 26.622 | 135.379 | 1.00 | 32.37 |
| ATOM | 1871 | CG2 | VAL | B | 116 | 112.433 | 27.595 | 137.653 | 1.00 | 35.38 |
| ATOM | 1872 | C | VAL | B | 116 | 111.296 | 29.035 | 134.251 | 1.00 | 37.90 |
| ATOM | 1873 | O | VAL | B | 116 | 110.076 | 28.899 | 134.131 | 1.00 | 37.90 |
| ATOM | 1874 | N | ALA | B | 117 | 112.102 | 29.215 | 133.206 | 1.00 | 38.53 |
| ATOM | 1875 | CA | ALA | B | 117 | 111.563 | 29.264 | 131.847 | 1.00 | 37.77 |
| ATOM | 1876 | CB | ALA | B | 117 | 111.060 | 30.683 | 131.543 | 1.00 | 37.53 |
| ATOM | 1877 | C | ALA | B | 117 | 112.568 | 28.839 | 130.782 | 1.00 | 37.82 |
| ATOM | 1878 | O | ALA | B | 117 | 113.770 | 28.957 | 130.977 | 1.00 | 37.72 |
| ATOM | 1879 | N | LEU | B | 118 | 112.066 | 28.355 | 129.650 | 1.00 | 37.80 |
| ATOM | 1880 | CA | LEU | B | 118 | 112.925 | 27.930 | 128.558 | 1.00 | 37.19 |
| ATOM | 1881 | CB | LEU | B | 118 | 112.734 | 26.439 | 128.292 | 1.00 | 36.09 |
| ATOM | 1882 | CG | LEU | B | 118 | 113.087 | 25.465 | 129.422 | 1.00 | 35.69 |
| ATOM | 1883 | CD1 | LEU | B | 118 | 112.965 | 24.001 | 128.912 | 1.00 | 31.91 |
| ATOM | 1884 | CD2 | LEU | B | 118 | 114.497 | 25.764 | 129.928 | 1.00 | 31.08 |
| ATOM | 1885 | C | LEU | B | 118 | 112.631 | 28.712 | 127.281 | 1.00 | 38.86 |
| ATOM | 1886 | O | LEU | B | 118 | 111.471 | 28.991 | 126.969 | 1.00 | 39.01 |
| ATOM | 1887 | N | LYS | B | 119 | 113.689 | 29.062 | 126.551 | 1.00 | 40.20 |
| ATOM | 1888 | CA | LYS | B | 119 | 113.570 | 29.798 | 125.296 | 1.00 | 41.60 |
| ATOM | 1889 | CB | LYS | B | 119 | 114.916 | 30.418 | 124.914 | 1.00 | 44.91 |
| ATOM | 1890 | CG | LYS | B | 119 | 115.443 | 31.523 | 125.817 | 1.00 | 46.42 |
| ATOM | 1891 | CD | LYS | B | 119 | 116.928 | 31.754 | 125.510 | 1.00 | 48.54 |
| ATOM | 1892 | CE | LYS | B | 119 | 117.424 | 33.128 | 125.955 | 1.00 | 49.92 |
| ATOM | 1893 | NZ | LYS | B | 119 | 116.958 | 34.230 | 125.056 | 1.00 | 51.60 |
| ATOM | 1894 | C | LYS | B | 119 | 113.147 | 28.852 | 124.174 | 1.00 | 42.37 |
| ATOM | 1895 | O | LYS | B | 119 | 113.285 | 27.626 | 124.296 | 1.00 | 40.67 |
| ATOM | 1896 | N | ARG | B | 120 | 112.656 | 29.436 | 123.078 | 1.00 | 44.22 |
| ATOM | 1897 | CA | ARG | B | 120 | 112.203 | 28.687 | 121.906 | 1.00 | 46.02 |
| ATOM | 1898 | CB | ARG | B | 120 | 111.619 | 29.677 | 120.874 | 1.00 | 48.48 |
| ATOM | 1899 | CG | ARG | B | 120 | 110.660 | 30.706 | 121.512 | 1.00 | 54.41 |
| ATOM | 1900 | CD | ARG | B | 120 | 109.937 | 31.661 | 120.535 | 1.00 | 58.66 |
| ATOM | 1901 | NE | ARG | B | 120 | 108.765 | 31.067 | 119.876 | 1.00 | 63.50 |
| ATOM | 1902 | CZ | ARG | B | 120 | 107.764 | 31.765 | 119.330 | 1.00 | 65.20 |
| ATOM | 1903 | NH1 | ARG | B | 120 | 107.778 | 33.094 | 119.368 | 1.00 | 64.73 |
| ATOM | 1904 | NH2 | ARG | B | 120 | 106.754 | 31.138 | 118.724 | 1.00 | 65.86 |
| ATOM | 1905 | C | ARG | B | 120 | 113.384 | 27.882 | 121.323 | 1.00 | 45.52 |
| ATOM | 1906 | O | ARG | B | 120 | 113.198 | 26.924 | 120.562 | 1.00 | 44.84 |
| ATOM | 1907 | N | THR | B | 121 | 114.594 | 28.265 | 121.734 | 1.00 | 45.23 |
| ATOM | 1908 | CA | THR | B | 121 | 115.844 | 27.638 | 121.294 | 1.00 | 43.96 |
| ATOM | 1909 | CB | THR | B | 121 | 116.992 | 28.637 | 121.360 | 1.00 | 42.69 |
| ATOM | 1910 | OG1 | THR | B | 121 | 117.419 | 28.774 | 122.723 | 1.00 | 41.94 |
| ATOM | 1911 | CG2 | THR | B | 121 | 116.534 | 29.992 | 120.844 | 1.00 | 42.10 |
| ATOM | 1912 | C | THR | B | 121 | 116.277 | 26.426 | 122.124 | 1.00 | 44.14 |
| ATOM | 1913 | O | THR | B | 121 | 117.222 | 25.723 | 121.759 | 1.00 | 43.98 |
| ATOM | 1914 | N | GLY | B | 122 | 115.611 | 26.198 | 123.252 | 1.00 | 44.98 |
| ATOM | 1915 | CA | GLY | B | 122 | 115.970 | 25.069 | 124.093 | 1.00 | 45.39 |
| ATOM | 1916 | C | GLY | B | 122 | 116.937 | 25.422 | 125.214 | 1.00 | 45.75 |

TABLE 1-continued

FGFR1 D2–D3 Complexed with FGF2

| | | | | | | | | | | |
|---|---|---|---|---|---|---|---|---|---|---|
| ATOM | 1917 | O | GLY | B | 122 | 117.535 | 24.541 | 125.828 | 1.00 | 45.93 |
| ATOM | 1918 | N | GLN | B | 123 | 117.099 | 26.707 | 125.492 | 1.00 | 45.97 |
| ATOM | 1919 | CA | GLN | B | 123 | 118.001 | 27.116 | 126.555 | 1.00 | 47.84 |
| ATOM | 1920 | CB | GLN | B | 123 | 119.074 | 28.046 | 126.012 | 1.00 | 51.23 |
| ATOM | 1921 | CG | GLN | B | 123 | 119.943 | 27.391 | 124.991 | 1.00 | 56.90 |
| ATOM | 1922 | CD | GLN | B | 123 | 120.689 | 28.407 | 124.187 | 1.00 | 61.76 |
| ATOM | 1923 | OE1 | GLN | B | 123 | 120.084 | 29.321 | 123.616 | 1.00 | 63.94 |
| ATOM | 1924 | NE2 | GLN | B | 123 | 122.015 | 28.266 | 124.129 | 1.00 | 63.33 |
| ATOM | 1925 | CG | LN | B | 123 | 117.209 | 27.829 | 127.618 | 1.00 | 46.32 |
| ATOM | 1926 | O | GLN | B | 123 | 116.221 | 28.495 | 127.310 | 1.00 | 46.58 |
| ATOM | 1927 | N | TYR | B | 124 | 117.635 | 27.701 | 128.869 | 1.00 | 43.86 |
| ATOM | 1928 | CA | TYR | B | 124 | 116.907 | 28.360 | 129.927 | 1.00 | 42.11 |
| ATOM | 1929 | CB | TYR | B | 124 | 117.518 | 28.026 | 131.294 | 1.00 | 41.58 |
| ATOM | 1930 | CG | TYR | B | 124 | 118.722 | 28.851 | 131.700 | 1.00 | 42.91 |
| ATOM | 1931 | CD1 | TYR | B | 124 | 118.594 | 30.204 | 132.041 | 1.00 | 42.19 |
| ATOM | 1932 | CE1 | TYR | B | 124 | 119.697 | 30.951 | 132.453 | 1.00 | 42.26 |
| ATOM | 1933 | CD2 | TYR | B | 124 | 119.989 | 28.269 | 131.781 | 1.00 | 42.35 |
| ATOM | 1934 | CE2 | TYR | B | 124 | 121.096 | 29.005 | 132.193 | 1.00 | 41.60 |
| ATOM | 1935 | CZ | TYR | B | 124 | 120.946 | 30.339 | 132.527 | 1.00 | 42.23 |
| ATOM | 1936 | OH | TYR | B | 124 | 122.046 | 31.048 | 132.944 | 1.00 | 41.91 |
| ATOM | 1937 | C | TYR | B | 124 | 116.889 | 29.866 | 129.672 | 1.00 | 41.35 |
| ATOM | 1938 | O | TYR | B | 124 | 117.800 | 30.423 | 129.065 | 1.00 | 40.98 |
| ATOM | 1939 | N | LYS | B | 125 | 115.821 | 30.507 | 130.126 | 1.00 | 40.27 |
| ATOM | 1940 | CA | LYS | B | 125 | 115.643 | 31.934 | 129.978 | 1.00 | 37.43 |
| ATOM | 1941 | CB | LYS | B | 125 | 114.227 | 32.210 | 129.493 | 1.00 | 37.31 |
| ATOM | 1942 | CG | LYS | B | 125 | 113.893 | 33.657 | 129.377 | 1.00 | 37.20 |
| ATOM | 1943 | CD | LYS | B | 125 | 112.614 | 33.812 | 128.619 | 1.00 | 39.57 |
| ATOM | 1944 | CE | LYS | B | 125 | 112.257 | 35.271 | 128.448 | 1.00 | 41.27 |
| ATOM | 1945 | NZ | LYS | B | 125 | 111.167 | 35.402 | 127.445 | 1.00 | 43.99 |
| ATOM | 1946 | C | LYS | B | 125 | 115.891 | 32.583 | 131.331 | 1.00 | 36.74 |
| ATOM | 1947 | O | LYS | B | 125 | 115.408 | 32.110 | 132.368 | 1.00 | 35.41 |
| ATOM | 1948 | N | LEU | B | 126 | 116.662 | 33.662 | 131.312 | 1.00 | 36.70 |
| ATOM | 1949 | CA | LEU | B | 126 | 117.005 | 34.383 | 132.522 | 1.00 | 36.52 |
| ATOM | 1950 | CB | LEU | B | 126 | 117.877 | 35.586 | 132.186 | 1.00 | 37.09 |
| ATOM | 1951 | CG | LEU | B | 126 | 119.375 | 35.336 | 132.036 | 1.00 | 37.50 |
| ATOM | 1952 | CD1 | LEU | B | 126 | 120.054 | 36.676 | 131.792 | 1.00 | 36.55 |
| ATOM | 1953 | CD2 | LEU | B | 126 | 119.933 | 34.674 | 133.298 | 1.00 | 36.86 |
| ATOM | 1954 | C | LEU | B | 126 | 115.802 | 34.859 | 133.298 | 1.00 | 36.94 |
| ATOM | 1955 | O | LEU | B | 126 | 114.878 | 35.432 | 132.732 | 1.00 | 38.21 |
| ATOM | 1956 | N | GLY | B | 127 | 115.823 | 34.635 | 134.603 | 1.00 | 36.87 |
| ATOM | 1957 | CA | GLY | B | 127 | 114.716 | 35.075 | 135.417 | 1.00 | 39.12 |
| ATOM | 1958 | C | GLY | B | 127 | 114.457 | 36.539 | 135.139 | 1.00 | 40.81 |
| ATOM | 1959 | O | GLY | B | 127 | 113.333 | 36.949 | 134.886 | 1.00 | 42.21 |
| ATOM | 1960 | N | SER | B | 128 | 115.515 | 37.332 | 135.174 | 1.00 | 42.67 |
| ATOM | 1961 | CA | SER | B | 128 | 115.409 | 38.761 | 134.929 | 1.00 | 44.81 |
| ATOM | 1962 | CB | SER | B | 128 | 116.826 | 39.362 | 134.873 | 1.00 | 46.60 |
| ATOM | 1963 | OG | SER | B | 128 | 117.725 | 38.527 | 134.145 | 1.00 | 48.48 |
| ATOM | 1964 | C | SER | B | 128 | 114.618 | 39.107 | 133.658 | 1.00 | 44.99 |
| ATOM | 1965 | O | SER | B | 128 | 114.206 | 40.256 | 133.465 | 1.00 | 44.55 |
| ATOM | 1966 | N | LYS | B | 129 | 114.393 | 38.113 | 132.803 | 1.00 | 45.58 |
| ATOM | 1967 | CA | LYS | B | 129 | 113.674 | 38.336 | 131.552 | 1.00 | 46.27 |
| ATOM | 1968 | CB | LYS | B | 129 | 114.514 | 37.864 | 130.358 | 1.00 | 46.90 |
| ATOM | 1969 | CG | LYS | B | 129 | 115.839 | 38.592 | 130.121 | 1.00 | 49.02 |
| ATOM | 1970 | CD | LYS | B | 129 | 116.341 | 38.312 | 128.697 | 1.00 | 49.89 |
| ATOM | 1971 | CE | LYS | B | 129 | 116.306 | 36.810 | 128.359 | 1.00 | 50.63 |
| ATOM | 1972 | NZ | LYS | B | 129 | 116.042 | 36.545 | 126.905 | 1.00 | 49.75 |
| ATOM | 1973 | C | LYS | B | 129 | 112.311 | 37.646 | 131.461 | 1.00 | 46.33 |
| ATOM | 1974 | O | LYS | B | 129 | 111.671 | 37.690 | 130.404 | 1.00 | 46.91 |
| ATOM | 1975 | N | THR | B | 130 | 111.860 | 37.018 | 132.544 | 1.00 | 44.73 |
| ATOM | 1976 | CA | THR | B | 130 | 110.581 | 36.307 | 132.517 | 1.00 | 43.35 |
| ATOM | 1977 | CB | THR | B | 130 | 110.621 | 35.062 | 133.386 | 1.00 | 41.73 |
| ATOM | 1978 | OG1 | THR | B | 130 | 110.608 | 35.455 | 134.763 | 1.00 | 39.55 |
| ATOM | 1979 | CG2 | THR | B | 130 | 111.874 | 34.249 | 133.090 | 1.00 | 41.36 |
| ATOM | 1980 | C | THR | B | 130 | 109.385 | 37.114 | 132.991 | 1.00 | 43.61 |
| ATOM | 1981 | O | THR | B | 130 | 109.473 | 37.861 | 133.959 | 1.00 | 43.97 |
| ATOM | 1982 | N | GLY | B | 131 | 108.259 | 36.927 | 132.314 | 1.00 | 43.39 |
| ATOM | 1983 | CA | GLY | B | 131 | 107.039 | 37.629 | 132.668 | 1.00 | 43.69 |
| ATOM | 1984 | C | GLY | B | 131 | 105.821 | 36.716 | 132.602 | 1.00 | 44.30 |
| ATOM | 1985 | O | GLY | B | 131 | 105.876 | 35.637 | 132.003 | 1.00 | 45.45 |
| ATOM | 1986 | N | PRO | B | 132 | 104.701 | 37.118 | 133.218 | 1.00 | 42.51 |
| ATOM | 1987 | CD | PRO | B | 132 | 104.560 | 38.310 | 134.066 | 1.00 | 40.46 |
| ATOM | 1988 | CA | PRO | B | 132 | 103.470 | 36.326 | 133.226 | 1.00 | 41.94 |
| ATOM | 1989 | CB | PRO | B | 132 | 102.560 | 37.119 | 134.155 | 1.00 | 42.03 |
| ATOM | 1990 | CG | PRO | B | 132 | 103.090 | 38.521 | 134.041 | 1.00 | 42.39 |
| ATOM | 1991 | C | PRO | B | 132 | 102.845 | 36.068 | 131.858 | 1.00 | 42.14 |
| ATOM | 1992 | O | PRO | B | 132 | 102.262 | 35.006 | 131.625 | 1.00 | 43.05 |
| ATOM | 1993 | N | GLY | B | 133 | 102.967 | 37.029 | 130.951 | 1.00 | 41.52 |

TABLE 1-continued

FGFR1 D2–D3 Complexed with FGF2

| | | | | | | | | | |
|---|---|---|---|---|---|---|---|---|---|
| ATOM | 1994 | CA | GLY | B | 133 | 102.398 | 36.844 | 129.632 | 1.00 | 40.35 |
| ATOM | 1995 | C | GLY | B | 133 | 103.299 | 36.031 | 128.728 | 1.00 | 39.56 |
| ATOM | 1996 | O | GLY | B | 133 | 103.087 | 35.995 | 127.526 | 1.00 | 41.25 |
| ATOM | 1997 | N | GLN | B | 134 | 104.293 | 35.361 | 129.298 | 1.00 | 38.32 |
| ATOM | 1998 | CA | GLN | B | 134 | 105.228 | 34.575 | 128.501 | 1.00 | 37.83 |
| ATOM | 1999 | CB | GLN | B | 134 | 106.643 | 34.795 | 129.015 | 1.00 | 36.88 |
| ATOM | 2000 | CG | GLN | B | 134 | 107.170 | 36.177 | 128.703 | 1.00 | 37.38 |
| ATOM | 2001 | CD | GLN | B | 134 | 108.506 | 36.441 | 129.351 | 1.00 | 37.57 |
| ATOM | 2002 | OE1 | GLN | B | 134 | 109.404 | 35.600 | 129.301 | 1.00 | 38.74 |
| ATOM | 2003 | NE2 | GLN | B | 134 | 108.651 | 37.614 | 129.960 | 1.00 | 34.92 |
| ATOM | 2004 | C | GLN | B | 134 | 104.969 | 33.079 | 128.378 | 1.00 | 38.13 |
| ATOM | 2005 | O | GLN | B | 134 | 104.701 | 32.387 | 129.362 | 1.00 | 39.42 |
| ATOM | 2006 | N | LYS | B | 135 | 105.084 | 32.595 | 127.146 | 1.00 | 37.17 |
| ATOM | 2007 | CA | LYS | B | 135 | 104.874 | 31.195 | 126.799 | 1.00 | 36.17 |
| ATOM | 2008 | CB | LYS | B | 135 | 104.796 | 31.095 | 125.273 | 1.00 | 35.42 |
| ATOM | 2009 | CG | LYS | B | 135 | 104.557 | 29.715 | 124.683 | 1.00 | 38.19 |
| ATOM | 2010 | CD | LYS | B | 135 | 104.243 | 29.862 | 123.193 | 1.00 | 40.23 |
| ATOM | 2011 | CE | LYS | B | 135 | 104.527 | 28.601 | 122.385 | 1.00 | 42.09 |
| ATOM | 2012 | NZ | LYS | B | 135 | 104.390 | 28.870 | 120.910 | 1.00 | 43.39 |
| ATOM | 2013 | C | LYS | B | 135 | 106.009 | 30.325 | 127.353 | 1.00 | 35.89 |
| ATOM | 2014 | O | LYS | B | 135 | 105.863 | 29.109 | 127.525 | 1.00 | 34.50 |
| ATOM | 2015 | N | ALA | B | 136 | 107.134 | 30.970 | 127.651 | 1.00 | 35.18 |
| ATOM | 2016 | CA | ALA | B | 136 | 108.310 | 30.278 | 128.170 | 1.00 | 34.66 |
| ATOM | 2017 | CB | ALA | B | 136 | 109.556 | 31.186 | 128.044 | 1.00 | 34.18 |
| ATOM | 2018 | C | ALA | B | 136 | 108.167 | 29.807 | 129.613 | 1.00 | 34.08 |
| ATOM | 2019 | O | ALA | B | 136 | 108.778 | 28.817 | 129.996 | 1.00 | 34.88 |
| ATOM | 2020 | N | ILE | B | 137 | 107.362 | 30.503 | 130.412 | 1.00 | 33.51 |
| ATOM | 2021 | CA | ILE | B | 137 | 107.206 | 30.131 | 131.813 | 1.00 | 31.04 |
| ATOM | 2022 | CB | ILE | B | 137 | 106.839 | 31.333 | 132.687 | 1.00 | 30.89 |
| ATOM | 2023 | CG2 | ILE | B | 137 | 107.918 | 32.402 | 132.550 | 1.00 | 30.26 |
| ATOM | 2024 | CG1 | ILE | B | 137 | 105.438 | 31.848 | 132.307 | 1.00 | 30.69 |
| ATOM | 2025 | CD1 | ILE | B | 137 | 104.692 | 32.539 | 133.443 | 1.00 | 26.19 |
| ATOM | 2026 | C | ILE | B | 137 | 106.176 | 29.064 | 132.071 | 1.00 | 29.74 |
| ATOM | 2027 | O | ILE | B | 137 | 106.022 | 28.617 | 133.206 | 1.00 | 31.83 |
| ATOM | 2028 | N | LEU | B | 138 | 105.478 | 28.642 | 131.030 | 1.00 | 28.62 |
| ATOM | 2029 | CA | LEU | B | 138 | 104.451 | 27.622 | 131.194 | 1.00 | 28.23 |
| ATOM | 2030 | CB | LEU | B | 138 | 103.284 | 27.930 | 130.259 | 1.00 | 29.47 |
| ATOM | 2031 | CG | LEU | B | 138 | 102.865 | 29.413 | 130.203 | 1.00 | 30.75 |
| ATOM | 2032 | CD1 | LEU | B | 138 | 101.796 | 29.566 | 129.128 | 1.00 | 29.77 |
| ATOM | 2033 | CD2 | LEU | B | 138 | 102.351 | 29.906 | 131.561 | 1.00 | 27.45 |
| ATOM | 2034 | C | LEU | B | 138 | 104.954 | 26.198 | 130.960 | 1.00 | 26.47 |
| ATOM | 2035 | O | LEU | B | 138 | 105.544 | 25.903 | 129.923 | 1.00 | 25.23 |
| ATOM | 2036 | N | PHE | B | 139 | 104.725 | 25.326 | 131.941 | 1.00 | 25.68 |
| ATOM | 2037 | CA | PHE | B | 139 | 105.131 | 23.923 | 131.846 | 1.00 | 25.87 |
| ATOM | 2038 | CB | PHE | B | 139 | 106.234 | 23.569 | 132.859 | 1.00 | 23.51 |
| ATOM | 2039 | CG | PHE | B | 139 | 107.506 | 24.311 | 132.656 | 1.00 | 21.66 |
| ATOM | 2040 | CD1 | PHE | B | 139 | 107.580 | 25.683 | 132.927 | 1.00 | 21.05 |
| ATOM | 2041 | CD2 | PHE | B | 139 | 108.625 | 23.657 | 132.148 | 1.00 | 20.83 |
| ATOM | 2042 | CE1 | PHE | B | 139 | 108.744 | 26.393 | 132.693 | 1.00 | 18.61 |
| ATOM | 2043 | CE2 | PHE | B | 139 | 109.801 | 24.358 | 131.908 | 1.00 | 19.33 |
| ATOM | 2044 | CZ | PHE | B | 139 | 109.859 | 25.732 | 132.181 | 1.00 | 20.03 |
| ATOM | 2045 | C | PHE | B | 139 | 103.951 | 23.010 | 132.110 | 1.00 | 26.53 |
| ATOM | 2046 | O | PHE | B | 139 | 102.993 | 23.380 | 132.786 | 1.00 | 27.10 |
| ATOM | 2047 | N | LEU | B | 140 | 104.050 | 21.800 | 131.588 | 1.00 | 28.27 |
| ATOM | 2048 | CA | LEU | B | 140 | 103.017 | 20.802 | 131.754 | 1.00 | 29.97 |
| ATOM | 2049 | CB | LEU | B | 140 | 102.468 | 20.429 | 130.382 | 1.00 | 30.53 |
| ATOM | 2050 | CG | LEU | B | 140 | 101.082 | 19.808 | 130.334 | 1.00 | 32.58 |
| ATOM | 2051 | CD1 | LEU | B | 140 | 100.063 | 20.784 | 130.918 | 1.00 | 33.58 |
| ATOM | 2052 | CD2 | LEU | B | 140 | 100.746 | 19.475 | 128.892 | 1.00 | 34.10 |
| ATOM | 2053 | C | LEU | B | 140 | 103.665 | 19.587 | 132.409 | 1.00 | 30.35 |
| ATOM | 2054 | O | LEU | B | 140 | 104.602 | 19.021 | 131.860 | 1.00 | 31.65 |
| ATOM | 2055 | N | PRO | B | 141 | 103.192 | 19.188 | 133.603 | 1.00 | 31.28 |
| ATOM | 2056 | CD | PRO | B | 141 | 102.215 | 19.891 | 134.457 | 1.00 | 31.64 |
| ATOM | 2057 | CA | PRO | B | 141 | 103.753 | 18.026 | 134.306 | 1.00 | 30.12 |
| ATOM | 2058 | CB | PRO | B | 141 | 103.109 | 18.105 | 135.693 | 1.00 | 29.44 |
| ATOM | 2059 | CG | PRO | B | 141 | 102.705 | 19.544 | 135.838 | 1.00 | 29.32 |
| ATOM | 2060 | C | PRO | B | 141 | 103.360 | 16.747 | 133.590 | 1.00 | 30.75 |
| ATOM | 2061 | O | PRO | B | 141 | 102.237 | 16.614 | 133.121 | 1.00 | 30.24 |
| ATOM | 2062 | N | MET | B | 142 | 104.282 | 15.801 | 133.509 | 1.00 | 33.53 |
| ATOM | 2063 | CA | MET | B | 142 | 104.011 | 14.533 | 132.847 | 1.00 | 35.21 |
| ATOM | 2064 | CB | MET | B | 142 | 104.585 | 14.543 | 131.428 | 1.00 | 35.75 |
| ATOM | 2065 | CG | MET | B | 142 | 103.932 | 15.558 | 130.502 | 1.00 | 40.96 |
| ATOM | 2066 | SD | MET | B | 142 | 104.611 | 15.593 | 128.806 | 1.00 | 48.60 |
| ATOM | 2067 | CE | MET | B | 142 | 103.935 | 14.039 | 128.108 | 1.00 | 46.52 |
| ATOM | 2068 | C | MET | B | 142 | 104.626 | 13.403 | 133.654 | 1.00 | 36.87 |
| ATOM | 2069 | O | MET | B | 142 | 105.849 | 13.302 | 133.791 | 1.00 | 36.47 |
| ATOM | 2070 | N | SER | B | 143 | 103.752 | 12.568 | 134.196 | 1.00 | 39.98 |

TABLE 1-continued

FGFR1 D2–D3 Complexed with FGF2

| ATOM | 2071 | CA | SER | B | 143 | 104.128 | 11.416 | 135.005 | 1.00 | 44.38 |
|---|---|---|---|---|---|---|---|---|---|---|
| ATOM | 2072 | CB | SER | B | 143 | 102.893 | 10.545 | 135.233 | 1.00 | 46.66 |
| ATOM | 2073 | OG | SER | B | 143 | 102.443 | 9.997 | 133.993 | 1.00 | 45.56 |
| ATOM | 2074 | C | SER | B | 143 | 105.188 | 40.565 | 134.310 | 1.00 | 46.01 |
| ATOM | 2075 | O | SER | B | 143 | 105.105 | 10.348 | 133.098 | 1.00 | 45.47 |
| ATOM | 2076 | N | ALA | B | 144 | 106.167 | 10.080 | 135.082 | 1.00 | 47.58 |
| ATOM | 2077 | CA | ALA | B | 144 | 107.235 | 9.220 | 134.557 | 1.00 | 47.58 |
| ATOM | 2078 | CB | ALA | B | 144 | 108.488 | 10.044 | 134.232 | 1.00 | 45.10 |
| ATOM | 2079 | C | ALA | B | 144 | 107.568 | 8.132 | 135.575 | 1.00 | 48.22 |
| ATOM | 2080 | O | ALA | B | 144 | 107.809 | 6.990 | 135.125 | 1.00 | 50.48 |
| ATOM | 2081 | CB | MET | C | 149 | 100.101 | 52.077 | 93.481 | 1.00 | 65.25 |
| ATOM | 2082 | CG | MET | C | 149 | 98.567 | 51.932 | 93.495 | 1.00 | 67.19 |
| ATOM | 2083 | SD | MET | C | 149 | 97.646 | 53.284 | 92.696 | 1.00 | 68.98 |
| ATOM | 2084 | CE | MET | C | 149 | 97.301 | 52.545 | 91.082 | 1.00 | 67.30 |
| ATOM | 2085 | C | MET | C | 149 | 99.985 | 53.283 | 95.664 | 1.00 | 60.59 |
| ATOM | 2086 | O | MET | C | 149 | 99.450 | 52.273 | 96.122 | 1.00 | 59.30 |
| ATOM | 2087 | N | MET | C | 149 | 102.131 | 53.199 | 94.388 | 1.00 | 62.84 |
| ATOM | 2088 | CA | MET | C | 149 | 100.638 | 53.271 | 94.282 | 1.00 | 62.68 |
| ATOM | 2089 | N | PRO | C | 150 | 100.005 | 54.441 | 96.338 | 1.00 | 58.42 |
| ATOM | 2090 | CD | PRO | C | 150 | 100.461 | 55.734 | 95.798 | 1.00 | 57.88 |
| ATOM | 2091 | CA | PRO | C | 150 | 99.424 | 54.610 | 97.675 | 1.00 | 56.45 |
| ATOM | 2092 | CB | PRO | C | 150 | 99.456 | 56.126 | 97.873 | 1.00 | 57.14 |
| ATOM | 2093 | CG | PRO | C | 150 | 100.633 | 56.551 | 97.044 | 1.00 | 57.64 |
| ATOM | 2094 | C | PRO | C | 150 | 98.005 | 54.048 | 97.816 | 1.00 | 53.83 |
| ATOM | 2095 | O | PRO | C | 150 | 97.107 | 54.416 | 97.055 | 1.00 | 53.21 |
| ATOM | 2096 | N | VAL | C | 151 | 97.816 | 53.165 | 98.796 | 1.00 | 50.88 |
| ATOM | 2097 | CA | VAL | C | 151 | 96.517 | 52.557 | 99.063 | 1.00 | 47.57 |
| ATOM | 2098 | CB | VAL | C | 151 | 96.416 | 51.143 | 98.490 | 1.00 | 48.19 |
| ATOM | 2099 | CG1 | VAL | C | 151 | 95.068 | 50.539 | 98.847 | 1.00 | 48.29 |
| ATOM | 2100 | CG2 | VAL | C | 151 | 96.594 | 51.184 | 96.983 | 1.00 | 50.20 |
| ATOM | 2101 | C | VAL | C | 151 | 96.272 | 52.448 | 100.554 | 1.00 | 45.11 |
| ATOM | 2102 | O | VAL | C | 151 | 97.118 | 51.951 | 101.287 | 1.00 | 43.01 |
| ATOM | 2103 | N | ALA | C | 152 | 95.110 | 52.927 | 100.993 | 1.00 | 44.71 |
| ATOM | 2104 | CA | ALA | C | 152 | 94.723 | 52.868 | 102.399 | 1.00 | 42.52 |
| ATOM | 2105 | CB | ALA | C | 152 | 93.535 | 53.769 | 102.656 | 1.00 | 40.04 |
| ATOM | 2106 | C | ALA | C | 152 | 94.359 | 51.418 | 102.712 | 1.00 | 41.56 |
| ATOM | 2107 | O | ALA | C | 152 | 93.933 | 50.671 | 101.827 | 1.00 | 41.60 |
| ATOM | 2108 | N | PRO | C | 153 | 94.526 | 50.995 | 103.974 | 1.00 | 40.07 |
| ATOM | 2109 | CD | PRO | C | 153 | 95.014 | 51.703 | 105.165 | 1.00 | 39.42 |
| ATOM | 2110 | CA | PRO | C | 153 | 94.186 | 49.607 | 104.289 | 1.00 | 38.59 |
| ATOM | 2111 | CB | PRO | C | 153 | 94.527 | 49.492 | 105.776 | 1.00 | 39.06 |
| ATOM | 2112 | CG | PRO | C | 153 | 94.411 | 50.890 | 106.270 | 1.00 | 41.48 |
| ATOM | 2113 | C | PRO | C | 153 | 92.747 | 49.217 | 103.964 | 1.00 | 37.37 |
| ATOM | 2114 | O | PRO | C | 153 | 91.816 | 50.015 | 104.083 | 1.00 | 38.28 |
| ATOM | 2115 | N | TYR | C | 154 | 92.579 | 47.981 | 103.522 | 1.00 | 35.32 |
| ATOM | 2116 | CA | TYR | C | 154 | 91.266 | 47.474 | 103.184 | 1.00 | 33.69 |
| ATOM | 2117 | CB | TYR | C | 154 | 90.978 | 47.693 | 101.702 | 1.00 | 32.71 |
| ATOM | 2118 | CG | TYR | C | 154 | 91.927 | 46.970 | 100.783 | 1.00 | 34.21 |
| ATOM | 2119 | CD1 | TYR | C | 154 | 93.190 | 47.490 | 100.492 | 1.00 | 34.37 |
| ATOM | 2120 | CE1 | TYR | C | 154 | 94.079 | 46.795 | 99.663 | 1.00 | 34.30 |
| ATOM | 2121 | CD2 | TYR | C | 154 | 91.576 | 45.743 | 100.228 | 1.00 | 34.12 |
| ATOM | 2122 | CE2 | TYR | C | 154 | 92.453 | 45.044 | 99.411 | 1.00 | 33.65 |
| ATOM | 2123 | CZ | TYR | C | 154 | 93.698 | 45.570 | 99.129 | 1.00 | 34.17 |
| ATOM | 2124 | OH | TYR | C | 154 | 94.547 | 44.866 | 98.308 | 1.00 | 34.07 |
| ATOM | 2125 | C | TYR | C | 154 | 91.185 | 45.986 | 103.517 | 1.00 | 32.85 |
| ATOM | 2126 | O | TYR | C | 154 | 92.190 | 45.273 | 103.508 | 1.00 | 30.45 |
| ATOM | 2127 | N | TRP | C | 155 | 89.981 | 45.523 | 102.814 | 1.00 | 32.07 |
| ATOM | 2128 | CA | TRP | C | 155 | 89.775 | 44.128 | 104.156 | 1.00 | 31.61 |
| ATOM | 2129 | CB | TRP | C | 155 | 88.371 | 43.940 | 104.721 | 1.00 | 27.53 |
| ATOM | 2130 | CG | TRP | C | 155 | 88.090 | 44.839 | 105.865 | 1.00 | 21.45 |
| ATOM | 2131 | CD2 | TRP | C | 155 | 88.848 | 44.946 | 107.074 | 1.00 | 18.68 |
| ATOM | 2132 | CE2 | TRP | C | 155 | 88.212 | 45.910 | 107.881 | 1.00 | 16.98 |
| ATOM | 2133 | CE3 | TRP | C | 155 | 90.005 | 44.319 | 107.553 | 1.00 | 14.94 |
| ATOM | 2134 | CD1 | TRP | C | 155 | 87.059 | 45.714 | 105.978 | 1.00 | 19.22 |
| ATOM | 2135 | NE1 | TRP | C | 155 | 87.122 | 46.365 | 107.188 | 1.00 | 19.31 |
| ATOM | 2136 | CZ2 | TRP | C | 155 | 88.687 | 46.264 | 109.143 | 1.00 | 15.29 |
| ATOM | 2137 | CZ3 | TRP | C | 155 | 90.478 | 44.670 | 108.803 | 1.00 | 13.39 |
| ATOM | 2138 | CH2 | TRP | C | 155 | 89.819 | 45.634 | 109.586 | 1.00 | 14.61 |
| ATOM | 2139 | C | TRP | C | 155 | 89.938 | 43.229 | 102.940 | 1.00 | 33.45 |
| ATOM | 2140 | O | TRP | C | 155 | 89.303 | 43.450 | 101.909 | 1.00 | 33.14 |
| ATOM | 2141 | N | THR | C | 156 | 90.782 | 42.209 | 103.071 | 1.00 | 35.38 |
| ATOM | 2142 | CA | THR | C | 156 | 90.996 | 41.265 | 101.985 | 1.00 | 36.52 |
| ATOM | 2143 | CB | THR | C | 156 | 92.456 | 40.730 | 101.936 | 1.00 | 33.61 |
| ATOM | 2144 | OG1 | THR | C | 156 | 92.835 | 40.196 | 103.207 | 1.00 | 32.46 |
| ATOM | 2145 | CG2 | THR | C | 156 | 93.401 | 41.832 | 101.566 | 1.00 | 34.29 |
| ATOM | 2146 | C | THR | C | 156 | 90.047 | 40.075 | 102.090 | 1.00 | 38.59 |
| ATOM | 2147 | O | THR | C | 156 | 89.808 | 39.388 | 101.103 | 1.00 | 38.35 |

TABLE 1-continued

FGFR1 D2–D3 Complexed with FGF2

| ATOM | 2148 | N | SER | C | 157 | 89.491 | 39.840 | 103.275 | 1.00 | 40.70 |
|---|---|---|---|---|---|---|---|---|---|---|
| ATOM | 2149 | CA | SER | C | 157 | 88.579 | 38.717 | 103.466 | 1.00 | 43.38 |
| ATOM | 2150 | CB | SER | C | 157 | 89.344 | 37.529 | 104.044 | 1.00 | 43.82 |
| ATOM | 2151 | OG | SER | C | 157 | 90.408 | 37.166 | 103.185 | 1.00 | 45.77 |
| ATOM | 2152 | C | SER | C | 157 | 87.420 | 39.060 | 104.383 | 1.00 | 44.72 |
| ATOM | 2153 | O | SER | C | 157 | 87.261 | 38.476 | 105.450 | 1.00 | 45.26 |
| ATOM | 2154 | N | PRO | C | 158 | 86.580 | 40.006 | 103.970 | 1.00 | 46.25 |
| ATOM | 2155 | CD | PRO | C | 158 | 86.466 | 40.509 | 102.593 | 1.00 | 46.97 |
| ATOM | 2156 | C | PRO | C | 158 | 85.429 | 40.426 | 104.774 | 1.00 | 46.67 |
| ATOM | 2157 | CB | PRO | C | 158 | 84.771 | 41.465 | 103.889 | 1.00 | 47.50 |
| ATOM | 2158 | CG | PRO | C | 158 | 85.000 | 40.879 | 102.520 | 1.00 | 48.42 |
| ATOM | 2159 | C | PRO | C | 158 | 84.491 | 39.267 | 105.075 | 1.00 | 47.02 |
| ATOM | 2160 | O | PRO | C | 158 | 83.680 | 39.332 | 106.001 | 1.00 | 46.75 |
| ATOM | 2161 | N | GLU | C | 159 | 84.605 | 38.212 | 104.272 | 1.00 | 48.26 |
| ATOM | 2162 | CA | GLU | C | 159 | 83.780 | 37.014 | 104.422 | 1.00 | 47.93 |
| ATOM | 2163 | CB | GLU | C | 159 | 84.023 | 36.060 | 103.250 | 1.00 | 48.14 |
| ATOM | 2164 | C | GLU | C | 159 | 84.116 | 36.300 | 105.725 | 1.00 | 47.69 |
| ATOM | 2165 | O | GLU | C | 159 | 83.256 | 35.678 | 106.347 | 1.00 | 48.83 |
| ATOM | 2166 | N | LYS | C | 160 | 85.380 | 36.395 | 106.127 | 1.00 | 46.16 |
| ATOM | 2167 | CA | LYS | C | 160 | 85.859 | 35.764 | 107.355 | 1.00 | 44.33 |
| ATOM | 2168 | CB | LYS | C | 160 | 87.342 | 35.382 | 107.208 | 1.00 | 41.06 |
| ATOM | 2169 | C | LYS | C | 160 | 85.686 | 36.662 | 108.587 | 1.00 | 42.94 |
| ATOM | 2170 | O | LYS | C | 160 | 86.342 | 36.456 | 109.604 | 1.00 | 42.81 |
| ATOM | 2171 | N | MET | C | 161 | 84.793 | 37.642 | 108.509 | 1.00 | 41.39 |
| ATOM | 2172 | CA | MET | C | 161 | 84.595 | 38.558 | 109.628 | 1.00 | 39.39 |
| ATOM | 2173 | CB | MET | C | 161 | 85.216 | 39.934 | 109.294 | 1.00 | 38.51 |
| ATOM | 2174 | CG | MET | C | 161 | 86.759 | 39.909 | 109.157 | 1.00 | 37.19 |
| ATOM | 2175 | SD | MET | C | 161 | 87.570 | 41.276 | 108.213 | 1.00 | 35.28 |
| ATOM | 2176 | CE | MET | C | 161 | 87.835 | 42.474 | 109.497 | 1.00 | 32.14 |
| ATOM | 2177 | C | MET | C | 161 | 83.128 | 38.711 | 110.002 | 1.00 | 38.73 |
| ATOM | 2178 | O | MET | C | 161 | 82.798 | 39.400 | 110.962 | 1.00 | 38.29 |
| ATOM | 2179 | N | GLU | C | 162 | 82.254 | 38.048 | 109.254 | 1.00 | 38.86 |
| ATOM | 2180 | CA | GLU | C | 162 | 80.812 | 38.108 | 109.503 | 1.00 | 38.59 |
| ATOM | 2181 | CB | GLU | C | 162 | 80.080 | 37.201 | 108.502 | 1.00 | 35.61 |
| ATOM | 2182 | C | GLU | C | 162 | 80.398 | 37.733 | 110.944 | 1.00 | 38.75 |
| ATOM | 2183 | O | GLU | C | 162 | 79.430 | 38.274 | 111.487 | 1.00 | 39.79 |
| ATOM | 2184 | N | LYS | C | 163 | 81.126 | 36.815 | 111.568 | 1.00 | 38.04 |
| ATOM | 2185 | CA | LYS | C | 163 | 80.793 | 36.386 | 112.926 | 1.00 | 36.88 |
| ATOM | 2186 | CB | LYS | C | 163 | 81.329 | 34.972 | 113.155 | 1.00 | 37.78 |
| ATOM | 2187 | CG | LYS | C | 163 | 81.010 | 34.345 | 114.504 | 1.00 | 37.86 |
| ATOM | 2188 | CD | LYS | C | 163 | 81.898 | 33.115 | 114.723 | 1.00 | 37.39 |
| ATOM | 2189 | CE | LYS | C | 163 | 82.049 | 32.836 | 116.206 | 1.00 | 41.05 |
| ATOM | 2190 | NZ | LYS | C | 163 | 83.124 | 31.856 | 116.549 | 1.00 | 43.85 |
| ATOM | 2191 | C | LYS | C | 163 | 81.369 | 37.344 | 113.959 | 1.00 | 36.41 |
| ATOM | 2192 | O | LYS | C | 163 | 82.474 | 37.129 | 114.464 | 1.00 | 38.35 |
| ATOM | 2193 | N | LYS | C | 164 | 80.618 | 38.399 | 114.271 | 1.00 | 34.77 |
| ATOM | 2194 | CA | LYS | C | 164 | 81.061 | 39.405 | 115.233 | 1.00 | 33.48 |
| ATOM | 2195 | CB | LYS | C | 164 | 80.155 | 40.645 | 115.153 | 1.00 | 31.00 |
| ATOM | 2196 | C | LYS | C | 164 | 81.141 | 38.879 | 116.677 | 1.00 | 33.76 |
| ATOM | 2197 | O | LYS | C | 164 | 82.067 | 39.239 | 117.410 | 1.00 | 34.50 |
| ATOM | 2198 | N | LEU | C | 165 | 80.192 | 38.026 | 117.081 | 1.00 | 33.68 |
| ATOM | 2199 | CA | LEU | C | 165 | 80.182 | 37.450 | 118.435 | 1.00 | 31.67 |
| ATOM | 2200 | CB | LEU | C | 165 | 78.764 | 37.376 | 118.989 | 1.00 | 32.15 |
| ATOM | 2201 | CG | LEU | C | 165 | 78.678 | 36.482 | 120.242 | 1.00 | 32.85 |
| ATOM | 2202 | CD1 | LEU | C | 165 | 79.467 | 37.102 | 121.383 | 1.00 | 30.15 |
| ATOM | 2203 | CD2 | LEU | C | 165 | 77.244 | 36.289 | 120.648 | 1.00 | 32.03 |
| ATOM | 2204 | C | LEU | C | 165 | 80.778 | 36.046 | 118.571 | 1.00 | 31.11 |
| ATOM | 2205 | O | LEU | C | 165 | 80.331 | 35.112 | 117.914 | 1.00 | 28.78 |
| ATOM | 2206 | N | HIS | C | 166 | 81.766 | 35.908 | 119.454 | 1.00 | 32.82 |
| ATOM | 2207 | CA | HIS | C | 166 | 82.404 | 34.618 | 119.736 | 1.00 | 33.88 |
| ATOM | 2208 | CB | HIS | C | 166 | 83.919 | 34.710 | 119.632 | 1.00 | 35.77 |
| ATOM | 2209 | CG | HIS | C | 166 | 84.413 | 34.914 | 118.243 | 1.00 | 41.33 |
| ATOM | 2210 | CD2 | HIS | C | 166 | 85.227 | 34.159 | 117.469 | 1.00 | 43.37 |
| ATOM | 2211 | ND1 | HIS | C | 166 | 84.069 | 36.015 | 117.487 | 1.00 | 42.96 |
| ATOM | 2212 | CE1 | HIS | C | 166 | 84.651 | 35.930 | 116.303 | 1.00 | 44.52 |
| ATOM | 2213 | NE2 | HIS | C | 166 | 85.360 | 34.814 | 116.267 | 1.00 | 45.66 |
| ATOM | 2214 | C | HIS | C | 166 | 82.068 | 34.159 | 121.151 | 1.00 | 33.19 |
| ATOM | 2215 | O | HIS | C | 166 | 82.627 | 34.669 | 122.132 | 1.00 | 30.45 |
| ATOM | 2216 | N | ALA | C | 167 | 81.152 | 33.198 | 121.249 | 1.00 | 32.79 |
| ATOM | 2217 | CA | ALA | C | 167 | 80.745 | 32.641 | 122.534 | 1.00 | 33.37 |
| ATOM | 2218 | CB | ALA | C | 167 | 79.227 | 32.558 | 122.627 | 1.00 | 32.85 |
| ATOM | 2219 | C | ALA | C | 167 | 81.352 | 31.252 | 122.595 | 1.00 | 33.26 |
| ATOM | 2220 | O | ALA | C | 167 | 81.205 | 30.459 | 121.654 | 1.00 | 32.87 |
| ATOM | 2221 | N | VAL | C | 168 | 82.027 | 30.955 | 123.702 | 1.00 | 32.58 |
| ATOM | 2222 | CA | VAL | C | 168 | 82.683 | 29.669 | 123.849 | 1.00 | 31.16 |
| ATOM | 2223 | CB | VAL | C | 168 | 84.114 | 29.747 | 123.277 | 1.00 | 30.30 |
| ATOM | 2224 | CG1 | VAL | C | 168 | 84.071 | 30.079 | 121.815 | 1.00 | 29.14 |

TABLE 1-continued

FGFR1 D2–D3 Complexed with FGF2

| ATOM | 2225 | CG2 | VAL | C | 168 | 84.911 | 30.820 | 124.018 | 1.00 | 29.56 |
|------|------|-----|-----|---|-----|--------|--------|---------|------|-------|
| ATOM | 2226 | C | VAL | C | 168 | 82.794 | 29.160 | 125.283 | 1.00 | 30.45 |
| ATOM | 2227 | O | VAL | C | 168 | 82.688 | 29.921 | 126.245 | 1.00 | 29.08 |
| ATOM | 2228 | N | PRO | C | 169 | 82.971 | 27.842 | 125.436 | 1.00 | 30.30 |
| ATOM | 2229 | CD | PRO | C | 169 | 82.654 | 26.785 | 124.457 | 1.00 | 28.93 |
| ATOM | 2230 | CA | PRO | C | 169 | 83.110 | 27.285 | 126.781 | 1.00 | 30.64 |
| ATOM | 2231 | CB | PRO | C | 169 | 82.783 | 25.806 | 126.581 | 1.00 | 28.08 |
| ATOM | 2232 | CG | PRO | C | 169 | 83.173 | 25.558 | 125.144 | 1.00 | 28.90 |
| ATOM | 2233 | C | PRO | C | 169 | 84.562 | 27.535 | 127.237 | 1.00 | 32.73 |
| ATOM | 2234 | O | PRO | C | 169 | 85.511 | 27.347 | 126.458 | 1.00 | 34.04 |
| ATOM | 2235 | N | ALA | C | 170 | 84.725 | 27.979 | 128.482 | 1.00 | 32.44 |
| ATOM | 2236 | CA | ALA | C | 170 | 86.039 | 28.261 | 129.046 | 1.00 | 31.35 |
| ATOM | 2237 | CB | ALA | C | 170 | 85.928 | 28.414 | 130.554 | 1.00 | 31.49 |
| ATOM | 2238 | C | ALA | C | 170 | 87.053 | 27.175 | 128.712 | 1.00 | 31.45 |
| ATOM | 2239 | O | ALA | C | 170 | 86.693 | 26.005 | 128.575 | 1.00 | 30.29 |
| ATOM | 2240 | N | ALA | C | 171 | 88.314 | 27.588 | 128.580 | 1.00 | 31.27 |
| ATOM | 2241 | CA | ALA | C | 171 | 89.436 | 26.705 | 128.280 | 1.00 | 31.34 |
| ATOM | 2242 | CB | ALA | C | 171 | 89.218 | 25.326 | 128.910 | 1.00 | 30.46 |
| ATOM | 2243 | C | ALA | C | 171 | 89.696 | 26.571 | 126.793 | 1.00 | 31.73 |
| ATOM | 2244 | O | ALA | C | 171 | 90.701 | 25.989 | 126.387 | 1.00 | 33.59 |
| ATOM | 2245 | N | LYS | C | 172 | 88.800 | 27.115 | 125.981 | 1.00 | 32.03 |
| ATOM | 2246 | CA | LYS | C | 172 | 88.960 | 27.043 | 124.533 | 1.00 | 32.88 |
| ATOM | 2247 | CB | LYS | C | 172 | 87.599 | 27.256 | 123.846 | 1.00 | 30.96 |
| ATOM | 2248 | C | LYS | C | 172 | 89.987 | 28.080 | 124.030 | 1.00 | 33.39 |
| ATOM | 2249 | O | LYS | C | 172 | 90.207 | 29.110 | 124.665 | 1.00 | 32.67 |
| ATOM | 2250 | N | THR | C | 173 | 90.623 | 27.773 | 122.902 | 1.00 | 33.31 |
| ATOM | 2251 | CA | THR | C | 173 | 91.600 | 28.649 | 122.261 | 1.00 | 32.28 |
| ATOM | 2252 | CB | THR | C | 173 | 92.572 | 27.846 | 121.364 | 1.00 | 33.35 |
| ATOM | 2253 | OG1 | THR | C | 173 | 93.408 | 27.012 | 122.176 | 1.00 | 36.76 |
| ATOM | 2254 | CG2 | THR | C | 173 | 93.419 | 28.780 | 120.513 | 1.00 | 30.69 |
| ATOM | 2255 | C | THR | C | 173 | 90.832 | 29.570 | 121.327 | 1.00 | 32.19 |
| ATOM | 2256 | O | THR | C | 173 | 90.104 | 29.097 | 120.463 | 1.00 | 31.00 |
| ATOM | 2257 | N | VAL | C | 174 | 91.002 | 30.877 | 121.486 | 1.00 | 33.05 |
| ATOM | 2258 | CA | VAL | C | 174 | 90.322 | 31.856 | 120.635 | 1.00 | 32.11 |
| ATOM | 2259 | CB | VAL | C | 174 | 89.621 | 32.944 | 121.499 | 1.00 | 30.78 |
| ATOM | 2260 | CG1 | VAL | C | 174 | 89.310 | 34.173 | 120.656 | 1.00 | 30.69 |
| ATOM | 2261 | CG2 | VAL | C | 174 | 88.335 | 32.393 | 122.085 | 1.00 | 30.31 |
| ATOM | 2262 | C | VAL | C | 174 | 91.287 | 32.555 | 119.664 | 1.00 | 31.79 |
| ATOM | 2263 | O | VAL | C | 174 | 92.390 | 32.929 | 120.049 | 1.00 | 32.17 |
| ATOM | 2264 | N | LYS | C | 175 | 90.865 | 32.728 | 118.410 | 1.00 | 31.18 |
| ATOM | 2265 | CA | LYS | C | 175 | 91.675 | 33.408 | 117.399 | 1.00 | 30.82 |
| ATOM | 2266 | CB | LYS | C | 175 | 92.271 | 32.392 | 116.408 | 1.00 | 26.76 |
| ATOM | 2267 | C | LYS | C | 175 | 90.801 | 34.409 | 116.641 | 1.00 | 31.23 |
| ATOM | 2268 | O | LYS | C | 175 | 89.760 | 34.048 | 116.119 | 1.00 | 31.11 |
| ATOM | 2269 | N | PHE | C | 176 | 91.216 | 35.671 | 116.606 | 1.00 | 33.39 |
| ATOM | 2270 | CA | PHE | C | 176 | 90.481 | 36.716 | 115.893 | 1.00 | 33.06 |
| ATOM | 2271 | CB | PHE | C | 176 | 90.184 | 37.888 | 116.820 | 1.00 | 30.10 |
| ATOM | 2272 | CG | PHE | C | 176 | 89.218 | 37.552 | 117.903 | 1.00 | 29.97 |
| ATOM | 2273 | CD1 | PHE | C | 176 | 88.000 | 36.942 | 117.597 | 1.00 | 28.34 |
| ATOM | 2274 | CD2 | PHE | C | 176 | 89.512 | 37.839 | 119.234 | 1.00 | 27.98 |
| ATOM | 2275 | CE1 | PHE | C | 176 | 87.096 | 36.627 | 118.606 | 1.00 | 27.80 |
| ATOM | 2276 | CE2 | PHE | C | 176 | 88.607 | 37.524 | 120.249 | 1.00 | 26.08 |
| ATOM | 2277 | CZ | PHE | C | 176 | 87.400 | 36.921 | 119.935 | 1.00 | 25.99 |
| ATOM | 2278 | C | PHE | C | 176 | 91.294 | 37.197 | 114.700 | 1.00 | 33.94 |
| ATOM | 2279 | O | PHE | C | 176 | 92.437 | 37.622 | 114.856 | 1.00 | 33.78 |
| ATOM | 2280 | N | LYS | C | 177 | 90.693 | 37.128 | 113.515 | 1.00 | 35.23 |
| ATOM | 2281 | CA | LYS | C | 177 | 91.364 | 37.530 | 112.284 | 1.00 | 35.59 |
| ATOM | 2282 | CB | LYS | C | 177 | 91.323 | 36.373 | 111.276 | 1.00 | 34.19 |
| ATOM | 2283 | C | LYS | C | 177 | 90.784 | 38.794 | 111.644 | 1.00 | 34.98 |
| ATOM | 2284 | O | LYS | C | 177 | 89.571 | 38.993 | 111.601 | 1.00 | 33.90 |
| ATOM | 2285 | N | CYS | C | 178 | 91.676 | 39.648 | 111.155 | 1.00 | 35.07 |
| ATOM | 2286 | CA | CYS | C | 178 | 91.300 | 40.888 | 110.475 | 1.00 | 35.44 |
| ATOM | 2287 | C | CYS | C | 178 | 92.115 | 41.000 | 109.186 | 1.00 | 35.69 |
| ATOM | 2288 | O | CYS | C | 178 | 92.889 | 41.941 | 109.003 | 1.00 | 32.89 |
| ATOM | 2289 | CB | CYS | C | 178 | 91.578 | 42.094 | 111.366 | 1.00 | 34.12 |
| ATOM | 2290 | SG | CYS | C | 178 | 90.402 | 42.228 | 112.746 | 1.00 | 36.50 |
| ATOM | 2291 | N | PRO | C | 179 | 91.940 | 40.032 | 108.273 | 1.00 | 36.77 |
| ATOM | 2292 | CD | PRO | C | 179 | 90.908 | 38.987 | 108.287 | 1.00 | 36.42 |
| ATOM | 2293 | CA | PRO | C | 179 | 92.665 | 40.019 | 107.003 | 1.00 | 38.32 |
| ATOM | 2294 | CB | PRO | C | 179 | 92.048 | 38.836 | 106.259 | 1.00 | 37.75 |
| ATOM | 2295 | CG | PRO | C | 179 | 91.493 | 37.977 | 107.357 | 1.00 | 37.51 |
| ATOM | 2296 | C | PRO | C | 179 | 92.456 | 41.324 | 106.259 | 1.00 | 39.57 |
| ATOM | 2297 | O | PRO | C | 179 | 91.340 | 41.645 | 105.845 | 1.00 | 39.56 |
| ATOM | 2298 | N | SER | C | 180 | 93.539 | 42.071 | 106.103 | 1.00 | 40.72 |
| ATOM | 2299 | CA | SER | C | 180 | 93.494 | 43.345 | 105.413 | 1.00 | 42.44 |
| ATOM | 2300 | CB | SER | C | 180 | 93.452 | 44.488 | 106.436 | 1.00 | 41.84 |
| ATOM | 2301 | OG | SER | C | 180 | 94.668 | 44.587 | 107.145 | 1.00 | 38.33 |

TABLE 1-continued

FGFR1 D2–D3 Complexed with FGF2

| ATOM | 2302 | C | SER | C | 180 | 94.719 | 43.493 | 104.513 | 1.00 | 43.44 |
|---|---|---|---|---|---|---|---|---|---|---|
| ATOM | 2303 | O | SER | C | 180 | 95.564 | 42.597 | 104.446 | 1.00 | 44.06 |
| ATOM | 2304 | N | SER | C | 181 | 94.809 | 44.626 | 103.821 | 1.00 | 43.27 |
| ATOM | 2305 | CA | SER | C | 181 | 95.936 | 44.892 | 102.941 | 1.00 | 42.03 |
| ATOM | 2306 | CB | SER | C | 181 | 95.782 | 44.108 | 101.635 | 1.00 | 40.63 |
| ATOM | 2307 | OG | SER | C | 181 | 96.947 | 44.184 | 100.837 | 1.00 | 38.12 |
| ATOM | 2308 | C | SER | C | 181 | 96.023 | 46.378 | 102.648 | 1.00 | 42.50 |
| ATOM | 2309 | O | SER | C | 181 | 95.125 | 47.143 | 102.995 | 1.00 | 41.78 |
| ATOM | 2310 | N | GLY | C | 182 | 97.120 | 46.777 | 102.014 | 1.00 | 44.44 |
| ATOM | 2311 | CA | GLY | C | 182 | 97.320 | 48.171 | 101.656 | 1.00 | 45.04 |
| ATOM | 2312 | C | GLY | C | 182 | 98.783 | 48.471 | 101.418 | 1.00 | 44.61 |
| ATOM | 2313 | O | GLY | C | 182 | 99.645 | 47.695 | 101.829 | 1.00 | 44.78 |
| ATOM | 2314 | N | THR | C | 183 | 99.070 | 49.577 | 100.735 | 1.00 | 44.98 |
| ATOM | 2315 | CA | THR | C | 183 | 100.456 | 49.970 | 100.486 | 1.00 | 43.50 |
| ATOM | 2316 | CB | THR | C | 183 | 100.890 | 49.698 | 99.019 | 1.00 | 42.33 |
| ATOM | 2317 | OG1 | THR | C | 183 | 100.264 | 50.645 | 98.148 | 1.00 | 43.45 |
| ATOM | 2318 | CG2 | THR | C | 183 | 100.513 | 48.279 | 98.599 | 1.00 | 39.10 |
| ATOM | 2319 | C | THR | C | 183 | 100.666 | 51.455 | 100.816 | 1.00 | 42.89 |
| ATOM | 2320 | O | THR | C | 183 | 99.935 | 52.329 | 100.345 | 1.00 | 42.37 |
| ATOM | 2321 | N | PRO | C | 184 | 101.659 | 51.749 | 101.670 | 1.00 | 43.03 |
| ATOM | 2322 | CD | PRO | C | 184 | 101.978 | 53.103 | 102.159 | 1.00 | 43.09 |
| ATOM | 2323 | CA | PRO | C | 184 | 102.540 | 50.755 | 102.290 | 1.00 | 42.57 |
| ATOM | 2324 | CB | PRO | C | 184 | 103.592 | 51.618 | 102.977 | 1.00 | 41.56 |
| ATOM | 2325 | CG | PRO | C | 184 | 102.811 | 52.817 | 103.396 | 1.00 | 41.09 |
| ATOM | 2326 | C | PRO | C | 184 | 101.825 | 49.814 | 103.268 | 1.00 | 43.39 |
| ATOM | 2327 | O | PRO | C | 184 | 100.795 | 50.162 | 103.861 | 1.00 | 43.41 |
| ATOM | 2328 | N | GLN | C | 185 | 102.386 | 48.619 | 103.418 | 1.00 | 43.86 |
| ATOM | 2329 | CA | GLN | C | 185 | 101.862 | 47.586 | 104.312 | 1.00 | 43.86 |
| ATOM | 2330 | CB | GLN | C | 185 | 102.944 | 46.527 | 104.538 | 1.00 | 45.08 |
| ATOM | 2331 | CG | GLN | C | 185 | 102.489 | 45.299 | 105.297 | 1.00 | 46.91 |
| ATOM | 2332 | CD | GLN | C | 185 | 101.676 | 44.346 | 104.437 | 1.00 | 48.43 |
| ATOM | 2333 | OE1 | GLN | C | 185 | 101.304 | 43.264 | 104.891 | 1.00 | 50.68 |
| ATOM | 2334 | NE2 | GLN | C | 185 | 101.397 | 44.741 | 103.192 | 1.00 | 46.11 |
| ATOM | 2335 | C | GLN | C | 185 | 101.446 | 48.171 | 105.660 | 1.00 | 42.38 |
| ATOM | 2336 | O | GLN | C | 185 | 102.272 | 48.724 | 106.381 | 1.00 | 43.07 |
| ATOM | 2337 | N | PRO | C | 186 | 100.157 | 48.053 | 106.021 | 1.00 | 41.59 |
| ATOM | 2338 | CD | PRO | C | 186 | 99.013 | 47.664 | 105.175 | 1.00 | 40.45 |
| ATOM | 2339 | CA | PRO | C | 186 | 99.704 | 48.599 | 107.308 | 1.00 | 40.23 |
| ATOM | 2340 | CB | PRO | C | 186 | 98.188 | 48.660 | 107.143 | 1.00 | 39.29 |
| ATOM | 2341 | CG | PRO | C | 186 | 97.905 | 47.553 | 106.177 | 1.00 | 40.98 |
| ATOM | 2342 | C | PRO | C | 186 | 100.143 | 47.865 | 108.583 | 1.00 | 39.30 |
| ATOM | 2343 | O | PRO | C | 186 | 100.686 | 46.758 | 108.545 | 1.00 | 39.33 |
| ATOM | 2344 | N | THR | C | 187 | 99.915 | 48.523 | 109.711 | 1.00 | 39.08 |
| ATOM | 2345 | CA | THR | C | 187 | 100.268 | 47.999 | 111.029 | 1.00 | 39.63 |
| ATOM | 2346 | CB | THR | C | 187 | 100.741 | 49.125 | 111.967 | 1.00 | 39.84 |
| ATOM | 2347 | OG1 | THR | C | 187 | 99.591 | 49.774 | 112.531 | 1.00 | 38.71 |
| ATOM | 2348 | CG2 | THR | C | 187 | 101.560 | 50.155 | 111.206 | 1.00 | 37.86 |
| ATOM | 2349 | C | THR | C | 187 | 99.025 | 47.407 | 111.684 | 1.00 | 39.39 |
| ATOM | 2350 | O | THR | C | 187 | 97.924 | 47.939 | 111.515 | 1.00 | 39.66 |
| ATOM | 2351 | N | LEU | C | 188 | 99.211 | 46.340 | 112.459 | 1.00 | 38.00 |
| ATOM | 2352 | CA | LEU | C | 188 | 98.103 | 45.682 | 113.148 | 1.00 | 36.36 |
| ATOM | 2353 | CB | LEU | C | 188 | 98.017 | 44.207 | 112.725 | 1.00 | 33.97 |
| ATOM | 2354 | CG | LEU | C | 188 | 96.738 | 43.357 | 112.848 | 1.00 | 31.46 |
| ATOM | 2355 | CD1 | LEU | C | 188 | 97.137 | 41.908 | 113.017 | 1.00 | 28.72 |
| ATOM | 2356 | CD2 | LEU | C | 188 | 95.886 | 43.779 | 114.021 | 1.00 | 33.12 |
| ATOM | 2357 | C | LEU | C | 188 | 98.298 | 45.731 | 114.661 | 1.00 | 36.78 |
| ATOM | 2358 | O | LEU | C | 188 | 99.316 | 45.271 | 115.176 | 1.00 | 37.59 |
| ATOM | 2359 | N | ARG | C | 189 | 97.332 | 46.297 | 115.371 | 1.00 | 37.19 |
| ATOM | 2360 | CA | ARG | C | 189 | 97.391 | 46.323 | 116.829 | 1.00 | 38.17 |
| ATOM | 2361 | CB | ARG | C | 189 | 97.843 | 47.685 | 117.345 | 1.00 | 39.09 |
| ATOM | 2362 | CG | ARG | C | 189 | 96.901 | 48.786 | 117.030 | 1.00 | 44.89 |
| ATOM | 2363 | CD | ARG | C | 189 | 97.431 | 50.096 | 117.534 | 1.00 | 50.33 |
| ATOM | 2364 | NE | ARG | C | 189 | 96.532 | 51.182 | 117.161 | 1.00 | 57.72 |
| ATOM | 2365 | CZ | ARG | C | 189 | 96.804 | 52.473 | 117.326 | 1.00 | 61.98 |
| ATOM | 2366 | NH1 | ARG | C | 189 | 97.960 | 52.847 | 117.863 | 1.00 | 65.57 |
| ATOM | 2367 | NH2 | ARG | C | 189 | 95.922 | 53.394 | 116.948 | 1.00 | 64.03 |
| ATOM | 2368 | C | ARG | C | 189 | 95.993 | 45.984 | 117.344 | 1.00 | 36.93 |
| ATOM | 2369 | O | ARG | C | 189 | 95.005 | 46.220 | 116.650 | 1.00 | 37.99 |
| ATOM | 2370 | N | TRP | C | 190 | 95.908 | 45.407 | 118.540 | 1.00 | 35.51 |
| ATOM | 2371 | CA | TRP | C | 190 | 94.613 | 45.041 | 119.111 | 1.00 | 33.97 |
| ATOM | 2372 | CB | TRP | C | 190 | 94.537 | 43.550 | 119.414 | 1.00 | 32.32 |
| ATOM | 2373 | CG | TRP | C | 190 | 94.615 | 42.690 | 118.212 | 1.00 | 33.64 |
| ATOM | 2374 | CD2 | TRP | C | 190 | 93.514 | 42.111 | 117.497 | 1.00 | 35.85 |
| ATOM | 2375 | CE2 | TRP | C | 190 | 94.057 | 41.391 | 116.409 | 1.00 | 34.62 |
| ATOM | 2376 | CE3 | TRP | C | 190 | 92.117 | 42.131 | 117.670 | 1.00 | 36.09 |
| ATOM | 2377 | CD1 | TRP | C | 190 | 95.741 | 42.309 | 117.549 | 1.00 | 32.67 |
| ATOM | 2378 | NE1 | TRP | C | 190 | 95.419 | 41.531 | 116.468 | 1.00 | 32.98 |

TABLE 1-continued

FGFR1 D2–D3 Complexed with FGF2

| ATOM | 2379 | CZ2 | TRP | C | 190 | 93.255 | 40.694 | 115.495 | 1.00 | 31.94 |
|---|---|---|---|---|---|---|---|---|---|---|
| ATOM | 2380 | CZ3 | TRP | C | 190 | 91.322 | 41.438 | 116.760 | 1.00 | 32.93 |
| ATOM | 2381 | CH2 | TRP | C | 190 | 91.898 | 40.730 | 115.688 | 1.00 | 33.05 |
| ATOM | 2382 | C | TRP | C | 190 | 94.301 | 45.793 | 120.382 | 1.00 | 34.67 |
| ATOM | 2383 | O | TRP | C | 190 | 95.201 | 46.292 | 121.059 | 1.00 | 35.92 |
| ATOM | 2384 | N | LEU | C | 191 | 93.014 | 45.860 | 120.705 | 1.00 | 34.12 |
| ATOM | 2385 | CA | LEU | C | 191 | 92.568 | 46.547 | 121.900 | 1.00 | 33.44 |
| ATOM | 2386 | CB | LEU | C | 191 | 91.985 | 47.911 | 121.546 | 1.00 | 33.52 |
| ATOM | 2387 | CG | LEU | C | 191 | 92.809 | 48.949 | 120.790 | 1.00 | 32.72 |
| ATOM | 2388 | CD1 | LEU | C | 191 | 91.974 | 50.219 | 120.686 | 1.00 | 30.58 |
| ATOM | 2389 | CD2 | LEU | C | 191 | 94.127 | 49.217 | 121.508 | 1.00 | 32.65 |
| ATOM | 2390 | C | LEU | C | 191 | 91.504 | 45.750 | 122.634 | 1.00 | 34.98 |
| ATOM | 2391 | O | LEU | C | 191 | 90.497 | 45.348 | 122.038 | 1.00 | 35.62 |
| ATOM | 2392 | N | LYS | C | 192 | 91.726 | 45.516 | 123.925 | 1.00 | 34.06 |
| ATOM | 2393 | CA | LYS | C | 192 | 90.749 | 44.804 | 124.737 | 1.00 | 32.83 |
| ATOM | 2394 | CB | LYS | C | 192 | 91.461 | 43.992 | 125.814 | 1.00 | 32.77 |
| ATOM | 2395 | CG | LYS | C | 192 | 90.590 | 43.068 | 126.641 | 1.00 | 30.53 |
| ATOM | 2396 | CD | LYS | C | 192 | 91.486 | 42.167 | 127.481 | 1.00 | 30.45 |
| ATOM | 2397 | CE | LYS | C | 192 | 90.737 | 41.003 | 128.119 | 1.00 | 29.54 |
| ATOM | 2398 | NZ | LYS | C | 192 | 89.698 | 41.499 | 129.062 | 1.00 | 29.96 |
| ATOM | 2399 | C | LYS | C | 192 | 89.900 | 45.906 | 125.357 | 1.00 | 33.41 |
| ATOM | 2400 | O | LYS | C | 192 | 90.403 | 46.752 | 126.100 | 1.00 | 33.66 |
| ATOM | 2401 | N | ASN | C | 193 | 88.620 | 45.909 | 125.011 | 1.00 | 34.21 |
| ATOM | 2402 | CA | ASN | C | 193 | 87.670 | 46.902 | 125.495 | 1.00 | 35.18 |
| ATOM | 2403 | CB | ASN | C | 193 | 87.418 | 46.694 | 126.982 | 1.00 | 36.87 |
| ATOM | 2404 | CG | ASN | C | 193 | 87.001 | 45.274 | 127.301 | 1.00 | 39.31 |
| ATOM | 2405 | OD1 | ASN | C | 193 | 86.035 | 44.750 | 126.742 | 1.00 | 41.66 |
| ATOM | 2406 | ND2 | ASN | C | 193 | 87.732 | 44.640 | 128.204 | 1.00 | 41.39 |
| ATOM | 2407 | C | ASN | C | 193 | 88.103 | 48.343 | 125.229 | 1.00 | 35.22 |
| ATOM | 2408 | O | ASN | C | 193 | 87.892 | 49.226 | 126.056 | 1.00 | 34.17 |
| ATOM | 2409 | N | GLY | C | 194 | 88.714 | 48.569 | 124.070 | 1.00 | 34.49 |
| ATOM | 2410 | CA | GLY | C | 194 | 89.139 | 49.910 | 123.719 | 1.00 | 36.02 |
| ATOM | 2411 | C | GLY | C | 194 | 90.462 | 50.383 | 124.290 | 1.00 | 35.90 |
| ATOM | 2412 | O | GLY | C | 194 | 90.927 | 51.468 | 123.948 | 1.00 | 36.63 |
| ATOM | 2413 | N | LYS | C | 195 | 91.083 | 49.582 | 125.145 | 1.00 | 34.82 |
| ATOM | 2414 | CA | LYS | C | 195 | 92.356 | 49.975 | 125.726 | 1.00 | 35.14 |
| ATOM | 2415 | CB | LYS | C | 195 | 92.303 | 49.785 | 127.246 | 1.00 | 33.76 |
| ATOM | 2416 | C | LYS | C | 195 | 93.526 | 49.184 | 125.136 | 1.00 | 35.43 |
| ATOM | 2417 | O | LYS | C | 195 | 93.327 | 48.132 | 124.530 | 1.00 | 35.33 |
| ATOM | 2418 | N | GLU | C | 196 | 94.741 | 49.705 | 125.292 | 1.00 | 36.75 |
| ATOM | 2419 | CA | GLU | C | 196 | 95.931 | 49.013 | 124.802 | 1.00 | 39.16 |
| ATOM | 2420 | CB | GLU | C | 196 | 97.214 | 49.728 | 125.252 | 1.00 | 38.19 |
| ATOM | 2421 | C | GLU | C | 196 | 95.883 | 47.609 | 125.405 | 1.00 | 40.34 |
| ATOM | 2422 | O | GLU | C | 196 | 95.549 | 47.435 | 126.575 | 1.00 | 40.73 |
| ATOM | 2423 | N | PHE | C | 197 | 96.223 | 46.612 | 124.603 | 1.00 | 41.32 |
| ATOM | 2424 | CA | PHE | C | 197 | 96.172 | 45.230 | 125.047 | 1.00 | 41.76 |
| ATOM | 2425 | CB | PHE | C | 197 | 95.207 | 44.461 | 124.137 | 1.00 | 39.22 |
| ATOM | 2426 | CG | PHE | C | 197 | 94.989 | 43.030 | 124.540 | 1.00 | 38.70 |
| ATOM | 2427 | CD1 | PHE | C | 197 | 94.817 | 42.047 | 123.575 | 1.00 | 37.21 |
| ATOM | 2428 | CD2 | PHE | C | 197 | 94.933 | 42.662 | 125.882 | 1.00 | 39.36 |
| ATOM | 2429 | CE1 | PHE | C | 197 | 94.593 | 40.723 | 123.930 | 1.00 | 36.13 |
| ATOM | 2430 | CE2 | PHE | C | 197 | 94.706 | 41.330 | 126.248 | 1.00 | 39.06 |
| ATOM | 2431 | CZ | PHE | C | 197 | 94.538 | 40.362 | 125.265 | 1.00 | 35.94 |
| ATOM | 2432 | C | PHE | C | 197 | 97.539 | 44.554 | 125.021 | 1.00 | 42.62 |
| ATOM | 2433 | O | PHE | C | 197 | 97.909 | 43.977 | 124.007 | 1.00 | 41.17 |
| ATOM | 2434 | N | LYS | C | 198 | 98.286 | 44.615 | 126.121 | 1.00 | 43.49 |
| ATOM | 2435 | CA | LYS | C | 198 | 99.600 | 43.971 | 126.152 | 1.00 | 44.01 |
| ATOM | 2436 | CB | LYS | C | 198 | 100.535 | 44.686 | 127.129 | 1.00 | 42.32 |
| ATOM | 2437 | C | LYS | C | 198 | 99.436 | 42.512 | 126.561 | 1.00 | 45.04 |
| ATOM | 2438 | O | LYS | C | 198 | 98.508 | 42.171 | 127.286 | 1.00 | 43.90 |
| ATOM | 2439 | N | PRO | C | 199 | 100.330 | 41.624 | 126.084 | 1.00 | 47.00 |
| ATOM | 2440 | CD | PRO | C | 199 | 101.396 | 41.853 | 125.097 | 1.00 | 47.32 |
| ATOM | 2441 | CA | PRO | C | 199 | 100.251 | 40.199 | 126.421 | 1.00 | 47.52 |
| ATOM | 2442 | CB | PRO | C | 199 | 101.345 | 39.568 | 125.555 | 1.00 | 46.71 |
| ATOM | 2443 | CG | PRO | C | 199 | 102.313 | 40.681 | 125.355 | 1.00 | 47.16 |
| ATOM | 2444 | C | PRO | C | 199 | 100.369 | 39.829 | 127.893 | 1.00 | 48.67 |
| ATOM | 2445 | O | PRO | C | 199 | 99.992 | 38.722 | 128.282 | 1.00 | 49.53 |
| ATOM | 2446 | N | ASP | C | 200 | 100.878 | 40.733 | 128.724 | 1.00 | 49.32 |
| ATOM | 2447 | CA | ASP | C | 200 | 100.991 | 40.428 | 130.143 | 1.00 | 49.39 |
| ATOM | 2448 | CB | ASP | C | 200 | 102.074 | 41.281 | 130.785 | 1.00 | 52.43 |
| ATOM | 2449 | CG | ASP | C | 200 | 103.436 | 41.042 | 130.149 | 1.00 | 55.59 |
| ATOM | 2450 | OD1 | ASP | C | 200 | 103.565 | 41.275 | 128.927 | 1.00 | 58.24 |
| ATOM | 2451 | OD2 | ASP | C | 200 | 104.370 | 40.607 | 130.866 | 1.00 | 56.58 |
| ATOM | 2452 | C | ASP | C | 200 | 99.651 | 40.664 | 130.808 | 1.00 | 48.50 |
| ATOM | 2453 | O | ASP | C | 200 | 99.503 | 40.490 | 132.022 | 1.00 | 49.38 |
| ATOM | 2454 | N | HIS | C | 201 | 98.668 | 41.046 | 130.003 | 1.00 | 46.95 |
| ATOM | 2455 | CA | HIS | C | 201 | 97.328 | 41.276 | 130.520 | 1.00 | 44.80 |

TABLE 1-continued

FGFR1 D2–D3 Complexed with FGF2

| ATOM | 2456 | CB | HIS | C | 201 | 96.488 | 42.086 | 129.558 | 1.00 | 45.08 |
|---|---|---|---|---|---|---|---|---|---|---|
| ATOM | 2457 | CG | HIS | C | 201 | 96.808 | 43.540 | 129.568 | 1.00 | 45.02 |
| ATOM | 2458 | CD2 | HIS | C | 201 | 96.109 | 44.598 | 130.026 | 1.00 | 44.68 |
| ATOM | 2459 | ND1 | HIS | C | 201 | 97.967 | 44.049 | 129.026 | 1.00 | 46.64 |
| ATOM | 2460 | CE1 | HIS | C | 201 | 97.972 | 45.361 | 129.144 | 1.00 | 45.48 |
| ATOM | 2461 | NE2 | HIS | C | 201 | 96.859 | 45.724 | 129.752 | 1.00 | 44.56 |
| ATOM | 2462 | C | HIS | C | 201 | 96.583 | 39.974 | 130.810 | 1.00 | 43.86 |
| ATOM | 2463 | O | HIS | C | 201 | 95.456 | 40.005 | 131.319 | 1.00 | 43.74 |
| ATOM | 2464 | N | ARG | C | 202 | 97.186 | 38.826 | 130.482 | 1.00 | 41.62 |
| ATOM | 2465 | CA | ARG | C | 202 | 96.542 | 37.554 | 130.763 | 1.00 | 40.68 |
| ATOM | 2466 | CB | ARG | C | 202 | 95.555 | 37.202 | 129.660 | 1.00 | 39.42 |
| ATOM | 2467 | CG | ARG | C | 202 | 96.157 | 36.684 | 128.370 | 1.00 | 37.72 |
| ATOM | 2468 | CD | ARG | C | 202 | 95.064 | 36.546 | 127.321 | 1.00 | 37.23 |
| ATOM | 2469 | NE | ARG | C | 202 | 94.048 | 35.571 | 127.694 | 1.00 | 34.77 |
| ATOM | 2470 | CZ | ARG | C | 202 | 94.172 | 34.262 | 127.510 | 1.00 | 37.24 |
| ATOM | 2471 | NH1 | ARG | C | 202 | 95.271 | 33.767 | 126.953 | 1.00 | 39.35 |
| ATOM | 2472 | NH2 | ARG | C | 202 | 93.197 | 33.444 | 127.882 | 1.00 | 34.91 |
| ATOM | 2473 | C | ARG | C | 202 | 97.589 | 36.476 | 130.874 | 1.00 | 42.16 |
| ATOM | 2474 | O | ARG | C | 202 | 98.590 | 36.509 | 130.160 | 1.00 | 43.04 |
| ATOM | 2475 | N | ILE | C | 203 | 97.359 | 35.524 | 131.772 | 1.00 | 42.53 |
| ATOM | 2476 | CA | ILE | C | 203 | 98.311 | 34.430 | 131.958 | 1.00 | 44.52 |
| ATOM | 2477 | CB | ILE | C | 203 | 97.821 | 33.391 | 133.016 | 1.00 | 45.70 |
| ATOM | 2478 | CG2 | ILE | C | 203 | 98.781 | 32.199 | 133.078 | 1.00 | 45.54 |
| ATOM | 2479 | CG1 | ILE | C | 203 | 97.776 | 34.034 | 134.403 | 1.00 | 48.01 |
| ATOM | 2480 | CD1 | ILE | C | 203 | 99.143 | 34.427 | 134.944 | 1.00 | 48.44 |
| ATOM | 2481 | C | ILE | C | 203 | 98.539 | 33.703 | 130.638 | 1.00 | 44.37 |
| ATOM | 2482 | O | ILE | C | 203 | 97.593 | 33.443 | 129.888 | 1.00 | 45.23 |
| ATOM | 2483 | N | GLY | C | 204 | 99.796 | 33.374 | 130.358 | 1.00 | 43.64 |
| ATOM | 2484 | CA | GLY | C | 204 | 100.115 | 32.691 | 129.118 | 1.00 | 42.70 |
| ATOM | 2485 | C | GLY | C | 204 | 100.151 | 33.673 | 127.964 | 1.00 | 41.41 |
| ATOM | 2486 | O | GLY | C | 204 | 100.620 | 33.346 | 126.881 | 1.00 | 40.04 |
| ATOM | 2487 | N | GLY | C | 205 | 99.643 | 34.880 | 128.208 | 1.00 | 41.20 |
| ATOM | 2488 | CA | GLY | C | 205 | 99.614 | 35.913 | 127.187 | 1.00 | 40.95 |
| ATOM | 2489 | C | GLY | C | 205 | 98.808 | 35.575 | 125.942 | 1.00 | 40.36 |
| ATOM | 2490 | O | GLY | C | 205 | 97.720 | 34.998 | 126.017 | 1.00 | 40.49 |
| ATOM | 2491 | N | TYR | C | 206 | 99.347 | 35.947 | 124.788 | 1.00 | 39.57 |
| ATOM | 2492 | CA | TYR | C | 206 | 98.691 | 35.683 | 123.515 | 1.00 | 38.69 |
| ATOM | 2493 | CB | TYR | C | 206 | 97.467 | 36.589 | 123.351 | 1.00 | 38.68 |
| ATOM | 2494 | CG | TYR | C | 206 | 97.801 | 38.060 | 123.281 | 1.00 | 38.74 |
| ATOM | 2495 | CD1 | TYR | C | 206 | 97.668 | 38.872 | 124.401 | 1.00 | 39.11 |
| ATOM | 2496 | CE1 | TYR | C | 206 | 97.957 | 40.217 | 124.339 | 1.00 | 39.50 |
| ATOM | 2497 | CD2 | TYR | C | 206 | 98.243 | 38.640 | 122.091 | 1.00 | 36.73 |
| ATOM | 2498 | CE2 | TYR | C | 206 | 98.538 | 39.973 | 122.022 | 1.00 | 37.36 |
| ATOM | 2499 | CZ | TYR | C | 206 | 98.393 | 40.761 | 123.148 | 1.00 | 40.01 |
| ATOM | 2500 | OH | TYR | C | 206 | 98.697 | 42.101 | 123.097 | 1.00 | 43.16 |
| ATOM | 2501 | C | TYR | C | 206 | 99.645 | 35.889 | 122.340 | 1.00 | 37.30 |
| ATOM | 2502 | O | TYR | C | 206 | 100.583 | 36.671 | 122.431 | 1.00 | 38.54 |
| ATOM | 2503 | N | LYS | C | 207 | 99.392 | 35.194 | 121.234 | 1.00 | 36.45 |
| ATOM | 2504 | CA | LYS | C | 207 | 100.237 | 35.300 | 120.046 | 1.00 | 36.87 |
| ATOM | 2505 | CB | LYS | C | 207 | 100.591 | 33.907 | 119.504 | 1.00 | 32.85 |
| ATOM | 2506 | C | LYS | C | 207 | 99.576 | 36.098 | 118.934 | 1.00 | 37.95 |
| ATOM | 2507 | O | LYS | C | 207 | 98.397 | 35.915 | 118.639 | 1.00 | 38.31 |
| ATOM | 2508 | N | VAL | C | 208 | 100.349 | 36.981 | 118.313 | 1.00 | 40.05 |
| ATOM | 2509 | CA | VAL | C | 208 | 99.850 | 37.796 | 117.207 | 1.00 | 41.07 |
| ATOM | 2510 | CD | VAL | C | 208 | 100.060 | 39.307 | 117.460 | 1.00 | 38.91 |
| ATOM | 2511 | CG1 | VAL | C | 208 | 99.653 | 40.100 | 116.237 | 1.00 | 38.42 |
| ATOM | 2512 | CG2 | VAL | C | 208 | 99.241 | 39.748 | 118.642 | 1.00 | 40.22 |
| ATOM | 2513 | C | VAL | C | 208 | 100.572 | 37.437 | 115.910 | 1.00 | 42.48 |
| ATOM | 2514 | O | VAL | C | 208 | 101.672 | 37.921 | 115.663 | 1.00 | 43.10 |
| ATOM | 2515 | N | ARG | C | 209 | 99.971 | 36.577 | 115.089 | 1.00 | 44.16 |
| ATOM | 2516 | CA | ARG | C | 209 | 100.587 | 36.204 | 113.811 | 1.00 | 45.44 |
| ATOM | 2517 | CB | ARG | C | 209 | 100.056 | 34.853 | 113.305 | 1.00 | 43.55 |
| ATOM | 2518 | C | ARG | C | 209 | 100.231 | 37.313 | 112.816 | 1.00 | 46.48 |
| ATOM | 2519 | O | ARG | C | 209 | 99.090 | 37.393 | 112.346 | 1.00 | 46.30 |
| ATOM | 2520 | N | TYR | C | 210 | 101.210 | 38.169 | 112.512 | 1.00 | 46.88 |
| ATOM | 2521 | CA | TYR | C | 210 | 101.003 | 39.299 | 111.605 | 1.00 | 46.66 |
| ATOM | 2522 | CB | TYR | C | 210 | 102.192 | 40.265 | 111.627 | 1.00 | 49.05 |
| ATOM | 2523 | CG | TYR | C | 210 | 102.532 | 40.780 | 113.008 | 1.00 | 54.11 |
| ATOM | 2524 | CD1 | TYR | C | 210 | 103.331 | 40.028 | 113.876 | 1.00 | 56.13 |
| ATOM | 2525 | CE1 | TYR | C | 210 | 103.602 | 40.468 | 115.170 | 1.00 | 57.60 |
| ATOM | 2526 | CD2 | TYR | C | 210 | 102.013 | 41.997 | 113.473 | 1.00 | 55.77 |
| ATOM | 2527 | CE2 | TYR | C | 210 | 102.275 | 42.447 | 114.765 | 1.00 | 57.07 |
| ATOM | 2528 | CZ | TYR | C | 210 | 103.069 | 41.676 | 115.608 | 1.00 | 58.31 |
| ATOM | 2529 | OH | TYR | C | 210 | 103.321 | 42.107 | 116.892 | 1.00 | 60.81 |
| ATOM | 2530 | C | TYR | C | 210 | 100.768 | 38.868 | 110.191 | 1.00 | 44.74 |
| ATOM | 2531 | O | TYR | C | 210 | 100.074 | 39.547 | 109.441 | 1.00 | 45.31 |
| ATOM | 2532 | N | ALA | C | 211 | 101.361 | 37.744 | 109.818 | 1.00 | 43.76 |

TABLE 1-continued

FGFR1 D2–D3 Complexed with FGF2

| | | | | | | | | | | |
|---|---|---|---|---|---|---|---|---|---|---|
| ATOM | 2533 | CA | ALA | C | 211 | 101.194 | 37.231 | 108.471 | 1.00 | 43.74 |
| ATOM | 2534 | CB | ALA | C | 211 | 102.120 | 36.057 | 108.252 | 1.00 | 43.87 |
| ATOM | 2535 | C | ALA | C | 211 | 99.740 | 36.812 | 108.266 | 1.00 | 43.16 |
| ATOM | 2536 | O | ALA | C | 211 | 99.255 | 36.747 | 107.144 | 1.00 | 42.29 |
| ATOM | 2537 | N | THR | C | 212 | 99.052 | 36.548 | 109.370 | 1.00 | 44.47 |
| ATOM | 2538 | CA | THR | C | 212 | 97.652 | 36.126 | 109.351 | 1.00 | 45.66 |
| ATOM | 2539 | CB | THR | C | 212 | 97.380 | 34.968 | 110.343 | 1.00 | 48.23 |
| ATOM | 2540 | OG1 | THR | C | 212 | 98.597 | 34.273 | 110.634 | 1.00 | 52.50 |
| ATOM | 2541 | CG2 | THR | C | 212 | 96.351 | 34.000 | 109.770 | 1.00 | 49.52 |
| ATOM | 2542 | C | THR | C | 212 | 96.712 | 37.246 | 109.780 | 1.00 | 44.59 |
| ATOM | 2543 | O | THR | C | 212 | 95.491 | 37.092 | 109.704 | 1.00 | 45.13 |
| ATOM | 2544 | N | TRP | C | 213 | 97.268 | 38.352 | 110.263 | 1.00 | 42.58 |
| ATOM | 2545 | CA | TRP | C | 213 | 96.436 | 39.456 | 110.703 | 1.00 | 40.90 |
| ATOM | 2546 | CB | TRP | C | 213 | 95.598 | 39.986 | 109.537 | 1.00 | 42.74 |
| ATOM | 2547 | CG | TRP | C | 213 | 96.411 | 40.547 | 108.437 | 1.00 | 42.12 |
| ATOM | 2548 | CD2 | TRP | C | 213 | 97.005 | 41.842 | 108.402 | 1.00 | 41.92 |
| ATOM | 2549 | CE2 | TRP | C | 213 | 97.714 | 41.942 | 107.187 | 1.00 | 42.84 |
| ATOM | 2550 | CE3 | TRP | C | 213 | 97.007 | 42.934 | 109.281 | 1.00 | 41.10 |
| ATOM | 2551 | CD1 | TRP | C | 213 | 96.767 | 39.924 | 107.281 | 1.00 | 42.59 |
| ATOM | 2552 | NE1 | TRP | C | 213 | 97.552 | 40.756 | 106.521 | 1.00 | 43.69 |
| ATOM | 2553 | CZ2 | TRP | C | 213 | 98.421 | 43.089 | 106.824 | 1.00 | 43.35 |
| ATOM | 2554 | CZ3 | TRP | C | 213 | 97.705 | 44.075 | 108.925 | 1.00 | 42.32 |
| ATOM | 2555 | CH2 | TRP | C | 213 | 98.405 | 44.145 | 107.704 | 1.00 | 43.55 |
| ATOM | 2556 | C | TRP | C | 213 | 95.508 | 38.954 | 111.788 | 1.00 | 39.39 |
| ATOM | 2557 | O | TRP | C | 213 | 94.321 | 39.294 | 111.817 | 1.00 | 38.02 |
| ATOM | 2558 | N | SER | C | 214 | 96.040 | 38.138 | 112.684 | 1.00 | 38.04 |
| ATOM | 2559 | CA | SER | C | 214 | 95.195 | 37.612 | 113.735 | 1.00 | 38.52 |
| ATOM | 2560 | CB | SER | C | 214 | 94.704 | 36.209 | 113.366 | 1.00 | 38.63 |
| ATOM | 2561 | OG | SER | C | 214 | 95.787 | 35.308 | 113.243 | 1.00 | 40.15 |
| ATOM | 2562 | C | SER | C | 214 | 95.831 | 37.588 | 115.109 | 1.00 | 37.44 |
| ATOM | 2563 | O | SER | C | 214 | 97.045 | 37.753 | 115.254 | 1.00 | 38.93 |
| ATOM | 2564 | N | ILE | C | 215 | 94.981 | 37.411 | 116.116 | 1.00 | 34.80 |
| ATOM | 2565 | CA | ILE | C | 215 | 95.423 | 37.335 | 117.497 | 1.00 | 32.54 |
| ATOM | 2566 | CB | ILE | C | 215 | 94.881 | 38.482 | 118.343 | 1.00 | 30.76 |
| ATOM | 2567 | CG2 | ILE | C | 215 | 93.351 | 38.494 | 118.285 | 1.00 | 27.37 |
| ATOM | 2568 | CG1 | ILE | C | 215 | 95.424 | 38.341 | 119.765 | 1.00 | 29.21 |
| ATOM | 2569 | CD1 | ILE | C | 215 | 95.232 | 39.566 | 120.634 | 1.00 | 31.69 |
| ATOM | 2570 | C | ILE | C | 215 | 94.872 | 36.034 | 118.044 | 1.00 | 32.55 |
| ATOM | 2571 | O | ILE | C | 215 | 93.739 | 35.654 | 117.753 | 1.00 | 32.98 |
| ATOM | 2572 | N | ILE | C | 216 | 95.670 | 35.347 | 118.843 | 1.00 | 30.59 |
| ATOM | 2573 | CA | ILE | C | 216 | 95.235 | 34.079 | 119.385 | 1.00 | 27.26 |
| ATOM | 2574 | CB | ILE | C | 216 | 96.011 | 32.945 | 118.732 | 1.00 | 27.82 |
| ATOM | 2575 | CG2 | ILE | C | 216 | 95.489 | 31.617 | 119.218 | 1.00 | 26.00 |
| ATOM | 2576 | CG1 | ILE | C | 216 | 95.889 | 33.072 | 117.210 | 1.00 | 30.26 |
| ATOM | 2577 | CD1 | ILE | C | 216 | 96.663 | 32.040 | 116.427 | 1.00 | 32.20 |
| ATOM | 2578 | C | ILE | C | 216 | 95.389 | 33.985 | 120.882 | 1.00 | 25.63 |
| ATOM | 2579 | O | ILE | C | 216 | 96.407 | 34.373 | 121.444 | 1.00 | 24.12 |
| ATOM | 2580 | N | MET | C | 217 | 94.357 | 33.482 | 121.533 | 1.00 | 25.01 |
| ATOM | 2581 | CA | MET | C | 217 | 94.405 | 33.312 | 122.968 | 1.00 | 26.49 |
| ATOM | 2582 | CB | MET | C | 217 | 93.450 | 34.270 | 123.668 | 1.00 | 25.10 |
| ATOM | 2583 | CG | MET | C | 217 | 93.780 | 35.714 | 123.453 | 1.00 | 26.08 |
| ATOM | 2584 | SD | MET | C | 217 | 92.719 | 36.763 | 124.435 | 1.00 | 28.69 |
| ATOM | 2585 | CE | MET | C | 217 | 91.386 | 36.979 | 123.321 | 1.00 | 29.90 |
| ATOM | 2586 | C | MET | C | 217 | 94.076 | 31.869 | 123.333 | 1.00 | 28.23 |
| ATOM | 2587 | O | MET | C | 217 | 93.113 | 31.271 | 122.843 | 1.00 | 28.32 |
| ATOM | 2588 | N | ASP | C | 218 | 94.910 | 31.300 | 124.190 | 1.00 | 29.55 |
| ATOM | 2589 | CA | ASP | C | 218 | 94.711 | 29.935 | 124.632 | 1.00 | 28.10 |
| ATOM | 2590 | CB | ASP | C | 218 | 96.044 | 29.248 | 124.890 | 1.00 | 26.11 |
| ATOM | 2591 | CG | ASP | C | 218 | 96.745 | 28.854 | 123.626 | 1.00 | 27.42 |
| ATOM | 2592 | OD1 | ASP | C | 218 | 96.054 | 28.374 | 122.698 | 1.00 | 25.60 |
| ATOM | 2593 | OD2 | ASP | C | 218 | 97.991 | 29.006 | 123.570 | 1.00 | 30.13 |
| ATOM | 2594 | C | ASP | C | 218 | 93.894 | 29.944 | 125.912 | 1.00 | 28.61 |
| ATOM | 2595 | O | ASP | C | 218 | 93.813 | 30.969 | 126.595 | 1.00 | 27.04 |
| ATOM | 2596 | N | SER | C | 219 | 93.297 | 28.793 | 126.224 | 1.00 | 29.67 |
| ATOM | 2597 | CA | SER | C | 219 | 92.480 | 28.607 | 127.425 | 1.00 | 29.41 |
| ATOM | 2598 | CB | SER | C | 219 | 93.314 | 27.972 | 128.534 | 1.00 | 29.13 |
| ATOM | 2599 | OG | SER | C | 219 | 92.485 | 27.653 | 129.642 | 1.00 | 30.01 |
| ATOM | 2600 | C | SER | C | 219 | 91.818 | 29.873 | 127.972 | 1.00 | 29.79 |
| ATOM | 2601 | O | SER | C | 219 | 92.176 | 30.372 | 129.041 | 1.00 | 27.97 |
| ATOM | 2602 | N | VAL | C | 220 | 90.829 | 30.374 | 127.239 | 1.00 | 31.22 |
| ATOM | 2603 | CA | VAL | C | 220 | 90.109 | 31.577 | 127.631 | 1.00 | 30.62 |
| ATOM | 2604 | CB | VAL | C | 220 | 89.239 | 32.075 | 126.481 | 1.00 | 27.62 |
| ATOM | 2605 | CG1 | VAL | C | 220 | 90.109 | 32.616 | 125.378 | 1.00 | 26.20 |
| ATOM | 2606 | CG2 | VAL | C | 220 | 88.413 | 30.946 | 125.956 | 1.00 | 29.75 |
| ATOM | 2607 | C | VAL | C | 220 | 89.235 | 31.393 | 128.870 | 1.00 | 31.94 |
| ATOM | 2608 | O | VAL | C | 220 | 88.472 | 30.434 | 128.994 | 1.00 | 32.79 |
| ATOM | 2609 | N | VAL | C | 221 | 89.353 | 32.334 | 129.791 | 1.00 | 32.13 |

TABLE 1-continued

FGFR1 D2–D3 Complexed with FGF2

| ATOM | 2610 | CA | VAL | C | 221 | 88.586 | 32.293 | 131.022 | 1.00 | 31.92 |
|---|---|---|---|---|---|---|---|---|---|---|
| ATOM | 2611 | CB | VAL | C | 221 | 89.533 | 32.287 | 132.267 | 1.00 | 31.72 |
| ATOM | 2612 | CG1 | VAL | C | 221 | 90.534 | 31.137 | 132.175 | 1.00 | 29.53 |
| ATOM | 2613 | CG2 | VAL | C | 221 | 90.269 | 33.608 | 132.365 | 1.00 | 31.11 |
| ATOM | 2614 | C | VAL | C | 221 | 87.682 | 33.537 | 131.046 | 1.00 | 32.11 |
| ATOM | 2615 | O | VAL | C | 221 | 87.858 | 34.446 | 130.229 | 1.00 | 31.15 |
| ATOM | 2616 | N | PRO | C | 222 | 86.707 | 33.597 | 131.982 | 1.00 | 31.23 |
| ATOM | 2617 | CD | PRO | C | 222 | 86.345 | 32.563 | 132.966 | 1.00 | 30.92 |
| ATOM | 2618 | CA | PRO | C | 222 | 85.784 | 34.731 | 132.105 | 1.00 | 30.47 |
| ATOM | 2619 | CB | PRO | C | 222 | 85.070 | 34.457 | 133.419 | 1.00 | 27.58 |
| ATOM | 2620 | CG | PRO | C | 222 | 84.953 | 33.014 | 133.399 | 1.00 | 29.80 |
| ATOM | 2621 | C | PRO | C | 222 | 86.424 | 36.114 | 132.096 | 1.00 | 31.43 |
| ATOM | 2622 | O | PRO | C | 222 | 85.848 | 37.055 | 131.548 | 1.00 | 30.86 |
| ATOM | 2623 | N | SER | C | 223 | 87.598 | 36.255 | 132.711 | 1.00 | 32.22 |
| ATOM | 2624 | CA | SER | C | 223 | 88.256 | 37.560 | 132.730 | 1.00 | 31.94 |
| ATOM | 2625 | CB | SER | C | 223 | 89.503 | 37.548 | 133.644 | 1.00 | 31.67 |
| ATOM | 2626 | OG | SER | C | 223 | 90.516 | 36.649 | 133.212 | 1.00 | 30.71 |
| ATOM | 2627 | C | SER | C | 223 | 88.619 | 38.009 | 131.305 | 1.00 | 32.23 |
| ATOM | 2628 | O | SER | C | 223 | 88.892 | 39.179 | 131.070 | 1.00 | 31.36 |
| ATOM | 2629 | N | ASP | C | 224 | 88.609 | 37.078 | 130.357 | 1.00 | 31.98 |
| ATOM | 2630 | CA | ASP | C | 224 | 88.912 | 37.412 | 128.978 | 1.00 | 32.72 |
| ATOM | 2631 | CB | ASP | C | 224 | 89.340 | 36.169 | 128.201 | 1.00 | 35.56 |
| ATOM | 2632 | CG | ASP | C | 224 | 90.740 | 35.736 | 128.537 | 1.00 | 37.51 |
| ATOM | 2633 | OD1 | ASP | C | 224 | 91.622 | 36.618 | 128.591 | 1.00 | 40.81 |
| ATOM | 2634 | OD2 | ASP | C | 224 | 90.964 | 34.525 | 128.736 | 1.00 | 37.64 |
| ATOM | 2635 | C | ASP | C | 224 | 87.691 | 38.002 | 128.312 | 1.00 | 32.18 |
| ATOM | 2636 | O | ASP | C | 224 | 87.799 | 38.675 | 127.298 | 1.00 | 32.48 |
| ATOM | 2637 | N | LYS | C | 225 | 86.521 | 37.725 | 128.872 | 1.00 | 31.98 |
| ATOM | 2638 | CA | LYS | C | 225 | 85.277 | 38.234 | 128.315 | 1.00 | 32.69 |
| ATOM | 2639 | CB | LYS | C | 225 | 84.128 | 38.037 | 129.314 | 1.00 | 33.13 |
| ATOM | 2640 | CG | LYS | C | 225 | 83.573 | 36.610 | 129.425 | 1.00 | 33.78 |
| ATOM | 2641 | CD | LYS | C | 225 | 82.107 | 36.644 | 129.872 | 1.00 | 33.61 |
| ATOM | 2642 | CE | LYS | C | 225 | 81.925 | 36.311 | 131.357 | 1.00 | 38.01 |
| ATOM | 2643 | NZ | LYS | C | 225 | 80.529 | 36.606 | 131.836 | 1.00 | 38.05 |
| ATOM | 2644 | C | LYS | C | 225 | 85.408 | 39.717 | 127.988 | 1.00 | 32.99 |
| ATOM | 2645 | O | LYS | C | 225 | 85.896 | 40.488 | 128.809 | 1.00 | 33.98 |
| ATOM | 26A6 | H | GLY | C | 226 | 84.979 | 40.124 | 126.798 | 1.00 | 32.15 |
| ATOM | 2647 | CA | GLY | C | 226 | 85.061 | 41.534 | 126.458 | 1.00 | 33.00 |
| ATOM | 2648 | C | GLY | C | 226 | 85.066 | 41.804 | 124.975 | 1.00 | 33.41 |
| ATOM | 2649 | O | GLY | C | 226 | 84.796 | 40.901 | 124.187 | 1.00 | 34.91 |
| ATOM | 2650 | N | ASN | C | 227 | 85.356 | 43.047 | 124.590 | 1.00 | 32.62 |
| ATOM | 2651 | CA | ASN | C | 227 | 85.419 | 43.406 | 123.176 | 1.00 | 31.01 |
| ATOM | 2652 | CB | ASN | C | 227 | 84.675 | 44.697 | 122.893 | 1.00 | 29.69 |
| ATOM | 2653 | CG | ASN | C | 227 | 83.219 | 44.595 | 123.210 | 1.00 | 28.50 |
| ATOM | 2654 | OD1 | ASN | C | 227 | 82.577 | 43.587 | 122.913 | 1.00 | 29.98 |
| ATOM | 2655 | HD2 | ASN | C | 227 | 82.675 | 45.642 | 123.808 | 1.00 | 25.67 |
| ATOM | 2656 | C | ASN | C | 227 | 86.855 | 43.576 | 122.730 | 1.00 | 31.54 |
| ATOM | 2657 | O | ASN | C | 227 | 87.668 | 44.181 | 123.411 | 1.00 | 33.57 |
| ATOM | 2658 | H | TYR | C | 228 | 87.173 | 43.027 | 121.576 | 1.00 | 31.42 |
| ATOM | 2659 | CA | TYR | C | 228 | 88.518 | 43.142 | 121.065 | 1.00 | 32.10 |
| ATOM | 2660 | CB | TYR | C | 228 | 89.162 | 41.765 | 120.962 | 1.00 | 31.62 |
| ATOM | 2661 | CG | TYR | C | 228 | 89.273 | 41.070 | 122.288 | 1.00 | 32.41 |
| ATOM | 2662 | CD1 | TYR | C | 228 | 88.138 | 40.585 | 122.954 | 1.00 | 32.91 |
| ATOM | 2663 | CE1 | TYR | C | 228 | 88.249 | 39.954 | 124.207 | 1.00 | 34.77 |
| ATOM | 2664 | CD2 | TYR | C | 228 | 90.516 | 40.912 | 122.899 | 1.00 | 34.65 |
| ATOM | 2665 | CE2 | TYR | C | 228 | 90.645 | 40.291 | 124.145 | 1.00 | 34.81 |
| ATOM | 2666 | CZ | TYR | C | 228 | 89.515 | 39.813 | 124.791 | 1.00 | 35.79 |
| ATOM | 2667 | OH | TYR | C | 228 | 89.674 | 39.179 | 126.001 | 1.00 | 36.37 |
| ATOM | 2668 | C | TYR | C | 228 | 88.426 | 43.807 | 119.707 | 1.00 | 32.91 |
| ATOM | 2669 | O | TYR | C | 228 | 87.634 | 43.397 | 118.852 | 1.00 | 31.39 |
| ATOM | 2670 | N | THR | C | 229 | 89.237 | 44.845 | 119.530 | 1.00 | 33.31 |
| ATOM | 2671 | CA | THR | C | 229 | 89.262 | 45.624 | 118.303 | 1.00 | 31.06 |
| ATOM | 2672 | CB | THR | C | 229 | 88.956 | 47.081 | 118.595 | 1.00 | 29.65 |
| ATOM | 2673 | OG1 | THR | C | 229 | 87.603 | 47.198 | 119.047 | 1.00 | 29.25 |
| ATOM | 2674 | CG2 | THR | C | 229 | 89.186 | 47.917 | 117.359 | 1.00 | 28.81 |
| ATOM | 2675 | C | THR | C | 229 | 90.608 | 45.585 | 117.622 | 1.00 | 29.85 |
| ATOM | 2676 | O | THR | C | 229 | 91.630 | 45.805 | 118.253 | 1.00 | 28.08 |
| ATOM | 2677 | H | CYS | C | 230 | 90.608 | 45.304 | 116.329 | 1.00 | 31.21 |
| ATOM | 2678 | CA | CYS | C | 230 | 91.852 | 45.282 | 115.586 | 1.00 | 31.56 |
| ATOM | 2679 | C | CYS | C | 230 | 91.929 | 46.617 | 114.874 | 1.00 | 31.07 |
| ATOM | 2680 | O | CYS | C | 230 | 90.911 | 47.161 | 114.443 | 1.00 | 30.73 |
| ATOM | 2681 | CB | CYS | C | 230 | 91.872 | 44.139 | 114.569 | 1.00 | 31.93 |
| ATOM | 2682 | SG | CYS | C | 230 | 90.535 | 44.169 | 113.337 | 1.00 | 29.76 |
| ATOM | 2683 | N | ILE | C | 231 | 93.135 | 47.156 | 114.784 | 1.00 | 31.08 |
| ATOM | 2684 | CA | ILE | C | 231 | 93.350 | 48.429 | 114.116 | 1.00 | 31.36 |
| ATOM | 2685 | CB | ILE | C | 231 | 93.746 | 49.525 | 115.108 | 1.00 | 29.07 |
| ATOM | 2686 | CG2 | ILE | C | 231 | 94.013 | 50.819 | 114.386 | 1.00 | 26.48 |

TABLE 1-continued

FGFR1 D2–D3 Complexed with FGF2

| ATOM | 2687 | CG1 | ILE | C | 231 | 92.615 | 49.733 | 116.096 | 1.00 | 29.41 |
|------|------|-----|-----|---|-----|--------|--------|---------|------|-------|
| ATOM | 2688 | CD1 | ILE | C | 231 | 92.982 | 50.640 | 117.222 | 1.00 | 32.64 |
| ATOM | 2689 | C | ILE | C | 231 | 94.459 | 48.265 | 113.097 | 1.00 | 33.74 |
| ATOM | 2690 | O | ILE | C | 231 | 95.646 | 48.143 | 113.450 | 1.00 | 34.89 |
| ATOM | 2691 | H | VAL | C | 232 | 94.055 | 48.227 | 111.831 | 1.00 | 34.68 |
| ATOM | 2692 | CA | VAL | C | 232 | 94.992 | 48.101 | 110.726 | 1.00 | 35.66 |
| ATOM | 2693 | CB | VAL | C | 232 | 94.437 | 47.244 | 109.614 | 1.00 | 34.43 |
| ATOM | 2694 | CG1 | VAL | C | 232 | 95.526 | 46.993 | 108.601 | 1.00 | 35.90 |
| ATOM | 2695 | CG2 | VAL | C | 232 | 93.887 | 45.966 | 110.174 | 1.00 | 31.80 |
| ATOM | 2696 | C | VAL | C | 232 | 95.174 | 49.498 | 110.184 | 1.00 | 37.27 |
| ATOM | 2697 | O | VAL | C | 232 | 94.204 | 50.168 | 109.831 | 1.00 | 37.78 |
| ATOM | 2698 | N | GLU | C | 233 | 96.413 | 49.945 | 110.094 | 1.00 | 39.96 |
| ATOM | 2699 | CA | GLU | C | 233 | 96.627 | 51.299 | 109.626 | 1.00 | 41.82 |
| ATOM | 2700 | CB | GLU | C | 233 | 96.523 | 52.239 | 110.825 | 1.00 | 42.88 |
| ATOM | 2701 | CG | GLU | C | 233 | 96.386 | 53.679 | 110.443 | 1.00 | 48.56 |
| ATOM | 2702 | CD | GLU | C | 233 | 96.259 | 54.578 | 111.642 | 1.00 | 51.10 |
| ATOM | 2703 | OE1 | GLU | C | 233 | 96.017 | 54.054 | 112.756 | 1.00 | 52.31 |
| ATOM | 2704 | OE2 | GLU | C | 233 | 96.393 | 55.810 | 111.457 | 1.00 | 53.25 |
| ATOM | 2705 | C | GLU | C | 233 | 97.930 | 51.572 | 108.876 | 1.00 | 40.67 |
| ATOM | 2706 | O | GLU | C | 233 | 98.935 | 50.889 | 109.076 | 1.00 | 40.71 |
| ATOM | 2707 | N | ASN | C | 234 | 97.879 | 52.567 | 107.994 | 1.00 | 39.72 |
| ATOM | 2708 | CA | ASN | C | 234 | 99.038 | 53.019 | 107.234 | 1.00 | 39.29 |
| ATOM | 2709 | CB | ASN | C | 234 | 99.203 | 52.272 | 105.884 | 1.00 | 36.35 |
| ATOM | 2710 | CG | ASN | C | 234 | 98.347 | 52.840 | 104.748 | 1.00 | 35.20 |
| ATOM | 2711 | OD1 | ASN | C | 234 | 97.750 | 53.905 | 104.859 | 1.00 | 33.07 |
| ATOM | 2712 | ND2 | ASN | C | 234 | 98.308 | 52.115 | 103.631 | 1.00 | 32.78 |
| ATOM | 2713 | C | ASN | C | 234 | 98.869 | 54.523 | 107.039 | 1.00 | 40.78 |
| ATOM | 2714 | O | ASN | C | 234 | 97.893 | 55.102 | 107.524 | 1.00 | 40.10 |
| ATOM | 2715 | N | GLU | C | 235 | 99.811 | 55.157 | 106.346 | 1.00 | 42.64 |
| ATOM | 2716 | CA | GLU | C | 235 | 99.763 | 56.606 | 106.133 | 1.00 | 42.97 |
| ATOM | 2717 | CB | GLU | C | 235 | 100.978 | 57.068 | 105.324 | 1.00 | 43.47 |
| ATOM | 2718 | C | GLU | C | 235 | 98.504 | 57.169 | 105.475 | 1.00 | 43.42 |
| ATOM | 2719 | O | GLU | C | 235 | 98.195 | 58.340 | 105.654 | 1.00 | 43.34 |
| ATOM | 2720 | N | TYR | C | 236 | 97.765 | 56.358 | 104.726 | 1.00 | 43.63 |
| ATOM | 2721 | CA | TYR | C | 236 | 96.581 | 56.882 | 104.050 | 1.00 | 43.35 |
| ATOM | 2722 | CB | TYR | C | 236 | 96.621 | 56.480 | 102.576 | 1.00 | 46.25 |
| ATOM | 2723 | CG | TYR | C | 236 | 97.982 | 56.709 | 101.961 | 1.00 | 49.41 |
| ATOM | 2724 | CD1 | TYR | C | 236 | 98.907 | 55.671 | 101.869 | 1.00 | 52.22 |
| ATOM | 2725 | CE1 | TYR | C | 236 | 100.179 | 55.882 | 101.350 | 1.00 | 54.00 |
| ATOM | 2726 | CD2 | TYR | C | 236 | 98.367 | 57.975 | 101.515 | 1.00 | 51.14 |
| ATOM | 2727 | CE2 | TYR | C | 236 | 99.643 | 58.202 | 100.994 | 1.00 | 52.30 |
| ATOM | 2728 | CZ | TYR | C | 236 | 100.543 | 57.152 | 100.917 | 1.00 | 54.30 |
| ATOM | 2729 | OH | TYR | C | 236 | 101.814 | 57.362 | 100.425 | 1.00 | 54.97 |
| ATOM | 2730 | C | TYR | C | 236 | 95.221 | 56.534 | 104.650 | 1.00 | 40.94 |
| ATOM | 2731 | O | TYR | C | 236 | 94.185 | 56.933 | 104.119 | 1.00 | 38.63 |
| ATOM | 2732 | N | GLY | C | 237 | 95.223 | 55.805 | 105.759 | 1.00 | 39.11 |
| ATOM | 2733 | CA | GLY | C | 237 | 93.969 | 55.451 | 106.390 | 1.00 | 37.11 |
| ATOM | 2734 | C | GLY | C | 237 | 94.078 | 54.300 | 107.367 | 1.00 | 36.57 |
| ATOM | 2735 | O | GLY | C | 237 | 95.119 | 53.650 | 107.478 | 1.00 | 36.30 |
| ATOM | 2736 | N | SER | C | 238 | 92.991 | 54.060 | 108.093 | 1.00 | 34.87 |
| ATOM | 2737 | CA | SER | C | 238 | 92.943 | 52.974 | 109.054 | 1.00 | 33.24 |
| ATOM | 2738 | CB | SER | C | 238 | 93.251 | 53.476 | 110.455 | 1.00 | 33.21 |
| ATOM | 2739 | OG | SER | C | 238 | 92.087 | 54.057 | 111.007 | 1.00 | 35.23 |
| ATOM | 2740 | C | SER | C | 238 | 91.552 | 52.375 | 109.074 | 1.00 | 31.13 |
| ATOM | 2741 | O | SER | C | 238 | 90.561 | 53.055 | 108.830 | 1.00 | 28.33 |
| ATOM | 2742 | N | ILE | C | 239 | 91.490 | 51.091 | 109.376 | 1.00 | 30.79 |
| ATOM | 2743 | CA | ILE | C | 239 | 90.224 | 50.401 | 109.467 | 1.00 | 30.00 |
| ATOM | 2744 | CB | ILE | C | 239 | 89.998 | 49.504 | 108.250 | 1.00 | 26.28 |
| ATOM | 2745 | CG2 | ILE | C | 239 | 89.705 | 50.375 | 107.026 | 1.00 | 25.43 |
| ATOM | 2746 | CG1 | ILE | C | 239 | 91.213 | 48.613 | 108.015 | 1.00 | 18.70 |
| ATOM | 2747 | CD1 | ILE | C | 239 | 90.999 | 47.657 | 106.886 | 1.00 | 13.24 |
| ATOM | 2748 | C | ILE | C | 239 | 90.284 | 49.581 | 110.735 | 1.00 | 31.43 |
| ATOM | 2749 | O | ILE | C | 239 | 91.370 | 49.232 | 111.196 | 1.00 | 33.06 |
| ATOM | 2750 | N | ASN | C | 240 | 89.122 | 49.296 | 111.309 | 1.00 | 31.88 |
| ATOM | 2751 | CA | ASN | C | 240 | 89.041 | 48.532 | 112.542 | 1.00 | 31.51 |
| ATOM | 2752 | CB | ASN | C | 240 | 88.890 | 49.482 | 113.707 | 1.00 | 31.92 |
| ATOM | 2753 | CG | ASN | C | 240 | 87.635 | 50.313 | 113.602 | 1.00 | 33.22 |
| ATOM | 2754 | OD1 | ASN | C | 240 | 87.546 | 51.386 | 114.171 | 1.00 | 36.26 |
| ATOM | 2755 | ND2 | ASN | C | 240 | 86.650 | 49.812 | 112.879 | 1.00 | 35.73 |
| ATOM | 2756 | C | ASN | C | 240 | 87.845 | 47.603 | 112.516 | 1.00 | 32.00 |
| ATOM | 2757 | O | ASN | C | 240 | 86.911 | 47.795 | 111.743 | 1.00 | 31.13 |
| ATOM | 2758 | N | HIS | C | 241 | 87.879 | 46.594 | 113.372 | 1.00 | 33.09 |
| ATOM | 2759 | CA | HIS | C | 241 | 86.787 | 45.644 | 113.468 | 1.00 | 32.20 |
| ATOM | 2760 | CB | HIS | C | 241 | 86.966 | 44.490 | 112.495 | 1.00 | 30.92 |
| ATOM | 2761 | CG | HIS | C | 241 | 85.779 | 43.585 | 112.436 | 1.00 | 31.46 |
| ATOM | 2762 | CD2 | HIS | C | 241 | 85.618 | 42.298 | 112.820 | 1.00 | 31.42 |
| ATOM | 2763 | ND1 | HIS | C | 241 | 84.557 | 43.998 | 111.949 | 1.00 | 28.62 |

TABLE 1-continued

FGFR1 D2–D3 Complexed with FGF2

| | | | | | | | | | |
|---|---|---|---|---|---|---|---|---|---|
| ATOM | 2764 | CE1 | HIS | C | 241 | 83.697 | 43.000 | 112.033 | 1.00 | 31.53 |
| ATOM | 2765 | NE2 | HIS | C | 241 | 84.314 | 41.957 | 112.559 | 1.00 | 31.80 |
| ATOM | 2766 | C | HIS | C | 241 | 86.795 | 45.107 | 114.874 | 1.00 | 31.49 |
| ATOM | 2767 | O | HIS | C | 241 | 87.848 | 44.785 | 115.406 | 1.00 | 32.43 |
| ATOM | 2768 | N | THR | C | 242 | 85.622 | 45.014 | 115.479 | 1.00 | 31.45 |
| ATOM | 2769 | CA | THR | C | 242 | 85.524 | 44.527 | 116.846 | 1.00 | 30.81 |
| ATOM | 2770 | CB | THR | C | 242 | 84.785 | 45.552 | 117.735 | 1.00 | 28.87 |
| ATOM | 2771 | OG1 | THR | C | 242 | 85.412 | 46.832 | 117.606 | 1.00 | 27.00 |
| ATOM | 2772 | CG2 | THR | C | 242 | 84.819 | 45.127 | 119.192 | 1.00 | 27.19 |
| ATOM | 2773 | C | THR | C | 242 | 84.806 | 43.180 | 116.943 | 1.00 | 31.09 |
| ATOM | 2774 | O | THR | C | 242 | 83.851 | 42.911 | 116.214 | 1.00 | 32.42 |
| ATOM | 2775 | N | TYR | C | 243 | 85.289 | 42.326 | 117.833 | 1.00 | 30.68 |
| ATOM | 2776 | CA | TYR | C | 243 | 84.679 | 41.025 | 118.049 | 1.00 | 30.08 |
| ATOM | 2777 | CB | TYR | C | 243 | 85.686 | 39.910 | 117.798 | 1.00 | 27.63 |
| ATOM | 2778 | CG | TYR | C | 243 | 86.089 | 39.769 | 116.356 | 1.00 | 26.41 |
| ATOM | 2779 | CD1 | TYR | C | 243 | 87.388 | 40.043 | 115.951 | 1.00 | 26.64 |
| ATOM | 2780 | CE1 | TYR | C | 243 | 87.776 | 39.888 | 114.621 | 1.00 | 25.57 |
| ATOM | 2781 | CD2 | TYR | C | 243 | 85.176 | 39.337 | 115.392 | 1.00 | 25.87 |
| ATOM | 2782 | CE2 | TYR | C | 243 | 85.553 | 39.179 | 114.064 | 1.00 | 23.60 |
| ATOM | 2783 | CZ | TYR | C | 243 | 86.856 | 39.458 | 113.687 | 1.00 | 24.34 |
| ATOM | 2784 | OH | TYR | C | 243 | 87.247 | 39.325 | 112.372 | 1.00 | 26.49 |
| ATOM | 2785 | C | TYR | C | 243 | 84.232 | 40.988 | 119.497 | 1.00 | 31.15 |
| ATOM | 2786 | O | TYR | C | 243 | 84.794 | 41.674 | 120.350 | 1.00 | 33.46 |
| ATOM | 2787 | N | GLN | C | 244 | 83.210 | 40.208 | 119.786 | 1.00 | 30.47 |
| ATOM | 2788 | CA | GLN | C | 244 | 82.761 | 40.129 | 121.150 | 1.00 | 31.36 |
| ATOM | 2789 | CB | GLN | C | 244 | 81.272 | 40.406 | 121.229 | 1.00 | 35.16 |
| ATOM | 2790 | CG | GLN | C | 244 | 80.774 | 40.695 | 122.627 | 1.00 | 42.83 |
| ATOM | 2791 | CD | GLN | C | 244 | 79.267 | 40.912 | 122.649 | 1.00 | 49.87 |
| ATOM | 2792 | OE1 | GLN | C | 244 | 78.681 | 41.359 | 121.649 | 1.00 | 51.89 |
| ATOM | 2793 | NE2 | GLN | C | 244 | 78.630 | 40.611 | 123.786 | 1.00 | 50.55 |
| ATOM | 2794 | C | GLN | C | 244 | 83.049 | 38.728 | 121.622 | 1.00 | 30.33 |
| ATOM | 2795 | O | GLN | C | 244 | 82.662 | 37.760 | 120.966 | 1.00 | 29.04 |
| ATOM | 2796 | N | LEU | C | 245 | 83.760 | 38.617 | 122.740 | 1.00 | 28.79 |
| ATOM | 2797 | CA | LEU | C | 245 | 84.066 | 37.312 | 123.296 | 1.00 | 28.04 |
| ATOM | 2798 | CB | LEU | C | 245 | 85.542 | 37.191 | 123.673 | 1.00 | 26.24 |
| ATOM | 2799 | CG | LEU | C | 245 | 85.901 | 35.821 | 124.266 | 1.00 | 25.15 |
| ATOM | 2800 | CD1 | LEU | C | 245 | 85.824 | 34.789 | 123.168 | 1.00 | 24.09 |
| ATOM | 2801 | CD2 | LEU | C | 245 | 87.290 | 35.826 | 124.892 | 1.00 | 25.19 |
| ATOM | 2802 | C | LEU | C | 245 | 83.220 | 37.063 | 124.531 | 1.00 | 28.41 |
| ATOM | 2803 | O | LEU | C | 245 | 83.077 | 37.919 | 125.405 | 1.00 | 27.19 |
| ATOM | 2804 | N | ASP | C | 246 | 82.634 | 35.882 | 124.581 | 1.00 | 30.12 |
| ATOM | 2805 | CA | ASP | C | 246 | 81.841 | 35.511 | 125.725 | 1.00 | 32.19 |
| ATOM | 2806 | CB | ASP | C | 246 | 80.360 | 35.611 | 125.400 | 1.00 | 32.80 |
| ATOM | 2807 | CG | ASP | C | 246 | 79.522 | 35.787 | 126.639 | 1.00 | 35.79 |
| ATOM | 2808 | OD1 | ASP | C | 246 | 78.374 | 36.272 | 126.521 | 1.00 | 37.26 |
| ATOM | 2809 | OD2 | ASP | C | 246 | 80.024 | 35.437 | 127.733 | 1.00 | 34.78 |
| ATOM | 2810 | C | ASP | C | 246 | 82.235 | 34.087 | 126.091 | 1.00 | 33.34 |
| ATOM | 2811 | O | ASP | C | 246 | 82.141 | 33.174 | 125.259 | 1.00 | 32.58 |
| ATOM | 2812 | N | VAL | C | 247 | 82.721 | 33.910 | 127.321 | 1.00 | 33.68 |
| ATOM | 2813 | CA | VAL | C | 247 | 83.135 | 32.590 | 127.788 | 1.00 | 32.59 |
| ATOM | 2814 | CB | VAL | C | 247 | 84.548 | 32.619 | 128.391 | 1.00 | 32.83 |
| ATOM | 2815 | CG1 | VAL | C | 247 | 84.938 | 31.224 | 128.835 | 1.00 | 32.26 |
| ATOM | 2816 | CG2 | VAL | C | 247 | 85.545 | 33.148 | 127.367 | 1.00 | 31.39 |
| ATOM | 2817 | C | VAL | C | 247 | 82.163 | 32.034 | 128.817 | 1.00 | 32.34 |
| ATOM | 2818 | O | VAL | C | 247 | 81.802 | 32.716 | 129.780 | 1.00 | 31.84 |
| ATOM | 2819 | N | VAL | C | 248 | 81.733 | 30.795 | 128.597 | 1.00 | 32.98 |
| ATOM | 2820 | CA | VAL | C | 248 | 80.793 | 30.136 | 129.498 | 1.00 | 33.49 |
| ATOM | 2821 | CB | VAL | C | 248 | 79.570 | 29.572 | 128.717 | 1.00 | 33.49 |
| ATOM | 2822 | CG1 | VAL | C | 248 | 78.692 | 28.737 | 129.622 | 1.00 | 33.78 |
| ATOM | 2823 | CG2 | VAL | C | 248 | 78.752 | 30.704 | 128.162 | 1.00 | 36.10 |
| ATOM | 2824 | C | VAL | C | 248 | 81.458 | 28.998 | 130.262 | 1.00 | 33.28 |
| ATOM | 2825 | O | VAL | C | 248 | 82.100 | 28.134 | 129.666 | 1.00 | 33.59 |
| ATOM | 2826 | N | GLU | C | 249 | 81.324 | 29.013 | 131.584 | 1.00 | 33.31 |
| ATOM | 2827 | CA | GLU | C | 249 | 81.876 | 27.943 | 132.412 | 1.00 | 34.53 |
| ATOM | 2828 | CB | GLU | C | 249 | 82.331 | 28.482 | 133.770 | 1.00 | 34.33 |
| ATOM | 2829 | CG | GLU | C | 249 | 83.429 | 29.528 | 133.694 | 1.00 | 37.57 |
| ATOM | 2830 | CD | GLU | C | 249 | 83.898 | 30.034 | 135.071 | 1.00 | 38.93 |
| ATOM | 2831 | OE1 | GLU | C | 249 | 83.103 | 30.664 | 135.805 | 1.00 | 38.35 |
| ATOM | 2832 | OE2 | GLU | C | 249 | 85.077 | 29.807 | 135.417 | 1.00 | 40.90 |
| ATOM | 2833 | C | GLU | C | 249 | 80.740 | 26.947 | 132.609 | 1.00 | 34.31 |
| ATOM | 2834 | O | GLU | C | 249 | 79.685 | 27.308 | 133.124 | 1.00 | 37.50 |
| ATOM | 2835 | N | ARG | C | 250 | 80.952 | 25.708 | 132.187 | 1.00 | 33.96 |
| ATOM | 2836 | CA | ARG | C | 250 | 79.945 | 24.657 | 132.297 | 1.00 | 35.77 |
| ATOM | 2837 | CB | ARG | C | 250 | 80.162 | 23.628 | 131.165 | 1.00 | 34.20 |
| ATOM | 2838 | CG | ARG | C | 250 | 80.369 | 24.218 | 129.755 | 1.00 | 30.74 |
| ATOM | 2839 | CD | ARG | C | 250 | 79.167 | 25.049 | 129.300 | 1.00 | 28.69 |
| ATOM | 2840 | NE | ARG | C | 250 | 77.936 | 24.261 | 129.347 | 1.00 | 29.35 |

TABLE 1-continued

FGFR1 D2–D3 Complexed with FGF2

| ATOM | 2841 | CZ | ARG | C | 250 | 77.572 | 23.362 | 128.433 | 1.00 | 29.10 |
|------|------|-----|-----|---|-----|--------|--------|---------|------|-------|
| ATOM | 2842 | NH1 | ARG | C | 250 | 78.331 | 23.134 | 127.366 | 1.00 | 28.71 |
| ATOM | 2843 | NH2 | ARG | C | 250 | 76.470 | 22.648 | 128.615 | 1.00 | 26.65 |
| ATOM | 2844 | C | ARG | C | 250 | 80.054 | 23.962 | 133.658 | 1.00 | 36.77 |
| ATOM | 2845 | O | ARG | C | 250 | 80.513 | 24.537 | 134.629 | 1.00 | 38.20 |
| ATOM | 2846 | N | SER | C | 251 | 79.778 | 22.667 | 133.676 | 1.00 | 37.38 |
| ATOM | 2847 | CA | SER | C | 251 | 79.798 | 21.906 | 134.923 | 1.00 | 37.80 |
| ATOM | 2848 | CB | SER | C | 251 | 78.832 | 22.507 | 135.964 | 1.00 | 37.79 |
| ATOM | 2849 | OG | SER | C | 251 | 79.340 | 23.672 | 136.592 | 1.00 | 37.54 |
| ATOM | 2850 | C | SER | C | 251 | 79.318 | 20.502 | 134.627 | 1.00 | 37.89 |
| ATOM | 2851 | O | SER | C | 251 | 78.154 | 20.183 | 134.867 | 1.00 | 38.84 |
| ATOM | 2852 | N | PRO | C | 252 | 80.198 | 19.648 | 134.096 | 1.00 | 37.82 |
| ATOM | 2853 | CD | PRO | C | 252 | 81.504 | 19.973 | 133.497 | 1.00 | 38.36 |
| ATOM | 2854 | CA | PRO | C | 252 | 79.799 | 18.277 | 133.785 | 1.00 | 37.98 |
| ATOM | 2855 | CB | PRO | C | 252 | 80.842 | 17.841 | 132.759 | 1.00 | 38.53 |
| ATOM | 2856 | CG | PRO | C | 252 | 82.055 | 18.608 | 133.169 | 1.00 | 38.58 |
| ATOM | 2857 | C | PRO | C | 252 | 79.719 | 17.357 | 134.998 | 1.00 | 38.19 |
| ATOM | 2858 | O | PRO | C | 252 | 80.529 | 16.450 | 135.177 | 1.00 | 37.38 |
| ATOM | 2859 | N | HIS | C | 253 | 78.726 | 17.613 | 135.838 | 1.00 | 39.36 |
| ATOM | 2860 | CA | HIS | C | 253 | 78.491 | 16.799 | 137.023 | 1.00 | 40.22 |
| ATOM | 2861 | CB | HIS | C | 253 | 79.254 | 17.347 | 138.247 | 1.00 | 41.83 |
| ATOM | 2862 | CG | HIS | C | 253 | 78.984 | 18.791 | 138.548 | 1.00 | 44.50 |
| ATOM | 2863 | CD2 | HIS | C | 253 | 79.828 | 19.820 | 138.801 | 1.00 | 45.38 |
| ATOM | 2864 | ND1 | HIS | C | 253 | 77.709 | 19.313 | 138.636 | 1.00 | 45.96 |
| ATOM | 2865 | CE1 | HIS | C | 253 | 77.783 | 20.602 | 138.926 | 1.00 | 46.89 |
| ATOM | 2866 | NE2 | HIS | C | 253 | 79.056 | 20.935 | 139.032 | 1.00 | 45.49 |
| ATOM | 2867 | C | HIS | C | 253 | 76.993 | 16.749 | 137.306 | 1.00 | 38.23 |
| ATOM | 2868 | O | HIS | C | 253 | 76.241 | 17.606 | 136.836 | 1.00 | 37.80 |
| ATOM | 2869 | N | ARG | C | 254 | 76.572 | 15.733 | 138.059 | 1.00 | 36.30 |
| ATOM | 2870 | CA | ARG | C | 254 | 75.168 | 15.556 | 138.421 | 1.00 | 34.25 |
| ATOM | 2871 | CB | ARG | C | 254 | 74.997 | 14.301 | 139.288 | 1.00 | 37.38 |
| ATOM | 2872 | CG | ARG | C | 254 | 75.649 | 14.336 | 140.668 | 1.00 | 39.79 |
| ATOM | 2873 | CD | ARG | C | 254 | 75.434 | 12.983 | 141.340 | 1.00 | 44.46 |
| ATOM | 2874 | NE | ARG | C | 254 | 75.468 | 13.019 | 142.806 | 1.00 | 50.17 |
| ATOM | 2875 | CZ | ARG | C | 254 | 76.573 | 13.142 | 143.541 | 1.00 | 53.52 |
| ATOM | 2876 | NH1 | ARG | C | 254 | 77.768 | 13.245 | 142.953 | 1.00 | 54.83 |
| ATOM | 2877 | NH2 | ARG | C | 254 | 76.483 | 13.154 | 144.871 | 1.00 | 52.76 |
| ATOM | 2878 | C | ARG | C | 254 | 74.654 | 16.786 | 139.158 | 1.00 | 30.25 |
| ATOM | 2879 | O | ARG | C | 254 | 75.437 | 17.596 | 139.622 | 1.00 | 28.91 |
| ATOM | 2880 | N | PRO | C | 255 | 73.323 | 16.940 | 139.276 | 1.00 | 29.24 |
| ATOM | 2881 | CD | PRO | C | 255 | 72.241 | 16.051 | 138.809 | 1.00 | 28.68 |
| ATOM | 2882 | CA | PRO | C | 255 | 72.769 | 18.117 | 139.970 | 1.00 | 28.11 |
| ATOM | 2883 | CB | PRO | C | 255 | 71.252 | 17.913 | 139.873 | 1.00 | 27.02 |
| ATOM | 2884 | CG | PRO | C | 255 | 71.093 | 17.022 | 138.647 | 1.00 | 27.40 |
| ATOM | 2885 | C | PRO | C | 255 | 73.237 | 18.283 | 141.416 | 1.00 | 27.39 |
| ATOM | 2886 | O | PRO | C | 255 | 73.644 | 17.323 | 142.068 | 1.00 | 27.72 |
| ATOM | 2887 | N | ILE | C | 256 | 73.187 | 19.515 | 141.902 | 1.00 | 27.12 |
| ATOM | 2888 | CA | ILE | C | 256 | 73.600 | 19.844 | 143.262 | 1.00 | 28.10 |
| ATOM | 2889 | CB | ILE | C | 256 | 74.789 | 20.863 | 143.273 | 1.00 | 28.02 |
| ATOM | 2890 | CG2 | ILE | C | 256 | 75.094 | 21.336 | 144.685 | 1.00 | 27.93 |
| ATOM | 2891 | CG1 | ILE | C | 256 | 76.019 | 20.237 | 142.642 | 1.00 | 27.41 |
| ATOM | 2892 | CD1 | ILE | C | 256 | 75.860 | 20.080 | 141.138 | 1.00 | 30.37 |
| ATOM | 2893 | C | ILE | C | 256 | 72.422 | 20.506 | 143.977 | 1.00 | 29.88 |
| ATOM | 2894 | O | ILE | C | 256 | 71.857 | 21.484 | 143.472 | 1.00 | 31.33 |
| ATOM | 2895 | N | LEU | C | 257 | 72.046 | 19.979 | 145.141 | 1.00 | 28.88 |
| ATOM | 2896 | CA | LEU | C | 257 | 70.948 | 20.565 | 145.906 | 1.00 | 28.81 |
| ATOM | 2897 | CB | LEU | C | 257 | 70.072 | 19.490 | 146.560 | 1.00 | 28.93 |
| ATOM | 2898 | CG | LEU | C | 257 | 69.503 | 18.267 | 145.841 | 1.00 | 29.79 |
| ATOM | 2899 | CD1 | LEU | C | 257 | 68.145 | 17.994 | 146.496 | 1.00 | 28.42 |
| ATOM | 2900 | CD2 | LEU | C | 257 | 69.358 | 18.471 | 144.328 | 1.00 | 28.81 |
| ATOM | 2901 | C | LEU | C | 257 | 71.543 | 21.420 | 147.022 | 1.00 | 28.68 |
| ATOM | 2902 | O | LEU | C | 257 | 72.554 | 21.050 | 147.619 | 1.00 | 26.80 |
| ATOM | 2903 | N | GLN | C | 258 | 70.930 | 22.563 | 147.316 | 1.00 | 29.62 |
| ATOM | 2904 | CA | GLN | C | 258 | 71.464 | 23.397 | 148.394 | 1.00 | 30.80 |
| ATOM | 2905 | CB | GLN | C | 258 | 70.655 | 24.690 | 148.565 | 1.00 | 26.27 |
| ATOM | 2906 | C | GLN | C | 258 | 71.387 | 22.572 | 149.675 | 1.00 | 31.63 |
| ATOM | 2907 | O | GLN | C | 258 | 70.370 | 21.923 | 149.955 | 1.00 | 33.97 |
| ATOM | 2908 | N | ALA | C | 259 | 72.475 | 22.566 | 150.434 | 1.00 | 31.33 |
| ATOM | 2909 | CA | ALA | C | 259 | 72.504 | 21.838 | 151.690 | 1.00 | 29.04 |
| ATOM | 2910 | CB | ALA | C | 259 | 73.877 | 21.924 | 152.309 | 1.00 | 26.39 |
| ATOM | 2911 | C | ALA | C | 259 | 71.488 | 22.494 | 152.615 | 1.00 | 29.26 |
| ATOM | 2912 | O | ALA | C | 259 | 71.310 | 23.715 | 152.578 | 1.00 | 28.97 |
| ATOM | 2913 | N | GLY | C | 260 | 70.814 | 21.687 | 153.430 | 1.00 | 28.01 |
| ATOM | 2914 | CA | GLY | C | 260 | 69.857 | 22.238 | 154.364 | 1.00 | 27.52 |
| ATOM | 2915 | C | GLY | C | 260 | 68.420 | 22.312 | 153.887 | 1.00 | 29.28 |
| ATOM | 2916 | O | GLY | C | 260 | 67.536 | 22.690 | 154.665 | 1.00 | 29.52 |
| ATOM | 2917 | N | LEU | C | 261 | 68.176 | 21.975 | 152.621 | 1.00 | 28.79 |

TABLE 1-continued

FGFR1 D2–D3 Complexed with FGF2

| | | | | | | | | | |
|---|---|---|---|---|---|---|---|---|---|
| ATOM | 2918 | CA | LEU | C | 261 | 66.821 | 21.992 | 152.083 | 1.00 | 27.73 |
| ATOM | 2919 | CB | LEU | C | 261 | 66.566 | 23.241 | 151.250 | 1.00 | 27.45 |
| ATOM | 2920 | CG | LEU | C | 261 | 66.738 | 24.596 | 151.931 | 1.00 | 25.25 |
| ATOM | 2921 | CD1 | LEU | C | 261 | 66.114 | 25.630 | 151.015 | 1.00 | 25.20 |
| ATOM | 2922 | CD2 | LEU | C | 261 | 66.070 | 24.621 | 153.307 | 1.00 | 20.64 |
| ATOM | 2923 | C | LEU | C | 261 | 66.552 | 20.767 | 151.232 | 1.00 | 28.46 |
| ATOM | 2924 | O | LEU | C | 261 | 67.408 | 20.334 | 150.456 | 1.00 | 29.87 |
| ATOM | 2925 | N | PRO | C | 262 | 65.348 | 20.191 | 151.361 | 1.00 | 28.64 |
| ATOM | 2926 | CD | PRO | C | 262 | 64.953 | 18.948 | 150.677 | 1.00 | 26.13 |
| ATOM | 2927 | CA | PRO | C | 262 | 64.280 | 20.653 | 152.254 | 1.00 | 28.75 |
| ATOM | 2928 | CB | PRO | C | 262 | 63.106 | 19.760 | 151.866 | 1.00 | 28.38 |
| ATOM | 2929 | CG | PRO | C | 262 | 63.782 | 18.489 | 151.513 | 1.00 | 27.61 |
| ATOM | 2930 | C | PRO | C | 262 | 64.689 | 20.467 | 153.702 | 1.00 | 28.93 |
| ATOM | 2931 | O | PRO | C | 262 | 65.559 | 19.653 | 154.003 | 1.00 | 31.23 |
| ATOM | 2932 | N | ALA | C | 263 | 64.063 | 21.215 | 154.599 | 1.00 | 29.04 |
| ATOM | 2933 | CA | ALA | C | 263 | 64.390 | 21.115 | 156.018 | 1.00 | 28.73 |
| ATOM | 2934 | CB | ALA | C | 263 | 64.586 | 22.507 | 156.600 | 1.00 | 28.57 |
| ATOM | 2935 | C | ALA | C | 263 | 63.294 | 20.393 | 156.778 | 1.00 | 28.84 |
| ATOM | 2936 | O | ALA | C | 263 | 62.130 | 20.427 | 156.390 | 1.00 | 28.55 |
| ATOM | 2937 | N | ASN | C | 264 | 63.665 | 19.728 | 157.859 | 1.00 | 29.84 |
| ATOM | 2938 | CA | ASN | C | 264 | 62.667 | 19.044 | 158.655 | 1.00 | 32.61 |
| ATOM | 2939 | CB | ASN | C | 264 | 63.339 | 18.304 | 159.818 | 1.00 | 32.86 |
| ATOM | 2940 | CG | ASN | C | 264 | 64.203 | 17.129 | 159.346 | 1.00 | 33.45 |
| ATOM | 2941 | OD1 | ASN | C | 264 | 63.767 | 16.300 | 158.540 | 1.00 | 33.24 |
| ATOM | 2942 | ND2 | ASN | C | 264 | 65.424 | 17.052 | 159.854 | 1.00 | 34.09 |
| ATOM | 2943 | C | ASN | C | 264 | 61.676 | 20.097 | 159.161 | 1.00 | 33.97 |
| ATOM | 2944 | O | ASN | C | 264 | 62.068 | 21.234 | 159.457 | 1.00 | 35.75 |
| ATOM | 2945 | N | LYS | C | 265 | 60.397 | 19.723 | 159.232 | 1.00 | 33.81 |
| ATOM | 2946 | CA | LYS | C | 265 | 59.340 | 20.626 | 159.683 | 1.00 | 32.75 |
| ATOM | 2947 | CB | LYS | C | 265 | 58.442 | 21.021 | 158.513 | 1.00 | 30.60 |
| ATOM | 2948 | CG | LYS | C | 265 | 59.151 | 21.251 | 157.207 | 1.00 | 28.61 |
| ATOM | 2949 | CD | LYS | C | 265 | 59.994 | 22.491 | 157.247 | 1.00 | 28.14 |
| ATOM | 2950 | CE | LYS | C | 265 | 59.395 | 23.532 | 156.356 | 1.00 | 29.00 |
| ATOM | 2951 | HZ | LYS | C | 265 | 59.110 | 22.963 | 155.024 | 1.00 | 29.54 |
| ATOM | 2952 | C | LYS | C | 265 | 58.452 | 19.952 | 160.715 | 1.00 | 33.94 |
| ATOM | 2953 | O | LYS | C | 265 | 58.007 | 18.829 | 160.506 | 1.00 | 35.83 |
| ATOM | 2954 | N | THR | C | 266 | 58.202 | 20.618 | 161.831 | 1.00 | 34.46 |
| ATOM | 2955 | CA | THR | C | 266 | 57.283 | 20.074 | 162.824 | 1.00 | 34.80 |
| ATOM | 2956 | CB | THR | C | 266 | 57.904 | 19.999 | 164.246 | 1.00 | 33.05 |
| ATOM | 2957 | OG1 | THR | C | 266 | 58.856 | 18.924 | 164.309 | 1.00 | 29.77 |
| ATOM | 2958 | CG2 | THR | C | 266 | 56.822 | 19.768 | 165.280 | 1.00 | 30.67 |
| ATOM | 2959 | C | THR | C | 266 | 56.116 | 21.060 | 162.809 | 1.00 | 36.69 |
| ATOM | 2960 | O | THR | C | 266 | 56.316 | 22.268 | 162.924 | 1.00 | 36.47 |
| ATOM | 2961 | N | VAL | C | 267 | 54.903 | 20.557 | 162.627 | 1.00 | 38.51 |
| ATOM | 2962 | CA | VAL | C | 267 | 53.744 | 21.435 | 162.585 | 1.00 | 41.41 |
| ATOM | 2963 | CB | VAL | C | 267 | 53.387 | 21.793 | 161.122 | 1.00 | 40.72 |
| ATOM | 2964 | CG1 | VAL | C | 267 | 54.591 | 22.437 | 160.440 | 1.00 | 40.16 |
| ATOM | 2965 | CG2 | VAL | C | 267 | 52.947 | 20.546 | 160.366 | 1.00 | 40.17 |
| ATOM | 2966 | C | VAL | C | 267 | 52.521 | 20.840 | 163.287 | 1.00 | 43.88 |
| ATOM | 2967 | O | VAL | C | 267 | 52.533 | 19.676 | 163.711 | 1.00 | 44.81 |
| ATOM | 2968 | N | ALA | C | 268 | 51.475 | 21.654 | 163.420 | 1.00 | 45.61 |
| ATOM | 2969 | CA | ALA | C | 268 | 50.246 | 21.229 | 164.075 | 1.00 | 46.72 |
| ATOM | 2970 | CB | ALA | C | 268 | 49.595 | 22.410 | 164.763 | 1.00 | 47.07 |
| ATOM | 2971 | C | ALA | C | 268 | 49.296 | 20.635 | 163.054 | 1.00 | 47.68 |
| ATOM | 2972 | O | ALA | C | 268 | 49.272 | 21.056 | 161.898 | 1.00 | 47.58 |
| ATOM | 2973 | N | LEU | C | 269 | 48.520 | 19.647 | 163.481 | 1.00 | 48.97 |
| ATOM | 2974 | CA | LEU | C | 269 | 47.563 | 19.008 | 162.593 | 1.00 | 49.91 |
| ATOM | 2975 | CB | LEU | C | 269 | 46.675 | 18.044 | 163.390 | 1.00 | 51.98 |
| ATOM | 2976 | CG | LEU | C | 269 | 45.568 | 17.292 | 162.645 | 1.00 | 54.75 |
| ATOM | 2977 | CD1 | LEU | C | 269 | 45.328 | 15.925 | 163.300 | 1.00 | 55.71 |
| ATOM | 2978 | CD2 | LEU | C | 269 | 44.290 | 18.139 | 162.639 | 1.00 | 55.58 |
| ATOM | 2979 | C | LEU | C | 269 | 46.721 | 20.087 | 161.923 | 1.00 | 48.50 |
| ATOM | 2980 | O | LEU | C | 269 | 46.225 | 20.987 | 162.584 | 1.00 | 48.65 |
| ATOM | 2981 | N | GLY | C | 270 | 46.592 | 20.016 | 160.607 | 1.00 | 48.14 |
| ATOM | 2982 | CA | GLY | C | 270 | 45.795 | 20.999 | 159.901 | 1.00 | 48.37 |
| ATOM | 2983 | C | GLY | C | 270 | 46.556 | 22.163 | 159.297 | 1.00 | 47.96 |
| ATOM | 2984 | O | GLY | C | 270 | 45.988 | 22.941 | 158.525 | 1.00 | 48.79 |
| ATOM | 2985 | N | SER | C | 271 | 47.834 | 22.285 | 159.632 | 1.00 | 47.43 |
| ATOM | 2986 | CA | SER | C | 271 | 48.664 | 23.371 | 159.109 | 1.00 | 47.85 |
| ATOM | 2987 | CB | SER | C | 271 | 50.043 | 23.337 | 159.769 | 1.00 | 45.66 |
| ATOM | 2988 | OG | SER | C | 271 | 49.938 | 23.210 | 161.171 | 1.00 | 44.73 |
| ATOM | 2989 | C | SER | C | 271 | 48.858 | 23.296 | 157.593 | 1.00 | 48.34 |
| ATOM | 2990 | O | SER | C | 271 | 48.412 | 22.363 | 156.936 | 1.00 | 48.78 |
| ATOM | 2991 | N | ASN | C | 272 | 49.541 | 24.291 | 157.050 | 1.00 | 48.71 |
| ATOM | 2992 | CA | ASN | C | 272 | 49.832 | 24.335 | 155.628 | 1.00 | 50.82 |
| ATOM | 2993 | CB | ASN | C | 272 | 49.206 | 25.563 | 154.969 | 1.00 | 53.33 |
| ATOM | 2994 | CG | ASN | C | 272 | 47.752 | 25.369 | 154.639 | 1.00 | 55.48 |

TABLE 1-continued

FGFR1 D2–D3 Complexed with FGF2

| ATOM | 2995 | OD1 | ASN | C | 272 | 47.377 | 24.398 | 153.983 | 1.00 | 57.95 |
|------|------|-----|-----|---|-----|--------|--------|---------|------|-------|
| ATOM | 2996 | ND2 | ASN | C | 272 | 46.919 | 26.303 | 155.078 | 1.00 | 57.55 |
| ATOM | 2997 | C | ASN | C | 272 | 51.337 | 24.437 | 155.474 | 1.00 | 50.91 |
| ATOM | 2998 | O | ASN | C | 272 | 51.885 | 25.539 | 155.492 | 1.00 | 52.42 |
| ATOM | 2999 | N | VAL | C | 273 | 52.011 | 23.304 | 155.320 | 1.00 | 48.89 |
| ATOM | 3000 | CA | VAL | C | 273 | 53.459 | 23.323 | 155.167 | 1.00 | 46.82 |
| ATOM | 3001 | CB | VAL | C | 273 | 54.099 | 22.146 | 155.931 | 1.00 | 47.39 |
| ATOM | 3002 | CG1 | VAL | C | 273 | 53.438 | 20.863 | 155.529 | 1.00 | 48.39 |
| ATOM | 3003 | CG2 | VAL | C | 273 | 55.587 | 22.079 | 155.654 | 1.00 | 48.76 |
| ATOM | 3004 | C | VAL | C | 273 | 53.874 | 23.265 | 153.702 | 1.00 | 44.84 |
| ATOM | 3005 | O | VAL | C | 273 | 53.117 | 22.783 | 152.858 | 1.00 | 45.60 |
| ATOM | 3006 | N | GLU | C | 274 | 55.060 | 23.794 | 153.402 | 1.00 | 42.50 |
| ATOM | 3007 | CA | GLU | C | 274 | 55.591 | 23.756 | 152.042 | 1.00 | 41.08 |
| ATOM | 3008 | CB | GLU | C | 274 | 55.197 | 25.008 | 151.260 | 1.00 | 42.81 |
| ATOM | 3009 | CG | GLU | C | 274 | 55.946 | 26.261 | 151.641 | 1.00 | 48.27 |
| ATOM | 3010 | CD | GLU | C | 274 | 55.372 | 27.499 | 150.969 | 1.00 | 50.91 |
| ATOM | 3011 | OE1 | GLU | C | 274 | 54.191 | 27.820 | 151.232 | 1.00 | 52.00 |
| ATOM | 3012 | OE2 | GLU | C | 274 | 56.093 | 28.149 | 150.179 | 1.00 | 52.04 |
| ATOM | 3013 | C | GLU | C | 274 | 57.112 | 23.606 | 152.093 | 1.00 | 38.22 |
| ATOM | 3014 | O | GLU | C | 274 | 57.798 | 24.370 | 152.764 | 1.00 | 35.80 |
| ATOM | 3015 | N | PHE | C | 275 | 57.623 | 22.597 | 151.391 | 1.00 | 35.82 |
| ATOM | 3016 | CA | PHE | C | 275 | 59.056 | 22.303 | 151.356 | 1.00 | 32.70 |
| ATOM | 3017 | CB | PHE | C | 275 | 59.286 | 20.793 | 151.208 | 1.00 | 27.90 |
| ATOM | 3018 | CG | PHE | C | 275 | 59.061 | 20.007 | 152.468 | 1.00 | 21.37 |
| ATOM | 3019 | CD1 | PHE | C | 275 | 60.002 | 20.013 | 153.479 | 1.00 | 19.05 |
| ATOM | 3020 | CD2 | PHE | C | 275 | 57.906 | 19.257 | 152.638 | 1.00 | 18.11 |
| ATOM | 3021 | CE1 | PHE | C | 275 | 59.792 | 19.283 | 154.643 | 1.00 | 18.55 |
| ATOM | 3022 | CE2 | PHE | C | 275 | 57.693 | 18.532 | 153.790 | 1.00 | 14.62 |
| ATOM | 3023 | CZ | PHE | C | 275 | 58.631 | 18.540 | 154.794 | 1.00 | 15.13 |
| ATOM | 3024 | C | PHE | C | 275 | 59.759 | 22.996 | 150.209 | 1.00 | 32.68 |
| ATOM | 3025 | O | PHE | C | 275 | 59.141 | 23.364 | 149.218 | 1.00 | 33.88 |
| ATOM | 3026 | N | MET | C | 276 | 61.065 | 23.157 | 150.340 | 1.00 | 32.88 |
| ATOM | 3027 | CA | MET | C | 276 | 61.841 | 23.775 | 149.285 | 1.00 | 33.50 |
| ATOM | 3028 | CB | MET | C | 276 | 62.421 | 25.098 | 149.737 | 1.00 | 36.46 |
| ATOM | 3029 | CG | MET | C | 276 | 61.437 | 26.185 | 150.011 | 1.00 | 40.85 |
| ATOM | 3030 | SD | MET | C | 276 | 62.424 | 27.650 | 150.433 | 1.00 | 48.53 |
| ATOM | 3031 | CE | MET | C | 276 | 62.803 | 28.305 | 148.751 | 1.00 | 46.73 |
| ATOM | 3032 | C | MET | C | 276 | 62.922 | 2.884 | 148.870 | 1.00 | 32.74 |
| ATOM | 3033 | O | MET | C | 276 | 63.441 | 22.022 | 149.619 | 1.00 | 32.54 |
| ATOM | 3034 | N | CYS | C | 277 | 63.481 | 23.120 | 147.668 | 1.00 | 31.31 |
| ATOM | 3035 | CA | CYS | C | 277 | 64.604 | 22.364 | 147.154 | 1.00 | 31.22 |
| ATOM | 3036 | C | CYS | C | 277 | 65.294 | 23.247 | 146.119 | 1.00 | 30.72 |
| ATOM | 3037 | O | CYS | C | 277 | 64.716 | 23.566 | 145.078 | 1.00 | 32.01 |
| ATOM | 3038 | CB | CYS | C | 277 | 64.109 | 21.078 | 146.521 | 1.00 | 30.12 |
| ATOM | 3039 | SG | CYS | C | 277 | 65.424 | 19.895 | 146.128 | 1.00 | 31.69 |
| ATOM | 3040 | N | LYS | C | 278 | 66.521 | 23.663 | 146.409 | 1.00 | 28.06 |
| ATOM | 3041 | CA | LYS | C | 278 | 67.227 | 24.529 | 145.488 | 1.00 | 25.72 |
| ATOM | 3042 | CB | LYS | C | 278 | 67.877 | 25.677 | 146.277 | 1.00 | 16.91 |
| ATOM | 3043 | C | LYS | C | 278 | 68.234 | 23.684 | 144.690 | 1.00 | 25.74 |
| ATOM | 3044 | O | LYS | C | 278 | 69.202 | 23.148 | 145.236 | 1.00 | 27.31 |
| ATOM | 3045 | N | VAL | C | 279 | 67.981 | 23.552 | 143.392 | 1.00 | 26.14 |
| ATOM | 3046 | CA | VAL | C | 279 | 68.839 | 22.742 | 142.518 | 1.00 | 26.68 |
| ATOM | 3047 | CB | VAL | C | 279 | 67.980 | 21.824 | 141.568 | 1.00 | 24.83 |
| ATOM | 3048 | CG1 | VAL | C | 279 | 68.870 | 20.894 | 140.757 | 1.00 | 22.99 |
| ATOM | 3049 | CG2 | VAL | C | 279 | 67.001 | 21.015 | 142.373 | 1.00 | 24.61 |
| ATOM | 3050 | C | VAL | C | 279 | 69.777 | 23.563 | 141.644 | 1.00 | 27.32 |
| ATOM | 3051 | O | VAL | C | 279 | 69.516 | 24.726 | 141.342 | 1.00 | 27.26 |
| ATOM | 3052 | N | TYR | C | 280 | 70.881 | 22.940 | 141.252 | 1.00 | 28.89 |
| ATOM | 3053 | CA | TYR | C | 280 | 71.851 | 23.568 | 140.370 | 1.00 | 29.97 |
| ATOM | 3054 | CB | TYR | C | 280 | 73.067 | 24.114 | 141.133 | 1.00 | 31.04 |
| ATOM | 3055 | CG | TYR | C | 280 | 74.121 | 24.607 | 140.172 | 1.00 | 32.86 |
| ATOM | 3056 | CD1 | TYR | C | 280 | 73.934 | 25.798 | 139.464 | 1.00 | 34.02 |
| ATOM | 3057 | CE1 | TYR | C | 280 | 74.795 | 26.177 | 138.430 | 1.00 | 33.55 |
| ATOM | 3058 | CD2 | TYR | C | 280 | 75.215 | 23.806 | 139.834 | 1.00 | 34.24 |
| ATOM | 3059 | CE2 | TYR | C | 280 | 76.081 | 24.170 | 138.799 | 1.00 | 36.13 |
| ATOM | 3060 | CZ | TYR | C | 280 | 75.856 | 25.359 | 138.098 | 1.00 | 36.27 |
| ATOM | 3061 | OH | TYR | C | 280 | 76.661 | 25.705 | 137.038 | 1.00 | 38.38 |
| ATOM | 3062 | C | TYR | C | 280 | 72.316 | 22.510 | 139.389 | 1.00 | 30.13 |
| ATOM | 3063 | O | TYR | C | 280 | 72.720 | 21.423 | 139.783 | 1.00 | 31.45 |
| ATOM | 3064 | N | SER | C | 281 | 72.264 | 22.829 | 138.109 | 1.00 | 31.21 |
| ATOM | 3065 | CA | SER | C | 281 | 72.697 | 21.882 | 137.099 | 1.00 | 31.69 |
| ATOM | 3066 | CB | SER | C | 281 | 71.584 | 20.857 | 136.851 | 1.00 | 31.08 |
| ATOM | 3067 | OG | SER | C | 281 | 71.973 | 19.883 | 135.902 | 1.00 | 30.86 |
| ATOM | 3068 | C | SER | C | 281 | 72.988 | 22.660 | 135.827 | 1.00 | 32.60 |
| ATOM | 3069 | O | SER | C | 281 | 72.254 | 23.597 | 135.493 | 1.00 | 31.43 |
| ATOM | 3070 | N | ASP | C | 282 | 74.073 | 22.305 | 135.140 | 1.00 | 34.32 |
| ATOM | 3071 | CA | ASP | C | 282 | 74.388 | 22.971 | 133.887 | 1.00 | 33.65 |

TABLE 1-continued

FGFR1 D2–D3 Complexed with FGF2

| ATOM | 3072 | CB | ASP | C | 282 | 75.809 | 22.650 | 133.424 | 1.00 | 37.97 |
|---|---|---|---|---|---|---|---|---|---|---|
| ATOM | 3073 | CG | ASP | C | 282 | 76.115 | 23.218 | 132.050 | 1.00 | 41.38 |
| ATOM | 3074 | OD1 | ASP | C | 282 | 77.316 | 23.423 | 131.752 | 1.00 | 41.95 |
| ATOM | 3075 | OD2 | ASP | C | 282 | 75.159 | 23.450 | 131.268 | 1.00 | 42.76 |
| ATOM | 3076 | C | ASP | C | 282 | 73.341 | 22.389 | 132.946 | 1.00 | 32.33 |
| ATOM | 3077 | O | ASP | C | 282 | 72.436 | 23.100 | 132.516 | 1.00 | 32.71 |
| ATOM | 3078 | N | PRO | C | 283 | 73.425 | 21.083 | 132.633 | 1.00 | 30.93 |
| ATOM | 3079 | CD | PRO | C | 283 | 74.459 | 20.080 | 132.962 | 1.00 | 30.14 |
| ATOM | 3080 | CA | PRO | C | 283 | 72.403 | 20.521 | 131.735 | 1.00 | 29.60 |
| ATOM | 3081 | CB | PRO | C | 283 | 72.932 | 19.120 | 131.434 | 1.00 | 29.84 |
| ATOM | 3082 | CG | PRO | C | 283 | 73.752 | 18.782 | 132.662 | 1.00 | 30.68 |
| ATOM | 3083 | C | PRO | C | 283 | 71.070 | 20.487 | 132.474 | 1.00 | 29.59 |
| ATOM | 3084 | O | PRO | C | 283 | 71.050 | 20.319 | 133.691 | 1.00 | 30.32 |
| ATOM | 3085 | N | GLN | C | 284 | 69.959 | 20.638 | 131.757 | 1.00 | 30.43 |
| ATOM | 3086 | CA | GLN | C | 284 | 68.641 | 20.647 | 132.406 | 1.00 | 29.42 |
| ATOM | 3087 | CB | GLN | C | 284 | 67.488 | 20.630 | 131.383 | 1.00 | 29.76 |
| ATOM | 3088 | CG | GLN | C | 284 | 67.422 | 21.820 | 130.459 | 1.00 | 30.05 |
| ATOM | 3089 | CD | GLN | C | 284 | 67.326 | 23.142 | 131.189 | 1.00 | 30.62 |
| ATOM | 3090 | OE1 | GLN | C | 284 | 67.695 | 24.177 | 130.648 | 1.00 | 33.73 |
| ATOM | 3091 | NE2 | GLN | C | 284 | 66.821 | 23.120 | 132.411 | 1.00 | 31.19 |
| ATOM | 3092 | C | GLN | C | 284 | 68.421 | 19.486 | 133.363 | 1.00 | 28.08 |
| ATOM | 3093 | O | GLN | C | 284 | 68.585 | 18.315 | 133.008 | 1.00 | 26.14 |
| ATOM | 3094 | N | PRO | C | 285 | 68.046 | 19.798 | 134.599 | 1.00 | 27.57 |
| ATOM | 3095 | CD | PRO | C | 285 | 68.156 | 21.115 | 135.249 | 1.00 | 27.54 |
| ATOM | 3096 | CA | PRO | C | 285 | 67.802 | 18.754 | 135.589 | 1.00 | 28.78 |
| ATOM | 3097 | CB | PRO | C | 285 | 68.239 | 19.411 | 136.883 | 1.00 | 28.36 |
| ATOM | 3098 | CG | PRO | C | 285 | 67.739 | 20.807 | 136.684 | 1.00 | 28.33 |
| ATOM | 3099 | C | PRO | C | 285 | 66.324 | 18.340 | 135.635 | 1.00 | 29.46 |
| ATOM | 3100 | O | PRO | C | 285 | 65.411 | 19.147 | 135.404 | 1.00 | 29.73 |
| ATOM | 3101 | N | HIS | C | 286 | 66.092 | 17.068 | 135.918 | 1.00 | 30.11 |
| ATOM | 3102 | CA | HIS | C | 286 | 64.733 | 16.581 | 136.036 | 1.00 | 30.34 |
| ATOM | 3103 | CB | HIS | C | 286 | 64.560 | 15.233 | 135.345 | 1.00 | 33.50 |
| ATOM | 3104 | CG | HIS | C | 286 | 63.137 | 14.776 | 135.305 | 1.00 | 37.45 |
| ATOM | 3105 | CD2 | HIS | C | 286 | 62.003 | 15.439 | 134.980 | 1.00 | 37.57 |
| ATOM | 3106 | ND1 | HIS | C | 286 | 62.749 | 13.500 | 135.654 | 1.00 | 37.58 |
| ATOM | 3107 | CE1 | HIS | C | 286 | 61.438 | 13.398 | 135.548 | 1.00 | 37.31 |
| ATOM | 3108 | NE2 | HIS | C | 286 | 60.962 | 14.560 | 135.140 | 1.00 | 38.77 |
| ATOM | 3109 | C | HIS | C | 286 | 64.476 | 16.425 | 137.525 | 1.00 | 28.51 |
| ATOM | 3110 | O | HIS | C | 286 | 65.063 | 15.555 | 138.170 | 1.00 | 28.43 |
| ATOM | 3111 | N | ILE | C | 287 | 63.616 | 17.286 | 138.064 | 1.00 | 27.36 |
| ATOM | 3112 | CA | ILE | C | 287 | 63.275 | 17.272 | 139.483 | 1.00 | 24.48 |
| ATOM | 3113 | CB | ILE | C | 287 | 63.139 | 18.705 | 140.019 | 1.00 | 22.01 |
| ATOM | 3114 | CG2 | ILE | C | 287 | 62.670 | 18.695 | 141.476 | 1.00 | 18.21 |
| ATOM | 3115 | CG1 | ILE | C | 287 | 64.475 | 19.418 | 139.841 | 1.00 | 17.88 |
| ATOM | 3116 | CD1 | ILE | C | 287 | 64.419 | 20.889 | 140.118 | 1.00 | 20.45 |
| ATOM | 3117 | C | ILE | C | 287 | 61.986 | 16.506 | 139.743 | 1.00 | 24.82 |
| ATOM | 3118 | O | ILE | C | 287 | 61.117 | 16.418 | 138.877 | 1.00 | 25.02 |
| ATOM | 3119 | N | GLN | C | 288 | 61.869 | 15.960 | 140.948 | 1.00 | 24.37 |
| ATOM | 3120 | CA | GLN | C | 288 | 60.704 | 15.183 | 141.314 | 1.00 | 23.98 |
| ATOM | 3121 | CB | GLN | C | 288 | 60.864 | 13.780 | 140.735 | 1.00 | 23.04 |
| ATOM | 3122 | CG | GLN | C | 288 | 59.666 | 12.871 | 140.893 | 1.00 | 24.04 |
| ATOM | 3123 | CD | GLN | C | 288 | 59.859 | 11.546 | 140.180 | 1.00 | 23.43 |
| ATOM | 3124 | OE1 | GLN | C | 288 | 59.223 | 11.266 | 139.155 | 1.00 | 21.63 |
| ATOM | 3125 | NE2 | GLN | C | 288 | 60.755 | 10.724 | 140.713 | 1.00 | 23.17 |
| ATOM | 3126 | C | GLN | C | 288 | 60.575 | 15.130 | 142.824 | 1.00 | 22.93 |
| ATOM | 3127 | O | GLN | C | 288 | 61.572 | 15.129 | 143.523 | 1.00 | 24.35 |
| ATOM | 3128 | N | TRP | C | 289 | 59.348 | 15.117 | 143.331 | 1.00 | 23.58 |
| ATOM | 3129 | CA | TRP | C | 289 | 59.142 | 15.036 | 144.775 | 1.00 | 25.79 |
| ATOM | 3130 | CB | TRP | C | 289 | 58.254 | 16.175 | 145.295 | 1.00 | 25.56 |
| ATOM | 3131 | CG | TRP | C | 289 | 58.933 | 17.506 | 145.344 | 1.00 | 25.50 |
| ATOM | 3132 | CD2 | TRP | C | 289 | 59.645 | 18.069 | 146.455 | 1.00 | 24.57 |
| ATOM | 3133 | CE2 | TRP | C | 289 | 60.132 | 19.331 | 146.042 | 1.00 | 24.75 |
| ATOM | 3134 | CE3 | TRP | C | 289 | 59.921 | 17.630 | 147.761 | 1.00 | 24.41 |
| ATOM | 3135 | CD1 | TRP | C | 289 | 59.015 | 18.421 | 144.331 | 1.00 | 25.66 |
| ATOM | 3136 | NE1 | TRP | C | 289 | 59.731 | 19.520 | 144.743 | 1.00 | 25.92 |
| ATOM | 3137 | CZ2 | TRP | C | 289 | 60.881 | 20.161 | 146.883 | 1.00 | 22.40 |
| ATOM | 3138 | CZ3 | TRP | C | 289 | 60.665 | 18.451 | 148.600 | 1.00 | 21.27 |
| ATOM | 3139 | CH2 | TRP | C | 289 | 61.137 | 19.706 | 148.152 | 1.00 | 24.99 |
| ATOM | 3140 | C | TRP | C | 289 | 58.502 | 13.709 | 145.125 | 1.00 | 25.97 |
| ATOM | 3141 | O | TRP | C | 289 | 57.590 | 13.261 | 144.437 | 1.00 | 27.01 |
| ATOM | 3142 | N | LEU | C | 290 | 58.983 | 13.089 | 146.198 | 1.00 | 26.09 |
| ATOM | 3143 | CA | LEU | C | 290 | 58.471 | 11.801 | 146.643 | 1.00 | 27.29 |
| ATOM | 3144 | CB | LEU | C | 290 | 59.505 | 10.698 | 146.424 | 1.00 | 29.58 |
| ATOM | 3145 | CG | LEU | C | 290 | 59.621 | 10.020 | 145.068 | 1.00 | 31.88 |
| ATOM | 3146 | CD1 | LEU | C | 290 | 59.875 | 11.031 | 143.947 | 1.00 | 33.27 |
| ATOM | 3147 | CD2 | LEU | C | 290 | 60.752 | 9.027 | 145.170 | 1.00 | 33.26 |
| ATOM | 3148 | C | LEU | C | 290 | 58.156 | 11.790 | 148.111 | 1.00 | 27.39 |

TABLE 1-continued

FGFR1 D2–D3 Complexed with FGF2

| ATOM | 3149 | O | LEU | C | 290 | 58.697 | 12.586 | 148.875 | 1.00 | 25.52 |
|---|---|---|---|---|---|---|---|---|---|---|
| ATOM | 3150 | N | LYS | C | 291 | 57.264 | 10.885 | 148.498 | 1.00 | 28.19 |
| ATOM | 3151 | CA | LYS | C | 291 | 56.981 | 10.704 | 149.907 | 1.00 | 29.65 |
| ATOM | 3152 | CB | LYS | C | 291 | 55.547 | 10.994 | 150.298 | 1.00 | 29.20 |
| ATOM | 3153 | CG | LYS | C | 291 | 55.458 | 10.873 | 151.802 | 1.00 | 28.12 |
| ATOM | 3154 | CD | LYS | C | 291 | 54.082 | 10.971 | 152.347 | 1.00 | 31.10 |
| ATOM | 3155 | CE | LYS | C | 291 | 54.147 | 10.840 | 153.863 | 1.00 | 34.01 |
| ATOM | 3156 | NZ | LYS | C | 291 | 52.799 | 10.966 | 154.488 | 1.00 | 38.80 |
| ATOM | 3157 | C | LYS | C | 291 | 57.260 | 9.245 | 150.201 | 1.00 | 30.38 |
| ATOM | 3158 | O | LYS | C | 291 | 56.877 | 8.369 | 149.429 | 1.00 | 30.70 |
| ATOM | 3159 | N | HIS | C | 292 | 57.934 | 8.984 | 151.311 | 1.00 | 31.17 |
| ATOM | 3160 | CA | HIS | C | 292 | 58.255 | 7.617 | 151.683 | 1.00 | 35.38 |
| ATOM | 3161 | CB | HIS | C | 292 | 59.533 | 7.606 | 152.500 | 1.00 | 33.90 |
| ATOM | 3162 | CG | HIS | C | 292 | 60.738 | 7.971 | 151.698 | 1.00 | 33.72 |
| ATOM | 3163 | CD2 | HIS | C | 292 | 61.298 | 9.173 | 151.428 | 1.00 | 33.65 |
| ATOM | 3164 | ND1 | HIS | C | 292 | 61.463 | 7.042 | 150.986 | 1.00 | 32.94 |
| ATOM | 3165 | CE1 | HIS | C | 292 | 62.418 | 7.656 | 150.311 | 1.00 | 32.86 |
| ATOM | 3166 | NE2 | HIS | C | 292 | 62.340 | 8.950 | 150.562 | 1.00 | 33.51 |
| ATOM | 3167 | C | HIS | C | 292 | 57.110 | 6.976 | 152.436 | 1.00 | 38.27 |
| ATOM | 3168 | O | HIS | C | 292 | 56.590 | 7.535 | 153.402 | 1.00 | 39.32 |
| ATOM | 3169 | N | ILE | C | 293 | 56.740 | 5.784 | 151.992 | 1.00 | 40.65 |
| ATOM | 3170 | CA | ILE | C | 293 | 55.616 | 5.069 | 152.565 | 1.00 | 43.55 |
| ATOM | 3171 | CB | ILE | C | 293 | 54.598 | 4.875 | 151.447 | 1.00 | 43.18 |
| ATOM | 3172 | CG2 | ILE | C | 293 | 53.368 | 4.172 | 151.951 | 1.00 | 44.52 |
| ATOM | 3173 | CG1 | ILE | C | 293 | 54.277 | 6.252 | 150.870 | 1.00 | 43.20 |
| ATOM | 3174 | CD1 | ILE | C | 293 | 53.296 | 6.236 | 149.748 | 1.00 | 48.45 |
| ATOM | 3175 | C | ILE | C | 293 | 55.914 | 3.737 | 153.279 | 1.00 | 45.41 |
| ATOM | 3176 | O | ILE | C | 293 | 56.903 | 3.058 | 152.976 | 1.00 | 45.28 |
| ATOM | 3177 | N | GLU | C | 294 | 55.068 | 3.391 | 154.252 | 1.00 | 47.39 |
| ATOM | 3178 | CA | GLU | C | 294 | 55.204 | 2.140 | 155.008 | 1.00 | 50.70 |
| ATOM | 3179 | CB | GLU | C | 294 | 55.286 | 2.436 | 156.512 | 1.00 | 48.39 |
| ATOM | 3180 | CG | GLU | C | 294 | 53.959 | 1.310 | 154.706 | 1.00 | 53.03 |
| ATOM | 3181 | O | GLU | C | 294 | 52.850 | 1.754 | 154.971 | 1.00 | 54.66 |
| ATOM | 3182 | N | VAL | C | 295 | 54.138 | 0.104 | 154.172 | 1.00 | 56.24 |
| ATOM | 3183 | CA | VAL | C | 295 | 53.010 | −0.777 | 153.810 | 1.00 | 59.45 |
| ATOM | 3184 | CB | VAL | C | 295 | 53.401 | −1.659 | 152.576 | 1.00 | 58.62 |
| ATOM | 3185 | CG1 | VAL | C | 295 | 52.315 | −2.666 | 152.255 | 1.00 | 58.90 |
| ATOM | 3186 | CG2 | VAL | C | 295 | 53.639 | −0.773 | 151.363 | 1.00 | 56.91 |
| ATOM | 3187 | C | VAL | C | 295 | 52.538 | −1.684 | 154.972 | 1.00 | 61.72 |
| ATOM | 3188 | O | VAL | C | 295 | 51.394 | −2.158 | 155.024 | 1.00 | 61.54 |
| ATOM | 3189 | N | ASN | C | 296 | 53.456 | −1.910 | 155.894 | 1.00 | 63.81 |
| ATOM | 3190 | CA | ASN | C | 296 | 53.269 | −2.698 | 157.106 | 1.00 | 65.79 |
| ATOM | 3191 | CB | ASN | C | 296 | 53.574 | −4.182 | 156.835 | 1.00 | 66.07 |
| ATOM | 3192 | CG | ASN | C | 296 | 54.812 | −4.374 | 155.927 | 1.00 | 68.22 |
| ATOM | 3193 | OD1 | ASN | C | 296 | 55.165 | −3.493 | 155.123 | 1.00 | 67.63 |
| ATOM | 3194 | ND2 | ASN | C | 296 | 55.463 | −5.543 | 156.041 | 1.00 | 69.60 |
| ATOM | 3195 | C | ASN | C | 296 | 54.325 | −2.053 | 157.992 | 1.00 | 66.21 |
| ATOM | 3196 | O | ASN | C | 296 | 54.159 | −0.911 | 158.405 | 1.00 | 66.39 |
| ATOM | 3197 | N | GLY | C | 297 | 55.423 | −2.736 | 158.269 | 1.00 | 66.33 |
| ATOM | 3198 | CA | GLY | C | 297 | 56.433 | −2.093 | 159.083 | 1.00 | 65.88 |
| ATOM | 3199 | C | GLY | C | 297 | 57.435 | −1.460 | 158.144 | 1.00 | 65.04 |
| ATOM | 3200 | O | GLY | C | 297 | 57.835 | −0.300 | 158.298 | 1.00 | 66.23 |
| ATOM | 3201 | N | SER | C | 298 | 57.778 | −2.241 | 157.125 | 1.00 | 63.11 |
| ATOM | 3202 | CA | SER | C | 298 | 58.756 | −1.883 | 156.112 | 1.00 | 60.17 |
| ATOM | 3203 | CB | SER | C | 298 | 58.975 | −3.063 | 155.157 | 1.00 | 60.95 |
| ATOM | 3204 | OG | SER | C | 298 | 57.808 | −3.351 | 154.398 | 1.00 | 61.30 |
| ATOM | 3205 | C | SER | C | 298 | 58.442 | −0.636 | 155.314 | 1.00 | 57.83 |
| ATOM | 3206 | O | SER | C | 298 | 57.289 | −0.362 | 154.962 | 1.00 | 55.90 |
| ATOM | 3207 | N | LYS | C | 299 | 59.506 | 0.125 | 155.073 | 1.00 | 55.35 |
| ATOM | 3208 | CA | LYS | C | 299 | 59.459 | 1.354 | 154.298 | 1.00 | 54.04 |
| ATOM | 3209 | CB | LYS | C | 299 | 60.202 | 2.486 | 155.025 | 1.00 | 55.85 |
| ATOM | 3210 | CG | LYS | C | 299 | 59.887 | 2.568 | 156.509 | 1.00 | 58.61 |
| ATOM | 3211 | CD | LYS | C | 299 | 59.571 | 3.993 | 156.978 | 1.00 | 61.21 |
| ATOM | 3212 | CE | LYS | C | 299 | 59.026 | 3.968 | 158.416 | 1.00 | 62.47 |
| ATOM | 3213 | HZ | LYS | C | 299 | 58.761 | 5.317 | 158.980 | 1.00 | 62.32 |
| ATOM | 3214 | C | LYS | C | 299 | 60.198 | 0.963 | 153.025 | 1.00 | 51.29 |
| ATOM | 3215 | O | LYS | C | 299 | 60.307 | 1.742 | 152.074 | 1.00 | 52.29 |
| ATOM | 3216 | N | ILE | C | 300 | 60.708 | −0.265 | 153.042 | 1.00 | 46.86 |
| ATOM | 3217 | CA | ILE | C | 300 | 61.421 | −0.842 | 151.915 | 1.00 | 43.84 |
| ATOM | 3218 | CB | ILE | C | 300 | 62.868 | −1.185 | 152.268 | 1.00 | 43.48 |
| ATOM | 3219 | CG2 | ILE | C | 300 | 63.514 | −1.946 | 151.117 | 1.00 | 42.81 |
| ATOM | 3220 | CG1 | ILE | C | 300 | 63.652 | 0.094 | 152.533 | 1.00 | 43.78 |
| ATOM | 3221 | CD1 | ILE | C | 300 | 65.137 | −0.146 | 152.707 | 1.00 | 45.12 |
| ATOM | 3222 | C | ILE | C | 300 | 60.725 | −2.125 | 151.483 | 1.00 | 40.85 |
| ATOM | 3223 | O | ILE | C | 300 | 60.277 | −2.900 | 152.316 | 1.00 | 40.80 |
| ATOM | 3224 | H | GLY | C | 301 | 60.653 | −2.352 | 150.178 | 1.00 | 38.10 |
| ATOM | 3225 | CA | GLY | C | 301 | 59.983 | −3.534 | 149.683 | 1.00 | 36.41 |

TABLE 1-continued

FGFR1 D2–D3 Complexed with FGF2

| ATOM | 3226 | C | GLY | C | 301 | 60.841 | −4.689 | 149.202 | 1.00 | 37.19 |
| --- | --- | --- | --- | --- | --- | --- | --- | --- | --- | --- |
| ATOM | 3227 | O | GLY | C | 301 | 62.071 | −4.647 | 149.266 | 1.00 | 35.86 |
| ATOM | 3228 | N | PRO | C | 302 | 60.186 | −5.752 | 148.701 | 1.00 | 37.20 |
| ATOM | 3229 | CD | PRO | C | 302 | 58.725 | −5.710 | 148.469 | 1.00 | 36.58 |
| ATOM | 3230 | CA | PRO | C | 302 | 60.758 | −6.993 | 148.171 | 1.00 | 35.86 |
| ATOM | 3231 | CB | PRO | C | 302 | 59.667 | −7.492 | 147.240 | 1.00 | 37.20 |
| ATOM | 3232 | CG | PRO | C | 302 | 58.415 | −7.102 | 147.979 | 1.00 | 36.35 |
| ATOM | 3233 | C | PRO | C | 302 | 62.065 | −6.784 | 147.433 | 1.00 | 36.22 |
| ATOM | 3234 | O | PRO | C | 302 | 63.050 | −7.480 | 147.677 | 1.00 | 37.38 |
| ATOM | 3235 | N | ASP | C | 303 | 62.053 | −5.819 | 146.522 | 1.00 | 36.04 |
| ATOM | 3236 | CA | ASP | C | 303 | 63.214 | −5.484 | 145.705 | 1.00 | 35.56 |
| ATOM | 3237 | CB | ASP | C | 303 | 62.766 | −4.668 | 144.496 | 1.00 | 36.91 |
| ATOM | 3238 | CG | ASP | C | 303 | 62.023 | −3.418 | 144.892 | 1.00 | 40.20 |
| ATOM | 3239 | OD1 | ASP | C | 303 | 61.054 | −3.523 | 145.685 | 1.00 | 42.73 |
| ATOM | 3240 | OD2 | ASP | C | 303 | 62.403 | −2.330 | 144.410 | 1.00 | 40.82 |
| ATOM | 3241 | C | ASP | C | 303 | 64.294 | −4.712 | 146.450 | 1.00 | 34.79 |
| ATOM | 3242 | O | ASP | C | 303 | 65.356 | −4.451 | 145.897 | 1.00 | 36.36 |
| ATOM | 3243 | N | ASN | C | 304 | 64.018 | −4.352 | 147.701 | 1.00 | 33.31 |
| ATOM | 3244 | CA | ASN | C | 304 | 64.945 | −3.589 | 148.552 | 1.00 | 30.86 |
| ATOM | 3245 | CB | ASN | C | 304 | 66.364 | −4.182 | 148.510 | 1.00 | 29.77 |
| ATOM | 3246 | CG | ASN | C | 304 | 67.167 | −3.841 | 149.758 | 1.00 | 28.46 |
| ATOM | 3247 | OD1 | ASN | C | 304 | 66.684 | −4.013 | 150.879 | 1.00 | 28.50 |
| ATOM | 3248 | ND2 | ASN | C | 304 | 68.391 | −3.362 | 149.572 | 1.00 | 27.02 |
| ATOM | 3249 | C | ASN | C | 304 | 64.993 | −2.090 | 148.219 | 1.00 | 28.19 |
| ATOM | 3250 | O | ASN | C | 304 | 65.943 | −1.382 | 148.570 | 1.00 | 26.02 |
| ATOM | 3251 | N | LEU | C | 305 | 63.960 | −1.627 | 147.525 | 1.00 | 26.97 |
| ATOM | 3252 | CA | LEU | C | 305 | 63.822 | −0.221 | 147.184 | 1.00 | 26.40 |
| ATOM | 3253 | CB | LEU | C | 305 | 63.367 | −0.049 | 145.746 | 1.00 | 25.25 |
| ATOM | 3254 | CG | LEU | C | 305 | 64.444 | −0.319 | 144.700 | 1.00 | 26.05 |
| ATOM | 3255 | CD1 | LEU | C | 305 | 63.876 | −0.007 | 143.342 | 1.00 | 23.07 |
| ATOM | 3256 | CD2 | LEU | C | 305 | 65.682 | 0.533 | 144.969 | 1.00 | 24.19 |
| ATOM | 3257 | C | LEU | C | 305 | 62.744 | 0.305 | 148.108 | 1.00 | 26.14 |
| ATOM | 3258 | O | LEU | C | 305 | 61.854 | −0.439 | 148.503 | 1.00 | 26.57 |
| ATOM | 3259 | N | PRO | C | 306 | 62.819 | 1.590 | 148.481 | 1.00 | 26.10 |
| ATOM | 3260 | CD | PRO | C | 306 | 63.836 | 2.588 | 148.101 | 1.00 | 25.28 |
| ATOM | 3261 | CA | PRO | C | 306 | 61.816 | 2.179 | 149.370 | 1.00 | 25.56 |
| ATOM | 3262 | CB | PRO | C | 306 | 62.455 | 3.501 | 149.762 | 1.00 | 24.30 |
| ATOM | 3263 | CG | PRO | C | 306 | 63.188 | 3.888 | 148.525 | 1.00 | 23.16 |
| ATOM | 3264 | C | PRO | C | 306 | 60.492 | 2.376 | 148.640 | 1.00 | 25.91 |
| ATOM | 3265 | O | PRO | C | 306 | 60.492 | 2.692 | 147.452 | 1.00 | 25.20 |
| ATOM | 3266 | N | TYR | C | 307 | 59.371 | 2.159 | 149.334 | 1.00 | 27.62 |
| ATOM | 3267 | CA | TYR | C | 307 | 58.062 | 2.369 | 148.715 | 1.00 | 28.20 |
| ATOM | 3268 | CB | TYR | C | 307 | 56.905 | 1.803 | 149.536 | 1.00 | 26.18 |
| ATOM | 3269 | CG | TYR | C | 307 | 56.993 | 0.348 | 149.908 | 1.00 | 27.94 |
| ATOM | 3270 | CD1 | TYR | C | 307 | 57.401 | −0.026 | 151.188 | 1.00 | 28.66 |
| ATOM | 3271 | CE1 | TYR | C | 307 | 57.417 | −1.348 | 151.585 | 1.00 | 29.63 |
| ATOM | 3272 | CD2 | TYR | C | 307 | 56.609 | −0.658 | 149.011 | 1.00 | 28.66 |
| ATOM | 3273 | CE2 | TYR | C | 307 | 56.626 | −2.010 | 149.395 | 1.00 | 30.48 |
| ATOM | 3274 | CZ | TYR | C | 307 | 57.031 | −2.344 | 150.697 | 1.00 | 31.89 |
| ATOM | 3275 | OH | TYR | C | 307 | 57.041 | −3.660 | 151.140 | 1.00 | 33.12 |
| ATOM | 3276 | C | TYR | C | 307 | 57.921 | 3.872 | 148.712 | 1.00 | 29.73 |
| ATOM | 3277 | O | TYR | C | 307 | 58.328 | 4.547 | 149.669 | 1.00 | 33.14. |
| ATOM | 3278 | N | VAL | C | 308 | 57.357 | 4.413 | 147.647 | 1.00 | 29.62 |
| ATOM | 3279 | CA | VAL | C | 308 | 57.198 | 5.854 | 147.574 | 1.00 | 30.67 |
| ATOM | 3280 | CB | VAL | C | 308 | 58.365 | 6.549 | 146.792 | 1.00 | 29.93 |
| ATOM | 3281 | CG1 | VAL | C | 308 | 59.674 | 6.405 | 147.548 | 1.00 | 27.84 |
| ATOM | 3282 | CG2 | VAL | C | 308 | 58.475 | 5.970 | 145.385 | 1.00 | 28.19 |
| ATOM | 3283 | C | VAL | C | 308 | 55.914 | 6.270 | 146.900 | 1.00 | 30.97 |
| ATOM | 3284 | O | VAL | C | 308 | 55.169 | 5.455 | 146.369 | 1.00 | 31.26 |
| ATOM | 3285 | N | GLN | C | 309 | 55.669 | 7.568 | 146.936 | 1.00 | 31.96 |
| ATOM | 3286 | CA | GLN | C | 309 | 54.507 | 8.143 | 146.301 | 1.00 | 32.13 |
| ATOM | 3287 | CB | GLN | C | 309 | 53.478 | 8.551 | 147.343 | 1.00 | 35.21 |
| ATOM | 3288 | CG | GLN | C | 309 | 52.068 | 8.678 | 146.790 | 1.00 | 39.73 |
| ATOM | 3289 | CD | GLN | C | 309 | 51.135 | 9.417 | 147.740 | 1.00 | 43.61 |
| ATOM | 3290 | OE1 | GLN | C | 309 | 51.085 | 9.130 | 148.951 | 1.00 | 43.88 |
| ATOM | 3291 | NE2 | GLN | C | 309 | 50.383 | 10.373 | 147.196 | 1.00 | 44.33 |
| ATOM | 3292 | C | GLN | C | 309 | 55.014 | 9.369 | 145.551 | 1.00 | 30.79 |
| ATOM | 3293 | O | GLN | C | 309 | 55.503 | 10.327 | 146.164 | 1.00 | 30.26 |
| ATOM | 3294 | N | ILE | C | 310 | 54.921 | 9.321 | 144.223 | 1.00 | 29.07 |
| ATOM | 3295 | CA | ILE | C | 310 | 55.371 | 10.426 | 143.383 | 1.00 | 27.14 |
| ATOM | 3296 | CB | ILE | C | 310 | 55.444 | 9.999 | 141.891 | 1.00 | 28.09 |
| ATOM | 3297 | CG2 | ILE | C | 310 | 55.996 | 11.139 | 141.033 | 1.00 | 26.15 |
| ATOM | 3298 | CG1 | ILE | C | 310 | 56.311 | 8.737 | 141.749 | 1.00 | 29.18 |
| ATOM | 3299 | CD1 | ILE | C | 310 | 57.788 | 8.919 | 142.119 | 1.00 | 28.63 |
| ATOM | 3300 | C | ILE | C | 310 | 54.390 | 11.576 | 143.537 | 1.00 | 25.01 |
| ATOM | 3301 | O | ILE | C | 310 | 53.251 | 11.490 | 143.105 | 1.00 | 25.36 |
| ATOM | 3302 | N | LEU | C | 311 | 54.841 | 12.653 | 144.157 | 1.00 | 24.70 |

TABLE 1-continued

FGFR1 D2–D3 Complexed with FGF2

| ATOM | 3303 | CA | LEU | C | 311 | 53.990 | 13.814 | 144.384 | 1.00 | 25.69 |
|------|------|-----|-----|---|-----|--------|--------|---------|------|-------|
| ATOM | 3304 | CB | LEU | C | 311 | 54.337 | 14.445 | 145.727 | 1.00 | 25.71 |
| ATOM | 3305 | CG | LEU | C | 311 | 54.135 | 13.504 | 146.904 | 1.00 | 26.24 |
| ATOM | 3306 | CD1 | LEU | C | 311 | 54.581 | 14.187 | 148.192 | 1.00 | 24.44 |
| ATOM | 3307 | CD2 | LEU | C | 311 | 52.662 | 13.085 | 146.951 | 1.00 | 24.28 |
| ATOM | 3308 | C | LEU | C | 311 | 54.055 | 14.897 | 143.320 | 1.00 | 25.46 |
| ATOM | 3309 | O | LEU | C | 311 | 53.068 | 15.573 | 143.059 | 1.00 | 24.77 |
| ATOM | 3310 | N | LYS | C | 312 | 55.221 | 15.064 | 142.713 | 1.00 | 28.01 |
| ATOM | 3311 | CA | LYS | C | 312 | 55.423 | 16.101 | 141.708 | 1.00 | 28.31 |
| ATOM | 3312 | CB | LYS | C | 312 | 55.815 | 17.390 | 142.416 | 1.00 | 26.66 |
| ATOM | 3313 | CG | LYS | C | 312 | 55.503 | 18.663 | 141.688 | 1.00 | 27.67 |
| ATOM | 3314 | CD | LYS | C | 312 | 55.802 | 19.812 | 142.648 | 1.00 | 31.49 |
| ATOM | 3315 | CE | LYS | C | 312 | 55.176 | 21.138 | 142.240 | 1.00 | 32.20 |
| ATOM | 3316 | NZ | LYS | C | 312 | 55.054 | 22.009 | 143.455 | 1.00 | 34.04 |
| ATOM | 3317 | C | LYS | C | 312 | 56.543 | 15.666 | 140.777 | 1.00 | 29.40 |
| ATOM | 3318 | O | LYS | C | 312 | 57.539 | 15.082 | 141.212 | 1.00 | 29.77 |
| ATOM | 3319 | N | THR | C | 313 | 56.384 | 15.957 | 139.494 | 1.00 | 31.02 |
| ATOM | 3320 | CA | THR | C | 313 | 57.379 | 15.571 | 138.498 | 1.00 | 30.41 |
| ATOM | 3321 | CB | THR | C | 313 | 56.977 | 14.268 | 137.775 | 1.00 | 28.36 |
| ATOM | 3322 | OG1 | THR | C | 313 | 56.976 | 13.177 | 138.699 | 1.00 | 28.72 |
| ATOM | 3323 | CG2 | THR | C | 313 | 57.938 | 13.963 | 136.667 | 1.00 | 28.33 |
| ATOM | 3324 | C | THR | C | 313 | 57.455 | 16.660 | 137.455 | 1.00 | 31.24 |
| ATOM | 3325 | O | THR | C | 313 | 56.443 | 17.004 | 136.836 | 1.00 | 32.10 |
| ATOM | 3326 | N | ALA | C | 314 | 58.652 | 17.193 | 137.252 | 1.00 | 31.41 |
| ATOM | 3327 | CA | ALA | C | 314 | 58.833 | 18.251 | 136.280 | 1.00 | 31.45 |
| ATOM | 3328 | CB | ALA | C | 314 | 60.237 | 18.823 | 136.386 | 1.00 | 33.93 |
| ATOM | 3329 | C | ALA | C | 314 | 58.562 | 17.751 | 134.867 | 1.00 | 31.70 |
| ATOM | 3330 | O | ALA | C | 314 | 58.722 | 16.564 | 134.553 | 1.00 | 29.10 |
| ATOM | 3331 | N | GLY | C | 315 | 58.139 | 18.685 | 134.024 | 1.00 | 32.86 |
| ATOM | 3332 | CA | GLY | C | 315 | 57.841 | 18.382 | 132.637 | 1.00 | 32.44 |
| ATOM | 3333 | C | GLY | C | 315 | 56.946 | 19.480 | 132.105 | 1.00 | 33.40 |
| ATOM | 3334 | O | GLY | C | 315 | 56.619 | 20.441 | 132.825 | 1.00 | 31.86 |
| ATOM | 3335 | N | VAL | C | 316 | 56.540 | 19.335 | 130.852 | 1.00 | 34.05 |
| ATOM | 3336 | CA | VAL | C | 316 | 55.671 | 20.308 | 130.209 | 1.00 | 35.92 |
| ATOM | 3337 | CB | VAL | C | 316 | 55.232 | 19.778 | 128.842 | 1.00 | 36.34 |
| ATOM | 3338 | CG1 | VAL | C | 316 | 54.425 | 20.823 | 128.120 | 1.00 | 39.31 |
| ATOM | 3339 | CG2 | VAL | C | 316 | 56.454 | 19.377 | 128.030 | 1.00 | 35.78 |
| ATOM | 3340 | C | VAL | C | 316 | 54.428 | 20.655 | 131.046 | 1.00 | 37.44 |
| ATOM | 3341 | O | VAL | C | 316 | 53.952 | 21.797 | 131.030 | 1.00 | 37.25 |
| ATOM | 3342 | N | ASN | C | 317 | 53.912 | 19.675 | 131.781 | 1.00 | 39.86 |
| ATOM | 3343 | CA | ASN | C | 317 | 52.724 | 19.890 | 132.605 | 1.00 | 42.60 |
| ATOM | 3344 | CB | ASN | C | 317 | 52.032 | 18.554 | 132.889 | 1.00 | 47.26 |
| ATOM | 3345 | CG | ASN | C | 317 | 51.391 | 17.949 | 131.647 | 1.00 | 51.28 |
| ATOM | 3346 | OD1 | ASN | C | 317 | 51.088 | 16.742 | 131.617 | 1.00 | 54.31 |
| ATOM | 3347 | ND2 | ASN | C | 317 | 51.169 | 18.780 | 130.617 | 1.00 | 48.94 |
| ATOM | 3348 | C | ASN | C | 317 | 53.043 | 20.581 | 133.917 | 1.00 | 41.85 |
| ATOM | 3349 | O | ASN | C | 317 | 52.172 | 21.186 | 134.542 | 1.00 | 43.36 |
| ATOM | 3350 | N | THR | C | 318 | 54.296 | 20.500 | 134.329 | 1.00 | 41.46 |
| ATOM | 3351 | CA | THR | C | 318 | 54.697 | 21.103 | 135.580 | 1.00 | 41.12 |
| ATOM | 3352 | CB | THR | C | 318 | 54.752 | 20.038 | 136.666 | 1.00 | 40.65 |
| ATOM | 3353 | OG1 | THR | C | 318 | 53.820 | 18.998 | 136.341 | 1.00 | 38.74 |
| ATOM | 3354 | CG2 | THR | C | 318 | 54.396 | 20.636 | 138.009 | 1.00 | 40.04 |
| ATOM | 3355 | C | THR | C | 318 | 56.074 | 21.665 | 135.354 | 1.00 | 41.10 |
| ATOM | 3356 | O | THR | C | 318 | 57.071 | 20.983 | 135.577 | 1.00 | 42.97 |
| ATOM | 3357 | N | THR | C | 319 | 56.115 | 22.907 | 134.893 | 1.00 | 40.14 |
| ATOM | 3358 | CA | THR | C | 319 | 57.358 | 23.602 | 134.593 | 1.00 | 39.06 |
| ATOM | 3359 | CB | THR | C | 319 | 57.024 | 24.935 | 133.912 | 1.00 | 39.04 |
| ATOM | 3360 | OG1 | THR | C | 319 | 56.341 | 24.643 | 132.692 | 1.00 | 38.77 |
| ATOM | 3361 | CG2 | THR | C | 319 | 58.280 | 25.752 | 133.604 | 1.00 | 40.60 |
| ATOM | 3362 | C | THR | C | 319 | 58.257 | 23.829 | 135.806 | 1.00 | 38.67 |
| ATOM | 3363 | O | THR | C | 319 | 57.785 | 23.867 | 136.950 | 1.00 | 38.34 |
| ATOM | 3364 | N | ASP | C | 320 | 59.558 | 23.966 | 135.543 | 1.00 | 38.76 |
| ATOM | 3365 | CA | ASP | C | 320 | 60.549 | 24.192 | 136.591 | 1.00 | 38.55 |
| ATOM | 3366 | CB | ASP | C | 320 | 61.916 | 24.518 | 135.966 | 1.00 | 39.25 |
| ATOM | 3367 | CG | ASP | C | 320 | 62.509 | 23.331 | 135.169 | 1.00 | 42.22 |
| ATOM | 3368 | OD1 | ASP | C | 320 | 62.255 | 22.158 | 135.537 | 1.00 | 40.72 |
| ATOM | 3369 | OD2 | ASP | C | 320 | 63.249 | 23.566 | 134.182 | 1.00 | 43.42 |
| ATOM | 3370 | C | ASP | C | 320 | 60.091 | 25.301 | 137.541 | 1.00 | 39.21 |
| ATOM | 3371 | O | ASP | C | 320 | 60.411 | 25.297 | 138.725 | 1.00 | 39.71 |
| ATOM | 3372 | N | LYS | C | 321 | 59.316 | 26.235 | 137.019 | 1.00 | 40.34 |
| ATOM | 3373 | CA | LYS | C | 321 | 58.786 | 27.326 | 137.816 | 1.00 | 42.35 |
| ATOM | 3374 | CB | LYS | C | 321 | 57.611 | 27.978 | 137.065 | 1.00 | 45.75 |
| ATOM | 3375 | CG | LYS | C | 321 | 57.946 | 28.373 | 135.620 | 1.00 | 48.28 |
| ATOM | 3376 | CD | LYS | C | 321 | 56.750 | 28.912 | 134.826 | 1.00 | 47.90 |
| ATOM | 3377 | CE | LYS | C | 321 | 57.182 | 29.250 | 133.386 | 1.00 | 48.35 |
| ATOM | 3378 | NZ | LYS | C | 321 | 56.043 | 29.601 | 132.490 | 1.00 | 47.69 |
| ATOM | 3379 | C | LYS | C | 321 | 58.299 | 26.824 | 139.177 | 1.00 | 42.50 |

TABLE 1-continued

FGFR1 D2–D3 Complexed with FGF2

| | | | | | | | | | | |
|---|---|---|---|---|---|---|---|---|---|---|
| ATOM | 3380 | O | LYS | C | 321 | 58.761 | 27.269 | 140.226 | 1.00 | 42.89 |
| ATOM | 3381 | N | GLU | C | 322 | 57.367 | 25.880 | 139.154 | 1.00 | 43.54 |
| ATOM | 3382 | CA | GLU | C | 322 | 56.795 | 25.348 | 140.392 | 1.00 | 44.10 |
| ATOM | 3383 | CB | GLU | C | 322 | 55.336 | 25.006 | 140.161 | 1.00 | 48.31 |
| ATOM | 3384 | CG | GLU | C | 322 | 55.136 | 24.231 | 138.883 | 1.00 | 53.89 |
| ATOM | 3385 | CD | GLU | C | 322 | 54.083 | 24.874 | 138.017 | 1.00 | 59.22 |
| ATOM | 3386 | OE1 | GLU | C | 322 | 52.923 | 24.926 | 138.477 | 1.00 | 62.81 |
| ATOM | 3387 | OE2 | GLU | C | 322 | 54.405 | 25.337 | 136.894 | 1.00 | 62.06 |
| ATOM | 3388 | C | GLU | C | 322 | 57.474 | 24.127 | 140.995 | 1.00 | 41.62 |
| ATOM | 3389 | O | GLU | C | 322 | 57.074 | 23.672 | 142.058 | 1.00 | 40.29 |
| ATOM | 3390 | N | MET | C | 323 | 58.504 | 23.608 | 140.336 | 1.00 | 40.18 |
| ATOM | 3391 | CA | MET | C | 323 | 59.192 | 22.413 | 140.820 | 1.00 | 39.72 |
| ATOM | 3392 | CB | MET | C | 323 | 59.988 | 21.774 | 139.680 | 1.00 | 39.74 |
| ATOM | 3393 | CG | MET | C | 323 | 59.121 | 21.110 | 138.625 | 1.00 | 39.00 |
| ATOM | 3394 | SD | MET | C | 323 | 57.926 | 20.007 | 139.397 | 1.00 | 39.79 |
| ATOM | 3395 | CE | MET | C | 323 | 59.044 | 18.760 | 140.122 | 1.00 | 39.54 |
| ATOM | 3396 | C | MET | C | 323 | 60.103 | 22.524 | 142.041 | 1.00 | 39.88 |
| ATOM | 3397 | O | MET | C | 323 | 60.452 | 21.507 | 142.639 | 1.00 | 38.86 |
| ATOM | 3398 | N | GLU | C | 324 | 60.482 | 23.738 | 142.421 | 1.00 | 40.42 |
| ATOM | 3399 | C | GLU | C | 324 | 61.373 | 23.914 | 143.557 | 1.00 | 41.47 |
| ATOM | 3400 | CB | GLU | C | 324 | 62.209 | 25.174 | 143.346 | 1.00 | 45.26 |
| ATOM | 3401 | CG | GLU | C | 324 | 63.055 | 25.135 | 142.076 | 1.00 | 50.92 |
| ATOM | 3402 | CD | GLU | C | 324 | 64.212 | 26.137 | 142.092 | 1.00 | 54.85 |
| ATOM | 3403 | OE1 | GLU | C | 324 | 63.950 | 27.366 | 142.190 | 1.00 | 54.81 |
| ATOM | 3404 | OE2 | GLU | C | 324 | 65.383 | 25.685 | 142.006 | 1.00 | 55.29 |
| ATOM | 3405 | C | GLU | C | 324 | 60.697 | 23.960 | 144.929 | 1.00 | 40.67 |
| ATOM | 3406 | O | GLU | C | 324 | 61.368 | 23.958 | 145.966 | 1.00 | 41.14 |
| ATOM | 3407 | N | VAL | C | 325 | 59.373 | 23.993 | 144.953 | 1.00 | 39.72 |
| ATOM | 3408 | CA | VAL | C | 325 | 58.682 | 24.040 | 146.232 | 1.00 | 38.08 |
| ATOM | 3409 | CB | VAL | C | 325 | 58.220 | 25.487 | 146.546 | 1.00 | 36.29 |
| ATOM | 3410 | CG1 | VAL | C | 325 | 57.039 | 25.857 | 145.672 | 1.00 | 36.51 |
| ATOM | 3411 | CG2 | VAL | C | 325 | 57.893 | 25.633 | 148.015 | 1.00 | 36.14 |
| ATOM | 3412 | C | VAL | C | 325 | 57.500 | 23.072 | 146.254 | 1.00 | 38.56 |
| ATOM | 3413 | O | VAL | C | 325 | 56.651 | 23.074 | 145.357 | 1.00 | 38.82 |
| ATOM | 3414 | N | LEU | C | 326 | 57.471 | 22.216 | 147.269 | 1.00 | 38.14 |
| ATOM | 3415 | CA | LEU | C | 326 | 56.389 | 21.255 | 147.400 | 1.00 | 37.67 |
| ATOM | 3416 | CB | LEU | C | 326 | 56.896 | 19.891 | 147.879 | 1.00 | 35.37 |
| ATOM | 3417 | CG | LEU | C | 326 | 55.745 | 18.891 | 148.008 | 1.00 | 31.23 |
| ATOM | 3418 | CD1 | LEU | C | 326 | 55.376 | 18.418 | 146.637 | 1.00 | 28.32 |
| ATOM | 3419 | CD2 | LEU | C | 326 | 56.132 | 17.727 | 148.891 | 1.00 | 31.14 |
| ATOM | 3420 | C | LEU | C | 326 | 55.396 | 21.796 | 148.403 | 1.00 | 37.92 |
| ATOM | 3421 | O | LEU | C | 326 | 55.751 | 22.088 | 149.544 | 1.00 | 36.88 |
| ATOM | 3422 | N | HIS | C | 327 | 54.148 | 21.917 | 147.969 | 1.00 | 39.27 |
| ATOM | 3423 | CA | HIS | C | 327 | 53.085 | 22.430 | 148.820 | 1.00 | 41.32 |
| ATOM | 3424 | CE | HIS | C | 327 | 52.188 | 23.363 | 148.021 | 1.00 | 41.71 |
| ATOM | 3425 | CG | HIS | C | 327 | 52.802 | 24.693 | 147.740 | 1.00 | 43.39 |
| ATOM | 3426 | CD2 | HIS | C | 327 | 53.144 | 25.288 | 146.573 | 1.00 | 43.33 |
| ATOM | 3427 | ND1 | HIS | C | 327 | 53.132 | 25.582 | 148.740 | 1.00 | 42.70 |
| ATOM | 3428 | CE1 | HIS | C | 327 | 53.653 | 26.669 | 148.200 | 1.00 | 43.09 |
| ATOM | 3429 | NE2 | HIS | C | 327 | 53.673 | 26.517 | 146.888 | 1.00 | 43.55 |
| ATOM | 3430 | C | HIS | C | 327 | 52.207 | 21.363 | 149.452 | 1.00 | 42.33 |
| ATOM | 3431 | O | HIS | C | 327 | 51.644 | 20.517 | 148.761 | 1.00 | 42.42 |
| ATOM | 3432 | N | LEU | C | 328 | 52.083 | 21.412 | 150.769 | 1.00 | 43.08 |
| ATOM | 3433 | CA | LEU | C | 328 | 51.236 | 20.473 | 151.471 | 1.00 | 45.11 |
| ATOM | 3434 | CB | LEU | C | 328 | 52.029 | 19.708 | 152.528 | 1.00 | 42.60 |
| ATOM | 3435 | CG | LEU | C | 328 | 53.090 | 18.732 | 152.010 | 1.00 | 42.77 |
| ATOM | 3436 | CD1 | LEU | C | 328 | 53.743 | 18.001 | 153.175 | 1.00 | 42.02 |
| ATOM | 3437 | CD2 | LEU | C | 328 | 52.450 | 17.730 | 151.064 | 1.00 | 41.50 |
| ATOM | 3438 | C | LEU | C | 328 | 50.160 | 21.315 | 152.127 | 1.00 | 48.64 |
| ATOM | 3439 | O | LEU | C | 328 | 50.415 | 21.977 | 153.134 | 1.00 | 49.49 |
| ATOM | 3440 | N | ARG | C | 329 | 48.963 | 21.302 | 151.540 | 1.00 | 51.46 |
| ATOM | 3441 | CA | ARG | C | 329 | 47.839 | 22.076 | 152.056 | 1.00 | 53.13 |
| ATOM | 3442 | CE | ARG | C | 329 | 46.903 | 22.470 | 150.913 | 1.00 | 53.63 |
| ATOM | 3443 | C | ARG | C | 329 | 47.057 | 21.332 | 153.132 | 1.00 | 54.77 |
| ATOM | 3444 | O | ARG | C | 329 | 46.577 | 20.220 | 152.916 | 1.00 | 55.60 |
| ATOM | 3445 | N | ASN | C | 330 | 46.942 | 21.963 | 154.296 | 1.00 | 56.97 |
| ATOM | 3446 | CA | ASN | C | 330 | 46.218 | 21.399 | 155.429 | 1.00 | 59.20 |
| ATOM | 3447 | CE | ASN | C | 330 | 44.717 | 21.477 | 155.161 | 1.00 | 60.58 |
| ATOM | 3448 | CG | ASN | C | 330 | 43.897 | 21.255 | 156.407 | 1.00 | 62.83 |
| ATOM | 3449 | OD1 | ASN | C | 330 | 44.112 | 20.292 | 157.148 | 1.00 | 63.10 |
| ATOM | 3450 | ND2 | ASN | C | 330 | 42.940 | 22.146 | 156.646 | 1.00 | 64.41 |
| ATOM | 3451 | C | ASN | C | 330 | 46.636 | 19.948 | 155.658 | 1.00 | 59.55 |
| ATOM | 3452 | O | ASN | C | 330 | 46.059 | 19.029 | 155.085 | 1.00 | 60.48 |
| ATOM | 3453 | N | VAL | C | 331 | 47.636 | 19.747 | 156.504 | 1.00 | 60.31 |
| ATOM | 3454 | CA | VAL | C | 331 | 48.146 | 18.409 | 156.771 | 1.00 | 60.52 |
| ATOM | 3455 | CE | VAL | C | 331 | 49.606 | 18.486 | 157.308 | 1.00 | 59.96 |
| ATOM | 3456 | CG1 | VAL | C | 331 | 50.527 | 19.031 | 156.223 | 1.00 | 58.15 |

TABLE 1-continued

FGFR1 D2–D3 Complexed with FGF2

| ATOM | 3457 | CG2 | VAL | C | 331 | 49.672 | 19.380 | 158.535 | 1.00 | 58.53 |
|---|---|---|---|---|---|---|---|---|---|---|
| ATOM | 3458 | C | VAL | C | 331 | 47.288 | 17.590 | 157.732 | 1.00 | 60.66 |
| ATOM | 3459 | O | VAL | C | 331 | 46.274 | 18.061 | 158.239 | 1.00 | 60.55 |
| ATOM | 3460 | N | SER | C | 332 | 47.709 | 16.354 | 157.960 | 1.00 | 61.41 |
| ATOM | 3461 | CA | SER | C | 332 | 47.022 | 15.436 | 158.852 | 1.00 | 62.88 |
| ATOM | 3462 | CE | SER | C | 332 | 45.915 | 14.709 | 158.101 | 1.00 | 64.75 |
| ATOM | 3463 | OG | SER | C | 332 | 46.449 | 14.058 | 156.962 | 1.00 | 66.80 |
| ATOM | 3464 | C | SER | C | 332 | 48.066 | 14.440 | 159.312 | 1.00 | 62.96 |
| ATOM | 3465 | O | SER | C | 332 | 49.115 | 14.323 | 158.692 | 1.00 | 63.04 |
| ATOM | 3466 | N | PHE | C | 333 | 47.790 | 13.724 | 160.394 | 1.00 | 64.54 |
| ATOM | 3467 | CA | PHE | C | 333 | 48.748 | 12.747 | 160.900 | 1.00 | 65.91 |
| ATOM | 3468 | CB | PHE | C | 333 | 48.126 | 11.899 | 162.011 | 1.00 | 68.96 |
| ATOM | 3469 | CG | PHE | C | 333 | 48.270 | 12.489 | 163.390 | 1.00 | 72.38 |
| ATOM | 3470 | CD1 | PHE | C | 333 | 48.503 | 11.654 | 164.493 | 1.00 | 73.39 |
| ATOM | 3471 | CD2 | PHE | C | 333 | 48.151 | 13.864 | 163.595 | 1.00 | 73.19 |
| ATOM | 3472 | CE1 | PHE | C | 333 | 48.613 | 12.178 | 165.782 | 1.00 | 74.33 |
| ATOM | 3473 | CE2 | PHE | C | 333 | 48.259 | 14.402 | 164.879 | 1.00 | 74.97 |
| ATOM | 3474 | CZ | PHE | C | 333 | 48.493 | 13.554 | 165.978 | 1.00 | 75.37 |
| ATOM | 3475 | C | PHE | C | 333 | 49.239 | 11.828 | 159.786 | 1.00 | 65.14 |
| ATOM | 3476 | O | PHE | C | 333 | 50.341 | 11.279 | 159.855 | 1.00 | 64.30 |
| ATOM | 3477 | N | GLU | C | 334 | 48.405 | 11.675 | 158.764 | 1.00 | 64.25 |
| ATOM | 3478 | CA | GLU | C | 334 | 48.708 | 10.831 | 157.615 | 1.00 | 63.39 |
| ATOM | 3479 | CB | GLU | C | 334 | 47.497 | 10.792 | 156.677 | 1.00 | 66.69 |
| ATOM | 3480 | CG | GLU | C | 334 | 46.149 | 11.068 | 157.374 | 1.00 | 70.10 |
| ATOM | 3481 | CD | GLU | C | 334 | 45.096 | 11.684 | 156.439 | 1.00 | 72.14 |
| ATOM | 3482 | OE1 | GLU | C | 334 | 43.985 | 12.006 | 156.924 | 1.00 | 72.03 |
| ATOM | 3483 | OE2 | GLU | C | 334 | 45.378 | 11.849 | 155.225 | 1.00 | 72.85 |
| ATOM | 3484 | C | GLU | C | 334 | 49.905 | 11.399 | 156.856 | 1.00 | 60.52 |
| ATOM | 3485 | O | GLU | C | 334 | 50.863 | 10.686 | 156.557 | 1.00 | 60.51 |
| ATOM | 3486 | N | ASP | C | 335 | 49.832 | 12.690 | 156.549 | 1.00 | 56.90 |
| ATOM | 3487 | CA | ASP | C | 335 | 50.882 | 13.388 | 155.811 | 1.00 | 53.14 |
| ATOM | 3488 | CB | ASP | C | 335 | 50.476 | 14.842 | 155.564 | 1.00 | 53.78 |
| ATOM | 3489 | CG | ASP | C | 335 | 49.223 | 14.968 | 154.723 | 1.00 | 54.03 |
| ATOM | 3490 | OD1 | ASP | C | 335 | 49.229 | 14.518 | 153.555 | 1.00 | 53.72 |
| ATOM | 3491 | OD2 | ASP | C | 335 | 48.231 | 15.530 | 155.235 | 1.00 | 55.24 |
| ATOM | 3492 | C | ASP | C | 335 | 52.261 | 13.376 | 156.476 | 1.00 | 50.25 |
| ATOM | 3493 | O | ASP | C | 335 | 53.261 | 13.720 | 155.846 | 1.00 | 49.76 |
| ATOM | 3494 | N | ALA | C | 336 | 52.327 | 13.006 | 157.748 | 1.00 | 45.93 |
| ATOM | 3495 | CA | ALA | C | 336 | 53.617 | 12.972 | 158.418 | 1.00 | 43.25 |
| ATOM | 3496 | CB | ALA | C | 336 | 53.462 | 12.516 | 159.863 | 1.00 | 44.14 |
| ATOM | 3497 | C | ALA | C | 336 | 54.498 | 12.002 | 157.656 | 1.00 | 41.41 |
| ATOM | 3498 | O | ALA | C | 336 | 54.009 | 11.154 | 156.921 | 1.00 | 41.75 |
| ATOM | 3499 | N | GLY | C | 337 | 55.803 | 12.120 | 157.825 | 1.00 | 39.43 |
| ATOM | 3500 | CA | GLY | C | 337 | 56.689 | 11.221 | 157.115 | 1.00 | 36.79 |
| ATOM | 3501 | C | GLY | C | 337 | 57.793 | 11.926 | 156.354 | 1.00 | 34.67 |
| ATOM | 3502 | O | GLY | C | 337 | 57.866 | 13.150 | 156.308 | 1.00 | 35.77 |
| ATOM | 3503 | N | GLU | C | 338 | 58.652 | 11.131 | 155.740 | 1.00 | 32.73 |
| ATOM | 3504 | CA | GLU | C | 338 | 59.788 | 11.632 | 154.982 | 1.00 | 30.27 |
| ATOM | 3505 | CB | GLU | C | 338 | 60.866 | 10.562 | 154.953 | 1.00 | 29.00 |
| ATOM | 3506 | CG | GLU | C | 338 | 62.067 | 10.917 | 154.143 | 1.00 | 30.51 |
| ATOM | 3507 | CD | GLU | C | 338 | 63.198 | 9.949 | 154.375 | 1.00 | 31.47 |
| ATOM | 3508 | OD1 | GLU | C | 338 | 62.982 | 8.743 | 154.134 | 1.00 | 29.99 |
| ATOM | 3509 | OE2 | GLU | C | 338 | 64.292 | 10.400 | 154.807 | 1.00 | 32.90 |
| ATOM | 3510 | C | GLU | C | 338 | 59.469 | 12.047 | 153.551 | 1.00 | 28.43 |
| ATOM | 3511 | O | GLU | C | 338 | 58.915 | 11.276 | 152.772 | 1.00 | 28.10 |
| ATOM | 3512 | N | TYR | C | 339 | 59.830 | 13.274 | 153.206 | 1.00 | 27.27 |
| ATOM | 3513 | CA | TYR | C | 339 | 59.613 | 13.768 | 151.857 | 1.00 | 25.56 |
| ATOM | 3514 | CB | TYR | C | 339 | 58.848 | 15.080 | 151.888 | 1.00 | 22.41 |
| ATOM | 3515 | CG | TYR | C | 339 | 57.407 | 14.869 | 152.267 | 1.00 | 20.77 |
| ATOM | 3516 | CD1 | TYR | C | 339 | 57.039 | 14.638 | 153.594 | 1.00 | 19.97 |
| ATOM | 3517 | CE1 | TYR | C | 339 | 55.719 | 14.387 | 153.937 | 1.00 | 19.82 |
| ATOM | 3518 | CD2 | TYR | C | 339 | 56.416 | 14.844 | 151.294 | 1.00 | 18.89 |
| ATOM | 3519 | CE2 | TYR | C | 339 | 55.104 | 14.593 | 151.623 | 1.00 | 19.97 |
| ATOM | 3520 | CZ | TYR | C | 339 | 54.755 | 14.363 | 152.945 | 1.00 | 20.30 |
| ATOM | 3521 | OH | TYR | C | 339 | 53.435 | 14.097 | 153.260 | 1.00 | 23.03 |
| ATOM | 3522 | C | TYR | C | 339 | 60.978 | 13.940 | 151.219 | 1.00 | 25.76 |
| ATOM | 3523 | O | TYR | C | 339 | 61.920 | 14.404 | 151.863 | 1.00 | 25.02 |
| ATOM | 3524 | N | THR | C | 340 | 61.077 | 13.560 | 149.950 | 1.00 | 25.99 |
| ATOM | 3525 | CA | THR | C | 340 | 62.345 | 13.606 | 149.241 | 1.00 | 26.36 |
| ATOM | 3526 | CB | THR | C | 340 | 62.814 | 12.168 | 148.890 | 1.00 | 24.39 |
| ATOM | 3527 | OG1 | THR | C | 340 | 63.094 | 11.447 | 150.095 | 1.00 | 23.87 |
| ATOM | 3528 | CG2 | THR | C | 340 | 64.059 | 12.204 | 148.046 | 1.00 | 24.52 |
| ATOM | 3529 | C | THR | C | 340 | 62.325 | 14.409 | 147.957 | 1.00 | 27.11 |
| ATOM | 3530 | O | THR | C | 340 | 61.365 | 14.350 | 147.189 | 1.00 | 27.36 |
| ATOM | 3531 | N | CYS | C | 341 | 63.403 | 15.152 | 147.731 | 1.00 | 26.79 |
| ATOM | 3532 | CA | CYS | C | 341 | 63.548 | 15.940 | 146.521 | 1.00 | 27.05 |
| ATOM | 3533 | C | CYS | C | 341 | 64.636 | 15.325 | 145.654 | 1.00 | 28.59 |

TABLE 1-continued

FGFR1 D2–D3 Complexed with FGF2

| ATOM | 3534 | O | CYS | C | 341 | 65.806 | 15.303 | 146.046 | 1.00 | 29.17 |
|---|---|---|---|---|---|---|---|---|---|---|
| ATOM | 3535 | CB | CYS | C | 341 | 63.946 | 17.365 | 146.853 | 1.00 | 25.54 |
| ATOM | 3536 | SG | CYS | C | 341 | 64.337 | 18.352 | 145.373 | 1.00 | 25.46 |
| ATOM | 3537 | N | LEU | C | 342 | 64.251 | 14.834 | 144.479 | 1.00 | 28.86 |
| ATOM | 3538 | CA | LEU | C | 342 | 65.187 | 14.216 | 143.538 | 1.00 | 29.91 |
| ATOM | 3539 | CB | LEU | C | 342 | 64.633 | 12.917 | 142.982 | 1.00 | 33.91 |
| ATOM | 3540 | CG | LEU | C | 342 | 64.729 | 11.650 | 143.789 | 1.00 | 38.17 |
| ATOM | 3541 | CD1 | LEU | C | 342 | 63.609 | 11.576 | 144.833 | 1.00 | 40.39 |
| ATOM | 3542 | CD2 | LEU | C | 342 | 64.614 | 10.515 | 142.788 | 1.00 | 43.03 |
| ATOM | 3543 | C | LEU | C | 342 | 65.477 | 15.076 | 142.333 | 1.00 | 27.85 |
| ATOM | 3544 | O | LEU | C | 342 | 64.571 | 15.662 | 141.750 | 1.00 | 27.94 |
| ATOM | 3545 | N | ALA | C | 343 | 66.733 | 15.092 | 141.921 | 1.00 | 25.07 |
| ATOM | 3546 | CA | ALA | C | 343 | 67.132 | 15.866 | 140.763 | 1.00 | 23.93 |
| ATOM | 3547 | CE | ALA | C | 343 | 67.638 | 17.236 | 141.218 | 1.00 | 22.00 |
| ATOM | 3548 | C | ALA | C | 343 | 68.224 | 15.112 | 140.007 | 1.00 | 23.67 |
| ATOM | 3549 | O | ALA | C | 343 | 69.215 | 14.672 | 140.604 | 1.00 | 22.52 |
| ATOM | 3550 | N | GLY | C | 344 | 68.050 | 14.958 | 138.700 | 1.00 | 21.73 |
| ATOM | 3551 | CA | GLY | C | 344 | 69.064 | 14.259 | 137.949 | 1.00 | 22.16 |
| ATOM | 3552 | C | GLY | C | 344 | 69.211 | 14.686 | 136.509 | 1.00 | 23.40 |
| ATOM | 3553 | O | GLY | C | 344 | 68.280 | 15.217 | 135.901 | 1.00 | 24.16 |
| ATOM | 3554 | N | ASN | C | 345 | 70.405 | 14.481 | 135.966 | 1.00 | 22.89 |
| ATOM | 3555 | CA | ASN | C | 345 | 70.649 | 14.786 | 134.572 | 1.00 | 23.31 |
| ATOM | 3556 | CE | ASN | C | 345 | 71.592 | 15.980 | 134.382 | 1.00 | 22.34 |
| ATOM | 3557 | CG | ASN | C | 345 | 72.844 | 15.920 | 135.254 | 1.00 | 21.82 |
| ATOM | 3558 | OD1 | ASN | C | 345 | 73.463 | 14.860 | 135.432 | 1.00 | 18.42 |
| ATOM | 3559 | ND2 | ASN | C | 345 | 73.243 | 17.090 | 135.776 | 1.00 | 13.77 |
| ATOM | 3560 | C | ASN | C | 345 | 71.251 | 13.538 | 133.996 | 1.00 | 26.08 |
| ATOM | 3561 | O | ASN | C | 345 | 71.276 | 12.506 | 134.669 | 1.00 | 26.21 |
| ATOM | 3562 | N | SER | C | 346 | 71.729 | 13.608 | 132.760 | 1.00 | 29.18 |
| ATOM | 3563 | CA | SER | C | 346 | 72.317 | 12.428 | 132.130 | 1.00 | 32.72 |
| ATOM | 3564 | CE | SER | C | 346 | 72.628 | 12.718 | 130.670 | 1.00 | 32.48 |
| ATOM | 3565 | OG | SER | C | 346 | 73.540 | 13.802 | 130.580 | 1.00 | 39.08 |
| ATOM | 3566 | C | SER | C | 346 | 73.598 | 11.990 | 132.846 | 1.00 | 33.36 |
| ATOM | 3567 | O | SER | C | 346 | 73.995 | 10.818 | 132.777 | 1.00 | 33.41 |
| ATOM | 3568 | N | ILE | C | 347 | 74.236 | 12.928 | 133.543 | 1.00 | 32.93 |
| ATOM | 3569 | CA | ILE | C | 347 | 75.474 | 12.619 | 134.246 | 1.00 | 32.67 |
| ATOM | 3570 | CE | ILE | C | 347 | 76.216 | 13.890 | 134.647 | 1.00 | 32.54 |
| ATOM | 3571 | CG2 | ILE | C | 347 | 77.521 | 13.533 | 135.317 | 1.00 | 30.57 |
| ATOM | 3572 | CG1 | ILE | C | 347 | 76.495 | 14.738 | 133.414 | 1.00 | 30.88 |
| ATOM | 3573 | CD1 | ILE | C | 347 | 77.034 | 16.100 | 133.747 | 1.00 | 30.35 |
| ATOM | 3574 | C | ILE | C | 347 | 75.252 | 11.790 | 135.499 | 1.00 | 33.46 |
| ATOM | 3575 | O | ILE | C | 347 | 75.934 | 10.788 | 135.716 | 1.00 | 34.67 |
| ATOM | 3576 | N | GLY | C | 348 | 74.309 | 12.207 | 136.334 | 1.00 | 34.14 |
| ATOM | 3577 | CA | GLY | C | 348 | 74.046 | 11.458 | 137.549 | 1.00 | 33.61 |
| ATOM | 3578 | C | GLY | C | 348 | 72.761 | 11.867 | 138.239 | 1.00 | 34.30 |
| ATOM | 3579 | O | GLY | C | 348 | 71.953 | 12.617 | 137.678 | 1.00 | 35.47 |
| ATOM | 3580 | N | LEU | C | 349 | 72.592 | 11.389 | 139.471 | 1.00 | 33.67 |
| ATOM | 3581 | CA | LEU | C | 349 | 71.409 | 11.672 | 140.269 | 1.00 | 31.92 |
| ATOM | 3582 | CB | LEU | C | 349 | 70.572 | 10.399 | 140.360 | 1.00 | 34.71 |
| ATOM | 3583 | CG | LEU | C | 349 | 69.175 | 10.536 | 140.962 | 1.00 | 38.25 |
| ATOM | 3584 | CD1 | LEU | C | 349 | 68.296 | 11.357 | 140.007 | 1.00 | 39.99 |
| ATOM | 3585 | CD2 | LEU | C | 349 | 68.586 | 9.156 | 141.191 | 1.00 | 37.78 |
| ATOM | 3586 | C | LEU | C | 349 | 71.721 | 12.182 | 141.687 | 1.00 | 30.62 |
| ATOM | 3587 | O | LEU | C | 349 | 72.719 | 11.795 | 142.298 | 1.00 | 29.04 |
| ATOM | 3588 | N | SER | C | 350 | 70.856 | 13.051 | 142.207 | 1.00 | 28.72 |
| ATOM | 3589 | CA | SER | C | 350 | 71.022 | 13.587 | 143.551 | 1.00 | 27.43 |
| ATOM | 3590 | CB | SER | C | 350 | 71.590 | 15.001 | 143.515 | 1.00 | 26.34 |
| ATOM | 3591 | OG | SER | C | 350 | 72.889 | 15.011 | 142.967 | 1.00 | 26.24 |
| ATOM | 3592 | C | SER | C | 350 | 69.667 | 13.636 | 144.204 | 1.00 | 28.04 |
| ATOM | 3593 | O | SER | C | 350 | 68.654 | 13.578 | 143.515 | 1.00 | 29.41 |
| ATOM | 3594 | N | HIS | C | 351 | 69.643 | 13.742 | 145.529 | 1.00 | 28.26 |
| ATOM | 3595 | CA | HIS | C | 351 | 68.386 | 13.832 | 146.258 | 1.00 | 28.95 |
| ATOM | 3596 | CB | HIS | C | 351 | 67.598 | 12.518 | 146.162 | 1.00 | 30.19 |
| ATOM | 3597 | CG | HIS | C | 351 | 68.160 | 11.405 | 146.995 | 1.00 | 33.01 |
| ATOM | 3598 | CD2 | HIS | C | 351 | 67.678 | 10.794 | 148.107 | 1.00 | 33.21 |
| ATOM | 3599 | ND1 | HIS | C | 351 | 69.373 | 10.805 | 146.725 | 1.00 | 31.59 |
| ATOM | 3600 | CE1 | HIS | C | 351 | 69.615 | 9.876 | 147.632 | 1.00 | 31.13 |
| ATOM | 3601 | NE2 | HIS | C | 351 | 68.602 | 9.849 | 148.481 | 1.00 | 33.01 |
| ATOM | 3602 | C | HIS | C | 351 | 68.632 | 14.167 | 147.716 | 1.00 | 29.78 |
| ATOM | 3603 | O | HIS | C | 351 | 69.599 | 13.698 | 148.302 | 1.00 | 31.58 |
| ATOM | 3604 | N | HIS | C | 352 | 67.764 | 15.001 | 148.284 | 1.00 | 29.61 |
| ATOM | 3605 | CA | HIS | C | 352 | 67.833 | 15.388 | 149.692 | 1.00 | 28.24 |
| ATOM | 3606 | CB | HIS | C | 352 | 68.020 | 16.900 | 149.845 | 1.00 | 26.76 |
| ATOM | 3607 | CG | HIS | C | 352 | 69.436 | 17.358 | 149.705 | 1.00 | 27.38 |
| ATOM | 3608 | CD2 | HIS | C | 352 | 70.582 | 16.670 | 149.488 | 1.00 | 27.13 |
| ATOM | 3609 | ND1 | HIS | C | 352 | 69.797 | 18.687 | 149.786 | 1.00 | 27.93 |
| ATOM | 3610 | CE1 | HIS | C | 352 | 71.103 | 18.798 | 149.625 | 1.00 | 27.53 |

TABLE 1-continued

| | | | | FGFR1 D2–D3 Complexed with FGF2 | | | | | |
|---|---|---|---|---|---|---|---|---|---|
| ATOM | 3611 | NE2 | HIS | C | 352 | 71.603 | 17.589 | 149.442 | 1.00 | 28.55 |
| ATOM | 3612 | C | HIS | C | 352 | 66.495 | 14.998 | 150.292 | 1.00 | 28.26 |
| ATOM | 3613 | O | HIS | C | 352 | 65.473 | 15.043 | 149.613 | 1.00 | 30.53 |
| ATOM | 3614 | N | SER | C | 353 | 66.479 | 14.605 | 151.552 | 1.00 | 28.24 |
| ATOM | 3615 | CA | SER | C | 353 | 65.214 | 14.244 | 152.157 | 1.00 | 29.01 |
| ATOM | 3616 | CB | SER | C | 353 | 65.188 | 12.761 | 152.490 | 1.00 | 26.29 |
| ATOM | 3617 | OG | SER | C | 353 | 65.387 | 12.004 | 151.310 | 1.00 | 26.32 |
| ATOM | 3618 | C | SER | C | 353 | 64.995 | 15.083 | 153.398 | 1.00 | 30.55 |
| ATOM | 3619 | O | SER | C | 353 | 65.937 | 15.663 | 153.932 | 1.00 | 33.17 |
| ATOM | 3620 | N | ALA | C | 354 | 63.742 | 15.188 | 153.824 | 1.00 | 31.52 |
| ATOM | 3621 | CA | ALA | C | 354 | 63.391 | 15.954 | 155.017 | 1.00 | 31.06 |
| ATOM | 3622 | CB | ALA | C | 354 | 62.994 | 17.374 | 154.657 | 1.00 | 30.66 |
| ATOM | 3623 | C | ALA | C | 354 | 62.240 | 15.247 | 155.702 | 1.00 | 31.47 |
| ATOM | 3624 | O | ALA | C | 354 | 61.521 | 14.447 | 155.082 | 1.00 | 29.46 |
| ATOM | 3625 | N | TRP | C | 355 | 62.069 | 15.523 | 156.988 | 1.00 | 32.19 |
| ATOM | 3626 | CA | TRP | C | 355 | 60.998 | 14.873 | 157.705 | 1.00 | 33.04 |
| ATOM | 3627 | CB | TRP | C | 355 | 61.538 | 14.043 | 158.856 | 1.00 | 36.34 |
| ATOM | 3628 | CG | TRP | C | 355 | 60.566 | 12.984 | 159.209 | 1.00 | 43.15 |
| ATOM | 3629 | CD2 | TRP | C | 355 | 60.660 | 11.598 | 158.868 | 1.00 | 46.13 |
| ATOM | 3630 | CE2 | TRP | C | 355 | 59.454 | 10.978 | 159.295 | 1.00 | 47.17 |
| ATOM | 3631 | CE3 | TRP | C | 355 | 61.646 | 10.818 | 158.240 | 1.00 | 47.31 |
| ATOM | 3632 | CD1 | TRP | C | 355 | 59.343 | 13.148 | 159.821 | 1.00 | 44.54 |
| ATOM | 3633 | NE1 | TRP | C | 355 | 58.672 | 11.946 | 159.872 | 1.00 | 46.02 |
| ATOM | 3634 | CZ2 | TRP | C | 355 | 59.208 | 9.609 | 159.113 | 1.00 | 47.00 |
| ATOM | 3635 | CZ3 | TRP | C | 355 | 61.403 | 9.456 | 158.060 | 1.00 | 48.50 |
| ATOM | 3636 | CR2 | TRP | C | 355 | 60.189 | 8.866 | 158.496 | 1.00 | 48.25 |
| ATOM | 3637 | C | TRP | C | 355 | 59.919 | 15.802 | 158.214 | 1.00 | 32.05 |
| ATOM | 3638 | O | TRP | C | 355 | 60.198 | 16.828 | 158.835 | 1.00 | 30.83 |
| ATOM | 3639 | N | LEU | C | 356 | 58.678 | 15.420 | 157.933 | 1.00 | 31.07 |
| ATOM | 3640 | CA | LEU | C | 356 | 57.524 | 16.183 | 158.352 | 1.00 | 30.97 |
| ATOM | 3641 | CB | LEU | C | 356 | 56.477 | 16.209 | 157.234 | 1.00 | 30.59 |
| ATOM | 3642 | CG | LEU | C | 356 | 55.497 | 17.398 | 157.177 | 1.00 | 30.85 |
| ATOM | 3643 | CD1 | LEU | C | 356 | 54.086 | 16.904 | 157.372 | 1.00 | 28.31 |
| ATOM | 3644 | CD2 | LEU | C | 356 | 55.863 | 18.464 | 158.228 | 1.00 | 29.07 |
| ATOM | 3645 | C | LEU | C | 356 | 56.946 | 15.542 | 159.599 | 1.00 | 31.35 |
| ATOM | 3646 | O | LEU | C | 356 | 56.465 | 14.413 | 159.556 | 1.00 | 32.90 |
| ATOM | 3647 | N | THR | C | 357 | 57.024 | 16.263 | 160.712 | 1.00 | 32.76 |
| ATOM | 3648 | CA | THR | C | 357 | 56.493 | 15.808 | 162.001 | 1.00 | 33.59 |
| ATOM | 3649 | CB | THR | C | 357 | 57.483 | 16.103 | 163.156 | 1.00 | 31.42 |
| ATOM | 3650 | OG1 | THR | C | 357 | 58.639 | 15.274 | 163.031 | 1.00 | 30.47 |
| ATOM | 3651 | CG2 | THR | C | 357 | 56.825 | 15.868 | 164.498 | 1.00 | 29.75 |
| ATOM | 3652 | C | THR | C | 357 | 55.199 | 16.580 | 162.280 | 1.00 | 35.63 |
| ATOM | 3653 | O | THR | C | 357 | 55.219 | 17.811 | 162.359 | 1.00 | 36.00 |
| ATOM | 3654 | N | VAL | C | 358 | 54.077 | 15.876 | 162.414 | 1.00 | 38.93 |
| ATOM | 3655 | CA | VAL | C | 358 | 52.801 | 16.548 | 162.697 | 1.00 | 41.15 |
| ATOM | 3656 | CB | VAL | C | 358 | 51.677 | 16.122 | 161.714 | 1.00 | 41.26 |
| ATOM | 3657 | CG1 | VAL | C | 358 | 50.328 | 16.600 | 162.225 | 1.00 | 41.80 |
| ATOM | 3658 | CG2 | VAL | C | 358 | 51.917 | 16.742 | 160.352 | 1.00 | 41.94 |
| ATOM | 3659 | C | VAL | C | 358 | 52.313 | 16.314 | 164.126 | 1.00 | 41.85 |
| ATOM | 3660 | O | VAL | C | 358 | 52.489 | 15.227 | 164.688 | 1.00 | 43.32 |
| ATOM | 3661 | N | LEU | C | 359 | 51.715 | 17.347 | 164.715 | 1.00 | 41.83 |
| ATOM | 3662 | CA | LEU | C | 359 | 51.192 | 17.256 | 166.074 | 1.00 | 41.63 |
| ATOM | 3663 | CB | LEU | C | 359 | 52.240 | 17.766 | 167.075 | 1.00 | 41.22 |
| ATOM | 3664 | CG | LEU | C | 359 | 53.580 | 17.017 | 167.141 | 1.00 | 41.29 |
| ATOM | 3665 | CD1 | LEU | C | 359 | 54.507 | 17.658 | 168.177 | 1.00 | 37.31 |
| ATOM | 3666 | CD2 | LEU | C | 359 | 53.319 | 15.552 | 167.480 | 1.00 | 41.10 |
| ATOM | 3667 | C | LEU | C | 359 | 49.889 | 18.051 | 166.202 | 1.00 | 40.98 |
| ATOM | 3668 | O | LEU | C | 359 | 49.037 | 17.618 | 167.011 | 1.00 | 42.00 |
| ATOM | 3669 | CB | MET | D | 149 | 110.758 | 21.323 | 85.925 | 1.00 | 69.15 |
| ATOM | 3670 | CG | MET | D | 149 | 112.000 | 21.050 | 86.762 | 1.00 | 74.74 |
| ATOM | 3671 | SD | MET | D | 149 | 113.256 | 20.101 | 85.852 | 1.00 | 81.81 |
| ATOM | 3672 | CE | MET | D | 149 | 114.238 | 21.463 | 85.114 | 1.00 | 78.77 |
| ATOM | 3673 | C | MET | D | 149 | 109.620 | 19.185 | 86.605 | 1.00 | 62.44 |
| ATOM | 3674 | O | MET | D | 149 | 109.529 | 19.656 | 87.741 | 1.00 | 62.89 |
| ATOM | 3675 | N | MET | D | 149 | 108.883 | 20.439 | 84.573 | 1.00 | 63.06 |
| ATOM | 3676 | CA | MET | D | 149 | 110.054 | 20.057 | 85.419 | 1.00 | 64.74 |
| ATOM | 3677 | N | PRO | D | 150 | 109.353 | 17.894 | 86.353 | 1.00 | 59.72 |
| ATOM | 3678 | CD | PRO | D | 150 | 109.422 | 17.240 | 85.034 | 1.00 | 59.01 |
| ATOM | 3679 | CA | PRO | D | 150 | 108.924 | 16.941 | 87.384 | 1.00 | 57.62 |
| ATOM | 3680 | CB | PRO | D | 150 | 109.001 | 15.600 | 86.662 | 1.00 | 57.11 |
| ATOM | 3681 | CG | PRO | D | 150 | 108.634 | 15.970 | 85.264 | 1.00 | 57.93 |
| ATOM | 3682 | C | PRO | D | 150 | 109.754 | 16.957 | 88.670 | 1.00 | 55.83 |
| ATOM | 3683 | O | PRO | D | 150 | 110.977 | 16.787 | 88.631 | 1.00 | 54.45 |
| ATOM | 3684 | N | VAL | D | 151 | 109.079 | 17.171 | 89.803 | 1.00 | 54.22 |
| ATOM | 3685 | CA | VAL | D | 151 | 109.734 | 17.182 | 91.120 | 1.00 | 51.14 |
| ATOM | 3686 | CB | VAL | D | 151 | 109.991 | 18.614 | 91.675 | 1.00 | 49.72 |
| ATOM | 3687 | CG1 | VAL | D | 151 | 110.768 | 18.530 | 92.980 | 1.00 | 47.94 |

TABLE 1-continued

FGFR1 D2–D3 Complexed with FGF2

| | | | | | | | | | | |
|---|---|---|---|---|---|---|---|---|---|---|
| ATOM | 3688 | CG2 | VAL | D | 151 | 110.778 | 19.431 | 90.685 | 1.00 | 51.03 |
| ATOM | 3689 | C | VAL | D | 151 | 108.679 | 16.454 | 92.144 | 1.00 | 49.31 |
| ATOM | 3690 | O | VAL | D | 151 | 107.679 | 16.711 | 92.263 | 1.00 | 49.40 |
| ATOM | 3691 | N | ALA | D | 152 | 109.507 | 15.539 | 92.874 | 1.00 | 47.24 |
| ATOM | 3692 | CA | ALA | D | 152 | 108.819 | 14.787 | 93.911 | 1.00 | 45.53 |
| ATOM | 3693 | CB | ALA | D | 152 | 109.658 | 13.586 | 94.330 | 1.00 | 46.23 |
| ATOM | 3694 | C | ALA | D | 152 | 108.599 | 15.726 | 95.100 | 1.00 | 44.08 |
| ATOM | 3695 | O | ALA | D | 152 | 109.352 | 16.683 | 95.303 | 1.00 | 43.55 |
| ATOM | 3696 | N | PRO | D | 153 | 107.565 | 15.463 | 95.904 | 1.00 | 42.50 |
| ATOM | 3697 | CD | PRO | D | 153 | 106.685 | 14.282 | 95.917 | 1.00 | 42.56 |
| ATOM | 3698 | CA | PRO | D | 153 | 107.308 | 16.332 | 97.053 | 1.00 | 41.65 |
| ATOM | 3699 | CB | PRO | D | 153 | 106.100 | 15.670 | 97.721 | 1.00 | 42.90 |
| ATOM | 3700 | CG | PRO | D | 153 | 106.266 | 14.218 | 97.360 | 1.00 | 44.02 |
| ATOM | 3701 | C | PRO | D | 153 | 108.499 | 16.481 | 98.001 | 1.00 | 40.45 |
| ATOM | 3702 | O | PRO | D | 153 | 109.251 | 15.530 | 98.237 | 1.00 | 39.50 |
| ATOM | 3703 | N | TYR | D | 154 | 108.668 | 17.685 | 98.535 | 1.00 | 38.89 |
| ATOM | 3704 | CA | TYR | D | 154 | 109.754 | 17.955 | 99.470 | 1.00 | 37.97 |
| ATOM | 3705 | CB | TYR | D | 154 | 110.957 | 18.508 | 98.727 | 1.00 | 36.16 |
| ATOM | 3706 | CG | TYR | D | 154 | 110.743 | 19.903 | 98.186 | 1.00 | 34.50 |
| ATOM | 3707 | CD1 | TYR | D | 154 | 110.255 | 20.109 | 96.900 | 1.00 | 34.15 |
| ATOM | 3708 | CE1 | TYR | D | 154 | 110.089 | 21.393 | 96.395 | 1.00 | 33.84 |
| ATOM | 3709 | CD2 | TYR | D | 154 | 111.050 | 21.019 | 98.959 | 1.00 | 34.16 |
| ATOM | 3710 | CE2 | TYR | D | 154 | 110.885 | 22.303 | 98.464 | 1.00 | 34.12 |
| ATOM | 3711 | CZ | TYR | D | 154 | 110.409 | 22.481 | 97.183 | 1.00 | 33.84 |
| ATOM | 3712 | OH | TYR | D | 154 | 110.276 | 23.751 | 96.689 | 1.00 | 35.14 |
| ATOM | 3713 | C | TYR | D | 154 | 109.298 | 18.972 | 100.524 | 1.00 | 38.33 |
| ATOM | 3714 | O | TYR | D | 154 | 108.449 | 19.830 | 100.243 | 1.00 | 39.41 |
| ATOM | 3715 | N | TRP | D | 155 | 109.863 | 18.892 | 101.727 | 1.00 | 36.71 |
| ATOM | 3716 | CA | TRP | D | 155 | 109.455 | 19.823 | 102.771 | 1.00 | 37.08 |
| ATOM | 3717 | CB | TRP | D | 155 | 109.894 | 19.355 | 104.170 | 1.00 | 35.10 |
| ATOM | 3718 | CG | TRP | D | 155 | 109.428 | 17.970 | 104.597 | 1.00 | 32.90 |
| ATOM | 3719 | CD2 | TRP | D | 155 | 108.072 | 17.482 | 104.711 | 1.00 | 33.50 |
| ATOM | 3720 | CE2 | TRP | D | 155 | 108.147 | 16.139 | 105.165 | 1.00 | 31.19 |
| ATOM | 3721 | CE3 | TRP | D | 155 | 106.809 | 18.045 | 104.473 | 1.00 | 35.19 |
| ATOM | 3722 | CD1 | TRP | D | 155 | 110.226 | 16.936 | 104.974 | 1.00 | 32.49 |
| ATOM | 3723 | NE1 | TRP | D | 155 | 109.467 | 15.835 | 105.316 | 1.00 | 32.97 |
| ATOM | 3724 | CZ2 | TRP | D | 155 | 107.014 | 15.352 | 105.386 | 1.00 | 31.24 |
| ATOM | 3725 | CZ3 | TRP | D | 155 | 105.668 | 17.253 | 104.696 | 1.00 | 33.46 |
| ATOM | 3726 | CR2 | TRP | D | 155 | 105.786 | 15.922 | 105.148 | 1.00 | 32.78 |
| ATOM | 3727 | C | TRP | D | 155 | 110.029 | 21.202 | 102.482 | 1.00 | 38.20 |
| ATOM | 3728 | O | TRP | D | 155 | 111.219 | 21.350 | 102.196 | 1.00 | 38.53 |
| ATOM | 3729 | N | THR | D | 156 | 109.161 | 22.202 | 102.554 | 1.00 | 38.98 |
| ATOM | 3730 | CA | THR | D | 156 | 109.531 | 23.577 | 102.303 | 1.00 | 40.31 |
| ATOM | 3731 | CB | THR | D | 156 | 108.352 | 24.311 | 101.685 | 1.00 | 40.82 |
| ATOM | 3732 | OG1 | THR | D | 156 | 107.322 | 24.493 | 102.665 | 1.00 | 40.84 |
| ATOM | 3733 | CG2 | THR | D | 156 | 107.797 | 23.490 | 100.548 | 1.00 | 40.35 |
| ATOM | 3734 | C | THR | D | 156 | 109.948 | 24.276 | 103.593 | 1.00 | 42.90 |
| ATOM | 3735 | O | THR | D | 156 | 110.677 | 25.269 | 103.560 | 1.00 | 43.06 |
| ATOM | 3736 | N | SER | D | 157 | 109.495 | 23.753 | 104.730 | 1.00 | 45.45 |
| ATOM | 3737 | CA | SER | D | 157 | 109.833 | 24.357 | 106.019 | 1.00 | 46.78 |
| ATOM | 3738 | CB | SER | D | 157 | 108.702 | 25.283 | 106.472 | 1.00 | 45.14 |
| ATOM | 3739 | OG | SER | D | 157 | 108.311 | 26.138 | 105.413 | 1.00 | 44.01 |
| ATOM | 3740 | C | SER | D | 157 | 110.111 | 23.305 | 107.091 | 1.00 | 47.76 |
| ATOM | 3741 | O | SER | D | 157 | 109.389 | 23.205 | 108.083 | 1.00 | 49.26 |
| ATOM | 3742 | N | PRO | D | 158 | 111.175 | 22.510 | 106.905 | 1.00 | 48.01 |
| ATOM | 3743 | CD | PRO | D | 158 | 112.209 | 22.622 | 105.862 | 1.00 | 47.15 |
| ATOM | 3744 | CA | PRO | D | 158 | 111.529 | 21.470 | 107.873 | 1.00 | 48.12 |
| ATOM | 3745 | CB | PRO | D | 158 | 112.760 | 20.830 | 107.245 | 1.00 | 47.44 |
| ATOM | 3746 | CG | PRO | D | 158 | 113.392 | 21.978 | 106.534 | 1.00 | 47.27 |
| ATOM | 3747 | C | PRO | D | 158 | 111.810 | 22.047 | 109.259 | 1.00 | 48.98 |
| ATOM | 3748 | O | PRO | D | 158 | 111.803 | 21.324 | 110.257 | 1.00 | 49.86 |
| ATOM | 3749 | N | GLU | D | 159 | 112.060 | 23.351 | 109.313 | 1.00 | 49.77 |
| ATOM | 3750 | CA | GLU | D | 159 | 112.339 | 24.023 | 110.577 | 1.00 | 50.29 |
| ATOM | 3751 | CB | GLU | D | 159 | 112.846 | 25.442 | 110.313 | 1.00 | 51.25 |
| ATOM | 3752 | C | GLU | D | 159 | 111.081 | 24.060 | 111.448 | 1.00 | 50.73 |
| ATOM | 3753 | O | GLU | D | 159 | 111.168 | 24.038 | 112.674 | 1.00 | 52.21 |
| ATOM | 3754 | N | LYS | D | 160 | 109.916 | 24.095 | 110.803 | 1.00 | 50.21 |
| ATOM | 3755 | CA | LYS | D | 160 | 108.624 | 24.127 | 111.493 | 1.00 | 48.11 |
| ATOM | 3756 | CB | LYS | D | 160 | 107.612 | 24.890 | 110.625 | 1.00 | 47.76 |
| ATOM | 3757 | C | LYS | D | 160 | 108.088 | 22.714 | 111.803 | 1.00 | 46.25 |
| ATOM | 3758 | O | LYS | D | 160 | 106.895 | 22.534 | 112.065 | 1.00 | 45.85 |
| ATOM | 3759 | N | MET | D | 161 | 108.973 | 21.721 | 111.793 | 1.00 | 44.07 |
| ATOM | 3760 | CA | MET | D | 161 | 108.570 | 20.337 | 112.033 | 1.00 | 41.94 |
| ATOM | 3761 | CB | MET | D | 161 | 108.721 | 19.531 | 110.743 | 1.00 | 41.09 |
| ATOM | 3762 | CG | MET | D | 161 | 108.422 | 20.324 | 109.491 | 1.00 | 40.86 |
| ATOM | 3763 | SD | MET | D | 161 | 108.201 | 19.267 | 108.062 | 1.00 | 41.70 |
| ATOM | 3764 | CE | MET | D | 161 | 106.479 | 18.779 | 108.274 | 1.00 | 40.72 |

TABLE 1-continued

FGFR1 D2–D3 Complexed with FGF2

| ATOM | 3765 | C | MET | D | 161 | 109.376 | 19.656 | 113.128 | 1.00 | 40.13 |
| ATOM | 3766 | O | MET | D | 161 | 109.080 | 18.532 | 113.514 | 1.00 | 39.25 |
| ATOM | 3767 | N | GLU | D | 162 | 110.394 | 20.339 | 113.624 | 1.00 | 39.93 |
| ATOM | 3768 | CA | GLU | D | 162 | 111.249 | 19.777 | 114.656 | 1.00 | 39.97 |
| ATOM | 3769 | CB | GLU | D | 162 | 112.330 | 20.803 | 115.035 | 1.00 | 41.29 |
| ATOM | 3770 | C | GLU | D | 162 | 110.504 | 19.276 | 115.912 | 1.00 | 39.38 |
| ATOM | 3771 | O | GLU | D | 162 | 110.942 | 18.317 | 116.555 | 1.00 | 39.93 |
| ATOM | 3772 | N | LYS | D | 163 | 109.387 | 19.912 | 116.256 | 1.00 | 37.75 |
| ATOM | 3773 | CA | LYS | D | 163 | 108.601 | 19.519 | 117.430 | 1.00 | 37.57 |
| ATOM | 3774 | CB | LYS | D | 163 | 107.739 | 20.699 | 117.879 | 1.00 | 38.91 |
| ATOM | 3775 | CG | LYS | D | 163 | 106.685 | 20.375 | 118.924 | 1.00 | 39.14 |
| ATOM | 3776 | CD | LYS | D | 163 | 105.919 | 21.641 | 119.271 | 1.00 | 42.01 |
| ATOM | 3777 | CE | LYS | D | 163 | 104.685 | 21.381 | 120.110 | 1.00 | 42.34 |
| ATOM | 3778 | NZ | LYS | D | 163 | 103.984 | 22.666 | 120.386 | 1.00 | 43.85 |
| ATOM | 3779 | C | LYS | D | 163 | 107.699 | 18.325 | 117.135 | 1.00 | 36.24 |
| ATOM | 3780 | O | LYS | D | 163 | 106.522 | 18.499 | 116.832 | 1.00 | 36.01 |
| ATOM | 3781 | N | LYS | D | 164 | 108.248 | 17.118 | 117.231 | 1.00 | 35.31 |
| ATOM | 3782 | CA | LYS | D | 164 | 107.482 | 15.908 | 116.949 | 1.00 | 34.73 |
| ATOM | 3783 | CB | LYS | D | 164 | 108.429 | 14.703 | 116.845 | 1.00 | 33.14 |
| ATOM | 3784 | C | LYS | D | 164 | 106.363 | 15.627 | 117.971 | 1.00 | 34.05 |
| ATOM | 3785 | O | LYS | D | 164 | 105.279 | 15.178 | 117.597 | 1.00 | 33.86 |
| ATOM | 3786 | N | LEU | D | 165 | 106.616 | 15.901 | 119.251 | 1.00 | 33.62 |
| ATOM | 3787 | CA | LEU | D | 165 | 105.614 | 15.668 | 120.299 | 1.00 | 32.88 |
| ATOM | 3788 | CB | LEU | D | 165 | 106.266 | 15.047 | 121.539 | 1.00 | 30.62 |
| ATOM | 3789 | CG | LEU | D | 165 | 105.369 | 14.968 | 122.780 | 1.00 | 29.12 |
| ATOM | 3790 | CD1 | LEU | D | 165 | 104.041 | 14.358 | 122.395 | 1.00 | 30.41 |
| ATOM | 3791 | CD2 | LEU | D | 165 | 106.033 | 14.148 | 123.875 | 1.00 | 28.30 |
| ATOM | 3792 | C | LEU | D | 165 | 104.825 | 16.900 | 120.749 | 1.00 | 32.89 |
| ATOM | 3793 | O | LEU | D | 165 | 105.403 | 17.880 | 121.214 | 1.00 | 31.55 |
| ATOM | 3794 | N | HIS | D | 166 | 103.502 | 16.839 | 120.623 | 1.00 | 34.11 |
| ATOM | 3795 | CA | HIS | D | 166 | 102.642 | 17.944 | 121.062 | 1.00 | 35.36 |
| ATOM | 3796 | CB | HIS | D | 166 | 101.697 | 18.406 | 119.938 | 1.00 | 36.03 |
| ATOM | 3797 | CG | HIS | D | 166 | 102.383 | 19.122 | 118.815 | 1.00 | 38.56 |
| ATOM | 3798 | CD2 | HIS | D | 166 | 102.166 | 20.346 | 118.275 | 1.00 | 39.15 |
| ATOM | 3799 | ND1 | HIS | D | 166 | 103.415 | 18.563 | 118.090 | 1.00 | 40.14 |
| ATOM | 3800 | CE1 | HIS | D | 166 | 103.805 | 19.411 | 117.153 | 1.00 | 40.03 |
| ATOM | 3801 | NE2 | HIS | D | 166 | 103.063 | 20.500 | 117.243 | 1.00 | 39.63 |
| ATOM | 3802 | C | HIS | D | 166 | 101.815 | 17.512 | 122.278 | 1.00 | 34.38 |
| ATOM | 3803 | O | HIS | D | 166 | 100.854 | 16.751 | 122.151 | 1.00 | 33.62 |
| ATOM | 3804 | N | ALA | D | 167 | 102.216 | 17.987 | 123.453 | 1.00 | 34.17 |
| ATOM | 3805 | CA | ALA | D | 167 | 101.512 | 17.683 | 124.693 | 1.00 | 34.33 |
| ATOM | 3806 | CB | ALA | D | 167 | 102.494 | 17.263 | 125.773 | 1.00 | 34.70 |
| ATOM | 3807 | C | ALA | D | 167 | 100.773 | 18.953 | 125.102 | 1.00 | 34.92 |
| ATOM | 3808 | O | ALA | D | 167 | 101.349 | 20.053 | 125.139 | 1.00 | 34.52 |
| ATOM | 3809 | N | VAL | D | 168 | 99.490 | 18.807 | 125.404 | 1.00 | 34.73 |
| ATOM | 3810 | CA | VAL | D | 168 | 98.687 | 19.961 | 125.772 | 1.00 | 35.77 |
| ATOM | 3811 | CB | VAL | D | 168 | 98.071 | 20.638 | 124.516 | 1.00 | 37.28 |
| ATOM | 3812 | CG1 | VAL | D | 168 | 99.167 | 21.236 | 123.661 | 1.00 | 39.06 |
| ATOM | 3813 | CG2 | VAL | D | 168 | 97.266 | 19.618 | 123.708 | 1.00 | 35.97 |
| ATOM | 3814 | C | VAL | D | 168 | 97.542 | 19.679 | 126.734 | 1.00 | 35.05 |
| ATOM | 3815 | O | VAL | D | 168 | 97.092 | 18.541 | 126.890 | 1.00 | 34.17 |
| ATOM | 3816 | N | PRO | D | 169 | 97.055 | 20.733 | 127.401 | 1.00 | 35.28 |
| ATOM | 3817 | CD | PRO | D | 169 | 97.554 | 22.122 | 127.403 | 1.00 | 36.03 |
| ATOM | 3818 | CA | PRO | D | 169 | 95.949 | 20.572 | 128.340 | 1.00 | 35.43 |
| ATOM | 3819 | CB | PRO | D | 169 | 96.026 | 21.851 | 129.173 | 1.00 | 35.77 |
| ATOM | 3820 | CG | PRO | D | 169 | 96.490 | 22.857 | 128.188 | 1.00 | 35.98 |
| ATOM | 3821 | C | PRO | D | 169 | 94.661 | 20.467 | 127.525 | 1.00 | 34.49 |
| ATOM | 3822 | O | PRO | D | 169 | 94.466 | 21.221 | 126.569 | 1.00 | 34.25 |
| ATOM | 3823 | N | ALA | D | 170 | 93.796 | 19.523 | 127.886 | 1.00 | 34.06 |
| ATOM | 3824 | CA | ALA | D | 170 | 92.532 | 19.332 | 127.174 | 1.00 | 33.00 |
| ATOM | 3825 | CB | ALA | D | 170 | 91.619 | 18.416 | 127.956 | 1.00 | 33.00 |
| ATOM | 3826 | C | ALA | D | 170 | 91.824 | 20.651 | 126.924 | 1.00 | 32.26 |
| ATOM | 3827 | O | ALA | D | 170 | 91.941 | 21.578 | 127.719 | 1.00 | 32.40 |
| ATOM | 3828 | N | ALA | D | 171 | 91.093 | 20.713 | 125.813 | 1.00 | 32.29 |
| ATOM | 3829 | CA | ALA | D | 171 | 90.327 | 21.892 | 125.398 | 1.00 | 32.27 |
| ATOM | 3830 | CB | ALA | D | 171 | 89.828 | 22.679 | 126.609 | 1.00 | 31.55 |
| ATOM | 3831 | C | ALA | D | 171 | 91.112 | 22.819 | 124.491 | 1.00 | 31.96 |
| ATOM | 3832 | O | ALA | D | 171 | 90.562 | 23.778 | 123.948 | 1.00 | 29.70 |
| ATOM | 3833 | N | LYS | D | 172 | 92.402 | 22.546 | 124.333 | 1.00 | 32.67 |
| ATOM | 3834 | CA | LYS | D | 172 | 93.217 | 23.384 | 123.473 | 1.00 | 33.52 |
| ATOM | 3835 | CB | LYS | D | 172 | 94.694 | 23.261 | 123.863 | 1.00 | 33.51 |
| ATOM | 3836 | CG | LYS | D | 172 | 95.611 | 24.093 | 122.988 | 1.00 | 34.75 |
| ATOM | 3837 | CD | LYS | D | 172 | 97.001 | 24.243 | 123.565 | 1.00 | 36.61 |
| ATOM | 3838 | CE | LYS | D | 172 | 97.944 | 24.853 | 122.526 | 1.00 | 37.04 |
| ATOM | 3839 | NZ | LYS | D | 172 | 97.361 | 26.069 | 121.884 | 1.00 | 37.00 |
| ATOM | 3840 | C | LYS | D | 172 | 93.019 | 23.029 | 121.987 | 1.00 | 34.04 |
| ATOM | 3841 | O | LYS | D | 172 | 92.652 | 21.896 | 121.647 | 1.00 | 33.27 |

TABLE 1-continued

FGFR1 D2–D3 Complexed with FGF2

| ATOM | 3842 | N | THR | D | 173 | 93.232 | 24.013 | 121.112 | 1.00 | 33.22 |
|---|---|---|---|---|---|---|---|---|---|---|
| ATOM | 3843 | CA | THR | D | 173 | 93.115 | 23.804 | 119.670 | 1.00 | 33.34 |
| ATOM | 3844 | CB | THR | D | 173 | 92.676 | 25.100 | 118.920 | 1.00 | 34.73 |
| ATOM | 3845 | OG1 | THR | D | 173 | 91.293 | 25.359 | 119.174 | 1.00 | 35.71 |
| ATOM | 3846 | CG2 | THR | D | 173 | 92.857 | 24.947 | 117.418 | 1.00 | 35.47 |
| ATOM | 3847 | C | THR | D | 173 | 94.484 | 23.379 | 119.161 | 1.00 | 32.51 |
| ATOM | 3848 | O | THR | D | 173 | 95.475 | 24.052 | 119.425 | 1.00 | 32.58 |
| ATOM | 3849 | N | VAL | D | 174 | 94.545 | 22.256 | 118.451 | 1.00 | 31.86 |
| ATOM | 3850 | CA | VAL | D | 174 | 95.814 | 21.779 | 117.920 | 1.00 | 31.60 |
| ATOM | 3851 | CB | VAL | D | 174 | 96.099 | 20.349 | 118.361 | 1.00 | 31.01 |
| ATOM | 3852 | CG1 | VAL | D | 174 | 97.430 | 19.890 | 117.769 | 1.00 | 32.36 |
| ATOM | 3853 | CG2 | VAL | D | 174 | 96.134 | 20.279 | 119.872 | 1.00 | 28.05 |
| ATOM | 3854 | C | VAL | D | 174 | 95.879 | 21.855 | 116.395 | 1.00 | 33.26 |
| ATOM | 3855 | O | VAL | D | 174 | 94.892 | 21.594 | 115.704 | 1.00 | 33.35 |
| ATOM | 3856 | N | LYS | D | 175 | 97.045 | 22.236 | 115.877 | 1.00 | 34.14 |
| ATOM | 3857 | CA | LYS | D | 175 | 97.235 | 22.345 | 114.433 | 1.00 | 34.10 |
| ATOM | 3858 | CB | LYS | D | 175 | 97.168 | 23.809 | 113.983 | 1.00 | 34.48 |
| ATOM | 3859 | C | LYS | D | 175 | 98.577 | 21.748 | 114.052 | 1.00 | 34.13 |
| ATOM | 3860 | O | LYS | D | 175 | 99.607 | 22.109 | 114.614 | 1.00 | 34.08 |
| ATOM | 3861 | N | PHE | D | 176 | 98.551 | 20.816 | 113.107 | 1.00 | 34.81 |
| ATOM | 3862 | CA | PHE | D | 176 | 99.764 | 20.157 | 112.639 | 1.00 | 36.16 |
| ATOM | 3863 | CB | PHE | D | 176 | 99.610 | 18.637 | 112.667 | 1.00 | 38.54 |
| ATOM | 3864 | CG | PHE | D | 176 | 99.406 | 18.067 | 114.038 | 1.00 | 42.17 |
| ATOM | 3865 | CD1 | PHE | D | 176 | 100.194 | 18.485 | 115.107 | 1.00 | 42.78 |
| ATOM | 3866 | CD2 | PHE | D | 176 | 98.451 | 17.074 | 114.256 | 1.00 | 42.56 |
| ATOM | 3867 | CE1 | PHE | D | 176 | 100.039 | 17.922 | 116.374 | 1.00 | 42.13 |
| ATOM | 3868 | CE2 | PHE | D | 176 | 98.290 | 16.506 | 115.519 | 1.00 | 42.31 |
| ATOM | 3869 | CZ | PHE | D | 176 | 99.087 | 16.932 | 116.577 | 1.00 | 42.63 |
| ATOM | 3870 | C | PHE | D | 176 | 100.070 | 20.590 | 111.214 | 1.00 | 36.23 |
| ATOM | 3871 | O | PHE | D | 176 | 99.227 | 20.441 | 110.322 | 1.00 | 34.78 |
| ATOM | 3872 | N | LYS | D | 177 | 101.283 | 21.101 | 111.005 | 1.00 | 35.54 |
| ATOM | 3873 | CA | LYS | D | 177 | 101.694 | 21.570 | 109.690 | 1.00 | 36.04 |
| ATOM | 3874 | CB | LYS | D | 177 | 102.157 | 23.032 | 109.801 | 1.00 | 34.13 |
| ATOM | 3875 | C | LYS | D | 177 | 102.784 | 20.706 | 109.033 | 1.00 | 36.18 |
| ATOM | 3876 | O | LYS | D | 177 | 103.714 | 20.248 | 109.698 | 1.00 | 35.87 |
| ATOM | 3877 | N | CYS | D | 178 | 102.637 | 20.474 | 107.728 | 1.00 | 37.01 |
| ATOM | 3878 | CA | CYS | D | 178 | 103.598 | 19.701 | 106.936 | 1.00 | 37.64 |
| ATOM | 3879 | C | CYS | D | 178 | 103.911 | 20.467 | 105.655 | 1.00 | 38.59 |
| ATOM | 3880 | O | CYS | D | 178 | 103.697 | 19.966 | 104.550 | 1.00 | 38.68 |
| ATOM | 3881 | CB | CYS | D | 178 | 103.031 | 18.330 | 106.578 | 1.00 | 36.26 |
| ATOM | 3882 | SG | CYS | D | 178 | 102.974 | 17.203 | 107.996 | 1.00 | 36.60 |
| ATOM | 3883 | N | PRO | D | 179 | 104.416 | 21.707 | 105.787 | 1.00 | 39.52 |
| ATOM | 3884 | CD | PRO | D | 179 | 104.675 | 22.481 | 107.015 | 1.00 | 39.06 |
| ATOM | 3885 | CA | PRO | D | 179 | 104.740 | 22.511 | 104.611 | 1.00 | 39.90 |
| ATOM | 3886 | CB | PRO | D | 179 | 105.401 | 23.747 | 105.217 | 1.00 | 38.21 |
| ATOM | 3887 | CG | PRO | D | 179 | 104.680 | 23.900 | 106.495 | 1.00 | 36.04 |
| ATOM | 3888 | C | PRO | D | 179 | 105.654 | 21.766 | 103.649 | 1.00 | 41.32 |
| ATOM | 3889 | O | PRO | D | 179 | 106.807 | 21.439 | 103.977 | 1.00 | 40.88 |
| ATOM | 3890 | N | SER | D | 180 | 105.119 | 21.485 | 102.466 | 1.00 | 42.71 |
| ATOM | 3891 | CA | SER | D | 180 | 105.875 | 20.790 | 101.437 | 1.00 | 44.82 |
| ATOM | 3892 | CB | SER | D | 180 | 105.529 | 19.292 | 101.413 | 1.00 | 45.46 |
| ATOM | 3893 | OG | SER | D | 180 | 104.130 | 19.082 | 101.432 | 1.00 | 48.11 |
| ATOM | 3894 | C | SER | D | 180 | 105.608 | 21.424 | 100.083 | 1.00 | 45.11 |
| ATOM | 3895 | O | SER | D | 180 | 104.881 | 22.425 | 99.988 | 1.00 | 45.08 |
| ATOM | 3896 | N | SER | D | 181 | 106.216 | 20.852 | 99.046 | 1.00 | 44.67 |
| ATOM | 3897 | CA | SER | D | 181 | 106.062 | 21.360 | 97.691 | 1.00 | 44.09 |
| ATOM | 3898 | CB | SER | D | 181 | 106.911 | 22.620 | 97.508 | 1.00 | 42.85 |
| ATOM | 3899 | OG | SER | D | 181 | 106.811 | 23.124 | 96.189 | 1.00 | 41.34 |
| ATOM | 3900 | C | SER | D | 181 | 106.499 | 20.317 | 96.680 | 1.00 | 44.51 |
| ATOM | 3901 | O | SER | D | 181 | 107.084 | 19.299 | 97.040 | 1.00 | 44.21 |
| ATOM | 3902 | N | GLY | D | 182 | 106.216 | 20.591 | 95.411 | 1.00 | 45.65 |
| ATOM | 3903 | CA | GLY | D | 182 | 106.592 | 19.692 | 94.336 | 1.00 | 45.68 |
| ATOM | 3904 | C | GLY | D | 182 | 105.741 | 19.934 | 93.103 | 1.00 | 46.72 |
| ATOM | 3905 | O | GLY | D | 182 | 104.697 | 20.588 | 93.180 | 1.00 | 47.72 |
| ATOM | 3906 | N | THR | D | 183 | 106.184 | 19.421 | 91.960 | 1.00 | 46.52 |
| ATOM | 3907 | CA | THR | D | 183 | 105.424 | 19.577 | 90.724 | 1.00 | 45.61 |
| ATOM | 3908 | CB | THR | D | 183 | 106.044 | 20.652 | 89.807 | 1.00 | 45.40 |
| ATOM | 3909 | OG1 | THR | D | 183 | 107.457 | 20.453 | 89.725 | 1.00 | 46.04 |
| ATOM | 3910 | CG2 | THR | D | 183 | 105.766 | 22.049 | 90.358 | 1.00 | 44.85 |
| ATOM | 3911 | C | THR | D | 183 | 105.339 | 18.251 | 89.978 | 1.00 | 44.73 |
| ATOM | 3912 | O | THR | D | 183 | 106.350 | 17.597 | 89.730 | 1.00 | 44.87 |
| ATOM | 3913 | N | PRO | D | 184 | 104.116 | 17.818 | 89.642 | 1.00 | 44.69 |
| ATOM | 3914 | CD | PRO | D | 184 | 103.857 | 16.493 | 89.049 | 1.00 | 43.56 |
| ATOM | 3915 | CA | PRO | D | 184 | 102.854 | 18.510 | 89.930 | 1.00 | 44.95 |
| ATOM | 3916 | CB | PRO | D | 184 | 101.829 | 17.645 | 89.213 | 1.00 | 43.90 |
| ATOM | 3917 | CG | PRO | D | 184 | 102.400 | 16.271 | 89.384 | 1.00 | 43.92 |
| ATOM | 3918 | C | PRO | D | 184 | 102.559 | 18.636 | 91.431 | 1.00 | 46.12 |

TABLE 1-continued

FGFR1 D2–D3 Complexed with FGF2

| ATOM | 3919 | O | PRO | D | 184 | 103.002 | 17.806 | 92.242 | 1.00 | 45.37 |
|------|------|-----|-----|---|-----|---------|--------|--------|------|-------|
| ATOM | 3920 | N | GLN | D | 185 | 101.804 | 19.677 | 91.785 | 1.00 | 48.01 |
| ATOM | 3921 | CA | GLN | D | 185 | 101.439 | 19.942 | 93.179 | 1.00 | 48.94 |
| ATOM | 3922 | CB | GLN | D | 185 | 100.386 | 21.050 | 93.269 | 1.00 | 50.69 |
| ATOM | 3923 | CG | GLN | D | 185 | 100.407 | 21.749 | 94.605 | 1.00 | 55.14 |
| ATOM | 3924 | CD | GLN | D | 185 | 101.796 | 22.271 | 94.959 | 1.00 | 58.21 |
| ATOM | 3925 | OE1 | GLN | D | 185 | 102.026 | 22.757 | 96.067 | 1.00 | 61.45 |
| ATOM | 3926 | NE2 | GLN | D | 185 | 102.727 | 22.177 | 94.014 | 1.00 | 58.46 |
| ATOM | 3927 | C | GLN | D | 185 | 100.927 | 18.677 | 93.851 | 1.00 | 47.51 |
| ATOM | 3928 | O | GLN | D | 185 | 99.975 | 18.049 | 93.374 | 1.00 | 48.35 |
| ATOM | 3929 | N | PRO | D | 186 | 101.558 | 18.283 | 94.970 | 1.00 | 44.84 |
| ATOM | 3930 | CD | PRO | D | 186 | 102.748 | 18.894 | 95.593 | 1.00 | 43.75 |
| ATOM | 3931 | CA | PRO | D | 186 | 101.150 | 17.072 | 95.686 | 1.00 | 42.59 |
| ATOM | 3932 | CB | PRO | D | 186 | 102.346 | 16.799 | 96.590 | 1.00 | 42.85 |
| ATOM | 3933 | CG | PRO | D | 186 | 102.830 | 18.176 | 96.915 | 1.00 | 43.55 |
| ATOM | 3934 | C | PRO | D | 186 | 99.835 | 17.148 | 96.460 | 1.00 | 41.51 |
| ATOM | 3935 | O | PRO | D | 186 | 99.275 | 18.221 | 96.670 | 1.00 | 40.81 |
| ATOM | 3936 | N | THR | D | 187 | 99.337 | 15.984 | 96.862 | 1.00 | 41.66 |
| ATOM | 3937 | CA | THR | D | 187 | 98.108 | 15.901 | 97.638 | 1.00 | 40.35 |
| ATOM | 3938 | CB | THR | D | 187 | 97.232 | 14.753 | 97.203 | 1.00 | 39.73 |
| ATOM | 3939 | OG1 | THR | D | 187 | 98.044 | 13.590 | 97.003 | 1.00 | 40.03 |
| ATOM | 3940 | CG2 | THR | D | 187 | 96.502 | 15.108 | 95.941 | 1.00 | 40.19 |
| ATOM | 3941 | C | THR | D | 187 | 98.468 | 15.671 | 99.092 | 1.00 | 41.68 |
| ATOM | 3942 | O | THR | D | 187 | 99.486 | 15.041 | 99.408 | 1.00 | 42.57 |
| ATOM | 3943 | N | LEU | D | 188 | 97.612 | 16.174 | 99.973 | 1.00 | 41.12 |
| ATOM | 3944 | CA | LEU | D | 188 | 97.833 | 16.066 | 101.401 | 1.00 | 39.93 |
| ATOM | 3945 | CB | LEU | D | 188 | 97.967 | 17.475 | 101.992 | 1.00 | 39.49 |
| ATOM | 3946 | CG | LEU | D | 188 | 98.640 | 17.685 | 103.352 | 1.00 | 38.54 |
| ATOM | 3947 | CD1 | LEU | D | 188 | 97.695 | 18.466 | 104.252 | 1.00 | 36.15 |
| ATOM | 3948 | CD2 | LEU | D | 188 | 99.031 | 16.351 | 103.972 | 1.00 | 37.43 |
| ATOM | 3949 | C | LEU | D | 188 | 96.690 | 15.317 | 102.076 | 1.00 | 39.41 |
| ATOM | 3950 | O | LEU | D | 188 | 95.525 | 15.693 | 101.944 | 1.00 | 39.82 |
| ATOM | 3951 | N | ARG | D | 189 | 97.033 | 14.254 | 102.795 | 1.00 | 38.29 |
| ATOM | 3952 | CA | ARG | D | 189 | 96.050 | 13.463 | 103.515 | 1.00 | 37.44 |
| ATOM | 3953 | CB | ARG | D | 189 | 95.760 | 12.168 | 102.751 | 1.00 | 37.63 |
| ATOM | 3954 | CG | ARG | D | 189 | 96.969 | 11.294 | 102.500 | 1.00 | 40.60 |
| ATOM | 3955 | CD | ARG | D | 189 | 96.551 | 9.935 | 101.942 | 1.00 | 41.74 |
| ATOM | 3956 | NE | ARG | D | 189 | 97.654 | 8.970 | 101.942 | 1.00 | 42.49 |
| ATOM | 3957 | CZ | ARG | D | 189 | 97.512 | 7.668 | 101.714 | 1.00 | 41.00 |
| ATOM | 3958 | C | ARG | D | 189 | 96.630 | 13.156 | 104.891 | 1.00 | 36.92 |
| ATOM | 3959 | O | ARG | D | 189 | 97.844 | 13.071 | 105.035 | 1.00 | 37.76 |
| ATOM | 3960 | N | TRP | D | 190 | 95.771 | 13.004 | 105.899 | 1.00 | 37.03 |
| ATOM | 3961 | CA | TRP | D | 190 | 96.218 | 12.715 | 107.260 | 1.00 | 35.13 |
| ATOM | 3962 | CB | TRP | D | 190 | 95.732 | 13.797 | 108.214 | 1.00 | 34.41 |
| ATOM | 3963 | CG | TRP | D | 190 | 96.297 | 15.173 | 107.933 | 1.00 | 35.57 |
| ATOM | 3964 | CD2 | TRP | D | 190 | 97.500 | 15.735 | 108.479 | 1.00 | 35.94 |
| ATOM | 3965 | CE2 | TRP | D | 190 | 97.604 | 17.060 | 107.984 | 1.00 | 34.87 |
| ATOM | 3966 | CE3 | TRP | D | 190 | 98.502 | 15.247 | 109.338 | 1.00 | 36.28 |
| ATOM | 3967 | CD1 | TRP | D | 190 | 95.744 | 16.149 | 107.146 | 1.00 | 33.94 |
| ATOM | 3968 | NE1 | TRP | D | 190 | 96.520 | 17.283 | 107.178 | 1.00 | 32.39 |
| ATOM | 3969 | CZ2 | TRP | D | 190 | 98.673 | 17.911 | 108.323 | 1.00 | 36.31 |
| ATOM | 3970 | CZ3 | TRP | D | 190 | 99.568 | 16.093 | 109.678 | 1.00 | 37.87 |
| ATOM | 3971 | CH2 | TRP | D | 190 | 99.642 | 17.414 | 109.167 | 1.00 | 37.94 |
| ATOM | 3972 | C | TRP | D | 190 | 95.750 | 11.361 | 107.773 | 1.00 | 35.45 |
| ATOM | 3973 | O | TRP | D | 190 | 94.747 | 10.822 | 107.322 | 1.00 | 35.52 |
| ATOM | 3974 | N | LEU | D | 191 | 96.484 | 10.821 | 108.734 | 1.00 | 36.10 |
| ATOM | 3975 | CA | LEU | D | 191 | 96.161 | 9.520 | 109.307 | 1.00 | 37.96 |
| ATOM | 3976 | CB | LEU | D | 191 | 97.143 | 8.455 | 108.812 | 1.00 | 39.10 |
| ATOM | 3977 | CG | LEU | D | 191 | 97.237 | 8.046 | 107.349 | 1.00 | 39.59 |
| ATOM | 3978 | CD1 | LEU | D | 191 | 98.320 | 6.988 | 107.239 | 1.00 | 40.57 |
| ATOM | 3979 | CD2 | LEU | D | 191 | 95.915 | 7.493 | 106.856 | 1.00 | 39.59 |
| ATOM | 3980 | C | LEU | D | 191 | 96.252 | 9.520 | 110.824 | 1.00 | 38.40 |
| ATOM | 3981 | O | LEU | D | 191 | 97.307 | 9.861 | 111.376 | 1.00 | 39.40 |
| ATOM | 3982 | N | LYS | D | 192 | 95.168 | 9.144 | 111.504 | 1.00 | 36.74 |
| ATOM | 3983 | CA | LYS | D | 192 | 95.237 | 9.056 | 112.957 | 1.00 | 34.76 |
| ATOM | 3984 | CB | LYS | D | 192 | 93.912 | 9.326 | 113.658 | 1.00 | 33.63 |
| ATOM | 3985 | CG | LYS | D | 192 | 94.034 | 8.999 | 115.137 | 1.00 | 31.25 |
| ATOM | 3986 | CD | LYS | D | 192 | 92.711 | 8.816 | 115.826 | 1.00 | 32.21 |
| ATOM | 3987 | CE | LYS | D | 192 | 92.027 | 10.142 | 116.087 | 1.00 | 32.40 |
| ATOM | 3988 | NZ | LYS | D | 192 | 91.606 | 10.260 | 117.511 | 1.00 | 29.92 |
| ATOM | 3989 | C | LYS | D | 192 | 95.633 | 7.623 | 113.239 | 1.00 | 34.69 |
| ATOM | 3990 | O | LYS | D | 192 | 94.914 | 6.684 | 112.883 | 1.00 | 33.43 |
| ATOM | 3991 | N | ASN | D | 193 | 96.788 | 7.468 | 113.874 | 1.00 | 35.21 |
| ATOM | 3992 | CA | ASN | D | 193 | 97.338 | 6.165 | 114.216 | 1.00 | 35.69 |
| ATOM | 3993 | CB | ASN | D | 193 | 96.534 | 5.508 | 115.331 | 1.00 | 34.53 |
| ATOM | 3994 | CG | ASN | D | 193 | 96.728 | 6.204 | 116.643 | 1.00 | 34.30 |
| ATOM | 3995 | OD1 | ASN | D | 193 | 97.855 | 6.551 | 117.004 | 1.00 | 31.94 |

TABLE 1-continued

FGFR1 D2–D3 Complexed with FGF2

| ATOM | 3996 | ND2 | ASN | D | 193 | 95.636 | 6.419 | 117.372 | 1.00 | 34.92 |
|---|---|---|---|---|---|---|---|---|---|---|
| ATOM | 3997 | C | ASN | D | 193 | 97.445 | 5.224 | 113.033 | 1.00 | 36.74 |
| ATOM | 3998 | O | ASN | D | 193 | 97.162 | 4.029 | 113.144 | 1.00 | 35.50 |
| ATOM | 3999 | N | GLY | D | 194 | 97.855 | 5.777 | 111.897 | 1.00 | 38.21 |
| ATOM | 4000 | CA | GLY | D | 194 | 98.039 | 4.969 | 110.707 | 1.00 | 38.61 |
| ATOM | 4001 | C | GLY | D | 194 | 96.803 | 4.626 | 109.908 | 1.00 | 38.67 |
| ATOM | 4002 | O | GLY | D | 194 | 96.913 | 4.006 | 108.856 | 1.00 | 39.28 |
| ATOM | 4003 | N | LYS | D | 195 | 95.628 | 5.013 | 110.382 | 1.00 | 38.69 |
| ATOM | 4004 | CA | LYS | D | 195 | 94.417 | 4.703 | 109.639 | 1.00 | 37.44 |
| ATOM | 4005 | CB | LYS | D | 195 | 93.403 | 4.009 | 110.553 | 1.00 | 36.65 |
| ATOM | 4006 | C | LYS | D | 195 | 93.811 | 5.959 | 109.018 | 1.00 | 37.35 |
| ATOM | 4007 | O | LYS | D | 195 | 94.169 | 7.081 | 109.380 | 1.00 | 36.18 |
| ATOM | 4008 | N | GLU | D | 196 | 92.917 | 5.759 | 108.056 | 1.00 | 39.04 |
| ATOM | 4009 | CA | GLU | D | 196 | 92.237 | 6.860 | 107.394 | 1.00 | 40.62 |
| ATOM | 4010 | CB | GLU | D | 196 | 91.150 | 6.317 | 106.463 | 1.00 | 41.16 |
| ATOM | 4011 | C | GLU | D | 196 | 91.612 | 7.697 | 108.500 | 1.00 | 42.49 |
| ATOM | 4012 | O | GLU | D | 196 | 91.058 | 7.154 | 109.457 | 1.00 | 42.76 |
| ATOM | 4013 | N | PHE | D | 197 | 91.704 | 9.016 | 108.380 | 1.00 | 45.15 |
| ATOM | 4014 | CA | PHE | D | 197 | 91.161 | 9.905 | 109.404 | 1.00 | 47.11 |
| ATOM | 4015 | CB | PHE | D | 197 | 92.281 | 10.763 | 109.997 | 1.00 | 48.35 |
| ATOM | 4016 | CG | PHE | D | 197 | 91.847 | 11.619 | 111.151 | 1.00 | 50.43 |
| ATOM | 4017 | CD1 | PHE | D | 197 | 92.496 | 12.818 | 111.422 | 1.00 | 51.39 |
| ATOM | 4018 | CD2 | PHE | D | 197 | 90.812 | 11.214 | 111.995 | 1.00 | 51.03 |
| ATOM | 4019 | CE1 | PHE | D | 197 | 92.122 | 13.601 | 112.522 | 1.00 | 51.27 |
| ATOM | 4020 | CE2 | PHE | D | 197 | 90.433 | 11.988 | 113.095 | 1.00 | 49.59 |
| ATOM | 4021 | CZ | PHE | D | 197 | 91.087 | 13.181 | 113.358 | 1.00 | 49.70 |
| ATOM | 4022 | C | PHE | D | 197 | 90.082 | 10.824 | 108.856 | 1.00 | 48.38 |
| ATOM | 4023 | O | PHE | D | 197 | 90.387 | 11.911 | 108.379 | 1.00 | 49.86 |
| ATOM | 4024 | N | LYS | D | 198 | 88.826 | 10.396 | 108.925 | 1.00 | 49.00 |
| ATOM | 4025 | CA | LYS | D | 198 | 87.725 | 11.217 | 108.433 | 1.00 | 49.34 |
| ATOM | 4026 | CB | LYS | D | 198 | 86.570 | 10.307 | 107.993 | 1.00 | 49.48 |
| ATOM | 4027 | C | LYS | D | 198 | 87.268 | 12.189 | 109.537 | 1.00 | 49.85 |
| ATOM | 4028 | O | LYS | D | 198 | 87.350 | 11.874 | 110.719 | 1.00 | 50.32 |
| ATOM | 4029 | N | PRO | D | 199 | 86.785 | 13.385 | 109.161 | 1.00 | 50.70 |
| ATOM | 4030 | CD | PRO | D | 199 | 86.568 | 13.840 | 107.780 | 1.00 | 51.66 |
| ATOM | 4031 | CA | PRO | D | 199 | 86.321 | 14.400 | 110.116 | 1.00 | 51.18 |
| ATOM | 4032 | CB | PRO | D | 199 | 85.886 | 15.551 | 109.217 | 1.00 | 51.42 |
| ATOM | 4033 | CG | PRO | D | 199 | 85.464 | 14.847 | 107.961 | 1.00 | 52.15 |
| ATOM | 4034 | C | PRO | D | 199 | 85.218 | 13.976 | 111.074 | 1.00 | 51.82 |
| ATOM | 4035 | O | PRO | D | 199 | 85.035 | 14.603 | 112.125 | 1.00 | 52.82 |
| ATOM | 4036 | N | ASP | D | 200 | 84.472 | 12.929 | 110.728 | 1.00 | 52.67 |
| ATOM | 4037 | CA | ASP | D | 200 | 83.397 | 12.455 | 111.609 | 1.00 | 52.73 |
| ATOM | 4038 | CB | ASP | D | 200 | 82.415 | 11.550 | 110.879 | 1.00 | 54.01 |
| ATOM | 4039 | CG | ASP | D | 200 | 81.571 | 12.301 | 109.917 | 1.00 | 56.59 |
| ATOM | 4040 | OD1 | ASP | D | 200 | 82.109 | 12.649 | 108.841 | 1.00 | 58.29 |
| ATOM | 4041 | OD2 | ASP | D | 200 | 80.386 | 12.552 | 110.257 | 1.00 | 57.25 |
| ATOM | 4042 | G | ASP | D | 200 | 83.986 | 11.647 | 112.731 | 1.00 | 51.43 |
| ATOM | 4043 | O | ASP | D | 200 | 83.264 | 11.159 | 113.606 | 1.00 | 51.56 |
| ATOM | 4044 | N | HIS | D | 201 | 85.296 | 11.482 | 112.683 | 1.00 | 50.04 |
| ATOM | 4045 | CA | HIS | D | 201 | 85.995 | 10.714 | 113.697 | 1.00 | 50.04 |
| ATOM | 4046 | CB | HIS | D | 201 | 87.400 | 10.355 | 113.216 | 1.00 | 54.12 |
| ATOM | 4047 | CG | HIS | D | 201 | 87.430 | 9.254 | 112.200 | 1.00 | 59.01 |
| ATOM | 4048 | CD2 | HIS | D | 201 | 88.217 | 8.159 | 112.102 | 1.00 | 60.50 |
| ATOM | 4049 | ND1 | HIS | D | 201 | 86.591 | 9.220 | 111.103 | 1.00 | 61.62 |
| ATOM | 4050 | CE1 | HIS | D | 201 | 86.857 | 8.148 | 110.373 | 1.00 | 61.43 |
| ATOM | 4051 | NE2 | HIS | D | 201 | 87.836 | 7.485 | 110.957 | 1.00 | 61.73 |
| ATOM | 4052 | G | HIS | D | 201 | 86.092 | 11.457 | 115.036 | 1.00 | 48.25 |
| ATOM | 4053 | O | HIS | D | 201 | 86.576 | 10.892 | 116.025 | 1.00 | 49.24 |
| ATOM | 4054 | N | ARG | D | 202 | 85.647 | 12.717 | 115.090 | 1.00 | 44.11 |
| ATOM | 4055 | CA | ARG | D | 202 | 85.673 | 13.443 | 116.354 | 1.00 | 42.29 |
| ATOM | 4056 | CB | ARG | D | 202 | 87.067 | 14.035 | 116.596 | 1.00 | 38.00 |
| ATOM | 4057 | CG | ARG | D | 202 | 87.460 | 15.167 | 115.659 | 1.00 | 33.51 |
| ATOM | 4058 | CD | ARG | D | 202 | 88.948 | 15.528 | 115.748 | 1.00 | 27.20 |
| ATOM | 4059 | NE | ARG | D | 202 | 89.348 | 15.969 | 117.079 | 1.00 | 22.95 |
| ATOM | 4060 | CZ | ARG | D | 202 | 89.011 | 17.130 | 117.633 | 1.00 | 18.84 |
| ATOM | 4061 | NH1 | ARG | D | 202 | 88.259 | 18.008 | 116.987 | 1.00 | 15.62 |
| ATOM | 4062 | NH2 | ARG | D | 202 | 89.432 | 17.411 | 118.851 | 1.00 | 17.58 |
| ATOM | 4063 | C | ARG | D | 202 | 84.622 | 14.532 | 116.313 | 1.00 | 43.43 |
| ATOM | 4064 | O | ARG | D | 202 | 84.375 | 15.108 | 115.254 | 1.00 | 44.47 |
| ATOM | 4065 | N | ILE | D | 203 | 84.001 | 14.806 | 117.459 | 1.00 | 43.13 |
| ATOM | 4066 | CA | ILE | D | 203 | 82.970 | 15.840 | 117.525 | 1.00 | 44.86 |
| ATOM | 4067 | CB | ILE | D | 203 | 82.374 | 15.992 | 118.974 | 1.00 | 45.77 |
| ATOM | 4068 | CG2 | ILE | D | 203 | 81.579 | 14.742 | 119.350 | 1.00 | 44.96 |
| ATOM | 4069 | CG1 | ILE | D | 203 | 83.484 | 16.303 | 119.990 | 1.00 | 45.71 |
| ATOM | 4070 | CD1 | ILE | D | 203 | 84.635 | 15.309 | 120.011 | 1.00 | 46.02 |
| ATOM | 4071 | C | ILE | D | 203 | 83.552 | 17.180 | 117.058 | 1.00 | 45.25 |
| ATOM | 4072 | O | ILE | D | 203 | 84.687 | 17.528 | 117.393 | 1.00 | 44.55 |

TABLE 1-continued

FGFR1 D2–D3 Complexed with FGF2

| | | | | | | | | | | |
|---|---|---|---|---|---|---|---|---|---|---|
| ATOM | 4073 | N | GLY | D | 204 | 82.776 | 17.921 | 116.269 | 1.00 | 45.78 |
| ATOM | 4074 | CA | GLY | D | 204 | 83.254 | 19.192 | 115.751 | 1.00 | 44.14 |
| ATOM | 4075 | C | GLY | D | 204 | 84.179 | 18.966 | 114.569 | 1.00 | 42.10 |
| ATOM | 4076 | O | GLY | D | 204 | 84.496 | 19.897 | 113.835 | 1.00 | 42.25 |
| ATOM | 4077 | N | GLY | D | 205 | 84.614 | 17.720 | 114.400 | 1.00 | 41.53 |
| ATOM | 4078 | CA | GLY | D | 205 | 85.494 | 17.359 | 113.300 | 1.00 | 42.52 |
| ATOM | 4079 | C | GLY | D | 205 | 86.826 | 18.076 | 113.305 | 1.00 | 43.08 |
| ATOM | 4080 | O | GLY | D | 205 | 87.429 | 18.274 | 114.367 | 1.00 | 43.80 |
| ATOM | 4081 | N | TYR | D | 206 | 87.284 | 18.468 | 112.118 | 1.00 | 42.12 |
| ATOM | 4082 | CA | TYR | D | 206 | 88.552 | 19.174 | 111.986 | 1.00 | 40.97 |
| ATOM | 4083 | CB | TYR | D | 206 | 89.701 | 18.194 | 112.168 | 1.00 | 43.57 |
| ATOM | 4084 | CG | TYR | D | 206 | 89.726 | 17.090 | 111.150 | 1.00 | 44.70 |
| ATOM | 4085 | CD1 | TYR | D | 206 | 89.353 | 15.795 | 111.490 | 1.00 | 46.53 |
| ATOM | 4086 | CE1 | TYR | D | 206 | 89.397 | 14.773 | 110.552 | 1.00 | 49.43 |
| ATOM | 4087 | CD2 | TYR | D | 206 | 90.138 | 17.341 | 109.845 | 1.00 | 47.44 |
| ATOM | 4088 | CE2 | TYR | D | 206 | 90.181 | 16.339 | 108.900 | 1.00 | 49.64 |
| ATOM | 4089 | CZ | TYR | D | 206 | 89.811 | 15.056 | 109.254 | 1.00 | 51.35 |
| ATOM | 4090 | OH | TYR | D | 206 | 89.844 | 14.073 | 108.292 | 1.00 | 53.81 |
| ATOM | 4091 | C | TYR | D | 206 | 88.682 | 19.858 | 110.629 | 1.00 | 40.00 |
| ATOM | 4092 | O | TYR | D | 206 | 88.095 | 19.410 | 109.645 | 1.00 | 39.98 |
| ATOM | 4093 | N | LYS | D | 207 | 89.458 | 20.936 | 110.577 | 1.00 | 39.38 |
| ATOM | 4094 | CA | LYS | D | 207 | 89.662 | 21.667 | 109.332 | 1.00 | 40.21 |
| ATOM | 4095 | CB | LYS | D | 207 | 89.458 | 23.173 | 109.563 | 1.00 | 38.02 |
| ATOM | 4096 | C | LYS | D | 207 | 91.054 | 21.400 | 108.736 | 1.00 | 41.63 |
| ATOM | 4097 | O | LYS | D | 207 | 92.067 | 21.362 | 109.454 | 1.00 | 41.52 |
| ATOM | 4098 | N | VAL | D | 208 | 91.090 | 21.206 | 107.418 | 1.00 | 42.22 |
| ATOM | 4099 | CA | VAL | D | 208 | 92.337 | 20.948 | 106.711 | 1.00 | 42.05 |
| ATOM | 4100 | CB | VAL | D | 208 | 92.261 | 19.614 | 105.919 | 1.00 | 41.48 |
| ATOM | 4101 | CD1 | VAL | D | 208 | 93.631 | 19.253 | 105.364 | 1.00 | 40.66 |
| ATOM | 4102 | CG2 | VAL | D | 208 | 91.745 | 18.505 | 106.816 | 1.00 | 40.29 |
| ATOM | 4103 | C | VAL | D | 208 | 92.626 | 22.081 | 105.736 | 1.00 | 42.09 |
| ATOM | 4104 | O | VAL | D | 208 | 92.114 | 22.079 | 104.626 | 1.00 | 43.46 |
| ATOM | 4105 | N | ARG | D | 209 | 93.429 | 23.053 | 106.151 | 1.00 | 42.59 |
| ATOM | 4106 | CA | ARG | D | 209 | 93.776 | 24.165 | 105.276 | 1.00 | 44.83 |
| ATOM | 4107 | CB | ARG | D | 209 | 94.227 | 25.362 | 106.117 | 1.00 | 44.83 |
| ATOM | 4108 | C | ARG | D | 209 | 94.904 | 23.678 | 104.354 | 1.00 | 45.93 |
| ATOM | 4109 | O | ARG | D | 209 | 96.055 | 23.561 | 104.783 | 1.00 | 46.40 |
| ATOM | 4110 | N | TYR | D | 210 | 94.562 | 23.382 | 103.097 | 1.00 | 46.61 |
| ATOM | 4111 | CA | TYR | D | 210 | 95.530 | 22.877 | 102.125 | 1.00 | 45.87 |
| ATOM | 4112 | CB | TYR | D | 210 | 94.814 | 22.377 | 100.882 | 1.00 | 45.46 |
| ATOM | 4113 | CG | TYR | D | 210 | 93.833 | 21.280 | 101.175 | 1.00 | 47.79 |
| ATOM | 4114 | CD1 | TYR | D | 210 | 92.470 | 21.552 | 101.287 | 1.00 | 48.81 |
| ATOM | 4115 | CE1 | TYR | D | 210 | 91.556 | 20.538 | 101.594 | 1.00 | 50.01 |
| ATOM | 4116 | CD2 | TYR | D | 210 | 94.268 | 19.966 | 101.376 | 1.00 | 48.67 |
| ATOM | 4117 | CE2 | TYR | D | 210 | 93.365 | 18.942 | 101.685 | 1.00 | 49.71 |
| ATOM | 4118 | CZ | TYR | D | 210 | 92.011 | 19.236 | 101.793 | 1.00 | 50.16 |
| ATOM | 4119 | OH | TYR | D | 210 | 91.117 | 18.233 | 102.101 | 1.00 | 51.87 |
| ATOM | 4120 | C | TYR | D | 210 | 96.573 | 23.899 | 101.725 | 1.00 | 44.94 |
| ATOM | 4121 | O | TYR | D | 210 | 97.716 | 23.545 | 101.414 | 1.00 | 44.92 |
| ATOM | 4122 | N | ALA | D | 211 | 96.178 | 25.168 | 101.728 | 1.00 | 43.47 |
| ATOM | 4123 | CA | ALA | D | 211 | 97.100 | 26.233 | 101.376 | 1.00 | 42.49 |
| ATOM | 4124 | CB | ALA | D | 211 | 96.368 | 27.551 | 101.316 | 1.00 | 41.51 |
| ATOM | 4125 | C | ALA | D | 211 | 98.206 | 26.301 | 102.415 | 1.00 | 42.14 |
| ATOM | 4126 | O | ALA | D | 211 | 99.284 | 26.815 | 102.153 | 1.00 | 42.30 |
| ATOM | 4127 | N | THR | D | 212 | 97.931 | 25.764 | 103.596 | 1.00 | 43.17 |
| ATOM | 4128 | CA | THR | D | 212 | 98.892 | 25.775 | 104.683 | 1.00 | 43.50 |
| ATOM | 4129 | CB | THR | D | 212 | 98.255 | 26.374 | 105.929 | 1.00 | 44.87 |
| ATOM | 4130 | OG1 | THR | D | 212 | 97.646 | 27.622 | 105.577 | 1.00 | 44.88 |
| ATOM | 4131 | CG2 | THR | D | 212 | 99.307 | 26.626 | 107.001 | 1.00 | 47.61 |
| ATOM | 4132 | C | THR | D | 212 | 99.459 | 24.392 | 104.994 | 1.00 | 42.04 |
| ATOM | 4133 | O | THR | D | 212 | 100.328 | 24.244 | 105.851 | 1.00 | 41.28 |
| ATOM | 4134 | N | TRP | D | 213 | 98.979 | 23.380 | 104.284 | 1.00 | 41.50 |
| ATOM | 4135 | CA | TRP | D | 213 | 99.477 | 22.030 | 104.499 | 1.00 | 41.66 |
| ATOM | 4136 | CB | TRP | D | 213 | 100.965 | 21.957 | 104.160 | 1.00 | 42.60 |
| ATOM | 4137 | CG | TRP | D | 213 | 101.248 | 22.323 | 102.770 | 1.00 | 44.75 |
| ATOM | 4138 | CD2 | TRP | D | 213 | 101.116 | 21.472 | 101.635 | 1.00 | 44.62 |
| ATOM | 4139 | CE2 | TRP | D | 213 | 101.425 | 22.245 | 100.498 | 1.00 | 45.13 |
| ATOM | 4140 | CE3 | TRP | D | 213 | 100.762 | 20.128 | 101.469 | 1.00 | 44.93 |
| ATOM | 4141 | CD1 | TRP | D | 213 | 101.623 | 23.548 | 102.299 | 1.00 | 45.15 |
| ATOM | 4142 | NE1 | TRP | D | 213 | 101.730 | 23.510 | 100.931 | 1.00 | 46.03 |
| ATOM | 4143 | CZ2 | TRP | D | 213 | 101.392 | 21.720 | 99.206 | 1.00 | 45.66 |
| ATOM | 4144 | CZ3 | TRP | D | 213 | 100.727 | 19.605 | 100.192 | 1.00 | 46.75 |
| ATOM | 4145 | CH2 | TRP | D | 213 | 101.042 | 20.402 | 99.071 | 1.00 | 46.85 |
| ATOM | 4146 | C | TRP | D | 213 | 99.309 | 21.671 | 105.953 | 1.00 | 40.31 |
| ATOM | 4147 | O | TRP | D | 213 | 100.199 | 21.085 | 106.565 | 1.00 | 40.74 |
| ATOM | 4148 | N | SER | D | 214 | 98.159 | 22.002 | 106.508 | 1.00 | 38.32 |
| ATOM | 4149 | CA | SER | D | 214 | 97.951 | 21.747 | 107.912 | 1.00 | 38.09 |

TABLE 1-continued

FGFR1 D2–D3 Complexed with FGF2

| ATOM | 4150 | CB | SER | D | 214 | 98.153 | 23.056 | 108.661 | 1.00 | 38.40 |
|---|---|---|---|---|---|---|---|---|---|---|
| ATOM | 4151 | OG | SER | D | 214 | 97.366 | 24.080 | 108.070 | 1.00 | 37.60 |
| ATOM | 4152 | C | SER | D | 214 | 96.591 | 21.177 | 108.268 | 1.00 | 37.89 |
| ATOM | 4153 | O | SER | D | 214 | 95.641 | 21.253 | 107.483 | 1.00 | 38.08 |
| ATOM | 4154 | N | ILE | D | 215 | 96.517 | 20.591 | 109.459 | 1.00 | 35.82 |
| ATOM | 4155 | CA | ILE | D | 215 | 95.268 | 20.055 | 109.961 | 1.00 | 34.85 |
| ATOM | 4156 | CB | ILE | D | 215 | 95.305 | 18.522 | 110.127 | 1.00 | 34.07 |
| ATOM | 4157 | CG2 | ILE | D | 215 | 96.448 | 18.109 | 111.040 | 1.00 | 33.74 |
| ATOM | 4158 | CG1 | ILE | D | 215 | 93.954 | 18.044 | 110.668 | 1.00 | 33.63 |
| ATOM | 4159 | CD1 | ILE | D | 215 | 93.741 | 16.544 | 110.588 | 1.00 | 31.56 |
| ATOM | 4160 | C | ILE | D | 215 | 95.051 | 20.732 | 111.306 | 1.00 | 34.51 |
| ATOM | 4161 | O | ILE | D | 215 | 95.996 | 20.944 | 112.068 | 1.00 | 34.28 |
| ATOM | 4162 | N | ILE | D | 216 | 93.804 | 21.086 | 111.588 | 1.00 | 33.79 |
| ATOM | 4163 | CA | ILE | D | 216 | 93.486 | 21.773 | 112.828 | 1.00 | 32.42 |
| ATOM | 4164 | CB | ILE | D | 216 | 93.075 | 23.230 | 112.515 | 1.00 | 32.82 |
| ATOM | 4165 | CG2 | ILE | D | 216 | 92.639 | 23.949 | 113.784 | 1.00 | 32.35 |
| ATOM | 4166 | CG1 | ILE | D | 216 | 94.249 | 23.947 | 111.848 | 1.00 | 31.96 |
| ATOM | 4167 | CD1 | ILE | D | 216 | 93.925 | 25.324 | 111.396 | 1.00 | 31.43 |
| ATOM | 4168 | C | ILE | D | 216 | 92.379 | 21.080 | 113.619 | 1.00 | 31.47 |
| ATOM | 4169 | O | ILE | D | 216 | 91.356 | 20.690 | 113.061 | 1.00 | 30.20 |
| ATOM | 4170 | N | MET | D | 217 | 92.601 | 20.932 | 114.921 | 1.00 | 30.40 |
| ATOM | 4171 | CA | MET | D | 217 | 91.639 | 20.307 | 115.808 | 1.00 | 31.05 |
| ATOM | 4172 | CB | MET | D | 217 | 92.220 | 19.030 | 116.405 | 1.00 | 31.90 |
| ATOM | 4173 | CG | MET | D | 217 | 92.655 | 18.028 | 115.372 | 1.00 | 34.20 |
| ATOM | 4174 | SD | MET | D | 217 | 92.974 | 16.395 | 116.081 | 1.00 | 39.57 |
| ATOM | 4175 | CE | MET | D | 217 | 94.743 | 16.222 | 115.824 | 1.00 | 33.97 |
| ATOM | 4176 | C | MET | D | 217 | 91.310 | 21.268 | 116.938 | 1.00 | 32.05 |
| ATOM | 4177 | O | MET | D | 217 | 92.201 | 21.789 | 117.604 | 1.00 | 30.41 |
| ATOM | 4178 | N | ASP | D | 218 | 90.019 | 21.482 | 117.150 | 1.00 | 34.51 |
| ATOM | 4179 | CA | ASP | D | 218 | 89.503 | 22.367 | 118.186 | 1.00 | 34.94 |
| ATOM | 4180 | CB | ASP | D | 218 | 88.201 | 22.968 | 117.642 | 1.00 | 35.60 |
| ATOM | 4181 | CG | ASP | D | 218 | 87.680 | 24.115 | 118.468 | 1.00 | 38.16 |
| ATOM | 4182 | OD1 | ASP | D | 218 | 87.193 | 23.858 | 119.592 | 1.00 | 40.42 |
| ATOM | 4183 | OD2 | ASP | D | 218 | 87.753 | 25.272 | 117.989 | 1.00 | 37.02 |
| ATOM | 4184 | C | ASP | D | 218 | 89.268 | 21.533 | 119.460 | 1.00 | 35.32 |
| ATOM | 4185 | O | ASP | D | 218 | 89.088 | 20.318 | 119.380 | 1.00 | 37.02 |
| ATOM | 4186 | N | SER | D | 219 | 89.294 | 22.181 | 120.623 | 1.00 | 35.62 |
| ATOM | 4187 | CA | SER | D | 219 | 89.073 | 21.525 | 121.916 | 1.00 | 36.41 |
| ATOM | 4188 | CB | SER | D | 219 | 87.616 | 21.757 | 122.361 | 1.00 | 37.09 |
| ATOM | 4189 | OG | SER | D | 219 | 87.424 | 21.434 | 123.736 | 1.00 | 40.88 |
| ATOM | 4190 | C | SER | D | 219 | 89.422 | 20.024 | 121.962 | 1.00 | 35.85 |
| ATOM | 4191 | O | SER | D | 219 | 88.535 | 19.165 | 122.012 | 1.00 | 35.43 |
| ATOM | 4192 | N | VAL | D | 220 | 90.721 | 19.729 | 121.951 | 1.00 | 35.38 |
| ATOM | 4193 | CA | VAL | D | 220 | 91.217 | 18.356 | 121.999 | 1.00 | 34.96 |
| ATOM | 4194 | CB | VAL | D | 220 | 92.725 | 18.305 | 121.745 | 1.00 | 34.89 |
| ATOM | 4195 | CG1 | VAL | D | 220 | 93.016 | 18.848 | 120.369 | 1.00 | 35.35 |
| ATOM | 4196 | CG2 | VAL | D | 220 | 93.471 | 19.095 | 122.824 | 1.00 | 34.72 |
| ATOM | 4197 | C | VAL | D | 220 | 90.940 | 17.663 | 123.329 | 1.00 | 34.86 |
| ATOM | 4198 | O | VAL | D | 220 | 91.165 | 18.204 | 124.403 | 1.00 | 35.98 |
| ATOM | 4199 | N | VAL | D | 221 | 90.470 | 16.437 | 123.227 | 1.00 | 34.78 |
| ATOM | 4200 | CA | VAL | D | 221 | 90.117 | 15.631 | 124.373 | 1.00 | 34.91 |
| ATOM | 4201 | CB | VAL | D | 221 | 88.632 | 15.251 | 124.235 | 1.00 | 34.42 |
| ATOM | 4202 | CG1 | VAL | D | 221 | 87.779 | 16.515 | 124.192 | 1.00 | 30.48 |
| ATOM | 4203 | CG2 | VAL | D | 221 | 88.423 | 14.475 | 122.935 | 1.00 | 30.80 |
| ATOM | 4204 | C | VAL | D | 221 | 91.000 | 14.374 | 124.353 | 1.00 | 35.97 |
| ATOM | 4205 | O | VAL | D | 221 | 91.607 | 14.056 | 123.332 | 1.00 | 37.52 |
| ATOM | 4206 | N | PRO | D | 222 | 91.068 | 13.637 | 125.469 | 1.00 | 35.56 |
| ATOM | 4207 | CD | PRO | D | 222 | 90.372 | 13.891 | 126.742 | 1.00 | 35.68 |
| ATOM | 4208 | CA | PRO | D | 222 | 91.883 | 12.419 | 125.555 | 1.00 | 34.78 |
| ATOM | 4209 | CB | PRO | D | 222 | 91.426 | 11.801 | 126.874 | 1.00 | 36.22 |
| ATOM | 4210 | CG | PRO | D | 222 | 91.150 | 13.011 | 127.712 | 1.00 | 36.43 |
| ATOM | 4211 | C | PRO | D | 222 | 91.714 | 11.458 | 124.383 | 1.00 | 33.09 |
| ATOM | 4212 | O | PRO | D | 222 | 92.682 | 10.842 | 123.935 | 1.00 | 33.47 |
| ATOM | 4213 | N | SER | D | 223 | 90.490 | 11.325 | 123.887 | 1.00 | 31.05 |
| ATOM | 4214 | CA | SER | D | 223 | 90.250 | 10.412 | 122.783 | 1.00 | 31.65 |
| ATOM | 4215 | CB | SER | D | 223 | 88.761 | 10.353 | 122.460 | 1.00 | 29.34 |
| ATOM | 4216 | OG | SER | D | 223 | 88.308 | 11.570 | 121.913 | 1.00 | 32.73 |
| ATOM | 4217 | C | SER | D | 223 | 91.041 | 10.824 | 121.545 | 1.00 | 32.52 |
| ATOM | 4218 | O | SER | D | 223 | 91.237 | 10.033 | 120.627 | 1.00 | 33.05 |
| ATOM | 4219 | N | ASP | D | 224 | 91.501 | 12.068 | 121.524 | 1.00 | 33.64 |
| ATOM | 4220 | CA | ASP | D | 224 | 92.276 | 12.556 | 120.394 | 1.00 | 33.83 |
| ATOM | 4221 | CB | ASP | D | 224 | 92.216 | 14.088 | 120.303 | 1.00 | 33.17 |
| ATOM | 4222 | CG | ASP | D | 224 | 90.866 | 14.593 | 119.820 | 1.00 | 33.79 |
| ATOM | 4223 | OD1 | ASP | D | 224 | 90.395 | 14.105 | 118.769 | 1.00 | 35.24 |
| ATOM | 4224 | OD2 | ASP | D | 224 | 90.278 | 15.478 | 120.482 | 1.00 | 32.14 |
| ATOM | 4225 | C | ASP | D | 224 | 93.723 | 12.116 | 120.515 | 1.00 | 34.68 |
| ATOM | 4226 | O | ASP | D | 224 | 94.450 | 12.112 | 119.531 | 1.00 | 35.14 |

TABLE 1-continued

FGFR1 D2–D3 Complexed with FGF2

| ATOM | 4227 | N | LYS | D | 225 | 94.146 | 11.753 | 121.722 | 1.00 | 35.77 |
|---|---|---|---|---|---|---|---|---|---|---|
| ATOM | 4228 | CA | LYS | D | 225 | 95.527 | 11.323 | 121.923 | 1.00 | 36.05 |
| ATOM | 4229 | CB | LYS | D | 225 | 95.731 | 10.715 | 123.315 | 1.00 | 39.64 |
| ATOM | 4230 | CG | LYS | D | 225 | 95.658 | 11.662 | 124.489 | 1.00 | 40.94 |
| ATOM | 4231 | CD | LYS | D | 225 | 96.158 | 10.947 | 125.731 | 1.00 | 42.47 |
| ATOM | 4232 | CE | LYS | D | 225 | 95.590 | 11.577 | 126.984 | 1.00 | 46.13 |
| ATOM | 4233 | NZ | LYS | D | 225 | 96.280 | 11.098 | 128.215 | 1.00 | 48.29 |
| ATOM | 4234 | C | LYS | D | 225 | 95.907 | 10.274 | 120.890 | 1.00 | 34.81 |
| ATOM | 4235 | O | LYS | D | 225 | 95.151 | 9.332 | 120.636 | 1.00 | 33.69 |
| ATOM | 4236 | N | GLY | D | 226 | 97.084 | 10.432 | 120.301 | 1.00 | 33.57 |
| ATOM | 4237 | CA | GLY | D | 226 | 97.522 | 9.469 | 119.309 | 1.00 | 34.57 |
| ATOM | 4238 | C | GLY | D | 226 | 98.568 | 10.003 | 118.352 | 1.00 | 34.49 |
| ATOM | 4239 | O | GLY | D | 226 | 99.121 | 11.087 | 118.561 | 1.00 | 34.89 |
| ATOM | 4240 | N | ASN | D | 227 | 98.840 | 9.231 | 117.303 | 1.00 | 33.54 |
| ATOM | 4241 | CA | ASN | D | 227 | 99.815 | 9.604 | 116.293 | 1.00 | 32.79 |
| ATOM | 4242 | CB | ASN | D | 227 | 100.679 | 8.401 | 115.923 | 1.00 | 32.45 |
| ATOM | 4243 | CG | ASN | D | 227 | 101.640 | 8.011 | 117.023 | 1.00 | 33.66 |
| ATOM | 4244 | OD1 | ASN | D | 227 | 102.419 | 8.841 | 117.511 | 1.00 | 34.74 |
| ATOM | 4245 | ND2 | ASN | D | 227 | 101.602 | 6.743 | 117.413 | 1.00 | 30.46 |
| ATOM | 4246 | C | ASN | D | 227 | 99.123 | 10.098 | 115.038 | 1.00 | 32.66 |
| ATOM | 4247 | O | ASN | D | 227 | 98.194 | 9.471 | 114.551 | 1.00 | 33.96 |
| ATOM | 4248 | N | TYR | D | 228 | 99.569 | 11.226 | 114.511 | 1.00 | 32.63 |
| ATOM | 4249 | CA | TYR | D | 228 | 98.977 | 11.735 | 113.289 | 1.00 | 32.20 |
| ATOM | 4250 | CB | TYR | D | 228 | 98.333 | 13.089 | 113.532 | 1.00 | 30.83 |
| ATOM | 4251 | CG | TYR | D | 228 | 97.209 | 12.983 | 114.498 | 1.00 | 28.79 |
| ATOM | 4252 | CD1 | TYR | D | 228 | 97.451 | 12.854 | 115.859 | 1.00 | 28.66 |
| ATOM | 4253 | CE1 | TYR | D | 228 | 96.417 | 12.689 | 116.748 | 1.00 | 30.07 |
| ATOM | 4254 | CD2 | TYR | D | 228 | 95.900 | 12.946 | 114.050 | 1.00 | 31.02 |
| ATOM | 4255 | CE2 | TYR | D | 228 | 94.851 | 12.782 | 114.929 | 1.00 | 31.42 |
| ATOM | 4256 | CZ | TYR | D | 228 | 95.115 | 12.656 | 116.273 | 1.00 | 31.27 |
| ATOM | 4257 | OH | TYR | D | 228 | 94.062 | 12.516 | 117.136 | 1.00 | 34.09 |
| ATOM | 4258 | C | TYR | D | 228 | 100.073 | 11.843 | 112.250 | 1.00 | 32.68 |
| ATOM | 4259 | O | TYR | D | 228 | 101.134 | 12.412 | 112.511 | 1.00 | 32.76 |
| ATOM | 4260 | N | THR | D | 229 | 99.815 | 11.278 | 111.075 | 1.00 | 32.13 |
| ATOM | 4261 | CA | THR | D | 229 | 100.785 | 11.305 | 109.992 | 1.00 | 30.62 |
| ATOM | 4262 | CB | THR | D | 229 | 101.199 | 9.891 | 109.600 | 1.00 | 30.56 |
| ATOM | 4263 | OG1 | THR | D | 229 | 101.602 | 9.176 | 110.770 | 1.00 | 31.01 |
| ATOM | 4264 | CG2 | THR | D | 229 | 102.357 | 9.934 | 108.629 | 1.00 | 31.89 |
| ATOM | 4265 | C | THR | D | 229 | 100.250 | 12.000 | 108.756 | 1.00 | 29.30 |
| ATOM | 4266 | O | THR | D | 229 | 99.148 | 11.716 | 108.309 | 1.00 | 28.58 |
| ATOM | 4267 | N | CYS | D | 230 | 101.028 | 12.928 | 108.217 | 1.00 | 30.51 |
| ATOM | 4268 | CA | CYS | D | 230 | 100.610 | 13.621 | 107.011 | 1.00 | 32.35 |
| ATOM | 4269 | C | CYS | D | 230 | 101.289 | 12.904 | 105.858 | 1.00 | 32.87 |
| ATOM | 4270 | O | CYS | D | 230 | 102.423 | 12.417 | 105.979 | 1.00 | 33.82 |
| ATOM | 4271 | CB | CYS | D | 230 | 101.026 | 15.088 | 107.029 | 1.00 | 32.58 |
| ATOM | 4272 | SG | CYS | D | 230 | 102.817 | 15.348 | 107.184 | 1.00 | 39.09 |
| ATOM | 4273 | N | ILE | D | 231 | 100.577 | 12.825 | 104.746 | 1.00 | 32.40 |
| ATOM | 4274 | CA | ILE | D | 231 | 101.081 | 12.154 | 103.574 | 1.00 | 32.93 |
| ATOM | 4275 | CB | ILE | D | 231 | 100.256 | 10.881 | 103.314 | 1.00 | 33.24 |
| ATOM | 4276 | CG2 | ILE | D | 231 | 100.826 | 10.114 | 102.137 | 1.00 | 31.63 |
| ATOM | 4277 | CG1 | ILE | D | 231 | 100.263 | 10.015 | 104.577 | 1.00 | 32.96 |
| ATOM | 4278 | CD1 | ILE | D | 231 | 99.708 | 8.642 | 104.375 | 1.00 | 34.35 |
| ATOM | 4279 | C | ILE | D | 231 | 100.958 | 13.100 | 102.401 | 1.00 | 33.48 |
| ATOM | 4280 | O | ILE | D | 231 | 99.849 | 13.355 | 101.922 | 1.00 | 33.16 |
| ATOM | 4281 | N | VAL | D | 232 | 102.094 | 13.645 | 101.971 | 1.00 | 33.93 |
| ATOM | 4282 | CA | VAL | D | 232 | 102.134 | 14.556 | 100.834 | 1.00 | 36.17 |
| ATOM | 4283 | CB | VAL | D | 232 | 103.091 | 15.718 | 101.072 | 1.00 | 34.31 |
| ATOM | 4284 | CG1 | VAL | D | 232 | 103.078 | 16.635 | 99.879 | 1.00 | 34.18 |
| ATOM | 4285 | CG2 | VAL | D | 232 | 102.691 | 16.462 | 102.324 | 1.00 | 34.98 |
| ATOM | 4286 | C | VAL | D | 232 | 102.647 | 13.721 | 99.678 | 1.00 | 39.40 |
| ATOM | 4287 | O | VAL | D | 232 | 103.707 | 13.092 | 99.775 | 1.00 | 39.92 |
| ATOM | 4288 | N | GLU | D | 233 | 101.907 | 13.709 | 98.579 | 1.00 | 42.11 |
| ATOM | 4289 | CA | GLU | D | 233 | 102.320 | 12.875 | 97.474 | 1.00 | 44.91 |
| ATOM | 4290 | CB | GLU | D | 233 | 101.752 | 11.482 | 97.710 | 1.00 | 46.98 |
| ATOM | 4291 | CG | GLU | D | 233 | 101.754 | 10.584 | 96.507 | 1.00 | 54.51 |
| ATOM | 4292 | CD | GLU | D | 233 | 101.552 | 9.132 | 96.892 | 1.00 | 59.37 |
| ATOM | 4293 | OE1 | GLU | D | 233 | 100.659 | 8.864 | 97.739 | 1.00 | 61.58 |
| ATOM | 4294 | OE2 | GLU | D | 233 | 102.288 | 8.267 | 96.348 | 1.00 | 59.83 |
| ATOM | 4295 | C | GLU | D | 233 | 101.941 | 13.363 | 96.090 | 1.00 | 45.68 |
| ATOM | 4296 | O | GLU | D | 233 | 100.961 | 14.096 | 95.926 | 1.00 | 45.02 |
| ATOM | 4297 | N | ASN | D | 234 | 102.747 | 12.958 | 95.105 | 1.00 | 45.84 |
| ATOM | 4298 | CA | ASN | D | 234 | 102.516 | 13.281 | 93.701 | 1.00 | 45.22 |
| ATOM | 4299 | CB | ASN | D | 234 | 103.183 | 14.614 | 93.314 | 1.00 | 45.24 |
| ATOM | 4300 | CG | ASN | D | 234 | 104.641 | 14.468 | 92.946 | 1.00 | 44.43 |
| ATOM | 4301 | OD1 | ASN | D | 234 | 105.256 | 13.422 | 93.165 | 1.00 | 44.59 |
| ATOM | 4302 | ND2 | ASN | D | 234 | 105.210 | 15.534 | 92.385 | 1.00 | 40.85 |
| ATOM | 4303 | C | ASN | D | 234 | 103.060 | 12.112 | 92.888 | 1.00 | 45.49 |

TABLE 1-continued

FGFR1 D2–D3 Complexed with FGF2

| ATOM | 4304 | O | ASN | D | 234 | 103.561 | 11.149 | 93.464 | 1.00 | 45.48 |
|---|---|---|---|---|---|---|---|---|---|---|
| ATOM | 4305 | N | GLU | D | 235 | 102.965 | 12.194 | 91.564 | 1.00 | 46.96 |
| ATOM | 4306 | CA | GLU | D | 235 | 103.410 | 11.110 | 90.687 | 1.00 | 47.27 |
| ATOM | 4307 | CB | GLU | D | 235 | 103.165 | 11.494 | 89.218 | 1.00 | 46.16 |
| ATOM | 4308 | C | GLU | D | 235 | 104.857 | 10.643 | 90.851 | 1.00 | 47.83 |
| ATOM | 4309 | O | GLU | D | 235 | 105.171 | 9.496 | 90.533 | 1.00 | 48.35 |
| ATOM | 4310 | N | TYR | D | 236 | 105.735 | 11.498 | 91.368 | 1.00 | 48.23 |
| ATOM | 4311 | CA | TYR | D | 236 | 107.139 | 11.110 | 91.492 | 1.00 | 48.07 |
| ATOM | 4312 | CB | TYR | D | 236 | 108.000 | 12.221 | 90.905 | 1.00 | 51.78 |
| ATOM | 4313 | CG | TYR | D | 236 | 107.449 | 12.674 | 89.579 | 1.00 | 56.38 |
| ATOM | 4314 | CD1 | TYR | D | 236 | 106.553 | 13.744 | 89.501 | 1.00 | 58.00 |
| ATOM | 4315 | CE1 | TYR | D | 236 | 105.976 | 14.112 | 88.286 | 1.00 | 60.31 |
| ATOM | 4316 | CD2 | TYR | D | 236 | 107.757 | 11.981 | 88.408 | 1.00 | 57.90 |
| ATOM | 4317 | CE2 | TYR | D | 236 | 107.184 | 12.337 | 87.190 | 1.00 | 60.14 |
| ATOM | 4318 | CZ | TYR | D | 236 | 106.298 | 13.401 | 87.135 | 1.00 | 61.38 |
| ATOM | 4319 | OH | TYR | D | 236 | 105.748 | 13.758 | 85.925 | 1.00 | 62.75 |
| ATOM | 4320 | C | TYR | D | 236 | 107.638 | 10.728 | 92.876 | 1.00 | 45.71 |
| ATOM | 4321 | O | TYR | D | 236 | 108.803 | 10.372 | 93.049 | 1.00 | 45.60 |
| ATOM | 4322 | N | GLY | D | 237 | 106.758 | 10.783 | 93.863 | 1.00 | 43.72 |
| ATOM | 4323 | CA | GLY | D | 237 | 107.177 | 10.429 | 95.202 | 1.00 | 42.52 |
| ATOM | 4324 | C | GLY | D | 237 | 106.233 | 10.922 | 96.275 | 1.00 | 42.32 |
| ATOM | 4325 | O | GLY | D | 237 | 105.280 | 11.661 | 95.996 | 1.00 | 42.37 |
| ATOM | 4326 | N | SER | D | 238 | 106.493 | 10.497 | 97.509 | 1.00 | 40.93 |
| ATOM | 4327 | CA | SER | D | 238 | 105.678 | 10.895 | 98.643 | 1.00 | 38.31 |
| ATOM | 4328 | CB | SER | D | 238 | 104.607 | 9.848 | 98.912 | 1.00 | 37.78 |
| ATOM | 4329 | OG | SER | D | 238 | 105.218 | 8.650 | 99.344 | 1.00 | 39.41 |
| ATOM | 4330 | C | SER | D | 238 | 106.559 | 11.027 | 99.871 | 1.00 | 37.41 |
| ATOM | 4331 | O | SER | D | 238 | 107.577 | 10.350 | 99.993 | 1.00 | 36.75 |
| ATOM | 4332 | N | ILE | D | 239 | 106.166 | 11.919 | 100.772 | 1.00 | 37.40 |
| ATOM | 4333 | CA | ILE | D | 239 | 106.885 | 12.138 | 102.028 | 1.00 | 37.41 |
| ATOM | 4334 | CB | ILE | D | 239 | 107.571 | 13.516 | 102.117 | 1.00 | 37.31 |
| ATOM | 4335 | CG2 | ILE | D | 239 | 109.017 | 13.429 | 101.703 | 1.00 | 36.88 |
| ATOM | 4336 | CG1 | ILE | D | 239 | 106.777 | 14.527 | 101.305 | 1.00 | 38.29 |
| ATOM | 4337 | CD1 | ILE | D | 239 | 107.409 | 15.895 | 101.252 | 1.00 | 42.39 |
| ATOM | 4338 | C | ILE | D | 239 | 105.828 | 12.151 | 103.098 | 1.00 | 38.18 |
| ATOM | 4339 | O | ILE | D | 239 | 104.672 | 12.502 | 102.825 | 1.00 | 38.68 |
| ATOM | 4340 | N | ASN | D | 240 | 106.220 | 11.777 | 104.311 | 1.00 | 38.07 |
| ATOM | 4341 | CA | ASN | D | 240 | 105.292 | 11.775 | 105.434 | 1.00 | 39.19 |
| ATOM | 4342 | CB | ASN | D | 240 | 104.696 | 10.375 | 105.660 | 1.00 | 41.17 |
| ATOM | 4343 | CG | ASN | D | 240 | 105.743 | 9.348 | 106.072 | 1.00 | 43.52 |
| ATOM | 4344 | CD1 | ASN | D | 240 | 106.601 | 9.622 | 106.912 | 1.00 | 47.31 |
| ATOM | 4345 | ND2 | ASN | D | 240 | 105.665 | 8.153 | 105.494 | 1.00 | 43.18 |
| ATOM | 4346 | C | ASN | D | 240 | 105.999 | 12.246 | 106.697 | 1.00 | 38.45 |
| ATOM | 4347 | O | ASN | D | 240 | 107.226 | 12.240 | 106.778 | 1.00 | 38.26 |
| ATOM | 4348 | N | HIS | D | 241 | 105.218 | 12.668 | 107.681 | 1.00 | 38.00 |
| ATOM | 4349 | CA | HIS | D | 241 | 105.777 | 13.125 | 108.945 | 1.00 | 37.35 |
| ATOM | 4350 | CB | HIS | D | 241 | 106.127 | 14.621 | 108.868 | 1.00 | 38.82 |
| ATOM | 4351 | CG | HIS | D | 241 | 106.784 | 15.166 | 110.104 | 1.00 | 40.90 |
| ATOM | 4352 | CD2 | HIS | D | 241 | 106.499 | 16.256 | 110.857 | 1.00 | 40.95 |
| ATOM | 4353 | ND1 | HIS | D | 241 | 107.897 | 14.588 | 110.680 | 1.00 | 41.06 |
| ATOM | 4354 | CE1 | HIS | D | 241 | 108.266 | 15.298 | 111.733 | 1.00 | 39.83 |
| ATOM | 4355 | NE2 | HIS | D | 241 | 107.434 | 16.315 | 111.861 | 1.00 | 40.11 |
| ATOM | 4356 | C | HIS | D | 241 | 104.713 | 12.873 | 109.996 | 1.00 | 36.27 |
| ATOM | 4357 | O | HIS | D | 241 | 103.531 | 13.167 | 109.784 | 1.00 | 36.50 |
| ATOM | 4358 | N | THR | D | 242 | 105.125 | 12.320 | 111.125 | 1.00 | 34.08 |
| ATOM | 4359 | CA | THR | D | 242 | 104.171 | 12.037 | 112.173 | 1.00 | 33.41 |
| ATOM | 4360 | CB | THR | D | 242 | 104.208 | 10.557 | 112.512 | 1.00 | 33.88 |
| ATOM | 4361 | OG1 | THR | D | 242 | 104.178 | 9.820 | 111.286 | 1.00 | 34.73 |
| ATOM | 4362 | CG2 | THR | D | 242 | 103.001 | 10.166 | 113.359 | 1.00 | 32.87 |
| ATOM | 4363 | C | THR | D | 242 | 104.390 | 12.880 | 113.422 | 1.00 | 32.39 |
| ATOM | 4364 | O | THR | D | 242 | 105.515 | 13.202 | 113.785 | 1.00 | 31.61 |
| ATOM | 4365 | N | TYR | D | 243 | 103.286 | 13.266 | 114.047 | 1.00 | 33.00 |
| ATOM | 4366 | CA | TYR | D | 243 | 103.308 | 14.064 | 115.267 | 1.00 | 33.46 |
| ATOM | 4367 | CB | TYR | D | 243 | 102.534 | 15.373 | 115.093 | 1.00 | 33.45 |
| ATOM | 4368 | CG | TYR | D | 243 | 103.207 | 16.364 | 114.190 | 1.00 | 32.79 |
| ATOM | 4369 | CD1 | TYR | D | 243 | 102.642 | 16.715 | 112.960 | 1.00 | 30.88 |
| ATOM | 4370 | CE1 | TYR | D | 243 | 103.287 | 17.616 | 112.106 | 1.00 | 31.50 |
| ATOM | 4371 | CD2 | TYR | D | 243 | 104.430 | 16.937 | 114.552 | 1.00 | 32.94 |
| ATOM | 4372 | CE2 | TYR | D | 243 | 105.086 | 17.842 | 113.706 | 1.00 | 33.56 |
| ATOM | 4373 | CZ | TYR | D | 243 | 104.511 | 18.175 | 112.482 | 1.00 | 32.47 |
| ATOM | 4374 | OH | TYR | D | 243 | 105.177 | 19.042 | 111.641 | 1.00 | 30.66 |
| ATOM | 4375 | C | TYR | D | 243 | 102.640 | 13.247 | 116.351 | 1.00 | 33.10 |
| ATOM | 4376 | O | TYR | D | 243 | 101.782 | 12.400 | 116.077 | 1.00 | 32.05 |
| ATOM | 4377 | N | GLN | D | 244 | 103.031 | 13.491 | 117.588 | 1.00 | 33.55 |
| ATOM | 4378 | CA | GLN | D | 244 | 102.424 | 12.745 | 118.661 | 1.00 | 35.12 |
| ATOM | 4379 | CB | GLN | D | 244 | 103.481 | 12.044 | 119.495 | 1.00 | 37.87 |
| ATOM | 4380 | CG | GLN | D | 244 | 102.937 | 10.835 | 120.198 | 1.00 | 43.93 |

TABLE 1-continued

FGFR1 D2–D3 Complexed with FGF2

| | | | | | | | | | | |
|---|---|---|---|---|---|---|---|---|---|---|
| ATOM | 4381 | CD | GLN | D | 244 | 103.911 | 10.283 | 121.205 | 1.00 | 48.46 |
| ATOM | 4382 | OE1 | GLN | D | 244 | 105.119 | 10.215 | 120.943 | 1.00 | 51.99 |
| ATOM | 4383 | NE2 | GLN | D | 244 | 103.398 | 9.879 | 122.367 | 1.00 | 47.54 |
| ATOM | 4384 | C | GLN | D | 244 | 101.642 | 13.719 | 119.507 | 1.00 | 33.39 |
| ATOM | 4385 | O | GLN | D | 244 | 102.172 | 14.740 | 119.947 | 1.00 | 31.94 |
| ATOM | 4386 | N | LEU | D | 245 | 100.365 | 13.419 | 119.699 | 1.00 | 31.77 |
| ATOM | 4387 | CA | LEU | D | 245 | 99.535 | 14.285 | 120.504 | 1.00 | 32.20 |
| ATOM | 4388 | CB | LEU | D | 245 | 98.189 | 14.607 | 119.818 | 1.00 | 32.50 |
| ATOM | 4389 | CG | LEU | D | 245 | 97.244 | 15.496 | 120.658 | 1.00 | 32.01 |
| ATOM | 4390 | CD1 | LEU | D | 245 | 97.931 | 16.802 | 120.993 | 1.00 | 31.78 |
| ATOM | 4391 | CD2 | LEU | D | 245 | 95.952 | 15.779 | 119.922 | 1.00 | 33.00 |
| ATOM | 4392 | C | LEU | D | 245 | 99.279 | 13.635 | 121.842 | 1.00 | 31.58 |
| ATOM | 4393 | O | LEU | D | 245 | 98.968 | 12.447 | 121.932 | 1.00 | 30.22 |
| ATOM | 4394 | N | ASP | D | 246 | 99.432 | 14.437 | 122.883 | 1.00 | 32.78 |
| ATOM | 4395 | CA | ASP | D | 246 | 99.199 | 13.994 | 124.239 | 1.00 | 33.03 |
| ATOM | 4396 | CB | ASP | D | 246 | 100.521 | 13.828 | 124.963 | 1.00 | 34.24 |
| ATOM | 4397 | CG | ASP | D | 246 | 100.369 | 13.061 | 126.240 | 1.00 | 38.04 |
| ATOM | 4398 | CD1 | ASP | D | 246 | 101.348 | 12.968 | 127.014 | 1.00 | 40.39 |
| ATOM | 4399 | CD2 | ASP | D | 246 | 99.255 | 12.544 | 126.464 | 1.00 | 41.31 |
| ATOM | 4400 | C | ASP | D | 246 | 98.369 | 15.077 | 124.915 | 1.00 | 33.21 |
| ATOM | 4401 | O | ASP | D | 246 | 98.793 | 16.233 | 124.987 | 1.00 | 33.23 |
| ATOM | 4402 | N | VAL | D | 247 | 97.181 | 14.702 | 125.388 | 1.00 | 34.04 |
| ATOM | 4403 | CA | VAL | D | 247 | 96.259 | 15.634 | 126.053 | 1.00 | 34.00 |
| ATOM | 4404 | CB | VAL | D | 247 | 94.819 | 15.478 | 125.507 | 1.00 | 33.34 |
| ATOM | 4405 | CG1 | VAL | D | 247 | 93.957 | 16.651 | 125.942 | 1.00 | 31.80 |
| ATOM | 4406 | CG2 | VAL | D | 247 | 94.849 | 15.355 | 123.997 | 1.00 | 35.20 |
| ATOM | 4407 | C | VAL | D | 247 | 96.204 | 15.358 | 127.557 | 1.00 | 34.12 |
| ATOM | 4408 | O | VAL | D | 247 | 95.933 | 14.228 | 127.970 | 1.00 | 32.75 |
| ATOM | 4409 | N | VAL | D | 248 | 96.438 | 16.394 | 128.365 | 1.00 | 33.95 |
| ATOM | 4410 | CA | VAL | D | 248 | 96.414 | 16.264 | 129.822 | 1.00 | 34.42 |
| ATOM | 4411 | CB | VAL | D | 248 | 97.650 | 16.919 | 130.475 | 1.00 | 33.86 |
| ATOM | 4412 | CG1 | VAL | D | 248 | 97.646 | 16.649 | 131.954 | 1.00 | 33.01 |
| ATOM | 4413 | CG2 | VAL | D | 248 | 98.925 | 16.407 | 129.844 | 1.00 | 35.22 |
| ATOM | 4414 | C | VAL | D | 248 | 95.202 | 16.965 | 130.415 | 1.00 | 35.72 |
| ATOM | 4415 | O | VAL | D | 248 | 94.969 | 18.134 | 130.116 | 1.00 | 35.44 |
| ATOM | 4416 | N | GLU | D | 249 | 94.438 | 16.255 | 131.246 | 1.00 | 36.91 |
| ATOM | 4417 | CA | GLU | D | 249 | 93.272 | 16.836 | 131.917 | 1.00 | 38.36 |
| ATOM | 4418 | CB | GLU | D | 249 | 92.182 | 15.787 | 132.122 | 1.00 | 41.10 |
| ATOM | 4419 | CG | GLU | D | 249 | 91.599 | 15.230 | 130.847 | 1.00 | 46.18 |
| ATOM | 4420 | CD | GLU | D | 249 | 90.669 | 14.058 | 131.103 | 1.00 | 48.79 |
| ATOM | 4421 | OE1 | GLU | D | 249 | 91.133 | 13.032 | 131.662 | 1.00 | 50.76 |
| ATOM | 4422 | OE2 | GLU | D | 249 | 89.476 | 14.166 | 130.743 | 1.00 | 49.83 |
| ATOM | 4423 | C | GLU | D | 249 | 93.773 | 17.262 | 133.289 | 1.00 | 37.17 |
| ATOM | 4424 | O | GLU | D | 249 | 94.255 | 16.417 | 134.030 | 1.00 | 37.43 |
| ATOM | 4425 | N | ARG | D | 250 | 93.675 | 18.544 | 133.648 | 1.00 | 36.72 |
| ATOM | 4426 | CA | ARG | D | 250 | 94.156 | 18.956 | 134.986 | 1.00 | 35.30 |
| ATOM | 4427 | CB | ARG | D | 250 | 94.622 | 20.427 | 135.022 | 1.00 | 32.09 |
| ATOM | 4428 | CG | ARG | D | 250 | 95.801 | 20.729 | 134.091 | 1.00 | 31.09 |
| ATOM | 4429 | CD | ARG | D | 250 | 96.960 | 19.717 | 134.237 | 1.00 | 27.53 |
| ATOM | 4430 | NE | ARG | D | 250 | 97.736 | 19.907 | 135.466 | 1.00 | 27.19 |
| ATOM | 4431 | CZ | ARG | D | 250 | 98.601 | 20.901 | 135.671 | 1.00 | 23.34 |
| ATOM | 4432 | NH1 | ARG | D | 250 | 98.819 | 21.807 | 134.733 | 1.00 | 24.08 |
| ATOM | 4433 | NH2 | ARG | D | 250 | 99.236 | 21.005 | 136.824 | 1.00 | 20.42 |
| ATOM | 4434 | C | ARG | D | 250 | 93.146 | 18.699 | 136.123 | 1.00 | 35.26 |
| ATOM | 4435 | O | ARG | D | 250 | 92.000 | 18.335 | 135.877 | 1.00 | 36.33 |
| ATOM | 4436 | N | SER | D | 251 | 93.642 | 18.752 | 137.373 | 1.00 | 36.16 |
| ATOM | 4437 | CA | SER | D | 251 | 92.839 | 18.539 | 138.596 | 1.00 | 35.07 |
| ATOM | 4438 | CB | SER | D | 251 | 93.267 | 17.254 | 139.308 | 1.00 | 33.85 |
| ATOM | 4439 | OG | SER | D | 251 | 93.280 | 16.152 | 138.433 | 1.00 | 33.32 |
| ATOM | 4440 | C | SER | D | 251 | 93.050 | 19.708 | 139.564 | 1.00 | 35.84 |
| ATOM | 4441 | O | SER | D | 251 | 93.706 | 19.560 | 140.601 | 1.00 | 36.47 |
| ATOM | 4442 | N | PRO | D | 252 | 92.505 | 20.888 | 139.235 | 1.00 | 36.42 |
| ATOM | 4443 | CD | PRO | D | 252 | 91.828 | 21.237 | 137.975 | 1.00 | 37.05 |
| ATOM | 4444 | CA | PRO | D | 252 | 92.655 | 22.070 | 140.088 | 1.00 | 36.24 |
| ATOM | 4445 | CB | PRO | D | 252 | 92.319 | 23.219 | 139.147 | 1.00 | 34.89 |
| ATOM | 4446 | CG | PRO | D | 252 | 91.286 | 22.625 | 138.277 | 1.00 | 37.22 |
| ATOM | 4447 | C | PRO | D | 252 | 91.790 | 22.066 | 141.334 | 1.00 | 36.91 |
| ATOM | 4448 | O | PRO | D | 252 | 90.850 | 22.854 | 141.469 | 1.00 | 36.54 |
| ATOM | 4449 | N | HIS | D | 253 | 92.122 | 21.166 | 142.247 | 1.00 | 37.49 |
| ATOM | 4450 | CA | HIS | D | 253 | 91.406 | 21.063 | 143.501 | 1.00 | 39.08 |
| ATOM | 4451 | CB | HIS | D | 253 | 90.229 | 20.073 | 143.366 | 1.00 | 42.98 |
| ATOM | 4452 | CG | HIS | D | 253 | 90.599 | 18.724 | 142.823 | 1.00 | 46.99 |
| ATOM | 4453 | CD2 | HIS | D | 253 | 90.222 | 18.090 | 141.686 | 1.00 | 48.65 |
| ATOM | 4454 | ND1 | HIS | D | 253 | 91.398 | 17.830 | 143.511 | 1.00 | 50.87 |
| ATOM | 4455 | CE1 | HIS | D | 253 | 91.492 | 16.703 | 142.823 | 1.00 | 51.49 |
| ATOM | 4456 | NE2 | HIS | D | 253 | 90.786 | 16.835 | 141.712 | 1.00 | 50.65 |
| ATOM | 4457 | C | HIS | D | 253 | 92.372 | 20.652 | 144.608 | 1.00 | 36.52 |

TABLE 1-continued

FGFR1 D2–D3 Complexed with FGF2

| ATOM | 4458 | O | HIS | D | 253 | 93.441 | 20.112 | 144.323 | 1.00 | 36.08 |
|---|---|---|---|---|---|---|---|---|---|---|
| ATOM | 4459 | N | ARG | D | 254 | 92.005 | 20.933 | 145.857 | 1.00 | 34.39 |
| ATOM | 4460 | CA | ARG | D | 254 | 92.838 | 20.590 | 147.000 | 1.00 | 32.02 |
| ATOM | 4461 | CB | ARG | D | 254 | 92.187 | 21.070 | 148.290 | 1.00 | 35.17 |
| ATOM | 4462 | CG | ARG | D | 254 | 90.937 | 20.319 | 148.714 | 1.00 | 40.73 |
| ATOM | 4463 | CD | ARG | D | 254 | 90.271 | 21.102 | 149.827 | 1.00 | 45.75 |
| ATOM | 4464 | NE | ARG | D | 254 | 89.412 | 20.288 | 150.677 | 1.00 | 51.38 |
| ATOM | 4465 | CZ | ARG | D | 254 | 88.375 | 19.586 | 150.237 | 1.00 | 55.43 |
| ATOM | 4466 | NH1 | ARG | D | 254 | 88.071 | 19.590 | 148.942 | 1.00 | 58.96 |
| ATOM | 4467 | NH2 | ARG | D | 254 | 87.624 | 18.904 | 151.094 | 1.00 | 55.71 |
| ATOM | 4468 | C | ARG | D | 254 | 93.059 | 19.092 | 147.045 | 1.00 | 29.52 |
| ATOM | 4469 | O | ARG | D | 254 | 92.338 | 18.342 | 146.393 | 1.00 | 30.17 |
| ATOM | 4470 | N | PRO | D | 255 | 94.071 | 18.634 | 147.803 | 1.00 | 27.73 |
| ATOM | 4471 | CD | PRO | D | 255 | 95.023 | 19.467 | 148.565 | 1.00 | 24.12 |
| ATOM | 4472 | CA | PRO | D | 255 | 94.392 | 17.199 | 147.926 | 1.00 | 25.71 |
| ATOM | 4473 | CB | PRO | D | 255 | 95.511 | 17.190 | 148.968 | 1.00 | 24.99 |
| ATOM | 4474 | CG | PRO | D | 255 | 96.191 | 18.531 | 148.754 | 1.00 | 24.65 |
| ATOM | 4475 | C | PRO | D | 255 | 93.213 | 16.314 | 148.344 | 1.00 | 25.05 |
| ATOM | 4476 | O | PRO | D | 255 | 92.296 | 16.770 | 149.018 | 1.00 | 24.12 |
| ATOM | 4477 | N | ILE | D | 256 | 93.241 | 15.050 | 147.931 | 1.00 | 26.53 |
| ATOM | 4478 | CA | ILE | D | 256 | 92.190 | 14.096 | 148.284 | 1.00 | 27.73 |
| ATOM | 4479 | CB | ILE | D | 256 | 91.420 | 13.556 | 147.047 | 1.00 | 26.74 |
| ATOM | 4480 | CG2 | ILE | D | 256 | 90.767 | 12.231 | 147.382 | 1.00 | 26.27 |
| ATOM | 4481 | CG1 | ILE | D | 256 | 90.341 | 14.553 | 146.621 | 1.00 | 24.87 |
| ATOM | 4482 | CD1 | ILE | D | 256 | 90.850 | 15.688 | 145.775 | 1.00 | 25.75 |
| ATOM | 4483 | C | ILE | D | 256 | 92.842 | 12.921 | 148.981 | 1.00 | 28.99 |
| ATOM | 4484 | O | ILE | D | 256 | 93.811 | 12.348 | 148.471 | 1.00 | 30.56 |
| ATOM | 4485 | N | LEU | D | 257 | 92.313 | 12.564 | 150.145 | 1.00 | 28.90 |
| ATOM | 4486 | CA | LEU | D | 257 | 92.862 | 11.449 | 150.909 | 1.00 | 29.82 |
| ATOM | 4487 | CB | LEU | D | 257 | 92.973 | 11.863 | 152.389 | 1.00 | 30.22 |
| ATOM | 4488 | CG | LEU | D | 257 | 93.644 | 13.245 | 152.571 | 1.00 | 33.19 |
| ATOM | 4489 | CD1 | LEU | D | 257 | 93.479 | 13.776 | 153.996 | 1.00 | 31.95 |
| ATOM | 4490 | CD2 | LEU | D | 257 | 95.113 | 13.146 | 152.208 | 1.00 | 32.87 |
| ATOM | 4491 | C | LEU | D | 257 | 91.945 | 10.240 | 150.709 | 1.00 | 28.77 |
| ATOM | 4492 | O | LEU | D | 257 | 90.729 | 10.401 | 150.619 | 1.00 | 28.70 |
| ATOM | 4493 | N | GLN | D | 258 | 92.512 | 9.041 | 150.596 | 1.00 | 27.83 |
| ATOM | 4494 | CA | GLN | D | 258 | 91.664 | 7.863 | 150.411 | 1.00 | 29.70 |
| ATOM | 4495 | CB | GLN | D | 258 | 92.497 | 6.580 | 150.272 | 1.00 | 28.42 |
| ATOM | 4496 | C | GLN | D | 258 | 90.763 | 7.762 | 151.632 | 1.00 | 29.85 |
| ATOM | 4497 | O | GLN | D | 258 | 91.226 | 7.912 | 152.773 | 1.00 | 31.42 |
| ATOM | 4498 | N | ALA | D | 259 | 89.475 | 7.536 | 151.401 | 1.00 | 27.97 |
| ATOM | 4499 | CA | ALA | D | 259 | 88.554 | 7.423 | 152.510 | 1.00 | 26.07 |
| ATOM | 4500 | CE | ALA | D | 259 | 87.146 | 7.384 | 152.001 | 1.00 | 24.75 |
| ATOM | 4501 | C | ALA | D | 259 | 88.903 | 6.141 | 153.252 | 1.00 | 27.29 |
| ATOM | 4502 | O | ALA | D | 259 | 89.340 | 5.165 | 152.640 | 1.00 | 26.71 |
| ATOM | 4503 | N | GLY | D | 260 | 88.747 | 6.159 | 154.573 | 1.00 | 27.98 |
| ATOM | 4504 | CA | GLY | D | 260 | 89.047 | 4.982 | 155.365 | 1.00 | 28.73 |
| ATOM | 4505 | C | GLY | D | 260 | 90.465 | 4.897 | 155.903 | 1.00 | 30.14 |
| ATOM | 4506 | O | GLY | D | 260 | 90.777 | 3.963 | 156.640 | 1.00 | 31.06 |
| ATOM | 4507 | N | LEU | D | 261 | 91.311 | 5.866 | 155.549 | 1.00 | 30.20 |
| ATOM | 4508 | CA | LEU | D | 261 | 92.714 | 5.900 | 155.979 | 1.00 | 30.06 |
| ATOM | 4509 | CB | LEU | D | 261 | 93.619 | 5.501 | 154.809 | 1.00 | 28.40 |
| ATOM | 4510 | CG | LEU | D | 261 | 93.420 | 4.108 | 154.217 | 1.00 | 27.35 |
| ATOM | 4511 | CD1 | LEU | D | 261 | 94.115 | 3.975 | 152.871 | 1.00 | 26.70 |
| ATOM | 4512 | CD2 | LEU | D | 261 | 93.945 | 3.097 | 155.199 | 1.00 | 23.13 |
| ATOM | 4513 | C | LEU | D | 261 | 93.120 | 7.298 | 156.440 | 1.00 | 30.61 |
| ATOM | 4514 | O | LEU | D | 261 | 92.839 | 8.275 | 155.753 | 1.00 | 33.23 |
| ATOM | 4515 | N | PRO | D | 262 | 93.804 | 7.413 | 157.593 | 1.00 | 30.88 |
| ATOM | 4516 | CD | PRO | D | 262 | 94.125 | 8.712 | 158.211 | 1.00 | 30.49 |
| ATOM | 4517 | CA | PRO | D | 262 | 94.210 | 6.314 | 158.478 | 1.00 | 30.82 |
| ATOM | 4518 | CB | PRO | D | 262 | 95.108 | 7.007 | 159.500 | 1.00 | 30.09 |
| ATOM | 4519 | CG | PRO | D | 262 | 94.453 | 8.323 | 159.648 | 1.00 | 29.04 |
| ATOM | 4520 | C | PRO | D | 262 | 92.988 | 5.705 | 159.132 | 1.00 | 29.98 |
| ATOM | 4521 | O | PRO | D | 262 | 91.935 | 6.341 | 159.211 | 1.00 | 29.28 |
| ATOM | 4522 | N | ALA | D | 263 | 93.123 | 4.469 | 159.594 | 1.00 | 29.91 |
| ATOM | 4523 | CA | ALA | D | 263 | 92.001 | 3.809 | 160.255 | 1.00 | 30.35 |
| ATOM | 4524 | CB | ALA | D | 263 | 91.743 | 2.421 | 159.641 | 1.00 | 28.77 |
| ATOM | 4525 | C | ALA | D | 263 | 92.250 | 3.684 | 161.750 | 1.00 | 29.36 |
| ATOM | 4526 | O | ALA | D | 263 | 93.392 | 3.646 | 162.206 | 1.00 | 27.15 |
| ATOM | 4527 | N | ASN | D | 264 | 91.168 | 3.651 | 162.514 | 1.00 | 30.53 |
| ATOM | 4528 | CA | ASN | D | 264 | 91.289 | 3.495 | 163.945 | 1.00 | 31.88 |
| ATOM | 4529 | CB | ASN | D | 264 | 89.917 | 3.445 | 164.598 | 1.00 | 31.69 |
| ATOM | 4530 | CG | ASN | D | 264 | 89.206 | 4.744 | 164.501 | 1.00 | 33.36 |
| ATOM | 4531 | OD1 | ASN | D | 264 | 89.845 | 5.797 | 164.471 | 1.00 | 34.00 |
| ATOM | 4532 | ND2 | ASN | D | 264 | 87.873 | 4.700 | 164.463 | 1.00 | 36.85 |
| ATOM | 4533 | C | ASN | D | 264 | 92.024 | 2.190 | 164.215 | 1.00 | 32.38 |
| ATOM | 4534 | O | ASN | D | 264 | 91.845 | 1.204 | 163.499 | 1.00 | 30.61 |

TABLE 1-continued

FGFR1 D2–D3 Complexed with FGF2

| ATOM | 4535 | N | LYS | D | 265 | 92.852 | 2.195 | 165.253 | 1.00 | 33.51 |
|---|---|---|---|---|---|---|---|---|---|---|
| ATOM | 4536 | CA | LYS | D | 265 | 93.620 | 1.023 | 165.624 | 1.00 | 34.84 |
| ATOM | 4537 | CB | LYS | D | 265 | 95.106 | 1.209 | 165.275 | 1.00 | 36.12 |
| ATOM | 4538 | CG | LYS | D | 265 | 95.388 | 1.866 | 163.932 | 1.00 | 38.63 |
| ATOM | 4539 | CD | LYS | D | 265 | 94.975 | 1.003 | 162.761 | 1.00 | 39.25 |
| ATOM | 4540 | CE | LYS | D | 265 | 96.191 | 0.440 | 162.060 | 1.00 | 39.05 |
| ATOM | 4541 | NZ | LYS | D | 265 | 97.026 | 1.523 | 161.471 | 1.00 | 39.06 |
| ATOM | 4542 | C | LYS | D | 265 | 93.524 | 0.788 | 167.121 | 1.00 | 36.31 |
| ATOM | 4543 | O | LYS | D | 265 | 93.691 | 1.715 | 167.911 | 1.00 | 38.31 |
| ATOM | 4544 | N | THR | D | 266 | 93.240 | 0.447 | 167.515 | 1.00 | 37.04 |
| ATOM | 4545 | CA | THR | D | 266 | 93.210 | 0.790 | 168.926 | 1.00 | 37.70 |
| ATOM | 4546 | CB | THR | D | 266 | 91.882 | 1.444 | 169.345 | 1.00 | 36.73 |
| ATOM | 4547 | OG1 | THR | D | 266 | 90.837 | 0.468 | 169.294 | 1.00 | 37.40 |
| ATOM | 4548 | CG2 | THR | D | 266 | 91.977 | 1.990 | 170.769 | 1.00 | 37.09 |
| ATOM | 4549 | C | THR | D | 266 | 94.349 | 1.794 | 169.078 | 1.00 | 39.32 |
| ATOM | 4550 | O | THR | D | 266 | 94.422 | 2.774 | 168.350 | 1.00 | 38.85 |
| ATOM | 4551 | N | VAL | D | 267 | 95.269 | 1.530 | 169.995 | 1.00 | 42.44 |
| ATOM | 4552 | CA | VAL | D | 267 | 96.386 | 2.444 | 170.201 | 1.00 | 44.11 |
| ATOM | 4553 | CB | VAL | D | 267 | 97.636 | 1.990 | 169.439 | 1.00 | 43.44 |
| ATOM | 4554 | CG1 | VAL | D | 267 | 97.387 | 2.084 | 167.942 | 1.00 | 43.56 |
| ATOM | 4555 | CG2 | VAL | D | 267 | 97.994 | 0.577 | 169.845 | 1.00 | 43.00 |
| ATOM | 4556 | C | VAL | D | 267 | 96.760 | 2.599 | 171.669 | 1.00 | 45.67 |
| ATOM | 4557 | O | VAL | D | 267 | 96.228 | 1.895 | 172.545 | 1.00 | 44.80 |
| ATOM | 4558 | N | ALA | D | 268 | 97.676 | 3.535 | 171.921 | 1.00 | 46.81 |
| ATOM | 4559 | CA | ALA | D | 268 | 98.153 | 3.831 | 173.270 | 1.00 | 46.58 |
| ATOM | 4560 | CB | ALA | D | 268 | 98.563 | 5.288 | 173.373 | 1.00 | 44.62 |
| ATOM | 4561 | C | ALA | D | 268 | 99.335 | 2.942 | 173.602 | 1.00 | 46.29 |
| ATOM | 4562 | O | ALA | D | 268 | 100.121 | 2.592 | 172.722 | 1.00 | 44.98 |
| ATOM | 4563 | N | LEU | D | 269 | 99.452 | 2.578 | 174.876 | 1.00 | 47.03 |
| ATOM | 4564 | CA | LEU | D | 269 | 100.548 | 1.731 | 175.334 | 1.00 | 47.97 |
| ATOM | 4565 | CB | LEU | D | 269 | 100.533 | 1.626 | 176.869 | 1.00 | 47.45 |
| ATOM | 4566 | CG | LEU | D | 269 | 101.303 | 0.473 | 177.541 | 1.00 | 48.73 |
| ATOM | 4567 | CD1 | LEU | D | 269 | 101.066 | 0.503 | 179.041 | 1.00 | 47.47 |
| ATOM | 4568 | CD2 | LEU | D | 269 | 102.800 | 0.570 | 177.240 | 1.00 | 49.24 |
| ATOM | 4569 | C | LEU | D | 269 | 101.859 | 2.354 | 174.861 | 1.00 | 48.02 |
| ATOM | 4570 | O | LEU | D | 269 | 102.082 | 3.548 | 175.052 | 1.00 | 48.67 |
| ATOM | 4571 | N | GLY | D | 270 | 102.712 | 1.551 | 174.230 | 1.00 | 47.32 |
| ATOM | 4572 | CA | GLY | D | 270 | 103.989 | 2.060 | 173.761 | 1.00 | 47.45 |
| ATOM | 4573 | C | GLY | D | 270 | 104.044 | 2.496 | 172.307 | 1.00 | 47.67 |
| ATOM | 4574 | O | GLY | D | 270 | 105.125 | 2.778 | 171.784 | 1.00 | 47.93 |
| ATOM | 4575 | N | SER | D | 271 | 102.895 | 2.552 | 171.643 | 1.00 | 47.17 |
| ATOM | 4576 | CA | SER | D | 271 | 102.861 | 2.965 | 170.246 | 1.00 | 46.98 |
| ATOM | 4577 | CB | SER | D | 271 | 101.416 | 3.160 | 169.795 | 1.00 | 46.79 |
| ATOM | 4578 | OG | SER | D | 271 | 100.759 | 4.117 | 170.611 | 1.00 | 50.01 |
| ATOM | 4579 | C | SER | D | 271 | 103.562 | 1.964 | 169.327 | 1.00 | 47.46 |
| ATOM | 4580 | O | SER | D | 271 | 104.065 | 0.933 | 169.770 | 1.00 | 47.22 |
| ATOM | 4581 | N | ASN | D | 272 | 103.602 | 2.288 | 168.042 | 1.00 | 47.66 |
| ATOM | 4582 | CA | ASN | D | 272 | 104.220 | 1.425 | 167.045 | 1.00 | 48.16 |
| ATOM | 4583 | CB | ASN | D | 272 | 105.418 | 2.118 | 166.394 | 1.00 | 47.89 |
| ATOM | 4584 | CG | ASN | D | 272 | 106.677 | 1.978 | 167.204 | 1.00 | 48.55 |
| ATOM | 4585 | OD1 | ASN | D | 272 | 107.266 | 0.901 | 167.263 | 1.00 | 49.20 |
| ATOM | 4586 | ND2 | ASN | D | 272 | 107.099 | 3.063 | 167.841 | 1.00 | 49.75 |
| ATOM | 4587 | C | ASN | D | 272 | 103.179 | 1.127 | 165.986 | 1.00 | 48.54 |
| ATOM | 4588 | O | ASN | D | 272 | 103.003 | 1.902 | 165.049 | 1.00 | 51.19 |
| ATOM | 4589 | N | VAL | D | 273 | 102.484 | 0.008 | 166.133 | 1.00 | 47.34 |
| ATOM | 4590 | CA | VAL | D | 273 | 101.452 | 0.368 | 165.172 | 1.00 | 47.18 |
| ATOM | 4591 | CB | VAL | D | 273 | 100.245 | 1.014 | 165.909 | 1.00 | 48.44 |
| ATOM | 4592 | CG1 | VAL | D | 273 | 100.692 | 2.319 | 166.584 | 1.00 | 49.44 |
| ATOM | 4593 | CG2 | VAL | D | 273 | 99.093 | 1.269 | 164.936 | 1.00 | 47.73 |
| ATOM | 4594 | C | VAL | D | 273 | 101.989 | 1.355 | 164.121 | 1.00 | 45.31 |
| ATOM | 4595 | O | VAL | D | 273 | 102.945 | 2.090 | 164.377 | 1.00 | 45.17 |
| ATOM | 4596 | N | GLU | D | 274 | 101.385 | 1.353 | 162.934 | 1.00 | 42.57 |
| ATOM | 4597 | CA | GLU | D | 274 | 101.778 | 2.281 | 161.876 | 1.00 | 40.24 |
| ATOM | 4598 | CB | GLU | D | 274 | 102.807 | 1.650 | 160.942 | 1.00 | 41.03 |
| ATOM | 4599 | CG | GLU | D | 274 | 102.204 | 0.676 | 159.951 | 1.00 | 43.76 |
| ATOM | 4600 | CD | GLU | D | 274 | 103.232 | 0.089 | 159.019 | 1.00 | 44.63 |
| ATOM | 4601 | OE1 | GLU | D | 274 | 104.294 | 0.338 | 159.533 | 1.00 | 47.63 |
| ATOM | 4602 | OE2 | GLU | D | 274 | 102.979 | 0.046 | 157.789 | 1.00 | 42.57 |
| ATOM | 4603 | C | GLU | D | 274 | 100.533 | 2.673 | 161.081 | 1.00 | 37.93 |
| ATOM | 4604 | O | GLU | D | 274 | 99.781 | 1.815 | 160.617 | 1.00 | 36.45 |
| ATOM | 4605 | N | PHE | D | 275 | 100.317 | 3.976 | 160.934 | 1.00 | 36.52 |
| ATOM | 4606 | CA | PHE | D | 275 | 99.155 | 4.499 | 160.210 | 1.00 | 33.93 |
| ATOM | 4607 | CB | PHE | D | 275 | 98.654 | 5.787 | 160.860 | 1.00 | 32.58 |
| ATOM | 4608 | CG | PHE | D | 275 | 98.012 | 5.585 | 162.206 | 1.00 | 29.81 |
| ATOM | 4609 | CD1 | PHE | D | 275 | 96.732 | 5.052 | 162.307 | 1.00 | 28.52 |
| ATOM | 4610 | CD2 | PHE | D | 275 | 98.682 | 5.950 | 163.373 | 1.00 | 26.90 |
| ATOM | 4611 | CE1 | PHE | D | 275 | 96.127 | 4.893 | 163.554 | 1.00 | 30.09 |

TABLE 1-continued

FGFR1 D2–D3 Complexed with FGF2

| ATOM | 4612 | CE2 | PHE | D | 275 | 98.088 | 5.794 | 164.619 | 1.00 | 26.27 |
|---|---|---|---|---|---|---|---|---|---|---|
| ATOM | 4613 | CZ | PHE | D | 275 | 96.811 | 5.267 | 164.713 | 1.00 | 28.01 |
| ATOM | 4614 | C | PHE | D | 275 | 99.465 | 4.779 | 158.758 | 1.00 | 33.21 |
| ATOM | 4615 | O | PHE | D | 275 | 100.619 | 4.954 | 158.380 | 1.00 | 32.57 |
| ATOM | 4616 | N | MET | D | 276 | 98.414 | 4.829 | 157.950 | 1.00 | 33.97 |
| ATOM | 4617 | CA | MET | D | 276 | 98.552 | 5.090 | 156.529 | 1.00 | 34.49 |
| ATOM | 4618 | CB | MET | D | 276 | 98.052 | 3.923 | 155.713 | 1.00 | 38.18 |
| ATOM | 4619 | CG | MET | D | 276 | 98.799 | 2.645 | 155.872 | 1.00 | 44.09 |
| ATOM | 4620 | SD | MET | D | 276 | 98.473 | 1.821 | 154.327 | 1.00 | 50.23 |
| ATOM | 4621 | CE | MET | D | 276 | 99.686 | 2.703 | 153.271 | 1.00 | 48.04 |
| ATOM | 4622 | C | MET | D | 276 | 97.724 | 6.274 | 156.107 | 1.00 | 34.32 |
| ATOM | 4623 | O | MET | D | 276 | 96.730 | 6.619 | 156.747 | 1.00 | 32.03 |
| ATOM | 4624 | N | CYS | D | 277 | 98.123 | 6.871 | 154.994 | 1.00 | 34.70 |
| ATOM | 4625 | CA | CYS | D | 277 | 97.408 | 8.007 | 154.442 | 1.00 | 34.96 |
| ATOM | 4626 | C | CYS | D | 277 | 97.704 | 8.032 | 152.943 | 1.00 | 33.55 |
| ATOM | 4627 | O | CYS | D | 277 | 98.843 | 8.224 | 152.529 | 1.00 | 34.70 |
| ATOM | 4628 | CB | CYS | D | 277 | 97.892 | 9.283 | 155.108 | 1.00 | 36.83 |
| ATOM | 4629 | SG | CYS | D | 277 | 96.863 | 10.744 | 154.794 | 1.00 | 39.87 |
| ATOM | 4630 | N | LYS | D | 278 | 96.682 | 7.820 | 152.130 | 1.00 | 31.82 |
| ATOM | 4631 | CA | LYS | D | 278 | 96.868 | 7.799 | 150.688 | 1.00 | 30.45 |
| ATOM | 4632 | CB | LYS | D | 278 | 96.086 | 6.611 | 150.107 | 1.00 | 33.60 |
| ATOM | 4633 | CG | LYS | D | 278 | 96.331 | 6.278 | 148.628 | 1.00 | 41.46 |
| ATOM | 4634 | CD | LYS | D | 278 | 95.614 | 7.246 | 147.632 | 1.00 | 43.28 |
| ATOM | 4635 | CE | LYS | D | 278 | 95.477 | 6.643 | 146.221 | 1.00 | 40.06 |
| ATOM | 4636 | NZ | LYS | D | 278 | 94.721 | 5.342 | 146.221 | 1.00 | 39.77 |
| ATOM | 4637 | C | LYS | D | 278 | 96.380 | 9.128 | 150.120 | 1.00 | 28.42 |
| ATOM | 4638 | O | LYS | D | 278 | 95.182 | 9.425 | 150.132 | 1.00 | 27.77 |
| ATOM | 4639 | N | VAL | D | 279 | 97.316 | 9.932 | 149.628 | 1.00 | 27.51 |
| ATOM | 4640 | CA | VAL | D | 279 | 96.987 | 11.240 | 149.078 | 1.00 | 26.96 |
| ATOM | 4641 | CB | VAL | D | 279 | 97.969 | 12.305 | 149.565 | 1.00 | 27.10 |
| ATOM | 4642 | CG1 | VAL | D | 279 | 97.531 | 13.683 | 149.075 | 1.00 | 28.38 |
| ATOM | 4643 | CG2 | VAL | D | 279 | 98.044 | 12.278 | 151.066 | 1.00 | 28.56 |
| ATOM | 4644 | C | VAL | D | 279 | 96.991 | 11.306 | 147.560 | 1.00 | 27.47 |
| ATOM | 4645 | O | VAL | D | 279 | 97.666 | 10.528 | 146.887 | 1.00 | 27.46 |
| ATOM | 4646 | N | TYR | D | 280 | 96.213 | 12.243 | 147.031 | 1.00 | 27.87 |
| ATOM | 4647 | CA | TYR | D | 280 | 96.140 | 12.481 | 145.590 | 1.00 | 27.91 |
| ATOM | 4648 | CB | TYR | D | 280 | 94.879 | 11.896 | 144.946 | 1.00 | 25.61 |
| ATOM | 4649 | CG | TYR | D | 280 | 94.783 | 12.292 | 143.492 | 1.00 | 20.03 |
| ATOM | 4650 | CD1 | TYR | D | 280 | 95.581 | 11.663 | 142.538 | 1.00 | 21.49 |
| ATOM | 4651 | CE1 | TYR | D | 280 | 95.641 | 12.113 | 141.214 | 1.00 | 20.60 |
| ATOM | 4652 | CD2 | TYR | D | 280 | 94.016 | 13.377 | 143.092 | 1.00 | 18.90 |
| ATOM | 4653 | CE2 | TYR | D | 280 | 94.064 | 13.843 | 141.766 | 1.00 | 22.69 |
| ATOM | 4654 | CZ | TYR | D | 280 | 94.894 | 13.206 | 140.834 | 1.00 | 23.31 |
| ATOM | 4655 | OH | TYR | D | 280 | 95.053 | 13.704 | 139.556 | 1.00 | 23.42 |
| ATOM | 4656 | C | TYR | D | 280 | 96.100 | 13.978 | 145.338 | 1.00 | 28.68 |
| ATOM | 4657 | O | TYR | D | 280 | 95.275 | 14.692 | 145.906 | 1.00 | 30.82 |
| ATOM | 4658 | N | SER | D | 281 | 96.921 | 4.462 | 144.493 | 1.00 | 28.17 |
| ATOM | 4659 | CA | SER | D | 281 | 96.984 | 15.870 | 144.171 | 1.00 | 28.04 |
| ATOM | 4660 | CB | SER | D | 281 | 97.625 | 16.709 | 145.275 | 1.00 | 28.85 |
| ATOM | 4661 | OG | SER | D | 281 | 97.563 | 18.093 | 144.954 | 1.00 | 27.99 |
| ATOM | 4662 | C | SER | D | 281 | 97.733 | 16.050 | 142.883 | 1.00 | 27.96 |
| ATOM | 4663 | O | SER | D | 281 | 98.740 | 15.372 | 142.645 | 1.00 | 26.52 |
| ATOM | 4664 | N | ASP | D | 282 | 97.211 | 16.942 | 142.040 | 1.00 | 28.40 |
| ATOM | 4665 | CA | ASP | D | 282 | 97.836 | 17.229 | 140.764 | 1.00 | 28.26 |
| ATOM | 4666 | CB | ASP | D | 282 | 96.869 | 18.031 | 139.871 | 1.00 | 26.72 |
| ATOM | 4667 | CG | ASP | D | 282 | 97.391 | 18.230 | 138.437 | 1.00 | 27.05 |
| ATOM | 4668 | OD1 | ASP | D | 282 | 96.605 | 18.670 | 137.565 | 1.00 | 23.35 |
| ATOM | 4669 | OD2 | ASP | D | 282 | 98.584 | 17.968 | 138.174 | 1.00 | 27.42 |
| ATOM | 4670 | C | ASP | D | 282 | 99.077 | 18.008 | 141.190 | 1.00 | 28.63 |
| ATOM | 4671 | O | ASP | D | 282 | 100.185 | 17.485 | 141.091 | 1.00 | 31.59 |
| ATOM | 4672 | N | PRO | D | 283 | 98.918 | 19.246 | 141.703 | 1.00 | 27.45 |
| ATOM | 4673 | CD | PRO | D | 283 | 97.721 | 20.080 | 141.912 | 1.00 | 27.15 |
| ATOM | 4674 | CA | PRO | D | 283 | 100.122 | 19.969 | 142.116 | 1.00 | 25.51 |
| ATOM | 4675 | CB | PRO | D | 283 | 99.612 | 21.377 | 142.350 | 1.00 | 22.95 |
| ATOM | 4676 | CG | PRO | D | 283 | 98.245 | 21.152 | 142.833 | 1.00 | 25.35 |
| ATOM | 4677 | C | PRO | D | 283 | 100.672 | 19.302 | 143.376 | 1.00 | 26.74 |
| ATOM | 4678 | O | PRO | D | 283 | 99.922 | 18.722 | 144.160 | 1.00 | 28.84 |
| ATOM | 4679 | N | GLN | D | 284 | 101.979 | 19.373 | 143.572 | 1.00 | 27.83 |
| ATOM | 4680 | CA | GLN | D | 284 | 102.595 | 18.719 | 144.719 | 1.00 | 27.59 |
| ATOM | 4681 | CB | GLN | D | 284 | 104.098 | 19.008 | 144.738 | 1.00 | 26.73 |
| ATOM | 4682 | CG | GLN | D | 284 | 104.824 | 18.393 | 143.540 | 1.00 | 26.87 |
| ATOM | 4683 | CD | GLN | D | 284 | 104.642 | 16.877 | 143.463 | 1.00 | 26.85 |
| ATOM | 4684 | OE1 | GLN | D | 284 | 104.782 | 16.273 | 142.400 | 1.00 | 29.56 |
| ATOM | 4685 | NE2 | GLN | D | 284 | 104.339 | 16.261 | 144.596 | 1.00 | 26.92 |
| ATOM | 4686 | C | GLN | D | 284 | 101.959 | 19.043 | 146.060 | 1.00 | 27.76 |
| ATOM | 4687 | O | GLN | D | 284 | 101.806 | 20.208 | 146.434 | 1.00 | 29.44 |
| ATOM | 4688 | N | PRO | D | 285 | 101.539 | 17.996 | 146.789 | 1.00 | 27.52 |

TABLE 1-continued

FGFR1 D2–D3 Complexed with FGF2

| ATOM | 4689 | CD | PRO | D | 285 | 101.201 | 16.657 | 146.273 | 1.00 | 26.12 |
|---|---|---|---|---|---|---|---|---|---|---|
| ATOM | 4690 | CA | PRO | D | 285 | 100.926 | 18.206 | 148.101 | 1.00 | 27.83 |
| ATOM | 4691 | CB | PRO | D | 285 | 99.948 | 17.034 | 148.196 | 1.00 | 26.21 |
| ATOM | 4692 | CG | PRO | D | 285 | 100.696 | 15.944 | 147.512 | 1.00 | 24.09 |
| ATOM | 4693 | C | PRO | D | 285 | 101.941 | 18.209 | 149.252 | 1.00 | 27.69 |
| ATOM | 4694 | O | PRO | D | 285 | 102.975 | 17.530 | 149.198 | 1.00 | 26.73 |
| ATOM | 4695 | N | HIS | D | 286 | 101.655 | 19.000 | 150.285 | 1.00 | 27.91 |
| ATOM | 4696 | CA | HIS | D | 286 | 102.515 | 19.025 | 151.450 | 1.00 | 25.77 |
| ATOM | 4697 | CB | HIS | D | 286 | 102.755 | 20.438 | 151.955 | 1.00 | 26.97 |
| ATOM | 4698 | CG | HIS | D | 286 | 103.809 | 20.511 | 153.016 | 1.00 | 27.05 |
| ATOM | 4699 | CD2 | HIS | D | 286 | 104.943 | 19.792 | 153.190 | 1.00 | 27.21 |
| ATOM | 4700 | ND1 | HIS | D | 286 | 103.740 | 21.386 | 154.080 | 1.00 | 25.97 |
| ATOM | 4701 | CE1 | HIS | D | 286 | 104.784 | 21.196 | 154.867 | 1.00 | 27.93 |
| ATOM | 4702 | NE2 | HIS | D | 286 | 105.529 | 20.234 | 154.350 | 1.00 | 27.84 |
| ATOM | 4703 | C | HIS | D | 286 | 101.779 | 18.234 | 152.510 | 1.00 | 25.23 |
| ATOM | 4704 | O | HIS | D | 286 | 100.719 | 18.645 | 152.981 | 1.00 | 24.71 |
| ATOM | 4705 | N | ILE | D | 287 | 102.342 | 17.087 | 152.867 | 1.00 | 26.15 |
| ATOM | 4706 | CA | ILE | D | 287 | 101.757 | 16.199 | 153.863 | 1.00 | 26.81 |
| ATOM | 4707 | CB | ILE | D | 287 | 101.949 | 14.728 | 153.477 | 1.00 | 26.82 |
| ATOM | 4708 | CG2 | ILE | D | 287 | 101.300 | 13.824 | 154.520 | 1.00 | 27.34 |
| ATOM | 4709 | CG1 | ILE | D | 287 | 101.340 | 14.471 | 152.107 | 1.00 | 24.98 |
| ATOM | 4710 | CD1 | ILE | D | 287 | 101.328 | 13.043 | 151.747 | 1.00 | 24.48 |
| ATOM | 4711 | C | ILE | D | 287 | 102.391 | 16.395 | 155.231 | 1.00 | 28.63 |
| ATOM | 4712 | O | ILE | D | 287 | 103.556 | 16.788 | 155.341 | 1.00 | 29.59 |
| ATOM | 4713 | N | GLN | D | 288 | 101.624 | 16.101 | 156.276 | 1.00 | 28.82 |
| ATOM | 4714 | CA | GLN | D | 288 | 102.121 | 16.250 | 157.630 | 1.00 | 28.67 |
| ATOM | 4715 | CB | GLN | D | 288 | 102.031 | 17.712 | 158.048 | 1.00 | 30.80 |
| ATOM | 4716 | CG | GLN | D | 288 | 102.553 | 17.995 | 159.436 | 1.00 | 34.16 |
| ATOM | 4717 | CD | GLN | D | 288 | 102.568 | 19.475 | 159.726 | 1.00 | 36.29 |
| ATOM | 4718 | OE1 | GLN | D | 288 | 103.584 | 20.032 | 160.156 | 1.00 | 36.96 |
| ATOM | 4719 | NE2 | GLN | D | 288 | 101.435 | 20.128 | 159.486 | 1.00 | 36.39 |
| ATOM | 4720 | C | GLN | D | 288 | 101.305 | 15.395 | 158.578 | 1.00 | 27.72 |
| ATOM | 4721 | O | GLN | D | 288 | 100.116 | 15.190 | 158.357 | 1.00 | 27.73 |
| ATOM | 4722 | N | TRP | D | 289 | 101.946 | 14.884 | 159.624 | 1.00 | 26.18 |
| ATOM | 4723 | CA | TRP | D | 289 | 101.247 | 14.077 | 160.608 | 1.00 | 25.04 |
| ATOM | 4724 | CB | TRP | D | 289 | 101.924 | 12.728 | 160.796 | 1.00 | 26.06 |
| ATOM | 4725 | CG | TRP | D | 289 | 101.747 | 11.809 | 159.652 | 1.00 | 24.37 |
| ATOM | 4726 | CD2 | TRP | D | 289 | 100.666 | 10.889 | 159.452 | 1.00 | 24.24 |
| ATOM | 4727 | CE2 | TRP | D | 289 | 100.911 | 10.219 | 158.236 | 1.00 | 23.33 |
| ATOM | 4728 | CE3 | TRP | D | 289 | 99.510 | 10.565 | 160.184 | 1.00 | 25.18 |
| ATOM | 4729 | CD1 | TRP | D | 289 | 102.572 | 11.674 | 158.588 | 1.00 | 23.31 |
| ATOM | 4730 | NE1 | TRP | D | 289 | 102.083 | 10.720 | 157.731 | 1.00 | 24.91 |
| ATOM | 4731 | CZ2 | TRP | D | 289 | 100.048 | 9.236 | 157.724 | 1.00 | 21.63 |
| ATOM | 4732 | CZ3 | TRP | D | 289 | 98.642 | 9.578 | 159.672 | 1.00 | 24.77 |
| ATOM | 4733 | CH2 | TRP | D | 289 | 98.925 | 8.930 | 158.452 | 1.00 | 22.51 |
| ATOM | 4734 | C | TRP | D | 289 | 101.202 | 14.802 | 161.940 | 1.00 | 25.00 |
| ATOM | 4735 | O | TRP | D | 289 | 102.193 | 15.374 | 162.373 | 1.00 | 26.08 |
| ATOM | 4736 | N | LEU | D | 290 | 100.042 | 14.762 | 162.586 | 1.00 | 25.25 |
| ATOM | 4737 | CA | LEU | D | 290 | 99.825 | 15.417 | 163.864 | 1.00 | 25.69 |
| ATOM | 4738 | CB | LEU | D | 290 | 98.788 | 16.514 | 163.722 | 1.00 | 25.43 |
| ATOM | 4739 | CG | LEU | D | 290 | 99.206 | 17.911 | 163.325 | 1.00 | 27.57 |
| ATOM | 4740 | CD1 | LEU | D | 290 | 100.063 | 17.843 | 162.068 | 1.00 | 31.13 |
| ATOM | 4741 | CD2 | LEU | D | 290 | 97.961 | 18.762 | 163.126 | 1.00 | 23.46 |
| ATOM | 4742 | C | LEU | D | 290 | 99.253 | 14.483 | 164.888 | 1.00 | 27.28 |
| ATOM | 4743 | O | LEU | D | 290 | 98.616 | 13.494 | 164.542 | 1.00 | 26.67 |
| ATOM | 4744 | N | LYS | D | 291 | 99.471 | 14.810 | 166.156 | 1.00 | 29.81 |
| ATOM | 4745 | CA | LYS | D | 291 | 98.848 | 14.057 | 167.233 | 1.00 | 32.14 |
| ATOM | 4746 | CB | LYS | D | 291 | 99.833 | 13.316 | 168.120 | 1.00 | 31.84 |
| ATOM | 4747 | CG | LYS | D | 291 | 99.077 | 12.575 | 169.210 | 1.00 | 33.10 |
| ATOM | 4748 | CD | LYS | D | 291 | 99.986 | 11.827 | 170.140 | 1.00 | 37.57 |
| ATOM | 4749 | CE | LYS | D | 291 | 99.193 | 11.164 | 171.249 | 1.00 | 37.27 |
| ATOM | 4750 | NZ | LYS | D | 291 | 100.141 | 10.473 | 172.162 | 1.00 | 38.20 |
| ATOM | 4751 | C | LYS | D | 291 | 98.120 | 15.096 | 168.072 | 1.00 | 33.93 |
| ATOM | 4752 | O | LYS | D | 291 | 98.684 | 16.153 | 168.387 | 1.00 | 33.14 |
| ATOM | 4753 | N | HIS | D | 292 | 96.866 | 14.804 | 168.413 | 1.00 | 35.56 |
| ATOM | 4754 | CA | HIS | D | 292 | 96.052 | 15.716 | 169.205 | 1.00 | 36.77 |
| ATOM | 4755 | CB | HIS | D | 292 | 94.576 | 15.433 | 168.953 | 1.00 | 37.96 |
| ATOM | 4756 | CG | HIS | D | 292 | 94.136 | 15.760 | 167.563 | 1.00 | 40.80 |
| ATOM | 4757 | CD2 | HIS | D | 292 | 93.785 | 14.962 | 166.526 | 1.00 | 42.12 |
| ATOM | 4758 | ND1 | HIS | D | 292 | 94.037 | 17.054 | 167.101 | 1.00 | 40.67 |
| ATOM | 4759 | CE1 | HIS | D | 292 | 93.641 | 17.040 | 165.840 | 1.00 | 41.85 |
| ATOM | 4760 | NE2 | HIS | D | 292 | 93.481 | 15.783 | 165.466 | 1.00 | 42.65 |
| ATOM | 4761 | C | HIS | D | 292 | 96.358 | 15.581 | 170.687 | 1.00 | 37.14 |
| ATOM | 4762 | O | HIS | D | 292 | 96.298 | 14.484 | 171.239 | 1.00 | 38.92 |
| ATOM | 4763 | N | VAL | D | 308 | 98.284 | 20.414 | 169.346 | 1.00 | 33.09 |
| ATOM | 4764 | CA | VAL | D | 308 | 98.821 | 19.295 | 168.570 | 1.00 | 33.71 |
| ATOM | 4765 | CB | VAL | D | 308 | 98.490 | 19.448 | 167.064 | 1.00 | 32.52 |

TABLE 1-continued

FGFR1 D2–D3 Complexed with FGF2

| ATOM | 4766 | CD1 | VAL | D | 308 | 97.010 | 19.502 | 166.862 | 1.00 | 29.95 |
|---|---|---|---|---|---|---|---|---|---|---|
| ATOM | 4767 | CG2 | VAL | D | 308 | 99.155 | 20.697 | 166.515 | 1.00 | 31.27 |
| ATOM | 4768 | C | VAL | D | 308 | 100.343 | 19.119 | 168.681 | 1.00 | 32.88 |
| ATOM | 4769 | O | VAL | D | 308 | 101.059 | 19.964 | 169.223 | 1.00 | 32.12 |
| ATOM | 4770 | N | GLN | D | 309 | 100.818 | 17.997 | 168.160 | 1.00 | 31.80 |
| ATOM | 4771 | CA | GLN | D | 309 | 102.234 | 17.703 | 168.150 | 1.00 | 30.85 |
| ATOM | 4772 | CB | GLN | D | 309 | 102.562 | 16.577 | 169.115 | 1.00 | 30.07 |
| ATOM | 4773 | CG | GLN | D | 309 | 103.829 | 15.882 | 168.709 | 1.00 | 32.83 |
| ATOM | 4774 | CD | GLN | D | 309 | 104.309 | 14.897 | 169.724 | 1.00 | 33.49 |
| ATOM | 4775 | OE1 | GLN | D | 309 | 103.538 | 14.072 | 170.224 | 1.00 | 35.52 |
| ATOM | 4776 | NE2 | GLN | D | 309 | 105.600 | 14.959 | 170.035 | 1.00 | 33.76 |
| ATOM | 4777 | C | GLN | D | 309 | 102.588 | 17.281 | 166.733 | 1.00 | 29.45 |
| ATOM | 4778 | O | GLN | D | 309 | 102.072 | 16.274 | 166.225 | 1.00 | 29.22 |
| ATOM | 4779 | N | ILE | D | 310 | 103.451 | 18.059 | 166.089 | 1.00 | 27.57 |
| ATOM | 4780 | CA | ILE | D | 310 | 103.862 | 17.752 | 164.721 | 1.00 | 25.83 |
| ATOM | 4781 | CB | ILE | D | 310 | 104.536 | 18.961 | 164.062 | 1.00 | 21.88 |
| ATOM | 4782 | CG2 | ILE | D | 310 | 104.713 | 18.710 | 162.584 | 1.00 | 21.49 |
| ATOM | 4783 | CG1 | ILE | D | 310 | 103.657 | 20.191 | 164.252 | 1.00 | 18.95 |
| ATOM | 4784 | CD1 | ILE | D | 310 | 102.170 | 19.948 | 163.940 | 1.00 | 17.06 |
| ATOM | 4785 | C | ILE | D | 310 | 104.805 | 16.563 | 164.740 | 1.00 | 24.75 |
| ATOM | 4786 | O | ILE | D | 310 | 105.919 | 16.654 | 165.236 | 1.00 | 25.81 |
| ATOM | 4787 | N | LEU | D | 311 | 104.342 | 15.442 | 164.207 | 1.00 | 23.85 |
| ATOM | 4788 | CA | LEU | D | 311 | 105.126 | 14.218 | 164.203 | 1.00 | 25.83 |
| ATOM | 4789 | CB | LEU | D | 311 | 104.192 | 13.019 | 164.353 | 1.00 | 25.27 |
| ATOM | 4790 | CG | LEU | D | 311 | 103.223 | 13.077 | 165.532 | 1.00 | 26.41 |
| ATOM | 4791 | CD1 | LEU | D | 311 | 102.098 | 12.051 | 165.348 | 1.00 | 21.64 |
| ATOM | 4792 | CD2 | LEU | D | 311 | 104.015 | 12.860 | 166.820 | 1.00 | 24.12 |
| ATOM | 4793 | C | LEU | D | 311 | 105.979 | 14.015 | 162.955 | 1.00 | 26.90 |
| ATOM | 4794 | O | LEU | D | 311 | 107.079 | 13.462 | 163.031 | 1.00 | 28.62 |
| ATOM | 4795 | N | LYS | D | 312 | 105.470 | 14.456 | 161.811 | 1.00 | 26.26 |
| ATOM | 4796 | CA | LYS | D | 312 | 106.174 | 14.270 | 160.558 | 1.00 | 26.36 |
| ATOM | 4797 | CB | LYS | D | 312 | 105.816 | 12.895 | 159.985 | 1.00 | 27.03 |
| ATOM | 4798 | CG | LYS | D | 312 | 106.793 | 12.339 | 158.963 | 1.00 | 26.95 |
| ATOM | 4799 | CD | LYS | D | 312 | 106.526 | 10.860 | 158.710 | 1.00 | 27.20 |
| ATOM | 4800 | CE | LYS | D | 312 | 107.679 | 10.201 | 157.954 | 1.00 | 27.96 |
| ATOM | 4801 | NZ | LYS | D | 312 | 107.554 | 8.713 | 157.955 | 1.00 | 26.09 |
| ATOM | 4802 | C | LYS | D | 312 | 105.751 | 15.358 | 159.596 | 1.00 | 26.99 |
| ATOM | 4803 | O | LYS | D | 312 | 104.595 | 15.780 | 159.596 | 1.00 | 26.20 |
| ATOM | 4804 | N | THR | D | 313 | 106.693 | 15.828 | 158.787 | 1.00 | 28.01 |
| ATOM | 4805 | CA | THR | D | 313 | 106.385 | 16.861 | 157.820 | 1.00 | 28.06 |
| ATOM | 4806 | CB | THR | D | 313 | 106.595 | 18.263 | 158.393 | 1.00 | 27.10 |
| ATOM | 4807 | OG1 | THR | D | 313 | 105.828 | 18.406 | 159.597 | 1.00 | 25.05 |
| ATOM | 4808 | CG2 | THR | D | 313 | 106.123 | 19.309 | 157.387 | 1.00 | 26.17 |
| ATOM | 4809 | C | THR | D | 313 | 107.246 | 16.677 | 156.592 | 1.00 | 29.26 |
| ATOM | 4810 | O | THR | D | 313 | 108.471 | 16.581 | 156.683 | 1.00 | 31.13 |
| ATOM | 4811 | N | ALA | D | 314 | 106.584 | 16.607 | 155.442 | 1.00 | 29.36 |
| ATOM | 4812 | CA | ALA | D | 314 | 107.257 | 16.420 | 154.166 | 1.00 | 29.34 |
| ATOM | 4813 | CB | ALA | D | 314 | 106.237 | 16.281 | 153.058 | 1.00 | 27.47 |
| ATOM | 4814 | C | ALA | D | 314 | 108.204 | 17.562 | 153.842 | 1.00 | 30.36 |
| ATOM | 4815 | O | ALA | D | 314 | 107.974 | 18.712 | 154.228 | 1.00 | 30.60 |
| ATOM | 4816 | N | GLY | D | 315 | 109.264 | 17.227 | 153.116 | 1.00 | 29.90 |
| ATOM | 4817 | CA | GLY | D | 315 | 110.252 | 18.211 | 152.727 | 1.00 | 29.95 |
| ATOM | 4818 | C | GLY | D | 315 | 111.524 | 17.495 | 152.343 | 1.00 | 30.80 |
| ATOM | 4819 | O | GLY | D | 315 | 111.577 | 16.265 | 152.353 | 1.00 | 31.54 |
| ATOM | 4820 | N | VAL | D | 316 | 112.555 | 18.254 | 152.004 | 1.00 | 30.69 |
| ATOM | 4821 | CA | VAL | D | 316 | 113.817 | 17.654 | 151.619 | 1.00 | 31.98 |
| ATOM | 4822 | CB | VAL | D | 316 | 114.869 | 18.739 | 151.357 | 1.00 | 32.20 |
| ATOM | 4823 | CG1 | VAL | D | 316 | 116.252 | 18.117 | 151.272 | 1.00 | 34.99 |
| ATOM | 4824 | CG2 | VAL | D | 316 | 114.548 | 19.455 | 150.058 | 1.00 | 33.78 |
| ATOM | 4825 | C | VAL | D | 316 | 114.355 | 16.654 | 152.655 | 1.00 | 32.59 |
| ATOM | 4826 | O | VAL | D | 316 | 115.014 | 15.681 | 152.301 | 1.00 | 33.55 |
| ATOM | 4827 | N | ASN | D | 317 | 114.071 | 16.891 | 153.929 | 1.00 | 32.95 |
| ATOM | 4828 | CA | ASN | D | 317 | 114.538 | 16.009 | 154.998 | 1.00 | 34.22 |
| ATOM | 4829 | CB | ASN | D | 317 | 114.477 | 16.711 | 156.355 | 1.00 | 34.35 |
| ATOM | 4830 | CG | ASN | D | 317 | 115.607 | 17.680 | 156.570 | 1.00 | 34.02 |
| ATOM | 4831 | OD1 | ASN | D | 317 | 115.668 | 18.340 | 157.608 | 1.00 | 34.37 |
| ATOM | 4832 | ND2 | ASN | D | 317 | 116.512 | 17.776 | 155.596 | 1.00 | 33.35 |
| ATOM | 4833 | C | ASN | D | 317 | 113.706 | 14.748 | 155.118 | 1.00 | 35.11 |
| ATOM | 4834 | O | ASN | D | 317 | 114.151 | 13.737 | 155.658 | 1.00 | 34.96 |
| ATOM | 4835 | N | THR | D | 318 | 112.476 | 14.815 | 154.647 | 1.00 | 36.25 |
| ATOM | 4836 | CA | THR | D | 318 | 111.599 | 13.670 | 154.729 | 1.00 | 35.45 |
| ATOM | 4837 | CB | THR | D | 318 | 110.737 | 13.758 | 155.994 | 1.00 | 35.52 |
| ATOM | 4838 | OG1 | THR | D | 318 | 111.563 | 13.517 | 157.140 | 1.00 | 33.24 |
| ATOM | 4839 | CG2 | THR | D | 318 | 109.633 | 12.743 | 155.963 | 1.00 | 36.91 |
| ATOM | 4840 | C | THR | D | 318 | 110.760 | 13.645 | 153.474 | 1.00 | 36.75 |
| ATOM | 4841 | O | THR | D | 318 | 109.685 | 14.233 | 153.403 | 1.00 | 38.77 |
| ATOM | 4842 | N | THR | D | 319 | 111.309 | 12.970 | 152.473 | 1.00 | 37.80 |

TABLE 1-continued

FGFR1 D2–D3 Complexed with FGF2

| ATOM | 4843 | CA | THR | D | 319 | 110.718 | 12.809 | 151.152 | 1.00 | 37.38 |
|---|---|---|---|---|---|---|---|---|---|---|
| ATOM | 4844 | CB | THR | D | 319 | 111.661 | 11.962 | 150.294 | 1.00 | 37.90 |
| ATOM | 4845 | OG1 | THR | D | 319 | 112.838 | 12.723 | 150.042 | 1.00 | 39.64 |
| ATOM | 4846 | CG2 | THR | D | 319 | 111.020 | 11.559 | 148.967 | 1.00 | 41.12 |
| ATOM | 4847 | C | THR | D | 319 | 109.347 | 12.154 | 151.164 | 1.00 | 36.69 |
| ATOM | 4848 | O | THR | D | 319 | 109.022 | 11.402 | 152.086 | 1.00 | 36.67 |
| ATOM | 4849 | N | ASP | D | 320 | 108.554 | 12.436 | 150.128 | 1.00 | 36.46 |
| ATOM | 4850 | CA | ASP | D | 320 | 107.216 | 11.859 | 149.997 | 1.00 | 35.83 |
| ATOM | 4851 | CB | ASP | D | 320 | 106.624 | 12.117 | 148.610 | 1.00 | 33.91 |
| ATOM | 4852 | CG | ASP | D | 320 | 106.286 | 13.570 | 148.373 | 1.00 | 34.35 |
| ATOM | 4853 | OD1 | ASP | D | 320 | 105.917 | 14.262 | 149.346 | 1.00 | 32.14 |
| ATOM | 4854 | OD2 | ASP | D | 320 | 106.374 | 14.015 | 147.205 | 1.00 | 34.66 |
| ATOM | 4855 | C | ASP | D | 320 | 107.271 | 10.359 | 150.206 | 1.00 | 35.84 |
| ATOM | 4856 | O | ASP | D | 320 | 106.323 | 9.759 | 150.695 | 1.00 | 36.05 |
| ATOM | 4857 | N | LYS | D | 321 | 108.385 | 9.752 | 149.821 | 1.00 | 37.45 |
| ATOM | 4858 | CA | LYS | D | 321 | 108.548 | 8.314 | 149.966 | 1.00 | 37.85 |
| ATOM | 4859 | CB | LYS | D | 321 | 110.014 | 7.931 | 149.794 | 1.00 | 39.71 |
| ATOM | 4860 | CG | LYS | D | 321 | 110.605 | 8.440 | 148.502 | 1.00 | 43.24 |
| ATOM | 4861 | CD | LYS | D | 321 | 112.123 | 8.263 | 148.471 | 1.00 | 47.56 |
| ATOM | 4862 | CE | LYS | D | 321 | 112.737 | 8.967 | 147.246 | 1.00 | 49.40 |
| ATOM | 4863 | NZ | LYS | D | 321 | 114.185 | 8.668 | 147.052 | 1.00 | 48.66 |
| ATOM | 4864 | C | LYS | D | 321 | 108.045 | 7.841 | 151.320 | 1.00 | 37.80 |
| ATOM | 4865 | O | LYS | D | 321 | 107.177 | 6.982 | 151.395 | 1.00 | 39.63 |
| ATOM | 4866 | N | GLU | D | 322 | 108.560 | 8.428 | 152.391 | 1.00 | 36.93 |
| ATOM | 4867 | CA | GLU | D | 322 | 108.173 | 8.021 | 153.732 | 1.00 | 36.01 |
| ATOM | 4868 | CB | GLU | D | 322 | 109.381 | 8.179 | 154.649 | 1.00 | 34.63 |
| ATOM | 4869 | CG | GLU | D | 322 | 109.979 | 9.585 | 154.627 | 1.00 | 32.89 |
| ATOM | 4870 | CD | GLU | D | 322 | 111.343 | 9.678 | 155.330 | 1.00 | 32.55 |
| ATOM | 4871 | OE1 | GLU | D | 322 | 111.467 | 9.187 | 156.479 | 1.00 | 28.33 |
| ATOM | 4872 | OE2 | GLU | D | 322 | 112.288 | 10.253 | 154.730 | 1.00 | 30.74 |
| ATOM | 4873 | CG | GLU | D | 322 | 106.983 | 8.747 | 154.345 | 1.00 | 36.20 |
| ATOM | 4874 | O | GLU | D | 322 | 106.546 | 8.393 | 155.433 | 1.00 | 36.13 |
| ATOM | 4875 | N | MET | D | 323 | 106.446 | 9.744 | 153.653 | 1.00 | 36.12 |
| ATOM | 4876 | CA | MET | D | 323 | 105.341 | 10.529 | 154.195 | 1.00 | 36.16 |
| ATOM | 4877 | CB | MET | D | 323 | 105.272 | 11.881 | 153.479 | 1.00 | 36.94 |
| ATOM | 4878 | CG | MET | D | 323 | 106.389 | 12.840 | 153.876 | 1.00 | 36.64 |
| ATOM | 4879 | SD | MET | D | 323 | 106.595 | 12.886 | 155.676 | 1.00 | 34.99 |
| ATOM | 4880 | CE | MET | D | 323 | 104.933 | 13.398 | 156.200 | 1.00 | 37.06 |
| ATOM | 4881 | C | MET | D | 323 | 103.940 | 9.935 | 154.259 | 1.00 | 36.22 |
| ATOM | 4882 | O | MET | D | 323 | 103.088 | 10.474 | 154.954 | 1.00 | 35.07 |
| ATOM | 4883 | N | GLU | D | 324 | 103.688 | 8.836 | 153.556 | 1.00 | 37.83 |
| ATOM | 4884 | CA | GLU | D | 324 | 102.352 | 8.250 | 153.574 | 1.00 | 37.78 |
| ATOM | 4885 | CB | GLU | D | 324 | 102.023 | 7.635 | 152.208 | 1.00 | 39.20 |
| ATOM | 4886 | CG | GLU | D | 324 | 101.867 | 8.691 | 151.115 | 1.00 | 45.52 |
| ATOM | 4887 | CD | GLU | D | 324 | 101.254 | 8.153 | 149.821 | 1.00 | 48.59 |
| ATOM | 4888 | OE1 | GLU | D | 324 | 101.736 | 7.109 | 149.325 | 1.00 | 52.60 |
| ATOM | 4889 | OE2 | GLU | D | 324 | 100.304 | 8.779 | 149.290 | 1.00 | 46.67 |
| ATOM | 4890 | C | GLU | D | 324 | 102.093 | 7.248 | 154.699 | 1.00 | 36.24 |
| ATOM | 4891 | O | GLU | D | 324 | 100.972 | 6.767 | 154.873 | 1.00 | 36.10 |
| ATOM | 4892 | N | VAL | D | 325 | 103.115 | 6.953 | 155.484 | 1.00 | 34.34 |
| ATOM | 4893 | CA | VAL | D | 325 | 102.945 | 6.021 | 156.582 | 1.00 | 35.57 |
| ATOM | 4894 | CB | VAL | D | 325 | 103.579 | 4.653 | 156.249 | 1.00 | 34.18 |
| ATOM | 4895 | CG1 | VAL | D | 325 | 105.095 | 4.781 | 156.198 | 1.00 | 32.54 |
| ATOM | 4896 | CG2 | VAL | D | 325 | 103.167 | 3.625 | 157.282 | 1.00 | 32.08 |
| ATOM | 4897 | C | VAL | D | 325 | 103.570 | 6.550 | 157.878 | 1.00 | 36.78 |
| ATOM | 4898 | O | VAL | D | 325 | 104.755 | 6.887 | 157.916 | 1.00 | 36.54 |
| ATOM | 4899 | N | LEU | D | 326 | 102.764 | 6.631 | 158.935 | 1.00 | 37.89 |
| ATOM | 4900 | CA | LEU | D | 326 | 103.243 | 7.097 | 160.235 | 1.00 | 38.72 |
| ATOM | 4901 | CB | LEU | D | 326 | 102.184 | 7.958 | 160.919 | 1.00 | 38.44 |
| ATOM | 4902 | CG | LEU | D | 326 | 102.598 | 8.517 | 162.283 | 1.00 | 38.99 |
| ATOM | 4903 | CD1 | LEU | D | 326 | 103.837 | 9.373 | 162.117 | 1.00 | 37.38 |
| ATOM | 4904 | CD2 | LEU | D | 326 | 101.465 | 9.344 | 162.883 | 1.00 | 38.01 |
| ATOM | 4905 | C | LEU | D | 326 | 103.564 | 5.890 | 161.114 | 1.00 | 39.59 |
| ATOM | 4906 | O | LEU | D | 326 | 102.700 | 5.069 | 161.401 | 1.00 | 38.62 |
| ATOM | 4907 | N | HIS | D | 327 | 104.814 | 5.794 | 161.540 | 1.00 | 41.75 |
| ATOM | 4908 | CA | HIS | D | 327 | 105.257 | 4.679 | 162.355 | 1.00 | 43.79 |
| ATOM | 4909 | CB | HIS | D | 327 | 106.648 | 4.249 | 161.914 | 1.00 | 46.71 |
| ATOM | 4910 | CG | HIS | D | 327 | 106.674 | 3.598 | 160.574 | 1.00 | 49.33 |
| ATOM | 4911 | CD2 | HIS | D | 327 | 107.068 | 4.062 | 159.365 | 1.00 | 50.34 |
| ATOM | 4912 | ND1 | HIS | D | 327 | 106.215 | 2.314 | 160.367 | 1.00 | 49.92 |
| ATOM | 4913 | CE1 | HIS | D | 327 | 106.324 | 2.015 | 159.085 | 1.00 | 51.65 |
| ATOM | 4914 | NE2 | HIS | D | 327 | 106.839 | 3.058 | 158.456 | 1.00 | 52.95 |
| ATOM | 4915 | C | HIS | D | 327 | 105.302 | 4.981 | 163.830 | 1.00 | 44.31 |
| ATOM | 4916 | O | HIS | D | 327 | 105.916 | 5.955 | 164.254 | 1.00 | 44.81 |
| ATOM | 4917 | N | LEU | D | 328 | 104.654 | 4.142 | 164.618 | 1.00 | 45.14 |
| ATOM | 4918 | CA | LEU | D | 328 | 104.688 | 4.322 | 166.055 | 1.00 | 47.78 |
| ATOM | 4919 | CB | LEU | D | 328 | 103.278 | 4.587 | 166.603 | 1.00 | 46.33 |

TABLE 1-continued

FGFR1 D2–D3 Complexed with FGF2

| ATOM | 4920 | CG | LEU | D | 328 | 102.642 | 5.872 | 166.044 | 1.00 | 43.57 |
| ATOM | 4921 | CD1 | LEU | D | 328 | 101.380 | 6.232 | 166.811 | 1.00 | 42.21 |
| ATOM | 4922 | CD2 | LEU | D | 328 | 103.631 | 7.000 | 166.136 | 1.00 | 39.43 |
| ATOM | 4923 | C | LEU | D | 328 | 105.310 | 3.046 | 166.615 | 1.00 | 50.07 |
| ATOM | 4924 | O | LEU | D | 328 | 104.682 | 1.987 | 166.642 | 1.00 | 51.11 |
| ATOM | 4925 | N | ARG | D | 329 | 106.571 | 3.164 | 167.022 | 1.00 | 52.33 |
| ATOM | 4926 | CA | ARG | D | 329 | 107.351 | 2.051 | 167.558 | 1.00 | 54.65 |
| ATOM | 4927 | CB | ARG | D | 329 | 108.842 | 2.324 | 167.336 | 1.00 | 54.25 |
| ATOM | 4928 | C | ARG | D | 329 | 107.095 | 1.820 | 169.043 | 1.00 | 56.39 |
| ATOM | 4929 | O | ARG | D | 329 | 107.316 | 2.716 | 169.857 | 1.00 | 57.26 |
| ATOM | 4930 | N | ASN | D | 330 | 106.649 | 0.612 | 169.389 | 1.00 | 58.57 |
| ATOM | 4931 | CA | ASN | D | 330 | 106.338 | 0.250 | 170.774 | 1.00 | 60.39 |
| ATOM | 4932 | CB | ASN | D | 330 | 107.607 | 0.066 | 171.560 | 1.00 | 63.16 |
| ATOM | 4933 | CG | ASN | D | 330 | 107.328 | 0.299 | 173.031 | 1.00 | 65.73 |
| ATOM | 4934 | 001 | ASN | D | 330 | 107.248 | 0.648 | 173.819 | 1.00 | 66.78 |
| ATOM | 4935 | ND2 | ASN | D | 330 | 107.155 | 1.562 | 173.406 | 1.00 | 67.36 |
| ATOM | 4936 | C | ASN | D | 330 | 105.565 | 1.355 | 171.477 | 1.00 | 60.09 |
| ATOM | 4937 | O | AEN | D | 330 | 106.147 | 2.282 | 172.041 | 1.00 | 60.19 |
| ATOM | 4938 | N | VAL | D | 331 | 104.244 | 1.244 | 171.450 | 1.00 | 59.65 |
| ATOM | 4939 | CA | VAL | D | 331 | 103.397 | 2.257 | 172.053 | 1.00 | 59.89 |
| ATOM | 4940 | CB | VAL | D | 331 | 101.979 | 2.227 | 171.431 | 1.00 | 58.63 |
| ATOM | 4941 | CG1 | VAL | D | 331 | 102.057 | 2.593 | 169.967 | 1.00 | 57.29 |
| ATOM | 4942 | CG2 | VAL | D | 331 | 101.370 | 0.851 | 171.580 | 1.00 | 57.94 |
| ATOM | 4943 | C | VAL | D | 331 | 103.288 | 2.155 | 173.565 | 1.00 | 60.47 |
| ATOM | 4944 | O | VAL | D | 331 | 103.862 | 1.267 | 174.187 | 1.00 | 61.22 |
| ATOM | 4945 | N | SER | D | 332 | 102.548 | 3.092 | 174.144 | 1.00 | 61.44 |
| ATOM | 4946 | CA | SER | D | 332 | 102.321 | 3.156 | 175.583 | 1.00 | 62.61 |
| ATOM | 4947 | CB | SER | D | 332 | 103.424 | 3.969 | 176.269 | 1.00 | 62.34 |
| ATOM | 4948 | OC | SER | D | 332 | 103.348 | 5.346 | 175.927 | 1.00 | 60.01 |
| ATOM | 4949 | C | SER | D | 332 | 100.923 | .868 | 175.766 | 1.00 | 63.67 |
| ATOM | 4950 | O | SER | D | 332 | 100.512 | 4.522 | 174.845 | 1.00 | 64.37 |
| ATOM | 4951 | N | PHE | D | 333 | 100.397 | 3.754 | 176.946 | 1.00 | 64.59 |
| ATOM | 4952 | CA | PHE | D | 333 | 99.122 | 4.413 | 177.199 | 1.00 | 65.42 |
| ATOM | 4953 | CB | PHE | D | 333 | 98.744 | 4.276 | 178.676 | 1.00 | 68.43 |
| ATOM | 4954 | CG | PHE | D | 333 | 98.278 | 2.896 | 179.054 | 1.00 | 72.42 |
| ATOM | 4955 | CD1 | PHE | D | 333 | 98.169 | 2.526 | 180.391 | 1.00 | 73.24 |
| ATOM | 4956 | CD2 | PHE | D | 333 | 97.933 | 1.966 | 178.069 | 1.00 | 74.01 |
| ATOM | 4957 | CE1 | PHE | D | 333 | 97.725 | 1.252 | 180.745 | 1.00 | 73.82 |
| ATOM | 4958 | CE2 | PHE | D | 333 | 97.488 | 0.691 | 178.413 | 1.00 | 74.79 |
| ATOM | 4959 | CZ | PHE | D | 333 | 97.384 | 0.334 | 179.754 | 1.00 | 74.53 |
| ATOM | 4960 | C | PHE | D | 333 | 99.180 | 5.882 | 176.809 | 1.00 | 64.25 |
| ATOM | 4961 | O | PHE | D | 333 | 98.161 | 6.494 | 176.488 | 1.00 | 63.25 |
| ATOM | 4962 | N | GLU | D | 334 | 100.386 | 6.436 | 176.830 | 1.00 | 63.41 |
| ATOM | 4963 | CA | GLU | D | 334 | 100.591 | 7.835 | 176.486 | 1.00 | 62.79 |
| ATOM | 4964 | CB | GLU | D | 334 | 102.032 | 8.235 | 176.794 | 1.00 | 65.85 |
| ATOM | 4965 | CG | GLU | D | 334 | 102.503 | 7.874 | 178.195 | 1.00 | 69.95 |
| ATOM | 4966 | CD | GLU | D | 334 | 104.013 | 8.031 | 178.345 | 1.00 | 73.26 |
| ATOM | 4967 | OE1 | GLU | D | 334 | 104.540 | 7.773 | 179.457 | 1.00 | 73.50 |
| ATOM | 4968 | OE2 | GLU | D | 334 | 104.669 | 8.410 | 177.342 | 1.00 | 73.62 |
| ATOM | 4969 | C | GLU | D | 334 | 100.293 | 8.067 | 175.002 | 1.00 | 59.92 |
| ATOM | 4970 | O | GLU | D | 334 | 99.578 | 9.003 | 174.643 | 1.00 | 59.28 |
| ATOM | 4971 | N | ASP | D | 335 | 100.839 | 7.198 | 174.154 | 1.00 | 55.93 |
| ATOM | 4972 | CA | ASP | D | 335 | 100.669 | 7.287 | 172.712 | 1.00 | 51.63 |
| ATOM | 4973 | CB | ASP | D | 335 | 101.515 | 6.217 | 172.037 | 1.00 | 49.63 |
| ATOM | 4974 | CG | ASP | D | 335 | 102.974 | 6.327 | 172.406 | 1.00 | 48.72 |
| ATOM | 4975 | OD1 | ASP | D | 335 | 103.514 | 7.444 | 172.311 | 1.00 | 46.64 |
| ATOM | 4976 | OD2 | ASP | D | 335 | 103.584 | 5.303 | 172.790 | 1.00 | 50.29 |
| ATOM | 4977 | C | ASP | D | 335 | 99.224 | 7.183 | 172.239 | 1.00 | 50.20 |
| ATOM | 4978 | O | ASP | D | 335 | 98.923 | 7.478 | 171.079 | 1.00 | 50.69 |
| ATOM | 4979 | N | ALA | D | 336 | 98.327 | 6.764 | 173.123 | 1.00 | 47.17 |
| ATOM | 4980 | CA | ALA | D | 336 | 96.924 | 6.659 | 172.750 | 1.00 | 44.10 |
| ATOM | 4981 | CB | ALA | D | 336 | 96.119 | 6.160 | 173.923 | 1.00 | 44.65 |
| ATOM | 4982 | C | ALA | D | 336 | 96.448 | 8.050 | 172.331 | 1.00 | 42.08 |
| ATOM | 4983 | O | ALA | D | 336 | 97.047 | 9.059 | 172.709 | 1.00 | 42.12 |
| ATOM | 4984 | N | GLY | D | 337 | 95.384 | 8.113 | 171.544 | 1.00 | 39.09 |
| ATOM | 4985 | CA | GLY | D | 337 | 94.900 | 9.406 | 171.116 | 1.00 | 36.28 |
| ATOM | 4986 | C | GLY | D | 337 | 94.650 | 9.494 | 169.627 | 1.00 | 35.30 |
| ATOM | 4987 | O | GLY | D | 337 | 94.873 | 8.550 | 168.874 | 1.00 | 37.23 |
| ATOM | 4988 | N | GLU | D | 338 | 94.199 | 10.661 | 169.203 | 1.00 | 34.06 |
| ATOM | 4989 | CA | GLU | D | 338 | 93.864 | 10.928 | 167.819 | 1.00 | 31.79 |
| ATOM | 4990 | CB | GLU | D | 338 | 92.743 | 11.964 | 167.823 | 1.00 | 32.76 |
| ATOM | 4991 | CG | GLU | D | 338 | 92.136 | 12.358 | 166.515 | 1.00 | 35.47 |
| ATOM | 4992 | CD | GLU | D | 338 | 90.919 | 13.237 | 166.746 | 1.00 | 38.92 |
| ATOM | 4993 | OE1 | GLU | D | 338 | 90.910 | 13.990 | 167.750 | 1.00 | 40.52 |
| ATOM | 4994 | OE2 | GLU | D | 338 | 89.972 | 13.183 | 165.937 | 1.00 | 40.80 |
| ATOM | 4995 | C | GLU | D | 338 | 95.058 | 11.401 | 166.987 | 1.00 | 30.61 |
| ATOM | 4996 | O | GLU | D | 338 | 95.751 | 12.362 | 167.336 | 1.00 | 28.27 |

TABLE 1-continued

FGFR1 D2–D3 Complexed with FGF2

| ATOM | 4997 | N | TYR | D | 339 | 95.301 | 10.701 | 165.886 | 1.00 | 29.87 |
|---|---|---|---|---|---|---|---|---|---|---|
| ATOM | 4998 | CA | TYR | D | 339 | 96.388 | 11.062 | 164.989 | 1.00 | 30.24 |
| ATOM | 4999 | CB | TYR | D | 339 | 97.305 | 9.865 | 164.711 | 1.00 | 30.60 |
| ATOM | 5000 | CG | TYR | D | 339 | 98.156 | 9.495 | 165.893 | 1.00 | 31.84 |
| ATOM | 5001 | CD1 | TYR | D | 339 | 97.613 | 8.807 | 166.984 | 1.00 | 33.22 |
| ATOM | 5002 | CE1 | TYR | D | 339 | 98.365 | 8.561 | 168.127 | 1.00 | 35.77 |
| ATOM | 5003 | CD2 | TYR | D | 339 | 99.478 | 9.917 | 165.970 | 1.00 | 33.47 |
| ATOM | 5004 | CE2 | TYR | D | 339 | 100.242 | 9.683 | 167.104 | 1.00 | 36.30 |
| ATOM | 5005 | CZ | TYR | D | 339 | 99.683 | 9.009 | 168.182 | 1.00 | 38.40 |
| ATOM | 5006 | OH | TYR | D | 339 | 100.439 | 8.829 | 169.323 | 1.00 | 41.10 |
| ATOM | 5007 | C | TYR | D | 339 | 95.747 | 11.557 | 163.711 | 1.00 | 29.89 |
| ATOM | 5008 | O | TYR | D | 339 | 94.753 | 10.998 | 163.249 | 1.00 | 28.60 |
| ATOM | 5009 | N | THR | D | 340 | 96.316 | 12.613 | 163.143 | 1.00 | 30.27 |
| ATOM | 5010 | CA | THR | D | 340 | 95.757 | 13.196 | 161.942 | 1.00 | 29.19 |
| ATOM | 5011 | CB | THR | D | 340 | 95.164 | 14.567 | 162.269 | 1.00 | 28.40 |
| ATOM | 5012 | OG1 | THR | D | 340 | 94.249 | 14.418 | 163.357 | 1.00 | 28.64 |
| ATOM | 5013 | CG2 | THR | D | 340 | 94.430 | 15.146 | 161.075 | 1.00 | 27.74 |
| ATOM | 5014 | C | THR | D | 340 | 96.747 | 13.328 | 160.799 | 1.00 | 29.78 |
| ATOM | 5015 | O | THR | D | 340 | 97.928 | 13.616 | 161.002 | 1.00 | 29.63 |
| ATOM | 5016 | N | CYS | D | 341 | 96.244 | 13.098 | 159.592 | 1.00 | 29.75 |
| ATOM | 5017 | CA | CYS | D | 341 | 97.052 | 13.222 | 158.397 | 1.00 | 31.36 |
| ATOM | 5018 | C | CYS | D | 341 | 96.573 | 14.424 | 157.580 | 1.00 | 30.34 |
| ATOM | 5019 | O | CYS | D | 341 | 95.439 | 14.427 | 157.095 | 1.00 | 31.13 |
| ATOM | 5020 | CB | CYS | D | 341 | 96.953 | 11.954 | 157.561 | 1.00 | 33.83 |
| ATOM | 5021 | SG | CYS | D | 341 | 97.798 | 12.118 | 155.958 | 1.00 | 38.30 |
| ATOM | 5022 | N | LEU | D | 342 | 97.429 | 15.440 | 157.443 | 1.00 | 28.14 |
| ATOM | 5023 | CA | LEU | D | 342 | 97.084 | 16.632 | 156.680 | 1.00 | 25.64 |
| ATOM | 5024 | CB | LEU | D | 342 | 97.421 | 17.909 | 157.433 | 1.00 | 29.80 |
| ATOM | 5025 | CG | LEU | D | 342 | 96.974 | 18.193 | 158.862 | 1.00 | 34.80 |
| ATOM | 5026 | CD1 | LEU | D | 342 | 96.751 | 19.704 | 158.943 | 1.00 | 34.66 |
| ATOM | 5027 | CD2 | LEU | D | 342 | 95.703 | 17.435 | 159.246 | 1.00 | 33.53 |
| ATOM | 5028 | C | LEU | D | 342 | 97.828 | 16.702 | 155.370 | 1.00 | 24.11 |
| ATOM | 5029 | O | LEU | D | 342 | 99.010 | 16.345 | 155.288 | 1.00 | 22.00 |
| ATOM | 5030 | N | ALA | D | 343 | 97.130 | 17.193 | 154.352 | 1.00 | 21.64 |
| ATOM | 5031 | CA | ALA | D | 343 | 97.711 | 17.364 | 153.031 | 1.00 | 20.61 |
| ATOM | 5032 | CB | ALA | D | 343 | 97.465 | 16.147 | 152.182 | 1.00 | 21.72 |
| ATOM | 5033 | C | ALA | D | 343 | 97.112 | 18.592 | 152.372 | 1.00 | 20.26 |
| ATOM | 5034 | O | ALA | D | 343 | 95.900 | 18.779 | 152.364 | 1.00 | 20.13 |
| ATOM | 5035 | N | GLY | D | 344 | 97.970 | 19.440 | 151.827 | 1.00 | 21.09 |
| ATOM | 5036 | CA | GLY | D | 344 | 97.473 | 20.634 | 151.181 | 1.00 | 22.38 |
| ATOM | 5037 | C | GLY | D | 344 | 98.345 | 21.160 | 150.060 | 1.00 | 23.80 |
| ATOM | 5038 | O | GLY | D | 344 | 99.540 | 20.857 | 149.971 | 1.00 | 23.92 |
| ATOM | 5039 | N | ASN | D | 345 | 97.720 | 21.919 | 149.167 | 1.00 | 23.54 |
| ATOM | 5040 | CA | ASN | D | 345 | 98.439 | 22.546 | 148.082 | 1.00 | 21.83 |
| ATOM | 5041 | CB | ASN | D | 345 | 98.150 | 21.895 | 146.733 | 1.00 | 21.01 |
| ATOM | 5042 | CG | ASN | D | 345 | 96.679 | 21.689 | 146.476 | 1.00 | 24.41 |
| ATOM | 5043 | CD1 | ASN | D | 345 | 95.861 | 22.605 | 146.636 | 1.00 | 26.37 |
| ATOM | 5044 | ND2 | ASN | D | 345 | 96.331 | 20.482 | 146.038 | 1.00 | 20.51 |
| ATOM | 5045 | C | ASN | D | 345 | 98.001 | 23.984 | 148.101 | 1.00 | 22.08 |
| ATOM | 5046 | O | ASN | D | 345 | 97.356 | 24.430 | 149.046 | 1.00 | 19.30 |
| ATOM | 5047 | N | SER | D | 346 | 98.356 | 24.727 | 147.075 | 1.00 | 24.23 |
| ATOM | 5048 | CA | SER | D | 346 | 97.991 | 26.123 | 147.061 | 1.00 | 27.91 |
| ATOM | 5049 | CB | SER | D | 346 | 98.779 | 26.857 | 145.969 | 1.00 | 30.80 |
| ATOM | 5050 | OG | SER | D | 346 | 98.859 | 26.091 | 144.773 | 1.00 | 37.69 |
| ATOM | 5051 | C | SER | D | 346 | 96.491 | 26.314 | 146.894 | 1.00 | 28.82 |
| ATOM | 5052 | O | SER | D | 346 | 95.952 | 27.355 | 147.250 | 1.00 | 29.53 |
| ATOM | 5053 | N | ILE | D | 347 | 95.806 | 25.299 | 146.381 | 1.00 | 30.08 |
| ATOM | 5054 | CA | ILE | D | 347 | 94.371 | 25.416 | 146.190 | 1.00 | 28.98 |
| ATOM | 5055 | CB | ILE | D | 347 | 93.870 | 24.403 | 145.169 | 1.00 | 26.99 |
| ATOM | 5056 | CG2 | ILE | D | 347 | 92.394 | 24.583 | 144.965 | 1.00 | 22.50 |
| ATOM | 5057 | CG1 | ILE | D | 347 | 94.606 | 24.621 | 143.851 | 1.00 | 26.44 |
| ATOM | 5058 | CD1 | ILE | D | 347 | 94.363 | 23.584 | 142.795 | 1.00 | 30.48 |
| ATOM | 5059 | C | ILE | D | 347 | 93.607 | 25.266 | 147.496 | 1.00 | 29.91 |
| ATOM | 5060 | O | ILE | D | 347 | 92.719 | 26.058 | 147.788 | 1.00 | 32.67 |
| ATOM | 5061 | N | GLY | D | 348 | 93.950 | 24.273 | 148.301 | 1.00 | 28.95 |
| ATOM | 5062 | CA | GLY | D | 348 | 93.239 | 24.114 | 149.554 | 1.00 | 30.13 |
| ATOM | 5063 | C | GLY | D | 348 | 93.890 | 23.115 | 150.483 | 1.00 | 30.97 |
| ATOM | 5064 | O | GLY | D | 348 | 95.017 | 22.680 | 150.241 | 1.00 | 31.52 |
| ATOM | 5065 | N | LEU | D | 349 | 93.179 | 22.749 | 151.545 | 1.00 | 30.91 |
| ATOM | 5066 | CA | LEU | D | 349 | 93.697 | 21.789 | 152.513 | 1.00 | 31.11 |
| ATOM | 5067 | CB | LEU | D | 349 | 94.104 | 22.517 | 153.796 | 1.00 | 31.40 |
| ATOM | 5068 | CG | LEU | D | 349 | 94.819 | 21.653 | 154.841 | 1.00 | 33.44 |
| ATOM | 5069 | CD1 | LEU | D | 349 | 96.170 | 21.198 | 154.305 | 1.00 | 31.52 |
| ATOM | 5070 | CD2 | LEU | D | 349 | 94.989 | 22.451 | 156.124 | 1.00 | 33.38 |
| ATOM | 5071 | C | LEU | D | 349 | 92.730 | 20.634 | 152.849 | 1.00 | 30.31 |
| ATOM | 5072 | O | LEU | D | 349 | 91.506 | 20.791 | 152.828 | 1.00 | 29.25 |
| ATOM | 5073 | N | SER | D | 350 | 93.297 | 19.470 | 153.151 | 1.00 | 29.32 |

TABLE 1-continued

FGFR1 D2–D3 Complexed with FGF2

| ATOM | 5074 | CA | SER | D | 350 | 92.513 | 18.290 | 153.495 | 1.00 | 29.59 |
|---|---|---|---|---|---|---|---|---|---|---|
| ATOM | 5075 | CB | SER | D | 350 | 92.461 | 17.312 | 152.325 | 1.00 | 28.63 |
| ATOM | 5076 | OG | SER | D | 350 | 91.629 | 17.795 | 151.287 | 1.00 | 32.28 |
| ATOM | 5077 | C | SER | D | 350 | 93.176 | 17.604 | 154.664 | 1.00 | 30.54 |
| ATOM | 5078 | O | SER | D | 350 | 94.345 | 17.856 | 154.943 | 1.00 | 30.95 |
| ATOM | 5079 | N | HIS | D | 351 | 92.430 | 16.740 | 155.346 | 1.00 | 31.83 |
| ATOM | 5080 | CA | HIS | D | 351 | 92.967 | 15.996 | 156.479 | 1.00 | 32.23 |
| ATOM | 5081 | CB | HIS | D | 351 | 93.269 | 16.930 | 157.642 | 1.00 | 35.19 |
| ATOM | 5082 | CG | HIS | D | 351 | 92.048 | 17.560 | 158.228 | 1.00 | 39.93 |
| ATOM | 5083 | CD2 | HIS | D | 351 | 91.287 | 17.204 | 159.290 | 1.00 | 40.95 |
| ATOM | 5084 | ND1 | HIS | D | 351 | 91.417 | 18.640 | 157.648 | 1.00 | 40.27 |
| ATOM | 5085 | CE1 | HIS | D | 351 | 90.319 | 18.919 | 158.326 | 1.00 | 41.63 |
| ATOM | 5086 | NE2 | HIS | D | 351 | 90.217 | 18.061 | 159.326 | 1.00 | 41.54 |
| ATOM | 5087 | C | HIS | D | 351 | 91.985 | 14.941 | 156.962 | 1.00 | 31.71 |
| ATOM | 5088 | O | HIS | D | 351 | 90.783 | 15.184 | 156.998 | 1.00 | 31.07 |
| ATOM | 5089 | N | HIS | D | 352 | 92.513 | 13.770 | 157.317 | 1.00 | 31.75 |
| ATOM | 5090 | CA | HIS | D | 352 | 91.722 | 12.661 | 157.851 | 1.00 | 30.61 |
| ATOM | 5091 | CB | HIS | D | 352 | 91.844 | 11.392 | 156.999 | 1.00 | 30.06 |
| ATOM | 5092 | CG | HIS | D | 352 | 91.018 | 11.396 | 155.750 | 1.00 | 30.96 |
| ATOM | 5093 | CD2 | HIS | D | 352 | 90.243 | 12.353 | 155.187 | 1.00 | 32.11 |
| ATOM | 5094 | ND1 | HIS | D | 352 | 90.957 | 10.310 | 154.901 | 1.00 | 30.90 |
| ATOM | 5095 | CE1 | HIS | D | 352 | 90.183 | 10.599 | 153.871 | 1.00 | 30.38 |
| ATOM | 5096 | NE2 | HIS | D | 352 | 89.737 | 11.833 | 154.019 | 1.00 | 30.27 |
| ATOM | 5097 | C | HIS | D | 352 | 92.323 | 12.357 | 159.216 | 1.00 | 31.42 |
| ATOM | 5098 | O | HIS | D | 352 | 93.540 | 12.467 | 159.400 | 1.00 | 31.56 |
| ATOM | 5099 | N | SER | D | 353 | 91.484 | 11.967 | 160.168 | 1.00 | 31.10 |
| ATOM | 5100 | CA | SER | D | 353 | 91.966 | 11.652 | 161.502 | 1.00 | 31.28 |
| ATOM | 5101 | CB | SER | D | 353 | 91.305 | 12.575 | 162.521 | 1.00 | 31.16 |
| ATOM | 5102 | OG | SER | D | 353 | 91.417 | 13.927 | 162.115 | 1.00 | 32.98 |
| ATOM | 5103 | C | SER | D | 353 | 91.639 | 10.211 | 161.839 | 1.00 | 31.23 |
| ATOM | 5104 | O | SER | D | 353 | 90.733 | 9.630 | 161.257 | 1.00 | 33.53 |
| ATOM | 5105 | N | ALA | D | 354 | 92.390 | 9.634 | 162.769 | 1.00 | 31.01 |
| ATOM | 5106 | CA | ALA | D | 354 | 92.170 | 8.262 | 163.203 | 1.00 | 30.47 |
| ATOM | 5107 | CB | ALA | D | 354 | 93.095 | 7.313 | 162.466 | 1.00 | 28.96 |
| ATOM | 5108 | C | ALA | D | 354 | 92.435 | 8.197 | 164.696 | 1.00 | 31.37 |
| ATOM | 5109 | O | ALA | D | 354 | 93.118 | 9.058 | 165.260 | 1.00 | 29.49 |
| ATOM | 5110 | N | TRP | D | 355 | 91.901 | 7.167 | 165.337 | 1.00 | 33.61 |
| ATOM | 5111 | CA | TRP | D | 355 | 92.080 | 7.025 | 166.765 | 1.00 | 34.51 |
| ATOM | 5112 | CB | TRP | D | 355 | 90.720 | 6.974 | 167.453 | 1.00 | 36.20 |
| ATOM | 5113 | CG | TRP | D | 355 | 90.724 | 7.824 | 168.658 | 1.00 | 42.37 |
| ATOM | 5114 | CD2 | TRP | D | 355 | 90.095 | 9.102 | 168.793 | 1.00 | 44.32 |
| ATOM | 5115 | CE2 | TRP | D | 355 | 90.483 | 9.626 | 170.055 | 1.00 | 44.27 |
| ATOM | 5116 | CE3 | TRP | D | 355 | 89.247 | 9.858 | 167.972 | 1.00 | 43.24 |
| ATOM | 5117 | CD1 | TRP | D | 355 | 91.439 | 7.619 | 169.815 | 1.00 | 44.23 |
| ATOM | 5118 | NE1 | TRP | D | 355 | 91.300 | 8.704 | 170.656 | 1.00 | 45.49 |
| ATOM | 5119 | CZ2 | TRP | D | 355 | 90.049 | 10.871 | 170.505 | 1.00 | 43.28 |
| ATOM | 5120 | CZ3 | TRP | D | 355 | 88.818 | 11.093 | 168.423 | 1.00 | 43.34 |
| ATOM | 5121 | CH2 | TRP | D | 355 | 89.221 | 11.589 | 169.679 | 1.00 | 43.92 |
| ATOM | 5122 | C | TRP | D | 355 | 92.887 | 5.812 | 167.178 | 1.00 | 33.47 |
| ATOM | 5123 | O | TRP | D | 355 | 92.590 | 4.693 | 166.765 | 1.00 | 33.00 |
| ATOM | 5124 | N | LEU | D | 356 | 93.908 | 6.044 | 167.998 | 1.00 | 32.81 |
| ATOM | 5125 | CA | LEU | D | 356 | 94.728 | 4.955 | 168.515 | 1.00 | 33.21 |
| ATOM | 5126 | CB | LEU | D | 356 | 96.194 | 5.347 | 168.594 | 1.00 | 34.73 |
| ATOM | 5127 | CG | LEU | D | 356 | 97.143 | 4.144 | 168.566 | 1.00 | 35.38 |
| ATOM | 5128 | CD1 | LEU | D | 356 | 98.543 | 4.609 | 168.923 | 1.00 | 35.96 |
| ATOM | 5129 | CD2 | LEU | D | 356 | 96.680 | 3.065 | 169.521 | 1.00 | 35.85 |
| ATOM | 5130 | C | LEU | D | 356 | 94.263 | 4.609 | 169.925 | 1.00 | 33.74 |
| ATOM | 5131 | O | LEU | D | 356 | 94.379 | 5.412 | 170.847 | 1.00 | 32.37 |
| ATOM | 5132 | N | THR | D | 357 | 93.735 | 3.404 | 170.081 | 1.00 | 35.42 |
| ATOM | 5133 | CA | THR | D | 357 | 93.265 | 2.931 | 171.375 | 1.00 | 37.14 |
| ATOM | 5134 | CB | THR | D | 357 | 91.875 | 2.264 | 171.250 | 1.00 | 37.60 |
| ATOM | 5135 | OG1 | THR | D | 357 | 90.965 | 3.173 | 170.610 | 1.00 | 36.16 |
| ATOM | 5136 | CG2 | THR | D | 357 | 91.342 | 1.876 | 172.632 | 1.00 | 34.23 |
| ATOM | 5137 | C | THR | D | 357 | 94.269 | 1.898 | 171.870 | 1.00 | 37.63 |
| ATOM | 5138 | O | THR | D | 357 | 94.509 | 0.900 | 171.196 | 1.00 | 38.36 |
| ATOM | 5139 | N | VAL | D | 358 | 94.857 | 2.138 | 173.039 | 1.00 | 38.60 |
| ATOM | 5140 | CA | VAL | D | 358 | 95.849 | 1.218 | 173.602 | 1.00 | 40.52 |
| ATOM | 5141 | CB | VAL | D | 358 | 97.132 | 1.996 | 174.025 | 1.00 | 40.83 |
| ATOM | 5142 | CG1 | VAL | D | 358 | 98.160 | 1.048 | 174.606 | 1.00 | 40.51 |
| ATOM | 5143 | CG2 | VAL | D | 358 | 97.708 | 2.739 | 172.828 | 1.00 | 39.34 |
| ATOM | 5144 | C | VAL | D | 358 | 95.308 | 0.444 | 174.814 | 1.00 | 40.94 |
| ATOM | 5145 | O | VAL | D | 358 | 94.574 | 0.998 | 175.640 | 1.00 | 40.87 |
| ATOM | 5146 | N | LEU | D | 359 | 95.673 | 0.834 | 174.909 | 1.00 | 40.73 |
| ATOM | 5147 | CA | LEU | D | 359 | 95.243 | 1.694 | 176.015 | 1.00 | 40.07 |
| ATOM | 5148 | CB | LEU | D | 359 | 94.083 | 2.584 | 175.567 | 1.00 | 37.19 |
| ATOM | 5149 | CG | LEU | D | 359 | 92.900 | 1.926 | 174.858 | 1.00 | 37.09 |
| ATOM | 5150 | CD1 | LEU | D | 359 | 91.866 | 2.983 | 174.499 | 1.00 | 34.94 |

TABLE 1-continued

FGFR1 D2–D3 Complexed with FGF2

| ATOM | 5151 | CD2 | LEU | D | 359 | 92.291 | 0.851 | 175.739 | 1.00 | 36.94 |
|---|---|---|---|---|---|---|---|---|---|---|
| ATOM | 5152 | C | LEU | D | 359 | 96.405 | 2.583 | 176.490 | 1.00 | 41.50 |
| ATOM | 5153 | O | LEU | D | 359 | 96.472 | 2.906 | 177.705 | 1.00 | 43.25 |
| HETATM | 5154 | S | SO4 | | 1 | 101.860 | 26.306 | 120.782 | 1.00 | 67.75 |
| HETATM | 5155 | O1 | SO4 | | 1 | 101.069 | 25.832 | 121.933 | 1.00 | 68.48 |
| HETATM | 5156 | O2 | SO4 | | 1 | 101.467 | 25.556 | 119.574 | 1.00 | 67.57 |
| HETATM | 5157 | O3 | SO4 | | 1 | 101.618 | 27.745 | 120.575 | 1.00 | 69.30 |
| HETATM | 5158 | O4 | SO4 | | 1 | 103.293 | 26.096 | 121.052 | 1.00 | 68.39 |
| HETATM | 5159 | S | SO4 | | 2 | 112.071 | 33.384 | 123.815 | 1.00 | 66.75 |
| HETATM | 5160 | O1 | SO4 | | 2 | 113.069 | 34.455 | 123.623 | 1.00 | 67.50 |
| HETATM | 5161 | O2 | SO4 | | 2 | 112.663 | 32.092 | 123.418 | 1.00 | 66.52 |
| HETATM | 5162 | O3 | SO4 | | 2 | 111.676 | 33.341 | 125.238 | 1.00 | 65.71 |
| HETATM | 5163 | O4 | SO4 | | 2 | 110.883 | 33.652 | 122.975 | 1.00 | 66.55 |
| HETATM | 5164 | S | SO4 | | 3 | 77.189 | 23.441 | 106.691 | 1.00 | 83.31 |
| HETATM | 5165 | O1 | SO4 | | 3 | 78.088 | 22.827 | 105.694 | 1.00 | 84.63 |
| HETATM | 5166 | O2 | SO4 | | 3 | 77.908 | 23.560 | 107.969 | 1.00 | 84.80 |
| HETATM | 5167 | O3 | SO4 | | 3 | 76.762 | 24.778 | 106.237 | 1.00 | 82.90 |
| HETATM | 5168 | O4 | SO4 | | 3 | 76.003 | 22.590 | 106.876 | 1.00 | 83.82 |
| HETATM | 5169 | S | SO4 | | 4 | 85.406 | 27.736 | 115.455 | 1.00 | 90.59 |
| HETATM | 5170 | O1 | SO4 | | 4 | 86.326 | 28.866 | 115.704 | 1.00 | 89.09 |
| HETATM | 5171 | O2 | SO4 | | 4 | 86.162 | 26.578 | 114.945 | 1.00 | 89.08 |
| HETATM | 5172 | O3 | SO4 | | 4 | 84.725 | 27.358 | 116.711 | 1.00 | 89.23 |
| HETATM | 5173 | O4 | SO4 | | 4 | 84.404 | 28.146 | 114.455 | 1.00 | 89.64 |

TABLE 2

FGFR1 D2–D3 Complexed with FGF1

| ATOM | 1 | CB | TYR | 8 | −6.051 | 51.528 | 11.919 | 1.00 | 28.44 |
|---|---|---|---|---|---|---|---|---|---|
| ATOM | 2 | CG | TYR | 8 | −6.818 | 50.221 | 12.093 | 1.00 | 27.45 |
| ATOM | 3 | CD1 | TYR | 8 | −8.094 | 50.053 | 11.541 | 1.00 | 24.63 |
| ATOM | 4 | CE1 | TYR | 8 | −8.834 | 48.901 | 11.773 | 1.00 | 20.69 |
| ATOM | 5 | CD2 | TYR | 8 | −6.302 | 49.185 | 12.876 | 1.00 | 25.25 |
| ATOM | 6 | CE2 | TYR | 8 | −7.038 | 48.029 | 13.114 | 1.00 | 22.59 |
| ATOM | 7 | CZ | TYR | 8 | −8.303 | 47.896 | 12.564 | 1.00 | 22.85 |
| ATOM | 8 | OH | TYR | 8 | −9.040 | 46.769 | 12.836 | 1.00 | 21.66 |
| ATOM | 9 | C | TYR | 8 | −8.095 | 52.815 | 12.656 | 1.00 | 32.48 |
| ATOM | 10 | O | TYR | 8 | −8.624 | 53.046 | 11.564 | 1.00 | 33.42 |
| ATOM | 11 | N | TYR | 8 | −6.151 | 52.546 | 14.217 | 1.00 | 28.27 |
| ATOM | 12 | CA | TYR | 8 | −6.567 | 52.705 | 12.782 | 1.00 | 31.41 |
| ATOM | 13 | N | LYS | 9 | −8.801 | 52.636 | 13.768 | 1.00 | 31.66 |
| ATOM | 14 | CA | LYS | 9 | −10.252 | 52.748 | 13.756 | 1.00 | 32.17 |
| ATOM | 15 | CB | LYS | 9 | −10.885 | 51.750 | 14.723 | 1.00 | 32.91 |
| ATOM | 16 | CG | LYS | 9 | −10.816 | 50.308 | 14.230 | 1.00 | 36.66 |
| ATOM | 17 | CD | LYS | 9 | −11.854 | 49.432 | 14.901 | 1.00 | 34.19 |
| ATOM | 18 | CE | LYS | 9 | −12.006 | 48.114 | 14.163 | 1.00 | 36.17 |
| ATOM | 19 | NZ | LYS | 9 | −13.244 | 47.392 | 14.591 | 1.00 | 36.62 |
| ATOM | 20 | C | LYS | 9 | −10.680 | 54.160 | 14.127 | 1.00 | 34.00 |
| ATOM | 21 | O | LYS | 9 | −11.772 | 54.598 | 13.773 | 1.00 | 37.26 |
| ATOM | 22 | N | LYS | 10 | −9.808 | 54.872 | 14.831 | 1.00 | 32.38 |
| ATOM | 23 | CA | LYS | 10 | −10.082 | 56.238 | 15.254 | 1.00 | 30.25 |
| ATOM | 24 | CB | LYS | 10 | −9.059 | 56.650 | 16.324 | 1.00 | 29.82 |
| ATOM | 25 | C | LYS | 10 | −10.044 | 57.227 | 14.079 | 1.00 | 28.52 |
| ATOM | 26 | O | LYS | 10 | −9.275 | 57.051 | 13.131 | 1.00 | 27.07 |
| ATOM | 27 | N | PRO | 11 | −10.880 | 58.281 | 14.129 | 1.00 | 27.69 |
| ATOM | 28 | CD | PRO | 11 | −11.964 | 58.562 | 15.084 | 1.00 | 26.12 |
| ATOM | 29 | CA | PRO | 11 | −10.885 | 59.261 | 13.035 | 1.00 | 27.89 |
| ATOM | 30 | GB | PRO | 11 | −12.094 | 60.145 | 13.357 | 1.00 | 26.47 |
| ATOM | 31 | CG | PRO | 11 | −12.967 | 59.261 | 14.206 | 1.00 | 27.98 |
| ATOM | 32 | C | PRO | 11 | −9.579 | 60.041 | 13.061 | 1.00 | 28.01 |
| ATOM | 33 | O | PRO | 11 | −9.038 | 60.303 | 14.126 | 1.00 | 31.43 |
| ATOM | 34 | N | LYS | 12 | −9.071 | 60.412 | 11.896 | 1.00 | 27.87 |
| ATOM | 35 | CA | LYS | 12 | −7.825 | 61.159 | 11.837 | 1.00 | 27.45 |
| ATOM | 36 | CB | LYS | 12 | −6.745 | 60.357 | 11.111 | 1.00 | 26.62 |
| ATOM | 37 | CG | LYS | 12 | −6.764 | 58.877 | 11.359 | 1.00 | 33.32 |
| ATOM | 38 | CD | LYS | 12 | −5.765 | 58.177 | 10.429 | 1.00 | 39.88 |
| ATOM | 39 | CE | LYS | 12 | −5.737 | 56.658 | 10.631 | 1.00 | 42.08 |
| ATOM | 40 | NZ | LYS | 12 | −4.753 | 56.011 | 9.717 | 1.00 | 45.02 |
| ATOM | 41 | C | LYS | 12 | −8.047 | 62.440 | 11.050 | 1.00 | 26.96 |
| ATOM | 42 | O | LYS | 12 | −9.171 | 62.785 | 10.684 | 1.00 | 27.06 |
| ATOM | 43 | N | LED | 13 | −6.950 | 63.137 | 10.797 | 1.00 | 22.89 |
| ATOM | 44 | CA | LED | 13 | −6.975 | 64.342 | 10.008 | 1.00 | 20.98 |
| ATOM | 45 | CB | LED | 13 | −6.530 | 65.547 | 10.828 | 1.00 | 18.90 |
| ATOM | 46 | CG | LED | 13 | −6.972 | 65.613 | 12.286 | 1.00 | 19.21 |

TABLE 2-continued

FGFR1 D2–D3 Complexed with FGF1

| ATOM | 47 | CD1 | LED | 13 | −6.081 | 66.620 | 13.034 | 1.00 | 17.37 |
|---|---|---|---|---|---|---|---|---|---|
| ATOM | 48 | CD2 | LED | 13 | −8.448 | 65.957 | 12.368 | 1.00 | 11.37 |
| ATOM | 49 | C | LEU | 13 | −5.916 | 64.030 | 8.962 | 1.00 | 23.04 |
| ATOM | 50 | O | LEU | 13 | −4.903 | 63.388 | 9.272 | 1.00 | 20.71 |
| ATOM | 51 | N | LED | 14 | −6.155 | 64.453 | 7.723 | 1.00 | 24.54 |
| ATOM | 52 | CA | LED | 14 | −5.192 | 64.230 | 6.657 | 1.00 | 25.10 |
| ATOM | 53 | CB | LEU | 14 | −5.877 | 63.676 | 5.395 | 1.00 | 26.61 |
| ATOM | 54 | CG | LED | 14 | −6.531 | 62.285 | 5.454 | 1.00 | 26.43 |
| ATOM | 55 | CD1 | LED | 14 | −6.795 | 61.800 | 4.037 | 1.00 | 26.12 |
| ATOM | 56 | CD2 | LED | 14 | −5.621 | 61.289 | 6.157 | 1.00 | 26.35 |
| ATOM | 57 | CB | LEU | 14 | −4.532 | 65.578 | 6.382 | 1.00 | 24.80 |
| ATOM | 58 | O | LEU | 14 | −5.057 | 66.414 | 5.650 | 1.00 | 29.43 |
| ATOM | 59 | N | TYR | 15 | −3.383 | 65.778 | 7.011 | 1.00 | 20.82 |
| ATOM | 60 | CA | TYR | 15 | −2.610 | 66.994 | 6.900 | 1.00 | 16.34 |
| ATOM | 61 | GB | TYR | 15 | −1.619 | 67.035 | 8.076 | 1.00 | 16.55 |
| ATOM | 62 | CG | TYR | 15 | −0.514 | 68.069 | 7.993 | 1.00 | 15.27 |
| ATOM | 63 | CD1 | TYR | 15 | 0.667 | 67.811 | 7.296 | 1.00 | 11.64 |
| ATOM | 64 | CE1 | TYR | 15 | 1.680 | 68.768 | 7.213 | 1.00 | 12.97 |
| ATOM | 65 | CD2 | TYR | 15 | −0.656 | 69.314 | 8.610 | 1.00 | 18.36 |
| ATOM | 66 | CE2 | TYR | 15 | 0.351 | 70.281 | 8.538 | 1.00 | 17.26 |
| ATOM | 67 | CZ | TYR | 15 | 1.513 | 70.005 | 7.838 | 1.00 | 16.66 |
| ATOM | 68 | OH | TYR | 15 | 2.497 | 70.973 | 7.754 | 1.00 | 17.84 |
| ATOM | 69 | C | TYR | 15 | −1.886 | 66.980 | 5.571 | 1.00 | 16.68 |
| ATOM | 70 | O | TYR | 15 | −1.275 | 65.984 | 5.215 | 1.00 | 16.87 |
| ATOM | 71 | N | CYS | 16 | −1.970 | 68.074 | 4.824 | 1.00 | 17.57 |
| ATOM | 72 | CA | CYS | 16 | −1.277 | 68.158 | 3.546 | 1.00 | 21.60 |
| ATOM | 73 | GB | CYS | 16 | −2.156 | 68.814 | 2.491 | 1.00 | 21.60 |
| ATOM | 74 | SG | CYS | 16 | −1.350 | 68.884 | 0.878 | 1.00 | 24.76 |
| ATOM | 75 | C | CYS | 16 | −0.019 | 68.991 | 3.739 | 1.00 | 24.96 |
| ATOM | 76 | O | CYS | 16 | −0.082 | 70.116 | 4.239 | 1.00 | 24.56 |
| ATOM | 77 | N | SER | 17 | 1.121 | 68.454 | 3.318 | 1.00 | 27.88 |
| ATOM | 78 | CA | SER | 17 | 2.396 | 69.146 | 3.507 | 1.00 | 32.13 |
| ATOM | 79 | GB | SER | 17 | 3.537 | 68.134 | 3.420 | 1.00 | 31.38 |
| ATOM | 80 | OG | SER | 17 | 3.423 | 67.359 | 2.243 | 1.00 | 37.53 |
| ATOM | 81 | C | SER | 17 | 2.697 | 70.337 | 2.596 | 1.00 | 33.49 |
| ATOM | 82 | O | SER | 17 | 3.683 | 71.055 | 2.805 | 1.00 | 34.92 |
| ATOM | 83 | N | ASN | 18 | 1.847 | 70.563 | 1.601 | 1.00 | 34.25 |
| ATOM | 84 | CA | ASN | 18 | 2.057 | 71.665 | 0.670 | 1.00 | 33.45 |
| ATOM | 85 | GB | ASN | 18 | 1.176 | 71.458 | −0.564 | 1.00 | 35.74 |
| ATOM | 86 | CG | ASN | 18 | 1.612 | 72.304 | −1.742 | 1.00 | 37.98 |
| ATOM | 87 | OD1 | ASN | 18 | 2.767 | 72.247 | −2.175 | 1.00 | 39.41 |
| ATOM | 88 | ND2 | ASN | 18 | 0.685 | 73.092 | −2.273 | 1.00 | 39.81 |
| ATOM | 89 | C | ASN | 18 | 1.814 | 73.057 | 1.285 | 1.00 | 31.98 |
| ATOM | 90 | O | ASN | 18 | 2.399 | 74.035 | 0.843 | 1.00 | 34.60 |
| ATOM | 91 | N | GLY | 19 | 0.971 | 73.150 | 2.306 | 1.00 | 29.15 |
| ATOM | 92 | CA | GLY | 19 | 0.714 | 74.441 | 2.921 | 1.00 | 25.91 |
| ATOM | 93 | C | GLY | 19 | 0.290 | 74.337 | 4.375 | 1.00 | 24.97 |
| ATOM | 94 | O | GLY | 19 | −0.056 | 75.331 | 5.025 | 1.00 | 20.29 |
| ATOM | 95 | N | GLY | 20 | 0.314 | 73.113 | 4.886 | 1.00 | 26.22 |
| ATOM | 96 | CA | GLY | 20 | −0.066 | 72.881 | 6.264 | 1.00 | 28.13 |
| ATOM | 97 | C | GLY | 20 | −1.565 | 72.825 | 6.474 | 1.00 | 29.03 |
| ATOM | 98 | O | GLY | 20 | −2.030 | 72.932 | 7.614 | 1.00 | 30.16 |
| ATOM | 99 | N | HIS | 21 | −2.320 | 72.643 | 5.388 | 1.00 | 28.28 |
| ATOM | 100 | CA | HIS | 21 | −3.783 | 72.580 | 5.463 | 1.00 | 26.97 |
| ATOM | 101 | GB | HIS | 21 | −4.428 | 73.093 | 4.167 | 1.00 | 26.00 |
| ATOM | 102 | CG | HIS | 21 | −4.145 | 74.534 | 3.875 | 1.00 | 27.23 |
| ATOM | 103 | CD2 | HIS | 21 | −4.774 | 75.664 | 4.281 | 1.00 | 26.36 |
| ATOM | 104 | ND1 | HIS | 21 | −3.095 | 74.941 | 3.080 | 1.00 | 24.16 |
| ATOM | 105 | CE1 | HIS | 21 | −3.090 | 76.261 | 3.005 | 1.00 | 26.23 |
| ATOM | 106 | NE2 | HIS | 21 | −4.098 | 76.724 | 3.725 | 1.00 | 28.72 |
| ATOM | 107 | C | HIS | 21 | −4.326 | 71.188 | 5.740 | 1.00 | 26.11 |
| ATOM | 108 | O | HIS | 21 | −3.840 | 70.195 | 5.198 | 1.00 | 25.92 |
| ATOM | 109 | N | PHE | 22 | −5.343 | 71.130 | 6.592 | 1.00 | 26.87 |
| ATOM | 110 | CA | PHE | 22 | −5.998 | 69.872 | 6.934 | 1.00 | 26.99 |
| ATOM | 111 | CB | PHE | 22 | −6.611 | 69.925 | 8.339 | 1.00 | 27.89 |
| ATOM | 112 | CG | PHE | 22 | −5.597 | 70.021 | 9.441 | 1.00 | 34.47 |
| ATOM | 113 | CD1 | PHE | 22 | −5.700 | 69.214 | 10.567 | 1.00 | 35.19 |
| ATOM | 114 | CD2 | PHE | 22 | −4.530 | 70.917 | 9.353 | 1.00 | 37.94 |
| ATOM | 115 | GE1 | PHE | 22 | −4.764 | 69.296 | 11.582 | 1.00 | 35.09 |
| ATOM | 116 | CE2 | PHE | 22 | −3.590 | 71.005 | 10.366 | 1.00 | 36.95 |
| ATOM | 117 | CZ | PHE | 22 | −3.708 | 70.191 | 11.482 | 1.00 | 36.26 |
| ATOM | 118 | C | PHE | 22 | −7.114 | 69.645 | 5.929 | 1.00 | 26.43 |
| ATOM | 119 | O | PHE | 22 | −7.964 | 70.519 | 5.728 | 1.00 | 24.41 |
| ATOM | 120 | N | LEU | 23 | −7.116 | 68.472 | 5.301 | 1.00 | 24.90 |
| ATOM | 121 | CA | LEU | 23 | −8.148 | 68.163 | 4.330 | 1.00 | 21.79 |
| ATOM | 122 | GB | LEU | 23 | −7.981 | 66.731 | 3.829 | 1.00 | 20.26 |
| ATOM | 123 | CG | LEU | 23 | −8.783 | 66.381 | 2.571 | 1.00 | 22.41 |

TABLE 2-continued

FGFR1 D2–D3 Complexed with FGF1

| ATOM | 124 | GD1 | LEU | 23 | −8.610 | 67.473 | 1.509 | 1.00 | 21.81 |
|---|---|---|---|---|---|---|---|---|---|
| ATOM | 125 | CD2 | LEU | 23 | −8.323 | 65.032 | 2.035 | 1.00 | 20.82 |
| ATOM | 126 | C | LEU | 23 | −9.507 | 68.365 | 4.999 | 1.00 | 20.18 |
| ATOM | 127 | O | LEU | 23 | −9.754 | 67.854 | 6.089 | 1.00 | 19.53 |
| ATOM | 128 | N | ARG | 24 | −10.371 | 69.137 | 4.341 | 1.00 | 21.33 |
| ATOM | 129 | CA | ARG | 24 | −11.710 | 69.460 | 4.848 | 1.00 | 21.46 |
| ATOM | 130 | GB | ARG | 24 | −11.778 | 70.954 | 5.211 | 1.00 | 21.37 |
| ATOM | 131 | CG | ARG | 24 | −13.175 | 71.469 | 5.476 | 1.00 | 18.70 |
| ATOM | 132 | CD | ARG | 24 | −13.176 | 72.825 | 6.148 | 1.00 | 19.39 |
| ATOM | 133 | NE | ARG | 24 | −12.566 | 73.877 | 5.331 | 1.00 | 21.99 |
| ATOM | 134 | GZ | ARG | 24 | −12.638 | 75.179 | 5.610 | 1.00 | 18.80 |
| ATOM | 135 | NH1 | ARG | 24 | −13.296 | 75.601 | 6.682 | 1.00 | 14.56 |
| ATOM | 136 | NH2 | ARG | 24 | −12.043 | 76.063 | 4.822 | 1.00 | 18.72 |
| ATOM | 137 | C | ARG | 24 | −12.835 | 69.142 | 3.871 | 1.00 | 21.12 |
| ATOM | 138 | O | ARG | 24 | −12.712 | 69.368 | 2.669 | 1.00 | 24.62 |
| ATOM | 139 | N | ILE | 25 | −13.937 | 68.625 | 4.390 | 1.00 | 20.99 |
| ATOM | 140 | GA | ILE | 25 | −15.091 | 68.314 | 3.548 | 1.00 | 24.24 |
| ATOM | 141 | GB | ILE | 25 | −15.446 | 66.799 | 3.576 | 1.00 | 25.03 |
| ATOM | 142 | CG2 | ILE | 25 | −16.653 | 66.530 | 2.679 | 1.00 | 24.51 |
| ATOM | 143 | CG1 | ILE | 25 | −14.253 | 65.962 | 3.103 | 1.00 | 23.59 |
| ATOM | 144 | CD1 | ILE | 25 | −14.524 | 64.470 | 3.093 | 1.00 | 20.41 |
| ATOM | 145 | C | ILE | 25 | −16.298 | 69.105 | 4.059 | 1.00 | 25.48 |
| ATOM | 146 | O | ILE | 25 | −17.031 | 68.632 | 4.935 | 1.00 | 27.47 |
| ATOM | 147 | N | LEU | 26 | −16.490 | 70.308 | 3.515 | 1.00 | 25.58 |
| ATOM | 148 | CA | LEU | 26 | −17.594 | 71.179 | 3.913 | 1.00 | 26.62 |
| ATOM | 149 | GB | LEU | 26 | −17.450 | 72.535 | 3.231 | 1.00 | 27.43 |
| ATOM | 150 | CG | LEU | 26 | −16.176 | 73.273 | 3.645 | 1.00 | 27.65 |
| ATOM | 151 | CD1 | LEU | 26 | −15.932 | 74.464 | 2.718 | 1.00 | 26.42 |
| ATOM | 152 | GD2 | LEU | 26 | −16.302 | 73.703 | 5.105 | 1.00 | 21.68 |
| ATOM | 153 | C | LEU | 26 | −18.935 | 70.551 | 3.563 | 1.00 | 27.42 |
| ATOM | 154 | O | LEU | 26 | −19.108 | 70.007 | 2.477 | 1.00 | 27.49 |
| ATOM | 155 | N | PRO | 27 | −19.910 | 70.640 | 4.489 | 1.00 | 27.87 |
| ATOM | 156 | GD | PRO | 27 | −19.797 | 71.543 | 5.639 | 1.00 | 26.97 |
| ATOM | 157 | CA | PRO | 27 | −21.274 | 70.095 | 4.389 | 1.00 | 28.57 |
| ATOM | 158 | GB | PRO | 27 | −21.965 | 70.683 | 5.622 | 1.00 | 27.09 |
| ATOM | 159 | CG | PRO | 27 | −21.225 | 71.945 | 5.862 | 1.00 | 27.51 |
| ATOM | 160 | C | PRO | 27 | −22.067 | 70.316 | 3.097 | 1.00 | 29.49 |
| ATOM | 161 | O | PRO | 27 | −23.089 | 69.674 | 2.871 | 1.00 | 31.43 |
| ATOM | 162 | N | ASP | 28 | −21.584 | 71.198 | 2.242 | 1.00 | 29.56 |
| ATOM | 163 | CA | ASP | 28 | −22.239 | 71.494 | 0.977 | 1.00 | 31.81 |
| ATOM | 164 | GB | ASP | 28 | −22.107 | 72.980 | 0.732 | 1.00 | 35.00 |
| ATOM | 165 | CG | ASP | 28 | −20.752 | 73.492 | 1.163 | 1.00 | 39.97 |
| ATOM | 166 | OD1 | ASP | 28 | −19.774 | 73.299 | 0.398 | 1.00 | 38.80 |
| ATOM | 167 | OD2 | ASP | 28 | −20.663 | 74.049 | 2.288 | 1.00 | 40.66 |
| ATOM | 168 | C | ASP | 28 | −21.578 | 70.720 | −0.165 | 1.00 | 32.77 |
| ATOM | 169 | O | ASP | 28 | −21.946 | 70.874 | −1.331 | 1.00 | 32.13 |
| ATOM | 170 | N | GLY | 29 | −20.592 | 69.897 | 0.174 | 1.00 | 32.44 |
| ATOM | 171 | GA | GLY | 29 | −19.894 | 69.126 | −0.834 | 1.00 | 32.39 |
| ATOM | 172 | C | GLY | 29 | −18.548 | 69.728 | −1.199 | 1.00 | 34.62 |
| ATOM | 173 | O | GLY | 29 | −17.768 | 69.108 | −1.923 | 1.00 | 35.14 |
| ATOM | 174 | N | THR | 30 | −18.264 | 70.931 | −0.700 | 1.00 | 34.26 |
| ATOM | 175 | GA | THR | 30 | −16.997 | 71.596 | −1.001 | 1.00 | 34.72 |
| ATOM | 176 | GB | THR | 30 | −17.054 | 73.104 | −0.641 | 1.00 | 36.00 |
| ATOM | 177 | OG1 | THR | 30 | −17.726 | 73.813 | −1.688 | 1.00 | 35.48 |
| ATOM | 178 | CG2 | THR | 30 | −15.643 | 73.684 | −0.453 | 1.00 | 35.94 |
| ATOM | 179 | C | THR | 30 | −15.803 | 70.971 | −0.289 | 1.00 | 34.24 |
| ATOM | 180 | O | THR | 30 | −15.786 | 70.875 | 0.939 | 1.00 | 36.02 |
| ATOM | 181 | N | VAL | 31 | −14.807 | 70.562 | −1.075 | 1.00 | 33.03 |
| ATOM | 182 | CA | VAL | 31 | −13.581 | 69.946 | −0.561 | 1.00 | 31.16 |
| ATOM | 183 | GB | VAL | 31 | −13.221 | 68.679 | −1.375 | 1.00 | 30.16 |
| ATOM | 184 | CG1 | VAL | 31 | −11.803 | 68.227 | −1.054 | 1.00 | 27.58 |
| ATOM | 185 | CG2 | VAL | 31 | −14.222 | 67.567 | −1.063 | 1.00 | 24.85 |
| ATOM | 186 | C | VAL | 31 | −12.426 | 70.945 | −0.618 | 1.00 | 30.88 |
| ATOM | 187 | O | VAL | 31 | −12.103 | 71.496 | −1.675 | 1.00 | 30.91 |
| ATOM | 188 | N | ASP | 32 | −11.797 | 71.171 | 0.526 | 1.00 | 30.08 |
| ATOM | 189 | CA | ASP | 32 | −10.710 | 72.143 | 0.603 | 1.00 | 29.27 |
| ATOM | 190 | GB | ASP | 32 | −11.295 | 73.551 | 0.712 | 1.00 | 26.28 |
| ATOM | 191 | CG | ASP | 32 | −11.861 | 73.839 | 2.100 | 1.00 | 24.69 |
| ATOM | 192 | OD1 | ASP | 32 | −12.213 | 72.887 | 2.838 | 1.00 | 24.75 |
| ATOM | 193 | OD2 | ASP | 32 | −11.960 | 75.022 | 2.460 | 1.00 | 26.59 |
| ATOM | 194 | C | ASP | 32 | −9.855 | 71.889 | 1.834 | 1.00 | 28.84 |
| ATOM | 195 | O | ASP | 32 | −9.974 | 70.850 | 2.484 | 1.00 | 25.70 |
| ATOM | 196 | N | GLY | 33 | −9.013 | 72.870 | 2.158 | 1.00 | 29.42 |
| ATOM | 197 | CA | GLY | 33 | −8.148 | 72.764 | 3.317 | 1.00 | 28.55 |
| ATOM | 198 | C | GLY | 33 | −8.264 | 73.951 | 4.252 | 1.00 | 26.20 |
| ATOM | 199 | O | GLY | 33 | −8.721 | 75.017 | 3.861 | 1.00 | 25.20 |
| ATOM | 200 | N | THR | 34 | −7.853 | 73.749 | 5.499 | 1.00 | 27.35 |

TABLE 2-continued

| FGFR1 D2–D3 Complexed with FGF1 | | | | | | | | |
|---|---|---|---|---|---|---|---|---|
| ATOM | 201 | CA | THR | 34 | −7.872 | 74.796 | 6.517 | 1.00 | 27.58 |
| ATOM | 202 | GB | THR | 34 | −9.186 | 74.802 | 7.313 | 1.00 | 27.59 |
| ATOM | 203 | OG1 | THR | 34 | −8.988 | 75.504 | 8.547 | 1.00 | 26.09 |
| ATOM | 204 | CG2 | THR | 34 | −9.642 | 73.387 | 7.605 | 1.00 | 30.18 |
| ATOM | 205 | C | THR | 34 | −6.730 | 74.588 | 7.500 | 1.00 | 28.50 |
| ATOM | 206 | O | THR | 34 | −6.192 | 73.485 | 7.611 | 1.00 | 31.02 |
| ATOM | 207 | N | ARG | 35 | −6.357 | 75.642 | 8.216 | 1.00 | 27.33 |
| ATOM | 208 | CA | ARG | 35 | −5.278 | 75.525 | 9.187 | 1.00 | 25.21 |
| ATOM | 209 | GB | ARG | 35 | −4.282 | 76.671 | 9.014 | 1.00 | 25.09 |
| ATOM | 210 | CG | ARG | 35 | −3.544 | 76.673 | 7.685 | 1.00 | 25.03 |
| ATOM | 211 | CD | ARG | 35 | −2.526 | 77.804 | 7.631 | 1.00 | 26.07 |
| ATOM | 212 | NE | ARG | 35 | −1.560 | 77.601 | 6.554 | 1.00 | 28.74 |
| ATOM | 213 | CZ | ARG | 35 | −1.337 | 78.472 | 5.572 | 1.00 | 32.52 |
| ATOM | 214 | NH1 | ARG | 35 | −2.003 | 79.624 | 5.517 | 1.00 | 32.37 |
| ATOM | 215 | NH2 | ARG | 35 | −0.457 | 78.185 | 4.628 | 1.00 | 34.71 |
| ATOM | 216 | C | ARG | 35 | −5.826 | 75.532 | 10.604 | 1.00 | 26.22 |
| ATOM | 217 | O | ARG | 35 | −5.095 | 75.788 | 11.550 | 1.00 | 28.51 |
| ATOM | 218 | N | ASP | 36 | −7.115 | 75.252 | 10.751 | 1.00 | 27.90 |
| ATOM | 219 | CA | ASP | 36 | −7.753 | 75.234 | 12.064 | 1.00 | 30.78 |
| ATOM | 220 | GB | ASP | 36 | −8.994 | 76.111 | 12.032 | 1.00 | 33.11 |
| ATOM | 221 | CG | ASP | 36 | −9.836 | 75.956 | 13.270 | 1.00 | 36.94 |
| ATOM | 222 | OD1 | ASP | 36 | −10.985 | 76.458 | 13.260 | 1.00 | 36.42 |
| ATOM | 223 | OD2 | ASP | 36 | −9.342 | 75.335 | 14.246 | 1.00 | 35.09 |
| ATOM | 224 | C | ASP | 36 | −8.141 | 73.817 | 12.523 | 1.00 | 32.42 |
| ATOM | 225 | O | ASP | 36 | −8.946 | 73.140 | 11.876 | 1.00 | 31.43 |
| ATOM | 226 | N | ARG | 37 | −7.587 | 73.386 | 13.657 | 1.00 | 32.70 |
| ATOM | 227 | CA | ARG | 37 | −7.863 | 72.046 | 14.173 | 1.00 | 30.63 |
| ATOM | 228 | GB | ARG | 37 | −6.715 | 71.530 | 15.053 | 1.00 | 28.29 |
| ATOM | 229 | CG | ARG | 37 | −5.446 | 71.235 | 14.284 | 1.00 | 30.34 |
| ATOM | 230 | CD | ARG | 37 | −4.372 | 70.546 | 15.121 | 1.00 | 28.87 |
| ATOM | 231 | NE | ARG | 37 | −4.700 | 69.167 | 15.474 | 1.00 | 26.36 |
| ATOM | 232 | CZ | ARG | 37 | −3.783 | 68.223 | 15.691 | 1.00 | 28.48 |
| ATOM | 233 | NH1 | ARG | 37 | −2.484 | 68.505 | 15.588 | 1.00 | 20.85 |
| ATOM | 234 | NH2 | ARG | 37 | −4.160 | 66.994 | 16.016 | 1.00 | 28.70 |
| ATOM | 235 | C | ARG | 37 | −9.143 | 71.938 | 14.951 | 1.00 | 28.28 |
| ATOM | 236 | O | ARG | 37 | −9.576 | 70.833 | 15.262 | 1.00 | 27.31 |
| ATOM | 237 | N | SER | 38 | −9.744 | 73.067 | 15.290 | 1.00 | 25.88 |
| ATOM | 238 | CA | SER | 38 | −10.984 | 72.998 | 16.036 | 1.00 | 28.07 |
| ATOM | 239 | GB | SER | 38 | −11.111 | 74.183 | 16.996 | 1.00 | 28.83 |
| ATOM | 240 | OG | SER | 38 | −10.866 | 75.412 | 16.344 | 1.00 | 34.41 |
| ATOM | 241 | C | SER | 38 | −12.161 | 72.939 | 15.070 | 1.00 | 27.66 |
| ATOM | 242 | O | SER | 38 | −13.306 | 72.723 | 15.489 | 1.00 | 28.69 |
| ATOM | 243 | N | ASP | 39 | −11.859 | 73.119 | 13.780 | 1.00 | 25.52 |
| ATOM | 244 | CA | ASP | 39 | −12.856 | 73.070 | 12.707 | 1.00 | 21.79 |
| ATOM | 245 | CB | ASP | 39 | −12.161 | 73.216 | 11.354 | 1.00 | 24.27 |
| ATOM | 246 | CG | ASP | 39 | −13.134 | 73.216 | 10.183 | 1.00 | 27.75 |
| ATOM | 247 | OD1 | ASP | 39 | −13.849 | 72.217 | 9.989 | 1.00 | 32.47 |
| ATOM | 248 | OD2 | ASP | 39 | −13.184 | 74.217 | 9.437 | 1.00 | 28.63 |
| ATOM | 249 | C | ASP | 39 | −13.529 | 71.716 | 12.800 | 1.00 | 21.20 |
| ATOM | 250 | O | ASP | 39 | −12.852 | 70.690 | 12.818 | 1.00 | 19.87 |
| ATOM | 251 | N | GLN | 40 | −14.857 | 71.710 | 12.859 | 1.00 | 22.40 |
| ATOM | 252 | CA | GLN | 40 | −15.617 | 70.467 | 12.988 | 1.00 | 23.65 |
| ATOM | 253 | CB | GLN | 40 | −17.051 | 70.781 | 13.402 | 1.00 | 23.78 |
| ATOM | 254 | C | GLN | 40 | −15.663 | 69.525 | 11.787 | 1.00 | 26.05 |
| ATOM | 255 | O | GLN | 40 | −16.152 | 68.407 | 11.922 | 1.00 | 28.44 |
| ATOM | 256 | N | HIS | 41 | −15.152 | 69.945 | 10.629 | 1.00 | 27.23 |
| ATOM | 257 | CA | HIS | 41 | −15.206 | 69.100 | 9.433 | 1.00 | 30.01 |
| ATOM | 258 | CB | HIS | 41 | −15.914 | 69.859 | 8.306 | 1.00 | 33.08 |
| ATOM | 259 | CG | HIS | 41 | −17.335 | 70.219 | 8.623 | 1.00 | 36.53 |
| ATOM | 260 | CD2 | HIS | 41 | −18.481 | 69.511 | 8.491 | 1.00 | 36.05 |
| ATOM | 261 | ND1 | HIS | 41 | −17.691 | 71.426 | 9.185 | 1.00 | 34.96 |
| ATOM | 262 | CE1 | HIS | 41 | −18.997 | 71.445 | 9.388 | 1.00 | 33.67 |
| ATOM | 263 | NE2 | HIS | 41 | −19.501 | 70.296 | 8.977 | 1.00 | 34.10 |
| ATOM | 264 | C | HIS | 41 | −13.900 | 68.500 | 8.883 | 1.00 | 30.83 |
| ATOM | 265 | O | HIS | 41 | −13.843 | 68.071 | 7.715 | 1.00 | 29.28 |
| ATOM | 266 | N | ILE | 42 | −12.859 | 68.455 | 9.709 | 1.00 | 29.98 |
| ATOM | 267 | CA | ILE | 42 | −11.578 | 67.899 | 9.274 | 1.00 | 27.41 |
| ATOM | 268 | CB | ILE | 42 | −10.392 | 68.785 | 9.737 | 1.00 | 26.47 |
| ATOM | 269 | CG2 | ILE | 42 | −10.168 | 69.898 | 8.740 | 1.00 | 28.37 |
| ATOM | 270 | CG1 | ILE | 42 | −10.658 | 69.351 | 11.133 | 1.00 | 22.43 |
| ATOM | 271 | CD1 | ILE | 42 | −9.469 | 70.047 | 11.736 | 1.00 | 21.79 |
| ATOM | 272 | C | ILE | 42 | −11.332 | 66.453 | 9.729 | 1.00 | 26.46 |
| ATOM | 273 | O | ILE | 42 | −10.399 | 65.801 | 9.247 | 1.00 | 25.66 |
| ATOM | 274 | N | GLN | 43 | −12.168 | 65.959 | 10.642 | 1.00 | 23.87 |
| ATOM | 275 | CA | GLN | 43 | −12.037 | 64.595 | 11.148 | 1.00 | 24.15 |
| ATOM | 276 | CB | GLN | 43 | −12.778 | 64.438 | 12.477 | 1.00 | 24.07 |
| ATOM | 277 | CC | GLN | 43 | −12.360 | 65.405 | 13.552 | 1.00 | 26.31 |

TABLE 2-continued

FGFR1 D2–D3 Complexed with FGF1

| | | | | | | | | | |
|---|---|---|---|---|---|---|---|---|---|
| ATOM | 278 | CD | GLN | 43 | −12.992 | 66.764 | 13.382 | 1.00 | 27.49 |
| ATOM | 279 | OE1 | GLN | 43 | −14.216 | 66.897 | 13.447 | 1.00 | 32.47 |
| ATOM | 280 | NE2 | GLN | 43 | −12.168 | 67.786 | 13.167 | 1.00 | 24.21 |
| ATOM | 281 | C | GLN | 43 | −12.577 | 63.562 | 10.157 | 1.00 | 22.64 |
| ATOM | 282 | O | GLN | 43 | −13.765 | 63.524 | 9.862 | 1.00 | 23.92 |
| ATOM | 283 | N | LEU | 44 | −11.698 | 62.697 | 9.686 | 1.00 | 21.43 |
| ATOM | 284 | CA | LEU | 44 | −12.072 | 61.691 | 8.715 | 1.00 | 22.69 |
| ATOM | 285 | CB | LEU | 44 | −11.224 | 61.871 | 7.452 | 1.00 | 18.32 |
| ATOM | 286 | CG | LEU | 44 | −10.987 | 63.346 | 7.110 | 1.00 | 17.15 |
| ATOM | 287 | CD1 | LEU | 44 | −9.968 | 63.467 | 5.977 | 1.00 | 12.49 |
| ATOM | 288 | CD2 | LEU | 44 | −12.322 | 64.014 | 6.773 | 1.00 | 11.74 |
| ATOM | 289 | C | LEU | 44 | −11.922 | 60.261 | 9.216 | 1.00 | 25.60 |
| ATOM | 290 | O | LEU | 44 | −11.048 | 59.943 | 10.031 | 1.00 | 27.19 |
| ATOM | 291 | N | GLN | 45 | −12.782 | 59.398 | 8.693 | 1.00 | 26.35 |
| ATOM | 292 | CA | GLN | 45 | −12.775 | 57.996 | 9.039 | 1.00 | 26.11 |
| ATOM | 293 | CB | GLN | 45 | −14.130 | 57.600 | 9.610 | 1.00 | 29.41 |
| ATOM | 294 | CC | GLN | 45 | −14.122 | 56.242 | 10.247 | 1.00 | 33.87 |
| ATOM | 295 | CD | GLN | 45 | −13.128 | 56.188 | 11.378 | 1.00 | 37.58 |
| ATOM | 296 | OE1 | GLN | 45 | −13.257 | 56.925 | 12.359 | 1.00 | 39.35 |
| ATOM | 297 | NE2 | GLN | 45 | −12.119 | 55.325 | 11.247 | 1.00 | 37.04 |
| ATOM | 298 | C | GLN | 45 | −12.481 | 57.173 | 7.781 | 1.00 | 26.30 |
| ATOM | 299 | O | GLN | 45 | −13.370 | 56.933 | 6.960 | 1.00 | 27.12 |
| ATOM | 300 | N | LEU | 46 | −11.228 | 56.752 | 7.637 | 1.00 | 23.91 |
| ATOM | 301 | CA | LEU | 46 | −10.806 | 55.954 | 6.502 | 1.00 | 21.84 |
| ATOM | 302 | GB | LEU | 46 | −9.293 | 56.072 | 6.312 | 1.00 | 21.30 |
| ATOM | 303 | CG | LEU | 46 | −8.801 | 57.321 | 5.564 | 1.00 | 22.12 |
| ATOM | 304 | CD1 | LEU | 46 | −9.167 | 58.593 | 6.300 | 1.00 | 19.17 |
| ATOM | 305 | CD2 | LEU | 46 | −7.308 | 57.221 | 5.386 | 1.00 | 24.79 |
| ATOM | 306 | C | LEU | 46 | −11.196 | 54.499 | 6.706 | 1.00 | 22.57 |
| ATOM | 307 | O | LEU | 46 | −11.141 | 53.992 | 7.821 | 1.00 | 21.81 |
| ATOM | 308 | N | SER | 47 | −11.598 | 53.835 | 5.624 | 1.00 | 25.02 |
| ATOM | 309 | CA | SER | 47 | −12.010 | 52.429 | 5.677 | 1.00 | 25.85 |
| ATOM | 310 | CB | SER | 47 | −13.529 | 52.328 | 5.762 | 1.00 | 23.77 |
| ATOM | 311 | OG | SER | 47 | −14.085 | 53.517 | 6.293 | 1.00 | 29.89 |
| ATOM | 312 | C | SER | 47 | −11.540 | 51.683 | 4.429 | 1.00 | 27.64 |
| ATOM | 313 | O | SER | 47 | −11.490 | 52.248 | 3.332 | 1.00 | 28.03 |
| ATOM | 314 | N | ALA | 48 | −11.207 | 50.408 | 4.588 | 1.00 | 28.72 |
| ATOM | 315 | CA | ALA | 48 | −10.755 | 49.618 | 3.456 | 1.00 | 31.22 |
| ATOM | 316 | GB | ALA | 48 | −9.605 | 48.716 | 3.875 | 1.00 | 31.58 |
| ATOM | 317 | C | ALA | 48 | −11.876 | 48.779 | 2.855 | 1.00 | 33.53 |
| ATOM | 318 | O | ALA | 48 | −12.469 | 47.938 | 3.528 | 1.00 | 34.12 |
| ATOM | 319 | N | GLU | 49 | −12.178 | 49.023 | 1.586 | 1.00 | 35.72 |
| ATOM | 320 | CA | GLU | 49 | −13.201 | 48.247 | 0.900 | 1.00 | 37.48 |
| ATOM | 321 | GB | GLU | 49 | −13.668 | 48.988 | −0.357 | 1.00 | 41.73 |
| ATOM | 322 | CG | GLU | 49 | −14.710 | 48.245 | −1.190 | 1.00 | 49.89 |
| ATOM | 323 | CD | GLU | 49 | −15.845 | 47.643 | −0.350 | 1.00 | 56.40 |
| ATOM | 324 | OE1 | GLU | 49 | −16.359 | 48.326 | 0.570 | 1.00 | 58.69 |
| ATOM | 325 | OE2 | GLU | 49 | −16.233 | 46.483 | −0.623 | 1.00 | 59.10 |
| ATOM | 326 | C | GLU | 49 | −12.510 | 46.938 | 0.519 | 1.00 | 36.22 |
| ATOM | 327 | O | GLU | 49 | −13.113 | 45.864 | 0.516 | 1.00 | 36.49 |
| ATOM | 328 | N | SER | 50 | −11.222 | 47.061 | 0.217 | 1.00 | 33.53 |
| ATOM | 329 | CA | SER | 50 | −10.369 | 45.950 | −0.175 | 1.00 | 29.49 |
| ATOM | 330 | GB | SER | 50 | −10.395 | 45.768 | −1.690 | 1.00 | 29.77 |
| ATOM | 331 | OG | SER | 50 | −11.727 | 45.725 | −2.174 | 1.00 | 33.14 |
| ATOM | 332 | C | SER | 50 | −8.976 | 46.376 | 0.242 | 1.00 | 28.11 |
| ATOM | 333 | O | SER | 50 | −8.779 | 47.531 | 0.625 | 1.00 | 29.53 |
| ATOM | 334 | N | VAL | 51 | −8.015 | 45.459 | 0.172 | 1.00 | 23.82 |
| ATOM | 335 | CA | VAL | 51 | −6.643 | 45.782 | 0.537 | 1.00 | 18.87 |
| ATOM | 336 | GB | VAL | 51 | −5.678 | 44.594 | 0.243 | 1.00 | 18.83 |
| ATOM | 337 | CG1 | VAL | 51 | −4.234 | 44.969 | 0.600 | 1.00 | 16.48 |
| ATOM | 338 | CG2 | VAL | 51 | −6.103 | 43.372 | 1.024 | 1.00 | 15.72 |
| ATOM | 339 | C | VAL | 51 | −6.197 | 46.982 | −0.294 | 1.00 | 18.34 |
| ATOM | 340 | O | VAL | 51 | −6.427 | 47.026 | −1.500 | 1.00 | 19.32 |
| ATOM | 341 | N | GLY | 52 | −5.582 | 47.961 | 0.357 | 1.00 | 17.24 |
| ATOM | 342 | CA | GLY | 52 | −5.085 | 49.135 | −0.344 | 1.00 | 16.86 |
| ATOM | 343 | C | GLY | 52 | −6.058 | 50.189 | −0.839 | 1.00 | 17.15 |
| ATOM | 344 | O | GLY | 52 | −5.634 | 51.293 | −1.154 | 1.00 | 16.89 |
| ATOM | 345 | N | GLU | 53 | −7.345 | 49.865 | −0.919 | 1.00 | 20.93 |
| ATOM | 346 | CA | GLU | 53 | −8.354 | 50.809 | −1.404 | 1.00 | 24.08 |
| ATOM | 347 | GB | GLU | 53 | −9.283 | 50.113 | −2.387 | 1.00 | 26.57 |
| ATOM | 348 | CG | GLU | 53 | −8.591 | 49.029 | −3.178 | 1.00 | 31.61 |
| ATOM | 349 | CD | GLU | 53 | −9.445 | 48.463 | −4.292 | 1.00 | 34.45 |
| ATOM | 350 | OE1 | GLU | 53 | −10.637 | 48.139 | −4.048 | 1.00 | 36.05 |
| ATOM | 351 | OE2 | GLU | 53 | −8.904 | 48.336 | −5.412 | 1.00 | 34.43 |
| ATOM | 352 | C | GLU | 53 | −9.153 | 51.321 | −0.224 | 1.00 | 25.65 |
| ATOM | 353 | O | GLU | 53 | −9.654 | 50.533 | 0.582 | 1.00 | 26.79 |
| ATOM | 354 | N | VAL | 54 | −9.306 | 52.637 | −0.132 | 1.00 | 25.28 |

TABLE 2-continued

FGFR1 D2–D3 Complexed with FGF1

| ATOM | 355 | CA  | VAL | 54 | −10.000 | 53.198 | 1.012  | 1.00 | 25.84 |
|------|-----|-----|-----|----|---------|--------|--------|------|-------|
| ATOM | 356 | GB  | VAL | 54 | −8.991  | 53.874 | 1.986  | 1.00 | 27.15 |
| ATOM | 357 | CG1 | VAL | 54 | −7.793  | 52.970 | 2.223  | 1.00 | 26.22 |
| ATOM | 358 | CG2 | VAL | 54 | −8.520  | 55.202 | 1.420  | 1.00 | 26.83 |
| ATOM | 359 | C   | VAL | 54 | −11.081 | 54.221 | 0.737  | 1.00 | 27.05 |
| ATOM | 360 | O   | VAL | 54 | −11.087 | 54.896 | −0.290 | 1.00 | 29.16 |
| ATOM | 361 | N   | TYR | 55 | −12.007 | 54.310 | 1.680  | 1.00 | 27.41 |
| ATOM | 362 | CA  | TYR | 55 | −13.063 | 55.305 | 1.642  | 1.00 | 26.40 |
| ATOM | 363 | CB  | TYR | 55 | −14.401 | 54.734 | 2.114  | 1.00 | 27.97 |
| ATOM | 364 | CG  | TYR | 55 | −15.119 | 53.901 | 1.079  | 1.00 | 31.95 |
| ATOM | 365 | CD1 | TYR | 55 | −15.442 | 54.432 | −0.174 | 1.00 | 30.89 |
| ATOM | 366 | CE1 | TYR | 55 | −16.139 | 53.686 | −1.113 | 1.00 | 29.38 |
| ATOM | 367 | CD2 | TYR | 55 | −15.511 | 52.594 | 1.364  | 1.00 | 32.02 |
| ATOM | 368 | CE2 | TYR | 55 | −16.211 | 51.840 | 0.432  | 1.00 | 33.83 |
| ATOM | 369 | CZ  | TYR | 55 | −16.525 | 52.390 | −0.806 | 1.00 | 31.97 |
| ATOM | 370 | OH  | TYR | 55 | −17.239 | 51.642 | −1.716 | 1.00 | 29.18 |
| ATOM | 371 | C   | TYR | 55 | −12.559 | 56.324 | 2.665  | 1.00 | 25.59 |
| ATOM | 372 | O   | TYR | 55 | −11.805 | 55.977 | 3.584  | 1.00 | 21.61 |
| ATOM | 373 | N   | ILE | 56 | −12.972 | 57.573 | 2.504  | 1.00 | 22.88 |
| ATOM | 374 | CA  | ILE | 56 | −12.547 | 58.628 | 3.398  | 1.00 | 20.19 |
| ATOM | 375 | CB  | ILE | 56 | −11.459 | 59.468 | 2.728  | 1.00 | 18.99 |
| ATOM | 376 | CG2 | ILE | 56 | −11.139 | 60.690 | 3.585  | 1.00 | 20.24 |
| ATOM | 377 | CG1 | ILE | 56 | −10.234 | 58.589 | 2.461  | 1.00 | 15.90 |
| ATOM | 378 | CD1 | ILE | 56 | −9.179  | 59.251 | 1.601  | 1.00 | 17.40 |
| ATOM | 379 | C   | ILE | 56 | −13.750 | 59.491 | 3.656  | 1.00 | 20.26 |
| ATOM | 380 | O   | ILE | 56 | −14.124 | 60.276 | 2.797  | 1.00 | 23.54 |
| ATOM | 381 | N   | LYS | 57 | −14.370 | 59.371 | 4.823  | 1.00 | 22.25 |
| ATOM | 382 | CA  | LYS | 57 | −15.556 | 60.189 | 5.055  | 1.00 | 26.24 |
| ATOM | 383 | CB  | LYS | 57 | −16.821 | 59.323 | 5.029  | 1.00 | 26.57 |
| ATOM | 384 | CG  | LYS | 57 | −17.092 | 58.562 | 6.298  | 1.00 | 28.92 |
| ATOM | 385 | CD  | LYS | 57 | −18.595 | 58.459 | 6.529  | 1.00 | 33.90 |
| ATOM | 386 | CE  | LYS | 57 | −18.903 | 57.855 | 7.894  | 1.00 | 36.61 |
| ATOM | 387 | NZ  | LYS | 57 | −20.284 | 58.199 | 8.350  | 1.00 | 38.42 |
| ATOM | 388 | C   | LYS | 57 | −15.590 | 61.058 | 6.301  | 1.00 | 26.39 |
| ATOM | 389 | O   | LYS | 57 | −15.146 | 60.663 | 7.374  | 1.00 | 24.91 |
| ATOM | 390 | N   | SER | 58 | −16.146 | 62.251 | 6.134  | 1.00 | 27.09 |
| ATOM | 391 | CA  | SER | 58 | −16.287 | 63.185 | 7.230  | 1.00 | 27.99 |
| ATOM | 392 | CB  | SER | 58 | −16.995 | 64.457 | 6.754  | 1.00 | 28.30 |
| ATOM | 393 | OG  | SER | 58 | −17.171 | 65.390 | 7.806  | 1.00 | 24.98 |
| ATOM | 394 | C   | SER | 58 | −17.118 | 62.508 | 8.309  | 1.00 | 29.22 |
| ATOM | 395 | O   | SER | 58 | −18.149 | 61.895 | 8.027  | 1.00 | 28.11 |
| ATOM | 396 | N   | THR | 59 | −16.653 | 62.616 | 9.545  | 1.00 | 31.50 |
| ATOM | 397 | CA  | THR | 59 | −17.344 | 62.033 | 10.684 | 1.00 | 32.90 |
| ATOM | 398 | CB  | THR | 59 | −16.410 | 61.942 | 11.879 | 1.00 | 35.91 |
| ATOM | 399 | OG1 | THR | 59 | −15.721 | 63.193 | 12.011 | 1.00 | 40.36 |
| ATOM | 400 | CG2 | THR | 59 | −15.397 | 60.808 | 11.694 | 1.00 | 39.43 |
| ATOM | 401 | C   | THR | 59 | −18.505 | 62.932 | 11.067 | 1.00 | 30.76 |
| ATOM | 402 | O   | THR | 59 | −19.514 | 62.474 | 11.589 | 1.00 | 28.04 |
| ATOM | 403 | N   | GLU | 60 | −18.347 | 64.221 | 10.793 | 1.00 | 31.18 |
| ATOM | 404 | CA  | GLU | 60 | −19.367 | 65.201 | 11.119 | 1.00 | 30.56 |
| ATOM | 405 | CB  | GLU | 60 | −18.790 | 66.614 | 10.998 | 1.00 | 32.59 |
| ATOM | 406 | CC  | GLU | 60 | −19.522 | 67.642 | 11.850 | 1.00 | 34.81 |
| ATOM | 407 | CD  | GLU | 60 | −19.646 | 67.193 | 13.304 | 1.00 | 36.76 |
| ATOM | 408 | OE1 | GLU | 60 | −18.625 | 66.744 | 13.885 | 1.00 | 38.08 |
| ATOM | 409 | OE2 | GLU | 60 | −20.760 | 67.288 | 13.864 | 1.00 | 33.66 |
| ATOM | 410 | C   | GLU | 60 | −20.603 | 65.087 | 10.244 | 1.00 | 29.55 |
| ATOM | 411 | O   | GLU | 60 | −21.719 | 64.952 | 10.744 | 1.00 | 27.43 |
| ATOM | 412 | N   | THR | 61 | −20.394 | 65.132 | 8.933  | 1.00 | 30.33 |
| ATOM | 413 | CA  | THR | 61 | −21.497 | 65.073 | 7.983  | 1.00 | 29.96 |
| ATOM | 414 | CB  | THR | 61 | −21.283 | 66.103 | 6.855  | 1.00 | 28.13 |
| ATOM | 415 | OG1 | THR | 61 | −20.209 | 65.682 | 6.013  | 1.00 | 28.36 |
| ATOM | 416 | CG2 | THR | 61 | −20.933 | 67.452 | 7.441  | 1.00 | 25.56 |
| ATOM | 417 | C   | THR | 61 | −21.775 | 63.702 | 7.355  | 1.00 | 31.53 |
| ATOM | 418 | O   | THR | 61 | −22.871 | 63.464 | 6.851  | 1.00 | 35.52 |
| ATOM | 419 | N   | GLY | 62 | −20.806 | 62.795 | 7.386  | 1.00 | 30.76 |
| ATOM | 420 | CA  | GLY | 62 | −21.038 | 61.492 | 6.791  | 1.00 | 28.64 |
| ATOM | 421 | C   | GLY | 62 | −20.905 | 61.548 | 5.276  | 1.00 | 28.22 |
| ATOM | 422 | O   | GLY | 62 | −21.453 | 60.718 | 4.555  | 1.00 | 26.62 |
| ATOM | 423 | N   | GLN | 63 | −20.182 | 62.548 | 4.788  | 1.00 | 27.17 |
| ATOM | 424 | CA  | GLN | 63 | −19.965 | 62.685 | 3.359  | 1.00 | 26.55 |
| ATOM | 425 | GB  | GLN | 63 | −19.825 | 64.150 | 2.950  | 1.00 | 26.28 |
| ATOM | 426 | CG  | GLN | 63 | −21.023 | 65.036 | 3.212  | 1.00 | 29.09 |
| ATOM | 427 | CD  | GLN | 63 | −20.740 | 66.481 | 2.825  | 1.00 | 30.75 |
| ATOM | 428 | OE1 | GLN | 63 | −20.734 | 66.832 | 1.639  | 1.00 | 30.33 |
| ATOM | 429 | NE2 | GLN | 63 | −20.478 | 67.320 | 3.823  | 1.00 | 26.29 |
| ATOM | 430 | C   | GLN | 63 | −18.670 | 61.975 | 3.010  | 1.00 | 25.88 |
| ATOM | 431 | O   | GLN | 63 | −17.733 | 61.958 | 3.812  | 1.00 | 27.47 |

TABLE 2-continued

| | | | FGFR1 D2–D3 Complexed with FGF1 | | | | | |
|---|---|---|---|---|---|---|---|---|
| ATOM | 432 | N | TYR | 64 | −18.620 | 61.397 | 1.813 | 1.00 | 23.34 |
| ATOM | 433 | CA | TYR | 64 | −17.426 | 60.706 | 1.350 | 1.00 | 21.48 |
| ATOM | 434 | GB | TYR | 64 | −17.786 | 59.442 | 0.568 | 1.00 | 20.38 |
| ATOM | 435 | CG | TYR | 64 | −18.377 | 58.359 | 1.426 | 1.00 | 20.27 |
| ATOM | 436 | CD1 | TYR | 64 | −19.697 | 58.430 | 1.864 | 1.00 | 19.31 |
| ATOM | 437 | CE1 | TYR | 64 | −20.225 | 57.466 | 2.711 | 1.00 | 18.93 |
| ATOM | 438 | CD2 | TYR | 64 | −17.601 | 57.289 | 1.853 | 1.00 | 21.00 |
| ATOM | 439 | CE2 | TYR | 64 | −18.124 | 56.317 | 2.701 | 1.00 | 20.56 |
| ATOM | 440 | CZ | TYR | 64 | −19.430 | 56.414 | 3.128 | 1.00 | 19.38 |
| ATOM | 441 | OH | TYR | 64 | −19.929 | 55.470 | 3.994 | 1.00 | 22.05 |
| ATOM | 442 | C | TYR | 64 | −16.622 | 61.626 | 0.459 | 1.00 | 20.42 |
| ATOM | 443 | O | TYR | 64 | −17.178 | 62.458 | −0.250 | 1.00 | 20.96 |
| ATOM | 444 | N | LEU | 65 | −15.306 | 61.500 | 0.525 | 1.00 | 19.55 |
| ATOM | 445 | CA | LEU | 65 | −14.455 | 62.310 | −0.307 | 1.00 | 20.09 |
| ATOM | 446 | GB | LEU | 65 | −13.037 | 62.355 | 0.250 | 1.00 | 20.85 |
| ATOM | 447 | CG | LEU | 65 | −11.985 | 63.017 | −0.650 | 1.00 | 23.92 |
| ATOM | 448 | CD1 | LEU | 65 | −12.249 | 64.512 | −0.740 | 1.00 | 22.56 |
| ATOM | 449 | CD2 | LEU | 65 | −10.591 | 62.749 | −0.104 | 1.00 | 23.40 |
| ATOM | 450 | C | LEU | 65 | −14.481 | 61.564 | −1.624 | 1.00 | 23.95 |
| ATOM | 451 | O | LEU | 65 | −14.342 | 60.340 | −1.659 | 1.00 | 25.36 |
| ATOM | 452 | N | ALA | 66 | −14.676 | 62.302 | −2.705 | 1.00 | 27.03 |
| ATOM | 453 | CA | ALA | 66 | −14.742 | 61.709 | −4.023 | 1.00 | 27.15 |
| ATOM | 454 | GB | ALA | 66 | −16.183 | 61.376 | −4.356 | 1.00 | 24.77 |
| ATOM | 455 | C | ALA | 66 | −14.159 | 62.648 | −5.071 | 1.00 | 30.07 |
| ATOM | 456 | O | ALA | 66 | −13.918 | 63.831 | −4.817 | 1.00 | 30.31 |
| ATOM | 457 | N | MET | 67 | −13.941 | 62.104 | −6.258 | 1.00 | 34.43 |
| ATOM | 458 | CA | MET | 67 | −13.382 | 62.857 | −7.367 | 1.00 | 36.96 |
| ATOM | 459 | GB | MET | 67 | −11.962 | 62.358 | −7.648 | 1.00 | 35.46 |
| ATOM | 460 | CG | MET | 67 | −11.258 | 63.064 | −8.787 | 1.00 | 38.86 |
| ATOM | 461 | SD | MET | 67 | −9.536 | 62.515 | −9.015 | 1.00 | 37.06 |
| ATOM | 462 | CE | MET | 67 | −8.656 | 63.791 | −8.190 | 1.00 | 37.88 |
| ATOM | 463 | C | MET | 67 | −14.280 | 62.676 | −8.599 | 1.00 | 38.79 |
| ATOM | 464 | O | MET | 67 | −14.544 | 61.546 | −9.021 | 1.00 | 40.47 |
| ATOM | 465 | N | ASP | 68 | −14.755 | 63.793 | −9.152 | 1.00 | 38.95 |
| ATOM | 466 | CA | ASP | 68 | −15.618 | 63.787 | −10.328 | 1.00 | 38.31 |
| ATOM | 467 | GB | ASP | 68 | −16.291 | 65.159 | −10.506 | 1.00 | 41.23 |
| ATOM | 468 | CG | ASP | 68 | −15.304 | 66.266 | −10.876 | 1.00 | 43.09 |
| ATOM | 469 | OD1 | ASP | 68 | −15.723 | 67.440 | −10.950 | 1.00 | 43.77 |
| ATOM | 470 | OD2 | ASP | 68 | −14.115 | 65.967 | −11.097 | 1.00 | 44.63 |
| ATOM | 471 | C | ASP | 68 | −14.794 | 63.448 | −11.561 | 1.00 | 37.61 |
| ATOM | 472 | O | ASP | 68 | −13.568 | 63.374 | −11.496 | 1.00 | 35.14 |
| ATOM | 473 | N | THR | 69 | −15.465 | 63.260 | −12.690 | 1.00 | 39.16 |
| ATOM | 474 | CA | THR | 69 | −14.761 | 62.924 | −13.920 | 1.00 | 40.40 |
| ATOM | 475 | GB | THR | 69 | −15.744 | 62.541 | −15.031 | 1.00 | 39.26 |
| ATOM | 476 | OG1 | THR | 69 | −16.749 | 61.668 | −14.497 | 1.00 | 41.34 |
| ATOM | 477 | CG2 | THR | 69 | −15.005 | 61.806 | −16.147 | 1.00 | 39.63 |
| ATOM | 478 | C | THR | 69 | −13.857 | 64.053 | −14.411 | 1.00 | 40.83 |
| ATOM | 479 | O | THR | 69 | −13.095 | 63.873 | −15.357 | 1.00 | 40.64 |
| ATOM | 480 | N | ASP | 70 | −13.936 | 65.213 | −13.760 | 1.00 | 42.39 |
| ATOM | 481 | CA | ASP | 70 | −13.109 | 66.372 | −14.114 | 1.00 | 41.09 |
| ATOM | 482 | GB | ASP | 70 | −13.790 | 67.681 | −13.702 | 1.00 | 46.08 |
| ATOM | 483 | CG | ASP | 70 | −14.998 | 68.015 | −14.553 | 1.00 | 51.55 |
| ATOM | 484 | OD1 | ASP | 70 | −15.830 | 68.826 | −14.092 | 1.00 | 52.51 |
| ATOM | 485 | OD2 | ASP | 70 | −15.113 | 67.483 | −15.680 | 1.00 | 54.94 |
| ATOM | 486 | C | ASP | 70 | −11.798 | 66.289 | −13.358 | 1.00 | 38.67 |
| ATOM | 487 | O | ASP | 70 | −10.768 | 66.769 | −13.817 | 1.00 | 37.28 |
| ATOM | 488 | N | GLY | 71 | −11.856 | 65.673 | −12.184 | 1.00 | 37.56 |
| ATOM | 489 | CA | GLY | 71 | −10.683 | 65.559 | −11.338 | 1.00 | 33.59 |
| ATOM | 490 | C | GLY | 71 | −10.841 | 66.565 | −10.219 | 1.00 | 29.81 |
| ATOM | 491 | O | GLY | 71 | −9.875 | 67.163 | −9.760 | 1.00 | 26.66 |
| ATOM | 492 | N | LEU | 72 | −12.085 | 66.755 | −9.795 | 1.00 | 28.78 |
| ATOM | 493 | CA | LEU | 72 | −12.399 | 67.697 | −8.742 | 1.00 | 29.10 |
| ATOM | 494 | CB | LEU | 72 | −13.393 | 68.739 | −9.246 | 1.00 | 28.03 |
| ATOM | 495 | CG | LEU | 72 | −12.841 | 69.618 | −10.364 | 1.00 | 29.44 |
| ATOM | 496 | CD1 | LEU | 72 | −13.782 | 70.807 | −10.572 | 1.00 | 30.22 |
| ATOM | 497 | CD2 | LEU | 72 | −11.440 | 70.103 | −10.003 | 1.00 | 28.57 |
| ATOM | 498 | C | LEU | 72 | −12.960 | 67.003 | −7.517 | 1.00 | 29.08 |
| ATOM | 499 | O | LEU | 72 | −13.933 | 66.252 | −7.600 | 1.00 | 27.03 |
| ATOM | 500 | N | LEU | 73 | −12.338 | 67.275 | −6.374 | 1.00 | 27.78 |
| ATOM | 501 | CA | LEU | 73 | −12.750 | 66.675 | −5.113 | 1.00 | 26.97 |
| ATOM | 502 | CB | LEU | 73 | −11.681 | 66.924 | −4.045 | 1.00 | 27.63 |
| ATOM | 503 | CG | LEU | 73 | −10.278 | 66.405 | −4.357 | 1.00 | 27.56 |
| ATOM | 504 | CD1 | LEU | 73 | −9.301 | 66.946 | −3.324 | 1.00 | 27.62 |
| ATOM | 505 | CD2 | LEU | 73 | −10.283 | 64.882 | −4.377 | 1.00 | 27.97 |
| ATOM | 506 | C | LEU | 73 | −14.080 | 67.248 | −4.652 | 1.00 | 25.28 |
| ATOM | 507 | O | LEU | 73 | −14.342 | 68.438 | −4.827 | 1.00 | 25.28 |
| ATOM | 508 | N | TYR | 74 | −14.918 | 66.399 | −4.064 | 1.00 | 21.91 |

TABLE 2-continued

FGFR1 D2–D3 Complexed with FGF1

| ATOM | 509 | CA | TYR | 74 | −16.212 | 66.844 | −3.579 | 1.00 | 18.97 |
|---|---|---|---|---|---|---|---|---|---|
| ATOM | 510 | CB | TYR | 74 | −17.169 | 66.991 | −4.755 | 1.00 | 17.95 |
| ATOM | 511 | CG | TYR | 74 | −17.592 | 65.673 | −5.361 | 1.00 | 16.96 |
| ATOM | 512 | CD1 | TYR | 74 | −18.741 | 65.008 | −4.905 | 1.00 | 15.81 |
| ATOM | 513 | CE1 | TYR | 74 | −19.112 | 63.783 | −5.424 | 1.00 | 12.54 |
| ATOM | 514 | CD2 | TYR | 74 | −16.832 | 65.071 | −6.359 | 1.00 | 15.33 |
| ATOM | 515 | CE2 | TYR | 74 | −17.196 | 63.839 | −6.888 | 1.00 | 14.99 |
| ATOM | 516 | CZ | TYR | 74 | −18.336 | 63.206 | −6.414 | 1.00 | 16.26 |
| ATOM | 517 | OH | TYR | 74 | −18.700 | 61.989 | −6.931 | 1.00 | 21.19 |
| ATOM | 518 | C | TYR | 74 | −16.777 | 65.857 | −2.562 | 1.00 | 19.47 |
| ATOM | 519 | O | TYR | 74 | −16.400 | 64.686 | −2.550 | 1.00 | 16.67 |
| ATOM | 520 | N | GLY | 75 | −17.676 | 66.337 | −1.707 | 1.00 | 19.57 |
| ATOM | 521 | CA | GLY | 75 | −18.275 | 65.475 | −0.707 | 1.00 | 22.20 |
| ATOM | 522 | C | GLY | 75 | −19.448 | 64.718 | −1.294 | 1.00 | 24.60 |
| ATOM | 523 | O | GLY | 75 | −20.259 | 65.294 | −2.020 | 1.00 | 27.99 |
| ATOM | 524 | N | SER | 76 | −19.552 | 63.433 | −0.978 | 1.00 | 22.61 |
| ATOM | 525 | CA | SER | 76 | −20.630 | 62.618 | −1.506 | 1.00 | 21.82 |
| ATOM | 526 | CB | SER | 76 | −20.035 | 61.486 | −2.348 | 1.00 | 20.60 |
| ATOM | 527 | OG | SER | 76 | −21.048 | 60.702 | −2.949 | 1.00 | 21.71 |
| ATOM | 528 | C | SER | 76 | −21.533 | 62.056 | −0.411 | 1.00 | 21.49 |
| ATOM | 529 | O | SER | 76 | −21.073 | 61.376 | 0.490 | 1.00 | 20.33 |
| ATOM | 530 | N | GLN | 77 | −22.826 | 62.335 | −0.508 | 1.00 | 24.07 |
| ATOM | 531 | CA | GLN | 77 | −23.798 | 61.869 | 0.479 | 1.00 | 28.51 |
| ATOM | 532 | CB | GLN | 77 | −25.205 | 62.352 | 0.098 | 1.00 | 34.41 |
| ATOM | 533 | CG | GLN | 77 | −25.326 | 63.863 | −0.168 | 1.00 | 45.41 |
| ATOM | 534 | CD | GLN | 77 | −24.368 | 64.366 | −1.267 | 1.00 | 54.19 |
| ATOM | 535 | OE1 | GLN | 77 | −24.358 | 63.851 | −2.396 | 1.00 | 55.96 |
| ATOM | 536 | NE2 | GLN | 77 | −23.560 | 65.379 | −0.932 | 1.00 | 56.37 |
| ATOM | 537 | C | GLN | 77 | −23.798 | 60.342 | 0.621 | 1.00 | 27.85 |
| ATOM | 538 | O | GLN | 77 | −24.117 | 59.810 | 1.681 | 1.00 | 27.20 |
| ATOM | 539 | N | THR | 78 | −23.453 | 59.645 | −0.456 | 1.00 | 27.43 |
| ATOM | 540 | CA | THR | 78 | −23.407 | 58.186 | −0.455 | 1.00 | 27.61 |
| ATOM | 541 | CB | THR | 78 | −24.645 | 57.547 | −1.165 | 1.00 | 27.98 |
| ATOM | 542 | OG1 | THR | 78 | −24.739 | 58.046 | −2.506 | 1.00 | 28.83 |
| ATOM | 543 | CG2 | THR | 78 | −25.937 | 57.861 | −0.417 | 1.00 | 26.27 |
| ATOM | 544 | C | THR | 78 | −22.152 | 57.751 | −1.202 | 1.00 | 27.82 |
| ATOM | 545 | O | THR | 78 | −21.729 | 58.408 | −2.150 | 1.00 | 23.73 |
| ATOM | 546 | N | PRO | 79 | −21.549 | 56.624 | −0.787 | 1.00 | 30.18 |
| ATOM | 547 | CD | PRO | 79 | −22.019 | 55.768 | 0.319 | 1.00 | 30.98 |
| ATOM | 548 | CA | PRO | 79 | −20.334 | 56.063 | −1.388 | 1.00 | 31.93 |
| ATOM | 549 | CB | PRO | 79 | −19.925 | 54.995 | −0.383 | 1.00 | 30.66 |
| ATOM | 550 | CG | PRO | 79 | −21.250 | 54.488 | 0.086 | 1.00 | 30.46 |
| ATOM | 551 | C | PRO | 79 | −20.541 | 55.483 | −2.783 | 1.00 | 32.59 |
| ATOM | 552 | O | PRO | 79 | −21.607 | 54.966 | −3.096 | 1.00 | 33.82 |
| ATOM | 553 | N | ASN | 80 | −19.509 | 55.564 | −3.612 | 1.00 | 33.04 |
| ATOM | 554 | CA | ASN | 80 | −19.572 | 55.039 | −4.971 | 1.00 | 33.28 |
| ATOM | 555 | CB | ASN | 80 | −20.420 | 55.936 | −5.859 | 1.00 | 29.97 |
| ATOM | 556 | CG | ASN | 80 | −20.002 | 57.386 | −5.784 | 1.00 | 29.20 |
| ATOM | 557 | OD1 | ASN | 80 | −20.748 | 58.214 | −5.269 | 1.00 | 30.68 |
| ATOM | 558 | ND2 | ASN | 80 | −18.803 | 57.704 | −6.291 | 1.00 | 23.38 |
| ATOM | 559 | C | ASN | 80 | −18.177 | 54.945 | −5.561 | 1.00 | 35.65 |
| ATOM | 560 | O | ASN | 80 | −17.189 | 55.300 | −4.909 | 1.00 | 35.39 |
| ATOM | 561 | N | GLU | 81 | −18.104 | 54.480 | −6.805 | 1.00 | 36.21 |
| ATOM | 562 | CA | GLU | 81 | −16.825 | 54.314 | −7.488 | 1.00 | 36.30 |
| ATOM | 563 | CB | GLU | 81 | −17.071 | 53.887 | −8.939 | 1.00 | 36.57 |
| ATOM | 564 | CG | GLU | 81 | −18.466 | 54.213 | −9.440 | 1.00 | 40.67 |
| ATOM | 565 | CD | GLU | 81 | −18.543 | 55.520 | −10.204 | 1.00 | 42.55 |
| ATOM | 566 | OE1 | GLU | 81 | −19.640 | 56.126 | −10.222 | 1.00 | 41.85 |
| ATOM | 567 | OE2 | GLU | 81 | −17.517 | 55.928 | −10.801 | 1.00 | 43.69 |
| ATOM | 568 | C | GLU | 81 | −15.943 | 55.561 | −7.425 | 1.00 | 34.33 |
| ATOM | 569 | O | GLU | 81 | −14.705 | 55.467 | −7.394 | 1.00 | 34.21 |
| ATOM | 570 | N | GLU | 82 | −16.576 | 56.726 | −7.375 | 1.00 | 31.15 |
| ATOM | 571 | CA | GLU | 82 | −15.826 | 57.967 | −7.317 | 1.00 | 31.48 |
| ATOM | 572 | CB | GLU | 82 | −16.699 | 59.121 | −7.786 | 1.00 | 32.95 |
| ATOM | 573 | CG | GLU | 82 | −17.301 | 58.921 | −9.159 | 1.00 | 32.36 |
| ATOM | 574 | CD | GLU | 82 | −17.451 | 60.229 | −9.903 | 1.00 | 33.17 |
| ATOM | 575 | OE1 | GLU | 82 | −18.079 | 61.161 | −9.340 | 1.00 | 28.95 |
| ATOM | 576 | OE2 | GLU | 82 | −16.932 | 60.321 | −11.045 | 1.00 | 35.17 |
| ATOM | 577 | C | GLU | 82 | −15.273 | 58.283 | −5.921 | 1.00 | 31.15 |
| ATOM | 578 | O | GLU | 82 | −14.557 | 59.262 | −5.745 | 1.00 | 29.43 |
| ATOM | 579 | N | CYS | 83 | −15.597 | 57.446 | −4.939 | 1.00 | 30.14 |
| ATOM | 580 | CA | CYS | 83 | −15.146 | 57.650 | −3.568 | 1.00 | 29.65 |
| ATOM | 581 | CB | CYS | 83 | −16.271 | 57.325 | −2.590 | 1.00 | 30.22 |
| ATOM | 582 | SG | CYS | 83 | −17.782 | 58.220 | −2.865 | 1.00 | 34.01 |
| ATOM | 583 | C | CYS | 83 | −13.929 | 56.816 | −3.179 | 1.00 | 30.18 |
| ATOM | 584 | O | CYS | 83 | −13.219 | 57.161 | −2.238 | 1.00 | 33.02 |
| ATOM | 585 | N | LEU | 84 | −13.701 | 55.717 | −3.888 | 1.00 | 29.32 |

TABLE 2-continued

| | | | FGFR1 D2–D3 Complexed with FGF1 | | | | | |
|---|---|---|---|---|---|---|---|---|
| ATOM | 586 | CA | LEU | 84 | −12.580 | 54.832 | −3.598 | 1.00 | 28.07 |
| ATOM | 587 | CB | LEU | 84 | −12.810 | 53.461 | −4.231 | 1.00 | 29.59 |
| ATOM | 588 | CG | LEU | 84 | −13.832 | 52.567 | −3.541 | 1.00 | 30.10 |
| ATOM | 589 | CD1 | LEU | 84 | −14.063 | 51.344 | −4.380 | 1.00 | 30.11 |
| ATOM | 590 | CD2 | LEU | 84 | −13.332 | 52.186 | −2.156 | 1.00 | 31.23 |
| ATOM | 591 | C | LEU | 84 | −11.233 | 55.361 | −4.057 | 1.00 | 27.57 |
| ATOM | 592 | O | LEU | 84 | −11.047 | 55.711 | −5.228 | 1.00 | 26.72 |
| ATOM | 593 | N | PHE | 85 | −10.289 | 55.390 | −3.122 | 1.00 | 24.59 |
| ATOM | 594 | CA | PHE | 85 | −8.946 | 55.860 | −3.405 | 1.00 | 24.16 |
| ATOM | 595 | CB | PHE | 85 | −8.681 | 57.157 | −2.635 | 1.00 | 23.67 |
| ATOM | 596 | CG | PHE | 85 | −9.458 | 58.333 | −3.148 | 1.00 | 22.06 |
| ATOM | 597 | CD1 | PHE | 85 | −8.978 | 59.084 | −4.220 | 1.00 | 22.74 |
| ATOM | 598 | CD2 | PHE | 85 | −10.694 | 58.658 | −2.598 | 1.00 | 17.88 |
| ATOM | 599 | GE1 | PHE | 85 | −9.723 | 60.139 | −4.738 | 1.00 | 18.93 |
| ATOM | 600 | CE2 | PHE | 85 | −11.443 | 59.703 | −3.106 | 1.00 | 15.03 |
| ATOM | 601 | CZ | PHE | 85 | −10.959 | 60.445 | −4.178 | 1.00 | 17.54 |
| ATOM | 602 | C | PHE | 85 | −7.887 | 54.819 | −3.043 | 1.00 | 25.51 |
| ATOM | 603 | O | PHE | 85 | −8.044 | 54.032 | −2.096 | 1.00 | 25.66 |
| ATOM | 604 | N | LEU | 86 | −6.805 | 54.818 | −3.814 | 1.00 | 24.59 |
| ATOM | 605 | CA | LEU | 86 | −5.707 | 53.905 | −3.579 | 1.00 | 23.48 |
| ATOM | 606 | CB | LEU | 86 | −5.006 | 53.591 | −4.891 | 1.00 | 21.27 |
| ATOM | 607 | CG | LEU | 86 | −5.915 | 52.794 | −5.824 | 1.00 | 21.04 |
| ATOM | 608 | CD1 | LEU | 86 | −5.175 | 52.438 | −7.087 | 1.00 | 19.70 |
| ATOM | 609 | CD2 | LEU | 86 | −6.395 | 51.541 | −5.105 | 1.00 | 19.85 |
| ATOM | 610 | C | LEU | 86 | −4.750 | 54.566 | −2.614 | 1.00 | 25.62 |
| ATOM | 611 | O | LEU | 86 | −4.183 | 55.615 | −2.925 | 1.00 | 25.42 |
| ATOM | 612 | N | GLU | 87 | −4.594 | 53.963 | −1.436 | 1.00 | 26.44 |
| ATOM | 613 | CA | GLU | 87 | −3.709 | 54.504 | −0.412 | 1.00 | 28.40 |
| ATOM | 614 | CB | GLU | 87 | −4.317 | 54.301 | 0.985 | 1.00 | 27.98 |
| ATOM | 615 | CG | GLU | 87 | −3.463 | 54.875 | 2.145 | 1.00 | 26.64 |
| ATOM | 616 | CD | GLU | 87 | −4.014 | 54.511 | 3.515 | 1.00 | 23.94 |
| ATOM | 617 | OE1 | GLU | 87 | −4.073 | 53.307 | 3.829 | 1.00 | 27.96 |
| ATOM | 618 | OE2 | GLU | 87 | −4.398 | 55.416 | 4.281 | 1.00 | 21.92 |
| ATOM | 619 | C | GLU | 87 | −2.330 | 53.860 | −0.465 | 1.00 | 28.13 |
| ATOM | 620 | O | GLU | 87 | −2.203 | 52.640 | −0.421 | 1.00 | 30.05 |
| ATOM | 621 | N | ARG | 88 | −1.296 | 54.681 | −0.571 | 1.00 | 27.67 |
| ATOM | 622 | CA | ARG | 88 | 0.050 | 54.147 | −0.598 | 1.00 | 31.22 |
| ATOM | 623 | CB | ARG | 88 | 0.628 | 54.133 | −2.018 | 1.00 | 34.68 |
| ATOM | 624 | CG | ARG | 88 | 1.956 | 53.371 | −2.084 | 1.00 | 41.67 |
| ATOM | 625 | CD | ARG | 88 | 2.837 | 53.733 | −3.277 | 1.00 | 45.98 |
| ATOM | 626 | NE | ARG | 88 | 4.232 | 53.379 | −3.000 | 1.00 | 51.46 |
| ATOM | 627 | CZ | ARG | 88 | 5.283 | 53.843 | −3.676 | 1.00 | 54.59 |
| ATOM | 628 | NH1 | ARG | 88 | 5.107 | 54.689 | −4.689 | 1.00 | 55.27 |
| ATOM | 629 | NH2 | ARG | 88 | 6.513 | 53.476 | −3.326 | 1.00 | 52.53 |
| ATOM | 630 | C | ARG | 88 | 0.976 | 54.949 | 0.303 | 1.00 | 30.54 |
| ATOM | 631 | O | ARG | 88 | 1.063 | 56.180 | 0.195 | 1.00 | 30.76 |
| ATOM | 632 | N | LEU | 89 | 1.650 | 54.239 | 1.204 | 1.00 | 27.05 |
| ATOM | 633 | CA | LEU | 89 | 2.604 | 54.857 | 2.108 | 1.00 | 25.80 |
| ATOM | 634 | CB | LEU | 89 | 2.762 | 54.006 | 3.374 | 1.00 | 26.00 |
| ATOM | 635 | CG | LEU | 89 | 3.853 | 54.360 | 4.399 | 1.00 | 25.93 |
| ATOM | 636 | CD1 | LEU | 89 | 4.031 | 55.866 | 4.547 | 1.00 | 24.56 |
| ATOM | 637 | CD2 | LEU | 89 | 3.474 | 53.740 | 5.727 | 1.00 | 26.66 |
| ATOM | 638 | C | LEU | 89 | 3.918 | 54.929 | 1.343 | 1.00 | 22.78 |
| ATOM | 639 | O | LEU | 89 | 4.587 | 53.927 | 1.166 | 1.00 | 23.03 |
| ATOM | 640 | N | GLU | 90 | 4.278 | 56.118 | 0.883 | 1.00 | 23.05 |
| ATOM | 641 | CA | GLU | 90 | 5.501 | 56.296 | 0.114 | 1.00 | 25.74 |
| ATOM | 642 | CB | GLU | 90 | 5.505 | 57.670 | −0.559 | 1.00 | 26.96 |
| ATOM | 643 | CG | GLU | 90 | 4.231 | 58.018 | −1.346 | 1.00 | 30.37 |
| ATOM | 644 | CD | GLU | 90 | 3.883 | 56.999 | −2.421 | 1.00 | 30.68 |
| ATOM | 645 | OE1 | GLU | 90 | 4.736 | 56.728 | −3.292 | 1.00 | 32.66 |
| ATOM | 646 | OE2 | GLU | 90 | 2.750 | 56.475 | −2.396 | 1.00 | 31.43 |
| ATOM | 647 | C | GLU | 90 | 6.804 | 56.128 | 0.901 | 1.00 | 27.47 |
| ATOM | 648 | O | GLU | 90 | 6.842 | 56.149 | 2.137 | 1.00 | 26.96 |
| ATOM | 649 | N | GLU | 91 | 7.880 | 55.961 | 0.153 | 1.00 | 28.46 |
| ATOM | 650 | CA | GLU | 91 | 9.197 | 55.802 | 0.733 | 1.00 | 30.58 |
| ATOM | 651 | CB | GLU | 91 | 10.204 | 55.557 | −0.388 | 1.00 | 36.00 |
| ATOM | 652 | CG | GLU | 91 | 9.820 | 54.367 | −1.251 | 1.00 | 44.17 |
| ATOM | 653 | CD | GLU | 91 | 10.713 | 54.198 | −2.463 | 1.00 | 49.46 |
| ATOM | 654 | OE1 | GLU | 91 | 10.435 | 53.284 | −3.277 | 1.00 | 50.63 |
| ATOM | 655 | OE2 | GLU | 91 | 11.687 | 54.977 | −2.601 | 1.00 | 52.77 |
| ATOM | 656 | C | GLU | 91 | 9.573 | 57.040 | 1.542 | 1.00 | 27.34 |
| ATOM | 657 | O | GLU | 91 | 10.241 | 56.941 | 2.567 | 1.00 | 28.42 |
| ATOM | 658 | N | ASN | 92 | 9.132 | 58.202 | 1.079 | 1.00 | 24.91 |
| ATOM | 659 | CA | ASN | 92 | 9.405 | 59.460 | 1.757 | 1.00 | 22.31 |
| ATOM | 660 | CB | ASN | 92 | 9.064 | 60.616 | 0.840 | 1.00 | 20.97 |
| ATOM | 661 | CG | ASN | 92 | 7.571 | 60.779 | 0.650 | 1.00 | 23.29 |
| ATOM | 662 | OD1 | ASN | 92 | 6.778 | 59.874 | 0.965 | 1.00 | 22.87 |

TABLE 2-continued

FGFR1 D2–D3 Complexed with FGF1

| ATOM | 663 | ND2 | ASN | 92 | 7.171 | 61.935 | 0.130 | 1.00 | 21.91 |
|------|-----|-----|-----|----|-------|--------|-------|------|-------|
| ATOM | 664 | C | ASN | 92 | 8.558 | 59.551 | 3.027 | 1.00 | 23.86 |
| ATOM | 665 | O | ASN | 92 | 8.481 | 60.600 | 3.666 | 1.00 | 25.03 |
| ATOM | 666 | N | HIS | 93 | 7.899 | 58.447 | 3.358 | 1.00 | 23.09 |
| ATOM | 667 | CA | HIS | 93 | 7.086 | 58.339 | 4.559 | 1.00 | 22.39 |
| ATOM | 668 | GB | HIS | 93 | 7.945 | 58.601 | 5.793 | 1.00 | 23.17 |
| ATOM | 669 | CG | HIS | 93 | 8.847 | 57.461 | 6.137 | 1.00 | 26.20 |
| ATOM | 670 | CD2 | HIS | 93 | 9.770 | 57.312 | 7.114 | 1.00 | 30.14 |
| ATOM | 671 | ND1 | HIS | 93 | 8.841 | 56.276 | 5.432 | 1.00 | 29.43 |
| ATOM | 672 | GE1 | HIS | 93 | 9.723 | 55.446 | 5.959 | 1.00 | 28.79 |
| ATOM | 673 | NE2 | HIS | 93 | 10.301 | 56.049 | 6.982 | 1.00 | 30.20 |
| ATOM | 674 | C | HIS | 93 | 5.825 | 59.166 | 4.612 | 1.00 | 22.28 |
| ATOM | 675 | O | HIS | 93 | 5.259 | 59.406 | 5.688 | 1.00 | 20.33 |
| ATOM | 676 | N | TYR | 94 | 5.372 | 59.585 | 3.440 | 1.00 | 22.58 |
| ATOM | 677 | CA | TYR | 94 | 4.141 | 60.348 | 3.345 | 1.00 | 20.96 |
| ATOM | 678 | GB | TYR | 94 | 4.348 | 61.593 | 2.489 | 1.00 | 18.29 |
| ATOM | 679 | CG | TYR | 94 | 4.940 | 62.749 | 3.243 | 1.00 | 16.89 |
| ATOM | 680 | CD1 | TYR | 94 | 4.159 | 63.484 | 4.136 | 1.00 | 17.65 |
| ATOM | 681 | CE1 | TYR | 94 | 4.707 | 64.543 | 4.861 | 1.00 | 16.95 |
| ATOM | 682 | CD2 | TYR | 94 | 6.293 | 63.098 | 3.090 | 1.00 | 13.56 |
| ATOM | 683 | CE2 | TYR | 94 | 6.849 | 64.146 | 3.808 | 1.00 | 10.87 |
| ATOM | 684 | CZ | TYR | 94 | 6.048 | 64.863 | 4.691 | 1.00 | 13.37 |
| ATOM | 685 | OH | TYR | 94 | 6.555 | 65.916 | 5.399 | 1.00 | 15.56 |
| ATOM | 686 | C | TYR | 94 | 3.125 | 59.438 | 2.682 | 1.00 | 21.15 |
| ATOM | 687 | O | TYR | 94 | 3.482 | 58.394 | 2.130 | 1.00 | 18.49 |
| ATOM | 688 | N | ASN | 95 | 1.859 | 59.827 | 2.757 | 1.00 | 20.46 |
| ATOM | 689 | CA | ASN | 95 | 0.801 | 59.067 | 2.119 | 1.00 | 20.78 |
| ATOM | 690 | GB | ASN | 95 | −0.413 | 58.915 | 3.033 | 1.00 | 18.65 |
| ATOM | 691 | CG | ASN | 95 | −0.316 | 57.709 | 3.915 | 1.00 | 22.19 |
| ATOM | 692 | OD1 | ASN | 95 | 0.564 | 56.848 | 3.716 | 1.00 | 22.07 |
| ATOM | 693 | ND2 | ASN | 95 | −1.225 | 57.616 | 4.899 | 1.00 | 13.47 |
| ATOM | 694 | C | ASN | 95 | 0.345 | 59.806 | 0.880 | 1.00 | 22.07 |
| ATOM | 695 | O | ASN | 95 | 0.415 | 61.040 | 0.806 | 1.00 | 24.43 |
| ATOM | 696 | N | THR | 96 | −0.104 | 59.050 | −0.107 | 1.00 | 19.08 |
| ATOM | 697 | CA | THR | 96 | −0.648 | 59.654 | −1.301 | 1.00 | 17.85 |
| ATOM | 698 | GB | THR | 96 | 0.293 | 59.564 | −2.494 | 1.00 | 13.90 |
| ATOM | 699 | OG1 | THR | 96 | 0.627 | 58.194 | −2.733 | 1.00 | 16.54 |
| ATOM | 700 | CG2 | THR | 96 | 1.534 | 60.388 | −2.245 | 1.00 | 8.64 |
| ATOM | 701 | C | THR | 96 | −1.905 | 58.870 | −1.604 | 1.00 | 19.75 |
| ATOM | 702 | O | THR | 96 | −1.952 | 57.656 | −1.398 | 1.00 | 19.27 |
| ATOM | 703 | N | TYR | 97 | −2.931 | 59.573 | −2.065 | 1.00 | 21.57 |
| ATOM | 704 | CA | TYR | 97 | −4.188 | 58.932 | −2.400 | 1.00 | 23.58 |
| ATOM | 705 | GB | TYR | 97 | −5.283 | 59.469 | −1.485 | 1.00 | 23.44 |
| ATOM | 706 | CG | TYR | 97 | −5.031 | 59.152 | −0.029 | 1.00 | 25.02 |
| ATOM | 707 | CD1 | TYR | 97 | −5.403 | 57.918 | 0.511 | 1.00 | 26.72 |
| ATOM | 708 | GE1 | TYR | 97 | −5.157 | 57.610 | 1.851 | 1.00 | 25.40 |
| ATOM | 709 | CD2 | TYR | 97 | −4.399 | 60.076 | 0.810 | 1.00 | 24.77 |
| ATOM | 710 | CE2 | TYR | 97 | −4.149 | 59.781 | 2.145 | 1.00 | 23.43 |
| ATOM | 711 | CZ | TYR | 97 | −4.532 | 58.547 | 2.660 | 1.00 | 25.51 |
| ATOM | 712 | OH | TYR | 97 | −4.299 | 58.253 | 3.984 | 1.00 | 25.72 |
| ATOM | 713 | C | TYR | 97 | −4.521 | 59.184 | −3.871 | 1.00 | 25.49 |
| ATOM | 714 | O | TYR | 97 | −4.761 | 60.322 | −4.281 | 1.00 | 26.61 |
| ATOM | 715 | N | ILE | 98 | −4.501 | 58.116 | −4.662 | 1.00 | 26.27 |
| ATOM | 716 | GA | ILE | 98 | −4.807 | 58.199 | −6.083 | 1.00 | 25.07 |
| ATOM | 717 | GB | ILE | 98 | −3.864 | 57.292 | −6.913 | 1.00 | 26.82 |
| ATOM | 718 | CG2 | ILE | 98 | −4.420 | 57.106 | −8.333 | 1.00 | 26.59 |
| ATOM | 719 | CG1 | ILE | 98 | −2.457 | 57.905 | −6.933 | 1.00 | 29.67 |
| ATOM | 720 | CD1 | ILE | 98 | −1.412 | 57.093 | −7.682 | 1.00 | 29.38 |
| ATOM | 721 | C | ILE | 98 | −6.239 | 57.757 | −6.333 | 1.00 | 24.20 |
| ATOM | 722 | O | ILE | 98 | −6.703 | 56.784 | −5.739 | 1.00 | 21.30 |
| ATOM | 723 | N | SER | 99 | −6.934 | 58.485 | −7.205 | 1.00 | 25.81 |
| ATOM | 724 | CA | SER | 99 | −8.312 | 58.143 | −7.564 | 1.00 | 25.53 |
| ATOM | 725 | GB | SER | 99 | −8.845 | 59.082 | −8.644 | 1.00 | 24.28 |
| ATOM | 726 | OG | SER | 99 | −9.827 | 58.425 | −9.419 | 1.00 | 25.10 |
| ATOM | 727 | C | SER | 99 | −8.310 | 56.729 | −8.115 | 1.00 | 26.04 |
| ATOM | 728 | O | SER | 99 | −7.602 | 56.432 | −9.084 | 1.00 | 23.70 |
| ATOM | 729 | N | LYS | 100 | −9.101 | 55.863 | −7.491 | 1.00 | 27.88 |
| ATOM | 730 | CA | LYS | 100 | −9.195 | 54.468 | −7.903 | 1.00 | 27.72 |
| ATOM | 731 | CB | LYS | 100 | −10.045 | 53.687 | −6.897 | 1.00 | 26.37 |
| ATOM | 732 | CG | LYS | 100 | −9.848 | 52.176 | −6.908 | 1.00 | 25.42 |
| ATOM | 733 | CD | LYS | 100 | −10.364 | 51.544 | −8.171 | 1.00 | 23.12 |
| ATOM | 734 | CE | LYS | 100 | −10.292 | 50.028 | −8.091 | 1.00 | 26.78 |
| ATOM | 735 | NZ | LYS | 100 | −11.136 | 49.473 | −6.995 | 1.00 | 27.99 |
| ATOM | 736 | C | LYS | 100 | −9.809 | 54.391 | −9.293 | 1.00 | 28.12 |
| ATOM | 737 | O | LYS | 100 | −9.402 | 53.571 | −10.113 | 1.00 | 27.55 |
| ATOM | 738 | N | LYS | 101 | −10.777 | 55.264 | −9.552 | 1.00 | 30.25 |
| ATOM | 739 | CA | LYS | 101 | −11.454 | 55.297 | −10.840 | 1.00 | 34.17 |

TABLE 2-continued

FGFR1 D2–D3 Complexed with FGF1

| ATOM | 740 | CE | LYS | 101 | −12.770 | 56.070 | −10.720 | 1.00 | 36.86 |
|---|---|---|---|---|---|---|---|---|---|
| ATOM | 741 | CG | LYS | 101 | −13.554 | 56.186 | −12.025 | 1.00 | 37.77 |
| ATOM | 742 | CD | LYS | 101 | −14.802 | 57.027 | −11.843 | 1.00 | 38.43 |
| ATOM | 743 | CE | LYS | 101 | −15.534 | 57.241 | −13.161 | 1.00 | 39.99 |
| ATOM | 744 | NZ | LYS | 101 | −16.726 | 58.124 | −12.996 | 1.00 | 39.40 |
| ATOM | 745 | C | LYS | 101 | −10.604 | 55.923 | −11.943 | 1.00 | 34.72 |
| ATOM | 746 | O | LYS | 101 | −10.696 | 55.536 | −13.102 | 1.00 | 35.47 |
| ATOM | 747 | N | HIS | 102 | −9.780 | 56.895 | −11.591 | 1.00 | 34.55 |
| ATOM | 748 | CA | HIS | 102 | −8.955 | 57.543 | −12.596 | 1.00 | 36.40 |
| ATOM | 749 | CB | HIS | 102 | −9.241 | 59.048 | −12.584 | 1.00 | 40.56 |
| ATOM | 750 | CG | HIS | 102 | −10.628 | 59.392 | −13.040 | 1.00 | 44.63 |
| ATOM | 751 | CD2 | HIS | 102 | −11.758 | 59.655 | −12.340 | 1.00 | 45.60 |
| ATOM | 752 | NO1 | HIS | 102 | −10.983 | 59.438 | −14.372 | 1.00 | 47.62 |
| ATOM | 753 | CE1 | HIS | 102 | −12.272 | 59.715 | −14.472 | 1.00 | 49.39 |
| ATOM | 754 | NE2 | HIS | 102 | −12.766 | 59.851 | −13.253 | 1.00 | 48.16 |
| ATOM | 755 | C | HIS | 102 | −7.471 | 57.249 | −12.393 | 1.00 | 35.09 |
| ATOM | 756 | O | HIS | 102 | −6.604 | 58.097 | −12.635 | 1.00 | 30.28 |
| ATOM | 757 | N | ALA | 103 | −7.198 | 56.019 | −11.962 | 1.00 | 35.43 |
| ATOM | 758 | CA | ALA | 103 | −5.842 | 55.561 | −11.705 | 1.00 | 37.35 |
| ATOM | 759 | CE | ALA | 103 | −5.871 | 54.138 | −11.211 | 1.00 | 34.67 |
| ATOM | 760 | C | ALA | 103 | −4.948 | 55.666 | −12.934 | 1.00 | 39.11 |
| ATOM | 761 | O | ALA | 103 | −3.886 | 56.287 | −12.887 | 1.00 | 41.02 |
| ATOM | 762 | N | GLU | 104 | −5.382 | 55.046 | −14.025 | 1.00 | 40.77 |
| ATOM | 763 | CA | GLU | 104 | −4.641 | 55.059 | −15.282 | 1.00 | 40.86 |
| ATOM | 764 | CE | GLU | 104 | −5.591 | 54.695 | −16.422 | 1.00 | 43.20 |
| ATOM | 765 | CG | GLU | 104 | −5.130 | 55.168 | −17.787 | 1.00 | 49.96 |
| ATOM | 766 | CD | GLU | 104 | −6.293 | 55.507 | −18.713 | 1.00 | 52.78 |
| ATOM | 767 | OE1 | GLU | 104 | −6.045 | 56.087 | −19.796 | 1.00 | 52.63 |
| ATOM | 768 | OE2 | GLU | 104 | −7.453 | 55.194 | −18.357 | 1.00 | 53.57 |
| ATOM | 769 | C | GLU | 104 | −3.971 | 56.408 | −15.569 | 1.00 | 39.23 |
| ATOM | 770 | O | GLU | 104 | −2.804 | 56.462 | −15.944 | 1.00 | 38.66 |
| ATOM | 771 | N | LYS | 105 | −4.714 | 57.493 | −15.390 | 1.00 | 39.54 |
| ATOM | 772 | CA | LYS | 105 | −4.192 | 58.833 | −15.641 | 1.00 | 38.83 |
| ATOM | 773 | CE | LYS | 105 | −5.345 | 59.814 | −15.842 | 1.00 | 35.41 |
| ATOM | 774 | CG | LYS | 105 | −6.562 | 59.186 | −16.484 | 1.00 | 34.90 |
| ATOM | 775 | CD | LYS | 105 | −7.832 | 59.953 | −16.147 | 1.00 | 36.61 |
| ATOM | 776 | CE | LYS | 105 | −9.058 | 59.174 | −16.584 | 1.00 | 37.07 |
| ATOM | 777 | NZ | LYS | 105 | −8.974 | 57.765 | −16.092 | 1.00 | 38.64 |
| ATOM | 778 | C | LYS | 105 | −3.340 | 59.314 | −14.473 | 1.00 | 39.73 |
| ATOM | 779 | O | LYS | 105 | −2.691 | 60.350 | −14.564 | 1.00 | 42.17 |
| ATOM | 780 | N | ASN | 106 | −3.345 | 58.568 | −13.375 | 1.00 | 39.76 |
| ATOM | 781 | CA | ASN | 106 | −2.586 | 58.962 | −12.194 | 1.00 | 41.17 |
| ATOM | 782 | CB | ASN | 106 | −1.099 | 59.080 | −12.538 | 1.00 | 41.89 |
| ATOM | 783 | CG | ASN | 106 | −0.386 | 57.741 | −12.474 | 1.00 | 45.65 |
| ATOM | 784 | OD1 | ASN | 106 | 0.626 | 57.531 | −13.143 | 1.00 | 48.02 |
| ATOM | 785 | ND2 | ASN | 106 | −0.908 | 56.827 | −11.653 | 1.00 | 44.93 |
| ATOM | 786 | C | ASN | 106 | −3.117 | 60.279 | −11.625 | 1.00 | 39.74 |
| ATOM | 787 | O | ASN | 106 | −2.413 | 61.281 | −11.557 | 1.00 | 39.43 |
| ATOM | 788 | N | TRP | 107 | −4.379 | 60.254 | −11.222 | 1.00 | 39.27 |
| ATOM | 789 | CA | TRP | 107 | −5.051 | 61.412 | −10.651 | 1.00 | 39.02 |
| ATOM | 790 | CB | TRP | 107 | −6.515 | 61.410 | −11.096 | 1.00 | 42.22 |
| ATOM | 791 | CG | TRP | 107 | −6.733 | 62.007 | −12.451 | 1.00 | 45.87 |
| ATOM | 792 | CD2 | TRP | 107 | −7.984 | 62.429 | −13.008 | 1.00 | 47.87 |
| ATOM | 793 | CE2 | TRP | 107 | −7.713 | 62.964 | −14.286 | 1.00 | 48.19 |
| ATOM | 794 | CE3 | TRP | 107 | −9.311 | 62.407 | −12.549 | 1.00 | 46.97 |
| ATOM | 795 | CD1 | TRP | 107 | −5.782 | 62.290 | −13.391 | 1.00 | 45.43 |
| ATOM | 796 | NE1 | TRP | 107 | −6.362 | 62.869 | −14.494 | 1.00 | 45.12 |
| ATOM | 797 | CZ2 | TRP | 107 | −8.723 | 63.475 | −15.113 | 1.00 | 49.27 |
| ATOM | 798 | CZ3 | TRP | 107 | −10.313 | 62.916 | −13.370 | 1.00 | 46.53 |
| ATOM | 799 | CH2 | TRP | 107 | −10.012 | 63.442 | −14.638 | 1.00 | 47.09 |
| ATOM | 800 | C | TRP | 107 | −4.958 | 61.385 | −9.123 | 1.00 | 36.02 |
| ATOM | 801 | O | TRP | 107 | −5.563 | 60.537 | −8.466 | 1.00 | 32.66 |
| ATOM | 802 | N | PHE | 108 | −4.205 | 62.322 | −8.560 | 1.00 | 33.43 |
| ATOM | 803 | CA | PHE | 108 | −4.021 | 62.364 | −7.118 | 1.00 | 29.53 |
| ATOM | 804 | GB | PHE | 108 | −2.617 | 62.854 | −6.747 | 1.00 | 25.07 |
| ATOM | 805 | CG | PHE | 108 | −1.501 | 62.011 | −7.278 | 1.00 | 24.26 |
| ATOM | 806 | CO1 | PHE | 108 | −0.959 | 62.263 | −8.544 | 1.00 | 20.53 |
| ATOM | 807 | CO2 | PHE | 108 | −0.965 | 60.982 | −6.502 | 1.00 | 23.65 |
| ATOM | 808 | GE1 | PHE | 108 | 0.098 | 61.511 | −9.030 | 1.00 | 19.10 |
| ATOM | 809 | CE2 | PHE | 108 | 0.098 | 60.215 | −6.977 | 1.00 | 23.67 |
| ATOM | 810 | CZ | PHE | 108 | 0.632 | 60.481 | −8.248 | 1.00 | 24.38 |
| ATOM | 811 | C | PHE | 108 | −4.990 | 63.268 | −6.394 | 1.00 | 29.53 |
| ATOM | 812 | O | PHE | 108 | −5.611 | 64.150 | −6.991 | 1.00 | 28.70 |
| ATOM | 813 | N | VAL | 109 | −5.095 | 63.021 | −5.087 | 1.00 | 28.71 |
| ATOM | 814 | CA | VAL | 109 | −5.885 | 63.833 | −4.181 | 1.00 | 28.24 |
| ATOM | 815 | GB | VAL | 109 | −6.384 | 63.036 | −2.966 | 1.00 | 28.28 |
| ATOM | 816 | CG1 | VAL | 109 | −6.582 | 63.972 | −1.794 | 1.00 | 28.81 |

TABLE 2-continued

FGFR1 D2–D3 Complexed with FGF1

| ATOM | 817 | CG2 | VAL | 109 | −7.703 | 62.347 | −3.289 | 1.00 | 29.67 |
|---|---|---|---|---|---|---|---|---|---|
| ATOM | 818 | C | VAL | 109 | −4.791 | 64.776 | −3.712 | 1.00 | 28.77 |
| ATOM | 819 | O | VAL | 109 | −3.783 | 64.334 | −3.162 | 1.00 | 30.15 |
| ATOM | 820 | N | GLY | 110 | −4.957 | 66.065 | −3.959 | 1.00 | 28.53 |
| ATOM | 821 | CA | GLY | 110 | −3.926 | 66.997 | −3.552 | 1.00 | 27.81 |
| ATOM | 822 | C | GLY | 110 | −4.525 | 68.296 | −3.079 | 1.00 | 27.32 |
| ATOM | 823 | O | GLY | 110 | −5.745 | 68.448 | −3.043 | 1.00 | 27.33 |
| ATOM | 824 | N | LEU | 111 | −3.667 | 69.237 | −2.711 | 1.00 | 25.62 |
| ATOM | 825 | CA | LEU | 111 | −4.128 | 70.530 | −2.246 | 1.00 | 25.47 |
| ATOM | 826 | GB | LEU | 111 | −4.374 | 70.482 | −0.738 | 1.00 | 25.49 |
| ATOM | 827 | CG | LEU | 111 | −5.595 | 69.678 | −0.277 | 1.00 | 25.80 |
| ATOM | 828 | CD1 | LEU | 111 | −5.407 | 69.184 | 1.157 | 1.00 | 21.96 |
| ATOM | 829 | CD2 | LEU | 111 | −6.845 | 70.561 | −0.400 | 1.00 | 24.98 |
| ATOM | 830 | C | LEU | 111 | −3.069 | 71.556 | −2.601 | 1.00 | 26.94 |
| ATOM | 831 | O | LEU | 111 | −1.868 | 71.270 | −2.575 | 1.00 | 25.36 |
| ATOM | 832 | N | LYS | 112 | −3.519 | 72.757 | −2.938 | 1.00 | 29.56 |
| ATOM | 833 | CA | LYS | 112 | −2.613 | 73.825 | −3.335 | 1.00 | 31.20 |
| ATOM | 834 | GB | LYS | 112 | −3.305 | 74.708 | −4.370 | 1.00 | 34.94 |
| ATOM | 835 | CG | LYS | 112 | −3.551 | 74.027 | −5.697 | 1.00 | 35.87 |
| ATOM | 836 | CD | LYS | 112 | −4.189 | 74.997 | −6.675 | 1.00 | 39.81 |
| ATOM | 837 | CE | LYS | 112 | −3.450 | 75.001 | −8.006 | 1.00 | 43.47 |
| ATOM | 838 | NZ | LYS | 112 | −4.076 | 75.931 | −8.996 | 1.00 | 46.95 |
| ATOM | 839 | C | LYS | 112 | −2.091 | 74.695 | −2.190 | 1.00 | 29.91 |
| ATOM | 840 | O | LYS | 112 | −2.672 | 74.727 | −1.111 | 1.00 | 27.10 |
| ATOM | 841 | N | LYS | 113 | −0.996 | 75.405 | −2.456 | 1.00 | 29.29 |
| ATOM | 842 | CA | LYS | 113 | −0.371 | 76.294 | −1.485 | 1.00 | 31.65 |
| ATOM | 843 | GB | LYS | 113 | 0.510 | 77.311 | −2.198 | 1.00 | 33.37 |
| ATOM | 844 | CG | LYS | 113 | 1.824 | 76.744 | −2.686 | 1.00 | 37.28 |
| ATOM | 845 | CD | LYS | 113 | 2.788 | 76.487 | −1.544 | 1.00 | 37.50 |
| ATOM | 846 | CE | LYS | 113 | 3.602 | 75.225 | −1.785 | 1.00 | 39.66 |
| ATOM | 847 | NZ | LYS | 113 | 4.235 | 75.174 | −3.133 | 1.00 | 40.46 |
| ATOM | 848 | C | LYS | 113 | −1.354 | 77.040 | −0.599 | 1.00 | 32.81 |
| ATOM | 849 | O | LYS | 113 | −1.047 | 77.354 | 0.544 | 1.00 | 34.94 |
| ATOM | 850 | N | ASN | 114 | −2.537 | 77.330 | −1.115 | 1.00 | 34.59 |
| ATOM | 851 | CA | ASN | 114 | −3.525 | 78.046 | −0.324 | 1.00 | 34.22 |
| ATOM | 852 | CD | ASN | 114 | −4.133 | 79.187 | −1.136 | 1.00 | 36.34 |
| ATOM | 853 | CG | ASN | 114 | −4.910 | 78.691 | −2.328 | 1.00 | 36.23 |
| ATOM | 854 | OD1 | ASN | 114 | −5.778 | 77.836 | −2.196 | 1.00 | 36.00 |
| ATOM | 855 | ND2 | ASN | 114 | −4.603 | 79.225 | −3.501 | 1.00 | 37.05 |
| ATOM | 856 | C | ASN | 114 | −4.636 | 77.133 | 0.168 | 1.00 | 33.79 |
| ATOM | 857 | O | ASN | 114 | −5.635 | 77.608 | 0.701 | 1.00 | 36.07 |
| ATOM | 858 | N | GLY | 115 | −4.480 | 75.830 | −0.037 | 1.00 | 32.03 |
| ATOM | 859 | CA | GLY | 115 | −5.474 | 74.885 | 0.444 | 1.00 | 34.61 |
| ATOM | 860 | C | GLY | 115 | −6.698 | 74.667 | −0.417 | 1.00 | 35.87 |
| ATOM | 861 | O | GLY | 115 | −7.632 | 73.962 | −0.035 | 1.00 | 34.51 |
| ATOM | 862 | N | SER | 116 | −6.700 | 75.280 | −1.586 | 1.00 | 38.93 |
| ATOM | 863 | CA | SER | 116 | −7.817 | 75.128 | −2.489 | 1.00 | 39.18 |
| ATOM | 864 | CB | SER | 116 | −7.872 | 76.303 | −3.462 | 1.00 | 38.46 |
| ATOM | 865 | OG | SER | 116 | −8.902 | 76.120 | −4.408 | 1.00 | 39.70 |
| ATOM | 866 | C | SER | 116 | −7.651 | 73.826 | −3.251 | 1.00 | 40.32 |
| ATOM | 867 | O | SER | 116 | −6.532 | 73.399 | −3.542 | 1.00 | 39.78 |
| ATOM | 868 | N | CYS | 117 | −8.785 | 73.201 | −3.549 | 1.00 | 42.63 |
| ATOM | 869 | CA | CYS | 117 | −8.829 | 71.951 | −4.290 | 1.00 | 44.43 |
| ATOM | 870 | CB | CYS | 117 | −10.261 | 71.738 | −4.788 | 1.00 | 42.26 |
| ATOM | 871 | SG | CYS | 117 | −10.434 | 70.534 | −6.094 | 1.00 | 42.90 |
| ATOM | 872 | C | CYS | 117 | −7.856 | 71.988 | −5.476 | 1.00 | 46.45 |
| ATOM | 873 | O | CYS | 117 | −7.838 | 72.964 | −6.223 | 1.00 | 49.26 |
| ATOM | 874 | N | LYS | 118 | −7.030 | 70.956 | −5.638 | 1.00 | 46.83 |
| ATOM | 875 | CA | LYS | 118 | −6.104 | 70.920 | −6.777 | 1.00 | 48.07 |
| ATOM | 876 | CB | LYS | 118 | −4.665 | 70.620 | −6.320 | 1.00 | 47.48 |
| ATOM | 877 | CG | LYS | 118 | −3.660 | 70.503 | −7.480 | 1.00 | 46.98 |
| ATOM | 878 | CD | LYS | 118 | −2.286 | 71.111 | −7.147 | 1.00 | 47.17 |
| ATOM | 879 | CE | LYS | 118 | −1.352 | 71.100 | −8.376 | 1.00 | 47.11 |
| ATOM | 880 | NZ | LYS | 118 | −0.079 | 71.867 | −8.193 | 1.00 | 41.89 |
| ATOM | 881 | C | LYS | 118 | −6.561 | 69.880 | −7.808 | 1.00 | 48.93 |
| ATOM | 882 | O | LYS | 118 | −6.445 | 68.677 | −7.587 | 1.00 | 49.49 |
| ATOM | 883 | N | ARG | 119 | −7.091 | 70.361 | −8.929 | 1.00 | 49.25 |
| ATOM | 884 | CA | ARG | 119 | −7.585 | 69.507 | −10.001 | 1.00 | 47.75 |
| ATOM | 885 | CD | ARG | 119 | −7.671 | 70.302 | −11.303 | 1.00 | 50.94 |
| ATOM | 886 | CG | ARG | 119 | −8.068 | 71.764 | −11.113 | 1.00 | 56.67 |
| ATOM | 887 | CD | ARC | 119 | −8.327 | 72.459 | −12.449 | 1.00 | 59.61 |
| ATOM | 888 | NE | ARC | 119 | −9.407 | 71.804 | −13.182 | 1.00 | 60.94 |
| ATOM | 889 | CZ | ARC | 119 | −9.241 | 71.117 | −14.308 | 1.00 | 61.86 |
| ATOM | 890 | NH1 | ARG | 119 | −8.031 | 71.000 | −14.844 | 1.00 | 63.34 |
| ATOM | 891 | NH2 | ARC | 119 | −10.283 | 70.533 | −14.887 | 1.00 | 60.50 |
| ATOM | 892 | C | ARC | 119 | −6.686 | 68.298 | −10.209 | 1.00 | 47.41 |
| ATOM | 893 | O | ARC | 119 | −5.503 | 68.437 | −10.504 | 1.00 | 46.81 |

TABLE 2-continued

| | | | FGFR1 D2–D3 Complexed with FGF1 | | | | | |
|---|---|---|---|---|---|---|---|---|
| ATOM | 894 | N | GLY | 120 | −7.257 | 67.110 | −10.056 | 1.00 | 47.81 |
| ATOM | 895 | CA | GLY | 120 | −6.497 | 65.886 | −10.236 | 1.00 | 48.33 |
| ATOM | 896 | C | GLY | 120 | −5.611 | 65.830 | −11.472 | 1.00 | 49.08 |
| ATOM | 897 | O | GLY | 120 | −4.489 | 65.339 | −11.387 | 1.00 | 49.07 |
| ATOM | 898 | N | PRO | 121 | −6.071 | 66.313 | −12.637 | 1.00 | 49.33 |
| ATOM | 899 | CD | PRO | 121 | −7.404 | 66.837 | −12.974 | 1.00 | 48.84 |
| ATOM | 900 | CA | PRO | 121 | −5.233 | 66.267 | −13.836 | 1.00 | 49.58 |
| ATOM | 901 | CB | PRO | 121 | −6.214 | 66.603 | −14.945 | 1.00 | 48.50 |
| ATOM | 902 | CC | PRO | 121 | −7.131 | 67.551 | −14.270 | 1.00 | 48.21 |
| ATOM | 903 | C | PRO | 121 | −4.032 | 67.209 | −13.828 | 1.00 | 50.68 |
| ATOM | 904 | O | PRO | 121 | −3.309 | 67.285 | −14.820 | 1.00 | 51.26 |
| ATOM | 905 | N | ARC | 122 | −3.821 | 67.927 | −12.727 | 1.00 | 51.69 |
| ATOM | 906 | CA | ARG | 122 | −2.681 | 68.847 | −12.629 | 1.00 | 51.88 |
| ATOM | 907 | CB | ARC | 122 | −3.148 | 70.286 | −12.367 | 1.00 | 56.07 |
| ATOM | 908 | CC | ARC | 122 | −4.602 | 70.587 | −12.723 | 1.00 | 61.69 |
| ATOM | 909 | CD | ARC | 122 | −4.904 | 70.420 | −14.211 | 1.00 | 67.71 |
| ATOM | 910 | NE | ARC | 122 | −4.299 | 71.449 | −15.057 | 1.00 | 70.79 |
| ATOM | 911 | CZ | ARG | 122 | −4.503 | 71.547 | −16.370 | 1.00 | 73.15 |
| ATOM | 912 | NH1 | ARG | 122 | −5.298 | 70.679 | −16.992 | 1.00 | 73.19 |
| ATOM | 913 | NH2 | ARG | 122 | −3.912 | 72.509 | −17.066 | 1.00 | 74.22 |
| ATOM | 914 | C | ARG | 122 | −1.748 | 68.408 | −11.492 | 1.00 | 50.05 |
| ATOM | 915 | O | ARG | 122 | −0.853 | 69.153 | −11.079 | 1.00 | 47.68 |
| ATOM | 916 | N | THR | 123 | −1.974 | 67.194 | −10.995 | 1.00 | 47.61 |
| ATOM | 917 | CA | THR | 123 | −1.172 | 66.638 | −9.919 | 1.00 | 45.19 |
| ATOM | 918 | GB | THR | 123 | −2.054 | 65.882 | −8.914 | 1.00 | 40.61 |
| ATOM | 919 | OG1 | THR | 123 | −2.418 | 64.611 | −9.453 | 1.00 | 34.32 |
| ATOM | 920 | CG2 | THR | 123 | −3.318 | 66.672 | −8.630 | 1.00 | 38.47 |
| ATOM | 921 | C | THR | 123 | −0.106 | 65.687 | −10.470 | 1.00 | 48.36 |
| ATOM | 922 | O | THR | 123 | −0.403 | 64.783 | −11.258 | 1.00 | 49.22 |
| ATOM | 923 | N | HIS | 124 | 1.136 | 65.899 | −10.043 | 1.00 | 51.15 |
| ATOM | 924 | CA | HIS | 124 | 2.269 | 65.091 | −10.485 | 1.00 | 52.99 |
| ATOM | 925 | GB | HIS | 124 | 3.333 | 66.001 | −11.121 | 1.00 | 57.19 |
| ATOM | 926 | CG | HIS | 124 | 4.480 | 65.262 | −11.739 | 1.00 | 61.62 |
| ATOM | 927 | CD2 | HIS | 124 | 4.886 | 65.165 | −13.029 | 1.00 | 64.23 |
| ATOM | 928 | ND1 | HIS | 124 | 5.363 | 64.501 | −11.003 | 1.00 | 64.57 |
| ATOM | 929 | CE1 | HIS | 124 | 6.262 | 63.965 | −11.811 | 1.00 | 64.97 |
| ATOM | 930 | NE2 | HIS | 124 | 5.994 | 64.354 | −13.046 | 1.00 | 66.03 |
| ATOM | 931 | C | HIS | 124 | 2.883 | 64.314 | −9.324 | 1.00 | 53.02 |
| ATOM | 932 | O | HIS | 124 | 2.746 | 64.698 | −8.162 | 1.00 | 52.95 |
| ATOM | 933 | N | TYR | 125 | 3.562 | 63.219 | −9.658 | 1.00 | 53.83 |
| ATOM | 934 | CA | TYR | 125 | 4.221 | 62.369 | −8.676 | 1.00 | 53.98 |
| ATOM | 935 | CB | TYR | 125 | 4.996 | 61.262 | −9.387 | 1.00 | 59.15 |
| ATOM | 936 | CG | TYR | 125 | 5.894 | 60.463 | −8.469 | 1.00 | 66.50 |
| ATOM | 937 | CD1 | TYR | 125 | 5.358 | 59.606 | −7.496 | 1.00 | 69.66 |
| ATOM | 938 | GE1 | TYR | 125 | 6.193 | 58.878 | −6.629 | 1.00 | 72.55 |
| ATOM | 939 | CD2 | TYR | 125 | 7.284 | 60.576 | −8.557 | 1.00 | 69.56 |
| ATOM | 940 | CE2 | TYR | 125 | 8.128 | 59.856 | −7.698 | 1.00 | 72.02 |
| ATOM | 941 | CZ | TYR | 125 | 7.579 | 59.011 | −6.740 | 1.00 | 73.15 |
| ATOM | 942 | OH | TYR | 125 | 8.417 | 58.301 | −5.906 | 1.00 | 73.04 |
| ATOM | 943 | C | TYR | 125 | 5.178 | 63.134 | −7.765 | 1.00 | 52.11 |
| ATOM | 944 | O | TYR | 125 | 5.307 | 62.812 | −6.583 | 1.00 | 53.02 |
| ATOM | 945 | N | GLY | 126 | 5.844 | 64.147 | −8.306 | 1.00 | 48.32 |
| ATOM | 946 | CA | GLY | 126 | 6.793 | 64.901 | −7.507 | 1.00 | 44.37 |
| ATOM | 947 | C | GLY | 126 | 6.261 | 66.128 | −6.790 | 1.00 | 42.58 |
| ATOM | 948 | O | GLY | 126 | 7.041 | 66.958 | −6.313 | 1.00 | 41.62 |
| ATOM | 949 | N | GLN | 127 | 4.944 | 66.249 | −6.688 | 1.00 | 39.00 |
| ATOM | 950 | CA | GLN | 127 | 4.369 | 67.411 | −6.031 | 1.00 | 35.99 |
| ATOM | 951 | GB | GLN | 127 | 3.023 | 67.747 | −6.678 | 1.00 | 36.59 |
| ATOM | 952 | CG | GLN | 127 | 3.098 | 67.961 | −8.183 | 1.00 | 36.01 |
| ATOM | 953 | CD | GLN | 127 | 1.862 | 68.646 | −8.737 | 1.00 | 37.86 |
| ATOM | 954 | OE1 | GLN | 127 | 0.737 | 68.196 | −8.512 | 1.00 | 39.21 |
| ATOM | 955 | NE2 | GLN | 127 | 2.066 | 69.742 | −9.468 | 1.00 | 39.34 |
| ATOM | 956 | C | GLN | 127 | 4.205 | 67.283 | −4.512 | 1.00 | 33.73 |
| ATOM | 957 | O | GLN | 127 | 4.070 | 66.184 | −3.970 | 1.00 | 32.12 |
| ATOM | 958 | N | LYS | 128 | 4.238 | 68.426 | −3.833 | 1.00 | 31.42 |
| ATOM | 959 | CA | LYS | 128 | 4.074 | 68.478 | −2.388 | 1.00 | 30.39 |
| ATOM | 960 | GB | LYS | 128 | 4.706 | 69.754 | −1.821 | 1.00 | 32.97 |
| ATOM | 961 | CG | LYS | 128 | 6.187 | 69.665 | −1.469 | 1.00 | 35.91 |
| ATOM | 962 | CD | LYS | 128 | 6.748 | 71.060 | −1.135 | 1.00 | 39.16 |
| ATOM | 963 | CE | LYS | 128 | 7.544 | 71.085 | 0.170 | 1.00 | 38.59 |
| ATOM | 964 | NZ | LYS | 128 | 6.677 | 70.905 | 1.383 | 1.00 | 36.98 |
| ATOM | 965 | C | LYS | 128 | 2.578 | 68.508 | −2.132 | 1.00 | 28.93 |
| ATOM | 966 | O | LYS | 128 | 2.105 | 68.196 | −1.039 | 1.00 | 27.14 |
| ATOM | 967 | N | ALA | 129 | 1.835 | 68.889 | −3.161 | 1.00 | 27.52 |
| ATOM | 968 | CA | ALA | 129 | 0.388 | 68.980 | −3.061 | 1.00 | 28.25 |
| ATOM | 969 | GB | ALA | 129 | −0.173 | 69.620 | −4.320 | 1.00 | 27.44 |
| ATOM | 970 | C | ALA | 129 | −0.299 | 67.638 | −2.812 | 1.00 | 27.33 |

TABLE 2-continued

| FGFR1 D2–D3 Complexed with FGF1 | | | | | | | | |
|---|---|---|---|---|---|---|---|---|
| ATOM | 971 | O | ALA | 129 | −1.341 | 67.591 | −2.156 | 1.00 | 25.70 |
| ATOM | 972 | N | ILE | 130 | 0.276 | 66.551 | −3.329 | 1.00 | 26.39 |
| ATOM | 973 | CA | ILE | 130 | −0.331 | 65.230 | −3.154 | 1.00 | 26.25 |
| ATOM | 974 | CB | ILE | 130 | −0.166 | 64.360 | −4.425 | 1.00 | 24.09 |
| ATOM | 975 | CG2 | ILE | 130 | −0.764 | 65.075 | −5.617 | 1.00 | 24.03 |
| ATOM | 976 | CG1 | ILE | 130 | 1.308 | 64.069 | −4.685 | 1.00 | 21.11 |
| ATOM | 977 | CD1 | ILE | 130 | 1.535 | 63.077 | −5.810 | 1.00 | 16.42 |
| ATOM | 978 | C | ILE | 130 | 0.172 | 64.435 | −1.948 | 1.00 | 25.50 |
| ATOM | 979 | O | ILE | 130 | −0.242 | 63.295 | −1.736 | 1.00 | 28.33 |
| ATOM | 980 | N | LEU | 131 | 1.054 | 65.039 | −1.159 | 1.00 | 23.92 |
| ATOM | 981 | CA | LEU | 131 | 1.608 | 64.389 | 0.023 | 1.00 | 19.80 |
| ATOM | 982 | CB | LEU | 131 | 3.050 | 64.848 | 0.248 | 1.00 | 15.70 |
| ATOM | 983 | CG | LEU | 131 | 4.031 | 64.395 | −0.838 | 1.00 | 13.31 |
| ATOM | 984 | CD1 | LEU | 131 | 5.388 | 65.061 | −0.640 | 1.00 | 12.10 |
| ATOM | 985 | CD2 | LEU | 131 | 4.163 | 62.885 | −0.791 | 1.00 | 7.44 |
| ATOM | 986 | C | LEU | 131 | 0.765 | 64.675 | 1.257 | 1.00 | 20.49 |
| ATOM | 987 | O | LEU | 131 | 0.506 | 65.834 | 1.609 | 1.00 | 20.71 |
| ATOM | 988 | N | PHE | 132 | 0.337 | 63.605 | 1.915 | 1.00 | 20.52 |
| ATOM | 989 | CA | PHE | 132 | −0.495 | 63.726 | 3.103 | 1.00 | 21.43 |
| ATOM | 990 | GB | PHE | 132 | −1.909 | 63.210 | 2.803 | 1.00 | 23.94 |
| ATOM | 991 | CG | PHE | 132 | −2.707 | 64.124 | 1.914 | 1.00 | 28.64 |
| ATOM | 992 | CD1 | PHE | 132 | −3.445 | 65.175 | 2.459 | 1.00 | 28.95 |
| ATOM | 993 | CD2 | PHE | 132 | −2.676 | 63.971 | 0.529 | 1.00 | 29.70 |
| ATOM | 994 | GE1 | PHE | 132 | −4.135 | 66.060 | 1.636 | 1.00 | 30.99 |
| ATOM | 995 | CE2 | PHE | 132 | −3.360 | 64.853 | −0.306 | 1.00 | 30.81 |
| ATOM | 996 | CZ | PHE | 132 | −4.092 | 65.899 | 0.245 | 1.00 | 32.10 |
| ATOM | 997 | C | PHE | 132 | 0.084 | 62.989 | 4.299 | 1.00 | 20.23 |
| ATOM | 998 | O | PHE | 132 | 0.827 | 62.026 | 4.157 | 1.00 | 21.47 |
| ATOM | 999 | N | LEU | 133 | −0.288 | 63.444 | 5.483 | 1.00 | 18.17 |
| ATOM | 1000 | CA | LEU | 133 | 0.198 | 62.854 | 6.703 | 1.00 | 18.68 |
| ATOM | 1001 | GB | LEU | 133 | 1.212 | 63.809 | 7.323 | 1.00 | 20.20 |
| ATOM | 1002 | CG | LEU | 133 | 2.279 | 63.282 | 8.266 | 1.00 | 20.39 |
| ATOM | 1003 | CD1 | LEU | 133 | 3.062 | 62.191 | 7.582 | 1.00 | 16.71 |
| ATOM | 1004 | CD2 | LEU | 133 | 3.202 | 64.429 | 8.661 | 1.00 | 21.39 |
| ATOM | 1005 | C | LEU | 133 | −0.974 | 62.635 | 7.651 | 1.00 | 20.10 |
| ATOM | 1006 | O | LEU | 133 | −1.768 | 63.550 | 7.878 | 1.00 | 19.72 |
| ATOM | 1007 | N | PRO | 134 | −1.121 | 61.411 | 8.196 | 1.00 | 21.14 |
| ATOM | 1008 | CD | PRO | 134 | −0.513 | 60.153 | 7.733 | 1.00 | 20.54 |
| ATOM | 1009 | CA | PRO | 134 | −2.226 | 61.133 | 9.125 | 1.00 | 21.38 |
| ATOM | 1010 | CB | PRO | 134 | −2.287 | 59.606 | 9.153 | 1.00 | 17.91 |
| ATOM | 1011 | CG | PRO | 134 | −1.654 | 59.200 | 7.863 | 1.00 | 19.11 |
| ATOM | 1012 | C | PRO | 134 | −1.902 | 61.710 | 10.508 | 1.00 | 21.87 |
| ATOM | 1013 | O | PRO | 134 | −0.785 | 61.575 | 10.990 | 1.00 | 22.43 |
| ATOM | 1014 | N | LEU | 135 | −2.866 | 62.369 | 11.138 | 1.00 | 22.87 |
| ATOM | 1015 | CA | LEU | 135 | −2.634 | 62.926 | 12.466 | 1.00 | 21.38 |
| ATOM | 1016 | GB | LEU | 135 | −2.405 | 64.438 | 12.426 | 1.00 | 17.99 |
| ATOM | 1017 | CG | LEU | 135 | −1.223 | 65.052 | 11.672 | 1.00 | 16.42 |
| ATOM | 1018 | GD1 | LEU | 135 | −0.994 | 66.466 | 12.186 | 1.00 | 9.72 |
| ATOM | 1019 | CD2 | LEU | 135 | 0.019 | 64.227 | 11.873 | 1.00 | 12.39 |
| ATOM | 1020 | C | LEU | 135 | −3.828 | 62.670 | 13.349 | 1.00 | 22.74 |
| ATOM | 1021 | O | LEU | 135 | −4.952 | 62.557 | 12.863 | 1.00 | 23.73 |
| ATOM | 1022 | N | PRO | 136 | −3.596 | 62.560 | 14.669 | 1.00 | 26.01 |
| ATOM | 1023 | CD | PRO | 136 | −2.263 | 62.410 | 15.279 | 1.00 | 25.14 |
| ATOM | 1024 | CA | PRO | 136 | −4.650 | 62.322 | 15.667 | 1.00 | 25.96 |
| ATOM | 1025 | GB | PRO | 136 | −3.860 | 62.059 | 16.944 | 1.00 | 26.54 |
| ATOM | 1026 | CG | PRO | 136 | −2.559 | 61.505 | 16.437 | 1.00 | 25.10 |
| ATOM | 1027 | C | PRO | 136 | −5.468 | 63.601 | 15.757 | 1.00 | 26.58 |
| ATOM | 1028 | O | PRO | 136 | −4.971 | 64.678 | 15.449 | 1.00 | 28.99 |
| ATOM | 1029 | N | VAL | 137 | −6.713 | 63.509 | 16.187 | 1.00 | 27.68 |
| ATOM | 1030 | CA | VAL | 137 | −7.523 | 64.717 | 16.244 | 1.00 | 27.15 |
| ATOM | 1031 | GB | VAL | 137 | −8.908 | 64.423 | 16.818 | 1.00 | 24.53 |
| ATOM | 1032 | CG1 | VAL | 137 | −9.665 | 65.719 | 17.015 | 1.00 | 26.11 |
| ATOM | 1033 | CG2 | VAL | 137 | −9.676 | 63.502 | 15.863 | 1.00 | 23.43 |
| ATOM | 1034 | C | VAL | 137 | −6.877 | 65.846 | 17.039 | 1.00 | 29.13 |
| ATOM | 1035 | O | VAL | 137 | −6.850 | 66.998 | 16.581 | 1.00 | 26.88 |
| ATOM | 1036 | N | SER | 138 | −6.350 | 65.502 | 18.218 | 1.00 | 32.45 |
| ATOM | 1037 | CA | SER | 138 | −5.708 | 66.464 | 19.128 | 1.00 | 32.31 |
| ATOM | 1038 | CB | SER | 138 | −6.133 | 66.176 | 20.575 | 1.00 | 30.03 |
| ATOM | 1039 | C | SER | 138 | −4.180 | 66.494 | 19.043 | 1.00 | 31.29 |
| ATOM | 1040 | O | SER | 138 | −3.602 | 67.477 | 19.570 | 1.00 | 30.54 |
| ATOM | 1041 | GB | TYR | 1008 | 12.631 | 46.833 | 26.062 | 1.00 | 31.16 |
| ATOM | 1042 | CG | TYR | 1008 | 13.713 | 47.571 | 25.287 | 1.00 | 30.94 |
| ATOM | 1043 | CD1 | TYR | 1008 | 15.010 | 47.693 | 25.793 | 1.00 | 27.23 |
| ATOM | 1044 | GE1 | TYR | 1008 | 15.977 | 48.436 | 25.124 | 1.00 | 25.79 |
| ATOM | 1045 | CD2 | TYR | 1008 | 13.421 | 48.207 | 24.076 | 1.00 | 30.33 |
| ATOM | 1046 | CE2 | TYR | 1008 | 14.385 | 48.956 | 23.403 | 1.00 | 26.73 |
| ATOM | 1047 | CZ | TYR | 1008 | 15.659 | 49.067 | 23.935 | 1.00 | 25.79 |

TABLE 2-continued

FGFR1 D2–D3 Complexed with FGF1

| ATOM | 1048 | OH | TYR | 1008 | 16.602 | 49.836 | 23.297 | 1.00 | 24.67 |
|---|---|---|---|---|---|---|---|---|---|
| ATOM | 1049 | C | TYR | 1008 | 13.192 | 48.186 | 28.111 | 1.00 | 35.73 |
| ATOM | 1050 | O | TYR | 1008 | 14.012 | 47.437 | 28.658 | 1.00 | 36.45 |
| ATOM | 1051 | N | TYR | 1008 | 11.123 | 48.698 | 26.792 | 1.00 | 32.07 |
| ATOM | 1052 | CA | TYR | 1008 | 12.049 | 47.614 | 27.261 | 1.00 | 34.16 |
| ATOM | 1053 | N | LYS | 1009 | 13.255 | 49.513 | 28.205 | 1.00 | 35.03 |
| ATOM | 1054 | CA | LYS | 1009 | 14.289 | 50.155 | 29.005 | 1.00 | 35.16 |
| ATOM | 1055 | CB | LYS | 1009 | 14.747 | 51.459 | 28.349 | 1.00 | 34.86 |
| ATOM | 1056 | CG | LYS | 1009 | 15.601 | 51.245 | 27.107 | 1.00 | 36.13 |
| ATOM | 1057 | CD | LYS | 1009 | 16.422 | 52.478 | 26.773 | 1.00 | 35.32 |
| ATOM | 1058 | CE | LYS | 1009 | 17.518 | 52.145 | 25.772 | 1.00 | 37.93 |
| ATOM | 1059 | NZ | LYS | 1009 | 18.571 | 53.214 | 25.709 | 1.00 | 39.50 |
| ATOM | 1060 | C | LYS | 1009 | 13.783 | 50.431 | 30.421 | 1.00 | 35.77 |
| ATOM | 1061 | O | LYS | 1009 | 14.569 | 50.561 | 31.361 | 1.00 | 37.64 |
| ATOM | 1062 | N | LYS | 1010 | 12.464 | 50.507 | 30.564 | 1.00 | 33.46 |
| ATOM | 1063 | CA | LYS | 1010 | 11.833 | 50.766 | 31.850 | 1.00 | 31.68 |
| ATOM | 1064 | GB | LYS | 1010 | 10.358 | 51.138 | 31.633 | 1.00 | 28.72 |
| ATOM | 1065 | C | LYS | 1010 | 11.941 | 49.557 | 32.788 | 1.00 | 31.01 |
| ATOM | 1066 | O | LYS | 1010 | 11.957 | 48.409 | 32.344 | 1.00 | 30.93 |
| ATOM | 1067 | N | PRO | 1011 | 12.029 | 49.805 | 34.103 | 1.00 | 30.79 |
| ATOM | 1068 | CD | PRO | 1011 | 12.250 | 51.089 | 34.788 | 1.00 | 29.71 |
| ATOM | 1069 | CA | PRO | 1011 | 12.131 | 48.687 | 35.047 | 1.00 | 30.41 |
| ATOM | 1070 | GB | PRO | 1011 | 12.464 | 49.376 | 36.373 | 1.00 | 30.93 |
| ATOM | 1071 | CG | PRO | 1011 | 13.115 | 50.667 | 35.943 | 1.00 | 32.31 |
| ATOM | 1072 | C | PRO | 1011 | 10.798 | 47.961 | 35.099 | 1.00 | 28.96 |
| ATOM | 1073 | O | PRO | 1011 | 9.759 | 48.592 | 34.985 | 1.00 | 31.83 |
| ATOM | 1074 | N | LYS | 1012 | 10.823 | 46.645 | 35.273 | 1.00 | 27.44 |
| ATOM | 1075 | GA | LYS | 1012 | 9.584 | 45.885 | 35.321 | 1.00 | 27.45 |
| ATOM | 1076 | GB | LYS | 1012 | 9.504 | 44.892 | 34.160 | 1.00 | 28.07 |
| ATOM | 1077 | CG | LYS | 1012 | 10.095 | 45.369 | 32.856 | 1.00 | 35.39 |
| ATOM | 1078 | CD | LYS | 1012 | 10.115 | 44.231 | 31.835 | 1.00 | 41.91 |
| ATOM | 1079 | CE | LYS | 1012 | 10.690 | 44.665 | 30.478 | 1.00 | 44.00 |
| ATOM | 1080 | NZ | LYS | 1012 | 10.707 | 43.530 | 29.503 | 1.00 | 45.76 |
| ATOM | 1081 | C | LYS | 1012 | 9.555 | 45.085 | 36.598 | 1.00 | 27.92 |
| ATOM | 1082 | O | LYS | 1012 | 10.420 | 45.224 | 37.462 | 1.00 | 27.67 |
| ATOM | 1083 | N | LEU | 1013 | 8.541 | 44.236 | 36.696 | 1.00 | 25.10 |
| ATOM | 1084 | CA | LEU | 1013 | 8.394 | 43.341 | 37.822 | 1.00 | 24.38 |
| ATOM | 1085 | GB | LEU | 1013 | 7.102 | 43.631 | 38.590 | 1.00 | 22.68 |
| ATOM | 1086 | CG | LEU | 1013 | 6.685 | 45.090 | 38.740 | 1.00 | 22.27 |
| ATOM | 1087 | CD1 | LEU | 1013 | 5.211 | 45.149 | 39.144 | 1.00 | 19.72 |
| ATOM | 1088 | CD2 | LEU | 1013 | 7.591 | 45.789 | 39.743 | 1.00 | 18.29 |
| ATOM | 1089 | C | LEU | 1013 | 8.271 | 41.988 | 37.120 | 1.00 | 26.07 |
| ATOM | 1090 | O | LEU | 1013 | 7.665 | 41.897 | 36.047 | 1.00 | 25.61 |
| ATOM | 1091 | N | LEU | 1014 | 8.864 | 40.948 | 37.697 | 1.00 | 26.39 |
| ATOM | 1092 | CA | LEU | 1014 | 8.771 | 39.617 | 37.121 | 1.00 | 24.33 |
| ATOM | 1093 | GB | LEU | 1014 | 10.144 | 38.933 | 37.087 | 1.00 | 23.95 |
| ATOM | 1094 | CG | LEU | 1014 | 11.238 | 39.533 | 36.193 | 1.00 | 24.67 |
| ATOM | 1095 | CD1 | LEU | 1014 | 12.344 | 38.511 | 36.017 | 1.00 | 23.77 |
| ATOM | 1096 | CD2 | LEU | 1014 | 10.677 | 39.904 | 34.823 | 1.00 | 27.16 |
| ATOM | 1097 | C | LEU | 1014 | 7.800 | 38.839 | 38.000 | 1.00 | 24.55 |
| ATOM | 1098 | O | LEU | 1014 | 8.175 | 38.290 | 39.032 | 1.00 | 29.11 |
| ATOM | 1099 | N | TYR | 1015 | 6.541 | 38.833 | 37.584 | 1.00 | 21.89 |
| ATOM | 1100 | CA | TYR | 1015 | 5.465 | 38.158 | 38.285 | 1.00 | 19.64 |
| ATOM | 1101 | GB | TYR | 1015 | 4.135 | 38.708 | 37.757 | 1.00 | 19.02 |
| ATOM | 1102 | CG | TYR | 1015 | 2.889 | 37.937 | 38.129 | 1.00 | 17.57 |
| ATOM | 1103 | CD1 | TYR | 1015 | 2.476 | 36.825 | 37.395 | 1.00 | 12.24 |
| ATOM | 1104 | GE1 | TYR | 1015 | 1.316 | 36.130 | 37.739 | 1.00 | 12.74 |
| ATOM | 1105 | CD2 | TYR | 1015 | 2.111 | 38.332 | 39.219 | 1.00 | 20.06 |
| ATOM | 1106 | CE2 | TYR | 1015 | 0.950 | 37.642 | 39.570 | 1.00 | 17.48 |
| ATOM | 1107 | GZ | TYR | 1015 | 0.560 | 36.544 | 38.832 | 1.00 | 14.74 |
| ATOM | 1108 | OH | TYR | 1015 | −0.574 | 35.866 | 39.224 | 1.00 | 17.22 |
| ATOM | 1109 | C | TYR | 1015 | 5.575 | 36.669 | 38.025 | 1.00 | 22.05 |
| ATOM | 1110 | O | TYR | 1015 | 5.731 | 36.254 | 36.880 | 1.00 | 23.85 |
| ATOM | 1111 | N | CYS | 1016 | 5.520 | 35.864 | 39.080 | 1.00 | 23.50 |
| ATOM | 1112 | CA | CYS | 1016 | 5.588 | 34.413 | 38.916 | 1.00 | 28.51 |
| ATOM | 1113 | GB | CYS | 1016 | 6.462 | 33.775 | 39.988 | 1.00 | 28.93 |
| ATOM | 1114 | SG | CYS | 1016 | 6.619 | 31.990 | 39.744 | 1.00 | 35.75 |
| ATOM | 1115 | C | CYS | 1016 | 4.177 | 33.848 | 39.020 | 1.00 | 30.00 |
| ATOM | 1116 | O | CYS | 1016 | 3.465 | 34.110 | 39.992 | 1.00 | 31.04 |
| ATOM | 1117 | N | SER | 1017 | 3.781 | 33.053 | 38.032 | 1.00 | 31.14 |
| ATOM | 1118 | CA | SER | 1017 | 2.426 | 32.504 | 38.005 | 1.00 | 33.96 |
| ATOM | 1119 | GB | SER | 1017 | 2.096 | 32.065 | 36.578 | 1.00 | 33.83 |
| ATOM | 1120 | OG | SER | 1017 | 3.123 | 31.238 | 36.061 | 1.00 | 37.73 |
| ATOM | 1121 | C | SER | 1017 | 2.102 | 31.369 | 38.987 | 1.00 | 35.14 |
| ATOM | 1122 | O | SER | 1017 | 0.934 | 30.988 | 39.142 | 1.00 | 34.27 |
| ATOM | 1123 | N | ASN | 1018 | 3.122 | 30.851 | 39.666 | 1.00 | 35.68 |
| ATOM | 1124 | CA | ASN | 1018 | 2.919 | 29.754 | 40.603 | 1.00 | 35.41 |

TABLE 2-continued

| | | | FGFR1 D2–D3 Complexed with FGF1 | | | | | |
|---|---|---|---|---|---|---|---|---|
| ATOM | 1125 | GB | ASN | 1018 | 4.271 | 29.121 | 40.947 | 1.00 | 37.23 |
| ATOM | 1126 | CG | ASN | 1018 | 4.131 | 27.744 | 41.565 | 1.00 | 36.80 |
| ATOM | 1127 | OD1 | ASN | 1018 | 3.520 | 26.843 | 40.987 | 1.00 | 36.57 |
| ATOM | 1128 | ND2 | ASN | 1018 | 4.704 | 27.575 | 42.748 | 1.00 | 40.08 |
| ATOM | 1129 | C | ASN | 1018 | 2.162 | 30.148 | 41.880 | 1.00 | 34.04 |
| ATOM | 1130 | O | ASN | 1018 | 1.490 | 29.314 | 42.485 | 1.00 | 36.26 |
| ATOM | 1131 | N | GLY | 1019 | 2.253 | 31.410 | 42.288 | 1.00 | 32.38 |
| ATOM | 1132 | CA | GLY | 1019 | 1.548 | 31.839 | 43.489 | 1.00 | 30.23 |
| ATOM | 1133 | C | GLY | 1019 | 1.185 | 33.313 | 43.472 | 1.00 | 30.12 |
| ATOM | 1134 | O | GLY | 1019 | 0.650 | 33.863 | 44.443 | 1.00 | 28.62 |
| ATOM | 1135 | N | GLY | 1020 | 1.487 | 33.958 | 42.353 | 1.00 | 30.37 |
| ATOM | 1136 | CA | GLY | 1020 | 1.196 | 35.369 | 42.217 | 1.00 | 32.01 |
| ATOM | 1137 | C | GLY | 1020 | 2.228 | 36.257 | 42.882 | 1.00 | 31.94 |
| ATOM | 1138 | O | GLY | 1020 | 1.955 | 37.437 | 43.120 | 1.00 | 34.75 |
| ATOM | 1139 | N | HIS | 1021 | 3.409 | 35.704 | 43.171 | 1.00 | 31.44 |
| ATOM | 1140 | CA | HIS | 1021 | 4.480 | 36.460 | 43.831 | 1.00 | 29.29 |
| ATOM | 1141 | CB | HIS | 1021 | 5.358 | 35.541 | 44.699 | 1.00 | 29.74 |
| ATOM | 1142 | CG | HIS | 1021 | 4.633 | 34.903 | 45.844 | 1.00 | 30.85 |
| ATOM | 1143 | CD2 | HIS | 1021 | 4.368 | 35.354 | 47.093 | 1.00 | 30.24 |
| ATOM | 1144 | ND1 | HIS | 1021 | 4.076 | 33.643 | 45.764 | 1.00 | 28.93 |
| ATOM | 1145 | GE1 | HIS | 1021 | 3.499 | 33.346 | 46.916 | 1.00 | 30.37 |
| ATOM | 1146 | NE2 | HIS | 1021 | 3.661 | 34.366 | 47.740 | 1.00 | 32.23 |
| ATOM | 1147 | C | HIS | 1021 | 5.389 | 37.194 | 42.867 | 1.00 | 27.47 |
| ATOM | 1148 | O | HIS | 1021 | 5.773 | 36.658 | 41.828 | 1.00 | 28.41 |
| ATOM | 1149 | N | PHE | 1022 | 5.741 | 38.421 | 43.229 | 1.00 | 26.08 |
| ATOM | 1150 | CA | PHE | 1022 | 6.637 | 39.234 | 42.422 | 1.00 | 26.98 |
| ATOM | 1151 | GB | PHE | 1022 | 6.378 | 40.726 | 42.652 | 1.00 | 29.06 |
| ATOM | 1152 | CG | PHE | 1022 | 5.044 | 41.194 | 42.152 | 1.00 | 33.42 |
| ATOM | 1153 | CD1 | PHE | 1022 | 4.942 | 42.356 | 41.399 | 1.00 | 35.57 |
| ATOM | 1154 | CD2 | PHE | 1022 | 3.887 | 40.472 | 42.430 | 1.00 | 36.07 |
| ATOM | 1155 | CE1 | PHE | 1022 | 3.713 | 42.791 | 40.930 | 1.00 | 35.49 |
| ATOM | 1156 | CE2 | PHE | 1022 | 2.655 | 40.899 | 41.966 | 1.00 | 36.57 |
| ATOM | 1157 | CZ | PHE | 1022 | 2.568 | 42.062 | 41.213 | 1.00 | 35.79 |
| ATOM | 1158 | C | PHE | 1022 | 8.058 | 38.916 | 42.842 | 1.00 | 27.74 |
| ATOM | 1159 | O | PHE | 1022 | 8.386 | 38.978 | 44.037 | 1.00 | 28.42 |
| ATOM | 1160 | N | LEU | 1023 | 8.905 | 38.586 | 41.869 | 1.00 | 26.44 |
| ATOM | 1161 | CA | LEU | 1023 | 10.294 | 38.278 | 42.173 | 1.00 | 25.87 |
| ATOM | 1162 | GB | LEU | 1023 | 11.070 | 38.015 | 40.885 | 1.00 | 22.37 |
| ATOM | 1163 | CG | LEU | 1023 | 12.441 | 37.371 | 41.093 | 1.00 | 24.38 |
| ATOM | 1164 | CD1 | LEU | 1023 | 12.332 | 36.176 | 42.043 | 1.00 | 20.70 |
| ATOM | 1165 | CD2 | LEU | 1023 | 13.002 | 36.951 | 39.743 | 1.00 | 23.30 |
| ATOM | 1166 | C | LEU | 1023 | 10.898 | 39.457 | 42.948 | 1.00 | 25.50 |
| ATOM | 1167 | O | LEU | 1023 | 10.807 | 40.608 | 42.516 | 1.00 | 24.70 |
| ATOM | 1168 | N | ARG | 1024 | 11.489 | 39.150 | 44.104 | 1.00 | 27.06 |
| ATOM | 1169 | CA | ARG | 1024 | 12.092 | 40.149 | 44.998 | 1.00 | 26.64 |
| ATOM | 1170 | CB | ARG | 1024 | 11.282 | 40.229 | 46.301 | 1.00 | 24.40 |
| ATOM | 1171 | CG | ARG | 1024 | 11.960 | 41.004 | 47.407 | 1.00 | 19.74 |
| ATOM | 1172 | CD | ARG | 1024 | 10.992 | 41.364 | 48.527 | 1.00 | 17.02 |
| ATOM | 1173 | NE | ARG | 1024 | 10.461 | 40.193 | 49.219 | 1.00 | 19.05 |
| ATOM | 1174 | CZ | ARG | 1024 | 9.777 | 40.245 | 50.363 | 1.00 | 21.94 |
| ATOM | 1175 | NH1 | ARG | 1024 | 9.541 | 41.407 | 50.955 | 1.00 | 20.91 |
| ATOM | 1176 | NH2 | ARG | 1024 | 9.310 | 39.137 | 50.919 | 1.00 | 25.83 |
| ATOM | 1177 | C | ARG | 1024 | 13.548 | 39.873 | 45.348 | 1.00 | 24.92 |
| ATOM | 1178 | O | ARG | 1024 | 13.932 | 38.729 | 45.586 | 1.00 | 27.55 |
| ATOM | 1179 | N | ILE | 1025 | 14.355 | 40.925 | 45.376 | 1.00 | 25.20 |
| ATOM | 1180 | CA | ILE | 1025 | 15.770 | 40.791 | 45.734 | 1.00 | 27.59 |
| ATOM | 1181 | GB | ILE | 1025 | 16.704 | 41.245 | 44.581 | 1.00 | 27.75 |
| ATOM | 1182 | CG2 | ILE | 1025 | 18.162 | 41.066 | 44.994 | 1.00 | 27.22 |
| ATOM | 1183 | CG1 | ILE | 1025 | 16.424 | 40.431 | 43.313 | 1.00 | 25.51 |
| ATOM | 1184 | CD1 | ILE | 1025 | 17.321 | 40.810 | 42.144 | 1.00 | 22.73 |
| ATOM | 1185 | C | ILE | 1025 | 16.059 | 41.656 | 46.966 | 1.00 | 27.93 |
| ATOM | 1186 | O | ILE | 1025 | 16.398 | 42.837 | 46.837 | 1.00 | 28.55 |
| ATOM | 1187 | N | LEU | 1026 | 15.901 | 41.067 | 48.152 | 1.00 | 29.13 |
| ATOM | 1188 | CA | LEU | 1026 | 16.133 | 41.764 | 49.420 | 1.00 | 30.12 |
| ATOM | 1189 | CB | LEU | 1026 | 15.744 | 40.864 | 50.583 | 1.00 | 30.24 |
| ATOM | 1190 | CG | LEU | 1026 | 14.253 | 40.510 | 50.579 | 1.00 | 30.34 |
| ATOM | 1191 | GD1 | LEU | 1026 | 13.980 | 39.378 | 51.578 | 1.00 | 29.27 |
| ATOM | 1192 | GD2 | LEU | 1026 | 13.432 | 41.759 | 50.909 | 1.00 | 24.29 |
| ATOM | 1193 | C | LEU | 1026 | 17.594 | 42.202 | 49.544 | 1.00 | 30.91 |
| ATOM | 1194 | O | LEU | 1026 | 18.512 | 41.436 | 49.235 | 1.00 | 29.93 |
| ATOM | 1195 | N | PRO | 1027 | 17.822 | 43.438 | 50.015 | 1.00 | 31.36 |
| ATOM | 1196 | CD | PRO | 1027 | 16.754 | 44.228 | 50.666 | 1.00 | 30.05 |
| ATOM | 1197 | CA | PRO | 1027 | 19.127 | 44.086 | 50.212 | 1.00 | 30.53 |
| ATOM | 1198 | GB | PRO | 1027 | 18.771 | 45.368 | 50.963 | 1.00 | 29.38 |
| ATOM | 1199 | CG | PRO | 1027 | 17.520 | 45.004 | 51.693 | 1.00 | 30.61 |
| ATOM | 1200 | C | PRO | 1027 | 20.250 | 43.282 | 50.879 | 1.00 | 30.41 |
| ATOM | 1201 | O | PRO | 1027 | 21.415 | 43.650 | 50.804 | 1.00 | 30.55 |

TABLE 2-continued

FGFR1 D2–D3 Complexed with FGF1

| ATOM | 1202 | N | ASP | 1028 | 19.897 | 42.175 | 51.509 | 1.00 | 31.88 |
|---|---|---|---|---|---|---|---|---|---|
| ATOM | 1203 | CA | ASP | 1028 | 20.865 | 41.316 | 52.175 | 1.00 | 33.73 |
| ATOM | 1204 | CB | ASP | 1028 | 20.212 | 40.774 | 53.421 | 1.00 | 36.11 |
| ATOM | 1205 | CG | ASP | 1028 | 18.770 | 40.437 | 53.182 | 1.00 | 40.54 |
| ATOM | 1206 | OD1 | ASP | 1028 | 18.502 | 39.362 | 52.595 | 1.00 | 39.57 |
| ATOM | 1207 | OD2 | ASP | 1028 | 17.907 | 41.273 | 53.546 | 1.00 | 44.85 |
| ATOM | 1208 | C | ASP | 1028 | 21.294 | 40.154 | 51.273 | 1.00 | 34.93 |
| ATOM | 1209 | O | ASP | 1028 | 22.074 | 39.292 | 51.679 | 1.00 | 35.53 |
| ATOM | 1210 | N | GLY | 1029 | 20.771 | 40.129 | 50.054 | 1.00 | 35.81 |
| ATOM | 1211 | CA | GLY | 1029 | 21.110 | 39.070 | 49.125 | 1.00 | 34.91 |
| ATOM | 1212 | C | GLY | 1029 | 20.015 | 38.025 | 49.017 | 1.00 | 35.42 |
| ATOM | 1213 | O | GLY | 1029 | 20.078 | 37.159 | 48.150 | 1.00 | 33.85 |
| ATOM | 1214 | N | THR | 1030 | 19.012 | 38.104 | 49.890 | 1.00 | 36.08 |
| ATOM | 1215 | CA | THR | 1030 | 17.907 | 37.143 | 49.885 | 1.00 | 36.46 |
| ATOM | 1216 | CB | THR | 1030 | 17.082 | 37.217 | 51.204 | 1.00 | 39.04 |
| ATOM | 1217 | OC1 | THR | 1030 | 17.765 | 36.484 | 52.229 | 1.00 | 37.14 |
| ATOM | 1218 | CG2 | THR | 1030 | 15.668 | 36.638 | 51.012 | 1.00 | 37.72 |
| ATOM | 1219 | C | THR | 1030 | 16.952 | 37.322 | 48.711 | 1.00 | 36.12 |
| ATOM | 1220 | O | THR | 1030 | 16.364 | 38.393 | 48.535 | 1.00 | 37.82 |
| ATOM | 1221 | N | VAL | 1031 | 16.797 | 36.256 | 47.925 | 1.00 | 34.66 |
| ATOM | 1222 | CA | VAL | 1031 | 15.914 | 36.241 | 46.757 | 1.00 | 32.25 |
| ATOM | 1223 | CB | VAL | 1031 | 16.622 | 35.588 | 45.557 | 1.00 | 32.21 |
| ATOM | 1224 | CG1 | VAL | 1031 | 15.617 | 35.305 | 44.443 | 1.00 | 28.71 |
| ATOM | 1225 | CG2 | VAL | 1031 | 17.742 | 36.502 | 45.069 | 1.00 | 27.43 |
| ATOM | 1226 | C | VAL | 1031 | 14.622 | 35.481 | 47.079 | 1.00 | 31.61 |
| ATOM | 1227 | O | VAL | 1031 | 14.644 | 34.315 | 47.485 | 1.00 | 31.86 |
| ATOM | 1228 | N | ASP | 1032 | 13.493 | 36.145 | 46.882 | 1.00 | 29.65 |
| ATOM | 1229 | CA | ASP | 1032 | 12.207 | 35.538 | 47.204 | 1.00 | 28.58 |
| ATOM | 1230 | GB | ASP | 1032 | 11.959 | 35.656 | 48.707 | 1.00 | 27.71 |
| ATOM | 1231 | CC | ASP | 1032 | 11.545 | 37.075 | 49.125 | 1.00 | 27.66 |
| ATOM | 1232 | OD1 | ASP | 1032 | 11.886 | 38.060 | 48.418 | 1.00 | 26.65 |
| ATOM | 1233 | OD2 | ASP | 1032 | 10.880 | 37.203 | 50.170 | 1.00 | 22.45 |
| ATOM | 1234 | C | ASP | 1032 | 11.082 | 36.258 | 46.471 | 1.00 | 28.37 |
| ATOM | 1235 | O | ASP | 1032 | 11.330 | 37.059 | 45.572 | 1.00 | 26.82 |
| ATOM | 1236 | N | GLY | 1033 | 9.847 | 35.986 | 46.892 | 1.00 | 27.76 |
| ATOM | 1237 | CA | GLY | 1033 | 8.698 | 36.612 | 46.267 | 1.00 | 26.49 |
| ATOM | 1238 | C | GLY | 1033 | 7.779 | 37.247 | 47.277 | 1.00 | 26.11 |
| ATOM | 1239 | O | GLY | 1033 | 7.820 | 36.912 | 48.458 | 1.00 | 27.57 |
| ATOM | 1240 | N | THR | 1034 | 6.956 | 38.178 | 46.805 | 1.00 | 26.39 |
| ATOM | 1241 | CA | THR | 1034 | 5.987 | 38.882 | 47.646 | 1.00 | 27.75 |
| ATOM | 1242 | GB | THR | 1034 | 6.576 | 40.181 | 48.236 | 1.00 | 28.31 |
| ATOM | 1243 | OG1 | THR | 1034 | 5.508 | 41.047 | 48.646 | 1.00 | 30.58 |
| ATOM | 1244 | CG2 | THR | 1034 | 7.439 | 40.890 | 47.216 | 1.00 | 30.03 |
| ATOM | 1245 | C | THR | 1034 | 4.742 | 39.247 | 46.846 | 1.00 | 27.63 |
| ATOM | 1246 | O | THR | 1034 | 4.775 | 39.294 | 45.619 | 1.00 | 31.50 |
| ATOM | 1247 | N | ARG | 1035 | 3.641 | 39.502 | 47.532 | 1.00 | 24.78 |
| ATOM | 1248 | CA | ARG | 1035 | 2.423 | 39.864 | 46.837 | 1.00 | 25.50 |
| ATOM | 1249 | GB | ARG | 1035 | 1.249 | 39.046 | 47.371 | 1.00 | 25.09 |
| ATOM | 1250 | CG | ARG | 1035 | 1.349 | 37.553 | 47.119 | 1.00 | 23.18 |
| ATOM | 1251 | CD | ARG | 1035 | 0.085 | 36.839 | 47.606 | 1.00 | 27.17 |
| ATOM | 1252 | NE | ARG | 1035 | −0.011 | 35.491 | 47.048 | 1.00 | 31.66 |
| ATOM | 1253 | CZ | ARG | 1035 | −0.103 | 34.377 | 47.771 | 1.00 | 33.76 |
| ATOM | 1254 | NM | ARC | 1035 | −0.122 | 34.422 | 49.101 | 1.00 | 34.54 |
| ATOM | 1255 | NH2 | ARG | 1035 | −0.146 | 33.204 | 47.162 | 1.00 | 35.20 |
| ATOM | 1256 | C | ARG | 1035 | 2.130 | 41.348 | 46.992 | 1.00 | 27.20 |
| ATOM | 1257 | O | ARG | 1035 | 1.005 | 41.785 | 46.805 | 1.00 | 28.13 |
| ATOM | 1258 | N | ASP | 1036 | 3.150 | 42.127 | 47.332 | 1.00 | 31.07 |
| ATOM | 1259 | CA | ASP | 1036 | 2.989 | 43.568 | 47.521 | 1.00 | 32.80 |
| ATOM | 1260 | GB | ASP | 1036 | 3.524 | 43.959 | 48.887 | 1.00 | 35.64 |
| ATOM | 1261 | CG | ASP | 1036 | 3.599 | 45.457 | 49.067 | 1.00 | 40.73 |
| ATOM | 1262 | OD1 | ASP | 1036 | 4.229 | 45.893 | 50.064 | 1.00 | 41.06 |
| ATOM | 1263 | OD2 | ASP | 1036 | 3.028 | 46.186 | 48.217 | 1.00 | 36.48 |
| ATOM | 1264 | C | ASP | 1036 | 3.699 | 44.396 | 46.445 | 1.00 | 33.66 |
| ATOM | 1265 | O | ASP | 1036 | 4.923 | 44.336 | 46.309 | 1.00 | 34.64 |
| ATOM | 1266 | N | ARG | 1037 | 2.931 | 45.185 | 45.700 | 1.00 | 33.72 |
| ATOM | 1267 | CA | ARG | 1037 | 3.496 | 46.000 | 44.626 | 1.00 | 32.18 |
| ATOM | 1268 | CE | ARG | 1037 | 2.438 | 46.321 | 43.563 | 1.00 | 31.11 |
| ATOM | 1269 | CG | ARG | 1037 | 2.015 | 45.120 | 42.750 | 1.00 | 31.44 |
| ATOM | 1270 | CD | ARG | 1037 | 1.118 | 45.481 | 41.571 | 1.00 | 32.91 |
| ATOM | 1271 | NE | ARG | 1037 | 1.828 | 46.167 | 40.492 | 1.00 | 32.28 |
| ATOM | 1272 | CZ | ARC | 1037 | 1.478 | 46.085 | 39.208 | 1.00 | 32.10 |
| ATOM | 1273 | NH1 | ARG | 1037 | 0.434 | 45.346 | 38.848 | 1.00 | 25.01 |
| ATOM | 1274 | NH2 | ARG | 1037 | 2.167 | 46.745 | 38.286 | 1.00 | 32.51 |
| ATOM | 1275 | C | ARC | 1037 | 4.120 | 47.295 | 45.087 | 1.00 | 31.28 |
| ATOM | 1276 | O | ARC | 1037 | 4.809 | 47.958 | 44.313 | 1.00 | 29.49 |
| ATOM | 1277 | N | SER | 1038 | 3.873 | 47.676 | 46.333 | 1.00 | 31.03 |
| ATOM | 1278 | CA | SER | 1038 | 4.458 | 48.912 | 46.818 | 1.00 | 31.59 |

TABLE 2-continued

| | | | | | | | | | |
|---|---|---|---|---|---|---|---|---|---|
| | | | FGFR1 D2–D3 Complexed with FGF1 | | | | | | |
| ATOM | 1279 | GB | SER | 1038 | 3.537 | 49.589 | 47.836 | 1.00 | 31.45 |
| ATOM | 1280 | CG | SER | 1038 | 3.109 | 48.682 | 48.832 | 1.00 | 37.63 |
| ATOM | 1281 | C | SER | 1038 | 5.833 | 48.621 | 47.413 | 1.00 | 31.52 |
| ATOM | 1282 | O | SER | 1038 | 6.585 | 49.549 | 47.745 | 1.00 | 34.45 |
| ATOM | 1283 | N | ASP | 1039 | 6.154 | 47.330 | 47.529 | 1.00 | 27.62 |
| ATOM | 1284 | CA | ASP | 1039 | 7.443 | 46.878 | 48.047 | 1.00 | 23.67 |
| ATOM | 1285 | CB | ASP | 1039 | 7.525 | 45.352 | 47.963 | 1.00 | 24.35 |
| ATOM | 1286 | CG | ASP | 1039 | 8.821 | 44.791 | 48.532 | 1.00 | 25.55 |
| ATOM | 1287 | OD1 | ASP | 1039 | 9.914 | 45.113 | 48.004 | 1.00 | 26.48 |
| ATOM | 1288 | OD2 | ASP | 1039 | 8.743 | 44.014 | 49.509 | 1.00 | 23.80 |
| ATOM | 1289 | C | ASP | 1039 | 8.522 | 47.516 | 47.179 | 1.00 | 22.77 |
| ATOM | 1290 | O | ASP | 1039 | 8.488 | 47.414 | 45.960 | 1.00 | 22.56 |
| ATOM | 1291 | N | GLN | 1040 | 9.480 | 48.180 | 47.810 | 1.00 | 25.29 |
| ATOM | 1292 | CA | GLN | 1040 | 10.551 | 48.861 | 47.084 | 1.00 | 25.09 |
| ATOM | 1293 | GB | GLN | 1040 | 11.270 | 49.828 | 48.027 | 1.00 | 24.45 |
| ATOM | 1294 | C | GLN | 1040 | 11.603 | 47.986 | 46.394 | 1.00 | 25.43 |
| ATOM | 1295 | O | GLN | 1040 | 12.423 | 48.509 | 45.645 | 1.00 | 26.66 |
| ATOM | 1296 | N | HIS | 1041 | 11.589 | 46.673 | 46.620 | 1.00 | 25.52 |
| ATOM | 1297 | CA | HIS | 1041 | 12.607 | 45.809 | 46.009 | 1.00 | 30.58 |
| ATOM | 1298 | GB | HIS | 1041 | 13.342 | 45.022 | 47.105 | 1.00 | 32.53 |
| ATOM | 1299 | CG | HIS | 1041 | 14.078 | 45.892 | 48.078 | 1.00 | 36.17 |
| ATOM | 1300 | CD2 | HIS | 1041 | 15.311 | 46.448 | 48.017 | 1.00 | 35.66 |
| ATOM | 1301 | ND1 | HIS | 1041 | 13.511 | 46.340 | 49.254 | 1.00 | 35.22 |
| ATOM | 1302 | CE1 | HIS | 1041 | 14.364 | 47.137 | 49.874 | 1.00 | 34.23 |
| ATOM | 1303 | NE2 | HIS | 1041 | 15.463 | 47.220 | 49.145 | 1.00 | 35.50 |
| ATOM | 1304 | C | HIS | 1041 | 12.176 | 44.833 | 44.898 | 1.00 | 31.64 |
| ATOM | 1305 | O | HIS | 1041 | 12.896 | 43.871 | 44.594 | 1.00 | 28.85 |
| ATOM | 1306 | N | ILE | 1042 | 11.018 | 45.079 | 44.288 | 1.00 | 32.50 |
| ATOM | 1307 | CA | ILE | 1042 | 10.533 | 44.212 | 43.215 | 1.00 | 30.50 |
| ATOM | 1308 | CB | ILE | 1042 | 9.023 | 43.908 | 43.374 | 1.00 | 29.31 |
| ATOM | 1309 | CG2 | ILE | 1042 | 8.834 | 42.728 | 44.303 | 1.00 | 31.07 |
| ATOM | 1310 | CG1 | ILE | 1042 | 8.285 | 45.135 | 43.909 | 1.00 | 25.07 |
| ATOM | 1311 | CD1 | ILE | 1042 | 6.785 | 44.986 | 43.893 | 1.00 | 24.73 |
| ATOM | 1312 | C | ILE | 1042 | 10.794 | 44.753 | 41.800 | 1.00 | 29.65 |
| ATOM | 1313 | O | ILE | 1042 | 10.647 | 44.015 | 40.819 | 1.00 | 29.85 |
| ATOM | 1314 | N | GLN | 1043 | 11.191 | 46.024 | 41.700 | 1.00 | 25.69 |
| ATOM | 1315 | CA | GLN | 1043 | 11.474 | 46.635 | 40.403 | 1.00 | 25.44 |
| ATOM | 1316 | CB | GLN | 1043 | 11.444 | 48.163 | 40.509 | 1.00 | 24.97 |
| ATOM | 1317 | CG | GLN | 1043 | 10.162 | 48.731 | 41.061 | 1.00 | 27.05 |
| ATOM | 1318 | CD | GLN | 1043 | 10.087 | 48.636 | 42.564 | 1.00 | 30.82 |
| ATOM | 1319 | OE1 | GLN | 1043 | 10.899 | 49.240 | 43.272 | 1.00 | 38.30 |
| ATOM | 1320 | NE2 | GLN | 1043 | 9.116 | 47.882 | 43.068 | 1.00 | 27.25 |
| ATOM | 1321 | C | GLN | 1043 | 12.831 | 46.194 | 39.840 | 1.00 | 23.37 |
| ATOM | 1322 | O | GLN | 1043 | 13.879 | 46.471 | 40.411 | 1.00 | 25.56 |
| ATOM | 1323 | N | LEU | 1044 | 12.805 | 45.540 | 38.692 | 1.00 | 21.81 |
| ATOM | 1324 | CA | LEU | 1044 | 14.027 | 45.049 | 38.088 | 1.00 | 21.98 |
| ATOM | 1325 | GB | LEU | 1044 | 13.942 | 43.530 | 37.937 | 1.00 | 17.13 |
| ATOM | 1326 | CG | LEU | 1044 | 13.249 | 42.869 | 39.132 | 1.00 | 18.26 |
| ATOM | 1327 | CD1 | LEU | 1044 | 12.988 | 41.382 | 38.843 | 1.00 | 15.17 |
| ATOM | 1328 | CD2 | LEU | 1044 | 14.101 | 43.081 | 40.389 | 1.00 | 12.40 |
| ATOM | 1329 | C | LEU | 1044 | 14.321 | 45.672 | 36.734 | 1.00 | 23.97 |
| ATOM | 1330 | O | LEU | 1044 | 13.411 | 46.042 | 35.983 | 1.00 | 24.06 |
| ATOM | 1331 | N | GLN | 1045 | 15.612 | 45.765 | 36.434 | 1.00 | 24.15 |
| ATOM | 1332 | CA | GLN | 1045 | 16.084 | 46.311 | 35.182 | 1.00 | 25.60 |
| ATOM | 1333 | CB | GLN | 1045 | 16.999 | 47.502 | 35.442 | 1.00 | 29.63 |
| ATOM | 1334 | CG | GLN | 1045 | 17.300 | 48.292 | 34.194 | 1.00 | 32.04 |
| ATOM | 1335 | CD | GLN | 1045 | 16.030 | 48.816 | 33.577 | 1.00 | 36.81 |
| ATOM | 1336 | OE1 | GLN | 1045 | 15.306 | 49.596 | 34.200 | 1.00 | 40.53 |
| ATOM | 1337 | NE2 | GLN | 1045 | 15.735 | 48.382 | 32.355 | 1.00 | 36.91 |
| ATOM | 1338 | C | GLN | 1045 | 16.856 | 45.230 | 34.423 | 1.00 | 26.34 |
| ATOM | 1339 | O | GLN | 1045 | 18.035 | 44.977 | 34.700 | 1.00 | 26.34 |
| ATOM | 1340 | N | LEU | 1046 | 16.185 | 44.597 | 33.464 | 1.00 | 25.58 |
| ATOM | 1341 | CA | LEU | 1046 | 16.806 | 43.549 | 32.666 | 1.00 | 23.78 |
| ATOM | 1342 | CB | LEU | 1046 | 15.732 | 42.647 | 32.046 | 1.00 | 22.97 |
| ATOM | 1343 | CG | LEU | 1046 | 15.147 | 41.560 | 32.960 | 1.00 | 23.09 |
| ATOM | 1344 | CD1 | LEU | 1046 | 14.469 | 42.162 | 34.174 | 1.00 | 17.46 |
| ATOM | 1345 | CD2 | LEU | 1046 | 14.167 | 40.733 | 32.163 | 1.00 | 25.21 |
| ATOM | 1346 | C | LEU | 1046 | 17.661 | 44.171 | 31.581 | 1.00 | 22.40 |
| ATOM | 1347 | O | LEU | 1046 | 17.311 | 45.223 | 31.047 | 1.00 | 19.22 |
| ATOM | 1348 | N | SER | 1047 | 18.782 | 43.524 | 31.269 | 1.00 | 23.55 |
| ATOM | 1349 | CA | SER | 1047 | 19.699 | 44.017 | 30.237 | 1.00 | 26.45 |
| ATOM | 1350 | CB | SER | 1047 | 20.830 | 44.820 | 30.871 | 1.00 | 21.82 |
| ATOM | 1351 | OG | SER | 1047 | 20.423 | 45.328 | 32.123 | 1.00 | 25.79 |
| ATOM | 1352 | C | SER | 1047 | 20.300 | 42.850 | 29.460 | 1.00 | 28.44 |
| ATOM | 1353 | O | SER | 1047 | 20.522 | 41.775 | 30.018 | 1.00 | 29.64 |
| ATOM | 1354 | N | ALA | 1048 | 20.578 | 43.064 | 28.178 | 1.00 | 30.05 |
| ATOM | 1355 | CA | ALA | 1048 | 21.158 | 42.009 | 27.358 | 1.00 | 31.08 |

TABLE 2-continued

FGFR1 D2–D3 Complexed with FGF1

| ATOM | 1356 | CB | ALA | 1048 | 20.510 | 42.002 | 25.973 | 1.00 | 29.58 |
|------|------|-----|-----|------|--------|--------|--------|------|-------|
| ATOM | 1357 | C | ALA | 1048 | 22.670 | 42.151 | 27.225 | 1.00 | 33.28 |
| ATOM | 1358 | O | ALA | 1048 | 23.180 | 43.165 | 26.741 | 1.00 | 33.23 |
| ATOM | 1359 | N | GLU | 1049 | 23.395 | 41.140 | 27.679 | 1.00 | 35.86 |
| ATOM | 1360 | CA | GLU | 1049 | 24.844 | 41.163 | 27.555 | 1.00 | 38.31 |
| ATOM | 1361 | GB | GLU | 1049 | 25.467 | 40.164 | 28.532 | 1.00 | 43.39 |
| ATOM | 1362 | CG | GLU | 1049 | 26.992 | 40.046 | 28.448 | 1.00 | 52.18 |
| ATOM | 1363 | CD | GLU | 1049 | 27.706 | 41.401 | 28.409 | 1.00 | 57.15 |
| ATOM | 1364 | OE1 | GLU | 1049 | 27.319 | 42.318 | 29.172 | 1.00 | 60.15 |
| ATOM | 1365 | OE2 | GLU | 1049 | 28.667 | 41.542 | 27.619 | 1.00 | 58.73 |
| ATOM | 1366 | C | GLU | 1049 | 25.121 | 40.746 | 26.111 | 1.00 | 36.83 |
| ATOM | 1367 | O | GLU | 1049 | 26.063 | 41.211 | 25.471 | 1.00 | 36.38 |
| ATOM | 1368 | N | SER | 1050 | 24.253 | 39.868 | 25.617 | 1.00 | 34.63 |
| ATOM | 1369 | CA | SER | 1050 | 24.316 | 39.328 | 24.271 | 1.00 | 30.69 |
| ATOM | 1370 | CB | SER | 1050 | 25.168 | 38.061 | 24.245 | 1.00 | 32.49 |
| ATOM | 1371 | OG | SER | 1050 | 26.415 | 38.268 | 24.883 | 1.00 | 36.39 |
| ATOM | 1372 | C | SER | 1050 | 22.880 | 38.962 | 23.939 | 1.00 | 29.47 |
| ATOM | 1373 | O | SER | 1050 | 22.015 | 39.005 | 24.818 | 1.00 | 27.73 |
| ATOM | 1374 | N | VAL | 1051 | 22.627 | 38.601 | 22.682 | 1.00 | 27.04 |
| ATOM | 1375 | CA | VAL | 1051 | 21.282 | 38.226 | 22.256 | 1.00 | 22.31 |
| ATOM | 1376 | CB | VAL | 1051 | 21.260 | 37.727 | 20.774 | 1.00 | 21.56 |
| ATOM | 1377 | CG1 | VAL | 1051 | 19.845 | 37.323 | 20.367 | 1.00 | 20.09 |
| ATOM | 1378 | CG2 | VAL | 1051 | 21.762 | 38.801 | 19.851 | 1.00 | 19.56 |
| ATOM | 1379 | C | VAL | 1051 | 20.812 | 37.093 | 23.157 | 1.00 | 21.36 |
| ATOM | 1380 | O | VAL | 1051 | 21.564 | 36.147 | 23.405 | 1.00 | 20.77 |
| ATOM | 1381 | N | GLY | 1052 | 19.589 | 37.206 | 23.666 | 1.00 | 20.09 |
| ATOM | 1382 | CA | GLY | 1052 | 19.023 | 36.166 | 24.512 | 1.00 | 20.83 |
| ATOM | 1383 | C | GLY | 1052 | 19.501 | 36.003 | 25.947 | 1.00 | 22.14 |
| ATOM | 1384 | O | GLY | 1052 | 18.819 | 35.359 | 26.744 | 1.00 | 21.79 |
| ATOM | 1385 | N | GLU | 1053 | 20.660 | 36.564 | 26.281 | 1.00 | 24.79 |
| ATOM | 1386 | CA | GLU | 1053 | 21.215 | 36.454 | 27.631 | 1.00 | 27.88 |
| ATOM | 1387 | CB | GLU | 1053 | 22.706 | 36.163 | 27.553 | 1.00 | 26.83 |
| ATOM | 1388 | CG | GLU | 1053 | 23.068 | 35.352 | 26.346 | 1.00 | 30.13 |
| ATOM | 1389 | CD | GLU | 1053 | 24.499 | 34.877 | 26.370 | 1.00 | 34.21 |
| ATOM | 1390 | OE1 | GLU | 1053 | 25.405 | 35.697 | 26.646 | 1.00 | 37.12 |
| ATOM | 1391 | OE2 | GLU | 1053 | 24.715 | 33.677 | 26.100 | 1.00 | 36.45 |
| ATOM | 1392 | C | GLU | 1053 | 20.988 | 37.767 | 28.370 | 1.00 | 29.37 |
| ATOM | 1393 | O | GLU | 1053 | 21.326 | 38.842 | 27.863 | 1.00 | 30.58 |
| ATOM | 1394 | N | VAL | 1054 | 20.446 | 37.684 | 29.579 | 1.00 | 27.70 |
| ATOM | 1395 | CA | VAL | 1054 | 20.139 | 38.896 | 30.313 | 1.00 | 26.97 |
| ATOM | 1396 | CB | VAL | 1054 | 18.602 | 39.150 | 30.335 | 1.00 | 27.40 |
| ATOM | 1397 | CG1 | VAL | 1054 | 18.023 | 38.965 | 28.954 | 1.00 | 29.21 |
| ATOM | 1398 | CG2 | VAL | 1054 | 17.916 | 38.209 | 31.313 | 1.00 | 25.23 |
| ATOM | 1399 | C | VAL | 1054 | 20.606 | 38.986 | 31.750 | 1.00 | 27.70 |
| ATOM | 1400 | O | VAL | 1054 | 20.793 | 37.983 | 32.432 | 1.00 | 29.51 |
| ATOM | 1401 | N | TYR | 1055 | 20.797 | 40.221 | 32.195 | 1.00 | 28.25 |
| ATOM | 1402 | CA | TYR | 1055 | 21.148 | 40.499 | 33.577 | 1.00 | 27.38 |
| ATOM | 1403 | CB | TYR | 1055 | 22.169 | 41.629 | 33.690 | 1.00 | 26.13 |
| ATOM | 1404 | CG | TYR | 1055 | 23.591 | 41.215 | 33.396 | 1.00 | 29.84 |
| ATOM | 1405 | CD1 | TYR | 1055 | 24.201 | 40.194 | 34.118 | 1.00 | 29.78 |
| ATOM | 1406 | GE1 | TYR | 1055 | 25.524 | 39.838 | 33.881 | 1.00 | 28.70 |
| ATOM | 1407 | GD2 | TYR | 1055 | 24.343 | 41.869 | 32.418 | 1.00 | 31.06 |
| ATOM | 1408 | CE2 | TYR | 1055 | 25.665 | 41.522 | 32.173 | 1.00 | 29.16 |
| ATOM | 1409 | CZ | TYR | 1055 | 26.251 | 40.508 | 32.910 | 1.00 | 29.44 |
| ATOM | 1410 | OH | TYR | 1055 | 27.570 | 40.179 | 32.696 | 1.00 | 29.79 |
| ATOM | 1411 | C | TYR | 1055 | 19.806 | 40.966 | 34.129 | 1.00 | 27.37 |
| ATOM | 1412 | O | TYR | 1055 | 18.952 | 41.460 | 33.376 | 1.00 | 24.82 |
| ATOM | 1413 | N | ILE | 1056 | 19.614 | 40.799 | 35.432 | 1.00 | 26.35 |
| ATOM | 1414 | CA | ILE | 1056 | 18.371 | 41.196 | 36.078 | 1.00 | 23.67 |
| ATOM | 1415 | GB | ILE | 1056 | 17.504 | 39.968 | 36.340 | 1.00 | 20.83 |
| ATOM | 1416 | CG2 | ILE | 1056 | 16.278 | 40.356 | 37.161 | 1.00 | 17.28 |
| ATOM | 1417 | CG1 | ILE | 1056 | 17.160 | 39.302 | 35.005 | 1.00 | 18.55 |
| ATOM | 1418 | CD1 | ILE | 1056 | 16.483 | 37.959 | 35.149 | 1.00 | 17.09 |
| ATOM | 1419 | C | ILE | 1056 | 18.747 | 41.822 | 37.403 | 1.00 | 26.11 |
| ATOM | 1420 | O | ILE | 1056 | 19.082 | 41.104 | 38.343 | 1.00 | 29.33 |
| ATOM | 1421 | N | LYS | 1057 | 18.698 | 43.146 | 37.506 | 1.00 | 26.46 |
| ATOM | 1422 | CA | LYS | 1057 | 19.098 | 43.749 | 38.769 | 1.00 | 27.70 |
| ATOM | 1423 | GB | LYS | 1057 | 20.449 | 44.459 | 38.622 | 1.00 | 30.03 |
| ATOM | 1424 | CG | LYS | 1057 | 20.379 | 45.835 | 37.990 | 1.00 | 32.95 |
| ATOM | 1425 | CD | LYS | 1057 | 21.436 | 46.748 | 38.597 | 1.00 | 36.32 |
| ATOM | 1426 | CE | LYS | 1057 | 21.260 | 48.182 | 38.120 | 1.00 | 38.81 |
| ATOM | 1427 | NZ | LYS | 1057 | 21.900 | 49.160 | 39.052 | 1.00 | 39.14 |
| ATOM | 1428 | C | LYS | 1057 | 18.124 | 44.698 | 39.429 | 1.00 | 27.84 |
| ATOM | 1429 | O | LYS | 1057 | 17.457 | 45.492 | 38.772 | 1.00 | 26.59 |
| ATOM | 1430 | N | SER | 1058 | 18.073 | 44.608 | 40.755 | 1.00 | 29.81 |
| ATOM | 1431 | CA | SER | 1058 | 17.217 | 45.459 | 41.558 | 1.00 | 30.48 |
| ATOM | 1432 | GB | SER | 1058 | 17.415 | 45.161 | 43.048 | 1.00 | 29.38 |

TABLE 2-continued

FGFR1 D2–D3 Complexed with FGF1

| ATOM | 1433 | OG  | SER | 1058 | 16.578 | 45.971 | 43.859 | 1.00 | 26.62 |
|------|------|-----|-----|------|--------|--------|--------|------|-------|
| ATOM | 1434 | C   | SER | 1058 | 17.599 | 46.901 | 41.271 | 1.00 | 31.88 |
| ATOM | 1435 | O   | SER | 1058 | 18.776 | 47.251 | 41.240 | 1.00 | 31.86 |
| ATOM | 1436 | N   | THR | 1059 | 16.593 | 47.730 | 41.040 | 1.00 | 33.83 |
| ATOM | 1437 | CA  | THR | 1059 | 16.815 | 49.143 | 40.770 | 1.00 | 36.28 |
| ATOM | 1438 | GB  | THR | 1059 | 15.576 | 49.768 | 40.137 | 1.00 | 36.90 |
| ATOM | 1439 | OG1 | THR | 1059 | 14.424 | 49.358 | 40.887 | 1.00 | 38.69 |
| ATOM | 1440 | CG2 | THR | 1059 | 15.437 | 49.339 | 38.676 | 1.00 | 38.15 |
| ATOM | 1441 | C   | THR | 1059 | 17.073 | 49.862 | 42.092 | 1.00 | 35.37 |
| ATOM | 1442 | O   | THR | 1059 | 17.759 | 50.882 | 42.144 | 1.00 | 33.67 |
| ATOM | 1443 | N   | GLU | 1060 | 16.508 | 49.315 | 43.161 | 1.00 | 34.77 |
| ATOM | 1444 | CA  | GLU | 1060 | 16.651 | 49.901 | 44.480 | 1.00 | 33.62 |
| ATOM | 1445 | GB  | GLU | 1060 | 15.634 | 49.270 | 45.439 | 1.00 | 35.37 |
| ATOM | 1446 | CG  | GLU | 1060 | 15.275 | 50.158 | 46.620 | 1.00 | 39.28 |
| ATOM | 1447 | CD  | GLU | 1060 | 14.878 | 51.559 | 46.176 | 1.00 | 42.79 |
| ATOM | 1448 | OE1 | GLU | 1060 | 14.036 | 51.679 | 45.251 | 1.00 | 45.51 |
| ATOM | 1449 | OE2 | GLU | 1060 | 15.408 | 52.538 | 46.750 | 1.00 | 43.34 |
| ATOM | 1450 | C   | GLU | 1060 | 18.053 | 49.732 | 45.045 | 1.00 | 31.82 |
| ATOM | 1451 | O   | GLU | 1060 | 18.696 | 50.707 | 45.428 | 1.00 | 29.86 |
| ATOM | 1452 | N   | THR | 1061 | 18.525 | 48.490 | 45.077 | 1.00 | 30.63 |
| ATOM | 1453 | CA  | THR | 1061 | 19.826 | 48.183 | 45.638 | 1.00 | 29.40 |
| ATOM | 1454 | CB  | THR | 1061 | 19.750 | 46.919 | 46.521 | 1.00 | 28.93 |
| ATOM | 1455 | OG1 | THR | 1061 | 19.569 | 45.764 | 45.697 | 1.00 | 28.79 |
| ATOM | 1456 | CG2 | THR | 1061 | 18.575 | 47.021 | 47.492 | 1.00 | 27.11 |
| ATOM | 1457 | C   | THR | 1061 | 20.962 | 48.005 | 44.647 | 1.00 | 29.99 |
| ATOM | 1458 | O   | THR | 1061 | 22.127 | 48.086 | 45.030 | 1.00 | 35.77 |
| ATOM | 1459 | N   | GLY | 1062 | 20.651 | 47.771 | 43.380 | 1.00 | 29.28 |
| ATOM | 1460 | CA  | GLY | 1062 | 21.719 | 47.585 | 42.409 | 1.00 | 26.00 |
| ATOM | 1461 | C   | GLY | 1062 | 22.337 | 46.199 | 42.511 | 1.00 | 25.76 |
| ATOM | 1462 | O   | GLY | 1062 | 23.469 | 45.975 | 42.098 | 1.00 | 21.22 |
| ATOM | 1463 | N   | GLN | 1063 | 21.589 | 45.262 | 43.083 | 1.00 | 28.51 |
| ATOM | 1464 | CA  | GLN | 1063 | 22.065 | 43.890 | 43.208 | 1.00 | 29.88 |
| ATOM | 1465 | CB  | GLN | 1063 | 21.497 | 43.212 | 44.457 | 1.00 | 32.67 |
| ATOM | 1466 | CG  | GLN | 1063 | 21.849 | 43.849 | 45.792 | 1.00 | 34.71 |
| ATOM | 1467 | CD  | GLN | 1063 | 21.175 | 43.122 | 46.942 | 1.00 | 35.28 |
| ATOM | 1468 | OE1 | GLN | 1063 | 21.609 | 42.044 | 47.343 | 1.00 | 34.42 |
| ATOM | 1469 | NE2 | GLN | 1063 | 20.088 | 43.697 | 47.458 | 1.00 | 35.06 |
| ATOM | 1470 | C   | GLN | 1063 | 21.587 | 43.106 | 41.992 | 1.00 | 29.02 |
| ATOM | 1471 | O   | GLN | 1063 | 20.494 | 43.358 | 41.478 | 1.00 | 30.23 |
| ATOM | 1472 | N   | TYR | 1064 | 22.405 | 42.159 | 41.544 | 1.00 | 26.69 |
| ATOM | 1473 | CA  | TYR | 1064 | 22.061 | 41.317 | 40.408 | 1.00 | 25.12 |
| ATOM | 1474 | CB  | TYR | 1064 | 23.292 | 41.014 | 39.557 | 1.00 | 23.81 |
| ATOM | 1475 | CG  | TYR | 1064 | 23.813 | 42.220 | 38.829 | 1.00 | 26.95 |
| ATOM | 1476 | CD1 | TYR | 1064 | 24.545 | 43.198 | 39.495 | 1.00 | 26.65 |
| ATOM | 1477 | CE1 | TYR | 1064 | 24.964 | 44.362 | 38.837 | 1.00 | 28.15 |
| ATOM | 1478 | CD2 | TYR | 1064 | 23.513 | 42.425 | 37.484 | 1.00 | 28.00 |
| ATOM | 1479 | CE2 | TYR | 1064 | 23.924 | 43.581 | 36.819 | 1.00 | 27.98 |
| ATOM | 1480 | CZ  | TYR | 1064 | 24.644 | 44.546 | 37.499 | 1.00 | 28.03 |
| ATOM | 1481 | OH  | TYR | 1064 | 25.022 | 45.699 | 36.846 | 1.00 | 28.06 |
| ATOM | 1482 | C   | TYR | 1064 | 21.474 | 40.011 | 40.902 | 1.00 | 24.50 |
| ATOM | 1483 | O   | TYR | 1064 | 21.851 | 39.517 | 41.957 | 1.00 | 25.42 |
| ATOM | 1484 | N   | LEU | 1065 | 20.523 | 39.473 | 40.153 | 1.00 | 24.42 |
| ATOM | 1485 | CA  | LEU | 1065 | 19.923 | 38.207 | 40.512 | 1.00 | 23.15 |
| ATOM | 1486 | CB  | LEU | 1065 | 18.582 | 38.035 | 39.814 | 1.00 | 23.90 |
| ATOM | 1487 | CG  | LEU | 1065 | 17.932 | 36.658 | 39.952 | 1.00 | 27.51 |
| ATOM | 1488 | CD1 | LEU | 1065 | 17.497 | 36.430 | 41.401 | 1.00 | 27.40 |
| ATOM | 1489 | CD2 | LEU | 1065 | 16.743 | 36.555 | 39.003 | 1.00 | 24.52 |
| ATOM | 1490 | C   | LEU | 1065 | 20.927 | 37.204 | 39.983 | 1.00 | 25.36 |
| ATOM | 1491 | O   | LEU | 1065 | 21.413 | 37.326 | 38.853 | 1.00 | 26.57 |
| ATOM | 1492 | N   | ALA | 1066 | 21.264 | 36.228 | 40.811 | 1.00 | 27.42 |
| ATOM | 1493 | CA  | ALA | 1066 | 22.236 | 35.221 | 40.429 | 1.00 | 27.55 |
| ATOM | 1494 | CB  | ALA | 1066 | 23.624 | 35.657 | 40.855 | 1.00 | 24.63 |
| ATOM | 1495 | C   | ALA | 1066 | 21.890 | 33.879 | 41.047 | 1.00 | 29.36 |
| ATOM | 1496 | O   | ALA | 1066 | 21.021 | 33.773 | 41.916 | 1.00 | 28.66 |
| ATOM | 1497 | N   | MET | 1067 | 22.579 | 32.852 | 40.581 | 1.00 | 33.15 |
| ATOM | 1498 | CA  | MET | 1067 | 22.351 | 31.500 | 41.058 | 1.00 | 37.68 |
| ATOM | 1499 | CB  | MET | 1067 | 21.655 | 30.681 | 39.961 | 1.00 | 38.84 |
| ATOM | 1500 | CG  | MET | 1067 | 21.367 | 29.234 | 40.328 | 1.00 | 41.87 |
| ATOM | 1501 | SD  | MET | 1067 | 20.485 | 28.324 | 39.025 | 1.00 | 44.00 |
| ATOM | 1502 | CE  | MET | 1067 | 18.807 | 28.413 | 39.652 | 1.00 | 41.60 |
| ATOM | 1503 | C   | MET | 1067 | 23.698 | 30.880 | 41.432 | 1.00 | 39.02 |
| ATOM | 1504 | O   | MET | 1067 | 24.624 | 30.844 | 40.611 | 1.00 | 38.23 |
| ATOM | 1505 | N   | ASP | 1068 | 23.798 | 30.412 | 42.678 | 1.00 | 39.88 |
| ATOM | 1506 | CA  | ASP | 1068 | 25.022 | 29.795 | 43.185 | 1.00 | 40.05 |
| ATOM | 1507 | CB  | ASP | 1068 | 24.975 | 29.714 | 44.717 | 1.00 | 41.63 |
| ATOM | 1508 | CG  | ASP | 1068 | 23.904 | 28.753 | 45.225 | 1.00 | 45.16 |
| ATOM | 1509 | OD1 | ASP | 1068 | 23.692 | 28.677 | 46.457 | 1.00 | 46.56 |

TABLE 2-continued

FGFR1 D2–D3 Complexed with FGF1

| ATOM | 1510 | OD2 | ASP | 1068 | 23.273 | 28.067 | 44.396 | 1.00 | 45.84 |
|---|---|---|---|---|---|---|---|---|---|
| ATOM | 1511 | C | ASP | 1068 | 25.175 | 28.400 | 42.586 | 1.00 | 39.62 |
| ATOM | 1512 | O | ASP | 1068 | 24.269 | 27.899 | 41.922 | 1.00 | 39.76 |
| ATOM | 1513 | N | THR | 1069 | 26.316 | 27.768 | 42.822 | 1.00 | 39.31 |
| ATOM | 1514 | CA | THR | 1069 | 26.543 | 26.434 | 42.286 | 1.00 | 40.50 |
| ATOM | 1515 | CB | THR | 1069 | 27.992 | 25.997 | 42.514 | 1.00 | 39.46 |
| ATOM | 1516 | OG1 | THR | 1069 | 28.868 | 27.080 | 42.171 | 1.00 | 42.34 |
| ATOM | 1517 | CG2 | THR | 1069 | 28.329 | 24.805 | 41.633 | 1.00 | 38.96 |
| ATOM | 1518 | C | THR | 1069 | 25.590 | 25.387 | 42.879 | 1.00 | 41.08 |
| ATOM | 1519 | O | THR | 1069 | 25.558 | 24.245 | 42.429 | 1.00 | 40.48 |
| ATOM | 1520 | N | ASP | 1070 | 24.810 | 25.784 | 43.879 | 1.00 | 42.31 |
| ATOM | 1521 | CA | ASP | 1070 | 23.845 | 24.888 | 44.516 | 1.00 | 42.77 |
| ATOM | 1522 | CB | ASP | 1070 | 23.551 | 25.331 | 45.955 | 1.00 | 49.36 |
| ATOM | 1523 | CG | ASP | 1070 | 24.715 | 25.094 | 46.897 | 1.00 | 54.58 |
| ATOM | 1524 | OD1 | ASP | 1070 | 24.731 | 25.724 | 47.979 | 1.00 | 56.34 |
| ATOM | 1525 | OD2 | ASP | 1070 | 25.602 | 24.275 | 46.564 | 1.00 | 57.54 |
| ATOM | 1526 | C | ASP | 1070 | 22.541 | 24.946 | 43.752 | 1.00 | 39.94 |
| ATOM | 1527 | O | ASP | 1070 | 21.787 | 23.977 | 43.715 | 1.00 | 39.21 |
| ATOM | 1528 | N | GLY | 1071 | 22.282 | 26.105 | 43.155 | 1.00 | 38.65 |
| ATOM | 1529 | CA | GLY | 1071 | 21.049 | 26.320 | 42.419 | 1.00 | 34.25 |
| ATOM | 1530 | C | GLY | 1071 | 20.160 | 27.176 | 43.292 | 1.00 | 30.47 |
| ATOM | 1531 | O | GLY | 1071 | 18.947 | 27.003 | 43.338 | 1.00 | 29.38 |
| ATOM | 1532 | N | LEU | 1072 | 20.789 | 28.099 | 44.008 | 1.00 | 29.55 |
| ATOM | 1533 | CA | LEU | 1072 | 20.076 | 28.991 | 44.903 | 1.00 | 30.81 |
| ATOM | 1534 | CB | LEU | 1072 | 20.583 | 28.827 | 46.339 | 1.00 | 30.75 |
| ATOM | 1535 | CG | LEU | 1072 | 20.306 | 27.440 | 46.929 | 1.00 | 32.71 |
| ATOM | 1536 | CD1 | LEU | 1072 | 20.558 | 27.471 | 48.430 | 1.00 | 32.26 |
| ATOM | 1537 | CD2 | LEU | 1072 | 18.856 | 27.025 | 46.643 | 1.00 | 29.92 |
| ATOM | 1538 | C | LEU | 1072 | 20.212 | 30.436 | 44.465 | 1.00 | 30.66 |
| ATOM | 1539 | O | LEU | 1072 | 21.319 | 30.944 | 44.273 | 1.00 | 28.03 |
| ATOM | 1540 | N | LEU | 1073 | 19.065 | 31.088 | 44.310 | 1.00 | 30.39 |
| ATOM | 1541 | CA | LEU | 1073 | 19.020 | 32.474 | 43.881 | 1.00 | 30.80 |
| ATOM | 1542 | CB | LEU | 1073 | 17.585 | 32.851 | 43.497 | 1.00 | 31.40 |
| ATOM | 1543 | CG | LEU | 1073 | 16.935 | 32.037 | 42.373 | 1.00 | 28.83 |
| ATOM | 1544 | CD1 | LEU | 1073 | 15.457 | 32.382 | 42.281 | 1.00 | 25.56 |
| ATOM | 1545 | CD2 | LEU | 1073 | 17.649 | 32.313 | 41.060 | 1.00 | 27.91 |
| ATOM | 1546 | C | LEU | 1073 | 19.515 | 33.389 | 44.990 | 1.00 | 30.29 |
| ATOM | 1547 | O | LEU | 1073 | 19.245 | 33.145 | 46.168 | 1.00 | 30.31 |
| ATOM | 1548 | N | TYR | 1074 | 20.227 | 34.447 | 44.609 | 1.00 | 27.89 |
| ATOM | 1549 | CA | TYR | 1074 | 20.752 | 35.392 | 45.583 | 1.00 | 26.07 |
| ATOM | 1550 | CB | TYR | 1074 | 21.977 | 34.790 | 46.263 | 1.00 | 22.93 |
| ATOM | 1551 | CG | TYR | 1074 | 23.177 | 34.697 | 45.358 | 1.00 | 18.75 |
| ATOM | 1552 | CD1 | TYR | 1074 | 24.101 | 35.741 | 45.293 | 1.00 | 17.28 |
| ATOM | 1553 | CE1 | TYR | 1074 | 25.199 | 35.673 | 44.451 | 1.00 | 19.02 |
| ATOM | 1554 | CD2 | TYR | 1074 | 23.380 | 33.580 | 44.552 | 1.00 | 17.20 |
| ATOM | 1555 | CE2 | TYR | 1074 | 24.475 | 33.502 | 43.701 | 1.00 | 18.58 |
| ATOM | 1556 | CZ | TYR | 1074 | 25.378 | 34.552 | 43.657 | 1.00 | 20.10 |
| ATOM | 1557 | OH | TYR | 1074 | 26.458 | 34.494 | 42.813 | 1.00 | 25.05 |
| ATOM | 1558 | C | TYR | 1074 | 21.130 | 36.711 | 44.917 | 1.00 | 26.56 |
| ATOM | 1559 | O | TYR | 1074 | 21.403 | 36.745 | 43.718 | 1.00 | 25.36 |
| ATOM | 1560 | N | GLY | 1075 | 21.142 | 37.791 | 45.699 | 1.00 | 26.90 |
| ATOM | 1561 | CA | GLY | 1075 | 21.508 | 39.093 | 45.164 | 1.00 | 27.88 |
| ATOM | 1562 | C | GLY | 1075 | 23.020 | 39.252 | 45.105 | 1.00 | 29.27 |
| ATOM | 1563 | O | GLY | 1075 | 23.724 | 38.873 | 46.046 | 1.00 | 32.09 |
| ATOM | 1564 | N | SER | 1076 | 23.530 | 39.806 | 44.011 | 1.00 | 26.40 |
| ATOM | 1565 | CA | SER | 1076 | 24.966 | 39.983 | 43.868 | 1.00 | 26.05 |
| ATOM | 1566 | CB | SER | 1076 | 25.465 | 39.180 | 42.673 | 1.00 | 24.24 |
| ATOM | 1567 | OG | SER | 1076 | 26.871 | 39.285 | 42.555 | 1.00 | 22.31 |
| ATOM | 1568 | C | SER | 1076 | 25.357 | 41.451 | 43.715 | 1.00 | 28.14 |
| ATOM | 1569 | O | SER | 1076 | 24.887 | 42.142 | 42.822 | 1.00 | 27.04 |
| ATOM | 1570 | N | GLN | 1077 | 26.234 | 41.917 | 44.593 | 1.00 | 31.22 |
| ATOM | 1571 | CA | GLN | 1077 | 26.679 | 43.305 | 44.579 | 1.00 | 34.21 |
| ATOM | 1572 | CB | GLN | 1077 | 27.692 | 43.535 | 45.709 | 1.00 | 39.89 |
| ATOM | 1573 | CG | GLN | 1077 | 27.220 | 43.090 | 47.109 | 1.00 | 49.08 |
| ATOM | 1574 | CD | GLN | 1077 | 26.818 | 41.604 | 47.183 | 1.00 | 53.27 |
| ATOM | 1575 | OE1 | GLN | 1077 | 27.597 | 40.713 | 46.825 | 1.00 | 54.54 |
| ATOM | 1576 | NE2 | GLN | 1077 | 25.596 | 41.340 | 47.652 | 1.00 | 54.11 |
| ATOM | 1577 | C | GLN | 1077 | 27.299 | 43.694 | 43.238 | 1.00 | 32.60 |
| ATOM | 1578 | O | GLN | 1077 | 27.238 | 44.851 | 42.832 | 1.00 | 32.95 |
| ATOM | 1579 | N | THR | 1078 | 27.909 | 42.729 | 42.562 | 1.00 | 32.16 |
| ATOM | 1580 | CA | THR | 1078 | 28.536 | 42.973 | 41.262 | 1.00 | 32.21 |
| ATOM | 1581 | CB | THR | 1078 | 30.094 | 43.044 | 41.359 | 1.00 | 32.67 |
| ATOM | 1582 | OG1 | THR | 1078 | 30.595 | 41.836 | 41.946 | 1.00 | 33.55 |
| ATOM | 1583 | CG2 | THR | 1078 | 30.540 | 44.231 | 42.199 | 1.00 | 30.31 |
| ATOM | 1584 | C | THR | 1078 | 28.170 | 41.816 | 40.335 | 1.00 | 32.63 |
| ATOM | 1585 | O | THR | 1078 | 28.027 | 40.681 | 40.779 | 1.00 | 30.17 |
| ATOM | 1586 | N | PRO | 1079 | 28.029 | 42.094 | 39.029 | 1.00 | 34.72 |

TABLE 2-continued

FGFR1 D2–D3 Complexed with FGF1

| ATOM | 1587 | CD | PRO | 1079 | 28.243 | 43.421 | 38.420 | 1.00 | 36.18 |
|------|------|------|------|------|--------|--------|--------|------|-------|
| ATOM | 1588 | CA | PRO | 1079 | 27.677 | 41.107 | 38.001 | 1.00 | 35.22 |
| ATOM | 1589 | CB | PRO | 1079 | 27.373 | 41.977 | 36.791 | 1.00 | 34.64 |
| ATOM | 1590 | CG | PRO | 1079 | 28.368 | 43.084 | 36.948 | 1.00 | 34.95 |
| ATOM | 1591 | C | PRO | 1079 | 28.780 | 40.100 | 37.707 | 1.00 | 35.41 |
| ATOM | 1592 | O | PRO | 1079 | 29.958 | 40.422 | 37.791 | 1.00 | 36.31 |
| ATOM | 1593 | N | ASN | 1080 | 28.387 | 38.882 | 37.352 | 1.00 | 36.45 |
| ATOM | 1594 | CA | ASN | 1080 | 29.341 | 37.823 | 37.032 | 1.00 | 36.47 |
| ATOM | 1595 | CB | ASN | 1080 | 29.990 | 37.285 | 38.303 | 1.00 | 33.73 |
| ATOM | 1596 | CG | ASN | 1080 | 28.968 | 36.896 | 39.358 | 1.00 | 33.02 |
| ATOM | 1597 | OD1 | ASN | 1080 | 28.868 | 37.543 | 40.396 | 1.00 | 33.03 |
| ATOM | 1598 | ND2 | ASN | 1080 | 28.197 | 35.841 | 39.093 | 1.00 | 31.80 |
| ATOM | 1599 | C | ASN | 1080 | 28.637 | 36.680 | 36.316 | 1.00 | 37.82 |
| ATOM | 1600 | O | ASN | 1080 | 27.420 | 36.719 | 36.106 | 1.00 | 38.73 |
| ATOM | 1601 | N | GLU | 1081 | 29.405 | 35.658 | 35.957 | 1.00 | 38.00 |
| ATOM | 1602 | CA | GLU | 1081 | 28.867 | 34.499 | 35.256 | 1.00 | 37.30 |
| ATOM | 1603 | CB | GLU | 1081 | 29.963 | 33.431 | 35.114 | 1.00 | 39.90 |
| ATOM | 1604 | CG | GLU | 1081 | 31.106 | 33.567 | 36.118 | 1.00 | 46.27 |
| ATOM | 1605 | CD | GLU | 1081 | 30.917 | 32.717 | 37.370 | 1.00 | 50.08 |
| ATOM | 1606 | OE1 | GLU | 1081 | 31.452 | 33.099 | 38.442 | 1.00 | 50.21 |
| ATOM | 1607 | OE2 | GLU | 1081 | 30.248 | 31.659 | 37.275 | 1.00 | 52.50 |
| ATOM | 1608 | C | GLU | 1081 | 27.614 | 33.919 | 35.924 | 1.00 | 35.43 |
| ATOM | 1609 | O | GLU | 1081 | 26.727 | 33.387 | 35.246 | 1.00 | 35.83 |
| ATOM | 1610 | N | GLU | 1082 | 27.525 | 34.044 | 37.243 | 1.00 | 31.71 |
| ATOM | 1611 | CA | GLU | 1082 | 26.372 | 33.524 | 37.961 | 1.00 | 31.35 |
| ATOM | 1612 | CB | GLU | 1082 | 26.724 | 33.323 | 39.431 | 1.00 | 31.86 |
| ATOM | 1613 | CG | GLU | 1082 | 27.935 | 32.455 | 39.661 | 1.00 | 32.37 |
| ATOM | 1614 | CD | GLU | 1082 | 27.808 | 31.638 | 40.927 | 1.00 | 35.13 |
| ATOM | 1615 | OE1 | GLU | 1082 | 27.576 | 32.245 | 41.998 | 1.00 | 34.64 |
| ATOM | 1616 | OE2 | GLU | 1082 | 27.931 | 30.388 | 40.851 | 1.00 | 37.63 |
| ATOM | 1617 | C | GLU | 1082 | 25.138 | 34.420 | 37.865 | 1.00 | 30.97 |
| ATOM | 1618 | O | GLU | 1082 | 24.083 | 34.078 | 38.387 | 1.00 | 28.54 |
| ATOM | 1619 | N | CYS | 1083 | 25.274 | 35.563 | 37.197 | 1.00 | 32.94 |
| ATOM | 1620 | CA | CYS | 1083 | 24.172 | 36.515 | 37.056 | 1.00 | 34.49 |
| ATOM | 1621 | GB | CYS | 1083 | 24.681 | 37.946 | 37.256 | 1.00 | 36.74 |
| ATOM | 1622 | SG | CYS | 1083 | 25.554 | 38.234 | 38.807 | 1.00 | 38.01 |
| ATOM | 1623 | C | CYS | 1083 | 23.461 | 36.440 | 35.709 | 1.00 | 34.35 |
| ATOM | 1624 | O | CYS | 1083 | 22.309 | 36.864 | 35.592 | 1.00 | 36.33 |
| ATOM | 1625 | N | LEU | 1084 | 24.151 | 35.920 | 34.694 | 1.00 | 33.18 |
| ATOM | 1626 | CA | LEU | 1084 | 23.583 | 35.802 | 33.349 | 1.00 | 31.59 |
| ATOM | 1627 | CB | LEU | 1084 | 24.693 | 35.598 | 32.326 | 1.00 | 29.82 |
| ATOM | 1628 | CG | LEU | 1084 | 25.519 | 36.830 | 31.998 | 1.00 | 29.05 |
| ATOM | 1629 | CD1 | LEU | 1084 | 26.668 | 36.436 | 31.117 | 1.00 | 31.19 |
| ATOM | 1630 | CD2 | LEU | 1084 | 24.649 | 37.856 | 31.310 | 1.00 | 30.96 |
| ATOM | 1631 | C | LEU | 1084 | 22.560 | 34.684 | 33.187 | 1.00 | 31.04 |
| ATOM | 1632 | O | LEU | 1084 | 22.835 | 33.521 | 33.488 | 1.00 | 31.52 |
| ATOM | 1633 | N | PHE | 1085 | 21.384 | 35.053 | 32.695 | 1.00 | 29.39 |
| ATOM | 1634 | CA | PHE | 1085 | 20.302 | 34.107 | 32.472 | 1.00 | 27.51 |
| ATOM | 1635 | CB | PHE | 1085 | 19.140 | 34.418 | 33.412 | 1.00 | 25.56 |
| ATOM | 1636 | CG | PHE | 1085 | 19.437 | 34.122 | 34.850 | 1.00 | 26.35 |
| ATOM | 1637 | CD1 | PHE | 1085 | 19.256 | 32.837 | 35.364 | 1.00 | 26.39 |
| ATOM | 1638 | CD2 | PHE | 1085 | 19.939 | 35.117 | 35.688 | 1.00 | 26.04 |
| ATOM | 1639 | GE1 | PHE | 1085 | 19.576 | 32.542 | 36.698 | 1.00 | 25.79 |
| ATOM | 1640 | CE2 | PHE | 1085 | 20.263 | 34.837 | 37.022 | 1.00 | 25.17 |
| ATOM | 1641 | CZ | PHE | 1085 | 20.081 | 33.546 | 37.526 | 1.00 | 24.81 |
| ATOM | 1642 | C | PHE | 1085 | 19.814 | 34.120 | 31.020 | 1.00 | 28.23 |
| ATOM | 1643 | O | PHE | 1085 | 19.846 | 35.148 | 30.326 | 1.00 | 26.28 |
| ATOM | 1644 | N | LEU | 1086 | 19.377 | 32.952 | 30.563 | 1.00 | 28.35 |
| ATOM | 1645 | CA | LEU | 1086 | 18.872 | 32.797 | 29.212 | 1.00 | 25.31 |
| ATOM | 1646 | GB | LEU | 1086 | 19.145 | 31.385 | 28.709 | 1.00 | 19.69 |
| ATOM | 1647 | CG | LEU | 1086 | 20.649 | 31.146 | 28.547 | 1.00 | 21.64 |
| ATOM | 1648 | CD1 | LEU | 1086 | 20.919 | 29.763 | 27.995 | 1.00 | 18.82 |
| ATOM | 1649 | CD2 | LEU | 1086 | 21.227 | 32.215 | 27.631 | 1.00 | 19.38 |
| ATOM | 1650 | C | LEU | 1086 | 17.391 | 33.073 | 29.255 | 1.00 | 25.89 |
| ATOM | 1651 | O | LEU | 1086 | 16.647 | 32.360 | 29.925 | 1.00 | 25.83 |
| ATOM | 1652 | N | GLU | 1087 | 16.974 | 34.131 | 28.562 | 1.00 | 26.76 |
| ATOM | 1653 | CA | GLU | 1087 | 15.570 | 34.511 | 28.527 | 1.00 | 28.92 |
| ATOM | 1654 | GB | GLU | 1087 | 15.428 | 36.039 | 28.538 | 1.00 | 28.77 |
| ATOM | 1655 | CG | GLU | 1087 | 13.976 | 36.543 | 28.523 | 1.00 | 27.49 |
| ATOM | 1656 | CD | GLU | 1087 | 13.883 | 38.060 | 28.352 | 1.00 | 29.97 |
| ATOM | 1657 | OE1 | GLU | 1087 | 14.340 | 38.573 | 27.306 | 1.00 | 30.86 |
| ATOM | 1658 | OE2 | GLU | 1087 | 13.357 | 38.747 | 29.261 | 1.00 | 31.30 |
| ATOM | 1659 | C | GLU | 1087 | 14.879 | 33.944 | 27.292 | 1.00 | 29.76 |
| ATOM | 1660 | O | GLU | 1087 | 15.336 | 34.141 | 26.164 | 1.00 | 30.29 |
| ATOM | 1661 | N | ARG | 1088 | 13.784 | 33.227 | 27.510 | 1.00 | 29.72 |
| ATOM | 1662 | CA | ARG | 1088 | 13.041 | 32.667 | 26.400 | 1.00 | 31.93 |
| ATOM | 1663 | CB | ARG | 1088 | 13.310 | 31.169 | 26.238 | 1.00 | 36.51 |

TABLE 2-continued

FGFR1 D2–D3 Complexed with FGF1

| ATOM | 1664 | CG | ARG | 1088 | 12.700 | 30.625 | 24.947 | 1.00 | 43.94 |
|---|---|---|---|---|---|---|---|---|---|
| ATOM | 1665 | CD | ARG | 1088 | 12.476 | 29.112 | 24.932 | 1.00 | 46.90 |
| ATOM | 1666 | NE | ARG | 1088 | 11.471 | 28.768 | 23.922 | 1.00 | 52.33 |
| ATOM | 1667 | CZ | ARG | 1088 | 10.807 | 27.614 | 23.867 | 1.00 | 54.24 |
| ATOM | 1668 | NH1 | ARG | 1088 | 11.037 | 26.664 | 24.770 | 1.00 | 53.32 |
| ATOM | 1669 | NH2 | ARG | 1088 | 9.894 | 27.421 | 22.916 | 1.00 | 52.86 |
| ATOM | 1670 | C | ARG | 1088 | 11.547 | 32.876 | 26.582 | 1.00 | 31.39 |
| ATOM | 1671 | O | ARG | 1088 | 10.975 | 32.525 | 27.628 | 1.00 | 31.35 |
| ATOM | 1672 | N | LEU | 1089 | 10.927 | 33.467 | 25.562 | 1.00 | 28.47 |
| ATOM | 1673 | C | LEU | 1089 | 9.490 | 33.706 | 25.564 | 1.00 | 26.29 |
| ATOM | 1674 | CB | LEU | 1089 | 9.145 | 34.879 | 24.641 | 1.00 | 23.74 |
| ATOM | 1675 | CG | LEU | 1089 | 7.675 | 35.197 | 24.343 | 1.00 | 21.80 |
| ATOM | 1676 | CD1 | LEU | 1089 | 6.774 | 34.974 | 25.559 | 1.00 | 23.10 |
| ATOM | 1677 | CD2 | LEU | 1089 | 7.599 | 36.636 | 23.880 | 1.00 | 23.12 |
| ATOM | 1678 | C | LEU | 1089 | 8.857 | 32.423 | 25.056 | 1.00 | 25.24 |
| ATOM | 1679 | O | LEU | 1089 | 8.916 | 32.122 | 23.870 | 1.00 | 26.06 |
| ATOM | 1680 | N | GLU | 1090 | 8.262 | 31.658 | 25.961 | 1.00 | 26.17 |
| ATOM | 1681 | CA | GLU | 1090 | 7.656 | 30.386 | 25.592 | 1.00 | 28.55 |
| ATOM | 1682 | GB | GLU | 1090 | 7.358 | 29.562 | 26.850 | 1.00 | 28.73 |
| ATOM | 1683 | CG | GLU | 1090 | 8.535 | 29.404 | 27.824 | 1.00 | 31.24 |
| ATOM | 1684 | CD | GLU | 1090 | 9.790 | 28.808 | 27.186 | 1.00 | 32.62 |
| ATOM | 1685 | OE1 | GLU | 1090 | 9.712 | 27.703 | 26.609 | 1.00 | 33.25 |
| ATOM | 1686 | OE2 | GLU | 1090 | 10.862 | 29.450 | 27.273 | 1.00 | 34.62 |
| ATOM | 1687 | C | GLU | 1090 | 6.379 | 30.490 | 24.754 | 1.00 | 30.27 |
| ATOM | 1688 | O | GLU | 1090 | 5.722 | 31.540 | 24.672 | 1.00 | 28.66 |
| ATOM | 1689 | N | GLU | 1091 | 6.034 | 29.368 | 24.138 | 1.00 | 29.86 |
| ATOM | 1690 | CA | GLU | 1091 | 4.847 | 29.289 | 23.316 | 1.00 | 30.85 |
| ATOM | 1691 | CB | GLU | 1091 | 4.759 | 27.895 | 22.706 | 1.00 | 36.47 |
| ATOM | 1692 | CG | GLU | 1091 | 6.007 | 27.536 | 21.924 | 1.00 | 44.98 |
| ATOM | 1693 | CD | GLU | 1091 | 6.014 | 26.099 | 21.445 | 1.00 | 49.97 |
| ATOM | 1694 | OE1 | GLU | 1091 | 7.041 | 25.680 | 20.859 | 1.00 | 53.36 |
| ATOM | 1695 | OE2 | GLU | 1091 | 4.998 | 25.393 | 21.654 | 1.00 | 52.79 |
| ATOM | 1696 | C | GLU | 1091 | 3.603 | 29.597 | 24.145 | 1.00 | 27.67 |
| ATOM | 1697 | O | GLU | 1091 | 2.643 | 30.181 | 23.644 | 1.00 | 26.96 |
| ATOM | 1698 | N | ASN | 1092 | 3.631 | 29.207 | 25.413 | 1.00 | 25.03 |
| ATOM | 1699 | CA | ASN | 1092 | 2.514 | 29.447 | 26.319 | 1.00 | 23.79 |
| ATOM | 1700 | CB | ASN | 1092 | 2.668 | 28.611 | 27.579 | 1.00 | 22.47 |
| ATOM | 1701 | CG | ASN | 1092 | 3.808 | 29.092 | 28.455 | 1.00 | 24.99 |
| ATOM | 1702 | OD1 | ASN | 1092 | 4.676 | 29.873 | 28.021 | 1.00 | 25.87 |
| ATOM | 1703 | ND2 | ASN | 1092 | 3.822 | 28.625 | 29.695 | 1.00 | 21.94 |
| ATOM | 1704 | C | ASN | 1092 | 2.480 | 30.921 | 26.698 | 1.00 | 24.29 |
| ATOM | 1705 | O | ASN | 1092 | 1.736 | 31.329 | 27.594 | 1.00 | 24.10 |
| ATOM | 1706 | N | HIS | 1093 | 3.319 | 31.703 | 26.026 | 1.00 | 24.15 |
| ATOM | 1707 | CA | HIS | 1093 | 3.387 | 33.146 | 26.231 | 1.00 | 25.70 |
| ATOM | 1708 | CB | HIS | 1093 | 2.019 | 33.769 | 25.943 | 1.00 | 27.08 |
| ATOM | 1709 | CG | HIS | 1093 | 1.703 | 33.844 | 24.484 | 1.00 | 27.45 |
| ATOM | 1710 | CD2 | HIS | 1093 | 0.603 | 34.280 | 23.828 | 1.00 | 29.81 |
| ATOM | 1711 | ND1 | HIS | 1093 | 2.604 | 33.463 | 23.514 | 1.00 | 28.03 |
| ATOM | 1712 | CE1 | HIS | 1093 | 2.074 | 33.662 | 22.320 | 1.00 | 27.38 |
| ATOM | 1713 | NE2 | HIS | 1093 | 0.860 | 34.158 | 22.483 | 1.00 | 28.82 |
| ATOM | 1714 | C | HIS | 1093 | 3.909 | 33.630 | 27.577 | 1.00 | 23.83 |
| ATOM | 1715 | O | HIS | 1093 | 3.659 | 34.766 | 27.993 | 1.00 | 21.91 |
| ATOM | 1716 | N | TYR | 1094 | 4.636 | 32.757 | 28.253 | 1.00 | 22.71 |
| ATOM | 1717 | CA | TYR | 1094 | 5.237 | 33.109 | 29.522 | 1.00 | 20.61 |
| ATOM | 1718 | CB | TYR | 1094 | 4.935 | 32.050 | 30.579 | 1.00 | 18.87 |
| ATOM | 1719 | CG | TYR | 1094 | 3.589 | 32.223 | 31.238 | 1.00 | 19.49 |
| ATOM | 1720 | CD1 | TYR | 1094 | 3.389 | 33.222 | 32.183 | 1.00 | 19.68 |
| ATOM | 1721 | CE1 | TYR | 1094 | 2.140 | 33.416 | 32.762 | 1.00 | 17.88 |
| ATOM | 1722 | CD2 | TYR | 1094 | 2.497 | 31.416 | 30.887 | 1.00 | 15.85 |
| ATOM | 1723 | CE2 | TYR | 1094 | 1.252 | 31.607 | 31.455 | 1.00 | 9.43 |
| ATOM | 1724 | CZ | TYR | 1094 | 1.081 | 32.603 | 32.390 | 1.00 | 14.46 |
| ATOM | 1725 | OH | TYR | 1094 | −0.140 | 32.793 | 32.988 | 1.00 | 17.63 |
| ATOM | 1726 | C | TYR | 1094 | 6.729 | 33.163 | 29.268 | 1.00 | 20.82 |
| ATOM | 1727 | O | TYR | 1094 | 7.210 | 32.712 | 28.221 | 1.00 | 18.07 |
| ATOM | 1728 | N | ASN | 1095 | 7.455 | 33.739 | 30.219 | 1.00 | 20.89 |
| ATOM | 1729 | CA | ASN | 1095 | 8.900 | 33.820 | 30.118 | 1.00 | 20.72 |
| ATOM | 1730 | CB | ASN | 1095 | 9.412 | 35.212 | 30.487 | 1.00 | 21.40 |
| ATOM | 1731 | CG | ASN | 1095 | 9.470 | 36.143 | 29.302 | 1.00 | 23.13 |
| ATOM | 1732 | OD1 | ASN | 1095 | 9.331 | 35.708 | 28.152 | 1.00 | 22.83 |
| ATOM | 1733 | ND2 | ASN | 1095 | 9.690 | 37.434 | 29.567 | 1.00 | 16.97 |
| ATOM | 1734 | C | ASN | 1095 | 9.494 | 32.835 | 31.091 | 1.00 | 19.44 |
| ATOM | 1735 | O | ASH | 1095 | 8.893 | 32.530 | 32.129 | 1.00 | 17.11 |
| ATOM | 1736 | N | THR | 1096 | 10.666 | 32.326 | 30.738 | 1.00 | 17.55 |
| ATOM | 1737 | CA | THR | 1096 | 11.389 | 31.419 | 31.610 | 1.00 | 17.03 |
| ATOM | 1738 | CB | THR | 1096 | 11.308 | 29.941 | 31.161 | 1.00 | 15.71 |
| ATOM | 1739 | OG1 | THR | 1096 | 11.824 | 29.804 | 29.829 | 1.00 | 16.36 |
| ATOM | 1740 | CG2 | THR | 1096 | 9.875 | 29.444 | 31.243 | 1.00 | 13.45 |

TABLE 2-continued

FGFR1 D2–D3 Complexed with FGF1

| ATOM | 1741 | C | THR | 1096 | 12.832 | 31.870 | 31.561 | 1.00 | 18.27 |
|---|---|---|---|---|---|---|---|---|---|
| ATOM | 1742 | O | THR | 1096 | 13.339 | 32.275 | 30.512 | 1.00 | 16.38 |
| ATOM | 1743 | N | TYR | 1097 | 13.490 | 31.816 | 32.708 | 1.00 | 21.55 |
| ATOM | 1744 | CA | TYR | 1097 | 14.880 | 32.223 | 32.780 | 1.00 | 23.69 |
| ATOM | 1745 | CB | TYR | 1097 | 15.000 | 33.436 | 33.703 | 1.00 | 22.27 |
| ATOM | 1746 | CG | TYR | 1097 | 14.243 | 34.642 | 33.181 | 1.00 | 23.09 |
| ATOM | 1747 | CD1 | TYR | 1097 | 14.825 | 35.505 | 32.247 | 1.00 | 22.94 |
| ATOM | 1748 | CE1 | TYR | 1097 | 14.135 | 36.604 | 31.756 | 1.00 | 22.15 |
| ATOM | 1749 | CD2 | TYR | 1097 | 12.940 | 34.912 | 33.607 | 1.00 | 21.24 |
| ATOM | 1750 | CE2 | TYR | 1097 | 12.241 | 36.003 | 33.122 | 1.00 | 22.31 |
| ATOM | 1751 | CZ | TYR | 1097 | 12.844 | 36.850 | 32.196 | 1.00 | 24.38 |
| ATOM | 1752 | OH | TYR | 1097 | 12.159 | 37.945 | 31.715 | 1.00 | 23.23 |
| ATOM | 1753 | C | TYR | 1097 | 15.730 | 31.058 | 33.273 | 1.00 | 25.03 |
| ATOM | 1754 | O | TYR | 1097 | 15.580 | 30.599 | 34.408 | 1.00 | 26.08 |
| ATOM | 1755 | N | ILE | 1098 | 16.601 | 30.566 | 32.399 | 1.00 | 24.39 |
| ATOM | 1756 | CA | ILE | 1098 | 17.478 | 29.459 | 32.736 | 1.00 | 25.51 |
| ATOM | 1757 | CB | ILE | 1098 | 17.591 | 28.452 | 31.553 | 1.00 | 27.69 |
| ATOM | 1758 | CG2 | ILE | 1098 | 18.784 | 27.513 | 31.761 | 1.00 | 26.48 |
| ATOM | 1759 | CG1 | ILE | 1098 | 16.283 | 27.664 | 31.422 | 1.00 | 29.30 |
| ATOM | 1760 | CD1 | ILE | 1098 | 16.250 | 26.691 | 30.265 | 1.00 | 30.50 |
| ATOM | 1761 | C | ILE | 1098 | 18.864 | 29.971 | 33.070 | 1.00 | 25.47 |
| ATOM | 1762 | O | ILE | 1098 | 19.371 | 30.864 | 32.397 | 1.00 | 26.03 |
| ATOM | 1763 | N | SER | 1099 | 19.471 | 29.411 | 34.115 | 1.00 | 27.10 |
| ATOM | 1764 | CA | SER | 1099 | 20.831 | 29.792 | 34.505 | 1.00 | 26.84 |
| ATOM | 1765 | CB | SER | 1099 | 21.329 | 28.937 | 35.672 | 1.00 | 25.96 |
| ATOM | 1766 | OG | SER | 1099 | 22.744 | 28.831 | 35.633 | 1.00 | 23.92 |
| ATOM | 1767 | C | SER | 1099 | 21.751 | 29.565 | 33.311 | 1.00 | 27.38 |
| ATOM | 1768 | O | SER | 1099 | 21.845 | 28.449 | 32.791 | 1.00 | 25.65 |
| ATOM | 1769 | N | LYS | 1100 | 22.423 | 30.627 | 32.881 | 1.00 | 28.81 |
| ATOM | 1770 | CA | LYS | 1100 | 23.329 | 30.556 | 31.746 | 1.00 | 27.88 |
| ATOM | 1771 | CB | LYS | 1100 | 23.814 | 31.958 | 31.381 | 1.00 | 25.82 |
| ATOM | 1772 | CG | LYS | 1100 | 24.366 | 32.105 | 29.973 | 1.00 | 23.03 |
| ATOM | 1773 | CD | LYS | 1100 | 25.670 | 31.382 | 29.798 | 1.00 | 21.49 |
| ATOM | 1774 | CE | LYS | 1100 | 26.291 | 31.684 | 28.444 | 1.00 | 27.52 |
| ATOM | 1775 | NZ | LYS | 1100 | 26.639 | 33.123 | 28.259 | 1.00 | 31.05 |
| ATOM | 1776 | C | LYS | 1100 | 24.510 | 29.664 | 32.095 | 1.00 | 29.65 |
| ATOM | 1777 | O | LYS | 1100 | 25.001 | 28.927 | 31.247 | 1.00 | 30.86 |
| ATOM | 1778 | N | LYS | 1101 | 24.952 | 29.722 | 33.347 | 1.00 | 33.14 |
| ATOM | 1779 | CA | LYS | 1101 | 26.081 | 28.916 | 33.799 | 1.00 | 36.59 |
| ATOM | 1780 | CB | LYS | 1101 | 26.655 | 29.498 | 35.090 | 1.00 | 39.16 |
| ATOM | 1781 | CG | LYS | 1101 | 27.824 | 28.710 | 35.665 | 1.00 | 40.87 |
| ATOM | 1782 | CD | LYS | 1101 | 28.258 | 29.283 | 37.004 | 1.00 | 43.27 |
| ATOM | 1783 | CE | LYS | 1101 | 29.356 | 28.445 | 37.645 | 1.00 | 43.89 |
| ATOM | 1784 | NZ | LYS | 1101 | 29.730 | 28.963 | 38.999 | 1.00 | 45.78 |
| ATOM | 1785 | C | LYS | 1101 | 25.703 | 27.451 | 34.030 | 1.00 | 38.74 |
| ATOM | 1786 | O | LYS | 1101 | 26.517 | 26.552 | 33.831 | 1.00 | 40.28 |
| ATOM | 1787 | N | HIS | 1102 | 24.473 | 27.203 | 34.452 | 1.00 | 39.44 |
| ATOM | 1788 | CA | HIS | 1102 | 24.056 | 25.831 | 34.700 | 1.00 | 42.07 |
| ATOM | 1789 | CB | HIS | 1102 | 23.574 | 25.706 | 36.149 | 1.00 | 46.14 |
| ATOM | 1790 | CG | HIS | 1102 | 24.667 | 25.893 | 37.156 | 1.00 | 50.07 |
| ATOM | 1791 | CD2 | HIS | 1102 | 25.043 | 26.978 | 37.877 | 1.00 | 52.28 |
| ATOM | 1792 | ND1 | HIS | 1102 | 25.564 | 24.895 | 37.474 | 1.00 | 53.13 |
| ATOM | 1793 | CE1 | HIS | 1102 | 26.444 | 25.357 | 38.346 | 1.00 | 54.05 |
| ATOM | 1794 | NE2 | HIS | 1102 | 26.151 | 26.620 | 38.606 | 1.00 | 52.81 |
| ATOM | 1795 | C | HIS | 1102 | 22.982 | 25.375 | 33.711 | 1.00 | 41.28 |
| ATOM | 1796 | O | HIS | 1102 | 22.063 | 24.619 | 34.061 | 1.00 | 37.39 |
| ATOM | 1797 | N | ALA | 1103 | 23.130 | 25.834 | 32.469 | 1.00 | 40.59 |
| ATOM | 1798 | CA | ALA | 1103 | 22.202 | 25.512 | 31.390 | 1.00 | 40.36 |
| ATOM | 1799 | CB | ALA | 1103 | 22.635 | 26.200 | 30.123 | 1.00 | 37.23 |
| ATOM | 1800 | C | ALA | 1103 | 22.096 | 24.014 | 31.149 | 1.00 | 42.23 |
| ATOM | 1801 | O | ALA | 1103 | 20.997 | 23.452 | 31.168 | 1.00 | 44.36 |
| ATOM | 1802 | N | GLU | 1104 | 23.238 | 23.375 | 30.912 | 1.00 | 43.40 |
| ATOM | 1803 | CA | GLU | 1104 | 23.292 | 21.937 | 30.665 | 1.00 | 42.56 |
| ATOM | 1804 | CB | GLU | 1104 | 24.719 | 21.447 | 30.890 | 1.00 | 43.94 |
| ATOM | 1805 | CG | GLU | 1104 | 24.823 | 19.969 | 31.196 | 1.00 | 50.47 |
| ATOM | 1806 | CD | GLU | 1104 | 25.984 | 19.649 | 32.132 | 1.00 | 53.87 |
| ATOM | 1807 | OE1 | GLU | 1104 | 26.065 | 18.492 | 32.608 | 1.00 | 53.33 |
| ATOM | 1808 | OE2 | GLU | 1104 | 26.815 | 20.555 | 32.389 | 1.00 | 56.91 |
| ATOM | 1809 | C | GLU | 1104 | 22.315 | 21.144 | 31.548 | 1.00 | 40.65 |
| ATOM | 1810 | O | GLU | 1104 | 21.601 | 20.270 | 31.071 | 1.00 | 40.37 |
| ATOM | 1811 | N | LYS | 1105 | 22.280 | 21.461 | 32.836 | 1.00 | 39.78 |
| ATOM | 1812 | CA | LYS | 1105 | 21.403 | 20.764 | 33.769 | 1.00 | 39.91 |
| ATOM | 1813 | CB | LYS | 1105 | 21.907 | 20.951 | 35.202 | 1.00 | 37.94 |
| ATOM | 1814 | CG | LYS | 1105 | 23.417 | 21.052 | 35.304 | 1.00 | 39.12 |
| ATOM | 1815 | CD | LYS | 1105 | 23.848 | 21.809 | 36.556 | 1.00 | 39.21 |
| ATOM | 1816 | CE | LYS | 1105 | 25.327 | 22.126 | 36.492 | 1.00 | 37.65 |
| ATOM | 1817 | NZ | LYS | 1105 | 25.661 | 22.762 | 35.185 | 1.00 | 38.50 |

TABLE 2-continued

| FGFR1 D2–D3 Complexed with FGF1 | | | | | | | | |
|---|---|---|---|---|---|---|---|---|
| ATOM | 1818 | C | LYS | 1105 | 19.979 | 21.296 | 33.685 | 1.00 | 40.75 |
| ATOM | 1819 | O | LYS | 1105 | 19.071 | 20.742 | 34.297 | 1.00 | 41.96 |
| ATOM | 1820 | N | ASN | 1106 | 19.784 | 22.376 | 32.937 | 1.00 | 41.18 |
| ATOM | 1821 | CA | ASN | 1106 | 18.462 | 22.981 | 32.820 | 1.00 | 41.14 |
| ATOM | 1822 | CB | ASN | 1106 | 17.475 | 21.971 | 32.234 | 1.00 | 44.79 |
| ATOM | 1823 | CG | ASN | 1106 | 17.528 | 21.926 | 30.715 | 1.00 | 49.01 |
| ATOM | 1824 | OD1 | ASN | 1106 | 17.201 | 20.907 | 30.096 | 1.00 | 49.41 |
| ATOM | 1825 | ND2 | ASN | 1106 | 17.930 | 23.044 | 30.102 | 1.00 | 48.31 |
| ATOM | 1826 | C | ASN | 1106 | 17.978 | 23.480 | 34.179 | 1.00 | 39.12 |
| ATOM | 1827 | O | ASN | 1106 | 16.973 | 23.021 | 34.711 | 1.00 | 36.06 |
| ATOM | 1828 | N | TRP | 1107 | 18.722 | 24.429 | 34.732 | 1.00 | 39.99 |
| ATOM | 1829 | CA | TRP | 1107 | 18.415 | 25.027 | 36.025 | 1.00 | 40.08 |
| ATOM | 1830 | CB | TRP | 1107 | 19.722 | 25.324 | 36.770 | 1.00 | 44.16 |
| ATOM | 1831 | CG | TRP | 1107 | 20.270 | 24.147 | 37.514 | 1.00 | 48.80 |
| ATOM | 1832 | CD2 | TRP | 1107 | 21.283 | 24.171 | 38.527 | 1.00 | 52.38 |
| ATOM | 1833 | CE2 | TRP | 1107 | 21.471 | 22.836 | 38.961 | 1.00 | 54.23 |
| ATOM | 1834 | CE3 | TRP | 1107 | 22.050 | 25.188 | 39.115 | 1.00 | 50.87 |
| ATOM | 1835 | CD1 | TRP | 1107 | 19.899 | 22.839 | 37.373 | 1.00 | 50.05 |
| ATOM | 1836 | NE1 | TRP | 1107 | 20.614 | 22.045 | 38.239 | 1.00 | 51.58 |
| ATOM | 1837 | CZ2 | TRP | 1107 | 22.402 | 22.494 | 39.959 | 1.00 | 53.29 |
| ATOM | 1838 | CZ3 | TRP | 1107 | 22.974 | 24.846 | 40.106 | 1.00 | 50.44 |
| ATOM | 1839 | CH2 | TRP | 1107 | 23.139 | 23.510 | 40.517 | 1.00 | 50.09 |
| ATOM | 1840 | C | TRP | 1107 | 17.612 | 26.312 | 35.836 | 1.00 | 36.90 |
| ATOM | 1841 | O | TRP | 1107 | 18.133 | 27.313 | 35.345 | 1.00 | 35.09 |
| ATOM | 1842 | N | PHE | 1108 | 16.346 | 26.283 | 36.234 | 1.00 | 34.05 |
| ATOM | 1843 | CA | PHE | 1108 | 15.482 | 27.447 | 36.071 | 1.00 | 32.57 |
| ATOM | 1844 | CB | PHE | 1108 | 14.032 | 27.035 | 35.789 | 1.00 | 29.87 |
| ATOM | 1845 | CG | PHE | 1108 | 13.851 | 26.207 | 34.556 | 1.00 | 31.30 |
| ATOM | 1846 | CD1 | PHE | 1108 | 13.946 | 24.813 | 34.617 | 1.00 | 29.28 |
| ATOM | 1847 | CD2 | PHE | 1108 | 13.563 | 26.812 | 33.333 | 1.00 | 30.16 |
| ATOM | 1848 | CE1 | PHE | 1108 | 13.755 | 24.037 | 33.483 | 1.00 | 27.25 |
| ATOM | 1849 | CE2 | PHE | 1108 | 13.370 | 26.042 | 32.189 | 1.00 | 27.77 |
| ATOM | 1850 | CZ | PHE | 1108 | 13.466 | 24.653 | 32.266 | 1.00 | 29.18 |
| ATOM | 1851 | C | PHE | 1108 | 15.426 | 28.371 | 37.270 | 1.00 | 32.28 |
| ATOM | 1852 | O | PHE | 1108 | 15.757 | 27.988 | 38.395 | 1.00 | 32.12 |
| ATOM | 1853 | N | VAL | 1109 | 14.993 | 29.599 | 36.993 | 1.00 | 30.24 |
| ATOM | 1854 | CA | VAL | 1109 | 14.771 | 30.608 | 38.009 | 1.00 | 28.78 |
| ATOM | 1855 | CB | VAL | 1109 | 14.916 | 32.040 | 37.455 | 1.00 | 27.91 |
| ATOM | 1856 | CG1 | VAL | 1109 | 14.061 | 32.986 | 38.269 | 1.00 | 28.52 |
| ATOM | 1857 | CG2 | VAL | 1109 | 16.369 | 32.493 | 37.506 | 1.00 | 26.43 |
| ATOM | 1858 | C | VAL | 1109 | 13.296 | 30.341 | 38.267 | 1.00 | 30.90 |
| ATOM | 1859 | O | VAL | 1109 | 12.478 | 30.445 | 37.348 | 1.00 | 34.02 |
| ATOM | 1860 | N | GLY | 1110 | 12.950 | 29.968 | 39.492 | 1.00 | 30.71 |
| ATOM | 1861 | CA | GLY | 1110 | 11.561 | 29.679 | 39.776 | 1.00 | 28.19 |
| ATOM | 1862 | C | GLY | 1110 | 11.182 | 30.147 | 41.153 | 1.00 | 27.88 |
| ATOM | 1863 | O | GLY | 1110 | 11.994 | 30.723 | 41.857 | 1.00 | 29.05 |
| ATOM | 1864 | N | LEU | 1111 | 9.939 | 29.899 | 41.537 | 1.00 | 27.28 |
| ATOM | 1865 | CA | LEU | 1111 | 9.455 | 30.294 | 42.841 | 1.00 | 25.79 |
| ATOM | 1866 | CB | LEU | 1111 | 8.924 | 31.720 | 42.780 | 1.00 | 26.52 |
| ATOM | 1867 | CG | LEU | 1111 | 9.968 | 32.830 | 42.641 | 1.00 | 26.50 |
| ATOM | 1868 | OD1 | LEU | 1111 | 9.340 | 34.076 | 42.009 | 1.00 | 24.70 |
| ATOM | 1869 | CD2 | LEU | 1111 | 10.546 | 33.151 | 44.029 | 1.00 | 26.77 |
| ATOM | 1870 | C | LEU | 1111 | 8.364 | 29.317 | 43.251 | 1.00 | 27.97 |
| ATOM | 1871 | O | LEU | 1111 | 7.591 | 28.842 | 42.415 | 1.00 | 26.75 |
| ATOM | 1872 | N | LYS | 1112 | 8.311 | 29.019 | 44.544 | 1.00 | 30.13 |
| ATOM | 1873 | CA | LYS | 1112 | 7.350 | 28.065 | 45.075 | 1.00 | 31.69 |
| ATOM | 1874 | CB | LYS | 1112 | 7.971 | 27.331 | 46.261 | 1.00 | 33.89 |
| ATOM | 1875 | CG | LYS | 1112 | 9.118 | 26.417 | 45.886 | 1.00 | 34.68 |
| ATOM | 1876 | CD | LYS | 1112 | 9.628 | 25.686 | 47.115 | 1.00 | 40.38 |
| ATOM | 1877 | CE | LYS | 1112 | 9.748 | 24.186 | 46.863 | 1.00 | 43.55 |
| ATOM | 1878 | NZ | LYS | 1112 | 10.244 | 23.444 | 48.060 | 1.00 | 47.64 |
| ATOM | 1879 | C | LYS | 1112 | 6.008 | 28.650 | 45.487 | 1.00 | 30.45 |
| ATOM | 1880 | O | LYS | 1112 | 5.893 | 29.841 | 45.709 | 1.00 | 30.59 |
| ATOM | 1881 | N | LYS | 1113 | 5.001 | 27.788 | 45.588 | 1.00 | 30.55 |
| ATOM | 1882 | CA | LYS | 1113 | 3.656 | 28.182 | 45.980 | 1.00 | 33.46 |
| ATOM | 1883 | CB | LYS | 1113 | 2.889 | 26.972 | 46.503 | 1.00 | 36.18 |
| ATOM | 1884 | CG | LYS | 1113 | 2.420 | 26.035 | 45.415 | 1.00 | 40.68 |
| ATOM | 1885 | CD | LYS | 1113 | 1.253 | 26.630 | 44.633 | 1.00 | 41.87 |
| ATOM | 1886 | CE | LYS | 1113 | 1.340 | 26.277 | 43.145 | 1.00 | 44.15 |
| ATOM | 1887 | NZ | LYS | 1113 | 1.559 | 24.825 | 42.892 | 1.00 | 42.02 |
| ATOM | 1888 | C | LYS | 1113 | 3.604 | 29.276 | 47.033 | 1.00 | 34.24 |
| ATOM | 1889 | O | LYS | 1113 | 2.659 | 30.056 | 47.071 | 1.00 | 34.86 |
| ATOM | 1890 | N | ASN | 1114 | 4.607 | 29.334 | 47.900 | 1.00 | 36.89 |
| ATOM | 1891 | CA | ASN | 1114 | 4.621 | 30.358 | 48.945 | 1.00 | 37.34 |
| ATOM | 1892 | CB | ASN | 1114 | 4.949 | 29.733 | 50.303 | 1.00 | 38.37 |
| ATOM | 1893 | CG | ASN | 1114 | 6.331 | 29.136 | 50.336 | 1.00 | 39.19 |
| ATOM | 1894 | OD1 | ASN | 1114 | 7.310 | 29.793 | 49.984 | 1.00 | 40.59 |

TABLE 2-continued

FGFR1 D2–D3 Complexed with FGF1

| ATOM | 1895 | ND2 | ASN | 1114 | 6.424 | 27.885 | 50.761 | 1.00 | 39.86 |
|---|---|---|---|---|---|---|---|---|---|
| ATOM | 1896 | C | ASN | 1114 | 5.619 | 31.472 | 48.652 | 1.00 | 35.57 |
| ATOM | 1897 | O | ASN | 1114 | 5.874 | 32.311 | 49.504 | 1.00 | 36.04 |
| ATOM | 1898 | N | GLY | 1115 | 6.200 | 31.458 | 47.459 | 1.00 | 34.06 |
| ATOM | 1899 | CA | GLY | 1115 | 7.134 | 32.502 | 47.080 | 1.00 | 36.04 |
| ATOM | 1900 | C | GLY | 1115 | 8.564 | 32.339 | 47.543 | 1.00 | 37.79 |
| ATOM | 1901 | O | GLY | 1115 | 9.403 | 33.217 | 47.340 | 1.00 | 36.95 |
| ATOM | 1902 | N | SER | 1116 | 8.852 | 31.213 | 48.171 | 1.00 | 40.51 |
| ATOM | 1903 | CA | SER | 1116 | 10.197 | 30.966 | 48.644 | 1.00 | 41.68 |
| ATOM | 1904 | CB | SER | 1116 | 10.181 | 29.933 | 49.772 | 1.00 | 41.90 |
| ATOM | 1905 | OG | SER | 1116 | 11.496 | 29.620 | 50.190 | 1.00 | 44.49 |
| ATOM | 1906 | C | SER | 1116 | 11.054 | 30.465 | 47.494 | 1.00 | 42.89 |
| ATOM | 1907 | O | SER | 1116 | 10.576 | 29.757 | 46.605 | 1.00 | 42.23 |
| ATOM | 1908 | N | CYS | 1117 | 12.323 | 30.855 | 47.523 | 1.00 | 45.02 |
| ATOM | 1909 | CA | CYS | 1117 | 13.295 | 30.453 | 46.519 | 1.00 | 46.88 |
| ATOM | 1910 | CB | CYS | 1117 | 14.695 | 30.722 | 47.075 | 1.00 | 43.60 |
| ATOM | 1911 | SC | CYS | 1117 | 16.032 | 29.895 | 46.216 | 1.00 | 48.25 |
| ATOM | 1912 | C | CYS | 1117 | 13.134 | 28.960 | 46.178 | 1.00 | 49.41 |
| ATOM | 1913 | O | CYS | 1117 | 13.038 | 28.134 | 47.084 | 1.00 | 52.69 |
| ATOM | 1914 | N | LYS | 1118 | 13.071 | 28.610 | 44.893 | 1.00 | 49.61 |
| ATOM | 1915 | CA | LYS | 1118 | 12.957 | 27.199 | 44.509 | 1.00 | 49.20 |
| ATOM | 1916 | CB | LYS | 1118 | 11.799 | 26.982 | 43.522 | 1.00 | 49.31 |
| ATOM | 1917 | CG | LYS | 1118 | 11.683 | 25.533 | 43.011 | 1.00 | 49.85 |
| ATOM | 1918 | CD | LYS | 1118 | 10.225 | 25.069 | 42.854 | 1.00 | 50.35 |
| ATOM | 1919 | CE | LYS | 1118 | 10.148 | 23.575 | 42.477 | 1.00 | 51.22 |
| ATOM | 1920 | NZ | LYS | 1118 | 8.760 | 22.996 | 42.520 | 1.00 | 51.56 |
| ATOM | 1921 | C | LYS | 1118 | 14.279 | 26.699 | 43.904 | 1.00 | 49.92 |
| ATOM | 1922 | O | LYS | 1118 | 14.640 | 27.045 | 42.777 | 1.00 | 50.66 |
| ATOM | 1923 | N | ARG | 1119 | 14.998 | 25.890 | 44.673 | 1.00 | 50.19 |
| ATOM | 1924 | CA | ARG | 1119 | 16.281 | 25.343 | 44.253 | 1.00 | 50.36 |
| ATOM | 1925 | CB | ARG | 1119 | 16.624 | 24.114 | 45.096 | 1.00 | 52.65 |
| ATOM | 1926 | CG | ARG | 1119 | 16.160 | 24.207 | 46.545 | 1.00 | 56.80 |
| ATOM | 1927 | CD | ARG | 1119 | 16.685 | 23.048 | 47.391 | 1.00 | 59.18 |
| ATOM | 1928 | NE | ARG | 1119 | 18.143 | 23.025 | 47.393 | 1.00 | 59.69 |
| ATOM | 1929 | CZ | ARG | 1119 | 18.880 | 22.090 | 46.802 | 1.00 | 61.21 |
| ATOM | 1930 | NH1 | ARG | 1119 | 18.298 | 21.084 | 46.162 | 1.00 | 59.96 |
| ATOM | 1931 | NH2 | ARG | 1119 | 20.204 | 22.171 | 46.838 | 1.00 | 61.64 |
| ATOM | 1932 | C | ARG | 1119 | 16.273 | 24.956 | 42.779 | 1.00 | 50.59 |
| ATOM | 1933 | O | ARG | 1119 | 15.477 | 24.124 | 42.349 | 1.00 | 49.28 |
| ATOM | 1934 | N | GLY | 1120 | 17.169 | 25.563 | 42.010 | 1.00 | 51.51 |
| ATOM | 1935 | CA | GLY | 1120 | 17.259 | 25.270 | 40.590 | 1.00 | 51.80 |
| ATOM | 1936 | C | GLY | 1120 | 17.227 | 23.796 | 40.210 | 1.00 | 52.28 |
| ATOM | 1937 | O | GLY | 1120 | 16.583 | 23.433 | 39.228 | 1.00 | 52.78 |
| ATOM | 1938 | N | PRO | 1121 | 17.912 | 22.914 | 40.954 | 1.00 | 52.45 |
| ATOM | 1939 | CD | PRO | 1121 | 18.817 | 23.151 | 42.088 | 1.00 | 52.24 |
| ATOM | 1940 | CA | PRO | 1121 | 17.897 | 21.492 | 40.607 | 1.00 | 52.16 |
| ATOM | 1941 | CB | PRO | 1121 | 19.020 | 20.926 | 41.463 | 1.00 | 51.38 |
| ATOM | 1942 | CG | PRO | 1121 | 18.929 | 21.770 | 42.682 | 1.00 | 51.92 |
| ATOM | 1943 | C | PRO | 1121 | 16.571 | 20.774 | 40.847 | 1.00 | 51.27 |
| ATOM | 1944 | O | PRO | 1121 | 16.486 | 19.565 | 40.648 | 1.00 | 51.20 |
| ATOM | 1945 | N | ARG | 1122 | 15.545 | 21.504 | 41.279 | 1.00 | 51.52 |
| ATOM | 1946 | CA | ARG | 1122 | 14.231 | 20.898 | 41.519 | 1.00 | 51.08 |
| ATOM | 1947 | CB | ARG | 1122 | 13.789 | 21.088 | 42.977 | 1.00 | 55.21 |
| ATOM | 1948 | CG | ARG | 1122 | 14.904 | 21.394 | 43.970 | 1.00 | 60.91 |
| ATOM | 1949 | CD | ARG | 1122 | 15.931 | 20.274 | 44.078 | 1.00 | 65.86 |
| ATOM | 1950 | NE | ARG | 1122 | 15.424 | 19.078 | 44.751 | 1.00 | 68.18 |
| ATOM | 1951 | CZ | ARG | 1122 | 16.174 | 18.016 | 45.044 | 1.00 | 70.69 |
| ATOM | 1952 | NH1 | ARG | 1122 | 17.466 | 17.993 | 44.726 | 1.00 | 70.77 |
| ATOM | 1953 | NH2 | ARG | 1122 | 15.635 | 16.975 | 45.663 | 1.00 | 72.96 |
| ATOM | 1954 | C | ARG | 1122 | 13.184 | 21.532 | 40.594 | 1.00 | 49.22 |
| ATOM | 1955 | O | ARG | 1122 | 11.973 | 21.357 | 40.784 | 1.00 | 47.14 |
| ATOM | 1956 | N | THR | 1123 | 13.665 | 22.271 | 39.596 | 1.00 | 46.78 |
| ATOM | 1957 | CA | THR | 1123 | 12.798 | 22.937 | 38.638 | 1.00 | 44.43 |
| ATOM | 1958 | CB | THR | 1123 | 13.306 | 24.351 | 38.326 | 1.00 | 40.55 |
| ATOM | 1959 | OG1 | THR | 1123 | 14.431 | 24.279 | 37.447 | 1.00 | 31.85 |
| ATOM | 1960 | CG2 | THR | 1123 | 13.727 | 25.048 | 39.613 | 1.00 | 40.32 |
| ATOM | 1961 | C | THR | 1123 | 12.710 | 22.137 | 37.339 | 1.00 | 47.64 |
| ATOM | 1962 | O | THR | 1123 | 13.731 | 21.753 | 36.754 | 1.00 | 45.66 |
| ATOM | 1963 | N | HIS | 1124 | 11.479 | 21.895 | 36.896 | 1.00 | 50.67 |
| ATOM | 1964 | CA | HIS | 1124 | 11.224 | 21.130 | 35.678 | 1.00 | 54.16 |
| ATOM | 1965 | CB | HIS | 1124 | 10.338 | 19.916 | 36.009 | 1.00 | 58.09 |
| ATOM | 1966 | CG | HIS | 1124 | 10.131 | 18.975 | 34.860 | 1.00 | 62.09 |
| ATOM | 1967 | CD2 | HIS | 1124 | 10.504 | 17.684 | 34.686 | 1.00 | 62.98 |
| ATOM | 1968 | ND1 | HIS | 1124 | 9.467 | 19.338 | 33.707 | 1.00 | 65.77 |
| ATOM | 1969 | CE1 | HIS | 1124 | 9.439 | 18.313 | 32.873 | 1.00 | 65.18 |
| ATOM | 1970 | NE2 | HIS | 1124 | 10.062 | 17.296 | 33.445 | 1.00 | 64.99 |
| ATOM | 1971 | C | HIS | 1124 | 10.549 | 21.986 | 34.609 | 1.00 | 54.27 |

TABLE 2-continued

| FGFR1 D2–D3 Complexed with FGF1 | | | | | | | | |
|---|---|---|---|---|---|---|---|---|
| ATOM | 1972 | O | HIS | 1124 | 9.888 | 22.980 | 34.918 | 1.00 | 54.50 |
| ATOM | 1973 | N | TYR | 1125 | 10.722 | 21.584 | 33.354 | 1.00 | 54.63 |
| ATOM | 1974 | CA | TYR | 1125 | 10.137 | 22.277 | 32.214 | 1.00 | 54.24 |
| ATOM | 1975 | CB | TYR | 1125 | 10.423 | 21.496 | 30.929 | 1.00 | 59.36 |
| ATOM | 1976 | CG | TYR | 1125 | 9.671 | 22.015 | 29.722 | 1.00 | 66.87 |
| ATOM | 1977 | CD1 | TYR | 1125 | 9.981 | 23.259 | 29.155 | 1.00 | 69.31 |
| ATOM | 1978 | CE1 | TYR | 1125 | 9.269 | 23.750 | 28.052 | 1.00 | 71.83 |
| ATOM | 1979 | CD2 | TYR | 1125 | 8.630 | 21.273 | 29.156 | 1.00 | 69.80 |
| ATOM | 1980 | CE2 | TYR | 1125 | 7.912 | 21.753 | 28.054 | 1.00 | 71.60 |
| ATOM | 1981 | CZ | TYR | 1125 | 8.235 | 22.988 | 27.508 | 1.00 | 72.61 |
| ATOM | 1982 | OH | TYR | 1125 | 7.527 | 23.451 | 26.420 | 1.00 | 73.01 |
| ATOM | 1983 | C | TYR | 1125 | 8.628 | 22.483 | 32.344 | 1.00 | 51.31 |
| ATOM | 1984 | O | TYR | 1125 | 8.091 | 23.494 | 31.894 | 1.00 | 52.27 |
| ATOM | 1985 | N | GLY | 1126 | 7.941 | 21.532 | 32.961 | 1.00 | 47.56 |
| ATOM | 1986 | CA | GLY | 1126 | 6.502 | 21.652 | 33.087 | 1.00 | 43.88 |
| ATOM | 1987 | C | GLY | 1126 | 5.985 | 22.296 | 34.354 | 1.00 | 42.13 |
| ATOM | 1988 | O | GLY | 1126 | 4.796 | 22.194 | 34.664 | 1.00 | 42.63 |
| ATOM | 1989 | N | GLN | 1127 | 6.853 | 22.974 | 35.090 | 1.00 | 39.48 |
| ATOM | 1990 | CA | GLN | 1127 | 6.416 | 23.601 | 36.330 | 1.00 | 36.35 |
| ATOM | 1991 | CB | GLN | 1127 | 7.569 | 23.611 | 37.332 | 1.00 | 36.34 |
| ATOM | 1992 | CG | GLN | 1127 | 8.169 | 22.237 | 37.592 | 1.00 | 39.71 |
| ATOM | 1993 | CD | GLN | 1127 | 9.057 | 22.204 | 38.832 | 1.00 | 42.52 |
| ATOM | 1994 | OE1 | GLN | 1127 | 10.011 | 22.983 | 38.952 | 1.00 | 42.90 |
| ATOM | 1995 | NE2 | GLN | 1127 | 8.745 | 21.297 | 39.763 | 1.00 | 42.62 |
| ATOM | 1996 | C | GLN | 1127 | 5.855 | 25.019 | 36.172 | 1.00 | 34.79 |
| ATOM | 1997 | O | GLN | 1127 | 6.207 | 25.751 | 35.246 | 1.00 | 35.39 |
| ATOM | 1998 | N | LYS | 1128 | 4.959 | 25.388 | 37.081 | 1.00 | 31.56 |
| ATOM | 1999 | CA | LYS | 1128 | 4.362 | 26.713 | 37.092 | 1.00 | 29.98 |
| ATOM | 2000 | CB | LYS | 1128 | 3.039 | 26.692 | 37.860 | 1.00 | 30.28 |
| ATOM | 2001 | CG | LYS | 1128 | 1.809 | 26.365 | 37.033 | 1.00 | 32.79 |
| ATOM | 2002 | CD | LYS | 1128 | 0.595 | 26.130 | 37.937 | 1.00 | 36.26 |
| ATOM | 2003 | CE | LYS | 1128 | −0.648 | 26.865 | 37.452 | 1.00 | 34.75 |
| ATOM | 2004 | NZ | LYS | 1128 | −0.529 | 28.348 | 37.611 | 1.00 | 37.92 |
| ATOM | 2005 | C | LYS | 1128 | 5.341 | 27.630 | 37.815 | 1.00 | 29.54 |
| ATOM | 2006 | O | LYS | 1128 | 5.296 | 28.852 | 37.675 | 1.00 | 28.37 |
| ATOM | 2007 | N | ALA | 1129 | 6.227 | 27.020 | 38.593 | 1.00 | 28.70 |
| ATOM | 2008 | CA | ALA | 1129 | 7.209 | 27.763 | 39.361 | 1.00 | 29.70 |
| ATOM | 2009 | CB | ALA | 1129 | 7.946 | 26.817 | 40.300 | 1.00 | 31.85 |
| ATOM | 2010 | C | ALA | 1129 | 8.212 | 28.537 | 38.501 | 1.00 | 28.04 |
| ATOM | 2011 | O | ALA | 1129 | 8.671 | 29.614 | 38.897 | 1.00 | 24.95 |
| ATOM | 2012 | N | ILE | 1130 | 8.548 | 27.997 | 37.331 | 1.00 | 25.55 |
| ATOM | 2013 | CA | ILE | 1130 | 9.512 | 28.668 | 36.460 | 1.00 | 25.84 |
| ATOM | 2014 | CB | ILE | 1130 | 10.408 | 27.648 | 35.730 | 1.00 | 24.07 |
| ATOM | 2015 | CG2 | ILE | 1130 | 11.103 | 26.771 | 36.743 | 1.00 | 25.87 |
| ATOM | 2016 | CG1 | ILE | 1130 | 9.576 | 26.785 | 34.783 | 1.00 | 22.30 |
| ATOM | 2017 | CD1 | ILE | 1130 | 10.421 | 25.886 | 33.896 | 1.00 | 18.90 |
| ATOM | 2018 | C | ILE | 1130 | 8.901 | 29.619 | 35.417 | 1.00 | 25.23 |
| ATOM | 2019 | O | ILE | 1130 | 9.620 | 30.188 | 34.585 | 1.00 | 23.60 |
| ATOM | 2020 | N | LEU | 1131 | 7.582 | 29.796 | 35.474 | 1.00 | 22.59 |
| ATOM | 2021 | CA | LEU | 1131 | 6.885 | 30.672 | 34.542 | 1.00 | 21.21 |
| ATOM | 2022 | CB | LEU | 1131 | 5.493 | 30.115 | 34.227 | 1.00 | 15.60 |
| ATOM | 2023 | CG | LEU | 1131 | 5.505 | 28.801 | 33.432 | 1.00 | 11.10 |
| ATOM | 2024 | CD1 | LEU | 1131 | 4.108 | 28.233 | 33.361 | 1.00 | 7.19 |
| ATOM | 2025 | CD2 | LEU | 1131 | 6.082 | 29.033 | 32.038 | 1.00 | 4.00 |
| ATOM | 2026 | C | LEU | 1131 | 6.774 | 32.086 | 35.086 | 1.00 | 23.55 |
| ATOM | 2027 | O | LEU | 1131 | 6.251 | 32.309 | 36.191 | 1.00 | 23.78 |
| ATOM | 2028 | N | PHE | 1132 | 7.265 | 33.042 | 34.298 | 1.00 | 23.72 |
| ATOM | 2029 | C | APHE | 1132 | 7.249 | 34.438 | 34.708 | 1.00 | 24.86 |
| ATOM | 2030 | CB | PHE | 1132 | 8.685 | 34.916 | 34.968 | 1.00 | 28.80 |
| ATOM | 2031 | CG | PHE | 1132 | 9.291 | 34.355 | 36.229 | 1.00 | 29.89 |
| ATOM | 2032 | CD1 | PHE | 1132 | 9.078 | 34.978 | 37.458 | 1.00 | 29.52 |
| ATOM | 2033 | CD2 | PHE | 1132 | 10.028 | 33.176 | 36.193 | 1.00 | 30.41 |
| ATOM | 2034 | CE1 | PHE | 1132 | 9.591 | 34.429 | 38.629 | 1.00 | 33.18 |
| ATOM | 2035 | CE2 | PHE | 1132 | 10.544 | 32.616 | 37.364 | 1.00 | 32.28 |
| ATOM | 2036 | CZ | PHE | 1132 | 10.328 | 33.240 | 38.582 | 1.00 | 32.37 |
| ATOM | 2037 | C | PHE | 1132 | 6.577 | 35.341 | 33.697 | 1.00 | 24.19 |
| ATOM | 2038 | O | PHE | 1132 | 6.553 | 35.050 | 32.505 | 1.00 | 28.10 |
| ATOM | 2039 | N | LEU | 1133 | 6.048 | 36.451 | 34.186 | 1.00 | 22.19 |
| ATOM | 2040 | CA | LEU | 1133 | 5.365 | 37.404 | 33.339 | 1.00 | 20.42 |
| ATOM | 2041 | CB | LEU | 1133 | 3.875 | 37.313 | 33.627 | 1.00 | 18.98 |
| ATOM | 2042 | CG | LEU | 1133 | 2.869 | 37.744 | 32.573 | 1.00 | 17.32 |
| ATOM | 2043 | CD1 | LEU | 1133 | 3.125 | 36.981 | 31.292 | 1.00 | 17.67 |
| ATOM | 2044 | CD2 | LEU | 1133 | 1.458 | 37.454 | 33.091 | 1.00 | 17.57 |
| ATOM | 2045 | C | LEU | 1133 | 5.872 | 38.816 | 33.636 | 1.00 | 21.21 |
| ATOM | 2046 | O | LEU | 1133 | 5.916 | 39.230 | 34.790 | 1.00 | 21.22 |
| ATOM | 2047 | N | PRO | 1134 | 6.298 | 39.558 | 32.602 | 1.00 | 22.31 |
| ATOM | 2048 | CD | PRO | 1134 | 6.657 | 39.079 | 31.256 | 1.00 | 21.79 |

TABLE 2-continued

FGFR1 D2–D3 Complexed with FGF1

| | | | | | | | | |
|---|---|---|---|---|---|---|---|---|
| ATOM | 2049 | CA | PRO | 1134 | 6.788 | 40.928 | 32.810 | 1.00 | 21.91 |
| ATOM | 2050 | CB | PRO | 1134 | 7.495 | 41.248 | 31.496 | 1.00 | 22.07 |
| ATOM | 2051 | CG | PRO | 1134 | 7.868 | 39.892 | 30.954 | 1.00 | 20.81 |
| ATOM | 2052 | C | PRO | 1134 | 5.603 | 41.874 | 33.046 | 1.00 | 21.75 |
| ATOM | 2053 | O | PRO | 1134 | 4.594 | 41.786 | 32.353 | 1.00 | 22.26 |
| ATOM | 2054 | N | LEU | 1135 | 5.710 | 42.761 | 34.028 | 1.00 | 22.32 |
| ATOM | 2055 | CA | LEU | 1135 | 4.632 | 43.708 | 34.297 | 1.00 | 21.76 |
| ATOM | 2056 | CB | LEU | 1135 | 3.785 | 43.304 | 35.512 | 1.00 | 17.50 |
| ATOM | 2057 | CG | LEU | 1135 | 2.990 | 41.993 | 35.546 | 1.00 | 14.52 |
| ATOM | 2058 | CD1 | LEU | 1135 | 1.923 | 42.095 | 36.624 | 1.00 | 4.60 |
| ATOM | 2059 | CD2 | LEU | 1135 | 2.341 | 41.732 | 34.208 | 1.00 | 10.88 |
| ATOM | 2060 | C | LEU | 1135 | 5.198 | 45.072 | 34.571 | 1.00 | 23.53 |
| ATOM | 2061 | O | LEU | 1135 | 6.331 | 45.199 | 35.037 | 1.00 | 24.94 |
| ATOM | 2062 | N | PRO | 1136 | 4.419 | 46.121 | 34.262 | 1.00 | 27.53 |
| ATOM | 2063 | CD | PRO | 1136 | 3.196 | 46.068 | 33.441 | 1.00 | 26.33 |
| ATOM | 2064 | CA | PRO | 1136 | 4.822 | 47.515 | 34.482 | 1.00 | 28.25 |
| ATOM | 2065 | CB | PRO | 1136 | 3.726 | 48.305 | 33.770 | 1.00 | 27.06 |
| ATOM | 2066 | CG | PRO | 1136 | 3.281 | 47.370 | 32.695 | 1.00 | 26.26 |
| ATOM | 2067 | C | PRO | 1136 | 4.805 | 47.742 | 35.993 | 1.00 | 28.67 |
| ATOM | 2068 | O | PRO | 1136 | 4.103 | 47.039 | 36.720 | 1.00 | 30.06 |
| ATOM | 2069 | N | VAL | 1137 | 5.560 | 48.713 | 36.480 | 1.00 | 29.29 |
| ATOM | 2070 | GA | VAL | 1137 | 5.580 | 48.936 | 37.916 | 1.00 | 27.70 |
| ATOM | 2071 | CB | VAL | 1137 | 6.458 | 50.136 | 38.273 | 1.00 | 25.31 |
| ATOM | 2072 | CG1 | VAL | 1137 | 6.339 | 50.425 | 39.749 | 1.00 | 26.58 |
| ATOM | 2073 | CG2 | VAL | 1137 | 7.921 | 49.830 | 37.914 | 1.00 | 23.39 |
| ATOM | 2074 | C | VAL | 1137 | 4.192 | 49.130 | 38.514 | 1.00 | 28.47 |
| ATOM | 2075 | O | VAL | 1137 | 3.862 | 48.516 | 39.536 | 1.00 | 27.14 |
| ATOM | 2076 | N | SER | 1138 | 3.385 | 49.970 | 37.863 | 1.00 | 32.03 |
| ATOM | 2077 | CA | SER | 1138 | 2.020 | 50.289 | 38.314 | 1.00 | 32.04 |
| ATOM | 2078 | CB | SER | 1138 | 1.746 | 51.789 | 38.143 | 1.00 | 30.10 |
| ATOM | 2079 | C | SER | 1138 | 0.918 | 49.500 | 37.613 | 1.00 | 31.47 |
| ATOM | 2080 | O | SER | 1138 | −0.213 | 49.518 | 38.157 | 1.00 | 33.77 |
| ATOM | 2081 | CB | ASN | 2147 | 26.814 | 102.975 | 10.017 | 1.00 | 45.18 |
| ATOM | 2082 | CG | ASN | 2147 | 28.252 | 103.343 | 9.748 | 1.00 | 51.54 |
| ATOM | 2083 | OD1 | ASN | 2147 | 28.630 | 103.582 | 8.603 | 1.00 | 53.81 |
| ATOM | 2084 | ND2 | ASN | 2147 | 29.060 | 103.421 | 10.803 | 1.00 | 52.12 |
| ATOM | 2085 | C | ASN | 2147 | 24.804 | 104.423 | 9.509 | 1.00 | 39.76 |
| ATOM | 2086 | O | ASN | 2147 | 24.748 | 105.461 | 8.872 | 1.00 | 42.25 |
| ATOM | 2087 | N | ASN | 2147 | 25.555 | 104.031 | 11.860 | 1.00 | 43.01 |
| ATOM | 2088 | CA | ASN | 2147 | 25.973 | 104.190 | 10.443 | 1.00 | 42.82 |
| ATOM | 2089 | N | ARG | 2148 | 23.848 | 103.510 | 9.442 | 1.00 | 35.64 |
| ATOM | 2090 | CA | ARG | 2148 | 22.695 | 103.737 | 8.568 | 1.00 | 33.55 |
| ATOM | 2091 | CB | ARG | 2148 | 22.484 | 102.544 | 7.640 | 1.00 | 33.03 |
| ATOM | 2092 | C | ARG | 2148 | 21.380 | 104.083 | 9.268 | 1.00 | 31.68 |
| ATOM | 2093 | O | ARG | 2148 | 21.238 | 103.902 | 10.481 | 1.00 | 31.50 |
| ATOM | 2094 | N | MET | 2149 | 20.425 | 104.579 | 8.485 | 1.00 | 29.10 |
| ATOM | 2095 | CA | MET | 2149 | 19.110 | 104.959 | 8.982 | 1.00 | 26.25 |
| ATOM | 2096 | CB | MET | 2149 | 18.219 | 105.397 | 7.824 | 1.00 | 27.33 |
| ATOM | 2097 | CG | MET | 2149 | 16.823 | 105.852 | 8.235 | 1.00 | 28.42 |
| ATOM | 2098 | SD | MET | 2149 | 16.815 | 107.525 | 8.910 | 1.00 | 36.58 |
| ATOM | 2099 | CE | MET | 2149 | 15.404 | 107.453 | 9.968 | 1.00 | 29.53 |
| ATOM | 2100 | C | MET | 2149 | 18.426 | 103.810 | 9.714 | 1.00 | 24.81 |
| ATOM | 2101 | O | MET | 2149 | 18.116 | 102.777 | 9.129 | 1.00 | 23.83 |
| ATOM | 2102 | N | PRO | 2150 | 18.161 | 103.987 | 11.015 | 1.00 | 23.19 |
| ATOM | 2103 | CD | PRO | 2150 | 18.459 | 105.161 | 11.850 | 1.00 | 22.29 |
| ATOM | 2104 | CA | PRO | 2150 | 17.503 | 102.942 | 11.807 | 1.00 | 21.50 |
| ATOM | 2105 | CB | PRO | 2150 | 17.247 | 103.630 | 13.143 | 1.00 | 20.73 |
| ATOM | 2106 | CG | PRO | 2150 | 18.411 | 104.582 | 13.242 | 1.00 | 20.31 |
| ATOM | 2107 | G | PRO | 2150 | 16.222 | 102.392 | 11.182 | 1.00 | 21.16 |
| ATOM | 2108 | O | PRO | 2150 | 15.409 | 103.138 | 10.618 | 1.00 | 19.67 |
| ATOM | 2109 | N | VAL | 2151 | 16.056 | 101.071 | 11.279 | 1.00 | 21.55 |
| ATOM | 2110 | GA | VAL | 2151 | 14.874 | 100.379 | 10.751 | 1.00 | 16.77 |
| ATOM | 2111 | CB | VAL | 2151 | 15.089 | 99.899 | 9.290 | 1.00 | 13.02 |
| ATOM | 2112 | CG1 | VAL | 2151 | 13.887 | 99.086 | 8.836 | 1.00 | 10.15 |
| ATOM | 2113 | CG2 | VAL | 2151 | 15.285 | 101.091 | 8.368 | 1.00 | 10.43 |
| ATOM | 2114 | C | VAL | 2151 | 14.537 | 99.164 | 11.606 | 1.00 | 15.22 |
| ATOM | 2115 | O | VAL | 2151 | 15.310 | 98.206 | 11.676 | 1.00 | 14.27 |
| ATOM | 2116 | N | ALA | 2152 | 13.388 | 99.207 | 12.268 | 1.00 | 14.49 |
| ATOM | 2117 | CA | ALA | 2152 | 12.980 | 98.083 | 13.104 | 1.00 | 15.15 |
| ATOM | 2118 | CB | ALA | 2152 | 11.655 | 98.394 | 13.793 | 1.00 | 11.10 |
| ATOM | 2119 | C | ALA | 2152 | 12.852 | 96.823 | 12.234 | 1.00 | 15.46 |
| ATOM | 2120 | O | ALA | 2152 | 12.463 | 96.896 | 11.064 | 1.00 | 14.12 |
| ATOM | 2121 | N | PRO | 2153 | 13.174 | 95.649 | 12.799 | 1.00 | 16.43 |
| ATOM | 2122 | CD | PRO | 2153 | 13.559 | 95.410 | 14.200 | 1.00 | 15.40 |
| ATOM | 2123 | GA | PRO | 2153 | 13.093 | 94.387 | 12.055 | 1.00 | 16.27 |
| ATOM | 2124 | CB | PRO | 2153 | 13.605 | 93.366 | 13.064 | 1.00 | 16.36 |
| ATOM | 2125 | CG | PRO | 2153 | 13.205 | 93.968 | 14.379 | 1.00 | 16.80 |

TABLE 2-continued

| | | | | FGFR1 D2–D3 Complexed with FGF1 | | | | | |
|---|---|---|---|---|---|---|---|---|---|
| ATOM | 2126 | C | PRO | 2153 | 11.709 | 94.043 | 11.516 | 1.00 | 15.96 |
| ATOM | 2127 | O | PRO | 2153 | 10.705 | 94.176 | 12.204 | 1.00 | 15.23 |
| ATOM | 2128 | N | TYR | 2154 | 11.675 | 93.596 | 10.268 | 1.00 | 19.71 |
| ATOM | 2129 | CA | TYR | 2154 | 10.424 | 93.224 | 9.606 | 1.00 | 21.43 |
| ATOM | 2130 | CB | TYR | 2154 | 9.933 | 94.369 | 8.743 | 1.00 | 18.91 |
| ATOM | 2131 | CG | TYR | 2154 | 10.926 | 94.732 | 7.678 | 1.00 | 16.22 |
| ATOM | 2132 | CD1 | TYR | 2154 | 12.161 | 95.274 | 8.011 | 1.00 | 14.25 |
| ATOM | 2133 | CE1 | TYR | 2154 | 13.087 | 95.600 | 7.029 | 1.00 | 17.02 |
| ATOM | 2134 | CD2 | TYR | 2154 | 10.638 | 94.521 | 6.332 | 1.00 | 17.27 |
| ATOM | 2135 | CE2 | TYR | 2154 | 11.559 | 94.842 | 5.340 | 1.00 | 14.79 |
| ATOM | 2136 | CZ | TYR | 2154 | 12.776 | 95.383 | 5.696 | 1.00 | 15.43 |
| ATOM | 2137 | OH | TYR | 2154 | 13.676 | 95.728 | 4.723 | 1.00 | 16.67 |
| ATOM | 2138 | C | TYR | 2154 | 10.571 | 91.995 | 8.711 | 1.00 | 22.61 |
| ATOM | 2139 | O | TYR | 2154 | 11.657 | 91.687 | 8.203 | 1.00 | 23.08 |
| ATOM | 2140 | N | TRP | 2155 | 9.452 | 91.316 | 8.502 | 1.00 | 24.53 |
| ATOM | 2141 | CA | TRP | 2155 | 9.404 | 90.115 | 7.677 | 1.00 | 25.22 |
| ATOM | 2142 | CB | TRP | 2155 | 8.017 | 89.493 | 7.786 | 1.00 | 20.66 |
| ATOM | 2143 | CG | TRP | 2155 | 7.600 | 89.146 | 9.194 | 1.00 | 16.41 |
| ATOM | 2144 | CD2 | TRP | 2155 | 8.402 | 88.535 | 10.208 | 1.00 | 12.68 |
| ATOM | 2145 | CE2 | TRP | 2155 | 7.571 | 88.351 | 11.344 | 1.00 | 14.74 |
| ATOM | 2146 | CE3 | TRP | 2155 | 9.737 | 88.123 | 10.273 | 1.00 | 13.09 |
| ATOM | 2147 | CD1 | TRP | 2155 | 6.352 | 89.305 | 9.741 | 1.00 | 18.18 |
| ATOM | 2148 | NE1 | TRP | 2155 | 6.328 | 88.829 | 11.029 | 1.00 | 14.03 |
| ATOM | 2149 | CZ2 | TRP | 2155 | 8.040 | 87.769 | 12.532 | 1.00 | 11.48 |
| ATOM | 2150 | CZ3 | TRP | 2155 | 10.203 | 87.541 | 11.459 | 1.00 | 12.94 |
| ATOM | 2151 | CH2 | TRP | 2155 | 9.353 | 87.373 | 12.569 | 1.00 | 14.66 |
| ATOM | 2152 | C | TRP | 2155 | 9.722 | 90.419 | 6.210 | 1.00 | 27.64 |
| ATOM | 2153 | O | TRP | 2155 | 9.326 | 91.454 | 5.679 | 1.00 | 27.23 |
| ATOM | 2154 | N | THR | 2156 | 10.433 | 89.503 | 5.560 | 1.00 | 30.07 |
| ATOM | 2155 | CA | THR | 2156 | 10.810 | 89.663 | 4.162 | 1.00 | 32.68 |
| ATOM | 2156 | CB | THR | 2156 | 12.334 | 89.496 | 3.996 | 1.00 | 33.62 |
| ATOM | 2157 | OG1 | THR | 2156 | 12.998 | 90.564 | 4.675 | 1.00 | 36.23 |
| ATOM | 2158 | CG2 | THR | 2156 | 12.737 | 89.532 | 2.531 | 1.00 | 40.06 |
| ATOM | 2159 | C | THR | 2156 | 10.083 | 88.642 | 3.289 | 1.00 | 34.34 |
| ATOM | 2160 | O | THR | 2156 | 10.241 | 88.617 | 2.069 | 1.00 | 34.49 |
| ATOM | 2161 | N | SER | 2157 | 9.272 | 87.803 | 3.918 | 1.00 | 35.53 |
| ATOM | 2162 | CA | SER | 2157 | 8.542 | 86.788 | 3.181 | 1.00 | 36.03 |
| ATOM | 2163 | CB | SER | 2157 | 9.490 | 85.632 | 2.860 | 1.00 | 37.70 |
| ATOM | 2164 | OG | SER | 2157 | 8.833 | 84.616 | 2.133 | 1.00 | 43.05 |
| ATOM | 2165 | C | SER | 2157 | 7.375 | 86.303 | 4.026 | 1.00 | 36.23 |
| ATOM | 2166 | O | SER | 2157 | 7.117 | 85.106 | 4.120 | 1.00 | 36.84 |
| ATOM | 2167 | N | PRO | 2158 | 6.639 | 87.242 | 4.639 | 1.00 | 36.88 |
| ATOM | 2168 | CD | PRO | 2158 | 6.668 | 88.673 | 4.292 | 1.00 | 35.23 |
| ATOM | 2169 | CA | PRO | 2158 | 5.487 | 86.950 | 5.498 | 1.00 | 37.16 |
| ATOM | 2170 | CB | PRO | 2158 | 4.713 | 88.262 | 5.489 | 1.00 | 36.26 |
| ATOM | 2171 | CG | PRO | 2158 | 5.790 | 89.271 | 5.347 | 1.00 | 36.76 |
| ATOM | 2172 | C | PRO | 2158 | 4.653 | 85.793 | 4.985 | 1.00 | 38.08 |
| ATOM | 2173 | O | PRO | 2158 | 4.120 | 84.997 | 5.759 | 1.00 | 37.13 |
| ATOM | 2174 | N | ALA | 2159 | 4.536 | 85.721 | 3.666 | 1.00 | 40.74 |
| ATOM | 2175 | CA | ALA | 2159 | 3.771 | 84.669 | 3.020 | 1.00 | 41.35 |
| ATOM | 2176 | CB | ALA | 2159 | 3.976 | 84.737 | 1.512 | 1.00 | 42.33 |
| ATOM | 2177 | C | ALA | 2159 | 4.214 | 83.310 | 3.549 | 1.00 | 41.99 |
| ATOM | 2178 | O | ALA | 2159 | 3.465 | 82.636 | 4.271 | 1.00 | 41.46 |
| ATOM | 2179 | N | ALA | 2160 | 5.439 | 82.922 | 3.196 | 1.00 | 40.06 |
| ATOM | 2180 | CA | ALA | 2160 | 5.992 | 81.640 | 3.615 | 1.00 | 41.70 |
| ATOM | 2181 | CB | ALA | 2160 | 7.505 | 81.629 | 3.395 | 1.00 | 40.83 |
| ATOM | 2182 | C | ALA | 2160 | 5.670 | 81.281 | 5.072 | 1.00 | 42.86 |
| ATOM | 2183 | O | ALA | 2160 | 5.556 | 80.101 | 5.418 | 1.00 | 45.81 |
| ATOM | 2184 | N | MET | 2161 | 5.505 | 82.292 | 5.919 | 1.00 | 41.09 |
| ATOM | 2185 | CA | MET | 2161 | 5.223 | 82.062 | 7.335 | 1.00 | 36.97 |
| ATOM | 2186 | CB | MET | 2161 | 5.658 | 83.287 | 8.152 | 1.00 | 35.45 |
| ATOM | 2187 | CG | MET | 2161 | 7.028 | 83.838 | 7.748 | 1.00 | 33.71 |
| ATOM | 2188 | SD | MET | 2161 | 7.574 | 85.241 | 8.737 | 1.00 | 28.89 |
| ATOM | 2189 | CE | MET | 2161 | 9.301 | 85.166 | 8.486 | 1.00 | 33.50 |
| ATOM | 2190 | C | MET | 2161 | 3.765 | 81.725 | 7.653 | 1.00 | 35.46 |
| ATOM | 2191 | O | MET | 2161 | 3.456 | 81.336 | 8.775 | 1.00 | 33.94 |
| ATOM | 2192 | N | ALA | 2162 | 2.871 | 81.866 | 6.677 | 1.00 | 35.20 |
| ATOM | 2193 | CA | ALA | 2162 | 1.449 | 81.575 | 6.900 | 1.00 | 34.67 |
| ATOM | 2194 | CB | ALA | 2162 | 0.669 | 81.773 | 5.601 | 1.00 | 37.06 |
| ATOM | 2195 | C | ALA | 2162 | 1.243 | 80.151 | 7.429 | 1.00 | 33.41 |
| ATOM | 2196 | O | ALA | 2162 | 0.459 | 79.922 | 8.353 | 1.00 | 29.20 |
| ATOM | 2197 | N | LYS | 2163 | 1.953 | 79.201 | 6.820 | 1.00 | 32.69 |
| ATOM | 2198 | CA | LYS | 2163 | 1.901 | 77.793 | 7.208 | 1.00 | 30.42 |
| ATOM | 2199 | CB | LYS | 2163 | 2.709 | 76.972 | 6.196 | 1.00 | 28.48 |
| ATOM | 2200 | CG | LYS | 2163 | 2.830 | 75.496 | 6.493 | 1.00 | 26.64 |
| ATOM | 2201 | CD | LYS | 2163 | 3.823 | 74.841 | 5.536 | 1.00 | 27.91 |
| ATOM | 2202 | CE | LYS | 2163 | 4.166 | 73.406 | 5.979 | 1.00 | 32.58 |

TABLE 2-continued

FGFR1 D2–D3 Complexed with FGF1

| ATOM | 2203 | NZ | LYS | 2163 | 5.262 | 72.761 | 5.179 | 1.00 | 29.98 |
|---|---|---|---|---|---|---|---|---|---|
| ATOM | 2204 | C | LYS | 2163 | 2.521 | 77.698 | 8.605 | 1.00 | 30.84 |
| ATOM | 2205 | O | LYS | 2163 | 3.747 | 77.594 | 8.744 | 1.00 | 29.90 |
| ATOM | 2206 | N | ALA | 2164 | 1.674 | 77.740 | 9.634 | 1.00 | 29.63 |
| ATOM | 2207 | CA | ALA | 2164 | 2.140 | 77.705 | 11.017 | 1.00 | 30.27 |
| ATOM | 2208 | CB | ALA | 2164 | 1.104 | 78.355 | 11.925 | 1.00 | 30.69 |
| ATOM | 2209 | C | ALA | 2164 | 2.503 | 76.329 | 11.550 | 1.00 | 31.68 |
| ATOM | 2210 | O | ALA | 2164 | 3.525 | 76.161 | 12.219 | 1.00 | 31.11 |
| ATOM | 2211 | N | LW | 2165 | 1.673 | 75.337 | 11.265 | 1.00 | 33.60 |
| ATOM | 2212 | CA | LEU | 2165 | 1.949 | 73.990 | 11.752 | 1.00 | 33.41 |
| ATOM | 2213 | CB | LEU | 2165 | 0.640 | 73.264 | 12.060 | 1.00 | 30.23 |
| ATOM | 2214 | CG | LEU | 2165 | 0.754 | 71.790 | 12.430 | 1.00 | 30.51 |
| ATOM | 2215 | CD1 | LEU | 2165 | 1.605 | 71.634 | 13.678 | 1.00 | 31.21 |
| ATOM | 2216 | CD2 | LEU | 2165 | −0.631 | 71.230 | 12.660 | 1.00 | 31.48 |
| ATOM | 2217 | C | LEU | 2165 | 2.782 | 73.149 | 10.788 | 1.00 | 34.43 |
| ATOM | 2218 | O | LEU | 2165 | 2.491 | 73.070 | 9.593 | 1.00 | 36.36 |
| ATOM | 2219 | N | HIS | 2166 | 3.831 | 72.532 | 11.316 | 1.00 | 33.16 |
| ATOM | 2220 | CA | HIS | 2166 | 4.678 | 71.669 | 10.517 | 1.00 | 32.38 |
| ATOM | 2221 | CB | HIS | 2166 | 6.144 | 72.100 | 10.596 | 1.00 | 32.21 |
| ATOM | 2222 | CG | HIS | 2166 | 6.515 | 73.170 | 9.620 | 1.00 | 32.42 |
| ATOM | 2223 | CD2 | HIS | 2166 | 7.354 | 73.155 | 8.558 | 1.00 | 31.95 |
| ATOM | 2224 | ND1 | HIS | 2166 | 6.009 | 74.451 | 9.690 | 1.00 | 33.80 |
| ATOM | 2225 | CE1 | HIS | 2166 | 6.521 | 75.178 | 8.712 | 1.00 | 32.14 |
| ATOM | 2226 | NE2 | HIS | 2166 | 7.340 | 74.416 | 8.012 | 1.00 | 31.06 |
| ATOM | 2227 | C | HIS | 2166 | 4.540 | 70.242 | 11.027 | 1.00 | 32.81 |
| ATOM | 2228 | O | HIS | 2166 | 5.107 | 69.874 | 12.059 | 1.00 | 33.23 |
| ATOM | 2229 | N | ALA | 2167 | 3.761 | 69.441 | 10.313 | 1.00 | 31.73 |
| ATOM | 2230 | CA | ALA | 2167 | 3.593 | 68.053 | 10.695 | 1.00 | 29.93 |
| ATOM | 2231 | CB | ALA | 2167 | 2.159 | 67.602 | 10.440 | 1.00 | 28.39 |
| ATOM | 2232 | C | ALA | 2167 | 4.584 | 67.267 | 9.842 | 1.00 | 27.89 |
| ATOM | 2233 | O | ALA | 2167 | 4.592 | 67.373 | 8.616 | 1.00 | 29.00 |
| ATOM | 2234 | N | VAL | 2168 | 5.433 | 66.490 | 10.495 | 1.00 | 26.21 |
| ATOM | 2235 | CA | VAL | 2168 | 6.442 | 65.720 | 9.782 | 1.00 | 24.32 |
| ATOM | 2236 | CB | VAL | 2168 | 7.831 | 66.432 | 9.911 | 1.00 | 22.47 |
| ATOM | 2237 | CG1 | VAL | 2168 | 8.943 | 65.438 | 10.278 | 1.00 | 21.29 |
| ATOM | 2238 | CG2 | VAL | 2168 | 8.157 | 67.140 | 8.617 | 1.00 | 15.49 |
| ATOM | 2239 | C | VAL | 2168 | 6.554 | 64.267 | 10.250 | 1.00 | 24.60 |
| ATOM | 2240 | O | VAL | 2168 | 6.384 | 63.948 | 11.436 | 1.00 | 23.00 |
| ATOM | 2241 | N | PRO | 2169 | 6.811 | 63.353 | 9.311 | 1.00 | 23.98 |
| ATOM | 2242 | CD | PRO | 2169 | 6.899 | 63.436 | 7.843 | 1.00 | 22.43 |
| ATOM | 2243 | CA | PRO | 2169 | 6.931 | 61.973 | 9.786 | 1.00 | 24.42 |
| ATOM | 2244 | CB | PRO | 2169 | 6.794 | 61.153 | 8.500 | 1.00 | 21.59 |
| ATOM | 2245 | CG | PRO | 2169 | 7.418 | 62.052 | 7.466 | 1.00 | 22.42 |
| ATOM | 2246 | C | PRO | 2169 | 8.316 | 61.854 | 10.450 | 1.00 | 23.60 |
| ATOM | 2247 | O | PRO | 2169 | 9.302 | 62.438 | 9.974 | 1.00 | 22.30 |
| ATOM | 2248 | N | ALA | 2170 | 8.378 | 61.129 | 11.564 | 1.00 | 20.63 |
| ATOM | 2249 | CA | ALA | 2170 | 9.627 | 60.950 | 12.281 | 1.00 | 16.73 |
| ATOM | 2250 | CB | ALA | 2170 | 9.474 | 59.839 | 13.294 | 1.00 | 16.46 |
| ATOM | 2251 | C | ALA | 2170 | 10.785 | 60.645 | 11.343 | 1.00 | 15.08 |
| ATOM | 2252 | O | ALA | 2170 | 10.613 | 59.952 | 10.340 | 1.00 | 14.72 |
| ATOM | 2253 | N | ALA | 2171 | 11.957 | 61.191 | 11.670 | 1.00 | 16.41 |
| ATOM | 2254 | CA | ALA | 2171 | 13.192 | 60.979 | 10.905 | 1.00 | 15.01 |
| ATOM | 2255 | CB | ALA | 2171 | 13.190 | 59.591 | 10.258 | 1.00 | 13.99 |
| ATOM | 2256 | C | ALA | 2171 | 13.491 | 62.022 | 9.854 | 1.00 | 14.60 |
| ATOM | 2257 | O | ALA | 2171 | 14.598 | 62.084 | 9.339 | 1.00 | 17.74 |
| ATOM | 2258 | N | ALA | 2172 | 12.519 | 62.847 | 9.519 | 1.00 | 17.17 |
| ATOM | 2259 | CA | ALA | 2172 | 12.768 | 63.859 | 8.509 | 1.00 | 18.37 |
| ATOM | 2260 | CB | ALA | 2172 | 11.451 | 64.297 | 7.866 | 1.00 | 16.27 |
| ATOM | 2261 | C | ALA | 2172 | 13.483 | 65.060 | 9.132 | 1.00 | 19.13 |
| ATOM | 2262 | O | ALA | 2172 | 13.337 | 65.338 | 10.322 | 1.00 | 16.21 |
| ATOM | 2263 | N | THR | 2173 | 14.290 | 65.739 | 8.320 | 1.00 | 21.04 |
| ATOM | 2264 | CA | THR | 2173 | 14.994 | 66.943 | 8.748 | 1.00 | 18.95 |
| ATOM | 2265 | CB | THR | 2173 | 16.176 | 67.288 | 7.801 | 1.00 | 18.71 |
| ATOM | 2266 | CG1 | THR | 2173 | 17.276 | 66.402 | 8.054 | 1.00 | 16.70 |
| ATOM | 2267 | CG2 | TER | 2173 | 16.629 | 68.736 | 7.998 | 1.00 | 16.01 |
| ATOM | 2268 | C | THR | 2173 | 13.956 | 68.055 | 8.655 | 1.00 | 20.09 |
| ATOM | 2269 | O | THR | 2173 | 13.250 | 68.178 | 7.651 | 1.00 | 18.76 |
| ATOM | 2270 | N | VAL | 2174 | 13.851 | 68.855 | 9.707 | 1.00 | 19.40 |
| ATOM | 2271 | CA | VAL | 2174 | 12.890 | 69.945 | 9.732 | 1.00 | 15.32 |
| ATOM | 2272 | CB | VAL | 2174 | 12.004 | 69.821 | 10.965 | 1.00 | 12.17 |
| ATOM | 2273 | CG1 | VAL | 2174 | 11.331 | 71.134 | 11.264 | 1.00 | 12.60 |
| ATOM | 2274 | CG2 | VAL | 2174 | 10.995 | 68.736 | 10.746 | 1.00 | 7.68 |
| ATOM | 2275 | C | VAL | 2174 | 13.585 | 71.297 | 9.768 | 1.00 | 16.49 |
| ATOM | 2276 | O | VAL | 2174 | 14.447 | 71.517 | 10.616 | 1.00 | 19.77 |
| ATOM | 2277 | N | ALA | 2175 | 13.223 | 72.195 | 8.854 | 1.00 | 15.74 |
| ATOM | 2278 | CA | ALA | 2175 | 13.807 | 73.542 | 8.845 | 1.00 | 17.01 |
| ATOM | 2279 | CB | ALA | 2175 | 14.499 | 73.798 | 7.524 | 1.00 | 14.10 |

TABLE 2-continued

FGFR1 D2–D3 Complexed with FGF1

| ATOM | 2280 | C | ALA | 2175 | 12.722 | 74.609 | 9.091 | 1.00 | 18.28 |
|---|---|---|---|---|---|---|---|---|---|
| ATOM | 2281 | O | ALA | 2175 | 11.594 | 74.452 | 8.638 | 1.00 | 21.48 |
| ATOM | 2282 | N | PHE | 2176 | 13.054 | 75.665 | 9.840 | 1.00 | 20.02 |
| ATOM | 2283 | CA | PHE | 2176 | 12.122 | 76.774 | 10.125 | 1.00 | 18.22 |
| ATOM | 2284 | CB | PHE | 2176 | 11.761 | 76.856 | 11.611 | 1.00 | 16.80 |
| ATOM | 2285 | CG | PHE | 2176 | 10.820 | 75.785 | 12.061 | 1.00 | 17.78 |
| ATOM | 2286 | CD1 | PHE | 2176 | 9.781 | 75.368 | 11.236 | 1.00 | 16.51 |
| ATOM | 2287 | CD2 | PHE | 2176 | 10.974 | 75.177 | 13.307 | 1.00 | 20.55 |
| ATOM | 2288 | CE1 | PHE | 2176 | 8.905 | 74.358 | 11.634 | 1.00 | 18.12 |
| ATOM | 2289 | CE2 | PEE | 2176 | 10.097 | 74.156 | 13.723 | 1.00 | 22.23 |
| ATOM | 2290 | CZ | PHE | 2176 | 9.058 | 73.746 | 12.880 | 1.00 | 18.85 |
| ATOM | 2291 | C | PHE | 2176 | 12.750 | 78.090 | 9.697 | 1.00 | 19.21 |
| ATOM | 2292 | O | PHE | 2176 | 13.904 | 78.371 | 9.998 | 1.00 | 19.63 |
| ATOM | 2293 | N | ALA | 2177 | 11.987 | 78.913 | 9.002 | 1.00 | 20.79 |
| ATOM | 2294 | CA | ALA | 2177 | 12.541 | 80.158 | 8.518 | 1.00 | 22.37 |
| ATOM | 2295 | CB | ALA | 2177 | 12.675 | 80.099 | 6.988 | 1.00 | 23.14 |
| ATOM | 2296 | C | ALA | 2177 | 11.750 | 81.385 | 8.930 | 1.00 | 23.63 |
| ATOM | 2297 | O | ALA | 2177 | 10.525 | 81.357 | 9.070 | 1.00 | 22.68 |
| ATOM | 2298 | N | CYS | 2178 | 12.487 | 82.465 | 9.130 | 1.00 | 24.40 |
| ATOM | 2299 | CA | CYS | 2178 | 11.920 | 83.740 | 9.505 | 1.00 | 25.73 |
| ATOM | 2300 | C | CYS | 2178 | 12.706 | 84.783 | 8.736 | 1.00 | 27.05 |
| ATOM | 2301 | O | CYS | 2178 | 13.464 | 85.557 | 9.313 | 1.00 | 27.60 |
| ATOM | 2302 | CB | CYS | 2178 | 12.055 | 83.971 | 11.013 | 1.00 | 26.41 |
| ATOM | 2303 | SG | CYS | 2178 | 10.976 | 82.891 | 12.010 | 1.00 | 35.82 |
| ATOM | 2304 | N | PRO | 2179 | 12.581 | 84.781 | 7.403 | 1.00 | 28.11 |
| ATOM | 2305 | CD | PRO | 2179 | 11.929 | 83.798 | 6.519 | 1.00 | 26.95 |
| ATOM | 2306 | CA | PRO | 2179 | 13.321 | 85.781 | 6.629 | 1.00 | 28.50 |
| ATOM | 2307 | CB | PRO | 2179 | 12.798 | 85.570 | 5.212 | 1.00 | 27.84 |
| ATOM | 2308 | CG | PRO | 2179 | 12.599 | 84.078 | 5.179 | 1.00 | 28.66 |
| ATOM | 2309 | C | PRO | 2179 | 12.988 | 87.160 | 7.188 | 1.00 | 28.64 |
| ATOM | 2310 | O | PRO | 2179 | 11.820 | 87.479 | 7.441 | 1.00 | 29.06 |
| ATOM | 2311 | N | SER | 2180 | 14.013 | 87.971 | 7.404 | 1.00 | 27.60 |
| ATOM | 2312 | CA | SER | 2180 | 13.784 | 89.287 | 7.961 | 1.00 | 27.62 |
| ATOM | 2313 | CB | SER | 2180 | 13.687 | 89.208 | 9.481 | 1.00 | 29.43 |
| ATOM | 2314 | OG | SER | 2180 | 12.714 | 88.260 | 9.868 | 1.00 | 34.19 |
| ATOM | 2315 | C | SER | 2180 | 14.880 | 90.243 | 7.600 | 1.00 | 25.26 |
| ATOM | 2316 | O | SER | 2180 | 15.938 | 89.859 | 7.128 | 1.00 | 24.71 |
| ATOM | 2317 | N | SER | 2181 | 14.612 | 91.508 | 7.844 | 1.00 | 25.59 |
| ATOM | 2318 | CA | SER | 2181 | 15.577 | 92.537 | 7.561 | 1.00 | 26.24 |
| ATOM | 2319 | CB | SER | 2181 | 15.329 | 93.100 | 6.163 | 1.00 | 29.28 |
| ATOM | 2320 | OG | SER | 2181 | 16.357 | 93.995 | 5.787 | 1.00 | 35.09 |
| ATOM | 2321 | C | SER | 2181 | 15.392 | 93.613 | 8.620 | 1.00 | 25.20 |
| ATOM | 2322 | O | SER | 2181 | 14.482 | 93.534 | 9.456 | 1.00 | 21.16 |
| ATOM | 2323 | N | GLY | 2182 | 16.260 | 94.612 | 8.577 | 1.00 | 25.62 |
| ATOM | 2324 | CA | GLY | 2182 | 16.198 | 95.701 | 9.529 | 1.00 | 25.11 |
| ATOM | 2325 | C | GLY | 2182 | 17.596 | 96.234 | 9.718 | 1.00 | 26.42 |
| ATOM | 2326 | O | GLY | 2182 | 18.577 | 95.509 | 9.504 | 1.00 | 26.03 |
| ATOM | 2327 | N | THR | 2183 | 17.701 | 97.502 | 10.102 | 1.00 | 27.07 |
| ATOM | 2328 | CA | THR | 2183 | 19.007 | 98.105 | 10.317 | 1.00 | 26.58 |
| ATOM | 2329 | CB | THR | 2183 | 19.416 | 99.018 | 9.125 | 1.00 | 25.81 |
| ATOM | 2330 | OG1 | THR | 2183 | 19.415 | 100.390 | 9.532 | 1.00 | 27.66 |
| ATOM | 2331 | CG2 | THR | 2183 | 18.450 | 98.843 | 7.967 | 1.00 | 26.30 |
| ATOM | 2332 | C | THR | 2183 | 19.039 | 98.892 | 11.621 | 1.00 | 25.95 |
| ATOM | 2333 | O | THR | 2183 | 18.092 | 99.604 | 11.948 | 1.00 | 26.68 |
| ATOM | 2334 | N | PRO | 2184 | 20.117 | 98.723 | 12.408 | 1.00 | 25.59 |
| ATOM | 2335 | CD | PRO | 2184 | 20.357 | 99.372 | 13.708 | 1.00 | 25.84 |
| ATOM | 2336 | CA | PRO | 2184 | 21.225 | 97.825 | 12.066 | 1.00 | 23.93 |
| ATOM | 2337 | CB | PRO | 2184 | 22.212 | 98.037 | 13.214 | 1.00 | 21.04 |
| ATOM | 2338 | CG | PRO | 2184 | 21.329 | 98.425 | 14.352 | 1.00 | 24.26 |
| ATOM | 2339 | C | PRO | 2184 | 20.711 | 96.390 | 11.954 | 1.00 | 22.28 |
| ATOM | 2340 | O | PRO | 2184 | 19.664 | 96.056 | 12.514 | 1.00 | 17.59 |
| ATOM | 2341 | N | ASN | 2185 | 21.437 | 95.563 | 11.210 | 1.00 | 24.05 |
| ATOM | 2342 | CA | ASN | 2185 | 21.041 | 94.184 | 10.981 | 1.00 | 25.57 |
| ATOM | 2343 | CB | ASN | 2185 | 22.129 | 93.439 | 10.223 | 1.00 | 30.66 |
| ATOM | 2344 | CG | ASN | 2185 | 21.560 | 92.367 | 9.317 | 1.00 | 38.00 |
| ATOM | 2345 | OD1 | ASN | 2185 | 21.167 | 91.285 | 9.771 | 1.00 | 40.23 |
| ATOM | 2346 | ND2 | ASN | 2185 | 21.490 | 92.672 | 8.022 | 1.00 | 41.44 |
| ATOM | 2347 | C | ASN | 2185 | 20.708 | 93.454 | 12.264 | 1.00 | 24.39 |
| ATOM | 2348 | O | ASN | 2185 | 21.550 | 93.300 | 13.142 | 1.00 | 24.40 |
| ATOM | 2349 | N | PRO | 2186 | 19.462 | 92.982 | 12.376 | 1.00 | 23.14 |
| ATOM | 2350 | CD | PRO | 2186 | 18.424 | 93.174 | 11.349 | 1.00 | 24.07 |
| ATOM | 2351 | CA | PRO | 2186 | 18.924 | 92.256 | 13.526 | 1.00 | 23.24 |
| ATOM | 2352 | CB | PRO | 2186 | 17.424 | 92.246 | 13.245 | 1.00 | 23.79 |
| ATOM | 2353 | CG | PRO | 2186 | 17.371 | 92.180 | 11.766 | 1.00 | 25.15 |
| ATOM | 2354 | C | PRO | 2186 | 19.477 | 90.856 | 13.838 | 1.00 | 25.08 |
| ATOM | 2355 | O | PRO | 2186 | 20.077 | 90.168 | 12.996 | 1.00 | 24.16 |
| ATOM | 2356 | N | THR | 2187 | 19.236 | 90.465 | 15.084 | 1.00 | 23.61 |

TABLE 2-continued

FGFR1 D2–D3 Complexed with FGF1

| ATOM | 2357 | CA | THR | 2187 | 19.658 | 89.208 | 15.665 | 1.00 | 21.54 |
|---|---|---|---|---|---|---|---|---|---|
| ATOM | 2358 | CB | THR | 2187 | 20.002 | 89.451 | 17.146 | 1.00 | 22.80 |
| ATOM | 2359 | OG1 | THR | 2187 | 21.405 | 89.687 | 17.244 | 1.00 | 23.78 |
| ATOM | 2360 | CG2 | THR | 2187 | 19.582 | 88.284 | 18.041 | 1.00 | 22.31 |
| ATOM | 2361 | C | THR | 2187 | 18.605 | 88.114 | 15.540 | 1.00 | 21.64 |
| ATOM | 2362 | O | THR | 2187 | 17.405 | 88.396 | 15.442 | 1.00 | 20.29 |
| ATOM | 2363 | N | LEU | 2188 | 19.069 | 86.863 | 15.556 | 1.00 | 19.99 |
| ATOM | 2364 | CA | LEU | 2188 | 18.183 | 85.711 | 15.439 | 1.00 | 15.85 |
| ATOM | 2365 | CB | LEU | 2188 | 18.385 | 85.017 | 14.085 | 1.00 | 10.64 |
| ATOM | 2366 | CG | LEU | 2188 | 17.236 | 84.247 | 13.404 | 1.00 | 8.83 |
| ATOM | 2367 | CD1 | LEU | 2188 | 17.850 | 83.322 | 12.369 | 1.00 | 3.96 |
| ATOM | 2368 | CD2 | LEU | 2188 | 16.401 | 83.443 | 14.407 | 1.00 | 5.07 |
| ATOM | 2369 | C | LEU | 2188 | 18.421 | 84.697 | 16.558 | 1.00 | 15.07 |
| ATOM | 2370 | O | LEU | 2188 | 19.482 | 84.086 | 16.652 | 1.00 | 12.76 |
| ATOM | 2371 | N | ALA | 2189 | 17.408 | 84.520 | 17.392 | 1.00 | 14.83 |
| ATOM | 2372 | CA | ALA | 2189 | 17.462 | 83.573 | 18.483 | 1.00 | 11.93 |
| ATOM | 2373 | CB | ALA | 2189 | 17.443 | 84.314 | 19.819 | 1.00 | 8.30 |
| ATOM | 2374 | C | ALA | 2189 | 16.230 | 82.667 | 18.340 | 1.00 | 13.71 |
| ATOM | 2375 | O | ALA | 2189 | 15.225 | 83.040 | 17.726 | 1.00 | 12.23 |
| ATOM | 2376 | N | TRP | 2190 | 16.308 | 81.476 | 18.915 | 1.00 | 14.95 |
| ATOM | 2377 | CA | TRP | 2190 | 15.213 | 80.538 | 18.839 | 1.00 | 15.29 |
| ATOM | 2378 | CB | TRP | 2190 | 15.593 | 79.413 | 17.888 | 1.00 | 17.24 |
| ATOM | 2379 | CG | TRP | 2190 | 15.495 | 79.760 | 16.430 | 1.00 | 16.08 |
| ATOM | 2380 | CD2 | TRP | 2190 | 14.320 | 79.682 | 15.622 | 1.00 | 13.35 |
| ATOM | 2381 | CE2 | TRP | 2190 | 14.696 | 80.029 | 14.305 | 1.00 | 12.00 |
| ATOM | 2382 | CE3 | TRP | 2190 | 12.985 | 79.347 | 15.883 | 1.00 | 14.59 |
| ATOM | 2383 | CD1 | TRP | 2190 | 16.511 | 80.151 | 15.597 | 1.00 | 13.49 |
| ATOM | 2384 | NE1 | TRP | 2190 | 16.036 | 80.310 | 14.320 | 1.00 | 11.50 |
| ATOM | 2385 | CZ2 | TRP | 2190 | 13.782 | 80.048 | 13.245 | 1.00 | 13.72 |
| ATOM | 2386 | CZ3 | TRP | 2190 | 12.073 | 79.362 | 14.827 | 1.00 | 19.35 |
| ATOM | 2387 | CH2 | TRP | 2190 | 12.480 | 79.712 | 13.521 | 1.00 | 15.59 |
| ATOM | 2388 | C | TRP | 2190 | 14.792 | 79.945 | 20.187 | 1.00 | 18.85 |
| ATOM | 2389 | O | TRP | 2190 | 15.628 | 79.608 | 21.032 | 1.00 | 20.20 |
| ATOM | 2390 | N | LEU | 2191 | 13.484 | 79.802 | 20.371 | 1.00 | 20.34 |
| ATOM | 2391 | CA | LEU | 2191 | 12.927 | 79.254 | 21.601 | 1.00 | 23.09 |
| ATOM | 2392 | CB | LEU | 2191 | 12.041 | 80.305 | 22.275 | 1.00 | 20.62 |
| ATOM | 2393 | CG | LEU | 2191 | 12.626 | 81.677 | 22.645 | 1.00 | 23.79 |
| ATOM | 2394 | CD1 | LEU | 2191 | 11.612 | 82.415 | 23.512 | 1.00 | 24.02 |
| ATOM | 2395 | CD2 | LEU | 2191 | 13.935 | 81.535 | 23.403 | 1.00 | 22.37 |
| ATOM | 2396 | C | LEU | 2191 | 12.100 | 77.972 | 21.377 | 1.00 | 27.29 |
| ATOM | 2397 | O | LEU | 2191 | 11.570 | 77.731 | 20.286 | 1.00 | 28.27 |
| ATOM | 2398 | N | LYS | 2192 | 12.002 | 77.144 | 22.412 | 1.00 | 28.16 |
| ATOM | 2399 | CA | LYS | 2192 | 11.206 | 75.926 | 22.335 | 1.00 | 29.20 |
| ATOM | 2400 | CB | LYS | 2192 | 12.098 | 74.678 | 22.406 | 1.00 | 29.35 |
| ATOM | 2401 | CG | LYS | 2192 | 11.347 | 73.338 | 22.326 | 1.00 | 26.72 |
| ATOM | 2402 | CD | LYS | 2192 | 12.309 | 72.213 | 21.933 | 1.00 | 31.20 |
| ATOM | 2403 | CE | LYS | 2192 | 11.843 | 70.819 | 22.387 | 1.00 | 34.93 |
| ATOM | 2404 | NZ | LYS | 2192 | 10.538 | 70.386 | 21.818 | 1.00 | 36.82 |
| ATOM | 2405 | C | LYS | 2192 | 10.247 | 75.981 | 23.517 | 1.00 | 29.33 |
| ATOM | 2406 | O | LYS | 2192 | 10.665 | 75.925 | 24.671 | 1.00 | 27.86 |
| ATOM | 2407 | N | ASN | 2193 | 8.963 | 76.120 | 23.220 | 1.00 | 30.20 |
| ATOM | 2408 | CA | ASN | 2193 | 7.938 | 76.210 | 24.252 | 1.00 | 33.58 |
| ATOM | 2409 | CB | ASN | 2193 | 7.739 | 74.852 | 24.930 | 1.00 | 34.59 |
| ATOM | 2410 | CG | ASN | 2193 | 7.488 | 73.738 | 23.940 | 1.00 | 38.32 |
| ATOM | 2411 | OD1 | ASN | 2193 | 6.630 | 73.849 | 23.072 | 1.00 | 39.46 |
| ATOM | 2412 | ND2 | ASN | 2193 | 8.239 | 72.648 | 24.070 | 1.00 | 42.12 |
| ATOM | 2413 | C | ASN | 2193 | 8.270 | 77.281 | 25.310 | 1.00 | 33.79 |
| ATOM | 2414 | O | ASN | 2193 | 8.216 | 77.023 | 26.512 | 1.00 | 34.33 |
| ATOM | 2415 | N | GLY | 2194 | 8.625 | 78.479 | 24.859 | 1.00 | 31.89 |
| ATOM | 2416 | CA | GLY | 2194 | 8.924 | 79.548 | 25.790 | 1.00 | 33.29 |
| ATOM | 2417 | C | GLY | 2194 | 10.344 | 79.649 | 26.322 | 1.00 | 34.90 |
| ATOM | 2418 | O | GLY | 2194 | 10.887 | 80.745 | 26.426 | 1.00 | 36.26 |
| ATOM | 2419 | N | ALA | 2195 | 10.951 | 78.523 | 26.674 | 1.00 | 34.28 |
| ATOM | 2420 | CA | ALA | 2195 | 12.304 | 78.546 | 27.206 | 1.00 | 33.63 |
| ATOM | 2421 | CB | ALA | 2195 | 12.550 | 77.298 | 28.049 | 1.00 | 31.67 |
| ATOM | 2422 | C | ALA | 2195 | 13.339 | 78.644 | 26.091 | 1.00 | 33.30 |
| ATOM | 2423 | O | ALA | 2195 | 13.018 | 78.470 | 24.917 | 1.00 | 32.47 |
| ATOM | 2424 | N | ALA | 2196 | 14.579 | 78.935 | 26.469 | 1.00 | 32.73 |
| ATOM | 2425 | CA | ALA | 2196 | 15.675 | 79.038 | 25.516 | 1.00 | 33.36 |
| ATOM | 2426 | CB | ALA | 2196 | 16.934 | 79.580 | 26.205 | 1.00 | 32.26 |
| ATOM | 2427 | C | ALA | 2196 | 15.926 | 77.638 | 24.982 | 1.00 | 33.13 |
| ATOM | 2428 | O | ALA | 2196 | 15.685 | 76.660 | 25.681 | 1.00 | 31.98 |
| ATOM | 2429 | N | PHE | 2197 | 16.409 | 77.545 | 23.747 | 1.00 | 35.16 |
| ATOM | 2430 | CA | PHE | 2197 | 16.671 | 76.254 | 23.116 | 1.00 | 36.83 |
| ATOM | 2431 | CB | PHE | 2197 | 15.835 | 76.118 | 21.838 | 1.00 | 38.27 |
| ATOM | 2432 | CG | PHE | 2197 | 15.884 | 74.751 | 21.211 | 1.00 | 40.02 |
| ATOM | 2433 | CD1 | PHE | 2197 | 15.880 | 74.610 | 19.821 | 1.00 | 41.65 |

TABLE 2-continued

FGFR1 D2–D3 Complexed with FGF1

| ATOM | 2434 | CD2 | PHE | 2197 | 15.881 | 73.601 | 22.000 | 1.00 | 41.91 |
|---|---|---|---|---|---|---|---|---|---|
| ATOM | 2435 | CE1 | PHE | 2197 | 15.867 | 73.341 | 19.218 | 1.00 | 42.05 |
| ATOM | 2436 | CE2 | PHE | 2197 | 15.869 | 72.327 | 21.413 | 1.00 | 41.84 |
| ATOM | 2437 | CZ | PHE | 2197 | 15.862 | 72.198 | 20.017 | 1.00 | 43.55 |
| ATOM | 2438 | C | PHE | 2197 | 18.139 | 76.103 | 22.755 | 1.00 | 37.43 |
| ATOM | 2439 | O | PHE | 2197 | 18.578 | 76.608 | 21.727 | 1.00 | 36.20 |
| ATOM | 2440 | N | ALA | 2198 | 18.903 | 75.415 | 23.595 | 1.00 | 37.88 |
| ATOM | 2441 | CA | ALA | 2198 | 20.315 | 75.205 | 23.301 | 1.00 | 38.43 |
| ATOM | 2442 | CB | ALA | 2198 | 21.125 | 75.160 | 24.598 | 1.00 | 39.27 |
| ATOM | 2443 | C | ALA | 2198 | 20.438 | 73.885 | 22.541 | 1.00 | 38.16 |
| ATOM | 2444 | O | ALA | 2198 | 19.693 | 72.942 | 22.804 | 1.00 | 37.17 |
| ATOM | 2445 | N | PRO | 2199 | 21.376 | 73.803 | 21.584 | 1.00 | 38.70 |
| ATOM | 2446 | CD | PRO | 2199 | 22.362 | 74.829 | 21.223 | 1.00 | 38.08 |
| ATOM | 2447 | CA | PRO | 2199 | 21.584 | 72.584 | 20.785 | 1.00 | 40.01 |
| ATOM | 2448 | CB | PRO | 2199 | 22.841 | 72.906 | 19.964 | 1.00 | 37.42 |
| ATOM | 2449 | CG | PRO | 2199 | 23.507 | 73.982 | 20.747 | 1.00 | 40.90 |
| ATOM | 2450 | C | PRO | 2199 | 21.708 | 71.275 | 21.560 | 1.00 | 39.78 |
| ATOM | 2451 | P | PRO | 2199 | 21.372 | 70.209 | 21.049 | 1.00 | 41.63 |
| ATOM | 2452 | N | ASP | 2200 | 22.170 | 71.358 | 22.797 | 1.00 | 40.44 |
| ATOM | 2453 | CA | ASP | 2200 | 22.333 | 70.172 | 23.625 | 1.00 | 40.38 |
| ATOM | 2454 | CG | ASP | 2200 | 23.300 | 70.493 | 24.760 | 1.00 | 44.62 |
| ATOM | 2455 | CG | ASP | 2200 | 24.196 | 71.674 | 24.428 | 1.00 | 48.63 |
| ATOM | 2456 | OD1 | ASP | 2200 | 24.973 | 71.579 | 23.448 | 1.00 | 49.39 |
| ATOM | 2457 | OD2 | ASP | 2200 | 24.107 | 72.703 | 25.137 | 1.00 | 52.60 |
| ATOM | 2458 | C | ASP | 2200 | 20.981 | 69.736 | 24.177 | 1.00 | 38.45 |
| ATOM | 2459 | O | ASP | 2200 | 20.864 | 68.689 | 24.811 | 1.00 | 37.39 |
| ATOM | 2460 | N | HIS | 2201 | 19.959 | 70.549 | 23.930 | 1.00 | 36.35 |
| ATOM | 2461 | CA | HIS | 2201 | 18.609 | 70.249 | 24.393 | 1.00 | 35.10 |
| ATOM | 2462 | CB | HIS | 2201 | 17.700 | 71.449 | 24.176 | 1.00 | 36.45 |
| ATOM | 2463 | CG | HIS | 2201 | 17.861 | 72.521 | 25.201 | 1.00 | 39.01 |
| ATOM | 2464 | CD2 | HIS | 2201 | 16.946 | 73.275 | 25.852 | 1.00 | 38.88 |
| ATOM | 2465 | ND1 | HIS | 2201 | 19.095 | 72.937 | 25.651 | 1.00 | 39.27 |
| ATOM | 2466 | CE1 | HIS | 2201 | 18.933 | 73.902 | 26.537 | 1.00 | 40.23 |
| ATOM | 2467 | NE2 | HIS | 2201 | 17.638 | 74.127 | 26.676 | 1.00 | 42.05 |
| ATOM | 2468 | C | HIS | 2201 | 18.004 | 69.064 | 23.665 | 1.00 | 34.79 |
| ATOM | 2469 | O | HIS | 2201 | 16.942 | 68.573 | 24.045 | 1.00 | 34.44 |
| ATOM | 2470 | N | ARG | 2202 | 18.665 | 68.615 | 22.605 | 1.00 | 34.15 |
| ATOM | 2471 | CA | ARG | 2202 | 18.151 | 67.499 | 21.831 | 1.00 | 32.50 |
| ATOM | 2472 | CB | ARG | 2202 | 17.194 | 68.004 | 20.752 | 1.00 | 30.12 |
| ATOM | 2473 | CG | ARG | 2202 | 17.869 | 68.809 | 19.654 | 1.00 | 28.46 |
| ATOM | 2474 | CD | ARG | 2202 | 16.895 | 69.065 | 18.525 | 1.00 | 27.89 |
| ATOM | 2475 | NE | ARG | 2202 | 16.329 | 67.818 | 18.025 | 1.00 | 25.16 |
| ATOM | 2476 | GZ | ARG | 2202 | 16.687 | 67.243 | 16.885 | 1.00 | 25.99 |
| ATOM | 2477 | NH1 | ARG | 2202 | 17.613 | 67.811 | 16.123 | 1.00 | 26.37 |
| ATOM | 2478 | NH2 | ARG | 2202 | 16.117 | 66.104 | 16.505 | 1.00 | 25.18 |
| ATOM | 2479 | C | ARG | 2202 | 19.268 | 66.726 | 21.162 | 1.00 | 33.59 |
| ATOM | 2480 | O | ARG | 2202 | 20.315 | 67.292 | 20.835 | 1.00 | 34.52 |
| ATOM | 2481 | N | ILE | 2203 | 19.041 | 65.432 | 20.954 | 1.00 | 31.54 |
| ATOM | 2482 | CA | ILE | 2203 | 20.036 | 64.613 | 20.292 | 1.00 | 29.88 |
| ATOM | 2483 | CB | ILE | 2203 | 19.659 | 63.133 | 20.330 | 1.00 | 28.99 |
| ATOM | 2484 | CG2 | ILE | 2203 | 20.840 | 62.288 | 19.849 | 1.00 | 27.29 |
| ATOM | 2485 | CG1 | ILE | 2203 | 19.263 | 62.747 | 21.759 | 1.00 | 27.78 |
| ATOM | 2486 | CD1 | ILE | 2203 | 18.829 | 61.320 | 21.917 | 1.00 | 25.32 |
| ATOM | 2487 | C | ILE | 2203 | 20.069 | 65.093 | 18.851 | 1.00 | 30.87 |
| ATOM | 2488 | O | ILE | 2203 | 19.024 | 65.374 | 18.258 | 1.00 | 30.90 |
| ATOM | 2489 | N | GLY | 2204 | 21.270 | 65.204 | 18.297 | 1.00 | 29.89 |
| ATOM | 2490 | CA | GLY | 2204 | 21.406 | 65.671 | 16.935 | 1.00 | 28.63 |
| ATOM | 2491 | C | GLY | 2204 | 21.812 | 67.129 | 16.955 | 1.00 | 29.63 |
| ATOM | 2492 | O | GLY | 2204 | 22.605 | 67.575 | 16.127 | 1.00 | 30.51 |
| ATOM | 2493 | N | GLY | 2205 | 21.279 | 67.875 | 17.917 | 1.00 | 28.98 |
| ATOM | 2494 | CA | GLY | 2205 | 21.604 | 69.285 | 18.023 | 1.00 | 30.12 |
| ATOM | 2495 | C | GLY | 2205 | 20.769 | 70.074 | 17.043 | 1.00 | 31.55 |
| ATOM | 2496 | O | GLY | 2205 | 19.588 | 69.777 | 16.862 | 1.00 | 34.37 |
| ATOM | 2497 | N | TYR | 2206 | 21.359 | 71.089 | 16.420 | 1.00 | 30.73 |
| ATOM | 2498 | CA | TYR | 2206 | 20.630 | 71.872 | 15.431 | 1.00 | 30.91 |
| ATOM | 2499 | CB | TYR | 2206 | 19.278 | 72.343 | 15.997 | 1.00 | 29.68 |
| ATOM | 2500 | CG | TYR | 2206 | 19.336 | 73.512 | 16.967 | 1.00 | 33.76 |
| ATOM | 2501 | CD1 | TYR | 2206 | 19.676 | 74.803 | 16.524 | 1.00 | 33.73 |
| ATOM | 2502 | CE1 | TYR | 2206 | 19.678 | 75.887 | 17.387 | 1.00 | 31.86 |
| ATOM | 2503 | CD2 | TYR | 2206 | 18.999 | 73.346 | 18.315 | 1.00 | 33.58 |
| ATOM | 2504 | CE2 | TYR | 2206 | 18.995 | 74.431 | 19.189 | 1.00 | 35.07 |
| ATOM | 2505 | CZ | TYR | 2206 | 19.334 | 75.697 | 18.710 | 1.00 | 36.17 |
| ATOM | 2506 | OH | TYR | 2206 | 19.325 | 76.779 | 19.546 | 1.00 | 38.63 |
| ATOM | 2507 | C | TYR | 2206 | 21.441 | 73.058 | 14.924 | 1.00 | 31.29 |
| ATOM | 2508 | O | TYR | 2206 | 22.090 | 73.752 | 15.692 | 1.00 | 32.10 |
| ATOM | 2509 | N | ALA | 2207 | 21.409 | 73.280 | 13.617 | 1.00 | 31.83 |
| ATOM | 2510 | CA | ALA | 2207 | 22.130 | 74.396 | 13.033 | 1.00 | 32.22 |

TABLE 2-continued

FGFR1 D2–D3 Complexed with FGF1

| ATOM | 2511 | CB | ALA | 2207 | 22.808 | 73.960 | 11.735 | 1.00 | 28.87 |
|------|------|-----|-----|------|--------|--------|--------|------|-------|
| ATOM | 2512 | C | ALA | 2207 | 21.188 | 75.580 | 12.771 | 1.00 | 33.96 |
| ATOM | 2513 | O | ALA | 2207 | 19.976 | 75.419 | 12.606 | 1.00 | 35.78 |
| ATOM | 2514 | N | VAL | 2208 | 21.758 | 76.777 | 12.756 | 1.00 | 34.58 |
| ATOM | 2515 | CA | VAL | 2208 | 21.004 | 77.992 | 12.493 | 1.00 | 33.03 |
| ATOM | 2516 | CB | VAL | 2208 | 20.940 | 78.912 | 13.745 | 1.00 | 31.00 |
| ATOM | 2517 | CG1 | VAL | 2208 | 20.155 | 80.170 | 13.427 | 1.00 | 31.63 |
| ATOM | 2518 | CG2 | VAL | 2208 | 20.300 | 78.173 | 14.905 | 1.00 | 29.43 |
| ATOM | 2519 | C | VAL | 2208 | 21.740 | 78.726 | 11.383 | 1.00 | 32.68 |
| ATOM | 2520 | O | VAL | 2208 | 22.846 | 79.210 | 11.589 | 1.00 | 36.08 |
| ATOM | 2521 | N | ALA | 2209 | 21.154 | 78.779 | 10.197 | 1.00 | 32.38 |
| ATOM | 2522 | CA | ALA | 2209 | 21.787 | 79.490 | 9.097 | 1.00 | 32.76 |
| ATOM | 2523 | CB | ALA | 2209 | 21.364 | 78.886 | 7.761 | 1.00 | 32.64 |
| ATOM | 2524 | C | ALA | 2209 | 21.350 | 80.952 | 9.196 | 1.00 | 32.21 |
| ATOM | 2525 | O | ALA | 2209 | 20.282 | 81.332 | 8.733 | 1.00 | 29.99 |
| ATOM | 2526 | N | TYR | 2210 | 22.181 | 81.768 | 9.824 | 1.00 | 35.12 |
| ATOM | 2527 | CA | TYR | 2210 | 21.858 | 83.178 | 9.992 | 1.00 | 39.15 |
| ATOM | 2528 | CB | TYR | 2210 | 22.958 | 83.874 | 10.808 | 1.00 | 38.97 |
| ATOM | 2529 | CG | TYR | 2210 | 23.195 | 83.199 | 12.135 | 1.00 | 42.16 |
| ATOM | 2530 | CD1 | TYR | 2210 | 24.109 | 82.145 | 12.254 | 1.00 | 43.86 |
| ATOM | 2531 | CE1 | TYR | 2210 | 24.281 | 81.469 | 13.466 | 1.00 | 44.27 |
| ATOM | 2532 | CD2 | TYR | 2210 | 22.460 | 83.566 | 13.263 | 1.00 | 43.66 |
| ATOM | 2533 | CE2 | TYR | 2210 | 22.624 | 82.899 | 14.483 | 1.00 | 46.54 |
| ATOM | 2534 | CZ | TYR | 2210 | 23.535 | 81.850 | 14.576 | 1.00 | 46.10 |
| ATOM | 2535 | OH | TYR | 2210 | 23.687 | 81.178 | 15.772 | 1.00 | 48.07 |
| ATOM | 2536 | C | TYR | 2210 | 21.644 | 83.883 | 8.650 | 1.00 | 38.16 |
| ATOM | 2537 | O | TYR | 2210 | 20.886 | 84.854 | 8.549 | 1.00 | 38.75 |
| ATOM | 2538 | N | ALA | 2211 | 22.294 | 83.385 | 7.610 | 1.00 | 36.97 |
| ATOM | 2539 | CA | ALA | 2211 | 22.137 | 83.998 | 6.308 | 1.00 | 34.88 |
| ATOM | 2540 | CB | ALA | 2211 | 23.155 | 83.417 | 5.344 | 1.00 | 34.58 |
| ATOM | 2541 | C | ALA | 2211 | 20.718 | 83.772 | 5.788 | 1.00 | 34.25 |
| ATOM | 2542 | O | ALA | 2211 | 20.147 | 84.624 | 5.120 | 1.00 | 35.50 |
| ATOM | 2543 | N | THR | 2212 | 20.140 | 82.627 | 6.127 | 1.00 | 33.86 |
| ATOM | 2544 | CA | THR | 2212 | 18.811 | 82.265 | 5.658 | 1.00 | 30.60 |
| ATOM | 2545 | CB | THR | 2212 | 18.827 | 80.848 | 5.114 | 1.00 | 32.70 |
| ATOM | 2546 | OG1 | THR | 2212 | 20.091 | 80.614 | 4.491 | 1.00 | 37.44 |
| ATOM | 2547 | CG2 | THR | 2212 | 17.732 | 80.651 | 4.086 | 1.00 | 34.56 |
| ATOM | 2548 | C | THR | 2212 | 17.730 | 82.334 | 6.710 | 1.00 | 28.90 |
| ATOM | 2549 | O | THR | 2212 | 16.688 | 81.712 | 6.556 | 1.00 | 27.43 |
| ATOM | 2550 | N | TRP | 2213 | 17.987 | 83.065 | 7.787 | 1.00 | 29.76 |
| ATOM | 2551 | CA | TRP | 2213 | 17.021 | 83.240 | 8.874 | 1.00 | 27.80 |
| ATOM | 2552 | CB | TRP | 2213 | 16.019 | 84.348 | 8.493 | 1.00 | 26.89 |
| ATOM | 2553 | CG | TRP | 2213 | 16.703 | 85.655 | 8.204 | 1.00 | 27.67 |
| ATOM | 2554 | CD2 | TRP | 2213 | 17.136 | 86.628 | 9.167 | 1.00 | 29.11 |
| ATOM | 2555 | CE2 | TRP | 2213 | 17.801 | 87.649 | 8.457 | 1.00 | 29.63 |
| ATOM | 2556 | CE3 | TRP | 2213 | 17.029 | 86.733 | 10.561 | 1.00 | 29.05 |
| ATOM | 2557 | CD1 | TRP | 2213 | 17.109 | 86.115 | 6.991 | 1.00 | 27.28 |
| ATOM | 2558 | NE1 | TRP | 2213 | 17.770 | 87.311 | 7.132 | 1.00 | 29.13 |
| ATOM | 2559 | CZ2 | TRP | 2213 | 18.357 | 88.764 | 9.093 | 1.00 | 31.44 |
| ATOM | 2560 | CZ3 | TRP | 2213 | 17.581 | 87.839 | 11.194 | 1.00 | 30.07 |
| ATOM | 2561 | CH2 | TRP | 2213 | 18.238 | 88.841 | 10.458 | 1.00 | 31.81 |
| ATOM | 2562 | C | TRP | 2213 | 16.287 | 81.961 | 9.264 | 1.00 | 24.83 |
| ATOM | 2563 | O | TRP | 2213 | 15.090 | 81.961 | 9.551 | 1.00 | 22.52 |
| ATOM | 2564 | N | SER | 2214 | 17.020 | 80.861 | 9.302 | 1.00 | 27.35 |
| ATOM | 2565 | CA | SER | 2214 | 16.394 | 79.591 | 9.642 | 1.00 | 29.71 |
| ATOM | 2566 | CB | SER | 2214 | 16.088 | 78.819 | 8.354 | 1.00 | 27.02 |
| ATOM | 2567 | OG | SER | 2214 | 17.209 | 78.851 | 7.494 | 1.00 | 27.71 |
| ATOM | 2568 | C | SER | 2214 | 17.195 | 78.710 | 10.601 | 1.00 | 28.94 |
| ATOM | 2569 | O | SER | 2214 | 18.374 | 78.960 | 10.877 | 1.00 | 28.56 |
| ATOM | 2570 | N | ILE | 2215 | 16.514 | 77.698 | 11.127 | 1.00 | 27.21 |
| ATOM | 2571 | CA | ILE | 2215 | 17.106 | 76.732 | 12.040 | 1.00 | 28.54 |
| ATOM | 2572 | CB | ILE | 2215 | 16.427 | 76.730 | 13.419 | 1.00 | 27.61 |
| ATOM | 2573 | CG2 | ILE | 2215 | 14.908 | 76.803 | 13.260 | 1.00 | 26.81 |
| ATOM | 2574 | CG1 | ILE | 2215 | 16.844 | 75.461 | 14.172 | 1.00 | 27.42 |
| ATOM | 2575 | CD1 | ILE | 2215 | 16.230 | 75.302 | 15.532 | 1.00 | 26.34 |
| ATOM | 2576 | C | ILE | 2215 | 16.891 | 75.362 | 11.410 | 1.00 | 29.14 |
| ATOM | 2577 | O | ILE | 2215 | 15.828 | 75.079 | 10.853 | 1.00 | 30.48 |
| ATOM | 2578 | N | ILE | 2216 | 17.885 | 74.499 | 11.510 | 1.00 | 26.76 |
| ATOM | 2579 | CA | ILE | 2216 | 17.747 | 73.206 | 10.892 | 1.00 | 27.79 |
| ATOM | 2580 | CB | ILE | 2216 | 18.734 | 73.078 | 9.715 | 1.00 | 27.12 |
| ATOM | 2581 | CG2 | ILE | 2216 | 18.621 | 71.708 | 9.083 | 1.00 | 28.89 |
| ATOM | 2582 | CG1 | ILE | 2216 | 18.418 | 74.153 | 8.671 | 1.00 | 27.77 |
| ATOM | 2583 | CD1 | ILE | 2216 | 19.258 | 74.069 | 7.413 | 1.00 | 28.95 |
| ATOM | 2584 | C | ILE | 2216 | 17.940 | 72.055 | 11.853 | 1.00 | 28.07 |
| ATOM | 2585 | O | ILE | 2216 | 19.017 | 71.907 | 12.441 | 1.00 | 29.76 |
| ATOM | 2586 | N | MET | 2217 | 16.891 | 71.241 | 12.004 | 1.00 | 25.11 |
| ATOM | 2587 | CA | MET | 2217 | 16.931 | 70.075 | 12.885 | 1.00 | 25.02 |

TABLE 2-continued

FGFR1 D2–D3 Complexed with FGF1

| ATOM | 2588 | CB  | MET | 2217 | 15.785 | 70.111 | 13.897 | 1.00 | 25.93 |
|------|------|-----|-----|------|--------|--------|--------|------|-------|
| ATOM | 2589 | CG  | MET | 2217 | 15.711 | 71.336 | 14.777 | 1.00 | 30.67 |
| ATOM | 2590 | SD  | MET | 2217 | 14.404 | 71.152 | 16.030 | 1.00 | 37.94 |
| ATOM | 2591 | CE  | MET | 2217 | 12.915 | 71.200 | 15.008 | 1.00 | 32.03 |
| ATOM | 2592 | C   | MET | 2217 | 16.840 | 68.748 | 12.127 | 1.00 | 23.05 |
| ATOM | 2593 | O   | MET | 2217 | 15.772 | 68.382 | 11.618 | 1.00 | 23.87 |
| ATOM | 2594 | N   | ASP | 2218 | 17.952 | 68.027 | 12.057 | 1.00 | 19.07 |
| ATOM | 2595 | CA  | ASP | 2218 | 17.967 | 66.734 | 11.395 | 1.00 | 17.04 |
| ATOM | 2596 | CB  | ASP | 2218 | 19.408 | 66.293 | 11.096 | 1.00 | 19.60 |
| ATOM | 2597 | CG  | ASP | 2218 | 19.938 | 66.862 | 9.781  | 1.00 | 26.60 |
| ATOM | 2598 | OD1 | ASP | 2218 | 19.482 | 67.956 | 9.391  | 1.00 | 30.39 |
| ATOM | 2599 | OD2 | ASP | 2218 | 20.818 | 66.232 | 9.137  | 1.00 | 29.07 |
| ATOM | 2600 | C   | ASP | 2218 | 17.266 | 65.682 | 12.266 | 1.00 | 15.55 |
| ATOM | 2601 | O   | ASP | 2218 | 17.126 | 65.829 | 13.480 | 1.00 | 9.21  |
| ATOM | 2602 | N   | SER | 2219 | 16.791 | 64.632 | 11.614 | 1.00 | 18.32 |
| ATOM | 2603 | CA  | SER | 2219 | 16.131 | 63.533 | 12.295 | 1.00 | 19.16 |
| ATOM | 2604 | CB  | SER | 2219 | 17.168 | 62.498 | 12.722 | 1.00 | 20.74 |
| ATOM | 2605 | CG  | SER | 2219 | 16.575 | 61.532 | 13.563 | 1.00 | 29.39 |
| ATOM | 2606 | C   | SER | 2219 | 15.305 | 63.939 | 13.497 | 1.00 | 17.12 |
| ATOM | 2607 | O   | SER | 2219 | 15.735 | 63.836 | 14.643 | 1.00 | 17.72 |
| ATOM | 2608 | N   | VAL | 2220 | 14.103 | 64.400 | 13.222 | 1.00 | 17.02 |
| ATOM | 2609 | CA  | VAL | 2220 | 13.202 | 64.799 | 14.276 | 1.00 | 18.02 |
| ATOM | 2610 | CB  | VAL | 2220 | 12.095 | 65.705 | 13.731 | 1.00 | 19.17 |
| ATOM | 2611 | CG1 | VAL | 2220 | 12.692 | 66.990 | 13.189 | 1.00 | 19.80 |
| ATOM | 2612 | CG2 | VAL | 2220 | 11.328 | 64.961 | 12.630 | 1.00 | 22.22 |
| ATOM | 2613 | C   | VAL | 2220 | 12.550 | 63.535 | 14.814 | 1.00 | 18.57 |
| ATOM | 2614 | O   | VAL | 2220 | 12.417 | 62.532 | 14.103 | 1.00 | 18.14 |
| ATOM | 2615 | N   | VAL | 2221 | 12.132 | 63.593 | 16.067 | 1.00 | 18.04 |
| ATOM | 2616 | CA  | VAL | 2221 | 11.463 | 62.469 | 16.704 | 1.00 | 18.22 |
| ATOM | 2617 | CB  | VAL | 2221 | 12.460 | 61.595 | 17.490 | 1.00 | 19.68 |
| ATOM | 2618 | CG1 | VAL | 2221 | 13.130 | 60.596 | 16.551 | 1.00 | 15.48 |
| ATOM | 2619 | CG2 | VAL | 2221 | 13.519 | 62.495 | 18.157 | 1.00 | 19.19 |
| ATOM | 2620 | C   | VAL | 2221 | 10.474 | 63.097 | 17.661 | 1.00 | 18.71 |
| ATOM | 2621 | O   | VAL | 2221 | 10.654 | 64.248 | 18.069 | 1.00 | 18.32 |
| ATOM | 2622 | N   | PRO | 2222 | 9.423  | 62.352 | 18.039 | 1.00 | 18.55 |
| ATOM | 2623 | CD  | PRO | 2222 | 9.259  | 60.918 | 17.752 | 1.00 | 17.61 |
| ATOM | 2624 | CA  | PRO | 2222 | 8.371  | 62.819 | 18.957 | 1.00 | 19.07 |
| ATOM | 2625 | CB  | PRO | 2222 | 7.801  | 61.515 | 19.508 | 1.00 | 16.37 |
| ATOM | 2626 | CG  | PRO | 2222 | 7.871  | 60.619 | 18.325 | 1.00 | 15.33 |
| ATOM | 2627 | C   | PRO | 2222 | 8.823  | 63.781 | 20.062 | 1.00 | 19.36 |
| ATOM | 2628 | O   | PRO | 2222 | 8.175  | 64.794 | 20.305 | 1.00 | 21.25 |
| ATOM | 2629 | N   | SER | 2223 | 9.933  | 63.475 | 20.721 | 1.00 | 20.13 |
| ATOM | 2630 | CA  | SER | 2223 | 10.429 | 64.341 | 21.782 | 1.00 | 20.49 |
| ATOM | 2631 | CB  | SER | 2223 | 11.736 | 63.787 | 22.364 | 1.00 | 16.62 |
| ATOM | 2632 | OG  | SER | 2223 | 12.840 | 64.105 | 21.535 | 1.00 | 16.05 |
| ATOM | 2633 | C   | SER | 2223 | 10.660 | 65.767 | 21.256 | 1.00 | 22.58 |
| ATOM | 2634 | O   | SER | 2223 | 10.679 | 66.725 | 22.036 | 1.00 | 23.81 |
| ATOM | 2635 | N   | ASP | 2224 | 10.830 | 65.905 | 19.941 | 1.00 | 21.50 |
| ATOM | 2636 | CA  | ASP | 2224 | 11.063 | 67.210 | 19.348 | 1.00 | 20.08 |
| ATOM | 2637 | CB  | ASP | 2224 | 11.709 | 67.073 | 17.970 | 1.00 | 22.89 |
| ATOM | 2638 | CG  | ASP | 2224 | 13.157 | 66.627 | 18.044 | 1.00 | 24.95 |
| ATOM | 2639 | OD1 | ASP | 2224 | 13.891 | 67.184 | 18.886 | 1.00 | 24.92 |
| ATOM | 2640 | OD2 | ASP | 2224 | 13.557 | 65.738 | 17.252 | 1.00 | 23.39 |
| ATOM | 2641 | C   | ASP | 2224 | 9.785  | 68.027 | 19.224 | 1.00 | 20.98 |
| ATOM | 2642 | O   | ASP | 2224 | 9.839  | 69.251 | 19.123 | 1.00 | 22.98 |
| ATOM | 2643 | N   | ALA | 2225 | 8.635  | 67.365 | 19.237 | 1.00 | 21.09 |
| ATOM | 2644 | CA  | ALA | 2225 | 7.356  | 68.071 | 19.115 | 1.00 | 22.05 |
| ATOM | 2645 | CB  | ALA | 2225 | 6.186  | 67.105 | 19.384 | 1.00 | 17.67 |
| ATOM | 2646 | C   | ALA | 2225 | 7.264  | 69.273 | 20.060 | 1.00 | 23.32 |
| ATOM | 2647 | O   | ALA | 2225 | 7.629  | 69.181 | 21.233 | 1.00 | 23.49 |
| ATOM | 2648 | N   | GLY | 2226 | 6.780  | 70.400 | 19.539 | 1.00 | 24.74 |
| ATOM | 2649 | CA  | GLY | 2226 | 6.620  | 71.594 | 20.354 | 1.00 | 24.38 |
| ATOM | 2650 | C   | GLY | 2226 | 6.560  | 72.886 | 19.554 | 1.00 | 26.79 |
| ATOM | 2651 | O   | GLY | 2226 | 6.673  | 72.886 | 18.323 | 1.00 | 27.32 |
| ATOM | 2652 | N   | ASN | 2227 | 6.382  | 74.001 | 20.258 | 1.00 | 26.78 |
| ATOM | 2653 | CA  | ASN | 2227 | 6.339  | 75.313 | 19.619 | 1.00 | 25.96 |
| ATOM | 2654 | CB  | ASN | 2227 | 5.554  | 76.310 | 20.466 | 1.00 | 24.91 |
| ATOM | 2655 | CG  | ASN | 2227 | 4.164  | 75.831 | 20.774 | 1.00 | 28.61 |
| ATOM | 2656 | OD1 | ASN | 2227 | 3.433  | 75.420 | 19.874 | 1.00 | 30.98 |
| ATOM | 2657 | ND2 | ASN | 2227 | 3.781  | 75.877 | 22.050 | 1.00 | 26.89 |
| ATOM | 2658 | C   | ASN | 2227 | 7.755  | 75.836 | 19.471 | 1.00 | 24.70 |
| ATOM | 2659 | O   | ASM | 2227 | 8.550  | 75.732 | 20.401 | 1.00 | 29.55 |
| ATOM | 2660 | N   | TYR | 2228 | 8.073  | 76.387 | 18.307 | 1.00 | 20.57 |
| ATOM | 2661 | CA  | TYR | 2228 | 9.386  | 76.947 | 18.075 | 1.00 | 18.55 |
| ATOM | 2662 | CB  | TYR | 2228 | 10.118 | 76.171 | 17.005 | 1.00 | 14.84 |
| ATOM | 2663 | CG  | TYR | 2228 | 10.521 | 74.819 | 17.498 | 1.00 | 18.09 |
| ATOM | 2664 | CD1 | TYR | 2228 | 9.564  | 73.807 | 17.684 | 1.00 | 16.76 |

TABLE 2-continued

FGFR1 D2–D3 Complexed with FGF1

| | | | | | | | | | |
|---|---|---|---|---|---|---|---|---|---|
| ATOM | 2665 | CE1 | TYR | 2228 | 9.934 | 72.535 | 18.143 | 1.00 | 18.01 |
| ATOM | 2666 | CD2 | TYR | 2228 | 11.862 | 74.537 | 17.787 | 1.00 | 17.90 |
| ATOM | 2667 | CE2 | TYR | 2228 | 12.248 | 73.273 | 18.245 | 1.00 | 21.76 |
| ATOM | 2668 | CZ | TYR | 2228 | 11.281 | 72.273 | 18.418 | 1.00 | 19.94 |
| ATOM | 2669 | OH | TYR | 2228 | 11.681 | 71.023 | 18.830 | 1.00 | 17.62 |
| ATOM | 2670 | C | TYR | 2228 | 9.227 | 78.396 | 17.679 | 1.00 | 21.31 |
| ATOM | 2671 | O | TYR | 2228 | 8.512 | 78.722 | 16.719 | 1.00 | 21.45 |
| ATOM | 2672 | N | THR | 2229 | 9.891 | 79.269 | 18.430 | 1.00 | 18.76 |
| ATOM | 2673 | CA | THR | 2229 | 9.777 | 80.681 | 18.177 | 1.00 | 18.04 |
| ATOM | 2674 | CB | THR | 2229 | 9.240 | 81.411 | 19.402 | 1.00 | 16.54 |
| ATOM | 2675 | OG1 | THR | 2229 | 7.945 | 80.894 | 19.727 | 1.00 | 15.07 |
| ATOM | 2676 | CG2 | THR | 2229 | 9.134 | 82.906 | 19.123 | 1.00 | 14.42 |
| ATOM | 2677 | C | THR | 2229 | 11.059 | 81.340 | 17.782 | 1.00 | 20.77 |
| ATOM | 2678 | O | THR | 2229 | 12.065 | 81.227 | 18.476 | 1.00 | 25.59 |
| ATOM | 2679 | N | CYS | 2230 | 11.033 | 82.030 | 16.653 | 1.00 | 21.16 |
| ATOM | 2680 | CA | GYS | 2230 | 12.218 | 82.746 | 16.246 | 1.00 | 21.18 |
| ATOM | 2681 | C | CYS | 2230 | 12.018 | 84.144 | 16.811 | 1.00 | 18.33 |
| ATOM | 2682 | O | CYS | 2230 | 10.890 | 84.620 | 16.942 | 1.00 | 15.60 |
| ATOM | 2683 | CB | GYS | 2230 | 12.348 | 82.797 | 14.723 | 1.00 | 21.87 |
| ATOM | 2684 | SG | CYS | 2230 | 10.999 | 83.670 | 13.892 | 1.00 | 30.17 |
| ATOM | 2685 | N | ILE | 2231 | 13.112 | 84.785 | 17.187 | 1.00 | 18.41 |
| ATOM | 2686 | CA | ILE | 2231 | 13.028 | 86.128 | 17.712 | 1.00 | 18.07 |
| ATOM | 2687 | CB | ILE | 2231 | 13.222 | 86.138 | 19.221 | 1.00 | 19.30 |
| ATOM | 2688 | CG2 | ILE | 2231 | 13.386 | 87.558 | 19.718 | 1.00 | 20.15 |
| ATOM | 2689 | CG1 | ILE | 2231 | 11.996 | 85.483 | 19.871 | 1.00 | 21.87 |
| ATOM | 2690 | CD1 | ILE | 2231 | 12.043 | 85.418 | 21.373 | 1.00 | 20.48 |
| ATOM | 2691 | C | ILE | 2231 | 14.063 | 86.988 | 17.037 | 1.00 | 17.55 |
| ATOM | 2692 | O | ILE | 2231 | 15.263 | 86.760 | 17.180 | 1.00 | 20.34 |
| ATOM | 2693 | N | VAL | 2232 | 13.576 | 87.960 | 16.274 | 1.00 | 16.63 |
| ATOM | 2694 | CA | VAL | 2232 | 14.417 | 88.888 | 15.536 | 1.00 | 16.78 |
| ATOM | 2695 | CB | VAL | 2232 | 13.937 | 89.017 | 14.075 | 1.00 | 16.85 |
| ATOM | 2696 | CG1 | VAL | 2232 | 14.824 | 89.995 | 13.316 | 1.00 | 14.47 |
| ATOM | 2697 | CG2 | VAL | 2232 | 13.936 | 87.644 | 13.408 | 1.00 | 12.11 |
| ATOM | 2698 | C | VAL | 2232 | 14.334 | 90.244 | 16.206 | 1.00 | 19.10 |
| ATOM | 2699 | O | VAL | 2232 | 13.240 | 90.736 | 16.512 | 1.00 | 18.37 |
| ATOM | 2700 | N | GLU | 2233 | 15.489 | 90.855 | 16.434 | 1.00 | 23.01 |
| ATOM | 2701 | CA | GLU | 2233 | 15.521 | 92.157 | 17.096 | 1.00 | 28.37 |
| ATOM | 2702 | CB | GLU | 2233 | 15.256 | 91.989 | 18.596 | 1.00 | 33.71 |
| ATOM | 2703 | CG | GLU | 2233 | 16.105 | 90.891 | 19.238 | 1.00 | 44.29 |
| ATOM | 2704 | CD | GLU | 2233 | 15.834 | 90.711 | 20.730 | 1.00 | 50.75 |
| ATOM | 2705 | OE1 | GLU | 2233 | 14.653 | 90.778 | 21.149 | 1.00 | 53.52 |
| ATOM | 2706 | OE2 | GLU | 2233 | 16.807 | 90.486 | 21.486 | 1.00 | 55.00 |
| ATOM | 2707 | C | GLU | 2233 | 16.834 | 92.902 | 16.932 | 1.00 | 27.80 |
| ATOM | 2708 | O | GLU | 2233 | 17.892 | 92.294 | 16.725 | 1.00 | 26.70 |
| ATOM | 2709 | N | ASN | 2234 | 16.741 | 94.228 | 17.021 | 1.00 | 25.44 |
| ATOM | 2710 | GA | ASN | 2234 | 17.898 | 95.111 | 16.954 | 1.00 | 23.06 |
| ATOM | 2711 | CB | ASN | 2234 | 18.136 | 95.666 | 15.536 | 1.00 | 20.37 |
| ATOM | 2712 | CG | ASN | 2234 | 16.960 | 96.474 | 14.996 | 1.00 | 19.88 |
| ATOM | 2713 | OD1 | ASN | 2234 | 16.098 | 96.928 | 15.744 | 1.00 | 17.91 |
| ATOM | 2714 | ND2 | ASN | 2234 | 16.939 | 96.672 | 13.677 | 1.00 | 18.95 |
| ATOM | 2715 | C | ASN | 2234 | 17.614 | 96.238 | 17.935 | 1.00 | 23.81 |
| ATOM | 2716 | O | ASN | 2234 | 16.611 | 96.192 | 18.662 | 1.00 | 18.78 |
| ATOM | 2717 | N | ALA | 2235 | 18.486 | 97.245 | 17.957 | 1.00 | 25.64 |
| ATOM | 2718 | GA | ALA | 2235 | 18.330 | 98.370 | 18.875 | 1.00 | 25.56 |
| ATOM | 2719 | CB | ALA | 2235 | 19.504 | 99.358 | 18.709 | 1.00 | 22.70 |
| ATOM | 2720 | C | ALA | 2235 | 17.005 | 99.099 | 18.684 | 1.00 | 25.28 |
| ATOM | 2721 | O | ALA | 2235 | 16.627 | 99.933 | 19.511 | 1.00 | 28.40 |
| ATOM | 2722 | N | TYR | 2236 | 16.279 | 98.773 | 17.619 | 1.00 | 23.67 |
| ATOM | 2723 | CA | TYR | 2236 | 15.031 | 99.472 | 17.364 | 1.00 | 22.28 |
| ATOM | 2724 | CB | TYR | 2236 | 15.168 | 100.255 | 16.073 | 1.00 | 23.73 |
| ATOM | 2725 | CG | TYR | 2236 | 16.263 | 101.272 | 16.171 | 1.00 | 27.43 |
| ATOM | 2726 | CD1 | TYR | 2236 | 17.591 | 100.918 | 15.944 | 1.00 | 31.32 |
| ATOM | 2727 | CE1 | TYR | 2236 | 18.616 | 101.851 | 16.106 | 1.00 | 35.39 |
| ATOM | 2728 | CD2 | TYR | 2236 | 15.982 | 102.579 | 16.562 | 1.00 | 28.54 |
| ATOM | 2729 | CE2 | TYR | 2236 | 16.989 | 103.513 | 16.728 | 1.00 | 32.14 |
| ATOM | 2730 | CZ | TYR | 2236 | 18.303 | 103.147 | 16.501 | 1.00 | 34.04 |
| ATOM | 2731 | OH | TYR | 2236 | 19.298 | 104.076 | 16.671 | 1.00 | 35.11 |
| ATOM | 2732 | C | TYR | 2236 | 13.734 | 98.691 | 17.354 | 1.00 | 20.69 |
| ATOM | 2733 | O | TYR | 2236 | 12.683 | 99.240 | 17.027 | 1.00 | 22.13 |
| ATOM | 2734 | N | GLY | 2237 | 13.791 | 97.420 | 17.713 | 1.00 | 18.34 |
| ATOM | 2735 | CA | GLY | 2237 | 12.579 | 96.641 | 17.735 | 1.00 | 18.42 |
| ATOM | 2736 | C | GLY | 2237 | 12.819 | 95.154 | 17.719 | 1.00 | 20.66 |
| ATOM | 2737 | O | GLY | 2237 | 13.910 | 94.685 | 17.397 | 1.00 | 22.88 |
| ATOM | 2738 | N | SER | 2238 | 11.779 | 94.410 | 18.069 | 1.00 | 21.30 |
| ATOM | 2739 | CA | SER | 2238 | 11.855 | 92.967 | 18.091 | 1.00 | 24.16 |
| ATOM | 2740 | CB | SER | 2238 | 12.138 | 92.473 | 19.503 | 1.00 | 27.04 |
| ATOM | 2741 | OG | SER | 2238 | 12.004 | 91.061 | 19.554 | 1.00 | 33.65 |

TABLE 2-continued

| FGFR1 D2–D3 Complexed with FGF1 | | | | | | | | |
|---|---|---|---|---|---|---|---|---|
| ATOM | 2742 | C | SER | 2238 | 10.549 | 92.368 | 17.619 | 1.00 | 24.16 |
| ATOM | 2743 | O | SER | 2238 | 9.478 | 92.735 | 18.094 | 1.00 | 24.16 |
| ATOM | 2744 | N | ILE | 2239 | 10.636 | 91.443 | 16.679 | 1.00 | 25.17 |
| ATOM | 2745 | CA | ILE | 2239 | 9.438 | 90.793 | 16.174 | 1.00 | 25.95 |
| ATOM | 2746 | CB | ILE | 2239 | 9.250 | 91.054 | 14.643 | 1.00 | 23.90 |
| ATOM | 2747 | CG2 | ILE | 2239 | 9.041 | 92.538 | 14.405 | 1.00 | 22.25 |
| ATOM | 2748 | CG1 | ILE | 2239 | 10.477 | 90.591 | 13.845 | 1.00 | 22.27 |
| ATOM | 2749 | CD1 | ILE | 2239 | 10.375 | 90.865 | 12.338 | 1.00 | 15.87 |
| ATOM | 2750 | C | ILE | 2239 | 9.606 | 89.314 | 16.463 | 1.00 | 26.02 |
| ATOM | 2751 | O | ILE | 2239 | 10.711 | 88.860 | 16.730 | 1.00 | 26.85 |
| ATOM | 2752 | N | ASN | 2240 | 8.515 | 88.566 | 16.440 | 1.00 | 27.54 |
| ATOM | 2753 | CA | ASN | 2240 | 8.599 | 87.137 | 16.708 | 1.00 | 28.36 |
| ATOM | 2754 | CB | ASN | 2240 | 8.358 | 86.858 | 18.184 | 1.00 | 31.11 |
| ATOM | 2755 | CG | ASN | 2240 | 7.026 | 87.392 | 18.654 | 1.00 | 34.41 |
| ATOM | 2756 | OD1 | ASN | 2240 | 6.017 | 87.293 | 17.950 | 1.00 | 39.95 |
| ATOM | 2757 | ND2 | ASN | 2240 | 7.008 | 87.958 | 19.852 | 1.00 | 36.18 |
| ATOM | 2758 | C | ASN | 2240 | 7.577 | 86.360 | 15.898 | 1.00 | 27.32 |
| ATOM | 2759 | O | ASN | 2240 | 6.670 | 86.931 | 15.289 | 1.00 | 26.19 |
| ATOM | 2760 | N | HIS | 2241 | 7.728 | 85.045 | 15.909 | 1.00 | 26.23 |
| ATOM | 2761 | CA | HIS | 2241 | 6.823 | 84.174 | 15.183 | 1.00 | 24.63 |
| ATOM | 2762 | CB | HIS | 2241 | 7.191 | 84.145 | 13.698 | 1.00 | 27.93 |
| ATOM | 2763 | CG | HIS | 2241 | 6.198 | 83.418 | 12.851 | 1.00 | 29.56 |
| ATOM | 2764 | CD2 | HIS | 2241 | 6.302 | 82.271 | 12.141 | 1.00 | 30.41 |
| ATOM | 2765 | ND1 | HIS | 2241 | 4.894 | 83.840 | 12.708 | 1.00 | 28.42 |
| ATOM | 2766 | CE1 | HIS | 2241 | 4.237 | 82.984 | 11.950 | 1.00 | 28.77 |
| ATOM | 2767 | NE2 | HIS | 2241 | 5.069 | 82.021 | 11.593 | 1.00 | 30.81 |
| ATOM | 2768 | C | HIS | 2241 | 6.977 | 82.798 | 15.775 | 1.00 | 20.79 |
| ATOM | 2769 | O | HIS | 2241 | 8.080 | 82.406 | 16.124 | 1.00 | 23.73 |
| ATOM | 2770 | N | THR | 2242 | 5.883 | 82.068 | 15.905 | 1.00 | 18.57 |
| ATOM | 2771 | CA | THR | 2242 | 5.967 | 80.732 | 16.469 | 1.00 | 19.34 |
| ATOM | 2772 | CB | THR | 2242 | 5.175 | 80.606 | 17.786 | 1.00 | 18.92 |
| ATOM | 2773 | OG1 | THR | 2242 | 5.654 | 81.569 | 18.737 | 1.00 | 19.94 |
| ATOM | 2774 | CG2 | THR | 2242 | 5.351 | 79.197 | 18.370 | 1.00 | 16.55 |
| ATOM | 2775 | C | THR | 2242 | 5.441 | 79.678 | 15.515 | 1.00 | 19.37 |
| ATOM | 2776 | O | THR | 2242 | 4.439 | 79.889 | 14.846 | 1.00 | 19.56 |
| ATOM | 2777 | N | TYR | 2243 | 6.131 | 78.545 | 15.467 | 1.00 | 19.59 |
| ATOM | 2778 | CA | TYR | 2243 | 5.744 | 77.426 | 14.626 | 1.00 | 18.65 |
| ATOM | 2779 | CB | TYR | 2243 | 6.871 | 77.032 | 13.671 | 1.00 | 18.22 |
| ATOM | 2780 | CG | TYR | 2243 | 7.181 | 78.003 | 12.559 | 1.00 | 21.98 |
| ATOM | 2781 | CD1 | TYR | 2243 | 8.262 | 78.879 | 12.653 | 1.00 | 26.03 |
| ATOM | 2782 | CE1 | TYR | 2243 | 8.585 | 79.749 | 11.605 | 1.00 | 27.45 |
| ATOM | 2783 | CD2 | TYR | 2243 | 6.421 | 78.020 | 11.392 | 1.00 | 22.51 |
| ATOM | 2784 | CE2 | TYR | 2243 | 6.728 | 78.879 | 10.336 | 1.00 | 23.43 |
| ATOM | 2785 | CZ | TYR | 2243 | 7.808 | 79.745 | 10.445 | 1.00 | 27.97 |
| ATOM | 2786 | OH | TYR | 2243 | 8.102 | 80.614 | 9.403 | 1.00 | 26.48 |
| ATOM | 2787 | C | TYR | 2243 | 5.439 | 76.206 | 15.489 | 1.00 | 20.69 |
| ATOM | 2788 | O | TYR | 2243 | 6.165 | 75.904 | 16.432 | 1.00 | 20.77 |
| ATOM | 2789 | N | ALA | 2244 | 4.364 | 75.494 | 15.171 | 1.00 | 24.28 |
| ATOM | 2790 | CA | ALA | 2244 | 4.044 | 74.268 | 15.904 | 1.00 | 24.29 |
| ATOM | 2791 | CB | ALA | 2244 | 2.528 | 74.036 | 15.923 | 1.00 | 21.88 |
| ATOM | 2792 | C | ALA | 2244 | 4.749 | 73.145 | 15.132 | 1.00 | 23.11 |
| ATOM | 2793 | O | ALA | 2244 | 4.847 | 73.204 | 13.903 | 1.00 | 22.54 |
| ATOM | 2794 | N | LEU | 2245 | 5.286 | 72.155 | 15.831 | 1.00 | 21.86 |
| ATOM | 2795 | CA | LEU | 2245 | 5.922 | 71.053 | 15.122 | 1.00 | 22.62 |
| ATOM | 2796 | CB | LEU | 2Z45 | 7.443 | 71.051 | 15.287 | 1.00 | 18.99 |
| ATOM | 2797 | CG | LEU | 2245 | 8.147 | 70.207 | 14.204 | 1.00 | 17.70 |
| ATOM | 2798 | CD1 | LEU | 2245 | 9.642 | 70.451 | 14.227 | 1.00 | 21.67 |
| ATOM | 2799 | CD2 | LEU | 2245 | 7.870 | 68.761 | 14.398 | 1.00 | 12.29 |
| ATOM | 2800 | C | LEU | 2245 | 5.362 | 69.730 | 15.612 | 1.00 | 24.97 |
| ATOM | 2801 | O | LEU | 2245 | 5.443 | 69.393 | 16.801 | 1.00 | 26.93 |
| ATOM | 2802 | N | ASP | 2246 | 4.769 | 68.982 | 14.698 | 1.00 | 23.77 |
| ATOM | 2803 | CA | ASP | 2246 | 4.244 | 67.695 | 15.080 | 1.00 | 26.78 |
| ATOM | 2804 | CB | ASP | 2246 | 2.742 | 67.632 | 14.827 | 1.00 | 32.54 |
| ATOM | 2805 | CG | ASP | 2246 | 2.116 | 66.391 | 15.412 | 1.00 | 38.06 |
| ATOM | 2806 | OD1 | ASP | 2246 | 2.401 | 66.068 | 16.586 | 1.00 | 43.40 |
| ATOM | 2807 | OD2 | ASP | 2246 | 1.334 | 65.733 | 14.700 | 1.00 | 43.40 |
| ATOM | 2808 | C | ASP | 2246 | 4.989 | 66.639 | 14.283 | 1.00 | 24.87 |
| ATOM | 2809 | O | ASP | 2246 | 5.301 | 66.843 | 13.109 | 1.00 | 24.14 |
| ATOM | 2810 | N | VAL | 2247 | 5.289 | 65.523 | 14.939 | 1.00 | 23.50 |
| ATOM | 2811 | CA | VAL | 2247 | 6.026 | 64.419 | 14.326 | 1.00 | 22.60 |
| ATOM | 2812 | CB | VAL | 2247 | 7.394 | 64.245 | 15.014 | 1.00 | 24.33 |
| ATOM | 2813 | CG1 | VAL | 2247 | 8.164 | 63.064 | 14.404 | 1.00 | 22.90 |
| ATOM | 2814 | CG2 | VAL | 2247 | 8.190 | 65.548 | 14.897 | 1.00 | 25.31 |
| ATOM | 2815 | C | VAL | 2247 | 5.250 | 63.123 | 14.457 | 1.00 | 20.96 |
| ATOM | 2816 | O | VAL | 2247 | 4.716 | 62.831 | 15.518 | 1.00 | 23.24 |
| ATOM | 2817 | N | VAL | 2248 | 5.185 | 62.342 | 13.385 | 1.00 | 21.02 |
| ATOM | 2818 | CA | VAL | 2248 | 4.459 | 61.071 | 13.428 | 1.00 | 20.10 |

TABLE 2-continued

| | | | FGFR1 D2–D3 Complexed with FGF1 | | | | | |
|---|---|---|---|---|---|---|---|---|
| ATOM | 2819 | CB   | VAL | 2248 |  3.209 | 61.096 | 12.523 | 1.00 | 22.52 |
| ATOM | 2820 | CG1  | VAL | 2248 |  2.433 | 59.817 | 12.680 | 1.00 | 24.17 |
| ATOM | 2821 | CG2  | VAL | 2248 |  2.337 | 62.271 | 12.875 | 1.00 | 24.94 |
| ATOM | 2822 | C    | VAL | 2248 |  5.336 | 59.929 | 12.960 | 1.00 | 18.71 |
| ATOM | 2823 | O    | VAL | 2248 |  5.854 | 59.952 | 11.843 | 1.00 | 17.85 |
| ATOM | 2824 | N    | GLU | 2249 |  5.499 | 58.931 | 13.821 | 1.00 | 19.07 |
| ATOM | 2825 | CA   | GLU | 2249 |  6.306 | 57.763 | 13.491 | 1.00 | 20.26 |
| ATOM | 2826 | CB   | GLU | 2249 |  6.647 | 56.980 | 14.764 | 1.00 | 23.63 |
| ATOM | 2827 | CG   | GLU | 2249 |  7.421 | 57.804 | 15.789 | 1.00 | 29.31 |
| ATOM | 2828 | CD   | GLU | 2249 |  7.621 | 57.095 | 17.110 | 1.00 | 30.62 |
| ATOM | 2829 | OE1  | GLU | 2249 |  6.622 | 56.608 | 17.688 | 1.00 | 31.42 |
| ATOM | 2830 | OE2  | GLU | 2249 |  8.783 | 57.043 | 17.573 | 1.00 | 35.73 |
| ATOM | 2831 | C    | GLU | 2249 |  5.478 | 56.904 | 12.553 | 1.00 | 20.02 |
| ATOM | 2832 | O    | GLU | 2249 |  4.380 | 56.483 | 12.910 | 1.00 | 21.25 |
| ATOM | 2833 | N    | ARG | 2250 |  5.991 | 56.667 | 11.348 | 1.00 | 19.31 |
| ATOM | 2834 | CA   | ARG | 2250 |  5.282 | 55.855 | 10.358 | 1.00 | 19.27 |
| ATOM | 2835 | CB   | ARG | 2250 |  5.516 | 56.389 |  8.929 | 1.00 | 14.30 |
| ATOM | 2836 | CG   | ARG | 2250 |  5.039 | 57.822 |  8.660 | 1.00 | 12.43 |
| ATOM | 2837 | CD   | ARG | 2250 |  3.621 | 58.089 |  9.162 | 1.00 | 12.56 |
| ATOM | 2838 | NE   | ARG | 2250 |  2.601 | 57.339 |  8.431 | 1.00 | 16.48 |
| ATOM | 2839 | CZ   | ARG | 2250 |  2.203 | 57.609 |  7.189 | 1.00 | 18.36 |
| ATOM | 2840 | NH1  | ARG | 2250 |  2.729 | 58.622 |  6.501 | 1.00 | 14.94 |
| ATOM | 2841 | NH2  | ARG | 2250 |  1.277 | 56.851 |  6.627 | 1.00 | 18.04 |
| ATOM | 2842 | C    | ARG | 2250 |  5.732 | 54.396 | 10.443 | 1.00 | 20.00 |
| ATOM | 2843 | O    | ARG | 2250 |  6.919 | 54.122 | 10.617 | 1.00 | 21.86 |
| ATOM | 2844 | N    | ALA | 2251 |  4.788 | 53.464 | 10.309 | 1.00 | 19.84 |
| ATOM | 2845 | CA   | ALA | 2251 |  5.104 | 52.039 | 10.388 | 1.00 | 17.49 |
| ATOM | 2846 | CB   | ALA | 2251 |  4.314 | 51.415 | 11.554 | 1.00 | 15.22 |
| ATOM | 2847 | C    | ALA | 2251 |  4.814 | 51.289 |  9.076 | 1.00 | 17.93 |
| ATOM | 2848 | O    | ALA | 2251 |  3.702 | 50.785 |  8.898 | 1.00 | 19.93 |
| ATOM | 2849 | N    | PRO | 2252 |  5.806 | 51.225 |  8.132 | 1.00 | 19.12 |
| ATOM | 2850 | CD   | PRO | 2252 |  7.021 | 52.074 |  8.124 | 1.00 | 16.50 |
| ATOM | 2851 | CA   | PRO | 2252 |  5.671 | 50.538 |  6.829 | 1.00 | 17.21 |
| ATOM | 2852 | CB   | PRO | 2252 |  6.666 | 51.290 |  5.945 | 1.00 | 16.08 |
| ATOM | 2853 | CG   | PRO | 2252 |  7.780 | 51.571 |  6.901 | 1.00 | 13.86 |
| ATOM | 2854 | C    | PRO | 2252 |  5.948 | 49.025 |  6.834 | 1.00 | 17.45 |
| ATOM | 2855 | O    | PRO | 2252 |  6.942 | 48.554 |  6.280 | 1.00 | 17.02 |
| ATOM | 2856 | N    | HIS | 2253 |  5.056 | 48.272 |  7.463 | 1.00 | 18.62 |
| ATOM | 2857 | CA   | HIS | 2253 |  5.165 | 46.822 |  7.543 | 1.00 | 20.04 |
| ATOM | 2858 | CB   | HIS | 2253 |  5.589 | 46.388 |  8.951 | 1.00 | 24.45 |
| ATOM | 2859 | CG   | HIS | 2253 |  6.666 | 47.238 |  9.545 | 1.00 | 29.28 |
| ATOM | 2860 | CD2  | HIS | 2253 |  6.641 | 48.105 | 10.585 | 1.00 | 28.96 |
| ATOM | 2861 | ND1  | HIS | 2253 |  7.938 | 47.313 |  9.010 | 1.00 | 30.02 |
| ATOM | 2862 | CE1  | HIS | 2253 |  8.646 | 48.197 |  9.691 | 1.00 | 29.21 |
| ATOM | 2863 | NE2  | HIS | 2253 |  7.884 | 48.693 | 10.650 | 1.00 | 32.56 |
| ATOM | 2864 | C    | HIS | 2253 |  3.749 | 46.333 |  7.291 | 1.00 | 21.36 |
| ATOM | 2865 | O    | HIS | 2253 |  2.817 | 47.138 |  7.261 | 1.00 | 20.08 |
| ATOM | 2866 | N    | ARG | 2254 |  3.572 | 45.026 |  7.109 | 1.00 | 22.26 |
| ATOM | 2867 | CA   | ARG | 2254 |  2.232 | 44.505 |  6.891 | 1.00 | 20.97 |
| ATOM | 2868 | CB   | ARG | 2254 |  2.268 | 43.046 |  6.396 | 1.00 | 24.88 |
| ATOM | 2869 | CG   | ARG | 2254 |  2.584 | 41.956 |  7.436 | 1.00 | 25.31 |
| ATOM | 2870 | CD   | ARG | 2254 |  4.068 | 41.905 |  7.797 | 1.00 | 31.05 |
| ATOM | 2871 | NE   | ARG | 2254 |  4.655 | 40.568 |  7.641 | 1.00 | 33.67 |
| ATOM | 2872 | CZ   | ARG | 2254 |  4.229 | 39.466 |  8.258 | 1.00 | 32.88 |
| ATOM | 2873 | NH1  | ARG | 2254 |  3.201 | 39.509 |  9.089 | 1.00 | 35.12 |
| ATOM | 2874 | NH2  | ARG | 2254 |  4.846 | 38.315 |  8.053 | 1.00 | 31.58 |
| ATOM | 2875 | C    | ARG | 2254 |  1.547 | 44.599 |  8.246 | 1.00 | 19.97 |
| ATOM | 2876 | O    | ARG | 2254 |  2.181 | 44.920 |  9.247 | 1.00 | 19.38 |
| ATOM | 2877 | N    | PRO | 2255 |  0.245 | 44.334 |  8.302 | 1.00 | 18.97 |
| ATOM | 2878 | CD   | PRO | 2255 | −0.704 | 43.973 |  7.236 | 1.00 | 17.39 |
| ATOM | 2879 | CA   | PRO | 2255 | −0.423 | 44.424 |  9.604 | 1.00 | 17.68 |
| ATOM | 2880 | CB   | PRO | 2255 | −1.884 | 44.080 |  9.266 | 1.00 | 19.06 |
| ATOM | 2881 | CG   | PRO | 2255 | −2.003 | 44.461 |  7.810 | 1.00 | 17.45 |
| ATOM | 2882 | C    | PRO | 2255 |  0.175 | 43.451 | 10.635 | 1.00 | 16.18 |
| ATOM | 2883 | O    | PRO | 2255 |  0.819 | 42.465 | 10.266 | 1.00 | 10.22 |
| ATOM | 2884 | N    | ILE | 2256 | −0.063 | 43.738 | 11.917 | 1.00 | 17.71 |
| ATOM | 2885 | CA   | ILE | 2256 |  0.401 | 42.905 | 13.031 | 1.00 | 20.17 |
| ATOM | 2886 | CB   | ILE | 2256 |  1.310 | 43.684 | 14.007 | 1.00 | 21.84 |
| ATOM | 2887 | CG2  | ILE | 2256 |  1.579 | 42.836 | 15.244 | 1.00 | 22.63 |
| ATOM | 2888 | CG1  | ILE | 2256 |  2.624 | 44.084 | 13.329 | 1.00 | 25.56 |
| ATOM | 2889 | CD1  | ILE | 2256 |  3.525 | 44.970 | 14.209 | 1.00 | 24.01 |
| ATOM | 2890 | C    | ILE | 2256 | −0.812 | 42.465 | 13.842 | 1.00 | 21.08 |
| ATOM | 2891 | O    | ILE | 2256 | −1.599 | 43.304 | 14.280 | 1.00 | 22.25 |
| ATOM | 2892 | N    | LEU | 2257 | −0.972 | 41.162 | 14.046 | 1.00 | 21.14 |
| ATOM | 2893 | CA   | LEU | 2257 | −2.099 | 40.673 | 14.836 | 1.00 | 23.57 |
| ATOM | 2894 | CB   | LEU | 2257 | −2.692 | 39.399 | 14.227 | 1.00 | 22.98 |
| ATOM | 2895 | CG   | LEU | 2257 | −3.161 | 39.361 | 12.773 | 1.00 | 20.53 |

TABLE 2-continued

| | | | | FGFR1 D2–D3 Complexed with FGF1 | | | | |
|---|---|---|---|---|---|---|---|---|
| ATOM | 2896 | CD1 | LEU | 2257 | −4.123 | 38.185 | 12.587 | 1.00 | 18.03 |
| ATOM | 2897 | CD2 | LEU | 2257 | −3.859 | 40.645 | 12.429 | 1.00 | 20.37 |
| ATOM | 2898 | C | LEU | 2257 | −1.620 | 40.356 | 16.250 | 1.00 | 26.64 |
| ATOM | 2899 | O | LEU | 2257 | −0.462 | 39.973 | 16.451 | 1.00 | 30.59 |
| ATOM | 2900 | N | GLN | 2258 | −2.499 | 40.508 | 17.235 | 1.00 | 27.95 |
| ATOM | 2901 | CA | GLN | 2258 | −2.114 | 40.217 | 18.609 | 1.00 | 26.66 |
| ATOM | 2902 | CB | GLN | 2258 | −3.163 | 40.734 | 19.587 | 1.00 | 27.37 |
| ATOM | 2903 | CG | GLN | 2258 | −2.854 | 40.381 | 21.026 | 1.00 | 31.81 |
| ATOM | 2904 | CD | GLN | 2258 | −1.476 | 40.870 | 21.458 | 1.00 | 36.00 |
| ATOM | 2905 | OE1 | GLN | 2258 | −1.223 | 42.080 | 21.521 | 1.00 | 36.76 |
| ATOM | 2906 | NE2 | GLN | 2258 | −0.574 | 39.929 | 21.751 | 1.00 | 35.05 |
| ATOM | 2907 | C | GLN | 2258 | −1.969 | 38.720 | 18.770 | 1.00 | 25.32 |
| ATOM | 2908 | O | GLN | 2258 | −2.907 | 37.978 | 18.506 | 1.00 | 28.43 |
| ATOM | 2909 | N | ALA | 2259 | −0.790 | 38.278 | 19.192 | 1.00 | 25.30 |
| ATOM | 2910 | CA | ALA | 2259 | −0.520 | 36.853 | 19.390 | 1.00 | 24.71 |
| ATOM | 2911 | CB | ALA | 2259 | 0.883 | 36.670 | 19.940 | 1.00 | 23.59 |
| ATOM | 2912 | C | ALA | 2259 | −1.544 | 36.230 | 20.342 | 1.00 | 25.40 |
| ATOM | 2913 | O | ALA | 2259 | −1.919 | 36.836 | 21.351 | 1.00 | 28.18 |
| ATOM | 2914 | N | GLY | 2260 | −2.001 | 35.023 | 20.022 | 1.00 | 23.57 |
| ATOM | 2915 | CA | GLY | 2260 | −2.987 | 34.372 | 20.867 | 1.00 | 22.17 |
| ATOM | 2916 | C | GLY | 2260 | −4.408 | 34.591 | 20.373 | 1.00 | 21.74 |
| ATOM | 2917 | O | GLY | 2260 | −5.311 | 33.807 | 20.682 | 1.00 | 21.27 |
| ATOM | 2918 | N | LEU | 2261 | −4.616 | 35.656 | 19.604 | 1.00 | 20.57 |
| ATOM | 2919 | CA | LEU | 2261 | −5.943 | 35.958 | 19.078 | 1.00 | 21.16 |
| ATOM | 2920 | CB | LEU | 2261 | −6.304 | 37.416 | 19.373 | 1.00 | 21.27 |
| ATOM | 2921 | CG | LEU | 2261 | −6.347 | 37.757 | 20.865 | 1.00 | 22.44 |
| ATOM | 2922 | CD1 | LEU | 2261 | −6.741 | 39.215 | 21.078 | 1.00 | 20.50 |
| ATOM | 2923 | CD2 | LEU | 2261 | −7.346 | 36.837 | 21.545 | 1.00 | 22.48 |
| ATOM | 2924 | C | LEU | 2261 | −6.034 | 35.674 | 17.574 | 1.00 | 19.70 |
| ATOM | 2925 | O | LEU | 2261 | −5.152 | 36.057 | 16.805 | 1.00 | 20.74 |
| ATOM | 2926 | N | PRO | 2262 | −7.111 | 34.998 | 17.139 | 1.00 | 17.08 |
| ATOM | 2927 | CD | PRO | 2262 | −7.354 | 34.649 | 15.729 | 1.00 | 16.05 |
| ATOM | 2928 | CA | PRO | 2262 | −8.192 | 34.503 | 17.999 | 1.00 | 16.51 |
| ATOM | 2929 | CB | PRO | 2262 | −9.293 | 34.169 | 17.001 | 1.00 | 14.07 |
| ATOM | 2930 | CG | PRO | 2262 | −8.508 | 33.673 | 15.828 | 1.00 | 16.76 |
| ATOM | 2931 | C | PRO | 2262 | −7.704 | 33.285 | 18.762 | 1.00 | 17.26 |
| ATOM | 2932 | O | PRO | 2262 | −6.675 | 32.708 | 18.415 | 1.00 | 20.94 |
| ATOM | 2933 | N | ALA | 2263 | −8.426 | 32.893 | 19.800 | 1.00 | 15.69 |
| ATOM | 2934 | CA | ALA | 2263 | −8.027 | 31.734 | 20.592 | 1.00 | 14.01 |
| ATOM | 2935 | CB | ALA | 2263 | −7.831 | 32.151 | 22.060 | 1.00 | 7.68 |
| ATOM | 2936 | C | ALA | 2263 | −9.059 | 30.602 | 20.496 | 1.00 | 13.49 |
| ATOM | 2937 | O | ALA | 2263 | −10.267 | 30.852 | 20.374 | 1.00 | 11.10 |
| ATOM | 2938 | N | ASN | 2264 | −8.579 | 29.364 | 20.547 | 1.00 | 13.00 |
| ATOM | 2939 | CA | ASN | 2264 | −9.467 | 28.212 | 20.492 | 1.00 | 15.21 |
| ATOM | 2940 | CB | ASN | 2264 | −8.732 | 26.932 | 20.806 | 1.00 | 9.73 |
| ATOM | 2941 | CG | ASN | 2264 | −7.559 | 26.746 | 19.947 | 1.00 | 13.05 |
| ATOM | 2942 | OD1 | ASN | 2264 | −7.503 | 27.281 | 18.833 | 1.00 | 18.74 |
| ATOM | 2943 | ND2 | ASN | 2264 | −6.598 | 25.977 | 20.428 | 1.00 | 12.71 |
| ATOM | 2944 | C | ASN | 2264 | −10.583 | 28.339 | 21.495 | 1.00 | 19.33 |
| ATOM | 2945 | O | ASN | 2264 | −10.459 | 29.022 | 22.503 | 1.00 | 19.67 |
| ATOM | 2946 | N | LYS | 2265 | −11.674 | 27.649 | 21.212 | 1.00 | 24.50 |
| ATOM | 2947 | CA | LYS | 2265 | −12.814 | 27.669 | 22.085 | 1.00 | 27.32 |
| ATOM | 2948 | CB | LYS | 2265 | −13.738 | 28.819 | 21.721 | 1.00 | 28.46 |
| ATOM | 2949 | CG | LYS | 2265 | −13.241 | 30.174 | 22.150 | 1.00 | 32.13 |
| ATOM | 2950 | CD | LYS | 2265 | −14.378 | 30.948 | 22.789 | 1.00 | 36.02 |
| ATOM | 2951 | CE | LYS | 2265 | −14.977 | 30.158 | 23.950 | 1.00 | 36.92 |
| ATOM | 2952 | NZ | LYS | 2265 | −16.151 | 30.833 | 24.580 | 1.00 | 40.08 |
| ATOM | 2953 | C | LYS | 2265 | −13.553 | 26.367 | 21.930 | 1.00 | 30.50 |
| ATOM | 2954 | O | LYS | 2265 | −13.573 | 25.776 | 20.848 | 1.00 | 31.20 |
| ATOM | 2955 | N | THR | 2266 | −14.133 | 25.915 | 23.035 | 1.00 | 33.40 |
| ATOM | 2956 | CA | THR | 2266 | −14.928 | 24.699 | 23.073 | 1.00 | 32.79 |
| ATOM | 2957 | CB | THR | 2266 | −14.324 | 23.639 | 24.013 | 1.00 | 31.95 |
| ATOM | 2958 | OG1 | THR | 2266 | −13.009 | 23.280 | 23.567 | 1.00 | 30.70 |
| ATOM | 2959 | CG2 | THR | 2266 | −15.182 | 22.396 | 24.019 | 1.00 | 34.16 |
| ATOM | 2960 | C | THR | 2266 | −16.248 | 25.197 | 23.642 | 1.00 | 34.06 |
| ATOM | 2961 | O | THR | 2266 | −16.261 | 25.945 | 24.619 | 1.00 | 33.77 |
| ATOM | 2962 | N | VAL | 2267 | −17.354 | 24.816 | 23.012 | 1.00 | 35.60 |
| ATOM | 2963 | CA | VAL | 2267 | −18.670 | 25.249 | 23.463 | 1.00 | 35.90 |
| ATOM | 2964 | CB | VAL | 2267 | −19.141 | 26.520 | 22.704 | 1.00 | 38.17 |
| ATOM | 2965 | CG1 | VAL | 2267 | −18.149 | 27.657 | 22.924 | 1.00 | 38.27 |
| ATOM | 2966 | CG2 | VAL | 2267 | −19.279 | 26.218 | 21.210 | 1.00 | 36.88 |
| ATOM | 2967 | C | VAL | 2267 | −19.700 | 24.150 | 23.250 | 1.00 | 35.89 |
| ATOM | 2968 | O | VAL | 2267 | −19.446 | 23.163 | 22.553 | 1.00 | 36.10 |
| ATOM | 2969 | N | ALA | 2268 | −20.869 | 24.338 | 23.850 | 1.00 | 34.73 |
| ATOM | 2970 | CA | ALA | 2268 | −21.946 | 23.369 | 23.751 | 1.00 | 33.00 |
| ATOM | 2971 | CB | ALA | 2268 | −22.767 | 23.370 | 25.025 | 1.00 | 27.28 |
| ATOM | 2972 | C | ALA | 2268 | −22.827 | 23.708 | 22.574 | 1.00 | 34.99 |

TABLE 2-continued

FGFR1 D2–D3 Complexed with FGF1

| ATOM | 2973 | O | ALA | 2268 | −22.923 | 24.879 | 22.179 | 1.00 | 34.44 |
|---|---|---|---|---|---|---|---|---|---|
| ATOM | 2974 | N | LEU | 2269 | −23.457 | 22.681 | 22.006 | 1.00 | 35.47 |
| ATOM | 2975 | CA | LEU | 2269 | −24.357 | 22.882 | 20.883 | 1.00 | 35.90 |
| ATOM | 2976 | CB | LEU | 2269 | −25.110 | 21.584 | 20.564 | 1.00 | 39.22 |
| ATOM | 2977 | CG | LEU | 2269 | −24.353 | 20.443 | 19.867 | 1.00 | 42.42 |
| ATOM | 2978 | CD1 | LEU | 2269 | −25.140 | 19.154 | 20.022 | 1.00 | 42.54 |
| ATOM | 2979 | CD2 | LEU | 2269 | −24.136 | 20.771 | 18.386 | 1.00 | 41.55 |
| ATOM | 2980 | C | LEU | 2269 | −25.352 | 23.967 | 21.280 | 1.00 | 34.29 |
| ATOM | 2981 | O | LEU | 2269 | −25.940 | 23.905 | 22.357 | 1.00 | 32.80 |
| ATOM | 2982 | N | GLY | 2270 | −25.517 | 24.968 | 20.419 | 1.00 | 34.69 |
| ATOM | 2983 | CA | GLY | 2270 | −26.459 | 26.037 | 20.699 | 1.00 | 38.43 |
| ATOM | 2984 | C | GLY | 2270 | −25.838 | 27.301 | 21.254 | 1.00 | 41.50 |
| ATOM | 2985 | O | GLY | 2270 | −26.441 | 28.376 | 21.184 | 1.00 | 41.72 |
| ATOM | 2986 | N | SER | 2271 | −24.632 | 27.173 | 21.805 | 1.00 | 43.37 |
| ATOM | 2987 | CA | SER | 2271 | −23.918 | 28.305 | 22.380 | 1.00 | 43.17 |
| ATOM | 2988 | CB | SER | 2271 | −22.628 | 27.834 | 23.067 | 1.00 | 47.15 |
| ATOM | 2989 | OG | SER | 2271 | −22.855 | 26.791 | 23.999 | 1.00 | 54.22 |
| ATOM | 2990 | C | SER | 2271 | −23.528 | 29.297 | 21.292 | 1.00 | 42.24 |
| ATOM | 2991 | O | SER | 2271 | −23.167 | 28.902 | 20.179 | 1.00 | 41.28 |
| ATOM | 2992 | N | ASN | 2272 | −23.600 | 30.583 | 21.611 | 1.00 | 39.22 |
| ATOM | 2993 | CA | ASN | 2272 | −23.181 | 31.593 | 20.654 | 1.00 | 36.32 |
| ATOM | 2994 | CB | ASN | 2272 | −23.903 | 32.906 | 20.906 | 1.00 | 38.38 |
| ATOM | 2995 | CG | ASN | 2272 | −25.394 | 32.722 | 20.967 | 1.00 | 43.80 |
| ATOM | 2996 | OD1 | ASN | 2272 | −25.965 | 31.944 | 20.193 | 1.00 | 43.87 |
| ATOM | 2997 | ND2 | ASN | 2272 | −26.046 | 33.435 | 21.887 | 1.00 | 48.37 |
| ATOM | 2998 | C | ASN | 2272 | −21.694 | 31.736 | 20.924 | 1.00 | 32.84 |
| ATOM | 2999 | O | ASN | 2272 | −21.222 | 31.390 | 22.007 | 1.00 | 30.83 |
| ATOM | 3000 | N | VAL | 2273 | −20.944 | 32.228 | 19.951 | 1.00 | 28.07 |
| ATOM | 3001 | CA | VAL | 2273 | −19.515 | 32.351 | 20.153 | 1.00 | 23.37 |
| ATOM | 3002 | CB | VAL | 2273 | −18.776 | 31.080 | 19.666 | 1.00 | 19.24 |
| ATOM | 3003 | CG1 | VAL | 2273 | −19.577 | 30.396 | 18.614 | 1.00 | 20.51 |
| ATOM | 3004 | CG2 | VAL | 2273 | −17.415 | 31.434 | 19.115 | 1.00 | 19.81 |
| ATOM | 3005 | C | VAL | 2273 | −18.950 | 33.569 | 19.478 | 1.00 | 23.80 |
| ATOM | 3006 | O | VAL | 2273 | −19.504 | 34.065 | 18.502 | 1.00 | 25.04 |
| ATOM | 3007 | N | GLU | 2274 | −17.844 | 34.058 | 20.026 | 1.00 | 23.55 |
| ATOM | 3008 | CA | GLU | 2274 | −17.179 | 35.231 | 19.496 | 1.00 | 23.82 |
| ATOM | 3009 | CB | GLU | 2274 | −17.520 | 36.465 | 20.340 | 1.00 | 26.77 |
| ATOM | 3010 | CG | GLU | 2274 | −18.990 | 36.883 | 20.323 | 1.00 | 31.02 |
| ATOM | 3011 | CD | GLU | 2274 | −19.278 | 38.065 | 21.256 | 1.00 | 36.36 |
| ATOM | 3012 | OE1 | GLU | 2274 | −19.314 | 37.871 | 22.493 | 1.00 | 38.44 |
| ATOM | 3013 | CE2 | GLU | 2274 | −19.461 | 39.196 | 20.754 | 1.00 | 38.11 |
| ATOM | 3014 | C | GLU | 2274 | −15.677 | 35.019 | 19.500 | 1.00 | 23.04 |
| ATOM | 3015 | O | GLU | 2274 | −15.092 | 34.559 | 20.481 | 1.00 | 23.32 |
| ATOM | 3016 | N | PHE | 2275 | −15.056 | 35.334 | 18.379 | 1.00 | 22.12 |
| ATOM | 3017 | CA | PHE | 2275 | −13.617 | 35.228 | 18.266 | 1.00 | 23.08 |
| ATOM | 3018 | CB | PHE | 2275 | −13.227 | 34.497 | 16.989 | 1.00 | 23.46 |
| ATOM | 3019 | CG | PHE | 2275 | −13.513 | 33.025 | 17.016 | 1.00 | 24.47 |
| ATOM | 3020 | CD1 | PHE | 2275 | −12.814 | 32.188 | 17.876 | 1.00 | 20.25 |
| ATOM | 3021 | CD2 | PHE | 2275 | −14.462 | 32.469 | 16.155 | 1.00 | 22.69 |
| ATOM | 3022 | CE1 | PHE | 2275 | −13.046 | 30.814 | 17.881 | 1.00 | 22.65 |
| ATOM | 3023 | CE2 | PHE | 2275 | −14.704 | 31.095 | 16.151 | 1.00 | 23.25 |
| ATOM | 3024 | CZ | PHE | 2275 | −13.994 | 30.264 | 17.017 | 1.00 | 22.55 |
| ATOM | 3025 | C | PHE | 2275 | −13.152 | 36.678 | 18.192 | 1.00 | 24.50 |
| ATOM | 3026 | O | PHE | 2275 | −13.847 | 37.518 | 17.612 | 1.00 | 22.70 |
| ATOM | 3027 | N | MET | 2276 | −11.996 | 36.972 | 18.792 | 1.00 | 23.05 |
| ATOM | 3028 | CA | MET | 2276 | −11.450 | 38.323 | 18.783 | 1.00 | 19.92 |
| ATOM | 3029 | CB | MET | 2276 | −11.051 | 38.767 | 20.188 | 1.00 | 23.46 |
| ATOM | 3030 | CG | MET | 2276 | −12.105 | 38.548 | 21.248 | 1.00 | 28.97 |
| ATOM | 3031 | SD | MET | 2276 | −11.548 | 39.133 | 22.847 | 1.00 | 35.29 |
| ATOM | 3032 | CE | MET | 2276 | −12.366 | 40.757 | 22.877 | 1.00 | 35.62 |
| ATOM | 3033 | C | MET | 2276 | −10.224 | 38.352 | 17.914 | 1.00 | 17.93 |
| ATOM | 3034 | O | MET | 2276 | −9.613 | 37.330 | 17.644 | 1.00 | 17.08 |
| ATOM | 3035 | N | CYS | 2277 | −9.857 | 39.541 | 17.486 | 1.00 | 19.16 |
| ATOM | 3036 | CA | CYS | 2277 | −8.693 | 39.705 | 16.647 | 1.00 | 21.43 |
| ATOM | 3037 | C | CYS | 2277 | −8.246 | 41.148 | 16.852 | 1.00 | 22.01 |
| ATOM | 3038 | O | CYS | 2277 | −9.059 | 42.072 | 16.737 | 1.00 | 21.65 |
| ATOM | 3039 | CB | CYS | 2277 | −9.080 | 39.461 | 15.189 | 1.00 | 23.00 |
| ATOM | 3040 | SG | CYS | 2277 | −7.702 | 39.378 | 13.994 | 1.00 | 33.53 |
| ATOM | 3041 | N | LYS | 2278 | −6.969 | 41.334 | 17.178 | 1.00 | 20.12 |
| ATOM | 3042 | CA | LYS | 2278 | −6.420 | 42.663 | 17.398 | 1.00 | 21.75 |
| ATOM | 3043 | CB | LYS | 2278 | −5.748 | 42.736 | 18.772 | 1.00 | 23.93 |
| ATOM | 3044 | CG | LYS | 2278 | −6.257 | 43.847 | 19.688 | 1.00 | 26.77 |
| ATOM | 3045 | CD | LYS | 2278 | −5.526 | 45.177 | 19.459 | 1.00 | 32.15 |
| ATOM | 3046 | CE | LYS | 2278 | −5.866 | 46.236 | 20.538 | 1.00 | 35.30 |
| ATOM | 3047 | NZ | LYS | 2278 | −5.502 | 45.849 | 21.953 | 1.00 | 36.06 |
| ATOM | 3048 | C | LYS | 2278 | −5.411 | 42.951 | 16.299 | 1.00 | 22.73 |
| ATOM | 3049 | O | LYS | 2278 | −4.437 | 42.218 | 16.122 | 1.00 | 24.81 |

TABLE 2-continued

FGFR1 D2–D3 Complexed with FGF1

| ATOM | 3050 | N | VAL | 2279 | −5.648 | 44.031 | 15.565 | 1.00 | 22.86 |
|---|---|---|---|---|---|---|---|---|---|
| ATOM | 3051 | CA | VAL | 2279 | −4.785 | 44.410 | 14.453 | 1.00 | 20.11 |
| ATOM | 3052 | CB | VAL | 2279 | −5.608 | 44.423 | 13.123 | 1.00 | 17.48 |
| ATOM | 3053 | CG1 | VAL | 2279 | −4.723 | 44.767 | 11.954 | 1.00 | 18.12 |
| ATOM | 3054 | CG2 | VAL | 2279 | −6.274 | 43.093 | 12.909 | 1.00 | 12.42 |
| ATOM | 3055 | C | VAL | 2279 | −4.478 | 45.800 | 14.657 | 1.00 | 20.73 |
| ATOM | 3056 | O | VAL | 2279 | −4.820 | 46.684 | 15.235 | 1.00 | 19.88 |
| ATOM | 3057 | N | TYR | 2280 | −2.931 | 45.971 | 14.214 | 1.00 | 19.94 |
| ATOM | 3058 | CA | TYR | 2280 | −2.259 | 47.266 | 14.260 | 1.00 | 20.90 |
| ATOM | 3059 | CB | TYR | 2280 | −1.065 | 47.313 | 15.211 | 1.00 | 22.44 |
| ATOM | 3060 | CG | TYR | 2280 | −0.219 | 48.575 | 14.960 | 1.00 | 24.80 |
| ATOM | 3061 | CD1 | TYR | 2280 | −0.544 | 49.802 | 15.568 | 1.00 | 24.50 |
| ATOM | 3062 | CE1 | TYR | 2280 | 0.139 | 50.979 | 15.239 | 1.00 | 21.31 |
| ATOM | 3063 | CD2 | TYR | 2280 | 0.826 | 48.569 | 14.021 | 1.00 | 21.65 |
| ATOM | 3064 | CE2 | TYR | 2280 | 1.509 | 49.746 | 13.686 | 1.00 | 19.85 |
| ATOM | 3065 | CZ | TYR | 2280 | 1.161 | 50.939 | 14.296 | 1.00 | 21.86 |
| ATOM | 3066 | OH | TYR | 2280 | 1.823 | 52.097 | 13.945 | 1.00 | 25.77 |
| ATOM | 3067 | C | TYR | 2280 | −1.724 | 47.475 | 12.858 | 1.00 | 20.64 |
| ATOM | 3068 | O | TYR | 2280 | −1.089 | 46.585 | 12.295 | 1.00 | 23.29 |
| ATOM | 3069 | N | SER | 2281 | −1.930 | 48.656 | 12.303 | 1.00 | 18.64 |
| ATOM | 3070 | CA | SER | 2281 | −1.466 | 48.882 | 10.954 | 1.00 | 21.14 |
| ATOM | 3071 | CB | SER | 2281 | −2.374 | 48.077 | 10.001 | 1.00 | 22.58 |
| ATOM | 3072 | OG | SER | 2281 | −2.013 | 48.208 | 8.639 | 1.00 | 23.27 |
| ATOM | 3073 | C | SER | 2281 | −1.501 | 50.367 | 10.616 | 1.00 | 21.23 |
| ATOM | 3074 | O | SER | 2281 | −2.566 | 50.977 | 10.658 | 1.00 | 23.17 |
| ATOM | 3075 | N | ASP | 2282 | −0.346 | 50.952 | 10.301 | 1.00 | 20.96 |
| ATOM | 3076 | CA | ASP | 2282 | −0.310 | 52.366 | 9.941 | 1.00 | 19.46 |
| ATOM | 3077 | CB | ASP | 2282 | 1.125 | 52.806 | 9.624 | 1.00 | 20.53 |
| ATOM | 3078 | CG | ASP | 2282 | 1.201 | 54.230 | 9.109 | 1.00 | 20.83 |
| ATOM | 3079 | OD1 | ASP | 2282 | 2.319 | 54.780 | 9.011 | 1.00 | 18.07 |
| ATOM | 3080 | OD2 | ASP | 2282 | 0.143 | 54.799 | 8.792 | 1.00 | 23.14 |
| ATOM | 3081 | C | ASP | 2282 | −1.249 | 52.531 | 8.736 | 1.00 | 18.46 |
| ATOM | 3082 | O | ASP | 2282 | −2.273 | 53.217 | 8.841 | 1.00 | 19.78 |
| ATOM | 3083 | N | PRO | 2283 | −0.930 | 51.912 | 7.577 | 1.00 | 17.09 |
| ATOM | 3084 | CD | PRO | 2283 | 0.299 | 51.262 | 7.094 | 1.00 | 15.57 |
| ATOM | 3085 | CA | PRO | 2283 | −1.880 | 52.098 | 6.470 | 1.00 | 16.82 |
| ATOM | 3086 | CB | PRO | 2283 | −1.123 | 51.546 | 5.264 | 1.00 | 14.12 |
| ATOM | 3087 | CG | PRO | 2283 | −0.186 | 50.572 | 5.853 | 1.00 | 14.51 |
| ATOM | 3088 | C | PRO | 2283 | −3.164 | 51.333 | 6.777 | 1.00 | 17.33 |
| ATOM | 3089 | O | PRO | 2283 | −3.134 | 50.362 | 7.529 | 1.00 | 18.94 |
| ATOM | 3090 | N | GLN | 2284 | −4.292 | 51.773 | 6.228 | 1.00 | 18.73 |
| ATOM | 3091 | CA | GLN | 2284 | −5.568 | 51.100 | 6.494 | 1.00 | 21.43 |
| ATOM | 3092 | CB | GLN | 2284 | −6.696 | 51.736 | 5.689 | 1.00 | 24.32 |
| ATOM | 3093 | CG | GLN | 2284 | −7.175 | 53.030 | 6.274 | 1.00 | 30.25 |
| ATOM | 3094 | CD | GLN | 2284 | −7.677 | 52.849 | 7.685 | 1.00 | 33.16 |
| ATOM | 3095 | OE1 | GLN | 2284 | −7.553 | 53.749 | 8.518 | 1.00 | 39.37 |
| ATOM | 3096 | NE2 | GLN | 2284 | −8.255 | 51.685 | 7.963 | 1.00 | 29.48 |
| ATOM | 3097 | C | GLN | 2284 | −5.572 | 49.606 | 6.223 | 1.00 | 20.62 |
| ATOM | 3098 | O | GLN | 2284 | −5.324 | 49.161 | 5.109 | 1.00 | 21.34 |
| ATOM | 3099 | N | PRO | 2285 | −5.864 | 48.808 | 7.252 | 1.00 | 20.67 |
| ATOM | 3100 | CD | PRO | 2285 | −6.022 | 49.206 | 8.663 | 1.00 | 22.25 |
| ATOM | 3101 | CA | PRO | 2285 | −5.905 | 47.350 | 7.122 | 1.00 | 20.42 |
| ATOM | 3102 | CB | PRO | 2285 | −5.621 | 46.883 | 8.540 | 1.00 | 18.80 |
| ATOM | 3103 | CG | PRO | 2285 | −6.401 | 47.878 | 9.337 | 1.00 | 20.07 |
| ATOM | 3104 | C | PRO | 2285 | −7.275 | 46.875 | 6.647 | 1.00 | 21.35 |
| ATOM | 3105 | O | PRO | 2285 | −8.301 | 47.483 | 6.956 | 1.00 | 19.43 |
| ATOM | 3106 | N | HIS | 2286 | −7.288 | 45.788 | 5.887 | 1.00 | 22.52 |
| ATOM | 3107 | CA | HIS | 2286 | −8.536 | 45.227 | 5.414 | 1.00 | 23.32 |
| ATOM | 3108 | CB | HIS | 2286 | −8.481 | 45.010 | 3.903 | 1.00 | 27.49 |
| ATOM | 3109 | CG | HIS | 2286 | −9.756 | 44.476 | 3.334 | 1.00 | 32.81 |
| ATOM | 3110 | CD2 | HIS | 2286 | −10.924 | 45.094 | 3.037 | 1.00 | 35.44 |
| ATOM | 3111 | ND1 | HIS | 2286 | −9.956 | 43.137 | 3.081 | 1.00 | 33.65 |
| ATOM | 3112 | CE1 | HIS | 2286 | −11.192 | 42.952 | 2.654 | 1.00 | 34.94 |
| ATOM | 3113 | NE2 | HIS | 2286 | −11.800 | 44.124 | 2.619 | 1.00 | 35.76 |
| ATOM | 3114 | C | HIS | 2286 | −8.661 | 43.904 | 6.154 | 1.00 | 21.23 |
| ATOM | 3115 | O | HIS | 2286 | −7.826 | 43.026 | 5.987 | 1.00 | 20.31 |
| ATOM | 3116 | N | ILE | 2287 | −9.691 | 43.768 | 6.981 | 1.00 | 19.86 |
| ATOM | 3117 | CA | ILE | 2287 | −9.862 | 42.558 | 7.773 | 1.00 | 21.24 |
| ATOM | 3118 | CB | ILE | 2287 | −10.142 | 42.888 | 9.277 | 1.00 | 19.88 |
| ATOM | 3119 | CG2 | ILE | 2287 | −10.647 | 41.653 | 10.001 | 1.00 | 20.88 |
| ATOM | 3120 | CG1 | ILE | 2287 | −8.859 | 43.337 | 9.978 | 1.00 | 20.91 |
| ATOM | 3121 | CD1 | ILE | 2287 | −8.405 | 44.721 | 9.624 | 1.00 | 25.87 |
| ATOM | 3122 | C | ILE | 2287 | −10.959 | 41.622 | 7.286 | 1.00 | 23.20 |
| ATOM | 3123 | O | ILE | 2287 | −12.073 | 42.049 | 6.994 | 1.00 | 24.53 |
| ATOM | 3124 | N | GLN | 2288 | −10.630 | 40.336 | 7.221 | 1.00 | 24.44 |
| ATOM | 3125 | CA | GLN | 2288 | −11.574 | 39.314 | 6.793 | 1.00 | 27.20 |
| ATOM | 3126 | CB | GLN | 2288 | −11.244 | 38.800 | 5.394 | 1.00 | 28.49 |

TABLE 2-continued

FGFR1 D2–D3 Complexed with FGF1

| ATOM | 3127 | CG | GLN | 2288 | −11.553 | 39.714 | 4.245 | 1.00 | 30.33 |
| ATOM | 3128 | CD | GLN | 2288 | −11.346 | 39.004 | 2.927 | 1.00 | 33.65 |
| ATOM | 3129 | OE1 | GLN | 2288 | −11.402 | 39.611 | 1.858 | 1.00 | 37.86 |
| ATOM | 3130 | NE2 | GLN | 2288 | −11.106 | 37.699 | 2.997 | 1.00 | 34.58 |
| ATOM | 3131 | C | GLN | 2288 | −11.497 | 38.122 | 7.713 | 1.00 | 27.19 |
| ATOM | 3132 | O | GLN | 2288 | −10.430 | 37.806 | 8.234 | 1.00 | 28.06 |
| ATOM | 3133 | N | TRP | 2289 | −12.625 | 37.457 | 7.911 | 1.00 | 26.54 |
| ATOM | 3134 | CA | TRP | 2289 | −12.634 | 36.253 | 8.722 | 1.00 | 28.32 |
| ATOM | 3135 | CB | TRP | 2289 | −13.750 | 36.299 | 9.761 | 1.00 | 25.38 |
| ATOM | 3136 | CG | TRP | 2289 | −13.409 | 37.180 | 10.925 | 1.00 | 27.68 |
| ATOM | 3137 | CD2 | TRP | 2289 | −12.744 | 36.787 | 12.136 | 1.00 | 27.55 |
| ATOM | 3138 | CE2 | TRP | 2289 | −12.626 | 37.947 | 12.943 | 1.00 | 26.89 |
| ATOM | 3139 | CE3 | TRP | 2289 | −12.237 | 35.571 | 12.614 | 1.00 | 24.06 |
| ATOM | 3140 | CD1 | TRP | 2289 | −13.656 | 38.520 | 11.046 | 1.00 | 27.89 |
| ATOM | 3141 | NE1 | TRP | 2289 | −13.189 | 38.986 | 12.258 | 1.00 | 25.77 |
| ATOM | 3142 | CZ2 | TRP | 2289 | −12.024 | 37.920 | 14.205 | 1.00 | 25.28 |
| ATOM | 3143 | CZ3 | TRP | 2289 | −11.643 | 35.547 | 13.864 | 1.00 | 23.82 |
| ATOM | 3144 | CH2 | TRP | 2289 | −11.542 | 36.717 | 14.647 | 1.00 | 25.25 |
| ATOM | 3145 | C | TRP | 2289 | −12.843 | 35.102 | 7.738 | 1.00 | 30.49 |
| ATOM | 3146 | O | TRP | 2289 | −13.627 | 35.228 | 6.794 | 1.00 | 30.51 |
| ATOM | 3147 | N | LEU | 2290 | −12.135 | 33.994 | 7.935 | 1.00 | 28.70 |
| ATOM | 3148 | CA | LEU | 2290 | −12.269 | 32.872 | 7.020 | 1.00 | 30.74 |
| ATOM | 3149 | CB | LEU | 2290 | −11.000 | 32.722 | 6.167 | 1.00 | 29.89 |
| ATOM | 3150 | CG | LEU | 2290 | −10.212 | 33.935 | 5.669 | 1.00 | 29.52 |
| ATOM | 3151 | CD1 | LEU | 2290 | −8.980 | 33.448 | 4.918 | 1.00 | 28.48 |
| ATOM | 3152 | CD2 | LEU | 2290 | −11.073 | 34.800 | 4.774 | 1.00 | 29.20 |
| ATOM | 3153 | C | LEU | 2290 | −12.521 | 31.541 | 7.718 | 1.00 | 32.74 |
| ATOM | 3154 | O | LEU | 2290 | −11.876 | 31.218 | 8.711 | 1.00 | 35.23 |
| ATOM | 3155 | N | LYS | 2291 | −13.456 | 30.762 | 7.186 | 1.00 | 32.99 |
| ATOM | 3156 | CA | LYS | 2291 | −13.726 | 29.441 | 7.729 | 1.00 | 33.14 |
| ATOM | 3157 | CB | LYS | 2291 | −15.224 | 29.138 | 7.695 | 1.00 | 33.79 |
| ATOM | 3158 | CG | LYS | 2291 | −15.591 | 27.702 | 8.118 | 1.00 | 35.06 |
| ATOM | 3159 | CD | LYS | 2291 | −15.159 | 27.402 | 9.548 | 1.00 | 38.44 |
| ATOM | 3160 | CE | LYS | 2291 | −15.732 | 26.092 | 10.073 | 1.00 | 40.01 |
| ATOM | 3161 | NZ | LYS | 2291 | −15.085 | 24.893 | 9.476 | 1.00 | 42.04 |
| ATOM | 3162 | C | LYS | 2291 | −12.978 | 28.455 | 6.833 | 1.00 | 33.08 |
| ATOM | 3163 | O | LYS | 2291 | −12.884 | 28.653 | 5.626 | 1.00 | 33.86 |
| ATOM | 3164 | N | HIS | 2292 | −12.423 | 27.406 | 7.417 | 1.00 | 33.75 |
| ATOM | 3165 | CA | HIS | 2292 | −1.715 | 26.419 | 6.621 | 1.00 | 36.27 |
| ATOM | 3166 | CB | HIS | 2292 | −10.565 | 25.839 | 7.437 | 1.00 | 36.83 |
| ATOM | 3167 | CC | HIS | 2292 | −9.474 | 26.827 | 7.704 | 1.00 | 40.26 |
| ATOM | 3168 | CD2 | HIS | 2292 | −9.432 | 27.902 | 8.527 | 1.00 | 42.43 |
| ATOM | 3169 | ND1 | HIS | 2292 | −8.277 | 26.818 | 7.024 | 1.00 | 41.03 |
| ATOM | 3170 | CE1 | HIS | 2292 | −7.541 | 27.844 | 7.413 | 1.00 | 40.49 |
| ATOM | 3171 | NE2 | HIS | 2292 | −8.220 | 28.518 | 8.325 | 1.00 | 42.70 |
| ATOM | 3172 | C | HIS | 2292 | −12.696 | 25.334 | 6.196 | 1.00 | 38.08 |
| ATOM | 3173 | O | HIS | 2292 | −13.502 | 24.868 | 7.000 | 1.00 | 39.31 |
| ATOM | 3174 | N | ILE | 2293 | −12.652 | 24.950 | 4.925 | 1.00 | 39.67 |
| ATOM | 3175 | CA | ILE | 2293 | −13.561 | 23.920 | 4.432 | 1.00 | 41.05 |
| ATOM | 3176 | CB | ILE | 2293 | −14.479 | 24.454 | 3.322 | 1.00 | 41.60 |
| ATOM | 3177 | CG2 | ILE | 2293 | −15.592 | 23.439 | 3.057 | 1.00 | 44.08 |
| ATOM | 3178 | CG1 | ILE | 2293 | −15.087 | 25.792 | 3.740 | 1.00 | 41.91 |
| ATOM | 3179 | CD1 | ILE | 2293 | −15.889 | 26.455 | 2.640 | 1.00 | 43.30 |
| ATOM | 3180 | C | ILE | 2293 | −12.799 | 22.730 | 3.875 | 1.00 | 39.31 |
| ATOM | 3181 | O | ILE | 2293 | −11.990 | 22.886 | 2.968 | 1.00 | 39.37 |
| ATOM | 3182 | N | ASN | 2304 | −1.041 | 23.913 | −2.561 | 1.00 | 62.05 |
| ATOM | 3183 | CA | ASN | 2304 | −0.699 | 23.331 | −1.272 | 1.00 | 64.32 |
| ATOM | 3184 | CB | ASN | 2304 | 0.817 | 23.290 | −1.124 | 1.00 | 67.23 |
| ATOM | 3185 | CG | ASN | 2304 | 1.255 | 22.401 | 0.024 | 1.00 | 70.61 |
| ATOM | 3186 | OD1 | ASN | 2304 | 0.870 | 21.221 | 0.110 | 1.00 | 72.36 |
| ATOM | 3187 | ND2 | ASN | 2304 | 2.089 | 22.962 | 0.911 | 1.00 | 71.52 |
| ATOM | 3188 | C | ASN | 2304 | −1.281 | 24.209 | −0.165 | 1.00 | 64.20 |
| ATOM | 3189 | O | ASN | 2304 | −0.764 | 24.302 | 0.942 | 1.00 | 64.52 |
| ATOM | 3190 | N | LEU | 2305 | −2.389 | 24.872 | −0.490 | 1.00 | 63.72 |
| ATOM | 3191 | CA | LEU | 2305 | −3.067 | 25.756 | 0.442 | 1.00 | 62.02 |
| ATOM | 3192 | CB | LEU | 2305 | −3.184 | 27.154 | −0.152 | 1.00 | 62.74 |
| ATOM | 3193 | CG | LEU | 2305 | −1.908 | 27.883 | −0.565 | 1.00 | 62.44 |
| ATOM | 3194 | CD1 | LEU | 2305 | −2.319 | 29.112 | −1.312 | 1.00 | 61.35 |
| ATOM | 3195 | CD2 | LEU | 2305 | −1.025 | 28.247 | 0.650 | 1.00 | 62.84 |
| ATOM | 3196 | C | LEU | 2305 | −4.473 | 25.244 | 0.704 | 1.00 | 61.44 |
| ATOM | 3197 | O | LEU | 2305 | −5.041 | 24.551 | −0.133 | 1.00 | 62.02 |
| ATOM | 3198 | N | PRO | 2306 | −5.073 | 25.623 | 1.836 | 1.00 | 60.02 |
| ATOM | 3199 | CD | PRO | 2306 | −4.615 | 26.411 | 2.990 | 1.00 | 59.73 |
| ATOM | 3200 | CA | PRO | 2306 | −6.431 | 25.139 | 2.106 | 1.00 | 57.82 |
| ATOM | 3201 | CB | PRO | 2306 | −6.466 | 25.124 | 3.595 | 1.00 | 59.06 |
| ATOM | 3202 | CG | PRO | 2306 | −5.874 | 26.399 | 3.869 | 1.00 | 60.01 |
| ATOM | 3203 | C | PRO | 2306 | −7.546 | 26.011 | 1.593 | 1.00 | 56.58 |

TABLE 2-continued

| FGFR1 D2–D3 Complexed with FGF1 | | | | | | | |
|---|---|---|---|---|---|---|---|
| ATOM | 3204 | O | PRO | 2306 | −7.399 | 27.228 | 1.445 | 1.00 | 58.04 |
| ATOM | 3205 | N | TYR | 2307 | −8.688 | 25.369 | 1.388 | 1.00 | 55.64 |
| ATOM | 3206 | CA | TYR | 2307 | −9.885 | 26.056 | 0.936 | 1.00 | 53.48 |
| ATOM | 3207 | CB | TYR | 2307 | −10.933 | 25.076 | 0.417 | 1.00 | 56.98 |
| ATOM | 3208 | CG | TYR | 2307 | −10.416 | 23.924 | −0.405 | 1.00 | 62.03 |
| ATOM | 3209 | CD1 | TYR | 2307 | −9.967 | 22.753 | 0.209 | 1.00 | 65.31 |
| ATOM | 3210 | CE1 | TYR | 2307 | −9.517 | 21.669 | −0.544 | 1.00 | 66.92 |
| ATOM | 3211 | CD2 | TYR | 2307 | −10.401 | 23.990 | −1.800 | 1.00 | 63.17 |
| ATOM | 3212 | CE2 | TYR | 2307 | −9.952 | 22.915 | −2.565 | 1.00 | 65.21 |
| ATOM | 3213 | CZ | TYR | 2307 | −9.511 | 21.758 | −1.929 | 1.00 | 67.11 |
| ATOM | 3214 | OH | TYR | 2307 | −9.067 | 20.689 | −2.671 | 1.00 | 67.96 |
| ATOM | 3215 | C | TYR | 2307 | −10.537 | 26.824 | 2.082 | 1.00 | 49.68 |
| ATOM | 3216 | O | TYR | 2307 | −10.633 | 26.335 | 3.207 | 1.00 | 49.15 |
| ATOM | 3217 | N | VAL | 2308 | −11.029 | 28.017 | 1.789 | 1.00 | 45.52 |
| ATOM | 3218 | CA | VAL | 2308 | −11.660 | 28.826 | 2.815 | 1.00 | 43.00 |
| ATOM | 3219 | CB | VAL | 2308 | −10.746 | 29.992 | 3.239 | 1.00 | 41.70 |
| ATOM | 3220 | CG1 | VAL | 2308 | −9.441 | 29.451 | 3.779 | 1.00 | 37.17 |
| ATOM | 3221 | CG2 | VAL | 2308 | −10.487 | 30.931 | 2.052 | 1.00 | 40.99 |
| ATOM | 3222 | C | VAL | 2308 | −12.978 | 29.390 | 2.331 | 1.00 | 41.87 |
| ATOM | 3223 | O | VAL | 2308 | −13.292 | 29.337 | 1.149 | 1.00 | 42.67 |
| ATOM | 3224 | N | GLN | 2309 | −13.739 | 29.935 | 3.264 | 1.00 | 41.93 |
| ATOM | 3225 | CA | GLN | 2309 | −15.021 | 30.520 | 2.963 | 1.00 | 42.91 |
| ATOM | 3226 | CB | GLN | 2309 | −16.127 | 29.659 | 3.562 | 1.00 | 44.89 |
| ATOM | 3227 | CG | GLN | 2309 | −7.516 | 30.053 | 3.136 | 1.00 | 52.27 |
| ATOM | 3228 | CD | GLN | 2309 | −18.587 | 29.456 | 4.026 | 1.00 | 56.02 |
| ATOM | 3229 | OE1 | GLN | 2309 | −18.606 | 28.247 | 4.283 | 1.00 | 57.05 |
| ATOM | 3230 | NE2 | GLN | 2309 | −19.491 | 30.305 | 4.503 | 1.00 | 58.93 |
| ATOM | 3231 | C | GLN | 2309 | −15.015 | 31.892 | 3.625 | 1.00 | 42.49 |
| ATOM | 3232 | O | GLN | 2309 | −14.979 | 31.989 | 4.851 | 1.00 | 43.27 |
| ATOM | 3233 | N | ILE | 2310 | −15.011 | 32.950 | 2.824 | 1.00 | 40.11 |
| ATOM | 3234 | CA | ILE | 2310 | −15.025 | 34.291 | 3.379 | 1.00 | 39.08 |
| ATOM | 3235 | CB | ILE | 2310 | −15.021 | 35.362 | 2.277 | 1.00 | 39.01 |
| ATOM | 3236 | CG2 | ILE | 2310 | −14.919 | 36.741 | 2.897 | 1.00 | 35.23 |
| ATOM | 3237 | CG1 | ILE | 2310 | −13.875 | 35.106 | 1.292 | 1.00 | 39.88 |
| ATOM | 3238 | CD1 | ILE | 2310 | −12.510 | 35.076 | 1.913 | 1.00 | 39.73 |
| ATOM | 3239 | C | ILE | 2310 | −16.323 | 34.424 | 4.170 | 1.00 | 41.83 |
| ATOM | 3240 | O | ILE | 2310 | −17.390 | 34.017 | 3.698 | 1.00 | 44.61 |
| ATOM | 3241 | N | LEU | 2311 | −16.233 | 34.982 | 5.372 | 1.00 | 41.88 |
| ATOM | 3242 | CA | LEU | 2311 | −17.402 | 35.159 | 6.216 | 1.00 | 41.44 |
| ATOM | 3243 | CB | LEU | 2311 | −17.148 | 34.545 | 7.594 | 1.00 | 42.77 |
| ATOM | 3244 | CG | LEU | 2311 | −16.996 | 33.022 | 7.590 | 1.00 | 42.18 |
| ATOM | 3245 | CD1 | LEU | 2311 | −16.751 | 32.506 | 8.990 | 1.00 | 39.93 |
| ATOM | 3246 | CD2 | LEU | 2311 | −18.259 | 32.408 | 7.018 | 1.00 | 42.17 |
| ATOM | 3247 | C | LEU | 2311 | −17.766 | 36.628 | 6.354 | 1.00 | 43.17 |
| ATOM | 3248 | O | LEU | 2311 | −18.897 | 37.024 | 6.061 | 1.00 | 44.43 |
| ATOM | 3249 | N | GLU | 2324 | −13.336 | 43.467 | 14.737 | 1.00 | 40.36 |
| ATOM | 3250 | CA | GLU | 2324 | −12.410 | 42.769 | 15.620 | 1.00 | 37.84 |
| ATOM | 3251 | CB | GLU | 2324 | −12.114 | 43.614 | 16.850 | 1.00 | 40.25 |
| ATOM | 3252 | CG | GLU | 2324 | −11.481 | 44.950 | 16.594 | 1.00 | 45.51 |
| ATOM | 3253 | CD | GLU | 2324 | −11.284 | 45.716 | 17.892 | 1.00 | 49.98 |
| ATOM | 3254 | OE1 | GLU | 2324 | −11.542 | 45.124 | 18.966 | 1.00 | 49.99 |
| ATOM | 3255 | OE2 | GLU | 2324 | −10.872 | 46.901 | 17.849 | 1.00 | 54.07 |
| ATOM | 3256 | C | GLU | 2324 | −12.970 | 41.428 | 16.095 | 1.00 | 35.83 |
| ATOM | 3257 | O | GLU | 2324 | −12.222 | 40.579 | 16.592 | 1.00 | 36.63 |
| ATOM | 3258 | N | VAL | 2325 | −14.281 | 41.238 | 15.975 | 1.00 | 30.19 |
| ATOM | 3259 | CA | VAL | 2325 | −14.858 | 39.985 | 16.421 | 1.00 | 27.54 |
| ATOM | 3260 | CB | VAL | 2325 | −15.710 | 40.181 | 17.717 | 1.00 | 25.42 |
| ATOM | 3261 | CG1 | VAL | 2325 | −15.364 | 41.502 | 18.371 | 1.00 | 22.35 |
| ATOM | 3262 | CG2 | VAL | 2325 | −17.187 | 40.080 | 17.419 | 1.00 | 22.54 |
| ATOM | 3263 | C | VAL | 2325 | −15.692 | 39.259 | 15.372 | 1.00 | 27.76 |
| ATOM | 3264 | O | VAL | 2325 | −16.371 | 39.875 | 14.553 | 1.00 | 28.36 |
| ATOM | 3265 | N | LEU | 2326 | −15.604 | 37.937 | 15.395 | 1.00 | 26.34 |
| ATOM | 3266 | CA | LEU | 2326 | −16.370 | 37.101 | 14.497 | 1.00 | 25.78 |
| ATOM | 3267 | CB | LEU | 2326 | −15.504 | 35.977 | 13.920 | 1.00 | 21.35 |
| ATOM | 3268 | CG | LEU | 2326 | −16.291 | 34.860 | 13.222 | 1.00 | 23.78 |
| ATOM | 3269 | CD1 | LEU | 2326 | −17.282 | 35.481 | 12.238 | 1.00 | 20.95 |
| ATOM | 3270 | CD2 | LEU | 2326 | −15.336 | 33.883 | 12.509 | 1.00 | 19.68 |
| ATOM | 3271 | C | LEU | 2326 | −17.458 | 36.534 | 15.389 | 1.00 | 26.83 |
| ATOM | 3272 | O | LEU | 2326 | −17.164 | 35.917 | 16.405 | 1.00 | 25.50 |
| ATOM | 3273 | N | HIS | 2327 | −18.717 | 36.761 | 15.032 | 1.00 | 30.43 |
| ATOM | 3274 | CA | HIS | 2327 | −19.802 | 36.256 | 15.861 | 1.00 | 33.90 |
| ATOM | 3275 | CB | HIS | 2327 | −20.720 | 37.416 | 16.252 | 1.00 | 36.22 |
| ATOM | 3276 | CG | HIS | 2327 | −21.558 | 37.140 | 17.460 | 1.00 | 42.95 |
| ATOM | 3277 | CD2 | HIS | 2327 | −21.860 | 35.978 | 18.092 | 1.00 | 46.12 |
| ATOM | 3278 | ND1 | HIS | 2327 | −22.221 | 38.131 | 18.151 | 1.00 | 45.91 |
| ATOM | 3279 | CE1 | HIS | 2327 | −22.897 | 37.596 | 19.153 | 1.00 | 46.22 |
| ATOM | 3280 | NE2 | HIS | 2327 | −22.694 | 36.289 | 19.137 | 1.00 | 48.55 |

TABLE 2-continued

FGFR1 D2–D3 Complexed with FGF1

| ATOM | 3281 | C | HIS | 2327 | −20.615 | 35.105 | 15.244 | 1.00 | 32.96 |
|------|------|------|-----|------|---------|--------|--------|------|-------|
| ATOM | 3282 | O | HIS | 2327 | −21.250 | 35.257 | 14.204 | 1.00 | 33.14 |
| ATOM | 3283 | N | LEU | 2328 | −20.569 | 33.945 | 15.891 | 1.00 | 32.03 |
| ATOM | 3284 | CA | LEU | 2328 | −21.308 | 32.776 | 15.434 | 1.00 | 32.84 |
| ATOM | 3285 | CB | LEU | 2328 | −20.440 | 31.522 | 15.566 | 1.00 | 29.75 |
| ATOM | 3286 | CG | LEU | 2328 | −19.062 | 31.620 | 14.895 | 1.00 | 31.56 |
| ATOM | 3287 | CD1 | LEU | 2328 | −18.254 | 30.378 | 15.207 | 1.00 | 30.02 |
| ATOM | 3288 | CD2 | LEU | 2328 | −19.206 | 31.797 | 13.387 | 1.00 | 31.02 |
| ATOM | 3289 | C | LEU | 2328 | −22.551 | 32.653 | 16.311 | 1.00 | 35.89 |
| ATOM | 3290 | O | LEU | 2328 | −22.447 | 32.540 | 17.537 | 1.00 | 36.66 |
| ATOM | 3291 | N | ARG | 2329 | −23.725 | 32.687 | 15.686 | 1.00 | 38.78 |
| ATOM | 3292 | CA | ARG | 2329 | −24.986 | 32.598 | 16.420 | 1.00 | 41.21 |
| ATOM | 3293 | CB | ARG | 2329 | −26.162 | 32.878 | 15.486 | 1.00 | 40.21 |
| ATOM | 3294 | C | ARG | 2329 | −25.188 | 31.252 | 17.116 | 1.00 | 44.19 |
| ATOM | 3295 | O | ARG | 2329 | −24.309 | 30.783 | 17.841 | 1.00 | 49.35 |
| ATOM | 3296 | N | ASN | 2330 | −26.344 | 30.632 | 16.899 | 1.00 | 44.19 |
| ATOM | 3297 | CA | ASN | 2330 | −26.664 | 29.361 | 17.540 | 1.00 | 43.74 |
| ATOM | 3298 | CB | ASN | 2330 | −28.167 | 29.103 | 17.455 | 1.00 | 46.78 |
| ATOM | 3299 | CG | ASN | 2330 | −28.602 | 27.936 | 18.313 | 1.00 | 51.73 |
| ATOM | 3300 | OD1 | ASN | 2330 | −28.521 | 26.770 | 17.901 | 1.00 | 51.92 |
| ATOM | 3301 | ND2 | ASN | 2330 | −29.054 | 28.240 | 19.529 | 1.00 | 54.52 |
| ATOM | 3302 | C | ASN | 2330 | −25.894 | 28.185 | 16.957 | 1.00 | 43.06 |
| ATOM | 3303 | O | ASN | 2330 | −26.439 | 27.343 | 16.245 | 1.00 | 43.14 |
| ATOM | 3304 | N | VAL | 2331 | −24.615 | 28.133 | 17.302 | 1.00 | 42.22 |
| ATOM | 3305 | CA | VAL | 2331 | −23.690 | 27.107 | 16.848 | 1.00 | 39.36 |
| ATOM | 3306 | CB | VAL | 2331 | −22.356 | 27.279 | 17.583 | 1.00 | 37.88 |
| ATOM | 3307 | CG1 | VAL | 2331 | −21.465 | 26.056 | 17.394 | 1.00 | 37.62 |
| ATOM | 3308 | CC2 | VAL | 2331 | −21.674 | 28.527 | 17.065 | 1.00 | 34.34 |
| ATOM | 3309 | C | VAL | 2331 | −24.145 | 25.659 | 16.966 | 1.00 | 39.83 |
| ATOM | 3310 | O | VAL | 2331 | −24.868 | 25.297 | 17.888 | 1.00 | 39.78 |
| ATOM | 3311 | N | SER | 2332 | −23.692 | 24.845 | 16.012 | 1.00 | 41.07 |
| ATOM | 3312 | CA | SER | 2332 | −23.981 | 23.411 | 15.947 | 1.00 | 43.66 |
| ATOM | 3313 | CB | SER | 2332 | −24.966 | 23.123 | 14.815 | 1.00 | 44.86 |
| ATOM | 3314 | OG | SER | 2332 | −24.356 | 23.342 | 13.549 | 1.00 | 44.80 |
| ATOM | 3315 | C | SER | 2332 | −22.665 | 22.662 | 15.670 | 1.00 | 44.87 |
| ATOM | 3316 | O | SER | 2332 | −21.589 | 23.272 | 15.648 | 1.00 | 45.34 |
| ATOM | 3317 | N | PHE | 2333 | −22.743 | 21.350 | 15.452 | 1.00 | 44.28 |
| ATOM | 3318 | CA | PHE | 2333 | −21.537 | 20.575 | 15.173 | 1.00 | 44.85 |
| ATOM | 3319 | CB | PHE | 2333 | −21.860 | 19.081 | 15.028 | 1.00 | 44.97 |
| ATOM | 3320 | CG | PHE | 2333 | −22.125 | 18.392 | 16.333 | 1.00 | 47.08 |
| ATOM | 3321 | CD1 | PHE | 2333 | −23.358 | 17.794 | 16.585 | 1.00 | 46.75 |
| ATOM | 3322 | CD2 | PHE | 2333 | −21.152 | 18.374 | 17.332 | 1.00 | 47.17 |
| ATOM | 3323 | CE1 | PHE | 2333 | −23.620 | 17.188 | 17.814 | 1.00 | 46.53 |
| ATOM | 3324 | CE2 | PHE | 2333 | −21.403 | 17.772 | 18.563 | 1.00 | 46.90 |
| ATOM | 3325 | CZ | PHE | 2333 | −22.640 | 17.179 | 18.804 | 1.00 | 47.14 |
| ATOM | 3326 | C | PHE | 2333 | −20.857 | 21.067 | 13.906 | 1.00 | 45.07 |
| ATOM | 3327 | O | PHE | 2333 | −19.639 | 21.222 | 13.869 | 1.00 | 43.84 |
| ATOM | 3328 | N | GLU | 2334 | −21.651 | 21.320 | 12.870 | 1.00 | 46.28 |
| ATOM | 3329 | CA | GLU | 2334 | −21.106 | 21.782 | 11.602 | 1.00 | 46.39 |
| ATOM | 3330 | CB | GLU | 2334 | −22.228 | 22.071 | 10.608 | 1.00 | 51.24 |
| ATOM | 3331 | CG | GLU | 2334 | −21.710 | 22.359 | 9.207 | 1.00 | 56.82 |
| ATOM | 3332 | CD | GLU | 2334 | −22.639 | 23.253 | 8.414 | 1.00 | 60.09 |
| ATOM | 3333 | OE1 | GLU | 2334 | −23.818 | 22.871 | 8.232 | 1.00 | 63.25 |
| ATOM | 3334 | OE2 | GLU | 2334 | −22.186 | 24.337 | 7.975 | 1.00 | 60.77 |
| ATOM | 3335 | C | GLU | 2334 | −20.261 | 23.037 | 11.783 | 1.00 | 43.51 |
| ATOM | 3336 | O | GLU | 2334 | −19.326 | 23.285 | 11.017 | 1.00 | 42.01 |
| ATOM | 3337 | N | ASP | 2335 | −20.598 | 23.832 | 12.795 | 1.00 | 40.98 |
| ATOM | 3338 | CA | ASP | 2335 | −19.856 | 25.053 | 13.070 | 1.00 | 37.84 |
| ATOM | 3339 | CB | ASP | 2335 | −20.596 | 25.895 | 14.110 | 1.00 | 39.60 |
| ATOM | 3340 | CG | ASP | 2335 | −21.918 | 26.431 | 13.599 | 1.00 | 41.51 |
| ATOM | 3341 | OD1 | ASP | 2335 | −21.910 | 27.153 | 12.581 | 1.00 | 44.36 |
| ATOM | 3342 | OD2 | ASP | 2335 | −22.967 | 26.141 | 14.212 | 1.00 | 42.62 |
| ATOM | 3343 | C | ASP | 2335 | −18.447 | 24.728 | 13.574 | 1.00 | 34.92 |
| ATOM | 3344 | O | ASP | 2335 | −17.545 | 25.558 | 13.511 | 1.00 | 35.75 |
| ATOM | 3345 | N | ALA | 2336 | −18.251 | 23.519 | 14.079 | 1.00 | 31.20 |
| ATOM | 3346 | CA | ALA | 2336 | −16.937 | 23.151 | 14.576 | 1.00 | 31.00 |
| ATOM | 3347 | CB | ALA | 2336 | −16.948 | 21.725 | 15.111 | 1.00 | 33.17 |
| ATOM | 3348 | C | ALA | 2336 | −15.934 | 23.279 | 13.449 | 1.00 | 29.61 |
| ATOM | 3349 | O | ALA | 2336 | −16.298 | 23.187 | 12.280 | 1.00 | 28.64 |
| ATOM | 3350 | N | GLY | 2337 | −14.676 | 23.518 | 13.805 | 1.00 | 29.46 |
| ATOM | 3351 | CA | GLY | 2337 | −13.639 | 23.642 | 12.799 | 1.00 | 27.88 |
| ATOM | 3352 | C | GLY | 2337 | −12.708 | 24.812 | 13.019 | 1.00 | 27.32 |
| ATOM | 3353 | O | GLY | 2337 | −12.816 | 25.533 | 14.010 | 1.00 | 27.38 |
| ATOM | 3354 | N | GLU | 2338 | 11.801 | 25.010 | 12.068 | 1.00 | 26.35 |
| ATOM | 3355 | CA | GLU | 2338 | 10.817 | 26.077 | 12.145 | 1.00 | 25.16 |
| ATOM | 3356 | CB | GLU | 2338 | −9.500 | 25.587 | 11.544 | 1.00 | 25.02 |
| ATOM | 3357 | CG | GLU | 2338 | −8.417 | 26.640 | 11.439 | 1.00 | 29.90 |

TABLE 2-continued

FGFR1 D2–D3 Complexed with FGF1

| ATOM | 3358 | CD | GLU | 2338 | −7.099 | 26.060 | 10.960 | 1.00 | 32.40 |
|---|---|---|---|---|---|---|---|---|---|
| ATOM | 3359 | OE1 | GLU | 2338 | −7.125 | 25.240 | 10.023 | 1.00 | 36.76 |
| ATOM | 3360 | OE2 | GLU | 2338 | −6.036 | 26.427 | 11.507 | 1.00 | 35.28 |
| ATOM | 3361 | C | GLU | 2338 | −11.227 | 27.389 | 11.485 | 1.00 | 23.81 |
| ATOM | 3362 | O | GLU | 2338 | −11.734 | 27.402 | 10.369 | 1.00 | 21.60 |
| ATOM | 3363 | N | TYR | 2339 | −10.999 | 28.490 | 12.199 | 1.00 | 25.63 |
| ATOM | 3364 | CA | TYR | 2339 | −11.306 | 29.827 | 11.696 | 1.00 | 26.09 |
| ATOM | 3365 | CB | TYR | 2339 | −12.348 | 30.517 | 12.567 | 1.00 | 26.10 |
| ATOM | 3366 | CC | TYR | 2339 | −13.696 | 29.861 | 12.514 | 1.00 | 28.36 |
| ATOM | 3367 | CD1 | TYR | 2339 | −13.937 | 28.673 | 13.195 | 1.00 | 29.75 |
| ATOM | 3368 | CE1 | TYR | 2339 | −15.179 | 28.044 | 13.123 | 1.00 | 33.66 |
| ATOM | 3369 | CD2 | TYR | 2339 | −14.731 | 30.415 | 11.758 | 1.00 | 30.60 |
| ATOM | 3370 | CE2 | TYR | 2339 | −15.980 | 29.798 | 11.677 | 1.00 | 30.79 |
| ATOM | 3371 | GZ | TYR | 2339 | 16.197 | 28.614 | 12.363 | 1.00 | 33.46 |
| ATOM | 3372 | OH | TYR | 2339 | 17.431 | 28.002 | 12.296 | 1.00 | 36.17 |
| ATOM | 3373 | C | TYR | 2339 | −10.049 | 30.686 | 11.645 | 1.00 | 25.83 |
| ATOM | 3374 | O | TYR | 2339 | −9.108 | 30.482 | 12.412 | 1.00 | 25.51 |
| ATOM | 3375 | N | THR | 2340 | −10.056 | 31.653 | 10.735 | 1.00 | 26.17 |
| ATOM | 3376 | CA | THR | 2340 | −8.930 | 32.550 | 10.539 | 1.00 | 26.13 |
| ATOM | 3377 | CB | THR | 2340 | −8.130 | 32.164 | 9.279 | 1.00 | 25.51 |
| ATOM | 3378 | OG1 | THR | 2340 | −7.397 | 30.965 | 9.540 | 1.00 | 25.93 |
| ATOM | 3379 | CG2 | THR | 2340 | −7.157 | 33.281 | 8.882 | 1.00 | 24.93 |
| ATOM | 3380 | C | THR | 2340 | −9.311 | 34.018 | 10.406 | 1.00 | 26.93 |
| ATOM | 3381 | O | THR | 2340 | −10.294 | 34.377 | 9.752 | 1.00 | 26.98 |
| ATOM | 3382 | N | CYS | 2341 | −8.507 | 34.861 | 11.039 | 1.00 | 27.65 |
| ATOM | 3383 | CA | CYS | 2341 | −8.697 | 36.290 | 10.977 | 1.00 | 27.53 |
| ATOM | 3384 | C | GYS | 2341 | −7.557 | 36.754 | 10.096 | 1.00 | 26.55 |
| ATOM | 3385 | O | CYS | 2341 | −6.396 | 36.552 | 10.436 | 1.00 | 26.68 |
| ATOM | 3386 | CB | CYS | 2341 | −8.580 | 36.922 | 12.364 | 1.00 | 27.67 |
| ATOM | 3387 | SG | GYS | 2341 | −8.642 | 38.740 | 12.303 | 1.00 | 35.81 |
| ATOM | 3388 | N | LEU | 2342 | −7.890 | 37.346 | 8.952 | 1.00 | 25.54 |
| ATOM | 3389 | CA | LEU | 2342 | −6.879 | 37.834 | 8.029 | 1.00 | 23.02 |
| ATOM | 3390 | CB | LEU | 2342 | −7.046 | 37.168 | 6.658 | 1.00 | 24.73 |
| ATOM | 3391 | CG | LEU | 2342 | −5.942 | 37.381 | 5.610 | 1.00 | 27.71 |
| ATOM | 3392 | CD1 | LEU | 2342 | −6.063 | 36.329 | 4.503 | 1.00 | 28.36 |
| ATOM | 3393 | CD2 | LEU | 2342 | −6.025 | 38.789 | 5.026 | 1.00 | 27.29 |
| ATOM | 3394 | C | LEU | 2342 | −6.968 | 39.349 | 7.881 | 1.00 | 22.27 |
| ATOM | 3395 | O | LEU | 2342 | −8.052 | 39.917 | 7.752 | 1.00 | 20.43 |
| ATOM | 3396 | N | ALA | 2343 | −5.807 | 39.991 | 7.920 | 1.00 | 21.01 |
| ATOM | 3397 | CA | ALA | 2343 | −5.702 | 41.432 | 7.766 | 1.00 | 20.11 |
| ATOM | 3398 | CB | ALA | 2343 | −5.360 | 42.086 | 9.098 | 1.00 | 23.64 |
| ATOM | 3399 | C | ALA | 2343 | −4.588 | 41.685 | 6.762 | 1.00 | 19.39 |
| ATOM | 3400 | O | ALA | 2343 | −3.566 | 40.987 | 6.775 | 1.00 | 20.25 |
| ATOM | 3401 | N | GLY | 2344 | −4.781 | 42.676 | 5.896 | 1.00 | 15.98 |
| ATOM | 3402 | CA | GLY | 2344 | −3.770 | 42.979 | 4.907 | 1.00 | 14.20 |
| ATOM | 3403 | C | GLY | 2344 | −3.752 | 44.440 | 4.503 | 1.00 | 17.89 |
| ATOM | 3404 | O | GLY | 2344 | −4.788 | 45.127 | 4.517 | 1.00 | 16.24 |
| ATOM | 3405 | N | ASN | 2345 | −2.563 | 44.927 | 4.164 | 1.00 | 17.17 |
| ATOM | 3406 | CA | ASN | 2345 | −2.428 | 46.298 | 3.721 | 1.00 | 21.03 |
| ATOM | 3407 | CB | ASN | 2345 | −1.805 | 47.193 | 4.806 | 1.00 | 23.74 |
| ATOM | 3408 | CG | ASN | 2345 | −0.399 | 46.784 | 5.174 | 1.00 | 24.91 |
| ATOM | 3409 | OD1 | ASN | 2345 | −0.431 | 46.504 | 4.305 | 1.00 | 23.61 |
| ATOM | 3410 | ND2 | ASN | 2345 | −0.113 | 46.768 | 6.475 | 1.00 | 25.23 |
| ATOM | 3411 | C | ASN | 2345 | −1.567 | 46.284 | 2.474 | 1.00 | 22.00 |
| ATOM | 3412 | O | ASN | 2345 | −1.140 | 45.224 | 2.027 | 1.00 | 22.16 |
| ATOM | 3413 | N | SER | 2346 | −1.303 | 47.458 | 1.916 | 1.00 | 21.88 |
| ATOM | 3414 | CA | SER | 2346 | −0.518 | 47.541 | 0.699 | 1.00 | 21.21 |
| ATOM | 3415 | CB | SER | 2346 | −0.334 | 48.992 | 0.283 | 1.00 | 24.16 |
| ATOM | 3416 | CG | SER | 2346 | 0.677 | 49.611 | 1.064 | 1.00 | 33.09 |
| ATOM | 3417 | C | SER | 2346 | 0.846 | 46.888 | 0.779 | 1.00 | 20.93 |
| ATOM | 3418 | O | SER | 2346 | 1.414 | 46.559 | −0.252 | 1.00 | 24.76 |
| ATOM | 3419 | N | ILE | 2347 | 1.393 | 46.706 | 1.977 | 1.00 | 19.77 |
| ATOM | 3420 | CA | ILE | 2347 | 2.718 | 46.087 | 2.082 | 1.00 | 19.53 |
| ATOM | 3421 | CB | ILE | 2347 | 3.476 | 46.527 | 3.386 | 1.00 | 19.85 |
| ATOM | 3422 | CG2 | ILE | 2347 | 4.732 | 45.668 | 3.573 | 1.00 | 18.89 |
| ATOM | 3423 | CG1 | ILE | 2347 | 3.948 | 47.985 | 3.286 | 1.00 | 14.77 |
| ATOM | 3424 | CD1 | ILE | 2347 | 2.872 | 48.970 | 2.968 | 1.00 | 14.56 |
| ATOM | 3425 | C | ILE | 2347 | 2.656 | 44.552 | 2.033 | 1.00 | 19.00 |
| ATOM | 3426 | O | ILE | 2347 | 3.401 | 43.908 | 1.294 | 1.00 | 18.70 |
| ATOM | 3427 | N | GLY | 2348 | 1.766 | 43.972 | 2.821 | 1.00 | 18.45 |
| ATOM | 3428 | CA | GLY | 2348 | 1.630 | 42.533 | 2.846 | 1.00 | 16.84 |
| ATOM | 3429 | C | GLY | 2348 | 0.423 | 42.154 | 3.673 | 1.00 | 19.06 |
| ATOM | 3430 | O | GLY | 2348 | −0.350 | 43.017 | 4.090 | 1.00 | 21.04 |
| ATOM | 3431 | N | LEU | 2349 | 0.232 | 40.866 | 3.915 | 1.00 | 21.40 |
| ATOM | 3432 | CA | LEU | 2349 | −0.917 | 40.472 | 4.710 | 1.00 | 23.92 |
| ATOM | 3433 | CB | LEU | 2349 | −2.002 | 39.887 | 3.802 | 1.00 | 24.93 |
| ATOM | 3434 | CG | LEU | 2349 | −1.783 | 38.567 | 3.089 | 1.00 | 25.84 |

TABLE 2-continued

FGFR1 D2–D3 Complexed with FGF1

| ATOM | 3435 | CD1 | LEU | 2349 | −2.053 | 37.427 | 4.071 | 1.00 | 27.55 |
|---|---|---|---|---|---|---|---|---|---|
| ATOM | 3436 | CD2 | LEU | 2349 | −2.734 | 38.466 | 1.902 | 1.00 | 24.89 |
| ATOM | 3437 | C | LEU | 2349 | −0.519 | 39.508 | 5.819 | 1.00 | 23.81 |
| ATOM | 3438 | O | LEU | 2349 | 0.536 | 38.881 | 5.752 | 1.00 | 22.86 |
| ATOM | 3439 | N | SER | 2350 | −1.353 | 39.411 | 6.849 | 1.00 | 25.20 |
| ATOM | 3440 | CA | SER | 2350 | −1.058 | 38.533 | 7.982 | 1.00 | 23.85 |
| ATOM | 3441 | CB | SER | 2350 | −0.478 | 39.356 | 9.129 | 1.00 | 26.37 |
| ATOM | 3442 | OG | SER | 2350 | 0.066 | 40.585 | 8.661 | 1.00 | 27.48 |
| ATOM | 3443 | C | SER | 2350 | −2.327 | 37.858 | 8.481 | 1.00 | 22.50 |
| ATOM | 3444 | O | SER | 2350 | −3.431 | 38.326 | 8.222 | 1.00 | 22.48 |
| ATOM | 3445 | N | HIS | 2351 | −2.170 | 36.762 | 9.205 | 1.00 | 23.35 |
| ATOM | 3446 | CA | HIS | 2351 | −3.330 | 36.078 | 9.766 | 1.00 | 25.91 |
| ATOM | 3447 | CB | HIS | 2351 | −4.119 | 35.351 | 8.676 | 1.00 | 24.75 |
| ATOM | 3448 | CG | HIS | 2351 | −3.378 | 34.217 | 8.053 | 1.00 | 25.15 |
| ATOM | 3449 | CD2 | HIS | 2351 | −3.516 | 32.877 | 8.191 | 1.00 | 25.62 |
| ATOM | 3450 | ND1 | HIS | 2351 | −2.353 | 34.407 | 7.151 | 1.00 | 26.72 |
| ATOM | 3451 | CE1 | HIS | 2351 | −1.893 | 33.232 | 6.759 | 1.00 | 25.94 |
| ATOM | 3452 | NE2 | HIS | 2351 | −2.582 | 32.287 | 7.374 | 1.00 | 26.06 |
| ATOM | 3453 | C | HIS | 2351 | −2.990 | 35.093 | 10.880 | 1.00 | 26.62 |
| ATOM | 3454 | O | HIS | 2351 | −1.873 | 34.585 | 10.973 | 1.00 | 27.45 |
| ATOM | 3455 | N | HIS | 2352 | −3.980 | 34.849 | 11.728 | 1.00 | 27.46 |
| ATOM | 3456 | CA | HIS | 2352 | −3.879 | 33.923 | 12.848 | 1.00 | 25.59 |
| ATOM | 3457 | CB | HIS | 2352 | −3.870 | 34.669 | 14.184 | 1.00 | 26.72 |
| ATOM | 3458 | CG | HIS | 2352 | −2.614 | 35.436 | 14.453 | 1.00 | 27.99 |
| ATOM | 3459 | GD2 | HIS | 2352 | −1.546 | 35.715 | 13.669 | 1.00 | 28.60 |
| ATOM | 3460 | ND1 | HIS | 2352 | −2.357 | 36.022 | 15.674 | 1.00 | 25.34 |
| ATOM | 3461 | CE1 | HIS | 2352 | −1.185 | 36.630 | 15.630 | 1.00 | 25.94 |
| ATOM | 3462 | NE2 | HIS | 2352 | −0.673 | 36.459 | 14.425 | 1.00 | 28.21 |
| ATOM | 3463 | C | HIS | 2352 | −5.141 | 33.078 | 12.777 | 1.00 | 25.00 |
| ATOM | 3464 | O | HIS | 2352 | −6.189 | 33.545 | 12.318 | 1.00 | 23.02 |
| ATOM | 3465 | N | SER | 2353 | −5.049 | 31.837 | 13.231 | 1.00 | 25.48 |
| ATOM | 3466 | CA | SER | 2353 | −6.209 | 30.962 | 13.207 | 1.00 | 26.14 |
| ATOM | 3467 | CB | SER | 2353 | −5.983 | 29.830 | 12.216 | 1.00 | 25.97 |
| ATOM | 3468 | OG | SER | 2353 | −5.596 | 30.359 | 10.961 | 1.00 | 30.37 |
| ATOM | 3469 | C | SER | 2353 | −6.488 | 30.394 | 14.577 | 1.00 | 25.96 |
| ATOM | 3470 | O | SER | 2353 | −5.682 | 30.529 | 15.493 | 1.00 | 27.63 |
| ATOM | 3471 | N | ALA | 2354 | −7.648 | 29.769 | 14.716 | 1.00 | 28.26 |
| ATOM | 3472 | CA | ALA | 2354 | −8.039 | 29.151 | 15.981 | 1.00 | 28.99 |
| ATOM | 3473 | CB | ALA | 2354 | −8.682 | 30.180 | 16.906 | 1.00 | 26.00 |
| ATOM | 3474 | C | ALA | 2354 | −9.014 | 28.026 | 15.677 | 1.00 | 28.34 |
| ATOM | 3475 | O | ALA | 2354 | −9.589 | 27.992 | 14.591 | 1.00 | 25.64 |
| ATOM | 3476 | N | TRP | 2355 | −9.200 | 27.111 | 16.626 | 1.00 | 30.54 |
| ATOM | 3477 | CA | TRP | 2355 | −10.107 | 25.978 | 16.429 | 1.00 | 31.68 |
| ATOM | 3478 | CB | TRP | 2355 | −9.349 | 24.650 | 16.576 | 1.00 | 35.96 |
| ATOM | 3479 | CG | TRP | 2355 | −9.671 | 23.674 | 15.485 | 1.00 | 44.14 |
| ATOM | 3480 | CD2 | TRP | 2355 | −10.745 | 22.713 | 15.477 | 1.00 | 46.89 |
| ATOM | 3481 | CE2 | TRP | 2355 | −10.700 | 22.050 | 14.225 | 1.00 | 47.34 |
| ATOM | 3482 | CE3 | TRP | 2355 | −11.739 | 22.350 | 16.402 | 1.00 | 49.33 |
| ATOM | 3483 | CD1 | TRP | 2355 | −9.038 | 23.554 | 14.273 | 1.00 | 45.62 |
| ATOM | 3484 | NE1 | TRP | 2355 | −9.654 | 22.579 | 13.514 | 1.00 | 47.04 |
| ATOM | 3485 | CZ2 | TRP | 2355 | −11.616 | 21.041 | 13.877 | 1.00 | 49.67 |
| ATOM | 3486 | CZ3 | TRP | 2355 | −12.658 | 21.336 | 16.053 | 1.00 | 50.10 |
| ATOM | 3487 | CH2 | TRP | 2355 | −12.583 | 20.698 | 14.799 | 1.00 | 51.09 |
| ATOM | 3488 | C | TRP | 2355 | −11.286 | 26.007 | 17.394 | 1.00 | 30.19 |
| ATOM | 3489 | O | TRP | 2355 | −11.110 | 26.198 | 18.613 | 1.00 | 29.45 |
| ATOM | 3490 | N | LEU | 2356 | −12.480 | 25.839 | 16.848 | 1.00 | 28.20 |
| ATOM | 3491 | CA | LEU | 2356 | −13.696 | 25.852 | 17.645 | 1.00 | 27.77 |
| ATOM | 3492 | CB | LEU | 2356 | −14.800 | 26.608 | 16.918 | 1.00 | 26.93 |
| ATOM | 3493 | CG | LEU | 2356 | −16.128 | 26.552 | 17.675 | 1.00 | 29.22 |
| ATOM | 3494 | CD1 | LEU | 2356 | −16.026 | 27.451 | 18.915 | 1.00 | 29.55 |
| ATOM | 3495 | CD2 | LEU | 2356 | −17.289 | 27.011 | 16.778 | 1.00 | 26.35 |
| ATOM | 3496 | C | LEU | 2356 | −14.162 | 24.436 | 17.901 | 1.00 | 27.46 |
| ATOM | 3497 | O | LEU | 2356 | −14.468 | 23.702 | 16.957 | 1.00 | 28.35 |
| ATOM | 3498 | N | THR | 2357 | −14.260 | 24.053 | 19.167 | 1.00 | 28.12 |
| ATOM | 3499 | CA | THR | 2357 | −14.697 | 22.710 | 19.490 | 1.00 | 28.42 |
| ATOM | 3500 | CB | THR | 2357 | −13.766 | 22.070 | 20.539 | 1.00 | 29.97 |
| ATOM | 3501 | OG1 | THR | 2357 | −12.397 | 22.232 | 20.124 | 1.00 | 34.87 |
| ATOM | 3502 | CG2 | THR | 2357 | −14.085 | 20.602 | 20.675 | 1.00 | 28.93 |
| ATOM | 3503 | C | THR | 2357 | −16.128 | 22.755 | 19.990 | 1.00 | 27.28 |
| ATOM | 3504 | O | THR | 2357 | −16.493 | 23.594 | 20.821 | 1.00 | 25.21 |
| ATOM | 3505 | N | VAL | 2358 | −16.948 | 21.853 | 19.473 | 1.00 | 26.50 |
| ATOM | 3506 | CA | VAL | 2358 | −18.345 | 21.841 | 19.880 | 1.00 | 27.27 |
| ATOM | 3507 | CB | VAL | 2358 | −19.239 | 22.101 | 18.692 | 1.00 | 28.10 |
| ATOM | 3508 | CG1 | VAL | 2358 | −20.639 | 22.433 | 19.174 | 1.00 | 31.58 |
| ATOM | 3509 | CG2 | VAL | 2358 | −18.646 | 23.239 | 17.861 | 1.00 | 27.73 |
| ATOM | 3510 | C | VAL | 2358 | −18.769 | 20.553 | 20.577 | 1.00 | 27.76 |
| ATOM | 3511 | O | VAL | 2358 | −18.437 | 19.453 | 20.141 | 1.00 | 27.86 |

TABLE 2-continued

| FGFR1 D2–D3 Complexed with FGF1 | | | | | | | | |
|---|---|---|---|---|---|---|---|---|
| ATOM | 3512 | N | LEU | 2359 | −19.524 | 20.709 | 21.661 | 1.00 | 29.50 |
| ATOM | 3513 | CA | LEU | 2359 | −19.960 | 19.576 | 22.466 | 1.00 | 29.73 |
| ATOM | 3514 | CB | LEU | 2359 | −19.235 | 19.650 | 23.817 | 1.00 | 28.52 |
| ATOM | 3515 | CG | LEU | 2359 | −17.709 | 19.655 | 23.682 | 1.00 | 24.43 |
| ATOM | 3516 | CD1 | LEU | 2359 | −17.073 | 19.819 | 25.063 | 1.00 | 22.37 |
| ATOM | 3517 | CD2 | LEU | 2359 | −17.264 | 18.353 | 22.992 | 1.00 | 18.11 |
| ATOM | 3518 | C | LEU | 2359 | −21.480 | 19.460 | 22.670 | 1.00 | 30.02 |
| ATOM | 3519 | O | LEU | 2359 | −22.142 | 20.532 | 22.683 | 1.00 | 29.26 |
| ATOM | 3520 | CB | ASN | 3147 | −34.933 | 22.064 | 55.418 | 1.00 | 44.07 |
| ATOM | 3521 | CG | ASN | 3147 | −36.079 | 21.137 | 55.075 | 1.00 | 49.07 |
| ATOM | 3522 | OD1 | ASN | 3147 | −35.963 | 19.925 | 55.207 | 1.00 | 51.17 |
| ATOM | 3523 | ND2 | ASN | 3147 | −37.193 | 21.708 | 54.646 | 1.00 | 49.27 |
| ATOM | 3524 | C | ASN | 3147 | −33.835 | 22.292 | 57.692 | 1.00 | 40.45 |
| ATOM | 3525 | O | ASN | 3147 | −33.964 | 21.572 | 58.683 | 1.00 | 40.68 |
| ATOM | 3526 | N | ASN | 3147 | −35.269 | 24.112 | 56.758 | 1.00 | 42.01 |
| ATOM | 3527 | CA | ASN | 3147 | −35.056 | 22.641 | 56.832 | 1.00 | 42.43 |
| ATOM | 3528 | N | ARG | 3148 | −32.658 | 22.799 | 57.342 | 1.00 | 37.62 |
| ATOM | 3529 | CA | ARG | 3148 | −31.470 | 22.483 | 58.148 | 1.00 | 36.21 |
| ATOM | 3530 | CB | ARG | 3148 | −30.346 | 21.952 | 57.257 | 1.00 | 34.96 |
| ATOM | 3531 | C | ARG | 3148 | −30.943 | 23.632 | 59.017 | 1.00 | 35.42 |
| ATOM | 3532 | O | ARG | 3148 | −31.315 | 24.798 | 58.836 | 1.00 | 36.26 |
| ATOM | 3533 | N | MET | 3149 | −30.101 | 23.277 | 59.987 | 1.00 | 31.28 |
| ATOM | 3534 | CA | MET | 3149 | −29.501 | 24.245 | 60.908 | 1.00 | 27.15 |
| ATOM | 3535 | CB | MET | 3149 | −28.481 | 23.554 | 61.808 | 1.00 | 28.45 |
| ATOM | 3536 | CG | MET | 3149 | −27.849 | 24.460 | 62.865 | 1.00 | 27.74 |
| ATOM | 3537 | D | MET | 3149 | −28.961 | 24.797 | 64.250 | 1.00 | 29.90 |
| ATOM | 3538 | CE | MET | 3149 | −28.319 | 26.362 | 64.772 | 1.00 | 26.73 |
| ATOM | 3539 | C | MET | 3149 | −28.806 | 25.378 | 60.171 | 1.00 | 23.68 |
| ATOM | 3540 | O | MET | 3149 | −27.832 | 25.153 | 59.462 | 1.00 | 24.57 |
| ATOM | 3541 | N | PRO | 3150 | −29.275 | 26.619 | 60.360 | 1.00 | 21.74 |
| ATOM | 3542 | CD | PRO | 3150 | −30.432 | 27.035 | 61.174 | 1.00 | 19.77 |
| ATOM | 3543 | CA | PRO | 3150 | −28.667 | 27.770 | 59.684 | 1.00 | 17.93 |
| ATOM | 3544 | CE | PRO | 3150 | −29.414 | 28.956 | 60.293 | 1.00 | 20.02 |
| ATOM | 3545 | CG | PRO | 3150 | −30.789 | 28.377 | 60.555 | 1.00 | 17.09 |
| ATOM | 3546 | C | PRO | 3150 | −27.163 | 27.877 | 59.863 | 1.00 | 13.71 |
| ATOM | 3547 | O | PRO | 3150 | −26.635 | 27.611 | 60.938 | 1.00 | 17.01 |
| ATOM | 3548 | N | VAL | 3151 | −26.474 | 28.248 | 58.791 | 1.00 | 12.06 |
| ATOM | 3549 | CA | VAL | 3151 | −25.019 | 28.410 | 58.810 | 1.00 | 11.74 |
| ATOM | 3550 | CB | VAL | 3151 | −24.276 | 27.099 | 58.419 | 1.00 | 9.82 |
| ATOM | 3551 | CG1 | VAL | 3151 | −22.767 | 27.358 | 58.290 | 1.00 | 2.10 |
| ATOM | 3552 | CG2 | VAL | 3151 | −24.539 | 26.019 | 59.467 | 1.00 | 7.23 |
| ATOM | 3553 | C | VAL | 3151 | −24.582 | 29.501 | 57.840 | 1.00 | 13.11 |
| ATOM | 3554 | O | VAL | 3151 | −24.724 | 29.355 | 56.622 | 1.00 | 12.79 |
| ATOM | 3555 | N | ALA | 3152 | −24.052 | 30.597 | 58.374 | 1.00 | 13.16 |
| ATOM | 3556 | CA | ALA | 3152 | −23.599 | 31.686 | 57.507 | 1.00 | 14.26 |
| ATOM | 3557 | CB | ALA | 3152 | −23.067 | 32.847 | 58.340 | 1.00 | 7.04 |
| ATOM | 3558 | C | ALA | 3152 | −22.519 | 31.170 | 56.535 | 1.00 | 13.45 |
| ATOM | 3559 | O | ALA | 3152 | −21.733 | 30.291 | 56.869 | 1.00 | 12.84 |
| ATOM | 3560 | N | PRO | 3153 | −22.481 | 31.717 | 55.315 | 1.00 | 15.40 |
| ATOM | 3561 | CD | PRO | 3153 | −23.320 | 32.814 | 54.796 | 1.00 | 14.82 |
| ATOM | 3562 | CA | PRO | 3153 | −21.498 | 31.292 | 54.318 | 1.00 | 16.14 |
| ATOM | 3563 | CB | PRO | 3153 | −21.883 | 32.114 | 53.089 | 1.00 | 16.95 |
| ATOM | 3564 | CG | PRO | 3153 | −22.470 | 33.360 | 53.690 | 1.00 | 17.38 |
| ATOM | 3565 | C | PRO | 3153 | −20.051 | 31.491 | 54.733 | 1.00 | 17.05 |
| ATOM | 3566 | O | PRO | 3153 | −19.689 | 32.528 | 55.275 | 1.00 | 16.99 |
| ATOM | 3567 | N | TYR | 3154 | −19.227 | 30.485 | 54.456 | 1.00 | 21.23 |
| ATOM | 3568 | CA | TYR | 3154 | −17.807 | 30.516 | 54.797 | 1.00 | 20.93 |
| ATOM | 3569 | CB | TYR | 3154 | −17.579 | 29.793 | 56.105 | 1.00 | 19.47 |
| ATOM | 3570 | CG | TYR | 3154 | −17.999 | 28.351 | 56.035 | 1.00 | 17.48 |
| ATOM | 3571 | CD1 | TYR | 3154 | −19.340 | 28.006 | 55.910 | 1.00 | 14.81 |
| ATOM | 3572 | CE1 | TYR | 3154 | −19.732 | 26.680 | 55.837 | 1.00 | 18.14 |
| ATOM | 3573 | CD2 | TYR | 3154 | −17.051 | 27.327 | 56.082 | 1.00 | 18.77 |
| ATOM | 3574 | CE2 | TYR | 3154 | −17.432 | 25.987 | 56.010 | 1.00 | 17.16 |
| ATOM | 3575 | GZ | TYR | 3154 | −18.770 | 25.672 | 55.888 | 1.00 | 19.28 |
| ATOM | 3576 | OH | TYR | 3154 | −19.146 | 24.352 | 55.828 | 1.00 | 21.94 |
| ATOM | 3577 | C | TYR | 3154 | −16.947 | 29.848 | 53.737 | 1.00 | 22.24 |
| ATOM | 3578 | O | TYR | 3154 | −17.401 | 28.963 | 53.015 | 1.00 | 24.32 |
| ATOM | 3579 | N | TRP | 3155 | −15.689 | 30.267 | 53.683 | 1.00 | 24.77 |
| ATOM | 3580 | CA | TRP | 3155 | −14.713 | 29.744 | 52.732 | 1.00 | 27.11 |
| ATOM | 3581 | CB | TRP | 3155 | −13.418 | 30.548 | 52.845 | 1.00 | 26.23 |
| ATOM | 3582 | CG | TRP | 3155 | −13.586 | 32.029 | 52.627 | 1.00 | 24.87 |
| ATOM | 3583 | CD2 | TRP | 3155 | −14.384 | 32.670 | 51.622 | 1.00 | 23.22 |
| ATOM | 3584 | CE2 | TRP | 3155 | −14.193 | 34.067 | 51.763 | 1.00 | 23.69 |
| ATOM | 3585 | CE3 | TRP | 3155 | −15.240 | 32.204 | 50.617 | 1.00 | 21.94 |
| ATOM | 3586 | CD1 | TRP | 3155 | −12.962 | 33.035 | 53.318 | 1.00 | 24.48 |
| ATOM | 3587 | NE1 | TRP | 3155 | −13.321 | 34.260 | 52.804 | 1.00 | 22.81 |
| ATOM | 3588 | CZ2 | TRP | 3155 | −14.830 | 35.003 | 50.932 | 1.00 | 21.14 |

TABLE 2-continued

| FGFR1 D2–D3 Complexed with FGF1 | | | | | | | | |
|---|---|---|---|---|---|---|---|---|
| ATOM | 3589 | CZ3 | TRP | 3155 | −15.872 | 33.135 | 49.789 | 1.00 | 21.61 |
| ATOM | 3590 | CH2 | TRP | 3155 | −15.661 | 34.519 | 49.954 | 1.00 | 22.70 |
| ATOM | 3591 | C | TRP | 3155 | −14.415 | 28.261 | 52.970 | 1.00 | 28.81 |
| ATOM | 3592 | O | TRP | 3155 | −14.352 | 27.804 | 54.108 | 1.00 | 29.07 |
| ATOM | 3593 | N | THR | 3156 | −14.221 | 27.520 | 51.886 | 1.00 | 31.49 |
| ATOM | 3594 | CA | THR | 3156 | −13.937 | 26.093 | 51.968 | 1.00 | 34.42 |
| ATOM | 3595 | CB | THR | 3156 | −14.935 | 25.292 | 51.097 | 1.00 | 36.07 |
| ATOM | 3596 | OG1 | THR | 3156 | −16.258 | 25.446 | 51.628 | 1.00 | 37.52 |
| ATOM | 3597 | CG2 | THR | 3156 | −14.574 | 23.812 | 51.068 | 1.00 | 38.45 |
| ATOM | 3598 | C | THR | 3156 | −12.515 | 25.811 | 51.496 | 1.00 | 36.62 |
| ATOM | 3599 | O | THR | 3156 | −12.059 | 24.672 | 51.493 | 1.00 | 38.31 |
| ATOM | 3600 | N | SER | 3157 | −11.809 | 26.859 | 51.100 | 1.00 | 38.06 |
| ATOM | 3601 | CA | SER | 3157 | −10.448 | 26.691 | 50.627 | 1.00 | 39.63 |
| ATOM | 3602 | CB | SER | 3157 | −10.474 | 26.163 | 49.192 | 1.00 | 42.04 |
| ATOM | 3603 | OG | SER | 3157 | −9.165 | 25.975 | 48.686 | 1.00 | 48.25 |
| ATOM | 3604 | C | SER | 3157 | −9.732 | 28.027 | 50.687 | 1.00 | 39.53 |
| ATOM | 3605 | O | SER | 3157 | −9.023 | 28.406 | 49.756 | 1.00 | 39.53 |
| ATOM | 3606 | N | PRO | 3158 | −9.894 | 28.750 | 51.807 | 1.00 | 40.33 |
| ATOM | 3607 | CD | PRO | 3158 | −10.415 | 28.203 | 53.072 | 1.00 | 38.84 |
| ATOM | 3608 | CA | PRO | 3158 | −9.283 | 30.066 | 52.031 | 1.00 | 41.05 |
| ATOM | 3609 | CB | PRO | 3158 | −9.298 | 30.193 | 53.552 | 1.00 | 39.82 |
| ATOM | 3610 | CG | PRO | 3158 | −10.514 | 29.428 | 53.933 | 1.00 | 39.18 |
| ATOM | 3611 | C | PRO | 3158 | −7.873 | 30.157 | 51.463 | 1.00 | 41.84 |
| ATOM | 3612 | O | PRO | 3158 | −7.460 | 31.194 | 50.938 | 1.00 | 40.53 |
| ATOM | 3613 | N | ALA | 3159 | −7.144 | 29.055 | 51.577 | 1.00 | 42.89 |
| ATOM | 3614 | CA | ALA | 3159 | −5.783 | 28.990 | 51.084 | 1.00 | 44.47 |
| ATOM | 3615 | CB | ALA | 3159 | −5.269 | 27.557 | 51.180 | 1.00 | 46.15 |
| ATOM | 3616 | C | ALA | 3159 | −5.727 | 29.475 | 49.641 | 1.00 | 44.76 |
| ATOM | 3617 | O | ALA | 3159 | −5.175 | 30.545 | 49.353 | 1.00 | 44.96 |
| ATOM | 3618 | N | ALA | 3160 | −6.312 | 28.685 | 48.743 | 1.00 | 42.87 |
| ATOM | 3619 | CA | ALA | 3160 | −6.328 | 29.011 | 47.324 | 1.00 | 42.85 |
| ATOM | 3620 | CB | ALA | 3160 | −7.370 | 28.152 | 46.607 | 1.00 | 41.03 |
| ATOM | 3621 | C | ALA | 3160 | −6.592 | 30.493 | 47.050 | 1.00 | 43.30 |
| ATOM | 3622 | O | ALA | 3160 | −6.115 | 31.035 | 46.050 | 1.00 | 46.42 |
| ATOM | 3623 | N | MET | 3161 | −7.328 | 31.153 | 47.942 | 1.00 | 41.04 |
| ATOM | 3624 | CA | MET | 3161 | −7.666 | 32.560 | 47.756 | 1.00 | 38.29 |
| ATOM | 3625 | CB | MET | 3161 | −8.936 | 32.890 | 48.545 | 1.00 | 36.52 |
| ATOM | 3626 | CG | MET | 3161 | −10.049 | 31.857 | 48.369 | 1.00 | 34.13 |
| ATOM | 3627 | SD | MET | 3161 | −11.553 | 32.242 | 49.278 | 1.00 | 30.96 |
| ATOM | 3628 | CE | MET | 3161 | −12.721 | 31.294 | 48.415 | 1.00 | 36.88 |
| ATOM | 3629 | C | MET | 3161 | −6.557 | 33.548 | 48.119 | 1.00 | 38.60 |
| ATOM | 3630 | O | MET | 3161 | −6.658 | 34.733 | 47.804 | 1.00 | 38.63 |
| ATOM | 3631 | N | ALA | 3162 | −5.499 | 33.066 | 48.766 | 1.00 | 38.98 |
| ATOM | 3632 | CA | ALA | 3162 | −4.386 | 33.932 | 49.166 | 1.00 | 37.98 |
| ATOM | 3633 | CB | ALA | 3162 | −3.288 | 33.097 | 49.821 | 1.00 | 40.89 |
| ATOM | 3634 | C | ALA | 3162 | −3.816 | 34.711 | 47.978 | 1.00 | 36.26 |
| ATOM | 3635 | O | ALA | 3162 | −3.553 | 35.911 | 48.081 | 1.00 | 34.15 |
| ATOM | 3636 | N | LYS | 3163 | −3.619 | 34.011 | 46.860 | 1.00 | 34.79 |
| ATOM | 3637 | CA | LYS | 3163 | −3.105 | 34.602 | 45.621 | 1.00 | 32.71 |
| ATOM | 3638 | CB | LYS | 3163 | −2.867 | 33.483 | 44.608 | 1.00 | 29.79 |
| ATOM | 3639 | CG | LYS | 3163 | −2.416 | 33.927 | 43.247 | 1.00 | 30.82 |
| ATOM | 3640 | CD | LYS | 3163 | −2.410 | 32.742 | 42.276 | 1.00 | 33.00 |
| ATOM | 3641 | CE | LYS | 3163 | −2.244 | 33.211 | 40.818 | 1.00 | 36.76 |
| ATOM | 3642 | NZ | LYS | 3163 | −2.375 | 32.119 | 39.797 | 1.00 | 33.68 |
| ATOM | 3643 | C | LYS | 3163 | −4.181 | 35.574 | 45.109 | 1.00 | 33.81 |
| ATOM | 3644 | O | LYS | 3163 | −5.115 | 35.165 | 44.407 | 1.00 | 32.40 |
| ATOM | 3645 | N | ALA | 3164 | −4.045 | 36.855 | 45.467 | 1.00 | 32.72 |
| ATOM | 3646 | CA | ALA | 3164 | −5.022 | 37.877 | 45.099 | 1.00 | 30.74 |
| ATOM | 3647 | CB | ALA | 3164 | −4.965 | 39.035 | 46.094 | 1.00 | 28.25 |
| ATOM | 3648 | C | ALA | 3164 | −4.900 | 38.409 | 43.680 | 1.00 | 31.97 |
| ATOM | 3649 | O | ALA | 3164 | −5.902 | 38.594 | 42.977 | 1.00 | 31.00 |
| ATOM | 3650 | N | LEU | 3165 | −3.678 | 38.659 | 43.244 | 1.00 | 32.83 |
| ATOM | 3651 | CA | LEU | 3165 | −3.494 | 39.182 | 41.895 | 1.00 | 34.12 |
| ATOM | 3652 | CB | LEU | 3165 | −2.321 | 40.164 | 41.864 | 1.00 | 31.66 |
| ATOM | 3653 | CG | LEU | 3165 | −1.902 | 40.675 | 40.489 | 1.00 | 29.85 |
| ATOM | 3654 | CD1 | LEU | 3165 | −3.047 | 41.426 | 39.852 | 1.00 | 28.92 |
| ATOM | 3655 | CD2 | LEU | 3165 | −0.692 | 41.575 | 40.636 | 1.00 | 32.73 |
| ATOM | 3656 | C | LEU | 3165 | −3.274 | 38.098 | 40.838 | 1.00 | 35.09 |
| ATOM | 3657 | O | LEU | 3165 | −2.440 | 37.200 | 40.994 | 1.00 | 35.48 |
| ATOM | 3658 | N | HIS | 3166 | −4.040 | 38.190 | 39.758 | 1.00 | 35.16 |
| ATOM | 3659 | CA | HIS | 3166 | −3.915 | 37.254 | 38.655 | 1.00 | 33.65 |
| ATOM | 3660 | CB | HIS | 3166 | −5.265 | 36.610 | 38.323 | 1.00 | 33.18 |
| ATOM | 3661 | CG | HIS | 3166 | −5.591 | 35.420 | 39.168 | 1.00 | 33.75 |
| ATOM | 3662 | CD2 | HIS | 3166 | −5.711 | 34.109 | 38.849 | 1.00 | 34.10 |
| ATOM | 3663 | ND1 | HIS | 3166 | −5.840 | 35.509 | 40.520 | 1.00 | 34.52 |
| ATOM | 3664 | CE1 | HIS | 3166 | −6.100 | 34.305 | 41.000 | 1.00 | 33.44 |
| ATOM | 3665 | NE2 | HIS | 3166 | −6.028 | 33.439 | 40.007 | 1.00 | 33.69 |

TABLE 2-continued

| | | | FGFR1 D2–D3 Complexed with FGF1 | | | | | |
|---|---|---|---|---|---|---|---|---|
| ATOM | 3666 | C | HIS | 3166 | −3.387 | 37.992 | 37.434 | 1.00 | 32.45 |
| ATOM | 3667 | O | HIS | 3166 | −4.116 | 38.715 | 36.750 | 1.00 | 31.98 |
| ATOM | 3668 | N | ALA | 3167 | −2.101 | 37.833 | 37.175 | 1.00 | 30.77 |
| ATOM | 3669 | CA | ALA | 3167 | −1.513 | 38.471 | 36.016 | 1.00 | 30.62 |
| ATOM | 3670 | CB | ALA | 3167 | −0.104 | 38.959 | 36.336 | 1.00 | 29.94 |
| ATOM | 3671 | C | ALA | 3167 | −1.496 | 37.405 | 34.920 | 1.00 | 29.25 |
| ATOM | 3672 | O | ALA | 3167 | −0.961 | 36.311 | 35.105 | 1.00 | 30.60 |
| ATOM | 3673 | N | VAL | 3168 | −2.094 | 37.722 | 33.781 | 1.00 | 26.81 |
| ATOM | 3674 | CA | VAL | 3168 | −2.164 | 36.769 | 32.684 | 1.00 | 24.17 |
| ATOM | 3675 | CB | VAL | 3168 | −3.602 | 36.150 | 32.624 | 1.00 | 23.29 |
| ATOM | 3676 | CG1 | VAL | 3168 | −4.154 | 36.141 | 31.198 | 1.00 | 22.64 |
| ATOM | 3677 | CG2 | VAL | 3168 | −3.574 | 34.757 | 33.180 | 1.00 | 19.45 |
| ATOM | 3678 | C | VAL | 3168 | −1.796 | 37.364 | 31.325 | 1.00 | 23.88 |
| ATOM | 3679 | O | VAL | 3168 | −2.079 | 38.534 | 31.028 | 1.00 | 23.24 |
| ATOM | 3680 | N | PRO | 3169 | −1.126 | 36.574 | 30.483 | 1.00 | 22.93 |
| ATOM | 3681 | CD | PRO | 3169 | −0.561 | 35.222 | 30.633 | 1.00 | 21.77 |
| ATOM | 3682 | CA | PRO | 3169 | −0.796 | 37.148 | 29.180 | 1.00 | 23.68 |
| ATOM | 3683 | CB | PRO | 3169 | 0.281 | 36.200 | 28.651 | 1.00 | 22.17 |
| ATOM | 3684 | CG | PRO | 3169 | −0.140 | 34.884 | 29.203 | 1.00 | 19.69 |
| ATOM | 3685 | C | PRO | 3169 | −2.093 | 37.132 | 28.344 | 1.00 | 23.78 |
| ATOM | 3686 | O | PRO | 3169 | −2.878 | 36.172 | 28.397 | 1.00 | 21.15 |
| ATOM | 3687 | N | ALA | 3170 | −2.326 | 38.204 | 27.597 | 1.00 | 23.56 |
| ATOM | 3688 | CA | ALA | 3170 | −3.525 | 38.315 | 26.773 | 1.00 | 21.30 |
| ATOM | 3689 | CB | ALA | 3170 | −3.358 | 39.449 | 25.776 | 1.00 | 18.95 |
| ATOM | 3690 | C | ALA | 3170 | −3.833 | 37.022 | 26.036 | 1.00 | 20.56 |
| ATOM | 3691 | O | ALA | 3170 | −2.917 | 36.315 | 25.595 | 1.00 | 19.94 |
| ATOM | 3692 | N | ALA | 3171 | −5.126 | 36.710 | 25.932 | 1.00 | 19.85 |
| ATOM | 3693 | CA | ALA | 3171 | −5.601 | 35.519 | 25.221 | 1.00 | 18.11 |
| ATOM | 3694 | CB | ALA | 3171 | −4.642 | 35.165 | 24.078 | 1.00 | 15.17 |
| ATOM | 3695 | C | ALA | 3171 | −5.834 | 34.295 | 26.081 | 1.00 | 17.89 |
| ATOM | 3696 | O | ALA | 3171 | −6.490 | 33.349 | 25.655 | 1.00 | 21.43 |
| ATOM | 3697 | N | ALA | 3172 | −5.296 | 34.290 | 27.287 | 1.00 | 18.71 |
| ATOM | 3698 | CA | ALA | 3172 | −5.489 | 33.137 | 28.140 | 1.00 | 18.57 |
| ATOM | 3699 | CB | ALA | 3172 | −4.399 | 33.084 | 29.188 | 1.00 | 15.97 |
| ATOM | 3700 | C | ALA | 317 | −6.867 | 33.173 | 28.797 | 1.00 | 21.38 |
| ATOM | 3701 | O | ALA | 3172 | −7.439 | 34.243 | 29.019 | 1.00 | 22.10 |
| ATOM | 3702 | N | THR | 3173 | −7.416 | 31.989 | 29.065 | 1.00 | 24.31 |
| ATOM | 3703 | CA | THR | 3173 | −8.710 | 31.876 | 29.740 | 1.00 | 23.82 |
| ATOM | 3704 | CB | THR | 3173 | −9.343 | 30.465 | 29.550 | 1.00 | 23.64 |
| ATOM | 3705 | OG1 | THR | 3173 | −9.900 | 30.368 | 28.234 | 1.00 | 26.07 |
| ATOM | 3706 | CG2 | THR | 3173 | −10.449 | 30.206 | 30.584 | 1.00 | 20.22 |
| ATOM | 3707 | C | THR | 3173 | −8.402 | 32.092 | 31.219 | 1.00 | 22.88 |
| ATOM | 3708 | O | THR | 3173 | −7.450 | 31.521 | 31.752 | 1.00 | 23.50 |
| ATOM | 3709 | N | VAL | 3174 | −9.196 | 32.921 | 31.877 | 1.00 | 19.83 |
| ATOM | 3710 | CA | VAL | 3174 | −8.976 | 33.200 | 33.282 | 1.00 | 16.83 |
| ATOM | 3711 | CB | VAL | 3174 | −8.822 | 34.708 | 33.493 | 1.00 | 15.67 |
| ATOM | 3712 | CG1 | VAL | 3174 | −9.055 | 35.062 | 34.940 | 1.00 | 17.37 |
| ATOM | 3713 | CG2 | VAL | 3174 | −7.450 | 35.143 | 33.052 | 1.00 | 12.57 |
| ATOM | 3714 | C | VAL | 3174 | −10.140 | 32.711 | 34.117 | 1.00 | 17.52 |
| ATOM | 3715 | O | VAL | 3174 | −11.284 | 33.032 | 33.810 | 1.00 | 21.82 |
| ATOM | 3716 | N | ALA | 3175 | −9.862 | 31.935 | 35.161 | 1.00 | 16.14 |
| ATOM | 3717 | CA | ALA | 3175 | −10.931 | 31.458 | 36.048 | 1.00 | 17.44 |
| ATOM | 3718 | CB | ALA | 3175 | −10.977 | 29.935 | 36.044 | 1.00 | 14.62 |
| ATOM | 3719 | C | ALA | 3175 | −10.715 | 31.983 | 37.483 | 1.00 | 19.37 |
| ATOM | 3720 | O | ALA | 3175 | −9.577 | 32.116 | 37.936 | 1.00 | 21.07 |
| ATOM | 3721 | N | PHE | 3176 | −11.803 | 32.316 | 38.180 | 1.00 | 21.52 |
| ATOM | 3722 | CA | PHE | 3176 | −11.730 | 32.800 | 39.572 | 1.00 | 22.20 |
| ATOM | 3723 | CB | PHE | 3176 | −12.181 | 34.271 | 39.710 | 1.00 | 21.08 |
| ATOM | 3724 | CG | PHE | 3176 | −11.178 | 35.263 | 39.195 | 1.00 | 17.44 |
| ATOM | 3725 | CD1 | PHE | 3176 | −9.820 | 35.061 | 39.403 | 1.00 | 13.20 |
| ATOM | 3726 | CD2 | PHE | 3176 | −11.590 | 36.378 | 38.471 | 1.00 | 19.12 |
| ATOM | 3727 | CE1 | PHE | 3176 | −8.881 | 35.945 | 38.896 | 1.00 | 15.24 |
| ATOM | 3728 | CE2 | PHE | 3176 | −10.652 | 37.282 | 37.951 | 1.00 | 20.36 |
| ATOM | 3729 | CZ | PHE | 3176 | −9.292 | 37.062 | 38.164 | 1.00 | 18.37 |
| ATOM | 3730 | C | PHE | 3176 | −12.613 | 31.932 | 40.453 | 1.00 | 23.14 |
| ATOM | 3731 | O | PHE | 3176 | −13.757 | 31.657 | 40.123 | 1.00 | 25.48 |
| ATOM | 3732 | N | ALA | 3177 | −12.092 | 31.517 | 41.592 | 1.00 | 24.72 |
| ATOM | 3733 | CA | ALA | 3177 | −12.860 | 30.652 | 42.460 | 1.00 | 26.07 |
| ATOM | 3734 | CB | ALA | 3177 | −12.216 | 29.256 | 42.483 | 1.00 | 25.30 |
| ATOM | 3735 | C | ALA | 3177 | −13.022 | 31.175 | 43.879 | 1.00 | 27.27 |
| ATOM | 3736 | O | ALA | 3177 | −12.136 | 31.830 | 44.440 | 1.00 | 26.09 |
| ATOM | 3737 | N | CYS | 3178 | −14.177 | 30.866 | 44.447 | 1.00 | 26.85 |
| ATOM | 3738 | CA | CYS | 3178 | −14.508 | 31.249 | 45.799 | 1.00 | 26.83 |
| ATOM | 3739 | C | CYS | 3178 | −15.230 | 30.059 | 46.399 | 1.00 | 26.94 |
| ATOM | 3740 | O | CYS | 3178 | −16.431 | 30.116 | 46.671 | 1.00 | 27.90 |
| ATOM | 3741 | CB | CYS | 3178 | −15.418 | 32.490 | 45.811 | 1.00 | 27.91 |
| ATOM | 3742 | SG | CYS | 3178 | −14.573 | 34.029 | 45.310 | 1.00 | 34.46 |

TABLE 2-continued

FGFR1 D2–D3 Complexed with FGF1

| ATOM | 3743 | N | PRO | 3179 | −14.520 | 28.936 | 46.563 | 1.00 | 26.83 |
|---|---|---|---|---|---|---|---|---|---|
| ATOM | 3744 | CD | PRO | 3179 | −13.163 | 28.607 | 46.096 | 1.00 | 24.75 |
| ATOM | 3745 | CA | PRO | 3179 | −15.180 | 27.763 | 47.150 | 1.00 | 28.17 |
| ATOM | 3746 | CB | PRO | 3179 | −14.031 | 26.784 | 47.344 | 1.00 | 26.22 |
| ATOM | 3747 | CG | PRO | 3179 | −13.171 | 27.086 | 46.151 | 1.00 | 27.38 |
| ATOM | 3748 | C | PRO | 3179 | −15.828 | 28.181 | 48.473 | 1.00 | 29.86 |
| ATOM | 3749 | O | PRO | 3179 | −15.203 | 28.851 | 49.308 | 1.00 | 30.65 |
| ATOM | 3750 | N | SER | 3180 | −17.082 | 27.802 | 48.662 | 1.00 | 28.44 |
| ATOM | 3751 | CA | SER | 3180 | −17.771 | 28.188 | 49.873 | 1.00 | 28.03 |
| ATOM | 3752 | CB | SER | 3180 | −18.368 | 29.578 | 49.710 | 1.00 | 30.25 |
| ATOM | 3753 | OG | SER | 3180 | −17.374 | 30.494 | 49.298 | 1.00 | 35.90 |
| ATOM | 3754 | C | SER | 3180 | −18.870 | 27.233 | 50.223 | 1.00 | 27.25 |
| ATOM | 3755 | O | SER | 3180 | −19.266 | 26.391 | 49.430 | 1.00 | 28.30 |
| ATOM | 3756 | N | SER | 3181 | −19.371 | 27.378 | 51.433 | 1.00 | 27.12 |
| ATOM | 3757 | CA | SER | 3181 | −20.441 | 26.530 | 51.890 | 1.00 | 27.21 |
| ATOM | 3758 | CB | SER | 3181 | −19.862 | 25.312 | 52.612 | 1.00 | 29.78 |
| ATOM | 3759 | OG | SER | 3181 | −20.880 | 24.385 | 52.940 | 1.00 | 35.40 |
| ATOM | 3760 | C | SER | 3181 | −21.294 | 27.366 | 52.827 | 1.00 | 25.72 |
| ATOM | 3761 | O | SER | 3181 | −20.961 | 28.518 | 53.126 | 1.00 | 23.32 |
| ATOM | 3762 | N | GLY | 3182 | −22.392 | 26.780 | 53.283 | 1.00 | 25.53 |
| ATOM | 3763 | CA | GLY | 3182 | −23.291 | 27.475 | 54.179 | 1.00 | 25.82 |
| ATOM | 3764 | C | GLY | 3182 | −24.686 | 26.946 | 53.961 | 1.00 | 25.46 |
| ATOM | 3765 | O | GLY | 3182 | −24.999 | 26.440 | 52.885 | 1.00 | 25.71 |
| ATOM | 3766 | N | THR | 3183 | −25.527 | 27.051 | 54.980 | 1.00 | 25.41 |
| ATOM | 3767 | CA | THR | 3183 | −26.889 | 26.569 | 54.864 | 1.00 | 24.64 |
| ATOM | 3768 | CB | THR | 3183 | −27.064 | 25.185 | 55.567 | 1.00 | 23.85 |
| ATOM | 3769 | OG1 | THR | 3183 | −27.889 | 25.318 | 56.727 | 1.00 | 25.02 |
| ATOM | 3770 | CG2 | THR | 3183 | −25.720 | 24.624 | 55.972 | 1.00 | 21.75 |
| ATOM | 3771 | C | THR | 3183 | −27.889 | 27.574 | 55.422 | 1.00 | 24.27 |
| ATOM | 3772 | O | THR | 3183 | −27.669 | 28.166 | 56.474 | 1.00 | 25.47 |
| ATOM | 3773 | N | PRO | 3184 | −28.986 | 27.816 | 54.686 | 1.00 | 25.01 |
| ATOM | 3774 | CD | PRO | 3184 | −30.069 | 28.743 | 55.036 | 1.00 | 24.48 |
| ATOM | 3775 | CA | PRO | 3184 | −29.250 | 27.171 | 53.393 | 1.00 | 23.19 |
| ATOM | 3776 | CB | PRO | 3184 | −30.614 | 27.724 | 53.004 | 1.00 | 21.27 |
| ATOM | 3777 | CG | PRO | 3184 | −30.648 | 29.052 | 53.681 | 1.00 | 25.55 |
| ATOM | 3778 | C | PRO | 3184 | −28.147 | 27.519 | 52.401 | 1.00 | 23.47 |
| ATOM | 3779 | O | PRO | 3184 | −27.450 | 28.519 | 52.571 | 1.00 | 21.98 |
| ATOM | 3780 | N | ASN | 3185 | −27.983 | 26.679 | 51.382 | 1.00 | 25.79 |
| ATOM | 3781 | CA | ASN | 3185 | −26.933 | 26.867 | 50.394 | 1.00 | 26.96 |
| ATOM | 3782 | CB | ASN | 3185 | −27.052 | 25.836 | 49.279 | 1.00 | 31.34 |
| ATOM | 3783 | CG | ASN | 3185 | −25.694 | 25.452 | 48.706 | 1.00 | 39.03 |
| ATOM | 3784 | OD1 | ASN | 3185 | −25.091 | 26.198 | 47.924 | 1.00 | 41.63 |
| ATOM | 3785 | ND2 | ASN | 3185 | −25.192 | 24.292 | 49.116 | 1.00 | 42.36 |
| ATOM | 3786 | C | ASN | 3185 | −26.929 | 28.262 | 49.817 | 1.00 | 25.86 |
| ATOM | 3787 | O | ASN | 3185 | −27.906 | 28.698 | 49.225 | 1.00 | 27.89 |
| ATOM | 3788 | N | PRO | 3186 | −25.811 | 28.981 | 49.984 | 1.00 | 24.67 |
| ATOM | 3789 | CD | PRO | 3186 | −24.632 | 28.493 | 50.723 | 1.00 | 24.39 |
| ATOM | 3790 | CA | PRO | 3186 | −25.596 | 30.351 | 49.517 | 1.00 | 25.60 |
| ATOM | 3791 | CB | PRO | 3186 | −24.317 | 30.761 | 50.241 | 1.00 | 25.99 |
| ATOM | 3792 | CG | PRO | 3186 | −23.568 | 29.479 | 50.326 | 1.00 | 24.50 |
| ATOM | 3793 | C | PRO | 3186 | −25.515 | 30.608 | 48.007 | 1.00 | 26.93 |
| ATOM | 3794 | O | PRO | 3186 | −25.245 | 29.710 | 47.197 | 1.00 | 26.83 |
| ATOM | 3795 | N | THR | 3187 | −25.738 | 31.876 | 47.675 | 1.00 | 23.65 |
| ATOM | 3796 | CA | THR | 3187 | −25.752 | 32.405 | 46.327 | 1.00 | 19.53 |
| ATOM | 3797 | CB | THR | 3187 | −26.787 | 33.531 | 46.263 | 1.00 | 19.53 |
| ATOM | 3798 | OG1 | THR | 3187 | −28.028 | 32.977 | 45.838 | 1.00 | 21.66 |
| ATOM | 3799 | CG2 | THR | 3187 | −26.355 | 34.664 | 45.348 | 1.00 | 19.57 |
| ATOM | 3800 | C | THR | 3187 | −24.390 | 32.921 | 45.883 | 1.00 | 20.94 |
| ATOM | 3801 | O | THR | 3187 | −23.563 | 33.303 | 46.714 | 1.00 | 22.44 |
| ATOM | 3802 | N | LEU | 3188 | −24.168 | 32.936 | 44.567 | 1.00 | 18.27 |
| ATOM | 3803 | CA | LEU | 3188 | −22.904 | 33.402 | 44.011 | 1.00 | 14.85 |
| ATOM | 3804 | CB | LEU | 3188 | −22.117 | 32.227 | 43.412 | 1.00 | 9.58 |
| ATOM | 3805 | CG | LEU | 3188 | −20.579 | 32.262 | 43.367 | 1.00 | 8.72 |
| ATOM | 3806 | CD1 | LEU | 3188 | −20.100 | 31.213 | 42.370 | 1.00 | 6.67 |
| ATOM | 3807 | CD2 | LEU | 3188 | −20.055 | 33.648 | 42.982 | 1.00 | 5.30 |
| ATOM | 3808 | C | LEU | 3188 | −23.130 | 34.454 | 42.929 | 1.00 | 15.82 |
| ATOM | 3809 | O | LEU | 3188 | −23.698 | 34.177 | 41.878 | 1.00 | 16.74 |
| ATOM | 3810 | N | ALA | 3189 | −22.666 | 35.662 | 43.199 | 1.00 | 15.51 |
| ATOM | 3811 | CA | ALA | 3189 | −22.780 | 36.761 | 42.262 | 1.00 | 14.78 |
| ATOM | 3812 | CB | ALA | 3189 | −23.719 | 37.826 | 42.820 | 1.00 | 9.44 |
| ATOM | 3813 | C | ALA | 3189 | −21.370 | 37.330 | 42.055 | 1.00 | 17.07 |
| ATOM | 3814 | O | ALA | 3189 | −20.496 | 37.188 | 42.915 | 1.00 | 16.25 |
| ATOM | 3815 | N | TRP | 3190 | −21.149 | 37.977 | 40.918 | 1.00 | 18.41 |
| ATOM | 3816 | CA | TRP | 3190 | −19.845 | 38.539 | 40.623 | 1.00 | 21.12 |
| ATOM | 3817 | CB | TRP | 3190 | −19.174 | 37.703 | 39.548 | 1.00 | 21.41 |
| ATOM | 3818 | CG | TRP | 3190 | −18.589 | 36.409 | 40.035 | 1.00 | 21.03 |
| ATOM | 3819 | CD2 | TRP | 3190 | −17.282 | 36.226 | 40.581 | 1.00 | 18.76 |

TABLE 2-continued

FGFR1 D2–D3 Complexed with FGF1

| ATOM | 3820 | CE2 | TRP | 3190 | −17.116 | 34.840 | 40.815 | 1.00 | 17.01 |
|---|---|---|---|---|---|---|---|---|---|
| ATOM | 3821 | CE3 | TRP | 3190 | −16.227 | 37.099 | 40.888 | 1.00 | 19.08 |
| ATOM | 3822 | CD1 | TRP | 3190 | −19.158 | 35.163 | 39.972 | 1.00 | 18.61 |
| ATOM | 3823 | NE1 | TRP | 3190 | −18.276 | 34.217 | 40.433 | 1.00 | 15.64 |
| ATOM | 3824 | CZ2 | TRP | 3190 | −15.936 | 34.304 | 41.343 | 1.00 | 15.99 |
| ATOM | 3825 | CZ3 | TRP | 3190 | −15.046 | 36.564 | 41.413 | 1.00 | 19.91 |
| ATOM | 3826 | CH2 | TRP | 3190 | −14.914 | 35.176 | 41.634 | 1.00 | 17.87 |
| ATOM | 3827 | C | TRP | 3190 | −19.868 | 40.005 | 40.188 | 1.00 | 22.99 |
| ATOM | 3828 | O | TRP | 3190 | −20.731 | 40.427 | 39.423 | 1.00 | 25.42 |
| ATOM | 3829 | N | LEU | 3191 | −18.895 | 40.772 | 40.668 | 1.00 | 24.94 |
| ATOM | 3830 | CA | LEU | 3191 | −18.794 | 42.193 | 40.355 | 1.00 | 26.37 |
| ATOM | 3831 | CB | LEU | 3191 | −18.926 | 43.023 | 41.642 | 1.00 | 25.49 |
| ATOM | 3832 | CG | LEU | 3191 | −20.162 | 42.870 | 42.541 | 1.00 | 28.84 |
| ATOM | 3833 | CD1 | LEU | 3191 | −20.127 | 43.967 | 43.607 | 1.00 | 28.14 |
| ATOM | 3834 | CD2 | LEU | 3191 | −21.447 | 42.979 | 41.728 | 1.00 | 27.31 |
| ATOM | 3835 | C | LEU | 3191 | −17.470 | 42.560 | 39.670 | 1.00 | 29.34 |
| ATOM | 3836 | O | LEU | 3191 | −16.453 | 41.874 | 39.821 | 1.00 | 31.79 |
| ATOM | 3837 | N | LYS | 3192 | −17.489 | 43.647 | 38.909 | 1.00 | 30.17 |
| ATOM | 3838 | CA | LYS | 3192 | −16.285 | 44.120 | 38.242 | 1.00 | 31.89 |
| ATOM | 3839 | CB | LYS | 3192 | −16.415 | 43.980 | 36.718 | 1.00 | 31.26 |
| ATOM | 3840 | CG | LYS | 3192 | −15.190 | 44.450 | 35.920 | 1.00 | 29.80 |
| ATOM | 3841 | CD | LYS | 3192 | −15.219 | 43.874 | 34.505 | 1.00 | 32.69 |
| ATOM | 3842 | CE | LYS | 3192 | −14.429 | 44.713 | 33.485 | 1.00 | 34.71 |
| ATOM | 3843 | NZ | LYS | 3192 | −12.968 | 44.837 | 33.773 | 1.00 | 34.92 |
| ATOM | 3844 | C | LYS | 3192 | −16.137 | 45.582 | 38.656 | 1.00 | 33.72 |
| ATOM | 3845 | O | LYS | 3192 | −16.972 | 46.426 | 38.325 | 1.00 | 34.33 |
| ATOM | 3846 | N | ASN | 3193 | −15.086 | 45.867 | 39.413 | 1.00 | 34.19 |
| ATOM | 3847 | CA | ASN | 3193 | −14.837 | 47.218 | 39.893 | 1.00 | 36.46 |
| ATOM | 3848 | CB | ASN | 3193 | −14.382 | 48.111 | 38.740 | 1.00 | 35.57 |
| ATOM | 3849 | CG | ASH | 3193 | −13.214 | 47.526 | 37.978 | 1.00 | 37.77 |
| ATOM | 3850 | OD1 | ASH | 3193 | −12.219 | 47.108 | 38.567 | 1.00 | 39.10 |
| ATOM | 3851 | ND2 | ASH | 3193 | −13.326 | 47.498 | 36.657 | 1.00 | 40.56 |
| ATOM | 3852 | C | ASN | 3193 | −16.069 | 47.834 | 40.575 | 1.00 | 37.56 |
| ATOM | 3853 | O | ASN | 3193 | −16.462 | 48.962 | 40.271 | 1.00 | 41.08 |
| ATOM | 3854 | N | GLY | 3194 | −16.685 | 47.090 | 41.488 | 1.00 | 34.84 |
| ATOM | 3855 | CA | GLY | 3194 | −17.833 | 47.615 | 42.201 | 1.00 | 33.97 |
| ATOM | 3856 | C | GLY | 3194 | −19.197 | 47.440 | 41.565 | 1.00 | 35.07 |
| ATOM | 3857 | O | GLY | 3194 | −20.161 | 47.117 | 42.258 | 1.00 | 34.48 |
| ATOM | 3858 | N | ALA | 3195 | −19.297 | 47.657 | 40.260 | 1.00 | 35.47 |
| ATOM | 3859 | CA | ALA | 3195 | −20.586 | 47.523 | 39.585 | 1.00 | 36.44 |
| ATOM | 3860 | CB | ALA | 3195 | −20.598 | 48.366 | 38.309 | 1.00 | 34.68 |
| ATOM | 3861 | C | ALA | 3195 | −20.904 | 46.066 | 39.255 | 1.00 | 36.34 |
| ATOM | 3862 | O | ALA | 3195 | −20.033 | 45.194 | 39.332 | 1.00 | 34.71 |
| ATOM | 3863 | N | ALA | 3196 | −22.161 | 45.808 | 38.903 | 1.00 | 35.91 |
| ATOM | 3864 | CA | ALA | 3196 | −22.592 | 44.465 | 38.536 | 1.00 | 36.77 |
| ATOM | 3865 | CB | ALA | 3196 | −24.109 | 44.435 | 38.340 | 1.00 | 35.46 |
| ATOM | 3866 | C | ALA | 3196 | −21.880 | 44.093 | 37.235 | 1.00 | 37.93 |
| ATOM | 3867 | O | ALA | 3196 | −21.557 | 44.966 | 36.430 | 1.00 | 39.51 |
| ATOM | 3868 | N | PHE | 3197 | −21.634 | 42.804 | 37.026 | 1.00 | 38.80 |
| ATOM | 3869 | CA | PHE | 3197 | −20.939 | 42.344 | 35.826 | 1.00 | 38.95 |
| ATOM | 3870 | CB | PHE | 3197 | −19.657 | 41.607 | 36.220 | 1.00 | 38.39 |
| ATOM | 3871 | CG | PHE | 3197 | −18.768 | 41.252 | 35.059 | 1.00 | 40.65 |
| ATOM | 3872 | CD1 | PHE | 3197 | −18.057 | 40.049 | 35.055 | 1.00 | 41.69 |
| ATOM | 3873 | CD2 | PHE | 3197 | −18.597 | 42.133 | 33.991 | 1.00 | 42.76 |
| ATOM | 3874 | CE1 | PHE | 3197 | −17.182 | 39.721 | 34.004 | 1.00 | 41.49 |
| ATOM | 3875 | CE2 | PHE | 3197 | −17.728 | 41.822 | 32.935 | 1.00 | 42.78 |
| ATOM | 3876 | CZ | PHE | 3197 | −17.018 | 40.610 | 32.943 | 1.00 | 43.47 |
| ATOM | 3877 | C | PHE | 3197 | −21.817 | 41.401 | 35.022 | 1.00 | 40.42 |
| ATOM | 3878 | O | PHE | 3197 | −21.913 | 40.222 | 35.347 | 1.00 | 40.89 |
| ATOM | 3879 | N | ALA | 3198 | −22.468 | 41.910 | 33.981 | 1.00 | 40.45 |
| ATOM | 3880 | CA | ALA | 3198 | −23.311 | 41.057 | 33.149 | 1.00 | 40.04 |
| ATOM | 3881 | CB | ALA | 3198 | −24.511 | 41.849 | 32.614 | 1.00 | 39.13 |
| ATOM | 3882 | C | ALA | 3198 | −22.435 | 40.543 | 32.002 | 1.00 | 39.08 |
| ATOM | 3883 | O | ALA | 3198 | −21.550 | 41.254 | 31.530 | 1.00 | 37.45 |
| ATOM | 3884 | N | PRO | 3199 | −22.662 | 39.296 | 31.550 | 1.00 | 38.58 |
| ATOM | 3885 | CD | PRO | 3199 | −23.725 | 38.385 | 31.994 | 1.00 | 38.44 |
| ATOM | 3886 | CA | PRO | 3199 | −21.886 | 38.688 | 30.462 | 1.00 | 39.44 |
| ATOM | 3887 | CB | PRO | 3199 | −22.601 | 37.356 | 30.224 | 1.00 | 38.24 |
| ATOM | 3888 | CG | PRO | 3199 | −23.973 | 37.596 | 30.754 | 1.00 | 40.50 |
| ATOM | 3889 | C | PRO | 3199 | −21.737 | 39.521 | 29.190 | 1.00 | 39.48 |
| ATOM | 3890 | O | PRO | 3199 | −20.756 | 39.388 | 28.458 | 1.00 | 39.70 |
| ATOM | 3891 | N | ASP | 3200 | −22.699 | 40.396 | 28.939 | 1.00 | 40.10 |
| ATOM | 3892 | CA | ASP | 3200 | −22.660 | 41.248 | 27.757 | 1.00 | 39.53 |
| ATOM | 3893 | CB | ASP | 3200 | −24.061 | 41.776 | 27.485 | 1.00 | 41.17 |
| ATOM | 3894 | CG | ASP | 3200 | −25.128 | 40.902 | 28.414 | 1.00 | 46.36 |
| ATOM | 3895 | OD1 | ASP | 3200 | −25.218 | 39.708 | 27.744 | 1.00 | 48.73 |
| ATOM | 3896 | OD2 | ASP | 3200 | −25.865 | 41.403 | 28.995 | 1.00 | 47.90 |

TABLE 2-continued

FGFR1 D2–D3 Complexed with FGF1

| ATOM | 3897 | C | ASP | 3200 | −21.686 | 42.402 | 27.979 | 1.00 | 37.25 |
|---|---|---|---|---|---|---|---|---|---|
| ATOM | 3898 | O | ASP | 3200 | −21.412 | 43.182 | 27.071 | 1.00 | 35.42 |
| ATOM | 3899 | N | HIS | 3201 | −21.165 | 42.500 | 29.198 | 1.00 | 36.00 |
| ATOM | 3900 | CA | HIS | 3201 | −20.219 | 43.552 | 29.555 | 1.00 | 35.44 |
| ATOM | 3901 | CB | HIS | 3201 | −19.992 | 43.579 | 31.059 | 1.00 | 36.77 |
| ATOM | 3902 | CG | HIS | 3201 | −21.091 | 44.239 | 31.825 | 1.00 | 37.96 |
| ATOM | 3903 | CD2 | HIS | 3201 | −21.052 | 45.092 | 32.874 | 1.00 | 39.27 |
| ATOM | 3904 | ND1 | HIS | 3201 | −22.423 | 44.025 | 31.550 | 1.00 | 36.90 |
| ATOM | 3905 | CE1 | HIS | 3201 | −23.160 | 44.721 | 32.397 | 1.00 | 39.05 |
| ATOM | 3906 | NE2 | HIS | 3201 | −22.353 | 45.376 | 33.211 | 1.00 | 40.51 |
| ATOM | 3907 | C | HIS | 3201 | −18.878 | 43.361 | 28.882 | 1.00 | 34.44 |
| ATOM | 3908 | O | HIS | 3201 | −18.025 | 44.238 | 28.941 | 1.00 | 33.90 |
| ATOM | 3909 | N | ARG | 3202 | −18.684 | 42.208 | 28.256 | 1.00 | 33.68 |
| ATOM | 3910 | CA | ARG | 3202 | −17.420 | 41.932 | 27.592 | 1.00 | 32.76 |
| ATOM | 3911 | CB | ARG | 3202 | −16.428 | 41.326 | 28.579 | 1.00 | 28.87 |
| ATOM | 3912 | CG | ARG | 3202 | −16.799 | 39.929 | 29.043 | 1.00 | 27.45 |
| ATOM | 3913 | CD | ARG | 3202 | −15.666 | 39.314 | 29.833 | 1.00 | 24.91 |
| ATOM | 3914 | NE | ARG | 3202 | −14.431 | 39.318 | 29.059 | 1.00 | 23.34 |
| ATOM | 3915 | CZ | ARG | 3202 | −13.899 | 38.242 | 28.491 | 1.00 | 25.12 |
| ATOM | 3916 | NH1 | ARG | 3202 | −14.499 | 37.066 | 28.618 | 1.00 | 26.45 |
| ATOM | 3917 | NH2 | ARG | 3202 | −12.771 | 38.337 | 27.791 | 1.00 | 24.21 |
| ATOM | 3918 | C | ARG | 3202 | −17.594 | 40.971 | 26.433 | 1.00 | 34.21 |
| ATOM | 3919 | O | ARG | 3202 | −18.490 | 40.125 | 26.442 | 1.00 | 37.16 |
| ATOM | 3920 | N | ILE | 3203 | −16.731 | 41.095 | 25.433 | 1.00 | 33.29 |
| ATOM | 3921 | CA | ILE | 3203 | −16.800 | 40.198 | 24.295 | 1.00 | 32.59 |
| ATOM | 3922 | CB | ILE | 3203 | −15.846 | 40.635 | 23.173 | 1.00 | 32.07 |
| ATOM | 3923 | CG2 | ILE | 3203 | −16.124 | 39.824 | 21.909 | 1.00 | 28.91 |
| ATOM | 3924 | CG1 | ILE | 3203 | −16.034 | 42.129 | 22.899 | 1.00 | 29.28 |
| ATOM | 3925 | CD1 | ILE | 3203 | −15.099 | 42.673 | 21.856 | 1.00 | 29.62 |
| ATOM | 3926 | C | ILE | 3203 | −16.374 | 38.835 | 24.821 | 1.00 | 32.99 |
| ATOM | 3927 | O | ILE | 3203 | −15.434 | 38.729 | 25.608 | 1.00 | 33.73 |
| ATOM | 3928 | N | GLY | 3204 | −17.072 | 37.796 | 24.387 | 1.00 | 32.52 |
| ATOM | 3929 | CA | GLY | 3204 | −16.759 | 36.460 | 24.848 | 1.00 | 30.79 |
| ATOM | 3930 | C | GLY | 3204 | −17.756 | 36.066 | 25.918 | 1.00 | 31.96 |
| ATOM | 3931 | O | GLY | 3204 | −18.175 | 34.911 | 25.991 | 1.00 | 30.10 |
| ATOM | 3932 | N | GLY | 3205 | −18.150 | 37.039 | 26.740 | 1.00 | 32.74 |
| ATOM | 3933 | CA | GLY | 3205 | −19.100 | 36.775 | 27.808 | 1.00 | 32.98 |
| ATOM | 3934 | C | GLY | 3205 | −18.375 | 36.147 | 28.975 | 1.00 | 33.96 |
| ATOM | 3935 | O | GLY | 3205 | −17.243 | 36.536 | 29.277 | 1.00 | 35.51 |
| ATOM | 3936 | N | TYR | 3206 | −19.010 | 35.189 | 29.643 | 1.00 | 33.42 |
| ATOM | 3937 | CA | TYR | 3206 | −18.360 | 34.507 | 30.760 | 1.00 | 33.07 |
| ATOM | 3938 | CB | TYR | 3206 | −17.815 | 35.531 | 31.779 | 1.00 | 29.93 |
| ATOM | 3939 | CG | TYR | 3206 | −18.845 | 36.172 | 32.686 | 1.00 | 30.96 |
| ATOM | 3940 | CD1 | TYR | 3206 | −19.494 | 35.426 | 33.682 | 1.00 | 31.46 |
| ATOM | 3941 | CE1 | TYR | 3206 | −20.397 | 36.012 | 34.552 | 1.00 | 27.77 |
| ATOM | 3942 | CD2 | TYR | 3206 | −19.142 | 37.532 | 32.585 | 1.00 | 31.20 |
| ATOM | 3943 | CE2 | TYR | 3206 | −20.047 | 38.129 | 33.458 | 1.00 | 30.81 |
| ATOM | 3944 | CZ | TYR | 3206 | −20.667 | 37.356 | 34.436 | 1.00 | 31.02 |
| ATOM | 3945 | OH | TYR | 3206 | −21.549 | 37.919 | 35.317 | 1.00 | 35.48 |
| ATOM | 3946 | C | TYR | 3206 | −19.280 | 33.509 | 31.445 | 1.00 | 32.14 |
| ATOM | 3947 | O | TYR | 3206 | −20.448 | 33.787 | 31.672 | 1.00 | 32.65 |
| ATOM | 3948 | N | ALA | 3207 | −18.752 | 32.337 | 31.770 | 1.00 | 33.10 |
| ATOM | 3949 | CA | ALA | 3207 | −19.554 | 31.326 | 32.440 | 1.00 | 33.85 |
| ATOM | 3950 | CB | ALA | 3207 | −19.270 | 29.947 | 31.841 | 1.00 | 31.32 |
| ATOM | 3951 | C | ALA | 3207 | −19.266 | 31.321 | 33.944 | 1.00 | 35.21 |
| ATOM | 3952 | O | ALA | 3207 | −18.191 | 31.727 | 34.396 | 1.00 | 38.16 |
| ATOM | 3953 | N | VAL | 3208 | −20.245 | 30.871 | 34.716 | 1.00 | 34.20 |
| ATOM | 3954 | CA | VAL | 3208 | −20.107 | 30.776 | 36.160 | 1.00 | 32.45 |
| ATOM | 3955 | CB | VAL | 3208 | −21.056 | 31.767 | 36.885 | 1.00 | 30.98 |
| ATOM | 3956 | CG1 | VAL | 3208 | −20.906 | 31.625 | 38.392 | 1.00 | 33.08 |
| ATOM | 3957 | CG2 | VAL | 3208 | −20.753 | 33.183 | 36.455 | 1.00 | 28.98 |
| ATOM | 3958 | C | VAL | 3208 | −20.487 | 29.348 | 36.551 | 1.00 | 32.33 |
| ATOM | 3959 | O | VAL | 3208 | −21.647 | 28.960 | 36.446 | 1.00 | 34.87 |
| ATOM | 3960 | N | ALA | 3209 | −19.514 | 28.552 | 36.967 | 1.00 | 30.63 |
| ATOM | 3961 | CA | ALA | 3209 | −19.821 | 27.194 | 37.383 | 1.00 | 31.14 |
| ATOM | 3962 | CB | ALA | 3209 | −18.619 | 26.293 | 37.167 | 1.00 | 32.43 |
| ATOM | 3963 | C | ALA | 3209 | −20.212 | 27.232 | 38.864 | 1.00 | 31.16 |
| ATOM | 3964 | O | ALA | 3209 | −19.363 | 27.196 | 39.748 | 1.00 | 29.00 |
| ATOM | 3965 | N | TYR | 3210 | −21.509 | 27.315 | 39.126 | 1.00 | 33.46 |
| ATOM | 3966 | CA | TYR | 3210 | −21.997 | 27.371 | 40.494 | 1.00 | 36.52 |
| ATOM | 3967 | CB | TYR | 3210 | −23.525 | 27.484 | 40.498 | 1.00 | 36.08 |
| ATOM | 3968 | CG | TYR | 3210 | −24.012 | 28.661 | 39.682 | 1.00 | 42.00 |
| ATOM | 3969 | CD1 | TYR | 3210 | −24.258 | 28.533 | 38.312 | 1.00 | 43.49 |
| ATOM | 3970 | CE1 | TYR | 3210 | −24.632 | 29.639 | 37.536 | 1.00 | 44.89 |
| ATOM | 3971 | CD2 | TYR | 3210 | −24.155 | 29.926 | 40.262 | 1.00 | 44.22 |
| ATOM | 3972 | CE2 | TYR | 3210 | −24.528 | 31.040 | 39.496 | 1.00 | 45.78 |
| ATOM | 3973 | CZ | TYR | 3210 | −24.761 | 30.887 | 38.136 | 1.00 | 46.22 |

TABLE 2-continued

FGFR1 D2–D3 Complexed with FGF1

| ATOM | 3974 | OH | TYR | 3210 | −25.109 | 31.983 | 37.377 | 1.00 | 47.71 |
|---|---|---|---|---|---|---|---|---|---|
| ATOM | 3975 | C | TYR | 3210 | −21.537 | 26.169 | 41.320 | 1.00 | 36.86 |
| ATOM | 3976 | O | TYR | 3210 | −21.359 | 26.259 | 42.535 | 1.00 | 38.85 |
| ATOM | 3977 | N | ALA | 3211 | −21.319 | 25.043 | 40.665 | 1.00 | 35.89 |
| ATOM | 3978 | CA | ALA | 3211 | −20.884 | 23.873 | 41.395 | 1.00 | 34.71 |
| ATOM | 3979 | CB | ALA | 3211 | −20.942 | 22.654 | 40.489 | 1.00 | 36.35 |
| ATOM | 3980 | C | ALA | 3211 | −19.463 | 24.079 | 41.923 | 1.00 | 34.75 |
| ATOM | 3981 | O | ALA | 3211 | −19.112 | 23.608 | 43.002 | 1.00 | 33.71 |
| ATOM | 3982 | N | THR | 3212 | −18.656 | 24.813 | 41.167 | 1.00 | 34.33 |
| ATOM | 3983 | CA | THR | 3212 | −17.263 | 25.044 | 41.532 | 1.00 | 32.16 |
| ATOM | 3984 | CB | THR | 3212 | −16.363 | 24.782 | 40.332 | 1.00 | 34.28 |
| ATOM | 3985 | OG1 | THR | 3212 | −16.919 | 23.714 | 39.561 | 1.00 | 40.52 |
| ATOM | 3986 | CG2 | THR | 3212 | −14.969 | 24.386 | 40.784 | 1.00 | 34.26 |
| ATOM | 3987 | C | THR | 3212 | −16.965 | 26.449 | 42.032 | 1.00 | 30.76 |
| ATOM | 3988 | O | THR | 3212 | −15.818 | 26.881 | 42.020 | 1.00 | 27.65 |
| ATOM | 3989 | N | TRP | 3213 | −18.001 | 27.166 | 42.447 | 1.00 | 31.81 |
| ATOM | 3990 | CA | TRP | 3213 | −17.857 | 28.525 | 42.968 | 1.00 | 29.81 |
| ATOM | 3991 | CB | TRP | 3213 | −17.441 | 28.457 | 44.447 | 1.00 | 28.25 |
| ATOM | 3992 | CG | TRP | 3213 | −18.421 | 27.688 | 45.280 | 1.00 | 27.86 |
| ATOM | 3993 | CD2 | TRP | 3213 | −19.641 | 28.189 | 45.843 | 1.00 | 28.56 |
| ATOM | 3994 | CE2 | TRP | 3213 | −20.288 | 27.104 | 46.470 | 1.00 | 27.84 |
| ATOM | 3995 | CE3 | TRP | 3213 | −20.248 | 29.450 | 45.879 | 1.00 | 28.08 |
| ATOM | 3996 | CD1 | TRP | 3213 | −18.380 | 26.360 | 45.580 | 1.00 | 27.37 |
| ATOM | 3997 | NE1 | TRP | 3213 | −19.497 | 26.001 | 46.293 | 1.00 | 27.93 |
| ATOM | 3998 | CZ2 | TRP | 3213 | −21.516 | 27.240 | 47.123 | 1.00 | 29.13 |
| ATOM | 3999 | CZ3 | TRP | 3213 | −21.468 | 29.586 | 46.526 | 1.00 | 28.50 |
| ATOM | 4000 | CH2 | TRP | 3213 | −22.088 | 28.487 | 47.141 | 1.00 | 29.91 |
| ATOM | 4001 | C | TRP | 3213 | −16.877 | 29.390 | 42.167 | 1.00 | 29.53 |
| ATOM | 4002 | O | TRP | 3213 | −16.084 | 30.166 | 42.716 | 1.00 | 26.76 |
| ATOM | 4003 | N | SER | 3214 | −16.949 | 29.274 | 40.851 | 1.00 | 30.34 |
| ATOM | 4004 | CA | SER | 3214 | −16.047 | 30.048 | 40.018 | 1.00 | 31.47 |
| ATOM | 4005 | CB | SER | 3214 | −14.866 | 29.167 | 39.594 | 1.00 | 31.73 |
| ATOM | 4006 | OG | SER | 3214 | −15.322 | 27.911 | 39.137 | 1.00 | 34.16 |
| ATOM | 4007 | C | SER | 3214 | −16.691 | 30.688 | 38.792 | 1.00 | 30.14 |
| ATOM | 4008 | O | SER | 3214 | −17.837 | 30.396 | 38.442 | 1.00 | 30.07 |
| ATOM | 4009 | N | ILE | 3215 | −15.941 | 31.595 | 38.173 | 1.00 | 28.38 |
| ATOM | 4010 | CA | ILE | 3215 | −16.368 | 32.294 | 36.970 | 1.00 | 27.47 |
| ATOM | 4011 | CB | ILE | 3215 | −16.488 | 33.817 | 37.180 | 1.00 | 28.53 |
| ATOM | 4012 | CG2 | ILE | 3215 | −15.297 | 34.338 | 37.991 | 1.00 | 29.31 |
| ATOM | 4013 | CG1 | ILE | 3215 | −16.568 | 34.502 | 35.809 | 1.00 | 27.46 |
| ATOM | 4014 | CD1 | ILE | 3215 | −16.680 | 35.996 | 35.844 | 1.00 | 24.34 |
| ATOM | 4015 | C | ILE | 3215 | −15.279 | 32.049 | 35.945 | 1.00 | 27.26 |
| ATOM | 4016 | O | ILE | 3215 | −14.087 | 32.067 | 36.264 | 1.00 | 28.20 |
| ATOM | 4017 | N | ILE | 3216 | −15.677 | 31.832 | 34.707 | 1.00 | 25.77 |
| ATOM | 4018 | CA | ILE | 3216 | −14.691 | 31.556 | 33.690 | 1.00 | 26.67 |
| ATOM | 4019 | CB | ILE | 3216 | −14.832 | 30.099 | 33.197 | 1.00 | 26.81 |
| ATOM | 4020 | CG2 | ILE | 3216 | −13.809 | 29.809 | 32.118 | 1.00 | 28.49 |
| ATOM | 4021 | CG1 | ILE | 3216 | −14.615 | 29.144 | 34.373 | 1.00 | 28.35 |
| ATOM | 4022 | CD1 | ILE | 3216 | −14.607 | 27.674 | 34.002 | 1.00 | 26.95 |
| ATOM | 4023 | C | ILE | 3216 | −14.762 | 32.504 | 32.511 | 1.00 | 26.79 |
| ATOM | 4024 | O | ILE | 3216 | −15.796 | 32.579 | 31.828 | 1.00 | 24.85 |
| ATOM | 4025 | N | MET | 3217 | −13.654 | 33.214 | 32.277 | 1.00 | 25.00 |
| ATOM | 4026 | CA | MET | 3217 | −13.559 | 34.166 | 31.174 | 1.00 | 25.44 |
| ATOM | 4027 | CE | MET | 3217 | −13.172 | 35.562 | 31.672 | 1.00 | 25.70 |
| ATOM | 4028 | CG | MET | 3217 | −14.091 | 36.180 | 32.710 | 1.00 | 29.30 |
| ATOM | 4029 | SD | MET | 3217 | −13.594 | 37.900 | 33.045 | 1.00 | 33.66 |
| ATOM | 4030 | CE | MET | 3217 | −12.001 | 37.656 | 33.913 | 1.00 | 30.93 |
| ATOM | 4031 | C | MET | 3217 | −12.530 | 33.740 | 30.137 | 1.00 | 24.78 |
| ATOM | 4032 | O | MET | 3217 | −11.321 | 33.788 | 30.391 | 1.00 | 27.30 |
| ATOM | 4033 | N | ASP | 3218 | −13.006 | 33.336 | 28.964 | 1.00 | 22.50 |
| ATOM | 4034 | CA | ASP | 3218 | −12.108 | 32.936 | 27.892 | 1.00 | 20.29 |
| ATOM | 4035 | CB | ASP | 3218 | −12.861 | 32.100 | 26.846 | 1.00 | 23.60 |
| ATOM | 4036 | CG | ASP | 3218 | −12.907 | 30.607 | 27.200 | 1.00 | 29.86 |
| ATOM | 4037 | OD1 | ASP | 3218 | −12.875 | 30.278 | 28.407 | 1.00 | 33.46 |
| ATOM | 4038 | OD2 | ASP | 3218 | −12.984 | 29.755 | 26.276 | 1.00 | 32.53 |
| ATOM | 4039 | C | ASP | 3218 | −11.498 | 34.175 | 27.239 | 1.00 | 18.77 |
| ATOM | 4040 | O | ASP | 3218 | −12.027 | 35.283 | 27.338 | 1.00 | 14.25 |
| ATOM | 4041 | N | SER | 3219 | −10.353 | 33.979 | 26.602 | 1.00 | 21.90 |
| ATOM | 4042 | CA | SER | 3219 | −9.656 | 35.047 | 25.905 | 1.00 | 22.27 |
| ATOM | 4043 | CB | SER | 3219 | −10.160 | 35.142 | 24.472 | 1.00 | 25.60 |
| ATOM | 4044 | OG | SER | 3219 | −9.655 | 36.309 | 23.851 | 1.00 | 33.16 |
| ATOM | 4045 | C | SER | 3219 | −9.782 | 36.404 | 26.556 | 1.00 | 21.83 |
| ATOM | 4046 | O | SER | 3219 | −10.606 | 37.233 | 26.169 | 1.00 | 22.35 |
| ATOM | 4047 | N | VAL | 3220 | −8.946 | 36.627 | 27.553 | 1.00 | 23.69 |
| ATOM | 4048 | CA | VAL | 3220 | −8.931 | 37.897 | 28.255 | 1.00 | 21.63 |
| ATOM | 4049 | CB | VAL | 3220 | −8.254 | 37.761 | 29.631 | 1.00 | 21.56 |
| ATOM | 4050 | CG1 | VAL | 3220 | −9.053 | 36.809 | 30.515 | 1.00 | 23.43 |

TABLE 2-continued

FGFR1 D2–D3 Complexed with FGF1

| ATOM | 4051 | CG2 | VAL | 3220 | −6.830 | 37.246 | 29.449 | 1.00 | 19.83 |
|---|---|---|---|---|---|---|---|---|---|
| ATOM | 4052 | C | VAL | 3220 | −8.104 | 38.860 | 27.419 | 1.00 | 20.60 |
| ATOM | 4053 | O | VAL | 3220 | −7.209 | 38.452 | 26.662 | 1.00 | 19.89 |
| ATOM | 4054 | N | VAL | 3221 | −8.409 | 40.139 | 27.561 | 1.00 | 19.29 |
| ATOM | 4055 | CA | VAL | 3221 | −7.684 | 41.179 | 26.851 | 1.00 | 19.94 |
| ATOM | 4056 | CE | VAL | 3221 | −8.402 | 41.569 | 25.548 | 1.00 | 21.60 |
| ATOM | 4057 | CG1 | VAL | 3221 | −8.003 | 40.600 | 24.424 | 1.00 | 17.47 |
| ATOM | 4058 | CG2 | VAL | 3221 | −9.919 | 41.548 | 25.778 | 1.00 | 18.75 |
| ATOM | 4059 | C | VAL | 3221 | −7.657 | 42.359 | 27.797 | 1.00 | 19.84 |
| ATOM | 4060 | O | VAL | 3221 | −8.501 | 42.446 | 28.698 | 1.00 | 18.89 |
| ATOM | 4061 | N | PRO | 3222 | −6.695 | 43.280 | 27.613 | 1.00 | 19.44 |
| ATOM | 4062 | CD | PRO | 3222 | −5.765 | 43.319 | 26.469 | 1.00 | 19.55 |
| ATOM | 4063 | CA | PRO | 3222 | −6.531 | 44.477 | 28.449 | 1.00 | 18.50 |
| ATOM | 4064 | CB | PRO | 3222 | −5.757 | 45.420 | 27.542 | 1.00 | 17.22 |
| ATOM | 4065 | CG | PRO | 3222 | −4.842 | 44.490 | 26.830 | 1.00 | 16.82 |
| ATOM | 4066 | C | PRO | 3222 | −7.825 | 45.091 | 28.980 | 1.00 | 19.70 |
| ATOM | 4067 | O | PRO | 3222 | −7.914 | 45.418 | 30.164 | 1.00 | 20.49 |
| ATOM | 4068 | N | SER | 3223 | −8.831 | 45.231 | 28.122 | 1.00 | 20.64 |
| ATOM | 4069 | CA | SER | 3223 | −10.106 | 45.805 | 28.552 | 1.00 | 22.52 |
| ATOM | 4070 | CB | SER | 3223 | −11.114 | 45.832 | 27.390 | 1.00 | 21.18 |
| ATOM | 4071 | OG | SER | 3223 | −11.721 | 44.565 | 27.215 | 1.00 | 22.75 |
| ATOM | 4072 | C | SER | 3223 | −10.698 | 45.001 | 29.717 | 1.00 | 24.89 |
| ATOM | 4073 | O | SER | 3223 | −11.542 | 45.502 | 30.473 | 1.00 | 27.76 |
| ATOM | 4074 | N | ASP | 3224 | −10.262 | 43.754 | 29.864 | 1.00 | 24.30 |
| ATOM | 4075 | CA | ASP | 3224 | −10.767 | 42.923 | 30.942 | 1.00 | 24.39 |
| ATOM | 4076 | CB | ASP | 3224 | −10.550 | 41.438 | 30.629 | 1.00 | 24.86 |
| ATOM | 4077 | CG | ASP | 3224 | −11.488 | 40.924 | 29.548 | 1.00 | 25.47 |
| ATOM | 4078 | OD1 | ASP | 3224 | −12.696 | 41.247 | 29.630 | 1.00 | 20.81 |
| ATOM | 4079 | OD2 | ASP | 3224 | −11.017 | 40.194 | 28.634 | 1.00 | 23.43 |
| ATOM | 4080 | C | ASP | 3224 | −10.139 | 43.260 | 32.289 | 1.00 | 24.51 |
| ATOM | 4081 | O | ASP | 3224 | −10.729 | 42.972 | 33.335 | 1.00 | 24.74 |
| ATOM | 4082 | N | ALA | 3225 | −8.955 | 43.873 | 32.270 | 1.00 | 24.04 |
| ATOM | 4083 | CA | ALA | 3225 | −8.258 | 44.230 | 33.509 | 1.00 | 23.28 |
| ATOM | 4084 | CB | ALA | 3225 | −7.059 | 45.133 | 33.199 | 1.00 | 19.86 |
| ATOM | 4085 | C | ALA | 3225 | −9.186 | 44.913 | 34.517 | 1.00 | 23.54 |
| ATOM | 4086 | O | ALA | 3225 | −9.977 | 45.792 | 34.155 | 1.00 | 23.35 |
| ATOM | 4087 | N | GLY | 3226 | −9.095 | 44.495 | 35.779 | 1.00 | 24.35 |
| ATOM | 4088 | CA | GLY | 3226 | −9.920 | 45.087 | 36.823 | 1.00 | 25.68 |
| ATOM | 4089 | C | GLY | 3226 | −10.098 | 44.208 | 38.049 | 1.00 | 27.63 |
| ATOM | 4090 | O | GLY | 3226 | −9.588 | 43.080 | 38.114 | 1.00 | 28.87 |
| ATOM | 4091 | N | ASN | 3227 | −10.817 | 44.728 | 39.037 | 1.00 | 27.73 |
| ATOM | 4092 | CA | ASN | 3227 | −11.081 | 43.971 | 40.258 | 1.00 | 28.14 |
| ATOM | 4093 | CB | ASN | 3227 | −11.330 | 44.902 | 41.444 | 1.00 | 27.66 |
| ATOM | 4094 | CG | ASN | 3227 | −10.204 | 45.866 | 41.659 | 1.00 | 33.30 |
| ATOM | 4095 | OD1 | ASN | 3227 | −9.038 | 45.467 | 41.717 | 1.00 | 34.86 |
| ATOM | 4096 | ND2 | ASN | 3227 | −10.535 | 47.155 | 41.777 | 1.00 | 35.26 |
| ATOM | 4097 | C | ASN | 3227 | −12.328 | 43.132 | 40.047 | 1.00 | 27.43 |
| ATOM | 4098 | O | ASN | 3227 | −13.320 | 43.615 | 39.500 | 1.00 | 29.97 |
| ATOM | 4099 | N | TYR | 3228 | −12.279 | 41.877 | 40.475 | 1.00 | 23.65 |
| ATOM | 4100 | CA | TYR | 3228 | −13.427 | 41.005 | 40.354 | 1.00 | 19.54 |
| ATOM | 4101 | CB | TYR | 3228 | −13.120 | 39.857 | 39.420 | 1.00 | 16.85 |
| ATOM | 4102 | CG | TYR | 3228 | −13.022 | 40.318 | 38.000 | 1.00 | 17.95 |
| ATOM | 4103 | CD1 | TYR | 3228 | −11.925 | 41.064 | 37.563 | 1.00 | 16.43 |
| ATOM | 4104 | CE1 | TYR | 3228 | −11.832 | 41.510 | 36.248 | 1.00 | 17.97 |
| ATOM | 4105 | CD2 | TYR | 3228 | −14.035 | 40.032 | 37.089 | 1.00 | 18.73 |
| ATOM | 4106 | CE2 | TYR | 3228 | −13.961 | 40.477 | 35.770 | 1.00 | 20.90 |
| ATOM | 4107 | CZ | TYR | 3228 | −12.855 | 41.214 | 35.350 | 1.00 | 20.24 |
| ATOM | 4108 | OH | TYR | 3228 | −12.764 | 41.617 | 34.030 | 1.00 | 18.53 |
| ATOM | 4109 | C | TYR | 3228 | −13.787 | 40.503 | 41.730 | 1.00 | 20.76 |
| ATOM | 4110 | O | TYR | 3228 | −12.956 | 39.934 | 42.440 | 1.00 | 20.32 |
| ATOM | 4111 | N | THR | 3229 | −15.039 | 40.723 | 42.107 | 1.00 | 19.38 |
| ATOM | 4112 | CA | THR | 3229 | −15.481 | 40.331 | 43.421 | 1.00 | 19.14 |
| ATOM | 4113 | CB | THR | 3229 | −15.972 | 41.555 | 44.229 | 1.00 | 19.74 |
| ATOM | 4114 | OG1 | THR | 3229 | −14.893 | 42.487 | 44.387 | 1.00 | 15.99 |
| ATOM | 4115 | CG2 | THR | 3229 | −16.465 | 41.122 | 45.611 | 1.00 | 18.22 |
| ATOM | 4116 | C | THR | 3229 | −16.581 | 39.314 | 43.413 | 1.00 | 20.02 |
| ATOM | 4117 | O | THR | 3229 | −17.611 | 39.495 | 42.764 | 1.00 | 21.54 |
| ATOM | 4118 | N | CYS | 3230 | −16.360 | 38.227 | 44.135 | 1.00 | 18.45 |
| ATOM | 4119 | CA | CYS | 3230 | −17.393 | 37.234 | 44.226 | 1.00 | 18.73 |
| ATOM | 4120 | C | CYS | 3230 | −18.151 | 37.601 | 45.487 | 1.00 | 16.50 |
| ATOM | 4121 | O | CYS | 3230 | −17.580 | 38.147 | 46.423 | 1.00 | 15.77 |
| ATOM | 4122 | CB | CYS | 3230 | −16.805 | 35.832 | 44.344 | 1.00 | 20.59 |
| ATOM | 4123 | SG | CYS | 3230 | −15.821 | 35.551 | 45.839 | 1.00 | 28.94 |
| ATOM | 4124 | N | ILE | 3231 | −19.447 | 37.339 | 45.497 | 1.00 | 15.83 |
| ATOM | 4125 | CA | ILE | 3231 | −20.240 | 37.632 | 46.663 | 1.00 | 16.36 |
| ATOM | 4126 | CB | ILE | 3231 | −21.087 | 38.880 | 46.449 | 1.00 | 17.80 |
| ATOM | 4127 | CG2 | ILE | 3231 | −22.099 | 39.031 | 47.572 | 1.00 | 17.03 |

TABLE 2-continued

FGFR1 D2–D3 Complexed with FGF1

| ATOM | 4128 | CG1 | ILE | 3231 | −20.155 | 40.096 | 46.402 | 1.00 | 17.70 |
|---|---|---|---|---|---|---|---|---|---|
| ATOM | 4129 | CD1 | ILE | 3231 | −20.854 | 41.396 | 46.183 | 1.00 | 17.16 |
| ATOM | 4130 | C | ILE | 3231 | −21.117 | 36.449 | 46.978 | 1.00 | 17.26 |
| ATOM | 4131 | O | ILE | 3231 | −22.016 | 36.111 | 46.209 | 1.00 | 21.97 |
| ATOM | 4132 | N | VAL | 3232 | −20.827 | 35.815 | 48.112 | 1.00 | 16.47 |
| ATOM | 4133 | CA | VAL | 3232 | −21.559 | 34.651 | 48.589 | 1.00 | 16.73 |
| ATOM | 4134 | CB | VAL | 3232 | −20.592 | 33.560 | 49.054 | 1.00 | 16.46 |
| ATOM | 4135 | CG1 | VAL | 3232 | −21.368 | 32.336 | 49.523 | 1.00 | 15.36 |
| ATOM | 4136 | CG2 | VAL | 3232 | −19.640 | 33.204 | 47.919 | 1.00 | 15.79 |
| ATOM | 4137 | C | VAL | 3232 | −22.446 | 35.062 | 49.752 | 1.00 | 19.52 |
| ATOM | 4138 | O | VAL | 3232 | −21.998 | 35.738 | 50.679 | 1.00 | 19.11 |
| ATOM | 4139 | N | GLU | 3233 | −23.710 | 34.660 | 49.703 | 1.00 | 23.22 |
| ATOM | 4140 | CA | GLU | 3233 | −24.640 | 35.027 | 50.761 | 1.00 | 28.85 |
| ATOM | 4141 | CB | GLU | 3233 | −25.045 | 36.495 | 50.607 | 1.00 | 35.57 |
| ATOM | 4142 | CG | GLU | 3233 | −25.465 | 36.859 | 49.189 | 1.00 | 45.86 |
| ATOM | 4143 | CD | GLU | 3233 | −25.881 | 38.318 | 49.041 | 1.00 | 52.61 |
| ATOM | 4144 | OE1 | GLU | 3233 | −25.205 | 39.196 | 49.625 | 1.00 | 56.75 |
| ATOM | 4145 | OE2 | GLU | 3233 | −26.876 | 38.591 | 48.328 | 1.00 | 57.00 |
| ATOM | 4146 | C | GLU | 3233 | −25.906 | 34.192 | 50.799 | 1.00 | 28.73 |
| ATOM | 4147 | O | GLU | 3233 | −26.337 | 33.642 | 49.779 | 1.00 | 27.70 |
| ATOM | 4148 | N | ASN | 3234 | −26.486 | 34.103 | 51.996 | 1.00 | 26.80 |
| ATOM | 4149 | CA | ASN | 3234 | −27.738 | 33.394 | 52.223 | 1.00 | 25.14 |
| ATOM | 4150 | CB | ASN | 3234 | −27.515 | 31.945 | 52.709 | 1.00 | 24.39 |
| ATOM | 4151 | CG | ASN | 3234 | −26.752 | 31.856 | 54.025 | 1.00 | 26.09 |
| ATOM | 4152 | OD1 | ASN | 3234 | −26.658 | 32.824 | 54.781 | 1.00 | 25.60 |
| ATOM | 4153 | ND2 | ASN | 3234 | −26.217 | 30.668 | 54.313 | 1.00 | 27.06 |
| ATOM | 4154 | C | ASN | 3234 | −28.500 | 34.206 | 53.260 | 1.00 | 25.03 |
| ATOM | 4155 | O | ASN | 3234 | −28.059 | 35.292 | 53.649 | 1.00 | 21.71 |
| ATOM | 4156 | N | ALA | 3235 | −29.639 | 33.688 | 53.710 | 1.00 | 25.62 |
| ATOM | 4157 | CA | ALA | 3235 | −30.454 | 34.396 | 54.692 | 1.00 | 23.50 |
| ATOM | 4158 | CB | ALA | 3235 | −31.732 | 33.593 | 54.997 | 1.00 | 22.56 |
| ATOM | 4159 | C | ALA | 3235 | −29.701 | 34.677 | 55.987 | 1.00 | 22.86 |
| ATOM | 4160 | O | ALA | 3235 | −30.190 | 35.405 | 56.846 | 1.00 | 25.91 |
| ATOM | 4161 | N | TYR | 3236 | −28.503 | 34.134 | 56.134 | 1.00 | 20.91 |
| ATOM | 4162 | CA | TYR | 3236 | −27.782 | 34.342 | 57.380 | 1.00 | 21.67 |
| ATOM | 4163 | CB | TYR | 3236 | −27.652 | 33.010 | 58.105 | 1.00 | 24.91 |
| ATOM | 4164 | CG | TYR | 3236 | −28.992 | 32.447 | 58.456 | 1.00 | 26.84 |
| ATOM | 4165 | CD1 | TYR | 3236 | −29.739 | 31.731 | 57.519 | 1.00 | 30.31 |
| ATOM | 4166 | CE1 | TYR | 3236 | −31.017 | 31.280 | 57.820 | 1.00 | 32.58 |
| ATOM | 4167 | CD2 | TYR | 3236 | −29.552 | 32.692 | 59.700 | 1.00 | 27.82 |
| ATOM | 4168 | CE2 | TYR | 3236 | −30.824 | 32.248 | 60.016 | 1.00 | 32.47 |
| ATOM | 4169 | CZ | TYR | 3236 | −31.554 | 31.545 | 59.075 | 1.00 | 34.13 |
| ATOM | 4170 | OH | TYR | 3236 | −32.822 | 31.132 | 59.398 | 1.00 | 34.11 |
| ATOM | 4171 | C | TYR | 3236 | −26.426 | 35.013 | 57.330 | 1.00 | 20.53 |
| ATOM | 4172 | O | TYR | 3236 | −25.739 | 35.076 | 58.345 | 1.00 | 17.76 |
| ATOM | 4173 | N | GLY | 3237 | −26.039 | 35.511 | 56.163 | 1.00 | 20.51 |
| ATOM | 4174 | CA | GLY | 3237 | −24.756 | 36.169 | 56.060 | 1.00 | 20.51 |
| ATOM | 4175 | C | GLY | 3237 | −24.249 | 36.284 | 54.644 | 1.00 | 22.21 |
| ATOM | 4176 | O | GLY | 3237 | −24.719 | 35.593 | 53.740 | 1.00 | 24.70 |
| ATOM | 4177 | N | SER | 3238 | −23.278 | 37.167 | 54.459 | 1.00 | 22.08 |
| ATOM | 4178 | CA | SER | 3238 | −22.687 | 37.385 | 53.159 | 1.00 | 23.41 |
| ATOM | 4179 | CB | SER | 3238 | −23.323 | 38.592 | 52.480 | 1.00 | 24.80 |
| ATOM | 4180 | OG | SER | 3238 | −22.605 | 38.916 | 51.301 | 1.00 | 29.81 |
| ATOM | 4181 | C | SER | 3238 | −21.206 | 37.637 | 53.312 | 1.00 | 23.57 |
| ATOM | 4182 | O | SER | 3238 | −20.793 | 38.467 | 54.109 | 1.00 | 25.04 |
| ATOM | 4183 | N | ILE | 3239 | −20.403 | 36.918 | 52.549 | 1.00 | 24.19 |
| ATOM | 4184 | CA | ILE | 3239 | −18.964 | 37.111 | 52.602 | 1.00 | 25.62 |
| ATOM | 4185 | CB | ILE | 3239 | −18.230 | 35.806 | 53.039 | 1.00 | 24.95 |
| ATOM | 4186 | CG2 | ILE | 3239 | −18.633 | 35.441 | 54.456 | 1.00 | 22.17 |
| ATOM | 4187 | CG1 | ILE | 3239 | −18.587 | 34.641 | 52.107 | 1.00 | 25.70 |
| ATOM | 4188 | CD1 | ILE | 3239 | −17.955 | 33.301 | 52.512 | 1.00 | 20.71 |
| ATOM | 4189 | C | ILE | 3239 | −18.542 | 37.528 | 51.207 | 1.00 | 26.33 |
| ATOM | 4190 | O | ILE | 3239 | −19.295 | 37.345 | 50.260 | 1.00 | 28.84 |
| ATOM | 4191 | N | ASN | 3240 | −17.360 | 38.112 | 51.073 | 1.00 | 27.41 |
| ATOM | 4192 | CA | ASN | 3240 | −16.892 | 38.537 | 49.759 | 1.00 | 28.02 |
| ATOM | 4193 | CB | ASN | 3240 | −17.263 | 39.990 | 49.501 | 1.00 | 31.85 |
| ATOM | 4194 | CG | ASN | 3240 | −16.718 | 40.912 | 50.555 | 1.00 | 34.70 |
| ATOM | 4195 | OD1 | ASN | 3240 | −15.580 | 40.756 | 51.006 | 1.00 | 38.73 |
| ATOM | 4196 | ND2 | ASN | 3240 | −17.522 | 41.890 | 50.956 | 1.00 | 38.85 |
| ATOM | 4197 | C | ASN | 3240 | −15.392 | 38.397 | 49.629 | 1.00 | 26.81 |
| ATOM | 4198 | O | ASN | 3240 | −14.688 | 38.163 | 50.610 | 1.00 | 27.58 |
| ATOM | 4199 | N | HIS | 3241 | −14.904 | 38.555 | 48.409 | 1.00 | 24.50 |
| ATOM | 4200 | CA | HIS | 3241 | −13.481 | 38.452 | 48.159 | 1.00 | 24.61 |
| ATOM | 4201 | CB | HIS | 3241 | −13.059 | 36.985 | 48.084 | 1.00 | 27.80 |
| ATOM | 4202 | CG | HIS | 3241 | −11.579 | 36.796 | 47.994 | 1.00 | 30.76 |
| ATOM | 4203 | CD2 | HIS | 3241 | −10.801 | 36.293 | 47.006 | 1.00 | 32.96 |
| ATOM | 4204 | ND1 | HIS | 3241 | −10.719 | 37.187 | 48.998 | 1.00 | 31.80 |

TABLE 2-continued

FGFR1 D2–D3 Complexed with FGF1

| ATOM | 4205 | CE1 | HIS | 3241 | −9.475 | 36.935 | 48.633 | 1.00 | 32.92 |
|------|------|-----|-----|------|--------|--------|--------|------|-------|
| ATOM | 4206 | NE2 | HIS | 3241 | −9.497 | 36.394 | 47.426 | 1.00 | 34.12 |
| ATOM | 4207 | C | HIS | 3241 | −13.234 | 39.125 | 46.837 | 1.00 | 22.95 |
| ATOM | 4208 | O | HIS | 3241 | −14.061 | 39.022 | 45.939 | 1.00 | 26.24 |
| ATOM | 4209 | N | THR | 3242 | −12.112 | 39.820 | 46.706 | 1.00 | 20.64 |
| ATOM | 4210 | CA | THR | 3242 | −11.828 | 40.499 | 45.453 | 1.00 | 21.13 |
| ATOM | 4211 | CB | THR | 3242 | −11.786 | 42.047 | 45.618 | 1.00 | 20.79 |
| ATOM | 4212 | OG1 | THR | 3242 | −13.034 | 42.514 | 46.145 | 1.00 | 20.51 |
| ATOM | 4213 | CG2 | THR | 3242 | −11.545 | 42.723 | 44.260 | 1.00 | 19.11 |
| ATOM | 4214 | C | THR | 3242 | −10.507 | 40.055 | 44.865 | 1.00 | 20.94 |
| ATOM | 4215 | O | THR | 3242 | −9.541 | 39.852 | 45.590 | 1.00 | 20.69 |
| ATOM | 4216 | N | TYR | 3243 | −10.482 | 39.909 | 43.542 | 1.00 | 20.75 |
| ATOM | 4217 | CA | TYR | 3243 | −9.283 | 39.510 | 42.821 | 1.00 | 20.72 |
| ATOM | 4218 | CB | TYR | 3243 | −9.511 | 38.227 | 42.024 | 1.00 | 19.39 |
| ATOM | 4219 | CG | TYR | 3243 | −9.685 | 36.958 | 42.823 | 1.00 | 23.05 |
| ATOM | 4220 | CD1 | TYR | 3243 | −10.953 | 36.433 | 43.067 | 1.00 | 24.01 |
| ATOM | 4221 | CE1 | TYR | 3243 | −11.113 | 35.229 | 43.758 | 1.00 | 25.82 |
| ATOM | 4222 | CD2 | TYR | 3243 | −8.572 | 36.249 | 43.296 | 1.00 | 22.82 |
| ATOM | 4223 | CE2 | TYR | 3243 | −8.719 | 35.047 | 43.987 | 1.00 | 21.94 |
| ATOM | 4224 | CZ | TYR | 3243 | −9.992 | 34.542 | 44.216 | 1.00 | 23.52 |
| ATOM | 4225 | OH | TYR | 3243 | −10.156 | 33.357 | 44.902 | 1.00 | 22.85 |
| ATOM | 4226 | C | TYR | 3243 | −8.899 | 40.593 | 41.828 | 1.00 | 21.98 |
| ATOM | 4227 | O | TYR | 3243 | −9.756 | 41.162 | 41.150 | 1.00 | 23.12 |
| ATOM | 4228 | N | ALA | 3244 | −7.609 | 40.882 | 41.731 | 1.00 | 24.08 |
| ATOM | 4229 | CA | ALA | 3244 | −7.152 | 41.874 | 40.766 | 1.00 | 23.35 |
| ATOM | 4230 | CB | ALA | 3244 | −5.918 | 42.613 | 41.300 | 1.00 | 20.36 |
| ATOM | 4231 | C | ALA | 3244 | −6.800 | 41.067 | 39.517 | 1.00 | 22.90 |
| ATOM | 4232 | O | ALA | 3244 | −6.313 | 39.942 | 39.621 | 1.00 | 21.75 |
| ATOM | 4233 | N | LEU | 3245 | −7.087 | 41.601 | 38.337 | 1.00 | 23.40 |
| ATOM | 4234 | CA | LEU | 3245 | −6.722 | 40.877 | 37.129 | 1.00 | 23.04 |
| ATOM | 4235 | CB | LEU | 3245 | −7.949 | 40.348 | 36.383 | 1.00 | 20.49 |
| ATOM | 4236 | CG | LEU | 3245 | −7.587 | 39.202 | 35.416 | 1.00 | 18.53 |
| ATOM | 4237 | CD1 | LEU | 3245 | −8.834 | 38.515 | 34.932 | 1.00 | 24.70 |
| ATOM | 4238 | CD2 | LEU | 3245 | −6.804 | 39.717 | 34.248 | 1.00 | 15.82 |
| ATOM | 4239 | C | LEU | 3245 | −5.906 | 41.759 | 36.202 | 1.00 | 22.88 |
| ATOM | 4240 | O | LEU | 3245 | −6.354 | 42.818 | 35.770 | 1.00 | 23.46 |
| ATOM | 4241 | N | ASP | 3246 | −4.693 | 41.327 | 35.910 | 1.00 | 22.07 |
| ATOM | 4242 | CA | ASP | 3246 | −3.872 | 42.098 | 35.014 | 1.00 | 26.75 |
| ATOM | 4243 | CB | ASP | 3246 | −2.591 | 42.552 | 35.706 | 1.00 | 32.91 |
| ATOM | 4244 | CG | ASP | 3246 | −1.813 | 43.540 | 34.871 | 1.00 | 38.77 |
| ATOM | 4245 | OD1 | ASP | 3246 | −2.431 | 44.502 | 34.348 | 1.00 | 42.43 |
| ATOM | 4246 | OD2 | ASP | 3246 | −0.586 | 43.353 | 34.738 | 1.00 | 43.87 |
| ATOM | 4247 | C | ASP | 3246 | −3.572 | 41.224 | 33.808 | 1.00 | 26.40 |
| ATOM | 4248 | O | ASP | 3246 | −3.356 | 40.017 | 33.942 | 1.00 | 24.28 |
| ATOM | 4249 | N | VAL | 3247 | −3.582 | 41.845 | 32.632 | 1.00 | 26.01 |
| ATOM | 4250 | CA | VAL | 3247 | −3.351 | 41.160 | 31.365 | 1.00 | 24.26 |
| ATOM | 4251 | CB | VAL | 3247 | −4.631 | 41.197 | 30.500 | 1.00 | 25.02 |
| ATOM | 4252 | CG1 | VAL | 3247 | −4.390 | 40.513 | 29.147 | 1.00 | 24.28 |
| ATOM | 4253 | CG2 | VAL | 3247 | −5.775 | 40.534 | 31.254 | 1.00 | 24.22 |
| ATOM | 4254 | C | VAL | 3247 | −2.228 | 41.828 | 30.592 | 1.00 | 23.02 |
| ATOM | 4255 | O | VAL | 3247 | −2.191 | 43.048 | 30.493 | 1.00 | 26.47 |
| ATOM | 4256 | N | VAL | 3248 | −1.317 | 41.037 | 30.041 | 1.00 | 21.59 |
| ATOM | 4257 | CA | VAL | 3248 | −0.208 | 41.596 | 29.274 | 1.00 | 21.39 |
| ATOM | 4258 | CB | VAL | 3248 | 1.146 | 41.351 | 29.974 | 1.00 | 22.58 |
| ATOM | 4259 | CG1 | VAL | 3248 | 2.256 | 42.033 | 29.211 | 1.00 | 24.91 |
| ATOM | 4260 | CG2 | VAL | 3248 | 1.101 | 41.872 | 31.376 | 1.00 | 25.63 |
| ATOM | 4261 | C | VAL | 3248 | −0.131 | 40.978 | 27.881 | 1.00 | 21.94 |
| ATOM | 4262 | O | VAL | 3248 | −0.018 | 39.749 | 27.728 | 1.00 | 22.78 |
| ATOM | 4263 | N | GLU | 3249 | −0.191 | 41.831 | 26.868 | 1.00 | 18.89 |
| ATOM | 4264 | CA | GLU | 3249 | 0.106 | 41.373 | 25.498 | 1.00 | 20.08 |
| ATOM | 4265 | CB | GLU | 3249 | −0.585 | 42.473 | 24.547 | 1.00 | 23.18 |
| ATOM | 4266 | CG | GLU | 3249 | −2.023 | 42.896 | 24.804 | 1.00 | 31.25 |
| ATOM | 4267 | CD | GLU | 3249 | −2.467 | 44.090 | 23.971 | 1.00 | 34.98 |
| ATOM | 4268 | OE1 | GLU | 3249 | −1.752 | 45.120 | 23.967 | 1.00 | 36.08 |
| ATOM | 4269 | OE2 | GLU | 3249 | −3.545 | 44.002 | 23.335 | 1.00 | 39.35 |
| ATOM | 4270 | C | GLU | 3249 | 1.355 | 41.047 | 25.230 | 1.00 | 20.01 |
| ATOM | 4271 | O | GLU | 3249 | 2.214 | 41.920 | 25.359 | 1.00 | 18.96 |
| ATOM | 4272 | N | ARG | 3250 | 1.637 | 39.790 | 24.874 | 1.00 | 19.49 |
| ATOM | 4273 | CA | ARG | 3250 | 3.010 | 39.363 | 24.589 | 1.00 | 17.58 |
| ATOM | 4274 | CB | ARG | 3250 | 3.246 | 37.913 | 25.063 | 1.00 | 15.61 |
| ATOM | 4275 | CG | ARG | 3250 | 3.047 | 37.673 | 26.568 | 1.00 | 15.26 |
| ATOM | 4276 | CD | ARG | 3250 | 3.778 | 38.702 | 27.435 | 1.00 | 13.10 |
| ATOM | 4277 | NE | ARG | 3250 | 5.231 | 38.616 | 27.308 | 1.00 | 15.86 |
| ATOM | 4278 | CZ | ARG | 3250 | 5.984 | 37.658 | 27.849 | 1.00 | 16.04 |
| ATOM | 4279 | NH1 | ARG | 3250 | 5.436 | 36.682 | 28.573 | 1.00 | 10.22 |
| ATOM | 4280 | NH2 | ARG | 3250 | 7.294 | 37.679 | 27.655 | 1.00 | 12.79 |
| ATOM | 4281 | C | ARG | 3250 | 3.303 | 39.487 | 23.096 | 1.00 | 15.82 |

TABLE 2-continued

FGFR1 D2–D3 Complexed with FGF1

| ATOM | 4282 | O | ARG | 3250 | 2.445 | 39.189 | 22.273 | 1.00 | 17.84 |
|---|---|---|---|---|---|---|---|---|---|
| ATOM | 4283 | N | ALA | 3251 | 4.513 | 39.930 | 22.753 | 1.00 | 15.48 |
| ATOM | 4284 | CA | ALA | 3251 | 4.898 | 40.119 | 21.354 | 1.00 | 14.42 |
| ATOM | 4285 | CB | ALA | 3251 | 5.215 | 41.580 | 21.090 | 1.00 | 13.95 |
| ATOM | 4286 | C | ALA | 3251 | 6.076 | 39.269 | 20.952 | 1.00 | 15.60 |
| ATOM | 4287 | O | ALA | 3251 | 7.224 | 39.691 | 21.019 | 1.00 | 17.78 |
| ATOM | 4288 | N | PRO | 3252 | 5.802 | 38.051 | 20.517 | 1.00 | 16.45 |
| ATOM | 4289 | CD | PRO | 3252 | 4.527 | 37.344 | 20.712 | 1.00 | 14.69 |
| ATOM | 4290 | CA | PRO | 3252 | 6.853 | 37.129 | 20.098 | 1.00 | 15.71 |
| ATOM | 4291 | CB | PRO | 3252 | 6.210 | 35.778 | 20.345 | 1.00 | 11.93 |
| ATOM | 4292 | CG | PRO | 3252 | 4.781 | 36.053 | 20.008 | 1.00 | 11.24 |
| ATOM | 4293 | C | PRO | 3252 | 7.317 | 37.305 | 18.656 | 1.00 | 16.31 |
| ATOM | 4294 | O | PRO | 3252 | 7.055 | 36.464 | 17.812 | 1.00 | 19.07 |
| ATOM | 4295 | N | HIS | 3253 | 8.005 | 38.406 | 18.380 | 1.00 | 18.22 |
| ATOM | 4296 | CA | HIS | 3253 | 8.536 | 38.693 | 17.048 | 1.00 | 18.62 |
| ATOM | 4297 | CB | HIS | 3253 | 7.727 | 39.798 | 16.362 | 1.00 | 20.70 |
| ATOM | 4298 | CG | HIS | 3253 | 6.250 | 39.679 | 16.556 | 1.00 | 25.37 |
| ATOM | 4299 | CD2 | HIS | 3253 | 5.376 | 40.459 | 17.236 | 1.00 | 26.10 |
| ATOM | 4300 | ND1 | HIS | 3253 | 5.519 | 30.617 | 16.066 | 1.00 | 27.46 |
| ATOM | 4301 | CE1 | HIS | 3253 | 4.256 | 38.744 | 16.441 | 1.00 | 28.08 |
| ATOM | 4302 | NE2 | HIS | 3253 | 4.143 | 39.852 | 17.152 | 1.00 | 29.83 |
| ATOM | 4303 | C | HIS | 3253 | 9.956 | 39.198 | 17.291 | 1.00 | 18.94 |
| ATOM | 4304 | O | HIS | 3253 | 10.344 | 39.428 | 18.438 | 1.00 | 15.09 |
| ATOM | 4305 | N | ARG | 3254 | 10.744 | 39.357 | 16.232 | 1.00 | 20.26 |
| ATOM | 4306 | CA | ARG | 3254 | 12.089 | 39.872 | 16.425 | 1.00 | 21.29 |
| ATOM | 4307 | CB | ARG | 3254 | 12.957 | 39.675 | 15.168 | 1.00 | 23.70 |
| ATOM | 4308 | CG | ARG | 3254 | 12.702 | 40.615 | 13.987 | 1.00 | 24.93 |
| ATOM | 4309 | CD | ARG | 3254 | 11.433 | 40.262 | 13.215 | 1.00 | 31.22 |
| ATOM | 4310 | NE | ARG | 3254 | 11.665 | 40.088 | 11.774 | 1.00 | 34.34 |
| ATOM | 4311 | CZ | ARG | 3254 | 12.155 | 41.024 | 10.961 | 1.00 | 34.35 |
| ATOM | 4312 | NH1 | ARG | 3254 | 12.483 | 42.222 | 11.425 | 1.00 | 37.58 |
| ATOM | 4313 | NH2 | ARG | 3254 | 12.304 | 40.771 | 9.674 | 1.00 | 30.94 |
| ATOM | 4314 | C | ARG | 3254 | 11.906 | 41.357 | 16.738 | 1.00 | 20.88 |
| ATOM | 4315 | O | ARG | 3254 | 10.789 | 41.878 | 16.686 | 1.00 | 18.88 |
| ATOM | 4316 | N | PRO | 3255 | 12.987 | 42.054 | 17.095 | 1.00 | 19.70 |
| ATOM | 4317 | CD | PRO | 3255 | 14.381 | 41.624 | 17.300 | 1.00 | 18.17 |
| ATOM | 4318 | CA | PRO | 3255 | 12.821 | 43.480 | 17.396 | 1.00 | 19.74 |
| ATOM | 4319 | CB | PRO | 3255 | 14.238 | 43.912 | 17.802 | 1.00 | 20.14 |
| ATOM | 4320 | CG | PRO | 3255 | 14.863 | 42.624 | 18.296 | 1.00 | 18.36 |
| ATOM | 4321 | C | PRO | 3255 | 12.299 | 44.281 | 16.188 | 1.00 | 16.87 |
| ATOM | 4322 | O | PRO | 3255 | 12.444 | 43.851 | 15.046 | 1.00 | 11.59 |
| ATOM | 4323 | N | ILE | 3256 | 11.703 | 45.441 | 16.460 | 1.00 | 16.70 |
| ATOM | 4324 | CA | ILE | 3256 | 11.184 | 46.338 | 15.423 | 1.00 | 18.17 |
| ATOM | 4325 | CB | ILE | 3256 | 9.686 | 46.638 | 15.607 | 1.00 | 20.28 |
| ATOM | 4326 | CG2 | ILE | 3256 | 9.261 | 47.740 | 14.640 | 1.00 | 19.60 |
| ATOM | 4327 | CG1 | ILE | 3256 | 8.842 | 45.380 | 15.397 | 1.00 | 22.58 |
| ATOM | 4328 | CD1 | ILE | 3256 | 7.345 | 45.596 | 15.681 | 1.00 | 17.47 |
| ATOM | 4329 | C | ILE | 3256 | 11.887 | 47.688 | 15.543 | 1.00 | 19.66 |
| ATOM | 4330 | O | ILE | 3256 | 11.850 | 48.311 | 16.603 | 1.00 | 22.49 |
| ATOM | 4331 | N | LEU | 3257 | 12.520 | 48.151 | 14.474 | 1.00 | 19.13 |
| ATOM | 4332 | CA | LEU | 3257 | 13.193 | 49.447 | 14.522 | 1.00 | 20.83 |
| ATOM | 4333 | CB | LEU | 3257 | 14.501 | 49.420 | 13.727 | 1.00 | 17.27 |
| ATOM | 4334 | CG | LEU | 3257 | 15.576 | 48.370 | 14.019 | 1.00 | 17.87 |
| ATOM | 4335 | CD1 | LEU | 3257 | 16.917 | 48.850 | 13.467 | 1.00 | 14.59 |
| ATOM | 4336 | CD2 | LEU | 3257 | 15.692 | 48.142 | 15.504 | 1.00 | 19.59 |
| ATOM | 4337 | C | LEU | 3257 | 12.275 | 50.510 | 13.924 | 1.00 | 25.22 |
| ATOM | 4338 | O | LEU | 3257 | 11.457 | 50.206 | 13.048 | 1.00 | 30.51 |
| ATOM | 4339 | N | GLN | 3258 | 12.401 | 51.753 | 14.382 | 1.00 | 26.92 |
| ATOM | 4340 | CA | GLN | 3258 | 11.567 | 52.825 | 13.848 | 1.00 | 23.92 |
| ATOM | 4341 | CB | GLN | 3258 | 11.650 | 54.072 | 14.719 | 1.00 | 24.97 |
| ATOM | 4342 | CG | GLN | 3258 | 10.876 | 55.240 | 14.161 | 1.00 | 30.42 |
| ATOM | 4343 | CD | GLN | 3258 | 9.412 | 54.897 | 13.910 | 1.00 | 35.39 |
| ATOM | 4344 | OE1 | GLN | 3258 | 8.653 | 54.619 | 14.845 | 1.00 | 36.83 |
| ATOM | 4345 | NE2 | GLN | 3258 | 9.011 | 54.910 | 12.641 | 1.00 | 35.58 |
| ATOM | 4346 | C | GLN | 3258 | 12.052 | 53.151 | 12.455 | 1.00 | 22.49 |
| ATOM | 4347 | O | GLN | 3258 | 13.225 | 53.444 | 12.260 | 1.00 | 23.57 |
| ATOM | 4348 | N | ALA | 3259 | 11.145 | 53.086 | 11.486 | 1.00 | 23.47 |
| ATOM | 4349 | CA | ALA | 3259 | 11.475 | 53.373 | 10.094 | 1.00 | 23.33 |
| ATOM | 4350 | CB | ALA | 3259 | 10.231 | 53.236 | 9.234 | 1.00 | 22.24 |
| ATOM | 4351 | C | ALA | 3259 | 12.063 | 54.782 | 9.962 | 1.00 | 23.53 |
| ATOM | 4352 | O | ALA | 3259 | 11.590 | 55.728 | 10.604 | 1.00 | 25.64 |
| ATOM | 4353 | N | GLY | 3260 | 13.098 | 54.923 | 9.140 | 1.00 | 21.38 |
| ATOM | 4354 | CA | GLY | 3260 | 13.718 | 56.224 | 8.973 | 1.00 | 19.46 |
| ATOM | 4355 | C | GLY | 3260 | 14.940 | 56.397 | 9.859 | 1.00 | 19.56 |
| ATOM | 4356 | O | GLY | 3260 | 15.831 | 57.190 | 9.548 | 1.00 | 18.36 |
| ATOM | 4357 | N | LEU | 3261 | 14.991 | 55.655 | 10.961 | 1.00 | 17.37 |
| ATOM | 4358 | CA | LEU | 3261 | 16.118 | 55.743 | 11.873 | 1.00 | 18.85 |

TABLE 2-continued

| | | | FGFR1 D2–D3 Complexed with FGF1 | | | | | |
|---|---|---|---|---|---|---|---|---|
| ATOM | 4359 | CB | LEU | 3261 | 15.607 | 55.920 | 13.303 | 1.00 | 20.55 |
| ATOM | 4360 | CG | LEU | 3261 | 14.753 | 57.166 | 13.510 | 1.00 | 21.64 |
| ATOM | 4361 | CD1 | LEU | 3261 | 14.286 | 57.268 | 14.959 | 1.00 | 20.59 |
| ATOM | 4362 | CD2 | LEU | 3261 | 15.584 | 58.385 | 13.125 | 1.00 | 21.95 |
| ATOM | 4363 | C | LEU | 3261 | 17.046 | 54.516 | 11.795 | 1.00 | 19.51 |
| ATOM | 4364 | O | LEU | 3261 | 16.584 | 53.370 | 11.773 | 1.00 | 19.28 |
| ATOM | 4365 | N | PRO | 3262 | 18.369 | 54.747 | 11.731 | 1.00 | 17.57 |
| ATOM | 4366 | CD | PRO | 3262 | 19.394 | 53.687 | 11.659 | 1.00 | 15.35 |
| ATOM | 4367 | CA | PRO | 3262 | 18.988 | 56.077 | 11.731 | 1.00 | 16.54 |
| ATOM | 4368 | CB | PRO | 3262 | 20.450 | 55.773 | 12.020 | 1.00 | 16.77 |
| ATOM | 4369 | CG | PRO | 3262 | 20.647 | 54.460 | 11.303 | 1.00 | 18.22 |
| ATOM | 4370 | C | PRO | 3262 | 18.791 | 56.732 | 10.365 | 1.00 | 16.01 |
| ATOM | 4371 | O | PRO | 3262 | 18.456 | 56.061 | 9.397 | 1.00 | 20.63 |
| ATOM | 4372 | N | ALA | 3263 | 18.995 | 58.035 | 10.285 | 1.00 | 14.64 |
| ATOM | 4373 | CA | ALA | 3263 | 18.824 | 58.752 | 9.028 | 1.00 | 10.82 |
| ATOM | 4374 | CB | ALA | 3263 | 17.789 | 59.866 | 9.207 | 1.00 | 2.08 |
| ATOM | 4375 | C | ALA | 3263 | 20.150 | 59.328 | 8.529 | 1.00 | 10.32 |
| ATOM | 4376 | O | ALA | 3263 | 21.013 | 59.716 | 9.321 | 1.00 | 9.06 |
| ATOM | 4377 | N | ASN | 3264 | 20.317 | 59.369 | 7.213 | 1.00 | 10.19 |
| ATOM | 4378 | CA | ASN | 3264 | 21.532 | 59.919 | 6.636 | 1.00 | 12.92 |
| ATOM | 4379 | CB | ASN | 3264 | 21.402 | 60.084 | 5.137 | 1.00 | 10.62 |
| ATOM | 4380 | CG | ASN | 3264 | 21.014 | 58.831 | 4.472 | 1.00 | 12.92 |
| ATOM | 4381 | OD1 | ASN | 3264 | 21.294 | 57.745 | 4.983 | 1.00 | 18.04 |
| ATOM | 4382 | ND2 | ASN | 3264 | 20.375 | 58.946 | 3.313 | 1.00 | 10.07 |
| ATOM | 4383 | C | ASN | 3264 | 21.831 | 61.285 | 7.208 | 1.00 | 16.47 |
| ATOM | 4384 | O | ASN | 3264 | 20.950 | 61.990 | 7.685 | 1.00 | 18.20 |
| ATOM | 4385 | N | LYS | 3265 | 23.091 | 61.664 | 7.127 | 1.00 | 21.11 |
| ATOM | 4386 | CA | LYS | 3265 | 23.513 | 62.947 | 7.615 | 1.00 | 23.74 |
| ATOM | 4387 | CB | LYS | 3265 | 23.887 | 62.853 | 9.082 | 1.00 | 26.87 |
| ATOM | 4388 | CG | LYS | 3265 | 22.704 | 62.759 | 10.018 | 1.00 | 34.24 |
| ATOM | 4389 | CD | LYS | 3265 | 22.894 | 63.716 | 11.179 | 1.00 | 36.62 |
| ATOM | 4390 | CE | LYS | 3265 | 23.130 | 65.140 | 10.667 | 1.00 | 38.76 |
| ATOM | 4391 | HZ | LYS | 3265 | 23.421 | 66.112 | 11.766 | 1.00 | 45.11 |
| ATOM | 4392 | C | LYS | 3265 | 24.712 | 63.383 | 6.827 | 1.00 | 26.80 |
| ATOM | 4393 | O | LYS | 3265 | 25.515 | 62.554 | 6.386 | 1.00 | 26.18 |
| ATOM | 4394 | N | THR | 3266 | 24.805 | 64.691 | 6.628 | 1.00 | 29.75 |
| ATOM | 4395 | CA | THR | 3266 | 25.926 | 65.300 | 5.931 | 1.00 | 31.69 |
| ATOM | 4396 | CB | THR | 3266 | 25.485 | 66.033 | 4.646 | 1.00 | 34.37 |
| ATOM | 4397 | OG1 | THR | 3266 | 24.834 | 65.111 | 3.755 | 1.00 | 36.34 |
| ATOM | 4398 | CG2 | THR | 3266 | 26.694 | 66.636 | 3.947 | 1.00 | 35.21 |
| ATOM | 4399 | C | THR | 3266 | 26.423 | 66.313 | 6.950 | 1.00 | 31.31 |
| ATOM | 4400 | O | THR | 3266 | 25.628 | 67.032 | 7.548 | 1.00 | 28.58 |
| ATOM | 4401 | N | VAL | 3267 | 27.731 | 66.342 | 7.178 | 1.00 | 33.41 |
| ATOM | 4402 | CA | VAL | 3267 | 28.315 | 67.264 | 8.146 | 1.00 | 31.55 |
| ATOM | 4403 | CB | VAL | 3267 | 28.479 | 66.602 | 9.544 | 1.00 | 32.83 |
| ATOM | 4404 | CG1 | VAL | 3267 | 27.126 | 66.138 | 10.058 | 1.00 | 31.71 |
| ATOM | 4405 | CG2 | VAL | 3267 | 29.454 | 65.425 | 9.463 | 1.00 | 32.77 |
| ATOM | 4406 | C | VAL | 3267 | 29.676 | 67.735 | 7.674 | 1.00 | 30.75 |
| ATOM | 4407 | O | VAL | 3267 | 30.250 | 67.180 | 6.731 | 1.00 | 30.39 |
| ATOM | 4408 | N | ALA | 3268 | 30.190 | 68.761 | 8.346 | 1.00 | 30.65 |
| ATOM | 4409 | CA | ALA | 3268 | 31.480 | 69.334 | 8.004 | 1.00 | 26.28 |
| ATOM | 4410 | CB | ALA | 3268 | 31.474 | 70.814 | 8.300 | 1.00 | 24.19 |
| ATOM | 4411 | C | ALA | 3268 | 32.562 | 68.651 | 8.801 | 1.00 | 26.26 |
| ATOM | 4412 | O | ALA | 3268 | 32.304 | 68.141 | 9.896 | 1.00 | 24.95 |
| ATOM | 4413 | N | LEU | 3269 | 33.769 | 68.630 | 8.242 | 1.00 | 26.36 |
| ATOM | 4414 | CA | LEU | 3269 | 34.910 | 68.039 | 8.917 | 1.00 | 27.81 |
| ATOM | 4415 | CB | LEU | 3269 | 36.190 | 68.351 | 8.146 | 1.00 | 28.05 |
| ATOM | 4416 | CG | LEU | 3269 | 36.472 | 67.600 | 6.845 | 1.00 | 32.65 |
| ATOM | 4417 | CD1 | LEU | 3269 | 37.560 | 68.322 | 6.079 | 1.00 | 31.75 |
| ATOM | 4418 | CD2 | LEU | 3269 | 36.885 | 66.145 | 7.146 | 1.00 | 32.96 |
| ATOM | 4419 | C | LEU | 3269 | 34.988 | 68.653 | 10.313 | 1.00 | 29.41 |
| ATOM | 4420 | O | LEU | 3269 | 34.945 | 69.875 | 10.454 | 1.00 | 30.14 |
| ATOM | 4421 | N | GLY | 3270 | 35.073 | 67.811 | 11.338 | 1.00 | 29.51 |
| ATOM | 4422 | CA | GLY | 3270 | 35.168 | 68.314 | 12.694 | 1.00 | 33.16 |
| ATOM | 4423 | C | GLY | 3270 | 33.867 | 68.301 | 13.465 | 1.00 | 36.49 |
| ATOM | 4424 | O | GLY | 3270 | 33.864 | 68.345 | 14.695 | 1.00 | 38.70 |
| ATOM | 4425 | N | SER | 3271 | 32.757 | 68.237 | 12.744 | 1.00 | 38.64 |
| ATOM | 4426 | CA | SER | 3271 | 31.439 | 68.211 | 13.368 | 1.00 | 38.36 |
| ATOM | 4427 | CB | SER | 3271 | 30.339 | 68.295 | 12.298 | 1.00 | 41.39 |
| ATOM | 4428 | OG | SER | 3271 | 30.542 | 69.365 | 11.392 | 1.00 | 46.90 |
| ATOM | 4429 | C | SER | 3271 | 31.238 | 66.915 | 14.141 | 1.00 | 36.54 |
| ATOM | 4430 | O | SER | 3271 | 31.698 | 65.847 | 13.714 | 1.00 | 35.98 |
| ATOM | 4431 | N | ASH | 3272 | 30.554 | 67.005 | 15.276 | 1.00 | 34.22 |
| ATOM | 4432 | CA | ASH | 3272 | 30.248 | 65.810 | 16.046 | 1.00 | 32.39 |
| ATOM | 4433 | CB | ASH | 3272 | 30.088 | 66.137 | 17.521 | 1.00 | 33.02 |
| ATOM | 4434 | CG | ASN | 3272 | 31.275 | 66.891 | 18.065 | 1.00 | 39.47 |
| ATOM | 4435 | OD1 | ASN | 3272 | 32.424 | 66.609 | 17.711 | 1.00 | 42.72 |

TABLE 2-continued

| FGFR1 D2–D3 Complexed with FGF1 | | | | | | | | | |
|---|---|---|---|---|---|---|---|---|---|
| ATOM | 4436 | ND2 | ASN | 3272 | 31.011 | 67.861 | 18.934 | 1.00 | 44.46 |
| ATOM | 4437 | C | ASH | 3272 | 28.931 | 65.325 | 15.453 | 1.00 | 30.76 |
| ATOM | 4438 | O | ASH | 3272 | 28.197 | 66.104 | 14.839 | 1.00 | 29.02 |
| ATOM | 4439 | N | VAL | 3273 | 28.628 | 64.044 | 15.607 | 1.00 | 27.27 |
| ATOM | 4440 | CA | VAL | 3273 | 27.408 | 63.530 | 15.027 | 1.00 | 21.00 |
| ATOM | 4441 | CB | VAL | 3273 | 27.663 | 62.986 | 13.604 | 1.00 | 18.45 |
| ATOM | 4442 | CG1 | VAL | 3273 | 29.088 | 62.570 | 13.473 | 1.00 | 17.09 |
| ATOM | 4443 | CG2 | VAL | 3273 | 26.745 | 61.818 | 13.303 | 1.00 | 16.60 |
| ATOM | 4444 | C | VAL | 3273 | 26.784 | 62.471 | 15.876 | 1.00 | 20.13 |
| ATOM | 4445 | O | VAL | 3273 | 27.464 | 61.776 | 16.617 | 1.00 | 17.90 |
| ATOM | 4446 | N | GLU | 3274 | 25.465 | 62.375 | 15.764 | 1.00 | 22.07 |
| ATOM | 4447 | CA | GLU | 3274 | 24.688 | 61.401 | 16.509 | 1.00 | 23.18 |
| ATOM | 4448 | CB | GLU | 3274 | 23.979 | 62.074 | 17.690 | 1.00 | 23.38 |
| ATOM | 4449 | CG | GLU | 3274 | 24.913 | 62.655 | 18.749 | 1.00 | 27.48 |
| ATOM | 4450 | CD | GLU | 3274 | 24.164 | 63.399 | 19.858 | 1.00 | 31.71 |
| ATOM | 4451 | OE1 | GLU | 3274 | 23.681 | 64.538 | 19.628 | 1.00 | 32.69 |
| ATOM | 4452 | OE2 | GLU | 3274 | 24.048 | 62.833 | 20.965 | 1.00 | 31.25 |
| ATOM | 4453 | C | GLU | 3274 | 23.649 | 60.737 | 15.610 | 1.00 | 21.95 |
| ATOM | 4454 | O | GLU | 3274 | 22.935 | 61.400 | 14.861 | 1.00 | 21.49 |
| ATOM | 4455 | N | PHE | 3275 | 23.597 | 59.418 | 15.672 | 1.00 | 19.24 |
| ATOM | 4456 | CA | PHE | 3275 | 22.626 | 58.674 | 14.916 | 1.00 | 19.23 |
| ATOM | 4457 | CB | PHE | 3275 | 23.287 | 57.514 | 14.191 | 1.00 | 19.10 |
| ATOM | 4458 | CG | PHE | 3275 | 24.127 | 57.924 | 13.024 | 1.00 | 19.09 |
| ATOM | 4459 | CD1 | PHE | 3275 | 23.549 | 58.509 | 11.903 | 1.00 | 16.19 |
| ATOM | 4460 | CD2 | PHE | 3275 | 25.502 | 57.691 | 13.032 | 1.00 | 18.92 |
| ATOM | 4461 | CE1 | PHE | 3275 | 24.327 | 58.856 | 10.798 | 1.00 | 19.77 |
| ATOM | 4462 | CE2 | PHE | 3275 | 26.296 | 58.033 | 11.930 | 1.00 | 19.55 |
| ATOM | 4463 | CZ | PHE | 3275 | 25.709 | 58.617 | 10.809 | 1.00 | 19.45 |
| ATOM | 4464 | C | PHE | 3275 | 21.674 | 58.146 | 15.976 | 1.00 | 21.86 |
| ATOM | 4465 | O | PHE | 3275 | 22.112 | 57.809 | 17.079 | 1.00 | 21.13 |
| ATOM | 4466 | N | MET | 3276 | 20.381 | 58.089 | 15.651 | 1.00 | 22.58 |
| ATOM | 4467 | CA | MET | 3276 | 19.374 | 57.594 | 16.581 | 1.00 | 20.39 |
| ATOM | 4468 | CB | MET | 3276 | 18.189 | 58.559 | 16.669 | 1.00 | 24.62 |
| ATOM | 4469 | CG | MET | 3276 | 18.569 | 60.006 | 16.901 | 1.00 | 28.34 |
| ATOM | 4470 | SD | MET | 3276 | 17.107 | 61.034 | 17.050 | 1.00 | 35.45 |
| ATOM | 4471 | CE | MET | 3276 | 16.966 | 61.152 | 18.854 | 1.00 | 30.79 |
| ATOM | 4472 | C | MET | 3276 | 18.875 | 56.255 | 16.096 | 1.00 | 17.79 |
| ATOM | 4473 | O | MET | 3276 | 19.039 | 55.897 | 14.940 | 1.00 | 18.35 |
| ATOM | 4474 | N | CYS | 3277 | 18.248 | 55.520 | 16.992 | 1.00 | 17.70 |
| ATOM | 4475 | CA | CYS | 3277 | 17.710 | 54.222 | 16.662 | 1.00 | 20.83 |
| ATOM | 4476 | C | CYS | 3277 | 16.625 | 53.942 | 17.694 | 1.00 | 20.81 |
| ATOM | 4477 | O | CYS | 3277 | 16.870 | 54.046 | 18.888 | 1.00 | 21.06 |
| ATOM | 4478 | CB | CYS | 3277 | 18.814 | 53.177 | 16.750 | 1.00 | 22.91 |
| ATOM | 4479 | SG | CYS | 3277 | 18.391 | 51.532 | 16.092 | 1.00 | 30.91 |
| ATOM | 4480 | N | LYS | 3278 | 15.424 | 53.617 | 17.232 | 1.00 | 21.63 |
| ATOM | 4481 | CA | LYS | 3278 | 14.317 | 53.330 | 18.133 | 1.00 | 22.79 |
| ATOM | 4482 | CB | LYS | 3278 | 13.116 | 54.204 | 17.774 | 1.00 | 22.66 |
| ATOM | 4483 | CG | LYS | 3278 | 12.549 | 55.036 | 18.920 | 1.00 | 25.77 |
| ATOM | 4484 | CD | LYS | 3278 | 11.525 | 54.270 | 19.754 | 1.00 | 27.26 |
| ATOM | 4485 | CE | LYS | 3278 | 10.787 | 55.171 | 20.761 | 1.00 | 32.36 |
| ATOM | 4486 | NZ | LYS | 3278 | 9.998 | 56.303 | 20.152 | 1.00 | 36.39 |
| ATOM | 4487 | C | LYS | 3278 | 13.964 | 51.854 | 17.991 | 1.00 | 22.92 |
| ATOM | 4488 | O | LYS | 3278 | 13.645 | 51.388 | 16.903 | 1.00 | 26.50 |
| ATOM | 4489 | N | VAL | 3279 | 14.010 | 51.128 | 19.101 | 1.00 | 19.71 |
| ATOM | 4490 | CA | VAL | 3279 | 13.740 | 49.699 | 19.101 | 1.00 | 17.12 |
| ATOM | 4491 | CB | VAL | 3279 | 15.001 | 48.917 | 19.619 | 1.00 | 17.18 |
| ATOM | 4492 | CG1 | VAL | 3279 | 14.748 | 47.431 | 19.611 | 1.00 | 16.48 |
| ATOM | 4493 | CG2 | VAL | 3279 | 16.218 | 49.251 | 18.782 | 1.00 | 14.76 |
| ATOM | 4494 | C | VAL | 3279 | 12.563 | 49.360 | 20.009 | 1.00 | 18.51 |
| ATOM | 4495 | O | VAL | 3279 | 12.359 | 50.014 | 21.036 | 1.00 | 17.83 |
| ATOM | 4496 | N | TYR | 3280 | 11.772 | 48.365 | 19.611 | 1.00 | 18.37 |
| ATOM | 4497 | CA | TYR | 3280 | 10.663 | 47.877 | 20.434 | 1.00 | 19.65 |
| ATOM | 4498 | CB | TYR | 3280 | 9.283 | 48.153 | 19.848 | 1.00 | 21.02 |
| ATOM | 4499 | CG | TYR | 3280 | 8.217 | 47.325 | 20.584 | 1.00 | 26.66 |
| ATOM | 4500 | CD1 | TYR | 3280 | 7.618 | 47.794 | 21.765 | 1.00 | 26.80 |
| ATOM | 4501 | CE1 | TYR | 3280 | 6.736 | 46.989 | 22.504 | 1.00 | 24.94 |
| ATOM | 4502 | CD2 | TYR | 3280 | 7.890 | 46.025 | 20.160 | 1.00 | 24.05 |
| ATOM | 4503 | CE2 | TYR | 3280 | 7.012 | 45.219 | 20.896 | 1.00 | 24.17 |
| ATOM | 4504 | CZ | TYR | 3280 | 6.442 | 45.706 | 22.064 | 1.00 | 25.11 |
| ATOM | 4505 | OH | TYR | 3280 | 5.602 | 44.905 | 22.807 | 1.00 | 26.64 |
| ATOM | 4506 | C | TYR | 3280 | 10.859 | 46.370 | 20.461 | 1.00 | 20.50 |
| ATOM | 4507 | O | TYR | 3280 | 11.101 | 45.749 | 19.423 | 1.00 | 20.46 |
| ATOM | 4508 | N | SER | 3281 | 10.724 | 45.771 | 21.632 | 1.00 | 18.62 |
| ATOM | 4509 | CA | SER | 3281 | 10.951 | 44.352 | 21.722 | 1.00 | 18.26 |
| ATOM | 4510 | CB | SER | 3281 | 12.446 | 44.103 | 21.521 | 1.00 | 13.72 |
| ATOM | 4511 | OG | SER | 3281 | 12.762 | 42.733 | 21.584 | 1.00 | 23.33 |
| ATOM | 4512 | C | SER | 3281 | 10.489 | 43.821 | 23.067 | 1.00 | 20.13 |

TABLE 2-continued

FGFR1 D2–D3 Complexed with FGF1

| ATOM | 4513 | O | SER | 3281 | 11.004 | 44.249 | 24.092 | 1.00 | 23.43 |
|---|---|---|---|---|---|---|---|---|---|
| ATOM | 4514 | N | ASP | 3282 | 9.506 | 42.915 | 23.071 | 1.00 | 21.92 |
| ATOM | 4515 | CA | ASP | 3282 | 9.023 | 42.327 | 24.319 | 1.00 | 18.13 |
| ATOM | 4516 | CB | ASP | 3282 | 7.911 | 41.313 | 24.046 | 1.00 | 17.35 |
| ATOM | 4517 | CG | ASP | 3282 | 7.463 | 40.592 | 25.297 | 1.00 | 23.20 |
| ATOM | 4518 | OD1 | ASP | 3282 | 6.423 | 39.898 | 25.266 | 1.00 | 21.51 |
| ATOM | 4519 | OD2 | ASP | 3282 | 8.160 | 40.709 | 26.324 | 1.00 | 29.34 |
| ATOM | 4520 | C | ASP | 3282 | 10.238 | 41.675 | 24.993 | 1.00 | 17.69 |
| ATOM | 4521 | O | ASP | 3282 | 10.647 | 42.102 | 26.072 | 1.00 | 18.82 |
| ATOM | 4522 | N | PRO | 3283 | 10.837 | 40.640 | 24.379 | 1.00 | 16.79 |
| ATOM | 4523 | CD | PRO | 3283 | 10.440 | 39.777 | 23.257 | 1.00 | 16.75 |
| ATOM | 4524 | CA | PRO | 3283 | 12.003 | 40.079 | 25.072 | 1.00 | 18.89 |
| ATOM | 4525 | CB | PRO | 3283 | 12.267 | 38.779 | 24.315 | 1.00 | 19.64 |
| ATOM | 4526 | CG | PRO | 3283 | 11.723 | 39.043 | 22.959 | 1.00 | 17.42 |
| ATOM | 4527 | C | PRO | 3283 | 13.165 | 41.070 | 24.982 | 1.00 | 18.93 |
| ATOM | 4528 | O | PRO | 3283 | 13.200 | 41.882 | 24.064 | 1.00 | 19.18 |
| ATOM | 4529 | N | GLN | 3284 | 14.100 | 41.017 | 25.927 | 1.00 | 20.79 |
| ATOM | 4530 | CA | GLN | 3284 | 15.228 | 41.954 | 25.923 | 1.00 | 23.12 |
| ATOM | 4531 | CB | GLN | 3284 | 16.190 | 41.670 | 27.079 | 1.00 | 26.64 |
| ATOM | 4532 | CG | GLN | 3284 | 15.686 | 42.185 | 28.403 | 1.00 | 31.18 |
| ATOM | 4533 | CD | GLN | 3284 | 15.444 | 43.677 | 28.369 | 1.00 | 33.51 |
| ATOM | 4534 | OE1 | GLN | 3284 | 14.530 | 44.187 | 29.025 | 1.00 | 37.06 |
| ATOM | 4535 | NE2 | GLN | 3284 | 16.270 | 44.392 | 27.611 | 1.00 | 30.56 |
| ATOM | 4536 | C | GLN | 3284 | 16.024 | 41.991 | 24.632 | 1.00 | 22.12 |
| ATOM | 4537 | O | GLN | 3284 | 16.584 | 40.984 | 24.198 | 1.00 | 22.15 |
| ATOM | 4538 | N | PRO | 3285 | 16.088 | 43.170 | 24.000 | 1.00 | 21.03 |
| ATOM | 4539 | CD | PRO | 3285 | 15.338 | 44.399 | 24.314 | 1.00 | 18.24 |
| ATOM | 4540 | CA | PRO | 3285 | 16.831 | 43.327 | 22.748 | 1.00 | 20.96 |
| ATOM | 4541 | CB | PRO | 3285 | 16.141 | 44.520 | 22.100 | 1.00 | 16.42 |
| ATOM | 4542 | CG | PRO | 3285 | 15.890 | 45.387 | 23.289 | 1.00 | 17.30 |
| ATOM | 4543 | C | PRO | 3285 | 18.308 | 43.614 | 23.016 | 1.00 | 19.61 |
| ATOM | 4544 | O | PRO | 3285 | 18.652 | 44.229 | 24.019 | 1.00 | 17.18 |
| ATOM | 4545 | N | HIS | 3286 | 19.172 | 43.159 | 22.122 | 1.00 | 18.93 |
| ATOM | 4546 | CA | HIS | 3286 | 20.590 | 43.421 | 22.256 | 1.00 | 21.50 |
| ATOM | 4547 | CB | HIS | 3286 | 21.386 | 42.122 | 22.155 | 1.00 | 24.23 |
| ATOM | 4548 | CG | HIS | 3286 | 22.858 | 42.309 | 22.322 | 1.00 | 31.35 |
| ATOM | 4549 | CD2 | HIS | 3286 | 23.614 | 42.468 | 23.436 | 1.00 | 35.30 |
| ATOM | 4550 | ND1 | HIS | 3286 | 23.725 | 42.413 | 21.255 | 1.00 | 33.71 |
| ATOM | 4551 | CE1 | HIS | 3286 | 24.949 | 42.629 | 21.702 | 1.00 | 35.42 |
| ATOM | 4552 | NE2 | HIS | 3286 | 24.909 | 42.667 | 23.023 | 1.00 | 36.55 |
| ATOM | 4553 | C | HIS | 3286 | 20.909 | 44.351 | 21.094 | 1.00 | 20.80 |
| ATOM | 4554 | O | HIS | 3286 | 20.759 | 43.969 | 19.941 | 1.00 | 23.48 |
| ATOM | 4555 | N | ILE | 3287 | 21.334 | 45.573 | 21.391 | 1.00 | 20.39 |
| ATOM | 4556 | CA | ILE | 3287 | 21.621 | 46.542 | 20.339 | 1.00 | 20.95 |
| ATOM | 4557 | CB | ILE | 3287 | 20.963 | 47.928 | 20.640 | 1.00 | 20.11 |
| ATOM | 4558 | CG2 | ILE | 3287 | 21.540 | 48.991 | 19.725 | 1.00 | 18.21 |
| ATOM | 4559 | CG1 | ILE | 3287 | 19.453 | 47.874 | 20.409 | 1.00 | 17.87 |
| ATOM | 4560 | CD1 | ILE | 3287 | 18.684 | 47.133 | 21.453 | 1.00 | 19.51 |
| ATOM | 4561 | G | ILE | 3287 | 23.098 | 46.781 | 20.079 | 1.00 | 22.79 |
| ATOM | 4562 | O | ILE | 3287 | 23.882 | 46.958 | 21.004 | 1.00 | 26.54 |
| ATOM | 4563 | N | GLN | 3288 | 23.465 | 46.802 | 18.803 | 1.00 | 24.49 |
| ATOM | 4564 | CA | GLN | 3288 | 24.847 | 47.044 | 18.394 | 1.00 | 26.54 |
| ATOM | 4565 | CB | GLN | 3288 | 25.519 | 45.772 | 17.891 | 1.00 | 27.11 |
| ATOM | 4566 | CG | GLN | 3288 | 25.897 | 44.755 | 18.923 | 1.00 | 29.11 |
| ATOM | 4567 | CD | GLN | 3288 | 26.700 | 43.633 | 18.300 | 1.00 | 32.97 |
| ATOM | 4568 | OE1 | GLN | 3288 | 26.985 | 42.623 | 18.942 | 1.00 | 36.15 |
| ATOM | 4569 | NE2 | GLN | 3288 | 27.077 | 43.809 | 17.035 | 1.00 | 34.32 |
| ATOM | 4570 | C | GLN | 3288 | 24.871 | 48.020 | 17.240 | 1.00 | 27.48 |
| ATOM | 4571 | O | GLN | 3288 | 23.938 | 48.058 | 16.432 | 1.00 | 28.66 |
| ATOM | 4572 | N | TRP | 3289 | 25.933 | 48.811 | 17.157 | 1.00 | 26.47 |
| ATOM | 4573 | CA | TRP | 3289 | 26.067 | 49.736 | 16.045 | 1.00 | 26.74 |
| ATOM | 4574 | CB | TRP | 3289 | 26.374 | 51.152 | 16.533 | 1.00 | 23.41 |
| ATOM | 4575 | CG | TRP | 3289 | 25.166 | 51.857 | 17.065 | 1.00 | 23.14 |
| ATOM | 4576 | CD2 | TRP | 3289 | 24.250 | 52.667 | 16.319 | 1.00 | 24.29 |
| ATOM | 4577 | CE2 | TRP | 3289 | 23.249 | 53.110 | 17.221 | 1.00 | 24.25 |
| ATOM | 4578 | CE3 | TRP | 3289 | 24.176 | 53.068 | 14.977 | 1.00 | 21.24 |
| ATOM | 4579 | CD1 | TRP | 3289 | 24.696 | 51.836 | 18.350 | 1.00 | 23.53 |
| ATOM | 4580 | NE1 | TRP | 3289 | 23.546 | 52.587 | 18.453 | 1.00 | 21.95 |
| ATOM | 4581 | CZ2 | TRP | 3289 | 22.191 | 53.930 | 16.821 | 1.00 | 21.61 |
| ATOM | 4582 | CZ3 | TRP | 3289 | 23.128 | 53.882 | 14.585 | 1.00 | 20.89 |
| ATOM | 4583 | CH2 | TRP | 3289 | 22.148 | 54.303 | 15.505 | 1.00 | 21.46 |
| ATOM | 4584 | C | TRP | 3289 | 27.209 | 49.187 | 15.212 | 1.00 | 27.47 |
| ATOM | 4585 | O | TRP | 3289 | 28.209 | 48.729 | 15.770 | 1.00 | 26.21 |
| ATOM | 4586 | N | LEU | 3290 | 27.062 | 49.206 | 13.890 | 1.00 | 27.19 |
| ATOM | 4587 | CA | LEU | 3290 | 28.112 | 48.670 | 13.030 | 1.00 | 30.23 |
| ATOM | 4588 | CB | LEU | 3290 | 27.654 | 47.363 | 12.364 | 1.00 | 30.65 |
| ATOM | 4589 | CG | LEU | 3290 | 26.744 | 46.363 | 13.088 | 1.00 | 32.74 |

TABLE 2-continued

FGFR1 D2–D3 Complexed with FGF1

| ATOM | 4590 | CD1 | LEU | 3290 | 26.405 | 45.229 | 12.126 | 1.00 | 32.45 |
|---|---|---|---|---|---|---|---|---|---|
| ATOM | 4591 | CD2 | LEU | 3290 | 27.415 | 45.814 | 14.331 | 1.00 | 31.09 |
| ATOM | 4592 | C | LEU | 3290 | 28.540 | 49.627 | 11.925 | 1.00 | 31.63 |
| ATOM | 4593 | O | LEU | 3290 | 27.706 | 50.259 | 11.281 | 1.00 | 32.46 |
| ATOM | 4594 | N | LYS | 3291 | 29.847 | 49.725 | 11.706 | 1.00 | 31.42 |
| ATOM | 4595 | CA | LYS | 3291 | 30.367 | 50.556 | 10.636 | 1.00 | 30.67 |
| ATOM | 4596 | CB | LYS | 3291 | 31.649 | 51.270 | 11.086 | 1.00 | 32.02 |
| ATOM | 4597 | CG | LYS | 3291 | 32.367 | 52.067 | 9.979 | 1.00 | 34.48 |
| ATOM | 4598 | CD | LYS | 3291 | 31.482 | 53.169 | 9.410 | 1.00 | 36.64 |
| ATOM | 4599 | CE | LYS | 3291 | 32.240 | 54.108 | 8.483 | 1.00 | 37.18 |
| ATOM | 4600 | NZ | LYS | 3291 | 32.575 | 53.496 | 7.171 | 1.00 | 40.53 |
| ATOM | 4601 | C | LYS | 3291 | 30.677 | 49.592 | 9.483 | 1.00 | 31.41 |
| ATOM | 4602 | O | LYS | 3291 | 31.101 | 48.457 | 9.703 | 1.00 | 32.63 |
| ATOM | 4603 | N | HIS | 3292 | 30.450 | 50.025 | 8.257 | 1.00 | 29.58 |
| ATOM | 4604 | CA | HIS | 3292 | 30.744 | 49.181 | 7.123 | 1.00 | 30.27 |
| ATOM | 4605 | CB | HIS | 3292 | 29.750 | 49.477 | 6.012 | 1.00 | 32.12 |
| ATOM | 4606 | CG | HIS | 3292 | 28.356 | 49.047 | 6.340 | 1.00 | 35.10 |
| ATOM | 4607 | CD2 | HIS | 3292 | 27.449 | 49.557 | 7.208 | 1.00 | 37.52 |
| ATOM | 4608 | ND1 | HIS | 3292 | 27.782 | 47.917 | 5.807 | 1.00 | 36.31 |
| ATOM | 4609 | CE1 | HIS | 3292 | 26.580 | 47.746 | 6.332 | 1.00 | 37.82 |
| ATOM | 4610 | NE2 | HIS | 3292 | 26.356 | 48.728 | 7.185 | 1.00 | 36.14 |
| ATOM | 4611 | C | HIS | 3292 | 32.167 | 49.447 | 6.674 | 1.00 | 33.55 |
| ATOM | 4612 | O | HIS | 3292 | 32.593 | 50.595 | 6.598 | 1.00 | 37.07 |
| ATOM | 4613 | N | ILE | 3293 | 32.923 | 48.393 | 6.403 | 1.00 | 36.32 |
| ATOM | 4614 | CA | ILE | 3293 | 34.305 | 48.570 | 5.961 | 1.00 | 38.28 |
| ATOM | 4615 | CB | ILE | 3293 | 35.306 | 47.935 | 6.941 | 1.00 | 38.79 |
| ATOM | 4616 | CG2 | ILE | 3293 | 36.727 | 48.397 | 6.594 | 1.00 | 39.12 |
| ATOM | 4617 | CG1 | ILE | 3293 | 34.959 | 48.331 | 8.374 | 1.00 | 40.05 |
| ATOM | 4618 | CD1 | ILE | 3293 | 35.815 | 47.629 | 9.413 | 1.00 | 42.09 |
| ATOM | 4619 | C | ILE | 3293 | 34.524 | 47.942 | 4.592 | 1.00 | 36.87 |
| ATOM | 4620 | O | ILE | 3293 | 34.286 | 46.754 | 4.413 | 1.00 | 35.64 |
| ATOM | 4621 | N | PRO | 3306 | 28.867 | 41.727 | 3.498 | 1.00 | 50.53 |
| ATOM | 4622 | CD | PRO | 3306 | 27.398 | 41.849 | 3.543 | 1.00 | 49.75 |
| ATOM | 4623 | CA | PRO | 3306 | 29.512 | 43.010 | 3.811 | 1.00 | 49.98 |
| ATOM | 4624 | CB | PRO | 3306 | 28.333 | 43.986 | 3.832 | 1.00 | 48.87 |
| ATOM | 4625 | CG | PRO | 3306 | 27.204 | 43.134 | 4.329 | 1.00 | 48.75 |
| ATOM | 4626 | C | PRO | 3306 | 30.270 | 42.985 | 5.142 | 1.00 | 49.99 |
| ATOM | 4627 | O | PRO | 3306 | 29.706 | 42.596 | 6.172 | 1.00 | 50.18 |
| ATOM | 4628 | N | TYR | 3307 | 31.541 | 43.393 | 5.126 | 1.00 | 49.25 |
| ATOM | 4629 | CA | TYR | 3307 | 32.328 | 43.399 | 6.363 | 1.00 | 49.05 |
| ATOM | 4630 | CB | TYR | 3307 | 33.815 | 43.615 | 6.087 | 1.00 | 53.62 |
| ATOM | 4631 | CG | TYR | 3307 | 34.323 | 42.890 | 4.877 | 1.00 | 58.69 |
| ATOM | 4632 | CD1 | TYR | 3307 | 34.194 | 43.454 | 3.605 | 1.00 | 61.80 |
| ATOM | 4633 | CE1 | TYR | 3307 | 34.648 | 42.790 | 2.470 | 1.00 | 63.44 |
| ATOM | 4634 | CD2 | TYR | 3307 | 34.919 | 41.633 | 4.991 | 1.00 | 60.87 |
| ATOM | 4635 | CE2 | TYR | 3307 | 35.376 | 40.952 | 3.861 | 1.00 | 63.67 |
| ATOM | 4636 | CZ | TYR | 3307 | 35.236 | 41.539 | 2.604 | 1.00 | 64.69 |
| ATOM | 4637 | OH | TYR | 3307 | 35.680 | 40.877 | 1.482 | 1.00 | 65.93 |
| ATOM | 4638 | C | TYR | 3307 | 31.841 | 44.510 | 7.274 | 1.00 | 46.00 |
| ATOM | 4639 | O | TYR | 3307 | 31.348 | 45.536 | 6.810 | 1.00 | 45.20 |
| ATOM | 4640 | N | VAL | 3308 | 31.977 | 44.305 | 8.574 | 1.00 | 42.35 |
| ATOM | 4641 | CA | VAL | 3308 | 31.540 | 45.311 | 9.514 | 1.00 | 42.49 |
| ATOM | 4642 | CB | VAL | 3308 | 30.100 | 45.020 | 10.042 | 1.00 | 41.34 |
| ATOM | 4643 | CG1 | VAL | 3308 | 29.126 | 44.929 | 8.875 | 1.00 | 38.13 |
| ATOM | 4644 | CG2 | VAL | 3308 | 30.076 | 43.740 | 10.854 | 1.00 | 39.99 |
| ATOM | 4645 | C | VAL | 3308 | 32.504 | 45.398 | 10.679 | 1.00 | 42.70 |
| ATOM | 4646 | O | VAL | 3308 | 33.301 | 44.492 | 10.919 | 1.00 | 41.81 |
| ATOM | 4647 | N | GLN | 3309 | 32.427 | 46.512 | 11.394 | 1.00 | 44.15 |
| ATOM | 4648 | CA | GLN | 3309 | 33.273 | 46.765 | 12.549 | 1.00 | 45.11 |
| ATOM | 4649 | CB | GLN | 3309 | 34.236 | 47.914 | 12.245 | 1.00 | 47.30 |
| ATOM | 4650 | CG | GLN | 3309 | 35.242 | 48.211 | 13.350 | 1.00 | 53.22 |
| ATOM | 4651 | CD | GLN | 3309 | 35.912 | 49.576 | 13.194 | 1.00 | 54.67 |
| ATOM | 4652 | OE1 | GLN | 3309 | 36.545 | 49.870 | 12.171 | 1.00 | 53.51 |
| ATOM | 4653 | NE2 | GLN | 3309 | 35.777 | 50.414 | 14.219 | 1.00 | 56.15 |
| ATOM | 4654 | C | GLN | 3309 | 32.346 | 47.156 | 13.691 | 1.00 | 45.06 |
| ATOM | 4655 | O | GLN | 3309 | 31.785 | 48.252 | 13.703 | 1.00 | 44.56 |
| ATOM | 4656 | N | ILE | 3310 | 32.157 | 46.242 | 14.637 | 1.00 | 44.25 |
| ATOM | 4657 | CA | ILE | 3310 | 31.300 | 46.520 | 15.779 | 1.00 | 43.66 |
| ATOM | 4658 | CB | ILE | 3310 | 31.339 | 45.393 | 16.829 | 1.00 | 43.39 |
| ATOM | 4659 | CG2 | ILE | 3310 | 30.367 | 45.716 | 17.973 | 1.00 | 42.44 |
| ATOM | 4660 | CG1 | ILE | 3310 | 31.027 | 44.054 | 16.167 | 1.00 | 44.49 |
| ATOM | 4661 | CD1 | ILE | 3310 | 29.676 | 43.946 | 15.554 | 1.00 | 45.12 |
| ATOM | 4662 | C | ILE | 3310 | 31.856 | 47.788 | 16.426 | 1.00 | 44.91 |
| ATOM | 4663 | O | ILE | 3310 | 33.062 | 47.895 | 16.668 | 1.00 | 47.75 |
| ATOM | 4664 | N | LEU | 3311 | 30.983 | 48.745 | 16.700 | 1.00 | 44.00 |
| ATOM | 4665 | CA | LEU | 3311 | 31.416 | 49.981 | 17.314 | 1.00 | 44.24 |
| ATOM | 4666 | CB | LEU | 3311 | 30.826 | 51.171 | 16.568 | 1.00 | 41.92 |

TABLE 2-continued

FGFR1 D2–D3 Complexed with FGF1

| ATOM | 4667 | CG | LEU | 3311 | 31.261 | 51.359 | 15.118 | 1.00 | 39.13 |
|---|---|---|---|---|---|---|---|---|---|
| ATOM | 4668 | CD1 | LEU | 3311 | 30.663 | 52.645 | 14.587 | 1.00 | 37.21 |
| ATOM | 4669 | CD2 | LEU | 3311 | 32.783 | 51.415 | 15.040 | 1.00 | 39.70 |
| ATOM | 4670 | C | LEU | 3311 | 30.994 | 50.028 | 18.777 | 1.00 | 47.49 |
| ATOM | 4671 | O | LEU | 3311 | 31.833 | 50.177 | 19.670 | 1.00 | 48.37 |
| ATOM | 4672 | N | LYS | 3312 | 29.692 | 49.894 | 19.011 | 1.00 | 50.65 |
| ATOM | 4673 | CA | LYS | 3312 | 29.133 | 49.913 | 20.362 | 1.00 | 54.46 |
| ATOM | 4674 | CB | LYS | 3312 | 28.221 | 51.136 | 20.515 | 1.00 | 53.77 |
| ATOM | 4675 | CG | LYS | 3312 | 28.241 | 51.855 | 21.869 | 1.00 | 52.70 |
| ATOM | 4676 | CD | LYS | 3312 | 27.424 | 53.137 | 21.769 | 1.00 | 51.76 |
| ATOM | 4677 | CE | LYS | 3312 | 27.481 | 53.952 | 23.049 | 1.00 | 52.83 |
| ATOM | 4678 | NZ | LYS | 3312 | 26.811 | 55.293 | 22.886 | 1.00 | 53.72 |
| ATOM | 4679 | C | LYS | 3312 | 28.343 | 48.607 | 20.616 | 1.00 | 57.49 |
| ATOM | 4680 | O | LYS | 3312 | 27.749 | 48.046 | 19.687 | 1.00 | 59.53 |
| ATOM | 4681 | N | THR | 3313 | 28.359 | 48.115 | 21.860 | 1.00 | 59.16 |
| ATOM | 4682 | CA | THR | 3313 | 27.664 | 46.873 | 22.244 | 1.00 | 60.02 |
| ATOM | 4683 | CB | THR | 3313 | 28.689 | 45.666 | 22.326 | 1.00 | 59.43 |
| ATOM | 4684 | OG1 | THR | 3313 | 29.391 | 45.525 | 21.079 | 1.00 | 56.36 |
| ATOM | 4685 | CG2 | THR | 3313 | 27.970 | 44.349 | 22.630 | 1.00 | 59.12 |
| ATOM | 4686 | C | THR | 3313 | 26.983 | 47.091 | 23.615 | 1.00 | 61.92 |
| ATOM | 4687 | O | THR | 3313 | 27.650 | 47.438 | 24.597 | 1.00 | 62.79 |
| ATOM | 4688 | N | ALA | 3314 | 25.661 | 46.915 | 23.686 | 1.00 | 63.68 |
| ATOM | 4689 | CA | ALA | 3314 | 24.932 | 47.099 | 24.951 | 1.00 | 64.89 |
| ATOM | 4690 | CB | ALA | 3314 | 23.410 | 47.023 | 24.709 | 1.00 | 63.92 |
| ATOM | 4691 | C | ALA | 3314 | 25.347 | 46.050 | 25.991 | 1.00 | 66.12 |
| ATOM | 4692 | O | ALA | 3314 | 25.748 | 44.927 | 25.650 | 1.00 | 67.50 |
| ATOM | 4693 | N | GLU | 3324 | 20.459 | 54.050 | 22.281 | 1.00 | 34.45 |
| ATOM | 4694 | CA | GLU | 3324 | 19.646 | 54.513 | 21.164 | 1.00 | 33.67 |
| ATOM | 4695 | CB | GLU | 3324 | 18.445 | 55.300 | 21.667 | 1.00 | 34.05 |
| ATOM | 4696 | CG | GLU | 3324 | 17.497 | 54.551 | 22.561 | 1.00 | 41.24 |
| ATOM | 4697 | CD | GLU | 3324 | 16.378 | 55.455 | 23.059 | 1.00 | 47.04 |
| ATOM | 4698 | OE1 | GLU | 3324 | 16.315 | 56.614 | 22.587 | 1.00 | 50.25 |
| ATOM | 4699 | OE2 | GLU | 3324 | 15.562 | 55.020 | 23.908 | 1.00 | 49.44 |
| ATOM | 4700 | C | GLU | 3324 | 20.436 | 55.413 | 20.221 | 1.00 | 32.17 |
| ATOM | 4701 | O | GLU | 3324 | 20.021 | 55.642 | 19.087 | 1.00 | 34.70 |
| ATOM | 4702 | N | VAL | 3325 | 21.566 | 55.939 | 20.675 | 1.00 | 28.22 |
| ATOM | 4703 | CA | VAL | 3325 | 22.332 | 56.815 | 19.808 | 1.00 | 26.02 |
| ATOM | 4704 | CB | VAL | 3325 | 22.258 | 56.306 | 20.284 | 1.00 | 25.39 |
| ATOM | 4705 | CG1 | VAL | 3325 | 21.084 | 58.494 | 21.229 | 1.00 | 19.03 |
| ATOM | 4706 | CG2 | VAL | 3325 | 23.565 | 58.739 | 20.923 | 1.00 | 22.06 |
| ATOM | 4707 | C | VAL | 3325 | 23.787 | 56.413 | 19.655 | 1.00 | 25.59 |
| ATOM | 4708 | O | VAL | 3325 | 24.409 | 55.904 | 20.582 | 1.00 | 22.40 |
| ATOM | 4709 | N | LEU | 3326 | 24.308 | 56.631 | 18.454 | 1.00 | 26.42 |
| ATOM | 4710 | CA | LEU | 3326 | 25.696 | 56.339 | 18.140 | 1.00 | 26.12 |
| ATOM | 4711 | CB | LEU | 3326 | 25.821 | 55.622 | 16.786 | 1.00 | 21.59 |
| ATOM | 4712 | CG | LEU | 3326 | 27.247 | 55.571 | 16.215 | 1.00 | 22.26 |
| ATOM | 4713 | CD1 | LEU | 3326 | 28.197 | 55.075 | 17.290 | 1.00 | 20.08 |
| ATOM | 4714 | CD2 | LEU | 3326 | 27.315 | 54.682 | 14.976 | 1.00 | 17.56 |
| ATOM | 4715 | C | LEU | 3326 | 26.333 | 57.708 | 18.075 | 1.00 | 27.14 |
| ATOM | 4716 | O | LEU | 3326 | 25.902 | 58.557 | 17.300 | 1.00 | 28.80 |
| ATOM | 4717 | N | HIS | 3327 | 27.350 | 57.940 | 18.892 | 1.00 | 30.53 |
| ATOM | 4718 | CA | HIS | 3327 | 27.980 | 59.253 | 18.896 | 1.00 | 32.36 |
| ATOM | 4719 | CB | HIS | 3327 | 27.952 | 59.818 | 20.318 | 1.00 | 34.97 |
| ATOM | 4720 | CG | HIS | 3327 | 28.135 | 61.304 | 20.380 | 1.00 | 42.68 |
| ATOM | 4721 | CD2 | HIS | 3327 | 28.575 | 62.189 | 19.457 | 1.00 | 45.04 |
| ATOM | 4722 | ND1 | HIS | 3327 | 27.860 | 62.038 | 21.515 | 1.00 | 45.87 |
| ATOM | 4723 | CE1 | HIS | 3327 | 28.124 | 63.313 | 21.284 | 1.00 | 45.71 |
| ATOM | 4724 | NE2 | HIS | 3327 | 28.560 | 63.433 | 20.045 | 1.00 | 44.63 |
| ATOM | 4725 | C | HIS | 3327 | 29.400 | 59.293 | 18.317 | 1.00 | 30.23 |
| ATOM | 4726 | O | HIS | 3327 | 30.319 | 58.662 | 18.826 | 1.00 | 29.19 |
| ATOM | 4727 | N | LEU | 3328 | 29.561 | 60.040 | 17.234 | 1.00 | 28.95 |
| ATOM | 4728 | CA | LEU | 3328 | 30.857 | 60.180 | 16.595 | 1.00 | 30.99 |
| ATOM | 4729 | CB | LEU | 3328 | 30.703 | 60.100 | 15.074 | 1.00 | 29.16 |
| ATOM | 4730 | CG | LEU | 3328 | 29.951 | 58.865 | 14.555 | 1.00 | 29.23 |
| ATOM | 4731 | CD1 | LEU | 3328 | 29.728 | 58.998 | 13.062 | 1.00 | 29.68 |
| ATOM | 4732 | CD2 | LEU | 3328 | 30.732 | 57.594 | 14.869 | 1.00 | 26.10 |
| ATOM | 4733 | C | LEU | 3328 | 31.422 | 61.534 | 17.007 | 1.00 | 33.81 |
| ATOM | 4734 | O | LEU | 3328 | 30.798 | 62.573 | 16.784 | 1.00 | 32.11 |
| ATOM | 4735 | N | ARG | 3329 | 32.600 | 61.518 | 17.623 | 1.00 | 37.31 |
| ATOM | 4736 | CA | ARG | 3329 | 33.235 | 62.750 | 18.077 | 1.00 | 39.81 |
| ATOM | 4737 | CB | ARG | 3329 | 34.451 | 62.424 | 18.939 | 1.00 | 40.20 |
| ATOM | 4738 | C | ARG | 3329 | 33.643 | 63.685 | 16.936 | 1.00 | 41.53 |
| ATOM | 4739 | O | ARG | 3329 | 32.839 | 63.984 | 16.052 | 1.00 | 43.65 |
| ATOM | 4740 | N | ASN | 3330 | 34.890 | 64.146 | 16.957 | 1.00 | 42.05 |
| ATOM | 4741 | CA | ASN | 3330 | 35.387 | 65.074 | 15.946 | 1.00 | 42.40 |
| ATOM | 4742 | CB | ASN | 3330 | 36.678 | 65.732 | 16.431 | 1.00 | 45.71 |
| ATOM | 4743 | CG | ASN | 3330 | 37.104 | 66.884 | 15.547 | 1.00 | 50.73 |

TABLE 2-continued

FGFR1 D2–D3 Complexed with FGF1

| ATOM | 4744 | OD1 | ASN | 3330 | 37.765 | 66.693 | 14.521 | 1.00 | 51.29 |
|---|---|---|---|---|---|---|---|---|---|
| ATOM | 4745 | ND2 | ASN | 3330 | 36.711 | 68.098 | 15.933 | 1.00 | 53.42 |
| ATOM | 4746 | C | ASN | 3330 | 35.612 | 64.418 | 14.595 | 1.00 | 40.92 |
| ATOM | 4747 | O | ASN | 3330 | 36.744 | 64.184 | 14.175 | 1.00 | 41.46 |
| ATOM | 4748 | N | VAL | 3331 | 34.506 | 64.154 | 13.916 | 1.00 | 39.86 |
| ATOM | 4749 | CA | VAL | 3331 | 34.482 | 63.510 | 12.612 | 1.00 | 38.36 |
| ATOM | 4750 | CB | VAL | 3331 | 33.044 | 63.514 | 12.083 | 1.00 | 36.46 |
| ATOM | 4751 | CG1 | VAL | 3331 | 33.009 | 63.151 | 10.607 | 1.00 | 35.11 |
| ATOM | 4752 | CG2 | VAL | 3331 | 32.221 | 62.536 | 12.897 | 1.00 | 35.94 |
| ATOM | 4753 | C | VAL | 3331 | 35.413 | 64.059 | 11.533 | 1.00 | 38.81 |
| ATOM | 4754 | O | VAL | 3331 | 35.677 | 65.254 | 11.476 | 1.00 | 39.52 |
| ATOM | 4755 | N | SER | 3332 | 35.900 | 63.155 | 10.684 | 1.00 | 39.14 |
| ATOM | 4756 | CA | SER | 3332 | 36.782 | 63.476 | 9.561 | 1.00 | 41.46 |
| ATOM | 4757 | CB | SER | 3332 | 38.215 | 63.009 | 9.842 | 1.00 | 42.72 |
| ATOM | 4758 | OG | SER | 3332 | 38.306 | 61.593 | 9.834 | 1.00 | 45.96 |
| ATOM | 4759 | C | SER | 3332 | 36.257 | 62.760 | 8.303 | 1.00 | 41.31 |
| ATOM | 4760 | O | SER | 3332 | 35.185 | 62.150 | 8.326 | 1.00 | 40.97 |
| ATOM | 4761 | N | PHE | 3333 | 37.006 | 62.832 | 7.208 | 1.00 | 39.77 |
| ATOM | 4762 | CA | PHE | 3333 | 36.580 | 62.170 | 5.984 | 1.00 | 40.03 |
| ATOM | 4763 | CB | PHE | 3333 | 37.557 | 62.455 | 4.838 | 1.00 | 40.48 |
| ATOM | 4764 | CG | PHE | 3333 | 37.425 | 63.836 | 4.262 | 1.00 | 42.80 |
| ATOM | 4765 | CD1 | PHE | 3333 | 38.497 | 64.724 | 4.291 | 1.00 | 44.08 |
| ATOM | 4766 | CD2 | PHE | 3333 | 36.218 | 64.261 | 3.710 | 1.00 | 41.76 |
| ATOM | 4767 | CE1 | PHE | 3333 | 38.366 | 66.017 | 3.783 | 1.00 | 43.95 |
| ATOM | 4768 | CE2 | PHE | 3333 | 36.080 | 65.549 | 3.201 | 1.00 | 40.09 |
| ATOM | 4769 | CZ | PHE | 3333 | 37.153 | 66.427 | 3.237 | 1.00 | 42.04 |
| ATOM | 4770 | C | PHE | 3333 | 36.470 | 60.668 | 6.192 | 1.00 | 40.10 |
| ATOM | 4771 | O | PHE | 3333 | 35.508 | 60.042 | 5.756 | 1.00 | 37.43 |
| ATOM | 4772 | N | GLU | 3334 | 37.459 | 60.093 | 6.869 | 1.00 | 41.76 |
| ATOM | 4773 | CA | GLU | 3334 | 37.462 | 58.660 | 7.115 | 1.00 | 41.91 |
| ATOM | 4774 | CB | GLU | 3334 | 38.665 | 58.259 | 7.963 | 1.00 | 44.33 |
| ATOM | 4775 | CG | GLU | 3334 | 38.832 | 56.755 | 8.062 | 1.00 | 51.69 |
| ATOM | 4776 | CD | GLU | 3334 | 39.519 | 56.324 | 9.340 | 1.00 | 56.76 |
| ATOM | 4777 | OE1 | GLU | 3334 | 40.658 | 56.776 | 9.582 | 1.00 | 59.33 |
| ATOM | 4778 | OE2 | GLU | 3334 | 38.919 | 55.531 | 10.104 | 1.00 | 59.43 |
| ATOM | 4779 | CG | GLU | 3334 | 36.179 | 58.214 | 7.810 | 1.00 | 39.11 |
| ATOM | 4780 | O | GLU | 3334 | 35.738 | 57.074 | 7.654 | 1.00 | 39.71 |
| ATOM | 4781 | N | ASP | 3335 | 35.582 | 59.111 | 8.579 | 1.00 | 35.54 |
| ATOM | 4782 | CA | ASP | 3335 | 34.349 | 58.788 | 9.280 | 1.00 | 33.54 |
| ATOM | 4783 | CB | ASP | 3335 | 34.019 | 59.886 | 10.300 | 1.00 | 36.08 |
| ATOM | 4784 | CG | ASP | 3335 | 35.021 | 59.951 | 11.438 | 1.00 | 37.24 |
| ATOM | 4785 | OD1 | ASP | 3335 | 35.176 | 58.940 | 12.148 | 1.00 | 38.81 |
| ATOM | 4786 | OD2 | ASP | 3335 | 35.651 | 61.012 | 11.628 | 1.00 | 36.88 |
| ATOM | 4787 | C | ASP | 3335 | 33.185 | 58.631 | 8.298 | 1.00 | 30.04 |
| ATOM | 4788 | O | ASP | 3335 | 32.156 | 58.029 | 8.616 | 1.00 | 27.28 |
| ATOM | 4789 | N | ALA | 3336 | 33.344 | 59.177 | 7.102 | 1.00 | 28.20 |
| ATOM | 4790 | CA | ALA | 3336 | 32.280 | 59.082 | 6.116 | 1.00 | 28.61 |
| ATOM | 4791 | CB | ALA | 3336 | 32.669 | 59.814 | 4.835 | 1.00 | 27.15 |
| ATOM | 4792 | C | ALA | 3336 | 32.003 | 57.614 | 5.827 | 1.00 | 27.66 |
| ATOM | 4793 | O | ALA | 3336 | 32.885 | 56.770 | 5.972 | 1.00 | 25.77 |
| ATOM | 4794 | N | GLY | 3337 | 30.767 | 57.311 | 5.440 | 1.00 | 26.67 |
| ATOM | 4795 | CA | GLY | 3337 | 30.417 | 55.942 | 5.130 | 1.00 | 25.15 |
| ATOM | 4796 | C | GLY | 3337 | 29.093 | 55.504 | 5.701 | 1.00 | 25.47 |
| ATOM | 4797 | O | GLY | 3337 | 28.368 | 56.292 | 6.303 | 1.00 | 26.07 |
| ATOM | 4798 | N | GLU | 3338 | 28.790 | 54.222 | 5.530 | 1.00 | 26.41 |
| ATOM | 4799 | CA | GLU | 3338 | 27.536 | 53.653 | 6.000 | 1.00 | 24.31 |
| ATOM | 4800 | CB | GLU | 3338 | 27.053 | 52.616 | 4.989 | 1.00 | 25.61 |
| ATOM | 4801 | CG | GLU | 3338 | 25.817 | 51.840 | 5.414 | 1.00 | 32.75 |
| ATOM | 4802 | CD | GLU | 3338 | 25.319 | 50.907 | 4.320 | 1.00 | 35.06 |
| ATOM | 4803 | OE1 | GLU | 3338 | 26.163 | 50.234 | 3.679 | 1.00 | 36.67 |
| ATOM | 4804 | OE2 | GLU | 3338 | 24.087 | 50.844 | 4.109 | 1.00 | 34.11 |
| ATOM | 4805 | C | GLU | 3338 | 27.583 | 53.034 | 7.398 | 1.00 | 23.74 |
| ATOM | 4806 | O | LEU | 3338 | 28.500 | 52.294 | 7.737 | 1.00 | 19.53 |
| ATOM | 4807 | N | TYR | 3339 | 26.574 | 53.351 | 8.204 | 1.00 | 24.95 |
| ATOM | 4808 | CA | TYR | 3339 | 26.474 | 52.825 | 9.554 | 1.00 | 23.86 |
| ATOM | 4809 | CB | TYR | 3339 | 26.518 | 53.952 | 10.585 | 1.00 | 24.35 |
| ATOM | 4810 | CG | TYR | 3339 | 27.847 | 54.638 | 10.645 | 1.00 | 26.70 |
| ATOM | 4811 | CD1 | TYR | 3339 | 28.227 | 55.545 | 9.659 | 1.00 | 27.89 |
| ATOM | 4812 | CE1 | TYR | 3339 | 29.474 | 56.161 | 9.692 | 1.00 | 32.57 |
| ATOM | 4813 | CD2 | TYR | 3339 | 28.747 | 54.359 | 11.674 | 1.00 | 28.26 |
| ATOM | 4814 | CE2 | TYR | 3339 | 30.002 | 54.965 | 11.721 | 1.00 | 30.08 |
| ATOM | 4815 | CZ | TYR | 3339 | 30.359 | 55.868 | 10.728 | 1.00 | 32.77 |
| ATOM | 4816 | OH | TYR | 3339 | 31.592 | 56.482 | 10.771 | 1.00 | 34.79 |
| ATOM | 4817 | C | TYR | 3339 | 25.181 | 52.059 | 9.715 | 1.00 | 23.89 |
| ATOM | 4818 | O | TYR | 3339 | 24.203 | 52.340 | 9.028 | 1.00 | 25.21 |
| ATOM | 4819 | N | THR | 3340 | 25.186 | 51.103 | 10.643 | 1.00 | 23.89 |
| ATOM | 4820 | CA | THR | 3340 | 24.028 | 50.265 | 10.916 | 1.00 | 22.98 |

TABLE 2-continued

FGFR1 D2–D3 Complexed with FGF1

| ATOM | 4821 | CB | THR | 3340 | 24.203 | 48.853 | 10.293 | 1.00 | 21.86 |
|---|---|---|---|---|---|---|---|---|---|
| ATOM | 4822 | OG1 | THR | 3340 | 24.075 | 48.934 | 8.874 | 1.00 | 18.87 |
| ATOM | 4823 | CG2 | THR | 3340 | 23.158 | 47.889 | 10.839 | 1.00 | 22.00 |
| ATOM | 4824 | C | THR | 3340 | 23.735 | 50.074 | 12.402 | 1.00 | 23.05 |
| ATOM | 4825 | O | THR | 3340 | 24.635 | 49.893 | 13.225 | 1.00 | 19.63 |
| ATOM | 4826 | N | CYS | 3341 | 22.452 | 50.114 | 12.722 | 1.00 | 25.37 |
| ATOM | 4827 | CA | CYS | 3341 | 21.991 | 49.893 | 14.076 | 1.00 | 27.60 |
| ATOM | 4828 | C | CYS | 3341 | 21.339 | 48.514 | 14.013 | 1.00 | 27.96 |
| ATOM | 4829 | O | CYS | 3341 | 20.367 | 48.316 | 13.290 | 1.00 | 28.46 |
| ATOM | 4830 | CB | CYS | 3341 | 20.951 | 50.938 | 14.484 | 1.00 | 28.73 |
| ATOM | 4831 | SG | CYS | 3341 | 20.192 | 50.580 | 16.106 | 1.00 | 35.79 |
| ATOM | 4832 | N | LEU | 3342 | 21.890 | 47.560 | 14.757 | 1.00 | 27.49 |
| ATOM | 4833 | CA | LEU | 3342 | 21.363 | 46.206 | 14.778 | 1.00 | 24.07 |
| ATOM | 4834 | CB | LEU | 3342 | 22.454 | 45.207 | 14.376 | 1.00 | 23.74 |
| ATOM | 4835 | CG | LEU | 3342 | 22.026 | 43.755 | 14.114 | 1.00 | 27.37 |
| ATOM | 4836 | CD1 | LEU | 3342 | 23.123 | 43.028 | 13.334 | 1.00 | 25.92 |
| ATOM | 4837 | CD2 | LEU | 3342 | 21.723 | 43.042 | 15.425 | 1.00 | 24.75 |
| ATOM | 4838 | C | LEU | 3342 | 20.827 | 45.860 | 16.159 | 1.00 | 22.92 |
| ATOM | 4839 | O | LEU | 3342 | 21.451 | 46.152 | 17.182 | 1.00 | 21.73 |
| ATOM | 4840 | N | ALA | 3343 | 19.650 | 45.249 | 16.169 | 1.00 | 21.21 |
| ATOM | 4841 | CA | ALA | 3343 | 18.997 | 44.826 | 17.393 | 1.00 | 20.79 |
| ATOM | 4842 | CB | ALA | 3343 | 17.799 | 45.726 | 17.692 | 1.00 | 21.86 |
| ATOM | 4843 | C | ALA | 3343 | 18.534 | 43.390 | 17.178 | 1.00 | 20.82 |
| ATOM | 4844 | O | ALA | 3343 | 18.058 | 43.039 | 16.088 | 1.00 | 21.13 |
| ATOM | 4845 | N | GLY | 3344 | 18.666 | 42.563 | 18.209 | 1.00 | 17.15 |
| ATOM | 4846 | CA | GLY | 3344 | 18.244 | 41.188 | 18.073 | 1.00 | 17.04 |
| ATOM | 4847 | C | GLY | 3344 | 17.772 | 40.569 | 19.365 | 1.00 | 18.04 |
| ATOM | 4848 | O | GLY | 3344 | 18.237 | 40.938 | 20.448 | 1.00 | 19.90 |
| ATOM | 4849 | N | ASN | 3345 | 16.824 | 39.644 | 19.257 | 1.00 | 16.54 |
| ATOM | 4850 | CA | ASN | 3345 | 16.337 | 38.950 | 20.429 | 1.00 | 20.08 |
| ATOM | 4851 | CB | ASN | 3345 | 14.943 | 39.451 | 20.852 | 1.00 | 23.76 |
| ATOM | 4852 | CG | ASN | 3345 | 13.883 | 39.209 | 19.807 | 1.00 | 25.69 |
| ATOM | 4853 | OD1 | ASN | 3345 | 13.806 | 38.125 | 19.226 | 1.00 | 27.26 |
| ATOM | 4854 | ND2 | ASN | 3345 | 13.039 | 40.214 | 19.572 | 1.00 | 24.39 |
| ATOM | 4855 | C | ASN | 3345 | 16.320 | 37.465 | 20.117 | 1.00 | 20.29 |
| ATOM | 4856 | O | ASN | 3345 | 16.736 | 37.047 | 19.039 | 1.00 | 19.27 |
| ATOM | 4857 | N | SER | 3346 | 15.838 | 36.666 | 21.060 | 1.00 | 20.72 |
| ATOM | 4858 | CA | SER | 3346 | 15.808 | 35.231 | 20.868 | 1.00 | 19.34 |
| ATOM | 4859 | CB | SER | 3346 | 15.228 | 34.551 | 22.095 | 1.00 | 20.12 |
| ATOM | 4860 | OG | SER | 3346 | 13.819 | 34.647 | 22.082 | 1.00 | 26.95 |
| ATOM | 4861 | C | SER | 3346 | 15.040 | 34.775 | 19.638 | 1.00 | 19.31 |
| ATOM | 4862 | O | SER | 3346 | 15.288 | 33.678 | 19.147 | 1.00 | 22.73 |
| ATOM | 4863 | N | ILE | 3347 | 14.109 | 35.585 | 19.141 | 1.00 | 17.32 |
| ATOM | 4864 | CA | ILE | 3347 | 13.347 | 35.189 | 17.954 | 1.00 | 17.57 |
| ATOM | 4865 | CB | ILE | 3347 | 11.964 | 35.906 | 17.878 | 1.00 | 17.04 |
| ATOM | 4866 | CG2 | ILE | 3347 | 11.324 | 35.644 | 16.520 | 1.00 | 14.02 |
| ATOM | 4867 | CG1 | ILE | 3347 | 11.008 | 35.366 | 18.946 | 1.00 | 15.83 |
| ATOM | 4868 | CD1 | ILE | 3347 | 11.542 | 35.388 | 20.341 | 1.00 | 16.40 |
| ATOM | 4869 | C | ILE | 3347 | 14.115 | 35.447 | 16.643 | 1.00 | 17.76 |
| ATOM | 4870 | O | ILE | 3347 | 14.223 | 34.569 | 15.787 | 1.00 | 18.04 |
| ATOM | 4871 | N | GLY | 3348 | 14.645 | 36.650 | 16.493 | 1.00 | 15.82 |
| ATOM | 4872 | CA | GLY | 3348 | 15.389 | 36.981 | 15.300 | 1.00 | 17.40 |
| ATOM | 4873 | C | GLY | 3348 | 16.071 | 38.324 | 15.475 | 1.00 | 19.13 |
| ATOM | 4874 | O | GLY | 3348 | 16.068 | 38.890 | 16.561 | 1.00 | 18.77 |
| ATOM | 4875 | N | LEU | 3349 | 16.658 | 38.853 | 14.415 | 1.00 | 20.47 |
| ATOM | 4876 | CA | LEU | 3349 | 17.314 | 40.130 | 14.552 | 1.00 | 21.34 |
| ATOM | 4877 | CB | LEU | 3349 | 18.831 | 39.928 | 14.590 | 1.00 | 22.11 |
| ATOM | 4878 | CG | LEU | 3349 | 19.598 | 39.437 | 13.373 | 1.00 | 20.52 |
| ATOM | 4879 | CD1 | LEU | 3349 | 19.815 | 40.602 | 12.421 | 1.00 | 23.69 |
| ATOM | 4880 | CD2 | LEU | 3349 | 20.940 | 38.868 | 13.815 | 1.00 | 19.06 |
| ATOM | 4881 | C | LEU | 3349 | 16.894 | 41.072 | 13.437 | 1.00 | 23.13 |
| ATOM | 4882 | O | LEU | 3349 | 16.408 | 40.628 | 12.406 | 1.00 | 23.32 |
| ATOM | 4883 | N | SER | 3350 | 17.061 | 42.376 | 13.657 | 1.00 | 25.95 |
| ATOM | 4884 | CA | SER | 3350 | 16.677 | 43.380 | 12.660 | 1.00 | 23.88 |
| ATOM | 4885 | CB | SER | 3350 | 15.323 | 43.989 | 13.024 | 1.00 | 22.02 |
| ATOM | 4886 | OG | SER | 3350 | 14.564 | 43.127 | 13.856 | 1.00 | 20.06 |
| ATOM | 4887 | C | SER | 3350 | 17.702 | 44.503 | 12.618 | 1.00 | 23.27 |
| ATOM | 4888 | O | SER | 3350 | 18.470 | 44.670 | 13.552 | 1.00 | 24.39 |
| ATOM | 4889 | N | HIS | 3351 | 17.708 | 45.273 | 11.538 | 1.00 | 23.70 |
| ATOM | 4890 | CA | HIS | 3351 | 18.622 | 46.403 | 11.439 | 1.00 | 25.12 |
| ATOM | 4891 | CB | HIS | 3351 | 20.066 | 45.935 | 11.248 | 1.00 | 26.03 |
| ATOM | 4892 | CG | HIS | 3351 | 20.311 | 45.254 | 9.942 | 1.00 | 28.05 |
| ATOM | 4893 | CD2 | HIS | 3351 | 20.947 | 45.670 | 8.821 | 1.00 | 28.57 |
| ATOM | 4894 | ND1 | HIS | 3351 | 19.876 | 43.973 | 9.683 | 1.00 | 28.17 |
| ATOM | 4895 | CE1 | HIS | 3351 | 20.236 | 43.626 | 8.461 | 1.00 | 25.88 |
| ATOM | 4896 | NE2 | HIS | 3351 | 20.888 | 44.636 | 7.916 | 1.00 | 27.45 |
| ATOM | 4897 | C | HIS | 3351 | 18.268 | 47.385 | 10.335 | 1.00 | 25.20 |

TABLE 2-continued

| | | | | | | | | | |
|---|---|---|---|---|---|---|---|---|---|
| FGFR1 D2–D3 Complexed with FGF1 | | | | | | | | | |
| ATOM | 4898 | O | HIS | 3351 | 17.614 | 47.038 | 9.355 | 1.00 | 27.97 |
| ATOM | 4899 | N | HIS | 3352 | 18.707 | 48.622 | 10.527 | 1.00 | 25.02 |
| ATOM | 4900 | CA | HIS | 3352 | 18.498 | 49.708 | 9.581 | 1.00 | 22.68 |
| ATOM | 4901 | CB | HIS | 3352 | 17.509 | 50.733 | 10.124 | 1.00 | 22.61 |
| ATOM | 4902 | CG | HIS | 3352 | 16.093 | 50.258 | 10.172 | 1.00 | 24.89 |
| ATOM | 4903 | CD2 | HIS | 3352 | 15.552 | 49.031 | 9.994 | 1.00 | 25.59 |
| ATOM | 4904 | ND1 | HIS | 3352 | 15.043 | 51.100 | 10.472 | 1.00 | 27.28 |
| ATOM | 4905 | CE1 | HIS | 3352 | 13.916 | 50.411 | 10.481 | 1.00 | 27.37 |
| ATOM | 4906 | NE2 | HIS | 3352 | 14.197 | 49.152 | 10.194 | 1.00 | 29.53 |
| ATOM | 4907 | C | HIS | 3352 | 19.856 | 50.369 | 9.435 | 1.00 | 22.26 |
| ATOM | 4908 | O | HIS | 3352 | 20.671 | 50.347 | 10.363 | 1.00 | 20.06 |
| ATOM | 4909 | N | SER | 3353 | 20.109 | 50.950 | 8.273 | 1.00 | 21.46 |
| ATOM | 4910 | CA | SER | 3353 | 21.382 | 51.606 | 8.047 | 1.00 | 22.89 |
| ATOM | 4911 | CB | SER | 3353 | 22.185 | 50.828 | 7.013 | 1.00 | 24.69 |
| ATOM | 4912 | OG | SER | 3353 | 22.276 | 49.466 | 7.388 | 1.00 | 27.42 |
| ATOM | 4913 | C | SER | 3353 | 21.180 | 53.035 | 7.580 | 1.00 | 23.21 |
| ATOM | 4914 | O | SER | 3353 | 20.061 | 53.441 | 7.281 | 1.00 | 24.15 |
| ATOM | 4915 | N | ALA | 3354 | 22.267 | 53.797 | 7.537 | 1.00 | 23.66 |
| ATOM | 4916 | CA | ALA | 3354 | 22.226 | 55.191 | 7.104 | 1.00 | 24.08 |
| ATOM | 4917 | CB | ALA | 3354 | 21.800 | 56.094 | 8.250 | 1.00 | 21.96 |
| ATOM | 4918 | C | ALA | 3354 | 23.610 | 55.569 | 6.613 | 1.00 | 23.61 |
| ATOM | 4919 | O | ALA | 3354 | 24.589 | 54.890 | 6.929 | 1.00 | 23.28 |
| ATOM | 4920 | N | TRP | 3355 | 23.688 | 56.634 | 5.816 | 1.00 | 25.31 |
| ATOM | 4921 | CA | TRP | 3355 | 24.971 | 57.084 | 5.265 | 1.00 | 28.33 |
| ATOM | 4922 | CB | TRP | 3355 | 24.919 | 57.091 | 3.733 | 1.00 | 34.37 |
| ATOM | 4923 | CG | TRP | 3355 | 26.122 | 56.457 | 3.088 | 1.00 | 41.09 |
| ATOM | 4924 | CD2 | TRP | 3355 | 27.356 | 57.106 | 2.749 | 1.00 | 43.54 |
| ATOM | 4925 | CE2 | TRP | 3355 | 28.230 | 56.113 | 2.244 | 1.00 | 44.52 |
| ATOM | 4926 | CE3 | TRP | 3355 | 27.814 | 58.433 | 2.824 | 1.00 | 46.23 |
| ATOM | 4927 | CD1 | TRP | 3355 | 26.289 | 55.130 | 2.778 | 1.00 | 42.95 |
| ATOM | 4928 | NE1 | TRP | 3355 | 27.552 | 54.918 | 2.271 | 1.00 | 44.11 |
| ATOM | 4929 | CZ2 | TRP | 3355 | 29.538 | 56.403 | 1.819 | 1.00 | 46.99 |
| ATOM | 4930 | CZ3 | TRP | 3355 | 29.125 | 58.725 | 2.395 | 1.00 | 46.82 |
| ATOM | 4931 | CH2 | TRP | 3355 | 29.966 | 57.710 | 1.903 | 1.00 | 47.21 |
| ATOM | 4932 | C | TRP | 3355 | 25.369 | 58.464 | 5.784 | 1.00 | 27.48 |
| ATOM | 4933 | O | TRP | 3355 | 24.548 | 59.400 | 5.818 | 1.00 | 24.86 |
| ATOM | 4934 | N | LEU | 3356 | 26.618 | 58.581 | 6.210 | 1.00 | 26.25 |
| ATOM | 4935 | CA | LEU | 3356 | 27.137 | 59.820 | 6.743 | 1.00 | 24.44 |
| ATOM | 4936 | CB | LEU | 3356 | 27.968 | 59.567 | 7.987 | 1.00 | 26.37 |
| ATOM | 4937 | CG | LEU | 3356 | 28.642 | 60.839 | 8.517 | 1.00 | 26.66 |
| ATOM | 4938 | CD1 | LEU | 3356 | 27.578 | 61.699 | 9.187 | 1.00 | 25.57 |
| ATOM | 4939 | CD2 | LEU | 3356 | 29.746 | 60.490 | 9.505 | 1.00 | 25.10 |
| ATOM | 4940 | C | LEU | 3356 | 28.003 | 60.498 | 5.710 | 1.00 | 23.94 |
| ATOM | 4941 | O | LEU | 3356 | 29.026 | 59.954 | 5.285 | 1.00 | 20.62 |
| ATOM | 4942 | N | THR | 3357 | 27.598 | 61.683 | 5.307 | 1.00 | 26.42 |
| ATOM | 4943 | CA | THR | 3357 | 28.376 | 62.416 | 4.323 | 1.00 | 26.09 |
| ATOM | 4944 | CB | THR | 3357 | 27.459 | 63.010 | 3.267 | 1.00 | 25.60 |
| ATOM | 4945 | OG1 | THR | 3357 | 26.573 | 61.984 | 2.793 | 1.00 | 30.06 |
| ATOM | 4946 | CG2 | THR | 3357 | 28.265 | 63.514 | 2.110 | 1.00 | 26.38 |
| ATOM | 4947 | C | THR | 3357 | 29.198 | 63.499 | 4.993 | 1.00 | 23.29 |
| ATOM | 4948 | O | THR | 3357 | 28.696 | 64.243 | 5.836 | 1.00 | 21.43 |
| ATOM | 4949 | N | VAL | 3358 | 30.465 | 63.579 | 4.618 | 1.00 | 20.55 |
| ATOM | 4950 | CA | VAL | 3358 | 31.325 | 64.568 | 5.231 | 1.00 | 22.35 |
| ATOM | 4951 | CB | VAL | 3358 | 32.469 | 63.889 | 5.973 | 1.00 | 23.52 |
| ATOM | 4952 | CG1 | VAL | 3358 | 33.132 | 64.901 | 6.887 | 1.00 | 24.27 |
| ATOM | 4953 | CG2 | VAL | 3358 | 31.934 | 62.693 | 6.755 | 1.00 | 20.28 |
| ATOM | 4954 | C | VAL | 3358 | 31.880 | 65.595 | 4.248 | 1.00 | 22.21 |
| ATOM | 4955 | O | VAL | 3358 | 32.343 | 65.253 | 3.155 | 1.00 | 16.76 |
| ATOM | 4956 | N | LEU | 3359 | 31.834 | 66.863 | 4.661 | 1.00 | 24.15 |
| ATOM | 4957 | CA | LEU | 3359 | 32.276 | 67.973 | 3.822 | 1.00 | 25.25 |
| ATOM | 4958 | CB | LEU | 3359 | 31.050 | 68.821 | 3.465 | 1.00 | 21.53 |
| ATOM | 4959 | CG | LEU | 3359 | 29.968 | 68.004 | 2.752 | 1.00 | 20.11 |
| ATOM | 4960 | CD1 | LEU | 3359 | 28.734 | 68.857 | 2.488 | 1.00 | 18.40 |
| ATOM | 4961 | CD2 | LEU | 3359 | 30.553 | 67.447 | 1.448 | 1.00 | 16.31 |
| ATOM | 4962 | C | LEU | 3359 | 33.383 | 68.851 | 4.404 | 1.00 | 26.37 |
| ATOM | 4963 | O | LEU | 3359 | 33.406 | 69.014 | 5.644 | 1.00 | 31.30 |
| ATOM | 4964 | S | SO4 | 4000 | 5.633 | 24.099 | 44.777 | 1.00 | 72.77 |
| ATOM | 4965 | O1 | SO4 | 4000 | 4.278 | 23.915 | 44.236 | 1.00 | 73.25 |
| ATOM | 4966 | O2 | SO4 | 4000 | 6.603 | 23.359 | 43.945 | 1.00 | 72.28 |
| ATOM | 4967 | O3 | SO4 | 4000 | 5.958 | 25.529 | 44.784 | 1.00 | 72.55 |
| ATOM | 4968 | O4 | SO4 | 4000 | 5.678 | 23.586 | 46.157 | 1.00 | 75.61 |
| ATOM | 4969 | S | SO4 | 4001 | 10.965 | 21.084 | 46.120 | 1.00 | 83.74 |
| ATOM | 4970 | O1 | SO4 | 4001 | 12.014 | 21.413 | 47.103 | 1.00 | 84.81 |
| ATOM | 4971 | O2 | SO4 | 4001 | 11.205 | 19.741 | 45.559 | 1.00 | 83.81 |
| ATOM | 4972 | O3 | SO4 | 4001 | 9.641 | 21.112 | 46.776 | 1.00 | 83.46 |
| ATOM | 4973 | O4 | SO4 | 4001 | 11.008 | 22.071 | 45.032 | 1.00 | 84.31 |
| ATOM | 4974 | S | SO4 | 4002 | −2.986 | 74.153 | −11.455 | 1.00 | 58.62 |

TABLE 2-continued

FGFR1 D2–D3 Complexed with FGF1

| ATOM | 4975 | O1 | SO4 | 4002 | −1.886 | 73.544 | −12.230 | 1.00 | 56.25 |
| ATOM | 4976 | O2 | SO4 | 4002 | −3.387 | 73.255 | −10.356 | 1.00 | 57.05 |
| ATOM | 4977 | O3 | SO4 | 4002 | −2.542 | 75.460 | −10.941 | 1.00 | 59.05 |
| ATOM | 4978 | O4 | SO4 | 4002 | −4.157 | 74.370 | −12.323 | 1.00 | 63.86 |
| ATOM | 4979 | S  | SO4 | 4003 |  0.500 | 75.090 |  −5.675 | 1.00 | 41.03 |
| ATOM | 4980 | O1 | SO4 | 4003 |  0.983 | 74.248 |  −6.786 | 1.00 | 39.49 |
| ATOM | 4981 | O2 | SO4 | 4003 |  0.212 | 74.253 |  −4.505 | 1.00 | 44.82 |
| ATOM | 4982 | O3 | SO4 | 4003 |  1.532 | 76.084 |  −5.344 | 1.00 | 46.05 |
| ATOM | 4983 | O4 | SO4 | 4003 | −0.732 | 75.799 |  −6.055 | 1.00 | 44.94 |

TABLE 3

FGFR2(D2–D3) Complexed with FGF2

```
HEADER   GROWTH FACTOR/GROWTH FACTOR RECEPTOR 19-APR-00 1EV2
TITLE    CRYSTAL STRUCTURE OF FGF2 IN COMPLEX WITH THE EXTRACELLULAR
TITLE    2 LIGAND BINDING DOMAIN OF FGF RECEPTOR 2 (FGFR2)
COMPND   MOL_ID: 1;
COMPND   2 MOLECULE: FIBROBLAST GROWTH FACTOR 2;
COMPND   3 CHAIN: A, B, C, D;
COMPND   4 FRAGMENT: THE B-TREFOIL CORE OF FIBROBLAST GROWTH FACTOR 2;
COMPND   5 SYNONYM: FGF2;
COMPND   6 ENGINEERED: YES;
COMPND   7 MUTATION: YES;
COMPND   8 MOL_ID: 2;
COMPND   9 MOLECULE: FIBROBLAST GROWTH FACTOR RECEPTOR 2;
COMPND   10 CHAIN: E, F, G, H;
COMPND   11 FRAGMENT: EXTRACELLULAR LIGAND BINDING DOMAIN OF FGF
COMPND   12 RECEPTOR 2 CONSISTING OF IMMUNOGLOBULIN LIKE DOMAINS II
COMPND   13 (D2) AND III (D3);
COMPND   14 SYNONYM: FGFR2;
COMPND   15 ENGINEERED: YES
SOURCE   MOL_ID: 1;
SOURCE   2 ORGANISM_SCIENTIFIC: HOMO SAPIENS;
SOURCE   3 ORGANISM_COMMON: HUMAN;
SOURCE   4 EXPRESSION_SYSTEM_COMMON: BACTERIA;
SOURCE   5 EXPRESSION_SYSTEM_VECTOR_TYPE: PLASMID;
SOURCE   6 EXPRESSION_SYSTEM_PLASMID: PET15B;
SOURCE   7 MOL_ID: 2;
SOURCE   8 ORGANISM_SCIENTIFIC: HOMO SAPIENS;
SOURCE   9 ORGANISM_COMMON: HUMAN;
SOURCE   10 EXPRESSION_SYSTEM_COMMON: BACTERIA;
SOURCE   11 EXPRESSION_SYSTEM_VECTOR_TYPE: PLASMID;
SOURCE   12 EXPRESSION_SYSTEM_PLASMID: PET28A
KEYWDS   IMMUNOGLOBULIN (IG)LIKE DOMAINS BELONGING TO THE I-SET
KEYWDS   2 SUBGROUP WITHIN IG-LIKE DOMAINS, B-TREFOIL FOLD
EXPDTA   X-RAY DIFFRACTION
AUTHOR   A. N. PLOTNIKOV, S. R. HUBBARD, J. SCHLESSINGER, M. MOHAMMADI
REVDAT   1   31-MAY-00   1EV2 0
JRNL     AUTH A. N. PLOTNIKOV, S. R. HUBBARD, J. SCHLESSINGER,
JRNL     AUTH 2 M. MOHAMMADI
JRNL     TITL CRYSTAL STRUCTURES OF TWO FGF-FGFR COMPLEXES
JRNL     TITL 2 REVEAL THE DETERMINANTS OF LIGAND-RECEPTOR
JRNL     TITL 3 SPECIFICITY
JRNL     REF   CELL (CAMBRIDGE,MASS.)   V. 101   413 2000
JRNL     REFN   ASTM CELLB5 US ISSN 0092-8674
REMARK   1
REMARK   2
REMARK   2 RESOLUTION. 2.2 ANGSTROMS.
REMARK   3
REMARK   3 REFINEMENT.
REMARK   3   PROGRAM   : CNS
REMARK   3   AUTHORS   : BRUNGER, ADAMS, CLORE, DELANO, GROS, GROSSE-
REMARK   3             : KUNSTLEVE, JIANG, KUSZEWSKI, NILGES, PANNU,
REMARK   3             : READ, RICE, SIMONSON, WARREN
REMARK   3
REMARK   3 REFINEMENT TARGET: ENGH & HUBER
REMARK   3
REMARK   3 DATA USED IN REFINEMENT.
REMARK   3   RESOLUTION RANGE HIGH (ANGSTROMS) : 2.20
REMARK   3   RESOLUTION RANGE LOW  (ANGSTROMS) : 25.00
REMARK   3   DATA CUTOFF        (SIGMA(F)) : 0.000
REMARK   3   OUTLIER CUTOFF HIGH (RMS(ABS(F))) : NULL
REMARK   3   COMPLETENESS (WORKING+TEST) (%) : 91.7
```

TABLE 3-continued

FGFR2(D2–D3) Complexed with FGF2

```
REMARK   3  NUMBER OF REFLECTIONS       : 84816
REMARK   3
REMARK   3
REMARK   3 FIT TO DATA USED IN REFINEMENT.
REMARK   3   CROSS-VALIDATION METHOD          : NULL
REMARK   3   FREE R VALUE TEST SET SELECTION  : RANDOM
REMARK   3   R VALUE       (WORKING SET) : 0.248
REMARK   3   FREE R VALUE                : 0.273
REMARK   3   FREE R VALUE TEST SET SIZE   (%) : NULL
REMARK   3   FREE R VALUE TEST SET COUNT      : 4291
REMARK   3   ESTIMATED ERROR OF FREE R VALUE : NULL
REMARK   3
REMARK   3 FIT IN THE HIGHEST RESOLUTION BIN.
REMARK   3   TOTAL NUMBER OF BINS USED           : NULL
REMARK   3   BIN RESOLUTION RANGE HIGH       (A) : NULL
REMARK   3   BIN RESOLUTION RANGE LOW        (A) : NULL
REMARK   3   BIN COMPLETENESS (WORKING+TEST) (%) : NULL
REMARK   3   REFLECTIONS IN BIN   (WORKING SET) : NULL
REMARK   3   BIN R VALUE         (WORKING SET) : NULL
REMARK   3   BIN FREE R VALUE                 : NULL
REMARK   3   BIN FREE R VALUE TEST SET SIZE (%) : NULL
REMARK   3   BIN FREE R VALUE TEST SET COUNT      : NULL
REMARK   3   ESTIMATED ERROR OF BIN FREE R VALUE : NULL
REMARK   3
REMARK   3 NUMBER OF NON-HYDROGEN ATOMS USED IN REFINEMENT.
REMARK   3   PROTEIN ATOMS      : 9818
REMARK   3   NUCLEIC ACID ATOMS    : 0
REMARK   3   HETEROGEN ATOMS       : 20
REMARK   3   SOLVENT ATOMS        : 263
REMARK   3
REMARK   3 B VALUES.
REMARK   3 FROM WILSON PLOT        (A**2) : NULL
REMARK   3 MEAN B VALUE      (OVERALL, A**2) : NULL
REMARK   3 OVERALL ANISOTROPIC B VALUE.
REMARK   3   B11 (A**2) : -14.90300
REMARK   3   B22 (A**2) : -0.98800
REMARK   3   B33 (A**2) : 15.89200
REMARK   3   B12 (A**2) : 0.00000
REMARK   3   B13 (A**2) : 0.00000
REMARK   3   B23 (A**2) : -0.65800
REMARK   3
REMARK   3 ESTIMATED COORDINATE ERROR.
REMARK   3   ESD FROM LUZZATI PLOT    (A) : NULL
REMARK   3   ESD FROM SIGMAA          (A) : NULL
REMARK   3   LOW RESOLUTION CUTOFF    (A) : NULL
REMARK   3
REMARK   3 CROSS-VALIDATED ESTIMATED COORDINATE ERROR.
REMARK   3   ESD FROM C-V LUZZATI PLOT  (A) : NULL
REMARK   3   ESD FROM C-V SIGMAA        (A) : NULL
REMARK   3
REMARK   3 RMS DEVIATIONS FROM IDEAL VALUES.
REMARK   3   BOND LENGTHS           (A) : 0.007
REMARK   3   BOND ANGLES       (DEGREES) : 1.33
REMARK   3   DIHEDRAL ANGLES   (DEGREES) : NULL
REMARK   3   IMPROPER ANGLES   (DEGREES) : 0.78
REMARK   3
REMARK   3 ISOTROPIC THERMAL MODEL : NULL
REMARK   3
REMARK   3 ISOTROPIC THERMAL FACTOR RESTRAINTS.    RMS    SIGMA
REMARK   3   MAIN-CHAIN BOND       (A**2) : 0.87 ; 1.500
REMARK   3   MAIN-CHAIN ANGLE      (A**2) : 1.53 ; 2.000
REMARK   3   SIDE-CHAIN BOND       (A**2) : 1.16 ; 2.000
REMARK   3   SIDE-CHAIN ANGLE      (A**2) : 1.79 ; 2.500
REMARK   3
REMARK   3
REMARK   3 BULK SOLVENT MODELING.
REMARK   3   METHOD USED : CNS
REMARK   3   KSOL    : 0.38
REMARK   3   BSOL    : 47.84
REMARK   3
REMARK   3 NCS MODEL : NULL
REMARK   3
REMARK   3 NCS RESTRAINTS.                RMS SIGMA/WEIGHT
REMARK   3   GROUP 1 POSITIONAL     (A) : NULL ; NULL
REMARK   3   GROUP 1 B-FACTOR      (A**2) : NULL ; NULL
REMARK   3
REMARK   3 PARAMETER FILE 1 : NULL
```

TABLE 3-continued

FGFR2(D2–D3) Complexed with FGF2

```
REMARK   3  TOPOLOGY FILE 1 : NULL
REMARK   3
REMARK   3  OTHER REFINEMENT REMARKS: NULL
REMARK   4
REMARK   4 1EV2 COMPLIES WITH FORMAT V. 2.3, 09-JULY-1998
REMARK 100
REMARK 100 THIS ENTRY HAS BEEN PROCESSED BY RCSB ON 26-APR-2000.
REMARK 100 THE RCSB ID CODE IS RCSB010917.
REMARK 200
REMARK 200 EXPERIMENTAL DETAILS
REMARK 200  EXPERIMENT TYPE          : X-RAY DIFFRACTION
REMARK 200  DATE OF DATA COLLECTION  : 22-SEP-1999
REMARK 200  TEMPERATURE      (KELVIN) : 110.0
REMARK 200  PH               : 7.50
REMARK 200  NUMBER OF CRYSTALS USED   : 1
REMARK 200
REMARK 200  SYNCHROTRON        (Y/N) : Y
REMARK 200  RADIATION SOURCE        : NSLS
REMARK 200  BEAMLINE         : X4A
REMARK 200  X-RAY GENERATOR MODEL      : NULL
REMARK 200  MONOCHROMATIC OR LAUE   (M/L) : M
REMARK 200  WAVELENGTH OR RANGE    (A) : 0.9789
REMARK 200  MONOCHROMATOR         : NULL
REMARK 200  OPTICS            : NULL
REMARK 200
REMARK 200  DETECTOR TYPE         : CCD
REMARK 200  DETECTOR MANUFACTURER    : SDMS
REMARK 200  INTENSITY-INTEGRATION SOFTWARE : SDMS
REMARK 200  DATA SCALING SOFTWARE     : SCALEPACK
REMARK 200
REMARK 200  NUMBER OF UNIQUE REFLECTIONS   : 206913
REMARK 200  RESOLUTION RANGE HIGH    (A) : 2.200
REMARK 200  RESOLUTION RANGE LOW     (A) : 25.000
REMARK 200  REJECTION CRITERIA (SIGMA(I)) : 0.000
REMARK 200
REMARK 200 OVERALL.
REMARK 200  COMPLETENESS FOR RANGE   (%) : 96.3
REMARK 200  DATA REDUNDANCY         : 2.200
REMARK 200  R MERGE          (I) : 0.04200
REMARK 200  R SYM            (I) : NULL
REMARK 200  <I/SIGMA(I)> FOR THE DATA SET : 16.3000
REMARK 200
REMARK 200 IN THE HIGHEST RESOLUTION SHELL.
REMARK 200  HIGHEST RESOLUTION SHELL, RANGE HIGH (A) : 2.20
REMARK 200  HIGHEST RESOLUTION SHELL, RANGE LOW (A) : 2.28
REMARK 200  COMPLETENESS FOR SHELL   (%) : 87.8
REMARK 200  DATA REDUNDANCY IN SHELL    : NULL
REMARK 200  R MERGE FOR SHELL      (I) : 0.24100
REMARK 200  R SYM FOR SHELL       (I) : NULL
REMARK 200  <I/SIGMA(I)> FOR SHELL     : NULL
REMARK 200
REMARK 200 DIFFRACTION PROTOCOL: SINGLE WAVELENGTH
REMARK 200 METHOD USED TO DETERMINE THE STRUCTURE: NULL
REMARK 200 SOFTWARE USED: AMORE
REMARK 200 STARTING MODEL: NULL
REMARK 200
REMARK 200 REMARK: NULL
REMARK 280
REMARK 280 CRYSTAL
REMARK 280 SOLVENT CONTENT, VS (%): NULL
REMARK 280 MATTHEWS COEFFICIENT, VM (ANGSTROMS**3/DA): NULL
REMARK 280
REMARK 280 CRYSTALLIZATION CONDITIONS: PEG 4000, ISOPROPANOL, HEPES-
REMARK 280  NAOH
REMARK 290
REMARK 290 CRYSTALLOGRAPHIC SYMMETRY
REMARK 290 SYMMETRY OPERATORS FOR SPACE GROUP: P 1
REMARK 290
REMARK 290    SYMOP   SYMMETRY
REMARK 290   NNNMMM OPERATOR
REMARK 290    1555   X,Y,Z
REMARK 290
REMARK 290   WHERE NNN -> OPERATOR NUMBER
REMARK 290       MMM -> TRANSLATION VECTOR
REMARK 290
REMARK 290 CRYSTALLOGRAPHIC SYMMETRY TRANSFORMATIONS
REMARK 290 THE FOLLOWING TRANSFORMATIONS OPERATE ON THE ATOM/HETATM
```

TABLE 3-continued

| FGFR2(D2–D3) Complexed with FGF2 |
|---|

```
REMARK 290 RECORDS IN THIS ENTRY TO PRODUCE CRYSTALLOGRAPHICALLY
REMARK 290 RELATED MOLECULES.
REMARK 290   SMTRY1   1 1.000000 0.000000 0.000000      0.00000
REMARK 290   SMTRY2   1 0.000000 1.000000 0.000000      0.00000
REMARK 290   SMTRY3   1 0.000000 0.000000 1.000000      0.00000
REMARK 290
REMARK 290 REMARK: NULL
REMARK 300
REMARK 300 BIOMOLECULE: 1
REMARK 300 THIS ENTRY CONTAINS THE CRYSTALLOGRAPHIC ASYMMETRIC UNIT
REMARK 300 WHICH CONSISTS OF 8 CHAIN(S). SEE REMARK 350 FOR
REMARK 300 INFORMATION ON GENERATING THE BIOLOGICAL MOLECULE(S).
REMARK 350
REMARK 350 GENERATING THE BIOMOLECULE
REMARK 350 COORDINATES FOR A COMPLETE MULTIMER REPRESENTING THE KNOWN
REMARK 350 BIOLOGICALLY SIGNIFICANT OLIGOMERIZATION STATE OF THE
REMARK 350 MOLECULE CAN BE GENERATED BY APPLYING BIOMT TRANSFORMATIONS
REMARK 350 GIVEN BELOW. BOTH NON-CRYSTALLOGRAPHIC AND
REMARK 350 CRYSTALLOGRAPHIC OPERATIONS ARE GIVEN.
REMARK 350
REMARK 350 BIOMOLECULE: 1
REMARK 350 APPLY THE FOLLOWING TO CHAINS: A, B, C, D, E, F, G, H
REMARK 350   BIOMT1   1 1.000000 0.000000 0.000000   0.00000
REMARK 350   BIOMT2   1 0.000000 1.000000 0.000000   0.00000
REMARK 350   BIOMT3   1 0.000000 0.000000 1.000000   0.00000
REMARK 465
REMARK 465 MISSING RESIDUES
REMARK 465 THE FOLLOWING RESIDUES WERE NOT LOCATED IN THE
REMARK 465 EXPERIMENT. (M=MODEL NUMBER; RES=RESIDUE NAME; C=CHAIN
REMARK 465 IDENTIFIER; SSSEQ=SEQUENCE NUMBER; I=INSERTION CODE.)
REMARK 465
REMARK 465   M RES C SSSEQI
REMARK 465     GLY A    15
REMARK 465     SER A   146
REMARK 465     GLY B    15
REMARK 465     SER B   146
REMARK 465     GLY C    15
REMARK 465     SER C   146
REMARK 465     GLY D    15
REMARK 465     SER D   146
REMARK 465     ASN E   147
REMARK 465     SER E   148
REMARK 465     ASN E   149
REMARK 465     THR E   268
REMARK 465     VAL E   269
REMARK 465     VAL E   270
REMARK 465     GLY E   271
REMARK 465     GLY E   272
REMARK 465     GLU E   295
REMARK 465     LYS E   296
REMARK 465     ASN E   297
REMARK 465     GLY E   298
REMARK 465     SER E   299
REMARK 465     LYS E   300
REMARK 465     TYR E   301
REMARK 465     GLY E   302
REMARK 465     PRO E   303
REMARK 465     ASP E   304
REMARK 465     GLY E   305
REMARK 465     LEU E   306
REMARK 465     PRO E   361
REMARK 465     ALA E   362
REMARK 465     PRO E   363
REMARK 465     GLY E   364
REMARK 465     ARG E   365
REMARK 465     GLU E   366
REMARK 465     ASN F   147
REMARK 465     SER F   148
REMARK 465     ASN F   149
REMARK 465     GLY F   272
REMARK 465     VAL F   294
REMARK 465     GLU F   295
REMARK 465     LYS F   296
REMARK 465     ASN F   297
REMARK 465     GLY F   298
REMARK 465     SER F   299
REMARK 465     LYS F   300
```

TABLE 3-continued

FGFR2(D2–D3) Complexed with FGF2

```
REMARK 465      TYR F   301
REMARK 465      GLY F   302
REMARK 465      PRO F   303
REMARK 465      ASP F   304
REMARK 465      GLY F   305
REMARK 465      LEU F   306
REMARK 465      PRO F   307
REMARK 465      LEU F   360
REMARK 465      PRO F   361
REMARK 465      ALA F   362
REMARK 465      PRO F   363
REMARK 465      GLY F   364
REMARK 465      ARG F   365
REMARK 465      GLU F   366
REMARK 465      ASN G   147
REMARK 465      SER G   148
REMARK 465      ASN G   149
REMARK 465      ASN G   150
REMARK 465      GLU G   295
REMARK 465      LYS G   296
REMARK 465      ASN G   297
REMARK 465      GLY G   298
REMARK 465      SER G   299
REMARK 465      LYS G   300
REMARK 465      TYR G   301
REMARK 465      GLY G   302
REMARK 465      PRO G   303
REMARK 465      ASP G   304
REMARK 465      GLY G   305
REMARK 465      LEU G   306
REMARK 465      PRO G   307
REMARK 465      GLY G   364
REMARK 465      ARG G   365
REMARK 465      GLU G   366
REMARK 465      ASN H   147
REMARK 465      SER H   148
REMARK 465      ASN H   149
REMARK 465      ASN H   150
REMARK 465      GLU H   295
REMARK 465      LYS H   296
REMARK 465      ASN H   297
REMARK 465      GLY H   298
REMARK 465      SER H   299
REMARK 465      LYS H   300
REMARK 465      TYR H   301
REMARK 465      GLY H   302
REMARK 465      PRO H   303
REMARK 465      ASP H   304
REMARK 465      GLY H   305
REMARK 465      LEU H   306
REMARK 465      GLY H   364
REMARK 465      ARG H   365
REMARK 465      GLU H   366
REMARK 470
REMARK 470 MISSING ATOM
REMARK 470 THE FOLLOWING RESIDUES HAVE MISSING ATOMS(M=MODEL NUMBER;
REMARK 470 RES=RESIDUE NAME; C=CHAIN IDENTIFIER; SSEQ=SEQUENCE NUMBER;
REMARK 470 I=INSERTION CODE):
REMARK 470   M RES CSSEQI ATOMS
REMARK 470     HIS A    16   CG   ND1  CD2  CE1  NE2
REMARK 470     ARG A    39   CG   CD   NE   CZ   NH1  NH2
REMARK 470     GLU A    45   CG   CD   OE1  OE2
REMARK 470     LYS A    46   CG   CD   CE   NZ
REMARK 470     SER A    47   OG
REMARK 470     ARG A    72   CG   CD   NE   CZ   NH1  NH2
REMARK 470     LYS A    77   CG   CD   CE   NZ
REMARK 470     GLU A    78   CG   CD   OE1  OE2
REMARK 470     ARG A    81   CG   CD   NE   CZ   NH1  NH2
REMARK 470     LYS A    86   CG   CD   CE   NZ
REMARK 470     GLU A    91   CG   CD   OE1  OE2
REMARK 470     LYS A   110   CG   CD   CE   NZ
REMARK 470     TRP A   114   CG   CD1  CD2  NE1  CE2  CE3  CZ2
REMARK 470     TRP A   114   CZ3  CH2
REMARK 470     LYS A   119   CG   CD   CE   NZ
REMARK 470     ARG A   120   CG   CD   NE   CZ   NH1  NH2
REMARK 470     LEU A   126   CG   CD1  CD2
REMARK 470     LYS A   129   CG   CD   CE   NZ
```

TABLE 3-continued

FGFR2(D2–D3) Complexed with FGF2

| | | | | | | | | |
|---|---|---|---|---|---|---|---|---|
| REMARK 470 | LYS A | 145 | CG | CD | CE | NZ | | |
| REMARK 470 | HIS B | 16 | CG | ND1 | CD2 | CE1 | NE2 | |
| REMARK 470 | LYS B | 46 | CG | CD | CE | NZ | | |
| REMARK 470 | HIS B | 50 | CG | ND1 | CD2 | CE1 | NE2 | |
| REMARK 470 | LYS B | 52 | CG | CD | CE | NZ | | |
| REMARK 470 | LYS B | 77 | CG | CD | CE | NZ | | |
| REMARK 470 | GLU B | 78 | CG | CD | OE1 | OE2 | | |
| REMARK 470 | ARG B | 81 | CG | CD | NE | CZ | NH1 | NH2 |
| REMARK 470 | LYS B | 86 | CG | CD | CE | NZ | | |
| REMARK 470 | GLU B | 91 | CG | CD | OE1 | OE2 | | |
| REMARK 470 | LYS B | 110 | CG | CD | CE | NZ | | |
| REMARK 470 | TYR B | 111 | CG | CD1 | CD2 | CE1 | CE2 | CZ | OH |
| REMARK 470 | TRP B | 114 | CG | CD1 | CD2 | NE1 | CE2 | CE3 | CZ2 |
| REMARK 470 | TRP B | 114 | CZ3 | CH2 | | | | |
| REMARK 470 | LYS B | 119 | CG | CD | CE | NZ | | |
| REMARK 470 | ARG B | 120 | CG | CD | NE | CZ | NH1 | NH2 |
| REMARK 470 | GLN B | 123 | CG | CD | OE1 | NE2 | | |
| REMARK 470 | LEU B | 126 | CG | CD1 | CD2 | | | |
| REMARK 470 | LYS B | 145 | CG | CD | CE | NZ | | |
| REMARK 470 | HIS C | 16 | CG | ND1 | CD2 | CE1 | NE2 | |
| REMARK 470 | HIS C | 35 | CG | ND1 | CD2 | CE1 | NE2 | |
| REMARK 470 | ARG C | 39 | CG | CD | NE | CZ | NH1 | NH2 |
| REMARK 470 | GLU C | 45 | CG | CD | OE1 | OE2 | | |
| REMARK 470 | LYS C | 46 | CG | CD | CE | NZ | | |
| REMARK 470 | SER C | 69 | OG | | | | | |
| REMARK 470 | GLU C | 78 | CG | CD | OE1 | OE2 | | |
| REMARK 470 | ARG C | 81 | CG | CD | NE | CZ | NH1 | NH2 |
| REMARK 470 | LYS C | 86 | CG | CD | CE | NZ | | |
| REMARK 470 | ASN C | 101 | CG | OD1 | ND2 | | | |
| REMARK 470 | ARG C | 120 | CG | CD | NE | CZ | NH1 | NH2 |
| REMARK 470 | LYS C | 129 | CG | CD | CE | NZ | | |
| REMARK 470 | LYS C | 145 | CG | CD | CE | NZ | | |
| REMARK 470 | HIS D | 16 | CG | ND1 | CD2 | CE1 | NE2 | |
| REMARK 470 | HIS D | 35 | CG | ND1 | CD2 | CE1 | NE2 | |
| REMARK 470 | GLU D | 45 | CG | CD | OE1 | OE2 | | |
| REMARK 470 | LYS D | 46 | CG | CD | CE | NZ | | |
| REMARK 470 | ASP D | 48 | CG | OD1 | OD2 | | | |
| REMARK 470 | SER D | 69 | OG | | | | | |
| REMARK 470 | GLU D | 78 | CG | CD | OE1 | OE2 | | |
| REMARK 470 | ARG D | 81 | CG | CD | NE | CZ | NH1 | NH2 |
| REMARK 470 | LYS D | 86 | CG | CD | CE | NZ | | |
| REMARK 470 | SER D | 87 | OG | | | | | |
| REMARK 470 | LYS D | 119 | CG | CD | CE | NZ | | |
| REMARK 470 | ARG D | 120 | CG | CD | NE | CZ | NH1 | NH2 |
| REMARK 470 | LYS D | 129 | CG | CD | CE | NZ | | |
| REMARK 470 | LYS D | 145 | CG | CD | CE | NZ | | |
| REMARK 470 | ASN E | 150 | CG | OD1 | ND2 | | | |
| REMARK 470 | LYS E | 151 | CG | CD | CE | NZ | | |
| REMARK 470 | GLU E | 160 | CG | CD | OE1 | OE2 | | |
| REMARK 470 | LYS E | 161 | CG | CD | CE | NZ | | |
| REMARK 470 | GLU E | 163 | CG | CD | OE1 | OE2 | | |
| REMARK 470 | ASN E | 184 | CG | OD1 | ND2 | | | |
| REMARK 470 | ARG E | 210 | CG | CD | NE | CZ | NH1 | NH2 |
| REMARK 470 | ASN E | 211 | CG | OD1 | ND2 | | | |
| REMARK 470 | GLN E | 212 | CG | CD | OE1 | NE2 | | |
| REMARK 470 | HIS E | 213 | CG | ND1 | CD2 | CE1 | NE2 | |
| REMARK 470 | GLU E | 234 | CG | CD | OE1 | OE2 | | |
| REMARK 470 | SER E | 267 | OG | | | | | |
| REMARK 470 | TYR E | 281 | CG | CD1 | CD2 | CE1 | CE2 | CZ | OH |
| REMARK 470 | LYS E | 292 | CG | CD | CE | NZ | | |
| REMARK 470 | HIS E | 293 | CG | ND1 | CD2 | CE1 | NE2 | |
| REMARK 470 | VAL E | 294 | CG1 | CG2 | | | | |
| REMARK 470 | TYR E | 308 | CG | CD1 | CD2 | CE1 | CE2 | CZ | OH |
| REMARK 470 | LYS E | 310 | CG | CD | CE | NZ | | |
| REMARK 470 | LYS E | 322 | CG | CD | CE | NZ | | |
| REMARK 470 | GLU E | 323 | CG | CD | OE1 | OE2 | | |
| REMARK 470 | ARG E | 330 | CG | CD | NE | CZ | NH1 | NH2 |
| REMARK 470 | ASN E | 331 | CG | OD1 | ND2 | | | |
| REMARK 470 | VAL E | 332 | CG1 | CG2 | | | | |
| REMARK 470 | THR E | 333 | OG1 | CG2 | | | | |
| REMARK 470 | PHE E | 334 | CG | CD1 | CD2 | CE1 | CE2 | CZ |
| REMARK 470 | GLU E | 335 | CG | CD | OE1 | OE2 | | |
| REMARK 470 | VAL E | 359 | CG1 | CG2 | | | | |
| REMARK 470 | LEU E | 360 | CG | CD1 | CD2 | | | |
| REMARK 470 | ASN F | 150 | CG | OD1 | ND2 | | | |
| REMARK 470 | LYS F | 151 | CG | CD | CE | NZ | | |
| REMARK 470 | GLU F | 160 | CG | CD | OE1 | OE2 | | |

TABLE 3-continued

FGFR2(D2–D3) Complexed with FGF2

| | | | | | | | | | |
|---|---|---|---|---|---|---|---|---|---|
| REMARK 470 | LYS F | 161 | CG | CD | CE | NZ | | | |
| REMARK 470 | GLU F | 163 | CG | CD | OE1 | OE2 | | | |
| REMARK 470 | ASN F | 184 | CG | OD1 | ND2 | | | | |
| REMARK 470 | ARG F | 210 | CG | CD | NE | CZ | NH1 | NH2 | |
| REMARK 470 | GLN F | 212 | CG | CD | OE1 | NE2 | | | |
| REMARK 470 | HIS F | 213 | CG | ND1 | CD2 | CE1 | NE2 | | |
| REMARK 470 | GLU F | 234 | CG | CD | OE1 | OE2 | | | |
| REMARK 470 | GLU F | 236 | CG | CD | OE1 | OE2 | | | |
| REMARK 470 | SER F | 267 | OG | | | | | | |
| REMARK 470 | VAL F | 269 | CG1 | CG2 | | | | | |
| REMARK 470 | VAL F | 270 | CG1 | CG2 | | | | | |
| REMARK 470 | HIS F | 293 | CG | ND1 | CD2 | CE1 | NE2 | | |
| REMARK 470 | TYR F | 308 | CG | CD1 | CD2 | CE1 | CE2 | CZ | OH |
| REMARK 470 | LYS F | 310 | CG | CD | CE | NZ | | | |
| REMARK 470 | LYS F | 322 | CG | CD | CE | NZ | | | |
| REMARK 470 | GLU F | 323 | CG | CD | OE1 | OE2 | | | |
| REMARK 470 | TYR F | 328 | CG | CD1 | CD2 | CE1 | CE2 | CZ | OH |
| REMARK 470 | ILE F | 329 | CG1 | CG2 | CD1 | | | | |
| REMARK 470 | ARG F | 330 | CG | CD | NE | CZ | NH1 | NH2 | |
| REMARK 470 | ASN F | 331 | CG | OD1 | ND2 | | | | |
| REMARK 470 | VAL F | 332 | CG1 | CG2 | | | | | |
| REMARK 470 | THR F | 333 | OG1 | CG2 | | | | | |
| REMARK 470 | PHE F | 334 | CG | CD1 | CD2 | CE1 | CE2 | CZ | |
| REMARK 470 | GLU F | 335 | CG | CD | OE1 | OE2 | | | |
| REMARK 470 | TRP F | 356 | CG | CD1 | CD2 | NE1 | CE2 | CE3 | CZ2 |
| REMARK 470 | TRP F | 356 | CZ3 | CH2 | | | | | |
| REMARK 470 | THR F | 358 | OG1 | CG2 | | | | | |
| REMARK 470 | VAL F | 359 | CG1 | CG2 | | | | | |
| REMARK 470 | LYS G | 151 | CG | CD | CE | NZ | | | |
| REMARK 470 | GLU G | 160 | CG | CD | OE1 | OE2 | | | |
| REMARK 470 | ARG G | 165 | CG | CD | NE | CZ | NH1 | NH2 | |
| REMARK 470 | LYS G | 176 | CG | CD | CE | NZ | | | |
| REMARK 470 | LYS G | 196 | CG | CD | CE | NZ | | | |
| REMARK 470 | ARG G | 203 | CG | CD | NE | CZ | NH1 | NH2 | |
| REMARK 470 | ARG G | 210 | CG | CD | NE | CZ | NH1 | NH2 | |
| REMARK 470 | GLN G | 212 | CG | CD | OE1 | NE2 | | | |
| REMARK 470 | HIS G | 213 | CG | ND1 | CD2 | CE1 | NE2 | | |
| REMARK 470 | LYS G | 226 | CG | CD | CE | NZ | | | |
| REMARK 470 | GLU G | 236 | CG | CD | OE1 | OE2 | | | |
| REMARK 470 | ASP G | 273 | CG | OD1 | OD2 | | | | |
| REMARK 470 | TYR G | 308 | CG | CD1 | CD2 | CE1 | CE2 | CZ | OH |
| REMARK 470 | LYS G | 310 | CG | CD | CE | NZ | | | |
| REMARK 470 | LYS G | 322 | CG | CD | CE | NZ | | | |
| REMARK 470 | GLU G | 323 | CG | CD | OE1 | OE2 | | | |
| REMARK 470 | GLU G | 335 | CG | CD | OE1 | OE2 | | | |
| REMARK 470 | LYS H | 151 | CG | CD | CE | NZ | | | |
| REMARK 470 | GLU H | 160 | CG | CD | OE1 | OE2 | | | |
| REMARK 470 | LYS H | 161 | CG | CD | CE | NZ | | | |
| REMARK 470 | ARG H | 165 | CG | CD | NE | CZ | NH1 | NH2 | |
| REMARK 470 | LYS H | 176 | CG | CD | CE | NZ | | | |
| REMARK 470 | LYS H | 196 | CG | CD | CE | NZ | | | |
| REMARK 470 | GLU H | 197 | CG | CD | OE1 | OE2 | | | |
| REMARK 470 | LYS H | 199 | CG | CD | CE | NZ | | | |
| REMARK 470 | ARG H | 210 | CG | CD | NE | CZ | NH1 | NH2 | |
| REMARK 470 | ASN H | 211 | CG | OD1 | ND2 | | | | |
| REMARK 470 | GLN H | 212 | CG | CD | OE1 | NE2 | | | |
| REMARK 470 | GLU H | 236 | CG | CD | OE1 | OE2 | | | |
| REMARK 470 | HIS H | 245 | CG | ND1 | CD2 | CE1 | NE2 | | |
| REMARK 470 | VAL H | 269 | CG1 | CG2 | | | | | |
| REMARK 470 | HIS H | 293 | CG | ND1 | CD2 | CE1 | NE2 | | |
| REMARK 470 | TYR H | 308 | CG | CD1 | CD2 | CE1 | CE2 | CZ | OH |
| REMARK 470 | LYS H | 310 | CG | CD | CE | NZ | | | |
| REMARK 470 | ASN H | 318 | CG | OD1 | ND2 | | | | |
| REMARK 470 | LYS H | 322 | CG | CD | CE | NZ | | | |
| REMARK 470 | GLU H | 323 | CG | CD | OE1 | OE2 | | | |
| REMARK 470 | PHE H | 334 | CG | CD1 | CD2 | CE1 | CE2 | CZ | |
| REMARK 470 | GLU H | 335 | CG | CD | OE1 | OE2 | | | |
| REMARK 470 | VAL H | 359 | CG1 | CG2 | | | | | |

REMARK 500
REMARK 500 GEOMETRY AND STEREOCHEMISTRY
REMARK 500 SUBTOPIC: COVALENT BOND LENGTHS
REMARK 500
REMARK 500 THE STEREOCHEMICAL PARAMETERS OF THE FOLLOWING RESIDUES
REMARK 500 HAVE VALUES WHICH DEVIATE FROM EXPECTED VALUES BY MORE
REMARK 500 THAN 6*RMSD (M=MODEL NUMBER; RES=RESIDUE NAME; C=CHAIN
REMARK 500 IDENTIFIER; SSEQ=SEQUENCE NUMBER; I=INSERTION CODE).
REMARK 500

TABLE 3-continued

FGFR2(D2–D3) Complexed with FGF2

```
REMARK  500 STANDARD TABLE:
REMARK  500 FORMAT: (10X,I3,1X,2(A3,1X,A1,I4,A1,1X,A4,3X),F6.3)
REMARK  500
REMARK  500 EXPECTED VALUES: ENGH AND HUBER, 1991
REMARK  500
REMARK  500 M RES CSSEQI ATM1   RES CSSEQI ATM2 DEVIATION
REMARK  500     MET A    76  CE    MET A    76  SD    0.046
REMARK  500     MET E   162  SD    MET E   162  CG    0.047
REMARK  500     MET E   189  CE    MET E   189  SD    0.050
REMARK  500     MET F   218  CE    MET F   218  SD   -0.073
REMARK  500     PRO F   286  CD    PRO F   286  CG    0.048
REMARK  500     PRO G   361  CG    PRO G   361  CB    0.061
REMARK  500     PRO G   363  CG    PRO G   363  CB    0.051
REMARK  500     PRO H   363  CG    PRO H   363  CB    0.048
REMARK  500
REMARK  500 GEOMETRY AND STEREOCHEMISTRY
REMARK  500 SUBTOPIC: COVALENT BOND ANGLES
REMARK  500
REMARK  500 THE STEREOCHEMICAL PARAMETERS OF THE FOLLOWING RESIDUES
REMARK  500 HAVE VALUES WHICH DEVIATE FROM EXPECTED VALUES BY MORE
REMARK  500 THAN 6*RMSD (M=MODEL NUMBER; RES=RESIDUE NAME; C=CHAIN
REMARK  500 IDENTIFIER; SSEQ=SEQUENCE NUMBER; I=INSERTION CODE).
REMARK  500
REMARK  500 STANDARD TABLE:
REMARK  500 FORMAT: (10X,I3,1X,A3,1X,A1,I4,A1,3(1X,A4,2X),12X,F5.1)
REMARK  500
REMARK  500 EXPECTED VALUES: ENGH AND HUBER, 1991
REMARK  500
REMARK  500 M RES CSSEQI ATM1 ATM2 ATM3
REMARK  500     ARG A    22   N - CA - C   ANGL. DEV. = -10.0 DEGREES
REMARK  500     SER A    64   N - CA - C   ANGL. DEV. = -9.7 DEGREES
REMARK  500     THR A   112   N - CA - C   ANGL. DEV. = 10.5 DEGREES
REMARK  500     VAL A   116   N - CA - C   ANGL. DEV. = -10.5 DEGREES
REMARK  500     ARG B    22   N - CA - C   ANGL. DEV. = = 10.2 DEGREES
REMARK  500     SER B    64   N - CA - C   ANGL. DEV. = -9.9 DEGREES
REMARK  500     THR B   112   N - CA - C   ANGL. DEV. = 10.8 DEGREES
REMARK  500     VAL B   116   N - CA - C   ANGL. DEV. = -10.1 DEGREES
REMARK  500     ARG C    22   N - CA - C   ANGL. DEV. = -9.5 DEGREES
REMARK  500     SER C    64   N - CA - C   ANGL. DEV. = -9.0 DEGREES
REMARK  500     THR C   112   N - CA - C   ANGL. DEV. = 10.7 DEGREES
REMARK  500     VAL C   116   N - CA - C   ANGL. DEV. = -9.8 DEGREES
REMARK  500     ARG D    22   N - CA - C   ANGL. DEV. = -9.6 DEGREES
REMARK  500     SER D    64   N - CA - C   ANGL. DEV. = -9.2 DEGREES
REMARK  500     THR D   112   N - CA - C   ANGL. DEV. = 10.6 DEGREES
REMARK  500     VAL D   116   N - CA - C   ANGL. DEV. = -10.1 DEGREES
REMARK  500     GLU E   234   N - CA - C   ANGL. DEV. = 8.0 DEGREES
REMARK  500     CYS E   342   N - CA - C   ANGL. DEV. = -8.2 DEGREES
REMARK  500     GLU F   234   N - CA - C   ANGL. DEV. = 8.2 DEGREES
REMARK  500     LEU F   258   CA - CB - CG ANGL. DEV. = 8.1 DEGREES
REMARK  500     CYS F   342   N - CA - C   ANGL. DEV. = -8.5 DEGREES
REMARK  500     GLU G   234   N - CA - C   ANGL. DEV. = 8.6 DEGREES
REMARK  500     ALA G   362   N - CA - C   ANGL. DEV. = 13.7 DEGREES
REMARK  500     PRO G   363   C - N - CA   ANGL. DEV. = -10.5 DEGREES
REMARK  500     GLU H   234   N - CA - C   ANGL. DEV. = 8.6 DEGREES
REMARK  500
REMARK  900 RELATED ENTRIES
REMARK  900 RELATED ID: 1CVS   RELATED DB: PDB
REMARK  900 CRYSTAL STRUCTURE OF FGF2 IN COMPLEX WITH THE EXTRACELLULAR
REMARK  900 LIGAND BINDING DOMAIN OF FGF RECEPTOR 1 (FGFR1)
REMARK  900 RELATED ID: 1EVT RELATED DB: PDB
REMARK  900 FGF1-FGFR1 COMPLEX
DBREF   1EV2 A    15   146 SWS  P09038  FGF2_HUMAN    24    155
DBREF   1EV2 B    15   146 SWS  P09038  FGF2_HUMAN    24    155
DBREF   1EV2 C    15   146 SWS  P09038  FGF2_HUMAN    24    155
DBREF   1EV2 D    15   146 SWS  P09038  FGF2_HUMAN    24    155
DBREF   1EV2 E   147   366 SWS  P21802  FGR2_HUMAN   147    366
DBREF   1EV2 F   147   366 SWS  P21802  FGR2_HUMAN   147    366
DEREF   1EV2 G   147   366 SWS  P21802  FGR2_HUMAN   147    366
DBREF   IEV2 H   147   366 SWS  P21802  FGR2_HUMAN   147    366
SEQADV  1EV2 SER A    69  SWS  P09038   CYS   78 ENGINEERED
SEQADV  1EV2 SER A    87  SWS  P09038   CYS   96 ENGINEERED
SEQADV  1EV2 SER B    69  SWS  P09038   CYS   78 ENGINEERED
SEQADV  1EV2 SER B    87  SWS  P09038   CYS   96 ENGINEERED
SEQADV  1EV2 SER C    69  SWS  P09038   CYS   78 ENGINEERED
SEQADV  1EV2 SER C    87  SWS  P09038   CYS   96 ENGINEERED
SEQADV  1EV2 SER D    69  SWS  P09038   CYS   78 ENGINEERED
SEQADV  1EV2 SER D    87  SWS  P09038   CYS   96 ENGINEERED
```

TABLE 3-continued

FGFR2(D2–D3) Complexed with FGF2

| | | | |
|---|---|---|---|
| SEQRES | 1 A | 132 | GLY HIS PHE LYS ASP PRO LYS ARG LEU TYR CYS LYS ASN |
| SEQRES | 2 A | 132 | GLY GLY PHE PHE LEU ARG ILE HIS PRO ASP GLY ARG VAL |
| SEQRES | 3 A | 132 | ASP GLY VAL ARG GLU LYS SER ASP PRO HIS ILE LYS LEU |
| SEQRES | 4 A | 132 | GLN LEU GLN ALA GLU GLU ARG GLY VAL VAL SER ILE LYS |
| SEQRES | 5 A | 132 | GLY VAL SER ALA ASN ARG TYR LEU ALA MET LYS GLU ASP |
| SEQRES | 6 A | 132 | GLY ARG LEU LEU ALA SER LYS SER VAL THR ASP GLU CYS |
| SEQRES | 7 A | 132 | PHE PHE PHE GLU ARG LEU GLU SER ASN ASN TYR ASN THR |
| SEQRES | 8 A | 132 | TYR ARG SER ARG LYS TYR THR SER TRP TYR VAL ALA LEU |
| SEQRES | 9 A | 132 | LYS ARG THR GLY GLN TYR LYS LEU GLY SER LYS THR GLY |
| SEQRES | 10 A | 132 | PRO GLY GLN LYS ALA ILE LEU PHE LEU PRO MET SER ALA |
| SEQRES | 11 A | 132 | LYS SER |
| SEQRES | 1 B | 132 | GLY HIS PHE LYS ASP PRO LYS ARG LEU TYR CYS LYS ASN |
| SEQRES | 2 B | 132 | GLY GLY PHE PHE LEU ARG ILE HIS PRO ASP GLY ARG VAL |
| SEQRES | 3 B | 132 | ASP GLY VAL ARG GLU LYS SER ASP PRO HIS ILE LYS LEU |
| SEQRES | 4 B | 132 | GLN LEU GLN ALA GLU GLU ARG GLY VAL VAL SER ILE LYS |
| SEQRES | 5 B | 132 | GLY VAL SER ALA ASN ARG TYR LEU ALA MET LYS GLU ASP |
| SEQRES | 6 B | 132 | GLY ARG LEU LEU ALA SER LYS SER VAL THR ASP GLU CYS |
| SEQRES | 7 B | 132 | PHE PHE PHE GLU ARG LEU GLU SER ASN ASN TYR ASN THR |
| SEQRES | 8 B | 132 | TYR ARG SER ARG LYS TYR THR SER TRP TYR VAL ALA LEU |
| SEQRES | 9 B | 132 | LYS ARG THR GLY GLN TYR LYS LEU GLY SER LYS THR GLY |
| SEQRES | 10 B | 132 | PRO GLY GLN LYS ALA ILE LEU PHE LEU PRO MET SER ALA |
| SEQRES | 11 B | 132 | LYS SER |
| SEQRES | 1 C | 132 | GLY HIS PHE LYS ASP PRO LYS ARG LEU TYR CYS LYS ASN |
| SEQRES | 2 C | 132 | GLY GLY PHE PHE LEU ARG ILE HIS PRO ASP GLY ARG VAL |
| SEQRES | 3 C | 132 | ASP GLY VAL ARG GLU LYS SER ASP PRO HIS ILE LYS LEU |
| SEQRES | 4 C | 132 | GLN LEU GLN ALA GLU GLU ARG GLY VAL VAL SER ILE LYS |
| SEQRES | 5 C | 132 | GLY VAL SER ALA ASN ARG TYR LEU ALA MET LYS GLU ASP |
| SEQRES | 6 C | 132 | GLY ARG LEU LEU ALA SER LYS SER VAL THR ASP GLU CYS |
| SEQRES | 7 C | 132 | PHE PHE PHE GLU ARG LEU GLU SER ASN ASN TYR ASN THR |
| SEQRES | 8 C | 132 | TYR ARG SER ARG LYS TYR THR SER TRP TYR VAL ALA LEU |
| SEQRES | 9 C | 132 | LYS ARG THR GLY GLN TYR LYS LEU GLY SER LYS THR GLY |
| SEQRES | 10 C | 132 | PRO GLY GLN LYS ALA ILE LEU PHE LEU PRO MET SER ALA |
| SEQRES | 11 C | 132 | LYS SER |
| SEQRES | 1 D | 132 | GLY HIS PHE LYS ASP PRO LYS ARG LEU TYR CYS LYS ASN |
| SEQRES | 2 D | 132 | GLY GLY PHE PHE LEU ARG ILE HIS PRO ASP GLY ARG VAL |
| SEQRES | 3 D | 132 | ASP GLY VAL ARG GLU LYS SER ASP PRO HIS ILE LYS LEU |
| SEQRES | 4 D | 132 | GLN LEU GLN ALA GLU GLU ARG GLY VAL VAL SER ILE LYS |
| SEQRES | 5 D | 132 | GLY VAL SER ALA ASN ARG TYR LEU ALA MET LYS GLU ASP |
| SEQRES | 6 D | 132 | GLY ARG LEU LEU ALA SER LYS SER VAL THR ASP GLU CYS |
| SEQRES | 7 D | 132 | PHE PHE PHE GLU ARG LEU GLU SER ASN ASN TYR ASN THR |
| SEQRES | 8 D | 132 | TYR ARG SER ARG LYS TYR THR SER TRP TYR VAL ALA LEU |
| SEQRES | 9 D | 132 | LYS ARG THR GLY GLN TYR LYS LEU GLY SER LYS THR GLY |
| SEQRES | 10 D | 132 | PRO GLY GLN LYS ALA ILE LEU PHE LEU PRO MET SER ALA |
| SEQRES | 11 D | 132 | LYS SER |
| SEQRES | 1 E | 220 | ASN SER ASN ASN LYS ARG ALA PRO TYR TRP THR ASN THR |
| SEQRES | 2 E | 220 | GLU LYS MET GLU LYS ARG LEU HIS ALA VAL PRO ALA ALA |
| SEQRES | 3 E | 220 | ASN THR VAL LYS PHE ARG CYS PRO ALA GLY GLY ASN PRO |
| SEQRES | 4 E | 220 | MET PRO THR MET ARG TRP LEU LYS ASN GLY LYS GLU PHE |
| SEQRES | 5 E | 220 | LYS GLN GLU HIS ARG ILE GLY GLY TYR LYS VAL ARG ASN |
| SEQRES | 6 E | 220 | GLN HIS TRP SER LEU ILE MET GLU SER VAL VAL PRO SER |
| SEQRES | 7 E | 220 | ASP LYS GLY ASN TYR THR CYS VAL VAL GLU ASN GLU TYR |
| SEQRES | 8 E | 220 | GLY SER ILE ASN HIS THR TYR HIS LEU ASP VAL VAL GLU |
| SEQRES | 9 E | 220 | ARG SER PRO HIS ARG PRO ILE LEU GLN ALA GLY LEU PRO |
| SEQRES | 10 E | 220 | ALA ASN ALA SER THR VAL VAL GLY GLY ASP VAL GLU PHE |
| SEQRES | 11 E | 220 | VAL CYS LYS VAL TYR SER ASP ALA GLN PRO HIS ILE GLN |
| SEQRES | 12 E | 220 | TRP ILE LYS HIS VAL GLU LYS ASN GLY SER LYS TYR GLY |
| SEQRES | 13 E | 220 | PRO ASP GLY LEU PRO TYR LEU LYS VAL LEU LYS ALA ALA |
| SEQRES | 14 E | 220 | GLY VAL ASN THR THR ASP LYS GLU ILE GLU VAL LEU TYR |
| SEQRES | 15 E | 220 | ILE ARG ASN VAL THR PHE GLU ASP ALA GLY GLU TYR THR |
| SEQRES | 16 E | 220 | CYS LEU ALA GLY ASN SER ILE GLY ILE SER PHE HIS SER |
| SEQRES | 17 E | 220 | ALA TRP LEU THR VAL LEU PRO ALA PRO GLY ARG GLU |
| SEQRES | 1 F | 220 | ASN SER ASN ASN LYS ARG ALA PRO TYR TRP THR ASN THR |
| SEQRES | 2 F | 220 | GLU LYS MET GLU LYS ARG LEU HIS ALA VAL PRO ALA ALA |
| SEQRES | 3 F | 220 | ASN THR VAL LYS PHE ARG CYS PRO ALA GLY GLY ASN PRO |
| SEQRES | 4 F | 220 | MET PRO THR MET ARG TRP LEU LYS ASN GLY LYS GLU PHE |
| SEQRES | 5 F | 220 | LYS GLN GLU HIS ARG ILE GLY GLY TYR LYS VAL ARG ASN |
| SEQRES | 6 F | 220 | GLN HIS TRP SER LEU ILE MET GLU SER VAL VAL PRO SER |
| SEQRES | 7 F | 220 | ASP LYS GLY ASN TYR THR CYS VAL VAL GLU ASN GLU TYR |
| SEQRES | 8 F | 220 | GLY SER ILE ASN HIS THR TYR HIS LEU ASP VAL VAL GLU |
| SEQRES | 9 F | 220 | ARG SER PRO HIS ARG PRO ILE LEU GLN ALA GLY LEU PRO |
| SEQRES | 10 F | 220 | ALA ASN ALA SER THR VAL VAL GLY GLY ASP VAL GLU PHE |
| SEQRES | 11 F | 220 | VAL CYS LYS VAL TYR SER ASP ALA GLN PRO HIS ILE GLN |
| SEQRES | 12 F | 220 | TRP ILE LYS HIS VAL GLU LYS ASN GLY SER LYS TYR GLY |
| SEQRES | 13 F | 220 | PRO ASP GLY LEU PRO TYR LEU LYS VAL LEU LYS ALA ALA |
| SEQRES | 14 F | 220 | GLY VAL ASN THR THR ASP LYS GLU ILE GLU VAL LEU TYR |
| SEQRES | 15 F | 220 | ILE ARG ASN VAL THR PHE GLU ASP ALA GLY GLU TYR THR |
| SEQRES | 16 F | 220 | CYS LEU ALA GLY ASN SER ILE GLY ILE SER PHE HIS SER |

TABLE 3-continued

FGFR2(D2–D3) Complexed with FGF2

| | | | | | | | | | | | | | |
|---|---|---|---|---|---|---|---|---|---|---|---|---|---|
| SEQRES | 17 F | 220 | ALA TRP LEU THR VAL LEU PRO ALA PRO GLY ARG GLU | | | | | | | | | | |
| SEQRES | 1 G | 220 | ASN SER ASN ASN LYS ARG ALA PRO TYR TRP THR ASN THR | | | | | | | | | | |
| SEQRES | 2 G | 220 | GLU LYS MET GLU LYS ARG LEU HIS ALA VAL PRO ALA ALA | | | | | | | | | | |
| SEQRES | 3 G | 220 | ASN THR VAL LYS PHE ARG CYS PRO ALA GLY GLY ASN PRO | | | | | | | | | | |
| SEQRES | 4 G | 220 | MET PRO THR MET ARG TRP LEU LYS ASN GLY LYS GLU PHE | | | | | | | | | | |
| SEQRES | 5 G | 220 | LYS GLN GLU HIS ARG ILE GLY GLY TYR LYS VAL ARG ASN | | | | | | | | | | |
| SEQRES | 6 G | 220 | GLN HIS TRP SER LEU ILE MET GLU SER VAL VAL PRO SER | | | | | | | | | | |
| SEQRES | 7 G | 220 | ASP LYS GLY ASN TYR THR CYS VAL VAL GLU ASN GLU TYR | | | | | | | | | | |
| SEQRES | 8 G | 220 | GLY SER ILE ASN HIS THR TYR HIS LEU ASP VAL VAL GLU | | | | | | | | | | |
| SEQRES | 9 G | 220 | ARG SER PRO HIS ARG PRO ILE LEU GLN ALA GLY LEU PRO | | | | | | | | | | |
| SEQRES | 10 G | 220 | ALA ASN ALA SER THR VAL VAL GLY GLY ASP VAL GLU PHE | | | | | | | | | | |
| SEQRES | 11 G | 220 | VAL CYS LYS VAL TYR SER ASP ALA GLN PRO HIS ILE GLN | | | | | | | | | | |
| SEQRES | 12 G | 220 | TRP ILE LYS HIS VAL GLU LYS ASN GLY SER LYS TYR GLY | | | | | | | | | | |
| SEQRES | 13 G | 220 | PRO ASP GLY LEU PRO TYR LEU LYS VAL LEU LYS ALA ALA | | | | | | | | | | |
| SEQRES | 14 G | 220 | GLY VAL ASN THR THR ASP LYS GLU ILE GLU VAL LEU TYR | | | | | | | | | | |
| SEQRES | 15 G | 220 | ILE ARG ASN VAL THR PHE GLU ASP ALA GLY GLU TYR THR | | | | | | | | | | |
| SEQRES | 16 G | 220 | CYS LEU ALA GLY ASN SER ILE GLY ILE SER PHE HIS SER | | | | | | | | | | |
| SEQRES | 17 G | 220 | ALA TRP LEU THR VAL LEU PRO ALA PRO GLY ARG GLU | | | | | | | | | | |
| SEQRES | 1 H | 220 | ASN SER ASN ASN LYS ARG ALA PRO TYR TRP THR ASN THR | | | | | | | | | | |
| SEQRES | 2 H | 220 | GLU LYS MET GLU LYS ARG LEU HIS ALA VAL PRO ALA ALA | | | | | | | | | | |
| SEQRES | 3 H | 220 | ASN THR VAL LYS PHE ARG CYS PRO ALA GLY GLY ASN PRO | | | | | | | | | | |
| SEQRES | 4 H | 220 | MET PRO THR MET ARG TRP LEU LYS ASN GLY LYS GLU PHE | | | | | | | | | | |
| SEQRES | 5 H | 220 | LYS GLN GLU HIS ARG ILE GLY GLY TYR LYS VAL ARG ASN | | | | | | | | | | |
| SEQRES | 6 H | 220 | GLN HIS TRP SER LEU ILE MET GLU SER VAL VAL PRO SER | | | | | | | | | | |
| SEQRES | 7 H | 220 | ASP LYS GLY ASN TYR THR CYS VAL VAL GLU ASN GLU TYR | | | | | | | | | | |
| SEQRES | 8 H | 220 | GLY SER ILE ASN HIS THR TYR HIS LEU ASP VAL VAL GLU | | | | | | | | | | |
| SEQRES | 9 H | 220 | ARG SER PRO HIS ARG PRO ILE LEU GLN ALA GLY LEU PRO | | | | | | | | | | |
| SEQRES | 10 H | 220 | ALA ASN ALA SER THR VAL VAL GLY GLY ASP VAL GLU PHE | | | | | | | | | | |
| SEQRES | 11 H | 220 | VAL CYS LYS VAL TYR SER ASP ALA GLN PRO HIS ILE GLN | | | | | | | | | | |
| SEQRES | 12 H | 220 | TRP ILE LYS HIS VAL GLU LYS ASN GLY SER LYS TYR GLY | | | | | | | | | | |
| SEQRES | 13 H | 220 | PRO ASP GLY LEU PRO TYR LEU LYS VAL LEU LYS ALA ALA | | | | | | | | | | |
| SEQRES | 14 H | 220 | GLY VAL ASN THR THR ASP LYS GLU ILE GLU VAL LEU TYR | | | | | | | | | | |
| SEQRES | 15 H | 220 | ILE ARG ASN VAL THR PHE GLU ASP ALA GLY GLU TYR THR | | | | | | | | | | |
| SEQRES | 16 H | 220 | CYS LEU ALA GLY ASN SER ILE GLY ILE SER PHE HIS SER | | | | | | | | | | |
| SEQRES | 17 H | 220 | ALA TRP LEU THR VAL LEU PRO ALA PRO GLY ARG GLU | | | | | | | | | | |
| HET | SO4 | 9001 | 5 | | | | | | | | | | |
| HET | SO4 | 9002 | 5 | | | | | | | | | | |
| HET | SO4 | 9003 | 5 | | | | | | | | | | |
| HET | SO4 | 9004 | 5 | | | | | | | | | | |
| HETNAM | SO4 SULFATE ION | | | | | | | | | | | | |
| FORMUL | 9 SO4 | 4(O4 S1 2-) | | | | | | | | | | | |
| FORMUL | 13 HOH | *263(H2 O1) | | | | | | | | | | | |
| HELIX | 1 | 1 | LEU A | 126 | THR A | 130 | 5 | | 5 | | | | |
| HELIX | 2 | 2 | LEU B | 126 | THR B | 130 | 5 | | 5 | | | | |
| HELIX | 3 | 3 | LEU C | 126 | THR C | 130 | 5 | | 5 | | | | |
| HELIX | 4 | 4 | LEU D | 126 | THR D | 130 | 5 | | 5 | | | | |
| HELIX | 5 | 5 | ASN E | 158 | GLU E | 163 | 5 | | 6 | | | | |
| HELIX | 6 | 6 | LYS E | 199 | ARG E | 203 | 5 | | 5 | | | | |
| HELIX | 7 | 7 | ASN E | 211 | HIS E | 213 | 5 | | 3 | | | | |
| HELIX | 8 | 8 | VAL E | 222 | LYS E | 226 | 5 | | 5 | | | | |
| HELIX | 9 | 9 | THR E | 333 | ALA E | 337 | 5 | | 5 | | | | |
| HELIX | 10 | 10 | ASN F | 158 | GLU F | 163 | 5 | | 6 | | | | |
| HELIX | 11 | 11 | LYS F | 199 | ARG F | 203 | 5 | | 5 | | | | |
| HELIX | 12 | 12 | ASN F | 211 | HIS F | 213 | 5 | | 3 | | | | |
| HELIX | 13 | 13 | VAL F | 222 | LYS F | 226 | 5 | | 5 | | | | |
| HELIX | 14 | 14 | THR F | 333 | ALA F | 337 | 5 | | 5 | | | | |
| HELIX | 15 | 15 | ASN G | 158 | GLU G | 163 | 5 | | 6 | | | | |
| HELIX | 16 | 16 | LYS G | 199 | ARG G | 203 | 5 | | 5 | | | | |
| HELIX | 17 | 17 | ASN G | 211 | HIS G | 213 | 5 | | 3 | | | | |
| HELIX | 18 | 18 | VAL G | 222 | LYS G | 226 | 5 | | 5 | | | | |
| HELIX | 19 | 19 | THR G | 333 | ALA G | 337 | 5 | | 5 | | | | |
| HELIX | 20 | 20 | ASN H | 158 | GLU H | 163 | 5 | | 6 | | | | |
| HELIX | 21 | 21 | LYS H | 199 | ARG H | 203 | 5 | | 5 | | | | |
| HELIX | 22 | 22 | ASN H | 211 | HIS H | 213 | 5 | | 3 | | | | |
| HELIX | 23 | 23 | VAL H | 222 | LYS H | 226 | 5 | | 5 | | | | |
| HELIX | 24 | 24 | THR H | 333 | ALA H | 337 | 5 | | 5 | | | | |
| SHEET | 1 | A 4 | VAL A | 40 | VAL A | 43 | 0 | | | | | | |
| SHEET | 2 | A 4 | PHE A | 30 | ILE A | 34 | −1 | N | PHE A | 31 | O | VAL A | 43 |
| SHEET | 3 | A 4 | LYS A | 21 | CYS A | 25 | −1 | O | LEU A | 23 | N | LEU A | 32 |
| SHEET | 4 | A 4 | PHE A | 139 | SER A | 143 | −1 | N | LEU A | 140 | O | TYR A | 24 |
| SHEET | 1 | B 4 | LEU A | 53 | GLU A | 59 | 0 | | | | | | |
| SHEET | 2 | B 4 | VAL A | 62 | GLY A | 67 | −1 | N | VAL A | 62 | O | GLU A | 59 |
| SHEET | 3 | B 4 | ARG A | 72 | MET A | 76 | −1 | O | ARG A | 72 | N | GLY A | 67 |
| SHEET | 4 | B 4 | LEU A | 82 | SER A | 85 | −1 | O | LEU A | 83 | N | ALA A | 75 |
| SHEET | 1 | C 4 | LEU A | 53 | GLU A | 59 | 0 | | | | | | |
| SHEET | 2 | C 4 | VAL A | 62 | GLY A | 67 | −1 | N | VAL A | 62 | O | GLU A | 59 |
| SHEET | 3 | C 4 | PHE A | 94 | LEU A | 98 | −1 | N | PHE A | 94 | O | VAL A | 63 |

TABLE 3-continued

FGFR2(D2–D3) Complexed with FGF2

| | | | | | | | | | | | | | |
|---|---|---|---|---|---|---|---|---|---|---|---|---|---|
| SHEET | 4 | C 4 | ASN A | 104 | SER A | 108 | −1 | O | THR A | 105 | N | ARG A | 97 |
| SHEET | 1 | D 4 | VAL B | 40 | VAL B | 43 | 0 | | | | | | |
| SHEET | 2 | D 4 | PHE B | 30 | ILE B | 34 | −1 | N | PHE B | 31 | O | VAL B | 43 |
| SHEET | 3 | D 4 | LYS B | 21 | CYS B | 25 | −1 | O | LEU B | 23 | N | LEU B | 32 |
| SHEET | 4 | D 4 | PHE B | 139 | SER B | 143 | −1 | N | LEU B | 140 | O | TYR B | 24 |
| SHEET | 1 | E 4 | LEU B | 53 | GLU B | 59 | 0 | | | | | | |
| SHEET | 2 | E 4 | VAL B | 62 | GLY B | 67 | −1 | N | VAL B | 62 | O | GLU B | 59 |
| SHEET | 3 | E 4 | ARG B | 72 | MET B | 76 | −1 | O | ARG B | 72 | N | GLY B | 67 |
| SHEET | 4 | E 4 | LEU B | 82 | SER B | 85 | −1 | O | LEU B | 83 | N | ALA B | 75 |
| SHEET | 1 | F 4 | LEU B | 53 | GLU B | 59 | 0 | | | | | | |
| SHEET | 2 | F 4 | VAL B | 62 | GLY B | 67 | −1 | N | VAL B | 62 | O | GLU B | 59 |
| SHEET | 3 | F 4 | PHE B | 94 | LEU B | 98 | −1 | N | PHE B | 94 | O | VAL B | 63 |
| SHEET | 4 | F 4 | ASN B | 104 | SER B | 108 | −1 | O | THR B | 105 | N | ARG B | 97 |
| SHEET | 1 | G 4 | VAL C | 40 | VAL C | 43 | 0 | | | | | | |
| SHEET | 2 | G 4 | PHE C | 30 | ILE C | 34 | −1 | N | PHE C | 31 | O | VAL C | 43 |
| SHEET | 3 | G 4 | LYS C | 21 | CYS C | 25 | −1 | O | LEU C | 23 | N | LEU C | 32 |
| SHEET | 4 | G 4 | PHE C | 139 | SER C | 143 | −1 | N | LEU C | 140 | O | TYR C | 24 |
| SHEET | 1 | H 4 | LEU C | 53 | GLU C | 59 | 0 | | | | | | |
| SHEET | 2 | H 4 | VAL C | 62 | GLY C | 67 | −1 | N | VAL C | 62 | O | GLU C | 59 |
| SHEET | 3 | H 4 | ARG C | 72 | MET C | 76 | −1 | O | ARG C | 72 | N | GLY C | 67 |
| SHEET | 4 | H 4 | LEU C | 82 | SER C | 85 | −1 | O | LEU C | 83 | N | ALA C | 75 |
| SHEET | 1 | I 4 | LEU C | 53 | GLU C | 59 | 0 | | | | | | |
| SHEET | 2 | I 4 | VAL C | 62 | GLY C | 67 | −1 | N | VAL C | 62 | O | GLU C | 59 |
| SHEET | 3 | I 4 | PHE C | 94 | LEU C | 98 | −1 | O | PHE C | 94 | N | VAL C | 63 |
| SHEET | 4 | I 4 | ASN C | 104 | SER C | 108 | −1 | O | THR C | 105 | N | ARG C | 97 |
| SHEET | 1 | J 4 | VAL D | 40 | VAL D | 43 | 0 | | | | | | |
| SHEET | 2 | J 4 | PHE D | 30 | ILE D | 34 | −1 | N | PHE D | 31 | O | VAL D | 43 |
| SHEET | 3 | J 4 | LYS D | 21 | CYS D | 25 | −1 | O | LEU D | 23 | N | LEU D | 32 |
| SHEET | 4 | J 4 | PHE D | 139 | SER D | 143 | −1 | N | LEU D | 140 | O | TYR D | 24 |
| SHEET | 1 | K 4 | LEU D | 53 | GLU D | 59 | 0 | | | | | | |
| SHEET | 2 | K 4 | VAL D | 62 | GLY D | 67 | −1 | N | VAL D | 62 | O | GLU D | 59 |
| SHEET | 3 | K 4 | ARG D | 72 | MET D | 76 | −1 | O | ARG D | 72 | N | GLY D | 67 |
| SHEET | 4 | K 4 | LEU D | 82 | SER D | 85 | −1 | O | LEU D | 83 | N | ALA D | 75 |
| SHEET | 1 | L 4 | LEU D | 53 | GLU D | 59 | 0 | | | | | | |
| SHEET | 2 | L 4 | VAL D | 62 | GLY D | 67 | −1 | N | VAL D | 62 | O | GLU D | 59 |
| SHEET | 3 | L 4 | PHE D | 94 | LEU D | 98 | −1 | N | PHE D | 94 | O | VAL D | 63 |
| SHEET | 4 | L 4 | ASN D | 104 | SER D | 108 | −1 | O | THR D | 105 | N | ARG D | 97 |
| SHEET | 1 | M 2 | ARG E | 152 | TRP E | 156 | 0 | | | | | | |
| SHEET | 2 | M 2 | ALA E | 181 | ASN E | 184 | −1 | N | GLY E | 182 | O | TYR E | 155 |
| SHEET | 1 | N 5 | LEU E | 166 | PRO E | 170 | 0 | | | | | | |
| SHEET | 2 | N 5 | GLY E | 238 | VAL E | 249 | 1 | O | HIS E | 245 | N | HIS E | 167 |
| SHEET | 3 | N 5 | GLY E | 227 | ASN E | 235 | −1 | O | GLY E | 227 | N | LEU E | 246 |
| SHEET | 4 | N 5 | THR E | 188 | LYS E | 193 | −1 | N | THR E | 188 | O | GLU E | 234 |
| SHEET | 5 | N 5 | LYS E | 196 | GLU E | 197 | −1 | O | LYS E | 196 | N | LYS E | 193 |
| SHEET | 1 | O 3 | VAL E | 175 | ARG E | 178 | 0 | | | | | | |
| SHEET | 2 | O 3 | SER E | 215 | MET E | 218 | −1 | O | LEU E | 216 | N | PHE E | 177 |
| SHEET | 3 | O 3 | LYS E | 208 | ARG E | 210 | −1 | O | LYS E | 208 | N | ILE E | 217 |
| SHEET | 1 | P 2 | ILE E | 257 | LEU E | 258 | 0 | | | | | | |
| SHEET | 2 | P 2 | VAL E | 280 | TYR E | 281 | −1 | O | TYR E | 281 | N | ILE E | 257 |
| SHEET | 1 | Q 2 | VAL E | 274 | VAL E | 277 | 0 | | | | | | |
| SHEET | 2 | Q 2 | VAL E | 326 | ILE E | 329 | −1 | N | LEU E | 327 | O | PHE E | 276 |
| SHEET | 1 | R 4 | LEU E | 309 | ALA E | 314 | 0 | | | | | | |
| SHEET | 2 | R 4 | HIS E | 287 | HIS E | 293 | −1 | N | TRP E | 290 | O | LYS E | 313 |
| SHEET | 3 | R 4 | GLY E | 338 | GLY E | 345 | −1 | O | GLU E | 339 | N | HIS E | 293 |
| SHEET | 4 | R 4 | ILE E | 350 | LEU E | 357 | −1 | O | SER E | 351 | N | ALA E | 344 |
| SHEET | 1 | S 2 | ARG F | 152 | TRP F | 156 | 0 | | | | | | |
| SHEET | 2 | S 2 | ALA F | 181 | ASN F | 184 | −1 | N | GLY F | 182 | O | TYR F | 155 |
| SHEET | 1 | T 5 | LEU F | 166 | PRO F | 170 | 0 | | | | | | |
| SHEET | 2 | T 5 | GLY F | 238 | VAL F | 249 | 1 | O | HIS F | 245 | N | HIS F | 167 |
| SHEET | 3 | T 5 | GLY F | 227 | ASN F | 235 | −1 | O | GLY F | 227 | N | LEU F | 246 |
| SHEET | 4 | T 5 | THR F | 188 | LYS F | 193 | −1 | N | THR F | 188 | O | GLU F | 234 |
| SHEET | 5 | T 5 | LYS F | 196 | GLU F | 197 | −1 | O | LYS F | 196 | N | LYS F | 193 |
| SHEET | 1 | U 3 | VAL F | 175 | ARG F | 178 | 0 | | | | | | |
| SHEET | 2 | U 3 | SER F | 215 | MET F | 218 | −1 | O | LEU F | 216 | N | PHE F | 177 |
| SHEET | 3 | U 3 | LYS F | 208 | ARG F | 210 | −1 | O | LYS F | 208 | N | ILE F | 217 |
| SHEET | 1 | V 2 | ILE F | 257 | LEU F | 258 | 0 | | | | | | |
| SHEET | 2 | V 2 | VAL F | 280 | TYR F | 281 | −1 | O | TYR F | 281 | N | ILE F | 257 |
| SHEET | 1 | W 5 | ALA F | 266 | SER F | 267 | 0 | | | | | | |
| SHEET | 2 | W 5 | ILE F | 350 | THR F | 358 | 1 | O | TRP F | 356 | N | ALA F | 266 |
| SHEET | 3 | W 5 | GLY F | 338 | GLY F | 345 | −1 | O | GLY F | 338 | N | LEU F | 357 |
| SHEET | 4 | W 5 | HIS F | 287 | LYS F | 292 | −1 | N | HIS F | 287 | O | GLY F | 345 |
| SHEET | 5 | W 5 | LYS F | 310 | ALA F | 314 | −1 | O | LYS F | 310 | N | LYS F | 292 |
| SHEET | 1 | X 2 | VAL F | 274 | VAL F | 277 | 0 | | | | | | |
| SHEET | 2 | X 2 | VAL F | 326 | ILE F | 329 | −1 | N | LEU F | 327 | O | PHE F | 276 |
| SHEET | 1 | Y 2 | ARG G | 152 | TRP G | 156 | 0 | | | | | | |
| SHEET | 2 | Y 2 | ALA G | 181 | ASN G | 184 | −1 | N | GLY G | 182 | O | TYR G | 155 |
| SHEET | 1 | Z 5 | LEU G | 166 | PRO G | 170 | 0 | | | | | | |

TABLE 3-continued

FGFR2(D2–D3) Complexed with FGF2

| | | | | | | | | | | | | | | |
|---|---|---|---|---|---|---|---|---|---|---|---|---|---|---|
| SHEET | 2 | Z | 5 | GLY G | 238 | VAL G | 249 | 1 | O | HIS G | 245 | N | HIS G | 167 |
| SHEET | 3 | Z | 5 | GLY G | 227 | ASN G | 235 | −1 | O | GLY G | 227 | N | LEU G | 246 |
| SHEET | 4 | Z | 5 | THR G | 188 | LYS G | 193 | −1 | N | THR G | 188 | O | LEU G | 234 |
| SHEET | 5 | Z | 5 | LYS G | 196 | GLU G | 197 | −1 | O | LYS G | 196 | N | LYS G | 193 |
| SHEET | 1 | AA | 3 | VAL G | 175 | ARG G | 178 | 0 | | | | | | |
| SHEET | 2 | AA | 3 | SER G | 215 | MET G | 218 | −1 | O | LEU G | 216 | N | PHE G | 177 |
| SHEET | 3 | AA | 3 | LYS G | 208 | ARG G | 210 | −1 | O | LYS G | 208 | N | ILE G | 217 |
| SHEET | 1 | AB | 2 | ILE G | 257 | LEU G | 258 | 0 | | | | | | |
| SHEET | 2 | AB | 2 | VAL G | 280 | TYR G | 281 | −1 | O | TYR G | 281 | N | ILE G | 257 |
| SHEET | 1 | AC | 5 | ALA G | 266 | VAL G | 269 | 0 | | | | | | |
| SHEET | 2 | AC | 5 | ILE G | 350 | LEU G | 360 | 1 | O | TRP G | 356 | N | ALA G | 266 |
| SHEET | 3 | AC | 5 | GLY G | 338 | GLY G | 345 | −1 | O | GLY G | 338 | N | LEU G | 357 |
| SHEET | 4 | AC | 5 | HIS G | 287 | HIS G | 293 | −1 | N | HIS G | 287 | O | GLY G | 345 |
| SHEET | 5 | AC | 5 | LEU G | 309 | ALA G | 314 | −1 | O | LYS G | 310 | N | LYS G | 292 |
| SHEET | 1 | AD | 2 | VAL G | 274 | VAL G | 277 | 0 | | | | | | |
| SHEET | 2 | AD | 2 | VAL G | 326 | ILE G | 329 | −1 | N | LEU G | 327 | O | PHE G | 276 |
| SHEET | 1 | AE | 2 | ARG H | 152 | TRP H | 156 | 0 | | | | | | |
| SHEET | 2 | AE | 2 | ALA H | 181 | ASN H | 184 | −1 | N | GLY H | 182 | O | TYR H | 155 |
| SHEET | 1 | AF | 5 | LEU H | 166 | PRO H | 170 | 0 | | | | | | |
| SHEET | 2 | AF | 5 | GLY H | 238 | VAL H | 249 | 1 | O | HIS H | 245 | N | HIS H | 167 |
| SHEET | 3 | AF | 5 | GLY H | 227 | ASN H | 235 | −1 | O | GLY H | 227 | N | LEU H | 246 |
| SHEET | 4 | AF | 5 | THR H | 188 | LYS H | 193 | −1 | N | THR H | 188 | O | GLU H | 234 |
| SHEET | 5 | AF | 5 | LYS H | 196 | GLU H | 197 | −1 | O | LYS H | 196 | N | LYS H | 193 |
| SHEET | 1 | AG | 3 | VAL H | 175 | ARG H | 178 | 0 | | | | | | |
| SHEET | 2 | AG | 3 | SER H | 215 | MET H | 218 | −1 | O | LEU H | 216 | N | PHE H | 177 |
| SHEET | 3 | AG | 3 | LYS H | 208 | ARG H | 210 | −1 | O | LYS H | 208 | N | ILE H | 217 |
| SHEET | 1 | AH | 2 | ILE H | 257 | LEU H | 258 | 0 | | | | | | |
| SHEET | 2 | AH | 2 | VAL H | 280 | TYR H | 281 | −1 | O | TYR H | 281 | N | ILE H | 257 |
| SHEET | 1 | AI | 5 | ALA H | 266 | VAL H | 269 | 0 | | | | | | |
| SHEET | 2 | AI | 5 | ILE H | 350 | LEU H | 360 | 1 | O | TRP H | 356 | N | ALA H | 266 |
| SHEET | 3 | AI | 5 | GLY H | 338 | GLY H | 345 | −1 | O | GLY H | 338 | N | LEU H | 357 |
| SHEET | 4 | AI | 5 | HIS H | 287 | HIS H | 293 | −1 | N | HIS H | 287 | O | GLY H | 345 |
| SHEET | 5 | AI | 5 | LEU H | 309 | ALA H | 314 | −1 | O | LYS H | 310 | N | LYS H | 292 |
| SHEET | 1 | AJ | 2 | VAL H | 274 | VAL H | 277 | 0 | | | | | | |
| SHEET | 2 | AJ | 2 | VAL H | 326 | ILE H | 329 | −1 | N | LEU H | 327 | O | PHE H | 276 |
| SSBOND | 1 | CYS E | | 179 | CYS E | | 231 | | | | | | | |
| SSBOND | 2 | CYS E | | 278 | CYS E | | 342 | | | | | | | |
| SSBOND | 3 | CYS F | | 179 | CYS F | | 231 | | | | | | | |
| SSBOND | 4 | CYS F | | 278 | CYS F | | 342 | | | | | | | |
| SSBOND | 5 | CYS G | | 179 | CYS G | | 231 | | | | | | | |
| SSBOND | 6 | CYS G | | 278 | CYS G | | 342 | | | | | | | |
| SSBOND | 7 | CYS H | | 179 | CYS H | | 231 | | | | | | | |
| SSBOND | 8 | CYS H | | 278 | CYS H | | 342 | | | | | | | |
| CISPEP | 1 | ASN E | | 184 | PRO E | | 185 | 0 | 0.40 | | | | | |
| CISPEP | 2 | LEU E | | 262 | PRO E | | 263 | 0 | −0.38 | | | | | |
| CISPEP | 3 | ASN F | | 184 | PRO F | | 185 | 0 | 0.15 | | | | | |
| CISPEP | 4 | LEU F | | 262 | PRO F | | 263 | 0 | −0.12 | | | | | |
| CISPEP | 5 | ASN G | | 184 | PRO G | | 185 | 0 | 0.49 | | | | | |
| CISPEP | 6 | LEU G | | 262 | PRO G | | 263 | 0 | −0.21 | | | | | |
| CISPEP | 7 | ASN H | | 184 | PRO H | | 185 | 0 | 0.32 | | | | | |
| CISPEP | 8 | LEU H | | 262 | PRO H | | 263 | 0 | 0.10 | | | | | |
| CRYST1 | 72.198 | 71.677 | 90.920 | 90.53 | 89.98 | 89.99 | P 1 | 4 | | | | | | |
| ORIGX1 | 1.000000 | 0.000000 | 0.000000 | 0.00000 | | | | | | | | | | |
| ORIGX2 | 0.000000 | 1.000000 | 0.000000 | 0.00000 | | | | | | | | | | |
| ORIGX3 | 0.000000 | 0.000000 | 1.000000 | 0.00000 | | | | | | | | | | |
| SCALE1 | 0.013851 | −0.000002 | −0.000005 | 0.00000 | | | | | | | | | | |
| SCALE2 | 0.000000 | 0.013951 | 0.000129 | 0.00000 | | | | | | | | | | |
| SCALE3 | 0.000000 | 0.000000 | 0.010999 | 0.00000 | | | | | | | | | | |
| ATOM | 1 | N | HIS | A | 16 | 65.781 | −6.823 | 6.422 | 1.00 | 40.96 | N | | | |
| ATOM | 2 | CA | HIS | A | 16 | 66.617 | −7.615 | 7.378 | 1.00 | 40.54 | C | | | |
| ATOM | 3 | C | HIS | A | 16 | 68.092 | −7.469 | 7.011 | 1.00 | 39.31 | C | | | |
| ATOM | 4 | O | HIS | A | 16 | 68.508 | −7.845 | 5.917 | 1.00 | 39.03 | O | | | |
| ATOM | 5 | CB | HIS | A | 16 | 66.208 | −9.095 | 7.337 | 1.00 | 41.05 | C | | | |
| ATOM | 6 | N | PHE | A | 17 | 68.872 | −6.932 | 7.942 | 1.00 | 38.01 | N | | | |
| ATOM | 7 | CA | PHE | A | 17 | 70.295 | −6.694 | 7.734 | 1.00 | 37.01 | C | | | |
| ATOM | 8 | C | PHE | A | 17 | 71.138 | −7.925 | 7.375 | 1.00 | 36.59 | C | | | |
| ATOM | 9 | O | PHE | A | 17 | 72.148 | −7.797 | 6.674 | 1.00 | 35.98 | O | | | |
| ATOM | 10 | CB | PHE | A | 17 | 70.876 | −6.008 | 8.975 | 1.00 | 35.65 | C | | | |
| ATOM | 11 | CG | PHE | A | 17 | 70.934 | −6.887 | 10.184 | 1.00 | 35.24 | C | | | |
| ATOM | 12 | CD1 | PHE | A | 17 | 72.061 | −7.659 | 10.442 | 1.00 | 35.09 | C | | | |
| ATOM | 13 | CD2 | PHE | A | 17 | 69.877 | −6.928 | 11.084 | 1.00 | 35.37 | C | | | |
| ATOM | 14 | CE1 | PHE | A | 17 | 72.139 | −8.452 | 11.578 | 1.00 | 35.43 | C | | | |
| ATOM | 15 | CE2 | PHE | A | 17 | 69.942 | −7.724 | 12.231 | 1.00 | 35.92 | C | | | |
| ATOM | 16 | CZ | PHE | A | 17 | 71.075 | −8.487 | 12.479 | 1.00 | 35.61 | C | | | |
| ATOM | 17 | N | LYS | A | 18 | 70.743 | −9.106 | 7.844 | 1.00 | 36.25 | N | | | |
| ATOM | 18 | CA | LYS | A | 18 | 71.527 | −10.296 | 7.529 | 1.00 | 37.09 | C | | | |

TABLE 3-continued

FGFR2(D2–D3) Complexed with FGF2

| ATOM | 19 | C | LYS | A | 18 | 71.279 | −10.894 | 6.143 | 1.00 | 37.63 | C |
|---|---|---|---|---|---|---|---|---|---|---|---|
| ATOM | 20 | O | LYS | A | 18 | 72.035 | −11.753 | 5.690 | 1.00 | 38.05 | O |
| ATOM | 21 | CB | LYS | A | 18 | 71.410 | −11.364 | 8.626 | 1.00 | 37.68 | C |
| ATOM | 22 | CG | LYS | A | 18 | 70.092 | −11.449 | 9.358 | 1.00 | 40.55 | C |
| ATOM | 23 | CD | LYS | A | 18 | 70.220 | −12.396 | 10.551 | 1.00 | 41.58 | C |
| ATOM | 24 | CE | LYS | A | 18 | 68.877 | −12.603 | 11.238 | 1.00 | 42.51 | C |
| ATOM | 25 | NZ | LYS | A | 18 | 68.252 | −11.308 | 11.616 | 1.00 | 43.74 | N |
| ATOM | 26 | N | ASP | A | 19 | 70.251 | −10.412 | 5.453 | 1.00 | 37.64 | N |
| ATOM | 27 | CA | ASP | A | 19 | 69.948 | −10.882 | 4.106 | 1.00 | 37.79 | C |
| ATOM | 28 | C | ASP | A | 19 | 70.899 | −10.289 | 3.067 | 1.00 | 37.96 | C |
| ATOM | 29 | O | ASP | A | 19 | 71.364 | −9.150 | 3.206 | 1.00 | 37.12 | O |
| ATOM | 30 | CB | ASP | A | 19 | 68.532 | −10.476 | 3.701 | 1.00 | 39.51 | C |
| ATOM | 31 | CG | ASP | A | 19 | 67.454 | −11.162 | 4.521 | 1.00 | 40.50 | C |
| ATOM | 32 | OD1 | ASP | A | 19 | 66.291 | −10.708 | 4.445 | 1.00 | 40.65 | O |
| ATOM | 33 | OD2 | ASP | A | 19 | 67.760 | −12.152 | 5.220 | 1.00 | 41.75 | O |
| ATOM | 34 | N | PRO | A | 20 | 71.209 | −11.066 | 2.011 | 1.00 | 38.07 | N |
| ATOM | 35 | CA | PRO | A | 20 | 72.092 | −10.620 | 0.929 | 1.00 | 37.64 | C |
| ATOM | 36 | C | PRO | A | 20 | 71.431 | −9.441 | 0.211 | 1.00 | 37.31 | C |
| ATOM | 37 | O | PRO | A | 20 | 70.217 | −9.264 | 0.300 | 1.00 | 36.68 | O |
| ATOM | 38 | CB | PRO | A | 20 | 72.208 | −11.860 | 0.033 | 1.00 | 38.78 | C |
| ATOM | 39 | CG | PRO | A | 20 | 70.966 | −12.663 | 0.352 | 1.00 | 39.38 | C |
| ATOM | 40 | CD | PRO | A | 20 | 70.850 | −12.489 | 1.845 | 1.00 | 38.63 | C |
| ATOM | 41 | N | LYS | A | 21 | 72.218 | −8.648 | −0.508 | 1.00 | 36.88 | N |
| ATOM | 42 | CA | LYS | A | 21 | 71.676 | −7.467 | −1.180 | 1.00 | 37.48 | C |
| ATOM | 43 | C | LYS | A | 21 | 72.379 | −7.166 | −2.476 | 1.00 | 37.29 | C |
| ATOM | 44 | O | LYS | A | 21 | 73.460 | −7.684 | −2.752 | 1.00 | 37.08 | O |
| ATOM | 45 | CB | LYS | A | 21 | 71.872 | −6.198 | −0.336 | 1.00 | 37.95 | C |
| ATOM | 46 | CG | LYS | A | 21 | 71.512 | −6.244 | 1.129 | 1.00 | 38.66 | C |
| ATOM | 47 | CD | LYS | A | 21 | 71.931 | −4.921 | 1.755 | 1.00 | 40.44 | C |
| ATOM | 48 | CE | LYS | A | 21 | 71.606 | −4.821 | 3.239 | 1.00 | 42.18 | C |
| ATOM | 49 | NZ | LYS | A | 21 | 71.769 | −3.412 | 3.691 | 1.00 | 42.97 | N |
| ATOM | 50 | N | ARG | A | 22 | 71.761 | −6.288 | −3.254 | 1.00 | 36.67 | N |
| ATOM | 51 | CA | ARG | A | 22 | 72.355 | −5.825 | −4.492 | 1.00 | 36.55 | C |
| ATOM | 52 | C | ARG | A | 22 | 72.707 | −4.390 | −4.132 | 1.00 | 35.63 | C |
| ATOM | 53 | O | ARG | A | 22 | 71.986 | −3.755 | −3.360 | 1.00 | 36.38 | O |
| ATOM | 54 | CB | ARG | A | 22 | 71.340 | −5.813 | −5.633 | 1.00 | 38.00 | C |
| ATOM | 55 | CG | ARG | A | 22 | 70.630 | −7.118 | −5.891 | 1.00 | 40.54 | C |
| ATOM | 56 | CD | ARG | A | 22 | 69.712 | −6.938 | −7.092 | 1.00 | 43.45 | C |
| ATOM | 57 | NE | ARG | A | 22 | 68.439 | −7.649 | −6.962 | 1.00 | 47.18 | N |
| ATOM | 58 | CZ | ARG | A | 22 | 68.163 | −8.822 | −7.524 | 1.00 | 48.01 | C |
| ATOM | 59 | NH1 | ARG | A | 22 | 69.072 | −9.436 | −8.267 | 1.00 | 50.26 | N |
| ATOM | 60 | NH2 | ARG | A | 22 | 66.971 | −9.381 | −7.348 | 1.00 | 48.58 | N |
| ATOM | 61 | N | LEU | A | 23 | 73.818 | −3.881 | −4.647 | 1.00 | 34.34 | N |
| ATOM | 62 | CA | LEU | A | 23 | 74.201 | −2.502 | −4.380 | 1.00 | 32.35 | C |
| ATOM | 63 | C | LEU | A | 23 | 74.093 | −1.739 | −5.696 | 1.00 | 32.62 | C |
| ATOM | 64 | O | LEU | A | 23 | 74.914 | −1.906 | −6.603 | 1.00 | 32.26 | O |
| ATOM | 65 | CB | LEU | A | 23 | 75.617 | −2.419 | −3.811 | 1.00 | 30.80 | C |
| ATOM | 66 | CG | LEU | A | 23 | 75.763 | −2.709 | −2.306 | 1.00 | 30.93 | C |
| ATOM | 67 | CD1 | LEU | A | 23 | 77.234 | −2.691 | −1.923 | 1.00 | 30.37 | C |
| ATOM | 68 | CD2 | LEU | A | 23 | 75.009 | −1.662 | −1.491 | 1.00 | 29.15 | C |
| ATOM | 69 | N | TYR | A | 24 | 73.051 | −0.910 | −5.783 | 1.00 | 31.86 | N |
| ATOM | 70 | CA | TYR | A | 24 | 72.740 | −0.103 | −6.965 | 1.00 | 31.06 | C |
| ATOM | 71 | C | TYR | A | 24 | 73.479 | 1.236 | −6.959 | 1.00 | 31.28 | C |
| ATOM | 72 | O | TYR | A | 24 | 73.373 | 2.008 | −6.011 | 1.00 | 31.13 | O |
| ATOM | 73 | CB | TYR | A | 24 | 71.207 | 0.107 | −7.032 | 1.00 | 30.62 | C |
| ATOM | 74 | CG | TYR | A | 24 | 70.689 | 1.069 | −8.092 | 1.00 | 29.13 | C |
| ATOM | 75 | CD1 | TYR | A | 24 | 70.769 | 2.450 | −7.906 | 1.00 | 29.62 | C |
| ATOM | 76 | CD2 | TYR | A | 24 | 70.099 | 0.599 | −9.268 | 1.00 | 29.08 | C |
| ATOM | 77 | CE1 | TYR | A | 24 | 70.271 | 3.346 | −8.864 | 1.00 | 29.47 | C |
| ATOM | 78 | CE2 | TYR | A | 24 | 69.598 | 1.484 | −10.236 | 1.00 | 29.62 | C |
| ATOM | 79 | CZ | TYR | A | 24 | 69.686 | 2.859 | −10.024 | 1.00 | 30.70 | C |
| ATOM | 80 | OH | TYR | A | 24 | 69.181 | 3.748 | −10.957 | 1.00 | 31.61 | O |
| ATOM | 81 | N | CYS | A | 25 | 74.236 | 1.510 | −8.020 | 1.00 | 31.62 | N |
| ATOM | 82 | CA | CYS | A | 25 | 74.975 | 2.767 | −8.097 | 1.00 | 32.94 | C |
| ATOM | 83 | C | CYS | A | 25 | 74.147 | 3.842 | −8.798 | 1.00 | 33.32 | C |
| ATOM | 84 | O | CYS | A | 25 | 73.684 | 3.650 | −9.921 | 1.00 | 33.93 | O |
| ATOM | 85 | CB | CYS | A | 25 | 76.311 | 2.581 | −8.836 | 1.00 | 32.09 | C |
| ATOM | 86 | SG | CYS | A | 25 | 77.380 | 4.066 | −8.811 | 1.00 | 34.82 | S |
| ATOM | 87 | N | LYS | A | 26 | 73.963 | 4.970 | −8.122 | 1.00 | 34.61 | N |
| ATOM | 88 | CA | LYS | A | 26 | 73.189 | 6.072 | −8.676 | 1.00 | 36.27 | C |
| ATOM | 89 | C | LYS | A | 26 | 73.786 | 6.512 | −10.018 | 1.00 | 37.44 | C |
| ATOM | 90 | O | LYS | A | 26 | 73.061 | 6.928 | −10.923 | 1.00 | 37.35 | O |
| ATOM | 91 | CB | LYS | A | 26 | 73.171 | 7.248 | −7.697 | 1.00 | 36.24 | C |
| ATOM | 92 | CG | LYS | A | 26 | 72.293 | 8.403 | −8.145 | 1.00 | 38.36 | C |
| ATOM | 93 | CD | LYS | A | 26 | 72.480 | 9.630 | −7.270 | 1.00 | 39.80 | C |
| ATOM | 94 | CE | LYS | A | 26 | 71.585 | 10.769 | −7.747 | 1.00 | 41.47 | C |
| ATOM | 95 | NZ | LYS | A | 26 | 71.853 | 12.023 | −6.987 | 1.00 | 42.04 | N |

TABLE 3-continued

FGFR2(D2–D3) Complexed with FGF2

| ATOM | 96 | N | ASN | A | 27 | 75.107 | 6.406 | −10.148 | 1.00 | 37.91 | N |
|---|---|---|---|---|---|---|---|---|---|---|---|
| ATOM | 97 | CA | ASN | A | 27 | 75.782 | 6.790 | −11.386 | 1.00 | 38.44 | C |
| ATOM | 98 | C | ASN | A | 27 | 75.509 | 5.753 | −12.479 | 1.00 | 38.53 | C |
| ATOM | 99 | O | ASN | A | 27 | 76.092 | 4.663 | −12.479 | 1.00 | 38.51 | O |
| ATOM | 100 | CB | ASN | A | 27 | 77.287 | 6.904 | −11.152 | 1.00 | 40.85 | C |
| ATOM | 101 | CG | ASN | A | 27 | 78.001 | 7.640 | −12.276 | 1.00 | 44.71 | C |
| ATOM | 102 | OD1 | ASN | A | 27 | 79.237 | 7.582 | −12.395 | 1.00 | 44.59 | O |
| ATOM | 103 | ND2 | ASN | A | 27 | 77.230 | 8.350 | −13.101 | 1.00 | 44.65 | N |
| ATOM | 104 | N | GLY | A | 28 | 74.606 | 6.081 | −13.397 | 1.00 | 37.85 | N |
| ATOM | 105 | CA | GLY | A | 28 | 74.285 | 5.170 | −14.481 | 1.00 | 37.25 | C |
| ATOM | 106 | C | GLY | A | 28 | 73.303 | 4.054 | −14.159 | 1.00 | 37.29 | C |
| ATOM | 107 | O | GLY | A | 28 | 72.750 | 3.427 | −15.065 | 1.00 | 37.26 | O |
| ATOM | 108 | N | GLY | A | 29 | 73.089 | 3.779 | −12.878 | 1.00 | 37.91 | N |
| ATOM | 109 | CA | GLY | A | 29 | 72.153 | 2.730 | −12.512 | 1.00 | 38.15 | C |
| ATOM | 110 | C | GLY | A | 29 | 72.674 | 1.313 | −12.685 | 1.00 | 38.39 | C |
| ATOM | 111 | O | GLY | A | 29 | 71.937 | 0.423 | −13.114 | 1.00 | 37.89 | O |
| ATOM | 112 | N | PHE | A | 30 | 73.946 | 1.100 | −12.353 | 1.00 | 39.32 | N |
| ATOM | 113 | CA | PHE | A | 30 | 74.562 | −0.225 | −12.458 | 1.00 | 39.93 | C |
| ATOM | 114 | C | PHE | A | 30 | 74.609 | −0.919 | −11.102 | 1.00 | 39.45 | C |
| ATOM | 115 | O | PHE | A | 30 | 74.773 | −0.275 | −10.070 | 1.00 | 40.04 | O |
| ATOM | 116 | CB | PHE | A | 30 | 76.002 | −0.123 | −12.971 | 1.00 | 40.37 | C |
| ATOM | 117 | CG | PHE | A | 30 | 76.124 | 0.432 | −14.354 | 1.00 | 41.36 | C |
| ATOM | 118 | CD1 | PHE | A | 30 | 76.436 | 1.774 | −14.554 | 1.00 | 40.94 | C |
| ATOM | 119 | CD2 | PHE | A | 30 | 75.941 | −0.393 | −15.465 | 1.00 | 41.73 | C |
| ATOM | 120 | CE1 | PHE | A | 30 | 76.568 | 2.291 | −15.841 | 1.00 | 41.63 | C |
| ATOM | 121 | CE2 | PHE | A | 30 | 76.070 | 0.111 | −16.760 | 1.00 | 41.47 | C |
| ATOM | 122 | CZ | PHE | A | 30 | 76.384 | 1.457 | −16.950 | 1.00 | 41.25 | C |
| ATOM | 123 | N | PHE | A | 31 | 74.473 | −2.236 | −11.113 | 1.00 | 39.36 | N |
| ATOM | 124 | CA | PHE | A | 31 | 74.540 | −3.020 | −9.893 | 1.00 | 38.71 | C |
| ATOM | 125 | C | PHE | A | 31 | 75.980 | −3.498 | −9.744 | 1.00 | 39.23 | C |
| ATOM | 126 | O | PHE | A | 31 | 76.546 | −4.047 | −10.688 | 1.00 | 39.27 | O |
| ATOM | 127 | CB | PHE | A | 31 | 73.599 | −4.204 | −10.006 | 1.00 | 38.16 | C |
| ATOM | 128 | CG | PHE | A | 31 | 72.164 | −3.837 | −9.855 | 1.00 | 37.93 | C |
| ATOM | 129 | CD1 | PHE | A | 31 | 71.654 | −3.494 | −8.605 | 1.00 | 36.22 | C |
| ATOM | 130 | CD2 | PHE | A | 31 | 71.315 | −3.821 | −10.958 | 1.00 | 38.03 | C |
| ATOM | 131 | CE1 | PHE | A | 31 | 70.317 | −3.143 | −8.454 | 1.00 | 36.77 | C |
| ATOM | 132 | CE2 | PHE | A | 31 | 69.965 | −3.467 | −10.815 | 1.00 | 38.19 | C |
| ATOM | 133 | CZ | PHE | A | 31 | 69.469 | −3.128 | −9.557 | 1.00 | 36.80 | C |
| ATOM | 134 | N | LEU | A | 32 | 76.580 | −3.279 | −8.575 | 1.00 | 39.11 | N |
| ATOM | 135 | CA | LEU | A | 32 | 77.959 | −3.707 | −8.352 | 1.00 | 39.72 | C |
| ATOM | 136 | C | LEU | A | 32 | 78.047 | −5.205 | −8.596 | 1.00 | 40.18 | C |
| ATOM | 137 | O | LEU | A | 32 | 77.254 | −5.972 | −8.048 | 1.00 | 40.08 | O |
| ATOM | 138 | CB | LEU | A | 32 | 78.403 | −3.395 | −6.922 | 1.00 | 40.02 | C |
| ATOM | 139 | CG | LEU | A | 32 | 79.896 | −3.576 | −6.645 | 1.00 | 39.28 | C |
| ATOM | 140 | CD1 | LEU | A | 32 | 80.700 | −2.659 | −7.556 | 1.00 | 39.53 | C |
| ATOM | 141 | CD2 | LEU | A | 32 | 80.194 | −3.263 | −5.187 | 1.00 | 39.11 | C |
| ATOM | 142 | N | ARG | A | 33 | 79.006 | −5.621 | −9.420 | 1.00 | 41.12 | N |
| ATOM | 143 | CA | ARG | A | 33 | 79.162 | −7.038 | −9.751 | 1.00 | 41.65 | C |
| ATOM | 144 | C | ARG | A | 33 | 80.543 | −7.605 | −9.427 | 1.00 | 41.77 | C |
| ATOM | 145 | O | ARG | A | 33 | 81.568 | −6.987 | −9.720 | 1.00 | 41.35 | O |
| ATOM | 146 | CB | ARG | A | 33 | 78.851 | −7.253 | −11.236 | 1.00 | 41.70 | C |
| ATOM | 147 | CG | ARG | A | 33 | 79.046 | −8.686 | −11.700 | 1.00 | 42.74 | C |
| ATOM | 148 | CD | ARG | A | 33 | 78.491 | −8.922 | −13.089 | 1.00 | 41.98 | C |
| ATOM | 149 | NE | ARG | A | 33 | 79.193 | −8.155 | −14.113 | 1.00 | 43.07 | N |
| ATOM | 150 | CZ | ARG | A | 33 | 78.905 | −8.208 | −15.413 | 1.00 | 43.19 | C |
| ATOM | 151 | NH1 | ARG | A | 33 | 77.927 | −8.996 | −15.848 | 1.00 | 42.00 | N |
| ATOM | 152 | NH2 | ARG | A | 33 | 79.590 | −7.469 | −16.279 | 1.00 | 42.32 | N |
| ATOM | 153 | N | ILE | A | 34 | 80.561 | −8.785 | −8.813 | 1.00 | 42.97 | N |
| ATOM | 154 | CA | ILE | A | 34 | 81.820 | −9.442 | −8.465 | 1.00 | 44.25 | C |
| ATOM | 155 | C | ILE | A | 34 | 81.917 | −10.784 | −9.186 | 1.00 | 45.31 | C |
| ATOM | 156 | O | ILE | A | 34 | 81.232 | −11.743 | −8.837 | 1.00 | 45.06 | O |
| ATOM | 157 | CB | ILE | A | 34 | 81.957 | −9.626 | −6.933 | 1.00 | 44.16 | C |
| ATOM | 158 | CG1 | ILE | A | 34 | 82.190 | −8.253 | −6.285 | 1.00 | 43.89 | C |
| ATOM | 159 | CG2 | ILE | A | 34 | 83.115 | −10.575 | −6.604 | 1.00 | 43.90 | C |
| ATOM | 160 | CD1 | ILE | A | 34 | 82.527 | −8.297 | −4.818 | 1.00 | 43.24 | C |
| ATOM | 161 | N | HIS | A | 35 | 82.766 | −10.819 | −10.213 | 1.00 | 47.73 | N |
| ATOM | 162 | CA | HIS | A | 35 | 82.984 | −12.008 | −11.044 | 1.00 | 49.67 | C |
| ATOM | 163 | C | HIS | A | 35 | 83.746 | −13.118 | −10.335 | 1.00 | 50.49 | C |
| ATOM | 164 | O | HIS | A | 35 | 84.558 | −12.859 | −9.442 | 1.00 | 50.08 | O |
| ATOM | 165 | CB | HIS | A | 35 | 83.761 | −11.638 | −12.307 | 1.00 | 50.99 | C |
| ATOM | 166 | CG | HIS | A | 35 | 83.016 | −10.736 | −13.239 | 1.00 | 52.80 | C |
| ATOM | 167 | ND1 | HIS | A | 35 | 81.950 | −11.167 | −13.998 | 1.00 | 53.66 | N |
| ATOM | 168 | CD2 | HIS | A | 35 | 83.200 | −9.432 | −13.551 | 1.00 | 53.29 | C |
| ATOM | 169 | CE1 | HIS | A | 35 | 81.511 | −10.167 | −14.741 | 1.00 | 54.14 | C |
| ATOM | 170 | NE2 | HIS | A | 35 | 82.252 | −9.102 | −14.488 | 1.00 | 54.32 | N |
| ATOM | 171 | N | PRO | A | 36 | 83.510 | −14.376 | −10.748 | 1.00 | 51.42 | N |
| ATOM | 172 | CA | PRO | A | 36 | 84.171 | −15.543 | −10.158 | 1.00 | 51.76 | C |

TABLE 3-continued

| FGFR2(D2–D3) Complexed with FGF2 | | | | | | | | | | |
|---|---|---|---|---|---|---|---|---|---|---|
| ATOM | 173 | C | PRO | A | 36 | 85.698 | −15.454 | −10.187 | 1.00 | 52.11 | C |
| ATOM | 174 | O | PRO | A | 36 | 86.365 | −15.951 | −9.281 | 1.00 | 52.27 | O |
| ATOM | 175 | CB | PRO | A | 36 | 83.632 | −16.700 | −10.998 | 1.00 | 52.08 | C |
| ATOM | 176 | CG | PRO | A | 36 | 82.239 | −16.235 | −11.327 | 1.00 | 52.48 | C |
| ATOM | 177 | CD | PRO | A | 36 | 82.487 | −14.795 | −11.725 | 1.00 | 51.66 | C |
| ATOM | 178 | N | ASP | A | 37 | 86.246 | −14.813 | −11.217 | 1.00 | 52.61 | N |
| ATOM | 179 | CA | ASP | A | 37 | 87.696 | −14.685 | −11.328 | 1.00 | 52.96 | C |
| ATOM | 180 | C | ASP | A | 37 | 88.259 | −13.462 | −10.616 | 1.00 | 52.62 | C |
| ATOM | 181 | O | ASP | A | 37 | 89.444 | −13.154 | −10.746 | 1.00 | 53.00 | O |
| ATOM | 182 | CB | ASP | A | 37 | 88.141 | −14.688 | −12.803 | 1.00 | 54.40 | C |
| ATOM | 183 | CG | ASP | A | 37 | 87.511 | −13.570 | −13.620 | 1.00 | 55.76 | C |
| ATOM | 184 | OD1 | ASP | A | 37 | 86.310 | −13.676 | −13.962 | 1.00 | 55.75 | O |
| ATOM | 185 | OD2 | ASP | A | 37 | 88.226 | −12.584 | −13.917 | 1.00 | 56.34 | O |
| ATOM | 186 | N | GLY | A | 38 | 87.410 | −12.761 | −9.868 | 1.00 | 52.10 | N |
| ATOM | 187 | CA | GLY | A | 38 | 87.874 | −11.601 | −9.126 | 1.00 | 50.89 | C |
| ATOM | 188 | C | GLY | A | 38 | 87.793 | −10.223 | −9.766 | 1.00 | 50.43 | C |
| ATOM | 189 | O | GLY | A | 38 | 88.254 | −9.248 | −9.168 | 1.00 | 51.26 | O |
| ATOM | 190 | N | ARG | A | 39 | 87.222 | −10.115 | −10.960 | 1.00 | 49.14 | N |
| ATOM | 191 | CA | ARG | A | 39 | 87.106 | −8.811 | −11.615 | 1.00 | 48.54 | C |
| ATOM | 192 | C | ARG | A | 39 | 85.884 | −8.066 | −11.060 | 1.00 | 47.80 | C |
| ATOM | 193 | O | ARG | A | 39 | 84.876 | −8.689 | −10.717 | 1.00 | 47.58 | O |
| ATOM | 194 | CB | ARG | A | 39 | 86.973 | −8.991 | −13.135 | 1.00 | 47.72 | C |
| ATOM | 195 | N | VAL | A | 40 | 85.975 | −6.740 | −10.976 | 1.00 | 46.88 | N |
| ATOM | 196 | CA | VAL | A | 40 | 84.872 | −5.940 | −10.455 | 1.00 | 46.37 | C |
| ATOM | 197 | C | VAL | A | 40 | 84.383 | −4.864 | −11.421 | 1.00 | 45.86 | C |
| ATOM | 198 | O | VAL | A | 40 | 85.169 | −4.049 | −11.909 | 1.00 | 45.70 | O |
| ATOM | 199 | CB | VAL | A | 40 | 85.268 | −5.258 | −9.127 | 1.00 | 46.76 | C |
| ATOM | 200 | CG1 | VAL | A | 40 | 84.140 | −4.323 | −8.648 | 1.00 | 46.23 | C |
| ATOM | 201 | CG2 | VAL | A | 40 | 85.559 | −6.324 | −8.075 | 1.00 | 46.01 | C |
| ATOM | 202 | N | ASP | A | 41 | 83.079 | −4.872 | −11.689 | 1.00 | 45.56 | N |
| ATOM | 203 | CA | ASP | A | 41 | 82.458 | −3.885 | −12.570 | 1.00 | 45.56 | C |
| ATOM | 204 | C | ASP | A | 41 | 80.972 | −3.757 | −12.231 | 1.00 | 45.60 | C |
| ATOM | 205 | O | ASP | A | 41 | 80.517 | −4.264 | −11.201 | 1.00 | 45.05 | O |
| ATOM | 206 | CB | ASP | A | 41 | 82.627 | −4.287 | −14.039 | 1.00 | 45.40 | C |
| ATOM | 207 | CG | ASP | A | 41 | 81.851 | −5.543 | −14.399 | 1.00 | 45.94 | C |
| ATOM | 208 | OD1 | ASP | A | 41 | 81.894 | −5.949 | −15.584 | 1.00 | 47.24 | O |
| ATOM | 209 | OD2 | ASP | A | 41 | 81.201 | −6.129 | −13.507 | 1.00 | 46.40 | O |
| ATOM | 210 | N | GLY | A | 42 | 80.226 | −3.082 | −13.103 | 1.00 | 45.52 | N |
| ATOM | 211 | CA | GLY | A | 42 | 78.803 | −2.902 | −12.885 | 1.00 | 45.62 | C |
| ATOM | 212 | C | GLY | A | 42 | 77.992 | −3.371 | −14.076 | 1.00 | 46.37 | C |
| ATOM | 213 | O | GLY | A | 42 | 78.498 | −3.432 | −15.194 | 1.00 | 46.33 | O |
| ATOM | 214 | N | VAL | A | 43 | 76.736 | −3.725 | −13.831 | 1.00 | 47.09 | N |
| ATOM | 215 | CA | VAL | A | 43 | 75.833 | −4.176 | −14.883 | 1.00 | 47.46 | C |
| ATOM | 216 | C | VAL | A | 43 | 74.413 | −3.793 | −14.527 | 1.00 | 47.90 | C |
| ATOM | 217 | O | VAL | A | 43 | 74.084 | −3.654 | −13.351 | 1.00 | 48.34 | O |
| ATOM | 218 | CB | VAL | A | 43 | 75.876 | −5.698 | −15.085 | 1.00 | 47.31 | C |
| ATOM | 219 | CG1 | VAL | A | 43 | 77.025 | −6.052 | −15.978 | 1.00 | 48.06 | C |
| ATOM | 220 | CG2 | VAL | A | 43 | 75.988 | −6.404 | −13.754 | 1.00 | 46.61 | C |
| ATOM | 221 | N | ARG | A | 44 | 73.573 | −3.634 | −15.542 | 1.00 | 48.06 | N |
| ATOM | 222 | CA | ARG | A | 44 | 72.192 | −3.243 | −15.319 | 1.00 | 48.74 | C |
| ATOM | 223 | C | ARG | A | 44 | 71.206 | −4.396 | −15.200 | 1.00 | 49.88 | C |
| ATOM | 224 | O | ARG | A | 44 | 70.122 | −4.220 | −14.648 | 1.00 | 50.17 | O |
| ATOM | 225 | CB | ARG | A | 44 | 71.749 | −2.268 | −16.412 | 1.00 | 47.88 | C |
| ATOM | 226 | CG | ARG | A | 44 | 72.389 | −0.900 | −16.258 | 1.00 | 47.04 | C |
| ATOM | 227 | CD | ARG | A | 44 | 72.229 | −0.029 | −17.481 | 1.00 | 45.80 | C |
| ATOM | 228 | NE | ARG | A | 44 | 72.842 | 1.279 | −17.268 | 1.00 | 45.57 | N |
| ATOM | 229 | CZ | ARG | A | 44 | 73.279 | 2.064 | −18.245 | 1.00 | 45.12 | C |
| ATOM | 230 | NH1 | ARG | A | 44 | 73.173 | 1.665 | −19.506 | 1.00 | 45.80 | N |
| ATOM | 231 | NH2 | ARG | A | 44 | 73.824 | 3.242 | −17.966 | 1.00 | 43.95 | N |
| ATOM | 232 | N | GLU | A | 45 | 71.578 | −5.576 | −15.687 | 1.00 | 50.58 | N |
| ATOM | 233 | CA | GLU | A | 45 | 70.686 | −6.731 | −15.619 | 1.00 | 52.24 | C |
| ATOM | 234 | C | GLU | A | 45 | 70.476 | −7.247 | −14.192 | 1.00 | 53.19 | C |
| ATOM | 235 | O | GLU | A | 45 | 71.344 | −7.911 | −13.617 | 1.00 | 53.26 | O |
| ATOM | 236 | CB | GLU | A | 45 | 71.215 | −7.865 | −16.505 | 1.00 | 52.83 | C |
| ATOM | 237 | N | LYS | A | 46 | 69.306 | −6.947 | −13.634 | 1.00 | 53.61 | N |
| ATOM | 238 | CA | LYS | A | 46 | 68.965 | −7.367 | −12.283 | 1.00 | 53.94 | C |
| ATOM | 239 | C | LYS | A | 46 | 69.011 | −8.886 | −12.097 | 1.00 | 53.99 | C |
| ATOM | 240 | O | LYS | A | 46 | 68.992 | −9.379 | −10.969 | 1.00 | 54.53 | O |
| ATOM | 241 | CB | LYS | A | 46 | 67.571 | −6.842 | −11.918 | 1.00 | 53.70 | C |
| ATOM | 242 | N | SER | A | 47 | 69.091 | −9.625 | −13.198 | 1.00 | 53.70 | N |
| ATOM | 243 | CA | SER | A | 47 | 69.110 | −11.086 | −13.132 | 1.00 | 53.88 | C |
| ATOM | 244 | C | SER | A | 47 | 70.499 | −11.699 | −12.976 | 1.00 | 53.81 | C |
| ATOM | 245 | O | SER | A | 47 | 70.630 | −12.877 | −12.648 | 1.00 | 54.39 | O |
| ATOM | 246 | CB | SER | A | 47 | 68.437 | −11.674 | −14.379 | 1.00 | 53.87 | C |
| ATOM | 247 | N | ASP | A | 48 | 71.537 | −10.904 | −13.209 | 1.00 | 53.60 | N |
| ATOM | 248 | CA | ASP | A | 48 | 72.902 | −11.401 | −13.100 | 1.00 | 53.26 | C |
| ATOM | 249 | C | ASP | A | 48 | 73.153 | −12.030 | −11.729 | 1.00 | 52.56 | C |

TABLE 3-continued

FGFR2(D2–D3) Complexed with FGF2

| ATOM | 250 | O | ASP | A | 48 | 72.925 | −11.403 | −10.694 | 1.00 | 52.29 | O |
|---|---|---|---|---|---|---|---|---|---|---|---|
| ATOM | 251 | CB | ASP | A | 48 | 73.895 | −10.259 | −13.363 | 1.00 | 54.16 | C |
| ATOM | 252 | CG | ASP | A | 48 | 75.329 | −10.746 | −13.472 | 1.00 | 55.48 | C |
| ATOM | 253 | OD1 | ASP | A | 48 | 76.155 | −10.039 | −14.093 | 1.00 | 56.03 | O |
| ATOM | 254 | OD2 | ASP | A | 48 | 75.633 | −11.831 | −12.931 | 1.00 | 56.13 | O |
| ATOM | 255 | N | PRO | A | 49 | 73.626 | −13.289 | −11.709 | 1.00 | 52.00 | N |
| ATOM | 256 | CA | PRO | A | 49 | 73.908 | −14.015 | −10.466 | 1.00 | 50.81 | C |
| ATOM | 257 | C | PRO | A | 49 | 75.125 | −13.514 | −9.687 | 1.00 | 49.76 | C |
| ATOM | 258 | O | PRO | A | 49 | 75.337 | −13.915 | −8.545 | 1.00 | 49.74 | O |
| ATOM | 259 | CB | PRO | A | 49 | 74.083 | −15.450 | −10.948 | 1.00 | 51.73 | C |
| ATOM | 260 | CG | PRO | A | 49 | 74.740 | −15.249 | −12.294 | 1.00 | 51.98 | C |
| ATOM | 261 | CD | PRO | A | 49 | 73.903 | −14.136 | −12.885 | 1.00 | 52.08 | C |
| ATOM | 262 | N | HIS | A | 50 | 75.913 | −12.630 | −10.288 | 1.00 | 48.41 | N |
| ATOM | 263 | CA | HIS | A | 50 | 77.100 | −12.118 | −9.611 | 1.00 | 47.20 | C |
| ATOM | 264 | C | HIS | A | 50 | 77.963 | −10.738 | −8.956 | 1.00 | 45.56 | C |
| ATOM | 265 | O | HIS | A | 50 | 77.965 | −10.094 | −8.645 | 1.00 | 44.52 | O |
| ATOM | 266 | CB | HIS | A | 50 | 78.280 | −12.116 | −10.578 | 1.00 | 48.84 | C |
| ATOM | 267 | CG | HIS | A | 50 | 78.506 | −13.439 | −11.238 | 1.00 | 50.65 | C |
| ATOM | 268 | ND1 | HIS | A | 50 | 78.526 | −14.625 | −10.535 | 1.00 | 51.45 | N |
| ATOM | 269 | CD2 | HIS | A | 50 | 78.703 | −13.765 | −12.536 | 1.00 | 50.93 | C |
| ATOM | 270 | CE1 | HIS | A | 50 | 78.725 | −15.626 | −11.374 | 1.00 | 51.59 | C |
| ATOM | 271 | NE2 | HIS | A | 50 | 78.834 | −15.131 | −12.594 | 1.00 | 51.88 | N |
| ATOM | 272 | N | ILE | A | 51 | 75.729 | −10.286 | −8.751 | 1.00 | 44.07 | N |
| ATOM | 273 | CA | ILE | A | 51 | 75.506 | −9.003 | −8.095 | 1.00 | 42.96 | C |
| ATOM | 274 | C | ILE | A | 51 | 74.869 | −9.212 | −6.724 | 1.00 | 42.25 | C |
| ATOM | 275 | O | ILE | A | 51 | 74.588 | −8.247 | −6.005 | 1.00 | 41.38 | O |
| ATOM | 276 | CB | ILE | A | 51 | 74.623 | −8.063 | −8.938 | 1.00 | 42.32 | C |
| ATOM | 277 | CG1 | ILE | A | 51 | 73.259 | −8.700 | −9.187 | 1.00 | 42.29 | C |
| ATOM | 278 | CG2 | ILE | A | 51 | 75.324 | −7.743 | −10.243 | 1.00 | 42.67 | C |
| ATOM | 279 | CD1 | ILE | A | 51 | 72.237 | −7.734 | −9.762 | 1.00 | 43.48 | C |
| ATOM | 280 | N | LYS | A | 52 | 74.636 | −10.475 | −6.370 | 1.00 | 41.29 | N |
| ATOM | 281 | CA | LYS | A | 52 | 74.070 | −10.805 | −5.068 | 1.00 | 40.84 | C |
| ATOM | 282 | C | LYS | A | 52 | 75.232 | −10.757 | −4.078 | 1.00 | 39.49 | C |
| ATOM | 283 | O | LYS | A | 52 | 76.151 | −11.580 | −4.143 | 1.00 | 39.35 | O |
| ATOM | 284 | CB | LYS | A | 52 | 73.442 | −12.196 | −5.099 | 1.00 | 42.75 | C |
| ATOM | 285 | CG | LYS | A | 52 | 72.764 | −12.568 | −3.808 | 1.00 | 45.60 | C |
| ATOM | 286 | CD | LYS | A | 52 | 72.076 | −13.923 | −3.898 | 1.00 | 47.67 | C |
| ATOM | 287 | CE | LYS | A | 52 | 71.517 | −14.326 | −2.541 | 1.00 | 49.65 | C |
| ATOM | 288 | NZ | LYS | A | 52 | 70.843 | −15.651 | −2.558 | 1.00 | 51.56 | N |
| ATOM | 289 | N | LEU | A | 53 | 75.198 | −9.776 | −3.180 | 1.00 | 36.84 | N |
| ATOM | 290 | CA | LEU | A | 53 | 76.270 | −9.589 | −2.213 | 1.00 | 34.80 | C |
| ATOM | 291 | C | LEU | A | 53 | 75.875 | −9.831 | −0.765 | 1.00 | 34.19 | C |
| ATOM | 292 | O | LEU | A | 53 | 74.700 | −9.783 | −0.406 | 1.00 | 35.12 | O |
| ATOM | 293 | CB | LEU | A | 53 | 76.820 | −8.178 | −2.348 | 1.00 | 34.31 | C |
| ATOM | 294 | CG | LEU | A | 53 | 77.297 | −7.809 | −3.744 | 1.00 | 33.98 | C |
| ATOM | 295 | CD1 | LEU | A | 53 | 77.548 | −6.324 | −3.823 | 1.00 | 33.55 | C |
| ATOM | 296 | CD2 | LEU | A | 53 | 78.561 | −8.590 | −4.056 | 1.00 | 34.91 | C |
| ATOM | 297 | N | GLN | A | 54 | 76.875 | −10.085 | 0.069 | 1.00 | 32.74 | N |
| ATOM | 298 | CA | GLN | A | 54 | 76.642 | −10.326 | 1.487 | 1.00 | 32.06 | C |
| ATOM | 299 | C | GLN | A | 54 | 77.473 | −9.353 | 2.305 | 1.00 | 31.38 | C |
| ATOM | 300 | O | GLN | A | 54 | 78.703 | −9.459 | 2.315 | 1.00 | 30.82 | O |
| ATOM | 301 | CB | GLN | A | 54 | 77.062 | −11.748 | 1.869 | 1.00 | 32.52 | C |
| ATOM | 302 | CG | GLN | A | 54 | 76.733 | −12.126 | 3.307 | 1.00 | 32.29 | C |
| ATOM | 303 | CD | GLN | A | 54 | 75.241 | −12.187 | 3.551 | 1.00 | 34.18 | C |
| ATOM | 304 | OE1 | GLN | A | 54 | 74.533 | −13.005 | 2.954 | 1.00 | 34.26 | O |
| ATOM | 305 | NE2 | GLN | A | 54 | 74.748 | −11.316 | 4.424 | 1.00 | 33.63 | N |
| ATOM | 306 | N | LEU | A | 55 | 76.822 | −8.410 | 2.985 | 1.00 | 30.29 | N |
| ATOM | 307 | CA | LEU | A | 55 | 77.561 | −7.456 | 3.816 | 1.00 | 30.86 | C |
| ATOM | 308 | C | LEU | A | 55 | 77.673 | −8.028 | 5.233 | 1.00 | 30.05 | C |
| ATOM | 309 | O | LEU | A | 55 | 76.807 | −8.780 | 5.679 | 1.00 | 29.32 | O |
| ATOM | 310 | CB | LEU | A | 55 | 76.862 | −6.086 | 3.852 | 1.00 | 31.28 | C |
| ATOM | 311 | CG | LEU | A | 55 | 76.483 | −5.369 | 2.537 | 1.00 | 33.52 | C |
| ATOM | 312 | CD1 | LEU | A | 55 | 76.469 | −3.868 | 2.778 | 1.00 | 32.75 | C |
| ATOM | 313 | CD2 | LEU | A | 55 | 77.478 | −5.687 | 1.427 | 1.00 | 33.68 | C |
| ATOM | 314 | N | GLN | A | 56 | 78.746 | −7.682 | 5.930 | 1.00 | 28.63 | N |
| ATOM | 315 | CA | GLN | A | 56 | 78.962 | −8.173 | 7.282 | 1.00 | 28.77 | C |
| ATOM | 316 | C | GLN | A | 56 | 79.827 | −7.164 | 8.016 | 1.00 | 29.04 | C |
| ATOM | 317 | O | GLN | A | 56 | 80.889 | −6.790 | 7.522 | 1.00 | 28.60 | O |
| ATOM | 318 | CB | GLN | A | 56 | 79.658 | −9.545 | 7.229 | 1.00 | 28.70 | C |
| ATOM | 319 | CG | GLN | A | 56 | 80.009 | −10.173 | 8.586 | 1.00 | 29.29 | C |
| ATOM | 320 | CD | GLN | A | 56 | 78.798 | −10.400 | 9.469 | 1.00 | 28.66 | C |
| ATOM | 321 | OE1 | GLN | A | 56 | 77.906 | −11.192 | 9.143 | 1.00 | 29.16 | O |
| ATOM | 322 | NE2 | GLN | A | 56 | 78.754 | −9.695 | 10.597 | 1.00 | 29.84 | N |
| ATOM | 323 | N | ALA | A | 57 | 79.362 | −6.714 | 9.178 | 1.00 | 29.57 | N |
| ATOM | 324 | CA | ALA | A | 57 | 80.104 | −5.744 | 9.977 | 1.00 | 30.66 | C |
| ATOM | 325 | C | ALA | A | 57 | 81.261 | −6.418 | 10.721 | 1.00 | 31.59 | C |
| ATOM | 326 | O | ALA | A | 57 | 81.094 | −7.491 | 11.295 | 1.00 | 31.05 | O |

TABLE 3-continued

FGFR2(D2–D3) Complexed with FGF2

| ATOM | 327 | CB | ALA | A | 57 | 79.162 | −5.072 | 10.977 | 1.00 | 30.28 | C |
|---|---|---|---|---|---|---|---|---|---|---|---|
| ATOM | 328 | N | GLU | A | 58 | 82.430 | −5.783 | 10.708 | 1.00 | 32.12 | N |
| ATOM | 329 | CA | GLU | A | 58 | 83.595 | −6.330 | 11.391 | 1.00 | 33.18 | C |
| ATOM | 330 | C | GLU | A | 58 | 83.752 | −5.580 | 12.713 | 1.00 | 33.89 | C |
| ATOM | 331 | O | GLU | A | 58 | 84.270 | −6.119 | 13.695 | 1.00 | 33.53 | O |
| ATOM | 332 | CB | GLU | A | 58 | 84.845 | −6.173 | 10.515 | 1.00 | 34.27 | C |
| ATOM | 333 | CG | GLU | A | 58 | 85.985 | −7.131 | 10.859 | 1.00 | 35.60 | C |
| ATOM | 334 | CD | GLU | A | 58 | 85.594 | −8.601 | 10.725 | 1.00 | 37.03 | C |
| ATOM | 335 | OE1 | GLU | A | 58 | 84.964 | −8.980 | 9.715 | 1.00 | 37.39 | O |
| ATOM | 336 | OE2 | GLU | A | 58 | 85.926 | −9.387 | 11.635 | 1.00 | 39.38 | O |
| ATOM | 337 | N | GLU | A | 59 | 83.309 | −4.325 | 12.710 | 1.00 | 34.07 | N |
| ATOM | 338 | CA | GLU | A | 59 | 83.308 | −3.467 | 13.891 | 1.00 | 34.95 | C |
| ATOM | 339 | C | GLU | A | 59 | 82.302 | −2.353 | 13.593 | 1.00 | 33.54 | C |
| ATOM | 340 | O | GLU | A | 59 | 81.825 | −2.236 | 12.465 | 1.00 | 33.43 | O |
| ATOM | 341 | CB | GLU | A | 59 | 84.707 | −2.904 | 14.195 | 1.00 | 36.91 | C |
| ATOM | 342 | CG | GLU | A | 59 | 85.182 | −1.759 | 13.322 | 1.00 | 40.94 | C |
| ATOM | 343 | CD | GLU | A | 59 | 86.539 | −1.224 | 13.774 | 1.00 | 43.27 | C |
| ATOM | 344 | OE1 | GLU | A | 59 | 87.532 | −1.977 | 13.689 | 1.00 | 45.02 | O |
| ATOM | 345 | OE2 | GLU | A | 59 | 86.615 | −0.058 | 14.225 | 1.00 | 44.36 | O |
| ATOM | 346 | N | ARG | A | 60 | 81.969 | −1.550 | 14.593 | 1.00 | 32.58 | N |
| ATOM | 347 | CA | ARG | A | 60 | 80.991 | −0.486 | 14.413 | 1.00 | 32.17 | C |
| ATOM | 348 | C | ARG | A | 60 | 81.227 | 0.369 | 13.154 | 1.00 | 31.15 | C |
| ATOM | 349 | O | ARG | A | 60 | 82.287 | 0.978 | 12.988 | 1.00 | 30.43 | O |
| ATOM | 350 | CB | ARG | A | 60 | 80.981 | 0.381 | 15.676 | 1.00 | 33.58 | C |
| ATOM | 351 | CG | ARG | A | 60 | 79.844 | 1.365 | 15.781 | 1.00 | 36.07 | C |
| ATOM | 352 | CD | ARG | A | 60 | 79.939 | 2.142 | 17.087 | 1.00 | 38.02 | C |
| ATOM | 353 | NE | ARG | A | 60 | 79.379 | 3.472 | 16.921 | 1.00 | 42.32 | N |
| ATOM | 354 | CZ | ARG | A | 60 | 80.065 | 4.601 | 17.059 | 1.00 | 44.12 | C |
| ATOM | 355 | NH1 | ARG | A | 60 | 81.351 | 4.574 | 17.384 | 1.00 | 44.60 | N |
| ATOM | 356 | NH2 | ARG | A | 60 | 79.466 | 5.761 | 16.829 | 1.00 | 46.46 | N |
| ATOM | 357 | N | GLY | A | 61 | 80.245 | 0.383 | 12.253 | 1.00 | 29.90 | N |
| ATOM | 358 | CA | GLY | A | 61 | 80.356 | 1.185 | 11.043 | 1.00 | 28.83 | C |
| ATOM | 359 | C | GLY | A | 61 | 81.330 | 0.720 | 9.972 | 1.00 | 28.80 | C |
| ATOM | 360 | O | GLY | A | 61 | 81.550 | 1.430 | 8.986 | 1.00 | 28.16 | O |
| ATOM | 361 | N | VAL | A | 62 | 81.913 | −0.467 | 10.148 | 1.00 | 28.29 | N |
| ATOM | 362 | CA | VAL | A | 62 | 82.861 | −1.000 | 9.171 | 1.00 | 27.10 | C |
| ATOM | 363 | C | VAL | A | 62 | 82.384 | −2.354 | 8.646 | 1.00 | 26.34 | C |
| ATOM | 364 | O | VAL | A | 62 | 82.059 | −3.248 | 9.422 | 1.00 | 25.88 | O |
| ATOM | 365 | CB | VAL | A | 62 | 84.265 | −1.161 | 9.799 | 1.00 | 28.53 | C |
| ATOM | 366 | CG1 | VAL | A | 62 | 85.279 | −1.603 | 8.723 | 1.00 | 29.17 | C |
| ATOM | 367 | CG2 | VAL | A | 62 | 84.702 | 0.152 | 10.450 | 1.00 | 28.29 | C |
| ATOM | 368 | N | VAL | A | 63 | 82.343 | −2.517 | 7.328 | 1.00 | 25.99 | N |
| ATOM | 369 | CA | VAL | A | 63 | 81.878 | −3.781 | 6.762 | 1.00 | 25.26 | C |
| ATOM | 370 | C | VAL | A | 63 | 82.788 | −4.378 | 5.695 | 1.00 | 26.19 | C |
| ATOM | 371 | O | VAL | A | 63 | 83.677 | −3.704 | 5.157 | 1.00 | 26.01 | O |
| ATOM | 372 | CB | VAL | A | 63 | 80.474 | −3.634 | 6.109 | 1.00 | 24.65 | C |
| ATOM | 373 | CG1 | VAL | A | 63 | 79.509 | −2.926 | 7.065 | 1.00 | 25.24 | C |
| ATOM | 374 | CG2 | VAL | A | 63 | 80.587 | −2.856 | 4.794 | 1.00 | 22.71 | C |
| ATOM | 375 | N | SER | A | 64 | 82.552 | −5.655 | 5.405 | 1.00 | 26.88 | N |
| ATOM | 376 | CA | SER | A | 64 | 83.263 | −6.358 | 4.341 | 1.00 | 27.68 | C |
| ATOM | 377 | C | SER | A | 64 | 82.119 | −6.687 | 3.375 | 1.00 | 27.92 | C |
| ATOM | 378 | O | SER | A | 64 | 80.979 | −6.878 | 3.804 | 1.00 | 28.11 | O |
| ATOM | 379 | CB | SER | A | 64 | 83.946 | −7.646 | 4.846 | 1.00 | 27.31 | C |
| ATOM | 380 | OG | SER | A | 64 | 83.020 | −8.615 | 5.315 | 1.00 | 27.80 | O |
| ATOM | 381 | N | ILE | A | 65 | 82.415 | −6.712 | 2.082 | 1.00 | 27.99 | N |
| ATOM | 382 | CA | ILE | A | 65 | 81.410 | −6.996 | 1.068 | 1.00 | 29.29 | C |
| ATOM | 383 | C | ILE | A | 65 | 81.827 | −8.241 | 0.264 | 1.00 | 31.00 | C |
| ATOM | 384 | O | ILE | A | 65 | 82.841 | −8.223 | −0.439 | 1.00 | 29.42 | O |
| ATOM | 385 | CB | ILE | A | 65 | 81.258 | −5.786 | 0.121 | 1.00 | 29.51 | C |
| ATOM | 386 | CG1 | ILE | A | 65 | 80.756 | −4.565 | 0.908 | 1.00 | 30.05 | C |
| ATOM | 387 | CG2 | ILE | A | 65 | 80.277 | −6.117 | −0.990 | 1.00 | 30.34 | C |
| ATOM | 388 | CD1 | ILE | A | 65 | 80.874 | −3.234 | 0.160 | 1.00 | 30.18 | C |
| ATOM | 389 | N | LYS | A | 66 | 81.032 | −9.306 | 0.356 | 1.00 | 31.83 | N |
| ATOM | 390 | CA | LYS | A | 66 | 81.353 | −10.560 | −0.317 | 1.00 | 34.62 | C |
| ATOM | 391 | C | LYS | A | 66 | 80.397 | −10.993 | −1.434 | 1.00 | 35.76 | C |
| ATOM | 392 | O | LYS | A | 66 | 79.179 | −11.031 | −1.251 | 1.00 | 34.62 | O |
| ATOM | 393 | CB | LYS | A | 66 | 81.451 | −11.681 | 0.737 | 1.00 | 35.88 | C |
| ATOM | 394 | CG | LYS | A | 66 | 81.735 | −13.089 | 0.193 | 1.00 | 36.63 | C |
| ATOM | 395 | CD | LYS | A | 66 | 81.757 | −14.123 | 1.321 | 1.00 | 37.90 | C |
| ATOM | 396 | CE | LYS | A | 66 | 81.989 | −15.544 | 0.806 | 1.00 | 39.28 | C |
| ATOM | 397 | NZ | LYS | A | 66 | 82.226 | −16.531 | 1.919 | 1.00 | 39.38 | N |
| ATOM | 398 | N | GLY | A | 67 | 80.961 | −11.316 | −2.597 | 1.00 | 37.32 | N |
| ATOM | 399 | CA | GLY | A | 67 | 80.146 | −11.789 | −3.707 | 1.00 | 39.35 | C |
| ATOM | 400 | C | GLY | A | 67 | 79.760 | −13.231 | −3.407 | 1.00 | 41.10 | C |
| ATOM | 401 | O | GLY | A | 67 | 80.625 | −14.104 | −3.319 | 1.00 | 41.10 | O |
| ATOM | 402 | N | VAL | A | 68 | 78.469 | −13.488 | −3.233 | 1.00 | 42.27 | N |
| ATOM | 403 | CA | VAL | A | 68 | 78.006 | −14.831 | −2.908 | 1.00 | 44.02 | C |

TABLE 3-continued

FGFR2(D2–D3) Complexed with FGF2

| ATOM | 404 | C | VAL | A | 68 | 78.433 | −15.881 | −3.933 | 1.00 | 45.16 | C |
|---|---|---|---|---|---|---|---|---|---|---|---|
| ATOM | 405 | O | VAL | A | 68 | 79.007 | −16.906 | −3.560 | 1.00 | 45.69 | O |
| ATOM | 406 | CB | VAL | A | 68 | 76.465 | −14.869 | −2.754 | 1.00 | 44.56 | C |
| ATOM | 407 | CG1 | VAL | A | 68 | 76.006 | −16.280 | −2.426 | 1.00 | 44.70 | C |
| ATOM | 408 | CG2 | VAL | A | 68 | 76.032 | −13.921 | −1.639 | 1.00 | 45.21 | C |
| ATOM | 409 | N | SER | A | 69 | 78.164 | −15.631 | −5.214 | 1.00 | 45.89 | N |
| ATOM | 410 | CA | SER | A | 69 | 78.533 | −16.582 | −6.270 | 1.00 | 46.52 | C |
| ATOM | 411 | C | SER | A | 69 | 80.036 | −16.769 | −6.398 | 1.00 | 46.52 | C |
| ATOM | 412 | O | SER | A | 69 | 80.538 | −17.889 | −6.308 | 1.00 | 46.68 | O |
| ATOM | 413 | CB | SER | A | 69 | 77.974 | −16.146 | −7.630 | 1.00 | 47.12 | C |
| ATOM | 414 | OG | SER | A | 69 | 76.629 | −16.568 | −7.798 | 1.00 | 47.66 | O |
| ATOM | 415 | N | ALA | A | 70 | 80.749 | −15.670 | −6.609 | 1.00 | 46.10 | N |
| ATOM | 416 | CA | ALA | A | 70 | 82.193 | −15.717 | −6.762 | 1.00 | 46.16 | C |
| ATOM | 417 | C | ALA | A | 70 | 82.905 | −16.199 | −5.498 | 1.00 | 46.34 | C |
| ATOM | 418 | O | ALA | A | 70 | 84.060 | −16.625 | −5.556 | 1.00 | 46.73 | O |
| ATOM | 419 | CB | ALA | A | 70 | 82.710 | −14.344 | −7.161 | 1.00 | 46.03 | C |
| ATOM | 420 | N | ASN | A | 71 | 82.214 | −16.134 | −4.362 | 1.00 | 46.13 | N |
| ATOM | 421 | CA | ASN | A | 71 | 82.791 | −16.540 | −3.080 | 1.00 | 46.22 | C |
| ATOM | 422 | C | ASN | A | 71 | 84.099 | −15.780 | −2.820 | 1.00 | 45.32 | C |
| ATOM | 423 | O | ASN | A | 71 | 85.074 | −16.345 | −2.323 | 1.00 | 44.86 | O |
| ATOM | 424 | CB | ASN | A | 71 | 83.025 | −18.061 | −3.059 | 1.00 | 47.52 | C |
| ATOM | 425 | CG | ASN | A | 71 | 83.496 | −18.578 | −1.692 | 1.00 | 49.37 | C |
| ATOM | 426 | OD1 | ASN | A | 71 | 82.985 | −18.172 | −0.639 | 1.00 | 49.71 | O |
| ATOM | 427 | ND2 | ASN | A | 71 | 84.464 | −19.494 | −1.709 | 1.00 | 49.93 | N |
| ATOM | 428 | N | ARG | A | 72 | 84.100 | −14.492 | −3.165 | 1.00 | 44.62 | N |
| ATOM | 429 | CA | ARG | A | 72 | 85.259 | −13.620 | −2.980 | 1.00 | 43.24 | C |
| ATOM | 430 | C | ARG | A | 72 | 84.849 | −12.325 | −2.265 | 1.00 | 43.09 | C |
| ATOM | 431 | O | ARG | A | 72 | 83.665 | −11.965 | −2.247 | 1.00 | 42.61 | O |
| ATOM | 432 | CB | ARG | A | 72 | 85.890 | −13.286 | −4.331 | 1.00 | 42.91 | C |
| ATOM | 433 | N | TYR | A | 73 | 85.836 | −11.637 | −1.684 | 1.00 | 41.68 | N |
| ATOM | 434 | CA | TYR | A | 73 | 85.616 | −10.398 | −0.941 | 1.00 | 40.49 | C |
| ATOM | 435 | C | TYR | A | 73 | 86.114 | −9.166 | −1.696 | 1.00 | 40.25 | C |
| ATOM | 436 | O | TYR | A | 73 | 87.253 | −9.145 | −2.180 | 1.00 | 40.29 | O |
| ATOM | 437 | CB | TYR | A | 73 | 86.337 | −10.447 | 0.417 | 1.00 | 39.59 | C |
| ATOM | 438 | CG | TYR | A | 73 | 85.871 | −11.523 | 1.371 | 1.00 | 39.87 | C |
| ATOM | 439 | CD1 | TYR | A | 73 | 86.428 | −12.813 | 1.341 | 1.00 | 40.03 | C |
| ATOM | 440 | CD2 | TYR | A | 73 | 84.869 | −11.260 | 2.310 | 1.00 | 39.69 | C |
| ATOM | 441 | CE1 | TYR | A | 73 | 85.988 | −13.818 | 2.228 | 1.00 | 39.43 | C |
| ATOM | 442 | CE2 | TYR | A | 73 | 84.422 | −12.252 | 3.196 | 1.00 | 39.45 | C |
| ATOM | 443 | CZ | TYR | A | 73 | 84.983 | −13.528 | 3.148 | 1.00 | 39.35 | C |
| ATOM | 444 | OH | TYR | A | 73 | 84.513 | −14.506 | 4.000 | 1.00 | 38.23 | O |
| ATOM | 445 | N | LEU | A | 74 | 85.273 | −8.137 | −1.780 | 1.00 | 39.02 | N |
| ATOM | 446 | CA | LEU | A | 74 | 85.656 | −6.899 | −2.460 | 1.00 | 38.07 | C |
| ATOM | 447 | C | LEU | A | 74 | 86.859 | −6.288 | −1.750 | 1.00 | 38.59 | C |
| ATOM | 448 | O | LEU | A | 74 | 86.963 | −6.346 | −0.524 | 1.00 | 38.50 | O |
| ATOM | 449 | CB | LEU | A | 74 | 84.515 | −5.887 | −2.435 | 1.00 | 36.96 | C |
| ATOM | 450 | CG | LEU | A | 74 | 84.825 | −4.568 | −3.149 | 1.00 | 37.24 | C |
| ATOM | 451 | CD1 | LEU | A | 74 | 84.673 | −4.774 | −4.656 | 1.00 | 35.39 | C |
| ATOM | 452 | CD2 | LEU | A | 74 | 83.870 | −3.465 | −2.661 | 1.00 | 35.55 | C |
| ATOM | 453 | N | ALA | A | 75 | 87.768 | −5.702 | −2.521 | 1.00 | 39.32 | N |
| ATOM | 454 | CA | ALA | A | 75 | 88.951 | −5.085 | −1.942 | 1.00 | 40.14 | C |
| ATOM | 455 | C | ALA | A | 75 | 89.471 | −3.946 | −2.809 | 1.00 | 40.56 | C |
| ATOM | 456 | O | ALA | A | 75 | 89.246 | −3.917 | −4.012 | 1.00 | 39.49 | O |
| ATOM | 457 | CB | ALA | A | 75 | 90.038 | −6.134 | −1.746 | 1.00 | 40.67 | C |
| ATOM | 458 | N | MET | A | 76 | 90.147 | −2.996 | −2.178 | 1.00 | 42.11 | N |
| ATOM | 459 | CA | MET | A | 76 | 90.722 | −1.874 | −2.898 | 1.00 | 44.44 | C |
| ATOM | 460 | C | MET | A | 76 | 92.229 | −1.900 | −2.681 | 1.00 | 45.54 | C |
| ATOM | 461 | O | MET | A | 76 | 92.697 | −1.861 | −1.541 | 1.00 | 45.20 | O |
| ATOM | 462 | CB | MET | A | 76 | 90.168 | −0.547 | −2.398 | 1.00 | 44.84 | C |
| ATOM | 463 | CG | MET | A | 76 | 90.637 | 0.619 | −3.253 | 1.00 | 46.00 | C |
| ATOM | 464 | SD | MET | A | 76 | 90.147 | 2.212 | −2.611 | 1.00 | 48.70 | S |
| ATOM | 465 | CE | MET | A | 76 | 88.435 | 2.315 | −3.268 | 1.00 | 47.92 | C |
| ATOM | 466 | N | LYS | A | 77 | 92.975 | −1.969 | −3.783 | 1.00 | 46.80 | N |
| ATOM | 467 | CA | LYS | A | 77 | 94.435 | −2.024 | −3.749 | 1.00 | 48.49 | C |
| ATOM | 468 | C | LYS | A | 77 | 95.082 | −0.653 | −3.525 | 1.00 | 49.55 | C |
| ATOM | 469 | O | LYS | A | 77 | 94.408 | 0.381 | −3.539 | 1.00 | 49.41 | O |
| ATOM | 470 | CB | LYS | A | 77 | 94.964 | −2.643 | −5.047 | 1.00 | 48.04 | C |
| ATOM | 471 | N | GLU | A | 78 | 96.397 | −0.658 | −3.323 | 1.00 | 50.66 | N |
| ATOM | 472 | CA | GLU | A | 78 | 97.152 | 0.568 | −3.073 | 1.00 | 51.87 | C |
| ATOM | 473 | C | GLU | A | 78 | 97.065 | 1.601 | −4.200 | 1.00 | 52.55 | C |
| ATOM | 474 | O | GLU | A | 78 | 97.148 | 2.804 | −3.947 | 1.00 | 53.06 | O |
| ATOM | 475 | CB | GLU | A | 78 | 98.625 | 0.235 | −2.798 | 1.00 | 51.76 | C |
| ATOM | 476 | N | ASP | A | 79 | 96.902 | 1.140 | −5.437 | 1.00 | 53.11 | N |
| ATOM | 477 | CA | ASP | A | 79 | 96.815 | 2.061 | −6.569 | 1.00 | 54.03 | C |
| ATOM | 478 | C | ASP | A | 79 | 95.384 | 2.535 | −6.819 | 1.00 | 53.96 | C |
| ATOM | 479 | O | ASP | A | 79 | 95.123 | 3.263 | −7.780 | 1.00 | 54.29 | O |
| ATOM | 480 | CB | ASP | A | 79 | 97.378 | 1.410 | −7.843 | 1.00 | 54.74 | C |

TABLE 3-continued

FGFR2(D2–D3) Complexed with FGF2

| ATOM | 481 | CG | ASP | A | 79 | 96.600 | 0.177 | −8.265 | 1.00 | 56.27 | C |
|---|---|---|---|---|---|---|---|---|---|---|---|
| ATOM | 482 | OD1 | ASP | A | 79 | 96.970 | −0.438 | −9.292 | 1.00 | 56.58 | O |
| ATOM | 483 | OD2 | ASP | A | 79 | 95.622 | −0.181 | −7.572 | 1.00 | 56.94 | O |
| ATOM | 484 | N | GLY | A | 80 | 94.462 | 2.116 | −5.954 | 1.00 | 53.27 | N |
| ATOM | 485 | CA | GLY | A | 80 | 93.072 | 2.516 | −6.089 | 1.00 | 52.72 | C |
| ATOM | 486 | C | GLY | A | 80 | 92.219 | 1.628 | −6.977 | 1.00 | 51.96 | C |
| ATOM | 487 | O | GLY | A | 80 | 91.103 | 1.994 | −7.330 | 1.00 | 52.61 | O |
| ATOM | 488 | N | ARG | A | 81 | 92.733 | 0.460 | −7.337 | 1.00 | 50.93 | N |
| ATOM | 489 | CA | ARG | A | 81 | 91.991 | −0.459 | −8.192 | 1.00 | 50.23 | C |
| ATOM | 490 | C | ARG | A | 81 | 91.097 | −1.379 | 7.362 | 1.00 | 49.57 | C |
| ATOM | 491 | O | ARG | A | 81 | 91.411 | −1.700 | 6.216 | 1.00 | 48.23 | O |
| ATOM | 492 | CB | ARG | A | 81 | 92.967 | −1.303 | −9.023 | 1.00 | 50.47 | C |
| ATOM | 493 | N | LEU | A | 82 | 89.983 | −1.807 | 7.942 | 1.00 | 49.42 | N |
| ATOM | 494 | CA | LEU | A | 82 | 89.078 | −2.697 | 7.228 | 1.00 | 49.88 | C |
| ATOM | 495 | C | LEU | A | 82 | 89.174 | −4.124 | 7.746 | 1.00 | 50.11 | C |
| ATOM | 496 | O | LEU | A | 82 | 89.298 | −4.352 | 8.950 | 1.00 | 50.11 | O |
| ATOM | 497 | CB | LEU | A | 82 | 87.624 | −2.217 | 7.339 | 1.00 | 49.49 | C |
| ATOM | 498 | CG | LEU | A | 82 | 87.231 | −0.941 | 6.587 | 1.00 | 49.70 | C |
| ATOM | 499 | CD1 | LEU | A | 82 | 85.707 | −0.868 | 6.496 | 1.00 | 49.71 | C |
| ATOM | 500 | CD2 | LEU | A | 82 | 87.834 | −0.946 | 5.186 | 1.00 | 49.10 | C |
| ATOM | 501 | N | LEU | A | 83 | 89.111 | −5.078 | 6.822 | 1.00 | 50.38 | N |
| ATOM | 502 | CA | LEU | A | 83 | 89.177 | −6.497 | 7.160 | 1.00 | 50.58 | C |
| ATOM | 503 | C | LEU | A | 83 | 88.544 | −7.305 | 6.020 | 1.00 | 49.82 | C |
| ATOM | 504 | O | LEU | A | 83 | 88.265 | −6.758 | 4.956 | 1.00 | 49.94 | O |
| ATOM | 505 | CB | LEU | A | 83 | 90.642 | −6.906 | −7.385 | 1.00 | 51.17 | C |
| ATOM | 506 | CG | LEU | A | 83 | 91.614 | −6.724 | −6.211 | 1.00 | 52.27 | C |
| ATOM | 507 | CD1 | LEU | A | 83 | 91.549 | −7.951 | −5.307 | 1.00 | 52.55 | C |
| ATOM | 508 | CD2 | LEU | A | 83 | 93.034 | −6.537 | −6.726 | 1.00 | 52.55 | C |
| ATOM | 509 | N | ALA | A | 84 | 88.307 | −8.594 | −6.250 | 1.00 | 49.65 | N |
| ATOM | 510 | CA | ALA | A | 84 | 87.704 | −9.466 | −5.240 | 1.00 | 49.61 | C |
| ATOM | 511 | C | ALA | A | 84 | 88.662 | −10.602 | −4.857 | 1.00 | 49.88 | C |
| ATOM | 512 | O | ALA | A | 84 | 89.048 | −11.414 | −5.701 | 1.00 | 49.96 | O |
| ATOM | 513 | CB | ALA | A | 84 | 86.403 | −10.038 | −5.769 | 1.00 | 49.70 | C |
| ATOM | 514 | N | SER | A | 85 | 89.018 | −10.659 | −3.576 | 1.00 | 49.72 | N |
| ATOM | 515 | CA | SER | A | 85 | 89.959 | −11.646 | −3.048 | 1.00 | 49.33 | C |
| ATOM | 516 | C | SER | A | 85 | 89.334 | −12.919 | −2.471 | 1.00 | 49.28 | C |
| ATOM | 517 | O | SER | A | 85 | 88.257 | −12.884 | −1.865 | 1.00 | 48.71 | O |
| ATOM | 518 | CB | SER | A | 85 | 90.827 | −10.977 | −1.973 | 1.00 | 49.44 | C |
| ATOM | 519 | OG | SER | A | 85 | 91.783 | −11.875 | −1.445 | 1.00 | 50.34 | O |
| ATOM | 520 | N | LYS | A | 86 | 90.031 | −14.039 | −2.652 | 1.00 | 48.86 | N |
| ATOM | 521 | CA | LYS | A | 86 | 89.572 | −15.329 | −2.142 | 1.00 | 48.51 | C |
| ATOM | 522 | C | LYS | A | 86 | 89.579 | −15.294 | −0.619 | 1.00 | 47.67 | C |
| ATOM | 523 | O | LYS | A | 86 | 88.656 | −15.787 | 0.032 | 1.00 | 47.20 | O |
| ATOM | 524 | CB | LYS | A | 86 | 90.488 | −16.462 | −2.624 | 1.00 | 48.89 | C |
| ATOM | 525 | N | SER | A | 87 | 90.626 | −14.710 | −0.052 | 1.00 | 46.44 | N |
| ATOM | 526 | CA | SER | A | 87 | 90.717 | −14.619 | 1.392 | 1.00 | 46.63 | C |
| ATOM | 527 | C | SER | A | 87 | 90.715 | −13.157 | 1.845 | 1.00 | 46.26 | C |
| ATOM | 528 | O | SER | A | 87 | 91.195 | −12.266 | 1.142 | 1.00 | 46.06 | O |
| ATOM | 529 | CB | SER | A | 87 | 91.969 | −15.349 | 1.913 | 1.00 | 47.09 | C |
| ATOM | 530 | OG | SER | A | 87 | 93.166 | −14.666 | 1.568 | 1.00 | 48.04 | O |
| ATOM | 531 | N | VAL | A | 88 | 90.169 | −12.930 | 3.035 | 1.00 | 45.87 | N |
| ATOM | 532 | CA | VAL | A | 88 | 90.054 | −11.599 | 3.618 | 1.00 | 45.54 | C |
| ATOM | 533 | C | VAL | A | 88 | 91.377 | −10.961 | 4.026 | 1.00 | 45.45 | C |
| ATOM | 534 | O | VAL | A | 88 | 92.168 | −11.576 | 4.729 | 1.00 | 45.96 | O |
| ATOM | 535 | CB | VAL | A | 88 | 89.149 | −11.634 | 4.872 | 1.00 | 45.92 | C |
| ATOM | 536 | CG1 | VAL | A | 88 | 88.924 | −10.222 | 5.400 | 1.00 | 46.37 | C |
| ATOM | 537 | CG2 | VAL | A | 88 | 87.833 | −12.306 | 4.542 | 1.00 | 45.73 | C |
| ATOM | 538 | N | THR | A | 89 | 91.609 | −9.725 | 3.583 | 1.00 | 45.26 | N |
| ATOM | 539 | CA | THR | A | 89 | 92.818 | −8.985 | 3.949 | 1.00 | 45.23 | C |
| ATOM | 540 | C | THR | A | 89 | 92.389 | −7.606 | 4.453 | 1.00 | 44.98 | C |
| ATOM | 541 | O | THR | A | 89 | 91.206 | −7.283 | 4.445 | 1.00 | 44.71 | O |
| ATOM | 542 | CB | THR | A | 89 | 93.794 | −8.799 | 2.761 | 1.00 | 45.77 | C |
| ATOM | 543 | OG1 | THR | A | 89 | 93.386 | −7.683 | 1.960 | 1.00 | 46.09 | O |
| ATOM | 544 | CG2 | THR | A | 89 | 93.825 | −10.059 | 1.896 | 1.00 | 46.51 | C |
| ATOM | 545 | N | ASP | A | 90 | 93.344 | −6.794 | 4.890 | 1.00 | 45.15 | N |
| ATOM | 546 | CA | ASP | A | 90 | 93.025 | −5.472 | 5.411 | 1.00 | 45.66 | C |
| ATOM | 547 | C | ASP | A | 90 | 92.492 | −4.491 | 4.366 | 1.00 | 44.55 | C |
| ATOM | 548 | O | ASP | A | 90 | 92.098 | −3.371 | 4.701 | 1.00 | 44.62 | O |
| ATOM | 549 | CB | ASP | A | 90 | 94.246 | −4.860 | 6.093 | 1.00 | 48.43 | C |
| ATOM | 550 | CG | ASP | A | 90 | 94.072 | −4.755 | 7.586 | 1.00 | 51.37 | C |
| ATOM | 551 | OD1 | ASP | A | 90 | 92.930 | −4.490 | 8.016 | 1.00 | 53.54 | O |
| ATOM | 552 | OD2 | ASP | A | 90 | 95.067 | −4.923 | 8.331 | 1.00 | 53.90 | O |
| ATOM | 553 | N | GLU | A | 91 | 92.494 | −4.906 | 3.106 | 1.00 | 42.88 | N |
| ATOM | 554 | CA | GLU | A | 91 | 92.010 | −4.063 | 2.020 | 1.00 | 41.63 | C |
| ATOM | 555 | C | GLU | A | 91 | 90.560 | −4.426 | 1.685 | 1.00 | 40.40 | C |
| ATOM | 556 | O | GLU | A | 91 | 90.006 | −3.965 | 0.686 | 1.00 | 39.79 | O |
| ATOM | 557 | CB | GLU | A | 91 | 92.896 | −4.256 | 0.778 | 1.00 | 40.78 | C |

TABLE 3-continued

FGFR2(D2–D3) Complexed with FGF2

| ATOM | 558 | N | CYS | A | 92 | 89.948 | −5.248 | 2.531 | 1.00 | 39.24 | N |
|---|---|---|---|---|---|---|---|---|---|---|---|
| ATOM | 559 | CA | CYS | A | 92 | 88.581 | −5.693 | 2.298 | 1.00 | 38.89 | C |
| ATOM | 560 | C | CYS | A | 92 | 87.542 | −5.075 | 3.240 | 1.00 | 37.51 | C |
| ATOM | 561 | O | CYS | A | 92 | 86.391 | −5.508 | 3.256 | 1.00 | 37.21 | O |
| ATOM | 562 | CB | CYS | A | 92 | 88.532 | −7.224 | 2.377 | 1.00 | 38.66 | C |
| ATOM | 563 | SG | CYS | A | 92 | 89.608 | −8.074 | 1.156 | 1.00 | 40.15 | S |
| ATOM | 564 | N | PHE | A | 93 | 87.948 | −4.065 | 4.007 | 1.00 | 36.12 | N |
| ATOM | 565 | CA | PHE | A | 93 | 87.052 | −3.400 | 4.953 | 1.00 | 36.26 | C |
| ATOM | 566 | C | PHE | A | 93 | 86.765 | −1.931 | 4.603 | 1.00 | 35.98 | C |
| ATOM | 567 | O | PHE | A | 93 | 87.683 | −1.162 | 4.292 | 1.00 | 35.24 | O |
| ATOM | 568 | CB | PHE | A | 93 | 87.622 | −3.514 | 6.366 | 1.00 | 36.32 | C |
| ATOM | 569 | CG | PHE | A | 93 | 87.740 | −4.929 | 6.837 | 1.00 | 37.73 | C |
| ATOM | 570 | CD1 | PHE | A | 93 | 86.599 | −5.710 | 7.001 | 1.00 | 36.77 | C |
| ATOM | 571 | CD2 | PHE | A | 93 | 88.994 | −5.510 | 7.040 | 1.00 | 37.62 | C |
| ATOM | 572 | CE1 | PHE | A | 93 | 86.694 | −7.053 | 7.354 | 1.00 | 38.45 | C |
| ATOM | 573 | CE2 | PHE | A | 93 | 89.104 | −6.855 | 7.394 | 1.00 | 38.74 | C |
| ATOM | 574 | CZ | PHE | A | 93 | 87.954 | −7.630 | 7.551 | 1.00 | 38.47 | C |
| ATOM | 575 | N | PHE | A | 94 | 85.486 | −1.552 | 4.682 | 1.00 | 34.88 | N |
| ATOM | 576 | CA | PHE | A | 94 | 85.050 | −0.204 | 4.329 | 1.00 | 33.78 | C |
| ATOM | 577 | C | PHE | A | 94 | 84.087 | 0.448 | 5.320 | 1.00 | 33.14 | C |
| ATOM | 578 | O | PHE | A | 94 | 83.169 | −0.196 | 5.834 | 1.00 | 33.33 | O |
| ATOM | 579 | CB | PHE | A | 94 | 84.357 | −0.238 | 2.969 | 1.00 | 34.11 | C |
| ATOM | 580 | CG | PHE | A | 94 | 85.166 | −0.885 | 1.889 | 1.00 | 34.92 | C |
| ATOM | 581 | CD1 | PHE | A | 94 | 86.025 | −0.130 | 1.101 | 1.00 | 33.99 | C |
| ATOM | 582 | CD2 | PHE | A | 94 | 85.074 | −2.261 | 1.664 | 1.00 | 35.17 | C |
| ATOM | 583 | CE1 | PHE | A | 94 | 86.785 | −0.733 | 0.097 | 1.00 | 34.50 | C |
| ATOM | 584 | CE2 | PHE | A | 94 | 85.833 | −2.874 | 0.662 | 1.00 | 35.02 | C |
| ATOM | 585 | CZ | PHE | A | 94 | 86.692 | −2.106 | −0.123 | 1.00 | 33.91 | C |
| ATOM | 586 | N | PHE | A | 95 | 84.294 | 1.732 | 5.575 | 1.00 | 31.91 | N |
| ATOM | 587 | CA | PHE | A | 95 | 83.402 | 2.477 | 6.457 | 1.00 | 31.86 | C |
| ATOM | 588 | C | PHE | A | 95 | 82.091 | 2.646 | 5.695 | 1.00 | 29.92 | C |
| ATOM | 589 | O | PHE | A | 95 | 82.086 | 3.158 | 4.579 | 1.00 | 28.74 | O |
| ATOM | 590 | CB | PHE | A | 95 | 83.964 | 3.875 | 6.771 | 1.00 | 32.18 | C |
| ATOM | 591 | CG | PHE | A | 95 | 85.103 | 3.880 | 7.751 | 1.00 | 34.26 | C |
| ATOM | 592 | CD1 | PHE | A | 95 | 86.421 | 3.966 | 7.315 | 1.00 | 34.86 | C |
| ATOM | 593 | CD2 | PHE | A | 95 | 84.856 | 3.838 | 9.117 | 1.00 | 34.93 | C |
| ATOM | 594 | CE1 | PHE | A | 95 | 87.475 | 4.019 | 8.232 | 1.00 | 35.24 | C |
| ATOM | 595 | CE2 | PHE | A | 95 | 85.907 | 3.887 | 10.037 | 1.00 | 36.08 | C |
| ATOM | 596 | CZ | PHE | A | 95 | 87.216 | 3.980 | 9.592 | 1.00 | 35.03 | C |
| ATOM | 597 | N | GLU | A | 96 | 80.992 | 2.193 | 6.282 | 1.00 | 29.95 | N |
| ATOM | 598 | CA | GLU | A | 96 | 79.684 | 2.328 | 5.647 | 1.00 | 30.89 | C |
| ATOM | 599 | C | GLU | A | 96 | 78.984 | 3.529 | 6.280 | 1.00 | 31.23 | C |
| ATOM | 600 | O | GLU | A | 96 | 78.910 | 3.637 | 7.500 | 1.00 | 30.95 | O |
| ATOM | 601 | CB | GLU | A | 96 | 78.843 | 1.059 | 5.855 | 1.00 | 29.09 | C |
| ATOM | 602 | CG | GLU | A | 96 | 77.449 | 1.150 | 5.233 | 1.00 | 29.15 | C |
| ATOM | 603 | CD | GLU | A | 96 | 76.613 | −0.107 | 5.441 | 1.00 | 29.45 | C |
| ATOM | 604 | OE1 | GLU | A | 96 | 76.354 | −0.451 | 6.609 | 1.00 | 30.47 | O |
| ATOM | 605 | OE2 | GLU | A | 96 | 76.218 | −0.749 | 4.438 | 1.00 | 28.03 | O |
| ATOM | 606 | N | ARG | A | 97 | 78.476 | 4.423 | 5.445 | 1.00 | 32.89 | N |
| ATOM | 607 | CA | ARG | A | 97 | 77.795 | 5.624 | 5.931 | 1.00 | 35.01 | C |
| ATOM | 608 | C | ARG | A | 97 | 76.514 | 5.940 | 5.156 | 1.00 | 35.02 | C |
| ATOM | 609 | O | ARG | A | 97 | 76.487 | 5.891 | 3.928 | 1.00 | 34.22 | O |
| ATOM | 610 | CB | ARG | A | 97 | 78.734 | 6.833 | 5.825 | 1.00 | 37.51 | C |
| ATOM | 611 | CG | ARG | A | 97 | 78.022 | 8.186 | 5.923 | 1.00 | 41.64 | C |
| ATOM | 612 | CD | ARG | A | 97 | 77.836 | 8.617 | 7.366 | 1.00 | 44.41 | C |
| ATOM | 613 | NE | ARG | A | 97 | 79.087 | 9.126 | 7.922 | 1.00 | 46.59 | N |
| ATOM | 614 | CZ | ARG | A | 97 | 79.681 | 10.245 | 7.513 | 1.00 | 48.01 | C |
| ATOM | 615 | NH1 | ARG | A | 97 | 79.131 | 10.976 | 6.544 | 1.00 | 48.75 | N |
| ATOM | 616 | NH2 | ARG | A | 97 | 80.825 | 10.633 | 8.068 | 1.00 | 47.89 | N |
| ATOM | 617 | N | LEU | A | 98 | 75.450 | 6.246 | 5.887 | 1.00 | 35.75 | N |
| ATOM | 618 | CA | LEU | A | 98 | 74.189 | 6.641 | 5.267 | 1.00 | 36.00 | C |
| ATOM | 619 | C | LEU | A | 98 | 74.273 | 8.168 | 5.164 | 1.00 | 35.58 | C |
| ATOM | 620 | O | LEU | A | 98 | 74.272 | 8.855 | 6.178 | 1.00 | 35.92 | O |
| ATOM | 621 | CB | LEU | A | 98 | 72.999 | 6.218 | 6.145 | 1.00 | 35.97 | C |
| ATOM | 622 | CG | LEU | A | 98 | 71.600 | 6.714 | 5.726 | 1.00 | 36.46 | C |
| ATOM | 623 | CD1 | LEU | A | 98 | 71.358 | 6.425 | 4.249 | 1.00 | 35.99 | C |
| ATOM | 624 | CD2 | LEU | A | 98 | 70.523 | 6.034 | 6.583 | 1.00 | 36.05 | C |
| ATOM | 625 | N | GLU | A | 99 | 74.384 | 8.691 | 3.948 | 1.00 | 36.12 | N |
| ATOM | 626 | CA | GLU | A | 99 | 74.493 | 10.132 | 3.755 | 1.00 | 36.63 | C |
| ATOM | 627 | C | GLU | A | 99 | 73.152 | 10.840 | 3.913 | 1.00 | 37.62 | C |
| ATOM | 628 | O | GLU | A | 99 | 72.088 | 10.206 | 3.864 | 1.00 | 35.83 | O |
| ATOM | 629 | CB | GLU | A | 99 | 75.081 | 10.437 | 2.379 | 1.00 | 37.25 | C |
| ATOM | 630 | CG | GLU | A | 99 | 76.460 | 9.820 | 2.153 | 1.00 | 38.74 | C |
| ATOM | 631 | CD | GLU | A | 99 | 77.476 | 10.222 | 3.217 | 1.00 | 39.43 | C |
| ATOM | 632 | OE1 | GLU | A | 99 | 78.589 | 9.666 | 3.192 | 1.00 | 40.37 | O |
| ATOM | 633 | OE2 | GLU | A | 99 | 77.173 | 11.088 | 4.070 | 1.00 | 39.18 | O |
| ATOM | 634 | N | SER | A | 100 | 73.212 | 12.159 | 4.099 | 1.00 | 38.04 | N |

TABLE 3-continued

FGFR2(D2–D3) Complexed with FGF2

| ATOM | 635 | CA | SER | A | 100 | 72.011 | 12.970 | 4.281 | 1.00 | 38.26 | C |
|---|---|---|---|---|---|---|---|---|---|---|---|
| ATOM | 636 | C | SER | A | 100 | 71.055 | 12.856 | 3.093 | 1.00 | 37.38 | C |
| ATOM | 637 | O | SER | A | 100 | 69.850 | 13.072 | 3.239 | 1.00 | 37.46 | O |
| ATOM | 638 | CB | SER | A | 100 | 72.394 | 14.438 | 4.527 | 1.00 | 38.36 | C |
| ATOM | 639 | OG | SER | A | 100 | 73.181 | 14.952 | 3.463 | 1.00 | 40.12 | O |
| ATOM | 640 | N | ASN | A | 101 | 71.590 | 12.506 | 1.925 | 1.00 | 36.22 | N |
| ATOM | 641 | CA | ASN | A | 101 | 70.767 | 12.341 | 0.728 | 1.00 | 34.84 | C |
| ATOM | 642 | C | ASN | A | 101 | 70.080 | 10.973 | 0.689 | 1.00 | 33.40 | C |
| ATOM | 643 | O | ASN | A | 101 | 69.352 | 10.667 | −0.254 | 1.00 | 33.62 | O |
| ATOM | 644 | CB | ASN | A | 101 | 71.620 | 12.516 | −0.526 | 1.00 | 35.95 | C |
| ATOM | 645 | CG | ASN | A | 101 | 72.956 | 11.783 | −0.434 | 1.00 | 38.04 | C |
| ATOM | 646 | OD1 | ASN | A | 101 | 73.042 | 10.666 | 0.091 | 1.00 | 36.23 | O |
| ATOM | 647 | ND2 | ASN | A | 101 | 74.008 | 12.412 | −0.959 | 1.00 | 38.32 | N |
| ATOM | 648 | N | ASN | A | 102 | 70.320 | 10.162 | 1.718 | 1.00 | 32.04 | N |
| ATOM | 649 | CA | ASN | A | 102 | 69.752 | 8.822 | 1.844 | 1.00 | 31.07 | C |
| ATOM | 650 | C | ASN | A | 102 | 70.351 | 7.711 | 0.971 | 1.00 | 30.18 | C |
| ATOM | 651 | O | ASN | A | 102 | 69.705 | 6.678 | 0.750 | 1.00 | 27.66 | O |
| ATOM | 652 | CB | ASN | A | 102 | 68.237 | 8.844 | 1.634 | 1.00 | 32.35 | C |
| ATOM | 653 | CG | ASN | A | 102 | 67.487 | 9.206 | 2.896 | 1.00 | 34.59 | C |
| ATOM | 654 | OD1 | ASN | A | 102 | 68.012 | 9.072 | 4.010 | 1.00 | 34.67 | O |
| ATOM | 655 | ND2 | ASN | A | 102 | 66.246 | 9.655 | 2.734 | 1.00 | 35.07 | N |
| ATOM | 656 | N | TYR | A | 103 | 71.564 | 7.934 | 0.466 | 1.00 | 28.14 | N |
| ATOM | 657 | CA | TYR | A | 103 | 72.280 | 6.916 | −0.309 | 1.00 | 27.47 | C |
| ATOM | 658 | C | TYR | A | 103 | 73.419 | 6.488 | 0.608 | 1.00 | 26.83 | C |
| ATOM | 659 | O | TYR | A | 103 | 73.727 | 7.195 | 1.568 | 1.00 | 25.26 | O |
| ATOM | 660 | CB | TYR | A | 103 | 72.874 | 7.485 | −1.600 | 1.00 | 27.20 | C |
| ATOM | 661 | CG | TYR | A | 103 | 71.882 | 7.684 | −2.719 | 1.00 | 28.12 | C |
| ATOM | 662 | CD1 | TYR | A | 103 | 71.564 | 6.640 | −3.586 | 1.00 | 27.59 | C |
| ATOM | 663 | CD2 | TYR | A | 103 | 71.281 | 8.930 | −2.932 | 1.00 | 27.54 | C |
| ATOM | 664 | CE1 | TYR | A | 103 | 70.685 | 6.830 | −4.638 | 1.00 | 28.35 | C |
| ATOM | 665 | CE2 | TYR | A | 103 | 70.395 | 9.130 | −3.981 | 1.00 | 28.24 | C |
| ATOM | 666 | CZ | TYR | A | 103 | 70.101 | 8.080 | −4.828 | 1.00 | 28.25 | C |
| ATOM | 667 | OH | TYR | A | 103 | 69.215 | 8.265 | −5.856 | 1.00 | 28.55 | O |
| ATOM | 668 | N | ASN | A | 104 | 74.032 | 5.343 | 0.313 | 1.00 | 25.83 | N |
| ATOM | 669 | CA | ASN | A | 104 | 75.146 | 4.842 | 1.112 | 1.00 | 25.48 | C |
| ATOM | 670 | C | ASN | A | 104 | 76.486 | 5.082 | 0.417 | 1.00 | 24.49 | C |
| ATOM | 671 | O | ASN | A | 104 | 76.544 | 5.176 | −0.803 | 1.00 | 24.92 | O |
| ATOM | 672 | CB | ASN | A | 104 | 75.006 | 3.333 | 1.337 | 1.00 | 25.94 | C |
| ATOM | 673 | CG | ASN | A | 104 | 73.980 | 2.983 | 2.400 | 1.00 | 27.69 | C |
| ATOM | 674 | OD1 | ASN | A | 104 | 73.342 | 3.860 | 2.998 | 1.00 | 25.70 | O |
| ATOM | 675 | ND2 | ASN | A | 104 | 73.819 | 1.680 | 2.646 | 1.00 | 26.43 | N |
| ATOM | 676 | N | THR | A | 105 | 77.555 | 5.186 | 1.198 | 1.00 | 24.18 | N |
| ATOM | 677 | CA | THR | A | 105 | 78.901 | 5.317 | 0.636 | 1.00 | 24.45 | C |
| ATOM | 678 | C | THR | A | 105 | 79.805 | 4.316 | 1.370 | 1.00 | 24.99 | C |
| ATOM | 679 | O | THR | A | 105 | 79.577 | 3.995 | 2.542 | 1.00 | 23.75 | O |
| ATOM | 680 | GB | THR | A | 105 | 79.534 | 6.703 | 0.838 | 1.00 | 23.48 | C |
| ATOM | 681 | OG1 | THR | A | 105 | 79.479 | 7.037 | 2.230 | 1.00 | 24.08 | O |
| ATOM | 682 | CG2 | THR | A | 105 | 78.852 | 7.752 | −0.026 | 1.00 | 23.94 | C |
| ATOM | 683 | N | TYR | A | 106 | 80.828 | 3.839 | 0.672 | 1.00 | 25.52 | N |
| ATOM | 684 | CA | TYR | A | 106 | 81.768 | 2.873 | 1.222 | 1.00 | 27.52 | C |
| ATOM | 685 | C | TYR | A | 106 | 83.191 | 3.402 | 1.052 | 1.00 | 29.31 | C |
| ATOM | 686 | O | TYR | A | 106 | 83.715 | 3.461 | −0.064 | 1.00 | 29.05 | O |
| ATOM | 687 | CB | TYR | A | 106 | 81.577 | 1.531 | 0.504 | 1.00 | 26.36 | C |
| ATOM | 688 | CG | TYR | A | 106 | 80.223 | 0.933 | 0.807 | 1.00 | 24.59 | C |
| ATOM | 689 | CD1 | TYR | A | 106 | 79.982 | 0.278 | 2.024 | 1.00 | 23.67 | C |
| ATOM | 690 | CD2 | TYR | A | 106 | 79.149 | 1.120 | −0.065 | 1.00 | 23.83 | C |
| ATOM | 691 | CE1 | TYR | A | 106 | 78.690 | −0.169 | 2.367 | 1.00 | 24.28 | C |
| ATOM | 692 | CE2 | TYR | A | 106 | 77.852 | 0.682 | 0.268 | 1.00 | 24.28 | C |
| ATOM | 693 | CZ | TYR | A | 106 | 77.628 | 0.044 | 1.479 | 1.00 | 23.75 | C |
| ATOM | 694 | OH | TYR | A | 106 | 76.338 | −0.348 | 1.807 | 1.00 | 23.41 | O |
| ATOM | 695 | N | ARG | A | 107 | 83.793 | 3.804 | 2.167 | 1.00 | 31.22 | N |
| ATOM | 696 | CA | ARG | A | 107 | 85.142 | 4.369 | 2.182 | 1.00 | 33.44 | C |
| ATOM | 697 | C | ARG | A | 107 | 86.175 | 3.400 | 2.788 | 1.00 | 33.71 | C |
| ATOM | 698 | O | ARG | A | 107 | 85.979 | 2.870 | 3.874 | 1.00 | 32.90 | O |
| ATOM | 699 | CB | ARG | A | 107 | 85.110 | 5.693 | 2.961 | 1.00 | 33.34 | C |
| ATOM | 700 | CG | ARG | A | 107 | 86.390 | 6.517 | 2.919 | 1.00 | 33.84 | C |
| ATOM | 701 | CD | ARG | A | 107 | 86.147 | 7.883 | 3.550 | 1.00 | 33.44 | C |
| ATOM | 702 | NE | ARG | A | 107 | 85.639 | 7.773 | 4.919 | 1.00 | 33.98 | N |
| ATOM | 703 | CZ | ARG | A | 107 | 86.396 | 7.548 | 5.991 | 1.00 | 35.38 | C |
| ATOM | 704 | NH1 | ARG | A | 107 | 87.712 | 7.415 | 5.861 | 1.00 | 37.25 | N |
| ATOM | 705 | NH2 | ARG | A | 107 | 85.840 | 7.418 | 7.191 | 1.00 | 34.53 | N |
| ATOM | 706 | N | SER | A | 108 | 87.266 | 3.177 | 2.060 | 1.00 | 36.11 | N |
| ATOM | 707 | CA | SER | A | 108 | 88.345 | 2.270 | 2.475 | 1.00 | 37.06 | C |
| ATOM | 708 | C | SER | A | 108 | 88.890 | 2.572 | 3.866 | 1.00 | 37.88 | C |
| ATOM | 709 | O | SER | A | 108 | 89.251 | 3.713 | 4.162 | 1.00 | 37.86 | O |
| ATOM | 710 | CB | SER | A | 108 | 89.494 | 2.342 | 1.464 | 1.00 | 37.14 | C |
| ATOM | 711 | OG | SER | A | 108 | 90.533 | 1.433 | 1.779 | 1.00 | 38.83 | O |

TABLE 3-continued

FGFR2(D2–D3) Complexed with FGF2

| ATOM | 712 | N | ARG | A | 109 | 88.957 | 1.555 | 4.724 | 1.00 | 38.90 | N |
|---|---|---|---|---|---|---|---|---|---|---|---|
| ATOM | 713 | CA | ARG | A | 109 | 89.485 | 1.779 | 6.063 | 1.00 | 40.45 | C |
| ATOM | 714 | C | ARG | A | 109 | 91.011 | 1.889 | 6.005 | 1.00 | 41.31 | C |
| ATOM | 715 | O | ARG | A | 109 | 91.630 | 2.487 | 6.886 | 1.00 | 40.95 | O |
| ATOM | 716 | CB | ARG | A | 109 | 89.078 | 0.657 | 7.020 | 1.00 | 40.32 | C |
| ATOM | 717 | CG | ARG | A | 109 | 89.395 | 0.986 | 8.476 | 1.00 | 41.68 | C |
| ATOM | 718 | CD | ARG | A | 109 | 88.858 | −0.060 | 9.446 | 1.00 | 42.89 | C |
| ATOM | 719 | NE | ARG | A | 109 | 89.418 | −1.384 | 9.187 | 1.00 | 45.20 | N |
| ATOM | 720 | CZ | ARG | A | 109 | 89.221 | −2.452 | 9.959 | 1.00 | 45.77 | C |
| ATOM | 721 | NH1 | ARG | A | 109 | 88.471 | −2.362 | 11.049 | 1.00 | 46.70 | N |
| ATOM | 722 | NH2 | ARG | A | 109 | 89.783 | −3.615 | 9.648 | 1.00 | 45.83 | N |
| ATOM | 723 | N | LYS | A | 110 | 91.604 | 1.319 | 4.959 | 1.00 | 42.40 | N |
| ATOM | 724 | CA | LYS | A | 110 | 93.061 | 1.363 | 4.779 | 1.00 | 44.16 | C |
| ATOM | 725 | C | LYS | A | 110 | 93.474 | 2.688 | 4.128 | 1.00 | 44.71 | C |
| ATOM | 726 | O | LYS | A | 110 | 94.231 | 3.472 | 4.711 | 1.00 | 44.66 | O |
| ATOM | 727 | CB | LYS | A | 110 | 93.522 | 0.188 | 3.908 | 1.00 | 43.41 | C |
| ATOM | 728 | N | TYR | A | 111 | 92.972 | 2.928 | 2.918 | 1.00 | 44.79 | N |
| ATOM | 729 | CA | TYR | A | 111 | 93.257 | 4.159 | 2.184 | 1.00 | 45.33 | C |
| ATOM | 730 | C | TYR | A | 111 | 92.041 | 5.041 | 2.440 | 1.00 | 45.58 | C |
| ATOM | 731 | O | TYR | A | 111 | 91.143 | 5.160 | 1.606 | 1.00 | 45.68 | O |
| ATOM | 732 | CB | TYR | A | 111 | 93.417 | 3.834 | 0.704 | 1.00 | 46.39 | C |
| ATOM | 733 | CG | TYR | A | 111 | 94.310 | 2.631 | 0.495 | 1.00 | 48.08 | C |
| ATOM | 734 | CD1 | TYR | A | 111 | 95.651 | 2.659 | 0.881 | 1.00 | 48.44 | C |
| ATOM | 735 | CD2 | TYR | A | 111 | 93.797 | 1.440 | −0.016 | 1.00 | 48.53 | C |
| ATOM | 736 | CE1 | TYR | A | 111 | 96.457 | 1.528 | 0.770 | 1.00 | 49.53 | C |
| ATOM | 737 | CE2 | TYR | A | 111 | 94.591 | 0.303 | −0.131 | 1.00 | 49.37 | C |
| ATOM | 738 | CZ | TYR | A | 111 | 95.920 | 0.351 | 0.266 | 1.00 | 50.10 | C |
| ATOM | 739 | OH | TYR | A | 111 | 96.695 | −0.787 | 0.186 | 1.00 | 50.23 | O |
| ATOM | 740 | N | THR | A | 112 | 92.037 | 5.652 | 3.620 | 1.00 | 45.88 | N |
| ATOM | 741 | CA | THR | A | 112 | 90.937 | 6.477 | 4.112 | 1.00 | 45.92 | C |
| ATOM | 742 | C | THR | A | 112 | 90.372 | 7.631 | 3.291 | 1.00 | 46.09 | C |
| ATOM | 743 | O | THR | A | 112 | 89.499 | 8.354 | 3.783 | 1.00 | 46.15 | O |
| ATOM | 744 | CB | THR | A | 112 | 91.274 | 7.047 | 5.485 | 1.00 | 45.93 | C |
| ATOM | 745 | OG1 | THR | A | 112 | 92.262 | 8.072 | 5.337 | 1.00 | 46.22 | O |
| ATOM | 746 | CG2 | THR | A | 112 | 91.805 | 5.952 | 6.395 | 1.00 | 46.03 | C |
| ATOM | 747 | N | SER | A | 113 | 90.826 | 7.819 | 2.059 | 1.00 | 45.29 | N |
| ATOM | 748 | CA | SER | A | 113 | 90.295 | 8.924 | 1.270 | 1.00 | 44.93 | C |
| ATOM | 749 | C | SER | A | 113 | 89.594 | 8.456 | 0.006 | 1.00 | 43.95 | C |
| ATOM | 750 | O | SER | A | 113 | 88.935 | 9.245 | −0.670 | 1.00 | 43.68 | O |
| ATOM | 751 | CB | SER | A | 113 | 91.417 | 9.870 | 0.869 | 1.00 | 46.51 | C |
| ATOM | 752 | OG | SER | A | 113 | 92.182 | 9.282 | −0.168 | 1.00 | 48.39 | O |
| ATOM | 753 | N | TRP | A | 114 | 89.746 | 7.177 | −0.319 | 1.00 | 42.46 | N |
| ATOM | 754 | CA | TRP | A | 114 | 89.140 | 6.628 | −1.521 | 1.00 | 41.49 | C |
| ATOM | 755 | C | TRP | A | 114 | 87.816 | 5.892 | −1.270 | 1.00 | 40.48 | C |
| ATOM | 756 | O | TRP | A | 114 | 87.626 | 5.255 | −0.233 | 1.00 | 39.86 | O |
| ATOM | 757 | CB | TRP | A | 114 | 90.136 | 5.697 | −2.227 | 1.00 | 41.54 | C |
| ATOM | 758 | N | TYR | A | 115 | 86.916 | 5.986 | −2.246 | 1.00 | 39.44 | N |
| ATOM | 759 | CA | TYR | A | 115 | 85.598 | 5.364 | −2.180 | 1.00 | 38.58 | C |
| ATOM | 760 | C | TYR | A | 115 | 85.381 | 4.306 | −3.250 | 1.00 | 37.61 | C |
| ATOM | 761 | O | TYR | A | 115 | 85.971 | 4.359 | −4.324 | 1.00 | 38.60 | O |
| ATOM | 762 | CB | TYR | A | 115 | 84.489 | 6.413 | −2.377 | 1.00 | 39.18 | C |
| ATOM | 763 | CG | TYR | A | 115 | 84.357 | 7.433 | −1.277 | 1.00 | 38.67 | C |
| ATOM | 764 | CD1 | TYR | A | 115 | 85.127 | 8.597 | −1.277 | 1.00 | 39.24 | C |
| ATOM | 765 | CD2 | TYR | A | 115 | 83.477 | 7.223 | −0.221 | 1.00 | 38.75 | C |
| ATOM | 766 | CE1 | TYR | A | 115 | 85.022 | 9.532 | −0.243 | 1.00 | 39.67 | C |
| ATOM | 767 | CE2 | TYR | A | 115 | 83.362 | 8.143 | 0.818 | 1.00 | 39.61 | C |
| ATOM | 768 | CZ | TYR | A | 115 | 84.137 | 9.300 | 0.804 | 1.00 | 40.08 | C |
| ATOM | 769 | OH | TYR | A | 115 | 84.014 | 10.209 | 1.836 | 1.00 | 39.83 | O |
| ATOM | 770 | N | VAL | A | 116 | 84.514 | 3.349 | −2.945 | 1.00 | 36.63 | N |
| ATOM | 771 | CA | VAL | A | 116 | 84.136 | 2.320 | −3.899 | 1.00 | 35.26 | C |
| ATOM | 772 | C | VAL | A | 116 | 83.257 | 3.123 | −4.847 | 1.00 | 36.10 | C |
| ATOM | 773 | O | VAL | A | 116 | 82.389 | 3.872 | −4.394 | 1.00 | 36.77 | O |
| ATOM | 774 | CB | VAL | A | 116 | 83.267 | 1.221 | −3.231 | 1.00 | 33.90 | C |
| ATOM | 775 | CG1 | VAL | A | 116 | 82.773 | 0.220 | −4.281 | 1.00 | 31.71 | C |
| ATOM | 776 | CG2 | VAL | A | 116 | 84.068 | 0.515 | −2.151 | 1.00 | 33.37 | C |
| ATOM | 777 | N | ALA | A | 117 | 83.463 | 2.980 | −6.147 | 1.00 | 36.82 | N |
| ATOM | 778 | CA | ALA | A | 117 | 82.676 | 3.747 | −7.096 | 1.00 | 37.68 | C |
| ATOM | 779 | C | ALA | A | 117 | 82.654 | 3.144 | −8.486 | 1.00 | 38.75 | C |
| ATOM | 780 | O | ALA | A | 117 | 83.542 | 2.378 | −8.866 | 1.00 | 38.92 | O |
| ATOM | 781 | CB | ALA | A | 117 | 83.212 | 5.180 | −7.161 | 1.00 | 37.78 | C |
| ATOM | 782 | N | LEU | A | 118 | 81.621 | 3.496 | −9.242 | 1.00 | 39.82 | N |
| ATOM | 783 | CA | LEU | A | 118 | 81.461 | 3.014 | −10.606 | 1.00 | 40.49 | C |
| ATOM | 784 | C | LEU | A | 118 | 81.371 | 4.200 | −11.551 | 1.00 | 41.61 | C |
| ATOM | 785 | O | LEU | A | 118 | 80.875 | 5.258 | −11.166 | 1.00 | 42.32 | O |
| ATOM | 786 | CB | LEU | A | 118 | 80.200 | 2.167 | −10.723 | 1.00 | 40.77 | C |
| ATOM | 787 | CG | LEU | A | 118 | 80.254 | 0.818 | −10.000 | 1.00 | 42.07 | C |
| ATOM | 788 | CD1 | LEU | A | 118 | 78.951 | 0.057 | −10.239 | 1.00 | 41.45 | C |

TABLE 3-continued

FGFR2(D2–D3) Complexed with FGF2

| ATOM | 789 | CD2 | LEU | A | 118 | 81.446 | 0.003 | −10.516 | 1.00 | 41.56 | C |
|------|-----|-----|-----|---|-----|--------|-------|---------|------|-------|---|
| ATOM | 790 | N | LYS | A | 119 | 81.858 | 4.022 | −12.778 | 1.00 | 42.45 | N |
| ATOM | 791 | CA | LYS | A | 119 | 81.834 | 5.078 | −13.788 | 1.00 | 43.49 | C |
| ATOM | 792 | C | LYS | A | 119 | 80.565 | 4.962 | −14.622 | 1.00 | 44.00 | C |
| ATOM | 793 | O | LYS | A | 119 | 79.932 | 3.905 | −14.655 | 1.00 | 44.67 | O |
| ATOM | 794 | CB | LYS | A | 119 | 83.063 | 4.968 | −14.708 | 1.00 | 42.89 | C |
| ATOM | 795 | N | ARG | A | 120 | 80.203 | 6.049 | −15.299 | 1.00 | 44.73 | N |
| ATOM | 796 | CA | ARG | A | 120 | 79.006 | 6.076 | −16.135 | 1.00 | 45.11 | C |
| ATOM | 797 | C | ARG | A | 120 | 79.049 | 4.988 | −17.199 | 1.00 | 45.13 | C |
| ATOM | 798 | O | ARG | A | 120 | 78.019 | 4.613 | −17.761 | 1.00 | 45.32 | O |
| ATOM | 799 | CB | ARG | A | 120 | 78.860 | 7.450 | −16.802 | 1.00 | 44.67 | C |
| ATOM | 800 | N | THR | A | 121 | 80.243 | 4.469 | −17.455 | 1.00 | 46.00 | N |
| ATOM | 801 | CA | THR | A | 121 | 80.428 | 3.437 | −18.466 | 1.00 | 46.87 | C |
| ATOM | 802 | C | THR | A | 121 | 80.083 | 2.048 | −17.950 | 1.00 | 47.24 | C |
| ATOM | 803 | O | THR | A | 121 | 79.722 | 1.159 | −18.720 | 1.00 | 47.43 | O |
| ATOM | 804 | CB | THR | A | 121 | 81.878 | 3.422 | −18.956 | 1.00 | 47.67 | C |
| ATOM | 805 | OG1 | THR | A | 121 | 82.719 | 2.880 | −17.929 | 1.00 | 48.94 | O |
| ATOM | 806 | CG2 | THR | A | 121 | 82.344 | 4.848 | −19.287 | 1.00 | 47.63 | C |
| ATOM | 807 | N | GLY | A | 122 | 80.194 | 1.857 | −16.643 | 1.00 | 48.13 | N |
| ATOM | 808 | CA | GLY | A | 122 | 79.900 | 0.554 | −16.076 | 1.00 | 48.96 | C |
| ATOM | 809 | C | GLY | A | 122 | 81.164 | −0.088 | −15.537 | 1.00 | 49.43 | C |
| ATOM | 810 | O | GLY | A | 122 | 81.137 | −1.182 | −14.966 | 1.00 | 49.53 | O |
| ATOM | 811 | N | GLN | A | 123 | 82.285 | 0.594 | −15.736 | 1.00 | 49.50 | N |
| ATOM | 812 | CA | GLN | A | 123 | 83.561 | 0.104 | −15.246 | 1.00 | 49.94 | C |
| ATOM | 813 | C | GLN | A | 123 | 83.794 | 0.816 | −13.918 | 1.00 | 49.63 | C |
| ATOM | 814 | O | GLN | A | 123 | 83.316 | 1.933 | −13.721 | 1.00 | 49.09 | O |
| ATOM | 815 | CB | GLN | A | 123 | 84.675 | 0.432 | −16.248 | 1.00 | 51.19 | C |
| ATOM | 816 | CG | GLN | A | 123 | 84.625 | −0.387 | −17.542 | 1.00 | 52.46 | C |
| ATOM | 817 | CD | GLN | A | 123 | 84.983 | −1.856 | −17.329 | 1.00 | 54.02 | C |
| ATOM | 818 | OE1 | GLN | A | 123 | 86.025 | −2.176 | −16.742 | 1.00 | 54.84 | O |
| ATOM | 819 | NE2 | GLN | A | 123 | 84.127 | −2.755 | −17.812 | 1.00 | 53.61 | N |
| ATOM | 820 | N | TYR | A | 124 | 84.508 | 0.174 | −12.998 | 1.00 | 49.42 | N |
| ATOM | 821 | CA | TYR | A | 124 | 84.753 | 0.804 | −11.709 | 1.00 | 49.47 | C |
| ATOM | 822 | C | TYR | A | 124 | 85.580 | 2.060 | −11.910 | 1.00 | 48.95 | C |
| ATOM | 823 | O | TYR | A | 124 | 86.123 | 2.286 | −12.988 | 1.00 | 48.14 | O |
| ATOM | 824 | CB | TYR | A | 124 | 85.463 | −0.162 | −10.749 | 1.00 | 51.35 | C |
| ATOM | 825 | CG | TYR | A | 124 | 86.908 | −0.453 | −11.080 | 1.00 | 52.93 | C |
| ATOM | 826 | CD1 | TYR | A | 124 | 87.909 | 0.477 | −10.798 | 1.00 | 53.68 | C |
| ATOM | 827 | CD2 | TYR | A | 124 | 87.278 | −1.664 | −11.662 | 1.00 | 54.20 | C |
| ATOM | 828 | CE1 | TYR | A | 124 | 89.241 | 0.211 | −11.085 | 1.00 | 54.73 | C |
| ATOM | 829 | CE2 | TYR | A | 124 | 88.612 | −1.941 | −11.954 | 1.00 | 55.22 | C |
| ATOM | 830 | CZ | TYR | A | 124 | 89.587 | −0.998 | −11.661 | 1.00 | 55.25 | C |
| ATOM | 831 | OH | TYR | A | 124 | 90.909 | −1.263 | −11.936 | 1.00 | 56.45 | O |
| ATOM | 832 | N | LYS | A | 125 | 85.667 | 2.875 | −10.865 | 1.00 | 48.65 | N |
| ATOM | 833 | CA | LYS | A | 125 | 86.417 | 4.120 | −10.914 | 1.00 | 49.19 | C |
| ATOM | 834 | C | LYS | A | 125 | 87.553 | 4.062 | −9.898 | 1.00 | 49.55 | C |
| ATOM | 835 | O | LYS | A | 125 | 87.334 | 3.697 | −8.740 | 1.00 | 49.81 | O |
| ATOM | 836 | CB | LYS | A | 125 | 85.483 | 5.295 | −10.598 | 1.00 | 49.88 | C |
| ATOM | 837 | CG | LYS | A | 125 | 86.112 | 6.672 | −10.754 | 1.00 | 50.85 | C |
| ATOM | 838 | CD | LYS | A | 125 | 85.061 | 7.782 | −10.628 | 1.00 | 51.23 | C |
| ATOM | 839 | CE | LYS | A | 125 | 85.663 | 9.162 | −10.862 | 1.00 | 51.49 | C |
| ATOM | 840 | NZ | LYS | A | 125 | 84.656 | 10.243 | −10.685 | 1.00 | 51.35 | N |
| ATOM | 841 | N | LEU | A | 126 | 88.762 | 4.409 | −10.331 | 1.00 | 49.75 | N |
| ATOM | 842 | CA | LEU | A | 126 | 89.926 | 4.381 | −9.455 | 1.00 | 50.08 | C |
| ATOM | 843 | C | LEU | A | 126 | 89.642 | 5.119 | −8.163 | 1.00 | 50.74 | C |
| ATOM | 844 | O | LEU | A | 126 | 89.212 | 6.271 | −8.181 | 1.00 | 50.88 | O |
| ATOM | 845 | CB | LEU | A | 126 | 91.133 | 5.015 | −10.150 | 1.00 | 50.72 | C |
| ATOM | 846 | N | GLY | A | 127 | 89.886 | 4.452 | −7.042 | 1.00 | 51.26 | N |
| ATOM | 847 | CA | GLY | A | 127 | 89.647 | 5.074 | −5.754 | 1.00 | 52.31 | C |
| ATOM | 848 | C | GLY | A | 127 | 90.309 | 6.432 | −5.628 | 1.00 | 53.41 | C |
| ATOM | 849 | O | GLY | A | 127 | 89.778 | 7.332 | −4.977 | 1.00 | 53.62 | O |
| ATOM | 850 | N | SER | A | 128 | 91.469 | 6.587 | −6.258 | 1.00 | 54.05 | N |
| ATOM | 851 | CA | SER | A | 128 | 92.212 | 7.841 | −6.196 | 1.00 | 54.57 | C |
| ATOM | 852 | C | SER | A | 128 | 91.509 | 9.002 | −6.902 | 1.00 | 54.32 | C |
| ATOM | 853 | O | SER | A | 128 | 91.834 | 10.167 | −6.670 | 1.00 | 54.14 | O |
| ATOM | 854 | CB | SER | A | 128 | 93.608 | 7.634 | −6.786 | 1.00 | 55.37 | C |
| ATOM | 855 | OG | SER | A | 128 | 93.545 | 6.824 | −7.945 | 1.00 | 57.14 | O |
| ATOM | 856 | N | LYS | A | 129 | 90.538 | 8.682 | −7.752 | 1.00 | 53.92 | N |
| ATOM | 857 | CA | LYS | A | 129 | 89.801 | 9.703 | −8.489 | 1.00 | 53.25 | C |
| ATOM | 858 | C | LYS | A | 129 | 88.405 | 9.964 | −7.909 | 1.00 | 52.55 | C |
| ATOM | 859 | O | LYS | A | 129 | 87.572 | 10.605 | −8.552 | 1.00 | 52.29 | O |
| ATOM | 860 | CB | LYS | A | 129 | 89.680 | 9.283 | −9.961 | 1.00 | 53.64 | C |
| ATOM | 861 | N | THR | A | 130 | 88.152 | 9.481 | −6.695 | 1.00 | 51.39 | N |
| ATOM | 862 | CA | THR | A | 130 | 86.847 | 9.674 | −6.072 | 1.00 | 50.01 | C |
| ATOM | 863 | C | THR | A | 130 | 86.860 | 10.805 | −5.058 | 1.00 | 50.56 | C |
| ATOM | 864 | O | THR | A | 130 | 87.914 | 11.188 | −4.546 | 1.00 | 51.07 | O |
| ATOM | 865 | CB | THR | A | 130 | 86.351 | 8.396 | −5.361 | 1.00 | 48.77 | C |

TABLE 3-continued

FGFR2(D2–D3) Complexed with FGF2

| ATOM | 866 | OG1 | THR | A | 130 | 87.193 | 8.114 | −4.237 | 1.00 | 46.90 | O |
|---|---|---|---|---|---|---|---|---|---|---|---|
| ATOM | 867 | CG2 | THR | A | 130 | 86.357 | 7.219 | −6.315 | 1.00 | 46.34 | C |
| ATOM | 868 | N | GLY | A | 131 | 85.670 | 11.330 | −4.775 | 1.00 | 50.61 | N |
| ATOM | 869 | CA | GLY | A | 131 | 85.526 | 12.424 | −3.830 | 1.00 | 50.27 | C |
| ATOM | 870 | C | GLY | A | 131 | 84.149 | 12.386 | −3.200 | 1.00 | 50.50 | C |
| ATOM | 871 | O | GLY | A | 131 | 83.225 | 11.829 | −3.793 | 1.00 | 50.45 | O |
| ATOM | 872 | N | PRO | A | 132 | 83.973 | 12.987 | −2.011 | 1.00 | 50.77 | N |
| ATOM | 873 | CA | PRO | A | 132 | 82.700 | 13.018 | −1.282 | 1.00 | 51.13 | C |
| ATOM | 874 | C | PRO | A | 132 | 81.453 | 13.563 | −1.979 | 1.00 | 51.41 | C |
| ATOM | 875 | O | PRO | A | 132 | 80.328 | 13.166 | −1.638 | 1.00 | 52.28 | O |
| ATOM | 876 | CB | PRO | A | 132 | 83.048 | 13.790 | −0.008 | 1.00 | 51.20 | C |
| ATOM | 877 | CG | PRO | A | 132 | 84.179 | 14.648 | −0.419 | 1.00 | 51.10 | C |
| ATOM | 878 | CD | PRO | A | 132 | 85.006 | 13.725 | −1.271 | 1.00 | 51.01 | C |
| ATOM | 879 | N | GLY | A | 133 | 81.629 | 14.445 | −2.956 | 1.00 | 50.67 | N |
| ATOM | 880 | CA | GLY | A | 133 | 80.466 | 14.997 | −3.626 | 1.00 | 49.53 | C |
| ATOM | 881 | C | GLY | A | 133 | 80.120 | 14.351 | −4.952 | 1.00 | 49.10 | C |
| ATOM | 882 | O | GLY | A | 133 | 79.163 | 14.769 | −5.608 | 1.00 | 49.41 | O |
| ATOM | 883 | N | GLN | A | 134 | 80.873 | 13.328 | −5.350 | 1.00 | 48.03 | N |
| ATOM | 884 | CA | GLN | A | 134 | 80.631 | 12.665 | −6.634 | 1.00 | 46.42 | C |
| ATOM | 885 | C | GLN | A | 134 | 79.401 | 11.764 | −6.653 | 1.00 | 45.21 | C |
| ATOM | 886 | O | GLN | A | 134 | 78.978 | 11.236 | −5.624 | 1.00 | 45.24 | O |
| ATOM | 887 | CB | GLN | A | 134 | 81.847 | 11.826 | −7.069 | 1.00 | 46.96 | C |
| ATOM | 888 | CG | GLN | A | 134 | 83.204 | 12.511 | −6.966 | 1.00 | 47.47 | C |
| ATOM | 889 | CD | GLN | A | 134 | 84.304 | 11.760 | −7.722 | 1.00 | 48.07 | C |
| ATOM | 890 | OE1 | GLN | A | 134 | 84.137 | 10.603 | −8.111 | 1.00 | 47.30 | O |
| ATOM | 891 | NE2 | GLN | A | 134 | 85.436 | 12.424 | −7.925 | 1.00 | 48.32 | N |
| ATOM | 892 | N | LYS | A | 135 | 78.849 | 11.586 | −7.848 | 1.00 | 43.48 | N |
| ATOM | 893 | CA | LYS | A | 135 | 77.683 | 10.736 | −8.060 | 1.00 | 42.04 | C |
| ATOM | 894 | C | LYS | A | 135 | 78.104 | 9.262 | −8.174 | 1.00 | 40.40 | C |
| ATOM | 895 | O | LYS | A | 135 | 77.295 | 8.355 | −7.952 | 1.00 | 39.47 | O |
| ATOM | 896 | CB | LYS | A | 135 | 76.958 | 11.165 | −9.339 | 1.00 | 42.66 | C |
| ATOM | 897 | CG | LYS | A | 135 | 75.740 | 10.333 | −9.657 | 1.00 | 44.25 | C |
| ATOM | 898 | CD | LYS | A | 135 | 74.998 | 10.872 | −10.872 | 1.00 | 46.61 | C |
| ATOM | 899 | CE | LYS | A | 135 | 73.761 | 10.029 | −11.161 | 1.00 | 46.93 | C |
| ATOM | 900 | NZ | LYS | A | 135 | 72.944 | 10.547 | −12.304 | 1.00 | 49.32 | N |
| ATOM | 901 | N | ALA | A | 136 | 79.373 | 9.040 | −8.512 | 1.00 | 38.08 | N |
| ATOM | 902 | CA | ALA | A | 136 | 79.924 | 7.695 | −8.678 | 1.00 | 36.96 | C |
| ATOM | 903 | C | ALA | A | 136 | 80.080 | 6.879 | −7.381 | 1.00 | 34.83 | C |
| ATOM | 904 | O | ALA | A | 136 | 80.202 | 5.653 | −7.438 | 1.00 | 35.66 | O |
| ATOM | 905 | CB | ALA | A | 136 | 81.275 | 7.781 | −9.407 | 1.00 | 36.48 | C |
| ATOM | 906 | N | ILE | A | 137 | 80.070 | 7.546 | −6.227 | 1.00 | 32.81 | N |
| ATOM | 907 | CA | ILE | A | 137 | 80.218 | 6.859 | −4.945 | 1.00 | 31.45 | C |
| ATOM | 908 | C | ILE | A | 137 | 78.891 | 6.572 | −4.214 | 1.00 | 30.17 | C |
| ATOM | 909 | O | ILE | A | 137 | 78.897 | 5.983 | −3.130 | 1.00 | 28.56 | O |
| ATOM | 910 | CB | ILE | A | 137 | 81.117 | 7.675 | −3.957 | 1.00 | 31.54 | C |
| ATOM | 911 | CG1 | ILE | A | 137 | 80.335 | 8.871 | −3.399 | 1.00 | 31.63 | C |
| ATOM | 912 | CG2 | ILE | A | 137 | 82.378 | 8.184 | −4.671 | 1.00 | 32.38 | C |
| ATOM | 913 | CD1 | ILE | A | 137 | 81.052 | 9.626 | −2.286 | 1.00 | 29.61 | C |
| ATOM | 914 | N | LEU | A | 138 | 77.765 | 6.983 | −4.795 | 1.00 | 29.06 | N |
| ATOM | 915 | CA | LEU | A | 138 | 76.462 | 6.786 | −4.139 | 1.00 | 28.39 | C |
| ATOM | 916 | C | LEU | A | 138 | 75.759 | 5.489 | −4.504 | 1.00 | 27.29 | C |
| ATOM | 917 | O | LEU | A | 138 | 75.437 | 5.253 | −5.667 | 1.00 | 26.85 | O |
| ATOM | 918 | CB | LEU | A | 138 | 75.535 | 7.969 | −4.431 | 1.00 | 26.97 | C |
| ATOM | 919 | CG | LEU | A | 138 | 76.149 | 9.310 | −4.017 | 1.00 | 28.21 | C |
| ATOM | 920 | CD1 | LEU | A | 138 | 75.281 | 10.467 | −4.525 | 1.00 | 27.23 | C |
| ATOM | 921 | CD2 | LEU | A | 138 | 76.293 | 9.368 | −2.497 | 1.00 | 27.43 | C |
| ATOM | 922 | N | PHE | A | 139 | 75.516 | 4.655 | −3.495 | 1.00 | 26.91 | N |
| ATOM | 923 | CA | PHE | A | 139 | 74.851 | 3.368 | −3.706 | 1.00 | 26.74 | C |
| ATOM | 924 | C | PHE | A | 139 | 73.584 | 3.210 | −2.866 | 1.00 | 27.02 | C |
| ATOM | 925 | O | PHE | A | 139 | 73.475 | 3.730 | −1.758 | 1.00 | 25.58 | O |
| ATOM | 926 | CB | PHE | A | 139 | 75.801 | 2.198 | −3.383 | 1.00 | 27.16 | C |
| ATOM | 927 | CG | PHE | A | 139 | 76.989 | 2.089 | −4.311 | 1.00 | 27.58 | C |
| ATOM | 928 | CD1 | PHE | A | 139 | 78.119 | 2.893 | −4.130 | 1.00 | 27.23 | C |
| ATOM | 929 | CD2 | PHE | A | 139 | 76.973 | 1.179 | −5.375 | 1.00 | 27.34 | C |
| ATOM | 930 | CE1 | PHE | A | 139 | 79.228 | 2.786 | −5.007 | 1.00 | 27.33 | C |
| ATOM | 931 | CE2 | PHE | A | 139 | 78.064 | 1.066 | −6.253 | 1.00 | 26.45 | C |
| ATOM | 932 | CZ | PHE | A | 139 | 79.192 | 1.868 | −6.070 | 1.00 | 26.09 | C |
| ATOM | 933 | N | LEU | A | 140 | 72.638 | 2.450 | −3.402 | 1.00 | 26.95 | N |
| ATOM | 934 | CA | LEU | A | 140 | 71.385 | 2.199 | −2.723 | 1.00 | 27.05 | C |
| ATOM | 935 | C | LEU | A | 140 | 71.262 | 0.701 | −2.504 | 1.00 | 27.88 | C |
| ATOM | 936 | O | LEU | A | 140 | 71.153 | −0.058 | −3.461 | 1.00 | 28.79 | O |
| ATOM | 937 | CB | LEU | A | 140 | 70.228 | 2.708 | −3.591 | 1.00 | 26.81 | C |
| ATOM | 938 | CG | LEU | A | 140 | 68.802 | 2.552 | −3.055 | 1.00 | 26.55 | C |
| ATOM | 939 | CD1 | LEU | A | 140 | 68.691 | 3.334 | −1.760 | 1.00 | 27.17 | C |
| ATOM | 940 | CD2 | LEU | A | 140 | 67.784 | 3.057 | −4.090 | 1.00 | 25.60 | C |
| ATOM | 941 | N | PRO | A | 141 | 71.287 | 0.246 | −1.239 | 1.00 | 28.65 | N |
| ATOM | 942 | CA | PRO | A | 141 | 71.171 | −1.201 | −1.015 | 1.00 | 30.03 | C |

TABLE 3-continued

| FGFR2(D2–D3) Complexed with FGF2 | | | | | | | | | | |
|---|---|---|---|---|---|---|---|---|---|---|
| ATOM | 943 | C | PRO | A | 141 | 69.762 | −1.677 | −1.358 | 1.00 | 30.80 | C |
| ATOM | 944 | O | PRO | A | 141 | 68.777 | −1.062 | −0.945 | 1.00 | 31.23 | O |
| ATOM | 945 | CB | PRO | A | 141 | 71.502 | −1.341 | 0.472 | 1.00 | 29.16 | C |
| ATOM | 946 | CG | PRO | A | 141 | 70.894 | −0.089 | 1.053 | 1.00 | 29.20 | C |
| ATOM | 947 | CD | PRO | A | 141 | 71.285 | 0.987 | 0.035 | 1.00 | 28.56 | C |
| ATOM | 948 | N | MET | A | 142 | 69.670 | −2.758 | −2.124 | 1.00 | 32.42 | N |
| ATOM | 949 | CA | MET | A | 142 | 68.378 | −3.298 | −2.531 | 1.00 | 34.31 | C |
| ATOM | 950 | C | MET | A | 142 | 68.296 | −4.795 | −2.277 | 1.00 | 35.79 | C |
| ATOM | 951 | O | MET | A | 142 | 69.318 | −5.486 | −2.227 | 1.00 | 36.15 | O |
| ATOM | 952 | CB | MET | A | 142 | 68.143 | −3.025 | −4.018 | 1.00 | 34.61 | C |
| ATOM | 953 | CG | MET | A | 142 | 68.149 | −1.553 | −4.402 | 1.00 | 33.78 | C |
| ATOM | 954 | SD | MET | A | 142 | 67.851 | −1.331 | −6.157 | 1.00 | 34.38 | S |
| ATOM | 955 | CE | MET | A | 142 | 66.113 | −1.835 | −6.255 | 1.00 | 34.37 | C |
| ATOM | 956 | N | SER | A | 143 | 67.075 | −5.291 | −2.132 | 1.00 | 37.37 | N |
| ATOM | 957 | CA | SER | A | 143 | 66.848 | −6.707 | −1.883 | 1.00 | 39.58 | C |
| ATOM | 958 | C | SER | A | 143 | 67.342 | −7.591 | −3.020 | 1.00 | 40.67 | C |
| ATOM | 959 | O | SER | A | 143 | 67.277 | −7.215 | −4.193 | 1.00 | 39.83 | O |
| ATOM | 960 | CB | SER | A | 143 | 65.360 | −6.966 | −1.652 | 1.00 | 39.84 | C |
| ATOM | 961 | OG | SER | A | 143 | 65.143 | −8.328 | −1.337 | 1.00 | 41.58 | O |
| ATOM | 962 | N | ALA | A | 144 | 67.842 | −8.770 | −2.662 | 1.00 | 42.94 | N |
| ATOM | 963 | CA | ALA | A | 144 | 68.327 | −9.715 | −3.659 | 1.00 | 45.52 | C |
| ATOM | 964 | C | ALA | A | 144 | 67.165 | −10.596 | −4.135 | 1.00 | 47.20 | C |
| ATOM | 965 | O | ALA | A | 144 | 67.364 | −11.740 | −4.528 | 1.00 | 48.00 | O |
| ATOM | 966 | CB | ALA | A | 144 | 69.453 | −10.571 | −3.083 | 1.00 | 44.42 | C |
| ATOM | 967 | N | LYS | A | 145 | 65.954 | −10.037 | −4.103 | 1.00 | 49.35 | N |
| ATOM | 968 | CA | LYS | A | 145 | 64.739 | −10.732 | −4.536 | 1.00 | 50.42 | C |
| ATOM | 969 | C | LYS | A | 145 | 64.599 | −12.067 | −3.830 | 1.00 | 51.05 | C |
| ATOM | 970 | O | LYS | A | 145 | 64.318 | −12.015 | −2.615 | 1.00 | 51.85 | O |
| ATOM | 971 | CB | LYS | A | 145 | 64.749 | −10.954 | −6.053 | 1.00 | 50.92 | C |
| TER | 972 | | LYS | A | 145 | | | | | | |
| ATOM | 973 | N | HIS | B | 16 | 29.691 | 59.874 | −5.987 | 1.00 | 41.20 | N |
| ATOM | 974 | CA | HIS | B | 16 | 30.532 | 60.667 | −6.938 | 1.00 | 40.87 | C |
| ATOM | 975 | C | HIS | B | 16 | 32.001 | 60.521 | −6.563 | 1.00 | 39.74 | C |
| ATOM | 976 | O | HIS | B | 16 | 32.413 | 60.901 | −5.467 | 1.00 | 39.06 | O |
| ATOM | 977 | CB | HIS | B | 16 | 30.131 | 62.149 | −6.894 | 1.00 | 41.47 | C |
| ATOM | 978 | N | PHE | B | 17 | 32.783 | 59.981 | −7.489 | 1.00 | 38.43 | N |
| ATOM | 979 | CA | PHE | B | 17 | 34.203 | 59.742 | −7.270 | 1.00 | 37.73 | C |
| ATOM | 980 | C | PHE | B | 17 | 35.047 | 60.975 | −6.928 | 1.00 | 37.15 | C |
| ATOM | 981 | O | PHE | B | 17 | 36.062 | 60.855 | −6.240 | 1.00 | 36.85 | O |
| ATOM | 982 | CB | PHE | B | 17 | 34.784 | 59.027 | −8.494 | 1.00 | 36.91 | C |
| ATOM | 983 | CG | PHE | B | 17 | 34.834 | 59.876 | −9.724 | 1.00 | 35.74 | C |
| ATOM | 984 | CD1 | PHE | B | 17 | 35.928 | 60.696 | −9.969 | 1.00 | 35.10 | C |
| ATOM | 985 | CD2 | PHE | B | 17 | 33.794 | 59.855 | −10.646 | 1.00 | 35.94 | C |
| ATOM | 986 | CE1 | PHE | B | 17 | 35.988 | 61.480 | −11.112 | 1.00 | 35.16 | C |
| ATOM | 987 | CE2 | PHE | B | 17 | 33.846 | 60.640 | −11.800 | 1.00 | 36.07 | C |
| ATOM | 988 | CZ | PHE | B | 17 | 34.944 | 61.453 | −12.032 | 1.00 | 35.19 | C |
| ATOM | 989 | N | LYS | B | 18 | 34.641 | 62.154 | −7.392 | 1.00 | 37.23 | N |
| ATOM | 990 | CA | LYS | B | 18 | 35.420 | 63.355 | −7.092 | 1.00 | 38.08 | C |
| ATOM | 991 | C | LYS | B | 18 | 35.185 | 63.943 | −5.698 | 1.00 | 38.08 | C |
| ATOM | 992 | O | LYS | B | 18 | 35.948 | 64.798 | −5.244 | 1.00 | 38.20 | O |
| ATOM | 993 | CB | LYS | B | 18 | 35.231 | 64.432 | −8.171 | 1.00 | 39.65 | C |
| ATOM | 994 | CG | LYS | B | 18 | 33.845 | 64.545 | −8.774 | 1.00 | 42.73 | C |
| ATOM | 995 | CD | LYS | B | 18 | 33.890 | 65.478 | −9.994 | 1.00 | 43.91 | C |
| ATOM | 996 | CE | LYS | B | 18 | 32.555 | 65.512 | −10.725 | 1.00 | 44.63 | C |
| ATOM | 997 | NZ | LYS | B | 18 | 32.139 | 64.155 | −11.160 | 1.00 | 46.27 | N |
| ATOM | 998 | N | ASP | B | 19 | 34.158 | 63.462 | −5.007 | 1.00 | 37.77 | N |
| ATOM | 999 | CA | ASP | B | 19 | 33.864 | 63.942 | −3.661 | 1.00 | 38.47 | C |
| ATOM | 1000 | C | ASP | B | 19 | 34.811 | 63.344 | −2.620 | 1.00 | 38.55 | C |
| ATOM | 1001 | O | ASP | B | 19 | 35.267 | 62.202 | −2.763 | 1.00 | 37.81 | O |
| ATOM | 1002 | CB | ASP | B | 19 | 32.431 | 63.580 | −3.263 | 1.00 | 39.90 | C |
| ATOM | 1003 | CG | ASP | B | 19 | 31.384 | 64.268 | −4.122 | 1.00 | 41.14 | C |
| ATOM | 1004 | OD1 | ASP | B | 19 | 30.214 | 63.826 | −4.091 | 1.00 | 41.72 | O |
| ATOM | 1005 | OD2 | ASP | B | 19 | 31.724 | 65.253 | −4.814 | 1.00 | 42.42 | O |
| ATOM | 1006 | N | PRO | B | 20 | 35.132 | 64.121 | −1.566 | 1.00 | 38.54 | N |
| ATOM | 1007 | CA | PRO | B | 20 | 36.016 | 63.650 | −0.497 | 1.00 | 38.26 | C |
| ATOM | 1008 | C | PRO | B | 20 | 35.346 | 62.480 | 0.226 | 1.00 | 37.93 | C |
| ATOM | 1009 | O | PRO | B | 20 | 34.129 | 62.302 | 0.135 | 1.00 | 37.55 | O |
| ATOM | 1010 | CB | PRO | B | 20 | 36.182 | 64.886 | 0.397 | 1.00 | 39.27 | C |
| ATOM | 1011 | CG | PRO | B | 20 | 34.945 | 65.690 | 0.133 | 1.00 | 39.95 | C |
| ATOM | 1012 | CD | PRO | B | 20 | 34.776 | 65.539 | −1.361 | 1.00 | 39.71 | C |
| ATOM | 1013 | N | LYS | B | 21 | 36.128 | 61.684 | 0.945 | 1.00 | 37.56 | N |
| ATOM | 1014 | CA | LYS | B | 21 | 35.566 | 60.514 | 1.624 | 1.00 | 38.03 | C |
| ATOM | 1015 | C | LYS | B | 21 | 36.277 | 60.213 | 2.922 | 1.00 | 37.58 | C |
| ATOM | 1016 | O | LYS | B | 21 | 37.356 | 60.736 | 3.195 | 1.00 | 37.36 | O |
| ATOM | 1017 | CB | LYS | B | 21 | 35.718 | 59.232 | 0.773 | 1.00 | 38.55 | C |
| ATOM | 1018 | CG | LYS | B | 21 | 35.458 | 59.310 | −0.726 | 1.00 | 40.40 | C |
| ATOM | 1019 | CD | LYS | B | 21 | 36.141 | 58.119 | −1.403 | 1.00 | 42.66 | C |

TABLE 3-continued

FGFR2(D2–D3) Complexed with FGF2

| ATOM | 1020 | CE | LYS | B | 21 | 36.004 | 58.118 | −2.931 | 1.00 | 45.28 | C |
|---|---|---|---|---|---|---|---|---|---|---|---|
| ATOM | 1021 | NZ | LYS | B | 21 | 34.693 | 57.570 | −3.390 | 1.00 | 46.79 | N |
| ATOM | 1022 | N | ARG | B | 22 | 35.660 | 59.338 | 3.705 | 1.00 | 36.89 | N |
| ATOM | 1023 | CA | ARG | B | 22 | 36.254 | 58.875 | 4.942 | 1.00 | 36.76 | C |
| ATOM | 1024 | C | ARG | B | 22 | 36.607 | 57.442 | 4.575 | 1.00 | 35.99 | C |
| ATOM | 1025 | O | ARG | B | 22 | 35.878 | 56.812 | 3.807 | 1.00 | 36.59 | O |
| ATOM | 1026 | CB | ARG | B | 22 | 35.244 | 58.835 | 6.088 | 1.00 | 37.88 | C |
| ATOM | 1027 | CG | ARG | B | 22 | 34.503 | 60.125 | 6.396 | 1.00 | 40.72 | C |
| ATOM | 1028 | CD | ARG | B | 22 | 33.663 | 59.899 | 7.650 | 1.00 | 42.38 | C |
| ATOM | 1029 | NE | ARG | B | 22 | 32.359 | 60.562 | 7.626 | 1.00 | 45.73 | N |
| ATOM | 1030 | CZ | ARG | B | 22 | 32.137 | 61.830 | 7.961 | 1.00 | 46.48 | C |
| ATOM | 1031 | NH1 | ARG | B | 22 | 33.137 | 62.608 | 8.355 | 1.00 | 48.50 | N |
| ATOM | 1032 | NH2 | ARG | B | 22 | 30.904 | 62.320 | 7.909 | 1.00 | 47.02 | N |
| ATOM | 1033 | N | LEU | B | 23 | 37.725 | 56.938 | 5.085 | 1.00 | 34.47 | N |
| ATOM | 1034 | CA | LEU | B | 23 | 38.119 | 55.559 | 4.824 | 1.00 | 32.66 | C |
| ATOM | 1035 | C | LEU | B | 23 | 37.990 | 54.799 | 6.142 | 1.00 | 33.01 | C |
| ATOM | 1036 | O | LEU | B | 23 | 38.799 | 54.979 | 7.059 | 1.00 | 33.02 | O |
| ATOM | 1037 | CB | LEU | B | 23 | 39.557 | 55.479 | 4.311 | 1.00 | 31.69 | C |
| ATOM | 1038 | CG | LEU | B | 23 | 39.832 | 55.862 | 2.851 | 1.00 | 31.92 | C |
| ATOM | 1039 | CD1 | LEU | B | 23 | 41.324 | 55.644 | 2.544 | 1.00 | 31.01 | C |
| ATOM | 1040 | CD2 | LEU | B | 23 | 38.968 | 55.019 | 1.914 | 1.00 | 30.24 | C |
| ATOM | 1041 | N | TYR | B | 24 | 36.957 | 53.958 | 6.223 | 1.00 | 31.84 | N |
| ATOM | 1042 | CA | TYR | B | 24 | 36.651 | 53.158 | 7.408 | 1.00 | 30.77 | C |
| ATOM | 1043 | C | TYR | B | 24 | 37.390 | 51.815 | 7.406 | 1.00 | 30.86 | C |
| ATOM | 1044 | O | TYR | B | 24 | 37.290 | 51.042 | 6.457 | 1.00 | 30.57 | O |
| ATOM | 1045 | CB | TYR | B | 24 | 35.118 | 52.950 | 7.489 | 1.00 | 29.83 | C |
| ATOM | 1046 | CG | TYR | B | 24 | 34.605 | 51.982 | 8.548 | 1.00 | 28.06 | C |
| ATOM | 1047 | CD1 | TYR | B | 24 | 34.689 | 50.601 | 8.359 | 1.00 | 29.06 | C |
| ATOM | 1048 | CD2 | TYR | B | 24 | 34.010 | 52.447 | 9.728 | 1.00 | 27.71 | C |
| ATOM | 1049 | CE1 | TYR | B | 24 | 34.191 | 49.701 | 9.314 | 1.00 | 28.51 | C |
| ATOM | 1050 | CE2 | TYR | B | 24 | 33.509 | 51.559 | 10.691 | 1.00 | 27.43 | C |
| ATOM | 1051 | CZ | TYR | B | 24 | 33.601 | 50.184 | 10.475 | 1.00 | 29.33 | C |
| ATOM | 1052 | OH | TYR | B | 24 | 33.092 | 49.285 | 11.398 | 1.00 | 29.90 | O |
| ATOM | 1053 | N | CYS | B | 25 | 38.135 | 51.537 | 8.471 | 1.00 | 30.52 | N |
| ATOM | 1054 | CA | CYS | B | 25 | 38.871 | 50.279 | 8.547 | 1.00 | 31.88 | C |
| ATOM | 1055 | C | CYS | B | 25 | 38.055 | 49.198 | 9.254 | 1.00 | 32.26 | C |
| ATOM | 1056 | O | CYS | B | 25 | 37.610 | 49.374 | 10.384 | 1.00 | 32.63 | O |
| ATOM | 1057 | CB | CYS | B | 25 | 40.216 | 50.459 | 9.272 | 1.00 | 30.70 | C |
| ATOM | 1058 | SG | CYS | B | 25 | 41.232 | 48.937 | 9.279 | 1.00 | 33.39 | S |
| ATOM | 1059 | N | LYS | B | 26 | 37.859 | 48.077 | 8.571 | 1.00 | 34.00 | N |
| ATOM | 1060 | CA | LYS | B | 26 | 37.091 | 46.978 | 9.135 | 1.00 | 35.65 | C |
| ATOM | 1061 | C | LYS | B | 26 | 37.692 | 46.542 | 10.477 | 1.00 | 36.77 | C |
| ATOM | 1062 | O | LYS | B | 26 | 36.969 | 46.136 | 11.383 | 1.00 | 36.34 | O |
| ATOM | 1063 | CB | LYS | B | 26 | 37.069 | 45.794 | 8.168 | 1.00 | 35.74 | C |
| ATOM | 1064 | CG | LYS | B | 26 | 36.256 | 44.622 | 8.690 | 1.00 | 37.36 | C |
| ATOM | 1065 | CD | LYS | B | 26 | 36.371 | 43.407 | 7.796 | 1.00 | 38.54 | C |
| ATOM | 1066 | CE | LYS | B | 26 | 35.480 | 42.287 | 8.311 | 1.00 | 40.15 | C |
| ATOM | 1067 | NZ | LYS | B | 26 | 35.677 | 41.049 | 7.509 | 1.00 | 41.23 | N |
| ATOM | 1068 | N | ASN | B | 27 | 39.014 | 46.636 | 10.602 | 1.00 | 37.35 | N |
| ATOM | 1069 | CA | ASN | B | 27 | 39.681 | 46.250 | 11.843 | 1.00 | 37.78 | C |
| ATOM | 1070 | C | ASN | B | 27 | 39.415 | 47.295 | 12.930 | 1.00 | 37.79 | C |
| ATOM | 1071 | O | ASN | B | 27 | 39.999 | 48.383 | 12.927 | 1.00 | 38.21 | O |
| ATOM | 1072 | CB | ASN | B | 27 | 41.187 | 46.103 | 11.617 | 1.00 | 39.72 | C |
| ATOM | 1073 | CG | ASN | B | 27 | 41.887 | 45.400 | 12.773 | 1.00 | 43.31 | C |
| ATOM | 1074 | OD1 | ASN | B | 27 | 43.125 | 45.404 | 12.872 | 1.00 | 43.49 | O |
| ATOM | 1075 | ND2 | ASN | B | 27 | 41.100 | 44.782 | 13.648 | 1.00 | 43.66 | N |
| ATOM | 1076 | N | GLY | B | 28 | 38.511 | 46.971 | 13.847 | 1.00 | 36.80 | N |
| ATOM | 1077 | CA | GLY | B | 28 | 38.188 | 47.883 | 14.926 | 1.00 | 36.61 | C |
| ATOM | 1078 | C | GLY | B | 28 | 37.208 | 48.999 | 14.605 | 1.00 | 36.56 | C |
| ATOM | 1079 | O | GLY | B | 28 | 36.657 | 49.622 | 15.511 | 1.00 | 36.62 | O |
| ATOM | 1080 | N | GLY | B | 29 | 36.992 | 49.272 | 13.324 | 1.00 | 37.24 | N |
| ATOM | 1081 | CA | GLY | B | 29 | 36.057 | 50.322 | 12.956 | 1.00 | 37.20 | C |
| ATOM | 1082 | C | GLY | B | 29 | 36.577 | 51.741 | 13.129 | 1.00 | 37.22 | C |
| ATOM | 1083 | O | GLY | B | 29 | 35.836 | 52.630 | 13.548 | 1.00 | 37.21 | O |
| ATOM | 1084 | N | PHE | B | 30 | 37.848 | 51.957 | 12.807 | 1.00 | 37.85 | N |
| ATOM | 1085 | CA | PHE | B | 30 | 38.458 | 53.288 | 12.919 | 1.00 | 38.68 | C |
| ATOM | 1086 | C | PHE | B | 30 | 38.508 | 53.977 | 11.559 | 1.00 | 38.10 | C |
| ATOM | 1087 | O | PHE | B | 30 | 38.687 | 53.325 | 10.536 | 1.00 | 38.20 | O |
| ATOM | 1088 | CB | PHE | B | 30 | 39.905 | 53.201 | 13.426 | 1.00 | 38.81 | C |
| ATOM | 1089 | CG | PHE | B | 30 | 40.049 | 52.642 | 14.812 | 1.00 | 39.31 | C |
| ATOM | 1090 | CD1 | PHE | B | 30 | 40.339 | 51.294 | 15.005 | 1.00 | 38.57 | C |
| ATOM | 1091 | CD2 | PHE | B | 30 | 39.932 | 53.473 | 15.923 | 1.00 | 38.57 | C |
| ATOM | 1092 | CE1 | PHE | B | 30 | 40.514 | 50.779 | 16.285 | 1.00 | 39.12 | C |
| ATOM | 1093 | CE2 | PHE | B | 30 | 40.105 | 52.972 | 17.211 | 1.00 | 38.92 | C |
| ATOM | 1094 | CZ | PHE | B | 30 | 40.397 | 51.621 | 17.396 | 1.00 | 38.67 | C |
| ATOM | 1095 | N | PHE | B | 31 | 38.365 | 55.295 | 11.559 | 1.00 | 38.30 | N |
| ATOM | 1096 | CA | PHE | B | 31 | 38.446 | 56.074 | 10.331 | 1.00 | 38.10 | C |

TABLE 3-continued

FGFR2(D2–D3) Complexed with FGF2

| ATOM | 1097 | C | PHE | B | 31 | 39.883 | 56.547 | 10.186 | 1.00 | 38.64 | C |
|---|---|---|---|---|---|---|---|---|---|---|---|
| ATOM | 1098 | O | PHE | B | 31 | 40.445 | 57.103 | 11.134 | 1.00 | 38.89 | O |
| ATOM | 1099 | CB | PHE | B | 31 | 37.531 | 57.280 | 10.421 | 1.00 | 37.10 | C |
| ATOM | 1100 | CG | PHE | B | 31 | 36.095 | 56.938 | 10.295 | 1.00 | 36.88 | C |
| ATOM | 1101 | CD1 | PHE | B | 31 | 35.551 | 56.637 | 9.047 | 1.00 | 34.97 | C |
| ATOM | 1102 | CD2 | PHE | B | 31 | 35.285 | 56.873 | 11.419 | 1.00 | 36.08 | C |
| ATOM | 1103 | CE1 | PHE | B | 31 | 34.217 | 56.277 | 8.928 | 1.00 | 35.59 | C |
| ATOM | 1104 | CE2 | PHE | B | 31 | 33.942 | 56.510 | 11.306 | 1.00 | 37.12 | C |
| ATOM | 1105 | CZ | PHE | B | 31 | 33.410 | 56.211 | 10.055 | 1.00 | 34.95 | C |
| ATOM | 1106 | N | LEU | B | 32 | 40.485 | 56.323 | 9.020 | 1.00 | 38.61 | N |
| ATOM | 1107 | CA | LEU | B | 32 | 41.870 | 56.749 | 8.791 | 1.00 | 38.97 | C |
| ATOM | 1108 | C | LEU | B | 32 | 41.958 | 58.253 | 9.036 | 1.00 | 39.72 | C |
| ATOM | 1109 | O | LEU | B | 32 | 41.170 | 59.023 | 8.482 | 1.00 | 39.68 | O |
| ATOM | 1110 | CB | LEU | B | 32 | 42.307 | 56.424 | 7.356 | 1.00 | 38.43 | C |
| ATOM | 1111 | CG | LEU | B | 32 | 43.787 | 56.609 | 6.994 | 1.00 | 38.14 | C |
| ATOM | 1112 | CD1 | LEU | B | 32 | 44.664 | 55.726 | 7.877 | 1.00 | 37.20 | C |
| ATOM | 1113 | CD2 | LEU | B | 32 | 44.004 | 56.257 | 5.530 | 1.00 | 37.43 | C |
| ATOM | 1114 | N | ARG | B | 33 | 42.910 | 58.672 | 9.870 | 1.00 | 40.78 | N |
| ATOM | 1115 | CA | ARG | B | 33 | 43.067 | 60.094 | 10.197 | 1.00 | 41.49 | C |
| ATOM | 1116 | C | ARG | B | 33 | 44.449 | 60.658 | 9.872 | 1.00 | 41.79 | C |
| ATOM | 1117 | O | ARG | B | 33 | 45.470 | 60.040 | 10.165 | 1.00 | 41.69 | O |
| ATOM | 1118 | CB | ARG | B | 33 | 42.753 | 60.316 | 11.683 | 1.00 | 41.87 | C |
| ATOM | 1119 | CG | ARG | B | 33 | 42.997 | 61.734 | 12.173 | 1.00 | 42.16 | C |
| ATOM | 1120 | CD | ARG | B | 33 | 42.468 | 61.952 | 13.587 | 1.00 | 41.66 | C |
| ATOM | 1121 | NE | ARG | B | 33 | 43.170 | 61.161 | 14.597 | 1.00 | 42.10 | N |
| ATOM | 1122 | CZ | ARG | B | 33 | 42.870 | 61.180 | 15.897 | 1.00 | 41.89 | C |
| ATOM | 1123 | NH1 | ARG | B | 33 | 41.884 | 61.947 | 16.341 | 1.00 | 39.60 | N |
| ATOM | 1124 | NH2 | ARG | B | 33 | 43.557 | 60.434 | 16.759 | 1.00 | 40.90 | N |
| ATOM | 1125 | N | ILE | B | 34 | 44.474 | 61.836 | 9.258 | 1.00 | 43.37 | N |
| ATOM | 1126 | CA | ILE | B | 34 | 45.733 | 62.497 | 8.904 | 1.00 | 44.60 | C |
| ATOM | 1127 | C | ILE | B | 34 | 45.829 | 63.834 | 9.632 | 1.00 | 45.66 | C |
| ATOM | 1128 | O | ILE | B | 34 | 45.142 | 64.793 | 9.290 | 1.00 | 45.68 | O |
| ATOM | 1129 | CB | ILE | B | 34 | 45.859 | 62.710 | 7.362 | 1.00 | 44.79 | C |
| ATOM | 1130 | CG1 | ILE | B | 34 | 46.101 | 61.357 | 6.680 | 1.00 | 44.68 | C |
| ATOM | 1131 | CG2 | ILE | B | 34 | 47.006 | 63.679 | 7.035 | 1.00 | 43.70 | C |
| ATOM | 1132 | CD1 | ILE | B | 34 | 46.242 | 61.429 | 5.182 | 1.00 | 45.23 | C |
| ATOM | 1133 | N | HIS | B | 35 | 46.683 | 63.865 | 10.654 | 1.00 | 47.90 | N |
| ATOM | 1134 | CA | HIS | B | 35 | 46.910 | 65.050 | 11.488 | 1.00 | 49.69 | C |
| ATOM | 1135 | C | HIS | B | 35 | 47.663 | 66.169 | 10.779 | 1.00 | 50.18 | C |
| ATOM | 1136 | O | HIS | B | 35 | 48.477 | 65.917 | 9.885 | 1.00 | 49.89 | O |
| ATOM | 1137 | CB | HIS | B | 35 | 47.708 | 64.667 | 12.733 | 1.00 | 50.95 | C |
| ATOM | 1138 | CG | HIS | B | 35 | 46.961 | 63.794 | 13.687 | 1.00 | 52.79 | C |
| ATOM | 1139 | ND1 | HIS | B | 35 | 45.939 | 64.266 | 14.483 | 1.00 | 53.73 | N |
| ATOM | 1140 | CD2 | HIS | B | 35 | 47.094 | 62.480 | 13.982 | 1.00 | 53.11 | C |
| ATOM | 1141 | CE1 | HIS | B | 35 | 45.476 | 63.280 | 15.230 | 1.00 | 54.07 | C |
| ATOM | 1142 | NE2 | HIS | B | 35 | 46.160 | 62.186 | 14.945 | 1.00 | 54.33 | N |
| ATOM | 1143 | N | PRO | B | 36 | 47.421 | 67.424 | 11.197 | 1.00 | 50.94 | N |
| ATOM | 1144 | CA | PRO | B | 36 | 48.080 | 68.588 | 10.601 | 1.00 | 51.39 | C |
| ATOM | 1145 | C | PRO | B | 36 | 49.603 | 68.500 | 10.634 | 1.00 | 51.71 | C |
| ATOM | 1146 | O | PRO | B | 36 | 50.266 | 68.999 | 9.729 | 1.00 | 51.94 | O |
| ATOM | 1147 | CB | PRO | B | 36 | 47.541 | 69.748 | 11.430 | 1.00 | 51.36 | C |
| ATOM | 1148 | CG | PRO | B | 36 | 46.158 | 69.284 | 11.773 | 1.00 | 51.50 | C |
| ATOM | 1149 | CD | PRO | B | 36 | 46.408 | 67.851 | 12.181 | 1.00 | 50.68 | C |
| ATOM | 1150 | N | ASP | B | 37 | 50.155 | 67.863 | 11.666 | 1.00 | 52.35 | N |
| ATOM | 1151 | CA | ASP | B | 37 | 51.607 | 67.736 | 11.767 | 1.00 | 53.06 | C |
| ATOM | 1152 | C | ASP | B | 37 | 52.169 | 66.505 | 11.064 | 1.00 | 52.67 | C |
| ATOM | 1153 | O | ASP | B | 37 | 53.354 | 66.194 | 11.192 | 1.00 | 52.98 | O |
| ATOM | 1154 | CB | ASP | B | 37 | 52.071 | 67.776 | 13.236 | 1.00 | 54.79 | C |
| ATOM | 1155 | CG | ASP | B | 37 | 51.464 | 66.676 | 14.086 | 1.00 | 56.33 | C |
| ATOM | 1156 | OD1 | ASP | B | 37 | 50.224 | 66.656 | 14.243 | 1.00 | 56.83 | O |
| ATOM | 1157 | OD2 | ASP | B | 37 | 52.236 | 65.837 | 14.607 | 1.00 | 57.53 | O |
| ATOM | 1158 | N | GLY | B | 38 | 51.318 | 65.804 | 10.318 | 1.00 | 52.01 | N |
| ATOM | 1159 | CA | GLY | B | 38 | 51.781 | 64.642 | 9.579 | 1.00 | 50.97 | C |
| ATOM | 1160 | C | GLY | B | 38 | 51.694 | 63.265 | 10.214 | 1.00 | 50.53 | C |
| ATOM | 1161 | O | GLY | B | 38 | 52.146 | 62.289 | 9.610 | 1.00 | 50.78 | O |
| ATOM | 1162 | N | ARG | B | 39 | 51.130 | 63.162 | 11.414 | 1.00 | 49.98 | N |
| ATOM | 1163 | CA | ARG | B | 39 | 51.006 | 61.857 | 12.069 | 1.00 | 50.01 | C |
| ATOM | 1164 | C | ARG | B | 39 | 49.785 | 61.117 | 11.513 | 1.00 | 48.98 | C |
| ATOM | 1165 | O | ARG | B | 39 | 48.775 | 61.743 | 11.176 | 1.00 | 48.74 | O |
| ATOM | 1166 | CB | ARG | B | 39 | 50.866 | 62.023 | 13.592 | 1.00 | 51.16 | C |
| ATOM | 1167 | CG | ARG | B | 39 | 52.179 | 62.313 | 14.318 | 1.00 | 53.76 | C |
| ATOM | 1168 | CD | ARG | B | 39 | 51.976 | 62.563 | 15.817 | 1.00 | 55.43 | C |
| ATOM | 1169 | NE | ARG | B | 39 | 51.143 | 63.738 | 16.080 | 1.00 | 57.14 | N |
| ATOM | 1170 | CZ | ARG | B | 39 | 49.822 | 63.706 | 16.244 | 1.00 | 57.89 | C |
| ATOM | 1171 | NH1 | ARG | B | 39 | 49.150 | 64.831 | 16.470 | 1.00 | 57.92 | N |
| ATOM | 1172 | NH2 | ARG | B | 39 | 49.172 | 62.549 | 16.201 | 1.00 | 58.81 | N |
| ATOM | 1173 | N | VAL | B | 40 | 49.879 | 59.793 | 11.423 | 1.00 | 47.61 | N |

TABLE 3-continued

FGFR2(D2–D3) Complexed with FGF2

| ATOM | 1174 | CA | VAL | B | 40 | 48.777 | 58.994 | 10.897 | 1.00 | 46.88 | C |
|---|---|---|---|---|---|---|---|---|---|---|---|
| ATOM | 1175 | C | VAL | B | 40 | 48.288 | 57.919 | 11.871 | 1.00 | 46.13 | C |
| ATOM | 1176 | O | VAL | B | 40 | 49.074 | 57.114 | 12.370 | 1.00 | 45.77 | O |
| ATOM | 1177 | CB | VAL | B | 40 | 49.176 | 58.321 | 9.550 | 1.00 | 46.91 | C |
| ATOM | 1178 | CG1 | VAL | B | 40 | 48.069 | 57.355 | 9.077 | 1.00 | 46.28 | C |
| ATOM | 1179 | CG2 | VAL | B | 40 | 49.421 | 59.399 | 8.493 | 1.00 | 45.41 | C |
| ATOM | 1180 | N | ASP | B | 41 | 46.983 | 57.923 | 12.132 | 1.00 | 45.81 | N |
| ATOM | 1181 | CA | ASP | B | 41 | 46.360 | 56.946 | 13.025 | 1.00 | 45.94 | C |
| ATOM | 1182 | C | ASP | B | 41 | 44.877 | 56.811 | 12.679 | 1.00 | 45.67 | C |
| ATOM | 1183 | O | ASP | B | 41 | 44.429 | 57.306 | 11.642 | 1.00 | 45.16 | O |
| ATOM | 1184 | CB | ASP | B | 41 | 46.515 | 57.376 | 14.490 | 1.00 | 45.68 | C |
| ATOM | 1185 | CG | ASP | B | 41 | 45.744 | 58.641 | 14.815 | 1.00 | 46.42 | C |
| ATOM | 1186 | OD1 | ASP | B | 41 | 45.810 | 59.094 | 15.981 | 1.00 | 47.24 | O |
| ATOM | 1187 | OD2 | ASP | B | 41 | 45.073 | 59.188 | 13.916 | 1.00 | 46.74 | O |
| ATOM | 1188 | N | GLY | B | 42 | 44.128 | 56.143 | 13.553 | 1.00 | 45.79 | N |
| ATOM | 1189 | CA | GLY | B | 42 | 42.707 | 55.956 | 13.333 | 1.00 | 45.89 | C |
| ATOM | 1190 | C | GLY | B | 42 | 41.901 | 56.424 | 14.527 | 1.00 | 46.60 | C |
| ATOM | 1191 | O | GLY | B | 42 | 42.416 | 56.488 | 15.644 | 1.00 | 46.61 | O |
| ATOM | 1192 | N | VAL | B | 43 | 40.643 | 56.774 | 14.286 | 1.00 | 47.12 | N |
| ATOM | 1193 | CA | VAL | B | 43 | 39.735 | 57.224 | 15.336 | 1.00 | 47.40 | C |
| ATOM | 1194 | C | VAL | B | 43 | 38.317 | 56.844 | 14.975 | 1.00 | 48.03 | C |
| ATOM | 1195 | O | VAL | B | 43 | 37.985 | 56.718 | 13.795 | 1.00 | 48.35 | O |
| ATOM | 1196 | CB | VAL | B | 43 | 39.767 | 58.745 | 15.542 | 1.00 | 47.09 | C |
| ATOM | 1197 | CG1 | VAL | B | 43 | 40.850 | 59.099 | 16.524 | 1.00 | 47.34 | C |
| ATOM | 1198 | CG2 | VAL | B | 43 | 39.976 | 59.452 | 14.219 | 1.00 | 45.89 | C |
| ATOM | 1199 | N | ARG | B | 44 | 37.480 | 56.684 | 15.991 | 1.00 | 48.67 | N |
| ATOM | 1200 | CA | ARG | B | 44 | 36.099 | 56.291 | 15.776 | 1.00 | 49.72 | C |
| ATOM | 1201 | C | ARG | B | 44 | 35.109 | 57.447 | 15.655 | 1.00 | 50.61 | C |
| ATOM | 1202 | O | ARG | B | 44 | 34.020 | 57.274 | 15.110 | 1.00 | 50.99 | O |
| ATOM | 1203 | CB | ARG | B | 44 | 35.671 | 55.316 | 16.879 | 1.00 | 49.25 | C |
| ATOM | 1204 | CG | ARG | B | 44 | 36.431 | 53.989 | 16.811 | 1.00 | 49.05 | C |
| ATOM | 1205 | CD | ARG | B | 44 | 36.035 | 53.017 | 17.909 | 1.00 | 48.64 | C |
| ATOM | 1206 | NE | ARG | B | 44 | 36.670 | 51.714 | 17.715 | 1.00 | 49.15 | N |
| ATOM | 1207 | CZ | ARG | B | 44 | 37.108 | 50.942 | 18.706 | 1.00 | 49.17 | C |
| ATOM | 1208 | NH1 | ARG | B | 44 | 36.982 | 51.347 | 19.965 | 1.00 | 49.60 | N |
| ATOM | 1209 | NH2 | ARG | B | 44 | 37.671 | 49.768 | 18.443 | 1.00 | 48.11 | N |
| ATOM | 1210 | N | GLU | B | 45 | 35.487 | 58.628 | 16.129 | 1.00 | 51.32 | N |
| ATOM | 1211 | CA | GLU | B | 45 | 34.590 | 59.770 | 16.061 | 1.00 | 52.99 | C |
| ATOM | 1212 | C | GLU | B | 45 | 34.382 | 60.301 | 14.639 | 1.00 | 53.72 | C |
| ATOM | 1213 | O | GLU | B | 45 | 35.247 | 60.970 | 14.067 | 1.00 | 53.64 | O |
| ATOM | 1214 | CB | GLU | B | 45 | 35.094 | 60.885 | 16.981 | 1.00 | 54.62 | C |
| ATOM | 1215 | CG | GLU | B | 45 | 34.103 | 62.022 | 17.153 | 1.00 | 56.11 | C |
| ATOM | 1216 | CD | GLU | B | 45 | 32.668 | 61.533 | 17.166 | 1.00 | 57.20 | C |
| ATOM | 1217 | OE1 | GLU | B | 45 | 32.367 | 60.568 | 17.904 | 1.00 | 58.01 | O |
| ATOM | 1218 | OE2 | GLU | B | 45 | 31.838 | 62.115 | 16.436 | 1.00 | 57.95 | O |
| ATOM | 1219 | N | LYS | B | 46 | 33.212 | 60.001 | 14.081 | 1.00 | 53.86 | N |
| ATOM | 1220 | CA | LYS | B | 46 | 32.863 | 60.425 | 12.732 | 1.00 | 54.06 | C |
| ATOM | 1221 | C | LYS | B | 46 | 32.912 | 61.941 | 12.542 | 1.00 | 54.13 | C |
| ATOM | 1222 | O | LYS | B | 46 | 32.890 | 62.429 | 11.411 | 1.00 | 54.29 | O |
| ATOM | 1223 | CB | LYS | B | 46 | 31.465 | 59.911 | 12.377 | 1.00 | 53.90 | C |
| ATOM | 1224 | N | SER | B | 47 | 32.993 | 62.682 | 13.641 | 1.00 | 54.05 | N |
| ATOM | 1225 | CA | SER | B | 47 | 33.013 | 64.142 | 13.573 | 1.00 | 54.44 | C |
| ATOM | 1226 | C | SER | B | 47 | 34.403 | 64.755 | 13.425 | 1.00 | 54.13 | C |
| ATOM | 1227 | O | SER | B | 47 | 34.536 | 65.932 | 13.092 | 1.00 | 54.74 | O |
| ATOM | 1228 | CB | SER | B | 47 | 32.328 | 64.728 | 14.811 | 1.00 | 55.19 | C |
| ATOM | 1229 | OG | SER | B | 47 | 32.215 | 66.138 | 14.708 | 1.00 | 57.49 | O |
| ATOM | 1230 | N | ASP | B | 48 | 35.438 | 63.964 | 13.668 | 1.00 | 53.76 | N |
| ATOM | 1231 | CA | ASP | B | 48 | 36.802 | 64.460 | 13.560 | 1.00 | 53.29 | C |
| ATOM | 1232 | C | ASP | B | 48 | 37.058 | 65.080 | 12.186 | 1.00 | 52.62 | C |
| ATOM | 1233 | O | ASP | B | 48 | 36.837 | 64.444 | 11.157 | 1.00 | 52.61 | O |
| ATOM | 1234 | CB | ASP | B | 48 | 37.790 | 63.320 | 13.832 | 1.00 | 54.05 | C |
| ATOM | 1235 | CG | ASP | B | 48 | 39.219 | 63.808 | 13.965 | 1.00 | 55.08 | C |
| ATOM | 1236 | OD1 | ASP | B | 48 | 39.994 | 63.167 | 14.711 | 1.00 | 55.65 | O |
| ATOM | 1237 | OD2 | ASP | B | 48 | 39.569 | 64.825 | 13.324 | 1.00 | 54.58 | O |
| ATOM | 1238 | N | PRO | B | 49 | 37.526 | 66.340 | 12.158 | 1.00 | 52.10 | N |
| ATOM | 1239 | CA | PRO | B | 49 | 37.813 | 67.060 | 10.910 | 1.00 | 50.74 | C |
| ATOM | 1240 | C | PRO | B | 49 | 39.037 | 66.568 | 10.134 | 1.00 | 49.71 | C |
| ATOM | 1241 | O | PRO | B | 49 | 39.256 | 66.979 | 8.997 | 1.00 | 50.41 | O |
| ATOM | 1242 | CB | PRO | B | 49 | 37.962 | 68.504 | 11.378 | 1.00 | 51.63 | C |
| ATOM | 1243 | CG | PRO | B | 49 | 38.574 | 68.337 | 12.738 | 1.00 | 51.61 | C |
| ATOM | 1244 | CD | PRO | B | 49 | 37.745 | 67.216 | 13.325 | 1.00 | 52.05 | C |
| ATOM | 1245 | N | HIS | B | 50 | 39.825 | 65.685 | 10.737 | 1.00 | 48.05 | N |
| ATOM | 1246 | CA | HIS | B | 50 | 41.026 | 65.163 | 10.088 | 1.00 | 46.32 | C |
| ATOM | 1247 | C | HIS | B | 50 | 40.866 | 63.790 | 9.411 | 1.00 | 44.99 | C |
| ATOM | 1248 | O | HIS | B | 50 | 41.856 | 63.141 | 9.085 | 1.00 | 44.20 | O |
| ATOM | 1249 | CB | HIS | B | 50 | 42.173 | 65.102 | 11.104 | 1.00 | 46.22 | C |
| ATOM | 1250 | N | ILE | B | 51 | 39.628 | 63.344 | 9.209 | 1.00 | 43.86 | N |

TABLE 3-continued

FGFR2(D2–D3) Complexed with FGF2

| ATOM | 1251 | CA | ILE | B | 51 | 39.394 | 62.066 | 8.544 | 1.00 | 42.57 | C |
|---|---|---|---|---|---|---|---|---|---|---|---|
| ATOM | 1252 | C | ILE | B | 51 | 38.772 | 62.280 | 7.163 | 1.00 | 41.66 | C |
| ATOM | 1253 | O | ILE | B | 51 | 38.504 | 61.316 | 6.441 | 1.00 | 40.77 | O |
| ATOM | 1254 | CB | ILE | B | 51 | 38.477 | 61.141 | 9.371 | 1.00 | 42.29 | C |
| ATOM | 1255 | CG1 | ILE | B | 51 | 37.116 | 61.801 | 9.584 | 1.00 | 42.59 | C |
| ATOM | 1256 | CG2 | ILE | B | 51 | 39.148 | 60.807 | 10.695 | 1.00 | 42.29 | C |
| ATOM | 1257 | CD1 | ILE | B | 51 | 36.040 | 60.839 | 10.067 | 1.00 | 44.12 | C |
| ATOM | 1258 | N | LYS | B | 52 | 38.536 | 63.542 | 6.804 | 1.00 | 40.51 | N |
| ATOM | 1259 | CA | LYS | B | 52 | 37.975 | 63.871 | 5.496 | 1.00 | 39.40 | C |
| ATOM | 1260 | C | LYS | B | 52 | 39.143 | 63.807 | 4.521 | 1.00 | 38.70 | C |
| ATOM | 1261 | O | LYS | B | 52 | 40.060 | 64.632 | 4.582 | 1.00 | 39.00 | O |
| ATOM | 1262 | CB | LYS | B | 52 | 37.360 | 65.276 | 5.492 | 1.00 | 38.94 | C |
| ATOM | 1263 | N | LEU | B | 53 | 39.107 | 62.824 | 3.622 | 1.00 | 36.69 | N |
| ATOM | 1264 | CA | LEU | B | 53 | 40.179 | 62.627 | 2.657 | 1.00 | 34.75 | C |
| ATOM | 1265 | C | LEU | B | 53 | 39.783 | 62.879 | 1.209 | 1.00 | 34.22 | C |
| ATOM | 1266 | O | LEU | B | 53 | 38.610 | 62.835 | 0.852 | 1.00 | 36.06 | O |
| ATOM | 1267 | CB | LEU | B | 53 | 40.710 | 61.203 | 2.775 | 1.00 | 34.22 | C |
| ATOM | 1268 | CG | LEU | B | 53 | 41.174 | 60.750 | 4.153 | 1.00 | 33.71 | C |
| ATOM | 1269 | CD1 | LEU | B | 53 | 41.431 | 59.259 | 4.133 | 1.00 | 33.62 | C |
| ATOM | 1270 | CD2 | LEU | B | 53 | 42.430 | 61.507 | 4.533 | 1.00 | 34.34 | C |
| ATOM | 1271 | N | GLN | B | 54 | 40.778 | 63.127 | 0.370 | 1.00 | 32.84 | N |
| ATOM | 1272 | CA | GLN | B | 54 | 40.533 | 63.363 | −1.044 | 1.00 | 31.93 | C |
| ATOM | 1273 | C | GLN | B | 54 | 41.373 | 62.404 | −1.865 | 1.00 | 31.30 | C |
| ATOM | 1274 | O | GLN | B | 54 | 42.598 | 62.530 | −1.886 | 1.00 | 30.03 | O |
| ATOM | 1275 | CB | GLN | B | 54 | 40.916 | 64.793 | −1.439 | 1.00 | 32.97 | C |
| ATOM | 1276 | CG | GLN | B | 54 | 40.549 | 65.155 | −2.877 | 1.00 | 33.02 | C |
| ATOM | 1277 | CD | GLN | B | 54 | 39.042 | 65.222 | −3.080 | 1.00 | 34.77 | C |
| ATOM | 1278 | OE1 | GLN | B | 54 | 38.352 | 66.036 | −2.455 | 1.00 | 35.07 | O |
| ATOM | 1279 | NE2 | GLN | B | 54 | 38.522 | 64.362 | −3.946 | 1.00 | 34.98 | N |
| ATOM | 1280 | N | LEU | B | 55 | 40.729 | 61.446 | −2.533 | 1.00 | 30.73 | N |
| ATOM | 1281 | CA | LEU | B | 55 | 41.475 | 60.498 | −3.375 | 1.00 | 31.57 | C |
| ATOM | 1282 | C | LEU | B | 55 | 41.591 | 61.069 | −4.786 | 1.00 | 30.56 | C |
| ATOM | 1283 | O | LEU | B | 55 | 40.724 | 61.818 | −5.234 | 1.00 | 30.71 | O |
| ATOM | 1284 | CB | LEU | B | 55 | 40.783 | 59.127 | −3.430 | 1.00 | 32.23 | C |
| ATOM | 1285 | CG | LEU | B | 55 | 40.429 | 58.411 | −2.113 | 1.00 | 35.23 | C |
| ATOM | 1286 | CD1 | LEU | B | 55 | 40.135 | 56.946 | −2.398 | 1.00 | 34.62 | C |
| ATOM | 1287 | CD2 | LEU | B | 55 | 41.576 | 58.513 | −1.118 | 1.00 | 34.97 | C |
| ATOM | 1288 | N | GLN | B | 56 | 42.666 | 60.721 | −5.482 | 1.00 | 30.02 | N |
| ATOM | 1289 | CA | GLN | B | 56 | 42.886 | 61.211 | −6.837 | 1.00 | 29.32 | C |
| ATOM | 1290 | C | GLN | B | 56 | 43.742 | 60.202 | −7.575 | 1.00 | 29.63 | C |
| ATOM | 1291 | O | GLN | B | 56 | 44.809 | 59.829 | −7.094 | 1.00 | 29.46 | O |
| ATOM | 1292 | CB | GLN | B | 56 | 43.597 | 62.579 | −6.789 | 1.00 | 29.41 | C |
| ATOM | 1293 | CG | GLN | B | 56 | 43.917 | 63.203 | −8.146 | 1.00 | 29.62 | C |
| ATOM | 1294 | CD | GLN | B | 56 | 42.684 | 63.475 | −8.982 | 1.00 | 28.94 | C |
| ATOM | 1295 | OE1 | GLN | B | 56 | 41.830 | 64.275 | −8.611 | 1.00 | 29.99 | O |
| ATOM | 1296 | NE2 | GLN | B | 56 | 42.583 | 62.799 | −10.122 | 1.00 | 30.33 | N |
| ATOM | 1297 | N | ALA | B | 57 | 43.272 | 59.749 | −8.733 | 1.00 | 29.97 | N |
| ATOM | 1298 | CA | ALA | B | 57 | 44.016 | 58.779 | −9.534 | 1.00 | 30.63 | C |
| ATOM | 1299 | C | ALA | B | 57 | 45.177 | 59.458 | −10.267 | 1.00 | 31.45 | C |
| ATOM | 1300 | O | ALA | B | 57 | 45.013 | 60.545 | −10.821 | 1.00 | 31.11 | O |
| ATOM | 1301 | CB | ALA | B | 57 | 43.082 | 58.116 | −10.545 | 1.00 | 29.39 | C |
| ATOM | 1302 | N | GLU | B | 58 | 46.342 | 58.816 | −10.262 | 1.00 | 32.00 | N |
| ATOM | 1303 | CA | GLU | B | 58 | 47.521 | 59.361 | −10.935 | 1.00 | 32.70 | C |
| ATOM | 1304 | C | GLU | B | 58 | 47.660 | 58.627 | −12.267 | 1.00 | 33.16 | C |
| ATOM | 1305 | O | GLU | B | 58 | 48.173 | 59.169 | −13.249 | 1.00 | 32.46 | O |
| ATOM | 1306 | CB | GLU | B | 58 | 48.769 | 59.141 | −10.075 | 1.00 | 34.03 | C |
| ATOM | 1307 | CG | GLU | B | 58 | 49.957 | 60.027 | −10.445 | 1.00 | 35.07 | C |
| ATOM | 1308 | CD | GLU | B | 58 | 49.636 | 61.517 | −10.331 | 1.00 | 36.28 | C |
| ATOM | 1309 | OE1 | GLU | B | 58 | 48.984 | 61.930 | −9.346 | 1.00 | 36.31 | O |
| ATOM | 1310 | OE2 | GLU | B | 58 | 50.041 | 62.280 | −11.231 | 1.00 | 38.59 | O |
| ATOM | 1311 | N | GLU | B | 59 | 47.221 | 57.372 | −12.264 | 1.00 | 33.20 | N |
| ATOM | 1312 | CA | GLU | B | 59 | 47.200 | 56.526 | −13.450 | 1.00 | 34.42 | C |
| ATOM | 1313 | C | GLU | B | 59 | 46.210 | 55.405 | −13.136 | 1.00 | 33.04 | C |
| ATOM | 1314 | O | GLU | B | 59 | 45.739 | 55.293 | −12.004 | 1.00 | 32.98 | O |
| ATOM | 1315 | CB | GLU | B | 59 | 48.591 | 55.983 | −13.806 | 1.00 | 36.51 | C |
| ATOM | 1316 | CG | GLU | B | 59 | 49.109 | 54.811 | −12.999 | 1.00 | 40.45 | C |
| ATOM | 1317 | CD | GLU | B | 59 | 50.435 | 54.299 | −13.555 | 1.00 | 42.69 | C |
| ATOM | 1318 | OE1 | GLU | B | 59 | 51.397 | 55.097 | −13.619 | 1.00 | 44.62 | O |
| ATOM | 1319 | OE2 | GLU | B | 59 | 50.519 | 53.112 | −13.939 | 1.00 | 43.75 | O |
| ATOM | 1320 | N | ARG | B | 60 | 45.878 | 54.599 | −14.133 | 1.00 | 32.15 | N |
| ATOM | 1321 | CA | ARG | B | 60 | 44.906 | 53.534 | −13.955 | 1.00 | 32.04 | C |
| ATOM | 1322 | C | ARG | B | 60 | 45.142 | 52.685 | −12.703 | 1.00 | 30.69 | C |
| ATOM | 1323 | O | ARG | B | 60 | 46.201 | 52.078 | −12.546 | 1.00 | 30.48 | O |
| ATOM | 1324 | CB | ARG | B | 60 | 44.896 | 52.664 | −15.217 | 1.00 | 33.28 | C |
| ATOM | 1325 | CG | ARG | B | 60 | 43.791 | 51.648 | −15.275 | 1.00 | 35.74 | C |
| ATOM | 1326 | CD | ARG | B | 60 | 43.852 | 50.864 | −16.568 | 1.00 | 37.31 | C |
| ATOM | 1327 | NE | ARG | B | 60 | 43.209 | 49.579 | −16.370 | 1.00 | 41.07 | N |

TABLE 3-continued

| | | | | FGFR2(D2–D3) Complexed with FGF2 | | | | | | |
|---|---|---|---|---|---|---|---|---|---|---|
| ATOM | 1328 | CZ | ARG | B | 60 | 43.776 | 48.408 | −16.628 | 1.00 | 42.59 | C |
| ATOM | 1329 | NH1 | ARG | B | 60 | 45.010 | 48.349 | −17.113 | 1.00 | 42.37 | N |
| ATOM | 1330 | NH2 | ARG | B | 60 | 43.113 | 47.292 | −16.359 | 1.00 | 44.09 | N |
| ATOM | 1331 | N | GLY | B | 61 | 44.160 | 52.670 | −11.802 | 1.00 | 29.44 | N |
| ATOM | 1332 | CA | GLY | B | 61 | 44.270 | 51.867 | −10.594 | 1.00 | 28.64 | C |
| ATOM | 1333 | C | GLY | B | 61 | 45.239 | 52.336 | −9.518 | 1.00 | 28.44 | C |
| ATOM | 1334 | O | GLY | B | 61 | 45.447 | 51.631 | −8.518 | 1.00 | 28.45 | O |
| ATOM | 1335 | N | VAL | B | 62 | 45.837 | 53.510 | −9.705 | 1.00 | 27.68 | N |
| ATOM | 1336 | CA | VAL | B | 62 | 46.772 | 54.041 | −8.716 | 1.00 | 27.03 | C |
| ATOM | 1337 | C | VAL | B | 62 | 46.289 | 55.398 | −8.188 | 1.00 | 26.84 | C |
| ATOM | 1338 | O | VAL | B | 62 | 45.970 | 56.298 | −8.961 | 1.00 | 27.29 | O |
| ATOM | 1339 | CB | VAL | B | 62 | 48.183 | 54.198 | −9.320 | 1.00 | 27.60 | C |
| ATOM | 1340 | CG1 | VAL | B | 62 | 49.179 | 54.609 | −8.220 | 1.00 | 27.44 | C |
| ATOM | 1341 | CG2 | VAL | B | 62 | 48.617 | 52.884 | −9.993 | 1.00 | 27.44 | C |
| ATOM | 1342 | N | VAL | B | 63 | 46.244 | 55.555 | −6.870 | 1.00 | 26.76 | N |
| ATOM | 1343 | CA | VAL | B | 63 | 45.775 | 56.816 | −6.296 | 1.00 | 26.49 | C |
| ATOM | 1344 | C | VAL | B | 63 | 46.693 | 57.419 | −5.240 | 1.00 | 27.04 | C |
| ATOM | 1345 | O | VAL | B | 63 | 47.592 | 56.750 | −4.717 | 1.00 | 26.79 | O |
| ATOM | 1346 | CB | VAL | B | 63 | 44.386 | 56.666 | −5.614 | 1.00 | 25.62 | C |
| ATOM | 1347 | CG1 | VAL | B | 63 | 43.406 | 55.941 | −6.535 | 1.00 | 25.75 | C |
| ATOM | 1348 | CG2 | VAL | B | 63 | 44.540 | 55.920 | −4.290 | 1.00 | 24.62 | C |
| ATOM | 1349 | N | SER | B | 64 | 46.444 | 58.693 | −4.942 | 1.00 | 26.91 | N |
| ATOM | 1350 | CA | SER | B | 64 | 47.163 | 59.413 | −3.896 | 1.00 | 27.65 | C |
| ATOM | 1351 | C | SER | B | 64 | 46.028 | 59.740 | −2.922 | 1.00 | 27.63 | C |
| ATOM | 1352 | O | SER | B | 64 | 44.887 | 59.936 | −3.341 | 1.00 | 27.72 | O |
| ATOM | 1353 | CB | SER | B | 64 | 47.819 | 60.706 | −4.431 | 1.00 | 27.51 | C |
| ATOM | 1354 | OG | SER | B | 64 | 46.879 | 61.733 | −4.711 | 1.00 | 26.28 | O |
| ATOM | 1355 | N | ILE | B | 65 | 46.328 | 59.758 | −1.631 | 1.00 | 27.50 | N |
| ATOM | 1356 | CA | ILE | B | 65 | 45.324 | 60.045 | −0.613 | 1.00 | 29.11 | C |
| ATOM | 1357 | C | ILE | B | 65 | 45.742 | 61.299 | 0.182 | 1.00 | 30.87 | C |
| ATOM | 1358 | O | ILE | B | 65 | 46.764 | 61.293 | 0.872 | 1.00 | 29.58 | O |
| ATOM | 1359 | CB | ILE | B | 65 | 45.186 | 58.844 | 0.348 | 1.00 | 28.40 | C |
| ATOM | 1360 | CG1 | ILE | B | 65 | 44.783 | 57.594 | −0.436 | 1.00 | 28.74 | C |
| ATOM | 1361 | CG2 | ILE | B | 65 | 44.151 | 59.146 | 1.414 | 1.00 | 29.28 | C |
| ATOM | 1362 | CD1 | ILE | B | 65 | 44.989 | 56.288 | 0.328 | 1.00 | 29.28 | C |
| ATOM | 1363 | N | LYS | B | 66 | 44.942 | 62.359 | 0.096 | 1.00 | 32.12 | N |
| ATOM | 1364 | CA | LYS | B | 66 | 45.261 | 63.615 | 0.764 | 1.00 | 34.36 | C |
| ATOM | 1365 | C | LYS | B | 66 | 44.308 | 64.046 | 1.881 | 1.00 | 35.58 | C |
| ATOM | 1366 | O | LYS | B | 66 | 43.091 | 64.094 | 1.693 | 1.00 | 35.20 | O |
| ATOM | 1367 | CB | LYS | B | 66 | 45.346 | 64.742 | −0.285 | 1.00 | 35.36 | C |
| ATOM | 1368 | CG | LYS | B | 66 | 45.677 | 66.133 | 0.280 | 1.00 | 35.59 | C |
| ATOM | 1369 | CD | LYS | B | 66 | 45.638 | 67.209 | −0.796 | 1.00 | 36.13 | C |
| ATOM | 1370 | CE | LYS | B | 66 | 46.129 | 68.554 | −0.264 | 1.00 | 38.60 | C |
| ATOM | 1371 | NZ | LYS | B | 66 | 46.176 | 69.640 | −1.304 | 1.00 | 37.62 | N |
| ATOM | 1372 | N | GLY | B | 67 | 44.871 | 64.365 | 3.046 | 1.00 | 37.05 | N |
| ATOM | 1373 | CA | GLY | B | 67 | 44.056 | 64.837 | 4.155 | 1.00 | 38.88 | C |
| ATOM | 1374 | C | GLY | B | 67 | 43.676 | 66.283 | 3.856 | 1.00 | 40.81 | C |
| ATOM | 1375 | O | GLY | B | 67 | 44.544 | 67.157 | 3.780 | 1.00 | 40.56 | O |
| ATOM | 1376 | N | VAL | B | 68 | 42.387 | 66.542 | 3.667 | 1.00 | 41.60 | N |
| ATOM | 1377 | CA | VAL | B | 68 | 41.929 | 67.886 | 3.343 | 1.00 | 43.50 | C |
| ATOM | 1378 | C | VAL | B | 68 | 42.352 | 68.934 | 4.371 | 1.00 | 44.85 | C |
| ATOM | 1379 | O | VAL | B | 68 | 42.928 | 69.957 | 4.000 | 1.00 | 45.14 | O |
| ATOM | 1380 | CB | VAL | B | 68 | 40.391 | 67.930 | 3.175 | 1.00 | 44.16 | C |
| ATOM | 1381 | CG1 | VAL | B | 68 | 39.946 | 69.329 | 2.778 | 1.00 | 44.07 | C |
| ATOM | 1382 | CG2 | VAL | B | 68 | 39.958 | 66.927 | 2.101 | 1.00 | 45.02 | C |
| ATOM | 1383 | N | SER | B | 69 | 42.080 | 68.683 | 5.651 | 1.00 | 45.53 | N |
| ATOM | 1384 | CA | SER | B | 69 | 42.448 | 69.632 | 6.709 | 1.00 | 46.56 | C |
| ATOM | 1385 | C | SER | B | 69 | 43.952 | 69.817 | 6.842 | 1.00 | 46.50 | C |
| ATOM | 1386 | O | SER | B | 69 | 44.451 | 70.938 | 6.752 | 1.00 | 46.70 | O |
| ATOM | 1387 | CB | SER | B | 69 | 41.880 | 69.193 | 8.062 | 1.00 | 47.39 | C |
| ATOM | 1388 | OG | SER | B | 69 | 40.546 | 69.648 | 8.225 | 1.00 | 48.53 | O |
| ATOM | 1389 | N | ALA | B | 70 | 44.668 | 68.717 | 7.059 | 1.00 | 46.13 | N |
| ATOM | 1390 | CA | ALA | B | 70 | 46.116 | 68.768 | 7.212 | 1.00 | 46.16 | C |
| ATOM | 1391 | C | ALA | B | 70 | 46.831 | 69.248 | 5.946 | 1.00 | 46.37 | C |
| ATOM | 1392 | O | ALA | B | 70 | 47.985 | 69.674 | 6.004 | 1.00 | 46.38 | O |
| ATOM | 1393 | CB | ALA | B | 70 | 46.641 | 67.397 | 7.612 | 1.00 | 45.59 | C |
| ATOM | 1394 | N | ASN | B | 71 | 46.141 | 69.181 | 4.810 | 1.00 | 46.18 | N |
| ATOM | 1395 | CA | ASN | B | 71 | 46.716 | 69.580 | 3.530 | 1.00 | 46.20 | C |
| ATOM | 1396 | C | ASN | B | 71 | 48.020 | 68.816 | 3.275 | 1.00 | 45.29 | C |
| ATOM | 1397 | O | ASN | B | 71 | 48.998 | 69.373 | 2.780 | 1.00 | 44.85 | O |
| ATOM | 1398 | CB | ASN | B | 71 | 46.967 | 71.094 | 3.501 | 1.00 | 47.58 | C |
| ATOM | 1399 | CG | ASN | B | 71 | 47.420 | 71.591 | 2.129 | 1.00 | 49.28 | C |
| ATOM | 1400 | OD1 | ASN | B | 71 | 46.896 | 71.171 | 1.090 | 1.00 | 50.06 | O |
| ATOM | 1401 | ND2 | ASN | B | 71 | 48.388 | 72.504 | 2.123 | 1.00 | 49.96 | N |
| ATOM | 1402 | N | ARG | B | 72 | 48.012 | 67.531 | 3.618 | 1.00 | 44.62 | N |
| ATOM | 1403 | CA | ARG | B | 72 | 49.169 | 66.654 | 3.443 | 1.00 | 43.83 | C |
| ATOM | 1404 | C | ARG | B | 72 | 48.766 | 65.366 | 2.719 | 1.00 | 43.20 | C |

TABLE 3-continued

FGFR2(D2–D3) Complexed with FGF2

| | | | | | | | | | | | |
|---|---|---|---|---|---|---|---|---|---|---|---|
| ATOM | 1405 | O | ARG | B | 72 | 47.586 | 65.001 | 2.702 | 1.00 | 42.97 | O |
| ATOM | 1406 | CB | ARG | B | 72 | 49.764 | 66.296 | 4.805 | 1.00 | 44.52 | C |
| ATOM | 1407 | CG | ARG | B | 72 | 50.427 | 67.453 | 5.555 | 1.00 | 45.96 | C |
| ATOM | 1408 | CD | ARG | B | 72 | 50.762 | 67.031 | 6.984 | 1.00 | 47.04 | C |
| ATOM | 1409 | NE | ARG | B | 72 | 51.594 | 68.003 | 7.687 | 1.00 | 47.76 | N |
| ATOM | 1410 | CZ | ARG | B | 72 | 52.921 | 68.062 | 7.593 | 1.00 | 48.23 | C |
| ATOM | 1411 | NH1 | ARG | B | 72 | 53.575 | 67.199 | 6.831 | 1.00 | 46.93 | N |
| ATOM | 1412 | NH2 | ARG | B | 72 | 53.593 | 68.996 | 8.256 | 1.00 | 48.72 | N |
| ATOM | 1413 | N | TYR | B | 73 | 49.752 | 64.681 | 2.134 | 1.00 | 41.62 | N |
| ATOM | 1414 | CA | TYR | B | 73 | 49.518 | 63.435 | 1.401 | 1.00 | 40.58 | C |
| ATOM | 1415 | C | TYR | B | 73 | 50.020 | 62.208 | 2.156 | 1.00 | 39.99 | C |
| ATOM | 1416 | O | TYR | B | 73 | 51.160 | 62.185 | 2.633 | 1.00 | 39.66 | O |
| ATOM | 1417 | CB | TYR | B | 73 | 50.215 | 63.446 | 0.029 | 1.00 | 40.09 | C |
| ATOM | 1418 | CG | TYR | B | 73 | 49.784 | 64.535 | −0.919 | 1.00 | 40.53 | C |
| ATOM | 1419 | CD1 | TYR | B | 73 | 50.373 | 65.807 | −0.872 | 1.00 | 40.88 | C |
| ATOM | 1420 | CD2 | TYR | B | 73 | 48.781 | 64.304 | −1.863 | 1.00 | 40.46 | C |
| ATOM | 1421 | CE1 | TYR | B | 73 | 49.971 | 66.826 | −1.747 | 1.00 | 40.70 | C |
| ATOM | 1422 | CE2 | TYR | B | 73 | 48.368 | 65.313 | −2.739 | 1.00 | 40.89 | C |
| ATOM | 1423 | CZ | TYR | B | 73 | 48.966 | 66.573 | −2.673 | 1.00 | 40.86 | C |
| ATOM | 1424 | OH | TYR | B | 73 | 48.535 | 67.573 | −3.511 | 1.00 | 40.19 | O |
| ATOM | 1425 | N | LEU | B | 74 | 49.179 | 61.180 | 2.244 | 1.00 | 38.79 | N |
| ATOM | 1426 | CA | LEU | B | 74 | 49.558 | 59.939 | 2.919 | 1.00 | 37.94 | C |
| ATOM | 1427 | C | LEU | B | 74 | 50.758 | 59.334 | 2.211 | 1.00 | 38.53 | C |
| ATOM | 1428 | O | LEU | B | 74 | 50.857 | 59.391 | 0.985 | 1.00 | 38.81 | O |
| ATOM | 1429 | CB | LEU | B | 74 | 48.416 | 58.926 | 2.890 | 1.00 | 36.70 | C |
| ATOM | 1430 | CG | LEU | B | 74 | 48.709 | 57.584 | 3.569 | 1.00 | 36.84 | C |
| ATOM | 1431 | CD1 | LEU | B | 74 | 48.555 | 57.742 | 5.082 | 1.00 | 35.17 | C |
| ATOM | 1432 | CD2 | LEU | B | 74 | 47.747 | 56.508 | 3.052 | 1.00 | 35.08 | C |
| ATOM | 1433 | N | ALA | B | 75 | 51.668 | 58.748 | 2.981 | 1.00 | 39.29 | N |
| ATOM | 1434 | CA | ALA | B | 75 | 52.854 | 58.131 | 2.402 | 1.00 | 40.25 | C |
| ATOM | 1435 | C | ALA | B | 75 | 53.373 | 56.988 | 3.262 | 1.00 | 40.75 | C |
| ATOM | 1436 | O | ALA | B | 75 | 53.151 | 56.962 | 4.467 | 1.00 | 39.83 | O |
| ATOM | 1437 | CB | ALA | B | 75 | 53.948 | 59.180 | 2.223 | 1.00 | 40.32 | C |
| ATOM | 1438 | N | MET | B | 76 | 54.047 | 56.035 | 2.632 | 1.00 | 42.15 | N |
| ATOM | 1439 | CA | MET | B | 76 | 54.620 | 54.920 | 3.365 | 1.00 | 44.74 | C |
| ATOM | 1440 | C | MET | B | 76 | 56.129 | 54.945 | 3.143 | 1.00 | 45.67 | C |
| ATOM | 1441 | O | MET | B | 76 | 56.600 | 54.917 | 2.000 | 1.00 | 44.81 | O |
| ATOM | 1442 | CB | MET | B | 76 | 54.050 | 53.580 | 2.898 | 1.00 | 45.53 | C |
| ATOM | 1443 | CG | MET | B | 76 | 54.433 | 52.434 | 3.831 | 1.00 | 47.11 | C |
| ATOM | 1444 | SD | MET | B | 76 | 54.068 | 50.811 | 3.162 | 1.00 | 50.36 | S |
| ATOM | 1445 | CE | MET | B | 76 | 52.275 | 50.720 | 3.489 | 1.00 | 49.90 | C |
| ATOM | 1446 | N | LYS | B | 77 | 56.873 | 55.014 | 4.246 | 1.00 | 47.14 | N |
| ATOM | 1447 | CA | LYS | B | 77 | 58.335 | 55.069 | 4.215 | 1.00 | 48.96 | C |
| ATOM | 1448 | C | LYS | B | 77 | 58.982 | 53.702 | 3.985 | 1.00 | 49.89 | C |
| ATOM | 1449 | O | LYS | B | 77 | 58.306 | 52.670 | 3.990 | 1.00 | 50.27 | O |
| ATOM | 1450 | CB | LYS | B | 77 | 58.856 | 55.684 | 5.520 | 1.00 | 48.58 | C |
| ATOM | 1451 | N | GLU | B | 78 | 60.295 | 53.707 | 3.783 | 1.00 | 51.15 | N |
| ATOM | 1452 | CA | GLU | B | 78 | 61.064 | 52.485 | 3.535 | 1.00 | 52.23 | C |
| ATOM | 1453 | C | GLU | B | 78 | 60.975 | 51.445 | 4.660 | 1.00 | 52.96 | C |
| ATOM | 1454 | O | GLU | B | 78 | 61.069 | 50.241 | 4.408 | 1.00 | 53.35 | O |
| ATOM | 1455 | CB | GLU | B | 78 | 62.536 | 52.844 | 3.295 | 1.00 | 52.49 | C |
| ATOM | 1456 | N | ASP | B | 79 | 60.806 | 51.903 | 5.897 | 1.00 | 53.48 | N |
| ATOM | 1457 | CA | ASP | B | 79 | 60.717 | 50.981 | 7.029 | 1.00 | 54.58 | C |
| ATOM | 1458 | C | ASP | B | 79 | 59.285 | 50.505 | 7.272 | 1.00 | 54.22 | C |
| ATOM | 1459 | O | ASP | B | 79 | 59.021 | 49.776 | 8.231 | 1.00 | 54.69 | O |
| ATOM | 1460 | CB | ASP | B | 79 | 61.269 | 51.638 | 8.302 | 1.00 | 55.62 | C |
| ATOM | 1461 | CG | ASP | B | 79 | 60.462 | 52.847 | 8.735 | 1.00 | 57.57 | C |
| ATOM | 1462 | OD1 | ASP | B | 79 | 60.791 | 53.445 | 9.785 | 1.00 | 58.50 | O |
| ATOM | 1463 | OD2 | ASP | B | 79 | 59.496 | 53.204 | 8.025 | 1.00 | 58.63 | O |
| ATOM | 1464 | N | GLY | B | 80 | 58.365 | 50.926 | 6.407 | 1.00 | 53.35 | N |
| ATOM | 1465 | CA | GLY | B | 80 | 56.975 | 50.522 | 6.542 | 1.00 | 52.30 | C |
| ATOM | 1466 | C | GLY | B | 80 | 56.125 | 51.410 | 7.433 | 1.00 | 51.35 | C |
| ATOM | 1467 | O | GLY | B | 80 | 55.015 | 51.036 | 7.795 | 1.00 | 51.92 | O |
| ATOM | 1468 | N | ARG | B | 81 | 56.635 | 52.583 | 7.788 | 1.00 | 50.11 | N |
| ATOM | 1469 | CA | ARG | B | 81 | 55.894 | 53.499 | 8.643 | 1.00 | 49.78 | C |
| ATOM | 1470 | C | ARG | B | 81 | 55.002 | 54.422 | 7.814 | 1.00 | 49.47 | C |
| ATOM | 1471 | O | ARG | B | 81 | 55.314 | 54.743 | 6.668 | 1.00 | 48.44 | O |
| ATOM | 1472 | CB | ARG | B | 81 | 56.866 | 54.342 | 9.482 | 1.00 | 49.85 | C |
| ATOM | 1473 | N | LEU | B | 82 | 53.891 | 54.854 | 8.392 | 1.00 | 49.08 | N |
| ATOM | 1474 | CA | LEU | B | 82 | 52.994 | 55.743 | 7.672 | 1.00 | 49.61 | C |
| ATOM | 1475 | C | LEU | B | 82 | 53.087 | 57.170 | 8.192 | 1.00 | 50.01 | C |
| ATOM | 1476 | O | LEU | B | 82 | 53.215 | 57.399 | 9.398 | 1.00 | 50.52 | O |
| ATOM | 1477 | CB | LEU | B | 82 | 51.547 | 55.258 | 7.774 | 1.00 | 48.91 | C |
| ATOM | 1478 | CG | LEU | B | 82 | 51.205 | 53.963 | 7.044 | 1.00 | 48.88 | C |
| ATOM | 1479 | CD1 | LEU | B | 82 | 49.688 | 53.840 | 6.948 | 1.00 | 49.36 | C |
| ATOM | 1480 | CD2 | LEU | B | 82 | 51.808 | 53.975 | 5.646 | 1.00 | 48.79 | C |
| ATOM | 1481 | N | LEU | B | 83 | 53.017 | 58.126 | 7.271 | 1.00 | 50.25 | N |

TABLE 3-continued

FGFR2(D2–D3) Complexed with FGF2

| ATOM | 1482 | CA | LEU | B | 83 | 53.084 | 59.541 | 7.615 | 1.00 | 50.82 | C |
|---|---|---|---|---|---|---|---|---|---|---|---|
| ATOM | 1483 | C | LEU | B | 83 | 52.456 | 60.346 | 6.474 | 1.00 | 50.21 | C |
| ATOM | 1484 | O | LEU | B | 83 | 52.188 | 59.796 | 5.408 | 1.00 | 50.58 | O |
| ATOM | 1485 | CB | LEU | B | 83 | 54.550 | 59.951 | 7.833 | 1.00 | 51.37 | C |
| ATOM | 1486 | CG | LEU | B | 83 | 55.481 | 59.846 | 6.619 | 1.00 | 52.48 | C |
| ATOM | 1487 | CD1 | LEU | B | 83 | 55.549 | 61.204 | 5.932 | 1.00 | 52.74 | C |
| ATOM | 1488 | CD2 | LEU | B | 83 | 56.876 | 59.411 | 7.049 | 1.00 | 53.20 | C |
| ATOM | 1489 | N | ALA | B | 84 | 52.212 | 61.635 | 6.703 | 1.00 | 49.99 | N |
| ATOM | 1490 | CA | ALA | B | 84 | 51.611 | 62.510 | 5.695 | 1.00 | 49.47 | C |
| ATOM | 1491 | C | ALA | B | 84 | 52.570 | 63.645 | 5.311 | 1.00 | 49.53 | C |
| ATOM | 1492 | O | ALA | B | 84 | 52.959 | 64.458 | 6.154 | 1.00 | 49.13 | O |
| ATOM | 1493 | CB | ALA | B | 84 | 50.308 | 63.083 | 6.224 | 1.00 | 49.30 | C |
| ATOM | 1494 | N | SER | B | 85 | 52.922 | 63.699 | 4.029 | 1.00 | 49.19 | N |
| ATOM | 1495 | CA | SER | B | 85 | 53.857 | 64.686 | 3.496 | 1.00 | 48.95 | C |
| ATOM | 1496 | C | SER | B | 85 | 53.234 | 65.961 | 2.929 | 1.00 | 48.92 | C |
| ATOM | 1497 | O | SER | B | 85 | 52.156 | 65.931 | 2.329 | 1.00 | 48.79 | O |
| ATOM | 1498 | CB | SER | B | 85 | 54.712 | 64.025 | 2.411 | 1.00 | 48.86 | C |
| ATOM | 1499 | OG | SER | B | 85 | 55.596 | 64.959 | 1.822 | 1.00 | 50.02 | O |
| ATOM | 1500 | N | LYS | B | 86 | 53.932 | 67.080 | 3.112 | 1.00 | 48.52 | N |
| ATOM | 1501 | CA | LYS | B | 86 | 53.471 | 68.368 | 2.604 | 1.00 | 48.28 | C |
| ATOM | 1502 | C | LYS | B | 86 | 53.483 | 68.336 | 1.083 | 1.00 | 47.46 | C |
| ATOM | 1503 | O | LYS | B | 86 | 52.561 | 68.836 | 0.429 | 1.00 | 47.12 | O |
| ATOM | 1504 | CB | LYS | B | 86 | 54.379 | 69.500 | 3.100 | 1.00 | 48.99 | C |
| ATOM | 1505 | N | SER | B | 87 | 54.528 | 67.747 | 0.517 | 1.00 | 46.34 | N |
| ATOM | 1506 | CA | SER | B | 87 | 54.618 | 67.660 | −0.929 | 1.00 | 46.63 | C |
| ATOM | 1507 | C | SER | B | 87 | 54.620 | 66.203 | −1.394 | 1.00 | 46.03 | C |
| ATOM | 1508 | O | SER | B | 87 | 55.100 | 65.309 | −0.697 | 1.00 | 46.08 | O |
| ATOM | 1509 | CB | SER | B | 87 | 55.862 | 68.409 | −1.446 | 1.00 | 47.20 | C |
| ATOM | 1510 | OG | SER | B | 87 | 57.069 | 67.802 | −1.015 | 1.00 | 47.87 | O |
| ATOM | 1511 | N | VAL | B | 88 | 54.071 | 65.986 | −2.585 | 1.00 | 45.84 | N |
| ATOM | 1512 | CA | VAL | B | 88 | 53.952 | 64.665 | −3.201 | 1.00 | 45.45 | C |
| ATOM | 1513 | C | VAL | B | 88 | 55.286 | 64.018 | −3.580 | 1.00 | 45.49 | C |
| ATOM | 1514 | O | VAL | B | 88 | 56.091 | 64.630 | −4.273 | 1.00 | 45.70 | O |
| ATOM | 1515 | CB | VAL | B | 88 | 53.097 | 64.753 | −4.495 | 1.00 | 45.62 | C |
| ATOM | 1516 | CG1 | VAL | B | 88 | 52.836 | 63.359 | −5.058 | 1.00 | 45.86 | C |
| ATOM | 1517 | CG2 | VAL | B | 88 | 51.796 | 65.483 | −4.214 | 1.00 | 45.53 | C |
| ATOM | 1518 | N | THR | B | 89 | 55.501 | 62.780 | −3.137 | 1.00 | 45.33 | N |
| ATOM | 1519 | CA | THR | B | 89 | 56.715 | 62.021 | −3.458 | 1.00 | 45.47 | C |
| ATOM | 1520 | C | THR | B | 89 | 56.293 | 60.648 | −3.994 | 1.00 | 45.02 | C |
| ATOM | 1521 | O | THR | B | 89 | 55.106 | 60.327 | −3.991 | 1.00 | 44.61 | O |
| ATOM | 1522 | CB | THR | B | 89 | 57.620 | 61.829 | −2.213 | 1.00 | 46.28 | C |
| ATOM | 1523 | OG1 | THR | B | 89 | 58.562 | 60.779 | −2.465 | 1.00 | 47.25 | O |
| ATOM | 1524 | CG2 | THR | B | 89 | 56.803 | 61.474 | −0.988 | 1.00 | 46.77 | C |
| ATOM | 1525 | N | ASP | B | 90 | 57.242 | 59.835 | −4.452 | 1.00 | 44.68 | N |
| ATOM | 1526 | CA | ASP | B | 90 | 56.878 | 58.529 | −4.992 | 1.00 | 45.02 | C |
| ATOM | 1527 | C | ASP | B | 90 | 56.392 | 57.533 | −3.932 | 1.00 | 44.14 | C |
| ATOM | 1528 | O | ASP | B | 90 | 56.014 | 56.408 | −4.260 | 1.00 | 44.94 | O |
| ATOM | 1529 | CB | ASP | B | 90 | 58.035 | 57.939 | −5.807 | 1.00 | 47.23 | C |
| ATOM | 1530 | CG | ASP | B | 90 | 59.237 | 57.589 | −4.952 | 1.00 | 49.81 | C |
| ATOM | 1531 | OD1 | ASP | B | 90 | 59.609 | 58.415 | −4.089 | 1.00 | 51.02 | O |
| ATOM | 1532 | OD2 | ASP | B | 90 | 59.818 | 56.494 | −5.150 | 1.00 | 51.45 | O |
| ATOM | 1533 | N | GLU | B | 91 | 56.387 | 57.950 | −2.671 | 1.00 | 42.82 | N |
| ATOM | 1534 | CA | GLU | B | 91 | 55.921 | 57.098 | −1.582 | 1.00 | 41.44 | C |
| ATOM | 1535 | C | GLU | B | 91 | 54.472 | 57.465 | −1.236 | 1.00 | 40.27 | C |
| ATOM | 1536 | O | GLU | B | 91 | 53.924 | 57.007 | −0.233 | 1.00 | 39.81 | O |
| ATOM | 1537 | CB | GLU | B | 91 | 56.812 | 57.292 | −0.345 | 1.00 | 41.01 | C |
| ATOM | 1538 | N | CYS | B | 92 | 53.860 | 58.288 | −2.083 | 1.00 | 39.09 | N |
| ATOM | 1539 | CA | CYS | B | 92 | 52.494 | 58.751 | −1.868 | 1.00 | 39.00 | C |
| ATOM | 1540 | C | CYS | B | 92 | 51.448 | 58.126 | −2.801 | 1.00 | 37.89 | C |
| ATOM | 1541 | O | CYS | B | 92 | 50.296 | 58.568 | −2.821 | 1.00 | 38.22 | O |
| ATOM | 1542 | CB | CYS | B | 92 | 52.460 | 60.278 | −2.013 | 1.00 | 38.86 | C |
| ATOM | 1543 | SG | CYS | B | 92 | 53.558 | 61.163 | −0.844 | 1.00 | 40.00 | S |
| ATOM | 1544 | N | PHE | B | 93 | 51.846 | 57.110 | −3.561 | 1.00 | 36.66 | N |
| ATOM | 1545 | CA | PHE | B | 93 | 50.941 | 56.452 | −4.502 | 1.00 | 36.71 | C |
| ATOM | 1546 | C | PHE | B | 93 | 50.664 | 54.981 | −4.148 | 1.00 | 36.83 | C |
| ATOM | 1547 | O | PHE | B | 93 | 51.586 | 54.218 | −3.829 | 1.00 | 36.31 | O |
| ATOM | 1548 | CB | PHE | B | 93 | 51.502 | 56.566 | −5.917 | 1.00 | 37.11 | C |
| ATOM | 1549 | CG | PHE | B | 93 | 51.653 | 57.984 | −6.385 | 1.00 | 38.68 | C |
| ATOM | 1550 | CD1 | PHE | B | 93 | 50.530 | 58.777 | −6.598 | 1.00 | 38.20 | C |
| ATOM | 1551 | CD2 | PHE | B | 93 | 52.919 | 58.542 | −6.573 | 1.00 | 38.94 | C |
| ATOM | 1552 | CE1 | PHE | B | 93 | 50.657 | 60.111 | −6.990 | 1.00 | 40.31 | C |
| ATOM | 1553 | CE2 | PHE | B | 93 | 53.060 | 59.873 | −6.965 | 1.00 | 40.19 | C |
| ATOM | 1554 | CZ | PHE | B | 93 | 51.926 | 60.662 | −7.174 | 1.00 | 40.04 | C |
| ATOM | 1555 | N | PHE | B | 94 | 49.389 | 54.594 | −4.230 | 1.00 | 35.09 | N |
| ATOM | 1556 | CA | PHE | B | 94 | 48.963 | 53.246 | −3.873 | 1.00 | 33.74 | C |
| ATOM | 1557 | C | PHE | B | 94 | 47.995 | 52.597 | −4.863 | 1.00 | 33.15 | C |
| ATOM | 1558 | O | PHE | B | 94 | 47.080 | 53.244 | −5.375 | 1.00 | 33.22 | O |

TABLE 3-continued

FGFR2(D2–D3) Complexed with FGF2

| ATOM | 1559 | CB | PHE | B | 94 | 48.271 | 53.275 | −2.508 | 1.00 | 34.11 | C |
|---|---|---|---|---|---|---|---|---|---|---|---|
| ATOM | 1560 | CG | PHE | B | 94 | 49.053 | 53.979 | −1.435 | 1.00 | 34.05 | C |
| ATOM | 1561 | CD1 | PHE | B | 94 | 49.905 | 53.268 | −0.596 | 1.00 | 33.30 | C |
| ATOM | 1562 | CD2 | PHE | B | 94 | 48.946 | 55.361 | −1.271 | 1.00 | 33.73 | C |
| ATOM | 1563 | CE1 | PHE | B | 94 | 50.645 | 53.924 | 0.395 | 1.00 | 33.49 | C |
| ATOM | 1564 | CE2 | PHE | B | 94 | 49.681 | 56.027 | −0.287 | 1.00 | 33.43 | C |
| ATOM | 1565 | CZ | PHE | B | 94 | 50.535 | 55.304 | 0.550 | 1.00 | 32.83 | C |
| ATOM | 1566 | N | PHE | B | 95 | 48.193 | 51.311 | −5.114 | 1.00 | 31.95 | N |
| ATOM | 1567 | CA | PHE | B | 95 | 47.290 | 50.575 | −5.992 | 1.00 | 31.76 | C |
| ATOM | 1568 | C | PHE | B | 95 | 45.979 | 50.411 | −5.241 | 1.00 | 30.17 | C |
| ATOM | 1569 | O | PHE | B | 95 | 45.963 | 49.892 | −4.134 | 1.00 | 29.41 | O |
| ATOM | 1570 | CB | PHE | B | 95 | 47.828 | 49.174 | −6.308 | 1.00 | 32.03 | C |
| ATOM | 1571 | CG | PHE | B | 95 | 48.937 | 49.158 | −7.303 | 1.00 | 33.35 | C |
| ATOM | 1572 | CD1 | PHE | B | 95 | 50.257 | 48.999 | −6.894 | 1.00 | 33.74 | C |
| ATOM | 1573 | CD2 | PHE | B | 95 | 48.666 | 49.293 | −8.656 | 1.00 | 33.65 | C |
| ATOM | 1574 | CE1 | PHE | B | 95 | 51.293 | 48.970 | −7.824 | 1.00 | 33.36 | C |
| ATOM | 1575 | CE2 | PHE | B | 95 | 49.696 | 49.267 | −9.591 | 1.00 | 34.75 | C |
| ATOM | 1576 | CZ | PHE | B | 95 | 51.014 | 49.103 | −9.172 | 1.00 | 33.46 | C |
| ATOM | 1577 | N | GLU | B | 96 | 44.886 | 50.870 | −5.829 | 1.00 | 30.27 | N |
| ATOM | 1578 | CA | GLU | B | 96 | 43.580 | 50.729 | −5.196 | 1.00 | 30.73 | C |
| ATOM | 1579 | C | GLU | B | 96 | 42.888 | 49.529 | −5.832 | 1.00 | 31.15 | C |
| ATOM | 1580 | O | GLU | B | 96 | 42.816 | 49.426 | −7.052 | 1.00 | 30.61 | O |
| ATOM | 1581 | CB | GLU | B | 96 | 42.725 | 51.989 | −5.401 | 1.00 | 28.79 | C |
| ATOM | 1582 | CG | GLU | B | 96 | 41.360 | 51.916 | −4.708 | 1.00 | 29.44 | C |
| ATOM | 1583 | CD | GLU | B | 96 | 40.476 | 53.138 | −4.981 | 1.00 | 29.62 | C |
| ATOM | 1584 | OE1 | GLU | B | 96 | 40.222 | 53.415 | −6.167 | 1.00 | 29.90 | O |
| ATOM | 1585 | OE2 | GLU | B | 96 | 40.039 | 53.816 | −4.016 | 1.00 | 28.37 | O |
| ATOM | 1586 | N | ARG | B | 97 | 42.380 | 48.634 | −4.996 | 1.00 | 32.72 | N |
| ATOM | 1587 | CA | ARG | B | 97 | 41.711 | 47.423 | −5.470 | 1.00 | 35.12 | C |
| ATOM | 1588 | C | ARG | B | 97 | 40.421 | 47.108 | −4.700 | 1.00 | 34.90 | C |
| ATOM | 1589 | O | ARG | B | 97 | 40.381 | 47.161 | −3.475 | 1.00 | 33.69 | O |
| ATOM | 1590 | CB | ARG | B | 97 | 42.672 | 46.229 | −5.336 | 1.00 | 37.75 | C |
| ATOM | 1591 | CG | ARG | B | 97 | 42.010 | 44.860 | −5.501 | 1.00 | 41.93 | C |
| ATOM | 1592 | CD | ARG | B | 97 | 41.947 | 44.440 | −6.962 | 1.00 | 44.56 | C |
| ATOM | 1593 | NE | ARG | B | 97 | 43.232 | 43.919 | −7.422 | 1.00 | 46.30 | N |
| ATOM | 1594 | CZ | ARG | B | 97 | 43.788 | 42.800 | −6.965 | 1.00 | 47.02 | C |
| ATOM | 1595 | NH1 | ARG | B | 97 | 43.173 | 42.080 | −6.032 | 1.00 | 46.95 | N |
| ATOM | 1596 | NH2 | ARG | B | 97 | 44.959 | 42.396 | −7.446 | 1.00 | 46.84 | N |
| ATOM | 1597 | N | LEU | B | 98 | 39.363 | 46.795 | −5.433 | 1.00 | 35.86 | N |
| ATOM | 1598 | CA | LEU | B | 98 | 38.097 | 46.407 | −4.823 | 1.00 | 35.99 | C |
| ATOM | 1599 | C | LEU | B | 98 | 38.170 | 44.881 | −4.716 | 1.00 | 35.59 | C |
| ATOM | 1600 | O | LEU | B | 98 | 38.142 | 44.190 | −5.729 | 1.00 | 36.32 | O |
| ATOM | 1601 | CE | LEU | B | 98 | 36.927 | 46.832 | −5.715 | 1.00 | 35.68 | C |
| ATOM | 1602 | CB | LEU | B | 98 | 35.532 | 46.361 | −5.272 | 1.00 | 36.69 | C |
| ATOM | 1603 | CD1 | LEU | B | 98 | 35.289 | 46.724 | −3.807 | 1.00 | 35.91 | C |
| ATOM | 1604 | CD2 | LEU | B | 98 | 34.474 | 46.998 | −6.161 | 1.00 | 35.80 | C |
| ATOM | 1605 | N | GLU | B | 99 | 38.294 | 44.363 | −3.501 | 1.00 | 36.08 | N |
| ATOM | 1606 | CA | GLU | B | 99 | 38.399 | 42.922 | −3.296 | 1.00 | 36.41 | C |
| ATOM | 1607 | C | GLU | B | 99 | 37.056 | 42.216 | −3.459 | 1.00 | 36.93 | C |
| ATOM | 1608 | O | GLU | B | 99 | 35.999 | 42.853 | −3.419 | 1.00 | 34.85 | O |
| ATOM | 1609 | CB | GLU | B | 99 | 38.985 | 42.640 | −1.909 | 1.00 | 36.69 | C |
| ATOM | 1610 | CG | GLU | B | 99 | 40.353 | 43.288 | −1.679 | 1.00 | 38.44 | C |
| ATOM | 1611 | CD | GLU | B | 99 | 41.396 | 42.871 | −2.711 | 1.00 | 38.96 | C |
| ATOM | 1612 | OE1 | GLU | B | 99 | 42.465 | 43.507 | −2.752 | 1.00 | 39.00 | O |
| ATOM | 1613 | OE2 | GLU | B | 99 | 41.158 | 41.912 | −3.478 | 1.00 | 39.79 | O |
| ATOM | 1614 | N | SER | B | 100 | 37.109 | 40.897 | −3.639 | 1.00 | 37.29 | N |
| ATOM | 1615 | CA | SER | B | 100 | 35.906 | 40.089 | −3.827 | 1.00 | 37.99 | C |
| ATOM | 1616 | C | SER | B | 100 | 34.949 | 40.199 | −2.642 | 1.00 | 37.08 | C |
| ATOM | 1617 | O | SER | B | 100 | 33.740 | 39.982 | −2.787 | 1.00 | 37.34 | O |
| ATOM | 1618 | CB | SER | B | 100 | 36.285 | 38.623 | −4.080 | 1.00 | 37.81 | C |
| ATOM | 1619 | OG | SER | B | 100 | 37.033 | 38.093 | −3.000 | 1.00 | 40.53 | O |
| ATOM | 1620 | N | ASN | B | 101 | 35.487 | 40.554 | −1.477 | 1.00 | 36.07 | N |
| ATOM | 1621 | CA | ASN | B | 101 | 34.680 | 40.717 | −0.269 | 1.00 | 34.55 | C |
| ATOM | 1622 | C | ASN | B | 101 | 33.980 | 42.084 | −0.230 | 1.00 | 33.39 | C |
| ATOM | 1623 | O | ASN | B | 101 | 33.245 | 42.387 | 0.713 | 1.00 | 33.54 | O |
| ATOM | 1624 | CB | ASN | B | 101 | 35.563 | 40.561 | 0.965 | 1.00 | 35.09 | C |
| ATOM | 1625 | CG | ASN | B | 101 | 36.845 | 41.385 | 0.877 | 1.00 | 37.41 | C |
| ATOM | 1626 | OD1 | ASN | B | 101 | 36.826 | 42.557 | 0.489 | 1.00 | 35.76 | O |
| ATOM | 1627 | ND2 | ASN | B | 101 | 37.970 | 40.772 | 1.255 | 1.00 | 38.82 | N |
| ATOM | 1628 | N | ASN | B | 102 | 34.215 | 42.893 | −1.261 | 1.00 | 31.93 | N |
| ATOM | 1629 | CA | ASN | B | 102 | 33.636 | 44.228 | −1.395 | 1.00 | 30.66 | C |
| ATOM | 1630 | C | ASN | B | 102 | 34.248 | 45.338 | −0.532 | 1.00 | 30.24 | C |
| ATOM | 1631 | O | ASN | B | 102 | 33.610 | 46.376 | −0.317 | 1.00 | 28.46 | O |
| ATOM | 1632 | CB | ASN | B | 102 | 32.120 | 44.197 | −1.171 | 1.00 | 31.25 | C |
| ATOM | 1633 | CG | ASN | B | 102 | 31.344 | 43.869 | −2.442 | 1.00 | 33.02 | C |
| ATOM | 1634 | OD1 | ASN | B | 102 | 31.813 | 44.124 | −3.558 | 1.00 | 33.52 | O |
| ATOM | 1635 | ND2 | ASN | B | 102 | 30.141 | 43.319 | −2.277 | 1.00 | 32.99 | N |

TABLE 3-continued

FGFR2(D2–D3) Complexed with FGF2

| ATOM | 1636 | N | TYR | B | 103 | 35.469 | 45.112 | −0.037 | 1.00 | 28.45 | N |
|---|---|---|---|---|---|---|---|---|---|---|---|
| ATOM | 1637 | CA | TYR | B | 103 | 36.197 | 46.126 | 0.742 | 1.00 | 27.56 | C |
| ATOM | 1638 | C | TYR | B | 103 | 37.332 | 46.566 | −0.167 | 1.00 | 27.29 | C |
| ATOM | 1639 | O | TYR | B | 103 | 37.645 | 45.865 | −1.132 | 1.00 | 26.21 | O |
| ATOM | 1640 | CB | TYR | B | 103 | 36.809 | 45.546 | 2.015 | 1.00 | 26.19 | C |
| ATOM | 1641 | CG | TYR | B | 103 | 35.830 | 45.340 | 3.127 | 1.00 | 26.10 | C |
| ATOM | 1642 | CD1 | TYR | B | 103 | 35.504 | 46.387 | 3.986 | 1.00 | 25.93 | C |
| ATOM | 1643 | CD2 | TYR | B | 103 | 35.239 | 44.087 | 3.345 | 1.00 | 25.66 | C |
| ATOM | 1644 | CE1 | TYR | B | 103 | 34.627 | 46.199 | 5.031 | 1.00 | 25.67 | C |
| ATOM | 1645 | CE2 | TYR | B | 103 | 34.355 | 43.891 | 4.393 | 1.00 | 25.55 | C |
| ATOM | 1646 | CZ | TYR | B | 103 | 34.056 | 44.951 | 5.232 | 1.00 | 25.68 | C |
| ATOM | 1647 | OH | TYR | B | 103 | 33.100 | 44.781 | 6.276 | 1.00 | 26.38 | O |
| ATOM | 1648 | N | ASN | B | 104 | 37.940 | 47.714 | 0.131 | 1.00 | 26.26 | N |
| ATOM | 1649 | CA | ASN | B | 104 | 39.053 | 48.213 | −0.672 | 1.00 | 26.34 | C |
| ATOM | 1650 | C | ASN | B | 104 | 40.394 | 47.962 | 0.026 | 1.00 | 25.99 | C |
| ATOM | 1651 | O | ASN | B | 104 | 40.455 | 47.867 | 1.254 | 1.00 | 26.46 | O |
| ATOM | 1652 | CB | ASN | B | 104 | 38.926 | 49.726 | −0.890 | 1.00 | 27.44 | C |
| ATOM | 1653 | CG | ASN | B | 104 | 37.931 | 50.098 | −1.986 | 1.00 | 28.73 | C |
| ATOM | 1654 | OD1 | ASN | B | 104 | 37.230 | 49.240 | −2.548 | 1.00 | 25.88 | O |
| ATOM | 1655 | ND2 | ASN | B | 104 | 37.869 | 51.392 | −2.293 | 1.00 | 26.81 | N |
| ATOM | 1656 | N | THR | B | 105 | 41.462 | 47.849 | −0.758 | 1.00 | 25.14 | N |
| ATOM | 1657 | CA | THR | B | 105 | 42.812 | 47.708 | −0.201 | 1.00 | 25.17 | C |
| ATOM | 1658 | C | THR | B | 105 | 43.709 | 48.719 | −0.924 | 1.00 | 25.62 | C |
| ATOM | 1659 | O | THR | B | 105 | 43.472 | 49.055 | −2.086 | 1.00 | 24.52 | O |
| ATOM | 1660 | CB | THR | B | 105 | 43.430 | 46.315 | −0.422 | 1.00 | 24.00 | C |
| ATOM | 1661 | OG1 | THR | B | 105 | 43.387 | 46.005 | −1.815 | 1.00 | 22.68 | O |
| ATOM | 1662 | CG2 | THR | B | 105 | 42.709 | 45.256 | 0.405 | 1.00 | 24.52 | C |
| ATOM | 1663 | N | TYR | B | 106 | 44.730 | 49.200 | −0.226 | 1.00 | 26.51 | N |
| ATOM | 1664 | CA | TYR | B | 106 | 45.665 | 50.176 | −0.776 | 1.00 | 28.14 | C |
| ATOM | 1665 | C | TYR | B | 106 | 47.093 | 49.648 | −0.605 | 1.00 | 29.96 | C |
| ATOM | 1666 | O | TYR | B | 106 | 47.626 | 49.593 | 0.506 | 1.00 | 28.79 | O |
| ATOM | 1667 | CB | TYR | B | 106 | 45.468 | 51.518 | −0.059 | 1.00 | 27.28 | C |
| ATOM | 1668 | CG | TYR | B | 106 | 44.113 | 52.112 | −0.362 | 1.00 | 25.83 | C |
| ATOM | 1669 | CD1 | TYR | B | 106 | 43.872 | 52.753 | −1.585 | 1.00 | 25.32 | C |
| ATOM | 1670 | CD2 | TYR | B | 106 | 43.039 | 51.929 | 0.508 | 1.00 | 25.16 | C |
| ATOM | 1671 | CE1 | TYR | B | 106 | 42.587 | 53.187 | −1.937 | 1.00 | 26.20 | C |
| ATOM | 1672 | CE2 | TYR | B | 106 | 41.742 | 52.355 | 0.167 | 1.00 | 24.66 | C |
| ATOM | 1673 | CZ | TYR | B | 106 | 41.524 | 52.976 | −1.055 | 1.00 | 25.22 | C |
| ATOM | 1674 | OH | TYR | B | 106 | 40.243 | 53.336 | −1.428 | 1.00 | 24.70 | O |
| ATOM | 1675 | N | ARG | B | 107 | 47.686 | 49.241 | −1.723 | 1.00 | 31.88 | N |
| ATOM | 1676 | CA | ARG | B | 107 | 49.032 | 48.673 | −1.744 | 1.00 | 34.65 | C |
| ATOM | 1677 | C | ARG | B | 107 | 50.066 | 49.651 | −2.341 | 1.00 | 34.73 | C |
| ATOM | 1678 | O | ARG | B | 107 | 49.866 | 50.185 | −3.429 | 1.00 | 33.56 | O |
| ATOM | 1679 | CB | ARG | B | 107 | 48.983 | 47.365 | −2.550 | 1.00 | 35.15 | C |
| ATOM | 1680 | CG | ARG | B | 107 | 50.231 | 46.500 | −2.494 | 1.00 | 35.99 | C |
| ATOM | 1681 | CD | ARG | B | 107 | 49.960 | 45.150 | −3.142 | 1.00 | 36.01 | C |
| ATOM | 1682 | NE | ARG | B | 107 | 49.470 | 45.273 | −4.514 | 1.00 | 36.49 | N |
| ATOM | 1683 | CZ | ARG | B | 107 | 50.233 | 45.574 | −5.560 | 1.00 | 37.81 | C |
| ATOM | 1684 | NH1 | ARG | B | 107 | 51.536 | 45.782 | −5.395 | 1.00 | 39.30 | N |
| ATOM | 1685 | NH2 | ARG | B | 107 | 49.698 | 45.681 | −6.774 | 1.00 | 37.32 | N |
| ATOM | 1686 | N | SER | B | 108 | 51.161 | 49.866 | −1.614 | 1.00 | 36.73 | N |
| ATOM | 1687 | CA | SER | B | 108 | 52.238 | 50.779 | −2.024 | 1.00 | 37.70 | C |
| ATOM | 1688 | C | SER | B | 108 | 52.788 | 50.470 | −3.410 | 1.00 | 38.57 | C |
| ATOM | 1689 | O | SER | B | 108 | 53.150 | 49.327 | −3.698 | 1.00 | 38.27 | O |
| ATOM | 1690 | CB | SER | B | 108 | 53.383 | 50.725 | −1.001 | 1.00 | 38.05 | C |
| ATOM | 1691 | OG | SER | B | 108 | 54.424 | 51.648 | −1.302 | 1.00 | 39.50 | O |
| ATOM | 1692 | N | ARG | B | 109 | 52.853 | 51.482 | −4.278 | 1.00 | 39.46 | N |
| ATOM | 1693 | CA | ARG | B | 109 | 53.392 | 51.241 | −5.608 | 1.00 | 40.70 | C |
| ATOM | 1694 | C | ARG | B | 109 | 54.917 | 51.140 | −5.551 | 1.00 | 41.47 | C |
| ATOM | 1695 | O | ARG | B | 109 | 55.534 | 50.547 | −6.434 | 1.00 | 41.17 | O |
| ATOM | 1696 | CB | ARG | B | 109 | 52.987 | 52.334 | −6.595 | 1.00 | 41.24 | C |
| ATOM | 1697 | CG | ARG | B | 109 | 53.367 | 51.964 | −8.020 | 1.00 | 43.16 | C |
| ATOM | 1698 | CD | ARG | B | 109 | 52.808 | 52.923 | −9.043 | 1.00 | 45.10 | C |
| ATOM | 1699 | NE | ARG | B | 109 | 53.312 | 54.279 | −8.854 | 1.00 | 47.60 | N |
| ATOM | 1700 | CZ | ARG | B | 109 | 53.086 | 55.279 | −9.702 | 1.00 | 49.05 | C |
| ATOM | 1701 | NH1 | ARG | B | 109 | 52.363 | 55.065 | −10.797 | 1.00 | 50.36 | N |
| ATOM | 1702 | NH2 | ARG | B | 109 | 53.575 | 56.490 | −9.459 | 1.00 | 49.22 | N |
| ATOM | 1703 | N | LYS | B | 110 | 55.513 | 51.715 | −4.507 | 1.00 | 42.37 | N |
| ATOM | 1704 | CA | LYS | B | 110 | 56.972 | 51.676 | −4.327 | 1.00 | 43.78 | C |
| ATOM | 1705 | C | LYS | B | 110 | 57.383 | 50.351 | −3.678 | 1.00 | 44.19 | C |
| ATOM | 1706 | O | LYS | B | 110 | 58.136 | 49.563 | −4.263 | 1.00 | 44.41 | O |
| ATOM | 1707 | CB | LYS | B | 110 | 57.436 | 52.843 | −3.447 | 1.00 | 42.84 | C |
| ATOM | 1708 | N | TYR | B | 111 | 56.887 | 50.124 | −2.463 | 1.00 | 43.84 | N |
| ATOM | 1709 | CA | TYR | B | 111 | 57.157 | 48.898 | −1.720 | 1.00 | 44.25 | C |
| ATOM | 1710 | C | TYR | B | 111 | 55.946 | 48.008 | −1.995 | 1.00 | 44.80 | C |
| ATOM | 1711 | O | TYR | B | 111 | 55.039 | 47.896 | −1.165 | 1.00 | 45.25 | O |
| ATOM | 1712 | CB | TYR | B | 111 | 57.263 | 49.210 | −0.226 | 1.00 | 43.80 | C |

TABLE 3-continued

FGFR2(D2–D3) Complexed with FGF2

| ATOM | 1713 | N | THR | B | 112 | 55.952 | 47.390 | -3.174 | 1.00 | 44.95 | N |
|---|---|---|---|---|---|---|---|---|---|---|---|
| ATOM | 1714 | CA | THR | B | 112 | 54.860 | 46.554 | -3.668 | 1.00 | 45.44 | C |
| ATOM | 1715 | C | THR | B | 112 | 54.283 | 45.401 | -2.841 | 1.00 | 45.64 | C |
| ATOM | 1716 | O | THR | B | 112 | 53.409 | 44.677 | -3.338 | 1.00 | 45.80 | O |
| ATOM | 1717 | CB | THR | B | 112 | 55.218 | 45.963 | -5.038 | 1.00 | 45.80 | C |
| ATOM | 1718 | OG1 | THR | B | 112 | 56.262 | 44.997 | -4.872 | 1.00 | 46.43 | O |
| ATOM | 1719 | CG2 | THR | B | 112 | 55.676 | 47.056 | -5.990 | 1.00 | 45.62 | C |
| ATOM | 1720 | N | SER | B | 113 | 54.731 | 45.213 | -1.603 | 1.00 | 44.63 | N |
| ATOM | 1721 | CA | SER | B | 113 | 54.188 | 44.111 | -0.813 | 1.00 | 44.47 | C |
| ATOM | 1722 | C | SER | B | 113 | 53.490 | 44.581 | 0.452 | 1.00 | 43.56 | C |
| ATOM | 1723 | O | SER | B | 113 | 52.829 | 43.792 | 1.125 | 1.00 | 43.26 | O |
| ATOM | 1724 | CB | SER | B | 113 | 55.292 | 43.132 | -0.413 | 1.00 | 46.21 | C |
| ATOM | 1725 | OG | SER | B | 113 | 56.054 | 43.657 | 0.663 | 1.00 | 48.08 | O |
| ATOM | 1726 | N | TRP | B | 114 | 53.644 | 45.860 | 0.774 | 1.00 | 42.13 | N |
| ATOM | 1727 | CA | TRP | B | 114 | 53.042 | 46.425 | 1.975 | 1.00 | 41.14 | C |
| ATOM | 1728 | C | TRP | B | 114 | 51.712 | 47.153 | 1.722 | 1.00 | 40.23 | C |
| ATOM | 1729 | O | TRP | B | 114 | 51.519 | 47.793 | 0.689 | 1.00 | 39.96 | O |
| ATOM | 1730 | CB | TRP | B | 114 | 54.037 | 47.380 | 2.653 | 1.00 | 40.97 | C |
| ATOM | 1731 | N | TYR | B | 115 | 50.815 | 47.061 | 2.697 | 1.00 | 38.98 | N |
| ATOM | 1732 | CA | TYR | B | 115 | 49.501 | 47.676 | 2.624 | 1.00 | 38.33 | C |
| ATOM | 1733 | C | TYR | B | 115 | 49.276 | 48.732 | 3.698 | 1.00 | 37.50 | C |
| ATOM | 1734 | O | TYR | B | 115 | 49.862 | 48.676 | 4.779 | 1.00 | 38.47 | O |
| ATOM | 1735 | CB | TYR | B | 115 | 48.403 | 46.615 | 2.801 | 1.00 | 39.08 | C |
| ATOM | 1736 | CG | TYR | B | 115 | 48.269 | 45.613 | 1.679 | 1.00 | 39.03 | C |
| ATOM | 1737 | CD1 | TYR | B | 115 | 49.141 | 44.527 | 1.571 | 1.00 | 39.34 | C |
| ATOM | 1738 | CD2 | TYR | B | 115 | 47.256 | 45.741 | 0.731 | 1.00 | 39.04 | C |
| ATOM | 1739 | CE1 | TYR | B | 115 | 49.002 | 43.587 | 0.541 | 1.00 | 39.95 | C |
| ATOM | 1740 | CE2 | TYR | B | 115 | 47.107 | 44.818 | -0.296 | 1.00 | 39.74 | C |
| ATOM | 1741 | CZ | TYR | B | 115 | 47.980 | 43.740 | -0.390 | 1.00 | 40.53 | C |
| ATOM | 1742 | OH | TYR | B | 115 | 47.809 | 42.817 | -1.404 | 1.00 | 40.54 | O |
| ATOM | 1743 | N | VAL | B | 116 | 48.415 | 49.693 | 3.390 | 1.00 | 36.06 | N |
| ATOM | 1744 | CA | VAL | B | 116 | 48.036 | 50.721 | 4.345 | 1.00 | 35.08 | C |
| ATOM | 1745 | C | VAL | B | 116 | 47.151 | 49.925 | 5.296 | 1.00 | 36.04 | C |
| ATOM | 1746 | O | VAL | B | 116 | 46.270 | 49.188 | 4.848 | 1.00 | 36.69 | O |
| ATOM | 1747 | CB | VAL | B | 116 | 47.181 | 51.821 | 3.669 | 1.00 | 33.88 | C |
| ATOM | 1748 | CG1 | VAL | B | 116 | 46.617 | 52.776 | 4.713 | 1.00 | 32.43 | C |
| ATOM | 1749 | CG2 | VAL | B | 116 | 48.021 | 52.570 | 2.655 | 1.00 | 33.57 | C |
| ATOM | 1750 | N | ALA | B | 117 | 47.368 | 50.059 | 6.595 | 1.00 | 36.87 | N |
| ATOM | 1751 | CA | ALA | B | 117 | 46.574 | 49.300 | 7.542 | 1.00 | 38.16 | C |
| ATOM | 1752 | C | ALA | B | 117 | 46.555 | 49.898 | 8.934 | 1.00 | 38.91 | C |
| ATOM | 1753 | O | ALA | B | 117 | 47.447 | 50.655 | 9.317 | 1.00 | 39.19 | O |
| ATOM | 1754 | CB | ALA | B | 117 | 47.093 | 47.863 | 7.600 | 1.00 | 39.05 | C |
| ATOM | 1755 | N | LEU | B | 118 | 45.520 | 49.550 | 9.687 | 1.00 | 40.06 | N |
| ATOM | 1756 | CA | LEU | B | 118 | 45.357 | 50.030 | 11.051 | 1.00 | 40.46 | C |
| ATOM | 1757 | C | LEU | B | 118 | 45.278 | 48.843 | 11.995 | 1.00 | 41.64 | C |
| ATOM | 1758 | O | LEU | B | 118 | 44.795 | 47.778 | 11.607 | 1.00 | 42.32 | O |
| ATOM | 1759 | CB | LEU | B | 118 | 44.083 | 50.856 | 11.170 | 1.00 | 40.02 | C |
| ATOM | 1760 | CG | LEU | B | 118 | 44.095 | 52.196 | 10.434 | 1.00 | 40.80 | C |
| ATOM | 1761 | CD1 | LEU | B | 118 | 42.780 | 52.926 | 10.683 | 1.00 | 39.59 | C |
| ATOM | 1762 | CD2 | LEU | B | 118 | 45.267 | 53.038 | 10.928 | 1.00 | 40.69 | C |
| ATOM | 1763 | N | LYS | B | 119 | 45.751 | 49.027 | 13.227 | 1.00 | 42.66 | N |
| ATOM | 1764 | CA | LYS | B | 119 | 45.727 | 47.972 | 14.238 | 1.00 | 43.23 | C |
| ATOM | 1765 | C | LYS | B | 119 | 44.458 | 48.088 | 15.072 | 1.00 | 43.75 | C |
| ATOM | 1766 | O | LYS | B | 119 | 43.825 | 49.146 | 15.111 | 1.00 | 43.74 | O |
| ATOM | 1767 | CB | LYS | B | 119 | 46.955 | 48.083 | 15.157 | 1.00 | 43.19 | C |
| ATOM | 1768 | N | ARG | B | 120 | 44.093 | 47.000 | 15.747 | 1.00 | 44.61 | N |
| ATOM | 1769 | CA | ARG | B | 120 | 42.896 | 46.980 | 16.583 | 1.00 | 44.95 | C |
| ATOM | 1770 | C | ARG | B | 120 | 42.940 | 48.066 | 17.647 | 1.00 | 45.06 | C |
| ATOM | 1771 | O | ARG | B | 120 | 41.909 | 48.441 | 18.204 | 1.00 | 45.18 | O |
| ATOM | 1772 | CB | ARG | B | 120 | 42.734 | 45.606 | 17.250 | 1.00 | 44.61 | C |
| ATOM | 1773 | N | THR | B | 121 | 44.135 | 48.583 | 17.913 | 1.00 | 45.91 | N |
| ATOM | 1774 | CA | THR | B | 121 | 44.321 | 49.618 | 18.924 | 1.00 | 46.59 | C |
| ATOM | 1775 | C | THR | B | 121 | 43.972 | 51.004 | 18.404 | 1.00 | 47.17 | C |
| ATOM | 1776 | O | THR | B | 121 | 43.613 | 51.891 | 19.177 | 1.00 | 47.58 | O |
| ATOM | 1777 | CB | THR | B | 121 | 45.778 | 49.672 | 19.405 | 1.00 | 47.28 | C |
| ATOM | 1778 | OG1 | THR | B | 121 | 46.562 | 50.406 | 18.454 | 1.00 | 48.03 | O |
| ATOM | 1779 | CG2 | THR | B | 121 | 46.352 | 48.258 | 19.546 | 1.00 | 47.34 | C |
| ATOM | 1780 | N | GLY | B | 122 | 44.089 | 51.196 | 17.096 | 1.00 | 47.80 | N |
| ATOM | 1781 | CA | GLY | B | 122 | 43.794 | 52.496 | 16.525 | 1.00 | 48.54 | C |
| ATOM | 1782 | C | GLY | B | 122 | 45.062 | 53.138 | 15.988 | 1.00 | 48.99 | C |
| ATOM | 1783 | O | GLY | B | 122 | 45.037 | 54.237 | 15.424 | 1.00 | 49.05 | O |
| ATOM | 1784 | N | GLN | B | 123 | 46.183 | 52.455 | 16.182 | 1.00 | 49.01 | N |
| ATOM | 1785 | CA | GLN | B | 123 | 47.464 | 52.944 | 15.696 | 1.00 | 48.87 | C |
| ATOM | 1786 | C | GLN | B | 123 | 47.693 | 52.235 | 14.371 | 1.00 | 48.83 | C |
| ATOM | 1787 | O | GLN | B | 123 | 47.209 | 51.120 | 14.173 | 1.00 | 48.65 | O |
| ATOM | 1788 | CB | GLN | B | 123 | 48.581 | 52.600 | 16.687 | 1.00 | 48.91 | C |
| ATOM | 1789 | N | TYR | B | 124 | 48.415 | 52.874 | 13.457 | 1.00 | 48.90 | N |

TABLE 3-continued

FGFR2(D2–D3) Complexed with FGF2

| | | | | | | | | | | | |
|---|---|---|---|---|---|---|---|---|---|---|---|
| ATOM | 1790 | CA | TYR | B | 124 | 48.660 | 52.250 | 12.166 | 1.00 | 48.84 | C |
| ATOM | 1791 | C | TYR | B | 124 | 49.484 | 50.992 | 12.359 | 1.00 | 48.25 | C |
| ATOM | 1792 | O | TYR | B | 124 | 50.020 | 50.755 | 13.436 | 1.00 | 47.23 | O |
| ATOM | 1793 | CB | TYR | B | 124 | 49.361 | 53.225 | 11.204 | 1.00 | 50.36 | C |
| ATOM | 1794 | CG | TYR | B | 124 | 50.824 | 53.505 | 11.482 | 1.00 | 52.03 | C |
| ATOM | 1795 | CD1 | TYR | B | 124 | 51.801 | 52.541 | 11.233 | 1.00 | 52.58 | C |
| ATOM | 1796 | CD2 | TYR | B | 124 | 51.237 | 54.754 | 11.949 | 1.00 | 53.04 | C |
| ATOM | 1797 | CE1 | TYR | B | 124 | 53.151 | 52.811 | 11.437 | 1.00 | 53.50 | C |
| ATOM | 1798 | CE2 | TYR | B | 124 | 52.588 | 55.035 | 12.155 | 1.00 | 53.93 | C |
| ATOM | 1799 | CZ | TYR | B | 124 | 53.537 | 54.056 | 11.894 | 1.00 | 53.72 | C |
| ATOM | 1800 | OH | TYR | B | 124 | 54.874 | 54.326 | 12.074 | 1.00 | 54.97 | O |
| ATOM | 1801 | N | LYS | B | 125 | 49.572 | 50.182 | 11.313 | 1.00 | 48.10 | N |
| ATOM | 1802 | CA | LYS | B | 125 | 50.325 | 48.943 | 11.368 | 1.00 | 48.65 | C |
| ATOM | 1803 | C | LYS | B | 125 | 51.458 | 48.994 | 10.349 | 1.00 | 49.32 | C |
| ATOM | 1804 | O | LYS | B | 125 | 51.242 | 49.359 | 9.192 | 1.00 | 49.64 | O |
| ATOM | 1805 | CB | LYS | B | 125 | 49.395 | 47.771 | 11.067 | 1.00 | 48.68 | C |
| ATOM | 1806 | CG | LYS | B | 125 | 50.039 | 46.410 | 11.184 | 1.00 | 48.74 | C |
| ATOM | 1807 | CD | LYS | B | 125 | 48.991 | 45.310 | 11.063 | 1.00 | 48.23 | C |
| ATOM | 1808 | CE | LYS | B | 125 | 49.618 | 43.930 | 11.202 | 1.00 | 48.26 | C |
| ATOM | 1809 | NZ | LYS | B | 125 | 48.602 | 42.842 | 11.144 | 1.00 | 47.68 | N |
| ATOM | 1810 | N | LEU | B | 126 | 52.664 | 48.638 | 10.783 | 1.00 | 50.14 | N |
| ATOM | 1811 | CA | LEU | B | 126 | 53.829 | 48.655 | 9.910 | 1.00 | 50.56 | C |
| ATOM | 1812 | C | LEU | B | 126 | 53.538 | 47.927 | 8.616 | 1.00 | 51.34 | C |
| ATOM | 1813 | O | LEU | B | 126 | 53.103 | 46.778 | 8.630 | 1.00 | 52.07 | O |
| ATOM | 1814 | CB | LEU | B | 126 | 55.023 | 47.996 | 10.603 | 1.00 | 51.34 | C |
| ATOM | 1815 | N | GLY | B | 127 | 53.783 | 48.593 | 7.494 | 1.00 | 51.69 | N |
| ATOM | 1816 | CA | GLY | B | 127 | 53.541 | 47.967 | 6.211 | 1.00 | 52.65 | C |
| ATOM | 1817 | C | GLY | B | 127 | 54.206 | 46.608 | 6.088 | 1.00 | 53.66 | C |
| ATOM | 1818 | O | GLY | B | 127 | 53.682 | 45.708 | 5.431 | 1.00 | 54.03 | O |
| ATOM | 1819 | N | SER | B | 128 | 55.361 | 46.454 | 6.728 | 1.00 | 54.20 | N |
| ATOM | 1820 | CA | SER | B | 128 | 56.113 | 45.204 | 6.680 | 1.00 | 54.84 | C |
| ATOM | 1821 | C | SER | B | 128 | 55.397 | 44.040 | 7.365 | 1.00 | 54.63 | C |
| ATOM | 1822 | O | SER | B | 128 | 55.717 | 42.878 | 7.118 | 1.00 | 54.52 | O |
| ATOM | 1823 | CB | SER | B | 128 | 57.481 | 45.409 | 7.334 | 1.00 | 56.09 | C |
| ATOM | 1824 | OG | SER | B | 128 | 57.335 | 45.937 | 8.642 | 1.00 | 57.87 | O |
| ATOM | 1825 | N | LYS | B | 129 | 54.433 | 44.358 | 8.225 | 1.00 | 54.30 | N |
| ATOM | 1826 | CA | LYS | B | 129 | 53.674 | 43.344 | 8.962 | 1.00 | 53.71 | C |
| ATOM | 1827 | C | LYS | B | 129 | 52.300 | 43.070 | 8.350 | 1.00 | 53.01 | C |
| ATOM | 1828 | O | LYS | B | 129 | 51.460 | 42.427 | 8.985 | 1.00 | 52.53 | O |
| ATOM | 1829 | CB | LYS | B | 129 | 53.407 | 43.802 | 10.392 | 1.00 | 54.98 | C |
| ATOM | 1830 | CG | LYS | B | 129 | 54.592 | 44.193 | 11.231 | 1.00 | 55.83 | C |
| ATOM | 1831 | CD | LYS | B | 129 | 54.083 | 44.822 | 12.529 | 1.00 | 56.88 | C |
| ATOM | 1832 | CE | LYS | B | 129 | 53.071 | 43.917 | 13.240 | 1.00 | 57.58 | C |
| ATOM | 1833 | NZ | LYS | B | 129 | 52.452 | 44.575 | 14.433 | 1.00 | 58.18 | N |
| ATOM | 1834 | N | THR | B | 130 | 52.055 | 43.567 | 7.143 | 1.00 | 51.75 | N |
| ATOM | 1835 | CA | THR | B | 130 | 50.757 | 43.373 | 6.511 | 1.00 | 50.23 | C |
| ATOM | 1836 | C | THR | B | 130 | 50.762 | 42.235 | 5.502 | 1.00 | 50.55 | C |
| ATOM | 1837 | O | THR | B | 130 | 51.814 | 41.848 | 4.989 | 1.00 | 50.97 | O |
| ATOM | 1838 | CB | THR | B | 130 | 50.285 | 44.656 | 5.800 | 1.00 | 49.10 | C |
| ATOM | 1839 | OG1 | THR | B | 130 | 51.169 | 44.953 | 4.713 | 1.00 | 47.52 | O |
| ATOM | 1840 | CG2 | THR | B | 130 | 50.258 | 45.826 | 6.771 | 1.00 | 47.14 | C |
| ATOM | 1841 | N | GLY | B | 131 | 49.570 | 41.712 | 5.223 | 1.00 | 50.29 | N |
| ATOM | 1842 | CA | GLY | B | 131 | 49.421 | 40.618 | 4.282 | 1.00 | 50.10 | C |
| ATOM | 1843 | C | GLY | B | 131 | 48.043 | 40.655 | 3.649 | 1.00 | 50.39 | C |
| ATOM | 1844 | O | GLY | B | 131 | 47.115 | 41.205 | 4.241 | 1.00 | 50.38 | O |
| ATOM | 1845 | N | PRO | B | 132 | 47.871 | 40.063 | 2.457 | 1.00 | 50.68 | N |
| ATOM | 1846 | CA | PRO | B | 132 | 46.598 | 40.031 | 1.729 | 1.00 | 51.12 | C |
| ATOM | 1847 | C | PRO | B | 132 | 45.353 | 39.484 | 2.429 | 1.00 | 51.40 | C |
| ATOM | 1848 | O | PRO | B | 132 | 44.229 | 39.882 | 2.090 | 1.00 | 52.15 | O |
| ATOM | 1849 | CB | PRO | B | 132 | 46.946 | 39.262 | 0.448 | 1.00 | 51.15 | C |
| ATOM | 1850 | CG | PRO | B | 132 | 48.128 | 38.453 | 0.826 | 1.00 | 50.96 | C |
| ATOM | 1851 | CD | PRO | B | 132 | 48.924 | 39.390 | 1.684 | 1.00 | 50.86 | C |
| ATOM | 1852 | N | GLY | B | 133 | 45.529 | 38.605 | 3.408 | 1.00 | 50.66 | N |
| ATOM | 1853 | CA | GLY | B | 133 | 44.365 | 38.051 | 4.078 | 1.00 | 49.54 | C |
| ATOM | 1854 | C | GLY | B | 133 | 44.015 | 38.694 | 5.404 | 1.00 | 49.16 | C |
| ATOM | 1855 | O | GLY | B | 133 | 43.060 | 38.275 | 6.061 | 1.00 | 49.29 | O |
| ATOM | 1856 | N | GLN | B | 134 | 44.775 | 39.713 | 5.800 | 1.00 | 48.04 | N |
| ATOM | 1857 | CA | GLN | B | 134 | 44.543 | 40.394 | 7.072 | 1.00 | 45.89 | C |
| ATOM | 1858 | C | GLN | B | 134 | 43.307 | 41.294 | 7.090 | 1.00 | 44.66 | C |
| ATOM | 1859 | O | GLN | B | 134 | 42.874 | 41.813 | 6.061 | 1.00 | 44.65 | O |
| ATOM | 1860 | CB | GLN | B | 134 | 45.777 | 41.230 | 7.462 | 1.00 | 46.36 | C |
| ATOM | 1861 | CG | GLN | B | 134 | 47.047 | 40.425 | 7.737 | 1.00 | 45.77 | C |
| ATOM | 1862 | CD | GLN | B | 134 | 48.201 | 41.282 | 8.269 | 1.00 | 45.99 | C |
| ATOM | 1863 | OE1 | GLN | B | 134 | 48.006 | 42.415 | 8.705 | 1.00 | 45.33 | O |
| ATOM | 1864 | NE2 | GLN | B | 134 | 49.405 | 40.725 | 8.250 | 1.00 | 45.77 | N |
| ATOM | 1865 | N | LYS | B | 135 | 42.762 | 41.474 | 8.287 | 1.00 | 42.83 | N |
| ATOM | 1866 | CA | LYS | B | 135 | 41.592 | 42.302 | 8.531 | 1.00 | 41.46 | C |

TABLE 3-continued

| | | | | | | | | | | | |
|---|---|---|---|---|---|---|---|---|---|---|---|
| ATOM | 1867 | C | LYS | B | 135 | 42.004 | 43.784 | 8.630 | 1.00 | 40.03 | C |
| ATOM | 1868 | O | LYS | B | 135 | 41.193 | 44.689 | 8.403 | 1.00 | 39.14 | O |
| ATOM | 1869 | CB | LYS | B | 135 | 40.960 | 41.825 | 9.837 | 1.00 | 41.75 | C |
| ATOM | 1870 | CG | LYS | B | 135 | 39.757 | 42.577 | 10.320 | 1.00 | 43.82 | C |
| ATOM | 1871 | CD | LYS | B | 135 | 39.174 | 41.833 | 11.529 | 1.00 | 45.84 | C |
| ATOM | 1872 | CE | LYS | B | 135 | 38.116 | 42.655 | 12.241 | 1.00 | 46.02 | C |
| ATOM | 1873 | NZ | LYS | B | 135 | 37.055 | 43.059 | 11.288 | 1.00 | 47.20 | N |
| ATOM | 1874 | N | ALA | B | 136 | 43.274 | 44.014 | 8.959 | 1.00 | 37.66 | N |
| ATOM | 1875 | CA | ALA | B | 136 | 43.815 | 45.360 | 9.120 | 1.00 | 36.75 | C |
| ATOM | 1876 | C | ALA | B | 136 | 43.970 | 46.171 | 7.824 | 1.00 | 34.98 | C |
| ATOM | 1877 | O | ALA | B | 136 | 44.069 | 47.398 | 7.880 | 1.00 | 35.66 | O |
| ATOM | 1878 | CB | ALA | B | 136 | 45.152 | 45.287 | 9.851 | 1.00 | 36.88 | C |
| ATOM | 1879 | N | ILE | B | 137 | 43.981 | 45.504 | 6.670 | 1.00 | 32.94 | N |
| ATOM | 1880 | CA | ILE | B | 137 | 44.122 | 46.198 | 5.389 | 1.00 | 31.61 | C |
| ATOM | 1881 | C | ILE | B | 137 | 42.798 | 46.482 | 4.660 | 1.00 | 30.44 | C |
| ATOM | 1882 | O | ILE | B | 137 | 42.809 | 47.069 | 3.570 | 1.00 | 29.05 | O |
| ATOM | 1883 | CB | ILE | B | 137 | 45.015 | 45.402 | 4.389 | 1.00 | 31.44 | C |
| ATOM | 1884 | CG1 | ILE | B | 137 | 44.243 | 44.200 | 3.829 | 1.00 | 32.15 | C |
| ATOM | 1885 | CG2 | ILE | B | 137 | 46.284 | 44.901 | 5.087 | 1.00 | 32.82 | C |
| ATOM | 1886 | CD1 | ILE | B | 137 | 45.055 | 43.337 | 2.865 | 1.00 | 30.55 | C |
| ATOM | 1887 | N | LEU | B | 138 | 41.672 | 46.081 | 5.249 | 1.00 | 28.88 | N |
| ATOM | 1888 | CA | LEU | B | 138 | 40.374 | 46.272 | 4.591 | 1.00 | 28.50 | C |
| ATOM | 1889 | C | LEU | B | 138 | 39.662 | 47.565 | 4.957 | 1.00 | 27.52 | C |
| ATOM | 1890 | O | LEU | B | 138 | 39.334 | 47.800 | 6.122 | 1.00 | 27.00 | O |
| ATOM | 1891 | CB | LEU | B | 138 | 39.466 | 45.067 | 4.874 | 1.00 | 26.78 | C |
| ATOM | 1892 | CG | LEU | B | 138 | 40.140 | 43.738 | 4.484 | 1.00 | 27.13 | C |
| ATOM | 1893 | CD1 | LEU | B | 138 | 39.256 | 42.552 | 4.855 | 1.00 | 27.13 | C |
| ATOM | 1894 | CD2 | LEU | B | 138 | 40.417 | 43.722 | 2.990 | 1.00 | 25.65 | C |
| ATOM | 1895 | N | PHE | B | 139 | 39.433 | 48.407 | 3.950 | 1.00 | 26.87 | N |
| ATOM | 1896 | CA | PHE | B | 139 | 38.753 | 49.683 | 4.162 | 1.00 | 26.76 | C |
| ATOM | 1897 | C | PHE | B | 139 | 37.482 | 49.836 | 3.318 | 1.00 | 27.04 | C |
| ATOM | 1898 | O | PHE | B | 139 | 37.370 | 49.311 | 2.210 | 1.00 | 26.13 | O |
| ATOM | 1899 | CB | PHE | B | 139 | 39.686 | 50.863 | 3.852 | 1.00 | 27.83 | C |
| ATOM | 1900 | CG | PHE | B | 139 | 40.900 | 50.946 | 4.746 | 1.00 | 29.10 | C |
| ATOM | 1901 | CD1 | PHE | B | 139 | 42.021 | 50.139 | 4.513 | 1.00 | 28.33 | C |
| ATOM | 1902 | CD2 | PHE | B | 139 | 40.917 | 51.825 | 5.835 | 1.00 | 28.94 | C |
| ATOM | 1903 | CE1 | PHE | B | 139 | 43.144 | 50.214 | 5.363 | 1.00 | 28.98 | C |
| ATOM | 1904 | CE2 | PHE | B | 139 | 42.033 | 51.904 | 6.687 | 1.00 | 27.99 | C |
| ATOM | 1905 | CZ | PHE | B | 139 | 43.142 | 51.102 | 6.453 | 1.00 | 27.54 | C |
| ATOM | 1906 | N | LEU | B | 140 | 36.536 | 50.597 | 3.850 | 1.00 | 27.21 | N |
| ATOM | 1907 | CA | LEU | B | 140 | 35.287 | 50.856 | 3.162 | 1.00 | 27.69 | C |
| ATOM | 1908 | C | LEU | B | 140 | 35.169 | 52.353 | 2.947 | 1.00 | 28.23 | C |
| ATOM | 1909 | O | LEU | B | 140 | 35.067 | 53.112 | 3.910 | 1.00 | 29.52 | O |
| ATOM | 1910 | CB | LEU | B | 140 | 34.113 | 50.362 | 4.017 | 1.00 | 27.73 | C |
| ATOM | 1911 | CG | LEU | B | 140 | 32.709 | 50.495 | 3.427 | 1.00 | 28.01 | C |
| ATOM | 1912 | CD1 | LEU | B | 140 | 32.632 | 49.651 | 2.161 | 1.00 | 29.66 | C |
| ATOM | 1913 | CD2 | LEU | B | 140 | 31.660 | 50.033 | 4.435 | 1.00 | 27.06 | C |
| ATOM | 1914 | N | PRO | B | 141 | 35.186 | 52.811 | 1.688 | 1.00 | 29.04 | N |
| ATOM | 1915 | CA | PRO | B | 141 | 35.069 | 54.255 | 1.461 | 1.00 | 30.00 | C |
| ATOM | 1916 | C | PRO | B | 141 | 33.656 | 54.740 | 1.805 | 1.00 | 31.46 | C |
| ATOM | 1917 | O | PRO | B | 141 | 32.664 | 54.133 | 1.391 | 1.00 | 31.39 | O |
| ATOM | 1918 | CB | PRO | B | 141 | 35.398 | 54.395 | −0.023 | 1.00 | 29.25 | C |
| ATOM | 1919 | CG | PRO | B | 141 | 34.816 | 53.137 | −0.603 | 1.00 | 30.27 | C |
| ATOM | 1920 | CD | PRO | B | 141 | 35.208 | 52.068 | 0.414 | 1.00 | 29.01 | C |
| ATOM | 1921 | N | MET | B | 142 | 33.567 | 55.818 | 2.574 | 1.00 | 32.79 | N |
| ATOM | 1922 | CA | MET | B | 142 | 32.274 | 56.367 | 2.970 | 1.00 | 34.51 | C |
| ATOM | 1923 | C | MET | B | 142 | 32.197 | 57.862 | 2.712 | 1.00 | 35.90 | C |
| ATOM | 1924 | O | MET | B | 142 | 33.222 | 58.551 | 2.660 | 1.00 | 36.05 | O |
| ATOM | 1925 | CB | MET | B | 142 | 32.019 | 56.111 | 4.452 | 1.00 | 34.55 | C |
| ATOM | 1926 | CG | MET | B | 142 | 32.004 | 54.649 | 4.832 | 1.00 | 34.06 | C |
| ATOM | 1927 | SD | MET | B | 142 | 31.760 | 54.424 | 6.588 | 1.00 | 34.95 | S |
| ATOM | 1928 | CE | MET | B | 142 | 29.969 | 54.769 | 6.691 | 1.00 | 34.56 | C |
| ATOM | 1929 | N | SER | B | 143 | 30.977 | 58.364 | 2.568 | 1.00 | 37.20 | N |
| ATOM | 1930 | CA | SER | B | 143 | 30.776 | 59.781 | 2.313 | 1.00 | 39.33 | C |
| ATOM | 1931 | C | SER | B | 143 | 31.251 | 60.661 | 3.460 | 1.00 | 40.56 | C |
| ATOM | 1932 | O | SER | B | 143 | 31.173 | 60.287 | 4.635 | 1.00 | 39.42 | O |
| ATOM | 1933 | CB | SER | B | 143 | 29.306 | 60.086 | 2.032 | 1.00 | 39.65 | C |
| ATOM | 1934 | OG | SER | B | 143 | 29.157 | 61.458 | 1.708 | 1.00 | 41.03 | O |
| ATOM | 1935 | N | ALA | B | 144 | 31.752 | 61.836 | 3.102 | 1.00 | 42.73 | N |
| ATOM | 1936 | CA | ALA | B | 144 | 32.230 | 62.781 | 4.098 | 1.00 | 45.56 | C |
| ATOM | 1937 | C | ALA | B | 144 | 31.066 | 63.652 | 4.578 | 1.00 | 47.26 | C |
| ATOM | 1938 | O | ALA | B | 144 | 31.263 | 64.793 | 4.983 | 1.00 | 47.91 | O |
| ATOM | 1939 | CB | ALA | B | 144 | 33.336 | 63.641 | 3.517 | 1.00 | 45.31 | C |
| ATOM | 1940 | N | LYS | B | 145 | 29.856 | 63.091 | 4.536 | 1.00 | 49.15 | N |
| ATOM | 1941 | CA | LYS | B | 145 | 28.638 | 63.782 | 4.968 | 1.00 | 50.17 | C |
| ATOM | 1942 | C | LYS | B | 145 | 28.504 | 65.124 | 4.277 | 1.00 | 50.66 | C |
| ATOM | 1943 | O | LYS | B | 145 | 28.219 | 65.081 | 3.063 | 1.00 | 51.61 | O |

TABLE 3-continued

FGFR2(D2–D3) Complexed with FGF2

| | | | | | | | | | | |
|---|---|---|---|---|---|---|---|---|---|---|
| ATOM | 1944 | CB | LYS | B | 145 | 28.629 | 63.982 | 6.488 | 1.00 | 50.30 | C |
| TER | 1945 | | LYS | B | 145 | | | | | |
| ATOM | 1946 | N | HIS | C | 16 | 18.017 | 33.163 | −14.374 | 1.00 | 39.92 | N |
| ATOM | 1947 | CA | HIS | C | 16 | 18.118 | 32.023 | −13.413 | 1.00 | 39.24 | C |
| ATOM | 1948 | C | HIS | C | 16 | 19.197 | 31.057 | −13.899 | 1.00 | 38.21 | C |
| ATOM | 1949 | O | HIS | C | 16 | 19.142 | 30.556 | −15.026 | 1.00 | 37.58 | O |
| ATOM | 1950 | CB | HIS | C | 16 | 16.770 | 31.305 | −13.295 | 1.00 | 40.25 | C |
| ATOM | 1951 | N | PHE | C | 17 | 20.177 | 30.801 | −13.035 | 1.00 | 37.36 | N |
| ATOM | 1952 | CA | PHE | C | 17 | 21.302 | 29.928 | −13.375 | 1.00 | 36.68 | C |
| ATOM | 1953 | C | PHE | C | 17 | 20.941 | 28.480 | −13.734 | 1.00 | 36.31 | C |
| ATOM | 1954 | O | PHE | C | 17 | 21.665 | 27.835 | −14.494 | 1.00 | 35.92 | O |
| ATOM | 1955 | CB | PHE | C | 17 | 22.360 | 29.960 | −12.250 | 1.00 | 35.03 | C |
| ATOM | 1956 | CG | PHE | C | 17 | 21.919 | 29.317 | −10.956 | 1.00 | 34.60 | C |
| ATOM | 1957 | CD1 | PHE | C | 17 | 22.194 | 27.974 | −10.698 | 1.00 | 33.86 | C |
| ATOM | 1958 | CD2 | PHE | C | 17 | 21.265 | 30.059 | −9.984 | 1.00 | 32.80 | C |
| ATOM | 1959 | CE1 | PHE | C | 17 | 21.826 | 27.380 | −9.478 | 1.00 | 34.30 | C |
| ATOM | 1960 | CE2 | PHE | C | 17 | 20.893 | 29.480 | −8.768 | 1.00 | 33.73 | C |
| ATOM | 1961 | CZ | PHE | C | 17 | 21.177 | 28.133 | −8.513 | 1.00 | 33.16 | C |
| ATOM | 1962 | N | LYS | C | 18 | 19.821 | 27.985 | −13.211 | 1.00 | 36.17 | N |
| ATOM | 1963 | CA | LYS | C | 18 | 19.374 | 26.617 | −13.481 | 1.00 | 36.04 | C |
| ATOM | 1964 | C | LYS | C | 18 | 18.752 | 26.413 | −14.865 | 1.00 | 36.36 | C |
| ATOM | 1965 | O | LYS | C | 18 | 18.632 | 25.282 | −15.334 | 1.00 | 37.03 | O |
| ATOM | 1966 | CB | LYS | C | 18 | 18.375 | 26.186 | −12.407 | 1.00 | 35.95 | C |
| ATOM | 1967 | CG | LYS | C | 18 | 18.991 | 26.092 | −11.027 | 1.00 | 36.63 | C |
| ATOM | 1968 | CD | LYS | C | 18 | 17.981 | 25.710 | −9.966 | 1.00 | 37.95 | C |
| ATOM | 1969 | CE | LYS | C | 18 | 16.931 | 26.797 | −9.778 | 1.00 | 38.74 | C |
| ATOM | 1970 | NZ | LYS | C | 18 | 16.200 | 26.619 | −8.501 | 1.00 | 36.65 | N |
| ATOM | 1971 | N | ASP | C | 19 | 18.351 | 27.503 | −15.513 | 1.00 | 36.06 | N |
| ATOM | 1972 | CA | ASP | C | 19 | 17.746 | 27.414 | −16.835 | 1.00 | 35.59 | C |
| ATOM | 1973 | C | ASP | C | 19 | 18.751 | 27.158 | −17.945 | 1.00 | 35.43 | C |
| ATOM | 1974 | O | ASP | C | 19 | 19.900 | 27.595 | −17.874 | 1.00 | 35.20 | O |
| ATOM | 1975 | CB | ASP | C | 19 | 17.003 | 28.703 | −17.174 | 1.00 | 35.67 | C |
| ATOM | 1976 | CG | ASP | C | 19 | 15.749 | 28.885 | −16.356 | 1.00 | 36.38 | C |
| ATOM | 1977 | OD1 | ASP | C | 19 | 15.225 | 30.011 | −16.343 | 1.00 | 33.91 | O |
| ATOM | 1978 | OD2 | ASP | C | 19 | 15.288 | 27.894 | −15.737 | 1.00 | 37.85 | O |
| ATOM | 1979 | N | PRO | C | 20 | 18.326 | 26.438 | −18.990 | 1.00 | 35.49 | N |
| ATOM | 1980 | CA | PRO | C | 20 | 19.204 | 26.143 | −20.123 | 1.00 | 35.29 | C |
| ATOM | 1981 | C | PRO | C | 20 | 19.551 | 27.448 | −20.834 | 1.00 | 35.29 | C |
| ATOM | 1982 | O | PRO | C | 20 | 18.855 | 28.448 | −20.668 | 1.00 | 34.84 | O |
| ATOM | 1983 | CB | PRO | C | 20 | 18.364 | 25.193 | −20.983 | 1.00 | 34.82 | C |
| ATOM | 1984 | CG | PRO | C | 20 | 16.953 | 25.511 | −20.597 | 1.00 | 36.19 | C |
| ATOM | 1985 | CD | PRO | C | 20 | 17.046 | 25.713 | −19.112 | 1.00 | 35.72 | C |
| ATOM | 1986 | N | LYS | C | 21 | 20.624 | 27.445 | −21.616 | 1.00 | 35.72 | N |
| ATOM | 1987 | CA | LYS | C | 21 | 21.045 | 28.660 | −22.304 | 1.00 | 36.28 | C |
| ATOM | 1988 | C | LYS | C | 21 | 21.677 | 28.399 | −23.648 | 1.00 | 36.33 | C |
| ATOM | 1989 | O | LYS | C | 21 | 22.015 | 27.265 | −23.982 | 1.00 | 36.72 | O |
| ATOM | 1990 | CB | LYS | C | 21 | 22.065 | 29.434 | −21.454 | 1.00 | 37.40 | C |
| ATOM | 1991 | CG | LYS | C | 21 | 21.619 | 29.715 | −20.043 | 1.00 | 39.17 | C |
| ATOM | 1992 | CD | LYS | C | 21 | 22.412 | 30.816 | −19.379 | 1.00 | 41.94 | C |
| ATOM | 1993 | CE | LYS | C | 21 | 21.957 | 30.947 | −17.932 | 1.00 | 43.48 | C |
| ATOM | 1994 | NZ | LYS | C | 21 | 20.497 | 31.251 | −17.926 | 1.00 | 43.44 | N |
| ATOM | 1995 | N | ARG | C | 22 | 21.824 | 29.465 | −24.425 | 1.00 | 36.01 | N |
| ATOM | 1996 | CA | ARG | C | 22 | 22.498 | 29.373 | −25.708 | 1.00 | 36.72 | C |
| ATOM | 1997 | C | ARG | C | 22 | 23.820 | 30.074 | −25.415 | 1.00 | 35.60 | C |
| ATOM | 1998 | O | ARG | C | 22 | 23.848 | 31.032 | −24.642 | 1.00 | 35.48 | O |
| ATOM | 1999 | CB | ARG | C | 22 | 21.772 | 30.163 | −26.805 | 1.00 | 38.56 | C |
| ATOM | 2000 | CG | ARG | C | 22 | 20.285 | 29.887 | −27.004 | 1.00 | 41.76 | C |
| ATOM | 2001 | CD | ARG | C | 22 | 19.823 | 30.641 | −28.247 | 1.00 | 44.38 | C |
| ATOM | 2002 | NE | ARG | C | 22 | 18.376 | 30.820 | −28.357 | 1.00 | 47.15 | N |
| ATOM | 2003 | CZ | ARG | C | 22 | 17.491 | 29.836 | −28.488 | 1.00 | 48.90 | C |
| ATOM | 2004 | NH1 | ARG | C | 22 | 17.887 | 28.565 | −28.519 | 1.00 | 49.62 | N |
| ATOM | 2005 | NH2 | ARG | C | 22 | 16.201 | 30.131 | −28.617 | 1.00 | 48.90 | N |
| ATOM | 2006 | N | LEU | C | 23 | 24.911 | 29.592 | −25.994 | 1.00 | 34.26 | N |
| ATOM | 2007 | CA | LEU | C | 23 | 26.205 | 30.244 | −25.804 | 1.00 | 33.19 | C |
| ATOM | 2008 | C | LEU | C | 23 | 26.579 | 30.892 | −27.121 | 1.00 | 32.28 | C |
| ATOM | 2009 | O | LEU | C | 23 | 26.933 | 30.214 | −28.076 | 1.00 | 32.68 | O |
| ATOM | 2010 | CB | LEU | C | 23 | 27.281 | 29.238 | −25.389 | 1.00 | 32.98 | C |
| ATOM | 2011 | CG | LEU | C | 23 | 27.159 | 28.667 | −23.974 | 1.00 | 34.44 | C |
| ATOM | 2012 | CD1 | LEU | C | 23 | 28.171 | 27.550 | −23.772 | 1.00 | 33.80 | C |
| ATOM | 2013 | CD2 | LEU | C | 23 | 27.363 | 29.788 | −22.950 | 1.00 | 33.91 | C |
| ATOM | 2014 | N | TYR | C | 24 | 26.490 | 32.214 | −27.155 | 1.00 | 31.86 | N |
| ATOM | 2015 | CA | TYR | C | 24 | 26.794 | 33.003 | −28.334 | 1.00 | 31.36 | C |
| ATOM | 2016 | C | TYR | C | 24 | 28.282 | 33.375 | −28.397 | 1.00 | 31.57 | C |
| ATOM | 2017 | O | TYR | C | 24 | 28.843 | 33.900 | −27.436 | 1.00 | 32.38 | O |
| ATOM | 2018 | CB | TYR | C | 24 | 25.903 | 34.249 | −28.311 | 1.00 | 29.63 | C |
| ATOM | 2019 | CG | TYR | C | 24 | 26.319 | 35.366 | −29.231 | 1.00 | 28.49 | C |
| ATOM | 2020 | CD1 | TYR | C | 24 | 27.325 | 36.257 | −28.863 | 1.00 | 27.87 | C |

TABLE 3-continued

FGFR2(D2–D3) Complexed with FGF2

| ATOM | 2021 | CD2 | TYR | C | 24 | 25.692 | 35.548 | −30.464 | 1.00 | 27.27 | C |
|---|---|---|---|---|---|---|---|---|---|---|---|
| ATOM | 2022 | CE1 | TYR | C | 24 | 27.698 | 37.313 | −29.697 | 1.00 | 26.83 | C |
| ATOM | 2023 | CE2 | TYR | C | 24 | 26.056 | 36.592 | −31.304 | 1.00 | 27.20 | C |
| ATOM | 2024 | CZ | TYR | C | 24 | 27.064 | 37.475 | −30.911 | 1.00 | 27.65 | C |
| ATOM | 2025 | OH | TYR | C | 24 | 27.433 | 38.517 | −31.732 | 1.00 | 26.72 | O |
| ATOM | 2026 | N | CYS | C | 25 | 28.918 | 33.101 | −29.530 | 1.00 | 31.53 | N |
| ATOM | 2027 | CA | CYS | C | 25 | 30.334 | 33.415 | −29.692 | 1.00 | 32.33 | C |
| ATOM | 2028 | C | CYS | C | 25 | 30.514 | 34.761 | −30.384 | 1.00 | 32.74 | C |
| ATOM | 2029 | O | CYS | C | 25 | 29.984 | 34.994 | −31.471 | 1.00 | 31.68 | O |
| ATOM | 2030 | CB | CYS | C | 25 | 31.038 | 32.319 | −30.498 | 1.00 | 31.99 | C |
| ATOM | 2031 | SG | CYS | C | 25 | 32.835 | 32.485 | −30.543 | 1.00 | 31.09 | S |
| ATOM | 2032 | N | LYS | C | 26 | 31.263 | 35.647 | −29.735 | 1.00 | 33.99 | N |
| ATOM | 2033 | CA | LYS | C | 26 | 31.522 | 36.972 | −30.270 | 1.00 | 34.44 | C |
| ATOM | 2034 | C | LYS | C | 26 | 32.167 | 36.871 | −31.652 | 1.00 | 35.28 | C |
| ATOM | 2035 | O | LYS | C | 26 | 31.939 | 37.717 | −32.521 | 1.00 | 35.06 | O |
| ATOM | 2036 | CB | LYS | C | 26 | 32.442 | 37.759 | −29.336 | 1.00 | 34.59 | C |
| ATOM | 2037 | CG | LYS | C | 26 | 32.498 | 39.236 | −29.715 | 1.00 | 35.12 | C |
| ATOM | 2038 | CD | LYS | C | 26 | 33.420 | 40.032 | −28.820 | 1.00 | 35.53 | C |
| ATOM | 2039 | CE | LYS | C | 26 | 33.366 | 41.500 | −29.176 | 1.00 | 35.99 | C |
| ATOM | 2040 | NZ | LYS | C | 26 | 34.484 | 42.228 | −28.523 | 1.00 | 38.19 | N |
| ATOM | 2041 | N | ASN | C | 27 | 32.968 | 35.830 | −31.854 | 1.00 | 35.47 | N |
| ATOM | 2042 | CA | ASN | C | 27 | 33.631 | 35.631 | −33.141 | 1.00 | 35.71 | C |
| ATOM | 2043 | C | ASN | C | 27 | 32.613 | 35.163 | −34.185 | 1.00 | 35.15 | C |
| ATOM | 2044 | O | ASN | C | 27 | 32.194 | 34.008 | −34.179 | 1.00 | 34.98 | O |
| ATOM | 2045 | CB | ASN | C | 27 | 34.756 | 34.591 | −33.007 | 1.00 | 35.80 | C |
| ATOM | 2046 | CG | ASN | C | 27 | 35.814 | 34.722 | −34.103 | 1.00 | 36.24 | C |
| ATOM | 2047 | OD1 | ASN | C | 27 | 36.616 | 33.811 | −34.331 | 1.00 | 35.61 | O |
| ATOM | 2048 | ND2 | ASN | C | 27 | 35.822 | 35.865 | −34.778 | 1.00 | 35.41 | N |
| ATOM | 2049 | N | GLY | C | 28 | 32.199 | 36.071 | −35.065 | 1.00 | 35.40 | N |
| ATOM | 2050 | CA | GLY | C | 28 | 31.241 | 35.713 | −36.101 | 1.00 | 35.14 | C |
| ATOM | 2051 | C | GLY | C | 28 | 29.775 | 35.667 | −35.683 | 1.00 | 35.73 | C |
| ATOM | 2052 | O | GLY | C | 28 | 28.888 | 35.664 | −36.530 | 1.00 | 35.03 | O |
| ATOM | 2053 | N | GLY | C | 29 | 29.507 | 35.616 | −34.385 | 1.00 | 36.14 | N |
| ATOM | 2054 | CA | GLY | C | 29 | 28.127 | 35.575 | −33.934 | 1.00 | 37.01 | C |
| ATOM | 2055 | C | GLY | C | 29 | 27.434 | 34.237 | −34.116 | 1.00 | 37.59 | C |
| ATOM | 2056 | O | GLY | C | 29 | 26.274 | 34.193 | −34.502 | 1.00 | 37.83 | O |
| ATOM | 2057 | N | PHE | C | 30 | 28.138 | 33.143 | −33.841 | 1.00 | 38.16 | N |
| ATOM | 2058 | CA | PHE | C | 30 | 27.554 | 31.808 | −33.962 | 1.00 | 38.35 | C |
| ATOM | 2059 | C | PHE | C | 30 | 27.167 | 31.274 | −32.580 | 1.00 | 38.48 | C |
| ATOM | 2060 | O | PHE | C | 30 | 27.818 | 31.582 | −31.582 | 1.00 | 38.33 | O |
| ATOM | 2061 | CB | PHE | C | 30 | 28.545 | 30.803 | −34.568 | 1.00 | 38.56 | C |
| ATOM | 2062 | CG | PHE | C | 30 | 29.103 | 31.195 | −35.905 | 1.00 | 39.05 | C |
| ATOM | 2063 | CD1 | PHE | C | 30 | 30.360 | 31.794 | −36.001 | 1.00 | 38.90 | C |
| ATOM | 2064 | CD2 | PHE | C | 30 | 28.415 | 30.886 | −37.077 | 1.00 | 39.67 | C |
| ATOM | 2065 | CE1 | PHE | C | 30 | 30.928 | 32.070 | −37.248 | 1.00 | 39.02 | C |
| ATOM | 2066 | CE2 | PHE | C | 30 | 28.970 | 31.159 | −38.329 | 1.00 | 39.02 | C |
| ATOM | 2067 | CZ | PHE | C | 30 | 30.230 | 31.750 | −38.413 | 1.00 | 39.48 | C |
| ATOM | 2068 | N | PHE | C | 31 | 26.114 | 30.466 | −32.535 | 1.00 | 38.05 | N |
| ATOM | 2069 | CA | PHE | C | 31 | 25.672 | 29.850 | −31.292 | 1.00 | 37.96 | C |
| ATOM | 2070 | C | PHE | C | 31 | 26.334 | 28.470 | −31.244 | 1.00 | 38.42 | C |
| ATOM | 2071 | O | PHE | C | 31 | 26.291 | 27.725 | −32.232 | 1.00 | 37.44 | O |
| ATOM | 2072 | CB | PHE | C | 31 | 24.145 | 29.680 | −31.277 | 1.00 | 38.03 | C |
| ATOM | 2073 | CG | PHE | C | 31 | 23.375 | 30.975 | −31.153 | 1.00 | 37.65 | C |
| ATOM | 2074 | CD1 | PHE | C | 31 | 23.471 | 31.752 | −30.003 | 1.00 | 37.96 | C |
| ATOM | 2075 | CD2 | PHE | C | 31 | 22.553 | 31.412 | −32.185 | 1.00 | 37.56 | C |
| ATOM | 2076 | CE1 | PHE | C | 31 | 22.761 | 32.949 | −29.878 | 1.00 | 37.78 | C |
| ATOM | 2077 | CE2 | PHE | C | 31 | 21.834 | 32.614 | −32.070 | 1.00 | 38.65 | C |
| ATOM | 2078 | CZ | PHE | C | 31 | 21.941 | 33.380 | −30.914 | 1.00 | 38.29 | C |
| ATOM | 2079 | N | LEU | C | 32 | 26.954 | 28.132 | −30.112 | 1.00 | 38.14 | N |
| ATOM | 2080 | CA | LEU | C | 32 | 27.603 | 26.828 | −29.973 | 1.00 | 38.60 | C |
| ATOM | 2081 | C | LEU | C | 32 | 26.556 | 25.736 | −30.182 | 1.00 | 38.90 | C |
| ATOM | 2082 | O | LEU | C | 32 | 25.507 | 25.754 | −29.545 | 1.00 | 39.37 | O |
| ATOM | 2083 | CB | LEU | C | 32 | 28.223 | 26.684 | −28.582 | 1.00 | 37.82 | C |
| ATOM | 2084 | CG | LEU | C | 32 | 29.052 | 25.416 | −28.349 | 1.00 | 37.38 | C |
| ATOM | 2085 | CD1 | LEU | C | 32 | 30.177 | 25.321 | −29.380 | 1.00 | 37.14 | C |
| ATOM | 2086 | CD2 | LEU | C | 32 | 29.626 | 25.447 | −26.948 | 1.00 | 37.29 | C |
| ATOM | 2087 | N | ARG | C | 33 | 26.842 | 24.784 | −31.063 | 1.00 | 39.19 | N |
| ATOM | 2088 | CA | ARG | C | 33 | 25.894 | 23.705 | −31.351 | 1.00 | 39.63 | C |
| ATOM | 2089 | C | ARG | C | 33 | 26.445 | 22.300 | −31.098 | 1.00 | 39.73 | C |
| ATOM | 2090 | O | ARG | C | 33 | 27.573 | 21.986 | −31.476 | 1.00 | 39.04 | O |
| ATOM | 2091 | CB | ARG | C | 33 | 25.411 | 23.804 | −32.807 | 1.00 | 38.58 | C |
| ATOM | 2092 | CG | ARG | C | 33 | 24.505 | 22.652 | −33.232 | 1.00 | 38.68 | C |
| ATOM | 2093 | CD | ARG | C | 33 | 23.823 | 22.919 | −34.566 | 1.00 | 37.94 | C |
| ATOM | 2094 | NE | ARG | C | 33 | 24.768 | 22.961 | −35.678 | 1.00 | 39.09 | N |
| ATOM | 2095 | CZ | ARG | C | 33 | 24.405 | 23.061 | −36.957 | 1.00 | 40.38 | C |
| ATOM | 2096 | NH1 | ARG | C | 33 | 23.113 | 23.131 | −37.277 | 1.00 | 40.24 | N |
| ATOM | 2097 | NH2 | ARG | C | 33 | 25.324 | 23.094 | −37.919 | 1.00 | 38.84 | N |

TABLE 3-continued

FGFR2(D2–D3) Complexed with FGF2

| ATOM | 2098 | N | ILE | C | 34 | 25.637 | 21.460 | −30.459 | 1.00 | 40.70 | N |
|---|---|---|---|---|---|---|---|---|---|---|---|
| ATOM | 2099 | CA | ILE | C | 34 | 26.033 | 20.085 | −30.163 | 1.00 | 42.62 | C |
| ATOM | 2100 | C | ILE | C | 34 | 25.067 | 19.125 | −30.867 | 1.00 | 44.12 | C |
| ATOM | 2101 | O | ILE | C | 34 | 23.924 | 18.952 | −30.439 | 1.00 | 44.15 | O |
| ATOM | 2102 | CB | ILE | C | 34 | 26.026 | 19.823 | −28.626 | 1.00 | 42.18 | C |
| ATOM | 2103 | CG1 | ILE | C | 34 | 27.040 | 20.743 | −27.934 | 1.00 | 41.54 | C |
| ATOM | 2104 | CG2 | ILE | C | 34 | 26.371 | 18.375 | −28.330 | 1.00 | 40.90 | C |
| ATOM | 2105 | CD1 | ILE | C | 34 | 27.035 | 20.641 | −26.415 | 1.00 | 41.02 | C |
| ATOM | 2106 | N | HIS | C | 35 | 25.542 | 18.512 | −31.949 | 1.00 | 45.92 | N |
| ATOM | 2107 | CA | HIS | C | 35 | 24.744 | 17.586 | −32.749 | 1.00 | 47.90 | C |
| ATOM | 2108 | C | HIS | C | 35 | 24.515 | 16.233 | −32.079 | 1.00 | 48.86 | C |
| ATOM | 2109 | O | HIS | C | 35 | 25.320 | 15.783 | −31.263 | 1.00 | 49.13 | O |
| ATOM | 2110 | CB | HIS | C | 35 | 25.391 | 17.383 | −34.124 | 1.00 | 47.30 | C |
| ATOM | 2111 | N | PRO | C | 36 | 23.402 | 15.563 | −32.429 | 1.00 | 50.20 | N |
| ATOM | 2112 | CA | PRO | C | 36 | 23.035 | 14.250 | −31.878 | 1.00 | 50.77 | C |
| ATOM | 2113 | C | PRO | C | 36 | 24.143 | 13.201 | −31.992 | 1.00 | 51.50 | C |
| ATOM | 2114 | O | PRO | C | 36 | 24.294 | 12.349 | −31.111 | 1.00 | 51.79 | O |
| ATOM | 2115 | CB | PRO | C | 36 | 21.806 | 13.867 | −32.698 | 1.00 | 50.84 | C |
| ATOM | 2116 | CG | PRO | C | 36 | 21.197 | 15.190 | −33.044 | 1.00 | 50.69 | C |
| ATOM | 2117 | CD | PRO | C | 36 | 22.400 | 16.016 | −33.411 | 1.00 | 50.54 | C |
| ATOM | 2118 | N | ASP | C | 37 | 24.915 | 13.265 | −33.077 | 1.00 | 51.91 | N |
| ATOM | 2119 | CA | ASP | C | 37 | 25.997 | 12.315 | −33.303 | 1.00 | 52.62 | C |
| ATOM | 2120 | C | ASP | C | 37 | 27.313 | 12.710 | −32.644 | 1.00 | 52.33 | C |
| ATOM | 2121 | O | ASP | C | 37 | 28.336 | 12.051 | −32.847 | 1.00 | 52.14 | O |
| ATOM | 2122 | CB | ASP | C | 37 | 26.231 | 12.111 | −34.805 | 1.00 | 54.39 | C |
| ATOM | 2123 | CG | ASP | C | 37 | 26.416 | 13.416 | −35.554 | 1.00 | 56.02 | C |
| ATOM | 2124 | OD1 | ASP | C | 37 | 25.401 | 14.098 | −35.811 | 1.00 | 57.55 | O |
| ATOM | 2125 | OD2 | ASP | C | 37 | 27.573 | 13.762 | −35.881 | 1.00 | 57.12 | O |
| ATOM | 2126 | N | GLY | C | 38 | 27.295 | 13.793 | −31.874 | 1.00 | 51.58 | N |
| ATOM | 2127 | CA | GLY | C | 38 | 28.504 | 14.214 | −31.191 | 1.00 | 50.83 | C |
| ATOM | 2128 | C | GLY | C | 38 | 29.416 | 15.231 | −31.858 | 1.00 | 49.91 | C |
| ATOM | 2129 | O | GLY | C | 38 | 30.478 | 15.545 | −31.319 | 1.00 | 50.15 | O |
| ATOM | 2130 | N | ARG | C | 39 | 29.034 | 15.750 | −33.018 | 1.00 | 48.93 | N |
| ATOM | 2131 | CA | ARG | C | 39 | 29.874 | 16.745 | −33.684 | 1.00 | 48.00 | C |
| ATOM | 2132 | C | ARG | C | 39 | 29.622 | 18.123 | −33.063 | 1.00 | 47.21 | C |
| ATOM | 2133 | O | ARG | C | 39 | 28.508 | 18.412 | −32.614 | 1.00 | 47.28 | O |
| ATOM | 2134 | CB | ARG | C | 39 | 29.571 | 16.786 | −35.186 | 1.00 | 47.46 | C |
| ATOM | 2135 | N | VAL | C | 40 | 30.648 | 18.968 | −33.029 | 1.00 | 45.62 | N |
| ATOM | 2136 | CA | VAL | C | 40 | 30.496 | 20.302 | −32.460 | 1.00 | 44.73 | C |
| ATOM | 2137 | C | VAL | C | 40 | 30.904 | 21.416 | −33.426 | 1.00 | 44.34 | C |
| ATOM | 2138 | O | VAL | C | 40 | 31.996 | 21.400 | −33.993 | 1.00 | 43.99 | O |
| ATOM | 2139 | CB | VAL | C | 40 | 31.310 | 20.451 | −31.139 | 1.00 | 44.63 | C |
| ATOM | 2140 | CG1 | VAL | C | 40 | 31.257 | 21.892 | −30.640 | 1.00 | 43.57 | C |
| ATOM | 2141 | CG2 | VAL | C | 40 | 30.753 | 19.517 | −30.078 | 1.00 | 43.53 | C |
| ATOM | 2142 | N | ASP | C | 41 | 30.006 | 22.380 | −33.603 | 1.00 | 43.77 | N |
| ATOM | 2143 | CA | ASP | C | 41 | 30.242 | 23.528 | −34.479 | 1.00 | 44.32 | C |
| ATOM | 2144 | C | ASP | C | 41 | 29.373 | 24.703 | −34.036 | 1.00 | 44.17 | C |
| ATOM | 2145 | O | ASP | C | 41 | 28.788 | 24.679 | −32.956 | 1.00 | 43.13 | O |
| ATOM | 2146 | CB | ASP | C | 41 | 29.919 | 23.178 | −35.944 | 1.00 | 44.59 | C |
| ATOM | 2147 | CG | ASP | C | 41 | 28.456 | 22.764 | −36.160 | 1.00 | 45.17 | C |
| ATOM | 2148 | OD1 | ASP | C | 41 | 28.115 | 22.409 | −37.313 | 1.00 | 45.54 | O |
| ATOM | 2149 | OD2 | ASP | C | 41 | 27.650 | 22.789 | −35.201 | 1.00 | 43.95 | O |
| ATOM | 2150 | N | GLY | C | 42 | 29.285 | 25.720 | −34.888 | 1.00 | 44.09 | N |
| ATOM | 2151 | CA | GLY | C | 42 | 28.478 | 26.879 | −34.577 | 1.00 | 44.88 | C |
| ATOM | 2152 | C | GLY | C | 42 | 27.509 | 27.198 | −35.701 | 1.00 | 45.42 | C |
| ATOM | 2153 | O | GLY | C | 42 | 27.751 | 26.837 | −36.846 | 1.00 | 45.76 | O |
| ATOM | 2154 | N | VAL | C | 43 | 26.400 | 27.853 | −35.367 | 1.00 | 45.71 | N |
| ATOM | 2155 | CA | VAL | C | 43 | 25.396 | 28.252 | −36.350 | 1.00 | 46.21 | C |
| ATOM | 2156 | C | VAL | C | 43 | 24.751 | 29.554 | −35.922 | 1.00 | 46.88 | C |
| ATOM | 2157 | O | VAL | C | 43 | 24.715 | 29.879 | −34.735 | 1.00 | 45.90 | O |
| ATOM | 2158 | CB | VAL | C | 43 | 24.262 | 27.209 | −36.537 | 1.00 | 45.90 | C |
| ATOM | 2159 | CG1 | VAL | C | 43 | 24.832 | 25.948 | −37.106 | 1.00 | 46.54 | C |
| ATOM | 2160 | CG2 | VAL | C | 43 | 23.533 | 26.952 | −35.223 | 1.00 | 44.87 | C |
| ATOM | 2161 | N | ARG | C | 44 | 24.230 | 30.289 | −36.898 | 1.00 | 47.36 | N |
| ATOM | 2162 | CA | ARG | C | 44 | 23.593 | 31.572 | −36.646 | 1.00 | 48.59 | C |
| ATOM | 2163 | C | ARG | C | 44 | 22.088 | 31.496 | −36.368 | 1.00 | 49.22 | C |
| ATOM | 2164 | O | ARG | C | 44 | 21.530 | 32.391 | −35.731 | 1.00 | 49.22 | O |
| ATOM | 2165 | CB | ARG | C | 44 | 23.829 | 32.511 | −37.838 | 1.00 | 48.96 | C |
| ATOM | 2166 | CG | ARG | C | 44 | 25.285 | 32.907 | −38.098 | 1.00 | 49.81 | C |
| ATOM | 2167 | CD | ARG | C | 44 | 25.352 | 34.051 | −39.117 | 1.00 | 50.07 | C |
| ATOM | 2168 | NE | ARG | C | 44 | 26.646 | 34.735 | −39.135 | 1.00 | 51.51 | N |
| ATOM | 2169 | CZ | ARG | C | 44 | 27.766 | 34.229 | −39.649 | 1.00 | 52.44 | C |
| ATOM | 2170 | NH1 | ARG | C | 44 | 27.765 | 33.024 | −40.199 | 1.00 | 53.50 | N |
| ATOM | 2171 | NH2 | ARG | C | 44 | 28.892 | 34.931 | −39.613 | 1.00 | 52.25 | N |
| ATOM | 2172 | N | GLU | C | 45 | 21.432 | 30.440 | −36.844 | 1.00 | 49.98 | N |
| ATOM | 2173 | CA | GLU | C | 45 | 19.983 | 30.291 | −36.665 | 1.00 | 50.43 | C |
| ATOM | 2174 | C | GLU | C | 45 | 19.553 | 30.052 | −35.214 | 1.00 | 50.75 | C |

TABLE 3-continued

| FGFR2(D2–D3) Complexed with FGF2 | | | | | | | | | | |
|---|---|---|---|---|---|---|---|---|---|---|
| ATOM | 2175 | O | GLU | C | 45 | 19.693 | 28.950 | −34.684 | 1.00 | 50.31 | O |
| ATOM | 2176 | CB | GLU | C | 45 | 19.456 | 29.157 | −37.553 | 1.00 | 49.68 | C |
| ATOM | 2177 | N | LYS | C | 46 | 19.015 | 31.095 | −34.588 | 1.00 | 51.13 | N |
| ATOM | 2178 | CA | LYS | C | 46 | 18.563 | 31.029 | −33.203 | 1.00 | 51.85 | C |
| ATOM | 2179 | C | LYS | C | 46 | 17.496 | 29.955 | −32.975 | 1.00 | 52.54 | C |
| ATOM | 2180 | O | LYS | C | 46 | 17.197 | 29.598 | −31.837 | 1.00 | 52.62 | O |
| ATOM | 2181 | CB | LYS | C | 46 | 18.013 | 32.393 | −32.771 | 1.00 | 50.92 | C |
| ATOM | 2182 | N | SER | C | 47 | 16.940 | 29.436 | −34.062 | 1.00 | 53.02 | N |
| ATOM | 2183 | CA | SER | C | 47 | 15.893 | 28.422 | −33.998 | 1.00 | 53.18 | C |
| ATOM | 2184 | C | SER | C | 47 | 16.393 | 26.980 | −33.894 | 1.00 | 52.59 | C |
| ATOM | 2185 | O | SER | C | 47 | 15.634 | 26.077 | −33.533 | 1.00 | 52.38 | O |
| ATOM | 2186 | CB | SER | C | 47 | 14.998 | 28.559 | −35.234 | 1.00 | 53.53 | C |
| ATOM | 2187 | OG | SER | C | 47 | 14.065 | 27.500 | −35.309 | 1.00 | 54.44 | O |
| ATOM | 2188 | N | ASP | C | 48 | 17.662 | 26.763 | −34.218 | 1.00 | 51.97 | N |
| ATOM | 2189 | CA | ASP | C | 48 | 18.233 | 25.422 | −34.168 | 1.00 | 51.11 | C |
| ATOM | 2190 | C | ASP | C | 48 | 18.029 | 24.762 | −32.809 | 1.00 | 50.64 | C |
| ATOM | 2191 | O | ASP | C | 48 | 18.398 | 25.322 | −31.777 | 1.00 | 51.03 | O |
| ATOM | 2192 | CB | ASP | C | 48 | 19.725 | 25.466 | −34.493 | 1.00 | 50.52 | C |
| ATOM | 2193 | CG | ASP | C | 48 | 20.324 | 24.084 | −34.659 | 1.00 | 50.05 | C |
| ATOM | 2194 | OD1 | ASP | C | 48 | 20.996 | 23.853 | −35.684 | 1.00 | 50.30 | O |
| ATOM | 2195 | OD2 | ASP | C | 48 | 20.123 | 23.228 | −33.773 | 1.00 | 49.16 | O |
| ATOM | 2196 | N | PRO | C | 49 | 17.436 | 23.555 | −32.794 | 1.00 | 50.16 | N |
| ATOM | 2197 | CA | PRO | C | 49 | 17.174 | 22.800 | −31.564 | 1.00 | 49.31 | C |
| ATOM | 2198 | C | PRO | C | 49 | 18.416 | 22.240 | −30.865 | 1.00 | 48.74 | C |
| ATOM | 2199 | O | PRO | C | 49 | 18.332 | 21.775 | −29.724 | 1.00 | 48.49 | O |
| ATOM | 2200 | CB | PRO | C | 49 | 16.242 | 21.685 | −32.036 | 1.00 | 49.47 | C |
| ATOM | 2201 | CG | PRO | C | 49 | 16.703 | 21.441 | −33.442 | 1.00 | 49.53 | C |
| ATOM | 2202 | CD | PRO | C | 49 | 16.876 | 22.853 | −33.964 | 1.00 | 49.76 | C |
| ATOM | 2203 | N | HIS | C | 50 | 19.563 | 22.281 | −31.537 | 1.00 | 47.05 | N |
| ATOM | 2204 | CA | HIS | C | 50 | 20.787 | 21.755 | −30.943 | 1.00 | 46.14 | C |
| ATOM | 2205 | C | HIS | C | 50 | 21.742 | 22.788 | −30.324 | 1.00 | 44.53 | C |
| ATOM | 2206 | O | HIS | C | 50 | 22.917 | 22.493 | −30.093 | 1.00 | 44.37 | O |
| ATOM | 2207 | CB | HIS | C | 50 | 21.525 | 20.893 | −31.972 | 1.00 | 46.67 | C |
| ATOM | 2208 | CG | HIS | C | 50 | 20.718 | 19.726 | −32.451 | 1.00 | 48.02 | C |
| ATOM | 2209 | ND1 | HIS | C | 50 | 20.261 | 18.741 | −31.602 | 1.00 | 48.41 | N |
| ATOM | 2210 | CD2 | HIS | C | 50 | 20.243 | 19.412 | −33.680 | 1.00 | 48.11 | C |
| ATOM | 2211 | CE1 | HIS | C | 50 | 19.537 | 17.874 | −32.285 | 1.00 | 48.32 | C |
| ATOM | 2212 | NE2 | HIS | C | 50 | 19.510 | 18.257 | −33.548 | 1.00 | 48.66 | N |
| ATOM | 2213 | N | ILE | C | 51 | 21.237 | 23.989 | −30.052 | 1.00 | 42.64 | N |
| ATOM | 2214 | CA | ILE | C | 51 | 22.047 | 25.042 | −29.430 | 1.00 | 41.45 | C |
| ATOM | 2215 | C | ILE | C | 51 | 21.567 | 25.291 | −28.001 | 1.00 | 40.92 | C |
| ATOM | 2216 | O | ILE | C | 51 | 22.129 | 26.113 | −27.278 | 1.00 | 40.64 | O |
| ATOM | 2217 | CB | ILE | C | 51 | 21.964 | 26.382 | −30.206 | 1.00 | 40.29 | C |
| ATOM | 2218 | CG1 | ILE | C | 51 | 20.518 | 26.884 | −30.221 | 1.00 | 39.12 | C |
| ATOM | 2219 | CG2 | ILE | C | 51 | 22.506 | 26.207 | −31.617 | 1.00 | 39.60 | C |
| ATOM | 2220 | CD1 | ILE | C | 51 | 20.303 | 28.100 | −31.071 | 1.00 | 37.67 | C |
| ATOM | 2221 | N | LYS | C | 52 | 20.508 | 24.593 | −27.604 | 1.00 | 40.16 | N |
| ATOM | 2222 | CA | LYS | C | 52 | 19.976 | 24.717 | −26.253 | 1.00 | 39.24 | C |
| ATOM | 2223 | C | LYS | C | 52 | 20.881 | 23.885 | −25.346 | 1.00 | 37.79 | C |
| ATOM | 2224 | O | LYS | C | 52 | 20.920 | 22.669 | −25.451 | 1.00 | 37.86 | O |
| ATOM | 2225 | CB | LYS | C | 52 | 18.539 | 24.200 | −26.209 | 1.00 | 40.26 | C |
| ATOM | 2226 | CG | LYS | C | 52 | 17.954 | 24.113 | −24.812 | 1.00 | 42.44 | C |
| ATOM | 2227 | CD | LYS | C | 52 | 16.433 | 24.038 | −24.863 | 1.00 | 44.69 | C |
| ATOM | 2228 | CE | LYS | C | 52 | 15.850 | 23.890 | −23.462 | 1.00 | 45.74 | C |
| ATOM | 2229 | NZ | LYS | C | 52 | 14.364 | 23.999 | −23.484 | 1.00 | 47.05 | N |
| ATOM | 2230 | N | LEU | C | 53 | 21.615 | 24.550 | −24.461 | 1.00 | 35.96 | N |
| ATOM | 2231 | CA | LEU | C | 53 | 22.556 | 23.865 | −23.585 | 1.00 | 34.34 | C |
| ATOM | 2232 | C | LEU | C | 53 | 22.210 | 23.958 | −22.106 | 1.00 | 33.68 | C |
| ATOM | 2233 | O | LEU | C | 53 | 21.478 | 24.845 | −21.674 | 1.00 | 34.17 | O |
| ATOM | 2234 | CB | LEU | C | 53 | 23.958 | 24.432 | −23.815 | 1.00 | 33.01 | C |
| ATOM | 2235 | CG | LEU | C | 53 | 24.375 | 24.500 | −25.285 | 1.00 | 33.28 | C |
| ATOM | 2236 | CD1 | LEU | C | 53 | 25.676 | 25.300 | −25.446 | 1.00 | 31.49 | C |
| ATOM | 2237 | CD2 | LEU | C | 53 | 24.518 | 23.078 | −25.826 | 1.00 | 32.99 | C |
| ATOM | 2238 | N | GLN | C | 54 | 22.748 | 23.032 | −21.328 | 1.00 | 32.23 | N |
| ATOM | 2239 | CA | GLN | C | 54 | 22.496 | 23.037 | −19.903 | 1.00 | 31.29 | C |
| ATOM | 2240 | C | GLN | C | 54 | 23.831 | 23.018 | −19.151 | 1.00 | 31.12 | C |
| ATOM | 2241 | O | GLN | C | 54 | 24.582 | 22.035 | −19.214 | 1.00 | 30.63 | O |
| ATOM | 2242 | CB | GLN | C | 54 | 21.616 | 21.831 | −19.527 | 1.00 | 30.23 | C |
| ATOM | 2243 | CG | GLN | C | 54 | 21.285 | 21.721 | −18.049 | 1.00 | 31.21 | C |
| ATOM | 2244 | CD | GLN | C | 54 | 20.529 | 22.939 | −17.505 | 1.00 | 33.60 | C |
| ATOM | 2245 | OE1 | GLN | C | 54 | 19.359 | 23.173 | −17.841 | 1.00 | 33.50 | O |
| ATOM | 2246 | NE2 | GLN | C | 54 | 21.203 | 23.721 | −16.660 | 1.00 | 32.61 | N |
| ATOM | 2247 | N | LEU | C | 55 | 24.132 | 24.117 | −18.458 | 1.00 | 30.81 | N |
| ATOM | 2248 | CA | LEU | C | 55 | 25.365 | 24.211 | −17.682 | 1.00 | 31.21 | C |
| ATOM | 2249 | C | LUE | C | 55 | 25.113 | 23.681 | −16.280 | 1.00 | 30.69 | C |
| ATOM | 2250 | O | LEU | C | 55 | 24.007 | 23.796 | −15.762 | 1.00 | 30.33 | O |
| ATOM | 2251 | CB | LEU | C | 55 | 25.858 | 25.662 | −17.569 | 1.00 | 31.94 | C |

TABLE 3-continued

FGFR2(D2–D3) Complexed with FGF2

| ATOM | 2252 | CG | LEU | C | 55 | 26.391 | 26.397 | −18.797 | 1.00 | 33.07 | C |
|---|---|---|---|---|---|---|---|---|---|---|---|
| ATOM | 2253 | CD1 | LEU | C | 55 | 27.101 | 27.684 | −18.361 | 1.00 | 33.51 | C |
| ATOM | 2254 | CD2 | LEU | C | 55 | 27.369 | 25.517 | −19.516 | 1.00 | 34.11 | C |
| ATOM | 2255 | N | GLN | C | 56 | 26.144 | 23.107 | −15.668 | 1.00 | 29.95 | N |
| ATOM | 2256 | CA | GLN | C | 56 | 26.040 | 22.572 | −14.313 | 1.00 | 30.16 | C |
| ATOM | 2257 | C | GLN | C | 56 | 27.417 | 22.621 | −13.646 | 1.00 | 29.98 | C |
| ATOM | 2258 | O | GLN | C | 56 | 28.396 | 22.125 | −14.193 | 1.00 | 28.97 | O |
| ATOM | 2259 | CB | GLN | C | 56 | 25.525 | 21.126 | −14.338 | 1.00 | 30.67 | C |
| ATOM | 2260 | CG | GLN | C | 56 | 25.592 | 20.398 | −12.979 | 1.00 | 30.83 | C |
| ATOM | 2261 | CD | GLN | C | 56 | 24.680 | 21.001 | −11.919 | 1.00 | 32.27 | C |
| ATOM | 2262 | OE1 | GLN | C | 56 | 23.456 | 21.059 | −12.090 | 1.00 | 30.94 | O |
| ATOM | 2263 | NE2 | GLN | C | 56 | 25.272 | 21.447 | −10.812 | 1.00 | 31.22 | N |
| ATOM | 2264 | N | ALA | C | 57 | 27.489 | 23.231 | −12.468 | 1.00 | 30.09 | N |
| ATOM | 2265 | CA | ALA | C | 57 | 28.761 | 23.334 | −11.762 | 1.00 | 31.02 | C |
| ATOM | 2266 | C | ALA | C | 57 | 29.104 | 22.006 | −11.088 | 1.00 | 30.87 | C |
| ATOM | 2267 | O | ALA | C | 57 | 28.238 | 21.361 | −10.493 | 1.00 | 30.82 | O |
| ATOM | 2268 | CB | ALA | C | 57 | 28.701 | 24.459 | −10.717 | 1.00 | 30.35 | C |
| ATOM | 2269 | N | GLU | C | 58 | 30.368 | 21.602 | −11.186 | 1.00 | 31.25 | N |
| ATOM | 2270 | CA | GLU | C | 58 | 30.831 | 20.348 | −10.583 | 1.00 | 31.67 | C |
| ATOM | 2271 | C | GLU | C | 58 | 31.549 | 20.697 | −9.277 | 1.00 | 32.32 | C |
| ATOM | 2272 | O | GLU | C | 58 | 31.546 | 19.927 | −8.312 | 1.00 | 32.40 | O |
| ATOM | 2273 | CB | GLU | C | 58 | 31.790 | 19.636 | −11.540 | 1.00 | 31.38 | C |
| ATOM | 2274 | CG | GLU | C | 58 | 32.028 | 18.164 | −11.239 | 1.00 | 33.29 | C |
| ATOM | 2275 | CD | GLU | C | 58 | 30.737 | 17.347 | −11.170 | 1.00 | 33.63 | C |
| ATOM | 2276 | OE1 | GLU | C | 58 | 29.779 | 17.659 | −11.907 | 1.00 | 32.82 | O |
| ATOM | 2277 | OE2 | GLU | C | 58 | 30.692 | 16.378 | −10.383 | 1.00 | 35.39 | O |
| ATOM | 2278 | N | GLU | C | 59 | 32.166 | 21.876 | −9.279 | 1.00 | 32.68 | N |
| ATOM | 2279 | CA | GLU | C | 59 | 32.892 | 22.422 | −8.140 | 1.00 | 33.77 | C |
| ATOM | 2280 | C | GLU | C | 59 | 32.978 | 23.932 | −8.400 | 1.00 | 33.03 | C |
| ATOM | 2281 | O | GLU | C | 59 | 32.665 | 24.395 | −9.504 | 1.00 | 32.28 | O |
| ATOM | 2282 | CB | GLU | C | 59 | 34.309 | 21.807 | −8.042 | 1.00 | 35.98 | C |
| ATOM | 2283 | CG | GLU | C | 59 | 35.430 | 22.589 | −8.751 | 1.00 | 39.17 | C |
| ATOM | 2284 | CD | GLU | C | 59 | 36.776 | 21.852 | −8.766 | 1.00 | 41.17 | C |
| ATOM | 2285 | OE1 | GLU | C | 59 | 36.912 | 20.863 | −9.509 | 1.00 | 40.92 | O |
| ATOM | 2286 | OE2 | GLU | C | 59 | 37.706 | 22.258 | −8.036 | 1.00 | 43.20 | O |
| ATOM | 2287 | N | ARG | C | 60 | 33.408 | 24.699 | −7.403 | 1.00 | 31.97 | N |
| ATOM | 2288 | CA | ARG | C | 60 | 33.497 | 26.146 | −7.569 | 1.00 | 32.57 | C |
| ATOM | 2289 | C | ARG | C | 60 | 34.213 | 26.577 | −8.855 | 1.00 | 32.05 | C |
| ATOM | 2290 | O | ARG | C | 60 | 35.356 | 26.198 | −9.095 | 1.00 | 31.53 | O |
| ATOM | 2291 | CB | ARG | C | 60 | 34.184 | 26.788 | −6.353 | 1.00 | 34.46 | C |
| ATOM | 2292 | CG | ARG | C | 60 | 34.301 | 28.305 | −6.462 | 1.00 | 36.45 | C |
| ATOM | 2293 | CD | ARG | C | 60 | 34.748 | 28.940 | −5.157 | 1.00 | 39.28 | C |
| ATOM | 2294 | NE | ARG | C | 60 | 35.277 | 30.277 | −5.390 | 1.00 | 43.60 | N |
| ATOM | 2295 | CZ | ARG | C | 60 | 36.568 | 30.565 | −5.524 | 1.00 | 44.35 | C |
| ATOM | 2296 | NH1 | ARG | C | 60 | 37.488 | 29.612 | −5.440 | 1.00 | 45.40 | N |
| ATOM | 2297 | NH2 | ARG | C | 60 | 36.939 | 31.813 | −5.762 | 1.00 | 46.19 | N |
| ATOM | 2298 | N | GLY | C | 61 | 33.524 | 27.360 | −9.684 | 1.00 | 31.00 | N |
| ATOM | 2299 | CA | GLY | C | 61 | 34.111 | 27.837 | −10.927 | 1.00 | 29.64 | C |
| ATOM | 2300 | C | GLY | C | 61 | 34.347 | 26.824 | −12.049 | 1.00 | 29.20 | C |
| ATOM | 2301 | O | GLY | C | 61 | 34.964 | 27.159 | −13.055 | 1.00 | 28.82 | O |
| ATOM | 2302 | N | VAL | C | 62 | 33.864 | 25.595 | −11.889 | 1.00 | 28.84 | N |
| ATOM | 2303 | CA | VAL | C | 62 | 34.033 | 24.562 | −12.907 | 1.00 | 28.12 | C |
| ATOM | 2304 | C | VAL | C | 62 | 32.683 | 24.014 | −13.363 | 1.00 | 28.05 | C |
| ATOM | 2305 | O | VAL | C | 62 | 31.858 | 23.613 | −12.543 | 1.00 | 27.91 | O |
| ATOM | 2306 | CB | VAL | C | 62 | 34.872 | 23.389 | −12.372 | 1.00 | 30.05 | C |
| ATOM | 2307 | CG1 | VAL | C | 62 | 34.900 | 22.249 | −13.396 | 1.00 | 29.55 | C |
| ATOM | 2308 | CG2 | VAL | C | 62 | 36.290 | 23.876 | −12.058 | 1.00 | 31.46 | C |
| ATOM | 2309 | N | VAL | C | 63 | 32.464 | 23.975 | −14.674 | 1.00 | 26.85 | N |
| ATOM | 2310 | CA | VAL | C | 63 | 31.194 | 23.489 | −15.194 | 1.00 | 25.70 | C |
| ATOM | 2311 | C | VAL | C | 63 | 31.299 | 22.425 | −16.288 | 1.00 | 26.60 | C |
| ATOM | 2312 | O | VAL | C | 63 | 32.358 | 22.231 | −16.906 | 1.00 | 25.54 | O |
| ATOM | 2313 | CB | VAL | C | 63 | 30.347 | 24.656 | −15.794 | 1.00 | 25.51 | C |
| ATOM | 2314 | CG1 | VAL | C | 63 | 30.211 | 25.805 | −14.787 | 1.00 | 24.24 | C |
| ATOM | 2315 | CG2 | VAL | C | 63 | 30.992 | 25.153 | −17.101 | 1.00 | 24.50 | C |
| ATOM | 2316 | N | SER | C | 64 | 30.177 | 21.737 | −16.502 | 1.00 | 26.80 | N |
| ATOM | 2317 | CA | SER | C | 64 | 30.036 | 20.748 | −17.563 | 1.00 | 27.74 | C |
| ATOM | 2318 | C | SER | C | 64 | 28.977 | 21.384 | −18.458 | 1.00 | 28.09 | C |
| ATOM | 2319 | O | SER | C | 64 | 28.063 | 22.044 | −17.961 | 1.00 | 28.39 | O |
| ATOM | 2320 | CB | SER | C | 64 | 29.522 | 19.405 | −17.023 | 1.00 | 28.22 | C |
| ATOM | 2321 | OG | SER | C | 64 | 28.186 | 19.471 | −16.558 | 1.00 | 28.00 | O |
| ATOM | 2322 | N | ILE | C | 65 | 29.101 | 21.211 | −19.766 | 1.00 | 28.42 | N |
| ATOM | 2323 | CA | ILE | C | 65 | 28.144 | 21.787 | −20.701 | 1.00 | 29.32 | C |
| ATOM | 2324 | C | ILE | C | 65 | 27.470 | 20.666 | −21.501 | 1.00 | 30.69 | C |
| ATOM | 2325 | O | ILE | C | 65 | 28.122 | 19.950 | −22.261 | 1.00 | 30.99 | O |
| ATOM | 2326 | CB | ILE | C | 65 | 28.863 | 22.778 | −21.640 | 1.00 | 28.28 | C |
| ATOM | 2327 | CG1 | ILE | C | 65 | 29.612 | 23.823 | −20.797 | 1.00 | 27.41 | C |
| ATOM | 2328 | CG2 | ILE | C | 65 | 27.856 | 23.442 | −22.574 | 1.00 | 28.34 | C |

TABLE 3-continued

FGFR2(D2–D3) Complexed with FGF2

| ATOM | 2329 | CD1 | ILE | C | 65 | 30.471 | 24.785 | −21.597 | 1.00 | 24.84 | C |
|---|---|---|---|---|---|---|---|---|---|---|---|
| ATOM | 2330 | N | LYS | C | 66 | 26.161 | 20.523 | −21.333 | 1.00 | 32.55 | N |
| ATOM | 2331 | CA | LYS | C | 66 | 25.421 | 19.447 | −21.995 | 1.00 | 34.96 | C |
| ATOM | 2332 | C | LYS | C | 66 | 24.381 | 19.875 | −23.027 | 1.00 | 35.82 | C |
| ATOM | 2333 | O | LYS | C | 66 | 23.536 | 20.726 | −22.753 | 1.00 | 36.26 | O |
| ATOM | 2334 | CB | LYS | C | 66 | 24.751 | 18.589 | −20.913 | 1.00 | 37.11 | C |
| ATOM | 2335 | CG | LYS | C | 66 | 23.960 | 17.367 | −21.383 | 1.00 | 38.86 | C |
| ATOM | 2336 | CD | LYS | C | 66 | 23.401 | 16.636 | −20.159 | 1.00 | 41.20 | C |
| ATOM | 2337 | CE | LYS | C | 66 | 22.492 | 15.473 | −20.527 | 1.00 | 42.68 | C |
| ATOM | 2338 | NZ | LYS | C | 66 | 21.233 | 15.954 | −21.158 | 1.00 | 44.01 | N |
| ATOM | 2339 | N | GLY | C | 67 | 24.454 | 19.284 | −24.218 | 1.00 | 37.05 | N |
| ATOM | 2340 | CA | GLY | C | 67 | 23.482 | 19.587 | −25.254 | 1.00 | 38.80 | C |
| ATOM | 2341 | C | GLY | C | 67 | 22.191 | 18.873 | −24.883 | 1.00 | 40.43 | C |
| ATOM | 2342 | O | GLY | C | 67 | 22.153 | 17.645 | −24.816 | 1.00 | 39.87 | O |
| ATOM | 2343 | N | VAL | C | 68 | 21.133 | 19.635 | −24.626 | 1.00 | 41.85 | N |
| ATOM | 2344 | CA | VAL | C | 68 | 19.856 | 19.047 | −24.236 | 1.00 | 43.71 | C |
| ATOM | 2345 | C | VAL | C | 68 | 19.313 | 18.054 | −25.264 | 1.00 | 44.52 | C |
| ATOM | 2346 | O | VAL | C | 68 | 18.976 | 16.921 | −24.914 | 1.00 | 45.01 | O |
| ATOM | 2347 | CB | VAL | C | 68 | 18.782 | 20.142 | −23.986 | 1.00 | 43.95 | C |
| ATOM | 2348 | CG1 | VAL | C | 68 | 17.489 | 19.498 | −23.480 | 1.00 | 44.00 | C |
| ATOM | 2349 | CG2 | VAL | C | 68 | 19.297 | 21.159 | −22.969 | 1.00 | 44.05 | C |
| ATOM | 2350 | N | SER | C | 69 | 19.232 | 18.472 | −26.527 | 1.00 | 45.03 | N |
| ATOM | 2351 | CA | SER | C | 69 | 18.714 | 17.599 | −27.585 | 1.00 | 45.87 | C |
| ATOM | 2352 | C | SER | C | 69 | 19.587 | 16.361 | −27.804 | 1.00 | 45.68 | C |
| ATOM | 2353 | O | SER | C | 69 | 19.114 | 15.227 | −27.700 | 1.00 | 45.84 | O |
| ATOM | 2354 | CB | SER | C | 69 | 18.575 | 18.378 | −28.901 | 1.00 | 44.99 | C |
| ATOM | 2355 | N | ALA | C | 70 | 20.864 | 16.588 | −28.093 | 1.00 | 45.74 | N |
| ATOM | 2356 | CA | ALA | C | 70 | 21.806 | 15.505 | −28.334 | 1.00 | 45.43 | C |
| ATOM | 2357 | C | ALA | C | 70 | 22.010 | 14.612 | −27.115 | 1.00 | 45.74 | C |
| ATOM | 2358 | O | ALA | C | 70 | 22.471 | 13.481 | −27.242 | 1.00 | 46.07 | O |
| ATOM | 2359 | CB | ALA | C | 70 | 23.135 | 16.081 | −28.770 | 1.00 | 46.08 | C |
| ATOM | 2360 | N | ASN | C | 71 | 21.661 | 15.122 | −25.937 | 1.00 | 45.57 | N |
| ATOM | 2361 | CA | ASN | C | 71 | 21.838 | 14.385 | −24.690 | 1.00 | 45.32 | C |
| ATOM | 2362 | C | ASN | C | 71 | 23.301 | 13.946 | −24.532 | 1.00 | 44.61 | C |
| ATOM | 2363 | O | ASN | C | 71 | 23.583 | 12.835 | −24.070 | 1.00 | 44.13 | O |
| ATOM | 2364 | CB | ASN | C | 71 | 20.911 | 13.160 | −24.637 | 1.00 | 45.62 | C |
| ATOM | 2365 | CG | ASN | C | 71 | 20.814 | 12.557 | −23.236 | 1.00 | 46.15 | C |
| ATOM | 2366 | OD1 | ASN | C | 71 | 20.546 | 13.264 | −22.254 | 1.00 | 46.61 | O |
| ATOM | 2367 | ND2 | ASN | C | 71 | 21.020 | 11.245 | −23.140 | 1.00 | 45.81 | N |
| ATOM | 2368 | N | ARG | C | 72 | 24.221 | 14.834 | −24.917 | 1.00 | 43.86 | N |
| ATOM | 2369 | CA | ARG | C | 72 | 25.662 | 14.577 | −24.824 | 1.00 | 43.26 | C |
| ATOM | 2370 | C | ARG | C | 72 | 26.375 | 15.733 | −24.125 | 1.00 | 42.40 | C |
| ATOM | 2371 | O | ARG | C | 72 | 25.853 | 16.848 | −24.070 | 1.00 | 42.22 | O |
| ATOM | 2372 | CB | ARG | C | 72 | 26.278 | 14.394 | −26.214 | 1.00 | 43.88 | C |
| ATOM | 2373 | CG | ARG | C | 72 | 25.953 | 13.084 | −26.921 | 1.00 | 44.93 | C |
| ATOM | 2374 | CD | ARG | C | 72 | 26.422 | 13.167 | −28.370 | 1.00 | 46.45 | C |
| ATOM | 2375 | NE | ARG | C | 72 | 26.143 | 11.964 | −29.152 | 1.00 | 47.61 | N |
| ATOM | 2376 | CZ | ARG | C | 72 | 27.012 | 10.977 | −29.346 | 1.00 | 48.45 | C |
| ATOM | 2377 | NH1 | ARG | C | 72 | 28.227 | 11.040 | −28.811 | 1.00 | 48.67 | N |
| ATOM | 2378 | NH2 | ARG | C | 72 | 26.671 | 9.930 | −30.091 | 1.00 | 48.13 | N |
| ATOM | 2379 | N | TYR | C | 73 | 27.576 | 15.457 | −23.614 | 1.00 | 40.54 | N |
| ATOM | 2380 | CA | TYR | C | 73 | 28.388 | 16.443 | −22.904 | 1.00 | 38.82 | C |
| ATOM | 2381 | C | TYR | C | 73 | 29.579 | 16.942 | −23.719 | 1.00 | 38.37 | C |
| ATOM | 2382 | O | TYR | C | 73 | 30.329 | 16.152 | −24.289 | 1.00 | 37.39 | O |
| ATOM | 2383 | CB | TYR | C | 73 | 28.899 | 15.851 | −21.586 | 1.00 | 37.69 | C |
| ATOM | 2384 | CG | TYR | C | 73 | 27.804 | 15.496 | −20.602 | 1.00 | 37.26 | C |
| ATOM | 2385 | CD1 | TYR | C | 73 | 27.081 | 14.305 | −20.717 | 1.00 | 36.64 | C |
| ATOM | 2386 | CD2 | TYR | C | 73 | 27.483 | 16.360 | −19.555 | 1.00 | 36.86 | C |
| ATOM | 2387 | CE1 | TYR | C | 73 | 26.066 | 13.986 | −19.806 | 1.00 | 37.14 | C |
| ATOM | 2388 | CE2 | TYR | C | 73 | 26.476 | 16.054 | −18.648 | 1.00 | 36.35 | C |
| ATOM | 2389 | CZ | TYR | C | 73 | 25.771 | 14.872 | −18.776 | 1.00 | 36.93 | C |
| ATOM | 2390 | OH | TYR | C | 73 | 24.762 | 14.607 | −17.880 | 1.00 | 36.77 | O |
| ATOM | 2391 | N | LEU | C | 74 | 29.754 | 18.259 | −23.762 | 1.00 | 37.92 | N |
| ATOM | 2392 | CA | LEU | C | 74 | 30.866 | 18.866 | −24.492 | 1.00 | 38.18 | C |
| ATOM | 2393 | C | LEU | C | 74 | 32.184 | 18.368 | −23.897 | 1.00 | 38.61 | C |
| ATOM | 2394 | O | LEU | C | 74 | 32.295 | 18.204 | −22.685 | 1.00 | 38.88 | O |
| ATOM | 2395 | CB | LEU | C | 74 | 30.797 | 20.396 | −24.376 | 1.00 | 38.05 | C |
| ATOM | 2396 | CG | LEU | C | 74 | 31.824 | 21.247 | −25.131 | 1.00 | 38.02 | C |
| ATOM | 2397 | CD1 | LEU | C | 74 | 31.495 | 21.250 | −26.622 | 1.00 | 37.84 | C |
| ATOM | 2398 | CD2 | LEU | C | 74 | 31.806 | 22.664 | −24.602 | 1.00 | 37.13 | C |
| ATOM | 2399 | N | ALA | C | 75 | 33.178 | 18.125 | −24.744 | 1.00 | 39.31 | N |
| ATOM | 2400 | CA | ALA | C | 75 | 34.475 | 17.653 | −24.274 | 1.00 | 40.12 | C |
| ATOM | 2401 | C | ALA | C | 75 | 35.599 | 18.081 | −25.200 | 1.00 | 40.53 | C |
| ATOM | 2402 | O | ALA | C | 75 | 35.389 | 18.295 | −26.393 | 1.00 | 39.68 | O |
| ATOM | 2403 | CB | ALA | C | 75 | 34.472 | 16.139 | −24.154 | 1.00 | 39.77 | C |
| ATOM | 2404 | N | MET | C | 76 | 36.793 | 18.215 | −24.638 | 1.00 | 41.78 | N |
| ATOM | 2405 | CA | MET | C | 76 | 37.960 | 18.577 | −25.428 | 1.00 | 43.24 | C |

TABLE 3-continued

FGFR2(D2–D3) Complexed with FGF2

| ATOM | 2406 | C | MET | C | 76 | 38.972 | 17.445 | −25.305 | 1.00 | 44.15 | C |
|---|---|---|---|---|---|---|---|---|---|---|---|
| ATOM | 2407 | O | MET | C | 76 | 39.382 | 17.086 | −24.200 | 1.00 | 43.31 | O |
| ATOM | 2408 | CB | MET | C | 76 | 38.588 | 19.870 | −24.928 | 1.00 | 42.60 | C |
| ATOM | 2409 | CG | MET | C | 76 | 39.730 | 20.330 | −25.796 | 1.00 | 43.03 | C |
| ATOM | 2410 | SD | MET | C | 76 | 40.561 | 21.749 | −25.111 | 1.00 | 43.66 | S |
| ATOM | 2411 | CE | MET | C | 76 | 39.365 | 23.044 | −25.475 | 1.00 | 43.55 | C |
| ATOM | 2412 | N | LYS | C | 77 | 39.361 | 16.894 | −26.451 | 1.00 | 45.65 | N |
| ATOM | 2413 | CA | LYS | C | 77 | 40.313 | 15.790 | −26.526 | 1.00 | 47.16 | C |
| ATOM | 2414 | C | LYS | C | 77 | 41.769 | 16.240 | −26.378 | 1.00 | 48.19 | C |
| ATOM | 2415 | O | LYS | C | 77 | 42.070 | 17.436 | −26.407 | 1.00 | 47.32 | O |
| ATOM | 2416 | CB | LYS | C | 77 | 40.131 | 15.075 | −27.860 | 1.00 | 48.29 | C |
| ATOM | 2417 | CG | LYS | C | 77 | 38.794 | 14.376 | −28.017 | 1.00 | 49.47 | C |
| ATOM | 2418 | CD | LYS | C | 77 | 38.813 | 13.040 | −27.294 | 1.00 | 50.83 | C |
| ATOM | 2419 | CE | LYS | C | 77 | 37.622 | 12.185 | −27.681 | 1.00 | 51.99 | C |
| ATOM | 2420 | NZ | LYS | C | 77 | 37.832 | 10.757 | −27.326 | 1.00 | 52.73 | N |
| ATOM | 2421 | N | GLU | C | 78 | 42.667 | 15.267 | −26.238 | 1.00 | 49.39 | N |
| ATOM | 2422 | CA | GLU | C | 78 | 44.095 | 15.528 | −26.078 | 1.00 | 50.46 | C |
| ATOM | 2423 | C | GLU | C | 78 | 44.721 | 16.329 | −27.224 | 1.00 | 51.02 | C |
| ATOM | 2424 | O | GLU | C | 78 | 45.667 | 17.083 | −27.006 | 1.00 | 51.07 | O |
| ATOM | 2425 | CB | GLU | C | 78 | 44.850 | 14.204 | −25.903 | 1.00 | 50.91 | C |
| ATOM | 2426 | N | ASP | C | 79 | 44.200 | 16.169 | −28.438 | 1.00 | 51.94 | N |
| ATOM | 2427 | CA | ASP | C | 79 | 44.732 | 16.894 | −29.593 | 1.00 | 52.77 | C |
| ATOM | 2428 | C | ASP | C | 79 | 44.094 | 18.271 | −29.747 | 1.00 | 52.81 | C |
| ATOM | 2429 | O | ASP | C | 79 | 44.385 | 18.993 | −30.702 | 1.00 | 53.53 | O |
| ATOM | 2430 | CB | ASP | C | 79 | 44.513 | 16.101 | −30.887 | 1.00 | 53.03 | C |
| ATOM | 2431 | CG | ASP | C | 79 | 43.048 | 15.907 | −31.210 | 1.00 | 53.54 | C |
| ATOM | 2432 | OD1 | ASP | C | 79 | 42.741 | 15.465 | −32.337 | 1.00 | 53.19 | O |
| ATOM | 2433 | OD2 | ASP | C | 79 | 42.201 | 16.191 | −30.335 | 1.00 | 54.33 | O |
| ATOM | 2434 | N | GLY | C | 80 | 43.213 | 18.624 | −28.816 | 1.00 | 52.60 | N |
| ATOM | 2435 | CA | GLY | C | 80 | 42.558 | 19.921 | −28.873 | 1.00 | 51.91 | C |
| ATOM | 2436 | C | GLY | C | 80 | 41.275 | 19.969 | −29.688 | 1.00 | 51.26 | C |
| ATOM | 2437 | O | GLY | C | 80 | 40.765 | 21.051 | −29.981 | 1.00 | 51.15 | O |
| ATOM | 2438 | N | ARG | C | 81 | 40.744 | 18.807 | −30.055 | 1.00 | 50.21 | N |
| ATOM | 2439 | CA | ARG | C | 81 | 39.512 | 18.763 | −30.836 | 1.00 | 49.98 | C |
| ATOM | 2440 | C | ARG | C | 81 | 38.295 | 18.757 | −29.922 | 1.00 | 49.17 | C |
| ATOM | 2441 | O | ARG | C | 81 | 38.356 | 18.262 | −28.800 | 1.00 | 48.55 | O |
| ATOM | 2442 | CB | ARG | C | 81 | 39.491 | 17.518 | −31.735 | 1.00 | 50.35 | C |
| ATOM | 2443 | N | LEU | C | 82 | 37.187 | 19.306 | −30.405 | 1.00 | 48.69 | N |
| ATOM | 2444 | CA | LEU | C | 82 | 35.960 | 19.348 | −29.613 | 1.00 | 48.32 | C |
| ATOM | 2445 | C | LEU | C | 82 | 34.941 | 18.320 | −30.099 | 1.00 | 48.64 | C |
| ATOM | 2446 | O | LEU | C | 82 | 34.789 | 18.102 | −31.304 | 1.00 | 48.30 | O |
| ATOM | 2447 | CB | LEU | C | 82 | 35.320 | 20.743 | −29.677 | 1.00 | 47.29 | C |
| ATOM | 2448 | CG | LEU | C | 82 | 36.026 | 21.976 | −29.098 | 1.00 | 47.17 | C |
| ATOM | 2449 | CD1 | LEU | C | 82 | 35.140 | 23.197 | −29.319 | 1.00 | 46.72 | C |
| ATOM | 2450 | CD2 | LEU | C | 82 | 36.298 | 21.796 | −27.612 | 1.00 | 46.26 | C |
| ATOM | 2451 | N | LEU | C | 83 | 34.250 | 17.690 | −29.154 | 1.00 | 48.75 | N |
| ATOM | 2452 | CA | LEU | C | 83 | 33.218 | 16.711 | −29.469 | 1.00 | 49.23 | C |
| ATOM | 2453 | C | LEU | C | 83 | 32.286 | 16.572 | −28.264 | 1.00 | 49.29 | C |
| ATOM | 2454 | O | LEU | C | 83 | 32.566 | 17.117 | −27.200 | 1.00 | 49.90 | O |
| ATOM | 2455 | CB | LEU | C | 83 | 33.847 | 15.365 | −29.832 | 1.00 | 49.75 | C |
| ATOM | 2456 | CG | LEU | C | 83 | 34.608 | 14.566 | −28.775 | 1.00 | 50.52 | C |
| ATOM | 2457 | CD1 | LEU | C | 83 | 33.657 | 13.956 | −27.745 | 1.00 | 50.21 | C |
| ATOM | 2458 | CD2 | LEU | C | 83 | 35.369 | 13.466 | −29.495 | 1.00 | 51.56 | C |
| ATOM | 2459 | N | ALA | C | 84 | 31.175 | 15.860 | −28.434 | 1.00 | 49.10 | N |
| ATOM | 2460 | CA | ALA | C | 84 | 30.219 | 15.668 | −27.347 | 1.00 | 48.92 | C |
| ATOM | 2461 | C | ALA | C | 84 | 30.058 | 14.186 | −27.004 | 1.00 | 48.88 | C |
| ATOM | 2462 | O | ALA | C | 84 | 29.679 | 13.379 | −27.852 | 1.00 | 49.38 | O |
| ATOM | 2463 | CB | ALA | C | 84 | 28.880 | 16.277 | −27.720 | 1.00 | 48.95 | C |
| ATOM | 2464 | N | SER | C | 85 | 30.336 | 13.851 | −25.748 | 1.00 | 48.54 | N |
| ATOM | 2465 | CA | SER | C | 85 | 30.277 | 12.484 | −25.249 | 1.00 | 48.57 | C |
| ATOM | 2466 | C | SER | C | 85 | 28.951 | 12.060 | −24.619 | 1.00 | 48.60 | C |
| ATOM | 2467 | O | SER | C | 85 | 28.278 | 12.852 | −23.959 | 1.00 | 48.21 | O |
| ATOM | 2468 | CB | SER | C | 85 | 31.387 | 12.281 | −24.221 | 1.00 | 47.92 | C |
| ATOM | 2469 | OG | SER | C | 85 | 31.239 | 11.031 | −23.585 | 1.00 | 49.89 | O |
| ATOM | 2470 | N | LYS | C | 86 | 28.598 | 10.793 | −24.809 | 1.00 | 48.12 | N |
| ATOM | 2471 | CA | LYS | C | 86 | 27.371 | 10.254 | −24.247 | 1.00 | 47.55 | C |
| ATOM | 2472 | C | LYS | C | 86 | 27.507 | 10.209 | −22.728 | 1.00 | 47.26 | C |
| ATOM | 2473 | O | LYS | C | 86 | 26.563 | 10.521 | −21.997 | 1.00 | 47.30 | O |
| ATOM | 2474 | CB | LYS | C | 86 | 27.112 | 8.849 | −24.795 | 1.00 | 47.10 | C |
| ATOM | 2475 | N | SER | C | 87 | 28.690 | 9.829 | −22.258 | 1.00 | 46.30 | N |
| ATOM | 2476 | CA | SER | C | 87 | 28.941 | 9.751 | −20.826 | 1.00 | 46.50 | C |
| ATOM | 2477 | C | SER | C | 87 | 30.011 | 10.757 | −20.395 | 1.00 | 45.67 | C |
| ATOM | 2478 | O | SER | C | 87 | 30.930 | 11.069 | −21.146 | 1.00 | 45.37 | O |
| ATOM | 2479 | CB | SER | C | 87 | 29.367 | 8.326 | −20.448 | 1.00 | 47.59 | C |
| ATOM | 2480 | OG | SER | C | 87 | 30.485 | 7.895 | −21.213 | 1.00 | 47.94 | O |
| ATOM | 2481 | N | VAL | C | 88 | 29.881 | 11.245 | −19.169 | 1.00 | 45.08 | N |
| ATOM | 2482 | CA | VAL | C | 88 | 30.794 | 12.226 | −18.603 | 1.00 | 44.44 | C |

TABLE 3-continued

FGFR2(D2–D3) Complexed with FGF2

| ATOM | 2483 | C | VAL | C | 88 | 32.196 | 11.683 | −18.306 | 1.00 | 44.01 | C |
|---|---|---|---|---|---|---|---|---|---|---|---|
| ATOM | 2484 | O | VAL | C | 88 | 32.337 | 10.651 | −17.660 | 1.00 | 44.28 | O |
| ATOM | 2485 | CB | VAL | C | 88 | 30.198 | 12.788 | −17.293 | 1.00 | 44.66 | C |
| ATOM | 2486 | CG1 | VAL | C | 88 | 31.119 | 13.850 | −16.699 | 1.00 | 44.31 | C |
| ATOM | 2487 | CG2 | VAL | C | 88 | 28.802 | 13.350 | −17.564 | 1.00 | 44.59 | C |
| ATOM | 2488 | N | THR | C | 89 | 33.223 | 12.383 | −18.781 | 1.00 | 43.00 | N |
| ATOM | 2489 | CA | THR | C | 89 | 34.608 | 11.992 | −18.524 | 1.00 | 42.40 | C |
| ATOM | 2490 | C | THR | C | 89 | 35.357 | 13.227 | −18.034 | 1.00 | 41.68 | C |
| ATOM | 2491 | O | THR | C | 89 | 34.782 | 14.309 | −17.974 | 1.00 | 40.99 | O |
| ATOM | 2492 | CB | THR | C | 89 | 35.313 | 11.464 | −19.783 | 1.00 | 42.09 | C |
| ATOM | 2493 | OG1 | THR | C | 89 | 35.446 | 12.524 | −20.734 | 1.00 | 42.86 | O |
| ATOM | 2494 | CG2 | THR | C | 89 | 34.519 | 10.318 | −20.400 | 1.00 | 42.59 | C |
| ATOM | 2495 | N | ASP | C | 90 | 36.633 | 13.066 | −17.689 | 1.00 | 41.15 | N |
| ATOM | 2496 | CA | ASP | C | 90 | 37.443 | 14.174 | −17.191 | 1.00 | 41.02 | C |
| ATOM | 2497 | C | ASP | C | 90 | 37.718 | 15.258 | −18.228 | 1.00 | 41.00 | C |
| ATOM | 2498 | O | ASP | C | 90 | 38.282 | 16.305 | −17.910 | 1.00 | 41.60 | O |
| ATOM | 2499 | CB | ASP | C | 90 | 38.776 | 13.652 | −16.628 | 1.00 | 40.89 | C |
| ATOM | 2500 | CG | ASP | C | 90 | 39.530 | 12.725 | −17.604 | 1.00 | 41.99 | C |
| ATOM | 2501 | OD1 | ASP | C | 90 | 39.161 | 12.634 | −18.802 | 1.00 | 40.96 | O |
| ATOM | 2502 | OD2 | ASP | C | 90 | 40.515 | 12.089 | −17.162 | 1.00 | 40.95 | O |
| ATOM | 2503 | N | GLU | C | 91 | 37.320 | 15.011 | −19.469 | 1.00 | 40.62 | N |
| ATOM | 2504 | CA | GLU | C | 91 | 37.542 | 15.989 | −20.529 | 1.00 | 40.60 | C |
| ATOM | 2505 | C | GLU | C | 91 | 36.272 | 16.810 | −20.769 | 1.00 | 38.90 | C |
| ATOM | 2506 | O | GLU | C | 91 | 36.183 | 17.563 | −21.733 | 1.00 | 38.75 | O |
| ATOM | 2507 | CB | GLU | C | 91 | 37.960 | 15.276 | −21.820 | 1.00 | 40.75 | C |
| ATOM | 2508 | CG | GLU | C | 91 | 39.061 | 14.251 | −21.627 | 1.00 | 40.73 | C |
| ATOM | 2509 | CD | GLU | C | 91 | 39.559 | 13.672 | −22.942 | 1.00 | 41.24 | C |
| ATOM | 2510 | OE1 | GLU | C | 91 | 38.728 | 13.210 | −23.755 | 1.00 | 39.80 | O |
| ATOM | 2511 | OE2 | GLU | C | 91 | 40.788 | 13.678 | −23.159 | 1.00 | 42.00 | O |
| ATOM | 2512 | N | CYS | C | 92 | 35.304 | 16.667 | −19.873 | 1.00 | 37.52 | N |
| ATOM | 2513 | CA | CYS | C | 92 | 34.032 | 17.374 | −19.989 | 1.00 | 37.32 | C |
| ATOM | 2514 | C | CYS | C | 92 | 33.843 | 18.530 | −18.996 | 1.00 | 36.94 | C |
| ATOM | 2515 | O | CYS | C | 92 | 32.738 | 19.064 | −18.875 | 1.00 | 36.38 | O |
| ATOM | 2516 | CB | CYS | C | 92 | 32.877 | 16.380 | −19.822 | 1.00 | 37.36 | C |
| ATOM | 2517 | SG | CYS | C | 92 | 32.820 | 15.037 | −21.053 | 1.00 | 37.79 | S |
| ATOM | 2518 | N | PHE | C | 93 | 34.915 | 18.918 | −18.301 | 1.00 | 36.25 | N |
| ATOM | 2519 | CA | PHE | C | 93 | 34.850 | 19.988 | −17.308 | 1.00 | 35.38 | C |
| ATOM | 2520 | C | PHE | C | 93 | 35.703 | 21.203 | −17.687 | 1.00 | 34.84 | C |
| ATOM | 2521 | O | PHE | C | 93 | 36.850 | 21.068 | −18.115 | 1.00 | 34.56 | O |
| ATOM | 2522 | CB | PHE | C | 93 | 35.241 | 19.415 | −15.938 | 1.00 | 36.14 | C |
| ATOM | 2523 | CG | PHE | C | 93 | 34.295 | 18.338 | −15.452 | 1.00 | 37.64 | C |
| ATOM | 2524 | CD1 | PHE | C | 93 | 32.993 | 18.660 | −15.077 | 1.00 | 36.97 | C |
| ATOM | 2525 | CD2 | PHE | C | 93 | 34.675 | 16.996 | −15.454 | 1.00 | 38.01 | C |
| ATOM | 2526 | CE1 | PHE | C | 93 | 32.077 | 17.670 | −14.718 | 1.00 | 38.43 | C |
| ATOM | 2527 | CE2 | PHE | C | 93 | 33.764 | 15.993 | −15.095 | 1.00 | 39.03 | C |
| ATOM | 2528 | CZ | PHE | C | 93 | 32.459 | 16.333 | −14.727 | 1.00 | 39.06 | C |
| ATOM | 2529 | N | PHE | C | 94 | 35.132 | 22.393 | −17.514 | 1.00 | 33.24 | N |
| ATOM | 2530 | CA | PHE | C | 94 | 35.802 | 23.627 | −17.893 | 1.00 | 32.55 | C |
| ATOM | 2531 | C | PHE | C | 94 | 35.689 | 24.748 | −16.862 | 1.00 | 33.00 | C |
| ATOM | 2532 | O | PHE | C | 94 | 34.622 | 24.949 | −16.262 | 1.00 | 32.17 | O |
| ATOM | 2533 | CB | PHE | C | 94 | 35.203 | 24.129 | −19.202 | 1.00 | 31.92 | C |
| ATOM | 2534 | CG | PHE | C | 94 | 35.190 | 23.103 | −20.300 | 1.00 | 31.77 | C |
| ATOM | 2535 | CD1 | PHE | C | 94 | 36.240 | 23.030 | −21.213 | 1.00 | 31.68 | C |
| ATOM | 2536 | CD2 | PHE | C | 94 | 34.123 | 22.209 | −20.424 | 1.00 | 31.56 | C |
| ATOM | 2537 | CE1 | PHE | C | 94 | 36.229 | 22.083 | −22.238 | 1.00 | 32.19 | C |
| ATOM | 2538 | CE2 | PHE | C | 94 | 34.099 | 21.256 | −21.442 | 1.00 | 31.45 | C |
| ATOM | 2539 | CZ | PHE | C | 94 | 35.156 | 21.193 | −22.354 | 1.00 | 32.41 | C |
| ATOM | 2540 | N | PHE | C | 95 | 36.788 | 25.479 | −16.672 | 1.00 | 31.65 | N |
| ATOM | 2541 | CA | PHE | C | 95 | 36.785 | 26.605 | −15.749 | 1.00 | 32.59 | C |
| ATOM | 2542 | C | PHE | C | 95 | 35.973 | 27.715 | −16.422 | 1.00 | 32.18 | C |
| ATOM | 2543 | O | PHE | C | 95 | 36.285 | 28.107 | −17.544 | 1.00 | 31.89 | O |
| ATOM | 2544 | CB | PHE | C | 95 | 38.203 | 27.153 | −15.502 | 1.00 | 32.78 | C |
| ATOM | 2545 | CG | PHE | C | 95 | 39.113 | 26.219 | −14.754 | 1.00 | 33.25 | C |
| ATOM | 2546 | CD1 | PHE | C | 95 | 40.174 | 25.588 | −15.406 | 1.00 | 33.55 | C |
| ATOM | 2547 | CD2 | PHE | C | 95 | 38.942 | 26.004 | −13.389 | 1.00 | 33.39 | C |
| ATOM | 2548 | CE1 | PHE | C | 95 | 41.060 | 24.752 | −14.701 | 1.00 | 33.84 | C |
| ATOM | 2549 | CE2 | PHE | C | 95 | 39.819 | 25.170 | −12.673 | 1.00 | 34.03 | C |
| ATOM | 2550 | CZ | PHE | C | 95 | 40.881 | 24.544 | −13.333 | 1.00 | 33.13 | C |
| ATOM | 2551 | N | GLU | C | 96 | 34.933 | 28.205 | −15.755 | 1.00 | 31.97 | N |
| ATOM | 2552 | CA | GLU | C | 96 | 34.145 | 29.292 | −16.321 | 1.00 | 32.01 | C |
| ATOM | 2553 | C | GLU | C | 96 | 34.593 | 30.582 | −15.667 | 1.00 | 32.86 | C |
| ATOM | 2554 | O | GLU | C | 96 | 34.685 | 30.674 | −14.438 | 1.00 | 31.69 | O |
| ATOM | 2555 | CB | GLU | C | 96 | 32.644 | 29.131 | −16.070 | 1.00 | 30.63 | C |
| ATOM | 2556 | CG | GLU | C | 96 | 31.826 | 30.275 | −16.687 | 1.00 | 30.23 | C |
| ATOM | 2557 | CD | GLU | C | 96 | 30.391 | 30.313 | −16.195 | 1.00 | 31.57 | C |
| ATOM | 2558 | OE1 | GLU | C | 96 | 30.191 | 30.709 | −15.029 | 1.00 | 31.17 | O |
| ATOM | 2559 | OE2 | GLU | C | 96 | 29.472 | 29.942 | −16.964 | 1.00 | 30.53 | O |

TABLE 3-continued

FGFR2(D2–D3) Complexed with FGF2

| ATOM | 2560 | N | ARG | C | 97 | 34.858 | 31.582 | −16.497 | 1.00 | 33.81 | N |
|---|---|---|---|---|---|---|---|---|---|---|---|
| ATOM | 2561 | CA | ARG | C | 97 | 35.288 | 32.876 | −15.996 | 1.00 | 36.12 | C |
| ATOM | 2562 | C | ARG | C | 97 | 34.610 | 34.050 | −16.699 | 1.00 | 34.78 | C |
| ATOM | 2563 | O | ARG | C | 97 | 34.470 | 34.063 | −17.915 | 1.00 | 34.00 | O |
| ATOM | 2564 | CB | ARG | C | 97 | 36.809 | 33.008 | −16.138 | 1.00 | 38.79 | C |
| ATOM | 2565 | CG | ARG | C | 97 | 37.343 | 34.362 | −15.710 | 1.00 | 42.82 | C |
| ATOM | 2566 | CD | ARG | C | 97 | 38.351 | 34.248 | −14.579 | 1.00 | 47.40 | C |
| ATOM | 2567 | NE | ARG | C | 97 | 39.732 | 34.315 | −15.050 | 1.00 | 50.42 | N |
| ATOM | 2568 | CZ | ARG | C | 97 | 40.229 | 35.309 | −15.785 | 1.00 | 51.99 | C |
| ATOM | 2569 | NH1 | ARG | C | 97 | 39.456 | 36.326 | −16.144 | 1.00 | 52.03 | N |
| ATOM | 2570 | NH2 | ARG | C | 97 | 41.508 | 35.293 | −16.153 | 1.00 | 53.32 | N |
| ATOM | 2571 | N | LEU | C | 98 | 34.168 | 35.023 | −15.914 | 1.00 | 35.44 | N |
| ATOM | 2572 | CA | LEU | C | 98 | 33.549 | 36.233 | −16.451 | 1.00 | 35.58 | C |
| ATOM | 2573 | C | LEU | C | 98 | 34.702 | 37.211 | −16.606 | 1.00 | 36.26 | C |
| ATOM | 2574 | O | LEU | C | 98 | 35.252 | 37.674 | −15.612 | 1.00 | 37.23 | O |
| ATOM | 2575 | CB | LEU | C | 98 | 32.537 | 36.816 | −15.469 | 1.00 | 34.84 | C |
| ATOM | 2576 | CG | LEU | C | 98 | 32.101 | 38.257 | −15.784 | 1.00 | 36.02 | C |
| ATOM | 2577 | CD1 | LEU | C | 98 | 31.366 | 38.301 | −17.119 | 1.00 | 34.57 | C |
| ATOM | 2578 | CD2 | LEU | C | 98 | 31.201 | 38.782 | −14.663 | 1.00 | 36.07 | C |
| ATOM | 2579 | N | GLU | C | 99 | 35.086 | 37.514 | −17.842 | 1.00 | 37.80 | N |
| ATOM | 2580 | CA | GLU | C | 99 | 36.204 | 38.433 | −18.084 | 1.00 | 38.69 | C |
| ATOM | 2581 | C | GLU | C | 99 | 35.808 | 39.884 | −17.844 | 1.00 | 39.79 | C |
| ATOM | 2582 | O | GLU | C | 99 | 34.619 | 40.226 | −17.785 | 1.00 | 39.34 | O |
| ATOM | 2583 | CB | GLU | C | 99 | 36.739 | 38.281 | −19.517 | 1.00 | 39.78 | C |
| ATOM | 2584 | CG | GLU | C | 99 | 37.157 | 36.852 | −19.908 | 1.00 | 42.32 | C |
| ATOM | 2585 | CD | GLU | C | 99 | 38.473 | 36.383 | −19.275 | 1.00 | 44.17 | C |
| ATOM | 2586 | OE1 | GLU | C | 99 | 38.778 | 35.171 | −19.365 | 1.00 | 44.05 | O |
| ATOM | 2587 | OE2 | GLU | C | 99 | 39.205 | 37.216 | −18.698 | 1.00 | 45.49 | O |
| ATOM | 2588 | N | SER | C | 100 | 36.821 | 40.738 | −17.713 | 1.00 | 40.51 | N |
| ATOM | 2589 | CA | SER | C | 100 | 36.617 | 42.165 | −17.470 | 1.00 | 40.62 | C |
| ATOM | 2590 | C | SER | C | 100 | 35.794 | 42.816 | −18.572 | 1.00 | 39.80 | C |
| ATOM | 2591 | O | SER | C | 100 | 35.152 | 43.848 | −18.353 | 1.00 | 41.01 | O |
| ATOM | 2592 | CB | SER | C | 100 | 37.971 | 42.882 | −17.356 | 1.00 | 42.46 | C |
| ATOM | 2593 | OG | SER | C | 100 | 38.653 | 42.906 | −18.603 | 1.00 | 43.81 | O |
| ATOM | 2594 | N | ASN | C | 101 | 35.821 | 42.222 | −19.763 | 1.00 | 38.39 | N |
| ATOM | 2595 | CA | ASN | C | 101 | 35.060 | 42.740 | −20.900 | 1.00 | 36.37 | C |
| ATOM | 2596 | C | ASN | C | 101 | 33.584 | 42.307 | −20.845 | 1.00 | 35.56 | C |
| ATOM | 2597 | O | ASN | C | 101 | 32.792 | 42.648 | −21.725 | 1.00 | 36.19 | O |
| ATOM | 2598 | CB | ASN | C | 101 | 35.683 | 42.244 | −22.210 | 1.00 | 37.90 | C |
| ATOM | 2599 | N | ASN | C | 102 | 33.237 | 41.549 | −19.810 | 1.00 | 33.69 | N |
| ATOM | 2600 | CA | ASN | C | 102 | 31.890 | 41.035 | −19.584 | 1.00 | 32.91 | C |
| ATOM | 2601 | C | ASN | C | 102 | 31.418 | 39.878 | −20.473 | 1.00 | 31.53 | C |
| ATOM | 2602 | O | ASN | C | 102 | 30.215 | 39.656 | −20.621 | 1.00 | 29.70 | O |
| ATOM | 2603 | CB | ASN | C | 102 | 30.851 | 42.162 | −19.599 | 1.00 | 33.64 | C |
| ATOM | 2604 | CG | ASN | C | 102 | 30.685 | 42.813 | −18.231 | 1.00 | 35.78 | C |
| ATOM | 2605 | OD1 | ASN | C | 102 | 30.944 | 42.182 | −17.197 | 1.00 | 36.62 | O |
| ATOM | 2606 | ND2 | ASN | C | 102 | 30.239 | 44.072 | −18.214 | 1.00 | 35.16 | N |
| ATOM | 2607 | N | TYR | C | 103 | 32.374 | 39.156 | −21.055 | 1.00 | 29.91 | N |
| ATOM | 2608 | CA | TYR | C | 103 | 32.090 | 37.975 | −21.870 | 1.00 | 29.05 | C |
| ATOM | 2609 | C | TYR | C | 103 | 32.597 | 36.788 | −21.031 | 1.00 | 28.17 | C |
| ATOM | 2610 | O | TYR | C | 103 | 33.392 | 36.972 | −20.113 | 1.00 | 28.49 | O |
| ATOM | 2611 | CB | TYR | C | 103 | 32.843 | 38.035 | −23.201 | 1.00 | 28.04 | C |
| ATOM | 2612 | CG | TYR | C | 103 | 32.186 | 38.901 | −24.268 | 1.00 | 28.96 | C |
| ATOM | 2613 | CD1 | TYR | C | 103 | 31.185 | 38.385 | −25.103 | 1.00 | 28.99 | C |
| ATOM | 2614 | CD2 | TYR | C | 103 | 32.568 | 40.232 | −24.450 | 1.00 | 28.27 | C |
| ATOM | 2615 | CE1 | TYR | C | 103 | 30.587 | 39.175 | −26.096 | 1.00 | 28.06 | C |
| ATOM | 2616 | CE2 | TYR | C | 103 | 31.976 | 41.027 | −25.434 | 1.00 | 27.36 | C |
| ATOM | 2617 | CZ | TYR | C | 103 | 30.995 | 40.495 | −26.249 | 1.00 | 28.17 | C |
| ATOM | 2618 | OH | TYR | C | 103 | 30.430 | 41.280 | −27.220 | 1.00 | 27.43 | O |
| ATOM | 2619 | N | ASN | C | 104 | 32.121 | 35.584 | −21.319 | 1.00 | 27.04 | N |
| ATOM | 2620 | CA | ASN | C | 104 | 32.556 | 34.393 | −20.583 | 1.00 | 26.71 | C |
| ATOM | 2621 | C | ASN | C | 104 | 33.604 | 33.620 | −21.378 | 1.00 | 25.89 | C |
| ATOM | 2622 | O | ASN | C | 104 | 33.641 | 33.709 | −22.606 | 1.00 | 24.27 | O |
| ATOM | 2623 | CB | ASN | C | 104 | 31.385 | 33.436 | −20.349 | 1.00 | 26.70 | C |
| ATOM | 2624 | CG | ASN | C | 104 | 30.573 | 33.778 | −19.126 | 1.00 | 27.03 | C |
| ATOM | 2625 | OD1 | ASN | C | 104 | 30.641 | 34.883 | −18.605 | 1.00 | 27.86 | O |
| ATOM | 2626 | ND2 | ASN | C | 104 | 29.784 | 32.817 | −18.663 | 1.00 | 27.30 | N |
| ATOM | 2627 | N | THR | C | 105 | 34.448 | 32.871 | −20.671 | 1.00 | 25.77 | N |
| ATOM | 2628 | CA | THR | C | 105 | 35.444 | 32.017 | −21.315 | 1.00 | 26.79 | C |
| ATOM | 2629 | C | THR | C | 105 | 35.374 | 30.659 | −20.626 | 1.00 | 27.22 | C |
| ATOM | 2630 | O | THR | C | 105 | 35.037 | 30.568 | −19.434 | 1.00 | 26.69 | O |
| ATOM | 2631 | CB | THR | C | 105 | 36.887 | 32.561 | −21.197 | 1.00 | 27.27 | C |
| ATOM | 2632 | OG1 | THR | C | 105 | 37.277 | 32.601 | −19.819 | 1.00 | 27.69 | O |
| ATOM | 2633 | CG2 | THR | C | 105 | 36.988 | 33.940 | −21.817 | 1.00 | 26.48 | C |
| ATOM | 2634 | N | TYR | C | 106 | 35.683 | 29.608 | −21.383 | 1.00 | 27.57 | N |
| ATOM | 2635 | CA | TYR | C | 106 | 35.649 | 28.245 | −20.868 | 1.00 | 28.53 | C |
| ATOM | 2636 | C | TYR | C | 106 | 36.980 | 27.560 | −21.138 | 1.00 | 29.84 | C |

TABLE 3-continued

FGFR2(D2–D3) Complexed with FGF2

| ATOM | 2637 | O | TYR | C | 106 | 37.298 | 27.243 | −22.279 | 1.00 | 30.42 | O |
|---|---|---|---|---|---|---|---|---|---|---|---|
| ATOM | 2638 | CB | TYR | C | 106 | 34.492 | 27.498 | −21.529 | 1.00 | 27.19 | C |
| ATOM | 2639 | CG | TYR | C | 106 | 33.178 | 28.086 | −21.100 | 1.00 | 26.37 | C |
| ATOM | 2640 | CD1 | TYR | C | 106 | 32.607 | 27.734 | −19.871 | 1.00 | 24.88 | C |
| ATOM | 2641 | CD2 | TYR | C | 106 | 32.562 | 29.082 | −21.856 | 1.00 | 24.49 | C |
| ATOM | 2642 | CE1 | TYR | C | 106 | 31.461 | 28.365 | −19.406 | 1.00 | 24.93 | C |
| ATOM | 2643 | CE2 | TYR | C | 106 | 31.419 | 29.720 | −21.397 | 1.00 | 24.64 | C |
| ATOM | 2644 | CZ | TYR | C | 106 | 30.878 | 29.364 | −20.173 | 1.00 | 24.07 | C |
| ATOM | 2645 | OH | TYR | C | 106 | 29.785 | 30.037 | −19.690 | 1.00 | 23.81 | O |
| ATOM | 2646 | N | ARG | C | 107 | 37.747 | 27.343 | −20.071 | 1.00 | 31.74 | N |
| ATOM | 2647 | CA | ARG | C | 107 | 39.068 | 26.728 | −20.159 | 1.00 | 33.10 | C |
| ATOM | 2648 | C | ARG | C | 107 | 39.093 | 25.297 | −19.606 | 1.00 | 33.48 | C |
| ATOM | 2649 | O | ARG | C | 107 | 38.622 | 25.033 | −18.503 | 1.00 | 33.37 | O |
| ATOM | 2650 | CB | ARG | C | 107 | 40.071 | 27.616 | −19.417 | 1.00 | 33.24 | C |
| ATOM | 2651 | CG | ARG | C | 107 | 41.514 | 27.177 | −19.479 | 1.00 | 34.14 | C |
| ATOM | 2652 | CD | ARG | C | 107 | 42.413 | 28.233 | −18.821 | 1.00 | 33.47 | C |
| ATOM | 2653 | NE | ARG | C | 107 | 41.977 | 28.538 | −17.461 | 1.00 | 32.49 | N |
| ATOM | 2654 | CZ | ARG | C | 107 | 42.333 | 27.851 | −16.382 | 1.00 | 33.45 | C |
| ATOM | 2655 | NH1 | ARG | C | 107 | 43.153 | 26.809 | −16.490 | 1.00 | 33.22 | N |
| ATOM | 2656 | NH2 | ARG | C | 107 | 41.850 | 28.191 | −15.192 | 1.00 | 32.96 | N |
| ATOM | 2657 | N | SER | C | 108 | 39.643 | 24.380 | −20.396 | 1.00 | 34.74 | N |
| ATOM | 2658 | CA | SER | C | 108 | 39.735 | 22.962 | −20.030 | 1.00 | 35.93 | C |
| ATOM | 2659 | C | SER | C | 108 | 40.408 | 22.738 | −18.680 | 1.00 | 36.71 | C |
| ATOM | 2660 | O | SER | C | 108 | 41.496 | 23.261 | −18.432 | 1.00 | 36.82 | O |
| ATOM | 2661 | CB | SER | C | 108 | 40.508 | 22.195 | −21.111 | 1.00 | 35.40 | C |
| ATOM | 2662 | OG | SER | C | 108 | 40.722 | 20.843 | −20.748 | 1.00 | 33.84 | O |
| ATOM | 2663 | N | ARG | C | 109 | 39.768 | 21.966 | −17.807 | 1.00 | 37.26 | N |
| ATOM | 2664 | CA | ARG | C | 109 | 40.369 | 21.695 | −16.507 | 1.00 | 38.94 | C |
| ATOM | 2665 | C | ARG | C | 109 | 41.478 | 20.654 | −16.664 | 1.00 | 40.40 | C |
| ATOM | 2666 | O | ARG | C | 109 | 42.385 | 20.583 | −15.835 | 1.00 | 41.02 | O |
| ATOM | 2667 | CB | ARG | C | 109 | 39.326 | 21.196 | −15.496 | 1.00 | 38.66 | C |
| ATOM | 2668 | CG | ARG | C | 109 | 39.879 | 21.084 | −14.063 | 1.00 | 37.85 | C |
| ATOM | 2669 | CD | ARG | C | 109 | 38.814 | 20.658 | −13.055 | 1.00 | 37.07 | C |
| ATOM | 2670 | NE | ARG | C | 109 | 38.218 | 19.369 | −13.402 | 1.00 | 37.11 | N |
| ATOM | 2671 | CZ | ARG | C | 109 | 37.403 | 18.673 | −12.612 | 1.00 | 37.27 | C |
| ATOM | 2672 | NH1 | ARG | C | 109 | 37.072 | 19.136 | −11.417 | 1.00 | 37.53 | N |
| ATOM | 2673 | NH2 | ARG | C | 109 | 36.926 | 17.500 | −13.009 | 1.00 | 37.87 | N |
| ATOM | 2674 | N | LYS | C | 110 | 41.410 | 19.857 | −17.732 | 1.00 | 41.49 | N |
| ATOM | 2675 | CA | LYS | C | 110 | 42.423 | 18.834 | −17.983 | 1.00 | 42.26 | C |
| ATOM | 2676 | C | LYS | C | 110 | 43.628 | 19.426 | −18.720 | 1.00 | 42.64 | C |
| ATOM | 2677 | O | LYS | C | 110 | 44.756 | 19.351 | −18.227 | 1.00 | 43.22 | O |
| ATOM | 2678 | CB | LYS | C | 110 | 41.822 | 17.668 | −18.775 | 1.00 | 43.33 | C |
| ATOM | 2679 | CG | LYS | C | 110 | 42.686 | 16.403 | −18.750 | 1.00 | 44.52 | C |
| ATOM | 2680 | CD | LYS | C | 110 | 41.816 | 15.148 | −18.694 | 1.00 | 45.95 | C |
| ATOM | 2681 | CE | LYS | C | 110 | 42.649 | 13.872 | −18.721 | 1.00 | 45.97 | C |
| ATOM | 2682 | NZ | LYS | C | 110 | 43.302 | 13.673 | −20.041 | 1.00 | 46.29 | N |
| ATOM | 2683 | N | TYR | C | 111 | 43.381 | 20.013 | −19.889 | 1.00 | 42.26 | N |
| ATOM | 2684 | CA | TYR | C | 111 | 44.421 | 20.650 | −20.692 | 1.00 | 42.11 | C |
| ATOM | 2685 | C | TYR | C | 111 | 44.252 | 22.137 | −20.374 | 1.00 | 41.74 | C |
| ATOM | 2686 | O | TYR | C | 111 | 43.661 | 22.897 | −21.144 | 1.00 | 41.37 | O |
| ATOM | 2687 | CB | TYR | C | 111 | 44.177 | 20.348 | −22.178 | 1.00 | 42.34 | C |
| ATOM | 2688 | CG | TYR | C | 111 | 43.874 | 18.884 | −22.420 | 1.00 | 43.43 | C |
| ATOM | 2689 | CD1 | TYR | C | 111 | 44.858 | 17.905 | −22.239 | 1.00 | 43.53 | C |
| ATOM | 2690 | CD2 | TYR | C | 111 | 42.576 | 18.462 | −22.723 | 1.00 | 43.58 | C |
| ATOM | 2691 | CE1 | TYR | C | 111 | 44.553 | 16.542 | −22.341 | 1.00 | 43.93 | C |
| ATOM | 2692 | CE2 | TYR | C | 111 | 42.256 | 17.098 | −22.826 | 1.00 | 43.90 | C |
| ATOM | 2693 | CZ | TYR | C | 111 | 43.248 | 16.144 | −22.630 | 1.00 | 44.13 | C |
| ATOM | 2694 | OH | TYR | C | 111 | 42.937 | 14.803 | −22.687 | 1.00 | 43.02 | O |
| ATOM | 2695 | N | THR | C | 112 | 44.785 | 22.525 | −19.219 | 1.00 | 41.67 | N |
| ATOM | 2696 | CA | THR | C | 112 | 44.666 | 23.880 | −18.681 | 1.00 | 42.15 | C |
| ATOM | 2697 | C | THR | C | 112 | 45.077 | 25.107 | −19.488 | 1.00 | 42.41 | C |
| ATOM | 2698 | O | THR | C | 112 | 45.018 | 26.214 | −18.969 | 1.00 | 42.75 | O |
| ATOM | 2699 | CB | THR | C | 112 | 45.365 | 23.973 | −17.310 | 1.00 | 41.69 | C |
| ATOM | 2700 | OG1 | THR | C | 112 | 46.748 | 23.631 | −17.453 | 1.00 | 40.08 | O |
| ATOM | 2701 | CG2 | THR | C | 112 | 44.696 | 23.028 | −16.311 | 1.00 | 40.24 | C |
| ATOM | 2702 | N | SER | C | 113 | 45.477 | 24.941 | −20.742 | 1.00 | 42.56 | N |
| ATOM | 2703 | CA | SER | C | 113 | 45.861 | 26.103 | −21.531 | 1.00 | 42.48 | C |
| ATOM | 2704 | C | SER | C | 113 | 44.964 | 26.331 | −22.738 | 1.00 | 41.74 | C |
| ATOM | 2705 | O | SER | C | 113 | 45.054 | 27.367 | −23.402 | 1.00 | 41.60 | O |
| ATOM | 2706 | CB | SER | C | 113 | 47.320 | 25.975 | −21.989 | 1.00 | 42.76 | C |
| ATOM | 2707 | OG | SER | C | 113 | 48.202 | 26.193 | −20.903 | 1.00 | 43.02 | O |
| ATOM | 2708 | N | TRP | C | 114 | 44.087 | 25.374 | −23.008 | 1.00 | 40.80 | N |
| ATOM | 2709 | CA | TRP | C | 114 | 43.211 | 25.476 | −24.163 | 1.00 | 40.67 | C |
| ATOM | 2710 | C | TRP | C | 114 | 41.782 | 25.918 | −23.831 | 1.00 | 39.23 | C |
| ATOM | 2711 | O | TRP | C | 114 | 41.236 | 25.565 | −22.787 | 1.00 | 39.47 | O |
| ATOM | 2712 | CB | TRP | C | 114 | 43.223 | 24.136 | −24.910 | 1.00 | 42.07 | C |
| ATOM | 2713 | CG | TRP | C | 114 | 44.638 | 23.683 | −25.263 | 1.00 | 44.13 | C |

TABLE 3-continued

| | | | | | | | | | | |
|---|---|---|---|---|---|---|---|---|---|---|
| ATOM | 2714 | CD1 | TRP | C | 114 | 45.764 | 24.473 | −25.344 | 1.00 | 44.09 | C |
| ATOM | 2715 | CD2 | TRP | C | 114 | 45.060 | 22.355 | −25.622 | 1.00 | 44.26 | C |
| ATOM | 2716 | NE1 | TRP | C | 114 | 46.850 | 23.719 | −25.729 | 1.00 | 44.28 | N |
| ATOM | 2717 | CE2 | TRP | C | 114 | 46.449 | 22.419 | −25.908 | 1.00 | 45.01 | C |
| ATOM | 2718 | CE3 | TRP | C | 114 | 44.403 | 21.122 | −25.732 | 1.00 | 45.00 | C |
| ATOM | 2719 | CZ2 | TRP | C | 114 | 47.190 | 21.293 | −26.297 | 1.00 | 44.84 | C |
| ATOM | 2720 | CZ3 | TRP | C | 114 | 45.145 | 19.994 | −26.120 | 1.00 | 45.55 | C |
| ATOM | 2721 | CH2 | TRP | C | 114 | 46.522 | 20.093 | −26.396 | 1.00 | 45.81 | C |
| ATOM | 2722 | N | TYR | C | 115 | 41.196 | 26.700 | −24.733 | 1.00 | 37.86 | N |
| ATOM | 2723 | CA | TYR | C | 115 | 39.843 | 27.225 | −24.573 | 1.00 | 37.08 | C |
| ATOM | 2724 | C | TYR | C | 115 | 38.845 | 26.691 | −25.595 | 1.00 | 36.26 | C |
| ATOM | 2725 | O | TYR | C | 115 | 39.210 | 26.330 | −26.710 | 1.00 | 36.31 | O |
| ATOM | 2726 | CB | TYR | C | 115 | 39.833 | 28.750 | −24.711 | 1.00 | 36.58 | C |
| ATOM | 2727 | CG | TYR | C | 115 | 40.567 | 29.525 | −23.645 | 1.00 | 36.87 | C |
| ATOM | 2728 | CD1 | TYR | C | 115 | 41.894 | 29.920 | −23.826 | 1.00 | 37.54 | C |
| ATOM | 2729 | CD2 | TYR | C | 115 | 39.921 | 29.907 | −22.470 | 1.00 | 36.57 | C |
| ATOM | 2730 | CE1 | TYR | C | 115 | 42.561 | 30.687 | −22.857 | 1.00 | 37.18 | C |
| ATOM | 2731 | CE2 | TYR | C | 115 | 40.577 | 30.670 | −21.498 | 1.00 | 37.62 | C |
| ATOM | 2732 | CZ | TYR | C | 115 | 41.896 | 31.058 | −21.700 | 1.00 | 37.00 | C |
| ATOM | 2733 | OH | TYR | C | 115 | 42.538 | 31.822 | −20.753 | 1.00 | 38.71 | O |
| ATOM | 2734 | N | VAL | C | 116 | 37.577 | 26.650 | −25.200 | 1.00 | 35.32 | N |
| ATOM | 2735 | CA | VAL | C | 116 | 36.518 | 26.241 | −26.113 | 1.00 | 34.41 | C |
| ATOM | 2736 | C | VAL | C | 116 | 36.406 | 27.472 | −27.018 | 1.00 | 34.62 | C |
| ATOM | 2737 | O | VAL | C | 116 | 36.361 | 28.599 | −26.529 | 1.00 | 33.71 | O |
| ATOM | 2738 | CB | VAL | C | 116 | 35.200 | 25.995 | −25.350 | 1.00 | 34.30 | C |
| ATOM | 2739 | CD1 | VAL | C | 116 | 34.048 | 25.822 | −26.330 | 1.00 | 33.87 | C |
| ATOM | 2740 | CG2 | VAL | C | 116 | 35.341 | 24.755 | −24.461 | 1.00 | 33.16 | C |
| ATOM | 2741 | N | ALA | C | 117 | 36.385 | 27.268 | −28.330 | 1.00 | 34.69 | N |
| ATOM | 2742 | CA | ALA | C | 117 | 36.341 | 28.404 | −29.241 | 1.00 | 35.58 | C |
| ATOM | 2743 | C | ALA | C | 117 | 35.799 | 28.052 | −30.618 | 1.00 | 36.71 | C |
| ATOM | 2744 | O | ALA | C | 117 | 35.830 | 26.895 | −31.040 | 1.00 | 36.73 | O |
| ATOM | 2745 | CB | ALA | C | 117 | 37.738 | 28.985 | −29.384 | 1.00 | 33.52 | C |
| ATOM | 2746 | N | LEU | C | 118 | 35.316 | 29.069 | −31.319 | 1.00 | 36.96 | N |
| ATOM | 2747 | CA | LEU | C | 118 | 34.790 | 28.882 | −32.657 | 1.00 | 38.21 | C |
| ATOM | 2748 | C | LEU | C | 118 | 35.525 | 29.796 | −33.626 | 1.00 | 39.32 | C |
| ATOM | 2749 | O | LEU | C | 118 | 35.980 | 30.871 | −33.247 | 1.00 | 39.31 | O |
| ATOM | 2750 | CB | LEU | C | 118 | 33.292 | 29.180 | −32.685 | 1.00 | 37.82 | C |
| ATOM | 2751 | CG | LEU | C | 118 | 32.420 | 28.177 | −31.925 | 1.00 | 37.61 | C |
| ATOM | 2752 | CD1 | LEU | C | 118 | 30.980 | 28.624 | −31.995 | 1.00 | 37.18 | C |
| ATOM | 2753 | CD2 | LEU | C | 118 | 32.583 | 26.778 | −32.517 | 1.00 | 36.37 | C |
| ATOM | 2754 | N | LYS | C | 119 | 35.643 | 29.355 | −34.876 | 1.00 | 40.72 | N |
| ATOM | 2755 | CA | LYS | C | 119 | 36.322 | 30.136 | −35.907 | 1.00 | 42.14 | C |
| ATOM | 2756 | C | LYS | C | 119 | 35.323 | 30.991 | −36.664 | 1.00 | 42.14 | C |
| ATOM | 2757 | O | LYS | C | 119 | 34.121 | 30.726 | −36.636 | 1.00 | 42.19 | O |
| ATOM | 2758 | CB | LYS | C | 119 | 37.068 | 29.212 | −36.880 | 1.00 | 43.11 | C |
| ATOM | 2759 | CG | LYS | C | 119 | 37.999 | 28.252 | −36.161 | 1.00 | 44.83 | C |
| ATOM | 2760 | CD | LYS | C | 119 | 39.198 | 27.812 | −36.994 | 1.00 | 46.40 | C |
| ATOM | 2761 | CE | LYS | C | 119 | 38.855 | 26.720 | −37.982 | 1.00 | 47.25 | C |
| ATOM | 2762 | NZ | LYS | C | 119 | 40.088 | 25.981 | −38.401 | 1.00 | 47.67 | N |
| ATOM | 2763 | N | ARG | C | 120 | 35.829 | 32.022 | −37.335 | 1.00 | 42.15 | N |
| ATOM | 2764 | CA | ARG | C | 120 | 34.991 | 32.935 | −38.107 | 1.00 | 42.88 | C |
| ATOM | 2765 | C | ARG | C | 120 | 34.147 | 32.185 | −39.129 | 1.00 | 43.19 | C |
| ATOM | 2766 | O | ARG | C | 120 | 33.133 | 32.691 | −39.598 | 1.00 | 43.38 | O |
| ATOM | 2767 | CB | ARG | C | 120 | 35.859 | 33.969 | −38.829 | 1.00 | 42.13 | C |
| ATOM | 2768 | N | THR | C | 121 | 34.571 | 30.972 | −39.463 | 1.00 | 44.11 | N |
| ATOM | 2769 | CA | THR | C | 121 | 33.868 | 30.148 | −40.437 | 1.00 | 44.82 | C |
| ATOM | 2770 | C | THR | C | 121 | 32.649 | 29.451 | −39.852 | 1.00 | 45.53 | C |
| ATOM | 2771 | O | THR | C | 121 | 31.703 | 29.138 | −40.572 | 1.00 | 46.25 | O |
| ATOM | 2772 | CB | THR | C | 121 | 34.795 | 29.057 | −41.031 | 1.00 | 45.19 | C |
| ATOM | 2773 | OG1 | THR | C | 121 | 35.257 | 28.190 | −39.987 | 1.00 | 44.99 | O |
| ATOM | 2774 | CG2 | THR | C | 121 | 35.990 | 29.692 | −41.719 | 1.00 | 44.57 | C |
| ATOM | 2775 | N | GLY | C | 122 | 32.664 | 29.208 | −38.549 | 1.00 | 45.46 | N |
| ATOM | 2776 | CA | GLY | C | 122 | 31.543 | 28.523 | −37.939 | 1.00 | 46.35 | C |
| ATOM | 2777 | C | GLY | C | 122 | 31.964 | 27.141 | −37.469 | 1.00 | 46.95 | C |
| ATOM | 2778 | O | GLY | C | 122 | 31.180 | 26.399 | −36.872 | 1.00 | 47.14 | O |
| ATOM | 2779 | N | GLN | C | 123 | 33.214 | 26.798 | −37.752 | 1.00 | 46.82 | N |
| ATOM | 2780 | CA | GLN | C | 123 | 33.784 | 25.524 | −37.343 | 1.00 | 47.12 | C |
| ATOM | 2781 | C | GLN | C | 123 | 34.530 | 25.790 | −36.041 | 1.00 | 47.36 | C |
| ATOM | 2782 | O | GLN | C | 123 | 35.039 | 26.897 | −35.828 | 1.00 | 46.67 | O |
| ATOM | 2783 | CB | GLN | C | 123 | 34.764 | 25.025 | −38.407 | 1.00 | 47.34 | C |
| ATOM | 2784 | CG | GLN | C | 123 | 34.134 | 24.871 | −39.785 | 1.00 | 48.83 | C |
| ATOM | 2785 | CD | GLN | C | 123 | 32.958 | 23.903 | −39.779 | 1.00 | 49.80 | C |
| ATOM | 2786 | OE1 | GLN | C | 123 | 33.134 | 22.705 | −39.550 | 1.00 | 50.77 | O |
| ATOM | 2787 | NE2 | GLN | C | 123 | 31.752 | 24.422 | −40.021 | 1.00 | 49.73 | N |
| ATOM | 2788 | N | TYR | C | 124 | 34.599 | 24.795 | −35.162 | 1.00 | 46.99 | N |
| ATOM | 2789 | CA | TYR | C | 124 | 35.301 | 25.002 | −33.907 | 1.00 | 47.03 | C |
| ATOM | 2790 | C | TYR | C | 124 | 36.778 | 25.268 | −34.187 | 1.00 | 46.35 | C |

TABLE 3-continued

FGFR2(D2–D3) Complexed with FGF2

| ATOM | 2791 | O | TYR | C | 124 | 37.256 | 25.057 | −35.297 | 1.00 | 45.97 | O |
|---|---|---|---|---|---|---|---|---|---|---|---|
| ATOM | 2792 | CB | TYR | C | 124 | 35.126 | 23.793 | −32.973 | 1.00 | 47.14 | C |
| ATOM | 2793 | CG | TYR | C | 124 | 35.846 | 22.531 | −33.392 | 1.00 | 47.82 | C |
| ATOM | 2794 | CD1 | TYR | C | 124 | 37.238 | 22.436 | −33.318 | 1.00 | 48.08 | C |
| ATOM | 2795 | CD2 | TYR | C | 124 | 35.137 | 21.427 | −33.854 | 1.00 | 48.30 | C |
| ATOM | 2796 | CE1 | TYR | C | 124 | 37.902 | 21.270 | −33.692 | 1.00 | 48.67 | C |
| ATOM | 2797 | CE2 | TYR | C | 124 | 35.790 | 20.256 | −34.228 | 1.00 | 49.35 | C |
| ATOM | 2798 | CZ | TYR | C | 124 | 37.172 | 20.187 | −34.146 | 1.00 | 49.55 | C |
| ATOM | 2799 | OH | TYR | C | 124 | 37.814 | 19.031 | −34.516 | 1.00 | 50.42 | O |
| ATOM | 2800 | N | LYS | C | 125 | 37.492 | 25.742 | −33.178 | 1.00 | 46.37 | N |
| ATOM | 2801 | CA | LYS | C | 125 | 38.906 | 26.043 | −33.314 | 1.00 | 46.94 | C |
| ATOM | 2802 | C | LYS | C | 125 | 39.699 | 25.130 | −32.379 | 1.00 | 48.01 | C |
| ATOM | 2803 | O | LYS | C | 125 | 39.342 | 24.989 | −31.206 | 1.00 | 47.58 | O |
| ATOM | 2804 | CB | LYS | C | 125 | 39.157 | 27.516 | −32.965 | 1.00 | 45.51 | C |
| ATOM | 2805 | CG | LYS | C | 125 | 40.595 | 27.960 | −33.137 | 1.00 | 44.49 | C |
| ATOM | 2806 | CD | LYS | C | 125 | 40.772 | 29.449 | −32.872 | 1.00 | 44.14 | C |
| ATOM | 2807 | CE | LYS | C | 125 | 42.203 | 29.865 | −33.188 | 1.00 | 44.33 | C |
| ATOM | 2808 | NZ | LYS | C | 125 | 42.480 | 31.317 | −33.012 | 1.00 | 44.72 | N |
| ATOM | 2809 | N | LEU | C | 126 | 40.755 | 24.498 | −32.901 | 1.00 | 48.86 | N |
| ATOM | 2810 | CA | LEU | C | 126 | 41.583 | 23.599 | −32.095 | 1.00 | 49.57 | C |
| ATOM | 2811 | C | LEU | C | 126 | 42.010 | 24.278 | −30.805 | 1.00 | 50.19 | C |
| ATOM | 2812 | O | LEU | C | 126 | 42.540 | 25.394 | −30.824 | 1.00 | 50.52 | O |
| ATOM | 2813 | CB | LEU | C | 126 | 42.838 | 23.163 | −32.859 | 1.00 | 49.28 | C |
| ATOM | 2814 | CG | LEU | C | 126 | 42.741 | 22.054 | −33.907 | 1.00 | 49.30 | C |
| ATOM | 2815 | CD1 | LEU | C | 126 | 44.132 | 21.783 | −34.451 | 1.00 | 49.33 | C |
| ATOM | 2816 | CD2 | LEU | C | 126 | 42.161 | 20.789 | −33.300 | 1.00 | 48.47 | C |
| ATOM | 2817 | N | GLY | C | 127 | 41.779 | 23.600 | −29.686 | 1.00 | 50.50 | N |
| ATOM | 2818 | CA | GLY | C | 127 | 42.146 | 24.159 | −28.400 | 1.00 | 51.25 | C |
| ATOM | 2819 | C | GLY | C | 127 | 43.596 | 24.597 | −28.357 | 1.00 | 51.49 | C |
| ATOM | 2820 | O | GLY | C | 127 | 43.936 | 25.587 | −27.706 | 1.00 | 51.40 | O |
| ATOM | 2821 | N | SER | C | 128 | 44.455 | 23.862 | −29.056 | 1.00 | 51.91 | N |
| ATOM | 2822 | CA | SER | C | 128 | 45.881 | 24.175 | −29.086 | 1.00 | 52.56 | C |
| ATOM | 2823 | C | SER | C | 128 | 46.204 | 25.499 | −29.781 | 1.00 | 52.60 | C |
| ATOM | 2824 | O | SER | C | 128 | 47.298 | 26.040 | −29.613 | 1.00 | 52.59 | O |
| ATOM | 2825 | CB | SER | C | 128 | 46.658 | 23.031 | −29.754 | 1.00 | 52.18 | C |
| ATOM | 2826 | OG | SER | C | 128 | 46.170 | 22.754 | −31.056 | 1.00 | 52.80 | O |
| ATOM | 2827 | N | LYS | C | 129 | 45.250 | 26.023 | −30.548 | 1.00 | 52.51 | N |
| ATOM | 2828 | CA | LYS | C | 129 | 45.457 | 27.279 | −31.260 | 1.00 | 52.09 | C |
| ATOM | 2829 | C | LYS | C | 129 | 44.745 | 28.456 | −30.596 | 1.00 | 51.76 | C |
| ATOM | 2830 | O | LYS | C | 129 | 44.621 | 29.527 | −31.195 | 1.00 | 52.11 | O |
| ATOM | 2831 | CB | LYS | C | 129 | 44.982 | 27.142 | −32.711 | 1.00 | 52.16 | C |
| ATOM | 2832 | N | THR | C | 130 | 44.285 | 28.264 | −29.362 | 1.00 | 50.68 | N |
| ATOM | 2833 | CA | THR | C | 130 | 43.578 | 29.324 | −28.640 | 1.00 | 49.50 | C |
| ATOM | 2834 | C | THR | C | 130 | 44.489 | 30.078 | −27.673 | 1.00 | 49.62 | C |
| ATOM | 2835 | O | THR | C | 130 | 45.534 | 29.570 | −27.254 | 1.00 | 49.24 | O |
| ATOM | 2836 | CB | THR | C | 130 | 42.370 | 28.767 | −27.828 | 1.00 | 48.35 | C |
| ATOM | 2837 | OG1 | THR | C | 130 | 42.837 | 27.886 | −26.801 | 1.00 | 46.67 | O |
| ATOM | 2838 | CG2 | THR | C | 130 | 41.419 | 28.006 | −28.737 | 1.00 | 47.87 | C |
| ATOM | 2839 | N | GLY | C | 131 | 44.074 | 31.294 | −27.327 | 1.00 | 49.58 | N |
| ATOM | 2840 | CA | GLY | C | 131 | 44.836 | 32.128 | −26.414 | 1.00 | 50.00 | C |
| ATOM | 2841 | C | GLY | C | 131 | 43.918 | 33.094 | −25.687 | 1.00 | 50.38 | C |
| ATOM | 2842 | O | GLY | C | 131 | 42.841 | 33.407 | −26.192 | 1.00 | 50.52 | O |
| ATOM | 2843 | N | PRO | C | 132 | 44.323 | 33.602 | −24.511 | 1.00 | 50.42 | N |
| ATOM | 2844 | CA | PRO | C | 132 | 43.564 | 34.541 | −23.677 | 1.00 | 50.80 | C |
| ATOM | 2845 | C | PRO | C | 132 | 43.042 | 35.821 | −24.328 | 1.00 | 50.86 | C |
| ATOM | 2846 | O | PRO | C | 132 | 42.005 | 36.347 | −23.916 | 1.00 | 51.41 | O |
| ATOM | 2847 | CB | PRO | C | 132 | 44.537 | 34.859 | −22.543 | 1.00 | 50.19 | C |
| ATOM | 2848 | CG | PRO | C | 132 | 45.333 | 33.615 | −22.426 | 1.00 | 50.69 | C |
| ATOM | 2849 | CD | PRO | C | 132 | 45.608 | 33.279 | −23.871 | 1.00 | 50.73 | C |
| ATOM | 2850 | N | GLY | C | 133 | 43.750 | 36.334 | −25.326 | 1.00 | 50.68 | N |
| ATOM | 2851 | CA | GLY | C | 133 | 43.301 | 37.569 | −25.950 | 1.00 | 50.31 | C |
| ATOM | 2852 | C | GLY | C | 133 | 42.495 | 37.425 | −27.231 | 1.00 | 49.78 | C |
| ATOM | 2853 | O | GLY | C | 133 | 42.092 | 38.426 | −27.832 | 1.00 | 50.24 | O |
| ATOM | 2854 | N | GLN | C | 134 | 42.242 | 36.188 | −27.645 | 1.00 | 48.18 | N |
| ATOM | 2855 | CA | GLN | C | 134 | 41.504 | 35.929 | −28.880 | 1.00 | 46.73 | C |
| ATOM | 2856 | C | GLN | C | 134 | 40.003 | 36.213 | −28.809 | 1.00 | 45.05 | C |
| ATOM | 2857 | O | GLN | C | 134 | 39.380 | 36.120 | −27.750 | 1.00 | 45.79 | O |
| ATOM | 2858 | CB | GLN | C | 134 | 41.719 | 34.476 | −29.312 | 1.00 | 46.87 | C |
| ATOM | 2859 | CG | GLN | C | 134 | 43.099 | 34.190 | −29.882 | 1.00 | 47.41 | C |
| ATOM | 2860 | CD | GLN | C | 134 | 43.388 | 32.707 | −29.971 | 1.00 | 47.95 | C |
| ATOM | 2861 | OE1 | GLN | C | 134 | 42.484 | 31.904 | −30.195 | 1.00 | 48.19 | O |
| ATOM | 2862 | NE2 | GLN | C | 134 | 44.654 | 32.335 | −29.804 | 1.00 | 47.92 | N |
| ATOM | 2863 | N | LYS | C | 135 | 39.434 | 36.548 | −29.960 | 1.00 | 42.11 | N |
| ATOM | 2864 | CA | LYS | C | 135 | 38.012 | 36.838 | −30.088 | 1.00 | 40.04 | C |
| ATOM | 2865 | C | LYS | C | 135 | 37.212 | 35.530 | −30.172 | 1.00 | 38.28 | C |
| ATOM | 2866 | O | LYS | C | 135 | 36.022 | 35.498 | −29.874 | 1.00 | 36.96 | O |
| ATOM | 2867 | CB | LYS | C | 135 | 37.779 | 37.668 | −31.353 | 1.00 | 39.93 | C |

TABLE 3-continued

FGFR2(D2–D3) Complexed with FGF2

| ATOM | 2868 | CG | LYS | C | 135 | 36.356 | 38.127 | −31.568 | 1.00 | 41.26 | C |
|---|---|---|---|---|---|---|---|---|---|---|---|
| ATOM | 2869 | CD | LYS | C | 135 | 36.252 | 38.964 | −32.836 | 1.00 | 42.03 | C |
| ATOM | 2870 | CE | LYS | C | 135 | 34.843 | 39.510 | −33.005 | 1.00 | 44.12 | C |
| ATOM | 2871 | NZ | LYS | C | 135 | 34.708 | 40.444 | −34.159 | 1.00 | 45.15 | N |
| ATOM | 2872 | N | ALA | C | 136 | 37.890 | 34.457 | −30.568 | 1.00 | 36.67 | N |
| ATOM | 2873 | CA | ALA | C | 136 | 37.278 | 33.143 | −30.732 | 1.00 | 35.40 | C |
| ATOM | 2874 | C | ALA | C | 136 | 36.852 | 32.448 | −29.442 | 1.00 | 34.50 | C |
| ATOM | 2875 | O | ALA | C | 136 | 36.033 | 31.534 | −29.478 | 1.00 | 34.22 | O |
| ATOM | 2876 | CB | ALA | C | 136 | 38.228 | 32.240 | −31.502 | 1.00 | 36.34 | C |
| ATOM | 2877 | N | ILE | C | 137 | 37.402 | 32.873 | −28.307 | 1.00 | 32.81 | N |
| ATOM | 2878 | CA | ILE | C | 137 | 37.068 | 32.253 | −27.026 | 1.00 | 31.85 | C |
| ATOM | 2879 | C | ILE | C | 137 | 36.030 | 33.019 | −26.185 | 1.00 | 30.74 | C |
| ATOM | 2880 | O | ILE | C | 137 | 35.693 | 32.594 | −25.076 | 1.00 | 29.55 | O |
| ATOM | 2881 | CB | ILE | C | 137 | 38.316 | 32.100 | −26.153 | 1.00 | 32.24 | C |
| ATOM | 2882 | CG1 | ILE | C | 137 | 38.781 | 33.480 | −25.679 | 1.00 | 32.05 | C |
| ATOM | 2883 | CG2 | ILE | C | 137 | 39.426 | 31.428 | −26.951 | 1.00 | 32.13 | C |
| ATOM | 2884 | CD1 | ILE | C | 137 | 39.787 | 33.421 | −24.527 | 1.00 | 31.70 | C |
| ATOM | 2885 | N | LEU | C | 138 | 35.523 | 34.132 | −26.709 | 1.00 | 29.05 | N |
| ATOM | 2886 | CA | LEU | C | 138 | 34.559 | 34.947 | −25.966 | 1.00 | 28.81 | C |
| ATOM | 2887 | C | LEU | C | 138 | 33.101 | 34.590 | −26.244 | 1.00 | 28.16 | C |
| ATOM | 2888 | O | LEU | C | 138 | 32.629 | 34.695 | −27.369 | 1.00 | 26.69 | O |
| ATOM | 2889 | CB | LEU | C | 138 | 34.800 | 36.422 | −26.263 | 1.00 | 28.20 | C |
| ATOM | 2890 | CG | LEU | C | 138 | 36.231 | 36.912 | −25.993 | 1.00 | 29.51 | C |
| ATOM | 2891 | CD1 | LEU | C | 138 | 36.375 | 38.314 | −26.550 | 1.00 | 29.14 | C |
| ATOM | 2892 | CD2 | LEU | C | 138 | 36.564 | 36.878 | −24.489 | 1.00 | 28.12 | C |
| ATOM | 2893 | N | PHE | C | 139 | 32.401 | 34.171 | −25.194 | 1.00 | 28.26 | N |
| ATOM | 2894 | CA | PHE | C | 139 | 31.003 | 33.770 | −25.294 | 1.00 | 28.24 | C |
| ATOM | 2895 | C | PHE | C | 139 | 30.087 | 34.593 | −24.402 | 1.00 | 28.66 | C |
| ATOM | 2896 | O | PHE | C | 139 | 30.485 | 35.048 | −23.329 | 1.00 | 28.09 | O |
| ATOM | 2897 | CB | PHE | C | 139 | 30.848 | 32.305 | −24.886 | 1.00 | 27.63 | C |
| ATOM | 2898 | CG | PHE | C | 139 | 31.420 | 31.329 | −25.871 | 1.00 | 28.77 | C |
| ATOM | 2899 | CD1 | PHE | C | 139 | 32.759 | 30.978 | −25.829 | 1.00 | 28.45 | C |
| ATOM | 2900 | CD2 | PHE | C | 139 | 30.604 | 30.760 | −26.853 | 1.00 | 28.64 | C |
| ATOM | 2901 | CE1 | PHE | C | 139 | 33.285 | 30.070 | −26.751 | 1.00 | 29.93 | C |
| ATOM | 2902 | CE2 | PHE | C | 139 | 31.119 | 29.857 | −27.780 | 1.00 | 28.93 | C |
| ATOM | 2903 | CZ | PHE | C | 139 | 32.463 | 29.510 | −27.729 | 1.00 | 29.11 | C |
| ATOM | 2904 | N | LEU | C | 140 | 28.843 | 34.746 | −24.833 | 1.00 | 28.67 | N |
| ATOM | 2905 | CA | LEU | C | 140 | 27.858 | 35.477 | −24.059 | 1.00 | 29.11 | C |
| ATOM | 2906 | C | LEU | C | 140 | 26.681 | 34.540 | −23.809 | 1.00 | 29.71 | C |
| ATOM | 2907 | O | LEU | C | 140 | 26.002 | 34.125 | −24.746 | 1.00 | 30.07 | O |
| ATOM | 2908 | CB | LEU | C | 140 | 27.397 | 36.711 | −24.836 | 1.00 | 30.72 | C |
| ATOM | 2909 | CG | LEU | C | 140 | 26.598 | 37.804 | −24.121 | 1.00 | 32.61 | C |
| ATOM | 2910 | CD1 | LEU | C | 140 | 27.455 | 38.462 | −23.036 | 1.00 | 34.13 | C |
| ATOM | 2911 | CD2 | LEU | C | 140 | 26.171 | 38.863 | −25.140 | 1.00 | 33.01 | C |
| ATOM | 2912 | N | PRO | C | 141 | 26.439 | 34.165 | −22.545 | 1.00 | 30.12 | N |
| ATOM | 2913 | CA | PRO | C | 141 | 25.309 | 33.270 | −22.279 | 1.00 | 31.30 | C |
| ATOM | 2914 | C | PRO | C | 141 | 23.979 | 33.993 | −22.542 | 1.00 | 32.79 | C |
| ATOM | 2915 | O | PRO | C | 141 | 23.788 | 35.138 | −22.113 | 1.00 | 32.92 | O |
| ATOM | 2916 | CB | PRO | C | 141 | 25.502 | 32.903 | −20.807 | 1.00 | 30.88 | C |
| ATOM | 2917 | CG | PRO | C | 141 | 26.136 | 34.135 | −20.251 | 1.00 | 32.30 | C |
| ATOM | 2918 | CD | PRO | C | 141 | 27.164 | 34.468 | −21.301 | 1.00 | 30.47 | C |
| ATOM | 2919 | N | MET | C | 142 | 23.078 | 33.335 | −23.270 | 1.00 | 33.37 | N |
| ATOM | 2920 | CA | MET | C | 142 | 21.774 | 33.925 | −23.588 | 1.00 | 35.47 | C |
| ATOM | 2921 | C | MET | C | 142 | 20.624 | 32.966 | −23.284 | 1.00 | 36.61 | C |
| ATOM | 2922 | O | MET | C | 142 | 20.794 | 31.743 | −23.269 | 1.00 | 36.18 | O |
| ATOM | 2923 | CB | MET | C | 142 | 21.704 | 34.330 | −25.070 | 1.00 | 35.37 | C |
| ATOM | 2924 | CG | MET | C | 142 | 22.608 | 35.496 | −25.470 | 1.00 | 35.81 | C |
| ATOM | 2925 | SD | MET | C | 142 | 22.635 | 35.805 | −27.272 | 1.00 | 36.85 | S |
| ATOM | 2926 | CE | MET | C | 142 | 21.354 | 37.092 | −27.421 | 1.00 | 36.14 | C |
| ATOM | 2927 | N | SER | C | 143 | 19.449 | 33.536 | −23.048 | 1.00 | 38.67 | N |
| ATOM | 2928 | CA | SER | C | 143 | 18.253 | 32.756 | −22.750 | 1.00 | 40.72 | C |
| ATOM | 2929 | C | SER | C | 143 | 17.892 | 31.800 | −23.874 | 1.00 | 41.63 | C |
| ATOM | 2930 | O | SER | C | 143 | 18.057 | 32.116 | −25.056 | 1.00 | 40.60 | O |
| ATOM | 2931 | CB | SER | C | 143 | 17.060 | 33.683 | −22.515 | 1.00 | 41.40 | C |
| ATOM | 2932 | OG | SER | C | 143 | 15.863 | 32.937 | −22.405 | 1.00 | 43.45 | O |
| ATOM | 2933 | N | ALA | C | 144 | 17.393 | 30.628 | −23.498 | 1.00 | 43.48 | N |
| ATOM | 2934 | CA | ALA | C | 144 | 16.977 | 29.637 | −24.475 | 1.00 | 45.83 | C |
| ATOM | 2935 | C | ALA | C | 144 | 15.525 | 29.918 | −24.880 | 1.00 | 47.20 | C |
| ATOM | 2936 | O | ALA | C | 144 | 14.797 | 29.011 | −25.274 | 1.00 | 47.66 | O |
| ATOM | 2937 | CB | ALA | C | 144 | 17.100 | 28.250 | −23.883 | 1.00 | 46.09 | C |
| ATOM | 2938 | N | LYS | C | 145 | 15.117 | 31.183 | −24.774 | 1.00 | 48.47 | N |
| ATOM | 2939 | CA | LYS | C | 145 | 13.762 | 31.598 | −25.136 | 1.00 | 49.70 | C |
| ATOM | 2940 | C | LYS | C | 145 | 12.717 | 30.794 | −24.379 | 1.00 | 50.25 | C |
| ATOM | 2941 | O | LYS | C | 145 | 12.639 | 31.010 | −23.149 | 1.00 | 51.81 | O |
| ATOM | 2942 | CB | LYS | C | 145 | 13.544 | 31.434 | −26.645 | 1.00 | 48.79 | C |
| TER | 2943 | | LYS | C | 145 | | | | | | |
| ATOM | 2944 | N | HIS | D | 16 | 54.126 | 19.899 | 14.823 | 1.00 | 38.67 | N |

TABLE 3-continued

| | | | | | | | | | | |
|---|---|---|---|---|---|---|---|---|---|---|
| FGFR2(D2–D3) Complexed with FGF2 | | | | | | | | | | |
| ATOM | 2945 | CA | HIS | D | 16 | 54.234 | 21.034 | 13.858 | 1.00 | 38.27 | C |
| ATOM | 2946 | C | HIS | D | 16 | 55.316 | 21.999 | 14.343 | 1.00 | 37.14 | C |
| ATOM | 2947 | O | HIS | D | 16 | 55.264 | 22.495 | 15.468 | 1.00 | 36.27 | O |
| ATOM | 2948 | CB | HIS | D | 16 | 52.888 | 21.755 | 13.734 | 1.00 | 39.12 | C |
| ATOM | 2949 | N | PHE | D | 17 | 56.295 | 22.258 | 13.480 | 1.00 | 36.78 | N |
| ATOM | 2950 | CA | PHE | D | 17 | 57.414 | 23.139 | 13.827 | 1.00 | 36.50 | C |
| ATOM | 2951 | C | PHE | D | 17 | 57.042 | 24.586 | 14.193 | 1.00 | 36.19 | C |
| ATOM | 2952 | O | PHE | D | 17 | 57.753 | 25.226 | 14.970 | 1.00 | 36.26 | O |
| ATOM | 2953 | CB | PHE | D | 17 | 58.472 | 23.128 | 12.704 | 1.00 | 35.56 | C |
| ATOM | 2954 | CG | PHE | D | 17 | 58.007 | 23.745 | 11.400 | 1.00 | 35.39 | C |
| ATOM | 2955 | CD1 | PHE | D | 17 | 58.315 | 25.068 | 11.092 | 1.00 | 34.82 | C |
| ATOM | 2956 | CD2 | PHE | D | 17 | 57.274 | 23.001 | 10.482 | 1.00 | 34.55 | C |
| ATOM | 2957 | CE1 | PHE | D | 17 | 57.902 | 25.643 | 9.879 | 1.00 | 34.72 | C |
| ATOM | 2958 | CE2 | PHE | D | 17 | 56.856 | 23.561 | 9.271 | 1.00 | 34.88 | C |
| ATOM | 2959 | CZ | PHE | D | 17 | 57.173 | 24.888 | 8.969 | 1.00 | 34.53 | C |
| ATOM | 2960 | N | LYS | D | 18 | 55.931 | 25.087 | 13.651 | 1.00 | 36.16 | N |
| ATOM | 2961 | CA | LYS | D | 18 | 55.465 | 26.451 | 13.919 | 1.00 | 35.93 | C |
| ATOM | 2962 | C | LYS | D | 18 | 54.863 | 26.648 | 15.307 | 1.00 | 36.04 | C |
| ATOM | 2963 | O | LYS | D | 18 | 54.742 | 27.773 | 15.782 | 1.00 | 35.87 | O |
| ATOM | 2964 | CB | LYS | D | 18 | 54.411 | 26.861 | 12.887 | 1.00 | 36.04 | C |
| ATOM | 2965 | CG | LYS | D | 18 | 54.918 | 27.006 | 11.464 | 1.00 | 37.00 | C |
| ATOM | 2966 | CD | LYS | D | 18 | 53.914 | 27.766 | 10.608 | 1.00 | 38.12 | C |
| ATOM | 2967 | CE | LYS | D | 18 | 52.666 | 26.940 | 10.305 | 1.00 | 38.98 | C |
| ATOM | 2968 | NZ | LYS | D | 18 | 52.845 | 26.089 | 9.097 | 1.00 | 38.63 | N |
| ATOM | 2969 | N | ASP | D | 19 | 54.466 | 25.556 | 15.951 | 1.00 | 36.18 | N |
| ATOM | 2970 | CA | ASP | D | 19 | 53.868 | 25.639 | 17.276 | 1.00 | 35.73 | C |
| ATOM | 2971 | C | ASP | D | 19 | 54.874 | 25.897 | 18.384 | 1.00 | 35.80 | C |
| ATOM | 2972 | O | ASP | D | 19 | 56.032 | 25.466 | 18.306 | 1.00 | 35.27 | O |
| ATOM | 2973 | CB | ASP | D | 19 | 53.121 | 24.347 | 17.595 | 1.00 | 36.20 | C |
| ATOM | 2974 | CG | ASP | D | 19 | 51.888 | 24.162 | 16.735 | 1.00 | 36.50 | C |
| ATOM | 2975 | OD1 | ASP | D | 19 | 51.395 | 23.022 | 16.662 | 1.00 | 35.39 | O |
| ATOM | 2976 | OD2 | ASP | D | 19 | 51.412 | 25.162 | 16.143 | 1.00 | 37.10 | O |
| ATOM | 2977 | N | PRO | D | 20 | 54.442 | 26.616 | 19.431 | 1.00 | 35.60 | N |
| ATOM | 2978 | CA | PRO | D | 20 | 55.310 | 26.919 | 20.572 | 1.00 | 35.68 | C |
| ATOM | 2979 | C | PRO | D | 20 | 55.664 | 25.610 | 21.271 | 1.00 | 35.52 | C |
| ATOM | 2980 | O | PRO | D | 20 | 54.985 | 24.598 | 21.086 | 1.00 | 34.34 | O |
| ATOM | 2981 | CB | PRO | D | 20 | 54.450 | 27.854 | 21.428 | 1.00 | 35.65 | C |
| ATOM | 2982 | CG | PRO | D | 20 | 53.052 | 27.478 | 21.060 | 1.00 | 36.50 | C |
| ATOM | 2983 | CD | PRO | D | 20 | 53.137 | 27.283 | 19.575 | 1.00 | 36.19 | C |
| ATOM | 2984 | N | LYS | D | 21 | 56.723 | 25.628 | 22.073 | 1.00 | 35.95 | N |
| ATOM | 2985 | CA | LYS | D | 21 | 57.174 | 24.416 | 22.743 | 1.00 | 36.41 | C |
| ATOM | 2986 | C | LYS | D | 21 | 57.799 | 24.676 | 24.090 | 1.00 | 36.32 | C |
| ATOM | 2987 | O | LYS | D | 21 | 58.139 | 25.811 | 24.422 | 1.00 | 36.96 | O |
| ATOM | 2988 | CB | LYS | D | 22 | 58.222 | 23.722 | 21.870 | 1.00 | 36.98 | C |
| ATOM | 2989 | CG | LYS | D | 22 | 57.658 | 23.001 | 20.680 | 1.00 | 39.76 | C |
| ATOM | 2990 | CD | LYS | D | 21 | 58.649 | 22.944 | 19.546 | 1.00 | 42.45 | C |
| ATOM | 2991 | CE | LYS | D | 21 | 58.146 | 22.000 | 18.458 | 1.00 | 44.33 | C |
| ATOM | 2992 | NZ | LYS | D | 21 | 56.697 | 22.198 | 18.191 | 1.00 | 44.06 | N |
| ATOM | 2993 | N | ARG | D | 22 | 57.944 | 23.610 | 24.866 | 1.00 | 35.71 | N |
| ATOM | 2994 | CA | ARG | D | 22 | 58.618 | 23.704 | 26.145 | 1.00 | 36.21 | C |
| ATOM | 2995 | C | ARG | D | 22 | 59.935 | 22.992 | 25.851 | 1.00 | 35.14 | C |
| ATOM | 2996 | O | ARG | D | 22 | 59.956 | 22.033 | 25.081 | 1.00 | 35.57 | O |
| ATOM | 2997 | CB | ARG | D | 22 | 57.877 | 22.941 | 27.246 | 1.00 | 37.73 | C |
| ATOM | 2998 | CG | ARG | D | 22 | 56.414 | 23.305 | 27.477 | 1.00 | 41.03 | C |
| ATOM | 2999 | CD | ARG | D | 22 | 55.986 | 22.704 | 28.804 | 1.00 | 43.60 | C |
| ATOM | 3000 | NE | ARG | D | 22 | 54.571 | 22.353 | 28.919 | 1.00 | 46.77 | N |
| ATOM | 3001 | CZ | ARG | D | 22 | 53.568 | 23.221 | 29.012 | 1.00 | 48.46 | C |
| ATOM | 3002 | NH1 | ARG | D | 22 | 53.800 | 24.533 | 28.993 | 1.00 | 49.57 | N |
| ATOM | 3003 | NH2 | ARG | D | 22 | 52.328 | 22.771 | 29.169 | 1.00 | 48.22 | N |
| ATOM | 3004 | N | LEU | D | 23 | 61.030 | 23.470 | 26.423 | 1.00 | 34.08 | N |
| ATOM | 3005 | CA | LEU | D | 23 | 62.327 | 22.822 | 26.234 | 1.00 | 32.93 | C |
| ATOM | 3006 | C | LEU | D | 23 | 62.703 | 22.179 | 27.556 | 1.00 | 32.48 | C |
| ATOM | 3007 | O | LEU | D | 23 | 63.053 | 22.865 | 28.514 | 1.00 | 31.86 | O |
| ATOM | 3008 | CB | LEU | D | 23 | 63.401 | 23.832 | 25.826 | 1.00 | 32.07 | C |
| ATOM | 3009 | CG | LEU | D | 23 | 63.322 | 24.421 | 24.417 | 1.00 | 33.42 | C |
| ATOM | 3010 | CD1 | LEU | D | 23 | 64.358 | 25.525 | 24.263 | 1.00 | 32.81 | C |
| ATOM | 3011 | CD2 | LEU | D | 23 | 63.541 | 23.314 | 23.382 | 1.00 | 33.14 | C |
| ATOM | 3012 | N | TYR | D | 24 | 62.621 | 20.855 | 27.590 | 1.00 | 32.58 | N |
| ATOM | 3013 | CA | TYR | D | 24 | 62.927 | 20.072 | 28.771 | 1.00 | 31.77 | C |
| ATOM | 3014 | C | TYR | D | 24 | 64.417 | 19.700 | 28.834 | 1.00 | 32.21 | C |
| ATOM | 3015 | O | TYR | D | 24 | 64.983 | 19.178 | 27.868 | 1.00 | 32.68 | O |
| ATOM | 3016 | CB | TYR | D | 24 | 62.042 | 18.828 | 28.749 | 1.00 | 30.62 | C |
| ATOM | 3017 | CG | TYR | D | 24 | 62.473 | 17.713 | 29.668 | 1.00 | 30.23 | C |
| ATOM | 3018 | CD1 | TYR | D | 24 | 63.520 | 16.864 | 29.321 | 1.00 | 28.85 | C |
| ATOM | 3019 | CD2 | TYR | D | 24 | 61.810 | 17.483 | 30.870 | 1.00 | 29.46 | C |
| ATOM | 3020 | CE1 | TYR | D | 24 | 63.893 | 15.804 | 30.147 | 1.00 | 28.77 | C |
| ATOM | 3021 | CE2 | TYR | D | 24 | 62.175 | 16.433 | 31.702 | 1.00 | 29.39 | C |

TABLE 3-continued

FGFR2(D2–D3) Complexed with FGF2

| | | | | | | | | | | |
|---|---|---|---|---|---|---|---|---|---|---|
| ATOM | 3022 | CZ | TYR | D | 24 | 63.217 | 15.593 | 31.331 | 1.00 | 28.77 | C |
| ATOM | 3023 | OH | TYR | D | 24 | 63.559 | 14.538 | 32.141 | 1.00 | 27.74 | O |
| ATOM | 3024 | N | CYS | D | 25 | 65.051 | 19.966 | 29.972 | 1.00 | 32.20 | N |
| ATOM | 3025 | CA | CYS | D | 25 | 66.467 | 19.642 | 30.133 | 1.00 | 32.62 | C |
| ATOM | 3026 | C | CYS | D | 25 | 66.643 | 18.290 | 30.822 | 1.00 | 33.02 | C |
| ATOM | 3027 | O | CYS | D | 25 | 66.117 | 18.059 | 31.915 | 1.00 | 32.11 | O |
| ATOM | 3028 | CB | CYS | D | 25 | 67.187 | 20.723 | 30.946 | 1.00 | 32.95 | C |
| ATOM | 3029 | SG | CYS | D | 25 | 69.001 | 20.532 | 30.972 | 1.00 | 31.97 | S |
| ATOM | 3030 | N | LYS | D | 26 | 67.382 | 17.400 | 30.169 | 1.00 | 34.05 | N |
| ATOM | 3031 | CA | LYS | D | 26 | 67.637 | 16.076 | 30.710 | 1.00 | 35.40 | C |
| ATOM | 3032 | C | LYS | D | 26 | 68.281 | 16.180 | 32.089 | 1.00 | 36.05 | C |
| ATOM | 3033 | O | LYS | D | 26 | 68.062 | 15.331 | 32.955 | 1.00 | 36.30 | O |
| ATOM | 3034 | CB | LYS | D | 26 | 68.559 | 15.281 | 29.785 | 1.00 | 35.59 | C |
| ATOM | 3035 | CG | LYS | D | 26 | 68.716 | 13.828 | 30.221 | 1.00 | 36.96 | C |
| ATOM | 3036 | CD | LYS | D | 26 | 69.634 | 13.048 | 29.297 | 1.00 | 37.22 | C |
| ATOM | 3037 | CE | LYS | D | 26 | 69.752 | 11.603 | 29.752 | 1.00 | 38.52 | C |
| ATOM | 3038 | NZ | LYS | D | 26 | 70.750 | 10.852 | 28.930 | 1.00 | 39.15 | N |
| ATOM | 3039 | N | ASN | D | 27 | 69.074 | 17.228 | 32.291 | 1.00 | 36.41 | N |
| ATOM | 3040 | CA | ASN | D | 27 | 69.750 | 17.436 | 33.568 | 1.00 | 36.38 | C |
| ATOM | 3041 | C | ASN | D | 27 | 68.740 | 17.901 | 34.617 | 1.00 | 36.08 | C |
| ATOM | 3042 | O | ASN | D | 27 | 68.336 | 19.066 | 34.615 | 1.00 | 35.53 | O |
| ATOM | 3043 | CB | ASN | D | 27 | 70.852 | 18.491 | 33.408 | 1.00 | 36.79 | C |
| ATOM | 3044 | CG | ASN | D | 27 | 71.929 | 18.379 | 34.482 | 1.00 | 37.99 | C |
| ATOM | 3045 | OD1 | ASN | D | 27 | 72.675 | 19.333 | 34.746 | 1.00 | 37.72 | O |
| ATOM | 3046 | ND2 | ASN | D | 27 | 72.024 | 17.207 | 35.096 | 1.00 | 37.35 | N |
| ATOM | 3047 | N | GLY | D | 28 | 68.326 | 16.989 | 35.500 | 1.00 | 35.93 | N |
| ATOM | 3048 | CA | GLY | D | 28 | 67.368 | 17.340 | 36.539 | 1.00 | 35.08 | C |
| ATOM | 3049 | C | GLY | D | 28 | 65.898 | 17.394 | 36.123 | 1.00 | 35.49 | C |
| ATOM | 3050 | O | GLY | D | 28 | 65.009 | 17.399 | 36.971 | 1.00 | 34.34 | O |
| ATOM | 3051 | N | GLY | D | 29 | 65.630 | 17.443 | 34.825 | 1.00 | 35.76 | N |
| ATOM | 3052 | CA | GLY | D | 29 | 64.252 | 17.489 | 34.373 | 1.00 | 36.75 | C |
| ATOM | 3053 | C | GLY | D | 29 | 63.562 | 18.835 | 34.551 | 1.00 | 37.21 | C |
| ATOM | 3054 | O | GLY | D | 29 | 62.400 | 18.880 | 34.942 | 1.00 | 37.24 | O |
| ATOM | 3055 | N | PHE | D | 30 | 64.269 | 19.928 | 34.276 | 1.00 | 37.20 | N |
| ATOM | 3056 | CA | PHE | D | 30 | 63.694 | 21.270 | 34.391 | 1.00 | 37.97 | C |
| ATOM | 3057 | C | PHE | D | 30 | 63.298 | 21.800 | 33.010 | 1.00 | 38.10 | C |
| ATOM | 3058 | O | PHE | D | 30 | 63.945 | 21.496 | 32.009 | 1.00 | 38.11 | O |
| ATOM | 3059 | CB | PHE | D | 30 | 64.695 | 22.287 | 34.963 | 1.00 | 37.64 | C |
| ATOM | 3060 | CG | PHE | D | 30 | 65.278 | 21.923 | 36.296 | 1.00 | 37.90 | C |
| ATOM | 3061 | CD1 | PHE | D | 30 | 66.540 | 21.334 | 36.381 | 1.00 | 37.94 | C |
| ATOM | 3062 | CD2 | PHE | D | 30 | 64.603 | 22.239 | 37.474 | 1.00 | 38.44 | C |
| ATOM | 3063 | CE1 | PHE | D | 30 | 67.126 | 21.074 | 37.626 | 1.00 | 37.98 | C |
| ATOM | 3064 | CE2 | PHE | D | 30 | 65.175 | 21.983 | 38.720 | 1.00 | 37.36 | C |
| ATOM | 3065 | CZ | PHE | D | 30 | 66.440 | 21.401 | 38.795 | 1.00 | 38.16 | C |
| ATOM | 3066 | N | PHE | D | 31 | 62.246 | 22.609 | 32.968 | 1.00 | 37.80 | N |
| ATOM | 3067 | CA | PHE | D | 31 | 61.799 | 23.226 | 31.726 | 1.00 | 37.80 | C |
| ATOM | 3068 | C | PHE | D | 31 | 62.462 | 24.603 | 31.677 | 1.00 | 38.08 | C |
| ATOM | 3069 | O | PHE | D | 31 | 62.414 | 25.343 | 32.661 | 1.00 | 37.41 | O |
| ATOM | 3070 | CB | PHE | D | 31 | 60.276 | 23.415 | 31.723 | 1.00 | 37.75 | C |
| ATOM | 3071 | CG | PHE | D | 31 | 59.493 | 22.134 | 31.584 | 1.00 | 37.85 | C |
| ATOM | 3072 | CD1 | PHE | D | 31 | 59.590 | 21.369 | 30.431 | 1.00 | 37.09 | C |
| ATOM | 3073 | CD2 | PHE | D | 31 | 58.645 | 21.707 | 32.601 | 1.00 | 38.01 | C |
| ATOM | 3074 | CE1 | PHE | D | 31 | 58.854 | 20.196 | 30.285 | 1.00 | 37.44 | C |
| ATOM | 3075 | CE2 | PHE | D | 31 | 57.901 | 20.528 | 32.465 | 1.00 | 38.66 | C |
| ATOM | 3076 | CZ | PHE | D | 31 | 58.007 | 19.774 | 31.301 | 1.00 | 38.10 | C |
| ATOM | 3077 | N | LEU | D | 32 | 63.085 | 24.942 | 30.550 | 1.00 | 38.06 | N |
| ATOM | 3078 | CA | LEU | D | 32 | 63.733 | 26.244 | 30.416 | 1.00 | 38.41 | C |
| ATOM | 3079 | C | LEU | D | 32 | 62.678 | 27.326 | 30.623 | 1.00 | 39.14 | C |
| ATOM | 3080 | O | LEU | D | 32 | 61.622 | 27.295 | 29.991 | 1.00 | 39.29 | O |
| ATOM | 3081 | CB | LEU | D | 32 | 64.357 | 26.399 | 29.029 | 1.00 | 37.69 | C |
| ATOM | 3082 | CG | LEU | D | 32 | 65.257 | 27.630 | 28.835 | 1.00 | 37.38 | C |
| ATOM | 3083 | CD1 | LEU | D | 32 | 66.368 | 27.640 | 29.887 | 1.00 | 36.99 | C |
| ATOM | 3084 | CD2 | LEU | D | 32 | 65.856 | 27.600 | 27.445 | 1.00 | 36.24 | C |
| ATOM | 3085 | N | ARG | D | 33 | 62.965 | 28.281 | 31.501 | 1.00 | 39.62 | N |
| ATOM | 3086 | CA | ARG | D | 33 | 62.019 | 29.355 | 31.799 | 1.00 | 40.13 | C |
| ATOM | 3087 | C | ARG | D | 33 | 62.569 | 30.759 | 31.540 | 1.00 | 40.47 | C |
| ATOM | 3088 | O | ARG | D | 33 | 63.702 | 31.069 | 31.908 | 1.00 | 40.15 | O |
| ATOM | 3089 | CB | ARG | D | 33 | 61.564 | 29.247 | 33.261 | 1.00 | 39.82 | C |
| ATOM | 3090 | CG | ARG | D | 33 | 60.565 | 30.316 | 33.681 | 1.00 | 40.22 | C |
| ATOM | 3091 | CD | ARG | D | 33 | 59.896 | 29.988 | 35.013 | 1.00 | 39.80 | C |
| ATOM | 3092 | NE | ARG | D | 33 | 60.834 | 29.991 | 36.131 | 1.00 | 40.49 | N |
| ATOM | 3093 | CZ | ARG | D | 33 | 60.468 | 29.978 | 37.413 | 1.00 | 41.41 | C |
| ATOM | 3094 | NH1 | ARG | D | 33 | 59.175 | 29.959 | 37.732 | 1.00 | 41.64 | N |
| ATOM | 3095 | NH2 | ARG | D | 33 | 61.386 | 29.991 | 38.378 | 1.00 | 39.88 | N |
| ATOM | 3096 | N | ILE | D | 34 | 61.758 | 31.602 | 30.905 | 1.00 | 41.17 | N |
| ATOM | 3097 | CA | ILE | D | 34 | 62.158 | 32.976 | 30.610 | 1.00 | 42.90 | C |
| ATOM | 3098 | C | ILE | D | 34 | 61.194 | 33.940 | 31.309 | 1.00 | 44.48 | C |

TABLE 3-continued

FGFR2(D2–D3) Complexed with FGF2

| ATOM | 3099 | O | ILE | D | 34 | 60.048 | 34.114 | 30.885 | 1.00 | 44.51 | O |
|---|---|---|---|---|---|---|---|---|---|---|---|
| ATOM | 3100 | CB | ILE | D | 34 | 62.159 | 33.243 | 29.082 | 1.00 | 42.66 | C |
| ATOM | 3101 | CG1 | ILE | D | 34 | 63.213 | 32.362 | 28.399 | 1.00 | 42.04 | C |
| ATOM | 3102 | CG2 | ILE | D | 34 | 62.453 | 34.701 | 28.800 | 1.00 | 41.35 | C |
| ATOM | 3103 | CD1 | ILE | D | 34 | 63.256 | 32.507 | 26.889 | 1.00 | 41.47 | C |
| ATOM | 3104 | N | HIS | D | 35 | 61.676 | 34.550 | 32.389 | 1.00 | 46.13 | N |
| ATOM | 3105 | CA | HIS | D | 35 | 60.890 | 35.482 | 33.193 | 1.00 | 48.17 | C |
| ATOM | 3106 | C | HIS | D | 35 | 60.651 | 36.828 | 32.514 | 1.00 | 49.27 | C |
| ATOM | 3107 | O | HIS | D | 35 | 61.449 | 37.273 | 31.687 | 1.00 | 49.41 | O |
| ATOM | 3108 | CB | HIS | D | 35 | 61.569 | 35.702 | 34.553 | 1.00 | 47.48 | C |
| ATOM | 3109 | N | PRO | D | 36 | 59.538 | 37.498 | 32.865 | 1.00 | 50.83 | N |
| ATOM | 3110 | CA | PRO | D | 36 | 59.169 | 38.804 | 32.300 | 1.00 | 51.53 | C |
| ATOM | 3111 | C | PRO | D | 36 | 60.272 | 39.859 | 32.420 | 1.00 | 52.04 | C |
| ATOM | 3112 | O | PRO | D | 36 | 60.417 | 40.713 | 31.543 | 1.00 | 52.40 | O |
| ATOM | 3113 | CB | PRO | D | 36 | 57.926 | 39.186 | 33.100 | 1.00 | 52.02 | C |
| ATOM | 3114 | CG | PRO | D | 36 | 57.314 | 37.859 | 33.428 | 1.00 | 51.73 | C |
| ATOM | 3115 | CD | PRO | D | 36 | 58.517 | 37.038 | 33.825 | 1.00 | 51.06 | C |
| ATOM | 3116 | N | ASP | D | 37 | 61.045 | 39.795 | 33.502 | 1.00 | 52.30 | N |
| ATOM | 3117 | CA | ASP | D | 37 | 62.124 | 40.746 | 33.738 | 1.00 | 52.98 | C |
| ATOM | 3118 | C | ASP | D | 37 | 63.442 | 40.350 | 33.082 | 1.00 | 52.81 | C |
| ATOM | 3119 | O | ASP | D | 37 | 64.467 | 41.003 | 33.298 | 1.00 | 52.83 | O |
| ATOM | 3120 | CB | ASP | D | 37 | 62.349 | 40.925 | 35.240 | 1.00 | 54.57 | C |
| ATOM | 3121 | CG | ASP | D | 37 | 62.536 | 39.607 | 35.956 | 1.00 | 56.00 | C |
| ATOM | 3122 | OD1 | ASP | D | 37 | 61.538 | 38.866 | 36.088 | 1.00 | 57.43 | O |
| ATOM | 3123 | OD2 | ASP | D | 37 | 63.675 | 39.307 | 36.376 | 1.00 | 56.89 | O |
| ATOM | 3124 | N | GLY | D | 38 | 63.427 | 39.270 | 32.307 | 1.00 | 52.15 | N |
| ATOM | 3125 | CA | GLY | D | 38 | 64.638 | 38.849 | 31.626 | 1.00 | 51.24 | C |
| ATOM | 3126 | C | GLY | D | 38 | 65.546 | 37.828 | 32.292 | 1.00 | 50.73 | C |
| ATOM | 3127 | O | GLY | D | 38 | 66.608 | 37.512 | 31.749 | 1.00 | 50.65 | O |
| ATOM | 3128 | N | ARG | D | 39 | 65.174 | 37.308 | 33.457 | 1.00 | 49.97 | N |
| ATOM | 3129 | CA | ARG | D | 39 | 66.029 | 36.309 | 34.093 | 1.00 | 49.69 | C |
| ATOM | 3130 | C | ARG | D | 39 | 65.758 | 34.932 | 33.492 | 1.00 | 48.51 | C |
| ATOM | 3131 | O | ARG | D | 39 | 64.637 | 34.643 | 33.061 | 1.00 | 48.43 | O |
| ATOM | 3132 | CB | ARG | D | 39 | 65.818 | 36.274 | 35.611 | 1.00 | 51.28 | C |
| ATOM | 3133 | CG | ARG | D | 39 | 66.829 | 37.120 | 36.384 | 1.00 | 54.09 | C |
| ATOM | 3134 | CD | ARG | D | 39 | 66.597 | 37.087 | 37.895 | 1.00 | 55.79 | C |
| ATOM | 3135 | NE | ARG | D | 39 | 65.250 | 37.530 | 38.246 | 1.00 | 58.04 | N |
| ATOM | 3136 | CZ | ARG | D | 39 | 64.186 | 36.733 | 38.292 | 1.00 | 58.99 | C |
| ATOM | 3137 | NH1 | ARG | D | 39 | 62.997 | 37.226 | 38.614 | 1.00 | 59.48 | N |
| ATOM | 3138 | NH2 | ARG | D | 39 | 64.311 | 35.437 | 38.038 | 1.00 | 60.22 | N |
| ATOM | 3139 | N | VAL | D | 40 | 66.786 | 34.091 | 33.447 | 1.00 | 46.54 | N |
| ATOM | 3140 | CA | VAL | D | 40 | 66.634 | 32.751 | 32.890 | 1.00 | 45.12 | C |
| ATOM | 3141 | C | VAL | D | 40 | 67.030 | 31.647 | 33.866 | 1.00 | 44.62 | C |
| ATOM | 3142 | O | VAL | D | 40 | 68.118 | 31.670 | 34.443 | 1.00 | 44.40 | O |
| ATOM | 3143 | CB | VAL | D | 40 | 67.471 | 32.571 | 31.596 | 1.00 | 44.81 | C |
| ATOM | 3144 | CG1 | VAL | D | 40 | 67.383 | 31.128 | 31.114 | 1.00 | 43.98 | C |
| ATOM | 3145 | CG2 | VAL | D | 40 | 66.973 | 33.508 | 30.510 | 1.00 | 44.13 | C |
| ATOM | 3146 | N | ASP | D | 41 | 66.134 | 30.680 | 34.039 | 1.00 | 43.92 | N |
| ATOM | 3147 | CA | ASP | D | 41 | 66.370 | 29.534 | 34.916 | 1.00 | 43.96 | C |
| ATOM | 3148 | C | ASP | D | 41 | 65.503 | 28.355 | 34.474 | 1.00 | 44.09 | C |
| ATOM | 3149 | O | ASP | D | 41 | 64.914 | 28.379 | 33.394 | 1.00 | 43.67 | O |
| ATOM | 3150 | CB | ASP | D | 41 | 66.066 | 29.881 | 36.389 | 1.00 | 43.15 | C |
| ATOM | 3151 | CG | ASP | D | 41 | 64.581 | 30.180 | 36.653 | 1.00 | 43.98 | C |
| ATOM | 3152 | OD1 | ASP | D | 41 | 64.233 | 30.406 | 37.840 | 1.00 | 43.89 | O |
| ATOM | 3153 | OD2 | ASP | D | 41 | 63.765 | 30.191 | 35.703 | 1.00 | 41.66 | O |
| ATOM | 3154 | N | GLY | D | 42 | 65.427 | 27.334 | 35.321 | 1.00 | 44.01 | N |
| ATOM | 3155 | CA | GLY | D | 42 | 64.630 | 26.167 | 35.011 | 1.00 | 44.61 | C |
| ATOM | 3156 | C | GLY | D | 42 | 63.653 | 25.867 | 36.130 | 1.00 | 45.13 | C |
| ATOM | 3157 | O | GLY | D | 42 | 63.891 | 26.232 | 37.274 | 1.00 | 45.40 | O |
| ATOM | 3158 | N | VAL | D | 43 | 62.553 | 25.200 | 35.796 | 1.00 | 45.41 | N |
| ATOM | 3159 | CA | VAL | D | 43 | 61.531 | 24.852 | 36.771 | 1.00 | 45.73 | C |
| ATOM | 3160 | C | VAL | D | 43 | 60.873 | 23.534 | 36.359 | 1.00 | 46.34 | C |
| ATOM | 3161 | O | VAL | D | 43 | 60.838 | 23.196 | 35.174 | 1.00 | 46.69 | O |
| ATOM | 3162 | CB | VAL | D | 43 | 60.469 | 25.995 | 36.875 | 1.00 | 45.11 | C |
| ATOM | 3163 | CG1 | VAL | D | 43 | 59.625 | 26.067 | 35.609 | 1.00 | 43.89 | C |
| ATOM | 3164 | CG2 | VAL | D | 43 | 59.596 | 25.789 | 38.092 | 1.00 | 45.21 | C |
| ATOM | 3165 | N | ARG | D | 44 | 60.359 | 22.795 | 37.339 | 1.00 | 47.07 | N |
| ATOM | 3166 | CA | ARG | D | 44 | 59.721 | 21.504 | 37.093 | 1.00 | 48.22 | C |
| ATOM | 3167 | C | ARG | D | 44 | 58.216 | 21.574 | 36.810 | 1.00 | 49.00 | C |
| ATOM | 3168 | O | ARG | D | 44 | 57.660 | 20.680 | 36.169 | 1.00 | 49.13 | O |
| ATOM | 3169 | CB | ARG | D | 44 | 59.947 | 20.570 | 38.296 | 1.00 | 48.25 | C |
| ATOM | 3170 | CG | ARG | D | 44 | 61.396 | 20.125 | 38.554 | 1.00 | 48.15 | C |
| ATOM | 3171 | CD | ARG | D | 44 | 61.425 | 19.003 | 39.600 | 1.00 | 47.68 | C |
| ATOM | 3172 | NE | ARG | D | 44 | 62.689 | 18.262 | 39.650 | 1.00 | 48.47 | N |
| ATOM | 3173 | CZ | ARG | D | 44 | 63.846 | 18.740 | 40.112 | 1.00 | 48.64 | C |
| ATOM | 3174 | NH1 | ARG | D | 44 | 63.932 | 19.977 | 40.579 | 1.00 | 49.00 | N |
| ATOM | 3175 | NH2 | ARG | D | 44 | 64.928 | 17.972 | 40.109 | 1.00 | 49.22 | N |

TABLE 3-continued

FGFR2(D2–D3) Complexed with FGF2

| ATOM | 3176 | N | GLU | D | 45 | 57.557 | 22.627 | 37.289 | 1.00 | 49.76 | N |
|---|---|---|---|---|---|---|---|---|---|---|---|
| ATOM | 3177 | CA | GLU | D | 45 | 56.109 | 22.773 | 37.106 | 1.00 | 50.30 | C |
| ATOM | 3178 | C | GLU | D | 45 | 55.680 | 23.011 | 35.656 | 1.00 | 50.71 | C |
| ATOM | 3179 | O | GLU | D | 45 | 55.824 | 24.112 | 35.121 | 1.00 | 50.47 | O |
| ATOM | 3180 | CB | GLU | D | 45 | 55.577 | 23.905 | 37.987 | 1.00 | 49.49 | C |
| ATOM | 3181 | N | LYS | D | 46 | 55.135 | 21.970 | 35.036 | 1.00 | 51.11 | N |
| ATOM | 3182 | CA | LYS | D | 46 | 54.685 | 22.040 | 33.652 | 1.00 | 51.83 | C |
| ATOM | 3183 | C | LYS | D | 46 | 53.616 | 23.116 | 33.430 | 1.00 | 52.71 | C |
| ATOM | 3184 | O | LYS | D | 46 | 53.309 | 23.470 | 32.289 | 1.00 | 52.71 | O |
| ATOM | 3185 | CB | LYS | D | 46 | 54.140 | 20.677 | 33.219 | 1.00 | 50.96 | C |
| ATOM | 3186 | N | SER | D | 47 | 53.057 | 23.641 | 34.517 | 1.00 | 53.19 | N |
| ATOM | 3187 | CA | SER | D | 47 | 52.015 | 24.657 | 34.418 | 1.00 | 53.48 | C |
| ATOM | 3188 | C | SER | D | 47 | 52.522 | 26.092 | 34.336 | 1.00 | 52.94 | C |
| ATOM | 3189 | O | SER | D | 47 | 51.762 | 26.996 | 33.983 | 1.00 | 52.87 | O |
| ATOM | 3190 | CB | SER | D | 47 | 51.048 | 24.543 | 35.601 | 1.00 | 54.05 | C |
| ATOM | 3191 | OG | SER | D | 47 | 51.734 | 24.698 | 36.833 | 1.00 | 56.01 | O |
| ATOM | 3192 | N | ASP | D | 48 | 53.794 | 26.310 | 34.664 | 1.00 | 52.50 | N |
| ATOM | 3193 | CA | ASP | D | 48 | 54.362 | 27.657 | 34.621 | 1.00 | 51.66 | C |
| ATOM | 3194 | C | ASP | D | 48 | 54.161 | 28.310 | 33.254 | 1.00 | 50.90 | C |
| ATOM | 3195 | O | ASP | D | 48 | 54.530 | 27.745 | 32.223 | 1.00 | 50.75 | O |
| ATOM | 3196 | CB | ASP | D | 48 | 55.858 | 27.629 | 34.961 | 1.00 | 51.83 | C |
| ATOM | 3197 | N | PRO | D | 49 | 53.567 | 29.516 | 33.232 | 1.00 | 50.14 | N |
| ATOM | 3198 | CA | PRO | D | 49 | 53.306 | 30.263 | 31.996 | 1.00 | 49.15 | C |
| ATOM | 3199 | C | PRO | D | 49 | 54.550 | 30.820 | 31.305 | 1.00 | 48.42 | C |
| ATOM | 3200 | O | PRO | D | 49 | 54.472 | 31.288 | 30.167 | 1.00 | 48.13 | O |
| ATOM | 3201 | CB | PRO | D | 49 | 52.373 | 31.380 | 32.457 | 1.00 | 49.52 | C |
| ATOM | 3202 | CG | PRO | D | 49 | 52.857 | 31.657 | 33.855 | 1.00 | 49.18 | C |
| ATOM | 3203 | CD | PRO | D | 49 | 53.052 | 30.251 | 34.406 | 1.00 | 50.05 | C |
| ATOM | 3204 | N | HIS | D | 50 | 55.696 | 30.773 | 31.981 | 1.00 | 46.75 | N |
| ATOM | 3205 | CA | HIS | D | 50 | 56.916 | 31.304 | 31.383 | 1.00 | 45.88 | C |
| ATOM | 3206 | C | HIS | D | 50 | 57.874 | 30.272 | 30.765 | 1.00 | 44.34 | C |
| ATOM | 3207 | O | HIS | D | 50 | 59.045 | 30.570 | 30.528 | 1.00 | 44.23 | O |
| ATOM | 3208 | CB | HIS | D | 50 | 57.638 | 32.185 | 32.405 | 1.00 | 45.79 | C |
| ATOM | 3209 | CG | HIS | D | 50 | 56.829 | 33.371 | 32.833 | 1.00 | 47.26 | C |
| ATOM | 3210 | ND1 | HIS | D | 50 | 56.501 | 34.395 | 31.970 | 1.00 | 47.30 | N |
| ATOM | 3211 | CD2 | HIS | D | 50 | 56.213 | 33.657 | 34.005 | 1.00 | 47.36 | C |
| ATOM | 3212 | CE1 | HIS | D | 50 | 55.715 | 35.257 | 32.589 | 1.00 | 47.33 | C |
| ATOM | 3213 | NE2 | HIS | D | 50 | 55.525 | 34.833 | 33.824 | 1.00 | 47.72 | N |
| ATOM | 3214 | N | ILE | D | 51 | 57.370 | 29.068 | 30.499 | 1.00 | 42.18 | N |
| ATOM | 3215 | CA | ILE | D | 51 | 58.177 | 28.016 | 29.871 | 1.00 | 41.06 | C |
| ATOM | 3216 | C | ILE | D | 51 | 57.698 | 27.771 | 28.442 | 1.00 | 40.46 | C |
| ATOM | 3217 | O | ILE | D | 51 | 58.264 | 26.950 | 27.721 | 1.00 | 40.26 | O |
| ATOM | 3218 | CB | ILE | D | 51 | 58.097 | 26.665 | 30.636 | 1.00 | 39.75 | C |
| ATOM | 3219 | CG1 | ILE | D | 51 | 56.647 | 26.181 | 30.697 | 1.00 | 38.79 | C |
| ATOM | 3220 | CG2 | ILE | D | 51 | 58.675 | 26.818 | 32.030 | 1.00 | 38.97 | C |
| ATOM | 3221 | CD1 | ILE | D | 51 | 56.457 | 24.914 | 31.485 | 1.00 | 37.44 | C |
| ATOM | 3222 | N | LYS | D | 52 | 56.639 | 28.471 | 28.043 | 1.00 | 39.78 | N |
| ATOM | 3223 | CA | LYS | D | 52 | 56.103 | 28.345 | 26.691 | 1.00 | 38.80 | C |
| ATOM | 3224 | C | LYS | D | 52 | 56.999 | 29.181 | 25.783 | 1.00 | 37.62 | C |
| ATOM | 3225 | O | LYS | D | 52 | 57.023 | 30.399 | 25.881 | 1.00 | 37.88 | O |
| ATOM | 3226 | CB | LYS | D | 52 | 54.663 | 28.851 | 26.649 | 1.00 | 39.06 | C |
| ATOM | 3227 | CG | LYS | D | 52 | 54.076 | 28.941 | 25.254 | 1.00 | 41.38 | C |
| ATOM | 3228 | CD | LYS | D | 52 | 52.551 | 29.006 | 25.306 | 1.00 | 43.38 | C |
| ATOM | 3229 | CE | LYS | D | 52 | 51.956 | 29.144 | 23.910 | 1.00 | 44.51 | C |
| ATOM | 3230 | NZ | LYS | D | 52 | 50.463 | 29.058 | 23.940 | 1.00 | 45.28 | N |
| ATOM | 3231 | N | LEU | D | 53 | 57.740 | 28.516 | 24.903 | 1.00 | 35.77 | N |
| ATOM | 3232 | CA | LEU | D | 53 | 58.677 | 29.198 | 24.023 | 1.00 | 34.05 | C |
| ATOM | 3233 | C | LEU | D | 53 | 58.325 | 29.103 | 22.546 | 1.00 | 33.69 | C |
| ATOM | 3234 | O | LEU | D | 53 | 57.587 | 28.220 | 22.120 | 1.00 | 33.77 | O |
| ATOM | 3235 | CB | LEU | D | 53 | 60.081 | 28.628 | 24.246 | 1.00 | 32.10 | C |
| ATOM | 3236 | CG | LEU | D | 53 | 60.438 | 28.457 | 25.722 | 1.00 | 32.46 | C |
| ATOM | 3237 | CD1 | LEU | D | 53 | 61.812 | 27.799 | 25.873 | 1.00 | 30.90 | C |
| ATOM | 3238 | CD2 | LEU | D | 53 | 60.396 | 29.827 | 26.405 | 1.00 | 31.78 | C |
| ATOM | 3239 | N | GLN | D | 54 | 58.859 | 30.030 | 21.763 | 1.00 | 32.79 | N |
| ATOM | 3240 | CA | GLN | D | 54 | 58.614 | 30.018 | 20.336 | 1.00 | 32.41 | C |
| ATOM | 3241 | C | GLN | D | 54 | 59.953 | 30.037 | 19.593 | 1.00 | 32.05 | C |
| ATOM | 3242 | O | GLN | D | 54 | 60.705 | 31.018 | 19.659 | 1.00 | 31.21 | O |
| ATOM | 3243 | CB | GLN | D | 54 | 57.748 | 31.215 | 19.920 | 1.00 | 31.73 | C |
| ATOM | 3244 | CG | GLN | D | 54 | 57.428 | 31.249 | 18.426 | 1.00 | 33.58 | C |
| ATOM | 3245 | CD | GLN | D | 54 | 56.543 | 30.082 | 17.970 | 1.00 | 35.55 | C |
| ATOM | 3246 | OE1 | GLN | D | 54 | 55.339 | 30.051 | 18.246 | 1.00 | 36.89 | O |
| ATOM | 3247 | NE2 | GLN | D | 54 | 57.144 | 29.116 | 17.272 | 1.00 | 35.05 | N |
| ATOM | 3248 | N | LEU | D | 55 | 60.247 | 28.940 | 18.896 | 1.00 | 31.92 | N |
| ATOM | 3249 | CA | LEU | D | 55 | 61.481 | 28.824 | 18.121 | 1.00 | 31.53 | C |
| ATOM | 3250 | C | LEU | D | 55 | 61.228 | 29.362 | 16.717 | 1.00 | 30.93 | C |
| ATOM | 3251 | O | LEU | D | 55 | 60.121 | 29.248 | 16.201 | 1.00 | 30.58 | O |
| ATOM | 3252 | CB | LEU | D | 55 | 61.910 | 27.355 | 18.008 | 1.00 | 32.24 | C |

TABLE 3-continued

FGFR2(D2–D3) Complexed with FGF2

| ATOM | 3253 | CG | LEU | D | 55 | 62.556 | 26.584 | 19.164 | 1.00 | 32.83 | C |
|---|---|---|---|---|---|---|---|---|---|---|---|
| ATOM | 3254 | CD1 | LEU | D | 55 | 64.047 | 26.722 | 19.085 | 1.00 | 33.91 | C |
| ATOM | 3255 | CD2 | LEU | D | 55 | 62.029 | 27.063 | 20.506 | 1.00 | 31.56 | C |
| ATOM | 3256 | N | GLN | D | 56 | 62.252 | 29.944 | 16.106 | 1.00 | 30.47 | N |
| ATOM | 3257 | CA | GLN | D | 56 | 62.141 | 30.473 | 14.749 | 1.00 | 30.30 | C |
| ATOM | 3258 | C | GLN | D | 56 | 63.520 | 30.438 | 14.088 | 1.00 | 30.10 | C |
| ATOM | 3259 | O | GLN | D | 56 | 64.496 | 30.946 | 14.636 | 1.00 | 29.40 | O |
| ATOM | 3260 | CB | GLN | D | 56 | 61.587 | 31.910 | 14.768 | 1.00 | 31.17 | C |
| ATOM | 3261 | CG | GLN | D | 56 | 61.602 | 32.646 | 13.415 | 1.00 | 31.41 | C |
| ATOM | 3262 | CD | GLN | D | 56 | 60.679 | 32.024 | 12.367 | 1.00 | 32.89 | C |
| ATOM | 3263 | OE1 | GLN | D | 56 | 59.470 | 31.897 | 12.585 | 1.00 | 32.67 | O |
| ATOM | 3264 | NE2 | GLN | D | 56 | 61.247 | 31.643 | 11.221 | 1.00 | 31.40 | N |
| ATOM | 3265 | N | ALA | D | 57 | 63.596 | 29.822 | 12.912 | 1.00 | 30.59 | N |
| ATOM | 3266 | CA | ALA | D | 57 | 64.863 | 29.722 | 12.191 | 1.00 | 31.46 | C |
| ATOM | 3267 | C | ALA | D | 57 | 65.208 | 31.047 | 11.514 | 1.00 | 31.50 | C |
| ATOM | 3268 | O | ALA | D | 57 | 64.337 | 31.689 | 10.915 | 1.00 | 31.96 | O |
| ATOM | 3269 | CB | ALA | D | 57 | 64.787 | 28.608 | 11.148 | 1.00 | 31.14 | C |
| ATOM | 3270 | N | GLU | D | 58 | 66.472 | 31.455 | 11.612 | 1.00 | 31.48 | N |
| ATOM | 3271 | CA | GLU | D | 58 | 66.937 | 32.708 | 11.003 | 1.00 | 31.93 | C |
| ATOM | 3272 | CG | GLU | D | 58 | 67.651 | 32.352 | 9.704 | 1.00 | 31.62 | C |
| ATOM | 3273 | O | GLU | D | 58 | 67.669 | 33.118 | 8.743 | 1.00 | 32.03 | O |
| ATOM | 3274 | CB | GLU | D | 58 | 67.902 | 33.423 | 11.950 | 1.00 | 31.82 | C |
| ATOM | 3275 | CG | GLU | D | 58 | 68.104 | 34.897 | 11.642 | 1.00 | 33.93 | C |
| ATOM | 3276 | CD | GLU | D | 58 | 66.805 | 35.697 | 11.682 | 1.00 | 33.77 | C |
| ATOM | 3277 | OE1 | GLU | D | 58 | 65.925 | 35.394 | 12.509 | 1.00 | 33.41 | O |
| ATOM | 3278 | OE2 | GLU | D | 58 | 66.673 | 36.649 | 10.891 | 1.00 | 36.68 | O |
| ATOM | 3279 | N | GLU | D | 59 | 68.261 | 31.174 | 9.707 | 1.00 | 32.39 | N |
| ATOM | 3280 | CA | GLU | D | 59 | 68.956 | 30.625 | 8.552 | 1.00 | 33.39 | C |
| ATOM | 3281 | C | GLU | D | 59 | 69.078 | 29.123 | 8.824 | 1.00 | 32.60 | C |
| ATOM | 3282 | O | GLU | D | 59 | 68.781 | 28.661 | 9.932 | 1.00 | 32.53 | O |
| ATOM | 3283 | CB | GLU | D | 59 | 70.336 | 31.275 | 8.365 | 1.00 | 34.87 | C |
| ATOM | 3284 | CG | GLU | D | 59 | 71.455 | 30.693 | 9.205 | 1.00 | 38.35 | C |
| ATOM | 3285 | CD | GLU | D | 59 | 72.766 | 31.445 | 9.016 | 1.00 | 40.56 | C |
| ATOM | 3286 | OE1 | GLU | D | 59 | 73.170 | 31.658 | 7.852 | 1.00 | 42.72 | O |
| ATOM | 3287 | OE2 | GLU | D | 59 | 73.394 | 31.823 | 10.028 | 1.00 | 40.49 | O |
| ATOM | 3288 | N | ARG | D | 60 | 69.503 | 28.357 | 7.826 | 1.00 | 32.00 | N |
| ATOM | 3289 | CA | ARG | D | 60 | 69.611 | 26.910 | 7.992 | 1.00 | 32.66 | C |
| ATOM | 3290 | C | ARG | D | 60 | 70.320 | 26.475 | 9.280 | 1.00 | 31.35 | C |
| ATOM | 3291 | O | ARG | D | 60 | 71.459 | 26.856 | 9.527 | 1.00 | 31.20 | O |
| ATOM | 3292 | CB | ARG | D | 60 | 70.306 | 26.295 | 6.768 | 1.00 | 33.95 | C |
| ATOM | 3293 | CG | ARG | D | 60 | 70.378 | 24.778 | 6.814 | 1.00 | 36.32 | C |
| ATOM | 3294 | CD | ARG | D | 60 | 70.800 | 24.196 | 5.477 | 1.00 | 38.66 | C |
| ATOM | 3295 | NE | ARG | D | 60 | 71.248 | 22.825 | 5.636 | 1.00 | 42.38 | N |
| ATOM | 3296 | CZ | ARG | D | 60 | 72.497 | 22.472 | 5.930 | 1.00 | 43.93 | C |
| ATOM | 3297 | NH1 | ARG | D | 60 | 73.440 | 23.392 | 6.083 | 1.00 | 44.45 | N |
| ATOM | 3298 | NH2 | ARG | D | 60 | 72.795 | 21.192 | 6.099 | 1.00 | 45.88 | N |
| ATOM | 3299 | N | GLY | D | 61 | 69.628 | 25.696 | 10.108 | 1.00 | 30.50 | N |
| ATOM | 3300 | CA | GLY | D | 61 | 70.211 | 25.213 | 11.354 | 1.00 | 29.35 | C |
| ATOM | 3301 | C | GLY | D | 61 | 70.450 | 26.224 | 12.478 | 1.00 | 29.03 | C |
| ATOM | 3302 | O | GLY | D | 61 | 71.051 | 25.882 | 13.491 | 1.00 | 28.44 | O |
| ATOM | 3303 | N | VAL | D | 62 | 69.981 | 27.459 | 12.311 | 1.00 | 28.42 | N |
| ATOM | 3304 | CA | VAL | D | 62 | 70.151 | 28.499 | 13.319 | 1.00 | 27.63 | C |
| ATOM | 3305 | C | VAL | D | 62 | 68.798 | 29.040 | 13.787 | 1.00 | 27.82 | C |
| ATOM | 3306 | O | VAL | D | 62 | 67.971 | 29.435 | 12.969 | 1.00 | 28.05 | O |
| ATOM | 3307 | CB | VAL | D | 62 | 70.971 | 29.674 | 12.755 | 1.00 | 28.71 | C |
| ATOM | 3308 | CG1 | VAL | D | 62 | 71.055 | 30.802 | 13.789 | 1.00 | 27.45 | C |
| ATOM | 3309 | CG2 | VAL | D | 62 | 72.370 | 29.183 | 12.349 | 1.00 | 29.28 | C |
| ATOM | 3310 | N | VAL | D | 63 | 68.580 | 29.082 | 15.098 | 1.00 | 27.12 | N |
| ATOM | 3311 | CA | VAL | D | 63 | 67.309 | 29.568 | 15.627 | 1.00 | 26.23 | C |
| ATOM | 3312 | C | VAL | D | 63 | 67.416 | 30.634 | 16.721 | 1.00 | 27.27 | C |
| ATOM | 3313 | O | VAL | D | 63 | 68.472 | 30.824 | 17.342 | 1.00 | 26.15 | O |
| ATOM | 3314 | CB | VAL | D | 63 | 66.472 | 28.413 | 16.250 | 1.00 | 26.29 | C |
| ATOM | 3315 | CG1 | VAL | D | 63 | 66.320 | 27.251 | 15.257 | 1.00 | 25.11 | C |
| ATOM | 3316 | CG2 | VAL | D | 63 | 67.135 | 27.936 | 17.552 | 1.00 | 25.13 | C |
| ATOM | 3317 | N | SER | D | 64 | 66.295 | 31.326 | 16.933 | 1.00 | 27.59 | N |
| ATOM | 3318 | CA | SER | D | 64 | 66.162 | 32.314 | 18.003 | 1.00 | 28.77 | C |
| ATOM | 3319 | C | SER | D | 64 | 65.100 | 31.675 | 18.897 | 1.00 | 28.82 | C |
| ATOM | 3320 | O | SER | D | 64 | 64.194 | 31.001 | 18.398 | 1.00 | 29.07 | O |
| ATOM | 3321 | CB | SER | D | 64 | 65.663 | 33.662 | 17.466 | 1.00 | 29.15 | C |
| ATOM | 3322 | OG | SER | D | 64 | 64.344 | 33.586 | 16.972 | 1.00 | 30.31 | O |
| ATOM | 3323 | N | ILE | D | 65 | 65.217 | 31.850 | 20.206 | 1.00 | 29.32 | N |
| ATOM | 3324 | CA | ILE | D | 65 | 64.256 | 31.269 | 21.140 | 1.00 | 30.33 | C |
| ATOM | 3325 | C | ILE | D | 65 | 63.588 | 32.396 | 21.941 | 1.00 | 31.89 | C |
| ATOM | 3326 | O | ILE | D | 65 | 64.252 | 33.113 | 22.697 | 1.00 | 32.70 | O |
| ATOM | 3327 | CB | ILE | D | 65 | 64.967 | 30.280 | 22.087 | 1.00 | 29.23 | C |
| ATOM | 3328 | CG1 | ILE | D | 65 | 65.685 | 29.209 | 21.262 | 1.00 | 29.54 | C |
| ATOM | 3329 | CG2 | ILE | D | 65 | 63.967 | 29.636 | 23.018 | 1.00 | 29.94 | C |

TABLE 3-continued

FGFR2(D2–D3) Complexed with FGF2

| ATOM | 3330 | CD1 | ILE | D | 65 | 66.525 | 28.236 | 22.086 | 1.00 | 28.65 | C |
|---|---|---|---|---|---|---|---|---|---|---|---|
| ATOM | 3331 | N | LYS | D | 66 | 62.277 | 32.544 | 21.778 | 1.00 | 33.04 | N |
| ATOM | 3332 | CA | LYS | D | 66 | 61.537 | 33.617 | 22.439 | 1.00 | 34.75 | C |
| ATOM | 3333 | C | LYS | D | 66 | 60.500 | 33.186 | 23.467 | 1.00 | 35.49 | C |
| ATOM | 3334 | O | LYS | D | 66 | 59.659 | 32.334 | 23.195 | 1.00 | 35.39 | O |
| ATOM | 3335 | CB | LYS | D | 66 | 60.859 | 34.481 | 21.365 | 1.00 | 36.40 | C |
| ATOM | 3336 | CG | LYS | D | 66 | 59.924 | 35.589 | 21.865 | 1.00 | 38.42 | C |
| ATOM | 3337 | CD | LYS | D | 66 | 59.419 | 36.412 | 20.674 | 1.00 | 41.42 | C |
| ATOM | 3338 | CE | LYS | D | 66 | 58.472 | 37.543 | 21.071 | 1.00 | 43.03 | C |
| ATOM | 3339 | NZ | LYS | D | 66 | 57.094 | 37.064 | 21.404 | 1.00 | 45.12 | N |
| ATOM | 3340 | N | GLY | D | 67 | 60.573 | 33.777 | 24.658 | 1.00 | 36.59 | N |
| ATOM | 3341 | CA | GLY | D | 67 | 59.603 | 33.471 | 25.695 | 1.00 | 38.30 | C |
| ATOM | 3342 | C | GLY | D | 67 | 58.311 | 34.187 | 25.329 | 1.00 | 39.98 | C |
| ATOM | 3343 | O | GLY | D | 67 | 58.275 | 35.415 | 25.269 | 1.00 | 39.06 | O |
| ATOM | 3344 | N | VAL | D | 68 | 57.251 | 33.428 | 25.075 | 1.00 | 41.48 | N |
| ATOM | 3345 | CA | VAL | D | 68 | 55.981 | 34.027 | 24.679 | 1.00 | 43.26 | C |
| ATOM | 3346 | C | VAL | D | 68 | 55.437 | 35.015 | 25.707 | 1.00 | 43.98 | C |
| ATOM | 3347 | O | VAL | D | 68 | 55.105 | 36.145 | 25.356 | 1.00 | 44.25 | O |
| ATOM | 3348 | CB | VAL | D | 68 | 54.903 | 32.942 | 24.392 | 1.00 | 43.86 | C |
| ATOM | 3349 | CG1 | VAL | D | 68 | 53.635 | 33.594 | 23.829 | 1.00 | 43.37 | C |
| ATOM | 3350 | CG2 | VAL | D | 68 | 55.447 | 31.920 | 23.400 | 1.00 | 43.79 | C |
| ATOM | 3351 | N | SER | D | 69 | 55.358 | 34.599 | 26.970 | 1.00 | 44.50 | N |
| ATOM | 3352 | CA | SER | D | 69 | 54.843 | 35.468 | 28.033 | 1.00 | 45.32 | C |
| ATOM | 3353 | C | SER | D | 69 | 55.714 | 36.707 | 28.248 | 1.00 | 45.20 | C |
| ATOM | 3354 | O | SER | D | 69 | 55.242 | 37.840 | 28.141 | 1.00 | 45.09 | O |
| ATOM | 3355 | CB | SER | D | 69 | 54.724 | 34.685 | 29.348 | 1.00 | 44.74 | C |
| ATOM | 3356 | N | ALA | D | 70 | 56.988 | 36.477 | 28.541 | 1.00 | 45.20 | N |
| ATOM | 3357 | CA | ALA | D | 70 | 57.942 | 37.551 | 28.772 | 1.00 | 44.77 | C |
| ATOM | 3358 | C | ALA | D | 70 | 58.131 | 38.448 | 27.555 | 1.00 | 45.28 | C |
| ATOM | 3359 | O | ALA | D | 70 | 58.580 | 39.586 | 27.681 | 1.00 | 45.68 | O |
| ATOM | 3360 | CB | ALA | D | 70 | 59.276 | 36.957 | 29.175 | 1.00 | 45.09 | C |
| ATOM | 3361 | N | ASN | D | 71 | 57.790 | 37.934 | 26.378 | 1.00 | 45.22 | N |
| ATOM | 3362 | CA | ASN | D | 71 | 57.956 | 38.679 | 25.136 | 1.00 | 45.09 | C |
| ATOM | 3363 | C | ASN | D | 71 | 59.421 | 39.113 | 24.974 | 1.00 | 44.75 | C |
| ATOM | 3364 | O | ASN | D | 71 | 59.706 | 40.226 | 24.510 | 1.00 | 44.98 | O |
| ATOM | 3365 | CB | ASN | D | 71 | 57.032 | 39.907 | 25.114 | 1.00 | 45.04 | C |
| ATOM | 3366 | CG | ASN | D | 71 | 56.922 | 40.529 | 23.729 | 1.00 | 45.44 | C |
| ATOM | 3367 | OD1 | ASN | D | 71 | 56.594 | 39.849 | 22.752 | 1.00 | 45.94 | O |
| ATOM | 3368 | ND2 | ASN | D | 71 | 57.188 | 41.826 | 23.638 | 1.00 | 45.88 | N |
| ATOM | 3369 | N | ARG | D | 72 | 60.341 | 38.226 | 25.357 | 1.00 | 43.91 | N |
| ATOM | 3370 | CA | ARG | D | 72 | 61.780 | 38.485 | 25.262 | 1.00 | 43.19 | C |
| ATOM | 3371 | C | ARG | D | 72 | 62.500 | 37.329 | 24.560 | 1.00 | 42.45 | C |
| ATOM | 3372 | O | ARG | D | 72 | 61.974 | 36.219 | 24.498 | 1.00 | 42.53 | O |
| ATOM | 3373 | CB | ARG | D | 72 | 62.381 | 38.669 | 26.658 | 1.00 | 43.38 | C |
| ATOM | 3374 | CG | ARG | D | 72 | 62.019 | 39.969 | 27.372 | 1.00 | 44.06 | C |
| ATOM | 3375 | CD | ARG | D | 72 | 62.333 | 39.815 | 28.854 | 1.00 | 45.57 | C |
| ATOM | 3376 | NE | ARG | D | 72 | 62.160 | 41.029 | 29.650 | 1.00 | 46.11 | N |
| ATOM | 3377 | CZ | ARG | D | 72 | 63.090 | 41.967 | 29.807 | 1.00 | 46.62 | C |
| ATOM | 3378 | NH1 | ARG | D | 72 | 64.271 | 41.847 | 29.218 | 1.00 | 46.83 | N |
| ATOM | 3379 | NH2 | ARG | D | 72 | 62.853 | 43.012 | 30.586 | 1.00 | 47.06 | N |
| ATOM | 3380 | N | TYR | D | 73 | 63.702 | 37.601 | 24.046 | 1.00 | 40.48 | N |
| ATOM | 3381 | CA | TYR | D | 73 | 64.516 | 36.604 | 23.347 | 1.00 | 39.21 | C |
| ATOM | 3382 | C | TYR | D | 73 | 65.706 | 36.118 | 24.165 | 1.00 | 38.88 | C |
| ATOM | 3383 | O | TYR | D | 73 | 66.448 | 36.918 | 24.731 | 1.00 | 38.06 | O |
| ATOM | 3384 | CB | TYR | D | 73 | 65.057 | 37.162 | 22.027 | 1.00 | 38.39 | C |
| ATOM | 3385 | CG | TYR | D | 73 | 63.982 | 37.544 | 21.043 | 1.00 | 38.49 | C |
| ATOM | 3386 | CD1 | TYR | D | 73 | 63.326 | 38.774 | 21.137 | 1.00 | 37.45 | C |
| ATOM | 3387 | CD2 | TYR | D | 73 | 63.599 | 36.664 | 20.029 | 1.00 | 37.61 | C |
| ATOM | 3388 | CE1 | TYR | D | 73 | 62.316 | 39.118 | 20.243 | 1.00 | 37.57 | C |
| ATOM | 3389 | CE2 | TYR | D | 73 | 62.590 | 36.996 | 19.134 | 1.00 | 37.51 | C |
| ATOM | 3390 | CZ | TYR | D | 73 | 61.953 | 38.223 | 19.245 | 1.00 | 37.70 | C |
| ATOM | 3391 | OH | TYR | D | 73 | 60.957 | 38.543 | 18.354 | 1.00 | 37.47 | O |
| ATOM | 3392 | N | LEU | D | 74 | 65.888 | 34.802 | 24.205 | 1.00 | 38.24 | N |
| ATOM | 3393 | CA | LEU | D | 74 | 67.000 | 34.185 | 24.328 | 1.00 | 38.30 | C |
| ATOM | 3394 | C | LEU | D | 74 | 68.311 | 34.681 | 24.328 | 1.00 | 38.42 | C |
| ATOM | 3395 | O | LEU | D | 74 | 68.423 | 34.834 | 23.118 | 1.00 | 38.39 | O |
| ATOM | 3396 | CB | LEU | D | 74 | 66.941 | 32.657 | 24.786 | 1.00 | 38.60 | C |
| ATOM | 3397 | CG | LEU | D | 74 | 67.984 | 31.822 | 25.537 | 1.00 | 38.75 | C |
| ATOM | 3398 | CD1 | LEU | D | 74 | 67.692 | 31.874 | 27.037 | 1.00 | 38.70 | C |
| ATOM | 3399 | CD2 | LEU | D | 74 | 67.946 | 30.384 | 25.049 | 1.00 | 38.55 | C |
| ATOM | 3400 | N | ALA | D | 75 | 69.301 | 34.932 | 25.174 | 1.00 | 39.28 | N |
| ATOM | 3401 | CA | ALA | D | 75 | 70.592 | 35.402 | 24.696 | 1.00 | 40.08 | C |
| ATOM | 3402 | C | ALA | D | 75 | 71.714 | 34.975 | 25.628 | 1.00 | 40.36 | C |
| ATOM | 3403 | O | ALA | D | 75 | 71.499 | 34.754 | 26.820 | 1.00 | 38.94 | O |
| ATOM | 3404 | CB | ALA | D | 75 | 70.580 | 36.918 | 24.567 | 1.00 | 40.17 | C |
| ATOM | 3405 | N | MET | D | 76 | 72.912 | 34.850 | 25.069 | 1.00 | 41.52 | N |
| ATOM | 3406 | CA | MET | D | 76 | 74.082 | 34.487 | 25.853 | 1.00 | 43.06 | C |

TABLE 3-continued

FGFR2(D2–D3) Complexed with FGF2

| ATOM | 3407 | C | MET | D | 76 | 75.094 | 35.620 | 25.732 | 1.00 | 44.08 | C |
|---|---|---|---|---|---|---|---|---|---|---|---|
| ATOM | 3408 | O | MET | D | 76 | 75.503 | 35.984 | 24.628 | 1.00 | 43.36 | O |
| ATOM | 3409 | CB | MET | D | 76 | 74.705 | 33.194 | 25.345 | 1.00 | 42.43 | C |
| ATOM | 3410 | CG | MET | D | 76 | 75.868 | 32.738 | 26.195 | 1.00 | 42.51 | C |
| ATOM | 3411 | SD | MET | D | 76 | 76.653 | 31.282 | 25.525 | 1.00 | 43.26 | S |
| ATOM | 3412 | CE | MET | D | 76 | 75.417 | 30.042 | 25.906 | 1.00 | 42.34 | C |
| ATOM | 3413 | N | LYS | D | 77 | 75.487 | 36.167 | 26.877 | 1.00 | 45.76 | N |
| ATOM | 3414 | CA | LYS | D | 77 | 76.437 | 37.272 | 26.941 | 1.00 | 47.47 | C |
| ATOM | 3415 | C | LYS | D | 77 | 77.891 | 36.817 | 26.796 | 1.00 | 48.42 | C |
| ATOM | 3416 | O | LYS | D | 77 | 78.186 | 35.619 | 26.823 | 1.00 | 47.92 | O |
| ATOM | 3417 | CB | LYS | D | 77 | 76.246 | 38.013 | 28.266 | 1.00 | 48.92 | C |
| ATOM | 3418 | CG | LYS | D | 77 | 74.901 | 38.733 | 28.408 | 1.00 | 49.43 | C |
| ATOM | 3419 | CD | LYS | D | 77 | 75.008 | 40.158 | 27.884 | 1.00 | 51.25 | C |
| ATOM | 3420 | CE | LYS | D | 77 | 73.707 | 40.920 | 28.072 | 1.00 | 52.60 | C |
| ATOM | 3421 | NZ | LYS | D | 77 | 73.836 | 42.337 | 27.620 | 1.00 | 53.85 | N |
| ATOM | 3422 | N | GLU | D | 78 | 78.794 | 37.785 | 26.648 | 1.00 | 49.49 | N |
| ATOM | 3423 | CA | GLU | D | 78 | 80.219 | 37.508 | 26.488 | 1.00 | 50.47 | C |
| ATOM | 3424 | C | GLU | D | 78 | 80.847 | 36.716 | 27.641 | 1.00 | 51.20 | C |
| ATOM | 3425 | O | GLU | D | 78 | 81.797 | 35.967 | 27.428 | 1.00 | 51.18 | O |
| ATOM | 3426 | CB | GLU | D | 78 | 80.988 | 38.819 | 26.290 | 1.00 | 50.83 | C |
| ATOM | 3427 | N | ASP | D | 79 | 80.325 | 36.875 | 28.855 | 1.00 | 51.96 | N |
| ATOM | 3428 | CA | ASP | D | 79 | 80.867 | 36.156 | 30.011 | 1.00 | 52.63 | C |
| ATOM | 3429 | C | ASP | D | 79 | 80.228 | 34.778 | 30.166 | 1.00 | 52.67 | C |
| ATOM | 3430 | O | ASP | D | 79 | 80.521 | 34.053 | 31.116 | 1.00 | 53.01 | O |
| ATOM | 3431 | CB | ASP | D | 79 | 80.646 | 36.957 | 31.300 | 1.00 | 52.97 | C |
| ATOM | 3432 | CG | ASP | D | 79 | 79.177 | 37.145 | 31.622 | 1.00 | 53.36 | C |
| ATOM | 3433 | OD1 | ASP | D | 79 | 78.861 | 37.653 | 32.718 | 1.00 | 53.30 | O |
| ATOM | 3434 | OD2 | ASP | D | 79 | 78.334 | 36.788 | 30.772 | 1.00 | 53.86 | O |
| ATOM | 3435 | N | GLY | D | 80 | 79.344 | 34.427 | 29.237 | 1.00 | 52.19 | N |
| ATOM | 3436 | CA | GLY | D | 80 | 78.691 | 33.130 | 29.298 | 1.00 | 51.48 | C |
| ATOM | 3437 | C | GLY | D | 80 | 77.404 | 33.082 | 30.105 | 1.00 | 50.93 | C |
| ATOM | 3438 | O | GLY | D | 80 | 76.886 | 32.000 | 30.383 | 1.00 | 50.90 | O |
| ATOM | 3439 | N | ARG | D | 81 | 76.875 | 34.243 | 30.480 | 1.00 | 50.15 | N |
| ATOM | 3440 | CA | ARG | D | 81 | 75.640 | 34.286 | 31.257 | 1.00 | 49.57 | C |
| ATOM | 3441 | C | ARG | D | 81 | 74.415 | 34.294 | 30.344 | 1.00 | 49.04 | C |
| ATOM | 3442 | O | ARG | D | 81 | 74.467 | 34.799 | 29.222 | 1.00 | 48.59 | O |
| ATOM | 3443 | CB | ARG | D | 81 | 75.622 | 35.528 | 32.161 | 1.00 | 49.50 | C |
| ATOM | 3444 | N | LEU | D | 82 | 73.310 | 33.732 | 30.824 | 1.00 | 48.27 | N |
| ATOM | 3445 | CA | LEU | D | 82 | 72.083 | 33.700 | 30.031 | 1.00 | 47.90 | C |
| ATOM | 3446 | C | LEU | D | 82 | 71.065 | 34.728 | 30.517 | 1.00 | 48.39 | C |
| ATOM | 3447 | O | LEU | D | 82 | 70.910 | 34.940 | 31.722 | 1.00 | 48.80 | O |
| ATOM | 3448 | CB | LEU | D | 82 | 71.436 | 32.309 | 30.081 | 1.00 | 46.28 | C |
| ATOM | 3449 | CG | LEU | D | 82 | 72.140 | 31.090 | 29.482 | 1.00 | 45.38 | C |
| ATOM | 3450 | CD1 | LEU | D | 82 | 71.198 | 29.896 | 29.554 | 1.00 | 44.72 | C |
| ATOM | 3451 | CD2 | LEU | D | 82 | 72.525 | 31.357 | 28.035 | 1.00 | 45.05 | C |
| ATOM | 3452 | N | LEU | D | 83 | 70.380 | 35.365 | 29.572 | 1.00 | 48.54 | N |
| ATOM | 3453 | CA | LEU | D | 83 | 69.351 | 36.349 | 29.888 | 1.00 | 49.02 | C |
| ATOM | 3454 | C | LEU | D | 83 | 68.410 | 36.479 | 28.690 | 1.00 | 49.02 | C |
| ATOM | 3455 | O | LEU | D | 83 | 68.683 | 35.925 | 27.628 | 1.00 | 49.46 | O |
| ATOM | 3456 | CB | LEU | D | 83 | 69.979 | 37.705 | 30.225 | 1.00 | 49.68 | C |
| ATOM | 3457 | CG | LEU | D | 83 | 70.659 | 38.558 | 29.145 | 1.00 | 50.40 | C |
| ATOM | 3458 | CD1 | LEU | D | 83 | 69.660 | 39.026 | 28.091 | 1.00 | 49.95 | C |
| ATOM | 3459 | CD2 | LEU | D | 83 | 71.283 | 39.773 | 29.829 | 1.00 | 51.61 | C |
| ATOM | 3460 | N | ALA | D | 84 | 67.304 | 37.202 | 28.859 | 1.00 | 48.84 | N |
| ATOM | 3461 | CA | ALA | D | 84 | 66.348 | 37.391 | 27.767 | 1.00 | 48.88 | C |
| ATOM | 3462 | C | ALA | D | 84 | 66.184 | 38.876 | 27.430 | 1.00 | 48.68 | C |
| ATOM | 3463 | O | ALA | D | 84 | 65.796 | 39.675 | 28.280 | 1.00 | 49.18 | O |
| ATOM | 3464 | CB | ALA | D | 84 | 65.001 | 36.773 | 28.128 | 1.00 | 48.28 | C |
| ATOM | 3465 | N | SER | D | 85 | 66.468 | 39.233 | 26.180 | 1.00 | 48.45 | N |
| ATOM | 3466 | CA | SER | D | 85 | 66.383 | 40.621 | 25.745 | 1.00 | 48.43 | C |
| ATOM | 3467 | C | SER | D | 85 | 65.078 | 41.014 | 25.071 | 1.00 | 48.54 | C |
| ATOM | 3468 | O | SER | D | 85 | 64.424 | 40.206 | 24.403 | 1.00 | 48.35 | O |
| ATOM | 3469 | CB | SER | D | 85 | 67.543 | 40.961 | 24.815 | 1.00 | 47.61 | C |
| ATOM | 3470 | OG | SER | D | 85 | 67.471 | 40.180 | 23.646 | 1.00 | 48.73 | O |
| ATOM | 3471 | N | LYS | D | 86 | 64.714 | 42.280 | 25.252 | 1.00 | 48.04 | N |
| ATOM | 3472 | CA | LYS | D | 86 | 63.493 | 42.814 | 24.675 | 1.00 | 47.48 | C |
| ATOM | 3473 | C | LYS | D | 86 | 63.627 | 42.857 | 23.160 | 1.00 | 47.38 | C |
| ATOM | 3474 | O | LYS | D | 86 | 62.678 | 42.541 | 22.431 | 1.00 | 47.31 | O |
| ATOM | 3475 | CB | LYS | D | 86 | 63.219 | 44.219 | 25.216 | 1.00 | 47.13 | C |
| ATOM | 3476 | N | SER | D | 87 | 64.811 | 43.236 | 22.689 | 1.00 | 46.35 | N |
| ATOM | 3477 | CA | SER | D | 87 | 65.062 | 43.316 | 21.258 | 1.00 | 46.37 | C |
| ATOM | 3478 | C | SER | D | 87 | 66.134 | 42.307 | 20.825 | 1.00 | 45.65 | C |
| ATOM | 3479 | O | SER | D | 87 | 67.060 | 42.003 | 21.572 | 1.00 | 45.52 | O |
| ATOM | 3480 | CB | SER | D | 87 | 65.494 | 44.741 | 20.888 | 1.00 | 47.49 | C |
| ATOM | 3481 | N | VAL | D | 88 | 66.000 | 41.807 | 19.606 | 1.00 | 45.23 | N |
| ATOM | 3482 | CA | VAL | D | 88 | 66.919 | 40.827 | 19.049 | 1.00 | 44.31 | C |
| ATOM | 3483 | C | VAL | D | 88 | 68.320 | 41.370 | 18.741 | 1.00 | 44.05 | C |

TABLE 3-continued

| FGFR2(D2–D3) Complexed with FGF2 | | | | | | | | | | |
|---|---|---|---|---|---|---|---|---|---|---|
| ATOM | 3484 | O | VAL | D | 88 | 68.455 | 42.397 | 18.083 | 1.00 | 44.55 | O |
| ATOM | 3485 | CB | VAL | D | 88 | 66.328 | 40.238 | 17.753 | 1.00 | 44.15 | C |
| ATOM | 3486 | CG1 | VAL | D | 88 | 67.261 | 39.174 | 17.182 | 1.00 | 43.40 | C |
| ATOM | 3487 | CG2 | VAL | D | 88 | 64.943 | 39.660 | 18.035 | 1.00 | 44.10 | C |
| ATOM | 3488 | N | THR | D | 89 | 69.353 | 40.677 | 19.219 | 1.00 | 42.84 | N |
| ATOM | 3489 | CA | THR | D | 89 | 70.739 | 41.067 | 18.952 | 1.00 | 42.13 | C |
| ATOM | 3490 | C | THR | D | 89 | 71.487 | 39.835 | 18.460 | 1.00 | 41.62 | C |
| ATOM | 3491 | O | THR | D | 89 | 70.918 | 38.752 | 18.403 | 1.00 | 41.27 | O |
| ATOM | 3492 | CB | THR | D | 89 | 71.468 | 41.580 | 20.203 | 1.00 | 41.82 | C |
| ATOM | 3493 | OG1 | THR | D | 89 | 71.848 | 40.468 | 21.024 | 1.00 | 41.87 | O |
| ATOM | 3494 | CG2 | THR | D | 89 | 70.567 | 42.513 | 21.001 | 1.00 | 42.55 | C |
| ATOM | 3495 | N | ASP | D | 90 | 72.761 | 39.999 | 18.114 | 1.00 | 41.36 | N |
| ATOM | 3496 | CA | ASP | D | 90 | 73.571 | 38.889 | 17.616 | 1.00 | 41.12 | C |
| ATOM | 3497 | C | ASP | D | 90 | 73.844 | 37.802 | 18.654 | 1.00 | 41.18 | C |
| ATOM | 3498 | O | ASP | D | 90 | 74.408 | 36.755 | 18.332 | 1.00 | 42.37 | O |
| ATOM | 3499 | CB | ASP | D | 90 | 74.907 | 39.412 | 17.064 | 1.00 | 41.11 | C |
| ATOM | 3500 | CG | ASP | D | 90 | 75.656 | 40.326 | 18.051 | 1.00 | 41.39 | C |
| ATOM | 3501 | OD1 | ASP | D | 90 | 75.268 | 40.402 | 19.239 | 1.00 | 40.75 | O |
| ATOM | 3502 | OD2 | ASP | D | 90 | 76.651 | 40.965 | 17.631 | 1.00 | 39.90 | O |
| ATOM | 3503 | N | GLU | D | 91 | 73.445 | 38.045 | 19.897 | 1.00 | 40.48 | N |
| ATOM | 3504 | CA | GLU | D | 91 | 73.662 | 37.072 | 20.965 | 1.00 | 40.42 | C |
| ATOM | 3505 | C | GLU | D | 91 | 72.391 | 36.250 | 21.201 | 1.00 | 38.92 | C |
| ATOM | 3506 | O | GLU | D | 91 | 72.300 | 35.498 | 22.172 | 1.00 | 38.93 | O |
| ATOM | 3507 | CB | GLU | D | 91 | 74.062 | 37.788 | 22.265 | 1.00 | 40.64 | C |
| ATOM | 3508 | CG | GLU | D | 91 | 75.140 | 38.852 | 22.089 | 1.00 | 41.05 | C |
| ATOM | 3509 | CD | GLU | D | 91 | 75.549 | 39.509 | 23.405 | 1.00 | 41.33 | C |
| ATOM | 3510 | OE1 | GLU | D | 91 | 74.670 | 40.048 | 24.112 | 1.00 | 40.56 | O |
| ATOM | 3511 | OE2 | GLU | D | 91 | 76.755 | 39.488 | 23.728 | 1.00 | 42.06 | O |
| ATOM | 3512 | N | CYS | D | 92 | 71.419 | 36.386 | 20.305 | 1.00 | 37.53 | N |
| ATOM | 3513 | CA | CYS | D | 92 | 70.155 | 35.662 | 20.434 | 1.00 | 37.33 | C |
| ATOM | 3514 | C | CYS | D | 92 | 69.965 | 34.523 | 19.428 | 1.00 | 37.35 | C |
| ATOM | 3515 | O | CYS | D | 92 | 68.857 | 33.998 | 19.289 | 1.00 | 37.11 | O |
| ATOM | 3516 | CB | CYS | D | 92 | 68.978 | 36.631 | 20.300 | 1.00 | 37.57 | C |
| ATOM | 3517 | SG | CYS | D | 92 | 68.952 | 37.991 | 21.499 | 1.00 | 36.54 | S |
| ATOM | 3518 | N | PHE | D | 93 | 71.040 | 34.133 | 18.742 | 1.00 | 36.58 | N |
| ATOM | 3519 | CA | PHE | D | 93 | 70.973 | 33.075 | 17.742 | 1.00 | 35.75 | C |
| ATOM | 3520 | C | PHE | D | 93 | 71.817 | 31.858 | 18.128 | 1.00 | 35.61 | C |
| ATOM | 3521 | O | PHE | D | 93 | 72.961 | 31.994 | 18.560 | 1.00 | 35.37 | O |
| ATOM | 3522 | CB | PHE | D | 93 | 71.393 | 33.654 | 16.386 | 1.00 | 35.89 | C |
| ATOM | 3523 | CG | PHE | D | 93 | 70.464 | 34.732 | 15.889 | 1.00 | 36.43 | C |
| ATOM | 3524 | CD1 | PHE | D | 93 | 69.186 | 34.414 | 15.442 | 1.00 | 36.23 | C |
| ATOM | 3525 | CD2 | PHE | D | 93 | 70.831 | 36.074 | 15.950 | 1.00 | 36.97 | C |
| ATOM | 3526 | CE1 | PHE | D | 93 | 68.281 | 35.411 | 15.069 | 1.00 | 36.80 | C |
| ATOM | 3527 | CE2 | PHE | D | 93 | 69.936 | 37.079 | 15.579 | 1.00 | 37.17 | C |
| ATOM | 3528 | CZ | PHE | D | 93 | 68.652 | 36.743 | 15.138 | 1.00 | 37.41 | C |
| ATOM | 3529 | N | PHE | D | 94 | 71.244 | 30.669 | 17.956 | 1.00 | 33.92 | N |
| ATOM | 3530 | CA | PHE | D | 94 | 71.906 | 29.435 | 18.344 | 1.00 | 33.26 | C |
| ATOM | 3531 | C | PHE | D | 94 | 71.802 | 28.315 | 17.300 | 1.00 | 33.32 | C |
| ATOM | 3532 | O | PHE | D | 94 | 70.737 | 28.117 | 16.689 | 1.00 | 32.41 | O |
| ATOM | 3533 | CB | PHE | D | 94 | 71.279 | 28.933 | 19.649 | 1.00 | 33.05 | C |
| ATOM | 3534 | CG | PHE | D | 94 | 71.288 | 29.944 | 20.775 | 1.00 | 33.05 | C |
| ATOM | 3535 | CD1 | PHE | D | 94 | 72.357 | 29.998 | 21.675 | 1.00 | 32.73 | C |
| ATOM | 3536 | CD2 | PHE | D | 94 | 70.217 | 30.824 | 20.952 | 1.00 | 32.88 | C |
| ATOM | 3537 | CE1 | PHE | D | 94 | 72.359 | 30.906 | 22.733 | 1.00 | 32.76 | C |
| ATOM | 3538 | CE2 | PHE | D | 94 | 70.206 | 31.739 | 22.006 | 1.00 | 32.89 | C |
| ATOM | 3539 | CZ | PHE | D | 94 | 71.279 | 31.780 | 22.901 | 1.00 | 33.32 | C |
| ATOM | 3540 | N | PHE | D | 95 | 72.899 | 27.582 | 17.109 | 1.00 | 31.85 | N |
| ATOM | 3541 | CA | PHE | D | 95 | 72.899 | 26.457 | 16.179 | 1.00 | 32.60 | C |
| ATOM | 3542 | C | PHE | D | 95 | 72.089 | 25.339 | 16.844 | 1.00 | 32.30 | C |
| ATOM | 3543 | O | PHE | D | 95 | 72.397 | 24.938 | 17.968 | 1.00 | 32.05 | O |
| ATOM | 3544 | CB | PHE | D | 95 | 74.324 | 25.934 | 15.923 | 1.00 | 33.10 | C |
| ATOM | 3545 | CG | PHE | D | 95 | 75.195 | 26.866 | 15.119 | 1.00 | 32.91 | C |
| ATOM | 3546 | CD1 | PHE | D | 95 | 76.261 | 27.535 | 15.721 | 1.00 | 33.04 | C |
| ATOM | 3547 | CD2 | PHE | D | 95 | 74.968 | 27.055 | 13.757 | 1.00 | 32.86 | C |
| ATOM | 3548 | CE1 | PHE | D | 95 | 77.097 | 28.381 | 14.971 | 1.00 | 33.29 | C |
| ATOM | 3549 | CE2 | PHE | D | 95 | 75.793 | 27.898 | 12.997 | 1.00 | 33.32 | C |
| ATOM | 3550 | CZ | PHE | D | 95 | 76.859 | 28.561 | 13.607 | 1.00 | 32.86 | C |
| ATOM | 3551 | N | GLU | D | 96 | 71.048 | 24.854 | 16.172 | 1.00 | 31.87 | N |
| ATOM | 3552 | CA | GLU | D | 96 | 70.254 | 23.766 | 16.733 | 1.00 | 32.18 | C |
| ATOM | 3553 | C | GLU | D | 96 | 70.703 | 22.471 | 16.084 | 1.00 | 33.15 | C |
| ATOM | 3554 | O | GLU | D | 96 | 70.798 | 22.377 | 14.858 | 1.00 | 32.44 | O |
| ATOM | 3555 | CB | GLU | D | 96 | 68.756 | 23.928 | 16.467 | 1.00 | 31.12 | C |
| ATOM | 3556 | CG | GLU | D | 96 | 67.933 | 22.775 | 17.062 | 1.00 | 29.98 | C |
| ATOM | 3557 | CD | GLU | D | 96 | 66.498 | 22.755 | 16.562 | 1.00 | 30.66 | C |
| ATOM | 3558 | OE1 | GLU | D | 96 | 66.294 | 22.331 | 15.406 | 1.00 | 30.70 | O |
| ATOM | 3559 | OE2 | GLU | D | 96 | 65.584 | 23.166 | 17.316 | 1.00 | 28.95 | O |
| ATOM | 3560 | N | ARG | D | 97 | 70.958 | 21.470 | 16.915 | 1.00 | 34.24 | N |

TABLE 3-continued

FGFR2(D2–D3) Complexed with FGF2

| ATOM | 3561 | CA | ARG | D | 97 | 71.398 | 20.178 | 16.420 | 1.00 | 35.69 | C |
|---|---|---|---|---|---|---|---|---|---|---|---|
| ATOM | 3562 | C | ARG | D | 97 | 70.717 | 19.011 | 17.133 | 1.00 | 34.61 | C |
| ATOM | 3563 | O | ARG | D | 97 | 70.569 | 19.013 | 18.353 | 1.00 | 33.67 | O |
| ATOM | 3564 | CB | ARG | D | 97 | 72.918 | 20.067 | 16.577 | 1.00 | 37.85 | C |
| ATOM | 3565 | CG | ARG | D | 97 | 73.515 | 18.742 | 16.123 | 1.00 | 41.19 | C |
| ATOM | 3566 | CD | ARG | D | 97 | 75.028 | 18.753 | 16.275 | 1.00 | 43.69 | C |
| ATOM | 3567 | NE | ARG | D | 97 | 75.620 | 17.424 | 16.122 | 1.00 | 45.78 | N |
| ATOM | 3568 | CZ | ARG | D | 97 | 76.905 | 17.149 | 16.339 | 1.00 | 47.38 | C |
| ATOM | 3569 | NH1 | ARG | D | 97 | 77.741 | 18.113 | 16.717 | 1.00 | 47.78 | N |
| ATOM | 3570 | NH2 | ARG | D | 97 | 77.357 | 15.908 | 16.191 | 1.00 | 48.28 | N |
| ATOM | 3571 | N | LEU | D | 98 | 70.281 | 18.035 | 16.350 | 1.00 | 34.95 | N |
| ATOM | 3572 | CA | LEU | D | 98 | 69.654 | 16.827 | 16.877 | 1.00 | 35.44 | C |
| ATOM | 3573 | C | LEU | D | 98 | 70.809 | 15.841 | 17.032 | 1.00 | 36.45 | C |
| ATOM | 3574 | O | LEU | D | 98 | 71.350 | 15.369 | 16.036 | 1.00 | 36.70 | O |
| ATOM | 3575 | CB | LEU | D | 98 | 68.644 | 16.268 | 15.880 | 1.00 | 34.55 | C |
| ATOM | 3576 | CG | LEU | D | 98 | 68.079 | 14.873 | 16.199 | 1.00 | 35.46 | C |
| ATOM | 3577 | CD1 | LEU | D | 98 | 67.448 | 14.843 | 17.582 | 1.00 | 32.80 | C |
| ATOM | 3578 | CD2 | LEU | D | 98 | 67.048 | 14.506 | 15.135 | 1.00 | 35.91 | C |
| ATOM | 3579 | N | GLU | D | 99 | 71.208 | 15.550 | 18.270 | 1.00 | 38.33 | N |
| ATOM | 3580 | CA | GLU | D | 99 | 72.325 | 14.628 | 18.518 | 1.00 | 38.88 | C |
| ATOM | 3581 | C | GLU | D | 99 | 71.920 | 13.181 | 18.270 | 1.00 | 40.14 | C |
| ATOM | 3582 | O | GLU | D | 99 | 70.729 | 12.846 | 18.213 | 1.00 | 39.39 | O |
| ATOM | 3583 | CB | GLU | D | 99 | 72.847 | 14.748 | 19.965 | 1.00 | 39.75 | C |
| ATOM | 3584 | CG | GLU | D | 99 | 73.198 | 16.162 | 20.442 | 1.00 | 41.74 | C |
| ATOM | 3585 | CD | GLU | D | 99 | 74.502 | 16.716 | 19.866 | 1.00 | 43.10 | C |
| ATOM | 3586 | OE1 | GLU | D | 99 | 74.743 | 17.936 | 20.020 | 1.00 | 42.78 | O |
| ATOM | 3587 | OE2 | GLU | D | 99 | 75.287 | 15.943 | 19.271 | 1.00 | 43.51 | O |
| ATOM | 3588 | N | SER | D | 100 | 72.928 | 12.321 | 18.143 | 1.00 | 40.94 | N |
| ATOM | 3589 | CA | SER | D | 100 | 72.715 | 10.898 | 17.900 | 1.00 | 40.80 | C |
| ATOM | 3590 | C | SER | D | 100 | 71.904 | 10.244 | 19.011 | 1.00 | 39.91 | C |
| ATOM | 3591 | O | SER | D | 100 | 71.263 | 9.208 | 18.803 | 1.00 | 40.88 | O |
| ATOM | 3592 | CB | SER | D | 100 | 74.071 | 10.190 | 17.741 | 1.00 | 42.60 | C |
| ATOM | 3593 | OG | SER | D | 100 | 74.947 | 10.490 | 18.817 | 1.00 | 44.54 | O |
| ATOM | 3594 | N | ASN | D | 101 | 71.932 | 10.845 | 20.195 | 1.00 | 38.36 | N |
| ATOM | 3595 | CA | ASN | D | 101 | 71.177 | 10.321 | 21.332 | 1.00 | 36.69 | C |
| ATOM | 3596 | C | ASN | D | 101 | 69.696 | 10.749 | 21.276 | 1.00 | 35.64 | C |
| ATOM | 3597 | O | ASN | D | 101 | 68.899 | 10.398 | 22.150 | 1.00 | 35.66 | O |
| ATOM | 3598 | CB | ASN | D | 101 | 71.804 | 10.803 | 22.651 | 1.00 | 38.65 | C |
| ATOM | 3599 | CG | ASN | D | 101 | 72.075 | 12.313 | 22.666 | 1.00 | 40.05 | C |
| ATOM | 3600 | CD1 | ASN | D | 101 | 71.369 | 13.092 | 22.022 | 1.00 | 41.26 | O |
| ATOM | 3601 | ND2 | ASN | D | 101 | 73.096 | 12.726 | 23.415 | 1.00 | 39.62 | N |
| ATOM | 3602 | N | ASN | D | 102 | 69.349 | 11.507 | 20.239 | 1.00 | 33.81 | N |
| ATOM | 3603 | CA | ASN | D | 102 | 68.002 | 12.019 | 20.009 | 1.00 | 32.56 | C |
| ATOM | 3604 | C | ASN | D | 102 | 67.522 | 13.171 | 20.899 | 1.00 | 31.26 | C |
| ATOM | 3605 | O | ASN | D | 102 | 66.317 | 13.381 | 21.053 | 1.00 | 29.28 | O |
| ATOM | 3606 | CB | ASN | D | 102 | 66.970 | 10.883 | 20.007 | 1.00 | 32.99 | C |
| ATOM | 3607 | CG | ASN | D | 102 | 66.878 | 10.190 | 18.649 | 1.00 | 35.04 | C |
| ATOM | 3608 | OD1 | ASN | D | 102 | 67.072 | 10.824 | 17.608 | 1.00 | 35.88 | O |
| ATOM | 3609 | ND2 | ASN | D | 102 | 66.571 | 8.894 | 18.654 | 1.00 | 35.03 | N |
| ATOM | 3610 | N | TYR | D | 103 | 68.476 | 13.907 | 21.474 | 1.00 | 29.52 | N |
| ATOM | 3611 | CA | TYR | D | 103 | 68.196 | 15.085 | 22.292 | 1.00 | 27.94 | C |
| ATOM | 3612 | C | TYR | D | 103 | 68.703 | 16.265 | 21.454 | 1.00 | 27.63 | C |
| ATOM | 3613 | O | TYR | D | 103 | 69.495 | 16.081 | 20.533 | 1.00 | 27.55 | O |
| ATOM | 3614 | CB | TYR | D | 103 | 68.960 | 15.030 | 23.615 | 1.00 | 26.70 | C |
| ATOM | 3615 | CG | TYR | D | 103 | 68.322 | 14.163 | 24.679 | 1.00 | 26.44 | C |
| ATOM | 3616 | CD1 | TYR | D | 103 | 67.350 | 14.677 | 25.540 | 1.00 | 26.62 | C |
| ATOM | 3617 | CD2 | TYR | D | 103 | 68.686 | 12.822 | 24.825 | 1.00 | 26.07 | C |
| ATOM | 3618 | CE1 | TYR | D | 103 | 66.759 | 13.869 | 26.525 | 1.00 | 26.64 | C |
| ATOM | 3619 | CE2 | TYR | D | 103 | 68.101 | 12.015 | 25.797 | 1.00 | 25.54 | C |
| ATOM | 3620 | CZ | TYR | D | 103 | 67.146 | 12.537 | 26.638 | 1.00 | 26.07 | C |
| ATOM | 3621 | OH | TYR | D | 103 | 66.562 | 11.727 | 27.578 | 1.00 | 26.51 | O |
| ATOM | 3622 | N | ASN | D | 104 | 68.248 | 17.472 | 21.757 | 1.00 | 27.05 | N |
| ATOM | 3623 | CA | ASN | D | 104 | 68.686 | 18.651 | 21.008 | 1.00 | 27.18 | C |
| ATOM | 3624 | C | ASN | D | 104 | 69.728 | 19.441 | 21.803 | 1.00 | 26.18 | C |
| ATOM | 3625 | O | ASN | D | 104 | 69.762 | 19.364 | 23.030 | 1.00 | 25.52 | O |
| ATOM | 3626 | CB | ASN | D | 104 | 67.497 | 19.581 | 20.732 | 1.00 | 28.01 | C |
| ATOM | 3627 | CG | ASN | D | 104 | 66.696 | 19.179 | 19.503 | 1.00 | 29.43 | C |
| ATOM | 3628 | OD1 | ASN | D | 104 | 66.739 | 18.037 | 19.054 | 1.00 | 29.97 | O |
| ATOM | 3629 | ND2 | ASN | D | 104 | 65.949 | 20.129 | 18.962 | 1.00 | 29.97 | N |
| ATOM | 3630 | N | THR | D | 105 | 70.583 | 20.177 | 21.095 | 1.00 | 25.93 | N |
| ATOM | 3631 | CA | THR | D | 105 | 71.567 | 21.047 | 21.745 | 1.00 | 26.23 | C |
| ATOM | 3632 | C | THR | D | 105 | 71.494 | 22.398 | 21.050 | 1.00 | 26.45 | C |
| ATOM | 3633 | O | THR | D | 105 | 71.169 | 22.481 | 19.858 | 1.00 | 25.80 | O |
| ATOM | 3634 | CB | THR | D | 105 | 73.027 | 20.518 | 21.667 | 1.00 | 26.04 | C |
| ATOM | 3635 | OG1 | THR | D | 105 | 73.457 | 20.456 | 20.300 | 1.00 | 26.82 | O |
| ATOM | 3636 | CG2 | THR | D | 105 | 73.132 | 19.158 | 22.319 | 1.00 | 26.71 | C |
| ATOM | 3637 | N | TYR | D | 106 | 71.792 | 23.453 | 21.804 | 1.00 | 27.12 | N |

TABLE 3-continued

FGFR2(D2–D3) Complexed with FGF2

| | | | | | | | | | | | |
|---|---|---|---|---|---|---|---|---|---|---|---|
| ATOM | 3638 | CA | TYR | D | 106 | 71.751 | 24.815 | 21.291 | 1.00 | 27.86 | C |
| ATOM | 3639 | C | TYR | D | 106 | 73.087 | 25.500 | 21.565 | 1.00 | 29.60 | C |
| ATOM | 3640 | O | TYR | D | 106 | 73.414 | 25.799 | 22.714 | 1.00 | 29.29 | O |
| ATOM | 3641 | CB | TYR | D | 106 | 70.590 | 25.551 | 21.966 | 1.00 | 26.16 | C |
| ATOM | 3642 | CG | TYR | D | 106 | 69.281 | 24.950 | 21.546 | 1.00 | 25.64 | C |
| ATOM | 3643 | CD1 | TYR | D | 106 | 68.707 | 25.285 | 20.316 | 1.00 | 24.14 | C |
| ATOM | 3644 | CD2 | TYR | D | 106 | 68.671 | 23.958 | 22.314 | 1.00 | 23.58 | C |
| ATOM | 3645 | CE1 | TYR | D | 106 | 67.567 | 24.636 | 19.856 | 1.00 | 25.46 | C |
| ATOM | 3646 | CE2 | TYR | D | 106 | 67.533 | 23.301 | 21.861 | 1.00 | 25.15 | C |
| ATOM | 3647 | CZ | TYR | D | 106 | 66.988 | 23.643 | 20.631 | 1.00 | 24.17 | C |
| ATOM | 3648 | OH | TYR | D | 106 | 65.902 | 22.965 | 20.148 | 1.00 | 24.91 | O |
| ATOM | 3649 | N | ARG | D | 107 | 73.845 | 25.732 | 20.494 | 1.00 | 31.16 | N |
| ATOM | 3650 | CA | ARG | D | 107 | 75.174 | 26.336 | 20.574 | 1.00 | 32.67 | C |
| ATOM | 3651 | C | ARG | D | 107 | 75.199 | 27.760 | 20.030 | 1.00 | 33.24 | C |
| ATOM | 3652 | O | ARG | D | 107 | 74.730 | 28.020 | 18.924 | 1.00 | 33.30 | O |
| ATOM | 3653 | CB | ARG | D | 107 | 76.158 | 25.463 | 19.798 | 1.00 | 32.67 | C |
| ATOM | 3654 | CG | ARG | D | 107 | 77.603 | 25.889 | 19.865 | 1.00 | 32.58 | C |
| ATOM | 3655 | CD | ARG | D | 107 | 78.476 | 24.804 | 19.241 | 1.00 | 31.51 | C |
| ATOM | 3656 | NE | ARG | D | 107 | 78.094 | 24.520 | 17.862 | 1.00 | 29.79 | N |
| ATOM | 3657 | CZ | ARG | D | 107 | 78.500 | 25.227 | 16.814 | 1.00 | 31.11 | C |
| ATOM | 3658 | NH1 | ARG | D | 107 | 79.311 | 26.267 | 16.989 | 1.00 | 31.22 | N |
| ATOM | 3659 | NH2 | ARG | D | 107 | 78.104 | 24.899 | 15.589 | 1.00 | 29.39 | N |
| ATOM | 3660 | N | SER | D | 108 | 75.752 | 28.676 | 20.822 | 1.00 | 34.39 | N |
| ATOM | 3661 | CA | SER | D | 108 | 75.843 | 30.091 | 20.456 | 1.00 | 35.36 | C |
| ATOM | 3662 | C | SER | D | 108 | 76.526 | 30.316 | 19.108 | 1.00 | 36.03 | C |
| ATOM | 3663 | O | SER | D | 108 | 77.611 | 29.789 | 18.861 | 1.00 | 36.15 | O |
| ATOM | 3664 | CB | SER | D | 108 | 76.600 | 30.858 | 21.551 | 1.00 | 35.17 | C |
| ATOM | 3665 | OG | SER | D | 108 | 76.895 | 32.186 | 21.163 | 1.00 | 33.39 | O |
| ATOM | 3666 | N | ARG | D | 109 | 75.889 | 31.092 | 18.233 | 1.00 | 36.63 | N |
| ATOM | 3667 | CA | ARG | D | 109 | 76.480 | 31.373 | 16.930 | 1.00 | 38.27 | C |
| ATOM | 3668 | C | ARG | D | 109 | 77.601 | 32.401 | 17.088 | 1.00 | 39.85 | C |
| ATOM | 3669 | O | ARG | D | 109 | 78.510 | 32.460 | 16.264 | 1.00 | 40.21 | O |
| ATOM | 3670 | CB | ARG | D | 109 | 75.426 | 31.906 | 15.946 | 1.00 | 37.43 | C |
| ATOM | 3671 | CG | ARG | D | 109 | 75.960 | 32.088 | 14.509 | 1.00 | 36.51 | C |
| ATOM | 3672 | CD | ARG | D | 109 | 74.879 | 32.531 | 13.518 | 1.00 | 35.80 | C |
| ATOM | 3673 | NE | ARG | D | 109 | 74.373 | 33.875 | 13.799 | 1.00 | 36.06 | N |
| ATOM | 3674 | CZ | ARG | D | 109 | 73.471 | 34.516 | 13.055 | 1.00 | 35.79 | C |
| ATOM | 3675 | NH1 | ARG | D | 109 | 72.962 | 33.941 | 11.977 | 1.00 | 35.72 | N |
| ATOM | 3676 | NH2 | ARG | D | 109 | 73.076 | 35.740 | 13.385 | 1.00 | 34.84 | N |
| ATOM | 3677 | N | LYS | D | 110 | 77.535 | 33.202 | 18.153 | 1.00 | 41.38 | N |
| ATOM | 3678 | CA | LYS | D | 110 | 78.548 | 34.224 | 18.409 | 1.00 | 42.34 | C |
| ATOM | 3679 | C | LYS | D | 110 | 79.756 | 33.629 | 19.142 | 1.00 | 42.60 | C |
| ATOM | 3680 | O | LYS | D | 110 | 80.887 | 33.701 | 18.654 | 1.00 | 42.50 | O |
| ATOM | 3681 | CB | LYS | D | 110 | 77.950 | 35.372 | 19.228 | 1.00 | 43.39 | C |
| ATOM | 3682 | CG | LYS | D | 110 | 78.764 | 36.671 | 19.157 | 1.00 | 45.14 | C |
| ATOM | 3683 | CD | LYS | D | 110 | 78.184 | 37.733 | 20.089 | 1.00 | 46.94 | C |
| ATOM | 3684 | CE | LYS | D | 110 | 78.868 | 39.075 | 19.907 | 1.00 | 46.68 | C |
| ATOM | 3685 | NZ | LYS | D | 110 | 78.587 | 39.607 | 18.551 | 1.00 | 48.63 | N |
| ATOM | 3686 | N | TYR | D | 111 | 79.505 | 33.048 | 20.313 | 1.00 | 42.45 | N |
| ATOM | 3687 | CA | TYR | D | 111 | 80.536 | 32.405 | 21.121 | 1.00 | 42.43 | C |
| ATOM | 3688 | C | TYR | D | 111 | 80.366 | 30.917 | 20.802 | 1.00 | 41.95 | C |
| ATOM | 3689 | O | TYR | D | 111 | 79.767 | 30.157 | 21.567 | 1.00 | 41.52 | O |
| ATOM | 3690 | CB | TYR | D | 111 | 80.276 | 32.716 | 22.604 | 1.00 | 42.93 | C |
| ATOM | 3691 | CG | TYR | D | 111 | 80.008 | 34.192 | 22.835 | 1.00 | 44.45 | C |
| ATOM | 3692 | CD1 | TYR | D | 111 | 81.028 | 35.142 | 22.685 | 1.00 | 44.58 | C |
| ATOM | 3693 | CD2 | TYR | D | 111 | 78.716 | 34.656 | 23.100 | 1.00 | 44.75 | C |
| ATOM | 3694 | CE1 | TYR | D | 111 | 80.763 | 36.515 | 22.779 | 1.00 | 44.52 | C |
| ATOM | 3695 | CE2 | TYR | D | 111 | 78.439 | 36.035 | 23.198 | 1.00 | 44.98 | C |
| ATOM | 3696 | CZ | TYR | D | 111 | 79.468 | 36.958 | 23.031 | 1.00 | 44.96 | C |
| ATOM | 3697 | OH | TYR | D | 111 | 79.198 | 38.313 | 23.072 | 1.00 | 43.46 | O |
| ATOM | 3698 | N | THR | D | 112 | 80.900 | 30.530 | 19.647 | 1.00 | 41.87 | N |
| ATOM | 3699 | CA | THR | D | 112 | 80.780 | 29.176 | 19.106 | 1.00 | 42.40 | C |
| ATOM | 3700 | C | THR | D | 112 | 81.192 | 27.950 | 19.913 | 1.00 | 42.28 | C |
| ATOM | 3701 | O | THR | D | 112 | 81.138 | 26.839 | 19.395 | 1.00 | 42.54 | O |
| ATOM | 3702 | CB | THR | D | 112 | 81.475 | 29.082 | 17.731 | 1.00 | 42.16 | C |
| ATOM | 3703 | OG1 | THR | D | 112 | 82.874 | 29.351 | 17.884 | 1.00 | 41.13 | O |
| ATOM | 3704 | CG2 | THR | D | 112 | 80.859 | 30.088 | 16.748 | 1.00 | 41.44 | C |
| ATOM | 3705 | N | SER | D | 113 | 81.587 | 28.118 | 21.168 | 1.00 | 42.10 | N |
| ATOM | 3706 | CA | SER | D | 113 | 81.975 | 26.954 | 21.955 | 1.00 | 42.41 | C |
| ATOM | 3707 | C | SER | D | 113 | 81.080 | 26.724 | 23.163 | 1.00 | 41.80 | C |
| ATOM | 3708 | O | SER | D | 113 | 81.165 | 25.685 | 23.822 | 1.00 | 41.36 | O |
| ATOM | 3709 | CB | SER | D | 113 | 83.435 | 27.081 | 22.409 | 1.00 | 42.58 | C |
| ATOM | 3710 | OG | SER | D | 113 | 84.313 | 26.966 | 21.300 | 1.00 | 42.66 | O |
| ATOM | 3711 | N | TRP | D | 114 | 80.213 | 27.686 | 23.445 | 1.00 | 41.58 | N |
| ATOM | 3712 | CA | TRP | D | 114 | 79.332 | 27.576 | 24.599 | 1.00 | 41.47 | C |
| ATOM | 3713 | C | TRP | D | 114 | 77.904 | 27.130 | 24.259 | 1.00 | 39.93 | C |
| ATOM | 3714 | O | TRP | D | 114 | 77.361 | 27.475 | 23.206 | 1.00 | 39.72 | O |

TABLE 3-continued

FGFR2(D2–D3) Complexed with FGF2

| ATOM | 3715 | CB | TRP | D | 114 | 79.332 | 28.910 | 25.356 | 1.00 | 43.57 | C |
|---|---|---|---|---|---|---|---|---|---|---|---|
| ATOM | 3716 | CG | TRP | D | 114 | 80.737 | 29.376 | 25.716 | 1.00 | 46.05 | C |
| ATOM | 3717 | CD1 | TRP | D | 114 | 81.863 | 28.593 | 25.827 | 1.00 | 46.16 | C |
| ATOM | 3718 | CD2 | TRP | D | 114 | 81.150 | 30.713 | 26.040 | 1.00 | 46.32 | C |
| ATOM | 3719 | NE1 | TRP | D | 114 | 82.943 | 29.363 | 26.198 | 1.00 | 46.71 | N |
| ATOM | 3720 | CE2 | TRP | D | 114 | 82.536 | 30.665 | 26.336 | 1.00 | 47.01 | C |
| ATOM | 3721 | CE3 | TRP | D | 114 | 80.486 | 31.947 | 26.110 | 1.00 | 47.32 | C |
| ATOM | 3722 | CZ2 | TRP | D | 114 | 83.265 | 31.805 | 26.699 | 1.00 | 47.13 | C |
| ATOM | 3723 | CZ3 | TRP | D | 114 | 81.216 | 33.085 | 26.469 | 1.00 | 47.34 | C |
| ATOM | 3724 | CH2 | TRP | D | 114 | 82.589 | 33.002 | 26.759 | 1.00 | 47.61 | C |
| ATOM | 3725 | N | TYR | D | 115 | 77.314 | 26.356 | 25.168 | 1.00 | 38.33 | N |
| ATOM | 3726 | CA | TYR | D | 115 | 75.960 | 25.828 | 25.006 | 1.00 | 36.97 | C |
| ATOM | 3727 | C | TYR | D | 115 | 74.963 | 26.369 | 26.025 | 1.00 | 36.33 | C |
| ATOM | 3728 | O | TYR | D | 115 | 75.331 | 26.736 | 27.138 | 1.00 | 35.87 | O |
| ATOM | 3729 | CB | TYR | D | 115 | 75.942 | 24.304 | 25.164 | 1.00 | 36.22 | C |
| ATOM | 3730 | CG | TYR | D | 115 | 76.677 | 23.519 | 24.111 | 1.00 | 36.66 | C |
| ATOM | 3731 | CD1 | TYR | D | 115 | 78.025 | 23.190 | 24.268 | 1.00 | 36.79 | C |
| ATOM | 3732 | CD2 | TYR | D | 115 | 76.019 | 23.076 | 22.965 | 1.00 | 36.10 | C |
| ATOM | 3733 | CE1 | TYR | D | 115 | 78.701 | 22.430 | 23.303 | 1.00 | 36.07 | C |
| ATOM | 3734 | CE2 | TYR | D | 115 | 76.683 | 22.319 | 21.998 | 1.00 | 36.64 | C |
| ATOM | 3735 | CZ | TYR | D | 115 | 78.024 | 22.001 | 22.174 | 1.00 | 36.29 | C |
| ATOM | 3736 | OH | TYR | D | 115 | 78.680 | 21.264 | 21.215 | 1.00 | 37.12 | O |
| ATOM | 3737 | N | VAL | D | 116 | 73.695 | 26.407 | 25.635 | 1.00 | 35.23 | N |
| ATOM | 3738 | CA | VAL | D | 116 | 72.642 | 26.819 | 26.551 | 1.00 | 34.37 | C |
| ATOM | 3739 | C | VAL | D | 116 | 72.531 | 25.584 | 27.446 | 1.00 | 34.42 | C |
| ATOM | 3740 | O | VAL | D | 116 | 72.486 | 24.459 | 26.952 | 1.00 | 34.27 | O |
| ATOM | 3741 | CB | VAL | D | 116 | 71.323 | 27.074 | 25.793 | 1.00 | 34.00 | C |
| ATOM | 3742 | CG1 | VAL | D | 116 | 70.193 | 27.308 | 26.770 | 1.00 | 33.39 | C |
| ATOM | 3743 | CG2 | VAL | D | 116 | 71.488 | 28.278 | 24.859 | 1.00 | 32.59 | C |
| ATOM | 3744 | N | ALA | D | 117 | 72.516 | 25.782 | 28.758 | 1.00 | 34.87 | N |
| ATOM | 3745 | CA | ALA | D | 117 | 72.467 | 24.649 | 29.670 | 1.00 | 35.64 | C |
| ATOM | 3746 | C | ALA | D | 117 | 71.928 | 25.005 | 31.042 | 1.00 | 36.78 | C |
| ATOM | 3747 | O | ALA | D | 117 | 71.969 | 26.163 | 31.464 | 1.00 | 37.35 | O |
| ATOM | 3748 | CB | ALA | D | 117 | 73.860 | 24.049 | 29.816 | 1.00 | 34.13 | C |
| ATOM | 3749 | N | LEU | D | 118 | 71.436 | 23.989 | 31.741 | 1.00 | 37.10 | N |
| ATOM | 3750 | CA | LEU | D | 118 | 70.900 | 24.169 | 33.077 | 1.00 | 38.06 | C |
| ATOM | 3751 | C | LEU | D | 118 | 71.645 | 23.263 | 34.048 | 1.00 | 38.81 | C |
| ATOM | 3752 | O | LEU | D | 118 | 72.098 | 22.184 | 33.670 | 1.00 | 39.30 | O |
| ATOM | 3753 | CB | LEU | D | 118 | 69.407 | 23.837 | 33.094 | 1.00 | 37.70 | C |
| ATOM | 3754 | CG | LEU | D | 118 | 68.470 | 24.742 | 32.287 | 1.00 | 37.45 | C |
| ATOM | 3755 | CD1 | LEU | D | 118 | 67.059 | 24.204 | 32.409 | 1.00 | 37.34 | C |
| ATOM | 3756 | CD2 | LEU | D | 118 | 68.536 | 26.189 | 32.801 | 1.00 | 37.18 | C |
| ATOM | 3757 | N | LYS | D | 119 | 71.773 | 23.709 | 35.294 | 1.00 | 40.12 | N |
| ATOM | 3758 | CA | LYS | D | 119 | 72.457 | 22.938 | 36.332 | 1.00 | 41.45 | C |
| ATOM | 3759 | C | LYS | D | 119 | 71.459 | 22.071 | 37.089 | 1.00 | 41.83 | C |
| ATOM | 3760 | O | LYS | D | 119 | 70.251 | 22.332 | 37.059 | 1.00 | 41.78 | O |
| ATOM | 3761 | CB | LYS | D | 119 | 73.172 | 23.882 | 37.311 | 1.00 | 41.32 | C |
| ATOM | 3762 | N | ARG | D | 120 | 71.967 | 21.044 | 37.767 | 1.00 | 41.92 | N |
| ATOM | 3763 | CA | ARG | D | 120 | 71.121 | 20.127 | 38.531 | 1.00 | 42.76 | C |
| ATOM | 3764 | C | ARG | D | 120 | 70.283 | 20.873 | 39.562 | 1.00 | 43.01 | C |
| ATOM | 3765 | O | ARG | D | 120 | 69.272 | 20.367 | 40.036 | 1.00 | 42.82 | O |
| ATOM | 3766 | CB | ARG | D | 120 | 71.977 | 19.066 | 39.232 | 1.00 | 41.45 | C |
| ATOM | 3767 | N | THR | D | 121 | 70.705 | 22.087 | 39.896 | 1.00 | 44.40 | N |
| ATOM | 3768 | CA | THR | D | 121 | 70.002 | 22.902 | 40.878 | 1.00 | 45.13 | C |
| ATOM | 3769 | C | THR | D | 121 | 68.783 | 23.614 | 40.294 | 1.00 | 45.85 | C |
| ATOM | 3770 | O | THR | D | 121 | 67.838 | 23.928 | 41.015 | 1.00 | 46.11 | O |
| ATOM | 3771 | CB | THR | D | 121 | 70.938 | 23.968 | 41.492 | 1.00 | 45.88 | C |
| ATOM | 3772 | OG1 | THR | D | 121 | 71.355 | 24.884 | 40.474 | 1.00 | 46.18 | O |
| ATOM | 3773 | CG2 | THR | D | 121 | 72.170 | 23.311 | 42.107 | 1.00 | 45.54 | C |
| ATOM | 3774 | N | GLY | D | 122 | 68.795 | 23.861 | 38.990 | 1.00 | 46.02 | N |
| ATOM | 3775 | CA | GLY | D | 122 | 67.676 | 24.550 | 38.380 | 1.00 | 46.48 | C |
| ATOM | 3776 | C | GLY | D | 122 | 68.100 | 25.922 | 37.901 | 1.00 | 47.04 | C |
| ATOM | 3777 | O | GLY | D | 122 | 67.324 | 26.662 | 37.291 | 1.00 | 47.14 | O |
| ATOM | 3778 | N | GLN | D | 123 | 69.348 | 26.269 | 38.191 | 1.00 | 47.07 | N |
| ATOM | 3779 | CA | GLN | D | 123 | 69.901 | 27.544 | 37.766 | 1.00 | 47.46 | C |
| ATOM | 3780 | C | GLN | D | 123 | 70.659 | 27.275 | 36.471 | 1.00 | 47.19 | C |
| ATOM | 3781 | O | GLN | D | 123 | 71.162 | 26.169 | 36.261 | 1.00 | 46.75 | O |
| ATOM | 3782 | CB | GLN | D | 123 | 70.844 | 28.091 | 38.841 | 1.00 | 48.11 | C |
| ATOM | 3783 | CG | GLN | D | 123 | 70.171 | 28.283 | 40.208 | 1.00 | 50.27 | C |
| ATOM | 3784 | CD | GLN | D | 123 | 68.986 | 29.255 | 40.164 | 1.00 | 51.25 | C |
| ATOM | 3785 | OE1 | GLN | D | 123 | 69.148 | 30.434 | 39.844 | 1.00 | 52.08 | O |
| ATOM | 3786 | NE2 | GLN | D | 123 | 67.792 | 28.758 | 40.488 | 1.00 | 52.19 | N |
| ATOM | 3787 | N | TYR | D | 124 | 70.728 | 28.266 | 35.589 | 1.00 | 46.86 | N |
| ATOM | 3788 | CA | TYR | D | 124 | 71.437 | 28.057 | 34.334 | 1.00 | 46.79 | C |
| ATOM | 3789 | C | TYR | D | 124 | 72.906 | 27.787 | 34.621 | 1.00 | 46.37 | C |
| ATOM | 3790 | O | TYR | D | 124 | 73.376 | 28.001 | 35.732 | 1.00 | 45.85 | O |
| ATOM | 3791 | CB | TYR | D | 124 | 71.280 | 29.267 | 33.392 | 1.00 | 46.13 | C |

TABLE 3-continued

| | | | | | FGFR2(D2–D3) Complexed with FGF2 | | | | | |
|---|---|---|---|---|---|---|---|---|---|---|
| ATOM | 3792 | CG | TYR | D | 124 | 71.982 | 30.538 | 33.819 | 1.00 | 46.17 | C |
| ATOM | 3793 | CD1 | TYR | D | 124 | 73.378 | 30.606 | 33.889 | 1.00 | 46.43 | C |
| ATOM | 3794 | CD2 | TYR | D | 124 | 71.255 | 31.679 | 34.141 | 1.00 | 46.18 | C |
| ATOM | 3795 | CE1 | TYR | D | 124 | 74.027 | 31.773 | 34.271 | 1.00 | 45.82 | C |
| ATOM | 3796 | CE2 | TYR | D | 124 | 71.895 | 32.855 | 34.525 | 1.00 | 46.61 | C |
| ATOM | 3797 | CZ | TYR | D | 124 | 73.281 | 32.893 | 34.588 | 1.00 | 46.75 | C |
| ATOM | 3798 | OH | TYR | D | 124 | 73.916 | 34.050 | 34.968 | 1.00 | 46.83 | O |
| ATOM | 3799 | N | LYS | D | 125 | 73.623 | 27.309 | 33.614 | 1.00 | 46.56 | N |
| ATOM | 3800 | CA | LYS | D | 125 | 75.037 | 27.012 | 33.753 | 1.00 | 46.99 | C |
| ATOM | 3801 | C | LYS | D | 125 | 75.827 | 27.925 | 32.810 | 1.00 | 48.06 | C |
| ATOM | 3802 | O | LYS | D | 125 | 75.468 | 28.063 | 31.639 | 1.00 | 47.64 | O |
| ATOM | 3803 | CB | LYS | D | 125 | 75.286 | 25.536 | 33.412 | 1.00 | 46.02 | C |
| ATOM | 3804 | CG | LYS | D | 125 | 76.737 | 25.092 | 33.511 | 1.00 | 44.48 | C |
| ATOM | 3805 | CD | LYS | D | 125 | 76.882 | 23.588 | 33.317 | 1.00 | 43.98 | C |
| ATOM | 3806 | CE | LYS | D | 125 | 78.340 | 23.164 | 33.502 | 1.00 | 44.57 | C |
| ATOM | 3807 | NZ | LYS | D | 125 | 78.571 | 21.693 | 33.380 | 1.00 | 44.60 | N |
| ATOM | 3808 | N | LEU | D | 126 | 76.885 | 28.557 | 33.326 | 1.00 | 49.01 | N |
| ATOM | 3809 | CA | LEU | D | 126 | 77.709 | 29.456 | 32.515 | 1.00 | 49.83 | C |
| ATOM | 3810 | C | LEU | D | 126 | 78.138 | 28.779 | 31.227 | 1.00 | 50.46 | C |
| ATOM | 3811 | O | LEU | D | 126 | 78.679 | 27.671 | 31.249 | 1.00 | 50.50 | O |
| ATOM | 3812 | CB | LEU | D | 126 | 78.961 | 29.896 | 33.275 | 1.00 | 50.45 | C |
| ATOM | 3813 | CG | LEU | D | 126 | 78.867 | 31.113 | 34.195 | 1.00 | 50.81 | C |
| ATOM | 3814 | CD1 | LEU | D | 126 | 80.256 | 31.435 | 34.713 | 1.00 | 51.18 | C |
| ATOM | 3815 | CD2 | LEU | D | 126 | 78.300 | 32.310 | 33.440 | 1.00 | 51.05 | C |
| ATOM | 3816 | N | GLY | D | 127 | 77.902 | 29.451 | 30.107 | 1.00 | 50.73 | N |
| ATOM | 3817 | CA | GLY | D | 127 | 78.273 | 28.887 | 28.825 | 1.00 | 51.40 | C |
| ATOM | 3818 | C | GLY | D | 127 | 79.724 | 28.447 | 28.784 | 1.00 | 51.76 | C |
| ATOM | 3819 | O | GLY | D | 127 | 80.065 | 27.458 | 28.135 | 1.00 | 51.74 | O |
| ATOM | 3820 | N | SER | D | 128 | 80.581 | 29.181 | 29.485 | 1.00 | 52.20 | N |
| ATOM | 3821 | CA | SER | D | 128 | 82.009 | 28.877 | 29.517 | 1.00 | 52.38 | C |
| ATOM | 3822 | C | SER | D | 128 | 82.332 | 27.552 | 30.204 | 1.00 | 52.36 | C |
| ATOM | 3823 | O | SER | D | 128 | 83.422 | 27.010 | 30.032 | 1.00 | 52.38 | O |
| ATOM | 3824 | CB | SER | D | 128 | 82.766 | 30.015 | 30.210 | 1.00 | 51.84 | C |
| ATOM | 3825 | OG | SER | D | 128 | 82.245 | 30.256 | 31.508 | 1.00 | 52.17 | O |
| ATOM | 3826 | N | LYS | D | 129 | 81.385 | 27.032 | 30.978 | 1.00 | 52.20 | N |
| ATOM | 3827 | CA | LYS | D | 129 | 81.603 | 25.778 | 31.679 | 1.00 | 51.76 | C |
| ATOM | 3828 | C | LYS | D | 129 | 80.881 | 24.603 | 31.022 | 1.00 | 51.64 | C |
| ATOM | 3829 | O | LYS | D | 129 | 80.761 | 23.531 | 31.626 | 1.00 | 51.64 | O |
| ATOM | 3830 | CB | LYS | D | 129 | 81.163 | 25.914 | 33.141 | 1.00 | 51.90 | C |
| ATOM | 3831 | N | THR | D | 130 | 80.414 | 24.795 | 29.788 | 1.00 | 50.58 | N |
| ATOM | 3832 | CA | THR | D | 130 | 79.702 | 23.732 | 29.073 | 1.00 | 49.71 | C |
| ATOM | 3833 | C | THR | D | 130 | 80.607 | 22.981 | 28.093 | 1.00 | 49.74 | C |
| ATOM | 3834 | O | THR | D | 130 | 81.644 | 23.495 | 27.668 | 1.00 | 49.14 | O |
| ATOM | 3835 | CB | THR | D | 130 | 78.464 | 24.285 | 28.296 | 1.00 | 48.64 | C |
| ATOM | 3836 | OG1 | THR | D | 130 | 78.893 | 25.121 | 27.217 | 1.00 | 47.18 | O |
| ATOM | 3837 | CG2 | THR | D | 130 | 77.579 | 25.098 | 29.223 | 1.00 | 47.63 | C |
| ATOM | 3838 | N | GLY | D | 131 | 80.197 | 21.763 | 27.748 | 1.00 | 49.99 | N |
| ATOM | 3839 | CA | GLY | D | 131 | 80.957 | 20.932 | 26.831 | 1.00 | 50.29 | C |
| ATOM | 3840 | C | GLY | D | 131 | 80.034 | 19.973 | 26.106 | 1.00 | 50.69 | C |
| ATOM | 3841 | O | GLY | D | 131 | 78.958 | 19.665 | 26.611 | 1.00 | 50.84 | O |
| ATOM | 3842 | N | PRO | D | 132 | 80.436 | 19.460 | 24.932 | 1.00 | 50.75 | N |
| ATOM | 3843 | CA | PRO | D | 132 | 79.650 | 18.532 | 24.114 | 1.00 | 50.96 | C |
| ATOM | 3844 | C | PRO | D | 132 | 79.156 | 17.236 | 24.755 | 1.00 | 50.84 | C |
| ATOM | 3845 | O | PRO | D | 132 | 78.126 | 16.697 | 24.342 | 1.00 | 51.32 | O |
| ATOM | 3846 | CB | PRO | D | 132 | 80.564 | 18.266 | 22.922 | 1.00 | 50.45 | C |
| ATOM | 3847 | CG | PRO | D | 132 | 81.915 | 18.352 | 23.534 | 1.00 | 51.47 | C |
| ATOM | 3848 | CD | PRO | D | 132 | 81.794 | 19.599 | 24.383 | 1.00 | 50.85 | C |
| ATOM | 3849 | N | GLY | D | 133 | 79.866 | 16.729 | 25.755 | 1.00 | 50.62 | N |
| ATOM | 3850 | CA | GLY | D | 133 | 79.423 | 15.487 | 26.368 | 1.00 | 50.28 | C |
| ATOM | 3851 | C | GLY | D | 133 | 78.620 | 15.632 | 27.653 | 1.00 | 49.91 | C |
| ATOM | 3852 | O | GLY | D | 133 | 78.214 | 14.631 | 28.251 | 1.00 | 50.17 | O |
| ATOM | 3853 | N | GLN | D | 134 | 78.365 | 16.868 | 28.072 | 1.00 | 48.40 | N |
| ATOM | 3854 | CA | GLN | D | 134 | 77.634 | 17.100 | 29.317 | 1.00 | 46.81 | C |
| ATOM | 3855 | C | GLN | D | 134 | 76.134 | 16.832 | 29.238 | 1.00 | 45.15 | C |
| ATOM | 3856 | O | GLN | D | 134 | 75.516 | 16.930 | 28.177 | 1.00 | 46.04 | O |
| ATOM | 3857 | CB | GLN | D | 134 | 77.873 | 18.531 | 29.811 | 1.00 | 46.96 | C |
| ATOM | 3858 | CG | GLN | D | 134 | 79.338 | 18.926 | 29.846 | 1.00 | 47.70 | C |
| ATOM | 3859 | CD | GLN | D | 134 | 79.558 | 20.326 | 30.386 | 1.00 | 47.89 | C |
| ATOM | 3860 | OE1 | GLN | D | 134 | 78.691 | 21.188 | 30.283 | 1.00 | 47.89 | O |
| ATOM | 3861 | NE2 | GLN | D | 134 | 80.735 | 20.562 | 30.948 | 1.00 | 48.55 | N |
| ATOM | 3862 | N | LYS | D | 135 | 75.561 | 16.497 | 30.386 | 1.00 | 42.43 | N |
| ATOM | 3863 | CA | LYS | D | 135 | 74.137 | 16.218 | 30.512 | 1.00 | 40.19 | C |
| ATOM | 3864 | C | LYS | D | 135 | 73.340 | 17.526 | 30.594 | 1.00 | 38.53 | C |
| ATOM | 3865 | O | LYS | D | 135 | 72.152 | 17.557 | 30.285 | 1.00 | 37.67 | O |
| ATOM | 3866 | CB | LYS | D | 135 | 73.897 | 15.394 | 31.777 | 1.00 | 40.03 | C |
| ATOM | 3867 | CG | LYS | D | 135 | 72.472 | 14.945 | 32.004 | 1.00 | 41.05 | C |
| ATOM | 3868 | CD | LYS | D | 135 | 72.397 | 14.061 | 33.240 | 1.00 | 42.04 | C |

TABLE 3-continued

| | | | | FGFR2(D2–D3) Complexed with FGF2 | | | | | | |
|---|---|---|---|---|---|---|---|---|---|---|
| ATOM | 3869 | CE | LYS | D | 135 | 71.022 | 13.439 | 33.391 | 1.00 | 44.23 | C |
| ATOM | 3870 | NZ | LYS | D | 135 | 70.910 | 12.597 | 34.613 | 1.00 | 44.81 | N |
| ATOM | 3871 | N | ALA | D | 136 | 74.015 | 18.599 | 30.999 | 1.00 | 36.85 | N |
| ATOM | 3872 | CA | ALA | D | 136 | 73.396 | 19.914 | 31.159 | 1.00 | 35.15 | C |
| ATOM | 3873 | C | ALA | D | 136 | 72.975 | 20.606 | 29.865 | 1.00 | 34.16 | C |
| ATOM | 3874 | O | ALA | D | 136 | 72.150 | 21.519 | 29.895 | 1.00 | 34.00 | O |
| ATOM | 3875 | CB | ALA | D | 136 | 74.333 | 20.825 | 31.935 | 1.00 | 35.72 | C |
| ATOM | 3876 | N | ILE | D | 137 | 73.531 | 20.180 | 28.733 | 1.00 | 32.28 | N |
| ATOM | 3877 | CA | ILE | D | 137 | 73.203 | 20.799 | 27.448 | 1.00 | 31.23 | C |
| ATOM | 3878 | C | ILE | D | 137 | 72.155 | 20.046 | 26.610 | 1.00 | 29.99 | C |
| ATOM | 3879 | O | ILE | D | 137 | 71.809 | 20.487 | 25.512 | 1.00 | 28.99 | O |
| ATOM | 3880 | CB | ILE | D | 137 | 74.457 | 20.948 | 26.562 | 1.00 | 31.38 | C |
| ATOM | 3881 | CG1 | ILE | D | 137 | 74.947 | 19.568 | 26.118 | 1.00 | 31.67 | C |
| ATOM | 3882 | CG2 | ILE | D | 137 | 75.565 | 21.644 | 27.333 | 1.00 | 31.93 | C |
| ATOM | 3883 | CD1 | ILE | D | 137 | 75.937 | 19.625 | 24.952 | 1.00 | 31.85 | C |
| ATOM | 3884 | N | LEU | D | 138 | 71.654 | 18.925 | 27.126 | 1.00 | 28.53 | N |
| ATOM | 3885 | CA | LEU | D | 138 | 70.688 | 18.110 | 26.390 | 1.00 | 28.11 | C |
| ATOM | 3886 | C | LEU | D | 138 | 69.227 | 18.469 | 26.674 | 1.00 | 27.53 | C |
| ATOM | 3887 | O | LEU | D | 138 | 68.759 | 18.376 | 27.804 | 1.00 | 26.19 | O |
| ATOM | 3888 | CB | LEU | D | 138 | 70.953 | 16.626 | 26.681 | 1.00 | 27.39 | C |
| ATOM | 3889 | CG | LEU | D | 138 | 72.392 | 16.167 | 26.347 | 1.00 | 27.32 | C |
| ATOM | 3890 | CD1 | LEU | D | 138 | 72.682 | 14.832 | 27.011 | 1.00 | 26.61 | C |
| ATOM | 3891 | CD2 | LEU | D | 138 | 72.600 | 16.079 | 24.829 | 1.00 | 25.73 | C |
| ATOM | 3892 | N | PHE | D | 139 | 68.521 | 18.878 | 25.622 | 1.00 | 27.78 | N |
| ATOM | 3893 | CA | PHE | D | 139 | 67.125 | 19.281 | 25.725 | 1.00 | 27.77 | C |
| ATOM | 3894 | C | PHE | D | 139 | 66.203 | 18.467 | 24.832 | 1.00 | 28.45 | C |
| ATOM | 3895 | O | PHE | D | 139 | 66.593 | 18.021 | 23.752 | 1.00 | 27.88 | O |
| ATOM | 3896 | CB | PHE | D | 139 | 66.977 | 20.753 | 25.336 | 1.00 | 27.55 | C |
| ATOM | 3897 | CG | PHE | D | 139 | 67.586 | 21.709 | 26.317 | 1.00 | 28.64 | C |
| ATOM | 3898 | CD1 | PHE | D | 139 | 68.936 | 22.036 | 26.249 | 1.00 | 28.56 | C |
| ATOM | 3899 | CD2 | PHE | D | 139 | 66.808 | 22.275 | 27.324 | 1.00 | 28.87 | C |
| ATOM | 3900 | CE1 | PHE | D | 139 | 69.504 | 22.913 | 27.173 | 1.00 | 30.32 | C |
| ATOM | 3901 | CE2 | PHE | D | 139 | 67.365 | 23.152 | 28.255 | 1.00 | 29.77 | C |
| ATOM | 3902 | CZ | PHE | D | 139 | 68.719 | 23.472 | 28.179 | 1.00 | 29.35 | C |
| ATOM | 3903 | N | LEU | D | 140 | 64.960 | 18.314 | 25.271 | 1.00 | 28.29 | N |
| ATOM | 3904 | CA | LEU | D | 140 | 63.966 | 17.586 | 24.501 | 1.00 | 28.59 | C |
| ATOM | 3905 | C | LEU | D | 140 | 62.785 | 18.526 | 24.250 | 1.00 | 29.50 | C |
| ATOM | 3906 | O | LEU | D | 140 | 62.099 | 18.943 | 25.187 | 1.00 | 29.38 | O |
| ATOM | 3907 | CB | LEU | D | 140 | 63.496 | 16.359 | 25.281 | 1.00 | 29.24 | C |
| ATOM | 3908 | CG | LEU | D | 140 | 62.673 | 15.280 | 24.567 | 1.00 | 31.29 | C |
| ATOM | 3909 | CD1 | LEU | D | 140 | 63.522 | 14.623 | 23.477 | 1.00 | 31.65 | C |
| ATOM | 3910 | CD2 | LEU | D | 140 | 62.212 | 14.221 | 25.592 | 1.00 | 30.86 | C |
| ATOM | 3911 | N | PRO | D | 141 | 62.548 | 18.903 | 22.985 | 1.00 | 30.09 | N |
| ATOM | 3912 | CA | PRO | D | 141 | 61.418 | 19.795 | 22.727 | 1.00 | 31.12 | C |
| ATOM | 3913 | C | PRO | D | 141 | 60.091 | 19.067 | 22.980 | 1.00 | 32.93 | C |
| ATOM | 3914 | O | PRO | D | 141 | 59.897 | 17.931 | 22.533 | 1.00 | 32.97 | O |
| ATOM | 3915 | CB | PRO | D | 141 | 61.607 | 20.184 | 21.260 | 1.00 | 30.79 | C |
| ATOM | 3916 | CG | PRO | D | 141 | 62.294 | 18.994 | 20.689 | 1.00 | 32.15 | C |
| ATOM | 3917 | CD | PRO | D | 141 | 63.310 | 18.658 | 21.747 | 1.00 | 29.91 | C |
| ATOM | 3918 | N | MET | D | 142 | 59.194 | 19.718 | 23.716 | 1.00 | 33.86 | N |
| ATOM | 3919 | CA | MET | D | 142 | 57.892 | 19.132 | 24.030 | 1.00 | 35.77 | C |
| ATOM | 3920 | C | MET | D | 142 | 56.747 | 20.096 | 23.728 | 1.00 | 36.97 | C |
| ATOM | 3921 | O | MET | D | 142 | 56.921 | 21.317 | 23.711 | 1.00 | 36.81 | O |
| ATOM | 3922 | CB | MET | D | 142 | 57.820 | 18.728 | 25.511 | 1.00 | 35.48 | C |
| ATOM | 3923 | CG | MET | D | 142 | 58.802 | 17.641 | 25.919 | 1.00 | 35.60 | C |
| ATOM | 3924 | SD | MET | D | 142 | 58.757 | 17.282 | 27.684 | 1.00 | 36.85 | S |
| ATOM | 3925 | CE | MET | D | 142 | 57.505 | 15.979 | 27.723 | 1.00 | 35.78 | C |
| ATOM | 3926 | N | SER | D | 143 | 55.572 | 19.529 | 23.499 | 1.00 | 38.75 | N |
| ATOM | 3927 | CA | SER | D | 143 | 54.375 | 20.304 | 23.202 | 1.00 | 40.93 | C |
| ATOM | 3928 | C | SER | D | 143 | 54.012 | 21.269 | 24.320 | 1.00 | 41.71 | C |
| ATOM | 3929 | O | SER | D | 143 | 54.180 | 20.966 | 25.502 | 1.00 | 40.96 | O |
| ATOM | 3930 | CB | SER | D | 143 | 53.194 | 19.362 | 22.976 | 1.00 | 41.49 | C |
| ATOM | 3931 | OG | SER | D | 143 | 51.973 | 20.068 | 23.054 | 1.00 | 43.53 | O |
| ATOM | 3932 | N | ALA | D | 144 | 53.508 | 22.435 | 23.939 | 1.00 | 43.61 | N |
| ATOM | 3933 | CA | ALA | D | 144 | 53.092 | 23.430 | 24.915 | 1.00 | 46.08 | C |
| ATOM | 3934 | C | ALA | D | 144 | 51.644 | 23.151 | 25.325 | 1.00 | 47.46 | C |
| ATOM | 3935 | O | ALA | D | 144 | 50.915 | 24.060 | 25.720 | 1.00 | 48.06 | O |
| ATOM | 3936 | CB | ALA | D | 144 | 53.210 | 24.815 | 24.319 | 1.00 | 46.29 | C |
| ATOM | 3937 | N | LYS | D | 145 | 51.239 | 21.885 | 25.223 | 1.00 | 48.83 | N |
| ATOM | 3938 | CA | LYS | D | 145 | 49.887 | 21.465 | 25.587 | 1.00 | 50.09 | C |
| ATOM | 3939 | C | LYS | D | 145 | 48.841 | 22.277 | 24.834 | 1.00 | 50.66 | C |
| ATOM | 3940 | O | LYS | D | 145 | 48.764 | 22.067 | 23.603 | 1.00 | 51.83 | O |
| ATOM | 3941 | CB | LYS | D | 145 | 49.679 | 21.615 | 27.099 | 1.00 | 49.26 | C |
| TER | 3942 | | LYS | D | 145 | | | | | | |
| ATOM | 3943 | N | ASN | E | 150 | 63.387 | 18.498 | −44.664 | 1.00 | 47.77 | N |
| ATOM | 3944 | CA | ASN | E | 150 | 63.113 | 19.128 | −43.338 | 1.00 | 46.93 | C |
| ATOM | 3945 | C | ASN | E | 150 | 62.016 | 18.447 | −42.513 | 1.00 | 46.19 | C |

TABLE 3-continued

FGFR2(D2–D3) Complexed with FGF2

| ATOM | 3946 | O | ASN | E | 150 | 62.081 | 18.424 | −41.284 | 1.00 | 46.58 | O |
|---|---|---|---|---|---|---|---|---|---|---|---|
| ATOM | 3947 | CB | ASN | E | 150 | 62.737 | 20.595 | −43.521 | 1.00 | 46.99 | C |
| ATOM | 3948 | N | LYS | E | 151 | 61.010 | 17.896 | −43.184 | 1.00 | 45.03 | N |
| ATOM | 3949 | CA | LYS | E | 151 | 59.899 | 17.209 | −42.519 | 1.00 | 43.69 | C |
| ATOM | 3950 | C | LYS | E | 151 | 60.297 | 15.780 | −42.130 | 1.00 | 43.11 | C |
| ATOM | 3951 | O | LYS | E | 151 | 60.737 | 14.997 | −42.972 | 1.00 | 42.16 | O |
| ATOM | 3952 | CB | LYS | E | 151 | 58.666 | 17.186 | −43.434 | 1.00 | 42.74 | C |
| ATOM | 3953 | N | ARG | E | 152 | 60.135 | 15.427 | −40.856 | 1.00 | 42.03 | N |
| ATOM | 3954 | CA | ARG | E | 152 | 60.542 | 14.090 | −40.419 | 1.00 | 40.41 | C |
| ATOM | 3955 | C | ARG | E | 152 | 59.854 | 13.582 | −39.156 | 1.00 | 39.14 | C |
| ATOM | 3956 | O | ARG | E | 152 | 59.402 | 14.355 | −38.305 | 1.00 | 38.94 | O |
| ATOM | 3957 | CB | ARG | E | 152 | 62.056 | 14.073 | −40.194 | 1.00 | 40.84 | C |
| ATOM | 3958 | CG | ARG | E | 152 | 62.522 | 15.098 | −39.163 | 1.00 | 41.74 | C |
| ATOM | 3959 | CD | ARG | E | 152 | 64.039 | 15.142 | −39.044 | 1.00 | 41.72 | C |
| ATOM | 3960 | NE | ARG | E | 152 | 64.597 | 13.867 | −38.601 | 1.00 | 41.23 | N |
| ATOM | 3961 | CZ | ARG | E | 152 | 65.873 | 13.691 | −38.262 | 1.00 | 41.68 | C |
| ATOM | 3962 | NH1 | ARG | E | 152 | 66.722 | 14.706 | −38.319 | 1.00 | 41.31 | N |
| ATOM | 3963 | NH2 | ARG | E | 152 | 66.304 | 12.507 | −37.851 | 1.00 | 41.80 | N |
| ATOM | 3964 | N | ALA | E | 153 | 59.790 | 12.262 | −39.050 | 1.00 | 37.40 | N |
| ATOM | 3965 | CA | ALA | E | 153 | 59.188 | 11.604 | −37.908 | 1.00 | 35.59 | C |
| ATOM | 3966 | C | ALA | E | 153 | 59.976 | 11.931 | −36.633 | 1.00 | 34.63 | C |
| ATOM | 3967 | O | ALA | E | 153 | 61.091 | 12.444 | −36.683 | 1.00 | 34.27 | O |
| ATOM | 3968 | CB | ALA | E | 153 | 59.153 | 10.086 | −38.147 | 1.00 | 35.29 | C |
| ATOM | 3969 | N | PRO | E | 154 | 59.396 | 11.629 | −35.467 | 1.00 | 33.84 | N |
| ATOM | 3970 | CA | PRO | E | 154 | 60.045 | 11.892 | −34.183 | 1.00 | 33.06 | C |
| ATOM | 3971 | C | PRO | E | 154 | 61.294 | 11.046 | −33.977 | 1.00 | 33.19 | C |
| ATOM | 3972 | O | PRO | E | 154 | 61.378 | 9.921 | −34.475 | 1.00 | 32.44 | O |
| ATOM | 3973 | CB | PRO | E | 154 | 58.954 | 11.553 | −33.185 | 1.00 | 33.37 | C |
| ATOM | 3974 | CG | PRO | E | 154 | 58.220 | 10.453 | −33.883 | 1.00 | 33.19 | C |
| ATOM | 3975 | CD | PRO | E | 154 | 58.098 | 10.962 | −35.274 | 1.00 | 32.82 | C |
| ATOM | 3976 | N | TYR | E | 155 | 62.260 | 11.596 | −33.247 | 1.00 | 33.51 | N |
| ATOM | 3977 | CA | TYR | E | 155 | 63.498 | 10.894 | −32.958 | 1.00 | 34.94 | C |
| ATOM | 3978 | C | TYR | E | 155 | 64.120 | 11.421 | −31.662 | 1.00 | 34.71 | C |
| ATOM | 3979 | O | TYR | E | 155 | 63.963 | 12.592 | −31.327 | 1.00 | 34.98 | O |
| ATOM | 3980 | CB | TYR | E | 155 | 64.481 | 11.049 | −34.127 | 1.00 | 36.16 | C |
| ATOM | 3981 | CG | TYR | E | 155 | 64.952 | 12.469 | −34.361 | 1.00 | 37.74 | C |
| ATOM | 3982 | CD1 | TYR | E | 155 | 64.101 | 13.430 | −34.914 | 1.00 | 38.83 | C |
| ATOM | 3983 | CD2 | TYR | E | 155 | 66.246 | 12.854 | −34.017 | 1.00 | 38.46 | C |
| ATOM | 3984 | CE1 | TYR | E | 155 | 64.532 | 14.740 | −35.117 | 1.00 | 39.50 | C |
| ATOM | 3985 | CE2 | TYR | E | 155 | 66.685 | 14.156 | −34.212 | 1.00 | 39.37 | C |
| ATOM | 3986 | CZ | TYR | E | 155 | 65.826 | 15.093 | −34.762 | 1.00 | 39.92 | C |
| ATOM | 3987 | OH | TYR | E | 155 | 66.273 | 16.380 | −34.954 | 1.00 | 41.10 | O |
| ATOM | 3988 | N | TRP | E | 156 | 64.812 | 10.548 | −30.935 | 1.00 | 34.75 | N |
| ATOM | 3989 | CA | TRP | E | 156 | 65.469 | 10.923 | −29.681 | 1.00 | 36.24 | C |
| ATOM | 3990 | C | TRP | E | 156 | 66.687 | 11.801 | −29.972 | 1.00 | 37.97 | C |
| ATOM | 3991 | O | TRP | E | 156 | 67.530 | 11.419 | −30.777 | 1.00 | 38.67 | O |
| ATOM | 3992 | CB | TRP | E | 156 | 65.934 | 9.663 | −28.944 | 1.00 | 33.60 | C |
| ATOM | 3993 | CG | TRP | E | 156 | 64.863 | 8.670 | −28.702 | 1.00 | 31.13 | C |
| ATOM | 3994 | CD1 | TRP | E | 156 | 64.932 | 7.336 | −28.928 | 1.00 | 29.72 | C |
| ATOM | 3995 | CD2 | TRP | E | 156 | 63.554 | 8.925 | −28.168 | 1.00 | 30.40 | C |
| ATOM | 3996 | NE1 | TRP | E | 156 | 63.755 | 6.732 | −28.572 | 1.00 | 29.08 | N |
| ATOM | 3997 | CE2 | TRP | E | 156 | 62.888 | 7.682 | −28.103 | 1.00 | 30.19 | C |
| ATOM | 3998 | CE3 | TRP | E | 156 | 62.881 | 10.082 | −27.737 | 1.00 | 29.65 | C |
| ATOM | 3999 | CZ2 | TRP | E | 156 | 61.575 | 7.554 | −27.625 | 1.00 | 29.52 | C |
| ATOM | 4000 | CZ3 | TRP | E | 156 | 61.574 | 9.962 | −27.261 | 1.00 | 29.43 | C |
| ATOM | 4001 | CH2 | TRP | E | 156 | 60.935 | 8.703 | −27.209 | 1.00 | 29.93 | C |
| ATOM | 4002 | N | THR | E | 157 | 66.782 | 12.957 | −29.314 | 1.00 | 40.28 | N |
| ATOM | 4003 | CA | THR | E | 157 | 67.902 | 13.875 | −29.521 | 1.00 | 42.16 | C |
| ATOM | 4004 | C | THR | E | 157 | 69.039 | 13.675 | −28.533 | 1.00 | 43.32 | C |
| ATOM | 4005 | O | THR | E | 157 | 70.058 | 14.349 | −28.620 | 1.00 | 44.81 | O |
| ATOM | 4006 | CB | THR | E | 157 | 67.461 | 15.348 | −29.435 | 1.00 | 42.71 | C |
| ATOM | 4007 | OG1 | THR | E | 157 | 66.867 | 15.605 | −28.154 | 1.00 | 43.09 | O |
| ATOM | 4008 | CG2 | THR | E | 157 | 66.473 | 15.672 | −30.544 | 1.00 | 43.30 | C |
| ATOM | 4009 | N | ASN | E | 158 | 68.872 | 12.757 | −27.590 | 1.00 | 44.89 | N |
| ATOM | 4010 | CA | ASN | E | 158 | 69.924 | 12.487 | −26.612 | 1.00 | 46.03 | C |
| ATOM | 4011 | C | ASN | E | 158 | 69.718 | 11.148 | −25.926 | 1.00 | 45.86 | C |
| ATOM | 4012 | O | ASN | E | 158 | 69.194 | 11.090 | −24.817 | 1.00 | 45.97 | O |
| ATOM | 4013 | CB | ASN | E | 158 | 69.979 | 13.589 | −25.551 | 1.00 | 47.13 | C |
| ATOM | 4014 | CG | ASN | E | 158 | 71.164 | 13.429 | −24.610 | 1.00 | 48.57 | C |
| ATOM | 4015 | OD1 | ASN | E | 158 | 71.263 | 12.448 | −23.865 | 1.00 | 48.99 | O |
| ATOM | 4016 | ND2 | ASN | E | 158 | 72.074 | 14.394 | −24.644 | 1.00 | 48.78 | N |
| ATOM | 4017 | N | THR | E | 159 | 70.146 | 10.075 | −26.586 | 1.00 | 45.97 | N |
| ATOM | 4018 | CA | THR | E | 159 | 69.996 | 8.730 | −26.040 | 1.00 | 46.61 | C |
| ATOM | 4019 | C | THR | E | 159 | 70.850 | 8.478 | −24.806 | 1.00 | 47.15 | C |
| ATOM | 4020 | O | THR | E | 159 | 70.583 | 7.542 | −24.051 | 1.00 | 47.10 | O |
| ATOM | 4021 | CB | THR | E | 159 | 70.339 | 7.634 | −27.087 | 1.00 | 47.22 | C |
| ATOM | 4022 | OG1 | THR | E | 159 | 71.646 | 7.868 | −27.626 | 1.00 | 48.06 | O |

TABLE 3-continued

FGFR2(D2–D3) Complexed with FGF2

| ATOM | 4023 | CG2 | THR | E | 159 | 69.318 | 7.629 | −28.221 | 1.00 | 47.67 | C |
|---|---|---|---|---|---|---|---|---|---|---|---|
| ATOM | 4024 | N | GLU | E | 160 | 71.877 | 9.303 | −24.612 | 1.00 | 47.12 | N |
| ATOM | 4025 | CA | GLU | E | 160 | 72.773 | 9.159 | −23.469 | 1.00 | 47.32 | C |
| ATOM | 4026 | C | GLU | E | 160 | 71.976 | 9.235 | −22.169 | 1.00 | 47.16 | C |
| ATOM | 4027 | O | GLU | E | 160 | 72.101 | 8.379 | −21.299 | 1.00 | 47.06 | O |
| ATOM | 4028 | CB | GLU | E | 160 | 73.837 | 10.265 | −23.494 | 1.00 | 47.70 | C |
| ATOM | 4029 | N | LYS | E | 161 | 71.144 | 10.265 | −22.065 | 1.00 | 46.66 | N |
| ATOM | 4030 | CA | LYS | E | 161 | 70.311 | 10.491 | −20.892 | 1.00 | 46.05 | C |
| ATOM | 4031 | C | LYS | E | 161 | 69.145 | 9.506 | −20.757 | 1.00 | 45.11 | C |
| ATOM | 4032 | O | LYS | E | 161 | 68.353 | 9.626 | −19.822 | 1.00 | 45.34 | O |
| ATOM | 4033 | CB | LYS | E | 161 | 69.756 | 11.923 | −20.926 | 1.00 | 46.21 | C |
| ATOM | 4034 | N | MET | E | 162 | 69.038 | 8.548 | −21.678 | 1.00 | 44.22 | N |
| ATOM | 4035 | CA | MET | E | 162 | 67.946 | 7.560 | −21.659 | 1.00 | 43.37 | C |
| ATOM | 4036 | C | MET | E | 162 | 68.428 | 6.130 | −21.400 | 1.00 | 43.15 | C |
| ATOM | 4037 | O | MET | E | 162 | 67.617 | 5.214 | −21.232 | 1.00 | 42.92 | O |
| ATOM | 4038 | CB | MET | E | 162 | 67.181 | 7.569 | −22.999 | 1.00 | 42.59 | C |
| ATOM | 4039 | CG | MET | E | 162 | 66.441 | 8.858 | −23.359 | 1.00 | 42.12 | C |
| ATOM | 4040 | SD | MET | E | 162 | 65.737 | 8.805 | −25.069 | 1.00 | 43.12 | S |
| ATOM | 4041 | CE | MET | E | 162 | 64.428 | 7.582 | −24.869 | 1.00 | 41.06 | C |
| ATOM | 4042 | N | GLU | E | 163 | 69.742 | 5.937 | −21.367 | 1.00 | 42.76 | N |
| ATOM | 4043 | CA | GLU | E | 163 | 70.316 | 4.605 | −21.163 | 1.00 | 42.46 | C |
| ATOM | 4044 | C | GLU | E | 163 | 69.991 | 3.951 | −19.814 | 1.00 | 41.50 | C |
| ATOM | 4045 | O | GLU | E | 163 | 69.837 | 2.728 | −19.727 | 1.00 | 41.96 | O |
| ATOM | 4046 | CB | GLU | E | 163 | 71.837 | 4.667 | −21.363 | 1.00 | 42.74 | C |
| ATOM | 4047 | N | LYS | E | 164 | 69.898 | 4.760 | −18.765 | 1.00 | 39.99 | N |
| ATOM | 4048 | CA | LYS | E | 164 | 69.585 | 4.270 | −17.422 | 1.00 | 38.16 | C |
| ATOM | 4049 | C | LYS | E | 164 | 68.083 | 3.937 | −17.381 | 1.00 | 37.14 | C |
| ATOM | 4050 | O | LYS | E | 164 | 67.256 | 4.827 | −17.185 | 1.00 | 37.33 | O |
| ATOM | 4051 | CB | LYS | E | 164 | 69.945 | 5.369 | −16.410 | 1.00 | 36.48 | C |
| ATOM | 4052 | CG | LYS | E | 164 | 69.679 | 5.058 | −14.947 | 1.00 | 36.37 | C |
| ATOM | 4053 | CD | LYS | E | 164 | 70.119 | 6.229 | −14.072 | 1.00 | 37.37 | C |
| ATOM | 4054 | CE | LYS | E | 164 | 69.633 | 6.106 | −12.638 | 1.00 | 38.14 | C |
| ATOM | 4055 | NZ | LYS | E | 164 | 69.990 | 7.292 | −11.803 | 1.00 | 38.47 | N |
| ATOM | 4056 | N | ARG | E | 165 | 67.739 | 2.664 | −17.580 | 1.00 | 36.23 | N |
| ATOM | 4057 | CA | ARG | E | 165 | 66.335 | 2.235 | −17.596 | 1.00 | 35.70 | C |
| ATOM | 4058 | C | ARG | E | 165 | 65.707 | 2.067 | −16.224 | 1.00 | 34.16 | C |
| ATOM | 4059 | O | ARG | E | 165 | 64.562 | 2.469 | −16.011 | 1.00 | 32.97 | O |
| ATOM | 4060 | CB | ARG | E | 165 | 66.172 | 0.936 | −18.392 | 1.00 | 36.74 | C |
| ATOM | 4061 | CG | ARG | E | 165 | 66.260 | 1.141 | −19.899 | 1.00 | 39.91 | C |
| ATOM | 4062 | CD | ARG | E | 165 | 66.310 | −0.183 | −20.631 | 1.00 | 41.98 | C |
| ATOM | 4063 | NE | ARG | E | 165 | 66.734 | −0.020 | −22.017 | 1.00 | 44.67 | N |
| ATOM | 4064 | CZ | ARG | E | 165 | 65.920 | 0.2482 | −3.035 | 1.00 | 46.24 | C |
| ATOM | 4065 | NH1 | ARG | E | 165 | 64.607 | 0.3822 | −2.840 | 1.00 | 46.06 | N |
| ATOM | 4066 | NH2 | ARG | E | 165 | 66.428 | 0.3922 | −4.253 | 1.00 | 46.74 | N |
| ATOM | 4067 | N | LEU | E | 166 | 66.456 | 1.466 | −15.305 | 1.00 | 33.11 | N |
| ATOM | 4068 | CA | LEU | E | 166 | 65.995 | 1.251 | −13.938 | 1.00 | 32.45 | C |
| ATOM | 4069 | C | LEU | E | 166 | 66.407 | 2.422 | −13.053 | 1.00 | 32.78 | C |
| ATOM | 4070 | O | LEU | E | 166 | 67.600 | 2.701 | −12.911 | 1.00 | 32.57 | O |
| ATOM | 4071 | CB | LEU | E | 166 | 66.603 | −0.034 | −13.363 | 1.00 | 30.72 | C |
| ATOM | 4072 | CG | LEU | E | 166 | 66.452 | −0.238 | −11.842 | 1.00 | 31.40 | C |
| ATOM | 4073 | CD1 | LEU | E | 166 | 64.982 | −0.336 | −11.443 | 1.00 | 29.68 | C |
| ATOM | 4074 | CD2 | LEU | E | 166 | 67.179 | −1.497 | −11.430 | 1.00 | 31.08 | C |
| ATOM | 4075 | N | HIS | E | 167 | 65.421 | 3.102 | −12.472 | 1.00 | 32.56 | N |
| ATOM | 4076 | CA | HIS | E | 167 | 65.657 | 4.223 | −11.563 | 1.00 | 32.60 | C |
| ATOM | 4077 | C | HIS | E | 167 | 65.250 | 3.782 | −10.170 | 1.00 | 32.67 | C |
| ATOM | 4078 | O | HIS | E | 167 | 64.053 | 3.731 | −9.863 | 1.00 | 32.64 | O |
| ATOM | 4079 | CB | HIS | E | 167 | 64.799 | 5.438 | −11.927 | 1.00 | 33.90 | C |
| ATOM | 4080 | CG | HIS | E | 167 | 65.393 | 6.322 | −12.975 | 1.00 | 35.97 | C |
| ATOM | 4081 | ND1 | HIS | E | 167 | 65.717 | 5.871 | −14.237 | 1.00 | 37.14 | N |
| ATOM | 4082 | CD2 | HIS | E | 167 | 65.711 | 7.638 | −12.950 | 1.00 | 35.95 | C |
| ATOM | 4083 | CE1 | HIS | E | 167 | 66.212 | 6.872 | −14.944 | 1.00 | 36.75 | C |
| ATOM | 4084 | NE2 | HIS | E | 167 | 66.217 | 7.954 | −14.185 | 1.00 | 36.35 | N |
| ATOM | 4085 | N | ALA | E | 168 | 66.234 | 3.456 | −9.337 | 1.00 | 31.87 | N |
| ATOM | 4086 | CA | ALA | E | 168 | 65.982 | 3.044 | −7.960 | 1.00 | 31.90 | C |
| ATOM | 4087 | C | ALA | E | 168 | 66.360 | 4.250 | −7.119 | 1.00 | 31.80 | C |
| ATOM | 4088 | O | ALA | E | 168 | 67.505 | 4.698 | −7.162 | 1.00 | 31.50 | O |
| ATOM | 4089 | CB | ALA | E | 168 | 66.863 | 1.855 | −7.586 | 1.00 | 32.12 | C |
| ATOM | 4090 | N | VAL | E | 169 | 65.413 | 4.770 | −6.351 | 1.00 | 31.54 | N |
| ATOM | 4091 | CA | VAL | E | 169 | 65.676 | 5.942 | −5.531 | 1.00 | 32.05 | C |
| ATOM | 4092 | C | VAL | E | 169 | 65.116 | 5.822 | −4.122 | 1.00 | 31.84 | C |
| ATOM | 4093 | O | VAL | E | 169 | 64.165 | 5.085 | −3.876 | 1.00 | 31.58 | O |
| ATOM | 4094 | CB | VAL | E | 169 | 65.058 | 7.209 | −6.158 | 1.00 | 33.04 | C |
| ATOM | 4095 | CG1 | VAL | E | 169 | 65.520 | 7.359 | −7.606 | 1.00 | 33.81 | C |
| ATOM | 4096 | CG2 | VAL | E | 169 | 63.536 | 7.135 | −6.077 | 1.00 | 32.98 | C |
| ATOM | 4097 | N | PRO | E | 170 | 65.705 | 6.564 | −3.177 | 1.00 | 31.48 | N |
| ATOM | 4098 | CA | PRO | E | 170 | 65.226 | 6.517 | −1.796 | 1.00 | 31.72 | C |
| ATOM | 4099 | C | PRO | E | 170 | 63.924 | 7.295 | −1.658 | 1.00 | 32.29 | C |

TABLE 3-continued

FGFR2(D2–D3) Complexed with FGF2

| ATOM | 4100 | O | PRO | E | 170 | 63.715 | 8.310 | −2.334 | 1.00 | 31.99 | O |
|---|---|---|---|---|---|---|---|---|---|---|---|
| ATOM | 4101 | CB | PRO | E | 170 | 66.380 | 7.135 | −1.015 | 1.00 | 31.55 | C |
| ATOM | 4102 | CG | PRO | E | 170 | 66.954 | 8.136 | −2.001 | 1.00 | 31.18 | C |
| ATOM | 4103 | CD | PRO | E | 170 | 66.904 | 7.408 | −3.314 | 1.00 | 30.68 | C |
| ATOM | 4104 | N | ALA | E | 171 | 63.038 | 6.804 | −0.795 | 1.00 | 33.07 | N |
| ATOM | 4105 | CA | ALA | E | 171 | 61.751 | 7.455 | −0.557 | 1.00 | 33.03 | C |
| ATOM | 4106 | C | ALA | E | 171 | 61.931 | 8.925 | −0.162 | 1.00 | 33.54 | C |
| ATOM | 4107 | O | ALA | E | 171 | 62.927 | 9.295 | 0.474 | 1.00 | 32.77 | O |
| ATOM | 4108 | CB | ALA | E | 171 | 60.988 | 6.718 | 0.534 | 1.00 | 32.87 | C |
| ATOM | 4109 | N | ALA | E | 172 | 60.964 | 9.754 | −0.560 | 1.00 | 33.21 | N |
| ATOM | 4110 | CA | ALA | E | 172 | 60.947 | 11.185 | −0.266 | 1.00 | 33.03 | C |
| ATOM | 4111 | C | ALA | E | 172 | 61.740 | 12.058 | −1.238 | 1.00 | 33.63 | C |
| ATOM | 4112 | O | ALA | E | 172 | 61.736 | 13.287 | −1.124 | 1.00 | 34.46 | O |
| ATOM | 4113 | CB | ALA | E | 172 | 61.400 | 11.443 | 1.187 | 1.00 | 34.01 | C |
| ATOM | 4114 | N | ASN | E | 173 | 62.415 | 11.435 | −2.196 | 1.00 | 33.56 | N |
| ATOM | 4115 | CA | ASN | E | 173 | 63.166 | 12.197 | −3.190 | 1.00 | 32.94 | C |
| ATOM | 4116 | C | ASN | E | 173 | 62.284 | 12.535 | −4.384 | 1.00 | 31.99 | C |
| ATOM | 4117 | O | ASN | E | 173 | 61.169 | 12.036 | −4.508 | 1.00 | 31.57 | O |
| ATOM | 4118 | CB | ASN | E | 173 | 64.391 | 11.405 | −3.662 | 1.00 | 33.95 | C |
| ATOM | 4119 | CG | ASN | E | 173 | 65.628 | 11.723 | −2.845 | 1.00 | 35.18 | C |
| ATOM | 4120 | OD1 | ASN | E | 173 | 65.561 | 11.861 | −1.625 | 1.00 | 34.81 | O |
| ATOM | 4121 | ND2 | ASN | E | 173 | 66.766 | 11.840 | −3.518 | 1.00 | 36.97 | N |
| ATOM | 4122 | N | THR | E | 174 | 62.789 | 13.401 | −5.249 | 1.00 | 31.28 | N |
| ATOM | 4123 | CA | THR | E | 174 | 62.086 | 13.781 | −6.462 | 1.00 | 30.65 | C |
| ATOM | 4124 | C | THR | E | 174 | 62.686 | 12.961 | −7.598 | 1.00 | 30.83 | C |
| ATOM | 4125 | O | THR | E | 174 | 63.902 | 12.760 | −7.639 | 1.00 | 31.45 | O |
| ATOM | 4126 | CB | THR | E | 174 | 62.282 | 15.275 | −6.779 | 1.00 | 29.35 | C |
| ATOM | 4127 | OG1 | THR | E | 174 | 61.465 | 16.058 | −5.904 | 1.00 | 30.67 | O |
| ATOM | 4128 | CG2 | THR | E | 174 | 61.914 | 15.568 | −8.217 | 1.00 | 29.28 | C |
| ATOM | 4129 | N | VAL | E | 175 | 61.845 | 12.473 | −8.507 | 1.00 | 30.88 | N |
| ATOM | 4130 | CA | VAL | E | 175 | 62.348 | 11.712 | −9.638 | 1.00 | 30.80 | C |
| ATOM | 4131 | C | VAL | E | 175 | 61.974 | 12.419 | −10.937 | 1.00 | 30.86 | C |
| ATOM | 4132 | O | VAL | E | 175 | 60.902 | 13.025 | −11.054 | 1.00 | 31.51 | O |
| ATOM | 4133 | CB | VAL | E | 175 | 61.821 | 10.248 | −9.627 | 1.00 | 31.74 | C |
| ATOM | 4134 | CG1 | VAL | E | 175 | 60.319 | 10.233 | −9.781 | 1.00 | 32.32 | C |
| ATOM | 4135 | CG2 | VAL | E | 175 | 62.495 | 9.445 | −10.738 | 1.00 | 31.70 | C |
| ATOM | 4136 | N | LYS | E | 176 | 62.878 | 12.374 | −11.905 | 1.00 | 30.11 | N |
| ATOM | 4137 | CA | LYS | E | 176 | 62.633 | 13.014 | −13.186 | 1.00 | 30.97 | C |
| ATOM | 4138 | C | LYS | E | 176 | 63.008 | 12.107 | −14.357 | 1.00 | 30.93 | C |
| ATOM | 4139 | O | LYS | E | 176 | 64.146 | 11.636 | −14.454 | 1.00 | 30.54 | O |
| ATOM | 4140 | CB | LYS | A | 176 | 63.421 | 14.331 | −13.269 | 1.00 | 32.52 | C |
| ATOM | 4141 | CG | LYS | A | 176 | 63.251 | 15.108 | −14.578 | 1.00 | 34.91 | C |
| ATOM | 4142 | CD | LYS | A | 176 | 63.964 | 16.489 | −14.539 | 1.00 | 36.19 | C |
| ATOM | 4143 | CE | LYS | A | 176 | 63.966 | 17.158 | −15.924 | 1.00 | 38.06 | C |
| ATOM | 4144 | NZ | LYS | E | 176 | 64.564 | 18.542 | −15.996 | 1.00 | 38.65 | N |
| ATOM | 4145 | N | PHE | E | 177 | 62.043 | 11.847 | −15.233 | 1.00 | 30.34 | N |
| ATOM | 4146 | CA | PHE | E | 177 | 62.293 | 11.022 | −16.405 | 1.00 | 29.82 | C |
| ATOM | 4147 | C | PHE | E | 177 | 62.299 | 11.931 | −17.615 | 1.00 | 29.71 | C |
| ATOM | 4148 | O | PHE | E | 177 | 61.473 | 12.834 | −17.713 | 1.00 | 30.29 | O |
| ATOM | 4149 | CB | PHE | E | 177 | 61.207 | 9.965 | −16.557 | 1.00 | 29.12 | C |
| ATOM | 4150 | CG | PHE | E | 177 | 61.217 | 8.934 | −15.469 | 1.00 | 29.66 | C |
| ATOM | 4151 | CD1 | PHE | E | 177 | 62.347 | 8.152 | −15.249 | 1.00 | 29.65 | C |
| ATOM | 4152 | CD2 | PHE | E | 177 | 60.095 | 8.725 | −14.680 | 1.00 | 29.44 | C |
| ATOM | 4153 | CE1 | PHE | E | 177 | 62.359 | 7.179 | −14.266 | 1.00 | 29.37 | C |
| ATOM | 4154 | CE2 | PHE | E | 177 | 60.095 | 7.752 | −13.690 | 1.00 | 30.37 | C |
| ATOM | 4155 | CZ | PHE | E | 177 | 61.235 | 6.973 | −13.484 | 1.00 | 29.78 | C |
| ATOM | 4156 | N | ARG | E | 178 | 63.232 | 11.700 | −18.531 | 1.00 | 29.90 | N |
| ATOM | 4157 | CA | ARG | E | 178 | 63.325 | 12.518 | −19.737 | 1.00 | 30.18 | C |
| ATOM | 4158 | C | ARG | E | 178 | 63.414 | 11.697 | −21.025 | 1.00 | 30.49 | C |
| ATOM | 4159 | O | ARG | E | 178 | 63.956 | 10.585 | −21.040 | 1.00 | 28.47 | O |
| ATOM | 4160 | CB | ARG | E | 178 | 64.544 | 13.443 | −19.659 | 1.00 | 31.50 | C |
| ATOM | 4161 | CG | ARG | E | 178 | 64.607 | 14.318 | −18.410 | 1.00 | 35.87 | C |
| ATOM | 4162 | CD | ARG | E | 178 | 65.695 | 15.381 | −18.567 | 1.00 | 37.95 | C |
| ATOM | 4163 | NE | ARG | E | 178 | 65.438 | 16.174 | −19.766 | 1.00 | 41.27 | N |
| ATOM | 4164 | CZ | ARG | E | 178 | 66.350 | 16.890 | −20.415 | 1.00 | 42.38 | C |
| ATOM | 4165 | NH1 | ARG | E | 178 | 67.609 | 16.929 | −19.983 | 1.00 | 43.71 | N |
| ATOM | 4166 | NH2 | ARG | E | 178 | 66.007 | 17.545 | −21.519 | 1.00 | 42.32 | N |
| ATOM | 4167 | N | CYS | E | 179 | 62.870 | 12.263 | −22.102 | 1.00 | 30.09 | N |
| ATOM | 4168 | CA | CYS | E | 179 | 62.900 | 11.645 | −23.415 | 1.00 | 31.40 | C |
| ATOM | 4169 | C | CYS | E | 179 | 63.079 | 12.753 | −24.455 | 1.00 | 31.54 | C |
| ATOM | 4170 | O | CYS | E | 179 | 62.190 | 13.026 | −25.260 | 1.00 | 30.99 | O |
| ATOM | 4171 | CB | CYS | E | 179 | 61.608 | 10.857 | −23.646 | 1.00 | 32.04 | C |
| ATOM | 4172 | SG | CYS | E | 179 | 61.472 | 9.459 | −22.503 | 1.00 | 33.20 | S |
| ATOM | 4173 | N | PRO | E | 180 | 64.253 | 13.412 | −24.436 | 1.00 | 32.00 | N |
| ATOM | 4174 | CA | PRO | E | 180 | 64.578 | 14.504 | −25.365 | 1.00 | 32.32 | C |
| ATOM | 4175 | C | PRO | E | 180 | 64.274 | 14.080 | −26.789 | 1.00 | 32.64 | C |
| ATOM | 4176 | O | PRO | E | 180 | 64.824 | 13.092 | −27.272 | 1.00 | 32.30 | O |

TABLE 3-continued

FGFR2(D2–D3) Complexed with FGF2

| ATOM | 4177 | CB | PRO | E | 180 | 66.076 | 14.713 | −25.137 | 1.00 | 31.72 | C |
|---|---|---|---|---|---|---|---|---|---|---|---|
| ATOM | 4178 | CG | PRO | E | 180 | 66.238 | 14.376 | −23.684 | 1.00 | 32.39 | C |
| ATOM | 4179 | CD | PRO | E | 180 | 65.394 | 13.113 | −23.550 | 1.00 | 31.38 | C |
| ATOM | 4180 | N | ALA | E | 181 | 63.405 | 14.821 | −27.466 | 1.00 | 33.54 | N |
| ATOM | 4181 | CA | ALA | E | 181 | 63.037 | 14.459 | −28.823 | 1.00 | 34.81 | C |
| ATOM | 4182 | C | ALA | E | 181 | 63.051 | 15.604 | −29.836 | 1.00 | 36.17 | C |
| ATOM | 4183 | O | ALA | E | 181 | 62.969 | 16.777 | −29.476 | 1.00 | 35.97 | O |
| ATOM | 4184 | CB | ALA | E | 181 | 61.662 | 13.803 | −28.806 | 1.00 | 33.94 | C |
| ATOM | 4185 | N | GLY | E | 182 | 63.149 | 15.228 | −31.109 | 1.00 | 37.42 | N |
| ATOM | 4186 | CA | GLY | E | 182 | 63.141 | 16.184 | −32.203 | 1.00 | 38.05 | C |
| ATOM | 4187 | C | GLY | E | 182 | 62.107 | 15.728 | −33.215 | 1.00 | 38.82 | C |
| ATOM | 4188 | O | GLY | E | 182 | 61.548 | 14.634 | −33.076 | 1.00 | 38.84 | O |
| ATOM | 4189 | N | GLY | E | 183 | 61.850 | 16.548 | −34.232 | 1.00 | 39.61 | N |
| ATOM | 4190 | CA | GLY | E | 183 | 60.873 | 16.194 | −35.248 | 1.00 | 39.37 | C |
| ATOM | 4191 | C | GLY | E | 183 | 60.209 | 17.403 | −35.886 | 1.00 | 40.34 | C |
| ATOM | 4192 | O | GLY | E | 183 | 60.126 | 18.472 | −35.276 | 1.00 | 39.97 | O |
| ATOM | 4193 | N | ASN | E | 184 | 59.735 | 17.239 | −37.118 | 1.00 | 40.45 | N |
| ATOM | 4194 | CA | ASN | E | 184 | 59.068 | 18.322 | −37.835 | 1.00 | 41.60 | C |
| ATOM | 4195 | C | ASN | E | 184 | 57.875 | 17.793 | −38.627 | 1.00 | 41.71 | C |
| ATOM | 4196 | O | ASN | E | 184 | 58.038 | 17.046 | −39.586 | 1.00 | 42.15 | O |
| ATOM | 4197 | CB | ASN | E | 184 | 60.054 | 19.020 | −38.781 | 1.00 | 41.57 | C |
| ATOM | 4198 | N | PRO | E | 185 | 56.657 | 18.206 | −38.258 | 1.00 | 42.39 | N |
| ATOM | 4199 | CA | PRO | E | 185 | 56.348 | 19.132 | −37.163 | 1.00 | 42.99 | C |
| ATOM | 4200 | C | PRO | E | 185 | 56.699 | 18.635 | −35.758 | 1.00 | 44.39 | C |
| ATOM | 4201 | O | PRO | E | 185 | 56.941 | 17.441 | −35.541 | 1.00 | 44.92 | O |
| ATOM | 4202 | CB | PRO | E | 185 | 54.850 | 19.384 | −37.343 | 1.00 | 42.48 | C |
| ATOM | 4203 | CG | PRO | E | 185 | 54.355 | 18.108 | −37.914 | 1.00 | 42.87 | C |
| ATOM | 4204 | CD | PRO | E | 185 | 55.424 | 17.771 | −38.938 | 1.00 | 42.74 | C |
| ATOM | 4205 | N | MET | E | 186 | 56.733 | 19.572 | −34.810 | 1.00 | 44.67 | N |
| ATOM | 4206 | CA | MET | E | 186 | 57.044 | 19.276 | −33.412 | 1.00 | 44.59 | C |
| ATOM | 4207 | C | MET | E | 186 | 56.137 | 18.167 | −32.883 | 1.00 | 43.62 | C |
| ATOM | 4208 | O | MET | E | 186 | 54.917 | 18.304 | −32.854 | 1.00 | 43.45 | O |
| ATOM | 4209 | CB | MET | E | 186 | 56.861 | 20.533 | −32.551 | 1.00 | 46.17 | C |
| ATOM | 4210 | CG | MET | E | 186 | 57.269 | 20.364 | −31.089 | 1.00 | 47.14 | C |
| ATOM | 4211 | SD | MET | E | 186 | 59.028 | 19.948 | −30.944 | 1.00 | 50.88 | S |
| ATOM | 4212 | CE | MET | E | 186 | 59.755 | 21.534 | −30.489 | 1.00 | 49.96 | C |
| ATOM | 4213 | N | PRO | E | 187 | 56.731 | 17.052 | −32.444 | 1.00 | 42.84 | N |
| ATOM | 4214 | CA | PRO | E | 187 | 55.937 | 15.936 | −31.925 | 1.00 | 42.11 | C |
| ATOM | 4215 | C | PRO | E | 187 | 55.327 | 16.199 | −30.551 | 1.00 | 41.39 | C |
| ATOM | 4216 | O | PRO | E | 187 | 55.850 | 16.997 | −29.771 | 1.00 | 40.66 | O |
| ATOM | 4217 | CB | PRO | E | 187 | 56.945 | 14.789 | −31.897 | 1.00 | 42.56 | C |
| ATOM | 4218 | CG | PRO | E | 187 | 58.229 | 15.478 | −31.584 | 1.00 | 42.73 | C |
| ATOM | 4219 | CD | PRO | E | 187 | 58.172 | 16.736 | −32.434 | 1.00 | 42.58 | C |
| ATOM | 4220 | N | THR | E | 188 | 54.213 | 15.533 | −30.261 | 1.00 | 40.80 | N |
| ATOM | 4221 | CA | THR | E | 188 | 53.570 | 15.694 | −28.967 | 1.00 | 40.77 | C |
| ATOM | 4222 | C | THR | E | 188 | 54.119 | 14.622 | −28.039 | 1.00 | 40.73 | C |
| ATOM | 4223 | O | THR | E | 188 | 54.756 | 13.660 | −28.476 | 1.00 | 40.10 | O |
| ATOM | 4224 | CB | THR | E | 188 | 52.042 | 15.522 | −29.027 | 1.00 | 40.84 | C |
| ATOM | 4225 | OG1 | THR | E | 188 | 51.728 | 14.136 | −29.201 | 1.00 | 41.02 | O |
| ATOM | 4226 | CG2 | THR | E | 188 | 51.453 | 16.330 | −30.169 | 1.00 | 40.27 | C |
| ATOM | 4227 | N | MET | E | 189 | 53.867 | 14.791 | −26.751 | 1.00 | 40.54 | N |
| ATOM | 4228 | CA | MET | E | 189 | 54.345 | 13.841 | −25.764 | 1.00 | 41.01 | C |
| ATOM | 4229 | C | MET | E | 189 | 53.263 | 13.438 | −24.781 | 1.00 | 39.45 | C |
| ATOM | 4230 | O | MET | E | 189 | 52.493 | 14.278 | −24.318 | 1.00 | 38.97 | O |
| ATOM | 4231 | CB | MET | E | 189 | 55.523 | 14.432 | −24.982 | 1.00 | 42.49 | C |
| ATOM | 4232 | CG | MET | E | 189 | 55.951 | 13.576 | −23.791 | 1.00 | 45.02 | C |
| ATOM | 4233 | SD | MET | E | 189 | 57.378 | 14.250 | −22.910 | 1.00 | 48.98 | S |
| ATOM | 4234 | CE | MET | E | 189 | 58.674 | 13.084 | −23.501 | 1.00 | 48.53 | C |
| ATOM | 4235 | N | ARG | E | 190 | 53.222 | 12.146 | −24.466 | 1.00 | 37.91 | N |
| ATOM | 4236 | CA | ARG | E | 190 | 52.264 | 11.603 | −23.509 | 1.00 | 36.69 | C |
| ATOM | 4237 | C | ARG | E | 190 | 53.002 | 10.599 | −22.625 | 1.00 | 34.83 | C |
| ATOM | 4238 | O | ARG | E | 190 | 53.896 | 9.891 | −23.103 | 1.00 | 33.14 | O |
| ATOM | 4239 | CB | ARG | E | 190 | 51.122 | 10.875 | −24.220 | 1.00 | 38.19 | C |
| ATOM | 4240 | CG | ARG | E | 190 | 50.527 | 11.607 | −25.410 | 1.00 | 41.65 | C |
| ATOM | 4241 | CD | ARG | E | 190 | 49.163 | 11.021 | −25.794 | 1.00 | 43.46 | C |
| ATOM | 4242 | NE | ARG | E | 190 | 49.161 | 9.560 | −25.891 | 1.00 | 44.29 | N |
| ATOM | 4243 | CZ | ARG | E | 190 | 49.719 | 8.866 | −26.878 | 1.00 | 45.19 | C |
| ATOM | 4244 | NH1 | ARG | E | 190 | 50.338 | 9.495 | −27.873 | 1.00 | 46.13 | N |
| ATOM | 4245 | NH2 | ARG | E | 190 | 49.653 | 7.540 | −26.874 | 1.00 | 44.60 | N |
| ATOM | 4246 | N | TRP | E | 191 | 52.639 | 10.539 | −21.343 | 1.00 | 31.83 | N |
| ATOM | 4247 | CA | TRP | E | 191 | 53.269 | 9.586 | −20.431 | 1.00 | 31.00 | C |
| ATOM | 4248 | C | TRP | E | 191 | 52.268 | 8.540 | −19.908 | 1.00 | 30.76 | C |
| ATOM | 4249 | O | TRP | E | 191 | 51.138 | 8.867 | −19.536 | 1.00 | 30.52 | O |
| ATOM | 4250 | CB | TRP | E | 191 | 53.937 | 10.301 | −19.246 | 1.00 | 29.62 | C |
| ATOM | 4251 | CG | TRP | E | 191 | 55.187 | 11.072 | −19.603 | 1.00 | 28.95 | C |
| ATOM | 4252 | CD1 | TRP | E | 191 | 55.259 | 12.337 | −20.128 | 1.00 | 29.00 | C |
| ATOM | 4253 | CD2 | TRP | E | 191 | 56.540 | 10.612 | −19.487 | 1.00 | 28.32 | C |

TABLE 3-continued

FGFR2(D2–D3) Complexed with FGF2

| ATOM | 4254 | NE1 | TRP | E | 191 | 56.572 | 12.688 | −20.344 | 1.00 | 28.22 | N |
|---|---|---|---|---|---|---|---|---|---|---|---|
| ATOM | 4255 | CE2 | TRP | E | 191 | 57.378 | 11.649 | −19.960 | 1.00 | 28.76 | C |
| ATOM | 4256 | CE3 | TRP | E | 191 | 57.125 | 9.423 | −19.030 | 1.00 | 29.22 | C |
| ATOM | 4257 | CZ2 | TRP | E | 191 | 58.775 | 11.533 | −19.985 | 1.00 | 29.04 | C |
| ATOM | 4258 | CZ3 | TRP | E | 191 | 58.520 | 9.306 | −19.060 | 1.00 | 30.17 | C |
| ATOM | 4259 | CH2 | TRP | E | 191 | 59.326 | 10.359 | −19.534 | 1.00 | 29.04 | C |
| ATOM | 4260 | N | LEU | E | 192 | 52.687 | 7.280 | −19.905 | 1.00 | 29.28 | N |
| ATOM | 4261 | CA | LEU | E | 192 | 51.840 | 6.197 | −19.421 | 1.00 | 29.58 | C |
| ATOM | 4262 | C | LEU | E | 192 | 52.428 | 5.583 | −18.143 | 1.00 | 29.57 | C |
| ATOM | 4263 | O | LEU | E | 192 | 53.645 | 5.571 | −17.958 | 1.00 | 30.74 | O |
| ATOM | 4264 | CB | LEU | E | 192 | 51.721 | 5.084 | −20.477 | 1.00 | 28.80 | C |
| ATOM | 4265 | CG | LEU | E | 192 | 51.382 | 5.339 | −21.958 | 1.00 | 30.27 | C |
| ATOM | 4266 | CD1 | LEU | E | 192 | 51.448 | 4.015 | −22.708 | 1.00 | 31.01 | C |
| ATOM | 4267 | CD2 | LEU | E | 192 | 49.998 | 5.950 | −22.115 | 1.00 | 29.80 | C |
| ATOM | 4268 | N | LYS | E | 193 | 51.559 | 5.097 | −17.260 | 1.00 | 28.96 | N |
| ATOM | 4269 | CA | LYS | E | 193 | 51.986 | 4.412 | −16.051 | 1.00 | 28.34 | C |
| ATOM | 4270 | C | LYS | E | 193 | 51.466 | 2.983 | −16.225 | 1.00 | 29.18 | C |
| ATOM | 4271 | O | LYS | E | 193 | 50.257 | 2.763 | −16.362 | 1.00 | 27.91 | O |
| ATOM | 4272 | CB | LYS | E | 193 | 51.371 | 5.023 | −14.794 | 1.00 | 27.85 | C |
| ATOM | 4273 | CG | LYS | E | 193 | 51.762 | 4.267 | −13.506 | 1.00 | 28.13 | C |
| ATOM | 4274 | CD | LYS | E | 193 | 51.139 | 4.882 | −12.254 | 1.00 | 29.87 | C |
| ATOM | 4275 | CE | LYS | E | 193 | 51.541 | 4.112 | −10.999 | 1.00 | 30.30 | C |
| ATOM | 4276 | NZ | LYS | E | 193 | 50.798 | 4.559 | −9.789 | 1.00 | 28.18 | N |
| ATOM | 4277 | N | ASN | E | 194 | 52.376 | 2.013 | −16.230 | 1.00 | 28.65 | N |
| ATOM | 4278 | CA | ASN | E | 194 | 51.990 | 0.620 | −16.417 | 1.00 | 29.49 | C |
| ATOM | 4279 | C | ASN | E | 194 | 51.132 | 0.450 | −17.682 | 1.00 | 30.66 | C |
| ATOM | 4280 | O | ASN | E | 194 | 50.069 | −0.168 | −17.642 | 1.00 | 30.92 | O |
| ATOM | 4281 | CB | ASN | E | 194 | 51.215 | 0.099 | −15.195 | 1.00 | 27.12 | C |
| ATOM | 4282 | CG | ASN | E | 194 | 52.064 | 0.051 | −13.934 | 1.00 | 27.31 | C |
| ATOM | 4283 | OD1 | ASN | E | 194 | 53.271 | −0.233 | −13.987 | 1.00 | 25.63 | O |
| ATOM | 4284 | ND2 | ASN | E | 194 | 51.433 | 0.310 | −12.783 | 1.00 | 24.35 | N |
| ATOM | 4285 | N | GLY | E | 195 | 51.595 | 1.022 | −18.792 | 1.00 | 31.66 | N |
| ATOM | 4286 | CA | GLY | E | 195 | 50.886 | 0.919 | −20.060 | 1.00 | 32.64 | C |
| ATOM | 4287 | C | GLY | E | 195 | 49.528 | 1.601 | −20.206 | 1.00 | 33.77 | C |
| ATOM | 4288 | O | GLY | E | 195 | 48.838 | 1.357 | −21.191 | 1.00 | 33.63 | O |
| ATOM | 4289 | N | LYS | E | 196 | 49.137 | 2.440 | −19.247 | 1.00 | 34.77 | N |
| ATOM | 4290 | CA | LYS | E | 196 | 47.845 | 3.132 | −19.314 | 1.00 | 36.07 | C |
| ATOM | 4291 | C | LYS | E | 196 | 48.029 | 4.615 | −19.042 | 1.00 | 35.87 | C |
| ATOM | 4292 | O | LYS | E | 196 | 49.003 | 5.011 | −18.405 | 1.00 | 35.40 | O |
| ATOM | 4293 | CB | LYS | E | 196 | 46.871 | 2.599 | −18.258 | 1.00 | 37.29 | C |
| ATOM | 4294 | CG | LYS | E | 196 | 47.072 | 1.156 | −17.820 | 1.00 | 40.01 | C |
| ATOM | 4295 | CD | LYS | E | 196 | 46.543 | 1.000 | −16.393 | 1.00 | 42.51 | C |
| ATOM | 4296 | CE | LYS | E | 196 | 47.036 | −0.269 | −15.718 | 1.00 | 43.43 | C |
| ATOM | 4297 | NZ | LYS | E | 196 | 46.738 | −0.231 | −14.254 | 1.00 | 44.06 | N |
| ATOM | 4298 | N | GLU | E | 197 | 47.082 | 5.429 | −19.504 | 1.00 | 36.09 | N |
| ATOM | 4299 | CA | GLU | E | 197 | 47.142 | 6.867 | −19.275 | 1.00 | 35.90 | C |
| ATOM | 4300 | C | GLU | E | 197 | 47.445 | 7.136 | −17.802 | 1.00 | 34.76 | C |
| ATOM | 4301 | O | GLU | E | 197 | 46.858 | 6.521 | −16.915 | 1.00 | 34.16 | O |
| ATOM | 4302 | CB | GLU | E | 197 | 45.815 | 7.533 | −19.672 | 1.00 | 37.72 | C |
| ATOM | 4303 | CG | GLU | E | 197 | 45.694 | 9.008 | −19.247 | 1.00 | 39.18 | C |
| ATOM | 4304 | CD | GLU | E | 197 | 44.430 | 9.698 | −19.778 | 1.00 | 41.13 | C |
| ATOM | 4305 | OE1 | GLU | E | 197 | 43.397 | 9.016 | −19.985 | 1.00 | 40.19 | O |
| ATOM | 4306 | OE2 | GLU | E | 197 | 44.470 | 10.933 | −19.969 | 1.00 | 40.93 | O |
| ATOM | 4307 | N | PHE | E | 198 | 48.384 | 8.046 | −17.564 | 1.00 | 34.33 | N |
| ATOM | 4308 | CA | PHE | E | 198 | 48.805 | 8.427 | −16.223 | 1.00 | 33.43 | C |
| ATOM | 4309 | C | PHE | E | 198 | 48.051 | 9.719 | −15.917 | 1.00 | 34.28 | C |
| ATOM | 4310 | O | PHE | E | 198 | 48.245 | 10.725 | −16.596 | 1.00 | 33.79 | O |
| ATOM | 4311 | CB | PHE | E | 198 | 50.321 | 8.669 | −16.229 | 1.00 | 31.88 | C |
| ATOM | 4312 | CG | PHE | E | 198 | 50.939 | 8.873 | −14.861 | 1.00 | 29.49 | C |
| ATOM | 4313 | CD1 | PHE | E | 198 | 52.201 | 9.455 | −14.750 | 1.00 | 28.38 | C |
| ATOM | 4314 | CD2 | PHE | E | 198 | 50.293 | 8.461 | −13.702 | 1.00 | 28.64 | C |
| ATOM | 4315 | CE1 | PHE | E | 198 | 52.816 | 9.625 | −13.494 | 1.00 | 27.94 | C |
| ATOM | 4316 | CE2 | PHE | E | 198 | 50.901 | 8.625 | −12.442 | 1.00 | 29.18 | C |
| ATOM | 4317 | CZ | PHE | E | 198 | 52.166 | 9.209 | −12.345 | 1.00 | 26.63 | C |
| ATOM | 4318 | N | LYS | E | 199 | 47.190 | 9.680 | −14.903 | 1.00 | 35.47 | N |
| ATOM | 4319 | CA | LYS | E | 199 | 46.383 | 10.841 | −14.515 | 1.00 | 36.46 | C |
| ATOM | 4320 | C | LYS | E | 199 | 46.855 | 11.457 | −13.209 | 1.00 | 36.29 | C |
| ATOM | 4321 | O | LYS | E | 199 | 47.434 | 10.772 | −12.368 | 1.00 | 35.86 | O |
| ATOM | 4322 | CB | LYS | E | 199 | 44.920 | 10.436 | −14.345 | 1.00 | 37.45 | C |
| ATOM | 4323 | CG | LYS | E | 199 | 44.182 | 10.086 | −15.625 | 1.00 | 39.26 | C |
| ATOM | 4324 | CD | LYS | E | 199 | 42.923 | 9.300 | −15.288 | 1.00 | 40.34 | C |
| ATOM | 4325 | CE | LYS | E | 199 | 41.879 | 9.432 | −16.383 | 1.00 | 42.06 | C |
| ATOM | 4326 | NZ | LYS | E | 199 | 42.480 | 9.246 | −17.726 | 1.00 | 42.43 | N |
| ATOM | 4327 | N | GLN | E | 200 | 46.572 | 12.746 | −13.035 | 1.00 | 35.97 | N |
| ATOM | 4328 | CA | GLN | E | 200 | 46.957 | 13.464 | −11.830 | 1.00 | 36.14 | C |
| ATOM | 4329 | C | GLN | E | 200 | 46.466 | 12.783 | −10.555 | 1.00 | 36.13 | C |
| ATOM | 4330 | O | GLN | E | 200 | 47.177 | 12.746 | −9.558 | 1.00 | 36.15 | O |

TABLE 3-continued

FGFR2(D2–D3) Complexed with FGF2

| ATOM | 4331 | CB | GLN | E | 200 | 46.428 | 14.905 | −11.881 | 1.00 | 35.07 | C |
|---|---|---|---|---|---|---|---|---|---|---|---|
| ATOM | 4332 | CG | GLN | E | 200 | 47.097 | 15.794 | −12.922 | 1.00 | 32.75 | C |
| ATOM | 4333 | CD | GLN | E | 200 | 48.565 | 16.049 | −12.629 | 1.00 | 31.75 | C |
| ATOM | 4334 | OE1 | GLN | E | 200 | 48.980 | 16.095 | −11.472 | 1.00 | 31.98 | O |
| ATOM | 4335 | NE2 | GLN | E | 200 | 49.352 | 16.238 | −13.677 | 1.00 | 31.84 | N |
| ATOM | 4336 | N | GLU | E | 201 | 45.260 | 12.228 | −10.590 | 1.00 | 36.20 | N |
| ATOM | 4337 | CA | GLU | E | 201 | 44.697 | 11.579 | −9.410 | 1.00 | 36.53 | C |
| ATOM | 4338 | C | GLU | E | 201 | 45.307 | 10.212 | −9.105 | 1.00 | 35.82 | C |
| ATOM | 4339 | O | GLU | E | 201 | 44.946 | 9.582 | −8.113 | 1.00 | 34.99 | O |
| ATOM | 4340 | CB | GLU | E | 201 | 43.183 | 11.421 | −9.569 | 1.00 | 37.47 | C |
| ATOM | 4341 | CG | GLU | E | 201 | 42.799 | 10.440 | −10.651 | 1.00 | 40.87 | C |
| ATOM | 4342 | CD | GLU | E | 201 | 42.124 | 11.104 | −11.834 | 1.00 | 43.50 | C |
| ATOM | 4343 | OE1 | GLU | E | 201 | 42.719 | 12.037 | −12.439 | 1.00 | 43.56 | O |
| ATOM | 4344 | OE2 | GLU | E | 201 | 40.990 | 10.681 | −12.154 | 1.00 | 44.02 | O |
| ATOM | 4345 | N | HIS | E | 202 | 46.216 | 9.746 | −9.957 | 1.00 | 35.29 | N |
| ATOM | 4346 | CA | HIS | E | 202 | 46.847 | 8.444 | −9.740 | 1.00 | 34.98 | C |
| ATOM | 4347 | C | HIS | E | 202 | 47.852 | 8.397 | −8.572 | 1.00 | 34.41 | C |
| ATOM | 4348 | O | HIS | E | 202 | 48.291 | 7.313 | −8.187 | 1.00 | 35.13 | O |
| ATOM | 4349 | CB | HIS | E | 202 | 47.514 | 7.940 | −11.029 | 1.00 | 34.01 | C |
| ATOM | 4350 | CG | HIS | E | 202 | 46.547 | 7.437 | −12.059 | 1.00 | 35.20 | C |
| ATOM | 4351 | ND1 | HIS | E | 202 | 45.353 | 6.825 | −11.729 | 1.00 | 35.20 | N |
| ATOM | 4352 | CD2 | HIS | E | 202 | 46.611 | 7.424 | −13.413 | 1.00 | 34.39 | C |
| ATOM | 4353 | CE1 | HIS | E | 202 | 44.725 | 6.462 | −12.833 | 1.00 | 33.57 | C |
| ATOM | 4354 | NE2 | HIS | E | 202 | 45.468 | 6.813 | −13.869 | 1.00 | 34.45 | N |
| ATOM | 4355 | N | ARG | E | 203 | 48.216 | 9.556 | −8.018 | 1.00 | 33.22 | N |
| ATOM | 4356 | CA | ARG | E | 203 | 49.130 | 9.613 | −6.867 | 1.00 | 32.51 | C |
| ATOM | 4357 | C | ARG | E | 203 | 48.912 | 10.907 | −6.080 | 1.00 | 32.39 | C |
| ATOM | 4358 | O | ARG | E | 203 | 48.459 | 11.906 | −6.635 | 1.00 | 31.51 | O |
| ATOM | 4359 | CB | ARG | E | 203 | 50.605 | 9.523 | −7.309 | 1.00 | 30.32 | C |
| ATOM | 4360 | CG | ARG | E | 203 | 51.174 | 10.814 | −7.895 | 1.00 | 29.22 | C |
| ATOM | 4361 | CD | ARG | E | 203 | 52.563 | 10.591 | −8.502 | 1.00 | 29.55 | C |
| ATOM | 4362 | NE | ARG | E | 203 | 53.557 | 10.178 | −7.508 | 1.00 | 28.00 | N |
| ATOM | 4363 | CZ | ARG | E | 203 | 54.259 | 11.013 | −6.749 | 1.00 | 26.43 | C |
| ATOM | 4364 | NH1 | ARG | E | 203 | 54.093 | 12.323 | −6.859 | 1.00 | 25.80 | N |
| ATOM | 4365 | NH2 | ARG | E | 203 | 55.117 | 10.536 | −5.860 | 1.00 | 27.50 | N |
| ATOM | 4366 | N | ILE | E | 204 | 49.215 | 10.880 | −4.787 | 1.00 | 32.99 | N |
| ATOM | 4367 | CA | ILE | E | 204 | 49.061 | 12.069 | −3.964 | 1.00 | 34.24 | C |
| ATOM | 4368 | C | ILE | E | 204 | 49.946 | 13.162 | −4.559 | 1.00 | 34.70 | C |
| ATOM | 4369 | O | ILE | E | 204 | 51.125 | 12.928 | −4.851 | 1.00 | 34.35 | O |
| ATOM | 4370 | CB | ILE | E | 204 | 49.496 | 11.810 | −2.503 | 1.00 | 35.02 | C |
| ATOM | 4371 | CG1 | ILE | E | 204 | 48.705 | 10.633 | −1.918 | 1.00 | 35.18 | C |
| ATOM | 4372 | CG2 | ILE | E | 204 | 49.296 | 13.083 | −1.664 | 1.00 | 36.10 | C |
| ATOM | 4373 | CD1 | ILE | E | 204 | 47.206 | 10.812 | −1.957 | 1.00 | 34.74 | C |
| ATOM | 4374 | N | GLY | E | 205 | 49.364 | 14.341 | −4.769 | 1.00 | 34.34 | N |
| ATOM | 4375 | CA | GLY | E | 205 | 50.115 | 15.454 | −5.327 | 1.00 | 34.71 | C |
| ATOM | 4376 | C | GLY | E | 205 | 50.338 | 15.406 | −6.832 | 1.00 | 34.80 | C |
| ATOM | 4377 | O | GLY | E | 205 | 50.963 | 16.308 | −7.397 | 1.00 | 35.12 | O |
| ATOM | 4378 | N | GLY | E | 206 | 49.840 | 14.362 | −7.490 | 1.00 | 33.63 | N |
| ATOM | 4379 | CA | GLY | E | 206 | 50.007 | 14.255 | −8.932 | 1.00 | 33.94 | C |
| ATOM | 4380 | C | GLY | E | 206 | 51.436 | 14.357 | −9.462 | 1.00 | 33.65 | C |
| ATOM | 4381 | O | GLY | E | 206 | 52.390 | 13.927 | −8.815 | 1.00 | 32.95 | O |
| ATOM | 4382 | N | TYR | E | 207 | 51.586 | 14.924 | −10.651 | 1.00 | 33.53 | N |
| ATOM | 4383 | CA | TYR | E | 207 | 52.904 | 15.080 | −11.239 | 1.00 | 34.03 | C |
| ATOM | 4384 | C | TYR | E | 207 | 52.992 | 16.344 | −12.079 | 1.00 | 34.49 | C |
| ATOM | 4385 | O | TYR | E | 207 | 51.989 | 17.036 | −12.283 | 1.00 | 34.71 | O |
| ATOM | 4386 | CB | TYR | E | 207 | 53.257 | 13.860 | −12.105 | 1.00 | 34.68 | C |
| ATOM | 4387 | CG | TYR | E | 207 | 52.320 | 13.631 | −13.271 | 1.00 | 34.71 | C |
| ATOM | 4388 | CD1 | TYR | E | 207 | 51.186 | 12.827 | −13.133 | 1.00 | 34.16 | C |
| ATOM | 4389 | CD2 | TYR | E | 207 | 52.557 | 14.237 | −14.508 | 1.00 | 34.98 | C |
| ATOM | 4390 | CE1 | TYR | E | 207 | 50.304 | 12.630 | −14.201 | 1.00 | 35.89 | C |
| ATOM | 4391 | CE2 | TYR | E | 207 | 51.673 | 14.049 | −15.592 | 1.00 | 35.73 | C |
| ATOM | 4392 | CZ | TYR | E | 207 | 50.551 | 13.248 | −15.424 | 1.00 | 35.64 | C |
| ATOM | 4393 | OH | TYR | E | 207 | 49.660 | 13.090 | −16.458 | 1.00 | 36.29 | O |
| ATOM | 4394 | N | LYS | E | 208 | 54.196 | 16.637 | −12.566 | 1.00 | 34.28 | N |
| ATOM | 4395 | CA | LYS | E | 208 | 54.440 | 17.814 | −13.391 | 1.00 | 35.05 | C |
| ATOM | 4396 | C | LYS | E | 208 | 55.157 | 17.431 | −14.677 | 1.00 | 37.11 | C |
| ATOM | 4397 | O | LYS | E | 208 | 55.993 | 16.526 | −14.690 | 1.00 | 36.91 | O |
| ATOM | 4398 | CB | LYS | E | 208 | 55.298 | 18.837 | −12.635 | 1.00 | 34.30 | C |
| ATOM | 4399 | CG | LYS | E | 208 | 54.680 | 19.377 | −11.362 | 1.00 | 33.60 | C |
| ATOM | 4400 | CD | LYS | E | 208 | 55.696 | 20.177 | −10.562 | 1.00 | 32.63 | C |
| ATOM | 4401 | CE | LYS | E | 208 | 55.100 | 20.639 | −9.241 | 1.00 | 32.80 | C |
| ATOM | 4402 | NZ | LYS | E | 208 | 56.080 | 21.379 | −8.404 | 1.00 | 32.69 | N |
| ATOM | 4403 | N | VAL | E | 209 | 54.824 | 18.119 | −15.761 | 1.00 | 38.97 | N |
| ATOM | 4404 | CA | VAL | E | 209 | 55.449 | 17.860 | −17.047 | 1.00 | 41.04 | C |
| ATOM | 4405 | C | VAL | E | 209 | 55.932 | 19.162 | −17.671 | 1.00 | 42.95 | C |
| ATOM | 4406 | O | VAL | E | 209 | 55.197 | 20.151 | −17.727 | 1.00 | 44.04 | O |
| ATOM | 4407 | CB | VAL | E | 209 | 54.476 | 17.152 | −18.026 | 1.00 | 40.56 | C |

TABLE 3-continued

FGFR2(D2–D3) Complexed with FGF2

| ATOM | 4408 | CG1 | VAL | E | 209 | 55.001 | 17.246 | −19.444 | 1.00 | 41.33 | C |
|---|---|---|---|---|---|---|---|---|---|---|---|
| ATOM | 4409 | CG2 | VAL | E | 209 | 54.320 | 15.689 | −17.637 | 1.00 | 39.57 | C |
| ATOM | 4410 | N | ARG | E | 210 | 57.182 | 19.158 | −18.118 | 1.00 | 44.27 | N |
| ATOM | 4411 | CA | ARG | E | 210 | 57.776 | 20.323 | −18.760 | 1.00 | 45.71 | C |
| ATOM | 4412 | C | ARG | E | 210 | 58.059 | 19.952 | −20.219 | 1.00 | 46.45 | C |
| ATOM | 4413 | O | ARG | E | 210 | 59.105 | 19.382 | −20.533 | 1.00 | 46.98 | O |
| ATOM | 4414 | CB | ARG | E | 210 | 59.073 | 20.718 | −18.047 | 1.00 | 45.37 | C |
| ATOM | 4415 | N | ASN | E | 211 | 57.114 | 20.266 | −21.103 | 1.00 | 47.44 | N |
| ATOM | 4416 | CA | ASN | E | 211 | 57.246 | 19.959 | −22.526 | 1.00 | 47.92 | C |
| ATOM | 4417 | C | ASN | E | 211 | 58.580 | 20.424 | −23.107 | 1.00 | 47.84 | C |
| ATOM | 4418 | O | ASN | E | 211 | 59.194 | 19.721 | −23.911 | 1.00 | 47.98 | O |
| ATOM | 4419 | CB | ASN | E | 211 | 56.093 | 20.588 | −23.313 | 1.00 | 47.89 | C |
| ATOM | 4420 | N | GLN | E | 212 | 59.028 | 21.605 | −22.693 | 1.00 | 47.52 | N |
| ATOM | 4421 | CA | GLN | E | 212 | 60.295 | 22.159 | −23.175 | 1.00 | 47.00 | C |
| ATOM | 4422 | C | GLN | E | 212 | 61.479 | 21.228 | −22.886 | 1.00 | 46.08 | C |
| ATOM | 4423 | O | GLN | E | 212 | 62.469 | 21.233 | −23.618 | 1.00 | 46.55 | O |
| ATOM | 4424 | CB | GLN | E | 212 | 60.552 | 23.534 | −22.540 | 1.00 | 46.95 | C |
| ATOM | 4425 | N | HIS | E | 213 | 61.380 | 20.429 | −21.826 | 1.00 | 44.00 | N |
| ATOM | 4426 | CA | HIS | E | 213 | 62.457 | 19.503 | −21.477 | 1.00 | 42.28 | C |
| ATOM | 4427 | C | HIS | E | 213 | 62.090 | 18.030 | −21.713 | 1.00 | 40.55 | C |
| ATOM | 4428 | O | HIS | E | 213 | 62.875 | 17.141 | −21.391 | 1.00 | 39.90 | O |
| ATOM | 4429 | CB | HIS | E | 213 | 62.862 | 19.694 | −20.010 | 1.00 | 42.11 | C |
| ATOM | 4430 | N | TRP | E | 214 | 60.907 | 17.783 | −22.277 | 1.00 | 38.70 | N |
| ATOM | 4431 | CA | TRP | E | 214 | 60.435 | 16.417 | −22.541 | 1.00 | 36.92 | C |
| ATOM | 4432 | C | TRP | E | 214 | 60.559 | 15.583 | −21.270 | 1.00 | 35.61 | C |
| ATOM | 4433 | O | TRP | E | 214 | 61.058 | 14.456 | −21.298 | 1.00 | 34.98 | O |
| ATOM | 4434 | CB | TRP | E | 214 | 61.273 | 15.768 | −23.653 | 1.00 | 36.91 | C |
| ATOM | 4435 | CG | TRP | E | 214 | 61.368 | 16.612 | −24.879 | 1.00 | 37.66 | C |
| ATOM | 4436 | CD1 | TRP | E | 214 | 62.336 | 17.538 | −25.172 | 1.00 | 37.83 | C |
| ATOM | 4437 | CD2 | TRP | E | 214 | 60.411 | 16.683 | −25.940 | 1.00 | 37.72 | C |
| ATOM | 4438 | NE1 | TRP | E | 214 | 62.032 | 18.184 | −26.347 | 1.00 | 37.30 | N |
| ATOM | 4439 | CE2 | TRP | E | 214 | 60.856 | 17.679 | −26.839 | 1.00 | 37.75 | C |
| ATOM | 4440 | CE3 | TRP | E | 214 | 59.215 | 16.003 | −26.219 | 1.00 | 37.31 | C |
| ATOM | 4441 | CZ2 | TRP | E | 214 | 60.149 | 18.012 | −27.997 | 1.00 | 37.75 | C |
| ATOM | 4442 | CZ3 | TRP | E | 214 | 58.513 | 16.333 | −27.370 | 1.00 | 37.71 | C |
| ATOM | 4443 | CH2 | TRP | E | 214 | 58.982 | 17.329 | −28.245 | 1.00 | 37.98 | C |
| ATOM | 4444 | N | SER | E | 215 | 60.090 | 16.125 | −20.154 | 1.00 | 33.93 | N |
| ATOM | 4445 | CA | SER | E | 215 | 60.230 | 15.427 | −18.885 | 1.00 | 32.72 | C |
| ATOM | 4446 | C | SER | E | 215 | 58.961 | 15.219 | −18.060 | 1.00 | 31.96 | C |
| ATOM | 4447 | O | SER | E | 215 | 57.983 | 15.968 | −18.180 | 1.00 | 31.78 | O |
| ATOM | 4448 | CB | SER | E | 215 | 61.244 | 16.180 | −18.034 | 1.00 | 32.88 | C |
| ATOM | 4449 | OG | SER | E | 215 | 60.780 | 17.503 | −17.814 | 1.00 | 32.58 | O |
| ATOM | 4450 | N | LEU | E | 216 | 59.020 | 14.200 | −17.206 | 1.00 | 30.06 | N |
| ATOM | 4451 | CA | LEU | E | 216 | 57.942 | 13.847 | −16.281 | 1.00 | 29.24 | C |
| ATOM | 4452 | C | LEU | E | 216 | 58.569 | 13.946 | −14.896 | 1.00 | 28.06 | C |
| ATOM | 4453 | O | LEU | E | 216 | 59.607 | 13.333 | −14.643 | 1.00 | 27.98 | O |
| ATOM | 4454 | CB | LEU | E | 216 | 57.464 | 12.408 | −16.511 | 1.00 | 28.20 | C |
| ATOM | 4455 | CG | LEU | E | 216 | 56.584 | 11.871 | −15.375 | 1.00 | 28.64 | C |
| ATOM | 4456 | CD1 | LEU | E | 216 | 55.273 | 12.639 | −15.364 | 1.00 | 28.75 | C |
| ATOM | 4457 | CD2 | LEU | E | 216 | 56.321 | 10.378 | −15.553 | 1.00 | 28.80 | C |
| ATOM | 4458 | N | ILE | E | 217 | 57.940 | 14.700 | −14.004 | 1.00 | 27.85 | N |
| ATOM | 4459 | CA | ILE | E | 217 | 58.445 | 14.903 | −12.648 | 1.00 | 27.94 | C |
| ATOM | 4460 | C | ILE | E | 217 | 57.496 | 14.452 | −11.543 | 1.00 | 28.38 | C |
| ATOM | 4461 | O | ILE | E | 217 | 56.320 | 14.838 | −11.532 | 1.00 | 27.95 | O |
| ATOM | 4462 | CB | ILE | E | 217 | 58.758 | 16.394 | −12.426 | 1.00 | 28.53 | C |
| ATOM | 4463 | CG1 | ILE | E | 217 | 59.912 | 16.804 | −13.343 | 1.00 | 29.98 | C |
| ATOM | 4464 | CG2 | ILE | E | 217 | 59.082 | 16.671 | −10.946 | 1.00 | 27.96 | C |
| ATOM | 4465 | CD1 | ILE | E | 217 | 60.168 | 18.306 | −13.386 | 1.00 | 31.27 | C |
| ATOM | 4466 | N | MET | E | 218 | 58.011 | 13.638 | −10.621 | 1.00 | 27.96 | N |
| ATOM | 4467 | CA | MET | E | 218 | 57.233 | 13.159 | −9.480 | 1.00 | 29.17 | C |
| ATOM | 4468 | C | MET | E | 218 | 58.005 | 13.504 | −8.198 | 1.00 | 29.88 | C |
| ATOM | 4469 | O | MET | E | 218 | 59.137 | 13.059 | −7.993 | 1.00 | 30.35 | O |
| ATOM | 4470 | CB | MET | E | 218 | 56.993 | 11.645 | −9.580 | 1.00 | 29.88 | C |
| ATOM | 4471 | CG | MET | E | 218 | 56.119 | 11.234 | −10.779 | 1.00 | 30.14 | C |
| ATOM | 4472 | SD | MET | E | 218 | 55.773 | 9.449 | −10.866 | 1.00 | 31.91 | S |
| ATOM | 4473 | CE | MET | E | 218 | 57.255 | 8.866 | −11.591 | 1.00 | 31.93 | C |
| ATOM | 4474 | N | GLU | E | 219 | 57.388 | 14.315 | −7.347 | 1.00 | 29.54 | N |
| ATOM | 4475 | CA | GLU | E | 219 | 58.007 | 14.744 | −6.097 | 1.00 | 29.59 | C |
| ATOM | 4476 | C | GLU | E | 219 | 57.629 | 13.851 | −4.917 | 1.00 | 29.81 | C |
| ATOM | 4477 | O | GLU | E | 219 | 56.560 | 13.242 | −4.915 | 1.00 | 29.98 | O |
| ATOM | 4478 | CB | GLU | E | 219 | 57.610 | 16.200 | −5.829 | 1.00 | 29.31 | C |
| ATOM | 4479 | CG | GLU | E | 219 | 58.021 | 17.135 | −6.972 | 1.00 | 29.10 | C |
| ATOM | 4480 | CD | GLU | E | 219 | 57.169 | 18.384 | −7.044 | 1.00 | 29.99 | C |
| ATOM | 4481 | OE1 | GLU | E | 219 | 55.943 | 18.253 | −6.868 | 1.00 | 28.69 | O |
| ATOM | 4482 | OE2 | GLU | E | 219 | 57.717 | 19.490 | −7.286 | 1.00 | 31.38 | O |
| ATOM | 4483 | N | SER | E | 220 | 58.528 | 13.764 | −3.935 | 1.00 | 29.65 | N |
| ATOM | 4484 | CA | SER | E | 220 | 58.333 | 12.967 | −2.723 | 1.00 | 30.35 | C |

TABLE 3-continued

FGFR2(D2–D3) Complexed with FGF2

| ATOM | 4485 | C | SER | E | 220 | 57.809 | 11.560 | −2.985 | 1.00 | 30.26 | C |
|---|---|---|---|---|---|---|---|---|---|---|---|
| ATOM | 4486 | O | SER | E | 220 | 56.751 | 11.182 | −2.480 | 1.00 | 29.71 | O |
| ATOM | 4487 | CB | SER | E | 220 | 57.376 | 13.689 | −1.764 | 1.00 | 31.53 | C |
| ATOM | 4488 | OG | SER | E | 220 | 57.815 | 15.014 | −1.511 | 1.00 | 32.75 | O |
| ATOM | 4489 | N | VAL | E | 221 | 58.559 | 10.775 | −3.750 | 1.00 | 29.92 | N |
| ATOM | 4490 | CA | VAL | E | 221 | 58.142 | 9.416 | −4.090 | 1.00 | 29.80 | C |
| ATOM | 4491 | C | VAL | E | 221 | 57.992 | 8.497 | −2.869 | 1.00 | 30.61 | C |
| ATOM | 4492 | O | VAL | E | 221 | 58.656 | 8.680 | −1.838 | 1.00 | 30.25 | O |
| ATOM | 4493 | CB | VAL | E | 221 | 59.125 | 8.776 | −5.120 | 1.00 | 30.18 | C |
| ATOM | 4494 | CG1 | VAL | E | 221 | 59.311 | 9.715 | −6.310 | 1.00 | 29.28 | C |
| ATOM | 4495 | CG2 | VAL | E | 221 | 60.476 | 8.496 | −4.475 | 1.00 | 29.72 | C |
| ATOM | 4496 | N | VAL | E | 222 | 57.092 | 7.524 | −2.994 | 1.00 | 30.94 | N |
| ATOM | 4497 | CA | VAL | E | 222 | 56.813 | 6.550 | −1.945 | 1.00 | 31.89 | C |
| ATOM | 4498 | C | VAL | E | 222 | 56.772 | 5.170 | −2.597 | 1.00 | 33.21 | C |
| ATOM | 4499 | O | VAL | E | 222 | 56.720 | 5.058 | −3.823 | 1.00 | 33.31 | O |
| ATOM | 4500 | CB | VAL | E | 222 | 55.434 | 6.823 | −1.235 | 1.00 | 32.49 | C |
| ATOM | 4501 | CG1 | VAL | E | 222 | 55.467 | 8.160 | −0.495 | 1.00 | 33.19 | C |
| ATOM | 4502 | CG2 | VAL | E | 222 | 54.295 | 6.816 | −2.257 | 1.00 | 31.82 | C |
| ATOM | 4503 | N | PRO | E | 223 | 56.811 | 4.100 | −1.784 | 1.00 | 34.13 | N |
| ATOM | 4504 | CA | PRO | E | 223 | 56.779 | 2.725 | −2.292 | 1.00 | 33.89 | C |
| ATOM | 4505 | C | PRO | E | 223 | 55.724 | 2.452 | −3.360 | 1.00 | 33.67 | C |
| ATOM | 4506 | O | PRO | E | 223 | 55.995 | 1.758 | −4.335 | 1.00 | 33.72 | O |
| ATOM | 4507 | CB | PRO | E | 223 | 56.548 | 1.903 | −1.023 | 1.00 | 34.43 | C |
| ATOM | 4508 | CG | PRO | E | 223 | 57.372 | 2.657 | −0.022 | 1.00 | 34.86 | C |
| ATOM | 4509 | CD | PRO | E | 223 | 56.978 | 4.105 | −0.319 | 1.00 | 34.62 | C |
| ATOM | 4510 | N | SER | E | 224 | 54.528 | 3.006 | −3.185 | 1.00 | 32.74 | N |
| ATOM | 4511 | CA | SER | E | 224 | 53.448 | 2.789 | −4.138 | 1.00 | 31.97 | C |
| ATOM | 4512 | C | SER | E | 224 | 53.709 | 3.334 | −5.549 | 1.00 | 31.69 | C |
| ATOM | 4513 | O | SER | E | 224 | 53.001 | 2.977 | −6.489 | 1.00 | 31.29 | O |
| ATOM | 4514 | CB | SER | E | 224 | 52.144 | 3.381 | −3.590 | 1.00 | 32.09 | C |
| ATOM | 4515 | OG | SER | E | 224 | 52.261 | 4.783 | −3.398 | 1.00 | 32.79 | O |
| ATOM | 4516 | N | ASP | E | 225 | 54.712 | 4.198 | −5.704 | 1.00 | 31.22 | N |
| ATOM | 4517 | CA | ASP | E | 225 | 55.037 | 4.758 | −7.023 | 1.00 | 30.43 | C |
| ATOM | 4518 | C | ASP | E | 225 | 55.774 | 3.757 | −7.928 | 1.00 | 30.38 | C |
| ATOM | 4519 | O | ASP | E | 225 | 55.958 | 4.002 | −9.125 | 1.00 | 29.76 | O |
| ATOM | 4520 | CB | ASP | E | 225 | 55.901 | 6.018 | −6.885 | 1.00 | 29.19 | C |
| ATOM | 4521 | CG | ASP | E | 225 | 55.128 | 7.221 | −6.357 | 1.00 | 28.97 | C |
| ATOM | 4522 | OD1 | ASP | E | 225 | 53.977 | 7.464 | −6.809 | 1.00 | 25.87 | O |
| ATOM | 4523 | OD2 | ASP | E | 225 | 55.694 | 7.940 | −5.505 | 1.00 | 26.42 | O |
| ATOM | 4524 | N | LYS | E | 226 | 56.206 | 2.639 | −7.350 | 1.00 | 30.23 | N |
| ATOM | 4525 | CA | LYS | E | 226 | 56.913 | 1.615 | −8.113 | 1.00 | 30.24 | C |
| ATOM | 4526 | C | LYS | E | 226 | 56.081 | 1.193 | −9.323 | 1.00 | 29.94 | C |
| ATOM | 4527 | O | LYS | E | 226 | 54.871 | 1.019 | −9.206 | 1.00 | 29.84 | O |
| ATOM | 4528 | CB | LYS | E | 226 | 57.202 | 0.399 | −7.223 | 1.00 | 29.99 | C |
| ATOM | 4529 | CG | LYS | E | 226 | 57.794 | −0.806 | −7.964 | 1.00 | 30.78 | C |
| ATOM | 4530 | CD | LYS | E | 226 | 58.129 | −1.933 | −6.992 | 1.00 | 30.41 | C |
| ATOM | 4531 | CE | LYS | E | 226 | 58.826 | −3.099 | −7.694 | 1.00 | 33.17 | C |
| ATOM | 4532 | NZ | LYS | E | 226 | 59.329 | −4.124 | −6.720 | 1.00 | 32.61 | N |
| ATOM | 4533 | N | GLY | E | 227 | 56.737 | 1.038 | −10.477 | 1.00 | 29.05 | N |
| ATOM | 4534 | CA | GLY | E | 227 | 56.046 | 0.638 | −11.693 | 1.00 | 28.94 | C |
| ATOM | 4535 | C | GLY | E | 227 | 56.776 | 1.071 | −12.957 | 1.00 | 29.12 | C |
| ATOM | 4536 | O | GLY | E | 227 | 57.935 | 1.490 | −12.903 | 1.00 | 28.36 | O |
| ATOM | 4537 | N | ASN | E | 228 | 56.109 | 0.956 | −14.100 | 1.00 | 28.95 | N |
| ATOM | 4538 | CA | ASN | E | 228 | 56.701 | 1.351 | −15.374 | 1.00 | 29.57 | C |
| ATOM | 4539 | C | ASN | E | 228 | 56.124 | 2.673 | −15.864 | 1.00 | 28.26 | C |
| ATOM | 4540 | O | ASN | E | 228 | 54.918 | 2.903 | −15.768 | 1.00 | 28.23 | O |
| ATOM | 4541 | CB | ASN | E | 228 | 56.455 | 0.294 | −16.458 | 1.00 | 32.45 | C |
| ATOM | 4542 | CG | ASN | E | 228 | 57.048 | −1.054 | −16.106 | 1.00 | 35.12 | C |
| ATOM | 4543 | OD1 | ASN | E | 228 | 58.112 | −1.139 | −15.503 | 1.00 | 36.41 | O |
| ATOM | 4544 | ND2 | ASN | E | 228 | 56.365 | −2.116 | −16.498 | 1.00 | 37.00 | N |
| ATOM | 4545 | N | TYR | E | 229 | 56.995 | 3.532 | −16.387 | 1.00 | 26.32 | N |
| ATOM | 4546 | CA | TYR | E | 229 | 56.591 | 4.827 | −16.921 | 1.00 | 25.19 | C |
| ATOM | 4547 | C | TYR | E | 229 | 57.097 | 4.935 | −18.350 | 1.00 | 25.34 | C |
| ATOM | 4548 | O | TYR | E | 229 | 58.306 | 4.882 | −18.616 | 1.00 | 24.46 | O |
| ATOM | 4549 | CB | TYR | E | 229 | 57.132 | 5.964 | −16.053 | 1.00 | 23.37 | C |
| ATOM | 4550 | CG | TYR | E | 229 | 56.572 | 5.928 | −14.650 | 1.00 | 24.79 | C |
| ATOM | 4551 | CD1 | TYR | E | 229 | 57.101 | 5.068 | −13.691 | 1.00 | 24.70 | C |
| ATOM | 4552 | CD2 | TYR | E | 229 | 55.447 | 6.689 | −14.306 | 1.00 | 24.93 | C |
| ATOM | 4553 | CE1 | TYR | E | 229 | 56.521 | 4.954 | −12.432 | 1.00 | 26.06 | C |
| ATOM | 4554 | CE2 | TYR | E | 229 | 54.865 | 6.586 | −13.059 | 1.00 | 23.86 | C |
| ATOM | 4555 | CZ | TYR | E | 229 | 55.396 | 5.714 | −12.126 | 1.00 | 26.06 | C |
| ATOM | 4556 | OH | TYR | E | 229 | 54.769 | 5.550 | −10.912 | 1.00 | 25.94 | O |
| ATOM | 4557 | N | THR | E | 230 | 56.150 | 5.085 | −19.271 | 1.00 | 25.17 | N |
| ATOM | 4558 | CA | THR | E | 230 | 56.454 | 5.151 | −20.694 | 1.00 | 24.43 | C |
| ATOM | 4559 | C | THR | E | 230 | 56.142 | 6.485 | −21.349 | 1.00 | 24.97 | C |
| ATOM | 4560 | O | THR | E | 230 | 55.070 | 7.064 | −21.156 | 1.00 | 24.36 | O |
| ATOM | 4561 | CB | THR | E | 230 | 55.666 | 4.071 | −21.457 | 1.00 | 24.48 | C |

TABLE 3-continued

FGFR2(D2–D3) Complexed with FGF2

| ATOM | 4562 | OG1 | THR | E | 230 | 55.930 | 2.795 | −20.863 | 1.00 | 24.81 | O |
|---|---|---|---|---|---|---|---|---|---|---|---|
| ATOM | 4563 | CG2 | THR | E | 230 | 56.057 | 4.055 | −22.931 | 1.00 | 22.29 | C |
| ATOM | 4564 | N | CYS | E | 231 | 57.086 | 6.963 | −22.144 | 1.00 | 26.19 | N |
| ATOM | 4565 | CA | CYS | E | 231 | 56.899 | 8.212 | −22.862 | 1.00 | 27.54 | C |
| ATOM | 4566 | C | CYS | E | 231 | 56.607 | 7.858 | −24.317 | 1.00 | 27.22 | C |
| ATOM | 4567 | O | CYS | E | 231 | 57.333 | 7.065 | −24.916 | 1.00 | 26.23 | O |
| ATOM | 4568 | CB | CYS | E | 231 | 58.168 | 9.062 | −22.783 | 1.00 | 27.82 | C |
| ATOM | 4569 | SG | CYS | E | 231 | 59.585 | 8.263 | −23.576 | 1.00 | 31.09 | S |
| ATOM | 4570 | N | VAL | E | 232 | 55.533 | 8.427 | −24.860 | 1.00 | 28.00 | N |
| ATOM | 4571 | CA | VAL | E | 232 | 55.136 | 8.214 | −26.249 | 1.00 | 29.12 | C |
| ATOM | 4572 | C | VAL | E | 232 | 55.235 | 9.563 | −26.970 | 1.00 | 29.74 | C |
| ATOM | 4573 | O | VAL | E | 232 | 54.641 | 10.541 | −26.546 | 1.00 | 31.15 | O |
| ATOM | 4574 | CB | VAL | E | 232 | 53.693 | 7.700 | −26.340 | 1.00 | 29.29 | C |
| ATOM | 4575 | CG1 | VAL | E | 232 | 53.306 | 7.485 | −27.798 | 1.00 | 28.53 | C |
| ATOM | 4576 | CG2 | VAL | E | 232 | 53.557 | 6.407 | −25.549 | 1.00 | 29.10 | C |
| ATOM | 4577 | N | VAL | E | 233 | 56.001 | 9.607 | −28.051 | 1.00 | 30.49 | N |
| ATOM | 4578 | CA | VAL | E | 233 | 56.202 | 10.833 | −28.807 | 1.00 | 31.77 | C |
| ATOM | 4579 | C | VAL | E | 233 | 55.755 | 10.626 | −30.254 | 1.00 | 32.47 | C |
| ATOM | 4580 | O | VAL | E | 233 | 56.157 | 9.651 | −30.903 | 1.00 | 32.76 | O |
| ATOM | 4581 | CB | VAL | E | 233 | 57.694 | 11.243 | −28.779 | 1.00 | 31.18 | C |
| ATOM | 4582 | CG1 | VAL | E | 233 | 57.866 | 12.612 | −29.379 | 1.00 | 33.05 | C |
| ATOM | 4583 | CG2 | VAL | E | 233 | 58.199 | 11.250 | −27.352 | 1.00 | 32.93 | C |
| ATOM | 4584 | N | GLU | E | 234 | 54.951 | 11.551 | −30.773 | 1.00 | 32.15 | N |
| ATOM | 4585 | CA | GLU | E | 234 | 54.444 | 11.390 | −32.129 | 1.00 | 33.60 | C |
| ATOM | 4586 | C | GLU | E | 234 | 54.082 | 12.639 | −32.948 | 1.00 | 33.59 | C |
| ATOM | 4587 | O | GLU | E | 234 | 53.832 | 13.713 | −32.405 | 1.00 | 33.70 | O |
| ATOM | 4588 | CB | GLU | E | 234 | 53.210 | 10.480 | −32.068 | 1.00 | 33.20 | C |
| ATOM | 4589 | N | ASN | E | 235 | 54.068 | 12.460 | −34.267 | 1.00 | 34.11 | N |
| ATOM | 4590 | CA | ASN | E | 235 | 53.657 | 13.483 | −35.233 | 1.00 | 34.29 | C |
| ATOM | 4591 | C | ASN | E | 235 | 53.084 | 12.694 | −36.411 | 1.00 | 35.08 | C |
| ATOM | 4592 | O | ASN | E | 235 | 52.958 | 11.470 | −36.314 | 1.00 | 34.59 | O |
| ATOM | 4593 | CB | ASN | E | 235 | 54.810 | 14.414 | −35.664 | 1.00 | 33.28 | C |
| ATOM | 4594 | CG | ASN | E | 235 | 55.900 | 13.708 | −36.447 | 1.00 | 33.88 | C |
| ATOM | 4595 | OD1 | ASN | E | 235 | 55.730 | 12.583 | −36.910 | 1.00 | 33.30 | O |
| ATOM | 4596 | ND2 | ASN | E | 235 | 57.036 | 14.385 | −36.609 | 1.00 | 34.18 | N |
| ATOM | 4597 | N | GLU | E | 236 | 52.738 | 13.358 | −37.512 | 1.00 | 36.42 | N |
| ATOM | 4598 | CA | GLU | E | 236 | 52.138 | 12.629 | −38.636 | 1.00 | 38.00 | C |
| ATOM | 4599 | C | GLU | E | 236 | 53.011 | 11.594 | −39.343 | 1.00 | 37.78 | C |
| ATOM | 4600 | O | GLU | E | 236 | 52.486 | 10.739 | −40.053 | 1.00 | 37.97 | O |
| ATOM | 4601 | CB | GLU | E | 236 | 51.531 | 13.595 | −39.664 | 1.00 | 40.24 | C |
| ATOM | 4602 | CG | GLU | E | 236 | 52.492 | 14.582 | −40.284 | 1.00 | 43.86 | C |
| ATOM | 4603 | CD | GLU | E | 236 | 51.790 | 15.531 | −41.242 | 1.00 | 46.25 | C |
| ATOM | 4604 | OE1 | GLU | E | 236 | 51.225 | 15.059 | −42.255 | 1.00 | 47.28 | O |
| ATOM | 4605 | OE2 | GLU | E | 236 | 51.803 | 16.750 | −40.976 | 1.00 | 47.49 | O |
| ATOM | 4606 | N | TYR | E | 237 | 54.323 | 11.640 | −39.121 | 1.00 | 37.33 | N |
| ATOM | 4607 | CA | TYR | E | 237 | 55.242 | 10.708 | −39.766 | 1.00 | 37.35 | C |
| ATOM | 4608 | C | TYR | E | 237 | 55.754 | 9.569 | −38.867 | 1.00 | 35.98 | C |
| ATOM | 4609 | O | TYR | E | 237 | 56.577 | 8.758 | −39.290 | 1.00 | 35.90 | O |
| ATOM | 4610 | CB | TYR | E | 237 | 56.415 | 11.508 | −40.346 | 1.00 | 38.92 | C |
| ATOM | 4611 | CG | TYR | E | 237 | 55.957 | 12.649 | −41.233 | 1.00 | 41.25 | C |
| ATOM | 4612 | CD1 | TYR | E | 237 | 56.460 | 13.943 | −41.059 | 1.00 | 43.19 | C |
| ATOM | 4613 | CD2 | TYR | E | 237 | 55.004 | 12.444 | −42.226 | 1.00 | 42.47 | C |
| ATOM | 4614 | CE1 | TYR | E | 237 | 56.018 | 15.008 | −41.855 | 1.00 | 44.62 | C |
| ATOM | 4615 | CE2 | TYR | E | 237 | 54.554 | 13.495 | −43.026 | 1.00 | 44.57 | C |
| ATOM | 4616 | CZ | TYR | E | 237 | 55.062 | 14.777 | −42.835 | 1.00 | 45.49 | C |
| ATOM | 4617 | OH | TYR | E | 237 | 54.598 | 15.822 | −43.609 | 1.00 | 46.29 | O |
| ATOM | 4618 | N | GLY | E | 238 | 55.275 | 9.497 | −37.632 | 1.00 | 34.97 | N |
| ATOM | 4619 | CA | GLY | E | 238 | 55.731 | 8.417 | −36.777 | 1.00 | 33.97 | C |
| ATOM | 4620 | C | GLY | E | 238 | 55.405 | 8.507 | −35.303 | 1.00 | 33.08 | C |
| ATOM | 4621 | O | GLY | E | 238 | 54.983 | 9.548 | −34.803 | 1.00 | 32.50 | O |
| ATOM | 4622 | N | SER | E | 239 | 55.617 | 7.390 | −34.612 | 1.00 | 32.34 | N |
| ATOM | 4623 | CA | SER | E | 239 | 55.369 | 7.282 | −33.181 | 1.00 | 31.81 | C |
| ATOM | 4624 | C | SER | E | 239 | 56.404 | 6.351 | −32.543 | 1.00 | 30.71 | C |
| ATOM | 4625 | O | SER | E | 239 | 56.567 | 5.211 | −32.980 | 1.00 | 30.65 | O |
| ATOM | 4626 | CB | SER | E | 239 | 53.954 | 6.739 | −32.942 | 1.00 | 30.90 | C |
| ATOM | 4627 | OG | SER | E | 239 | 53.628 | 6.735 | −31.563 | 1.00 | 33.07 | O |
| ATOM | 4628 | N | ILE | E | 240 | 57.091 | 6.834 | −31.510 | 1.00 | 29.56 | N |
| ATOM | 4629 | CA | ILE | E | 240 | 58.112 | 6.042 | −30.827 | 1.00 | 28.65 | C |
| ATOM | 4630 | C | ILE | E | 240 | 57.935 | 6.162 | −29.318 | 1.00 | 28.96 | C |
| ATOM | 4631 | O | ILE | E | 240 | 57.382 | 7.152 | −28.830 | 1.00 | 30.00 | O |
| ATOM | 4632 | CB | ILE | E | 240 | 59.528 | 6.514 | −31.210 | 1.00 | 28.14 | C |
| ATOM | 4633 | CG1 | ILE | E | 240 | 59.726 | 7.960 | −30.758 | 1.00 | 28.72 | C |
| ATOM | 4634 | CG2 | ILE | E | 240 | 59.712 | 6.435 | −32.729 | 1.00 | 26.24 | C |
| ATOM | 4635 | CD1 | ILE | E | 240 | 61.132 | 8.520 | −31.032 | 1.00 | 29.86 | C |
| ATOM | 4636 | N | ASN | E | 241 | 58.405 | 5.157 | −28.582 | 1.00 | 27.76 | N |
| ATOM | 4637 | CA | ASN | E | 241 | 58.284 | 5.147 | −27.136 | 1.00 | 26.27 | C |
| ATOM | 4638 | C | ASN | E | 241 | 59.499 | 4.531 | −26.439 | 1.00 | 26.41 | C |

TABLE 3-continued

FGFR2(D2–D3) Complexed with FGF2

| ATOM | 4639 | O | ASN | E | 241 | 60.301 | 3.815 | −27.058 | 1.00 | 25.18 | O |
|---|---|---|---|---|---|---|---|---|---|---|---|
| ATOM | 4640 | CB | ASN | E | 241 | 57.018 | 4.384 | −26.711 | 1.00 | 25.29 | C |
| ATOM | 4641 | CG | ASN | E | 241 | 56.946 | 2.983 | −27.311 | 1.00 | 27.08 | C |
| ATOM | 4642 | OD1 | ASN | E | 241 | 56.345 | 2.769 | −28.374 | 1.00 | 29.98 | O |
| ATOM | 4643 | ND2 | ASN | E | 241 | 57.578 | 2.032 | −26.652 | 1.00 | 26.55 | N |
| ATOM | 4644 | N | HIS | E | 242 | 59.610 | 4.819 | −25.145 | 1.00 | 26.04 | N |
| ATOM | 4645 | CA | HIS | E | 242 | 60.693 | 4.317 | −24.309 | 1.00 | 27.09 | C |
| ATOM | 4646 | C | HIS | E | 242 | 60.130 | 4.097 | −22.913 | 1.00 | 26.68 | C |
| ATOM | 4647 | O | HIS | E | 242 | 59.274 | 4.865 | −22.464 | 1.00 | 26.32 | O |
| ATOM | 4648 | CB | HIS | E | 242 | 61.833 | 5.325 | −24.233 | 1.00 | 28.10 | C |
| ATOM | 4649 | CG | HIS | E | 242 | 62.957 | 4.888 | −23.352 | 1.00 | 29.54 | C |
| ATOM | 4650 | ND1 | HIS | E | 242 | 63.851 | 3.904 | −23.716 | 1.00 | 30.25 | N |
| ATOM | 4651 | CD2 | HIS | E | 242 | 63.341 | 5.309 | −22.124 | 1.00 | 31.00 | C |
| ATOM | 4652 | CE1 | HIS | E | 242 | 64.742 | 3.744 | −22.754 | 1.00 | 32.05 | C |
| ATOM | 4653 | NE2 | HIS | E | 242 | 64.455 | 4.585 | −21.778 | 1.00 | 32.16 | N |
| ATOM | 4654 | N | THR | E | 243 | 60.617 | 3.068 | −22.225 | 1.00 | 26.12 | N |
| ATOM | 4655 | CA | THR | E | 243 | 60.112 | 2.759 | −20.893 | 1.00 | 26.90 | C |
| ATOM | 4656 | C | THR | E | 243 | 61.134 | 2.756 | −19.770 | 1.00 | 27.39 | C |
| ATOM | 4657 | O | THR | E | 243 | 62.219 | 2.202 | −19.908 | 1.00 | 27.23 | O |
| ATOM | 4658 | CB | THR | E | 243 | 59.377 | 1.381 | −20.871 | 1.00 | 26.77 | C |
| ATOM | 4659 | OG1 | THR | E | 243 | 58.225 | 1.439 | −21.716 | 1.00 | 25.38 | O |
| ATOM | 4660 | CG2 | THR | E | 243 | 58.917 | 1.032 | −19.449 | 1.00 | 26.06 | C |
| ATOM | 4661 | N | TYR | E | 244 | 60.757 | 3.390 | −18.662 | 1.00 | 27.91 | N |
| ATOM | 4662 | CA | TYR | E | 244 | 61.581 | 3.460 | −17.465 | 1.00 | 29.32 | C |
| ATOM | 4663 | C | TYR | E | 244 | 60.898 | 2.640 | −16.370 | 1.00 | 30.85 | C |
| ATOM | 4664 | O | TYR | E | 244 | 59.677 | 2.506 | −16.354 | 1.00 | 30.71 | O |
| ATOM | 4665 | CB | TYR | E | 244 | 61.723 | 4.899 | −16.960 | 1.00 | 27.74 | C |
| ATOM | 4666 | CG | TYR | E | 244 | 62.566 | 5.802 | −17.828 | 1.00 | 27.95 | C |
| ATOM | 4667 | CD1 | TYR | E | 244 | 61.987 | 6.840 | −18.564 | 1.00 | 26.62 | C |
| ATOM | 4668 | CD2 | TYR | E | 244 | 63.951 | 5.640 | −17.888 | 1.00 | 26.74 | C |
| ATOM | 4669 | CE1 | TYR | E | 244 | 62.769 | 7.696 | −19.334 | 1.00 | 27.44 | C |
| ATOM | 4670 | CE2 | TYR | E | 244 | 64.739 | 6.481 | −18.651 | 1.00 | 27.77 | C |
| ATOM | 4671 | CZ | TYR | E | 244 | 64.147 | 7.511 | −19.371 | 1.00 | 28.12 | C |
| ATOM | 4672 | OH | TYR | E | 244 | 64.943 | 8.350 | −20.107 | 1.00 | 27.83 | O |
| ATOM | 4673 | N | HIS | E | 245 | 61.693 | 2.088 | −15.464 | 1.00 | 31.97 | N |
| ATOM | 4674 | CA | HIS | E | 245 | 61.161 | 1.322 | −14.349 | 1.00 | 33.12 | C |
| ATOM | 4675 | C | HIS | E | 245 | 61.552 | 2.073 | −13.083 | 1.00 | 33.00 | C |
| ATOM | 4676 | O | HIS | E | 245 | 62.706 | 2.472 | −12.929 | 1.00 | 32.70 | O |
| ATOM | 4677 | CB | HIS | E | 245 | 61.760 | −0.085 | −14.341 | 1.00 | 34.97 | C |
| ATOM | 4678 | CG | HIS | E | 245 | 61.552 | −0.826 | −15.629 | 1.00 | 37.68 | C |
| ATOM | 4679 | ND1 | HIS | E | 245 | 60.342 | −1.378 | −15.982 | 1.00 | 38.21 | N |
| ATOM | 4680 | CD2 | HIS | E | 245 | 62.396 | −1.081 | −16.657 | 1.00 | 39.69 | C |
| ATOM | 4681 | CE1 | HIS | E | 245 | 60.444 | −1.941 | −17.175 | 1.00 | 38.71 | C |
| ATOM | 4682 | NE2 | HIS | E | 245 | 61.684 | −1.772 | −17.607 | 1.00 | 39.57 | N |
| ATOM | 4683 | N | LEU | E | 246 | 60.594 | 2.292 | −12.190 | 1.00 | 32.23 | N |
| ATOM | 4684 | CA | LEU | E | 246 | 60.886 | 3.001 | −10.951 | 1.00 | 32.14 | C |
| ATOM | 4685 | C | LEU | E | 246 | 60.742 | 2.103 | −9.728 | 1.00 | 33.28 | C |
| ATOM | 4686 | O | LEU | E | 246 | 59.802 | 1.309 | −9.628 | 1.00 | 34.04 | O |
| ATOM | 4687 | CB | LEU | E | 246 | 59.974 | 4.228 | −10.794 | 1.00 | 29.30 | C |
| ATOM | 4688 | CG | LEU | E | 246 | 60.035 | 4.965 | −9.443 | 1.00 | 28.46 | C |
| ATOM | 4689 | CD1 | LEU | E | 246 | 61.416 | 5.654 | −9.272 | 1.00 | 27.02 | C |
| ATOM | 4690 | CD2 | LEU | E | 246 | 58.903 | 6.010 | −9.365 | 1.00 | 24.91 | C |
| ATOM | 4691 | N | ASP | E | 247 | 61.690 | 2.224 | −8.804 | 1.00 | 34.64 | N |
| ATOM | 4692 | CA | ASP | E | 247 | 61.653 | 1.454 | −7.564 | 1.00 | 36.26 | C |
| ATOM | 4693 | C | ASP | E | 247 | 62.022 | 2.415 | −6.441 | 1.00 | 36.40 | C |
| ATOM | 4694 | O | ASP | E | 247 | 62.929 | 3.242 | −6.597 | 1.00 | 36.83 | O |
| ATOM | 4695 | CB | ASP | E | 247 | 62.637 | 0.269 | −7.619 | 1.00 | 37.20 | C |
| ATOM | 4696 | CG | ASP | E | 247 | 62.243 | −0.872 | −6.670 | 1.00 | 39.20 | C |
| ATOM | 4697 | OD1 | ASP | E | 247 | 62.687 | −2.025 | −6.884 | 1.00 | 40.40 | O |
| ATOM | 4698 | OD2 | ASP | E | 247 | 61.494 | −0.621 | −5.703 | 1.00 | 39.88 | O |
| ATOM | 4699 | N | VAL | E | 248 | 61.309 | 2.327 | −5.322 | 1.00 | 36.45 | N |
| ATOM | 4700 | CA | VAL | E | 248 | 61.563 | 3.204 | −4.194 | 1.00 | 36.17 | C |
| ATOM | 4701 | C | VAL | E | 248 | 61.964 | 2.413 | −2.959 | 1.00 | 36.51 | C |
| ATOM | 4702 | O | VAL | E | 248 | 61.353 | 1.391 | −2.637 | 1.00 | 37.11 | O |
| ATOM | 4703 | CB | VAL | E | 248 | 60.328 | 4.060 | −3.891 | 1.00 | 36.50 | C |
| ATOM | 4704 | CG1 | VAL | E | 248 | 60.629 | 5.054 | −2.775 | 1.00 | 35.40 | C |
| ATOM | 4705 | CG2 | VAL | E | 248 | 59.904 | 4.785 | −5.156 | 1.00 | 36.50 | C |
| ATOM | 4706 | N | VAL | E | 249 | 63.000 | 2.897 | −2.279 | 1.00 | 35.72 | N |
| ATOM | 4707 | CA | VAL | E | 249 | 63.534 | 2.253 | −1.085 | 1.00 | 35.92 | C |
| ATOM | 4708 | C | VAL | E | 249 | 63.487 | 3.191 | 0.121 | 1.00 | 36.10 | C |
| ATOM | 4709 | O | VAL | E | 249 | 64.017 | 4.301 | 0.080 | 1.00 | 35.27 | O |
| ATOM | 4710 | CB | VAL | E | 249 | 65.019 | 1.824 | −1.313 | 1.00 | 35.97 | C |
| ATOM | 4711 | CG1 | VAL | E | 249 | 65.575 | 1.161 | −0.060 | 1.00 | 35.72 | C |
| ATOM | 4712 | CG2 | VAL | E | 249 | 65.118 | 0.890 | −2.500 | 1.00 | 35.65 | C |
| ATOM | 4713 | N | GLU | E | 250 | 62.866 | 2.739 | 1.199 | 1.00 | 36.41 | N |
| ATOM | 4714 | CA | GLU | E | 250 | 62.776 | 3.555 | 2.402 | 1.00 | 37.64 | C |
| ATOM | 4715 | C | GLU | E | 250 | 64.031 | 3.372 | 3.246 | 1.00 | 36.43 | C |

TABLE 3-continued

FGFR2(D2–D3) Complexed with FGF2

| ATOM | 4716 | O | GLU | E | 250 | 64.413 | 2.252 | 3.553 | 1.00 | 36.31 | O |
|---|---|---|---|---|---|---|---|---|---|---|---|
| ATOM | 4717 | CB | GLU | E | 250 | 61.523 | 3.156 | 3.189 | 1.00 | 39.76 | C |
| ATOM | 4718 | CG | GLU | E | 250 | 60.238 | 3.451 | 2.429 | 1.00 | 43.74 | C |
| ATOM | 4719 | CD | GLU | E | 250 | 58.994 | 2.886 | 3.103 | 1.00 | 46.43 | C |
| ATOM | 4720 | OE1 | GLU | E | 250 | 58.842 | 1.644 | 3.131 | 1.00 | 47.52 | O |
| ATOM | 4721 | OE2 | GLU | E | 250 | 58.173 | 3.691 | 3.602 | 1.00 | 47.61 | O |
| ATOM | 4722 | N | ARG | E | 251 | 64.673 | 4.479 | 3.605 | 1.00 | 35.83 | N |
| ATOM | 4723 | CA | ARG | E | 251 | 65.887 | 4.452 | 4.410 | 1.00 | 34.82 | C |
| ATOM | 4724 | C | ARG | E | 251 | 65.534 | 4.841 | 5.837 | 1.00 | 35.98 | C |
| ATOM | 4725 | O | ARG | E | 251 | 64.655 | 5.659 | 6.048 | 1.00 | 36.11 | O |
| ATOM | 4726 | CB | ARG | E | 251 | 66.912 | 5.434 | 3.848 | 1.00 | 32.96 | C |
| ATOM | 4727 | CG | ARG | E | 251 | 67.309 | 5.148 | 2.405 | 1.00 | 30.43 | C |
| ATOM | 4728 | CD | ARG | E | 251 | 67.624 | 3.661 | 2.208 | 1.00 | 28.89 | C |
| ATOM | 4729 | NE | ARG | E | 251 | 68.650 | 3.166 | 3.125 | 1.00 | 25.79 | N |
| ATOM | 4730 | CZ | ARG | E | 251 | 69.962 | 3.342 | 2.973 | 1.00 | 24.83 | C |
| ATOM | 4731 | NH1 | ARG | E | 251 | 70.448 | 4.011 | 1.934 | 1.00 | 24.17 | N |
| ATOM | 4732 | NH2 | ARG | E | 251 | 70.798 | 2.812 | 3.854 | 1.00 | 25.42 | N |
| ATOM | 4733 | N | SER | E | 252 | 66.208 | 4.261 | 6.821 | 1.00 | 35.82 | N |
| ATOM | 4734 | CA | SER | E | 252 | 65.943 | 4.546 | 8.227 | 1.00 | 36.14 | C |
| ATOM | 4735 | C | SER | E | 252 | 67.213 | 5.007 | 8.944 | 1.00 | 36.13 | C |
| ATOM | 4736 | O | SER | E | 252 | 68.037 | 4.196 | 9.349 | 1.00 | 35.73 | O |
| ATOM | 4737 | CB | SER | E | 252 | 65.379 | 3.291 | 8.901 | 1.00 | 36.34 | C |
| ATOM | 4738 | OG | SER | E | 252 | 65.345 | 3.445 | 10.308 | 1.00 | 39.29 | O |
| ATOM | 4739 | N | PRO | E | 253 | 67.384 | 6.319 | 9.112 | 1.00 | 36.78 | N |
| ATOM | 4740 | CA | PRO | E | 253 | 68.579 | 6.842 | 9.782 | 1.00 | 37.06 | C |
| ATOM | 4741 | C | PRO | E | 253 | 68.593 | 6.740 | 11.310 | 1.00 | 37.49 | C |
| ATOM | 4742 | O | PRO | E | 253 | 68.899 | 7.715 | 11.992 | 1.00 | 38.41 | O |
| ATOM | 4743 | CB | PRO | E | 253 | 68.644 | 8.285 | 9.289 | 1.00 | 37.46 | C |
| ATOM | 4744 | CG | PRO | E | 253 | 67.196 | 8.649 | 9.163 | 1.00 | 37.04 | C |
| ATOM | 4745 | CD | PRO | E | 253 | 66.576 | 7.413 | 8.535 | 1.00 | 36.82 | C |
| ATOM | 4746 | N | HIS | E | 254 | 68.263 | 5.572 | 11.849 | 1.00 | 37.59 | N |
| ATOM | 4747 | CA | HIS | E | 254 | 68.281 | 5.390 | 13.299 | 1.00 | 37.95 | C |
| ATOM | 4748 | C | HIS | E | 254 | 69.383 | 4.430 | 13.742 | 1.00 | 36.67 | C |
| ATOM | 4749 | O | HIS | E | 254 | 69.880 | 3.632 | 12.956 | 1.00 | 35.85 | O |
| ATOM | 4750 | CB | HIS | E | 254 | 66.943 | 4.851 | 13.814 | 1.00 | 40.15 | C |
| ATOM | 4751 | CG | HIS | E | 254 | 65.788 | 5.774 | 13.584 | 1.00 | 43.58 | C |
| ATOM | 4752 | ND1 | HIS | E | 254 | 65.029 | 5.746 | 12.431 | 1.00 | 45.48 | N |
| ATOM | 4753 | CD2 | HIS | E | 254 | 65.270 | 6.761 | 14.352 | 1.00 | 44.54 | C |
| ATOM | 4754 | CE1 | HIS | E | 254 | 64.092 | 6.675 | 12.500 | 1.00 | 45.14 | C |
| ATOM | 4755 | NE2 | HIS | E | 254 | 64.216 | 7.305 | 13.656 | 1.00 | 46.03 | N |
| ATOM | 4756 | N | ARG | E | 255 | 69.773 | 4.526 | 15.004 | 1.00 | 35.96 | N |
| ATOM | 4757 | CA | ARG | E | 255 | 70.767 | 3.615 | 15.534 | 1.00 | 35.50 | C |
| ATOM | 4758 | C | ARG | E | 255 | 70.008 | 2.282 | 15.656 | 1.00 | 34.66 | C |
| ATOM | 4759 | O | ARG | E | 255 | 68.777 | 2.262 | 15.560 | 1.00 | 34.53 | O |
| ATOM | 4760 | CB | ARG | E | 255 | 71.261 | 4.102 | 16.897 | 1.00 | 37.29 | C |
| ATOM | 4761 | CG | ARG | E | 255 | 70.222 | 4.051 | 17.999 | 1.00 | 39.20 | C |
| ATOM | 4762 | CD | ARG | E | 255 | 70.851 | 4.379 | 19.349 | 1.00 | 41.59 | C |
| ATOM | 4763 | NE | ARG | E | 255 | 69.966 | 4.025 | 20.454 | 1.00 | 44.03 | N |
| ATOM | 4764 | CZ | ARG | E | 255 | 68.825 | 4.649 | 20.734 | 1.00 | 45.95 | C |
| ATOM | 4765 | NH1 | ARG | E | 255 | 68.425 | 5.675 | 19.992 | 1.00 | 47.53 | N |
| ATOM | 4766 | NH2 | ARG | E | 255 | 68.070 | 4.236 | 21.745 | 1.00 | 46.53 | N |
| ATOM | 4767 | N | PRO | E | 256 | 70.716 | 1.162 | 15.855 | 1.00 | 33.03 | N |
| ATOM | 4768 | CA | PRO | E | 256 | 70.046 | −0.141 | 15.974 | 1.00 | 32.21 | C |
| ATOM | 4769 | C | PRO | E | 256 | 68.968 | −0.207 | 17.055 | 1.00 | 31.23 | C |
| ATOM | 4770 | O | PRO | E | 256 | 69.136 | 0.340 | 18.136 | 1.00 | 31.38 | O |
| ATOM | 4771 | CB | PRO | E | 256 | 71.198 | −1.101 | 16.271 | 1.00 | 31.81 | C |
| ATOM | 4772 | CG | PRO | E | 256 | 72.384 | −0.432 | 15.589 | 1.00 | 32.06 | C |
| ATOM | 4773 | CD | PRO | E | 256 | 72.177 | 1.016 | 15.984 | 1.00 | 33.61 | C |
| ATOM | 4774 | N | ILE | E | 257 | 67.865 | −0.882 | 16.749 | 1.00 | 30.78 | N |
| ATOM | 4775 | CA | ILE | E | 257 | 66.775 | −1.047 | 17.705 | 1.00 | 31.56 | C |
| ATOM | 4776 | C | ILE | E | 257 | 66.654 | −2.528 | 18.123 | 1.00 | 31.18 | C |
| ATOM | 4777 | O | ILE | E | 257 | 66.677 | −3.417 | 17.276 | 1.00 | 30.43 | O |
| ATOM | 4778 | CB | ILE | E | 257 | 65.449 | −0.540 | 17.092 | 1.00 | 33.43 | C |
| ATOM | 4779 | CG1 | ILE | E | 257 | 65.520 | 0.985 | 16.923 | 1.00 | 34.39 | C |
| ATOM | 4780 | CG2 | ILE | E | 257 | 64.281 | −0.937 | 17.967 | 1.00 | 33.57 | C |
| ATOM | 4781 | CD1 | ILE | E | 257 | 64.240 | 1.624 | 16.450 | 1.00 | 36.23 | C |
| ATOM | 4782 | N | LEU | E | 258 | 66.566 | −2.785 | 19.429 | 1.00 | 30.38 | N |
| ATOM | 4783 | CA | LEU | E | 258 | 66.448 | −4.154 | 19.930 | 1.00 | 30.95 | C |
| ATOM | 4784 | C | LEU | E | 258 | 65.035 | −4.436 | 20.434 | 1.00 | 31.23 | C |
| ATOM | 4785 | O | LEU | E | 258 | 64.336 | −3.525 | 20.884 | 1.00 | 30.88 | O |
| ATOM | 4786 | CB | LEU | E | 258 | 67.429 | −4.409 | 21.081 | 1.00 | 29.89 | C |
| ATOM | 4787 | CG | LEU | E | 258 | 68.918 | −4.041 | 20.966 | 1.00 | 32.11 | C |
| ATOM | 4788 | CD1 | LEU | E | 258 | 69.709 | −4.974 | 21.852 | 1.00 | 29.79 | C |
| ATOM | 4789 | CD2 | LEU | E | 258 | 69.422 | −4.144 | 19.535 | 1.00 | 31.84 | C |
| ATOM | 4790 | N | GLN | E | 259 | 64.625 | −5.696 | 20.367 | 1.00 | 31.39 | N |
| ATOM | 4791 | CA | GLN | E | 259 | 63.303 | −6.084 | 20.839 | 1.00 | 32.44 | C |
| ATOM | 4792 | C | GLN | E | 259 | 63.272 | −6.063 | 22.372 | 1.00 | 32.23 | C |

TABLE 3-continued

FGFR2(D2–D3) Complexed with FGF2

| ATOM | 4793 | O | GLN | E | 259 | 64.172 | −6.598 | 23.035 | 1.00 | 31.48 | O |
|---|---|---|---|---|---|---|---|---|---|---|---|
| ATOM | 4794 | CB | GLN | E | 259 | 62.947 | −7.485 | 20.339 | 1.00 | 33.89 | C |
| ATOM | 4795 | CG | GLN | E | 259 | 61.577 | −7.972 | 20.778 | 1.00 | 36.67 | C |
| ATOM | 4796 | CD | GLN | E | 259 | 61.402 | −9.462 | 20.547 | 1.00 | 38.34 | C |
| ATOM | 4797 | OE1 | GLN | E | 259 | 61.645 | −9.961 | 19.451 | 1.00 | 39.45 | O |
| ATOM | 4798 | NE2 | GLN | E | 259 | 60.980 | −10.178 | 21.580 | 1.00 | 39.08 | N |
| ATOM | 4799 | N | ALA | E | 260 | 62.238 | −5.443 | 22.931 | 1.00 | 31.78 | N |
| ATOM | 4800 | CA | ALA | E | 260 | 62.103 | −5.366 | 24.386 | 1.00 | 32.73 | C |
| ATOM | 4801 | C | ALA | E | 260 | 61.931 | −6.757 | 24.992 | 1.00 | 32.75 | C |
| ATOM | 4802 | O | ALA | E | 260 | 61.249 | −7.600 | 24.427 | 1.00 | 33.21 | O |
| ATOM | 4803 | CB | ALA | E | 260 | 60.905 | −4.475 | 24.765 | 1.00 | 32.81 | C |
| ATOM | 4804 | N | GLY | E | 261 | 62.565 | −6.991 | 26.137 | 1.00 | 32.60 | N |
| ATOM | 4805 | CA | GLY | E | 261 | 62.457 | −8.282 | 26.792 | 1.00 | 33.01 | C |
| ATOM | 4806 | C | GLY | E | 261 | 63.577 | −9.258 | 26.473 | 1.00 | 33.86 | C |
| ATOM | 4807 | O | GLY | E | 261 | 63.711 | −10.282 | 27.139 | 1.00 | 33.46 | O |
| ATOM | 4808 | N | LEU | E | 262 | 64.380 | −8.952 | 25.456 | 1.00 | 34.46 | N |
| ATOM | 4809 | CA | LEU | E | 262 | 65.478 | −9.836 | 25.060 | 1.00 | 34.63 | C |
| ATOM | 4810 | C | LEU | E | 262 | 66.821 | −9.128 | 25.125 | 1.00 | 35.41 | C |
| ATOM | 4811 | O | LEU | E | 262 | 66.963 | −7.999 | 24.668 | 1.00 | 35.68 | O |
| ATOM | 4812 | CB | LEU | E | 262 | 65.253 | −10.367 | 23.647 | 1.00 | 34.06 | C |
| ATOM | 4813 | CG | LEU | E | 262 | 64.042 | −11.289 | 23.456 | 1.00 | 35.07 | C |
| ATOM | 4814 | CD1 | LEU | E | 262 | 63.957 | −11.728 | 21.988 | 1.00 | 32.19 | C |
| ATOM | 4815 | CD2 | LEU | E | 262 | 64.177 | −12.513 | 24.369 | 1.00 | 33.00 | C |
| ATOM | 4816 | N | PRO | E | 263 | 67.835 | −9.794 | 25.690 | 1.00 | 36.61 | N |
| ATOM | 4817 | CA | PRO | E | 263 | 67.751 | −11.144 | 26.256 | 1.00 | 36.99 | C |
| ATOM | 4818 | C | PRO | E | 263 | 66.947 | −11.202 | 27.552 | 1.00 | 37.76 | C |
| ATOM | 4819 | O | PRO | E | 263 | 66.684 | −10.180 | 28.181 | 1.00 | 37.69 | O |
| ATOM | 4820 | CB | PRO | E | 263 | 69.216 | −11.505 | 26.464 | 1.00 | 37.44 | C |
| ATOM | 4821 | CG | PRO | E | 263 | 69.809 | −10.185 | 26.849 | 1.00 | 36.22 | C |
| ATOM | 4822 | CD | PRO | E | 263 | 69.197 | −9.254 | 25.830 | 1.00 | 36.32 | C |
| ATOM | 4823 | N | ALA | E | 264 | 66.561 | −12.406 | 27.949 | 1.00 | 39.07 | N |
| ATOM | 4824 | CA | ALA | E | 264 | 65.789 | −12.588 | 29.173 | 1.00 | 40.24 | C |
| ATOM | 4825 | C | ALA | E | 264 | 66.647 | −13.176 | 30.284 | 1.00 | 40.74 | C |
| ATOM | 4826 | O | ALA | E | 264 | 67.602 | −13.911 | 30.024 | 1.00 | 40.98 | O |
| ATOM | 4827 | CB | ALA | E | 264 | 64.586 | −13.497 | 28.905 | 1.00 | 40.12 | C |
| ATOM | 4828 | N | ASN | E | 265 | 66.308 | −12.833 | 31.523 | 1.00 | 42.19 | N |
| ATOM | 4829 | CA | ASN | E | 265 | 67.027 | −13.352 | 32.680 | 1.00 | 43.62 | C |
| ATOM | 4830 | C | ASN | E | 265 | 66.936 | −14.880 | 32.650 | 1.00 | 44.58 | C |
| ATOM | 4831 | O | ASN | E | 265 | 65.966 | −15.445 | 32.124 | 1.00 | 44.42 | O |
| ATOM | 4832 | CB | ASN | E | 265 | 66.399 | −12.817 | 33.969 | 1.00 | 44.05 | C |
| ATOM | 4833 | CG | ASN | E | 265 | 67.055 | −11.536 | 34.456 | 1.00 | 45.16 | C |
| ATOM | 4834 | OD1 | ASN | E | 265 | 67.185 | −10.557 | 33.718 | 1.00 | 44.14 | O |
| ATOM | 4835 | ND2 | ASN | E | 265 | 67.471 | −11.540 | 35.716 | 1.00 | 46.55 | N |
| ATOM | 4836 | N | ALA | E | 266 | 67.947 | −15.545 | 33.198 | 1.00 | 45.09 | N |
| ATOM | 4837 | CA | ALA | E | 266 | 67.955 | −17.004 | 33.230 | 1.00 | 46.13 | C |
| ATOM | 4838 | C | ALA | E | 266 | 68.539 | −17.506 | 34.545 | 1.00 | 46.86 | C |
| ATOM | 4839 | O | ALA | E | 266 | 69.381 | −16.842 | 35.162 | 1.00 | 46.71 | O |
| ATOM | 4840 | CB | ALA | E | 266 | 68.750 | −17.556 | 32.046 | 1.00 | 45.45 | C |
| ATOM | 4841 | N | SER | E | 267 | 68.077 | −18.679 | 34.971 | 1.00 | 47.77 | N |
| ATOM | 4842 | CA | SER | E | 267 | 68.538 | −19.290 | 36.212 | 1.00 | 48.84 | C |
| ATOM | 4843 | C | SER | E | 267 | 68.774 | −20.781 | 35.989 | 1.00 | 49.84 | C |
| ATOM | 4844 | O | SER | E | 267 | 68.054 | −21.425 | 35.214 | 1.00 | 50.77 | O |
| ATOM | 4845 | CB | SER | E | 267 | 67.502 | −19.090 | 37.323 | 1.00 | 48.70 | C |
| ATOM | 4846 | N | ASP | E | 273 | 72.922 | −25.916 | 31.411 | 1.00 | 52.50 | N |
| ATOM | 4847 | CA | ASP | E | 273 | 73.121 | −25.160 | 30.177 | 1.00 | 52.79 | C |
| ATOM | 4848 | C | ASP | E | 273 | 72.109 | −24.024 | 30.024 | 1.00 | 52.36 | C |
| ATOM | 4849 | O | ASP | E | 273 | 70.968 | −24.115 | 30.493 | 1.00 | 52.76 | O |
| ATOM | 4850 | CB | ASP | E | 273 | 73.069 | −26.097 | 28.964 | 1.00 | 53.36 | C |
| ATOM | 4851 | CG | ASP | E | 273 | 74.391 | −26.816 | 28.729 | 1.00 | 53.74 | C |
| ATOM | 4852 | OD1 | ASP | E | 273 | 75.031 | −27.208 | 29.723 | 1.00 | 54.01 | O |
| ATOM | 4853 | OD2 | ASP | E | 273 | 74.786 | −26.998 | 27.557 | 1.00 | 53.01 | O |
| ATOM | 4854 | N | VAL | E | 274 | 72.535 | −22.949 | 29.367 | 1.00 | 51.31 | N |
| ATOM | 4855 | CA | VAL | E | 274 | 71.671 | −21.785 | 29.182 | 1.00 | 50.20 | C |
| ATOM | 4856 | C | VAL | E | 274 | 71.954 | −21.011 | 27.891 | 1.00 | 49.58 | C |
| ATOM | 4857 | O | VAL | E | 274 | 72.997 | −21.178 | 27.255 | 1.00 | 49.28 | O |
| ATOM | 4858 | CB | VAL | E | 274 | 71.830 | −20.800 | 30.366 | 1.00 | 49.84 | C |
| ATOM | 4859 | CG1 | VAL | E | 274 | 73.191 | −20.125 | 30.298 | 1.00 | 49.41 | C |
| ATOM | 4860 | CG2 | VAL | E | 274 | 70.720 | −19.770 | 30.349 | 1.00 | 50.22 | C |
| ATOM | 4861 | N | GLU | E | 275 | 71.010 | −20.159 | 27.509 | 1.00 | 48.78 | N |
| ATOM | 4862 | CA | GLU | E | 275 | 71.183 | −19.335 | 26.329 | 1.00 | 47.91 | C |
| ATOM | 4863 | C | GLU | E | 275 | 70.564 | −17.960 | 26.526 | 1.00 | 46.62 | C |
| ATOM | 4864 | O | GLU | E | 275 | 69.689 | −17.765 | 27.368 | 1.00 | 46.91 | O |
| ATOM | 4865 | CB | GLU | E | 275 | 70.570 | −19.993 | 25.099 | 1.00 | 48.23 | C |
| ATOM | 4866 | CG | GLU | E | 275 | 69.073 | −20.101 | 25.150 | 1.00 | 49.42 | C |
| ATOM | 4867 | CD | GLU | E | 275 | 68.487 | −20.457 | 23.802 | 1.00 | 50.68 | C |
| ATOM | 4868 | OE1 | GLU | E | 275 | 69.158 | −21.191 | 23.039 | 1.00 | 51.67 | O |
| ATOM | 4869 | OE2 | GLU | E | 275 | 67.356 | −20.011 | 23.510 | 1.00 | 51.40 | O |

TABLE 3-continued

FGFR2(D2–D3) Complexed with FGF2

| ATOM | 4870 | N | PHE | E | 276 | 71.051 | −17.005 | 25.746 | 1.00 | 44.96 | N |
|---|---|---|---|---|---|---|---|---|---|---|---|
| ATOM | 4871 | CA | PHE | E | 276 | 70.557 | −15.642 | 25.781 | 1.00 | 43.18 | C |
| ATOM | 4872 | C | PHE | E | 276 | 70.298 | −15.259 | 24.342 | 1.00 | 42.01 | C |
| ATOM | 4873 | O | PHE | E | 276 | 71.174 | −15.394 | 23.488 | 1.00 | 41.08 | O |
| ATOM | 4874 | CB | PHE | E | 276 | 71.595 | −14.715 | 26.398 | 1.00 | 44.88 | C |
| ATOM | 4875 | CG | PHE | E | 276 | 71.764 | −14.901 | 27.878 | 1.00 | 46.37 | C |
| ATOM | 4876 | CD1 | PHE | E | 276 | 70.721 | −14.605 | 28.749 | 1.00 | 46.80 | C |
| ATOM | 4877 | CD2 | PHE | E | 276 | 72.977 | −15.350 | 28.402 | 1.00 | 46.66 | C |
| ATOM | 4878 | CE1 | PHE | E | 276 | 70.883 | −14.749 | 30.129 | 1.00 | 48.86 | C |
| ATOM | 4879 | CE2 | PHE | E | 276 | 73.154 | −15.499 | 29.775 | 1.00 | 48.80 | C |
| ATOM | 4880 | CZ | PHE | E | 276 | 72.104 | −15.198 | 30.648 | 1.00 | 48.50 | C |
| ATOM | 4881 | N | VAL | E | 277 | 69.084 | −14.799 | 24.072 | 1.00 | 40.85 | N |
| ATOM | 4882 | CA | VAL | E | 277 | 68.710 | −14.420 | 22.722 | 1.00 | 40.07 | C |
| ATOM | 4883 | C | VAL | E | 277 | 68.559 | −12.922 | 22.573 | 1.00 | 39.63 | C |
| ATOM | 4884 | O | VAL | E | 277 | 68.187 | −12.216 | 23.512 | 1.00 | 40.44 | O |
| ATOM | 4885 | CB | VAL | E | 277 | 67.393 | −15.087 | 22.303 | 1.00 | 39.97 | C |
| ATOM | 4886 | CG1 | VAL | E | 277 | 67.072 | −14.742 | 20.862 | 1.00 | 39.49 | C |
| ATOM | 4887 | CG2 | VAL | E | 277 | 67.503 | −16.591 | 22.484 | 1.00 | 40.06 | C |
| ATOM | 4888 | N | CYS | E | 278 | 68.850 | −12.438 | 21.376 | 1.00 | 38.95 | N |
| ATOM | 4889 | CA | CYS | E | 278 | 68.744 | −11.023 | 21.092 | 1.00 | 38.48 | C |
| ATOM | 4890 | C | CYS | E | 278 | 68.168 | −10.848 | 19.694 | 1.00 | 37.35 | C |
| ATOM | 4891 | O | CYS | E | 278 | 68.469 | −11.642 | 18.809 | 1.00 | 37.61 | O |
| ATOM | 4892 | CB | CYS | E | 278 | 70.122 | −10.375 | 21.170 | 1.00 | 39.85 | C |
| ATOM | 4893 | SG | CYS | E | 278 | 70.048 | −8.589 | 21.045 | 1.00 | 44.17 | S |
| ATOM | 4894 | N | LYS | E | 279 | 67.334 | −9.825 | 19.506 | 1.00 | 35.62 | N |
| ATOM | 4895 | CA | LYS | E | 279 | 66.729 | −9.538 | 18.198 | 1.00 | 34.29 | C |
| ATOM | 4896 | C | LYS | E | 279 | 66.988 | −8.093 | 17.770 | 1.00 | 33.03 | C |
| ATOM | 4897 | O | LYS | E | 279 | 66.437 | −7.149 | 18.356 | 1.00 | 31.92 | O |
| ATOM | 4898 | CB | LYS | E | 279 | 65.214 | −9.788 | 18.220 | 1.00 | 34.84 | C |
| ATOM | 4899 | CG | LYS | E | 279 | 64.798 | −11.190 | 17.806 | 1.00 | 37.35 | C |
| ATOM | 4900 | CD | LYS | E | 279 | 65.191 | −11.495 | 16.349 | 1.00 | 37.45 | C |
| ATOM | 4901 | CE | LYS | E | 279 | 64.485 | −10.561 | 15.370 | 1.00 | 38.22 | C |
| ATOM | 4902 | NZ | LYS | E | 279 | 64.821 | −10.836 | 13.944 | 1.00 | 36.90 | N |
| ATOM | 4903 | N | VAL | E | 280 | 67.799 | −7.933 | 16.727 | 1.00 | 31.70 | N |
| ATOM | 4904 | CA | VAL | E | 280 | 68.179 | −6.614 | 16.223 | 1.00 | 30.63 | C |
| ATOM | 4905 | C | VAL | E | 280 | 67.595 | −6.185 | 14.877 | 1.00 | 30.67 | C |
| ATOM | 4906 | O | VAL | E | 280 | 67.388 | −7.000 | 13.972 | 1.00 | 30.96 | O |
| ATOM | 4907 | CB | VAL | E | 280 | 69.721 | −6.510 | 16.128 | 1.00 | 31.01 | C |
| ATOM | 4908 | CG1 | VAL | E | 280 | 70.128 | −5.143 | 15.601 | 1.00 | 30.63 | C |
| ATOM | 4909 | CG2 | VAL | E | 280 | 70.344 | −6.785 | 17.501 | 1.00 | 30.60 | C |
| ATOM | 4910 | N | TYR | E | 281 | 67.340 | −4.883 | 14.758 | 1.00 | 30.41 | N |
| ATOM | 4911 | CA | TYR | E | 281 | 66.812 | −4.277 | 13.534 | 1.00 | 30.43 | C |
| ATOM | 4912 | C | TYR | E | 281 | 67.654 | −3.033 | 13.214 | 1.00 | 29.51 | C |
| ATOM | 4913 | O | TYR | E | 281 | 67.939 | −2.232 | 14.101 | 1.00 | 30.49 | O |
| ATOM | 4914 | CB | TYR | E | 281 | 65.341 | −3.885 | 13.726 | 1.00 | 30.72 | C |
| ATOM | 4915 | N | SER | E | 282 | 68.059 | −2.881 | 11.959 | 1.00 | 28.51 | N |
| ATOM | 4916 | CA | SER | E | 282 | 68.873 | −1.743 | 11.541 | 1.00 | 28.49 | C |
| ATOM | 4917 | C | SER | E | 282 | 68.981 | −1.649 | 10.016 | 1.00 | 28.34 | C |
| ATOM | 4918 | O | SER | E | 282 | 68.990 | −2.670 | 9.335 | 1.00 | 28.39 | O |
| ATOM | 4919 | CB | SER | E | 282 | 70.276 | −1.872 | 12.144 | 1.00 | 28.98 | C |
| ATOM | 4920 | OG | SER | E | 282 | 71.129 | −0.841 | 11.680 | 1.00 | 27.93 | O |
| ATOM | 4921 | N | ASP | E | 283 | 69.053 | −0.425 | 9.489 | 1.00 | 28.16 | N |
| ATOM | 4922 | CA | ASP | E | 283 | 69.186 | −0.203 | 8.043 | 1.00 | 27.48 | C |
| ATOM | 4923 | C | ASP | E | 283 | 70.686 | −0.255 | 7.763 | 1.00 | 27.69 | C |
| ATOM | 4924 | O | ASP | E | 283 | 71.153 | −1.114 | 7.020 | 1.00 | 27.69 | O |
| ATOM | 4925 | CB | ASP | E | 283 | 68.635 | 1.173 | 7.652 | 1.00 | 27.30 | C |
| ATOM | 4926 | CG | ASP | E | 283 | 68.615 | 1.398 | 6.138 | 1.00 | 26.87 | C |
| ATOM | 4927 | OD1 | ASP | E | 283 | 69.363 | 0.720 | 5.396 | 1.00 | 26.10 | O |
| ATOM | 4928 | OD2 | ASP | E | 283 | 67.847 | 2.276 | 5.689 | 1.00 | 26.11 | O |
| ATOM | 4929 | N | ALA | E | 284 | 71.432 | 0.671 | 8.363 | 1.00 | 26.91 | N |
| ATOM | 4930 | CA | ALA | E | 284 | 72.885 | 0.684 | 8.230 | 1.00 | 27.55 | C |
| ATOM | 4931 | C | ALA | E | 284 | 73.342 | −0.636 | 8.860 | 1.00 | 27.06 | C |
| ATOM | 4932 | O | ALA | E | 284 | 72.814 | −1.034 | 9.903 | 1.00 | 26.87 | O |
| ATOM | 4933 | CB | ALA | E | 284 | 73.485 | 1.859 | 9.011 | 1.00 | 26.70 | C |
| ATOM | 4934 | N | GLN | E | 285 | 74.303 | −1.320 | 8.241 | 1.00 | 26.18 | N |
| ATOM | 4935 | CA | GLN | E | 285 | 74.783 | −2.598 | 8.807 | 1.00 | 26.17 | C |
| ATOM | 4936 | C | GLN | E | 285 | 75.162 | −2.456 | 10.277 | 1.00 | 25.13 | C |
| ATOM | 4937 | O | GLN | E | 285 | 75.998 | −1.627 | 10.636 | 1.00 | 25.37 | O |
| ATOM | 4938 | CB | GLN | E | 285 | 76.004 | −3.168 | 8.062 | 1.00 | 26.14 | C |
| ATOM | 4939 | CG | GLN | E | 285 | 75.734 | −3.808 | 6.714 | 1.00 | 27.73 | C |
| ATOM | 4940 | CD | GLN | E | 285 | 74.706 | −4.913 | 6.765 | 1.00 | 27.55 | C |
| ATOM | 4941 | OE1 | GLN | E | 285 | 73.663 | −4.815 | 6.136 | 1.00 | 29.93 | O |
| ATOM | 4942 | NE2 | GLN | E | 285 | 74.992 | −5.973 | 7.516 | 1.00 | 29.65 | N |
| ATOM | 4943 | N | PRO | E | 286 | 74.543 | −3.274 | 11.141 | 1.00 | 24.69 | N |
| ATOM | 4944 | CA | PRO | E | 286 | 74.825 | −3.245 | 12.580 | 1.00 | 25.25 | C |
| ATOM | 4945 | C | PRO | E | 286 | 75.918 | −4.237 | 12.992 | 1.00 | 25.84 | C |
| ATOM | 4946 | O | PRO | E | 286 | 76.096 | −5.270 | 12.359 | 1.00 | 27.46 | O |

TABLE 3-continued

FGFR2(D2–D3) Complexed with FGF2

| ATOM | 4947 | CB | PRO | E | 286 | 73.467 | −3.605 | 13.181 | 1.00 | 24.49 | C |
|---|---|---|---|---|---|---|---|---|---|---|---|
| ATOM | 4948 | CG | PRO | E | 286 | 72.960 | −4.655 | 12.225 | 1.00 | 23.95 | C |
| ATOM | 4949 | CD | PRO | E | 286 | 73.349 | −4.085 | 10.851 | 1.00 | 24.51 | C |
| ATOM | 4950 | N | HIS | E | 287 | 76.654 | −3.911 | 14.052 | 1.00 | 26.68 | N |
| ATOM | 4951 | CA | HIS | E | 287 | 77.702 | −4.786 | 14.571 | 1.00 | 27.28 | C |
| ATOM | 4952 | C | HIS | E | 287 | 77.250 | −5.261 | 15.950 | 1.00 | 27.80 | C |
| ATOM | 4953 | O | HIS | E | 287 | 77.062 | −4.458 | 16.868 | 1.00 | 27.59 | O |
| ATOM | 4954 | CB | HIS | E | 287 | 79.044 | −4.055 | 14.680 | 1.00 | 27.34 | C |
| ATOM | 4955 | CG | HIS | E | 287 | 80.167 | −4.937 | 15.139 | 1.00 | 28.97 | C |
| ATOM | 4956 | ND1 | HIS | E | 287 | 80.689 | −4.880 | 16.416 | 1.00 | 29.15 | N |
| ATOM | 4957 | CD2 | HIS | E | 287 | 80.832 | −5.935 | 14.506 | 1.00 | 28.29 | C |
| ATOM | 4958 | CE1 | HIS | E | 287 | 81.625 | −5.803 | 16.551 | 1.00 | 29.45 | C |
| ATOM | 4959 | NE2 | HIS | E | 287 | 81.731 | −6.459 | 15.406 | 1.00 | 29.06 | N |
| ATOM | 4960 | N | ILE | E | 288 | 77.061 | −6.570 | 16.081 | 1.00 | 28.01 | N |
| ATOM | 4961 | CA | ILE | E | 288 | 76.584 | −7.159 | 17.323 | 1.00 | 29.20 | C |
| ATOM | 4962 | C | ILE | E | 288 | 77.650 | −7.931 | 18.104 | 1.00 | 30.30 | C |
| ATOM | 4963 | O | ILE | E | 288 | 78.469 | −8.645 | 17.521 | 1.00 | 31.71 | O |
| ATOM | 4964 | CB | ILE | E | 288 | 75.385 | −8.087 | 17.018 | 1.00 | 27.76 | C |
| ATOM | 4965 | CG1 | ILE | E | 288 | 74.285 | −7.278 | 16.316 | 1.00 | 28.76 | C |
| ATOM | 4966 | CG2 | ILE | E | 288 | 74.850 | −8.717 | 18.290 | 1.00 | 27.88 | C |
| ATOM | 4967 | CD1 | ILE | E | 288 | 73.227 | −8.141 | 15.623 | 1.00 | 25.74 | C |
| ATOM | 4968 | N | GLN | E | 289 | 77.641 | −7.771 | 19.426 | 1.00 | 31.39 | N |
| ATOM | 4969 | CA | GLN | E | 289 | 78.580 | −8.475 | 20.292 | 1.00 | 33.14 | C |
| ATOM | 4970 | C | GLN | E | 289 | 77.924 | −8.769 | 21.633 | 1.00 | 33.52 | C |
| ATOM | 4971 | O | GLN | E | 289 | 76.961 | −8.102 | 22.018 | 1.00 | 34.50 | O |
| ATOM | 4972 | CB | GLN | E | 289 | 79.861 | −7.650 | 20.495 | 1.00 | 34.53 | C |
| ATOM | 4973 | CG | GLN | E | 289 | 79.655 | −6.240 | 21.025 | 1.00 | 35.38 | C |
| ATOM | 4974 | CD | GLN | E | 289 | 80.970 | −5.538 | 21.279 | 1.00 | 37.44 | C |
| ATOM | 4975 | OE1 | GLN | E | 289 | 81.851 | −6.087 | 21.938 | 1.00 | 39.19 | O |
| ATOM | 4976 | NE2 | GLN | E | 289 | 81.113 | −4.319 | 20.765 | 1.00 | 37.44 | N |
| ATOM | 4977 | N | TRP | E | 290 | 78.425 | −9.789 | 22.323 | 1.00 | 33.78 | N |
| ATOM | 4978 | CA | TRP | E | 290 | 77.902 | −10.171 | 23.628 | 1.00 | 34.30 | C |
| ATOM | 4979 | C | TRP | E | 290 | 78.965 | −9.867 | 24.670 | 1.00 | 35.91 | C |
| ATOM | 4980 | O | TRP | E | 290 | 80.131 | −10.253 | 24.515 | 1.00 | 36.39 | O |
| ATOM | 4981 | CB | TRP | E | 290 | 77.537 | −11.663 | 23.669 | 1.00 | 32.84 | C |
| ATOM | 4982 | CG | TRP | E | 290 | 76.254 | −12.011 | 22.953 | 1.00 | 31.62 | C |
| ATOM | 4983 | CD1 | TRP | E | 290 | 76.120 | −12.430 | 21.659 | 1.00 | 32.53 | C |
| ATOM | 4984 | CD2 | TRP | E | 290 | 74.931 | −11.985 | 23.503 | 1.00 | 30.60 | C |
| ATOM | 4985 | NE1 | TRP | E | 290 | 74.796 | −12.673 | 21.369 | 1.00 | 30.76 | N |
| ATOM | 4986 | CE2 | TRP | E | 290 | 74.045 | −12.406 | 22.484 | 1.00 | 31.02 | C |
| ATOM | 4987 | CE3 | TRP | E | 290 | 74.406 | −11.644 | 24.757 | 1.00 | 30.73 | C |
| ATOM | 4988 | CZ2 | TRP | E | 290 | 72.661 | −12.497 | 22.680 | 1.00 | 30.30 | C |
| ATOM | 4989 | CZ3 | TRP | E | 290 | 73.029 | −11.736 | 24.955 | 1.00 | 30.32 | C |
| ATOM | 4990 | CH2 | TRP | E | 290 | 72.173 | −12.159 | 23.918 | 1.00 | 31.09 | C |
| ATOM | 4991 | N | ILE | E | 291 | 78.561 | −9.176 | 25.731 | 1.00 | 37.47 | N |
| ATOM | 4992 | CA | ILE | E | 291 | 79.487 | −8.787 | 26.785 | 1.00 | 39.92 | C |
| ATOM | 4993 | C | ILE | E | 291 | 79.075 | −9.239 | 28.185 | 1.00 | 41.83 | C |
| ATOM | 4994 | O | ILE | E | 291 | 77.892 | −9.260 | 28.529 | 1.00 | 41.92 | O |
| ATOM | 4995 | CB | ILE | E | 291 | 79.658 | −7.263 | 26.808 | 1.00 | 39.84 | C |
| ATOM | 4996 | CG1 | ILE | E | 291 | 80.151 | −6.777 | 25.442 | 1.00 | 39.98 | C |
| ATOM | 4997 | CG2 | ILE | E | 291 | 80.619 | −6.867 | 27.912 | 1.00 | 39.95 | C |
| ATOM | 4998 | CD1 | ILE | E | 291 | 80.132 | −5.274 | 25.295 | 1.00 | 40.10 | C |
| ATOM | 4999 | N | LYS | E | 292 | 80.073 | −9.601 | 28.988 | 1.00 | 43.20 | N |
| ATOM | 5000 | CA | LYS | E | 292 | 79.856 | −10.022 | 30.366 | 1.00 | 44.66 | C |
| ATOM | 5001 | C | LYS | E | 292 | 80.471 | −8.948 | 31.251 | 1.00 | 45.75 | C |
| ATOM | 5002 | O | LYS | E | 292 | 81.609 | −8.523 | 31.028 | 1.00 | 45.37 | O |
| ATOM | 5003 | CB | LYS | E | 292 | 80.536 | −11.362 | 30.649 | 1.00 | 44.86 | C |
| ATOM | 5004 | N | HIS | E | 293 | 79.714 | −8.506 | 32.250 | 1.00 | 47.10 | N |
| ATOM | 5005 | CA | HIS | E | 293 | 80.183 | −7.476 | 33.167 | 1.00 | 48.94 | C |
| ATOM | 5006 | C | HIS | E | 293 | 81.057 | −8.107 | 34.242 | 1.00 | 50.05 | C |
| ATOM | 5007 | O | HIS | E | 293 | 80.555 | −8.806 | 35.125 | 1.00 | 50.26 | O |
| ATOM | 5008 | CB | HIS | E | 293 | 78.988 | −6.768 | 33.816 | 1.00 | 48.54 | C |
| ATOM | 5009 | N | VAL | E | 294 | 82.363 | −7.861 | 34.155 | 1.00 | 51.57 | N |
| ATOM | 5010 | CA | VAL | E | 294 | 83.319 | −8.401 | 35.115 | 1.00 | 53.36 | C |
| ATOM | 5011 | C | VAL | E | 294 | 83.961 | −7.281 | 35.930 | 1.00 | 54.68 | C |
| ATOM | 5012 | O | VAL | E | 294 | 84.546 | −7.524 | 36.986 | 1.00 | 56.28 | O |
| ATOM | 5013 | CB | VAL | E | 294 | 84.436 | −9.201 | 34.407 | 1.00 | 53.01 | C |
| ATOM | 5014 | N | PRO | E | 307 | 83.804 | 0.595 | 34.001 | 1.00 | 60.83 | N |
| ATOM | 5015 | CA | PRO | E | 307 | 83.190 | −0.739 | 34.037 | 1.00 | 60.46 | C |
| ATOM | 5016 | C | PRO | E | 307 | 84.063 | −1.813 | 33.386 | 1.00 | 59.98 | C |
| ATOM | 5017 | O | PRO | E | 307 | 84.386 | −1.725 | 32.199 | 1.00 | 60.20 | O |
| ATOM | 5018 | CB | PRO | E | 307 | 81.880 | −0.530 | 33.280 | 1.00 | 60.75 | C |
| ATOM | 5019 | CG | PRO | E | 307 | 82.275 | 0.476 | 32.231 | 1.00 | 60.65 | C |
| ATOM | 5020 | CD | PRO | E | 307 | 83.107 | 1.468 | 33.037 | 1.00 | 61.05 | C |
| ATOM | 5021 | N | TYR | E | 308 | 84.441 | −2.822 | 34.166 | 1.00 | 58.80 | N |
| ATOM | 5022 | CA | TYR | E | 308 | 85.266 | −3.917 | 33.655 | 1.00 | 57.71 | C |
| ATOM | 5023 | C | TYR | E | 308 | 84.411 | −4.844 | 32.796 | 1.00 | 56.51 | C |

TABLE 3-continued

FGFR2(D2–D3) Complexed with FGF2

| ATOM | 5024 | O | TYR | E | 308 | 83.524 | −5.533 | 33.301 | 1.00 | 57.08 | O |
|---|---|---|---|---|---|---|---|---|---|---|---|
| ATOM | 5025 | CB | TYR | E | 308 | 85.887 | −4.707 | 34.815 | 1.00 | 57.74 | C |
| ATOM | 5026 | N | LEU | E | 309 | 84.689 | −4.865 | 31.497 | 1.00 | 55.13 | N |
| ATOM | 5027 | CA | LEU | E | 309 | 83.926 | −5.690 | 30.570 | 1.00 | 53.60 | C |
| ATOM | 5028 | C | LEU | E | 309 | 84.771 | −6.784 | 29.916 | 1.00 | 52.13 | C |
| ATOM | 5029 | O | LEU | E | 309 | 85.991 | −6.664 | 29.813 | 1.00 | 52.33 | O |
| ATOM | 5030 | CB | LEU | E | 309 | 83.313 | −4.788 | 29.496 | 1.00 | 53.76 | C |
| ATOM | 5031 | CG | LEU | E | 309 | 82.632 | −3.528 | 30.042 | 1.00 | 54.69 | C |
| ATOM | 5032 | CD1 | LEU | E | 309 | 82.231 | −2.615 | 28.886 | 1.00 | 55.37 | C |
| ATOM | 5033 | CD2 | LEU | E | 309 | 81.426 | −3.910 | 30.889 | 1.00 | 54.17 | C |
| ATOM | 5034 | N | LYS | E | 310 | 84.111 | −7.852 | 29.483 | 1.00 | 49.92 | N |
| ATOM | 5035 | CA | LYS | E | 310 | 84.784 | −8.963 | 28.812 | 1.00 | 47.92 | C |
| ATOM | 5036 | C | LYS | E | 310 | 83.957 | −9.383 | 27.596 | 1.00 | 46.18 | C |
| ATOM | 5037 | O | LYS | E | 310 | 82.791 | −9.760 | 27.733 | 1.00 | 45.41 | O |
| ATOM | 5038 | CB | LYS | E | 310 | 84.934 | −10.151 | 29.766 | 1.00 | 47.80 | C |
| ATOM | 5039 | N | VAL | E | 311 | 84.561 | −9.321 | 26.412 | 1.00 | 44.53 | N |
| ATOM | 5040 | CA | VAL | E | 311 | 83.864 | −9.690 | 25.178 | 1.00 | 42.94 | C |
| ATOM | 5041 | C | VAL | E | 311 | 83.812 | −11.197 | 24.979 | 1.00 | 42.70 | C |
| ATOM | 5042 | O | VAL | E | 311 | 84.837 | −11.841 | 24.753 | 1.00 | 43.13 | O |
| ATOM | 5043 | CB | VAL | E | 311 | 84.539 | −9.071 | 23.934 | 1.00 | 42.45 | C |
| ATOM | 5044 | CG1 | VAL | E | 311 | 83.833 | −9.550 | 22.661 | 1.00 | 40.98 | C |
| ATOM | 5045 | CG2 | VAL | E | 311 | 84.511 | −7.557 | 24.029 | 1.00 | 41.52 | C |
| ATOM | 5046 | N | LEU | E | 312 | 82.609 | −11.753 | 25.041 | 1.00 | 41.79 | N |
| ATOM | 5047 | CA | LEU | E | 312 | 82.418 | −13.188 | 24.869 | 1.00 | 40.92 | C |
| ATOM | 5048 | C | LEU | E | 312 | 82.405 | −13.596 | 23.405 | 1.00 | 40.03 | C |
| ATOM | 5049 | O | LEU | E | 312 | 82.932 | −14.643 | 23.040 | 1.00 | 40.10 | O |
| ATOM | 5050 | CB | LEU | E | 312 | 81.102 | −13.625 | 25.519 | 1.00 | 42.05 | C |
| ATOM | 5051 | CG | LEU | E | 312 | 80.890 | −13.141 | 26.956 | 1.00 | 43.75 | C |
| ATOM | 5052 | CD1 | LEU | E | 312 | 79.784 | −13.962 | 27.606 | 1.00 | 42.68 | C |
| ATOM | 5053 | CD2 | LEU | E | 312 | 82.187 | −13.289 | 27.748 | 1.00 | 44.25 | C |
| ATOM | 5054 | N | LYS | E | 313 | 81.771 | −12.785 | 22.569 | 1.00 | 38.60 | N |
| ATOM | 5055 | CA | LYS | E | 313 | 81.715 | −13.069 | 21.146 | 1.00 | 37.54 | C |
| ATOM | 5056 | C | LYS | E | 313 | 81.341 | −11.805 | 20.395 | 1.00 | 36.63 | C |
| ATOM | 5057 | O | LYS | E | 313 | 80.612 | −10.952 | 20.910 | 1.00 | 36.09 | O |
| ATOM | 5058 | CB | LYS | E | 313 | 80.741 | −14.216 | 20.832 | 1.00 | 38.37 | C |
| ATOM | 5059 | CG | LYS | E | 313 | 79.283 | −13.881 | 20.927 | 1.00 | 40.25 | C |
| ATOM | 5060 | CD | LYS | E | 313 | 78.434 | −15.110 | 20.642 | 1.00 | 41.30 | C |
| ATOM | 5061 | CE | LYS | E | 313 | 78.667 | −15.657 | 19.245 | 1.00 | 42.13 | C |
| ATOM | 5062 | NZ | LYS | E | 313 | 77.712 | −16.764 | 18.931 | 1.00 | 43.04 | N |
| ATOM | 5063 | N | ALA | E | 314 | 81.871 | −11.679 | 19.181 | 1.00 | 34.76 | N |
| ATOM | 5064 | CA | ALA | E | 314 | 81.633 | −10.501 | 18.362 | 1.00 | 33.57 | C |
| ATOM | 5065 | C | ALA | E | 314 | 81.531 | −10.845 | 16.883 | 1.00 | 33.42 | C |
| ATOM | 5066 | O | ALA | E | 314 | 82.287 | −11.684 | 16.371 | 1.00 | 33.25 | O |
| ATOM | 5067 | CB | ALA | E | 314 | 82.744 | −9.494 | 18.588 | 1.00 | 33.65 | C |
| ATOM | 5068 | N | ALA | E | 315 | 80.595 | −10.185 | 16.201 | 1.00 | 32.14 | N |
| ATOM | 5069 | CA | ALA | E | 315 | 80.353 | −10.398 | 14.780 | 1.00 | 31.01 | C |
| ATOM | 5070 | C | ALA | E | 315 | 81.549 | −10.035 | 13.903 | 1.00 | 30.72 | C |
| ATOM | 5071 | O | ALA | E | 315 | 82.361 | −9.177 | 14.257 | 1.00 | 30.48 | O |
| ATOM | 5072 | CB | ALA | E | 315 | 79.121 | −9.607 | 14.335 | 1.00 | 30.66 | C |
| ATOM | 5073 | N | GLY | E | 316 | 81.631 | −10.694 | 12.751 | 1.00 | 30.24 | N |
| ATOM | 5074 | CA | GLY | E | 316 | 82.708 | −10.456 | 11.816 | 1.00 | 31.94 | C |
| ATOM | 5075 | C | GLY | E | 316 | 82.770 | −11.540 | 10.755 | 1.00 | 33.59 | C |
| ATOM | 5076 | O | GLY | E | 316 | 81.899 | −12.405 | 10.683 | 1.00 | 32.55 | O |
| ATOM | 5077 | N | VAL | E | 317 | 83.802 | −11.479 | 9.925 | 1.00 | 35.48 | N |
| ATOM | 5078 | CA | VAL | E | 317 | 84.013 | −12.449 | 8.860 | 1.00 | 38.38 | C |
| ATOM | 5079 | C | VAL | E | 317 | 84.061 | −13.890 | 9.384 | 1.00 | 39.34 | C |
| ATOM | 5080 | O | VAL | E | 317 | 83.570 | −14.810 | 8.732 | 1.00 | 39.08 | O |
| ATOM | 5081 | CB | VAL | E | 317 | 85.339 | −12.140 | 8.121 | 1.00 | 39.18 | C |
| ATOM | 5082 | CG1 | VAL | E | 317 | 85.814 | −13.363 | 7.350 | 1.00 | 41.23 | C |
| ATOM | 5083 | CG2 | VAL | E | 317 | 85.133 | −10.970 | 7.157 | 1.00 | 39.65 | C |
| ATOM | 5084 | N | ASN | E | 318 | 84.649 | −14.073 | 10.563 | 1.00 | 41.02 | N |
| ATOM | 5085 | CA | ASN | E | 318 | 84.772 | −15.397 | 11.165 | 1.00 | 42.81 | C |
| ATOM | 5086 | C | ASN | E | 318 | 83.640 | −15.765 | 12.112 | 1.00 | 43.44 | C |
| ATOM | 5087 | O | ASN | E | 318 | 83.595 | −16.879 | 12.635 | 1.00 | 43.81 | O |
| ATOM | 5088 | CB | ASN | E | 318 | 86.113 | −15.511 | 11.885 | 1.00 | 43.79 | C |
| ATOM | 5089 | CG | ASN | E | 318 | 87.251 | −15.783 | 10.928 | 1.00 | 44.65 | C |
| ATOM | 5090 | OD1 | ASN | E | 318 | 88.377 | −15.342 | 11.140 | 1.00 | 46.43 | O |
| ATOM | 5091 | ND2 | ASN | E | 318 | 86.961 | −16.526 | 9.863 | 1.00 | 45.45 | N |
| ATOM | 5092 | N | THR | E | 319 | 82.728 | −14.825 | 12.336 | 1.00 | 43.23 | N |
| ATOM | 5093 | CA | THR | E | 319 | 81.585 | −15.058 | 13.207 | 1.00 | 42.64 | C |
| ATOM | 5094 | C | THR | E | 319 | 80.401 | −14.304 | 12.607 | 1.00 | 42.30 | C |
| ATOM | 5095 | O | THR | E | 319 | 80.025 | −13.224 | 13.070 | 1.00 | 41.73 | O |
| ATOM | 5096 | CB | THR | E | 319 | 81.845 | −14.542 | 14.629 | 1.00 | 42.95 | C |
| ATOM | 5097 | OG1 | THR | E | 319 | 83.161 | −14.923 | 15.053 | 1.00 | 43.57 | O |
| ATOM | 5098 | CG2 | THR | E | 319 | 80.829 | −15.132 | 15.583 | 1.00 | 42.54 | C |
| ATOM | 5099 | N | THR | E | 320 | 79.841 | −14.898 | 11.561 | 1.00 | 41.32 | N |
| ATOM | 5100 | CA | THR | E | 320 | 78.713 | −14.381 | 10.791 | 1.00 | 41.14 | C |

TABLE 3-continued

FGFR2(D2–D3) Complexed with FGF2

| ATOM | 5101 | C | THR | E | 320 | 77.460 | −13.982 | 11.580 | 1.00 | 40.79 | C |
|---|---|---|---|---|---|---|---|---|---|---|---|
| ATOM | 5102 | O | THR | E | 320 | 77.228 | −14.481 | 12.679 | 1.00 | 40.11 | O |
| ATOM | 5103 | CB | THR | E | 320 | 78.327 | −15.445 | 9.717 | 1.00 | 40.88 | C |
| ATOM | 5104 | OG1 | THR | E | 320 | 79.269 | −15.385 | 8.642 | 1.00 | 41.69 | O |
| ATOM | 5105 | CG2 | THR | E | 320 | 76.926 | −15.235 | 9.186 | 1.00 | 41.14 | C |
| ATOM | 5106 | N | ASP | E | 321 | 76.652 | −13.091 | 10.995 | 1.00 | 40.17 | N |
| ATOM | 5107 | CA | ASP | E | 321 | 75.402 | −12.634 | 11.608 | 1.00 | 40.26 | C |
| ATOM | 5108 | C | ASP | E | 321 | 74.370 | −13.760 | 11.740 | 1.00 | 40.48 | C |
| ATOM | 5109 | O | ASP | E | 321 | 73.453 | −13.671 | 12.551 | 1.00 | 40.99 | O |
| ATOM | 5110 | CB | ASP | E | 321 | 74.761 | −11.492 | 10.785 | 1.00 | 40.57 | C |
| ATOM | 5111 | CG | ASP | E | 321 | 75.508 | −10.164 | 10.911 | 1.00 | 40.77 | C |
| ATOM | 5112 | CD1 | ASP | E | 321 | 76.166 | −9.942 | 11.943 | 1.00 | 41.36 | O |
| ATOM | 5113 | OD2 | ASP | E | 321 | 75.421 | −9.334 | 9.980 | 1.00 | 40.77 | O |
| ATOM | 5114 | N | LYS | E | 322 | 74.513 | −14.812 | 10.941 | 1.00 | 40.71 | N |
| ATOM | 5115 | CA | LYS | E | 322 | 73.561 | −15.922 | 10.970 | 1.00 | 40.47 | C |
| ATOM | 5116 | C | LYS | E | 322 | 73.340 | −16.497 | 12.366 | 1.00 | 40.34 | C |
| ATOM | 5117 | O | LYS | E | 322 | 72.213 | −16.817 | 12.739 | 1.00 | 40.39 | O |
| ATOM | 5118 | CB | LYS | E | 322 | 74.014 | −17.038 | 10.024 | 1.00 | 40.54 | C |
| ATOM | 5119 | N | GLU | E | 323 | 74.410 | −16.605 | 13.146 | 1.00 | 39.99 | N |
| ATOM | 5120 | CA | GLU | E | 323 | 74.304 | −17.172 | 14.486 | 1.00 | 40.42 | C |
| ATOM | 5121 | C | GLU | E | 323 | 74.793 | −16.255 | 15.616 | 1.00 | 40.12 | C |
| ATOM | 5122 | O | GLU | E | 323 | 74.975 | −16.705 | 16.752 | 1.00 | 40.19 | O |
| ATOM | 5123 | CB | GLU | E | 323 | 75.079 | −18.497 | 14.539 | 1.00 | 41.39 | C |
| ATOM | 5124 | N | ILE | E | 324 | 74.980 | −14.974 | 15.315 | 1.00 | 39.32 | N |
| ATOM | 5125 | CA | ILE | E | 324 | 75.472 | −14.016 | 16.304 | 1.00 | 38.63 | C |
| ATOM | 5126 | C | ILE | E | 324 | 74.426 | −13.586 | 17.349 | 1.00 | 37.71 | C |
| ATOM | 5127 | O | ILE | E | 324 | 74.780 | −13.190 | 18.455 | 1.00 | 36.93 | O |
| ATOM | 5128 | CB | ILE | E | 324 | 76.038 | −12.750 | 15.577 | 1.00 | 39.58 | C |
| ATOM | 5129 | CG1 | ILE | E | 324 | 77.275 | −12.216 | 16.305 | 1.00 | 40.68 | C |
| ATOM | 5130 | CG2 | ILE | E | 324 | 74.959 | −11.683 | 15.445 | 1.00 | 38.88 | C |
| ATOM | 5131 | CD1 | ILE | E | 324 | 77.023 | −11.669 | 17.672 | 1.00 | 42.53 | C |
| ATOM | 5132 | N | GLU | E | 325 | 73.144 | −13.681 | 17.010 | 1.00 | 37.22 | N |
| ATOM | 5133 | CA | GLU | E | 325 | 72.085 | −13.264 | 17.932 | 1.00 | 38.65 | C |
| ATOM | 5134 | C | GLU | E | 325 | 71.729 | −14.213 | 19.085 | 1.00 | 39.26 | C |
| ATOM | 5135 | O | GLU | E | 325 | 70.838 | −13.921 | 19.883 | 1.00 | 38.60 | O |
| ATOM | 5136 | CB | GLU | E | 325 | 70.816 | −12.907 | 17.138 | 1.00 | 38.87 | C |
| ATOM | 5137 | CG | GLU | E | 325 | 70.909 | −11.561 | 16.393 | 1.00 | 40.03 | C |
| ATOM | 5138 | CD | GLU | E | 325 | 69.746 | −11.319 | 15.432 | 1.00 | 41.78 | C |
| ATOM | 5139 | OE1 | GLU | E | 325 | 69.663 | −12.037 | 14.413 | 1.00 | 42.23 | O |
| ATOM | 5140 | OE2 | GLU | E | 325 | 68.913 | −10.415 | 15.693 | 1.00 | 42.02 | O |
| ATOM | 5141 | N | VAL | E | 326 | 72.414 | −15.347 | 19.182 | 1.00 | 40.15 | N |
| ATOM | 5142 | CA | VAL | E | 326 | 72.149 | −16.281 | 20.270 | 1.00 | 41.03 | C |
| ATOM | 5143 | C | VAL | E | 326 | 73.467 | −16.648 | 20.937 | 1.00 | 41.51 | C |
| ATOM | 5144 | O | VAL | E | 326 | 74.438 | −16.974 | 20.264 | 1.00 | 41.62 | O |
| ATOM | 5145 | CB | VAL | E | 326 | 71.456 | −17.559 | 19.763 | 1.00 | 41.93 | C |
| ATOM | 5146 | CG1 | VAL | E | 326 | 71.125 | −18.469 | 20.942 | 1.00 | 42.60 | C |
| ATOM | 5147 | CG2 | VAL | E | 326 | 70.193 | −17.195 | 19.007 | 1.00 | 41.45 | C |
| ATOM | 5148 | N | LEU | E | 327 | 73.502 | −16.565 | 22.261 | 1.00 | 42.31 | N |
| ATOM | 5149 | CA | LEU | E | 327 | 74.705 | −16.881 | 23.024 | 1.00 | 43.48 | C |
| ATOM | 5150 | C | LEU | E | 327 | 74.463 | −18.120 | 23.880 | 1.00 | 44.60 | C |
| ATOM | 5151 | O | LEU | E | 327 | 73.572 | −18.122 | 24.732 | 1.00 | 44.30 | O |
| ATOM | 5152 | CB | LEU | E | 327 | 75.064 | −15.709 | 23.936 | 1.00 | 43.12 | C |
| ATOM | 5153 | CG | LEU | E | 327 | 76.273 | −15.926 | 24.848 | 1.00 | 43.38 | C |
| ATOM | 5154 | CD1 | LEU | E | 327 | 77.547 | −15.913 | 24.007 | 1.00 | 43.75 | C |
| ATOM | 5155 | CD2 | LEU | E | 327 | 76.331 | −14.839 | 25.913 | 1.00 | 42.65 | C |
| ATOM | 5156 | N | TYR | E | 328 | 75.264 | −19.161 | 23.662 | 1.00 | 45.83 | N |
| ATOM | 5157 | CA | TYR | E | 328 | 75.130 | −20.409 | 24.409 | 1.00 | 47.51 | C |
| ATOM | 5158 | C | TYR | E | 328 | 76.203 | −20.539 | 25.480 | 1.00 | 48.60 | C |
| ATOM | 5159 | O | TYR | E | 328 | 77.367 | −20.219 | 25.239 | 1.00 | 49.02 | O |
| ATOM | 5160 | CB | TYR | E | 328 | 75.230 | −21.604 | 23.465 | 1.00 | 48.05 | C |
| ATOM | 5161 | CG | TYR | E | 328 | 74.175 | −21.633 | 22.389 | 1.00 | 49.56 | C |
| ATOM | 5162 | CD1 | TYR | E | 328 | 74.428 | −21.111 | 21.118 | 1.00 | 50.39 | C |
| ATOM | 5163 | CD2 | TYR | E | 328 | 72.916 | −22.174 | 22.641 | 1.00 | 50.10 | C |
| ATOM | 5164 | CE1 | TYR | E | 328 | 73.451 | −21.132 | 20.121 | 1.00 | 50.75 | C |
| ATOM | 5165 | CE2 | TYR | E | 328 | 71.930 | −22.199 | 21.654 | 1.00 | 50.95 | C |
| ATOM | 5166 | CZ | TYR | E | 328 | 72.205 | −21.679 | 20.397 | 1.00 | 51.33 | C |
| ATOM | 5167 | OH | TYR | E | 328 | 71.234 | −21.720 | 19.416 | 1.00 | 52.19 | O |
| ATOM | 5168 | N | ILE | E | 329 | 75.808 | −21.025 | 26.653 | 1.00 | 50.10 | N |
| ATOM | 5169 | CA | ILE | E | 329 | 76.719 | −21.217 | 27.784 | 1.00 | 51.70 | C |
| ATOM | 5170 | C | ILE | E | 329 | 76.424 | −22.593 | 28.398 | 1.00 | 53.13 | C |
| ATOM | 5171 | O | ILE | E | 329 | 75.392 | −22.759 | 29.053 | 1.00 | 53.28 | O |
| ATOM | 5172 | CB | ILE | E | 329 | 76.466 | −20.124 | 28.857 | 1.00 | 51.99 | C |
| ATOM | 5173 | CG1 | ILE | E | 329 | 76.483 | −18.739 | 28.201 | 1.00 | 52.28 | C |
| ATOM | 5174 | CG2 | ILE | E | 329 | 77.518 | −20.203 | 29.953 | 1.00 | 52.51 | C |
| ATOM | 5175 | CD1 | ILE | E | 329 | 76.166 | −17.593 | 29.145 | 1.00 | 52.93 | C |
| ATOM | 5176 | N | ARG | E | 330 | 77.320 | −23.566 | 28.198 | 1.00 | 54.31 | N |
| ATOM | 5177 | CA | ARG | E | 330 | 77.128 | −24.929 | 28.713 | 1.00 | 54.98 | C |

TABLE 3-continued

FGFR2(D2–D3) Complexed with FGF2

| ATOM | 5178 | C | ARG | E | 330 | 77.949 | −25.259 | 29.959 | 1.00 | 55.26 | C |
|---|---|---|---|---|---|---|---|---|---|---|---|
| ATOM | 5179 | O | ARG | E | 330 | 79.005 | −24.666 | 30.184 | 1.00 | 55.44 | O |
| ATOM | 5180 | CB | ARG | E | 330 | 77.465 | −25.940 | 27.612 | 1.00 | 54.90 | C |
| ATOM | 5181 | N | ASN | E | 331 | 77.461 | −26.212 | 30.755 | 1.00 | 55.70 | N |
| ATOM | 5182 | CA | ASN | E | 331 | 78.154 | −26.636 | 31.970 | 1.00 | 56.20 | C |
| ATOM | 5183 | C | ASN | E | 331 | 78.593 | −25.414 | 32.768 | 1.00 | 56.64 | C |
| ATOM | 5184 | O | ASN | E | 331 | 79.781 | −25.231 | 33.039 | 1.00 | 56.90 | O |
| ATOM | 5185 | CB | ASN | E | 331 | 79.383 | −27.480 | 31.603 | 1.00 | 55.73 | C |
| ATOM | 5186 | N | VAL | E | 332 | 77.627 | −24.583 | 33.147 | 1.00 | 57.11 | N |
| ATOM | 5187 | CA | VAL | E | 332 | 77.916 | −23.357 | 33.884 | 1.00 | 57.24 | C |
| ATOM | 5188 | C | VAL | E | 332 | 78.510 | −23.565 | 35.271 | 1.00 | 57.22 | C |
| ATOM | 5189 | O | VAL | E | 332 | 78.233 | −24.556 | 35.940 | 1.00 | 57.43 | O |
| ATOM | 5190 | CB | VAL | E | 332 | 76.647 | −22.487 | 34.031 | 1.00 | 57.41 | C |
| ATOM | 5191 | N | THR | E | 333 | 79.334 | −22.612 | 35.688 | 1.00 | 57.10 | N |
| ATOM | 5192 | CA | THR | E | 333 | 79.963 | −22.634 | 37.001 | 1.00 | 57.30 | C |
| ATOM | 5193 | C | THR | E | 333 | 79.383 | −21.436 | 37.746 | 1.00 | 57.39 | C |
| ATOM | 5194 | O | THR | E | 333 | 78.661 | −20.632 | 37.155 | 1.00 | 57.78 | O |
| ATOM | 5195 | CB | THR | E | 333 | 81.493 | −22.459 | 36.901 | 1.00 | 57.30 | C |
| ATOM | 5196 | N | PHE | E | 334 | 79.684 | −21.309 | 39.033 | 1.00 | 57.05 | N |
| ATOM | 5197 | CA | PHE | E | 334 | 79.170 | −20.175 | 39.796 | 1.00 | 56.67 | C |
| ATOM | 5198 | C | PHE | E | 334 | 79.828 | −18.894 | 39.280 | 1.00 | 55.98 | C |
| ATOM | 5199 | O | PHE | E | 334 | 79.302 | −17.794 | 39.455 | 1.00 | 55.93 | O |
| ATOM | 5200 | CB | PHE | E | 334 | 79.456 | −20.357 | 41.292 | 1.00 | 57.08 | C |
| ATOM | 5201 | N | GLU | E | 335 | 80.977 | −19.052 | 38.633 | 1.00 | 54.82 | N |
| ATOM | 5202 | CA | GLU | E | 335 | 81.707 | −17.917 | 38.087 | 1.00 | 54.10 | C |
| ATOM | 5203 | C | GLU | E | 335 | 80.959 | −17.274 | 36.911 | 1.00 | 53.27 | C |
| ATOM | 5204 | O | GLU | E | 335 | 81.119 | −16.082 | 36.642 | 1.00 | 52.91 | O |
| ATOM | 5205 | CB | GLU | E | 335 | 83.102 | −18.368 | 37.634 | 1.00 | 54.01 | C |
| ATOM | 5206 | N | ASP | E | 336 | 80.140 | −18.060 | 36.217 | 1.00 | 52.36 | N |
| ATOM | 5207 | CA | ASP | E | 336 | 79.394 | −17.540 | 35.074 | 1.00 | 51.65 | C |
| ATOM | 5208 | C | ASP | E | 336 | 78.263 | −16.596 | 35.459 | 1.00 | 50.65 | C |
| ATOM | 5209 | O | ASP | E | 336 | 77.808 | −15.814 | 34.632 | 1.00 | 50.46 | O |
| ATOM | 5210 | CB | ASP | E | 336 | 78.829 | −18.678 | 34.221 | 1.00 | 51.50 | C |
| ATOM | 5211 | CG | ASP | E | 336 | 79.914 | −19.483 | 33.546 | 1.00 | 51.96 | C |
| ATOM | 5212 | OD1 | ASP | E | 336 | 80.862 | −18.865 | 33.010 | 1.00 | 50.96 | O |
| ATOM | 5213 | OD2 | ASP | E | 336 | 79.817 | −20.728 | 33.549 | 1.00 | 51.31 | O |
| ATOM | 5214 | N | ALA | E | 337 | 77.808 | −16.671 | 36.704 | 1.00 | 49.76 | N |
| ATOM | 5215 | CA | ALA | E | 337 | 76.731 | −15.803 | 37.167 | 1.00 | 49.26 | C |
| ATOM | 5216 | C | ALA | E | 337 | 77.085 | −14.351 | 36.894 | 1.00 | 49.07 | C |
| ATOM | 5217 | O | ALA | E | 337 | 78.259 | −13.976 | 36.914 | 1.00 | 49.31 | O |
| ATOM | 5218 | CB | ALA | E | 337 | 76.496 | −16.005 | 38.658 | 1.00 | 49.40 | C |
| ATOM | 5219 | N | GLY | E | 338 | 76.072 | −13.529 | 36.636 | 1.00 | 48.46 | N |
| ATOM | 5220 | CA | GLY | E | 338 | 76.341 | −12.127 | 36.366 | 1.00 | 47.35 | C |
| ATOM | 5221 | C | GLY | E | 338 | 75.481 | −11.508 | 35.280 | 1.00 | 46.17 | C |
| ATOM | 5222 | O | GLY | E | 338 | 74.546 | −12.134 | 34.772 | 1.00 | 45.24 | O |
| ATOM | 5223 | N | GLU | E | 339 | 75.818 | −10.270 | 34.924 | 1.00 | 44.77 | N |
| ATOM | 5224 | CA | GLU | E | 339 | 75.089 | −9.513 | 33.916 | 1.00 | 44.35 | C |
| ATOM | 5225 | C | GLU | E | 339 | 75.652 | −9.701 | 32.496 | 1.00 | 42.94 | C |
| ATOM | 5226 | O | GLU | E | 339 | 76.840 | −9.459 | 32.249 | 1.00 | 41.99 | O |
| ATOM | 5227 | CB | GLU | E | 339 | 75.121 | −8.028 | 34.296 | 1.00 | 44.65 | C |
| ATOM | 5228 | CG | GLU | E | 339 | 74.100 | −7.163 | 33.591 | 1.00 | 46.70 | C |
| ATOM | 5229 | CD | GLU | E | 339 | 74.220 | −5.708 | 33.992 | 1.00 | 47.49 | C |
| ATOM | 5230 | OE1 | GLU | E | 339 | 74.666 | −5.448 | 35.127 | 1.00 | 48.94 | O |
| ATOM | 5231 | OE2 | GLU | E | 339 | 73.862 | −4.823 | 33.186 | 1.00 | 48.65 | O |
| ATOM | 5232 | N | TYR | E | 340 | 74.790 | −10.145 | 31.579 | 1.00 | 41.66 | N |
| ATOM | 5233 | CA | TYR | E | 340 | 75.160 | −10.339 | 30.172 | 1.00 | 40.54 | C |
| ATOM | 5234 | C | TYR | E | 340 | 74.485 | −9.267 | 29.314 | 1.00 | 39.53 | C |
| ATOM | 5235 | O | TYR | E | 340 | 73.307 | −8.955 | 29.504 | 1.00 | 39.67 | O |
| ATOM | 5236 | CB | TYR | E | 340 | 74.754 | −11.736 | 29.687 | 1.00 | 40.75 | C |
| ATOM | 5237 | CG | TYR | E | 340 | 75.595 | −12.833 | 30.302 | 1.00 | 43.00 | C |
| ATOM | 5238 | CD1 | TYR | E | 340 | 75.423 | −13.199 | 31.637 | 1.00 | 43.39 | C |
| ATOM | 5239 | CD2 | TYR | E | 340 | 76.624 | −13.446 | 29.576 | 1.00 | 42.97 | C |
| ATOM | 5240 | CE1 | TYR | E | 340 | 76.260 | −14.144 | 32.246 | 1.00 | 43.85 | C |
| ATOM | 5241 | CE2 | TYR | E | 340 | 77.465 | −14.391 | 30.172 | 1.00 | 44.16 | C |
| ATOM | 5242 | CZ | TYR | E | 340 | 77.279 | −14.732 | 31.513 | 1.00 | 44.42 | C |
| ATOM | 5243 | OH | TYR | E | 340 | 78.124 | −15.631 | 32.126 | 1.00 | 43.97 | O |
| ATOM | 5244 | N | THR | E | 341 | 75.225 | −8.718 | 28.356 | 1.00 | 37.76 | N |
| ATOM | 5245 | CA | THR | E | 341 | 74.692 | −7.661 | 27.514 | 1.00 | 36.11 | C |
| ATOM | 5246 | C | THR | E | 341 | 74.844 | −7.882 | 26.013 | 1.00 | 35.29 | C |
| ATOM | 5247 | O | THR | E | 341 | 75.913 | −8.245 | 25.535 | 1.00 | 35.15 | O |
| ATOM | 5248 | CB | THR | E | 341 | 75.384 | −6.311 | 27.837 | 1.00 | 35.87 | C |
| ATOM | 5249 | OG1 | THR | E | 341 | 75.114 | −5.936 | 29.192 | 1.00 | 36.17 | O |
| ATOM | 5250 | CG2 | THR | E | 341 | 74.901 | −5.219 | 26.902 | 1.00 | 35.45 | C |
| ATOM | 5251 | N | CYS | E | 342 | 73.765 | −7.667 | 25.273 | 1.00 | 34.30 | N |
| ATOM | 5252 | CA | CYS | E | 342 | 73.838 | −7.755 | 23.820 | 1.00 | 33.50 | C |
| ATOM | 5253 | C | CYS | E | 342 | 73.962 | −6.303 | 23.397 | 1.00 | 32.08 | C |
| ATOM | 5254 | O | CYS | E | 342 | 73.088 | −5.491 | 23.685 | 1.00 | 31.94 | O |

TABLE 3-continued

| | | | | | FGFR2(D2–D3) Complexed with FGF2 | | | | | |
|---|---|---|---|---|---|---|---|---|---|---|
| ATOM | 5255 | CB | CYS | E | 342 | 72.577 | −8.347 | 23.201 | 1.00 | 33.31 | C |
| ATOM | 5256 | SG | CYS | E | 342 | 72.527 | −8.113 | 21.399 | 1.00 | 35.61 | S |
| ATOM | 5257 | N | LEU | E | 343 | 75.056 | −5.977 | 22.724 | 1.00 | 31.56 | N |
| ATOM | 5258 | CA | LEU | E | 343 | 75.292 | −4.610 | 22.278 | 1.00 | 30.17 | C |
| ATOM | 5259 | C | LEU | E | 343 | 75.366 | −4.522 | 20.758 | 1.00 | 29.58 | C |
| ATOM | 5260 | O | LEU | E | 343 | 76.132 | −5.245 | 20.121 | 1.00 | 29.15 | O |
| ATOM | 5261 | CB | LEU | E | 343 | 76.581 | −4.080 | 22.913 | 1.00 | 29.36 | C |
| ATOM | 5262 | CG | LEU | E | 343 | 76.957 | −2.619 | 22.680 | 1.00 | 28.90 | C |
| ATOM | 5263 | CD1 | LEU | E | 343 | 77.509 | −2.017 | 23.964 | 1.00 | 29.70 | C |
| ATOM | 5264 | CD2 | LEU | E | 343 | 77.972 | −2.529 | 21.551 | 1.00 | 29.96 | C |
| ATOM | 5265 | N | ALA | E | 344 | 74.552 | −3.633 | 20.189 | 1.00 | 28.85 | N |
| ATOM | 5266 | CA | ALA | E | 344 | 74.505 | −3.430 | 18.751 | 1.00 | 28.63 | C |
| ATOM | 5267 | C | ALA | E | 344 | 74.810 | −1.983 | 18.371 | 1.00 | 28.87 | C |
| ATOM | 5268 | O | ALA | E | 344 | 74.230 | −1.039 | 18.915 | 1.00 | 29.04 | O |
| ATOM | 5269 | CB | ALA | E | 344 | 73.138 | −3.837 | 18.206 | 1.00 | 28.59 | C |
| ATOM | 5270 | N | GLY | E | 345 | 75.725 | −1.806 | 17.425 | 1.00 | 28.49 | N |
| ATOM | 5271 | CA | GLY | E | 345 | 76.060 | −0.465 | 16.998 | 1.00 | 27.62 | C |
| ATOM | 5272 | C | GLY | E | 345 | 76.246 | −0.322 | 15.499 | 1.00 | 27.14 | C |
| ATOM | 5273 | O | GLY | E | 345 | 76.625 | −1.281 | 14.821 | 1.00 | 25.46 | O |
| ATOM | 5274 | N | ASN | E | 346 | 75.922 | 0.869 | 14.986 | 1.00 | 26.69 | N |
| ATOM | 5275 | CA | ASN | E | 346 | 76.132 | 1.217 | 13.579 | 1.00 | 27.69 | C |
| ATOM | 5276 | C | ASN | E | 346 | 76.744 | 2.621 | 13.563 | 1.00 | 28.33 | C |
| ATOM | 5277 | O | ASN | E | 346 | 77.004 | 3.190 | 14.623 | 1.00 | 27.30 | O |
| ATOM | 5278 | CB | ASN | E | 346 | 74.836 | 1.164 | 12.736 | 1.00 | 27.21 | C |
| ATOM | 5279 | CG | ASN | E | 346 | 73.761 | 2.145 | 13.206 | 1.00 | 27.40 | C |
| ATOM | 5280 | OD1 | ASN | E | 346 | 74.058 | 3.212 | 13.742 | 1.00 | 26.31 | O |
| ATOM | 5281 | ND2 | ASN | E | 346 | 72.497 | 1.787 | 12.974 | 1.00 | 24.84 | N |
| ATOM | 5282 | N | SER | E | 347 | 76.985 | 3.178 | 12.378 | 1.00 | 31.00 | N |
| ATOM | 5283 | CA | SER | E | 347 | 77.602 | 4.505 | 12.281 | 1.00 | 33.49 | C |
| ATOM | 5284 | C | SER | E | 347 | 76.856 | 5.605 | 13.024 | 1.00 | 34.58 | C |
| ATOM | 5285 | O | SER | E | 347 | 77.469 | 6.572 | 13.463 | 1.00 | 34.82 | O |
| ATOM | 5286 | CB | SER | E | 347 | 77.772 | 4.942 | 10.816 | 1.00 | 35.65 | C |
| ATOM | 5287 | OG | SER | E | 347 | 76.530 | 5.254 | 10.203 | 1.00 | 38.30 | O |
| ATOM | 5288 | N | ILE | E | 348 | 75.541 | 5.466 | 13.168 | 1.00 | 34.99 | N |
| ATOM | 5289 | CA | ILE | E | 348 | 74.751 | 6.483 | 13.864 | 1.00 | 35.50 | C |
| ATOM | 5290 | C | ILE | E | 348 | 74.840 | 6.414 | 15.387 | 1.00 | 35.19 | C |
| ATOM | 5291 | O | ILE | E | 348 | 74.938 | 7.444 | 16.048 | 1.00 | 36.08 | O |
| ATOM | 5292 | CB | ILE | E | 348 | 73.265 | 6.399 | 13.462 | 1.00 | 36.91 | C |
| ATOM | 5293 | CG1 | ILE | E | 348 | 73.135 | 6.618 | 11.955 | 1.00 | 37.03 | C |
| ATOM | 5294 | CG2 | ILE | E | 348 | 72.451 | 7.433 | 14.235 | 1.00 | 37.40 | C |
| ATOM | 5295 | CD1 | ILE | E | 348 | 71.779 | 6.275 | 11.412 | 1.00 | 39.10 | C |
| ATOM | 5296 | N | GLY | E | 349 | 74.800 | 5.209 | 15.945 | 1.00 | 34.48 | N |
| ATOM | 5297 | CA | GLY | E | 349 | 74.871 | 5.074 | 17.388 | 1.00 | 33.86 | C |
| ATOM | 5298 | C | GLY | E | 349 | 74.870 | 3.648 | 17.923 | 1.00 | 33.75 | C |
| ATOM | 5299 | O | GLY | E | 349 | 74.922 | 2.681 | 17.165 | 1.00 | 33.05 | O |
| ATOM | 5300 | N | ILE | E | 350 | 74.789 | 3.532 | 19.247 | 1.00 | 33.83 | N |
| ATOM | 5301 | CA | ILE | E | 350 | 74.804 | 2.248 | 19.935 | 1.00 | 33.98 | C |
| ATOM | 5302 | C | ILE | E | 350 | 73.567 | 1.992 | 20.808 | 1.00 | 34.07 | C |
| ATOM | 5303 | O | ILE | E | 350 | 73.010 | 2.912 | 21.408 | 1.00 | 34.17 | O |
| ATOM | 5304 | CB | ILE | E | 350 | 76.056 | 2.133 | 20.838 | 1.00 | 33.87 | C |
| ATOM | 5305 | CG1 | ILE | E | 350 | 77.320 | 2.329 | 20.004 | 1.00 | 34.32 | C |
| ATOM | 5306 | CG2 | ILE | E | 350 | 76.088 | 0.779 | 21.531 | 1.00 | 35.06 | C |
| ATOM | 5307 | CD1 | ILE | E | 350 | 78.577 | 2.477 | 20.839 | 1.00 | 35.18 | C |
| ATOM | 5308 | N | SER | E | 351 | 73.153 | 0.729 | 20.864 | 1.00 | 33.25 | N |
| ATOM | 5309 | CA | SER | E | 351 | 72.019 | 0.296 | 21.682 | 1.00 | 33.20 | C |
| ATOM | 5310 | C | SER | E | 351 | 72.410 | −1.014 | 22.363 | 1.00 | 32.62 | C |
| ATOM | 5311 | O | SER | E | 351 | 73.214 | −1.775 | 21.821 | 1.00 | 32.18 | O |
| ATOM | 5312 | CB | SER | E | 351 | 70.778 | 0.064 | 20.817 | 1.00 | 34.11 | C |
| ATOM | 5313 | OG | SER | E | 351 | 70.292 | 1.276 | 20.274 | 1.00 | 37.01 | O |
| ATOM | 5314 | N | PHE | E | 352 | 71.858 | −1.275 | 23.544 | 1.00 | 32.40 | N |
| ATOM | 5315 | CA | PHE | E | 352 | 72.163 | −2.513 | 24.260 | 1.00 | 33.36 | C |
| ATOM | 5316 | C | PHE | E | 352 | 71.119 | −2.886 | 25.311 | 1.00 | 33.02 | C |
| ATOM | 5317 | O | PHE | E | 352 | 70.558 | −2.018 | 25.977 | 1.00 | 33.29 | O |
| ATOM | 5318 | CB | PHE | E | 352 | 73.558 | −2.413 | 24.913 | 1.00 | 34.47 | C |
| ATOM | 5319 | CG | PHE | E | 352 | 73.690 | −1.297 | 25.921 | 1.00 | 36.24 | C |
| ATOM | 5320 | CD1 | PHE | E | 352 | 73.218 | −1.450 | 27.225 | 1.00 | 37.18 | C |
| ATOM | 5321 | CD2 | PHE | E | 352 | 74.281 | −0.091 | 25.564 | 1.00 | 36.74 | C |
| ATOM | 5322 | CE1 | PHE | E | 352 | 73.335 | −0.413 | 28.160 | 1.00 | 38.09 | C |
| ATOM | 5323 | CE2 | PHE | E | 352 | 74.403 | 0.948 | 26.484 | 1.00 | 38.13 | C |
| ATOM | 5324 | CZ | PHE | E | 352 | 73.929 | 0.788 | 27.785 | 1.00 | 38.23 | C |
| ATOM | 5325 | N | HIS | E | 353 | 70.856 | −4.182 | 25.443 | 1.00 | 33.31 | N |
| ATOM | 5326 | CA | HIS | E | 353 | 69.904 | −4.687 | 26.438 | 1.00 | 34.40 | C |
| ATOM | 5327 | C | HIS | E | 353 | 70.655 | −5.730 | 27.274 | 1.00 | 35.40 | C |
| ATOM | 5328 | O | HIS | E | 353 | 71.478 | −6.484 | 26.741 | 1.00 | 35.06 | O |
| ATOM | 5329 | CB | HIS | E | 353 | 68.670 | −5.332 | 25.777 | 1.00 | 33.36 | C |
| ATOM | 5330 | CG | HIS | E | 353 | 67.700 | −4.351 | 25.187 | 1.00 | 33.71 | C |
| ATOM | 5331 | ND1 | HIS | E | 353 | 66.500 | −4.735 | 24.622 | 1.00 | 33.31 | N |

TABLE 3-continued

FGFR2(D2–D3) Complexed with FGF2

| ATOM | 5332 | CD2 | HIS | E | 353 | 67.745 | −2.999 | 25.075 | 1.00 | 32.51 | C |
|---|---|---|---|---|---|---|---|---|---|---|---|
| ATOM | 5333 | CE1 | HIS | E | 353 | 65.851 | −3.668 | 24.192 | 1.00 | 31.00 | C |
| ATOM | 5334 | NE2 | HIS | E | 353 | 66.586 | −2.603 | 24.455 | 1.00 | 31.60 | N |
| ATOM | 5335 | N | SER | E | 354 | 70.374 | −5.766 | 28.576 | 1.00 | 36.20 | N |
| ATOM | 5336 | CA | SER | E | 354 | 71.045 | −6.698 | 29.479 | 1.00 | 37.46 | C |
| ATOM | 5337 | C | SER | E | 354 | 70.112 | −7.646 | 30.221 | 1.00 | 38.17 | C |
| ATOM | 5338 | O | SER | E | 354 | 68.928 | −7.364 | 30.425 | 1.00 | 37.52 | O |
| ATOM | 5339 | CB | SER | E | 354 | 71.873 | −5.928 | 30.507 | 1.00 | 37.67 | C |
| ATOM | 5340 | OG | SER | E | 354 | 72.763 | −5.031 | 29.869 | 1.00 | 40.40 | O |
| ATOM | 5341 | N | ALA | E | 355 | 70.670 | −8.779 | 30.631 | 1.00 | 39.18 | N |
| ATOM | 5342 | CA | ALA | E | 355 | 69.919 | −9.779 | 31.375 | 1.00 | 40.68 | C |
| ATOM | 5343 | C | ALA | E | 355 | 70.850 | −10.349 | 32.437 | 1.00 | 41.59 | C |
| ATOM | 5344 | O | ALA | E | 355 | 72.072 | −10.179 | 32.359 | 1.00 | 42.09 | O |
| ATOM | 5345 | CB | ALA | E | 355 | 69.428 | −10.886 | 30.438 | 1.00 | 40.51 | C |
| ATOM | 5346 | N | TRP | E | 356 | 70.273 | −11.023 | 33.425 | 1.00 | 42.87 | N |
| ATOM | 5347 | CA | TRP | E | 356 | 71.055 | −11.597 | 34.508 | 1.00 | 44.67 | C |
| ATOM | 5348 | C | TRP | E | 356 | 71.021 | −13.119 | 34.519 | 1.00 | 44.89 | C |
| ATOM | 5349 | O | TRP | E | 356 | 69.995 | −13.734 | 34.237 | 1.00 | 44.45 | O |
| ATOM | 5350 | CB | TRP | E | 356 | 70.542 | −11.068 | 35.856 | 1.00 | 46.66 | C |
| ATOM | 5351 | CG | TRP | E | 356 | 71.644 | −10.589 | 36.745 | 1.00 | 48.84 | C |
| ATOM | 5352 | CD1 | TRP | E | 356 | 72.536 | −11.360 | 37.436 | 1.00 | 49.57 | C |
| ATOM | 5353 | CD2 | TRP | E | 356 | 72.051 | −9.229 | 36.940 | 1.00 | 49.66 | C |
| ATOM | 5354 | NE1 | TRP | E | 356 | 73.483 | −10.563 | 38.041 | 1.00 | 50.48 | N |
| ATOM | 5355 | CE2 | TRP | E | 356 | 73.209 | −9.251 | 37.752 | 1.00 | 50.21 | C |
| ATOM | 5356 | CE3 | TRP | E | 356 | 71.551 | −7.992 | 36.501 | 1.00 | 50.27 | C |
| ATOM | 5357 | CZ2 | TRP | E | 356 | 73.883 | −8.080 | 38.137 | 1.00 | 50.52 | C |
| ATOM | 5358 | CZ3 | TRP | E | 356 | 72.221 | −6.824 | 36.883 | 1.00 | 50.86 | C |
| ATOM | 5359 | CH2 | TRP | E | 356 | 73.375 | −6.881 | 37.693 | 1.00 | 50.85 | C |
| ATOM | 5360 | N | LEU | E | 357 | 72.163 | −13.719 | 34.835 | 1.00 | 45.24 | N |
| ATOM | 5361 | CA | LEU | E | 357 | 72.275 | −15.165 | 34.929 | 1.00 | 46.28 | C |
| ATOM | 5362 | C | LEU | E | 357 | 72.416 | −15.529 | 36.404 | 1.00 | 47.03 | C |
| ATOM | 5363 | O | LEU | E | 357 | 73.362 | −15.085 | 37.064 | 1.00 | 47.09 | O |
| ATOM | 5364 | CB | LEU | E | 357 | 73.516 | −15.662 | 34.180 | 1.00 | 46.24 | C |
| ATOM | 5365 | CG | LEU | E | 357 | 73.855 | −17.138 | 34.418 | 1.00 | 46.22 | C |
| ATOM | 5366 | CD1 | LEU | E | 357 | 72.722 | −18.004 | 33.879 | 1.00 | 45.74 | C |
| ATOM | 5367 | CD2 | LEU | E | 357 | 75.184 | −17.493 | 33.742 | 1.00 | 45.83 | C |
| ATOM | 5368 | N | THR | E | 358 | 71.481 | −16.323 | 36.920 | 1.00 | 47.80 | N |
| ATOM | 5369 | CA | THR | E | 358 | 71.525 | −16.754 | 38.317 | 1.00 | 49.40 | C |
| ATOM | 5370 | C | THR | E | 358 | 71.935 | −18.221 | 38.360 | 1.00 | 49.88 | C |
| ATOM | 5371 | O | THR | E | 358 | 71.300 | −19.067 | 37.725 | 1.00 | 49.63 | O |
| ATOM | 5372 | CB | THR | E | 358 | 70.144 | −16.626 | 39.010 | 1.00 | 50.27 | C |
| ATOM | 5373 | OG1 | THR | E | 358 | 69.709 | −15.263 | 38.980 | 1.00 | 51.35 | O |
| ATOM | 5374 | CG2 | THR | E | 358 | 70.231 | −17.083 | 40.466 | 1.00 | 51.00 | C |
| ATOM | 5375 | N | VAL | E | 359 | 72.995 | −18.515 | 39.108 | 1.00 | 50.99 | N |
| ATOM | 5376 | CA | VAL | E | 359 | 73.496 | −19.878 | 39.239 | 1.00 | 52.26 | C |
| ATOM | 5377 | C | VAL | E | 359 | 73.291 | −20.372 | 40.671 | 1.00 | 53.50 | C |
| ATOM | 5378 | O | VAL | E | 359 | 73.879 | −19.828 | 41.617 | 1.00 | 53.34 | O |
| ATOM | 5379 | CB | VAL | E | 359 | 75.001 | −19.954 | 38.883 | 1.00 | 52.03 | C |
| ATOM | 5380 | N | LEU | E | 360 | 72.454 | −21.405 | 40.806 | 1.00 | 54.72 | N |
| ATOM | 5381 | CA | LEU | E | 360 | 72.118 | −22.014 | 42.095 | 1.00 | 55.76 | C |
| ATOM | 5382 | C | LEU | E | 360 | 73.006 | −23.217 | 42.403 | 1.00 | 56.27 | C |
| ATOM | 5383 | O | LEU | E | 360 | 73.018 | −24.147 | 41.566 | 1.00 | 56.89 | O |
| ATOM | 5384 | CB | LEU | E | 360 | 70.650 | −22.456 | 42.095 | 1.00 | 55.94 | C |
| TER | 5385 | | LEU | E | 360 | | | | | | |
| ATOM | 5386 | N | ASN | F | 150 | 27.465 | 32.706 | 43.234 | 1.00 | 47.18 | N |
| ATOM | 5387 | CA | ASN | F | 150 | 26.839 | 33.873 | 43.929 | 1.00 | 46.68 | C |
| ATOM | 5388 | C | ASN | F | 150 | 25.823 | 34.566 | 43.015 | 1.00 | 45.81 | C |
| ATOM | 5389 | O | ASN | F | 150 | 25.993 | 34.593 | 41.797 | 1.00 | 46.29 | O |
| ATOM | 5390 | CB | ASN | F | 150 | 27.924 | 34.872 | 44.357 | 1.00 | 46.26 | C |
| ATOM | 5391 | N | LYS | F | 151 | 24.769 | 35.116 | 43.612 | 1.00 | 45.07 | N |
| ATOM | 5392 | CA | LYS | F | 151 | 23.717 | 35.815 | 42.874 | 1.00 | 43.78 | C |
| ATOM | 5393 | C | LYS | F | 151 | 24.148 | 37.251 | 42.548 | 1.00 | 43.34 | C |
| ATOM | 5394 | O | LYS | F | 151 | 24.545 | 38.007 | 43.432 | 1.00 | 42.87 | O |
| ATOM | 5395 | CB | LYS | F | 151 | 22.421 | 35.835 | 43.695 | 1.00 | 43.03 | C |
| ATOM | 5396 | N | ARG | F | 152 | 24.073 | 37.627 | 41.274 | 1.00 | 42.12 | N |
| ATOM | 5397 | CA | ARG | F | 152 | 24.472 | 38.973 | 40.878 | 1.00 | 40.51 | C |
| ATOM | 5398 | C | ARG | F | 152 | 23.794 | 39.481 | 39.608 | 1.00 | 39.03 | C |
| ATOM | 5399 | O | ARG | F | 152 | 23.353 | 38.706 | 38.754 | 1.00 | 38.69 | O |
| ATOM | 5400 | CB | ARG | F | 152 | 25.988 | 39.035 | 40.701 | 1.00 | 40.57 | C |
| ATOM | 5401 | CG | ARG | F | 152 | 26.528 | 38.034 | 39.696 | 1.00 | 41.38 | C |
| ATOM | 5402 | CD | ARG | F | 152 | 28.045 | 38.053 | 39.645 | 1.00 | 40.83 | C |
| ATOM | 5403 | NE | ARG | F | 152 | 28.574 | 39.325 | 39.162 | 1.00 | 40.31 | N |
| ATOM | 5404 | CZ | ARG | F | 152 | 29.816 | 39.487 | 38.712 | 1.00 | 40.01 | C |
| ATOM | 5405 | NH1 | ARG | F | 152 | 30.657 | 38.461 | 38.693 | 1.00 | 39.33 | N |
| ATOM | 5406 | NH2 | ARG | F | 152 | 30.211 | 40.665 | 38.250 | 1.00 | 40.37 | N |
| ATOM | 5407 | N | ALA | F | 153 | 23.725 | 40.802 | 39.503 | 1.00 | 37.59 | N |
| ATOM | 5408 | CA | ALA | F | 153 | 23.127 | 41.470 | 38.361 | 1.00 | 36.00 | C |

TABLE 3-continued

FGFR2(D2–D3) Complexed with FGF2

| ATOM | 5409 | C | ALA | F | 153 | 23.905 | 41.142 | 37.085 | 1.00 | 34.93 | C |
|---|---|---|---|---|---|---|---|---|---|---|---|
| ATOM | 5410 | O | ALA | F | 153 | 25.018 | 40.633 | 37.139 | 1.00 | 34.72 | O |
| ATOM | 5411 | CB | ALA | F | 153 | 23.105 | 42.987 | 38.604 | 1.00 | 35.68 | C |
| ATOM | 5412 | N | PRO | F | 154 | 23.322 | 41.436 | 35.916 | 1.00 | 34.45 | N |
| ATOM | 5413 | CA | PRO | F | 154 | 23.987 | 41.158 | 34.640 | 1.00 | 33.61 | C |
| ATOM | 5414 | C | PRO | F | 154 | 25.229 | 42.013 | 34.427 | 1.00 | 33.12 | C |
| ATOM | 5415 | O | PRO | F | 154 | 25.312 | 43.137 | 34.922 | 1.00 | 32.79 | O |
| ATOM | 5416 | CB | PRO | F | 154 | 22.894 | 41.447 | 33.624 | 1.00 | 33.95 | C |
| ATOM | 5417 | CG | PRO | F | 154 | 22.131 | 42.546 | 34.284 | 1.00 | 34.26 | C |
| ATOM | 5418 | CD | PRO | F | 154 | 22.018 | 42.086 | 35.698 | 1.00 | 33.81 | C |
| ATOM | 5419 | N | TYR | F | 155 | 26.194 | 41.465 | 33.697 | 1.00 | 33.26 | N |
| ATOM | 5420 | CA | TYR | F | 155 | 27.432 | 42.171 | 33.406 | 1.00 | 34.23 | C |
| ATOM | 5421 | C | TYR | F | 155 | 28.054 | 41.642 | 32.109 | 1.00 | 34.53 | C |
| ATOM | 5422 | O | TYR | F | 155 | 27.912 | 40.466 | 31.786 | 1.00 | 34.70 | O |
| ATOM | 5423 | CB | TYR | F | 155 | 28.416 | 42.010 | 34.571 | 1.00 | 35.21 | C |
| ATOM | 5424 | CG | TYR | F | 155 | 28.879 | 40.587 | 34.807 | 1.00 | 36.38 | C |
| ATOM | 5425 | CD1 | TYR | F | 155 | 28.033 | 39.637 | 35.387 | 1.00 | 37.46 | C |
| ATOM | 5426 | CD2 | TYR | F | 155 | 30.153 | 40.183 | 34.422 | 1.00 | 36.66 | C |
| ATOM | 5427 | CE1 | TYR | F | 155 | 28.450 | 38.317 | 35.573 | 1.00 | 37.51 | C |
| ATOM | 5428 | CE2 | TYR | F | 155 | 30.579 | 38.871 | 34.602 | 1.00 | 37.68 | C |
| ATOM | 5429 | CZ | TYR | F | 155 | 29.725 | 37.944 | 35.172 | 1.00 | 38.34 | C |
| ATOM | 5430 | OH | TYR | F | 155 | 30.150 | 36.637 | 35.313 | 1.00 | 39.80 | O |
| ATOM | 5431 | N | TRP | F | 156 | 28.731 | 42.519 | 31.373 | 1.00 | 34.56 | N |
| ATOM | 5432 | CA | TRP | F | 156 | 29.385 | 42.141 | 30.123 | 1.00 | 36.40 | C |
| ATOM | 5433 | C | TRP | F | 156 | 30.610 | 41.270 | 30.415 | 1.00 | 38.32 | C |
| ATOM | 5434 | O | TRP | F | 156 | 31.454 | 41.648 | 31.229 | 1.00 | 39.35 | O |
| ATOM | 5435 | CB | TRP | F | 156 | 29.828 | 43.402 | 29.369 | 1.00 | 34.91 | C |
| ATOM | 5436 | CG | TRP | F | 156 | 28.743 | 44.408 | 29.136 | 1.00 | 33.24 | C |
| ATOM | 5437 | CD1 | TRP | F | 156 | 28.809 | 45.743 | 29.385 | 1.00 | 32.54 | C |
| ATOM | 5438 | CD2 | TRP | F | 156 | 27.434 | 44.162 | 28.598 | 1.00 | 32.50 | C |
| ATOM | 5439 | NE1 | TRP | F | 156 | 27.630 | 46.352 | 29.041 | 1.00 | 31.97 | N |
| ATOM | 5440 | CE2 | TRP | F | 156 | 26.764 | 45.409 | 28.553 | 1.00 | 32.15 | C |
| ATOM | 5441 | CE3 | TRP | F | 156 | 26.761 | 43.011 | 28.147 | 1.00 | 31.76 | C |
| ATOM | 5442 | CZ2 | TRP | F | 156 | 25.447 | 45.544 | 28.079 | 1.00 | 31.23 | C |
| ATOM | 5443 | CZ3 | TRP | F | 156 | 25.445 | 43.143 | 27.670 | 1.00 | 31.94 | C |
| ATOM | 5444 | CH2 | TRP | F | 156 | 24.806 | 44.404 | 27.642 | 1.00 | 31.30 | C |
| ATOM | 5445 | N | THR | F | 157 | 30.710 | 40.121 | 29.748 | 1.00 | 40.38 | N |
| ATOM | 5446 | CA | THR | F | 157 | 31.826 | 39.198 | 29.952 | 1.00 | 42.48 | C |
| ATOM | 5447 | C | THR | F | 157 | 32.970 | 39.388 | 28.967 | 1.00 | 43.74 | C |
| ATOM | 5448 | O | THR | F | 157 | 33.988 | 38.708 | 29.059 | 1.00 | 44.97 | O |
| ATOM | 5449 | CB | THR | F | 157 | 31.353 | 37.738 | 29.878 | 1.00 | 43.02 | C |
| ATOM | 5450 | OG1 | THR | F | 157 | 30.716 | 37.495 | 28.613 | 1.00 | 43.13 | O |
| ATOM | 5451 | CG2 | THR | F | 157 | 30.371 | 37.453 | 31.004 | 1.00 | 43.29 | C |
| ATOM | 5452 | N | ASN | F | 158 | 32.808 | 40.306 | 28.022 | 1.00 | 45.46 | N |
| ATOM | 5453 | CA | ASN | F | 158 | 33.862 | 40.578 | 27.046 | 1.00 | 46.50 | C |
| ATOM | 5454 | C | ASN | F | 158 | 33.649 | 41.918 | 26.355 | 1.00 | 46.39 | C |
| ATOM | 5455 | O | ASN | F | 158 | 33.122 | 41.974 | 25.246 | 1.00 | 46.75 | O |
| ATOM | 5456 | CB | ASN | F | 158 | 33.936 | 39.472 | 25.988 | 1.00 | 48.38 | C |
| ATOM | 5457 | CG | ASN | F | 158 | 35.162 | 39.613 | 25.080 | 1.00 | 50.17 | C |
| ATOM | 5458 | OD1 | ASN | F | 158 | 35.297 | 40.586 | 24.326 | 1.00 | 50.24 | O |
| ATOM | 5459 | ND2 | ASN | F | 158 | 36.063 | 38.640 | 25.158 | 1.00 | 50.64 | N |
| ATOM | 5460 | N | THR | F | 159 | 34.075 | 42.992 | 27.015 | 1.00 | 46.28 | N |
| ATOM | 5461 | CA | THR | F | 159 | 33.927 | 44.340 | 26.480 | 1.00 | 46.80 | C |
| ATOM | 5462 | C | THR | F | 159 | 34.772 | 44.588 | 25.240 | 1.00 | 47.39 | C |
| ATOM | 5463 | O | THR | F | 159 | 34.495 | 45.516 | 24.479 | 1.00 | 47.37 | O |
| ATOM | 5464 | CB | THR | F | 159 | 34.302 | 45.422 | 27.530 | 1.00 | 47.53 | C |
| ATOM | 5465 | OG1 | THR | F | 159 | 35.591 | 45.130 | 28.084 | 1.00 | 48.04 | O |
| ATOM | 5466 | CG2 | THR | F | 159 | 33.269 | 45.471 | 28.657 | 1.00 | 48.15 | C |
| ATOM | 5467 | N | GLU | F | 160 | 35.807 | 43.770 | 25.048 | 1.00 | 47.49 | N |
| ATOM | 5468 | CA | GLU | F | 160 | 36.695 | 43.913 | 23.900 | 1.00 | 47.50 | C |
| ATOM | 5469 | C | GLU | F | 160 | 35.894 | 43.832 | 22.602 | 1.00 | 47.37 | C |
| ATOM | 5470 | O | GLU | F | 160 | 36.019 | 44.683 | 21.727 | 1.00 | 47.28 | O |
| ATOM | 5471 | CB | GLU | F | 160 | 37.764 | 42.812 | 23.922 | 1.00 | 47.86 | C |
| ATOM | 5472 | N | LYS | F | 161 | 35.058 | 42.805 | 22.505 | 1.00 | 46.88 | N |
| ATOM | 5473 | CA | LYS | F | 161 | 34.225 | 42.574 | 21.335 | 1.00 | 46.63 | C |
| ATOM | 5474 | C | LYS | F | 161 | 33.062 | 43.566 | 21.194 | 1.00 | 45.96 | C |
| ATOM | 5475 | O | LYS | F | 161 | 32.268 | 43.452 | 20.261 | 1.00 | 45.92 | O |
| ATOM | 5476 | CB | LYS | F | 161 | 33.663 | 41.144 | 21.386 | 1.00 | 47.58 | C |
| ATOM | 5477 | N | MET | F | 162 | 32.962 | 44.528 | 22.111 | 1.00 | 45.07 | N |
| ATOM | 5478 | CA | MET | F | 162 | 31.876 | 45.514 | 22.088 | 1.00 | 44.13 | C |
| ATOM | 5479 | C | MET | F | 162 | 32.350 | 46.941 | 21.834 | 1.00 | 43.91 | C |
| ATOM | 5480 | O | MET | F | 162 | 31.532 | 47.852 | 21.671 | 1.00 | 43.60 | O |
| ATOM | 5481 | CB | MET | F | 162 | 31.110 | 45.491 | 23.417 | 1.00 | 43.45 | C |
| ATOM | 5482 | CG | MET | F | 162 | 30.339 | 44.215 | 23.708 | 1.00 | 42.75 | C |
| ATOM | 5483 | SD | MET | F | 162 | 29.681 | 44.224 | 25.407 | 1.00 | 44.78 | S |
| ATOM | 5484 | CE | MET | F | 162 | 28.618 | 45.682 | 25.364 | 1.00 | 42.60 | C |
| ATOM | 5485 | N | GLU | F | 163 | 33.663 | 47.139 | 21.796 | 1.00 | 43.66 | N |

TABLE 3-continued

FGFR2(D2–D3) Complexed with FGF2

| ATOM | 5486 | CA | GLU | F | 163 | 34.228 | 48.474 | 21.595 | 1.00 | 43.05 | C |
|---|---|---|---|---|---|---|---|---|---|---|---|
| ATOM | 5487 | C | GLU | F | 163 | 33.900 | 49.117 | 20.245 | 1.00 | 42.02 | C |
| ATOM | 5488 | O | GLU | F | 163 | 33.747 | 50.336 | 20.150 | 1.00 | 42.39 | O |
| ATOM | 5489 | CB | GLU | F | 163 | 35.748 | 48.432 | 21.790 | 1.00 | 43.51 | C |
| ATOM | 5490 | N | LYS | F | 164 | 33.801 | 48.302 | 19.201 | 1.00 | 40.60 | N |
| ATOM | 5491 | CA | LYS | F | 164 | 33.482 | 48.806 | 17.866 | 1.00 | 38.52 | C |
| ATOM | 5492 | C | LYS | F | 164 | 31.982 | 49.137 | 17.821 | 1.00 | 37.22 | C |
| ATOM | 5493 | O | LYS | F | 164 | 31.152 | 48.253 | 17.609 | 1.00 | 36.84 | O |
| ATOM | 5494 | CB | LYS | F | 164 | 33.835 | 47.742 | 16.820 | 1.00 | 37.86 | C |
| ATOM | 5495 | CG | LYS | F | 164 | 33.861 | 48.266 | 15.410 | 1.00 | 37.96 | C |
| ATOM | 5496 | CD | LYS | F | 164 | 34.340 | 47.228 | 14.408 | 1.00 | 37.78 | C |
| ATOM | 5497 | CE | LYS | F | 164 | 33.188 | 46.490 | 13.757 | 1.00 | 38.14 | C |
| ATOM | 5498 | NZ | LYS | F | 164 | 33.621 | 45.853 | 12.478 | 1.00 | 39.11 | N |
| ATOM | 5499 | N | ARG | F | 165 | 31.644 | 50.407 | 18.025 | 1.00 | 35.96 | N |
| ATOM | 5500 | CA | ARG | F | 165 | 30.247 | 50.843 | 18.044 | 1.00 | 35.34 | C |
| ATOM | 5501 | C | ARG | F | 165 | 29.614 | 51.005 | 16.672 | 1.00 | 33.90 | C |
| ATOM | 5502 | O | ARG | F | 165 | 28.468 | 50.609 | 16.466 | 1.00 | 32.97 | O |
| ATOM | 5503 | CB | ARG | F | 165 | 30.110 | 52.151 | 18.833 | 1.00 | 36.33 | C |
| ATOM | 5504 | CG | ARG | F | 165 | 30.254 | 51.954 | 20.333 | 1.00 | 39.65 | C |
| ATOM | 5505 | CD | ARG | F | 165 | 30.371 | 53.273 | 21.066 | 1.00 | 42.36 | C |
| ATOM | 5506 | NE | ARG | F | 165 | 30.713 | 53.076 | 22.472 | 1.00 | 45.53 | N |
| ATOM | 5507 | CZ | ARG | F | 165 | 29.837 | 52.783 | 23.429 | 1.00 | 47.06 | C |
| ATOM | 5508 | NH1 | ARG | F | 165 | 28.540 | 52.656 | 23.148 | 1.00 | 47.85 | N |
| ATOM | 5509 | NH2 | ARG | F | 165 | 30.262 | 52.607 | 24.671 | 1.00 | 47.69 | N |
| ATOM | 5510 | N | LEU | F | 166 | 30.364 | 51.593 | 15.746 | 1.00 | 33.06 | N |
| ATOM | 5511 | CA | LEU | F | 166 | 29.905 | 51.808 | 14.379 | 1.00 | 32.49 | C |
| ATOM | 5512 | C | LEU | F | 166 | 30.309 | 50.638 | 13.497 | 1.00 | 32.80 | C |
| ATOM | 5513 | O | LEU | F | 166 | 31.498 | 50.360 | 13.350 | 1.00 | 32.69 | O |
| ATOM | 5514 | CB | LEU | F | 166 | 30.528 | 53.083 | 13.801 | 1.00 | 30.33 | C |
| ATOM | 5515 | CG | LEU | F | 166 | 30.342 | 53.309 | 12.288 | 1.00 | 31.08 | C |
| ATOM | 5516 | CD1 | LEU | F | 166 | 28.859 | 53.376 | 11.924 | 1.00 | 28.89 | C |
| ATOM | 5517 | CD2 | LEU | F | 166 | 31.033 | 54.592 | 11.879 | 1.00 | 28.85 | C |
| ATOM | 5518 | N | HIS | F | 167 | 29.322 | 49.957 | 12.918 | 1.00 | 32.67 | N |
| ATOM | 5519 | CA | HIS | F | 167 | 29.565 | 48.837 | 12.015 | 1.00 | 32.58 | C |
| ATOM | 5520 | C | HIS | F | 167 | 29.153 | 49.268 | 10.614 | 1.00 | 33.20 | C |
| ATOM | 5521 | O | HIS | F | 167 | 27.959 | 49.316 | 10.302 | 1.00 | 33.21 | O |
| ATOM | 5522 | CB | HIS | F | 167 | 28.737 | 47.609 | 12.413 | 1.00 | 33.93 | C |
| ATOM | 5523 | CG | HIS | F | 167 | 29.317 | 46.814 | 13.541 | 1.00 | 35.95 | C |
| ATOM | 5524 | ND1 | HIS | F | 167 | 29.561 | 47.350 | 14.788 | 1.00 | 37.05 | N |
| ATOM | 5525 | CD2 | HIS | F | 167 | 29.699 | 45.516 | 13.609 | 1.00 | 35.66 | C |
| ATOM | 5526 | CE1 | HIS | F | 167 | 30.070 | 46.418 | 15.574 | 1.00 | 36.41 | C |
| ATOM | 5527 | NE2 | HIS | F | 167 | 30.164 | 45.296 | 14.882 | 1.00 | 36.24 | N |
| ATOM | 5528 | N | ALA | F | 168 | 30.135 | 49.601 | 9.782 | 1.00 | 32.49 | N |
| ATOM | 5529 | CA | ALA | F | 168 | 29.872 | 50.015 | 8.408 | 1.00 | 32.62 | C |
| ATOM | 5530 | C | ALA | F | 168 | 30.255 | 48.815 | 7.562 | 1.00 | 32.27 | C |
| ATOM | 5531 | O | ALA | F | 168 | 31.394 | 48.362 | 7.614 | 1.00 | 32.31 | O |
| ATOM | 5532 | CB | ALA | F | 168 | 30.739 | 51.224 | 8.040 | 1.00 | 33.46 | C |
| ATOM | 5533 | N | VAL | F | 169 | 29.310 | 48.299 | 6.786 | 1.00 | 31.84 | N |
| ATOM | 5534 | CA | VAL | F | 169 | 29.574 | 47.125 | 5.965 | 1.00 | 31.85 | C |
| ATOM | 5535 | C | VAL | F | 169 | 29.011 | 47.239 | 4.557 | 1.00 | 31.61 | C |
| ATOM | 5536 | O | VAL | F | 169 | 28.063 | 47.977 | 4.311 | 1.00 | 31.56 | O |
| ATOM | 5537 | CB | VAL | F | 169 | 28.959 | 45.859 | 6.596 | 1.00 | 32.55 | C |
| ATOM | 5538 | CG1 | VAL | F | 169 | 29.416 | 45.725 | 8.046 | 1.00 | 33.61 | C |
| ATOM | 5539 | CG2 | VAL | F | 169 | 27.441 | 45.928 | 6.515 | 1.00 | 31.02 | C |
| ATOM | 5540 | N | PRO | F | 170 | 29.592 | 46.491 | 3.616 | 1.00 | 31.38 | N |
| ATOM | 5541 | CA | PRO | F | 170 | 29.123 | 46.525 | 2.234 | 1.00 | 31.61 | C |
| ATOM | 5542 | C | PRO | F | 170 | 27.809 | 45.763 | 2.103 | 1.00 | 32.21 | C |
| ATOM | 5543 | O | PRO | F | 170 | 27.585 | 44.761 | 2.789 | 1.00 | 31.90 | O |
| ATOM | 5544 | CB | PRO | F | 170 | 30.267 | 45.863 | 1.472 | 1.00 | 31.99 | C |
| ATOM | 5545 | CG | PRO | F | 170 | 30.758 | 44.824 | 2.463 | 1.00 | 31.40 | C |
| ATOM | 5546 | CD | PRO | F | 170 | 30.722 | 45.556 | 3.784 | 1.00 | 30.53 | C |
| ATOM | 5547 | N | ALA | F | 171 | 26.931 | 46.251 | 1.234 | 1.00 | 33.14 | N |
| ATOM | 5548 | CA | ALA | F | 171 | 25.640 | 45.606 | 1.009 | 1.00 | 33.63 | C |
| ATOM | 5549 | C | ALA | F | 171 | 25.821 | 44.140 | 0.596 | 1.00 | 33.79 | C |
| ATOM | 5550 | O | ALA | F | 171 | 26.811 | 43.779 | −0.049 | 1.00 | 32.97 | O |
| ATOM | 5551 | CB | ALA | F | 171 | 24.863 | 46.362 | −0.063 | 1.00 | 33.56 | C |
| ATOM | 5552 | N | ALA | F | 172 | 24.863 | 43.303 | 1.001 | 1.00 | 33.61 | N |
| ATOM | 5553 | CA | ALA | F | 172 | 24.849 | 41.872 | 0.699 | 1.00 | 33.16 | C |
| ATOM | 5554 | C | ALA | F | 172 | 25.643 | 41.011 | 1.684 | 1.00 | 33.77 | C |
| ATOM | 5555 | O | ALA | F | 172 | 25.654 | 39.778 | 1.579 | 1.00 | 33.75 | O |
| ATOM | 5556 | CB | ALA | F | 172 | 25.328 | 41.622 | −0.744 | 1.00 | 33.35 | C |
| ATOM | 5557 | N | ASN | F | 173 | 26.310 | 41.640 | 2.642 | 1.00 | 33.18 | N |
| ATOM | 5558 | CA | ASN | F | 173 | 27.061 | 40.866 | 3.629 | 1.00 | 33.48 | C |
| ATOM | 5559 | C | ASN | F | 173 | 26.191 | 40.528 | 4.839 | 1.00 | 32.36 | C |
| ATOM | 5560 | O | ASN | F | 173 | 25.077 | 41.033 | 4.980 | 1.00 | 31.26 | O |
| ATOM | 5561 | CB | ASN | F | 173 | 28.314 | 41.636 | 4.062 | 1.00 | 34.43 | C |
| ATOM | 5562 | CG | ASN | F | 173 | 29.483 | 41.423 | 3.108 | 1.00 | 36.77 | C |

TABLE 3-continued

FGFR2(D2–D3) Complexed with FGF2

| ATOM | 5563 | OD1 | ASN | F | 173 | 29.307 | 41.276 | 1.890 | 1.00 | 37.96 | O |
|---|---|---|---|---|---|---|---|---|---|---|---|
| ATOM | 5564 | ND2 | ASN | F | 173 | 30.683 | 41.413 | 3.657 | 1.00 | 38.51 | N |
| ATOM | 5565 | N | THR | F | 174 | 26.698 | 39.648 | 5.693 | 1.00 | 31.64 | N |
| ATOM | 5566 | CA | THR | F | 174 | 26.000 | 39.268 | 6.913 | 1.00 | 30.65 | C |
| ATOM | 5567 | C | THR | F | 174 | 26.589 | 40.107 | 8.047 | 1.00 | 30.96 | C |
| ATOM | 5568 | O | THR | F | 174 | 27.799 | 40.333 | 8.083 | 1.00 | 31.98 | O |
| ATOM | 5569 | CB | THR | F | 174 | 26.217 | 37.779 | 7.249 | 1.00 | 29.86 | C |
| ATOM | 5570 | OG1 | THR | F | 174 | 25.397 | 36.961 | 6.402 | 1.00 | 30.18 | O |
| ATOM | 5571 | CG2 | THR | F | 174 | 25.869 | 37.507 | 8.692 | 1.00 | 29.82 | C |
| ATOM | 5572 | N | VAL | F | 175 | 25.741 | 40.573 | 8.961 | 1.00 | 30.45 | N |
| ATOM | 5573 | CA | VAL | F | 175 | 26.200 | 41.363 | 10.100 | 1.00 | 30.13 | C |
| ATOM | 5574 | C | VAL | F | 175 | 25.868 | 40.632 | 11.394 | 1.00 | 30.00 | C |
| ATOM | 5575 | O | VAL | F | 175 | 24.807 | 40.009 | 11.514 | 1.00 | 29.84 | O |
| ATOM | 5576 | CB | VAL | F | 175 | 25.521 | 42.754 | 10.153 | 1.00 | 30.57 | C |
| ATOM | 5577 | CG1 | VAL | F | 175 | 26.040 | 43.542 | 11.348 | 1.00 | 31.35 | C |
| ATOM | 5578 | CG2 | VAL | F | 175 | 25.807 | 43.510 | 8.890 | 1.00 | 30.75 | C |
| ATOM | 5579 | N | LYS | F | 176 | 26.775 | 40.693 | 12.360 | 1.00 | 29.06 | N |
| ATOM | 5580 | CA | LYS | F | 176 | 26.538 | 40.047 | 13.640 | 1.00 | 29.99 | C |
| ATOM | 5581 | C | LYS | F | 176 | 26.914 | 40.962 | 14.805 | 1.00 | 30.49 | C |
| ATOM | 5582 | O | LYS | F | 176 | 28.048 | 41.443 | 14.894 | 1.00 | 30.73 | O |
| ATOM | 5583 | CB | LYS | F | 176 | 27.328 | 38.734 | 13.733 | 1.00 | 32.08 | C |
| ATOM | 5584 | CG | LYS | F | 176 | 27.054 | 37.893 | 15.000 | 1.00 | 34.61 | C |
| ATOM | 5585 | CD | LYS | F | 176 | 27.852 | 36.559 | 15.005 | 1.00 | 35.52 | C |
| ATOM | 5586 | CE | LYS | F | 176 | 27.675 | 35.791 | 16.324 | 1.00 | 38.38 | C |
| ATOM | 5587 | NZ | LYS | F | 176 | 28.376 | 34.451 | 16.397 | 1.00 | 37.91 | N |
| ATOM | 5588 | N | PHE | F | 177 | 25.953 | 41.213 | 15.688 | 1.00 | 29.86 | N |
| ATOM | 5589 | CA | PHE | F | 177 | 26.198 | 42.038 | 16.861 | 1.00 | 29.32 | C |
| ATOM | 5590 | C | PHE | F | 177 | 26.219 | 41.125 | 18.065 | 1.00 | 29.40 | C |
| ATOM | 5591 | O | PHE | F | 177 | 25.412 | 40.210 | 18.156 | 1.00 | 30.08 | O |
| ATOM | 5592 | CB | PHE | F | 177 | 25.095 | 43.080 | 17.024 | 1.00 | 28.12 | C |
| ATOM | 5593 | CG | PHE | F | 177 | 25.075 | 44.108 | 15.931 | 1.00 | 28.38 | C |
| ATOM | 5594 | CD1 | PHE | F | 177 | 26.193 | 44.903 | 15.689 | 1.00 | 27.55 | C |
| ATOM | 5595 | CD2 | PHE | F | 177 | 23.929 | 44.306 | 15.163 | 1.00 | 28.25 | C |
| ATOM | 5596 | CE1 | PHE | F | 177 | 26.170 | 45.877 | 14.709 | 1.00 | 27.35 | C |
| ATOM | 5597 | CE2 | PHE | F | 177 | 23.897 | 45.285 | 14.176 | 1.00 | 28.12 | C |
| ATOM | 5598 | CZ | PHE | F | 177 | 25.021 | 46.073 | 13.949 | 1.00 | 28.28 | C |
| ATOM | 5599 | N | ARG | F | 178 | 27.142 | 41.371 | 18.988 | 1.00 | 29.44 | N |
| ATOM | 5600 | CA | ARG | F | 178 | 27.254 | 40.549 | 20.187 | 1.00 | 29.63 | C |
| ATOM | 5601 | C | ARG | F | 178 | 27.345 | 41.365 | 21.481 | 1.00 | 29.59 | C |
| ATOM | 5602 | O | ARG | F | 178 | 27.910 | 42.467 | 21.513 | 1.00 | 27.47 | O |
| ATOM | 5603 | CB | ARG | F | 178 | 28.489 | 39.639 | 20.097 | 1.00 | 30.99 | C |
| ATOM | 5604 | CG | ARG | F | 178 | 28.567 | 38.762 | 18.847 | 1.00 | 36.16 | C |
| ATOM | 5605 | CD | ARG | F | 178 | 29.692 | 37.737 | 18.978 | 1.00 | 38.76 | C |
| ATOM | 5606 | NE | ARG | F | 178 | 29.502 | 36.952 | 20.194 | 1.00 | 43.37 | N |
| ATOM | 5607 | CZ | ARG | F | 178 | 30.425 | 36.178 | 20.760 | 1.00 | 45.05 | C |
| ATOM | 5608 | NH1 | ARG | F | 178 | 31.636 | 36.065 | 20.222 | 1.00 | 46.10 | N |
| ATOM | 5609 | NH2 | ARG | F | 178 | 30.138 | 35.537 | 21.888 | 1.00 | 45.60 | N |
| ATOM | 5610 | N | CYS | F | 179 | 26.790 | 40.799 | 22.549 | 1.00 | 28.88 | N |
| ATOM | 5611 | CA | CYS | F | 179 | 26.820 | 41.419 | 23.863 | 1.00 | 30.56 | C |
| ATOM | 5612 | C | CYS | F | 179 | 27.008 | 40.310 | 24.903 | 1.00 | 30.82 | C |
| ATOM | 5613 | O | CYS | F | 179 | 26.125 | 40.044 | 25.719 | 1.00 | 30.14 | O |
| ATOM | 5614 | CB | CYS | F | 179 | 25.522 | 42.197 | 24.090 | 1.00 | 31.07 | C |
| ATOM | 5615 | SG | CYS | F | 179 | 25.381 | 43.590 | 22.916 | 1.00 | 32.29 | S |
| ATOM | 5616 | N | PRO | F | 180 | 28.178 | 39.646 | 24.877 | 1.00 | 31.38 | N |
| ATOM | 5617 | CA | PRO | F | 180 | 28.499 | 38.554 | 25.806 | 1.00 | 31.88 | C |
| ATOM | 5618 | C | PRO | F | 180 | 28.193 | 38.983 | 27.228 | 1.00 | 31.88 | C |
| ATOM | 5619 | O | PRO | F | 180 | 28.736 | 39.975 | 27.700 | 1.00 | 31.46 | O |
| ATOM | 5620 | CB | PRO | F | 180 | 29.997 | 38.330 | 25.572 | 1.00 | 31.52 | C |
| ATOM | 5621 | CG | PRO | F | 180 | 30.177 | 38.721 | 24.136 | 1.00 | 31.75 | C |
| ATOM | 5622 | CD | PRO | F | 180 | 29.353 | 39.988 | 24.049 | 1.00 | 30.52 | C |
| ATOM | 5623 | N | ALA | F | 181 | 27.325 | 38.242 | 27.908 | 1.00 | 33.13 | N |
| ATOM | 5624 | CA | ALA | F | 181 | 26.956 | 38.600 | 29.271 | 1.00 | 34.09 | C |
| ATOM | 5625 | C | ALA | F | 181 | 26.984 | 37.457 | 30.285 | 1.00 | 35.33 | C |
| ATOM | 5626 | O | ALA | F | 181 | 26.913 | 36.283 | 29.931 | 1.00 | 35.01 | O |
| ATOM | 5627 | CB | ALA | F | 181 | 25.573 | 39.242 | 29.261 | 1.00 | 33.08 | C |
| ATOM | 5628 | N | GLY | F | 182 | 27.078 | 37.836 | 31.558 | 1.00 | 37.02 | N |
| ATOM | 5629 | CA | GLY | F | 182 | 27.078 | 36.882 | 32.653 | 1.00 | 37.61 | C |
| ATOM | 5630 | C | GLY | F | 182 | 26.039 | 37.337 | 33.661 | 1.00 | 38.86 | C |
| ATOM | 5631 | O | GLY | F | 182 | 25.473 | 38.427 | 33.512 | 1.00 | 39.18 | O |
| ATOM | 5632 | N | GLY | F | 183 | 25.787 | 36.523 | 34.684 | 1.00 | 39.21 | N |
| ATOM | 5633 | CA | GLY | F | 183 | 24.808 | 36.877 | 35.696 | 1.00 | 39.07 | C |
| ATOM | 5634 | C | GLY | F | 183 | 24.147 | 35.664 | 36.334 | 1.00 | 39.97 | C |
| ATOM | 5635 | O | GLY | F | 183 | 24.067 | 34.593 | 35.724 | 1.00 | 39.49 | O |
| ATOM | 5636 | N | ASN | F | 184 | 23.669 | 35.833 | 37.563 | 1.00 | 40.16 | N |
| ATOM | 5637 | CA | ASN | F | 184 | 23.009 | 34.753 | 38.289 | 1.00 | 41.28 | C |
| ATOM | 5638 | C | ASN | F | 184 | 21.817 | 35.278 | 39.081 | 1.00 | 41.39 | C |
| ATOM | 5639 | O | ASN | F | 184 | 21.978 | 36.018 | 40.042 | 1.00 | 41.84 | O |

TABLE 3-continued

| | | | | | | | | | | | |
|---|---|---|---|---|---|---|---|---|---|---|---|
| FGFR2(D2–D3) Complexed with FGF2 | | | | | | | | | | | |
| ATOM | 5640 | CB | ASN | F | 184 | 24.000 | 34.069 | 39.239 | 1.00 | 40.91 | C |
| ATOM | 5641 | N | PRO | F | 185 | 20.602 | 34.861 | 38.713 | 1.00 | 42.38 | N |
| ATOM | 5642 | CA | PRO | F | 185 | 20.293 | 33.939 | 37.617 | 1.00 | 42.85 | C |
| ATOM | 5643 | C | PRO | F | 185 | 20.635 | 34.437 | 36.212 | 1.00 | 44.15 | C |
| ATOM | 5644 | O | PRO | F | 185 | 20.856 | 35.633 | 35.990 | 1.00 | 44.57 | O |
| ATOM | 5645 | CB | PRO | F | 185 | 18.798 | 33.686 | 37.794 | 1.00 | 42.29 | C |
| ATOM | 5646 | CG | PRO | F | 185 | 18.307 | 34.969 | 38.373 | 1.00 | 42.96 | C |
| ATOM | 5647 | CD | PRO | F | 185 | 19.370 | 35.301 | 39.391 | 1.00 | 42.46 | C |
| ATOM | 5648 | N | MET | F | 186 | 20.681 | 33.495 | 35.273 | 1.00 | 44.62 | N |
| ATOM | 5649 | CA | MET | F | 186 | 20.972 | 33.778 | 33.873 | 1.00 | 44.74 | C |
| ATOM | 5650 | C | MET | F | 186 | 20.074 | 34.892 | 33.347 | 1.00 | 43.80 | C |
| ATOM | 5651 | O | MET | F | 186 | 18.852 | 34.763 | 33.322 | 1.00 | 43.60 | O |
| ATOM | 5652 | CB | MET | F | 186 | 20.750 | 32.518 | 33.040 | 1.00 | 46.95 | C |
| ATOM | 5653 | CG | MET | F | 186 | 22.018 | 31.918 | 32.466 | 1.00 | 49.12 | C |
| ATOM | 5654 | SD | MET | F | 186 | 22.712 | 32.953 | 31.179 | 1.00 | 50.87 | S |
| ATOM | 5655 | CE | MET | F | 186 | 24.474 | 32.841 | 31.516 | 1.00 | 50.04 | C |
| ATOM | 5656 | N | PRO | F | 187 | 20.676 | 36.002 | 32.905 | 1.00 | 42.90 | N |
| ATOM | 5657 | CA | PRO | F | 187 | 19.878 | 37.117 | 32.387 | 1.00 | 42.25 | C |
| ATOM | 5658 | C | PRO | F | 187 | 19.261 | 36.852 | 31.009 | 1.00 | 41.47 | C |
| ATOM | 5659 | O | PRO | F | 187 | 19.778 | 36.048 | 30.228 | 1.00 | 40.21 | O |
| ATOM | 5660 | CB | PRO | F | 187 | 20.881 | 38.268 | 32.368 | 1.00 | 42.05 | C |
| ATOM | 5661 | CG | PRO | F | 187 | 22.173 | 37.575 | 32.047 | 1.00 | 42.87 | C |
| ATOM | 5662 | CD | PRO | F | 187 | 22.118 | 36.317 | 32.891 | 1.00 | 42.21 | C |
| ATOM | 5663 | N | THR | F | 188 | 18.145 | 37.522 | 30.728 | 1.00 | 40.55 | N |
| ATOM | 5664 | CA | THR | F | 188 | 17.483 | 37.381 | 29.440 | 1.00 | 40.68 | C |
| ATOM | 5665 | C | THR | F | 188 | 18.042 | 38.446 | 28.505 | 1.00 | 40.77 | C |
| ATOM | 5666 | O | THR | F | 188 | 18.683 | 39.409 | 28.936 | 1.00 | 39.68 | O |
| ATOM | 5667 | CB | THR | F | 188 | 15.957 | 37.599 | 29.524 | 1.00 | 40.57 | C |
| ATOM | 5668 | OG1 | THR | F | 188 | 15.692 | 38.944 | 29.937 | 1.00 | 40.81 | O |
| ATOM | 5669 | CG2 | THR | F | 188 | 15.321 | 36.621 | 30.493 | 1.00 | 39.87 | C |
| ATOM | 5670 | N | MET | F | 189 | 17.782 | 38.272 | 27.219 | 1.00 | 40.70 | N |
| ATOM | 5671 | CA | MET | F | 189 | 18.267 | 39.206 | 26.220 | 1.00 | 40.97 | C |
| ATOM | 5672 | C | MET | F | 189 | 17.187 | 39.622 | 25.233 | 1.00 | 39.67 | C |
| ATOM | 5673 | O | MET | F | 189 | 16.418 | 38.789 | 24.758 | 1.00 | 39.80 | O |
| ATOM | 5674 | CB | MET | F | 189 | 19.424 | 38.574 | 25.444 | 1.00 | 42.23 | C |
| ATOM | 5675 | CG | MET | F | 189 | 19.761 | 39.298 | 24.151 | 1.00 | 44.84 | C |
| ATOM | 5676 | SD | MET | F | 189 | 21.320 | 38.752 | 23.419 | 1.00 | 49.58 | S |
| ATOM | 5677 | CE | MET | F | 189 | 22.406 | 40.078 | 24.039 | 1.00 | 47.75 | C |
| ATOM | 5678 | N | ARG | F | 190 | 17.146 | 40.912 | 24.922 | 1.00 | 37.90 | N |
| ATOM | 5679 | CA | ARG | F | 190 | 16.190 | 41.442 | 23.957 | 1.00 | 37.20 | C |
| ATOM | 5680 | C | ARG | F | 190 | 16.918 | 42.458 | 23.076 | 1.00 | 35.36 | C |
| ATOM | 5681 | O | ARG | F | 190 | 17.806 | 43.176 | 23.553 | 1.00 | 34.22 | O |
| ATOM | 5682 | CB | ARG | F | 190 | 15.033 | 42.143 | 24.661 | 1.00 | 38.85 | C |
| ATOM | 5683 | CG | ARG | F | 190 | 14.391 | 41.342 | 25.768 | 1.00 | 41.45 | C |
| ATOM | 5684 | CD | ARG | F | 190 | 13.371 | 42.202 | 26.488 | 1.00 | 43.93 | C |
| ATOM | 5685 | NE | ARG | F | 190 | 13.785 | 43.603 | 26.530 | 1.00 | 45.35 | N |
| ATOM | 5686 | CZ | ARG | F | 190 | 13.242 | 44.517 | 27.324 | 1.00 | 46.53 | C |
| ATOM | 5687 | NH1 | ARG | F | 190 | 12.262 | 44.177 | 28.152 | 1.00 | 47.49 | N |
| ATOM | 5688 | NH2 | ARG | F | 190 | 13.677 | 45.771 | 27.295 | 1.00 | 47.13 | N |
| ATOM | 5689 | N | TRP | F | 191 | 16.554 | 42.516 | 21.797 | 1.00 | 32.45 | N |
| ATOM | 5690 | CA | TRP | F | 191 | 17.175 | 43.468 | 20.881 | 1.00 | 30.87 | C |
| ATOM | 5691 | C | TRP | F | 191 | 16.179 | 44.513 | 20.361 | 1.00 | 30.74 | C |
| ATOM | 5692 | O | TRP | F | 191 | 15.050 | 44.182 | 19.983 | 1.00 | 30.08 | O |
| ATOM | 5693 | CB | TRP | F | 191 | 17.822 | 42.747 | 19.691 | 1.00 | 29.23 | C |
| ATOM | 5694 | CG | TRP | F | 191 | 19.069 | 41.961 | 20.031 | 1.00 | 27.86 | C |
| ATOM | 5695 | CD1 | TRP | F | 191 | 19.136 | 40.676 | 20.505 | 1.00 | 28.00 | C |
| ATOM | 5696 | CD2 | TRP | F | 191 | 20.419 | 42.424 | 19.945 | 1.00 | 26.19 | C |
| ATOM | 5697 | NE1 | TRP | F | 191 | 20.447 | 40.314 | 20.716 | 1.00 | 26.72 | N |
| ATOM | 5698 | CE2 | TRP | F | 191 | 21.255 | 41.368 | 20.378 | 1.00 | 26.84 | C |
| ATOM | 5699 | CE3 | TRP | F | 191 | 21.007 | 43.629 | 19.542 | 1.00 | 26.52 | C |
| ATOM | 5700 | CZ2 | TRP | F | 191 | 22.651 | 41.484 | 20.415 | 1.00 | 27.25 | C |
| ATOM | 5701 | CZ3 | TRP | F | 191 | 22.393 | 43.746 | 19.581 | 1.00 | 27.35 | C |
| ATOM | 5702 | CH2 | TRP | F | 191 | 23.200 | 42.677 | 20.015 | 1.00 | 26.74 | C |
| ATOM | 5703 | N | LEU | F | 192 | 16.599 | 45.776 | 20.357 | 1.00 | 29.31 | N |
| ATOM | 5704 | CA | LEU | F | 192 | 15.753 | 46.855 | 19.869 | 1.00 | 29.21 | C |
| ATOM | 5705 | C | LEU | F | 192 | 16.342 | 47.464 | 18.597 | 1.00 | 29.29 | C |
| ATOM | 5706 | O | LEU | F | 192 | 17.563 | 47.476 | 18.411 | 1.00 | 30.46 | O |
| ATOM | 5707 | CB | LEU | F | 192 | 15.635 | 47.979 | 20.913 | 1.00 | 28.58 | C |
| ATOM | 5708 | CG | LEU | F | 192 | 15.310 | 47.719 | 22.389 | 1.00 | 29.75 | C |
| ATOM | 5709 | CD1 | LEU | F | 192 | 15.487 | 49.003 | 23.168 | 1.00 | 30.04 | C |
| ATOM | 5710 | CD2 | LEU | F | 192 | 13.895 | 47.195 | 22.555 | 1.00 | 28.67 | C |
| ATOM | 5711 | N | LYS | F | 193 | 15.472 | 47.940 | 17.712 | 1.00 | 28.31 | N |
| ATOM | 5712 | CA | LYS | F | 193 | 15.902 | 48.633 | 16.508 | 1.00 | 28.68 | C |
| ATOM | 5713 | C | LYS | F | 193 | 15.378 | 50.065 | 16.685 | 1.00 | 29.44 | C |
| ATOM | 5714 | O | LYS | F | 193 | 14.165 | 50.283 | 16.814 | 1.00 | 28.28 | O |
| ATOM | 5715 | CB | LYS | F | 193 | 15.296 | 48.028 | 15.243 | 1.00 | 28.12 | C |
| ATOM | 5716 | CG | LYS | F | 193 | 15.691 | 48.806 | 13.977 | 1.00 | 28.39 | C |

TABLE 3-continued

FGFR2(D2–D3) Complexed with FGF2

| ATOM | 5717 | CD  | LYS | F | 193 | 15.047 | 48.252 | 12.710 | 1.00 | 30.20 | C |
|------|------|-----|-----|---|-----|--------|--------|--------|------|-------|---|
| ATOM | 5718 | CE  | LYS | F | 193 | 15.479 | 49.044 | 11.469 | 1.00 | 31.28 | C |
| ATOM | 5719 | NZ  | LYS | F | 193 | 14.810 | 48.560 | 10.212 | 1.00 | 31.21 | N |
| ATOM | 5720 | N   | ASN | F | 194 | 16.287 | 51.035 | 16.693 | 1.00 | 29.56 | N |
| ATOM | 5721 | CA  | ASN | F | 194 | 15.899 | 52.424 | 16.883 | 1.00 | 30.70 | C |
| ATOM | 5722 | C   | ASN | F | 194 | 15.035 | 52.598 | 18.138 | 1.00 | 31.61 | C |
| ATOM | 5723 | O   | ASN | F | 194 | 13.974 | 53.210 | 18.091 | 1.00 | 32.50 | O |
| ATOM | 5724 | CB  | ASN | F | 194 | 15.141 | 52.947 | 15.659 | 1.00 | 28.93 | C |
| ATOM | 5725 | CG  | ASN | F | 194 | 15.998 | 52.970 | 14.409 | 1.00 | 28.90 | C |
| ATOM | 5726 | OD1 | ASN | F | 194 | 17.194 | 53.287 | 14.464 | 1.00 | 26.90 | O |
| ATOM | 5727 | ND2 | ASN | F | 194 | 15.389 | 52.645 | 13.266 | 1.00 | 27.33 | N |
| ATOM | 5728 | N   | GLY | F | 195 | 15.492 | 52.028 | 19.250 | 1.00 | 32.59 | N |
| ATOM | 5729 | CA  | GLY | F | 195 | 14.785 | 52.139 | 20.518 | 1.00 | 32.86 | C |
| ATOM | 5730 | C   | GLY | F | 195 | 13.434 | 51.455 | 20.666 | 1.00 | 33.71 | C |
| ATOM | 5731 | O   | GLY | F | 195 | 12.741 | 51.692 | 21.648 | 1.00 | 33.71 | O |
| ATOM | 5732 | N   | LYS | F | 196 | 13.051 | 50.612 | 19.712 | 1.00 | 34.46 | N |
| ATOM | 5733 | CA  | LYS | F | 196 | 11.759 | 49.927 | 19.783 | 1.00 | 35.48 | C |
| ATOM | 5734 | C   | LYS | F | 196 | 11.935 | 48.442 | 19.500 | 1.00 | 35.38 | C |
| ATOM | 5735 | O   | LYS | F | 196 | 12.905 | 48.042 | 18.867 | 1.00 | 34.41 | O |
| ATOM | 5736 | CB  | LYS | F | 196 | 10.795 | 50.528 | 18.749 | 1.00 | 36.77 | C |
| ATOM | 5737 | CG  | LYS | F | 196 | 10.686 | 52.047 | 18.820 | 1.00 | 38.24 | C |
| ATOM | 5738 | CD  | LYS | F | 196 | 10.084 | 52.649 | 17.555 | 1.00 | 39.91 | C |
| ATOM | 5739 | CE  | LYS | F | 196 | 10.911 | 52.325 | 16.318 | 1.00 | 40.90 | C |
| ATOM | 5740 | NZ  | LYS | F | 196 | 10.542 | 53.178 | 15.150 | 1.00 | 41.25 | N |
| ATOM | 5741 | N   | GLU | F | 197 | 10.991 | 47.630 | 19.963 | 1.00 | 35.86 | N |
| ATOM | 5742 | CA  | GLU | F | 197 | 11.047 | 46.194 | 19.735 | 1.00 | 36.04 | C |
| ATOM | 5743 | C   | GLU | F | 197 | 11.352 | 45.921 | 18.264 | 1.00 | 35.04 | C |
| ATOM | 5744 | O   | GLU | F | 197 | 10.765 | 46.539 | 17.372 | 1.00 | 33.77 | O |
| ATOM | 5745 | CB  | GLU | F | 197 | 9.718  | 45.535 | 20.138 | 1.00 | 37.85 | C |
| ATOM | 5746 | CG  | GLU | F | 197 | 9.555  | 44.092 | 19.646 | 1.00 | 40.50 | C |
| ATOM | 5747 | CD  | GLU | F | 197 | 8.268  | 43.420 | 20.142 | 1.00 | 42.49 | C |
| ATOM | 5748 | OE1 | GLU | F | 197 | 7.216  | 44.098 | 20.218 | 1.00 | 43.04 | O |
| ATOM | 5749 | OE2 | GLU | F | 197 | 8.311  | 42.207 | 20.437 | 1.00 | 42.34 | O |
| ATOM | 5750 | N   | PHE | F | 198 | 12.297 | 45.013 | 18.033 | 1.00 | 34.31 | N |
| ATOM | 5751 | CA  | PHE | F | 198 | 12.721 | 44.626 | 16.695 | 1.00 | 33.94 | C |
| ATOM | 5752 | C   | PHE | F | 198 | 11.964 | 43.334 | 16.386 | 1.00 | 34.49 | C |
| ATOM | 5753 | O   | PHE | F | 198 | 12.159 | 42.328 | 17.062 | 1.00 | 33.96 | O |
| ATOM | 5754 | CB  | PHE | F | 198 | 14.234 | 44.373 | 16.708 | 1.00 | 32.03 | C |
| ATOM | 5755 | CG  | PHE | F | 198 | 14.851 | 44.172 | 15.345 | 1.00 | 30.37 | C |
| ATOM | 5756 | CD1 | PHE | F | 198 | 16.076 | 43.523 | 15.223 | 1.00 | 29.72 | C |
| ATOM | 5757 | CD2 | PHE | F | 198 | 14.238 | 44.659 | 14.195 | 1.00 | 29.77 | C |
| ATOM | 5758 | CE1 | PHE | F | 198 | 16.688 | 43.359 | 13.965 | 1.00 | 29.73 | C |
| ATOM | 5759 | CE2 | PHE | F | 198 | 14.840 | 44.500 | 12.936 | 1.00 | 30.25 | C |
| ATOM | 5760 | CZ  | PHE | F | 198 | 16.071 | 43.847 | 12.828 | 1.00 | 28.74 | C |
| ATOM | 5761 | N   | LYS | F | 199 | 11.099 | 43.372 | 15.377 | 1.00 | 35.60 | N |
| ATOM | 5762 | CA  | LYS | F | 199 | 10.304 | 42.204 | 14.994 | 1.00 | 36.11 | C |
| ATOM | 5763 | C   | LYS | F | 199 | 10.760 | 41.601 | 13.675 | 1.00 | 35.77 | C |
| ATOM | 5764 | O   | LYS | F | 199 | 11.331 | 42.293 | 12.836 | 1.00 | 35.67 | O |
| ATOM | 5765 | CB  | LYS | F | 199 | 8.825  | 42.584 | 14.896 | 1.00 | 36.91 | C |
| ATOM | 5766 | CG  | LYS | F | 199 | 8.226  | 43.120 | 16.196 | 1.00 | 38.98 | C |
| ATOM | 5767 | CD  | LYS | F | 199 | 6.748  | 43.447 | 16.026 | 1.00 | 40.85 | C |
| ATOM | 5768 | CE  | LYS | F | 199 | 6.103  | 43.833 | 17.358 | 1.00 | 42.06 | C |
| ATOM | 5769 | NZ  | LYS | F | 199 | 4.614  | 43.950 | 17.244 | 1.00 | 42.75 | N |
| ATOM | 5770 | N   | GLN | F | 200 | 10.490 | 40.308 | 13.502 | 1.00 | 35.69 | N |
| ATOM | 5771 | CA  | GLN | F | 200 | 10.855 | 39.582 | 12.295 | 1.00 | 35.41 | C |
| ATOM | 5772 | C   | GLN | F | 200 | 10.372 | 40.266 | 11.021 | 1.00 | 35.51 | C |
| ATOM | 5773 | O   | GLN | F | 200 | 11.083 | 40.306 | 10.027 | 1.00 | 35.58 | O |
| ATOM | 5774 | CB  | GLN | F | 200 | 10.288 | 38.155 | 12.351 | 1.00 | 34.06 | C |
| ATOM | 5775 | CG  | GLN | F | 200 | 10.978 | 37.228 | 13.347 | 1.00 | 31.65 | C |
| ATOM | 5776 | CD  | GLN | F | 200 | 12.453 | 37.037 | 13.039 | 1.00 | 29.88 | C |
| ATOM | 5777 | OE1 | GLN | F | 200 | 12.855 | 37.003 | 11.878 | 1.00 | 29.84 | O |
| ATOM | 5778 | NE2 | GLN | F | 200 | 13.261 | 36.889 | 14.080 | 1.00 | 29.62 | N |
| ATOM | 5779 | N   | GLU | F | 201 | 9.166  | 40.821 | 11.059 | 1.00 | 36.04 | N |
| ATOM | 5780 | CA  | GLU | F | 201 | 8.593  | 41.469 | 9.887  | 1.00 | 36.60 | C |
| ATOM | 5781 | C   | GLU | F | 201 | 9.204  | 42.833 | 9.576  | 1.00 | 35.96 | C |
| ATOM | 5782 | O   | GLU | F | 201 | 8.845  | 43.461 | 8.579  | 1.00 | 35.12 | O |
| ATOM | 5783 | CB  | GLU | F | 201 | 7.082  | 41.619 | 10.071 | 1.00 | 37.56 | C |
| ATOM | 5784 | CG  | GLU | F | 201 | 6.709  | 42.533 | 11.220 | 1.00 | 41.31 | C |
| ATOM | 5785 | CD  | GLU | F | 201 | 6.054  | 41.798 | 12.385 | 1.00 | 44.04 | C |
| ATOM | 5786 | OE1 | GLU | F | 201 | 6.638  | 40.813 | 12.917 | 1.00 | 43.75 | O |
| ATOM | 5787 | OE2 | GLU | F | 201 | 4.945  | 42.224 | 12.775 | 1.00 | 45.55 | O |
| ATOM | 5788 | N   | HIS | F | 202 | 10.124 | 43.296 | 10.420 | 1.00 | 35.49 | N |
| ATOM | 5789 | CA  | HIS | F | 202 | 10.751 | 44.597 | 10.196 | 1.00 | 35.12 | C |
| ATOM | 5790 | C   | HIS | F | 202 | 11.755 | 44.647 | 9.038  | 1.00 | 34.73 | C |
| ATOM | 5791 | O   | HIS | F | 202 | 12.200 | 45.730 | 8.653  | 1.00 | 35.10 | O |
| ATOM | 5792 | CB  | HIS | F | 202 | 11.409 | 45.115 | 11.481 | 1.00 | 35.18 | C |
| ATOM | 5793 | CG  | HIS | F | 202 | 10.434 | 45.600 | 12.513 | 1.00 | 35.87 | C |

TABLE 3-continued

FGFR2(D2–D3) Complexed with FGF2

| ATOM | 5794 | ND1 | HIS | F | 202 | 9.222 | 46.175 | 12.185 | 1.00 | 36.51 | N |
|---|---|---|---|---|---|---|---|---|---|---|---|
| ATOM | 5795 | CD2 | HIS | F | 202 | 10.504 | 45.623 | 13.866 | 1.00 | 34.64 | C |
| ATOM | 5796 | CE1 | HIS | F | 202 | 8.590 | 46.527 | 13.289 | 1.00 | 35.55 | C |
| ATOM | 5797 | NE2 | HIS | F | 202 | 9.348 | 46.204 | 14.324 | 1.00 | 35.01 | N |
| ATOM | 5798 | N | ARG | F | 203 | 12.115 | 43.487 | 8.488 | 1.00 | 33.96 | N |
| ATOM | 5799 | CA | ARG | F | 203 | 13.035 | 43.430 | 7.341 | 1.00 | 33.38 | C |
| ATOM | 5800 | C | ARG | F | 203 | 12.815 | 42.138 | 6.550 | 1.00 | 33.55 | C |
| ATOM | 5801 | O | ARG | F | 203 | 12.358 | 41.135 | 7.103 | 1.00 | 32.74 | O |
| ATOM | 5802 | CB | ARG | F | 203 | 14.512 | 43.525 | 7.795 | 1.00 | 30.83 | C |
| ATOM | 5803 | CG | ARG | F | 203 | 15.093 | 42.255 | 8.435 | 1.00 | 29.74 | C |
| ATOM | 5804 | CD | ARG | F | 203 | 16.514 | 42.509 | 8.978 | 1.00 | 29.31 | C |
| ATOM | 5805 | NE | ARG | F | 203 | 17.452 | 42.893 | 7.923 | 1.00 | 26.83 | N |
| ATOM | 5806 | CZ | ARG | F | 203 | 18.149 | 42.032 | 7.186 | 1.00 | 25.96 | C |
| ATOM | 5807 | NH1 | ARG | F | 203 | 18.030 | 40.728 | 7.391 | 1.00 | 24.85 | N |
| ATOM | 5808 | NH2 | ARG | F | 203 | 18.945 | 42.473 | 6.221 | 1.00 | 26.60 | N |
| ATOM | 5809 | N | ILE | F | 204 | 13.128 | 42.168 | 5.257 | 1.00 | 34.22 | N |
| ATOM | 5810 | CA | ILE | F | 204 | 12.976 | 40.982 | 4.427 | 1.00 | 35.18 | C |
| ATOM | 5811 | C | ILE | F | 204 | 13.856 | 39.882 | 5.023 | 1.00 | 35.19 | C |
| ATOM | 5812 | O | ILE | F | 204 | 15.038 | 40.109 | 5.311 | 1.00 | 34.84 | O |
| ATOM | 5813 | CB | ILE | F | 204 | 13.431 | 41.235 | 2.976 | 1.00 | 35.88 | C |
| ATOM | 5814 | CG1 | ILE | F | 204 | 12.668 | 42.424 | 2.379 | 1.00 | 36.13 | C |
| ATOM | 5815 | CG2 | ILE | F | 204 | 13.229 | 39.962 | 2.149 | 1.00 | 36.91 | C |
| ATOM | 5816 | CD1 | ILE | F | 204 | 11.167 | 42.264 | 2.392 | 1.00 | 36.71 | C |
| ATOM | 5817 | N | GLY | F | 205 | 13.269 | 38.705 | 5.233 | 1.00 | 34.69 | N |
| ATOM | 5818 | CA | GLY | F | 205 | 14.012 | 37.588 | 5.793 | 1.00 | 34.34 | C |
| ATOM | 5819 | C | GLY | F | 205 | 14.237 | 37.647 | 7.299 | 1.00 | 34.39 | C |
| ATOM | 5820 | O | GLY | F | 205 | 14.865 | 36.755 | 7.869 | 1.00 | 34.69 | O |
| ATOM | 5821 | N | GLY | F | 206 | 13.734 | 38.690 | 7.952 | 1.00 | 32.99 | N |
| ATOM | 5822 | CA | GLY | F | 206 | 13.901 | 38.800 | 9.393 | 1.00 | 33.37 | C |
| ATOM | 5823 | C | GLY | F | 206 | 15.328 | 38.694 | 9.924 | 1.00 | 33.23 | C |
| ATOM | 5824 | O | GLY | F | 206 | 16.289 | 39.114 | 9.276 | 1.00 | 32.48 | O |
| ATOM | 5825 | N | TYR | F | 207 | 15.472 | 38.136 | 11.117 | 1.00 | 32.64 | N |
| ATOM | 5826 | CA | TYR | F | 207 | 16.790 | 37.986 | 11.711 | 1.00 | 33.77 | C |
| ATOM | 5827 | C | TYR | F | 207 | 16.896 | 36.712 | 12.548 | 1.00 | 34.46 | C |
| ATOM | 5828 | O | TYR | F | 207 | 15.899 | 36.020 | 12.764 | 1.00 | 34.79 | O |
| ATOM | 5829 | CB | TYR | F | 207 | 17.118 | 39.209 | 12.583 | 1.00 | 33.55 | C |
| ATOM | 5830 | CG | TYR | F | 207 | 16.153 | 39.441 | 13.732 | 1.00 | 32.75 | C |
| ATOM | 5831 | CD1 | TYR | F | 207 | 15.015 | 40.246 | 13.571 | 1.00 | 32.44 | C |
| ATOM | 5832 | CD2 | TYR | F | 207 | 16.374 | 38.850 | 14.979 | 1.00 | 33.03 | C |
| ATOM | 5833 | CE1 | TYR | F | 207 | 14.119 | 40.460 | 14.628 | 1.00 | 32.42 | C |
| ATOM | 5834 | CE2 | TYR | F | 207 | 15.477 | 39.052 | 16.054 | 1.00 | 32.73 | C |
| ATOM | 5835 | CZ | TYR | F | 207 | 14.355 | 39.856 | 15.865 | 1.00 | 33.10 | C |
| ATOM | 5836 | OH | TYR | F | 207 | 13.462 | 40.028 | 16.896 | 1.00 | 31.83 | O |
| ATOM | 5837 | N | LYS | F | 208 | 18.107 | 36.419 | 13.019 | 1.00 | 34.55 | N |
| ATOM | 5838 | CA | LYS | F | 208 | 18.361 | 35.237 | 13.840 | 1.00 | 35.20 | C |
| ATOM | 5839 | C | LYS | F | 208 | 19.072 | 35.628 | 15.129 | 1.00 | 37.32 | C |
| ATOM | 5840 | O | LYS | F | 208 | 19.902 | 36.539 | 15.139 | 1.00 | 37.39 | O |
| ATOM | 5841 | CB | LYS | F | 208 | 19.236 | 34.236 | 13.083 | 1.00 | 33.89 | C |
| ATOM | 5842 | CG | LYS | F | 208 | 18.622 | 33.695 | 11.804 | 1.00 | 33.01 | C |
| ATOM | 5843 | CD | LYS | F | 208 | 19.638 | 32.897 | 11.002 | 1.00 | 31.73 | C |
| ATOM | 5844 | CE | LYS | F | 208 | 19.003 | 32.362 | 9.729 | 1.00 | 31.93 | C |
| ATOM | 5845 | NZ | LYS | F | 208 | 19.951 | 31.576 | 8.907 | 1.00 | 31.98 | N |
| ATOM | 5846 | N | VAL | F | 209 | 18.742 | 34.941 | 16.216 | 1.00 | 39.09 | N |
| ATOM | 5847 | CA | VAL | F | 209 | 19.364 | 35.204 | 17.507 | 1.00 | 41.34 | C |
| ATOM | 5848 | C | VAL | F | 209 | 19.850 | 33.902 | 18.134 | 1.00 | 43.43 | C |
| ATOM | 5849 | O | VAL | F | 209 | 19.107 | 32.916 | 18.204 | 1.00 | 44.61 | O |
| ATOM | 5850 | CB | VAL | F | 209 | 18.384 | 35.897 | 18.489 | 1.00 | 40.99 | C |
| ATOM | 5851 | CG1 | VAL | F | 209 | 18.955 | 35.882 | 19.897 | 1.00 | 41.66 | C |
| ATOM | 5852 | CG2 | VAL | F | 209 | 18.143 | 37.332 | 18.060 | 1.00 | 40.70 | C |
| ATOM | 5853 | N | ARG | F | 210 | 21.105 | 33.897 | 18.572 | 1.00 | 44.15 | N |
| ATOM | 5854 | CA | ARG | F | 210 | 21.688 | 32.727 | 19.216 | 1.00 | 45.63 | C |
| ATOM | 5855 | C | ARG | F | 210 | 21.983 | 33.107 | 20.671 | 1.00 | 46.74 | C |
| ATOM | 5856 | O | ARG | F | 210 | 23.029 | 33.684 | 20.979 | 1.00 | 46.52 | O |
| ATOM | 5857 | CB | ARG | F | 210 | 22.972 | 32.302 | 18.499 | 1.00 | 45.37 | C |
| ATOM | 5858 | N | ASN | F | 211 | 21.044 | 32.794 | 21.560 | 1.00 | 48.22 | N |
| ATOM | 5859 | CA | ASN | F | 211 | 21.191 | 33.119 | 22.974 | 1.00 | 49.06 | C |
| ATOM | 5860 | C | ASN | F | 211 | 22.512 | 32.641 | 23.558 | 1.00 | 48.57 | C |
| ATOM | 5861 | O | ASN | F | 211 | 23.121 | 33.336 | 24.370 | 1.00 | 48.61 | O |
| ATOM | 5862 | CB | ASN | F | 211 | 20.019 | 32.552 | 23.774 | 1.00 | 50.40 | C |
| ATOM | 5863 | CG | ASN | F | 211 | 18.688 | 33.151 | 23.348 | 1.00 | 52.24 | C |
| ATOM | 5864 | OD1 | ASN | F | 211 | 18.489 | 34.370 | 23.409 | 1.00 | 53.07 | O |
| ATOM | 5865 | ND2 | ASN | F | 211 | 17.773 | 32.296 | 22.906 | 1.00 | 52.36 | N |
| ATOM | 5866 | N | GLN | F | 212 | 22.960 | 31.463 | 23.136 | 1.00 | 47.95 | N |
| ATOM | 5867 | CA | GLN | F | 212 | 24.222 | 30.906 | 23.622 | 1.00 | 47.07 | C |
| ATOM | 5868 | C | GLN | F | 212 | 25.408 | 31.839 | 23.341 | 1.00 | 46.07 | C |
| ATOM | 5869 | O | GLN | F | 212 | 26.396 | 31.832 | 24.076 | 1.00 | 46.29 | O |
| ATOM | 5870 | CB | GLN | F | 212 | 24.479 | 29.536 | 22.981 | 1.00 | 47.25 | C |

TABLE 3-continued

| FGFR2(D2–D3) Complexed with FGF2 | | | | | | | | | | |
|---|---|---|---|---|---|---|---|---|---|---|
| ATOM | 5871 | N | HIS | F | 213 | 25.312 | 32.638 | 22.279 | 1.00 | 43.99 | N |
| ATOM | 5872 | CA | HIS | F | 213 | 26.384 | 33.569 | 21.932 | 1.00 | 41.91 | C |
| ATOM | 5873 | C | HIS | F | 213 | 26.008 | 35.040 | 22.164 | 1.00 | 40.31 | C |
| ATOM | 5874 | O | HIS | F | 213 | 26.784 | 35.938 | 21.833 | 1.00 | 39.47 | O |
| ATOM | 5875 | CB | HIS | F | 213 | 26.796 | 33.384 | 20.467 | 1.00 | 42.21 | C |
| ATOM | 5876 | N | TRP | F | 214 | 24.825 | 35.280 | 22.733 | 1.00 | 38.43 | N |
| ATOM | 5877 | CA | TRP | F | 214 | 24.343 | 36.647 | 22.988 | 1.00 | 36.90 | C |
| ATOM | 5878 | C | TRP | F | 214 | 24.485 | 37.477 | 21.710 | 1.00 | 35.65 | C |
| ATOM | 5879 | O | TRP | F | 214 | 24.998 | 38.596 | 21.732 | 1.00 | 34.83 | O |
| ATOM | 5880 | CB | TRP | F | 214 | 25.156 | 37.310 | 24.117 | 1.00 | 37.32 | C |
| ATOM | 5881 | CG | TRP | F | 214 | 25.253 | 36.467 | 25.357 | 1.00 | 38.36 | C |
| ATOM | 5882 | CD1 | TRP | F | 214 | 26.254 | 35.591 | 25.680 | 1.00 | 39.05 | C |
| ATOM | 5883 | CD2 | TRP | F | 214 | 24.268 | 36.348 | 26.391 | 1.00 | 38.90 | C |
| ATOM | 5884 | NE1 | TRP | F | 214 | 25.947 | 34.929 | 26.846 | 1.00 | 38.91 | N |
| ATOM | 5885 | CE2 | TRP | F | 214 | 24.735 | 35.374 | 27.304 | 1.00 | 39.07 | C |
| ATOM | 5886 | CE3 | TRP | F | 214 | 23.032 | 36.968 | 26.635 | 1.00 | 39.11 | C |
| ATOM | 5887 | CZ2 | TRP | F | 214 | 24.011 | 35.005 | 28.443 | 1.00 | 39.13 | C |
| ATOM | 5888 | CZ3 | TRP | F | 214 | 22.310 | 36.600 | 27.769 | 1.00 | 39.21 | C |
| ATOM | 5889 | CH2 | TRP | F | 214 | 22.803 | 35.627 | 28.658 | 1.00 | 39.44 | C |
| ATOM | 5890 | N | SER | F | 215 | 24.018 | 36.929 | 20.594 | 1.00 | 34.42 | N |
| ATOM | 5891 | CA | SER | F | 215 | 24.159 | 37.615 | 19.321 | 1.00 | 33.05 | C |
| ATOM | 5892 | C | SER | F | 215 | 22.886 | 37.824 | 18.506 | 1.00 | 32.30 | C |
| ATOM | 5893 | O | SER | F | 215 | 21.909 | 37.071 | 18.633 | 1.00 | 31.69 | O |
| ATOM | 5894 | CB | SER | F | 215 | 25.167 | 36.853 | 18.457 | 1.00 | 34.47 | C |
| ATOM | 5895 | OG | SER | F | 215 | 24.645 | 35.578 | 18.095 | 1.00 | 34.50 | O |
| ATOM | 5896 | N | LEU | F | 216 | 22.936 | 38.850 | 17.653 | 1.00 | 30.67 | N |
| ATOM | 5897 | CA | LEU | F | 216 | 21.854 | 39.202 | 16.735 | 1.00 | 29.22 | C |
| ATOM | 5898 | C | LEU | F | 216 | 22.477 | 39.122 | 15.347 | 1.00 | 28.34 | C |
| ATOM | 5899 | O | LEU | F | 216 | 23.507 | 39.757 | 15.086 | 1.00 | 27.30 | O |
| ATOM | 5900 | CB | LEU | F | 216 | 21.358 | 40.633 | 16.967 | 1.00 | 28.18 | C |
| ATOM | 5901 | CG | LEU | F | 216 | 20.462 | 41.142 | 15.821 | 1.00 | 28.87 | C |
| ATOM | 5902 | CD1 | LEU | F | 216 | 19.159 | 40.357 | 15.846 | 1.00 | 29.36 | C |
| ATOM | 5903 | CD2 | LEU | F | 216 | 20.176 | 42.639 | 15.964 | 1.00 | 28.49 | C |
| ATOM | 5904 | N | ILE | F | 217 | 21.853 | 38.357 | 14.456 | 1.00 | 28.20 | N |
| ATOM | 5905 | CA | ILE | F | 217 | 22.364 | 38.187 | 13.098 | 1.00 | 28.31 | C |
| ATOM | 5906 | C | ILE | F | 217 | 21.402 | 38.618 | 12.000 | 1.00 | 28.13 | C |
| ATOM | 5907 | O | ILE | F | 217 | 20.230 | 38.227 | 11.999 | 1.00 | 27.90 | O |
| ATOM | 5908 | CB | ILE | F | 217 | 22.779 | 36.718 | 12.872 | 1.00 | 28.75 | C |
| ATOM | 5909 | CG1 | ILE | F | 217 | 24.022 | 36.418 | 13.716 | 1.00 | 30.55 | C |
| ATOM | 5910 | CG2 | ILE | F | 217 | 23.053 | 36.452 | 11.397 | 1.00 | 28.99 | C |
| ATOM | 5911 | CD1 | ILE | F | 217 | 24.513 | 34.974 | 13.624 | 1.00 | 32.18 | C |
| ATOM | 5912 | N | MET | F | 218 | 21.909 | 39.432 | 11.074 | 1.00 | 27.45 | N |
| ATOM | 5913 | CA | MET | F | 218 | 21.129 | 39.915 | 9.933 | 1.00 | 29.12 | C |
| ATOM | 5914 | C | MET | F | 218 | 21.899 | 39.570 | 8.646 | 1.00 | 29.98 | C |
| ATOM | 5915 | O | MET | F | 218 | 23.030 | 40.027 | 8.436 | 1.00 | 29.81 | O |
| ATOM | 5916 | CB | MET | F | 218 | 20.905 | 41.434 | 10.047 | 1.00 | 29.43 | C |
| ATOM | 5917 | CG | MET | F | 218 | 19.911 | 41.835 | 11.138 | 1.00 | 28.75 | C |
| ATOM | 5918 | SD | MET | F | 218 | 19.910 | 43.607 | 11.546 | 1.00 | 29.55 | S |
| ATOM | 5919 | CE | MET | F | 218 | 19.497 | 44.305 | 10.031 | 1.00 | 29.23 | C |
| ATOM | 5920 | N | GLU | F | 219 | 21.285 | 38.752 | 7.795 | 1.00 | 29.80 | N |
| ATOM | 5921 | CA | GLU | F | 219 | 21.907 | 38.325 | 6.542 | 1.00 | 29.89 | C |
| ATOM | 5922 | C | GLU | F | 219 | 21.525 | 39.213 | 5.365 | 1.00 | 29.76 | C |
| ATOM | 5923 | O | GLU | F | 219 | 20.452 | 39.815 | 5.360 | 1.00 | 29.81 | O |
| ATOM | 5924 | CB | GLU | F | 219 | 21.512 | 36.872 | 6.259 | 1.00 | 30.00 | C |
| ATOM | 5925 | CG | GLU | F | 219 | 21.882 | 35.928 | 7.401 | 1.00 | 30.20 | C |
| ATOM | 5926 | CD | GLU | F | 219 | 21.026 | 34.680 | 7.437 | 1.00 | 30.77 | C |
| ATOM | 5927 | OE1 | GLU | F | 219 | 19.794 | 34.814 | 7.316 | 1.00 | 31.01 | O |
| ATOM | 5928 | OE2 | GLU | F | 219 | 21.581 | 33.571 | 7.598 | 1.00 | 31.65 | O |
| ATOM | 5929 | N | SER | F | 220 | 22.420 | 39.301 | 4.383 | 1.00 | 29.62 | N |
| ATOM | 5930 | CA | SER | F | 220 | 22.210 | 40.096 | 3.175 | 1.00 | 29.82 | C |
| ATOM | 5931 | C | SER | F | 220 | 21.701 | 41.506 | 3.441 | 1.00 | 29.76 | C |
| ATOM | 5932 | O | SER | F | 220 | 20.651 | 41.897 | 2.921 | 1.00 | 29.19 | O |
| ATOM | 5933 | CB | SER | F | 220 | 21.219 | 39.388 | 2.240 | 1.00 | 30.67 | C |
| ATOM | 5934 | OG | SER | F | 220 | 21.669 | 38.089 | 1.907 | 1.00 | 31.43 | O |
| ATOM | 5935 | N | VAL | F | 221 | 22.451 | 42.283 | 4.217 | 1.00 | 28.67 | N |
| ATOM | 5936 | CA | VAL | F | 221 | 22.021 | 43.637 | 4.541 | 1.00 | 28.32 | C |
| ATOM | 5937 | C | VAL | F | 221 | 21.880 | 44.555 | 3.323 | 1.00 | 29.51 | C |
| ATOM | 5938 | O | VAL | F | 221 | 22.542 | 44.370 | 2.293 | 1.00 | 29.53 | O |
| ATOM | 5939 | CB | VAL | F | 221 | 22.971 | 44.284 | 5.594 | 1.00 | 28.01 | C |
| ATOM | 5940 | CG1 | VAL | F | 221 | 23.139 | 43.337 | 6.781 | 1.00 | 26.11 | C |
| ATOM | 5941 | CG2 | VAL | F | 221 | 24.324 | 44.609 | 4.983 | 1.00 | 26.82 | C |
| ATOM | 5942 | N | VAL | F | 222 | 20.988 | 45.533 | 3.449 | 1.00 | 29.96 | N |
| ATOM | 5943 | CA | VAL | F | 222 | 20.716 | 46.507 | 2.404 | 1.00 | 31.14 | C |
| ATOM | 5944 | C | VAL | F | 222 | 20.671 | 47.892 | 3.056 | 1.00 | 32.51 | C |
| ATOM | 5945 | O | VAL | F | 222 | 20.606 | 48.007 | 4.281 | 1.00 | 32.13 | O |
| ATOM | 5946 | CB | VAL | F | 222 | 19.341 | 46.236 | 1.704 | 1.00 | 31.92 | C |
| ATOM | 5947 | CG1 | VAL | F | 222 | 19.393 | 44.934 | 0.889 | 1.00 | 32.22 | C |

TABLE 3-continued

FGFR2(D2–D3) Complexed with FGF2

| ATOM | 5948 | CG2 | VAL | F | 222 | 18.229 | 46.149 | 2.749 | 1.00 | 30.96 | C |
|---|---|---|---|---|---|---|---|---|---|---|---|
| ATOM | 5949 | N | PRO | F | 223 | 20.717 | 48.961 | 2.242 | 1.00 | 33.33 | N |
| ATOM | 5950 | CA | PRO | F | 223 | 20.678 | 50.337 | 2.744 | 1.00 | 33.05 | C |
| ATOM | 5951 | C | PRO | F | 223 | 19.621 | 50.612 | 3.808 | 1.00 | 32.75 | C |
| ATOM | 5952 | O | PRO | F | 223 | 19.888 | 51.306 | 4.779 | 1.00 | 31.69 | O |
| ATOM | 5953 | CB | PRO | F | 223 | 20.449 | 51.149 | 1.472 | 1.00 | 32.99 | C |
| ATOM | 5954 | CG | PRO | F | 223 | 21.301 | 50.414 | 0.489 | 1.00 | 33.35 | C |
| ATOM | 5955 | CD | PRO | F | 223 | 20.963 | 48.949 | 0.786 | 1.00 | 33.24 | C |
| ATOM | 5956 | N | SER | F | 224 | 18.428 | 50.051 | 3.636 | 1.00 | 32.51 | N |
| ATOM | 5957 | CA | SER | F | 224 | 17.348 | 50.278 | 4.584 | 1.00 | 31.69 | C |
| ATOM | 5958 | C | SER | F | 224 | 17.599 | 49.727 | 5.999 | 1.00 | 31.73 | C |
| ATOM | 5959 | O | SER | F | 224 | 16.884 | 50.077 | 6.937 | 1.00 | 31.16 | O |
| ATOM | 5960 | CB | SER | F | 224 | 16.057 | 49.697 | 4.013 | 1.00 | 31.66 | C |
| ATOM | 5961 | OG | SER | F | 224 | 16.199 | 48.307 | 3.774 | 1.00 | 32.99 | O |
| ATOM | 5962 | N | ASP | F | 225 | 18.604 | 48.867 | 6.160 | 1.00 | 31.38 | N |
| ATOM | 5963 | CA | ASP | F | 225 | 18.912 | 48.311 | 7.484 | 1.00 | 30.26 | C |
| ATOM | 5964 | C | ASP | F | 225 | 19.669 | 49.309 | 8.378 | 1.00 | 30.11 | C |
| ATOM | 5965 | O | ASP | F | 225 | 19.874 | 49.068 | 9.570 | 1.00 | 28.77 | O |
| ATOM | 5966 | CB | ASP | F | 225 | 19.741 | 47.028 | 7.364 | 1.00 | 29.82 | C |
| ATOM | 5967 | CG | ASP | F | 225 | 18.952 | 45.864 | 6.793 | 1.00 | 29.68 | C |
| ATOM | 5968 | OD1 | ASP | F | 225 | 17.802 | 45.623 | 7.242 | 1.00 | 28.36 | O |
| ATOM | 5969 | OD2 | ASP | F | 225 | 19.500 | 45.174 | 5.909 | 1.00 | 27.10 | O |
| ATOM | 5970 | N | LYS | F | 226 | 20.089 | 50.429 | 7.797 | 1.00 | 30.34 | N |
| ATOM | 5971 | CA | LYS | F | 226 | 20.809 | 51.438 | 8.566 | 1.00 | 30.46 | C |
| ATOM | 5972 | C | LYS | F | 226 | 19.980 | 51.868 | 9.778 | 1.00 | 30.07 | C |
| ATOM | 5973 | O | LYS | F | 226 | 18.763 | 52.049 | 9.667 | 1.00 | 29.46 | O |
| ATOM | 5974 | CB | LYS | F | 226 | 21.134 | 52.656 | 7.691 | 1.00 | 31.03 | C |
| ATOM | 5975 | CG | LYS | F | 226 | 21.782 | 53.802 | 8.481 | 1.00 | 32.45 | C |
| ATOM | 5976 | CD | LYS | F | 226 | 22.034 | 55.040 | 7.619 | 1.00 | 33.36 | C |
| ATOM | 5977 | CE | LYS | F | 226 | 22.717 | 56.153 | 8.434 | 1.00 | 34.79 | C |
| ATOM | 5978 | NZ | LYS | F | 226 | 23.090 | 57.326 | 7.587 | 1.00 | 35.90 | N |
| ATOM | 5979 | N | GLY | F | 227 | 20.644 | 52.018 | 10.928 | 1.00 | 28.53 | N |
| ATOM | 5980 | CA | GLY | F | 227 | 19.955 | 52.421 | 12.142 | 1.00 | 28.88 | C |
| ATOM | 5981 | C | GLY | F | 227 | 20.679 | 51.982 | 13.403 | 1.00 | 29.17 | C |
| ATOM | 5982 | O | GLY | F | 227 | 21.838 | 51.556 | 13.346 | 1.00 | 28.63 | O |
| ATOM | 5983 | N | ASN | F | 228 | 20.012 | 52.102 | 14.546 | 1.00 | 28.73 | N |
| ATOM | 5984 | CA | ASN | F | 228 | 20.608 | 51.697 | 15.815 | 1.00 | 29.18 | C |
| ATOM | 5985 | C | ASN | F | 228 | 20.029 | 50.382 | 16.314 | 1.00 | 28.27 | C |
| ATOM | 5986 | O | ASN | F | 228 | 18.821 | 50.157 | 16.229 | 1.00 | 28.24 | O |
| ATOM | 5987 | CB | ASN | F | 228 | 20.386 | 52.755 | 16.888 | 1.00 | 31.52 | C |
| ATOM | 5988 | CG | ASN | F | 228 | 20.888 | 54.112 | 16.469 | 1.00 | 33.14 | C |
| ATOM | 5989 | OD1 | ASN | F | 228 | 21.966 | 54.241 | 15.897 | 1.00 | 34.19 | O |
| ATOM | 5990 | ND2 | ASN | F | 228 | 20.108 | 55.138 | 16.760 | 1.00 | 34.39 | N |
| ATOM | 5991 | N | TYR | F | 229 | 20.902 | 49.521 | 16.832 | 1.00 | 26.46 | N |
| ATOM | 5992 | CA | TYR | F | 229 | 20.502 | 48.229 | 17.374 | 1.00 | 25.52 | C |
| ATOM | 5993 | C | TYR | F | 229 | 21.014 | 48.118 | 18.801 | 1.00 | 25.73 | C |
| ATOM | 5994 | O | TYR | F | 229 | 22.227 | 48.156 | 19.062 | 1.00 | 25.37 | O |
| ATOM | 5995 | CB | TYR | F | 229 | 21.034 | 47.088 | 16.505 | 1.00 | 23.62 | C |
| ATOM | 5996 | CG | TYR | F | 229 | 20.487 | 47.141 | 15.104 | 1.00 | 24.17 | C |
| ATOM | 5997 | CD1 | TYR | F | 229 | 21.007 | 48.028 | 14.167 | 1.00 | 24.31 | C |
| ATOM | 5998 | CD2 | TYR | F | 229 | 19.383 | 46.368 | 14.735 | 1.00 | 24.16 | C |
| ATOM | 5999 | CE1 | TYR | F | 229 | 20.429 | 48.154 | 12.901 | 1.00 | 25.39 | C |
| ATOM | 6000 | CE2 | TYR | F | 229 | 18.811 | 46.482 | 13.488 | 1.00 | 22.86 | C |
| ATOM | 6001 | CZ | TYR | F | 229 | 19.325 | 47.374 | 12.576 | 1.00 | 24.60 | C |
| ATOM | 6002 | OH | TYR | F | 229 | 18.706 | 47.529 | 11.356 | 1.00 | 26.12 | O |
| ATOM | 6003 | N | THR | F | 230 | 20.069 | 47.979 | 19.724 | 1.00 | 25.46 | N |
| ATOM | 6004 | CA | THR | F | 230 | 20.374 | 47.917 | 21.148 | 1.00 | 24.62 | C |
| ATOM | 6005 | C | THR | F | 230 | 20.056 | 46.583 | 21.807 | 1.00 | 25.10 | C |
| ATOM | 6006 | O | THR | F | 230 | 18.980 | 46.005 | 21.613 | 1.00 | 24.11 | O |
| ATOM | 6007 | CB | THR | F | 230 | 19.587 | 49.004 | 21.896 | 1.00 | 23.96 | C |
| ATOM | 6008 | OG1 | THR | F | 230 | 19.859 | 50.274 | 21.289 | 1.00 | 23.10 | O |
| ATOM | 6009 | CG2 | THR | F | 230 | 19.961 | 49.021 | 23.373 | 1.00 | 22.18 | C |
| ATOM | 6010 | N | CYS | F | 231 | 21.004 | 46.099 | 22.598 | 1.00 | 25.89 | N |
| ATOM | 6011 | CA | CYS | F | 231 | 20.822 | 44.855 | 23.315 | 1.00 | 26.87 | C |
| ATOM | 6012 | C | CYS | F | 231 | 20.512 | 45.213 | 24.771 | 1.00 | 27.21 | C |
| ATOM | 6013 | O | CYS | F | 231 | 21.214 | 46.020 | 25.370 | 1.00 | 26.18 | O |
| ATOM | 6014 | CB | CYS | F | 231 | 22.099 | 44.007 | 23.237 | 1.00 | 27.34 | C |
| ATOM | 6015 | SG | CYS | F | 231 | 23.556 | 44.785 | 24.032 | 1.00 | 27.77 | S |
| ATOM | 6016 | N | VAL | F | 232 | 19.443 | 44.631 | 25.315 | 1.00 | 27.93 | N |
| ATOM | 6017 | CA | VAL | F | 232 | 19.050 | 44.853 | 26.705 | 1.00 | 29.90 | C |
| ATOM | 6018 | C | VAL | F | 232 | 19.155 | 43.504 | 27.432 | 1.00 | 30.42 | C |
| ATOM | 6019 | O | VAL | F | 232 | 18.573 | 42.517 | 27.006 | 1.00 | 31.57 | O |
| ATOM | 6020 | CB | VAL | F | 232 | 17.609 | 45.396 | 26.778 | 1.00 | 30.35 | C |
| ATOM | 6021 | CG1 | VAL | F | 232 | 17.246 | 45.772 | 28.211 | 1.00 | 29.59 | C |
| ATOM | 6022 | CG2 | VAL | F | 232 | 17.482 | 46.603 | 25.853 | 1.00 | 29.86 | C |
| ATOM | 6023 | N | VAL | F | 233 | 19.921 | 43.464 | 28.516 | 1.00 | 31.25 | N |
| ATOM | 6024 | CA | VAL | F | 233 | 20.130 | 42.231 | 29.269 | 1.00 | 32.28 | C |

TABLE 3-continued

FGFR2(D2–D3) Complexed with FGF2

| ATOM | 6025 | C | VAL | F | 233 | 19.688 | 42.432 | 30.716 | 1.00 | 32.94 | C |
|---|---|---|---|---|---|---|---|---|---|---|---|
| ATOM | 6026 | O | VAL | F | 233 | 20.094 | 43.403 | 31.363 | 1.00 | 32.94 | O |
| ATOM | 6027 | CB | VAL | F | 233 | 21.624 | 41.825 | 29.239 | 1.00 | 31.65 | C |
| ATOM | 6028 | CG1 | VAL | F | 233 | 21.830 | 40.525 | 29.969 | 1.00 | 33.89 | C |
| ATOM | 6029 | CG2 | VAL | F | 233 | 22.088 | 41.687 | 27.817 | 1.00 | 33.22 | C |
| ATOM | 6030 | N | GLU | F | 234 | 18.879 | 41.510 | 31.236 | 1.00 | 32.73 | N |
| ATOM | 6031 | CA | GLU | F | 234 | 18.375 | 41.667 | 32.590 | 1.00 | 34.27 | C |
| ATOM | 6032 | C | GLU | F | 234 | 18.012 | 40.423 | 33.407 | 1.00 | 34.49 | C |
| ATOM | 6033 | O | GLU | F | 234 | 17.763 | 39.344 | 32.865 | 1.00 | 34.80 | O |
| ATOM | 6034 | CB | GLU | F | 234 | 17.139 | 42.573 | 32.539 | 1.00 | 34.06 | C |
| ATOM | 6035 | N | ASN | F | 235 | 18.003 | 40.607 | 34.725 | 1.00 | 35.03 | N |
| ATOM | 6036 | CA | ASN | F | 235 | 17.590 | 39.585 | 35.690 | 1.00 | 35.08 | C |
| ATOM | 6037 | C | ASN | F | 235 | 17.034 | 40.378 | 36.868 | 1.00 | 35.26 | C |
| ATOM | 6038 | O | ASN | F | 235 | 16.921 | 41.603 | 36.781 | 1.00 | 34.94 | O |
| ATOM | 6039 | CB | ASN | F | 235 | 18.734 | 38.635 | 36.108 | 1.00 | 34.70 | C |
| ATOM | 6040 | CG | ASN | F | 235 | 19.857 | 39.323 | 36.869 | 1.00 | 35.25 | C |
| ATOM | 6041 | OD1 | ASN | F | 235 | 19.681 | 40.395 | 37.436 | 1.00 | 35.24 | O |
| ATOM | 6042 | ND2 | ASN | F | 235 | 21.019 | 38.678 | 36.909 | 1.00 | 35.44 | N |
| ATOM | 6043 | N | GLU | F | 236 | 16.679 | 39.700 | 37.952 | 1.00 | 36.51 | N |
| ATOM | 6044 | CA | GLU | F | 236 | 16.100 | 40.364 | 39.123 | 1.00 | 37.07 | C |
| ATOM | 6045 | C | GLU | F | 236 | 16.963 | 41.442 | 39.798 | 1.00 | 37.35 | C |
| ATOM | 6046 | O | GLU | F | 236 | 16.432 | 42.300 | 40.503 | 1.00 | 37.63 | O |
| ATOM | 6047 | CB | GLU | F | 236 | 15.704 | 39.305 | 40.162 | 1.00 | 37.52 | C |
| ATOM | 6048 | N | TYR | F | 237 | 18.276 | 41.407 | 39.578 | 1.00 | 37.29 | N |
| ATOM | 6049 | CA | TYR | F | 237 | 19.180 | 42.367 | 40.215 | 1.00 | 37.37 | C |
| ATOM | 6050 | C | TYR | F | 237 | 19.685 | 43.499 | 39.317 | 1.00 | 36.07 | C |
| ATOM | 6051 | O | TYR | F | 237 | 20.510 | 44.312 | 39.737 | 1.00 | 35.50 | O |
| ATOM | 6052 | CB | TYR | F | 237 | 20.362 | 41.603 | 40.822 | 1.00 | 39.38 | C |
| ATOM | 6053 | CG | TYR | F | 237 | 19.925 | 40.411 | 41.654 | 1.00 | 41.87 | C |
| ATOM | 6054 | CD1 | TYR | F | 237 | 20.347 | 39.114 | 41.334 | 1.00 | 42.98 | C |
| ATOM | 6055 | CD2 | TYR | F | 237 | 19.066 | 40.574 | 42.738 | 1.00 | 42.55 | C |
| ATOM | 6056 | CE1 | TYR | F | 237 | 19.920 | 38.010 | 42.075 | 1.00 | 44.44 | C |
| ATOM | 6057 | CE2 | TYR | F | 237 | 18.633 | 39.484 | 43.482 | 1.00 | 44.45 | C |
| ATOM | 6058 | CZ | TYR | F | 237 | 19.062 | 38.205 | 43.146 | 1.00 | 45.27 | C |
| ATOM | 6059 | OH | TYR | F | 237 | 18.618 | 37.126 | 43.877 | 1.00 | 47.09 | O |
| ATOM | 6060 | N | GLY | F | 238 | 19.202 | 43.563 | 38.082 | 1.00 | 34.94 | N |
| ATOM | 6061 | CA | GLY | F | 238 | 19.656 | 44.642 | 37.223 | 1.00 | 34.17 | C |
| ATOM | 6062 | C | GLY | F | 238 | 19.327 | 44.554 | 35.746 | 1.00 | 33.32 | C |
| ATOM | 6063 | O | GLY | F | 238 | 18.889 | 43.521 | 35.243 | 1.00 | 32.51 | O |
| ATOM | 6064 | N | SER | F | 239 | 19.543 | 45.669 | 35.058 | 1.00 | 32.77 | N |
| ATOM | 6065 | CA | SER | F | 239 | 19.303 | 45.767 | 33.628 | 1.00 | 32.73 | C |
| ATOM | 6066 | C | SER | F | 239 | 20.334 | 46.705 | 33.004 | 1.00 | 31.60 | C |
| ATOM | 6067 | O | SER | F | 239 | 20.501 | 47.836 | 33.457 | 1.00 | 31.83 | O |
| ATOM | 6068 | CB | SER | F | 239 | 17.885 | 46.290 | 33.362 | 1.00 | 32.31 | C |
| ATOM | 6069 | OG | SER | F | 239 | 17.611 | 46.293 | 31.973 | 1.00 | 34.81 | O |
| ATOM | 6070 | N | ILE | F | 240 | 21.009 | 46.234 | 31.958 | 1.00 | 30.55 | N |
| ATOM | 6071 | CA | ILE | F | 240 | 22.032 | 47.020 | 31.277 | 1.00 | 29.37 | C |
| ATOM | 6072 | C | ILE | F | 240 | 21.857 | 46.909 | 29.766 | 1.00 | 28.68 | C |
| ATOM | 6073 | O | ILE | F | 240 | 21.298 | 45.928 | 29.274 | 1.00 | 29.57 | O |
| ATOM | 6074 | CB | ILE | F | 240 | 23.441 | 46.524 | 31.671 | 1.00 | 28.30 | C |
| ATOM | 6075 | CG1 | ILE | F | 240 | 23.599 | 45.056 | 31.276 | 1.00 | 29.24 | C |
| ATOM | 6076 | CG2 | ILE | F | 240 | 23.632 | 46.649 | 33.186 | 1.00 | 26.87 | C |
| ATOM | 6077 | CD1 | ILE | F | 240 | 25.001 | 44.480 | 31.564 | 1.00 | 30.18 | C |
| ATOM | 6078 | N | ASN | F | 241 | 22.330 | 47.913 | 29.031 | 1.00 | 27.35 | N |
| ATOM | 6079 | CA | ASN | F | 241 | 22.214 | 47.917 | 27.579 | 1.00 | 25.92 | C |
| ATOM | 6080 | C | ASN | F | 241 | 23.425 | 48.525 | 26.885 | 1.00 | 26.07 | C |
| ATOM | 6081 | O | ASN | F | 241 | 24.235 | 49.227 | 27.503 | 1.00 | 24.87 | O |
| ATOM | 6082 | CB | ASN | F | 241 | 20.957 | 48.672 | 27.141 | 1.00 | 24.51 | C |
| ATOM | 6083 | CG | ASN | F | 241 | 20.884 | 50.075 | 27.724 | 1.00 | 25.67 | C |
| ATOM | 6084 | OD1 | ASN | F | 241 | 20.311 | 50.290 | 28.796 | 1.00 | 28.27 | O |
| ATOM | 6085 | ND2 | ASN | F | 241 | 21.488 | 51.033 | 27.036 | 1.00 | 24.93 | N |
| ATOM | 6086 | N | HIS | F | 242 | 23.527 | 48.243 | 25.589 | 1.00 | 25.58 | N |
| ATOM | 6087 | CA | HIS | F | 242 | 24.613 | 48.730 | 24.747 | 1.00 | 25.88 | C |
| ATOM | 6088 | C | HIS | F | 242 | 24.040 | 48.965 | 23.356 | 1.00 | 26.14 | C |
| ATOM | 6089 | O | HIS | F | 242 | 23.170 | 48.213 | 22.907 | 1.00 | 25.21 | O |
| ATOM | 6090 | CB | HIS | F | 242 | 25.726 | 47.695 | 24.656 | 1.00 | 26.14 | C |
| ATOM | 6091 | CG | HIS | F | 242 | 26.838 | 48.095 | 23.741 | 1.00 | 26.54 | C |
| ATOM | 6092 | ND1 | HIS | F | 242 | 27.732 | 49.097 | 24.052 | 1.00 | 26.56 | N |
| ATOM | 6093 | CD2 | HIS | F | 242 | 27.196 | 47.632 | 22.521 | 1.00 | 27.55 | C |
| ATOM | 6094 | CE1 | HIS | F | 242 | 28.598 | 49.231 | 23.063 | 1.00 | 28.63 | C |
| ATOM | 6095 | NE2 | HIS | F | 242 | 28.296 | 48.353 | 22.122 | 1.00 | 28.19 | N |
| ATOM | 6096 | N | THR | F | 243 | 24.542 | 49.980 | 22.663 | 1.00 | 25.54 | N |
| ATOM | 6097 | CA | THR | F | 243 | 24.025 | 50.303 | 21.342 | 1.00 | 26.51 | C |
| ATOM | 6098 | C | THR | F | 243 | 25.042 | 50.299 | 20.210 | 1.00 | 27.85 | C |
| ATOM | 6099 | O | THR | F | 243 | 26.136 | 50.842 | 20.343 | 1.00 | 28.40 | O |
| ATOM | 6100 | CB | THR | F | 243 | 23.316 | 51.690 | 21.356 | 1.00 | 26.25 | C |
| ATOM | 6101 | OG1 | THR | F | 243 | 22.214 | 51.657 | 22.273 | 1.00 | 24.68 | O |

TABLE 3-continued

FGFR2(D2–D3) Complexed with FGF2

| ATOM | 6102 | CG2 | THR | F | 243 | 22.793 | 52.048 | 19.958 | 1.00 | 26.04 | C |
|---|---|---|---|---|---|---|---|---|---|---|---|
| ATOM | 6103 | N | TYR | F | 244 | 24.664 | 49.664 | 19.103 | 1.00 | 28.22 | N |
| ATOM | 6104 | CA | TYR | F | 244 | 25.496 | 49.602 | 17.909 | 1.00 | 29.85 | C |
| ATOM | 6105 | C | TYR | F | 244 | 24.807 | 50.413 | 16.816 | 1.00 | 31.08 | C |
| ATOM | 6106 | O | TYR | F | 244 | 23.583 | 50.536 | 16.800 | 1.00 | 30.67 | O |
| ATOM | 6107 | CB | TYR | F | 244 | 25.659 | 48.168 | 17.398 | 1.00 | 29.24 | C |
| ATOM | 6108 | CG | TYR | F | 244 | 26.503 | 47.274 | 18.264 | 1.00 | 29.23 | C |
| ATOM | 6109 | CD1 | TYR | F | 244 | 25.934 | 46.213 | 18.969 | 1.00 | 28.57 | C |
| ATOM | 6110 | CD2 | TYR | F | 244 | 27.882 | 47.476 | 18.370 | 1.00 | 28.39 | C |
| ATOM | 6111 | CE1 | TYR | F | 244 | 26.715 | 45.370 | 19.754 | 1.00 | 28.64 | C |
| ATOM | 6112 | CE2 | TYR | F | 244 | 28.669 | 46.644 | 19.158 | 1.00 | 29.07 | C |
| ATOM | 6113 | CZ | TYR | F | 244 | 28.081 | 45.593 | 19.846 | 1.00 | 28.99 | C |
| ATOM | 6114 | OH | TYR | F | 244 | 28.859 | 44.775 | 20.630 | 1.00 | 30.62 | O |
| ATOM | 6115 | N | HIS | F | 245 | 25.601 | 50.973 | 15.913 | 1.00 | 32.15 | N |
| ATOM | 6116 | CA | HIS | F | 245 | 25.069 | 51.741 | 14.797 | 1.00 | 33.59 | C |
| ATOM | 6117 | C | HIS | F | 245 | 25.457 | 50.986 | 13.534 | 1.00 | 33.68 | C |
| ATOM | 6118 | O | HIS | F | 245 | 26.611 | 50.581 | 13.387 | 1.00 | 33.99 | O |
| ATOM | 6119 | CB | HIS | F | 245 | 25.674 | 53.145 | 14.786 | 1.00 | 34.56 | C |
| ATOM | 6120 | CG | HIS | F | 245 | 25.480 | 53.882 | 16.077 | 1.00 | 37.38 | C |
| ATOM | 6121 | ND1 | HIS | F | 245 | 24.287 | 54.476 | 16.421 | 1.00 | 37.28 | N |
| ATOM | 6122 | CD2 | HIS | F | 245 | 26.310 | 54.066 | 17.132 | 1.00 | 39.21 | C |
| ATOM | 6123 | CE1 | HIS | F | 245 | 24.385 | 54.991 | 17.636 | 1.00 | 37.94 | C |
| ATOM | 6124 | NE2 | HIS | F | 245 | 25.606 | 54.753 | 18.090 | 1.00 | 38.49 | N |
| ATOM | 6125 | N | LEU | F | 246 | 24.499 | 50.777 | 12.638 | 1.00 | 33.16 | N |
| ATOM | 6126 | CA | LEU | F | 246 | 24.778 | 50.063 | 11.399 | 1.00 | 33.00 | C |
| ATOM | 6127 | C | LEU | F | 246 | 24.638 | 50.957 | 10.174 | 1.00 | 34.03 | C |
| ATOM | 6128 | O | LEU | F | 246 | 23.694 | 51.746 | 10.065 | 1.00 | 34.12 | O |
| ATOM | 6129 | CB | LEU | F | 246 | 23.842 | 48.854 | 11.246 | 1.00 | 31.62 | C |
| ATOM | 6130 | CG | LEU | F | 246 | 23.884 | 48.127 | 9.894 | 1.00 | 31.04 | C |
| ATOM | 6131 | CD1 | LEU | F | 246 | 25.269 | 47.475 | 9.679 | 1.00 | 30.18 | C |
| ATOM | 6132 | CD2 | LEU | F | 246 | 22.789 | 47.071 | 9.849 | 1.00 | 29.52 | C |
| ATOM | 6133 | N | ASP | F | 247 | 25.592 | 50.834 | 9.257 | 1.00 | 34.91 | N |
| ATOM | 6134 | CA | ASP | F | 247 | 25.560 | 51.598 | 8.018 | 1.00 | 36.30 | C |
| ATOM | 6135 | C | ASP | F | 247 | 25.917 | 50.642 | 6.887 | 1.00 | 36.31 | C |
| ATOM | 6136 | O | ASP | F | 247 | 26.820 | 49.813 | 7.036 | 1.00 | 36.41 | O |
| ATOM | 6137 | CB | ASP | F | 247 | 26.540 | 52.777 | 8.075 | 1.00 | 36.95 | C |
| ATOM | 6138 | CG | ASP | F | 247 | 26.118 | 53.919 | 7.161 | 1.00 | 38.99 | C |
| ATOM | 6139 | OD1 | ASP | F | 247 | 26.603 | 55.059 | 7.335 | 1.00 | 39.74 | O |
| ATOM | 6140 | OD2 | ASP | F | 247 | 25.288 | 53.672 | 6.262 | 1.00 | 40.23 | O |
| ATOM | 6141 | N | VAL | F | 248 | 25.196 | 50.740 | 5.771 | 1.00 | 36.55 | N |
| ATOM | 6142 | CA | VAL | F | 248 | 25.430 | 49.864 | 4.633 | 1.00 | 36.46 | C |
| ATOM | 6143 | C | VAL | F | 248 | 25.844 | 50.650 | 3.400 | 1.00 | 36.82 | C |
| ATOM | 6144 | O | VAL | F | 248 | 25.231 | 51.664 | 3.070 | 1.00 | 37.84 | O |
| ATOM | 6145 | CB | VAL | F | 248 | 24.167 | 49.053 | 4.312 | 1.00 | 36.17 | C |
| ATOM | 6146 | CG1 | VAL | F | 248 | 24.465 | 48.007 | 3.249 | 1.00 | 34.16 | C |
| ATOM | 6147 | CG2 | VAL | F | 248 | 23.643 | 48.411 | 5.592 | 1.00 | 35.63 | C |
| ATOM | 6148 | N | VAL | F | 249 | 26.889 | 50.171 | 2.726 | 1.00 | 36.57 | N |
| ATOM | 6149 | CA | VAL | F | 249 | 27.415 | 50.820 | 1.527 | 1.00 | 36.43 | C |
| ATOM | 6150 | C | VAL | F | 249 | 27.369 | 49.875 | 0.325 | 1.00 | 36.89 | C |
| ATOM | 6151 | O | VAL | F | 249 | 27.897 | 48.761 | 0.371 | 1.00 | 36.55 | O |
| ATOM | 6152 | CB | VAL | F | 249 | 28.898 | 51.264 | 1.735 | 1.00 | 36.50 | C |
| ATOM | 6153 | CG1 | VAL | F | 249 | 29.419 | 51.953 | 0.480 | 1.00 | 35.80 | C |
| ATOM | 6154 | CG2 | VAL | F | 249 | 29.013 | 52.186 | 2.933 | 1.00 | 35.90 | C |
| ATOM | 6155 | N | GLU | F | 250 | 26.750 | 50.323 | −0.756 | 1.00 | 36.94 | N |
| ATOM | 6156 | CA | GLU | F | 250 | 26.664 | 49.503 | −1.953 | 1.00 | 36.91 | C |
| ATOM | 6157 | C | GLU | F | 250 | 27.923 | 49.681 | −2.792 | 1.00 | 35.51 | C |
| ATOM | 6158 | O | GLU | F | 250 | 28.315 | 50.796 | −3.100 | 1.00 | 35.05 | O |
| ATOM | 6159 | CB | GLU | F | 250 | 25.419 | 49.902 | −2.747 | 1.00 | 39.01 | C |
| ATOM | 6160 | CG | GLU | F | 250 | 24.131 | 49.722 | −1.952 | 1.00 | 42.23 | C |
| ATOM | 6161 | CD | GLU | F | 250 | 22.889 | 50.095 | −2.742 | 1.00 | 43.94 | C |
| ATOM | 6162 | OE1 | GLU | F | 250 | 22.643 | 51.304 | −2.949 | 1.00 | 44.73 | O |
| ATOM | 6163 | OE2 | GLU | F | 250 | 22.165 | 49.169 | −3.159 | 1.00 | 44.81 | O |
| ATOM | 6164 | N | ARG | F | 251 | 28.561 | 48.573 | −3.149 | 1.00 | 34.53 | N |
| ATOM | 6165 | CA | ARG | F | 251 | 29.776 | 48.607 | −3.948 | 1.00 | 33.88 | C |
| ATOM | 6166 | C | ARG | F | 251 | 29.417 | 48.222 | −5.380 | 1.00 | 35.00 | C |
| ATOM | 6167 | O | ARG | F | 251 | 28.527 | 47.416 | −5.595 | 1.00 | 34.89 | O |
| ATOM | 6168 | CB | ARG | F | 251 | 30.804 | 47.628 | −3.379 | 1.00 | 31.60 | C |
| ATOM | 6169 | CG | ARG | F | 251 | 31.185 | 47.893 | −1.923 | 1.00 | 28.57 | C |
| ATOM | 6170 | CD | ARG | F | 251 | 31.457 | 49.373 | −1.673 | 1.00 | 26.81 | C |
| ATOM | 6171 | NE | ARG | F | 251 | 32.497 | 49.913 | −2.550 | 1.00 | 24.43 | N |
| ATOM | 6172 | CZ | ARG | F | 251 | 33.800 | 49.670 | −2.431 | 1.00 | 22.96 | C |
| ATOM | 6173 | NH1 | ARG | F | 251 | 34.269 | 48.885 | −1.463 | 1.00 | 24.68 | N |
| ATOM | 6174 | NH2 | ARG | F | 251 | 34.642 | 50.229 | −3.280 | 1.00 | 24.66 | N |
| ATOM | 6175 | N | SER | F | 252 | 30.098 | 48.796 | −6.362 | 1.00 | 35.23 | N |
| ATOM | 6176 | CA | SER | F | 252 | 29.834 | 48.520 | −7.772 | 1.00 | 36.16 | C |
| ATOM | 6177 | C | SER | F | 252 | 31.103 | 48.052 | −8.482 | 1.00 | 36.13 | C |
| ATOM | 6178 | O | SER | F | 252 | 31.930 | 48.859 | −8.882 | 1.00 | 36.17 | O |

TABLE 3-continued

FGFR2(D2–D3) Complexed with FGF2

| ATOM | 6179 | CB | SER | F | 252 | 29.299 | 49.794 | −8.433 | 1.00 | 36.21 | C |
|------|------|-----|-----|---|-----|--------|--------|--------|------|-------|---|
| ATOM | 6180 | OG | SER | F | 252 | 29.342 | 49.697 | −9.841 | 1.00 | 37.53 | O |
| ATOM | 6181 | N | PRO | F | 253 | 31.269 | 46.739 | −8.660 | 1.00 | 37.26 | N |
| ATOM | 6182 | CA | PRO | F | 253 | 32.471 | 46.219 | −9.326 | 1.00 | 37.37 | C |
| ATOM | 6183 | C | PRO | F | 253 | 32.490 | 46.310 | −10.859 | 1.00 | 37.89 | C |
| ATOM | 6184 | O | PRO | F | 253 | 32.809 | 45.334 | −11.539 | 1.00 | 39.08 | O |
| ATOM | 6185 | CB | PRO | F | 253 | 32.539 | 44.784 | −8.820 | 1.00 | 38.19 | C |
| ATOM | 6186 | CG | PRO | F | 253 | 31.080 | 44.407 | −8.743 | 1.00 | 37.95 | C |
| ATOM | 6187 | CD | PRO | F | 253 | 30.429 | 45.643 | −8.134 | 1.00 | 37.11 | C |
| ATOM | 6188 | N | HIS | F | 254 | 32.153 | 47.479 | −11.400 | 1.00 | 37.46 | N |
| ATOM | 6189 | CA | HIS | F | 254 | 32.164 | 47.669 | −12.847 | 1.00 | 37.94 | C |
| ATOM | 6190 | C | HIS | F | 254 | 33.273 | 48.623 | −13.293 | 1.00 | 36.74 | C |
| ATOM | 6191 | O | HIS | F | 254 | 33.769 | 49.419 | −12.504 | 1.00 | 36.07 | O |
| ATOM | 6192 | CB | HIS | F | 254 | 30.828 | 48.236 | −13.339 | 1.00 | 39.88 | C |
| ATOM | 6193 | CG | HIS | F | 254 | 29.663 | 47.320 | −13.131 | 1.00 | 43.40 | C |
| ATOM | 6194 | ND1 | HIS | F | 254 | 28.911 | 47.319 | −11.973 | 1.00 | 45.10 | N |
| ATOM | 6195 | CD2 | HIS | F | 254 | 29.129 | 46.364 | −13.928 | 1.00 | 43.84 | C |
| ATOM | 6196 | CE1 | HIS | F | 254 | 27.962 | 46.404 | −12.068 | 1.00 | 44.84 | C |
| ATOM | 6197 | NE2 | HIS | F | 254 | 28.072 | 45.811 | −13.244 | 1.00 | 45.80 | N |
| ATOM | 6198 | N | ARG | F | 255 | 33.665 | 48.530 | −14.559 | 1.00 | 35.84 | N |
| ATOM | 6199 | CA | ARG | F | 255 | 34.663 | 49.440 | −15.092 | 1.00 | 35.46 | C |
| ATOM | 6200 | C | ARG | F | 255 | 33.904 | 50.769 | −15.210 | 1.00 | 34.55 | C |
| ATOM | 6201 | O | ARG | F | 255 | 32.676 | 50.787 | −15.132 | 1.00 | 34.11 | O |
| ATOM | 6202 | CB | ARG | F | 255 | 35.151 | 48.974 | −16.463 | 1.00 | 37.28 | C |
| ATOM | 6203 | CG | ARG | F | 255 | 34.118 | 49.080 | −17.581 | 1.00 | 39.45 | C |
| ATOM | 6204 | CD | ARG | F | 255 | 34.768 | 48.839 | −18.938 | 1.00 | 41.55 | C |
| ATOM | 6205 | NE | ARG | F | 255 | 33.868 | 49.155 | −20.044 | 1.00 | 43.96 | N |
| ATOM | 6206 | CZ | ARG | F | 255 | 32.917 | 48.343 | −20.504 | 1.00 | 45.46 | C |
| ATOM | 6207 | NH1 | ARG | F | 255 | 32.733 | 47.144 | −19.959 | 1.00 | 45.92 | N |
| ATOM | 6208 | NH2 | ARG | F | 255 | 32.133 | 48.741 | −21.499 | 1.00 | 46.26 | N |
| ATOM | 6209 | N | PRO | F | 256 | 34.617 | 51.895 | −15.389 | 1.00 | 33.51 | N |
| ATOM | 6210 | CA | PRO | F | 256 | 33.905 | 53.176 | −15.498 | 1.00 | 32.69 | C |
| ATOM | 6211 | C | PRO | F | 256 | 32.861 | 53.255 | −16.609 | 1.00 | 31.51 | C |
| ATOM | 6212 | O | PRO | F | 256 | 33.050 | 52.718 | −17.692 | 1.00 | 31.64 | O |
| ATOM | 6213 | CB | PRO | F | 256 | 35.037 | 54.201 | −15.656 | 1.00 | 32.52 | C |
| ATOM | 6214 | CG | PRO | F | 256 | 36.175 | 53.394 | −16.206 | 1.00 | 34.71 | C |
| ATOM | 6215 | CD | PRO | F | 256 | 36.072 | 52.086 | −15.469 | 1.00 | 33.91 | C |
| ATOM | 6216 | N | ILE | F | 257 | 31.749 | 53.917 | −16.313 | 1.00 | 31.13 | N |
| ATOM | 6217 | CA | ILE | F | 257 | 30.666 | 54.087 | −17.274 | 1.00 | 31.66 | C |
| ATOM | 6218 | C | ILE | F | 257 | 30.536 | 55.570 | −17.682 | 1.00 | 31.23 | C |
| ATOM | 6219 | O | ILE | F | 257 | 30.545 | 56.453 | −16.826 | 1.00 | 30.88 | O |
| ATOM | 6220 | CB | ILE | F | 257 | 29.349 | 53.559 | −16.662 | 1.00 | 32.97 | C |
| ATOM | 6221 | CG1 | ILE | F | 257 | 29.440 | 52.035 | −16.513 | 1.00 | 33.66 | C |
| ATOM | 6222 | CG2 | ILE | F | 257 | 28.168 | 53.949 | −17.520 | 1.00 | 33.20 | C |
| ATOM | 6223 | CD1 | ILE | F | 257 | 28.245 | 51.397 | −15.849 | 1.00 | 35.77 | C |
| ATOM | 6224 | N | LEU | F | 258 | 30.459 | 55.836 | −18.987 | 1.00 | 30.39 | N |
| ATOM | 6225 | CA | LEU | F | 258 | 30.332 | 57.212 | −19.481 | 1.00 | 31.22 | C |
| ATOM | 6226 | C | LEU | F | 258 | 28.921 | 57.482 | −19.989 | 1.00 | 31.52 | C |
| ATOM | 6227 | O | LEU | F | 258 | 28.228 | 56.570 | −20.453 | 1.00 | 30.67 | O |
| ATOM | 6228 | CB | LEU | F | 258 | 31.300 | 57.502 | −20.638 | 1.00 | 30.74 | C |
| ATOM | 6229 | CG | LEU | F | 258 | 32.788 | 57.122 | −20.641 | 1.00 | 33.91 | C |
| ATOM | 6230 | CD1 | LEU | F | 258 | 33.515 | 58.017 | −21.628 | 1.00 | 32.56 | C |
| ATOM | 6231 | CD2 | LEU | F | 258 | 33.403 | 57.258 | −19.266 | 1.00 | 33.90 | C |
| ATOM | 6232 | N | GLN | F | 259 | 28.504 | 58.740 | −19.917 | 1.00 | 31.91 | N |
| ATOM | 6233 | CA | GLN | F | 259 | 27.183 | 59.120 | −20.396 | 1.00 | 32.58 | C |
| ATOM | 6234 | C | GLN | F | 259 | 27.157 | 59.096 | −21.928 | 1.00 | 32.23 | C |
| ATOM | 6235 | O | GLN | F | 259 | 28.054 | 59.630 | −22.585 | 1.00 | 31.49 | O |
| ATOM | 6236 | CB | GLN | F | 259 | 26.818 | 60.517 | −19.911 | 1.00 | 33.90 | C |
| ATOM | 6237 | CG | GLN | F | 259 | 25.487 | 61.010 | −20.429 | 1.00 | 36.31 | C |
| ATOM | 6238 | CD | GLN | F | 259 | 25.313 | 62.486 | −20.182 | 1.00 | 38.12 | C |
| ATOM | 6239 | OE1 | GLN | F | 259 | 25.448 | 62.954 | −19.055 | 1.00 | 39.31 | O |
| ATOM | 6240 | NE2 | GLN | F | 259 | 25.017 | 63.234 | −21.237 | 1.00 | 39.46 | N |
| ATOM | 6241 | N | ALA | F | 260 | 26.128 | 58.475 | −22.492 | 1.00 | 31.76 | N |
| ATOM | 6242 | CA | ALA | F | 260 | 26.003 | 58.406 | −23.946 | 1.00 | 32.37 | C |
| ATOM | 6243 | C | ALA | F | 260 | 25.815 | 59.798 | −24.551 | 1.00 | 32.72 | C |
| ATOM | 6244 | O | ALA | F | 260 | 25.125 | 60.644 | −23.986 | 1.00 | 32.74 | O |
| ATOM | 6245 | CB | ALA | F | 260 | 24.836 | 57.495 | −24.337 | 1.00 | 32.31 | C |
| ATOM | 6246 | N | GLY | F | 261 | 26.448 | 60.033 | −25.697 | 1.00 | 32.61 | N |
| ATOM | 6247 | CA | GLY | F | 261 | 26.335 | 61.326 | −26.350 | 1.00 | 33.50 | C |
| ATOM | 6248 | C | GLY | F | 261 | 27.459 | 62.302 | −26.036 | 1.00 | 34.44 | C |
| ATOM | 6249 | O | GLY | F | 261 | 27.607 | 63.312 | −26.722 | 1.00 | 34.82 | O |
| ATOM | 6250 | N | LEU | F | 262 | 28.251 | 62.011 | −25.006 | 1.00 | 34.98 | N |
| ATOM | 6251 | CA | LEU | F | 262 | 29.355 | 62.891 | −24.617 | 1.00 | 34.75 | C |
| ATOM | 6252 | C | LEU | F | 262 | 30.702 | 62.179 | −24.682 | 1.00 | 35.24 | C |
| ATOM | 6253 | O | LEU | F | 262 | 30.838 | 61.045 | −24.233 | 1.00 | 35.56 | O |
| ATOM | 6254 | CB | LEU | F | 262 | 29.132 | 63.427 | −23.201 | 1.00 | 34.91 | C |
| ATOM | 6255 | CG | LEU | F | 262 | 27.927 | 64.352 | −22.989 | 1.00 | 35.98 | C |

TABLE 3-continued

FGFR2(D2–D3) Complexed with FGF2

| ATOM | 6256 | CD1 | LEU | F | 262 | 27.868 | 64.788 | −21.524 | 1.00 | 33.73 | C |
|---|---|---|---|---|---|---|---|---|---|---|---|
| ATOM | 6257 | CD2 | LEU | F | 262 | 28.049 | 65.581 | −23.898 | 1.00 | 34.07 | C |
| ATOM | 6258 | N | PRO | F | 263 | 31.719 | 62.840 | −25.252 | 1.00 | 36.31 | N |
| ATOM | 6259 | CA | PRO | F | 263 | 31.645 | 64.190 | −25.821 | 1.00 | 36.64 | C |
| ATOM | 6260 | C | PRO | F | 263 | 30.835 | 64.242 | −27.118 | 1.00 | 37.59 | C |
| ATOM | 6261 | O | PRO | F | 263 | 30.571 | 63.214 | −27.744 | 1.00 | 37.44 | O |
| ATOM | 6262 | CB | PRO | F | 263 | 33.114 | 64.546 | −26.041 | 1.00 | 36.68 | C |
| ATOM | 6263 | CG | PRO | F | 263 | 33.717 | 63.220 | −26.402 | 1.00 | 35.47 | C |
| ATOM | 6264 | CD | PRO | F | 263 | 33.079 | 62.284 | −25.395 | 1.00 | 35.79 | C |
| ATOM | 6265 | N | ALA | F | 264 | 30.446 | 65.444 | −27.518 | 1.00 | 38.85 | N |
| ATOM | 6266 | CA | ALA | F | 264 | 29.673 | 65.619 | −28.742 | 1.00 | 40.21 | C |
| ATOM | 6267 | C | ALA | F | 264 | 30.528 | 66.217 | −29.850 | 1.00 | 40.87 | C |
| ATOM | 6268 | O | ALA | F | 264 | 31.480 | 66.958 | −29.588 | 1.00 | 41.01 | O |
| ATOM | 6269 | CB | ALA | F | 264 | 28.456 | 66.512 | −28.477 | 1.00 | 40.32 | C |
| ATOM | 6270 | N | ASN | F | 265 | 30.192 | 65.881 | −31.093 | 1.00 | 42.16 | N |
| ATOM | 6271 | CA | ASN | F | 265 | 30.925 | 66.408 | −32.237 | 1.00 | 43.51 | C |
| ATOM | 6272 | C | ASN | F | 265 | 30.826 | 67.928 | −32.203 | 1.00 | 44.31 | C |
| ATOM | 6273 | O | ASN | F | 265 | 29.859 | 68.485 | −31.678 | 1.00 | 44.07 | O |
| ATOM | 6274 | CB | ASN | F | 265 | 30.334 | 65.901 | −33.560 | 1.00 | 43.88 | C |
| ATOM | 6275 | CG | ASN | F | 265 | 30.430 | 64.392 | −33.709 | 1.00 | 45.38 | C |
| ATOM | 6276 | OD1 | ASN | F | 265 | 31.428 | 63.776 | −33.337 | 1.00 | 43.80 | O |
| ATOM | 6277 | ND2 | ASN | F | 265 | 29.392 | 63.792 | −34.277 | 1.00 | 46.59 | N |
| ATOM | 6278 | N | ALA | F | 266 | 31.832 | 68.595 | −32.753 | 1.00 | 45.27 | N |
| ATOM | 6279 | CA | ALA | F | 266 | 31.835 | 70.052 | −32.792 | 1.00 | 46.52 | C |
| ATOM | 6280 | C | ALA | F | 266 | 32.421 | 70.556 | −34.111 | 1.00 | 47.37 | C |
| ATOM | 6281 | O | ALA | F | 266 | 33.250 | 69.883 | −34.732 | 1.00 | 47.43 | O |
| ATOM | 6282 | CB | ALA | F | 266 | 32.623 | 70.610 | −31.609 | 1.00 | 45.85 | C |
| ATOM | 6283 | N | SER | F | 267 | 31.968 | 71.734 | −34.532 | 1.00 | 49.00 | N |
| ATOM | 6284 | CA | SER | F | 267 | 32.423 | 72.370 | −35.771 | 1.00 | 51.19 | C |
| ATOM | 6285 | C | SER | F | 267 | 32.706 | 73.849 | −35.469 | 1.00 | 52.95 | C |
| ATOM | 6286 | O | SER | F | 267 | 31.914 | 74.499 | −34.782 | 1.00 | 53.04 | O |
| ATOM | 6287 | CB | SER | F | 267 | 31.340 | 72.264 | −36.853 | 1.00 | 50.75 | C |
| ATOM | 6288 | N | THR | F | 268 | 33.844 | 74.373 | −35.941 | 1.00 | 55.40 | N |
| ATOM | 6289 | CA | THR | F | 268 | 34.232 | 75.777 | −35.692 | 1.00 | 58.15 | C |
| ATOM | 6290 | C | THR | F | 268 | 34.768 | 76.485 | −36.953 | 1.00 | 59.75 | C |
| ATOM | 6291 | O | THR | F | 268 | 34.357 | 76.170 | −38.069 | 1.00 | 60.60 | O |
| ATOM | 6292 | CB | THR | F | 268 | 35.320 | 75.880 | −34.580 | 1.00 | 58.09 | C |
| ATOM | 6293 | OG1 | THR | F | 268 | 34.939 | 75.080 | −33.455 | 1.00 | 59.93 | O |
| ATOM | 6294 | CG2 | THR | F | 268 | 35.477 | 77.321 | −34.105 | 1.00 | 58.09 | C |
| ATOM | 6295 | H | VAL | F | 269 | 35.698 | 77.424 | −36.775 | 1.00 | 61.40 | N |
| ATOM | 6296 | CA | VAL | F | 269 | 36.251 | 78.165 | −37.901 | 1.00 | 62.82 | C |
| ATOM | 6297 | C | VAL | F | 269 | 37.752 | 78.435 | −37.833 | 1.00 | 64.22 | C |
| ATOM | 6298 | O | VAL | F | 269 | 38.540 | 77.810 | −38.553 | 1.00 | 64.66 | O |
| ATOM | 6299 | CB | VAL | F | 269 | 35.531 | 79.508 | −38.057 | 1.00 | 62.42 | C |
| ATOM | 6300 | N | VAL | F | 270 | 38.153 | 79.376 | −36.985 | 1.00 | 65.60 | N |
| ATOM | 6301 | CA | VAL | F | 270 | 39.572 | 79.711 | −36.876 | 1.00 | 66.74 | C |
| ATOM | 6302 | C | VAL | F | 270 | 39.911 | 80.441 | −35.578 | 1.00 | 67.67 | C |
| ATOM | 6303 | O | VAL | F | 270 | 41.053 | 80.815 | −35.342 | 1.00 | 67.88 | O |
| ATOM | 6304 | CB | VAL | F | 270 | 40.035 | 80.596 | −38.049 | 1.00 | 66.63 | C |
| ATOM | 6305 | N | GLY | F | 271 | 38.909 | 80.640 | −34.738 | 1.00 | 68.56 | N |
| ATOM | 6306 | CA | GLY | F | 271 | 39.123 | 81.314 | −33.470 | 1.00 | 69.14 | C |
| ATOM | 6307 | C | GLY | F | 271 | 38.476 | 80.536 | −32.347 | 1.00 | 70.00 | C |
| ATOM | 6308 | O | GLY | F | 271 | 38.561 | 79.312 | −32.314 | 1.00 | 70.36 | O |
| ATOM | 6309 | N | ASP | F | 273 | 36.760 | 78.957 | −30.970 | 1.00 | 53.40 | N |
| ATOM | 6310 | CA | ASP | F | 273 | 36.988 | 78.210 | −29.739 | 1.00 | 53.60 | C |
| ATOM | 6311 | C | ASP | F | 273 | 35.983 | 77.068 | −29.585 | 1.00 | 53.06 | C |
| ATOM | 6312 | O | ASP | F | 273 | 34.844 | 77.157 | −30.052 | 1.00 | 53.49 | O |
| ATOM | 6313 | CB | ASP | F | 273 | 36.917 | 79.147 | −28.527 | 1.00 | 54.74 | C |
| ATOM | 6314 | CG | ASP | F | 273 | 38.227 | 79.891 | −28.287 | 1.00 | 56.07 | C |
| ATOM | 6315 | OD1 | ASP | F | 273 | 38.832 | 80.363 | −29.271 | 1.00 | 56.61 | O |
| ATOM | 6316 | OD2 | ASP | F | 273 | 38.649 | 80.014 | −27.116 | 1.00 | 55.76 | O |
| ATOM | 6317 | N | VAL | F | 274 | 36.408 | 75.991 | −28.929 | 1.00 | 51.73 | N |
| ATOM | 6318 | CA | VAL | F | 274 | 35.535 | 74.839 | −28.740 | 1.00 | 50.50 | C |
| ATOM | 6319 | C | VAL | F | 274 | 35.823 | 74.060 | −27.455 | 1.00 | 49.86 | C |
| ATOM | 6320 | O | VAL | F | 274 | 36.870 | 74.227 | −26.824 | 1.00 | 49.68 | O |
| ATOM | 6321 | CB | VAL | F | 274 | 35.653 | 73.865 | −29.931 | 1.00 | 50.21 | C |
| ATOM | 6322 | CG1 | VAL | F | 274 | 36.962 | 73.093 | −29.849 | 1.00 | 49.57 | C |
| ATOM | 6323 | CG2 | VAL | F | 274 | 34.466 | 72.925 | −29.949 | 1.00 | 51.04 | C |
| ATOM | 6324 | N | GLU | F | 275 | 34.880 | 73.208 | −27.070 | 1.00 | 49.12 | N |
| ATOM | 6325 | CA | GLU | F | 275 | 35.046 | 72.382 | −25.888 | 1.00 | 48.19 | C |
| ATOM | 6326 | C | GLU | F | 275 | 34.438 | 71.004 | −26.089 | 1.00 | 47.10 | C |
| ATOM | 6327 | O | GLU | F | 275 | 33.559 | 70.808 | −26.928 | 1.00 | 47.91 | O |
| ATOM | 6328 | CB | GLU | F | 275 | 34.413 | 73.037 | −24.663 | 1.00 | 48.81 | C |
| ATOM | 6329 | CG | GLU | F | 275 | 32.915 | 73.193 | −24.749 | 1.00 | 49.77 | C |
| ATOM | 6330 | CD | GLU | F | 275 | 32.298 | 73.481 | −23.397 | 1.00 | 50.13 | C |
| ATOM | 6331 | OE1 | GLU | F | 275 | 32.974 | 74.114 | −22.553 | 1.00 | 50.91 | O |
| ATOM | 6332 | OE2 | GLU | F | 275 | 31.136 | 73.083 | −23.185 | 1.00 | 50.57 | O |

TABLE 3-continued

FGFR2(D2–D3) Complexed with FGF2

| ATOM | 6333 | N | PHE | F | 276 | 34.934 | 70.050 | −25.312 | 1.00 | 45.40 | N |
|---|---|---|---|---|---|---|---|---|---|---|---|
| ATOM | 6334 | CA | PHE | F | 276 | 34.458 | 68.680 | −25.342 | 1.00 | 42.98 | C |
| ATOM | 6335 | C | PHE | F | 276 | 34.182 | 68.306 | −23.899 | 1.00 | 41.88 | C |
| ATOM | 6336 | O | PHE | F | 276 | 35.051 | 68.445 | −23.042 | 1.00 | 40.61 | O |
| ATOM | 6337 | CB | PHE | F | 276 | 35.529 | 67.759 | −25.918 | 1.00 | 44.18 | C |
| ATOM | 6338 | CG | PHE | F | 276 | 35.672 | 67.858 | −27.405 | 1.00 | 45.07 | C |
| ATOM | 6339 | CD1 | PHE | F | 276 | 34.645 | 67.426 | −28.242 | 1.00 | 45.08 | C |
| ATOM | 6340 | CD2 | PHE | F | 276 | 36.838 | 68.367 | −27.972 | 1.00 | 45.06 | C |
| ATOM | 6341 | CE1 | PHE | F | 276 | 34.776 | 67.496 | −29.625 | 1.00 | 46.84 | C |
| ATOM | 6342 | CE2 | PHE | F | 276 | 36.985 | 68.443 | −29.352 | 1.00 | 46.77 | C |
| ATOM | 6343 | CZ | PHE | F | 276 | 35.950 | 68.006 | −30.187 | 1.00 | 46.46 | C |
| ATOM | 6344 | N | VAL | F | 277 | 32.969 | 67.842 | −23.630 | 1.00 | 40.76 | N |
| ATOM | 6345 | CA | VAL | F | 277 | 32.597 | 67.471 | −22.278 | 1.00 | 40.08 | C |
| ATOM | 6346 | C | VAL | F | 277 | 32.449 | 65.969 | −22.130 | 1.00 | 39.86 | C |
| ATOM | 6347 | O | VAL | F | 277 | 32.090 | 65.262 | −23.075 | 1.00 | 40.39 | O |
| ATOM | 6348 | CB | VAL | F | 277 | 31.283 | 68.161 | −21.857 | 1.00 | 39.97 | C |
| ATOM | 6349 | CG1 | VAL | F | 277 | 30.900 | 67.749 | −20.444 | 1.00 | 40.02 | C |
| ATOM | 6350 | CG2 | VAL | F | 277 | 31.451 | 69.675 | −21.935 | 1.00 | 40.07 | C |
| ATOM | 6351 | N | CYS | F | 278 | 32.735 | 65.483 | −20.932 | 1.00 | 38.84 | N |
| ATOM | 6352 | CA | CYS | F | 278 | 32.625 | 64.068 | −20.649 | 1.00 | 38.38 | C |
| ATOM | 6353 | C | CYS | F | 278 | 32.048 | 63.891 | −19.253 | 1.00 | 37.50 | C |
| ATOM | 6354 | O | CYS | F | 278 | 32.347 | 64.685 | −18.361 | 1.00 | 37.83 | O |
| ATOM | 6355 | CB | CYS | F | 278 | 33.999 | 63.410 | −20.730 | 1.00 | 39.41 | C |
| ATOM | 6356 | SG | CYS | F | 278 | 33.903 | 61.622 | −20.662 | 1.00 | 42.56 | S |
| ATOM | 6357 | N | LYS | F | 279 | 31.217 | 62.865 | −19.068 | 1.00 | 35.92 | N |
| ATOM | 6358 | CA | LYS | F | 279 | 30.609 | 62.579 | −17.764 | 1.00 | 34.91 | C |
| ATOM | 6359 | C | LYS | F | 279 | 30.873 | 61.137 | −17.332 | 1.00 | 33.60 | C |
| ATOM | 6360 | O | LYS | F | 279 | 30.325 | 60.190 | −17.921 | 1.00 | 32.70 | O |
| ATOM | 6361 | CB | LYS | F | 279 | 29.094 | 62.816 | −17.798 | 1.00 | 35.37 | C |
| ATOM | 6362 | CG | LYS | F | 279 | 28.663 | 64.219 | −17.399 | 1.00 | 38.47 | C |
| ATOM | 6363 | CD | LYS | F | 279 | 29.108 | 64.582 | −15.965 | 1.00 | 37.93 | C |
| ATOM | 6364 | CE | LYS | F | 279 | 28.428 | 63.709 | −14.913 | 1.00 | 38.82 | C |
| ATOM | 6365 | NZ | LYS | F | 279 | 28.779 | 64.089 | −13.513 | 1.00 | 37.70 | N |
| ATOM | 6366 | N | VAL | F | 280 | 31.679 | 60.977 | −16.281 | 1.00 | 31.94 | N |
| ATOM | 6367 | CA | VAL | F | 280 | 32.053 | 59.653 | −15.778 | 1.00 | 29.99 | C |
| ATOM | 6368 | C | VAL | F | 280 | 31.469 | 59.231 | −14.432 | 1.00 | 30.83 | C |
| ATOM | 6369 | O | VAL | F | 280 | 31.258 | 60.050 | −13.534 | 1.00 | 30.77 | O |
| ATOM | 6370 | CB | VAL | F | 280 | 33.600 | 59.531 | −15.683 | 1.00 | 29.69 | C |
| ATOM | 6371 | CG1 | VAL | F | 280 | 33.992 | 58.184 | −15.095 | 1.00 | 29.19 | C |
| ATOM | 6372 | CG2 | VAL | F | 280 | 34.231 | 59.738 | −17.073 | 1.00 | 28.52 | C |
| ATOM | 6373 | N | TYR | F | 281 | 31.213 | 57.931 | −14.310 | 1.00 | 31.35 | N |
| ATOM | 6374 | CA | TYR | F | 281 | 30.701 | 57.320 | −13.082 | 1.00 | 32.39 | C |
| ATOM | 6375 | C | TYR | F | 281 | 31.546 | 56.084 | −12.767 | 1.00 | 30.82 | C |
| ATOM | 6376 | O | TYR | F | 281 | 31.819 | 55.279 | −13.652 | 1.00 | 31.49 | O |
| ATOM | 6377 | CB | TYR | F | 281 | 29.246 | 56.882 | −13.239 | 1.00 | 35.65 | C |
| ATOM | 6378 | CG | TYR | F | 281 | 28.314 | 57.977 | −13.697 | 1.00 | 39.56 | C |
| ATOM | 6379 | CD1 | TYR | F | 281 | 28.202 | 58.313 | −15.054 | 1.00 | 41.11 | C |
| ATOM | 6380 | CD2 | TYR | F | 281 | 27.532 | 58.672 | −12.779 | 1.00 | 41.01 | C |
| ATOM | 6381 | CE1 | TYR | F | 281 | 27.330 | 59.311 | −15.479 | 1.00 | 42.28 | C |
| ATOM | 6382 | CE2 | TYR | F | 281 | 26.658 | 59.675 | −13.195 | 1.00 | 43.31 | C |
| ATOM | 6383 | CZ | TYR | F | 281 | 26.560 | 59.986 | −14.546 | 1.00 | 43.29 | C |
| ATOM | 6384 | OH | TYR | F | 281 | 25.675 | 60.962 | −14.951 | 1.00 | 45.14 | O |
| ATOM | 6385 | N | SER | F | 282 | 31.958 | 55.935 | −11.516 | 1.00 | 29.47 | N |
| ATOM | 6386 | CA | SER | F | 282 | 32.762 | 54.789 | −11.105 | 1.00 | 28.89 | C |
| ATOM | 6387 | C | SER | F | 282 | 32.877 | 54.700 | −9.579 | 1.00 | 28.68 | C |
| ATOM | 6388 | O | SER | F | 282 | 32.899 | 55.722 | −8.897 | 1.00 | 28.67 | O |
| ATOM | 6389 | CB | SER | F | 282 | 34.158 | 54.890 | −11.734 | 1.00 | 28.94 | C |
| ATOM | 6390 | OG | SER | F | 282 | 35.021 | 53.879 | −11.237 | 1.00 | 28.16 | O |
| ATOM | 6391 | N | ASP | F | 283 | 32.940 | 53.478 | −9.050 | 1.00 | 28.16 | N |
| ATOM | 6392 | CA | ASP | F | 283 | 33.070 | 53.258 | −7.605 | 1.00 | 27.16 | C |
| ATOM | 6393 | C | ASP | F | 283 | 34.568 | 53.311 | −7.323 | 1.00 | 27.79 | C |
| ATOM | 6394 | O | ASP | F | 283 | 35.035 | 54.178 | −6.589 | 1.00 | 27.96 | O |
| ATOM | 6395 | CB | ASP | F | 283 | 32.502 | 51.890 | −7.229 | 1.00 | 26.32 | C |
| ATOM | 6396 | CG | ASP | F | 283 | 32.484 | 51.639 | −5.723 | 1.00 | 25.14 | C |
| ATOM | 6397 | OD1 | ASP | F | 283 | 31.759 | 50.709 | −5.315 | 1.00 | 25.10 | O |
| ATOM | 6398 | OD2 | ASP | F | 283 | 33.175 | 52.338 | −4.947 | 1.00 | 22.71 | O |
| ATOM | 6399 | N | ALA | F | 284 | 35.310 | 52.376 | −7.918 | 1.00 | 27.44 | N |
| ATOM | 6400 | CA | ALA | F | 284 | 36.757 | 52.357 | −7.786 | 1.00 | 27.90 | C |
| ATOM | 6401 | C | ALA | F | 284 | 37.213 | 53.672 | −8.427 | 1.00 | 27.70 | C |
| ATOM | 6402 | O | ALA | F | 284 | 36.701 | 54.064 | −9.481 | 1.00 | 27.71 | O |
| ATOM | 6403 | CB | ALA | F | 284 | 37.349 | 51.171 | −8.552 | 1.00 | 27.12 | C |
| ATOM | 6404 | N | GLN | F | 285 | 38.159 | 54.356 | −7.795 | 1.00 | 26.74 | N |
| ATOM | 6405 | CA | GLN | F | 285 | 38.652 | 55.631 | −8.327 | 1.00 | 27.03 | C |
| ATOM | 6406 | C | GLN | F | 285 | 39.040 | 55.505 | −9.810 | 1.00 | 25.88 | C |
| ATOM | 6407 | O | GLN | F | 285 | 39.871 | 54.673 | −10.180 | 1.00 | 25.70 | O |
| ATOM | 6408 | CB | GLN | F | 285 | 39.842 | 56.111 | −7.487 | 1.00 | 26.84 | C |
| ATOM | 6409 | CG | GLN | F | 285 | 39.982 | 57.622 | −7.332 | 1.00 | 27.07 | C |

TABLE 3-continued

FGFR2(D2–D3) Complexed with FGF2

| ATOM | 6410 | CD | GLN | F | 285 | 38.761 | 58.293 | −6.718 | 1.00 | 26.94 | C |
|---|---|---|---|---|---|---|---|---|---|---|---|
| ATOM | 6411 | OE1 | GLN | F | 285 | 38.175 | 57.792 | −5.760 | 1.00 | 25.31 | O |
| ATOM | 6412 | NE2 | GLN | F | 285 | 38.381 | 59.452 | −7.269 | 1.00 | 27.07 | N |
| ATOM | 6413 | N | PRO | F | 286 | 38.422 | 56.327 | −10.677 | 1.00 | 26.08 | N |
| ATOM | 6414 | CA | PRO | F | 286 | 38.702 | 56.308 | −12.117 | 1.00 | 26.74 | C |
| ATOM | 6415 | C | PRO | F | 286 | 39.795 | 57.301 | −12.539 | 1.00 | 27.03 | C |
| ATOM | 6416 | O | PRO | F | 286 | 39.980 | 58.335 | −11.902 | 1.00 | 27.72 | O |
| ATOM | 6417 | CB | PRO | F | 286 | 37.338 | 56.653 | −12.726 | 1.00 | 26.78 | C |
| ATOM | 6418 | CG | PRO | F | 286 | 36.815 | 57.707 | −11.769 | 1.00 | 26.69 | C |
| ATOM | 6419 | CD | PRO | F | 286 | 37.252 | 57.182 | −10.376 | 1.00 | 26.14 | C |
| ATOM | 6420 | N | HIS | F | 287 | 40.518 | 56.976 | −13.606 | 1.00 | 27.57 | N |
| ATOM | 6421 | CA | HIS | F | 287 | 41.559 | 57.854 | −14.119 | 1.00 | 27.86 | C |
| ATOM | 6422 | C | HIS | F | 287 | 41.125 | 58.318 | −15.508 | 1.00 | 28.19 | C |
| ATOM | 6423 | O | HIS | F | 287 | 40.935 | 57.510 | −16.423 | 1.00 | 27.70 | O |
| ATOM | 6424 | CB | HIS | F | 287 | 42.904 | 57.142 | −14.188 | 1.00 | 28.47 | C |
| ATOM | 6425 | CG | HIS | F | 287 | 44.023 | 58.038 | −14.607 | 1.00 | 30.28 | C |
| ATOM | 6426 | ND1 | HIS | F | 287 | 44.491 | 58.089 | −15.902 | 1.00 | 30.79 | N |
| ATOM | 6427 | CD2 | HIS | F | 287 | 44.723 | 58.971 | −13.915 | 1.00 | 29.73 | C |
| ATOM | 6428 | CE1 | HIS | F | 287 | 45.430 | 59.015 | −15.993 | 1.00 | 31.36 | C |
| ATOM | 6429 | NE2 | HIS | F | 287 | 45.588 | 59.568 | −14.802 | 1.00 | 30.56 | N |
| ATOM | 6430 | N | ILE | F | 288 | 40.948 | 59.626 | −15.644 | 1.00 | 27.95 | N |
| ATOM | 6431 | CA | ILE | F | 288 | 40.477 | 60.214 | −16.890 | 1.00 | 28.99 | C |
| ATOM | 6432 | C | ILE | F | 288 | 41.541 | 60.990 | −17.665 | 1.00 | 30.28 | C |
| ATOM | 6433 | O | ILE | F | 288 | 42.351 | 61.713 | −17.084 | 1.00 | 30.94 | O |
| ATOM | 6434 | CB | ILE | F | 288 | 39.277 | 61.150 | −16.600 | 1.00 | 27.26 | C |
| ATOM | 6435 | CG1 | ILE | F | 288 | 38.228 | 60.385 | −15.786 | 1.00 | 27.85 | C |
| ATOM | 6436 | CG2 | ILE | F | 288 | 38.678 | 61.671 | −17.889 | 1.00 | 27.58 | C |
| ATOM | 6437 | CD1 | ILE | F | 288 | 37.120 | 61.269 | −15.233 | 1.00 | 24.83 | C |
| ATOM | 6438 | N | GLN | F | 289 | 41.537 | 60.823 | −18.982 | 1.00 | 31.52 | N |
| ATOM | 6439 | CA | GLN | F | 289 | 42.470 | 61.533 | −19.849 | 1.00 | 33.66 | C |
| ATOM | 6440 | C | GLN | F | 289 | 41.800 | 61.828 | −21.185 | 1.00 | 33.68 | C |
| ATOM | 6441 | O | GLN | F | 289 | 40.826 | 61.175 | −21.560 | 1.00 | 33.89 | O |
| ATOM | 6442 | CB | GLN | F | 289 | 43.757 | 60.715 | −20.065 | 1.00 | 35.33 | C |
| ATOM | 6443 | CG | GLN | F | 289 | 43.567 | 59.332 | −20.668 | 1.00 | 37.11 | C |
| ATOM | 6444 | CD | GLN | F | 289 | 44.875 | 58.559 | −20.767 | 1.00 | 39.44 | C |
| ATOM | 6445 | OE1 | GLN | F | 289 | 45.823 | 59.003 | −21.418 | 1.00 | 41.60 | O |
| ATOM | 6446 | NE2 | GLN | F | 289 | 44.934 | 57.397 | −20.119 | 1.00 | 39.39 | N |
| ATOM | 6447 | N | TRP | F | 290 | 42.307 | 62.838 | −21.879 | 1.00 | 34.29 | N |
| ATOM | 6448 | CA | TRP | F | 290 | 41.785 | 63.227 | −23.182 | 1.00 | 35.09 | C |
| ATOM | 6449 | C | TRP | F | 290 | 42.849 | 62.919 | −24.225 | 1.00 | 36.73 | C |
| ATOM | 6450 | O | TRP | F | 290 | 44.013 | 63.311 | −24.073 | 1.00 | 36.45 | O |
| ATOM | 6451 | CB | TRP | F | 290 | 41.442 | 64.720 | −23.205 | 1.00 | 34.27 | C |
| ATOM | 6452 | CG | TRP | F | 290 | 40.162 | 65.060 | −22.494 | 1.00 | 33.19 | C |
| ATOM | 6453 | CD1 | TRP | F | 290 | 40.019 | 65.480 | −21.202 | 1.00 | 33.69 | C |
| ATOM | 6454 | CD2 | TRP | F | 290 | 38.839 | 65.012 | −23.048 | 1.00 | 32.32 | C |
| ATOM | 6455 | NE1 | TRP | F | 290 | 38.688 | 65.702 | −20.916 | 1.00 | 31.67 | N |
| ATOM | 6456 | CE2 | TRP | F | 290 | 37.944 | 65.419 | −22.030 | 1.00 | 32.16 | C |
| ATOM | 6457 | CE3 | TRP | F | 290 | 38.325 | 64.661 | −24.300 | 1.00 | 32.46 | C |
| ATOM | 6458 | CZ2 | TRP | F | 290 | 36.565 | 65.488 | −22.229 | 1.00 | 31.05 | C |
| ATOM | 6459 | CZ3 | TRP | F | 290 | 36.953 | 64.730 | −24.501 | 1.00 | 32.67 | C |
| ATOM | 6460 | CH2 | TRP | F | 290 | 36.088 | 65.141 | −23.466 | 1.00 | 33.18 | C |
| ATOM | 6461 | N | ILE | F | 291 | 42.448 | 62.217 | −25.281 | 1.00 | 38.06 | N |
| ATOM | 6462 | CA | ILE | F | 291 | 43.372 | 61.828 | −26.336 | 1.00 | 40.00 | C |
| ATOM | 6463 | C | ILE | F | 291 | 42.960 | 62.279 | −27.740 | 1.00 | 41.89 | C |
| ATOM | 6464 | O | ILE | F | 291 | 41.778 | 62.297 | −28.086 | 1.00 | 42.04 | O |
| ATOM | 6465 | CB | ILE | F | 291 | 43.551 | 60.297 | −26.352 | 1.00 | 39.88 | C |
| ATOM | 6466 | CG1 | ILE | F | 291 | 44.070 | 59.823 | −24.988 | 1.00 | 39.61 | C |
| ATOM | 6467 | CG2 | ILE | F | 291 | 44.500 | 59.891 | −27.473 | 1.00 | 39.23 | C |
| ATOM | 6468 | CD1 | ILE | F | 291 | 44.104 | 58.317 | −24.832 | 1.00 | 40.37 | C |
| ATOM | 6469 | N | LYS | F | 292 | 43.956 | 62.641 | −28.542 | 1.00 | 43.38 | N |
| ATOM | 6470 | CA | LYS | F | 292 | 43.734 | 63.066 | −29.918 | 1.00 | 45.28 | C |
| ATOM | 6471 | C | LYS | F | 292 | 44.359 | 62.001 | −30.811 | 1.00 | 46.12 | C |
| ATOM | 6472 | O | LYS | F | 292 | 45.498 | 61.586 | −30.585 | 1.00 | 46.03 | O |
| ATOM | 6473 | CB | LYS | F | 292 | 44.397 | 64.416 | −30.166 | 1.00 | 45.89 | C |
| ATOM | 6474 | CG | LYS | F | 292 | 43.655 | 65.304 | −31.149 | 1.00 | 47.53 | C |
| ATOM | 6475 | CD | LYS | F | 292 | 44.127 | 65.104 | −32.576 | 1.00 | 48.59 | C |
| ATOM | 6476 | CE | LYS | F | 292 | 43.530 | 66.187 | −33.472 | 1.00 | 48.61 | C |
| ATOM | 6477 | NZ | LYS | F | 292 | 44.350 | 66.408 | −34.692 | 1.00 | 49.06 | N |
| ATOM | 6478 | N | HIS | F | 293 | 43.603 | 61.546 | −31.804 | 1.00 | 47.10 | N |
| ATOM | 6479 | CA | HIS | F | 293 | 44.085 | 60.517 | −32.719 | 1.00 | 47.96 | C |
| ATOM | 6480 | C | HIS | F | 293 | 44.955 | 61.142 | −33.804 | 1.00 | 47.99 | C |
| ATOM | 6481 | O | HIS | F | 293 | 44.450 | 61.845 | −34.678 | 1.00 | 48.84 | O |
| ATOM | 6482 | CB | HIS | F | 293 | 42.897 | 59.790 | −33.358 | 1.00 | 47.51 | C |
| ATOM | 6483 | N | TYR | F | 308 | 48.337 | 55.850 | −33.701 | 1.00 | 56.86 | N |
| ATOM | 6484 | CA | TYR | F | 308 | 49.140 | 56.969 | −33.210 | 1.00 | 56.77 | C |
| ATOM | 6485 | C | TYR | F | 308 | 48.287 | 57.894 | −32.341 | 1.00 | 56.10 | C |
| ATOM | 6486 | O | TYR | F | 308 | 47.397 | 58.586 | −32.841 | 1.00 | 56.75 | O |

TABLE 3-continued

FGFR2(D2–D3) Complexed with FGF2

| ATOM | 6487 | CB | TYR | F | 308 | 49.724 | 57.759 | −34.387 | 1.00 | 56.75 | C |
|---|---|---|---|---|---|---|---|---|---|---|---|
| ATOM | 6488 | N | LEU | F | 309 | 48.575 | 57.916 | −31.044 | 1.00 | 54.88 | N |
| ATOM | 6489 | CA | LEU | F | 309 | 47.818 | 58.737 | −30.108 | 1.00 | 53.64 | C |
| ATOM | 6490 | C | LEU | F | 309 | 48.662 | 59.831 | −29.461 | 1.00 | 52.36 | C |
| ATOM | 6491 | O | LEU | F | 309 | 49.884 | 59.709 | −29.362 | 1.00 | 52.73 | O |
| ATOM | 6492 | CB | LEU | F | 309 | 47.231 | 57.836 | −29.025 | 1.00 | 53.75 | C |
| ATOM | 6493 | CG | LEU | F | 309 | 46.554 | 56.586 | −29.590 | 1.00 | 54.37 | C |
| ATOM | 6494 | CD1 | LEU | F | 309 | 46.186 | 55.641 | −28.454 | 1.00 | 55.15 | C |
| ATOM | 6495 | CD2 | LEU | F | 309 | 45.330 | 56.990 | −30.403 | 1.00 | 54.08 | C |
| ATOM | 6496 | N | LYS | F | 310 | 48.002 | 60.898 | −29.026 | 1.00 | 50.33 | N |
| ATOM | 6497 | CA | LYS | F | 310 | 48.675 | 62.011 | −28.361 | 1.00 | 48.17 | C |
| ATOM | 6498 | C | LYS | F | 310 | 47.847 | 62.434 | −27.150 | 1.00 | 46.65 | C |
| ATOM | 6499 | O | LYS | F | 310 | 46.684 | 62.822 | −27.291 | 1.00 | 45.61 | O |
| ATOM | 6500 | CB | LYS | F | 310 | 48.826 | 63.194 | −29.316 | 1.00 | 48.37 | C |
| ATOM | 6501 | N | VAL | F | 311 | 48.449 | 62.362 | −25.964 | 1.00 | 44.95 | N |
| ATOM | 6502 | CA | VAL | F | 311 | 47.753 | 62.729 | −24.731 | 1.00 | 43.52 | C |
| ATOM | 6503 | C | VAL | F | 311 | 47.706 | 64.238 | −24.530 | 1.00 | 42.93 | C |
| ATOM | 6504 | O | VAL | F | 311 | 48.733 | 64.881 | −24.312 | 1.00 | 43.27 | O |
| ATOM | 6505 | CB | VAL | F | 311 | 48.422 | 62.093 | −23.486 | 1.00 | 43.34 | C |
| ATOM | 6506 | CG1 | VAL | F | 311 | 47.686 | 62.534 | −22.219 | 1.00 | 41.56 | C |
| ATOM | 6507 | CG2 | VAL | F | 311 | 48.420 | 60.575 | −23.608 | 1.00 | 42.02 | C |
| ATOM | 6508 | N | LEU | F | 312 | 46.505 | 64.798 | −24.588 | 1.00 | 41.63 | N |
| ATOM | 6509 | CA | LEU | F | 312 | 46.342 | 66.233 | −24.417 | 1.00 | 40.85 | C |
| ATOM | 6510 | C | LEU | F | 312 | 46.282 | 66.655 | −22.962 | 1.00 | 39.66 | C |
| ATOM | 6511 | O | LEU | F | 312 | 46.784 | 67.714 | −22.597 | 1.00 | 39.35 | O |
| ATOM | 6512 | CB | LEU | F | 312 | 45.061 | 66.709 | −25.108 | 1.00 | 41.96 | C |
| ATOM | 6513 | CG | LEU | F | 312 | 44.861 | 66.260 | −26.556 | 1.00 | 43.95 | C |
| ATOM | 6514 | CD1 | LEU | F | 312 | 43.761 | 67.101 | −27.185 | 1.00 | 43.41 | C |
| ATOM | 6515 | CD2 | LEU | F | 312 | 46.163 | 66.417 | −27.342 | 1.00 | 44.19 | C |
| ATOM | 6516 | N | LYS | F | 313 | 45.679 | 65.812 | −22.131 | 1.00 | 38.22 | N |
| ATOM | 6517 | CA | LYS | F | 313 | 45.478 | 66.140 | −20.730 | 1.00 | 37.23 | C |
| ATOM | 6518 | C | LYS | F | 313 | 45.204 | 64.855 | −19.957 | 1.00 | 36.19 | C |
| ATOM | 6519 | O | LYS | F | 313 | 44.510 | 63.969 | −20.462 | 1.00 | 36.44 | O |
| ATOM | 6520 | CB | LYS | F | 313 | 44.261 | 67.069 | −20.661 | 1.00 | 37.39 | C |
| ATOM | 6521 | CG | LYS | F | 313 | 43.925 | 67.678 | −19.334 | 1.00 | 38.92 | C |
| ATOM | 6522 | CD | LYS | F | 313 | 42.674 | 68.528 | −19.501 | 1.00 | 39.81 | C |
| ATOM | 6523 | CE | LYS | F | 313 | 42.284 | 69.241 | −18.217 | 1.00 | 41.61 | C |
| ATOM | 6524 | NZ | LYS | F | 313 | 40.973 | 69.945 | −18.387 | 1.00 | 41.89 | N |
| ATOM | 6525 | N | ALA | F | 314 | 45.731 | 64.755 | −18.738 | 1.00 | 33.97 | N |
| ATOM | 6526 | CA | ALA | F | 314 | 45.535 | 63.563 | −17.917 | 1.00 | 32.58 | C |
| ATOM | 6527 | C | ALA | F | 314 | 45.420 | 63.900 | −16.432 | 1.00 | 32.38 | C |
| ATOM | 6528 | O | ALA | F | 314 | 46.160 | 64.752 | −15.911 | 1.00 | 31.85 | O |
| ATOM | 6529 | CB | ALA | F | 314 | 46.674 | 62.590 | −18.148 | 1.00 | 32.22 | C |
| ATOM | 6530 | N | ALA | F | 315 | 44.486 | 63.229 | −15.757 | 1.00 | 31.35 | N |
| ATOM | 6531 | CA | ALA | F | 315 | 44.232 | 63.436 | −14.331 | 1.00 | 30.87 | C |
| ATOM | 6532 | C | ALA | F | 315 | 45.429 | 63.080 | −13.452 | 1.00 | 30.61 | C |
| ATOM | 6533 | O | ALA | F | 315 | 46.245 | 62.226 | −13.804 | 1.00 | 30.29 | O |
| ATOM | 6534 | CB | ALA | F | 315 | 43.004 | 62.623 | −13.891 | 1.00 | 30.19 | C |
| ATOM | 6535 | N | GLY | F | 316 | 45.520 | 63.750 | −12.309 | 1.00 | 30.74 | N |
| ATOM | 6536 | CA | GLY | F | 316 | 46.598 | 63.512 | −11.374 | 1.00 | 32.31 | C |
| ATOM | 6537 | C | GLY | F | 316 | 46.654 | 64.590 | −10.309 | 1.00 | 34.07 | C |
| ATOM | 6538 | O | GLY | F | 316 | 45.778 | 65.449 | −10.234 | 1.00 | 33.07 | O |
| ATOM | 6539 | N | VAL | F | 317 | 47.686 | 64.535 | −9.479 | 1.00 | 35.99 | N |
| ATOM | 6540 | CA | VAL | F | 317 | 47.876 | 65.509 | −8.412 | 1.00 | 38.96 | C |
| ATOM | 6541 | C | VAL | F | 317 | 47.938 | 66.947 | −8.941 | 1.00 | 39.46 | C |
| ATOM | 6542 | O | VAL | F | 317 | 47.459 | 67.868 | −8.291 | 1.00 | 39.05 | O |
| ATOM | 6543 | CB | VAL | F | 317 | 49.170 | 65.196 | −7.629 | 1.00 | 39.98 | C |
| ATOM | 6544 | CG1 | VAL | F | 317 | 49.543 | 66.364 | −6.738 | 1.00 | 42.38 | C |
| ATOM | 6545 | CG2 | VAL | F | 317 | 48.962 | 63.936 | −6.776 | 1.00 | 40.44 | C |
| ATOM | 6546 | N | ASN | F | 318 | 48.519 | 67.127 | −10.124 | 1.00 | 41.29 | N |
| ATOM | 6547 | CA | ASN | F | 318 | 48.641 | 68.457 | −10.716 | 1.00 | 43.00 | C |
| ATOM | 6548 | C | ASN | F | 318 | 47.511 | 68.828 | −11.665 | 1.00 | 43.30 | C |
| ATOM | 6549 | O | ASN | F | 318 | 47.473 | 69.939 | −12.184 | 1.00 | 43.85 | O |
| ATOM | 6550 | CB | ASN | F | 318 | 49.977 | 68.598 | −11.442 | 1.00 | 44.26 | C |
| ATOM | 6551 | CG | ASN | F | 318 | 51.132 | 68.755 | −10.482 | 1.00 | 45.68 | C |
| ATOM | 6552 | OD1 | ASN | F | 318 | 51.083 | 69.578 | −9.571 | 1.00 | 46.62 | O |
| ATOM | 6553 | ND2 | ASN | F | 318 | 52.182 | 67.968 | −10.680 | 1.00 | 47.19 | N |
| ATOM | 6554 | N | THR | F | 319 | 46.603 | 67.891 | −11.901 | 1.00 | 42.99 | N |
| ATOM | 6555 | CA | THR | F | 319 | 45.457 | 68.141 | −12.765 | 1.00 | 42.33 | C |
| ATOM | 6556 | C | THR | F | 319 | 44.283 | 67.370 | −12.167 | 1.00 | 41.92 | C |
| ATOM | 6557 | O | THR | F | 319 | 43.915 | 66.291 | −12.637 | 1.00 | 41.66 | O |
| ATOM | 6558 | CB | THR | F | 319 | 45.709 | 67.671 | −14.218 | 1.00 | 42.29 | C |
| ATOM | 6559 | OG1 | THR | F | 319 | 46.962 | 68.179 | −14.689 | 1.00 | 42.83 | O |
| ATOM | 6560 | CG2 | THR | F | 319 | 44.618 | 68.191 | −15.126 | 1.00 | 41.88 | C |
| ATOM | 6561 | N | THR | F | 320 | 43.721 | 67.951 | −11.114 | 1.00 | 41.14 | N |
| ATOM | 6562 | CA | THR | F | 320 | 42.604 | 67.406 | −10.347 | 1.00 | 40.93 | C |
| ATOM | 6563 | C | THR | F | 320 | 41.342 | 67.029 | −11.133 | 1.00 | 40.66 | C |

TABLE 3-continued

FGFR2(D2–D3) Complexed with FGF2

| ATOM | 6564 | O | THR | F | 320 | 41.114 | 67.531 | −12.234 | 1.00 | 40.21 | O |
|---|---|---|---|---|---|---|---|---|---|---|---|
| ATOM | 6565 | CB | THR | F | 320 | 42.246 | 68.416 | −9.215 | 1.00 | 40.83 | C |
| ATOM | 6566 | OG1 | THR | F | 320 | 43.268 | 68.369 | −8.217 | 1.00 | 41.48 | O |
| ATOM | 6567 | CG2 | THR | F | 320 | 40.905 | 68.104 | −8.572 | 1.00 | 41.34 | C |
| ATOM | 6568 | N | ASP | F | 321 | 40.530 | 66.141 | −10.550 | 1.00 | 39.85 | N |
| ATOM | 6569 | CA | ASP | F | 321 | 39.279 | 65.691 | −11.164 | 1.00 | 40.39 | C |
| ATOM | 6570 | C | ASP | F | 321 | 38.250 | 66.816 | −11.303 | 1.00 | 40.53 | C |
| ATOM | 6571 | O | ASP | F | 321 | 37.332 | 66.725 | −12.117 | 1.00 | 40.60 | O |
| ATOM | 6572 | CB | ASP | F | 321 | 38.623 | 64.566 | −10.341 | 1.00 | 40.53 | C |
| ATOM | 6573 | CG | ASP | F | 321 | 39.375 | 63.252 | −10.417 | 1.00 | 40.72 | C |
| ATOM | 6574 | OD1 | ASP | F | 321 | 40.091 | 63.029 | −11.411 | 1.00 | 40.02 | O |
| ATOM | 6575 | OD2 | ASP | F | 321 | 39.230 | 62.434 | −9.483 | 1.00 | 40.69 | O |
| ATOM | 6576 | N | LYS | F | 322 | 38.389 | 67.863 | −10.497 | 1.00 | 40.77 | N |
| ATOM | 6577 | CA | LYS | F | 322 | 37.443 | 68.979 | −10.526 | 1.00 | 40.58 | C |
| ATOM | 6578 | C | LYS | F | 322 | 37.221 | 69.549 | −11.922 | 1.00 | 40.18 | C |
| ATOM | 6579 | O | LYS | F | 322 | 36.099 | 69.875 | −12.291 | 1.00 | 40.21 | O |
| ATOM | 6580 | CB | LYS | F | 322 | 37.914 | 70.098 | −9.589 | 1.00 | 40.95 | C |
| ATOM | 6581 | N | GLU | F | 323 | 38.288 | 69.653 | −12.704 | 1.00 | 40.02 | N |
| ATOM | 6582 | CA | GLU | F | 323 | 38.184 | 70.221 | −14.046 | 1.00 | 40.16 | C |
| ATOM | 6583 | C | GLU | F | 323 | 38.671 | 69.305 | −15.174 | 1.00 | 40.12 | C |
| ATOM | 6584 | O | GLU | F | 323 | 38.862 | 69.755 | −16.308 | 1.00 | 39.87 | O |
| ATOM | 6585 | CB | GLU | F | 323 | 38.971 | 71.537 | −14.096 | 1.00 | 40.79 | C |
| ATOM | 6586 | N | ILE | F | 324 | 38.856 | 68.024 | −14.872 | 1.00 | 39.58 | N |
| ATOM | 6587 | CA | ILE | F | 324 | 39.353 | 67.066 | −15.857 | 1.00 | 38.68 | C |
| ATOM | 6588 | C | ILE | F | 324 | 38.302 | 66.638 | −16.897 | 1.00 | 37.55 | C |
| ATOM | 6589 | O | ILE | F | 324 | 38.649 | 66.236 | −18.002 | 1.00 | 36.91 | O |
| ATOM | 6590 | CB | ILE | F | 324 | 39.925 | 65.801 | −15.118 | 1.00 | 39.46 | C |
| ATOM | 6591 | CG1 | ILE | F | 324 | 41.225 | 65.329 | −15.772 | 1.00 | 40.20 | C |
| ATOM | 6592 | CG2 | ILE | F | 324 | 38.890 | 64.689 | −15.079 | 1.00 | 39.11 | C |
| ATOM | 6593 | CD1 | ILE | F | 324 | 41.097 | 64.896 | −17.187 | 1.00 | 40.48 | C |
| ATOM | 6594 | N | GLU | F | 325 | 37.024 | 66.742 | −16.560 | 1.00 | 37.08 | N |
| ATOM | 6595 | CA | GLU | F | 325 | 35.976 | 66.321 | −17.489 | 1.00 | 38.65 | C |
| ATOM | 6596 | C | GLU | F | 325 | 35.615 | 67.265 | −18.641 | 1.00 | 39.40 | C |
| ATOM | 6597 | O | GLU | F | 325 | 34.725 | 66.964 | −19.440 | 1.00 | 39.05 | O |
| ATOM | 6598 | CB | GLU | F | 325 | 34.710 | 65.951 | −16.713 | 1.00 | 38.67 | C |
| ATOM | 6599 | CG | GLU | F | 325 | 34.796 | 64.584 | −16.035 | 1.00 | 39.54 | C |
| ATOM | 6600 | CD | GLU | F | 325 | 33.660 | 64.342 | −15.059 | 1.00 | 40.30 | C |
| ATOM | 6601 | OE1 | GLU | F | 325 | 33.587 | 65.078 | −14.055 | 1.00 | 41.21 | O |
| ATOM | 6602 | OE2 | GLU | F | 325 | 32.840 | 63.424 | −15.288 | 1.00 | 41.44 | O |
| ATOM | 6603 | N | VAL | F | 326 | 36.292 | 68.402 | −18.735 | 1.00 | 39.99 | N |
| ATOM | 6604 | CA | VAL | F | 326 | 36.025 | 69.327 | −19.833 | 1.00 | 40.92 | C |
| ATOM | 6605 | C | VAL | F | 326 | 37.345 | 69.692 | −20.492 | 1.00 | 41.51 | C |
| ATOM | 6606 | O | VAL | F | 326 | 38.309 | 70.024 | −19.813 | 1.00 | 41.96 | O |
| ATOM | 6607 | CB | VAL | F | 326 | 35.331 | 70.608 | −19.343 | 1.00 | 41.03 | C |
| ATOM | 6608 | CG1 | VAL | F | 326 | 35.075 | 71.542 | −20.522 | 1.00 | 41.22 | C |
| ATOM | 6609 | CG2 | VAL | F | 326 | 34.028 | 70.253 | −18.646 | 1.00 | 40.81 | C |
| ATOM | 6610 | N | LEU | F | 327 | 37.390 | 69.602 | −21.816 | 1.00 | 42.42 | N |
| ATOM | 6611 | CA | LEU | F | 327 | 38.595 | 69.920 | −22.579 | 1.00 | 43.76 | C |
| ATOM | 6612 | C | LEU | F | 327 | 38.346 | 71.154 | −23.442 | 1.00 | 44.79 | C |
| ATOM | 6613 | O | LEU | F | 327 | 37.456 | 71.144 | −24.295 | 1.00 | 44.63 | O |
| ATOM | 6614 | CB | LEU | F | 327 | 38.968 | 68.742 | −23.486 | 1.00 | 44.26 | C |
| ATOM | 6615 | CG | LEU | F | 327 | 40.164 | 68.970 | −24.420 | 1.00 | 44.64 | C |
| ATOM | 6616 | CD1 | LEU | F | 327 | 41.459 | 68.949 | −23.619 | 1.00 | 44.42 | C |
| ATOM | 6617 | CD2 | LEU | F | 327 | 40.195 | 67.903 | −25.495 | 1.00 | 44.68 | C |
| ATOM | 6618 | N | TYR | F | 328 | 39.138 | 72.203 | −23.225 | 1.00 | 45.43 | N |
| ATOM | 6619 | CA | TYR | F | 328 | 38.996 | 73.448 | −23.974 | 1.00 | 46.80 | C |
| ATOM | 6620 | C | TYR | F | 328 | 40.084 | 73.598 | −25.033 | 1.00 | 47.92 | C |
| ATOM | 6621 | O | TYR | F | 328 | 41.247 | 73.287 | −24.781 | 1.00 | 48.34 | O |
| ATOM | 6622 | CB | TYR | F | 328 | 39.045 | 74.636 | −23.010 | 1.00 | 46.06 | C |
| ATOM | 6623 | N | ILE | F | 329 | 39.697 | 74.065 | −26.218 | 1.00 | 49.45 | N |
| ATOM | 6624 | CA | ILE | F | 329 | 40.630 | 74.285 | −27.328 | 1.00 | 51.14 | C |
| ATOM | 6625 | C | ILE | F | 329 | 40.308 | 75.646 | −27.957 | 1.00 | 52.51 | C |
| ATOM | 6626 | O | ILE | F | 329 | 39.272 | 75.797 | −28.611 | 1.00 | 52.52 | O |
| ATOM | 6627 | CB | ILE | F | 329 | 40.488 | 73.191 | −28.414 | 1.00 | 50.82 | C |
| ATOM | 6628 | N | ARG | F | 330 | 41.193 | 76.626 | −27.762 | 1.00 | 54.06 | N |
| ATOM | 6629 | CA | ARG | F | 330 | 40.991 | 77.982 | −28.283 | 1.00 | 54.82 | C |
| ATOM | 6630 | C | ARG | F | 330 | 41.824 | 78.308 | −29.522 | 1.00 | 55.21 | C |
| ATOM | 6631 | O | ARG | F | 330 | 42.884 | 77.714 | −29.739 | 1.00 | 55.27 | O |
| ATOM | 6632 | CB | ARG | F | 330 | 41.301 | 79.001 | −27.182 | 1.00 | 55.05 | C |
| ATOM | 6633 | N | ASN | F | 331 | 41.341 | 79.260 | −30.321 | 1.00 | 55.59 | N |
| ATOM | 6634 | CA | ASN | F | 331 | 42.038 | 79.685 | −31.535 | 1.00 | 56.01 | C |
| ATOM | 6635 | C | ASN | F | 331 | 42.474 | 78.463 | −32.333 | 1.00 | 56.52 | C |
| ATOM | 6636 | O | ASN | F | 331 | 43.660 | 78.282 | −32.613 | 1.00 | 56.89 | O |
| ATOM | 6637 | CB | ASN | F | 331 | 43.268 | 80.526 | −31.167 | 1.00 | 55.05 | C |
| ATOM | 6638 | N | VAL | F | 332 | 41.507 | 77.631 | −32.704 | 1.00 | 56.90 | N |
| ATOM | 6639 | CA | VAL | F | 332 | 41.789 | 76.407 | −33.441 | 1.00 | 57.07 | C |
| ATOM | 6640 | C | VAL | F | 332 | 42.386 | 76.615 | −34.827 | 1.00 | 57.17 | C |

TABLE 3-continued

FGFR2(D2–D3) Complexed with FGF2

| ATOM | 6641 | O   | VAL | F | 332 | 42.114 | 77.608 | −35.494 | 1.00 | 57.28 | O |
|------|------|-----|-----|---|-----|--------|--------|---------|------|-------|---|
| ATOM | 6642 | CB  | VAL | F | 332 | 40.513 | 75.551 | −33.590 | 1.00 | 56.97 | C |
| ATOM | 6643 | N   | THR | F | 333 | 43.212 | 75.662 | −35.245 | 1.00 | 57.38 | N |
| ATOM | 6644 | CA  | THR | F | 333 | 43.837 | 75.689 | −36.562 | 1.00 | 57.57 | C |
| ATOM | 6645 | C   | THR | F | 333 | 43.264 | 74.484 | −37.305 | 1.00 | 57.51 | C |
| ATOM | 6646 | O   | THR | F | 333 | 42.549 | 73.677 | −36.712 | 1.00 | 57.93 | O |
| ATOM | 6647 | CB  | THR | F | 333 | 45.372 | 75.542 | −36.466 | 1.00 | 57.59 | C |
| ATOM | 6648 | N   | PHE | F | 334 | 43.562 | 74.357 | −38.593 | 1.00 | 57.10 | N |
| ATOM | 6649 | CA  | PHE | F | 334 | 43.054 | 73.222 | −39.355 | 1.00 | 56.54 | C |
| ATOM | 6650 | C   | PHE | F | 334 | 43.709 | 71.939 | −38.841 | 1.00 | 56.06 | C |
| ATOM | 6651 | O   | PHE | F | 334 | 43.181 | 70.838 | −39.017 | 1.00 | 56.04 | O |
| ATOM | 6652 | CB  | PHE | F | 334 | 43.341 | 73.407 | −40.850 | 1.00 | 56.71 | C |
| ATOM | 6653 | N   | GLU | F | 335 | 44.858 | 72.091 | −38.192 | 1.00 | 55.14 | N |
| ATOM | 6654 | CA  | GLU | F | 335 | 45.583 | 70.950 | −37.650 | 1.00 | 54.37 | C |
| ATOM | 6655 | C   | GLU | F | 335 | 44.838 | 70.313 | −36.470 | 1.00 | 53.76 | C |
| ATOM | 6656 | O   | GLU | F | 335 | 45.003 | 69.123 | −36.193 | 1.00 | 53.58 | O |
| ATOM | 6657 | CB  | GLU | F | 335 | 46.986 | 71.383 | −37.204 | 1.00 | 54.78 | C |
| ATOM | 6658 | N   | ASP | F | 336 | 44.018 | 71.102 | −35.779 | 1.00 | 52.59 | N |
| ATOM | 6659 | CA  | ASP | F | 336 | 43.274 | 70.588 | −34.631 | 1.00 | 51.94 | C |
| ATOM | 6660 | C   | ASP | F | 336 | 42.146 | 69.642 | −35.007 | 1.00 | 50.68 | C |
| ATOM | 6661 | O   | ASP | F | 336 | 41.697 | 68.861 | −34.176 | 1.00 | 50.39 | O |
| ATOM | 6662 | CB  | ASP | F | 336 | 42.716 | 71.735 | −33.786 | 1.00 | 52.17 | C |
| ATOM | 6663 | CG  | ASP | F | 336 | 43.806 | 72.534 | −33.113 | 1.00 | 52.82 | C |
| ATOM | 6664 | OD1 | ASP | F | 336 | 44.685 | 71.904 | −32.483 | 1.00 | 52.36 | O |
| ATOM | 6665 | OD2 | ASP | F | 336 | 43.785 | 73.781 | −33.216 | 1.00 | 52.92 | O |
| ATOM | 6666 | N   | ALA | F | 337 | 41.688 | 69.714 | −36.252 | 1.00 | 49.61 | N |
| ATOM | 6667 | CA  | ALA | F | 337 | 40.614 | 68.846 | −36.721 | 1.00 | 48.83 | C |
| ATOM | 6668 | C   | ALA | F | 337 | 40.971 | 67.392 | −36.450 | 1.00 | 48.43 | C |
| ATOM | 6669 | O   | ALA | F | 337 | 42.145 | 67.018 | −36.477 | 1.00 | 48.75 | O |
| ATOM | 6670 | CB  | ALA | F | 337 | 40.381 | 69.056 | −38.219 | 1.00 | 48.56 | C |
| ATOM | 6671 | N   | GLY | F | 338 | 39.961 | 66.569 | −36.188 | 1.00 | 47.59 | N |
| ATOM | 6672 | CA  | GLY | F | 338 | 40.228 | 65.166 | −35.925 | 1.00 | 46.62 | C |
| ATOM | 6673 | C   | GLY | F | 338 | 39.363 | 64.546 | −34.844 | 1.00 | 45.72 | C |
| ATOM | 6674 | O   | GLY | F | 338 | 38.417 | 65.166 | −34.346 | 1.00 | 44.55 | O |
| ATOM | 6675 | N   | GLU | F | 339 | 39.707 | 63.315 | −34.477 | 1.00 | 45.00 | N |
| ATOM | 6676 | CA  | GLU | F | 339 | 38.975 | 62.560 | −33.470 | 1.00 | 44.63 | C |
| ATOM | 6677 | C   | GLU | F | 339 | 39.539 | 62.748 | −32.054 | 1.00 | 43.23 | C |
| ATOM | 6678 | O   | GLU | F | 339 | 40.725 | 62.501 | −31.812 | 1.00 | 42.62 | O |
| ATOM | 6679 | CB  | GLU | F | 339 | 39.001 | 61.075 | −33.847 | 1.00 | 45.50 | C |
| ATOM | 6680 | CG  | GLU | F | 339 | 38.029 | 60.198 | −33.080 | 1.00 | 46.92 | C |
| ATOM | 6681 | CD  | GLU | F | 339 | 38.054 | 58.768 | −33.569 | 1.00 | 47.70 | C |
| ATOM | 6682 | OE1 | GLU | F | 339 | 38.295 | 58.565 | −34.775 | 1.00 | 48.96 | O |
| ATOM | 6683 | OE2 | GLU | F | 339 | 37.821 | 57.845 | −32.762 | 1.00 | 50.13 | O |
| ATOM | 6684 | N   | TYR | F | 340 | 38.678 | 63.194 | −31.136 | 1.00 | 42.09 | N |
| ATOM | 6685 | CA  | TYR | F | 340 | 39.044 | 63.388 | −29.732 | 1.00 | 40.89 | C |
| ATOM | 6686 | C   | TYR | F | 340 | 38.365 | 62.319 | −28.872 | 1.00 | 39.87 | C |
| ATOM | 6687 | O   | TYR | F | 340 | 37.190 | 62.004 | −29.067 | 1.00 | 40.00 | O |
| ATOM | 6688 | CB  | TYR | F | 340 | 38.646 | 64.789 | −29.262 | 1.00 | 41.78 | C |
| ATOM | 6689 | CG  | TYR | F | 340 | 39.494 | 65.868 | −29.898 | 1.00 | 43.99 | C |
| ATOM | 6690 | CD1 | TYR | F | 340 | 39.330 | 66.207 | −31.241 | 1.00 | 44.23 | C |
| ATOM | 6691 | CD2 | TYR | F | 340 | 40.522 | 66.492 | −29.180 | 1.00 | 44.40 | C |
| ATOM | 6692 | CE1 | TYR | F | 340 | 40.171 | 67.132 | −31.862 | 1.00 | 44.75 | C |
| ATOM | 6693 | CE2 | TYR | F | 340 | 41.368 | 67.416 | −29.787 | 1.00 | 45.18 | C |
| ATOM | 6694 | CZ  | TYR | F | 340 | 41.190 | 67.730 | −31.135 | 1.00 | 45.70 | C |
| ATOM | 6695 | OH  | TYR | F | 340 | 42.047 | 68.613 | −31.759 | 1.00 | 45.46 | O |
| ATOM | 6696 | N   | THR | F | 341 | 39.104 | 61.770 | −27.911 | 1.00 | 38.19 | N |
| ATOM | 6697 | CA  | THR | F | 341 | 38.578 | 60.709 | −27.065 | 1.00 | 36.42 | C |
| ATOM | 6698 | C   | THR | F | 341 | 38.723 | 60.932 | −25.570 | 1.00 | 35.91 | C |
| ATOM | 6699 | O   | THR | F | 341 | 39.788 | 61.304 | −25.091 | 1.00 | 35.96 | O |
| ATOM | 6700 | CB  | THR | F | 341 | 39.293 | 59.378 | −27.379 | 1.00 | 36.28 | C |
| ATOM | 6701 | OG1 | THR | F | 341 | 39.008 | 58.985 | −28.724 | 1.00 | 36.27 | O |
| ATOM | 6702 | CG2 | THR | F | 341 | 38.866 | 58.284 | −26.418 | 1.00 | 35.37 | C |
| ATOM | 6703 | N   | CYS | F | 342 | 37.644 | 60.704 | −24.833 | 1.00 | 35.02 | N |
| ATOM | 6704 | CA  | CYS | F | 342 | 37.707 | 60.793 | −23.382 | 1.00 | 34.15 | C |
| ATOM | 6705 | C   | CYS | F | 342 | 37.847 | 59.344 | −22.965 | 1.00 | 33.29 | C |
| ATOM | 6706 | O   | CYS | F | 342 | 36.980 | 58.520 | −23.268 | 1.00 | 34.08 | O |
| ATOM | 6707 | CB  | CYS | F | 342 | 36.426 | 61.349 | −22.777 | 1.00 | 33.61 | C |
| ATOM | 6708 | SG  | CYS | F | 342 | 36.368 | 61.103 | −20.981 | 1.00 | 33.75 | S |
| ATOM | 6709 | N   | LEU | F | 343 | 38.937 | 59.025 | −22.282 | 1.00 | 32.19 | N |
| ATOM | 6710 | CA  | LEU | F | 343 | 39.173 | 57.658 | −21.842 | 1.00 | 30.69 | C |
| ATOM | 6711 | C   | LEU | F | 343 | 39.254 | 57.567 | −20.320 | 1.00 | 30.23 | C |
| ATOM | 6712 | O   | LEU | F | 343 | 40.019 | 58.291 | −19.680 | 1.00 | 29.47 | O |
| ATOM | 6713 | CB  | LEU | F | 343 | 40.446 | 57.130 | −22.504 | 1.00 | 29.92 | C |
| ATOM | 6714 | CG  | LEU | F | 343 | 40.882 | 55.695 | −22.237 | 1.00 | 29.64 | C |
| ATOM | 6715 | CD1 | LEU | F | 343 | 41.521 | 55.097 | −23.494 | 1.00 | 29.38 | C |
| ATOM | 6716 | CD2 | LEU | F | 343 | 41.847 | 55.684 | −21.070 | 1.00 | 29.69 | C |
| ATOM | 6717 | N   | ALA | F | 344 | 38.444 | 56.673 | −19.753 | 1.00 | 29.04 | N |

TABLE 3-continued

FGFR2(D2–D3) Complexed with FGF2

| ATOM | 6718 | CA | ALA | F | 344 | 38.374 | 56.471 | −18.319 | 1.00 | 28.61 | C |
|---|---|---|---|---|---|---|---|---|---|---|---|
| ATOM | 6719 | C | ALA | F | 344 | 38.688 | 55.031 | −17.927 | 1.00 | 28.64 | C |
| ATOM | 6720 | O | ALA | F | 344 | 38.107 | 54.086 | −18.463 | 1.00 | 29.32 | O |
| ATOM | 6721 | CB | ALA | F | 344 | 36.982 | 56.850 | −17.818 | 1.00 | 27.84 | C |
| ATOM | 6722 | N | GLY | F | 345 | 39.600 | 54.861 | −16.977 | 1.00 | 27.93 | N |
| ATOM | 6723 | CA | GLY | F | 345 | 39.933 | 53.517 | −16.551 | 1.00 | 26.97 | C |
| ATOM | 6724 | C | GLY | F | 345 | 40.122 | 53.366 | −15.052 | 1.00 | 26.41 | C |
| ATOM | 6725 | O | GLY | F | 345 | 40.504 | 54.320 | −14.367 | 1.00 | 24.61 | O |
| ATOM | 6726 | N | ASN | F | 346 | 39.803 | 52.175 | −14.544 | 1.00 | 25.72 | N |
| ATOM | 6727 | CA | ASN | F | 346 | 40.019 | 51.828 | −13.135 | 1.00 | 27.21 | C |
| ATOM | 6728 | C | ASN | F | 346 | 40.644 | 50.424 | −13.115 | 1.00 | 27.92 | C |
| ATOM | 6729 | O | ASN | F | 346 | 40.917 | 49.855 | −14.176 | 1.00 | 26.78 | O |
| ATOM | 6730 | CB | ASN | F | 346 | 38.722 | 51.866 | −12.293 | 1.00 | 26.34 | C |
| ATOM | 6731 | CG | ASN | F | 346 | 37.637 | 50.911 | −12.800 | 1.00 | 26.84 | C |
| ATOM | 6732 | OD1 | ASN | F | 346 | 37.935 | 49.865 | −13.375 | 1.00 | 24.75 | O |
| ATOM | 6733 | ND2 | ASN | F | 346 | 36.368 | 51.269 | −12.563 | 1.00 | 24.95 | N |
| ATOM | 6734 | N | SER | F | 347 | 40.879 | 49.866 | −11.931 | 1.00 | 29.98 | N |
| ATOM | 6735 | CA | SER | F | 347 | 41.499 | 48.539 | −11.837 | 1.00 | 32.45 | C |
| ATOM | 6736 | C | SER | F | 347 | 40.738 | 47.443 | −12.569 | 1.00 | 33.80 | C |
| ATOM | 6737 | O | SER | F | 347 | 41.347 | 46.475 | −13.005 | 1.00 | 34.43 | O |
| ATOM | 6738 | CB | SER | F | 347 | 41.695 | 48.102 | −10.375 | 1.00 | 34.30 | C |
| ATOM | 6739 | OG | SER | F | 347 | 40.460 | 47.838 | −9.725 | 1.00 | 37.06 | O |
| ATOM | 6740 | N | ILE | F | 348 | 39.419 | 47.582 | −12.712 | 1.00 | 34.07 | N |
| ATOM | 6741 | CA | ILE | F | 348 | 38.638 | 46.556 | −13.415 | 1.00 | 34.74 | C |
| ATOM | 6742 | C | ILE | F | 348 | 38.746 | 46.629 | −14.942 | 1.00 | 34.67 | C |
| ATOM | 6743 | O | ILE | F | 348 | 38.858 | 45.603 | −15.606 | 1.00 | 34.73 | O |
| ATOM | 6744 | CB | ILE | F | 348 | 37.117 | 46.608 | −13.080 | 1.00 | 35.89 | C |
| ATOM | 6745 | CG1 | ILE | F | 348 | 36.872 | 46.336 | −11.594 | 1.00 | 36.06 | C |
| ATOM | 6746 | CG2 | ILE | F | 348 | 36.370 | 45.572 | −13.931 | 1.00 | 36.09 | C |
| ATOM | 6747 | CD1 | ILE | F | 348 | 37.101 | 47.530 | −10.702 | 1.00 | 38.46 | C |
| ATOM | 6748 | N | GLY | F | 349 | 38.690 | 47.834 | −15.502 | 1.00 | 34.21 | N |
| ATOM | 6749 | CA | GLY | F | 349 | 38.766 | 47.970 | −16.946 | 1.00 | 33.77 | C |
| ATOM | 6750 | C | GLY | F | 349 | 38.755 | 49.395 | −17.477 | 1.00 | 33.75 | C |
| ATOM | 6751 | O | GLY | F | 349 | 38.798 | 50.361 | −16.711 | 1.00 | 33.67 | O |
| ATOM | 6752 | N | ILE | F | 350 | 38.670 | 49.511 | −18.801 | 1.00 | 33.27 | N |
| ATOM | 6753 | CA | ILE | F | 350 | 38.683 | 50.794 | −19.498 | 1.00 | 33.45 | C |
| ATOM | 6754 | C | ILE | F | 350 | 37.449 | 51.057 | −20.370 | 1.00 | 33.70 | C |
| ATOM | 6755 | O | ILE | F | 350 | 36.901 | 50.142 | −20.983 | 1.00 | 33.76 | O |
| ATOM | 6756 | CB | ILE | F | 350 | 39.926 | 50.894 | −20.411 | 1.00 | 33.49 | C |
| ATOM | 6757 | CG1 | ILE | F | 350 | 41.198 | 50.775 | −19.567 | 1.00 | 34.27 | C |
| ATOM | 6758 | CG2 | ILE | F | 350 | 39.907 | 52.199 | −21.187 | 1.00 | 34.40 | C |
| ATOM | 6759 | CD1 | ILE | F | 350 | 42.482 | 50.712 | −20.381 | 1.00 | 36.09 | C |
| ATOM | 6760 | N | SER | F | 351 | 37.029 | 52.321 | −20.418 | 1.00 | 32.59 | N |
| ATOM | 6761 | CA | SER | F | 351 | 35.903 | 52.764 | −21.240 | 1.00 | 32.30 | C |
| ATOM | 6762 | C | SER | F | 351 | 36.291 | 54.075 | −21.921 | 1.00 | 32.43 | C |
| ATOM | 6763 | O | SER | F | 351 | 37.085 | 54.848 | −21.378 | 1.00 | 31.37 | O |
| ATOM | 6764 | CB | SER | F | 351 | 34.655 | 53.006 | −20.394 | 1.00 | 32.47 | C |
| ATOM | 6765 | CG | SER | F | 351 | 34.115 | 51.793 | −19.920 | 1.00 | 34.26 | O |
| ATOM | 6766 | N | PHE | F | 352 | 35.735 | 54.329 | −23.104 | 1.00 | 32.25 | N |
| ATOM | 6767 | CA | PHE | F | 352 | 36.039 | 55.561 | −23.828 | 1.00 | 33.49 | C |
| ATOM | 6768 | C | PHE | F | 352 | 34.990 | 55.930 | −24.873 | 1.00 | 33.58 | C |
| ATOM | 6769 | O | PHE | F | 352 | 34.419 | 55.057 | −25.537 | 1.00 | 33.77 | O |
| ATOM | 6770 | CB | PHE | F | 352 | 37.414 | 55.455 | −24.504 | 1.00 | 34.61 | C |
| ATOM | 6771 | CG | PHE | F | 352 | 37.525 | 54.317 | −25.491 | 1.00 | 36.55 | C |
| ATOM | 6772 | CD1 | PHE | F | 352 | 37.059 | 54.453 | −26.797 | 1.00 | 38.08 | C |
| ATOM | 6773 | CD2 | PHE | F | 352 | 38.093 | 53.109 | −25.109 | 1.00 | 37.89 | C |
| ATOM | 6774 | CE1 | PHE | F | 352 | 37.161 | 53.396 | −27.711 | 1.00 | 39.20 | C |
| ATOM | 6775 | CE2 | PHE | F | 352 | 38.201 | 52.047 | −26.010 | 1.00 | 38.88 | C |
| ATOM | 6776 | CZ | PHE | F | 352 | 37.734 | 52.191 | −27.313 | 1.00 | 39.32 | C |
| ATOM | 6777 | N | HIS | F | 353 | 34.737 | 57.227 | −25.011 | 1.00 | 33.60 | N |
| ATOM | 6778 | CA | HIS | F | 353 | 33.787 | 57.731 | −26.004 | 1.00 | 34.44 | C |
| ATOM | 6779 | C | HIS | F | 353 | 34.539 | 58.773 | −26.831 | 1.00 | 35.35 | C |
| ATOM | 6780 | O | HIS | F | 353 | 35.359 | 59.528 | −26.295 | 1.00 | 35.17 | O |
| ATOM | 6781 | CB | HIS | F | 353 | 32.559 | 58.386 | −25.351 | 1.00 | 34.07 | C |
| ATOM | 6782 | CG | HIS | F | 353 | 31.579 | 57.416 | −24.759 | 1.00 | 34.66 | C |
| ATOM | 6783 | ND1 | HIS | F | 353 | 30.424 | 57.821 | −24.121 | 1.00 | 33.93 | N |
| ATOM | 6784 | CD2 | HIS | F | 353 | 31.571 | 56.059 | −24.713 | 1.00 | 34.45 | C |
| ATOM | 6785 | CE1 | HIS | F | 353 | 29.750 | 56.762 | −23.711 | 1.00 | 32.42 | C |
| ATOM | 6786 | NE2 | HIS | F | 353 | 30.424 | 55.682 | −24.058 | 1.00 | 33.28 | N |
| ATOM | 6787 | N | SER | F | 354 | 34.261 | 58.806 | −28.133 | 1.00 | 35.90 | N |
| ATOM | 6788 | CA | SER | F | 354 | 34.931 | 59.739 | −29.032 | 1.00 | 36.78 | C |
| ATOM | 6789 | C | SER | F | 354 | 33.997 | 60.684 | −29.777 | 1.00 | 37.44 | C |
| ATOM | 6790 | O | SER | F | 354 | 32.812 | 60.406 | −29.968 | 1.00 | 36.86 | O |
| ATOM | 6791 | CB | SER | F | 354 | 35.770 | 58.963 | −30.045 | 1.00 | 36.92 | C |
| ATOM | 6792 | OG | SER | F | 354 | 36.682 | 58.111 | −29.379 | 1.00 | 38.08 | O |
| ATOM | 6793 | N | ALA | F | 355 | 34.551 | 61.816 | −30.187 | 1.00 | 38.59 | N |
| ATOM | 6794 | CA | ALA | F | 355 | 33.801 | 62.813 | −30.938 | 1.00 | 40.11 | C |

TABLE 3-continued

FGFR2(D2–D3) Complexed with FGF2

| ATOM | 6795 | C | ALA | F | 355 | 34.737 | 63.388 | −31.994 | 1.00 | 41.10 | C |
|---|---|---|---|---|---|---|---|---|---|---|---|
| ATOM | 6796 | O | ALA | F | 355 | 35.963 | 63.223 | −31.910 | 1.00 | 41.45 | O |
| ATOM | 6797 | CB | ALA | F | 355 | 33.294 | 63.917 | −30.008 | 1.00 | 39.80 | C |
| ATOM | 6798 | N | TRP | F | 356 | 34.166 | 64.055 | −32.990 | 1.00 | 42.22 | N |
| ATOM | 6799 | CA | TRP | F | 356 | 34.970 | 64.638 | −34.056 | 1.00 | 43.25 | C |
| ATOM | 6800 | C | TRP | F | 356 | 34.915 | 66.155 | −34.069 | 1.00 | 43.67 | C |
| ATOM | 6801 | O | TRP | F | 356 | 33.884 | 66.760 | −33.791 | 1.00 | 43.60 | O |
| ATOM | 6802 | CB | TRP | F | 356 | 34.523 | 64.108 | −35.424 | 1.00 | 43.57 | C |
| ATOM | 6803 | N | LEU | F | 357 | 36.050 | 66.763 | −34.383 | 1.00 | 44.42 | N |
| ATOM | 6804 | CA | LEU | F | 357 | 36.142 | 68.208 | −34.472 | 1.00 | 45.85 | C |
| ATOM | 6805 | C | LEU | F | 357 | 36.305 | 68.570 | −35.951 | 1.00 | 46.42 | C |
| ATOM | 6806 | O | LEU | F | 357 | 37.254 | 68.123 | −36.605 | 1.00 | 46.43 | O |
| ATOM | 6807 | CB | LEU | F | 357 | 37.342 | 68.708 | −33.656 | 1.00 | 46.03 | C |
| ATOM | 6808 | CG | LEU | F | 357 | 37.664 | 70.206 | −33.652 | 1.00 | 46.53 | C |
| ATOM | 6809 | CD1 | LEU | F | 357 | 38.430 | 70.582 | −34.910 | 1.00 | 47.10 | C |
| ATOM | 6810 | CD2 | LEU | F | 357 | 36.371 | 71.007 | −33.527 | 1.00 | 46.18 | C |
| ATOM | 6811 | N | THR | F | 358 | 35.369 | 69.359 | −36.473 | 1.00 | 46.98 | N |
| ATOM | 6812 | CA | THR | F | 358 | 35.417 | 69.782 | −37.870 | 1.00 | 48.32 | C |
| ATOM | 6813 | C | THR | F | 358 | 35.811 | 71.256 | −37.925 | 1.00 | 48.82 | C |
| ATOM | 6814 | O | THR | F | 358 | 35.167 | 72.098 | −37.293 | 1.00 | 48.73 | O |
| ATOM | 6815 | CB | THR | F | 358 | 34.042 | 69.594 | −38.558 | 1.00 | 48.28 | C |
| ATOM | 6816 | N | VAL | F | 359 | 36.874 | 71.559 | −38.667 | 1.00 | 49.50 | N |
| ATOM | 6817 | CA | VAL | F | 359 | 37.359 | 72.929 | −38.803 | 1.00 | 50.61 | C |
| ATOM | 6818 | C | VAL | F | 359 | 37.176 | 73.433 | −40.236 | 1.00 | 51.09 | C |
| ATOM | 6819 | O | VAL | F | 359 | 37.789 | 72.839 | −41.149 | 1.00 | 51.86 | O |
| ATOM | 6820 | CB | VAL | F | 359 | 38.858 | 73.036 | −38.419 | 1.00 | 50.22 | C |
| TER | 6821 | | VAL | F | 359 | | | | | | |
| ATOM | 6822 | N | LYS | G | 151 | 32.215 | 55.396 | −63.632 | 1.00 | 37.93 | N |
| ATOM | 6823 | CA | LYS | G | 151 | 30.832 | 55.516 | −63.096 | 1.00 | 39.08 | C |
| ATOM | 6824 | C | LYS | G | 151 | 30.226 | 54.131 | −62.828 | 1.00 | 39.20 | C |
| ATOM | 6825 | O | LYS | G | 151 | 30.223 | 53.272 | −63.708 | 1.00 | 39.64 | O |
| ATOM | 6826 | CB | LYS | G | 151 | 29.955 | 56.276 | −64.098 | 1.00 | 39.20 | C |
| ATOM | 6827 | N | ARG | G | 152 | 29.735 | 53.910 | −61.610 | 1.00 | 38.69 | N |
| ATOM | 6828 | CA | ARG | G | 152 | 29.115 | 52.633 | −61.251 | 1.00 | 38.05 | C |
| ATOM | 6829 | C | ARG | G | 152 | 28.255 | 52.699 | −59.993 | 1.00 | 36.80 | C |
| ATOM | 6830 | O | ARG | G | 152 | 28.428 | 53.570 | −59.139 | 1.00 | 36.86 | O |
| ATOM | 6831 | CB | ARG | G | 152 | 30.172 | 51.535 | −61.076 | 1.00 | 38.73 | C |
| ATOM | 6832 | CG | ARG | G | 152 | 31.158 | 51.774 | −59.951 | 1.00 | 39.40 | C |
| ATOM | 6833 | CD | ARG | G | 152 | 32.297 | 50.750 | −59.968 | 1.00 | 40.41 | C |
| ATOM | 6834 | NE | ARG | G | 152 | 31.888 | 49.426 | −59.504 | 1.00 | 39.75 | N |
| ATOM | 6835 | CZ | ARG | G | 152 | 32.740 | 48.476 | −59.120 | 1.00 | 40.46 | C |
| ATOM | 6836 | NH1 | ARG | G | 152 | 34.048 | 48.702 | −59.147 | 1.00 | 40.01 | N |
| ATOM | 6837 | NH2 | ARG | G | 152 | 32.289 | 47.303 | −58.692 | 1.00 | 39.42 | N |
| ATOM | 6838 | N | ALA | G | 153 | 27.332 | 51.750 | −59.901 | 1.00 | 35.27 | N |
| ATOM | 6839 | CA | ALA | G | 153 | 26.412 | 51.632 | −58.780 | 1.00 | 34.38 | C |
| ATOM | 6840 | C | ALA | G | 153 | 27.175 | 51.335 | −57.484 | 1.00 | 33.88 | C |
| ATOM | 6841 | O | ALA | G | 153 | 28.335 | 50.936 | −57.519 | 1.00 | 33.72 | O |
| ATOM | 6842 | CB | ALA | G | 153 | 25.406 | 50.512 | −59.066 | 1.00 | 32.93 | C |
| ATOM | 6843 | N | PRO | G | 154 | 26.520 | 51.508 | −56.322 | 1.00 | 33.31 | N |
| ATOM | 6844 | CA | PRO | G | 154 | 27.177 | 51.247 | −55.035 | 1.00 | 33.08 | C |
| ATOM | 6845 | C | PRO | G | 154 | 27.519 | 49.772 | −54.870 | 1.00 | 33.05 | C |
| ATOM | 6846 | O | PRO | G | 154 | 26.828 | 48.901 | −55.397 | 1.00 | 32.66 | O |
| ATOM | 6847 | CB | PRO | G | 154 | 26.136 | 51.697 | −54.001 | 1.00 | 32.74 | C |
| ATOM | 6848 | CG | PRO | G | 154 | 25.197 | 52.610 | −54.786 | 1.00 | 33.49 | C |
| ATOM | 6849 | CD | PRO | G | 154 | 25.120 | 51.911 | −56.118 | 1.00 | 33.51 | C |
| ATOM | 6850 | N | TYR | G | 155 | 28.585 | 49.503 | −54.131 | 1.00 | 32.79 | N |
| ATOM | 6851 | CA | TYR | G | 155 | 29.015 | 48.139 | −53.876 | 1.00 | 33.67 | C |
| ATOM | 6852 | C | TYR | G | 155 | 29.807 | 48.061 | −52.568 | 1.00 | 33.41 | C |
| ATOM | 6853 | O | TYR | G | 155 | 30.494 | 49.013 | −52.205 | 1.00 | 33.82 | O |
| ATOM | 6854 | CB | TYR | G | 155 | 29.866 | 47.622 | −55.045 | 1.00 | 33.62 | C |
| ATOM | 6855 | CG | TYR | G | 155 | 31.211 | 48.304 | −55.215 | 1.00 | 34.56 | C |
| ATOM | 6856 | CD1 | TYR | G | 155 | 31.304 | 49.566 | −55.793 | 1.00 | 35.11 | C |
| ATOM | 6857 | CD2 | TYR | G | 155 | 32.391 | 47.677 | −54.811 | 1.00 | 35.26 | C |
| ATOM | 6858 | CE1 | TYR | G | 155 | 32.536 | 50.189 | −55.975 | 1.00 | 36.15 | C |
| ATOM | 6859 | CE2 | TYR | G | 155 | 33.636 | 48.294 | −54.986 | 1.00 | 35.66 | C |
| ATOM | 6860 | CZ | TYR | G | 155 | 33.695 | 49.551 | −55.571 | 1.00 | 36.50 | C |
| ATOM | 6861 | OH | TYR | G | 155 | 34.905 | 50.172 | −55.769 | 1.00 | 38.56 | O |
| ATOM | 6862 | N | TRP | G | 156 | 29.702 | 46.938 | −51.861 | 1.00 | 33.53 | N |
| ATOM | 6863 | CA | TRP | G | 156 | 30.424 | 46.757 | −50.596 | 1.00 | 34.85 | C |
| ATOM | 6864 | C | TRP | G | 156 | 31.911 | 46.557 | −50.862 | 1.00 | 36.39 | C |
| ATOM | 6865 | O | TRP | G | 156 | 32.288 | 45.709 | −51.664 | 1.00 | 36.88 | O |
| ATOM | 6866 | CB | TRP | G | 156 | 29.887 | 45.538 | −49.827 | 1.00 | 32.98 | C |
| ATOM | 6867 | CG | TRP | G | 156 | 28.412 | 45.584 | −49.563 | 1.00 | 31.32 | C |
| ATOM | 6868 | CD1 | TRP | G | 156 | 27.509 | 44.581 | −49.784 | 1.00 | 29.97 | C |
| ATOM | 6869 | CD2 | TRP | G | 156 | 27.665 | 46.694 | −49.055 | 1.00 | 29.82 | C |
| ATOM | 6870 | NE1 | TRP | G | 156 | 26.245 | 45.001 | −49.450 | 1.00 | 29.21 | N |
| ATOM | 6871 | CE2 | TRP | G | 156 | 26.310 | 46.293 | −48.999 | 1.00 | 29.86 | C |

TABLE 3-continued

| | | | FGFR2(D2–D3) Complexed with FGF2 | | | | | | | |
|---|---|---|---|---|---|---|---|---|---|---|
| ATOM | 6872 | CE3 | TRP | G | 156 | 28.007 | 47.987 | −48.643 | 1.00 | 29.96 | C |
| ATOM | 6873 | CZ2 | TRP | G | 156 | 25.294 | 47.142 | −48.548 | 1.00 | 29.44 | C |
| ATOM | 6874 | CZ3 | TRP | G | 156 | 26.992 | 48.840 | −48.191 | 1.00 | 30.20 | C |
| ATOM | 6875 | CH2 | TRP | G | 156 | 25.653 | 48.410 | −48.149 | 1.00 | 30.96 | C |
| ATOM | 6876 | N | THR | G | 157 | 32.754 | 47.329 | −50.182 | 1.00 | 38.26 | N |
| ATOM | 6877 | CA | THR | G | 157 | 34.203 | 47.226 | −50.366 | 1.00 | 40.35 | C |
| ATOM | 6878 | C | THR | C | 157 | 34.873 | 46.270 | −49.392 | 1.00 | 42.46 | C |
| ATOM | 6879 | O | THR | G | 157 | 36.078 | 46.046 | −49.484 | 1.00 | 43.05 | O |
| ATOM | 6880 | CB | THR | G | 157 | 34.930 | 48.602 | −50.213 | 1.00 | 39.64 | C |
| ATOM | 6881 | OG1 | THR | G | 157 | 34.635 | 49.174 | −48.933 | 1.00 | 38.76 | O |
| ATOM | 6882 | CG2 | THR | G | 157 | 34.515 | 49.570 | −51.308 | 1.00 | 39.60 | C |
| ATOM | 6883 | N | ASN | G | 158 | 34.103 | 45.706 | −48.466 | 1.00 | 43.84 | N |
| ATOM | 6884 | CA | ASN | G | 158 | 34.670 | 44.792 | −47.482 | 1.00 | 45.69 | C |
| ATOM | 6885 | C | ASN | G | 158 | 33.595 | 43.928 | −46.828 | 1.00 | 45.42 | C |
| ATOM | 6886 | O | ASN | G | 158 | 33.163 | 44.209 | −45.716 | 1.00 | 45.32 | O |
| ATOM | 6887 | CB | ASN | G | 158 | 35.410 | 45.601 | −46.408 | 1.00 | 47.44 | C |
| ATOM | 6888 | CG | ASN | G | 158 | 36.131 | 44.719 | −45.403 | 1.00 | 50.56 | C |
| ATOM | 6889 | OD1 | ASN | G | 158 | 35.508 | 43.939 | −44.678 | 1.00 | 52.48 | O |
| ATOM | 6890 | ND2 | ASN | G | 158 | 37.457 | 44.834 | −45.360 | 1.00 | 51.45 | N |
| ATOM | 6891 | N | THR | G | 159 | 33.178 | 42.874 | −47.520 | 1.00 | 46.07 | N |
| ATOM | 6892 | CA | THR | G | 159 | 32.146 | 41.968 | −47.020 | 1.00 | 46.62 | C |
| ATOM | 6893 | C | THR | G | 159 | 32.564 | 41.185 | −45.781 | 1.00 | 46.29 | C |
| ATOM | 6894 | O | THR | G | 159 | 31.711 | 40.716 | −45.029 | 1.00 | 46.39 | O |
| ATOM | 6895 | CB | THR | G | 159 | 31.751 | 40.953 | −48.096 | 1.00 | 46.81 | C |
| ATOM | 6896 | OG1 | THR | G | 159 | 32.913 | 40.207 | −48.495 | 1.00 | 47.00 | O |
| ATOM | 6897 | CG2 | THR | G | 159 | 31.172 | 41.663 | −49.297 | 1.00 | 46.53 | C |
| ATOM | 6898 | N | GLU | G | 160 | 33.871 | 41.032 | −45.579 | 1.00 | 46.49 | N |
| ATOM | 6899 | CA | GLU | G | 160 | 34.393 | 40.294 | −44.429 | 1.00 | 46.06 | C |
| ATOM | 6900 | C | GLU | G | 160 | 33.858 | 40.887 | −43.129 | 1.00 | 46.02 | C |
| ATOM | 6901 | O | GLU | G | 160 | 33.367 | 40.164 | −42.264 | 1.00 | 45.54 | O |
| ATOM | 6902 | CB | GLU | G | 160 | 35.920 | 40.335 | −44.413 | 1.00 | 46.21 | C |
| ATOM | 6903 | N | LYS | G | 161 | 33.951 | 42.209 | −43.007 | 1.00 | 45.89 | N |
| ATOM | 6904 | CA | LYS | G | 161 | 33.483 | 42.926 | −41.822 | 1.00 | 45.83 | C |
| ATOM | 6905 | C | LYS | G | 161 | 31.959 | 42.991 | −41.700 | 1.00 | 45.38 | C |
| ATOM | 6906 | O | LYS | G | 161 | 31.445 | 43.581 | −40.753 | 1.00 | 45.49 | O |
| ATOM | 6907 | CB | LYS | G | 161 | 34.026 | 44.363 | −41.819 | 1.00 | 46.64 | C |
| ATOM | 6908 | CG | LYS | G | 161 | 35.547 | 44.475 | −41.765 | 1.00 | 48.45 | C |
| ATOM | 6909 | CD | LYS | G | 161 | 35.984 | 45.937 | −41.698 | 1.00 | 49.04 | C |
| ATOM | 6910 | CE | LYS | G | 161 | 37.496 | 46.060 | −41.529 | 1.00 | 50.22 | C |
| ATOM | 6911 | NZ | LYS | G | 161 | 37.949 | 47.487 | −41.526 | 1.00 | 50.00 | N |
| ATOM | 6912 | N | MET | G | 162 | 31.237 | 42.402 | −42.650 | 1.00 | 44.59 | N |
| ATOM | 6913 | CA | MET | G | 162 | 29.773 | 42.436 | −42.624 | 1.00 | 43.97 | C |
| ATOM | 6914 | C | MET | G | 162 | 29.138 | 41.062 | −42.425 | 1.00 | 43.84 | C |
| ATOM | 6915 | O | MET | G | 162 | 27.921 | 40.954 | −42.286 | 1.00 | 44.07 | O |
| ATOM | 6916 | CB | MET | G | 162 | 29.240 | 43.050 | −43.928 | 1.00 | 42.91 | C |
| ATOM | 6917 | CG | MET | G | 162 | 29.687 | 44.487 | −44.197 | 1.00 | 40.62 | C |
| ATOM | 6918 | SD | MET | G | 162 | 29.237 | 45.043 | −45.875 | 1.00 | 39.77 | S |
| ATOM | 6919 | CE | MET | G | 162 | 27.459 | 45.242 | −45.697 | 1.00 | 39.45 | C |
| ATOM | 6920 | N | GLU | G | 163 | 29.960 | 40.018 | −42.405 | 1.00 | 44.03 | N |
| ATOM | 6921 | CA | GLU | G | 163 | 29.468 | 38.651 | −42.247 | 1.00 | 43.93 | C |
| ATOM | 6922 | C | GLU | G | 163 | 28.762 | 38.384 | −40.915 | 1.00 | 42.61 | C |
| ATOM | 6923 | O | GLU | G | 163 | 27.810 | 37.613 | −40.870 | 1.00 | 42.58 | O |
| ATOM | 6924 | CB | GLU | G | 163 | 30.625 | 37.660 | −42.431 | 1.00 | 45.99 | C |
| ATOM | 6925 | CG | GLU | G | 163 | 31.400 | 37.853 | −43.733 | 1.00 | 49.23 | C |
| ATOM | 6926 | CD | GLU | G | 163 | 32.552 | 36.870 | −43.893 | 1.00 | 51.45 | C |
| ATOM | 6927 | OE1 | GLU | G | 163 | 33.169 | 36.510 | −42.865 | 1.00 | 52.67 | O |
| ATOM | 6928 | OE2 | GLU | G | 163 | 32.853 | 36.471 | −45.045 | 1.00 | 52.43 | O |
| ATOM | 6929 | N | LYS | G | 164 | 29.234 | 39.008 | −39.837 | 1.00 | 41.12 | N |
| ATOM | 6930 | CA | LYS | G | 164 | 28.631 | 38.836 | −38.509 | 1.00 | 39.70 | C |
| ATOM | 6931 | C | LYS | G | 164 | 27.307 | 39.618 | −38.484 | 1.00 | 38.39 | C |
| ATOM | 6932 | O | LYS | G | 164 | 27.299 | 40.830 | −38.274 | 1.00 | 38.68 | O |
| ATOM | 6933 | CB | LYS | G | 164 | 29.591 | 39.363 | −37.418 | 1.00 | 39.23 | C |
| ATOM | 6934 | CG | LYS | G | 164 | 29.140 | 39.093 | −35.962 | 1.00 | 38.82 | C |
| ATOM | 6935 | CD | LYS | G | 164 | 30.121 | 39.706 | −34.939 | 1.00 | 38.47 | C |
| ATOM | 6936 | CE | LYS | G | 164 | 29.622 | 39.572 | −33.506 | 1.00 | 37.66 | C |
| ATOM | 6937 | NZ | LYS | G | 164 | 30.524 | 40.217 | −32.490 | 1.00 | 37.42 | N |
| ATOM | 6938 | N | ARG | G | 165 | 26.192 | 38.924 | −38.695 | 1.00 | 36.91 | N |
| ATOM | 6939 | CA | ARG | G | 165 | 24.884 | 39.580 | −38.738 | 1.00 | 36.31 | C |
| ATOM | 6940 | C | ARG | G | 165 | 24.287 | 39.864 | −37.370 | 1.00 | 35.60 | C |
| ATOM | 6941 | O | ARG | G | 165 | 23.715 | 40.934 | −37.146 | 1.00 | 34.92 | O |
| ATOM | 6942 | CB | ARG | G | 165 | 23.899 | 38.746 | −39.572 | 1.00 | 36.23 | C |
| ATOM | 6943 | N | LEU | G | 166 | 24.406 | 38.903 | −36.460 | 1.00 | 35.23 | N |
| ATOM | 6944 | CA | LEU | G | 166 | 23.887 | 39.075 | −35.113 | 1.00 | 34.50 | C |
| ATOM | 6945 | C | LEU | G | 166 | 24.981 | 39.588 | −34.171 | 1.00 | 34.23 | C |
| ATOM | 6946 | O | LEU | G | 166 | 26.028 | 38.956 | −34.004 | 1.00 | 34.46 | O |
| ATOM | 6947 | CB | LEU | G | 166 | 23.306 | 37.757 | −34.596 | 1.00 | 34.17 | C |
| ATOM | 6948 | CG | LEU | G | 166 | 23.006 | 37.689 | −33.090 | 1.00 | 35.92 | C |

TABLE 3-continued

| | | | | | | | | | | |
|---|---|---|---|---|---|---|---|---|---|---|
| | FGFR2(D2–D3) Complexed with FGF2 |

| ATOM | 6949 | CD1 | LEU | G | 166 | 22.123 | 38.851 | −32.648 | 1.00 | 34.55 | C |
|---|---|---|---|---|---|---|---|---|---|---|---|
| ATOM | 6950 | CD2 | LEU | G | 166 | 22.348 | 36.362 | −32.777 | 1.00 | 35.42 | C |
| ATOM | 6951 | N | HIS | G | 167 | 24.733 | 40.753 | −33.582 | 1.00 | 33.90 | N |
| ATOM | 6952 | CA | HIS | G | 167 | 25.652 | 41.369 | −32.625 | 1.00 | 34.03 | C |
| ATOM | 6953 | C | HIS | G | 167 | 25.037 | 41.301 | −31.238 | 1.00 | 34.08 | C |
| ATOM | 6954 | O | HIS | G | 167 | 24.132 | 42.078 | −30.919 | 1.00 | 34.22 | O |
| ATOM | 6955 | CB | HIS | G | 167 | 25.897 | 42.842 | −32.949 | 1.00 | 34.75 | C |
| ATOM | 6956 | CG | HIS | G | 167 | 26.975 | 43.069 | −33.954 | 1.00 | 35.95 | C |
| ATOM | 6957 | ND1 | HIS | G | 167 | 26.910 | 42.576 | −35.239 | 1.00 | 36.61 | N |
| ATOM | 6958 | CD2 | HIS | G | 167 | 28.160 | 43.715 | −33.857 | 1.00 | 36.49 | C |
| ATOM | 6959 | CE1 | HIS | G | 167 | 28.010 | 42.906 | −35.891 | 1.00 | 36.40 | C |
| ATOM | 6960 | NE2 | HIS | G | 167 | 28.786 | 43.597 | −35.074 | 1.00 | 37.07 | N |
| ATOM | 6961 | N | ALA | G | 168 | 25.505 | 40.370 | −30.418 | 1.00 | 33.10 | N |
| ATOM | 6962 | CA | ALA | G | 168 | 24.996 | 40.259 | −29.061 | 1.00 | 32.60 | C |
| ATOM | 6963 | C | ALA | G | 168 | 26.108 | 40.801 | −28.175 | 1.00 | 32.87 | C |
| ATOM | 6964 | O | ALA | G | 168 | 27.237 | 40.302 | −28.212 | 1.00 | 33.14 | O |
| ATOM | 6965 | CB | ALA | G | 168 | 24.682 | 38.809 | −28.725 | 1.00 | 33.23 | C |
| ATOM | 6966 | N | VAL | G | 169 | 25.799 | 41.838 | −27.402 | 1.00 | 32.15 | N |
| ATOM | 6967 | CA | VAL | G | 169 | 26.798 | 42.454 | −26.546 | 1.00 | 33.09 | C |
| ATOM | 6968 | C | VAL | G | 169 | 26.284 | 42.769 | −25.156 | 1.00 | 33.02 | C |
| ATOM | 6969 | O | VAL | G | 169 | 25.087 | 42.930 | −24.935 | 1.00 | 33.52 | O |
| ATOM | 6970 | CB | VAL | G | 169 | 27.341 | 43.768 | −27.167 | 1.00 | 34.37 | C |
| ATOM | 6971 | CG1 | VAL | G | 169 | 27.788 | 43.514 | −28.609 | 1.00 | 35.12 | C |
| ATOM | 6972 | CG2 | VAL | G | 169 | 26.268 | 44.858 | −27.117 | 1.00 | 34.22 | C |
| ATOM | 6973 | N | PRO | G | 170 | 27.198 | 42.859 | −24.192 | 1.00 | 32.91 | N |
| ATOM | 6974 | CA | PRO | G | 170 | 26.867 | 43.159 | −22.800 | 1.00 | 32.72 | C |
| ATOM | 6975 | C | PRO | G | 170 | 26.401 | 44.612 | −22.658 | 1.00 | 34.03 | C |
| ATOM | 6976 | O | PRO | G | 170 | 26.931 | 45.508 | −23.333 | 1.00 | 33.46 | O |
| ATOM | 6977 | CB | PRO | G | 170 | 28.192 | 42.936 | −22.075 | 1.00 | 32.27 | C |
| ATOM | 6978 | CG | PRO | G | 170 | 28.917 | 41.954 | −22.950 | 1.00 | 33.28 | C |
| ATOM | 6979 | CD | PRO | G | 170 | 28.616 | 42.475 | −24.323 | 1.00 | 33.23 | C |
| ATOM | 6980 | N | ALA | G | 171 | 25.430 | 44.840 | −21.776 | 1.00 | 33.75 | N |
| ATOM | 6981 | CA | ALA | G | 171 | 24.909 | 46.177 | −21.524 | 1.00 | 34.33 | C |
| ATOM | 6982 | C | ALA | G | 171 | 26.050 | 47.100 | −21.120 | 1.00 | 34.09 | C |
| ATOM | 6983 | O | ALA | G | 171 | 27.022 | 46.646 | −20.512 | 1.00 | 33.95 | O |
| ATOM | 6984 | CB | ALA | G | 171 | 23.859 | 46.130 | −20.408 | 1.00 | 34.12 | C |
| ATOM | 6985 | N | ALA | G | 172 | 25.931 | 48.380 | −21.487 | 1.00 | 33.12 | N |
| ATOM | 6986 | CA | ALA | G | 172 | 26.914 | 49.411 | −21.157 | 1.00 | 33.26 | C |
| ATOM | 6987 | C | ALA | G | 172 | 28.082 | 49.537 | −22.136 | 1.00 | 33.48 | C |
| ATOM | 6988 | O | ALA | G | 172 | 28.915 | 50.442 | −22.014 | 1.00 | 34.33 | O |
| ATOM | 6989 | CB | ALA | G | 172 | 27.446 | 49.198 | −19.729 | 1.00 | 32.38 | C |
| ATOM | 6990 | N | ASN | G | 173 | 28.155 | 48.634 | −23.101 | 1.00 | 33.22 | N |
| ATOM | 6991 | CA | ASN | G | 173 | 29.225 | 48.679 | −24.091 | 1.00 | 33.37 | C |
| ATOM | 6992 | C | ASN | G | 173 | 28.840 | 49.566 | −25.272 | 1.00 | 32.71 | C |
| ATOM | 6993 | O | ASN | G | 173 | 27.684 | 49.962 | −25.423 | 1.00 | 32.68 | O |
| ATOM | 6994 | CB | ASN | G | 173 | 29.524 | 47.269 | −24.629 | 1.00 | 34.62 | C |
| ATOM | 6995 | CG | ASN | G | 173 | 30.296 | 46.404 | −23.640 | 1.00 | 34.28 | C |
| ATOM | 6996 | OD1 | ASN | G | 173 | 30.170 | 46.554 | −22.433 | 1.00 | 37.26 | O |
| ATOM | 6997 | ND2 | ASN | G | 173 | 31.080 | 45.481 | −24.158 | 1.00 | 34.66 | N |
| ATOM | 6998 | N | THR | G | 174 | 29.830 | 49.873 | −26.102 | 1.00 | 31.59 | N |
| ATOM | 6999 | CA | THR | G | 174 | 29.627 | 50.659 | −27.311 | 1.00 | 30.98 | C |
| ATOM | 7000 | C | THR | G | 174 | 29.460 | 49.669 | −28.472 | 1.00 | 30.95 | C |
| ATOM | 7001 | O | THR | G | 174 | 30.179 | 48.669 | −28.544 | 1.00 | 30.81 | O |
| ATOM | 7002 | CB | THR | G | 174 | 30.860 | 51.529 | −27.626 | 1.00 | 30.59 | C |
| ATOM | 7003 | OG1 | THR | G | 174 | 30.907 | 52.642 | −26.730 | 1.00 | 31.56 | O |
| ATOM | 7004 | CG2 | THR | G | 174 | 30.812 | 52.029 | −29.074 | 1.00 | 29.92 | C |
| ATOM | 7005 | N | VAL | G | 175 | 28.523 | 49.939 | −29.376 | 1.00 | 30.17 | N |
| ATOM | 7006 | CA | VAL | G | 175 | 28.311 | 49.068 | −30.530 | 1.00 | 29.66 | C |
| ATOM | 7007 | C | VAL | G | 175 | 28.583 | 49.851 | −31.809 | 1.00 | 28.77 | C |
| ATOM | 7008 | O | VAL | G | 175 | 28.223 | 51.024 | −31.913 | 1.00 | 28.77 | O |
| ATOM | 7009 | CB | VAL | G | 175 | 26.853 | 48.534 | −30.583 | 1.00 | 29.73 | C |
| ATOM | 7010 | CG1 | VAL | G | 175 | 26.675 | 47.614 | −31.785 | 1.00 | 30.00 | C |
| ATOM | 7011 | CG2 | VAL | G | 175 | 26.530 | 47.784 | −29.320 | 1.00 | 31.31 | C |
| ATOM | 7012 | N | LYS | G | 176 | 29.229 | 49.214 | −32.776 | 1.00 | 28.41 | N |
| ATOM | 7013 | CA | LYS | G | 176 | 29.519 | 49.876 | −34.046 | 1.00 | 28.60 | C |
| ATOM | 7014 | C | LYS | G | 176 | 29.178 | 48.979 | −35.240 | 1.00 | 29.11 | C |
| ATOM | 7015 | O | LYS | G | 176 | 29.671 | 47.856 | −35.342 | 1.00 | 28.32 | O |
| ATOM | 7016 | CB | LYS | G | 176 | 30.991 | 50.284 | −34.117 | 1.00 | 29.21 | C |
| ATOM | 7017 | N | PHE | G | 177 | 28.313 | 49.473 | −36.123 | 1.00 | 28.71 | N |
| ATOM | 7018 | CA | PHE | G | 177 | 27.929 | 48.736 | −37.325 | 1.00 | 29.28 | C |
| ATOM | 7019 | C | PHE | G | 177 | 28.592 | 49.414 | −38.521 | 1.00 | 29.86 | C |
| ATOM | 7020 | O | PHE | G | 177 | 28.617 | 50.645 | −38.610 | 1.00 | 29.26 | O |
| ATOM | 7021 | CB | PHE | G | 177 | 26.401 | 48.741 | −37.522 | 1.00 | 28.70 | C |
| ATOM | 7022 | CG | PHE | G | 177 | 25.641 | 47.975 | −36.464 | 1.00 | 29.03 | C |
| ATOM | 7023 | CD1 | PHE | G | 177 | 25.956 | 46.649 | −36.186 | 1.00 | 28.61 | C |
| ATOM | 7024 | CD2 | PHE | G | 177 | 24.617 | 48.578 | −35.746 | 1.00 | 27.96 | C |
| ATOM | 7025 | CE1 | PHE | G | 177 | 25.264 | 45.942 | −35.210 | 1.00 | 28.90 | C |

TABLE 3-continued

FGFR2(D2–D3) Complexed with FGF2

| ATOM | 7026 | CE2 | PHE | G | 177 | 23.921 | 47.881 | −34.771 | 1.00 | 27.66 | C |
|---|---|---|---|---|---|---|---|---|---|---|---|
| ATOM | 7027 | CZ | PHE | G | 177 | 24.245 | 46.563 | −34.502 | 1.00 | 28.37 | C |
| ATOM | 7028 | N | ARG | G | 178 | 29.127 | 48.617 | −39.439 | 1.00 | 30.54 | N |
| ATOM | 7029 | CA | ARG | G | 178 | 29.780 | 49.169 | −40.613 | 1.00 | 31.47 | C |
| ATOM | 7030 | C | ARG | G | 178 | 29.292 | 48.544 | −41.914 | 1.00 | 30.95 | C |
| ATOM | 7031 | O | ARG | G | 178 | 28.922 | 47.374 | −41.949 | 1.00 | 29.97 | O |
| ATOM | 7032 | CB | ARG | G | 178 | 31.298 | 48.984 | −40.515 | 1.00 | 34.36 | C |
| ATOM | 7033 | CG | ARG | G | 178 | 31.931 | 49.644 | −39.295 | 1.00 | 39.90 | C |
| ATOM | 7034 | CD | ARG | G | 178 | 33.447 | 49.738 | −39.439 | 1.00 | 43.10 | C |
| ATOM | 7035 | NE | ARG | G | 178 | 33.818 | 50.394 | −40.693 | 1.00 | 47.10 | N |
| ATOM | 7036 | CZ | ARG | G | 178 | 35.069 | 50.570 | −41.119 | 1.00 | 49.58 | C |
| ATOM | 7037 | NH1 | ARG | G | 178 | 36.096 | 50.141 | −40.390 | 1.00 | 50.61 | N |
| ATOM | 7038 | NH2 | ARG | G | 178 | 35.292 | 51.172 | −42.284 | 1.00 | 50.68 | N |
| ATOM | 7039 | N | CYS | G | 179 | 29.300 | 49.348 | −42.976 | 1.00 | 30.10 | N |
| ATOM | 7040 | CA | CYS | G | 179 | 28.925 | 48.904 | −44.315 | 1.00 | 31.02 | C |
| ATOM | 7041 | C | CYS | G | 179 | 29.848 | 49.628 | −45.305 | 1.00 | 31.31 | C |
| ATOM | 7042 | O | CYS | G | 179 | 29.406 | 50.479 | −46.087 | 1.00 | 28.70 | O |
| ATOM | 7043 | CB | CYS | G | 179 | 27.453 | 49.233 | −44.593 | 1.00 | 31.15 | C |
| ATOM | 7044 | SG | CYS | G | 179 | 26.323 | 48.376 | −43.429 | 1.00 | 33.32 | S |
| ATOM | 7045 | N | PRO | G | 180 | 31.154 | 49.303 | −45.268 | 1.00 | 31.92 | N |
| ATOM | 7046 | CA | PRO | G | 180 | 32.110 | 49.953 | −46.173 | 1.00 | 32.72 | C |
| ATOM | 7047 | C | PRO | G | 180 | 31.664 | 49.828 | −47.620 | 1.00 | 33.18 | C |
| ATOM | 7048 | O | PRO | G | 180 | 31.438 | 48.731 | −48.125 | 1.00 | 33.64 | O |
| ATOM | 7049 | CB | PRO | G | 180 | 33.442 | 49.269 | −45.843 | 1.00 | 32.69 | C |
| ATOM | 7050 | CG | PRO | G | 180 | 33.050 | 47.991 | −45.187 | 1.00 | 33.71 | C |
| ATOM | 7051 | CD | PRO | G | 180 | 31.832 | 48.342 | −44.386 | 1.00 | 31.74 | C |
| ATOM | 7052 | N | ALA | G | 181 | 31.507 | 50.974 | −48.275 | 1.00 | 33.47 | N |
| ATOM | 7053 | CA | ALA | G | 181 | 31.027 | 50.985 | −49.650 | 1.00 | 34.74 | C |
| ATOM | 7054 | C | ALA | G | 181 | 31.848 | 51.813 | −50.628 | 1.00 | 35.80 | C |
| ATOM | 7055 | O | ALA | G | 181 | 32.599 | 52.709 | −50.239 | 1.00 | 35.32 | O |
| ATOM | 7056 | CB | ALA | G | 181 | 29.575 | 51.473 | −49.674 | 1.00 | 33.88 | C |
| ATOM | 7057 | N | GLY | G | 182 | 31.668 | 51.498 | −51.909 | 1.00 | 36.73 | N |
| ATOM | 7058 | CA | GLY | G | 182 | 32.338 | 52.206 | −52.983 | 1.00 | 37.08 | C |
| ATOM | 7059 | C | GLY | G | 182 | 31.282 | 52.606 | −53.999 | 1.00 | 38.28 | C |
| ATOM | 7060 | O | GLY | G | 182 | 30.121 | 52.197 | −53.884 | 1.00 | 37.01 | O |
| ATOM | 7061 | N | GLY | G | 183 | 31.674 | 53.404 | −54.989 | 1.00 | 38.76 | N |
| ATOM | 7062 | CA | GLY | G | 183 | 30.734 | 53.838 | −56.010 | 1.00 | 39.76 | C |
| ATOM | 7063 | C | GLY | G | 183 | 31.086 | 55.189 | −56.613 | 1.00 | 40.59 | C |
| ATOM | 7064 | O | GLY | G | 183 | 31.746 | 56.011 | −55.979 | 1.00 | 40.19 | O |
| ATOM | 7065 | N | ASN | G | 184 | 30.636 | 55.424 | −57.841 | 1.00 | 41.17 | N |
| ATOM | 7066 | CA | ASN | G | 184 | 30.909 | 56.678 | −58.529 | 1.00 | 41.73 | C |
| ATOM | 7067 | C | ASN | G | 184 | 29.700 | 57.116 | −59.342 | 1.00 | 41.90 | C |
| ATOM | 7068 | O | ASN | G | 184 | 29.334 | 56.478 | −60.321 | 1.00 | 41.81 | O |
| ATOM | 7069 | CB | ASN | G | 184 | 32.140 | 56.527 | −59.433 | 1.00 | 42.19 | C |
| ATOM | 7070 | CG | ASN | G | 184 | 32.410 | 57.766 | −60.279 | 1.00 | 43.50 | C |
| ATOM | 7071 | OD1 | ASN | G | 184 | 31.973 | 58.875 | −59.953 | 1.00 | 44.29 | O |
| ATOM | 7072 | ND2 | ASN | G | 184 | 33.147 | 57.581 | −61.368 | 1.00 | 43.66 | N |
| ATOM | 7073 | N | PRO | G | 185 | 29.088 | 58.245 | −58.962 | 1.00 | 42.45 | N |
| ATOM | 7074 | CA | PRO | G | 185 | 29.466 | 59.115 | −57.846 | 1.00 | 43.00 | C |
| ATOM | 7075 | C | PRO | G | 185 | 29.365 | 58.488 | −56.455 | 1.00 | 43.89 | C |
| ATOM | 7076 | O | PRO | G | 185 | 28.707 | 57.457 | −56.261 | 1.00 | 44.36 | O |
| ATOM | 7077 | CB | PRO | G | 185 | 28.522 | 60.303 | −58.012 | 1.00 | 43.19 | C |
| ATOM | 7078 | CG | PRO | G | 185 | 27.292 | 59.663 | −58.551 | 1.00 | 43.35 | C |
| ATOM | 7079 | CD | PRO | G | 185 | 27.844 | 58.720 | −59.594 | 1.00 | 42.63 | C |
| ATOM | 7080 | N | MET | G | 186 | 30.021 | 59.128 | −55.492 | 1.00 | 44.05 | N |
| ATOM | 7081 | CA | MET | G | 186 | 30.020 | 58.666 | −54.111 | 1.00 | 44.25 | C |
| ATOM | 7082 | C | MET | G | 186 | 28.606 | 58.465 | −53.600 | 1.00 | 42.98 | C |
| ATOM | 7083 | O | MET | G | 186 | 27.810 | 59.403 | −53.552 | 1.00 | 42.87 | O |
| ATOM | 7084 | CB | MET | G | 186 | 30.738 | 59.675 | −53.214 | 1.00 | 46.35 | C |
| ATOM | 7085 | CG | MET | G | 186 | 32.139 | 59.258 | −52.808 | 1.00 | 50.04 | C |
| ATOM | 7086 | SD | MET | G | 186 | 32.148 | 57.751 | −51.802 | 1.00 | 52.71 | S |
| ATOM | 7087 | CE | MET | G | 186 | 32.923 | 56.587 | −52.955 | 1.00 | 51.94 | C |
| ATOM | 7088 | N | PRO | G | 187 | 28.267 | 57.232 | −53.213 | 1.00 | 41.91 | N |
| ATOM | 7089 | CA | PRO | G | 187 | 26.917 | 56.975 | −52.708 | 1.00 | 41.20 | C |
| ATOM | 7090 | C | PRO | G | 187 | 26.649 | 57.562 | −51.319 | 1.00 | 40.70 | C |
| ATOM | 7091 | O | PRO | G | 187 | 27.570 | 57.776 | −50.530 | 1.00 | 39.93 | O |
| ATOM | 7092 | CB | PRO | G | 187 | 26.816 | 55.447 | −52.737 | 1.00 | 41.16 | C |
| ATOM | 7093 | CG | PRO | G | 187 | 28.227 | 55.001 | −52.572 | 1.00 | 41.50 | C |
| ATOM | 7094 | CD | PRO | G | 187 | 28.999 | 55.971 | −53.438 | 1.00 | 41.38 | C |
| ATOM | 7095 | N | THR | G | 188 | 25.378 | 57.839 | −51.044 | 1.00 | 40.29 | N |
| ATOM | 7096 | CA | THR | G | 188 | 24.976 | 58.375 | −49.754 | 1.00 | 40.62 | C |
| ATOM | 7097 | C | THR | G | 188 | 24.623 | 57.203 | −48.849 | 1.00 | 40.45 | C |
| ATOM | 7098 | O | THR | G | 188 | 24.425 | 56.084 | −49.322 | 1.00 | 40.89 | O |
| ATOM | 7099 | CB | THR | G | 188 | 23.747 | 59.299 | −49.892 | 1.00 | 40.91 | C |
| ATOM | 7100 | OG1 | THR | G | 188 | 22.685 | 58.591 | −50.544 | 1.00 | 41.24 | O |
| ATOM | 7101 | CG2 | THR | G | 188 | 24.103 | 60.538 | −50.704 | 1.00 | 40.28 | C |
| ATOM | 7102 | N | MET | G | 189 | 24.552 | 57.459 | −47.551 | 1.00 | 40.54 | N |

TABLE 3-continued

FGFR2(D2–D3) Complexed with FGF2

| ATOM | 7103 | CA | MET | G | 189 | 24.218 | 56.414 | −46.603 | 1.00 | 40.70 | C |
|---|---|---|---|---|---|---|---|---|---|---|---|
| ATOM | 7104 | C | MET | G | 189 | 23.158 | 56.852 | −45.613 | 1.00 | 40.06 | C |
| ATOM | 7105 | O | MET | G | 189 | 23.178 | 57.983 | −45.124 | 1.00 | 40.47 | O |
| ATOM | 7106 | CB | MET | G | 189 | 25.454 | 55.958 | −45.836 | 1.00 | 43.01 | C |
| ATOM | 7107 | CG | MET | G | 189 | 25.120 | 54.977 | −44.729 | 1.00 | 46.26 | C |
| ATOM | 7108 | SD | MET | G | 189 | 26.578 | 54.334 | −43.921 | 1.00 | 51.42 | S |
| ATOM | 7109 | CE | MET | G | 189 | 26.573 | 52.656 | −44.569 | 1.00 | 48.28 | C |
| ATOM | 7110 | N | ARG | G | 190 | 22.229 | 55.944 | −45.331 | 1.00 | 38.37 | N |
| ATOM | 7111 | CA | ARG | G | 190 | 21.156 | 56.193 | −44.379 | 1.00 | 37.86 | C |
| ATOM | 7112 | C | ARG | G | 190 | 20.976 | 54.940 | −43.522 | 1.00 | 35.87 | C |
| ATOM | 7113 | O | ARG | G | 190 | 21.118 | 53.823 | −44.029 | 1.00 | 35.22 | O |
| ATOM | 7114 | CB | ARG | G | 190 | 19.846 | 56.487 | −45.108 | 1.00 | 39.91 | C |
| ATOM | 7115 | CG | ARG | G | 190 | 19.989 | 57.359 | −46.335 | 1.00 | 44.33 | C |
| ATOM | 7116 | CD | ARG | G | 190 | 18.650 | 58.006 | −46.693 | 1.00 | 47.36 | C |
| ATOM | 7117 | NE | ARG | G | 190 | 17.538 | 57.053 | −46.736 | 1.00 | 49.72 | N |
| ATOM | 7118 | CZ | ARG | G | 190 | 17.388 | 56.103 | −47.657 | 1.00 | 50.89 | C |
| ATOM | 7119 | NH1 | ARG | G | 190 | 18.283 | 55.960 | −48.627 | 1.00 | 51.57 | N |
| ATOM | 7120 | NH2 | ARG | G | 190 | 16.329 | 55.303 | −47.617 | 1.00 | 51.62 | N |
| ATOM | 7121 | N | TRP | G | 191 | 20.658 | 55.127 | −42.242 | 1.00 | 33.21 | N |
| ATOM | 7122 | CA | TRP | G | 191 | 20.450 | 54.005 | −41.329 | 1.00 | 32.38 | C |
| ATOM | 7123 | C | TRP | G | 191 | 19.009 | 53.896 | −40.842 | 1.00 | 31.73 | C |
| ATOM | 7124 | O | TRP | G | 191 | 18.397 | 54.893 | −40.474 | 1.00 | 32.66 | O |
| ATOM | 7125 | CB | TRP | G | 191 | 21.373 | 54.140 | −40.118 | 1.00 | 32.19 | C |
| ATOM | 7126 | CG | TRP | G | 191 | 22.800 | 53.886 | −40.446 | 1.00 | 32.15 | C |
| ATOM | 7127 | CD1 | TRP | G | 191 | 23.724 | 54.792 | −40.894 | 1.00 | 32.51 | C |
| ATOM | 7128 | CD2 | TRP | G | 191 | 23.468 | 52.627 | −40.378 | 1.00 | 31.70 | C |
| ATOM | 7129 | NE1 | TRP | G | 191 | 24.929 | 54.166 | −41.108 | 1.00 | 32.76 | N |
| ATOM | 7130 | CE2 | TRP | G | 191 | 24.798 | 52.837 | −40.797 | 1.00 | 31.62 | C |
| ATOM | 7131 | CE3 | TRP | G | 191 | 23.068 | 51.338 | −40.007 | 1.00 | 31.89 | C |
| ATOM | 7132 | CZ2 | TRP | G | 191 | 25.734 | 51.805 | −40.848 | 1.00 | 31.49 | C |
| ATOM | 7133 | CZ3 | TRP | G | 191 | 23.994 | 50.313 | −40.058 | 1.00 | 30.94 | C |
| ATOM | 7134 | CH2 | TRP | G | 191 | 25.317 | 50.554 | −40.477 | 1.00 | 31.73 | C |
| ATOM | 7135 | N | LEU | G | 192 | 18.470 | 52.684 | −40.827 | 1.00 | 30.78 | N |
| ATOM | 7136 | CA | LEU | G | 192 | 17.109 | 52.480 | −40.368 | 1.00 | 31.16 | C |
| ATOM | 7137 | C | LEU | G | 192 | 17.086 | 51.589 | −39.129 | 1.00 | 31.29 | C |
| ATOM | 7138 | O | LEU | G | 192 | 17.950 | 50.721 | −38.956 | 1.00 | 31.14 | O |
| ATOM | 7139 | CB | LEU | G | 192 | 16.268 | 51.819 | −41.468 | 1.00 | 31.89 | C |
| ATOM | 7140 | CG | LEU | G | 192 | 16.364 | 52.423 | −42.873 | 1.00 | 32.22 | C |
| ATOM | 7141 | CD1 | LEU | G | 192 | 15.550 | 51.569 | −43.842 | 1.00 | 32.92 | C |
| ATOM | 7142 | CD2 | LEU | G | 192 | 15.869 | 53.877 | −42.859 | 1.00 | 31.73 | C |
| ATOM | 7143 | N | LYS | G | 193 | 16.111 | 51.824 | −38.255 | 1.00 | 30.53 | N |
| ATOM | 7144 | CA | LYS | G | 193 | 15.942 | 50.994 | −37.079 | 1.00 | 30.93 | C |
| ATOM | 7145 | C | LYS | G | 193 | 14.587 | 50.325 | −37.276 | 1.00 | 31.82 | C |
| ATOM | 7146 | O | LYS | G | 193 | 13.568 | 51.007 | −37.385 | 1.00 | 32.06 | O |
| ATOM | 7147 | CB | LYS | G | 193 | 15.939 | 51.812 | −35.787 | 1.00 | 29.89 | C |
| ATOM | 7148 | CG | LYS | G | 193 | 15.739 | 50.917 | −34.559 | 1.00 | 30.55 | C |
| ATOM | 7149 | CD | LYS | G | 193 | 15.637 | 51.684 | −33.249 | 1.00 | 31.57 | C |
| ATOM | 7150 | CE | LYS | G | 193 | 15.409 | 50.732 | −32.072 | 1.00 | 31.81 | C |
| ATOM | 7151 | NZ | LYS | G | 193 | 15.123 | 51.443 | −30.793 | 1.00 | 32.09 | N |
| ATOM | 7152 | N | ASN | G | 194 | 14.580 | 48.998 | −37.327 | 1.00 | 32.57 | N |
| ATOM | 7153 | CA | ASN | G | 194 | 13.350 | 48.248 | −37.535 | 1.00 | 34.51 | C |
| ATOM | 7154 | C | ASN | G | 194 | 12.611 | 48.785 | −38.785 | 1.00 | 35.41 | C |
| ATOM | 7155 | O | ASN | G | 194 | 11.406 | 49.008 | −38.743 | 1.00 | 34.59 | O |
| ATOM | 7156 | CB | ASN | G | 194 | 12.430 | 48.361 | −36.315 | 1.00 | 35.04 | C |
| ATOM | 7157 | CG | ASN | G | 194 | 13.044 | 47.770 | −35.072 | 1.00 | 36.73 | C |
| ATOM | 7158 | OD1 | ASN | G | 194 | 13.762 | 46.756 | −35.131 | 1.00 | 36.07 | O |
| ATOM | 7159 | ND2 | ASN | G | 194 | 12.760 | 48.387 | −33.926 | 1.00 | 36.25 | N |
| ATOM | 7160 | N | GLY | G | 195 | 13.357 | 48.879 | −39.881 | 1.00 | 35.42 | N |
| ATOM | 7161 | CA | GLY | G | 195 | 12.792 | 49.307 | −41.150 | 1.00 | 35.86 | C |
| ATOM | 7162 | C | GLY | G | 195 | 12.275 | 50.730 | −41.289 | 1.00 | 36.25 | C |
| ATOM | 7163 | O | GLY | G | 195 | 11.630 | 51.046 | −42.287 | 1.00 | 36.76 | O |
| ATOM | 7164 | N | LYS | G | 196 | 12.542 | 51.591 | −40.313 | 1.00 | 36.25 | N |
| ATOM | 7165 | CA | LYS | G | 196 | 12.081 | 52.973 | −40.384 | 1.00 | 36.21 | C |
| ATOM | 7166 | C | LYS | G | 196 | 13.219 | 53.913 | −40.029 | 1.00 | 36.72 | C |
| ATOM | 7167 | O | LYS | G | 196 | 14.177 | 53.515 | −39.371 | 1.00 | 36.32 | O |
| ATOM | 7168 | CB | LYS | G | 196 | 10.905 | 53.205 | −39.422 | 1.00 | 36.17 | C |
| ATOM | 7169 | N | GLU | G | 197 | 13.104 | 55.163 | −40.462 | 1.00 | 37.23 | N |
| ATOM | 7170 | CA | GLU | G | 197 | 14.127 | 56.157 | −40.185 | 1.00 | 38.95 | C |
| ATOM | 7171 | C | GLU | G | 197 | 14.525 | 56.124 | −38.715 | 1.00 | 38.68 | C |
| ATOM | 7172 | O | GLU | G | 197 | 13.670 | 56.072 | −37.833 | 1.00 | 38.67 | O |
| ATOM | 7173 | CB | GLU | G | 197 | 13.627 | 57.554 | −40.539 | 1.00 | 40.62 | C |
| ATOM | 7174 | CG | GLU | G | 197 | 14.594 | 58.641 | −40.127 | 1.00 | 44.22 | C |
| ATOM | 7175 | CD | GLU | G | 197 | 14.039 | 60.023 | −40.356 | 1.00 | 46.08 | C |
| ATOM | 7176 | OE1 | GLU | G | 197 | 12.815 | 60.199 | −40.157 | 1.00 | 46.92 | O |
| ATOM | 7177 | OE2 | GLU | G | 197 | 14.825 | 60.930 | −40.718 | 1.00 | 46.94 | O |
| ATOM | 7178 | N | PHE | G | 198 | 15.834 | 56.146 | −38.474 | 1.00 | 38.58 | N |
| ATOM | 7179 | CA | PHE | G | 198 | 16.411 | 56.120 | −37.131 | 1.00 | 38.05 | C |

TABLE 3-continued

FGFR2(D2–D3) Complexed with FGF2

| ATOM | 7180 | C   | PHE | G | 198 | 16.716 | 57.575 | −36.776 | 1.00 | 38.47 | C |
|------|------|-----|-----|---|-----|--------|--------|---------|------|-------|---|
| ATOM | 7181 | O   | PHE | G | 198 | 17.557 | 58.210 | −37.418 | 1.00 | 38.57 | O |
| ATOM | 7182 | CB  | PHE | G | 198 | 17.714 | 55.307 | −37.156 | 1.00 | 38.22 | C |
| ATOM | 7183 | CG  | PHE | G | 198 | 18.332 | 55.058 | −35.794 | 1.00 | 38.04 | C |
| ATOM | 7184 | CD1 | PHE | G | 198 | 19.673 | 54.676 | −35.695 | 1.00 | 37.65 | C |
| ATOM | 7185 | CD2 | PHE | G | 198 | 17.579 | 55.153 | −34.628 | 1.00 | 37.37 | C |
| ATOM | 7186 | CE1 | PHE | G | 198 | 20.256 | 54.392 | −34.455 | 1.00 | 37.94 | C |
| ATOM | 7187 | CE2 | PHE | G | 198 | 18.147 | 54.870 | −33.384 | 1.00 | 38.19 | C |
| ATOM | 7188 | CZ  | PHE | G | 198 | 19.488 | 54.487 | −33.295 | 1.00 | 38.35 | C |
| ATOM | 7189 | N   | LYS | G | 199 | 16.035 | 58.096 | −35.760 | 1.00 | 38.43 | N |
| ATOM | 7190 | CA  | LYS | G | 199 | 16.215 | 59.479 | −35.332 | 1.00 | 39.45 | C |
| ATOM | 7191 | C   | LYS | G | 199 | 16.990 | 59.590 | −34.016 | 1.00 | 39.07 | C |
| ATOM | 7192 | O   | LYS | G | 199 | 16.950 | 58.680 | −33.190 | 1.00 | 38.70 | O |
| ATOM | 7193 | CB  | LYS | G | 199 | 14.847 | 60.142 | −35.143 | 1.00 | 41.28 | C |
| ATOM | 7194 | CG  | LYS | G | 199 | 13.883 | 60.012 | −36.318 | 1.00 | 43.58 | C |
| ATOM | 7195 | CD  | LYS | G | 199 | 12.657 | 60.899 | −36.082 | 1.00 | 45.84 | C |
| ATOM | 7196 | CE  | LYS | G | 199 | 11.660 | 60.854 | −37.242 | 1.00 | 46.93 | C |
| ATOM | 7197 | NZ  | LYS | G | 199 | 10.503 | 61.786 | −37.021 | 1.00 | 47.65 | N |
| ATOM | 7198 | N   | GLN | G | 200 | 17.677 | 60.714 | −33.819 | 1.00 | 38.63 | N |
| ATOM | 7199 | CA  | GLN | G | 200 | 18.447 | 60.941 | −32.597 | 1.00 | 38.68 | C |
| ATOM | 7200 | C   | GLN | G | 200 | 17.597 | 60.759 | −31.338 | 1.00 | 39.23 | C |
| ATOM | 7201 | O   | GLN | G | 200 | 18.073 | 60.228 | −30.337 | 1.00 | 39.32 | O |
| ATOM | 7202 | CB  | GLN | G | 200 | 19.047 | 62.355 | −32.573 | 1.00 | 38.64 | C |
| ATOM | 7203 | CG  | GLN | G | 200 | 20.185 | 62.623 | −33.561 | 1.00 | 38.51 | C |
| ATOM | 7204 | CD  | GLN | G | 200 | 21.456 | 61.819 | −33.266 | 1.00 | 39.24 | C |
| ATOM | 7205 | OE1 | GLN | G | 200 | 21.841 | 61.627 | −32.104 | 1.00 | 38.68 | O |
| ATOM | 7206 | NE2 | GLN | G | 200 | 22.119 | 61.363 | −34.320 | 1.00 | 38.44 | N |
| ATOM | 7207 | N   | GLU | G | 201 | 16.340 | 61.191 | −31.380 | 1.00 | 39.57 | N |
| ATOM | 7208 | CA  | GLU | G | 201 | 15.485 | 61.075 | −30.201 | 1.00 | 39.85 | C |
| ATOM | 7209 | C   | GLU | G | 201 | 14.982 | 59.656 | −29.939 | 1.00 | 39.23 | C |
| ATOM | 7210 | O   | GLU | G | 201 | 14.292 | 59.411 | −28.952 | 1.00 | 38.51 | O |
| ATOM | 7211 | CB  | GLU | G | 201 | 14.283 | 62.026 | −30.299 | 1.00 | 41.90 | C |
| ATOM | 7212 | CG  | GLU | G | 201 | 13.335 | 61.713 | −31.445 | 1.00 | 45.60 | C |
| ATOM | 7213 | CD  | GLU | G | 201 | 13.526 | 62.640 | −32.627 | 1.00 | 47.66 | C |
| ATOM | 7214 | OE1 | GLU | G | 201 | 14.694 | 62.871 | −33.025 | 1.00 | 48.51 | O |
| ATOM | 7215 | OE2 | GLU | G | 201 | 12.500 | 63.132 | −33.158 | 1.00 | 49.36 | O |
| ATOM | 7216 | N   | HIS | G | 202 | 15.335 | 58.716 | −30.809 | 1.00 | 39.29 | N |
| ATOM | 7217 | CA  | HIS | G | 202 | 14.892 | 57.339 | −30.637 | 1.00 | 38.89 | C |
| ATOM | 7218 | C   | HIS | G | 202 | 15.560 | 56.598 | −29.466 | 1.00 | 38.13 | C |
| ATOM | 7219 | O   | HIS | G | 202 | 15.130 | 55.499 | −29.099 | 1.00 | 37.78 | O |
| ATOM | 7220 | CB  | HIS | G | 202 | 15.095 | 56.552 | −31.934 | 1.00 | 40.98 | C |
| ATOM | 7221 | CG  | HIS | G | 202 | 14.088 | 56.862 | −33.000 | 1.00 | 43.91 | C |
| ATOM | 7222 | ND1 | HIS | G | 202 | 12.890 | 57.500 | −32.740 | 1.00 | 43.84 | N |
| ATOM | 7223 | CD2 | HIS | G | 202 | 14.085 | 56.586 | −34.328 | 1.00 | 44.08 | C |
| ATOM | 7224 | CE1 | HIS | G | 202 | 12.197 | 57.602 | −33.860 | 1.00 | 44.30 | C |
| ATOM | 7225 | NE2 | HIS | G | 202 | 12.899 | 57.056 | −34.838 | 1.00 | 44.94 | N |
| ATOM | 7226 | N   | ARG | G | 203 | 16.602 | 57.195 | −28.883 | 1.00 | 37.18 | N |
| ATOM | 7227 | CA  | ARG | G | 203 | 17.312 | 56.589 | −27.748 | 1.00 | 36.74 | C |
| ATOM | 7228 | C   | ARG | G | 203 | 18.032 | 57.642 | −26.908 | 1.00 | 36.51 | C |
| ATOM | 7229 | O   | ARG | G | 203 | 18.412 | 58.695 | −27.411 | 1.00 | 35.86 | O |
| ATOM | 7230 | CB  | ARG | G | 203 | 18.345 | 55.561 | −28.236 | 1.00 | 37.01 | C |
| ATOM | 7231 | N   | ILE | G | 204 | 18.224 | 57.358 | −25.624 | 1.00 | 36.85 | N |
| ATOM | 7232 | CA  | ILE | G | 204 | 18.925 | 58.297 | −24.749 | 1.00 | 37.60 | C |
| ATOM | 7233 | C   | ILE | G | 204 | 20.325 | 58.518 | −25.334 | 1.00 | 37.66 | C |
| ATOM | 7234 | O   | ILE | G | 204 | 21.041 | 57.553 | −25.629 | 1.00 | 37.54 | O |
| ATOM | 7235 | CB  | ILE | G | 204 | 19.074 | 57.736 | −23.302 | 1.00 | 38.46 | C |
| ATOM | 7236 | CG1 | ILE | G | 204 | 17.712 | 57.316 | −22.748 | 1.00 | 39.56 | C |
| ATOM | 7237 | CG2 | ILE | G | 204 | 19.677 | 58.800 | −22.375 | 1.00 | 39.44 | C |
| ATOM | 7238 | CD1 | ILE | G | 204 | 16.709 | 58.438 | −22.672 | 1.00 | 40.21 | C |
| ATOM | 7239 | N   | GLY | G | 205 | 20.708 | 59.778 | −25.515 | 1.00 | 37.64 | N |
| ATOM | 7240 | CA  | GLY | G | 205 | 22.021 | 60.082 | −26.062 | 1.00 | 37.39 | C |
| ATOM | 7241 | C   | GLY | G | 205 | 22.170 | 59.934 | −27.567 | 1.00 | 36.81 | C |
| ATOM | 7242 | O   | GLY | G | 205 | 23.245 | 60.185 | −28.109 | 1.00 | 37.10 | O |
| ATOM | 7243 | N   | GLY | G | 206 | 21.101 | 59.525 | −28.246 | 1.00 | 36.83 | N |
| ATOM | 7244 | CA  | GLY | G | 206 | 21.154 | 59.373 | −29.692 | 1.00 | 35.77 | C |
| ATOM | 7245 | C   | GLY | G | 206 | 22.266 | 58.480 | −30.216 | 1.00 | 35.37 | C |
| ATOM | 7246 | O   | GLY | G | 206 | 22.643 | 57.496 | −29.581 | 1.00 | 33.92 | O |
| ATOM | 7247 | N   | TYR | G | 207 | 22.794 | 58.831 | −31.383 | 1.00 | 35.95 | N |
| ATOM | 7248 | CA  | TYR | G | 207 | 23.841 | 58.042 | −32.003 | 1.00 | 36.65 | C |
| ATOM | 7249 | C   | TYR | G | 207 | 24.812 | 58.905 | −32.809 | 1.00 | 37.12 | C |
| ATOM | 7250 | O   | TYR | G | 207 | 24.598 | 60.104 | −32.982 | 1.00 | 36.47 | O |
| ATOM | 7251 | CB  | TYR | G | 207 | 23.207 | 56.980 | −32.907 | 1.00 | 37.46 | C |
| ATOM | 7252 | CG  | TYR | G | 207 | 22.328 | 57.548 | −33.999 | 1.00 | 38.06 | C |
| ATOM | 7253 | CD1 | TYR | G | 207 | 20.953 | 57.716 | −33.813 | 1.00 | 38.07 | C |
| ATOM | 7254 | CD2 | TYR | G | 207 | 22.880 | 57.942 | −35.218 | 1.00 | 38.57 | C |
| ATOM | 7255 | CE1 | TYR | G | 207 | 20.148 | 58.268 | −34.827 | 1.00 | 38.11 | C |
| ATOM | 7256 | CE2 | TYR | G | 207 | 22.097 | 58.496 | −36.227 | 1.00 | 38.57 | C |

TABLE 3-continued

FGFR2(D2–D3) Complexed with FGF2

| ATOM | 7257 | CZ | TYR | G | 207 | 20.737 | 58.661 | −36.031 | 1.00 | 39.30 | C |
|---|---|---|---|---|---|---|---|---|---|---|---|
| ATOM | 7258 | OH | TYR | G | 207 | 19.994 | 59.266 | −37.028 | 1.00 | 40.42 | O |
| ATOM | 7259 | N | LYS | G | 208 | 25.880 | 58.284 | −33.300 | 1.00 | 37.02 | N |
| ATOM | 7260 | CA | LYS | G | 208 | 26.874 | 58.997 | −34.088 | 1.00 | 38.49 | C |
| ATOM | 7261 | C | LYS | G | 208 | 27.150 | 58.251 | −35.396 | 1.00 | 39.32 | C |
| ATOM | 7262 | O | LYS | G | 208 | 27.144 | 57.019 | −35.437 | 1.00 | 38.90 | O |
| ATOM | 7263 | CB | LYS | G | 208 | 28.174 | 59.150 | −33.285 | 1.00 | 38.12 | C |
| ATOM | 7264 | CG | LYS | G | 208 | 28.008 | 59.852 | −31.932 | 1.00 | 38.59 | C |
| ATOM | 7265 | CD | LYS | G | 208 | 29.342 | 59.926 | −31.187 | 1.00 | 37.31 | C |
| ATOM | 7266 | CE | LYS | G | 208 | 29.213 | 60.616 | −29.838 | 1.00 | 37.57 | C |
| ATOM | 7267 | NZ | LYS | G | 208 | 30.504 | 60.595 | −29.087 | 1.00 | 36.21 | N |
| ATOM | 7268 | N | VAL | G | 209 | 27.385 | 59.007 | −36.464 | 1.00 | 40.76 | N |
| ATOM | 7269 | CA | VAL | G | 209 | 27.668 | 58.431 | −37.776 | 1.00 | 42.75 | C |
| ATOM | 7270 | C | VAL | G | 209 | 28.932 | 59.040 | −38.363 | 1.00 | 44.10 | C |
| ATOM | 7271 | O | VAL | G | 209 | 29.083 | 60.260 | −38.399 | 1.00 | 44.90 | O |
| ATOM | 7272 | CB | VAL | G | 209 | 26.500 | 58.673 | −38.774 | 1.00 | 42.78 | C |
| ATOM | 7273 | CG1 | VAL | G | 209 | 26.929 | 58.275 | −40.184 | 1.00 | 43.23 | C |
| ATOM | 7274 | CG2 | VAL | G | 209 | 25.276 | 57.864 | −38.360 | 1.00 | 42.54 | C |
| ATOM | 7275 | N | ARG | G | 210 | 29.844 | 58.184 | −38.809 | 1.00 | 45.61 | N |
| ATOM | 7276 | CA | ARG | G | 210 | 31.092 | 58.632 | −39.422 | 1.00 | 46.69 | C |
| ATOM | 7277 | C | ARG | G | 210 | 31.070 | 58.207 | −40.890 | 1.00 | 47.12 | C |
| ATOM | 7278 | O | ARG | G | 210 | 31.463 | 57.091 | −41.222 | 1.00 | 47.50 | O |
| ATOM | 7279 | CB | ARG | G | 210 | 32.297 | 57.997 | −38.716 | 1.00 | 46.16 | C |
| ATOM | 7280 | N | ASN | G | 211 | 30.596 | 59.097 | −41.759 | 1.00 | 47.91 | N |
| ATOM | 7281 | CA | ASN | G | 211 | 30.513 | 58.819 | −43.191 | 1.00 | 48.52 | C |
| ATOM | 7282 | C | ASN | G | 211 | 31.803 | 58.251 | −43.771 | 1.00 | 48.05 | C |
| ATOM | 7283 | O | ASN | G | 211 | 31.772 | 57.335 | −44.592 | 1.00 | 47.81 | O |
| ATOM | 7284 | CB | ASN | G | 211 | 30.132 | 60.088 | −43.950 | 1.00 | 49.91 | C |
| ATOM | 7285 | CG | ASN | G | 211 | 28.724 | 60.549 | −43.636 | 1.00 | 51.73 | C |
| ATOM | 7286 | CD1 | ASN | G | 211 | 27.756 | 59.808 | −43.832 | 1.00 | 53.25 | O |
| ATOM | 7287 | ND2 | ASN | G | 211 | 28.597 | 61.779 | −43.146 | 1.00 | 52.48 | N |
| ATOM | 7288 | N | GLN | G | 212 | 32.937 | 58.791 | −43.336 | 1.00 | 47.63 | N |
| ATOM | 7289 | CA | GLN | G | 212 | 34.231 | 58.327 | −43.823 | 1.00 | 46.56 | C |
| ATOM | 7290 | C | GLN | G | 212 | 34.453 | 56.835 | −43.559 | 1.00 | 45.40 | C |
| ATOM | 7291 | O | GLN | G | 212 | 35.177 | 56.172 | −44.296 | 1.00 | 46.16 | O |
| ATOM | 7292 | CB | GLN | G | 212 | 35.354 | 59.149 | −43.185 | 1.00 | 46.95 | C |
| ATOM | 7293 | N | HIS | G | 213 | 33.823 | 56.305 | −42.514 | 1.00 | 43.32 | N |
| ATOM | 7294 | CA | HIS | G | 213 | 33.971 | 54.894 | −42.180 | 1.00 | 41.09 | C |
| ATOM | 7295 | C | HIS | G | 213 | 32.695 | 54.078 | −42.437 | 1.00 | 38.71 | C |
| ATOM | 7296 | O | HIS | G | 213 | 32.653 | 52.878 | −42.149 | 1.00 | 37.89 | O |
| ATOM | 7297 | CB | HIS | G | 213 | 34.401 | 54.757 | −40.712 | 1.00 | 41.66 | C |
| ATOM | 7298 | N | TRP | G | 214 | 31.675 | 54.732 | −42.991 | 1.00 | 36.16 | N |
| ATOM | 7299 | CA | TRP | G | 214 | 30.386 | 54.094 | −43.288 | 1.00 | 34.68 | C |
| ATOM | 7300 | C | TRP | G | 214 | 29.892 | 53.347 | −42.056 | 1.00 | 33.39 | C |
| ATOM | 7301 | O | TRP | G | 214 | 29.474 | 52.189 | −42.132 | 1.00 | 32.36 | O |
| ATOM | 7302 | CB | TRP | G | 214 | 30.523 | 53.123 | −44.465 | 1.00 | 34.65 | C |
| ATOM | 7303 | CG | TRP | G | 214 | 31.183 | 53.713 | −45.677 | 1.00 | 35.68 | C |
| ATOM | 7304 | CD1 | TRP | G | 214 | 32.509 | 53.657 | −45.992 | 1.00 | 35.69 | C |
| ATOM | 7305 | CD2 | TRP | G | 214 | 30.552 | 54.467 | −46.723 | 1.00 | 35.33 | C |
| ATOM | 7306 | NE1 | TRP | G | 214 | 32.744 | 54.329 | −47.168 | 1.00 | 36.32 | N |
| ATOM | 7307 | CE2 | TRP | G | 214 | 31.561 | 54.837 | −47.637 | 1.00 | 35.75 | C |
| ATOM | 7308 | CE3 | TRP | G | 214 | 29.232 | 54.867 | −46.975 | 1.00 | 36.44 | C |
| ATOM | 7309 | CZ2 | TRP | G | 214 | 31.293 | 55.592 | −48.790 | 1.00 | 35.48 | C |
| ATOM | 7310 | CZ3 | TRP | G | 214 | 28.963 | 55.620 | −48.128 | 1.00 | 36.36 | C |
| ATOM | 7311 | CH2 | TRP | G | 214 | 29.993 | 55.972 | −49.017 | 1.00 | 35.54 | C |
| ATOM | 7312 | N | SER | G | 215 | 29.918 | 54.032 | −40.918 | 1.00 | 32.58 | N |
| ATOM | 7313 | CA | SER | G | 215 | 29.522 | 53.412 | −39.665 | 1.00 | 31.88 | C |
| ATOM | 7314 | C | SER | G | 215 | 28.440 | 54.113 | −38.852 | 1.00 | 31.15 | C |
| ATOM | 7315 | O | SER | G | 215 | 28.246 | 55.321 | −38.949 | 1.00 | 31.31 | O |
| ATOM | 7316 | CB | SER | G | 215 | 30.758 | 53.283 | −38.786 | 1.00 | 32.21 | C |
| ATOM | 7317 | OG | SER | G | 215 | 31.302 | 54.577 | −38.596 | 1.00 | 32.73 | O |
| ATOM | 7318 | N | LEU | G | 216 | 27.761 | 53.319 | −38.028 | 1.00 | 30.57 | N |
| ATOM | 7319 | CA | LEU | G | 216 | 26.729 | 53.798 | −37.111 | 1.00 | 29.12 | C |
| ATOM | 7320 | C | LEU | G | 216 | 27.234 | 53.394 | −35.724 | 1.00 | 27.81 | C |
| ATOM | 7321 | O | LEU | G | 216 | 27.577 | 52.231 | −35.506 | 1.00 | 26.76 | O |
| ATOM | 7322 | CB | LEU | G | 216 | 25.382 | 53.120 | −37.391 | 1.00 | 29.27 | C |
| ATOM | 7323 | CG | LEU | G | 216 | 24.282 | 53.271 | −36.319 | 1.00 | 29.94 | C |
| ATOM | 7324 | CD1 | LEU | G | 216 | 23.772 | 54.696 | −36.292 | 1.00 | 28.63 | C |
| ATOM | 7325 | CD2 | LEU | G | 216 | 23.128 | 52.337 | −36.620 | 1.00 | 28.50 | C |
| ATOM | 7326 | N | ILE | G | 217 | 27.277 | 54.347 | −34.798 | 1.00 | 27.49 | N |
| ATOM | 7327 | CA | ILE | G | 217 | 27.759 | 54.084 | −33.433 | 1.00 | 27.69 | C |
| ATOM | 7328 | C | ILE | G | 217 | 26.751 | 54.413 | −32.329 | 1.00 | 28.49 | C |
| ATOM | 7329 | O | ILE | G | 217 | 26.180 | 55.515 | −32.293 | 1.00 | 27.54 | O |
| ATOM | 7330 | CB | ILE | G | 217 | 29.057 | 54.888 | −33.145 | 1.00 | 29.03 | C |
| ATOM | 7331 | CG1 | ILE | G | 217 | 30.190 | 54.373 | −34.025 | 1.00 | 29.08 | C |
| ATOM | 7332 | CG2 | ILE | G | 217 | 29.447 | 54.777 | −31.676 | 1.00 | 28.67 | C |
| ATOM | 7333 | CD1 | ILE | G | 217 | 31.406 | 55.232 | −33.972 | 1.00 | 30.72 | C |

TABLE 3-continued

FGFR2(D2–D3) Complexed with FGF2

| ATOM | 7334 | N   | MET | G | 218 | 26.534 | 53.452 | −31.430 | 1.00 | 28.14 | N |
|------|------|-----|-----|---|-----|--------|--------|---------|------|-------|---|
| ATOM | 7335 | CA  | MET | G | 218 | 25.636 | 53.638 | −30.295 | 1.00 | 29.05 | C |
| ATOM | 7336 | C   | MET | G | 218 | 26.429 | 53.316 | −29.019 | 1.00 | 30.12 | C |
| ATOM | 7337 | O   | MET | G | 218 | 26.945 | 52.206 | −28.856 | 1.00 | 29.60 | O |
| ATOM | 7338 | CB  | MET | G | 218 | 24.391 | 52.736 | −30.397 | 1.00 | 28.75 | C |
| ATOM | 7339 | CG  | MET | G | 218 | 23.349 | 53.184 | −31.437 | 1.00 | 30.25 | C |
| ATOM | 7340 | SD  | MET | G | 218 | 21.994 | 51.978 | −31.723 | 1.00 | 31.16 | S |
| ATOM | 7341 | CE  | MET | G | 218 | 22.916 | 50.662 | −32.561 | 1.00 | 31.17 | C |
| ATOM | 7342 | N   | GLU | G | 219 | 26.534 | 54.300 | −28.132 | 1.00 | 29.92 | N |
| ATOM | 7343 | CA  | GLU | G | 219 | 27.273 | 54.150 | −26.882 | 1.00 | 30.46 | C |
| ATOM | 7344 | C   | GLU | G | 219 | 26.370 | 53.744 | −25.722 | 1.00 | 31.49 | C |
| ATOM | 7345 | O   | GLU | G | 219 | 25.172 | 54.041 | −25.718 | 1.00 | 32.13 | O |
| ATOM | 7346 | CB  | GLU | G | 219 | 27.991 | 55.463 | −26.546 | 1.00 | 31.02 | C |
| ATOM | 7347 | CG  | GLU | G | 219 | 28.927 | 55.949 | −27.656 | 1.00 | 30.31 | C |
| ATOM | 7348 | CD  | GLU | G | 219 | 29.071 | 57.461 | −27.685 | 1.00 | 31.67 | C |
| ATOM | 7349 | OE1 | GLU | G | 219 | 28.054 | 58.150 | −27.465 | 1.00 | 30.77 | O |
| ATOM | 7350 | OE2 | GLU | G | 219 | 30.189 | 57.964 | −27.951 | 1.00 | 32.04 | O |
| ATOM | 7351 | N   | SER | G | 220 | 26.953 | 53.035 | −24.756 | 1.00 | 31.30 | N |
| ATOM | 7352 | CA  | SER | G | 220 | 26.254 | 52.572 | −23.561 | 1.00 | 31.39 | C |
| ATOM | 7353 | C   | SER | G | 220 | 24.907 | 51.908 | −23.847 | 1.00 | 31.55 | C |
| ATOM | 7354 | O   | SER | G | 220 | 23.869 | 52.337 | −23.324 | 1.00 | 31.32 | O |
| ATOM | 7355 | CB  | SER | G | 220 | 26.054 | 53.752 | −22.615 | 1.00 | 31.91 | C |
| ATOM | 7356 | OG  | SER | G | 220 | 27.249 | 54.506 | −22.530 | 1.00 | 33.28 | O |
| ATOM | 7357 | N   | VAL | G | 221 | 24.923 | 50.843 | −24.643 | 1.00 | 30.54 | N |
| ATOM | 7358 | CA  | VAL | G | 221 | 23.681 | 50.167 | −24.998 | 1.00 | 31.16 | C |
| ATOM | 7359 | C   | VAL | G | 221 | 22.921 | 49.566 | −23.818 | 1.00 | 32.05 | C |
| ATOM | 7360 | O   | VAL | G | 221 | 23.508 | 49.195 | −22.792 | 1.00 | 31.21 | O |
| ATOM | 7361 | CB  | VAL | G | 221 | 23.908 | 49.060 | −26.065 | 1.00 | 29.94 | C |
| ATOM | 7362 | CG1 | VAL | G | 221 | 24.596 | 49.656 | −27.279 | 1.00 | 30.06 | C |
| ATOM | 7363 | CG2 | VAL | G | 221 | 24.719 | 47.916 | −25.486 | 1.00 | 30.26 | C |
| ATOM | 7364 | N   | VAL | G | 222 | 21.602 | 49.472 | −23.985 | 1.00 | 32.24 | N |
| ATOM | 7365 | CA  | VAL | G | 222 | 20.721 | 48.926 | −22.965 | 1.00 | 32.79 | C |
| ATOM | 7366 | C   | VAL | G | 222 | 19.743 | 47.970 | −23.629 | 1.00 | 33.65 | C |
| ATOM | 7367 | O   | VAL | G | 222 | 19.616 | 47.951 | −24.855 | 1.00 | 33.38 | O |
| ATOM | 7368 | CB  | VAL | G | 222 | 19.942 | 50.049 | −22.257 | 1.00 | 32.50 | C |
| ATOM | 7369 | CG1 | VAL | G | 222 | 20.904 | 50.904 | −21.451 | 1.00 | 32.43 | C |
| ATOM | 7370 | CG2 | VAL | G | 222 | 19.224 | 50.913 | −23.282 | 1.00 | 32.13 | C |
| ATOM | 7371 | N   | PRO | G | 223 | 19.043 | 47.151 | −22.832 | 1.00 | 34.22 | N |
| ATOM | 7372 | CA  | PRO | G | 223 | 18.076 | 46.193 | −23.376 | 1.00 | 34.37 | C |
| ATOM | 7373 | C   | PRO | G | 223 | 17.116 | 46.751 | −24.430 | 1.00 | 34.67 | C |
| ATOM | 7374 | O   | PRO | G | 223 | 16.834 | 46.079 | −25.418 | 1.00 | 35.07 | O |
| ATOM | 7375 | CB  | PRO | G | 223 | 17.353 | 45.699 | −22.128 | 1.00 | 34.63 | C |
| ATOM | 7376 | CG  | PRO | G | 223 | 18.475 | 45.652 | −21.127 | 1.00 | 34.57 | C |
| ATOM | 7377 | CD  | PRO | G | 223 | 19.208 | 46.963 | −21.376 | 1.00 | 34.70 | C |
| ATOM | 7378 | N   | SER | G | 224 | 16.619 | 47.973 | −24.240 | 1.00 | 34.52 | N |
| ATOM | 7379 | CA  | SER | G | 224 | 15.690 | 48.548 | −25.214 | 1.00 | 34.43 | C |
| ATOM | 7380 | C   | SER | G | 224 | 16.277 | 48.819 | −26.607 | 1.00 | 34.27 | C |
| ATOM | 7381 | O   | SER | G | 224 | 15.532 | 49.086 | −27.550 | 1.00 | 33.93 | O |
| ATOM | 7382 | CB  | SER | G | 224 | 15.047 | 49.830 | −24.659 | 1.00 | 35.29 | C |
| ATOM | 7383 | OG  | SER | G | 224 | 16.016 | 50.750 | −24.181 | 1.00 | 37.46 | O |
| ATOM | 7384 | N   | ASP | G | 225 | 17.602 | 48.745 | −26.748 | 1.00 | 34.38 | N |
| ATOM | 7385 | CA  | ASP | G | 225 | 18.246 | 48.966 | −28.047 | 1.00 | 33.59 | C |
| ATOM | 7386 | C   | ASP | G | 225 | 18.114 | 47.746 | −28.976 | 1.00 | 33.29 | C |
| ATOM | 7387 | O   | ASP | G | 225 | 18.444 | 47.810 | −30.160 | 1.00 | 33.56 | O |
| ATOM | 7388 | CB  | ASP | G | 225 | 19.731 | 49.312 | −27.860 | 1.00 | 33.90 | C |
| ATOM | 7389 | CG  | ASP | G | 225 | 19.940 | 50.698 | −27.272 | 1.00 | 34.04 | C |
| ATOM | 7390 | OD1 | ASP | G | 225 | 19.312 | 51.661 | −27.760 | 1.00 | 34.35 | O |
| ATOM | 7391 | OD2 | ASP | G | 225 | 20.744 | 50.832 | −26.328 | 1.00 | 33.86 | O |
| ATOM | 7392 | N   | LYS | G | 226 | 17.634 | 46.630 | −28.436 | 1.00 | 33.97 | N |
| ATOM | 7393 | CA  | LYS | G | 226 | 17.460 | 45.415 | −29.238 | 1.00 | 33.58 | C |
| ATOM | 7394 | C   | LYS | G | 226 | 16.601 | 45.713 | −30.452 | 1.00 | 32.76 | C |
| ATOM | 7395 | O   | LYS | G | 226 | 15.591 | 46.410 | −30.348 | 1.00 | 33.24 | O |
| ATOM | 7396 | CB  | LYS | G | 226 | 16.782 | 44.311 | −28.420 | 1.00 | 34.76 | C |
| ATOM | 7397 | N   | GLY | G | 227 | 17.002 | 45.187 | −31.604 | 1.00 | 31.91 | N |
| ATOM | 7398 | CA  | GLY | G | 227 | 16.240 | 45.404 | −32.818 | 1.00 | 31.44 | C |
| ATOM | 7399 | C   | GLY | G | 227 | 17.077 | 45.219 | −34.073 | 1.00 | 32.34 | C |
| ATOM | 7400 | O   | GLY | G | 227 | 18.197 | 44.694 | −34.010 | 1.00 | 32.28 | O |
| ATOM | 7401 | N   | ASN | G | 228 | 16.533 | 45.643 | −35.211 | 1.00 | 31.51 | N |
| ATOM | 7402 | CA  | ASN | G | 228 | 17.231 | 45.543 | −36.485 | 1.00 | 31.35 | C |
| ATOM | 7403 | C   | ASN | G | 228 | 17.734 | 46.889 | −36.940 | 1.00 | 30.18 | C |
| ATOM | 7404 | O   | ASN | G | 228 | 17.019 | 47.885 | −36.845 | 1.00 | 31.12 | O |
| ATOM | 7405 | CB  | ASN | G | 228 | 16.316 | 44.998 | −37.568 | 1.00 | 32.51 | C |
| ATOM | 7406 | CG  | ASN | G | 228 | 15.927 | 43.586 | −37.311 | 1.00 | 34.95 | C |
| ATOM | 7407 | OD1 | ASN | G | 228 | 16.696 | 42.829 | −36.730 | 1.00 | 35.67 | O |
| ATOM | 7408 | ND2 | ASN | G | 228 | 14.732 | 43.206 | −37.745 | 1.00 | 36.62 | N |
| ATOM | 7409 | N   | TYR | G | 229 | 18.965 | 46.911 | −37.436 | 1.00 | 28.15 | N |
| ATOM | 7410 | CA  | TYR | G | 229 | 19.568 | 48.135 | −37.933 | 1.00 | 28.01 | C |

TABLE 3-continued

FGFR2(D2–D3) Complexed with FGF2

| ATOM | 7411 | C | TYR | G | 229 | 20.032 | 47.899 | −39.365 | 1.00 | 27.46 | C |
|---|---|---|---|---|---|---|---|---|---|---|---|
| ATOM | 7412 | O | TYR | G | 229 | 20.885 | 47.053 | −39.630 | 1.00 | 26.42 | O |
| ATOM | 7413 | CB | TYR | G | 229 | 20.721 | 48.568 | −37.021 | 1.00 | 28.59 | C |
| ATOM | 7414 | CG | TYR | G | 229 | 20.240 | 48.915 | −35.629 | 1.00 | 29.21 | C |
| ATOM | 7415 | CD1 | TYR | G | 229 | 20.033 | 47.925 | −34.672 | 1.00 | 29.80 | C |
| ATOM | 7416 | CD2 | TYR | G | 229 | 19.915 | 50.229 | −35.293 | 1.00 | 30.39 | C |
| ATOM | 7417 | CE1 | TYR | G | 229 | 19.505 | 48.236 | −33.415 | 1.00 | 30.65 | C |
| ATOM | 7418 | CE2 | TYR | G | 229 | 19.391 | 50.553 | −34.040 | 1.00 | 29.83 | C |
| ATOM | 7419 | CZ | TYR | G | 229 | 19.188 | 49.552 | −33.108 | 1.00 | 30.76 | C |
| ATOM | 7420 | OH | TYR | G | 229 | 18.659 | 49.867 | −31.872 | 1.00 | 32.33 | O |
| ATOM | 7421 | N | THR | G | 230 | 19.449 | 48.666 | −40.282 | 1.00 | 26.96 | N |
| ATOM | 7422 | CA | THR | G | 230 | 19.729 | 48.536 | −41.705 | 1.00 | 26.33 | C |
| ATOM | 7423 | C | THR | G | 230 | 20.432 | 49.731 | −42.326 | 1.00 | 26.67 | C |
| ATOM | 7424 | O | THR | G | 230 | 20.049 | 50.878 | −42.097 | 1.00 | 26.83 | O |
| ATOM | 7425 | CB | THR | G | 230 | 18.405 | 48.316 | −42.456 | 1.00 | 27.36 | C |
| ATOM | 7426 | OG1 | THR | G | 230 | 17.794 | 47.102 | −41.986 | 1.00 | 27.11 | O |
| ATOM | 7427 | CG2 | THR | G | 230 | 18.624 | 48.262 | −43.966 | 1.00 | 26.38 | C |
| ATOM | 7428 | N | CYS | G | 231 | 21.463 | 49.466 | −43.120 | 1.00 | 27.19 | N |
| ATOM | 7429 | CA | CYS | G | 231 | 22.168 | 50.549 | −43.802 | 1.00 | 27.64 | C |
| ATOM | 7430 | C | CYS | G | 231 | 21.734 | 50.506 | −45.268 | 1.00 | 27.64 | C |
| ATOM | 7431 | O | CYS | G | 231 | 21.714 | 49.442 | −45.889 | 1.00 | 27.09 | O |
| ATOM | 7432 | CB | CYS | G | 231 | 23.687 | 50.362 | −43.715 | 1.00 | 29.07 | C |
| ATOM | 7433 | SG | CYS | G | 231 | 24.273 | 48.894 | −44.592 | 1.00 | 31.30 | S |
| ATOM | 7434 | N | VAL | G | 232 | 21.361 | 51.665 | −45.802 | 1.00 | 28.82 | N |
| ATOM | 7435 | CA | VAL | G | 232 | 20.943 | 51.801 | −47.200 | 1.00 | 29.71 | C |
| ATOM | 7436 | C | VAL | G | 232 | 21.951 | 52.730 | −47.897 | 1.00 | 30.46 | C |
| ATOM | 7437 | O | VAL | G | 232 | 22.177 | 53.858 | −47.457 | 1.00 | 29.38 | O |
| ATOM | 7438 | CB | VAL | G | 232 | 19.520 | 52.421 | −47.317 | 1.00 | 29.90 | C |
| ATOM | 7439 | CG1 | VAL | G | 232 | 19.074 | 52.407 | −48.776 | 1.00 | 29.33 | C |
| ATOM | 7440 | CG2 | VAL | G | 232 | 18.529 | 51.641 | −46.448 | 1.00 | 29.15 | C |
| ATOM | 7441 | N | VAL | G | 233 | 22.557 | 52.247 | −48.978 | 1.00 | 30.43 | N |
| ATOM | 7442 | CA | VAL | G | 233 | 23.561 | 53.021 | −49.695 | 1.00 | 31.82 | C |
| ATOM | 7443 | C | VAL | G | 233 | 23.155 | 53.193 | −51.154 | 1.00 | 32.71 | C |
| ATOM | 7444 | O | VAL | G | 233 | 22.792 | 52.223 | −51.819 | 1.00 | 33.76 | O |
| ATOM | 7445 | CB | VAL | G | 233 | 24.949 | 52.333 | −49.554 | 1.00 | 30.72 | C |
| ATOM | 7446 | CG1 | VAL | G | 233 | 26.000 | 53.059 | −50.359 | 1.00 | 30.29 | C |
| ATOM | 7447 | CG2 | VAL | G | 233 | 25.353 | 52.328 | −48.070 | 1.00 | 30.62 | C |
| ATOM | 7448 | N | GLU | G | 234 | 23.201 | 54.424 | −51.653 | 1.00 | 33.51 | N |
| ATOM | 7449 | CA | GLU | G | 234 | 22.775 | 54.655 | −53.025 | 1.00 | 35.10 | C |
| ATOM | 7450 | C | GLU | G | 234 | 23.320 | 55.855 | −53.796 | 1.00 | 34.23 | C |
| ATOM | 7451 | O | GLU | G | 234 | 23.822 | 56.826 | −53.229 | 1.00 | 34.30 | O |
| ATOM | 7452 | CB | GLU | G | 234 | 21.246 | 54.698 | −53.068 | 1.00 | 37.35 | C |
| ATOM | 7453 | CG | GLU | G | 234 | 20.648 | 55.776 | −52.190 | 1.00 | 40.83 | C |
| ATOM | 7454 | CD | GLU | G | 234 | 19.198 | 55.499 | −51.810 | 1.00 | 44.47 | C |
| ATOM | 7455 | OE1 | GLU | G | 234 | 18.643 | 56.288 | −51.012 | 1.00 | 44.70 | O |
| ATOM | 7456 | OE2 | GLU | G | 234 | 18.616 | 54.496 | −52.295 | 1.00 | 44.42 | O |
| ATOM | 7457 | N | ASN | G | 235 | 23.221 | 55.737 | −55.116 | 1.00 | 34.32 | N |
| ATOM | 7458 | CA | ASN | G | 235 | 23.623 | 56.772 | −56.065 | 1.00 | 34.06 | C |
| ATOM | 7459 | C | ASN | G | 235 | 22.688 | 56.604 | −57.264 | 1.00 | 34.55 | C |
| ATOM | 7460 | O | ASN | G | 235 | 21.763 | 55.780 | −57.216 | 1.00 | 33.77 | O |
| ATOM | 7461 | CB | ASN | G | 235 | 25.116 | 56.656 | −56.474 | 1.00 | 32.59 | C |
| ATOM | 7462 | CG | ASN | G | 235 | 25.446 | 55.400 | −57.288 | 1.00 | 32.92 | C |
| ATOM | 7463 | OD1 | ASN | G | 235 | 24.578 | 54.736 | −57.843 | 1.00 | 32.10 | O |
| ATOM | 7464 | ND2 | ASN | G | 235 | 26.738 | 55.095 | −57.382 | 1.00 | 32.83 | N |
| ATOM | 7465 | N | GLU | G | 236 | 22.917 | 57.366 | −58.330 | 1.00 | 35.00 | N |
| ATOM | 7466 | CA | GLU | G | 236 | 22.070 | 57.312 | −59.524 | 1.00 | 35.86 | C |
| ATOM | 7467 | C | GLU | G | 236 | 21.952 | 55.943 | −60.214 | 1.00 | 36.60 | C |
| ATOM | 7468 | O | GLU | G | 236 | 20.968 | 55.684 | −60.910 | 1.00 | 36.50 | O |
| ATOM | 7469 | CB | GLU | G | 236 | 22.558 | 58.340 | −60.557 | 1.00 | 35.14 | C |
| ATOM | 7470 | N | TYR | G | 237 | 22.944 | 55.073 | −60.028 | 1.00 | 36.16 | N |
| ATOM | 7471 | CA | TYR | G | 237 | 22.919 | 53.755 | −60.665 | 1.00 | 36.25 | C |
| ATOM | 7472 | C | TYR | G | 237 | 22.503 | 52.583 | −59.780 | 1.00 | 35.75 | C |
| ATOM | 7473 | O | TYR | G | 237 | 22.574 | 51.436 | −60.215 | 1.00 | 35.24 | O |
| ATOM | 7474 | CB | TYR | G | 237 | 24.284 | 53.425 | −61.279 | 1.00 | 36.51 | C |
| ATOM | 7475 | CG | TYR | G | 237 | 24.811 | 54.520 | −62.154 | 1.00 | 38.18 | C |
| ATOM | 7476 | CD1 | TYR | G | 237 | 25.831 | 55.355 | −61.708 | 1.00 | 38.95 | C |
| ATOM | 7477 | CD2 | TYR | G | 237 | 24.239 | 54.775 | −63.400 | 1.00 | 37.89 | C |
| ATOM | 7478 | CE1 | TYR | G | 237 | 26.270 | 56.421 | −62.478 | 1.00 | 40.57 | C |
| ATOM | 7479 | CE2 | TYR | G | 237 | 24.661 | 55.836 | −64.174 | 1.00 | 39.83 | C |
| ATOM | 7480 | CZ | TYR | G | 237 | 25.680 | 56.663 | −63.705 | 1.00 | 41.20 | C |
| ATOM | 7481 | OH | TYR | G | 237 | 26.095 | 57.745 | −64.450 | 1.00 | 42.74 | O |
| ATOM | 7482 | N | GLY | G | 238 | 22.082 | 52.842 | −58.548 | 1.00 | 34.93 | N |
| ATOM | 7483 | CA | GLY | G | 238 | 21.677 | 51.723 | −57.719 | 1.00 | 34.22 | C |
| ATOM | 7484 | C | GLY | G | 238 | 21.493 | 51.987 | −56.242 | 1.00 | 33.59 | C |
| ATOM | 7485 | O | GLY | G | 238 | 21.898 | 53.026 | −55.719 | 1.00 | 34.04 | O |
| ATOM | 7486 | N | SER | G | 239 | 20.887 | 51.011 | −55.575 | 1.00 | 32.54 | N |
| ATOM | 7487 | CA | SER | G | 239 | 20.616 | 51.076 | −54.146 | 1.00 | 32.28 | C |

TABLE 3-continued

FGFR2(D2–D3) Complexed with FGF2

| ATOM | 7488 | C | SER | G | 239 | 20.735 | 49.675 | −53.544 | 1.00 | 31.72 | C |
|---|---|---|---|---|---|---|---|---|---|---|---|
| ATOM | 7489 | O | SER | G | 239 | 20.105 | 48.735 | −54.029 | 1.00 | 31.16 | O |
| ATOM | 7490 | CB | SER | G | 239 | 19.210 | 51.617 | −53.908 | 1.00 | 32.19 | C |
| ATOM | 7491 | OG | SER | G | 239 | 18.886 | 51.583 | −52.532 | 1.00 | 34.32 | O |
| ATOM | 7492 | N | ILE | G | 240 | 21.551 | 49.538 | −52.498 | 1.00 | 30.28 | N |
| ATOM | 7493 | CA | ILE | G | 240 | 21.747 | 48.247 | −51.835 | 1.00 | 28.68 | C |
| ATOM | 7494 | C | ILE | G | 240 | 21.654 | 48.410 | −50.321 | 1.00 | 28.11 | C |
| ATOM | 7495 | O | ILE | G | 240 | 21.912 | 49.483 | −49.798 | 1.00 | 28.31 | O |
| ATOM | 7496 | CB | ILE | G | 240 | 23.128 | 47.621 | −52.181 | 1.00 | 27.78 | C |
| ATOM | 7497 | CG1 | ILE | G | 240 | 24.268 | 48.533 | −51.702 | 1.00 | 27.45 | C |
| ATOM | 7498 | CG2 | ILE | G | 240 | 23.219 | 47.361 | −53.663 | 1.00 | 26.24 | C |
| ATOM | 7499 | CD1 | ILE | G | 240 | 25.679 | 48.024 | −52.049 | 1.00 | 26.01 | C |
| ATOM | 7500 | N | ASN | G | 241 | 21.279 | 47.343 | −49.623 | 1.00 | 28.01 | N |
| ATOM | 7501 | CA | ASN | G | 241 | 21.152 | 47.393 | −48.170 | 1.00 | 27.97 | C |
| ATOM | 7502 | C | ASN | G | 241 | 21.662 | 46.128 | −47.474 | 1.00 | 27.84 | C |
| ATOM | 7503 | O | ASN | G | 241 | 21.829 | 45.082 | −48.098 | 1.00 | 27.55 | O |
| ATOM | 7504 | CB | ASN | G | 241 | 19.693 | 47.622 | −47.773 | 1.00 | 27.81 | C |
| ATOM | 7505 | CG | ASN | G | 241 | 18.771 | 46.552 | −48.317 | 1.00 | 29.79 | C |
| ATOM | 7506 | OD1 | ASN | G | 241 | 18.122 | 46.736 | −49.362 | 1.00 | 31.16 | O |
| ATOM | 7507 | ND2 | ASN | G | 241 | 18.717 | 45.419 | −47.630 | 1.00 | 28.96 | N |
| ATOM | 7508 | N | HIS | G | 242 | 21.884 | 46.245 | −46.167 | 1.00 | 27.95 | N |
| ATOM | 7509 | CA | HIS | G | 242 | 22.367 | 45.146 | −45.334 | 1.00 | 27.69 | C |
| ATOM | 7510 | C | HIS | G | 242 | 21.748 | 45.312 | −43.949 | 1.00 | 26.95 | C |
| ATOM | 7511 | O | HIS | G | 242 | 21.585 | 46.421 | −43.474 | 1.00 | 26.62 | O |
| ATOM | 7512 | CB | HIS | G | 242 | 23.888 | 45.223 | −45.226 | 1.00 | 28.03 | C |
| ATOM | 7513 | CG | HIS | G | 242 | 24.485 | 44.178 | −44.337 | 1.00 | 29.55 | C |
| ATOM | 7514 | ND1 | HIS | G | 242 | 24.727 | 42.889 | −44.762 | 1.00 | 29.30 | N |
| ATOM | 7515 | CD2 | HIS | G | 242 | 24.886 | 44.231 | −43.043 | 1.00 | 29.73 | C |
| ATOM | 7516 | CE1 | HIS | G | 242 | 25.252 | 42.193 | −43.769 | 1.00 | 29.52 | C |
| ATOM | 7517 | NE2 | HIS | G | 242 | 25.359 | 42.983 | −42.716 | 1.00 | 29.51 | N |
| ATOM | 7518 | N | THR | G | 243 | 21.418 | 44.214 | −43.286 | 1.00 | 27.81 | N |
| ATOM | 7519 | CA | THR | G | 243 | 20.789 | 44.322 | −41.983 | 1.00 | 28.78 | C |
| ATOM | 7520 | C | THR | G | 243 | 21.498 | 43.589 | −40.853 | 1.00 | 29.90 | C |
| ATOM | 7521 | O | THR | G | 243 | 21.907 | 42.432 | −40.994 | 1.00 | 29.15 | O |
| ATOM | 7522 | CB | THR | G | 243 | 19.318 | 43.848 | −42.051 | 1.00 | 29.58 | C |
| ATOM | 7523 | OG1 | THR | G | 243 | 18.584 | 44.714 | −42.931 | 1.00 | 28.66 | O |
| ATOM | 7524 | CG2 | THR | G | 243 | 18.681 | 43.873 | −40.670 | 1.00 | 27.96 | C |
| ATOM | 7525 | N | TYR | G | 244 | 21.639 | 44.300 | −39.736 | 1.00 | 30.30 | N |
| ATOM | 7526 | CA | TYR | G | 244 | 22.269 | 43.789 | −38.530 | 1.00 | 32.40 | C |
| ATOM | 7527 | C | TYR | G | 244 | 21.192 | 43.618 | −37.463 | 1.00 | 34.01 | C |
| ATOM | 7528 | O | TYR | G | 244 | 20.216 | 44.379 | −37.433 | 1.00 | 33.67 | O |
| ATOM | 7529 | CB | TYR | G | 244 | 23.304 | 44.789 | −38.004 | 1.00 | 33.37 | C |
| ATOM | 7530 | CG | TYR | G | 244 | 24.582 | 44.848 | −38.803 | 1.00 | 34.79 | C |
| ATOM | 7531 | CD1 | TYR | G | 244 | 24.986 | 46.029 | −39.422 | 1.00 | 34.97 | C |
| ATOM | 7532 | CD2 | TYR | G | 244 | 25.396 | 43.719 | −38.935 | 1.00 | 34.57 | C |
| ATOM | 7533 | CE1 | TYR | G | 244 | 26.180 | 46.089 | −40.158 | 1.00 | 35.52 | C |
| ATOM | 7534 | CE2 | TYR | G | 244 | 26.584 | 43.764 | −39.661 | 1.00 | 35.11 | C |
| ATOM | 7535 | CZ | TYR | G | 244 | 26.970 | 44.950 | −40.269 | 1.00 | 35.69 | C |
| ATOM | 7536 | OH | TYR | G | 244 | 28.147 | 45.001 | −40.973 | 1.00 | 35.60 | O |
| ATOM | 7537 | N | HIS | G | 245 | 21.376 | 42.635 | −36.590 | 1.00 | 34.92 | N |
| ATOM | 7538 | CA | HIS | G | 245 | 20.442 | 42.396 | −35.491 | 1.00 | 36.03 | C |
| ATOM | 7539 | C | HIS | G | 245 | 21.217 | 42.634 | −34.196 | 1.00 | 35.26 | C |
| ATOM | 7540 | O | HIS | G | 245 | 22.309 | 42.093 | −34.019 | 1.00 | 34.39 | O |
| ATOM | 7541 | CB | HIS | G | 245 | 19.919 | 40.953 | −35.545 | 1.00 | 38.91 | C |
| ATOM | 7542 | CG | HIS | G | 245 | 19.299 | 40.594 | −36.864 | 1.00 | 42.97 | C |
| ATOM | 7543 | ND1 | HIS | G | 245 | 18.057 | 41.050 | −37.249 | 1.00 | 45.08 | N |
| ATOM | 7544 | CD2 | HIS | G | 245 | 19.777 | 39.882 | −37.912 | 1.00 | 44.45 | C |
| ATOM | 7545 | CE1 | HIS | G | 245 | 17.797 | 40.643 | −38.483 | 1.00 | 44.93 | C |
| ATOM | 7546 | NE2 | HIS | G | 245 | 18.831 | 39.935 | −38.908 | 1.00 | 45.92 | N |
| ATOM | 7547 | N | LEU | G | 246 | 20.667 | 43.456 | −33.306 | 1.00 | 34.64 | N |
| ATOM | 7548 | CA | LEU | G | 246 | 21.333 | 43.748 | −32.043 | 1.00 | 34.91 | C |
| ATOM | 7549 | C | LEU | G | 246 | 20.606 | 43.181 | −30.825 | 1.00 | 35.69 | C |
| ATOM | 7550 | O | LEU | G | 246 | 19.384 | 43.278 | −30.713 | 1.00 | 35.58 | O |
| ATOM | 7551 | CB | LEU | G | 246 | 21.494 | 45.260 | −31.862 | 1.00 | 35.44 | C |
| ATOM | 7552 | CG | LEU | G | 246 | 22.063 | 45.734 | −30.517 | 1.00 | 36.47 | C |
| ATOM | 7553 | CD1 | LEU | G | 246 | 23.469 | 45.183 | −30.336 | 1.00 | 36.34 | C |
| ATOM | 7554 | CD2 | LEU | G | 246 | 22.076 | 47.253 | −30.460 | 1.00 | 35.04 | C |
| ATOM | 7555 | N | ASP | G | 247 | 21.369 | 42.587 | −29.913 | 1.00 | 36.18 | N |
| ATOM | 7556 | CA | ASP | G | 247 | 20.816 | 42.051 | −28.681 | 1.00 | 37.30 | C |
| ATOM | 7557 | C | ASP | G | 247 | 21.720 | 42.476 | −27.527 | 1.00 | 37.80 | C |
| ATOM | 7558 | O | ASP | G | 247 | 22.947 | 42.445 | −27.638 | 1.00 | 37.40 | O |
| ATOM | 7559 | CB | ASP | G | 247 | 20.715 | 40.532 | −28.732 | 1.00 | 39.92 | C |
| ATOM | 7560 | CG | ASP | G | 247 | 19.307 | 40.044 | −28.452 | 1.00 | 41.73 | C |
| ATOM | 7561 | OD1 | ASP | G | 247 | 18.633 | 39.593 | −29.404 | 1.00 | 42.63 | O |
| ATOM | 7562 | OD2 | ASP | G | 247 | 18.871 | 40.127 | −27.282 | 1.00 | 42.31 | O |
| ATOM | 7563 | N | VAL | G | 248 | 21.111 | 42.891 | −26.423 | 1.00 | 37.48 | N |
| ATOM | 7564 | CA | VAL | G | 248 | 21.876 | 43.331 | −25.268 | 1.00 | 37.97 | C |

TABLE 3-continued

FGFR2(D2–D3) Complexed with FGF2

| ATOM | 7565 | C | VAL | G | 248 | 21.620 | 42.443 | −24.059 | 1.00 | 38.56 | C |
|---|---|---|---|---|---|---|---|---|---|---|---|
| ATOM | 7566 | O | VAL | G | 248 | 20.473 | 42.099 | −23.762 | 1.00 | 38.74 | O |
| ATOM | 7567 | CB | VAL | G | 248 | 21.530 | 44.796 | −24.904 | 1.00 | 38.63 | C |
| ATOM | 7568 | CG1 | VAL | G | 248 | 22.373 | 45.261 | −23.724 | 1.00 | 37.78 | C |
| ATOM | 7569 | CG2 | VAL | G | 248 | 21.775 | 45.695 | −26.110 | 1.00 | 38.73 | C |
| ATOM | 7570 | N | VAL | G | 249 | 22.696 | 42.078 | −23.364 | 1.00 | 38.33 | N |
| ATOM | 7571 | CA | VAL | G | 249 | 22.595 | 41.228 | −22.186 | 1.00 | 38.35 | C |
| ATOM | 7572 | C | VAL | G | 249 | 23.224 | 41.900 | −20.964 | 1.00 | 38.07 | C |
| ATOM | 7573 | O | VAL | G | 249 | 24.374 | 42.338 | −21.000 | 1.00 | 37.99 | O |
| ATOM | 7574 | CB | VAL | G | 249 | 23.286 | 39.868 | −22.422 | 1.00 | 39.59 | C |
| ATOM | 7575 | CG1 | VAL | G | 249 | 23.101 | 38.982 | −21.209 | 1.00 | 40.52 | C |
| ATOM | 7576 | CG2 | VAL | G | 249 | 22.708 | 39.192 | −23.662 | 1.00 | 39.36 | C |
| ATOM | 7577 | N | GLU | G | 250 | 22.462 | 41.991 | −19.880 | 1.00 | 37.91 | N |
| ATOM | 7578 | CA | GLU | G | 250 | 22.974 | 42.605 | −18.665 | 1.00 | 37.55 | C |
| ATOM | 7579 | C | GLU | G | 250 | 23.748 | 41.569 | −17.876 | 1.00 | 37.14 | C |
| ATOM | 7580 | O | GLU | G | 250 | 23.253 | 40.469 | −17.621 | 1.00 | 36.70 | O |
| ATOM | 7581 | CB | GLU | G | 250 | 21.837 | 43.154 | −17.798 | 1.00 | 39.01 | C |
| ATOM | 7582 | CG | GLU | G | 250 | 21.151 | 44.384 | −18.372 | 1.00 | 41.78 | C |
| ATOM | 7583 | CD | GLU | G | 250 | 19.883 | 44.749 | −17.620 | 1.00 | 43.62 | C |
| ATOM | 7584 | OE1 | GLU | G | 250 | 18.917 | 43.948 | −17.651 | 1.00 | 44.58 | O |
| ATOM | 7585 | OE2 | GLU | G | 250 | 19.858 | 45.831 | −17.000 | 1.00 | 44.67 | O |
| ATOM | 7586 | N | ARG | G | 251 | 24.972 | 41.916 | −17.501 | 1.00 | 35.77 | N |
| ATOM | 7587 | CA | ARG | G | 251 | 25.795 | 41.008 | −16.730 | 1.00 | 35.07 | C |
| ATOM | 7588 | C | ARG | G | 251 | 25.875 | 41.462 | −15.282 | 1.00 | 35.93 | C |
| ATOM | 7589 | O | ARG | G | 251 | 25.762 | 42.656 | −14.981 | 1.00 | 36.05 | O |
| ATOM | 7590 | CB | ARG | G | 251 | 27.218 | 40.907 | −17.314 | 1.00 | 33.17 | C |
| ATOM | 7591 | CG | ARG | G | 251 | 27.311 | 40.440 | −18.771 | 1.00 | 30.95 | C |
| ATOM | 7592 | CD | ARG | G | 251 | 26.466 | 39.204 | −19.068 | 1.00 | 29.63 | C |
| ATOM | 7593 | NE | ARG | G | 251 | 26.826 | 38.035 | −18.268 | 1.00 | 27.31 | N |
| ATOM | 7594 | CZ | ARG | G | 251 | 27.877 | 37.261 | −18.507 | 1.00 | 28.64 | C |
| ATOM | 7595 | NH1 | ARG | G | 251 | 28.683 | 37.530 | −19.528 | 1.00 | 29.00 | N |
| ATOM | 7596 | NH2 | ARG | G | 251 | 28.120 | 36.206 | −17.732 | 1.00 | 28.89 | N |
| ATOM | 7597 | N | SER | G | 252 | 26.071 | 40.477 | −14.404 | 1.00 | 36.15 | N |
| ATOM | 7598 | CA | SER | G | 252 | 26.204 | 40.717 | −12.978 | 1.00 | 36.84 | C |
| ATOM | 7599 | C | SER | G | 252 | 27.497 | 40.097 | −12.438 | 1.00 | 37.21 | C |
| ATOM | 7600 | O | SER | G | 252 | 27.544 | 38.919 | −12.112 | 1.00 | 37.64 | O |
| ATOM | 7601 | CB | SER | G | 252 | 25.020 | 40.122 | −12.217 | 1.00 | 36.67 | C |
| ATOM | 7602 | OG | SER | G | 252 | 25.289 | 40.169 | −10.825 | 1.00 | 38.12 | O |
| ATOM | 7603 | N | PRO | G | 253 | 28.562 | 40.897 | −12.319 | 1.00 | 37.48 | N |
| ATOM | 7604 | CA | PRO | G | 253 | 29.847 | 40.407 | −11.816 | 1.00 | 37.21 | C |
| ATOM | 7605 | C | PRO | G | 253 | 29.925 | 40.268 | −10.288 | 1.00 | 37.55 | C |
| ATOM | 7606 | O | PRO | G | 253 | 30.909 | 40.681 | −9.678 | 1.00 | 37.38 | O |
| ATOM | 7607 | CB | PRO | G | 253 | 30.820 | 41.462 | −12.329 | 1.00 | 37.06 | C |
| ATOM | 7608 | CG | PRO | G | 253 | 30.026 | 42.718 | −12.121 | 1.00 | 37.41 | C |
| ATOM | 7609 | CD | PRO | G | 253 | 28.639 | 42.336 | −12.640 | 1.00 | 37.48 | C |
| ATOM | 7610 | N | HIS | G | 254 | 28.907 | 39.686 | −9.667 | 1.00 | 37.32 | N |
| ATOM | 7611 | CA | HIS | G | 254 | 28.918 | 39.538 | −8.214 | 1.00 | 37.41 | C |
| ATOM | 7612 | C | HIS | G | 254 | 29.057 | 38.081 | −7.782 | 1.00 | 35.91 | C |
| ATOM | 7613 | O | HIS | G | 254 | 28.788 | 37.161 | −8.558 | 1.00 | 34.13 | O |
| ATOM | 7614 | CB | HIS | G | 254 | 27.624 | 40.098 | −7.606 | 1.00 | 39.83 | C |
| ATOM | 7615 | CG | HIS | G | 254 | 27.299 | 41.496 | −8.033 | 1.00 | 43.05 | C |
| ATOM | 7616 | ND1 | HIS | G | 254 | 26.937 | 41.818 | −9.325 | 1.00 | 44.40 | N |
| ATOM | 7617 | CD2 | HIS | G | 254 | 27.256 | 42.655 | −7.332 | 1.00 | 44.17 | C |
| ATOM | 7618 | CE1 | HIS | G | 254 | 26.680 | 43.114 | −9.400 | 1.00 | 44.30 | C |
| ATOM | 7619 | NE2 | HIS | G | 254 | 26.866 | 43.644 | −8.205 | 1.00 | 44.52 | N |
| ATOM | 7620 | N | ARG | G | 255 | 29.493 | 37.874 | −6.544 | 1.00 | 34.42 | N |
| ATOM | 7621 | CA | ARG | G | 255 | 29.588 | 36.515 | −6.015 | 1.00 | 34.16 | C |
| ATOM | 7622 | C | ARG | G | 255 | 28.121 | 36.111 | −5.763 | 1.00 | 32.44 | C |
| ATOM | 7623 | O | ARG | G | 255 | 27.234 | 36.966 | −5.773 | 1.00 | 31.37 | O |
| ATOM | 7624 | CB | ARG | G | 255 | 30.409 | 36.501 | −4.717 | 1.00 | 35.31 | C |
| ATOM | 7625 | CG | ARG | G | 255 | 29.797 | 37.258 | −3.545 | 1.00 | 39.42 | C |
| ATOM | 7626 | CD | ARG | G | 255 | 30.819 | 37.447 | −2.406 | 1.00 | 43.10 | C |
| ATOM | 7627 | NE | ARG | G | 255 | 30.168 | 37.650 | −1.109 | 1.00 | 47.00 | N |
| ATOM | 7628 | CZ | ARG | G | 255 | 29.348 | 38.659 | −0.816 | 1.00 | 47.84 | C |
| ATOM | 7629 | NH1 | ARG | G | 255 | 29.068 | 39.587 | −1.722 | 1.00 | 48.73 | N |
| ATOM | 7630 | NH2 | ARG | G | 255 | 28.776 | 38.722 | −0.379 | 1.00 | 49.38 | N |
| ATOM | 7631 | N | PRO | G | 256 | 27.844 | 34.815 | −5.537 | 1.00 | 31.88 | N |
| ATOM | 7632 | CA | PRO | G | 256 | 26.449 | 34.411 | −5.304 | 1.00 | 31.34 | C |
| ATOM | 7633 | C | PRO | G | 256 | 25.767 | 35.139 | −4.142 | 1.00 | 30.86 | C |
| ATOM | 7634 | O | PRO | G | 256 | 26.384 | 35.404 | −3.113 | 1.00 | 30.32 | O |
| ATOM | 7635 | CB | PRO | G | 256 | 26.559 | 32.906 | −5.026 | 1.00 | 30.69 | C |
| ATOM | 7636 | CG | PRO | G | 256 | 27.860 | 32.509 | −5.643 | 1.00 | 30.92 | C |
| ATOM | 7637 | CD | PRO | G | 256 | 28.749 | 33.677 | −5.306 | 1.00 | 31.69 | C |
| ATOM | 7638 | N | ILE | G | 257 | 24.487 | 35.452 | −4.318 | 1.00 | 30.45 | N |
| ATOM | 7639 | CA | ILE | G | 257 | 23.695 | 36.120 | −3.290 | 1.00 | 31.29 | C |
| ATOM | 7640 | C | ILE | G | 257 | 22.616 | 35.161 | −2.753 | 1.00 | 31.09 | C |
| ATOM | 7641 | O | ILE | G | 257 | 21.915 | 34.514 | −3.529 | 1.00 | 30.89 | O |

TABLE 3-continued

FGFR2(D2–D3) Complexed with FGF2

| ATOM | 7642 | CB | ILE | G | 257 | 23.023 | 37.378 | −3.880 | 1.00 | 33.41 | C |
|---|---|---|---|---|---|---|---|---|---|---|---|
| ATOM | 7643 | CG1 | ILE | G | 257 | 24.071 | 38.488 | −4.033 | 1.00 | 34.71 | C |
| ATOM | 7644 | CG2 | ILE | G | 257 | 21.853 | 37.830 | −3.008 | 1.00 | 33.59 | C |
| ATOM | 7645 | CD1 | ILE | G | 257 | 23.570 | 39.723 | −4.772 | 1.00 | 36.23 | C |
| ATOM | 7646 | N | LEU | G | 258 | 22.496 | 35.044 | −1.434 | 1.00 | 30.76 | N |
| ATOM | 7647 | CA | LEU | G | 258 | 21.473 | 34.171 | −0.853 | 1.00 | 30.21 | C |
| ATOM | 7648 | C | LEU | G | 258 | 20.361 | 34.984 | −0.214 | 1.00 | 30.61 | C |
| ATOM | 7649 | O | LEU | G | 258 | 20.577 | 36.106 | 0.249 | 1.00 | 30.83 | O |
| ATOM | 7650 | CB | LEU | G | 258 | 22.045 | 33.250 | 0.226 | 1.00 | 29.39 | C |
| ATOM | 7651 | CG | LEU | G | 258 | 23.313 | 32.433 | 0.000 | 1.00 | 30.50 | C |
| ATOM | 7652 | CD1 | LEU | G | 258 | 23.439 | 31.416 | 1.128 | 1.00 | 29.89 | C |
| ATOM | 7653 | CD2 | LEU | G | 258 | 23.274 | 31.740 | −1.323 | 1.00 | 31.22 | C |
| ATOM | 7654 | N | GLN | G | 259 | 19.169 | 34.400 | −0.176 | 1.00 | 30.63 | N |
| ATOM | 7655 | CA | GLN | G | 259 | 18.007 | 35.044 | 0.430 | 1.00 | 30.35 | C |
| ATOM | 7656 | C | GLN | G | 259 | 18.169 | 35.089 | 1.957 | 1.00 | 29.51 | C |
| ATOM | 7657 | O | GLN | G | 259 | 18.481 | 34.082 | 2.585 | 1.00 | 28.56 | O |
| ATOM | 7658 | CB | GLN | G | 259 | 16.742 | 34.248 | 0.056 | 1.00 | 30.66 | C |
| ATOM | 7659 | CG | GLN | G | 259 | 15.410 | 34.765 | 0.645 | 1.00 | 31.63 | C |
| ATOM | 7660 | CD | GLN | G | 259 | 14.201 | 33.887 | 0.256 | 1.00 | 32.94 | C |
| ATOM | 7661 | OE1 | GLN | G | 259 | 14.012 | 33.548 | −0.915 | 1.00 | 30.95 | O |
| ATOM | 7662 | NE2 | GLN | G | 259 | 13.380 | 33.529 | 1.245 | 1.00 | 32.93 | N |
| ATOM | 7663 | N | ALA | G | 260 | 17.941 | 36.258 | 2.545 | 1.00 | 29.30 | N |
| ATOM | 7664 | CA | ALA | G | 260 | 18.036 | 36.430 | 3.992 | 1.00 | 30.20 | C |
| ATOM | 7665 | C | ALA | G | 260 | 17.020 | 35.540 | 4.715 | 1.00 | 30.29 | C |
| ATOM | 7666 | O | ALA | G | 260 | 15.900 | 35.402 | 4.261 | 1.00 | 30.30 | O |
| ATOM | 7667 | CB | ALA | G | 260 | 17.772 | 37.890 | 4.344 | 1.00 | 29.19 | C |
| ATOM | 7668 | N | GLY | G | 261 | 17.410 | 34.944 | 5.838 | 1.00 | 30.71 | N |
| ATOM | 7669 | CA | GLY | G | 261 | 16.485 | 34.103 | 6.580 | 1.00 | 31.64 | C |
| ATOM | 7670 | C | GLY | G | 261 | 16.518 | 32.621 | 6.241 | 1.00 | 32.25 | C |
| ATOM | 7671 | O | GLY | G | 261 | 15.954 | 31.802 | 6.970 | 1.00 | 32.41 | O |
| ATOM | 7672 | N | LEU | G | 262 | 17.179 | 32.267 | 5.144 | 1.00 | 32.52 | N |
| ATOM | 7673 | CA | LEU | G | 262 | 17.267 | 30.871 | 4.733 | 1.00 | 32.03 | C |
| ATOM | 7674 | C | LEU | G | 262 | 18.710 | 30.396 | 4.629 | 1.00 | 32.97 | C |
| ATOM | 7675 | O | LEU | G | 262 | 19.570 | 31.082 | 4.067 | 1.00 | 32.65 | O |
| ATOM | 7676 | CB | LEU | G | 262 | 16.563 | 30.672 | 3.387 | 1.00 | 31.14 | C |
| ATOM | 7677 | CG | LEU | G | 262 | 15.043 | 30.883 | 3.387 | 1.00 | 31.83 | C |
| ATOM | 7678 | CD1 | LEU | G | 262 | 14.494 | 30.812 | 1.956 | 1.00 | 29.95 | C |
| ATOM | 7679 | CD2 | LEU | G | 262 | 14.391 | 29.819 | 4.274 | 1.00 | 30.39 | C |
| ATOM | 7680 | N | PRO | G | 263 | 18.996 | 29.203 | 5.159 | 1.00 | 33.16 | N |
| ATOM | 7681 | CA | PRO | G | 263 | 18.042 | 28.315 | 5.835 | 1.00 | 34.27 | C |
| ATOM | 7682 | C | PRO | G | 263 | 17.585 | 28.826 | 7.205 | 1.00 | 34.96 | C |
| ATOM | 7683 | O | PRO | G | 263 | 18.212 | 29.698 | 7.802 | 1.00 | 35.11 | O |
| ATOM | 7684 | CB | PRO | G | 263 | 18.812 | 26.999 | 5.920 | 1.00 | 33.84 | C |
| ATOM | 7685 | CG | PRO | G | 263 | 20.232 | 27.461 | 6.068 | 1.00 | 33.03 | C |
| ATOM | 7686 | CD | PRO | G | 263 | 20.318 | 28.568 | 5.048 | 1.00 | 33.06 | C |
| ATOM | 7687 | N | ALA | G | 264 | 16.480 | 28.281 | 7.698 | 1.00 | 36.21 | N |
| ATOM | 7688 | CA | ALA | G | 264 | 15.943 | 28.691 | 8.989 | 1.00 | 37.11 | C |
| ATOM | 7689 | C | ALA | G | 264 | 16.253 | 27.668 | 10.069 | 1.00 | 37.99 | C |
| ATOM | 7690 | O | ALA | G | 264 | 16.396 | 26.480 | 9.782 | 1.00 | 37.70 | O |
| ATOM | 7691 | CB | ALA | G | 264 | 14.452 | 28.878 | 8.884 | 1.00 | 36.73 | C |
| ATOM | 7692 | N | ASN | G | 265 | 16.376 | 28.133 | 11.308 | 1.00 | 38.67 | N |
| ATOM | 7693 | CA | ASN | G | 265 | 16.628 | 27.231 | 12.420 | 1.00 | 39.92 | C |
| ATOM | 7694 | C | ASN | G | 265 | 15.461 | 26.251 | 12.498 | 1.00 | 41.13 | C |
| ATOM | 7695 | O | ASN | G | 265 | 14.341 | 26.565 | 12.087 | 1.00 | 40.63 | O |
| ATOM | 7696 | CB | ASN | G | 265 | 16.722 | 27.992 | 13.745 | 1.00 | 38.98 | C |
| ATOM | 7697 | CG | ASN | G | 265 | 17.911 | 28.931 | 13.802 | 1.00 | 39.26 | C |
| ATOM | 7698 | OD1 | ASN | G | 265 | 19.043 | 28.545 | 13.504 | 1.00 | 37.60 | O |
| ATOM | 7699 | ND2 | ASN | G | 265 | 17.660 | 30.173 | 14.199 | 1.00 | 39.35 | N |
| ATOM | 7700 | N | ALA | G | 266 | 15.731 | 25.063 | 13.019 | 1.00 | 42.71 | N |
| ATOM | 7701 | CA | ALA | G | 266 | 14.699 | 24.046 | 13.150 | 1.00 | 44.36 | C |
| ATOM | 7702 | C | ALA | G | 266 | 14.875 | 23.271 | 14.449 | 1.00 | 45.34 | C |
| ATOM | 7703 | O | ALA | G | 266 | 15.987 | 23.126 | 14.966 | 1.00 | 45.07 | O |
| ATOM | 7704 | CB | ALA | G | 266 | 14.737 | 23.100 | 11.955 | 1.00 | 44.26 | C |
| ATOM | 7705 | N | SER | G | 267 | 13.760 | 22.783 | 14.977 | 1.00 | 46.57 | N |
| ATOM | 7706 | CA | SER | G | 267 | 13.777 | 22.033 | 16.218 | 1.00 | 47.52 | C |
| ATOM | 7707 | C | SER | G | 267 | 12.839 | 20.837 | 16.111 | 1.00 | 47.89 | C |
| ATOM | 7708 | O | SER | G | 267 | 11.818 | 20.890 | 15.416 | 1.00 | 47.62 | O |
| ATOM | 7709 | CB | SER | G | 267 | 13.355 | 22.953 | 17.365 | 1.00 | 47.81 | C |
| ATOM | 7710 | OG | SER | G | 267 | 13.657 | 22.380 | 18.623 | 1.00 | 50.08 | O |
| ATOM | 7711 | N | THR | G | 268 | 13.187 | 19.766 | 16.815 | 1.00 | 47.83 | N |
| ATOM | 7712 | CA | THR | G | 268 | 12.378 | 18.555 | 16.799 | 1.00 | 48.09 | C |
| ATOM | 7713 | C | THR | G | 268 | 12.770 | 17.581 | 17.902 | 1.00 | 48.10 | C |
| ATOM | 7714 | O | THR | G | 268 | 13.812 | 17.728 | 18.546 | 1.00 | 48.04 | O |
| ATOM | 7715 | CB | THR | G | 268 | 12.498 | 17.821 | 15.439 | 1.00 | 48.25 | C |
| ATOM | 7716 | OG1 | THR | G | 268 | 11.534 | 16.765 | 15.384 | 1.00 | 49.55 | O |
| ATOM | 7717 | CG2 | THR | G | 268 | 13.892 | 17.228 | 15.264 | 1.00 | 47.43 | C |
| ATOM | 7718 | N | VAL | G | 269 | 11.916 | 16.587 | 18.117 | 1.00 | 48.14 | N |

TABLE 3-continued

| | | | | FGFR2(D2–D3) Complexed with FGF2 | | | | | | | |
|---|---|---|---|---|---|---|---|---|---|---|---|
| ATOM | 7719 | CA | VAL | G | 269 | 12.168 | 15.558 | 19.117 | 1.00 | 47.99 | C |
| ATOM | 7720 | C | VAL | G | 269 | 12.913 | 14.430 | 18.408 | 1.00 | 48.08 | C |
| ATOM | 7721 | O | VAL | G | 269 | 12.789 | 14.276 | 17.191 | 1.00 | 47.63 | O |
| ATOM | 7722 | CB | VAL | G | 269 | 10.843 | 15.000 | 19.699 | 1.00 | 48.00 | C |
| ATOM | 7723 | CG1 | VAL | G | 269 | 10.074 | 16.103 | 20.404 | 1.00 | 48.03 | C |
| ATOM | 7724 | CG2 | VAL | G | 269 | 10.000 | 14.402 | 18.590 | 1.00 | 47.84 | C |
| ATOM | 7725 | N | VAL | G | 270 | 13.692 | 13.658 | 19.160 | 1.00 | 48.46 | N |
| ATOM | 7726 | CA | VAL | G | 270 | 14.439 | 12.537 | 18.589 | 1.00 | 49.38 | C |
| ATOM | 7727 | C | VAL | G | 270 | 13.463 | 11.695 | 17.768 | 1.00 | 49.64 | C |
| ATOM | 7728 | O | VAL | G | 270 | 12.339 | 11.449 | 18.205 | 1.00 | 49.06 | O |
| ATOM | 7729 | CB | VAL | G | 270 | 15.051 | 11.647 | 19.703 | 1.00 | 49.87 | C |
| ATOM | 7730 | CG1 | VAL | G | 270 | 15.969 | 10.597 | 19.103 | 1.00 | 50.47 | C |
| ATOM | 7731 | CG2 | VAL | G | 270 | 15.809 | 12.499 | 20.683 | 1.00 | 50.03 | C |
| ATOM | 7732 | N | GLY | G | 271 | 13.883 | 11.274 | 16.579 | 1.00 | 50.39 | N |
| ATOM | 7733 | CA | GLY | G | 271 | 13.014 | 10.468 | 15.741 | 1.00 | 51.54 | C |
| ATOM | 7734 | C | GLY | G | 271 | 12.218 | 11.253 | 14.707 | 1.00 | 52.36 | C |
| ATOM | 7735 | O | GLY | G | 271 | 11.567 | 10.661 | 13.843 | 1.00 | 53.06 | O |
| ATOM | 7736 | N | GLY | G | 272 | 12.269 | 12.582 | 14.781 | 1.00 | 52.39 | N |
| ATOM | 7737 | CA | GLY | G | 272 | 11.535 | 13.405 | 13.828 | 1.00 | 52.21 | C |
| ATOM | 7738 | C | GLY | G | 272 | 12.212 | 13.623 | 12.479 | 1.00 | 51.67 | C |
| ATOM | 7739 | O | GLY | G | 272 | 13.307 | 13.113 | 12.227 | 1.00 | 51.44 | O |
| ATOM | 7740 | N | ASP | G | 273 | 11.544 | 14.377 | 11.608 | 1.00 | 51.20 | N |
| ATOM | 7741 | CA | ASP | G | 273 | 12.050 | 14.697 | 10.275 | 1.00 | 51.38 | C |
| ATOM | 7742 | C | ASP | G | 273 | 12.204 | 16.219 | 10.132 | 1.00 | 51.14 | C |
| ATOM | 7743 | O | ASP | G | 273 | 11.428 | 16.988 | 10.708 | 1.00 | 51.64 | O |
| ATOM | 7744 | CB | ASP | G | 273 | 11.080 | 14.169 | 9.213 | 1.00 | 51.73 | C |
| ATOM | 7745 | N | VAL | G | 274 | 13.193 | 16.658 | 9.357 | 1.00 | 49.98 | N |
| ATOM | 7746 | CA | VAL | G | 274 | 13.422 | 18.088 | 9.182 | 1.00 | 48.38 | C |
| ATOM | 7747 | C | VAL | G | 274 | 14.020 | 18.447 | 7.817 | 1.00 | 47.58 | C |
| ATOM | 7748 | O | VAL | G | 274 | 14.531 | 17.584 | 7.098 | 1.00 | 47.16 | O |
| ATOM | 7749 | CB | VAL | G | 274 | 14.347 | 18.616 | 10.319 | 1.00 | 48.53 | C |
| ATOM | 7750 | CG1 | VAL | G | 274 | 15.745 | 18.033 | 10.179 | 1.00 | 47.61 | C |
| ATOM | 7751 | CG2 | VAL | G | 274 | 14.386 | 20.124 | 10.309 | 1.00 | 49.38 | C |
| ATOM | 7752 | N | GLU | G | 275 | 13.936 | 19.725 | 7.460 | 1.00 | 45.89 | N |
| ATOM | 7753 | CA | GLU | G | 275 | 14.483 | 20.203 | 6.199 | 1.00 | 44.90 | C |
| ATOM | 7754 | C | GLU | G | 275 | 15.115 | 21.587 | 6.350 | 1.00 | 43.37 | C |
| ATOM | 7755 | O | GLU | G | 275 | 14.771 | 22.348 | 7.256 | 1.00 | 42.50 | O |
| ATOM | 7756 | CB | GLU | G | 275 | 13.389 | 20.277 | 5.133 | 1.00 | 45.32 | C |
| ATOM | 7757 | CG | GLU | G | 275 | 12.250 | 21.234 | 5.466 | 1.00 | 46.56 | C |
| ATOM | 7758 | CD | GLU | G | 275 | 11.430 | 21.615 | 4.237 | 1.00 | 47.38 | C |
| ATOM | 7759 | OE1 | GLU | G | 275 | 11.349 | 20.793 | 3.306 | 1.00 | 47.81 | O |
| ATOM | 7760 | OE2 | GLU | G | 275 | 10.860 | 22.732 | 4.204 | 1.00 | 47.98 | O |
| ATOM | 7761 | N | PHE | G | 276 | 16.045 | 21.895 | 5.455 | 1.00 | 41.29 | N |
| ATOM | 7762 | CA | PHE | G | 276 | 16.721 | 23.183 | 5.436 | 1.00 | 38.87 | C |
| ATOM | 7763 | C | PHE | G | 276 | 16.654 | 23.656 | 3.997 | 1.00 | 38.05 | C |
| ATOM | 7764 | O | PHE | G | 276 | 17.060 | 22.945 | 3.082 | 1.00 | 36.88 | O |
| ATOM | 7765 | CB | PHE | G | 276 | 18.174 | 23.038 | 5.889 | 1.00 | 37.78 | C |
| ATOM | 7766 | CG | PHE | G | 276 | 18.322 | 22.791 | 7.361 | 1.00 | 37.18 | C |
| ATOM | 7767 | CD1 | PHE | G | 276 | 17.937 | 23.761 | 8.283 | 1.00 | 36.53 | C |
| ATOM | 7768 | CD2 | PHE | G | 276 | 18.831 | 21.583 | 7.830 | 1.00 | 37.14 | C |
| ATOM | 7769 | CE1 | PHE | G | 276 | 18.057 | 23.531 | 9.652 | 1.00 | 36.90 | C |
| ATOM | 7770 | CE2 | PHE | G | 276 | 18.955 | 21.340 | 9.201 | 1.00 | 36.45 | C |
| ATOM | 7771 | CZ | PHE | G | 276 | 18.569 | 22.312 | 10.114 | 1.00 | 36.22 | C |
| ATOM | 7772 | N | VAL | G | 277 | 16.124 | 24.855 | 3.806 | 1.00 | 36.92 | N |
| ATOM | 7773 | CA | VAL | G | 277 | 15.967 | 25.413 | 2.482 | 1.00 | 36.11 | C |
| ATOM | 7774 | C | VAL | G | 277 | 16.952 | 26.540 | 2.235 | 1.00 | 35.68 | C |
| ATOM | 7775 | O | VAL | G | 277 | 17.307 | 27.287 | 3.144 | 1.00 | 36.03 | O |
| ATOM | 7776 | CB | VAL | G | 277 | 14.533 | 25.961 | 2.300 | 1.00 | 36.01 | C |
| ATOM | 7777 | CG1 | VAL | G | 277 | 14.322 | 26.425 | 0.861 | 1.00 | 34.54 | C |
| ATOM | 7778 | CG2 | VAL | G | 277 | 13.526 | 24.890 | 2.684 | 1.00 | 35.65 | C |
| ATOM | 7779 | N | CYS | G | 278 | 17.376 | 26.666 | 0.989 | 1.00 | 35.24 | N |
| ATOM | 7780 | CA | CYS | G | 278 | 18.304 | 27.710 | 0.605 | 1.00 | 35.03 | C |
| ATOM | 7781 | C | CYS | G | 278 | 17.871 | 28.279 | −0.743 | 1.00 | 34.25 | C |
| ATOM | 7782 | O | CYS | G | 278 | 17.392 | 27.535 | −1.596 | 1.00 | 34.32 | O |
| ATOM | 7783 | CB | CYS | G | 278 | 19.711 | 27.126 | 0.499 | 1.00 | 34.63 | C |
| ATOM | 7784 | SG | CYS | G | 278 | 20.943 | 28.361 | 0.107 | 1.00 | 37.73 | S |
| ATOM | 7785 | N | LYS | G | 279 | 18.032 | 29.585 | −0.934 | 1.00 | 33.28 | N |
| ATOM | 7786 | CA | LYS | G | 279 | 17.663 | 30.229 | −2.199 | 1.00 | 32.54 | C |
| ATOM | 7787 | C | LYS | G | 279 | 18.828 | 31.074 | −2.750 | 1.00 | 31.77 | C |
| ATOM | 7788 | O | LYS | G | 279 | 19.179 | 32.127 | −2.198 | 1.00 | 31.51 | O |
| ATOM | 7789 | CB | LYS | G | 279 | 16.410 | 31.088 | −2.007 | 1.00 | 32.60 | C |
| ATOM | 7790 | CG | LYS | G | 279 | 15.881 | 31.721 | −3.289 | 1.00 | 32.83 | C |
| ATOM | 7791 | CD | LYS | G | 279 | 15.501 | 30.677 | −4.328 | 1.00 | 33.81 | C |
| ATOM | 7792 | CE | LYS | G | 279 | 15.072 | 31.338 | −5.656 | 1.00 | 34.37 | C |
| ATOM | 7793 | NZ | LYS | G | 279 | 15.047 | 30.360 | −6.799 | 1.00 | 33.91 | N |
| ATOM | 7794 | N | VAL | G | 280 | 19.402 | 30.602 | −3.851 | 1.00 | 30.58 | N |
| ATOM | 7795 | CA | VAL | G | 280 | 20.551 | 31.229 | −4.495 | 1.00 | 30.54 | C |

TABLE 3-continued

| FGFR2(D2–D3) Complexed with FGF2 | | | | | | | | | | | |
|---|---|---|---|---|---|---|---|---|---|---|---|
| ATOM | 7796 | C | VAL | G | 280 | 20.312 | 31.988 | −5.819 | 1.00 | 30.94 | C |
| ATOM | 7797 | O | VAL | G | 280 | 19.504 | 31.573 | −6.653 | 1.00 | 31.37 | O |
| ATOM | 7798 | CB | VAL | G | 280 | 21.629 | 30.144 | −4.764 | 1.00 | 30.35 | C |
| ATOM | 7799 | CG1 | VAL | G | 280 | 22.840 | 30.753 | −5.462 | 1.00 | 28.62 | C |
| ATOM | 7800 | CG2 | VAL | G | 280 | 22.024 | 29.465 | −3.441 | 1.00 | 28.95 | C |
| ATOM | 7801 | N | TYR | G | 281 | 21.039 | 33.091 | −5.994 | 1.00 | 30.49 | N |
| ATOM | 7802 | CA | TYR | G | 281 | 20.996 | 33.904 | −7.212 | 1.00 | 30.69 | C |
| ATOM | 7803 | C | TYR | G | 281 | 22.451 | 34.164 | −7.679 | 1.00 | 29.61 | C |
| ATOM | 7804 | O | TYR | G | 281 | 23.311 | 34.519 | −6.876 | 1.00 | 28.43 | O |
| ATOM | 7805 | CB | TYR | G | 281 | 20.301 | 35.261 | −6.965 | 1.00 | 32.89 | C |
| ATOM | 7806 | CG | TYR | G | 281 | 18.838 | 35.163 | −6.557 | 1.00 | 34.84 | C |
| ATOM | 7807 | CD1 | TYR | G | 281 | 18.475 | 35.110 | −5.210 | 1.00 | 34.37 | C |
| ATOM | 7808 | CD2 | TYR | G | 281 | 17.825 | 35.046 | −7.523 | 1.00 | 35.01 | C |
| ATOM | 7809 | CE1 | TYR | G | 281 | 17.155 | 34.933 | −4.823 | 1.00 | 35.59 | C |
| ATOM | 7810 | CE2 | TYR | G | 281 | 16.485 | 34.863 | −7.142 | 1.00 | 36.56 | C |
| ATOM | 7811 | CZ | TYR | G | 281 | 16.164 | 34.806 | −5.785 | 1.00 | 36.55 | C |
| ATOM | 7812 | OH | TYR | G | 281 | 14.866 | 34.587 | −5.379 | 1.00 | 37.46 | O |
| ATOM | 7813 | N | SER | G | 282 | 22.717 | 33.977 | −8.969 | 1.00 | 29.00 | N |
| ATOM | 7814 | CA | SER | G | 282 | 24.051 | 34.202 | −9.526 | 1.00 | 29.05 | C |
| ATOM | 7815 | C | SER | G | 282 | 24.029 | 34.209 | −11.056 | 1.00 | 29.48 | C |
| ATOM | 7816 | O | SER | G | 282 | 23.231 | 33.512 | −11.680 | 1.00 | 29.98 | O |
| ATOM | 7817 | CB | SER | G | 282 | 25.036 | 33.123 | −9.036 | 1.00 | 29.21 | C |
| ATOM | 7818 | OG | SER | G | 282 | 26.365 | 33.368 | −9.502 | 1.00 | 27.34 | O |
| ATOM | 7819 | N | ASP | G | 283 | 24.909 | 35.005 | −11.647 | 1.00 | 29.24 | N |
| ATOM | 7820 | CA | ASP | G | 283 | 25.040 | 35.106 | −13.095 | 1.00 | 29.48 | C |
| ATOM | 7821 | C | ASP | G | 283 | 26.001 | 33.974 | −13.493 | 1.00 | 29.82 | C |
| ATOM | 7822 | O | ASP | G | 283 | 25.638 | 33.038 | −14.209 | 1.00 | 30.25 | O |
| ATOM | 7823 | CB | ASP | G | 283 | 25.625 | 36.484 | −13.436 | 1.00 | 30.69 | C |
| ATOM | 7824 | CG | ASP | G | 283 | 25.872 | 36.673 | −14.918 | 1.00 | 32.09 | C |
| ATOM | 7825 | OD1 | ASP | G | 283 | 26.122 | 37.829 | −15.329 | 1.00 | 31.64 | O |
| ATOM | 7826 | OD2 | ASP | G | 283 | 25.829 | 35.677 | −15.670 | 1.00 | 32.66 | O |
| ATOM | 7827 | N | ALA | G | 284 | 27.231 | 34.072 | −13.011 | 1.00 | 28.90 | N |
| ATOM | 7828 | CA | ALA | G | 284 | 28.228 | 33.049 | −13.264 | 1.00 | 29.34 | C |
| ATOM | 7829 | C | ALA | G | 284 | 27.691 | 31.796 | −12.571 | 1.00 | 29.13 | C |
| ATOM | 7830 | O | ALA | G | 284 | 27.174 | 31.878 | −11.460 | 1.00 | 29.66 | O |
| ATOM | 7831 | CB | ALA | G | 284 | 29.573 | 33.464 | −12.641 | 1.00 | 29.05 | C |
| ATOM | 7832 | N | GLN | G | 285 | 27.809 | 30.649 | −13.224 | 1.00 | 28.43 | N |
| ATOM | 7833 | CA | GLN | G | 285 | 27.326 | 29.393 | −12.668 | 1.00 | 28.02 | C |
| ATOM | 7834 | C | GLN | G | 285 | 27.783 | 29.198 | −11.216 | 1.00 | 27.99 | C |
| ATOM | 7835 | O | GLN | G | 285 | 28.985 | 29.185 | −10.936 | 1.00 | 27.38 | O |
| ATOM | 7836 | CB | GLN | G | 285 | 27.857 | 28.239 | −13.518 | 1.00 | 27.67 | C |
| ATOM | 7837 | CG | GLN | G | 285 | 26.911 | 27.072 | −13.569 | 1.00 | 27.62 | C |
| ATOM | 7838 | CD | GLN | G | 285 | 25.564 | 27.477 | −14.144 | 1.00 | 27.85 | C |
| ATOM | 7839 | OE1 | GLN | G | 285 | 24.538 | 26.853 | −13.851 | 1.00 | 27.45 | O |
| ATOM | 7840 | NE2 | GLN | G | 285 | 25.562 | 28.519 | −14.975 | 1.00 | 25.85 | N |
| ATOM | 7841 | N | PRO | G | 286 | 26.839 | 29.047 | −10.270 | 1.00 | 27.55 | N |
| ATOM | 7842 | CA | PRO | G | 286 | 27.209 | 28.853 | −8.865 | 1.00 | 27.38 | C |
| ATOM | 7843 | C | PRO | G | 286 | 27.281 | 27.368 | −8.474 | 1.00 | 28.25 | C |
| ATOM | 7844 | O | PRO | G | 286 | 26.605 | 26.523 | −9.069 | 1.00 | 28.01 | O |
| ATOM | 7845 | CB | PRO | G | 286 | 26.096 | 29.563 | −8.129 | 1.00 | 27.57 | C |
| ATOM | 7846 | CG | PRO | G | 286 | 24.902 | 29.135 | −8.945 | 1.00 | 28.55 | C |
| ATOM | 7847 | CD | PRO | G | 286 | 25.402 | 29.355 | −10.382 | 1.00 | 28.43 | C |
| ATOM | 7848 | N | HIS | G | 287 | 28.105 | 27.065 | −7.476 | 1.00 | 28.63 | N |
| ATOM | 7849 | CA | HIS | G | 287 | 28.255 | 25.700 | −6.980 | 1.00 | 29.45 | C |
| ATOM | 7850 | C | HIS | G | 287 | 27.755 | 25.668 | −5.544 | 1.00 | 29.49 | C |
| ATOM | 7851 | O | HIS | G | 287 | 28.299 | 26.330 | −4.667 | 1.00 | 28.79 | O |
| ATOM | 7852 | CB | HIS | G | 287 | 29.712 | 25.238 | −7.034 | 1.00 | 29.44 | C |
| ATOM | 7853 | CG | HIS | G | 287 | 29.896 | 23.844 | −6.533 | 1.00 | 30.98 | C |
| ATOM | 7854 | ND1 | HIS | G | 287 | 30.438 | 23.563 | −5.299 | 1.00 | 31.86 | N |
| ATOM | 7855 | CD2 | HIS | G | 287 | 29.527 | 22.652 | −7.062 | 1.00 | 31.38 | C |
| ATOM | 7856 | CE1 | HIS | G | 287 | 30.391 | 22.258 | −5.088 | 1.00 | 32.41 | C |
| ATOM | 7857 | NE2 | HIS | G | 287 | 29.840 | 21.684 | −6.142 | 1.00 | 31.49 | N |
| ATOM | 7858 | N | ILE | G | 288 | 26.711 | 24.881 | −5.322 | 1.00 | 29.94 | N |
| ATOM | 7859 | CA | ILE | G | 288 | 26.064 | 24.781 | −4.029 | 1.00 | 30.32 | C |
| ATOM | 7860 | C | ILE | G | 288 | 26.328 | 23.478 | −3.266 | 1.00 | 31.50 | C |
| ATOM | 7861 | O | ILE | G | 288 | 26.301 | 22.385 | −3.843 | 1.00 | 31.99 | O |
| ATOM | 7862 | CB | ILE | G | 288 | 24.545 | 24.944 | −4.230 | 1.00 | 29.55 | C |
| ATOM | 7863 | CG1 | ILE | G | 288 | 24.280 | 26.221 | −5.043 | 1.00 | 31.03 | C |
| ATOM | 7864 | CG2 | ILE | G | 288 | 23.845 | 24.967 | −2.899 | 1.00 | 30.04 | C |
| ATOM | 7865 | CD1 | ILE | G | 288 | 22.817 | 26.443 | −5.448 | 1.00 | 30.30 | C |
| ATOM | 7866 | N | GLN | G | 289 | 26.577 | 23.594 | −1.967 | 1.00 | 32.07 | N |
| ATOM | 7867 | CA | GLN | G | 289 | 26.793 | 22.420 | −1.131 | 1.00 | 33.10 | C |
| ATOM | 7868 | C | GLN | G | 289 | 26.274 | 22.691 | 0.276 | 1.00 | 32.96 | C |
| ATOM | 7869 | O | GLN | G | 289 | 26.144 | 23.846 | 0.688 | 1.00 | 32.94 | O |
| ATOM | 7870 | CB | GLN | G | 289 | 28.276 | 22.047 | −1.079 | 1.00 | 33.70 | C |
| ATOM | 7871 | CG | GLN | G | 289 | 29.190 | 23.136 | −0.572 | 1.00 | 34.69 | C |
| ATOM | 7872 | CD | GLN | G | 289 | 30.652 | 22.724 | −0.607 | 1.00 | 35.78 | C |

TABLE 3-continued

FGFR2(D2–D3) Complexed with FGF2

| ATOM | 7873 | OE1 | GLN | G | 289 | 31.045 | 21.754 | 0.034 | 1.00 | 36.22 | O |
|---|---|---|---|---|---|---|---|---|---|---|---|
| ATOM | 7874 | NE2 | GLN | G | 289 | 31.465 | 23.461 | −1.360 | 1.00 | 36.39 | N |
| ATOM | 7875 | N | TRP | G | 290 | 25.951 | 21.618 | 0.993 | 1.00 | 32.34 | N |
| ATOM | 7876 | CA | TRP | G | 290 | 25.460 | 21.719 | 2.359 | 1.00 | 32.63 | C |
| ATOM | 7877 | C | TRP | G | 290 | 26.526 | 21.162 | 3.292 | 1.00 | 34.01 | C |
| ATOM | 7878 | O | TRP | G | 290 | 27.037 | 20.062 | 3.073 | 1.00 | 33.74 | O |
| ATOM | 7879 | CB | TRP | G | 290 | 24.157 | 20.936 | 2.536 | 1.00 | 29.96 | C |
| ATOM | 7880 | CG | TRP | G | 290 | 22.947 | 21.591 | 1.917 | 1.00 | 27.97 | C |
| ATOM | 7881 | CD1 | TRP | G | 290 | 22.447 | 21.367 | 0.673 | 1.00 | 27.32 | C |
| ATOM | 7882 | CD2 | TRP | G | 290 | 22.077 | 22.554 | 2.533 | 1.00 | 26.53 | C |
| ATOM | 7883 | NE1 | TRP | G | 290 | 21.313 | 22.122 | 0.470 | 1.00 | 27.22 | N |
| ATOM | 7884 | CE2 | TRP | G | 290 | 21.064 | 22.862 | 1.596 | 1.00 | 27.22 | C |
| ATOM | 7885 | CE3 | TRP | G | 290 | 22.053 | 23.185 | 3.783 | 1.00 | 25.74 | C |
| ATOM | 7886 | CZ2 | TRP | G | 290 | 20.031 | 23.775 | 1.873 | 1.00 | 25.60 | C |
| ATOM | 7887 | CZ3 | TRP | G | 290 | 21.030 | 24.091 | 4.057 | 1.00 | 26.27 | C |
| ATOM | 7888 | CH2 | TRP | G | 290 | 20.032 | 24.376 | 3.104 | 1.00 | 24.97 | C |
| ATOM | 7889 | N | ILE | G | 291 | 26.847 | 21.921 | 4.335 | 1.00 | 36.02 | N |
| ATOM | 7890 | CA | ILE | G | 291 | 27.879 | 21.533 | 5.289 | 1.00 | 39.06 | C |
| ATOM | 7891 | C | ILE | G | 291 | 27.419 | 21.474 | 6.745 | 1.00 | 40.67 | C |
| ATOM | 7892 | O | ILE | G | 291 | 26.645 | 22.310 | 7.203 | 1.00 | 40.96 | O |
| ATOM | 7893 | CB | ILE | G | 291 | 29.065 | 22.517 | 5.242 | 1.00 | 38.79 | C |
| ATOM | 7894 | CG1 | ILE | G | 291 | 29.506 | 22.748 | 3.796 | 1.00 | 40.06 | C |
| ATOM | 7895 | CG2 | ILE | G | 291 | 30.209 | 21.977 | 6.079 | 1.00 | 39.37 | C |
| ATOM | 7896 | CD1 | ILE | G | 291 | 30.620 | 23.789 | 3.648 | 1.00 | 40.28 | C |
| ATOM | 7897 | N | LYS | G | 292 | 27.920 | 20.483 | 7.471 | 1.00 | 42.52 | N |
| ATOM | 7898 | CA | LYS | G | 292 | 27.612 | 20.323 | 8.890 | 1.00 | 43.88 | C |
| ATOM | 7899 | C | LYS | G | 292 | 28.903 | 20.642 | 9.645 | 1.00 | 45.12 | C |
| ATOM | 7900 | O | LYS | G | 292 | 29.974 | 20.147 | 9.278 | 1.00 | 44.35 | O |
| ATOM | 7901 | CB | LYS | G | 292 | 27.197 | 18.881 | 9.184 | 1.00 | 44.16 | C |
| ATOM | 7902 | CG | LYS | G | 292 | 26.972 | 18.573 | 10.669 | 1.00 | 44.42 | C |
| ATOM | 7903 | CD | LYS | G | 292 | 25.542 | 18.855 | 11.097 | 1.00 | 44.52 | C |
| ATOM | 7904 | CE | LYS | G | 292 | 25.429 | 19.071 | 12.610 | 1.00 | 44.44 | C |
| ATOM | 7905 | NZ | LYS | G | 292 | 25.810 | 17.882 | 13.428 | 1.00 | 43.93 | N |
| ATOM | 7906 | N | HIS | G | 293 | 28.813 | 21.480 | 10.672 | 1.00 | 46.77 | N |
| ATOM | 7907 | CA | HIS | G | 293 | 29.994 | 21.830 | 11.452 | 1.00 | 49.11 | C |
| ATOM | 7908 | C | HIS | G | 293 | 30.218 | 20.751 | 12.510 | 1.00 | 49.79 | C |
| ATOM | 7909 | O | HIS | G | 293 | 29.460 | 20.639 | 13.471 | 1.00 | 50.32 | O |
| ATOM | 7910 | CB | HIS | G | 293 | 29.826 | 23.207 | 12.112 | 1.00 | 51.00 | C |
| ATOM | 7911 | CG | HIS | G | 293 | 29.596 | 24.320 | 11.133 | 1.00 | 52.88 | C |
| ATOM | 7912 | ND1 | HIS | G | 293 | 30.353 | 25.473 | 11.123 | 1.00 | 53.54 | N |
| ATOM | 7913 | CD2 | HIS | G | 293 | 28.680 | 24.464 | 10.142 | 1.00 | 53.28 | C |
| ATOM | 7914 | CE1 | HIS | G | 293 | 29.916 | 26.278 | 10.169 | 1.00 | 54.40 | C |
| ATOM | 7915 | NE2 | HIS | G | 293 | 28.901 | 25.689 | 9.559 | 1.00 | 54.63 | N |
| ATOM | 7916 | N | VAL | G | 294 | 31.249 | 19.938 | 12.309 | 1.00 | 50.90 | N |
| ATOM | 7917 | CA | VAL | G | 294 | 31.557 | 18.859 | 13.242 | 1.00 | 51.86 | C |
| ATOM | 7918 | C | VAL | G | 294 | 32.912 | 19.083 | 13.907 | 1.00 | 52.55 | C |
| ATOM | 7919 | O | VAL | G | 294 | 33.369 | 18.263 | 14.708 | 1.00 | 53.84 | O |
| ATOM | 7920 | CB | VAL | G | 294 | 31.579 | 17.488 | 12.521 | 1.00 | 51.46 | C |
| ATOM | 7921 | CG1 | VAL | G | 294 | 31.594 | 16.363 | 13.543 | 1.00 | 52.54 | C |
| ATOM | 7922 | CG2 | VAL | G | 294 | 30.371 | 17.356 | 11.610 | 1.00 | 51.18 | C |
| ATOM | 7923 | N | TYR | G | 308 | 36.328 | 22.019 | 11.808 | 1.00 | 56.06 | N |
| ATOM | 7924 | CA | TYR | G | 308 | 36.049 | 20.672 | 11.322 | 1.00 | 55.65 | C |
| ATOM | 7925 | C | TYR | G | 308 | 34.711 | 20.650 | 10.588 | 1.00 | 55.26 | C |
| ATOM | 7926 | O | TYR | G | 308 | 33.652 | 20.803 | 11.202 | 1.00 | 55.16 | O |
| ATOM | 7927 | CB | TYR | G | 308 | 36.013 | 19.686 | 12.491 | 1.00 | 55.81 | C |
| ATOM | 7928 | N | LEU | G | 309 | 34.766 | 20.450 | 9.275 | 1.00 | 54.19 | N |
| ATOM | 7929 | CA | LEU | G | 309 | 33.558 | 20.422 | 8.459 | 1.00 | 52.78 | C |
| ATOM | 7930 | C | LEU | G | 309 | 33.294 | 19.063 | 7.829 | 1.00 | 51.35 | C |
| ATOM | 7931 | O | LEU | G | 309 | 34.214 | 18.275 | 7.625 | 1.00 | 52.19 | O |
| ATOM | 7932 | CB | LEU | G | 309 | 33.662 | 21.458 | 7.342 | 1.00 | 52.85 | C |
| ATOM | 7933 | CG | LEU | G | 309 | 33.916 | 22.913 | 7.738 | 1.00 | 52.82 | C |
| ATOM | 7934 | CD1 | LEU | G | 309 | 33.961 | 23.762 | 6.474 | 1.00 | 53.14 | C |
| ATOM | 7935 | CD2 | LEU | G | 309 | 32.824 | 23.401 | 8.687 | 1.00 | 53.39 | C |
| ATOM | 7936 | N | LYS | G | 310 | 32.028 | 18.796 | 7.523 | 1.00 | 49.05 | N |
| ATOM | 7937 | CA | LYS | G | 310 | 31.633 | 17.547 | 6.880 | 1.00 | 46.61 | C |
| ATOM | 7938 | C | LYS | G | 310 | 30.630 | 17.867 | 5.771 | 1.00 | 44.89 | C |
| ATOM | 7939 | O | LYS | G | 310 | 29.576 | 18.457 | 6.022 | 1.00 | 43.71 | O |
| ATOM | 7940 | CB | LYS | G | 310 | 31.003 | 16.589 | 7.893 | 1.00 | 47.16 | C |
| ATOM | 7941 | N | VAL | G | 311 | 30.964 | 17.481 | 4.543 | 1.00 | 43.13 | N |
| ATOM | 7942 | CA | VAL | G | 311 | 30.095 | 17.745 | 3.401 | 1.00 | 41.87 | C |
| ATOM | 7943 | C | VAL | G | 311 | 28.961 | 16.736 | 3.304 | 1.00 | 41.16 | C |
| ATOM | 7944 | O | VAL | G | 311 | 29.183 | 15.551 | 3.055 | 1.00 | 41.76 | O |
| ATOM | 7945 | CB | VAL | G | 311 | 30.884 | 17.735 | 2.068 | 1.00 | 41.62 | C |
| ATOM | 7946 | CG1 | VAL | G | 311 | 29.927 | 18.000 | 0.894 | 1.00 | 41.69 | C |
| ATOM | 7947 | CG2 | VAL | G | 311 | 31.985 | 18.793 | 2.105 | 1.00 | 40.64 | C |
| ATOM | 7948 | N | LEU | G | 312 | 27.739 | 17.217 | 3.488 | 1.00 | 39.89 | N |
| ATOM | 7949 | CA | LEU | G | 312 | 26.566 | 16.359 | 3.433 | 1.00 | 39.38 | C |

TABLE 3-continued

| FGFR2(D2–D3) Complexed with FGF2 | | | | | | | | | | |
|---|---|---|---|---|---|---|---|---|---|---|
| ATOM | 7950 | C | LEU | G | 312 | 26.091 | 16.102 | 2.012 | 1.00 | 38.89 | C |
| ATOM | 7951 | O | LEU | G | 312 | 25.671 | 14.994 | 1.675 | 1.00 | 39.49 | O |
| ATOM | 7952 | CB | LEU | G | 312 | 25.422 | 16.989 | 4.231 | 1.00 | 38.49 | C |
| ATOM | 7953 | CG | LEU | G | 312 | 25.760 | 17.379 | 5.669 | 1.00 | 38.22 | C |
| ATOM | 7954 | CD1 | LEU | G | 312 | 24.515 | 17.907 | 6.351 | 1.00 | 37.54 | C |
| ATOM | 7955 | CD2 | LEU | G | 312 | 26.313 | 16.166 | 6.419 | 1.00 | 37.98 | C |
| ATOM | 7956 | N | LYS | G | 313 | 26.164 | 17.131 | 1.181 | 1.00 | 37.96 | N |
| ATOM | 7957 | CA | LYS | G | 313 | 25.701 | 17.027 | −0.192 | 1.00 | 36.96 | C |
| ATOM | 7958 | C | LYS | G | 313 | 26.312 | 18.159 | −1.011 | 1.00 | 35.75 | C |
| ATOM | 7959 | O | LYS | G | 313 | 26.484 | 19.270 | −0.509 | 1.00 | 35.15 | O |
| ATOM | 7960 | CB | LYS | G | 313 | 24.167 | 17.112 | −0.202 | 1.00 | 37.92 | C |
| ATOM | 7961 | CG | LYS | G | 313 | 23.531 | 17.036 | −1.570 | 1.00 | 39.69 | C |
| ATOM | 7962 | CD | LYS | G | 313 | 22.017 | 16.829 | −1.483 | 1.00 | 40.66 | C |
| ATOM | 7963 | CE | LYS | G | 313 | 21.293 | 17.981 | −0.808 | 1.00 | 40.96 | C |
| ATOM | 7964 | NZ | LYS | G | 313 | 19.819 | 17.832 | −0.980 | 1.00 | 39.90 | N |
| ATOM | 7965 | N | ALA | G | 314 | 26.651 | 17.871 | −2.263 | 1.00 | 34.32 | N |
| ATOM | 7966 | CA | ALA | G | 314 | 27.245 | 18.873 | −3.139 | 1.00 | 33.49 | C |
| ATOM | 7967 | C | ALA | G | 314 | 26.785 | 18.714 | −4.585 | 1.00 | 33.13 | C |
| ATOM | 7968 | O | ALA | G | 314 | 26.636 | 17.594 | −5.092 | 1.00 | 32.02 | O |
| ATOM | 7969 | CB | ALA | G | 314 | 28.773 | 18.817 | −3.057 | 1.00 | 33.39 | C |
| ATOM | 7970 | N | ALA | G | 315 | 26.565 | 19.852 | −5.242 | 1.00 | 32.55 | N |
| ATOM | 7971 | CA | ALA | G | 315 | 26.100 | 19.882 | −6.624 | 1.00 | 32.03 | C |
| ATOM | 7972 | C | ALA | G | 315 | 27.094 | 19.282 | −7.617 | 1.00 | 31.77 | C |
| ATOM | 7973 | O | ALA | G | 315 | 28.311 | 19.307 | −7.409 | 1.00 | 30.61 | O |
| ATOM | 7974 | CB | ALA | G | 315 | 25.767 | 21.310 | −7.026 | 1.00 | 31.94 | C |
| ATOM | 7975 | N | GLY | G | 316 | 26.555 | 18.754 | −8.709 | 1.00 | 32.02 | N |
| ATOM | 7976 | CA | GLY | G | 316 | 27.384 | 18.159 | −9.739 | 1.00 | 33.55 | C |
| ATOM | 7977 | C | GLY | G | 316 | 26.536 | 17.392 | −10.734 | 1.00 | 35.51 | C |
| ATOM | 7978 | O | GLY | G | 316 | 25.302 | 17.438 | −10.687 | 1.00 | 34.55 | O |
| ATOM | 7979 | N | VAL | G | 317 | 27.201 | 16.691 | −11.645 | 1.00 | 37.19 | N |
| ATOM | 7980 | CA | VAL | G | 317 | 26.511 | 15.903 | −12.657 | 1.00 | 39.87 | C |
| ATOM | 7981 | C | VAL | G | 317 | 25.586 | 14.844 | −12.050 | 1.00 | 41.07 | C |
| ATOM | 7982 | O | VAL | G | 317 | 24.526 | 14.543 | −12.605 | 1.00 | 41.25 | O |
| ATOM | 7983 | CB | VAL | G | 317 | 27.521 | 15.211 | −13.594 | 1.00 | 40.14 | C |
| ATOM | 7984 | CG1 | VAL | G | 317 | 26.841 | 14.078 | −14.339 | 1.00 | 41.69 | C |
| ATOM | 7985 | CG2 | VAL | G | 317 | 28.075 | 16.226 | −14.589 | 1.00 | 40.07 | C |
| ATOM | 7986 | N | ASN | G | 318 | 25.981 | 14.296 | −10.905 | 1.00 | 41.95 | N |
| ATOM | 7987 | CA | ASN | G | 318 | 25.189 | 13.268 | −10.248 | 1.00 | 44.07 | C |
| ATOM | 7988 | C | ASN | G | 318 | 24.232 | 13.814 | −9.187 | 1.00 | 44.24 | C |
| ATOM | 7989 | O | ASN | G | 318 | 23.456 | 13.063 | −8.608 | 1.00 | 45.18 | O |
| ATOM | 7990 | CB | ASN | G | 318 | 26.136 | 12.228 | −9.646 | 1.00 | 46.50 | C |
| ATOM | 7991 | CG | ASN | G | 318 | 27.129 | 11.694 | −10.676 | 1.00 | 48.73 | C |
| ATOM | 7992 | OD1 | ASN | G | 318 | 28.332 | 11.580 | −10.408 | 1.00 | 49.64 | O |
| ATOM | 7993 | ND2 | ASN | G | 318 | 26.626 | 11.372 | −11.866 | 1.00 | 48.81 | N |
| ATOM | 7994 | N | THR | G | 319 | 24.290 | 15.119 | −8.939 | 1.00 | 43.75 | N |
| ATOM | 7995 | CA | THR | G | 319 | 23.417 | 15.766 | −7.959 | 1.00 | 42.90 | C |
| ATOM | 7996 | C | THR | G | 319 | 23.090 | 17.152 | −8.532 | 1.00 | 42.35 | C |
| ATOM | 7997 | O | THR | G | 319 | 23.662 | 18.163 | −8.116 | 1.00 | 41.85 | O |
| ATOM | 7998 | CB | THR | G | 319 | 24.136 | 15.917 | −6.601 | 1.00 | 44.24 | C |
| ATOM | 7999 | OG1 | THR | G | 319 | 24.688 | 14.653 | −6.211 | 1.00 | 45.37 | O |
| ATOM | 8000 | CG2 | THR | G | 319 | 23.162 | 16.379 | −5.521 | 1.00 | 44.23 | C |
| ATOM | 8001 | N | THR | G | 320 | 22.167 | 17.177 | −9.493 | 1.00 | 40.79 | N |
| ATOM | 8002 | CA | THR | G | 320 | 21.777 | 18.396 | −10.196 | 1.00 | 40.16 | C |
| ATOM | 8003 | C | THR | G | 320 | 21.215 | 19.525 | −9.339 | 1.00 | 39.45 | C |
| ATOM | 8004 | O | THR | G | 320 | 20.789 | 19.319 | −8.200 | 1.00 | 38.71 | O |
| ATOM | 8005 | CB | THR | G | 320 | 20.781 | 18.091 | −11.345 | 1.00 | 40.38 | C |
| ATOM | 8006 | OG1 | THR | G | 320 | 19.532 | 17.644 | −10.800 | 1.00 | 40.05 | O |
| ATOM | 8007 | CG2 | THR | G | 320 | 21.348 | 17.013 | −12.262 | 1.00 | 40.03 | C |
| ATOM | 8008 | N | ASP | G | 321 | 21.229 | 20.733 | −9.905 | 1.00 | 38.20 | N |
| ATOM | 8009 | CA | ASP | G | 321 | 20.737 | 21.912 | −9.205 | 1.00 | 37.69 | C |
| ATOM | 8010 | C | ASP | G | 321 | 19.228 | 21.894 | −8.944 | 1.00 | 37.99 | C |
| ATOM | 8011 | O | ASP | G | 321 | 18.745 | 22.613 | −8.076 | 1.00 | 37.70 | O |
| ATOM | 8012 | CB | ASP | G | 321 | 21.119 | 23.181 | −9.970 | 1.00 | 36.07 | C |
| ATOM | 8013 | CG | ASP | G | 321 | 22.612 | 23.470 | −9.941 | 1.00 | 35.06 | C |
| ATOM | 8014 | OD1 | ASP | G | 321 | 23.293 | 22.992 | −9.008 | 1.00 | 32.54 | O |
| ATOM | 8015 | OD2 | ASP | G | 321 | 23.097 | 24.187 | −10.842 | 1.00 | 33.95 | O |
| ATOM | 8016 | N | LYS | G | 322 | 18.486 | 21.072 | −9.684 | 1.00 | 37.99 | N |
| ATOM | 8017 | CA | LYS | G | 322 | 17.039 | 20.989 | −9.514 | 1.00 | 37.74 | C |
| ATOM | 8018 | C | LYS | G | 322 | 16.623 | 20.737 | −8.065 | 1.00 | 37.41 | C |
| ATOM | 8019 | O | LYS | G | 322 | 15.651 | 21.326 | −7.578 | 1.00 | 36.98 | O |
| ATOM | 8020 | CB | LYS | G | 322 | 16.456 | 19.891 | −10.413 | 1.00 | 38.14 | C |
| ATOM | 8021 | N | GLU | G | 323 | 17.363 | 19.880 | −7.367 | 1.00 | 36.92 | N |
| ATOM | 8022 | CA | GLU | G | 323 | 17.026 | 19.562 | −5.981 | 1.00 | 37.04 | C |
| ATOM | 8023 | C | GLU | G | 323 | 18.139 | 19.831 | −4.955 | 1.00 | 37.04 | C |
| ATOM | 8024 | O | GLU | G | 323 | 18.041 | 19.395 | −3.804 | 1.00 | 35.73 | O |
| ATOM | 8025 | CB | GLU | G | 323 | 16.584 | 18.097 | −5.879 | 1.00 | 37.49 | C |
| ATOM | 8026 | N | ILE | G | 324 | 19.175 | 20.564 | −5.359 | 1.00 | 36.64 | N |

TABLE 3-continued

FGFR2(D2–D3) Complexed with FGF2

| ATOM | 8027 | CA | ILE | G | 324 | 20.283 | 20.850 | −4.457 | 1.00 | 36.36 | C |
|---|---|---|---|---|---|---|---|---|---|---|---|
| ATOM | 8028 | C | ILE | G | 324 | 19.974 | 21.894 | −3.374 | 1.00 | 36.39 | C |
| ATOM | 8029 | O | ILE | G | 324 | 20.609 | 21.890 | −2.325 | 1.00 | 36.32 | O |
| ATOM | 8030 | CB | ILE | G | 324 | 21.564 | 21.298 | −5.236 | 1.00 | 35.97 | C |
| ATOM | 8031 | CG1 | ILE | G | 324 | 22.778 | 21.242 | −4.304 | 1.00 | 36.15 | C |
| ATOM | 8032 | CG2 | ILE | G | 324 | 21.418 | 22.724 | −5.775 | 1.00 | 35.04 | C |
| ATOM | 8033 | CD1 | ILE | G | 324 | 23.201 | 19.838 | −3.928 | 1.00 | 35.22 | C |
| ATOM | 8034 | N | GLU | G | 325 | 18.995 | 22.763 | −3.610 | 1.00 | 36.24 | N |
| ATOM | 8035 | CA | GLU | G | 325 | 18.666 | 23.800 | −2.636 | 1.00 | 37.40 | C |
| ATOM | 8036 | C | GLU | G | 325 | 17.861 | 23.396 | −1.400 | 1.00 | 37.97 | C |
| ATOM | 8037 | O | GLU | G | 325 | 17.570 | 24.235 | −0.549 | 1.00 | 37.80 | O |
| ATOM | 8038 | CB | GLU | G | 325 | 17.984 | 24.965 | −3.344 | 1.00 | 37.95 | C |
| ATOM | 8039 | CG | GLU | G | 325 | 18.949 | 25.748 | −4.228 | 1.00 | 39.17 | C |
| ATOM | 8040 | CD | GLU | G | 325 | 18.247 | 26.738 | −5.131 | 1.00 | 40.30 | C |
| ATOM | 8041 | OE1 | GLU | G | 325 | 17.453 | 26.298 | −5.998 | 1.00 | 40.14 | O |
| ATOM | 8042 | OE2 | GLU | G | 325 | 18.488 | 27.953 | −4.972 | 1.00 | 40.10 | O |
| ATOM | 8043 | N | VAL | G | 326 | 17.496 | 22.125 | −1.292 | 1.00 | 38.24 | N |
| ATOM | 8044 | CA | VAL | G | 326 | 16.767 | 21.668 | −0.116 | 1.00 | 39.31 | C |
| ATOM | 8045 | C | VAL | G | 326 | 17.461 | 20.438 | 0.460 | 1.00 | 39.67 | C |
| ATOM | 8046 | O | VAL | G | 326 | 17.779 | 19.506 | −0.270 | 1.00 | 39.75 | O |
| ATOM | 8047 | CB | VAL | G | 326 | 15.279 | 21.339 | −0.443 | 1.00 | 39.91 | C |
| ATOM | 8048 | CG1 | VAL | G | 326 | 15.188 | 20.261 | −1.530 | 1.00 | 40.97 | C |
| ATOM | 8049 | CG2 | VAL | G | 326 | 14.573 | 20.871 | 0.820 | 1.00 | 39.23 | C |
| ATOM | 8050 | N | LEU | G | 327 | 17.725 | 20.457 | 1.763 | 1.00 | 40.13 | N |
| ATOM | 8051 | CA | LEU | G | 327 | 18.387 | 19.341 | 2.435 | 1.00 | 40.28 | C |
| ATOM | 8052 | C | LEU | G | 327 | 17.418 | 18.677 | 3.397 | 1.00 | 41.91 | C |
| ATOM | 8053 | O | LEU | G | 327 | 16.891 | 19.327 | 4.306 | 1.00 | 41.63 | O |
| ATOM | 8054 | CB | LEU | G | 327 | 19.612 | 19.821 | 3.219 | 1.00 | 39.29 | C |
| ATOM | 8055 | CG | LEU | G | 327 | 20.320 | 18.778 | 4.096 | 1.00 | 38.07 | C |
| ATOM | 8056 | CD1 | LEU | G | 327 | 21.037 | 17.746 | 3.225 | 1.00 | 36.50 | C |
| ATOM | 8057 | CD2 | LEU | G | 327 | 21.315 | 19.476 | 5.007 | 1.00 | 37.17 | C |
| ATOM | 8058 | N | TYR | G | 328 | 17.190 | 17.382 | 3.196 | 1.00 | 42.74 | N |
| ATOM | 8059 | CA | TYR | G | 328 | 16.283 | 16.622 | 4.050 | 1.00 | 43.93 | C |
| ATOM | 8060 | C | TYR | G | 328 | 17.039 | 15.708 | 5.022 | 1.00 | 45.77 | C |
| ATOM | 8061 | O | TYR | G | 328 | 18.049 | 15.097 | 4.664 | 1.00 | 45.73 | O |
| ATOM | 8062 | CB | TYR | G | 328 | 15.317 | 15.773 | 3.196 | 1.00 | 41.69 | C |
| ATOM | 8063 | CG | TYR | G | 328 | 14.348 | 16.574 | 2.342 | 1.00 | 39.94 | C |
| ATOM | 8064 | CD1 | TYR | G | 328 | 14.572 | 16.760 | 0.976 | 1.00 | 38.82 | C |
| ATOM | 8065 | CD2 | TYR | G | 328 | 13.224 | 17.176 | 2.910 | 1.00 | 39.08 | C |
| ATOM | 8066 | CE1 | TYR | G | 328 | 13.695 | 17.531 | 0.192 | 1.00 | 38.26 | C |
| ATOM | 8067 | CE2 | TYR | G | 328 | 12.345 | 17.953 | 2.144 | 1.00 | 38.56 | C |
| ATOM | 8068 | CZ | TYR | G | 328 | 12.585 | 18.127 | 0.789 | 1.00 | 38.92 | C |
| ATOM | 8069 | OH | TYR | G | 328 | 11.731 | 18.924 | 0.053 | 1.00 | 39.12 | O |
| ATOM | 8070 | N | ILE | G | 329 | 16.553 | 15.635 | 6.258 | 1.00 | 47.90 | N |
| ATOM | 8071 | CA | ILE | G | 329 | 17.151 | 14.768 | 7.272 | 1.00 | 49.82 | C |
| ATOM | 8072 | C | ILE | G | 329 | 16.029 | 14.083 | 8.047 | 1.00 | 51.30 | C |
| ATOM | 8073 | O | ILE | G | 329 | 15.304 | 14.727 | 8.802 | 1.00 | 51.47 | O |
| ATOM | 8074 | CB | ILE | G | 329 | 18.032 | 15.547 | 8.242 | 1.00 | 49.44 | C |
| ATOM | 8075 | CG1 | ILE | G | 329 | 19.170 | 16.205 | 7.472 | 1.00 | 48.78 | C |
| ATOM | 8076 | CG2 | ILE | G | 329 | 18.581 | 14.607 | 9.308 | 1.00 | 49.28 | C |
| ATOM | 8077 | CD1 | ILE | G | 329 | 19.913 | 17.229 | 8.276 | 1.00 | 50.09 | C |
| ATOM | 8078 | N | ARG | G | 330 | 15.891 | 12.773 | 7.848 | 1.00 | 53.05 | N |
| ATOM | 8079 | CA | ARG | G | 330 | 14.836 | 12.000 | 8.503 | 1.00 | 54.65 | C |
| ATOM | 8080 | C | ARG | G | 330 | 15.320 | 11.157 | 9.683 | 1.00 | 54.87 | C |
| ATOM | 8081 | O | ARG | G | 330 | 16.498 | 10.798 | 9.773 | 1.00 | 54.39 | O |
| ATOM | 8082 | CB | ARG | G | 330 | 14.141 | 11.072 | 7.495 | 1.00 | 56.47 | C |
| ATOM | 8083 | CG | ARG | G | 330 | 13.435 | 11.757 | 6.328 | 1.00 | 58.62 | C |
| ATOM | 8084 | CD | ARG | G | 330 | 11.920 | 11.737 | 6.477 | 1.00 | 59.82 | C |
| ATOM | 8085 | NE | ARG | G | 330 | 11.244 | 11.856 | 5.182 | 1.00 | 61.36 | N |
| ATOM | 8086 | CZ | ARG | G | 330 | 9.944 | 12.094 | 5.022 | 1.00 | 62.24 | C |
| ATOM | 8087 | NH1 | ARG | G | 330 | 9.162 | 12.243 | 6.078 | 1.00 | 62.98 | N |
| ATOM | 8088 | NH2 | ARG | G | 330 | 9.424 | 12.167 | 3.803 | 1.00 | 62.21 | N |
| ATOM | 8089 | N | ASN | G | 331 | 14.386 | 10.840 | 10.580 | 1.00 | 55.35 | N |
| ATOM | 8090 | CA | ASN | G | 331 | 14.669 | 10.035 | 11.765 | 1.00 | 55.98 | C |
| ATOM | 8091 | C | ASN | G | 331 | 15.949 | 10.543 | 12.431 | 1.00 | 56.14 | C |
| ATOM | 8092 | O | ASN | G | 331 | 16.923 | 9.804 | 12.597 | 1.00 | 56.20 | O |
| ATOM | 8093 | CB | ASN | G | 331 | 14.798 | 8.552 | 11.365 | 1.00 | 56.59 | C |
| ATOM | 8094 | CG | ASN | G | 331 | 14.834 | 7.620 | 12.569 | 1.00 | 57.23 | C |
| ATOM | 8095 | OD1 | ASN | G | 331 | 14.715 | 8.049 | 13.717 | 1.00 | 57.90 | O |
| ATOM | 8096 | ND2 | ASN | G | 331 | 15.000 | 6.330 | 12.305 | 1.00 | 56.52 | N |
| ATOM | 8097 | N | VAL | G | 332 | 15.929 | 11.814 | 12.820 | 1.00 | 56.01 | N |
| ATOM | 8098 | CA | VAL | G | 332 | 17.085 | 12.451 | 13.442 | 1.00 | 55.69 | C |
| ATOM | 8099 | C | VAL | G | 332 | 17.479 | 11.870 | 14.793 | 1.00 | 55.65 | C |
| ATOM | 8100 | O | VAL | G | 332 | 16.636 | 11.384 | 15.551 | 1.00 | 55.23 | O |
| ATOM | 8101 | CB | VAL | G | 332 | 16.853 | 13.966 | 13.631 | 1.00 | 55.69 | C |
| ATOM | 8102 | CG1 | VAL | G | 332 | 16.411 | 14.596 | 12.318 | 1.00 | 55.96 | C |
| ATOM | 8103 | CG2 | VAL | G | 332 | 15.820 | 14.201 | 14.709 | 1.00 | 55.79 | C |

TABLE 3-continued

| | | | | FGFR2(D2–D3) Complexed with FGF2 | | | | | | |
|---|---|---|---|---|---|---|---|---|---|---|
| ATOM | 8104 | N | THR | G | 333 | 18.777 | 11.927 | 15.078 | 1.00 | 55.48 | N |
| ATOM | 8105 | CA | THR | G | 333 | 19.331 | 11.454 | 16.341 | 1.00 | 55.59 | C |
| ATOM | 8106 | C | THR | G | 333 | 19.872 | 12.695 | 17.044 | 1.00 | 55.87 | C |
| ATOM | 8107 | O | THR | G | 333 | 19.893 | 13.777 | 16.453 | 1.00 | 55.99 | O |
| ATOM | 8108 | CB | THR | G | 333 | 20.504 | 10.472 | 16.126 | 1.00 | 55.46 | C |
| ATOM | 8109 | OG1 | THR | G | 333 | 21.557 | 11.134 | 15.414 | 1.00 | 54.62 | O |
| ATOM | 8110 | CG2 | THR | G | 333 | 20.050 | 9.250 | 15.338 | 1.00 | 55.51 | C |
| ATOM | 8111 | N | PHE | G | 334 | 20.302 | 12.550 | 18.297 | 1.00 | 55.79 | N |
| ATOM | 8112 | CA | PHE | G | 334 | 20.855 | 13.689 | 19.030 | 1.00 | 55.65 | C |
| ATOM | 8113 | C | PHE | G | 334 | 22.155 | 14.123 | 18.356 | 1.00 | 55.18 | C |
| ATOM | 8114 | O | PHE | G | 334 | 22.590 | 15.270 | 18.486 | 1.00 | 54.88 | O |
| ATOM | 8115 | CB | PHE | G | 334 | 21.172 | 13.325 | 20.489 | 1.00 | 56.25 | C |
| ATOM | 8116 | CG | PHE | G | 334 | 19.962 | 13.177 | 21.371 | 1.00 | 57.08 | C |
| ATOM | 8117 | CD1 | PHE | G | 334 | 19.411 | 11.920 | 21.614 | 1.00 | 57.54 | C |
| ATOM | 8118 | CD2 | PHE | G | 334 | 19.393 | 14.288 | 21.986 | 1.00 | 56.80 | C |
| ATOM | 8119 | CE1 | PHE | G | 334 | 18.313 | 11.771 | 22.463 | 1.00 | 57.99 | C |
| ATOM | 8120 | CE2 | PHE | G | 334 | 18.295 | 14.151 | 22.833 | 1.00 | 57.37 | C |
| ATOM | 8121 | CZ | PHE | G | 334 | 17.754 | 12.891 | 23.075 | 1.00 | 57.64 | C |
| ATOM | 8122 | N | GLU | G | 335 | 22.778 | 13.190 | 17.643 | 1.00 | 54.14 | N |
| ATOM | 8123 | CA | GLU | G | 335 | 24.035 | 13.467 | 16.958 | 1.00 | 53.66 | C |
| ATOM | 8124 | C | GLU | G | 335 | 23.856 | 14.452 | 15.796 | 1.00 | 52.54 | C |
| ATOM | 8125 | O | GLU | G | 335 | 24.793 | 15.164 | 15.432 | 1.00 | 52.06 | O |
| ATOM | 8126 | CB | GLU | G | 335 | 24.658 | 12.161 | 16.444 | 1.00 | 53.19 | C |
| ATOM | 8127 | N | ASP | G | 336 | 22.654 | 14.497 | 15.227 | 1.00 | 51.27 | N |
| ATOM | 8128 | CA | ASP | G | 336 | 22.378 | 15.393 | 14.109 | 1.00 | 50.05 | C |
| ATOM | 8129 | C | ASP | G | 336 | 22.310 | 16.866 | 14.511 | 1.00 | 49.15 | C |
| ATOM | 8130 | O | ASP | G | 336 | 22.448 | 17.747 | 13.665 | 1.00 | 48.99 | O |
| ATOM | 8131 | CB | ASP | G | 336 | 21.083 | 14.981 | 13.407 | 1.00 | 49.53 | C |
| ATOM | 8132 | CG | ASP | G | 336 | 21.184 | 13.617 | 12.754 | 1.00 | 49.48 | C |
| ATOM | 8133 | OD1 | ASP | G | 336 | 22.212 | 13.353 | 12.092 | 1.00 | 49.51 | O |
| ATOM | 8134 | OD2 | ASP | G | 336 | 20.236 | 12.813 | 12.893 | 1.00 | 49.11 | O |
| ATOM | 8135 | N | ALA | G | 337 | 22.097 | 17.129 | 15.797 | 1.00 | 47.92 | N |
| ATOM | 8136 | CA | ALA | G | 337 | 22.034 | 18.501 | 16.291 | 1.00 | 47.56 | C |
| ATOM | 8137 | C | ALA | G | 337 | 23.294 | 19.263 | 15.878 | 1.00 | 47.01 | C |
| ATOM | 8138 | O | ALA | G | 337 | 24.372 | 18.678 | 15.764 | 1.00 | 47.18 | O |
| ATOM | 8139 | CB | ALA | G | 337 | 21.906 | 18.502 | 17.809 | 1.00 | 46.58 | C |
| ATOM | 8140 | N | GLY | G | 338 | 23.161 | 20.566 | 15.653 | 1.00 | 46.08 | N |
| ATOM | 8141 | CA | GLY | G | 338 | 24.320 | 21.356 | 15.274 | 1.00 | 44.93 | C |
| ATOM | 8142 | C | GLY | G | 338 | 24.059 | 22.424 | 14.225 | 1.00 | 44.14 | C |
| ATOM | 8143 | O | GLY | G | 338 | 22.911 | 22.675 | 13.842 | 1.00 | 43.26 | O |
| ATOM | 8144 | N | GLU | G | 339 | 25.137 | 23.050 | 13.758 | 1.00 | 43.05 | N |
| ATOM | 8145 | CA | GLU | G | 339 | 25.042 | 24.108 | 12.758 | 1.00 | 42.49 | C |
| ATOM | 8146 | C | GLU | G | 339 | 25.165 | 23.588 | 11.332 | 1.00 | 41.35 | C |
| ATOM | 8147 | O | GLU | G | 339 | 26.131 | 22.910 | 10.997 | 1.00 | 41.27 | O |
| ATOM | 8148 | CB | GLU | G | 339 | 26.123 | 25.173 | 12.991 | 1.00 | 42.71 | C |
| ATOM | 8149 | CG | GLU | G | 339 | 25.894 | 26.437 | 12.179 | 1.00 | 44.12 | C |
| ATOM | 8150 | CD | GLU | G | 339 | 26.770 | 27.608 | 12.610 | 1.00 | 45.91 | C |
| ATOM | 8151 | OE1 | GLU | G | 339 | 26.323 | 28.766 | 12.455 | 1.00 | 46.01 | O |
| ATOM | 8152 | OE2 | GLU | G | 339 | 27.901 | 27.379 | 13.090 | 1.00 | 46.77 | O |
| ATOM | 8153 | N | TYR | G | 340 | 24.172 | 23.910 | 10.505 | 1.00 | 40.08 | N |
| ATOM | 8154 | CA | TYR | G | 340 | 24.157 | 23.519 | 9.097 | 1.00 | 38.55 | C |
| ATOM | 8155 | C | TYR | G | 340 | 24.345 | 24.757 | 8.220 | 1.00 | 37.99 | C |
| ATOM | 8156 | O | TYR | G | 340 | 23.751 | 25.817 | 8.470 | 1.00 | 37.78 | O |
| ATOM | 8157 | CB | TYR | G | 340 | 22.837 | 22.844 | 8.732 | 1.00 | 39.39 | C |
| ATOM | 8158 | CG | TYR | G | 340 | 22.666 | 21.468 | 9.332 | 1.00 | 40.42 | C |
| ATOM | 8159 | CD1 | TYR | G | 340 | 22.521 | 21.298 | 10.711 | 1.00 | 40.04 | C |
| ATOM | 8160 | CD2 | TYR | G | 340 | 22.636 | 20.336 | 8.518 | 1.00 | 40.28 | C |
| ATOM | 8161 | CE1 | TYR | G | 340 | 22.346 | 20.031 | 11.268 | 1.00 | 41.01 | C |
| ATOM | 8162 | CE2 | TYR | G | 340 | 22.464 | 19.067 | 9.058 | 1.00 | 41.27 | C |
| ATOM | 8163 | CZ | TYR | G | 340 | 22.319 | 18.918 | 10.437 | 1.00 | 41.70 | C |
| ATOM | 8164 | OH | TYR | G | 340 | 22.156 | 17.657 | 10.974 | 1.00 | 41.92 | O |
| ATOM | 8165 | N | THR | G | 341 | 25.161 | 24.626 | 7.184 | 1.00 | 36.18 | N |
| ATOM | 8166 | CA | THR | G | 341 | 25.418 | 25.753 | 6.311 | 1.00 | 35.17 | C |
| ATOM | 8167 | C | THR | G | 341 | 25.232 | 25.489 | 4.830 | 1.00 | 34.76 | C |
| ATOM | 8168 | O | THR | G | 341 | 25.667 | 24.464 | 4.310 | 1.00 | 35.27 | O |
| ATOM | 8169 | CB | THR | G | 341 | 26.859 | 26.294 | 6.505 | 1.00 | 34.51 | C |
| ATOM | 8170 | OG1 | THR | G | 341 | 26.998 | 26.830 | 7.823 | 1.00 | 34.37 | O |
| ATOM | 8171 | CG2 | THR | G | 341 | 27.175 | 27.385 | 5.475 | 1.00 | 33.51 | C |
| ATOM | 8172 | N | CYS | G | 342 | 24.559 | 26.418 | 4.161 | 1.00 | 33.38 | N |
| ATOM | 8173 | CA | CYS | G | 342 | 24.403 | 26.331 | 2.721 | 1.00 | 33.42 | C |
| ATOM | 8174 | C | CYS | G | 342 | 25.495 | 27.251 | 2.187 | 1.00 | 32.22 | C |
| ATOM | 8175 | O | CYS | G | 342 | 25.525 | 28.445 | 2.507 | 1.00 | 31.86 | O |
| ATOM | 8176 | CB | CYS | G | 342 | 23.043 | 26.838 | 2.255 | 1.00 | 32.91 | C |
| ATOM | 8177 | SG | CYS | G | 342 | 23.023 | 27.056 | 0.461 | 1.00 | 36.06 | S |
| ATOM | 8178 | N | LEU | G | 343 | 26.403 | 26.698 | 1.395 | 1.00 | 31.33 | N |
| ATOM | 8179 | CA | LEU | G | 343 | 27.503 | 27.487 | 0.851 | 1.00 | 29.84 | C |
| ATOM | 8180 | C | LEU | G | 343 | 27.470 | 27.498 | −0.673 | 1.00 | 29.17 | C |

TABLE 3-continued

FGFR2(D2–D3) Complexed with FGF2

| ATOM | 8181 | O | LEU | G | 343 | 27.415 | 26.442 | −1.317 | 1.00 | 28.70 | O |
|---|---|---|---|---|---|---|---|---|---|---|---|
| ATOM | 8182 | CB | LEU | G | 343 | 28.838 | 26.933 | 1.359 | 1.00 | 29.41 | C |
| ATOM | 8183 | CG | LEU | G | 343 | 30.090 | 27.722 | 0.963 | 1.00 | 30.02 | C |
| ATOM | 8184 | CD1 | LEU | G | 343 | 31.213 | 27.426 | 1.928 | 1.00 | 30.53 | C |
| ATOM | 8185 | CD2 | LEU | G | 343 | 30.487 | 27.367 | −0.468 | 1.00 | 31.57 | C |
| ATOM | 8186 | N | ALA | G | 344 | 27.493 | 28.706 | −1.234 | 1.00 | 28.06 | N |
| ATOM | 8187 | CA | ALA | G | 344 | 27.450 | 28.920 | −2.677 | 1.00 | 28.04 | C |
| ATOM | 8188 | C | ALA | G | 344 | 28.666 | 29.689 | −3.166 | 1.00 | 28.21 | C |
| ATOM | 8189 | O | ALA | G | 344 | 28.988 | 30.763 | −2.648 | 1.00 | 28.24 | O |
| ATOM | 8190 | CB | ALA | G | 344 | 26.177 | 29.695 | −3.064 | 1.00 | 24.87 | C |
| ATOM | 8191 | N | GLY | G | 345 | 29.331 | 29.153 | −4.182 | 1.00 | 28.21 | N |
| ATOM | 8192 | CA | GLY | G | 345 | 30.485 | 29.841 | −4.721 | 1.00 | 28.10 | C |
| ATOM | 8193 | C | GLY | G | 345 | 30.563 | 29.818 | −6.232 | 1.00 | 27.62 | C |
| ATOM | 8194 | O | GLY | G | 345 | 30.088 | 28.880 | −6.866 | 1.00 | 27.30 | O |
| ATOM | 8195 | N | ASN | G | 346 | 31.136 | 30.875 | −6.801 | 1.00 | 28.40 | N |
| ATOM | 8196 | CA | ASN | G | 346 | 31.365 | 30.979 | −8.238 | 1.00 | 29.46 | C |
| ATOM | 8197 | C | ASN | G | 346 | 32.806 | 31.503 | −8.405 | 1.00 | 29.97 | C |
| ATOM | 8198 | O | ASN | G | 346 | 33.516 | 31.688 | −7.411 | 1.00 | 28.93 | O |
| ATOM | 8199 | CB | ASN | G | 346 | 30.332 | 31.913 | −8.910 | 1.00 | 29.29 | C |
| ATOM | 8200 | CG | ASN | G | 346 | 30.356 | 33.346 | −8.363 | 1.00 | 31.68 | C |
| ATOM | 8201 | OD1 | ASN | G | 346 | 31.400 | 33.876 | −7.995 | 1.00 | 32.04 | O |
| ATOM | 8202 | ND2 | ASN | G | 346 | 29.189 | 33.987 | −8.347 | 1.00 | 33.14 | N |
| ATOM | 8203 | N | SER | G | 347 | 33.232 | 31.737 | −9.645 | 1.00 | 31.49 | N |
| ATOM | 8204 | CA | SER | G | 347 | 34.582 | 32.229 | −9.933 | 1.00 | 32.37 | C |
| ATOM | 8205 | C | SER | G | 347 | 34.951 | 33.528 | −9.197 | 1.00 | 33.15 | C |
| ATOM | 8206 | O | SER | G | 347 | 36.117 | 33.755 | −8.877 | 1.00 | 33.62 | O |
| ATOM | 8207 | CB | SER | G | 347 | 34.736 | 32.425 | −11.449 | 1.00 | 32.93 | C |
| ATOM | 8208 | OG | SER | G | 347 | 33.785 | 33.349 | −11.969 | 1.00 | 33.21 | O |
| ATOM | 8209 | N | ILE | G | 348 | 33.962 | 34.374 | −8.918 | 1.00 | 33.11 | N |
| ATOM | 8210 | CA | ILE | G | 348 | 34.218 | 35.639 | −8.233 | 1.00 | 33.33 | C |
| ATOM | 8211 | C | ILE | G | 348 | 34.392 | 35.516 | −6.717 | 1.00 | 33.98 | C |
| ATOM | 8212 | O | ILE | G | 348 | 35.285 | 36.146 | −6.139 | 1.00 | 34.53 | O |
| ATOM | 8213 | CB | ILE | G | 348 | 33.097 | 36.656 | −8.537 | 1.00 | 33.03 | C |
| ATOM | 8214 | CG1 | ILE | G | 348 | 33.069 | 36.952 | −10.038 | 1.00 | 32.51 | C |
| ATOM | 8215 | CG2 | ILE | G | 348 | 33.331 | 37.942 | −7.771 | 1.00 | 32.83 | C |
| ATOM | 8216 | CD1 | ILE | G | 348 | 31.686 | 37.154 | −10.592 | 1.00 | 33.67 | C |
| ATOM | 8217 | N | GLY | G | 349 | 33.549 | 34.711 | −6.073 | 1.00 | 33.74 | N |
| ATOM | 8218 | CA | GLY | G | 349 | 33.651 | 34.554 | −4.634 | 1.00 | 33.15 | C |
| ATOM | 8219 | C | GLY | G | 349 | 32.691 | 33.558 | −4.005 | 1.00 | 33.68 | C |
| ATOM | 8220 | O | GLY | G | 349 | 31.941 | 32.868 | −4.698 | 1.00 | 33.59 | O |
| ATOM | 8221 | N | ILE | G | 350 | 32.700 | 33.528 | −2.672 | 1.00 | 34.04 | N |
| ATOM | 8222 | CA | ILE | G | 350 | 31.895 | 32.614 | −1.864 | 1.00 | 33.81 | C |
| ATOM | 8223 | C | ILE | G | 350 | 30.926 | 33.311 | −0.907 | 1.00 | 34.33 | C |
| ATOM | 8224 | O | ILE | G | 350 | 31.259 | 34.340 | −0.327 | 1.00 | 34.64 | O |
| ATOM | 8225 | CB | ILE | G | 350 | 32.828 | 31.741 | −0.999 | 1.00 | 34.32 | C |
| ATOM | 8226 | CG1 | ILE | G | 350 | 33.708 | 30.871 | −1.898 | 1.00 | 34.38 | C |
| ATOM | 8227 | CG2 | ILE | G | 350 | 32.022 | 30.935 | 0.015 | 1.00 | 34.43 | C |
| ATOM | 8228 | CD1 | ILE | G | 350 | 34.723 | 30.023 | −1.133 | 1.00 | 34.20 | C |
| ATOM | 8229 | N | SER | G | 351 | 29.740 | 32.728 | −0.736 | 1.00 | 33.67 | N |
| ATOM | 8230 | CA | SER | G | 351 | 28.720 | 33.241 | 0.179 | 1.00 | 32.95 | C |
| ATOM | 8231 | C | SER | G | 351 | 28.097 | 32.051 | 0.917 | 1.00 | 32.49 | C |
| ATOM | 8232 | O | SER | G | 351 | 28.025 | 30.957 | 0.363 | 1.00 | 31.80 | O |
| ATOM | 8233 | CB | SER | G | 351 | 27.636 | 34.000 | −0.595 | 1.00 | 33.61 | C |
| ATOM | 8234 | OG | SER | G | 351 | 28.168 | 35.162 | −1.207 | 1.00 | 33.50 | O |
| ATOM | 8235 | N | PHE | G | 352 | 27.659 | 32.257 | 2.157 | 1.00 | 31.29 | N |
| ATOM | 8236 | CA | PHE | G | 352 | 27.060 | 31.177 | 2.930 | 1.00 | 31.63 | C |
| ATOM | 8237 | C | PHE | G | 352 | 26.168 | 31.651 | 4.080 | 1.00 | 32.23 | C |
| ATOM | 8238 | O | PHE | G | 352 | 26.469 | 32.652 | 4.737 | 1.00 | 32.63 | O |
| ATOM | 8239 | CB | PHE | G | 352 | 28.167 | 30.260 | 3.476 | 1.00 | 31.01 | C |
| ATOM | 8240 | CG | PHE | G | 352 | 29.075 | 30.920 | 4.486 | 1.00 | 31.43 | C |
| ATOM | 8241 | CD1 | PHE | G | 352 | 28.670 | 31.081 | 5.812 | 1.00 | 31.71 | C |
| ATOM | 8242 | CD2 | PHE | G | 352 | 30.338 | 31.384 | 4.111 | 1.00 | 31.71 | C |
| ATOM | 8243 | CE1 | PHE | G | 352 | 29.512 | 31.694 | 6.756 | 1.00 | 32.54 | C |
| ATOM | 8244 | CE2 | PHE | G | 352 | 31.186 | 32.000 | 5.045 | 1.00 | 31.96 | C |
| ATOM | 8245 | CZ | PHE | G | 352 | 30.776 | 32.154 | 6.364 | 1.00 | 31.67 | C |
| ATOM | 8246 | N | HIS | G | 353 | 25.067 | 30.934 | 4.307 | 1.00 | 32.19 | N |
| ATOM | 8247 | CA | HIS | G | 353 | 24.131 | 31.235 | 5.400 | 1.00 | 32.95 | C |
| ATOM | 8248 | C | HIS | G | 353 | 24.019 | 29.976 | 6.266 | 1.00 | 33.83 | C |
| ATOM | 8249 | O | HIS | G | 353 | 23.995 | 28.854 | 5.745 | 1.00 | 33.62 | O |
| ATOM | 8250 | CB | HIS | G | 353 | 22.725 | 31.590 | 4.887 | 1.00 | 31.45 | C |
| ATOM | 8251 | CG | HIS | G | 353 | 22.598 | 32.972 | 4.314 | 1.00 | 31.24 | C |
| ATOM | 8252 | ND1 | HIS | G | 353 | 21.390 | 33.479 | 3.874 | 1.00 | 28.98 | N |
| ATOM | 8253 | CD2 | HIS | G | 353 | 23.519 | 33.939 | 4.085 | 1.00 | 31.47 | C |
| ATOM | 8254 | CE1 | HIS | G | 353 | 21.575 | 34.698 | 3.396 | 1.00 | 29.98 | C |
| ATOM | 8255 | NE2 | HIS | G | 353 | 22.857 | 35.003 | 3.509 | 1.00 | 29.58 | N |
| ATOM | 8256 | N | SER | G | 354 | 23.925 | 30.162 | 7.582 | 1.00 | 34.43 | N |
| ATOM | 8257 | CA | SER | G | 354 | 23.841 | 29.040 | 8.505 | 1.00 | 35.16 | C |

TABLE 3-continued

FGFR2(D2–D3) Complexed with FGF2

| ATOM | 8258 | C | SER | G | 354 | 22.591 | 29.026 | 9.371 | 1.00 | 36.14 | C |
|---|---|---|---|---|---|---|---|---|---|---|---|
| ATOM | 8259 | O | SER | G | 354 | 21.977 | 30.058 | 9.621 | 1.00 | 36.56 | O |
| ATOM | 8260 | CB | SER | G | 354 | 25.070 | 29.035 | 9.407 | 1.00 | 35.17 | C |
| ATOM | 8261 | OG | SER | G | 354 | 26.245 | 29.081 | 8.632 | 1.00 | 35.00 | O |
| ATOM | 8262 | N | ALA | G | 355 | 22.222 | 27.834 | 9.825 | 1.00 | 37.15 | N |
| ATOM | 8263 | CA | ALA | G | 355 | 21.054 | 27.658 | 10.676 | 1.00 | 38.86 | C |
| ATOM | 8264 | C | ALA | G | 355 | 21.394 | 26.584 | 11.695 | 1.00 | 39.80 | C |
| ATOM | 8265 | O | ALA | G | 355 | 22.340 | 25.816 | 11.513 | 1.00 | 39.82 | O |
| ATOM | 8266 | CB | ALA | G | 355 | 19.846 | 27.235 | 9.843 | 1.00 | 37.20 | C |
| ATOM | 8267 | N | TRP | G | 356 | 20.626 | 26.525 | 12.770 | 1.00 | 41.54 | N |
| ATOM | 8268 | CA | TRP | G | 356 | 20.881 | 25.531 | 13.800 | 1.00 | 43.64 | C |
| ATOM | 8269 | C | TRP | G | 356 | 19.751 | 24.523 | 13.935 | 1.00 | 43.65 | C |
| ATOM | 8270 | O | TRP | G | 356 | 18.573 | 24.860 | 13.788 | 1.00 | 43.22 | O |
| ATOM | 8271 | CB | TRP | G | 356 | 21.114 | 26.225 | 15.141 | 1.00 | 46.44 | C |
| ATOM | 8272 | CG | TRP | G | 356 | 22.511 | 26.086 | 15.662 | 1.00 | 49.88 | C |
| ATOM | 8273 | CD1 | TRP | G | 356 | 23.063 | 24.983 | 16.258 | 1.00 | 51.44 | C |
| ATOM | 8274 | CD2 | TRP | G | 356 | 23.535 | 27.086 | 15.640 | 1.00 | 51.37 | C |
| ATOM | 8275 | NE1 | TRP | G | 356 | 24.371 | 25.238 | 16.612 | 1.00 | 52.49 | N |
| ATOM | 8276 | CE2 | TRP | G | 356 | 24.686 | 26.520 | 16.244 | 1.00 | 52.66 | C |
| ATOM | 8277 | CE3 | TRP | G | 356 | 23.595 | 28.405 | 15.171 | 1.00 | 52.35 | C |
| ATOM | 8278 | CZ2 | TRP | G | 356 | 25.884 | 27.231 | 16.391 | 1.00 | 53.68 | C |
| ATOM | 8279 | CZ3 | TRP | G | 356 | 24.785 | 29.117 | 15.318 | 1.00 | 53.49 | C |
| ATOM | 8280 | CH2 | TRP | G | 356 | 25.914 | 28.526 | 15.924 | 1.00 | 54.51 | C |
| ATOM | 8281 | N | LEU | G | 357 | 20.123 | 23.276 | 14.191 | 1.00 | 43.63 | N |
| ATOM | 8282 | CA | LEU | G | 357 | 19.140 | 22.227 | 14.387 | 1.00 | 44.46 | C |
| ATOM | 8283 | C | LEU | G | 357 | 19.162 | 21.828 | 15.854 | 1.00 | 45.26 | C |
| ATOM | 8284 | O | LEU | G | 357 | 20.201 | 21.426 | 16.381 | 1.00 | 45.00 | O |
| ATOM | 8285 | CB | LEU | G | 357 | 19.452 | 21.003 | 13.526 | 1.00 | 43.98 | C |
| ATOM | 8286 | CG | LEU | G | 357 | 18.610 | 19.760 | 13.838 | 1.00 | 43.52 | C |
| ATOM | 8287 | CD1 | LEU | G | 357 | 17.133 | 20.042 | 13.592 | 1.00 | 43.52 | C |
| ATOM | 8288 | CD2 | LEU | G | 357 | 19.076 | 18.604 | 12.980 | 1.00 | 43.08 | C |
| ATOM | 8289 | N | THR | G | 358 | 18.017 | 21.963 | 16.516 | 1.00 | 46.65 | N |
| ATOM | 8290 | CA | THR | G | 358 | 17.895 | 21.582 | 17.923 | 1.00 | 47.93 | C |
| ATOM | 8291 | C | THR | G | 358 | 17.109 | 20.284 | 18.028 | 1.00 | 48.09 | C |
| ATOM | 8292 | O | THR | G | 358 | 16.003 | 20.177 | 17.499 | 1.00 | 48.24 | O |
| ATOM | 8293 | CB | THR | G | 358 | 17.159 | 22.659 | 18.768 | 1.00 | 48.22 | C |
| ATOM | 8294 | OG1 | THR | G | 358 | 17.958 | 23.846 | 18.850 | 1.00 | 48.40 | O |
| ATOM | 8295 | CG2 | THR | G | 358 | 16.902 | 22.140 | 20.183 | 1.00 | 48.34 | C |
| ATOM | 8296 | N | VAL | G | 359 | 17.691 | 19.297 | 18.703 | 1.00 | 48.99 | N |
| ATOM | 8297 | CA | VAL | G | 359 | 17.040 | 17.997 | 18.889 | 1.00 | 50.41 | C |
| ATOM | 8298 | C | VAL | G | 359 | 16.756 | 17.800 | 20.378 | 1.00 | 51.86 | C |
| ATOM | 8299 | O | VAL | G | 359 | 17.685 | 17.740 | 21.187 | 1.00 | 51.15 | O |
| ATOM | 8300 | CB | VAL | G | 359 | 17.931 | 16.836 | 18.384 | 1.00 | 49.92 | C |
| ATOM | 8301 | CG1 | VAL | G | 359 | 17.222 | 15.503 | 18.595 | 1.00 | 49.38 | C |
| ATOM | 8302 | CG2 | VAL | G | 359 | 18.246 | 17.029 | 16.915 | 1.00 | 49.42 | C |
| ATOM | 8303 | N | LEU | G | 360 | 15.480 | 17.688 | 20.741 | 1.00 | 53.56 | N |
| ATOM | 8304 | CA | LEU | G | 360 | 15.070 | 17.535 | 22.138 | 1.00 | 54.99 | C |
| ATOM | 8305 | C | LEU | G | 360 | 14.742 | 16.092 | 22.563 | 1.00 | 56.44 | C |
| ATOM | 8306 | O | LEU | G | 360 | 14.593 | 15.216 | 21.713 | 1.00 | 55.74 | O |
| ATOM | 8307 | CB | LEU | G | 360 | 13.838 | 18.408 | 22.376 | 1.00 | 54.30 | C |
| ATOM | 8308 | CG | LEU | G | 360 | 13.939 | 19.838 | 21.853 | 1.00 | 54.34 | C |
| ATOM | 8309 | CD1 | LEU | G | 360 | 12.560 | 20.487 | 21.838 | 1.00 | 53.64 | C |
| ATOM | 8310 | CD2 | LEU | G | 360 | 14.903 | 20.630 | 22.725 | 1.00 | 53.91 | C |
| ATOM | 8311 | N | PRO | G | 361 | 14.638 | 15.837 | 23.893 | 1.00 | 58.35 | N |
| ATOM | 8312 | CA | PRO | G | 361 | 14.320 | 14.519 | 24.477 | 1.00 | 60.10 | C |
| ATOM | 8313 | C | PRO | G | 361 | 13.075 | 13.925 | 23.790 | 1.00 | 61.58 | C |
| ATOM | 8314 | O | PRO | G | 361 | 12.479 | 14.587 | 22.946 | 1.00 | 62.32 | O |
| ATOM | 8315 | CB | PRO | G | 361 | 14.132 | 14.826 | 25.973 | 1.00 | 59.69 | C |
| ATOM | 8316 | CG | PRO | G | 361 | 14.047 | 16.375 | 26.043 | 1.00 | 59.70 | C |
| ATOM | 8317 | CD | PRO | G | 361 | 14.970 | 16.805 | 24.956 | 1.00 | 58.52 | C |
| ATOM | 8318 | N | ALA | G | 362 | 12.644 | 12.721 | 24.119 | 1.00 | 63.49 | N |
| ATOM | 8319 | CA | ALA | G | 362 | 11.508 | 12.198 | 23.366 | 1.00 | 65.19 | C |
| ATOM | 8320 | C | ALA | G | 362 | 10.312 | 11.461 | 23.982 | 1.00 | 66.25 | C |
| ATOM | 8321 | O | ALA | G | 362 | 10.011 | 10.348 | 23.530 | 1.00 | 67.02 | O |
| ATOM | 8322 | CB | ALA | G | 362 | 12.049 | 11.335 | 22.194 | 1.00 | 64.93 | C |
| ATOM | 8323 | N | PRO | G | 363 | 9.635 | 12.014 | 25.008 | 1.00 | 66.83 | N |
| ATOM | 8324 | CA | PRO | G | 363 | 8.510 | 11.171 | 25.448 | 1.00 | 67.25 | C |
| ATOM | 8325 | C | PRO | G | 363 | 7.314 | 11.363 | 24.506 | 1.00 | 67.60 | C |
| ATOM | 8326 | O | PRO | G | 363 | 7.514 | 11.250 | 23.265 | 1.00 | 67.94 | O |
| ATOM | 8327 | CB | PRO | G | 363 | 8.195 | 11.695 | 26.849 | 1.00 | 67.25 | C |
| ATOM | 8328 | CG | PRO | G | 363 | 9.583 | 12.157 | 27.339 | 1.00 | 67.51 | C |
| ATOM | 8329 | CD | PRO | G | 363 | 10.079 | 12.901 | 26.099 | 1.00 | 67.27 | C |
| TER | 8330 | | PRO | G | 363 | | | | | | |
| ATOM | 8331 | N | LYS | H | 151 | 68.361 | −2.336 | 64.009 | 1.00 | 37.79 | N |
| ATOM | 8332 | CA | LYS | H | 151 | 66.948 | −2.442 | 63.538 | 1.00 | 38.61 | C |
| ATOM | 8333 | C | LYS | H | 151 | 66.342 | −1.053 | 63.268 | 1.00 | 38.86 | C |
| ATOM | 8334 | O | LYS | H | 151 | 66.335 | −0.190 | 64.150 | 1.00 | 39.10 | O |

TABLE 3-continued

| | | | | | FGFR2(D2–D3) Complexed with FGF2 | | | | | |
|---|---|---|---|---|---|---|---|---|---|---|
| ATOM | 8335 | CB | LYS | H | 151 | 66.104 | −3.180 | 64.586 | 1.00 | 38.89 | C |
| ATOM | 8336 | N | ARG | H | 152 | 65.854 | −0.836 | 62.047 | 1.00 | 38.23 | N |
| ATOM | 8337 | CA | ARG | H | 152 | 65.246 | 0.443 | 61.680 | 1.00 | 37.61 | C |
| ATOM | 8338 | C | ARG | H | 152 | 64.375 | 0.372 | 60.432 | 1.00 | 36.65 | C |
| ATOM | 8339 | O | ARG | H | 152 | 64.543 | −0.509 | 59.582 | 1.00 | 36.15 | O |
| ATOM | 8340 | CB | ARG | H | 152 | 66.321 | 1.519 | 61.477 | 1.00 | 38.33 | C |
| ATOM | 8341 | CG | ARG | H | 152 | 67.309 | 1.232 | 60.365 | 1.00 | 39.54 | C |
| ATOM | 8342 | CD | ARG | H | 152 | 68.455 | 2.260 | 60.323 | 1.00 | 40.17 | C |
| ATOM | 8343 | NE | ARG | H | 152 | 68.034 | 3.574 | 59.837 | 1.00 | 38.82 | N |
| ATOM | 8344 | CZ | ARG | H | 152 | 68.873 | 4.573 | 59.563 | 1.00 | 39.74 | C |
| ATOM | 8345 | NH1 | ARG | H | 152 | 70.179 | 4.406 | 59.727 | 1.00 | 39.28 | N |
| ATOM | 8346 | NH2 | ARG | H | 152 | 68.414 | 5.739 | 59.121 | 1.00 | 38.90 | N |
| ATOM | 8347 | N | ALA | H | 153 | 63.447 | 1.321 | 60.342 | 1.00 | 35.00 | N |
| ATOM | 8348 | CA | ALA | H | 153 | 62.519 | 1.433 | 59.225 | 1.00 | 33.97 | C |
| ATOM | 8349 | C | ALA | H | 153 | 63.284 | 1.736 | 57.935 | 1.00 | 33.19 | C |
| ATOM | 8350 | O | ALA | H | 153 | 64.443 | 2.139 | 57.976 | 1.00 | 33.04 | O |
| ATOM | 8351 | CB | ALA | H | 153 | 61.518 | 2.548 | 59.514 | 1.00 | 33.10 | C |
| ATOM | 8352 | N | PRO | H | 154 | 62.635 | 1.561 | 56.771 | 1.00 | 32.28 | N |
| ATOM | 8353 | CA | PRO | H | 154 | 63.303 | 1.831 | 55.490 | 1.00 | 32.17 | C |
| ATOM | 8354 | C | PRO | H | 154 | 63.644 | 3.308 | 55.319 | 1.00 | 32.24 | C |
| ATOM | 8355 | O | PRO | H | 154 | 62.956 | 4.181 | 55.849 | 1.00 | 31.70 | O |
| ATOM | 8356 | CB | PRO | H | 154 | 62.279 | 1.377 | 54.443 | 1.00 | 31.52 | C |
| ATOM | 8357 | CG | PRO | H | 154 | 61.340 | 0.453 | 55.213 | 1.00 | 32.11 | C |
| ATOM | 8358 | CD | PRO | H | 154 | 61.245 | 1.131 | 56.555 | 1.00 | 32.39 | C |
| ATOM | 8359 | N | TYR | H | 155 | 64.708 | 3.578 | 54.574 | 1.00 | 32.18 | N |
| ATOM | 8360 | CA | TYR | H | 155 | 65.129 | 4.944 | 54.310 | 1.00 | 32.80 | C |
| ATOM | 8361 | C | TYR | H | 155 | 65.922 | 5.019 | 53.004 | 1.00 | 32.74 | C |
| ATOM | 8362 | O | TYR | H | 155 | 66.623 | 4.073 | 52.644 | 1.00 | 33.34 | O |
| ATOM | 8363 | CB | TYR | H | 155 | 65.975 | 5.483 | 55.470 | 1.00 | 32.80 | C |
| ATOM | 8364 | CG | TYR | H | 155 | 67.319 | 4.811 | 55.635 | 1.00 | 34.02 | C |
| ATOM | 8365 | CD1 | TYR | H | 155 | 67.411 | 3.508 | 56.115 | 1.00 | 34.87 | C |
| ATOM | 8366 | CD2 | TYR | H | 155 | 68.499 | 5.477 | 55.307 | 1.00 | 34.83 | C |
| ATOM | 8367 | CE1 | TYR | H | 155 | 68.642 | 2.879 | 56.264 | 1.00 | 36.26 | C |
| ATOM | 8368 | CE2 | TYR | H | 155 | 69.744 | 4.854 | 55.453 | 1.00 | 35.52 | C |
| ATOM | 8369 | CZ | TYR | H | 155 | 69.802 | 3.557 | 55.931 | 1.00 | 36.36 | C |
| ATOM | 8370 | OH | TYR | H | 155 | 71.014 | 2.927 | 56.083 | 1.00 | 39.04 | O |
| ATOM | 8371 | N | TRP | H | 156 | 65.806 | 6.137 | 52.293 | 1.00 | 32.88 | N |
| ATOM | 8372 | CA | TRP | H | 156 | 66.529 | 6.309 | 51.031 | 1.00 | 34.25 | C |
| ATOM | 8373 | C | TRP | H | 156 | 68.018 | 6.515 | 51.302 | 1.00 | 36.20 | C |
| ATOM | 8374 | O | TRP | H | 156 | 68.391 | 7.360 | 52.112 | 1.00 | 36.60 | O |
| ATOM | 8375 | CB | TRP | H | 156 | 65.995 | 7.516 | 50.248 | 1.00 | 31.44 | C |
| ATOM | 8376 | CG | TRP | H | 156 | 64.525 | 7.485 | 50.003 | 1.00 | 29.10 | C |
| ATOM | 8377 | CD1 | TRP | H | 156 | 63.649 | 8.505 | 50.207 | 1.00 | 27.47 | C |
| ATOM | 8378 | CD2 | TRP | H | 156 | 63.751 | 6.374 | 49.528 | 1.00 | 27.11 | C |
| ATOM | 8379 | NE1 | TRP | H | 156 | 62.372 | 8.101 | 49.894 | 1.00 | 27.08 | N |
| ATOM | 8380 | CE2 | TRP | H | 156 | 62.405 | 6.800 | 49.475 | 1.00 | 26.90 | C |
| ATOM | 8381 | CE3 | TRP | H | 156 | 64.064 | 5.064 | 49.145 | 1.00 | 27.16 | C |
| ATOM | 8382 | CZ2 | TRP | H | 156 | 61.368 | 5.960 | 49.053 | 1.00 | 26.39 | C |
| ATOM | 8383 | CZ3 | TRP | H | 156 | 63.027 | 4.220 | 48.726 | 1.00 | 27.16 | C |
| ATOM | 8384 | CH2 | TRP | H | 156 | 61.695 | 4.676 | 48.685 | 1.00 | 27.77 | C |
| ATOM | 8385 | N | THR | H | 157 | 68.863 | 5.749 | 50.617 | 1.00 | 38.27 | N |
| ATOM | 8386 | CA | THR | H | 157 | 70.312 | 5.860 | 50.803 | 1.00 | 40.64 | C |
| ATOM | 8387 | C | THR | H | 157 | 70.982 | 6.820 | 49.834 | 1.00 | 42.78 | C |
| ATOM | 8388 | O | THR | H | 157 | 72.187 | 7.048 | 49.929 | 1.00 | 43.27 | O |
| ATOM | 8389 | CB | THR | H | 157 | 71.056 | 4.490 | 50.659 | 1.00 | 39.80 | C |
| ATOM | 8390 | OG1 | THR | H | 157 | 70.746 | 3.889 | 49.395 | 1.00 | 39.61 | O |
| ATOM | 8391 | CG2 | THR | H | 157 | 70.685 | 3.545 | 51.786 | 1.00 | 39.19 | C |
| ATOM | 8392 | N | ASN | H | 158 | 70.214 | 7.382 | 48.906 | 1.00 | 44.33 | N |
| ATOM | 8393 | CA | ASN | H | 158 | 70.779 | 8.304 | 47.930 | 1.00 | 46.06 | C |
| ATOM | 8394 | C | ASN | H | 158 | 69.702 | 9.157 | 47.268 | 1.00 | 46.05 | C |
| ATOM | 8395 | O | ASN | H | 158 | 69.271 | 8.871 | 46.157 | 1.00 | 46.11 | O |
| ATOM | 8396 | CB | ASN | H | 158 | 71.546 | 7.510 | 46.868 | 1.00 | 47.77 | C |
| ATOM | 8397 | CG | ASN | H | 158 | 72.210 | 8.405 | 45.838 | 1.00 | 50.73 | C |
| ATOM | 8398 | OD1 | ASN | H | 158 | 71.537 | 9.123 | 45.091 | 1.00 | 53.07 | O |
| ATOM | 8399 | ND2 | ASN | H | 158 | 73.540 | 8.374 | 45.798 | 1.00 | 51.21 | N |
| ATOM | 8400 | N | THR | H | 159 | 69.278 | 10.212 | 47.957 | 1.00 | 46.64 | N |
| ATOM | 8401 | CA | THR | H | 159 | 68.243 | 11.102 | 47.448 | 1.00 | 46.95 | C |
| ATOM | 8402 | C | THR | H | 159 | 68.667 | 11.891 | 46.221 | 1.00 | 46.70 | C |
| ATOM | 8403 | O | THR | H | 159 | 67.816 | 12.360 | 45.471 | 1.00 | 47.12 | O |
| ATOM | 8404 | CB | THR | H | 159 | 67.819 | 12.111 | 48.506 | 1.00 | 47.09 | C |
| ATOM | 8405 | OG1 | THR | H | 159 | 68.968 | 12.859 | 48.928 | 1.00 | 48.35 | O |
| ATOM | 8406 | CG2 | THR | H | 159 | 67.202 | 11.403 | 49.689 | 1.00 | 47.23 | C |
| ATOM | 8407 | N | GLU | H | 160 | 69.972 | 12.053 | 46.024 | 1.00 | 46.63 | N |
| ATOM | 8408 | CA | GLU | H | 160 | 70.471 | 12.805 | 44.877 | 1.00 | 46.12 | C |
| ATOM | 8409 | C | GLU | H | 160 | 69.952 | 12.202 | 43.575 | 1.00 | 46.04 | C |
| ATOM | 8410 | O | GLU | H | 160 | 69.453 | 12.915 | 42.713 | 1.00 | 45.59 | O |
| ATOM | 8411 | CB | GLU | H | 160 | 72.000 | 12.830 | 44.869 | 1.00 | 46.26 | C |

TABLE 3-continued

FGFR2(D2–D3) Complexed with FGF2

| ATOM | 8412 | N | LYS | H | 161 | 70.054 | 10.882 | 43.450 | 1.00 | 45.79 | H |
|---|---|---|---|---|---|---|---|---|---|---|---|
| ATOM | 8413 | CA | LYS | H | 161 | 69.600 | 10.179 | 42.256 | 1.00 | 45.35 | C |
| ATOM | 8414 | C | LYS | H | 161 | 68.072 | 10.089 | 42.139 | 1.00 | 45.08 | C |
| ATOM | 8415 | O | LYS | H | 161 | 67.561 | 9.494 | 41.192 | 1.00 | 45.43 | O |
| ATOM | 8416 | CB | LYS | H | 161 | 70.201 | 8.764 | 42.224 | 1.00 | 45.41 | C |
| ATOM | 8417 | N | MET | H | 162 | 67.346 | 10.677 | 43.088 | 1.00 | 44.29 | N |
| ATOM | 8418 | CA | MET | H | 162 | 65.880 | 10.636 | 43.067 | 1.00 | 43.74 | C |
| ATOM | 8419 | C | MET | H | 162 | 65.245 | 12.014 | 42.864 | 1.00 | 43.76 | C |
| ATOM | 8420 | O | MET | H | 162 | 64.025 | 12.122 | 42.728 | 1.00 | 43.56 | O |
| ATOM | 8421 | CB | MET | H | 162 | 65.344 | 10.032 | 44.377 | 1.00 | 42.48 | C |
| ATOM | 8422 | CG | MET | H | 162 | 65.754 | 8.586 | 44.645 | 1.00 | 40.88 | C |
| ATOM | 8423 | SD | MET | H | 162 | 65.344 | 8.030 | 46.334 | 1.00 | 40.08 | S |
| ATOM | 8424 | CE | MET | H | 162 | 63.553 | 7.764 | 46.172 | 1.00 | 39.02 | C |
| ATOM | 8425 | N | GLU | H | 163 | 66.064 | 13.062 | 42.842 | 1.00 | 43.95 | N |
| ATOM | 8426 | CA | GLU | H | 163 | 65.557 | 14.425 | 42.683 | 1.00 | 44.14 | C |
| ATOM | 8427 | C | GLU | H | 163 | 64.862 | 14.695 | 41.348 | 1.00 | 42.70 | C |
| ATOM | 8428 | O | GLU | H | 163 | 63.919 | 15.476 | 41.292 | 1.00 | 42.78 | O |
| ATOM | 8429 | CB | GLU | H | 163 | 66.691 | 15.430 | 42.882 | 1.00 | 46.35 | C |
| ATOM | 8430 | CG | GLU | H | 163 | 67.440 | 15.228 | 44.188 | 1.00 | 50.14 | C |
| ATOM | 8431 | CD | GLU | H | 163 | 68.535 | 16.253 | 44.405 | 1.00 | 51.96 | C |
| ATOM | 8432 | OE1 | GLU | H | 163 | 69.034 | 16.808 | 43.402 | 1.00 | 53.14 | O |
| ATOM | 8433 | OE2 | GLU | H | 163 | 68.906 | 16.490 | 45.578 | 1.00 | 53.48 | O |
| ATOM | 8434 | N | LYS | H | 164 | 65.333 | 14.062 | 40.278 | 1.00 | 41.20 | N |
| ATOM | 8435 | CA | LYS | H | 164 | 64.739 | 14.233 | 38.947 | 1.00 | 39.43 | C |
| ATOM | 8436 | C | LYS | H | 164 | 63.413 | 13.454 | 38.920 | 1.00 | 38.51 | C |
| ATOM | 8437 | O | LYS | H | 164 | 63.398 | 12.239 | 38.710 | 1.00 | 38.56 | O |
| ATOM | 8438 | CB | LYS | H | 164 | 65.701 | 13.694 | 37.872 | 1.00 | 38.67 | C |
| ATOM | 8439 | CG | LYS | H | 164 | 65.256 | 13.935 | 36.426 | 1.00 | 38.08 | C |
| ATOM | 8440 | CD | LYS | H | 164 | 66.199 | 13.274 | 35.408 | 1.00 | 37.42 | C |
| ATOM | 8441 | CE | LYS | H | 164 | 65.701 | 13.467 | 33.983 | 1.00 | 36.65 | C |
| ATOM | 8442 | NZ | LYS | H | 164 | 66.459 | 12.694 | 32.942 | 1.00 | 35.87 | N |
| ATOM | 8443 | N | ARG | H | 165 | 62.305 | 14.158 | 39.126 | 1.00 | 37.03 | N |
| ATOM | 8444 | CA | ARG | H | 165 | 60.990 | 13.521 | 39.167 | 1.00 | 36.21 | C |
| ATOM | 8445 | C | ARG | H | 165 | 60.399 | 13.209 | 37.799 | 1.00 | 35.48 | C |
| ATOM | 8446 | O | ARG | H | 165 | 59.831 | 12.132 | 37.582 | 1.00 | 35.58 | O |
| ATOM | 8447 | CB | ARG | H | 165 | 60.021 | 14.405 | 39.958 | 1.00 | 35.31 | C |
| ATOM | 8448 | N | LEU | H | 166 | 60.513 | 14.164 | 36.882 | 1.00 | 34.91 | N |
| ATOM | 8449 | CA | LEU | H | 166 | 59.999 | 13.991 | 35.536 | 1.00 | 34.26 | C |
| ATOM | 8450 | C | LEU | H | 166 | 61.087 | 13.485 | 34.600 | 1.00 | 33.85 | C |
| ATOM | 8451 | O | LEU | H | 166 | 62.127 | 14.124 | 34.432 | 1.00 | 34.10 | O |
| ATOM | 8452 | CB | LEU | H | 166 | 59.427 | 15.308 | 35.011 | 1.00 | 34.41 | C |
| ATOM | 8453 | CG | LEU | H | 166 | 59.113 | 15.352 | 33.509 | 1.00 | 36.55 | C |
| ATOM | 8454 | CD1 | LEU | H | 166 | 58.077 | 14.286 | 33.105 | 1.00 | 34.87 | C |
| ATOM | 8455 | CD2 | LEU | H | 166 | 58.612 | 16.746 | 33.184 | 1.00 | 37.30 | C |
| ATOM | 8456 | N | HIS | H | 167 | 60.839 | 12.319 | 34.011 | 1.00 | 33.98 | N |
| ATOM | 8457 | CA | HIS | H | 167 | 61.754 | 11.697 | 33.064 | 1.00 | 34.35 | C |
| ATOM | 8458 | C | HIS | H | 167 | 61.144 | 11.760 | 31.669 | 1.00 | 34.53 | C |
| ATOM | 8459 | O | HIS | H | 167 | 60.244 | 10.975 | 31.341 | 1.00 | 34.24 | O |
| ATOM | 8460 | CB | HIS | H | 167 | 62.002 | 10.226 | 33.414 | 1.00 | 34.98 | C |
| ATOM | 8461 | CG | HIS | H | 167 | 63.101 | 10.016 | 34.403 | 1.00 | 36.61 | C |
| ATOM | 8462 | ND1 | HIS | H | 167 | 63.021 | 10.452 | 35.707 | 1.00 | 37.72 | N |
| ATOM | 8463 | CD2 | HIS | H | 167 | 64.328 | 9.462 | 34.264 | 1.00 | 37.02 | C |
| ATOM | 8464 | CE1 | HIS | H | 167 | 64.156 | 10.180 | 36.330 | 1.00 | 37.52 | C |
| ATOM | 8465 | NE2 | HIS | H | 167 | 64.965 | 9.580 | 35.475 | 1.00 | 37.37 | N |
| ATOM | 8466 | N | ALA | H | 168 | 61.611 | 12.699 | 30.854 | 1.00 | 33.25 | N |
| ATOM | 8467 | CA | ALA | H | 168 | 61.112 | 12.811 | 29.492 | 1.00 | 32.55 | C |
| ATOM | 8468 | C | ALA | H | 168 | 62.219 | 12.260 | 28.618 | 1.00 | 32.58 | C |
| ATOM | 8469 | O | ALA | H | 168 | 63.343 | 12.762 | 28.648 | 1.00 | 32.79 | O |
| ATOM | 8470 | CB | ALA | H | 168 | 60.824 | 14.255 | 29.149 | 1.00 | 32.66 | C |
| ATOM | 8471 | N | VAL | H | 169 | 61.908 | 11.221 | 27.851 | 1.00 | 32.15 | N |
| ATOM | 8472 | CA | VAL | H | 169 | 62.904 | 10.593 | 27.001 | 1.00 | 33.27 | C |
| ATOM | 8473 | C | VAL | H | 169 | 62.395 | 10.294 | 25.599 | 1.00 | 33.21 | C |
| ATOM | 8474 | O | VAL | H | 169 | 61.200 | 10.126 | 25.376 | 1.00 | 33.45 | O |
| ATOM | 8475 | CB | VAL | H | 169 | 63.403 | 9.258 | 27.627 | 1.00 | 34.54 | C |
| ATOM | 8476 | CG1 | VAL | H | 169 | 63.759 | 9.472 | 29.110 | 1.00 | 34.94 | C |
| ATOM | 8477 | CG2 | VAL | H | 169 | 62.324 | 8.176 | 27.497 | 1.00 | 34.37 | C |
| ATOM | 8478 | N | PRO | H | 170 | 63.312 | 10.221 | 24.631 | 1.00 | 32.96 | N |
| ATOM | 8479 | CA | PRO | H | 170 | 62.909 | 9.930 | 23.258 | 1.00 | 32.75 | C |
| ATOM | 8480 | C | PRO | H | 170 | 62.512 | 8.468 | 23.093 | 1.00 | 33.59 | C |
| ATOM | 8481 | O | PRO | H | 170 | 63.074 | 7.579 | 23.746 | 1.00 | 33.16 | O |
| ATOM | 8482 | CB | PRO | H | 170 | 64.139 | 10.317 | 22.447 | 1.00 | 32.54 | C |
| ATOM | 8483 | CG | PRO | H | 170 | 65.258 | 10.129 | 23.389 | 1.00 | 33.31 | C |
| ATOM | 8484 | CD | PRO | H | 170 | 64.724 | 10.627 | 24.698 | 1.00 | 33.12 | C |
| ATOM | 8485 | N | ALA | H | 171 | 61.523 | 8.234 | 22.233 | 1.00 | 33.29 | N |
| ATOM | 8486 | CA | ALA | H | 171 | 61.026 | 6.892 | 21.964 | 1.00 | 33.83 | C |
| ATOM | 8487 | C | ALA | H | 171 | 62.169 | 5.976 | 21.563 | 1.00 | 33.64 | C |
| ATOM | 8488 | O | ALA | H | 171 | 63.141 | 6.435 | 20.963 | 1.00 | 33.64 | O |

TABLE 3-continued

FGFR2(D2–D3) Complexed with FGF2

| | | | | | | | | | | | |
|---|---|---|---|---|---|---|---|---|---|---|---|
| ATOM | 8489 | CB | ALA | H | 171 | 59.971 | 6.934 | 20.840 | 1.00 | 33.62 | C |
| ATOM | 8490 | N | ALA | H | 172 | 62.049 | 4.694 | 21.920 | 1.00 | 33.14 | N |
| ATOM | 8491 | CA | ALA | H | 172 | 63.037 | 3.661 | 21.596 | 1.00 | 33.03 | C |
| ATOM | 8492 | C | ALA | H | 172 | 64.201 | 3.536 | 22.575 | 1.00 | 33.25 | C |
| ATOM | 8493 | O | ALA | H | 172 | 65.023 | 2.628 | 22.458 | 1.00 | 34.34 | O |
| ATOM | 8494 | CB | ALA | H | 172 | 63.571 | 3.862 | 20.169 | 1.00 | 31.77 | C |
| ATOM | 8495 | N | ASN | H | 173 | 64.276 | 4.443 | 23.534 | 1.00 | 33.52 | N |
| ATOM | 8496 | CA | ASN | H | 173 | 65.337 | 4.412 | 24.534 | 1.00 | 33.97 | C |
| ATOM | 8497 | C | ASN | H | 173 | 64.952 | 3.510 | 25.709 | 1.00 | 33.74 | C |
| ATOM | 8498 | O | ASN | H | 173 | 63.795 | 3.098 | 25.848 | 1.00 | 34.12 | O |
| ATOM | 8499 | CB | ASN | H | 173 | 65.590 | 5.827 | 25.092 | 1.00 | 35.64 | C |
| ATOM | 8500 | CG | ASN | H | 173 | 66.456 | 6.694 | 24.176 | 1.00 | 35.73 | C |
| ATOM | 8501 | OD1 | ASN | H | 173 | 66.444 | 6.554 | 22.960 | 1.00 | 37.95 | O |
| ATOM | 8502 | ND2 | ASN | H | 173 | 67.190 | 7.612 | 24.772 | 1.00 | 36.54 | N |
| ATOM | 8503 | N | THR | H | 174 | 65.938 | 3.206 | 26.546 | 1.00 | 32.58 | N |
| ATOM | 8504 | CA | THR | H | 174 | 65.715 | 2.413 | 27.752 | 1.00 | 31.55 | C |
| ATOM | 8505 | C | THR | H | 174 | 65.553 | 3.405 | 28.910 | 1.00 | 30.88 | C |
| ATOM | 8506 | O | THR | H | 174 | 66.265 | 4.407 | 28.976 | 1.00 | 30.12 | O |
| ATOM | 8507 | CB | THR | H | 174 | 66.927 | 1.524 | 28.093 | 1.00 | 31.44 | C |
| ATOM | 8508 | OG1 | THR | H | 174 | 67.034 | 0.468 | 27.137 | 1.00 | 32.92 | O |
| ATOM | 8509 | CG2 | THR | H | 174 | 66.785 | 0.935 | 29.500 | 1.00 | 31.57 | C |
| ATOM | 8510 | N | VAL | H | 175 | 64.620 | 3.130 | 29.814 | 1.00 | 29.88 | N |
| ATOM | 8511 | CA | VAL | H | 175 | 64.406 | 3.994 | 30.969 | 1.00 | 29.48 | C |
| ATOM | 8512 | C | VAL | H | 175 | 64.687 | 3.217 | 32.256 | 1.00 | 28.35 | C |
| ATOM | 8513 | O | VAL | H | 175 | 64.333 | 2.042 | 32.373 | 1.00 | 28.18 | O |
| ATOM | 8514 | CB | VAL | H | 175 | 62.956 | 4.515 | 31.013 | 1.00 | 29.63 | C |
| ATOM | 8515 | CG1 | VAL | H | 175 | 62.767 | 5.425 | 32.227 | 1.00 | 29.99 | C |
| ATOM | 8516 | CG2 | VAL | H | 175 | 62.642 | 5.272 | 29.743 | 1.00 | 30.62 | C |
| ATOM | 8517 | N | LYS | H | 176 | 65.333 | 3.862 | 33.219 | 1.00 | 28.20 | N |
| ATOM | 8518 | CA | LYS | H | 176 | 65.646 | 3.214 | 34.488 | 1.00 | 28.67 | C |
| ATOM | 8519 | C | LYS | H | 176 | 65.293 | 4.100 | 35.689 | 1.00 | 29.19 | C |
| ATOM | 8520 | O | LYS | H | 176 | 65.775 | 5.230 | 35.804 | 1.00 | 28.15 | O |
| ATOM | 8521 | CB | LYS | H | 176 | 67.133 | 2.848 | 34.547 | 1.00 | 28.72 | C |
| ATOM | 8522 | N | PHE | H | 177 | 64.434 | 3.588 | 36.568 | 1.00 | 28.89 | N |
| ATOM | 8523 | CA | PHE | H | 177 | 64.042 | 4.322 | 37.765 | 1.00 | 29.43 | C |
| ATOM | 8524 | C | PHE | H | 177 | 64.709 | 3.653 | 38.956 | 1.00 | 30.25 | C |
| ATOM | 8525 | O | PHE | H | 177 | 64.759 | 2.424 | 39.037 | 1.00 | 29.85 | O |
| ATOM | 8526 | CB | PHE | H | 177 | 62.515 | 4.304 | 37.952 | 1.00 | 28.61 | C |
| ATOM | 8527 | CG | PHE | H | 177 | 61.759 | 5.072 | 36.894 | 1.00 | 27.90 | C |
| ATOM | 8528 | CD1 | PHE | H | 177 | 62.108 | 6.378 | 36.584 | 1.00 | 27.39 | C |
| ATOM | 8529 | CD2 | PHE | H | 177 | 60.697 | 4.488 | 36.215 | 1.00 | 27.63 | C |
| ATOM | 8530 | CE1 | PHE | H | 177 | 61.416 | 7.090 | 35.615 | 1.00 | 27.68 | C |
| ATOM | 8531 | CE2 | PHE | H | 177 | 59.996 | 5.189 | 35.246 | 1.00 | 26.69 | C |
| ATOM | 8532 | CZ | PHE | H | 177 | 60.353 | 6.491 | 34.944 | 1.00 | 27.27 | C |
| ATOM | 8533 | N | ARG | H | 178 | 65.224 | 4.457 | 39.878 | 1.00 | 31.24 | N |
| ATOM | 8534 | CA | ARG | H | 178 | 65.885 | 3.907 | 41.052 | 1.00 | 31.69 | C |
| ATOM | 8535 | C | ARG | H | 178 | 65.415 | 4.535 | 42.356 | 1.00 | 30.80 | C |
| ATOM | 8536 | O | ARG | H | 178 | 65.060 | 5.709 | 42.396 | 1.00 | 29.30 | O |
| ATOM | 8537 | CB | ARG | H | 178 | 67.404 | 4.075 | 40.930 | 1.00 | 33.79 | C |
| ATOM | 8538 | CG | ARG | H | 178 | 68.001 | 3.388 | 39.718 | 1.00 | 38.62 | C |
| ATOM | 8539 | CD | ARG | H | 178 | 69.510 | 3.228 | 39.866 | 1.00 | 41.50 | C |
| ATOM | 8540 | NE | ARG | H | 178 | 69.851 | 2.593 | 41.137 | 1.00 | 45.13 | N |
| ATOM | 8541 | CZ | ARG | H | 178 | 71.029 | 2.039 | 41.415 | 1.00 | 47.50 | C |
| ATOM | 8542 | NH1 | ARG | H | 178 | 71.997 | 2.030 | 40.503 | 1.00 | 48.51 | N |
| ATOM | 8543 | NH2 | ARG | H | 178 | 71.240 | 1.490 | 42.607 | 1.00 | 48.12 | N |
| ATOM | 8544 | N | CYS | H | 179 | 65.420 | 3.727 | 43.420 | 1.00 | 30.39 | N |
| ATOM | 8545 | CA | CYS | H | 179 | 65.042 | 4.166 | 44.756 | 1.00 | 31.12 | C |
| ATOM | 8546 | C | CYS | H | 179 | 65.958 | 3.453 | 45.753 | 1.00 | 31.65 | C |
| ATOM | 8547 | O | CYS | H | 179 | 65.517 | 2.600 | 46.535 | 1.00 | 29.30 | O |
| ATOM | 8548 | CB | CYS | H | 179 | 63.582 | 3.810 | 45.039 | 1.00 | 32.01 | C |
| ATOM | 8549 | SG | CYS | H | 179 | 62.446 | 4.620 | 43.899 | 1.00 | 33.46 | S |
| ATOM | 8550 | N | PRO | H | 180 | 67.260 | 3.794 | 45.730 | 1.00 | 31.88 | N |
| ATOM | 8551 | CA | PRO | H | 180 | 68.246 | 3.178 | 46.628 | 1.00 | 32.79 | C |
| ATOM | 8552 | C | PRO | H | 180 | 67.774 | 3.257 | 48.072 | 1.00 | 32.81 | C |
| ATOM | 8553 | O | PRO | H | 180 | 67.543 | 4.345 | 48.594 | 1.00 | 32.89 | O |
| ATOM | 8554 | CB | PRO | H | 180 | 69.501 | 4.008 | 46.378 | 1.00 | 32.58 | C |
| ATOM | 8555 | CG | PRO | H | 180 | 69.347 | 4.405 | 44.941 | 1.00 | 32.95 | C |
| ATOM | 8556 | CD | PRO | H | 180 | 67.894 | 4.811 | 44.879 | 1.00 | 32.19 | C |
| ATOM | 8557 | N | ALA | H | 181 | 67.621 | 2.106 | 48.717 | 1.00 | 33.06 | N |
| ATOM | 8558 | CA | ALA | H | 181 | 67.143 | 2.102 | 50.094 | 1.00 | 35.06 | C |
| ATOM | 8559 | C | ALA | H | 181 | 67.959 | 1.268 | 51.070 | 1.00 | 36.08 | C |
| ATOM | 8560 | O | ALA | H | 181 | 68.712 | 0.371 | 50.681 | 1.00 | 35.98 | O |
| ATOM | 8561 | CB | ALA | H | 181 | 65.681 | 1.646 | 50.138 | 1.00 | 34.31 | C |
| ATOM | 8562 | N | GLY | H | 182 | 67.779 | 1.584 | 52.350 | 1.00 | 36.73 | N |
| ATOM | 8563 | CA | GLY | H | 182 | 68.449 | 0.874 | 53.423 | 1.00 | 37.41 | C |
| ATOM | 8564 | C | GLY | H | 182 | 67.396 | 0.466 | 54.438 | 1.00 | 38.30 | C |
| ATOM | 8565 | O | GLY | H | 182 | 66.236 | 0.872 | 54.319 | 1.00 | 37.63 | O |

TABLE 3-continued

FGFR2(D2–D3) Complexed with FGF2

| ATOM | 8566 | N | GLY | H | 183 | 67.786 | −0.331 | 55.430 | 1.00 | 38.77 | N |
|---|---|---|---|---|---|---|---|---|---|---|---|
| ATOM | 8567 | CA | GLY | H | 183 | 66.843 | −0.768 | 56.447 | 1.00 | 39.20 | C |
| ATOM | 8568 | C | GLY | H | 183 | 67.203 | −2.112 | 57.061 | 1.00 | 40.18 | C |
| ATOM | 8569 | O | GLY | H | 183 | 67.873 | −2.932 | 56.436 | 1.00 | 40.21 | O |
| ATOM | 8570 | N | ASN | H | 184 | 66.740 | −2.347 | 58.284 | 1.00 | 40.96 | N |
| ATOM | 8571 | CA | ASN | H | 184 | 67.026 | −3.584 | 58.993 | 1.00 | 41.48 | C |
| ATOM | 8572 | C | ASN | H | 184 | 65.809 | −4.038 | 59.785 | 1.00 | 41.66 | C |
| ATOM | 8573 | O | ASN | H | 184 | 65.433 | −3.406 | 60.764 | 1.00 | 41.94 | O |
| ATOM | 8574 | CB | ASN | H | 184 | 68.209 | −3.365 | 59.942 | 1.00 | 41.99 | C |
| ATOM | 8575 | CG | ASN | H | 184 | 68.613 | −4.627 | 60.689 | 1.00 | 43.13 | C |
| ATOM | 8576 | OD1 | ASN | H | 184 | 69.569 | −4.612 | 61.464 | 1.00 | 43.80 | O |
| ATOM | 8577 | ND2 | ASN | H | 184 | 67.889 | −5.720 | 60.463 | 1.00 | 43.04 | N |
| ATOM | 8578 | N | PRO | H | 185 | 65.207 | −5.171 | 59.400 | 1.00 | 42.08 | N |
| ATOM | 8579 | CA | PRO | H | 185 | 65.603 | −6.036 | 58.287 | 1.00 | 42.78 | C |
| ATOM | 8580 | C | PRO | H | 185 | 65.487 | −5.416 | 56.893 | 1.00 | 43.55 | C |
| ATOM | 8581 | O | PRO | H | 185 | 64.825 | −4.387 | 56.701 | 1.00 | 43.80 | O |
| ATOM | 8582 | CB | PRO | H | 185 | 64.694 | −7.253 | 58.469 | 1.00 | 42.73 | C |
| ATOM | 8583 | CG | PRO | H | 185 | 63.469 | −6.662 | 59.064 | 1.00 | 42.91 | C |
| ATOM | 8584 | CD | PRO | H | 185 | 64.032 | −5.724 | 60.094 | 1.00 | 41.94 | C |
| ATOM | 8585 | N | MET | H | 186 | 66.148 | −6.050 | 55.927 | 1.00 | 43.56 | N |
| ATOM | 8586 | CA | MET | H | 186 | 66.137 | −5.585 | 54.547 | 1.00 | 43.87 | C |
| ATOM | 8587 | C | MET | H | 186 | 64.720 | −5.393 | 54.045 | 1.00 | 42.88 | C |
| ATOM | 8588 | O | MET | H | 186 | 63.924 | −6.333 | 54.010 | 1.00 | 42.19 | O |
| ATOM | 8589 | CB | MET | H | 186 | 66.854 | −6.582 | 53.638 | 1.00 | 45.83 | C |
| ATOM | 8590 | CG | MET | H | 186 | 68.277 | −6.195 | 53.298 | 1.00 | 48.98 | C |
| ATOM | 8591 | SD | MET | H | 186 | 68.350 | −4.713 | 52.263 | 1.00 | 51.20 | S |
| ATOM | 8592 | CE | MET | H | 186 | 68.901 | −3.490 | 53.482 | 1.00 | 51.08 | C |
| ATOM | 8593 | N | PRO | H | 187 | 64.380 | −4.163 | 53.653 | 1.00 | 41.92 | N |
| ATOM | 8594 | CA | PRO | H | 187 | 63.027 | −3.912 | 53.156 | 1.00 | 41.63 | C |
| ATOM | 8595 | C | PRO | H | 187 | 62.761 | −4.492 | 51.763 | 1.00 | 41.02 | C |
| ATOM | 8596 | O | PRO | H | 187 | 63.684 | −4.696 | 50.971 | 1.00 | 40.91 | O |
| ATOM | 8597 | CB | PRO | H | 187 | 62.917 | −2.388 | 53.201 | 1.00 | 41.73 | C |
| ATOM | 8598 | CG | PRO | H | 187 | 64.321 | −1.939 | 52.994 | 1.00 | 42.27 | C |
| ATOM | 8599 | CD | PRO | H | 187 | 65.117 | −2.902 | 53.846 | 1.00 | 41.98 | C |
| ATOM | 8600 | N | THR | H | 188 | 61.492 | −4.773 | 51.487 | 1.00 | 40.31 | N |
| ATOM | 8601 | CA | THR | H | 188 | 61.086 | −5.305 | 50.197 | 1.00 | 40.35 | C |
| ATOM | 8602 | C | THR | H | 188 | 60.740 | −4.127 | 49.291 | 1.00 | 40.63 | C |
| ATOM | 8603 | O | THR | H | 188 | 60.550 | −3.010 | 49.761 | 1.00 | 41.57 | O |
| ATOM | 8604 | CB | THR | H | 188 | 59.875 | −6.242 | 50.340 | 1.00 | 39.84 | C |
| ATOM | 8605 | OG1 | THR | H | 188 | 58.766 | −5.523 | 50.894 | 1.00 | 40.00 | O |
| ATOM | 8606 | CG2 | THR | H | 188 | 60.223 | −7.405 | 51.254 | 1.00 | 38.95 | C |
| ATOM | 8607 | N | MET | H | 189 | 60.646 | −4.390 | 47.997 | 1.00 | 40.93 | N |
| ATOM | 8608 | CA | MET | H | 189 | 60.376 | −3.356 | 47.013 | 1.00 | 41.37 | C |
| ATOM | 8609 | C | MET | H | 189 | 59.282 | −3.777 | 46.036 | 1.00 | 40.54 | C |
| ATOM | 8610 | O | MET | H | 189 | 59.279 | −4.906 | 45.551 | 1.00 | 40.87 | O |
| ATOM | 8611 | CB | MET | H | 189 | 61.684 | −3.076 | 46.258 | 1.00 | 43.68 | C |
| ATOM | 8612 | CG | MET | H | 189 | 61.549 | −2.518 | 44.858 | 1.00 | 47.65 | C |
| ATOM | 8613 | SD | MET | H | 189 | 61.934 | −0.765 | 44.822 | 1.00 | 53.13 | S |
| ATOM | 8614 | CE | MET | H | 189 | 60.298 | −0.119 | 45.325 | 1.00 | 51.14 | C |
| ATOM | 8615 | N | ARG | H | 190 | 58.357 | −2.863 | 45.758 | 1.00 | 39.03 | N |
| ATOM | 8616 | CA | ARG | H | 190 | 57.272 | −3.111 | 44.815 | 1.00 | 38.27 | C |
| ATOM | 8617 | C | ARG | H | 190 | 57.087 | −1.863 | 43.955 | 1.00 | 36.15 | C |
| ATOM | 8618 | O | ARG | H | 190 | 57.212 | −0.750 | 44.462 | 1.00 | 35.06 | O |
| ATOM | 8619 | CB | ARG | H | 190 | 55.962 | −3.388 | 45.551 | 1.00 | 40.41 | C |
| ATOM | 8620 | CG | ARG | H | 190 | 56.086 | −4.286 | 46.753 | 1.00 | 44.73 | C |
| ATOM | 8621 | CD | ARG | H | 190 | 54.723 | −4.863 | 47.109 | 1.00 | 47.23 | C |
| ATOM | 8622 | NE | ARG | H | 190 | 53.677 | −3.841 | 47.119 | 1.00 | 50.38 | N |
| ATOM | 8623 | CZ | ARG | H | 190 | 53.563 | −2.882 | 48.035 | 1.00 | 51.38 | C |
| ATOM | 8624 | NH1 | ARG | H | 190 | 54.432 | −2.803 | 49.036 | 1.00 | 52.06 | N |
| ATOM | 8625 | NH2 | ARG | H | 190 | 52.576 | −1.999 | 47.949 | 1.00 | 52.44 | N |
| ATOM | 8626 | N | TRP | H | 191 | 56.790 | −2.046 | 42.669 | 1.00 | 34.17 | N |
| ATOM | 8627 | CA | TRP | H | 191 | 56.575 | −0.912 | 41.770 | 1.00 | 33.18 | C |
| ATOM | 8628 | C | TRP | H | 191 | 55.133 | −0.826 | 41.275 | 1.00 | 32.69 | C |
| ATOM | 8629 | O | TRP | H | 191 | 54.528 | −1.831 | 40.913 | 1.00 | 33.43 | O |
| ATOM | 8630 | CB | TRP | H | 191 | 57.512 | −0.987 | 40.569 | 1.00 | 33.46 | C |
| ATOM | 8631 | CG | TRP | H | 191 | 58.941 | −0.736 | 40.908 | 1.00 | 33.49 | C |
| ATOM | 8632 | CD1 | TRP | H | 191 | 59.846 | −1.645 | 41.370 | 1.00 | 33.78 | C |
| ATOM | 8633 | CD2 | TRP | H | 191 | 59.628 | 0.519 | 40.836 | 1.00 | 32.79 | C |
| ATOM | 8634 | NE1 | TRP | H | 191 | 61.059 | −1.034 | 41.589 | 1.00 | 34.46 | N |
| ATOM | 8635 | CE2 | TRP | H | 191 | 60.955 | 0.293 | 41.271 | 1.00 | 32.88 | C |
| ATOM | 8636 | CE3 | TRP | H | 191 | 59.252 | 1.811 | 40.450 | 1.00 | 31.84 | C |
| ATOM | 8637 | CZ2 | TRP | H | 191 | 61.909 | 1.313 | 41.331 | 1.00 | 32.39 | C |
| ATOM | 8638 | CZ3 | TRP | H | 191 | 60.199 | 2.829 | 40.512 | 1.00 | 31.53 | C |
| ATOM | 8639 | CH2 | TRP | H | 191 | 61.516 | 2.571 | 40.949 | 1.00 | 32.25 | C |
| ATOM | 8640 | N | LEU | H | 192 | 54.591 | 0.382 | 41.256 | 1.00 | 31.74 | N |
| ATOM | 8641 | CA | LEU | H | 192 | 53.225 | 0.590 | 40.808 | 1.00 | 31.83 | C |
| ATOM | 8642 | C | LEU | H | 192 | 53.202 | 1.484 | 39.575 | 1.00 | 31.69 | C |

TABLE 3-continued

| | | | | | FGFR2(D2–D3) Complexed with FGF2 | | | | | |
|---|---|---|---|---|---|---|---|---|---|---|
| ATOM | 8643 | O | LEU | H | 192 | 54.067 | 2.356 | 39.411 | 1.00 | 31.36 | O |
| ATOM | 8644 | CB | LEU | H | 192 | 52.405 | 1.258 | 41.922 | 1.00 | 32.15 | C |
| ATOM | 8645 | CG | LEU | H | 192 | 52.519 | 0.633 | 43.320 | 1.00 | 33.26 | C |
| ATOM | 8646 | CD1 | LEU | H | 192 | 51.813 | 1.518 | 44.342 | 1.00 | 33.37 | C |
| ATOM | 8647 | CD2 | LEU | H | 192 | 51.928 | −0.774 | 43.308 | 1.00 | 32.33 | C |
| ATOM | 8648 | N | LYS | H | 193 | 52.228 | 1.247 | 38.700 | 1.00 | 31.27 | N |
| ATOM | 8649 | CA | LYS | H | 193 | 52.056 | 2.078 | 37.521 | 1.00 | 31.38 | C |
| ATOM | 8650 | C | LYS | H | 193 | 50.704 | 2.745 | 37.724 | 1.00 | 32.24 | C |
| ATOM | 8651 | O | LYS | H | 193 | 49.682 | 2.061 | 37.839 | 1.00 | 32.34 | O |
| ATOM | 8652 | CB | LYS | H | 193 | 52.032 | 1.263 | 36.230 | 1.00 | 30.70 | C |
| ATOM | 8653 | CG | LYS | H | 193 | 51.719 | 2.146 | 35.016 | 1.00 | 31.36 | C |
| ATOM | 8654 | CD | LYS | H | 193 | 51.678 | 1.383 | 33.707 | 1.00 | 32.10 | C |
| ATOM | 8655 | CE | LYS | H | 193 | 51.375 | 2.330 | 32.542 | 1.00 | 32.57 | C |
| ATOM | 8656 | NZ | LYS | H | 193 | 51.390 | 1.655 | 31.212 | 1.00 | 31.31 | N |
| ATOM | 8657 | N | ASN | H | 194 | 50.700 | 4.073 | 37.775 | 1.00 | 32.87 | N |
| ATOM | 8658 | CA | ASN | H | 194 | 49.466 | 4.821 | 37.980 | 1.00 | 34.49 | C |
| ATOM | 8659 | C | ASN | H | 194 | 48.725 | 4.323 | 39.225 | 1.00 | 35.42 | C |
| ATOM | 8660 | O | ASN | H | 194 | 47.523 | 4.050 | 39.177 | 1.00 | 34.66 | O |
| ATOM | 8661 | CB | ASN | H | 194 | 48.558 | 4.699 | 36.757 | 1.00 | 35.20 | C |
| ATOM | 8662 | CG | ASN | H | 194 | 49.175 | 5.295 | 35.520 | 1.00 | 37.23 | C |
| ATOM | 8663 | OD1 | ASN | H | 194 | 49.780 | 6.377 | 35.566 | 1.00 | 37.24 | O |
| ATOM | 8664 | ND2 | ASN | H | 194 | 49.021 | 4.604 | 34.396 | 1.00 | 38.07 | N |
| ATOM | 8665 | N | GLY | H | 195 | 49.465 | 4.185 | 40.324 | 1.00 | 35.49 | N |
| ATOM | 8666 | CA | GLY | H | 195 | 48.894 | 3.755 | 41.588 | 1.00 | 35.87 | C |
| ATOM | 8667 | C | GLY | H | 195 | 48.380 | 2.331 | 41.728 | 1.00 | 36.60 | C |
| ATOM | 8668 | O | GLY | H | 195 | 47.733 | 2.012 | 42.726 | 1.00 | 37.28 | O |
| ATOM | 8669 | N | LYS | H | 196 | 48.659 | 1.470 | 40.756 | 1.00 | 36.84 | N |
| ATOM | 8670 | CA | LYS | H | 196 | 48.200 | 0.083 | 40.813 | 1.00 | 36.47 | C |
| ATOM | 8671 | C | LYS | H | 196 | 49.342 | −0.859 | 40.468 | 1.00 | 36.66 | C |
| ATOM | 8672 | O | LYS | H | 196 | 50.306 | −0.458 | 39.813 | 1.00 | 36.79 | O |
| ATOM | 8673 | CB | LYS | H | 196 | 47.047 | −0.144 | 39.826 | 1.00 | 36.59 | C |
| ATOM | 8674 | N | GLU | H | 197 | 49.224 | −2.110 | 40.898 | 1.00 | 36.27 | N |
| ATOM | 8675 | CA | GLU | H | 197 | 50.250 | −3.111 | 40.628 | 1.00 | 36.93 | C |
| ATOM | 8676 | C | GLU | H | 197 | 50.646 | −3.071 | 39.159 | 1.00 | 37.24 | C |
| ATOM | 8677 | O | GLU | H | 197 | 49.788 | −3.011 | 38.277 | 1.00 | 37.37 | O |
| ATOM | 8678 | CB | GLU | H | 197 | 49.743 | −4.513 | 40.978 | 1.00 | 36.22 | C |
| ATOM | 8679 | N | PHE | H | 198 | 51.955 | −3.088 | 38.912 | 1.00 | 37.40 | N |
| ATOM | 8680 | CA | PHE | H | 198 | 52.519 | −3.059 | 37.564 | 1.00 | 37.00 | C |
| ATOM | 8681 | C | PHE | H | 198 | 52.834 | −4.508 | 37.209 | 1.00 | 38.01 | C |
| ATOM | 8682 | O | PHE | H | 198 | 53.680 | −5.140 | 37.850 | 1.00 | 38.55 | O |
| ATOM | 8683 | CB | PHE | H | 198 | 53.810 | −2.225 | 37.557 | 1.00 | 36.91 | C |
| ATOM | 8684 | CG | PHE | H | 198 | 54.419 | −2.007 | 36.182 | 1.00 | 36.86 | C |
| ATOM | 8685 | CD1 | PHE | H | 198 | 55.758 | −1.631 | 36.062 | 1.00 | 36.29 | C |
| ATOM | 8686 | CD2 | PHE | H | 198 | 53.660 | −2.138 | 35.020 | 1.00 | 36.71 | C |
| ATOM | 8687 | CE1 | PHE | H | 198 | 56.335 | −1.386 | 34.809 | 1.00 | 36.73 | C |
| ATOM | 8688 | CE2 | PHE | H | 198 | 54.224 | −1.895 | 33.759 | 1.00 | 37.32 | C |
| ATOM | 8689 | CZ | PHE | H | 198 | 55.565 | −1.518 | 33.653 | 1.00 | 37.03 | C |
| ATOM | 8690 | N | LYS | H | 199 | 52.152 | −5.037 | 36.197 | 1.00 | 38.20 | N |
| ATOM | 8691 | CA | LYS | H | 199 | 52.361 | −6.417 | 35.775 | 1.00 | 38.43 | C |
| ATOM | 8692 | C | LYS | H | 199 | 53.114 | −6.528 | 34.449 | 1.00 | 38.45 | C |
| ATOM | 8693 | O | LYS | H | 199 | 53.064 | −5.622 | 33.615 | 1.00 | 37.89 | O |
| ATOM | 8694 | CB | LYS | H | 199 | 51.011 | −7.130 | 35.653 | 1.00 | 39.27 | C |
| ATOM | 8695 | N | GLN | H | 200 | 53.808 | −7.646 | 34.256 | 1.00 | 38.02 | N |
| ATOM | 8696 | CA | GLN | H | 200 | 54.568 | −7.875 | 33.032 | 1.00 | 38.31 | C |
| ATOM | 8697 | C | GLN | H | 200 | 53.728 | −7.698 | 31.768 | 1.00 | 39.07 | C |
| ATOM | 8698 | O | GLN | H | 200 | 54.214 | −7.170 | 30.765 | 1.00 | 39.42 | O |
| ATOM | 8699 | CB | GLN | H | 200 | 55.172 | −9.286 | 33.015 | 1.00 | 37.92 | C |
| ATOM | 8700 | CG | GLN | H | 200 | 56.330 | −9.514 | 33.978 | 1.00 | 37.78 | C |
| ATOM | 8701 | CD | GLN | H | 200 | 57.578 | −8.707 | 33.622 | 1.00 | 37.85 | C |
| ATOM | 8702 | OE1 | GLN | H | 200 | 57.985 | −8.634 | 32.455 | 1.00 | 37.06 | O |
| ATOM | 8703 | NE2 | GLN | H | 200 | 58.197 | −8.111 | 34.632 | 1.00 | 37.78 | N |
| ATOM | 8704 | N | GLU | H | 201 | 52.473 | −8.136 | 31.803 | 1.00 | 39.36 | N |
| ATOM | 8705 | CA | GLU | H | 201 | 51.623 | −8.020 | 30.621 | 1.00 | 39.62 | C |
| ATOM | 8706 | C | GLU | H | 201 | 51.113 | −6.596 | 30.366 | 1.00 | 39.23 | C |
| ATOM | 8707 | O | GLU | H | 201 | 50.416 | −6.350 | 29.381 | 1.00 | 38.74 | O |
| ATOM | 8708 | CB | GLU | H | 201 | 50.431 | −8.986 | 30.713 | 1.00 | 41.36 | C |
| ATOM | 8709 | CG | GLU | H | 201 | 49.343 | −8.550 | 31.678 | 1.00 | 44.13 | C |
| ATOM | 8710 | CD | GLU | H | 201 | 49.234 | −9.456 | 32.888 | 1.00 | 46.42 | C |
| ATOM | 8711 | OE1 | GLU | H | 201 | 50.276 | −9.701 | 33.541 | 1.00 | 47.29 | O |
| ATOM | 8712 | OE2 | GLU | H | 201 | 48.105 | −9.916 | 33.189 | 1.00 | 47.42 | O |
| ATOM | 8713 | N | HIS | H | 202 | 51.465 | −5.656 | 31.236 | 1.00 | 39.09 | N |
| ATOM | 8714 | CA | HIS | H | 202 | 51.015 | −4.281 | 31.060 | 1.00 | 38.39 | C |
| ATOM | 8715 | C | HIS | H | 202 | 51.687 | −3.527 | 29.901 | 1.00 | 37.42 | C |
| ATOM | 8716 | O | HIS | H | 202 | 51.258 | −2.427 | 29.541 | 1.00 | 36.70 | O |
| ATOM | 8717 | CB | HIS | H | 202 | 51.164 | −3.515 | 32.376 | 1.00 | 40.07 | C |
| ATOM | 8718 | CG | HIS | H | 202 | 50.119 | −3.863 | 33.391 | 1.00 | 42.25 | C |
| ATOM | 8719 | ND1 | HIS | H | 202 | 48.978 | −4.575 | 33.072 | 1.00 | 41.73 | N |

TABLE 3-continued

FGFR2(D2–D3) Complexed with FGF2

| ATOM | 8720 | CD2 | HIS | H | 202 | 50.017 | −3.563 | 34.709 | 1.00 | 42.67 | C |
|---|---|---|---|---|---|---|---|---|---|---|---|
| ATOM | 8721 | CE1 | HIS | H | 202 | 48.222 | −4.695 | 34.148 | 1.00 | 42.51 | C |
| ATOM | 8722 | NE2 | HIS | H | 202 | 48.827 | −4.090 | 35.155 | 1.00 | 43.17 | N |
| ATOM | 8723 | N | ARG | H | 203 | 52.731 | −4.120 | 29.315 | 1.00 | 36.47 | N |
| ATOM | 8724 | CA | ARG | H | 203 | 53.429 | −3.508 | 28.169 | 1.00 | 35.54 | C |
| ATOM | 8725 | C | ARG | H | 203 | 54.157 | −4.563 | 27.339 | 1.00 | 35.60 | C |
| ATOM | 8726 | O | ARG | H | 203 | 54.540 | −5.614 | 27.850 | 1.00 | 35.55 | O |
| ATOM | 8727 | CB | ARG | H | 203 | 54.445 | −2.438 | 28.617 | 1.00 | 34.59 | C |
| ATOM | 8728 | CG | ARG | H | 203 | 55.832 | −2.971 | 29.006 | 1.00 | 33.37 | C |
| ATOM | 8729 | CD | ARG | H | 203 | 56.737 | −1.854 | 29.562 | 1.00 | 32.84 | C |
| ATOM | 8730 | NE | ARG | H | 203 | 57.270 | −0.955 | 28.533 | 1.00 | 30.57 | N |
| ATOM | 8731 | CZ | ARG | H | 203 | 58.413 | −1.159 | 27.882 | 1.00 | 29.72 | C |
| ATOM | 8732 | NH1 | ARG | H | 203 | 59.147 | −2.234 | 28.150 | 1.00 | 29.07 | N |
| ATOM | 8733 | NH2 | ARG | H | 203 | 58.829 | −0.285 | 26.973 | 1.00 | 29.38 | N |
| ATOM | 8734 | N | ILE | H | 204 | 54.345 | −4.284 | 26.054 | 1.00 | 35.87 | N |
| ATOM | 8735 | CA | ILE | H | 204 | 55.050 | −5.221 | 25.181 | 1.00 | 37.45 | C |
| ATOM | 8736 | C | ILE | H | 204 | 56.449 | −5.450 | 25.769 | 1.00 | 37.69 | C |
| ATOM | 8737 | O | ILE | H | 204 | 57.172 | −4.492 | 26.053 | 1.00 | 37.77 | O |
| ATOM | 8738 | CB | ILE | H | 204 | 55.232 | −4.654 | 23.741 | 1.00 | 38.36 | C |
| ATOM | 8739 | CG1 | ILE | H | 204 | 53.878 | −4.332 | 23.099 | 1.00 | 39.88 | C |
| ATOM | 8740 | CG2 | ILE | H | 204 | 55.968 | −5.673 | 22.876 | 1.00 | 39.29 | C |
| ATOM | 8741 | CD1 | ILE | H | 204 | 53.061 | −5.548 | 22.712 | 1.00 | 40.07 | C |
| ATOM | 8742 | N | GLY | H | 205 | 56.824 | −6.709 | 25.958 | 1.00 | 37.43 | N |
| ATOM | 8743 | CA | GLY | H | 205 | 58.138 | −7.011 | 26.500 | 1.00 | 37.45 | C |
| ATOM | 8744 | C | GLY | H | 205 | 58.290 | −6.855 | 28.002 | 1.00 | 37.05 | C |
| ATOM | 8745 | O | GLY | H | 205 | 59.377 | −7.089 | 28.538 | 1.00 | 37.32 | O |
| ATOM | 8746 | N | GLY | H | 206 | 57.217 | −6.456 | 28.683 | 1.00 | 36.41 | N |
| ATOM | 8747 | CA | GLY | H | 206 | 57.271 | −6.298 | 30.129 | 1.00 | 35.85 | C |
| ATOM | 8748 | C | GLY | H | 206 | 58.381 | −5.406 | 30.661 | 1.00 | 35.30 | C |
| ATOM | 8749 | O | GLY | H | 206 | 58.754 | −4.416 | 30.034 | 1.00 | 34.59 | O |
| ATOM | 8750 | N | TYR | H | 207 | 58.907 | −5.757 | 31.830 | 1.00 | 36.01 | N |
| ATOM | 8751 | CA | TYR | H | 207 | 59.967 | −4.974 | 32.448 | 1.00 | 36.69 | C |
| ATOM | 8752 | C | TYR | H | 207 | 60.936 | −5.836 | 33.257 | 1.00 | 36.92 | C |
| ATOM | 8753 | O | TYR | H | 207 | 60.720 | −7.037 | 33.437 | 1.00 | 35.87 | O |
| ATOM | 8754 | CB | TYR | H | 207 | 59.362 | −3.901 | 33.352 | 1.00 | 37.45 | C |
| ATOM | 8755 | CG | TYR | H | 207 | 58.487 | −4.456 | 34.449 | 1.00 | 38.55 | C |
| ATOM | 8756 | CD1 | TYR | H | 207 | 57.111 | −4.617 | 34.267 | 1.00 | 38.56 | C |
| ATOM | 8757 | CD2 | TYR | H | 207 | 59.040 | −4.837 | 35.673 | 1.00 | 39.04 | C |
| ATOM | 8758 | CE1 | TYR | H | 207 | 56.302 | −5.144 | 35.289 | 1.00 | 39.03 | C |
| ATOM | 8759 | CE2 | TYR | H | 207 | 58.253 | −5.367 | 36.692 | 1.00 | 39.41 | C |
| ATOM | 8760 | CZ | TYR | H | 207 | 56.886 | −5.518 | 36.499 | 1.00 | 40.67 | C |
| ATOM | 8761 | OH | TYR | H | 207 | 56.119 | −6.041 | 37.523 | 1.00 | 41.90 | O |
| ATOM | 8762 | N | LYS | H | 208 | 62.005 | −5.210 | 33.744 | 1.00 | 36.64 | N |
| ATOM | 8763 | CA | LYS | H | 208 | 62.998 | −5.917 | 34.533 | 1.00 | 37.93 | C |
| ATOM | 8764 | C | LYS | H | 208 | 63.275 | −5.173 | 35.839 | 1.00 | 38.82 | C |
| ATOM | 8765 | O | LYS | H | 208 | 63.281 | −3.942 | 35.879 | 1.00 | 38.86 | O |
| ATOM | 8766 | CB | LYS | H | 208 | 64.296 | −6.076 | 33.729 | 1.00 | 37.63 | C |
| ATOM | 8767 | CG | LYS | H | 208 | 64.115 | −6.787 | 32.381 | 1.00 | 37.50 | C |
| ATOM | 8768 | CD | LYS | H | 208 | 65.439 | −6.901 | 31.637 | 1.00 | 35.87 | C |
| ATOM | 8769 | CE | LYS | H | 208 | 65.296 | −7.633 | 30.323 | 1.00 | 34.97 | C |
| ATOM | 8770 | NZ | LYS | H | 208 | 66.601 | −7.668 | 29.613 | 1.00 | 35.16 | N |
| ATOM | 8771 | N | VAL | H | 209 | 63.499 | −5.931 | 36.906 | 1.00 | 40.16 | N |
| ATOM | 8772 | CA | VAL | H | 209 | 63.782 | −5.357 | 38.218 | 1.00 | 42.42 | C |
| ATOM | 8773 | C | VAL | H | 209 | 65.049 | −5.964 | 38.793 | 1.00 | 43.29 | C |
| ATOM | 8774 | O | VAL | H | 209 | 65.201 | −7.181 | 38.817 | 1.00 | 44.11 | O |
| ATOM | 8775 | CB | VAL | H | 209 | 62.623 | −5.625 | 39.221 | 1.00 | 42.75 | C |
| ATOM | 8776 | CG1 | VAL | H | 209 | 63.016 | −5.146 | 40.611 | 1.00 | 43.25 | C |
| ATOM | 8777 | CG2 | VAL | H | 209 | 61.355 | −4.912 | 38.768 | 1.00 | 42.93 | C |
| ATOM | 8778 | N | ARG | H | 210 | 65.960 | −5.109 | 39.244 | 1.00 | 44.93 | N |
| ATOM | 8779 | CA | ARG | H | 210 | 67.213 | −5.556 | 39.851 | 1.00 | 45.95 | C |
| ATOM | 8780 | C | ARG | H | 210 | 67.195 | −5.131 | 41.323 | 1.00 | 46.32 | C |
| ATOM | 8781 | O | ARG | H | 210 | 67.588 | −4.016 | 41.656 | 1.00 | 46.91 | O |
| ATOM | 8782 | CB | ARG | H | 210 | 68.412 | −4.920 | 39.135 | 1.00 | 45.23 | C |
| ATOM | 8783 | N | ASN | H | 211 | 66.722 | −6.025 | 42.188 | 1.00 | 46.95 | N |
| ATOM | 8784 | CA | ASN | H | 211 | 66.635 | −5.771 | 43.626 | 1.00 | 47.41 | C |
| ATOM | 8785 | C | ASN | H | 211 | 67.921 | −5.174 | 44.200 | 1.00 | 47.38 | C |
| ATOM | 8786 | O | ASN | H | 211 | 67.883 | −4.252 | 45.015 | 1.00 | 47.66 | O |
| ATOM | 8787 | CB | ASN | H | 211 | 66.315 | −7.079 | 44.354 | 1.00 | 46.75 | C |
| ATOM | 8788 | N | GLN | H | 212 | 69.056 | −5.711 | 43.765 | 1.00 | 47.31 | N |
| ATOM | 8789 | CA | GLN | H | 212 | 70.361 | −5.251 | 44.226 | 1.00 | 46.65 | C |
| ATOM | 8790 | C | GLN | H | 212 | 70.569 | −3.754 | 43.988 | 1.00 | 45.86 | C |
| ATOM | 8791 | O | GLN | H | 212 | 71.284 | −3.095 | 44.744 | 1.00 | 46.53 | O |
| ATOM | 8792 | CB | GLN | H | 212 | 71.464 | −6.046 | 43.517 | 1.00 | 46.71 | C |
| ATOM | 8793 | N | HIS | H | 213 | 69.947 | −3.223 | 42.938 | 1.00 | 44.51 | N |
| ATOM | 8794 | CA | HIS | H | 213 | 70.082 | −1.804 | 42.617 | 1.00 | 43.04 | C |
| ATOM | 8795 | C | HIS | H | 213 | 68.806 | −0.997 | 42.882 | 1.00 | 39.85 | C |
| ATOM | 8796 | O | HIS | H | 213 | 68.765 | 0.201 | 42.598 | 1.00 | 38.79 | O |

TABLE 3-continued

| | | | | | FGFR2(D2–D3) Complexed with FGF2 | | | | | |
|---|---|---|---|---|---|---|---|---|---|---|
| ATOM | 8797 | CB | HIS | H | 213 | 70.487 | −1.631 | 41.146 | 1.00 | 46.42 | C |
| ATOM | 8798 | CG | HIS | H | 213 | 71.713 | −2.398 | 40.757 | 1.00 | 49.71 | C |
| ATOM | 8799 | ND1 | HIS | H | 213 | 72.887 | −2.345 | 41.479 | 1.00 | 51.34 | N |
| ATOM | 8800 | CD2 | HIS | H | 213 | 71.948 | −3.230 | 39.715 | 1.00 | 50.77 | C |
| ATOM | 8801 | CE1 | HIS | H | 213 | 73.791 | −3.115 | 40.899 | 1.00 | 52.07 | C |
| ATOM | 8802 | NE2 | HIS | H | 213 | 73.247 | −3.663 | 39.827 | 1.00 | 51.31 | N |
| ATOM | 8803 | N | TRP | H | 214 | 67.788 | −1.650 | 43.441 | 1.00 | 36.77 | N |
| ATOM | 8804 | CA | TRP | H | 214 | 66.497 | −1.009 | 43.730 | 1.00 | 34.70 | C |
| ATOM | 8805 | C | TRP | H | 214 | 66.008 | −0.263 | 42.493 | 1.00 | 33.04 | C |
| ATOM | 8806 | O | TRP | H | 214 | 65.596 | 0.896 | 42.565 | 1.00 | 31.58 | O |
| ATOM | 8807 | CB | TRP | H | 214 | 66.618 | −0.032 | 44.906 | 1.00 | 34.83 | C |
| ATOM | 8808 | CG | TRP | H | 214 | 67.262 | −0.625 | 46.124 | 1.00 | 35.66 | C |
| ATOM | 8809 | CD1 | TRP | H | 214 | 68.591 | −0.632 | 46.420 | 1.00 | 35.53 | C |
| ATOM | 8810 | CD2 | TRP | H | 214 | 66.610 | −1.344 | 47.184 | 1.00 | 35.05 | C |
| ATOM | 8811 | NE1 | TRP | H | 214 | 68.810 | −1.310 | 47.594 | 1.00 | 36.05 | N |
| ATOM | 8812 | CE2 | TRP | H | 214 | 67.612 | −1.760 | 48.083 | 1.00 | 35.32 | C |
| ATOM | 8813 | CE3 | TRP | H | 214 | 65.276 | −1.677 | 47.457 | 1.00 | 36.06 | C |
| ATOM | 8814 | CZ2 | TRP | H | 214 | 67.326 | −2.496 | 49.242 | 1.00 | 35.08 | C |
| ATOM | 8815 | CZ3 | TRP | H | 214 | 64.987 | −2.412 | 48.610 | 1.00 | 35.94 | C |
| ATOM | 8816 | CH2 | TRP | H | 214 | 66.012 | −2.812 | 49.487 | 1.00 | 35.22 | C |
| ATOM | 8817 | N | SER | H | 215 | 66.035 | −0.949 | 41.356 | 1.00 | 32.01 | N |
| ATOM | 8818 | CA | SER | H | 215 | 65.645 | −0.330 | 40.100 | 1.00 | 31.21 | C |
| ATOM | 8819 | C | SER | H | 215 | 64.560 | −1.030 | 39.289 | 1.00 | 30.29 | C |
| ATOM | 8820 | O | SER | H | 215 | 64.356 | −2.242 | 39.399 | 1.00 | 30.47 | O |
| ATOM | 8821 | CB | SER | H | 215 | 66.878 | −0.211 | 39.218 | 1.00 | 31.16 | C |
| ATOM | 8822 | OG | SER | H | 215 | 67.349 | −1.511 | 38.910 | 1.00 | 31.69 | O |
| ATOM | 8823 | N | LEU | H | 216 | 63.888 | −0.240 | 38.455 | 1.00 | 29.28 | N |
| ATOM | 8824 | CA | LEU | H | 216 | 62.857 | −0.728 | 37.539 | 1.00 | 27.87 | C |
| ATOM | 8825 | C | LEU | H | 216 | 63.351 | −0.322 | 36.152 | 1.00 | 26.76 | C |
| ATOM | 8826 | O | LEU | H | 216 | 63.692 | 0.839 | 35.932 | 1.00 | 26.11 | O |
| ATOM | 8827 | CB | LEU | H | 216 | 61.499 | −0.066 | 37.800 | 1.00 | 28.18 | C |
| ATOM | 8828 | CG | LEU | H | 216 | 60.431 | −0.226 | 36.700 | 1.00 | 27.88 | C |
| ATOM | 8829 | CD1 | LEU | H | 216 | 59.966 | −1.669 | 36.632 | 1.00 | 27.76 | C |
| ATOM | 8830 | CD2 | LEU | H | 216 | 59.244 | 0.672 | 36.992 | 1.00 | 27.10 | C |
| ATOM | 8831 | N | ILE | H | 217 | 63.382 | −1.276 | 35.224 | 1.00 | 26.12 | N |
| ATOM | 8832 | CA | ILE | H | 217 | 63.859 | −1.009 | 33.867 | 1.00 | 26.88 | C |
| ATOM | 8833 | C | ILE | H | 217 | 62.852 | −1.336 | 32.761 | 1.00 | 27.40 | C |
| ATOM | 8834 | O | ILE | H | 217 | 62.284 | −2.434 | 32.718 | 1.00 | 26.58 | O |
| ATOM | 8835 | CB | ILE | H | 217 | 65.145 | −1.806 | 33.572 | 1.00 | 27.88 | C |
| ATOM | 8836 | CG1 | ILE | H | 217 | 66.264 | −1.355 | 34.505 | 1.00 | 28.58 | C |
| ATOM | 8837 | CG2 | ILE | H | 217 | 65.553 | −1.626 | 32.120 | 1.00 | 27.63 | C |
| ATOM | 8838 | CD1 | ILE | H | 217 | 67.515 | −2.173 | 34.340 | 1.00 | 30.18 | C |
| ATOM | 8839 | N | MET | H | 218 | 62.642 | −0.374 | 31.866 | 1.00 | 27.21 | N |
| ATOM | 8840 | CA | MET | H | 218 | 61.744 | −0.548 | 30.729 | 1.00 | 28.46 | C |
| ATOM | 8841 | C | MET | H | 218 | 62.535 | −0.223 | 29.462 | 1.00 | 29.47 | C |
| ATOM | 8842 | O | MET | H | 218 | 63.041 | 0.890 | 29.300 | 1.00 | 29.05 | O |
| ATOM | 8843 | CB | MET | H | 218 | 60.512 | 0.362 | 30.838 | 1.00 | 28.18 | C |
| ATOM | 8844 | CG | MET | H | 218 | 59.474 | −0.101 | 31.867 | 1.00 | 29.87 | C |
| ATOM | 8845 | SD | MET | H | 218 | 58.118 | 1.083 | 32.139 | 1.00 | 31.17 | S |
| ATOM | 8846 | CE | MET | H | 218 | 58.975 | 2.346 | 33.116 | 1.00 | 32.28 | C |
| ATOM | 8847 | N | GLU | H | 219 | 62.646 | −1.213 | 28.580 | 1.00 | 29.76 | N |
| ATOM | 8848 | CA | GLU | H | 219 | 63.386 | −1.085 | 27.329 | 1.00 | 30.45 | C |
| ATOM | 8849 | C | GLU | H | 219 | 62.485 | −0.672 | 26.166 | 1.00 | 31.67 | C |
| ATOM | 8850 | O | GLU | H | 219 | 61.289 | −0.983 | 26.157 | 1.00 | 31.77 | O |
| ATOM | 8851 | CB | GLU | H | 219 | 64.067 | −2.427 | 27.017 | 1.00 | 30.73 | C |
| ATOM | 8852 | CG | GLU | H | 219 | 64.930 | −2.941 | 28.176 | 1.00 | 30.88 | C |
| ATOM | 8853 | CD | GLU | H | 219 | 65.103 | −4.453 | 28.183 | 1.00 | 32.39 | C |
| ATOM | 8854 | OE1 | GLU | H | 219 | 64.093 | −5.162 | 27.990 | 1.00 | 32.44 | O |
| ATOM | 8855 | OE2 | GLU | H | 219 | 66.240 | −4.937 | 28.404 | 1.00 | 32.35 | O |
| ATOM | 8856 | N | SER | H | 220 | 63.068 | 0.040 | 25.198 | 1.00 | 31.54 | N |
| ATOM | 8857 | CA | SER | H | 220 | 62.367 | 0.504 | 24.001 | 1.00 | 32.05 | C |
| ATOM | 8858 | C | SER | H | 220 | 61.024 | 1.162 | 24.283 | 1.00 | 32.14 | C |
| ATOM | 8859 | O | SER | H | 220 | 59.996 | 0.720 | 23.764 | 1.00 | 32.54 | O |
| ATOM | 8860 | CB | SER | H | 220 | 62.153 | −0.668 | 23.057 | 1.00 | 33.03 | C |
| ATOM | 8861 | OG | SER | H | 220 | 63.347 | −1.411 | 22.927 | 1.00 | 35.98 | O |
| ATOM | 8862 | N | VAL | H | 221 | 61.035 | 2.227 | 25.080 | 1.00 | 31.04 | N |
| ATOM | 8863 | CA | VAL | H | 221 | 59.801 | 2.909 | 25.443 | 1.00 | 31.01 | C |
| ATOM | 8864 | C | VAL | H | 221 | 59.039 | 3.497 | 24.254 | 1.00 | 31.75 | C |
| ATOM | 8865 | O | VAL | H | 221 | 59.632 | 3.864 | 23.229 | 1.00 | 31.26 | O |
| ATOM | 8866 | CB | VAL | H | 221 | 60.058 | 4.033 | 26.481 | 1.00 | 28.69 | C |
| ATOM | 8867 | CG1 | VAL | H | 221 | 60.706 | 3.452 | 27.714 | 1.00 | 29.39 | C |
| ATOM | 8868 | CG2 | VAL | H | 221 | 60.936 | 5.115 | 25.883 | 1.00 | 30.09 | C |
| ATOM | 8869 | N | VAL | H | 222 | 57.718 | 3.587 | 24.418 | 1.00 | 31.66 | N |
| ATOM | 8870 | CA | VAL | H | 222 | 56.827 | 4.121 | 23.398 | 1.00 | 32.31 | C |
| ATOM | 8871 | C | VAL | H | 222 | 55.855 | 5.081 | 24.067 | 1.00 | 33.19 | C |
| ATOM | 8872 | O | VAL | H | 222 | 55.736 | 5.102 | 25.294 | 1.00 | 33.57 | O |
| ATOM | 8873 | CB | VAL | H | 222 | 56.028 | 2.987 | 22.702 | 1.00 | 32.00 | C |

TABLE 3-continued

FGFR2(D2–D3) Complexed with FGF2

| ATOM | 8874 | CG1 | VAL | H | 222 | 56.954 | 2.170 | 21.815 | 1.00 | 32.20 | C |
|---|---|---|---|---|---|---|---|---|---|---|---|
| ATOM | 8875 | CG2 | VAL | H | 222 | 55.384 | 2.081 | 23.739 | 1.00 | 30.79 | C |
| ATOM | 8876 | N | PRO | H | 223 | 55.151 | 5.895 | 23.271 | 1.00 | 34.18 | N |
| ATOM | 8877 | CA | PRO | H | 223 | 54.185 | 6.863 | 23.800 | 1.00 | 34.61 | C |
| ATOM | 8878 | C | PRO | H | 223 | 53.232 | 6.316 | 24.859 | 1.00 | 34.84 | C |
| ATOM | 8879 | O | PRO | H | 223 | 52.960 | 6.988 | 25.848 | 1.00 | 35.37 | O |
| ATOM | 8880 | CB | PRO | H | 223 | 53.461 | 7.341 | 22.544 | 1.00 | 34.95 | C |
| ATOM | 8881 | CG | PRO | H | 223 | 54.580 | 7.344 | 21.527 | 1.00 | 34.86 | C |
| ATOM | 8882 | CD | PRO | H | 223 | 55.285 | 6.029 | 21.804 | 1.00 | 34.68 | C |
| ATOM | 8883 | N | SER | H | 224 | 52.734 | 5.096 | 24.667 | 1.00 | 35.09 | N |
| ATOM | 8884 | CA | SER | H | 224 | 51.811 | 4.509 | 25.637 | 1.00 | 34.94 | C |
| ATOM | 8885 | C | SER | H | 224 | 52.397 | 4.247 | 27.039 | 1.00 | 34.92 | C |
| ATOM | 8886 | O | SER | H | 224 | 51.646 | 3.985 | 27.977 | 1.00 | 34.65 | O |
| ATOM | 8887 | CB | SER | H | 224 | 51.206 | 3.215 | 25.077 | 1.00 | 35.60 | C |
| ATOM | 8888 | OG | SER | H | 224 | 52.203 | 2.360 | 24.545 | 1.00 | 37.29 | O |
| ATOM | 8889 | N | ASP | H | 225 | 53.723 | 4.322 | 27.186 | 1.00 | 34.37 | N |
| ATOM | 8890 | CA | ASP | H | 225 | 54.361 | 4.107 | 28.491 | 1.00 | 33.89 | C |
| ATOM | 8891 | C | ASP | H | 225 | 54.233 | 5.318 | 29.422 | 1.00 | 33.37 | C |
| ATOM | 8892 | O | ASP | H | 225 | 54.572 | 5.252 | 30.604 | 1.00 | 33.39 | O |
| ATOM | 8893 | CB | ASP | H | 225 | 55.844 | 3.754 | 28.318 | 1.00 | 34.24 | C |
| ATOM | 8894 | CG | ASP | H | 225 | 56.045 | 2.352 | 27.793 | 1.00 | 35.08 | C |
| ATOM | 8895 | OD1 | ASP | H | 225 | 55.378 | 1.430 | 28.311 | 1.00 | 34.26 | O |
| ATOM | 8896 | OD2 | ASP | H | 225 | 56.871 | 2.164 | 26.876 | 1.00 | 35.90 | O |
| ATOM | 8897 | N | LYS | H | 226 | 53.758 | 6.430 | 28.875 | 1.00 | 33.82 | N |
| ATOM | 8898 | CA | LYS | H | 226 | 53.559 | 7.653 | 29.648 | 1.00 | 33.74 | C |
| ATOM | 8899 | C | LYS | H | 226 | 52.706 | 7.352 | 30.881 | 1.00 | 32.86 | C |
| ATOM | 8900 | O | LYS | H | 226 | 51.705 | 6.643 | 30.783 | 1.00 | 33.43 | O |
| ATOM | 8901 | CB | LYS | H | 226 | 52.846 | 8.679 | 28.772 | 1.00 | 35.12 | C |
| ATOM | 8902 | CG | LYS | H | 226 | 52.420 | 9.954 | 29.475 | 1.00 | 36.96 | C |
| ATOM | 8903 | CD | LYS | H | 226 | 51.656 | 10.846 | 28.506 | 1.00 | 38.84 | C |
| ATOM | 8904 | CE | LYS | H | 226 | 51.319 | 12.178 | 29.139 | 1.00 | 41.97 | C |
| ATOM | 8905 | NZ | LYS | H | 226 | 52.566 | 12.900 | 29.517 | 1.00 | 43.84 | N |
| ATOM | 8906 | N | GLY | H | 227 | 53.102 | 7.882 | 32.035 | 1.00 | 32.12 | N |
| ATOM | 8907 | CA | GLY | H | 227 | 52.342 | 7.664 | 33.256 | 1.00 | 31.37 | C |
| ATOM | 8908 | C | GLY | H | 227 | 53.187 | 7.849 | 34.509 | 1.00 | 31.81 | C |
| ATOM | 8909 | O | GLY | H | 227 | 54.310 | 8.355 | 34.435 | 1.00 | 31.79 | O |
| ATOM | 8910 | N | ASN | H | 228 | 52.646 | 7.447 | 35.655 | 1.00 | 31.03 | N |
| ATOM | 8911 | CA | ASN | H | 226 | 53.354 | 7.550 | 36.921 | 1.00 | 30.85 | C |
| ATOM | 8912 | C | ASN | H | 228 | 53.845 | 6.187 | 37.376 | 1.00 | 29.72 | C |
| ATOM | 8913 | O | ASN | H | 228 | 53.123 | 5.191 | 37.279 | 1.00 | 30.39 | O |
| ATOM | 8914 | CB | ASN | H | 228 | 52.454 | 8.138 | 38.002 | 1.00 | 32.32 | C |
| ATOM | 8915 | CG | ASN | H | 228 | 52.044 | 9.561 | 37.700 | 1.00 | 34.94 | C |
| ATOM | 8916 | OD1 | ASN | H | 228 | 52.877 | 10.394 | 37.331 | 1.00 | 35.94 | O |
| ATOM | 8917 | ND2 | ASN | H | 228 | 50.757 | 9.853 | 37.855 | 1.00 | 35.31 | N |
| ATOM | 8918 | N | TYR | H | 229 | 55.080 | 6.155 | 37.866 | 1.00 | 27.72 | N |
| ATOM | 8919 | CA | TYR | H | 229 | 55.689 | 4.928 | 38.362 | 1.00 | 27.25 | C |
| ATOM | 8920 | C | TYR | H | 229 | 56.153 | 5.166 | 39.799 | 1.00 | 27.25 | C |
| ATOM | 8921 | O | TYR | H | 229 | 57.006 | 6.020 | 40.061 | 1.00 | 26.34 | O |
| ATOM | 8922 | CB | TYR | H | 229 | 56.846 | 4.512 | 37.447 | 1.00 | 26.74 | C |
| ATOM | 8923 | CG | TYR | H | 229 | 56.372 | 4.151 | 36.054 | 1.00 | 26.75 | C |
| ATOM | 8924 | CD1 | TYR | H | 229 | 56.148 | 5.131 | 35.081 | 1.00 | 26.36 | C |
| ATOM | 8925 | CD2 | TYR | H | 229 | 56.083 | 2.830 | 35.725 | 1.00 | 26.67 | C |
| ATOM | 8926 | CE1 | TYR | H | 229 | 55.645 | 4.793 | 33.817 | 1.00 | 25.79 | C |
| ATOM | 8927 | CE2 | TYR | H | 229 | 55.584 | 2.488 | 34.474 | 1.00 | 25.91 | C |
| ATOM | 8928 | CZ | TYR | H | 229 | 55.368 | 3.464 | 33.528 | 1.00 | 26.33 | C |
| ATOM | 8929 | OH | TYR | H | 229 | 54.882 | 3.082 | 32.287 | 1.00 | 27.87 | O |
| ATOM | 8930 | N | THR | H | 230 | 55.568 | 4.405 | 40.722 | 1.00 | 26.69 | N |
| ATOM | 8931 | CA | THR | H | 230 | 55.852 | 4.537 | 42.145 | 1.00 | 26.63 | C |
| ATOM | 8932 | C | THR | H | 230 | 56.543 | 3.338 | 42.766 | 1.00 | 26.70 | C |
| ATOM | 8933 | O | THR | H | 230 | 56.150 | 2.194 | 42.548 | 1.00 | 26.96 | O |
| ATOM | 8934 | CB | THR | H | 230 | 54.550 | 4.774 | 42.930 | 1.00 | 27.14 | C |
| ATOM | 8935 | OG1 | THR | H | 230 | 53.916 | 5.970 | 42.454 | 1.00 | 28.26 | O |
| ATOM | 8936 | CG2 | THR | H | 230 | 54.834 | 4.896 | 44.425 | 1.00 | 27.42 | C |
| ATOM | 8937 | N | CYS | H | 231 | 57.568 | 3.611 | 43.562 | 1.00 | 27.11 | N |
| ATOM | 8938 | CA | CYS | H | 231 | 58.291 | 2.547 | 44.247 | 1.00 | 27.77 | C |
| ATOM | 8939 | C | CYS | H | 231 | 57.852 | 2.567 | 45.713 | 1.00 | 27.56 | C |
| ATOM | 8940 | O | CYS | H | 231 | 57.845 | 3.617 | 46.344 | 1.00 | 26.94 | O |
| ATOM | 8941 | CB | CYS | H | 231 | 59.803 | 2.791 | 44.160 | 1.00 | 28.81 | C |
| ATOM | 8942 | SG | CYS | H | 231 | 60.369 | 4.264 | 45.054 | 1.00 | 29.74 | S |
| ATOM | 8943 | N | VAL | H | 232 | 57.464 | 1.405 | 46.234 | 1.00 | 29.02 | N |
| ATOM | 8944 | CA | VAL | H | 232 | 57.048 | 1.257 | 47.632 | 1.00 | 30.32 | C |
| ATOM | 8945 | C | VAL | H | 232 | 58.065 | 0.337 | 48.328 | 1.00 | 31.10 | C |
| ATOM | 8946 | O | VAL | H | 232 | 58.294 | −0.792 | 47.888 | 1.00 | 30.52 | O |
| ATOM | 8947 | CB | VAL | H | 232 | 55.634 | 0.617 | 47.747 | 1.00 | 30.65 | C |
| ATOM | 8948 | CG1 | VAL | H | 232 | 55.164 | 0.652 | 49.189 | 1.00 | 29.14 | C |
| ATOM | 8949 | CG2 | VAL | H | 232 | 54.644 | 1.368 | 46.855 | 1.00 | 30.28 | C |
| ATOM | 8950 | N | VAL | H | 233 | 58.664 | 0.822 | 49.415 | 1.00 | 31.38 | N |

TABLE 3-continued

FGFR2(D2–D3) Complexed with FGF2

| ATOM | 8951 | CA | VAL | H | 233 | 59.678 | 0.057 | 50.131 | 1.00 | 32.74 | C |
|---|---|---|---|---|---|---|---|---|---|---|---|
| ATOM | 8952 | C | VAL | H | 233 | 59.271 | −0.123 | 51.583 | 1.00 | 33.12 | C |
| ATOM | 8953 | O | VAL | H | 233 | 58.919 | 0.846 | 52.253 | 1.00 | 34.28 | O |
| ATOM | 8954 | CB | VAL | H | 233 | 61.044 | 0.775 | 50.016 | 1.00 | 32.49 | C |
| ATOM | 8955 | CG1 | VAL | H | 233 | 62.095 | 0.072 | 50.830 | 1.00 | 33.55 | C |
| ATOM | 8956 | CG2 | VAL | H | 233 | 61.462 | 0.815 | 48.550 | 1.00 | 32.77 | C |
| ATOM | 8957 | N | GLU | H | 234 | 59.322 | −1.354 | 52.082 | 1.00 | 33.62 | N |
| ATOM | 8958 | CA | GLU | H | 234 | 58.884 | −1.588 | 53.453 | 1.00 | 34.62 | C |
| ATOM | 8959 | C | GLU | H | 234 | 59.435 | −2.781 | 54.233 | 1.00 | 33.75 | C |
| ATOM | 8960 | O | GLU | H | 234 | 59.942 | −3.754 | 53.671 | 1.00 | 33.82 | O |
| ATOM | 8961 | CB | GLU | H | 234 | 57.358 | −1.656 | 53.465 | 1.00 | 36.46 | C |
| ATOM | 8962 | CG | GLU | H | 234 | 56.794 | −2.727 | 52.553 | 1.00 | 39.69 | C |
| ATOM | 8963 | CD | GLU | H | 234 | 55.327 | −2.489 | 52.180 | 1.00 | 43.48 | C |
| ATOM | 8964 | OE1 | GLU | H | 234 | 54.753 | −3.359 | 51.485 | 1.00 | 43.83 | O |
| ATOM | 8965 | OE2 | GLU | H | 234 | 54.751 | −1.436 | 52.564 | 1.00 | 43.30 | O |
| ATOM | 8966 | N | ASN | H | 235 | 59.337 | −2.660 | 55.554 | 1.00 | 33.27 | N |
| ATOM | 8967 | CA | ASN | H | 235 | 59.739 | −3.701 | 56.500 | 1.00 | 33.61 | C |
| ATOM | 8968 | C | ASN | H | 235 | 58.806 | −3.533 | 57.700 | 1.00 | 33.99 | C |
| ATOM | 8969 | O | ASN | H | 235 | 57.882 | −2.713 | 57.655 | 1.00 | 33.48 | O |
| ATOM | 8970 | CB | ASN | H | 235 | 61.225 | −3.584 | 56.917 | 1.00 | 32.09 | C |
| ATOM | 8971 | CG | ASN | H | 235 | 61.535 | −2.342 | 57.754 | 1.00 | 31.97 | C |
| ATOM | 8972 | OD1 | ASN | H | 235 | 60.664 | −1.759 | 58.388 | 1.00 | 31.33 | O |
| ATOM | 8973 | ND2 | ASN | H | 235 | 62.807 | −1.961 | 57.780 | 1.00 | 31.28 | N |
| ATOM | 8974 | N | GLU | H | 236 | 59.039 | −4.293 | 58.764 | 1.00 | 34.43 | N |
| ATOM | 8975 | CA | GLU | H | 236 | 58.196 | −4.242 | 59.961 | 1.00 | 35.26 | C |
| ATOM | 8976 | C | GLU | H | 236 | 58.071 | −2.876 | 60.657 | 1.00 | 35.71 | C |
| ATOM | 8977 | O | GLU | H | 236 | 57.095 | −2.626 | 61.367 | 1.00 | 35.11 | O |
| ATOM | 8978 | CB | GLU | H | 236 | 58.695 | −5.275 | 60.983 | 1.00 | 34.81 | C |
| ATOM | 8979 | N | TYR | H | 237 | 59.051 | −1.998 | 60.462 | 1.00 | 35.47 | N |
| ATOM | 8980 | CA | TYR | H | 237 | 59.024 | −0.684 | 61.103 | 1.00 | 35.87 | C |
| ATOM | 8981 | C | TYR | H | 237 | 58.606 | 0.489 | 60.216 | 1.00 | 35.74 | C |
| ATOM | 8982 | O | TYR | H | 237 | 58.679 | 1.636 | 60.645 | 1.00 | 35.72 | O |
| ATOM | 8983 | CB | TYR | H | 237 | 60.391 | −0.351 | 61.703 | 1.00 | 36.51 | C |
| ATOM | 8984 | CG | TYR | H | 237 | 60.972 | −1.460 | 62.527 | 1.00 | 38.57 | C |
| ATOM | 8985 | CD1 | TYR | H | 237 | 62.116 | −2.128 | 62.105 | 1.00 | 39.34 | C |
| ATOM | 8986 | CD2 | TYR | H | 237 | 60.372 | −1.857 | 63.723 | 1.00 | 38.70 | C |
| ATOM | 8987 | CE1 | TYR | H | 237 | 62.655 | −3.164 | 62.854 | 1.00 | 41.42 | C |
| ATOM | 8988 | CE2 | TYR | H | 237 | 60.895 | −2.889 | 64.475 | 1.00 | 40.61 | C |
| ATOM | 8989 | CZ | TYR | H | 237 | 62.043 | −3.540 | 64.036 | 1.00 | 41.94 | C |
| ATOM | 8990 | OH | TYR | H | 237 | 62.593 | −4.558 | 64.780 | 1.00 | 44.10 | O |
| ATOM | 8991 | N | GLY | H | 238 | 58.187 | 0.230 | 58.985 | 1.00 | 34.67 | N |
| ATOM | 8992 | CA | GLY | H | 238 | 57.784 | 1.352 | 58.160 | 1.00 | 34.62 | C |
| ATOM | 8993 | C | GLY | H | 238 | 57.605 | 1.088 | 56.682 | 1.00 | 34.06 | C |
| ATOM | 8994 | O | GLY | H | 238 | 58.008 | 0.046 | 56.163 | 1.00 | 34.41 | O |
| ATOM | 8995 | N | SER | H | 239 | 56.997 | 2.062 | 56.010 | 1.00 | 33.16 | N |
| ATOM | 8996 | CA | SER | H | 239 | 56.734 | 1.997 | 54.579 | 1.00 | 32.94 | C |
| ATOM | 8997 | C | SER | H | 239 | 56.846 | 3.394 | 53.977 | 1.00 | 32.43 | C |
| ATOM | 8998 | O | SER | H | 239 | 56.203 | 4.333 | 54.451 | 1.00 | 32.53 | O |
| ATOM | 8999 | CB | SER | H | 239 | 55.336 | 1.443 | 54.330 | 1.00 | 33.10 | C |
| ATOM | 9000 | OG | SER | H | 239 | 55.033 | 1.451 | 52.946 | 1.00 | 35.89 | O |
| ATOM | 9001 | N | ILE | H | 240 | 57.670 | 3.533 | 52.940 | 1.00 | 30.73 | N |
| ATOM | 9002 | CA | ILE | H | 240 | 57.865 | 4.823 | 52.277 | 1.00 | 29.58 | C |
| ATOM | 9003 | C | ILE | H | 240 | 57.766 | 4.656 | 50.764 | 1.00 | 28.89 | C |
| ATOM | 9004 | O | ILE | H | 240 | 58.017 | 3.574 | 50.248 | 1.00 | 28.79 | O |
| ATOM | 9005 | CB | ILE | H | 240 | 59.259 | 5.443 | 52.611 | 1.00 | 28.35 | C |
| ATOM | 9006 | CG1 | ILE | H | 240 | 60.386 | 4.527 | 52.114 | 1.00 | 28.29 | C |
| ATOM | 9007 | CG2 | ILE | H | 240 | 59.378 | 5.683 | 54.109 | 1.00 | 27.34 | C |
| ATOM | 9008 | CD1 | ILE | H | 240 | 61.810 | 5.006 | 52.476 | 1.00 | 27.28 | C |
| ATOM | 9009 | N | ASN | H | 241 | 57.402 | 5.726 | 50.060 | 1.00 | 28.56 | N |
| ATOM | 9010 | CA | ASN | H | 241 | 57.281 | 5.676 | 48.604 | 1.00 | 28.26 | C |
| ATOM | 9011 | C | ASN | H | 241 | 57.780 | 6.944 | 47.911 | 1.00 | 28.17 | C |
| ATOM | 9012 | O | ASN | H | 241 | 57.936 | 7.995 | 48.534 | 1.00 | 28.13 | O |
| ATOM | 9013 | CB | ASN | H | 241 | 55.830 | 5.428 | 48.199 | 1.00 | 28.67 | C |
| ATOM | 9014 | CG | ASN | H | 241 | 54.884 | 6.490 | 48.733 | 1.00 | 30.86 | C |
| ATOM | 9015 | OD1 | ASN | H | 241 | 54.186 | 6.281 | 49.737 | 1.00 | 32.41 | O |
| ATOM | 9016 | ND2 | ASN | H | 241 | 54.864 | 7.639 | 48.078 | 1.00 | 30.28 | N |
| ATOM | 9017 | N | HIS | H | 242 | 58.008 | 6.829 | 46.605 | 1.00 | 27.60 | N |
| ATOM | 9018 | CA | HIS | H | 242 | 58.491 | 7.932 | 45.774 | 1.00 | 27.16 | C |
| ATOM | 9019 | C | HIS | H | 242 | 57.861 | 7.760 | 44.386 | 1.00 | 26.91 | C |
| ATOM | 9020 | O | HIS | H | 242 | 57.694 | 6.648 | 43.916 | 1.00 | 26.35 | O |
| ATOM | 9021 | CB | HIS | H | 242 | 60.019 | 7.852 | 45.658 | 1.00 | 26.94 | C |
| ATOM | 9022 | CG | HIS | H | 242 | 60.628 | 8.925 | 44.811 | 1.00 | 27.19 | C |
| ATOM | 9023 | ND1 | HIS | H | 242 | 60.842 | 10.206 | 45.269 | 1.00 | 27.39 | N |
| ATOM | 9024 | CD2 | HIS | H | 242 | 61.083 | 8.903 | 43.533 | 1.00 | 28.28 | C |
| ATOM | 9025 | CE1 | HIS | H | 242 | 61.404 | 10.927 | 44.316 | 1.00 | 27.31 | C |
| ATOM | 9026 | NE2 | HIS | H | 242 | 61.561 | 10.162 | 43.252 | 1.00 | 27.69 | N |
| ATOM | 9027 | N | THR | H | 243 | 57.526 | 8.859 | 43.725 | 1.00 | 27.18 | N |

TABLE 3-continued

| | | | | | FGFR2(D2–D3) Complexed with FGF2 | | | | | | |
|---|---|---|---|---|---|---|---|---|---|---|---|
| ATOM | 9028 | CA | THR | H | 243 | 56.894 | 8.755 | 42.423 | 1.00 | 28.17 | C |
| ATOM | 9029 | C | THR | H | 243 | 57.613 | 9.480 | 41.300 | 1.00 | 29.37 | C |
| ATOM | 9030 | O | THR | H | 243 | 58.041 | 10.629 | 41.452 | 1.00 | 28.73 | O |
| ATOM | 9031 | CB | THR | H | 243 | 55.421 | 9.242 | 42.492 | 1.00 | 28.46 | C |
| ATOM | 9032 | OG1 | THR | H | 243 | 54.657 | 8.327 | 43.295 | 1.00 | 26.48 | O |
| ATOM | 9033 | CG2 | THR | H | 243 | 54.814 | 9.327 | 41.091 | 1.00 | 27.09 | C |
| ATOM | 9034 | N | TYR | H | 244 | 57.744 | 8.773 | 40.179 | 1.00 | 29.94 | N |
| ATOM | 9035 | CA | TYR | H | 244 | 58.381 | 9.285 | 38.973 | 1.00 | 32.10 | C |
| ATOM | 9036 | C | TYR | H | 244 | 57.305 | 9.454 | 37.901 | 1.00 | 33.21 | C |
| ATOM | 9037 | O | TYR | H | 244 | 56.330 | 8.698 | 37.869 | 1.00 | 33.58 | O |
| ATOM | 9038 | CB | TYR | H | 244 | 59.422 | 8.283 | 38.448 | 1.00 | 32.60 | C |
| ATOM | 9039 | CG | TYR | H | 244 | 60.686 | 8.203 | 39.265 | 1.00 | 33.86 | C |
| ATOM | 9040 | CD1 | TYR | H | 244 | 61.081 | 7.005 | 39.862 | 1.00 | 34.01 | C |
| ATOM | 9041 | CD2 | TYR | H | 244 | 61.504 | 9.323 | 39.424 | 1.00 | 33.69 | C |
| ATOM | 9042 | CE1 | TYR | H | 244 | 62.274 | 6.922 | 40.601 | 1.00 | 34.99 | C |
| ATOM | 9043 | CE2 | TYR | H | 244 | 62.691 | 9.254 | 40.153 | 1.00 | 34.59 | C |
| ATOM | 9044 | CZ | TYR | H | 244 | 63.068 | 8.053 | 40.737 | 1.00 | 35.17 | C |
| ATOM | 9045 | OH | TYR | H | 244 | 64.233 | 7.992 | 41.452 | 1.00 | 34.83 | O |
| ATOM | 9046 | N | HIS | H | 245 | 57.485 | 10.436 | 37.025 | 1.00 | 33.44 | N |
| ATOM | 9047 | CA | HIS | H | 245 | 56.551 | 10.656 | 35.920 | 1.00 | 33.62 | C |
| ATOM | 9048 | C | HIS | H | 245 | 57.334 | 10.420 | 34.634 | 1.00 | 33.53 | C |
| ATOM | 9049 | O | HIS | H | 245 | 58.431 | 10.961 | 34.463 | 1.00 | 33.32 | O |
| ATOM | 9050 | CB | HIS | H | 245 | 56.005 | 12.087 | 35.939 | 1.00 | 33.59 | C |
| ATOM | 9051 | N | LEU | H | 246 | 56.783 | 9.605 | 33.741 | 1.00 | 33.25 | N |
| ATOM | 9052 | CA | LEU | H | 246 | 57.442 | 9.303 | 32.478 | 1.00 | 33.94 | C |
| ATOM | 9053 | C | LEU | H | 246 | 56.714 | 9.881 | 31.265 | 1.00 | 34.90 | C |
| ATOM | 9054 | O | LEU | H | 246 | 55.488 | 9.787 | 31.156 | 1.00 | 35.11 | O |
| ATOM | 9055 | CB | LEU | H | 246 | 57.581 | 7.786 | 32.301 | 1.00 | 33.54 | C |
| ATOM | 9056 | CG | LEU | H | 246 | 58.149 | 7.294 | 30.961 | 1.00 | 34.43 | C |
| ATOM | 9057 | CD1 | LEU | H | 246 | 59.585 | 7.792 | 30.785 | 1.00 | 33.01 | C |
| ATOM | 9058 | CD2 | LEU | H | 246 | 58.089 | 5.777 | 30.910 | 1.00 | 32.50 | C |
| ATOM | 9059 | N | ASP | H | 247 | 57.482 | 10.465 | 30.353 | 1.00 | 35.61 | N |
| ATOM | 9060 | CA | ASP | H | 247 | 56.944 | 11.033 | 29.127 | 1.00 | 37.11 | C |
| ATOM | 9061 | C | ASP | H | 247 | 57.832 | 10.602 | 27.964 | 1.00 | 37.48 | C |
| ATOM | 9062 | O | ASP | H | 247 | 59.058 | 10.634 | 28.066 | 1.00 | 37.54 | O |
| ATOM | 9063 | CB | ASP | H | 247 | 56.912 | 12.550 | 29.224 | 1.00 | 39.91 | C |
| ATOM | 9064 | CG | ASP | H | 247 | 55.542 | 13.115 | 28.940 | 1.00 | 42.18 | C |
| ATOM | 9065 | OD1 | ASP | H | 247 | 55.139 | 14.058 | 29.651 | 1.00 | 44.55 | O |
| ATOM | 9066 | OD2 | ASP | H | 247 | 54.875 | 12.622 | 28.004 | 1.00 | 43.69 | O |
| ATOM | 9067 | N | VAL | H | 248 | 57.219 | 10.188 | 26.861 | 1.00 | 37.77 | N |
| ATOM | 9068 | CA | VAL | H | 248 | 57.981 | 9.745 | 25.701 | 1.00 | 38.35 | C |
| ATOM | 9069 | C | VAL | H | 248 | 57.724 | 10.631 | 24.490 | 1.00 | 38.52 | C |
| ATOM | 9070 | O | VAL | H | 248 | 56.577 | 10.963 | 24.189 | 1.00 | 38.82 | O |
| ATOM | 9071 | CB | VAL | H | 248 | 57.628 | 8.281 | 25.332 | 1.00 | 39.24 | C |
| ATOM | 9072 | CG1 | VAL | H | 248 | 58.433 | 7.835 | 24.126 | 1.00 | 38.91 | C |
| ATOM | 9073 | CG2 | VAL | H | 248 | 57.909 | 7.366 | 26.516 | 1.00 | 39.39 | C |
| ATOM | 9074 | N | VAL | H | 249 | 58.797 | 11.010 | 23.797 | 1.00 | 38.34 | N |
| ATOM | 9075 | CA | VAL | H | 249 | 58.692 | 11.855 | 22.616 | 1.00 | 38.12 | C |
| ATOM | 9076 | C | VAL | H | 249 | 59.333 | 11.186 | 21.406 | 1.00 | 37.91 | C |
| ATOM | 9077 | O | VAL | H | 249 | 60.488 | 10.757 | 21.447 | 1.00 | 37.97 | O |
| ATOM | 9078 | CB | VAL | H | 249 | 59.370 | 13.225 | 22.835 | 1.00 | 39.72 | C |
| ATOM | 9079 | CG1 | VAL | H | 249 | 59.227 | 14.079 | 21.589 | 1.00 | 40.27 | C |
| ATOM | 9080 | CG2 | VAL | H | 249 | 58.741 | 13.936 | 24.022 | 1.00 | 39.98 | C |
| ATOM | 9081 | N | GLU | H | 250 | 58.574 | 11.092 | 20.323 | 1.00 | 37.93 | N |
| ATOM | 9082 | CA | GLU | H | 250 | 59.083 | 10.475 | 19.110 | 1.00 | 37.74 | C |
| ATOM | 9083 | C | GLU | H | 250 | 59.862 | 11.506 | 18.317 | 1.00 | 37.23 | C |
| ATOM | 9084 | O | GLU | H | 250 | 59.373 | 12.608 | 18.060 | 1.00 | 37.25 | O |
| ATOM | 9085 | CB | GLU | H | 250 | 57.934 | 9.925 | 18.259 | 1.00 | 39.21 | C |
| ATOM | 9086 | CG | GLU | H | 250 | 57.283 | 8.677 | 18.835 | 1.00 | 41.78 | C |
| ATOM | 9087 | CD | GLU | H | 250 | 55.943 | 8.362 | 18.197 | 1.00 | 43.45 | C |
| ATOM | 9088 | OE1 | GLU | H | 250 | 55.029 | 9.217 | 18.283 | 1.00 | 43.91 | O |
| ATOM | 9089 | OE2 | GLU | H | 250 | 55.803 | 7.261 | 17.621 | 1.00 | 44.35 | O |
| ATOM | 9090 | N | ARG | H | 251 | 61.084 | 11.157 | 17.943 | 1.00 | 36.00 | N |
| ATOM | 9091 | CA | ARG | H | 251 | 61.907 | 12.065 | 17.173 | 1.00 | 35.19 | C |
| ATOM | 9092 | C | ARG | H | 251 | 61.992 | 11.611 | 15.725 | 1.00 | 35.81 | C |
| ATOM | 9093 | O | ARG | H | 251 | 61.891 | 10.416 | 15.422 | 1.00 | 36.37 | O |
| ATOM | 9094 | CB | ARG | H | 251 | 63.329 | 12.170 | 17.760 | 1.00 | 33.44 | C |
| ATOM | 9095 | CG | ARG | H | 251 | 63.431 | 12.648 | 19.220 | 1.00 | 30.61 | C |
| ATOM | 9096 | CD | ARG | H | 251 | 62.608 | 13.895 | 19.515 | 1.00 | 29.36 | C |
| ATOM | 9097 | NE | ARG | H | 251 | 62.964 | 15.055 | 18.698 | 1.00 | 26.84 | N |
| ATOM | 9098 | CZ | ARG | H | 251 | 64.011 | 15.844 | 18.926 | 1.00 | 26.71 | C |
| ATOM | 9099 | NH1 | ARG | H | 251 | 64.819 | 15.599 | 19.953 | 1.00 | 27.05 | N |
| ATOM | 9100 | NH2 | ARG | H | 251 | 64.237 | 16.895 | 18.145 | 1.00 | 25.96 | N |
| ATOM | 9101 | N | SER | H | 252 | 62.181 | 12.595 | 14.848 | 1.00 | 36.27 | N |
| ATOM | 9102 | CA | SER | H | 252 | 62.311 | 12.341 | 13.425 | 1.00 | 36.60 | C |
| ATOM | 9103 | C | SER | H | 252 | 63.600 | 12.969 | 12.887 | 1.00 | 36.76 | C |
| ATOM | 9104 | O | SER | H | 252 | 63.639 | 14.146 | 12.563 | 1.00 | 36.31 | O |

TABLE 3-continued

FGFR2(D2–D3) Complexed with FGF2

| ATOM | 9105 | CB | SER | H | 252 | 61.112 | 12.915 | 12.673 | 1.00 | 36.51 | C |
|---|---|---|---|---|---|---|---|---|---|---|---|
| ATOM | 9106 | OG | SER | H | 252 | 61.353 | 12.873 | 11.278 | 1.00 | 37.79 | O |
| ATOM | 9107 | N | PRO | H | 253 | 64.669 | 12.170 | 12.764 | 1.00 | 37.26 | N |
| ATOM | 9108 | CA | PRO | H | 253 | 65.954 | 12.668 | 12.263 | 1.00 | 37.69 | C |
| ATOM | 9109 | C | PRO | H | 253 | 66.035 | 12.810 | 10.735 | 1.00 | 37.97 | C |
| ATOM | 9110 | O | PRO | H | 253 | 67.026 | 12.412 | 10.128 | 1.00 | 38.17 | O |
| ATOM | 9111 | CB | PRO | H | 253 | 66.931 | 11.618 | 12.781 | 1.00 | 37.61 | C |
| ATOM | 9112 | CG | PRO | H | 253 | 66.150 | 10.361 | 12.554 | 1.00 | 37.62 | C |
| ATOM | 9113 | CD | PRO | H | 253 | 64.749 | 10.726 | 13.053 | 1.00 | 37.15 | C |
| ATOM | 9114 | N | HIS | H | 254 | 65.010 | 13.375 | 10.107 | 1.00 | 37.79 | N |
| ATOM | 9115 | CA | HIS | H | 254 | 65.036 | 13.527 | 8.654 | 1.00 | 37.61 | C |
| ATOM | 9116 | C | HIS | H | 254 | 65.157 | 14.984 | 8.220 | 1.00 | 36.26 | C |
| ATOM | 9117 | O | HIS | H | 254 | 64.863 | 15.904 | 8.987 | 1.00 | 35.10 | O |
| ATOM | 9118 | CB | HIS | H | 254 | 63.768 | 12.945 | 8.013 | 1.00 | 39.78 | C |
| ATOM | 9119 | CG | HIS | H | 254 | 63.513 | 11.506 | 8.348 | 1.00 | 43.24 | C |
| ATOM | 9120 | ND1 | HIS | H | 254 | 62.942 | 11.106 | 9.539 | 1.00 | 44.40 | N |
| ATOM | 9121 | CD2 | HIS | H | 254 | 63.732 | 10.373 | 7.638 | 1.00 | 44.25 | C |
| ATOM | 9122 | CE1 | HIS | H | 254 | 62.814 | 9.790 | 9.547 | 1.00 | 44.51 | C |
| ATOM | 9123 | NE2 | HIS | H | 254 | 63.286 | 9.320 | 8.405 | 1.00 | 45.34 | N |
| ATOM | 9124 | N | ARG | H | 255 | 65.602 | 15.190 | 6.986 | 1.00 | 34.70 | N |
| ATOM | 9125 | CA | ARG | H | 255 | 65.697 | 16.543 | 6.450 | 1.00 | 34.66 | C |
| ATOM | 9126 | C | ARG | H | 255 | 64.234 | 16.947 | 6.199 | 1.00 | 32.87 | C |
| ATOM | 9127 | O | ARG | H | 255 | 63.348 | 16.094 | 6.220 | 1.00 | 31.68 | O |
| ATOM | 9128 | CB | ARG | H | 255 | 66.516 | 16.545 | 5.147 | 1.00 | 36.11 | C |
| ATOM | 9129 | CG | ARG | H | 255 | 65.923 | 15.740 | 3.992 | 1.00 | 39.33 | C |
| ATOM | 9130 | CD | ARG | H | 255 | 66.925 | 15.610 | 2.830 | 1.00 | 43.41 | C |
| ATOM | 9131 | NE | ARG | H | 255 | 66.255 | 15.594 | 1.526 | 1.00 | 47.20 | N |
| ATOM | 9132 | CZ | ARG | H | 255 | 65.493 | 14.602 | 1.065 | 1.00 | 48.68 | C |
| ATOM | 9133 | NH1 | ARG | H | 255 | 65.293 | 13.509 | 1.790 | 1.00 | 49.44 | N |
| ATOM | 9134 | NH2 | ARG | H | 255 | 64.897 | 14.719 | −0.117 | 1.00 | 50.48 | N |
| ATOM | 9135 | N | PRO | H | 256 | 63.956 | 18.238 | 5.962 | 1.00 | 32.44 | N |
| ATOM | 9136 | CA | PRO | H | 256 | 62.562 | 18.655 | 5.727 | 1.00 | 31.90 | C |
| ATOM | 9137 | C | PRO | H | 256 | 61.879 | 17.921 | 4.567 | 1.00 | 31.51 | C |
| ATOM | 9138 | O | PRO | H | 256 | 62.496 | 17.656 | 3.541 | 1.00 | 31.23 | O |
| ATOM | 9139 | CB | PRO | H | 256 | 62.681 | 20.160 | 5.437 | 1.00 | 31.84 | C |
| ATOM | 9140 | CG | PRO | H | 256 | 63.959 | 20.555 | 6.105 | 1.00 | 32.24 | C |
| ATOM | 9141 | CD | PRO | H | 256 | 64.870 | 19.381 | 5.788 | 1.00 | 31.98 | C |
| ATOM | 9142 | N | ILE | H | 257 | 60.603 | 17.601 | 4.745 | 1.00 | 30.89 | N |
| ATOM | 9143 | CA | ILE | H | 257 | 59.809 | 16.922 | 3.727 | 1.00 | 31.20 | C |
| ATOM | 9144 | C | ILE | H | 257 | 58.727 | 17.884 | 3.195 | 1.00 | 30.90 | C |
| ATOM | 9145 | O | ILE | H | 257 | 58.043 | 18.540 | 3.977 | 1.00 | 30.53 | O |
| ATOM | 9146 | CB | ILE | H | 257 | 59.143 | 15.659 | 4.338 | 1.00 | 32.99 | C |
| ATOM | 9147 | CG1 | ILE | H | 257 | 60.180 | 14.530 | 4.439 | 1.00 | 33.63 | C |
| ATOM | 9148 | CG2 | ILE | H | 257 | 57.922 | 15.231 | 3.521 | 1.00 | 33.41 | C |
| ATOM | 9149 | CD1 | ILE | H | 257 | 59.668 | 13.271 | 5.144 | 1.00 | 34.78 | C |
| ATOM | 9150 | N | LEU | H | 258 | 58.594 | 17.992 | 1.872 | 1.00 | 29.84 | N |
| ATOM | 9151 | CA | LEU | H | 258 | 57.578 | 18.870 | 1.293 | 1.00 | 29.28 | C |
| ATOM | 9152 | C | LEU | H | 258 | 56.468 | 18.062 | 0.652 | 1.00 | 29.66 | C |
| ATOM | 9153 | O | LEU | H | 258 | 56.679 | 16.938 | 0.197 | 1.00 | 29.28 | O |
| ATOM | 9154 | CB | LEU | H | 258 | 58.157 | 19.789 | 0.222 | 1.00 | 27.98 | C |
| ATOM | 9155 | CG | LEU | H | 258 | 59.413 | 20.606 | 0.512 | 1.00 | 29.09 | C |
| ATOM | 9156 | CD1 | LEU | H | 258 | 59.627 | 21.596 | −0.628 | 1.00 | 28.96 | C |
| ATOM | 9157 | CD2 | LEU | H | 258 | 59.287 | 21.334 | 1.808 | 1.00 | 29.25 | C |
| ATOM | 9158 | ND | GLN | H | 259 | 55.280 | 18.656 | 0.607 | 1.00 | 30.32 | N |
| ATOM | 9159 | CA | GLN | H | 259 | 54.109 | 18.021 | 0.003 | 1.00 | 30.43 | C |
| ATOM | 9160 | C | GLN | H | 259 | 54.277 | 17.965 | −1.518 | 1.00 | 29.17 | C |
| ATOM | 9161 | O | GLN | H | 259 | 54.605 | 18.967 | −2.147 | 1.00 | 28.86 | O |
| ATOM | 9162 | CB | GLN | H | 259 | 52.846 | 18.834 | 0.363 | 1.00 | 31.05 | C |
| ATOM | 9163 | CG | GLN | H | 259 | 51.519 | 18.315 | −0.222 | 1.00 | 31.55 | C |
| ATOM | 9164 | CD | GLN | H | 259 | 50.304 | 19.180 | 0.162 | 1.00 | 32.40 | C |
| ATOM | 9165 | OE1 | GLN | H | 259 | 50.084 | 19.480 | 1.336 | 1.00 | 31.59 | O |
| ATOM | 9166 | NE2 | GLN | H | 259 | 49.510 | 19.569 | −0.835 | 1.00 | 32.80 | N |
| ATOM | 9167 | N | ALA | H | 260 | 54.050 | 16.795 | −2.102 | 1.00 | 28.89 | N |
| ATOM | 9168 | CA | ALA | H | 260 | 54.155 | 16.627 | −3.549 | 1.00 | 29.45 | C |
| ATOM | 9169 | C | ALA | H | 260 | 53.130 | 17.505 | −4.268 | 1.00 | 29.81 | C |
| ATOM | 9170 | O | ALA | H | 260 | 52.011 | 17.648 | −3.801 | 1.00 | 29.56 | O |
| ATOM | 9171 | CB | ALA | H | 260 | 53.922 | 15.174 | −3.905 | 1.00 | 28.68 | C |
| ATOM | 9172 | N | GLY | H | 261 | 53.514 | 18.093 | −5.397 | 1.00 | 30.77 | N |
| ATOM | 9173 | CA | GLY | H | 261 | 52.595 | 18.934 | −6.148 | 1.00 | 31.72 | C |
| ATOM | 9174 | C | GLY | H | 261 | 52.630 | 20.414 | −5.805 | 1.00 | 32.63 | C |
| ATOM | 9175 | O | GLY | H | 261 | 52.069 | 21.230 | −6.535 | 1.00 | 32.86 | O |
| ATOM | 9176 | N | LEU | H | 262 | 53.279 | 20.769 | −4.699 | 1.00 | 33.34 | N |
| ATOM | 9177 | CA | LEU | H | 262 | 53.364 | 22.169 | −4.294 | 1.00 | 33.16 | C |
| ATOM | 9178 | C | LEU | H | 262 | 54.810 | 22.636 | −4.198 | 1.00 | 33.78 | C |
| ATOM | 9179 | O | LEU | H | 262 | 55.663 | 21.937 | −3.653 | 1.00 | 34.08 | O |
| ATOM | 9180 | CB | LEU | H | 262 | 52.654 | 22.372 | −2.949 | 1.00 | 32.41 | C |
| ATOM | 9181 | CG | LEU | H | 262 | 51.125 | 22.199 | −2.974 | 1.00 | 32.91 | C |

TABLE 3-continued

FGFR2(D2–D3) Complexed with FGF2

| ATOM | 9182 | CD1 | LEU | H | 262 | 50.548 | 22.321 | −1.561 | 1.00 | 31.68 | C |
|---|---|---|---|---|---|---|---|---|---|---|---|
| ATOM | 9183 | CD2 | LEU | H | 262 | 50.515 | 23.261 | −3.897 | 1.00 | 32.35 | C |
| ATOM | 9184 | N | PRO | H | 263 | 55.106 | 23.828 | −4.730 | 1.00 | 33.86 | N |
| ATOM | 9185 | CA | PRO | H | 263 | 54.162 | 24.731 | −5.398 | 1.00 | 34.62 | C |
| ATOM | 9186 | C | PRO | H | 263 | 53.692 | 24.210 | −6.762 | 1.00 | 35.16 | C |
| ATOM | 9187 | O | PRO | H | 263 | 54.308 | 23.324 | −7.353 | 1.00 | 35.17 | O |
| ATOM | 9188 | CB | PRO | H | 263 | 54.965 | 26.022 | −5.514 | 1.00 | 34.70 | C |
| ATOM | 9189 | CG | PRO | H | 263 | 56.368 | 25.509 | −5.724 | 1.00 | 34.09 | C |
| ATOM | 9190 | CD | PRO | H | 263 | 56.456 | 24.412 | −4.689 | 1.00 | 33.37 | C |
| ATOM | 9191 | N | ALA | H | 264 | 52.593 | 24.767 | −7.257 | 1.00 | 35.96 | N |
| ATOM | 9192 | CA | ALA | H | 264 | 52.052 | 24.354 | −8.547 | 1.00 | 37.08 | C |
| ATOM | 9193 | C | ALA | H | 264 | 52.357 | 25.379 | −9.637 | 1.00 | 37.85 | C |
| ATOM | 9194 | O | ALA | H | 264 | 52.493 | 26.572 | −9.361 | 1.00 | 37.83 | O |
| ATOM | 9195 | CB | ALA | H | 264 | 50.559 | 24.159 | −8.435 | 1.00 | 36.46 | C |
| ATOM | 9196 | N | ASN | H | 265 | 52.484 | 24.907 | −10.872 | 1.00 | 38.58 | N |
| ATOM | 9197 | CA | ASN | H | 265 | 52.730 | 25.800 | −11.995 | 1.00 | 39.78 | C |
| ATOM | 9198 | C | ASN | H | 265 | 51.564 | 26.790 | −12.067 | 1.00 | 41.26 | C |
| ATOM | 9199 | O | ASN | H | 265 | 50.443 | 26.486 | −11.653 | 1.00 | 40.55 | O |
| ATOM | 9200 | CB | ASN | H | 265 | 52.808 | 25.025 | −13.317 | 1.00 | 38.66 | C |
| ATOM | 9201 | CG | ASN | H | 265 | 54.022 | 24.103 | −13.399 | 1.00 | 38.73 | C |
| ATOM | 9202 | OD1 | ASN | H | 265 | 55.143 | 24.494 | −13.074 | 1.00 | 36.98 | O |
| ATOM | 9203 | ND2 | ASN | H | 265 | 53.799 | 22.877 | −13.856 | 1.00 | 38.25 | N |
| ATOM | 9204 | N | ALA | H | 266 | 51.836 | 27.975 | −12.595 | 1.00 | 42.81 | N |
| ATOM | 9205 | CA | ALA | H | 266 | 50.817 | 29.005 | −12.714 | 1.00 | 44.32 | C |
| ATOM | 9206 | C | ALA | H | 266 | 50.978 | 29.762 | −14.022 | 1.00 | 45.43 | C |
| ATOM | 9207 | O | ALA | H | 266 | 52.088 | 29.900 | −14.547 | 1.00 | 44.88 | O |
| ATOM | 9208 | CB | ALA | H | 266 | 50.921 | 29.970 | −11.545 | 1.00 | 44.47 | C |
| ATOM | 9209 | N | SER | H | 267 | 49.861 | 30.253 | −14.544 | 1.00 | 46.44 | N |
| ATOM | 9210 | CA | SER | H | 267 | 49.873 | 31.010 | −15.784 | 1.00 | 47.36 | C |
| ATOM | 9211 | C | SER | H | 267 | 48.937 | 32.207 | −15.656 | 1.00 | 47.83 | C |
| ATOM | 9212 | O | SER | H | 267 | 47.907 | 32.136 | −14.976 | 1.00 | 47.58 | O |
| ATOM | 9213 | CB | SER | H | 267 | 49.441 | 30.110 | −16.939 | 1.00 | 47.43 | C |
| ATOM | 9214 | OG | SER | H | 267 | 49.592 | 30.777 | −18.179 | 1.00 | 49.15 | O |
| ATOM | 9215 | N | THR | H | 268 | 49.295 | 33.304 | −16.313 | 1.00 | 47.79 | N |
| ATOM | 9216 | CA | THR | H | 268 | 48.477 | 34.512 | −16.264 | 1.00 | 48.27 | C |
| ATOM | 9217 | C | THR | H | 268 | 48.836 | 35.504 | −17.371 | 1.00 | 48.78 | C |
| ATOM | 9218 | O | THR | H | 268 | 49.878 | 35.383 | −18.021 | 1.00 | 48.83 | O |
| ATOM | 9219 | CB | THR | H | 268 | 48.627 | 35.225 | −14.899 | 1.00 | 47.98 | C |
| ATOM | 9220 | OG1 | THR | H | 268 | 47.774 | 36.374 | −14.866 | 1.00 | 48.48 | O |
| ATOM | 9221 | CG2 | THR | H | 268 | 50.065 | 35.663 | −14.677 | 1.00 | 47.38 | C |
| ATOM | 9222 | N | VAL | H | 269 | 47.961 | 36.481 | −17.588 | 1.00 | 48.82 | N |
| ATOM | 9223 | CA | VAL | H | 269 | 48.196 | 37.507 | −18.596 | 1.00 | 48.68 | C |
| ATOM | 9224 | C | VAL | H | 269 | 48.993 | 38.625 | −17.919 | 1.00 | 48.43 | C |
| ATOM | 9225 | O | VAL | H | 269 | 48.927 | 38.781 | −16.698 | 1.00 | 47.74 | O |
| ATOM | 9226 | CB | VAL | H | 269 | 46.858 | 38.082 | −19.132 | 1.00 | 48.31 | C |
| ATOM | 9227 | N | VAL | H | 270 | 49.759 | 39.381 | −18.699 | 1.00 | 48.71 | N |
| ATOM | 9228 | CA | VAL | H | 270 | 50.541 | 40.484 | −18.142 | 1.00 | 49.74 | C |
| ATOM | 9229 | C | VAL | H | 270 | 49.587 | 41.324 | −17.294 | 1.00 | 50.18 | C |
| ATOM | 9230 | O | VAL | H | 270 | 48.443 | 41.548 | −17.689 | 1.00 | 50.16 | O |
| ATOM | 9231 | CB | VAL | H | 270 | 51.152 | 41.381 | −19.264 | 1.00 | 49.84 | C |
| ATOM | 9232 | CG1 | VAL | H | 270 | 51.888 | 42.557 | −18.654 | 1.00 | 50.08 | C |
| ATOM | 9233 | CG2 | VAL | H | 270 | 52.109 | 40.574 | −20.128 | 1.00 | 49.80 | C |
| ATOM | 9234 | N | GLY | H | 271 | 50.044 | 41.764 | −16.124 | 1.00 | 51.04 | N |
| ATOM | 9235 | CA | GLY | H | 271 | 49.195 | 42.573 | −15.265 | 1.00 | 52.18 | C |
| ATOM | 9236 | C | GLY | H | 271 | 48.353 | 41.793 | −14.266 | 1.00 | 53.14 | C |
| ATOM | 9237 | O | GLY | H | 271 | 47.632 | 42.386 | −13.459 | 1.00 | 53.93 | O |
| ATOM | 9238 | N | GLY | H | 272 | 48.439 | 40.467 | −14.305 | 1.00 | 53.00 | N |
| ATOM | 9239 | CA | GLY | H | 272 | 47.662 | 39.658 | −13.379 | 1.00 | 53.12 | C |
| ATOM | 9240 | C | GLY | H | 272 | 48.330 | 39.423 | −12.034 | 1.00 | 52.85 | C |
| ATOM | 9241 | O | GLY | H | 272 | 49.427 | 39.919 | −11.770 | 1.00 | 52.78 | O |
| ATOM | 9242 | N | ASP | H | 273 | 47.653 | 38.665 | −11.178 | 1.00 | 52.73 | N |
| ATOM | 9243 | CA | ASP | H | 273 | 48.156 | 38.333 | −9.850 | 1.00 | 53.33 | C |
| ATOM | 9244 | C | ASP | H | 273 | 48.303 | 36.815 | −9.706 | 1.00 | 52.50 | C |
| ATOM | 9245 | O | ASP | H | 273 | 47.527 | 36.050 | −10.287 | 1.00 | 52.84 | O |
| ATOM | 9246 | CB | ASP | H | 273 | 47.191 | 38.870 | −8.792 | 1.00 | 55.38 | C |
| ATOM | 9247 | CG | ASP | H | 273 | 47.200 | 40.384 | −8.719 | 1.00 | 57.47 | C |
| ATOM | 9248 | OD1 | ASP | H | 273 | 47.256 | 41.024 | −9.793 | 1.00 | 58.51 | O |
| ATOM | 9249 | OD2 | ASP | H | 273 | 47.144 | 40.934 | −7.597 | 1.00 | 59.33 | O |
| ATOM | 9250 | N | VAL | H | 274 | 49.285 | 36.377 | −8.923 | 1.00 | 50.85 | N |
| ATOM | 9251 | CA | VAL | H | 274 | 49.512 | 34.953 | −8.746 | 1.00 | 48.93 | C |
| ATOM | 9252 | C | VAL | H | 274 | 50.120 | 34.592 | −7.386 | 1.00 | 47.83 | C |
| ATOM | 9253 | O | VAL | H | 274 | 50.644 | 35.450 | −6.674 | 1.00 | 47.74 | O |
| ATOM | 9254 | CB | VAL | H | 274 | 50.413 | 34.433 | −9.893 | 1.00 | 49.11 | C |
| ATOM | 9255 | CG1 | VAL | H | 274 | 51.810 | 35.040 | −9.781 | 1.00 | 48.48 | C |
| ATOM | 9256 | CG2 | VAL | H | 274 | 50.456 | 32.929 | −9.879 | 1.00 | 49.90 | C |
| ATOM | 9257 | N | GLU | H | 275 | 50.029 | 33.318 | −7.022 | 1.00 | 46.20 | N |
| ATOM | 9258 | CA | GLU | H | 275 | 50.580 | 32.847 | −5.763 | 1.00 | 45.12 | C |

TABLE 3-continued

FGFR2(D2–D3) Complexed with FGF2

| ATOM | 9259 | C | GLU | H | 275 | 51.209 | 31.461 | −5.912 | 1.00 | 43.67 | C |
|---|---|---|---|---|---|---|---|---|---|---|---|
| ATOM | 9260 | O | GLU | H | 275 | 50.865 | 30.702 | −6.817 | 1.00 | 43.08 | O |
| ATOM | 9261 | CB | GLU | H | 275 | 49.491 | 32.791 | −4.683 | 1.00 | 45.59 | C |
| ATOM | 9262 | CG | GLU | H | 275 | 48.336 | 31.821 | −4.962 | 1.00 | 46.75 | C |
| ATOM | 9263 | CD | GLU | H | 275 | 47.542 | 31.474 | −3.696 | 1.00 | 47.38 | C |
| ATOM | 9264 | OE1 | GLU | H | 275 | 47.397 | 32.353 | −2.829 | 1.00 | 48.10 | O |
| ATOM | 9265 | OE2 | GLU | H | 275 | 47.056 | 30.328 | −3.563 | 1.00 | 48.30 | O |
| ATOM | 9266 | N | PHE | H | 276 | 52.141 | 31.150 | −5.019 | 1.00 | 41.69 | N |
| ATOM | 9267 | CA | PHE | H | 276 | 52.808 | 29.857 | −5.003 | 1.00 | 39.52 | C |
| ATOM | 9268 | C | PHE | H | 276 | 52.755 | 29.386 | −3.564 | 1.00 | 39.03 | C |
| ATOM | 9269 | O | PHE | H | 276 | 53.170 | 30.100 | −2.648 | 1.00 | 38.10 | O |
| ATOM | 9270 | CB | PHE | H | 276 | 54.249 | 29.988 | −5.481 | 1.00 | 38.65 | C |
| ATOM | 9271 | CG | PHE | H | 276 | 54.369 | 30.243 | −6.951 | 1.00 | 38.48 | C |
| ATOM | 9272 | CD1 | PHE | H | 276 | 54.031 | 29.256 | −7.872 | 1.00 | 38.27 | C |
| ATOM | 9273 | CD2 | PHE | H | 276 | 54.800 | 31.476 | −7.421 | 1.00 | 38.58 | C |
| ATOM | 9274 | CE1 | PHE | H | 276 | 54.121 | 29.495 | −9.243 | 1.00 | 38.00 | C |
| ATOM | 9275 | CE2 | PHE | H | 276 | 54.894 | 31.724 | −8.790 | 1.00 | 38.36 | C |
| ATOM | 9276 | CZ | PHE | H | 276 | 54.554 | 30.732 | −9.702 | 1.00 | 37.74 | C |
| ATOM | 9277 | N | VAL | H | 277 | 52.224 | 28.185 | −3.368 | 1.00 | 37.80 | N |
| ATOM | 9278 | CA | VAL | H | 277 | 52.069 | 27.633 | −2.037 | 1.00 | 37.39 | C |
| ATOM | 9279 | C | VAL | H | 277 | 53.056 | 26.509 | −1.791 | 1.00 | 36.85 | C |
| ATOM | 9280 | O | VAL | H | 277 | 53.412 | 25.765 | −2.700 | 1.00 | 37.31 | O |
| ATOM | 9281 | CB | VAL | H | 277 | 50.638 | 27.071 | −1.835 | 1.00 | 37.65 | C |
| ATOM | 9282 | CG1 | VAL | H | 277 | 50.423 | 26.681 | −0.379 | 1.00 | 36.24 | C |
| ATOM | 9283 | CG2 | VAL | H | 277 | 49.608 | 28.097 | −2.299 | 1.00 | 38.51 | C |
| ATOM | 9284 | N | CYS | H | 278 | 53.483 | 26.386 | −0.544 | 1.00 | 36.31 | N |
| ATOM | 9285 | CA | CYS | H | 278 | 54.421 | 25.348 | −0.161 | 1.00 | 35.95 | C |
| ATOM | 9286 | C | CYS | H | 278 | 53.983 | 24.777 | 1.183 | 1.00 | 34.83 | C |
| ATOM | 9287 | O | CYS | H | 278 | 53.500 | 25.519 | 2.034 | 1.00 | 34.27 | O |
| ATOM | 9288 | GB | CYS | H | 278 | 55.818 | 25.945 | −0.043 | 1.00 | 35.67 | C |
| ATOM | 9289 | SG | CYS | H | 278 | 57.046 | 24.702 | 0.310 | 1.00 | 39.57 | S |
| ATOM | 9290 | N | LYS | H | 279 | 54.155 | 23.471 | 1.370 | 1.00 | 33.39 | N |
| ATOM | 9291 | CA | LYS | H | 279 | 53.774 | 22.810 | 2.619 | 1.00 | 33.07 | C |
| ATOM | 9292 | C | LYS | H | 279 | 54.944 | 21.983 | 3.186 | 1.00 | 32.16 | C |
| ATOM | 9293 | O | LYS | H | 279 | 55.314 | 20.936 | 2.635 | 1.00 | 31.95 | O |
| ATOM | 9294 | CB | LYS | H | 279 | 52.564 | 21.911 | 2.367 | 1.00 | 34.19 | C |
| ATOM | 9295 | CG | LYS | H | 279 | 51.451 | 22.094 | 3.369 | 1.00 | 36.03 | C |
| ATOM | 9296 | CD | LYS | H | 279 | 51.912 | 21.792 | 4.767 | 1.00 | 36.39 | C |
| ATOM | 9297 | CE | LYS | H | 279 | 50.854 | 22.200 | 5.779 | 1.00 | 36.81 | C |
| ATOM | 9298 | NZ | LYS | H | 279 | 51.292 | 21.982 | 7.178 | 1.00 | 36.20 | N |
| ATOM | 9299 | N | VAL | H | 280 | 55.495 | 22.450 | 4.301 | 1.00 | 31.18 | N |
| ATOM | 9300 | CA | VAL | H | 280 | 56.648 | 21.825 | 4.946 | 1.00 | 31.20 | C |
| ATOM | 9301 | C | VAL | H | 280 | 56.417 | 21.072 | 6.264 | 1.00 | 31.10 | C |
| ATOM | 9302 | O | VAL | H | 280 | 55.619 | 21.489 | 7.094 | 1.00 | 31.08 | O |
| ATOM | 9303 | CB | VAL | H | 280 | 57.727 | 22.903 | 5.221 | 1.00 | 30.51 | C |
| ATOM | 9304 | CG1 | VAL | H | 280 | 58.967 | 22.269 | 5.838 | 1.00 | 30.03 | C |
| ATOM | 9305 | CG2 | VAL | H | 280 | 58.068 | 23.632 | 3.926 | 1.00 | 30.17 | C |
| ATOM | 9306 | N | TYR | H | 281 | 57.150 | 19.971 | 6.442 | 1.00 | 31.13 | N |
| ATOM | 9307 | CA | TYR | H | 281 | 57.110 | 19.165 | 7.666 | 1.00 | 31.35 | C |
| ATOM | 9308 | C | TYR | H | 281 | 58.557 | 18.911 | 8.126 | 1.00 | 30.45 | C |
| ATOM | 9309 | O | TYR | H | 281 | 59.417 | 18.558 | 7.317 | 1.00 | 29.54 | O |
| ATOM | 9310 | CB | TYR | H | 281 | 56.426 | 17.805 | 7.433 | 1.00 | 34.05 | C |
| ATOM | 9311 | CG | TYR | H | 281 | 54.983 | 17.892 | 6.985 | 1.00 | 35.89 | C |
| ATOM | 9312 | CD1 | TYR | H | 281 | 54.661 | 17.969 | 5.632 | 1.00 | 36.41 | C |
| ATOM | 9313 | CD2 | TYR | H | 281 | 53.945 | 17.962 | 7.919 | 1.00 | 36.66 | C |
| ATOM | 9314 | CE1 | TYR | H | 281 | 53.347 | 18.123 | 5.208 | 1.00 | 37.37 | C |
| ATOM | 9315 | CE2 | TYR | H | 281 | 52.615 | 18.118 | 7.509 | 1.00 | 37.92 | C |
| ATOM | 9316 | CZ | TYR | H | 281 | 52.327 | 18.201 | 6.147 | 1.00 | 38.00 | C |
| ATOM | 9317 | OH | TYR | H | 281 | 51.033 | 18.403 | 5.726 | 1.00 | 38.37 | O |
| ATOM | 9318 | N | SER | H | 282 | 58.821 | 19.090 | 9.417 | 1.00 | 29.51 | N |
| ATOM | 9319 | CA | SER | H | 282 | 60.159 | 18.875 | 9.962 | 1.00 | 29.67 | C |
| ATOM | 9320 | C | SER | H | 282 | 60.142 | 18.858 | 11.497 | 1.00 | 29.90 | C |
| ATOM | 9321 | O | SER | H | 282 | 59.332 | 19.538 | 12.126 | 1.00 | 30.45 | O |
| ATOM | 9322 | CB | SER | H | 282 | 61.110 | 19.977 | 9.456 | 1.00 | 29.57 | C |
| ATOM | 9323 | OG | SER | H | 282 | 62.438 | 19.767 | 9.908 | 1.00 | 29.13 | O |
| ATOM | 9324 | N | ASP | H | 283 | 61.024 | 18.065 | 12.091 | 1.00 | 29.63 | N |
| ATOM | 9325 | CA | ASP | H | 283 | 61.143 | 17.975 | 13.549 | 1.00 | 30.15 | C |
| ATOM | 9326 | C | ASP | H | 283 | 62.118 | 19.096 | 13.941 | 1.00 | 30.23 | C |
| ATOM | 9327 | O | ASP | H | 283 | 61.775 | 20.029 | 14.665 | 1.00 | 31.19 | O |
| ATOM | 9328 | CB | ASP | H | 283 | 61.704 | 16.594 | 13.929 | 1.00 | 31.41 | C |
| ATOM | 9329 | CG | ASP | H | 283 | 61.957 | 16.438 | 15.422 | 1.00 | 32.47 | C |
| ATOM | 9330 | OD1 | ASP | H | 283 | 62.102 | 15.275 | 15.869 | 1.00 | 31.49 | O |
| ATOM | 9331 | OD2 | ASP | H | 283 | 62.022 | 17.460 | 16.145 | 1.00 | 32.81 | O |
| ATOM | 9332 | N | ALA | H | 284 | 63.342 | 18.985 | 13.451 | 1.00 | 29.34 | N |
| ATOM | 9333 | CA | ALA | H | 284 | 64.356 | 19.997 | 13.683 | 1.00 | 29.14 | C |
| ATOM | 9334 | C | ALA | H | 284 | 63.812 | 21.267 | 13.005 | 1.00 | 28.51 | C |
| ATOM | 9335 | O | ALA | H | 284 | 63.304 | 21.194 | 11.897 | 1.00 | 28.63 | O |

TABLE 3-continued

FGFR2(D2–D3) Complexed with FGF2

| ATOM | 9336 | CB | ALA | H | 284 | 65.669 | 19.559 | 13.014 | 1.00 | 27.52 | C |
|---|---|---|---|---|---|---|---|---|---|---|---|
| ATOM | 9337 | N | GLN | H | 285 | 63.917 | 22.414 | 13.663 | 1.00 | 28.67 | N |
| ATOM | 9338 | CA | GLN | H | 285 | 63.416 | 23.671 | 13.111 | 1.00 | 28.52 | C |
| ATOM | 9339 | C | GLN | H | 285 | 63.883 | 23.876 | 11.662 | 1.00 | 28.22 | C |
| ATOM | 9340 | O | GLN | H | 285 | 65.083 | 23.898 | 11.391 | 1.00 | 28.44 | O |
| ATOM | 9341 | CB | GLN | H | 285 | 63.912 | 24.822 | 13.984 | 1.00 | 29.12 | C |
| ATOM | 9342 | CG | GLN | H | 285 | 62.896 | 25.925 | 14.200 | 1.00 | 28.42 | C |
| ATOM | 9343 | CD | GLN | H | 285 | 61.558 | 25.395 | 14.677 | 1.00 | 28.46 | C |
| ATOM | 9344 | OE1 | GLN | H | 285 | 61.491 | 24.469 | 15.496 | 1.00 | 28.03 | O |
| ATOM | 9345 | NE2 | GLN | H | 285 | 60.482 | 25.991 | 14.177 | 1.00 | 26.08 | N |
| ATOM | 9346 | N | PRO | H | 286 | 62.946 | 24.020 | 10.712 | 1.00 | 27.62 | N |
| ATOM | 9347 | CA | PRO | H | 286 | 63.296 | 24.219 | 9.299 | 1.00 | 27.16 | C |
| ATOM | 9348 | C | PRO | H | 286 | 63.381 | 25.703 | 8.907 | 1.00 | 28.07 | C |
| ATOM | 9349 | O | PRO | H | 286 | 62.701 | 26.545 | 9.496 | 1.00 | 28.41 | O |
| ATOM | 9350 | CB | PRO | H | 286 | 62.155 | 23.533 | 8.577 | 1.00 | 27.57 | C |
| ATOM | 9351 | CG | PRO | H | 286 | 60.981 | 23.969 | 9.420 | 1.00 | 27.78 | C |
| ATOM | 9352 | CD | PRO | H | 286 | 61.502 | 23.752 | 10.851 | 1.00 | 28.09 | C |
| ATOM | 9353 | N | HIS | H | 287 | 64.212 | 26.012 | 7.915 | 1.00 | 27.90 | N |
| ATOM | 9354 | CA | HIS | H | 287 | 64.355 | 27.382 | 7.425 | 1.00 | 28.46 | C |
| ATOM | 9355 | C | HIS | H | 287 | 63.843 | 27.395 | 5.989 | 1.00 | 28.05 | C |
| ATOM | 9356 | O | HIS | H | 287 | 64.366 | 26.710 | 5.122 | 1.00 | 27.07 | O |
| ATOM | 9357 | CB | HIS | H | 287 | 65.817 | 27.854 | 7.471 | 1.00 | 27.74 | C |
| ATOM | 9358 | CG | HIS | H | 287 | 65.993 | 29.265 | 7.010 | 1.00 | 29.87 | C |
| ATOM | 9359 | ND1 | HIS | H | 287 | 66.529 | 29.587 | 5.782 | 1.00 | 31.80 | N |
| ATOM | 9360 | CD2 | HIS | H | 287 | 65.626 | 30.441 | 7.579 | 1.00 | 30.30 | C |
| ATOM | 9361 | CE1 | HIS | H | 287 | 66.479 | 30.898 | 5.611 | 1.00 | 31.47 | C |
| ATOM | 9362 | NE2 | HIS | H | 287 | 65.934 | 31.440 | 6.687 | 1.00 | 30.23 | N |
| ATOM | 9363 | N | ILE | H | 288 | 62.806 | 28.185 | 5.753 | 1.00 | 29.18 | N |
| ATOM | 9364 | CA | ILE | H | 288 | 62.169 | 28.263 | 4.448 | 1.00 | 29.25 | C |
| ATOM | 9365 | C | ILE | H | 288 | 62.433 | 29.573 | 3.689 | 1.00 | 30.96 | C |
| ATOM | 9366 | O | ILE | H | 288 | 62.399 | 30.664 | 4.266 | 1.00 | 31.51 | O |
| ATOM | 9367 | CB | ILE | H | 288 | 60.642 | 28.082 | 4.621 | 1.00 | 28.49 | C |
| ATOM | 9368 | CG1 | ILE | H | 288 | 60.373 | 26.832 | 5.481 | 1.00 | 29.99 | C |
| ATOM | 9369 | CG2 | ILE | H | 288 | 59.969 | 27.980 | 3.269 | 1.00 | 28.50 | C |
| ATOM | 9370 | CD1 | ILE | H | 288 | 58.884 | 26.559 | 5.795 | 1.00 | 28.45 | C |
| ATOM | 9371 | N | GLN | H | 289 | 62.696 | 29.460 | 2.390 | 1.00 | 31.82 | N |
| ATOM | 9372 | CA | GLN | H | 289 | 62.923 | 30.631 | 1.552 | 1.00 | 32.69 | C |
| ATOM | 9373 | C | GLN | H | 289 | 62.388 | 30.368 | 0.156 | 1.00 | 32.57 | C |
| ATOM | 9374 | O | GLN | H | 289 | 62.260 | 29.212 | −0.254 | 1.00 | 32.41 | O |
| ATOM | 9375 | CB | GLN | H | 289 | 64.414 | 30.963 | 1.458 | 1.00 | 33.25 | C |
| ATOM | 9376 | CG | GLN | H | 289 | 65.269 | 29.878 | 0.859 | 1.00 | 33.75 | C |
| ATOM | 9377 | CD | GLN | H | 289 | 66.744 | 30.258 | 0.825 | 1.00 | 35.50 | C |
| ATOM | 9378 | OE1 | GLN | H | 289 | 67.139 | 31.179 | 0.112 | 1.00 | 36.06 | O |
| ATOM | 9379 | NE2 | GLN | H | 289 | 67.564 | 29.547 | 1.602 | 1.00 | 34.39 | N |
| ATOM | 9380 | N | TRP | H | 290 | 62.060 | 31.440 | −0.559 | 1.00 | 31.53 | N |
| ATOM | 9381 | CA | TRP | H | 290 | 61.570 | 31.333 | −1.922 | 1.00 | 32.53 | C |
| ATOM | 9382 | C | TRP | H | 290 | 62.642 | 31.893 | −2.848 | 1.00 | 33.98 | C |
| ATOM | 9383 | O | TRP | H | 290 | 63.164 | 32.985 | −2.617 | 1.00 | 33.48 | O |
| ATOM | 9384 | CB | TRP | H | 290 | 60.265 | 32.108 | −2.102 | 1.00 | 30.04 | C |
| ATOM | 9385 | CG | TRP | H | 290 | 59.055 | 31.426 | −1.495 | 1.00 | 28.03 | C |
| ATOM | 9386 | CD1 | TRP | H | 290 | 58.547 | 31.625 | −0.250 | 1.00 | 27.08 | C |
| ATOM | 9387 | CD2 | TRP | H | 290 | 58.199 | 30.459 | −2.128 | 1.00 | 26.37 | C |
| ATOM | 9388 | NE1 | TRP | H | 290 | 57.422 | 30.852 | −0.064 | 1.00 | 26.17 | N |
| ATOM | 9389 | CE2 | TRP | H | 290 | 57.186 | 30.126 | −1.201 | 1.00 | 26.79 | C |
| ATOM | 9390 | CE3 | TRP | H | 290 | 58.186 | 29.850 | −3.390 | 1.00 | 25.93 | C |
| ATOM | 9391 | CZ2 | TRP | H | 290 | 56.159 | 29.205 | −1.498 | 1.00 | 25.61 | C |
| ATOM | 9392 | CZ3 | TRP | H | 290 | 57.170 | 28.937 | −3.685 | 1.00 | 26.82 | C |
| ATOM | 9393 | CH2 | TRP | H | 290 | 56.166 | 28.627 | −2.737 | 1.00 | 25.68 | C |
| ATOM | 9394 | N | ILE | H | 291 | 62.955 | 31.138 | −3.896 | 1.00 | 35.66 | N |
| ATOM | 9395 | CA | ILE | H | 291 | 63.989 | 31.515 | −4.844 | 1.00 | 39.09 | C |
| ATOM | 9396 | C | ILE | H | 291 | 63.525 | 31.573 | −6.304 | 1.00 | 40.97 | C |
| ATOM | 9397 | O | ILE | H | 291 | 62.742 | 30.736 | −6.759 | 1.00 | 41.16 | O |
| ATOM | 9398 | CB | ILE | H | 291 | 65.171 | 30.518 | −4.771 | 1.00 | 38.90 | C |
| ATOM | 9399 | CG1 | ILE | H | 291 | 65.583 | 30.296 | −3.311 | 1.00 | 40.33 | C |
| ATOM | 9400 | CG2 | ILE | H | 291 | 66.337 | 31.044 | −5.587 | 1.00 | 39.19 | C |
| ATOM | 9401 | CD1 | ILE | H | 291 | 66.613 | 29.197 | −3.115 | 1.00 | 40.21 | C |
| ATOM | 9402 | N | LYS | H | 292 | 64.030 | 32.561 | −7.034 | 1.00 | 42.59 | N |
| ATOM | 9403 | CA | LYS | H | 292 | 63.716 | 32.732 | −8.449 | 1.00 | 44.15 | C |
| ATOM | 9404 | C | LYS | H | 292 | 65.004 | 32.417 | −9.215 | 1.00 | 44.86 | C |
| ATOM | 9405 | O | LYS | H | 292 | 66.073 | 32.920 | −8.859 | 1.00 | 44.43 | O |
| ATOM | 9406 | CB | LYS | H | 292 | 63.294 | 34.179 | −8.708 | 1.00 | 44.79 | C |
| ATOM | 9407 | CG | LYS | H | 292 | 62.216 | 34.374 | −9.782 | 1.00 | 46.10 | C |
| ATOM | 9408 | CD | LYS | H | 292 | 62.752 | 34.216 | −11.188 | 1.00 | 46.60 | C |
| ATOM | 9409 | CE | LYS | H | 292 | 61.676 | 34.580 | −12.217 | 1.00 | 46.77 | C |
| ATOM | 9410 | NZ | LYS | H | 292 | 62.245 | 34.792 | −13.575 | 1.00 | 46.44 | N |
| ATOM | 9411 | N | HIS | H | 293 | 64.916 | 31.571 | −10.239 | 1.00 | 46.05 | N |
| ATOM | 9412 | CA | HIS | H | 293 | 66.097 | 31.225 | −11.031 | 1.00 | 47.50 | C |

TABLE 3-continued

FGFR2(D2–D3) Complexed with FGF2

| ATOM | 9413 | C | HIS | H | 293 | 66.315 | 32.299 | −12.092 | 1.00 | 48.23 | C |
|---|---|---|---|---|---|---|---|---|---|---|---|
| ATOM | 9414 | O | HIS | H | 293 | 65.552 | 32.398 | −13.044 | 1.00 | 49.00 | O |
| ATOM | 9415 | CB | HIS | H | 293 | 65.919 | 29.857 | −11.699 | 1.00 | 47.52 | C |
| ATOM | 9416 | N | VAL | H | 294 | 67.349 | 33.114 | −11.925 | 1.00 | 49.24 | N |
| ATOM | 9417 | CA | VAL | H | 294 | 67.626 | 34.182 | −12.886 | 1.00 | 49.93 | C |
| ATOM | 9418 | C | VAL | H | 294 | 68.978 | 33.999 | −13.575 | 1.00 | 50.69 | C |
| ATOM | 9419 | O | VAL | H | 294 | 69.468 | 34.901 | −14.265 | 1.00 | 52.03 | O |
| ATOM | 9420 | CB | VAL | H | 294 | 67.604 | 35.562 | −12.196 | 1.00 | 49.74 | C |
| ATOM | 9421 | CG1 | VAL | H | 294 | 66.247 | 35.806 | −11.558 | 1.00 | 49.61 | C |
| ATOM | 9422 | CG2 | VAL | H | 294 | 68.700 | 35.631 | −11.142 | 1.00 | 50.11 | C |
| ATOM | 9423 | N | PRO | H | 307 | 74.376 | 28.181 | −11.083 | 1.00 | 60.18 | N |
| ATOM | 9424 | CA | PRO | H | 307 | 73.015 | 28.699 | −11.266 | 1.00 | 59.57 | C |
| ATOM | 9425 | C | PRO | H | 307 | 72.797 | 30.049 | −10.589 | 1.00 | 58.87 | C |
| ATOM | 9426 | O | PRO | H | 307 | 72.977 | 30.187 | −9.378 | 1.00 | 58.70 | O |
| ATOM | 9427 | CB | PRO | H | 307 | 72.141 | 27.600 | −10.661 | 1.00 | 59.86 | C |
| ATOM | 9428 | CG | PRO | H | 307 | 73.005 | 27.068 | −9.555 | 1.00 | 60.24 | C |
| ATOM | 9429 | CD | PRO | H | 307 | 74.370 | 26.983 | −10.222 | 1.00 | 60.69 | C |
| ATOM | 9430 | N | TYR | H | 308 | 72.419 | 31.045 | −11.387 | 1.00 | 57.90 | N |
| ATOM | 9431 | CA | TYR | H | 308 | 72.163 | 32.385 | −10.878 | 1.00 | 56.75 | C |
| ATOM | 9432 | C | TYR | H | 308 | 70.820 | 32.403 | −10.157 | 1.00 | 56.02 | C |
| ATOM | 9433 | O | TYR | H | 308 | 69.766 | 32.244 | −10.780 | 1.00 | 55.98 | O |
| ATOM | 9434 | CB | TYR | H | 308 | 72.148 | 33.398 | −12.025 | 1.00 | 57.22 | C |
| ATOM | 9435 | N | LEU | H | 309 | 70.865 | 32.605 | −8.843 | 1.00 | 54.51 | N |
| ATOM | 9436 | CA | LEU | H | 309 | 69.653 | 32.631 | −8.034 | 1.00 | 52.98 | C |
| ATOM | 9437 | C | LEU | H | 309 | 69.388 | 33.991 | −7.398 | 1.00 | 51.39 | C |
| ATOM | 9438 | O | LEU | H | 309 | 70.307 | 34.780 | −7.194 | 1.00 | 52.19 | O |
| ATOM | 9439 | CB | LEU | H | 309 | 69.738 | 31.569 | −6.936 | 1.00 | 53.03 | C |
| ATOM | 9440 | CG | LEU | H | 309 | 69.988 | 30.127 | −7.391 | 1.00 | 53.20 | C |
| ATOM | 9441 | CD1 | LEU | H | 309 | 70.038 | 29.221 | −6.170 | 1.00 | 53.52 | C |
| ATOM | 9442 | CD2 | LEU | H | 309 | 68.886 | 29.679 | −8.349 | 1.00 | 53.46 | C |
| ATOM | 9443 | N | LYS | H | 310 | 68.122 | 34.256 | −7.095 | 1.00 | 48.98 | N |
| ATOM | 9444 | CA | LYS | H | 310 | 67.719 | 35.502 | −6.453 | 1.00 | 46.80 | C |
| ATOM | 9445 | C | LYS | H | 310 | 66.721 | 35.182 | −5.341 | 1.00 | 45.04 | C |
| ATOM | 9446 | O | LYS | H | 310 | 65.668 | 34.594 | −5.592 | 1.00 | 43.73 | O |
| ATOM | 9447 | CB | LYS | H | 310 | 67.071 | 36.446 | −7.470 | 1.00 | 47.70 | C |
| ATOM | 9448 | N | VAL | H | 311 | 67.060 | 35.568 | −4.114 | 1.00 | 43.31 | N |
| ATOM | 9449 | CA | VAL | H | 311 | 66.203 | 35.317 | −2.961 | 1.00 | 41.81 | C |
| ATOM | 9450 | C | VAL | H | 311 | 65.068 | 36.326 | −2.870 | 1.00 | 41.18 | C |
| ATOM | 9451 | O | VAL | H | 311 | 65.292 | 37.513 | −2.631 | 1.00 | 41.93 | O |
| ATOM | 9452 | CB | VAL | H | 311 | 67.014 | 35.361 | −1.641 | 1.00 | 41.66 | C |
| ATOM | 9453 | CG1 | VAL | H | 311 | 66.072 | 35.199 | −0.438 | 1.00 | 41.45 | C |
| ATOM | 9454 | CG2 | VAL | H | 311 | 68.075 | 34.265 | −1.649 | 1.00 | 40.22 | C |
| ATOM | 9455 | N | LEU | H | 312 | 63.846 | 35.846 | −3.047 | 1.00 | 39.47 | N |
| ATOM | 9456 | CA | LEU | H | 312 | 62.678 | 36.712 | −2.997 | 1.00 | 39.06 | C |
| ATOM | 9457 | C | LEU | H | 312 | 62.191 | 36.958 | −1.580 | 1.00 | 38.82 | C |
| ATOM | 9458 | O | LEU | H | 312 | 61.750 | 38.059 | −1.246 | 1.00 | 39.00 | O |
| ATOM | 9459 | CB | LEU | H | 312 | 61.530 | 36.093 | −3.795 | 1.00 | 38.04 | C |
| ATOM | 9460 | CG | LEU | H | 312 | 61.868 | 35.589 | −5.194 | 1.00 | 38.09 | C |
| ATOM | 9461 | CD1 | LEU | H | 312 | 60.606 | 35.046 | −5.840 | 1.00 | 37.34 | C |
| ATOM | 9462 | CD2 | LEU | H | 312 | 62.478 | 36.724 | −6.030 | 1.00 | 38.16 | C |
| ATOM | 9463 | N | LYS | H | 313 | 62.294 | 35.935 | −0.741 | 1.00 | 38.00 | N |
| ATOM | 9464 | CA | LYS | H | 313 | 61.788 | 36.022 | 0.615 | 1.00 | 36.74 | C |
| ATOM | 9465 | C | LYS | H | 313 | 62.424 | 34.902 | 1.447 | 1.00 | 35.97 | C |
| ATOM | 9466 | O | LYS | H | 313 | 62.619 | 33.790 | 0.949 | 1.00 | 35.18 | O |
| ATOM | 9467 | CB | LYS | H | 313 | 60.271 | 35.853 | 0.496 | 1.00 | 36.72 | C |
| ATOM | 9468 | CG | LYS | H | 313 | 59.418 | 35.909 | 1.718 | 1.00 | 37.50 | C |
| ATOM | 9469 | CD | LYS | H | 313 | 57.995 | 35.679 | 1.221 | 1.00 | 37.93 | C |
| ATOM | 9470 | CE | LYS | H | 313 | 56.951 | 35.675 | 2.312 | 1.00 | 38.60 | C |
| ATOM | 9471 | NZ | LYS | H | 313 | 55.667 | 35.265 | 1.685 | 1.00 | 37.65 | N |
| ATOM | 9472 | N | ALA | H | 314 | 62.751 | 35.196 | 2.703 | 1.00 | 34.47 | N |
| ATOM | 9473 | CA | ALA | H | 314 | 63.368 | 34.208 | 3.583 | 1.00 | 33.45 | C |
| ATOM | 9474 | C | ALA | H | 314 | 62.896 | 34.356 | 5.021 | 1.00 | 32.58 | C |
| ATOM | 9475 | O | ALA | H | 314 | 62.744 | 35.470 | 5.532 | 1.00 | 31.18 | O |
| ATOM | 9476 | CB | ALA | H | 314 | 64.905 | 34.312 | 3.519 | 1.00 | 33.76 | C |
| ATOM | 9477 | N | ALA | H | 315 | 62.679 | 33.213 | 5.670 | 1.00 | 31.78 | N |
| ATOM | 9478 | CA | ALA | H | 315 | 62.209 | 33.164 | 7.051 | 1.00 | 31.19 | C |
| ATOM | 9479 | C | ALA | H | 315 | 63.200 | 33.782 | 8.041 | 1.00 | 31.17 | C |
| ATOM | 9480 | O | ALA | H | 315 | 64.415 | 33.771 | 7.825 | 1.00 | 29.04 | O |
| ATOM | 9481 | CB | ALA | H | 315 | 61.929 | 31.722 | 7.444 | 1.00 | 31.28 | C |
| ATOM | 9482 | N | GLY | H | 316 | 62.659 | 34.308 | 9.133 | 1.00 | 31.15 | N |
| ATOM | 9483 | CA | GLY | H | 316 | 63.481 | 34.920 | 10.158 | 1.00 | 33.15 | C |
| ATOM | 9484 | C | GLY | H | 316 | 62.631 | 35.677 | 11.161 | 1.00 | 35.11 | C |
| ATOM | 9485 | O | GLY | H | 316 | 61.394 | 35.625 | 11.113 | 1.00 | 34.36 | O |
| ATOM | 9486 | N | VAL | H | 317 | 63.292 | 36.379 | 12.075 | 1.00 | 36.85 | N |
| ATOM | 9487 | CA | VAL | H | 317 | 62.585 | 37.151 | 13.091 | 1.00 | 39.38 | C |
| ATOM | 9488 | C | VAL | H | 317 | 61.681 | 38.230 | 12.482 | 1.00 | 40.23 | C |
| ATOM | 9489 | O | VAL | H | 317 | 60.631 | 38.547 | 13.039 | 1.00 | 40.13 | O |

TABLE 3-continued

FGFR2(D2–D3) Complexed with FGF2

| ATOM | 9490 | CB | VAL | H | 317 | 63.575 | 37.798 | 14.081 | 1.00 | 39.91 | C |
|------|------|-----|-----|---|-----|--------|--------|--------|------|-------|---|
| ATOM | 9491 | CG1 | VAL | H | 317 | 62.938 | 39.022 | 14.731 | 1.00 | 41.41 | C |
| ATOM | 9492 | CG2 | VAL | H | 317 | 63.956 | 36.784 | 15.158 | 1.00 | 39.67 | C |
| ATOM | 9493 | N | ASN | H | 318 | 62.081 | 38.777 | 11.335 | 1.00 | 41.18 | N |
| ATOM | 9494 | CA | ASN | H | 318 | 61.285 | 39.805 | 10.676 | 1.00 | 42.85 | C |
| ATOM | 9495 | C | ASN | H | 318 | 60.330 | 39.246 | 9.621 | 1.00 | 43.52 | C |
| ATOM | 9496 | O | ASN | H | 318 | 59.555 | 39.994 | 9.038 | 1.00 | 45.16 | O |
| ATOM | 9497 | CB | ASN | H | 318 | 62.203 | 40.852 | 10.031 | 1.00 | 43.45 | C |
| ATOM | 9498 | N | THR | H | 319 | 60.393 | 37.940 | 9.372 | 1.00 | 43.55 | N |
| ATOM | 9499 | CA | THR | H | 319 | 59.522 | 37.289 | 8.390 | 1.00 | 42.98 | C |
| ATOM | 9500 | C | THR | H | 319 | 59.194 | 35.906 | 8.959 | 1.00 | 42.78 | C |
| ATOM | 9501 | O | THR | H | 319 | 59.766 | 34.895 | 8.550 | 1.00 | 42.38 | O |
| ATOM | 9502 | CB | THR | H | 319 | 60.234 | 37.120 | 7.028 | 1.00 | 43.83 | C |
| ATOM | 9503 | OG1 | THR | H | 319 | 60.967 | 38.310 | 6.712 | 1.00 | 44.68 | O |
| ATOM | 9504 | CG2 | THR | H | 319 | 59.213 | 36.859 | 5.921 | 1.00 | 42.87 | C |
| ATOM | 9505 | N | THR | H | 320 | 58.271 | 35.892 | 9.914 | 1.00 | 42.01 | N |
| ATOM | 9506 | CA | THR | H | 320 | 57.839 | 34.694 | 10.628 | 1.00 | 42.17 | C |
| ATOM | 9507 | C | THR | H | 320 | 57.305 | 33.541 | 9.773 | 1.00 | 40.98 | C |
| ATOM | 9508 | O | THR | H | 320 | 56.901 | 33.738 | 8.627 | 1.00 | 40.68 | O |
| ATOM | 9509 | CB | THR | H | 320 | 56.792 | 35.101 | 11.700 | 1.00 | 43.14 | C |
| ATOM | 9510 | OG1 | THR | H | 320 | 57.448 | 35.887 | 12.702 | 1.00 | 45.22 | O |
| ATOM | 9511 | CG2 | THR | H | 320 | 56.151 | 33.889 | 12.360 | 1.00 | 45.06 | C |
| ATOM | 9512 | N | ASP | H | 321 | 57.318 | 32.333 | 10.342 | 1.00 | 39.70 | N |
| ATOM | 9513 | CA | ASP | H | 321 | 56.835 | 31.149 | 9.639 | 1.00 | 38.81 | C |
| ATOM | 9514 | C | ASP | H | 321 | 55.326 | 31.172 | 9.375 | 1.00 | 38.85 | C |
| ATOM | 9515 | O | ASP | H | 321 | 54.837 | 30.461 | 8.507 | 1.00 | 38.89 | O |
| ATOM | 9516 | CB | ASP | H | 321 | 57.197 | 29.874 | 10.411 | 1.00 | 37.34 | C |
| ATOM | 9517 | CG | ASP | H | 321 | 58.693 | 29.589 | 10.407 | 1.00 | 36.21 | C |
| ATOM | 9518 | OD1 | ASP | H | 321 | 59.383 | 30.100 | 9.500 | 1.00 | 35.02 | O |
| ATOM | 9519 | OD2 | ASP | H | 321 | 59.166 | 28.843 | 11.296 | 1.00 | 33.81 | O |
| ATOM | 9520 | N | LYS | H | 322 | 54.590 | 31.993 | 10.120 | 1.00 | 38.99 | N |
| ATOM | 9521 | CA | LYS | H | 322 | 53.143 | 32.083 | 9.953 | 1.00 | 38.60 | C |
| ATOM | 9522 | C | LYS | H | 322 | 52.720 | 32.329 | 8.499 | 1.00 | 37.91 | C |
| ATOM | 9523 | O | LYS | H | 322 | 51.747 | 31.742 | 8.015 | 1.00 | 36.72 | O |
| ATOM | 9524 | CB | LYS | H | 322 | 52.580 | 33.199 | 10.846 | 1.00 | 38.53 | C |
| ATOM | 9525 | N | GLU | H | 323 | 53.458 | 33.182 | 7.797 | 1.00 | 37.47 | N |
| ATOM | 9526 | CA | GLU | H | 323 | 53.112 | 33.495 | 6.419 | 1.00 | 37.78 | C |
| ATOM | 9527 | C | GLU | H | 323 | 54.225 | 33.234 | 5.394 | 1.00 | 37.88 | C |
| ATOM | 9528 | O | GLU | H | 323 | 54.135 | 33.667 | 4.244 | 1.00 | 37.65 | O |
| ATOM | 9529 | CB | GLU | H | 323 | 52.645 | 34.953 | 6.336 | 1.00 | 37.67 | C |
| ATOM | 9530 | N | ILE | H | 324 | 55.257 | 32.502 | 5.801 | 1.00 | 37.50 | N |
| ATOM | 9531 | CA | ILE | H | 324 | 56.370 | 32.225 | 4.904 | 1.00 | 37.08 | C |
| ATOM | 9532 | C | ILE | H | 324 | 56.077 | 31.163 | 3.821 | 1.00 | 36.29 | C |
| ATOM | 9533 | O | ILE | H | 324 | 56.713 | 31.166 | 2.773 | 1.00 | 35.74 | O |
| ATOM | 9534 | CB | ILE | H | 324 | 57.631 | 31.849 | 5.737 | 1.00 | 37.12 | C |
| ATOM | 9535 | CG1 | ILE | H | 324 | 58.866 | 32.552 | 5.159 | 1.00 | 38.18 | C |
| ATOM | 9536 | CG2 | ILE | H | 324 | 57.798 | 30.336 | 5.816 | 1.00 | 36.42 | C |
| ATOM | 9537 | CD1 | ILE | H | 324 | 59.214 | 32.162 | 3.758 | 1.00 | 38.53 | C |
| ATOM | 9538 | N | GLU | H | 325 | 55.097 | 30.291 | 4.048 | 1.00 | 35.93 | N |
| ATOM | 9539 | CA | GLU | H | 325 | 54.785 | 29.252 | 3.069 | 1.00 | 36.88 | C |
| ATOM | 9540 | C | GLU | H | 325 | 53.963 | 29.653 | 1.841 | 1.00 | 37.34 | C |
| ATOM | 9541 | O | GLU | H | 325 | 53.660 | 28.815 | 0.996 | 1.00 | 36.84 | O |
| ATOM | 9542 | CB | GLU | H | 325 | 54.137 | 28.064 | 3.769 | 1.00 | 37.33 | C |
| ATOM | 9543 | CG | GLU | H | 325 | 55.112 | 27.279 | 4.649 | 1.00 | 38.42 | C |
| ATOM | 9544 | CD | GLU | H | 325 | 54.409 | 26.228 | 5.498 | 1.00 | 39.29 | C |
| ATOM | 9545 | OE1 | GLU | H | 325 | 53.518 | 26.613 | 6.291 | 1.00 | 39.31 | O |
| ATOM | 9546 | OE2 | GLU | H | 325 | 54.742 | 25.029 | 5.368 | 1.00 | 37.77 | O |
| ATOM | 9547 | N | VAL | H | 326 | 53.603 | 30.925 | 1.728 | 1.00 | 37.78 | N |
| ATOM | 9548 | CA | VAL | H | 326 | 52.862 | 31.373 | 0.556 | 1.00 | 39.52 | C |
| ATOM | 9549 | C | VAL | H | 326 | 53.555 | 32.610 | −0.020 | 1.00 | 39.99 | C |
| ATOM | 9550 | O | VAL | H | 326 | 53.880 | 33.536 | 0.714 | 1.00 | 40.78 | O |
| ATOM | 9551 | CB | VAL | H | 326 | 51.375 | 31.676 | 0.903 | 1.00 | 40.06 | C |
| ATOM | 9552 | CG1 | VAL | H | 326 | 51.289 | 32.735 | 2.006 | 1.00 | 41.95 | C |
| ATOM | 9553 | CG2 | VAL | H | 326 | 50.638 | 32.143 | −0.342 | 1.00 | 39.31 | C |
| ATOM | 9554 | N | LEU | H | 327 | 53.817 | 32.597 | −1.326 | 1.00 | 40.27 | N |
| ATOM | 9555 | CA | LEU | H | 327 | 54.478 | 33.712 | −2.006 | 1.00 | 40.64 | C |
| ATOM | 9556 | C | LEU | H | 327 | 53.508 | 34.372 | −2.970 | 1.00 | 42.00 | C |
| ATOM | 9557 | O | LEU | H | 327 | 52.989 | 33.720 | −3.882 | 1.00 | 41.64 | O |
| ATOM | 9558 | CB | LEU | H | 327 | 55.700 | 33.238 | −2.803 | 1.00 | 38.86 | C |
| ATOM | 9559 | CG | LEU | H | 327 | 56.432 | 34.300 | −3.636 | 1.00 | 37.79 | C |
| ATOM | 9560 | CD1 | LEU | H | 327 | 57.253 | 35.215 | −2.718 | 1.00 | 36.93 | C |
| ATOM | 9561 | CD2 | LEU | H | 327 | 57.346 | 33.624 | −4.645 | 1.00 | 36.04 | C |
| ATOM | 9562 | N | TYR | H | 328 | 53.277 | 35.666 | −2.769 | 1.00 | 42.93 | N |
| ATOM | 9563 | CA | TYR | H | 328 | 52.371 | 36.427 | −3.624 | 1.00 | 44.15 | C |
| ATOM | 9564 | C | TYR | H | 328 | 53.129 | 37.341 | −4.591 | 1.00 | 45.79 | C |
| ATOM | 9565 | O | TYR | H | 328 | 54.136 | 37.956 | −4.226 | 1.00 | 45.90 | O |
| ATOM | 9566 | CB | TYR | H | 328 | 51.400 | 37.278 | −2.770 | 1.00 | 42.30 | C |

TABLE 3-continued

FGFR2(D2–D3) Complexed with FGF2

| ATOM | 9567 | CG | TYR | H | 328 | 50.434 | 36.476 | -1.911 | 1.00 | 41.07 | C |
|---|---|---|---|---|---|---|---|---|---|---|---|
| ATOM | 9568 | CD1 | TYR | H | 328 | 50.642 | 36.331 | -0.532 | 1.00 | 40.43 | C |
| ATOM | 9569 | CD2 | TYR | H | 328 | 49.340 | 35.820 | -2.484 | 1.00 | 40.34 | C |
| ATOM | 9570 | CE1 | TYR | H | 328 | 49.784 | 35.548 | 0.254 | 1.00 | 39.51 | C |
| ATOM | 9571 | CE2 | TYR | H | 328 | 48.483 | 35.031 | -1.714 | 1.00 | 39.61 | C |
| ATOM | 9572 | CZ | TYR | H | 328 | 48.712 | 34.897 | -0.349 | 1.00 | 40.54 | C |
| ATOM | 9573 | OH | TYR | H | 328 | 47.891 | 34.077 | 0.398 | 1.00 | 41.41 | O |
| ATOM | 9574 | N | ILE | H | 329 | 52.649 | 37.407 | -5.832 | 1.00 | 47.90 | N |
| ATOM | 9575 | CA | ILE | H | 329 | 53.243 | 38.277 | -6.849 | 1.00 | 49.69 | C |
| ATOM | 9576 | C | ILE | H | 329 | 52.121 | 38.962 | -7.620 | 1.00 | 51.11 | C |
| ATOM | 9577 | O | ILE | H | 329 | 51.392 | 38.317 | -8.372 | 1.00 | 50.96 | O |
| ATOM | 9578 | CB | ILE | H | 329 | 54.107 | 37.512 | -7.844 | 1.00 | 49.40 | C |
| ATOM | 9579 | CG1 | ILE | H | 329 | 55.273 | 36.854 | -7.113 | 1.00 | 49.02 | C |
| ATOM | 9580 | CG2 | ILE | H | 329 | 54.619 | 38.469 | -8.911 | 1.00 | 48.86 | C |
| ATOM | 9581 | CD1 | ILE | H | 329 | 56.103 | 35.964 | -7.994 | 1.00 | 49.85 | C |
| ATOM | 9582 | N | ARG | H | 330 | 51.987 | 40.270 | -7.425 | 1.00 | 52.65 | N |
| ATOM | 9583 | CA | ARG | H | 330 | 50.937 | 41.026 | -8.092 | 1.00 | 54.33 | C |
| ATOM | 9584 | C | ARG | H | 330 | 51.419 | 41.888 | -9.254 | 1.00 | 54.53 | C |
| ATOM | 9585 | O | ARG | H | 330 | 52.595 | 42.253 | -9.340 | 1.00 | 53.97 | O |
| ATOM | 9586 | CB | ARG | H | 330 | 50.177 | 41.898 | -7.084 | 1.00 | 56.10 | C |
| ATOM | 9587 | CG | ARG | H | 330 | 49.459 | 41.108 | -5.994 | 1.00 | 58.20 | C |
| ATOM | 9588 | CD | ARG | H | 330 | 48.308 | 41.898 | -5.396 | 1.00 | 59.84 | C |
| ATOM | 9589 | NE | ARG | H | 330 | 47.443 | 41.061 | -4.564 | 1.00 | 62.08 | N |
| ATOM | 9590 | CZ | ARG | H | 330 | 46.223 | 41.403 | -4.156 | 1.00 | 62.89 | C |
| ATOM | 9591 | NH1 | ARG | H | 330 | 45.706 | 42.574 | -4.498 | 1.00 | 63.06 | N |
| ATOM | 9592 | NH2 | ARG | H | 330 | 45.515 | 40.569 | -3.406 | 1.00 | 63.25 | N |
| ATOM | 9593 | N | ASN | H | 331 | 50.489 | 42.193 | -10.158 | 1.00 | 55.19 | N |
| ATOM | 9594 | CA | ASN | H | 331 | 50.777 | 43.016 | -11.326 | 1.00 | 55.80 | C |
| ATOM | 9595 | C | ASN | H | 331 | 52.050 | 42.499 | -12.001 | 1.00 | 56.05 | C |
| ATOM | 9596 | O | ASN | H | 331 | 53.023 | 43.237 | -12.177 | 1.00 | 55.89 | O |
| ATOM | 9597 | CB | ASN | H | 331 | 50.937 | 44.480 | -10.877 | 1.00 | 56.20 | C |
| ATOM | 9598 | CG | ASN | H | 331 | 50.917 | 45.455 | -12.038 | 1.00 | 56.60 | C |
| ATOM | 9599 | OD1 | ASN | H | 331 | 50.701 | 45.075 | -13.187 | 1.00 | 57.12 | O |
| ATOM | 9600 | ND2 | ASN | H | 331 | 51.137 | 46.730 | -11.737 | 1.00 | 55.92 | N |
| ATOM | 9601 | N | VAL | H | 332 | 52.029 | 41.224 | -12.387 | 1.00 | 56.09 | N |
| ATOM | 9602 | CA | VAL | H | 332 | 53.188 | 40.593 | -13.014 | 1.00 | 55.89 | C |
| ATOM | 9603 | C | VAL | H | 332 | 53.578 | 41.172 | -14.367 | 1.00 | 55.80 | C |
| ATOM | 9604 | O | VAL | H | 332 | 52.735 | 41.652 | -15.127 | 1.00 | 55.56 | O |
| ATOM | 9605 | CB | VAL | H | 332 | 52.988 | 39.067 | -13.197 | 1.00 | 55.93 | C |
| ATOM | 9606 | CG1 | VAL | H | 332 | 52.608 | 38.419 | -11.872 | 1.00 | 56.01 | C |
| ATOM | 9607 | CG2 | VAL | H | 332 | 51.930 | 38.803 | -14.240 | 1.00 | 56.49 | C |
| ATOM | 9608 | N | THR | H | 333 | 54.876 | 41.117 | -14.648 | 1.00 | 55.86 | N |
| ATOM | 9609 | CA | THR | H | 333 | 55.437 | 41.591 | -15.905 | 1.00 | 55.84 | C |
| ATOM | 9610 | C | THR | H | 333 | 55.973 | 40.347 | -16.606 | 1.00 | 55.98 | C |
| ATOM | 9611 | O | THR | H | 333 | 55.989 | 39.265 | -16.015 | 1.00 | 55.70 | O |
| ATOM | 9612 | CB | THR | H | 333 | 56.610 | 42.576 | -15.667 | 1.00 | 56.00 | C |
| ATOM | 9613 | OG1 | THR | H | 333 | 57.707 | 41.887 | -15.053 | 1.00 | 55.64 | O |
| ATOM | 9614 | CG2 | THR | H | 333 | 56.171 | 43.716 | -14.757 | 1.00 | 56.17 | C |
| ATOM | 9615 | N | PHE | H | 334 | 56.402 | 40.489 | -17.856 | 1.00 | 55.64 | N |
| ATOM | 9616 | CA | PHE | H | 334 | 56.943 | 39.354 | -18.595 | 1.00 | 55.14 | C |
| ATOM | 9617 | C | PHE | H | 334 | 58.255 | 38.924 | -17.935 | 1.00 | 54.70 | C |
| ATOM | 9618 | O | PHE | H | 334 | 58.697 | 37.778 | -18.072 | 1.00 | 54.50 | O |
| ATOM | 9619 | CB | PHE | H | 334 | 57.188 | 39.744 | -20.059 | 1.00 | 54.92 | C |
| ATOM | 9620 | N | GLU | H | 335 | 58.867 | 39.853 | -17.209 | 1.00 | 53.71 | N |
| ATOM | 9621 | CA | GLU | H | 335 | 60.128 | 39.585 | -16.529 | 1.00 | 53.18 | C |
| ATOM | 9622 | C | GLU | H | 335 | 59.956 | 38.597 | -15.372 | 1.00 | 52.08 | C |
| ATOM | 9623 | O | GLU | H | 335 | 60.894 | 37.889 | -15.010 | 1.00 | 51.65 | O |
| ATOM | 9624 | CB | GLU | H | 335 | 60.734 | 40.896 | -16.009 | 1.00 | 52.71 | C |
| ATOM | 9625 | N | ASP | H | 336 | 58.753 | 38.550 | -14.802 | 1.00 | 50.89 | N |
| ATOM | 9626 | CA | ASP | H | 336 | 58.477 | 37.653 | -13.685 | 1.00 | 49.91 | C |
| ATOM | 9627 | C | ASP | H | 336 | 58.419 | 36.179 | -14.084 | 1.00 | 49.25 | C |
| ATOM | 9628 | O | ASP | H | 336 | 58.576 | 35.301 | -13.238 | 1.00 | 48.81 | O |
| ATOM | 9629 | CB | ASP | H | 336 | 57.177 | 38.060 | -12.991 | 1.00 | 49.37 | C |
| ATOM | 9630 | CG | ASP | H | 336 | 57.285 | 39.410 | -12.313 | 1.00 | 49.80 | C |
| ATOM | 9631 | OD1 | ASP | H | 336 | 58.295 | 39.634 | -11.609 | 1.00 | 50.47 | O |
| ATOM | 9632 | OD2 | ASP | H | 336 | 56.364 | 40.243 | -12.470 | 1.00 | 49.20 | O |
| ATOM | 9633 | N | ALA | H | 337 | 58.197 | 35.913 | -15.369 | 1.00 | 48.17 | N |
| ATOM | 9634 | CA | ALA | H | 337 | 58.143 | 34.539 | -15.865 | 1.00 | 47.58 | C |
| ATOM | 9635 | C | ALA | H | 337 | 59.401 | 33.780 | -15.447 | 1.00 | 46.88 | C |
| ATOM | 9636 | O | ALA | H | 337 | 60.477 | 34.365 | -15.339 | 1.00 | 46.85 | O |
| ATOM | 9637 | CB | ALA | H | 337 | 58.025 | 34.533 | -17.390 | 1.00 | 47.07 | C |
| ATOM | 9638 | N | GLY | H | 338 | 59.268 | 32.479 | -15.216 | 1.00 | 45.84 | N |
| ATOM | 9639 | CA | GLY | H | 338 | 60.428 | 31.694 | -14.837 | 1.00 | 44.74 | C |
| ATOM | 9640 | C | GLY | H | 338 | 60.166 | 30.625 | -13.791 | 1.00 | 44.03 | C |
| ATOM | 9641 | O | GLY | H | 338 | 59.018 | 30.370 | -13.408 | 1.00 | 43.61 | O |
| ATOM | 9642 | N | GLU | H | 339 | 61.245 | 30.004 | -13.323 | 1.00 | 42.77 | N |
| ATOM | 9643 | CA | GLU | H | 339 | 61.152 | 28.942 | -12.324 | 1.00 | 42.35 | C |

TABLE 3-continued

FGFR2(D2–D3) Complexed with FGF2

| ATOM | 9644 | C | GLU | H | 339 | 61.277 | 29.461 | −10.895 | 1.00 | 40.94 | C |
|---|---|---|---|---|---|---|---|---|---|---|---|
| ATOM | 9645 | O | GLU | H | 339 | 62.246 | 30.136 | −10.558 | 1.00 | 40.42 | O |
| ATOM | 9646 | CB | GLU | H | 339 | 62.233 | 27.880 | −12.572 | 1.00 | 42.79 | C |
| ATOM | 9647 | CG | GLU | H | 339 | 62.137 | 26.664 | −11.645 | 1.00 | 44.52 | C |
| ATOM | 9648 | CD | GLU | H | 339 | 63.097 | 25.539 | −12.030 | 1.00 | 46.13 | C |
| ATOM | 9649 | OE1 | GLU | H | 339 | 64.315 | 25.798 | −12.120 | 1.00 | 47.18 | O |
| ATOM | 9650 | OE2 | GLU | H | 339 | 62.636 | 24.394 | −12.237 | 1.00 | 46.84 | O |
| ATOM | 9651 | N | TYR | H | 340 | 60.280 | 29.146 | −10.072 | 1.00 | 39.59 | N |
| ATOM | 9652 | CA | TYR | H | 340 | 60.259 | 29.531 | −8.664 | 1.00 | 38.28 | C |
| ATOM | 9653 | C | TYR | H | 340 | 60.448 | 28.290 | −7.784 | 1.00 | 37.55 | C |
| ATOM | 9654 | O | TYR | H | 340 | 59.855 | 27.229 | −8.034 | 1.00 | 37.22 | O |
| ATOM | 9655 | CB | TYR | H | 340 | 58.940 | 30.212 | −8.305 | 1.00 | 38.61 | C |
| ATOM | 9656 | CG | TYR | H | 340 | 58.797 | 31.603 | −8.884 | 1.00 | 39.74 | C |
| ATOM | 9657 | CD1 | TYR | H | 340 | 58.677 | 31.799 | −10.262 | 1.00 | 39.98 | C |
| ATOM | 9658 | CD2 | TYR | H | 340 | 58.775 | 32.724 | −8.054 | 1.00 | 39.49 | C |
| ATOM | 9659 | CE1 | TYR | H | 340 | 58.536 | 33.077 | −10.800 | 1.00 | 40.79 | C |
| ATOM | 9660 | CE2 | TYR | H | 340 | 58.637 | 34.002 | −8.578 | 1.00 | 40.34 | C |
| ATOM | 9661 | CZ | TYR | H | 340 | 58.517 | 34.176 | −9.952 | 1.00 | 41.35 | C |
| ATOM | 9662 | OH | TYR | H | 340 | 58.382 | 35.445 | −10.475 | 1.00 | 42.00 | O |
| ATOM | 9663 | N | THR | H | 341 | 61.266 | 28.425 | −6.748 | 1.00 | 35.65 | N |
| ATOM | 9664 | CA | THR | H | 341 | 61.536 | 27.301 | −5.872 | 1.00 | 34.71 | C |
| ATOM | 9665 | C | THR | H | 341 | 61.341 | 27.567 | −4.387 | 1.00 | 34.35 | C |
| ATOM | 9666 | O | THR | H | 341 | 61.777 | 28.592 | −3.864 | 1.00 | 33.93 | O |
| ATOM | 9667 | CB | THR | H | 341 | 62.985 | 26.800 | −6.053 | 1.00 | 33.92 | C |
| ATOM | 9668 | OG1 | THR | H | 341 | 63.166 | 26.323 | −7.388 | 1.00 | 34.09 | O |
| ATOM | 9669 | CG2 | THR | H | 341 | 63.306 | 25.687 | −5.053 | 1.00 | 33.25 | C |
| ATOM | 9670 | N | CYS | H | 342 | 60.667 | 26.638 | −3.720 | 1.00 | 33.12 | N |
| ATOM | 9671 | CA | CYS | H | 342 | 60.506 | 26.724 | −2.278 | 1.00 | 33.28 | C |
| ATOM | 9672 | C | CYS | H | 342 | 61.601 | 25.807 | −1.741 | 1.00 | 32.46 | C |
| ATOM | 9673 | O | CYS | H | 342 | 61.624 | 24.608 | −2.048 | 1.00 | 32.40 | O |
| ATOM | 9674 | CB | CYS | H | 342 | 59.148 | 26.204 | −1.818 | 1.00 | 33.42 | C |
| ATOM | 9675 | SG | CYS | H | 342 | 59.108 | 26.023 | −0.019 | 1.00 | 36.87 | S |
| ATOM | 9676 | N | LEU | H | 343 | 62.514 | 26.366 | −0.958 | 1.00 | 31.35 | N |
| ATOM | 9677 | CA | LEU | H | 343 | 63.617 | 25.586 | −0.408 | 1.00 | 30.39 | C |
| ATOM | 9678 | C | LEU | H | 343 | 63.578 | 25.559 | 1.117 | 1.00 | 29.88 | C |
| ATOM | 9679 | O | LEU | H | 343 | 63.520 | 26.605 | 1.768 | 1.00 | 29.41 | O |
| ATOM | 9680 | CB | LEU | H | 343 | 64.946 | 26.166 | −0.890 | 1.00 | 31.72 | C |
| ATOM | 9681 | CG | LEU | H | 343 | 66.223 | 25.422 | −0.480 | 1.00 | 33.14 | C |
| ATOM | 9682 | CD1 | LEU | H | 343 | 67.337 | 25.785 | −1.432 | 1.00 | 34.29 | C |
| ATOM | 9683 | CD2 | LEU | H | 343 | 66.600 | 25.767 | 0.962 | 1.00 | 34.27 | C |
| ATOM | 9684 | N | ALA | H | 344 | 63.606 | 24.351 | 1.678 | 1.00 | 28.52 | N |
| ATOM | 9685 | CA | ALA | H | 344 | 63.565 | 24.152 | 3.119 | 1.00 | 28.66 | C |
| ATOM | 9686 | C | ALA | H | 344 | 64.776 | 23.376 | 3.607 | 1.00 | 28.75 | C |
| ATOM | 9687 | O | ALA | H | 344 | 65.087 | 22.298 | 3.091 | 1.00 | 28.52 | O |
| ATOM | 9688 | CB | ALA | H | 344 | 62.290 | 23.402 | 3.519 | 1.00 | 26.24 | C |
| ATOM | 9689 | N | GLY | H | 345 | 65.451 | 23.917 | 4.616 | 1.00 | 28.93 | N |
| ATOM | 9690 | CA | GLY | H | 345 | 66.605 | 23.230 | 5.158 | 1.00 | 28.63 | C |
| ATOM | 9691 | C | GLY | H | 345 | 66.671 | 23.246 | 6.672 | 1.00 | 28.33 | C |
| ATOM | 9692 | O | GLY | H | 345 | 66.179 | 24.181 | 7.305 | 1.00 | 27.94 | O |
| ATOM | 9693 | N | ASN | H | 346 | 67.244 | 22.183 | 7.238 | 1.00 | 28.29 | N |
| ATOM | 9694 | CA | ASN | H | 346 | 67.470 | 22.061 | 8.677 | 1.00 | 29.80 | C |
| ATOM | 9695 | C | ASN | H | 346 | 68.912 | 21.547 | 8.843 | 1.00 | 30.24 | C |
| ATOM | 9696 | O | ASN | H | 346 | 69.619 | 21.360 | 7.849 | 1.00 | 28.99 | O |
| ATOM | 9697 | CB | ASN | H | 346 | 66.455 | 21.099 | 9.340 | 1.00 | 29.39 | C |
| ATOM | 9698 | CG | ASN | H | 346 | 66.493 | 19.675 | 8.768 | 1.00 | 31.32 | C |
| ATOM | 9699 | OD1 | ASN | H | 346 | 67.527 | 19.196 | 8.307 | 1.00 | 30.86 | O |
| ATOM | 9700 | ND2 | ASN | H | 346 | 65.354 | 18.985 | 8.829 | 1.00 | 32.58 | N |
| ATOM | 9701 | N | SER | H | 347 | 69.339 | 21.323 | 10.084 | 1.00 | 32.25 | N |
| ATOM | 9702 | CA | SER | H | 347 | 70.694 | 20.839 | 10.374 | 1.00 | 33.21 | C |
| ATOM | 9703 | C | SER | H | 347 | 71.072 | 19.546 | 9.641 | 1.00 | 33.84 | C |
| ATOM | 9704 | O | SER | H | 347 | 72.235 | 19.323 | 9.328 | 1.00 | 34.09 | O |
| ATOM | 9705 | CB | SER | H | 347 | 70.844 | 20.629 | 11.887 | 1.00 | 34.51 | C |
| ATOM | 9706 | OG | SER | H | 347 | 69.870 | 19.718 | 12.394 | 1.00 | 34.95 | O |
| ATOM | 9707 | N | ILE | H | 348 | 70.084 | 18.699 | 9.367 | 1.00 | 34.13 | N |
| ATOM | 9708 | CA | ILE | H | 348 | 70.318 | 17.434 | 8.686 | 1.00 | 33.98 | C |
| ATOM | 9709 | C | ILE | H | 348 | 70.498 | 17.551 | 7.167 | 1.00 | 34.47 | C |
| ATOM | 9710 | O | ILE | H | 348 | 71.387 | 16.911 | 6.591 | 1.00 | 34.96 | O |
| ATOM | 9711 | CB | ILE | H | 348 | 69.168 | 16.454 | 9.014 | 1.00 | 34.31 | C |
| ATOM | 9712 | CG1 | ILE | H | 348 | 69.134 | 16.207 | 10.525 | 1.00 | 33.70 | C |
| ATOM | 9713 | CG2 | ILE | H | 348 | 69.363 | 15.145 | 8.273 | 1.00 | 35.12 | C |
| ATOM | 9714 | CD1 | ILE | H | 348 | 67.761 | 15.971 | 11.081 | 1.00 | 35.74 | C |
| ATOM | 9715 | N | GLY | H | 349 | 69.667 | 18.364 | 6.520 | 1.00 | 34.17 | N |
| ATOM | 9716 | CA | GLY | H | 349 | 69.769 | 18.514 | 5.081 | 1.00 | 33.60 | C |
| ATOM | 9717 | C | GLY | H | 349 | 68.802 | 19.506 | 4.452 | 1.00 | 34.04 | C |
| ATOM | 9718 | O | GLY | H | 349 | 68.050 | 20.191 | 5.147 | 1.00 | 33.36 | O |
| ATOM | 9719 | N | ILE | H | 350 | 68.813 | 19.540 | 3.119 | 1.00 | 34.41 | N |
| ATOM | 9720 | CA | ILE | H | 350 | 68.006 | 20.452 | 2.308 | 1.00 | 34.58 | C |

TABLE 3-continued

| FGFR2(D2–D3) Complexed with FGF2 | | | | | | | | | | |
|---|---|---|---|---|---|---|---|---|---|---|
| ATOM | 9721 | C | ILE | H | 350 | 67.033 | 19.750 | 1.354 | 1.00 | 35.06 | C |
| ATOM | 9722 | O | ILE | H | 350 | 67.360 | 18.715 | 0.780 | 1.00 | 35.43 | O |
| ATOM | 9723 | CB | ILE | H | 350 | 68.947 | 21.326 | 1.442 | 1.00 | 34.97 | C |
| ATOM | 9724 | CG1 | ILE | H | 350 | 69.814 | 22.211 | 2.342 | 1.00 | 35.77 | C |
| ATOM | 9725 | CG2 | ILE | H | 350 | 68.148 | 22.131 | 0.424 | 1.00 | 34.94 | C |
| ATOM | 9726 | CD1 | ILE | H | 350 | 70.890 | 23.018 | 1.587 | 1.00 | 36.05 | C |
| ATOM | 9727 | N | SER | H | 351 | 65.850 | 20.336 | 1.180 | 1.00 | 34.68 | N |
| ATOM | 9728 | CA | SER | H | 351 | 64.824 | 19.816 | 0.269 | 1.00 | 33.71 | C |
| ATOM | 9729 | C | SER | H | 351 | 64.217 | 21.007 | −0.467 | 1.00 | 33.16 | C |
| ATOM | 9730 | O | SER | H | 351 | 64.169 | 22.107 | 0.087 | 1.00 | 32.26 | O |
| ATOM | 9731 | CB | SER | H | 351 | 63.719 | 19.081 | 1.046 | 1.00 | 33.92 | C |
| ATOM | 9732 | OG | SER | H | 351 | 64.195 | 17.873 | 1.612 | 1.00 | 33.92 | O |
| ATOM | 9733 | N | PHE | H | 352 | 63.762 | 20.796 | −1.703 | 1.00 | 32.29 | N |
| ATOM | 9734 | CA | PHE | H | 352 | 63.168 | 21.878 | −2.483 | 1.00 | 32.43 | C |
| ATOM | 9735 | C | PHE | H | 352 | 62.276 | 21.395 | −3.633 | 1.00 | 32.72 | C |
| ATOM | 9736 | O | PHE | H | 352 | 62.574 | 20.387 | −4.281 | 1.00 | 31.63 | O |
| ATOM | 9737 | CB | PHE | H | 352 | 64.277 | 22.793 | −3.031 | 1.00 | 33.11 | C |
| ATOM | 9738 | CG | PHE | H | 352 | 65.161 | 22.141 | −4.067 | 1.00 | 34.50 | C |
| ATOM | 9739 | CD1 | PHE | H | 352 | 64.707 | 21.946 | −5.376 | 1.00 | 35.60 | C |
| ATOM | 9740 | CD2 | PHE | H | 352 | 66.445 | 21.710 | −3.735 | 1.00 | 35.05 | C |
| ATOM | 9741 | CE1 | PHE | H | 352 | 65.517 | 21.330 | −6.341 | 1.00 | 35.94 | C |
| ATOM | 9742 | CE2 | PHE | H | 352 | 67.267 | 21.090 | −4.690 | 1.00 | 35.60 | C |
| ATOM | 9743 | CZ | PHE | H | 352 | 66.804 | 20.900 | −5.992 | 1.00 | 35.75 | C |
| ATOM | 9744 | N | HIS | H | 353 | 61.183 | 22.124 | −3.870 | 1.00 | 32.24 | N |
| ATOM | 9745 | CA | HIS | H | 353 | 60.230 | 21.828 | −4.947 | 1.00 | 32.60 | C |
| ATOM | 9746 | C | HIS | H | 353 | 60.123 | 23.081 | −5.818 | 1.00 | 33.51 | C |
| ATOM | 9747 | O | HIS | H | 353 | 60.099 | 24.204 | −5.297 | 1.00 | 33.35 | O |
| ATOM | 9748 | CB | HIS | H | 353 | 58.831 | 21.511 | −4.398 | 1.00 | 30.97 | C |
| ATOM | 9749 | CG | HIS | H | 353 | 58.667 | 20.116 | −3.881 | 1.00 | 29.85 | C |
| ATOM | 9750 | ND1 | HIS | H | 353 | 57.445 | 19.623 | −3.469 | 1.00 | 28.49 | N |
| ATOM | 9751 | CD2 | HIS | H | 353 | 59.563 | 19.121 | −3.673 | 1.00 | 30.21 | C |
| ATOM | 9752 | CE1 | HIS | H | 353 | 57.597 | 18.387 | −3.028 | 1.00 | 28.83 | C |
| ATOM | 9753 | NE2 | HIS | H | 353 | 58.872 | 18.056 | −3.139 | 1.00 | 27.96 | N |
| ATOM | 9754 | N | SER | H | 354 | 60.033 | 22.892 | −7.133 | 1.00 | 33.84 | N |
| ATOM | 9755 | CA | SER | H | 354 | 59.951 | 24.011 | −8.064 | 1.00 | 34.71 | C |
| ATOM | 9756 | C | SER | H | 354 | 58.698 | 24.018 | −8.927 | 1.00 | 35.83 | C |
| ATOM | 9757 | O | SER | H | 354 | 58.082 | 22.982 | −9.173 | 1.00 | 36.45 | O |
| ATOM | 9758 | CB | SER | H | 354 | 61.177 | 24.014 | −8.979 | 1.00 | 33.91 | C |
| ATOM | 9759 | OG | SER | H | 354 | 62.365 | 24.081 | −8.222 | 1.00 | 32.77 | O |
| ATOM | 9760 | N | ALA | H | 355 | 58.333 | 25.205 | −9.387 | 1.00 | 36.67 | N |
| ATOM | 9761 | CA | ALA | H | 355 | 57.164 | 25.382 | −10.236 | 1.00 | 38.27 | C |
| ATOM | 9762 | C | ALA | H | 355 | 57.507 | 26.462 | −11.256 | 1.00 | 39.56 | C |
| ATOM | 9763 | O | ALA | H | 355 | 58.456 | 27.231 | −11.068 | 1.00 | 38.77 | O |
| ATOM | 9764 | CB | ALA | H | 355 | 55.963 | 25.804 | −9.398 | 1.00 | 36.50 | C |
| ATOM | 9765 | N | TRP | H | 356 | 56.741 | 26.518 | −12.335 | 1.00 | 41.08 | N |
| ATOM | 9766 | CA | TRP | H | 356 | 56.986 | 27.507 | −13.370 | 1.00 | 43.37 | C |
| ATOM | 9767 | C | TRP | H | 356 | 55.856 | 28.520 | −13.500 | 1.00 | 43.51 | C |
| ATOM | 9768 | O | TRP | H | 356 | 54.678 | 28.181 | −13.360 | 1.00 | 42.74 | O |
| ATOM | 9769 | CB | TRP | H | 356 | 57.195 | 26.809 | −14.713 | 1.00 | 46.21 | C |
| ATOM | 9770 | CG | TRP | H | 356 | 58.585 | 26.940 | −15.259 | 1.00 | 49.86 | C |
| ATOM | 9771 | CD1 | TRP | H | 356 | 59.119 | 28.023 | −15.910 | 1.00 | 51.19 | C |
| ATOM | 9772 | CD2 | TRP | H | 356 | 59.622 | 25.955 | −15.199 | 1.00 | 51.39 | C |
| ATOM | 9773 | NE1 | TRP | H | 356 | 60.428 | 27.770 | −16.259 | 1.00 | 52.44 | N |
| ATOM | 9774 | CE2 | TRP | H | 356 | 60.761 | 26.508 | −15.834 | 1.00 | 52.70 | C |
| ATOM | 9775 | CE3 | TRP | H | 356 | 59.700 | 24.659 | −14.670 | 1.00 | 52.30 | C |
| ATOM | 9776 | CZ2 | TRP | H | 356 | 61.967 | 25.805 | −15.956 | 1.00 | 53.75 | C |
| ATOM | 9777 | CZ3 | TRP | H | 356 | 60.899 | 23.957 | −14.790 | 1.00 | 53.65 | C |
| ATOM | 9778 | CH2 | TRP | H | 356 | 62.016 | 24.533 | −15.430 | 1.00 | 54.68 | C |
| ATOM | 9779 | N | LEU | H | 357 | 56.228 | 29.771 | −13.749 | 1.00 | 43.57 | N |
| ATOM | 9780 | CA | LEU | H | 357 | 55.241 | 30.821 | −13.948 | 1.00 | 44.37 | C |
| ATOM | 9781 | C | LEU | H | 357 | 55.264 | 31.210 | −15.419 | 1.00 | 44.97 | C |
| ATOM | 9782 | O | LEU | H | 357 | 56.306 | 31.606 | −15.943 | 1.00 | 44.95 | O |
| ATOM | 9783 | CB | LEU | H | 357 | 55.553 | 32.063 | −13.102 | 1.00 | 43.75 | C |
| ATOM | 9784 | CG | LEU | H | 357 | 54.647 | 33.275 | −13.395 | 1.00 | 43.33 | C |
| ATOM | 9785 | CD1 | LEU | H | 357 | 53.199 | 32.930 | −13.065 | 1.00 | 42.94 | C |
| ATOM | 9786 | CD2 | LEU | H | 357 | 55.097 | 34.483 | −12.592 | 1.00 | 42.64 | C |
| ATOM | 9787 | N | THR | H | 358 | 54.125 | 31.072 | −16.088 | 1.00 | 46.14 | N |
| ATOM | 9788 | CA | THR | H | 358 | 54.021 | 31.455 | −17.494 | 1.00 | 47.09 | C |
| ATOM | 9789 | C | THR | H | 358 | 53.217 | 32.748 | −17.602 | 1.00 | 47.54 | C |
| ATOM | 9790 | O | THR | H | 358 | 52.111 | 32.851 | −17.070 | 1.00 | 47.65 | O |
| ATOM | 9791 | CB | THR | H | 358 | 53.347 | 30.355 | −18.357 | 1.00 | 47.36 | C |
| ATOM | 9792 | OG1 | THR | H | 358 | 54.224 | 29.223 | −18.454 | 1.00 | 46.99 | O |
| ATOM | 9793 | CG2 | THR | H | 358 | 53.059 | 30.880 | −19.769 | 1.00 | 47.09 | C |
| ATOM | 9794 | N | VAL | H | 359 | 53.798 | 33.739 | −18.273 | 1.00 | 48.63 | N |
| ATOM | 9795 | CA | VAL | H | 359 | 53.150 | 35.035 | −18.462 | 1.00 | 50.08 | C |
| ATOM | 9796 | C | VAL | H | 359 | 52.862 | 35.241 | −19.946 | 1.00 | 51.19 | C |
| ATOM | 9797 | O | VAL | H | 359 | 53.779 | 35.297 | −20.764 | 1.00 | 50.62 | O |

TABLE 3-continued

| | | | FGFR2(D2–D3) Complexed with FGF2 | | | | | | | |
|---|---|---|---|---|---|---|---|---|---|---|
| ATOM | 9798 | CB | VAL | H | 359 | 54.040 | 36.198 | −17.960 | 1.00 | 49.65 | C |
| ATOM | 9799 | N | LEU | H | 360 | 51.576 | 35.351 | −20.280 | 1.00 | 52.47 | N |
| ATOM | 9800 | CA | LEU | H | 360 | 51.122 | 35.539 | −21.659 | 1.00 | 53.75 | C |
| ATOM | 9801 | C | LEU | H | 360 | 50.855 | 37.013 | −21.990 | 1.00 | 54.89 | C |
| ATOM | 9802 | O | LEU | H | 360 | 50.672 | 37.836 | −21.086 | 1.00 | 54.42 | O |
| ATOM | 9803 | CB | LEU | H | 360 | 49.859 | 34.711 | −21.882 | 1.00 | 52.68 | C |
| ATOM | 9804 | CG | LEU | H | 360 | 50.030 | 33.232 | −21.527 | 1.00 | 52.35 | C |
| ATOM | 9805 | CD1 | LEU | H | 360 | 48.682 | 32.530 | −21.579 | 1.00 | 51.71 | C |
| ATOM | 9806 | CD2 | LEU | H | 360 | 51.018 | 32.582 | −22.494 | 1.00 | 51.91 | C |
| ATOM | 9807 | N | PRO | H | 361 | 50.829 | 37.360 | −23.292 | 1.00 | 56.57 | N |
| ATOM | 9808 | CA | PRO | H | 361 | 50.587 | 38.734 | −23.759 | 1.00 | 57.88 | C |
| ATOM | 9809 | C | PRO | H | 361 | 49.152 | 39.223 | −23.536 | 1.00 | 59.14 | C |
| ATOM | 9810 | O | PRO | H | 361 | 48.215 | 38.421 | −23.432 | 1.00 | 58.75 | O |
| ATOM | 9811 | CB | PRO | H | 361 | 50.945 | 38.653 | −25.241 | 1.00 | 57.63 | C |
| ATOM | 9812 | CG | PRO | H | 361 | 50.519 | 37.252 | −25.605 | 1.00 | 57.72 | C |
| ATOM | 9813 | CD | PRO | H | 361 | 51.068 | 36.459 | −24.436 | 1.00 | 56.77 | C |
| ATOM | 9814 | N | ALA | H | 362 | 48.988 | 40.540 | −23.458 | 1.00 | 60.86 | N |
| ATOM | 9815 | CA | ALA | H | 362 | 47.671 | 41.137 | −23.245 | 1.00 | 62.45 | C |
| ATOM | 9816 | C | ALA | H | 362 | 47.003 | 41.386 | −24.592 | 1.00 | 63.55 | C |
| ATOM | 9817 | O | ALA | H | 362 | 47.664 | 41.329 | −25.630 | 1.00 | 63.78 | O |
| ATOM | 9818 | CB | ALA | H | 362 | 47.810 | 42.457 | −22.470 | 1.00 | 62.08 | C |
| ATOM | 9819 | N | PRO | H | 363 | 45.687 | 41.657 | −24.605 | 1.00 | 64.64 | N |
| ATOM | 9820 | CA | PRO | H | 363 | 44.919 | 41.923 | −25.837 | 1.00 | 65.06 | C |
| ATOM | 9821 | C | PRO | H | 363 | 44.966 | 43.393 | −26.248 | 1.00 | 65.26 | C |
| ATOM | 9822 | O | PRO | H | 363 | 45.828 | 43.746 | −27.072 | 1.00 | 65.96 | O |
| ATOM | 9823 | CB | PRO | H | 363 | 43.491 | 41.523 | −25.462 | 1.00 | 65.00 | C |
| ATOM | 9824 | CG | PRO | H | 363 | 43.656 | 40.661 | −24.196 | 1.00 | 65.12 | C |
| ATOM | 9825 | CD | PRO | H | 363 | 44.777 | 41.349 | −23.490 | 1.00 | 64.84 | C |
| HETATM | 9927 | S | SO4 | | 9001 | 46.360 | 43.651 | 14.525 | 1.00 | 80.11 | S |
| HETATM | 9828 | O1 | SO4 | | 9001 | 45.130 | 42.976 | 14.081 | 1.00 | 80.85 | O |
| HETATM | 9829 | O2 | SO4 | | 9001 | 46.043 | 45.024 | 14.953 | 1.00 | 79.61 | O |
| HETATM | 9830 | O3 | SO4 | | 9001 | 46.944 | 42.914 | 15.659 | 1.00 | 80.93 | O |
| HETATM | 9831 | O4 | SO4 | | 9001 | 47.320 | 43.674 | 13.407 | 1.00 | 79.94 | O |
| HETATM | 9832 | S | SO4 | | 9002 | 39.893 | 32.643 | −36.234 | 1.00 | 57.87 | S |
| NETATM | 9833 | O1 | SO4 | | 9002 | 40.848 | 33.615 | −36.811 | 1.00 | 58.67 | O |
| HETATM | 9834 | O2 | SO4 | | 9002 | 40.300 | 31.273 | −36.580 | 1.00 | 58.27 | O |
| HETATM | 9835 | O3 | SO4 | | 9002 | 39.894 | 32.781 | −34.766 | 1.00 | 57.83 | O |
| HETATM | 9836 | O4 | SO4 | | 9002 | 38.548 | 32.894 | −36.778 | 1.00 | 57.44 | O |
| HETATM | 9837 | S | SO4 | | 9003 | 76.012 | 20.398 | 36.658 | 1.00 | 64.33 | S |
| HETATM | 9838 | O1 | SO4 | | 9003 | 76.273 | 20.228 | 35.214 | 1.00 | 64.38 | O |
| HETATM | 9839 | O2 | SO4 | | 9003 | 76.984 | 19.588 | 37.421 | 1.00 | 65.03 | O |
| HETATM | 9840 | O3 | SO4 | | 9003 | 76.155 | 21.819 | 37.013 | 1.00 | 64.70 | O |
| HETATM | 9841 | O4 | SO4 | | 9003 | 74.644 | 19.964 | 36.986 | 1.00 | 63.96 | O |
| HETATM | 9842 | S | SO4 | | 9004 | 82.383 | 9.280 | −14.072 | 1.00 | 88.97 | S |
| HETATM | 9843 | O1 | SO4 | | 9004 | 82.503 | 10.218 | −15.201 | 1.00 | 89.47 | O |
| HETATM | 9844 | O2 | SO4 | | 9004 | 83.325 | 8.161 | −14.260 | 1.00 | 88.96 | O |
| HETATM | 9845 | O3 | SO4 | | 9004 | 82.686 | 9.986 | −12.808 | 1.00 | 88.61 | O |
| HETATM | 9846 | O4 | SO4 | | 9004 | 81.009 | 8.751 | −14.037 | 1.00 | 89.30 | O |
| HETATM | 9847 | O | HOH | | 8001 | 30.583 | 19.182 | −20.544 | 1.00 | 21.98 | O |
| HETATM | 9848 | O | HOH | | 8002 | 76.423 | −6.864 | 9.843 | 1.00 | 23.00 | O |
| HETATM | 9849 | O | HOH | | 8003 | 19.265 | 31.410 | 1.209 | 1.00 | 22.84 | O |
| HETATM | 9850 | O | HOH | | 8004 | 61.744 | −4.031 | 28.962 | 1.00 | 22.37 | O |
| HETATM | 9851 | O | HOH | | 8005 | 66.826 | 33.841 | 20.938 | 1.00 | 23.18 | O |
| HETATM | 9852 | O | HOH | | 8006 | 18.482 | 37.390 | 8.210 | 1.00 | 23.45 | O |
| HETATM | 9853 | O | HOH | | 8007 | 54.625 | 15.653 | −7.780 | 1.00 | 22.48 | O |
| HETATM | 9854 | O | HOH | | 8008 | 59.923 | 9.805 | 49.344 | 1.00 | 26.25 | O |
| HETATM | 9855 | O | HOH | | 8009 | 72.094 | 23.144 | 24.607 | 1.00 | 19.78 | O |
| HETATM | 9856 | O | HOH | | 8010 | 14.982 | 26.494 | 6.291 | 1.00 | 21.68 | O |
| HETATM | 9857 | O | HOH | | 8011 | 40.246 | 59.911 | −9.530 | 1.00 | 24.78 | O |
| HETATM | 9858 | O | HOH | | 8012 | 15.805 | 46.501 | 5.661 | 1.00 | 29.73 | O |
| HETATM | 9859 | O | HOH | | 8013 | 55.380 | 21.613 | −0.817 | 1.00 | 23.35 | O |
| HETATM | 9860 | O | HOH | | 8014 | 16.573 | 46.338 | 9.812 | 1.00 | 24.34 | O |
| HETATM | 9861 | O | HOH | | 8015 | 51.751 | 6.536 | −5.223 | 1.00 | 27.38 | O |
| HETATM | 9862 | O | HOH | | 8016 | 36.033 | 29.962 | −24.110 | 1.00 | 23.25 | O |
| HETATM | 9863 | O | HOH | | 8017 | 25.606 | 57.088 | −28.459 | 1.00 | 22.89 | O |
| HETATM | 9864 | O | HOH | | 8018 | 73.859 | −2.056 | 4.603 | 1.00 | 19.45 | O |
| HETATM | 9865 | O | HOH | | 8019 | 51.125 | 26.594 | −5.604 | 1.00 | 24.70 | O |
| HETATM | 9866 | O | HOH | | 8020 | 66.880 | 25.381 | 9.858 | 1.00 | 28.68 | O |
| HETATM | 9867 | O | HOH | | 8021 | 38.023 | 25.055 | −28.614 | 1.00 | 22.96 | O |
| HETATM | 9868 | O | HOH | | 8022 | 26.996 | 30.474 | −16.396 | 1.00 | 23.98 | O |
| HETATM | 9869 | O | HOH | | 8023 | 25.809 | 19.877 | −17.801 | 1.00 | 24.38 | O |
| HETATM | 9870 | O | HOH | | 8024 | 45.339 | 47.075 | −3.217 | 1.00 | 24.47 | O |
| HETATM | 9871 | O | HOH | | 8025 | 58.457 | 26.484 | 18.703 | 1.00 | 28.38 | O |
| HETATM | 9872 | O | HOH | | 8026 | 37.737 | 55.122 | −4.166 | 1.00 | 21.76 | O |
| HETATM | 9873 | O | HOH | | 8027 | 62.668 | 37.972 | 3.726 | 1.00 | 37.90 | O |
| HETATM | 9874 | O | HOH | | 8028 | 76.437 | −7.756 | 13.648 | 1.00 | 21.50 | O |
| HETATM | 9875 | O | HOH | | 8029 | 52.710 | 6.639 | −9.379 | 1.00 | 25.02 | O |

TABLE 3-continued

FGFR2(D2–D3) Complexed with FGF2

| HETATM | 9876 | O | HOH | 8030 | 81.344 | 5.935 | 3.580 | 1.00 | 25.92 | O |
|---|---|---|---|---|---|---|---|---|---|---|
| HETATM | 9877 | O | HOH | 8031 | 23.909 | 43.293 | −49.084 | 1.00 | 22.88 | O |
| HETATM | 9878 | O | HOH | 8032 | 24.078 | 33.069 | 8.400 | 1.00 | 30.55 | O |
| HETATM | 9879 | O | HOH | 8033 | 49.020 | 60.054 | −0.925 | 1.00 | 30.74 | O |
| HETATM | 9880 | O | HOH | 8034 | 74.099 | 28.029 | 29.070 | 1.00 | 28.15 | O |
| HETATM | 9881 | O | HOH | 8035 | 65.801 | 0.287 | 24.875 | 1.00 | 34.23 | O |
| HETATM | 9882 | O | HOH | 8036 | 58.785 | 1.057 | −24.404 | 1.00 | 24.39 | O |
| HETATM | 9883 | O | HOH | 8037 | 28.568 | 14.884 | −9.616 | 1.00 | 34.53 | O |
| HETATM | 9884 | O | HOH | 8038 | 54.116 | 2.380 | −18.860 | 1.00 | 29.41 | O |
| HETATM | 9885 | O | HOH | 8039 | 30.881 | 27.679 | −9.394 | 1.00 | 27.68 | O |
| HETATM | 9886 | O | HOH | 8040 | 65.552 | 4.439 | 59.031 | 1.00 | 25.86 | O |
| HETATM | 9887 | O | HOH | 8041 | 65.513 | 10.326 | −17.439 | 1.00 | 30.59 | O |
| HETATM | 9888 | O | HOH | 8042 | 17.929 | 50.681 | 19.191 | 1.00 | 28.19 | O |
| HETATM | 9889 | O | HOH | 8043 | 68.778 | 6.931 | 16.604 | 1.00 | 39.86 | O |
| HETATM | 9890 | O | HOH | 8044 | 67.164 | 12.773 | 5.516 | 1.00 | 33.07 | O |
| HETATM | 9891 | O | HOH | 8045 | 55.249 | 8.894 | 45.955 | 1.00 | 29.25 | O |
| HETATM | 9892 | O | HOH | 8046 | 22.665 | 51.933 | 24.883 | 1.00 | 28.14 | O |
| HETATM | 9893 | O | HOH | 8047 | 37.888 | 61.108 | −2.570 | 1.00 | 31.13 | O |
| HETATM | 9894 | O | HOH | 8048 | 49.282 | 61.990 | −14.155 | 1.00 | 36.20 | O |
| HETATM | 9895 | O | HOH | 8049 | 79.384 | −12.820 | −6.839 | 1.00 | 37.30 | O |
| HETATM | 9896 | O | HOH | 8050 | 26.570 | 15.111 | −3.236 | 1.00 | 37.60 | O |
| HETATM | 9897 | O | HOH | 8051 | 19.038 | 44.180 | −45.467 | 1.00 | 26.94 | O |
| HETATM | 9898 | O | HOH | 8052 | 60.388 | 25.333 | 28.267 | 1.00 | 27.06 | O |
| HETATM | 9899 | O | HOH | 8053 | 23.414 | 15.233 | 9.873 | 1.00 | 34.15 | O |
| HETATM | 9900 | O | HOH | 8054 | 66.392 | 27.654 | 3.426 | 1.00 | 31.42 | O |
| HETATM | 9901 | O | HOH | 8055 | 62.016 | 33.264 | 18.060 | 1.00 | 33.13 | O |
| HETATM | 9902 | O | HOH | 8056 | 43.462 | 65.933 | 7.208 | 1.00 | 44.73 | O |
| HETATM | 9903 | O | HOH | 8057 | 69.239 | 2.254 | 10.867 | 1.00 | 38.73 | O |
| HETATM | 9904 | O | HOH | 8058 | 14.577 | 44.517 | 4.008 | 1.00 | 33.29 | O |
| HETATM | 9905 | O | HOH | 8059 | 85.110 | −7.051 | 1.368 | 1.00 | 35.88 | O |
| HETATM | 9906 | O | HOH | 8060 | 45.130 | 48.451 | 2.474 | 1.00 | 30.78 | O |
| HETATM | 9907 | O | HOH | 8061 | 63.059 | 22.563 | 16.774 | 1.00 | 23.95 | O |
| HETATM | 9908 | O | HOH | 8062 | 73.904 | −8.163 | 3.078 | 1.00 | 36.65 | O |
| HETATM | 9909 | O | HOH | 8063 | 53.387 | 0.804 | 26.358 | 1.00 | 32.68 | O |
| HETATM | 9910 | O | HOH | 8064 | 13.296 | 34.466 | 4.116 | 1.00 | 29.56 | O |
| HETATM | 9911 | O | HOH | 8065 | 29.710 | 52.865 | −24.449 | 1.00 | 30.83 | O |
| HETATM | 9912 | O | HOH | 8066 | 67.684 | 22.717 | 12.581 | 1.00 | 28.39 | O |
| HETATM | 9913 | O | HOH | 8067 | 18.064 | 52.076 | −30.370 | 1.00 | 32.76 | O |
| HETATM | 9914 | O | HOH | 8068 | 85.007 | −9.066 | 15.009 | 1.00 | 43.17 | O |
| HETATM | 9915 | O | HOH | 8069 | 15.569 | 35.041 | 9.972 | 1.00 | 31.63 | O |
| HETATM | 9916 | O | HOH | 8070 | 17.191 | 52.234 | −25.947 | 1.00 | 35.07 | O |
| HETATM | 9917 | O | HOH | 8071 | 30.314 | 25.533 | −3.007 | 1.00 | 32.66 | O |
| HETATM | 9918 | O | HOH | 8072 | 47.442 | 66.967 | −17.665 | 1.00 | 31.12 | O |
| HETATM | 9919 | O | HOH | 8073 | 34.258 | 51.896 | −24.228 | 1.00 | 34.62 | O |
| HETATM | 9920 | O | HOH | 8074 | 66.403 | −0.525 | 21.596 | 1.00 | 30.11 | O |
| HETATM | 9921 | O | HOH | 8075 | 17.325 | 49.223 | 0.994 | 1.00 | 37.88 | O |
| HETATM | 9922 | O | HOH | 8076 | 59.434 | 37.817 | −9.613 | 1.00 | 27.94 | O |
| HETATM | 9923 | O | HOH | 8077 | 27.027 | 41.793 | 38.232 | 1.00 | 37.52 | O |
| HETATM | 9924 | O | HOH | 8078 | 40.302 | 60.801 | −13.194 | 1.00 | 22.94 | O |
| HETATM | 9925 | O | HOH | 8079 | 81.263 | −10.005 | 4.030 | 1.00 | 29.81 | O |
| HETATM | 9926 | O | HOH | 8080 | 27.556 | 33.013 | −16.634 | 1.00 | 31.61 | O |
| HETATM | 9927 | O | HOH | 8081 | 53.479 | 3.973 | −0.763 | 1.00 | 40.24 | O |
| HETATM | 9928 | O | HOH | 8082 | 29.612 | 42.889 | 17.699 | 1.00 | 34.12 | O |
| HETATM | 9929 | O | HOH | 8083 | 31.582 | 30.335 | −12.062 | 1.00 | 31.47 | O |
| HETATM | 9930 | O | HOH | 8084 | 69.184 | 6.616 | −7.967 | 1.00 | 37.68 | O |
| HETATM | 9931 | O | HOH | 8085 | 56.292 | 20.021 | 11.107 | 1.00 | 29.89 | O |
| HETATM | 9932 | O | HOH | 8086 | 25.472 | 24.891 | −11.314 | 1.00 | 30.53 | O |
| HETATM | 9933 | O | HOH | 8087 | 81.124 | 4.621 | −1.975 | 1.00 | 28.02 | O |
| HETATM | 9934 | O | HOH | 8088 | 78.096 | −1.640 | 12.197 | 1.00 | 29.00 | O |
| HETATM | 9935 | O | HOH | 8089 | 13.865 | 47.316 | 7.506 | 1.00 | 32.89 | O |
| HETATM | 9936 | O | HOH | 8090 | 61.310 | 28.601 | 8.211 | 1.00 | 24.59 | O |
| HETATM | 9937 | O | HOH | 8091 | 17.421 | 23.402 | −6.076 | 1.00 | 34.31 | O |
| HETATM | 9938 | O | HOH | 8092 | 57.812 | 10.445 | 0.414 | 1.00 | 28.37 | O |
| HETATM | 9939 | O | HOH | 8093 | 58.384 | 32.757 | 14.907 | 1.00 | 33.51 | O |
| HETATM | 9940 | O | HOH | 8094 | 24.207 | 27.604 | −27.914 | 1.00 | 28.18 | O |
| HETATM | 9941 | O | HOH | 8095 | 63.100 | 11.384 | −37.852 | 1.00 | 39.50 | O |
| HETATM | 9942 | O | HOH | 8096 | 71.145 | 17.722 | 1.891 | 1.00 | 42.96 | O |
| HETATM | 9943 | O | HOH | 8097 | 29.409 | 48.671 | −58.806 | 1.00 | 28.48 | O |
| HETATM | 9944 | O | HOH | 8098 | 26.815 | 49.289 | 28.620 | 1.00 | 27.67 | O |
| HETATM | 9945 | O | HOH | 8099 | 63.739 | 20.042 | 17.105 | 1.00 | 29.92 | O |
| HETATM | 9946 | O | HOH | 8100 | 16.197 | 48.146 | −40.012 | 1.00 | 36.11 | O |
| HETATM | 9947 | O | HOH | 8101 | 28.797 | 19.484 | −13.783 | 1.00 | 30.27 | O |
| HETATM | 9948 | O | HOH | 8102 | 74.942 | −5.515 | −6.685 | 1.00 | 32.65 | O |
| HETATM | 9949 | O | HOH | 8103 | 25.351 | 24.480 | −7.993 | 1.00 | 26.19 | O |
| HETATM | 9950 | O | HOH | 8104 | 74.186 | 34.192 | 19.566 | 1.00 | 29.84 | O |
| HETATM | 9951 | O | HOH | 8105 | 83.633 | −13.959 | 18.198 | 1.00 | 32.48 | O |
| HETATM | 9952 | O | HOH | 8106 | 52.144 | 19.807 | −15.029 | 1.00 | 47.82 | O |

TABLE 3-continued

FGFR2(D2–D3) Complexed with FGF2

| | | | | | | | | | | | |
|---|---|---|---|---|---|---|---|---|---|---|---|
| HETATM | 9953 | O | HOH | 8107 | 79.030 | −3.693 | 18.591 | 1.00 | 37.03 | O |
| HETATM | 9954 | O | HOH | 8108 | 15.025 | 52.871 | −28.124 | 1.00 | 35.88 | O |
| HETATM | 9955 | O | HOH | 8109 | 55.203 | 14.515 | 1.204 | 1.00 | 26.74 | O |
| HETATM | 9956 | O | HOH | 8110 | 50.909 | 12.754 | −20.344 | 1.00 | 35.29 | O |
| HETATM | 9957 | O | HOH | 8111 | 48.196 | 16.287 | −16.372 | 1.00 | 36.40 | O |
| HETATM | 9958 | O | HOH | 8112 | 45.057 | 63.127 | −3.521 | 1.00 | 28.95 | O |
| HETATM | 9959 | O | HOH | 8113 | 66.876 | 9.858 | −36.882 | 1.00 | 29.60 | O |
| HETATM | 9960 | O | HOH | 8114 | 51.733 | 17.941 | −9.585 | 1.00 | 32.25 | O |
| HETATM | 9961 | O | HOH | 8115 | 14.959 | 24.873 | 8.383 | 1.00 | 31.68 | O |
| HETATM | 9962 | O | HOH | 8116 | 54.406 | 3.719 | 51.786 | 1.00 | 34.52 | O |
| HETATM | 9963 | O | HOH | 8117 | 47.786 | 29.136 | −13.190 | 1.00 | 43.19 | O |
| HETATM | 9964 | O | HOH | 8118 | 16.528 | 42.222 | 4.279 | 1.00 | 29.03 | O |
| HETATM | 9965 | O | HOH | 8119 | 22.165 | 20.253 | −14.491 | 1.00 | 32.49 | O |
| HETATM | 9966 | O | HOH | 8120 | 38.018 | 18.783 | −19.030 | 1.00 | 29.87 | O |
| HETATM | 9967 | O | HOH | 8121 | 12.676 | 52.034 | 13.008 | 1.00 | 33.57 | O |
| HETATM | 9968 | O | HOH | 8122 | 30.241 | 53.649 | −21.241 | 1.00 | 31.91 | O |
| HETATM | 9969 | O | HOH | 8123 | 40.855 | 50.843 | −9.251 | 1.00 | 36.33 | O |
| HETATM | 9970 | O | HOH | 8124 | 16.414 | 33.295 | 15.556 | 1.00 | 39.62 | O |
| HETATM | 9971 | O | HOH | 8125 | 18.353 | 48.759 | 30.683 | 1.00 | 35.44 | O |
| HETATM | 9972 | O | HOH | 8126 | 27.919 | 64.251 | −31.560 | 1.00 | 39.39 | O |
| HETATM | 9973 | O | HOH | 8127 | 54.074 | 11.927 | −1.836 | 1.00 | 20.42 | O |
| HETATM | 9974 | O | HOH | 8128 | 67.489 | 10.620 | −5.827 | 1.00 | 24.90 | O |
| HETATM | 9975 | O | HOH | 8129 | 56.468 | 32.717 | −20.169 | 1.00 | 34.22 | O |
| HETATM | 9976 | O | HOH | 8130 | 37.565 | 9.799 | −16.847 | 1.00 | 39.96 | O |
| HETATM | 9977 | O | HOH | 8131 | 76.829 | 1.988 | 9.827 | 1.00 | 41.86 | O |
| HETATM | 9978 | O | HOH | 8132 | 43.003 | 56.760 | −18.029 | 1.00 | 32.10 | O |
| HETATM | 9979 | O | HOH | 8133 | 33.394 | 50.852 | −10.344 | 1.00 | 45.63 | O |
| HETATM | 9980 | O | HOH | 8134 | 57.923 | 33.762 | 28.761 | 1.00 | 35.78 | O |
| HETATM | 9981 | O | HOH | 8135 | 63.084 | −8.959 | 36.290 | 1.00 | 42.92 | O |
| HETATM | 9982 | O | HOH | 8136 | 21.708 | 42.750 | 0.109 | 1.00 | 32.64 | O |
| HETATM | 9983 | O | HOH | 8137 | 48.251 | −2.260 | 29.824 | 1.00 | 47.66 | O |
| HETATM | 9984 | O | HOH | 8138 | 64.982 | 33.645 | 14.162 | 1.00 | 32.84 | O |
| HETATM | 9985 | O | HOH | 8139 | 37.774 | 30.276 | −18.377 | 1.00 | 25.37 | O |
| HETATM | 9986 | O | HOH | 8140 | 20.175 | 20.176 | 20.621 | 1.00 | 40.03 | O |
| HETATM | 9987 | O | HOH | 8141 | 15.210 | 32.340 | 9.751 | 1.00 | 30.63 | O |
| HETATM | 9988 | O | HOH | 8142 | 53.556 | 29.620 | 6.545 | 1.00 | 35.87 | O |
| HETATM | 9989 | O | HOH | 8143 | 52.402 | 5.039 | 40.375 | 1.00 | 36.45 | O |
| HETATM | 9990 | O | HOH | 8144 | 41.944 | 54.575 | −11.736 | 1.00 | 25.88 | O |
| HETATM | 9991 | O | HOH | 8145 | 14.808 | 40.343 | 20.475 | 1.00 | 36.26 | O |
| HETATM | 9992 | O | HOH | 8146 | 36.235 | 53.078 | −4.162 | 1.00 | 24.78 | O |
| HETATM | 9993 | O | HOH | 8147 | 51.322 | 20.699 | −9.253 | 1.00 | 34.49 | O |
| HETATM | 9994 | O | HOH | 8148 | 44.258 | 30.807 | −17.555 | 1.00 | 46.92 | O |
| HETATM | 9995 | O | HOH | 8149 | 11.904 | 21.107 | 9.147 | 1.00 | 41.29 | O |
| HETATM | 9996 | O | HOH | 8150 | 72.373 | −0.009 | 4.822 | 1.00 | 28.51 | O |
| HETATM | 9997 | O | HOH | 8151 | 20.170 | 33.123 | −10.615 | 1.00 | 28.26 | O |
| HETATM | 9998 | O | HOH | 8152 | 60.563 | −6.573 | 58.339 | 1.00 | 43.96 | O |
| HETATM | 9999 | O | HOH | 8153 | 57.895 | 28.648 | 13.774 | 1.00 | 30.15 | O |
| HETATM | 10000 | O | HON | 8154 | 53.947 | 23.638 | 7.544 | 1.00 | 41.95 | O |
| HETATM | 10001 | O | HOH | 8155 | 13.166 | 53.396 | −31.308 | 1.00 | 44.46 | O |
| HETATM | 10002 | O | HOH | 8156 | 38.690 | 58.693 | 7.177 | 1.00 | 27.24 | O |
| HETATM | 10003 | O | HOH | 8157 | 51.253 | 0.008 | 28.416 | 1.00 | 35.72 | O |
| HETATM | 10004 | O | HOH | 8158 | 18.004 | 41.137 | 2.217 | 1.00 | 20.61 | O |
| HETATM | 10005 | O | HOH | 8159 | 54.755 | 37.212 | −0.604 | 1.00 | 29.83 | O |
| HETATM | 10006 | O | HOH | 8160 | 18.580 | 15.949 | 0.946 | 1.00 | 34.15 | O |
| HETATM | 10007 | O | HOH | 8161 | 57.339 | −4.703 | 41.534 | 1.00 | 33.68 | O |
| HETATM | 10008 | O | HOH | 8162 | 68.790 | 10.518 | 33.158 | 1.00 | 44.07 | O |
| HETATM | 10009 | O | HOH | 8163 | 48.266 | 4.423 | −10.271 | 1.00 | 23.22 | O |
| HETATM | 10010 | O | HOH | 8164 | 32.688 | 42.614 | −32.515 | 1.00 | 43.90 | O |
| HETATM | 10011 | O | HOH | 8165 | 64.899 | 38.193 | 10.025 | 1.00 | 34.17 | O |
| HETATM | 10012 | O | HOH | 8166 | 19.100 | 38.573 | −0.767 | 1.00 | 25.16 | O |
| HETATM | 10013 | O | HOH | 8167 | 64.226 | 8.781 | −37.188 | 1.00 | 26.93 | O |
| HETATM | 10014 | O | HOH | 8168 | 29.180 | 37.941 | 4.587 | 1.00 | 30.90 | O |
| HETATM | 10015 | O | HOH | 8169 | 63.251 | 7.981 | −34.694 | 1.00 | 20.84 | O |
| HETATM | 10016 | O | HOH | 8170 | 32.539 | 48.870 | −25.937 | 1.00 | 40.48 | O |
| HETATM | 10017 | O | HOH | 8171 | 55.576 | 29.806 | 14.321 | 1.00 | 25.66 | O |
| HETATM | 10018 | O | HOH | 8172 | 21.748 | 19.472 | −28.189 | 1.00 | 30.89 | O |
| HETATM | 10019 | O | HOH | 8173 | 48.653 | 0.885 | −12.564 | 1.00 | 33.10 | O |
| HETATM | 10020 | O | HOH | 8174 | 50.731 | 8.561 | −3.840 | 1.00 | 26.40 | O |
| HETATM | 10021 | O | HOH | 8175 | 67.331 | 8.027 | 58.226 | 1.00 | 26.20 | O |
| HETATM | 10022 | O | HOH | 8176 | 64.354 | 3.045 | −26.220 | 1.00 | 32.54 | O |
| HETATM | 10023 | O | HOH | 8177 | 39.113 | 62.755 | −7.021 | 1.00 | 27.10 | O |
| HETATM | 10024 | O | HOH | 8178 | 46.583 | 45.195 | −4.701 | 1.00 | 30.19 | O |
| HETATM | 10025 | O | HOH | 8179 | 31.224 | 45.086 | −57.745 | 1.00 | 26.44 | O |
| HETATM | 10026 | O | HOH | 8180 | 67.620 | 7.867 | −17.944 | 1.00 | 33.64 | O |
| HETATM | 10027 | O | HOH | 8181 | 68.440 | 4.360 | 25.981 | 1.00 | 38.96 | O |
| HETATM | 10028 | O | HOH | 8182 | 24.285 | 56.988 | −21.046 | 1.00 | 34.78 | O |
| HETATM | 10029 | O | HOH | 8183 | 60.110 | 20.079 | −7.760 | 1.00 | 31.63 | O |

TABLE 3-continued

FGFR2(D2–D3) Complexed with FGF2

| HETATM | 10030 | O | HOH | 8184 | 21.199 | 57.796 | −41.110 | 1.00 | 37.92 | O |
|---|---|---|---|---|---|---|---|---|---|---|
| HETATM | 10031 | O | HOH | 8185 | 59.503 | 24.146 | 17.040 | 1.00 | 28.08 | O |
| HETATM | 10032 | O | HOH | 8186 | 60.538 | −3.909 | 21.754 | 1.00 | 33.98 | O |
| HETATM | 10033 | O | HOH | 8187 | 50.010 | 5.646 | −7.056 | 1.00 | 28.66 | O |
| HETATM | 10034 | O | HOH | 8188 | 86.579 | 2.282 | −6.040 | 1.00 | 38.85 | O |
| HETATM | 10035 | O | HOH | 8189 | 35.299 | 34.821 | −1.319 | 1.00 | 36.49 | O |
| HETATM | 10036 | O | HOH | 8190 | 83.307 | −8.029 | 7.975 | 1.00 | 29.74 | O |
| HETATM | 10037 | O | HOH | 8191 | 44.187 | 65.659 | −4.506 | 1.00 | 31.35 | O |
| HETATM | 10038 | O | HOH | 8192 | 30.932 | 40.093 | −5.050 | 1.00 | 33.10 | O |
| HETATM | 10039 | O | HOH | 8193 | 56.018 | 31.976 | 28.056 | 1.00 | 33.87 | O |
| HETATM | 10040 | O | HOH | 8194 | 27.127 | 45.046 | 35.049 | 1.00 | 24.02 | O |
| HETATM | 10041 | O | HOH | 8195 | 73.921 | 22.935 | 18.943 | 1.00 | 29.41 | O |
| HETATM | 10042 | O | HOH | 8196 | 18.153 | 50.887 | 32.927 | 1.00 | 43.89 | O |
| HETATM | 10043 | O | HOH | 8197 | 64.984 | 6.884 | 58.308 | 1.00 | 27.06 | O |
| HETATM | 10044 | O | HOH | 8198 | 23.014 | 13.926 | 7.613 | 1.00 | 40.19 | O |
| HETATM | 10045 | O | HOH | 8199 | 48.401 | 26.009 | −5.169 | 1.00 | 30.24 | O |
| HETATM | 10046 | O | HOH | 8200 | 66.865 | −7.653 | 21.825 | 1.00 | 30.37 | O |
| HETATM | 10047 | O | HOH | 8201 | 45.045 | 48.534 | −8.439 | 1.00 | 34.67 | O |
| HETATM | 10048 | O | HOH | 8202 | 17.155 | 51.924 | 0.154 | 1.00 | 41.46 | O |
| HETATM | 10049 | O | HOH | 8203 | 43.366 | 53.992 | −17.926 | 1.00 | 35.60 | O |
| HETATM | 10050 | O | HOH | 8204 | 17.215 | 35.488 | 26.426 | 1.00 | 45.03 | O |
| HETATM | 10051 | O | HOH | 8205 | 61.642 | 28.204 | 11.796 | 1.00 | 29.48 | O |
| HETATM | 10052 | O | HOH | 8206 | 60.187 | 42.226 | 22.209 | 1.00 | 40.71 | O |
| HETATM | 10053 | O | HOH | 8207 | 77.953 | 27.539 | 35.830 | 1.00 | 34.42 | O |
| HETATM | 10054 | O | HOH | 8208 | 25.995 | 34.365 | 7.024 | 1.00 | 28.38 | O |
| HETATM | 10055 | O | HOH | 8209 | 15.844 | 31.108 | 11.675 | 1.00 | 33.02 | O |
| HETATM | 10056 | O | HOH | 8210 | 12.732 | 15.752 | 6.140 | 1.00 | 40.56 | O |
| HETATM | 10057 | O | HOH | 8211 | 62.907 | 2.915 | 62.753 | 1.00 | 30.92 | O |
| HETATM | 10058 | O | HOH | 8212 | 24.044 | 10.937 | −21.880 | 1.00 | 42.40 | O |
| HETATM | 10059 | O | HOH | 8213 | 79.343 | −1.121 | 18.453 | 1.00 | 33.07 | O |
| HETATM | 10060 | O | HOH | 8214 | 68.004 | 33.744 | 5.930 | 1.00 | 33.70 | O |
| HETATM | 10061 | O | HOH | 8215 | 76.210 | 17.950 | 33.459 | 1.00 | 38.92 | O |
| HETATM | 10062 | O | HOH | 8216 | 41.987 | 23.581 | −37.300 | 1.00 | 44.75 | O |
| HETATM | 10063 | O | HOH | 8217 | 80.531 | 11.139 | −10.855 | 1.00 | 40.75 | O |
| HETATM | 10064 | O | HOH | 8218 | 61.409 | 0.815 | −24.031 | 1.00 | 29.53 | O |
| HETATM | 10065 | O | HOH | 8219 | 65.745 | 12.430 | −11.075 | 1.00 | 34.48 | O |
| HETATM | 10066 | O | HOH | 8220 | 17.792 | 29.223 | −7.156 | 1.00 | 34.49 | O |
| HETATM | 10067 | O | HOH | 8221 | 50.809 | 25.767 | 6.138 | 1.00 | 33.13 | O |
| HETATM | 10068 | O | HOH | 8222 | 16.549 | 52.909 | 10.612 | 1.00 | 32.50 | O |
| HETATM | 10069 | O | HOH | 8223 | 47.243 | 61.049 | −7.633 | 1.00 | 29.91 | O |
| HETATM | 10070 | O | HOH | 8224 | 28.774 | 46.253 | −57.672 | 1.00 | 27.24 | O |
| HETATM | 10071 | O | HOH | 8225 | 12.249 | 27.080 | 5.705 | 1.00 | 33.04 | O |
| HETATM | 10072 | O | HOH | 8226 | 46.668 | 57.243 | −23.318 | 1.00 | 40.27 | O |
| HETATM | 10073 | O | HOH | 8227 | 82.077 | −14.452 | 5.876 | 1.00 | 36.27 | O |
| HETATM | 10074 | O | HOH | 8228 | 40.389 | 30.876 | −17.266 | 1.00 | 30.97 | O |
| HETATM | 10075 | O | HOH | 8229 | 49.327 | 18.630 | −3.627 | 1.00 | 27.94 | O |
| HETATM | 10076 | O | HOH | 8230 | 30.848 | 43.282 | 37.200 | 1.00 | 29.75 | O |
| HETATM | 10077 | O | HOH | 8231 | 27.538 | 34.519 | 36.719 | 1.00 | 43.67 | O |
| HETATM | 10078 | O | HOH | 8232 | 14.545 | 35.316 | −2.739 | 1.00 | 36.62 | O |
| HETATM | 10079 | O | HOH | 8233 | 34.553 | 42.907 | −11.613 | 1.00 | 38.00 | O |
| HETATM | 10080 | O | HOH | 8234 | 50.214 | 50.520 | 6.739 | 1.00 | 38.64 | O |
| HETATM | 10081 | O | HOH | 8235 | 19.251 | 23.087 | −13.713 | 1.00 | 28.03 | O |
| HETATM | 10082 | O | HOH | 8236 | 30.812 | 60.706 | −21.436 | 1.00 | 28.95 | O |
| HETATM | 10083 | O | HOH | 8237 | 66.757 | 11.655 | −26.300 | 1.00 | 39.69 | O |
| HETATM | 10084 | O | HOH | 8238 | 35.046 | 35.455 | −12.734 | 1.00 | 39.15 | O |
| HETATM | 10085 | O | HOH | 8239 | 23.172 | 32.494 | −15.018 | 1.00 | 36.10 | O |
| HETATM | 10086 | O | HOH | 8240 | 12.204 | 48.652 | 10.766 | 1.00 | 31.97 | O |
| HETATM | 10087 | O | HOH | 8241 | 32.636 | 46.110 | −16.084 | 1.00 | 33.67 | O |
| HETATM | 10088 | O | HOH | 8242 | 23.375 | 28.819 | −16.529 | 1.00 | 28.89 | O |
| HETATM | 10089 | O | HOH | 8243 | 33.092 | 46.467 | 8.373 | 1.00 | 34.92 | O |
| HETATM | 10090 | O | HOH | 8244 | 75.191 | −15.210 | 1.700 | 1.00 | 34.77 | O |
| HETATM | 10091 | O | HOH | 8245 | 51.102 | 7.512 | −30.877 | 1.00 | 39.35 | O |
| HETATM | 10092 | O | HOH | 8246 | 29.649 | 40.776 | 11.607 | 1.00 | 36.74 | O |
| HETATM | 10093 | O | HOH | 8247 | 64.241 | −11.167 | 31.991 | 1.00 | 36.77 | O |
| HETATM | 10094 | O | HOH | 8248 | 35.807 | 52.227 | −37.837 | 1.00 | 42.89 | O |
| HETATM | 10095 | O | HOH | 8249 | 21.004 | 47.633 | −18.472 | 1.00 | 43.58 | O |
| HETATM | 10096 | O | HOH | 8250 | 20.104 | 21.077 | −27.523 | 1.00 | 37.70 | O |
| HETATM | 10097 | O | HOH | 8251 | 82.131 | −14.102 | −15.373 | 1.00 | 46.38 | O |
| HETATM | 10098 | O | HOH | 8252 | 52.596 | 0.316 | −10.214 | 1.00 | 33.07 | O |
| HETATM | 10099 | O | HOH | 8253 | 54.192 | 1.046 | 30.601 | 1.00 | 35.61 | O |
| HETATM | 10100 | O | HOH | 8254 | 28.240 | 44.984 | −53.215 | 1.00 | 30.80 | O |
| HETATM | 10101 | O | HOH | 8255 | 64.550 | −3.466 | −2.475 | 1.00 | 37.95 | O |
| HETATM | 10102 | O | HOH | 8256 | 16.260 | 21.918 | −28.169 | 1.00 | 42.28 | O |
| HETATM | 10103 | O | HOH | 8257 | 31.591 | 44.914 | 17.918 | 1.00 | 30.56 | O |
| HETATM | 10104 | O | HOH | 8258 | 63.725 | 18.485 | −36.455 | 1.00 | 41.83 | O |
| HETATM | 10105 | O | HOH | 8259 | 54.594 | 4.317 | −30.127 | 1.00 | 36.36 | O |
| HETATM | 10106 | O | HOH | 8260 | 12.031 | 48.610 | 15.939 | 1.00 | 34.32 | O |

TABLE 3-continued

FGFR2(D2–D3) Complexed with FGF2

| HETATM | 10107 | O | HOH | 8261 | 62.047 | 0.039 | 1.306 | 1.00 | 40.89 | O |
| --- | --- | --- | --- | --- | --- | --- | --- | --- | --- | --- |
| HETATM | 10108 | O | HOH | 8262 | 63.743 | 26.826 | 40.506 | 1.00 | 38.51 | O |
| HETATM | 10109 | O | HOH | 8263 | 80.317 | −12.708 | 5.435 | 1.00 | 35.75 | O |

```
CONECT 4172 4569
CONECT 4569 4172
CONECT 4893 5256
CONECT 5256 4893
CONECT 5615 6015
CONECT 6015 5615
CONECT 6356 6708
CONECT 6708 6356
CONECT 7044 7433
CONECT 7433 7044
CONECT 7784 8177
CONECT 8177 7784
CONECT 8549 8942
CONECT 8942 8549
CONECT 9289 9675
CONECT 9675 9289
CONECT 9827 9828 9829 9830 9831
CONECT 9828 9827
CONECT 9829 9827
CONECT 9830 9827
CONECT 9831 9827
CONECT 9832 9833 9834 9835 9836
CONECT 9833 9832
CONECT 9834 9832
CONECT 9835 9832
CONECT 9836 9832
CONECT 9837 9838 9839 9840 9841
CONECT 9838 9837
CONECT 9839 9837
CONECT 9840 9837
CONECT 9841 9837
CONECT 9842 9843 9844 9845 9846
CONECT 9843 9842
CONECT 9844 9842
CONECT 9845 9842
CONECT 9846 9842
MASTER    540    0    4   24  123    0    0  610101    8   36  112
```

TABLE 4

Stem Cell Factor Dimer

| | | | | | |
| --- | --- | --- | --- | --- | --- |
| HEADER | | HORMONE/GROWTH FACTOR | | 05-MAY-00 | 1EXZ |
| TITLE | | STRUCTURE OF STEM CELL FACTOR | | | |
| COMPND | | MOL_ID: 1; | | | |
| COMPND | 2 | MOLECULE: STEM CELL FACTOR; | | | |
| COMPND | 3 | CHAIN: A, B, C, D; | | | |
| COMPND | 4 | FRAGMENT: 26–166; | | | |
| COMPND | 5 | SYNONYM: SCF; | | | |
| COMPND | 6 | ENGINEERED: YES | | | |
| SOURCE | | MOL_ID: 1; | | | |
| SOURCE | 2 | ORGANISM_SCIENTIFIC: *HOMO SAPIENS*; | | | |
| SOURCE | 3 | ORGANISM_COMMON: HUMAN; | | | |
| SOURCE | 4 | EXPRESSION_SYSTEM: *ESCHERICHIA COLI*; | | | |
| SOURCE | 5 | EXPRESSION_SYSTEM_COMMON: BACTERIA | | | |
| KEYWDS | | SCF | | | |
| EXPDTA | | X-RAY DIFFRACTION | | | |
| AUTHOR | | Z.ZHANG,R.ZHANG,A.JOACHIMIAK,J.SCHLESSINGER,X.KONG | | | |
| REVDAT | 1 | 06-JUL-00 1EXZ 0 | | | |
| JRNL | | AUTH | Z.ZHANG,R.ZHANG,A.JOACHIMIAK,J.SCHLESSINGER,X.KONG | | |
| JRNL | | TITL | CRYSTAL STRUCTURE OF HUMAN STEM CELL FACTOR: | | |
| JRNL | | TITL 2 | IMPLICATION FOR STEM CELL FACTOR RECEPTOR | | |
| JRNL | | TITL 3 | DIMERIZATION AND ACTIVATION. | | |
| JRNL | | REF | PROC.NAT.ACAD.SCI.USA V. 97 7732 2000 | | |
| JRNL | | REFN | ASTM PNASA6 US ISSN 0027-8424 | | |
| REMARK | 1 | | | | |
| REMARK | 2 | | | | |
| REMARK | 2 | RESOLUTION. 2.30 ANGSTROMS. | | | |
| REMARK | 3 | | | | |
| REMARK | 3 | REFINEMENT. | | | |

TABLE 4-continued

Stem Cell Factor Dimer

```
REMARK   3     PROGRAM       : CNS
REMARK   3     AUTHORS       : BRUNGER,ADAMS,CLORE,DELANO,GROS,GROSSE-
REMARK   3                   : KUNSTLEVE,JIANG,KUSZEWSKI,NILGES, PANNU,
REMARK   3                   : READ,RICE,SIMONSON,WARREN
REMARK   3
REMARK   3     REFINEMENT TARGET : MLF
REMARK   3
REMARK   3     DATA USED IN REFINEMENT.
REMARK   3       RESOLUTION RANGE HIGH      (ANGSTROMS) : 2.30
REMARK   3       RESOLUTION RANGE LOW       (ANGSTROMS) : 40.00
REMARK   3       DATA CUTOFF                (SIGMA(F)) : 2.000
REMARK   3       OUTLIER CUTOFF HIGH        (RMS(ABS(F))) : NULL
REMARK   3       COMPLETENESS (WORKING+TEST)      (%) : 10.0
REMARK   3       NUMBER OF REFLECTIONS               : 21494
REMARK   3
REMARK   3
REMARK   3     FIT TO DATA USED IN REFINEMENT.
REMARK   3       CROSS-VALIDATION METHOD         : NULL
REMARK   3       FREE R VALUE TEST SET SELECTION : RANDOMLY SELECTED 10%
REMARK   3                                         OF REFLECTIONS
REMARK   3       R VALUE            (WORKING SET) : 0.223
REMARK   3       FREE R VALUE                     : 0.294
REMARK   3       FREE R VALUE TEST SET SIZE   (%) : NULL
REMARK   3       FREE R VALUE TEST SET COUNT      : 2133
REMARK   3       ESTIMATED ERROR OF FREE R VALUE  : NULL
REMARK   3
REMARK   3     FIT IN THE HIGHEST RESOLUTION BIN.
REMARK   3       TOTAL NUMBER OF BINS USED                : NULL
REMARK   3       BIN RESOLUTION RANGE HIGH         (A) : NULL
REMARK   3       BIN RESOLUTION RANGE LOW          (A) : NULL
REMARK   3       BIN COMPLETENESS (WORKING+TEST)   (%) : NULL
REMARK   3       REFLECTIONS IN BIN       (WORKING SET) : NULL
REMARK   3       BIN R VALUE              (WORKING SET) : NULL
REMARK   3       BIN FREE R VALUE                        : NULL
REMARK   3       BIN FREE R VALUE TEST SET SIZE    (%) : NULL
REMARK   3       BIN FREE R VALUE TEST SET COUNT       : NULL
REMARK   3       ESTIMATED ERROR OF BIN FREE R VALUE   : NULL
REMARK   3
REMARK   3     NUMBER OF NON-HYDROGEN ATOMS USED IN REFINEMENT.
REMARK   3       PROTEIN ATOMS          : 4090
REMARK   3       NUCLEIC ACID ATOMS     : 0
REMARK   3       HETEROGEN ATOMS        : 14
REMARK   3       SOLVENT ATOMS          : 132
REMARK   3
REMARK   3     B VALUES.
REMARK   3       FROM WILSON PLOT             (A**2) : 45.00
REMARK   3       MEAN B VALUE      (OVERALL, A**2) : NULL
REMARK   3       OVERALL ANISOTROPIC B VALUE.
REMARK   3         B11 (A**2) : NULL
REMARK   3         B22 (A**2) : NULL
REMARK   3         B33 (A**2) : NULL
REMARK   3         B12 (A**2) : NULL
REMARK   3         B13 (A**2) : NULL
REMARK   3         B23 (A**2) : NULL
REMARK   3
REMARK   3     ESTIMATED COORDINATE ERROR.
REMARK   3       ESD FROM LUZZATI PLOT        (A) : NULL
REMARK   3       ESD FROM SIGMAA              (A) : NULL
REMARK   3       LOW RESOLUTION CUTOFF        (A) : NULL
REMARK   3
REMARK   3     CROSS-VALIDATED ESTIMATED COORDINATE ERROR.
REMARK   3       ESD FROM C-V LUZZATI PLOT    (A) : NULL
REMARK   3       ESD FROM C-V SIGMAA          (A) : NULL
REMARK   3
REMARK   3     RMS DEVIATIONS FROM IDEAL VALUES.
REMARK   3       BOND LENGTHS                 (A) : 0.007
REMARK   3       BOND ANGLES            (DEGREES) : 1.22
REMARK   3       DIHEDRAL ANGLES        (DEGREES) : NULL
REMARK   3       IMPROPER ANGLES        (DEGREES) : NULL
REMARK   3
REMARK   3     ISOTROPIC THERMAL MODEL : NULL
REMARK   3
REMARK   3     ISOTROPIC THERMAL FACTOR RESTRAINTS.     RMS    SIGMA
REMARK   3       MAIN-CHAIN BOND            (A**2) : NULL ; NULL
REMARK   3       MAIN-CHAIN ANGLE           (A**2) : NULL ; NULL
REMARK   3       SIDE-CHAIN BOND            (A**2) : NULL ; NULL
REMARK   3       SIDE-CHAIN ANGLE           (A**2) : NULL ; NULL
```

TABLE 4-continued

Stem Cell Factor Dimer

| | | | | |
|---|---|---|---|---|
| REMARK | 3 | | | |
| REMARK | 3 | | | |
| REMARK | 3 | BULK SOLVENT MODELING. | | |
| REMARK | 3 | METHOD USED : NULL | | |
| REMARK | 3 | KSOL : NULL | | |
| REMARK | 3 | BSOL : NULL | | |
| REMARK | 3 | | | |
| REMARK | 3 | NCS MODEL : NULL | | |
| REMARK | 3 | | | |
| REMARK | 3 | NCS RESTRAINTS. | RMS | SIGMA/WEIGHT |
| REMARK | 3 | GROUP 1 POSITIONAL | (A) : NULL ; NULL | |
| REMARK | 3 | GROUP 1 B-FACTOR | (A**2) : NULL ; NULL | |
| REMARK | 3 | | | |
| REMARK | 3 | PARAMETER FILE 1 : NULL | | |
| REMARK | 3 | TOPOLOGY FILE 1 : NULL | | |
| REMARK | 3 | | | |
| REMARK | 3 | OTHER REFINEMENT REMARKS: MAXIMUM LIKELIHOOD TARGET USING | | |
| REMARK | 3 | AMPLITUDES | | |
| REMARK | 4 | | | |
| REMARK | 4 | 1EXZ COMPLIES WITH FORMAT V. 2.3, 09-JULY-1998 | | |
| REMARK | 100 | | | |
| REMARK | 100 | THIS ENTRY HAS BEEN PROCESSED BY RCSB ON 12-MAY-2000. | | |
| REMARK | 100 | THE RCSB ID CODE IS RCSB011008. | | |
| REMARK | 200 | | | |
| REMARK | 200 | EXPERIMENTAL DETAILS | | |
| REMARK | 200 | EXPERIMENT TYPE | : X-RAY DIFFRACTION | |
| REMARK | 200 | DATE OF DATA COLLECTION | : 26-NOV-1999 | |
| REMARK | 200 | TEMPERATURE | (KELVIN) : 100.0 | |
| REMARK | 200 | PH | : 7.00 | |
| REMARK | 200 | NUMBER OF CRYSTALS USED | : 1 | |
| REMARK | 200 | | | |
| REMARK | 200 | SYNCHROTRON | (Y/N) : Y; Y | |
| REMARK | 200 | RADIATION SOURCE | : APS ; APS | |
| REMARK | 200 | BEAMLINE | : 19ID; 19ID | |
| REMARK | 200 | X-RAY GENERATOR MODEL | : NULL | |
| REMARK | 200 | MONOCHROMATIC OR LAUE | (M/L) : M | |
| REMARK | 200 | WAVELENGTH OR RANGE | (A) : 1.03; 1.55 | |
| REMARK | 200 | MONOCHROMATOR | : NULL | |
| REMARK | 200 | OPTICS | : NULL | |
| REMARK | 200 | | | |
| REMARK | 200 | DETECTOR TYPE | : CCD | |
| REMARK | 200 | DETECTOR MANUFACTURER | : BRANDEIS | |
| REMARK | 200 | INTENSITY-INTEGRATION SOFTWARE | : DENZO | |
| REMARK | 200 | DATA SCALING SOFTWARE | : SCALEPACK | |
| REMARK | 200 | | | |
| REMARK | 200 | NUMBER OF UNIQUE REFLECTIONS | : 21454 | |
| REMARK | 200 | RESOLUTION RANGE HIGH | (A) : 2.300 | |
| REMARK | 200 | RESOLUTION RANGE LOW | (A) : 40.000 | |
| REMARK | 200 | REJECTION CRITERIA | (SIGMA(I)) : 2.000 | |
| REMARK | 200 | | | |
| REMARK | 200 | OVERALL. | | |
| REMARK | 200 | COMPLETENESS FOR RANGE | (%) : 99.5 | |
| REMARK | 200 | DATA REDUNDANCY | : 8.000 | |
| REMARK | 200 | R MERGE | (I) : 0.05800 | |
| REMARK | 200 | R SYM | (I) : NULL | |
| REMARK | 200 | <I/SIGMA(I)> FOR THE DATA SET | : 29.0000 | |
| REMARK | 200 | | | |
| REMARK | 200 | IN THE HIGHEST RESOLUTION SHELL. | | |
| REMARK | 200 | HIGHEST RESOLUTION SHELL, RANGE HIGH | (A) : 2.30 | |
| REMARK | 200 | HIGHEST RESOLUTION SHELL, RANGE LOW | (A) : 2.38 | |
| REMARK | 200 | COMPLETENESS FOR SHELL | (%) : 90.1 | |
| REMARK | 200 | DATA REDUNDANCY IN SHELL | : 7.00 | |
| REMARK | 200 | R MERGE FOR SHELL | (I) : 0.25000 | |
| REMARK | 200 | R SYM FOR SHELL | (I) : NULL | |
| REMARK | 200 | <I/SIGMA(I)> FOR SHELL | : NULL | |
| REMARK | 200 | | | |
| REMARK | 200 | DIFFRACTION PROTOCOL: SINGLE WAVELENGTH | | |
| REMARK | 200 | METHOD USED TO DETERMINE THE STRUCTURE: NULL | | |
| REMARK | 200 | SOFTWARE USED: PHASES | | |
| REMARK | 200 | STARTING MODEL: NULL | | |
| REMARK | 200 | | | |
| REMARK | 200 | REMARK: NULL | | |
| REMARK | 280 | | | |
| REMARK | 280 | CRYSTAL | | |
| REMARK | 280 | SOLVENT CONTENT, VS (%): NULL | | |
| REMARK | 280 | MATTHEWS COEFFICIENT, VM (ANGSTROMS**3/DA): NULL | | |
| REMARK | 280 | | | |

TABLE 4-continued

Stem Cell Factor Dimer

| | |
|---|---|
| REMARK 280 | CRYSTALLIZATION CONDITIONS: 28% PEG 400, 250 MM CACL2, 1 |
| REMARK 280 | MM SMCL3 |
| REMARK 290 | |
| REMARK 290 | CRYSTALLOGRAPHIC SYMMETRY |
| REMARK 290 | SYMMETRY OPERATORS FOR SPACE GROUP: P 1 21 1 |
| REMARK 290 | |
| REMARK 290 | SYMOP SYMMETRY |
| REMARK 290 | NNNMMM OPERATOR |
| REMARK 290 | 1555 X,Y,Z |
| REMARK 290 | 2555 −X,1/2+Y,−Z |
| REMARK 290 | |
| REMARK 290 | WHERE NNN → OPERATOR NUMBER |
| REMARK 290 | MMM → TRANSLATION VECTOR |
| REMARK 290 | |
| REMARK 290 | CRYSTALLOGRAPHIC SYMMETRY TRANSFORMATIONS |
| REMARK 290 | THE FOLLOWING TRANSFORMATIONS OPERATE ON THE ATOM/HETATM |
| REMARK 290 | RECORDS IN THIS ENTRY TO PRODUCE CRYSTALLOGRAPHICALLY |
| REMARK 290 | RELATED MOLECULES. |
| REMARK 290 | SMTRY1   1    1.000000   0.000000   0.000000   0.00000 |
| REMARK 290 | SMTRY2   1    0.000000   1.000000   0.000000   0.00000 |
| REMARK 290 | SMTRY3   1    0.000000   0.000000   1.000000   0.00000 |
| REMARK 290 | SMTRY1   2   −1.000000   0.000000   0.000000   0.00000 |
| REMARK 290 | SMTRY2   2    0.000000   1.000000   0.000000  43.76300 |
| REMARK 290 | SMTRY3   2    0.000000   0.000000  −1.000000   0.00000 |
| REMARK 290 | |
| REMARK 290 | REMARK: NULL |
| REMARK 300 | |
| REMARK 300 | BIOMOLECULE: 1, 2 |
| REMARK 300 | THIS ENTRY CONTAINS THE CRYSTALLOGRAPHIC ASYMMETRIC UNIT |
| REMARK 300 | WHICH CONSISTS OF 4 CHAIN(S). SEE REMARK 350 FOR |
| REMARK 300 | INFORMATION ON GENERATING THE BIOLOGICAL MOLECULE(S). |
| REMARK 350 | |
| REMARK 350 | GENERATING THE BIOMOLECULE |
| REMARK 350 | COORDINATES FOR A COMPLETE MULTIMER REPRESENTING THE KNOWN |
| REMARK 350 | BIOLOGICALLY SIGNIFICANT OLIGOMERIZATION STATE OF THE |
| REMARK 350 | MOLECULE CAN BE GENERATED BY APPLYING BIOMT TRANSFORMATIONS |
| REMARK 350 | GIVEN BELOW. BOTH NON-CRYSTALLOGRAPHIC AND |
| REMARK 350 | CRYSTALLOGRAPHIC OPERATIONS ARE GIVEN. |
| REMARK 350 | |
| REMARK 350 | BIOMOLECULE: 1 |
| REMARK 350 | APPLY THE FOLLOWING TO CHAINS: A, B |
| REMARK 350 | BIOMT1   1   1.000000   0.000000   0.000000   0.00000 |
| REMARK 350 | BIOMT2   1   0.000000   1.000000   0.000000   0.00000 |
| REMARK 350 | BIOMT3   1   0.000000   0.000000   1.000000   0.00000 |
| REMARK 350 | BIOMOLECULE: 2 |
| REMARK 350 | APPLY THE FOLLOWING TO CHAINS: C, D |
| REMARK 350 | BIOMT1   2   1.000000   0.000000   0.000000   0.00000 |
| REMARK 350 | BIOMT2   2   0.000000   1.000000   0.000000   0.00000 |
| REMARK 350 | BIOMT3   2   0.000000   0.000000   1.000000   0.00000 |
| REMARK 465 | |
| REMARK 465 | MISSING RESIDUES |
| REMARK 465 | THE FOLLOWING RESIDUES WERE NOT LOCATED IN THE |
| REMARK 465 | EXPERIMENT. (M=MODEL NUMBER; RES=RESIDUE NAME; C=CHAIN |
| REMARK 465 | IDENTIFIER; SSSEQ=SEQUENCE NUMBER; I=INSERTION CODE.) |
| REMARK 465 | |
| REMARK 465 | M   RES   C   SSSEQI |
| REMARK 465 | GLU   A     1 |
| REMARK 465 | GLY   A     2 |
| REMARK 465 | ILE   A     3 |
| REMARK 465 | GLU   A   134 |
| REMARK 465 | THR   A   135 |
| REMARK 465 | SER   A   136 |
| REMARK 465 | VAL   A   140 |
| REMARK 465 | SER   A   141 |
| REMARK 465 | GLU   B   201 |
| REMARK 465 | GLU   C   401 |
| REMARK 465 | GLY   C   402 |
| REMARK 465 | ILE   C   403 |
| REMARK 465 | CYS   C   404 |
| REMARK 465 | ARG   C   405 |
| REMARK 465 | ASN   C   406 |
| REMARK 465 | ARG   C   407 |
| REMARK 465 | VAL   C   408 |
| REMARK 465 | VAL   C   540 |
| REMARK 465 | SER   C   541 |
| REMARK 465 | GLU   D   601 |
| REMARK 465 | GLY   D   602 |

TABLE 4-continued

Stem Cell Factor Dimer

| | | | | | | | | |
|---|---|---|---|---|---|---|---|---|
| REMARK 465 | | ILE | D | 603 | | | | |
| REMARK 465 | | CYS | D | 604 | | | | |
| REMARK 465 | | ARG | D | 605 | | | | |
| REMARK 465 | | ASN | D | 606 | | | | |
| REMARK 465 | | ARG | D | 607 | | | | |
| REMARK 465 | | VAL | D | 608 | | | | |
| REMARK 465 | | SER | D | 733 | | | | |
| REMARK 465 | | GLU | D | 734 | | | | |
| REMARK 465 | | THR | D | 735 | | | | |
| REMARK 465 | | SER | D | 736 | | | | |
| REMARK 465 | | ASP | D | 737 | | | | |
| REMARK 465 | | CYS | D | 738 | | | | |
| REMARK 465 | | VAL | D | 739 | | | | |
| REMARK 465 | | VAL | D | 740 | | | | |
| REMARK 465 | | SER | D | 741 | | | | |
| REMARK 470 | | | | | | | | |
| REMARK 470 | MISSING ATOM | | | | | | | |
| REMARK 470 | THE FOLLOWING RESIDUES HAVE MISSING ATOMS (M=MODEL NUMBER; | | | | | | | |
| REMARK 470 | RES=RESIDUE NAME; C=CHAIN IDENTIFIER; SSEQ=SEQUENCE NUMBER; | | | | | | | |
| REMARK 470 | I=INSERTION CODE): | | | | | | | |
| REMARK 470 | M | RES | CSSEQI | ATOMS | | | | |
| REMARK 470 | | ARG | A 5 | CG | CD | NE | CZ | NH1 NH2 |
| REMARK 470 | | ARG | A 7 | CG | CD | NE | CZ | NH1 NH2 |
| REMARK 470 | | ASN | A 10 | CG | OD1 | ND2 | | |
| REMARK 470 | | GLU | B 292 | CG | CD | OE1 | OE2 | |
| REMARK 470 | | ASN | B 293 | CG | OD1 | ND2 | | |
| REMARK 470 | | SER | B 294 | OG | | | | |
| REMARK 470 | | SER | B 295 | OG | | | | |
| REMARK 470 | | LYS | B 296 | CG | CD | CE | NZ | |
| REMARK 470 | | ASP | B 297 | CG | OD1 | OD2 | | |
| REMARK 470 | | LEU | B 298 | CG | CD1 | CD2 | | |
| REMARK 470 | | LYS | B 299 | CG | CD | CE | NZ | |
| REMARK 470 | | LYS | B 300 | CG | CD | CE | NZ | |
| REMARK 470 | | SER | B 301 | OG | | | | |
| REMARK 470 | | PHE | B 302 | CG | CD1 | CD2 | CE1 | CE2 CZ |
| REMARK 470 | | LYS | B 303 | CG | CD | CE | NZ | |
| REMARK 470 | | SER | B 341 | OG | | | | |
| REMARK 470 | | ASN | C 410 | CG | OD1 | ND2 | | |
| REMARK 470 | | LYS | C 413 | CG | CD | CE | NZ | |
| REMARK 470 | | LYS | C 491 | CG | CD | CE | NZ | |
| REMARK 470 | | GLU | C 492 | CG | CD | OE1 | OE2 | |
| REMARK 470 | | ASN | C 493 | CG | OD1 | ND2 | | |
| REMARK 470 | | SER | C 494 | OG | | | | |
| REMARK 470 | | SER | C 495 | OG | | | | |
| REMARK 470 | | LYS | C 496 | CG | CD | CE | NZ | |
| REMARK 470 | | ASP | C 497 | CG | OD1 | OD2 | | |
| REMARK 470 | | LEU | C 498 | CG | CD1 | CD2 | | |
| REMARK 470 | | LYS | C 499 | CG | CD | CE | NZ | |
| REMARK 470 | | LYS | C 500 | CG | CD | CE | NZ | |
| REMARK 470 | | SER | C 501 | OG | | | | |
| REMARK 470 | | PHE | C 502 | CG | CD1 | CD2 | CE1 | CE2 CZ |
| REMARK 470 | | LYS | D 696 | CG | CD | CE | NZ | |
| REMARK 470 | | LYS | D 699 | CG | CD | CE | NZ | |
| REMARK 470 | | LYS | D 700 | CG | CD | CE | NZ | |
| REMARK 470 | | SER | D 701 | OG | | | | |
| REMARK 470 | | PHE | D 702 | CG | CD1 | CD2 | CE1 | CE2 CZ |
| REMARK 470 | | LYS | D 703 | CG | CD | CE | NZ | |
| REMARK 500 | | | | | | | | |
| REMARK 500 | GEOMETRY AND STEREOCHEMISTRY | | | | | | | |
| REMARK 500 | SUBTOPIC: CLOSE CONTACTS IN SAME ASYMMETRIC UNIT | | | | | | | |
| REMARK 500 | | | | | | | | |
| REMARK 500 | THE FOLLOWING ATOMS ARE IN CLOSE CONTACT. | | | | | | | |
| REMARK 500 | | | | | | | | |
| REMARK 500 | ATM1 | RES | C | SSEQI | ATM2 | RES | C | SSEQI |
| REMARK 500 | SM | SM | C | 801 | O | HOH | | 946   1.92 |
| REMARK 500 | | | | | | | | |
| REMARK 500 | GEOMETRY AND STEREOCHEMISTRY | | | | | | | |
| REMARK 500 | SUBTOPIC: CLOSE CONTACTS | | | | | | | |
| REMARK 500 | | | | | | | | |
| REMARK 500 | THE FOLLOWING ATOMS THAT ARE RELATED BY CRYSTALLOGRAPHIC | | | | | | | |
| REMARK 500 | SYMMETRY ARE IN CLOSE CONTACT. AN ATOM LOCATED WITHIN 0.15 | | | | | | | |
| REMARK 500 | ANGSTROMS OF A SYMMETRY RELATED ATOM IS ASSUMED TO BE ON A | | | | | | | |
| REMARK 500 | SPECIAL POSITION AND IS, THEREFORE, LISTED IN REMARK 375 | | | | | | | |
| REMARK 500 | INSTEAD OF REMARK 500. ATOMS WITH NON-BLANK ALTERNATE | | | | | | | |
| REMARK 500 | LOCATION INDICATORS ARE NOT INCLUDED IN THE CALCULATIONS. | | | | | | | |
| REMARK 500 | | | | | | | | |

TABLE 4-continued

Stem Cell Factor Dimer

```
REMARK 500    DISTANCE CUTOFF:
REMARK 500    2.2 ANGSTROMS FOR CONTACTS NOT INVOLVING HYDROGEN ATOMS
REMARK 500    1.6 ANGSTROMS FOR CONTACTS INVOLVING HYDROGEN ATOMS
REMARK 500
REMARK 500      ATM1   RES  C   SSEQI   ATM2   RES  C   SSEQI   SSYMOP   DISTANCE
REMARK 500      OE1    GLU  D   713     SM     SM   B   803     2645     2.12
REMARK 500      OE2    GLU  A   88      SM     SM   C   801     2656     2.17
REMARK 500
REMARK 500    GEOMETRY AND STEREOCHEMISTRY
REMARK 500    SUBTOPIC: COVALENT BOND LENGTHS
REMARK 500
REMARK 500    THE STEREOCHEMICAL PARAMETERS OF THE FOLLOWING RESIDUES
REMARK 500    HAVE VALUES WHICH DEVIATE FROM EXPECTED VALUES BY MORE
REMARK 500    THAN 6*RMSD (M=MODEL NUMBER; RES=RESIDUE NAME; C=CHAIN
REMARK 500    IDENTIFIER; SSEQ=SEQUENCE NUMBER; I=INSERTION CODE).
REMARK 500
REMARK 500    STANDARD TABLE:
REMARK 500    FORMAT: (10X,I3,1X,2(A3,1X,A1,I4,A1,1X,A4,3X),F6.3)
REMARK 500
REMARK 500    EXPECTED VALUES: ENGH AND HUBER, 1991
REMARK 500
REMARK 500      M   RES   CSSEQI   ATM1    RES   CSSEQI   ATM2   DEVIATION
REMARK 500          PRO   A  23    CG      PRO   A  23    CB      0.046
REMARK 500          MET   A  48    CE      MET   A  48    SD     -0.081
REMARK 500          MET   C 448    SD      MET   C 448    CG      0.040
REMARK 500          PRO   C 512    CG      PRO   C 512    CB      0.058
REMARK 500
REMARK 500    GEOMETRY AND STEREOCHEMISTRY
REMARK 500    SUBTOPIC: COVALENT BOND ANGLES
REMARK 500
REMARK 500    THE STEREOCHEMICAL PARAMETERS OF THE FOLLOWING RESIDUES
REMARK 500    HAVE VALUES WHICH DEVIATE FROM EXPECTED VALUES BY MORE
REMARK 500    THAN 6*RMSD (M=MODEL NUMBER; RES=RESIDUE NAME; C=CHAIN
REMARK 500    IDENTIFIER; SSEQ=SEQUENCE NUMBER; I=INSERTION CODE).
REMARK 500
REMARK 500    STANDARD TABLE:
REMARK 500    FORMAT: (10X,I3,1X,A3,1X,A1,I4,A1,3(1X,A4,2X),12X,F5.1)
REMARK 500
REMARK 500    EXPECTED VALUES: ENGH AND HUBER, 1991
REMARK 500
REMARK 500      M   RES   CSSEQI    ATM1        ATM2        ATM3
REMARK 500          THR   A 111     N      -    CA     -    C      ANGL. DEV. = -7.7 DEGREES
REMARK 500          ARG   A 117     N      -    CA     -    C      ANGL. DEV. = -7.7 DEGREES
REMARK 500          PRO   B 234     N      -    CA     -    C      ANGL. DEV. = 10.2 DEGREES
REMARK 500          ILE   B 245     N      -    CA     -    C      ANGL. DEV. =  8.5 DEGREES
REMARK 500          ARG   B 317     N      -    CA     -    C      ANGL. DEV. = -8.0 DEGREES
REMARK 500          LYS   C 413     N      -    CA     -    C      ANGL. DEV. = -8.0 DEGREES
REMARK 500          ASP   C 414     N      -    CA     -    C      ANGL. DEV. = -8.4 DEGREES
REMARK 500          ASP   C 437     N      -    CA     -    C      ANGL. DEV. =  7.6 DEGREES
REMARK 500          TRP   C 444     N      -    CA     -    C      ANGL. DEV. = 10.9 DEGREES
REMARK 500          ILE   C 445     N      -    CA     -    C      ANGL. DEV. =  7.2 DEGREES
REMARK 500          ASP   C 528     N      -    CA     -    C      ANGL. DEV. = 11.9 DEGREES
REMARK 500          VAL   C 530     N      -    CA     -    C      ANGL. DEV. =  8.9 DEGREES
REMARK 500          THR   D 711     N      -    CA     -    C      ANGL. DEV. = -8.6 DEGREES
REMARK 500          ARG   D 717     N      -    CA     -    C      ANGL. DEV. = -8.1 DEGREES
REMARK 500
REMARK 500    GEOMETRY AND STEREOCHEMISTRY
REMARK 500    SUBTOPIC: TORSION ANGLES
REMARK 500
REMARK 500    TORSION ANGLES OUTSIDE THE EXPECTED RAMACHANDRAN REGIONS:
REMARK 500    (M=MODEL NUMBER; RES=RESIDUE NAME; C=CHAIN IDENTIFIER;
REMARK 500    SSEQ=SEQUENCE NUMBER; I=INSERTION CODE).
REMARK 500
REMARK 500    STANDARD TABLE:
REMARK 500    FORMAT: (10X,I3,1X,A3,1X,A1,I4,A1,4X,F7.2,3X,F7.2)
REMARK 500
REMARK 500      M   RES   CSSEQI     PSI       PHI
REMARK 500          SER A 101     104.88      120.52
REMARK 500          PHE A 102      78.79     -100.99
REMARK 500          PHE B 302      50.55      -96.61
REMARK 500          PHE C 502      54.70      -95.94
REMARK 500          ASP C 528      25.52     -113.66
REMARK 500          VAL C 530      33.44      113.93
REMARK 500          ILE D 645      61.98      -60.00
DBREF  1EXZ   A     1    141  SWS    P21583   SCF_HUMAN   26   166
DBREF  1EXZ   B   201    341  SWS    P21583   SCF_HUMAN   26   166
```

TABLE 4-continued

Stem Cell Factor Dimer

| | | | | | | |
|---|---|---|---|---|---|---|
| DBREF | 1EXZ | C | 401 | 541 | SWS | P21583 SCF_HUMAN 26 166 |
| DBREF | 1EXZ | D | 601 | 741 | SWS | P21583 SCF_HUMAN 26 166 |
| SEQRES | 1 | A | 141 | GLU GLY ILE CYS ARG ASN ARG VAL THR ASN ASN VAL LYS | | |
| SEQRES | 2 | A | 141 | ASP VAL THR LYS LEU VAL ALA ASN LEU PRO LYS ASP TYR | | |
| SEQRES | 3 | A | 141 | MET ILE THR LEU LYS TYR VAL PRO GLY MET ASP VAL LEU | | |
| SEQRES | 4 | A | 141 | PRO SER HIS CYS TRP ILE SER GLU MET VAL VAL GLN LEU | | |
| SEQRES | 5 | A | 141 | SER ASP SER LEU THR ASP LEU LEU ASP LYS PHE SER ASN | | |
| SEQRES | 6 | A | 141 | ILE SER GLU GLY LEU SER ASN TYR SER ILE ILE ASP LYS | | |
| SEQRES | 7 | A | 141 | LEU VAL ASN ILE VAL ASP ASP LEU VAL GLU CYS VAL LYS | | |
| SEQRES | 8 | A | 141 | GLU ASN SER SER LYS ASP LEU LYS LYS SER PHE LYS SER | | |
| SEQRES | 9 | A | 141 | PRO GLU PRO ARG LEU PHE THR PRO GLU GLU PHE PHE ARG | | |
| SEQRES | 10 | A | 141 | ILE PHE ASN ARG SER ILE ASP ALA PHE LYS ASP PHE VAL | | |
| SEQRES | 11 | A | 141 | VAL ALA SER GLU THR SER ASP CYS VAL VAL SER | | |
| SEQRES | 1 | B | 141 | GLU GLY ILE CYS ARG ASN ARG VAL THR ASN ASN VAL LYS | | |
| SEQRES | 2 | B | 141 | ASP VAL THR LYS LEU VAL ALA ASN LEU PRO LYS ASP TYR | | |
| SEQRES | 3 | B | 141 | MET ILE THR LEU LYS TYR VAL PRO GLY MET ASP VAL LEU | | |
| SEQRES | 4 | B | 141 | PRO SER HIS CYS TRP ILE SER GLU MET VAL VAL GLN LEU | | |
| SEQRES | 5 | B | 141 | SER ASP SER LEU THR ASP LEU LEU ASP LYS PHE SER ASN | | |
| SEQRES | 6 | B | 141 | ILE SER GLU GLY LEU SER ASN TYR SER ILE ILE ASP LYS | | |
| SEQRES | 7 | B | 141 | LEU VAL ASN ILE VAL ASP ASP LEU VAL GLU CYS VAL LYS | | |
| SEQRES | 8 | B | 141 | GLU ASN SER SER LYS ASP LEU LYS LYS SER PHE LYS SER | | |
| SEQRES | 9 | B | 141 | PRO GLU PRO ARG LEU PHE THR PRO GLU GLU PHE PHE ARG | | |
| SEQRES | 10 | B | 141 | ILE PHE ASN ARG SER ILE ASP ALA PHE LYS ASP PHE VAL | | |
| SEQRES | 11 | B | 141 | VAL ALA SER GLU THR SER ASP CYS VAL VAL SER | | |
| SEQRES | 1 | C | 141 | GLU GLY ILE CYS ARG ASN ARG VAL THR ASN ASN VAL LYS | | |
| SEQRES | 2 | C | 141 | ASP VAL THR LYS LEU VAL ALA ASN LEU PRO LYS ASP TYR | | |
| SEQRES | 3 | C | 141 | MET ILE THR LEU LYS TYR VAL PRO GLY MET ASP VAL LEU | | |
| SEQRES | 4 | C | 141 | PRO SER HIS CYS TRP ILE SER GLU MET VAL VAL GLN LEU | | |
| SEQRES | 5 | C | 141 | SER ASP SER LEU THR ASP LEU LEU ASP LYS PHE SER ASN | | |
| SEQRES | 6 | C | 141 | ILE SER GLU GLY LEU SER ASN TYR SER ILE ILE ASP LYS | | |
| SEQRES | 7 | C | 141 | LEU VAL ASN ILE VAL ASP ASP LEU VAL GLU CYS VAL LYS | | |
| SEQRES | 8 | C | 141 | GLU ASN SER SER LYS ASP LEU LYS LYS SER PHE LYS SER | | |
| SEQRES | 9 | C | 141 | PRO GLU PRO ARG LEU PHE THR PRO GLU GLU PHE PHE ARG | | |
| SEQRES | 10 | C | 141 | ILE PHE ASN ARG SER ILE ASP ALA PHE LYS ASP PHE VAL | | |
| SEQRES | 11 | C | 141 | VAL ALA SER GLU THR SER ASP CYS VAL VAL SER | | |
| SEQRES | 1 | D | 141 | GLU GLY ILE CYS ARG ASN ARG VAL THR ASN ASN VAL LYS | | |
| SEQRES | 2 | D | 141 | ASP VAL THR LYS LEU VAL ALA ASN LEU PRO LYS ASP TYR | | |
| SEQRES | 3 | D | 141 | MET ILE THR LEU LYS TYR VAL PRO GLY MET ASP VAL LEU | | |
| SEQRES | 4 | D | 141 | PRO SER HIS CYS TRP ILE SER GLU MET VAL VAL GLN LEU | | |
| SEQRES | 5 | D | 141 | SER ASP SER LEU THR ASP LEU LEU ASP LYS PHE SER ASN | | |
| SEQRES | 6 | D | 141 | ILE SER GLU GLY LEU SER ASN TYR SER ILE ILE ASP LYS | | |
| SEQRES | 7 | D | 141 | LEU VAL ASN ILE VAL ASP ASP LEU VAL GLU CYS VAL LYS | | |
| SEQRES | 8 | D | 141 | GLU ASN SER SER LYS ASP LEU LYS LYS SER PHE LYS SER | | |
| SEQRES | 9 | D | 141 | PRO GLU PRO ARG LEU PHE THR PRO GLU GLU PHE PHE ARG | | |
| SEQRES | 10 | D | 141 | ILE PHE ASN ARG SER ILE ASP ALA PHE LYS ASP PHE VAL | | |
| SEQRES | 11 | D | 141 | VAL ALA SER GLU THR SER ASP CYS VAL VAL SER | | |
| HET | SM | C | 801 | 1 | | |
| HET | SM | | 802 | 1 | | |
| HET | SM | B | 803 | 1 | | |
| HET | SM | | 804 | 1 | | |
| HET | CA | C | 805 | 1 | | |
| HET | CA | A | 806 | 1 | | |
| HET | TRS | | 807 | 8 | | |
| HETNAM | | SM SAMARIUM (III) ION | | | | |
| HETNAM | | CA CALCIUM ION | | | | |
| HETNAM | | TRS 2-AMINO-2-HYDROXYMETHYL-PROPANE-1,3-DIOL | | | | |
| HETSYN | | TRS TRIS BUFFER | | | | |
| FORMUL | 5 | SM | 4(SM1 3+) | | | |
| FORMUL | 9 | CA | 2(CA1 2+) | | | |
| FORMUL | 11 | TRS | C4 H12 N1 O3 1+ | | | |
| FORMUL | 12 | HOH | *132(H2 O1) | | | |
| HELIX | 1 | 1 | ASN | A | 11 | ASN A 21 1 | 11 |
| HELIX | 2 | 2 | PRO | A | 40 | CYS A 43 5 | 4 |
| HELIX | 3 | 3 | TRP | A | 44 | ASP A 61 1 | 18 |
| HELIX | 4 | 4 | SER | A | 71 | ASN A 93 1 | 23 |
| HELIX | 5 | 5 | THR | A | 111 | ASP A 128 1 | 18 |
| HELIX | 6 | 6 | ASN | B | 211 | ASN B 221 1 | 11 |
| HELIX | 7 | 7 | PRO | B | 240 | CYS B 243 5 | 4 |
| HELIX | 8 | 8 | TRP | B | 244 | ASP B 261 1 | 18 |
| HELIX | 9 | 9 | SER | B | 271 | VAL B 290 1 | 20 |
| HELIX | 10 | 10 | THR | B | 311 | ALA B 325 1 | 15 |
| HELIX | 11 | 11 | LYS | C | 413 | ASN C 421 1 | 9 |
| HELIX | 12 | 12 | PRO | C | 440 | CYS C 443 5 | 4 |
| HELIX | 13 | 13 | TRP | C | 444 | ASP C 461 1 | 18 |
| HELIX | 14 | 14 | SER | C | 471 | LYS C 491 1 | 21 |
| HELIX | 15 | 15 | THR | C | 511 | ALA C 525 1 | 15 |
| HELIX | 16 | 16 | VAL | D | 612 | ASN D 621 1 | 10 |

TABLE 4-continued

Stem Cell Factor Dimer

| HELIX | 17 | 17 | ILE | D | 645 | ASP | D | 661 | 1 | | | | | | | | 17 |
|---|---|---|---|---|---|---|---|---|---|---|---|---|---|---|---|---|---|
| HELIX | 18 | 18 | SER | D | 671 | ASN | D | 693 | 1 | | | | | | | | 23 |
| HELIX | 19 | 19 | THR | D | 711 | LYS | D | 727 | 1 | | | | | | | | 17 |
| SHEET | 1 | A | 2 | ILE | A | 28 | TYR | A | 32 | 0 | | | | | | | |
| SHEET | 2 | A | 2 | GLU | A | 106 | PHE | A | 110 | −1 | O | GLU | A | 106 | N | TYR | A | 32 |
| SHEET | 1 | B | 2 | ILE | B | 228 | LYS | B | 231 | 0 | | | | | | | |
| SHEET | 2 | B | 2 | PRO | B | 307 | PHE | B | 310 | −1 | O | ARG | B | 308 | N | LEU | B | 230 |
| SHEET | 1 | C | 2 | ILE | C | 428 | LYS | C | 431 | 0 | | | | | | | |
| SHEET | 2 | C | 2 | PRO | C | 507 | PHE | C | 510 | −1 | O | ARG | C | 508 | N | LEU | C | 430 |
| SHEET | 1 | D | 2 | ILE | D | 628 | LYS | D | 631 | 0 | | | | | | | |
| SHEET | 2 | D | 2 | PRO | D | 707 | PHE | D | 710 | −1 | N | ARG | D | 708 | O | LEU | D | 630 |
| SSBOND | 1 | CYS | A | 4 | CYS | A | 89 | | | | | | | | | | |
| SSBOND | 2 | CYS | A | 43 | CYS | A | 138 | | | | | | | | | | |
| SSBOND | 3 | CYS | B | 204 | CYS | B | 289 | | | | | | | | | | |
| SSBOND | 4 | CYS | B | 243 | CYS | B | 338 | | | | | | | | | | |
| SSBOND | 5 | CYS | C | 443 | CYS | C | 538 | | | | | | | | | | |
| LINK | | SM | SM B | 803 | | | | OD2 ASP B 337 | | | | | | | | | |
| CRYST1 | 36.154 | | 87.526 | | 79.434 | | 90.00 | | 97.76 | 90.00 P 1 21 1 | | | | | | 8 | |
| ORIGX1 | | 1.000000 | 0.000000 | 0.000000 | 0.00000 | | | | | | | | | | | | |
| ORIGX2 | | 0.000000 | 1.000000 | 0.000000 | 0.00000 | | | | | | | | | | | | |
| ORIGX3 | | 0.000000 | 0.000000 | 1.000000 | 0.00000 | | | | | | | | | | | | |
| SCALE1 | | 0.027659 | 0.000000 | 0.003769 | 0.00000 | | | | | | | | | | | | |
| SCALE2 | | 0.000000 | 0.011425 | 0.000000 | 0.00000 | | | | | | | | | | | | |
| SCALE3 | | 0.000000 | 0.000000 | 0.012705 | 0.00000 | | | | | | | | | | | | |
| ATOM | 1 | N | CYS | A | 4 | 24.179 | 55.019 | 52.849 | 1.00 | 86.63 | N |
| ATOM | 2 | CA | CYS | A | 4 | 23.377 | 56.276 | 52.833 | 1.00 | 86.89 | C |
| ATOM | 3 | C | CYS | A | 4 | 21.900 | 55.949 | 52.656 | 1.00 | 88.25 | C |
| ATOM | 4 | O | CYS | A | 4 | 21.366 | 56.071 | 51.554 | 1.00 | 88.58 | O |
| ATOM | 5 | CB | CYS | A | 4 | 23.837 | 57.181 | 51.687 | 1.00 | 84.65 | C |
| ATOM | 6 | SG | CYS | A | 4 | 25.616 | 57.570 | 51.706 | 1.00 | 80.96 | S |
| ATOM | 7 | N | ARG | A | 5 | 21.259 | 55.533 | 53.748 | 1.00 | 89.34 | N |
| ATOM | 8 | CA | ARG | A | 5 | 19.840 | 55.170 | 53.770 | 1.00 | 90.15 | C |
| ATOM | 9 | C | ARG | A | 5 | 19.129 | 55.410 | 52.443 | 1.00 | 90.43 | C |
| ATOM | 10 | O | ARG | A | 5 | 18.685 | 54.466 | 51.786 | 1.00 | 90.05 | O |
| ATOM | 11 | CB | ARG | A | 5 | 19.131 | 55.932 | 54.884 | 1.00 | 90.62 | C |
| ATOM | 12 | N | ASN | A | 6 | 19.019 | 56.678 | 52.059 | 1.00 | 90.83 | N |
| ATOM | 13 | CA | ASN | A | 6 | 18.372 | 57.045 | 50.806 | 1.00 | 91.40 | C |
| ATOM | 14 | C | ASN | A | 6 | 19.348 | 56.829 | 49.647 | 1.00 | 91.43 | C |
| ATOM | 15 | O | ASN | A | 6 | 20.345 | 57.544 | 49.516 | 1.00 | 90.94 | O |
| ATOM | 16 | CB | ASN | A | 6 | 17.927 | 58.509 | 50.851 | 1.00 | 91.94 | C |
| ATOM | 17 | CG | ASN | A | 6 | 16.999 | 58.870 | 49.709 | 1.00 | 92.27 | C |
| ATOM | 18 | OD1 | ASN | A | 6 | 17.376 | 58.797 | 48.541 | 1.00 | 92.40 | O |
| ATOM | 19 | ND2 | ASN | A | 6 | 15.773 | 59.259 | 50.043 | 1.00 | 92.61 | N |
| ATOM | 20 | N | ARG | A | 7 | 19.051 | 55.832 | 48.815 | 1.00 | 91.42 | N |
| ATOM | 21 | CA | ARG | A | 7 | 19.894 | 55.494 | 47.672 | 1.00 | 90.97 | C |
| ATOM | 22 | C | ARG | A | 7 | 19.230 | 55.836 | 46.340 | 1.00 | 90.59 | C |
| ATOM | 23 | O | ARG | A | 7 | 19.817 | 55.635 | 45.278 | 1.00 | 91.32 | O |
| ATOM | 24 | CB | ARG | A | 7 | 20.247 | 54.006 | 47.712 | 1.00 | 91.02 | C |
| ATOM | 25 | N | VAL | A | 8 | 18.005 | 56.349 | 46.401 | 1.00 | 89.85 | N |
| ATOM | 26 | CA | VAL | A | 8 | 17.257 | 56.729 | 45.203 | 1.00 | 88.72 | C |
| ATOM | 27 | C | VAL | A | 8 | 16.890 | 55.511 | 44.345 | 1.00 | 87.92 | C |
| ATOM | 28 | O | VAL | A | 8 | 16.539 | 55.648 | 43.170 | 1.00 | 87.06 | O |
| ATOM | 29 | CB | VAL | A | 8 | 18.062 | 57.740 | 44.338 | 1.00 | 88.56 | C |
| ATOM | 30 | CG1 | VAL | A | 8 | 17.170 | 58.340 | 43.261 | 1.00 | 88.77 | C |
| ATOM | 31 | CG2 | VAL | A | 8 | 18.636 | 58.840 | 45.219 | 1.00 | 88.36 | C |
| ATOM | 32 | N | THR | A | 9 | 16.964 | 54.325 | 44.944 | 1.00 | 86.61 | N |
| ATOM | 33 | CA | THR | A | 9 | 16.635 | 53.081 | 44.249 | 1.00 | 85.51 | C |
| ATOM | 34 | C | THR | A | 9 | 17.126 | 53.090 | 42.802 | 1.00 | 84.43 | C |
| ATOM | 35 | O | THR | A | 9 | 16.415 | 53.524 | 41.895 | 1.00 | 84.69 | O |
| ATOM | 36 | CB | THR | A | 9 | 15.108 | 52.823 | 44.248 | 1.00 | 85.48 | C |
| ATOM | 37 | OG1 | THR | A | 9 | 14.629 | 52.757 | 45.598 | 1.00 | 85.34 | O |
| ATOM | 38 | CG2 | THR | A | 9 | 14.788 | 51.510 | 43.546 | 1.00 | 85.22 | C |
| ATOM | 39 | N | ASN | A | 10 | 18.345 | 52.605 | 42.596 | 1.00 | 83.25 | N |
| ATOM | 40 | CA | ASN | A | 10 | 18.935 | 52.552 | 41.265 | 1.00 | 81.58 | C |
| ATOM | 41 | C | ASN | A | 10 | 18.944 | 51.119 | 40.754 | 1.00 | 80.41 | C |
| ATOM | 42 | O | ASN | A | 10 | 19.903 | 50.696 | 40.108 | 1.00 | 80.59 | O |
| ATOM | 43 | CB | ASN | A | 10 | 20.356 | 53.091 | 41.308 | 1.00 | 81.52 | C |
| ATOM | 44 | N | ASN | A | 11 | 17.878 | 50.377 | 41.047 | 1.00 | 78.05 | N |
| ATOM | 45 | CA | ASN | A | 11 | 17.777 | 48.985 | 40.622 | 1.00 | 75.63 | C |
| ATOM | 46 | C | ASN | A | 11 | 18.070 | 48.776 | 39.142 | 1.00 | 73.02 | C |
| ATOM | 47 | O | ASN | A | 11 | 17.862 | 49.669 | 38.317 | 1.00 | 71.57 | O |
| ATOM | 48 | CB | ASN | A | 11 | 16.397 | 48.417 | 40.958 | 1.00 | 77.49 | C |
| ATOM | 49 | CG | ASN | A | 11 | 16.269 | 48.032 | 42.418 | 1.00 | 78.14 | C |
| ATOM | 50 | OD1 | ASN | A | 11 | 17.084 | 47.269 | 42.944 | 1.00 | 78.66 | O |
| ATOM | 51 | ND2 | ASN | A | 11 | 15.240 | 48.552 | 43.080 | 1.00 | 78.86 | N |
| ATOM | 52 | N | VAL | A | 12 | 18.549 | 47.576 | 38.823 | 1.00 | 70.35 | N |
| ATOM | 53 | CA | VAL | A | 12 | 18.911 | 47.209 | 37.460 | 1.00 | 66.91 | C |

TABLE 4-continued

Stem Cell Factor Dimer

| ATOM | 54 | C | VAL | A | 12 | 17.720 | 47.300 | 36.511 | 1.00 | 63.29 | C |
|---|---|---|---|---|---|---|---|---|---|---|---|
| ATOM | 55 | O | VAL | A | 12 | 17.827 | 46.969 | 35.334 | 1.00 | 63.69 | O |
| ATOM | 56 | CB | VAL | A | 12 | 19.492 | 45.777 | 37.411 | 1.00 | 67.69 | C |
| ATOM | 57 | CG1 | VAL | A | 12 | 20.358 | 45.608 | 36.170 | 1.00 | 68.11 | C |
| ATOM | 58 | CG2 | VAL | A | 12 | 20.306 | 45.503 | 38.665 | 1.00 | 68.37 | C |
| ATOM | 59 | N | LYS | A | 13 | 16.584 | 47.747 | 37.030 | 1.00 | 58.49 | N |
| ATOM | 60 | CA | LYS | A | 13 | 15.386 | 47.899 | 36.220 | 1.00 | 55.37 | C |
| ATOM | 61 | C | LYS | A | 13 | 15.729 | 48.723 | 34.978 | 1.00 | 52.98 | C |
| ATOM | 62 | O | LYS | A | 13 | 15.588 | 48.259 | 33.843 | 1.00 | 52.47 | O |
| ATOM | 63 | CB | LYS | A | 13 | 14.299 | 48.609 | 37.036 | 1.00 | 56.53 | C |
| ATOM | 64 | CG | LYS | A | 13 | 14.811 | 49.848 | 37.769 | 1.00 | 58.27 | C |
| ATOM | 65 | CD | LYS | A | 13 | 13.702 | 50.667 | 38.398 | 1.00 | 59.14 | C |
| ATOM | 66 | CE | LYS | A | 13 | 14.263 | 51.947 | 39.006 | 1.00 | 60.60 | C |
| ATOM | 67 | NZ | LYS | A | 13 | 13.191 | 52.883 | 39.456 | 1.00 | 60.73 | N |
| ATOM | 68 | N | ASP | A | 14 | 16.192 | 49.949 | 35.205 | 1.00 | 49.63 | N |
| ATOM | 69 | CA | ASP | A | 14 | 16.558 | 50.841 | 34.117 | 1.00 | 46.02 | C |
| ATOM | 70 | C | ASP | A | 14 | 17.959 | 50.521 | 33.575 | 1.00 | 40.96 | C |
| ATOM | 71 | O | ASP | A | 14 | 18.231 | 50.731 | 32.394 | 1.00 | 38.69 | O |
| ATOM | 72 | CB | ASP | A | 14 | 16.477 | 52.294 | 34.591 | 1.00 | 50.58 | C |
| ATOM | 73 | CG | ASP | A | 14 | 17.233 | 52.528 | 35.886 | 1.00 | 56.43 | C |
| ATOM | 74 | OD1 | ASP | A | 14 | 16.804 | 52.008 | 36.943 | 1.00 | 59.62 | O |
| ATOM | 75 | OD2 | ASP | A | 14 | 18.263 | 53.233 | 35.845 | 1.00 | 59.80 | O |
| ATOM | 76 | N | VAL | A | 15 | 18.832 | 50.004 | 34.437 | 1.00 | 34.36 | N |
| ATOM | 77 | CA | VAL | A | 15 | 20.187 | 49.638 | 34.033 | 1.00 | 32.14 | C |
| ATOM | 78 | C | VAL | A | 15 | 20.136 | 48.524 | 32.989 | 1.00 | 31.17 | C |
| ATOM | 79 | O | VAL | A | 15 | 20.816 | 48.581 | 31.961 | 1.00 | 29.80 | O |
| ATOM | 80 | CB | VAL | A | 15 | 21.036 | 49.157 | 35.241 | 1.00 | 29.72 | C |
| ATOM | 81 | CG1 | VAL | A | 15 | 22.346 | 48.563 | 34.753 | 1.00 | 30.51 | C |
| ATOM | 82 | CG2 | VAL | A | 15 | 21.316 | 50.312 | 36.176 | 1.00 | 24.91 | C |
| ATOM | 83 | N | THR | A | 16 | 19.312 | 47.518 | 33.259 | 1.00 | 31.37 | N |
| ATOM | 84 | CA | THR | A | 16 | 19.137 | 46.390 | 32.355 | 1.00 | 31.24 | C |
| ATOM | 85 | C | THR | A | 16 | 18.692 | 46.881 | 30.978 | 1.00 | 31.26 | C |
| ATOM | 86 | O | THR | A | 16 | 19.159 | 46.389 | 29.952 | 1.00 | 32.04 | O |
| ATOM | 87 | CB | THR | A | 16 | 18.091 | 45.408 | 32.919 | 1.00 | 33.12 | C |
| ATOM | 88 | OG1 | THR | A | 16 | 18.636 | 44.757 | 34.072 | 1.00 | 30.67 | O |
| ATOM | 89 | CG2 | THR | A | 16 | 17.705 | 44.364 | 31.875 | 1.00 | 33.49 | C |
| ATOM | 90 | N | LYS | A | 17 | 17.791 | 47.857 | 30.963 | 1.00 | 31.79 | N |
| ATOM | 91 | CA | LYS | A | 17 | 17.316 | 48.419 | 29.711 | 1.00 | 33.62 | C |
| ATOM | 92 | C | LYS | A | 17 | 18.479 | 49.133 | 29.017 | 1.00 | 32.83 | C |
| ATOM | 93 | O | LYS | A | 17 | 18.739 | 48.904 | 27.832 | 1.00 | 33.50 | O |
| ATOM | 94 | CB | LYS | A | 17 | 16.173 | 49.406 | 29.967 | 1.00 | 38.18 | C |
| ATOM | 95 | CG | LYS | A | 17 | 15.430 | 49.840 | 28.698 | 1.00 | 41.80 | C |
| ATOM | 96 | CD | LYS | A | 17 | 14.288 | 50.804 | 29.014 | 1.00 | 43.51 | C |
| ATOM | 97 | CE | LYS | A | 17 | 13.416 | 51.080 | 27.783 | 1.00 | 46.10 | C |
| ATOM | 98 | NZ | LYS | A | 17 | 14.145 | 51.735 | 26.648 | 1.00 | 45.83 | N |
| ATOM | 99 | N | LEU | A | 18 | 19.192 | 49.976 | 29.763 | 1.00 | 30.88 | N |
| ATOM | 100 | CA | LEU | A | 18 | 20.333 | 50.716 | 29.205 | 1.00 | 28.79 | C |
| ATOM | 101 | C | LEU | A | 18 | 21.328 | 49.767 | 28.545 | 1.00 | 25.72 | C |
| ATOM | 102 | O | LEU | A | 18 | 21.734 | 49.973 | 27.408 | 1.00 | 23.33 | O |
| ATOM | 103 | CB | LEU | A | 18 | 21.060 | 51.494 | 30.298 | 1.00 | 27.65 | C |
| ATOM | 104 | CG | LEU | A | 18 | 21.681 | 52.831 | 29.903 | 1.00 | 28.11 | C |
| ATOM | 105 | CD1 | LEU | A | 18 | 22.621 | 53.255 | 31.012 | 1.00 | 27.08 | C |
| ATOM | 106 | CD2 | LEU | A | 18 | 22.398 | 52.747 | 28.579 | 1.00 | 23.78 | C |
| ATOM | 107 | N | VAL | A | 19 | 21.722 | 48.731 | 29.278 | 1.00 | 26.84 | N |
| ATOM | 108 | CA | VAL | A | 19 | 22.661 | 47.740 | 28.765 | 1.00 | 25.57 | C |
| ATOM | 109 | C | VAL | A | 19 | 22.113 | 47.044 | 27.513 | 1.00 | 27.11 | C |
| ATOM | 110 | O | VAL | A | 19 | 22.869 | 46.674 | 26.612 | 1.00 | 27.07 | O |
| ATOM | 111 | CB | VAL | A | 19 | 22.987 | 46.691 | 29.855 | 1.00 | 26.55 | C |
| ATOM | 112 | CG1 | VAL | A | 19 | 23.796 | 45.507 | 29.265 | 1.00 | 22.88 | C |
| ATOM | 113 | CG2 | VAL | A | 19 | 23.775 | 47.355 | 30.960 | 1.00 | 23.60 | C |
| ATOM | 114 | N | ALA | A | 20 | 20.798 | 46.880 | 27.443 | 1.00 | 27.84 | N |
| ATOM | 115 | CA | ALA | A | 20 | 20.195 | 46.227 | 26.287 | 1.00 | 29.20 | C |
| ATOM | 116 | C | ALA | A | 20 | 20.309 | 47.120 | 25.050 | 1.00 | 30.00 | C |
| ATOM | 117 | O | ALA | A | 20 | 20.302 | 46.636 | 23.914 | 1.00 | 30.00 | O |
| ATOM | 118 | CB | ALA | A | 20 | 18.725 | 45.906 | 26.577 | 1.00 | 29.27 | C |
| ATOM | 119 | N | ASN | A | 21 | 20.436 | 48.424 | 25.276 | 1.00 | 28.74 | N |
| ATOM | 120 | CA | ASN | A | 21 | 20.527 | 49.375 | 24.179 | 1.00 | 28.64 | C |
| ATOM | 121 | C | ASN | A | 21 | 21.868 | 50.041 | 23.929 | 1.00 | 27.97 | C |
| ATOM | 122 | O | ASN | A | 21 | 21.957 | 50.999 | 23.159 | 1.00 | 30.28 | O |
| ATOM | 123 | CB | ASN | A | 21 | 19.433 | 50.424 | 24.331 | 1.00 | 30.91 | C |
| ATOM | 124 | CG | ASN | A | 21 | 18.088 | 49.889 | 23.918 | 1.00 | 34.80 | C |
| ATOM | 125 | OD1 | ASN | A | 21 | 17.787 | 49.800 | 22.721 | 1.00 | 34.75 | O |
| ATOM | 126 | ND2 | ASN | A | 21 | 17.278 | 49.487 | 24.900 | 1.00 | 35.75 | N |
| ATOM | 127 | N | LEU | A | 22 | 22.910 | 49.541 | 24.579 | 1.00 | 26.09 | N |
| ATOM | 128 | CA | LEU | A | 22 | 24.259 | 50.055 | 24.359 | 1.00 | 24.16 | C |
| ATOM | 129 | C | LEU | A | 22 | 24.997 | 48.954 | 23.614 | 1.00 | 23.68 | C |
| ATOM | 130 | O | LEU | A | 22 | 24.936 | 47.802 | 24.002 | 1.00 | 25.86 | O |

TABLE 4-continued

Stem Cell Factor Dimer

| ATOM | 131 | CB | LEU | A | 22 | 24.970 | 50.339 | 25.677 | 1.00 | 21.67 | C |
|---|---|---|---|---|---|---|---|---|---|---|---|
| ATOM | 132 | CG | LEU | A | 22 | 24.581 | 51.606 | 26.436 | 1.00 | 23.31 | C |
| ATOM | 133 | CD1 | LEU | A | 22 | 25.367 | 51.654 | 27.735 | 1.00 | 22.70 | C |
| ATOM | 134 | CD2 | LEU | A | 22 | 24.863 | 52.849 | 25.576 | 1.00 | 22.30 | C |
| ATOM | 135 | N | PRO | A | 23 | 25.699 | 49.293 | 22.530 | 1.00 | 25.53 | N |
| ATOM | 136 | CA | PRO | A | 23 | 26.411 | 48.232 | 21.803 | 1.00 | 26.11 | C |
| ATOM | 137 | C | PRO | A | 23 | 27.359 | 47.413 | 22.679 | 1.00 | 27.55 | C |
| ATOM | 138 | O | PRO | A | 23 | 28.058 | 47.961 | 23.541 | 1.00 | 24.70 | O |
| ATOM | 139 | CB | PRO | A | 23 | 27.123 | 48.985 | 20.674 | 1.00 | 24.80 | C |
| ATOM | 140 | CG | PRO | A | 23 | 27.176 | 50.440 | 21.169 | 1.00 | 27.41 | C |
| ATOM | 141 | CD | PRO | A | 23 | 25.897 | 50.620 | 21.917 | 1.00 | 24.42 | C |
| ATOM | 142 | N | LYS | A | 24 | 27.371 | 46.099 | 22.458 | 1.00 | 27.34 | N |
| ATOM | 143 | CA | LYS | A | 24 | 28.220 | 45.195 | 23.242 | 1.00 | 30.02 | C |
| ATOM | 144 | C | LYS | A | 24 | 29.719 | 45.471 | 23.142 | 1.00 | 30.51 | C |
| ATOM | 145 | O | LYS | A | 24 | 30.450 | 45.308 | 24.121 | 1.00 | 30.43 | O |
| ATOM | 146 | CB | LYS | A | 24 | 27.961 | 43.742 | 22.840 | 1.00 | 30.74 | C |
| ATOM | 147 | CG | LYS | A | 24 | 26.542 | 43.262 | 23.107 | 1.00 | 34.37 | C |
| ATOM | 148 | CD | LYS | A | 24 | 26.346 | 41.840 | 22.584 | 1.00 | 41.43 | C |
| ATOM | 149 | CE | LYS | A | 24 | 24.910 | 41.362 | 22.785 | 1.00 | 43.00 | C |
| ATOM | 150 | NZ | LYS | A | 24 | 24.527 | 41.438 | 24.225 | 1.00 | 47.05 | N |
| ATOM | 151 | N | ASP | A | 25 | 30.173 | 45.879 | 21.960 | 1.00 | 30.41 | N |
| ATOM | 152 | CA | ASP | A | 25 | 31.587 | 46.155 | 21.734 | 1.00 | 31.71 | C |
| ATOM | 153 | C | ASP | A | 25 | 31.951 | 47.631 | 21.953 | 1.00 | 33.42 | C |
| ATOM | 154 | O | ASP | A | 25 | 33.007 | 48.091 | 21.522 | 1.00 | 33.11 | O |
| ATOM | 155 | CB | ASP | A | 25 | 31.977 | 45.711 | 20.313 | 1.00 | 31.70 | C |
| ATOM | 156 | CG | ASP | A | 25 | 31.118 | 46.358 | 19.237 | 1.00 | 35.19 | C |
| ATOM | 157 | OD1 | ASP | A | 25 | 30.109 | 47.007 | 19.581 | 1.00 | 36.20 | O |
| ATOM | 158 | OD2 | ASP | A | 25 | 31.446 | 46.211 | 18.041 | 1.00 | 37.53 | O |
| ATOM | 159 | N | TYR | A | 26 | 31.075 | 48.372 | 22.622 | 1.00 | 33.64 | N |
| ATOM | 160 | CA | TYR | A | 26 | 31.342 | 49.782 | 22.895 | 1.00 | 34.35 | C |
| ATOM | 161 | C | TYR | A | 26 | 32.009 | 49.905 | 24.262 | 1.00 | 34.80 | C |
| ATOM | 162 | O | TYR | A | 26 | 31.402 | 49.628 | 25.297 | 1.00 | 35.59 | O |
| ATOM | 163 | CB | TYR | A | 26 | 30.045 | 50.588 | 22.879 | 1.00 | 33.06 | C |
| ATOM | 164 | CG | TYR | A | 26 | 30.249 | 52.049 | 23.176 | 1.00 | 34.30 | C |
| ATOM | 165 | CD1 | TYR | A | 26 | 31.007 | 52.855 | 22.327 | 1.00 | 35.11 | C |
| ATOM | 166 | CD2 | TYR | A | 26 | 29.677 | 52.631 | 24.306 | 1.00 | 33.42 | C |
| ATOM | 167 | CE1 | TYR | A | 26 | 31.188 | 54.208 | 22.597 | 1.00 | 36.03 | C |
| ATOM | 168 | CE2 | TYR | A | 26 | 29.847 | 53.974 | 24.585 | 1.00 | 35.98 | C |
| ATOM | 169 | CZ | TYR | A | 26 | 30.602 | 54.761 | 23.729 | 1.00 | 37.37 | C |
| ATOM | 170 | OH | TYR | A | 26 | 30.745 | 56.101 | 24.003 | 1.00 | 38.88 | O |
| ATOM | 171 | N | MET | A | 27 | 33.263 | 50.334 | 24.258 | 1.00 | 35.01 | N |
| ATOM | 172 | CA | MET | A | 27 | 34.022 | 50.467 | 25.483 | 1.00 | 35.27 | C |
| ATOM | 173 | C | MET | A | 27 | 33.797 | 51.783 | 26.227 | 1.00 | 33.91 | C |
| ATOM | 174 | O | MET | A | 27 | 33.930 | 52.866 | 25.661 | 1.00 | 35.37 | O |
| ATOM | 175 | CB | MET | A | 27 | 35.509 | 50.295 | 25.173 | 1.00 | 38.11 | C |
| ATOM | 176 | CG | MET | A | 27 | 35.827 | 48.994 | 24.473 | 1.00 | 40.65 | C |
| ATOM | 177 | SD | MET | A | 27 | 35.230 | 47.613 | 25.440 | 1.00 | 45.39 | S |
| ATOM | 178 | CE | MET | A | 27 | 36.529 | 47.464 | 26.649 | 1.00 | 44.54 | C |
| ATOM | 179 | N | ILE | A | 28 | 33.452 | 51.666 | 27.504 | 1.00 | 32.21 | N |
| ATOM | 180 | CA | ILE | A | 28 | 33.235 | 52.812 | 28.377 | 1.00 | 29.60 | C |
| ATOM | 181 | C | ILE | A | 28 | 34.472 | 52.920 | 29.264 | 1.00 | 28.54 | C |
| ATOM | 182 | O | ILE | A | 28 | 34.956 | 51.908 | 29.776 | 1.00 | 26.71 | O |
| ATOM | 183 | CB | ILE | A | 28 | 32.008 | 52.611 | 29.299 | 1.00 | 27.09 | C |
| ATOM | 184 | CG1 | ILE | A | 28 | 30.735 | 52.462 | 28.467 | 1.00 | 22.92 | C |
| ATOM | 185 | CG2 | ILE | A | 28 | 31.883 | 53.801 | 30.253 | 1.00 | 28.05 | C |
| ATOM | 186 | CD1 | ILE | A | 28 | 29.551 | 51.907 | 29.255 | 1.00 | 19.41 | C |
| ATOM | 187 | N | THR | A | 29 | 34.986 | 54.134 | 29.439 | 1.00 | 27.86 | N |
| ATOM | 188 | CA | THR | A | 29 | 36.168 | 54.339 | 30.274 | 1.00 | 30.19 | C |
| ATOM | 189 | C | THR | A | 29 | 35.818 | 54.633 | 31.728 | 1.00 | 27.73 | C |
| ATOM | 190 | O | THR | A | 29 | 34.914 | 55.412 | 32.022 | 1.00 | 26.96 | O |
| ATOM | 191 | CB | THR | A | 29 | 37.053 | 55.491 | 29.736 | 1.00 | 32.36 | C |
| ATOM | 192 | OG1 | THR | A | 29 | 37.714 | 55.061 | 28.537 | 1.00 | 37.55 | O |
| ATOM | 193 | CG2 | THR | A | 29 | 38.107 | 55.892 | 30.769 | 1.00 | 32.81 | C |
| ATOM | 194 | N | LEU | A | 30 | 36.548 | 53.998 | 32.635 | 1.00 | 26.14 | N |
| ATOM | 195 | CA | LEU | A | 30 | 36.332 | 54.181 | 34.061 | 1.00 | 27.37 | C |
| ATOM | 196 | C | LEU | A | 30 | 37.639 | 54.031 | 34.835 | 1.00 | 28.61 | C |
| ATOM | 197 | O | LEU | A | 30 | 38.371 | 53.054 | 34.666 | 1.00 | 27.18 | O |
| ATOM | 198 | CB | LEU | A | 30 | 35.320 | 53.153 | 34.584 | 1.00 | 24.35 | C |
| ATOM | 199 | CG | LEU | A | 30 | 35.225 | 53.000 | 36.107 | 1.00 | 24.14 | C |
| ATOM | 200 | CD1 | LEU | A | 30 | 34.569 | 54.255 | 36.734 | 1.00 | 22.13 | C |
| ATOM | 201 | CD2 | LEU | A | 30 | 34.428 | 51.746 | 36.437 | 1.00 | 21.25 | C |
| ATOM | 202 | N | LYS | A | 31 | 37.934 | 55.015 | 35.677 | 1.00 | 30.12 | N |
| ATOM | 203 | CA | LYS | A | 31 | 39.126 | 54.949 | 36.504 | 1.00 | 31.06 | C |
| ATOM | 204 | C | LYS | A | 31 | 38.734 | 54.049 | 37.662 | 1.00 | 31.36 | C |
| ATOM | 205 | O | LYS | A | 31 | 38.219 | 54.489 | 38.688 | 1.00 | 30.60 | O |
| ATOM | 206 | CB | LYS | A | 31 | 39.527 | 56.351 | 36.968 | 1.00 | 30.41 | C |
| ATOM | 207 | CG | LYS | A | 31 | 40.114 | 57.159 | 35.829 | 1.00 | 32.85 | C |

TABLE 4-continued

Stem Cell Factor Dimer

| ATOM | 208 | CD | LYS | A | 31 | 40.245 | 58.636 | 36.136 | 1.00 | 37.32 | C |
|---|---|---|---|---|---|---|---|---|---|---|---|
| ATOM | 209 | CE | LYS | A | 31 | 40.798 | 59.359 | 34.910 | 1.00 | 41.56 | C |
| ATOM | 210 | NZ | LYS | A | 31 | 40.802 | 60.837 | 35.049 | 1.00 | 48.16 | N |
| ATOM | 211 | N | TYR | A | 32 | 38.951 | 52.760 | 37.441 | 1.00 | 33.38 | N |
| ATOM | 212 | CA | TYR | A | 32 | 38.637 | 51.702 | 38.391 | 1.00 | 33.81 | C |
| ATOM | 213 | C | TYR | A | 32 | 39.514 | 51.758 | 39.638 | 1.00 | 34.38 | C |
| ATOM | 214 | O | TYR | A | 32 | 40.725 | 51.937 | 39.538 | 1.00 | 35.35 | O |
| ATOM | 215 | CB | TYR | A | 32 | 38.839 | 50.357 | 37.689 | 1.00 | 36.33 | C |
| ATOM | 216 | CG | TYR | A | 32 | 38.578 | 49.136 | 38.534 | 1.00 | 36.76 | C |
| ATOM | 217 | CD1 | TYR | A | 32 | 37.278 | 48.761 | 38.858 | 1.00 | 36.76 | C |
| ATOM | 218 | CD2 | TYR | A | 32 | 39.629 | 48.337 | 38.983 | 1.00 | 37.06 | C |
| ATOM | 219 | CE1 | TYR | A | 32 | 37.021 | 47.620 | 39.606 | 1.00 | 39.37 | C |
| ATOM | 220 | CE2 | TYR | A | 32 | 39.386 | 47.182 | 39.740 | 1.00 | 37.96 | C |
| ATOM | 221 | CZ | TYR | A | 32 | 38.075 | 46.833 | 40.046 | 1.00 | 39.51 | C |
| ATOM | 222 | OH | TYR | A | 32 | 37.804 | 45.715 | 40.798 | 1.00 | 39.29 | O |
| ATOM | 223 | N | VAL | A | 33 | 38.908 | 51.617 | 40.813 | 1.00 | 34.07 | N |
| ATOM | 224 | CA | VAL | A | 33 | 39.692 | 51.607 | 42.037 | 1.00 | 36.48 | C |
| ATOM | 225 | C | VAL | A | 33 | 40.079 | 50.159 | 42.291 | 1.00 | 39.60 | C |
| ATOM | 226 | O | VAL | A | 33 | 39.234 | 49.324 | 42.609 | 1.00 | 39.23 | O |
| ATOM | 227 | CB | VAL | A | 33 | 38.909 | 52.124 | 43.259 | 1.00 | 35.71 | C |
| ATOM | 228 | CG1 | VAL | A | 33 | 39.733 | 51.913 | 44.518 | 1.00 | 35.41 | C |
| ATOM | 229 | CG2 | VAL | A | 33 | 38.597 | 53.611 | 43.095 | 1.00 | 36.35 | C |
| ATOM | 230 | N | PRO | A | 34 | 41.367 | 49.837 | 42.130 | 1.00 | 42.06 | N |
| ATOM | 231 | CA | PRO | A | 34 | 41.817 | 48.463 | 42.357 | 1.00 | 43.30 | C |
| ATOM | 232 | C | PRO | A | 34 | 41.602 | 48.070 | 43.815 | 1.00 | 44.25 | C |
| ATOM | 233 | O | PRO | A | 34 | 41.793 | 48.885 | 44.719 | 1.00 | 45.62 | O |
| ATOM | 234 | CB | PRO | A | 34 | 43.290 | 48.515 | 41.953 | 1.00 | 44.82 | C |
| ATOM | 235 | CG | PRO | A | 34 | 43.685 | 49.927 | 42.293 | 1.00 | 46.23 | C |
| ATOM | 236 | CD | PRO | A | 34 | 42.498 | 50.730 | 41.812 | 1.00 | 43.18 | C |
| ATOM | 237 | N | GLY | A | 35 | 41.186 | 46.828 | 44.037 | 1.00 | 44.70 | N |
| ATOM | 238 | CA | GLY | A | 35 | 40.941 | 46.361 | 45.390 | 1.00 | 44.83 | C |
| ATOM | 239 | C | GLY | A | 35 | 39.453 | 46.290 | 45.676 | 1.00 | 45.03 | C |
| ATOM | 240 | O | GLY | A | 35 | 39.026 | 45.681 | 46.656 | 1.00 | 44.02 | O |
| ATOM | 241 | N | MET | A | 36 | 38.666 | 46.909 | 44.798 | 1.00 | 46.50 | N |
| ATOM | 242 | CA | MET | A | 36 | 37.212 | 46.942 | 44.929 | 1.00 | 47.66 | C |
| ATOM | 243 | C | MET | A | 36 | 36.600 | 45.553 | 45.023 | 1.00 | 48.06 | C |
| ATOM | 244 | O | MET | A | 36 | 35.488 | 45.393 | 45.521 | 1.00 | 47.40 | O |
| ATOM | 245 | CB | MET | A | 36 | 36.587 | 47.657 | 43.731 | 1.00 | 47.93 | C |
| ATOM | 246 | CG | MET | A | 36 | 35.075 | 47.720 | 43.805 | 1.00 | 50.30 | C |
| ATOM | 247 | SD | MET | A | 36 | 34.244 | 48.051 | 42.237 | 1.00 | 51.54 | S |
| ATOM | 248 | CE | MET | A | 36 | 32.603 | 47.354 | 42.593 | 1.00 | 48.10 | C |
| ATOM | 249 | N | ASP | A | 37 | 37.326 | 44.553 | 44.535 | 1.00 | 49.01 | N |
| ATOM | 250 | CA | ASP | A | 37 | 36.843 | 43.177 | 44.534 | 1.00 | 50.28 | C |
| ATOM | 251 | C | ASP | A | 37 | 37.333 | 42.330 | 45.705 | 1.00 | 50.50 | C |
| ATOM | 252 | O | ASP | A | 37 | 37.091 | 41.123 | 45.737 | 1.00 | 51.60 | O |
| ATOM | 253 | CB | ASP | A | 37 | 37.235 | 42.506 | 43.215 | 1.00 | 51.52 | C |
| ATOM | 254 | CG | ASP | A | 37 | 38.739 | 42.529 | 42.968 | 1.00 | 53.79 | C |
| ATOM | 255 | OD1 | ASP | A | 37 | 39.378 | 43.583 | 43.202 | 1.00 | 53.58 | O |
| ATOM | 256 | OD2 | ASP | A | 37 | 39.283 | 41.492 | 42.524 | 1.00 | 54.54 | O |
| ATOM | 257 | N | VAL | A | 38 | 38.010 | 42.957 | 46.666 | 1.00 | 49.28 | N |
| ATOM | 258 | CA | VAL | A | 38 | 38.536 | 42.236 | 47.825 | 1.00 | 47.15 | C |
| ATOM | 259 | C | VAL | A | 38 | 38.533 | 43.060 | 49.106 | 1.00 | 46.60 | C |
| ATOM | 260 | O | VAL | A | 38 | 38.300 | 42.534 | 50.194 | 1.00 | 44.87 | O |
| ATOM | 261 | CB | VAL | A | 38 | 39.980 | 41.772 | 47.576 | 1.00 | 45.99 | C |
| ATOM | 262 | CG1 | VAL | A | 38 | 39.992 | 40.604 | 46.617 | 1.00 | 47.70 | C |
| ATOM | 263 | CG2 | VAL | A | 38 | 40.797 | 42.923 | 47.016 | 1.00 | 45.04 | C |
| ATOM | 264 | N | LEU | A | 39 | 38.811 | 44.350 | 48.977 | 1.00 | 45.27 | N |
| ATOM | 265 | CA | LEU | A | 39 | 38.844 | 45.226 | 50.136 | 1.00 | 45.37 | C |
| ATOM | 266 | C | LEU | A | 39 | 37.446 | 45.557 | 50.649 | 1.00 | 45.34 | C |
| ATOM | 267 | O | LEU | A | 39 | 36.455 | 45.427 | 49.928 | 1.00 | 43.74 | O |
| ATOM | 268 | CB | LEU | A | 39 | 39.559 | 46.532 | 49.786 | 1.00 | 45.66 | C |
| ATOM | 269 | CG | LEU | A | 39 | 41.085 | 46.576 | 49.709 | 1.00 | 47.47 | C |
| ATOM | 270 | CD1 | LEU | A | 39 | 41.610 | 45.445 | 48.841 | 1.00 | 49.34 | C |
| ATOM | 271 | CD2 | LEU | A | 39 | 41.513 | 47.931 | 49.150 | 1.00 | 45.50 | C |
| ATOM | 272 | N | PRO | A | 40 | 37.348 | 45.973 | 51.921 | 1.00 | 45.95 | N |
| ATOM | 273 | CA | PRO | A | 40 | 36.039 | 46.324 | 52.471 | 1.00 | 45.59 | C |
| ATOM | 274 | C | PRO | A | 40 | 35.600 | 47.603 | 51.763 | 1.00 | 44.61 | C |
| ATOM | 275 | O | PRO | A | 40 | 36.436 | 48.364 | 51.274 | 1.00 | 42.94 | O |
| ATOM | 276 | CB | PRO | A | 40 | 36.331 | 46.528 | 53.954 | 1.00 | 47.00 | C |
| ATOM | 277 | CG | PRO | A | 40 | 37.764 | 46.999 | 53.946 | 1.00 | 48.81 | C |
| ATOM | 278 | CD | PRO | A | 40 | 38.395 | 46.070 | 52.951 | 1.00 | 45.63 | C |
| ATOM | 279 | N | SER | A | 41 | 34.294 | 47.831 | 51.708 | 1.00 | 44.09 | N |
| ATOM | 280 | CA | SER | A | 41 | 33.745 | 48.988 | 51.019 | 1.00 | 44.85 | C |
| ATOM | 281 | C | SER | A | 41 | 34.251 | 50.349 | 51.471 | 1.00 | 44.18 | C |
| ATOM | 282 | O | SER | A | 41 | 34.469 | 51.233 | 50.637 | 1.00 | 44.01 | O |
| ATOM | 283 | CB | SER | A | 41 | 32.221 | 48.971 | 51.109 | 1.00 | 46.19 | C |
| ATOM | 284 | OG | SER | A | 41 | 31.801 | 49.153 | 52.447 | 1.00 | 50.69 | O |

TABLE 4-continued

Stem Cell Factor Dimer

| ATOM | 285 | N | HIS | A | 42 | 34.450 | 50.528 | 52.774 | 1.00 | 43.90 | N |
| ATOM | 286 | CA | HIS | A | 42 | 34.907 | 51.824 | 53.275 | 1.00 | 43.39 | C |
| ATOM | 287 | C | HIS | A | 42 | 36.261 | 52.205 | 52.717 | 1.00 | 41.97 | C |
| ATOM | 288 | O | HIS | A | 42 | 36.696 | 53.344 | 52.870 | 1.00 | 41.77 | O |
| ATOM | 289 | CB | HIS | A | 42 | 34.969 | 51.846 | 54.809 | 1.00 | 45.03 | C |
| ATOM | 290 | CG | HIS | A | 42 | 36.162 | 51.148 | 55.383 | 1.00 | 46.34 | C |
| ATOM | 291 | ND1 | HIS | A | 42 | 36.161 | 49.806 | 55.699 | 1.00 | 47.87 | N |
| ATOM | 292 | CD2 | HIS | A | 42 | 37.399 | 51.607 | 55.689 | 1.00 | 47.30 | C |
| ATOM | 293 | CE1 | HIS | A | 42 | 37.346 | 49.468 | 56.176 | 1.00 | 48.29 | C |
| ATOM | 294 | NE2 | HIS | A | 42 | 38.116 | 50.542 | 56.180 | 1.00 | 48.92 | N |
| ATOM | 295 | N | CYS | A | 43 | 36.919 | 51.252 | 52.065 | 1.00 | 39.35 | N |
| ATOM | 296 | CA | CYS | A | 43 | 38.234 | 51.492 | 51.487 | 1.00 | 39.79 | C |
| ATOM | 297 | C | CYS | A | 43 | 38.171 | 51.960 | 50.045 | 1.00 | 37.47 | C |
| ATOM | 298 | O | CYS | A | 43 | 39.160 | 52.448 | 49.513 | 1.00 | 34.98 | O |
| ATOM | 299 | CB | CYS | A | 43 | 39.090 | 50.221 | 51.533 | 1.00 | 45.85 | C |
| ATOM | 300 | SG | CYS | A | 43 | 39.570 | 49.651 | 53.193 | 1.00 | 51.16 | S |
| ATOM | 301 | N | TRP | A | 44 | 37.016 | 51.823 | 49.404 | 1.00 | 34.72 | N |
| ATOM | 302 | CA | TRP | A | 44 | 36.931 | 52.221 | 48.006 | 1.00 | 32.06 | C |
| ATOM | 303 | C | TRP | A | 44 | 35.641 | 52.893 | 47.534 | 1.00 | 30.52 | C |
| ATOM | 304 | O | TRP | A | 44 | 35.642 | 53.590 | 46.521 | 1.00 | 27.80 | O |
| ATOM | 305 | CB | TRP | A | 44 | 37.188 | 50.994 | 47.127 | 1.00 | 31.65 | C |
| ATOM | 306 | CG | TRP | A | 44 | 36.299 | 49.824 | 47.460 | 1.00 | 29.05 | C |
| ATOM | 307 | CD1 | TRP | A | 44 | 36.620 | 48.743 | 48.226 | 1.00 | 32.56 | C |
| ATOM | 308 | CD2 | TRP | A | 44 | 34.948 | 49.624 | 47.030 | 1.00 | 27.71 | C |
| ATOM | 309 | NE1 | TRP | A | 44 | 35.552 | 47.874 | 48.298 | 1.00 | 32.12 | N |
| ATOM | 310 | CE2 | TRP | A | 44 | 34.513 | 48.392 | 47.572 | 1.00 | 28.95 | C |
| ATOM | 311 | CE3 | TRP | A | 44 | 34.061 | 50.366 | 46.237 | 1.00 | 29.91 | C |
| ATOM | 312 | CZ2 | TRP | A | 44 | 33.230 | 47.883 | 47.348 | 1.00 | 29.41 | C |
| ATOM | 313 | CZ3 | TRP | A | 44 | 32.781 | 49.863 | 46.010 | 1.00 | 30.10 | C |
| ATOM | 314 | CH2 | TRP | A | 44 | 32.378 | 48.629 | 46.565 | 1.00 | 29.97 | C |
| ATOM | 315 | N | ILE | A | 45 | 34.552 | 52.693 | 48.264 | 1.00 | 31.20 | N |
| ATOM | 316 | CA | ILE | A | 45 | 33.268 | 53.236 | 47.850 | 1.00 | 32.95 | C |
| ATOM | 317 | C | ILE | A | 45 | 33.283 | 54.722 | 47.516 | 1.00 | 34.02 | C |
| ATOM | 318 | O | ILE | A | 45 | 32.658 | 55.144 | 46.543 | 1.00 | 33.17 | O |
| ATOM | 319 | CB | ILE | A | 45 | 32.178 | 52.922 | 48.903 | 1.00 | 35.47 | C |
| ATOM | 320 | CG1 | ILE | A | 45 | 30.810 | 52.896 | 48.221 | 1.00 | 37.51 | C |
| ATOM | 321 | CG2 | ILE | A | 45 | 32.220 | 53.935 | 50.052 | 1.00 | 34.79 | C |
| ATOM | 322 | CD1 | ILE | A | 45 | 29.720 | 52.293 | 49.086 | 1.00 | 39.88 | C |
| ATOM | 323 | N | SER | A | 46 | 34.022 | 55.509 | 48.293 | 1.00 | 34.50 | N |
| ATOM | 324 | CA | SER | A | 46 | 34.108 | 56.945 | 48.062 | 1.00 | 34.72 | C |
| ATOM | 325 | C | SER | A | 46 | 34.660 | 57.298 | 46.682 | 1.00 | 33.50 | C |
| ATOM | 326 | O | SER | A | 46 | 34.049 | 58.059 | 45.931 | 1.00 | 35.31 | O |
| ATOM | 327 | CB | SER | A | 46 | 34.979 | 57.599 | 49.139 | 1.00 | 37.01 | C |
| ATOM | 328 | OG | SER | A | 46 | 35.062 | 59.004 | 48.952 | 1.00 | 36.66 | O |
| ATOM | 329 | N | GLU | A | 47 | 35.817 | 56.752 | 46.342 | 1.00 | 32.45 | N |
| ATOM | 330 | CA | GLU | A | 47 | 36.426 | 57.052 | 45.051 | 1.00 | 30.79 | C |
| ATOM | 331 | C | GLU | A | 47 | 35.655 | 56.407 | 43.898 | 1.00 | 28.80 | C |
| ATOM | 332 | O | GLU | A | 47 | 35.560 | 56.967 | 42.815 | 1.00 | 28.45 | O |
| ATOM | 333 | CB | GLU | A | 47 | 37.890 | 56.586 | 45.047 | 1.00 | 32.29 | C |
| ATOM | 334 | CG | GLU | A | 47 | 38.739 | 57.103 | 43.885 | 1.00 | 33.02 | C |
| ATOM | 335 | CD | GLU | A | 47 | 38.694 | 58.623 | 43.750 | 1.00 | 35.38 | C |
| ATOM | 336 | OE1 | GLU | A | 47 | 38.484 | 59.322 | 44.765 | 1.00 | 34.56 | O |
| ATOM | 337 | OE2 | GLU | A | 47 | 38.880 | 59.121 | 42.622 | 1.00 | 37.44 | O |
| ATOM | 338 | N | MET | A | 48 | 35.102 | 55.224 | 44.125 | 1.00 | 28.98 | N |
| ATOM | 339 | CA | MET | A | 48 | 34.347 | 54.563 | 43.067 | 1.00 | 29.38 | C |
| ATOM | 340 | C | MET | A | 48 | 33.124 | 55.371 | 42.661 | 1.00 | 26.16 | C |
| ATOM | 341 | O | MET | A | 48 | 32.835 | 55.548 | 41.474 | 1.00 | 25.57 | O |
| ATOM | 342 | CB | MET | A | 48 | 33.929 | 53.163 | 43.510 | 1.00 | 30.17 | C |
| ATOM | 343 | CG | MET | A | 48 | 34.984 | 52.140 | 43.181 | 1.00 | 35.54 | C |
| ATOM | 344 | SD | MET | A | 48 | 35.418 | 52.268 | 41.419 | 1.00 | 41.72 | S |
| ATOM | 345 | CE | MET | A | 48 | 34.088 | 51.459 | 40.712 | 1.00 | 37.21 | C |
| ATOM | 346 | N | VAL | A | 49 | 32.419 | 55.877 | 43.658 | 1.00 | 24.72 | N |
| ATOM | 347 | CA | VAL | A | 49 | 31.230 | 56.664 | 43.415 | 1.00 | 26.13 | C |
| ATOM | 348 | C | VAL | A | 49 | 31.571 | 57.936 | 42.627 | 1.00 | 26.91 | C |
| ATOM | 349 | O | VAL | A | 49 | 30.843 | 58.328 | 41.720 | 1.00 | 26.96 | O |
| ATOM | 350 | CB | VAL | A | 49 | 30.536 | 56.929 | 44.775 | 1.00 | 27.95 | C |
| ATOM | 351 | CG1 | VAL | A | 49 | 30.127 | 58.356 | 44.919 | 1.00 | 31.34 | C |
| ATOM | 352 | CG2 | VAL | A | 49 | 29.345 | 55.986 | 44.912 | 1.00 | 26.79 | C |
| ATOM | 353 | N | VAL | A | 50 | 32.711 | 58.547 | 42.940 | 1.00 | 28.46 | N |
| ATOM | 354 | CA | VAL | A | 50 | 33.167 | 59.755 | 42.246 | 1.00 | 26.04 | C |
| ATOM | 355 | C | VAL | A | 50 | 33.530 | 59.456 | 40.795 | 1.00 | 24.79 | C |
| ATOM | 356 | O | VAL | A | 50 | 33.280 | 60.268 | 39.888 | 1.00 | 24.49 | O |
| ATOM | 357 | CB | VAL | A | 50 | 34.434 | 60.343 | 42.927 | 1.00 | 28.79 | C |
| ATOM | 358 | CG1 | VAL | A | 50 | 35.064 | 61.428 | 42.034 | 1.00 | 31.79 | C |
| ATOM | 359 | CG2 | VAL | A | 50 | 34.076 | 60.916 | 44.283 | 1.00 | 30.83 | C |
| ATOM | 360 | N | GLN | A | 51 | 34.149 | 58.299 | 40.575 | 1.00 | 21.97 | N |
| ATOM | 361 | CA | GLN | A | 51 | 34.556 | 57.921 | 39.230 | 1.00 | 20.73 | C |

TABLE 4-continued

Stem Cell Factor Dimer

| ATOM | 362 | C | GLN | A | 51 | 33.372 | 57.469 | 38.376 | 1.00 | 20.16 | C |
|------|-----|-----|-----|---|----|--------|--------|--------|------|-------|---|
| ATOM | 363 | O | GLN | A | 51 | 33.330 | 57.730 | 37.169 | 1.00 | 18.64 | O |
| ATOM | 364 | CB | GLN | A | 51 | 35.624 | 56.820 | 39.281 | 1.00 | 23.46 | C |
| ATOM | 365 | CG | GLN | A | 51 | 36.954 | 57.225 | 39.943 | 1.00 | 25.10 | C |
| ATOM | 366 | CD | GLN | A | 51 | 37.537 | 58.540 | 39.407 | 1.00 | 26.66 | C |
| ATOM | 367 | OE1 | GLN | A | 51 | 37.426 | 58.857 | 38.220 | 1.00 | 26.21 | O |
| ATOM | 368 | NE2 | GLN | A | 51 | 38.175 | 59.302 | 40.291 | 1.00 | 27.46 | N |
| ATOM | 369 | N | LEU | A | 52 | 32.413 | 56.779 | 38.988 | 1.00 | 19.42 | N |
| ATOM | 370 | CA | LEU | A | 52 | 31.234 | 56.348 | 38.233 | 1.00 | 20.76 | C |
| ATOM | 371 | C | LEU | A | 52 | 30.499 | 57.613 | 37.797 | 1.00 | 22.46 | C |
| ATOM | 372 | O | LEU | A | 52 | 29.989 | 57.688 | 36.684 | 1.00 | 25.99 | O |
| ATOM | 373 | CB | LEU | A | 52 | 30.316 | 55.470 | 39.098 | 1.00 | 14.75 | C |
| ATOM | 374 | CG | LEU | A | 52 | 30.913 | 54.124 | 39.544 | 1.00 | 16.56 | C |
| ATOM | 375 | CD1 | LEU | A | 52 | 30.008 | 53.506 | 40.584 | 1.00 | 13.24 | C |
| ATOM | 376 | CD2 | LEU | A | 52 | 31.094 | 53.187 | 38.341 | 1.00 | 11.80 | C |
| ATOM | 377 | N | SER | A | 53 | 30.463 | 58.613 | 38.671 | 1.00 | 24.81 | N |
| ATOM | 378 | CA | SER | A | 53 | 29.795 | 59.877 | 38.353 | 1.00 | 28.85 | C |
| ATOM | 379 | C | SER | A | 53 | 30.403 | 60.571 | 37.142 | 1.00 | 29.16 | C |
| ATOM | 380 | O | SER | A | 53 | 29.681 | 61.037 | 36.260 | 1.00 | 30.24 | O |
| ATOM | 381 | CB | SER | A | 53 | 29.842 | 60.826 | 39.552 | 1.00 | 29.60 | C |
| ATOM | 382 | OG | SER | A | 53 | 29.572 | 62.150 | 39.138 | 1.00 | 32.77 | O |
| ATOM | 383 | N | ASP | A | 54 | 31.729 | 60.638 | 37.097 | 1.00 | 30.41 | N |
| ATOM | 384 | CA | ASP | A | 54 | 32.415 | 61.273 | 35.980 | 1.00 | 31.60 | C |
| ATOM | 385 | C | ASP | A | 54 | 32.275 | 60.481 | 34.681 | 1.00 | 31.53 | C |
| ATOM | 386 | O | ASP | A | 54 | 32.151 | 61.060 | 33.595 | 1.00 | 31.38 | O |
| ATOM | 387 | CB | ASP | A | 54 | 33.904 | 61.465 | 36.296 | 1.00 | 36.88 | C |
| ATOM | 388 | CG | ASP | A | 54 | 34.685 | 62.011 | 35.101 | 1.00 | 43.96 | C |
| ATOM | 389 | OD1 | ASP | A | 54 | 34.214 | 62.999 | 34.483 | 1.00 | 45.13 | O |
| ATOM | 390 | OD2 | ASP | A | 54 | 35.767 | 61.459 | 34.780 | 1.00 | 47.18 | O |
| ATOM | 391 | N | SER | A | 55 | 32.304 | 59.158 | 34.775 | 1.00 | 29.76 | N |
| ATOM | 392 | CA | SER | A | 55 | 32.166 | 58.350 | 33.571 | 1.00 | 28.65 | C |
| ATOM | 393 | C | SER | A | 55 | 30.763 | 58.498 | 32.994 | 1.00 | 27.32 | C |
| ATOM | 394 | O | SER | A | 55 | 30.593 | 58.691 | 31.791 | 1.00 | 25.98 | O |
| ATOM | 395 | CB | SER | A | 55 | 32.441 | 56.878 | 33.877 | 1.00 | 29.08 | C |
| ATOM | 396 | OG | SER | A | 55 | 33.829 | 56.635 | 33.964 | 1.00 | 30.44 | O |
| ATOM | 397 | N | LEU | A | 56 | 29.765 | 58.410 | 33.869 | 1.00 | 26.64 | N |
| ATOM | 398 | CA | LEU | A | 56 | 28.367 | 58.520 | 33.466 | 1.00 | 25.98 | C |
| ATOM | 399 | C | LEU | A | 56 | 28.066 | 59.885 | 32.882 | 1.00 | 27.34 | C |
| ATOM | 400 | O | LEU | A | 56 | 27.374 | 59.987 | 31.875 | 1.00 | 27.45 | O |
| ATOM | 401 | CB | LEU | A | 56 | 27.447 | 58.255 | 34.663 | 1.00 | 23.93 | C |
| ATOM | 402 | CG | LEU | A | 56 | 27.346 | 56.784 | 35.086 | 1.00 | 24.56 | C |
| ATOM | 403 | CD1 | LEU | A | 56 | 26.606 | 56.659 | 36.417 | 1.00 | 23.11 | C |
| ATOM | 404 | CD2 | LEU | A | 56 | 26.643 | 55.990 | 33.987 | 1.00 | 16.90 | C |
| ATOM | 405 | N | THR | A | 57 | 28.596 | 60.934 | 33.507 | 1.00 | 27.77 | N |
| ATOM | 406 | CA | THR | A | 57 | 28.356 | 62.286 | 33.012 | 1.00 | 30.04 | C |
| ATOM | 407 | C | THR | A | 57 | 28.983 | 62.441 | 31.630 | 1.00 | 30.98 | C |
| ATOM | 408 | O | THR | A | 57 | 28.386 | 63.039 | 30.743 | 1.00 | 29.51 | O |
| ATOM | 409 | CB | THR | A | 57 | 28.936 | 63.363 | 33.960 | 1.00 | 29.71 | C |
| ATOM | 410 | OG1 | THR | A | 57 | 28.451 | 63.150 | 35.289 | 1.00 | 30.34 | O |
| ATOM | 411 | CG2 | THR | A | 57 | 28.492 | 64.742 | 33.514 | 1.00 | 33.01 | C |
| ATOM | 412 | N | ASP | A | 58 | 30.184 | 61.898 | 31.447 | 1.00 | 34.63 | N |
| ATOM | 413 | CA | ASP | A | 58 | 30.853 | 61.973 | 30.151 | 1.00 | 36.67 | C |
| ATOM | 414 | C | ASP | A | 58 | 30.102 | 61.115 | 29.124 | 1.00 | 37.45 | C |
| ATOM | 415 | O | ASP | A | 58 | 30.080 | 61.429 | 27.934 | 1.00 | 37.92 | O |
| ATOM | 416 | CB | ASP | A | 58 | 32.307 | 61.487 | 30.267 | 1.00 | 38.61 | C |
| ATOM | 417 | CG | ASP | A | 58 | 33.184 | 62.428 | 31.097 | 1.00 | 44.86 | C |
| ATOM | 418 | OD1 | ASP | A | 58 | 34.403 | 62.165 | 31.223 | 1.00 | 46.37 | O |
| ATOM | 419 | OD2 | ASP | A | 58 | 32.662 | 63.433 | 31.630 | 1.00 | 48.63 | O |
| ATOM | 420 | N | LEU | A | 59 | 29.481 | 60.036 | 29.594 | 1.00 | 37.77 | N |
| ATOM | 421 | CA | LEU | A | 59 | 28.735 | 59.128 | 28.719 | 1.00 | 37.88 | C |
| ATOM | 422 | C | LEU | A | 59 | 27.447 | 59.817 | 28.283 | 1.00 | 38.34 | C |
| ATOM | 423 | O | LEU | A | 59 | 26.964 | 59.634 | 27.165 | 1.00 | 35.35 | O |
| ATOM | 424 | CB | LEU | A | 59 | 28.423 | 57.828 | 29.476 | 1.00 | 37.16 | C |
| ATOM | 425 | CG | LEU | A | 59 | 28.103 | 56.510 | 28.750 | 1.00 | 39.59 | C |
| ATOM | 426 | CD1 | LEU | A | 59 | 26.637 | 56.374 | 28.565 | 1.00 | 37.24 | C |
| ATOM | 427 | CD2 | LEU | A | 59 | 28.831 | 56.428 | 27.414 | 1.00 | 38.18 | C |
| ATOM | 428 | N | LEU | A | 60 | 26.914 | 60.632 | 29.182 | 1.00 | 39.99 | N |
| ATOM | 429 | CA | LEU | A | 60 | 25.685 | 61.364 | 28.938 | 1.00 | 42.03 | C |
| ATOM | 430 | C | LEU | A | 60 | 25.788 | 62.336 | 27.760 | 1.00 | 43.49 | C |
| ATOM | 431 | O | LEU | A | 60 | 24.829 | 62.522 | 27.010 | 1.00 | 43.75 | O |
| ATOM | 432 | CB | LEU | A | 60 | 25.291 | 62.118 | 30.208 | 1.00 | 41.27 | C |
| ATOM | 433 | CG | LEU | A | 60 | 23.996 | 62.931 | 30.171 | 1.00 | 43.03 | C |
| ATOM | 434 | CD1 | LEU | A | 60 | 22.830 | 62.045 | 29.746 | 1.00 | 40.00 | C |
| ATOM | 435 | CD2 | LEU | A | 60 | 23.746 | 63.519 | 31.556 | 1.00 | 41.13 | C |
| ATOM | 436 | N | ASP | A | 61 | 26.949 | 62.955 | 27.587 | 1.00 | 45.27 | N |
| ATOM | 437 | CA | ASP | A | 61 | 27.116 | 63.904 | 26.491 | 1.00 | 46.56 | C |
| ATOM | 438 | C | ASP | A | 61 | 27.148 | 63.215 | 25.128 | 1.00 | 45.61 | C |

TABLE 4-continued

Stem Cell Factor Dimer

| ATOM | 439 | O | ASP | A | 61 | 27.019 | 63.866 | 24.087 | 1.00 | 43.88 | O |
|---|---|---|---|---|---|---|---|---|---|---|---|
| ATOM | 440 | CB | ASP | A | 61 | 28.397 | 64.715 | 26.694 | 1.00 | 51.20 | C |
| ATOM | 441 | CG | ASP | A | 61 | 28.573 | 65.800 | 25.644 | 1.00 | 56.47 | C |
| ATOM | 442 | OD1 | ASP | A | 61 | 28.936 | 65.473 | 24.490 | 1.00 | 57.52 | O |
| ATOM | 443 | OD2 | ASP | A | 61 | 28.340 | 66.984 | 25.975 | 1.00 | 59.41 | O |
| ATOM | 444 | N | LYS | A | 62 | 27.299 | 61.893 | 25.136 | 1.00 | 43.35 | N |
| ATOM | 445 | CA | LYS | A | 62 | 27.368 | 61.130 | 23.897 | 1.00 | 42.66 | C |
| ATOM | 446 | C | LYS | A | 62 | 26.016 | 60.770 | 23.290 | 1.00 | 41.38 | C |
| ATOM | 447 | O | LYS | A | 62 | 25.952 | 60.226 | 22.190 | 1.00 | 39.37 | O |
| ATOM | 448 | CB | LYS | A | 62 | 28.203 | 59.869 | 24.122 | 1.00 | 43.03 | C |
| ATOM | 449 | CG | LYS | A | 62 | 29.589 | 60.198 | 24.636 | 1.00 | 44.02 | C |
| ATOM | 450 | CD | LYS | A | 62 | 30.413 | 58.960 | 24.877 | 1.00 | 47.44 | C |
| ATOM | 451 | CE | LYS | A | 62 | 31.784 | 59.335 | 25.411 | 1.00 | 47.28 | C |
| ATOM | 452 | NZ | LYS | A | 62 | 32.464 | 60.280 | 24.484 | 1.00 | 43.52 | N |
| ATOM | 453 | N | PHE | A | 63 | 24.938 | 61.091 | 23.998 | 1.00 | 41.93 | N |
| ATOM | 454 | CA | PHE | A | 63 | 23.595 | 60.796 | 23.507 | 1.00 | 43.46 | C |
| ATOM | 455 | C | PHE | A | 63 | 22.748 | 62.065 | 23.432 | 1.00 | 46.25 | C |
| ATOM | 456 | O | PHE | A | 63 | 22.971 | 63.017 | 24.178 | 1.00 | 46.18 | O |
| ATOM | 457 | CB | PHE | A | 63 | 22.900 | 59.768 | 24.417 | 1.00 | 40.85 | C |
| ATOM | 458 | CG | PHE | A | 63 | 23.607 | 58.442 | 24.492 | 1.00 | 38.31 | C |
| ATOM | 459 | CD1 | PHE | A | 63 | 24.746 | 58.286 | 25.274 | 1.00 | 39.31 | C |
| ATOM | 460 | CD2 | PHE | A | 63 | 23.149 | 57.353 | 23.757 | 1.00 | 39.73 | C |
| ATOM | 461 | CE1 | PHE | A | 63 | 25.420 | 57.065 | 25.325 | 1.00 | 38.30 | C |
| ATOM | 462 | CE2 | PHE | A | 63 | 23.816 | 56.128 | 23.800 | 1.00 | 38.66 | C |
| ATOM | 463 | CZ | PHE | A | 63 | 24.954 | 55.987 | 24.586 | 1.00 | 38.08 | C |
| ATOM | 464 | N | SER | A | 64 | 21.776 | 62.074 | 22.526 | 1.00 | 48.63 | N |
| ATOM | 465 | CA | SER | A | 64 | 20.890 | 63.218 | 22.370 | 1.00 | 50.37 | C |
| ATOM | 466 | C | SER | A | 64 | 19.587 | 62.934 | 23.102 | 1.00 | 52.06 | C |
| ATOM | 467 | O | SER | A | 64 | 19.213 | 61.780 | 23.296 | 1.00 | 51.64 | O |
| ATOM | 468 | CB | SER | A | 64 | 20.621 | 63.479 | 20.893 | 1.00 | 49.86 | C |
| ATOM | 469 | OG | SER | A | 64 | 21.835 | 63.733 | 20.205 | 1.00 | 52.62 | O |
| ATOM | 470 | N | ASN | A | 65 | 18.890 | 63.992 | 23.493 | 1.00 | 54.25 | N |
| ATOM | 471 | CA | ASN | A | 65 | 17.649 | 63.856 | 24.239 | 1.00 | 57.80 | C |
| ATOM | 472 | C | ASN | A | 65 | 16.454 | 63.355 | 23.425 | 1.00 | 59.71 | C |
| ATOM | 473 | O | ASN | A | 65 | 16.451 | 63.421 | 22.195 | 1.00 | 60.42 | O |
| ATOM | 474 | CB | ASN | A | 65 | 17.315 | 65.198 | 24.894 | 1.00 | 59.02 | C |
| ATOM | 475 | CG | ASN | A | 65 | 16.637 | 65.042 | 26.241 | 1.00 | 60.67 | C |
| ATOM | 476 | OD1 | ASN | A | 65 | 16.614 | 65.975 | 27.050 | 1.00 | 61.56 | O |
| ATOM | 477 | ND2 | ASN | A | 65 | 16.074 | 63.865 | 26.490 | 1.00 | 61.15 | N |
| ATOM | 478 | N | ILE | A | 66 | 15.459 | 62.843 | 24.153 | 1.00 | 61.50 | N |
| ATOM | 479 | CA | ILE | A | 66 | 14.186 | 62.305 | 23.643 | 1.00 | 62.44 | C |
| ATOM | 480 | C | ILE | A | 66 | 13.529 | 61.546 | 24.806 | 1.00 | 63.95 | C |
| ATOM | 481 | O | ILE | A | 66 | 12.870 | 60.519 | 24.616 | 1.00 | 64.12 | O |
| ATOM | 482 | CB | ILE | A | 66 | 14.365 | 61.321 | 22.447 | 1.00 | 61.28 | C |
| ATOM | 483 | CG1 | ILE | A | 66 | 15.643 | 60.496 | 22.623 | 1.00 | 61.28 | C |
| ATOM | 484 | CG2 | ILE | A | 66 | 14.337 | 62.085 | 21.132 | 1.00 | 61.26 | C |
| ATOM | 485 | CD1 | ILE | A | 66 | 15.873 | 59.478 | 21.519 | 1.00 | 59.60 | C |
| ATOM | 486 | N | SER | A | 67 | 13.718 | 62.085 | 26.009 | 1.00 | 65.07 | N |
| ATOM | 487 | CA | SER | A | 67 | 13.213 | 61.514 | 27.262 | 1.00 | 65.71 | C |
| ATOM | 488 | C | SER | A | 67 | 11.736 | 61.136 | 27.338 | 1.00 | 65.66 | C |
| ATOM | 489 | O | SER | A | 67 | 11.220 | 60.882 | 28.431 | 1.00 | 65.09 | O |
| ATOM | 490 | CB | SER | A | 67 | 13.534 | 62.467 | 28.420 | 1.00 | 66.10 | C |
| ATOM | 491 | OG | SER | A | 67 | 12.963 | 63.747 | 28.205 | 1.00 | 64.67 | O |
| ATOM | 492 | N | GLU | A | 68 | 11.058 | 61.086 | 26.196 | 1.00 | 65.62 | N |
| ATOM | 493 | CA | GLU | A | 68 | 9.641 | 60.736 | 26.182 | 1.00 | 65.03 | C |
| ATOM | 494 | C | GLU | A | 68 | 9.419 | 59.263 | 25.815 | 1.00 | 63.78 | C |
| ATOM | 495 | O | GLU | A | 68 | 8.519 | 58.935 | 25.040 | 1.00 | 63.37 | O |
| ATOM | 496 | CB | GLU | A | 68 | 8.898 | 61.640 | 25.197 | 1.00 | 65.93 | C |
| ATOM | 497 | CG | GLU | A | 68 | 7.406 | 61.729 | 25.450 | 1.00 | 67.61 | C |
| ATOM | 498 | CD | GLU | A | 68 | 6.706 | 62.641 | 24.464 | 1.00 | 68.82 | C |
| ATOM | 499 | OE1 | GLU | A | 68 | 6.517 | 62.225 | 23.299 | 1.00 | 68.58 | O |
| ATOM | 500 | OE2 | GLU | A | 68 | 6.356 | 63.776 | 24.857 | 1.00 | 68.78 | O |
| ATOM | 501 | N | GLY | A | 69 | 10.242 | 58.380 | 26.376 | 1.00 | 62.73 | N |
| ATOM | 502 | CA | GLY | A | 69 | 10.112 | 56.960 | 26.089 | 1.00 | 60.38 | C |
| ATOM | 503 | C | GLY | A | 69 | 11.318 | 56.129 | 26.496 | 1.00 | 58.08 | C |
| ATOM | 504 | O | GLY | A | 69 | 11.721 | 55.220 | 25.766 | 1.00 | 57.97 | O |
| ATOM | 505 | N | LEU | A | 70 | 11.891 | 56.449 | 27.659 | 1.00 | 55.78 | N |
| ATOM | 506 | CA | LEU | A | 70 | 13.061 | 55.748 | 28.204 | 1.00 | 51.80 | C |
| ATOM | 507 | C | LEU | A | 70 | 14.243 | 55.633 | 27.242 | 1.00 | 49.05 | C |
| ATOM | 508 | O | LEU | A | 70 | 14.664 | 54.529 | 26.895 | 1.00 | 47.57 | O |
| ATOM | 509 | CB | LEU | A | 70 | 12.670 | 54.344 | 28.669 | 1.00 | 53.32 | C |
| ATOM | 510 | CG | LEU | A | 70 | 11.781 | 54.192 | 29.902 | 1.00 | 54.23 | C |
| ATOM | 511 | CD1 | LEU | A | 70 | 11.330 | 52.742 | 30.021 | 1.00 | 55.04 | C |
| ATOM | 512 | CD2 | LEU | A | 70 | 12.542 | 54.631 | 31.143 | 1.00 | 53.18 | C |
| ATOM | 513 | N | SER | A | 71 | 14.776 | 56.770 | 26.812 | 1.00 | 45.73 | N |
| ATOM | 514 | CA | SER | A | 71 | 15.924 | 56.781 | 25.912 | 1.00 | 41.79 | C |
| ATOM | 515 | C | SER | A | 71 | 17.195 | 56.580 | 26.741 | 1.00 | 38.39 | C |

TABLE 4-continued

Stem Cell Factor Dimer

| ATOM | 516 | O | SER | A | 71 | 17.169 | 56.692 | 27.962 | 1.00 | 36.09 | O |
|---|---|---|---|---|---|---|---|---|---|---|---|
| ATOM | 517 | CB | SER | A | 71 | 16.004 | 58.122 | 25.182 | 1.00 | 40.37 | C |
| ATOM | 518 | OG | SER | A | 71 | 16.164 | 59.185 | 26.107 | 1.00 | 40.70 | O |
| ATOM | 519 | N | ASN | A | 72 | 18.307 | 56.286 | 26.078 | 1.00 | 36.35 | N |
| ATOM | 520 | CA | ASN | A | 72 | 19.559 | 56.102 | 26.794 | 1.00 | 34.21 | C |
| ATOM | 521 | C | ASN | A | 72 | 19.874 | 57.380 | 27.554 | 1.00 | 32.13 | C |
| ATOM | 522 | O | ASN | A | 72 | 20.222 | 57.343 | 28.734 | 1.00 | 32.02 | O |
| ATOM | 523 | CB | ASN | A | 72 | 20.699 | 55.750 | 25.823 | 1.00 | 33.32 | C |
| ATOM | 524 | CG | ASN | A | 72 | 20.574 | 54.334 | 25.271 | 1.00 | 34.31 | C |
| ATOM | 525 | OD1 | ASN | A | 72 | 19.927 | 53.489 | 25.878 | 1.00 | 34.94 | O |
| ATOM | 526 | ND2 | ASN | A | 72 | 21.205 | 54.068 | 24.128 | 1.00 | 36.96 | N |
| ATOM | 527 | N | TYR | A | 73 | 19.723 | 58.511 | 26.880 | 1.00 | 32.21 | N |
| ATOM | 528 | CA | TYR | A | 73 | 19.986 | 59.810 | 27.490 | 1.00 | 33.90 | C |
| ATOM | 529 | C | TYR | A | 73 | 19.269 | 59.956 | 28.833 | 1.00 | 34.77 | C |
| ATOM | 530 | O | TYR | A | 73 | 19.876 | 60.292 | 29.854 | 1.00 | 35.67 | O |
| ATOM | 531 | CB | TYR | A | 73 | 19.522 | 60.941 | 26.557 | 1.00 | 34.65 | C |
| ATOM | 532 | CG | TYR | A | 73 | 19.867 | 62.324 | 27.081 | 1.00 | 35.46 | C |
| ATOM | 533 | CD1 | TYR | A | 73 | 21.042 | 62.965 | 26.695 | 1.00 | 36.50 | C |
| ATOM | 534 | CD2 | TYR | A | 73 | 19.057 | 62.951 | 28.024 | 1.00 | 36.48 | C |
| ATOM | 535 | CE1 | TYR | A | 73 | 21.402 | 64.196 | 27.242 | 1.00 | 40.10 | C |
| ATOM | 536 | CE2 | TYR | A | 73 | 19.408 | 64.175 | 28.580 | 1.00 | 37.06 | C |
| ATOM | 537 | CZ | TYR | A | 73 | 20.578 | 64.793 | 28.189 | 1.00 | 40.24 | C |
| ATOM | 538 | OH | TYR | A | 73 | 20.931 | 65.999 | 28.757 | 1.00 | 44.57 | O |
| ATOM | 539 | N | SER | A | 74 | 17.967 | 59.702 | 28.820 | 1.00 | 34.84 | N |
| ATOM | 540 | CA | SER | A | 74 | 17.142 | 59.827 | 30.014 | 1.00 | 35.51 | C |
| ATOM | 541 | C | SER | A | 74 | 17.541 | 58.899 | 31.151 | 1.00 | 33.42 | C |
| ATOM | 542 | O | SER | A | 74 | 17.619 | 59.317 | 32.310 | 1.00 | 34.04 | O |
| ATOM | 543 | CB | SER | A | 74 | 15.674 | 59.599 | 29.642 | 1.00 | 38.11 | C |
| ATOM | 544 | OG | SER | A | 74 | 15.547 | 58.459 | 28.803 | 1.00 | 42.69 | O |
| ATOM | 545 | N | ILE | A | 75 | 17.785 | 57.637 | 30.825 | 1.00 | 31.51 | N |
| ATOM | 546 | CA | ILE | A | 75 | 18.167 | 56.660 | 31.833 | 1.00 | 28.28 | C |
| ATOM | 547 | C | ILE | A | 75 | 19.512 | 57.029 | 32.469 | 1.00 | 28.34 | C |
| ATOM | 548 | O | ILE | A | 75 | 19.673 | 56.975 | 33.688 | 1.00 | 28.58 | O |
| ATOM | 549 | CB | ILE | A | 75 | 18.243 | 55.254 | 31.203 | 1.00 | 28.45 | C |
| ATOM | 550 | CG1 | ILE | A | 75 | 16.832 | 54.800 | 30.812 | 1.00 | 27.74 | C |
| ATOM | 551 | CG2 | ILE | A | 75 | 18.895 | 54.269 | 32.174 | 1.00 | 25.94 | C |
| ATOM | 552 | CD1 | ILE | A | 75 | 16.796 | 53.502 | 30.039 | 1.00 | 26.89 | C |
| ATOM | 553 | N | ILE | A | 76 | 20.471 | 57.400 | 31.632 | 1.00 | 27.29 | N |
| ATOM | 554 | CA | ILE | A | 76 | 21.788 | 57.787 | 32.095 | 1.00 | 27.88 | C |
| ATOM | 555 | C | ILE | A | 76 | 21.663 | 59.010 | 32.997 | 1.00 | 29.70 | C |
| ATOM | 556 | O | ILE | A | 76 | 22.229 | 59.046 | 34.100 | 1.00 | 27.15 | O |
| ATOM | 557 | CB | ILE | A | 76 | 22.694 | 58.113 | 30.904 | 1.00 | 26.65 | C |
| ATOM | 558 | CG1 | ILE | A | 76 | 22.845 | 56.863 | 30.028 | 1.00 | 24.16 | C |
| ATOM | 559 | CG2 | ILE | A | 76 | 24.053 | 58.595 | 31.397 | 1.00 | 28.04 | C |
| ATOM | 560 | CD1 | ILE | A | 76 | 23.625 | 57.094 | 28.747 | 1.00 | 21.67 | C |
| ATOM | 561 | N | ASP | A | 77 | 20.914 | 60.009 | 32.537 | 1.00 | 32.01 | N |
| ATOM | 562 | CA | ASP | A | 77 | 20.709 | 61.219 | 33.338 | 1.00 | 34.74 | C |
| ATOM | 563 | C | ASP | A | 77 | 20.169 | 60.786 | 34.701 | 1.00 | 33.99 | C |
| ATOM | 564 | O | ASP | A | 77 | 20.594 | 61.286 | 35.738 | 1.00 | 34.81 | O |
| ATOM | 565 | CB | ASP | A | 77 | 19.710 | 62.158 | 32.650 | 1.00 | 38.27 | C |
| ATOM | 566 | CG | ASP | A | 77 | 19.685 | 63.550 | 33.273 | 1.00 | 41.20 | C |
| ATOM | 567 | OD1 | ASP | A | 77 | 18.592 | 63.993 | 33.692 | 1.00 | 40.44 | O |
| ATOM | 568 | OD2 | ASP | A | 77 | 20.754 | 64.204 | 33.338 | 1.00 | 40.25 | O |
| ATOM | 569 | N | LYS | A | 78 | 19.249 | 59.828 | 34.698 | 1.00 | 33.71 | N |
| ATOM | 570 | CA | LYS | A | 78 | 18.682 | 59.336 | 35.952 | 1.00 | 34.96 | C |
| ATOM | 571 | C | LYS | A | 78 | 19.762 | 58.680 | 36.824 | 1.00 | 34.39 | C |
| ATOM | 572 | O | LYS | A | 78 | 19.722 | 58.768 | 38.060 | 1.00 | 33.35 | O |
| ATOM | 573 | CB | LYS | A | 78 | 17.569 | 58.319 | 35.685 | 1.00 | 35.88 | C |
| ATOM | 574 | CG | LYS | A | 78 | 16.930 | 57.796 | 36.968 | 1.00 | 41.99 | C |
| ATOM | 575 | CD | LYS | A | 78 | 16.212 | 56.471 | 36.767 | 1.00 | 46.87 | C |
| ATOM | 576 | CE | LYS | A | 78 | 15.618 | 55.961 | 38.080 | 1.00 | 50.42 | C |
| ATOM | 577 | NZ | LYS | A | 78 | 16.653 | 55.759 | 39.140 | 1.00 | 51.21 | N |
| ATOM | 578 | N | LEU | A | 79 | 20.717 | 58.013 | 36.182 | 1.00 | 31.75 | N |
| ATOM | 579 | CA | LEU | A | 79 | 21.791 | 57.358 | 36.921 | 1.00 | 32.48 | C |
| ATOM | 580 | C | LEU | A | 79 | 22.852 | 58.371 | 37.357 | 1.00 | 31.83 | C |
| ATOM | 581 | O | LEU | A | 79 | 23.494 | 58.205 | 38.392 | 1.00 | 31.52 | O |
| ATOM | 582 | CB | LEU | A | 79 | 22.410 | 56.244 | 36.074 | 1.00 | 29.79 | C |
| ATOM | 583 | CG | LEU | A | 79 | 21.396 | 55.148 | 35.706 | 1.00 | 27.89 | C |
| ATOM | 584 | CD1 | LEU | A | 79 | 22.032 | 54.135 | 34.757 | 1.00 | 29.30 | C |
| ATOM | 585 | CD2 | LEU | A | 79 | 20.899 | 54.470 | 36.978 | 1.00 | 25.77 | C |
| ATOM | 586 | N | VAL | A | 80 | 23.025 | 59.427 | 36.573 | 1.00 | 32.63 | N |
| ATOM | 587 | CA | VAL | A | 80 | 23.982 | 60.460 | 36.928 | 1.00 | 33.72 | C |
| ATOM | 588 | C | VAL | A | 80 | 23.559 | 61.094 | 38.251 | 1.00 | 34.77 | C |
| ATOM | 589 | O | VAL | A | 80 | 24.379 | 61.298 | 39.149 | 1.00 | 35.56 | O |
| ATOM | 590 | CB | VAL | A | 80 | 24.049 | 61.562 | 35.861 | 1.00 | 34.70 | C |
| ATOM | 591 | CG1 | VAL | A | 80 | 24.734 | 62.792 | 36.435 | 1.00 | 35.98 | C |
| ATOM | 592 | CG2 | VAL | A | 80 | 24.812 | 61.065 | 34.653 | 1.00 | 34.16 | C |

TABLE 4-continued

Stem Cell Factor Dimer

| ATOM | 593 | N | ASN | A | 81 | 22.269 | 61.390 | 38.373 | 1.00 | 34.14 | N |
| ATOM | 594 | CA | ASN | A | 81 | 21.747 | 62.008 | 39.584 | 1.00 | 33.35 | C |
| ATOM | 595 | C | ASN | A | 81 | 21.853 | 61.128 | 40.824 | 1.00 | 32.98 | C |
| ATOM | 596 | O | ASN | A | 81 | 22.174 | 61.610 | 41.914 | 1.00 | 32.45 | O |
| ATOM | 597 | CB | ASN | A | 81 | 20.300 | 62.432 | 39.355 | 1.00 | 35.05 | C |
| ATOM | 598 | CG | ASN | A | 81 | 20.147 | 63.289 | 38.115 | 1.00 | 36.59 | C |
| ATOM | 599 | OD1 | ASN | A | 81 | 20.902 | 64.240 | 37.906 | 1.00 | 35.13 | O |
| ATOM | 600 | ND2 | ASN | A | 81 | 19.169 | 62.955 | 37.282 | 1.00 | 39.80 | N |
| ATOM | 601 | N | ILE | A | 82 | 21.584 | 59.840 | 40.672 | 1.00 | 33.56 | N |
| ATOM | 602 | CA | ILE | A | 82 | 21.676 | 58.927 | 41.806 | 1.00 | 33.86 | C |
| ATOM | 603 | C | ILE | A | 82 | 23.092 | 58.918 | 42.372 | 1.00 | 32.61 | C |
| ATOM | 604 | O | ILE | A | 82 | 23.281 | 59.059 | 43.576 | 1.00 | 32.75 | O |
| ATOM | 605 | CB | ILE | A | 82 | 21.334 | 57.482 | 41.408 | 1.00 | 34.33 | C |
| ATOM | 606 | CG1 | ILE | A | 82 | 19.888 | 57.396 | 40.932 | 1.00 | 36.95 | C |
| ATOM | 607 | CG2 | ILE | A | 82 | 21.536 | 56.563 | 42.593 | 1.00 | 35.34 | C |
| ATOM | 608 | CD1 | ILE | A | 82 | 19.521 | 56.046 | 40.357 | 1.00 | 36.95 | C |
| ATOM | 609 | N | VAL | A | 83 | 24.077 | 58.767 | 41.489 | 1.00 | 32.99 | N |
| ATOM | 610 | CA | VAL | A | 83 | 25.484 | 58.701 | 41.887 | 1.00 | 33.17 | C |
| ATOM | 611 | C | VAL | A | 83 | 26.003 | 60.031 | 42.447 | 1.00 | 33.20 | C |
| ATOM | 612 | O | VAL | A | 83 | 26.795 | 60.046 | 43.391 | 1.00 | 31.86 | O |
| ATOM | 613 | CB | VAL | A | 83 | 26.369 | 58.204 | 40.689 | 1.00 | 32.36 | C |
| ATOM | 614 | CG1 | VAL | A | 83 | 26.508 | 59.288 | 39.642 | 1.00 | 34.69 | C |
| ATOM | 615 | CG2 | VAL | A | 83 | 27.724 | 57.756 | 41.176 | 1.00 | 32.84 | C |
| ATOM | 616 | N | ASP | A | 84 | 25.556 | 61.147 | 41.881 | 1.00 | 33.98 | N |
| ATOM | 617 | CA | ASP | A | 84 | 25.985 | 62.445 | 42.392 | 1.00 | 34.87 | C |
| ATOM | 618 | C | ASP | A | 84 | 25.539 | 62.619 | 43.830 | 1.00 | 33.82 | C |
| ATOM | 619 | O | ASP | A | 84 | 26.292 | 63.135 | 44.649 | 1.00 | 33.58 | O |
| ATOM | 620 | CB | ASP | A | 84 | 25.428 | 63.600 | 41.556 | 1.00 | 37.69 | C |
| ATOM | 621 | CG | ASP | A | 84 | 26.204 | 63.817 | 40.275 | 1.00 | 41.84 | C |
| ATOM | 622 | OD1 | ASP | A | 84 | 27.410 | 63.473 | 40.255 | 1.00 | 44.26 | O |
| ATOM | 623 | OD2 | ASP | A | 84 | 25.620 | 64.341 | 39.298 | 1.00 | 42.50 | O |
| ATOM | 624 | N | ASP | A | 85 | 24.319 | 62.195 | 44.147 | 1.00 | 33.77 | N |
| ATOM | 625 | CA | ASP | A | 85 | 23.843 | 62.330 | 45.516 | 1.00 | 34.83 | C |
| ATOM | 626 | C | ASP | A | 85 | 24.598 | 61.405 | 46.453 | 1.00 | 34.94 | C |
| ATOM | 627 | O | ASP | A | 85 | 24.789 | 61.722 | 47.622 | 1.00 | 35.58 | O |
| ATOM | 628 | CB | ASP | A | 85 | 22.338 | 62.056 | 45.621 | 1.00 | 34.28 | C |
| ATOM | 629 | CG | ASP | A | 85 | 21.494 | 63.238 | 45.159 | 1.00 | 34.19 | C |
| ATOM | 630 | OD1 | ASP | A | 85 | 21.834 | 64.409 | 45.479 | 1.00 | 35.35 | O |
| ATOM | 631 | OD2 | ASP | A | 85 | 20.480 | 62.995 | 44.483 | 1.00 | 31.86 | O |
| ATOM | 632 | N | LEU | A | 86 | 25.021 | 60.253 | 45.950 | 1.00 | 35.16 | N |
| ATOM | 633 | CA | LEU | A | 86 | 25.779 | 59.331 | 46.776 | 1.00 | 35.91 | C |
| ATOM | 634 | C | LEU | A | 86 | 27.117 | 60.003 | 47.051 | 1.00 | 37.76 | C |
| ATOM | 635 | O | LEU | A | 86 | 27.698 | 59.853 | 48.126 | 1.00 | 38.30 | O |
| ATOM | 636 | CB | LEU | A | 86 | 25.988 | 58.007 | 46.043 | 1.00 | 38.20 | C |
| ATOM | 637 | CG | LEU | A | 86 | 24.740 | 57.137 | 45.912 | 1.00 | 37.91 | C |
| ATOM | 638 | CD1 | LEU | A | 86 | 25.039 | 55.940 | 45.016 | 1.00 | 36.31 | C |
| ATOM | 639 | CD2 | LEU | A | 86 | 24.288 | 56.696 | 47.308 | 1.00 | 36.80 | C |
| ATOM | 640 | N | VAL | A | 87 | 27.602 | 60.748 | 46.066 | 1.00 | 38.12 | N |
| ATOM | 641 | CA | VAL | A | 87 | 28.853 | 61.468 | 46.223 | 1.00 | 42.55 | C |
| ATOM | 642 | C | VAL | A | 87 | 28.661 | 62.462 | 47.362 | 1.00 | 45.41 | C |
| ATOM | 643 | O | VAL | A | 87 | 29.497 | 62.575 | 48.259 | 1.00 | 44.45 | O |
| ATOM | 644 | CB | VAL | A | 87 | 29.208 | 62.266 | 44.956 | 1.00 | 42.27 | C |
| ATOM | 645 | CG1 | VAL | A | 87 | 30.362 | 63.207 | 45.250 | 1.00 | 42.69 | C |
| ATOM | 646 | CG2 | VAL | A | 87 | 29.549 | 61.319 | 43.817 | 1.00 | 41.63 | C |
| ATOM | 647 | N | GLU | A | 88 | 27.550 | 63.191 | 47.309 | 1.00 | 48.56 | N |
| ATOM | 648 | CA | GLU | A | 88 | 27.239 | 64.179 | 48.330 | 1.00 | 52.09 | C |
| ATOM | 649 | C | GLU | A | 88 | 27.298 | 63.531 | 49.699 | 1.00 | 54.56 | C |
| ATOM | 650 | O | GLU | A | 88 | 28.064 | 63.956 | 50.560 | 1.00 | 54.23 | O |
| ATOM | 651 | CB | GLU | A | 88 | 25.847 | 64.761 | 48.089 | 1.00 | 53.28 | C |
| ATOM | 652 | CG | GLU | A | 88 | 25.791 | 65.815 | 46.995 | 1.00 | 54.41 | C |
| ATOM | 653 | CD | GLU | A | 88 | 24.377 | 66.096 | 46.532 | 1.00 | 55.68 | C |
| ATOM | 654 | OE1 | GLU | A | 88 | 23.475 | 66.192 | 47.387 | 1.00 | 58.43 | O |
| ATOM | 655 | OE2 | GLU | A | 88 | 24.166 | 66.230 | 45.312 | 1.00 | 58.39 | O |
| ATOM | 656 | N | CYS | A | 89 | 26.499 | 62.490 | 49.890 | 1.00 | 57.50 | N |
| ATOM | 657 | CA | CYS | A | 89 | 26.467 | 61.792 | 51.161 | 1.00 | 62.27 | C |
| ATOM | 658 | C | CYS | A | 89 | 27.866 | 61.420 | 51.647 | 1.00 | 62.66 | C |
| ATOM | 659 | O | CYS | A | 89 | 28.289 | 61.839 | 52.724 | 1.00 | 62.85 | O |
| ATOM | 660 | CB | CYS | A | 89 | 25.601 | 60.536 | 51.050 | 1.00 | 67.26 | C |
| ATOM | 661 | SG | CYS | A | 89 | 25.709 | 59.436 | 52.501 | 1.00 | 78.05 | S |
| ATOM | 662 | N | VAL | A | 90 | 28.583 | 60.638 | 50.849 | 1.00 | 62.27 | N |
| ATOM | 663 | CA | VAL | A | 90 | 29.927 | 60.210 | 51.214 | 1.00 | 63.33 | C |
| ATOM | 664 | C | VAL | A | 90 | 30.805 | 61.341 | 51.768 | 1.00 | 62.95 | C |
| ATOM | 665 | O | VAL | A | 90 | 31.500 | 61.159 | 52.765 | 1.00 | 61.82 | O |
| ATOM | 666 | CB | VAL | A | 90 | 30.628 | 59.537 | 50.010 | 1.00 | 63.19 | C |
| ATOM | 667 | CG1 | VAL | A | 90 | 32.103 | 59.345 | 50.300 | 1.00 | 64.89 | C |
| ATOM | 668 | CG2 | VAL | A | 90 | 29.981 | 58.191 | 49.732 | 1.00 | 61.96 | C |
| ATOM | 669 | N | LYS | A | 91 | 30.773 | 62.504 | 51.126 | 1.00 | 63.59 | N |

TABLE 4-continued

Stem Cell Factor Dimer

| ATOM | 670 | CA | LYS | A | 91 | 31.563 | 63.642 | 51.587 | 1.00 | 64.50 | C |
|---|---|---|---|---|---|---|---|---|---|---|---|
| ATOM | 671 | C | LYS | A | 91 | 31.004 | 64.194 | 52.893 | 1.00 | 65.68 | C |
| ATOM | 672 | O | LYS | A | 91 | 31.742 | 64.743 | 53.712 | 1.00 | 65.73 | O |
| ATOM | 673 | CB | LYS | A | 91 | 31.553 | 64.766 | 50.553 | 1.00 | 64.42 | C |
| ATOM | 674 | CG | LYS | A | 91 | 32.276 | 64.464 | 49.263 | 1.00 | 65.33 | C |
| ATOM | 675 | CD | LYS | A | 91 | 32.184 | 65.663 | 48.337 | 1.00 | 66.20 | C |
| ATOM | 676 | CE | LYS | A | 91 | 32.915 | 65.423 | 47.028 | 1.00 | 67.45 | C |
| ATOM | 677 | NZ | LYS | A | 91 | 32.938 | 66.661 | 46.200 | 1.00 | 67.45 | N |
| ATOM | 678 | N | GLU | A | 92 | 29.697 | 64.047 | 53.080 | 1.00 | 66.60 | N |
| ATOM | 679 | CA | GLU | A | 92 | 29.037 | 64.553 | 54.274 | 1.00 | 68.25 | C |
| ATOM | 680 | C | GLU | A | 92 | 29.061 | 63.561 | 55.430 | 1.00 | 68.30 | C |
| ATOM | 681 | O | GLU | A | 92 | 29.281 | 63.944 | 56.575 | 1.00 | 68.42 | O |
| ATOM | 682 | CB | GLU | A | 92 | 27.591 | 64.950 | 53.940 | 1.00 | 68.61 | C |
| ATOM | 683 | CG | GLU | A | 92 | 27.496 | 65.964 | 52.791 | 1.00 | 71.45 | C |
| ATOM | 684 | CD | GLU | A | 92 | 26.065 | 66.347 | 52.416 | 1.00 | 72.08 | C |
| ATOM | 685 | OE1 | GLU | A | 92 | 25.233 | 65.437 | 52.196 | 1.00 | 70.81 | O |
| ATOM | 686 | OE2 | GLU | A | 92 | 25.782 | 67.564 | 52.327 | 1.00 | 71.57 | O |
| ATOM | 687 | N | ASN | A | 93 | 28.843 | 62.286 | 55.129 | 1.00 | 69.10 | N |
| ATOM | 688 | CA | ASN | A | 93 | 28.832 | 61.254 | 56.161 | 1.00 | 69.73 | C |
| ATOM | 689 | C | ASN | A | 93 | 30.151 | 60.498 | 56.216 | 1.00 | 69.75 | C |
| ATOM | 690 | O | ASN | A | 93 | 30.178 | 59.269 | 56.140 | 1.00 | 67.54 | O |
| ATOM | 691 | CB | ASN | A | 93 | 27.677 | 60.282 | 55.914 | 1.00 | 70.14 | C |
| ATOM | 692 | CG | ASN | A | 93 | 26.317 | 60.936 | 56.107 | 1.00 | 71.63 | C |
| ATOM | 693 | OD1 | ASN | A | 93 | 26.000 | 61.420 | 57.193 | 1.00 | 71.75 | O |
| ATOM | 694 | ND2 | ASN | A | 93 | 25.510 | 60.956 | 55.052 | 1.00 | 71.69 | N |
| ATOM | 695 | N | SER | A | 94 | 31.239 | 61.250 | 56.366 | 1.00 | 71.08 | N |
| ATOM | 696 | CA | SER | A | 94 | 32.582 | 60.680 | 56.420 | 1.00 | 72.71 | C |
| ATOM | 697 | C | SER | A | 94 | 33.074 | 60.398 | 57.841 | 1.00 | 72.70 | C |
| ATOM | 698 | O | SER | A | 94 | 32.984 | 61.248 | 58.730 | 1.00 | 72.27 | O |
| ATOM | 699 | CB | SER | A | 94 | 33.568 | 61.608 | 55.703 | 1.00 | 73.81 | C |
| ATOM | 700 | OG | SER | A | 94 | 33.476 | 62.940 | 56.181 | 1.00 | 75.51 | O |
| ATOM | 701 | N | SER | A | 95 | 33.599 | 59.189 | 58.031 | 1.00 | 72.69 | N |
| ATOM | 702 | CA | SER | A | 95 | 34.111 | 58.721 | 59.316 | 1.00 | 72.24 | C |
| ATOM | 703 | C | SER | A | 95 | 34.363 | 57.224 | 59.161 | 1.00 | 72.10 | C |
| ATOM | 704 | O | SER | A | 95 | 33.463 | 56.484 | 58.757 | 1.00 | 72.07 | O |
| ATOM | 705 | CB | SER | A | 95 | 33.078 | 58.963 | 60.421 | 1.00 | 72.42 | C |
| ATOM | 706 | OG | SER | A | 95 | 31.836 | 58.353 | 60.102 | 1.00 | 71.47 | O |
| ATOM | 707 | N | LYS | A | 96 | 35.581 | 56.781 | 59.473 | 1.00 | 71.80 | N |
| ATOM | 708 | CA | LYS | A | 96 | 35.948 | 55.369 | 59.334 | 1.00 | 70.97 | C |
| ATOM | 709 | C | LYS | A | 96 | 35.941 | 55.055 | 57.840 | 1.00 | 70.26 | C |
| ATOM | 710 | O | LYS | A | 96 | 36.373 | 53.990 | 57.404 | 1.00 | 69.79 | O |
| ATOM | 711 | CB | LYS | A | 96 | 34.929 | 54.470 | 60.043 | 1.00 | 71.97 | C |
| ATOM | 712 | CG | LYS | A | 96 | 34.719 | 54.773 | 61.518 | 1.00 | 72.65 | C |
| ATOM | 713 | CD | LYS | A | 96 | 33.535 | 53.988 | 62.067 | 1.00 | 72.31 | C |
| ATOM | 714 | CE | LYS | A | 96 | 33.365 | 54.197 | 63.563 | 1.00 | 72.18 | C |
| ATOM | 715 | NZ | LYS | A | 96 | 34.501 | 53.627 | 64.341 | 1.00 | 72.30 | N |
| ATOM | 716 | N | ASP | A | 97 | 35.435 | 56.015 | 57.073 | 1.00 | 70.01 | N |
| ATOM | 717 | CA | ASP | A | 97 | 35.321 | 55.930 | 55.623 | 1.00 | 69.44 | C |
| ATOM | 718 | C | ASP | A | 97 | 36.425 | 56.795 | 55.011 | 1.00 | 68.15 | C |
| ATOM | 719 | O | ASP | A | 97 | 36.615 | 57.937 | 55.427 | 1.00 | 67.24 | O |
| ATOM | 720 | CB | ASP | A | 97 | 33.937 | 56.449 | 55.215 | 1.00 | 70.94 | C |
| ATOM | 721 | CG | ASP | A | 97 | 33.650 | 56.265 | 53.745 | 1.00 | 72.18 | C |
| ATOM | 722 | OD1 | ASP | A | 97 | 34.271 | 56.973 | 52.923 | 1.00 | 73.65 | O |
| ATOM | 723 | OD2 | ASP | A | 97 | 32.800 | 55.408 | 53.415 | 1.00 | 72.87 | O |
| ATOM | 724 | N | LEU | A | 98 | 37.157 | 56.256 | 54.038 | 1.00 | 67.60 | N |
| ATOM | 725 | CA | LEU | A | 98 | 38.240 | 57.017 | 53.415 | 1.00 | 68.68 | C |
| ATOM | 726 | C | LEU | A | 98 | 37.741 | 58.216 | 52.616 | 1.00 | 69.78 | C |
| ATOM | 727 | O | LEU | A | 98 | 38.022 | 58.334 | 51.423 | 1.00 | 69.16 | O |
| ATOM | 728 | CB | LEU | A | 98 | 39.096 | 56.121 | 52.507 | 1.00 | 67.38 | C |
| ATOM | 729 | CG | LEU | A | 98 | 40.061 | 55.113 | 53.148 | 1.00 | 67.16 | C |
| ATOM | 730 | CD1 | LEU | A | 98 | 41.063 | 54.637 | 52.097 | 1.00 | 65.06 | C |
| ATOM | 731 | CD2 | LEU | A | 98 | 40.807 | 55.758 | 54.311 | 1.00 | 66.45 | C |
| ATOM | 732 | N | LYS | A | 99 | 37.010 | 59.106 | 53.284 | 1.00 | 71.95 | N |
| ATOM | 733 | CA | LYS | A | 99 | 36.470 | 60.300 | 52.641 | 1.00 | 73.06 | C |
| ATOM | 734 | C | LYS | A | 99 | 37.514 | 60.934 | 51.733 | 1.00 | 73.45 | C |
| ATOM | 735 | O | LYS | A | 99 | 38.408 | 61.647 | 52.188 | 1.00 | 74.34 | O |
| ATOM | 736 | CB | LYS | A | 99 | 36.013 | 61.324 | 53.689 | 1.00 | 73.26 | C |
| ATOM | 737 | CG | LYS | A | 99 | 37.123 | 61.846 | 54.598 | 1.00 | 76.26 | C |
| ATOM | 738 | CD | LYS | A | 99 | 36.663 | 63.051 | 55.420 | 1.00 | 78.03 | C |
| ATOM | 739 | CE | LYS | A | 99 | 37.794 | 63.598 | 56.295 | 1.00 | 78.42 | C |
| ATOM | 740 | NZ | LYS | A | 99 | 37.377 | 64.795 | 57.091 | 1.00 | 77.23 | N |
| ATOM | 741 | N | LYS | A | 100 | 37.397 | 60.657 | 50.440 | 1.00 | 74.11 | N |
| ATOM | 742 | CA | LYS | A | 100 | 38.320 | 61.197 | 49.453 | 1.00 | 73.86 | C |
| ATOM | 743 | C | LYS | A | 100 | 39.731 | 60.728 | 49.762 | 1.00 | 73.67 | C |
| ATOM | 744 | O | LYS | A | 100 | 39.917 | 59.744 | 50.475 | 1.00 | 73.41 | O |
| ATOM | 745 | CB | LYS | A | 100 | 38.255 | 62.727 | 49.453 | 1.00 | 74.51 | C |
| ATOM | 746 | CG | LYS | A | 100 | 38.514 | 63.373 | 48.097 | 1.00 | 75.16 | C |

TABLE 4-continued

Stem Cell Factor Dimer

| ATOM | 747 | CD | LYS | A | 100 | 38.165 | 64.857 | 48.144 | 1.00 | 76.21 | C |
|---|---|---|---|---|---|---|---|---|---|---|---|
| ATOM | 748 | CE | LYS | A | 100 | 38.280 | 65.517 | 46.776 | 1.00 | 75.62 | C |
| ATOM | 749 | NZ | LYS | A | 100 | 37.939 | 66.967 | 46.843 | 1.00 | 74.24 | N |
| ATOM | 750 | N | SER | A | 101 | 40.705 | 61.454 | 49.222 | 1.00 | 73.99 | N |
| ATOM | 751 | CA | SER | A | 101 | 42.134 | 61.174 | 49.366 | 1.00 | 74.29 | C |
| ATOM | 752 | C | SER | A | 101 | 42.577 | 60.588 | 48.037 | 1.00 | 75.40 | C |
| ATOM | 753 | O | SER | A | 101 | 42.055 | 59.561 | 47.595 | 1.00 | 75.14 | O |
| ATOM | 754 | CB | SER | A | 101 | 42.424 | 60.165 | 50.478 | 1.00 | 73.98 | C |
| ATOM | 755 | OG | SER | A | 101 | 42.249 | 58.840 | 50.009 | 1.00 | 70.78 | O |
| ATOM | 756 | N | PHE | A | 102 | 43.532 | 61.255 | 47.398 | 1.00 | 76.34 | N |
| ATOM | 757 | CA | PHE | A | 102 | 44.047 | 60.822 | 46.108 | 1.00 | 76.69 | C |
| ATOM | 758 | C | PHE | A | 102 | 43.071 | 61.231 | 45.006 | 1.00 | 76.76 | C |
| ATOM | 759 | O | PHE | A | 102 | 43.028 | 62.394 | 44.595 | 1.00 | 76.40 | O |
| ATOM | 760 | CB | PHE | A | 102 | 44.237 | 59.299 | 46.092 | 1.00 | 75.92 | C |
| ATOM | 761 | CG | PHE | A | 102 | 45.223 | 58.823 | 45.069 | 1.00 | 77.00 | C |
| ATOM | 762 | CD1 | PHE | A | 102 | 46.583 | 59.073 | 45.231 | 1.00 | 77.34 | C |
| ATOM | 763 | CD2 | PHE | A | 102 | 44.799 | 58.129 | 43.945 | 1.00 | 76.96 | C |
| ATOM | 764 | CE1 | PHE | A | 102 | 47.507 | 58.638 | 44.289 | 1.00 | 77.66 | C |
| ATOM | 765 | CE2 | PHE | A | 102 | 45.714 | 57.688 | 42.994 | 1.00 | 78.03 | C |
| ATOM | 766 | CZ | PHE | A | 102 | 47.073 | 57.944 | 43.167 | 1.00 | 78.07 | C |
| ATOM | 767 | N | LYS | A | 103 | 42.278 | 60.265 | 44.555 | 1.00 | 76.89 | N |
| ATOM | 768 | CA | LYS | A | 103 | 41.300 | 60.467 | 43.489 | 1.00 | 75.84 | C |
| ATOM | 769 | C | LYS | A | 103 | 42.016 | 60.600 | 42.151 | 1.00 | 74.97 | C |
| ATOM | 770 | O | LYS | A | 103 | 42.033 | 61.670 | 41.538 | 1.00 | 75.72 | O |
| ATOM | 771 | CB | LYS | A | 103 | 40.434 | 61.706 | 43.754 | 1.00 | 76.14 | C |
| ATOM | 772 | CG | LYS | A | 103 | 39.321 | 61.908 | 42.727 | 1.00 | 75.38 | C |
| ATOM | 773 | CD | LYS | A | 103 | 38.326 | 62.977 | 43.159 | 1.00 | 75.24 | C |
| ATOM | 774 | CE | LYS | A | 103 | 37.647 | 62.607 | 44.470 | 1.00 | 76.66 | C |
| ATOM | 775 | NZ | LYS | A | 103 | 36.670 | 63.644 | 44.905 | 1.00 | 77.05 | N |
| ATOM | 776 | N | SER | A | 104 | 42.621 | 59.496 | 41.720 | 1.00 | 73.25 | N |
| ATOM | 777 | CA | SER | A | 104 | 43.343 | 59.435 | 40.457 | 1.00 | 70.83 | C |
| ATOM | 778 | C | SER | A | 104 | 43.823 | 58.012 | 40.156 | 1.00 | 68.77 | C |
| ATOM | 779 | O | SER | A | 104 | 44.997 | 57.790 | 39.849 | 1.00 | 67.79 | O |
| ATOM | 780 | CB | SER | A | 104 | 44.536 | 60.396 | 40.478 | 1.00 | 71.12 | C |
| ATOM | 781 | OG | SER | A | 104 | 45.419 | 60.096 | 41.542 | 1.00 | 72.02 | O |
| ATOM | 782 | N | PRO | A | 105 | 42.918 | 57.023 | 40.255 | 1.00 | 66.86 | N |
| ATOM | 783 | CA | PRO | A | 105 | 43.317 | 55.641 | 39.971 | 1.00 | 64.75 | C |
| ATOM | 784 | C | PRO | A | 105 | 43.604 | 55.486 | 38.481 | 1.00 | 61.83 | C |
| ATOM | 785 | O | PRO | A | 105 | 43.587 | 56.464 | 37.738 | 1.00 | 60.17 | O |
| ATOM | 786 | CB | PRO | A | 105 | 42.104 | 54.830 | 40.429 | 1.00 | 64.56 | C |
| ATOM | 787 | CG | PRO | A | 105 | 40.969 | 55.755 | 40.161 | 1.00 | 65.66 | C |
| ATOM | 788 | CD | PRO | A | 105 | 41.499 | 57.085 | 40.652 | 1.00 | 66.17 | C |
| ATOM | 789 | N | GLU | A | 106 | 43.864 | 54.261 | 38.045 | 1.00 | 60.87 | N |
| ATOM | 790 | CA | GLU | A | 106 | 44.160 | 54.022 | 36.640 | 1.00 | 59.84 | C |
| ATOM | 791 | C | GLU | A | 106 | 42.910 | 53.757 | 35.812 | 1.00 | 57.01 | C |
| ATOM | 792 | O | GLU | A | 106 | 42.089 | 52.900 | 36.151 | 1.00 | 55.55 | O |
| ATOM | 793 | CB | GLU | A | 106 | 45.109 | 52.838 | 36.477 | 1.00 | 62.12 | C |
| ATOM | 794 | CG | GLU | A | 106 | 45.608 | 52.680 | 35.053 | 1.00 | 64.12 | C |
| ATOM | 795 | CD | GLU | A | 106 | 45.997 | 51.260 | 34.728 | 1.00 | 64.48 | C |
| ATOM | 796 | OE1 | GLU | A | 106 | 46.598 | 51.047 | 33.656 | 1.00 | 65.35 | O |
| ATOM | 797 | OE2 | GLU | A | 106 | 45.694 | 50.358 | 35.539 | 1.00 | 64.07 | O |
| ATOM | 798 | N | PRO | A | 107 | 42.765 | 54.486 | 34.700 | 1.00 | 54.46 | N |
| ATOM | 799 | CA | PRO | A | 107 | 41.633 | 54.374 | 33.781 | 1.00 | 53.06 | C |
| ATOM | 800 | C | PRO | A | 107 | 41.696 | 53.166 | 32.851 | 1.00 | 50.35 | C |
| ATOM | 801 | O | PRO | A | 107 | 42.691 | 52.962 | 32.162 | 1.00 | 49.73 | O |
| ATOM | 802 | CB | PRO | A | 107 | 41.702 | 55.684 | 33.005 | 1.00 | 55.58 | C |
| ATOM | 803 | CG | PRO | A | 107 | 43.183 | 55.913 | 32.905 | 1.00 | 54.79 | C |
| ATOM | 804 | CD | PRO | A | 107 | 43.654 | 55.595 | 34.303 | 1.00 | 54.48 | C |
| ATOM | 805 | N | ARG | A | 108 | 40.640 | 52.359 | 32.844 | 1.00 | 47.27 | N |
| ATOM | 806 | CA | ARG | A | 108 | 40.589 | 51.216 | 31.945 | 1.00 | 45.13 | C |
| ATOM | 807 | C | ARG | A | 108 | 39.271 | 51.171 | 31.180 | 1.00 | 42.72 | C |
| ATOM | 808 | O | ARG | A | 108 | 38.344 | 51.927 | 31.469 | 1.00 | 41.21 | O |
| ATOM | 809 | CB | ARG | A | 108 | 40.839 | 49.895 | 32.688 | 1.00 | 46.99 | C |
| ATOM | 810 | CG | ARG | A | 108 | 40.379 | 49.829 | 34.119 | 1.00 | 47.99 | C |
| ATOM | 811 | CD | ARG | A | 108 | 40.904 | 48.555 | 34.807 | 1.00 | 49.01 | C |
| ATOM | 812 | NE | ARG | A | 108 | 40.328 | 47.316 | 34.274 | 1.00 | 48.82 | N |
| ATOM | 813 | CZ | ARG | A | 108 | 40.335 | 46.146 | 34.918 | 1.00 | 49.68 | C |
| ATOM | 814 | NH1 | ARG | A | 108 | 40.887 | 46.047 | 36.121 | 1.00 | 47.24 | N |
| ATOM | 815 | NH2 | ARG | A | 108 | 39.775 | 45.074 | 34.370 | 1.00 | 47.63 | N |
| ATOM | 816 | N | LEU | A | 109 | 39.196 | 50.289 | 30.192 | 1.00 | 40.92 | N |
| ATOM | 817 | CA | LEU | A | 109 | 38.001 | 50.174 | 29.375 | 1.00 | 38.05 | C |
| ATOM | 818 | C | LEU | A | 109 | 37.110 | 49.010 | 29.788 | 1.00 | 36.27 | C |
| ATOM | 819 | O | LEU | A | 109 | 37.594 | 47.933 | 30.134 | 1.00 | 36.26 | O |
| ATOM | 820 | CB | LEU | A | 109 | 38.400 | 50.037 | 27.909 | 1.00 | 38.61 | C |
| ATOM | 821 | CG | LEU | A | 109 | 39.249 | 51.180 | 27.345 | 1.00 | 38.72 | C |
| ATOM | 822 | CD1 | LEU | A | 109 | 39.475 | 50.955 | 25.851 | 1.00 | 38.93 | C |
| ATOM | 823 | CD2 | LEU | A | 109 | 38.545 | 52.508 | 27.566 | 1.00 | 38.92 | C |

TABLE 4-continued

Stem Cell Factor Dimer

| ATOM | 824 | N | PHE | A | 110 | 35.801 | 49.245 | 29.766 | 1.00 | 33.35 | N |
|---|---|---|---|---|---|---|---|---|---|---|---|
| ATOM | 825 | CA | PHE | A | 110 | 34.830 | 48.221 | 30.135 | 1.00 | 31.65 | C |
| ATOM | 826 | C | PHE | A | 110 | 33.674 | 48.129 | 29.146 | 1.00 | 31.77 | C |
| ATOM | 827 | O | PHE | A | 110 | 33.274 | 49.127 | 28.520 | 1.00 | 29.31 | O |
| ATOM | 828 | CB | PHE | A | 110 | 34.231 | 48.494 | 31.525 | 1.00 | 30.30 | C |
| ATOM | 829 | CG | PHE | A | 110 | 35.226 | 48.441 | 32.643 | 1.00 | 29.40 | C |
| ATOM | 830 | CD1 | PHE | A | 110 | 35.999 | 49.560 | 32.963 | 1.00 | 30.14 | C |
| ATOM | 831 | CD2 | PHE | A | 110 | 35.427 | 47.260 | 33.353 | 1.00 | 29.90 | C |
| ATOM | 832 | CE1 | PHE | A | 110 | 36.964 | 49.498 | 33.976 | 1.00 | 29.02 | C |
| ATOM | 833 | CE2 | PHE | A | 110 | 36.392 | 47.184 | 34.372 | 1.00 | 28.63 | C |
| ATOM | 834 | CZ | PHE | A | 110 | 37.160 | 48.304 | 34.681 | 1.00 | 29.05 | C |
| ATOM | 835 | N | THR | A | 111 | 33.144 | 46.920 | 29.003 | 1.00 | 28.64 | N |
| ATOM | 836 | CA | THR | A | 111 | 31.988 | 46.710 | 28.139 | 1.00 | 27.53 | C |
| ATOM | 837 | C | THR | A | 111 | 30.832 | 47.280 | 28.946 | 1.00 | 24.61 | C |
| ATOM | 838 | O | THR | A | 111 | 30.939 | 47.436 | 30.166 | 1.00 | 23.79 | O |
| ATOM | 839 | CB | THR | A | 111 | 31.709 | 45.207 | 27.917 | 1.00 | 27.63 | C |
| ATOM | 840 | OG1 | THR | A | 111 | 30.479 | 45.049 | 27.198 | 1.00 | 37.58 | O |
| ATOM | 841 | CG2 | THR | A | 111 | 31.560 | 44.509 | 29.240 | 1.00 | 27.65 | C |
| ATOM | 842 | N | PRO | A | 112 | 29.718 | 47.618 | 28.289 | 1.00 | 24.99 | N |
| ATOM | 843 | CA | PRO | A | 112 | 28.607 | 48.158 | 29.078 | 1.00 | 25.57 | C |
| ATOM | 844 | C | PRO | A | 112 | 28.216 | 47.186 | 30.206 | 1.00 | 27.59 | C |
| ATOM | 845 | O | PRO | A | 112 | 27.982 | 47.593 | 31.348 | 1.00 | 27.07 | O |
| ATOM | 846 | CB | PRO | A | 112 | 27.514 | 48.340 | 28.032 | 1.00 | 25.52 | C |
| ATOM | 847 | CG | PRO | A | 112 | 28.320 | 48.756 | 26.798 | 1.00 | 24.47 | C |
| ATOM | 848 | CD | PRO | A | 112 | 29.480 | 47.776 | 26.840 | 1.00 | 24.44 | C |
| ATOM | 849 | N | GLU | A | 113 | 28.183 | 45.898 | 29.880 | 1.00 | 29.83 | N |
| ATOM | 850 | CA | GLU | A | 113 | 27.837 | 44.850 | 30.839 | 1.00 | 33.19 | C |
| ATOM | 851 | C | GLU | A | 113 | 28.733 | 44.907 | 32.079 | 1.00 | 30.68 | C |
| ATOM | 852 | O | GLU | A | 113 | 28.243 | 44.928 | 33.204 | 1.00 | 30.34 | O |
| ATOM | 853 | CB | GLU | A | 113 | 27.981 | 43.475 | 30.174 | 1.00 | 37.00 | C |
| ATOM | 854 | CG | GLU | A | 113 | 26.730 | 42.612 | 30.231 | 1.00 | 45.69 | C |
| ATOM | 855 | CD | GLU | A | 113 | 26.314 | 42.255 | 31.651 | 1.00 | 50.82 | C |
| ATOM | 856 | OE1 | GLU | A | 113 | 25.922 | 43.167 | 32.418 | 1.00 | 52.22 | O |
| ATOM | 857 | OE2 | GLU | A | 113 | 26.379 | 41.054 | 31.997 | 1.00 | 54.13 | O |
| ATOM | 858 | N | GLU | A | 114 | 30.044 | 44.907 | 31.852 | 1.00 | 29.98 | N |
| ATOM | 859 | CA | GLU | A | 114 | 31.041 | 44.969 | 32.918 | 1.00 | 29.70 | C |
| ATOM | 860 | C | GLU | A | 114 | 30.951 | 46.295 | 33.662 | 1.00 | 27.58 | C |
| ATOM | 861 | O | GLU | A | 114 | 30.993 | 46.331 | 34.887 | 1.00 | 25.96 | O |
| ATOM | 862 | CB | GLU | A | 114 | 32.446 | 44.825 | 32.332 | 1.00 | 33.04 | C |
| ATOM | 863 | CG | GLU | A | 114 | 32.800 | 43.427 | 31.863 | 1.00 | 37.74 | C |
| ATOM | 864 | CD | GLU | A | 114 | 34.018 | 43.395 | 30.940 | 1.00 | 39.47 | C |
| ATOM | 865 | OE1 | GLU | A | 114 | 34.524 | 42.280 | 30.682 | 1.00 | 42.15 | O |
| ATOM | 866 | OE2 | GLU | A | 114 | 34.461 | 44.471 | 30.467 | 1.00 | 37.94 | O |
| ATOM | 867 | N | PHE | A | 115 | 30.833 | 47.388 | 32.920 | 1.00 | 26.11 | N |
| ATOM | 868 | CA | PHE | A | 115 | 30.741 | 48.694 | 33.555 | 1.00 | 27.02 | C |
| ATOM | 869 | C | PHE | A | 115 | 29.579 | 48.772 | 34.542 | 1.00 | 26.62 | C |
| ATOM | 870 | O | PHE | A | 115 | 29.754 | 49.149 | 35.700 | 1.00 | 25.93 | O |
| ATOM | 871 | CB | PHE | A | 115 | 30.556 | 49.794 | 32.521 | 1.00 | 26.88 | C |
| ATOM | 872 | CG | PHE | A | 115 | 30.456 | 51.163 | 33.128 | 1.00 | 30.78 | C |
| ATOM | 873 | CD1 | PHE | A | 115 | 31.591 | 51.970 | 33.254 | 1.00 | 30.44 | C |
| ATOM | 874 | CD2 | PHE | A | 115 | 29.236 | 51.635 | 33.616 | 1.00 | 30.33 | C |
| ATOM | 875 | CE1 | PHE | A | 115 | 31.509 | 53.230 | 33.857 | 1.00 | 29.53 | C |
| ATOM | 876 | CE2 | PHE | A | 115 | 29.143 | 52.891 | 34.221 | 1.00 | 31.72 | C |
| ATOM | 877 | CZ | PHE | A | 115 | 30.284 | 53.691 | 34.341 | 1.00 | 30.73 | C |
| ATOM | 878 | N | PHE | A | 116 | 28.385 | 48.424 | 34.083 | 1.00 | 26.41 | N |
| ATOM | 879 | CA | PHE | A | 116 | 27.225 | 48.499 | 34.950 | 1.00 | 24.93 | C |
| ATOM | 880 | C | PHE | A | 116 | 27.144 | 47.446 | 36.050 | 1.00 | 26.82 | C |
| ATOM | 881 | O | PHE | A | 116 | 26.349 | 47.561 | 36.985 | 1.00 | 26.48 | O |
| ATOM | 882 | CB | PHE | A | 116 | 25.972 | 48.548 | 34.093 | 1.00 | 21.48 | C |
| ATOM | 883 | CG | PHE | A | 116 | 25.814 | 49.857 | 33.376 | 1.00 | 22.31 | C |
| ATOM | 884 | CD1 | PHE | A | 116 | 26.231 | 50.004 | 32.050 | 1.00 | 21.26 | C |
| ATOM | 885 | CD2 | PHE | A | 116 | 25.298 | 50.972 | 34.048 | 1.00 | 19.11 | C |
| ATOM | 886 | CE1 | PHE | A | 116 | 26.136 | 51.232 | 31.406 | 1.00 | 21.62 | C |
| ATOM | 887 | CE2 | PHE | A | 116 | 25.201 | 52.210 | 33.409 | 1.00 | 18.12 | C |
| ATOM | 888 | CZ | PHE | A | 116 | 25.614 | 52.348 | 32.095 | 1.00 | 17.80 | C |
| ATOM | 889 | N | ARG | A | 117 | 28.000 | 46.436 | 35.958 | 1.00 | 29.44 | N |
| ATOM | 890 | CA | ARG | A | 117 | 28.061 | 45.400 | 36.979 | 1.00 | 31.66 | C |
| ATOM | 891 | C | ARG | A | 117 | 28.838 | 46.065 | 38.115 | 1.00 | 32.46 | C |
| ATOM | 892 | O | ARG | A | 117 | 28.516 | 45.900 | 39.294 | 1.00 | 32.67 | O |
| ATOM | 893 | CB | ARG | A | 117 | 28.832 | 44.194 | 36.438 | 1.00 | 35.82 | C |
| ATOM | 894 | CG | ARG | A | 117 | 28.651 | 42.903 | 37.210 | 1.00 | 39.66 | C |
| ATOM | 895 | CD | ARG | A | 117 | 28.987 | 41.725 | 36.308 | 1.00 | 43.82 | C |
| ATOM | 896 | NE | ARG | A | 117 | 30.354 | 41.798 | 35.792 | 1.00 | 47.67 | N |
| ATOM | 897 | CZ | ARG | A | 117 | 30.746 | 41.285 | 34.627 | 1.00 | 49.48 | C |
| ATOM | 898 | NH1 | ARG | A | 117 | 29.878 | 40.660 | 33.842 | 1.00 | 50.53 | N |
| ATOM | 899 | NH2 | ARG | A | 117 | 32.010 | 41.398 | 34.245 | 1.00 | 50.55 | N |
| ATOM | 900 | N | ILE | A | 118 | 29.867 | 46.821 | 37.737 | 1.00 | 29.93 | N |

TABLE 4-continued

Stem Cell Factor Dimer

| ATOM | 901 | CA | ILE | A | 118 | 30.689 | 47.549 | 38.694 | 1.00 | 29.90 | C |
|---|---|---|---|---|---|---|---|---|---|---|---|
| ATOM | 902 | C | ILE | A | 118 | 29.807 | 48.629 | 39.316 | 1.00 | 29.75 | C |
| ATOM | 903 | O | ILE | A | 118 | 29.908 | 48.929 | 40.503 | 1.00 | 29.74 | O |
| ATOM | 904 | CB | ILE | A | 118 | 31.892 | 48.211 | 37.989 | 1.00 | 28.84 | C |
| ATOM | 905 | CG1 | ILE | A | 118 | 32.917 | 47.144 | 37.613 | 1.00 | 30.83 | C |
| ATOM | 906 | CG2 | ILE | A | 118 | 32.513 | 49.279 | 38.881 | 1.00 | 26.59 | C |
| ATOM | 907 | CD1 | ILE | A | 118 | 33.987 | 47.647 | 36.674 | 1.00 | 31.10 | C |
| ATOM | 908 | N | PHE | A | 119 | 28.931 | 49.203 | 38.501 | 1.00 | 30.34 | N |
| ATOM | 909 | CA | PHE | A | 119 | 28.010 | 50.233 | 38.959 | 1.00 | 31.08 | C |
| ATOM | 910 | C | PHE | A | 119 | 27.031 | 49.710 | 40.019 | 1.00 | 32.65 | C |
| ATOM | 911 | O | PHE | A | 119 | 26.774 | 50.371 | 41.027 | 1.00 | 31.33 | O |
| ATOM | 912 | CB | PHE | A | 119 | 27.208 | 50.772 | 37.776 | 1.00 | 31.48 | C |
| ATOM | 913 | CG | PHE | A | 119 | 26.095 | 51.693 | 38.176 | 1.00 | 32.42 | C |
| ATOM | 914 | CD1 | PHE | A | 119 | 26.270 | 53.069 | 38.142 | 1.00 | 31.11 | C |
| ATOM | 915 | CD2 | PHE | A | 119 | 24.878 | 51.181 | 38.625 | 1.00 | 31.66 | C |
| ATOM | 916 | CE1 | PHE | A | 119 | 25.252 | 53.930 | 38.551 | 1.00 | 30.46 | C |
| ATOM | 917 | CE2 | PHE | A | 119 | 23.862 | 52.027 | 39.034 | 1.00 | 33.26 | C |
| ATOM | 918 | CZ | PHE | A | 119 | 24.051 | 53.412 | 38.997 | 1.00 | 32.00 | C |
| ATOM | 919 | N | ASN | A | 120 | 26.465 | 48.532 | 39.769 | 1.00 | 33.86 | N |
| ATOM | 920 | CA | ASN | A | 120 | 25.497 | 47.933 | 40.684 | 1.00 | 32.06 | C |
| ATOM | 921 | C | ASN | A | 120 | 26.118 | 47.493 | 42.009 | 1.00 | 31.89 | C |
| ATOM | 922 | O | ASN | A | 120 | 25.499 | 47.628 | 43.066 | 1.00 | 27.46 | O |
| ATOM | 923 | CB | ASN | A | 120 | 24.813 | 46.740 | 40.009 | 1.00 | 32.78 | C |
| ATOM | 924 | CG | ASN | A | 120 | 23.845 | 47.164 | 38.909 | 1.00 | 33.81 | C |
| ATOM | 925 | OD1 | ASN | A | 120 | 23.476 | 46.363 | 38.050 | 1.00 | 33.86 | O |
| ATOM | 926 | ND2 | ASN | A | 120 | 23.419 | 48.420 | 38.944 | 1.00 | 35.07 | N |
| ATOM | 927 | N | ARG | A | 121 | 27.332 | 46.956 | 41.949 | 1.00 | 31.62 | N |
| ATOM | 928 | CA | ARG | A | 121 | 28.012 | 46.519 | 43.157 | 1.00 | 34.36 | C |
| ATOM | 929 | C | ARG | A | 121 | 28.363 | 47.722 | 44.023 | 1.00 | 35.61 | C |
| ATOM | 930 | O | ARG | A | 121 | 28.255 | 47.666 | 45.249 | 1.00 | 33.43 | O |
| ATOM | 931 | CB | ARG | A | 121 | 29.274 | 45.711 | 42.814 | 1.00 | 37.30 | C |
| ATOM | 932 | CG | ARG | A | 121 | 28.962 | 44.255 | 42.456 | 1.00 | 44.29 | C |
| ATOM | 933 | CD | ARG | A | 121 | 30.205 | 43.407 | 42.180 | 1.00 | 51.94 | C |
| ATOM | 934 | NE | ARG | A | 121 | 30.815 | 43.668 | 40.873 | 1.00 | 57.49 | N |
| ATOM | 935 | CZ | ARG | A | 121 | 31.775 | 42.916 | 40.334 | 1.00 | 61.41 | C |
| ATOM | 936 | NH1 | ARG | A | 121 | 32.236 | 41.852 | 40.990 | 1.00 | 62.64 | N |
| ATOM | 937 | NH2 | ARG | A | 121 | 32.275 | 43.216 | 39.137 | 1.00 | 62.08 | N |
| ATOM | 938 | N | SER | A | 122 | 28.768 | 48.816 | 43.384 | 1.00 | 36.07 | N |
| ATOM | 939 | CA | SER | A | 122 | 29.113 | 50.026 | 44.119 | 1.00 | 37.98 | C |
| ATOM | 940 | C | SER | A | 122 | 27.882 | 50.557 | 44.857 | 1.00 | 39.98 | C |
| ATOM | 941 | O | SER | A | 122 | 27.950 | 50.914 | 46.037 | 1.00 | 37.20 | O |
| ATOM | 942 | CB | SER | A | 122 | 29.647 | 51.086 | 43.155 | 1.00 | 38.15 | C |
| ATOM | 943 | OG | SER | A | 122 | 30.806 | 50.621 | 42.481 | 1.00 | 36.97 | O |
| ATOM | 944 | N | ILE | A | 123 | 26.747 | 50.600 | 44.169 | 1.00 | 42.51 | N |
| ATOM | 945 | CA | ILE | A | 123 | 25.533 | 51.095 | 44.802 | 1.00 | 46.25 | C |
| ATOM | 946 | C | ILE | A | 123 | 24.993 | 50.111 | 45.829 | 1.00 | 47.13 | C |
| ATOM | 947 | O | ILE | A | 123 | 24.503 | 50.507 | 46.888 | 1.00 | 46.85 | O |
| ATOM | 948 | CB | ILE | A | 123 | 24.463 | 51.434 | 43.751 | 1.00 | 47.26 | C |
| ATOM | 949 | CG1 | ILE | A | 123 | 24.838 | 52.765 | 43.090 | 1.00 | 50.91 | C |
| ATOM | 950 | CG2 | ILE | A | 123 | 23.084 | 51.506 | 44.392 | 1.00 | 47.45 | C |
| ATOM | 951 | CD1 | ILE | A | 123 | 23.836 | 53.277 | 42.098 | 1.00 | 54.97 | C |
| ATOM | 952 | N | ASP | A | 124 | 25.096 | 48.827 | 45.529 | 1.00 | 49.20 | N |
| ATOM | 953 | CA | ASP | A | 124 | 24.630 | 47.819 | 46.467 | 1.00 | 52.74 | C |
| ATOM | 954 | C | ASP | A | 124 | 25.502 | 47.921 | 47.717 | 1.00 | 54.58 | C |
| ATOM | 955 | O | ASP | A | 124 | 25.087 | 47.545 | 48.810 | 1.00 | 55.49 | O |
| ATOM | 956 | CB | ASP | A | 124 | 24.741 | 46.422 | 45.842 | 1.00 | 52.44 | C |
| ATOM | 957 | CG | ASP | A | 124 | 24.404 | 45.313 | 46.819 | 1.00 | 54.83 | C |
| ATOM | 958 | OD1 | ASP | A | 124 | 23.274 | 45.302 | 47.361 | 1.00 | 55.33 | O |
| ATOM | 959 | OD2 | ASP | A | 124 | 25.275 | 44.446 | 47.042 | 1.00 | 54.45 | O |
| ATOM | 960 | N | ALA | A | 125 | 26.707 | 48.455 | 47.550 | 1.00 | 57.11 | N |
| ATOM | 961 | CA | ALA | A | 125 | 27.642 | 48.602 | 48.660 | 1.00 | 60.02 | C |
| ATOM | 962 | C | ALA | A | 125 | 27.048 | 49.443 | 49.780 | 1.00 | 62.57 | C |
| ATOM | 963 | O | ALA | A | 125 | 27.347 | 49.220 | 50.950 | 1.00 | 61.70 | O |
| ATOM | 964 | CB | ALA | A | 125 | 28.947 | 49.222 | 48.179 | 1.00 | 58.07 | C |
| ATOM | 965 | N | PHE | A | 126 | 26.217 | 50.417 | 49.431 | 1.00 | 65.62 | N |
| ATOM | 966 | CA | PHE | A | 126 | 25.600 | 51.236 | 50.461 | 1.00 | 70.24 | C |
| ATOM | 967 | C | PHE | A | 126 | 24.527 | 50.415 | 51.154 | 1.00 | 73.56 | C |
| ATOM | 968 | O | PHE | A | 126 | 24.498 | 50.330 | 52.381 | 1.00 | 74.48 | O |
| ATOM | 969 | CB | PHE | A | 126 | 24.978 | 52.494 | 49.866 | 1.00 | 69.43 | C |
| ATOM | 970 | CG | PHE | A | 126 | 25.981 | 53.477 | 49.356 | 1.00 | 69.16 | C |
| ATOM | 971 | CD1 | PHE | A | 126 | 26.601 | 53.285 | 48.127 | 1.00 | 69.83 | C |
| ATOM | 972 | CD2 | PHE | A | 126 | 26.312 | 54.597 | 50.107 | 1.00 | 68.36 | C |
| ATOM | 973 | CE1 | PHE | A | 126 | 27.539 | 54.200 | 47.649 | 1.00 | 70.13 | C |
| ATOM | 974 | CE2 | PHE | A | 126 | 27.248 | 55.517 | 49.641 | 1.00 | 69.60 | C |
| ATOM | 975 | CZ | PHE | A | 126 | 27.863 | 55.319 | 48.410 | 1.00 | 70.07 | C |
| ATOM | 976 | N | LYS | A | 127 | 23.654 | 49.807 | 50.357 | 1.00 | 77.43 | N |
| ATOM | 977 | CA | LYS | A | 127 | 22.572 | 48.974 | 50.875 | 1.00 | 80.53 | C |

TABLE 4-continued

Stem Cell Factor Dimer

| ATOM | 978 | C | LYS | A | 127 | 22.998 | 48.235 | 52.138 | 1.00 | 82.15 | C |
|------|-----|-----|-----|---|-----|--------|--------|--------|------|--------|---|
| ATOM | 979 | O | LYS | A | 127 | 22.474 | 48.481 | 53.225 | 1.00 | 82.37 | O |
| ATOM | 980 | CB | LYS | A | 127 | 22.144 | 47.946 | 49.823 | 1.00 | 81.53 | C |
| ATOM | 981 | CG | LYS | A | 127 | 21.483 | 48.530 | 48.588 | 1.00 | 83.56 | C |
| ATOM | 982 | CD | LYS | A | 127 | 20.069 | 49.007 | 48.884 | 1.00 | 84.91 | C |
| ATOM | 983 | CE | LYS | A | 127 | 19.376 | 49.490 | 47.618 | 1.00 | 85.48 | C |
| ATOM | 984 | NZ | LYS | A | 127 | 17.966 | 49.903 | 47.871 | 1.00 | 86.48 | N |
| ATOM | 985 | N | ASP | A | 128 | 23.961 | 47.334 | 51.980 | 1.00 | 84.12 | N |
| ATOM | 986 | CA | ASP | A | 128 | 24.461 | 46.531 | 53.087 | 1.00 | 85.76 | C |
| ATOM | 987 | C | ASP | A | 128 | 25.830 | 47.036 | 53.547 | 1.00 | 86.14 | C |
| ATOM | 988 | O | ASP | A | 128 | 26.860 | 46.439 | 53.234 | 1.00 | 86.66 | O |
| ATOM | 989 | CB | ASP | A | 128 | 24.551 | 45.067 | 52.641 | 1.00 | 87.18 | C |
| ATOM | 990 | CG | ASP | A | 128 | 23.279 | 44.586 | 51.946 | 1.00 | 88.36 | C |
| ATOM | 991 | OD1 | ASP | A | 128 | 22.226 | 44.474 | 52.614 | 1.00 | 87.93 | O |
| ATOM | 992 | OD2 | ASP | A | 128 | 23.333 | 44.326 | 50.725 | 1.00 | 89.41 | O |
| ATOM | 993 | N | PHE | A | 129 | 25.834 | 48.134 | 54.297 | 1.00 | 86.40 | N |
| ATOM | 994 | CA | PHE | A | 129 | 27.075 | 48.730 | 54.780 | 1.00 | 87.11 | C |
| ATOM | 995 | C | PHE | A | 129 | 26.903 | 49.423 | 56.131 | 1.00 | 89.71 | C |
| ATOM | 996 | O | PHE | A | 129 | 26.196 | 50.427 | 56.232 | 1.00 | 90.14 | O |
| ATOM | 997 | CB | PHE | A | 129 | 27.583 | 49.737 | 53.745 | 1.00 | 84.15 | C |
| ATOM | 998 | CG | PHE | A | 129 | 28.741 | 50.573 | 54.213 | 1.00 | 81.11 | C |
| ATOM | 999 | CD1 | PHE | A | 129 | 29.943 | 49.983 | 54.580 | 1.00 | 79.96 | C |
| ATOM | 1000 | CD2 | PHE | A | 129 | 28.631 | 51.958 | 54.267 | 1.00 | 80.34 | C |
| ATOM | 1001 | CE1 | PHE | A | 129 | 31.025 | 50.764 | 54.994 | 1.00 | 79.71 | C |
| ATOM | 1002 | CE2 | PHE | A | 129 | 29.705 | 52.747 | 54.678 | 1.00 | 78.88 | C |
| ATOM | 1003 | CZ | PHE | A | 129 | 30.903 | 52.150 | 55.042 | 1.00 | 78.87 | C |
| ATOM | 1004 | N | VAL | A | 130 | 27.557 | 48.889 | 57.162 | 1.00 | 92.58 | N |
| ATOM | 1005 | CA | VAL | A | 130 | 27.481 | 49.464 | 58.504 | 1.00 | 95.55 | C |
| ATOM | 1006 | C | VAL | A | 130 | 28.826 | 49.438 | 59.224 | 1.00 | 97.26 | C |
| ATOM | 1007 | O | VAL | A | 130 | 29.171 | 50.375 | 59.945 | 1.00 | 97.26 | O |
| ATOM | 1008 | CB | VAL | A | 130 | 26.460 | 48.717 | 59.389 | 1.00 | 95.85 | C |
| ATOM | 1009 | CG1 | VAL | A | 130 | 25.068 | 48.824 | 58.786 | 1.00 | 96.51 | C |
| ATOM | 1010 | CG2 | VAL | A | 130 | 26.872 | 47.262 | 59.543 | 1.00 | 96.16 | C |
| ATOM | 1011 | N | VAL | A | 131 | 29.579 | 48.360 | 59.029 | 1.00 | 99.84 | N |
| ATOM | 1012 | CA | VAL | A | 131 | 30.882 | 48.210 | 59.668 | 1.00 | 102.46 | C |
| ATOM | 1013 | C | VAL | A | 131 | 32.028 | 48.784 | 58.836 | 1.00 | 103.49 | C |
| ATOM | 1014 | O | VAL | A | 131 | 32.706 | 48.060 | 58.104 | 1.00 | 103.21 | O |
| ATOM | 1015 | CB | VAL | A | 131 | 31.184 | 46.719 | 59.985 | 1.00 | 102.88 | C |
| ATOM | 1016 | CG1 | VAL | A | 131 | 30.277 | 46.235 | 61.104 | 1.00 | 103.34 | C |
| ATOM | 1017 | CG2 | VAL | A | 131 | 30.980 | 45.861 | 58.743 | 1.00 | 103.19 | C |
| ATOM | 1018 | N | ALA | A | 132 | 32.239 | 50.091 | 58.957 | 1.00 | 105.08 | N |
| ATOM | 1019 | CA | ALA | A | 132 | 33.305 | 50.763 | 58.226 | 1.00 | 106.69 | C |
| ATOM | 1020 | C | ALA | A | 132 | 34.662 | 50.287 | 58.740 | 1.00 | 107.70 | C |
| ATOM | 1021 | O | ALA | A | 132 | 35.053 | 49.142 | 58.505 | 1.00 | 108.08 | O |
| ATOM | 1022 | CB | ALA | A | 132 | 33.179 | 52.273 | 58.390 | 1.00 | 107.04 | C |
| ATOM | 1023 | N | SER | A | 133 | 35.374 | 51.162 | 59.443 | 1.00 | 108.41 | N |
| ATOM | 1024 | CA | SER | A | 133 | 36.683 | 50.814 | 59.985 | 1.00 | 108.93 | C |
| ATOM | 1025 | C | SER | A | 133 | 36.553 | 49.949 | 61.233 | 1.00 | 109.08 | C |
| ATOM | 1026 | O | SER | A | 133 | 37.146 | 48.873 | 61.316 | 1.00 | 109.42 | O |
| ATOM | 1027 | CB | SER | A | 133 | 37.474 | 52.080 | 60.319 | 1.00 | 109.04 | C |
| ATOM | 1028 | OG | SER | A | 133 | 37.762 | 52.822 | 59.149 | 1.00 | 109.34 | O |
| ATOM | 1029 | N | ASP | A | 137 | 41.268 | 48.968 | 58.587 | 1.00 | 83.95 | N |
| ATOM | 1030 | CA | ASP | A | 137 | 42.374 | 49.562 | 57.843 | 1.00 | 83.77 | C |
| ATOM | 1031 | C | ASP | A | 137 | 42.267 | 49.218 | 56.364 | 1.00 | 81.65 | C |
| ATOM | 1032 | O | ASP | A | 137 | 41.504 | 48.332 | 55.981 | 1.00 | 81.87 | O |
| ATOM | 1033 | CB | ASP | A | 137 | 43.717 | 49.065 | 58.394 | 1.00 | 86.05 | C |
| ATOM | 1034 | CG | ASP | A | 137 | 43.883 | 47.557 | 58.272 | 1.00 | 88.47 | C |
| ATOM | 1035 | OD1 | ASP | A | 137 | 43.812 | 47.033 | 57.138 | 1.00 | 88.58 | O |
| ATOM | 1036 | OD2 | ASP | A | 137 | 44.091 | 46.894 | 59.313 | 1.00 | 89.29 | O |
| ATOM | 1037 | N | CYS | A | 138 | 43.040 | 49.917 | 55.538 | 1.00 | 78.93 | N |
| ATOM | 1038 | CA | CYS | A | 138 | 43.023 | 49.683 | 54.096 | 1.00 | 76.20 | C |
| ATOM | 1039 | C | CYS | A | 138 | 44.422 | 49.466 | 53.512 | 1.00 | 77.44 | C |
| ATOM | 1040 | O | CYS | A | 138 | 44.569 | 49.241 | 52.307 | 1.00 | 77.09 | O |
| ATOM | 1041 | CB | CYS | A | 138 | 42.353 | 50.862 | 53.382 | 1.00 | 70.43 | C |
| ATOM | 1042 | SG | CYS | A | 138 | 40.648 | 51.212 | 53.925 | 1.00 | 63.65 | S |
| ATOM | 1043 | N | VAL | A | 139 | 45.439 | 49.536 | 54.370 | 1.00 | 78.37 | N |
| ATOM | 1044 | CA | VAL | A | 139 | 46.833 | 49.358 | 53.962 | 1.00 | 78.39 | C |
| ATOM | 1045 | C | VAL | A | 139 | 47.356 | 50.580 | 53.213 | 1.00 | 78.35 | C |
| ATOM | 1046 | O | VAL | A | 139 | 47.151 | 50.719 | 52.007 | 1.00 | 78.45 | O |
| ATOM | 1047 | CB | VAL | A | 139 | 47.005 | 48.108 | 53.067 | 1.00 | 78.28 | C |
| ATOM | 1048 | CG1 | VAL | A | 139 | 48.422 | 48.043 | 52.523 | 1.00 | 79.62 | C |
| ATOM | 1049 | CG2 | VAL | A | 139 | 46.692 | 46.856 | 53.867 | 1.00 | 78.33 | C |
| TER | 1050 |  | VAL | A | 139 |  |  |  |  |  |  |
| ATOM | 1051 | N | GLY | B | 202 | 5.074 | 53.926 | −9.864 | 1.00 | 55.94 | N |
| ATOM | 1052 | CA | GLY | B | 202 | 5.956 | 53.732 | −8.727 | 1.00 | 56.16 | C |
| ATOM | 1053 | C | GLY | B | 202 | 7.260 | 53.075 | −9.131 | 1.00 | 56.05 | C |
| ATOM | 1054 | O | GLY | B | 202 | 7.265 | 52.063 | −9.833 | 1.00 | 55.94 | O |

TABLE 4-continued

Stem Cell Factor Dimer

| ATOM | 1055 | N | ILE | B | 203 | 8.373 | 53.652 | -8.692 | 1.00 | 56.92 | N |
|---|---|---|---|---|---|---|---|---|---|---|---|
| ATOM | 1056 | CA | ILE | B | 203 | 9.686 | 53.106 | -9.017 | 1.00 | 57.39 | C |
| ATOM | 1057 | C | ILE | B | 203 | 10.204 | 52.286 | -7.842 | 1.00 | 59.41 | C |
| ATOM | 1058 | O | ILE | B | 203 | 10.614 | 52.862 | -6.828 | 1.00 | 60.09 | O |
| ATOM | 1059 | CB | ILE | B | 203 | 10.706 | 54.226 | -9.298 | 1.00 | 56.02 | C |
| ATOM | 1060 | CG1 | ILE | B | 203 | 10.124 | 55.231 | -10.295 | 1.00 | 55.36 | C |
| ATOM | 1061 | CG2 | ILE | B | 203 | 12.004 | 53.619 | -9.838 | 1.00 | 55.71 | C |
| ATOM | 1062 | CD1 | ILE | B | 203 | 11.049 | 56.410 | -10.594 | 1.00 | 53.98 | C |
| ATOM | 1063 | N | CYS | B | 204 | 10.192 | 50.957 | -7.978 | 1.00 | 60.84 | N |
| ATOM | 1064 | CA | CYS | B | 204 | 10.667 | 50.061 | -6.915 | 1.00 | 62.54 | C |
| ATOM | 1065 | C | CYS | B | 204 | 10.340 | 50.704 | -5.563 | 1.00 | 61.09 | C |
| ATOM | 1066 | O | CYS | B | 204 | 11.195 | 50.815 | -4.683 | 1.00 | 61.84 | O |
| ATOM | 1067 | CB | CYS | B | 204 | 12.191 | 49.818 | -7.068 | 1.00 | 66.33 | C |
| ATOM | 1068 | SG | CYS | B | 204 | 13.033 | 48.997 | -5.663 | 1.00 | 73.54 | S |
| ATOM | 1069 | N | ARG | B | 205 | 9.092 | 51.148 | -5.423 | 1.00 | 59.31 | N |
| ATOM | 1070 | CA | ARG | B | 205 | 8.623 | 51.799 | -4.200 | 1.00 | 57.61 | C |
| ATOM | 1071 | C | ARG | B | 205 | 7.697 | 50.895 | -3.390 | 1.00 | 58.14 | C |
| ATOM | 1072 | O | ARG | B | 205 | 6.770 | 51.363 | -2.723 | 1.00 | 58.84 | O |
| ATOM | 1073 | CB | ARG | B | 205 | 7.897 | 53.103 | -4.548 | 1.00 | 55.04 | C |
| ATOM | 1074 | CG | ARG | B | 205 | 8.829 | 54.255 | -4.882 | 1.00 | 53.30 | C |
| ATOM | 1075 | CD | ARG | B | 205 | 9.663 | 54.623 | -3.662 | 1.00 | 51.85 | C |
| ATOM | 1076 | NE | ARG | B | 205 | 10.694 | 55.614 | -3.959 | 1.00 | 51.10 | N |
| ATOM | 1077 | CZ | ARG | B | 205 | 10.455 | 56.878 | -4.304 | 1.00 | 52.18 | C |
| ATOM | 1078 | NH1 | ARG | B | 205 | 9.207 | 57.326 | -4.402 | 1.00 | 50.83 | N |
| ATOM | 1079 | NH2 | ARG | B | 205 | 11.470 | 57.699 | -4.549 | 1.00 | 51.90 | N |
| ATOM | 1080 | N | ASN | B | 206 | 7.963 | 49.597 | -3.457 | 1.00 | 57.68 | N |
| ATOM | 1081 | CA | ASN | B | 206 | 7.177 | 48.600 | -2.747 | 1.00 | 57.99 | C |
| ATOM | 1082 | C | ASN | B | 206 | 7.799 | 48.464 | -1.372 | 1.00 | 58.60 | C |
| ATOM | 1083 | O | ASN | B | 206 | 8.941 | 48.009 | -1.256 | 1.00 | 59.53 | O |
| ATOM | 1084 | CB | ASN | B | 206 | 7.265 | 47.275 | -3.490 | 1.00 | 58.87 | C |
| ATOM | 1085 | CG | ASN | B | 206 | 7.246 | 47.465 | -4.991 | 1.00 | 60.42 | C |
| ATOM | 1086 | OD1 | ASN | B | 206 | 6.220 | 47.837 | -5.568 | 1.00 | 60.92 | O |
| ATOM | 1087 | ND2 | ASN | B | 206 | 8.393 | 47.234 | -5.634 | 1.00 | 61.57 | N |
| ATOM | 1088 | N | ARG | B | 207 | 7.054 | 48.859 | -0.340 | 1.00 | 57.82 | N |
| ATOM | 1089 | CA | ARG | B | 207 | 7.544 | 48.808 | 1.037 | 1.00 | 57.03 | C |
| ATOM | 1090 | C | ARG | B | 207 | 8.912 | 49.498 | 1.053 | 1.00 | 58.08 | C |
| ATOM | 1091 | O | ARG | B | 207 | 9.773 | 49.210 | 1.894 | 1.00 | 57.11 | O |
| ATOM | 1092 | CB | ARG | B | 207 | 7.649 | 47.346 | 1.521 | 1.00 | 55.63 | C |
| ATOM | 1093 | CG | ARG | B | 207 | 8.750 | 46.525 | 0.856 | 1.00 | 52.82 | C |
| ATOM | 1094 | CD | ARG | B | 207 | 8.631 | 45.020 | 1.100 | 1.00 | 52.16 | C |
| ATOM | 1095 | NE | ARG | B | 207 | 8.902 | 44.625 | 2.480 | 1.00 | 49.34 | N |
| ATOM | 1096 | CZ | ARG | B | 207 | 9.331 | 43.414 | 2.827 | 1.00 | 50.30 | C |
| ATOM | 1097 | NH1 | ARG | B | 207 | 9.544 | 42.494 | 1.892 | 1.00 | 51.49 | N |
| ATOM | 1098 | NH2 | ARG | B | 207 | 9.533 | 43.112 | 4.104 | 1.00 | 51.05 | N |
| ATOM | 1099 | N | VAL | B | 208 | 9.089 | 50.422 | 0.107 | 1.00 | 58.69 | N |
| ATOM | 1100 | CA | VAL | B | 208 | 10.338 | 51.161 | -0.043 | 1.00 | 59.57 | C |
| ATOM | 1101 | C | VAL | B | 208 | 10.269 | 52.566 | 0.556 | 1.00 | 60.47 | C |
| ATOM | 1102 | O | VAL | B | 208 | 10.764 | 53.535 | -0.031 | 1.00 | 59.70 | O |
| ATOM | 1103 | CB | VAL | B | 208 | 10.732 | 51.256 | -1.535 | 1.00 | 58.68 | C |
| ATOM | 1104 | CG1 | VAL | B | 208 | 12.100 | 51.912 | -1.687 | 1.00 | 56.09 | C |
| ATOM | 1105 | CG2 | VAL | B | 208 | 10.752 | 49.864 | -2.142 | 1.00 | 56.94 | C |
| ATOM | 1106 | N | THR | B | 209 | 9.648 | 52.674 | 1.727 | 1.00 | 61.79 | N |
| ATOM | 1107 | CA | THR | B | 209 | 9.543 | 53.957 | 2.411 | 1.00 | 64.19 | C |
| ATOM | 1108 | C | THR | B | 209 | 10.441 | 53.909 | 3.638 | 1.00 | 65.48 | C |
| ATOM | 1109 | O | THR | B | 209 | 10.082 | 53.327 | 4.666 | 1.00 | 66.03 | O |
| ATOM | 1110 | CB | THR | B | 209 | 8.096 | 54.249 | 2.850 | 1.00 | 64.54 | C |
| ATOM | 1111 | OG1 | THR | B | 209 | 7.258 | 54.339 | 1.691 | 1.00 | 66.58 | O |
| ATOM | 1112 | CG2 | THR | B | 209 | 8.025 | 55.563 | 3.619 | 1.00 | 64.63 | C |
| ATOM | 1113 | N | ASN | B | 210 | 11.616 | 54.519 | 3.514 | 1.00 | 67.03 | N |
| ATOM | 1114 | CA | ASN | B | 210 | 12.600 | 54.555 | 4.592 | 1.00 | 68.22 | C |
| ATOM | 1115 | C | ASN | B | 210 | 12.085 | 55.139 | 5.907 | 1.00 | 69.19 | C |
| ATOM | 1116 | O | ASN | B | 210 | 12.135 | 54.478 | 6.948 | 1.00 | 69.69 | O |
| ATOM | 1117 | CB | ASN | B | 210 | 13.836 | 55.330 | 4.132 | 1.00 | 67.77 | C |
| ATOM | 1118 | CG | ASN | B | 210 | 14.748 | 55.710 | 5.280 | 1.00 | 68.67 | C |
| ATOM | 1119 | OD1 | ASN | B | 210 | 14.953 | 54.931 | 6.212 | 1.00 | 67.36 | O |
| ATOM | 1120 | ND2 | ASN | B | 210 | 15.312 | 56.913 | 5.214 | 1.00 | 69.95 | N |
| ATOM | 1121 | N | ASN | B | 211 | 11.599 | 56.376 | 5.862 | 1.00 | 69.70 | N |
| ATOM | 1122 | CA | ASN | B | 211 | 11.089 | 57.040 | 7.059 | 1.00 | 69.97 | C |
| ATOM | 1123 | C | ASN | B | 211 | 12.224 | 57.278 | 8.050 | 1.00 | 69.52 | C |
| ATOM | 1124 | O | ASN | B | 211 | 12.468 | 56.470 | 8.950 | 1.00 | 69.57 | O |
| ATOM | 1125 | CB | ASN | B | 211 | 10.000 | 56.188 | 7.707 | 1.00 | 70.79 | C |
| ATOM | 1126 | CG | ASN | B | 211 | 8.873 | 55.870 | 6.750 | 1.00 | 71.27 | C |
| ATOM | 1127 | OD1 | ASN | B | 211 | 8.127 | 56.757 | 6.334 | 1.00 | 71.14 | O |
| ATOM | 1128 | ND2 | ASN | B | 211 | 8.751 | 54.601 | 6.385 | 1.00 | 71.65 | N |
| ATOM | 1129 | N | VAL | B | 212 | 12.914 | 58.398 | 7.867 | 1.00 | 68.75 | N |
| ATOM | 1130 | CA | VAL | B | 212 | 14.036 | 58.772 | 8.719 | 1.00 | 67.00 | C |
| ATOM | 1131 | C | VAL | B | 212 | 13.647 | 59.074 | 10.168 | 1.00 | 65.19 | C |

TABLE 4-continued

Stem Cell Factor Dimer

| ATOM | 1132 | O | VAL | B | 212 | 14.513 | 59.328 | 11.001 | 1.00 | 63.87 | O |
|---|---|---|---|---|---|---|---|---|---|---|---|
| ATOM | 1133 | CB | VAL | B | 212 | 14.785 | 59.994 | 8.133 | 1.00 | 67.35 | C |
| ATOM | 1134 | CG1 | VAL | B | 212 | 15.791 | 59.537 | 7.087 | 1.00 | 67.33 | C |
| ATOM | 1135 | CG2 | VAL | B | 212 | 13.789 | 60.957 | 7.503 | 1.00 | 66.47 | C |
| ATOM | 1136 | N | LYS | B | 213 | 12.350 | 59.049 | 10.465 | 1.00 | 63.78 | N |
| ATOM | 1137 | CA | LYS | B | 213 | 11.880 | 59.307 | 11.827 | 1.00 | 61.90 | C |
| ATOM | 1138 | C | LYS | B | 213 | 12.570 | 58.335 | 12.778 | 1.00 | 59.48 | C |
| ATOM | 1139 | O | LYS | B | 213 | 13.009 | 58.715 | 13.866 | 1.00 | 58.25 | O |
| ATOM | 1140 | CB | LYS | B | 213 | 10.360 | 59.119 | 11.922 | 1.00 | 63.24 | C |
| ATOM | 1141 | CG | LYS | B | 213 | 9.551 | 60.117 | 11.096 | 1.00 | 66.28 | C |
| ATOM | 1142 | CD | LYS | B | 213 | 8.053 | 59.861 | 11.206 | 1.00 | 66.69 | C |
| ATOM | 1143 | CE | LYS | B | 213 | 7.264 | 60.822 | 10.327 | 1.00 | 66.77 | C |
| ATOM | 1144 | NZ | LYS | B | 213 | 5.829 | 60.439 | 10.227 | 1.00 | 66.50 | N |
| ATOM | 1145 | N | ASP | B | 214 | 12.664 | 57.079 | 12.352 | 1.00 | 56.30 | N |
| ATOM | 1146 | CA | ASP | B | 214 | 13.302 | 56.043 | 13.152 | 1.00 | 53.09 | C |
| ATOM | 1147 | C | ASP | B | 214 | 14.816 | 56.184 | 13.114 | 1.00 | 49.43 | C |
| ATOM | 1148 | O | ASP | B | 214 | 15.497 | 55.934 | 14.107 | 1.00 | 48.27 | O |
| ATOM | 1149 | CB | ASP | B | 214 | 12.897 | 54.660 | 12.642 | 1.00 | 55.83 | C |
| ATOM | 1150 | CG | ASP | B | 214 | 11.399 | 54.413 | 12.750 | 1.00 | 57.66 | C |
| ATOM | 1151 | OD1 | ASP | B | 214 | 10.834 | 54.665 | 13.838 | 1.00 | 57.31 | O |
| ATOM | 1152 | OD2 | ASP | B | 214 | 10.793 | 53.961 | 11.751 | 1.00 | 58.37 | O |
| ATOM | 1153 | N | VAL | B | 215 | 15.338 | 56.595 | 11.966 | 1.00 | 45.60 | N |
| ATOM | 1154 | CA | VAL | B | 215 | 16.770 | 56.767 | 11.807 | 1.00 | 44.22 | C |
| ATOM | 1155 | C | VAL | B | 215 | 17.346 | 57.816 | 12.758 | 1.00 | 43.86 | C |
| ATOM | 1156 | O | VAL | B | 215 | 18.345 | 57.562 | 13.430 | 1.00 | 44.52 | O |
| ATOM | 1157 | CB | VAL | B | 215 | 17.117 | 57.143 | 10.360 | 1.00 | 43.83 | C |
| ATOM | 1158 | CG1 | VAL | B | 215 | 18.617 | 57.350 | 10.213 | 1.00 | 44.99 | C |
| ATOM | 1159 | CG2 | VAL | B | 215 | 16.657 | 56.041 | 9.429 | 1.00 | 46.16 | C |
| ATOM | 1160 | N | THR | B | 216 | 16.714 | 58.984 | 12.835 | 1.00 | 42.82 | N |
| ATOM | 1161 | CA | THR | B | 216 | 17.217 | 60.035 | 13.712 | 1.00 | 41.68 | C |
| ATOM | 1162 | C | THR | B | 216 | 17.180 | 59.558 | 15.155 | 1.00 | 40.38 | C |
| ATOM | 1163 | O | THR | B | 216 | 18.121 | 59.782 | 15.919 | 1.00 | 40.92 | O |
| ATOM | 1164 | CB | THR | B | 216 | 16.390 | 61.352 | 13.591 | 1.00 | 41.64 | C |
| ATOM | 1165 | OG1 | THR | B | 216 | 15.206 | 61.258 | 14.387 | 1.00 | 42.85 | O |
| ATOM | 1166 | CG2 | THR | B | 216 | 15.992 | 61.603 | 12.149 | 1.00 | 40.73 | C |
| ATOM | 1167 | N | LYS | B | 217 | 16.090 | 58.892 | 15.520 | 1.00 | 39.71 | N |
| ATOM | 1168 | CA | LYS | B | 217 | 15.932 | 58.371 | 16.871 | 1.00 | 38.63 | C |
| ATOM | 1169 | C | LYS | B | 217 | 17.064 | 57.411 | 17.236 | 1.00 | 35.12 | C |
| ATOM | 1170 | O | LYS | B | 217 | 17.544 | 57.413 | 18.369 | 1.00 | 32.67 | O |
| ATOM | 1171 | CB | LYS | B | 217 | 14.590 | 57.646 | 17.004 | 1.00 | 42.48 | C |
| ATOM | 1172 | CG | LYS | B | 217 | 13.393 | 58.572 | 16.969 | 1.00 | 48.85 | C |
| ATOM | 1173 | CD | LYS | B | 217 | 12.093 | 57.817 | 17.224 | 1.00 | 50.93 | C |
| ATOM | 1174 | CE | LYS | B | 217 | 10.903 | 58.768 | 17.218 | 1.00 | 52.56 | C |
| ATOM | 1175 | NZ | LYS | B | 217 | 9.633 | 58.065 | 17.555 | 1.00 | 53.57 | N |
| ATOM | 1176 | N | LEU | B | 218 | 17.477 | 56.592 | 16.271 | 1.00 | 32.67 | N |
| ATOM | 1177 | CA | LEU | B | 218 | 18.551 | 55.622 | 16.482 | 1.00 | 32.18 | C |
| ATOM | 1178 | C | LEU | B | 218 | 19.886 | 56.328 | 16.639 | 1.00 | 31.65 | C |
| ATOM | 1179 | O | LEU | B | 218 | 20.659 | 56.006 | 17.536 | 1.00 | 30.79 | O |
| ATOM | 1180 | CB | LEU | B | 218 | 18.638 | 54.648 | 15.306 | 1.00 | 30.41 | C |
| ATOM | 1181 | CG | LEU | B | 218 | 19.718 | 53.570 | 15.339 | 1.00 | 26.12 | C |
| ATOM | 1182 | CD1 | LEU | B | 218 | 19.499 | 52.659 | 16.520 | 1.00 | 26.45 | C |
| ATOM | 1183 | CD2 | LEU | B | 218 | 19.671 | 52.771 | 14.039 | 1.00 | 28.84 | C |
| ATOM | 1184 | N | VAL | B | 219 | 20.166 | 57.280 | 15.757 | 1.00 | 31.46 | N |
| ATOM | 1185 | CA | VAL | B | 219 | 21.417 | 58.015 | 15.853 | 1.00 | 32.60 | C |
| ATOM | 1186 | C | VAL | B | 219 | 21.466 | 58.673 | 17.242 | 1.00 | 32.42 | C |
| ATOM | 1187 | O | VAL | B | 219 | 22.508 | 58.701 | 17.893 | 1.00 | 32.49 | O |
| ATOM | 1188 | CB | VAL | B | 219 | 21.507 | 59.077 | 14.737 | 1.00 | 35.95 | C |
| ATOM | 1189 | CG1 | VAL | B | 219 | 22.780 | 59.917 | 14.893 | 1.00 | 37.54 | C |
| ATOM | 1190 | CG2 | VAL | B | 219 | 21.497 | 58.385 | 13.379 | 1.00 | 35.28 | C |
| ATOM | 1191 | N | ALA | B | 220 | 20.318 | 59.171 | 17.691 | 1.00 | 30.69 | N |
| ATOM | 1192 | CA | ALA | B | 220 | 20.186 | 59.809 | 19.002 | 1.00 | 31.19 | C |
| ATOM | 1193 | C | ALA | B | 220 | 20.382 | 58.804 | 20.140 | 1.00 | 31.91 | C |
| ATOM | 1194 | O | ALA | B | 220 | 20.742 | 59.174 | 21.265 | 1.00 | 30.98 | O |
| ATOM | 1195 | CB | ALA | B | 220 | 18.801 | 60.440 | 19.125 | 1.00 | 28.27 | C |
| ATOM | 1196 | N | ASN | B | 221 | 20.136 | 57.531 | 19.848 | 1.00 | 30.80 | N |
| ATOM | 1197 | CA | ASN | B | 221 | 20.261 | 56.498 | 20.864 | 1.00 | 31.97 | C |
| ATOM | 1198 | C | ASN | B | 221 | 21.549 | 55.694 | 20.723 | 1.00 | 31.15 | C |
| ATOM | 1199 | O | ASN | B | 221 | 21.739 | 54.673 | 21.377 | 1.00 | 30.13 | O |
| ATOM | 1200 | CB | ASN | B | 221 | 19.055 | 55.578 | 20.800 | 1.00 | 33.04 | C |
| ATOM | 1201 | CG | ASN | B | 221 | 18.673 | 55.058 | 22.142 | 1.00 | 37.25 | C |
| ATOM | 1202 | OD1 | ASN | B | 221 | 18.517 | 55.829 | 23.087 | 1.00 | 38.33 | O |
| ATOM | 1203 | ND2 | ASN | B | 221 | 18.514 | 53.743 | 22.249 | 1.00 | 39.86 | N |
| ATOM | 1204 | N | LEU | B | 222 | 22.425 | 56.178 | 19.856 | 1.00 | 30.64 | N |
| ATOM | 1205 | CA | LEU | B | 222 | 23.709 | 55.557 | 19.609 | 1.00 | 31.59 | C |
| ATOM | 1206 | C | LEU | B | 222 | 24.774 | 56.559 | 20.047 | 1.00 | 33.54 | C |
| ATOM | 1207 | O | LEU | B | 222 | 24.679 | 57.753 | 19.748 | 1.00 | 34.13 | O |
| ATOM | 1208 | CB | LEU | B | 222 | 23.858 | 55.266 | 18.118 | 1.00 | 31.84 | C |

TABLE 4-continued

Stem Cell Factor Dimer

| ATOM | 1209 | CG | LEU | B | 222 | 23.960 | 53.842 | 17.562 | 1.00 | 32.43 | C |
|---|---|---|---|---|---|---|---|---|---|---|---|
| ATOM | 1210 | CD1 | LEU | B | 222 | 23.326 | 52.794 | 18.478 | 1.00 | 29.84 | C |
| ATOM | 1211 | CD2 | LEU | B | 222 | 23.292 | 53.866 | 16.202 | 1.00 | 31.79 | C |
| ATOM | 1212 | N | PRO | B | 223 | 25.785 | 56.100 | 20.789 | 1.00 | 34.21 | N |
| ATOM | 1213 | CA | PRO | B | 223 | 26.819 | 57.049 | 21.209 | 1.00 | 34.42 | C |
| ATOM | 1214 | C | PRO | B | 223 | 27.514 | 57.665 | 19.989 | 1.00 | 35.75 | C |
| ATOM | 1215 | O | PRO | B | 223 | 27.888 | 56.949 | 19.049 | 1.00 | 34.36 | O |
| ATOM | 1216 | CB | PRO | B | 223 | 27.759 | 56.190 | 22.062 | 1.00 | 34.97 | C |
| ATOM | 1217 | CG | PRO | B | 223 | 27.518 | 54.775 | 21.556 | 1.00 | 35.82 | C |
| ATOM | 1218 | CD | PRO | B | 223 | 26.041 | 54.747 | 21.314 | 1.00 | 34.53 | C |
| ATOM | 1219 | N | LYS | B | 224 | 27.660 | 58.991 | 19.998 | 1.00 | 35.36 | N |
| ATOM | 1220 | CA | LYS | B | 224 | 28.309 | 59.711 | 18.897 | 1.00 | 38.46 | C |
| ATOM | 1221 | C | LYS | B | 224 | 29.735 | 59.206 | 18.791 | 1.00 | 38.58 | C |
| ATOM | 1222 | O | LYS | B | 224 | 30.443 | 59.479 | 17.829 | 1.00 | 39.76 | O |
| ATOM | 1223 | CB | LYS | B | 224 | 28.344 | 61.216 | 19.182 | 1.00 | 40.17 | C |
| ATOM | 1224 | CG | LYS | B | 224 | 27.035 | 61.801 | 19.670 | 1.00 | 44.14 | C |
| ATOM | 1225 | CD | LYS | B | 224 | 27.237 | 63.221 | 20.168 | 1.00 | 47.87 | C |
| ATOM | 1226 | CE | LYS | B | 224 | 25.980 | 63.755 | 20.843 | 1.00 | 51.17 | C |
| ATOM | 1227 | NZ | LYS | B | 224 | 26.174 | 65.142 | 21.361 | 1.00 | 52.59 | N |
| ATOM | 1228 | N | ASP | B | 225 | 30.132 | 58.468 | 19.815 | 1.00 | 40.23 | N |
| ATOM | 1229 | CA | ASP | B | 225 | 31.456 | 57.890 | 19.951 | 1.00 | 41.59 | C |
| ATOM | 1230 | C | ASP | B | 225 | 31.577 | 56.525 | 19.244 | 1.00 | 39.50 | C |
| ATOM | 1231 | O | ASP | B | 225 | 32.676 | 56.097 | 18.888 | 1.00 | 37.57 | O |
| ATOM | 1232 | CB | ASP | B | 225 | 31.726 | 57.712 | 21.448 | 1.00 | 44.75 | C |
| ATOM | 1233 | CG | ASP | B | 225 | 33.193 | 57.637 | 21.777 | 1.00 | 49.61 | C |
| ATOM | 1234 | OD1 | ASP | B | 225 | 33.918 | 56.837 | 21.145 | 1.00 | 54.59 | O |
| ATOM | 1235 | OD2 | ASP | B | 225 | 33.620 | 58.376 | 22.687 | 1.00 | 52.53 | O |
| ATOM | 1236 | N | TYR | B | 226 | 30.448 | 55.847 | 19.045 | 1.00 | 37.50 | N |
| ATOM | 1237 | CA | TYR | B | 226 | 30.445 | 54.514 | 18.442 | 1.00 | 36.48 | C |
| ATOM | 1238 | C | TYR | B | 226 | 30.892 | 54.451 | 16.991 | 1.00 | 35.68 | C |
| ATOM | 1239 | O | TYR | B | 226 | 30.374 | 55.169 | 16.143 | 1.00 | 35.54 | O |
| ATOM | 1240 | CB | TYR | B | 226 | 29.053 | 53.886 | 18.560 | 1.00 | 37.65 | C |
| ATOM | 1241 | CG | TYR | B | 226 | 29.037 | 52.396 | 18.288 | 1.00 | 38.60 | C |
| ATOM | 1242 | CD1 | TYR | B | 226 | 28.039 | 51.822 | 17.500 | 1.00 | 37.85 | C |
| ATOM | 1243 | CD2 | TYR | B | 226 | 30.007 | 51.556 | 18.842 | 1.00 | 37.09 | C |
| ATOM | 1244 | CE1 | TYR | B | 226 | 28.005 | 50.440 | 17.270 | 1.00 | 38.79 | C |
| ATOM | 1245 | CE2 | TYR | B | 226 | 29.986 | 50.179 | 18.621 | 1.00 | 39.41 | C |
| ATOM | 1246 | CZ | TYR | B | 226 | 28.981 | 49.626 | 17.833 | 1.00 | 38.69 | C |
| ATOM | 1247 | OH | TYR | B | 226 | 28.957 | 48.268 | 17.607 | 1.00 | 39.90 | O |
| ATOM | 1248 | N | MET | B | 227 | 31.838 | 53.562 | 16.706 | 1.00 | 36.10 | N |
| ATOM | 1249 | CA | MET | B | 227 | 32.356 | 53.406 | 15.351 | 1.00 | 37.09 | C |
| ATOM | 1250 | C | MET | B | 227 | 31.756 | 52.198 | 14.641 | 1.00 | 36.12 | C |
| ATOM | 1251 | O | MET | B | 227 | 31.842 | 51.066 | 15.123 | 1.00 | 33.71 | O |
| ATOM | 1252 | CB | MET | B | 227 | 33.881 | 53.290 | 15.382 | 1.00 | 41.32 | C |
| ATOM | 1253 | CG | MET | B | 227 | 34.600 | 54.437 | 14.688 | 1.00 | 48.18 | C |
| ATOM | 1254 | SD | MET | B | 227 | 33.881 | 56.053 | 15.088 | 1.00 | 54.24 | S |
| ATOM | 1255 | CE | MET | B | 227 | 34.682 | 56.402 | 16.647 | 1.00 | 56.04 | C |
| ATOM | 1256 | N | ILE | B | 228 | 31.156 | 52.454 | 13.481 | 1.00 | 35.08 | N |
| ATOM | 1257 | CA | ILE | B | 228 | 30.521 | 51.416 | 12.683 | 1.00 | 33.44 | C |
| ATOM | 1258 | C | ILE | B | 228 | 31.320 | 51.080 | 11.425 | 1.00 | 33.56 | C |
| ATOM | 1259 | O | ILE | B | 228 | 31.733 | 51.971 | 10.687 | 1.00 | 32.95 | O |
| ATOM | 1260 | CB | ILE | B | 228 | 29.107 | 51.859 | 12.262 | 1.00 | 31.75 | C |
| ATOM | 1261 | CG1 | ILE | B | 228 | 28.248 | 52.077 | 13.509 | 1.00 | 30.42 | C |
| ATOM | 1262 | CG2 | ILE | B | 228 | 28.493 | 50.832 | 11.320 | 1.00 | 30.01 | C |
| ATOM | 1263 | CD1 | ILE | B | 228 | 26.900 | 52.710 | 13.224 | 1.00 | 28.35 | C |
| ATOM | 1264 | N | THR | B | 229 | 31.513 | 49.789 | 11.172 | 1.00 | 33.75 | N |
| ATOM | 1265 | CA | THR | B | 229 | 32.257 | 49.355 | 9.993 | 1.00 | 35.22 | C |
| ATOM | 1266 | C | THR | B | 229 | 31.384 | 49.209 | 8.744 | 1.00 | 36.26 | C |
| ATOM | 1267 | O | THR | B | 229 | 30.273 | 48.666 | 8.791 | 1.00 | 34.96 | O |
| ATOM | 1268 | CB | THR | B | 229 | 32.970 | 48.018 | 10.248 | 1.00 | 36.26 | C |
| ATOM | 1269 | OG1 | THR | B | 229 | 33.897 | 48.172 | 11.333 | 1.00 | 39.29 | O |
| ATOM | 1270 | CG2 | THR | B | 229 | 33.718 | 47.566 | 8.995 | 1.00 | 35.93 | C |
| ATOM | 1271 | N | LEU | B | 230 | 31.910 | 49.692 | 7.624 | 1.00 | 35.74 | N |
| ATOM | 1272 | CA | LEU | B | 230 | 31.212 | 49.633 | 6.353 | 1.00 | 35.46 | C |
| ATOM | 1273 | C | LEU | B | 230 | 32.210 | 49.587 | 5.190 | 1.00 | 37.16 | C |
| ATOM | 1274 | O | LEU | B | 230 | 33.125 | 50.416 | 5.114 | 1.00 | 37.17 | O |
| ATOM | 1275 | CB | LEU | B | 230 | 30.297 | 50.859 | 6.212 | 1.00 | 33.47 | C |
| ATOM | 1276 | CG | LEU | B | 230 | 29.543 | 51.079 | 4.889 | 1.00 | 33.44 | C |
| ATOM | 1277 | CD1 | LEU | B | 230 | 28.564 | 49.935 | 4.637 | 1.00 | 27.86 | C |
| ATOM | 1278 | CD2 | LEU | B | 230 | 28.809 | 52.419 | 4.932 | 1.00 | 31.24 | C |
| ATOM | 1279 | N | LYS | B | 231 | 32.054 | 48.605 | 4.302 | 1.00 | 38.67 | N |
| ATOM | 1280 | CA | LYS | B | 231 | 32.927 | 48.512 | 3.134 | 1.00 | 41.23 | C |
| ATOM | 1281 | C | LYS | B | 231 | 32.424 | 49.588 | 2.183 | 1.00 | 42.27 | C |
| ATOM | 1282 | O | LYS | B | 231 | 31.504 | 49.364 | 1.398 | 1.00 | 41.26 | O |
| ATOM | 1283 | CB | LYS | B | 231 | 32.829 | 47.133 | 2.481 | 1.00 | 41.80 | C |
| ATOM | 1284 | CG | LYS | B | 231 | 33.541 | 46.035 | 3.257 | 1.00 | 45.00 | C |
| ATOM | 1285 | CD | LYS | B | 231 | 33.579 | 44.737 | 2.459 | 1.00 | 48.11 | C |

TABLE 4-continued

Stem Cell Factor Dimer

| ATOM | 1286 | CE | LYS | B | 231 | 34.274 | 43.619 | 3.231 | 1.00 | 50.40 | C |
|---|---|---|---|---|---|---|---|---|---|---|---|
| ATOM | 1287 | NZ | LYS | B | 231 | 33.580 | 43.304 | 4.511 | 1.00 | 51.63 | N |
| ATOM | 1288 | N | TYR | B | 232 | 33.043 | 50.760 | 2.283 | 1.00 | 44.81 | N |
| ATOM | 1289 | CA | TYR | B | 232 | 32.683 | 51.943 | 1.508 | 1.00 | 47.65 | C |
| ATOM | 1290 | C | TYR | B | 232 | 33.298 | 52.021 | 0.109 | 1.00 | 50.22 | C |
| ATOM | 1291 | O | TYR | B | 232 | 34.508 | 51.822 | −0.063 | 1.00 | 50.37 | O |
| ATOM | 1292 | CB | TYR | B | 232 | 33.090 | 53.179 | 2.317 | 1.00 | 48.36 | C |
| ATOM | 1293 | CG | TYR | B | 232 | 32.681 | 54.521 | 1.748 | 1.00 | 50.47 | C |
| ATOM | 1294 | CD1 | TYR | B | 232 | 31.438 | 55.084 | 2.048 | 1.00 | 51.76 | C |
| ATOM | 1295 | CD2 | TYR | B | 232 | 33.564 | 55.261 | 0.962 | 1.00 | 51.08 | C |
| ATOM | 1296 | CE1 | TYR | B | 232 | 31.088 | 56.361 | 1.584 | 1.00 | 50.40 | C |
| ATOM | 1297 | CE2 | TYR | B | 232 | 33.226 | 56.534 | 0.492 | 1.00 | 50.25 | C |
| ATOM | 1298 | CZ | TYR | B | 232 | 31.992 | 57.079 | 0.809 | 1.00 | 51.25 | C |
| ATOM | 1299 | OH | TYR | B | 232 | 31.677 | 58.350 | 0.369 | 1.00 | 50.44 | O |
| ATOM | 1300 | N | VAL | B | 233 | 32.456 | 52.319 | −0.883 | 1.00 | 51.48 | N |
| ATOM | 1301 | CA | VAL | B | 233 | 32.911 | 52.472 | −2.265 | 1.00 | 53.29 | C |
| ATOM | 1302 | C | VAL | B | 233 | 33.562 | 53.856 | −2.389 | 1.00 | 54.21 | C |
| ATOM | 1303 | O | VAL | B | 233 | 32.896 | 54.884 | −2.255 | 1.00 | 54.14 | O |
| ATOM | 1304 | CB | VAL | B | 233 | 31.741 | 52.378 | −3.272 | 1.00 | 53.48 | C |
| ATOM | 1305 | CG1 | VAL | B | 233 | 32.276 | 52.433 | −4.690 | 1.00 | 52.85 | C |
| ATOM | 1306 | CG2 | VAL | B | 233 | 30.969 | 51.089 | −3.060 | 1.00 | 54.00 | C |
| ATOM | 1307 | N | PRO | B | 234 | 34.876 | 53.888 | −2.658 | 1.00 | 55.55 | N |
| ATOM | 1308 | CA | PRO | B | 234 | 35.736 | 55.064 | −2.815 | 1.00 | 56.44 | C |
| ATOM | 1309 | C | PRO | B | 234 | 35.161 | 56.459 | −3.101 | 1.00 | 57.04 | C |
| ATOM | 1310 | O | PRO | B | 234 | 35.372 | 57.379 | −2.305 | 1.00 | 57.54 | O |
| ATOM | 1311 | CB | PRO | B | 234 | 36.720 | 54.606 | −3.874 | 1.00 | 57.14 | C |
| ATOM | 1312 | CG | PRO | B | 234 | 36.989 | 53.204 | −3.415 | 1.00 | 56.28 | C |
| ATOM | 1313 | CD | PRO | B | 234 | 35.595 | 52.676 | −3.100 | 1.00 | 55.40 | C |
| ATOM | 1314 | N | GLY | B | 235 | 34.447 | 56.642 | −4.208 | 1.00 | 56.12 | N |
| ATOM | 1315 | CA | GLY | B | 235 | 33.943 | 57.979 | −4.490 | 1.00 | 54.89 | C |
| ATOM | 1316 | C | GLY | B | 235 | 32.469 | 58.134 | −4.786 | 1.00 | 53.88 | C |
| ATOM | 1317 | O | GLY | B | 235 | 32.083 | 58.925 | −5.646 | 1.00 | 55.02 | O |
| ATOM | 1318 | N | MET | B | 236 | 31.635 | 57.405 | −4.062 | 1.00 | 53.22 | N |
| ATOM | 1319 | CA | MET | B | 236 | 30.200 | 57.471 | −4.283 | 1.00 | 52.92 | C |
| ATOM | 1320 | C | MET | B | 236 | 29.595 | 58.845 | −4.028 | 1.00 | 52.29 | C |
| ATOM | 1321 | O | MET | B | 236 | 28.406 | 59.054 | −4.250 | 1.00 | 51.46 | O |
| ATOM | 1322 | CB | MET | B | 236 | 29.495 | 56.428 | −3.419 | 1.00 | 53.98 | C |
| ATOM | 1323 | CG | MET | B | 236 | 29.893 | 56.458 | −1.957 | 1.00 | 55.72 | C |
| ATOM | 1324 | SD | MET | B | 236 | 28.808 | 55.402 | −0.984 | 1.00 | 58.44 | S |
| ATOM | 1325 | CE | MET | B | 236 | 27.500 | 56.579 | −0.565 | 1.00 | 54.06 | C |
| ATOM | 1326 | N | ASP | B | 237 | 30.409 | 59.786 | −3.567 | 1.00 | 53.17 | N |
| ATOM | 1327 | CA | ASP | B | 237 | 29.912 | 61.130 | −3.294 | 1.00 | 53.05 | C |
| ATOM | 1328 | C | ASP | B | 237 | 29.905 | 62.043 | −4.522 | 1.00 | 51.90 | C |
| ATOM | 1329 | O | ASP | B | 237 | 29.208 | 63.058 | −4.529 | 1.00 | 52.18 | O |
| ATOM | 1330 | CB | ASP | B | 237 | 30.724 | 61.772 | −2.168 | 1.00 | 54.57 | C |
| ATOM | 1331 | CG | ASP | B | 237 | 32.211 | 61.560 | −2.333 | 1.00 | 56.22 | C |
| ATOM | 1332 | OD1 | ASP | B | 237 | 32.628 | 60.389 | −2.453 | 1.00 | 56.92 | O |
| ATOM | 1333 | OD2 | ASP | B | 237 | 32.962 | 62.557 | −2.336 | 1.00 | 56.33 | O |
| ATOM | 1334 | N | VAL | B | 238 | 30.661 | 61.676 | −5.559 | 1.00 | 49.93 | N |
| ATOM | 1335 | CA | VAL | B | 238 | 30.725 | 62.476 | −6.788 | 1.00 | 47.50 | C |
| ATOM | 1336 | C | VAL | B | 238 | 30.455 | 61.658 | −8.047 | 1.00 | 46.36 | C |
| ATOM | 1337 | O | VAL | B | 238 | 30.350 | 62.204 | −9.141 | 1.00 | 44.99 | O |
| ATOM | 1338 | CB | VAL | B | 238 | 32.105 | 63.155 | −6.955 | 1.00 | 47.44 | C |
| ATOM | 1339 | CG1 | VAL | B | 238 | 32.315 | 64.193 | −5.855 | 1.00 | 46.51 | C |
| ATOM | 1340 | CG2 | VAL | B | 238 | 33.209 | 62.103 | −6.921 | 1.00 | 46.60 | C |
| ATOM | 1341 | N | LEU | B | 239 | 30.343 | 60.346 | −7.886 | 1.00 | 45.32 | N |
| ATOM | 1342 | CA | LEU | B | 239 | 30.097 | 59.456 | −9.009 | 1.00 | 44.11 | C |
| ATOM | 1343 | C | LEU | B | 239 | 28.614 | 59.154 | −9.221 | 1.00 | 42.87 | C |
| ATOM | 1344 | O | LEU | B | 239 | 27.823 | 59.163 | −8.275 | 1.00 | 41.17 | O |
| ATOM | 1345 | CB | LEU | B | 239 | 30.866 | 58.150 | −8.797 | 1.00 | 45.39 | C |
| ATOM | 1346 | CG | LEU | B | 239 | 32.213 | 57.947 | −9.500 | 1.00 | 47.31 | C |
| ATOM | 1347 | CD1 | LEU | B | 239 | 32.895 | 59.280 | −9.784 | 1.00 | 50.44 | C |
| ATOM | 1348 | CD2 | LEU | B | 239 | 33.085 | 57.056 | −8.633 | 1.00 | 47.46 | C |
| ATOM | 1349 | N | PRO | B | 240 | 28.211 | 58.909 | −10.481 | 1.00 | 42.22 | N |
| ATOM | 1350 | CA | PRO | B | 240 | 26.802 | 58.602 | −10.748 | 1.00 | 40.41 | C |
| ATOM | 1351 | C | PRO | B | 240 | 26.413 | 57.361 | −9.947 | 1.00 | 38.81 | C |
| ATOM | 1352 | O | PRO | B | 240 | 27.230 | 56.461 | −9.758 | 1.00 | 35.05 | O |
| ATOM | 1353 | CB | PRO | B | 240 | 26.768 | 58.385 | −12.265 | 1.00 | 40.21 | C |
| ATOM | 1354 | CG | PRO | B | 240 | 28.185 | 58.015 | −12.615 | 1.00 | 40.16 | C |
| ATOM | 1355 | CD | PRO | B | 240 | 28.993 | 58.931 | −11.730 | 1.00 | 42.24 | C |
| ATOM | 1356 | N | SER | B | 241 | 25.170 | 57.328 | −9.477 | 1.00 | 39.89 | N |
| ATOM | 1357 | CA | SER | B | 241 | 24.683 | 56.229 | −8.653 | 1.00 | 41.17 | C |
| ATOM | 1358 | C | SER | B | 241 | 24.862 | 54.823 | −9.217 | 1.00 | 41.84 | C |
| ATOM | 1359 | O | SER | B | 241 | 25.099 | 53.887 | −8.459 | 1.00 | 40.78 | O |
| ATOM | 1360 | CB | SER | B | 241 | 23.211 | 56.456 | −8.285 | 1.00 | 40.90 | C |
| ATOM | 1361 | OG | SER | B | 241 | 22.370 | 56.370 | −9.418 | 1.00 | 41.89 | O |
| ATOM | 1362 | N | HIS | B | 242 | 24.769 | 54.662 | −10.534 | 1.00 | 42.79 | N |

TABLE 4-continued

Stem Cell Factor Dimer

| ATOM | 1363 | CA | HIS | B | 242 | 24.915 | 53.329 | −11.106 | 1.00 | 44.00 | C |
|---|---|---|---|---|---|---|---|---|---|---|---|
| ATOM | 1364 | C | HIS | B | 242 | 26.308 | 52.745 | −10.861 | 1.00 | 44.18 | C |
| ATOM | 1365 | O | HIS | B | 242 | 26.528 | 51.548 | −11.051 | 1.00 | 44.48 | O |
| ATOM | 1366 | CB | HIS | B | 242 | 24.609 | 53.337 | −12.615 | 1.00 | 44.68 | C |
| ATOM | 1367 | CG | HIS | B | 242 | 25.728 | 53.856 | −13.463 | 1.00 | 45.88 | C |
| ATOM | 1368 | ND1 | HIS | B | 242 | 25.938 | 55.201 | −13.682 | 1.00 | 45.63 | N |
| ATOM | 1369 | CD2 | HIS | B | 242 | 26.734 | 53.210 | −14.100 | 1.00 | 45.13 | C |
| ATOM | 1370 | CE1 | HIS | B | 242 | 27.028 | 55.359 | −14.413 | 1.00 | 45.31 | C |
| ATOM | 1371 | NE2 | HIS | B | 242 | 27.529 | 54.167 | −14.679 | 1.00 | 44.52 | N |
| ATOM | 1372 | N | CYS | B | 243 | 27.244 | 53.585 | −10.436 | 1.00 | 44.41 | N |
| ATOM | 1373 | CA | CYS | B | 243 | 28.610 | 53.134 | −10.180 | 1.00 | 46.06 | C |
| ATOM | 1374 | C | CYS | B | 243 | 28.830 | 52.503 | −8.806 | 1.00 | 45.03 | C |
| ATOM | 1375 | O | CYS | B | 243 | 29.813 | 51.795 | −8.607 | 1.00 | 45.32 | O |
| ATOM | 1376 | CB | CYS | B | 243 | 29.600 | 54.299 | −10.302 | 1.00 | 50.08 | C |
| ATOM | 1377 | SG | CYS | B | 243 | 29.818 | 55.061 | −11.942 | 1.00 | 54.23 | S |
| ATOM | 1378 | N | TRP | B | 244 | 27.930 | 52.751 | −7.860 | 1.00 | 44.29 | N |
| ATOM | 1379 | CA | TRP | B | 244 | 28.119 | 52.237 | −6.503 | 1.00 | 43.92 | C |
| ATOM | 1380 | C | TRP | B | 244 | 26.914 | 51.634 | −5.792 | 1.00 | 44.54 | C |
| ATOM | 1381 | O | TRP | B | 244 | 27.070 | 50.819 | −4.881 | 1.00 | 44.86 | O |
| ATOM | 1382 | CB | TRP | B | 244 | 28.656 | 53.356 | −5.617 | 1.00 | 41.38 | C |
| ATOM | 1383 | CG | TRP | B | 244 | 27.859 | 54.654 | −5.700 | 1.00 | 40.51 | C |
| ATOM | 1384 | CD1 | TRP | B | 244 | 28.097 | 55.721 | −6.539 | 1.00 | 39.35 | C |
| ATOM | 1385 | CD2 | TRP | B | 244 | 26.752 | 55.042 | −4.872 | 1.00 | 38.13 | C |
| ATOM | 1386 | NE1 | TRP | B | 244 | 27.213 | 56.743 | −6.269 | 1.00 | 37.91 | N |
| ATOM | 1387 | CE2 | TRP | B | 244 | 26.380 | 56.355 | −5.254 | 1.00 | 37.29 | C |
| ATOM | 1388 | CE3 | TRP | B | 244 | 26.040 | 54.409 | −3.845 | 1.00 | 37.72 | C |
| ATOM | 1389 | CZ2 | TRP | B | 244 | 25.334 | 57.042 | −4.642 | 1.00 | 37.77 | C |
| ATOM | 1390 | CZ3 | TRP | B | 244 | 24.994 | 55.096 | −3.235 | 1.00 | 37.27 | C |
| ATOM | 1391 | CH2 | TRP | B | 244 | 24.653 | 56.398 | −3.635 | 1.00 | 39.15 | C |
| ATOM | 1392 | N | ILE | B | 245 | 25.727 | 52.053 | −6.207 | 1.00 | 43.54 | N |
| ATOM | 1393 | CA | ILE | B | 245 | 24.472 | 51.626 | −5.614 | 1.00 | 45.80 | C |
| ATOM | 1394 | C | ILE | B | 245 | 24.233 | 50.133 | −5.326 | 1.00 | 45.86 | C |
| ATOM | 1395 | O | ILE | B | 245 | 23.612 | 49.797 | −4.319 | 1.00 | 46.72 | O |
| ATOM | 1396 | CB | ILE | B | 245 | 23.280 | 52.184 | −6.451 | 1.00 | 47.09 | C |
| ATOM | 1397 | CG1 | ILE | B | 245 | 22.333 | 52.971 | −5.541 | 1.00 | 47.92 | C |
| ATOM | 1398 | CG2 | ILE | B | 245 | 22.551 | 51.062 | −7.179 | 1.00 | 47.16 | C |
| ATOM | 1399 | CD1 | ILE | B | 245 | 21.883 | 52.218 | −4.318 | 1.00 | 46.52 | C |
| ATOM | 1400 | N | SER | B | 246 | 24.701 | 49.238 | −6.187 | 1.00 | 45.14 | N |
| ATOM | 1401 | CA | SER | B | 246 | 24.467 | 47.816 | −5.950 | 1.00 | 45.76 | C |
| ATOM | 1402 | C | SER | B | 246 | 25.338 | 47.305 | −4.809 | 1.00 | 45.59 | C |
| ATOM | 1403 | O | SER | B | 246 | 24.867 | 46.612 | −3.907 | 1.00 | 43.82 | O |
| ATOM | 1404 | CB | SER | B | 246 | 24.763 | 47.003 | −7.207 | 1.00 | 45.52 | C |
| ATOM | 1405 | OG | SER | B | 246 | 26.162 | 46.838 | −7.370 | 1.00 | 51.00 | O |
| ATOM | 1406 | N | GLU | B | 247 | 26.616 | 47.653 | −4.864 | 1.00 | 45.29 | N |
| ATOM | 1407 | CA | GLU | B | 247 | 27.578 | 47.244 | −3.853 | 1.00 | 45.41 | C |
| ATOM | 1408 | C | GLU | B | 247 | 27.260 | 47.850 | −2.483 | 1.00 | 43.93 | C |
| ATOM | 1409 | O | GLU | B | 247 | 27.327 | 47.170 | −1.460 | 1.00 | 44.47 | O |
| ATOM | 1410 | CB | GLU | B | 247 | 28.983 | 47.675 | −4.285 | 1.00 | 46.51 | C |
| ATOM | 1411 | CG | GLU | B | 247 | 30.072 | 47.322 | −3.295 | 1.00 | 50.56 | C |
| ATOM | 1412 | CD | GLU | B | 247 | 30.319 | 45.831 | −3.220 | 1.00 | 52.10 | C |
| ATOM | 1413 | OE1 | GLU | B | 247 | 31.108 | 45.396 | −2.354 | 1.00 | 51.67 | O |
| ATOM | 1414 | OE2 | GLU | B | 247 | 29.725 | 45.096 | −4.037 | 1.00 | 54.23 | O |
| ATOM | 1415 | N | MET | B | 248 | 26.914 | 49.130 | −2.474 | 1.00 | 40.71 | N |
| ATOM | 1416 | CA | MET | B | 248 | 26.621 | 49.826 | −1.233 | 1.00 | 41.30 | C |
| ATOM | 1417 | C | MET | B | 248 | 25.356 | 49.309 | −0.552 | 1.00 | 39.73 | C |
| ATOM | 1418 | O | MET | B | 248 | 25.319 | 49.149 | 0.670 | 1.00 | 39.87 | O |
| ATOM | 1419 | CB | MET | B | 248 | 26.513 | 51.332 | −1.505 | 1.00 | 41.78 | C |
| ATOM | 1420 | CG | MET | B | 248 | 26.557 | 52.221 | −0.264 | 1.00 | 43.87 | C |
| ATOM | 1421 | SD | MET | B | 248 | 28.138 | 52.280 | 0.660 | 1.00 | 43.67 | S |
| ATOM | 1422 | CE | MET | B | 248 | 29.247 | 51.363 | −0.411 | 1.00 | 38.63 | C |
| ATOM | 1423 | N | VAL | B | 249 | 24.317 | 49.050 | −1.336 | 1.00 | 37.21 | N |
| ATOM | 1424 | CA | VAL | B | 249 | 23.074 | 48.547 | −0.776 | 1.00 | 35.20 | C |
| ATOM | 1425 | C | VAL | B | 249 | 23.379 | 47.212 | −0.107 | 1.00 | 36.30 | C |
| ATOM | 1426 | O | VAL | B | 249 | 22.807 | 46.872 | 0.930 | 1.00 | 35.65 | O |
| ATOM | 1427 | CB | VAL | B | 249 | 22.011 | 48.392 | −1.887 | 1.00 | 36.29 | C |
| ATOM | 1428 | CG1 | VAL | B | 249 | 20.977 | 47.367 | −1.512 | 1.00 | 36.41 | C |
| ATOM | 1429 | CG2 | VAL | B | 249 | 21.322 | 49.722 | −2.110 | 1.00 | 32.75 | C |
| ATOM | 1430 | N | VAL | B | 250 | 24.317 | 46.478 | −0.693 | 1.00 | 35.39 | N |
| ATOM | 1431 | CA | VAL | B | 250 | 24.738 | 45.184 | −0.175 | 1.00 | 35.29 | C |
| ATOM | 1432 | C | VAL | B | 250 | 25.599 | 45.302 | 1.088 | 1.00 | 35.84 | C |
| ATOM | 1433 | O | VAL | B | 250 | 25.484 | 44.487 | 2.004 | 1.00 | 35.78 | O |
| ATOM | 1434 | CB | VAL | B | 250 | 25.527 | 44.408 | −1.244 | 1.00 | 33.99 | C |
| ATOM | 1435 | CG1 | VAL | B | 250 | 26.122 | 43.136 | −0.654 | 1.00 | 33.25 | C |
| ATOM | 1436 | CG2 | VAL | B | 250 | 24.599 | 44.063 | −2.403 | 1.00 | 35.34 | C |
| ATOM | 1437 | N | GLN | B | 251 | 26.455 | 46.318 | 1.135 | 1.00 | 34.16 | N |
| ATOM | 1438 | CA | GLN | B | 251 | 27.330 | 46.521 | 2.278 | 1.00 | 32.34 | C |
| ATOM | 1439 | C | GLN | B | 251 | 26.570 | 47.124 | 3.438 | 1.00 | 30.64 | C |

TABLE 4-continued

Stem Cell Factor Dimer

| ATOM | 1440 | O | GLN | B | 251 | 26.868 | 46.846 | 4.599 | 1.00 | 31.74 | O |
|---|---|---|---|---|---|---|---|---|---|---|---|
| ATOM | 1441 | CB | GLN | B | 251 | 28.508 | 47.422 | 1.895 | 1.00 | 33.40 | C |
| ATOM | 1442 | CG | GLN | B | 251 | 29.467 | 46.789 | 0.894 | 1.00 | 35.25 | C |
| ATOM | 1443 | CD | GLN | B | 251 | 30.008 | 45.442 | 1.359 | 1.00 | 37.38 | C |
| ATOM | 1444 | OE1 | GLN | B | 251 | 30.213 | 45.215 | 2.555 | 1.00 | 38.82 | O |
| ATOM | 1445 | NE2 | GLN | B | 251 | 30.263 | 44.550 | 0.410 | 1.00 | 37.16 | N |
| ATOM | 1446 | N | LEU | B | 252 | 25.592 | 47.962 | 3.131 | 1.00 | 29.22 | N |
| ATOM | 1447 | CA | LEU | B | 252 | 24.788 | 48.553 | 4.187 | 1.00 | 30.07 | C |
| ATOM | 1448 | C | LEU | B | 252 | 24.074 | 47.411 | 4.910 | 1.00 | 30.49 | C |
| ATOM | 1449 | O | LEU | B | 252 | 24.083 | 47.338 | 6.137 | 1.00 | 31.62 | O |
| ATOM | 1450 | CB | LEU | B | 252 | 23.775 | 49.541 | 3.595 | 1.00 | 26.58 | C |
| ATOM | 1451 | CG | LEU | B | 252 | 24.396 | 50.889 | 3.162 | 1.00 | 29.74 | C |
| ATOM | 1452 | CD1 | LEU | B | 252 | 23.367 | 51.781 | 2.452 | 1.00 | 25.72 | C |
| ATOM | 1453 | CD2 | LEU | B | 252 | 24.940 | 51.602 | 4.403 | 1.00 | 28.99 | C |
| ATOM | 1454 | N | SER | B | 253 | 23.475 | 46.512 | 4.135 | 1.00 | 29.43 | N |
| ATOM | 1455 | CA | SER | B | 253 | 22.763 | 45.372 | 4.687 | 1.00 | 29.35 | C |
| ATOM | 1456 | C | SER | B | 253 | 23.689 | 44.541 | 5.575 | 1.00 | 29.60 | C |
| ATOM | 1457 | O | SER | B | 253 | 23.324 | 44.162 | 6.685 | 1.00 | 27.14 | O |
| ATOM | 1458 | CB | SER | B | 253 | 22.216 | 44.501 | 3.559 | 1.00 | 29.62 | C |
| ATOM | 1459 | OG | SER | B | 253 | 21.469 | 43.417 | 4.082 | 1.00 | 32.53 | O |
| ATOM | 1460 | N | ASP | B | 254 | 24.897 | 44.278 | 5.094 | 1.00 | 29.62 | N |
| ATOM | 1461 | CA | ASP | B | 254 | 25.847 | 43.494 | 5.871 | 1.00 | 31.92 | C |
| ATOM | 1462 | C | ASP | B | 254 | 26.192 | 44.203 | 7.192 | 1.00 | 31.13 | C |
| ATOM | 1463 | O | ASP | B | 254 | 26.277 | 43.575 | 8.248 | 1.00 | 25.96 | O |
| ATOM | 1464 | CB | ASP | B | 254 | 27.130 | 43.271 | 5.070 | 1.00 | 35.93 | C |
| ATOM | 1465 | CG | ASP | B | 254 | 28.066 | 42.273 | 5.737 | 1.00 | 41.42 | C |
| ATOM | 1466 | OD1 | ASP | B | 254 | 29.303 | 42.391 | 5.568 | 1.00 | 43.83 | O |
| ATOM | 1467 | OD2 | ASP | B | 254 | 27.559 | 41.356 | 6.423 | 1.00 | 46.70 | O |
| ATOM | 1468 | N | SER | B | 255 | 26.399 | 45.513 | 7.131 | 1.00 | 28.26 | N |
| ATOM | 1469 | CA | SER | B | 255 | 26.752 | 46.247 | 8.335 | 1.00 | 28.88 | C |
| ATOM | 1470 | C | SER | B | 255 | 25.616 | 46.261 | 9.357 | 1.00 | 28.38 | C |
| ATOM | 1471 | O | SER | B | 255 | 25.843 | 46.036 | 10.549 | 1.00 | 28.04 | O |
| ATOM | 1472 | CB | SER | B | 255 | 27.165 | 47.682 | 7.985 | 1.00 | 28.35 | C |
| ATOM | 1473 | OG | SER | B | 255 | 28.356 | 47.692 | 7.214 | 1.00 | 28.87 | O |
| ATOM | 1474 | N | LEU | B | 256 | 24.397 | 46.512 | 8.890 | 1.00 | 26.63 | N |
| ATOM | 1475 | CA | LEU | B | 256 | 23.257 | 46.563 | 9.787 | 1.00 | 26.15 | C |
| ATOM | 1476 | C | LEU | B | 256 | 22.955 | 45.218 | 10.407 | 1.00 | 26.03 | C |
| ATOM | 1477 | O | LEU | B | 256 | 22.582 | 45.138 | 11.572 | 1.00 | 26.78 | O |
| ATOM | 1478 | CB | LEU | B | 256 | 22.024 | 47.095 | 9.060 | 1.00 | 23.91 | C |
| ATOM | 1479 | CG | LEU | B | 256 | 22.081 | 48.604 | 8.804 | 1.00 | 25.22 | C |
| ATOM | 1480 | CD1 | LEU | B | 256 | 20.923 | 49.019 | 7.915 | 1.00 | 25.03 | C |
| ATOM | 1481 | CD2 | LEU | B | 256 | 22.038 | 49.358 | 10.134 | 1.00 | 23.13 | C |
| ATOM | 1482 | N | THR | B | 257 | 23.121 | 44.166 | 9.623 | 1.00 | 27.10 | N |
| ATOM | 1483 | CA | THR | B | 257 | 22.861 | 42.822 | 10.094 | 1.00 | 28.54 | C |
| ATOM | 1484 | C | THR | B | 257 | 23.806 | 42.465 | 11.227 | 1.00 | 27.76 | C |
| ATOM | 1485 | O | THR | B | 257 | 23.397 | 41.834 | 12.201 | 1.00 | 27.18 | O |
| ATOM | 1486 | CB | THR | B | 257 | 23.012 | 41.797 | 8.948 | 1.00 | 30.71 | C |
| ATOM | 1487 | OG1 | THR | B | 257 | 22.062 | 42.103 | 7.916 | 1.00 | 30.14 | O |
| ATOM | 1488 | CG2 | THR | B | 257 | 22.758 | 40.372 | 9.461 | 1.00 | 30.87 | C |
| ATOM | 1489 | N | ASP | B | 258 | 25.061 | 42.882 | 11.098 | 1.00 | 28.20 | N |
| ATOM | 1490 | CA | ASP | B | 258 | 26.078 | 42.619 | 12.112 | 1.00 | 30.16 | C |
| ATOM | 1491 | C | ASP | B | 258 | 25.849 | 43.377 | 13.414 | 1.00 | 29.71 | C |
| ATOM | 1492 | O | ASP | B | 258 | 26.229 | 42.901 | 14.485 | 1.00 | 28.76 | O |
| ATOM | 1493 | CB | ASP | B | 258 | 27.467 | 42.993 | 11.597 | 1.00 | 34.00 | C |
| ATOM | 1494 | CG | ASP | B | 258 | 27.970 | 42.046 | 10.554 | 1.00 | 38.03 | C |
| ATOM | 1495 | OD1 | ASP | B | 258 | 27.752 | 40.827 | 10.720 | 1.00 | 40.72 | O |
| ATOM | 1496 | OD2 | ASP | B | 258 | 28.598 | 42.521 | 9.576 | 1.00 | 43.37 | O |
| ATOM | 1497 | N | LEU | B | 259 | 25.265 | 44.565 | 13.318 | 1.00 | 29.27 | N |
| ATOM | 1498 | CA | LEU | B | 259 | 25.002 | 45.382 | 14.502 | 1.00 | 31.85 | C |
| ATOM | 1499 | C | LEU | B | 259 | 23.948 | 44.734 | 15.380 | 1.00 | 30.57 | C |
| ATOM | 1500 | O | LEU | B | 259 | 23.878 | 44.994 | 16.585 | 1.00 | 27.66 | O |
| ATOM | 1501 | CB | LEU | B | 259 | 24.521 | 46.784 | 14.106 | 1.00 | 34.32 | C |
| ATOM | 1502 | CG | LEU | B | 259 | 25.565 | 47.720 | 13.506 | 1.00 | 36.30 | C |
| ATOM | 1503 | CD1 | LEU | B | 259 | 24.940 | 49.089 | 13.226 | 1.00 | 38.89 | C |
| ATOM | 1504 | CD2 | LEU | B | 259 | 26.727 | 47.858 | 14.483 | 1.00 | 38.73 | C |
| ATOM | 1505 | N | LEU | B | 260 | 23.122 | 43.906 | 14.755 | 1.00 | 30.02 | N |
| ATOM | 1506 | CA | LEU | B | 260 | 22.060 | 43.202 | 15.456 | 1.00 | 33.18 | C |
| ATOM | 1507 | C | LEU | B | 260 | 22.669 | 42.436 | 16.621 | 1.00 | 33.45 | C |
| ATOM | 1508 | O | LEU | B | 260 | 22.136 | 42.424 | 17.728 | 1.00 | 34.54 | O |
| ATOM | 1509 | CB | LEU | B | 260 | 21.366 | 42.244 | 14.488 | 1.00 | 32.08 | C |
| ATOM | 1510 | CG | LEU | B | 260 | 19.867 | 42.456 | 14.273 | 1.00 | 35.36 | C |
| ATOM | 1511 | CD1 | LEU | B | 260 | 19.477 | 43.920 | 14.465 | 1.00 | 29.63 | C |
| ATOM | 1512 | CD2 | LEU | B | 260 | 19.513 | 41.959 | 12.882 | 1.00 | 33.62 | C |
| ATOM | 1513 | N | ASP | B | 261 | 23.807 | 41.813 | 16.346 | 1.00 | 35.20 | N |
| ATOM | 1514 | CA | ASP | B | 261 | 24.550 | 41.030 | 17.326 | 1.00 | 37.38 | C |
| ATOM | 1515 | C | ASP | B | 261 | 24.929 | 41.883 | 18.549 | 1.00 | 34.81 | C |
| ATOM | 1516 | O | ASP | B | 261 | 25.082 | 41.358 | 19.650 | 1.00 | 36.03 | O |

TABLE 4-continued

Stem Cell Factor Dimer

| ATOM | 1517 | CB | ASP | B | 261 | 25.834 | 40.495 | 16.665 | 1.00 | 40.33 | C |
|---|---|---|---|---|---|---|---|---|---|---|---|
| ATOM | 1518 | CG | ASP | B | 261 | 26.245 | 39.132 | 17.183 | 1.00 | 46.67 | C |
| ATOM | 1519 | OD1 | ASP | B | 261 | 27.295 | 38.623 | 16.727 | 1.00 | 49.65 | O |
| ATOM | 1520 | OD2 | ASP | B | 261 | 25.525 | 38.560 | 18.035 | 1.00 | 50.57 | O |
| ATOM | 1521 | N | LYS | B | 262 | 25.069 | 43.193 | 18.355 | 1.00 | 30.45 | N |
| ATOM | 1522 | CA | LYS | B | 262 | 25.479 | 44.082 | 19.442 | 1.00 | 28.46 | C |
| ATOM | 1523 | C | LYS | B | 262 | 24.379 | 44.578 | 20.367 | 1.00 | 26.76 | C |
| ATOM | 1524 | O | LYS | B | 262 | 24.654 | 45.301 | 21.320 | 1.00 | 25.35 | O |
| ATOM | 1525 | CB | LYS | B | 262 | 26.241 | 45.297 | 18.878 | 1.00 | 27.07 | C |
| ATOM | 1526 | CG | LYS | B | 262 | 27.357 | 44.951 | 17.908 | 1.00 | 26.01 | C |
| ATOM | 1527 | CD | LYS | B | 262 | 28.235 | 43.836 | 18.449 | 1.00 | 26.80 | C |
| ATOM | 1528 | CE | LYS | B | 262 | 29.377 | 43.499 | 17.490 | 1.00 | 31.35 | C |
| ATOM | 1529 | NZ | LYS | B | 262 | 28.856 | 43.052 | 16.172 | 1.00 | 35.54 | N |
| ATOM | 1530 | N | PHE | B | 263 | 23.135 | 44.209 | 20.094 | 1.00 | 27.38 | N |
| ATOM | 1531 | CA | PHE | B | 263 | 22.043 | 44.663 | 20.942 | 1.00 | 27.79 | C |
| ATOM | 1532 | C | PHE | B | 263 | 21.155 | 43.523 | 21.406 | 1.00 | 28.66 | C |
| ATOM | 1533 | O | PHE | B | 263 | 21.239 | 42.408 | 20.889 | 1.00 | 25.25 | O |
| ATOM | 1534 | CB | PHE | B | 263 | 21.207 | 45.721 | 20.217 | 1.00 | 27.15 | C |
| ATOM | 1535 | CG | PHE | B | 263 | 22.005 | 46.916 | 19.764 | 1.00 | 29.50 | C |
| ATOM | 1536 | CD1 | PHE | B | 263 | 22.613 | 46.930 | 18.512 | 1.00 | 29.29 | C |
| ATOM | 1537 | CD2 | PHE | B | 263 | 22.197 | 48.006 | 20.615 | 1.00 | 28.89 | C |
| ATOM | 1538 | CE1 | PHE | B | 263 | 23.406 | 48.012 | 18.113 | 1.00 | 32.10 | C |
| ATOM | 1539 | CE2 | PHE | B | 263 | 22.986 | 49.090 | 20.231 | 1.00 | 29.79 | C |
| ATOM | 1540 | CZ | PHE | B | 263 | 23.593 | 49.096 | 18.981 | 1.00 | 31.21 | C |
| ATOM | 1541 | N | SER | B | 264 | 20.323 | 43.813 | 22.405 | 1.00 | 29.66 | N |
| ATOM | 1542 | CA | SER | B | 264 | 19.401 | 42.825 | 22.946 | 1.00 | 33.35 | C |
| ATOM | 1543 | C | SER | B | 264 | 17.994 | 43.082 | 22.411 | 1.00 | 35.50 | C |
| ATOM | 1544 | O | SER | B | 264 | 17.558 | 44.231 | 22.303 | 1.00 | 35.16 | O |
| ATOM | 1545 | CB | SER | B | 264 | 19.413 | 42.875 | 24.474 | 1.00 | 33.43 | C |
| ATOM | 1546 | OG | SER | B | 264 | 18.310 | 42.178 | 25.024 | 1.00 | 34.18 | O |
| ATOM | 1547 | N | ASN | B | 265 | 17.306 | 41.998 | 22.066 | 1.00 | 38.20 | N |
| ATOM | 1548 | CA | ASN | B | 265 | 15.952 | 42.036 | 21.528 | 1.00 | 42.52 | C |
| ATOM | 1549 | C | ASN | B | 265 | 14.929 | 42.090 | 22.667 | 1.00 | 44.22 | C |
| ATOM | 1550 | O | ASN | B | 265 | 13.727 | 41.959 | 22.449 | 1.00 | 44.33 | O |
| ATOM | 1551 | CB | ASN | B | 265 | 15.734 | 40.791 | 20.648 | 1.00 | 47.43 | C |
| ATOM | 1552 | CG | ASN | B | 265 | 14.377 | 40.769 | 19.969 | 1.00 | 52.30 | C |
| ATOM | 1553 | OD1 | ASN | B | 265 | 13.347 | 40.580 | 20.618 | 1.00 | 55.95 | O |
| ATOM | 1554 | ND2 | ASN | B | 265 | 14.368 | 40.958 | 18.654 | 1.00 | 55.04 | N |
| ATOM | 1555 | N | ILE | B | 266 | 15.408 | 42.275 | 23.890 | 1.00 | 46.53 | N |
| ATOM | 1556 | CA | ILE | B | 266 | 14.512 | 42.366 | 25.037 | 1.00 | 50.41 | C |
| ATOM | 1557 | C | ILE | B | 266 | 14.555 | 43.783 | 25.583 | 1.00 | 51.79 | C |
| ATOM | 1558 | O | ILE | B | 266 | 15.475 | 44.151 | 26.313 | 1.00 | 53.00 | O |
| ATOM | 1559 | CB | ILE | B | 266 | 14.906 | 41.378 | 26.162 | 1.00 | 52.11 | C |
| ATOM | 1560 | CG1 | ILE | B | 266 | 14.621 | 39.942 | 25.711 | 1.00 | 52.25 | C |
| ATOM | 1561 | CG2 | ILE | B | 266 | 14.125 | 41.703 | 27.446 | 1.00 | 51.47 | C |
| ATOM | 1562 | CD1 | ILE | B | 266 | 14.977 | 38.896 | 26.741 | 1.00 | 52.80 | C |
| ATOM | 1563 | N | SER | B | 267 | 13.554 | 44.575 | 25.220 | 1.00 | 52.82 | N |
| ATOM | 1564 | CA | SER | B | 267 | 13.479 | 45.960 | 25.655 | 1.00 | 53.92 | C |
| ATOM | 1565 | C | SER | B | 267 | 12.101 | 46.529 | 25.332 | 1.00 | 54.57 | C |
| ATOM | 1566 | O | SER | B | 267 | 11.650 | 46.470 | 24.184 | 1.00 | 55.28 | O |
| ATOM | 1567 | CB | SER | B | 267 | 14.566 | 46.780 | 24.944 | 1.00 | 53.43 | C |
| ATOM | 1568 | OG | SER | B | 267 | 14.486 | 48.159 | 25.265 | 1.00 | 53.30 | O |
| ATOM | 1569 | N | GLU | B | 268 | 11.427 | 47.063 | 26.346 | 1.00 | 54.63 | N |
| ATOM | 1570 | CA | GLU | B | 268 | 10.110 | 47.662 | 26.149 | 1.00 | 55.91 | C |
| ATOM | 1571 | C | GLU | B | 268 | 10.305 | 49.051 | 25.546 | 1.00 | 55.23 | C |
| ATOM | 1572 | O | GLU | B | 268 | 11.338 | 49.686 | 25.750 | 1.00 | 55.02 | O |
| ATOM | 1573 | CB | GLU | B | 268 | 9.365 | 47.811 | 27.483 | 1.00 | 57.62 | C |
| ATOM | 1574 | CG | GLU | B | 268 | 9.238 | 46.541 | 28.301 | 1.00 | 60.87 | C |
| ATOM | 1575 | CD | GLU | B | 268 | 8.565 | 46.781 | 29.645 | 1.00 | 63.06 | C |
| ATOM | 1576 | OE1 | GLU | B | 268 | 9.020 | 47.675 | 30.391 | 1.00 | 63.52 | O |
| ATOM | 1577 | OE2 | GLU | B | 268 | 7.584 | 46.072 | 29.960 | 1.00 | 65.17 | O |
| ATOM | 1578 | N | GLY | B | 269 | 9.307 | 49.520 | 24.808 | 1.00 | 55.14 | N |
| ATOM | 1579 | CA | GLY | B | 269 | 9.387 | 50.842 | 24.214 | 1.00 | 53.65 | C |
| ATOM | 1580 | C | GLY | B | 269 | 10.535 | 51.025 | 23.245 | 1.00 | 51.69 | C |
| ATOM | 1581 | O | GLY | B | 269 | 10.726 | 50.214 | 22.339 | 1.00 | 52.57 | O |
| ATOM | 1582 | N | LEU | B | 270 | 11.302 | 52.094 | 23.444 | 1.00 | 48.68 | N |
| ATOM | 1583 | CA | LEU | B | 270 | 12.434 | 52.417 | 22.578 | 1.00 | 46.00 | C |
| ATOM | 1584 | C | LEU | B | 270 | 13.481 | 51.300 | 22.540 | 1.00 | 43.42 | C |
| ATOM | 1585 | O | LEU | B | 270 | 14.198 | 51.074 | 23.524 | 1.00 | 43.72 | O |
| ATOM | 1586 | CB | LEU | B | 270 | 13.097 | 53.719 | 23.050 | 1.00 | 46.90 | C |
| ATOM | 1587 | CG | LEU | B | 270 | 13.922 | 54.527 | 22.034 | 1.00 | 48.10 | C |
| ATOM | 1588 | CD1 | LEU | B | 270 | 14.701 | 55.614 | 22.781 | 1.00 | 48.00 | C |
| ATOM | 1589 | CD2 | LEU | B | 270 | 14.885 | 53.621 | 21.261 | 1.00 | 49.29 | C |
| ATOM | 1590 | N | SER | B | 271 | 13.585 | 50.622 | 21.398 | 1.00 | 39.34 | N |
| ATOM | 1591 | CA | SER | B | 271 | 14.549 | 49.534 | 21.246 | 1.00 | 33.02 | C |
| ATOM | 1592 | C | SER | B | 271 | 15.455 | 49.723 | 20.043 | 1.00 | 29.95 | C |
| ATOM | 1593 | O | SER | B | 271 | 14.979 | 49.829 | 18.916 | 1.00 | 30.47 | O |

TABLE 4-continued

Stem Cell Factor Dimer

| ATOM | 1594 | CB | SER | B | 271 | 13.818 | 48.198 | 21.107 | 1.00 | 33.58 | C |
|------|------|-----|-----|---|-----|--------|--------|--------|------|-------|---|
| ATOM | 1595 | OG | SER | B | 271 | 14.740 | 47.135 | 20.920 | 1.00 | 29.31 | O |
| ATOM | 1596 | N | ASN | B | 272 | 16.763 | 49.756 | 20.270 | 1.00 | 27.19 | N |
| ATOM | 1597 | CA | ASN | B | 272 | 17.689 | 49.906 | 19.155 | 1.00 | 26.28 | C |
| ATOM | 1598 | C | ASN | B | 272 | 17.677 | 48.657 | 18.270 | 1.00 | 24.35 | C |
| ATOM | 1599 | O | ASN | B | 272 | 17.806 | 48.761 | 17.047 | 1.00 | 24.38 | O |
| ATOM | 1600 | CB | ASN | B | 272 | 19.112 | 50.191 | 19.649 | 1.00 | 28.40 | C |
| ATOM | 1601 | CG | ASN | B | 272 | 19.314 | 51.656 | 20.074 | 1.00 | 31.26 | C |
| ATOM | 1602 | OD1 | ASN | B | 272 | 18.490 | 52.525 | 19.775 | 1.00 | 29.59 | O |
| ATOM | 1603 | ND2 | ASN | B | 272 | 20.422 | 51.927 | 20.763 | 1.00 | 27.16 | N |
| ATOM | 1604 | N | TYR | B | 273 | 17.526 | 47.480 | 18.879 | 1.00 | 22.77 | N |
| ATOM | 1605 | CA | TYR | B | 273 | 17.478 | 46.233 | 18.105 | 1.00 | 22.69 | C |
| ATOM | 1606 | C | TYR | B | 273 | 16.283 | 46.306 | 17.142 | 1.00 | 20.30 | C |
| ATOM | 1607 | O | TYR | B | 273 | 16.387 | 45.988 | 15.959 | 1.00 | 18.57 | O |
| ATOM | 1608 | CB | TYR | B | 273 | 17.305 | 45.005 | 19.029 | 1.00 | 19.03 | C |
| ATOM | 1609 | CG | TYR | B | 273 | 17.499 | 43.665 | 18.325 | 1.00 | 19.58 | C |
| ATOM | 1610 | CD1 | TYR | B | 273 | 18.711 | 42.976 | 18.410 | 1.00 | 21.34 | C |
| ATOM | 1611 | CD2 | TYR | B | 273 | 16.475 | 43.098 | 17.555 | 1.00 | 21.61 | C |
| ATOM | 1612 | CE1 | TYR | B | 273 | 18.905 | 41.749 | 17.739 | 1.00 | 21.50 | C |
| ATOM | 1613 | CE2 | TYR | B | 273 | 16.654 | 41.870 | 16.879 | 1.00 | 20.21 | C |
| ATOM | 1614 | CZ | TYR | B | 273 | 17.870 | 41.208 | 16.974 | 1.00 | 21.89 | C |
| ATOM | 1615 | OH | TYR | B | 273 | 18.072 | 40.025 | 16.282 | 1.00 | 24.18 | O |
| ATOM | 1616 | N | SER | B | 274 | 15.148 | 46.743 | 17.663 | 1.00 | 22.80 | N |
| ATOM | 1617 | CA | SER | B | 274 | 13.927 | 46.832 | 16.863 | 1.00 | 27.21 | C |
| ATOM | 1618 | C | SER | B | 274 | 14.050 | 47.772 | 15.667 | 1.00 | 27.36 | C |
| ATOM | 1619 | O | SER | B | 274 | 13.613 | 47.449 | 14.563 | 1.00 | 30.53 | O |
| ATOM | 1620 | CB | SER | B | 274 | 12.764 | 47.274 | 17.744 | 1.00 | 28.04 | C |
| ATOM | 1621 | OG | SER | B | 274 | 11.648 | 47.587 | 16.945 | 1.00 | 36.14 | O |
| ATOM | 1622 | N | ILE | B | 275 | 14.643 | 48.936 | 15.884 | 1.00 | 26.70 | N |
| ATOM | 1623 | CA | ILE | B | 275 | 14.807 | 49.898 | 14.807 | 1.00 | 25.74 | C |
| ATOM | 1624 | C | ILE | B | 275 | 15.759 | 49.382 | 13.737 | 1.00 | 28.05 | C |
| ATOM | 1625 | O | ILE | B | 275 | 15.490 | 49.521 | 12.544 | 1.00 | 30.55 | O |
| ATOM | 1626 | CB | ILE | B | 275 | 15.301 | 51.240 | 15.372 | 1.00 | 27.01 | C |
| ATOM | 1627 | CG1 | ILE | B | 275 | 14.177 | 51.848 | 16.230 | 1.00 | 25.40 | C |
| ATOM | 1628 | CG2 | ILE | B | 275 | 15.706 | 52.193 | 14.243 | 1.00 | 25.64 | C |
| ATOM | 1629 | CD1 | ILE | B | 275 | 14.599 | 53.071 | 17.034 | 1.00 | 29.62 | C |
| ATOM | 1630 | N | ILE | B | 276 | 16.861 | 48.767 | 14.156 | 1.00 | 27.36 | N |
| ATOM | 1631 | CA | ILE | B | 276 | 17.828 | 48.242 | 13.210 | 1.00 | 26.58 | C |
| ATOM | 1632 | C | ILE | B | 276 | 17.194 | 47.141 | 12.367 | 1.00 | 28.05 | C |
| ATOM | 1633 | O | ILE | B | 276 | 17.449 | 47.048 | 11.158 | 1.00 | 26.42 | O |
| ATOM | 1634 | CB | ILE | B | 276 | 19.077 | 47.682 | 13.940 | 1.00 | 27.08 | C |
| ATOM | 1635 | CG1 | ILE | B | 276 | 19.794 | 48.818 | 14.676 | 1.00 | 29.78 | C |
| ATOM | 1636 | CG2 | ILE | B | 276 | 20.012 | 47.018 | 12.946 | 1.00 | 21.94 | C |
| ATOM | 1637 | CD1 | ILE | B | 276 | 20.973 | 48.376 | 15.530 | 1.00 | 31.10 | C |
| ATOM | 1638 | N | ASP | B | 277 | 16.375 | 46.307 | 13.006 | 1.00 | 28.02 | N |
| ATOM | 1639 | CA | ASP | B | 277 | 15.697 | 45.216 | 12.308 | 1.00 | 31.09 | C |
| ATOM | 1640 | C | ASP | B | 277 | 14.875 | 45.762 | 11.134 | 1.00 | 31.45 | C |
| ATOM | 1641 | O | ASP | B | 277 | 14.986 | 45.272 | 10.013 | 1.00 | 32.87 | O |
| ATOM | 1642 | CB | ASP | B | 277 | 14.778 | 44.448 | 13.271 | 1.00 | 34.57 | C |
| ATOM | 1643 | CG | ASP | B | 277 | 13.996 | 43.344 | 12.575 | 1.00 | 36.69 | C |
| ATOM | 1644 | OD1 | ASP | B | 277 | 14.621 | 42.396 | 12.063 | 1.00 | 37.70 | O |
| ATOM | 1645 | OD2 | ASP | B | 277 | 12.751 | 43.427 | 12.526 | 1.00 | 42.12 | O |
| ATOM | 1646 | N | LYS | B | 278 | 14.054 | 46.775 | 11.394 | 1.00 | 31.81 | N |
| ATOM | 1647 | CA | LYS | B | 278 | 13.241 | 47.388 | 10.346 | 1.00 | 33.40 | C |
| ATOM | 1648 | C | LYS | B | 278 | 14.132 | 47.982 | 9.259 | 1.00 | 33.30 | C |
| ATOM | 1649 | O | LYS | B | 278 | 13.841 | 47.849 | 8.075 | 1.00 | 33.52 | O |
| ATOM | 1650 | CB | LYS | B | 278 | 12.348 | 48.484 | 10.938 | 1.00 | 34.87 | C |
| ATOM | 1651 | CG | LYS | B | 278 | 11.222 | 47.948 | 11.806 | 1.00 | 39.50 | C |
| ATOM | 1652 | CD | LYS | B | 278 | 10.764 | 48.949 | 12.865 | 1.00 | 44.74 | C |
| ATOM | 1653 | CE | LYS | B | 278 | 9.850 | 48.261 | 13.896 | 1.00 | 47.34 | C |
| ATOM | 1654 | NZ | LYS | B | 278 | 9.637 | 49.060 | 15.144 | 1.00 | 49.68 | N |
| ATOM | 1655 | N | LEU | B | 279 | 15.227 | 48.623 | 9.662 | 1.00 | 33.17 | N |
| ATOM | 1656 | CA | LEU | B | 279 | 16.136 | 49.219 | 8.694 | 1.00 | 33.76 | C |
| ATOM | 1657 | C | LEU | B | 279 | 16.735 | 48.144 | 7.801 | 1.00 | 35.27 | C |
| ATOM | 1658 | O | LEU | B | 279 | 16.949 | 48.367 | 6.611 | 1.00 | 35.16 | O |
| ATOM | 1659 | CB | LEU | B | 279 | 17.254 | 49.994 | 9.397 | 1.00 | 31.81 | C |
| ATOM | 1660 | CG | LEU | B | 279 | 16.830 | 51.213 | 10.221 | 1.00 | 31.76 | C |
| ATOM | 1661 | CD1 | LEU | B | 279 | 18.076 | 51.978 | 10.657 | 1.00 | 27.74 | C |
| ATOM | 1662 | CD2 | LEU | B | 279 | 15.910 | 52.117 | 9.396 | 1.00 | 27.79 | C |
| ATOM | 1663 | N | VAL | B | 280 | 17.011 | 46.981 | 8.384 | 1.00 | 36.33 | N |
| ATOM | 1664 | CA | VAL | B | 280 | 17.566 | 45.859 | 7.640 | 1.00 | 36.53 | C |
| ATOM | 1665 | C | VAL | B | 280 | 16.589 | 45.355 | 6.575 | 1.00 | 36.86 | C |
| ATOM | 1666 | O | VAL | B | 280 | 16.991 | 44.953 | 5.489 | 1.00 | 36.16 | O |
| ATOM | 1667 | CB | VAL | B | 280 | 17.903 | 44.688 | 8.585 | 1.00 | 39.05 | C |
| ATOM | 1668 | CG1 | VAL | B | 280 | 18.312 | 43.460 | 7.775 | 1.00 | 40.46 | C |
| ATOM | 1669 | CG2 | VAL | B | 280 | 19.018 | 45.094 | 9.527 | 1.00 | 37.37 | C |
| ATOM | 1670 | N | ASN | B | 281 | 15.298 | 45.380 | 6.884 | 1.00 | 37.81 | N |

TABLE 4-continued

Stem Cell Factor Dimer

| ATOM | 1671 | CA | ASN | B | 281 | 14.303 | 44.910 | 5.937 | 1.00 | 37.92 | C |
|---|---|---|---|---|---|---|---|---|---|---|---|
| ATOM | 1672 | C | ASN | B | 281 | 14.111 | 45.832 | 4.742 | 1.00 | 39.69 | C |
| ATOM | 1673 | O | ASN | B | 281 | 13.937 | 45.358 | 3.623 | 1.00 | 40.54 | O |
| ATOM | 1674 | CB | ASN | B | 281 | 12.968 | 44.680 | 6.638 | 1.00 | 36.79 | C |
| ATOM | 1675 | CG | ASN | B | 281 | 13.007 | 43.487 | 7.570 | 1.00 | 35.96 | C |
| ATOM | 1676 | OD1 | ASN | B | 281 | 13.696 | 42.501 | 7.305 | 1.00 | 34.67 | O |
| ATOM | 1677 | ND2 | ASN | B | 281 | 12.255 | 43.563 | 8.660 | 1.00 | 35.46 | N |
| ATOM | 1678 | N | ILE | B | 282 | 14.135 | 47.141 | 4.962 | 1.00 | 41.96 | N |
| ATOM | 1679 | CA | ILE | B | 282 | 13.977 | 48.063 | 3.844 | 1.00 | 43.76 | C |
| ATOM | 1680 | C | ILE | B | 282 | 15.178 | 47.930 | 2.908 | 1.00 | 43.59 | C |
| ATOM | 1681 | O | ILE | B | 282 | 15.023 | 47.878 | 1.684 | 1.00 | 42.87 | O |
| ATOM | 1682 | CB | ILE | B | 282 | 13.837 | 49.528 | 4.322 | 1.00 | 46.35 | C |
| ATOM | 1683 | CG1 | ILE | B | 282 | 14.904 | 49.847 | 5.364 | 1.00 | 49.26 | C |
| ATOM | 1684 | CG2 | ILE | B | 282 | 12.450 | 49.755 | 4.895 | 1.00 | 46.46 | C |
| ATOM | 1685 | CD1 | ILE | B | 282 | 14.775 | 51.227 | 5.969 | 1.00 | 52.73 | C |
| ATOM | 1686 | N | VAL | B | 283 | 16.369 | 47.834 | 3.490 | 1.00 | 42.61 | N |
| ATOM | 1687 | CA | VAL | B | 283 | 17.591 | 47.701 | 2.707 | 1.00 | 44.18 | C |
| ATOM | 1688 | C | VAL | B | 283 | 17.683 | 46.332 | 2.039 | 1.00 | 45.95 | C |
| ATOM | 1689 | O | VAL | B | 283 | 18.330 | 46.180 | 1.005 | 1.00 | 44.64 | O |
| ATOM | 1690 | CB | VAL | B | 283 | 18.836 | 47.902 | 3.586 | 1.00 | 44.07 | C |
| ATOM | 1691 | CG1 | VAL | B | 283 | 20.078 | 47.992 | 2.729 | 1.00 | 45.78 | C |
| ATOM | 1692 | CG2 | VAL | B | 283 | 18.682 | 49.152 | 4.404 | 1.00 | 47.56 | C |
| ATOM | 1693 | N | ASP | B | 284 | 17.052 | 45.327 | 2.634 | 1.00 | 48.15 | N |
| ATOM | 1694 | CA | ASP | B | 284 | 17.088 | 43.999 | 2.043 | 1.00 | 50.89 | C |
| ATOM | 1695 | C | ASP | B | 284 | 16.085 | 43.925 | 0.905 | 1.00 | 51.42 | C |
| ATOM | 1696 | O | ASP | B | 284 | 16.235 | 43.124 | −0.014 | 1.00 | 50.07 | O |
| ATOM | 1697 | CB | ASP | B | 284 | 16.816 | 42.928 | 3.102 | 1.00 | 52.73 | C |
| ATOM | 1698 | CG | ASP | B | 284 | 18.063 | 42.590 | 3.910 | 1.00 | 54.77 | C |
| ATOM | 1699 | OD1 | ASP | B | 284 | 19.064 | 43.328 | 3.782 | 1.00 | 53.52 | O |
| ATOM | 1700 | OD2 | ASP | B | 284 | 18.048 | 41.596 | 4.671 | 1.00 | 56.89 | O |
| ATOM | 1701 | N | ASP | B | 285 | 15.065 | 44.773 | 0.962 | 1.00 | 53.52 | N |
| ATOM | 1702 | CA | ASP | B | 285 | 14.077 | 44.813 | −0.103 | 1.00 | 56.78 | C |
| ATOM | 1703 | C | ASP | B | 285 | 14.748 | 45.412 | −1.336 | 1.00 | 57.85 | C |
| ATOM | 1704 | O | ASP | B | 285 | 14.447 | 45.029 | −2.466 | 1.00 | 57.90 | O |
| ATOM | 1705 | CB | ASP | B | 285 | 12.872 | 45.664 | 0.303 | 1.00 | 57.84 | C |
| ATOM | 1706 | CG | ASP | B | 285 | 11.864 | 44.888 | 1.126 | 1.00 | 60.65 | C |
| ATOM | 1707 | OD1 | ASP | B | 285 | 11.413 | 43.820 | 0.658 | 1.00 | 62.40 | O |
| ATOM | 1708 | OD2 | ASP | B | 285 | 11.515 | 45.344 | 2.235 | 1.00 | 62.92 | O |
| ATOM | 1709 | N | LEU | B | 286 | 15.669 | 46.345 | −1.106 | 1.00 | 59.05 | N |
| ATOM | 1710 | CA | LEU | B | 286 | 16.389 | 46.993 | −2.194 | 1.00 | 61.21 | C |
| ATOM | 1711 | C | LEU | B | 286 | 17.308 | 46.003 | −2.903 | 1.00 | 62.73 | C |
| ATOM | 1712 | O | LEU | B | 286 | 17.385 | 45.991 | −4.131 | 1.00 | 63.40 | O |
| ATOM | 1713 | CB | LEU | B | 286 | 17.215 | 48.172 | −1.667 | 1.00 | 59.77 | C |
| ATOM | 1714 | CG | LEU | B | 286 | 16.469 | 49.304 | −0.952 | 1.00 | 59.72 | C |
| ATOM | 1715 | CD1 | LEU | B | 286 | 17.479 | 50.311 | −0.430 | 1.00 | 60.06 | C |
| ATOM | 1716 | CD2 | LEU | B | 286 | 15.485 | 49.975 | −1.895 | 1.00 | 58.38 | C |
| ATOM | 1717 | N | VAL | B | 287 | 18.003 | 45.173 | −2.128 | 1.00 | 65.19 | N |
| ATOM | 1718 | CA | VAL | B | 287 | 18.915 | 44.181 | −2.695 | 1.00 | 67.52 | C |
| ATOM | 1719 | C | VAL | B | 287 | 18.151 | 43.272 | −3.651 | 1.00 | 69.85 | C |
| ATOM | 1720 | O | VAL | B | 287 | 18.746 | 42.490 | −4.390 | 1.00 | 70.28 | O |
| ATOM | 1721 | CB | VAL | B | 287 | 19.587 | 43.321 | −1.586 | 1.00 | 66.53 | C |
| ATOM | 1722 | CG1 | VAL | B | 287 | 20.507 | 42.285 | −2.208 | 1.00 | 65.22 | C |
| ATOM | 1723 | CG2 | VAL | B | 287 | 20.383 | 44.211 | −0.647 | 1.00 | 64.95 | C |
| ATOM | 1724 | N | GLU | B | 288 | 16.826 | 43.387 | −3.636 | 1.00 | 72.56 | N |
| ATOM | 1725 | CA | GLU | B | 288 | 15.985 | 42.594 | −4.521 | 1.00 | 75.05 | C |
| ATOM | 1726 | C | GLU | B | 288 | 15.773 | 43.293 | −5.863 | 1.00 | 76.15 | C |
| ATOM | 1727 | O | GLU | B | 288 | 15.887 | 42.654 | −6.905 | 1.00 | 76.95 | O |
| ATOM | 1728 | CB | GLU | B | 288 | 14.631 | 42.303 | −3.870 | 1.00 | 75.38 | C |
| ATOM | 1729 | CG | GLU | B | 288 | 14.703 | 41.368 | −2.676 | 1.00 | 76.07 | C |
| ATOM | 1730 | CD | GLU | B | 288 | 13.334 | 40.869 | −2.260 | 1.00 | 76.91 | C |
| ATOM | 1731 | OE1 | GLU | B | 288 | 12.663 | 40.230 | −3.100 | 1.00 | 76.61 | O |
| ATOM | 1732 | OE2 | GLU | B | 288 | 12.928 | 41.116 | −1.102 | 1.00 | 77.21 | O |
| ATOM | 1733 | N | CYS | B | 289 | 15.465 | 44.592 | −5.847 | 1.00 | 77.68 | N |
| ATOM | 1734 | CA | CYS | B | 289 | 15.266 | 45.326 | −7.102 | 1.00 | 79.66 | C |
| ATOM | 1735 | C | CYS | B | 289 | 16.567 | 45.273 | −7.896 | 1.00 | 81.37 | C |
| ATOM | 1736 | O | CYS | B | 289 | 16.607 | 45.643 | −9.069 | 1.00 | 82.35 | O |
| ATOM | 1737 | CB | CYS | B | 289 | 14.862 | 46.798 | −6.853 | 1.00 | 78.42 | C |
| ATOM | 1738 | SG | CYS | B | 289 | 13.190 | 47.024 | −6.149 | 1.00 | 78.81 | S |
| ATOM | 1739 | N | VAL | B | 290 | 17.626 | 44.802 | −7.244 | 1.00 | 83.34 | N |
| ATOM | 1740 | CA | VAL | B | 290 | 18.939 | 44.678 | −7.868 | 1.00 | 85.04 | C |
| ATOM | 1741 | C | VAL | B | 290 | 19.114 | 43.291 | −8.477 | 1.00 | 86.93 | C |
| ATOM | 1742 | O | VAL | B | 290 | 19.836 | 43.121 | −9.458 | 1.00 | 87.33 | O |
| ATOM | 1743 | CB | VAL | B | 290 | 20.068 | 44.912 | −6.840 | 1.00 | 84.62 | C |
| ATOM | 1744 | CG1 | VAL | B | 290 | 21.422 | 44.610 | −7.465 | 1.00 | 84.22 | C |
| ATOM | 1745 | CG2 | VAL | B | 290 | 20.027 | 46.347 | −6.348 | 1.00 | 84.06 | C |
| ATOM | 1746 | N | LYS | B | 291 | 18.450 | 42.302 | −7.888 | 1.00 | 89.27 | N |
| ATOM | 1747 | CA | LYS | B | 291 | 18.538 | 40.931 | −8.375 | 1.00 | 91.52 | C |

TABLE 4-continued

Stem Cell Factor Dimer

| ATOM | 1748 | C | LYS | B | 291 | 18.122 | 40.793 | −9.836 | 1.00 | 92.26 | C |
|---|---|---|---|---|---|---|---|---|---|---|---|
| ATOM | 1749 | O | LYS | B | 291 | 18.958 | 40.871 | −10.737 | 1.00 | 92.64 | O |
| ATOM | 1750 | CB | LYS | B | 291 | 17.676 | 40.003 | −7.518 | 1.00 | 92.27 | C |
| ATOM | 1751 | CG | LYS | B | 291 | 18.450 | 39.217 | −6.475 | 1.00 | 93.39 | C |
| ATOM | 1752 | CD | LYS | B | 291 | 17.635 | 38.021 | −6.007 | 1.00 | 94.40 | C |
| ATOM | 1753 | CE | LYS | B | 291 | 18.452 | 37.076 | −5.146 | 1.00 | 93.52 | C |
| ATOM | 1754 | NZ | LYS | B | 291 | 17.667 | 35.850 | −4.845 | 1.00 | 93.70 | N |
| ATOM | 1755 | N | GLU | B | 292 | 16.829 | 40.583 | −10.061 | 1.00 | 93.06 | N |
| ATOM | 1756 | CA | GLU | B | 292 | 16.289 | 40.422 | −11.407 | 1.00 | 93.90 | C |
| ATOM | 1757 | C | GLU | B | 292 | 16.822 | 41.477 | −12.370 | 1.00 | 94.28 | C |
| ATOM | 1758 | O | GLU | B | 292 | 16.905 | 41.237 | −13.575 | 1.00 | 94.59 | O |
| ATOM | 1759 | CB | GLU | B | 292 | 14.764 | 40.479 | −11.366 | 1.00 | 93.97 | C |
| ATOM | 1760 | N | ASN | B | 293 | 17.180 | 42.639 | −11.829 | 1.00 | 94.51 | N |
| ATOM | 1761 | CA | ASN | B | 293 | 17.700 | 43.752 | −12.620 | 1.00 | 94.89 | C |
| ATOM | 1762 | C | ASN | B | 293 | 18.486 | 43.306 | −13.847 | 1.00 | 95.25 | C |
| ATOM | 1763 | O | ASN | B | 293 | 19.547 | 42.691 | −13.732 | 1.00 | 94.68 | O |
| ATOM | 1764 | CB | ASN | B | 293 | 18.569 | 44.647 | −11.748 | 1.00 | 94.54 | C |
| ATOM | 1765 | N | SER | B | 294 | 17.947 | 43.622 | −15.021 | 1.00 | 96.10 | N |
| ATOM | 1766 | CA | SER | B | 294 | 18.578 | 43.279 | −16.291 | 1.00 | 96.82 | C |
| ATOM | 1767 | C | SER | B | 294 | 19.260 | 44.516 | −16.862 | 1.00 | 97.43 | C |
| ATOM | 1768 | O | SER | B | 294 | 19.786 | 44.493 | −17.976 | 1.00 | 97.54 | O |
| ATOM | 1769 | CB | SER | B | 294 | 17.534 | 42.760 | −17.272 | 1.00 | 96.87 | C |
| ATOM | 1770 | N | SER | B | 295 | 19.234 | 45.599 | −16.091 | 1.00 | 97.82 | N |
| ATOM | 1771 | CA | SER | B | 295 | 19.850 | 46.851 | −16.505 | 1.00 | 98.14 | C |
| ATOM | 1772 | C | SER | B | 295 | 21.360 | 46.757 | −16.330 | 1.00 | 98.75 | C |
| ATOM | 1773 | O | SER | B | 295 | 21.849 | 46.322 | −15.287 | 1.00 | 98.85 | O |
| ATOM | 1774 | CB | SER | B | 295 | 19.297 | 48.007 | −15.680 | 1.00 | 97.18 | C |
| ATOM | 1775 | N | LYS | B | 296 | 22.094 | 47.157 | −17.361 | 1.00 | 99.70 | N |
| ATOM | 1776 | CA | LYS | B | 296 | 23.549 | 47.124 | −17.320 | 1.00 | 100.08 | C |
| ATOM | 1777 | C | LYS | B | 296 | 24.090 | 48.545 | −17.201 | 1.00 | 100.40 | C |
| ATOM | 1778 | O | LYS | B | 296 | 23.910 | 49.370 | −18.099 | 1.00 | 100.26 | O |
| ATOM | 1779 | CB | LYS | B | 296 | 24.095 | 46.454 | −18.577 | 1.00 | 100.16 | C |
| ATOM | 1780 | N | ASP | B | 297 | 24.747 | 48.826 | −16.082 | 1.00 | 100.71 | N |
| ATOM | 1781 | CA | ASP | B | 297 | 25.315 | 50.143 | −15.840 | 1.00 | 101.31 | C |
| ATOM | 1782 | C | ASP | B | 297 | 26.625 | 50.000 | −15.070 | 1.00 | 101.82 | C |
| ATOM | 1783 | O | ASP | B | 297 | 27.622 | 50.650 | −15.392 | 1.00 | 101.90 | O |
| ATOM | 1784 | CB | ASP | B | 297 | 24.327 | 50.997 | −15.053 | 1.00 | 101.33 | C |
| ATOM | 1785 | N | LEU | B | 298 | 26.607 | 49.137 | −14.058 | 1.00 | 102.10 | N |
| ATOM | 1786 | CA | LEU | B | 298 | 27.770 | 48.870 | −13.217 | 1.00 | 102.11 | C |
| ATOM | 1787 | C | LEU | B | 298 | 27.299 | 48.176 | −11.949 | 1.00 | 102.30 | C |
| ATOM | 1788 | O | LEU | B | 298 | 28.019 | 48.131 | −10.952 | 1.00 | 102.51 | O |
| ATOM | 1789 | CB | LEU | B | 298 | 28.489 | 50.171 | −12.863 | 1.00 | 102.08 | C |
| ATOM | 1790 | N | LYS | B | 299 | 26.081 | 47.641 | −11.997 | 1.00 | 102.53 | N |
| ATOM | 1791 | CA | LYS | B | 299 | 25.492 | 46.946 | −10.855 | 1.00 | 102.73 | C |
| ATOM | 1792 | C | LYS | B | 299 | 26.278 | 45.687 | −10.495 | 1.00 | 103.02 | C |
| ATOM | 1793 | O | LYS | B | 299 | 25.780 | 44.568 | −10.633 | 1.00 | 103.10 | O |
| ATOM | 1794 | CB | LYS | B | 299 | 24.039 | 46.591 | −11.157 | 1.00 | 102.10 | C |
| ATOM | 1795 | N | LYS | B | 300 | 27.508 | 45.877 | −10.030 | 1.00 | 103.14 | N |
| ATOM | 1796 | CA | LYS | B | 300 | 28.365 | 44.763 | −9.650 | 1.00 | 103.42 | C |
| ATOM | 1797 | C | LYS | B | 300 | 29.427 | 45.224 | −8.656 | 1.00 | 103.57 | C |
| ATOM | 1798 | O | LYS | B | 300 | 29.379 | 44.873 | −7.475 | 1.00 | 103.46 | O |
| ATOM | 1799 | CB | LYS | B | 300 | 29.026 | 44.173 | −10.887 | 1.00 | 103.35 | C |
| ATOM | 1800 | N | SER | B | 301 | 30.378 | 46.014 | −9.149 | 1.00 | 103.66 | N |
| ATOM | 1801 | CA | SER | B | 301 | 31.474 | 46.548 | −8.342 | 1.00 | 103.79 | C |
| ATOM | 1802 | C | SER | B | 301 | 32.583 | 45.521 | −8.121 | 1.00 | 103.79 | C |
| ATOM | 1803 | O | SER | B | 301 | 33.224 | 45.505 | −7.069 | 1.00 | 103.66 | O |
| ATOM | 1804 | CB | SER | B | 301 | 30.947 | 47.053 | −6.996 | 1.00 | 103.60 | C |
| ATOM | 1805 | N | PHE | B | 302 | 32.805 | 44.670 | −9.120 | 1.00 | 103.61 | N |
| ATOM | 1806 | CA | PHE | B | 302 | 33.839 | 43.640 | −9.051 | 1.00 | 103.14 | C |
| ATOM | 1807 | C | PHE | B | 302 | 33.752 | 42.815 | −7.768 | 1.00 | 102.53 | C |
| ATOM | 1808 | O | PHE | B | 302 | 32.978 | 41.859 | −7.687 | 1.00 | 102.07 | O |
| ATOM | 1809 | CB | PHE | B | 302 | 35.222 | 44.283 | −9.172 | 1.00 | 103.18 | C |
| ATOM | 1810 | N | LYS | B | 303 | 34.554 | 43.189 | −6.772 | 1.00 | 101.84 | N |
| ATOM | 1811 | CA | LYS | B | 303 | 34.577 | 42.495 | −5.488 | 1.00 | 100.63 | C |
| ATOM | 1812 | C | LYS | B | 303 | 33.991 | 43.369 | −4.375 | 1.00 | 99.62 | C |
| ATOM | 1813 | O | LYS | B | 303 | 32.952 | 44.003 | −4.557 | 1.00 | 99.74 | O |
| ATOM | 1814 | CB | LYS | B | 303 | 36.007 | 42.092 | −5.144 | 1.00 | 100.68 | C |
| ATOM | 1815 | N | SER | B | 304 | 34.657 | 43.398 | −3.223 | 1.00 | 98.02 | N |
| ATOM | 1816 | CA | SER | B | 304 | 34.189 | 44.197 | −2.093 | 1.00 | 96.12 | C |
| ATOM | 1817 | C | SER | B | 304 | 35.197 | 45.287 | −1.746 | 1.00 | 94.26 | C |
| ATOM | 1818 | O | SER | B | 304 | 36.399 | 45.035 | −1.693 | 1.00 | 94.27 | O |
| ATOM | 1819 | CB | SER | B | 304 | 33.957 | 43.306 | −0.870 | 1.00 | 96.03 | C |
| ATOM | 1820 | OG | SER | B | 304 | 35.168 | 42.716 | −0.438 | 1.00 | 96.47 | O |
| ATOM | 1821 | N | PRO | B | 305 | 34.713 | 46.517 | −1.507 | 1.00 | 92.25 | N |
| ATOM | 1822 | CA | PRO | B | 305 | 35.564 | 47.660 | −1.163 | 1.00 | 90.03 | C |
| ATOM | 1823 | C | PRO | B | 305 | 36.325 | 47.470 | 0.143 | 1.00 | 87.64 | C |
| ATOM | 1824 | O | PRO | B | 305 | 36.170 | 46.462 | 0.832 | 1.00 | 87.52 | O |

TABLE 4-continued

Stem Cell Factor Dimer

| ATOM | 1825 | CB | PRO | B | 305 | 34.571 | 48.818 | −1.073 | 1.00 | 90.88 | C |
|---|---|---|---|---|---|---|---|---|---|---|---|
| ATOM | 1826 | CG | PRO | B | 305 | 33.485 | 48.412 | −2.014 | 1.00 | 91.99 | C |
| ATOM | 1827 | CD | PRO | B | 305 | 33.317 | 46.952 | −1.683 | 1.00 | 92.24 | C |
| ATOM | 1828 | N | GLU | B | 306 | 37.149 | 48.458 | 0.469 | 1.00 | 84.58 | N |
| ATOM | 1829 | CA | GLU | B | 306 | 37.944 | 48.447 | 1.687 | 1.00 | 80.75 | C |
| ATOM | 1830 | C | GLU | B | 306 | 37.022 | 48.847 | 2.842 | 1.00 | 76.69 | C |
| ATOM | 1831 | O | GLU | B | 306 | 36.143 | 49.693 | 2.677 | 1.00 | 75.73 | O |
| ATOM | 1832 | CB | GLU | B | 306 | 39.095 | 49.451 | 1.540 | 1.00 | 82.18 | C |
| ATOM | 1833 | CG | GLU | B | 306 | 40.088 | 49.503 | 2.690 | 1.00 | 83.86 | C |
| ATOM | 1834 | CD | GLU | B | 306 | 41.032 | 50.696 | 2.582 | 1.00 | 85.10 | C |
| ATOM | 1835 | OE1 | GLU | B | 306 | 41.781 | 50.786 | 1.584 | 1.00 | 85.38 | O |
| ATOM | 1836 | OE2 | GLU | B | 306 | 41.020 | 51.553 | 3.494 | 1.00 | 85.08 | O |
| ATOM | 1837 | N | PRO | B | 307 | 37.193 | 48.223 | 4.017 | 1.00 | 73.12 | N |
| ATOM | 1838 | CA | PRO | B | 307 | 36.360 | 48.539 | 5.185 | 1.00 | 69.76 | C |
| ATOM | 1839 | C | PRO | B | 307 | 36.742 | 49.878 | 5.824 | 1.00 | 66.56 | C |
| ATOM | 1840 | O | PRO | B | 307 | 37.926 | 50.193 | 5.957 | 1.00 | 64.97 | O |
| ATOM | 1841 | CB | PRO | B | 307 | 36.628 | 47.368 | 6.136 | 1.00 | 70.02 | C |
| ATOM | 1842 | CG | PRO | B | 307 | 37.091 | 46.264 | 5.224 | 1.00 | 71.66 | C |
| ATOM | 1843 | CD | PRO | B | 307 | 37.970 | 46.996 | 4.253 | 1.00 | 72.14 | C |
| ATOM | 1844 | N | ARG | B | 308 | 35.742 | 50.663 | 6.217 | 1.00 | 63.07 | N |
| ATOM | 1845 | CA | ARG | B | 308 | 35.998 | 51.948 | 6.860 | 1.00 | 59.50 | C |
| ATOM | 1846 | C | ARG | B | 308 | 35.120 | 52.134 | 8.088 | 1.00 | 56.46 | C |
| ATOM | 1847 | O | ARG | B | 308 | 34.031 | 51.566 | 8.183 | 1.00 | 55.95 | O |
| ATOM | 1848 | CB | ARG | B | 308 | 35.745 | 53.109 | 5.896 | 1.00 | 60.12 | C |
| ATOM | 1849 | CG | ARG | B | 308 | 36.675 | 53.175 | 4.704 | 1.00 | 62.24 | C |
| ATOM | 1850 | CD | ARG | B | 308 | 36.430 | 54.452 | 3.914 | 1.00 | 64.63 | C |
| ATOM | 1851 | NE | ARG | B | 308 | 37.145 | 54.461 | 2.640 | 1.00 | 67.72 | N |
| ATOM | 1852 | CZ | ARG | B | 308 | 37.166 | 55.491 | 1.797 | 1.00 | 68.01 | C |
| ATOM | 1853 | NH1 | ARG | B | 308 | 36.513 | 56.609 | 2.091 | 1.00 | 68.04 | N |
| ATOM | 1854 | NH2 | ARG | B | 308 | 37.831 | 55.399 | 0.652 | 1.00 | 68.32 | N |
| ATOM | 1855 | N | LEU | B | 309 | 35.603 | 52.934 | 9.030 | 1.00 | 52.29 | N |
| ATOM | 1856 | CA | LEU | B | 309 | 34.857 | 53.212 | 10.244 | 1.00 | 48.71 | C |
| ATOM | 1857 | C | LEU | B | 309 | 34.053 | 54.486 | 10.070 | 1.00 | 46.92 | C |
| ATOM | 1858 | O | LEU | B | 309 | 34.495 | 55.419 | 9.398 | 1.00 | 47.41 | O |
| ATOM | 1859 | CB | LEU | B | 309 | 35.809 | 53.358 | 11.429 | 1.00 | 47.87 | C |
| ATOM | 1860 | CG | LEU | B | 309 | 36.441 | 52.060 | 11.931 | 1.00 | 47.25 | C |
| ATOM | 1861 | CD1 | LEU | B | 309 | 37.403 | 52.377 | 13.069 | 1.00 | 48.09 | C |
| ATOM | 1862 | CD2 | LEU | B | 309 | 35.352 | 51.098 | 12.399 | 1.00 | 45.50 | C |
| ATOM | 1863 | N | PHE | B | 310 | 32.867 | 54.520 | 10.673 | 1.00 | 44.70 | N |
| ATOM | 1864 | CA | PHE | B | 310 | 31.987 | 55.685 | 10.591 | 1.00 | 41.73 | C |
| ATOM | 1865 | C | PHE | B | 310 | 31.218 | 55.854 | 11.889 | 1.00 | 40.76 | C |
| ATOM | 1866 | O | PHE | B | 310 | 30.862 | 54.865 | 12.524 | 1.00 | 42.19 | O |
| ATOM | 1867 | CB | PHE | B | 310 | 30.956 | 55.522 | 9.465 | 1.00 | 41.12 | C |
| ATOM | 1868 | CG | PHE | B | 310 | 31.552 | 55.318 | 8.105 | 1.00 | 38.93 | C |
| ATOM | 1869 | CD1 | PHE | B | 310 | 31.986 | 54.064 | 7.702 | 1.00 | 37.47 | C |
| ATOM | 1870 | CD2 | PHE | B | 310 | 31.683 | 56.390 | 7.223 | 1.00 | 40.56 | C |
| ATOM | 1871 | CE1 | PHE | B | 310 | 32.542 | 53.878 | 6.444 | 1.00 | 37.92 | C |
| ATOM | 1872 | CE2 | PHE | B | 310 | 32.242 | 56.212 | 5.961 | 1.00 | 37.25 | C |
| ATOM | 1873 | CZ | PHE | B | 310 | 32.671 | 54.955 | 5.573 | 1.00 | 36.90 | C |
| ATOM | 1874 | N | THR | B | 311 | 30.955 | 57.100 | 12.281 | 1.00 | 38.12 | N |
| ATOM | 1875 | CA | THR | B | 311 | 30.174 | 57.345 | 13.489 | 1.00 | 35.14 | C |
| ATOM | 1876 | C | THR | B | 311 | 28.716 | 57.104 | 13.087 | 1.00 | 33.93 | C |
| ATOM | 1877 | O | THR | B | 311 | 28.398 | 56.982 | 11.894 | 1.00 | 33.31 | O |
| ATOM | 1878 | CB | THR | B | 311 | 30.296 | 58.803 | 14.007 | 1.00 | 34.64 | C |
| ATOM | 1879 | OG1 | THR | B | 311 | 29.566 | 59.673 | 13.139 | 1.00 | 34.01 | O |
| ATOM | 1880 | CG2 | THR | B | 311 | 31.753 | 59.251 | 14.063 | 1.00 | 34.36 | C |
| ATOM | 1881 | N | PRO | B | 312 | 27.807 | 57.034 | 14.070 | 1.00 | 32.38 | N |
| ATOM | 1882 | CA | PRO | B | 312 | 26.414 | 56.799 | 13.686 | 1.00 | 31.44 | C |
| ATOM | 1883 | C | PRO | B | 312 | 25.847 | 57.830 | 12.720 | 1.00 | 31.83 | C |
| ATOM | 1884 | O | PRO | B | 312 | 25.191 | 57.468 | 11.738 | 1.00 | 29.74 | O |
| ATOM | 1885 | CB | PRO | B | 312 | 25.695 | 56.764 | 15.026 | 1.00 | 30.31 | C |
| ATOM | 1886 | CG | PRO | B | 312 | 26.727 | 56.090 | 15.904 | 1.00 | 31.27 | C |
| ATOM | 1887 | CD | PRO | B | 312 | 27.996 | 56.828 | 15.518 | 1.00 | 30.88 | C |
| ATOM | 1888 | N | GLU | B | 313 | 26.092 | 59.109 | 12.968 | 1.00 | 32.84 | N |
| ATOM | 1889 | CA | GLU | B | 313 | 25.552 | 60.102 | 12.048 | 1.00 | 36.95 | C |
| ATOM | 1890 | C | GLU | B | 313 | 26.130 | 59.936 | 10.647 | 1.00 | 35.86 | C |
| ATOM | 1891 | O | GLU | B | 313 | 25.399 | 60.028 | 9.666 | 1.00 | 37.73 | O |
| ATOM | 1892 | CB | GLU | B | 313 | 25.768 | 61.533 | 12.572 | 1.00 | 40.35 | C |
| ATOM | 1893 | CG | GLU | B | 313 | 27.158 | 61.866 | 13.072 | 1.00 | 48.07 | C |
| ATOM | 1894 | CD | GLU | B | 313 | 28.160 | 62.071 | 11.956 | 1.00 | 53.14 | C |
| ATOM | 1895 | OE1 | GLU | B | 313 | 27.739 | 62.435 | 10.835 | 1.00 | 56.07 | O |
| ATOM | 1896 | OE2 | GLU | B | 313 | 29.373 | 61.893 | 12.208 | 1.00 | 56.39 | O |
| ATOM | 1897 | N | GLU | B | 314 | 27.430 | 59.669 | 10.548 | 1.00 | 35.90 | N |
| ATOM | 1898 | CA | GLU | B | 314 | 28.065 | 59.487 | 9.243 | 1.00 | 36.50 | C |
| ATOM | 1899 | C | GLU | B | 314 | 27.489 | 58.270 | 8.507 | 1.00 | 36.42 | C |
| ATOM | 1900 | O | GLU | B | 314 | 27.220 | 58.332 | 7.307 | 1.00 | 33.77 | O |
| ATOM | 1901 | CB | GLU | B | 314 | 29.587 | 59.291 | 9.387 | 1.00 | 39.57 | C |

TABLE 4-continued

Stem Cell Factor Dimer

| ATOM | 1902 | CG | GLU | B | 314 | 30.356 | 60.423 | 10.075 | 1.00 | 43.63 | C |
|---|---|---|---|---|---|---|---|---|---|---|---|
| ATOM | 1903 | CD | GLU | B | 314 | 31.860 | 60.150 | 10.172 | 1.00 | 46.74 | C |
| ATOM | 1904 | OE1 | GLU | B | 314 | 32.247 | 59.041 | 10.607 | 1.00 | 44.49 | O |
| ATOM | 1905 | OE2 | GLU | B | 314 | 32.658 | 61.049 | 9.817 | 1.00 | 48.52 | O |
| ATOM | 1906 | N | PHE | B | 315 | 27.313 | 57.164 | 9.232 | 1.00 | 34.16 | N |
| ATOM | 1907 | CA | PHE | B | 315 | 26.803 | 55.931 | 8.637 | 1.00 | 32.79 | C |
| ATOM | 1908 | C | PHE | B | 315 | 25.391 | 56.068 | 8.077 | 1.00 | 33.32 | C |
| ATOM | 1909 | O | PHE | B | 315 | 25.111 | 55.653 | 6.946 | 1.00 | 32.68 | O |
| ATOM | 1910 | CB | PHE | B | 315 | 26.818 | 54.797 | 9.670 | 1.00 | 30.68 | C |
| ATOM | 1911 | CG | PHE | B | 315 | 26.395 | 53.459 | 9.112 | 1.00 | 30.52 | C |
| ATOM | 1912 | CD1 | PHE | B | 315 | 27.344 | 52.569 | 8.595 | 1.00 | 28.74 | C |
| ATOM | 1913 | CD2 | PHE | B | 315 | 25.049 | 53.085 | 9.105 | 1.00 | 28.69 | C |
| ATOM | 1914 | CE1 | PHE | B | 315 | 26.960 | 51.331 | 8.086 | 1.00 | 27.98 | C |
| ATOM | 1915 | CE2 | PHE | B | 315 | 24.650 | 51.844 | 8.596 | 1.00 | 26.95 | C |
| ATOM | 1916 | CZ | PHE | B | 315 | 25.603 | 50.967 | 8.088 | 1.00 | 29.41 | C |
| ATOM | 1917 | N | PHE | B | 316 | 24.497 | 56.652 | 8.860 | 1.00 | 33.65 | N |
| ATOM | 1918 | CA | PHE | B | 316 | 23.130 | 56.777 | 8.405 | 1.00 | 36.80 | C |
| ATOM | 1919 | C | PHE | B | 316 | 22.885 | 57.866 | 7.381 | 1.00 | 39.29 | C |
| ATOM | 1920 | O | PHE | B | 316 | 21.802 | 57.948 | 6.804 | 1.00 | 40.21 | O |
| ATOM | 1921 | CB | PHE | B | 316 | 22.195 | 56.888 | 9.608 | 1.00 | 35.12 | C |
| ATOM | 1922 | CG | PHE | B | 316 | 22.153 | 55.627 | 10.421 | 1.00 | 34.42 | C |
| ATOM | 1923 | CD1 | PHE | B | 316 | 23.028 | 55.441 | 11.491 | 1.00 | 33.83 | C |
| ATOM | 1924 | CD2 | PHE | B | 316 | 21.312 | 54.578 | 10.049 | 1.00 | 32.73 | C |
| ATOM | 1925 | CE1 | PHE | B | 316 | 23.072 | 54.222 | 12.176 | 1.00 | 35.74 | C |
| ATOM | 1926 | CE2 | PHE | B | 316 | 21.346 | 53.353 | 10.723 | 1.00 | 31.66 | C |
| ATOM | 1927 | CZ | PHE | B | 316 | 22.225 | 53.170 | 11.786 | 1.00 | 32.51 | C |
| ATOM | 1928 | N | ARG | B | 317 | 23.890 | 58.703 | 7.147 | 1.00 | 40.85 | N |
| ATOM | 1929 | CA | ARG | B | 317 | 23.758 | 59.723 | 6.122 | 1.00 | 42.36 | C |
| ATOM | 1930 | C | ARG | B | 317 | 24.001 | 58.947 | 4.825 | 1.00 | 41.17 | C |
| ATOM | 1931 | O | ARG | B | 317 | 23.232 | 59.056 | 3.871 | 1.00 | 41.74 | O |
| ATOM | 1932 | CB | ARG | B | 317 | 24.799 | 60.832 | 6.319 | 1.00 | 45.58 | C |
| ATOM | 1933 | CG | ARG | B | 317 | 24.458 | 61.797 | 7.460 | 1.00 | 51.23 | C |
| ATOM | 1934 | CD | ARG | B | 317 | 25.622 | 62.740 | 7.790 | 1.00 | 54.05 | C |
| ATOM | 1935 | NE | ARG | B | 317 | 25.270 | 63.743 | 8.798 | 1.00 | 54.75 | N |
| ATOM | 1936 | CZ | ARG | B | 317 | 26.132 | 64.607 | 9.338 | 1.00 | 56.14 | C |
| ATOM | 1937 | NH1 | ARG | B | 317 | 27.410 | 64.599 | 8.977 | 1.00 | 57.31 | N |
| ATOM | 1938 | NH2 | ARG | B | 317 | 25.715 | 65.490 | 10.236 | 1.00 | 56.15 | N |
| ATOM | 1939 | N | ILE | B | 318 | 25.055 | 58.133 | 4.816 | 1.00 | 39.36 | N |
| ATOM | 1940 | CA | ILE | B | 318 | 25.391 | 57.306 | 3.657 | 1.00 | 38.03 | C |
| ATOM | 1941 | C | ILE | B | 318 | 24.245 | 56.340 | 3.371 | 1.00 | 36.22 | C |
| ATOM | 1942 | O | ILE | B | 318 | 24.029 | 55.926 | 2.232 | 1.00 | 36.42 | O |
| ATOM | 1943 | CB | ILE | B | 318 | 26.676 | 56.476 | 3.911 | 1.00 | 39.68 | C |
| ATOM | 1944 | CG1 | ILE | B | 318 | 27.919 | 57.346 | 3.707 | 1.00 | 40.60 | C |
| ATOM | 1945 | CG2 | ILE | B | 318 | 26.723 | 55.270 | 2.973 | 1.00 | 37.16 | C |
| ATOM | 1946 | CD1 | ILE | B | 318 | 27.986 | 58.564 | 4.591 | 1.00 | 44.51 | C |
| ATOM | 1947 | N | PHE | B | 319 | 23.525 | 55.978 | 4.425 | 1.00 | 34.28 | N |
| ATOM | 1948 | CA | PHE | B | 319 | 22.397 | 55.066 | 4.334 | 1.00 | 33.54 | C |
| ATOM | 1949 | C | PHE | B | 319 | 21.210 | 55.724 | 3.615 | 1.00 | 34.34 | C |
| ATOM | 1950 | O | PHE | B | 319 | 20.709 | 55.209 | 2.609 | 1.00 | 30.32 | O |
| ATOM | 1951 | CB | PHE | B | 319 | 21.985 | 54.645 | 5.747 | 1.00 | 32.93 | C |
| ATOM | 1952 | CG | PHE | B | 319 | 20.712 | 53.853 | 5.806 | 1.00 | 32.12 | C |
| ATOM | 1953 | CD1 | PHE | B | 319 | 20.717 | 52.481 | 5.585 | 1.00 | 35.73 | C |
| ATOM | 1954 | CD2 | PHE | B | 319 | 19.510 | 54.473 | 6.128 | 1.00 | 32.66 | C |
| ATOM | 1955 | CE1 | PHE | B | 319 | 19.542 | 51.734 | 5.695 | 1.00 | 32.65 | C |
| ATOM | 1956 | CE2 | PHE | B | 319 | 18.328 | 53.734 | 6.237 | 1.00 | 31.79 | C |
| ATOM | 1957 | CZ | PHE | B | 319 | 18.347 | 52.364 | 6.022 | 1.00 | 32.56 | C |
| ATOM | 1958 | N | ASN | B | 320 | 20.757 | 56.858 | 4.139 | 1.00 | 35.81 | N |
| ATOM | 1959 | CA | ASN | B | 320 | 19.631 | 57.559 | 3.536 | 1.00 | 39.77 | C |
| ATOM | 1960 | C | ASN | B | 320 | 19.920 | 57.913 | 2.083 | 1.00 | 41.47 | C |
| ATOM | 1961 | O | ASN | B | 320 | 19.079 | 57.720 | 1.211 | 1.00 | 39.25 | O |
| ATOM | 1962 | CB | ASN | B | 320 | 19.304 | 58.824 | 4.324 | 1.00 | 39.83 | C |
| ATOM | 1963 | CG | ASN | B | 320 | 18.825 | 58.527 | 5.731 | 1.00 | 42.12 | C |
| ATOM | 1964 | OD1 | ASN | B | 320 | 17.933 | 57.699 | 5.941 | 1.00 | 43.16 | O |
| ATOM | 1965 | ND2 | ASN | B | 320 | 19.407 | 59.214 | 6.706 | 1.00 | 43.50 | N |
| ATOM | 1966 | N | ARG | B | 321 | 21.119 | 58.420 | 1.823 | 1.00 | 45.27 | N |
| ATOM | 1967 | CA | ARG | B | 321 | 21.498 | 58.780 | 0.464 | 1.00 | 50.92 | C |
| ATOM | 1968 | C | ARG | B | 321 | 21.341 | 57.581 | −0.461 | 1.00 | 51.05 | C |
| ATOM | 1969 | O | ARG | B | 321 | 20.706 | 57.674 | −1.510 | 1.00 | 50.54 | O |
| ATOM | 1970 | CB | ARG | B | 321 | 22.946 | 59.269 | 0.436 | 1.00 | 54.83 | C |
| ATOM | 1971 | CG | ARG | B | 321 | 23.177 | 60.518 | 1.268 | 1.00 | 61.05 | C |
| ATOM | 1972 | CD | ARG | B | 321 | 24.652 | 60.702 | 1.601 | 1.00 | 65.80 | C |
| ATOM | 1973 | NE | ARG | B | 321 | 24.847 | 61.701 | 2.650 | 1.00 | 69.86 | N |
| ATOM | 1974 | CZ | ARG | B | 321 | 25.967 | 61.839 | 3.353 | 1.00 | 71.34 | C |
| ATOM | 1975 | NH1 | ARG | B | 321 | 27.004 | 61.040 | 3.124 | 1.00 | 71.44 | N |
| ATOM | 1976 | NH2 | ARG | B | 321 | 26.049 | 62.775 | 4.289 | 1.00 | 72.83 | N |
| ATOM | 1977 | N | SER | B | 322 | 21.918 | 56.452 | −0.060 | 1.00 | 52.87 | N |
| ATOM | 1978 | CA | SER | B | 322 | 21.851 | 55.230 | −0.855 | 1.00 | 53.43 | C |

TABLE 4-continued

Stem Cell Factor Dimer

| ATOM | 1979 | C | SER | B | 322 | 20.407 | 54.836 | −1.151 | 1.00 | 55.25 | C |
|------|------|-----|-----|---|-----|--------|--------|--------|------|-------|---|
| ATOM | 1980 | O | SER | B | 322 | 20.074 | 54.476 | −2.281 | 1.00 | 55.67 | O |
| ATOM | 1981 | CB | SER | B | 322 | 22.565 | 54.090 | −0.128 | 1.00 | 52.66 | C |
| ATOM | 1982 | OG | SER | B | 322 | 23.935 | 54.388 | 0.064 | 1.00 | 50.92 | O |
| ATOM | 1983 | N | ILE | B | 323 | 19.552 | 54.900 | −0.136 | 1.00 | 56.46 | N |
| ATOM | 1984 | CA | ILE | B | 323 | 18.148 | 54.563 | −0.319 | 1.00 | 58.62 | C |
| ATOM | 1985 | C | ILE | B | 323 | 17.528 | 55.554 | −1.292 | 1.00 | 60.36 | C |
| ATOM | 1986 | O | ILE | B | 323 | 16.926 | 55.166 | −2.292 | 1.00 | 60.43 | O |
| ATOM | 1987 | CB | ILE | B | 323 | 17.380 | 54.619 | 1.017 | 1.00 | 59.22 | C |
| ATOM | 1988 | CG1 | ILE | B | 323 | 17.757 | 53.408 | 1.873 | 1.00 | 58.94 | C |
| ATOM | 1989 | CG2 | ILE | B | 323 | 15.879 | 54.662 | 0.765 | 1.00 | 58.59 | C |
| ATOM | 1990 | CD1 | ILE | B | 323 | 17.075 | 53.382 | 3.210 | 1.00 | 59.07 | C |
| ATOM | 1991 | N | ASP | B | 324 | 17.685 | 56.839 | −0.991 | 1.00 | 62.51 | N |
| ATOM | 1992 | CA | ASP | B | 324 | 17.157 | 57.896 | −1.841 | 1.00 | 64.88 | C |
| ATOM | 1993 | C | ASP | B | 324 | 17.688 | 57.746 | −3.270 | 1.00 | 65.15 | C |
| ATOM | 1994 | O | ASP | B | 324 | 17.095 | 58.260 | −4.218 | 1.00 | 63.55 | O |
| ATOM | 1995 | CB | ASP | B | 324 | 17.549 | 59.267 | −1.277 | 1.00 | 67.65 | C |
| ATOM | 1996 | CG | ASP | B | 324 | 16.784 | 59.626 | −0.004 | 1.00 | 70.52 | C |
| ATOM | 1997 | OD1 | ASP | B | 324 | 16.844 | 58.866 | 0.989 | 1.00 | 71.17 | O |
| ATOM | 1998 | OD2 | ASP | B | 324 | 16.120 | 60.685 | 0.005 | 1.00 | 73.09 | O |
| ATOM | 1999 | N | ALA | B | 325 | 18.800 | 57.029 | −3.417 | 1.00 | 65.84 | N |
| ATOM | 2000 | CA | ALA | B | 325 | 19.409 | 56.810 | −4.726 | 1.00 | 68.05 | C |
| ATOM | 2001 | C | ALA | B | 325 | 18.540 | 55.957 | −5.648 | 1.00 | 69.79 | C |
| ATOM | 2002 | O | ALA | B | 325 | 18.808 | 55.860 | −6.845 | 1.00 | 70.12 | O |
| ATOM | 2003 | CB | ALA | B | 325 | 20.778 | 56.168 | −4.566 | 1.00 | 67.52 | C |
| ATOM | 2004 | N | PHE | B | 326 | 17.506 | 55.332 | −5.095 | 1.00 | 71.53 | N |
| ATOM | 2005 | CA | PHE | B | 326 | 16.612 | 54.512 | −5.901 | 1.00 | 73.81 | C |
| ATOM | 2006 | C | PHE | B | 326 | 15.510 | 55.341 | −6.538 | 1.00 | 76.59 | C |
| ATOM | 2007 | O | PHE | B | 326 | 14.521 | 54.802 | −7.031 | 1.00 | 77.23 | O |
| ATOM | 2008 | CB | PHE | B | 326 | 15.994 | 53.398 | −5.060 | 1.00 | 73.16 | C |
| ATOM | 2009 | CG | PHE | B | 326 | 16.857 | 52.184 | −4.953 | 1.00 | 72.21 | C |
| ATOM | 2010 | CD1 | PHE | B | 326 | 18.058 | 52.229 | −4.260 | 1.00 | 71.61 | C |
| ATOM | 2011 | CD2 | PHE | B | 326 | 16.488 | 51.003 | −5.583 | 1.00 | 72.42 | C |
| ATOM | 2012 | CE1 | PHE | B | 326 | 18.882 | 51.116 | −4.198 | 1.00 | 71.32 | C |
| ATOM | 2013 | CE2 | PHE | B | 326 | 17.308 | 49.880 | −5.528 | 1.00 | 72.69 | C |
| ATOM | 2014 | CZ | PHE | B | 326 | 18.508 | 49.938 | −4.834 | 1.00 | 71.79 | C |
| ATOM | 2015 | N | LYS | B | 327 | 15.685 | 56.657 | −6.515 | 1.00 | 79.77 | N |
| ATOM | 2016 | CA | LYS | B | 327 | 14.725 | 57.579 | −7.107 | 1.00 | 82.73 | C |
| ATOM | 2017 | C | LYS | B | 327 | 15.459 | 58.374 | −8.176 | 1.00 | 84.67 | C |
| ATOM | 2018 | O | LYS | B | 327 | 14.960 | 58.570 | −9.285 | 1.00 | 85.16 | O |
| ATOM | 2019 | CB | LYS | B | 327 | 14.174 | 58.536 | −6.047 | 1.00 | 83.44 | C |
| ATOM | 2020 | CG | LYS | B | 327 | 13.281 | 59.630 | −6.619 | 1.00 | 85.27 | C |
| ATOM | 2021 | CD | LYS | B | 327 | 12.887 | 60.652 | −5.562 | 1.00 | 86.20 | C |
| ATOM | 2022 | CE | LYS | B | 327 | 12.049 | 61.772 | −6.169 | 1.00 | 86.76 | C |
| ATOM | 2023 | NZ | LYS | B | 327 | 11.690 | 62.816 | −5.163 | 1.00 | 86.99 | N |
| ATOM | 2024 | N | ASP | B | 328 | 16.656 | 58.824 | −7.821 | 1.00 | 87.12 | N |
| ATOM | 2025 | CA | ASP | B | 328 | 17.493 | 59.601 | −8.720 | 1.00 | 89.44 | C |
| ATOM | 2026 | C | ASP | B | 328 | 18.422 | 58.694 | −9.523 | 1.00 | 89.84 | C |
| ATOM | 2027 | O | ASP | B | 328 | 19.617 | 58.966 | −9.647 | 1.00 | 89.93 | O |
| ATOM | 2028 | CB | ASP | B | 328 | 18.311 | 60.617 | −7.916 | 1.00 | 91.16 | C |
| ATOM | 2029 | CG | ASP | B | 328 | 17.436 | 61.629 | −7.194 | 1.00 | 92.98 | C |
| ATOM | 2030 | OD1 | ASP | B | 328 | 16.764 | 62.428 | −7.880 | 1.00 | 93.99 | O |
| ATOM | 2031 | OD2 | ASP | B | 328 | 17.413 | 61.623 | −5.944 | 1.00 | 93.57 | O |
| ATOM | 2032 | N | PHE | B | 329 | 17.864 | 57.616 | −10.063 | 1.00 | 90.47 | N |
| ATOM | 2033 | CA | PHE | B | 329 | 18.635 | 56.669 | −10.862 | 1.00 | 91.54 | C |
| ATOM | 2034 | C | PHE | B | 329 | 17.788 | 56.160 | −12.024 | 1.00 | 91.50 | C |
| ATOM | 2035 | O | PHE | B | 329 | 17.420 | 54.984 | −12.076 | 1.00 | 91.13 | O |
| ATOM | 2036 | CB | PHE | B | 329 | 19.094 | 55.493 | −9.995 | 1.00 | 92.88 | C |
| ATOM | 2037 | CG | PHE | B | 329 | 19.963 | 54.497 | −10.719 | 1.00 | 94.37 | C |
| ATOM | 2038 | CD1 | PHE | B | 329 | 20.407 | 53.354 | −10.068 | 1.00 | 95.79 | C |
| ATOM | 2039 | CD2 | PHE | B | 329 | 20.331 | 54.692 | −12.048 | 1.00 | 95.63 | C |
| ATOM | 2040 | CE1 | PHE | B | 329 | 21.201 | 52.419 | −10.725 | 1.00 | 96.80 | C |
| ATOM | 2041 | CE2 | PHE | B | 329 | 21.123 | 53.765 | −12.715 | 1.00 | 96.49 | C |
| ATOM | 2042 | CZ | PHE | B | 329 | 21.559 | 52.625 | −12.052 | 1.00 | 97.15 | C |
| ATOM | 2043 | N | VAL | B | 330 | 17.489 | 57.056 | −12.957 | 1.00 | 91.01 | N |
| ATOM | 2044 | CA | VAL | B | 330 | 16.687 | 56.715 | −14.123 | 1.00 | 90.86 | C |
| ATOM | 2045 | C | VAL | B | 330 | 17.532 | 56.789 | −15.395 | 1.00 | 90.35 | C |
| ATOM | 2046 | O | VAL | B | 330 | 17.000 | 56.915 | −16.500 | 1.00 | 90.30 | O |
| ATOM | 2047 | CB | VAL | B | 330 | 15.477 | 57.673 | −14.259 | 1.00 | 91.42 | C |
| ATOM | 2048 | CG1 | VAL | B | 330 | 14.548 | 57.510 | −13.063 | 1.00 | 91.85 | C |
| ATOM | 2049 | CG2 | VAL | B | 330 | 15.959 | 59.117 | −14.359 | 1.00 | 91.34 | C |
| ATOM | 2050 | N | VAL | B | 331 | 18.849 | 56.700 | −15.232 | 1.00 | 88.83 | N |
| ATOM | 2051 | CA | VAL | B | 331 | 19.766 | 56.771 | −16.364 | 1.00 | 87.12 | C |
| ATOM | 2052 | C | VAL | B | 331 | 21.032 | 55.949 | −16.132 | 1.00 | 85.40 | C |
| ATOM | 2053 | O | VAL | B | 331 | 21.325 | 55.551 | −15.004 | 1.00 | 85.03 | O |
| ATOM | 2054 | CB | VAL | B | 331 | 20.168 | 58.237 | −16.643 | 1.00 | 87.73 | C |
| ATOM | 2055 | CG1 | VAL | B | 331 | 18.994 | 58.993 | −17.249 | 1.00 | 88.14 | C |

TABLE 4-continued

Stem Cell Factor Dimer

| | | | | | | | | | | | |
|---|---|---|---|---|---|---|---|---|---|---|---|
| ATOM | 2056 | CG2 | VAL | B | 331 | 20.600 | 58.911 | −15.347 | 1.00 | 87.18 | C |
| ATOM | 2057 | N | ALA | B | 332 | 21.776 | 55.698 | −17.207 | 1.00 | 83.14 | N |
| ATOM | 2058 | CA | ALA | B | 332 | 23.015 | 54.927 | −17.128 | 1.00 | 81.00 | C |
| ATOM | 2059 | C | ALA | B | 332 | 23.944 | 55.274 | −18.288 | 1.00 | 79.56 | C |
| ATOM | 2060 | O | ALA | B | 332 | 25.117 | 55.595 | −18.086 | 1.00 | 78.95 | O |
| ATOM | 2061 | CB | ALA | B | 332 | 22.706 | 53.436 | −17.135 | 1.00 | 81.62 | C |
| ATOM | 2062 | N | SER | B | 333 | 23.417 | 55.201 | −19.505 | 1.00 | 77.72 | N |
| ATOM | 2063 | CA | SER | B | 333 | 24.196 | 55.519 | −20.696 | 1.00 | 75.21 | C |
| ATOM | 2064 | C | SER | B | 333 | 24.292 | 57.035 | −20.825 | 1.00 | 73.63 | C |
| ATOM | 2065 | O | SER | B | 333 | 25.081 | 57.555 | −21.618 | 1.00 | 72.74 | O |
| ATOM | 2066 | CB | SER | B | 333 | 23.519 | 54.944 | −21.941 | 1.00 | 74.54 | C |
| ATOM | 2067 | OG | SER | B | 333 | 23.284 | 53.556 | −21.797 | 1.00 | 74.58 | O |
| ATOM | 2068 | N | GLU | B | 334 | 23.481 | 57.732 | −20.032 | 1.00 | 71.81 | N |
| ATOM | 2069 | CA | GLU | B | 334 | 23.440 | 59.191 | −20.038 | 1.00 | 70.21 | C |
| ATOM | 2070 | C | GLU | B | 334 | 24.158 | 59.803 | −18.841 | 1.00 | 67.79 | C |
| ATOM | 2071 | O | GLU | B | 334 | 23.853 | 60.922 | −18.432 | 1.00 | 66.60 | O |
| ATOM | 2072 | CB | GLU | B | 334 | 21.987 | 59.671 | −20.057 | 1.00 | 71.91 | C |
| ATOM | 2073 | CG | GLU | B | 334 | 21.201 | 59.220 | −21.274 | 1.00 | 73.77 | C |
| ATOM | 2074 | CD | GLU | B | 334 | 19.738 | 59.608 | −21.199 | 1.00 | 75.72 | C |
| ATOM | 2075 | OE1 | GLU | B | 334 | 19.039 | 59.128 | −20.282 | 1.00 | 76.13 | O |
| ATOM | 2076 | OE2 | GLU | B | 334 | 19.286 | 60.395 | −22.057 | 1.00 | 77.49 | O |
| ATOM | 2077 | N | THR | B | 335 | 25.106 | 59.067 | −18.277 | 1.00 | 65.94 | N |
| ATOM | 2078 | CA | THR | B | 335 | 25.866 | 59.566 | −17.136 | 1.00 | 64.40 | C |
| ATOM | 2079 | C | THR | B | 335 | 27.359 | 59.421 | −17.398 | 1.00 | 63.02 | C |
| ATOM | 2080 | O | THR | B | 335 | 27.773 | 58.942 | −18.458 | 1.00 | 63.10 | O |
| ATOM | 2081 | CB | THR | B | 335 | 25.515 | 58.810 | −15.832 | 1.00 | 64.99 | C |
| ATOM | 2082 | OG1 | THR | B | 335 | 25.922 | 57.441 | −15.946 | 1.00 | 63.15 | O |
| ATOM | 2083 | CG2 | THR | B | 335 | 24.016 | 58.874 | −15.565 | 1.00 | 63.98 | C |
| ATOM | 2084 | N | SER | B | 336 | 28.164 | 59.823 | −16.423 | 1.00 | 60.77 | N |
| ATOM | 2085 | CA | SER | B | 336 | 29.609 | 59.761 | −16.557 | 1.00 | 59.57 | C |
| ATOM | 2086 | C | SER | B | 336 | 30.201 | 58.391 | −16.236 | 1.00 | 58.18 | C |
| ATOM | 2087 | O | SER | B | 336 | 29.493 | 57.462 | −15.848 | 1.00 | 56.96 | O |
| ATOM | 2088 | CB | SER | B | 336 | 30.249 | 60.808 | −15.650 | 1.00 | 60.02 | C |
| ATOM | 2089 | OG | SER | B | 336 | 29.972 | 60.524 | −14.291 | 1.00 | 61.00 | O |
| ATOM | 2090 | N | ASP | B | 337 | 31.514 | 58.288 | −16.406 | 1.00 | 56.54 | N |
| ATOM | 2091 | CA | ASP | B | 337 | 32.246 | 57.064 | −16.128 | 1.00 | 56.72 | C |
| ATOM | 2092 | C | ASP | B | 337 | 32.198 | 56.783 | −14.625 | 1.00 | 56.84 | C |
| ATOM | 2093 | O | ASP | B | 337 | 31.476 | 57.451 | −13.882 | 1.00 | 56.58 | O |
| ATOM | 2094 | CB | ASP | B | 337 | 33.700 | 57.215 | −16.588 | 1.00 | 55.51 | C |
| ATOM | 2095 | CG | ASP | B | 337 | 34.432 | 58.327 | −15.857 | 1.00 | 54.76 | C |
| ATOM | 2096 | OD1 | ASP | B | 337 | 35.542 | 58.699 | −16.292 | 1.00 | 55.99 | O |
| ATOM | 2097 | OD2 | ASP | B | 337 | 33.904 | 58.828 | −14.842 | 1.00 | 52.06 | O |
| ATOM | 2098 | N | CYS | B | 338 | 32.975 | 55.804 | −14.177 | 1.00 | 55.69 | N |
| ATOM | 2099 | CA | CYS | B | 338 | 32.994 | 55.454 | −12.764 | 1.00 | 57.24 | C |
| ATOM | 2100 | C | CYS | B | 338 | 34.349 | 55.696 | −12.110 | 1.00 | 57.23 | C |
| ATOM | 2101 | O | CYS | B | 338 | 34.680 | 55.079 | −11.099 | 1.00 | 56.86 | O |
| ATOM | 2102 | CB | CYS | B | 338 | 32.580 | 53.993 | −12.579 | 1.00 | 56.06 | C |
| ATOM | 2103 | SG | CYS | B | 338 | 30.835 | 53.650 | −12.996 | 1.00 | 59.59 | S |
| ATOM | 2104 | N | VAL | B | 339 | 35.118 | 56.612 | −12.686 | 1.00 | 57.28 | N |
| ATOM | 2105 | CA | VAL | B | 339 | 36.438 | 56.950 | −12.173 | 1.00 | 58.39 | C |
| ATOM | 2106 | C | VAL | B | 339 | 36.526 | 58.443 | −11.854 | 1.00 | 58.18 | C |
| ATOM | 2107 | O | VAL | B | 339 | 35.728 | 59.237 | −12.345 | 1.00 | 57.22 | O |
| ATOM | 2108 | CB | VAL | B | 339 | 37.529 | 56.586 | −13.211 | 1.00 | 59.55 | C |
| ATOM | 2109 | CG1 | VAL | B | 339 | 38.908 | 56.959 | −12.689 | 1.00 | 59.58 | C |
| ATOM | 2110 | CG2 | VAL | B | 339 | 37.466 | 55.101 | −13.522 | 1.00 | 60.35 | C |
| ATOM | 2111 | N | VAL | B | 340 | 37.497 | 58.815 | −11.024 | 1.00 | 58.73 | N |
| ATOM | 2112 | CA | VAL | B | 340 | 37.704 | 60.207 | −10.652 | 1.00 | 59.48 | C |
| ATOM | 2113 | C | VAL | B | 340 | 39.150 | 60.612 | −10.941 | 1.00 | 61.15 | C |
| ATOM | 2114 | O | VAL | B | 340 | 40.067 | 60.225 | −10.216 | 1.00 | 61.61 | O |
| ATOM | 2115 | CB | VAL | B | 340 | 37.420 | 60.440 | −9.151 | 1.00 | 58.62 | C |
| ATOM | 2116 | CG1 | VAL | B | 340 | 37.637 | 61.912 | −8.798 | 1.00 | 56.58 | C |
| ATOM | 2117 | CG2 | VAL | B | 340 | 36.010 | 60.011 | −8.818 | 1.00 | 57.68 | C |
| ATOM | 2118 | N | SER | B | 341 | 39.345 | 61.390 | −12.002 | 1.00 | 62.42 | N |
| ATOM | 2119 | CA | SER | B | 341 | 40.674 | 61.858 | −12.389 | 1.00 | 64.38 | C |
| ATOM | 2120 | C | SER | B | 341 | 40.636 | 62.455 | −13.790 | 1.00 | 65.42 | C |
| ATOM | 2121 | O | SER | B | 341 | 40.753 | 61.734 | −14.784 | 1.00 | 66.24 | O |
| ATOM | 2122 | CB | SER | B | 341 | 41.681 | 60.707 | −12.346 | 1.00 | 64.35 | C |
| TER | 2123 | | SER | B | 341 | | | | | | |
| ATOM | 2124 | N | THR | C | 409 | 25.721 | 30.038 | 33.359 | 1.00 | 119.52 | N |
| ATOM | 2125 | CA | THR | C | 409 | 24.769 | 31.115 | 33.121 | 1.00 | 119.16 | C |
| ATOM | 2126 | C | THR | C | 409 | 24.295 | 31.124 | 31.671 | 1.00 | 118.62 | C |
| ATOM | 2127 | O | THR | C | 409 | 25.071 | 30.866 | 30.750 | 1.00 | 118.27 | O |
| ATOM | 2128 | CB | THR | C | 409 | 25.389 | 32.489 | 33.456 | 1.00 | 119.49 | C |
| ATOM | 2129 | OG1 | THR | C | 409 | 25.640 | 32.569 | 34.863 | 1.00 | 119.51 | O |
| ATOM | 2130 | CG2 | THR | C | 409 | 24.454 | 33.616 | 33.052 | 1.00 | 119.66 | C |
| ATOM | 2131 | N | ASN | C | 410 | 23.011 | 31.417 | 31.484 | 1.00 | 117.91 | N |
| ATOM | 2132 | CA | ASN | C | 410 | 22.409 | 31.476 | 30.157 | 1.00 | 116.50 | C |

TABLE 4-continued

Stem Cell Factor Dimer

| ATOM | 2133 | C | ASN | C | 410 | 22.569 | 32.882 | 29.600 | 1.00 | 115.36 | C |
|---|---|---|---|---|---|---|---|---|---|---|---|
| ATOM | 2134 | O | ASN | C | 410 | 21.656 | 33.702 | 29.701 | 1.00 | 115.48 | O |
| ATOM | 2135 | CB | ASN | C | 410 | 20.935 | 31.116 | 30.238 | 1.00 | 116.84 | C |
| ATOM | 2136 | N | ASN | C | 411 | 23.734 | 33.154 | 29.018 | 1.00 | 113.54 | N |
| ATOM | 2137 | CA | ASN | C | 411 | 24.026 | 34.466 | 28.451 | 1.00 | 111.04 | C |
| ATOM | 2138 | C | ASN | C | 411 | 23.019 | 34.864 | 27.380 | 1.00 | 108.27 | C |
| ATOM | 2139 | O | ASN | C | 411 | 22.802 | 34.135 | 26.412 | 1.00 | 108.21 | O |
| ATOM | 2140 | CB | ASN | C | 411 | 25.442 | 34.486 | 27.873 | 1.00 | 112.37 | C |
| ATOM | 2141 | CG | ASN | C | 411 | 26.505 | 34.328 | 28.941 | 1.00 | 113.08 | C |
| ATOM | 2142 | OD1 | ASN | C | 411 | 26.606 | 35.145 | 29.857 | 1.00 | 113.31 | O |
| ATOM | 2143 | ND2 | ASN | C | 411 | 27.301 | 33.271 | 28.833 | 1.00 | 113.72 | N |
| ATOM | 2144 | N | VAL | C | 412 | 22.412 | 36.032 | 27.571 | 1.00 | 104.37 | N |
| ATOM | 2145 | CA | VAL | C | 412 | 21.410 | 36.554 | 26.651 | 1.00 | 99.13 | C |
| ATOM | 2146 | C | VAL | C | 412 | 21.977 | 36.814 | 25.260 | 1.00 | 94.12 | C |
| ATOM | 2147 | O | VAL | C | 412 | 22.346 | 37.938 | 24.915 | 1.00 | 94.18 | O |
| ATOM | 2148 | CB | VAL | C | 412 | 20.787 | 37.854 | 27.205 | 1.00 | 100.42 | C |
| ATOM | 2149 | CG1 | VAL | C | 412 | 19.645 | 38.317 | 26.309 | 1.00 | 100.54 | C |
| ATOM | 2150 | CG2 | VAL | C | 412 | 20.291 | 37.615 | 28.621 | 1.00 | 100.43 | C |
| ATOM | 2151 | N | LYS | C | 413 | 22.042 | 35.742 | 24.479 | 1.00 | 87.81 | N |
| ATOM | 2152 | CA | LYS | C | 413 | 22.533 | 35.751 | 23.105 | 1.00 | 80.16 | C |
| ATOM | 2153 | C | LYS | C | 413 | 21.637 | 34.732 | 22.408 | 1.00 | 74.79 | C |
| ATOM | 2154 | O | LYS | C | 413 | 21.057 | 35.003 | 21.350 | 1.00 | 72.74 | O |
| ATOM | 2155 | CB | LYS | C | 413 | 23.992 | 35.301 | 23.060 | 1.00 | 81.15 | C |
| ATOM | 2156 | N | ASP | C | 414 | 21.540 | 33.554 | 23.025 | 1.00 | 67.32 | N |
| ATOM | 2157 | CA | ASP | C | 414 | 20.687 | 32.486 | 22.535 | 1.00 | 58.95 | C |
| ATOM | 2158 | C | ASP | C | 414 | 19.291 | 33.054 | 22.731 | 1.00 | 50.71 | C |
| ATOM | 2159 | O | ASP | C | 414 | 18.411 | 32.926 | 21.877 | 1.00 | 48.37 | O |
| ATOM | 2160 | CB | ASP | C | 414 | 20.842 | 31.235 | 23.405 | 1.00 | 64.38 | C |
| ATOM | 2161 | CG | ASP | C | 414 | 22.196 | 30.571 | 23.249 | 1.00 | 68.30 | C |
| ATOM | 2162 | OD1 | ASP | C | 414 | 22.477 | 30.055 | 22.140 | 1.00 | 69.88 | O |
| ATOM | 2163 | OD2 | ASP | C | 414 | 22.973 | 30.563 | 24.235 | 1.00 | 69.38 | O |
| ATOM | 2164 | N | VAL | C | 415 | 19.116 | 33.689 | 23.883 | 1.00 | 40.98 | N |
| ATOM | 2165 | CA | VAL | C | 415 | 17.858 | 34.308 | 24.253 | 1.00 | 35.05 | C |
| ATOM | 2166 | C | VAL | C | 415 | 17.410 | 35.298 | 23.173 | 1.00 | 34.05 | C |
| ATOM | 2167 | O | VAL | C | 415 | 16.262 | 35.254 | 22.722 | 1.00 | 32.19 | O |
| ATOM | 2168 | CB | VAL | C | 415 | 17.997 | 35.011 | 25.627 | 1.00 | 31.93 | C |
| ATOM | 2169 | CG1 | VAL | C | 415 | 16.824 | 35.919 | 25.891 | 1.00 | 32.40 | C |
| ATOM | 2170 | CG2 | VAL | C | 415 | 18.084 | 33.953 | 26.727 | 1.00 | 28.81 | C |
| ATOM | 2171 | N | THR | C | 416 | 18.317 | 36.177 | 22.748 | 1.00 | 31.45 | N |
| ATOM | 2172 | CA | THR | C | 416 | 17.995 | 37.152 | 21.717 | 1.00 | 29.58 | C |
| ATOM | 2173 | C | THR | C | 416 | 17.517 | 36.432 | 20.456 | 1.00 | 29.53 | C |
| ATOM | 2174 | O | THR | C | 416 | 16.511 | 36.813 | 19.855 | 1.00 | 26.91 | O |
| ATOM | 2175 | CB | THR | C | 416 | 19.223 | 38.066 | 21.386 | 1.00 | 30.06 | C |
| ATOM | 2176 | OG1 | THR | C | 416 | 19.345 | 39.083 | 22.390 | 1.00 | 30.21 | O |
| ATOM | 2177 | CG2 | THR | C | 416 | 19.055 | 38.750 | 20.016 | 1.00 | 28.63 | C |
| ATOM | 2178 | N | LYS | C | 417 | 18.238 | 35.388 | 20.061 | 1.00 | 29.46 | N |
| ATOM | 2179 | CA | LYS | C | 417 | 17.868 | 34.611 | 18.880 | 1.00 | 29.39 | C |
| ATOM | 2180 | C | LYS | C | 417 | 16.489 | 33.965 | 19.050 | 1.00 | 27.59 | C |
| ATOM | 2181 | O | LYS | C | 417 | 15.664 | 33.995 | 18.136 | 1.00 | 28.30 | O |
| ATOM | 2182 | CB | LYS | C | 417 | 18.903 | 33.509 | 18.617 | 1.00 | 30.97 | C |
| ATOM | 2183 | CG | LYS | C | 417 | 19.825 | 33.786 | 17.439 | 1.00 | 34.65 | C |
| ATOM | 2184 | CD | LYS | C | 417 | 20.818 | 34.894 | 17.729 | 1.00 | 36.75 | C |
| ATOM | 2185 | CE | LYS | C | 417 | 22.175 | 34.311 | 18.094 | 1.00 | 40.95 | C |
| ATOM | 2186 | NZ | LYS | C | 417 | 22.774 | 33.558 | 16.953 | 1.00 | 39.53 | N |
| ATOM | 2187 | N | LEU | C | 418 | 16.251 | 33.377 | 20.219 | 1.00 | 23.37 | N |
| ATOM | 2188 | CA | LEU | C | 418 | 14.983 | 32.715 | 20.495 | 1.00 | 22.30 | C |
| ATOM | 2189 | C | LEU | C | 418 | 13.811 | 33.686 | 20.457 | 1.00 | 20.70 | C |
| ATOM | 2190 | O | LEU | C | 418 | 12.722 | 33.338 | 20.017 | 1.00 | 21.55 | C |
| ATOM | 2191 | CB | LEU | C | 418 | 15.038 | 32.026 | 21.860 | 1.00 | 19.71 | C |
| ATOM | 2192 | CG | LEU | C | 418 | 13.758 | 31.375 | 22.391 | 1.00 | 20.40 | C |
| ATOM | 2193 | CD1 | LEU | C | 418 | 13.230 | 30.356 | 21.403 | 1.00 | 15.96 | C |
| ATOM | 2194 | CD2 | LEU | C | 418 | 14.051 | 30.703 | 23.733 | 1.00 | 16.28 | C |
| ATOM | 2195 | N | VAL | C | 419 | 14.039 | 34.907 | 20.921 | 1.00 | 21.24 | N |
| ATOM | 2196 | CA | VAL | C | 419 | 12.986 | 35.909 | 20.934 | 1.00 | 19.24 | C |
| ATOM | 2197 | C | VAL | C | 419 | 12.647 | 36.402 | 19.525 | 1.00 | 18.54 | C |
| ATOM | 2198 | O | VAL | C | 419 | 11.477 | 36.632 | 19.196 | 1.00 | 20.16 | O |
| ATOM | 2199 | CB | VAL | C | 419 | 13.382 | 37.067 | 21.861 | 1.00 | 18.08 | C |
| ATOM | 2200 | CG1 | VAL | C | 419 | 12.374 | 38.219 | 21.751 | 1.00 | 21.66 | C |
| ATOM | 2201 | CG2 | VAL | C | 419 | 13.376 | 36.554 | 23.302 | 1.00 | 15.68 | C |
| ATOM | 2202 | N | ALA | C | 420 | 13.672 | 36.533 | 18.693 | 1.00 | 15.15 | N |
| ATOM | 2203 | CA | ALA | C | 420 | 13.508 | 36.963 | 17.317 | 1.00 | 17.52 | C |
| ATOM | 2204 | C | ALA | C | 420 | 12.814 | 35.852 | 16.522 | 1.00 | 18.92 | C |
| ATOM | 2205 | O | ALA | C | 420 | 12.155 | 36.123 | 15.518 | 1.00 | 20.02 | O |
| ATOM | 2206 | CB | ALA | C | 420 | 14.886 | 37.273 | 16.699 | 1.00 | 16.86 | C |
| ATOM | 2207 | N | ASN | C | 421 | 12.979 | 34.608 | 16.975 | 1.00 | 17.25 | N |
| ATOM | 2208 | CA | ASN | C | 421 | 12.378 | 33.447 | 16.327 | 1.00 | 20.11 | C |
| ATOM | 2209 | C | ASN | C | 421 | 11.025 | 32.989 | 16.861 | 1.00 | 18.94 | C |

TABLE 4-continued

Stem Cell Factor Dimer

| ATOM | 2210 | O | ASN | C | 421 | 10.490 | 31.998 | 16.396 | 1.00 | 22.70 | O |
|---|---|---|---|---|---|---|---|---|---|---|---|
| ATOM | 2211 | CB | ASN | C | 421 | 13.329 | 32.252 | 16.363 | 1.00 | 20.49 | C |
| ATOM | 2212 | CG | ASN | C | 421 | 14.273 | 32.226 | 15.184 | 1.00 | 23.76 | C |
| ATOM | 2213 | OD1 | ASN | C | 421 | 13.956 | 32.733 | 14.111 | 1.00 | 22.84 | O |
| ATOM | 2214 | ND2 | ASN | C | 421 | 15.434 | 31.610 | 15.370 | 1.00 | 26.43 | N |
| ATOM | 2215 | N | LEU | C | 422 | 10.485 | 33.684 | 17.850 | 1.00 | 21.69 | N |
| ATOM | 2216 | CA | LEU | C | 422 | 9.165 | 33.347 | 18.402 | 1.00 | 21.52 | C |
| ATOM | 2217 | C | LEU | C | 422 | 8.226 | 34.462 | 17.951 | 1.00 | 22.96 | C |
| ATOM | 2218 | O | LEU | C | 422 | 8.628 | 35.627 | 17.929 | 1.00 | 22.14 | O |
| ATOM | 2219 | CB | LEU | C | 422 | 9.204 | 33.318 | 19.930 | 1.00 | 17.36 | C |
| ATOM | 2220 | CG | LEU | C | 422 | 9.994 | 32.173 | 20.569 | 1.00 | 19.51 | C |
| ATOM | 2221 | CD1 | LEU | C | 422 | 10.204 | 32.467 | 22.063 | 1.00 | 16.94 | C |
| ATOM | 2222 | CD2 | LEU | C | 422 | 9.237 | 30.842 | 20.358 | 1.00 | 15.76 | C |
| ATOM | 2223 | N | PRO | C | 423 | 6.975 | 34.124 | 17.568 | 1.00 | 24.23 | N |
| ATOM | 2224 | CA | PRO | C | 423 | 6.047 | 35.183 | 17.127 | 1.00 | 25.36 | C |
| ATOM | 2225 | C | PRO | C | 423 | 5.772 | 36.202 | 18.228 | 1.00 | 25.17 | C |
| ATOM | 2226 | O | PRO | C | 423 | 5.462 | 35.831 | 19.353 | 1.00 | 27.09 | O |
| ATOM | 2227 | CB | PRO | C | 423 | 4.792 | 34.413 | 16.691 | 1.00 | 22.59 | C |
| ATOM | 2228 | CG | PRO | C | 423 | 4.928 | 33.041 | 17.347 | 1.00 | 23.46 | C |
| ATOM | 2229 | CD | PRO | C | 423 | 6.406 | 32.778 | 17.368 | 1.00 | 24.55 | C |
| ATOM | 2230 | N | LYS | C | 424 | 5.903 | 37.484 | 17.898 | 1.00 | 27.84 | N |
| ATOM | 2231 | CA | LYS | C | 424 | 5.699 | 38.562 | 18.870 | 1.00 | 29.74 | C |
| ATOM | 2232 | C | LYS | C | 424 | 4.366 | 38.469 | 19.606 | 1.00 | 28.96 | C |
| ATOM | 2233 | O | LYS | C | 424 | 4.251 | 38.908 | 20.744 | 1.00 | 25.75 | O |
| ATOM | 2234 | CB | LYS | C | 424 | 5.783 | 39.927 | 18.191 | 1.00 | 29.72 | C |
| ATOM | 2235 | CG | LYS | C | 424 | 7.117 | 40.251 | 17.574 | 1.00 | 37.16 | C |
| ATOM | 2236 | CD | LYS | C | 424 | 6.952 | 41.363 | 16.524 | 1.00 | 40.32 | C |
| ATOM | 2237 | CE | LYS | C | 424 | 8.218 | 41.569 | 15.698 | 1.00 | 42.47 | C |
| ATOM | 2238 | NZ | LYS | C | 424 | 7.945 | 42.406 | 14.488 | 1.00 | 43.47 | N |
| ATOM | 2239 | N | ASP | C | 425 | 3.360 | 37.902 | 18.957 | 1.00 | 28.50 | N |
| ATOM | 2240 | CA | ASP | C | 425 | 2.059 | 37.791 | 19.590 | 1.00 | 32.00 | C |
| ATOM | 2241 | C | ASP | C | 425 | 1.843 | 36.416 | 20.215 | 1.00 | 28.99 | C |
| ATOM | 2242 | O | ASP | C | 425 | 0.725 | 36.053 | 20.534 | 1.00 | 29.58 | O |
| ATOM | 2243 | CB | ASP | C | 425 | 0.951 | 38.097 | 18.569 | 1.00 | 32.89 | C |
| ATOM | 2244 | CG | ASP | C | 425 | 0.984 | 37.156 | 17.385 | 1.00 | 36.03 | C |
| ATOM | 2245 | OD1 | ASP | C | 425 | 2.071 | 36.612 | 17.101 | 1.00 | 34.79 | O |
| ATOM | 2246 | OD2 | ASP | C | 425 | −0.062 | 36.968 | 16.729 | 1.00 | 40.18 | O |
| ATOM | 2247 | N | TYR | C | 426 | 2.910 | 35.647 | 20.388 | 1.00 | 28.20 | N |
| ATOM | 2248 | CA | TYR | C | 426 | 2.769 | 34.326 | 20.996 | 1.00 | 27.47 | C |
| ATOM | 2249 | C | TYR | C | 426 | 2.865 | 34.459 | 22.518 | 1.00 | 28.12 | C |
| ATOM | 2250 | O | TYR | C | 426 | 3.865 | 34.949 | 23.044 | 1.00 | 31.37 | O |
| ATOM | 2251 | CB | TYR | C | 426 | 3.861 | 33.378 | 20.478 | 1.00 | 26.08 | C |
| ATOM | 2252 | CG | TYR | C | 426 | 3.674 | 31.949 | 20.945 | 1.00 | 26.36 | C |
| ATOM | 2253 | CD1 | TYR | C | 426 | 2.494 | 31.256 | 20.671 | 1.00 | 24.85 | C |
| ATOM | 2254 | CD2 | TYR | C | 426 | 4.653 | 31.302 | 21.688 | 1.00 | 24.72 | C |
| ATOM | 2255 | CE1 | TYR | C | 426 | 2.295 | 29.961 | 21.130 | 1.00 | 25.05 | C |
| ATOM | 2256 | CE2 | TYR | C | 426 | 4.461 | 29.997 | 22.151 | 1.00 | 23.79 | C |
| ATOM | 2257 | CZ | TYR | C | 426 | 3.283 | 29.341 | 21.869 | 1.00 | 24.37 | C |
| ATOM | 2258 | OH | TYR | C | 426 | 3.083 | 28.066 | 22.327 | 1.00 | 25.86 | O |
| ATOM | 2259 | N | MET | C | 427 | 1.833 | 34.023 | 23.232 | 1.00 | 28.78 | N |
| ATOM | 2260 | CA | MET | C | 427 | 1.830 | 34.132 | 24.686 | 1.00 | 28.41 | C |
| ATOM | 2261 | C | MET | C | 427 | 2.356 | 32.893 | 25.398 | 1.00 | 27.73 | C |
| ATOM | 2262 | O | MET | C | 427 | 2.018 | 31.767 | 25.059 | 1.00 | 25.73 | O |
| ATOM | 2263 | CB | MET | C | 427 | 0.421 | 34.445 | 25.194 | 1.00 | 31.71 | C |
| ATOM | 2264 | CG | MET | C | 427 | −0.223 | 35.679 | 24.555 | 1.00 | 36.93 | C |
| ATOM | 2265 | SD | MET | C | 427 | 0.761 | 37.196 | 24.702 | 1.00 | 41.33 | S |
| ATOM | 2266 | CE | MET | C | 427 | 0.357 | 37.679 | 26.390 | 1.00 | 39.85 | C |
| ATOM | 2267 | N | ILE | C | 428 | 3.185 | 33.124 | 26.406 | 1.00 | 27.81 | N |
| ATOM | 2268 | CA | ILE | C | 428 | 3.768 | 32.052 | 27.196 | 1.00 | 26.77 | C |
| ATOM | 2269 | C | ILE | C | 428 | 3.160 | 32.148 | 28.590 | 1.00 | 26.18 | C |
| ATOM | 2270 | O | ILE | C | 428 | 3.040 | 33.233 | 29.145 | 1.00 | 24.71 | O |
| ATOM | 2271 | CB | ILE | C | 428 | 5.305 | 32.216 | 27.295 | 1.00 | 28.58 | C |
| ATOM | 2272 | CG1 | ILE | C | 428 | 5.927 | 32.138 | 25.893 | 1.00 | 27.33 | C |
| ATOM | 2273 | CG2 | ILE | C | 428 | 5.889 | 31.165 | 28.238 | 1.00 | 26.23 | C |
| ATOM | 2274 | CD1 | ILE | C | 428 | 7.422 | 32.453 | 25.850 | 1.00 | 25.32 | C |
| ATOM | 2275 | N | THR | C | 429 | 2.769 | 31.011 | 29.149 | 1.00 | 26.38 | N |
| ATOM | 2276 | CA | THR | C | 429 | 2.177 | 30.999 | 30.479 | 1.00 | 26.90 | C |
| ATOM | 2277 | C | THR | C | 429 | 3.231 | 30.882 | 31.556 | 1.00 | 25.21 | C |
| ATOM | 2278 | O | THR | C | 429 | 4.150 | 30.068 | 31.461 | 1.00 | 24.68 | O |
| ATOM | 2279 | CB | THR | C | 429 | 1.209 | 29.811 | 30.676 | 1.00 | 28.90 | C |
| ATOM | 2280 | OG1 | THR | C | 429 | 0.203 | 29.835 | 29.657 | 1.00 | 34.43 | O |
| ATOM | 2281 | CG2 | THR | C | 429 | 0.536 | 29.910 | 32.047 | 1.00 | 30.79 | C |
| ATOM | 2282 | N | LEU | C | 430 | 3.081 | 31.694 | 32.591 | 1.00 | 24.21 | N |
| ATOM | 2283 | CA | LEU | C | 430 | 4.001 | 31.668 | 33.710 | 1.00 | 23.59 | C |
| ATOM | 2284 | C | LEU | C | 430 | 3.270 | 32.006 | 35.007 | 1.00 | 25.18 | C |
| ATOM | 2285 | O | LEU | C | 430 | 2.629 | 33.050 | 35.125 | 1.00 | 24.57 | O |
| ATOM | 2286 | CB | LEU | C | 430 | 5.156 | 32.659 | 33.483 | 1.00 | 22.49 | C |

TABLE 4-continued

Stem Cell Factor Dimer

| ATOM | 2287 | CG | LEU | C | 430 | 6.101 | 32.909 | 34.673 | 1.00 | 21.79 | C |
| ATOM | 2288 | CD1 | LEU | C | 430 | 6.910 | 31.647 | 34.969 | 1.00 | 19.59 | C |
| ATOM | 2289 | CD2 | LEU | C | 430 | 7.026 | 34.079 | 34.368 | 1.00 | 20.81 | C |
| ATOM | 2290 | N | LYS | C | 431 | 3.347 | 31.102 | 35.973 | 1.00 | 26.18 | N |
| ATOM | 2291 | CA | LYS | C | 431 | 2.737 | 31.349 | 37.267 | 1.00 | 29.32 | C |
| ATOM | 2292 | C | LYS | C | 431 | 3.719 | 32.292 | 37.972 | 1.00 | 29.35 | C |
| ATOM | 2293 | O | LYS | C | 431 | 4.625 | 31.868 | 38.692 | 1.00 | 28.17 | O |
| ATOM | 2294 | CB | LYS | C | 431 | 2.564 | 30.035 | 38.034 | 1.00 | 31.78 | C |
| ATOM | 2295 | CG | LYS | C | 431 | 1.679 | 28.986 | 37.322 | 1.00 | 30.55 | C |
| ATOM | 2296 | CD | LYS | C | 431 | 1.500 | 27.732 | 38.201 | 1.00 | 33.93 | C |
| ATOM | 2297 | CE | LYS | C | 431 | 0.721 | 26.599 | 37.514 | 1.00 | 34.68 | C |
| ATOM | 2298 | NZ | LYS | C | 431 | 1.518 | 25.866 | 36.470 | 1.00 | 36.88 | N |
| ATOM | 2299 | N | TYR | C | 432 | 3.530 | 33.581 | 37.710 | 1.00 | 31.52 | N |
| ATOM | 2300 | CA | TYR | C | 432 | 4.352 | 34.664 | 38.240 | 1.00 | 33.55 | C |
| ATOM | 2301 | C | TYR | C | 432 | 4.262 | 34.779 | 39.761 | 1.00 | 35.80 | C |
| ATOM | 2302 | O | TYR | C | 432 | 3.169 | 34.748 | 40.330 | 1.00 | 36.29 | O |
| ATOM | 2303 | CB | TYR | C | 432 | 3.905 | 35.982 | 37.588 | 1.00 | 34.63 | C |
| ATOM | 2304 | CG | TYR | C | 432 | 4.649 | 37.223 | 38.040 | 1.00 | 36.39 | C |
| ATOM | 2305 | CD1 | TYR | C | 432 | 5.912 | 37.532 | 37.531 | 1.00 | 36.97 | C |
| ATOM | 2306 | CD2 | TYR | C | 432 | 4.098 | 38.080 | 38.993 | 1.00 | 35.09 | C |
| ATOM | 2307 | CE1 | TYR | C | 432 | 6.610 | 38.666 | 37.965 | 1.00 | 37.33 | C |
| ATOM | 2308 | CE2 | TYR | C | 432 | 4.786 | 39.212 | 39.433 | 1.00 | 34.43 | C |
| ATOM | 2309 | CZ | TYR | C | 432 | 6.039 | 39.498 | 38.917 | 1.00 | 36.21 | C |
| ATOM | 2310 | OH | TYR | C | 432 | 6.732 | 40.599 | 39.363 | 1.00 | 37.69 | O |
| ATOM | 2311 | N | VAL | C | 433 | 5.417 | 34.909 | 40.411 | 1.00 | 36.29 | N |
| ATOM | 2312 | CA | VAL | C | 433 | 5.486 | 35.055 | 41.862 | 1.00 | 35.95 | C |
| ATOM | 2313 | C | VAL | C | 433 | 5.433 | 36.547 | 42.195 | 1.00 | 37.68 | C |
| ATOM | 2314 | O | VAL | C | 433 | 6.337 | 37.303 | 41.846 | 1.00 | 37.86 | O |
| ATOM | 2315 | CB | VAL | C | 433 | 6.799 | 34.455 | 42.421 | 1.00 | 36.60 | C |
| ATOM | 2316 | CG1 | VAL | C | 433 | 6.947 | 34.777 | 43.906 | 1.00 | 31.64 | C |
| ATOM | 2317 | CG2 | VAL | C | 433 | 6.805 | 32.956 | 42.199 | 1.00 | 35.80 | C |
| ATOM | 2318 | N | PRO | C | 434 | 4.356 | 36.993 | 42.856 | 1.00 | 39.99 | N |
| ATOM | 2319 | CA | PRO | C | 434 | 4.209 | 38.408 | 43.221 | 1.00 | 43.19 | C |
| ATOM | 2320 | C | PRO | C | 434 | 5.296 | 38.906 | 44.160 | 1.00 | 45.66 | C |
| ATOM | 2321 | O | PRO | C | 434 | 5.646 | 38.237 | 45.126 | 1.00 | 46.94 | O |
| ATOM | 2322 | CB | PRO | C | 434 | 2.820 | 38.460 | 43.850 | 1.00 | 42.20 | C |
| ATOM | 2323 | CG | PRO | C | 434 | 2.634 | 37.050 | 44.389 | 1.00 | 41.37 | C |
| ATOM | 2324 | CD | PRO | C | 434 | 3.173 | 36.216 | 43.267 | 1.00 | 38.44 | C |
| ATOM | 2325 | N | GLY | C | 435 | 5.828 | 40.086 | 43.867 | 1.00 | 48.42 | N |
| ATOM | 2326 | CA | GLY | C | 435 | 6.875 | 40.653 | 44.694 | 1.00 | 51.65 | C |
| ATOM | 2327 | C | GLY | C | 435 | 8.220 | 40.622 | 43.994 | 1.00 | 53.74 | C |
| ATOM | 2328 | O | GLY | C | 435 | 9.183 | 41.234 | 44.451 | 1.00 | 54.21 | O |
| ATOM | 2329 | N | MET | C | 436 | 8.267 | 39.905 | 42.875 | 1.00 | 55.58 | N |
| ATOM | 2330 | CA | MET | C | 436 | 9.467 | 39.746 | 42.053 | 1.00 | 57.85 | C |
| ATOM | 2331 | C | MET | C | 436 | 10.171 | 41.077 | 41.781 | 1.00 | 57.97 | C |
| ATOM | 2332 | O | MET | C | 436 | 11.366 | 41.104 | 41.499 | 1.00 | 57.90 | O |
| ATOM | 2333 | CB | MET | C | 436 | 9.073 | 39.086 | 40.716 | 1.00 | 60.24 | C |
| ATOM | 2334 | CG | MET | C | 436 | 10.117 | 38.170 | 40.061 | 1.00 | 62.63 | C |
| ATOM | 2335 | SD | MET | C | 436 | 11.294 | 38.958 | 38.921 | 1.00 | 66.70 | S |
| ATOM | 2336 | CE | MET | C | 436 | 10.350 | 39.014 | 37.425 | 1.00 | 65.33 | C |
| ATOM | 2337 | N | ASP | C | 437 | 9.435 | 42.179 | 41.884 | 1.00 | 58.78 | N |
| ATOM | 2338 | CA | ASP | C | 437 | 10.000 | 43.494 | 41.596 | 1.00 | 59.01 | C |
| ATOM | 2339 | C | ASP | C | 437 | 10.399 | 44.398 | 42.766 | 1.00 | 58.17 | C |
| ATOM | 2340 | O | ASP | C | 437 | 11.122 | 45.370 | 42.564 | 1.00 | 58.63 | O |
| ATOM | 2341 | CB | ASP | C | 437 | 9.056 | 44.253 | 40.652 | 1.00 | 59.84 | C |
| ATOM | 2342 | CG | ASP | C | 437 | 7.672 | 44.451 | 41.239 | 1.00 | 61.99 | C |
| ATOM | 2343 | OD1 | ASP | C | 437 | 7.187 | 43.548 | 41.953 | 1.00 | 62.11 | O |
| ATOM | 2344 | OD2 | ASP | C | 437 | 7.058 | 45.507 | 40.971 | 1.00 | 63.72 | O |
| ATOM | 2345 | N | VAL | C | 438 | 9.957 | 44.100 | 43.982 | 1.00 | 57.08 | N |
| ATOM | 2346 | CA | VAL | C | 438 | 10.333 | 44.949 | 45.113 | 1.00 | 57.03 | C |
| ATOM | 2347 | C | VAL | C | 438 | 10.929 | 44.203 | 46.306 | 1.00 | 56.72 | C |
| ATOM | 2348 | O | VAL | C | 438 | 11.658 | 44.789 | 47.110 | 1.00 | 56.31 | O |
| ATOM | 2349 | CB | VAL | C | 438 | 9.134 | 45.800 | 45.619 | 1.00 | 57.87 | C |
| ATOM | 2350 | CG1 | VAL | C | 438 | 8.678 | 46.761 | 44.529 | 1.00 | 58.76 | C |
| ATOM | 2351 | CG2 | VAL | C | 438 | 7.991 | 44.898 | 46.059 | 1.00 | 57.18 | C |
| ATOM | 2352 | N | LEU | C | 439 | 10.625 | 42.916 | 46.425 | 1.00 | 55.85 | N |
| ATOM | 2353 | CA | LEU | C | 439 | 11.146 | 42.132 | 47.534 | 1.00 | 55.27 | C |
| ATOM | 2354 | C | LEU | C | 439 | 12.559 | 41.640 | 47.258 | 1.00 | 54.28 | C |
| ATOM | 2355 | O | LEU | C | 439 | 12.969 | 41.499 | 46.104 | 1.00 | 53.11 | O |
| ATOM | 2356 | CB | LEU | C | 439 | 10.243 | 40.924 | 47.816 | 1.00 | 55.76 | C |
| ATOM | 2357 | CG | LEU | C | 439 | 8.888 | 41.175 | 48.477 | 1.00 | 56.88 | C |
| ATOM | 2358 | CD1 | LEU | C | 439 | 8.011 | 42.009 | 47.559 | 1.00 | 59.05 | C |
| ATOM | 2359 | CD2 | LEU | C | 439 | 8.218 | 39.851 | 48.783 | 1.00 | 56.52 | C |
| ATOM | 2360 | N | PRO | C | 440 | 13.333 | 41.387 | 48.324 | 1.00 | 53.74 | N |
| ATOM | 2361 | CA | PRO | C | 440 | 14.699 | 40.902 | 48.121 | 1.00 | 52.02 | C |
| ATOM | 2362 | C | PRO | C | 440 | 14.682 | 39.494 | 47.528 | 1.00 | 50.04 | C |
| ATOM | 2363 | O | PRO | C | 440 | 13.806 | 38.682 | 47.833 | 1.00 | 48.79 | O |

TABLE 4-continued

Stem Cell Factor Dimer

| ATOM | 2364 | CB | PRO | C | 440 | 15.299 | 40.948 | 49.529 | 1.00 | 52.43 | C |
|---|---|---|---|---|---|---|---|---|---|---|---|
| ATOM | 2365 | CG | PRO | C | 440 | 14.116 | 40.725 | 50.414 | 1.00 | 52.90 | C |
| ATOM | 2366 | CD | PRO | C | 440 | 13.050 | 41.583 | 49.759 | 1.00 | 53.29 | C |
| ATOM | 2367 | N | SER | C | 441 | 15.653 | 39.234 | 46.665 | 1.00 | 48.29 | N |
| ATOM | 2368 | CA | SER | C | 441 | 15.818 | 37.957 | 45.984 | 1.00 | 46.16 | C |
| ATOM | 2369 | C | SER | C | 441 | 15.447 | 36.715 | 46.802 | 1.00 | 44.55 | C |
| ATOM | 2370 | O | SER | C | 441 | 14.661 | 35.887 | 46.361 | 1.00 | 41.81 | O |
| ATOM | 2371 | CB | SER | C | 441 | 17.267 | 37.852 | 45.500 | 1.00 | 45.60 | C |
| ATOM | 2372 | OG | SER | C | 441 | 17.634 | 36.516 | 45.230 | 1.00 | 52.84 | O |
| ATOM | 2373 | N | HIS | C | 442 | 16.006 | 36.587 | 47.998 | 1.00 | 46.27 | N |
| ATOM | 2374 | CA | HIS | C | 442 | 15.732 | 35.417 | 48.823 | 1.00 | 47.87 | C |
| ATOM | 2375 | C | HIS | C | 442 | 14.251 | 35.235 | 49.123 | 1.00 | 47.05 | C |
| ATOM | 2376 | O | HIS | C | 442 | 13.819 | 34.172 | 49.573 | 1.00 | 46.64 | O |
| ATOM | 2377 | CB | HIS | C | 442 | 16.550 | 35.478 | 50.125 | 1.00 | 49.97 | C |
| ATOM | 2378 | CG | HIS | C | 442 | 16.105 | 36.539 | 51.085 | 1.00 | 51.99 | C |
| ATOM | 2379 | ND1 | HIS | C | 442 | 15.059 | 36.357 | 51.966 | 1.00 | 52.74 | N |
| ATOM | 2380 | CD2 | HIS | C | 442 | 16.582 | 37.786 | 51.318 | 1.00 | 51.71 | C |
| ATOM | 2381 | CE1 | HIS | C | 442 | 14.913 | 37.446 | 52.702 | 1.00 | 52.93 | C |
| ATOM | 2382 | NE2 | HIS | C | 442 | 15.824 | 38.327 | 52.329 | 1.00 | 52.63 | N |
| ATOM | 2383 | N | CYS | C | 443 | 13.467 | 36.270 | 48.861 | 1.00 | 46.79 | N |
| ATOM | 2384 | CA | CYS | C | 443 | 12.042 | 36.181 | 49.113 | 1.00 | 47.55 | C |
| ATOM | 2385 | C | CYS | C | 443 | 11.280 | 35.549 | 47.957 | 1.00 | 44.52 | C |
| ATOM | 2386 | O | CYS | C | 443 | 10.168 | 35.066 | 48.156 | 1.00 | 44.07 | O |
| ATOM | 2387 | CB | CYS | C | 443 | 11.449 | 37.564 | 49.396 | 1.00 | 52.06 | C |
| ATOM | 2388 | SG | CYS | C | 443 | 11.991 | 38.314 | 50.959 | 1.00 | 59.63 | S |
| ATOM | 2389 | N | TRP | C | 444 | 11.872 | 35.526 | 46.762 | 1.00 | 41.20 | N |
| ATOM | 2390 | CA | TRP | C | 444 | 11.158 | 34.974 | 45.611 | 1.00 | 38.57 | C |
| ATOM | 2391 | C | TRP | C | 444 | 11.831 | 34.011 | 44.615 | 1.00 | 36.90 | C |
| ATOM | 2392 | O | TRP | C | 444 | 11.136 | 33.181 | 44.039 | 1.00 | 34.96 | O |
| ATOM | 2393 | CB | TRP | C | 444 | 10.539 | 36.129 | 44.812 | 1.00 | 35.62 | C |
| ATOM | 2394 | CG | TRP | C | 444 | 11.547 | 37.163 | 44.372 | 1.00 | 32.01 | C |
| ATOM | 2395 | CD1 | TRP | C | 444 | 11.911 | 38.298 | 45.043 | 1.00 | 32.10 | C |
| ATOM | 2396 | CD2 | TRP | C | 444 | 12.341 | 37.131 | 43.180 | 1.00 | 28.95 | C |
| ATOM | 2397 | NE1 | TRP | C | 444 | 12.887 | 38.973 | 44.343 | 1.00 | 27.58 | N |
| ATOM | 2398 | CE2 | TRP | C | 444 | 13.171 | 38.279 | 43.199 | 1.00 | 26.83 | C |
| ATOM | 2399 | CE3 | TRP | C | 444 | 12.434 | 36.245 | 42.098 | 1.00 | 28.17 | C |
| ATOM | 2400 | CZ2 | TRP | C | 444 | 14.082 | 38.560 | 42.182 | 1.00 | 25.62 | C |
| ATOM | 2401 | CZ3 | TRP | C | 444 | 13.344 | 36.523 | 41.083 | 1.00 | 26.33 | C |
| ATOM | 2402 | CH2 | TRP | C | 444 | 14.157 | 37.672 | 41.134 | 1.00 | 28.83 | C |
| ATOM | 2403 | N | ILE | C | 445 | 13.143 | 34.110 | 44.388 | 1.00 | 36.37 | N |
| ATOM | 2404 | CA | ILE | C | 445 | 13.792 | 33.226 | 43.408 | 1.00 | 37.21 | C |
| ATOM | 2405 | C | ILE | C | 445 | 13.515 | 31.735 | 43.484 | 1.00 | 36.05 | C |
| ATOM | 2406 | O | ILE | C | 445 | 13.457 | 31.075 | 42.449 | 1.00 | 35.39 | O |
| ATOM | 2407 | CB | ILE | C | 445 | 15.343 | 33.377 | 43.367 | 1.00 | 40.95 | C |
| ATOM | 2408 | CG1 | ILE | C | 445 | 15.898 | 33.609 | 44.772 | 1.00 | 41.41 | C |
| ATOM | 2409 | CG2 | ILE | C | 445 | 15.735 | 34.437 | 42.348 | 1.00 | 41.56 | C |
| ATOM | 2410 | CD1 | ILE | C | 445 | 15.849 | 32.377 | 45.652 | 1.00 | 40.58 | C |
| ATOM | 2411 | N | SER | C | 446 | 13.359 | 31.194 | 44.686 | 1.00 | 35.89 | N |
| ATOM | 2412 | CA | SER | C | 446 | 13.104 | 29.766 | 44.828 | 1.00 | 36.80 | C |
| ATOM | 2413 | C | SER | C | 446 | 11.899 | 29.348 | 43.999 | 1.00 | 36.19 | C |
| ATOM | 2414 | O | SER | C | 446 | 12.014 | 28.507 | 43.105 | 1.00 | 37.02 | O |
| ATOM | 2415 | CB | SER | C | 446 | 12.870 | 29.404 | 46.297 | 1.00 | 39.47 | C |
| ATOM | 2416 | OG | SER | C | 446 | 12.486 | 28.044 | 46.444 | 1.00 | 37.74 | O |
| ATOM | 2417 | N | GLU | C | 447 | 10.744 | 29.933 | 44.292 | 1.00 | 33.96 | N |
| ATOM | 2418 | CA | GLU | C | 447 | 9.532 | 29.606 | 43.551 | 1.00 | 32.24 | C |
| ATOM | 2419 | C | GLU | C | 447 | 9.635 | 30.046 | 42.080 | 1.00 | 29.53 | C |
| ATOM | 2420 | O | GLU | C | 447 | 9.181 | 29.339 | 41.183 | 1.00 | 28.78 | O |
| ATOM | 2421 | CB | GLU | C | 447 | 8.309 | 30.266 | 44.211 | 1.00 | 34.77 | C |
| ATOM | 2422 | CG | GLU | C | 447 | 6.975 | 29.899 | 43.567 | 1.00 | 39.16 | C |
| ATOM | 2423 | CD | GLU | C | 447 | 6.655 | 28.416 | 43.690 | 1.00 | 42.43 | C |
| ATOM | 2424 | OE1 | GLU | C | 447 | 5.783 | 27.919 | 42.945 | 1.00 | 43.28 | O |
| ATOM | 2425 | OE2 | GLU | C | 447 | 7.275 | 27.744 | 44.541 | 1.00 | 46.08 | O |
| ATOM | 2426 | N | MET | C | 448 | 10.240 | 31.201 | 41.825 | 1.00 | 27.08 | N |
| ATOM | 2427 | CA | MET | C | 448 | 10.352 | 31.670 | 40.449 | 1.00 | 28.04 | C |
| ATOM | 2428 | C | MET | C | 448 | 11.130 | 30.707 | 39.567 | 1.00 | 27.17 | C |
| ATOM | 2429 | O | MET | C | 448 | 10.719 | 30.399 | 38.446 | 1.00 | 26.96 | O |
| ATOM | 2430 | CB | MET | C | 448 | 11.009 | 33.047 | 40.381 | 1.00 | 28.47 | C |
| ATOM | 2431 | CG | MET | C | 448 | 10.954 | 33.671 | 38.987 | 1.00 | 33.18 | C |
| ATOM | 2432 | SD | MET | C | 448 | 9.381 | 34.531 | 38.559 | 1.00 | 40.53 | S |
| ATOM | 2433 | CE | MET | C | 448 | 8.128 | 33.296 | 38.951 | 1.00 | 38.78 | C |
| ATOM | 2434 | N | VAL | C | 449 | 12.264 | 30.248 | 40.073 | 1.00 | 25.81 | N |
| ATOM | 2435 | CA | VAL | C | 449 | 13.104 | 29.322 | 39.339 | 1.00 | 26.02 | C |
| ATOM | 2436 | C | VAL | C | 449 | 12.311 | 28.054 | 39.050 | 1.00 | 26.19 | C |
| ATOM | 2437 | O | VAL | C | 449 | 12.356 | 27.520 | 37.936 | 1.00 | 27.20 | O |
| ATOM | 2438 | CB | VAL | C | 449 | 14.398 | 29.025 | 40.150 | 1.00 | 28.96 | C |
| ATOM | 2439 | CG1 | VAL | C | 449 | 14.830 | 27.598 | 39.989 | 1.00 | 30.72 | C |
| ATOM | 2440 | CG2 | VAL | C | 449 | 15.506 | 29.964 | 39.682 | 1.00 | 28.33 | C |

TABLE 4-continued

Stem Cell Factor Dimer

| ATOM | 2441 | N | VAL | C | 450 | 11.560 | 27.588 | 40.041 | 1.00 | 24.17 | N |
| ATOM | 2442 | CA | VAL | C | 450 | 10.753 | 26.391 | 39.861 | 1.00 | 24.70 | C |
| ATOM | 2443 | C | VAL | C | 450 | 9.697 | 26.627 | 38.788 | 1.00 | 24.32 | C |
| ATOM | 2444 | O | VAL | C | 450 | 9.442 | 25.756 | 37.946 | 1.00 | 24.90 | O |
| ATOM | 2445 | CB | VAL | C | 450 | 10.056 | 25.976 | 41.182 | 1.00 | 26.76 | C |
| ATOM | 2446 | CG1 | VAL | C | 450 | 8.980 | 24.935 | 40.914 | 1.00 | 24.89 | C |
| ATOM | 2447 | CG2 | VAL | C | 450 | 11.077 | 25.404 | 42.141 | 1.00 | 25.53 | C |
| ATOM | 2448 | N | GLN | C | 451 | 9.094 | 27.809 | 38.802 | 1.00 | 23.10 | N |
| ATOM | 2449 | CA | GLN | C | 451 | 8.063 | 28.114 | 37.819 | 1.00 | 21.98 | C |
| ATOM | 2450 | C | GLN | C | 451 | 8.625 | 28.401 | 36.437 | 1.00 | 19.81 | C |
| ATOM | 2451 | O | GLN | C | 451 | 7.993 | 28.077 | 35.437 | 1.00 | 21.40 | O |
| ATOM | 2452 | CB | GLN | C | 451 | 7.196 | 29.283 | 38.294 | 1.00 | 22.86 | C |
| ATOM | 2453 | CG | GLN | C | 451 | 6.279 | 28.940 | 39.480 | 1.00 | 24.71 | C |
| ATOM | 2454 | CD | GLN | C | 451 | 5.431 | 27.670 | 39.270 | 1.00 | 25.91 | C |
| ATOM | 2455 | OE1 | GLN | C | 451 | 5.034 | 27.346 | 38.152 | 1.00 | 24.23 | O |
| ATOM | 2456 | NE2 | GLN | C | 451 | 5.139 | 26.965 | 40.362 | 1.00 | 23.67 | N |
| ATOM | 2457 | N | LEU | C | 452 | 9.809 | 29.006 | 36.376 | 1.00 | 20.61 | N |
| ATOM | 2458 | CA | LEU | C | 452 | 10.432 | 29.306 | 35.095 | 1.00 | 19.29 | C |
| ATOM | 2459 | C | LEU | C | 452 | 10.823 | 27.985 | 34.454 | 1.00 | 21.21 | C |
| ATOM | 2460 | O | LEU | C | 452 | 10.801 | 27.842 | 33.247 | 1.00 | 21.48 | O |
| ATOM | 2461 | CB | LEU | C | 452 | 11.672 | 30.179 | 35.285 | 1.00 | 20.34 | C |
| ATOM | 2462 | CG | LEU | C | 452 | 11.460 | 31.667 | 35.608 | 1.00 | 22.71 | C |
| ATOM | 2463 | CD1 | LEU | C | 452 | 12.782 | 32.308 | 36.035 | 1.00 | 19.44 | C |
| ATOM | 2464 | CD2 | LEU | C | 452 | 10.882 | 32.382 | 34.384 | 1.00 | 20.12 | C |
| ATOM | 2465 | N | SER | C | 453 | 11.179 | 27.014 | 35.280 | 1.00 | 22.75 | N |
| ATOM | 2466 | CA | SER | C | 453 | 11.559 | 25.702 | 34.784 | 1.00 | 23.36 | C |
| ATOM | 2467 | C | SER | C | 453 | 10.345 | 25.013 | 34.175 | 1.00 | 21.69 | C |
| ATOM | 2468 | O | SER | C | 453 | 10.426 | 24.423 | 33.102 | 1.00 | 22.03 | O |
| ATOM | 2469 | CB | SER | C | 453 | 12.109 | 24.852 | 35.927 | 1.00 | 23.97 | C |
| ATOM | 2470 | OG | SER | C | 453 | 12.431 | 23.548 | 35.475 | 1.00 | 30.62 | O |
| ATOM | 2471 | N | ASP | C | 454 | 9.211 | 25.092 | 34.861 | 1.00 | 23.68 | N |
| ATOM | 2472 | CA | ASP | C | 454 | 7.999 | 24.456 | 34.353 | 1.00 | 23.36 | C |
| ATOM | 2473 | C | ASP | C | 454 | 7.540 | 25.068 | 33.026 | 1.00 | 23.44 | C |
| ATOM | 2474 | O | ASP | C | 454 | 7.067 | 24.342 | 32.140 | 1.00 | 18.28 | O |
| ATOM | 2475 | CB | ASP | C | 454 | 6.849 | 24.559 | 35.357 | 1.00 | 23.97 | C |
| ATOM | 2476 | CG | ASP | C | 454 | 5.574 | 23.933 | 34.818 | 1.00 | 28.33 | C |
| ATOM | 2477 | OD1 | ASP | C | 454 | 5.591 | 22.720 | 34.540 | 1.00 | 30.65 | O |
| ATOM | 2478 | OD2 | ASP | C | 454 | 4.559 | 24.643 | 34.646 | 1.00 | 32.30 | O |
| ATOM | 2479 | N | SER | C | 455 | 7.657 | 26.398 | 32.911 | 1.00 | 20.75 | N |
| ATOM | 2480 | CA | SER | C | 455 | 7.250 | 27.105 | 31.693 | 1.00 | 22.16 | C |
| ATOM | 2481 | C | SER | C | 455 | 8.123 | 26.745 | 30.504 | 1.00 | 19.56 | C |
| ATOM | 2482 | O | SER | C | 455 | 7.617 | 26.526 | 29.402 | 1.00 | 18.40 | O |
| ATOM | 2483 | CB | SER | C | 455 | 7.293 | 28.630 | 31.885 | 1.00 | 21.64 | C |
| ATOM | 2484 | OG | SER | C | 455 | 6.236 | 29.060 | 32.720 | 1.00 | 24.44 | O |
| ATOM | 2485 | N | LEU | C | 456 | 9.432 | 26.700 | 30.723 | 1.00 | 20.20 | N |
| ATOM | 2486 | CA | LEU | C | 456 | 10.343 | 26.366 | 29.639 | 1.00 | 22.64 | C |
| ATOM | 2487 | C | LEU | C | 456 | 10.101 | 24.929 | 29.182 | 1.00 | 22.40 | C |
| ATOM | 2488 | O | LEU | C | 456 | 10.031 | 24.656 | 27.977 | 1.00 | 21.78 | O |
| ATOM | 2489 | CB | LEU | C | 456 | 11.799 | 26.558 | 30.076 | 1.00 | 26.72 | C |
| ATOM | 2490 | CG | LEU | C | 456 | 12.394 | 27.982 | 30.077 | 1.00 | 30.48 | C |
| ATOM | 2491 | CD1 | LEU | C | 456 | 12.340 | 28.603 | 28.678 | 1.00 | 31.06 | C |
| ATOM | 2492 | CD2 | LEU | C | 456 | 11.635 | 28.836 | 31.022 | 1.00 | 31.14 | C |
| ATOM | 2493 | N | THR | C | 457 | 9.956 | 24.018 | 30.138 | 1.00 | 22.09 | N |
| ATOM | 2494 | CA | THR | C | 457 | 9.707 | 22.618 | 29.810 | 1.00 | 27.16 | C |
| ATOM | 2495 | C | THR | C | 457 | 8.389 | 22.472 | 29.049 | 1.00 | 27.09 | C |
| ATOM | 2496 | O | THR | C | 457 | 8.306 | 21.682 | 28.109 | 1.00 | 29.28 | O |
| ATOM | 2497 | CB | THR | C | 457 | 9.671 | 21.726 | 31.077 | 1.00 | 29.54 | C |
| ATOM | 2498 | OG1 | THR | C | 457 | 10.934 | 21.797 | 31.748 | 1.00 | 34.82 | O |
| ATOM | 2499 | CG2 | THR | C | 457 | 9.408 | 20.276 | 30.702 | 1.00 | 31.05 | C |
| ATOM | 2500 | N | ASP | C | 458 | 7.361 | 23.221 | 29.444 | 1.00 | 25.79 | N |
| ATOM | 2501 | CA | ASP | C | 458 | 6.087 | 23.149 | 28.731 | 1.00 | 25.04 | C |
| ATOM | 2502 | C | ASP | C | 458 | 6.288 | 23.698 | 27.322 | 1.00 | 24.70 | C |
| ATOM | 2503 | O | ASP | C | 458 | 5.719 | 23.198 | 26.357 | 1.00 | 23.65 | O |
| ATOM | 2504 | CB | ASP | C | 458 | 5.003 | 24.004 | 29.399 | 1.00 | 26.32 | C |
| ATOM | 2505 | CG | ASP | C | 458 | 4.630 | 23.524 | 30.782 | 1.00 | 27.77 | C |
| ATOM | 2506 | OD1 | ASP | C | 458 | 4.830 | 22.333 | 31.084 | 1.00 | 31.33 | O |
| ATOM | 2507 | OD2 | ASP | C | 458 | 4.111 | 24.348 | 31.567 | 1.00 | 28.00 | O |
| ATOM | 2508 | N | LEU | C | 459 | 7.083 | 24.756 | 27.215 | 1.00 | 25.26 | N |
| ATOM | 2509 | CA | LEU | C | 459 | 7.337 | 25.393 | 25.919 | 1.00 | 27.22 | C |
| ATOM | 2510 | C | LEU | C | 459 | 8.099 | 24.451 | 24.982 | 1.00 | 28.01 | C |
| ATOM | 2511 | O | LEU | C | 459 | 7.850 | 24.404 | 23.776 | 1.00 | 27.24 | O |
| ATOM | 2512 | CB | LEU | C | 459 | 8.137 | 26.690 | 26.122 | 1.00 | 24.90 | C |
| ATOM | 2513 | CG | LEU | C | 459 | 8.385 | 27.586 | 24.908 | 1.00 | 26.22 | C |
| ATOM | 2514 | CD1 | LEU | C | 459 | 7.047 | 28.089 | 24.381 | 1.00 | 29.21 | C |
| ATOM | 2515 | CD2 | LEU | C | 459 | 9.266 | 28.784 | 25.291 | 1.00 | 27.97 | C |
| ATOM | 2516 | N | LEU | C | 460 | 9.024 | 23.689 | 25.551 | 1.00 | 29.41 | N |
| ATOM | 2517 | CA | LEU | C | 460 | 9.831 | 22.770 | 24.764 | 1.00 | 30.45 | C |

TABLE 4-continued

Stem Cell Factor Dimer

| ATOM | 2518 | C | LEU | C | 460 | 8.951 | 21.882 | 23.891 | 1.00 | 30.83 | C |
|---|---|---|---|---|---|---|---|---|---|---|---|
| ATOM | 2519 | O | LEU | C | 460 | 9.204 | 21.730 | 22.697 | 1.00 | 32.84 | O |
| ATOM | 2520 | CB | LEU | C | 460 | 10.691 | 21.921 | 25.700 | 1.00 | 29.64 | C |
| ATOM | 2521 | CG | LEU | C | 460 | 11.838 | 21.136 | 25.083 | 1.00 | 28.50 | C |
| ATOM | 2522 | CD1 | LEU | C | 460 | 12.846 | 22.088 | 24.450 | 1.00 | 24.94 | C |
| ATOM | 2523 | CD2 | LEU | C | 460 | 12.495 | 20.312 | 26.177 | 1.00 | 28.74 | C |
| ATOM | 2524 | N | ASP | C | 461 | 7.906 | 21.315 | 24.480 | 1.00 | 31.68 | N |
| ATOM | 2525 | CA | ASP | C | 461 | 6.988 | 20.445 | 23.746 | 1.00 | 33.28 | C |
| ATOM | 2526 | C | ASP | C | 461 | 6.234 | 21.096 | 22.581 | 1.00 | 31.27 | C |
| ATOM | 2527 | O | ASP | C | 461 | 5.533 | 20.412 | 21.834 | 1.00 | 30.90 | O |
| ATOM | 2528 | CB | ASP | C | 461 | 5.974 | 19.822 | 24.708 | 1.00 | 38.72 | C |
| ATOM | 2529 | CG | ASP | C | 461 | 6.624 | 18.885 | 25.705 | 1.00 | 46.26 | C |
| ATOM | 2530 | OD1 | ASP | C | 461 | 7.253 | 19.374 | 26.674 | 1.00 | 48.70 | O |
| ATOM | 2531 | OD2 | ASP | C | 461 | 6.521 | 17.653 | 25.510 | 1.00 | 50.00 | O |
| ATOM | 2532 | N | LYS | C | 462 | 6.359 | 22.408 | 22.425 | 1.00 | 27.57 | N |
| ATOM | 2533 | CA | LYS | C | 462 | 5.680 | 23.080 | 21.327 | 1.00 | 25.35 | C |
| ATOM | 2534 | C | LYS | C | 462 | 6.564 | 23.086 | 20.079 | 1.00 | 23.43 | C |
| ATOM | 2535 | O | LYS | C | 462 | 6.146 | 23.532 | 19.019 | 1.00 | 24.64 | O |
| ATOM | 2536 | CB | LYS | C | 462 | 5.324 | 24.518 | 21.716 | 1.00 | 24.71 | C |
| ATOM | 2537 | CG | LYS | C | 462 | 4.388 | 24.630 | 22.919 | 1.00 | 25.36 | C |
| ATOM | 2538 | CD | LYS | C | 462 | 3.081 | 23.877 | 22.675 | 1.00 | 29.01 | C |
| ATOM | 2539 | CE | LYS | C | 462 | 2.079 | 24.115 | 23.800 | 1.00 | 31.24 | C |
| ATOM | 2540 | NZ | LYS | C | 462 | 2.665 | 23.788 | 25.129 | 1.00 | 34.34 | N |
| ATOM | 2541 | N | PHE | C | 463 | 7.781 | 22.580 | 20.214 | 1.00 | 23.53 | N |
| ATOM | 2542 | CA | PHE | C | 463 | 8.726 | 22.543 | 19.101 | 1.00 | 25.78 | C |
| ATOM | 2543 | C | PHE | C | 463 | 9.330 | 21.166 | 18.891 | 1.00 | 26.15 | C |
| ATOM | 2544 | O | PHE | C | 463 | 9.116 | 20.259 | 19.690 | 1.00 | 22.61 | O |
| ATOM | 2545 | CB | PHE | C | 463 | 9.871 | 23.544 | 19.334 | 1.00 | 25.16 | C |
| ATOM | 2546 | CG | PHE | C | 463 | 9.401 | 24.955 | 19.555 | 1.00 | 25.81 | C |
| ATOM | 2547 | CD1 | PHE | C | 463 | 9.080 | 25.403 | 20.834 | 1.00 | 25.56 | C |
| ATOM | 2548 | CD2 | PHE | C | 463 | 9.218 | 25.813 | 18.479 | 1.00 | 21.79 | C |
| ATOM | 2549 | CE1 | PHE | C | 463 | 8.581 | 26.681 | 21.037 | 1.00 | 21.95 | C |
| ATOM | 2550 | CE2 | PHE | C | 463 | 8.719 | 27.095 | 18.671 | 1.00 | 23.55 | C |
| ATOM | 2551 | CZ | PHE | C | 463 | 8.399 | 27.527 | 19.955 | 1.00 | 25.05 | C |
| ATOM | 2552 | N | SER | C | 464 | 10.082 | 21.030 | 17.801 | 1.00 | 28.14 | N |
| ATOM | 2553 | CA | SER | C | 464 | 10.765 | 19.791 | 17.481 | 1.00 | 32.33 | C |
| ATOM | 2554 | C | SER | C | 464 | 12.166 | 20.179 | 17.031 | 1.00 | 32.53 | C |
| ATOM | 2555 | O | SER | C | 464 | 12.357 | 21.206 | 16.388 | 1.00 | 34.11 | O |
| ATOM | 2556 | CB | SER | C | 464 | 10.025 | 19.021 | 16.377 | 1.00 | 33.88 | C |
| ATOM | 2557 | OG | SER | C | 464 | 10.234 | 19.586 | 15.099 | 1.00 | 37.24 | O |
| ATOM | 2558 | N | ASN | C | 465 | 13.151 | 19.364 | 17.388 | 1.00 | 35.11 | N |
| ATOM | 2559 | CA | ASN | C | 465 | 14.531 | 19.654 | 17.041 | 1.00 | 36.23 | C |
| ATOM | 2560 | C | ASN | C | 465 | 14.801 | 19.559 | 15.541 | 1.00 | 38.36 | C |
| ATOM | 2561 | O | ASN | C | 465 | 14.064 | 18.907 | 14.798 | 1.00 | 35.10 | O |
| ATOM | 2562 | CB | ASN | C | 465 | 15.469 | 18.716 | 17.797 | 1.00 | 36.73 | C |
| ATOM | 2563 | CG | ASN | C | 465 | 16.803 | 19.363 | 18.112 | 1.00 | 38.14 | C |
| ATOM | 2564 | OD1 | ASN | C | 465 | 17.235 | 20.283 | 17.424 | 1.00 | 38.06 | O |
| ATOM | 2565 | ND2 | ASN | C | 465 | 17.466 | 18.876 | 19.151 | 1.00 | 39.58 | N |
| ATOM | 2566 | N | ILE | C | 466 | 15.868 | 20.225 | 15.111 | 1.00 | 41.35 | N |
| ATOM | 2567 | CA | ILE | C | 466 | 16.273 | 20.254 | 13.711 | 1.00 | 45.74 | C |
| ATOM | 2568 | C | ILE | C | 466 | 17.754 | 19.893 | 13.603 | 1.00 | 49.28 | C |
| ATOM | 2569 | O | ILE | C | 466 | 18.561 | 20.290 | 14.449 | 1.00 | 49.27 | O |
| ATOM | 2570 | CB | ILE | C | 466 | 16.052 | 21.655 | 13.114 | 1.00 | 45.87 | C |
| ATOM | 2571 | CG1 | ILE | C | 466 | 14.573 | 22.030 | 13.223 | 1.00 | 46.31 | C |
| ATOM | 2572 | CG2 | ILE | C | 466 | 16.517 | 21.688 | 11.668 | 1.00 | 46.14 | C |
| ATOM | 2573 | CD1 | ILE | C | 466 | 14.243 | 23.442 | 12.767 | 1.00 | 46.65 | C |
| ATOM | 2574 | N | SER | C | 467 | 18.108 | 19.154 | 12.555 | 1.00 | 51.80 | N |
| ATOM | 2575 | CA | SER | C | 467 | 19.492 | 18.723 | 12.354 | 1.00 | 55.48 | C |
| ATOM | 2576 | C | SER | C | 467 | 20.470 | 19.880 | 12.114 | 1.00 | 56.29 | C |
| ATOM | 2577 | O | SER | C | 467 | 21.443 | 20.044 | 12.856 | 1.00 | 57.94 | O |
| ATOM | 2578 | CB | SER | C | 467 | 19.561 | 17.732 | 11.188 | 1.00 | 56.27 | C |
| ATOM | 2579 | OG | SER | C | 467 | 20.812 | 17.065 | 11.150 | 1.00 | 59.43 | O |
| ATOM | 2580 | N | GLU | C | 468 | 20.217 | 20.676 | 11.078 | 1.00 | 56.47 | N |
| ATOM | 2581 | CA | GLU | C | 468 | 21.085 | 21.810 | 10.766 | 1.00 | 56.36 | C |
| ATOM | 2582 | C | GLU | C | 468 | 20.504 | 23.113 | 11.309 | 1.00 | 54.13 | C |
| ATOM | 2583 | O | GLU | C | 468 | 19.343 | 23.432 | 11.055 | 1.00 | 55.55 | O |
| ATOM | 2584 | CB | GLU | C | 468 | 21.257 | 21.951 | 9.253 | 1.00 | 58.77 | C |
| ATOM | 2585 | CG | GLU | C | 468 | 21.898 | 20.764 | 8.562 | 1.00 | 63.85 | C |
| ATOM | 2586 | CD | GLU | C | 468 | 21.942 | 20.944 | 7.053 | 1.00 | 66.73 | C |
| ATOM | 2587 | OE1 | GLU | C | 468 | 20.860 | 20.938 | 6.422 | 1.00 | 67.58 | O |
| ATOM | 2588 | OE2 | GLU | C | 468 | 23.055 | 21.102 | 6.500 | 1.00 | 67.99 | O |
| ATOM | 2589 | N | GLY | C | 469 | 21.309 | 23.862 | 12.055 | 1.00 | 50.79 | N |
| ATOM | 2590 | CA | GLY | C | 469 | 20.842 | 25.131 | 12.586 | 1.00 | 47.17 | C |
| ATOM | 2591 | C | GLY | C | 469 | 20.508 | 25.143 | 14.065 | 1.00 | 45.11 | C |
| ATOM | 2592 | O | GLY | C | 469 | 20.180 | 24.108 | 14.649 | 1.00 | 44.06 | O |
| ATOM | 2593 | N | LEU | C | 470 | 20.589 | 26.325 | 14.670 | 1.00 | 41.53 | N |
| ATOM | 2594 | CA | LEU | C | 470 | 20.282 | 26.483 | 16.085 | 1.00 | 39.49 | C |

TABLE 4-continued

Stem Cell Factor Dimer

| ATOM | 2595 | C | LEU | C | 470 | 18.775 | 26.660 | 16.302 | 1.00 | 36.77 | C |
| ATOM | 2596 | O | LEU | C | 470 | 18.283 | 27.779 | 16.444 | 1.00 | 38.40 | O |
| ATOM | 2597 | CB | LEU | C | 470 | 21.028 | 27.688 | 16.653 | 1.00 | 40.94 | C |
| ATOM | 2598 | CG | LEU | C | 470 | 20.817 | 27.897 | 18.152 | 1.00 | 44.12 | C |
| ATOM | 2599 | CD1 | LEU | C | 470 | 21.261 | 26.630 | 18.898 | 1.00 | 45.02 | C |
| ATOM | 2600 | CD2 | LEU | C | 470 | 21.587 | 29.121 | 18.629 | 1.00 | 41.73 | C |
| ATOM | 2601 | N | SER | C | 471 | 18.063 | 25.539 | 16.343 | 1.00 | 31.88 | N |
| ATOM | 2602 | CA | SER | C | 471 | 16.620 | 25.505 | 16.525 | 1.00 | 27.37 | C |
| ATOM | 2603 | C | SER | C | 471 | 16.139 | 26.114 | 17.835 | 1.00 | 24.48 | C |
| ATOM | 2604 | O | SER | C | 471 | 16.896 | 26.240 | 18.796 | 1.00 | 24.37 | O |
| ATOM | 2605 | CB | SER | C | 471 | 16.130 | 24.055 | 16.462 | 1.00 | 27.40 | C |
| ATOM | 2606 | OG | SER | C | 471 | 16.464 | 23.358 | 17.658 | 1.00 | 23.30 | O |
| ATOM | 2607 | N | ASN | C | 472 | 14.864 | 26.480 | 17.874 | 1.00 | 22.24 | N |
| ATOM | 2608 | CA | ASN | C | 472 | 14.288 | 27.036 | 19.095 | 1.00 | 22.64 | C |
| ATOM | 2609 | C | ASN | C | 472 | 14.289 | 25.927 | 20.135 | 1.00 | 20.43 | C |
| ATOM | 2610 | O | ASN | C | 472 | 14.493 | 26.166 | 21.323 | 1.00 | 19.53 | O |
| ATOM | 2611 | CB | ASN | C | 472 | 12.852 | 27.518 | 18.854 | 1.00 | 20.78 | C |
| ATOM | 2612 | CG | ASN | C | 472 | 12.795 | 28.860 | 18.139 | 1.00 | 21.60 | C |
| ATOM | 2613 | OD1 | ASN | C | 472 | 11.747 | 29.262 | 17.624 | 1.00 | 25.78 | O |
| ATOM | 2614 | ND2 | ASN | C | 472 | 13.912 | 29.563 | 18.118 | 1.00 | 21.36 | N |
| ATOM | 2615 | N | TYR | C | 473 | 14.062 | 24.705 | 19.674 | 1.00 | 21.65 | N |
| ATOM | 2616 | CA | TYR | C | 473 | 14.039 | 23.551 | 20.562 | 1.00 | 20.71 | C |
| ATOM | 2617 | C | TYR | C | 473 | 15.352 | 23.414 | 21.344 | 1.00 | 19.56 | C |
| ATOM | 2618 | O | TYR | C | 473 | 15.355 | 23.365 | 22.585 | 1.00 | 17.41 | O |
| ATOM | 2619 | CB | TYR | C | 473 | 13.786 | 22.275 | 19.753 | 1.00 | 22.94 | C |
| ATOM | 2620 | CG | TYR | C | 473 | 13.765 | 21.026 | 20.598 | 1.00 | 24.69 | C |
| ATOM | 2621 | CD1 | TYR | C | 473 | 12.580 | 20.570 | 21.166 | 1.00 | 25.55 | C |
| ATOM | 2622 | CD2 | TYR | C | 473 | 14.940 | 20.329 | 20.872 | 1.00 | 25.72 | C |
| ATOM | 2623 | CE1 | TYR | C | 473 | 12.559 | 19.454 | 21.991 | 1.00 | 27.45 | C |
| ATOM | 2624 | CE2 | TYR | C | 473 | 14.930 | 19.213 | 21.695 | 1.00 | 30.34 | C |
| ATOM | 2625 | CZ | TYR | C | 473 | 13.735 | 18.784 | 22.253 | 1.00 | 28.31 | C |
| ATOM | 2626 | OH | TYR | C | 473 | 13.722 | 17.700 | 23.101 | 1.00 | 34.15 | O |
| ATOM | 2627 | N | SER | C | 474 | 16.475 | 23.365 | 20.636 | 1.00 | 20.25 | N |
| ATOM | 2628 | CA | SER | C | 474 | 17.757 | 23.212 | 21.331 | 1.00 | 23.68 | C |
| ATOM | 2629 | C | SER | C | 474 | 18.106 | 24.402 | 22.224 | 1.00 | 22.92 | C |
| ATOM | 2630 | O | SER | C | 474 | 18.703 | 24.227 | 23.290 | 1.00 | 23.47 | O |
| ATOM | 2631 | CB | SER | C | 474 | 18.894 | 22.932 | 20.336 | 1.00 | 23.74 | C |
| ATOM | 2632 | OG | SER | C | 474 | 19.008 | 23.954 | 19.372 | 1.00 | 33.18 | O |
| ATOM | 2633 | N | ILE | C | 475 | 17.732 | 25.610 | 21.810 | 1.00 | 22.40 | N |
| ATOM | 2634 | CA | ILE | C | 475 | 18.004 | 26.785 | 22.638 | 1.00 | 20.76 | C |
| ATOM | 2635 | C | ILE | C | 475 | 17.202 | 26.653 | 23.925 | 1.00 | 21.49 | C |
| ATOM | 2636 | O | ILE | C | 475 | 17.721 | 26.876 | 25.025 | 1.00 | 19.81 | O |
| ATOM | 2637 | CB | ILE | C | 475 | 17.582 | 28.102 | 21.956 | 1.00 | 21.73 | C |
| ATOM | 2638 | CG1 | ILE | C | 475 | 18.446 | 28.365 | 20.727 | 1.00 | 19.99 | C |
| ATOM | 2639 | CG2 | ILE | C | 475 | 17.707 | 29.265 | 22.940 | 1.00 | 19.73 | C |
| ATOM | 2640 | CD1 | ILE | C | 475 | 18.116 | 29.694 | 20.032 | 1.00 | 24.22 | C |
| ATOM | 2641 | N | ILE | C | 476 | 15.933 | 26.280 | 23.800 | 1.00 | 21.24 | N |
| ATOM | 2642 | CA | ILE | C | 476 | 15.104 | 26.129 | 24.997 | 1.00 | 20.97 | C |
| ATOM | 2643 | C | ILE | C | 476 | 15.642 | 24.986 | 25.853 | 1.00 | 20.70 | C |
| ATOM | 2644 | O | ILE | C | 476 | 15.673 | 25.079 | 27.084 | 1.00 | 19.30 | O |
| ATOM | 2645 | CB | ILE | C | 476 | 13.619 | 25.815 | 24.654 | 1.00 | 21.79 | C |
| ATOM | 2646 | CG1 | ILE | C | 476 | 12.958 | 27.026 | 24.002 | 1.00 | 22.13 | C |
| ATOM | 2647 | CG2 | ILE | C | 476 | 12.860 | 25.435 | 25.925 | 1.00 | 16.53 | C |
| ATOM | 2648 | CD1 | ILE | C | 476 | 11.744 | 26.657 | 23.170 | 1.00 | 21.09 | C |
| ATOM | 2649 | N | ASP | C | 477 | 16.061 | 23.907 | 25.200 | 1.00 | 23.82 | N |
| ATOM | 2650 | CA | ASP | C | 477 | 16.578 | 22.740 | 25.918 | 1.00 | 25.99 | C |
| ATOM | 2651 | C | ASP | C | 477 | 17.739 | 23.163 | 26.820 | 1.00 | 26.65 | C |
| ATOM | 2652 | O | ASP | C | 477 | 17.831 | 22.725 | 27.966 | 1.00 | 27.58 | O |
| ATOM | 2653 | CB | ASP | C | 477 | 17.027 | 21.670 | 24.925 | 1.00 | 30.12 | C |
| ATOM | 2654 | CG | ASP | C | 477 | 17.187 | 20.295 | 25.568 | 1.00 | 36.38 | C |
| ATOM | 2655 | OD1 | ASP | C | 477 | 17.789 | 19.407 | 24.919 | 1.00 | 39.97 | O |
| ATOM | 2656 | OD2 | ASP | C | 477 | 16.707 | 20.094 | 26.708 | 1.00 | 36.57 | O |
| ATOM | 2657 | N | LYS | C | 478 | 18.612 | 24.030 | 26.317 | 1.00 | 27.68 | N |
| ATOM | 2658 | CA | LYS | C | 478 | 19.736 | 24.519 | 27.119 | 1.00 | 29.23 | C |
| ATOM | 2659 | C | LYS | C | 478 | 19.227 | 25.353 | 28.300 | 1.00 | 29.75 | C |
| ATOM | 2660 | O | LYS | C | 478 | 19.727 | 25.230 | 29.427 | 1.00 | 31.70 | O |
| ATOM | 2661 | CB | LYS | C | 478 | 20.673 | 25.398 | 26.284 | 1.00 | 30.85 | C |
| ATOM | 2662 | CG | LYS | C | 478 | 21.161 | 24.782 | 24.983 | 1.00 | 38.41 | C |
| ATOM | 2663 | CD | LYS | C | 478 | 22.194 | 23.690 | 25.197 | 1.00 | 42.83 | C |
| ATOM | 2664 | CE | LYS | C | 478 | 22.812 | 23.268 | 23.867 | 1.00 | 46.03 | C |
| ATOM | 2665 | NZ | LYS | C | 478 | 23.965 | 22.340 | 24.062 | 1.00 | 50.46 | N |
| ATOM | 2666 | N | LEU | C | 479 | 18.244 | 26.213 | 28.053 | 1.00 | 27.40 | N |
| ATOM | 2667 | CA | LEU | C | 479 | 17.719 | 27.045 | 29.135 | 1.00 | 28.07 | C |
| ATOM | 2668 | C | LEU | C | 479 | 17.145 | 26.193 | 30.258 | 1.00 | 24.73 | C |
| ATOM | 2669 | O | LEU | C | 479 | 17.341 | 26.498 | 31.434 | 1.00 | 22.84 | O |
| ATOM | 2670 | CB | LEU | C | 479 | 16.655 | 28.020 | 28.611 | 1.00 | 26.25 | C |
| ATOM | 2671 | CG | LEU | C | 479 | 17.165 | 29.012 | 27.560 | 1.00 | 31.77 | C |

TABLE 4-continued

Stem Cell Factor Dimer

| ATOM | 2672 | CD1 | LEU | C | 479 | 16.070 | 30.035 | 27.264 | 1.00 | 31.46 | C |
|---|---|---|---|---|---|---|---|---|---|---|---|
| ATOM | 2673 | CD2 | LEU | C | 479 | 18.437 | 29.712 | 28.056 | 1.00 | 29.08 | C |
| ATOM | 2674 | N | VAL | C | 480 | 16.449 | 25.121 | 29.889 | 1.00 | 26.01 | N |
| ATOM | 2675 | CA | VAL | C | 480 | 15.858 | 24.200 | 30.861 | 1.00 | 26.10 | C |
| ATOM | 2676 | C | VAL | C | 480 | 16.934 | 23.591 | 31.754 | 1.00 | 28.41 | C |
| ATOM | 2677 | O | VAL | C | 480 | 16.794 | 23.536 | 32.981 | 1.00 | 30.02 | O |
| ATOM | 2678 | CB | VAL | C | 480 | 15.101 | 23.033 | 30.150 | 1.00 | 27.48 | C |
| ATOM | 2679 | CG1 | VAL | C | 480 | 14.709 | 21.944 | 31.174 | 1.00 | 22.70 | C |
| ATOM | 2680 | CG2 | VAL | C | 480 | 13.847 | 23.573 | 29.438 | 1.00 | 22.45 | C |
| ATOM | 2681 | N | ASN | C | 481 | 18.015 | 23.134 | 31.138 | 1.00 | 29.31 | N |
| ATOM | 2682 | CA | ASN | C | 481 | 19.091 | 22.523 | 31.904 | 1.00 | 31.74 | C |
| ATOM | 2683 | C | ASN | C | 481 | 19.737 | 23.501 | 32.855 | 1.00 | 32.23 | C |
| ATOM | 2684 | O | ASN | C | 481 | 20.096 | 23.137 | 33.968 | 1.00 | 34.43 | O |
| ATOM | 2685 | CB | ASN | C | 481 | 20.135 | 21.926 | 30.968 | 1.00 | 31.52 | C |
| ATOM | 2686 | CG | ASN | C | 481 | 19.678 | 20.618 | 30.381 | 1.00 | 36.47 | C |
| ATOM | 2687 | OD1 | ASN | C | 481 | 19.393 | 19.673 | 31.118 | 1.00 | 37.95 | O |
| ATOM | 2688 | ND2 | ASN | C | 481 | 19.592 | 20.549 | 29.050 | 1.00 | 38.74 | N |
| ATOM | 2689 | N | ILE | C | 482 | 19.890 | 24.745 | 32.424 | 1.00 | 31.94 | N |
| ATOM | 2690 | CA | ILE | C | 482 | 20.473 | 25.739 | 33.296 | 1.00 | 32.92 | C |
| ATOM | 2691 | C | ILE | C | 482 | 19.513 | 26.004 | 34.445 | 1.00 | 33.63 | C |
| ATOM | 2692 | O | ILE | C | 482 | 19.916 | 26.019 | 35.612 | 1.00 | 33.56 | O |
| ATOM | 2693 | CB | ILE | C | 482 | 20.737 | 27.064 | 32.550 | 1.00 | 35.61 | C |
| ATOM | 2694 | CG1 | ILE | C | 482 | 21.821 | 26.853 | 31.489 | 1.00 | 36.13 | C |
| ATOM | 2695 | CG2 | ILE | C | 482 | 21.172 | 28.145 | 33.544 | 1.00 | 37.84 | C |
| ATOM | 2696 | CD1 | ILE | C | 482 | 22.014 | 28.027 | 30.560 | 1.00 | 35.81 | C |
| ATOM | 2697 | N | VAL | C | 483 | 18.235 | 26.194 | 34.125 | 1.00 | 33.38 | N |
| ATOM | 2698 | CA | VAL | C | 483 | 17.268 | 26.490 | 35.170 | 1.00 | 34.28 | C |
| ATOM | 2699 | C | VAL | C | 483 | 17.063 | 25.317 | 36.115 | 1.00 | 34.62 | C |
| ATOM | 2700 | O | VAL | C | 483 | 16.742 | 25.518 | 37.283 | 1.00 | 31.29 | O |
| ATOM | 2701 | CB | VAL | C | 483 | 15.911 | 26.951 | 34.586 | 1.00 | 35.64 | C |
| ATOM | 2702 | CG1 | VAL | C | 483 | 14.940 | 27.255 | 35.710 | 1.00 | 36.63 | C |
| ATOM | 2703 | CG2 | VAL | C | 483 | 16.109 | 28.199 | 33.745 | 1.00 | 36.55 | C |
| ATOM | 2704 | N | ASP | C | 484 | 17.240 | 24.096 | 35.616 | 1.00 | 36.84 | N |
| ATOM | 2705 | CA | ASP | C | 484 | 17.106 | 22.922 | 36.473 | 1.00 | 39.62 | C |
| ATOM | 2706 | C | ASP | C | 484 | 18.272 | 22.892 | 37.450 | 1.00 | 38.62 | C |
| ATOM | 2707 | O | ASP | C | 484 | 18.115 | 22.499 | 38.603 | 1.00 | 39.47 | O |
| ATOM | 2708 | CB | ASP | C | 484 | 17.099 | 21.629 | 35.658 | 1.00 | 42.89 | C |
| ATOM | 2709 | CG | ASP | C | 484 | 15.742 | 21.319 | 35.072 | 1.00 | 47.18 | C |
| ATOM | 2710 | OD1 | ASP | C | 484 | 14.742 | 21.900 | 35.549 | 1.00 | 50.05 | O |
| ATOM | 2711 | OD2 | ASP | C | 484 | 15.673 | 20.483 | 34.143 | 1.00 | 52.07 | O |
| ATOM | 2712 | N | ASP | C | 485 | 19.446 | 23.303 | 36.988 | 1.00 | 38.05 | N |
| ATOM | 2713 | CA | ASP | C | 485 | 20.607 | 23.337 | 37.865 | 1.00 | 40.50 | C |
| ATOM | 2714 | C | ASP | C | 485 | 20.321 | 24.271 | 39.035 | 1.00 | 41.55 | C |
| ATOM | 2715 | O | ASP | C | 485 | 20.628 | 23.949 | 40.186 | 1.00 | 42.39 | O |
| ATOM | 2716 | CB | ASP | C | 485 | 21.843 | 23.830 | 37.117 | 1.00 | 42.31 | C |
| ATOM | 2717 | CG | ASP | C | 485 | 22.286 | 22.873 | 36.036 | 1.00 | 46.90 | C |
| ATOM | 2718 | OD1 | ASP | C | 485 | 21.953 | 21.672 | 36.148 | 1.00 | 46.07 | O |
| ATOM | 2719 | OD2 | ASP | C | 485 | 22.974 | 23.316 | 35.086 | 1.00 | 47.88 | O |
| ATOM | 2720 | N | LEU | C | 486 | 19.735 | 25.427 | 38.730 | 1.00 | 41.28 | N |
| ATOM | 2721 | CA | LEU | C | 486 | 19.388 | 26.415 | 39.746 | 1.00 | 42.01 | C |
| ATOM | 2722 | C | LEU | C | 486 | 18.341 | 25.867 | 40.703 | 1.00 | 41.60 | C |
| ATOM | 2723 | O | LEU | C | 486 | 18.346 | 26.190 | 41.888 | 1.00 | 40.42 | O |
| ATOM | 2724 | CB | LEU | C | 486 | 18.857 | 27.691 | 39.091 | 1.00 | 41.85 | C |
| ATOM | 2725 | CG | LEU | C | 486 | 19.868 | 28.389 | 38.185 | 1.00 | 43.42 | C |
| ATOM | 2726 | CD1 | LEU | C | 486 | 19.212 | 29.559 | 37.452 | 1.00 | 43.01 | C |
| ATOM | 2727 | CD2 | LEU | C | 486 | 21.042 | 28.856 | 39.034 | 1.00 | 42.44 | C |
| ATOM | 2728 | N | VAL | C | 487 | 17.440 | 25.039 | 40.190 | 1.00 | 42.89 | N |
| ATOM | 2729 | CA | VAL | C | 487 | 16.413 | 24.465 | 41.045 | 1.00 | 45.33 | C |
| ATOM | 2730 | C | VAL | C | 487 | 17.095 | 23.559 | 42.063 | 1.00 | 48.13 | C |
| ATOM | 2731 | O | VAL | C | 487 | 16.747 | 23.581 | 43.248 | 1.00 | 46.85 | O |
| ATOM | 2732 | CB | VAL | C | 487 | 15.377 | 23.647 | 40.241 | 1.00 | 43.87 | C |
| ATOM | 2733 | CG1 | VAL | C | 487 | 14.393 | 22.976 | 41.185 | 1.00 | 40.38 | C |
| ATOM | 2734 | CG2 | VAL | C | 487 | 14.637 | 24.553 | 39.285 | 1.00 | 43.12 | C |
| ATOM | 2735 | N | GLU | C | 488 | 18.074 | 22.779 | 41.605 | 1.00 | 50.31 | N |
| ATOM | 2736 | CA | GLU | C | 488 | 18.808 | 21.883 | 42.498 | 1.00 | 54.58 | C |
| ATOM | 2737 | C | GLU | C | 488 | 19.626 | 22.667 | 43.527 | 1.00 | 56.13 | C |
| ATOM | 2738 | O | GLU | C | 488 | 19.730 | 22.262 | 44.678 | 1.00 | 56.58 | O |
| ATOM | 2739 | CB | GLU | C | 488 | 19.755 | 20.965 | 41.712 | 1.00 | 56.04 | C |
| ATOM | 2740 | CG | GLU | C | 488 | 19.088 | 20.057 | 40.682 | 1.00 | 59.98 | C |
| ATOM | 2741 | CD | GLU | C | 488 | 19.720 | 18.669 | 40.620 | 1.00 | 62.60 | C |
| ATOM | 2742 | OE1 | GLU | C | 488 | 19.446 | 17.861 | 41.533 | 1.00 | 61.75 | O |
| ATOM | 2743 | OE2 | GLU | C | 488 | 20.493 | 18.385 | 39.671 | 1.00 | 63.45 | O |
| ATOM | 2744 | N | CYS | C | 489 | 20.204 | 23.787 | 43.107 | 1.00 | 59.19 | N |
| ATOM | 2745 | CA | CYS | C | 489 | 21.023 | 24.614 | 43.991 | 1.00 | 62.50 | C |
| ATOM | 2746 | C | CYS | C | 489 | 20.217 | 25.331 | 45.065 | 1.00 | 64.25 | C |
| ATOM | 2747 | O | CYS | C | 489 | 20.748 | 25.686 | 46.117 | 1.00 | 62.95 | O |
| ATOM | 2748 | CB | CYS | C | 489 | 21.784 | 25.651 | 43.175 | 1.00 | 64.14 | C |

TABLE 4-continued

Stem Cell Factor Dimer

| ATOM | 2749 | SG | CYS | C | 489 | 22.738 | 24.935 | 41.835 | 1.00 | 70.99 | S |
|---|---|---|---|---|---|---|---|---|---|---|---|
| ATOM | 2750 | N | VAL | C | 490 | 18.938 | 25.557 | 44.788 | 1.00 | 66.42 | N |
| ATOM | 2751 | CA | VAL | C | 490 | 18.065 | 26.231 | 45.736 | 1.00 | 68.53 | C |
| ATOM | 2752 | C | VAL | C | 490 | 17.555 | 25.246 | 46.785 | 1.00 | 70.15 | C |
| ATOM | 2753 | O | VAL | C | 490 | 17.107 | 25.650 | 47.858 | 1.00 | 70.55 | O |
| ATOM | 2754 | CB | VAL | C | 490 | 16.864 | 26.885 | 45.012 | 1.00 | 69.36 | C |
| ATOM | 2755 | CG1 | VAL | C | 490 | 15.909 | 27.505 | 46.023 | 1.00 | 69.33 | C |
| ATOM | 2756 | CG2 | VAL | C | 490 | 17.365 | 27.948 | 44.043 | 1.00 | 68.45 | C |
| ATOM | 2757 | N | LYS | C | 491 | 17.638 | 23.955 | 46.473 | 1.00 | 71.74 | N |
| ATOM | 2758 | CA | LYS | C | 491 | 17.183 | 22.911 | 47.387 | 1.00 | 73.62 | C |
| ATOM | 2759 | C | LYS | C | 491 | 18.264 | 22.538 | 48.396 | 1.00 | 75.55 | C |
| ATOM | 2760 | O | LYS | C | 491 | 18.383 | 21.376 | 48.785 | 1.00 | 75.66 | O |
| ATOM | 2761 | CB | LYS | C | 491 | 16.755 | 21.681 | 46.603 | 1.00 | 72.92 | C |
| ATOM | 2762 | N | GLU | C | 492 | 19.042 | 23.535 | 48.814 | 1.00 | 78.00 | N |
| ATOM | 2763 | CA | GLU | C | 492 | 20.121 | 23.351 | 49.782 | 1.00 | 79.84 | C |
| ATOM | 2764 | C | GLU | C | 492 | 21.012 | 24.589 | 49.802 | 1.00 | 81.20 | C |
| ATOM | 2765 | O | GLU | C | 492 | 22.126 | 24.564 | 49.283 | 1.00 | 81.52 | O |
| ATOM | 2766 | CB | GLU | C | 492 | 20.951 | 22.119 | 49.425 | 1.00 | 80.18 | C |
| ATOM | 2767 | N | ASN | C | 493 | 20.518 | 25.669 | 50.401 | 1.00 | 83.14 | N |
| ATOM | 2768 | CA | ASN | C | 493 | 21.277 | 26.916 | 50.481 | 1.00 | 84.85 | C |
| ATOM | 2769 | C | ASN | C | 493 | 21.948 | 27.097 | 51.845 | 1.00 | 86.58 | C |
| ATOM | 2770 | O | ASN | C | 493 | 23.088 | 26.670 | 52.050 | 1.00 | 86.98 | O |
| ATOM | 2771 | CB | ASN | C | 493 | 20.362 | 28.100 | 50.190 | 1.00 | 84.61 | C |
| ATOM | 2772 | N | SER | C | 494 | 21.238 | 27.736 | 52.772 | 1.00 | 88.38 | N |
| ATOM | 2773 | CA | SER | C | 494 | 21.759 | 27.980 | 54.116 | 1.00 | 89.76 | C |
| ATOM | 2774 | C | SER | C | 494 | 20.629 | 27.992 | 55.145 | 1.00 | 90.86 | C |
| ATOM | 2775 | O | SER | C | 494 | 20.509 | 27.076 | 55.961 | 1.00 | 91.08 | O |
| ATOM | 2776 | CB | SER | C | 494 | 22.509 | 29.309 | 54.150 | 1.00 | 89.25 | C |
| ATOM | 2777 | N | SER | C | 495 | 19.808 | 29.037 | 55.095 | 1.00 | 91.91 | N |
| ATOM | 2778 | CA | SER | C | 495 | 18.678 | 29.195 | 56.006 | 1.00 | 92.32 | C |
| ATOM | 2779 | C | SER | C | 495 | 17.985 | 30.529 | 55.729 | 1.00 | 92.84 | C |
| ATOM | 2780 | O | SER | C | 495 | 16.815 | 30.720 | 56.075 | 1.00 | 92.80 | O |
| ATOM | 2781 | CB | SER | C | 495 | 19.159 | 29.141 | 57.455 | 1.00 | 91.90 | C |
| ATOM | 2782 | N | LYS | C | 496 | 18.718 | 31.445 | 55.102 | 1.00 | 92.97 | N |
| ATOM | 2783 | CA | LYS | C | 496 | 18.194 | 32.766 | 54.770 | 1.00 | 92.97 | C |
| ATOM | 2784 | C | LYS | C | 496 | 17.581 | 32.773 | 53.372 | 1.00 | 92.72 | C |
| ATOM | 2785 | O | LYS | C | 496 | 18.022 | 33.512 | 52.488 | 1.00 | 92.28 | O |
| ATOM | 2786 | CB | LYS | C | 496 | 19.309 | 33.808 | 54.859 | 1.00 | 93.19 | C |
| ATOM | 2787 | N | ASP | C | 497 | 16.563 | 31.939 | 53.183 | 1.00 | 92.13 | N |
| ATOM | 2788 | CA | ASP | C | 497 | 15.865 | 31.833 | 51.908 | 1.00 | 92.02 | C |
| ATOM | 2789 | C | ASP | C | 497 | 14.435 | 31.359 | 52.156 | 1.00 | 92.20 | C |
| ATOM | 2790 | O | ASP | C | 497 | 14.203 | 30.458 | 52.964 | 1.00 | 92.35 | O |
| ATOM | 2791 | CB | ASP | C | 497 | 16.593 | 30.858 | 50.989 | 1.00 | 91.57 | C |
| ATOM | 2792 | N | LEU | C | 498 | 13.478 | 31.970 | 51.464 | 1.00 | 92.05 | N |
| ATOM | 2793 | CA | LEU | C | 498 | 12.075 | 31.605 | 51.622 | 1.00 | 91.73 | C |
| ATOM | 2794 | C | LEU | C | 498 | 11.645 | 30.576 | 50.580 | 1.00 | 91.81 | C |
| ATOM | 2795 | O | LEU | C | 498 | 11.058 | 30.924 | 49.555 | 1.00 | 92.52 | O |
| ATOM | 2796 | CB | LEU | C | 498 | 11.198 | 32.850 | 51.521 | 1.00 | 91.53 | C |
| ATOM | 2797 | N | LYS | C | 499 | 11.941 | 29.308 | 50.845 | 1.00 | 91.61 | N |
| ATOM | 2798 | CA | LYS | C | 499 | 11.579 | 28.233 | 49.930 | 1.00 | 91.43 | C |
| ATOM | 2799 | C | LYS | C | 499 | 10.117 | 27.847 | 50.133 | 1.00 | 91.66 | C |
| ATOM | 2800 | O | LYS | C | 499 | 9.603 | 26.949 | 49.466 | 1.00 | 91.71 | O |
| ATOM | 2801 | CB | LYS | C | 499 | 12.478 | 27.025 | 50.159 | 1.00 | 90.82 | C |
| ATOM | 2802 | N | LYS | C | 500 | 9.455 | 28.538 | 51.056 | 1.00 | 92.00 | N |
| ATOM | 2803 | CA | LYS | C | 500 | 8.050 | 28.282 | 51.362 | 1.00 | 92.42 | C |
| ATOM | 2804 | C | LYS | C | 500 | 7.141 | 28.565 | 50.165 | 1.00 | 92.65 | C |
| ATOM | 2805 | O | LYS | C | 500 | 7.499 | 28.274 | 49.020 | 1.00 | 93.28 | O |
| ATOM | 2806 | CB | LYS | C | 500 | 7.618 | 29.126 | 52.559 | 1.00 | 92.24 | C |
| ATOM | 2807 | N | SER | C | 501 | 5.968 | 29.133 | 50.439 | 1.00 | 92.35 | N |
| ATOM | 2808 | CA | SER | C | 501 | 4.985 | 29.453 | 49.404 | 1.00 | 91.78 | C |
| ATOM | 2809 | C | SER | C | 501 | 4.381 | 28.168 | 48.836 | 1.00 | 91.55 | C |
| ATOM | 2810 | O | SER | C | 501 | 3.246 | 28.167 | 48.348 | 1.00 | 90.99 | O |
| ATOM | 2811 | CB | SER | C | 501 | 5.637 | 30.273 | 48.284 | 1.00 | 91.58 | C |
| ATOM | 2812 | N | PHE | C | 502 | 5.149 | 27.081 | 48.917 | 1.00 | 91.35 | N |
| ATOM | 2813 | CA | PHE | C | 502 | 4.736 | 25.767 | 48.425 | 1.00 | 90.43 | C |
| ATOM | 2814 | C | PHE | C | 502 | 4.320 | 25.841 | 46.961 | 1.00 | 89.44 | C |
| ATOM | 2815 | O | PHE | C | 502 | 5.155 | 25.771 | 46.058 | 1.00 | 89.03 | O |
| ATOM | 2816 | CB | PHE | C | 502 | 3.584 | 25.227 | 49.274 | 1.00 | 90.98 | C |
| ATOM | 2817 | N | LYS | C | 503 | 3.019 | 25.976 | 46.740 | 1.00 | 88.39 | N |
| ATOM | 2818 | CA | LYS | C | 503 | 2.464 | 26.081 | 45.400 | 1.00 | 87.51 | C |
| ATOM | 2819 | C | LYS | C | 503 | 1.156 | 26.860 | 45.503 | 1.00 | 86.08 | C |
| ATOM | 2820 | O | LYS | C | 503 | 0.238 | 26.451 | 46.220 | 1.00 | 86.05 | O |
| ATOM | 2821 | CB | LYS | C | 503 | 2.202 | 24.691 | 44.814 | 1.00 | 88.05 | C |
| ATOM | 2822 | CG | LYS | C | 503 | 1.839 | 24.711 | 43.336 | 1.00 | 88.57 | C |
| ATOM | 2823 | CD | LYS | C | 503 | 1.419 | 23.338 | 42.832 | 1.00 | 88.37 | C |
| ATOM | 2824 | CE | LYS | C | 503 | 0.106 | 22.899 | 43.452 | 1.00 | 87.87 | C |
| ATOM | 2825 | NZ | LYS | C | 503 | −0.417 | 21.679 | 42.790 | 1.00 | 87.78 | N |

TABLE 4-continued

Stem Cell Factor Dimer

| ATOM | 2826 | N | SER | C | 504 | 1.083 | 27.987 | 44.800 | 1.00 | 83.62 | N |
|---|---|---|---|---|---|---|---|---|---|---|---|
| ATOM | 2827 | CA | SER | C | 504 | −0.109 | 28.826 | 44.821 | 1.00 | 80.69 | C |
| ATOM | 2828 | C | SER | C | 504 | −0.033 | 30.080 | 43.944 | 1.00 | 77.49 | C |
| ATOM | 2829 | O | SER | C | 504 | −0.748 | 31.050 | 44.190 | 1.00 | 78.09 | O |
| ATOM | 2830 | CB | SER | C | 504 | −0.423 | 29.238 | 46.266 | 1.00 | 82.35 | C |
| ATOM | 2831 | OG | SER | C | 504 | 0.708 | 29.822 | 46.895 | 1.00 | 83.35 | O |
| ATOM | 2832 | N | PRO | C | 505 | 0.830 | 30.087 | 42.914 | 1.00 | 73.98 | N |
| ATOM | 2833 | CA | PRO | C | 505 | 0.891 | 31.293 | 42.082 | 1.00 | 70.42 | C |
| ATOM | 2834 | C | PRO | C | 505 | −0.127 | 31.246 | 40.945 | 1.00 | 66.52 | C |
| ATOM | 2835 | O | PRO | C | 505 | −0.414 | 30.176 | 40.411 | 1.00 | 66.27 | O |
| ATOM | 2836 | CB | PRO | C | 505 | 2.326 | 31.277 | 41.581 | 1.00 | 70.47 | C |
| ATOM | 2837 | CG | PRO | C | 505 | 2.546 | 29.816 | 41.349 | 1.00 | 73.11 | C |
| ATOM | 2838 | CD | PRO | C | 505 | 1.926 | 29.160 | 42.571 | 1.00 | 73.18 | C |
| ATOM | 2839 | N | GLU | C | 506 | −0.672 | 32.402 | 40.579 | 1.00 | 62.89 | N |
| ATOM | 2840 | CA | GLU | C | 506 | −1.659 | 32.459 | 39.504 | 1.00 | 60.06 | C |
| ATOM | 2841 | C | GLU | C | 506 | −0.999 | 32.543 | 38.125 | 1.00 | 56.43 | C |
| ATOM | 2842 | O | GLU | C | 506 | −0.067 | 33.321 | 37.909 | 1.00 | 53.61 | O |
| ATOM | 2843 | CB | GLU | C | 506 | −2.597 | 33.657 | 39.686 | 1.00 | 60.85 | C |
| ATOM | 2844 | CG | GLU | C | 506 | −2.055 | 34.963 | 39.137 | 1.00 | 63.66 | C |
| ATOM | 2845 | CD | GLU | C | 506 | −3.083 | 36.074 | 39.155 | 1.00 | 66.22 | C |
| ATOM | 2846 | OE1 | GLU | C | 506 | −4.181 | 35.889 | 38.591 | 1.00 | 66.44 | O |
| ATOM | 2847 | OE2 | GLU | C | 506 | −2.791 | 37.141 | 39.732 | 1.00 | 69.61 | O |
| ATOM | 2848 | N | PRO | C | 507 | −1.483 | 31.730 | 37.174 | 1.00 | 53.50 | N |
| ATOM | 2849 | CA | PRO | C | 507 | −0.959 | 31.696 | 35.808 | 1.00 | 50.59 | C |
| ATOM | 2850 | C | PRO | C | 507 | −1.172 | 33.025 | 35.096 | 1.00 | 47.75 | C |
| ATOM | 2851 | O | PRO | C | 507 | −2.249 | 33.617 | 35.170 | 1.00 | 47.48 | O |
| ATOM | 2852 | CB | PRO | C | 507 | −1.762 | 30.569 | 35.155 | 1.00 | 51.01 | C |
| ATOM | 2853 | CG | PRO | C | 507 | −2.109 | 29.678 | 36.309 | 1.00 | 52.55 | C |
| ATOM | 2854 | CD | PRO | C | 507 | −2.491 | 30.672 | 37.371 | 1.00 | 52.89 | C |
| ATOM | 2855 | N | ARG | C | 508 | −0.142 | 33.497 | 34.408 | 1.00 | 43.60 | N |
| ATOM | 2856 | CA | ARG | C | 508 | −0.245 | 34.750 | 33.675 | 1.00 | 39.58 | C |
| ATOM | 2857 | C | ARG | C | 508 | 0.357 | 34.575 | 32.294 | 1.00 | 35.30 | C |
| ATOM | 2858 | O | ARG | C | 508 | 1.231 | 33.738 | 32.102 | 1.00 | 31.03 | O |
| ATOM | 2859 | CB | ARG | C | 508 | 0.471 | 35.870 | 34.427 | 1.00 | 40.31 | C |
| ATOM | 2860 | CG | ARG | C | 508 | −0.213 | 36.255 | 35.716 | 1.00 | 44.11 | C |
| ATOM | 2861 | CD | ARG | C | 508 | 0.431 | 37.486 | 36.326 | 1.00 | 48.76 | C |
| ATOM | 2862 | NE | ARG | C | 508 | 0.731 | 38.514 | 35.328 | 1.00 | 47.99 | N |
| ATOM | 2863 | CZ | ARG | C | 508 | 1.181 | 39.729 | 35.631 | 1.00 | 50.50 | C |
| ATOM | 2864 | NH1 | ARG | C | 508 | 1.371 | 40.059 | 36.904 | 1.00 | 50.11 | N |
| ATOM | 2865 | NH2 | ARG | C | 508 | 1.457 | 40.609 | 34.670 | 1.00 | 49.02 | N |
| ATOM | 2866 | N | LEU | C | 509 | −0.126 | 35.362 | 31.339 | 1.00 | 32.29 | N |
| ATOM | 2867 | CA | LEU | C | 509 | 0.359 | 35.294 | 29.965 | 1.00 | 31.11 | C |
| ATOM | 2868 | C | LEU | C | 509 | 1.333 | 36.427 | 29.663 | 1.00 | 28.63 | C |
| ATOM | 2869 | O | LEU | C | 509 | 1.058 | 37.603 | 29.941 | 1.00 | 24.90 | O |
| ATOM | 2870 | CB | LEU | C | 509 | −0.810 | 35.359 | 28.978 | 1.00 | 31.46 | C |
| ATOM | 2871 | CG | LEU | C | 509 | −1.865 | 34.252 | 29.051 | 1.00 | 34.91 | C |
| ATOM | 2872 | CD1 | LEU | C | 509 | −2.915 | 34.504 | 27.975 | 1.00 | 34.69 | C |
| ATOM | 2873 | CD2 | LEU | C | 509 | −1.217 | 32.878 | 28.873 | 1.00 | 33.71 | C |
| ATOM | 2874 | N | PHE | C | 510 | 2.471 | 36.058 | 29.085 | 1.00 | 24.62 | N |
| ATOM | 2875 | CA | PHE | C | 510 | 3.498 | 37.025 | 28.742 | 1.00 | 22.42 | C |
| ATOM | 2876 | C | PHE | C | 510 | 3.965 | 36.840 | 27.304 | 1.00 | 22.59 | C |
| ATOM | 2877 | O | PHE | C | 510 | 3.922 | 35.730 | 26.756 | 1.00 | 21.95 | O |
| ATOM | 2878 | CB | PHE | C | 510 | 4.716 | 36.862 | 29.659 | 1.00 | 20.32 | C |
| ATOM | 2879 | CG | PHE | C | 510 | 4.406 | 36.967 | 31.114 | 1.00 | 19.85 | C |
| ATOM | 2880 | CD1 | PHE | C | 510 | 3.987 | 35.850 | 31.834 | 1.00 | 21.32 | C |
| ATOM | 2881 | CD2 | PHE | C | 510 | 4.546 | 38.188 | 31.782 | 1.00 | 24.49 | C |
| ATOM | 2882 | CE1 | PHE | C | 510 | 3.714 | 35.940 | 33.195 | 1.00 | 19.00 | C |
| ATOM | 2883 | CE2 | PHE | C | 510 | 4.273 | 38.294 | 33.153 | 1.00 | 23.56 | C |
| ATOM | 2884 | CZ | PHE | C | 510 | 3.857 | 37.162 | 33.859 | 1.00 | 24.09 | C |
| ATOM | 2885 | N | THR | C | 511 | 4.408 | 37.933 | 26.691 | 1.00 | 21.70 | N |
| ATOM | 2886 | CA | THR | C | 511 | 4.946 | 37.873 | 25.338 | 1.00 | 20.39 | C |
| ATOM | 2887 | C | THR | C | 511 | 6.326 | 37.241 | 25.515 | 1.00 | 18.81 | C |
| ATOM | 2888 | O | THR | C | 511 | 6.872 | 37.228 | 26.620 | 1.00 | 18.27 | O |
| ATOM | 2889 | CB | THR | C | 511 | 5.156 | 39.274 | 24.770 | 1.00 | 21.47 | C |
| ATOM | 2890 | OG1 | THR | C | 511 | 6.103 | 39.966 | 25.597 | 1.00 | 25.55 | O |
| ATOM | 2891 | CG2 | THR | C | 511 | 3.841 | 40.058 | 24.746 | 1.00 | 23.54 | C |
| ATOM | 2892 | N | PRO | C | 512 | 6.912 | 36.704 | 24.440 | 1.00 | 20.33 | N |
| ATOM | 2893 | CA | PRO | C | 512 | 8.240 | 36.102 | 24.617 | 1.00 | 21.52 | C |
| ATOM | 2894 | C | PRO | C | 512 | 9.239 | 37.093 | 25.237 | 1.00 | 22.84 | C |
| ATOM | 2895 | O | PRO | C | 512 | 10.008 | 36.750 | 26.134 | 1.00 | 23.45 | O |
| ATOM | 2896 | CB | PRO | C | 512 | 8.607 | 35.689 | 23.198 | 1.00 | 20.44 | C |
| ATOM | 2897 | CG | PRO | C | 512 | 7.223 | 35.291 | 22.624 | 1.00 | 18.41 | C |
| ATOM | 2898 | CD | PRO | C | 512 | 6.364 | 36.422 | 23.098 | 1.00 | 19.58 | C |
| ATOM | 2899 | N | GLU | C | 513 | 9.199 | 38.330 | 24.770 | 1.00 | 24.25 | N |
| ATOM | 2900 | CA | GLU | C | 513 | 10.091 | 39.378 | 25.261 | 1.00 | 26.40 | C |
| ATOM | 2901 | C | GLU | C | 513 | 9.920 | 39.624 | 26.762 | 1.00 | 26.10 | C |
| ATOM | 2902 | O | GLU | C | 513 | 10.906 | 39.771 | 27.500 | 1.00 | 25.11 | C |

TABLE 4-continued

Stem Cell Factor Dimer

| ATOM | 2903 | CB | GLU | C | 513 | 9.822 | 40.669 | 24.489 | 1.00 | 29.08 | C |
| ATOM | 2904 | CG | GLU | C | 513 | 10.850 | 41.753 | 24.712 | 1.00 | 35.84 | C |
| ATOM | 2905 | CD | GLU | C | 513 | 10.469 | 43.040 | 24.011 | 1.00 | 41.11 | C |
| ATOM | 2906 | OE1 | GLU | C | 513 | 10.021 | 42.961 | 22.841 | 1.00 | 40.55 | C |
| ATOM | 2907 | OE2 | GLU | C | 513 | 10.623 | 44.121 | 24.626 | 1.00 | 43.50 | O |
| ATOM | 2908 | N | GLU | C | 514 | 8.664 | 39.682 | 27.202 | 1.00 | 26.40 | N |
| ATOM | 2909 | CA | GLU | C | 514 | 8.324 | 39.886 | 28.606 | 1.00 | 25.38 | C |
| ATOM | 2910 | C | GLU | C | 514 | 8.777 | 38.681 | 29.433 | 1.00 | 23.79 | C |
| ATOM | 2911 | O | GLU | C | 514 | 9.386 | 38.831 | 30.501 | 1.00 | 23.81 | O |
| ATOM | 2912 | CB | GLU | C | 514 | 6.807 | 40.069 | 28.755 | 1.00 | 29.33 | C |
| ATOM | 2913 | CG | GLU | C | 514 | 6.315 | 41.527 | 28.727 | 1.00 | 33.14 | C |
| ATOM | 2914 | CD | GLU | C | 514 | 4.861 | 41.672 | 28.261 | 1.00 | 33.03 | C |
| ATOM | 2915 | OE1 | GLU | C | 514 | 4.007 | 40.829 | 28.611 | 1.00 | 31.80 | O |
| ATOM | 2916 | OE2 | GLU | C | 514 | 4.568 | 42.649 | 27.542 | 1.00 | 38.85 | O |
| ATOM | 2917 | N | PHE | C | 515 | 8.479 | 37.484 | 28.941 | 1.00 | 21.59 | N |
| ATOM | 2918 | CA | PHE | C | 515 | 8.859 | 36.270 | 29.660 | 1.00 | 19.64 | C |
| ATOM | 2919 | C | PHE | C | 515 | 10.360 | 36.198 | 29.901 | 1.00 | 17.78 | C |
| ATOM | 2920 | O | PHE | C | 515 | 10.808 | 35.987 | 31.026 | 1.00 | 17.87 | O |
| ATOM | 2921 | CB | PHE | C | 515 | 8.415 | 35.018 | 28.890 | 1.00 | 18.51 | C |
| ATOM | 2922 | CG | PHE | C | 515 | 8.822 | 33.730 | 29.550 | 1.00 | 20.90 | C |
| ATOM | 2923 | CD1 | PHE | C | 515 | 8.068 | 33.197 | 30.596 | 1.00 | 19.79 | C |
| ATOM | 2924 | CD2 | PHE | C | 515 | 9.972 | 33.053 | 29.141 | 1.00 | 21.28 | C |
| ATOM | 2925 | CE1 | PHE | C | 515 | 8.445 | 32.010 | 31.226 | 1.00 | 16.33 | C |
| ATOM | 2926 | CE2 | PHE | C | 515 | 10.361 | 31.859 | 29.766 | 1.00 | 21.22 | C |
| ATOM | 2927 | CZ | PHE | C | 515 | 9.597 | 31.339 | 30.807 | 1.00 | 20.73 | C |
| ATOM | 2928 | N | PHE | C | 516 | 11.151 | 36.381 | 28.852 | 1.00 | 18.00 | N |
| ATOM | 2929 | CA | PHE | C | 516 | 12.593 | 36.296 | 29.035 | 1.00 | 20.74 | C |
| ATOM | 2930 | C | PHE | C | 516 | 13.251 | 37.427 | 29.813 | 1.00 | 22.35 | C |
| ATOM | 2931 | O | PHE | C | 516 | 14.369 | 37.273 | 30.288 | 1.00 | 23.89 | O |
| ATOM | 2932 | CB | PHE | C | 516 | 13.272 | 36.053 | 27.692 | 1.00 | 19.59 | C |
| ATOM | 2933 | CG | PHE | C | 516 | 13.052 | 34.667 | 27.182 | 1.00 | 21.15 | C |
| ATOM | 2934 | CD1 | PHE | C | 516 | 12.038 | 34.398 | 26.259 | 1.00 | 19.55 | C |
| ATOM | 2935 | CD2 | PHE | C | 516 | 13.795 | 33.603 | 27.702 | 1.00 | 21.51 | C |
| ATOM | 2936 | CE1 | PHE | C | 516 | 11.766 | 33.090 | 25.862 | 1.00 | 22.18 | C |
| ATOM | 2937 | CE2 | PHE | C | 516 | 13.533 | 32.287 | 27.313 | 1.00 | 21.46 | C |
| ATOM | 2938 | CZ | PHE | C | 516 | 12.516 | 32.027 | 26.390 | 1.00 | 18.99 | C |
| ATOM | 2939 | N | ARG | C | 517 | 12.548 | 38.545 | 29.972 | 1.00 | 25.99 | N |
| ATOM | 2940 | CA | ARG | C | 517 | 13.058 | 39.674 | 30.756 | 1.00 | 27.38 | C |
| ATOM | 2941 | C | ARG | C | 517 | 12.968 | 39.224 | 32.218 | 1.00 | 27.00 | C |
| ATOM | 2942 | O | ARG | C | 517 | 13.789 | 39.594 | 33.061 | 1.00 | 27.39 | O |
| ATOM | 2943 | CB | ARG | C | 517 | 12.187 | 40.924 | 30.547 | 1.00 | 25.75 | C |
| ATOM | 2944 | CG | ARG | C | 517 | 12.627 | 42.145 | 31.360 | 1.00 | 30.62 | C |
| ATOM | 2945 | CD | ARG | C | 517 | 11.810 | 43.412 | 31.008 | 1.00 | 32.07 | C |
| ATOM | 2946 | NE | ARG | C | 517 | 11.927 | 43.761 | 29.592 | 1.00 | 37.76 | N |
| ATOM | 2947 | CZ | ARG | C | 517 | 10.896 | 43.869 | 28.754 | 1.00 | 40.99 | C |
| ATOM | 2948 | NH1 | ARG | C | 517 | 9.658 | 43.663 | 29.188 | 1.00 | 41.55 | N |
| ATOM | 2949 | NH2 | ARG | C | 517 | 11.100 | 44.161 | 27.473 | 1.00 | 41.63 | N |
| ATOM | 2950 | N | ILE | C | 518 | 11.948 | 38.424 | 32.509 | 1.00 | 25.97 | N |
| ATOM | 2951 | CA | ILE | C | 518 | 11.752 | 37.897 | 33.850 | 1.00 | 22.48 | C |
| ATOM | 2952 | C | ILE | C | 518 | 12.750 | 36.756 | 34.045 | 1.00 | 22.93 | C |
| ATOM | 2953 | O | ILE | C | 518 | 13.337 | 36.616 | 35.111 | 1.00 | 24.47 | O |
| ATOM | 2954 | CB | ILE | C | 518 | 10.314 | 37.394 | 34.020 | 1.00 | 22.76 | C |
| ATOM | 2955 | CG1 | ILE | C | 518 | 9.360 | 38.592 | 34.014 | 1.00 | 21.65 | C |
| ATOM | 2956 | CG2 | ILE | C | 518 | 10.178 | 36.567 | 35.298 | 1.00 | 17.95 | C |
| ATOM | 2957 | CD1 | ILE | C | 518 | 7.884 | 38.197 | 33.877 | 1.00 | 23.44 | C |
| ATOM | 2958 | N | PHE | C | 519 | 12.938 | 35.951 | 33.004 | 1.00 | 22.45 | N |
| ATOM | 2959 | CA | PHE | C | 519 | 13.895 | 34.848 | 33.032 | 1.00 | 23.48 | C |
| ATOM | 2960 | C | PHE | C | 519 | 15.262 | 35.437 | 33.393 | 1.00 | 26.08 | C |
| ATOM | 2961 | O | PHE | C | 519 | 15.886 | 35.047 | 34.388 | 1.00 | 26.78 | O |
| ATOM | 2962 | CB | PHE | C | 519 | 13.969 | 34.194 | 31.647 | 1.00 | 22.04 | C |
| ATOM | 2963 | CG | PHE | C | 519 | 15.114 | 33.228 | 31.479 | 1.00 | 23.71 | C |
| ATOM | 2964 | CD1 | PHE | C | 519 | 14.985 | 31.889 | 31.864 | 1.00 | 23.22 | C |
| ATOM | 2965 | CD2 | PHE | C | 519 | 16.326 | 33.657 | 30.938 | 1.00 | 21.19 | C |
| ATOM | 2966 | CE1 | PHE | C | 519 | 16.049 | 30.998 | 31.713 | 1.00 | 21.76 | C |
| ATOM | 2967 | CE2 | PHE | C | 519 | 17.397 | 32.779 | 30.783 | 1.00 | 21.63 | C |
| ATOM | 2968 | CZ | PHE | C | 519 | 17.261 | 31.443 | 31.171 | 1.00 | 23.53 | C |
| ATOM | 2969 | N | ASN | C | 520 | 15.712 | 36.388 | 32.581 | 1.00 | 26.37 | N |
| ATOM | 2970 | CA | ASN | C | 520 | 17.002 | 37.043 | 32.784 | 1.00 | 28.23 | C |
| ATOM | 2971 | C | ASN | C | 520 | 17.169 | 37.639 | 34.165 | 1.00 | 29.17 | C |
| ATOM | 2972 | O | ASN | C | 520 | 18.227 | 37.507 | 34.788 | 1.00 | 30.03 | O |
| ATOM | 2973 | CB | ASN | C | 520 | 17.195 | 38.183 | 31.786 | 1.00 | 26.87 | C |
| ATOM | 2974 | CG | ASN | C | 520 | 17.631 | 37.711 | 30.442 | 1.00 | 26.27 | C |
| ATOM | 2975 | OD1 | ASN | C | 520 | 17.659 | 38.489 | 29.495 | 1.00 | 32.70 | O |
| ATOM | 2976 | ND2 | ASN | C | 520 | 17.975 | 36.435 | 30.335 | 1.00 | 26.28 | N |
| ATOM | 2977 | N | ARG | C | 521 | 16.141 | 38.338 | 34.623 | 1.00 | 29.19 | N |
| ATOM | 2978 | CA | ARG | C | 521 | 16.209 | 38.973 | 35.926 | 1.00 | 32.82 | C |
| ATOM | 2979 | C | ARG | C | 521 | 16.368 | 37.912 | 37.014 | 1.00 | 33.74 | C |

TABLE 4-continued

Stem Cell Factor Dimer

| ATOM | 2980 | O | ARG | C | 521 | 17.122 | 38.108 | 37.974 | 1.00 | 33.01 | O |
|---|---|---|---|---|---|---|---|---|---|---|---|
| ATOM | 2981 | CB | ARG | C | 521 | 14.958 | 39.820 | 36.161 | 1.00 | 33.12 | C |
| ATOM | 2982 | CG | ARG | C | 521 | 15.070 | 40.788 | 37.325 | 1.00 | 39.00 | C |
| ATOM | 2983 | CD | ARG | C | 521 | 13.914 | 41.782 | 37.299 | 1.00 | 45.11 | C |
| ATOM | 2984 | NE | ARG | C | 521 | 13.822 | 42.459 | 36.003 | 1.00 | 51.59 | N |
| ATOM | 2985 | CZ | ARG | C | 521 | 14.702 | 43.352 | 35.547 | 1.00 | 53.90 | C |
| ATOM | 2986 | NH1 | ARG | C | 521 | 15.755 | 43.697 | 36.285 | 1.00 | 53.08 | N |
| ATOM | 2987 | NH2 | ARG | C | 521 | 14.535 | 43.892 | 34.341 | 1.00 | 52.06 | N |
| ATOM | 2988 | N | SER | C | 522 | 15.681 | 36.781 | 36.848 | 1.00 | 33.44 | N |
| ATOM | 2989 | CA | SER | C | 522 | 15.759 | 35.702 | 37.825 | 1.00 | 34.99 | C |
| ATOM | 2990 | C | SER | C | 522 | 17.150 | 35.074 | 37.814 | 1.00 | 38.06 | C |
| ATOM | 2991 | O | SER | C | 522 | 17.710 | 34.800 | 38.872 | 1.00 | 36.91 | O |
| ATOM | 2992 | CB | SER | C | 522 | 14.694 | 34.633 | 37.539 | 1.00 | 33.27 | C |
| ATOM | 2993 | OG | SER | C | 522 | 13.387 | 35.186 | 37.572 | 1.00 | 28.25 | O |
| ATOM | 2994 | N | ILE | C | 523 | 17.706 | 34.849 | 36.623 | 1.00 | 41.24 | N |
| ATOM | 2995 | CA | ILE | C | 523 | 19.042 | 34.265 | 36.513 | 1.00 | 44.88 | C |
| ATOM | 2996 | C | ILE | C | 523 | 20.053 | 35.232 | 37.132 | 1.00 | 47.92 | C |
| ATOM | 2997 | O | ILE | C | 523 | 20.921 | 34.824 | 37.905 | 1.00 | 46.65 | O |
| ATOM | 2998 | CB | ILE | C | 523 | 19.420 | 33.959 | 35.024 | 1.00 | 44.62 | C |
| ATOM | 2999 | CG1 | ILE | C | 523 | 19.259 | 32.462 | 34.740 | 1.00 | 43.86 | C |
| ATOM | 3000 | CG2 | ILE | C | 523 | 20.874 | 34.354 | 34.735 | 1.00 | 43.36 | C |
| ATOM | 3001 | CD1 | ILE | C | 523 | 17.872 | 31.937 | 34.937 | 1.00 | 43.79 | C |
| ATOM | 3002 | N | ASP | C | 524 | 19.927 | 36.512 | 36.797 | 1.00 | 51.02 | N |
| ATOM | 3003 | CA | ASP | C | 524 | 20.815 | 37.536 | 37.336 | 1.00 | 56.14 | C |
| ATOM | 3004 | C | ASP | C | 524 | 20.646 | 37.669 | 38.847 | 1.00 | 58.19 | C |
| ATOM | 3005 | O | ASP | C | 524 | 21.623 | 37.653 | 39.595 | 1.00 | 58.67 | O |
| ATOM | 3006 | CB | ASP | C | 524 | 20.532 | 38.889 | 36.675 | 1.00 | 57.90 | C |
| ATOM | 3007 | CG | ASP | C | 524 | 21.483 | 39.191 | 35.524 | 1.00 | 61.27 | C |
| ATOM | 3008 | OD1 | ASP | C | 524 | 21.759 | 38.275 | 34.717 | 1.00 | 61.38 | O |
| ATOM | 3009 | OD2 | ASP | C | 524 | 21.945 | 40.351 | 35.422 | 1.00 | 62.25 | O |
| ATOM | 3010 | N | ALA | C | 525 | 19.398 | 37.800 | 39.287 | 1.00 | 61.09 | N |
| ATOM | 3011 | CA | ALA | C | 525 | 19.091 | 37.949 | 40.705 | 1.00 | 63.58 | C |
| ATOM | 3012 | C | ALA | C | 525 | 19.268 | 36.637 | 41.449 | 1.00 | 65.20 | C |
| ATOM | 3013 | O | ALA | C | 525 | 18.631 | 36.402 | 42.475 | 1.00 | 65.19 | O |
| ATOM | 3014 | CB | ALA | C | 525 | 17.667 | 38.458 | 40.880 | 1.00 | 64.99 | C |
| ATOM | 3015 | N | PHE | C | 526 | 20.125 | 35.777 | 40.915 | 1.00 | 67.33 | N |
| ATOM | 3016 | CA | PHE | C | 526 | 20.404 | 34.492 | 41.535 | 1.00 | 69.35 | C |
| ATOM | 3017 | C | PHE | C | 526 | 21.797 | 34.596 | 42.141 | 1.00 | 70.48 | C |
| ATOM | 3018 | O | PHE | C | 526 | 22.145 | 33.875 | 43.076 | 1.00 | 71.00 | O |
| ATOM | 3019 | CB | PHE | C | 526 | 20.348 | 33.377 | 40.490 | 1.00 | 69.78 | C |
| ATOM | 3020 | CG | PHE | C | 526 | 20.536 | 32.011 | 41.062 | 1.00 | 70.50 | C |
| ATOM | 3021 | CD1 | PHE | C | 526 | 21.810 | 31.529 | 41.341 | 1.00 | 70.53 | C |
| ATOM | 3022 | CD2 | PHE | C | 526 | 19.436 | 31.218 | 41.367 | 1.00 | 71.41 | C |
| ATOM | 3023 | CE1 | PHE | C | 526 | 21.987 | 30.276 | 41.920 | 1.00 | 70.93 | C |
| ATOM | 3024 | CE2 | PHE | C | 526 | 19.602 | 29.962 | 41.946 | 1.00 | 71.39 | C |
| ATOM | 3025 | CZ | PHE | C | 526 | 20.881 | 29.491 | 42.223 | 1.00 | 71.33 | C |
| ATOM | 3026 | N | LYS | C | 527 | 22.577 | 35.527 | 41.603 | 1.00 | 71.19 | N |
| ATOM | 3027 | CA | LYS | C | 527 | 23.938 | 35.784 | 42.056 | 1.00 | 71.55 | C |
| ATOM | 3028 | C | LYS | C | 527 | 24.080 | 37.277 | 42.371 | 1.00 | 70.63 | C |
| ATOM | 3029 | O | LYS | C | 527 | 23.788 | 37.731 | 43.481 | 1.00 | 70.51 | O |
| ATOM | 3030 | CB | LYS | C | 527 | 24.923 | 35.378 | 40.955 | 1.00 | 72.89 | C |
| ATOM | 3031 | CG | LYS | C | 527 | 24.520 | 35.863 | 39.557 | 1.00 | 74.66 | C |
| ATOM | 3032 | CD | LYS | C | 527 | 25.500 | 35.400 | 38.482 | 1.00 | 75.46 | C |
| ATOM | 3033 | CE | LYS | C | 527 | 25.039 | 35.801 | 37.080 | 1.00 | 75.93 | C |
| ATOM | 3034 | NZ | LYS | C | 527 | 24.995 | 37.279 | 36.867 | 1.00 | 75.87 | N |
| ATOM | 3035 | N | ASP | C | 528 | 24.539 | 38.015 | 41.366 | 1.00 | 69.13 | N |
| ATOM | 3036 | CA | ASP | C | 528 | 24.734 | 39.461 | 41.396 | 1.00 | 68.02 | C |
| ATOM | 3037 | C | ASP | C | 528 | 24.981 | 40.243 | 42.687 | 1.00 | 66.87 | C |
| ATOM | 3038 | O | ASP | C | 528 | 26.018 | 40.086 | 43.333 | 1.00 | 66.97 | O |
| ATOM | 3039 | CB | ASP | C | 528 | 23.588 | 40.129 | 40.631 | 1.00 | 68.86 | C |
| ATOM | 3040 | CG | ASP | C | 528 | 23.707 | 39.940 | 39.135 | 1.00 | 70.61 | C |
| ATOM | 3041 | OD1 | ASP | C | 528 | 23.897 | 38.787 | 38.697 | 1.00 | 73.33 | O |
| ATOM | 3042 | OD2 | ASP | C | 528 | 23.611 | 40.941 | 38.394 | 1.00 | 72.34 | O |
| ATOM | 3043 | N | PHE | C | 529 | 24.018 | 41.092 | 43.044 | 1.00 | 65.50 | N |
| ATOM | 3044 | CA | PHE | C | 529 | 24.132 | 41.995 | 44.197 | 1.00 | 62.92 | C |
| ATOM | 3045 | C | PHE | C | 529 | 22.753 | 42.435 | 44.704 | 1.00 | 62.89 | C |
| ATOM | 3046 | O | PHE | C | 529 | 22.271 | 41.972 | 45.744 | 1.00 | 60.70 | O |
| ATOM | 3047 | CB | PHE | C | 529 | 24.910 | 43.223 | 43.722 | 1.00 | 59.24 | C |
| ATOM | 3048 | CG | PHE | C | 529 | 24.861 | 43.402 | 42.223 | 1.00 | 54.32 | C |
| ATOM | 3049 | CD1 | PHE | C | 529 | 23.632 | 43.532 | 41.561 | 1.00 | 53.79 | C |
| ATOM | 3050 | CD2 | PHE | C | 529 | 26.026 | 43.334 | 41.457 | 1.00 | 52.93 | C |
| ATOM | 3051 | CE1 | PHE | C | 529 | 23.562 | 43.584 | 40.155 | 1.00 | 51.16 | C |
| ATOM | 3052 | CE2 | PHE | C | 529 | 25.973 | 43.385 | 40.048 | 1.00 | 51.37 | C |
| ATOM | 3053 | CZ | PHE | C | 529 | 24.738 | 43.508 | 39.397 | 1.00 | 50.72 | C |
| ATOM | 3054 | N | VAL | C | 530 | 22.164 | 43.362 | 43.944 | 1.00 | 62.87 | N |
| ATOM | 3055 | CA | VAL | C | 530 | 20.843 | 43.962 | 44.159 | 1.00 | 62.88 | C |
| ATOM | 3056 | C | VAL | C | 530 | 20.321 | 44.182 | 45.584 | 1.00 | 62.22 | C |

TABLE 4-continued

Stem Cell Factor Dimer

| ATOM | 3057 | O | VAL | C | 530 | 20.044 | 43.233 | 46.322 | 1.00 | 62.00 | O |
|---|---|---|---|---|---|---|---|---|---|---|---|
| ATOM | 3058 | CB | VAL | C | 530 | 19.749 | 43.182 | 43.368 | 1.00 | 62.92 | C |
| ATOM | 3059 | CG1 | VAL | C | 530 | 18.449 | 43.993 | 43.332 | 1.00 | 62.70 | C |
| ATOM | 3060 | CG2 | VAL | C | 530 | 20.233 | 42.889 | 41.953 | 1.00 | 63.00 | C |
| ATOM | 3061 | N | VAL | C | 531 | 20.175 | 45.458 | 45.937 | 1.00 | 61.98 | N |
| ATOM | 3062 | CA | VAL | C | 531 | 19.655 | 45.895 | 47.235 | 1.00 | 62.79 | C |
| ATOM | 3063 | C | VAL | C | 531 | 20.097 | 45.061 | 48.452 | 1.00 | 63.46 | C |
| ATOM | 3064 | O | VAL | C | 531 | 21.066 | 44.295 | 48.387 | 1.00 | 62.89 | O |
| ATOM | 3065 | CB | VAL | C | 531 | 18.090 | 45.964 | 47.182 | 1.00 | 62.86 | C |
| ATOM | 3066 | CG1 | VAL | C | 531 | 17.532 | 46.734 | 48.382 | 1.00 | 61.05 | C |
| ATOM | 3067 | CG2 | VAL | C | 531 | 17.648 | 46.632 | 45.878 | 1.00 | 60.79 | C |
| ATOM | 3068 | N | ALA | C | 532 | 19.377 | 45.239 | 49.561 | 1.00 | 64.26 | N |
| ATOM | 3069 | CA | ALA | C | 532 | 19.643 | 44.550 | 50.822 | 1.00 | 64.32 | C |
| ATOM | 3070 | C | ALA | C | 532 | 19.598 | 43.036 | 50.673 | 1.00 | 64.57 | C |
| ATOM | 3071 | O | ALA | C | 532 | 18.581 | 42.404 | 50.966 | 1.00 | 64.60 | O |
| ATOM | 3072 | CB | ALA | C | 532 | 18.634 | 44.998 | 51.876 | 1.00 | 63.34 | C |
| ATOM | 3073 | N | SER | C | 533 | 20.714 | 42.464 | 50.227 | 1.00 | 65.18 | N |
| ATOM | 3074 | CA | SER | C | 533 | 20.824 | 41.024 | 50.029 | 1.00 | 65.29 | C |
| ATOM | 3075 | C | SER | C | 533 | 20.772 | 40.247 | 51.344 | 1.00 | 65.38 | C |
| ATOM | 3076 | O | SER | C | 533 | 21.684 | 40.342 | 52.171 | 1.00 | 65.59 | O |
| ATOM | 3077 | CB | SER | C | 533 | 22.129 | 40.690 | 49.296 | 1.00 | 64.84 | C |
| ATOM | 3078 | OG | SER | C | 533 | 23.259 | 41.063 | 50.069 | 1.00 | 65.94 | O |
| ATOM | 3079 | N | GLU | C | 534 | 19.696 | 39.484 | 51.527 | 1.00 | 65.95 | N |
| ATOM | 3080 | CA | GLU | C | 534 | 19.506 | 38.661 | 52.718 | 1.00 | 65.76 | C |
| ATOM | 3081 | C | GLU | C | 534 | 19.243 | 39.481 | 53.975 | 1.00 | 66.75 | C |
| ATOM | 3082 | O | GLU | C | 534 | 19.342 | 38.965 | 55.089 | 1.00 | 67.37 | O |
| ATOM | 3083 | CB | GLU | C | 534 | 20.734 | 37.782 | 52.930 | 1.00 | 65.02 | C |
| ATOM | 3084 | CG | GLU | C | 534 | 21.167 | 37.039 | 51.676 | 1.00 | 64.99 | C |
| ATOM | 3085 | CD | GLU | C | 534 | 22.532 | 36.403 | 51.828 | 1.00 | 64.29 | C |
| ATOM | 3086 | OE1 | GLU | C | 534 | 22.681 | 35.521 | 52.700 | 1.00 | 65.53 | O |
| ATOM | 3087 | OE2 | GLU | C | 534 | 23.454 | 36.791 | 51.080 | 1.00 | 64.02 | O |
| ATOM | 3088 | N | THR | C | 535 | 18.908 | 40.757 | 53.803 | 1.00 | 67.44 | N |
| ATOM | 3089 | CA | THR | C | 535 | 18.637 | 41.614 | 54.950 | 1.00 | 68.00 | C |
| ATOM | 3090 | C | THR | C | 535 | 17.165 | 41.545 | 55.332 | 1.00 | 68.22 | C |
| ATOM | 3091 | O | THR | C | 535 | 16.756 | 40.678 | 56.104 | 1.00 | 68.54 | O |
| ATOM | 3092 | CB | THR | C | 535 | 19.008 | 43.088 | 54.666 | 1.00 | 67.35 | C |
| ATOM | 3093 | OG1 | THR | C | 535 | 20.403 | 43.179 | 54.347 | 1.00 | 67.95 | O |
| ATOM | 3094 | CG2 | THR | C | 535 | 18.725 | 43.952 | 55.891 | 1.00 | 67.69 | C |
| ATOM | 3095 | N | SER | C | 536 | 16.372 | 42.458 | 54.786 | 1.00 | 69.72 | N |
| ATOM | 3096 | CA | SER | C | 536 | 14.946 | 42.495 | 55.083 | 1.00 | 71.58 | C |
| ATOM | 3097 | C | SER | C | 536 | 14.277 | 41.143 | 54.839 | 1.00 | 72.98 | C |
| ATOM | 3098 | O | SER | C | 536 | 14.316 | 40.601 | 53.731 | 1.00 | 72.00 | O |
| ATOM | 3099 | CB | SER | C | 536 | 14.255 | 43.588 | 54.254 | 1.00 | 70.94 | C |
| ATOM | 3100 | OG | SER | C | 536 | 14.513 | 43.434 | 52.870 | 1.00 | 71.43 | O |
| ATOM | 3101 | N | ASP | C | 537 | 13.673 | 40.605 | 55.896 | 1.00 | 75.05 | N |
| ATOM | 3102 | CA | ASP | C | 537 | 12.979 | 39.324 | 55.839 | 1.00 | 76.57 | C |
| ATOM | 3103 | C | ASP | C | 537 | 11.798 | 39.383 | 54.873 | 1.00 | 76.67 | C |
| ATOM | 3104 | O | ASP | C | 537 | 11.556 | 40.407 | 54.228 | 1.00 | 76.41 | O |
| ATOM | 3105 | CB | ASP | C | 537 | 12.486 | 38.949 | 57.236 | 1.00 | 78.26 | C |
| ATOM | 3106 | CG | ASP | C | 537 | 11.586 | 40.013 | 57.839 | 1.00 | 79.16 | C |
| ATOM | 3107 | OD1 | ASP | C | 537 | 10.455 | 40.193 | 57.339 | 1.00 | 81.11 | O |
| ATOM | 3108 | OD2 | ASP | C | 537 | 12.014 | 40.676 | 58.809 | 1.00 | 79.18 | O |
| ATOM | 3109 | N | CYS | C | 538 | 11.055 | 38.286 | 54.784 | 1.00 | 76.63 | N |
| ATOM | 3110 | CA | CYS | C | 538 | 9.914 | 38.230 | 53.880 | 1.00 | 76.72 | C |
| ATOM | 3111 | C | CYS | C | 538 | 8.594 | 38.162 | 54.640 | 1.00 | 78.73 | C |
| ATOM | 3112 | O | CYS | C | 538 | 8.361 | 37.248 | 55.432 | 1.00 | 79.12 | O |
| ATOM | 3113 | CB | CYS | C | 538 | 10.057 | 37.025 | 52.948 | 1.00 | 72.63 | C |
| ATOM | 3114 | SG | CYS | C | 538 | 11.753 | 36.812 | 52.310 | 1.00 | 67.17 | S |
| ATOM | 3115 | N | VAL | C | 539 | 7.734 | 39.144 | 54.388 | 1.00 | 80.68 | N |
| ATOM | 3116 | CA | VAL | C | 539 | 6.433 | 39.228 | 55.040 | 1.00 | 82.30 | C |
| ATOM | 3117 | C | VAL | C | 539 | 5.325 | 38.748 | 54.109 | 1.00 | 82.61 | C |
| ATOM | 3118 | O | VAL | C | 539 | 4.232 | 38.402 | 54.557 | 1.00 | 83.44 | O |
| ATOM | 3119 | CB | VAL | C | 539 | 6.130 | 40.680 | 55.469 | 1.00 | 82.60 | C |
| ATOM | 3120 | CG1 | VAL | C | 539 | 4.789 | 40.748 | 56.187 | 1.00 | 83.10 | C |
| ATOM | 3121 | CG2 | VAL | C | 539 | 7.249 | 41.197 | 56.358 | 1.00 | 83.03 | C |
| TER | 3122 | | VAL | C | 539 | | | | | | |
| ATOM | 3123 | N | THR | D | 609 | 9.249 | 28.401 | −7.677 | 1.00 | 104.80 | N |
| ATOM | 3124 | CA | THR | D | 609 | 9.697 | 27.034 | −7.441 | 1.00 | 104.82 | C |
| ATOM | 3125 | C | THR | D | 609 | 10.982 | 27.017 | −6.632 | 1.00 | 104.32 | C |
| ATOM | 3126 | O | THR | D | 609 | 12.058 | 27.291 | −7.165 | 1.00 | 104.68 | O |
| ATOM | 3127 | CB | THR | D | 609 | 9.955 | 26.295 | −8.763 | 1.00 | 105.25 | C |
| ATOM | 3128 | OG1 | THR | D | 609 | 8.723 | 26.158 | −9.480 | 1.00 | 106.41 | O |
| ATOM | 3129 | CG2 | THR | D | 609 | 10.544 | 24.916 | −8.499 | 1.00 | 105.53 | C |
| ATOM | 3130 | N | ASN | D | 610 | 10.871 | 26.689 | −5.348 | 1.00 | 103.19 | N |
| ATOM | 3131 | CA | ASN | D | 610 | 12.049 | 26.644 | −4.494 | 1.00 | 101.47 | C |
| ATOM | 3132 | C | ASN | D | 610 | 11.835 | 25.834 | −3.214 | 1.00 | 99.54 | C |
| ATOM | 3133 | O | ASN | D | 610 | 11.326 | 24.712 | −3.253 | 1.00 | 99.25 | O |

TABLE 4-continued

Stem Cell Factor Dimer

| ATOM | 3134 | CB | ASN | D | 610 | 12.490 | 28.070 | -4.146 | 1.00 | 102.29 | C |
| --- | --- | --- | --- | --- | --- | --- | --- | --- | --- | --- | --- |
| ATOM | 3135 | CG | ASN | D | 610 | 13.967 | 28.158 | -3.805 | 1.00 | 103.02 | C |
| ATOM | 3136 | OD1 | ASN | D | 610 | 14.436 | 27.541 | -2.848 | 1.00 | 103.61 | O |
| ATOM | 3137 | ND2 | ASN | D | 610 | 14.710 | 28.931 | -4.592 | 1.00 | 103.09 | N |
| ATOM | 3138 | N | ASN | D | 611 | 12.225 | 26.423 | -2.087 | 1.00 | 97.01 | N |
| ATOM | 3139 | CA | ASN | D | 611 | 12.128 | 25.792 | -0.774 | 1.00 | 93.50 | C |
| ATOM | 3140 | C | ASN | D | 611 | 10.939 | 24.875 | -0.529 | 1.00 | 90.18 | C |
| ATOM | 3141 | O | ASN | D | 611 | 9.862 | 25.040 | -1.103 | 1.00 | 90.09 | O |
| ATOM | 3142 | CB | ASN | D | 611 | 12.170 | 26.857 | 0.324 | 1.00 | 94.97 | C |
| ATOM | 3143 | CG | ASN | D | 611 | 13.502 | 27.574 | 0.385 | 1.00 | 95.78 | C |
| ATOM | 3144 | OD1 | ASN | D | 611 | 14.553 | 26.944 | 0.507 | 1.00 | 95.59 | O |
| ATOM | 3145 | ND2 | ASN | D | 611 | 13.466 | 28.901 | 0.304 | 1.00 | 96.69 | N |
| ATOM | 3146 | N | VAL | D | 612 | 11.174 | 23.907 | 0.350 | 1.00 | 85.29 | N |
| ATOM | 3147 | CA | VAL | D | 612 | 10.198 | 22.909 | 0.760 | 1.00 | 80.19 | C |
| ATOM | 3148 | C | VAL | D | 612 | 10.842 | 22.227 | 1.960 | 1.00 | 75.88 | C |
| ATOM | 3149 | O | VAL | D | 612 | 10.165 | 21.708 | 2.844 | 1.00 | 74.52 | O |
| ATOM | 3150 | CB | VAL | D | 612 | 9.935 | 21.873 | -0.358 | 1.00 | 81.35 | C |
| ATOM | 3151 | CG1 | VAL | D | 612 | 11.238 | 21.205 | -0.772 | 1.00 | 82.50 | C |
| ATOM | 3152 | CG2 | VAL | D | 612 | 8.925 | 20.839 | 0.118 | 1.00 | 80.43 | C |
| ATOM | 3153 | N | LYS | D | 613 | 12.170 | 22.243 | 1.975 | 1.00 | 71.51 | N |
| ATOM | 3154 | CA | LYS | D | 613 | 12.933 | 21.670 | 3.072 | 1.00 | 67.34 | C |
| ATOM | 3155 | C | LYS | D | 613 | 12.999 | 22.749 | 4.149 | 1.00 | 62.33 | C |
| ATOM | 3156 | O | LYS | D | 613 | 13.083 | 22.450 | 5.339 | 1.00 | 61.50 | O |
| ATOM | 3157 | CB | LYS | D | 613 | 14.343 | 21.297 | 2.613 | 1.00 | 69.74 | C |
| ATOM | 3158 | CG | LYS | D | 613 | 15.170 | 22.469 | 2.107 | 1.00 | 72.74 | C |
| ATOM | 3159 | CD | LYS | D | 613 | 16.618 | 22.067 | 1.847 | 1.00 | 74.87 | C |
| ATOM | 3160 | CE | LYS | D | 613 | 17.369 | 21.759 | 3.144 | 1.00 | 76.97 | C |
| ATOM | 3161 | NZ | LYS | D | 613 | 16.829 | 20.579 | 3.884 | 1.00 | 77.27 | N |
| ATOM | 3162 | N | ASP | D | 614 | 12.973 | 24.006 | 3.715 | 1.00 | 56.07 | N |
| ATOM | 3163 | CA | ASP | D | 614 | 12.984 | 25.137 | 4.639 | 1.00 | 49.70 | C |
| ATOM | 3164 | C | ASP | D | 614 | 11.604 | 25.175 | 5.282 | 1.00 | 44.24 | C |
| ATOM | 3165 | O | ASP | D | 614 | 11.444 | 25.616 | 6.419 | 1.00 | 40.58 | O |
| ATOM | 3166 | CB | ASP | D | 614 | 13.248 | 26.446 | 3.886 | 1.00 | 51.87 | C |
| ATOM | 3167 | CG | ASP | D | 614 | 14.726 | 26.831 | 3.870 | 1.00 | 53.98 | C |
| ATOM | 3168 | OD1 | ASP | D | 614 | 15.580 | 25.965 | 4.162 | 1.00 | 56.47 | O |
| ATOM | 3169 | OD2 | ASP | D | 614 | 15.034 | 28.003 | 3.557 | 1.00 | 56.08 | O |
| ATOM | 3170 | N | VAL | D | 615 | 10.609 | 24.697 | 4.537 | 1.00 | 38.54 | N |
| ATOM | 3171 | CA | VAL | D | 615 | 9.247 | 24.656 | 5.036 | 1.00 | 35.71 | C |
| ATOM | 3172 | C | VAL | D | 615 | 9.154 | 23.643 | 6.175 | 1.00 | 33.47 | C |
| ATOM | 3173 | O | VAL | D | 615 | 8.494 | 23.903 | 7.177 | 1.00 | 31.02 | O |
| ATOM | 3174 | CB | VAL | D | 615 | 8.237 | 24.282 | 3.928 | 1.00 | 34.45 | C |
| ATOM | 3175 | CG1 | VAL | D | 615 | 6.851 | 24.119 | 4.523 | 1.00 | 31.21 | C |
| ATOM | 3176 | CG2 | VAL | D | 615 | 8.221 | 25.363 | 2.848 | 1.00 | 32.22 | C |
| ATOM | 3177 | N | THR | D | 616 | 9.823 | 22.501 | 6.037 | 1.00 | 31.98 | N |
| ATOM | 3178 | CA | THR | D | 616 | 9.786 | 21.503 | 7.102 | 1.00 | 32.69 | C |
| ATOM | 3179 | C | THR | D | 616 | 10.533 | 22.047 | 8.318 | 1.00 | 30.76 | C |
| ATOM | 3180 | O | THR | D | 616 | 10.155 | 21.793 | 9.460 | 1.00 | 30.94 | O |
| ATOM | 3181 | CB | THR | D | 616 | 10.428 | 20.162 | 6.672 | 1.00 | 35.33 | C |
| ATOM | 3182 | OG1 | THR | D | 616 | 11.846 | 20.328 | 6.547 | 1.00 | 41.34 | O |
| ATOM | 3183 | CG2 | THR | D | 616 | 9.852 | 19.699 | 5.334 | 1.00 | 35.34 | C |
| ATOM | 3184 | N | LYS | D | 617 | 11.589 | 22.816 | 8.076 | 1.00 | 29.35 | N |
| ATOM | 3185 | CA | LYS | D | 617 | 12.344 | 23.393 | 9.180 | 1.00 | 29.05 | C |
| ATOM | 3186 | C | LYS | D | 617 | 11.499 | 24.469 | 9.849 | 1.00 | 26.16 | C |
| ATOM | 3187 | O | LYS | D | 617 | 11.512 | 24.613 | 11.068 | 1.00 | 25.52 | O |
| ATOM | 3188 | CB | LYS | D | 617 | 13.660 | 24.007 | 8.684 | 1.00 | 31.88 | C |
| ATOM | 3189 | CG | LYS | D | 617 | 14.657 | 22.995 | 8.131 | 1.00 | 36.84 | C |
| ATOM | 3190 | CD | LYS | D | 617 | 15.973 | 23.669 | 7.729 | 1.00 | 40.64 | C |
| ATOM | 3191 | CE | LYS | D | 617 | 16.962 | 22.657 | 7.167 | 1.00 | 42.08 | C |
| ATOM | 3192 | NZ | LYS | D | 617 | 18.285 | 23.281 | 6.866 | 1.00 | 47.70 | N |
| ATOM | 3193 | N | LEU | D | 618 | 10.761 | 25.219 | 9.042 | 1.00 | 23.72 | N |
| ATOM | 3194 | CA | LEU | D | 618 | 9.913 | 26.274 | 9.562 | 1.00 | 23.58 | C |
| ATOM | 3195 | C | LEU | D | 618 | 8.825 | 25.676 | 10.458 | 1.00 | 22.78 | C |
| ATOM | 3196 | O | LEU | D | 618 | 8.595 | 26.150 | 11.565 | 1.00 | 22.16 | O |
| ATOM | 3197 | CB | LEU | D | 618 | 9.277 | 27.050 | 8.404 | 1.00 | 25.27 | C |
| ATOM | 3198 | CG | LEU | D | 618 | 8.511 | 28.330 | 8.742 | 1.00 | 22.16 | C |
| ATOM | 3199 | CD1 | LEU | D | 618 | 9.457 | 29.310 | 9.442 | 1.00 | 25.36 | C |
| ATOM | 3200 | CD2 | LEU | D | 618 | 7.941 | 28.948 | 7.474 | 1.00 | 21.74 | C |
| ATOM | 3201 | N | VAL | D | 619 | 8.153 | 24.634 | 9.981 | 1.00 | 21.60 | N |
| ATOM | 3202 | CA | VAL | D | 619 | 7.111 | 24.014 | 10.780 | 1.00 | 21.20 | C |
| ATOM | 3203 | C | VAL | D | 619 | 7.722 | 23.610 | 12.114 | 1.00 | 19.91 | C |
| ATOM | 3204 | O | VAL | D | 619 | 7.151 | 23.880 | 13.177 | 1.00 | 21.08 | O |
| ATOM | 3205 | CB | VAL | D | 619 | 6.510 | 22.772 | 10.072 | 1.00 | 22.52 | C |
| ATOM | 3206 | CG1 | VAL | D | 619 | 5.569 | 22.012 | 11.020 | 1.00 | 20.69 | C |
| ATOM | 3207 | CG2 | VAL | D | 619 | 5.761 | 23.208 | 8.828 | 1.00 | 22.01 | C |
| ATOM | 3208 | N | ALA | D | 620 | 8.898 | 22.995 | 12.058 | 1.00 | 19.29 | N |
| ATOM | 3209 | CA | ALA | D | 620 | 9.593 | 22.559 | 13.271 | 1.00 | 22.19 | C |
| ATOM | 3210 | C | ALA | D | 620 | 9.941 | 23.708 | 14.212 | 1.00 | 21.87 | C |

TABLE 4-continued

Stem Cell Factor Dimer

| ATOM | 3211 | O | ALA | D | 620 | 9.997 | 23.527 | 15.431 | 1.00 | 22.55 | O |
|---|---|---|---|---|---|---|---|---|---|---|---|
| ATOM | 3212 | CB | ALA | D | 620 | 10.882 | 21.791 | 12.900 | 1.00 | 22.64 | C |
| ATOM | 3213 | N | ASN | D | 621 | 10.180 | 24.886 | 13.642 | 1.00 | 20.77 | N |
| ATOM | 3214 | CA | ASN | D | 621 | 10.545 | 26.044 | 14.429 | 1.00 | 21.13 | C |
| ATOM | 3215 | C | ASN | D | 621 | 9.398 | 26.989 | 14.776 | 1.00 | 22.18 | C |
| ATOM | 3216 | O | ASN | D | 621 | 9.635 | 28.126 | 15.172 | 1.00 | 25.05 | O |
| ATOM | 3217 | CB | ASN | D | 621 | 11.658 | 26.814 | 13.721 | 1.00 | 21.85 | C |
| ATOM | 3218 | CG | ASN | D | 621 | 12.794 | 27.178 | 14.664 | 1.00 | 23.02 | C |
| ATOM | 3219 | OD1 | ASN | D | 621 | 13.183 | 26.377 | 15.522 | 1.00 | 22.74 | O |
| ATOM | 3220 | ND2 | ASN | D | 621 | 13.341 | 28.381 | 14.506 | 1.00 | 24.14 | N |
| ATOM | 3221 | N | LEU | D | 622 | 8.161 | 26.524 | 14.626 | 1.00 | 20.56 | N |
| ATOM | 3222 | CA | LEU | D | 622 | 6.988 | 27.328 | 14.965 | 1.00 | 20.70 | C |
| ATOM | 3223 | C | LEU | D | 622 | 6.262 | 26.587 | 16.081 | 1.00 | 19.87 | C |
| ATOM | 3224 | O | LEU | D | 622 | 6.276 | 25.357 | 16.109 | 1.00 | 20.57 | O |
| ATOM | 3225 | CB | LEU | D | 622 | 6.076 | 27.504 | 13.739 | 1.00 | 19.75 | C |
| ATOM | 3226 | CG | LEU | D | 622 | 6.608 | 28.485 | 12.679 | 1.00 | 20.96 | C |
| ATOM | 3227 | CD1 | LEU | D | 622 | 5.782 | 28.448 | 11.379 | 1.00 | 18.20 | C |
| ATOM | 3228 | CD2 | LEU | D | 622 | 6.600 | 29.879 | 13.291 | 1.00 | 21.02 | C |
| ATOM | 3229 | N | PRO | D | 623 | 5.645 | 27.317 | 17.038 | 1.00 | 17.52 | N |
| ATOM | 3230 | CA | PRO | D | 623 | 4.947 | 26.611 | 18.119 | 1.00 | 20.47 | C |
| ATOM | 3231 | C | PRO | D | 623 | 3.795 | 25.789 | 17.543 | 1.00 | 22.37 | C |
| ATOM | 3232 | O | PRO | D | 623 | 3.043 | 26.292 | 16.697 | 1.00 | 19.83 | O |
| ATOM | 3233 | CB | PRO | D | 623 | 4.435 | 27.740 | 19.016 | 1.00 | 18.11 | C |
| ATOM | 3234 | CG | PRO | D | 623 | 5.272 | 28.928 | 18.638 | 1.00 | 17.91 | C |
| ATOM | 3235 | CD | PRO | D | 623 | 5.440 | 28.770 | 17.153 | 1.00 | 16.64 | C |
| ATOM | 3236 | N | LYS | D | 624 | 3.668 | 24.538 | 17.994 | 1.00 | 21.53 | N |
| ATOM | 3237 | CA | LYS | D | 624 | 2.596 | 23.661 | 17.521 | 1.00 | 26.57 | C |
| ATOM | 3238 | C | LYS | D | 624 | 1.207 | 24.258 | 17.776 | 1.00 | 27.64 | C |
| ATOM | 3239 | O | LYS | D | 624 | 0.252 | 23.910 | 17.093 | 1.00 | 30.00 | O |
| ATOM | 3240 | CB | LYS | D | 624 | 2.665 | 22.282 | 18.204 | 1.00 | 25.86 | C |
| ATOM | 3241 | CG | LYS | D | 624 | 3.908 | 21.478 | 17.876 | 1.00 | 31.06 | C |
| ATOM | 3242 | CD | LYS | D | 624 | 3.932 | 20.129 | 18.594 | 1.00 | 31.72 | C |
| ATOM | 3243 | CE | LYS | D | 624 | 5.322 | 19.472 | 18.497 | 1.00 | 33.07 | C |
| ATOM | 3244 | NZ | LYS | D | 624 | 5.356 | 18.078 | 19.056 | 1.00 | 31.48 | N |
| ATOM | 3245 | N | ASP | D | 625 | 1.085 | 25.149 | 18.756 | 1.00 | 28.70 | N |
| ATOM | 3246 | CA | ASP | D | 625 | −0.221 | 25.724 | 19.052 | 1.00 | 30.74 | C |
| ATOM | 3247 | C | ASP | D | 625 | −0.429 | 27.166 | 18.560 | 1.00 | 30.14 | C |
| ATOM | 3248 | O | ASP | D | 625 | −1.396 | 27.828 | 18.933 | 1.00 | 29.70 | O |
| ATOM | 3249 | CB | ASP | D | 625 | −0.527 | 25.596 | 20.562 | 1.00 | 30.51 | C |
| ATOM | 3250 | CG | ASP | D | 625 | 0.474 | 26.333 | 21.439 | 1.00 | 34.32 | C |
| ATOM | 3251 | OD1 | ASP | D | 625 | 1.687 | 26.271 | 21.158 | 1.00 | 33.59 | O |
| ATOM | 3252 | OD2 | ASP | D | 625 | 0.046 | 26.964 | 22.432 | 1.00 | 40.39 | O |
| ATOM | 3253 | N | TYR | D | 626 | 0.465 | 27.648 | 17.705 | 1.00 | 29.06 | N |
| ATOM | 3254 | CA | TYR | D | 626 | 0.308 | 28.988 | 17.171 | 1.00 | 27.36 | C |
| ATOM | 3255 | C | TYR | D | 626 | −0.647 | 28.868 | 15.976 | 1.00 | 28.81 | C |
| ATOM | 3256 | O | TYR | D | 626 | −0.432 | 28.055 | 15.078 | 1.00 | 29.03 | O |
| ATOM | 3257 | CB | TYR | D | 626 | 1.657 | 29.530 | 16.724 | 1.00 | 27.84 | C |
| ATOM | 3258 | CG | TYR | D | 626 | 1.641 | 30.989 | 16.344 | 1.00 | 24.37 | C |
| ATOM | 3259 | CD1 | TYR | D | 626 | 1.307 | 31.969 | 17.270 | 1.00 | 24.30 | C |
| ATOM | 3260 | CD2 | TYR | D | 626 | 1.999 | 31.389 | 15.062 | 1.00 | 25.35 | C |
| ATOM | 3261 | CE1 | TYR | D | 626 | 1.338 | 33.326 | 16.922 | 1.00 | 22.03 | C |
| ATOM | 3262 | CE2 | TYR | D | 626 | 2.029 | 32.719 | 14.706 | 1.00 | 21.86 | C |
| ATOM | 3263 | CZ | TYR | D | 626 | 1.705 | 33.684 | 15.635 | 1.00 | 22.40 | C |
| ATOM | 3264 | OH | TYR | D | 626 | 1.793 | 35.010 | 15.270 | 1.00 | 26.81 | O |
| ATOM | 3265 | N | MET | D | 627 | −1.712 | 29.660 | 15.979 | 1.00 | 27.81 | N |
| ATOM | 3266 | CA | MET | D | 627 | −2.692 | 29.614 | 14.902 | 1.00 | 27.77 | C |
| ATOM | 3267 | C | MET | D | 627 | −2.414 | 30.687 | 13.879 | 1.00 | 26.69 | C |
| ATOM | 3268 | O | MET | D | 627 | −2.155 | 31.847 | 14.229 | 1.00 | 27.26 | O |
| ATOM | 3269 | CB | MET | D | 627 | −4.111 | 29.795 | 15.449 | 1.00 | 29.13 | C |
| ATOM | 3270 | CG | MET | D | 627 | −4.483 | 28.783 | 16.530 | 1.00 | 33.45 | C |
| ATOM | 3271 | SD | MET | D | 627 | −4.081 | 27.094 | 16.044 | 1.00 | 39.63 | S |
| ATOM | 3272 | CE | MET | D | 627 | −5.527 | 26.652 | 15.050 | 1.00 | 38.53 | C |
| ATOM | 3273 | N | ILE | D | 628 | −2.451 | 30.292 | 12.612 | 1.00 | 24.67 | N |
| ATOM | 3274 | CA | ILE | D | 628 | −2.219 | 31.221 | 11.522 | 1.00 | 25.62 | C |
| ATOM | 3275 | C | ILE | D | 628 | −3.526 | 31.385 | 10.757 | 1.00 | 26.27 | C |
| ATOM | 3276 | O | ILE | D | 628 | −4.167 | 30.395 | 10.386 | 1.00 | 22.16 | O |
| ATOM | 3277 | CB | ILE | D | 628 | −1.144 | 30.692 | 10.547 | 1.00 | 25.29 | C |
| ATOM | 3278 | CG1 | ILE | D | 628 | 0.138 | 30.346 | 11.315 | 1.00 | 26.17 | C |
| ATOM | 3279 | CG2 | ILE | D | 628 | −0.851 | 31.753 | 9.485 | 1.00 | 25.31 | C |
| ATOM | 3280 | CD1 | ILE | D | 628 | 1.186 | 29.612 | 10.487 | 1.00 | 22.59 | C |
| ATOM | 3281 | N | THR | D | 629 | −3.912 | 32.633 | 10.515 | 1.00 | 28.09 | N |
| ATOM | 3282 | CA | THR | D | 629 | −5.144 | 32.912 | 9.779 | 1.00 | 31.02 | C |
| ATOM | 3283 | C | THR | D | 629 | −4.949 | 32.944 | 8.271 | 1.00 | 30.20 | C |
| ATOM | 3284 | O | THR | D | 629 | −3.988 | 33.518 | 7.755 | 1.00 | 27.82 | O |
| ATOM | 3285 | CB | THR | D | 629 | −5.756 | 34.250 | 10.162 | 1.00 | 32.14 | C |
| ATOM | 3286 | OG1 | THR | D | 629 | −5.718 | 34.408 | 11.582 | 1.00 | 37.56 | O |
| ATOM | 3287 | CG2 | THR | D | 629 | −7.202 | 34.295 | 9.697 | 1.00 | 36.14 | C |

TABLE 4-continued

Stem Cell Factor Dimer

| ATOM | 3288 | N | LEU | D | 630 | −5.898 | 32.341 | 7.574 | 1.00 | 30.44 | N |
|---|---|---|---|---|---|---|---|---|---|---|---|
| ATOM | 3289 | CA | LEU | D | 630 | −5.866 | 32.271 | 6.131 | 1.00 | 32.20 | C |
| ATOM | 3290 | C | LEU | D | 630 | −7.297 | 32.212 | 5.629 | 1.00 | 34.56 | C |
| ATOM | 3291 | O | LEU | D | 630 | −8.097 | 31.390 | 6.092 | 1.00 | 33.39 | O |
| ATOM | 3292 | CB | LEU | D | 630 | −5.113 | 31.002 | 5.670 | 1.00 | 28.93 | C |
| ATOM | 3293 | CG | LEU | D | 630 | −5.202 | 30.639 | 4.177 | 1.00 | 27.21 | C |
| ATOM | 3294 | CD1 | LEU | D | 630 | −4.440 | 31.676 | 3.365 | 1.00 | 22.63 | C |
| ATOM | 3295 | CD2 | LEU | D | 630 | −4.641 | 29.232 | 3.916 | 1.00 | 25.04 | C |
| ATOM | 3296 | N | LYS | D | 631 | −7.629 | 33.088 | 4.692 | 1.00 | 37.84 | N |
| ATOM | 3297 | CA | LYS | D | 631 | −8.963 | 33.058 | 4.118 | 1.00 | 42.10 | C |
| ATOM | 3298 | C | LYS | D | 631 | −8.918 | 31.896 | 3.135 | 1.00 | 44.08 | C |
| ATOM | 3299 | O | LYS | D | 631 | −8.337 | 31.993 | 2.054 | 1.00 | 41.39 | O |
| ATOM | 3300 | CB | LYS | D | 631 | −9.276 | 34.379 | 3.418 | 1.00 | 42.62 | C |
| ATOM | 3301 | CG | LYS | D | 631 | −9.395 | 35.528 | 4.403 | 1.00 | 44.88 | C |
| ATOM | 3302 | CD | LYS | D | 631 | −9.531 | 36.864 | 3.707 | 1.00 | 47.80 | C |
| ATOM | 3303 | CE | LYS | D | 631 | −9.388 | 37.990 | 4.711 | 1.00 | 49.65 | C |
| ATOM | 3304 | NZ | LYS | D | 631 | −9.271 | 39.314 | 4.048 | 1.00 | 54.29 | N |
| ATOM | 3305 | N | TYR | D | 632 | −9.500 | 30.782 | 3.558 | 1.00 | 48.07 | N |
| ATOM | 3306 | CA | TYR | D | 632 | −9.534 | 29.566 | 2.771 | 1.00 | 53.34 | C |
| ATOM | 3307 | C | TYR | D | 632 | −10.583 | 29.681 | 1.665 | 1.00 | 55.29 | C |
| ATOM | 3308 | O | TYR | D | 632 | −11.699 | 30.154 | 1.899 | 1.00 | 55.86 | O |
| ATOM | 3309 | CB | TYR | D | 632 | −9.865 | 28.389 | 3.691 | 1.00 | 57.34 | C |
| ATOM | 3310 | CG | TYR | D | 632 | −9.485 | 27.026 | 3.154 | 1.00 | 61.63 | C |
| ATOM | 3311 | CD1 | TYR | D | 632 | −8.150 | 26.674 | 2.976 | 1.00 | 62.09 | C |
| ATOM | 3312 | CD2 | TYR | D | 632 | −10.462 | 26.077 | 2.850 | 1.00 | 64.00 | C |
| ATOM | 3313 | CE1 | TYR | D | 632 | −7.795 | 25.414 | 2.513 | 1.00 | 64.69 | C |
| ATOM | 3314 | CE2 | TYR | D | 632 | −10.117 | 24.810 | 2.383 | 1.00 | 65.21 | C |
| ATOM | 3315 | CZ | TYR | D | 632 | −8.781 | 24.485 | 2.218 | 1.00 | 65.98 | C |
| ATOM | 3316 | OH | TYR | D | 632 | −8.430 | 23.239 | 1.748 | 1.00 | 66.91 | O |
| ATOM | 3317 | N | VAL | D | 633 | −10.217 | 29.260 | 0.458 | 1.00 | 56.89 | N |
| ATOM | 3318 | CA | VAL | D | 633 | −11.136 | 29.296 | −0.675 | 1.00 | 58.30 | C |
| ATOM | 3319 | C | VAL | D | 633 | −12.053 | 28.073 | −0.623 | 1.00 | 59.02 | C |
| ATOM | 3320 | O | VAL | D | 633 | −11.609 | 26.969 | −0.320 | 1.00 | 58.72 | O |
| ATOM | 3321 | CB | VAL | D | 633 | −10.363 | 29.322 | −2.019 | 1.00 | 58.62 | C |
| ATOM | 3322 | CG1 | VAL | D | 633 | −11.200 | 28.713 | −3.130 | 1.00 | 59.35 | C |
| ATOM | 3323 | CG2 | VAL | D | 633 | −10.009 | 30.757 | −2.378 | 1.00 | 57.39 | C |
| ATOM | 3324 | N | PRO | D | 634 | −13.350 | 28.264 | −0.920 | 1.00 | 61.02 | N |
| ATOM | 3325 | CA | PRO | D | 634 | −14.383 | 27.223 | −0.923 | 1.00 | 62.30 | C |
| ATOM | 3326 | C | PRO | D | 634 | −13.921 | 25.775 | −1.086 | 1.00 | 62.35 | C |
| ATOM | 3327 | O | PRO | D | 634 | −13.371 | 25.184 | −0.155 | 1.00 | 62.18 | O |
| ATOM | 3328 | CB | PRO | D | 634 | −15.302 | 27.677 | −2.048 | 1.00 | 62.26 | C |
| ATOM | 3329 | CG | PRO | D | 634 | −15.345 | 29.157 | −1.802 | 1.00 | 63.32 | C |
| ATOM | 3330 | CD | PRO | D | 634 | −13.881 | 29.509 | −1.511 | 1.00 | 62.09 | C |
| ATOM | 3331 | N | GLY | D | 635 | −14.154 | 25.202 | −2.262 | 1.00 | 62.41 | N |
| ATOM | 3332 | CA | GLY | D | 635 | −13.767 | 23.818 | −2.482 | 1.00 | 64.17 | C |
| ATOM | 3333 | C | GLY | D | 635 | −12.385 | 23.654 | −3.073 | 1.00 | 64.49 | C |
| ATOM | 3334 | O | GLY | D | 635 | −12.181 | 22.822 | −3.962 | 1.00 | 64.76 | O |
| ATOM | 3335 | N | MET | D | 636 | −11.433 | 24.434 | −2.566 | 1.00 | 64.65 | N |
| ATOM | 3336 | CA | MET | D | 636 | −10.062 | 24.402 | −3.065 | 1.00 | 64.78 | C |
| ATOM | 3337 | C | MET | D | 636 | −9.326 | 23.086 | −2.823 | 1.00 | 64.92 | C |
| ATOM | 3338 | O | MET | D | 636 | −8.104 | 23.031 | −2.953 | 1.00 | 65.98 | O |
| ATOM | 3339 | CB | MET | D | 636 | −9.242 | 25.537 | −2.446 | 1.00 | 65.11 | C |
| ATOM | 3340 | CG | MET | D | 636 | −8.795 | 25.268 | −1.013 | 1.00 | 65.13 | C |
| ATOM | 3341 | SD | MET | D | 636 | −7.160 | 25.975 | −0.639 | 1.00 | 67.60 | S |
| ATOM | 3342 | CE | MET | D | 636 | −6.056 | 24.678 | −1.286 | 1.00 | 63.14 | C |
| ATOM | 3343 | N | ASP | D | 637 | −10.046 | 22.029 | −2.469 | 1.00 | 64.44 | N |
| ATOM | 3344 | CA | ASP | D | 637 | −9.382 | 20.754 | −2.230 | 1.00 | 64.50 | C |
| ATOM | 3345 | C | ASP | D | 637 | −9.855 | 19.712 | −3.229 | 1.00 | 63.89 | C |
| ATOM | 3346 | O | ASP | D | 637 | −9.095 | 18.826 | −3.620 | 1.00 | 63.15 | O |
| ATOM | 3347 | CB | ASP | D | 637 | −9.662 | 20.263 | −0.808 | 1.00 | 65.45 | C |
| ATOM | 3348 | CG | ASP | D | 637 | −10.970 | 19.508 | −0.702 | 1.00 | 66.50 | C |
| ATOM | 3349 | OD1 | ASP | D | 637 | −11.989 | 20.007 | −1.229 | 1.00 | 67.34 | O |
| ATOM | 3350 | OD2 | ASP | D | 637 | −10.979 | 18.418 | −0.087 | 1.00 | 67.32 | O |
| ATOM | 3351 | N | VAL | D | 638 | −11.113 | 19.827 | −3.643 | 1.00 | 64.62 | N |
| ATOM | 3352 | CA | VAL | D | 638 | −11.693 | 18.880 | −4.588 | 1.00 | 65.92 | C |
| ATOM | 3353 | C | VAL | D | 638 | −11.757 | 19.406 | −6.020 | 1.00 | 69.41 | C |
| ATOM | 3354 | O | VAL | D | 638 | −11.298 | 18.737 | −6.948 | 1.00 | 69.69 | O |
| ATOM | 3355 | CB | VAL | D | 638 | −13.114 | 18.455 | −4.147 | 1.00 | 62.82 | C |
| ATOM | 3356 | CG1 | VAL | D | 638 | −13.034 | 17.657 | −2.857 | 1.00 | 61.12 | C |
| ATOM | 3357 | CG2 | VAL | D | 638 | −13.997 | 19.681 | −3.957 | 1.00 | 60.81 | C |
| ATOM | 3358 | N | LEU | D | 639 | −12.327 | 20.595 | −6.201 | 1.00 | 73.26 | N |
| ATOM | 3359 | CA | LEU | D | 639 | −12.439 | 21.184 | −7.530 | 1.00 | 78.29 | C |
| ATOM | 3360 | C | LEU | D | 639 | −11.082 | 21.251 | −8.225 | 1.00 | 86.56 | C |
| ATOM | 3361 | O | LEU | D | 639 | −10.036 | 21.192 | −7.575 | 1.00 | 86.40 | O |
| ATOM | 3362 | CB | LEU | D | 639 | −13.046 | 22.588 | −7.446 | 1.00 | 73.68 | C |
| ATOM | 3363 | CG | LEU | D | 639 | −14.565 | 22.684 | −7.275 | 1.00 | 69.04 | C |
| ATOM | 3364 | CD1 | LEU | D | 639 | −14.983 | 22.060 | −5.955 | 1.00 | 66.96 | C |

TABLE 4-continued

Stem Cell Factor Dimer

| ATOM | 3365 | CD2 | LEU | D | 639 | −14.986 | 24.148 | −7.336 | 1.00 | 66.40 | C |
|---|---|---|---|---|---|---|---|---|---|---|---|
| ATOM | 3366 | N | PRO | D | 640 | −11.083 | 21.379 | −9.562 | 1.00 | 90.46 | N |
| ATOM | 3367 | CA | PRO | D | 640 | −9.840 | 21.451 | −10.334 | 1.00 | 96.88 | C |
| ATOM | 3368 | C | PRO | D | 640 | −8.972 | 22.651 | −9.965 | 1.00 | 101.73 | C |
| ATOM | 3369 | O | PRO | D | 640 | −9.476 | 23.684 | −9.522 | 1.00 | 102.12 | O |
| ATOM | 3370 | CB | PRO | D | 640 | −10.339 | 21.518 | −11.774 | 1.00 | 97.23 | C |
| ATOM | 3371 | CG | PRO | D | 640 | −11.635 | 22.257 | −11.637 | 1.00 | 96.90 | C |
| ATOM | 3372 | CD | PRO | D | 640 | −12.251 | 21.575 | −10.440 | 1.00 | 92.55 | C |
| ATOM | 3373 | N | SER | D | 641 | −7.665 | 22.499 | −10.156 | 1.00 | 105.53 | N |
| ATOM | 3374 | CA | SER | D | 641 | −6.705 | 23.553 | −9.854 | 1.00 | 109.37 | C |
| ATOM | 3375 | C | SER | D | 641 | −6.828 | 24.693 | −10.861 | 1.00 | 110.52 | C |
| ATOM | 3376 | O | SER | D | 641 | −5.826 | 25.215 | −11.353 | 1.00 | 111.81 | O |
| ATOM | 3377 | CB | SER | D | 641 | −5.281 | 22.990 | −9.888 | 1.00 | 111.58 | C |
| ATOM | 3378 | OG | SER | D | 641 | −4.914 | 22.597 | −11.198 | 1.00 | 114.18 | O |
| ATOM | 3379 | N | HIS | D | 642 | −8.066 | 25.066 | −11.166 | 1.00 | 110.97 | N |
| ATOM | 3380 | CA | HIS | D | 642 | −8.343 | 26.142 | −12.107 | 1.00 | 110.40 | C |
| ATOM | 3381 | C | HIS | D | 642 | −9.260 | 27.140 | −11.423 | 1.00 | 108.41 | C |
| ATOM | 3382 | O | HIS | D | 642 | −9.047 | 28.350 | −11.491 | 1.00 | 108.42 | O |
| ATOM | 3383 | CB | HIS | D | 642 | −9.027 | 25.587 | −13.357 | 1.00 | 112.21 | C |
| ATOM | 3384 | CG | HIS | D | 642 | −8.258 | 24.495 | −14.030 | 1.00 | 113.95 | C |
| ATOM | 3385 | ND1 | HIS | D | 642 | −6.974 | 24.669 | −14.499 | 1.00 | 114.98 | N |
| ATOM | 3386 | CD2 | HIS | D | 642 | −8.591 | 23.213 | −14.313 | 1.00 | 114.86 | C |
| ATOM | 3387 | CE1 | HIS | D | 642 | −6.548 | 23.542 | −15.042 | 1.00 | 115.59 | C |
| ATOM | 3388 | NE2 | HIS | D | 642 | −7.511 | 22.643 | −14.942 | 1.00 | 115.50 | N |
| ATOM | 3389 | N | CYS | D | 643 | −10.285 | 26.616 | −10.763 | 1.00 | 105.86 | N |
| ATOM | 3390 | CA | CYS | D | 643 | −11.241 | 27.445 | −10.049 | 1.00 | 102.95 | C |
| ATOM | 3391 | C | CYS | D | 643 | −10.504 | 28.309 | −9.031 | 1.00 | 100.68 | C |
| ATOM | 3392 | O | CYS | D | 643 | −10.472 | 29.535 | −9.152 | 1.00 | 100.62 | O |
| ATOM | 3393 | CB | CYS | D | 643 | −12.275 | 26.563 | −9.342 | 1.00 | 103.59 | C |
| ATOM | 3394 | SG | CYS | D | 643 | −13.485 | 25.768 | −10.448 | 1.00 | 102.50 | S |
| ATOM | 3395 | N | TRP | D | 644 | −9.908 | 27.663 | −8.033 | 1.00 | 97.42 | N |
| ATOM | 3396 | CA | TRP | D | 644 | −9.167 | 28.377 | −7.000 | 1.00 | 93.72 | C |
| ATOM | 3397 | C | TRP | D | 644 | −7.741 | 28.703 | −7.445 | 1.00 | 90.99 | C |
| ATOM | 3398 | O | TRP | D | 644 | −7.532 | 29.219 | −8.542 | 1.00 | 91.82 | O |
| ATOM | 3399 | CB | TRP | D | 644 | −9.144 | 27.564 | −5.698 | 1.00 | 93.17 | C |
| ATOM | 3400 | CG | TRP | D | 644 | −8.830 | 26.110 | −5.874 | 1.00 | 92.17 | C |
| ATOM | 3401 | CD1 | TRP | D | 644 | −9.645 | 25.153 | −6.409 | 1.00 | 92.07 | C |
| ATOM | 3402 | CD2 | TRP | D | 644 | −7.613 | 25.446 | −5.516 | 1.00 | 91.66 | C |
| ATOM | 3403 | NE1 | TRP | D | 644 | −9.011 | 23.934 | −6.405 | 1.00 | 91.70 | N |
| ATOM | 3404 | CE2 | TRP | D | 644 | −7.762 | 24.085 | −5.864 | 1.00 | 91.39 | C |
| ATOM | 3405 | CE3 | TRP | D | 644 | −6.409 | 25.868 | −4.935 | 1.00 | 91.54 | C |
| ATOM | 3406 | CZ2 | TRP | D | 644 | −6.752 | 23.142 | −5.651 | 1.00 | 91.23 | C |
| ATOM | 3407 | CZ3 | TRP | D | 644 | −5.402 | 24.929 | −4.723 | 1.00 | 91.15 | C |
| ATOM | 3408 | CH2 | TRP | D | 644 | −5.582 | 23.581 | −5.081 | 1.00 | 91.44 | C |
| ATOM | 3409 | N | ILE | D | 645 | −6.771 | 28.404 | −6.588 | 1.00 | 87.01 | N |
| ATOM | 3410 | CA | ILE | D | 645 | −5.364 | 28.668 | −6.873 | 1.00 | 82.82 | C |
| ATOM | 3411 | C | ILE | D | 645 | −5.059 | 30.145 | −7.063 | 1.00 | 79.68 | C |
| ATOM | 3412 | O | ILE | D | 645 | −4.244 | 30.714 | −6.338 | 1.00 | 78.71 | O |
| ATOM | 3413 | CB | ILE | D | 645 | −4.881 | 27.907 | −8.121 | 1.00 | 83.33 | C |
| ATOM | 3414 | CG1 | ILE | D | 645 | −4.632 | 26.444 | −7.761 | 1.00 | 83.90 | C |
| ATOM | 3415 | CG2 | ILE | D | 645 | −3.609 | 28.546 | −8.668 | 1.00 | 83.53 | C |
| ATOM | 3416 | CD1 | ILE | D | 645 | −3.919 | 25.666 | −8.839 | 1.00 | 85.34 | C |
| ATOM | 3417 | N | SER | D | 646 | −5.697 | 30.763 | −8.049 | 1.00 | 76.22 | N |
| ATOM | 3418 | CA | SER | D | 646 | −5.477 | 32.176 | −8.308 | 1.00 | 72.36 | C |
| ATOM | 3419 | C | SER | D | 646 | −5.791 | 32.968 | −7.044 | 1.00 | 68.74 | C |
| ATOM | 3420 | O | SER | D | 646 | −5.033 | 33.854 | −6.651 | 1.00 | 67.25 | O |
| ATOM | 3421 | CB | SER | D | 646 | −6.364 | 32.652 | −9.457 | 1.00 | 73.20 | C |
| ATOM | 3422 | OG | SER | D | 646 | −6.150 | 34.028 | −9.719 | 1.00 | 72.80 | O |
| ATOM | 3423 | N | GLU | D | 647 | −6.907 | 32.636 | −6.404 | 1.00 | 65.08 | N |
| ATOM | 3424 | CA | GLU | D | 647 | −7.306 | 33.317 | −5.181 | 1.00 | 62.17 | C |
| ATOM | 3425 | C | GLU | D | 647 | −6.456 | 32.834 | −4.007 | 1.00 | 59.05 | C |
| ATOM | 3426 | O | GLU | D | 647 | −5.992 | 33.633 | −3.193 | 1.00 | 56.23 | O |
| ATOM | 3427 | CB | GLU | D | 647 | −8.788 | 33.067 | −4.894 | 1.00 | 63.15 | C |
| ATOM | 3428 | CG | GLU | D | 647 | −9.310 | 33.796 | −3.662 | 1.00 | 66.05 | C |
| ATOM | 3429 | CD | GLU | D | 647 | −9.198 | 35.310 | −3.773 | 1.00 | 68.11 | C |
| ATOM | 3430 | OE1 | GLU | D | 647 | −9.806 | 35.891 | −4.699 | 1.00 | 69.38 | O |
| ATOM | 3431 | OE2 | GLU | D | 647 | −8.504 | 35.918 | −2.929 | 1.00 | 68.44 | O |
| ATOM | 3432 | N | MET | D | 648 | −6.250 | 31.523 | −3.925 | 1.00 | 56.89 | N |
| ATOM | 3433 | CA | MET | D | 648 | −5.442 | 30.963 | −2.852 | 1.00 | 55.25 | C |
| ATOM | 3434 | C | MET | D | 648 | −4.088 | 31.644 | −2.788 | 1.00 | 53.08 | C |
| ATOM | 3435 | O | MET | D | 648 | −3.683 | 32.139 | −1.737 | 1.00 | 53.75 | O |
| ATOM | 3436 | CB | MET | D | 648 | −5.237 | 29.468 | −3.050 | 1.00 | 55.54 | C |
| ATOM | 3437 | CG | MET | D | 648 | −6.100 | 28.619 | −2.147 | 1.00 | 60.03 | C |
| ATOM | 3438 | SD | MET | D | 648 | −5.943 | 29.094 | −0.401 | 1.00 | 63.69 | S |
| ATOM | 3439 | CE | MET | D | 648 | −7.335 | 30.206 | −0.245 | 1.00 | 58.42 | C |
| ATOM | 3440 | N | VAL | D | 649 | −3.391 | 31.667 | −3.919 | 1.00 | 49.36 | N |
| ATOM | 3441 | CA | VAL | D | 649 | −2.077 | 32.285 | −3.988 | 1.00 | 46.89 | C |

TABLE 4-continued

Stem Cell Factor Dimer

| ATOM | 3442 | C | VAL | D | 649 | −2.086 | 33.707 | −3.437 | 1.00 | 44.43 | C |
|---|---|---|---|---|---|---|---|---|---|---|---|
| ATOM | 3443 | O | VAL | D | 649 | −1.139 | 34.121 | −2.774 | 1.00 | 44.35 | O |
| ATOM | 3444 | CB | VAL | D | 649 | −1.541 | 32.275 | −5.437 | 1.00 | 47.15 | C |
| ATOM | 3445 | CG1 | VAL | D | 649 | −0.321 | 33.168 | −5.554 | 1.00 | 49.44 | C |
| ATOM | 3446 | CG2 | VAL | D | 649 | −1.166 | 30.847 | −5.831 | 1.00 | 47.73 | C |
| ATOM | 3447 | N | VAL | D | 650 | −3.153 | 34.454 | −3.705 | 1.00 | 41.65 | N |
| ATOM | 3448 | CA | VAL | D | 650 | −3.261 | 35.817 | −3.199 | 1.00 | 38.93 | C |
| ATOM | 3449 | C | VAL | D | 650 | −3.440 | 35.780 | −1.688 | 1.00 | 36.51 | C |
| ATOM | 3450 | O | VAL | D | 650 | −2.888 | 36.611 | −0.966 | 1.00 | 38.35 | O |
| ATOM | 3451 | CB | VAL | D | 650 | −4.468 | 36.562 | −3.818 | 1.00 | 40.92 | C |
| ATOM | 3452 | CG1 | VAL | D | 650 | −4.664 | 37.924 | −3.131 | 1.00 | 36.92 | C |
| ATOM | 3453 | CG2 | VAL | D | 650 | −4.249 | 36.741 | −5.306 | 1.00 | 39.66 | C |
| ATOM | 3454 | N | GLN | D | 651 | −4.220 | 34.814 | −1.219 | 1.00 | 34.68 | N |
| ATOM | 3455 | CA | GLN | D | 651 | −4.477 | 34.652 | 0.206 | 1.00 | 35.25 | C |
| ATOM | 3456 | C | GLN | D | 651 | −3.260 | 34.147 | 0.977 | 1.00 | 33.77 | C |
| ATOM | 3457 | O | GLN | D | 651 | −3.045 | 34.530 | 2.122 | 1.00 | 33.36 | O |
| ATOM | 3458 | CB | GLN | D | 651 | −5.654 | 33.704 | 0.423 | 1.00 | 35.38 | C |
| ATOM | 3459 | CG | GLN | D | 651 | −6.992 | 34.289 | −0.005 | 1.00 | 39.24 | C |
| ATOM | 3460 | CD | GLN | D | 651 | −7.201 | 35.707 | 0.514 | 1.00 | 39.71 | C |
| ATOM | 3461 | OE1 | GLN | D | 651 | −6.848 | 36.026 | 1.651 | 1.00 | 41.62 | O |
| ATOM | 3462 | NE2 | GLN | D | 651 | −7.779 | 36.562 | −0.320 | 1.00 | 41.54 | N |
| ATOM | 3463 | N | LEU | D | 652 | −2.473 | 33.282 | 0.350 | 1.00 | 32.28 | N |
| ATOM | 3464 | CA | LEU | D | 652 | −1.278 | 32.749 | 0.989 | 1.00 | 32.03 | C |
| ATOM | 3465 | C | LEU | D | 652 | −0.255 | 33.850 | 1.164 | 1.00 | 31.64 | C |
| ATOM | 3466 | O | LEU | D | 652 | 0.453 | 33.899 | 2.160 | 1.00 | 32.05 | O |
| ATOM | 3467 | CB | LEU | D | 652 | −0.671 | 31.636 | 0.143 | 1.00 | 31.97 | C |
| ATOM | 3468 | CG | LEU | D | 652 | −1.391 | 30.298 | 0.254 | 1.00 | 30.73 | C |
| ATOM | 3469 | CD1 | LEU | D | 652 | −0.879 | 29.344 | −0.811 | 1.00 | 30.88 | C |
| ATOM | 3470 | CD2 | LEU | D | 652 | −1.164 | 29.740 | 1.649 | 1.00 | 30.69 | C |
| ATOM | 3471 | N | SER | D | 653 | −0.180 | 34.740 | 0.188 | 1.00 | 32.28 | N |
| ATOM | 3472 | CA | SER | D | 653 | 0.767 | 35.831 | 0.264 | 1.00 | 34.28 | C |
| ATOM | 3473 | C | SER | D | 653 | 0.393 | 36.792 | 1.390 | 1.00 | 35.52 | C |
| ATOM | 3474 | O | SER | D | 653 | 1.260 | 37.317 | 2.083 | 1.00 | 35.54 | O |
| ATOM | 3475 | CB | SER | D | 653 | 0.819 | 36.568 | −1.074 | 1.00 | 34.23 | C |
| ATOM | 3476 | OG | SER | D | 653 | 1.768 | 37.617 | −1.021 | 1.00 | 35.34 | O |
| ATOM | 3477 | N | ASP | D | 654 | −0.899 | 37.036 | 1.576 | 1.00 | 37.08 | N |
| ATOM | 3478 | CA | ASP | D | 654 | −1.315 | 37.931 | 2.647 | 1.00 | 38.55 | C |
| ATOM | 3479 | C | ASP | D | 654 | −1.021 | 37.290 | 3.990 | 1.00 | 36.67 | C |
| ATOM | 3480 | O | ASP | D | 654 | −0.482 | 37.937 | 4.887 | 1.00 | 37.06 | O |
| ATOM | 3481 | CB | ASP | D | 654 | −2.805 | 38.266 | 2.540 | 1.00 | 43.76 | C |
| ATOM | 3482 | CG | ASP | D | 654 | −3.066 | 39.469 | 1.647 | 1.00 | 50.69 | C |
| ATOM | 3483 | OD1 | ASP | D | 654 | −2.380 | 40.504 | 1.835 | 1.00 | 55.30 | O |
| ATOM | 3484 | OD2 | ASP | D | 654 | −3.954 | 39.389 | 0.765 | 1.00 | 53.94 | O |
| ATOM | 3485 | N | SER | D | 655 | −1.371 | 36.016 | 4.127 | 1.00 | 33.71 | N |
| ATOM | 3486 | CA | SER | D | 655 | −1.119 | 35.299 | 5.375 | 1.00 | 32.76 | C |
| ATOM | 3487 | C | SER | D | 655 | 0.370 | 35.228 | 5.703 | 1.00 | 32.30 | C |
| ATOM | 3488 | O | SER | D | 655 | 0.759 | 35.327 | 6.867 | 1.00 | 33.34 | O |
| ATOM | 3489 | CB | SER | D | 655 | −1.695 | 33.883 | 5.303 | 1.00 | 29.84 | C |
| ATOM | 3490 | OG | SER | D | 655 | −3.108 | 33.915 | 5.437 | 1.00 | 32.16 | O |
| ATOM | 3491 | N | LEU | D | 656 | 1.196 | 35.049 | 4.677 | 1.00 | 31.24 | N |
| ATOM | 3492 | CA | LEU | D | 656 | 2.641 | 34.959 | 4.863 | 1.00 | 30.45 | C |
| ATOM | 3493 | C | LEU | D | 656 | 3.198 | 36.325 | 5.205 | 1.00 | 29.81 | C |
| ATOM | 3494 | O | LEU | D | 656 | 4.071 | 36.455 | 6.063 | 1.00 | 30.17 | O |
| ATOM | 3495 | CB | LEU | D | 656 | 3.308 | 34.424 | 3.596 | 1.00 | 30.74 | C |
| ATOM | 3496 | CG | LEU | D | 656 | 3.135 | 32.926 | 3.337 | 1.00 | 31.26 | C |
| ATOM | 3497 | CD1 | LEU | D | 656 | 3.629 | 32.574 | 1.937 | 1.00 | 29.15 | C |
| ATOM | 3498 | CD2 | LEU | D | 656 | 3.896 | 32.144 | 4.403 | 1.00 | 30.48 | C |
| ATOM | 3499 | N | THR | D | 657 | 2.681 | 37.344 | 4.535 | 1.00 | 30.26 | N |
| ATOM | 3500 | CA | THR | D | 657 | 3.104 | 38.712 | 4.783 | 1.00 | 32.29 | C |
| ATOM | 3501 | C | THR | D | 657 | 2.778 | 39.138 | 6.213 | 1.00 | 32.55 | C |
| ATOM | 3502 | O | THR | D | 657 | 3.583 | 39.802 | 6.862 | 1.00 | 34.64 | O |
| ATOM | 3503 | CB | THR | D | 657 | 2.432 | 39.677 | 3.802 | 1.00 | 34.30 | C |
| ATOM | 3504 | OG1 | THR | D | 657 | 2.838 | 39.345 | 2.471 | 1.00 | 32.27 | O |
| ATOM | 3505 | CG2 | THR | D | 657 | 2.826 | 41.122 | 4.110 | 1.00 | 33.78 | C |
| ATOM | 3506 | N | ASP | D | 658 | 1.601 | 38.763 | 6.702 | 1.00 | 34.08 | N |
| ATOM | 3507 | CA | ASP | D | 658 | 1.199 | 39.097 | 8.071 | 1.00 | 33.18 | C |
| ATOM | 3508 | C | ASP | D | 658 | 2.129 | 38.357 | 9.031 | 1.00 | 31.81 | C |
| ATOM | 3509 | O | ASP | D | 658 | 2.603 | 38.903 | 10.027 | 1.00 | 30.73 | O |
| ATOM | 3510 | CB | ASP | D | 658 | −0.239 | 38.636 | 8.347 | 1.00 | 38.52 | C |
| ATOM | 3511 | CG | ASP | D | 658 | −1.272 | 39.288 | 7.424 | 1.00 | 44.07 | C |
| ATOM | 3512 | OD1 | ASP | D | 658 | −2.462 | 38.886 | 7.501 | 1.00 | 44.99 | O |
| ATOM | 3513 | OD2 | ASP | D | 658 | −0.908 | 40.195 | 6.634 | 1.00 | 47.21 | O |
| ATOM | 3514 | N | LEU | D | 659 | 2.380 | 37.094 | 8.721 | 1.00 | 29.64 | N |
| ATOM | 3515 | CA | LEU | D | 659 | 3.234 | 36.260 | 9.550 | 1.00 | 29.57 | C |
| ATOM | 3516 | C | LEU | D | 659 | 4.643 | 36.850 | 9.684 | 1.00 | 30.44 | C |
| ATOM | 3517 | O | LEU | D | 659 | 5.180 | 36.946 | 10.780 | 1.00 | 28.18 | O |
| ATOM | 3518 | CB | LEU | D | 659 | 3.294 | 34.856 | 8.952 | 1.00 | 27.20 | C |

TABLE 4-continued

Stem Cell Factor Dimer

| ATOM | 3519 | CG | LEU | D | 659 | 3.988 | 33.762 | 9.749 | 1.00 | 28.07 | C |
|---|---|---|---|---|---|---|---|---|---|---|---|
| ATOM | 3520 | CD1 | LEU | D | 659 | 3.273 | 33.547 | 11.073 | 1.00 | 24.43 | C |
| ATOM | 3521 | CD2 | LEU | D | 659 | 3.992 | 32.481 | 8.929 | 1.00 | 26.60 | C |
| ATOM | 3522 | N | LEU | D | 660 | 5.223 | 37.263 | 8.561 | 1.00 | 32.08 | N |
| ATOM | 3523 | CA | LEU | D | 660 | 6.566 | 37.839 | 8.542 | 1.00 | 32.91 | C |
| ATOM | 3524 | C | LEU | D | 660 | 6.762 | 38.890 | 9.628 | 1.00 | 34.49 | C |
| ATOM | 3525 | O | LEU | D | 660 | 7.775 | 38.895 | 10.326 | 1.00 | 36.94 | O |
| ATOM | 3526 | CB | LEU | D | 660 | 6.844 | 38.458 | 7.169 | 1.00 | 32.39 | C |
| ATOM | 3527 | CG | LEU | D | 660 | 8.290 | 38.718 | 6.733 | 1.00 | 32.52 | C |
| ATOM | 3528 | CD1 | LEU | D | 660 | 9.087 | 37.429 | 6.762 | 1.00 | 32.35 | C |
| ATOM | 3529 | CD2 | LEU | D | 660 | 8.301 | 39.308 | 5.333 | 1.00 | 32.10 | C |
| ATOM | 3530 | N | ASP | D | 661 | 5.792 | 39.778 | 9.783 | 1.00 | 36.15 | N |
| ATOM | 3531 | CA | ASP | D | 661 | 5.894 | 40.832 | 10.785 | 1.00 | 34.98 | C |
| ATOM | 3532 | C | ASP | D | 661 | 5.908 | 40.354 | 12.243 | 1.00 | 32.23 | C |
| ATOM | 3533 | O | ASP | D | 661 | 6.042 | 41.165 | 13.153 | 1.00 | 33.01 | O |
| ATOM | 3534 | CB | ASP | D | 661 | 4.773 | 41.863 | 10.578 | 1.00 | 37.81 | C |
| ATOM | 3535 | CG | ASP | D | 661 | 5.132 | 42.913 | 9.528 | 1.00 | 43.94 | C |
| ATOM | 3536 | OD1 | ASP | D | 661 | 6.117 | 43.651 | 9.758 | 1.00 | 46.95 | O |
| ATOM | 3537 | OD2 | ASP | D | 661 | 4.443 | 43.006 | 8.479 | 1.00 | 44.46 | O |
| ATOM | 3538 | N | LYS | D | 662 | 5.783 | 39.050 | 12.475 | 1.00 | 27.57 | N |
| ATOM | 3539 | CA | LYS | D | 662 | 5.805 | 38.531 | 13.848 | 1.00 | 25.47 | C |
| ATOM | 3540 | C | LYS | D | 662 | 7.216 | 38.116 | 14.290 | 1.00 | 25.22 | C |
| ATOM | 3541 | O | LYS | D | 662 | 7.436 | 37.750 | 15.449 | 1.00 | 24.24 | O |
| ATOM | 3542 | CB | LYS | D | 662 | 4.864 | 37.328 | 13.975 | 1.00 | 23.70 | C |
| ATOM | 3543 | CG | LYS | D | 662 | 3.433 | 37.635 | 13.543 | 1.00 | 26.08 | C |
| ATOM | 3544 | CD | LYS | D | 662 | 2.815 | 38.689 | 14.439 | 1.00 | 27.79 | C |
| ATOM | 3545 | CE | LYS | D | 662 | 1.554 | 39.262 | 13.821 | 1.00 | 30.66 | C |
| ATOM | 3546 | NZ | LYS | D | 662 | 0.627 | 38.194 | 13.388 | 1.00 | 35.04 | N |
| ATOM | 3547 | N | PHE | D | 663 | 8.165 | 38.167 | 13.360 | 1.00 | 22.40 | N |
| ATOM | 3548 | CA | PHE | D | 663 | 9.538 | 37.784 | 13.662 | 1.00 | 24.06 | C |
| ATOM | 3549 | C | PHE | D | 663 | 10.503 | 38.921 | 13.350 | 1.00 | 23.21 | C |
| ATOM | 3550 | O | PHE | D | 663 | 10.111 | 39.918 | 12.759 | 1.00 | 23.66 | O |
| ATOM | 3551 | CB | PHE | D | 663 | 9.915 | 36.520 | 12.861 | 1.00 | 25.53 | C |
| ATOM | 3552 | CG | PHE | D | 663 | 9.010 | 35.335 | 13.133 | 1.00 | 26.81 | C |
| ATOM | 3553 | CD1 | PHE | D | 663 | 7.894 | 35.091 | 12.331 | 1.00 | 27.78 | C |
| ATOM | 3554 | CD2 | PHE | D | 663 | 9.244 | 34.499 | 14.226 | 1.00 | 22.65 | C |
| ATOM | 3555 | CE1 | PHE | D | 663 | 7.021 | 34.022 | 12.617 | 1.00 | 26.90 | C |
| ATOM | 3556 | CE2 | PHE | D | 663 | 8.384 | 33.443 | 14.518 | 1.00 | 24.82 | C |
| ATOM | 3557 | CZ | PHE | D | 663 | 7.273 | 33.202 | 13.714 | 1.00 | 25.89 | C |
| ATOM | 3558 | N | SER | D | 664 | 11.756 | 38.773 | 13.774 | 1.00 | 24.44 | N |
| ATOM | 3559 | CA | SER | D | 664 | 12.791 | 39.775 | 13.527 | 1.00 | 25.43 | C |
| ATOM | 3560 | C | SER | D | 664 | 14.016 | 39.062 | 12.985 | 1.00 | 24.80 | C |
| ATOM | 3561 | O | SER | D | 664 | 14.173 | 37.855 | 13.153 | 1.00 | 25.13 | O |
| ATOM | 3562 | CB | SER | D | 664 | 13.204 | 40.487 | 14.825 | 1.00 | 26.59 | C |
| ATOM | 3563 | OG | SER | D | 664 | 12.087 | 40.922 | 15.569 | 1.00 | 31.80 | O |
| ATOM | 3564 | N | ASN | D | 665 | 14.894 | 39.821 | 12.350 | 1.00 | 24.87 | N |
| ATOM | 3565 | CA | ASN | D | 665 | 16.136 | 39.277 | 11.819 | 1.00 | 24.88 | C |
| ATOM | 3566 | C | ASN | D | 665 | 17.097 | 39.010 | 12.969 | 1.00 | 24.12 | C |
| ATOM | 3567 | O | ASN | D | 665 | 16.887 | 39.477 | 14.089 | 1.00 | 21.58 | O |
| ATOM | 3568 | CB | ASN | D | 665 | 16.785 | 40.284 | 10.871 | 1.00 | 26.92 | C |
| ATOM | 3569 | CG | ASN | D | 665 | 15.990 | 40.484 | 9.610 | 1.00 | 24.93 | C |
| ATOM | 3570 | OD1 | ASN | D | 665 | 16.013 | 39.646 | 8.718 | 1.00 | 28.79 | O |
| ATOM | 3571 | ND2 | ASN | D | 665 | 15.269 | 41.594 | 9.533 | 1.00 | 27.05 | N |
| ATOM | 3572 | N | ILE | D | 666 | 18.149 | 38.252 | 12.680 | 1.00 | 24.28 | N |
| ATOM | 3573 | CA | ILE | D | 666 | 19.182 | 37.947 | 13.661 | 1.00 | 26.69 | C |
| ATOM | 3574 | C | ILE | D | 666 | 20.530 | 38.117 | 12.965 | 1.00 | 28.56 | C |
| ATOM | 3575 | O | ILE | D | 666 | 20.594 | 38.244 | 11.746 | 1.00 | 29.39 | O |
| ATOM | 3576 | CB | ILE | D | 666 | 19.058 | 36.494 | 14.213 | 1.00 | 26.87 | C |
| ATOM | 3577 | CG1 | ILE | D | 666 | 19.111 | 35.480 | 13.061 | 1.00 | 24.65 | C |
| ATOM | 3578 | CG2 | ILE | D | 666 | 17.764 | 36.348 | 15.000 | 1.00 | 24.84 | C |
| ATOM | 3579 | CD1 | ILE | D | 666 | 19.048 | 34.021 | 13.530 | 1.00 | 27.83 | C |
| ATOM | 3580 | N | SER | D | 667 | 21.606 | 38.116 | 13.735 | 1.00 | 33.18 | N |
| ATOM | 3581 | CA | SER | D | 667 | 22.940 | 38.287 | 13.167 | 1.00 | 36.42 | C |
| ATOM | 3582 | C | SER | D | 667 | 23.378 | 37.109 | 12.290 | 1.00 | 36.58 | C |
| ATOM | 3583 | O | SER | D | 667 | 24.070 | 37.301 | 11.288 | 1.00 | 38.40 | O |
| ATOM | 3584 | CB | SER | D | 667 | 23.959 | 38.511 | 14.292 | 1.00 | 39.38 | C |
| ATOM | 3585 | OG | SER | D | 667 | 25.231 | 38.838 | 13.760 | 1.00 | 46.92 | O |
| ATOM | 3586 | N | GLU | D | 668 | 22.993 | 35.892 | 12.667 | 1.00 | 34.88 | N |
| ATOM | 3587 | CA | GLU | D | 668 | 23.356 | 34.711 | 11.882 | 1.00 | 34.52 | C |
| ATOM | 3588 | C | GLU | D | 668 | 22.581 | 33.481 | 12.320 | 1.00 | 31.66 | C |
| ATOM | 3589 | O | GLU | D | 668 | 21.932 | 33.497 | 13.353 | 1.00 | 29.21 | O |
| ATOM | 3590 | CB | GLU | D | 668 | 24.870 | 34.424 | 11.971 | 1.00 | 38.03 | C |
| ATOM | 3591 | CG | GLU | D | 668 | 25.628 | 35.126 | 13.108 | 1.00 | 44.35 | C |
| ATOM | 3592 | CD | GLU | D | 668 | 25.293 | 34.587 | 14.486 | 1.00 | 48.70 | C |
| ATOM | 3593 | OE1 | GLU | D | 668 | 24.088 | 34.510 | 14.817 | 1.00 | 51.51 | O |
| ATOM | 3594 | OE2 | GLU | D | 668 | 26.237 | 34.253 | 15.243 | 1.00 | 49.33 | O |
| ATOM | 3595 | N | GLY | D | 669 | 22.655 | 32.418 | 11.526 | 1.00 | 31.97 | N |

TABLE 4-continued

Stem Cell Factor Dimer

| ATOM | 3596 | CA | GLY | D | 669 | 21.967 | 31.179 | 11.860 | 1.00 | 32.06 | C |
|---|---|---|---|---|---|---|---|---|---|---|---|
| ATOM | 3597 | C | GLY | D | 669 | 20.536 | 31.057 | 11.364 | 1.00 | 32.25 | C |
| ATOM | 3598 | O | GLY | D | 669 | 20.025 | 31.933 | 10.665 | 1.00 | 33.15 | O |
| ATOM | 3599 | N | LEU | D | 670 | 19.890 | 29.956 | 11.742 | 1.00 | 33.75 | N |
| ATOM | 3600 | CA | LEU | D | 670 | 18.504 | 29.657 | 11.368 | 1.00 | 32.29 | C |
| ATOM | 3601 | C | LEU | D | 670 | 17.562 | 30.800 | 11.776 | 1.00 | 30.44 | C |
| ATOM | 3602 | O | LEU | D | 670 | 17.341 | 31.042 | 12.974 | 1.00 | 30.45 | O |
| ATOM | 3603 | CB | LEU | D | 670 | 18.061 | 28.363 | 12.058 | 1.00 | 35.46 | C |
| ATOM | 3604 | CG | LEU | D | 670 | 16.981 | 27.492 | 11.395 | 1.00 | 37.43 | C |
| ATOM | 3605 | CD1 | LEU | D | 670 | 16.490 | 26.458 | 12.406 | 1.00 | 37.83 | C |
| ATOM | 3606 | CD2 | LEU | D | 670 | 15.826 | 28.346 | 10.919 | 1.00 | 40.46 | C |
| ATOM | 3607 | N | SER | D | 671 | 17.001 | 31.482 | 10.778 | 1.00 | 25.84 | N |
| ATOM | 3608 | CA | SER | D | 671 | 16.094 | 32.615 | 11.007 | 1.00 | 23.68 | C |
| ATOM | 3609 | C | SER | D | 671 | 14.693 | 32.368 | 10.446 | 1.00 | 23.41 | C |
| ATOM | 3610 | O | SER | D | 671 | 14.529 | 32.194 | 9.236 | 1.00 | 21.63 | O |
| ATOM | 3611 | CB | SER | D | 671 | 16.675 | 33.871 | 10.356 | 1.00 | 23.21 | C |
| ATOM | 3612 | OG | SER | D | 671 | 15.746 | 34.934 | 10.338 | 1.00 | 25.59 | O |
| ATOM | 3613 | N | ASN | D | 672 | 13.689 | 32.349 | 11.320 | 1.00 | 21.36 | N |
| ATOM | 3614 | CA | ASN | D | 672 | 12.308 | 32.143 | 10.875 | 1.00 | 22.35 | C |
| ATOM | 3615 | C | ASN | D | 672 | 11.912 | 33.258 | 9.902 | 1.00 | 22.21 | C |
| ATOM | 3616 | O | ASN | D | 672 | 11.157 | 33.032 | 8.950 | 1.00 | 24.69 | O |
| ATOM | 3617 | CB | ASN | D | 672 | 11.337 | 32.149 | 12.065 | 1.00 | 20.58 | C |
| ATOM | 3618 | CG | ASN | D | 672 | 11.329 | 30.833 | 12.837 | 1.00 | 21.92 | C |
| ATOM | 3619 | OD1 | ASN | D | 672 | 12.025 | 29.886 | 12.480 | 1.00 | 19.61 | O |
| ATOM | 3620 | ND2 | ASN | D | 672 | 10.534 | 30.776 | 13.908 | 1.00 | 17.38 | N |
| ATOM | 3621 | N | TYR | D | 673 | 12.432 | 34.456 | 10.145 | 1.00 | 21.48 | N |
| ATOM | 3622 | CA | TYR | D | 673 | 12.149 | 35.619 | 9.304 | 1.00 | 21.97 | C |
| ATOM | 3623 | C | TYR | D | 673 | 12.655 | 35.459 | 7.864 | 1.00 | 21.83 | C |
| ATOM | 3624 | O | TYR | D | 673 | 11.902 | 35.648 | 6.903 | 1.00 | 20.20 | O |
| ATOM | 3625 | CB | TYR | D | 673 | 12.784 | 36.886 | 9.904 | 1.00 | 23.46 | C |
| ATOM | 3626 | CG | TYR | D | 673 | 12.445 | 38.150 | 9.131 | 1.00 | 26.59 | C |
| ATOM | 3627 | CD1 | TYR | D | 673 | 11.410 | 38.985 | 9.543 | 1.00 | 26.58 | C |
| ATOM | 3628 | CD2 | TYR | D | 673 | 13.081 | 38.442 | 7.920 | 1.00 | 30.47 | C |
| ATOM | 3629 | CE1 | TYR | D | 673 | 11.005 | 40.066 | 8.768 | 1.00 | 28.11 | C |
| ATOM | 3630 | CE2 | TYR | D | 673 | 12.679 | 39.522 | 7.134 | 1.00 | 28.23 | C |
| ATOM | 3631 | CZ | TYR | D | 673 | 11.639 | 40.322 | 7.565 | 1.00 | 27.76 | C |
| ATOM | 3632 | OH | TYR | D | 673 | 11.205 | 41.353 | 6.771 | 1.00 | 30.64 | O |
| ATOM | 3633 | N | SER | D | 674 | 13.929 | 35.121 | 7.701 | 1.00 | 22.90 | N |
| ATOM | 3634 | CA | SER | D | 674 | 14.463 | 34.997 | 6.352 | 1.00 | 25.20 | C |
| ATOM | 3635 | C | SER | D | 674 | 13.767 | 33.896 | 5.585 | 1.00 | 24.29 | C |
| ATOM | 3636 | O | SER | D | 674 | 13.400 | 34.080 | 4.425 | 1.00 | 25.42 | O |
| ATOM | 3637 | CB | SER | D | 674 | 15.985 | 34.779 | 6.373 | 1.00 | 26.07 | C |
| ATOM | 3638 | OG | SER | D | 674 | 16.352 | 33.749 | 7.265 | 1.00 | 33.54 | O |
| ATOM | 3639 | N | ILE | D | 675 | 13.568 | 32.753 | 6.227 | 1.00 | 23.44 | N |
| ATOM | 3640 | CA | ILE | D | 675 | 12.878 | 31.653 | 5.558 | 1.00 | 25.04 | C |
| ATOM | 3641 | C | ILE | D | 675 | 11.495 | 32.101 | 5.075 | 1.00 | 23.96 | C |
| ATOM | 3642 | O | ILE | D | 675 | 11.128 | 31.875 | 3.924 | 1.00 | 24.31 | O |
| ATOM | 3643 | CB | ILE | D | 675 | 12.701 | 30.456 | 6.493 | 1.00 | 26.81 | C |
| ATOM | 3644 | CG1 | ILE | D | 675 | 14.068 | 29.859 | 6.822 | 1.00 | 27.96 | C |
| ATOM | 3645 | CG2 | ILE | D | 675 | 11.794 | 29.421 | 5.849 | 1.00 | 29.47 | C |
| ATOM | 3646 | CD1 | ILE | D | 675 | 14.017 | 28.844 | 7.936 | 1.00 | 31.50 | C |
| ATOM | 3647 | N | ILE | D | 676 | 10.738 | 32.749 | 5.949 | 1.00 | 24.69 | N |
| ATOM | 3648 | CA | ILE | D | 676 | 9.406 | 33.209 | 5.581 | 1.00 | 26.76 | C |
| ATOM | 3649 | C | ILE | D | 676 | 9.490 | 34.244 | 4.466 | 1.00 | 28.81 | C |
| ATOM | 3650 | O | ILE | D | 676 | 8.621 | 34.297 | 3.595 | 1.00 | 28.83 | O |
| ATOM | 3651 | CB | ILE | D | 676 | 8.677 | 33.815 | 6.811 | 1.00 | 26.99 | C |
| ATOM | 3652 | CG1 | ILE | D | 676 | 8.440 | 32.719 | 7.858 | 1.00 | 22.68 | C |
| ATOM | 3653 | CG2 | ILE | D | 676 | 7.356 | 34.476 | 6.388 | 1.00 | 23.23 | C |
| ATOM | 3654 | CD1 | ILE | D | 676 | 7.799 | 33.227 | 9.159 | 1.00 | 17.83 | C |
| ATOM | 3655 | N | ASP | D | 677 | 10.547 | 35.056 | 4.485 | 1.00 | 31.95 | N |
| ATOM | 3656 | CA | ASP | D | 677 | 10.729 | 36.089 | 3.468 | 1.00 | 32.21 | C |
| ATOM | 3657 | C | ASP | D | 677 | 10.961 | 35.454 | 2.095 | 1.00 | 32.22 | C |
| ATOM | 3658 | O | ASP | D | 677 | 10.474 | 35.965 | 1.092 | 1.00 | 29.94 | O |
| ATOM | 3659 | CB | ASP | D | 677 | 11.909 | 37.006 | 3.826 | 1.00 | 34.63 | C |
| ATOM | 3660 | CG | ASP | D | 677 | 11.887 | 38.319 | 3.049 | 1.00 | 33.89 | C |
| ATOM | 3661 | OD1 | ASP | D | 677 | 12.959 | 38.922 | 2.860 | 1.00 | 36.85 | O |
| ATOM | 3662 | OD2 | ASP | D | 677 | 10.795 | 38.759 | 2.634 | 1.00 | 36.66 | O |
| ATOM | 3663 | N | LYS | D | 678 | 11.711 | 34.352 | 2.051 | 1.00 | 33.09 | N |
| ATOM | 3664 | CA | LYS | D | 678 | 11.957 | 33.651 | 0.790 | 1.00 | 36.81 | C |
| ATOM | 3665 | C | LYS | D | 678 | 10.578 | 33.231 | 0.270 | 1.00 | 36.33 | C |
| ATOM | 3666 | O | LYS | D | 678 | 10.234 | 33.482 | −0.874 | 1.00 | 39.07 | O |
| ATOM | 3667 | CB | LYS | D | 678 | 12.785 | 32.371 | 0.993 | 1.00 | 36.47 | C |
| ATOM | 3668 | CG | LYS | D | 678 | 13.982 | 32.472 | 1.912 | 1.00 | 43.59 | C |
| ATOM | 3669 | CD | LYS | D | 678 | 15.174 | 33.140 | 1.250 | 1.00 | 45.20 | C |
| ATOM | 3670 | CE | LYS | D | 678 | 16.381 | 33.135 | 2.182 | 1.00 | 46.75 | C |
| ATOM | 3671 | NZ | LYS | D | 678 | 17.522 | 33.918 | 1.623 | 1.00 | 48.88 | N |
| ATOM | 3672 | N | LEU | D | 679 | 9.800 | 32.579 | 1.124 | 1.00 | 36.79 | N |

TABLE 4-continued

Stem Cell Factor Dimer

| ATOM | 3673 | CA | LEU | D | 679 | 8.462 | 32.130 | 0.756 | 1.00 | 37.88 | C |
|---|---|---|---|---|---|---|---|---|---|---|---|
| ATOM | 3674 | C | LEU | D | 679 | 7.656 | 33.264 | 0.145 | 1.00 | 37.94 | C |
| ATOM | 3675 | O | LEU | D | 679 | 7.076 | 33.116 | −0.919 | 1.00 | 37.41 | O |
| ATOM | 3676 | CB | LEU | D | 679 | 7.731 | 31.587 | 1.981 | 1.00 | 36.90 | C |
| ATOM | 3677 | CG | LEU | D | 679 | 7.811 | 30.078 | 2.212 | 1.00 | 40.44 | C |
| ATOM | 3678 | CD1 | LEU | D | 679 | 9.228 | 29.591 | 1.984 | 1.00 | 38.86 | C |
| ATOM | 3679 | CD2 | LEU | D | 679 | 7.322 | 29.751 | 3.619 | 1.00 | 38.47 | C |
| ATOM | 3680 | N | VAL | D | 680 | 7.607 | 34.398 | 0.827 | 1.00 | 38.68 | N |
| ATOM | 3681 | CA | VAL | D | 680 | 6.869 | 35.524 | 0.293 | 1.00 | 40.58 | C |
| ATOM | 3682 | C | VAL | D | 680 | 7.385 | 35.883 | −1.101 | 1.00 | 42.70 | C |
| ATOM | 3683 | O | VAL | D | 680 | 6.610 | 36.250 | −1.977 | 1.00 | 40.04 | O |
| ATOM | 3684 | CB | VAL | D | 680 | 6.991 | 36.752 | 1.197 | 1.00 | 41.30 | C |
| ATOM | 3685 | CG1 | VAL | D | 680 | 6.397 | 37.959 | 0.498 | 1.00 | 38.50 | C |
| ATOM | 3686 | CG2 | VAL | D | 680 | 6.278 | 36.489 | 2.535 | 1.00 | 40.52 | C |
| ATOM | 3687 | N | ASN | D | 681 | 8.694 | 35.767 | −1.308 | 1.00 | 44.70 | N |
| ATOM | 3688 | CA | ASN | D | 681 | 9.268 | 36.092 | −2.605 | 1.00 | 47.19 | C |
| ATOM | 3689 | C | ASN | D | 681 | 8.870 | 35.115 | −3.699 | 1.00 | 49.09 | C |
| ATOM | 3690 | O | ASN | D | 681 | 8.402 | 35.526 | −4.758 | 1.00 | 49.55 | O |
| ATOM | 3691 | CB | ASN | D | 681 | 10.793 | 36.183 | −2.517 | 1.00 | 46.42 | C |
| ATOM | 3692 | CG | ASN | D | 681 | 11.255 | 37.431 | −1.788 | 1.00 | 47.04 | C |
| ATOM | 3693 | OD1 | ASN | D | 681 | 10.559 | 38.447 | −1.786 | 1.00 | 46.74 | O |
| ATOM | 3694 | ND2 | ASN | D | 681 | 12.438 | 37.369 | −1.179 | 1.00 | 47.65 | N |
| ATOM | 3695 | N | ILE | D | 682 | 9.034 | 33.823 | −3.443 | 1.00 | 52.35 | N |
| ATOM | 3696 | CA | ILE | D | 682 | 8.689 | 32.820 | −4.444 | 1.00 | 56.10 | C |
| ATOM | 3697 | C | ILE | D | 682 | 7.199 | 32.786 | −4.778 | 1.00 | 58.45 | C |
| ATOM | 3698 | O | ILE | D | 682 | 6.812 | 32.342 | −5.860 | 1.00 | 60.06 | O |
| ATOM | 3699 | CB | ILE | D | 682 | 9.155 | 31.390 | −4.017 | 1.00 | 55.79 | C |
| ATOM | 3700 | CG1 | ILE | D | 682 | 7.956 | 30.505 | −3.664 | 1.00 | 56.27 | C |
| ATOM | 3701 | CG2 | ILE | D | 682 | 10.125 | 31.480 | −2.854 | 1.00 | 55.49 | C |
| ATOM | 3702 | CD1 | ILE | D | 682 | 7.271 | 30.852 | −2.363 | 1.00 | 57.94 | C |
| ATOM | 3703 | N | VAL | D | 683 | 6.367 | 33.260 | −3.858 | 1.00 | 60.52 | N |
| ATOM | 3704 | CA | VAL | D | 683 | 4.925 | 33.257 | −4.074 | 1.00 | 63.15 | C |
| ATOM | 3705 | C | VAL | D | 683 | 4.446 | 34.534 | −4.752 | 1.00 | 65.06 | C |
| ATOM | 3706 | O | VAL | D | 683 | 3.555 | 34.497 | −5.596 | 1.00 | 65.30 | O |
| ATOM | 3707 | CB | VAL | D | 683 | 4.161 | 33.064 | −2.740 | 1.00 | 63.35 | C |
| ATOM | 3708 | CG1 | VAL | D | 683 | 4.430 | 34.228 | −1.804 | 1.00 | 64.93 | C |
| ATOM | 3709 | CG2 | VAL | D | 683 | 2.676 | 32.928 | −3.005 | 1.00 | 63.39 | C |
| ATOM | 3710 | N | ASP | D | 684 | 5.038 | 35.664 | −4.384 | 1.00 | 67.27 | N |
| ATOM | 3711 | CA | ASP | D | 684 | 4.660 | 36.934 | −4.986 | 1.00 | 69.50 | C |
| ATOM | 3712 | C | ASP | D | 684 | 4.993 | 36.934 | −6.472 | 1.00 | 71.59 | C |
| ATOM | 3713 | O | ASP | D | 684 | 4.454 | 37.735 | −7.237 | 1.00 | 71.99 | O |
| ATOM | 3714 | CB | ASP | D | 684 | 5.367 | 38.091 | −4.276 | 1.00 | 68.58 | C |
| ATOM | 3715 | CG | ASP | D | 684 | 4.664 | 38.495 | −2.991 | 1.00 | 69.72 | C |
| ATOM | 3716 | OD1 | ASP | D | 684 | 4.179 | 37.594 | −2.273 | 1.00 | 70.09 | O |
| ATOM | 3717 | OD2 | ASP | D | 684 | 4.599 | 39.708 | −2.692 | 1.00 | 69.37 | O |
| ATOM | 3718 | N | ASP | D | 685 | 5.880 | 36.032 | −6.880 | 1.00 | 73.80 | N |
| ATOM | 3719 | CA | ASP | D | 685 | 6.251 | 35.929 | −8.285 | 1.00 | 75.57 | C |
| ATOM | 3720 | C | ASP | D | 685 | 5.175 | 35.127 | −9.001 | 1.00 | 76.68 | C |
| ATOM | 3721 | O | ASP | D | 685 | 4.844 | 35.398 | −10.156 | 1.00 | 77.13 | O |
| ATOM | 3722 | CB | ASP | D | 685 | 7.608 | 35.243 | −8.442 | 1.00 | 75.95 | C |
| ATOM | 3723 | CG | ASP | D | 685 | 8.738 | 36.038 | −7.821 | 1.00 | 77.23 | C |
| ATOM | 3724 | OD1 | ASP | D | 685 | 8.823 | 37.260 | −8.075 | 1.00 | 76.55 | O |
| ATOM | 3725 | OD2 | ASP | D | 685 | 9.548 | 35.439 | −7.084 | 1.00 | 78.99 | O |
| ATOM | 3726 | N | LEU | D | 686 | 4.628 | 34.134 | −8.311 | 1.00 | 77.72 | N |
| ATOM | 3727 | CA | LEU | D | 686 | 3.570 | 33.321 | −8.892 | 1.00 | 79.71 | C |
| ATOM | 3728 | C | LEU | D | 686 | 2.360 | 34.228 | −9.082 | 1.00 | 80.70 | C |
| ATOM | 3729 | O | LEU | D | 686 | 1.616 | 34.099 | −10.053 | 1.00 | 80.11 | O |
| ATOM | 3730 | CB | LEU | D | 686 | 3.215 | 32.163 | −7.959 | 1.00 | 79.55 | C |
| ATOM | 3731 | CG | LEU | D | 686 | 4.346 | 31.181 | −7.646 | 1.00 | 80.42 | C |
| ATOM | 3732 | CD1 | LEU | D | 686 | 3.840 | 30.122 | −6.676 | 1.00 | 80.91 | C |
| ATOM | 3733 | CD2 | LEU | D | 686 | 4.849 | 30.537 | −8.929 | 1.00 | 79.73 | C |
| ATOM | 3734 | N | VAL | D | 687 | 2.182 | 35.151 | −8.142 | 1.00 | 82.79 | N |
| ATOM | 3735 | CA | VAL | D | 687 | 1.080 | 36.103 | −8.185 | 1.00 | 85.25 | C |
| ATOM | 3736 | C | VAL | D | 687 | 1.232 | 36.965 | −9.433 | 1.00 | 86.98 | C |
| ATOM | 3737 | O | VAL | D | 687 | 0.248 | 37.366 | −10.053 | 1.00 | 87.41 | O |
| ATOM | 3738 | CB | VAL | D | 687 | 1.088 | 37.025 | −6.943 | 1.00 | 85.38 | C |
| ATOM | 3739 | CG1 | VAL | D | 687 | −0.095 | 37.983 | −6.993 | 1.00 | 85.62 | C |
| ATOM | 3740 | CG2 | VAL | D | 687 | 1.049 | 36.191 | −5.673 | 1.00 | 84.82 | C |
| ATOM | 3741 | N | GLU | D | 688 | 2.480 | 37.242 | −9.792 | 1.00 | 89.00 | N |
| ATOM | 3742 | CA | GLU | D | 688 | 2.786 | 38.048 | −10.964 | 1.00 | 91.27 | C |
| ATOM | 3743 | C | GLU | D | 688 | 2.228 | 37.366 | −12.213 | 1.00 | 92.66 | C |
| ATOM | 3744 | O | GLU | D | 688 | 1.660 | 38.020 | −13.092 | 1.00 | 92.59 | O |
| ATOM | 3745 | CB | GLU | D | 688 | 4.305 | 38.227 | −11.075 | 1.00 | 91.61 | C |
| ATOM | 3746 | CG | GLU | D | 688 | 4.768 | 39.112 | −12.217 | 1.00 | 92.97 | C |
| ATOM | 3747 | CD | GLU | D | 688 | 6.227 | 39.507 | −12.081 | 1.00 | 93.95 | C |
| ATOM | 3748 | OE1 | GLU | D | 688 | 7.074 | 38.610 | −11.886 | 1.00 | 94.46 | O |
| ATOM | 3749 | OE2 | GLU | D | 688 | 6.529 | 40.716 | −12.171 | 1.00 | 94.79 | O |

TABLE 4-continued

Stem Cell Factor Dimer

| ATOM | 3750 | N | CYS | D | 689 | 2.381 | 36.046 | −12.277 | 1.00 | 94.04 | N |
|---|---|---|---|---|---|---|---|---|---|---|---|
| ATOM | 3751 | CA | CYS | D | 689 | 1.887 | 35.268 | −13.408 | 1.00 | 95.48 | C |
| ATOM | 3752 | C | CYS | D | 689 | 0.356 | 35.271 | −13.421 | 1.00 | 96.12 | C |
| ATOM | 3753 | O | CYS | D | 689 | −0.268 | 34.972 | −14.442 | 1.00 | 96.57 | O |
| ATOM | 3754 | CB | CYS | D | 689 | 2.409 | 33.829 | −13.321 | 1.00 | 95.86 | C |
| ATOM | 3755 | SG | CYS | D | 689 | 2.002 | 32.775 | −14.743 | 1.00 | 96.55 | S |
| ATOM | 3756 | N | VAL | D | 690 | −0.242 | 35.613 | −12.282 | 1.00 | 96.33 | N |
| ATOM | 3757 | CA | VAL | D | 690 | −1.697 | 35.661 | −12.154 | 1.00 | 96.28 | C |
| ATOM | 3758 | C | VAL | D | 690 | −2.238 | 37.003 | −12.642 | 1.00 | 95.97 | C |
| ATOM | 3759 | O | VAL | D | 690 | −3.206 | 37.050 | −13.402 | 1.00 | 95.87 | O |
| ATOM | 3760 | CB | VAL | D | 690 | −2.134 | 35.450 | −10.688 | 1.00 | 96.58 | C |
| ATOM | 3761 | CG1 | VAL | D | 690 | −3.649 | 35.491 | −10.586 | 1.00 | 96.64 | C |
| ATOM | 3762 | CG2 | VAL | D | 690 | −1.604 | 34.123 | −10.174 | 1.00 | 96.70 | C |
| ATOM | 3763 | N | LYS | D | 691 | −1.615 | 38.089 | −12.192 | 1.00 | 95.50 | N |
| ATOM | 3764 | CA | LYS | D | 691 | −2.017 | 39.432 | −12.601 | 1.00 | 95.00 | C |
| ATOM | 3765 | C | LYS | D | 691 | −1.937 | 39.497 | −14.123 | 1.00 | 94.21 | C |
| ATOM | 3766 | O | LYS | D | 691 | −2.702 | 40.207 | −14.777 | 1.00 | 94.03 | O |
| ATOM | 3767 | CB | LYS | D | 691 | −1.075 | 40.469 | −11.982 | 1.00 | 95.64 | C |
| ATOM | 3768 | CG | LYS | D | 691 | −1.254 | 41.892 | −12.501 | 1.00 | 96.98 | C |
| ATOM | 3769 | CD | LYS | D | 691 | −2.627 | 42.458 | −12.175 | 1.00 | 97.92 | C |
| ATOM | 3770 | CE | LYS | D | 691 | −2.757 | 43.889 | −12.679 | 1.00 | 98.61 | C |
| ATOM | 3771 | NZ | LYS | D | 691 | −4.089 | 44.483 | −12.373 | 1.00 | 99.33 | N |
| ATOM | 3772 | N | GLU | D | 692 | −0.996 | 38.731 | −14.667 | 1.00 | 93.18 | N |
| ATOM | 3773 | CA | GLU | D | 692 | −0.762 | 38.642 | −16.103 | 1.00 | 91.81 | C |
| ATOM | 3774 | C | GLU | D | 692 | −1.879 | 37.862 | −16.791 | 1.00 | 91.95 | C |
| ATOM | 3775 | O | GLU | D | 692 | −2.336 | 38.229 | −17.876 | 1.00 | 91.71 | O |
| ATOM | 3776 | CB | GLU | D | 692 | 0.576 | 37.944 | −16.347 | 1.00 | 90.32 | C |
| ATOM | 3777 | CG | GLU | D | 692 | 0.773 | 37.422 | −17.752 | 1.00 | 88.30 | C |
| ATOM | 3778 | CD | GLU | D | 692 | 2.032 | 36.591 | −17.881 | 1.00 | 87.50 | C |
| ATOM | 3779 | OE1 | GLU | D | 692 | 3.132 | 37.138 | −17.656 | 1.00 | 86.63 | O |
| ATOM | 3780 | OE2 | GLU | D | 692 | 1.923 | 35.390 | −18.203 | 1.00 | 87.16 | O |
| ATOM | 3781 | N | ASN | D | 693 | −2.312 | 36.783 | −16.146 | 1.00 | 92.11 | N |
| ATOM | 3782 | CA | ASN | D | 693 | −3.365 | 35.924 | −16.676 | 1.00 | 92.10 | C |
| ATOM | 3783 | C | ASN | D | 693 | −4.707 | 36.645 | −16.786 | 1.00 | 92.44 | C |
| ATOM | 3784 | O | ASN | D | 693 | −5.733 | 36.024 | −17.068 | 1.00 | 92.48 | O |
| ATOM | 3785 | CB | ASN | D | 693 | −3.519 | 34.688 | −15.787 | 1.00 | 91.67 | C |
| ATOM | 3786 | CG | ASN | D | 693 | −4.404 | 33.629 | −16.411 | 1.00 | 91.37 | C |
| ATOM | 3787 | OD1 | ASN | D | 693 | −4.050 | 33.029 | −17.427 | 1.00 | 91.61 | O |
| ATOM | 3788 | ND2 | ASN | D | 693 | −5.565 | 33.397 | −15.808 | 1.00 | 90.95 | N |
| ATOM | 3789 | N | SER | D | 694 | −4.701 | 37.955 | −16.559 | 1.00 | 92.92 | N |
| ATOM | 3790 | CA | SER | D | 694 | −5.927 | 38.740 | −16.653 | 1.00 | 93.70 | C |
| ATOM | 3791 | C | SER | D | 694 | −6.313 | 38.895 | −18.123 | 1.00 | 94.44 | C |
| ATOM | 3792 | O | SER | D | 694 | −7.191 | 39.689 | −18.464 | 1.00 | 94.58 | O |
| ATOM | 3793 | CB | SER | D | 694 | −5.726 | 40.122 | −16.021 | 1.00 | 93.44 | C |
| ATOM | 3794 | OG | SER | D | 694 | −4.747 | 40.873 | −16.720 | 1.00 | 92.64 | O |
| ATOM | 3795 | N | SER | D | 695 | −5.649 | 38.125 | −18.984 | 1.00 | 95.04 | N |
| ATOM | 3796 | CA | SER | D | 695 | −5.895 | 38.169 | −20.423 | 1.00 | 95.13 | C |
| ATOM | 3797 | C | SER | D | 695 | −6.702 | 36.972 | −20.935 | 1.00 | 95.56 | C |
| ATOM | 3798 | O | SER | D | 695 | −6.197 | 35.848 | −20.998 | 1.00 | 95.95 | O |
| ATOM | 3799 | CB | SER | D | 695 | −4.562 | 38.258 | −21.180 | 1.00 | 94.47 | C |
| ATOM | 3800 | OG | SER | D | 695 | −3.711 | 37.166 | −20.871 | 1.00 | 93.11 | O |
| ATOM | 3801 | N | LYS | D | 696 | −7.957 | 37.236 | −21.297 | 1.00 | 95.46 | N |
| ATOM | 3802 | CA | LYS | D | 696 | −8.879 | 36.227 | −21.824 | 1.00 | 94.89 | C |
| ATOM | 3803 | C | LYS | D | 696 | −8.843 | 34.878 | −21.101 | 1.00 | 94.36 | C |
| ATOM | 3804 | O | LYS | D | 696 | −9.328 | 33.871 | −21.625 | 1.00 | 93.84 | O |
| ATOM | 3805 | CB | LYS | D | 696 | −8.622 | 36.025 | −23.319 | 1.00 | 94.98 | C |
| ATOM | 3806 | N | ASP | D | 697 | −8.277 | 34.859 | −19.898 | 1.00 | 93.56 | N |
| ATOM | 3807 | CA | ASP | D | 697 | −8.186 | 33.630 | −19.118 | 1.00 | 92.68 | C |
| ATOM | 3808 | C | ASP | D | 697 | −8.977 | 33.819 | −17.827 | 1.00 | 91.92 | C |
| ATOM | 3809 | O | ASP | D | 697 | −8.590 | 34.609 | −16.965 | 1.00 | 91.14 | O |
| ATOM | 3810 | CB | ASP | D | 697 | −6.717 | 33.320 | −18.800 | 1.00 | 93.02 | C |
| ATOM | 3811 | CG | ASP | D | 697 | −6.447 | 31.827 | −18.644 | 1.00 | 93.69 | C |
| ATOM | 3812 | OD1 | ASP | D | 697 | −7.092 | 31.181 | −17.789 | 1.00 | 93.85 | O |
| ATOM | 3813 | OD2 | ASP | D | 697 | −5.580 | 31.299 | −19.378 | 1.00 | 93.74 | O |
| ATOM | 3814 | N | LEU | D | 698 | −10.087 | 33.098 | −17.700 | 1.00 | 91.37 | N |
| ATOM | 3815 | CA | LEU | D | 698 | −10.930 | 33.205 | −16.514 | 1.00 | 91.28 | C |
| ATOM | 3816 | C | LEU | D | 698 | −10.404 | 32.357 | −15.357 | 1.00 | 92.32 | C |
| ATOM | 3817 | O | LEU | D | 698 | −9.417 | 31.633 | −15.497 | 1.00 | 91.67 | O |
| ATOM | 3818 | CB | LEU | D | 698 | −12.371 | 32.795 | −16.848 | 1.00 | 89.61 | C |
| ATOM | 3819 | CG | LEU | D | 698 | −13.450 | 33.088 | −15.795 | 1.00 | 88.07 | C |
| ATOM | 3820 | CD1 | LEU | D | 698 | −13.535 | 34.588 | −15.547 | 1.00 | 86.94 | C |
| ATOM | 3821 | CD2 | LEU | D | 698 | −14.792 | 32.557 | −16.267 | 1.00 | 86.97 | C |
| ATOM | 3822 | N | LYS | D | 699 | −11.075 | 32.465 | −14.213 | 1.00 | 94.08 | N |
| ATOM | 3823 | CA | LYS | D | 699 | −10.717 | 31.732 | −13.002 | 1.00 | 95.68 | C |
| ATOM | 3824 | C | LYS | D | 699 | −11.705 | 32.139 | −11.917 | 1.00 | 96.86 | C |
| ATOM | 3825 | O | LYS | D | 699 | −11.381 | 32.941 | −11.038 | 1.00 | 97.13 | O |
| ATOM | 3826 | CB | LYS | D | 699 | −9.291 | 32.078 | −12.573 | 1.00 | 95.48 | C |

TABLE 4-continued

Stem Cell Factor Dimer

| ATOM | 3827 | N | LYS | D | 700 | −12.913 | 31.586 | −11.986 | 1.00 | 98.29 | N |
|------|------|----|-----|---|-----|---------|--------|---------|------|--------|---|
| ATOM | 3828 | CA | LYS | D | 700 | −13.960 | 31.911 | −11.023 | 1.00 | 99.67 | C |
| ATOM | 3829 | C | LYS | D | 700 | −14.250 | 30.798 | −10.021 | 1.00 | 100.65 | C |
| ATOM | 3830 | O | LYS | D | 700 | −14.552 | 29.664 | −10.401 | 1.00 | 101.39 | O |
| ATOM | 3831 | CB | LYS | D | 700 | −15.241 | 32.286 | −11.761 | 1.00 | 99.60 | C |
| ATOM | 3832 | N | SER | D | 701 | −14.161 | 31.148 | −8.739 | 1.00 | 100.84 | N |
| ATOM | 3833 | CA | SER | D | 701 | −14.412 | 30.230 | −7.630 | 1.00 | 100.59 | C |
| ATOM | 3834 | C | SER | D | 701 | −13.874 | 30.848 | −6.348 | 1.00 | 100.43 | C |
| ATOM | 3835 | O | SER | D | 701 | −13.041 | 30.254 | −5.663 | 1.00 | 100.66 | O |
| ATOM | 3836 | CB | SER | D | 701 | −13.737 | 28.894 | −7.879 | 1.00 | 100.76 | C |
| ATOM | 3837 | N | PHE | D | 702 | −14.351 | 32.048 | −6.030 | 1.00 | 99.83 | N |
| ATOM | 3838 | CA | PHE | D | 702 | −13.910 | 32.748 | −4.830 | 1.00 | 98.88 | C |
| ATOM | 3839 | C | PHE | D | 702 | −14.937 | 33.780 | −4.372 | 1.00 | 97.79 | C |
| ATOM | 3840 | O | PHE | D | 702 | −14.829 | 34.964 | −4.697 | 1.00 | 97.98 | O |
| ATOM | 3841 | CB | PHE | D | 702 | −12.566 | 33.429 | −5.089 | 1.00 | 98.81 | C |
| ATOM | 3842 | N | LYS | D | 703 | −15.935 | 33.323 | −3.620 | 1.00 | 95.97 | N |
| ATOM | 3843 | CA | LYS | D | 703 | −16.972 | 34.214 | −3.111 | 1.00 | 93.51 | C |
| ATOM | 3844 | C | LYS | D | 703 | −16.330 | 35.178 | −2.122 | 1.00 | 91.41 | C |
| ATOM | 3845 | O | LYS | D | 703 | −15.883 | 36.264 | −2.493 | 1.00 | 91.96 | O |
| ATOM | 3846 | CB | LYS | D | 703 | −18.071 | 33.406 | −2.426 | 1.00 | 93.25 | C |
| ATOM | 3847 | N | SER | D | 704 | −16.287 | 34.767 | −0.861 | 1.00 | 88.69 | N |
| ATOM | 3848 | CA | SER | D | 704 | −15.684 | 35.562 | 0.201 | 1.00 | 85.20 | C |
| ATOM | 3849 | C | SER | D | 704 | −14.912 | 34.587 | 1.077 | 1.00 | 82.83 | C |
| ATOM | 3850 | O | SER | D | 704 | −15.429 | 34.111 | 2.089 | 1.00 | 83.42 | O |
| ATOM | 3851 | CB | SER | D | 704 | −16.763 | 36.259 | 1.035 | 1.00 | 84.52 | C |
| ATOM | 3852 | OG | SER | D | 704 | −17.574 | 37.096 | 0.234 | 1.00 | 82.90 | O |
| ATOM | 3853 | N | PRO | D | 705 | −13.668 | 34.259 | 0.688 | 1.00 | 79.97 | N |
| ATOM | 3854 | CA | PRO | D | 705 | −12.863 | 33.325 | 1.476 | 1.00 | 76.91 | C |
| ATOM | 3855 | C | PRO | D | 705 | −12.953 | 33.616 | 2.972 | 1.00 | 74.02 | C |
| ATOM | 3856 | O | PRO | D | 705 | −12.356 | 34.567 | 3.467 | 1.00 | 74.68 | O |
| ATOM | 3857 | CB | PRO | D | 705 | −11.460 | 33.535 | 0.916 | 1.00 | 76.37 | C |
| ATOM | 3858 | CG | PRO | D | 705 | −11.733 | 33.807 | −0.522 | 1.00 | 77.44 | C |
| ATOM | 3859 | CD | PRO | D | 705 | −12.896 | 34.776 | −0.457 | 1.00 | 78.70 | C |
| ATOM | 3860 | N | GLU | D | 706 | −13.720 | 32.797 | 3.683 | 1.00 | 71.23 | N |
| ATOM | 3861 | CA | GLU | D | 706 | −13.886 | 32.963 | 5.121 | 1.00 | 67.86 | C |
| ATOM | 3862 | C | GLU | D | 706 | −12.562 | 32.719 | 5.851 | 1.00 | 63.69 | C |
| ATOM | 3863 | O | GLU | D | 706 | −11.985 | 31.632 | 5.768 | 1.00 | 62.35 | O |
| ATOM | 3864 | CB | GLU | D | 706 | −14.953 | 31.987 | 5.645 | 1.00 | 70.07 | C |
| ATOM | 3865 | CG | GLU | D | 706 | −15.132 | 31.997 | 7.167 | 1.00 | 72.39 | C |
| ATOM | 3866 | CD | GLU | D | 706 | −16.106 | 30.933 | 7.670 | 1.00 | 75.20 | C |
| ATOM | 3867 | OE1 | GLU | D | 706 | −17.334 | 31.081 | 7.449 | 1.00 | 75.30 | O |
| ATOM | 3868 | OE2 | GLU | D | 706 | −15.638 | 29.945 | 8.287 | 1.00 | 74.89 | O |
| ATOM | 3869 | N | PRO | D | 707 | −12.060 | 33.735 | 6.572 | 1.00 | 59.49 | N |
| ATOM | 3870 | CA | PRO | D | 707 | −10.800 | 33.583 | 7.308 | 1.00 | 56.04 | C |
| ATOM | 3871 | C | PRO | D | 707 | −10.896 | 32.465 | 8.339 | 1.00 | 51.97 | C |
| ATOM | 3872 | O | PRO | D | 707 | −11.812 | 32.437 | 9.158 | 1.00 | 50.54 | O |
| ATOM | 3873 | CB | PRO | D | 707 | −10.599 | 34.958 | 7.949 | 1.00 | 56.55 | C |
| ATOM | 3874 | CG | PRO | D | 707 | −11.999 | 35.492 | 8.074 | 1.00 | 57.25 | C |
| ATOM | 3875 | CD | PRO | D | 707 | −12.619 | 35.084 | 6.762 | 1.00 | 58.60 | C |
| ATOM | 3876 | N | ARG | D | 708 | −9.948 | 31.540 | 8.277 | 1.00 | 48.78 | N |
| ATOM | 3877 | CA | ARG | D | 708 | −9.907 | 30.406 | 9.183 | 1.00 | 46.21 | C |
| ATOM | 3878 | C | ARG | D | 708 | −8.555 | 30.341 | 9.879 | 1.00 | 43.96 | C |
| ATOM | 3879 | O | ARG | D | 708 | −7.595 | 30.996 | 9.466 | 1.00 | 42.60 | O |
| ATOM | 3880 | CB | ARG | D | 708 | −10.154 | 29.109 | 8.407 | 1.00 | 48.71 | C |
| ATOM | 3881 | CG | ARG | D | 708 | −11.570 | 28.961 | 7.884 | 1.00 | 52.85 | C |
| ATOM | 3882 | CD | ARG | D | 708 | −11.704 | 27.807 | 6.891 | 1.00 | 56.82 | C |
| ATOM | 3883 | NE | ARG | D | 708 | −11.230 | 26.528 | 7.420 | 1.00 | 59.99 | N |
| ATOM | 3884 | CZ | ARG | D | 708 | −11.349 | 25.365 | 6.782 | 1.00 | 61.51 | C |
| ATOM | 3885 | NH1 | ARG | D | 708 | −11.933 | 25.317 | 5.590 | 1.00 | 63.09 | N |
| ATOM | 3886 | NH2 | ARG | D | 708 | −10.867 | 24.251 | 7.322 | 1.00 | 61.87 | N |
| ATOM | 3887 | N | LEU | D | 709 | −8.485 | 29.556 | 10.946 | 1.00 | 41.48 | N |
| ATOM | 3888 | CA | LEU | D | 709 | −7.247 | 29.412 | 11.688 | 1.00 | 39.42 | C |
| ATOM | 3889 | C | LEU | D | 709 | −6.624 | 28.053 | 11.395 | 1.00 | 36.66 | C |
| ATOM | 3890 | O | LEU | D | 709 | −7.319 | 27.038 | 11.339 | 1.00 | 35.31 | O |
| ATOM | 3891 | CB | LEU | D | 709 | −7.502 | 29.582 | 13.188 | 1.00 | 38.48 | C |
| ATOM | 3892 | CG | LEU | D | 709 | −7.990 | 30.975 | 13.600 | 1.00 | 39.85 | C |
| ATOM | 3893 | CD1 | LEU | D | 709 | −8.041 | 31.071 | 15.111 | 1.00 | 39.71 | C |
| ATOM | 3894 | CD2 | LEU | D | 709 | −7.064 | 32.045 | 13.094 | 1.00 | 39.94 | C |
| ATOM | 3895 | N | PHE | D | 710 | −5.310 | 28.047 | 11.194 | 1.00 | 33.55 | N |
| ATOM | 3896 | CA | PHE | D | 710 | −4.590 | 26.816 | 10.896 | 1.00 | 31.41 | C |
| ATOM | 3897 | C | PHE | D | 710 | −3.347 | 26.700 | 11.758 | 1.00 | 29.90 | C |
| ATOM | 3898 | O | PHE | D | 710 | −2.717 | 27.710 | 12.080 | 1.00 | 27.69 | O |
| ATOM | 3899 | CB | PHE | D | 710 | −4.174 | 26.784 | 9.419 | 1.00 | 31.40 | C |
| ATOM | 3900 | CG | PHE | D | 710 | −5.334 | 26.816 | 8.450 | 1.00 | 34.01 | C |
| ATOM | 3901 | CD1 | PHE | D | 710 | −6.004 | 28.010 | 8.173 | 1.00 | 34.43 | C |
| ATOM | 3902 | CD2 | PHE | D | 710 | −5.771 | 25.649 | 7.831 | 1.00 | 33.62 | C |
| ATOM | 3903 | CE1 | PHE | D | 710 | −7.092 | 28.042 | 7.297 | 1.00 | 31.45 | C |

TABLE 4-continued

Stem Cell Factor Dimer

| ATOM | 3904 | CE2 | PHE | D | 710 | −6.861 | 25.672 | 6.951 | 1.00 | 34.68 | C |
|---|---|---|---|---|---|---|---|---|---|---|---|
| ATOM | 3905 | CZ | PHE | D | 710 | −7.520 | 26.876 | 6.687 | 1.00 | 33.49 | C |
| ATOM | 3906 | N | THR | D | 711 | −3.002 | 25.478 | 12.160 | 1.00 | 29.11 | N |
| ATOM | 3907 | CA | THR | D | 711 | −1.778 | 25.303 | 12.932 | 1.00 | 27.42 | C |
| ATOM | 3908 | C | THR | D | 711 | −0.691 | 25.389 | 11.860 | 1.00 | 26.26 | C |
| ATOM | 3909 | O | THR | D | 711 | −0.999 | 25.330 | 10.667 | 1.00 | 25.34 | O |
| ATOM | 3910 | CB | THR | D | 711 | −1.713 | 23.934 | 13.642 | 1.00 | 26.97 | C |
| ATOM | 3911 | OG1 | THR | D | 711 | −1.979 | 22.894 | 12.704 | 1.00 | 24.41 | O |
| ATOM | 3912 | CG2 | THR | D | 711 | −2.716 | 23.871 | 14.776 | 1.00 | 25.72 | C |
| ATOM | 3913 | N | PRO | D | 712 | 0.581 | 25.565 | 12.255 | 1.00 | 26.02 | N |
| ATOM | 3914 | CA | PRO | D | 712 | 1.616 | 25.649 | 11.215 | 1.00 | 26.21 | C |
| ATOM | 3915 | C | PRO | D | 712 | 1.557 | 24.444 | 10.281 | 1.00 | 28.47 | C |
| ATOM | 3916 | O | PRO | D | 712 | 1.554 | 24.586 | 9.047 | 1.00 | 25.16 | O |
| ATOM | 3917 | CB | PRO | D | 712 | 2.902 | 25.718 | 12.026 | 1.00 | 22.24 | C |
| ATOM | 3918 | CG | PRO | D | 712 | 2.469 | 26.544 | 13.205 | 1.00 | 23.05 | C |
| ATOM | 3919 | CD | PRO | D | 712 | 1.134 | 25.912 | 13.576 | 1.00 | 23.09 | C |
| ATOM | 3920 | N | GLU | D | 713 | 1.490 | 23.266 | 10.891 | 1.00 | 29.14 | N |
| ATOM | 3921 | CA | GLU | D | 713 | 1.407 | 22.007 | 10.164 | 1.00 | 32.67 | C |
| ATOM | 3922 | C | GLU | D | 713 | 0.417 | 22.064 | 8.999 | 1.00 | 31.32 | C |
| ATOM | 3923 | O | GLU | D | 713 | 0.785 | 21.884 | 7.842 | 1.00 | 32.51 | O |
| ATOM | 3924 | CB | GLU | D | 713 | 0.971 | 20.889 | 11.118 | 1.00 | 34.67 | C |
| ATOM | 3925 | CG | GLU | D | 713 | 1.911 | 19.705 | 11.123 | 1.00 | 41.80 | C |
| ATOM | 3926 | CD | GLU | D | 713 | 1.433 | 18.571 | 12.007 | 1.00 | 40.60 | C |
| ATOM | 3927 | OE1 | GLU | D | 713 | 2.151 | 17.559 | 12.077 | 1.00 | 45.79 | O |
| ATOM | 3928 | OE2 | GLU | D | 713 | 0.352 | 18.682 | 12.621 | 1.00 | 39.13 | O |
| ATOM | 3929 | N | GLU | D | 714 | −0.844 | 22.328 | 9.307 | 1.00 | 30.43 | N |
| ATOM | 3930 | CA | GLU | D | 714 | −1.849 | 22.344 | 8.264 | 1.00 | 30.71 | C |
| ATOM | 3931 | C | GLU | D | 714 | −1.754 | 23.559 | 7.339 | 1.00 | 28.77 | C |
| ATOM | 3932 | O | GLU | D | 714 | −2.101 | 23.480 | 6.155 | 1.00 | 28.54 | O |
| ATOM | 3933 | CB | GLU | D | 714 | −3.247 | 22.191 | 8.900 | 1.00 | 31.99 | C |
| ATOM | 3934 | CG | GLU | D | 714 | −3.625 | 23.269 | 9.896 | 1.00 | 37.31 | C |
| ATOM | 3935 | CD | GLU | D | 714 | −4.553 | 22.772 | 11.002 | 1.00 | 39.58 | C |
| ATOM | 3936 | OE1 | GLU | D | 714 | −5.266 | 23.612 | 11.597 | 1.00 | 38.58 | O |
| ATOM | 3937 | OE2 | GLU | D | 714 | −4.555 | 21.552 | 11.290 | 1.00 | 40.23 | O |
| ATOM | 3938 | N | PHE | D | 715 | −1.266 | 24.684 | 7.847 | 1.00 | 27.44 | N |
| ATOM | 3939 | CA | PHE | D | 715 | −1.145 | 25.849 | 6.980 | 1.00 | 24.07 | C |
| ATOM | 3940 | C | PHE | D | 715 | −0.157 | 25.559 | 5.856 | 1.00 | 24.36 | C |
| ATOM | 3941 | O | PHE | D | 715 | −0.419 | 25.855 | 4.690 | 1.00 | 21.57 | O |
| ATOM | 3942 | CB | PHE | D | 715 | −0.649 | 27.075 | 7.746 | 1.00 | 23.21 | C |
| ATOM | 3943 | CG | PHE | D | 715 | −0.450 | 28.296 | 6.871 | 1.00 | 22.37 | C |
| ATOM | 3944 | CD1 | PHE | D | 715 | −1.496 | 29.183 | 6.640 | 1.00 | 22.39 | C |
| ATOM | 3945 | CD2 | PHE | D | 715 | 0.778 | 28.546 | 6.272 | 1.00 | 21.02 | C |
| ATOM | 3946 | CE1 | PHE | D | 715 | −1.319 | 30.312 | 5.824 | 1.00 | 26.50 | C |
| ATOM | 3947 | CE2 | PHE | D | 715 | 0.970 | 29.666 | 5.452 | 1.00 | 22.98 | C |
| ATOM | 3948 | CZ | PHE | D | 715 | −0.082 | 30.555 | 5.229 | 1.00 | 24.25 | C |
| ATOM | 3949 | N | PHE | D | 716 | 0.987 | 24.981 | 6.203 | 1.00 | 25.04 | N |
| ATOM | 3950 | CA | PHE | D | 716 | 1.989 | 24.714 | 5.184 | 1.00 | 28.02 | C |
| ATOM | 3951 | C | PHE | D | 716 | 1.745 | 23.514 | 4.276 | 1.00 | 29.77 | C |
| ATOM | 3952 | O | PHE | D | 716 | 2.322 | 23.426 | 3.192 | 1.00 | 30.86 | O |
| ATOM | 3953 | CB | PHE | D | 716 | 3.379 | 24.673 | 5.817 | 1.00 | 20.28 | C |
| ATOM | 3954 | CG | PHE | D | 716 | 3.882 | 26.036 | 6.199 | 1.00 | 21.93 | C |
| ATOM | 3955 | CD1 | PHE | D | 716 | 3.804 | 26.482 | 7.515 | 1.00 | 19.71 | C |
| ATOM | 3956 | CD2 | PHE | D | 716 | 4.351 | 26.913 | 5.217 | 1.00 | 19.54 | C |
| ATOM | 3957 | CE1 | PHE | D | 716 | 4.174 | 27.769 | 7.850 | 1.00 | 19.20 | C |
| ATOM | 3958 | CE2 | PHE | D | 716 | 4.725 | 28.208 | 5.536 | 1.00 | 19.96 | C |
| ATOM | 3959 | CZ | PHE | D | 716 | 4.638 | 28.644 | 6.857 | 1.00 | 20.24 | C |
| ATOM | 3960 | N | ARG | D | 717 | 0.879 | 22.603 | 4.689 | 1.00 | 32.19 | N |
| ATOM | 3961 | CA | ARG | D | 717 | 0.581 | 21.475 | 3.821 | 1.00 | 36.18 | C |
| ATOM | 3962 | C | ARG | D | 717 | −0.269 | 22.103 | 2.716 | 1.00 | 35.80 | C |
| ATOM | 3963 | O | ARG | D | 717 | −0.186 | 21.727 | 1.545 | 1.00 | 35.14 | O |
| ATOM | 3964 | CB | ARG | D | 717 | −0.209 | 20.400 | 4.570 | 1.00 | 39.40 | C |
| ATOM | 3965 | CG | ARG | D | 717 | −0.437 | 19.144 | 3.743 | 1.00 | 42.14 | C |
| ATOM | 3966 | CD | ARG | D | 717 | −1.206 | 18.102 | 4.518 | 1.00 | 43.31 | C |
| ATOM | 3967 | NE | ARG | D | 717 | −2.413 | 18.664 | 5.117 | 1.00 | 48.20 | N |
| ATOM | 3968 | CZ | ARG | D | 717 | −3.359 | 17.940 | 5.714 | 1.00 | 50.40 | C |
| ATOM | 3969 | NH1 | ARG | D | 717 | −3.240 | 16.618 | 5.787 | 1.00 | 48.68 | N |
| ATOM | 3970 | NH2 | ARG | D | 717 | −4.415 | 18.536 | 6.251 | 1.00 | 51.09 | N |
| ATOM | 3971 | N | ILE | D | 718 | −1.074 | 23.086 | 3.110 | 1.00 | 36.09 | N |
| ATOM | 3972 | CA | ILE | D | 718 | −1.919 | 23.817 | 2.175 | 1.00 | 33.20 | C |
| ATOM | 3973 | C | ILE | D | 718 | −1.019 | 24.658 | 1.290 | 1.00 | 32.86 | C |
| ATOM | 3974 | O | ILE | D | 718 | −1.242 | 24.769 | 0.085 | 1.00 | 32.44 | O |
| ATOM | 3975 | CB | ILE | D | 718 | −2.893 | 24.749 | 2.913 | 1.00 | 32.66 | C |
| ATOM | 3976 | CG1 | ILE | D | 718 | −3.916 | 23.917 | 3.686 | 1.00 | 32.71 | C |
| ATOM | 3977 | CG2 | ILE | D | 718 | −3.596 | 25.668 | 1.924 | 1.00 | 31.11 | C |
| ATOM | 3978 | CD1 | ILE | D | 718 | −4.837 | 24.749 | 4.545 | 1.00 | 30.41 | C |
| ATOM | 3979 | N | PHE | D | 719 | −0.003 | 25.265 | 1.895 | 1.00 | 34.20 | N |
| ATOM | 3980 | CA | PHE | D | 719 | 0.935 | 26.083 | 1.138 | 1.00 | 34.51 | C |

TABLE 4-continued

Stem Cell Factor Dimer

| ATOM | 3981 | C | PHE | D | 719 | 1.675 | 25.248 | 0.093 | 1.00 | 36.52 | C |
| ATOM | 3982 | O | PHE | D | 719 | 1.831 | 25.669 | -1.050 | 1.00 | 36.77 | O |
| ATOM | 3983 | CB | PHE | D | 719 | 1.965 | 26.715 | 2.057 | 1.00 | 32.83 | C |
| ATOM | 3984 | CG | PHE | D | 719 | 3.112 | 27.338 | 1.321 | 1.00 | 32.14 | C |
| ATOM | 3985 | CD1 | PHE | D | 719 | 2.998 | 28.614 | 0.783 | 1.00 | 32.64 | C |
| ATOM | 3986 | CD2 | PHE | D | 719 | 4.303 | 26.640 | 1.150 | 1.00 | 29.99 | C |
| ATOM | 3987 | CE1 | PHE | D | 719 | 4.060 | 29.193 | 0.085 | 1.00 | 31.46 | C |
| ATOM | 3988 | CE2 | PHE | D | 719 | 5.363 | 27.201 | 0.459 | 1.00 | 32.01 | C |
| ATOM | 3989 | CZ | PHE | D | 719 | 5.243 | 28.486 | -0.076 | 1.00 | 31.65 | C |
| ATOM | 3990 | N | ASN | D | 720 | 2.148 | 24.075 | 0.501 | 1.00 | 38.51 | N |
| ATOM | 3991 | CA | ASN | D | 720 | 2.871 | 23.185 | -0.402 | 1.00 | 40.99 | C |
| ATOM | 3992 | C | ASN | D | 720 | 1.975 | 22.710 | -1.540 | 1.00 | 42.05 | C |
| ATOM | 3993 | O | ASN | D | 720 | 2.318 | 22.856 | -2.715 | 1.00 | 38.56 | O |
| ATOM | 3994 | CB | ASN | D | 720 | 3.406 | 21.975 | 0.365 | 1.00 | 41.82 | C |
| ATOM | 3995 | CG | ASN | D | 720 | 4.676 | 22.282 | 1.128 | 1.00 | 43.96 | C |
| ATOM | 3996 | OD1 | ASN | D | 720 | 5.114 | 21.492 | 1.962 | 1.00 | 47.53 | O |
| ATOM | 3997 | ND2 | ASN | D | 720 | 5.283 | 23.423 | 0.838 | 1.00 | 45.70 | N |
| ATOM | 3998 | N | ARG | D | 721 | 0.831 | 22.134 | -1.183 | 1.00 | 44.34 | N |
| ATOM | 3999 | CA | ARG | D | 721 | -0.119 | 21.655 | -2.174 | 1.00 | 48.41 | C |
| ATOM | 4000 | C | ARG | D | 721 | -0.392 | 22.795 | -3.147 | 1.00 | 50.49 | C |
| ATOM | 4001 | O | ARG | D | 721 | -0.153 | 22.679 | -4.349 | 1.00 | 51.59 | O |
| ATOM | 4002 | CB | ARG | D | 721 | -1.427 | 21.230 | -1.494 | 1.00 | 50.30 | C |
| ATOM | 4003 | CG | ARG | D | 721 | -2.511 | 20.736 | -2.446 | 1.00 | 54.70 | C |
| ATOM | 4004 | CD | ARG | D | 721 | -2.278 | 19.294 | -2.895 | 1.00 | 60.17 | C |
| ATOM | 4005 | NE | ARG | D | 721 | -2.917 | 18.317 | -2.009 | 1.00 | 63.19 | N |
| ATOM | 4006 | CZ | ARG | D | 721 | -2.833 | 16.996 | -2.160 | 1.00 | 64.19 | C |
| ATOM | 4007 | NH1 | ARG | D | 721 | -2.131 | 16.482 | -3.165 | 1.00 | 65.14 | N |
| ATOM | 4008 | NH2 | ARG | D | 721 | -3.457 | 16.185 | -1.313 | 1.00 | 63.41 | N |
| ATOM | 4009 | N | SER | D | 722 | -0.874 | 23.908 | -2.611 | 1.00 | 52.95 | N |
| ATOM | 4010 | CA | SER | D | 722 | -1.202 | 25.075 | -3.418 | 1.00 | 55.12 | C |
| ATOM | 4011 | C | SER | D | 722 | -0.090 | 25.474 | -4.380 | 1.00 | 57.42 | C |
| ATOM | 4012 | O | SER | D | 722 | -0.344 | 25.754 | -5.553 | 1.00 | 57.12 | O |
| ATOM | 4013 | CB | SER | D | 722 | -1.546 | 26.256 | -2.508 | 1.00 | 54.05 | C |
| ATOM | 4014 | OG | SER | D | 722 | -1.776 | 27.426 | -3.268 | 1.00 | 54.05 | O |
| ATOM | 4015 | N | ILE | D | 723 | 1.142 | 25.503 | -3.889 | 1.00 | 60.20 | N |
| ATOM | 4016 | CA | ILE | D | 723 | 2.266 | 25.876 | -4.734 | 1.00 | 64.22 | C |
| ATOM | 4017 | C | ILE | D | 723 | 2.435 | 24.918 | -5.904 | 1.00 | 67.18 | C |
| ATOM | 4018 | O | ILE | D | 723 | 2.520 | 25.350 | -7.052 | 1.00 | 67.37 | O |
| ATOM | 4019 | CB | ILE | D | 723 | 3.581 | 25.930 | -3.933 | 1.00 | 63.96 | C |
| ATOM | 4020 | CG1 | ILE | D | 723 | 3.561 | 27.136 | -2.992 | 1.00 | 64.48 | C |
| ATOM | 4021 | CG2 | ILE | D | 723 | 4.765 | 26.014 | -4.876 | 1.00 | 63.91 | C |
| ATOM | 4022 | CD1 | ILE | D | 723 | 3.337 | 28.464 | -3.695 | 1.00 | 64.40 | C |
| ATOM | 4023 | N | ASP | D | 724 | 2.476 | 23.621 | -5.620 | 1.00 | 70.57 | N |
| ATOM | 4024 | CA | ASP | D | 724 | 2.639 | 22.643 | -6.685 | 1.00 | 74.58 | C |
| ATOM | 4025 | C | ASP | D | 724 | 1.443 | 22.705 | -7.628 | 1.00 | 76.51 | C |
| ATOM | 4026 | O | ASP | D | 724 | 1.563 | 22.438 | -8.823 | 1.00 | 76.39 | O |
| ATOM | 4027 | CB | ASP | D | 724 | 2.786 | 21.230 | -6.110 | 1.00 | 76.01 | C |
| ATOM | 4028 | CG | ASP | D | 724 | 3.246 | 20.221 | -7.157 | 1.00 | 78.85 | C |
| ATOM | 4029 | OD1 | ASP | D | 724 | 2.468 | 19.935 | -8.099 | 1.00 | 79.06 | O |
| ATOM | 4030 | OD2 | ASP | D | 724 | 4.390 | 19.723 | -7.044 | 1.00 | 79.21 | O |
| ATOM | 4031 | N | ALA | D | 725 | 0.287 | 23.063 | -7.083 | 1.00 | 79.26 | N |
| ATOM | 4032 | CA | ALA | D | 725 | -0.916 | 23.169 | -7.888 | 1.00 | 82.39 | C |
| ATOM | 4033 | C | ALA | D | 725 | -0.727 | 24.306 | -8.876 | 1.00 | 85.18 | C |
| ATOM | 4034 | O | ALA | D | 725 | -1.228 | 24.257 | -9.996 | 1.00 | 85.62 | O |
| ATOM | 4035 | CB | ALA | D | 725 | -2.115 | 23.442 | -7.005 | 1.00 | 82.12 | C |
| ATOM | 4036 | N | PHE | D | 726 | 0.007 | 25.329 | -8.453 | 1.00 | 88.76 | N |
| ATOM | 4037 | CA | PHE | D | 726 | 0.258 | 26.479 | -9.307 | 1.00 | 92.49 | C |
| ATOM | 4038 | C | PHE | D | 726 | 1.285 | 26.121 | -10.365 | 1.00 | 94.74 | C |
| ATOM | 4039 | O | PHE | D | 726 | 1.358 | 26.761 | -11.412 | 1.00 | 95.57 | O |
| ATOM | 4040 | CB | PHE | D | 726 | 0.766 | 27.664 | -8.488 | 1.00 | 93.45 | C |
| ATOM | 4041 | CG | PHE | D | 726 | 0.704 | 28.970 | -9.224 | 1.00 | 94.42 | C |
| ATOM | 4042 | CD1 | PHE | D | 726 | -0.505 | 29.643 | -9.366 | 1.00 | 94.75 | C |
| ATOM | 4043 | CD2 | PHE | D | 726 | 1.846 | 29.512 | -9.804 | 1.00 | 94.94 | C |
| ATOM | 4044 | CE1 | PHE | D | 726 | -0.577 | 30.839 | -10.076 | 1.00 | 94.86 | C |
| ATOM | 4045 | CE2 | PHE | D | 726 | 1.785 | 30.708 | -10.517 | 1.00 | 95.15 | C |
| ATOM | 4046 | CZ | PHE | D | 726 | 0.571 | 31.372 | -10.653 | 1.00 | 94.93 | C |
| ATOM | 4047 | N | LYS | D | 727 | 2.091 | 25.103 | -10.085 | 1.00 | 97.62 | N |
| ATOM | 4048 | CA | LYS | D | 727 | 3.096 | 24.659 | -11.040 | 1.00 | 100.84 | C |
| ATOM | 4049 | C | LYS | D | 727 | 2.390 | 23.922 | -12.169 | 1.00 | 102.89 | C |
| ATOM | 4050 | O | LYS | D | 727 | 3.026 | 23.230 | -12.962 | 1.00 | 103.74 | O |
| ATOM | 4051 | CB | LYS | D | 727 | 4.102 | 23.715 | -10.378 | 1.00 | 100.90 | C |
| ATOM | 4052 | CG | LYS | D | 727 | 5.054 | 24.382 | -9.402 | 1.00 | 102.65 | C |
| ATOM | 4053 | CD | LYS | D | 727 | 6.110 | 23.394 | -8.915 | 1.00 | 103.29 | C |
| ATOM | 4054 | CE | LYS | D | 727 | 7.109 | 24.056 | -7.977 | 1.00 | 103.25 | C |
| ATOM | 4055 | NZ | LYS | D | 727 | 8.168 | 23.108 | -7.526 | 1.00 | 103.06 | N |
| ATOM | 4056 | N | ASP | D | 728 | 1.070 | 24.073 | -12.229 | 1.00 | 105.08 | N |
| ATOM | 4057 | CA | ASP | D | 728 | 0.259 | 23.419 | -13.251 | 1.00 | 106.79 | C |

TABLE 4-continued

Stem Cell Factor Dimer

| ATOM | 4058 | C | ASP | D | 728 | −1.023 | 24.211 | −13.512 | 1.00 | 107.51 | C |
|---|---|---|---|---|---|---|---|---|---|---|---|
| ATOM | 4059 | O | ASP | D | 728 | −2.032 | 23.640 | −13.923 | 1.00 | 107.48 | O |
| ATOM | 4060 | CB | ASP | D | 728 | −0.113 | 22.002 | −12.799 | 1.00 | 107.76 | C |
| ATOM | 4061 | CG | ASP | D | 728 | 1.090 | 21.189 | −12.353 | 1.00 | 108.44 | C |
| ATOM | 4062 | OD1 | ASP | D | 728 | 1.982 | 20.930 | −13.188 | 1.00 | 109.36 | O |
| ATOM | 4063 | OD2 | ASP | D | 728 | 1.142 | 20.810 | −11.163 | 1.00 | 108.52 | O |
| ATOM | 4064 | N | PHE | D | 729 | −0.983 | 25.518 | −13.271 | 1.00 | 108.65 | N |
| ATOM | 4065 | CA | PHE | D | 729 | −2.156 | 26.365 | −13.475 | 1.00 | 110.01 | C |
| ATOM | 4066 | C | PHE | D | 729 | −2.757 | 26.176 | −14.865 | 1.00 | 110.93 | C |
| ATOM | 4067 | O | PHE | D | 729 | −3.705 | 25.409 | −15.036 | 1.00 | 111.27 | O |
| ATOM | 4068 | CB | PHE | D | 729 | −1.796 | 27.838 | −13.250 | 1.00 | 109.77 | C |
| ATOM | 4069 | CG | PHE | D | 729 | −2.965 | 28.773 | −13.382 | 1.00 | 109.64 | C |
| ATOM | 4070 | CD1 | PHE | D | 729 | −4.185 | 28.470 | −12.786 | 1.00 | 109.79 | C |
| ATOM | 4071 | CG2 | PHE | D | 729 | −2.848 | 29.957 | −14.097 | 1.00 | 109.96 | C |
| ATOM | 4072 | CE1 | PHE | D | 729 | −5.273 | 29.332 | −12.903 | 1.00 | 109.64 | C |
| ATOM | 4073 | CE2 | PHE | D | 729 | −3.931 | 30.828 | −14.219 | 1.00 | 110.09 | C |
| ATOM | 4074 | CZ | PHE | D | 729 | −5.146 | 30.513 | −13.621 | 1.00 | 109.50 | C |
| ATOM | 4075 | N | VAL | D | 730 | −2.214 | 26.882 | −15.852 | 1.00 | 111.95 | N |
| ATOM | 4076 | CA | VAL | D | 730 | −2.696 | 26.766 | −17.226 | 1.00 | 112.76 | C |
| ATOM | 4077 | C | VAL | D | 730 | −1.608 | 26.079 | −18.051 | 1.00 | 113.09 | C |
| ATOM | 4078 | O | VAL | D | 730 | −1.622 | 26.110 | −19.281 | 1.00 | 113.21 | O |
| ATOM | 4079 | CB | VAL | D | 730 | −3.017 | 28.158 | −17.838 | 1.00 | 113.05 | C |
| ATOM | 4080 | CG1 | VAL | D | 730 | −3.632 | 28.001 | −19.222 | 1.00 | 113.29 | C |
| ATOM | 4081 | CG2 | VAL | D | 730 | −3.979 | 28.911 | −16.939 | 1.00 | 112.88 | C |
| ATOM | 4082 | N | VAL | D | 731 | −0.664 | 25.454 | −17.352 | 1.00 | 113.55 | N |
| ATOM | 4083 | CA | VAL | D | 731 | 0.442 | 24.749 | −17.992 | 1.00 | 113.65 | C |
| ATOM | 4084 | C | VAL | D | 731 | 0.119 | 23.263 | −18.121 | 1.00 | 113.98 | C |
| ATOM | 4085 | O | VAL | D | 731 | 0.510 | 22.614 | −19.090 | 1.00 | 114.23 | O |
| ATOM | 4086 | CB | VAL | D | 731 | 1.750 | 24.907 | −17.178 | 1.00 | 113.39 | C |
| ATOM | 4087 | CG1 | VAL | D | 731 | 2.888 | 24.165 | −17.864 | 1.00 | 112.68 | C |
| ATOM | 4088 | CG2 | VAL | D | 731 | 2.092 | 26.380 | −17.029 | 1.00 | 113.00 | C |
| ATOM | 4089 | N | ALA | D | 732 | −8.151 | 23.191 | −20.446 | 1.00 | 112.99 | N |
| ATOM | 4090 | CA | ALA | D | 732 | −8.781 | 23.296 | −19.136 | 1.00 | 112.99 | C |
| ATOM | 4091 | C | ALA | D | 732 | −10.158 | 23.942 | −19.244 | 1.00 | 112.89 | C |
| ATOM | 4092 | O | ALA | D | 732 | −11.068 | 23.624 | −18.476 | 1.00 | 112.43 | O |
| ATOM | 4093 | CB | ALA | D | 732 | −7.895 | 24.105 | −18.199 | 1.00 | 113.07 | C |
| TER | 4094 | | ALA | D | 732 | | | | | | |
| HETATM | 4095 | SM | SM | C | 801 | 3.382 | 22.913 | 33.418 | 1.00 | 1.01 | SM |
| HETATM | 4096 | SM | SM | | 802 | 12.310 | 41.103 | 1.729 | 1.00 | 46.23 | SM |
| HETATM | 4097 | SM | SM | B | 803 | 34.722 | 60.629 | −13.944 | 1.00 | 31.85 | SM |
| HETATM | 4098 | SM | SM | | 804 | 23.452 | 43.030 | 48.466 | 1.00 | 29.22 | SM |
| HETATM | 4099 | CA | CA | C | 805 | 10.432 | 45.369 | 22.564 | 1.00 | 13.16 | CA |
| HETATM | 4100 | CA | CA | A | 806 | 35.803 | 63.939 | 33.610 | 1.00 | 29.63 | CA |
| HETATM | 4101 | C | TRS | | 807 | 12.090 | 38.542 | −7.133 | 1.00 | 65.56 | C |
| HETATM | 4102 | C1 | TRS | | 807 | 11.580 | 37.873 | −5.842 | 1.00 | 65.64 | C |
| HETATM | 4103 | C2 | TRS | | 807 | 12.288 | 37.549 | −8.116 | 1.00 | 66.45 | C |
| HETATM | 4104 | C3 | TRS | | 807 | 13.335 | 39.347 | −6.731 | 1.00 | 65.43 | C |
| HETATM | 4105 | N | TRS | | 807 | 11.058 | 39.471 | −7.617 | 1.00 | 65.22 | N |
| HETATM | 4106 | O1 | TRS | | 807 | 12.450 | 36.961 | −5.333 | 1.00 | 66.42 | O |
| HETATM | 4107 | O2 | TRS | | 807 | 13.351 | 36.656 | −7.967 | 1.00 | 66.52 | O |
| HETATM | 4108 | O3 | TRS | | 807 | 13.974 | 40.049 | −7.756 | 1.00 | 67.00 | O |
| HETATM | 4109 | O | HOH | | 811 | 8.606 | 30.195 | 16.587 | 1.00 | 16.28 | O |
| HETATM | 4110 | O | HOH | | 812 | 15.796 | 28.952 | 16.244 | 1.00 | 25.74 | O |
| HETATM | 4111 | O | HOH | | 813 | 8.996 | 37.339 | 20.117 | 1.00 | 20.66 | O |
| HETATM | 4112 | O | HOH | | 814 | 36.198 | 57.554 | 35.884 | 1.00 | 24.36 | O |
| HETATM | 4113 | O | HOH | | 815 | 15.748 | 41.466 | 32.458 | 1.00 | 25.24 | O |
| HETATM | 4114 | O | HOH | | 816 | 12.670 | 24.054 | 17.321 | 1.00 | 25.31 | O |
| HETATM | 4115 | O | HOH | | 817 | 25.605 | 46.320 | 26.127 | 1.00 | 20.83 | O |
| HETATM | 4116 | O | HOH | | 818 | 29.793 | 46.559 | 4.826 | 1.00 | 27.80 | O |
| HETATM | 4117 | O | HOH | | 820 | 23.636 | 52.838 | 21.810 | 1.00 | 29.62 | O |
| HETATM | 4118 | O | HOH | | 821 | −5.477 | 35.005 | 4.087 | 1.00 | 38.64 | O |
| HETATM | 4119 | O | HOH | | 822 | 9.263 | 22.777 | 37.596 | 1.00 | 30.45 | O |
| HETATM | 4120 | O | HOH | | 823 | 18.824 | 65.144 | 45.840 | 1.00 | 28.91 | O |
| HETATM | 4121 | O | HOH | | 824 | 41.938 | 49.349 | 29.824 | 1.00 | 36.33 | O |
| HETATM | 4122 | O | HOH | | 825 | 14.204 | 35.302 | 12.661 | 1.00 | 26.09 | O |
| HETATM | 4123 | O | HOH | | 826 | 5.154 | 28.366 | 35.565 | 1.00 | 27.41 | O |
| HETATM | 4124 | O | HOH | | 827 | 17.420 | 47.026 | 21.845 | 1.00 | 27.81 | O |
| HETATM | 4125 | O | HOH | | 828 | 29.550 | 40.761 | 7.680 | 1.00 | 35.99 | O |
| HETATM | 4126 | O | HOH | | 829 | 28.265 | 45.994 | 11.706 | 1.00 | 32.91 | O |
| HETATM | 4127 | O | HOH | | 830 | 12.962 | 31.889 | 47.898 | 1.00 | 42.72 | O |
| HETATM | 4128 | O | HOH | | 831 | 16.808 | 31.403 | 5.277 | 1.00 | 43.76 | O |
| HETATM | 4129 | O | HOH | | 832 | 32.631 | 57.885 | 29.873 | 1.00 | 37.74 | O |
| HETATM | 4130 | O | HOH | | 833 | 2.250 | 27.901 | 24.836 | 1.00 | 43.13 | O |
| HETATM | 4131 | O | HOH | | 834 | 29.990 | 44.971 | 9.328 | 1.00 | 31.81 | O |
| HETATM | 4132 | O | HOH | | 835 | −1.600 | 20.408 | 13.679 | 1.00 | 43.79 | O |
| HETATM | 4133 | O | HOH | | 836 | 11.220 | 47.746 | 7.580 | 1.00 | 30.14 | O |
| HETATM | 4134 | O | HOH | | 837 | 20.724 | 44.044 | 29.836 | 1.00 | 30.56 | O |

TABLE 4-continued

Stem Cell Factor Dimer

| HETATM | 4135 | O | HOH | 838 | 2.173 | 22.432 | 13.281 | 1.00 | 22.54 | O |
|---|---|---|---|---|---|---|---|---|---|---|
| HETATM | 4136 | O | HOH | 839 | 17.557 | 36.992 | 9.840 | 1.00 | 31.87 | O |
| HETATM | 4137 | O | HOH | 840 | 4.550 | 23.994 | 14.170 | 1.00 | 27.46 | O |
| HETATM | 4138 | O | HOH | 841 | 25.281 | 39.695 | 6.782 | 1.00 | 41.84 | O |
| HETATM | 4139 | O | HOH | 842 | 9.383 | 42.930 | 6.783 | 1.00 | 47.18 | O |
| HETATM | 4140 | O | HOH | 843 | 6.361 | 42.296 | 24.220 | 1.00 | 37.78 | O |
| HETATM | 4141 | O | HOH | 844 | 39.382 | 57.416 | 48.330 | 1.00 | 48.52 | O |
| HETATM | 4142 | O | HOH | 845 | 32.247 | 41.153 | 5.687 | 1.00 | 41.83 | O |
| HETATM | 4143 | O | HOH | 846 | 26.125 | 49.499 | −8.757 | 1.00 | 30.11 | O |
| HETATM | 4144 | O | HOH | 847 | 0.290 | 30.022 | 23.939 | 1.00 | 50.00 | O |
| HETATM | 4145 | O | HOH | 848 | 8.376 | 42.541 | 9.479 | 1.00 | 43.80 | O |
| HETATM | 4146 | O | HOH | 849 | 19.958 | 38.970 | 5.910 | 1.00 | 46.78 | O |
| HETATM | 4147 | O | HOH | 850 | 22.162 | 39.657 | 21.182 | 1.00 | 33.34 | O |
| HETATM | 4148 | O | HOH | 851 | 8.230 | 39.327 | 21.959 | 1.00 | 33.00 | O |
| HETATM | 4149 | O | HOH | 852 | 23.921 | 60.495 | 19.790 | 1.00 | 35.77 | O |
| HETATM | 4150 | O | HOH | 853 | 6.817 | 22.716 | 16.090 | 1.00 | 27.55 | O |
| HETATM | 4151 | O | HOH | 854 | 34.018 | 56.401 | 28.113 | 1.00 | 34.61 | O |
| HETATM | 4152 | O | HOH | 856 | 27.581 | 39.513 | 34.077 | 1.00 | 42.95 | O |
| HETATM | 4153 | O | HOH | 857 | −0.751 | 35.172 | 8.963 | 1.00 | 32.87 | O |
| HETATM | 4154 | O | HOH | 859 | 32.429 | 60.073 | −13.200 | 1.00 | 23.38 | O |
| HETATM | 4155 | O | HOH | 860 | −7.012 | 24.072 | 13.604 | 1.00 | 34.71 | O |
| HETATM | 4156 | O | HOH | 861 | 39.074 | 63.063 | 33.662 | 1.00 | 58.21 | O |
| HETATM | 4157 | O | HOH | 862 | 21.440 | 42.915 | 27.714 | 1.00 | 22.95 | O |
| HETATM | 4158 | O | HOH | 864 | 37.581 | 61.643 | 36.898 | 1.00 | 39.63 | O |
| HETATM | 4159 | O | HOH | 865 | 0.685 | 21.698 | 15.184 | 1.00 | 28.66 | O |
| HETATM | 4160 | O | HOH | 866 | 22.254 | 64.084 | 49.555 | 1.00 | 44.64 | O |
| HETATM | 4161 | O | HOH | 867 | 35.264 | 53.161 | 23.559 | 1.00 | 43.70 | O |
| HETATM | 4162 | O | HOH | 868 | 6.596 | 44.632 | 15.034 | 1.00 | 59.30 | O |
| HETATM | 4163 | O | HOH | 869 | 22.825 | 56.530 | −12.218 | 1.00 | 52.42 | O |
| HETATM | 4164 | O | HOH | 870 | 31.995 | 63.552 | 10.190 | 1.00 | 36.82 | O |
| HETATM | 4165 | O | HOH | 871 | 0.793 | 40.178 | 0.296 | 1.00 | 48.61 | O |
| HETATM | 4166 | O | HOH | 872 | 23.300 | 60.113 | −7.891 | 1.00 | 49.86 | O |
| HETATM | 4167 | O | HOH | 873 | 11.054 | 40.390 | 18.125 | 1.00 | 48.30 | O |
| HETATM | 4168 | O | HOH | 874 | 13.243 | 21.325 | 37.798 | 1.00 | 32.31 | O |
| HETATM | 4169 | O | HOH | 875 | −1.787 | 35.888 | 19.682 | 1.00 | 48.97 | O |
| HETATM | 4170 | O | HOH | 876 | 24.682 | 67.138 | 31.722 | 1.00 | 50.20 | O |
| HETATM | 4171 | O | HOH | 877 | −1.307 | 36.711 | 41.965 | 1.00 | 50.56 | O |
| HETATM | 4172 | O | HOH | 878 | −0.438 | 34.252 | 13.488 | 1.00 | 46.62 | O |
| HETATM | 4173 | O | HOH | 879 | 27.258 | 44.610 | 27.195 | 1.00 | 30.34 | O |
| HETATM | 4174 | O | HOH | 880 | 25.059 | 58.789 | 17.500 | 1.00 | 24.33 | O |
| HETATM | 4175 | O | HOH | 881 | 15.549 | 41.179 | 5.494 | 1.00 | 27.27 | O |
| HETATM | 4176 | O | HOH | 882 | 6.184 | 20.441 | 14.801 | 1.00 | 33.01 | O |
| HETATM | 4177 | O | HOH | 884 | 35.838 | 55.016 | 50.740 | 1.00 | 26.63 | O |
| HETATM | 4178 | O | HOH | 885 | 15.613 | 16.978 | 24.799 | 1.00 | 46.01 | O |
| HETATM | 4179 | O | HOH | 886 | 18.940 | 41.747 | 27.441 | 1.00 | 43.83 | O |
| HETATM | 4180 | O | HOH | 887 | 21.025 | 38.556 | 16.332 | 1.00 | 25.23 | O |
| HETATM | 4181 | O | HOH | 888 | 7.893 | 19.264 | 12.842 | 1.00 | 38.30 | O |
| HETATM | 4182 | O | HOH | 889 | 33.533 | 59.350 | 3.597 | 1.00 | 47.44 | O |
| HETATM | 4183 | O | HOH | 890 | 9.571 | 38.165 | 17.010 | 1.00 | 31.45 | O |
| HETATM | 4184 | O | HOH | 891 | 28.775 | 35.831 | 14.058 | 1.00 | 40.18 | O |
| HETATM | 4185 | O | HOH | 892 | 26.247 | 53.039 | −17.253 | 1.00 | 46.82 | O |
| HETATM | 4186 | O | HOH | 893 | 32.415 | 61.335 | 17.452 | 1.00 | 38.77 | O |
| HETATM | 4187 | O | HOH | 894 | 23.460 | 45.149 | 24.354 | 1.00 | 26.05 | O |
| HETATM | 4188 | O | HOH | 895 | 3.991 | 24.967 | 37.153 | 1.00 | 42.80 | O |
| HETATM | 4189 | O | HOH | 896 | 19.794 | 41.241 | 31.566 | 1.00 | 50.67 | O |
| HETATM | 4190 | O | HOH | 897 | 19.768 | 25.882 | 9.816 | 1.00 | 44.44 | O |
| HETATM | 4191 | O | HOH | 898 | 27.528 | 39.803 | 14.126 | 1.00 | 40.31 | O |
| HETATM | 4192 | O | HOH | 899 | 15.999 | 61.065 | 33.673 | 1.00 | 40.88 | O |
| HETATM | 4193 | O | HOH | 900 | 15.539 | 19.636 | 28.723 | 1.00 | 47.29 | O |
| HETATM | 4194 | O | HOH | 901 | 38.498 | 54.225 | 8.757 | 1.00 | 30.13 | O |
| HETATM | 4195 | O | HOH | 902 | 32.463 | 48.114 | 54.923 | 1.00 | 38.66 | O |
| HETATM | 4196 | O | HOH | 903 | −2.634 | 37.278 | 32.151 | 1.00 | 35.03 | O |
| HETATM | 4197 | O | HOH | 904 | 29.906 | 38.640 | 9.627 | 1.00 | 38.75 | O |
| HETATM | 4198 | O | HOH | 905 | 2.033 | 18.537 | 15.351 | 1.00 | 26.34 | O |
| HETATM | 4199 | O | HOH | 906 | 27.804 | 65.306 | 43.860 | 1.00 | 32.86 | O |
| HETATM | 4200 | O | HOH | 907 | 18.984 | 58.578 | 24.142 | 1.00 | 29.87 | O |
| HETATM | 4201 | O | HOH | 908 | 21.742 | 28.140 | 13.049 | 1.00 | 30.99 | O |
| HETATM | 4202 | O | HOH | 909 | 20.378 | 21.642 | 23.293 | 1.00 | 39.19 | O |
| HETATM | 4203 | O | HOH | 910 | −6.019 | 39.244 | 2.216 | 1.00 | 34.77 | O |
| HETATM | 4204 | O | HOH | 911 | 17.624 | 66.255 | 35.268 | 1.00 | 51.56 | O |
| HETATM | 4205 | O | HOH | 912 | 3.763 | 20.127 | 13.752 | 1.00 | 30.70 | O |
| HETATM | 4206 | O | HOH | 913 | 3.362 | 27.348 | 33.755 | 1.00 | 23.36 | O |
| HETATM | 4207 | O | HOH | 914 | 24.559 | 28.693 | 12.265 | 1.00 | 43.09 | O |
| HETATM | 4208 | O | HOH | 915 | 36.824 | 59.818 | 47.570 | 1.00 | 30.39 | O |
| HETATM | 4209 | O | HOH | 916 | 22.924 | 22.342 | 40.503 | 1.00 | 44.39 | O |
| HETATM | 4210 | O | HOH | 917 | 4.702 | 18.252 | 11.499 | 1.00 | 32.74 | O |
| HETATM | 4211 | O | HOH | 918 | 3.467 | 17.089 | 17.532 | 1.00 | 39.40 | O |

TABLE 4-continued

Stem Cell Factor Dimer

| HETATM | 4212 | O | HOH | 919 | 29.413 | 49.496 | −7.485 | 1.00 | 47.21 | O |
|---|---|---|---|---|---|---|---|---|---|---|
| HETATM | 4213 | O | HOH | 920 | 34.259 | 51.561 | 21.638 | 1.00 | 37.97 | O |
| HETATM | 4214 | O | HOH | 921 | 32.610 | 44.187 | 35.494 | 1.00 | 38.79 | O |
| HETATM | 4215 | O | HOH | 922 | 32.804 | 43.191 | 23.362 | 1.00 | 49.05 | O |
| HETATM | 4216 | O | HOH | 923 | 22.149 | 37.679 | 18.847 | 1.00 | 30.70 | O |
| HETATM | 4217 | O | HOH | 924 | 17.587 | 59.642 | 39.191 | 1.00 | 43.12 | O |
| HETATM | 4218 | O | HOH | 925 | 22.812 | 24.637 | 9.520 | 1.00 | 46.83 | O |
| HETATM | 4219 | O | HOH | 926 | 22.586 | 61.146 | 9.839 | 1.00 | 30.25 | O |
| HETATM | 4220 | O | HOH | 927 | 20.143 | 20.685 | 34.805 | 1.00 | 32.86 | O |
| HETATM | 4221 | O | HOH | 928 | −0.129 | 30.047 | 26.719 | 1.00 | 41.23 | O |
| HETATM | 4222 | O | HOH | 929 | 18.693 | 64.441 | 43.617 | 1.00 | 26.18 | O |
| HETATM | 4223 | O | HOH | 930 | 3.316 | 26.782 | 31.229 | 1.00 | 30.65 | O |
| HETATM | 4224 | O | HOH | 931 | 8.782 | 41.756 | 37.184 | 1.00 | 38.10 | O |
| HETATM | 4225 | O | HOH | 932 | 26.815 | 65.475 | 31.026 | 1.00 | 37.12 | O |
| HETATM | 4226 | O | HOH | 933 | 8.096 | 48.366 | 22.796 | 1.00 | 45.13 | O |
| HETATM | 4227 | O | HOH | 934 | 4.661 | 27.558 | 28.897 | 1.00 | 33.72 | O |
| HETATM | 4228 | O | HOH | 935 | 40.351 | 55.087 | 47.376 | 1.00 | 47.23 | O |
| HETATM | 4229 | O | HOH | 936 | 7.950 | 32.677 | 47.497 | 1.00 | 39.88 | O |
| HETATM | 4230 | O | HOH | 937 | 12.548 | 44.676 | 21.718 | 1.00 | 34.89 | O |
| HETATM | 4231 | O | HOH | 938 | −8.820 | 40.219 | 1.469 | 1.00 | 49.47 | O |
| HETATM | 4232 | O | HOH | 939 | 7.489 | 53.321 | 8.112 | 1.00 | 49.45 | O |
| HETATM | 4233 | O | HOH | 940 | 19.944 | 39.180 | 44.418 | 1.00 | 45.27 | O |
| HETATM | 4234 | O | HOH | 941 | 29.508 | 64.292 | 41.649 | 1.00 | 47.23 | O |
| HETATM | 4235 | O | HOH | 942 | 47.050 | 56.585 | 38.269 | 1.00 | 50.59 | O |
| HETATM | 4236 | O | HOH | 943 | 7.616 | 45.571 | 21.859 | 1.00 | 39.67 | O |
| HETATM | 4237 | O | HOH | 944 | 7.909 | 44.216 | 26.286 | 1.00 | 48.09 | O |
| HETATM | 4238 | O | HOH | 945 | 30.114 | 47.882 | 12.560 | 1.00 | 44.31 | O |
| HETATM | 4239 | O | HOH | 946 | 2.782 | 22.874 | 35.242 | 1.00 | 41.79 | O |
| HETATM | 4240 | O | HOH | 947 | 16.770 | 62.683 | 36.910 | 1.00 | 41.79 | O |
| CONECT | 6 | 661 | | | | | | | | |
| CONECT | 300 | 1042 | | | | | | | | |
| CONECT | 661 | 6 | | | | | | | | |
| CONECT | 1042 | 300 | | | | | | | | |
| CONECT | 1068 | 1738 | | | | | | | | |
| CONECT | 1377 | 2103 | | | | | | | | |
| CONECT | 1738 | 1068 | | | | | | | | |
| CONECT | 2097 | 4097 | | | | | | | | |
| CONECT | 2103 | 1377 | | | | | | | | |
| CONECT | 2388 | 3114 | | | | | | | | |
| CONECT | 3114 | 2388 | | | | | | | | |
| CONECT | 4097 | 2097 | | | | | | | | |
| CONECT | 4101 | 4102 | 4103 | 4104 | 4105 | | | | | |
| CONECT | 4102 | 4101 | 4106 | | | | | | | |
| CONECT | 4103 | 4101 | 4107 | | | | | | | |
| CONECT | 4104 | 4101 | 4108 | | | | | | | |
| CONECT | 4105 | 4101 | | | | | | | | |
| CONECT | 4106 | 4102 | | | | | | | | |
| CONECT | 4107 | 4103 | | | | | | | | |
| CONECT | 4108 | 4104 | | | | | | | | |
| MASTER | | 385 | 0 | 7 | 19 | 8 | 0 | 0 | 6 | 4236 | 4 | 20 | 44 |

TABLE 6

FGF2/FGFR1/Heparin Ternary Complex

REMARK coordinates from simulated annealing refinement
REMARK refinement resolution: 25.0 – 3.0 A
REMARK starting    r= 0.2340 free_r= 0.2850
REMARK final       r=0.2310 free_r= 0.2893
REMARK rmsd bonds= 0.008843 rmsd angles= 1.48262
REMARK wa_initial= 5.38223 wa_dynamics= 5.24774 wa_final= 5.67599
REMARK target= mlf md-method= cartesian annealing schedule= slowcool
REMARK starting temperature= 2500 total md steps= 100 * 50
REMARK sg= P4(1)2(1)2 a= 98.888 b= 98.888 c= 196.292 alpha= 90 beta=90 gamma= 90
REMARK parameter file 1 : CNS_TOPPAR:protein_rep.param
REMARK parameter file 2 : CNS_TOPPAR:dna-rna.param
REMARK parameter file 3 : CNS_TOPPAR:water_rep.param
REMARK parameter file 4 : CNS_TOPPAR:ion.param
REMARK parameter file 5 : hexa.param
REMARK molecular structure file: deca2_8.mtf
REMARK input coordinates: deca2_8XB.pdb
REMARK reflection file= 23bdec2.hklt
REMARK ncs= restrain ncs file= ncs.def
REMARK B-correction resolution: 6.0 – 3.0

TABLE 6-continued

FGF2/FGFR1/Heparin Ternary Complex

REMARK initial B-factor correction applied to fobs:
REMARK B11= −10.663 B22= −10.663 B33= 21.325
REMARK B12=   0.000 B13=   0.000 B23=  0.000
REMARK B-factor correction applied to coordinate array B: 1.815
REMARK bulk solvent: density level= 0.295271 e/A^3, B-factor= 10 A^2
REMARK reflections with |Fobs|/sigma_F < 0.0 rejected
REMARK reflections with |Fobs| > 10000 * rms(Fobs) rejected
REMARK theoretical total number of refl. in resol. range:        20197 (100.0%)
REMARK number of unobserved reflections (no entry or |F|=0):      1892 (9.4%)
REMARX number of reflections rejected:                                0 (0.0%)
REMARK total number of reflections used:                         18305 (90.6%)
REMARK number of reflections in working set:                     17419 (86.2%)
REMARK number of reflections in test set:                          886 (4.4%)
CRYST1   98.888   98.888   196.292   90.00   90.00   90.00   P 41  21  2
REMARK FILENAME="deca2_8XBA_1.pdb"
REMARK DATE: 26-Jun-00   16:58:39            created by user: mohammad
REMARK VERSION: 0.5

| ATOM | 1  | CB  | HIS | 16 | 69.300 | 30.458 | 136.592 | 1.00 | 53.12 |
|------|----|-----|-----|----|--------|--------|---------|------|-------|
| ATOM | 2  | CG  | HIS | 16 | 68.282 | 29.746 | 137.434 | 1.00 | 53.81 |
| ATOM | 3  | CD2 | HIS | 16 | 68.024 | 29.802 | 138.763 | 1.00 | 53.82 |
| ATOM | 4  | ND1 | HIS | 16 | 67.400 | 28.821 | 136.918 | 1.00 | 53.71 |
| ATOM | 5  | CE1 | HIS | 16 | 66.646 | 28.337 | 137.890 | 1.00 | 52.39 |
| ATOM | 6  | NE2 | HIS | 16 | 67.004 | 28.917 | 139.019 | 1.00 | 52.97 |
| ATOM | 7  | C   | HIS | 16 | 69.392 | 28.671 | 134.893 | 1.00 | 53.57 |
| ATOM | 8  | O   | HIS | 16 | 69.057 | 29.086 | 133.779 | 1.00 | 54.30 |
| ATOM | 9  | N   | HIS | 16 | 71.340 | 30.243 | 135.155 | 1.00 | 53.53 |
| ATOM | 10 | CA  | HIS | 16 | 70.228 | 29.513 | 135.838 | 1.00 | 53.43 |
| ATOM | 11 | N   | PHE | 17 | 69.038 | 27.478 | 135.354 | 1.00 | 53.60 |
| ATOM | 12 | CA  | PHE | 17 | 68.267 | 26.563 | 134.527 | 1.00 | 52.77 |
| ATOM | 13 | CB  | PHE | 17 | 68.347 | 25.142 | 135.112 | 1.00 | 50.35 |
| ATOM | 14 | CG  | PHE | 17 | 67.444 | 24.910 | 136.279 | 1.00 | 49.67 |
| ATOM | 15 | CD1 | PHE | 17 | 66.154 | 24.417 | 136.087 | 1.00 | 48.74 |
| ATOM | 16 | CD2 | PHE | 17 | 67.865 | 25.204 | 137.570 | 1.00 | 49.40 |
| ATOM | 17 | CE1 | PHE | 17 | 65.293 | 24.221 | 137.164 | 1.00 | 47.80 |
| ATOM | 18 | CE2 | PHE | 17 | 67.007 | 25.012 | 138.659 | 1.00 | 49.12 |
| ATOM | 19 | CZ  | PHE | 17 | 65.718 | 24.519 | 138.451 | 1.00 | 47.95 |
| ATOM | 20 | C   | PHE | 17 | 66.813 | 27.007 | 134.268 | 1.00 | 52.61 |
| ATOM | 21 | O   | PHE | 17 | 66.198 | 26.567 | 133.294 | 1.00 | 53.57 |
| ATOM | 22 | N   | LYS | 18 | 66.275 | 27.895 | 135.104 | 1.00 | 51.30 |
| ATOM | 23 | CA  | LYS | 18 | 64.909 | 28.375 | 134.913 | 1.00 | 50.46 |
| ATOM | 24 | CB  | LYS | 18 | 64.275 | 28.772 | 136.248 | 1.00 | 49.68 |
| ATOM | 25 | C   | LYS | 18 | 64.821 | 29.555 | 133.936 | 1.00 | 50.17 |
| ATOM | 26 | O   | LYS | 18 | 63.792 | 29.745 | 133.289 | 1.00 | 50.91 |
| ATOM | 27 | N   | ASP | 19 | 65.889 | 30.344 | 133.822 | 1.00 | 48.70 |
| ATOM | 28 | CA  | ASP | 19 | 65.888 | 31.486 | 132.910 | 1.00 | 47.03 |
| ATOM | 29 | CB  | ASP | 19 | 67.043 | 32.421 | 133.234 | 1.00 | 48.46 |
| ATOM | 30 | CG  | ASP | 19 | 67.278 | 32.545 | 134.709 | 1.00 | 50.22 |
| ATOM | 31 | OD1 | ASP | 19 | 66.272 | 32.491 | 135.453 | 1.00 | 50.85 |
| ATOM | 32 | OD2 | ASP | 19 | 68.455 | 32.701 | 135.120 | 1.00 | 51.12 |
| ATOM | 33 | C   | ASP | 19 | 66.022 | 31.021 | 131.469 | 1.00 | 45.37 |
| ATOM | 34 | O   | ASP | 19 | 66.485 | 29.913 | 131.210 | 1.00 | 46.46 |
| ATOM | 35 | N   | PRO | 20 | 65.598 | 31.857 | 130.508 | 1.00 | 43.28 |
| ATOM | 36 | CD  | PRO | 20 | 64.692 | 33.003 | 130.659 | 1.00 | 42.19 |
| ATOM | 37 | CA  | PRO | 20 | 65.701 | 31.485 | 129.097 | 1.00 | 41.14 |
| ATOM | 38 | CB  | PRO | 20 | 64.948 | 32.602 | 128.399 | 1.00 | 39.82 |
| ATOM | 39 | CG  | PRO | 20 | 63.907 | 32.939 | 129.376 | 1.00 | 40.47 |
| ATOM | 40 | C   | PRO | 20 | 67.160 | 31.434 | 128.676 | 1.00 | 39.83 |
| ATOM | 41 | O   | PRO | 20 | 68.037 | 31.887 | 129.405 | 1.00 | 40.57 |
| ATOM | 42 | N   | LYS | 21 | 67.415 | 30.867 | 127.506 | 1.00 | 37.64 |
| ATOM | 43 | CA  | LYS | 21 | 68.766 | 30.776 | 126.980 | 1.00 | 34.69 |
| ATOM | 44 | CB  | LYS | 21 | 69.352 | 29.384 | 127.208 | 1.00 | 33.35 |
| ATOM | 45 | CG  | LYS | 21 | 69.626 | 29.032 | 128.645 | 1.00 | 33.21 |
| ATOM | 46 | CD  | LYS | 21 | 70.484 | 27.781 | 128.733 | 1.00 | 33.06 |
| ATOM | 47 | CE  | LYS | 21 | 70.796 | 27.418 | 130.183 | 1.00 | 34.73 |
| ATOM | 48 | NZ  | LYS | 21 | 71.677 | 26.215 | 130.332 | 1.00 | 33.57 |
| ATOM | 49 | C   | LYS | 21 | 68.742 | 31.041 | 125.490 | 1.00 | 33.43 |
| ATOM | 50 | O   | LYS | 21 | 67.694 | 30.975 | 124.852 | 1.00 | 33.06 |
| ATOM | 51 | N   | ARG | 22 | 69.897 | 31.370 | 124.937 | 1.00 | 32.25 |
| ATOM | 52 | CA  | ARG | 22 | 70.004 | 31.581 | 123.506 | 1.00 | 31.08 |
| ATOM | 53 | CB  | ARG | 22 | 70.687 | 32.911 | 123.203 | 1.00 | 32.57 |
| ATOM | 54 | CG  | ARG | 22 | 69.732 | 34.071 | 122.957 | 1.00 | 34.47 |
| ATOM | 55 | CD  | ARG | 22 | 70.516 | 35.341 | 122.616 | 1.00 | 36.93 |
| ATOM | 56 | NE  | ARG | 22 | 70.829 | 36.139 | 123.798 | 1.00 | 38.72 |
| ATOM | 57 | CZ  | ARG | 22 | 70.073 | 37.138 | 124.238 | 1.00 | 40.61 |
| ATOM | 58 | NH1 | ARG | 22 | 68.965 | 37.475 | 123.587 | 1.00 | 40.39 |
| ATOM | 59 | NH2 | ARG | 22 | 70.402 | 37.775 | 125.353 | 1.00 | 41.63 |
| ATOM | 60 | C   | ARG | 22 | 70.890 | 30.421 | 123.081 | 1.00 | 28.84 |

TABLE 6-continued

| | | | FGF2/FGFR1/Heparin Ternary Complex | | | | | |
|---|---|---|---|---|---|---|---|---|
| ATOM | 61 | O | ARG | 22 | 71.770 | 30.019 | 123.845 | 1.00 | 28.33 |
| ATOM | 62 | N | LEU | 23 | 70.658 | 29.856 | 121.900 | 1.00 | 25.80 |
| ATOM | 63 | CA | LEU | 23 | 71.496 | 28.743 | 121.464 | 1.00 | 23.35 |
| ATOM | 64 | CB | LEU | 23 | 70.652 | 27.528 | 121.105 | 1.00 | 20.30 |
| ATOM | 65 | CG | LEU | 23 | 70.055 | 26.819 | 122.315 | 1.00 | 17.64 |
| ATOM | 66 | CD1 | LEU | 23 | 69.385 | 25.554 | 121.854 | 1.00 | 16.44 |
| ATOM | 67 | CD2 | LEU | 23 | 71.145 | 26.494 | 123.314 | 1.00 | 17.15 |
| ATOM | 68 | C | LEU | 23 | 72.400 | 29.113 | 120.305 | 1.00 | 23.17 |
| ATOM | 69 | O | LEU | 23 | 71.997 | 29.062 | 119.151 | 1.00 | 23.67 |
| ATOM | 70 | N | TYR | 24 | 73.633 | 29.479 | 120.641 | 1.00 | 22.61 |
| ATOM | 71 | CA | TYR | 24 | 74.639 | 29.894 | 119.677 | 1.00 | 22.55 |
| ATOM | 72 | CB | TYR | 24 | 75.674 | 30.742 | 120.411 | 1.00 | 21.56 |
| ATOM | 73 | CG | TYR | 24 | 76.854 | 31.226 | 119.591 | 1.00 | 22.00 |
| ATOM | 74 | CD1 | TYR | 24 | 78.021 | 30.475 | 119.496 | 1.00 | 20.66 |
| ATOM | 75 | CE1 | TYR | 24 | 79.133 | 30.959 | 118.835 | 1.00 | 20.25 |
| ATOM | 76 | CD2 | TYR | 24 | 76.835 | 32.477 | 118.981 | 1.00 | 22.00 |
| ATOM | 77 | CE2 | TYR | 24 | 77.949 | 32.966 | 118.309 | 1.00 | 21.75 |
| ATOM | 78 | CZ | TYR | 24 | 79.092 | 32.202 | 118.246 | 1.00 | 21.10 |
| ATOM | 79 | OH | TYR | 24 | 80.206 | 32.694 | 117.607 | 1.00 | 22.44 |
| ATOM | 80 | C | TYR | 24 | 75.285 | 28.697 | 118.989 | 1.00 | 23.15 |
| ATOM | 81 | O | TYR | 24 | 76.038 | 27.946 | 119.605 | 1.00 | 23.41 |
| ATOM | 82 | N | CYS | 25 | 74.986 | 28.524 | 117.707 | 1.00 | 23.63 |
| ATOM | 83 | CA | CYS | 25 | 75.524 | 27.401 | 116.945 | 1.00 | 24.20 |
| ATOM | 84 | CB | CYS | 25 | 74.661 | 27.110 | 115.727 | 1.00 | 24.21 |
| ATOM | 85 | SG | CYS | 25 | 75.389 | 25.850 | 114.684 | 1.00 | 26.18 |
| ATOM | 86 | C | CYS | 25 | 76.944 | 27.630 | 116.473 | 1.00 | 23.32 |
| ATOM | 87 | O | CYS | 25 | 77.215 | 28.599 | 115.788 | 1.00 | 24.36 |
| ATOM | 88 | N | LYS | 26 | 77.832 | 26.709 | 116.814 | 1.00 | 22.03 |
| ATOM | 89 | CA | LYS | 26 | 79.234 | 26.804 | 116.434 | 1.00 | 21.70 |
| ATOM | 90 | CB | LYS | 26 | 79.948 | 25.505 | 116.809 | 1.00 | 19.91 |
| ATOM | 91 | CG | LYS | 26 | 81.443 | 25.475 | 116.512 | 1.00 | 19.56 |
| ATOM | 92 | CD | LYS | 26 | 82.119 | 24.288 | 117.228 | 1.00 | 20.95 |
| ATOM | 93 | CE | LYS | 26 | 83.649 | 24.402 | 117.274 | 1.00 | 19.82 |
| ATOM | 94 | NZ | LYS | 26 | 84.326 | 23.753 | 116.099 | 1.00 | 20.63 |
| ATOM | 95 | C | LYS | 26 | 79.455 | 27.086 | 114.954 | 1.00 | 22.52 |
| ATOM | 96 | O | LYS | 26 | 80.424 | 27.743 | 114.591 | 1.00 | 23.05 |
| ATOM | 97 | N | ASN | 27 | 78.559 | 26.591 | 114.104 | 1.00 | 22.60 |
| ATOM | 98 | CA | ASN | 27 | 78.712 | 26.775 | 112.668 | 1.00 | 22.64 |
| ATOM | 99 | CB | ASN | 27 | 77.983 | 25.661 | 111.909 | 1.00 | 21.87 |
| ATOM | 100 | CG | ASN | 27 | 78.352 | 25.622 | 110.431 | 1.00 | 21.71 |
| ATOM | 101 | OD1 | ASN | 27 | 79.459 | 25.995 | 110.046 | 1.00 | 20.77 |
| ATOM | 102 | ND2 | ASN | 27 | 77.433 | 25.148 | 109.603 | 1.00 | 20.65 |
| ATOM | 103 | C | ASN | 27 | 78.253 | 28.128 | 112.156 | 1.00 | 23.27 |
| ATOM | 104 | O | ASN | 27 | 77.146 | 28.273 | 111.647 | 1.00 | 24.11 |
| ATOM | 105 | N | GLY | 28 | 79.118 | 29.124 | 112.292 | 1.00 | 23.45 |
| ATOM | 106 | CA | GLY | 28 | 78.781 | 30.449 | 111.809 | 1.00 | 23.50 |
| ATOM | 107 | C | GLY | 28 | 78.349 | 31.457 | 112.849 | 1.00 | 22.32 |
| ATOM | 108 | O | GLY | 28 | 78.227 | 32.638 | 112.545 | 1.00 | 22.80 |
| ATOM | 109 | N | GLY | 29 | 78.113 | 31.011 | 114.072 | 1.00 | 21.39 |
| ATOM | 110 | CA | GLY | 29 | 77.698 | 31.935 | 115.107 | 1.00 | 20.23 |
| ATOM | 111 | C | GLY | 29 | 76.240 | 32.346 | 115.001 | 1.00 | 20.30 |
| ATOM | 112 | O | GLY | 29 | 75.852 | 33.405 | 115.468 | 1.00 | 20.85 |
| ATOM | 113 | N | PHE | 30 | 75.419 | 31.516 | 114.382 | 1.00 | 19.92 |
| ATOM | 114 | CA | PHE | 30 | 74.012 | 31.827 | 114.266 | 1.00 | 18.77 |
| ATOM | 115 | CB | PHE | 30 | 73.413 | 31.150 | 113.044 | 1.00 | 19.08 |
| ATOM | 116 | CG | PHE | 30 | 73.998 | 31.622 | 111.751 | 1.00 | 18.63 |
| ATOM | 117 | CD1 | PHE | 30 | 75.294 | 31.279 | 111.398 | 1.00 | 18.35 |
| ATOM | 118 | CD2 | PHE | 30 | 73.271 | 32.454 | 110.910 | 1.00 | 17.69 |
| ATOM | 119 | CE1 | PHE | 30 | 75.855 | 31.755 | 110.240 | 1.00 | 18.97 |
| ATOM | 120 | CE2 | PHE | 30 | 73.826 | 32.938 | 109.746 | 1.00 | 17.78 |
| ATOM | 121 | CZ | PHE | 30 | 75.117 | 32.591 | 109.408 | 1.00 | 18.74 |
| ATOM | 122 | C | PHE | 30 | 73.286 | 31.328 | 115.493 | 1.00 | 18.17 |
| ATOM | 123 | O | PHE | 30 | 73.516 | 30.208 | 115.926 | 1.00 | 18.61 |
| ATOM | 124 | N | PHE | 31 | 72.425 | 32.168 | 116.058 | 1.00 | 18.34 |
| ATOM | 125 | CA | PHE | 31 | 71.634 | 31.800 | 117.226 | 1.00 | 17.11 |
| ATOM | 126 | CB | PHE | 31 | 71.139 | 33.029 | 117.976 | 1.00 | 14.87 |
| ATOM | 127 | CG | PHE | 31 | 72.204 | 33.774 | 118.690 | 1.00 | 14.67 |
| ATOM | 128 | CD1 | PHE | 31 | 72.730 | 33.286 | 119.887 | 1.00 | 14.59 |
| ATOM | 129 | CD2 | PHE | 31 | 72.692 | 34.970 | 118.166 | 1.00 | 13.25 |
| ATOM | 130 | CE1 | PHE | 31 | 73.727 | 33.973 | 120.554 | 1.00 | 13.47 |
| ATOM | 131 | CE2 | PHE | 31 | 73.690 | 35.667 | 118.819 | 1.00 | 12.61 |
| ATOM | 132 | CZ | PHE | 31 | 74.212 | 35.167 | 120.016 | 1.00 | 13.50 |
| ATOM | 133 | C | PHE | 31 | 70.424 | 31.087 | 116.688 | 1.00 | 17.61 |
| ATOM | 134 | O | PHE | 31 | 69.829 | 31.546 | 115.719 | 1.00 | 18.12 |
| ATOM | 135 | N | LEU | 32 | 70.049 | 29.975 | 117.306 | 1.00 | 17.96 |
| ATOM | 136 | CA | LEU | 32 | 68.878 | 29.250 | 116.847 | 1.00 | 18.36 |
| ATOM | 137 | CB | LEU | 32 | 68.697 | 27.951 | 117.627 | 1.00 | 17.45 |

TABLE 6-continued

FGF2/FGFR1/Heparin Ternary Complex

| ATOM | 138 | CG | LEU | 32 | 67.534 | 27.082 | 117.137 | 1.00 | 17.14 |
|---|---|---|---|---|---|---|---|---|---|
| ATOM | 139 | CD1 | LEU | 32 | 67.753 | 26.717 | 115.686 | 1.00 | 16.23 |
| ATOM | 140 | CD2 | LEU | 32 | 67.422 | 25.821 | 117.984 | 1.00 | 17.14 |
| ATOM | 141 | C | LEU | 32 | 67.672 | 30.148 | 117.062 | 1.00 | 18.83 |
| ATOM | 142 | O | LEU | 32 | 67.453 | 30.660 | 118.150 | 1.00 | 19.06 |
| ATOM | 143 | N | ARG | 33 | 66.886 | 30.330 | 116.017 | 1.00 | 19.84 |
| ATOM | 144 | CA | ARG | 33 | 65.721 | 31.185 | 116.084 | 1.00 | 21.62 |
| ATOM | 145 | CB | ARG | 33 | 65.930 | 32.375 | 115.158 | 1.00 | 19.43 |
| ATOM | 146 | CG | ARG | 33 | 64.697 | 33.208 | 114.964 | 1.00 | 17.69 |
| ATOM | 147 | CD | ARG | 33 | 65.026 | 34.490 | 114.237 | 1.00 | 16.18 |
| ATOM | 148 | NE | ARG | 33 | 65.443 | 34.278 | 112.861 | 1.00 | 13.18 |
| ATOM | 149 | CZ | ARG | 33 | 65.745 | 35.265 | 112.031 | 1.00 | 12.69 |
| ATOM | 150 | NH1 | ARG | 33 | 65.676 | 36.511 | 112.455 | 1.00 | 9.98 |
| ATOM | 151 | NH2 | ARG | 33 | 66.124 | 35.013 | 110.782 | 1.00 | 14.90 |
| ATOM | 152 | C | ARG | 33 | 64.395 | 30.529 | 115.724 | 1.00 | 23.39 |
| ATOM | 153 | O | ARG | 33 | 64.300 | 29.769 | 114.763 | 1.00 | 23.37 |
| ATOM | 154 | N | ILE | 34 | 63.368 | 30.846 | 116.499 | 1.00 | 24.83 |
| ATOM | 155 | CA | ILE | 34 | 62.043 | 30.326 | 116.239 | 1.00 | 27.05 |
| ATOM | 156 | CB | ILE | 34 | 61.503 | 29.555 | 117.423 | 1.00 | 26.29 |
| ATOM | 157 | CG2 | ILE | 34 | 60.127 | 29.035 | 117.090 | 1.00 | 25.19 |
| ATOM | 158 | CG1 | ILE | 34 | 62.453 | 28.415 | 117.771 | 1.00 | 25.48 |
| ATOM | 159 | CD1 | ILE | 34 | 62.082 | 27.694 | 119.040 | 1.00 | 25.09 |
| ATOM | 160 | C | ILE | 34 | 61.115 | 31.504 | 115.959 | 1.00 | 29.23 |
| ATOM | 161 | O | ILE | 34 | 60.862 | 32.338 | 116.834 | 1.00 | 30.21 |
| ATOM | 162 | N | HIS | 35 | 60.628 | 31.572 | 114.725 | 1.00 | 30.40 |
| ATOM | 163 | CA | HIS | 35 | 59.727 | 32.630 | 114.301 | 1.00 | 30.70 |
| ATOM | 164 | CB | HIS | 35 | 59.619 | 32.664 | 112.775 | 1.00 | 31.64 |
| ATOM | 165 | CG | HIS | 35 | 60.916 | 32.944 | 112.082 | 1.00 | 33.81 |
| ATOM | 166 | CD2 | HIS | 35 | 61.745 | 32.136 | 111.379 | 1.00 | 34.56 |
| ATOM | 167 | ND1 | HIS | 35 | 61.517 | 34.184 | 112.104 | 1.00 | 34.42 |
| ATOM | 168 | CE1 | HIS | 35 | 62.663 | 34.127 | 111.447 | 1.00 | 34.81 |
| ATOM | 169 | NE2 | HIS | 35 | 62.825 | 32.895 | 110.998 | 1.00 | 35.40 |
| ATOM | 170 | C | HIS | 35 | 58.353 | 32.356 | 114.874 | 1.00 | 30.61 |
| ATOM | 171 | O | HIS | 35 | 57.996 | 31.209 | 115.132 | 1.00 | 30.59 |
| ATOM | 172 | N | PRO | 36 | 57.560 | 33.411 | 115.084 | 1.00 | 30.75 |
| ATOM | 173 | CD | PRO | 36 | 57.903 | 34.836 | 114.961 | 1.00 | 30.69 |
| ATOM | 174 | CA | PRO | 36 | 56.216 | 33.247 | 115.628 | 1.00 | 30.14 |
| ATOM | 175 | CB | PRO | 36 | 55.726 | 34.683 | 115.757 | 1.00 | 29.29 |
| ATOM | 176 | CG | PRO | 36 | 56.990 | 35.460 | 115.966 | 1.00 | 29.66 |
| ATOM | 177 | C | PRO | 36 | 55.346 | 32.422 | 114.680 | 1.00 | 30.78 |
| ATOM | 178 | O | PRO | 36 | 54.359 | 31.823 | 115.096 | 1.00 | 29.83 |
| ATOM | 179 | N | ASP | 37 | 55.716 | 32.391 | 113.404 | 1.00 | 31.83 |
| ATOM | 180 | CA | ASP | 37 | 54.933 | 31.637 | 112.436 | 1.00 | 32.95 |
| ATOM | 181 | CB | ASP | 37 | 54.958 | 32.305 | 111.057 | 1.00 | 32.63 |
| ATOM | 182 | CG | ASP | 37 | 56.341 | 32.377 | 110.461 | 1.00 | 34.16 |
| ATOM | 183 | OD1 | ASP | 37 | 57.108 | 31.398 | 110.570 | 1.00 | 34.89 |
| ATOM | 184 | OD2 | ASP | 37 | 56.654 | 33.420 | 109.856 | 1.00 | 35.19 |
| ATOM | 185 | C | ASP | 37 | 55.351 | 30.181 | 112.305 | 1.00 | 33.57 |
| ATOM | 186 | O | ASP | 37 | 54.767 | 29.435 | 111.523 | 1.00 | 33.17 |
| ATOM | 187 | N | GLY | 38 | 56.362 | 29.775 | 113.065 | 1.00 | 33.49 |
| ATOM | 188 | CA | GLY | 38 | 56.798 | 28.394 | 113.000 | 1.00 | 32.49 |
| ATOM | 189 | C | GLY | 38 | 58.094 | 28.128 | 112.262 | 1.00 | 31.52 |
| ATOM | 190 | O | GLY | 38 | 58.666 | 27.056 | 112.399 | 1.00 | 30.69 |
| ATOM | 191 | N | ARG | 39 | 58.566 | 29.080 | 111.472 | 1.00 | 31.26 |
| ATOM | 192 | CA | ARG | 39 | 59.810 | 28.869 | 110.752 | 1.00 | 31.69 |
| ATOM | 193 | CB | ARG | 39 | 60.053 | 30.008 | 109.758 | 1.00 | 31.81 |
| ATOM | 194 | CG | ARG | 39 | 59.171 | 29.980 | 108.515 | 1.00 | 32.81 |
| ATOM | 195 | CD | ARG | 39 | 59.377 | 31.207 | 107.634 | 1.00 | 31.85 |
| ATOM | 196 | NE | ARG | 39 | 58.932 | 32.417 | 108.317 | 1.00 | 34.13 |
| ATOM | 197 | CZ | ARG | 39 | 59.088 | 33.652 | 107.847 | 1.00 | 35.53 |
| ATOM | 198 | NH1 | ARG | 39 | 58.649 | 34.687 | 108.553 | 1.00 | 35.87 |
| ATOM | 199 | NH2 | ARG | 39 | 59.681 | 33.860 | 106.678 | 1.00 | 35.37 |
| ATOM | 200 | C | ARG | 39 | 60.973 | 28.797 | 111.732 | 1.00 | 32.08 |
| ATOM | 201 | O | ARG | 39 | 60.947 | 29.431 | 112.784 | 1.00 | 32.13 |
| ATOM | 202 | N | VAL | 40 | 61.991 | 28.008 | 111.395 | 1.00 | 32.00 |
| ATOM | 203 | CA | VAL | 40 | 63.174 | 27.902 | 112.244 | 1.00 | 30.66 |
| ATOM | 204 | CB | VAL | 40 | 63.271 | 26.564 | 112.974 | 1.00 | 29.32 |
| ATOM | 205 | CG1 | VAL | 40 | 64.335 | 26.668 | 114.031 | 1.00 | 30.19 |
| ATOM | 206 | CG2 | VAL | 40 | 61.961 | 26.210 | 113.611 | 1.00 | 28.68 |
| ATOM | 207 | C | VAL | 40 | 64.443 | 28.083 | 111.422 | 1.00 | 29.72 |
| ATOM | 208 | O | VAL | 40 | 64.609 | 27.476 | 110.374 | 1.00 | 29.97 |
| ATOM | 209 | N | ASP | 41 | 65.335 | 28.930 | 111.912 | 1.00 | 28.45 |
| ATOM | 210 | CA | ASP | 41 | 66.579 | 29.216 | 111.226 | 1.00 | 27.57 |
| ATOM | 211 | CB | ASP | 41 | 66.326 | 30.164 | 110.058 | 1.00 | 26.38 |
| ATOM | 212 | CG | ASP | 41 | 65.642 | 31.437 | 110.487 | 1.00 | 25.63 |
| ATOM | 213 | OD1 | ASP | 41 | 65.557 | 32.379 | 109.683 | 1.00 | 26.72 |
| ATOM | 214 | OD2 | ASP | 41 | 65.181 | 31.496 | 111.633 | 1.00 | 26.67 |

TABLE 6-continued

FGF2/FGFR1/Heparin Ternary Complex

| | | | | | | | | |
|---|---|---|---|---|---|---|---|---|
| ATOM | 215 | C | ASP | 41 | 67.507 | 29.880 | 112.218 | 1.00 | 27.61 |
| ATOM | 216 | O | ASP | 41 | 67.252 | 29.853 | 113.410 | 1.00 | 29.10 |
| ATOM | 217 | N | GLY | 42 | 68.576 | 30.487 | 111.726 | 1.00 | 27.57 |
| ATOM | 218 | CA | GLY | 42 | 69.501 | 31.154 | 112.616 | 1.00 | 27.36 |
| ATOM | 219 | C | GLY | 42 | 69.678 | 32.631 | 112.314 | 1.00 | 27.75 |
| ATOM | 220 | O | GLY | 42 | 69.395 | 33.102 | 111.210 | 1.00 | 27.79 |
| ATOM | 221 | N | VAL | 43 | 70.142 | 33.363 | 113.319 | 1.00 | 27.36 |
| ATOM | 222 | CA | VAL | 43 | 70.406 | 34.787 | 113.199 | 1.00 | 28.43 |
| ATOM | 223 | CB | VAL | 43 | 69.276 | 35.663 | 113.756 | 1.00 | 27.62 |
| ATOM | 224 | CG1 | VAL | 43 | 68.588 | 36.385 | 112.645 | 1.00 | 27.23 |
| ATOM | 225 | CG2 | VAL | 43 | 68.308 | 34.824 | 114.551 | 1.00 | 29.14 |
| ATOM | 226 | C | VAL | 43 | 71.610 | 35.090 | 114.048 | 1.00 | 29.73 |
| ATOM | 227 | O | VAL | 43 | 71.684 | 34.675 | 115.197 | 1.00 | 29.49 |
| ATOM | 228 | N | ARG | 44 | 72.557 | 35.823 | 113.494 | 1.00 | 32.24 |
| ATOM | 229 | CA | ARG | 44 | 73.723 | 36.175 | 114.270 | 1.00 | 34.28 |
| ATOM | 230 | CB | ARG | 44 | 74.868 | 36.543 | 113.347 | 1.00 | 35.61 |
| ATOM | 231 | CG | ARG | 44 | 75.389 | 35.358 | 112.587 | 1.00 | 38.73 |
| ATOM | 232 | CD | ARG | 44 | 76.387 | 35.790 | 111.550 | 1.00 | 40.80 |
| ATOM | 233 | NE | ARG | 44 | 77.205 | 34.667 | 111.133 | 1.00 | 43.26 |
| ATOM | 234 | CZ | ARG | 44 | 77.965 | 34.665 | 110.047 | 1.00 | 45.68 |
| ATOM | 235 | NH1 | ARG | 44 | 78.005 | 35.734 | 109.267 | 1.00 | 46.13 |
| ATOM | 236 | NH2 | ARG | 44 | 78.683 | 33.591 | 109.743 | 1.00 | 47.63 |
| ATOM | 237 | C | ARG | 44 | 73.423 | 37.320 | 115.230 | 1.00 | 34.49 |
| ATOM | 238 | O | ARG | 44 | 74.102 | 37.469 | 116.238 | 1.00 | 34.82 |
| ATOM | 239 | N | GLU | 45 | 72.401 | 38.116 | 114.936 | 1.00 | 34.24 |
| ATOM | 240 | CA | GLU | 45 | 72.063 | 39.234 | 115.806 | 1.00 | 34.89 |
| ATOM | 241 | CB | GLU | 45 | 71.032 | 40.136 | 115.135 | 1.00 | 36.45 |
| ATOM | 242 | CG | GLU | 45 | 71.511 | 40.716 | 113.831 | 1.00 | 38.67 |
| ATOM | 243 | CD | GLU | 45 | 72.789 | 41.508 | 113.990 | 1.00 | 40.75 |
| ATOM | 244 | OE1 | GLU | 45 | 73.443 | 41.780 | 112.958 | 1.00 | 40.01 |
| ATOM | 245 | OE2 | GLU | 45 | 73.137 | 41.861 | 115.142 | 1.00 | 43.18 |
| ATOM | 246 | C | GLU | 45 | 71.553 | 38.809 | 117.175 | 1.00 | 34.59 |
| ATOM | 247 | O | GLU | 45 | 70.457 | 38.273 | 117.308 | 1.00 | 35.36 |
| ATOM | 248 | N | LYS | 46 | 72.356 | 39.072 | 118.198 | 1.00 | 33.75 |
| ATOM | 249 | CA | LYS | 46 | 71.997 | 38.715 | 119.565 | 1.00 | 32.50 |
| ATOM | 250 | CB | LYS | 46 | 73.173 | 39.001 | 120.508 | 1.00 | 30.55 |
| ATOM | 251 | CG | LYS | 46 | 72.914 | 38.640 | 121.976 | 1.00 | 29.99 |
| ATOM | 252 | CD | LYS | 46 | 74.222 | 38.563 | 122.762 | 1.00 | 29.49 |
| ATOM | 253 | CE | LYS | 46 | 74.038 | 38.100 | 124.212 | 1.00 | 30.06 |
| ATOM | 254 | NZ | LYS | 46 | 73.784 | 39.231 | 125.169 | 1.00 | 30.34 |
| ATOM | 255 | C | LYS | 46 | 70.741 | 39.431 | 120.067 | 1.00 | 32.59 |
| ATOM | 256 | O | LYS | 46 | 70.109 | 38.991 | 121.028 | 1.00 | 32.11 |
| ATOM | 257 | N | SER | 47 | 70.374 | 40.524 | 119.409 | 1.00 | 32.29 |
| ATOM | 258 | CA | SER | 47 | 69.210 | 41.290 | 119.816 | 1.00 | 32.73 |
| ATOM | 259 | CB | SER | 47 | 69.417 | 42.755 | 119.468 | 1.00 | 31.79 |
| ATOM | 260 | OG | SER | 47 | 69.643 | 42.912 | 118.083 | 1.00 | 34.24 |
| ATOM | 261 | C | SER | 47 | 67.913 | 40.793 | 119.192 | 1.00 | 33.36 |
| ATOM | 262 | O | SER | 47 | 66.833 | 41.292 | 119.499 | 1.00 | 32.79 |
| ATOM | 263 | N | ASP | 48 | 68.014 | 39.806 | 118.313 | 1.00 | 34.12 |
| ATOM | 264 | CA | ASP | 48 | 66.830 | 39.255 | 117.665 | 1.00 | 34.15 |
| ATOM | 265 | CB | ASP | 48 | 67.200 | 37.982 | 116.916 | 1.00 | 34.62 |
| ATOM | 266 | CG | ASP | 48 | 66.148 | 37.573 | 115.922 | 1.00 | 36.63 |
| ATOM | 267 | OD1 | ASP | 48 | 66.138 | 38.139 | 114.809 | 1.00 | 37.75 |
| ATOM | 268 | OD2 | ASP | 48 | 65.324 | 36.696 | 116.256 | 1.00 | 37.73 |
| ATOM | 269 | C | ASP | 48 | 65.756 | 38.933 | 118.701 | 1.00 | 33.53 |
| ATOM | 270 | O | ASP | 48 | 66.033 | 38.311 | 119.722 | 1.00 | 35.73 |
| ATOM | 271 | N | PRO | 49 | 64.514 | 39.347 | 118.449 | 1.00 | 31.91 |
| ATOM | 272 | CD | PRO | 49 | 64.085 | 40.209 | 117.336 | 1.00 | 30.21 |
| ATOM | 273 | CA | PRO | 49 | 63.404 | 39.096 | 119.370 | 1.00 | 31.23 |
| ATOM | 274 | CB | PRO | 49 | 62.319 | 40.035 | 118.845 | 1.00 | 30.48 |
| ATOM | 275 | CG | PRO | 49 | 62.596 | 40.079 | 117.398 | 1.00 | 29.71 |
| ATOM | 276 | C | PRO | 49 | 62.926 | 37.638 | 119.456 | 1.00 | 31.07 |
| ATOM | 277 | O | PRO | 49 | 62.094 | 37.291 | 120.299 | 1.00 | 31.40 |
| ATOM | 278 | N | HIS | 50 | 63.462 | 36.781 | 118.596 | 1.00 | 30.80 |
| ATOM | 279 | CA | HIS | 50 | 63.033 | 35.392 | 118.575 | 1.00 | 29.86 |
| ATOM | 280 | CB | HIS | 50 | 62.436 | 35.068 | 117.216 | 1.00 | 28.95 |
| ATOM | 281 | CG | HIS | 50 | 61.474 | 36.098 | 116.736 | 1.00 | 28.18 |
| ATOM | 282 | CD2 | HIS | 50 | 61.543 | 36.966 | 115.701 | 1.00 | 27.42 |
| ATOM | 283 | ND1 | HIS | 50 | 60.284 | 36.357 | 117.380 | 1.00 | 28.66 |
| ATOM | 284 | CE1 | HIS | 50 | 59.660 | 37.341 | 116.760 | 1.00 | 28.45 |
| ATOM | 285 | NE2 | HIS | 50 | 60.404 | 37.728 | 115.740 | 1.00 | 28.50 |
| ATOM | 286 | C | HIS | 50 | 64.108 | 34.374 | 118.875 | 1.00 | 29.05 |
| ATOM | 287 | O | HIS | 50 | 63.992 | 33.227 | 118.457 | 1.00 | 30.34 |
| ATOM | 288 | N | ILE | 51 | 65.158 | 34.767 | 119.580 | 1.00 | 26.57 |
| ATOM | 289 | CA | ILE | 51 | 66.172 | 33.794 | 119.882 | 1.00 | 25.39 |
| ATOM | 290 | CB | ILE | 51 | 67.546 | 34.274 | 119.458 | 1.00 | 23.16 |
| ATOM | 291 | CG2 | ILE | 51 | 67.625 | 34.288 | 117.949 | 1.00 | 23.31 |

TABLE 6-continued

FGF2/FGFR1/Heparin Ternary Complex

| ATOM | 292 | GG1 | ILE | 51 | 67.824 | 35.655 | 120.035 | 1.00 | 22.31 |
|---|---|---|---|---|---|---|---|---|---|
| ATOM | 293 | CD1 | ILE | 51 | 69.234 | 36.124 | 119.788 | 1.00 | 19.90 |
| ATOM | 294 | C | ILE | 51 | 66.179 | 33.368 | 121.343 | 1.00 | 26.50 |
| ATOM | 295 | O | ILE | 51 | 66.994 | 32.538 | 121.746 | 1.00 | 27.21 |
| ATOM | 296 | N | LYS | 52 | 65.263 | 33.914 | 122.137 | 1.00 | 26.83 |
| ATOM | 297 | CA | LYS | 52 | 65.179 | 33.530 | 123.546 | 1.00 | 28.13 |
| ATOM | 298 | CB | LYS | 52 | 64.509 | 34.613 | 124.390 | 1.00 | 28.54 |
| ATOM | 299 | CG | LYS | 52 | 65.446 | 35.713 | 124.844 | 1.00 | 30.65 |
| ATOM | 300 | CD | LYS | 52 | 64.666 | 37.003 | 125.105 | 1.00 | 33.21 |
| ATOM | 301 | CE | LYS | 52 | 65.556 | 38.156 | 125.566 | 1.00 | 32.45 |
| ATOM | 302 | NZ | LYS | 52 | 66.103 | 37.936 | 126.935 | 1.00 | 33.76 |
| ATOM | 303 | C | LYS | 52 | 64.383 | 32.240 | 123.653 | 1.00 | 28.24 |
| ATOM | 304 | O | LYS | 52 | 63.161 | 32.227 | 123.455 | 1.00 | 28.10 |
| ATOM | 305 | N | LEU | 53 | 65.092 | 31.159 | 123.972 | 1.00 | 27.84 |
| ATOM | 306 | CA | LEU | 53 | 64.492 | 29.835 | 124.095 | 1.00 | 26.95 |
| ATOM | 307 | CB | LEU | 53 | 65.350 | 28.802 | 123.374 | 1.00 | 26.01 |
| ATOM | 308 | CG | LEU | 53 | 65.980 | 29.249 | 122.066 | 1.00 | 24.73 |
| ATOM | 309 | CD1 | LEU | 53 | 66.738 | 28.085 | 121.481 | 1.00 | 23.64 |
| ATOM | 310 | CD2 | LEU | 53 | 64.907 | 29.757 | 121.120 | 1.00 | 23.87 |
| ATOM | 311 | C | LEU | 53 | 64.356 | 29.395 | 125.535 | 1.00 | 26.85 |
| ATOM | 312 | O | LEU | 53 | 65.211 | 29.695 | 126.369 | 1.00 | 27.66 |
| ATOM | 313 | N | GLN | 54 | 63.284 | 28.663 | 125.811 | 1.00 | 25.84 |
| ATOM | 314 | CA | GLN | 54 | 63.020 | 28.140 | 127.142 | 1.00 | 25.74 |
| ATOM | 315 | CB | GLN | 54 | 61.586 | 28.471 | 127.535 | 1.00 | 25.45 |
| ATOM | 316 | CG | GLN | 54 | 61.179 | 28.035 | 128.921 | 1.00 | 27.24 |
| ATOM | 317 | CD | GLN | 54 | 61.995 | 28.697 | 130.012 | 1.00 | 29.91 |
| ATOM | 318 | OE1 | GLN | 54 | 62.193 | 29.911 | 130.016 | 1.00 | 28.79 |
| ATOM | 319 | NE2 | GLN | 54 | 62.462 | 27.896 | 130.960 | 1.00 | 33.80 |
| ATOM | 320 | C | GLN | 54 | 63.221 | 26.626 | 127.070 | 1.00 | 25.53 |
| ATOM | 321 | O | GLN | 54 | 62.354 | 25.906 | 126.584 | 1.00 | 26.86 |
| ATOM | 322 | N | LEU | 55 | 64.375 | 26.142 | 127.516 | 1.00 | 24.71 |
| ATOM | 323 | CA | LEU | 55 | 64.627 | 24.710 | 127.481 | 1.00 | 24.05 |
| ATOM | 324 | CB | LEU | 55 | 66.127 | 24.421 | 127.413 | 1.00 | 22.59 |
| ATOM | 325 | CG | LEU | 55 | 66.902 | 25.117 | 126.306 | 1.00 | 22.36 |
| ATOM | 326 | CD1 | LEU | 55 | 67.955 | 24.190 | 125.754 | 1.00 | 22.98 |
| ATOM | 327 | CD2 | LEU | 55 | 65.968 | 25.493 | 125.204 | 1.00 | 23.14 |
| ATOM | 328 | C | LEU | 55 | 64.040 | 24.082 | 128.731 | 1.00 | 24.22 |
| ATOM | 329 | O | LEU | 55 | 64.347 | 24.503 | 129.852 | 1.00 | 24.57 |
| ATOM | 330 | N | GLN | 56 | 63.179 | 23.091 | 128.544 | 1.00 | 23.12 |
| ATOM | 331 | CA | GLN | 56 | 62.577 | 22.422 | 129.676 | 1.00 | 24.28 |
| ATOM | 332 | CB | GLN | 56 | 61.063 | 22.595 | 129.670 | 1.00 | 22.45 |
| ATOM | 333 | CG | GLN | 56 | 60.349 | 21.779 | 130.733 | 1.00 | 20.68 |
| ATOM | 334 | CD | GLN | 56 | 60.688 | 22.203 | 132.155 | 1.00 | 21.65 |
| ATOM | 335 | OE1 | GLN | 56 | 60.452 | 23.345 | 132.552 | 1.00 | 20.04 |
| ATOM | 336 | NE2 | GLN | 56 | 61.234 | 21.276 | 132.933 | 1.00 | 23.27 |
| ATOM | 337 | C | GLN | 56 | 62.921 | 20.963 | 129.569 | 1.00 | 25.91 |
| ATOM | 338 | O | GLN | 56 | 62.989 | 20.426 | 128.468 | 1.00 | 28.11 |
| ATOM | 339 | N | ALA | 57 | 63.157 | 20.318 | 130.701 | 1.00 | 26.95 |
| ATOM | 340 | CA | ALA | 57 | 63.483 | 18.902 | 130.677 | 1.00 | 28.44 |
| ATOM | 341 | CB | ALA | 57 | 64.433 | 18.549 | 131.819 | 1.00 | 29.12 |
| ATOM | 342 | C | ALA | 57 | 62.185 | 18.150 | 130.830 | 1.00 | 29.10 |
| ATOM | 343 | O | ALA | 57 | 61.320 | 18.559 | 131.605 | 1.00 | 28.67 |
| ATOM | 344 | N | GLU | 58 | 62.029 | 17.070 | 130.072 | 1.00 | 29.83 |
| ATOM | 345 | CA | GLU | 58 | 60.820 | 16.274 | 130.181 | 1.00 | 30.65 |
| ATOM | 346 | CB | GLU | 58 | 60.346 | 15.824 | 128.811 | 1.00 | 31.00 |
| ATOM | 347 | CG | GLU | 58 | 58.857 | 15.539 | 128.757 | 1.00 | 32.60 |
| ATOM | 348 | CD | GLU | 58 | 58.027 | 16.723 | 129.207 | 1.00 | 33.58 |
| ATOM | 349 | OE1 | GLU | 58 | 58.392 | 17.869 | 128.858 | 1.00 | 33.56 |
| ATOM | 350 | OE2 | GLU | 58 | 57.008 | 16.506 | 129.901 | 1.00 | 35.63 |
| ATOM | 351 | C | GLU | 58 | 61.188 | 15.078 | 131.036 | 1.00 | 30.91 |
| ATOM | 352 | O | GLU | 58 | 60.333 | 14.344 | 131.515 | 1.00 | 30.95 |
| ATOM | 353 | N | GLU | 59 | 62.489 | 14.916 | 131.232 | 1.00 | 31.82 |
| ATOM | 354 | CA | GLU | 59 | 63.040 | 13.841 | 132.031 | 1.00 | 31.78 |
| ATOM | 355 | CB | GLU | 59 | 62.496 | 12.499 | 131.578 | 1.00 | 33.64 |
| ATOM | 356 | CG | GLU | 59 | 63.031 | 12.038 | 130.260 | 1.00 | 36.93 |
| ATOM | 357 | CD | GLU | 59 | 62.664 | 10.602 | 129.993 | 1.00 | 39.85 |
| ATOM | 358 | OE1 | GLU | 59 | 61.461 | 10.331 | 129.790 | 1.00 | 42.02 |
| ATOM | 359 | OE2 | GLU | 59 | 63.571 | 9.741 | 129.999 | 1.00 | 41.11 |
| ATOM | 360 | C | GLU | 59 | 64.529 | 13.873 | 131.821 | 1.00 | 30.93 |
| ATOM | 361 | O | GLU | 59 | 65.005 | 14.502 | 130.880 | 1.00 | 31.63 |
| ATOM | 362 | N | ARG | 60 | 65.259 | 13.186 | 132.688 | 1.00 | 29.47 |
| ATOM | 363 | CA | ARG | 60 | 66.710 | 13.123 | 132.609 | 1.00 | 28.68 |
| ATOM | 364 | CB | ARG | 60 | 67.196 | 11.887 | 133.344 | 1.00 | 30.06 |
| ATOM | 365 | CG | ARG | 60 | 68.340 | 12.140 | 134.272 | 1.00 | 34.02 |
| ATOM | 366 | CD | ARG | 60 | 68.351 | 11.091 | 135.363 | 1.00 | 38.00 |
| ATOM | 367 | NE | ARG | 60 | 68.988 | 9.853 | 134.937 | 1.00 | 41.17 |
| ATOM | 368 | CZ | ARG | 60 | 70.275 | 9.754 | 134.610 | 1.00 | 43.17 |

TABLE 6-continued

FGF2/FGFR1/Heparin Ternary Complex

| ATOM | 369 | NH1 | ARG | 60 | 71.064 | 10.819 | 134.653 | 1.00 | 43.52 |
|---|---|---|---|---|---|---|---|---|---|
| ATOM | 370 | NH2 | ARG | 60 | 70.787 | 8.579 | 134.266 | 1.00 | 45.60 |
| ATOM | 371 | C | ARG | 60 | 67.236 | 13.083 | 131.181 | 1.00 | 27.56 |
| ATOM | 372 | O | ARG | 60 | 66.915 | 12.163 | 130.420 | 1.00 | 26.74 |
| ATOM | 373 | N | GLY | 61 | 68.036 | 14.093 | 130.834 | 1.00 | 25.42 |
| ATOM | 374 | CA | GLY | 61 | 68.650 | 14.179 | 129.521 | 1.00 | 23.18 |
| ATOM | 375 | C | GLY | 61 | 67.769 | 14.499 | 128.336 | 1.00 | 22.45 |
| ATOM | 376 | O | GLY | 61 | 68.255 | 14.571 | 127.206 | 1.00 | 22.39 |
| ATOM | 377 | N | VAL | 62 | 66.480 | 14.696 | 128.576 | 1.00 | 21.70 |
| ATOM | 378 | CA | VAL | 62 | 65.559 | 14.991 | 127.488 | 1.00 | 21.36 |
| ATOM | 379 | CB | VAL | 62 | 64.467 | 13.948 | 127.390 | 1.00 | 21.25 |
| ATOM | 380 | CG1 | VAL | 62 | 63.545 | 14.300 | 126.255 | 1.00 | 20.20 |
| ATOM | 381 | CG2 | VAL | 62 | 65.086 | 12.578 | 127.184 | 1.00 | 22.19 |
| ATOM | 382 | C | VAL | 62 | 64.891 | 16.330 | 127.660 | 1.00 | 21.42 |
| ATOM | 383 | O | VAL | 62 | 64.329 | 16.625 | 128.718 | 1.00 | 21.01 |
| ATOM | 384 | N | VAL | 63 | 64.922 | 17.131 | 126.607 | 1.00 | 21.21 |
| ATOM | 385 | CA | VAL | 63 | 64.331 | 18.451 | 126.684 | 1.00 | 22.02 |
| ATOM | 386 | CB | VAL | 63 | 65.419 | 19.536 | 126.680 | 1.00 | 21.49 |
| ATOM | 387 | CG1 | VAL | 63 | 66.481 | 19.213 | 127.704 | 1.00 | 21.73 |
| ATOM | 388 | CG2 | VAL | 63 | 66.026 | 19.650 | 125.290 | 1.00 | 20.18 |
| ATOM | 389 | C | VAL | 63 | 63.387 | 18.808 | 125.553 | 1.00 | 23.18 |
| ATOM | 390 | O | VAL | 63 | 63.413 | 18.210 | 124.477 | 1.00 | 23.67 |
| ATOM | 391 | N | SER | 64 | 62.550 | 19.798 | 125.827 | 1.00 | 23.91 |
| ATOM | 392 | CA | SER | 64 | 61.649 | 20.350 | 124.839 | 1.00 | 25.35 |
| ATOM | 393 | CB | SER | 64 | 60.254 | 20.585 | 125.427 | 1.00 | 25.45 |
| ATOM | 394 | OG | SER | 64 | 60.157 | 21.858 | 126.047 | 1.00 | 25.74 |
| ATOM | 395 | C | SER | 64 | 62.380 | 21.686 | 124.670 | 1.00 | 26.31 |
| ATOM | 396 | O | SER | 64 | 63.103 | 22.105 | 125.584 | 1.00 | 26.97 |
| ATOM | 397 | N | ILE | 65 | 62.243 | 22.333 | 123.516 | 1.00 | 25.31 |
| ATOM | 398 | CA | ILE | 65 | 62.889 | 23.624 | 123.302 | 1.00 | 23.48 |
| ATOM | 399 | CB | ILE | 65 | 63.965 | 23.536 | 122.239 | 1.00 | 21.26 |
| ATOM | 400 | CG2 | ILE | 65 | 64.493 | 24.913 | 121.921 | 1.00 | 20.99 |
| ATOM | 401 | CG1 | ILE | 65 | 65.087 | 22.637 | 122.730 | 1.00 | 19.95 |
| ATOM | 402 | CD1 | ILE | 65 | 66.175 | 22.427 | 121.710 | 1.00 | 18.86 |
| ATOM | 403 | C | ILE | 65 | 61.793 | 24.551 | 122.833 | 1.00 | 24.23 |
| ATOM | 404 | O | ILE | 65 | 61.307 | 24.432 | 121.717 | 1.00 | 26.34 |
| ATOM | 405 | N | LYS | 66 | 61.398 | 25.476 | 123.688 | 1.00 | 23.45 |
| ATOM | 406 | CA | LYS | 66 | 60.315 | 26.376 | 123.347 | 1.00 | 24.16 |
| ATOM | 407 | CB | LYS | 66 | 59.308 | 26.366 | 124.490 | 1.00 | 25.18 |
| ATOM | 408 | CG | LYS | 66 | 58.083 | 27.234 | 124.309 | 1.00 | 26.80 |
| ATOM | 409 | CD | LYS | 66 | 57.169 | 27.059 | 125.526 | 1.00 | 28.71 |
| ATOM | 410 | CE | LYS | 66 | 56.044 | 28.085 | 125.597 | 1.00 | 29.36 |
| ATOM | 411 | NZ | LYS | 66 | 55.434 | 28.077 | 126.956 | 1.00 | 30.03 |
| ATOM | 412 | C | LYS | 66 | 60.743 | 27.801 | 123.049 | 1.00 | 24.99 |
| ATOM | 413 | O | LYS | 66 | 61.398 | 28.451 | 123.861 | 1.00 | 26.36 |
| ATOM | 414 | N | GLY | 67 | 60.383 | 28.288 | 121.871 | 1.00 | 24.39 |
| ATOM | 415 | CA | GLY | 67 | 60.721 | 29.649 | 121.535 | 1.00 | 23.66 |
| ATOM | 416 | C | GLY | 67 | 59.802 | 30.486 | 122.394 | 1.00 | 23.71 |
| ATOM | 417 | O | GLY | 67 | 58.590 | 30.370 | 122.280 | 1.00 | 23.31 |
| ATOM | 418 | N | VAL | 68 | 60.363 | 31.325 | 123.253 | 1.00 | 24.43 |
| ATOM | 419 | CA | VAL | 68 | 59.538 | 32.137 | 124.143 | 1.00 | 25.58 |
| ATOM | 420 | CB | VAL | 68 | 60.412 | 32.961 | 125.102 | 1.00 | 24.89 |
| ATOM | 421 | CG1 | VAL | 68 | 59.547 | 33.906 | 125.913 | 1.00 | 24.50 |
| ATOM | 422 | CG2 | VAL | 68 | 61.163 | 32.038 | 126.026 | 1.00 | 23.51 |
| ATOM | 423 | C | VAL | 68 | 58.569 | 33.075 | 123.425 | 1.00 | 27.13 |
| ATOM | 424 | O | VAL | 68 | 57.374 | 33.093 | 123.725 | 1.00 | 27.43 |
| ATOM | 425 | N | SER | 69 | 59.097 | 33.845 | 122.480 | 1.00 | 27.71 |
| ATOM | 426 | CA | SER | 69 | 58.318 | 34.802 | 121.706 | 1.00 | 27.80 |
| ATOM | 427 | CB | SER | 69 | 59.279 | 35.657 | 120.871 | 1.00 | 26.55 |
| ATOM | 428 | OG | SER | 69 | 58.652 | 36.153 | 119.712 | 1.00 | 23.62 |
| ATOM | 429 | C | SER | 69 | 57.293 | 34.135 | 120.791 | 1.00 | 28.43 |
| ATOM | 430 | O | SER | 69 | 56.116 | 34.493 | 120.784 | 1.00 | 27.80 |
| ATOM | 431 | N | ALA | 70 | 57.754 | 33.161 | 120.019 | 1.00 | 29.44 |
| ATOM | 432 | CA | ALA | 70 | 56.890 | 32.455 | 119.085 | 1.00 | 30.39 |
| ATOM | 433 | CB | ALA | 70 | 57.739 | 31.672 | 118.090 | 1.00 | 30.34 |
| ATOM | 434 | C | ALA | 70 | 55.911 | 31.526 | 119.793 | 1.00 | 30.53 |
| ATOM | 435 | O | ALA | 70 | 54.949 | 31.043 | 119.197 | 1.00 | 30.39 |
| ATOM | 436 | N | ASN | 71 | 56.147 | 31.285 | 121.071 | 1.00 | 30.77 |
| ATOM | 437 | CA | ASN | 71 | 55.271 | 30.407 | 121.817 | 1.00 | 32.78 |
| ATOM | 438 | CB | ASN | 71 | 53.970 | 31.137 | 122.123 | 1.00 | 32.63 |
| ATOM | 439 | CG | ASN | 71 | 53.257 | 30.571 | 123.330 | 1.00 | 33.86 |
| ATOM | 440 | OD1 | ASN | 71 | 53.857 | 30.378 | 124.386 | 1.00 | 35.51 |
| ATOM | 441 | ND2 | ASN | 71 | 51.968 | 30.315 | 123.186 | 1.00 | 34.15 |
| ATOM | 442 | C | ASN | 71 | 54.996 | 29.129 | 121.008 | 1.00 | 33.89 |
| ATOM | 443 | O | ASN | 71 | 53.848 | 28.735 | 120.803 | 1.00 | 33.35 |
| ATOM | 444 | N | ARG | 72 | 56.074 | 28.502 | 120.543 | 1.00 | 34.56 |
| ATOM | 445 | CA | ARG | 72 | 56.014 | 27.271 | 119.764 | 1.00 | 34.30 |

TABLE 6-continued

| FGF2/FGFR1/Heparin Ternary Complex | | | | | | | | |
|---|---|---|---|---|---|---|---|---|
| ATOM | 446 | CB | ARG | 72 | 56.245 | 27.545 | 118.280 | 1.00 | 33.36 |
| ATOM | 447 | CG | ARG | 72 | 55.174 | 28.321 | 117.553 | 1.00 | 33.71 |
| ATOM | 448 | CD | ARG | 72 | 55.635 | 28.572 | 116.110 | 1.00 | 34.74 |
| ATOM | 449 | NE | ARG | 72 | 54.624 | 29.232 | 115.290 | 1.00 | 35.27 |
| ATOM | 450 | CZ | ARG | 72 | 53.545 | 28.632 | 114.798 | 1.00 | 33.89 |
| ATOM | 451 | NH1 | ARG | 72 | 53.327 | 27.349 | 115.028 | 1.00 | 33.02 |
| ATOM | 452 | NH2 | ARG | 72 | 52.670 | 29.324 | 114.089 | 1.00 | 34.07 |
| ATOM | 453 | C | ARG | 72 | 57.138 | 26.369 | 120.242 | 1.00 | 34.85 |
| ATOM | 454 | O | ARG | 72 | 58.046 | 26.819 | 120.934 | 1.00 | 35.82 |
| ATOM | 455 | N | TYR | 73 | 57.092 | 25.102 | 119.846 | 1.00 | 34.88 |
| ATOM | 456 | CA | TYR | 73 | 58.120 | 24.149 | 120.233 | 1.00 | 33.16 |
| ATOM | 457 | CB | TYR | 73 | 57.488 | 22.981 | 120.971 | 1.00 | 29.48 |
| ATOM | 458 | CG | TYR | 73 | 56.795 | 23.390 | 122.244 | 1.00 | 27.00 |
| ATOM | 459 | CD1 | TYR | 73 | 55.509 | 23.920 | 122.224 | 1.00 | 25.62 |
| ATOM | 460 | CE1 | TYR | 73 | 54.878 | 24.301 | 123.396 | 1.00 | 23.39 |
| ATOM | 461 | CD2 | TYR | 73 | 57.432 | 23.258 | 123.474 | 1.00 | 25.71 |
| ATOM | 462 | CE2 | TYR | 73 | 56.812 | 23.640 | 124.645 | 1.00 | 23.18 |
| ATOM | 463 | CZ | TYR | 73 | 55.537 | 24.158 | 124.601 | 1.00 | 22.75 |
| ATOM | 464 | OH | TYR | 73 | 54.923 | 24.525 | 125.770 | 1.00 | 22.37 |
| ATOM | 465 | C | TYR | 73 | 58.909 | 23.638 | 119.045 | 1.00 | 33.61 |
| ATOM | 466 | O | TYR | 73 | 58.339 | 23.297 | 118.019 | 1.00 | 34.53 |
| ATOM | 467 | N | LEU | 74 | 60.225 | 23.595 | 119.184 | 1.00 | 33.83 |
| ATOM | 468 | CA | LEU | 74 | 61.077 | 23.108 | 118.113 | 1.00 | 35.21 |
| ATOM | 469 | CB | LEU | 74 | 62.538 | 23.322 | 118.471 | 1.00 | 32.63 |
| ATOM | 470 | CG | LEU | 74 | 63.465 | 22.385 | 117.715 | 1.00 | 30.54 |
| ATOM | 471 | CD1 | LEU | 74 | 63.375 | 22.702 | 116.241 | 1.00 | 30.96 |
| ATOM | 472 | CD2 | LEU | 74 | 64.871 | 22.523 | 118.226 | 1.00 | 29.71 |
| ATOM | 473 | C | LEU | 74 | 60.835 | 21.621 | 117.924 | 1.00 | 37.36 |
| ATOM | 474 | O | LEU | 74 | 61.081 | 20.837 | 118.839 | 1.00 | 39.11 |
| ATOM | 475 | N | ALA | 75 | 60.358 | 21.231 | 116.747 | 1.00 | 38.42 |
| ATOM | 476 | CA | ALA | 75 | 60.097 | 19.825 | 116.460 | 1.00 | 39.22 |
| ATOM | 477 | CB | ALA | 75 | 58.609 | 19.583 | 116.394 | 1.00 | 37.95 |
| ATOM | 478 | C | ALA | 75 | 60.751 | 19.431 | 115.146 | 1.00 | 40.58 |
| ATOM | 479 | O | ALA | 75 | 60.800 | 20.231 | 114.208 | 1.00 | 41.93 |
| ATOM | 480 | N | MET | 76 | 61.268 | 18.207 | 115.084 | 1.00 | 41.48 |
| ATOM | 481 | CA | MET | 76 | 61.908 | 17.717 | 113.868 | 1.00 | 42.71 |
| ATOM | 482 | CB | MET | 76 | 63.269 | 17.129 | 114.179 | 1.00 | 41.17 |
| ATOM | 483 | CG | MET | 76 | 64.039 | 16.797 | 112.949 | 1.00 | 40.91 |
| ATOM | 484 | SD | MET | 76 | 65.732 | 16.444 | 113.338 | 1.00 | 43.31 |
| ATOM | 485 | CE | MET | 76 | 65.586 | 14.747 | 113.794 | 1.00 | 43.79 |
| ATOM | 486 | C | MET | 76 | 61.037 | 16.649 | 113.222 | 1.00 | 44.35 |
| ATOM | 487 | O | MET | 76 | 60.809 | 15.591 | 113.799 | 1.00 | 44.28 |
| ATOM | 488 | N | LYS | 77 | 60.554 | 16.941 | 112.019 | 1.00 | 45.83 |
| ATOM | 489 | CA | LYS | 77 | 59.697 | 16.029 | 111.280 | 1.00 | 47.28 |
| ATOM | 490 | CB | LYS | 77 | 59.056 | 16.770 | 110.112 | 1.00 | 47.05 |
| ATOM | 491 | CG | LYS | 77 | 58.522 | 18.160 | 110.444 | 1.00 | 45.60 |
| ATOM | 492 | CD | LYS | 77 | 57.128 | 18.135 | 111.039 | 1.00 | 44.56 |
| ATOM | 493 | CE | LYS | 77 | 57.155 | 17.746 | 112.499 | 1.00 | 44.94 |
| ATOM | 494 | NZ | LYS | 77 | 55.799 | 17.813 | 113.127 | 1.00 | 45.37 |
| ATOM | 495 | C | LYS | 77 | 60.496 | 14.843 | 110.749 | 1.00 | 49.12 |
| ATOM | 496 | O | LYS | 77 | 61.725 | 14.839 | 110.805 | 1.00 | 48.68 |
| ATOM | 497 | N | GLU | 78 | 59.793 | 13.846 | 110.211 | 1.00 | 51.45 |
| ATOM | 498 | CA | GLU | 78 | 60.444 | 12.643 | 109.690 | 1.00 | 53.04 |
| ATOM | 499 | CB | GLU | 78 | 59.407 | 11.583 | 109.288 | 1.00 | 54.65 |
| ATOM | 500 | CG | GLU | 78 | 58.566 | 11.923 | 108.071 | 1.00 | 58.25 |
| ATOM | 501 | CD | GLU | 78 | 57.760 | 13.198 | 108.258 | 1.00 | 61.11 |
| ATOM | 502 | OE1 | GLU | 78 | 57.160 | 13.370 | 109.350 | 1.00 | 62.28 |
| ATOM | 503 | OE2 | GLU | 78 | 57.719 | 14.022 | 107.313 | 1.00 | 61.51 |
| ATOM | 504 | C | GLU | 78 | 61.425 | 12.855 | 108.539 | 1.00 | 52.66 |
| ATOM | 505 | O | GLU | 78 | 62.398 | 12.115 | 108.432 | 1.00 | 53.96 |
| ATOM | 506 | N | ASP | 79 | 61.195 | 13.836 | 107.671 | 1.00 | 51.02 |
| ATOM | 507 | CA | ASP | 79 | 62.141 | 14.049 | 106.579 | 1.00 | 49.50 |
| ATOM | 508 | CB | ASP | 79 | 61.517 | 14.883 | 105.461 | 1.00 | 49.01 |
| ATOM | 509 | CG | ASP | 79 | 60.976 | 16.197 | 105.951 | 1.00 | 48.61 |
| ATOM | 510 | OD1 | ASP | 79 | 60.637 | 17.053 | 105.106 | 1.00 | 47.79 |
| ATOM | 511 | OD2 | ASP | 79 | 60.885 | 16.368 | 107.182 | 1.00 | 48.70 |
| ATOM | 512 | C | ASP | 79 | 63.414 | 14.722 | 107.089 | 1.00 | 48.99 |
| ATOM | 513 | O | ASP | 79 | 64.396 | 14.861 | 106.356 | 1.00 | 48.58 |
| ATOM | 514 | N | GLY | 80 | 63.389 | 15.132 | 108.355 | 1.00 | 48.23 |
| ATOM | 515 | CA | GLY | 80 | 64.549 | 15.764 | 108.953 | 1.00 | 46.48 |
| ATOM | 516 | C | CLY | 80 | 64.545 | 17.274 | 108.901 | 1.00 | 44.84 |
| ATOM | 517 | O | GLY | 80 | 65.590 | 17.900 | 109.054 | 1.00 | 44.26 |
| ATOM | 518 | N | ARG | 81 | 63.382 | 17.871 | 108.679 | 1.00 | 44.21 |
| ATOM | 519 | CA | ARG | 81 | 63.302 | 19.323 | 108.624 | 1.00 | 43.88 |
| ATOM | 520 | CB | ARG | 81 | 62.362 | 19.781 | 107.507 | 1.00 | 45.36 |
| ATOM | 521 | CG | ARG | 81 | 60.896 | 19.485 | 107.762 | 1.00 | 49.01 |
| ATOM | 522 | CD | ARG | 81 | 60.009 | 19.877 | 106.574 | 1.00 | 50.98 |

TABLE 6-continued

FGF2/FGFR1/Heparin Ternary Complex

| ATOM | 523 | NE | ARG | 81 | 58.581 | 19.778 | 106.901 | 1.00 | 53.79 |
|---|---|---|---|---|---|---|---|---|---|
| ATOM | 524 | CZ | ARG | 81 | 57.880 | 18.643 | 106.965 | 1.00 | 55.03 |
| ATOM | 525 | NH1 | ARG | 81 | 58.455 | 17.471 | 106.718 | 1.00 | 55.84 |
| ATOM | 526 | NH2 | ARG | 81 | 56.593 | 18.676 | 107.294 | 1.00 | 55.29 |
| ATOM | 527 | C | ARG | 81 | 62.815 | 19.841 | 109.965 | 1.00 | 42.86 |
| ATOM | 528 | O | ARG | 81 | 62.109 | 19.139 | 110.693 | 1.00 | 42.39 |
| ATOM | 529 | N | LEU | 82 | 63.207 | 21.068 | 110.290 | 1.00 | 41.62 |
| ATOM | 530 | CA | LEU | 82 | 62.827 | 21.686 | 111.551 | 1.00 | 40.80 |
| ATOM | 531 | CB | LEU | 82 | 63.985 | 22.512 | 112.111 | 1.00 | 40.02 |
| ATOM | 532 | CG | LEU | 82 | 65.360 | 21.870 | 112.203 | 1.00 | 39.83 |
| ATOM | 533 | CD1 | LEU | 82 | 66.278 | 22.836 | 112.890 | 1.00 | 40.26 |
| ATOM | 534 | CD2 | LEU | 82 | 65.294 | 20.567 | 112.976 | 1.00 | 40.58 |
| ATOM | 535 | C | LEU | 82 | 61.628 | 22.599 | 111.388 | 1.00 | 40.36 |
| ATOM | 536 | O | LEU | 82 | 61.335 | 23.064 | 110.292 | 1.00 | 40.36 |
| ATOM | 537 | N | LEU | 83 | 60.957 | 22.862 | 112.501 | 1.00 | 39.84 |
| ATOM | 538 | CA | LEU | 83 | 59.800 | 23.739 | 112.536 | 1.00 | 40.98 |
| ATOM | 539 | CB | LEU | 83 | 58.700 | 23.201 | 111.618 | 1.00 | 40.74 |
| ATOM | 540 | CG | LEU | 83 | 58.065 | 21.838 | 111.904 | 1.00 | 40.46 |
| ATOM | 541 | CD1 | LEU | 83 | 57.117 | 21.904 | 113.096 | 1.00 | 39.09 |
| ATOM | 542 | CD2 | LEU | 83 | 57.299 | 21.417 | 110.677 | 1.00 | 40.49 |
| ATOM | 543 | C | LEU | 83 | 59.319 | 23.791 | 113.980 | 1.00 | 41.84 |
| ATOM | 544 | O | LEU | 83 | 59.698 | 22.952 | 114.787 | 1.00 | 42.18 |
| ATOM | 545 | N | ALA | 84 | 58.490 | 24.764 | 114.320 | 1.00 | 42.49 |
| ATOM | 546 | CA | ALA | 84 | 58.021 | 24.841 | 115.689 | 1.00 | 44.12 |
| ATOM | 547 | CB | ALA | 84 | 58.524 | 26.109 | 116.332 | 1.00 | 44.63 |
| ATOM | 548 | C | ALA | 84 | 56.506 | 24.738 | 115.812 | 1.00 | 45.19 |
| ATOM | 549 | O | ALA | 84 | 55.766 | 25.592 | 115.327 | 1.00 | 45.45 |
| ATOM | 550 | N | SER | 85 | 56.060 | 23.674 | 116.470 | 1.00 | 45.94 |
| ATOM | 551 | CA | SER | 85 | 54.643 | 23.411 | 116.679 | 1.00 | 46.93 |
| ATOM | 552 | CB | SER | 85 | 54.452 | 21.952 | 117.092 | 1.00 | 47.72 |
| ATOM | 553 | OG | SER | 85 | 53.104 | 21.693 | 117.446 | 1.00 | 49.98 |
| ATOM | 554 | C | SER | 85 | 54.054 | 24.329 | 117.746 | 1.00 | 47.26 |
| ATOM | 555 | O | SER | 85 | 54.763 | 24.775 | 118.642 | 1.00 | 48.27 |
| ATOM | 556 | N | LYS | 86 | 52.757 | 24.607 | 117.654 | 1.00 | 47.10 |
| ATOM | 557 | CA | LYS | 86 | 52.108 | 25.478 | 118.624 | 1.00 | 46.39 |
| ATOM | 558 | CB | LYS | 86 | 50.780 | 25.993 | 118.070 | 1.00 | 46.39 |
| ATOM | 559 | CG | LYS | 86 | 50.321 | 27.340 | 118.643 | 1.00 | 46.15 |
| ATOM | 560 | CD | LYS | 86 | 51.221 | 28.504 | 118.183 | 1.00 | 46.01 |
| ATOM | 561 | CE | LYS | 86 | 50.611 | 29.888 | 118.462 | 1.00 | 43.88 |
| ATOM | 562 | NZ | LYS | 86 | 50.529 | 30.273 | 119.903 | 1.00 | 42.01 |
| ATOM | 563 | C | LYS | 86 | 51.864 | 24.689 | 119.902 | 1.00 | 46.17 |
| ATOM | 564 | O | LYS | 86 | 51.822 | 25.250 | 120.997 | 1.00 | 46.38 |
| ATOM | 565 | N | SER | 87 | 51.702 | 23.380 | 119.752 | 1.00 | 45.54 |
| ATOM | 566 | CA | SER | 87 | 51.470 | 22.500 | 120.886 | 1.00 | 44.56 |
| ATOM | 567 | CB | SER | 87 | 50.066 | 21.899 | 120.825 | 1.00 | 45.04 |
| ATOM | 568 | OG | SER | 87 | 49.925 | 21.045 | 119.706 | 1.00 | 45.18 |
| ATOM | 569 | C | SER | 87 | 52.502 | 21.390 | 120.842 | 1.00 | 43.71 |
| ATOM | 570 | O | SER | 87 | 53.014 | 21.054 | 119.783 | 1.00 | 42.09 |
| ATOM | 571 | N | VAL | 88 | 52.799 | 20.814 | 121.997 | 1.00 | 43.56 |
| ATOM | 572 | CA | VAL | 88 | 53.796 | 19.769 | 122.068 | 1.00 | 43.63 |
| ATOM | 573 | CB | VAL | 88 | 54.184 | 19.513 | 123.528 | 1.00 | 42.66 |
| ATOM | 574 | CG1 | VAL | 88 | 55.281 | 18.477 | 123.602 | 1.00 | 42.15 |
| ATOM | 575 | CG2 | VAL | 88 | 54.634 | 20.807 | 124.167 | 1.00 | 41.54 |
| ATOM | 576 | C | VAL | 88 | 53.357 | 18.461 | 121.422 | 1.00 | 43.94 |
| ATOM | 577 | O | VAL | 88 | 52.185 | 18.107 | 121.455 | 1.00 | 43.53 |
| ATOM | 578 | N | THR | 89 | 54.318 | 17.765 | 120.816 | 1.00 | 44.55 |
| ATOM | 579 | CA | THR | 89 | 54.099 | 16.471 | 120.170 | 1.00 | 44.50 |
| ATOM | 580 | CB | THR | 89 | 53.913 | 16.585 | 118.633 | 1.00 | 44.01 |
| ATOM | 581 | OG1 | THR | 89 | 55.144 | 16.271 | 117.973 | 1.00 | 43.88 |
| ATOM | 582 | CG2 | THR | 89 | 53.496 | 17.982 | 118.240 | 1.00 | 43.75 |
| ATOM | 583 | C | THR | 89 | 55.356 | 15.647 | 120.446 | 1.00 | 45.06 |
| ATOM | 584 | O | THR | 89 | 56.395 | 16.193 | 120.823 | 1.00 | 45.26 |
| ATOM | 585 | N | ASP | 90 | 55.272 | 14.338 | 120.249 | 1.00 | 45.27 |
| ATOM | 586 | CA | ASP | 90 | 56.410 | 13.466 | 120.522 | 1.00 | 46.21 |
| ATOM | 587 | CB | ASP | 90 | 56.028 | 12.033 | 120.226 | 1.00 | 47.52 |
| ATOM | 588 | CG | ASP | 90 | 55.814 | 11.808 | 118.763 | 1.00 | 49.35 |
| ATOM | 589 | OD1 | ASP | 90 | 55.095 | 12.628 | 118.155 | 1.00 | 50.55 |
| ATOM | 590 | OD2 | ASP | 90 | 56.363 | 10.826 | 118.220 | 1.00 | 50.71 |
| ATOM | 591 | C | ASP | 90 | 57.654 | 13.809 | 119.715 | 1.00 | 46.06 |
| ATOM | 592 | O | ASP | 90 | 58.696 | 13.179 | 119.887 | 1.00 | 46.36 |
| ATOM | 593 | N | GLU | 91 | 57.547 | 14.808 | 118.844 | 1.00 | 45.13 |
| ATOM | 594 | CA | GLU | 91 | 58.662 | 15.210 | 117.996 | 1.00 | 43.57 |
| ATOM | 595 | CB | GLU | 91 | 58.169 | 15.435 | 116.566 | 1.00 | 44.39 |
| ATOM | 596 | CG | GLU | 91 | 57.638 | 14.181 | 115.872 | 1.00 | 43.82 |
| ATOM | 597 | CD | GLU | 91 | 56.971 | 14.484 | 114.543 | 1.00 | 43.03 |
| ATOM | 598 | OE1 | GLU | 91 | 55.925 | 15.170 | 114.547 | 1.00 | 41.30 |
| ATOM | 599 | OE2 | GLU | 91 | 57.495 | 14.037 | 113.499 | 1.00 | 42.95 |

TABLE 6-continued

FGF2/FGFR1/Heparin Ternary Complex

| ATOM | 600 | C | GLU | 91 | 59.342 | 16.466 | 118.492 | 1.00 | 42.39 |
|---|---|---|---|---|---|---|---|---|---|
| ATOM | 601 | O | GLU | 91 | 60.227 | 17.001 | 117.830 | 1.00 | 42.51 |
| ATOM | 602 | N | CYS | 92 | 58.923 | 16.936 | 119.659 | 1.00 | 40.94 |
| ATOM | 603 | CA | CYS | 92 | 59.488 | 18.143 | 120.243 | 1.00 | 38.73 |
| ATOM | 604 | CB | CYS | 92 | 58.368 | 19.010 | 120.809 | 1.00 | 38.75 |
| ATOM | 605 | SG | CYS | 92 | 57.090 | 19.469 | 119.614 | 1.00 | 38.94 |
| ATOM | 606 | C | CYS | 92 | 60.472 | 17.819 | 121.353 | 1.00 | 37.23 |
| ATOM | 607 | O | CYS | 92 | 60.824 | 18.691 | 122.145 | 1.00 | 38.15 |
| ATOM | 608 | N | PHE | 93 | 60.920 | 16.569 | 121.405 | 1.00 | 34.63 |
| ATOM | 609 | CA | PHE | 93 | 61.849 | 16.135 | 122.440 | 1.00 | 31.83 |
| ATOM | 610 | CB | PHE | 93 | 61.211 | 15.016 | 123.245 | 1.00 | 29.72 |
| ATOM | 611 | CG | PHE | 93 | 60.004 | 15.465 | 123.981 | 1.00 | 28.43 |
| ATOM | 612 | CD1 | PHE | 93 | 60.119 | 16.385 | 125.010 | 1.00 | 27.56 |
| ATOM | 613 | CD2 | PHE | 93 | 58.743 | 15.071 | 123.577 | 1.00 | 29.45 |
| ATOM | 614 | CE1 | PHE | 93 | 58.998 | 16.919 | 125.623 | 1.00 | 27.01 |
| ATOM | 615 | CE2 | PHE | 93 | 57.609 | 15.601 | 124.185 | 1.00 | 29.35 |
| ATOM | 616 | CZ | PHE | 93 | 57.741 | 16.530 | 125.210 | 1.00 | 27.87 |
| ATOM | 617 | C | PHE | 93 | 63.192 | 15.719 | 121.894 | 1.00 | 30.86 |
| ATOM | 618 | O | PHE | 93 | 63.277 | 15.007 | 120.899 | 1.00 | 31.92 |
| ATOM | 619 | N | PHE | 94 | 64.250 | 16.173 | 122.556 | 1.00 | 28.82 |
| ATOM | 620 | CA | PHE | 94 | 65.600 | 15.883 | 122.101 | 1.00 | 26.91 |
| ATOM | 621 | CB | PHE | 94 | 66.194 | 17.127 | 121.430 | 1.00 | 23.96 |
| ATOM | 622 | CG | PHE | 94 | 65.297 | 17.758 | 120.413 | 1.00 | 19.13 |
| ATOM | 623 | CD1 | PHE | 94 | 65.571 | 17.636 | 119.056 | 1.00 | 19.27 |
| ATOM | 624 | CD2 | PHE | 94 | 64.168 | 18.466 | 120.810 | 1.00 | 17.15 |
| ATOM | 625 | CE1 | PHE | 94 | 64.728 | 18.214 | 118.097 | 1.00 | 18.35 |
| ATOM | 626 | CE2 | PHE | 94 | 63.323 | 19.043 | 119.874 | 1.00 | 16.33 |
| ATOM | 627 | CZ | PHE | 94 | 63.601 | 18.919 | 118.509 | 1.00 | 16.51 |
| ATOM | 628 | C | PHE | 94 | 66.508 | 15.486 | 123.239 | 1.00 | 27.27 |
| ATOM | 629 | O | PHE | 94 | 66.255 | 15.840 | 124.392 | 1.00 | 28.75 |
| ATOM | 630 | N | PHE | 95 | 67.565 | 14.750 | 122.918 | 1.00 | 26.55 |
| ATOM | 631 | CA | PHE | 95 | 68.525 | 14.365 | 123.938 | 1.00 | 27.50 |
| ATOM | 632 | CB | PHE | 95 | 69.277 | 13.085 | 123.576 | 1.00 | 29.60 |
| ATOM | 633 | CG | PHE | 95 | 68.417 | 11.870 | 123.536 | 1.00 | 32.07 |
| ATOM | 634 | CD1 | PHE | 95 | 67.912 | 11.399 | 122.330 | 1.00 | 33.27 |
| ATOM | 635 | CD2 | PHE | 95 | 68.062 | 11.222 | 124.711 | 1.00 | 33.12 |
| ATOM | 636 | CE1 | PHE | 95 | 67.064 | 10.306 | 122.294 | 1.00 | 33.11 |
| ATOM | 637 | CE2 | PHE | 95 | 67.215 | 10.131 | 124.687 | 1.00 | 33.28 |
| ATOM | 638 | CZ | PHE | 95 | 66.715 | 9.672 | 123.473 | 1.00 | 33.45 |
| ATOM | 639 | C | PHE | 95 | 69.529 | 15.490 | 124.021 | 1.00 | 27.10 |
| ATOM | 640 | O | PHE | 95 | 70.296 | 15.722 | 123.085 | 1.00 | 27.95 |
| ATOM | 641 | N | GLU | 96 | 69.519 | 16.209 | 125.131 | 1.00 | 25.84 |
| ATOM | 642 | CA | GLU | 96 | 70.471 | 17.287 | 125.287 | 1.00 | 24.93 |
| ATOM | 643 | CB | GLU | 96 | 69.956 | 18.367 | 126.236 | 1.00 | 24.70 |
| ATOM | 644 | CG | GLU | 96 | 70.903 | 19.538 | 126.346 | 1.00 | 23.98 |
| ATOM | 645 | CD | GLU | 96 | 70.418 | 20.572 | 127.321 | 1.00 | 26.19 |
| ATOM | 646 | OE1 | GLU | 96 | 70.168 | 20.199 | 128.490 | 1.00 | 27.67 |
| ATOM | 647 | OE2 | GLU | 96 | 70.290 | 21.754 | 126.926 | 1.00 | 25.82 |
| ATOM | 648 | C | GLU | 96 | 71.722 | 16.681 | 125.865 | 1.00 | 24.41 |
| ATOM | 649 | O | GLU | 96 | 71.684 | 16.038 | 126.916 | 1.00 | 24.25 |
| ATOM | 650 | N | ARG | 97 | 72.833 | 16.881 | 125.177 | 1.00 | 24.39 |
| ATOM | 651 | CA | ARG | 97 | 74.077 | 16.334 | 125.657 | 1.00 | 25.15 |
| ATOM | 652 | CB | ARG | 97 | 74.467 | 15.097 | 124.858 | 1.00 | 29.19 |
| ATOM | 653 | CG | ARG | 97 | 75.774 | 14.467 | 125.319 | 1.00 | 32.87 |
| ATOM | 654 | CD | ARG | 97 | 76.419 | 13.730 | 124.172 | 1.00 | 36.29 |
| ATOM | 655 | NE | ARG | 97 | 77.556 | 12.929 | 124.599 | 1.00 | 40.01 |
| ATOM | 656 | CZ | ARG | 97 | 77.479 | 11.948 | 125.492 | 1.00 | 42.01 |
| ATOM | 657 | NH1 | ARG | 97 | 76.315 | 11.653 | 126.058 | 1.00 | 42.21 |
| ATOM | 658 | NH2 | ARG | 97 | 78.564 | 11.251 | 125.809 | 1.00 | 42.97 |
| ATOM | 659 | C | ARG | 97 | 75.217 | 17.312 | 125.608 | 1.00 | 23.59 |
| ATOM | 660 | O | ARG | 97 | 75.457 | 17.962 | 124.599 | 1.00 | 23.46 |
| ATOM | 661 | N | LEU | 98 | 75.919 | 17.410 | 126.724 | 1.00 | 22.64 |
| ATOM | 662 | CA | LEU | 98 | 77.077 | 18.268 | 126.810 | 1.00 | 22.94 |
| ATOM | 663 | CB | LEU | 98 | 77.318 | 18.714 | 128.255 | 1.00 | 20.45 |
| ATOM | 664 | CG | LEU | 98 | 78.670 | 19.366 | 128.567 | 1.00 | 19.51 |
| ATOM | 665 | CD1 | LEU | 98 | 79.144 | 20.253 | 127.430 | 1.00 | 19.49 |
| ATOM | 666 | CD2 | LEU | 98 | 78.530 | 20.154 | 129.839 | 1.00 | 18.78 |
| ATOM | 667 | C | LEU | 98 | 78.224 | 17.404 | 126.312 | 1.00 | 23.89 |
| ATOM | 668 | O | LEU | 98 | 78.681 | 16.502 | 127.008 | 1.00 | 25.47 |
| ATOM | 669 | N | GLU | 99 | 78.663 | 17.667 | 125.091 | 1.00 | 24.74 |
| ATOM | 670 | CA | GLU | 99 | 79.739 | 16.904 | 124.484 | 1.00 | 25.77 |
| ATOM | 671 | CB | GLU | 99 | 79.810 | 17.220 | 122.995 | 1.00 | 26.71 |
| ATOM | 672 | CG | GLU | 99 | 78.533 | 16.859 | 122.253 | 1.00 | 27.60 |
| ATOM | 673 | CD | GLU | 99 | 78.266 | 15.370 | 122.263 | 1.00 | 28.48 |
| ATOM | 674 | OE1 | GLU | 99 | 77.207 | 14.956 | 121.744 | 1.00 | 28.01 |
| ATOM | 675 | OE2 | GLU | 99 | 79.120 | 14.613 | 122.786 | 1.00 | 29.35 |
| ATOM | 676 | C | GLU | 99 | 81.072 | 17.185 | 125.145 | 1.00 | 25.65 |

TABLE 6-continued

| | | | | FGF2/FGFR1/Heparin Ternary Complex | | | | | |
|---|---|---|---|---|---|---|---|---|---|
| ATOM | 677 | O | GLU | 99 | 81.206 | 18.144 | 125.894 | 1.00 | 25.21 |
| ATOM | 678 | N | SER | 100 | 82.053 | 16.333 | 124.864 | 1.00 | 26.16 |
| ATOM | 679 | CA | SER | 100 | 83.387 | 16.470 | 125.439 | 1.00 | 26.22 |
| ATOM | 680 | CB | SER | 100 | 84.270 | 15.298 | 125.018 | 1.00 | 27.81 |
| ATOM | 681 | OG | SER | 100 | 84.343 | 15.198 | 123.607 | 1.00 | 31.25 |
| ATOM | 682 | C | SER | 100 | 84.096 | 17.762 | 125.083 | 1.00 | 24.49 |
| ATOM | 683 | O | SER | 100 | 84.991 | 18.181 | 125.796 | 1.00 | 24.71 |
| ATOM | 684 | N | ASN | 101 | 83.721 | 18.394 | 123.980 | 1.00 | 23.73 |
| ATOM | 685 | CA | ASN | 101 | 84.377 | 19.644 | 123.630 | 1.00 | 22.99 |
| ATOM | 686 | CB | ASN | 101 | 84.550 | 19.800 | 122.115 | 1.00 | 21.76 |
| ATOM | 687 | CG | ASN | 101 | 83.251 | 19.952 | 121.397 | 1.00 | 20.18 |
| ATOM | 688 | OD1 | ASN | 101 | 82.199 | 20.037 | 122.022 | 1.00 | 19.80 |
| ATOM | 689 | ND2 | ASN | 101 | 83.308 | 19.997 | 120.072 | 1.00 | 18.87 |
| ATOM | 690 | C | ASN | 101 | 83.641 | 20.847 | 124.210 | 1.00 | 22.97 |
| ATOM | 691 | O | ASN | 101 | 83.962 | 21.987 | 123.904 | 1.00 | 23.31 |
| ATOM | 692 | N | ASN | 102 | 82.662 | 20.581 | 125.062 | 1.00 | 22.48 |
| ATOM | 693 | CA | ASN | 102 | 81.911 | 21.634 | 125.716 | 1.00 | 22.01 |
| ATOM | 694 | CB | ASN | 102 | 82.855 | 22.686 | 126.284 | 1.00 | 22.23 |
| ATOM | 695 | CG | ASN | 102 | 83.420 | 22.294 | 127.629 | 1.00 | 22.57 |
| ATOM | 696 | OD1 | ASN | 102 | 82.696 | 21.846 | 128.511 | 1.00 | 22.39 |
| ATOM | 697 | ND2 | ASN | 102 | 84.717 | 22.477 | 127.798 | 1.00 | 23.63 |
| ATOM | 698 | C | ASN | 102 | 80.813 | 22.334 | 124.934 | 1.00 | 21.28 |
| ATOM | 699 | O | ASN | 102 | 80.351 | 23.395 | 125.338 | 1.00 | 21.93 |
| ATOM | 700 | N | TYR | 103 | 80.402 | 21.777 | 123.809 | 1.00 | 20.20 |
| ATOM | 701 | CA | TYR | 103 | 79.303 | 22.378 | 123.082 | 1.00 | 19.42 |
| ATOM | 702 | CB | TYR | 103 | 79.633 | 22.530 | 121.594 | 1.00 | 18.57 |
| ATOM | 703 | CG | TYR | 103 | 80.564 | 23.697 | 121.266 | 1.00 | 18.66 |
| ATOM | 704 | CD1 | TYR | 103 | 80.088 | 24.845 | 120.640 | 1.00 | 18.26 |
| ATOM | 705 | CE1 | TYR | 103 | 80.933 | 25.902 | 120.332 | 1.00 | 16.61 |
| ATOM | 706 | CD2 | TYR | 103 | 81.920 | 23.642 | 121.576 | 1.00 | 18.47 |
| ATOM | 707 | CE2 | TYR | 103 | 82.770 | 24.697 | 121.276 | 1.00 | 17.49 |
| ATOM | 708 | CZ | TYR | 103 | 82.271 | 25.822 | 120.652 | 1.00 | 17.62 |
| ATOM | 709 | OH | TYR | 103 | 83.116 | 26.864 | 120.326 | 1.00 | 16.79 |
| ATOM | 710 | C | TYR | 103 | 78.166 | 21.391 | 123.326 | 1.00 | 20.73 |
| ATOM | 711 | O | TYR | 103 | 78.393 | 20.289 | 123.818 | 1.00 | 21.64 |
| ATOM | 712 | N | ASN | 104 | 76.939 | 21.788 | 123.031 | 1.00 | 21.46 |
| ATOM | 713 | CA | ASN | 104 | 75.804 | 20.905 | 123.242 | 1.00 | 21.95 |
| ATOM | 714 | CB | ASN | 104 | 74.694 | 21.645 | 123.992 | 1.00 | 22.16 |
| ATOM | 715 | CG | ASN | 104 | 75.008 | 21.824 | 125.460 | 1.00 | 21.47 |
| ATOM | 716 | OD1 | ASN | 104 | 76.162 | 21.957 | 125.837 | 1.00 | 22.13 |
| ATOM | 717 | ND2 | ASN | 104 | 73.983 | 21.842 | 126.288 | 1.00 | 20.81 |
| ATOM | 718 | C | ASN | 104 | 75.269 | 20.379 | 121.925 | 1.00 | 22.94 |
| ATOM | 719 | O | ASN | 104 | 75.466 | 20.989 | 120.872 | 1.00 | 22.22 |
| ATOM | 720 | N | THR | 105 | 74.604 | 19.231 | 121.989 | 1.00 | 23.66 |
| ATOM | 721 | CA | THR | 105 | 74.026 | 18.620 | 120.802 | 1.00 | 23.95 |
| ATOM | 722 | CB | THR | 105 | 74.781 | 17.357 | 120.377 | 1.00 | 22.66 |
| ATOM | 723 | OG1 | THR | 105 | 74.811 | 16.443 | 121.475 | 1.00 | 24.98 |
| ATOM | 724 | CG2 | THR | 105 | 76.202 | 17.696 | 119.964 | 1.00 | 21.44 |
| ATOM | 725 | C | THR | 105 | 72.610 | 18.229 | 121.130 | 1.00 | 24.19 |
| ATOM | 726 | O | TRR | 105 | 72.356 | 17.580 | 122.142 | 1.00 | 23.89 |
| ATOM | 727 | N | TYR | 106 | 71.685 | 18.626 | 120.273 | 1.00 | 24.68 |
| ATOM | 728 | CA | TYR | 106 | 70.291 | 18.298 | 120.501 | 1.00 | 25.37 |
| ATOM | 729 | CB | TYR | 106 | 69.462 | 19.574 | 120.412 | 1.00 | 21.41 |
| ATOM | 730 | CG | TYR | 106 | 69.796 | 20.501 | 121.544 | 1.00 | 17.07 |
| ATOM | 731 | CD1 | TYR | 106 | 69.210 | 20.328 | 122.793 | 1.00 | 16.65 |
| ATOM | 732 | CE1 | TYR | 106 | 69.608 | 21.088 | 123.888 | 1.00 | 15.13 |
| ATOM | 733 | CD2 | TYR | 106 | 70.786 | 21.466 | 121.412 | 1.00 | 15.18 |
| ATOM | 734 | CE2 | TYR | 106 | 71.196 | 22.232 | 122.502 | 1.00 | 14.37 |
| ATOM | 735 | CZ | TYR | 106 | 70.604 | 22.033 | 123.736 | 1.00 | 14.28 |
| ATOM | 736 | OH | TYR | 106 | 71.020 | 22.747 | 124.828 | 1.00 | 12.09 |
| ATOM | 737 | C | TYR | 106 | 69.846 | 17.252 | 119.499 | 1.00 | 27.76 |
| ATOM | 738 | O | TYR | 106 | 69.475 | 17.574 | 118.371 | 1.00 | 28.60 |
| ATOM | 739 | N | ARG | 107 | 69.905 | 15.993 | 119.931 | 1.00 | 29.65 |
| ATOM | 740 | CA | ARG | 107 | 69.552 | 14.846 | 119.103 | 1.00 | 30.86 |
| ATOM | 741 | CB | ARG | 107 | 70.457 | 13.674 | 119.468 | 1.00 | 31.13 |
| ATOM | 742 | CG | ARG | 107 | 70.380 | 12.485 | 118.532 | 1.00 | 32.41 |
| ATOM | 743 | CD | ARG | 107 | 71.598 | 11.571 | 118.713 | 1.00 | 32.66 |
| ATOM | 744 | NE | ARG | 107 | 71.750 | 11.094 | 120.090 | 1.00 | 32.94 |
| ATOM | 745 | CZ | ARG | 107 | 70.903 | 10.264 | 120.697 | 1.00 | 31.97 |
| ATOM | 746 | NH1 | ARG | 107 | 69.837 | 9.805 | 120.055 | 1.00 | 31.43 |
| ATOM | 747 | NH2 | ARG | 107 | 71.117 | 9.904 | 121.952 | 1.00 | 31.53 |
| ATOM | 748 | C | ARG | 107 | 68.105 | 14.445 | 119.279 | 1.00 | 31.79 |
| ATOM | 749 | O | ARG | 107 | 67.663 | 14.203 | 120.399 | 1.00 | 33.20 |
| ATOM | 750 | N | SER | 108 | 67.373 | 14.376 | 118.170 | 1.00 | 32.91 |
| ATOM | 751 | CA | SER | 108 | 65.957 | 14.007 | 118.183 | 1.00 | 33.98 |
| ATOM | 752 | CB | SER | 108 | 65.401 | 13.981 | 116.758 | 1.00 | 33.63 |
| ATOM | 753 | OG | SER | 108 | 64.127 | 13.364 | 116.710 | 1.00 | 32.09 |

TABLE 6-continued

FGF2/FGFR1/Heparin Ternary Complex

| ATOM | 754 | C | SER | 108 | 65.725 | 12.649 | 118.814 | 1.00 | 34.53 |
|---|---|---|---|---|---|---|---|---|---|
| ATOM | 755 | O | SER | 108 | 66.249 | 11.640 | 118.345 | 1.00 | 33.98 |
| ATOM | 756 | N | ARG | 109 | 64.926 | 12.625 | 119.873 | 1.00 | 35.10 |
| ATOM | 757 | CA | ARG | 109 | 64.636 | 11.375 | 120.543 | 1.00 | 36.45 |
| ATOM | 758 | CB | ARG | 109 | 63.858 | 11.615 | 121.835 | 1.00 | 35.72 |
| ATOM | 759 | CG | ARG | 109 | 63.582 | 10.324 | 122.577 | 1.00 | 36.42 |
| ATOM | 760 | CD | ARG | 109 | 63.037 | 10.536 | 123.967 | 1.00 | 35.39 |
| ATOM | 761 | NE | ARG | 109 | 61.713 | 11.129 | 123.936 | 1.00 | 35.74 |
| ATOM | 762 | CZ | ARG | 109 | 60.951 | 11.273 | 125.011 | 1.00 | 36.28 |
| ATOM | 763 | NH1 | ARG | 109 | 61.397 | 10.855 | 126.191 | 1.00 | 36.06 |
| ATOM | 764 | NH2 | ARG | 109 | 59.761 | 11.854 | 124.909 | 1.00 | 36.38 |
| ATOM | 765 | C | ARG | 109 | 63.841 | 10.444 | 119.641 | 1.00 | 37.21 |
| ATOM | 766 | O | ARG | 109 | 63.930 | 9.223 | 119.773 | 1.00 | 36.80 |
| ATOM | 767 | N | LYS | 110 | 63.068 | 11.019 | 118.723 | 1.00 | 38.39 |
| ATOM | 768 | CA | LYS | 110 | 62.265 | 10.213 | 117.811 | 1.00 | 38.92 |
| ATOM | 769 | CB | LYS | 110 | 61.102 | 11.021 | 117.235 | 1.00 | 38.55 |
| ATOM | 770 | CG | LYS | 110 | 59.967 | 10.156 | 116.715 | 1.00 | 38.82 |
| ATOM | 771 | CD | LYS | 110 | 58.748 | 10.977 | 116.290 | 1.00 | 39.89 |
| ATOM | 772 | CE | LYS | 110 | 57.679 | 10.121 | 115.564 | 1.00 | 40.04 |
| ATOM | 773 | NZ | LYS | 110 | 57.046 | 9.064 | 116.420 | 1.00 | 37.08 |
| ATOM | 774 | C | LYS | 110 | 63.144 | 9.673 | 116.689 | 1.00 | 39.37 |
| ATOM | 775 | O | LYS | 110 | 63.311 | 8.465 | 116.558 | 1.00 | 40.36 |
| ATOM | 776 | N | TYR | 111 | 63.721 | 10.557 | 115.890 | 1.00 | 39.00 |
| ATOM | 777 | CA | TYR | 111 | 64.593 | 10.121 | 114.810 | 1.00 | 38.93 |
| ATOM | 778 | CB | TYR | 111 | 64.395 | 11.063 | 113.634 | 1.00 | 40.33 |
| ATOM | 779 | CG | TYR | 111 | 62.920 | 11.319 | 113.371 | 1.00 | 41.38 |
| ATOM | 780 | CD1 | TYR | 111 | 62.035 | 10.264 | 113.185 | 1.00 | 41.70 |
| ATOM | 781 | CE1 | TYR | 111 | 60.680 | 10.487 | 112.971 | 1.00 | 41.29 |
| ATOM | 782 | CD2 | TYR | 111 | 62.406 | 12.611 | 113.337 | 1.00 | 41.72 |
| ATOM | 783 | CE2 | TYR | 111 | 61.055 | 12.842 | 113.126 | 1.00 | 41.20 |
| ATOM | 784 | CZ | TYR | 111 | 60.197 | 11.775 | 112.943 | 1.00 | 41.51 |
| ATOM | 785 | OH | TYR | 111 | 58.855 | 11.995 | 112.729 | 1.00 | 41.98 |
| ATOM | 786 | C | TYR | 111 | 66.037 | 10.119 | 115.322 | 1.00 | 38.59 |
| ATOM | 787 | O | TYR | 111 | 66.914 | 10.793 | 114.796 | 1.00 | 38.33 |
| ATOM | 788 | N | THR | 112 | 66.232 | 9.325 | 116.368 | 1.00 | 38.84 |
| ATOM | 789 | CA | THR | 112 | 67.476 | 9.136 | 117.111 | 1.00 | 39.06 |
| ATOM | 790 | CB | THR | 112 | 67.467 | 7.763 | 117.777 | 1.00 | 38.66 |
| ATOM | 791 | OG1 | THR | 112 | 67.757 | 6.756 | 116.796 | 1.00 | 38.25 |
| ATOM | 792 | CG2 | THR | 112 | 66.102 | 7.496 | 118.398 | 1.00 | 38.36 |
| ATOM | 793 | C | THR | 112 | 68.856 | 9.287 | 116.478 | 1.00 | 39.58 |
| ATOM | 794 | O | THR | 112 | 69.862 | 9.252 | 117.191 | 1.00 | 39.45 |
| ATOM | 795 | N | SER | 113 | 68.936 | 9.443 | 115.168 | 1.00 | 39.83 |
| ATOM | 796 | CA | SER | 113 | 70.246 | 9.565 | 114.543 | 1.00 | 39.71 |
| ATOM | 797 | CB | SER | 113 | 70.385 | 8.511 | 113.448 | 1.00 | 38.44 |
| ATOM | 798 | OG | SER | 113 | 69.216 | 8.475 | 112.648 | 1.00 | 37.77 |
| ATOM | 799 | C | SER | 113 | 70.488 | 10.947 | 113.967 | 1.00 | 39.75 |
| ATOM | 800 | O | SER | 113 | 71.540 | 11.213 | 113.393 | 1.00 | 39.88 |
| ATOM | 801 | N | TRP | 114 | 69.514 | 11.830 | 114.142 | 1.00 | 39.62 |
| ATOM | 802 | CA | TRP | 114 | 69.609 | 13.181 | 113.618 | 1.00 | 39.62 |
| ATOM | 803 | CB | TRP | 114 | 68.412 | 13.458 | 112.729 | 1.00 | 41.59 |
| ATOM | 804 | CG | TRP | 114 | 68.217 | 12.435 | 111.675 | 1.00 | 42.65 |
| ATOM | 805 | CD2 | TRP | 114 | 67.041 | 12.237 | 110.895 | 1.00 | 42.92 |
| ATOM | 806 | CE2 | TRP | 114 | 67.335 | 11.235 | 109.948 | 1.00 | 43.49 |
| ATOM | 807 | CE3 | TRP | 114 | 65.767 | 12.814 | 110.899 | 1.00 | 42.96 |
| ATOM | 808 | CD1 | TRP | 114 | 69.150 | 11.568 | 111.193 | 1.00 | 43.51 |
| ATOM | 809 | NE1 | TRP | 114 | 68.631 | 10.845 | 110.154 | 1.00 | 44.02 |
| ATOM | 810 | CZ2 | TRP | 114 | 66.399 | 10.793 | 109.010 | 1.00 | 42.90 |
| ATOM | 811 | CZ3 | TRP | 114 | 64.838 | 12.379 | 109.968 | 1.00 | 43.00 |
| ATOM | 812 | CH2 | TRP | 114 | 65.160 | 11.376 | 109.033 | 1.00 | 43.09 |
| ATOM | 813 | C | TRP | 114 | 69.673 | 14.249 | 114.686 | 1.00 | 38.97 |
| ATOM | 814 | O | TRP | 114 | 69.102 | 14.104 | 115.760 | 1.00 | 38.94 |
| ATOM | 815 | N | TYR | 115 | 70.350 | 15.342 | 114.370 | 1.00 | 38.45 |
| ATOM | 816 | CA | TYR | 115 | 70.500 | 16.439 | 115.312 | 1.00 | 37.45 |
| ATOM | 817 | CB | TYR | 115 | 71.981 | 16.730 | 115.566 | 1.00 | 38.19 |
| ATOM | 818 | CG | TYR | 115 | 72.769 | 15.592 | 116.159 | 1.00 | 38.70 |
| ATOM | 819 | CD1 | TYR | 115 | 73.235 | 14.555 | 115.364 | 1.00 | 40.21 |
| ATOM | 820 | CE1 | TYR | 115 | 73.971 | 13.518 | 115.901 | 1.00 | 40.15 |
| ATOM | 821 | CD2 | TYR | 115 | 73.059 | 15.559 | 117.513 | 1.00 | 38.42 |
| ATOM | 822 | CE2 | TYR | 115 | 73.792 | 14.530 | 118.057 | 1.00 | 38.96 |
| ATOM | 823 | CZ | TYR | 115 | 74.247 | 13.512 | 117.246 | 1.00 | 39.54 |
| ATOM | 824 | OH | TYR | 115 | 74.993 | 12.488 | 117.782 | 1.00 | 40.88 |
| ATOM | 825 | C | TYR | 115 | 69.860 | 17.725 | 114.825 | 1.00 | 35.83 |
| ATOM | 826 | O | TYR | 115 | 69.512 | 17.869 | 113.657 | 1.00 | 36.40 |
| ATOM | 827 | N | VAL | 116 | 69.704 | 18.661 | 115.745 | 1.00 | 33.23 |
| ATOM | 828 | CA | VAL | 116 | 69.180 | 19.953 | 115.392 | 1.00 | 31.90 |
| ATOM | 829 | CB | VAL | 116 | 68.616 | 20.675 | 116.608 | 1.00 | 29.60 |
| ATOM | 830 | CG1 | VAL | 116 | 68.190 | 22.046 | 116.218 | 1.00 | 29.66 |

TABLE 6-continued

FGF2/FGFR1/Heparin Ternary Complex

| ATOM | 831 | CG2 | VAL | 116 | 67.448 | 19.915 | 117.165 | 1.00 | 28.27 |
|---|---|---|---|---|---|---|---|---|---|
| ATOM | 832 | C | VAL | 116 | 70.443 | 20.660 | 114.934 | 1.00 | 32.35 |
| ATOM | 833 | O | VAL | 116 | 71.470 | 20.575 | 115.609 | 1.00 | 33.68 |
| ATOM | 834 | N | ALA | 117 | 70.402 | 21.326 | 113.787 | 1.00 | 31.51 |
| ATOM | 835 | CA | ALA | 117 | 71.596 | 22.021 | 113.329 | 1.00 | 30.34 |
| ATOM | 836 | CB | ALA | 117 | 72.566 | 21.035 | 112.689 | 1.00 | 29.37 |
| ATOM | 837 | C | ALA | 117 | 71.322 | 23.168 | 112.381 | 1.00 | 30.52 |
| ATOM | 838 | O | ALA | 117 | 70.261 | 23.270 | 111.785 | 1.00 | 29.89 |
| ATOM | 839 | N | LEU | 118 | 72.301 | 24.044 | 112.254 | 1.00 | 31.70 |
| ATOM | 840 | CA | LEU | 118 | 72.171 | 25.171 | 111.365 | 1.00 | 33.07 |
| ATOM | 841 | CB | LEU | 118 | 72.120 | 26.469 | 112.177 | 1.00 | 31.15 |
| ATOM | 842 | CG | LEU | 118 | 70.863 | 26.628 | 113.034 | 1.00 | 29.10 |
| ATOM | 843 | CD1 | LEU | 118 | 70.940 | 27.882 | 113.846 | 1.00 | 29.11 |
| ATOM | 844 | CD2 | LEU | 118 | 69.653 | 26.689 | 112.142 | 1.00 | 29.28 |
| ATOM | 845 | C | LEU | 118 | 73.336 | 25.179 | 110.382 | 1.00 | 34.94 |
| ATOM | 846 | O | LEU | 118 | 74.452 | 24.780 | 110.717 | 1.00 | 34.42 |
| ATOM | 847 | N | LYS | 119 | 73.061 | 25.606 | 109.155 | 1.00 | 37.22 |
| ATOM | 848 | CA | LYS | 119 | 74.088 | 25.682 | 108.127 | 1.00 | 39.12 |
| ATOM | 849 | CB | LYS | 119 | 73.449 | 25.678 | 106.742 | 1.00 | 39.24 |
| ATOM | 850 | CG | LYS | 119 | 72.650 | 24.423 | 106.458 | 1.00 | 39.74 |
| ATOM | 851 | CD | LYS | 119 | 72.649 | 24.116 | 104.977 | 1.00 | 41.15 |
| ATOM | 852 | CE | LYS | 119 | 71.540 | 24.836 | 104.224 | 1.00 | 42.85 |
| ATOM | 853 | NZ | LYS | 119 | 79.288 | 24.014 | 104.176 | 1.00 | 43.50 |
| ATOM | 854 | C | LYS | 119 | 74.874 | 26.962 | 108.339 | 1.00 | 40.49 |
| ATOM | 855 | O | LYS | 119 | 74.448 | 27.835 | 109.104 | 1.00 | 41.69 |
| ATOM | 856 | N | ARG | 120 | 76.023 | 27.094 | 107.686 | 1.00 | 41.30 |
| ATOM | 857 | CA | ARG | 120 | 76.798 | 28.313 | 107.878 | 1.00 | 42.48 |
| ATOM | 858 | CB | ARG | 120 | 78.283 | 28.124 | 107.520 | 1.00 | 42.64 |
| ATOM | 859 | CG | ARG | 120 | 78.605 | 27.689 | 106.101 | 1.00 | 43.83 |
| ATOM | 860 | CD | ARG | 120 | 78.594 | 26.175 | 105.955 | 1.00 | 43.47 |
| ATOM | 861 | NE | ARG | 120 | 79.014 | 25.722 | 104.629 | 1.00 | 43.21 |
| ATOM | 862 | CZ | ARG | 120 | 80.246 | 25.846 | 104.151 | 1.00 | 44.61 |
| ATOM | 863 | NH1 | ARG | 120 | 81.190 | 26.415 | 104.884 | 1.00 | 46.17 |
| ATOM | 864 | NH2 | ARG | 120 | 80.539 | 25.382 | 102.949 | 1.00 | 45.84 |
| ATOM | 865 | C | ARG | 120 | 76.183 | 29.446 | 107.075 | 1.00 | 43.28 |
| ATOM | 866 | O | ARG | 120 | 76.752 | 30.531 | 106.968 | 1.00 | 43.69 |
| ATOM | 867 | N | THR | 121 | 74.994 | 29.186 | 106.539 | 1.00 | 43.43 |
| ATOM | 868 | CA | THR | 121 | 74.271 | 30.170 | 105.756 | 1.00 | 42.23 |
| ATOM | 869 | CB | THR | 121 | 73.772 | 29.564 | 104.465 | 1.00 | 41.98 |
| ATOM | 870 | OG1 | THR | 121 | 72.714 | 28.640 | 104.743 | 1.00 | 42.99 |
| ATOM | 871 | CG2 | THR | 121 | 74.896 | 28.826 | 103.795 | 1.00 | 43.36 |
| ATOM | 872 | C | THR | 121 | 73.082 | 30.735 | 106.518 | 1.00 | 42.08 |
| ATOM | 873 | O | THR | 121 | 72.351 | 31.573 | 106.001 | 1.00 | 42.51 |
| ATOM | 874 | N | GLY | 122 | 72.873 | 30.264 | 107.740 | 1.00 | 41.44 |
| ATOM | 875 | CA | GLY | 122 | 71.779 | 30.792 | 108.525 | 1.00 | 41.27 |
| ATOM | 876 | C | GLY | 122 | 70.490 | 30.014 | 108.498 | 1.00 | 40.70 |
| ATOM | 877 | O | GLY | 122 | 69.527 | 30.412 | 109.143 | 1.00 | 40.68 |
| ATOM | 878 | N | GLN | 123 | 70.451 | 28.922 | 107.746 | 1.00 | 41.11 |
| ATOM | 879 | CA | GLN | 123 | 69.242 | 28.100 | 107.697 | 1.00 | 41.82 |
| ATOM | 880 | CB | GLN | 123 | 68.797 | 27.824 | 106.270 | 1.00 | 43.37 |
| ATOM | 881 | CG | GLN | 123 | 68.604 | 29.048 | 105.438 | 1.00 | 46.68 |
| ATOM | 882 | CD | GLN | 123 | 68.160 | 28.697 | 104.051 | 1.00 | 49.75 |
| ATOM | 883 | OE1 | GLN | 123 | 68.680 | 27.753 | 103.442 | 1.00 | 52.33 |
| ATOM | 884 | NE2 | GLN | 123 | 67.200 | 29.456 | 103.526 | 1.00 | 51.17 |
| ATOM | 885 | C | GLN | 123 | 69.566 | 26.783 | 108.348 | 1.00 | 40.53 |
| ATOM | 886 | O | GLN | 123 | 70.731 | 26.404 | 108.432 | 1.00 | 40.36 |
| ATOM | 887 | N | TYR | 124 | 68.544 | 26.071 | 108.797 | 1.00 | 39.08 |
| ATOM | 888 | CA | TYR | 124 | 68.801 | 24.797 | 109.443 | 1.00 | 38.47 |
| ATOM | 889 | CB | TYR | 124 | 67.533 | 24.254 | 110.123 | 1.00 | 34.77 |
| ATOM | 890 | CG | TYR | 124 | 66.425 | 23.813 | 109.199 | 1.00 | 32.38 |
| ATOM | 891 | CD1 | TYR | 124 | 66.589 | 22.732 | 108.348 | 1.00 | 31.29 |
| ATOM | 892 | CE1 | TYR | 124 | 65.565 | 22.315 | 107.502 | 1.00 | 30.22 |
| ATOM | 893 | CD2 | TYR | 124 | 65.201 | 24.472 | 109.185 | 1.00 | 32.42 |
| ATOM | 894 | CE2 | TYR | 124 | 64.168 | 24.061 | 108.345 | 1.00 | 31.68 |
| ATOM | 895 | CZ | TYR | 124 | 64.361 | 22.981 | 107.504 | 1.00 | 30.66 |
| ATOM | 896 | OH | TYR | 124 | 63.359 | 22.578 | 106.654 | 1.00 | 30.68 |
| ATOM | 897 | C | TYR | 124 | 69.346 | 23.782 | 108.447 | 1.00 | 39.35 |
| ATOM | 898 | O | TYR | 124 | 69.467 | 24.066 | 107.256 | 1.00 | 39.98 |
| ATOM | 899 | N | LYS | 125 | 69.696 | 22.604 | 108.948 | 1.00 | 39.17 |
| ATOM | 900 | CA | LYS | 125 | 70.204 | 21.536 | 108.111 | 1.00 | 37.57 |
| ATOM | 901 | CB | LYS | 125 | 71.654 | 21.227 | 108.452 | 1.00 | 35.65 |
| ATOM | 902 | CG | LYS | 125 | 72.138 | 19.941 | 107.813 | 1.00 | 34.29 |
| ATOM | 903 | CD | LYS | 125 | 73.516 | 19.523 | 108.292 | 1.00 | 33.86 |
| ATOM | 904 | CE | LYS | 125 | 74.590 | 20.498 | 107.865 | 1.00 | 33.07 |
| ATOM | 905 | NZ | LYS | 125 | 75.942 | 19.930 | 108.107 | 1.00 | 32.09 |
| ATOM | 906 | C | LYS | 125 | 69.363 | 20.302 | 108.358 | 1.00 | 38.02 |
| ATOM | 907 | O | LYS | 125 | 69.148 | 19.914 | 109.500 | 1.00 | 37.99 |

TABLE 6-continued

| FGF2/FGFR1/Heparin Ternary Complex | | | | | | | | |
|---|---|---|---|---|---|---|---|---|
| ATOM | 908 | N | LEU | 126 | 68.886 | 19.688 | 107.285 | 1.00 | 38.80 |
| ATOM | 909 | CA | LEU | 126 | 68.070 | 18.487 | 107.399 | 1.00 | 39.48 |
| ATOM | 910 | CB | LEU | 126 | 67.865 | 17.850 | 106.026 | 1.00 | 38.69 |
| ATOM | 911 | CG | LEU | 126 | 66.712 | 18.390 | 105.187 | 1.00 | 37.82 |
| ATOM | 912 | CD1 | LEU | 126 | 66.513 | 17.471 | 104.001 | 1.00 | 37.53 |
| ATOM | 913 | CD2 | LEU | 126 | 65.434 | 18.447 | 106.011 | 1.00 | 38.14 |
| ATOM | 914 | C | LEU | 126 | 68.699 | 17.464 | 108.324 | 1.00 | 39.57 |
| ATOM | 915 | O | LEU | 126 | 69.841 | 17.073 | 108.122 | 1.00 | 39.43 |
| ATOM | 916 | N | GLY | 127 | 67.949 | 17.037 | 109.334 | 1.00 | 40.17 |
| ATOM | 917 | CA | GLY | 127 | 68.463 | 16.056 | 110.269 | 1.00 | 42.23 |
| ATOM | 918 | C | GLY | 127 | 69.083 | 14.909 | 109.501 | 1.00 | 43.38 |
| ATOM | 919 | O | GLY | 127 | 70.170 | 14.426 | 109.827 | 1.00 | 43.71 |
| ATOM | 920 | N | SER | 128 | 68.386 | 14.480 | 108.458 | 1.00 | 43.71 |
| ATOM | 921 | CA | SER | 128 | 68.864 | 13.391 | 107.618 | 1.00 | 43.74 |
| ATOM | 922 | CB | SER | 128 | 67.888 | 13.146 | 106.458 | 1.00 | 43.62 |
| ATOM | 923 | OG | SER | 128 | 67.540 | 14.343 | 105.778 | 1.00 | 42.70 |
| ATOM | 924 | C | SER | 128 | 70.252 | 13.668 | 107.063 | 1.00 | 43.90 |
| ATOM | 925 | O | SER | 128 | 70.899 | 12.781 | 106.524 | 1.00 | 44.67 |
| ATOM | 926 | N | LYS | 129 | 70.710 | 14.901 | 107.216 | 1.00 | 44.72 |
| ATOM | 927 | CA | LYS | 129 | 72.011 | 15.315 | 106.717 | 1.00 | 45.28 |
| ATOM | 928 | CB | LYS | 129 | 71.787 | 16.519 | 105.792 | 1.00 | 46.93 |
| ATOM | 929 | CG | LYS | 129 | 73.011 | 17.141 | 105.138 | 1.00 | 52.08 |
| ATOM | 930 | CD | LYS | 129 | 72.582 | 18.374 | 104.302 | 1.00 | 55.55 |
| ATOM | 931 | CE | LYS | 129 | 73.575 | 19.559 | 104.376 | 1.00 | 57.33 |
| ATOM | 932 | NZ | LYS | 129 | 74.751 | 19.461 | 103.456 | 1.00 | 57.35 |
| ATOM | 933 | C | LYS | 129 | 72.975 | 15.644 | 107.871 | 1.00 | 44.19 |
| ATOM | 934 | O | LYS | 129 | 74.142 | 15.968 | 107.645 | 1.00 | 43.60 |
| ATOM | 935 | N | THR | 130 | 72.490 | 15.542 | 109.106 | 1.00 | 42.55 |
| ATOM | 936 | CA | THR | 130 | 73.315 | 15.846 | 110.268 | 1.00 | 42.68 |
| ATOM | 937 | CB | THR | 130 | 72.451 | 16.296 | 111.446 | 1.00 | 42.81 |
| ATOM | 938 | OG1 | THR | 130 | 71.463 | 15.299 | 111.729 | 1.00 | 43.32 |
| ATOM | 939 | CG2 | THR | 130 | 71.765 | 17.599 | 111.113 | 1.00 | 42.84 |
| ATOM | 940 | C | THR | 130 | 74.163 | 14.656 | 110.691 | 1.00 | 42.45 |
| ATOM | 941 | O | THR | 130 | 73.840 | 13.517 | 110.369 | 1.00 | 42.53 |
| ATOM | 942 | N | GLY | 131 | 75.248 | 14.925 | 111.415 | 1.00 | 42.09 |
| ATOM | 943 | CA | GLY | 131 | 76.129 | 13.852 | 111.842 | 1.00 | 41.59 |
| ATOM | 944 | C | GLY | 131 | 77.166 | 14.229 | 112.887 | 1.00 | 40.79 |
| ATOM | 945 | O | GLY | 131 | 77.635 | 15.363 | 112.932 | 1.00 | 40.05 |
| ATOM | 946 | N | PRO | 132 | 77.557 | 13.268 | 113.732 | 1.00 | 40.57 |
| ATOM | 947 | CD | PRO | 132 | 77.066 | 11.884 | 113.594 | 1.00 | 39.61 |
| ATOM | 948 | CA | PRO | 132 | 78.526 | 13.349 | 114.825 | 1.00 | 40.58 |
| ATOM | 949 | CB | PRO | 132 | 78.920 | 11.898 | 115.009 | 1.00 | 40.55 |
| ATOM | 950 | CG | PRO | 132 | 77.615 | 11.214 | 114.830 | 1.00 | 39.59 |
| ATOM | 951 | C | PRO | 132 | 79.736 | 14.258 | 114.635 | 1.00 | 40.69 |
| ATOM | 952 | O | PRO | 132 | 80.051 | 15.084 | 115.501 | 1.00 | 40.87 |
| ATOM | 953 | N | GLY | 133 | 80.424 | 14.106 | 113.512 | 1.00 | 40.45 |
| ATOM | 954 | CA | GLY | 133 | 81.594 | 14.935 | 113.282 | 1.00 | 40.40 |
| ATOM | 955 | C | GLY | 133 | 81.340 | 16.358 | 112.800 | 1.00 | 39.70 |
| ATOM | 956 | O | GLY | 133 | 82.288 | 17.133 | 112.660 | 1.00 | 39.58 |
| ATOM | 957 | N | GLN | 134 | 80.076 | 16.711 | 112.566 | 1.00 | 39.01 |
| ATOM | 958 | CA | GLN | 134 | 79.709 | 18.038 | 112.056 | 1.00 | 38.30 |
| ATOM | 959 | CB | GLN | 134 | 78.320 | 17.985 | 111.431 | 1.00 | 38.69 |
| ATOM | 960 | CG | GLN | 134 | 78.259 | 17.176 | 110.162 | 1.00 | 40.00 |
| ATOM | 961 | CD | GLN | 134 | 76.850 | 17.017 | 109.655 | 1.00 | 40.48 |
| ATOM | 962 | OE1 | GLN | 134 | 76.103 | 17.988 | 109.552 | 1.00 | 40.40 |
| ATOM | 963 | NE2 | GLN | 134 | 76.478 | 15.787 | 109.325 | 1.00 | 40.61 |
| ATOM | 964 | C | GLN | 134 | 79.736 | 19.205 | 113.031 | 1.00 | 37.24 |
| ATOM | 965 | O | GLN | 134 | 79.481 | 19.039 | 114.222 | 1.00 | 37.79 |
| ATOM | 966 | N | LYS | 135 | 80.032 | 20.390 | 112.494 | 1.00 | 35.77 |
| ATOM | 967 | CA | LYS | 135 | 80.076 | 21.634 | 113.258 | 1.00 | 34.42 |
| ATOM | 968 | CB | LYS | 135 | 80.967 | 22.667 | 112.580 | 1.00 | 36.21 |
| ATOM | 969 | CG | LYS | 135 | 82.413 | 22.278 | 112.522 | 1.00 | 40.14 |
| ATOM | 970 | CD | LYS | 135 | 83.278 | 23.415 | 112.041 | 1.00 | 41.89 |
| ATOM | 971 | CE | LYS | 135 | 84.747 | 22.995 | 112.065 | 1.00 | 45.11 |
| ATOM | 972 | NZ | LYS | 135 | 85.048 | 21.792 | 111.216 | 1.00 | 47.95 |
| ATOM | 973 | C | LYS | 135 | 78.694 | 22.231 | 113.366 | 1.00 | 32.96 |
| ATOM | 974 | O | LYS | 135 | 78.436 | 23.039 | 114.242 | 1.00 | 32.00 |
| ATOM | 975 | N | ALA | 136 | 77.810 | 21.831 | 112.461 | 1.00 | 32.01 |
| ATOM | 976 | CA | ALA | 136 | 76.441 | 22.329 | 112.437 | 1.00 | 30.91 |
| ATOM | 977 | CB | ALA | 136 | 75.736 | 21.844 | 111.179 | 1.00 | 29.19 |
| ATOM | 978 | C | ALA | 136 | 75.631 | 21.921 | 113.655 | 1.00 | 30.28 |
| ATOM | 979 | O | ALA | 136 | 74.732 | 22.640 | 114.072 | 1.00 | 31.03 |
| ATOM | 980 | N | ILE | 137 | 75.950 | 20.770 | 114.228 | 1.00 | 29.98 |
| ATOM | 981 | CA | ILE | 137 | 75.199 | 20.272 | 115.380 | 1.00 | 28.90 |
| ATOM | 982 | CB | ILE | 137 | 75.272 | 18.738 | 115.500 | 1.00 | 28.83 |
| ATOM | 983 | CG2 | ILE | 137 | 74.575 | 18.091 | 114.307 | 1.00 | 28.65 |
| ATOM | 984 | CG1 | ILE | 137 | 76.736 | 18.310 | 115.642 | 1.00 | 28.11 |

TABLE 6-continued

FGF2/FGFR1/Heparin Ternary Complex

| ATOM | 985 | CD1 | ILE | 137 | 76.919 | 16.849 | 115.872 | 1.00 | 28.77 |
|---|---|---|---|---|---|---|---|---|---|
| ATOM | 986 | C | ILE | 137 | 75.599 | 20.833 | 116.726 | 1.00 | 27.60 |
| ATOM | 987 | O | ILE | 137 | 74.818 | 20.762 | 117.668 | 1.00 | 28.34 |
| ATOM | 988 | N | LEU | 138 | 76.803 | 21.388 | 116.818 | 1.00 | 25.80 |
| ATOM | 989 | CA | LEU | 138 | 77.297 | 21.939 | 118.078 | 1.00 | 24.32 |
| ATOM | 990 | CB | LEU | 138 | 78.804 | 22.137 | 118.003 | 1.00 | 20.98 |
| ATOM | 991 | CG | LEU | 138 | 79.595 | 20.913 | 117.602 | 1.00 | 17.84 |
| ATOM | 992 | CD1 | LEU | 138 | 81.051 | 21.189 | 117.842 | 1.00 | 16.51 |
| ATOM | 993 | CD2 | LEU | 138 | 79.128 | 19.720 | 118.404 | 1.00 | 17.39 |
| ATOM | 994 | C | LEU | 138 | 76.665 | 23.262 | 118.478 | 1.00 | 24.83 |
| ATOM | 995 | O | LEU | 138 | 76.710 | 24.234 | 117.727 | 1.00 | 26.01 |
| ATOM | 996 | N | PHE | 139 | 76.089 | 23.307 | 119.673 | 1.00 | 24.34 |
| ATOM | 997 | CA | PHE | 139 | 75.464 | 24.529 | 120.156 | 1.00 | 23.84 |
| ATOM | 998 | CB | PHE | 139 | 73.953 | 24.367 | 120.264 | 1.00 | 22.28 |
| ATOM | 999 | CG | PHE | 139 | 73.261 | 24.395 | 118.957 | 1.00 | 22.93 |
| ATOM | 1000 | CD1 | PHE | 139 | 73.124 | 23.241 | 118.209 | 1.00 | 22.66 |
| ATOM | 1001 | CD2 | PHE | 139 | 72.787 | 25.599 | 118.441 | 1.00 | 23.82 |
| ATOM | 1002 | CE1 | PHE | 139 | 72.528 | 23.280 | 116.959 | 1.00 | 23.77 |
| ATOM | 1003 | CE2 | PHE | 139 | 72.187 | 25.657 | 117.188 | 1.00 | 23.07 |
| ATOM | 1004 | CZ | PHE | 139 | 72.057 | 24.496 | 116.447 | 1.00 | 24.52 |
| ATOM | 1005 | C | PHE | 139 | 76.000 | 24.938 | 121.508 | 1.00 | 24.57 |
| ATOM | 1006 | O | PHE | 139 | 76.331 | 24.088 | 122.331 | 1.00 | 25.29 |
| ATOM | 1007 | N | LEU | 140 | 76.080 | 26.246 | 121.734 | 1.00 | 24.86 |
| ATOM | 1008 | CA | LEU | 140 | 76.561 | 26.778 | 123.000 | 1.00 | 24.03 |
| ATOM | 1009 | CB | LEU | 140 | 77.732 | 27.720 | 122.767 | 1.00 | 23.49 |
| ATOM | 1010 | CG | LEU | 140 | 78.316 | 28.286 | 124.056 | 1.00 | 24.43 |
| ATOM | 1011 | CD1 | LEU | 140 | 78.869 | 27.149 | 124.901 | 1.00 | 24.94 |
| ATOM | 1012 | CD2 | LEU | 140 | 79.403 | 29.293 | 123.725 | 1.00 | 25.05 |
| ATOM | 1013 | C | LEU | 140 | 75.442 | 27.528 | 123.696 | 1.00 | 23.97 |
| ATOM | 1014 | O | LEU | 140 | 74.984 | 28.559 | 123.218 | 1.00 | 24.09 |
| ATOM | 1015 | N | PRO | 141 | 74.972 | 27.012 | 124.835 | 1.00 | 25.23 |
| ATOM | 1016 | CD | PRO | 141 | 75.348 | 25.765 | 125.523 | 1.00 | 26.10 |
| ATOM | 1017 | CA | PRO | 141 | 73.893 | 27.692 | 125.550 | 1.00 | 24.64 |
| ATOM | 1018 | CB | PRO | 141 | 73.431 | 26.642 | 126.546 | 1.00 | 24.01 |
| ATOM | 1019 | CG | PRO | 141 | 74.697 | 25.950 | 126.879 | 1.00 | 25.83 |
| ATOM | 1020 | C | PRO | 141 | 74.411 | 28.940 | 126.225 | 1.00 | 24.54 |
| ATOM | 1021 | O | PRO | 141 | 75.468 | 28.921 | 126.840 | 1.00 | 24.16 |
| ATOM | 1022 | N | MET | 142 | 73.656 | 30.023 | 126.095 | 1.00 | 25.83 |
| ATOM | 1023 | CA | MET | 142 | 74.021 | 31.302 | 126.684 | 1.00 | 26.94 |
| ATOM | 1024 | CB | MET | 142 | 74.467 | 32.259 | 125.590 | 1.00 | 26.73 |
| ATOM | 1025 | CG | MET | 142 | 75.681 | 31.797 | 124.828 | 1.00 | 26.52 |
| ATOM | 1026 | SD | MET | 142 | 75.825 | 32.695 | 123.291 | 1.00 | 28.68 |
| ATOM | 1027 | CE | MET | 142 | 76.028 | 34.375 | 123.889 | 1.00 | 30.05 |
| ATOM | 1028 | C | MET | 142 | 72.841 | 31.898 | 127.439 | 1.00 | 28.78 |
| ATOM | 1029 | O | MET | 142 | 71.691 | 31.797 | 127.008 | 1.00 | 30.16 |
| ATOM | 1030 | N | SER | 143 | 73.144 | 32.533 | 128.561 | 1.00 | 30.18 |
| ATOM | 1031 | CA | SER | 143 | 72.141 | 33.137 | 129.428 | 1.00 | 31.33 |
| ATOM | 1032 | CB | SER | 143 | 72.815 | 33.782 | 130.635 | 1.00 | 33.94 |
| ATOM | 1033 | OG | SER | 143 | 73.513 | 34.964 | 130.241 | 1.00 | 34.85 |
| ATOM | 1034 | C | SER | 143 | 71.316 | 34.201 | 128.753 | 1.00 | 32.07 |
| ATOM | 1035 | O | SER | 143 | 71.709 | 34.760 | 127.723 | 1.00 | 33.01 |
| ATOM | 1036 | N | ALA | 144 | 70.184 | 34.504 | 129.378 | 1.00 | 32.11 |
| ATOM | 1037 | CA | ALA | 144 | 69.272 | 35.514 | 128.877 | 1.00 | 33.33 |
| ATOM | 1038 | CB | ALA | 144 | 68.459 | 34.950 | 127.712 | 1.00 | 31.68 |
| ATOM | 1039 | C | ALA | 144 | 68.354 | 35.953 | 130.012 | 1.00 | 33.81 |
| ATOM | 1040 | O | ALA | 144 | 68.722 | 36.947 | 130.676 | 1.00 | 35.06 |
| ATOM | 1041 | CB | HIS | 1016 | 101.518 | 8.804 | 140.892 | 1.00 | 59.01 |
| ATOM | 1042 | CG | HIS | 1016 | 101.606 | 8.263 | 142.280 | 1.00 | 61.41 |
| ATOM | 1043 | CD2 | HIS | 1016 | 101.132 | 7.115 | 142.818 | 1.00 | 62.71 |
| ATOM | 1044 | ND1 | HIS | 1016 | 102.190 | 8.962 | 143.315 | 1.00 | 61.90 |
| ATOM | 1045 | CE1 | HIS | 1016 | 102.065 | 8.269 | 144.433 | 1.00 | 63.14 |
| ATOM | 1046 | NE2 | HIS | 1016 | 101.428 | 7.145 | 144.159 | 1.00 | 63.99 |
| ATOM | 1047 | C | HIS | 1016 | 101.836 | 11.252 | 141.291 | 1.00 | 57.42 |
| ATOM | 1048 | O | HIS | 1016 | 102.845 | 11.510 | 140.626 | 1.00 | 56.67 |
| ATOM | 1049 | N | HIS | 1016 | 100.399 | 10.408 | 139.406 | 1.00 | 56.36 |
| ATOM | 1050 | CA | HIS | 1016 | 100.844 | 10.175 | 140.811 | 1.00 | 57.59 |
| ATOM | 1051 | N | PHE | 1017 | 101.561 | 11.859 | 142.448 | 1.00 | 57.43 |
| ATOM | 1052 | CA | PHE | 1017 | 102.428 | 12.900 | 143.019 | 1.00 | 57.26 |
| ATOM | 1053 | CB | PHE | 1017 | 101.756 | 13.525 | 144.262 | 1.00 | 59.29 |
| ATOM | 1054 | CG | PHE | 1017 | 101.888 | 12.691 | 145.536 | 1.00 | 61.69 |
| ATOM | 1055 | CD1 | PHE | 1017 | 103.100 | 12.628 | 146.234 | 1.00 | 62.85 |
| ATOM | 1056 | CD2 | PHE | 1017 | 100.804 | 11.962 | 146.029 | 1.00 | 61.97 |
| ATOM | 1057 | CE1 | PHE | 1017 | 103.226 | 11.848 | 147.402 | 1.00 | 63.09 |
| ATOM | 1058 | CE2 | PHE | 1017 | 100.922 | 11.184 | 147.193 | 1.00 | 62.16 |
| ATOM | 1059 | CZ | PHE | 1017 | 102.134 | 11.128 | 147.877 | 1.00 | 62.36 |
| ATOM | 1060 | C | PHE | 1017 | 103.817 | 12.377 | 143.418 | 1.00 | 56.18 |
| ATOM | 1061 | O | PHE | 1017 | 104.793 | 13.137 | 143.454 | 1.00 | 56.25 |

TABLE 6-continued

FGF2/FGFR1/Heparin Ternary Complex

| ATOM | 1062 | N | LYS | 1018 | 103.893 | 11.084 | 143.738 | 1.00 | 54.65 |
|---|---|---|---|---|---|---|---|---|---|
| ATOM | 1063 | CA | LYS | 1018 | 105.148 | 10.462 | 144.160 | 1.00 | 52.68 |
| ATOM | 1064 | CS | LYS | 1018 | 104.867 | 9.246 | 145.051 | 1.00 | 51.33 |
| ATOM | 1065 | C | LYS | 1018 | 106.050 | 10.046 | 142.998 | 1.00 | 51.79 |
| ATOM | 1066 | O | LYS | 1018 | 107.274 | 10.033 | 143.143 | 1.00 | 52.60 |
| ATOM | 1067 | N | ASP | 1019 | 105.452 | 9.703 | 141.856 | 1.00 | 50.23 |
| ATOM | 1068 | CA | ASP | 1019 | 106.215 | 9.298 | 140.669 | 1.00 | 48.35 |
| ATOM | 1069 | CB | ASP | 1019 | 105.298 | 8.704 | 139.591 | 1.00 | 48.73 |
| ATOM | 1070 | CG | ASP | 1019 | 104.915 | 7.266 | 139.862 | 1.00 | 49.14 |
| ATOM | 1071 | OD1 | ASP | 1019 | 105.830 | 6.437 | 140.063 | 1.00 | 49.01 |
| ATOM | 1072 | OD2 | ASP | 1019 | 103.698 | 6.968 | 139.856 | 1.00 | 49.31 |
| ATOM | 1073 | C | ASP | 1019 | 106.930 | 10.486 | 140.040 | 1.00 | 46.68 |
| ATOM | 1074 | O | ASP | 1019 | 106.536 | 11.632 | 140.237 | 1.00 | 47.50 |
| ATOM | 1075 | N | PRO | 1020 | 107.992 | 10.227 | 139.266 | 1.00 | 44.76 |
| ATOM | 1076 | CD | PRO | 1020 | 108.718 | 8.957 | 139.111 | 1.00 | 45.04 |
| ATOM | 1077 | CA | PRO | 1020 | 108.724 | 11.314 | 138.618 | 1.00 | 43.38 |
| ATOM | 1078 | CB | PRO | 1020 | 109.937 | 10.609 | 138.016 | 1.00 | 43.53 |
| ATOM | 1079 | CG | PRO | 1020 | 110.133 | 9.436 | 138.912 | 1.00 | 44.61 |
| ATOM | 1080 | C | PRO | 1020 | 107.838 | 11.904 | 137.532 | 1.00 | 41.94 |
| ATOM | 1081 | O | PRO | 1020 | 106.804 | 11.332 | 137.188 | 1.00 | 42.82 |
| ATOM | 1082 | N | LYS | 1021 | 108.251 | 13.040 | 136.990 | 1.00 | 39.67 |
| ATOM | 1083 | CA | LYS | 1021 | 107.504 | 13.687 | 135.931 | 1.00 | 37.28 |
| ATOM | 1084 | CB | LYS | 1021 | 106.621 | 14.775 | 136.527 | 1.00 | 37.64 |
| ATOM | 1085 | CG | LYS | 1021 | 105.772 | 14.264 | 137.667 | 1.00 | 38.77 |
| ATOM | 1086 | CD | LYS | 1021 | 104.743 | 15.284 | 138.098 | 1.00 | 39.71 |
| ATOM | 1087 | CE | LYS | 1021 | 103.909 | 14.744 | 139.244 | 1.00 | 40.35 |
| ATOM | 1088 | NZ | LYS | 1021 | 102.948 | 15.773 | 139.724 | 1.00 | 42.34 |
| ATOM | 1089 | C | LYS | 1021 | 108.473 | 14.287 | 134.927 | 1.00 | 35.45 |
| ATOM | 1090 | O | LYS | 1021 | 109.651 | 14.454 | 135.221 | 1.00 | 34.78 |
| ATOM | 1091 | N | ARG | 1022 | 107.986 | 14.569 | 133.728 | 1.00 | 34.49 |
| ATOM | 1092 | CA | ARG | 1022 | 108.807 | 15.208 | 132.703 | 1.00 | 33.99 |
| ATOM | 1093 | CB | ARG | 1022 | 108.688 | 14.506 | 131.346 | 1.00 | 35.90 |
| ATOM | 1094 | CG | ARG | 1022 | 108.969 | 13.004 | 131.299 | 1.00 | 38.98 |
| ATOM | 1095 | CD | ARG | 1022 | 108.848 | 12.540 | 129.843 | 1.00 | 41.25 |
| ATOM | 1096 | NE | ARG | 1022 | 108.420 | 11.152 | 129.670 | 1.00 | 42.83 |
| ATOM | 1097 | CZ | ARG | 1022 | 109.222 | 10.093 | 129.748 | 1.00 | 44.82 |
| ATOM | 1098 | NH1 | ARG | 1022 | 110.518 | 10.248 | 130.005 | 1.00 | 46.32 |
| ATOM | 1099 | NH2 | ARG | 1022 | 108.731 | 8.875 | 129.547 | 1.00 | 44.61 |
| ATOM | 1100 | C | ARG | 1022 | 108.168 | 16.588 | 132.589 | 1.00 | 32.26 |
| ATOM | 1101 | O | ARG | 1022 | 106.947 | 16.714 | 132.720 | 1.00 | 32.02 |
| ATOM | 1102 | N | LEU | 1023 | 108.960 | 17.629 | 132.361 | 1.00 | 29.70 |
| ATOM | 1103 | CA | LEU | 1023 | 108.364 | 18.952 | 132.240 | 1.00 | 27.31 |
| ATOM | 1104 | CB | LEU | 1023 | 109.045 | 19.915 | 133.216 | 1.00 | 27.24 |
| ATOM | 1105 | CG | LEU | 1023 | 108.723 | 19.725 | 134.711 | 1.00 | 26.31 |
| ATOM | 1106 | CD1 | LEU | 1023 | 109.524 | 20.709 | 135.531 | 1.00 | 25.75 |
| ATOM | 1107 | CD2 | LEU | 1023 | 107.240 | 19.937 | 134.980 | 1.00 | 23.99 |
| ATOM | 1108 | C | LEU | 1023 | 108.418 | 19.486 | 130.810 | 1.00 | 25.84 |
| ATOM | 1109 | O | LEU | 1023 | 109.410 | 20.081 | 130.399 | 1.00 | 26.23 |
| ATOM | 1110 | N | TYR | 1024 | 107.339 | 19.264 | 130.064 | 1.00 | 23.83 |
| ATOM | 1111 | CA | TYR | 1024 | 107.228 | 19.690 | 128.671 | 1.00 | 22.57 |
| ATOM | 1112 | CB | TYR | 1024 | 106.120 | 18.899 | 127.983 | 1.00 | 20.06 |
| ATOM | 1113 | CG | TYR | 1024 | 105.878 | 19.250 | 126.529 | 1.00 | 19.18 |
| ATOM | 1114 | CD1 | TYR | 1024 | 105.143 | 20.378 | 126.169 | 1.00 | 18.27 |
| ATOM | 1115 | CE1 | TYR | 1024 | 104.860 | 20.657 | 124.833 | 1.00 | 18.14 |
| ATOM | 1116 | CD2 | TYR | 1024 | 106.335 | 18.414 | 125.509 | 1.00 | 18.75 |
| ATOM | 1117 | CE2 | TYR | 1024 | 106.062 | 18.684 | 124.172 | 1.00 | 18.37 |
| ATOM | 1118 | CZ | TYR | 1024 | 105.324 | 19.802 | 123.836 | 1.00 | 19.29 |
| ATOM | 1119 | OH | TYR | 1024 | 105.039 | 20.050 | 122.506 | 1.00 | 19.56 |
| ATOM | 1120 | C | TYR | 1024 | 106.929 | 21.173 | 128.558 | 1.00 | 23.20 |
| ATOM | 1121 | O | TYR | 1024 | 105.830 | 21.614 | 128.880 | 1.00 | 22.70 |
| ATOM | 1122 | N | CYS | 1025 | 107.905 | 21.939 | 128.087 | 1.00 | 23.90 |
| ATOM | 1123 | CA | CYS | 1025 | 107.724 | 23.378 | 127.947 | 1.00 | 24.69 |
| ATOM | 1124 | CB | CYS | 1025 | 109.076 | 24.078 | 127.978 | 1.00 | 24.85 |
| ATOM | 1125 | SG | CYS | 1025 | 108.936 | 25.801 | 127.521 | 1.00 | 28.12 |
| ATOM | 1126 | C | CYS | 1025 | 106.977 | 23.755 | 126.675 | 1.00 | 24.46 |
| ATOM | 1127 | O | CYS | 1025 | 107.374 | 23.377 | 125.577 | 1.00 | 25.06 |
| ATOM | 1128 | N | LYS | 1026 | 105.902 | 24.519 | 126.825 | 1.00 | 24.76 |
| ATOM | 1129 | CA | LYS | 1026 | 105.080 | 24.932 | 125.686 | 1.00 | 25.07 |
| ATOM | 1130 | CB | LYS | 1026 | 103.983 | 25.901 | 126.131 | 1.00 | 23.49 |
| ATOM | 1131 | CG | LYS | 1026 | 103.154 | 26.435 | 124.979 | 1.00 | 21.62 |
| ATOM | 1132 | CD | LYS | 1026 | 102.026 | 27.292 | 125.466 | 1.00 | 20.45 |
| ATOM | 1133 | CE | LYS | 1026 | 101.077 | 27.578 | 124.341 | 1.00 | 20.75 |
| ATOM | 1134 | NZ | LYS | 1026 | 99.757 | 27.987 | 124.874 | 1.00 | 20.11 |
| ATOM | 1135 | C | LYS | 1026 | 105.858 | 25.574 | 124.543 | 1.00 | 25.60 |
| ATOM | 1136 | O | LYS | 1026 | 105.474 | 25.466 | 123.381 | 1.00 | 24.78 |
| ATOM | 1137 | N | ASN | 1027 | 106.954 | 26.238 | 124.877 | 1.00 | 26.80 |
| ATOM | 1138 | CA | ASN | 1027 | 107.759 | 26.920 | 123.879 | 1.00 | 27.49 |

TABLE 6-continued

FGF2/FGFR1/Heparin Ternary Complex

| ATOM | 1139 | CB | ASN | 1027 | 108.581 | 28.012 | 124.561 | 1.00 | 29.75 |
|---|---|---|---|---|---|---|---|---|---|
| ATOM | 1140 | CG | ASN | 1027 | 109.111 | 29.032 | 123.586 | 1.00 | 31.30 |
| ATOM | 1141 | OD1 | ASN | 1027 | 109.855 | 28.701 | 122.672 | 1.00 | 32.40 |
| ATOM | 1142 | ND2 | ASN | 1027 | 108.722 | 30.283 | 123.776 | 1.00 | 32.49 |
| ATOM | 1143 | C | ASN | 1027 | 108.688 | 25.993 | 123.109 | 1.00 | 27.16 |
| ATOM | 1144 | O | ASN | 1027 | 109.874 | 25.906 | 123.416 | 1.00 | 26.88 |
| ATOM | 1145 | N | GLY | 1028 | 108.157 | 25.307 | 122.104 | 1.00 | 26.67 |
| ATOM | 1146 | CA | GLY | 1028 | 108.997 | 24.423 | 121.318 | 1.00 | 25.66 |
| ATOM | 1147 | C | GLY | 1028 | 108.874 | 22.946 | 121.623 | 1.00 | 25.00 |
| ATOM | 1148 | O | GLY | 1028 | 109.349 | 22.114 | 120.856 | 1.00 | 24.79 |
| ATOM | 1149 | N | GLY | 1029 | 108.247 | 22.611 | 122.742 | 1.00 | 24.17 |
| ATOM | 1150 | CA | GLY | 1029 | 108.083 | 21.215 | 123.077 | 1.00 | 23.89 |
| ATOM | 1151 | C | GLY | 1029 | 109.342 | 20.605 | 123.639 | 1.00 | 24.58 |
| ATOM | 1152 | O | GLY | 1029 | 109.561 | 19.394 | 123.530 | 1.00 | 25.56 |
| ATOM | 1153 | N | PHE | 1030 | 110.185 | 21.438 | 124.234 | 1.00 | 24.21 |
| ATOM | 1154 | CA | PHE | 1030 | 111.408 | 20.923 | 124.818 | 1.00 | 24.60 |
| ATOM | 1155 | CB | PHE | 1030 | 112.506 | 21.994 | 124.833 | 1.00 | 27.19 |
| ATOM | 1156 | CG | PHE | 1030 | 113.013 | 22.370 | 123.471 | 1.00 | 28.03 |
| ATOM | 1157 | CD1 | PHE | 1030 | 112.293 | 23.243 | 122.656 | 1.00 | 28.82 |
| ATOM | 1158 | CD2 | PHE | 1030 | 114.186 | 21.810 | 122.977 | 1.00 | 28.15 |
| ATOM | 1159 | CE1 | PHE | 1030 | 112.735 | 23.547 | 121.361 | 1.00 | 28.58 |
| ATOM | 1160 | CE2 | PHE | 1030 | 114.634 | 22.104 | 121.688 | 1.00 | 27.55 |
| ATOM | 1161 | CZ | PHE | 1030 | 113.905 | 22.975 | 120.879 | 1.00 | 28.04 |
| ATOM | 1162 | C | PHE | 1030 | 111.114 | 20.483 | 126.240 | 1.00 | 24.03 |
| ATOM | 1163 | O | PHE | 1030 | 110.433 | 21.194 | 126.984 | 1.00 | 24.19 |
| ATOM | 1164 | N | PHE | 1031 | 111.607 | 19.306 | 126.606 | 1.00 | 23.11 |
| ATOM | 1165 | CA | PHE | 1031 | 111.420 | 18.799 | 127.957 | 1.00 | 23.93 |
| ATOM | 1166 | CB | PHE | 1031 | 111.553 | 17.284 | 127.985 | 1.00 | 23.81 |
| ATOM | 1167 | CG | PHE | 1031 | 110.423 | 16.563 | 127.342 | 1.00 | 24.08 |
| ATOM | 1168 | CD1 | PHE | 1031 | 109.186 | 16.491 | 127.965 | 1.00 | 24.04 |
| ATOM | 1169 | CD2 | PHE | 1031 | 110.609 | 15.902 | 126.133 | 1.00 | 24.06 |
| ATOM | 1170 | CE1 | PHE | 1031 | 108.138 | 15.759 | 127.392 | 1.00 | 25.00 |
| ATOM | 1171 | CE2 | PHE | 1031 | 109.578 | 15.171 | 125.551 | 1.00 | 23.76 |
| ATOM | 1172 | CZ | PHE | 1031 | 108.336 | 15.096 | 126.181 | 1.00 | 24.63 |
| ATOM | 1173 | C | PHE | 1031 | 112.544 | 19.391 | 128.782 | 1.00 | 24.04 |
| ATOM | 1174 | O | PHE | 1031 | 113.694 | 19.372 | 128.348 | 1.00 | 24.45 |
| ATOM | 1175 | N | LEU | 1032 | 112.222 | 19.914 | 129.962 | 1.00 | 24.19 |
| ATOM | 1176 | CA | LEU | 1032 | 113.249 | 20.483 | 130.828 | 1.00 | 24.56 |
| ATOM | 1177 | CB | LEU | 1032 | 112.627 | 21.058 | 132.102 | 1.00 | 25.47 |
| ATOM | 1178 | CG | LEU | 1032 | 113.620 | 21.473 | 133.186 | 1.00 | 25.35 |
| ATOM | 1179 | CD1 | LEU | 1032 | 114.612 | 22.467 | 132.624 | 1.00 | 25.37 |
| ATOM | 1180 | CD2 | LEU | 1032 | 112.856 | 22.069 | 134.351 | 1.00 | 26.44 |
| ATOM | 1181 | C | LEU | 1032 | 114.227 | 19.382 | 131.204 | 1.00 | 24.51 |
| ATOM | 1182 | O | LEU | 1032 | 113.820 | 18.325 | 131.683 | 1.00 | 24.03 |
| ATOM | 1183 | N | ARG | 1033 | 115.513 | 19.618 | 130.988 | 1.00 | 25.35 |
| ATOM | 1184 | CA | ARG | 1033 | 116.480 | 18.600 | 131.333 | 1.00 | 27.36 |
| ATOM | 1185 | CB | ARG | 1033 | 117.053 | 17.938 | 130.099 | 1.00 | 29.33 |
| ATOM | 1186 | CG | ARG | 1033 | 118.195 | 17.018 | 130.427 | 1.00 | 30.80 |
| ATOM | 1187 | CD | ARG | 1033 | 118.837 | 16.584 | 129.155 | 1.00 | 33.61 |
| ATOM | 1188 | NE | ARG | 1033 | 119.158 | 17.738 | 128.327 | 1.00 | 34.72 |
| ATOM | 1189 | CZ | ARG | 1033 | 119.497 | 17.657 | 127.047 | 1.00 | 36.13 |
| ATOM | 1190 | NH1 | ARG | 1033 | 119.557 | 16.469 | 126.453 | 1.00 | 35.83 |
| ATOM | 1191 | NH2 | ARG | 1033 | 119.766 | 18.764 | 126.363 | 1.00 | 36.25 |
| ATOM | 1192 | C | ARG | 1033 | 117.617 | 19.067 | 132.206 | 1.00 | 28.28 |
| ATOM | 1193 | O | ARG | 1033 | 118.128 | 20.192 | 132.074 | 1.00 | 27.87 |
| ATOM | 1194 | N | ILE | 1034 | 118.004 | 18.165 | 133.102 | 1.00 | 28.57 |
| ATOM | 1195 | CA | ILE | 1034 | 119.077 | 18.413 | 134.042 | 1.00 | 29.81 |
| ATOM | 1196 | CB | ILE | 1034 | 118.602 | 18.182 | 135.503 | 1.00 | 29.73 |
| ATOM | 1197 | CG2 | ILE | 1034 | 119.672 | 18.645 | 136.479 | 1.00 | 29.55 |
| ATOM | 1198 | CG1 | ILE | 1034 | 117.292 | 18.927 | 135.770 | 1.00 | 28.20 |
| ATOM | 1199 | CD1 | ILE | 1034 | 117.417 | 20.419 | 135.788 | 1.00 | 28.36 |
| ATOM | 1200 | C | ILE | 1034 | 120.197 | 17.427 | 133.741 | 1.00 | 31.51 |
| ATOM | 1201 | O | ILE | 1034 | 120.023 | 16.216 | 133.901 | 1.00 | 32.11 |
| ATOM | 1202 | N | HIS | 1035 | 121.337 | 17.951 | 133.297 | 1.00 | 33.05 |
| ATOM | 1203 | CA | HIS | 1035 | 122.508 | 17.136 | 132.989 | 1.00 | 34.19 |
| ATOM | 1204 | CB | HIS | 1035 | 123.489 | 17.942 | 132.145 | 1.00 | 36.64 |
| ATOM | 1205 | CG | HIS | 1035 | 123.020 | 18.181 | 130.747 | 1.00 | 40.58 |
| ATOM | 1206 | CD2 | HIS | 1035 | 122.613 | 19.311 | 130.122 | 1.00 | 42.17 |
| ATOM | 1207 | ND1 | HIS | 1035 | 122.911 | 17.166 | 129.818 | 1.00 | 42.83 |
| ATOM | 1208 | CE1 | HIS | 1035 | 122.456 | 17.663 | 128.679 | 1.00 | 43.39 |
| ATOM | 1209 | NE2 | HIS | 1035 | 122.267 | 18.962 | 128.837 | 1.00 | 44.24 |
| ATOM | 1210 | C | HIS | 1035 | 123.177 | 16.729 | 134.292 | 1.00 | 33.79 |
| ATOM | 1211 | O | HIS | 1035 | 123.072 | 17.435 | 135.292 | 1.00 | 33.45 |
| ATOM | 1212 | N | PRO | 1036 | 123.857 | 15.576 | 134.306 | 1.00 | 34.09 |
| ATOM | 1213 | CD | PRO | 1036 | 123.803 | 14.488 | 133.312 | 1.00 | 34.23 |
| ATOM | 1214 | CA | PRO | 1036 | 124.531 | 15.133 | 135.535 | 1.00 | 34.98 |
| ATOM | 1215 | CB | PRO | 1036 | 125.088 | 13.763 | 135.148 | 1.00 | 34.75 |

TABLE 6-continued

FGF2/FGFR1/Heparin Ternary Complex

| ATOM | 1216 | CG  | PRO | 1036 | 124.066 | 13.264 | 134.168 | 1.00 | 34.74 |
|------|------|-----|-----|------|---------|--------|---------|------|-------|
| ATOM | 1217 | C   | PRO | 1036 | 125.630 | 16.116 | 135.968 | 1.00 | 35.63 |
| ATOM | 1218 | O   | PRO | 1036 | 126.026 | 16.155 | 137.137 | 1.00 | 34.88 |
| ATOM | 1219 | N   | ASP | 1037 | 126.104 | 16.916 | 135.017 | 1.00 | 36.45 |
| ATOM | 1220 | CA  | ASP | 1037 | 127.151 | 17.890 | 135.289 | 1.00 | 38.23 |
| ATOM | 1221 | CB  | ASP | 1037 | 127.973 | 18.131 | 134.024 | 1.00 | 40.95 |
| ATOM | 1222 | CG  | ASP | 1037 | 127.209 | 18.925 | 132.975 | 1.00 | 43.34 |
| ATOM | 1223 | OD1 | ASP | 1037 | 126.783 | 20.060 | 133.279 | 1.00 | 44.61 |
| ATOM | 1224 | OD2 | ASP | 1037 | 127.039 | 18.418 | 131.844 | 1.00 | 44.86 |
| ATOM | 1225 | C   | ASP | 1037 | 126.621 | 19.233 | 135.793 | 1.00 | 39.23 |
| ATOM | 1226 | O   | ASP | 1037 | 127.403 | 20.138 | 136.091 | 1.00 | 40.23 |
| ATOM | 1227 | N   | GLY | 1038 | 125.301 | 19.382 | 135.863 | 1.00 | 39.39 |
| ATOM | 1228 | CA  | GLY | 1038 | 124.740 | 20.635 | 136.342 | 1.00 | 38.48 |
| ATOM | 1229 | C   | GLY | 1038 | 124.132 | 21.533 | 135.278 | 1.00 | 38.00 |
| ATOM | 1230 | O   | GLY | 1038 | 123.409 | 22.474 | 135.606 | 1.00 | 37.99 |
| ATOM | 1231 | N   | ARG | 1039 | 124.419 | 21.273 | 134.008 | 1.00 | 37.82 |
| ATOM | 1232 | CA  | ARG | 1039 | 123.848 | 22.100 | 132.951 | 1.00 | 38.07 |
| ATOM | 1233 | CB  | ARG | 1039 | 124.432 | 21.739 | 131.591 | 1.00 | 40.33 |
| ATOM | 1234 | CG  | ARG | 1039 | 125.856 | 22.173 | 131.337 | 1.00 | 42.49 |
| ATOM | 1235 | CD  | ARG | 1039 | 126.235 | 21.758 | 129.924 | 1.00 | 45.35 |
| ATOM | 1236 | NE  | ARG | 1039 | 126.170 | 20.303 | 129.755 | 1.00 | 48.54 |
| ATOM | 1237 | CZ  | ARG | 1039 | 125.744 | 19.683 | 128.653 | 1.00 | 49.62 |
| ATOM | 1238 | NH1 | ARG | 1039 | 125.735 | 18.354 | 128.605 | 1.00 | 49.36 |
| ATOM | 1239 | NH2 | ARG | 1039 | 125.311 | 20.383 | 127.606 | 1.00 | 48.98 |
| ATOM | 1240 | C   | ARG | 1039 | 122.346 | 21.882 | 132.887 | 1.00 | 37.46 |
| ATOM | 1241 | O   | ARG | 1039 | 121.852 | 20.793 | 133.187 | 1.00 | 37.66 |
| ATOM | 1242 | N   | VAL | 1040 | 121.620 | 22.917 | 132.487 | 1.00 | 36.66 |
| ATOM | 1243 | CA  | VAL | 1040 | 120.168 | 22.832 | 132.359 | 1.00 | 35.75 |
| ATOM | 1244 | CB  | VAL | 1040 | 119.461 | 23.634 | 133.479 | 1.00 | 35.63 |
| ATOM | 1245 | CG1 | VAL | 1040 | 117.970 | 23.515 | 133.343 | 1.00 | 35.65 |
| ATOM | 1246 | CG2 | VAL | 1040 | 119.904 | 23.138 | 134.832 | 1.00 | 35.67 |
| ATOM | 1247 | C   | VAL | 1040 | 119.737 | 23.392 | 130.994 | 1.00 | 35.53 |
| ATOM | 1248 | O   | VAL | 1040 | 120.135 | 24.496 | 130.596 | 1.00 | 36.39 |
| ATOM | 1249 | N   | ASP | 1041 | 118.929 | 22.626 | 130.274 | 1.00 | 33.97 |
| ATOM | 1250 | CA  | ASP | 1041 | 118.447 | 23.046 | 128.967 | 1.00 | 32.42 |
| ATOM | 1251 | CB  | ASP | 1041 | 119.534 | 22.848 | 127.916 | 1.00 | 32.62 |
| ATOM | 1252 | CG  | ASP | 1041 | 120.015 | 21.411 | 127.843 | 1.00 | 32.94 |
| ATOM | 1253 | OD1 | ASP | 1041 | 120.810 | 21.104 | 126.933 | 1.00 | 33.43 |
| ATOM | 1254 | OD2 | ASP | 1041 | 119.605 | 20.591 | 128.695 | 1.00 | 32.32 |
| ATOM | 1255 | C   | ASP | 1041 | 117.255 | 22.175 | 128.632 | 1.00 | 31.66 |
| ATOM | 1256 | O   | ASP | 1041 | 116.714 | 21.500 | 129.510 | 1.00 | 32.29 |
| ATOM | 1257 | N   | GLY | 1042 | 116.853 | 22.177 | 127.367 | 1.00 | 30.54 |
| ATOM | 1258 | CA  | GLY | 1042 | 115.727 | 21.364 | 126.962 | 1.00 | 29.69 |
| ATOM | 1259 | C   | GLY | 1042 | 116.060 | 20.372 | 125.866 | 1.00 | 29.53 |
| ATOM | 1260 | O   | GLY | 1042 | 117.030 | 20.527 | 125.146 | 1.00 | 29.47 |
| ATOM | 1261 | N   | VAL | 1043 | 115.248 | 19.334 | 125.756 | 1.00 | 30.48 |
| ATOM | 1262 | CA  | VAL | 1043 | 115.418 | 18.319 | 124.732 | 1.00 | 31.18 |
| ATOM | 1263 | CB  | VAL | 1043 | 116.175 | 17.097 | 125.222 | 1.00 | 30.95 |
| ATOM | 1264 | CG1 | VAL | 1043 | 117.582 | 17.153 | 124.723 | 1.00 | 31.45 |
| ATOM | 1265 | CG2 | VAL | 1043 | 116.136 | 17.031 | 126.740 | 1.00 | 31.50 |
| ATOM | 1266 | C   | VAL | 1043 | 114.048 | 17.855 | 124.350 | 1.00 | 33.51 |
| ATOM | 1267 | O   | VAL | 1043 | 113.209 | 17.590 | 125.212 | 1.00 | 35.18 |
| ATOM | 1268 | N   | ARG | 1044 | 113.814 | 17.763 | 123.054 | 1.00 | 34.82 |
| ATOM | 1269 | CA  | ARG | 1044 | 112.530 | 17.319 | 122.564 | 1.00 | 36.01 |
| ATOM | 1270 | CB  | ARG | 1044 | 112.392 | 17.677 | 121.088 | 1.00 | 35.77 |
| ATOM | 1271 | CG  | ARG | 1044 | 112.204 | 19.145 | 120.799 | 1.00 | 36.67 |
| ATOM | 1272 | CD  | ARG | 1044 | 111.240 | 19.275 | 119.629 | 1.00 | 36.95 |
| ATOM | 1273 | NE  | ARG | 1044 | 111.264 | 20.585 | 118.999 | 1.00 | 36.46 |
| ATOM | 1274 | CZ  | ARG | 1044 | 112.322 | 21.071 | 118.376 | 1.00 | 37.37 |
| ATOM | 1275 | NH1 | ARG | 1044 | 113.429 | 20.344 | 118.317 | 1.00 | 38.72 |
| ATOM | 1276 | NH2 | ARG | 1044 | 112.269 | 22.265 | 117.804 | 1.00 | 38.11 |
| ATOM | 1277 | C   | ARG | 1044 | 112.379 | 15.806 | 122.730 | 1.00 | 36.56 |
| ATOM | 1278 | O   | ARG | 1044 | 111.267 | 15.293 | 122.861 | 1.00 | 37.22 |
| ATOM | 1279 | N   | GLU | 1045 | 113.501 | 15.098 | 122.725 | 1.00 | 37.07 |
| ATOM | 1280 | CA  | GLU | 1045 | 113.479 | 13.648 | 122.830 | 1.00 | 39.00 |
| ATOM | 1281 | CB  | GLU | 1045 | 114.880 | 13.103 | 122.589 | 1.00 | 41.67 |
| ATOM | 1282 | CG  | GLU | 1045 | 114.959 | 11.601 | 122.703 | 1.00 | 45.67 |
| ATOM | 1283 | CD  | GLU | 1045 | 113.987 | 10.909 | 121.774 | 1.00 | 47.99 |
| ATOM | 1284 | OE1 | GLU | 1045 | 114.065 | 11.168 | 120.552 | 1.00 | 48.20 |
| ATOM | 1285 | OE2 | GLU | 1045 | 113.152 | 10.112 | 122.266 | 1.00 | 49.71 |
| ATOM | 1286 | C   | GLU | 1045 | 112.934 | 13.125 | 124.157 | 1.00 | 39.22 |
| ATOM | 1287 | O   | GLU | 1045 | 113.573 | 13.254 | 125.204 | 1.00 | 39.70 |
| ATOM | 1288 | N   | LYS | 1046 | 111.755 | 12.511 | 124.098 | 1.00 | 39.02 |
| ATOM | 1289 | CA  | LYS | 1046 | 111.095 | 11.980 | 125.284 | 1.00 | 38.99 |
| ATOM | 1290 | CB  | LYS | 1046 | 109.712 | 11.453 | 124.903 | 1.00 | 40.13 |
| ATOM | 1291 | CG  | LYS | 1046 | 108.760 | 11.275 | 126.072 | 1.00 | 41.18 |
| ATOM | 1292 | CD  | LYS | 1046 | 107.452 | 10.664 | 125.597 | 1.00 | 41.92 |

TABLE 6-continued

FGF2/FGFR1/Heparin Ternary Complex

| ATOM | 1293 | CE | LYS | 1046 | 106.445 | 10.538 | 126.724 | 1.00 | 42.22 |
|---|---|---|---|---|---|---|---|---|---|
| ATOM | 1294 | NZ | LYS | 1046 | 105.377 | 9.565 | 126.377 | 1.00 | 41.59 |
| ATOM | 1295 | C | LYS | 1046 | 111.895 | 10.869 | 125.947 | 1.00 | 38.27 |
| ATOM | 1296 | O | LYS | 1046 | 111.705 | 10.572 | 127.127 | 1.00 | 38.11 |
| ATOM | 1297 | N | SER | 1047 | 112.798 | 10.257 | 125.194 | 1.00 | 37.78 |
| ATOM | 1298 | CA | SER | 1047 | 113.587 | 9.169 | 125.745 | 1.00 | 37.54 |
| ATOM | 1299 | CB | SER | 1047 | 113.930 | 8.157 | 124.653 | 1.00 | 37.91 |
| ATOM | 1300 | OG | SER | 1047 | 114.816 | 8.722 | 123.704 | 1.00 | 38.67 |
| ATOM | 1301 | C | SER | 1047 | 114.865 | 9.632 | 126.425 | 1.00 | 37.38 |
| ATOM | 1302 | O | SER | 1047 | 115.596 | 8.818 | 126.987 | 1.00 | 37.63 |
| ATOM | 1303 | N | ASP | 1048 | 115.142 | 10.931 | 126.391 | 1.00 | 37.33 |
| ATOM | 1304 | CA | ASP | 1048 | 116.364 | 11.406 | 127.023 | 1.00 | 37.51 |
| ATOM | 1305 | CB | ASP | 1048 | 116.451 | 12.924 | 127.034 | 1.00 | 38.35 |
| ATOM | 1306 | CG | ASP | 1048 | 117.766 | 13.401 | 127.603 | 1.00 | 39.91 |
| ATOM | 1307 | OD1 | ASP | 1048 | 118.706 | 13.622 | 126.817 | 1.00 | 41.96 |
| ATOM | 1308 | OD2 | ASP | 1048 | 117.878 | 13.519 | 128.841 | 1.00 | 39.65 |
| ATOM | 1309 | C | ASP | 1048 | 116.464 | 10.892 | 128.456 | 1.00 | 36.69 |
| ATOM | 1310 | O | ASP | 1048 | 115.500 | 10.915 | 129.213 | 1.00 | 37.46 |
| ATOM | 1311 | N | PRO | 1049 | 117.648 | 10.436 | 128.855 | 1.00 | 36.45 |
| ATOM | 1312 | CD | PRO | 1049 | 118.917 | 10.515 | 128.109 | 1.00 | 37.50 |
| ATOM | 1313 | CA | PRO | 1049 | 117.871 | 9.905 | 130.203 | 1.00 | 36.97 |
| ATOM | 1314 | CB | PRO | 1049 | 119.215 | 9.221 | 130.069 | 1.00 | 37.74 |
| ATOM | 1315 | CG | PRO | 1049 | 119.951 | 10.220 | 129.195 | 1.00 | 38.33 |
| ATOM | 1316 | C | PRO | 1049 | 117.900 | 10.947 | 131.327 | 1.00 | 37.11 |
| ATOM | 1317 | O | PRO | 1049 | 117.942 | 10.590 | 132.506 | 1.00 | 36.40 |
| ATOM | 1318 | N | HIS | 1050 | 117.872 | 12.227 | 130.971 | 1.00 | 36.89 |
| ATOM | 1319 | CA | HIS | 1050 | 117.946 | 13.275 | 131.978 | 1.00 | 36.16 |
| ATOM | 1320 | CB | HIS | 1050 | 119.217 | 14.092 | 131.740 | 1.00 | 38.30 |
| ATOM | 1321 | CG | HIS | 1050 | 120.450 | 13.251 | 131.642 | 1.00 | 41.46 |
| ATOM | 1322 | CD2 | HIS | 1050 | 121.244 | 12.953 | 130.588 | 1.00 | 42.61 |
| ATOM | 1323 | ND1 | HIS | 1050 | 120.952 | 12.537 | 132.710 | 1.00 | 42.99 |
| ATOM | 1324 | CE1 | HIS | 1050 | 121.998 | 11.833 | 132.319 | 1.00 | 41.93 |
| ATOM | 1325 | NE2 | HIS | 1050 | 122.197 | 12.067 | 131.035 | 1.00 | 42.82 |
| ATOM | 1326 | C | HIS | 1050 | 116.731 | 14.194 | 132.059 | 1.00 | 35.30 |
| ATOM | 1327 | O | HIS | 1050 | 116.842 | 15.336 | 132.526 | 1.00 | 35.31 |
| ATOM | 1328 | N | ILE | 1051 | 115.572 | 13.714 | 131.617 | 1.00 | 33.53 |
| ATOM | 1329 | CA | ILE | 1051 | 114.381 | 14.550 | 131.688 | 1.00 | 32.37 |
| ATOM | 1330 | CB | ILE | 1051 | 113.604 | 14.576 | 130.346 | 1.00 | 32.31 |
| ATOM | 1331 | CG2 | ILE | 1051 | 114.456 | 15.166 | 129.279 | 1.00 | 33.43 |
| ATOM | 1332 | CG1 | ILE | 1051 | 113.173 | 13.168 | 129.944 | 1.00 | 33.19 |
| ATOM | 1333 | CD1 | ILE | 1051 | 112.059 | 13.153 | 128.925 | 1.00 | 35.55 |
| ATOM | 1334 | C | ILE | 1051 | 113.420 | 14.119 | 132.800 | 1.00 | 31.45 |
| ATOM | 1335 | O | ILE | 1051 | 112.386 | 14.766 | 133.007 | 1.00 | 30.74 |
| ATOM | 1336 | N | LYS | 1052 | 113.753 | 13.031 | 133.499 | 1.00 | 30.01 |
| ATOM | 1337 | CA | LYS | 1052 | 112.911 | 12.539 | 134.589 | 1.00 | 29.82 |
| ATOM | 1338 | CB | LYS | 1052 | 113.178 | 11.056 | 134.836 | 1.00 | 29.20 |
| ATOM | 1339 | CG | LYS | 1052 | 112.119 | 10.160 | 134.223 | 1.00 | 30.35 |
| ATOM | 1340 | CD | LYS | 1052 | 112.543 | 8.688 | 134.198 | 1.00 | 32.59 |
| ATOM | 1341 | CE | LYS | 1052 | 111.398 | 7.744 | 133.745 | 1.00 | 33.09 |
| ATOM | 1342 | NZ | LYS | 1052 | 110.379 | 7.422 | 134.818 | 1.00 | 32.19 |
| ATOM | 1343 | C | LYS | 1052 | 113.178 | 13.355 | 135.856 | 1.00 | 30.43 |
| ATOM | 1344 | O | LYS | 1052 | 114.215 | 13.204 | 136.507 | 1.00 | 30.77 |
| ATOM | 1345 | N | LEU | 1053 | 112.225 | 14.219 | 136.198 | 1.00 | 29.79 |
| ATOM | 1346 | CA | LEU | 1053 | 112.352 | 15.100 | 137.349 | 1.00 | 29.36 |
| ATOM | 1347 | CB | LEU | 1053 | 111.990 | 16.532 | 136.939 | 1.00 | 29.08 |
| ATOM | 1348 | CG | LEU | 1053 | 112.364 | 16.937 | 135.507 | 1.00 | 28.41 |
| ATOM | 1349 | CD1 | LEU | 1053 | 111.923 | 18.366 | 135.238 | 1.00 | 28.73 |
| ATOM | 1350 | CD2 | LEU | 1053 | 113.852 | 16.785 | 135.299 | 1.00 | 27.13 |
| ATOM | 1351 | C | LEU | 1053 | 111.474 | 14.680 | 138.518 | 1.00 | 29.19 |
| ATOM | 1352 | O | LEU | 1053 | 110.356 | 14.209 | 138.337 | 1.00 | 30.04 |
| ATOM | 1353 | N | GLN | 1054 | 111.988 | 14.865 | 139.725 | 1.00 | 28.59 |
| ATOM | 1354 | CA | GLN | 1054 | 111.252 | 14.522 | 140.927 | 1.00 | 27.99 |
| ATOM | 1355 | CB | GLN | 1054 | 112.114 | 13.674 | 141.848 | 1.00 | 30.24 |
| ATOM | 1356 | CG | GLN | 1054 | 111.328 | 12.989 | 142.939 | 1.00 | 33.29 |
| ATOM | 1357 | CD | GLN | 1054 | 110.286 | 12.031 | 142.386 | 1.00 | 35.36 |
| ATOM | 1358 | OE1 | GLN | 1054 | 110.615 | 11.090 | 141.656 | 1.00 | 35.98 |
| ATOM | 1359 | NE2 | GLN | 1054 | 109.020 | 12.263 | 142.733 | 1.00 | 37.07 |
| ATOM | 1360 | C | GLN | 1054 | 110.877 | 15.823 | 141.615 | 1.00 | 27.38 |
| ATOM | 1361 | O | GLN | 1054 | 111.707 | 16.470 | 142.255 | 1.00 | 26.70 |
| ATOM | 1362 | N | LEU | 1055 | 109.624 | 16.224 | 141.455 | 1.00 | 27.43 |
| ATOM | 1363 | CA | LEU | 1055 | 109.174 | 17.464 | 142.062 | 1.00 | 27.22 |
| ATOM | 1364 | CB | LEU | 1055 | 108.036 | 18.086 | 141.253 | 1.00 | 26.41 |
| ATOM | 1365 | CG | LEU | 1055 | 108.096 | 18.061 | 139.724 | 1.00 | 25.53 |
| ATOM | 1366 | CD1 | LEU | 1055 | 107.477 | 19.348 | 139.210 | 1.00 | 26.11 |
| ATOM | 1367 | CD2 | LEU | 1055 | 109.516 | 17.932 | 139.224 | 1.00 | 25.01 |
| ATOM | 1368 | C | LEU | 1055 | 108.717 | 17.155 | 143.477 | 1.00 | 27.58 |
| ATOM | 1369 | O | LEU | 1055 | 107.894 | 16.266 | 143.705 | 1.00 | 28.23 |

TABLE 6-continued

FGF2/FGFR1/Heparin Ternary Complex

| ATOM | 1370 | N | GLN | 1056 | 109.282 | 17.883 | 144.430 | 1.00 | 27.30 |
|---|---|---|---|---|---|---|---|---|---|
| ATOM | 1371 | CA | GLN | 1056 | 108.973 | 17.686 | 145.834 | 1.00 | 26.90 |
| ATOM | 1372 | CB | GLN | 1056 | 110.237 | 17.290 | 146.587 | 1.00 | 25.90 |
| ATOM | 1373 | CG | GLN | 1056 | 110.053 | 17.177 | 148.068 | 1.00 | 25.61 |
| ATOM | 1374 | CD | GLN | 1056 | 109.254 | 15.962 | 148.458 | 1.00 | 25.90 |
| ATOM | 1375 | OE1 | GLN | 1056 | 109.647 | 14.830 | 148.180 | 1.00 | 26.01 |
| ATOM | 1376 | NE2 | GLN | 1056 | 108.125 | 16.188 | 149.109 | 1.00 | 26.29 |
| ATOM | 1377 | C | GLN | 1056 | 108.470 | 18.997 | 146.373 | 1.00 | 27.81 |
| ATOM | 1378 | O | GLN | 1056 | 108.977 | 20.057 | 146.004 | 1.00 | 28.43 |
| ATOM | 1379 | N | ALA | 1057 | 107.470 | 18.942 | 147.239 | 1.00 | 28.38 |
| ATOM | 1380 | CA | ALA | 1057 | 106.955 | 20.170 | 147.813 | 1.00 | 29.08 |
| ATOM | 1381 | CB | ALA | 1057 | 105.489 | 20.034 | 148.133 | 1.00 | 28.76 |
| ATOM | 1382 | C | ALA | 1057 | 107.733 | 20.419 | 149.080 | 1.00 | 29.91 |
| ATOM | 1383 | O | ALA | 1057 | 108.043 | 19.482 | 149.818 | 1.00 | 28.98 |
| ATOM | 1384 | N | GLU | 1058 | 108.083 | 21.674 | 149.326 | 1.00 | 31.39 |
| ATOM | 1385 | CA | GLU | 1058 | 108.793 | 21.986 | 150.553 | 1.00 | 32.34 |
| ATOM | 1386 | CB | GLU | 1058 | 109.930 | 22.975 | 150.309 | 1.00 | 32.18 |
| ATOM | 1387 | CG | GLU | 1058 | 110.960 | 22.983 | 151.429 | 1.00 | 31.46 |
| ATOM | 1388 | CD | GLU | 1058 | 111.597 | 21.618 | 151.657 | 1.00 | 32.73 |
| ATOM | 1389 | OE1 | GLU | 1058 | 111.898 | 20.928 | 150.655 | 1.00 | 33.37 |
| ATOM | 1390 | OE2 | GLU | 1058 | 111.810 | 21.239 | 152.833 | 1.00 | 31.34 |
| ATOM | 1391 | C | GLU | 1058 | 107.741 | 22.574 | 151.478 | 1.00 | 32.21 |
| ATOM | 1392 | O | GLU | 1058 | 107.961 | 22.715 | 152.672 | 1.00 | 33.06 |
| ATOM | 1393 | N | GLU | 1059 | 106.586 | 22.889 | 150.896 | 1.00 | 32.19 |
| ATOM | 1394 | CA | GLU | 1059 | 105.437 | 23.419 | 151.617 | 1.00 | 32.10 |
| ATOM | 1395 | CB | GLU | 1059 | 105.829 | 24.600 | 152.491 | 1.00 | 35.18 |
| ATOM | 1396 | CG | GLU | 1059 | 106.378 | 25.769 | 151.712 | 1.00 | 40.63 |
| ATOM | 1397 | CD | GLU | 1059 | 106.664 | 26.957 | 152.598 | 1.00 | 43.35 |
| ATOM | 1398 | OE1 | GLU | 1059 | 107.449 | 26.789 | 153.562 | 1.00 | 44.97 |
| ATOM | 1399 | OE2 | GLU | 1059 | 106.106 | 28.048 | 152.331 | 1.00 | 45.15 |
| ATOM | 1400 | C | GLU | 1059 | 104.420 | 23.858 | 150.589 | 1.00 | 30.54 |
| ATOM | 1401 | O | GLU | 1059 | 104.743 | 23.981 | 149.414 | 1.00 | 30.71 |
| ATOM | 1402 | N | ARG | 1060 | 103.192 | 24.094 | 151.027 | 1.00 | 29.55 |
| ATOM | 1403 | CA | ARG | 1060 | 102.133 | 24.519 | 150.117 | 1.00 | 29.30 |
| ATOM | 1404 | CB | ARG | 1060 | 101.011 | 25.229 | 150.866 | 1.00 | 30.12 |
| ATOM | 1405 | CG | ARG | 1060 | 100.039 | 24.290 | 151.508 | 1.00 | 35.96 |
| ATOM | 1406 | CD | ARG | 1060 | 98.847 | 25.021 | 152.089 | 1.00 | 40.51 |
| ATOM | 1407 | NE | ARG | 1060 | 98.154 | 25.824 | 151.087 | 1.00 | 44.34 |
| ATOM | 1408 | CZ | ARG | 1060 | 96.887 | 26.214 | 151.196 | 1.00 | 46.43 |
| ATOM | 1409 | NH1 | ARG | 1060 | 96.173 | 25.870 | 152.264 | 1.00 | 47.36 |
| ATOM | 1410 | NH2 | ARG | 1060 | 96.330 | 26.944 | 150.236 | 1.00 | 47.74 |
| ATOM | 1411 | C | ARG | 1060 | 102.596 | 25.440 | 149.009 | 1.00 | 28.18 |
| ATOM | 1412 | O | ARG | 1060 | 103.131 | 26.515 | 149.271 | 1.00 | 28.69 |
| ATOM | 1413 | N | GLY | 1061 | 102.386 | 24.997 | 147.772 | 1.00 | 26.61 |
| ATOM | 1414 | CA | GLY | 1061 | 102.726 | 25.789 | 146.607 | 1.00 | 23.35 |
| ATOM | 1415 | C | GLY | 1061 | 104.187 | 25.978 | 146.276 | 1.00 | 22.25 |
| ATOM | 1416 | O | GLY | 1061 | 104.512 | 26.659 | 145.297 | 1.00 | 22.12 |
| ATOM | 1417 | N | VAL | 1062 | 105.073 | 25.379 | 147.063 | 1.00 | 20.62 |
| ATOM | 1418 | CA | VAL | 1062 | 106.500 | 25.543 | 146.817 | 1.00 | 20.40 |
| ATOM | 1419 | CB | VAL | 1062 | 107.221 | 26.212 | 148.004 | 1.00 | 20.05 |
| ATOM | 1420 | CG1 | VAL | 1062 | 108.671 | 26.449 | 147.641 | 1.00 | 19.63 |
| ATOM | 1421 | CG2 | VAL | 1062 | 106.542 | 27.513 | 148.382 | 1.00 | 19.04 |
| ATOM | 1422 | C | VAL | 1062 | 107.181 | 24.225 | 146.593 | 1.00 | 20.43 |
| ATOM | 1423 | O | VAL | 1062 | 107.045 | 23.306 | 147.398 | 1.00 | 22.34 |
| ATOM | 1424 | N | VAL | 1063 | 107.946 | 24.133 | 145.520 | 1.00 | 19.65 |
| ATOM | 1425 | CA | VAL | 1063 | 108.633 | 22.895 | 145.251 | 1.00 | 20.40 |
| ATOM | 1426 | CB | VAL | 1063 | 107.990 | 22.162 | 144.062 | 1.00 | 20.01 |
| ATOM | 1427 | CG1 | VAL | 1063 | 106.540 | 21.905 | 144.340 | 1.00 | 19.91 |
| ATOM | 1428 | CG2 | VAL | 1063 | 108.143 | 22.981 | 142.797 | 1.00 | 19.44 |
| ATOM | 1429 | C | VAL | 1063 | 110.117 | 23.034 | 144.955 | 1.00 | 21.75 |
| ATOM | 1430 | O | VAL | 1063 | 110.634 | 24.123 | 144.701 | 1.00 | 20.92 |
| ATOM | 1431 | N | SER | 1064 | 110.792 | 21.895 | 145.024 | 1.00 | 22.70 |
| ATOM | 1432 | CA | SER | 1064 | 112.197 | 21.774 | 144.683 | 1.00 | 24.22 |
| ATOM | 1433 | CB | SER | 1064 | 112.945 | 20.909 | 145.687 | 1.00 | 24.50 |
| ATOM | 1434 | OG | SER | 1064 | 112.712 | 19.526 | 145.427 | 1.00 | 25.23 |
| ATOM | 1435 | C | SER | 1064 | 112.001 | 20.949 | 143.418 | 1.00 | 26.06 |
| ATOM | 1436 | O | SER | 1064 | 110.987 | 20.260 | 143.287 | 1.00 | 27.26 |
| ATOM | 1437 | N | ILE | 1065 | 112.936 | 21.019 | 142.481 | 1.00 | 26.78 |
| ATOM | 1438 | CA | ILE | 1065 | 112.830 | 20.241 | 141.244 | 1.00 | 26.41 |
| ATOM | 1439 | CB | ILE | 1065 | 112.670 | 21.159 | 140.002 | 1.00 | 26.08 |
| ATOM | 1440 | CG2 | ILE | 1065 | 112.846 | 20.365 | 138.726 | 1.00 | 25.26 |
| ATOM | 1441 | CG1 | ILE | 1065 | 111.283 | 21.810 | 140.014 | 1.00 | 26.82 |
| ATOM | 1442 | CD1 | ILE | 1065 | 111.098 | 22.875 | 138.958 | 1.00 | 25.95 |
| ATOM | 1443 | C | ILE | 1065 | 114.137 | 19.494 | 141.164 | 1.00 | 26.94 |
| ATOM | 1444 | O | ILE | 1065 | 115.187 | 20.095 | 140.953 | 1.00 | 27.36 |
| ATOM | 1445 | N | LYS | 1066 | 114.078 | 18.184 | 141.350 | 1.00 | 27.63 |
| ATOM | 1446 | CA | LYS | 1066 | 115.291 | 17.384 | 141.338 | 1.00 | 28.04 |

TABLE 6-continued

FGF2/FGFR1/Heparin Ternary Complex

| ATOM | 1447 | CB | LYS | 1066 | 115.335 | 16.508 | 142.587 | 1.00 | 29.73 |
| --- | --- | --- | --- | --- | --- | --- | --- | --- | --- |
| ATOM | 1448 | CG | LYS | 1066 | 116.610 | 15.692 | 142.743 | 1.00 | 32.05 |
| ATOM | 1449 | CD | LYS | 1066 | 116.683 | 15.055 | 144.129 | 1.00 | 33.02 |
| ATOM | 1450 | CE | LYS | 1066 | 117.803 | 14.032 | 144.218 | 1.00 | 34.21 |
| ATOM | 1451 | NZ | LYS | 1066 | 117.779 | 13.299 | 145.517 | 1.00 | 35.54 |
| ATOM | 1452 | C | LYS | 1066 | 115.442 | 16.506 | 140.127 | 1.00 | 27.29 |
| ATOM | 1453 | O | LYS | 1066 | 114.572 | 15.695 | 139.858 | 1.00 | 28.65 |
| ATOM | 1454 | N | GLY | 1067 | 116.543 | 16.670 | 139.394 | 1.00 | 26.76 |
| ATOM | 1455 | CA | GLY | 1067 | 116.786 | 15.826 | 138.237 | 1.00 | 26.32 |
| ATOM | 1456 | C | GLY | 1067 | 117.139 | 14.470 | 138.810 | 1.00 | 25.76 |
| ATOM | 1457 | O | GLY | 1067 | 118.123 | 14.341 | 139.526 | 1.00 | 25.98 |
| ATOM | 1458 | N | VAL | 1068 | 116.329 | 13.461 | 138.527 | 1.00 | 26.18 |
| ATOM | 1459 | CA | VAL | 1068 | 116.568 | 12.125 | 139.068 | 1.00 | 26.58 |
| ATOM | 1460 | CB | VAL | 1068 | 115.472 | 11.134 | 138.596 | 1.00 | 24.83 |
| ATOM | 1461 | CG1 | VAL | 1068 | 115.872 | 9.712 | 138.916 | 1.00 | 22.24 |
| ATOM | 1462 | CG2 | VAL | 1068 | 114.157 | 11.472 | 139.260 | 1.00 | 22.15 |
| ATOM | 1463 | C | VAL | 1068 | 117.938 | 11.549 | 138.723 | 1.00 | 28.21 |
| ATOM | 1464 | O | VAL | 1068 | 118.682 | 11.132 | 139.614 | 1.00 | 27.21 |
| ATOM | 1465 | N | SER | 1069 | 118.273 | 11.530 | 137.434 | 1.00 | 30.07 |
| ATOM | 1466 | CA | SER | 1069 | 119.557 | 10.969 | 137.008 | 1.00 | 32.16 |
| ATOM | 1467 | CB | SER | 1069 | 119.589 | 10.758 | 135.492 | 1.00 | 32.96 |
| ATOM | 1468 | OG | SER | 1069 | 119.730 | 11.997 | 134.813 | 1.00 | 35.81 |
| ATOM | 1469 | C | SER | 1069 | 120.761 | 11.815 | 137.429 | 1.00 | 32.02 |
| ATOM | 1470 | O | SER | 1069 | 121.749 | 11.284 | 137.930 | 1.00 | 31.07 |
| ATOM | 1471 | N | ALA | 1070 | 120.668 | 13.125 | 137.230 | 1.00 | 32.98 |
| ATOM | 1472 | CA | ALA | 1070 | 121.747 | 14.042 | 137.577 | 1.00 | 33.74 |
| ATOM | 1473 | CB | ALA | 1070 | 121.487 | 15.401 | 136.955 | 1.00 | 35.08 |
| ATOM | 1474 | C | ALA | 1070 | 121.892 | 14.196 | 139.076 | 1.00 | 34.28 |
| ATOM | 1475 | O | ALA | 1070 | 122.900 | 14.702 | 139.563 | 1.00 | 33.83 |
| ATOM | 1476 | N | AEN | 1071 | 120.884 | 13.749 | 139.811 | 1.00 | 35.69 |
| ATOM | 1477 | CA | ASN | 1071 | 120.904 | 13.876 | 141.256 | 1.00 | 36.90 |
| ATOM | 1478 | CB | ASN | 1071 | 121.828 | 12.840 | 141.884 | 1.00 | 38.21 |
| ATOM | 1479 | CG | ASN | 1071 | 121.792 | 12.885 | 143.398 | 1.00 | 40.11 |
| ATOM | 1480 | OD1 | ASN | 1071 | 120.725 | 12.788 | 144.008 | 1.00 | 39.64 |
| ATOM | 1481 | ND2 | ASN | 1071 | 122.960 | 13.037 | 144.016 | 1.00 | 42.09 |
| ATOM | 1482 | C | ASN | 1071 | 121.364 | 15.278 | 141.641 | 1.00 | 37.10 |
| ATOM | 1483 | O | ASN | 1071 | 122.301 | 15.452 | 142.418 | 1.00 | 36.45 |
| ATOM | 1484 | N | ARG | 1072 | 120.699 | 16.273 | 141.063 | 1.00 | 38.23 |
| ATOM | 1485 | CA | ARG | 1072 | 120.979 | 17.681 | 141.333 | 1.00 | 40.56 |
| ATOM | 1486 | CB | ARG | 1072 | 121.832 | 18.286 | 140.214 | 1.00 | 43.40 |
| ATOM | 1487 | CG | ARG | 1072 | 123.263 | 17.796 | 140.149 | 1.00 | 47.03 |
| ATOM | 1488 | CD | ARG | 1072 | 124.011 | 18.408 | 138.956 | 1.00 | 49.83 |
| ATOM | 1489 | NE | ARG | 1072 | 125.429 | 18.055 | 138.983 | 1.00 | 53.54 |
| ATOM | 1490 | CZ | ARG | 1072 | 126.318 | 18.595 | 139.814 | 1.00 | 55.37 |
| ATOM | 1491 | NH1 | ARG | 1072 | 125.947 | 19.528 | 140.684 | 1.00 | 56.73 |
| ATOM | 1492 | NH2 | ARG | 1072 | 127.575 | 18.177 | 139.802 | 1.00 | 56.12 |
| ATOM | 1493 | C | ARG | 1072 | 119.645 | 18.430 | 141.412 | 1.00 | 40.46 |
| ATOM | 1494 | O | ARG | 1072 | 118.611 | 17.911 | 140.997 | 1.00 | 40.54 |
| ATOM | 1495 | N | TYR | 1073 | 119.672 | 19.653 | 141.926 | 1.00 | 40.46 |
| ATOM | 1496 | CA | TYR | 1073 | 118.462 | 20.456 | 142.055 | 1.00 | 40.39 |
| ATOM | 1497 | CB | TYR | 1073 | 118.286 | 20.915 | 143.499 | 1.00 | 42.52 |
| ATOM | 1498 | CG | TYR | 1073 | 118.051 | 19.769 | 144.437 | 1.00 | 46.38 |
| ATOM | 1499 | CD1 | TYR | 1073 | 119.089 | 18.919 | 144.805 | 1.00 | 47.67 |
| ATOM | 1500 | CE1 | TYR | 1073 | 118.856 | 17.824 | 145.630 | 1.00 | 49.63 |
| ATOM | 1501 | CD2 | TYR | 1073 | 116.773 | 19.495 | 144.918 | 1.00 | 47.71 |
| ATOM | 1502 | CE2 | TYR | 1073 | 116.530 | 18.402 | 145.738 | 1.00 | 48.59 |
| ATOM | 1503 | CZ | TYR | 1073 | 117.571 | 17.571 | 146.093 | 1.00 | 49.39 |
| ATOM | 1504 | OH | TYR | 1073 | 117.320 | 16.483 | 146.903 | 1.00 | 50.55 |
| ATOM | 1505 | C | TYR | 1073 | 118.474 | 21.673 | 141.161 | 1.00 | 39.53 |
| ATOM | 1506 | O | TYR | 1073 | 119.457 | 22.397 | 141.092 | 1.00 | 38.34 |
| ATOM | 1507 | N | LEU | 1074 | 117.368 | 21.910 | 140.477 | 1.00 | 39.81 |
| ATOM | 1508 | CA | LEU | 1074 | 117.285 | 23.072 | 139.607 | 1.00 | 40.61 |
| ATOM | 1509 | CB | LEU | 1074 | 116.026 | 23.010 | 138.750 | 1.00 | 41.25 |
| ATOM | 1510 | CG | LEU | 1074 | 115.821 | 24.151 | 137.755 | 1.00 | 41.64 |
| ATOM | 1511 | CD1 | LEU | 1074 | 116.927 | 24.113 | 136.718 | 1.00 | 42.78 |
| ATOM | 1512 | CD2 | LEU | 1074 | 114.461 | 24.018 | 137.074 | 1.00 | 42.53 |
| ATOM | 1513 | C | LEU | 1074 | 117.258 | 24.334 | 140.460 | 1.00 | 41.43 |
| ATOM | 1514 | O | LEU | 1074 | 116.326 | 24.548 | 141.243 | 1.00 | 41.50 |
| ATOM | 1515 | N | ALA | 1075 | 118.289 | 25.161 | 140.311 | 1.00 | 42.19 |
| ATOM | 1516 | CA | ALA | 1075 | 118.391 | 26.412 | 141.058 | 1.00 | 42.44 |
| ATOM | 1517 | CB | ALA | 1075 | 119.536 | 26.329 | 142.046 | 1.00 | 41.88 |
| ATOM | 1518 | C | ALA | 1075 | 118.608 | 27.590 | 140.106 | 1.00 | 43.17 |
| ATOM | 1519 | O | ALA | 1075 | 119.308 | 27.459 | 139.101 | 1.00 | 42.34 |
| ATOM | 1520 | N | MET | 1076 | 117.993 | 28.732 | 140.416 | 1.00 | 44.63 |
| ATOM | 1521 | CA | MET | 1076 | 118.134 | 29.932 | 139.595 | 1.00 | 46.04 |
| ATOM | 1522 | CB | MET | 1076 | 116.769 | 30.543 | 139.269 | 1.00 | 47.68 |
| ATOM | 1523 | CG | MET | 1076 | 116.832 | 31.817 | 138.414 | 1.00 | 49.54 |

TABLE 6-continued

| | | | FGF2/FGFR1/Heparin Ternary Complex | | | | | |
|---|---|---|---|---|---|---|---|---|
| ATOM | 1524 | SD | MET | 1076 | 115.200 | 32.466 | 137.860 | 1.00 | 50.79 |
| ATOM | 1525 | CE | MET | 1076 | 114.834 | 33.601 | 139.156 | 1.00 | 48.61 |
| ATOM | 1526 | C | MET | 1076 | 118.972 | 30.942 | 140.354 | 1.00 | 47.36 |
| ATOM | 1527 | O | MET | 1076 | 118.577 | 31.417 | 141.422 | 1.00 | 47.71 |
| ATOM | 1528 | N | LYS | 1077 | 120.138 | 31.257 | 139.799 | 1.00 | 48.65 |
| ATOM | 1529 | CA | LYS | 1077 | 121.054 | 32.204 | 140.411 | 1.00 | 50.09 |
| ATOM | 1530 | CB | LYS | 1077 | 122.428 | 32.063 | 139.774 | 1.00 | 49.88 |
| ATOM | 1531 | CG | LYS | 1077 | 122.892 | 30.620 | 139.686 | 1.00 | 49.37 |
| ATOM | 1532 | CD | LYS | 1077 | 122.854 | 29.934 | 141.044 | 1.00 | 49.96 |
| ATOM | 1533 | CE | LYS | 1077 | 123.705 | 30.668 | 142.081 | 1.00 | 49.24 |
| ATOM | 1534 | NZ | LYS | 1077 | 123.839 | 29.874 | 143.343 | 1.00 | 49.00 |
| ATOM | 1535 | C | LYS | 1077 | 120.536 | 33.627 | 140.256 | 1.00 | 51.61 |
| ATOM | 1536 | O | LYS | 1077 | 119.554 | 33.863 | 139.548 | 1.00 | 51.81 |
| ATOM | 1537 | N | GLU | 1078 | 121.202 | 34.570 | 140.918 | 1.00 | 53.33 |
| ATOM | 1538 | CA | GLU | 1078 | 120.805 | 35.980 | 140.892 | 1.00 | 54.67 |
| ATOM | 1539 | CB | GLU | 1078 | 121.730 | 36.793 | 141.789 | 1.00 | 56.39 |
| ATOM | 1540 | CG | GLU | 1078 | 123.154 | 36.855 | 141.286 | 1.00 | 60.41 |
| ATOM | 1541 | CD | GLU | 1078 | 124.030 | 37.707 | 142.175 | 1.00 | 63.75 |
| ATOM | 1542 | OE1 | GLU | 1078 | 123.617 | 38.851 | 142.485 | 1.00 | 64.51 |
| ATOM | 1543 | OE2 | GLU | 1078 | 125.127 | 37.234 | 142.559 | 1.00 | 65.35 |
| ATOM | 1544 | C | GLU | 1078 | 120.756 | 36.641 | 139.512 | 1.00 | 54.55 |
| ATOM | 1545 | O | GLU | 1078 | 119.907 | 37.499 | 139.270 | 1.00 | 54.10 |
| ATOM | 1546 | N | ASP | 1079 | 121.663 | 36.269 | 138.612 | 1.00 | 53.83 |
| ATOM | 1547 | CA | ASP | 1079 | 121.658 | 36.875 | 137.279 | 1.00 | 53.00 |
| ATOM | 1548 | CB | ASP | 1079 | 122.962 | 36.564 | 136.539 | 1.00 | 52.34 |
| ATOM | 1549 | CG | ASP | 1079 | 123.172 | 35.087 | 136.347 | 1.00 | 52.66 |
| ATOM | 1550 | OD1 | ASP | 1079 | 124.074 | 34.708 | 135.574 | 1.00 | 52.13 |
| ATOM | 1551 | OD2 | ASP | 1079 | 122.434 | 34.304 | 136.981 | 1.00 | 52.70 |
| ATOM | 1552 | C | ASP | 1079 | 120.472 | 36.359 | 136.460 | 1.00 | 52.05 |
| ATOM | 1553 | O | ASP | 1079 | 120.171 | 36.877 | 135.377 | 1.00 | 51.50 |
| ATOM | 1554 | N | GLY | 1080 | 119.807 | 35.331 | 136.984 | 1.00 | 50.75 |
| ATOM | 1555 | CA | GLY | 1080 | 118.668 | 34.752 | 136.295 | 1.00 | 48.77 |
| ATOM | 1556 | C | GLY | 1080 | 119.015 | 33.559 | 135.426 | 1.00 | 47.34 |
| ATOM | 1557 | O | GLY | 1080 | 118.249 | 33.205 | 134.532 | 1.00 | 46.65 |
| ATOM | 1558 | N | ARG | 1081 | 120.165 | 32.939 | 135.679 | 1.00 | 46.16 |
| ATOM | 1559 | CA | ARG | 1081 | 120.579 | 31.780 | 134.903 | 1.00 | 45.71 |
| ATOM | 1560 | CB | ARG | 1081 | 122.084 | 31.834 | 134.626 | 1.00 | 47.53 |
| ATOM | 1561 | CG | ARG | 1081 | 122.955 | 31.772 | 135.864 | 1.00 | 49.72 |
| ATOM | 1562 | CD | ARG | 1081 | 124.439 | 31.920 | 135.531 | 1.00 | 50.75 |
| ATOM | 1563 | NE | ARG | 1081 | 125.286 | 31.647 | 136.692 | 1.00 | 52.82 |
| ATOM | 1564 | CZ | ARG | 1081 | 125.373 | 32.422 | 137.772 | 1.00 | 53.14 |
| ATOM | 1565 | NH1 | ARG | 1081 | 124.671 | 33.542 | 137.858 | 1.00 | 52.95 |
| ATOM | 1566 | NH2 | ARG | 1081 | 126.154 | 32.064 | 138.783 | 1.00 | 54.10 |
| ATOM | 1567 | C | ARG | 1081 | 120.229 | 30.518 | 135.671 | 1.00 | 43.90 |
| ATOM | 1568 | O | ARG | 1081 | 120.166 | 30.535 | 136.891 | 1.00 | 44.30 |
| ATOM | 1569 | N | LEU | 1082 | 119.988 | 29.430 | 134.953 | 1.00 | 42.56 |
| ATOM | 1570 | CA | LEU | 1082 | 119.632 | 28.168 | 135.586 | 1.00 | 41.88 |
| ATOM | 1571 | CB | LEU | 1082 | 118.513 | 27.464 | 134.804 | 1.00 | 39.65 |
| ATOM | 1572 | CG | LEU | 1082 | 117.245 | 28.286 | 134.563 | 1.00 | 38.35 |
| ATOM | 1573 | CD1 | LEU | 1082 | 116.291 | 27.517 | 133.699 | 1.00 | 36.79 |
| ATOM | 1574 | CD2 | LEU | 1082 | 116.597 | 28.642 | 135.889 | 1.00 | 38.70 |
| ATOM | 1575 | C | LEU | 1082 | 120.830 | 27.246 | 135.682 | 1.00 | 41.96 |
| ATOM | 1576 | O | LEU | 1082 | 121.814 | 27.411 | 134.972 | 1.00 | 41.58 |
| ATOM | 1577 | N | LEU | 1083 | 120.725 | 26.275 | 136.576 | 1.00 | 43.51 |
| ATOM | 1578 | CA | LEU | 1083 | 121.767 | 25.277 | 136.804 | 1.00 | 45.29 |
| ATOM | 1579 | CB | LEU | 1083 | 123.088 | 25.941 | 137.202 | 1.00 | 47.13 |
| ATOM | 1580 | CG | LEU | 1083 | 123.080 | 26.795 | 138.471 | 1.00 | 49.20 |
| ATOM | 1581 | CD1 | LEU | 1083 | 123.140 | 25.887 | 139.699 | 1.00 | 50.34 |
| ATOM | 1582 | CD2 | LEU | 1083 | 124.273 | 27.751 | 138.452 | 1.00 | 49.30 |
| ATOM | 1583 | C | LEU | 1083 | 121.282 | 24.366 | 137.917 | 1.00 | 45.30 |
| ATOM | 1584 | O | LEU | 1083 | 120.358 | 24.719 | 138.655 | 1.00 | 45.86 |
| ATOM | 1585 | N | ALA | 1084 | 121.904 | 23.204 | 138.057 | 1.00 | 45.08 |
| ATOM | 1586 | CA | ALA | 1084 | 121.466 | 22.273 | 139.082 | 1.00 | 46.14 |
| ATOM | 1587 | CB | ALA | 1084 | 121.001 | 20.983 | 138.434 | 1.00 | 45.94 |
| ATOM | 1588 | C | ALA | 1084 | 122.528 | 21.980 | 140.128 | 1.00 | 46.93 |
| ATOM | 1589 | O | ALA | 1084 | 123.569 | 21.401 | 139.822 | 1.00 | 47.13 |
| ATOM | 1590 | N | SER | 1085 | 122.246 | 22.383 | 141.366 | 1.00 | 48.12 |
| ATOM | 1591 | CA | SER | 1085 | 123.152 | 22.174 | 142.489 | 1.00 | 48.98 |
| ATOM | 1592 | CB | SER | 1085 | 122.752 | 23.072 | 143.655 | 1.00 | 48.95 |
| ATOM | 1593 | OG | SER | 1085 | 123.625 | 22.857 | 144.751 | 1.00 | 52.03 |
| ATOM | 1594 | C | SER | 1085 | 123.143 | 20.717 | 142.954 | 1.00 | 49.51 |
| ATOM | 1595 | O | SER | 1085 | 122.150 | 20.008 | 142.780 | 1.00 | 50.20 |
| ATOM | 1596 | N | LYS | 1086 | 124.246 | 20.270 | 143.550 | 1.00 | 49.42 |
| ATOM | 1597 | CA | LYS | 1086 | 124.327 | 18.897 | 144.022 | 1.00 | 49.13 |
| ATOM | 1598 | CB | LYS | 1086 | 125.782 | 18.477 | 144.221 | 1.00 | 50.70 |
| ATOM | 1599 | CG | LYS | 1086 | 125.969 | 16.970 | 144.344 | 1.00 | 52.87 |
| ATOM | 1600 | CD | LYS | 1086 | 125.581 | 16.261 | 143.049 | 1.00 | 54.61 |

TABLE 6-continued

FGF2/FGFR1/Heparin Ternary Complex

| ATOM | 1601 | CE | LYS | 1086 | 125.953 | 14.777 | 143.073 | 1.00 | 55.42 |
|------|------|------|-----|------|---------|--------|---------|------|-------|
| ATOM | 1602 | NZ | LYS | 1086 | 125.678 | 14.111 | 141.762 | 1.00 | 55.89 |
| ATOM | 1603 | C | LYS | 1086 | 123.573 | 18.783 | 145.334 | 1.00 | 48.17 |
| ATOM | 1604 | O | LYS | 1086 | 123.048 | 17.721 | 145.671 | 1.00 | 48.36 |
| ATOM | 1605 | N | SER | 1087 | 123.528 | 19.883 | 146.076 | 1.00 | 46.90 |
| ATOM | 1606 | CA | SER | 1087 | 122.822 | 19.917 | 147.351 | 1.00 | 46.76 |
| ATOM | 1607 | CB | SER | 1087 | 123.809 | 20.024 | 148.523 | 1.00 | 47.35 |
| ATOM | 1608 | OG | SER | 1087 | 124.816 | 20.994 | 148.282 | 1.00 | 49.65 |
| ATOM | 1609 | C | SER | 1087 | 121.857 | 21.088 | 147.336 | 1.00 | 46.01 |
| ATOM | 1610 | O | SER | 1087 | 122.063 | 22.067 | 146.636 | 1.00 | 46.35 |
| ATOM | 1611 | N | VAL | 1088 | 120.793 | 20.989 | 148.108 | 1.00 | 46.03 |
| ATOM | 1612 | CA | VAL | 1088 | 119.792 | 22.038 | 148.112 | 1.00 | 46.71 |
| ATOM | 1613 | CB | VAL | 1088 | 118.524 | 21.563 | 148.840 | 1.00 | 46.96 |
| ATOM | 1614 | CG1 | VAL | 1088 | 117.427 | 22.596 | 148.709 | 1.00 | 47.19 |
| ATOM | 1615 | CG2 | VAL | 1088 | 118.069 | 20.241 | 148.253 | 1.00 | 48.07 |
| ATOM | 1616 | C | VAL | 1088 | 120.254 | 23.350 | 148.722 | 1.00 | 47.27 |
| ATOM | 1617 | O | VAL | 1088 | 121.065 | 23.370 | 149.651 | 1.00 | 48.46 |
| ATOM | 1618 | N | THR | 1089 | 119.730 | 24.444 | 148.178 | 1.00 | 47.34 |
| ATOM | 1619 | CA | THR | 1089 | 120.035 | 25.792 | 148.650 | 1.00 | 48.06 |
| ATOM | 1620 | CB | THR | 1089 | 121.104 | 26.468 | 147.793 | 1.00 | 49.46 |
| ATOM | 1621 | OG1 | THR | 1089 | 120.468 | 27.273 | 146.790 | 1.00 | 50.85 |
| ATOM | 1622 | CG2 | THR | 1089 | 121.990 | 25.417 | 147.122 | 1.00 | 49.79 |
| ATOM | 1623 | C | THR | 1089 | 118.750 | 26.596 | 148.517 | 1.00 | 47.80 |
| ATOM | 1624 | O | THR | 1089 | 117.827 | 26.181 | 147.820 | 1.00 | 47.73 |
| ATOM | 1625 | N | ASP | 1090 | 118.693 | 27.753 | 149.163 | 1.00 | 48.02 |
| ATOM | 1626 | CA | ASP | 1090 | 117.488 | 28.575 | 149.127 | 1.00 | 49.32 |
| ATOM | 1627 | CB | ASP | 1090 | 117.664 | 29.796 | 150.035 | 1.00 | 51.84 |
| ATOM | 1628 | CG | ASP | 1090 | 118.986 | 30.499 | 149.811 | 1.00 | 54.89 |
| ATOM | 1629 | OD1 | ASP | 1090 | 119.108 | 31.227 | 148.801 | 1.00 | 56.63 |
| ATOM | 1630 | OD2 | ASP | 1090 | 119.905 | 30.309 | 150.642 | 1.00 | 56.50 |
| ATOM | 1631 | C | ASP | 1090 | 117.083 | 29.021 | 147.731 | 1.00 | 48.91 |
| ATOM | 1632 | O | ASP | 1090 | 116.061 | 29.689 | 147.557 | 1.00 | 49.18 |
| ATOM | 1633 | N | GLU | 1091 | 117.878 | 28.646 | 146.736 | 1.00 | 48.37 |
| ATOM | 1634 | CA | GLU | 1091 | 117.596 | 29.023 | 145.350 | 1.00 | 47.47 |
| ATOM | 1635 | CB | GLU | 1091 | 118.876 | 29.494 | 144.635 | 1.00 | 49.80 |
| ATOM | 1636 | CG | GLU | 1091 | 119.301 | 30.935 | 144.886 | 1.00 | 50.93 |
| ATOM | 1637 | CD | GLU | 1091 | 120.616 | 31.274 | 144.195 | 1.00 | 51.80 |
| ATOM | 1638 | OE1 | GLU | 1091 | 121.626 | 30.605 | 144.502 | 1.00 | 52.38 |
| ATOM | 1639 | OE2 | GLU | 1091 | 120.640 | 32.202 | 143.351 | 1.00 | 51.13 |
| ATOM | 1640 | C | GLU | 1091 | 117.012 | 27.871 | 144.555 | 1.00 | 45.38 |
| ATOM | 1641 | O | GLU | 1091 | 116.833 | 27.983 | 143.348 | 1.00 | 45.82 |
| ATOM | 1642 | N | CYS | 1092 | 116.733 | 26.759 | 145.219 | 1.00 | 43.43 |
| ATOM | 1643 | CA | CYS | 1092 | 116.182 | 25.607 | 144.525 | 1.00 | 41.85 |
| ATOM | 1644 | CB | CYS | 1092 | 116.895 | 24.332 | 144.968 | 1.00 | 43.23 |
| ATOM | 1645 | SG | CYS | 1092 | 118.677 | 24.412 | 144.713 | 1.00 | 49.74 |
| ATOM | 1646 | C | CYS | 1092 | 114.698 | 25.479 | 144.777 | 1.00 | 39.04 |
| ATOM | 1647 | O | CYS | 1092 | 114.115 | 24.426 | 144.546 | 1.00 | 39.56 |
| ATOM | 1648 | N | PHE | 1093 | 114.085 | 26.559 | 145.235 | 1.00 | 36.22 |
| ATOM | 1649 | CA | PHE | 1093 | 112.663 | 26.534 | 145.532 | 1.00 | 35.29 |
| ATOM | 1650 | CB | PHE | 1093 | 112.437 | 26.872 | 147.012 | 1.00 | 35.35 |
| ATOM | 1651 | CG | PHE | 1093 | 113.179 | 25.953 | 147.953 | 1.00 | 36.46 |
| ATOM | 1652 | CD1 | PHE | 1093 | 113.031 | 24.570 | 147.858 | 1.00 | 36.94 |
| ATOM | 1653 | CD2 | PHE | 1093 | 114.069 | 26.460 | 148.894 | 1.00 | 36.72 |
| ATOM | 1654 | CE1 | PHE | 1093 | 113.763 | 23.708 | 148.680 | 1.00 | 36.12 |
| ATOM | 1655 | CE2 | PHE | 1093 | 114.803 | 25.602 | 149.719 | 1.00 | 36.60 |
| ATOM | 1656 | CZ | PHE | 1093 | 114.647 | 24.227 | 149.607 | 1.00 | 36.17 |
| ATOM | 1657 | C | PHE | 1093 | 111.873 | 27.464 | 144.632 | 1.00 | 34.61 |
| ATOM | 1658 | O | PHE | 1093 | 112.259 | 28.610 | 144.400 | 1.00 | 35.53 |
| ATOM | 1659 | N | PHE | 1094 | 110.757 | 26.958 | 144.120 | 1.00 | 32.86 |
| ATOM | 1660 | CA | PHE | 1094 | 109.937 | 27.740 | 143.218 | 1.00 | 31.49 |
| ATOM | 1661 | CB | PHE | 1094 | 110.168 | 27.247 | 141.793 | 1.00 | 33.20 |
| ATOM | 1662 | CG | PHE | 1094 | 111.613 | 27.080 | 141.432 | 1.00 | 32.78 |
| ATOM | 1663 | CD1 | PHE | 1094 | 112.212 | 27.930 | 140.520 | 1.00 | 33.09 |
| ATOM | 1664 | CD2 | PHE | 1094 | 112.365 | 26.057 | 141.987 | 1.00 | 33.53 |
| ATOM | 1665 | CE1 | PHE | 1094 | 113.538 | 27.761 | 140.162 | 1.00 | 34.51 |
| ATOM | 1666 | CE2 | PHE | 1094 | 113.695 | 25.875 | 141.640 | 1.00 | 34.65 |
| ATOM | 1667 | CZ | PHE | 1094 | 114.286 | 26.726 | 140.724 | 1.00 | 34.52 |
| ATOM | 1668 | C | PHE | 1094 | 108.456 | 27.645 | 143.551 | 1.00 | 30.07 |
| ATOM | 1669 | O | PHE | 1094 | 108.011 | 26.683 | 144.165 | 1.00 | 30.00 |
| ATOM | 1670 | N | PHE | 1095 | 107.697 | 28.656 | 143.150 | 1.00 | 29.18 |
| ATOM | 1671 | CA | PHE | 1095 | 106.258 | 28.654 | 143.367 | 1.00 | 29.08 |
| ATOM | 1672 | CB | PHE | 1095 | 105.678 | 30.075 | 143.330 | 1.00 | 30.70 |
| ATOM | 1673 | CG | PHE | 1095 | 105.982 | 30.902 | 144.540 | 1.00 | 32.10 |
| ATOM | 1674 | CD1 | PHE | 1095 | 106.302 | 32.251 | 144.405 | 1.00 | 32.20 |
| ATOM | 1675 | CD2 | PHE | 1095 | 105.943 | 30.353 | 145.814 | 1.00 | 32.82 |
| ATOM | 1676 | CE1 | PHE | 1095 | 106.581 | 33.039 | 145.521 | 1.00 | 31.63 |
| ATOM | 1677 | CE2 | PHE | 1095 | 106.223 | 31.142 | 146.943 | 1.00 | 32.55 |

TABLE 6-continued

| FGF2/FGFR1/Heparin Ternary Complex | | | | | | | | |
|---|---|---|---|---|---|---|---|---|
| ATOM | 1678 | CZ | PHE | 1095 | 106.542 | 32.482 | 146.789 | 1.00 | 31.42 |
| ATOM | 1679 | C | PHE | 1095 | 105.674 | 27.896 | 142.190 | 1.00 | 28.62 |
| ATOM | 1680 | O | PHE | 1095 | 105.714 | 28.378 | 141.052 | 1.00 | 28.80 |
| ATOM | 1681 | N | GLU | 1096 | 105.147 | 26.707 | 142.442 | 1.00 | 27.22 |
| ATOM | 1682 | CA | GLU | 1096 | 104.543 | 25.963 | 141.361 | 1.00 | 25.98 |
| ATOM | 1683 | CB | GLU | 1096 | 104.605 | 24.475 | 141.632 | 1.00 | 25.73 |
| ATOM | 1684 | CG | GLU | 1096 | 104.008 | 23.669 | 140.521 | 1.00 | 23.45 |
| ATOM | 1685 | CD | GLU | 1096 | 103.987 | 22.226 | 140.855 | 1.00 | 22.74 |
| ATOM | 1686 | OE1 | GLU | 1096 | 103.359 | 21.875 | 141.877 | 1.00 | 23.44 |
| ATOM | 1687 | OE2 | GLU | 1096 | 104.607 | 21.449 | 140.108 | 1.00 | 22.66 |
| ATOM | 1688 | C | GLU | 1096 | 103.096 | 26.427 | 141.272 | 1.00 | 25.50 |
| ATOM | 1689 | O | GLU | 1096 | 102.356 | 26.399 | 142.254 | 1.00 | 25.24 |
| ATOM | 1690 | N | ARG | 1097 | 102.699 | 26.866 | 140.090 | 1.00 | 25.40 |
| ATOM | 1691 | CA | ARG | 1097 | 101.358 | 27.364 | 139.908 | 1.00 | 26.28 |
| ATOM | 1692 | CB | ARG | 1097 | 101.390 | 28.886 | 139.876 | 1.00 | 29.12 |
| ATOM | 1693 | CG | ARG | 1097 | 100.057 | 29.523 | 139.621 | 1.00 | 32.88 |
| ATOM | 1694 | CD | ARG | 1097 | 100.215 | 31.021 | 139.479 | 1.00 | 36.76 |
| ATOM | 1695 | NE | ARG | 1097 | 98.950 | 31.673 | 139.134 | 1.00 | 40.51 |
| ATOM | 1696 | CZ | ARG | 1097 | 97.952 | 31.895 | 139.989 | 1.00 | 40.70 |
| ATOM | 1697 | NH1 | ARG | 1097 | 98.069 | 31.519 | 141.262 | 1.00 | 40.49 |
| ATOM | 1698 | NH2 | ARG | 1097 | 96.835 | 32.482 | 139.565 | 1.00 | 38.85 |
| ATOM | 1699 | C | ARG | 1097 | 100.684 | 26.845 | 138.656 | 1.00 | 25.40 |
| ATOM | 1700 | O | ARG | 1097 | 101.218 | 26.930 | 137.557 | 1.00 | 25.12 |
| ATOM | 1701 | N | LEU | 1098 | 99.501 | 26.291 | 138.847 | 1.00 | 24.84 |
| ATOM | 1702 | CA | LEU | 1098 | 98.699 | 25.771 | 137.765 | 1.00 | 24.97 |
| ATOM | 1703 | CB | LEU | 1098 | 97.751 | 24.707 | 138.332 | 1.00 | 23.50 |
| ATOM | 1704 | CG | LEU | 1098 | 96.656 | 24.214 | 137.391 | 1.00 | 23.67 |
| ATOM | 1705 | CD1 | LEU | 1098 | 97.270 | 23.896 | 136.041 | 1.00 | 23.41 |
| ATOM | 1706 | CD2 | LEU | 1098 | 95.951 | 23.008 | 137.988 | 1.00 | 22.84 |
| ATOM | 1707 | C | LEU | 1098 | 97.939 | 26.994 | 137.227 | 1.00 | 25.39 |
| ATOM | 1708 | O | LEU | 1098 | 96.951 | 27.446 | 137.818 | 1.00 | 25.72 |
| ATOM | 1709 | N | GLU | 1099 | 98.419 | 27.546 | 136.118 | 1.00 | 25.13 |
| ATOM | 1710 | CA | GLU | 1099 | 97.805 | 28.732 | 135.530 | 1.00 | 24.71 |
| ATOM | 1711 | CB | GLU | 1099 | 98.692 | 29.296 | 134.429 | 1.00 | 22.34 |
| ATOM | 1712 | CG | GLU | 1099 | 100.048 | 29.735 | 134.924 | 1.00 | 21.66 |
| ATOM | 1713 | CD | GLU | 1099 | 99.965 | 30.849 | 135.934 | 1.00 | 22.92 |
| ATOM | 1714 | OE1 | GLU | 1099 | 101.012 | 31.195 | 136.520 | 1.00 | 22.60 |
| ATOM | 1715 | OE2 | GLU | 1099 | 98.852 | 31.387 | 136.140 | 1.00 | 25.85 |
| ATOM | 1716 | C | GLU | 1099 | 96.435 | 28.441 | 134.980 | 1.00 | 25.92 |
| ATOM | 1717 | O | GLU | 1099 | 96.065 | 27.287 | 134.814 | 1.00 | 27.25 |
| ATOM | 1718 | N | SER | 1100 | 95.681 | 29.495 | 134.689 | 1.00 | 27.31 |
| ATOM | 1719 | CA | SER | 1100 | 94.330 | 29.326 | 134.169 | 1.00 | 27.39 |
| ATOM | 1720 | CB | SER | 1100 | 93.592 | 30.670 | 134.125 | 1.00 | 28.14 |
| ATOM | 1721 | OG | SER | 1100 | 94.405 | 31.699 | 133.591 | 1.00 | 31.03 |
| ATOM | 1722 | C | SER | 1100 | 94.263 | 28.646 | 132.813 | 1.00 | 26.49 |
| ATOM | 1723 | O | SER | 1100 | 93.225 | 28.116 | 132.450 | 1.00 | 28.60 |
| ATOM | 1724 | N | ASN | 1101 | 95.365 | 28.643 | 132.075 | 1.00 | 25.73 |
| ATOM | 1725 | CA | ASN | 1101 | 95.415 | 28.013 | 130.760 | 1.00 | 24.86 |
| ATOM | 1726 | CB | ASN | 1101 | 96.489 | 28.684 | 129.938 | 1.00 | 23.07 |
| ATOM | 1727 | CG | ASN | 1101 | 97.768 | 28.790 | 130.700 | 1.00 | 22.42 |
| ATOM | 1728 | OD1 | ASN | 1101 | 97.889 | 28.230 | 131.790 | 1.00 | 20.74 |
| ATOM | 1729 | ND2 | ASN | 1101 | 98.733 | 29.503 | 130.152 | 1.00 | 24.80 |
| ATOM | 1730 | C | ASN | 1101 | 95.781 | 26.545 | 130.902 | 1.00 | 24.40 |
| ATOM | 1731 | O | ASN | 1101 | 95.906 | 25.841 | 129.915 | 1.00 | 25.58 |
| ATOM | 1732 | N | ASN | 1102 | 96.005 | 26.109 | 132.132 | 1.00 | 23.54 |
| ATOM | 1733 | CA | ASN | 1102 | 96.354 | 24.731 | 132.411 | 1.00 | 23.40 |
| ATOM | 1734 | CB | ASN | 1102 | 95.420 | 23.812 | 131.654 | 1.00 | 26.98 |
| ATOM | 1735 | CG | ASN | 1102 | 93.998 | 23.998 | 132.080 | 1.00 | 30.54 |
| ATOM | 1736 | OD1 | ASN | 1102 | 93.680 | 23.887 | 133.265 | 1.00 | 33.07 |
| ATOM | 1737 | ND2 | ASN | 1102 | 93.124 | 24.297 | 131.125 | 1.00 | 32.71 |
| ATOM | 1738 | C | ASN | 1102 | 97.803 | 24.331 | 132.180 | 1.00 | 22.35 |
| ATOM | 1739 | O | ASN | 1102 | 98.130 | 23.152 | 132.074 | 1.00 | 22.20 |
| ATOM | 1740 | N | TYR | 1103 | 98.676 | 25.321 | 132.109 | 1.00 | 21.25 |
| ATOM | 1741 | CA | TYR | 1103 | 100.098 | 25.064 | 131.960 | 1.00 | 21.42 |
| ATOM | 1742 | CB | TYR | 1103 | 100.707 | 25.993 | 130.904 | 1.00 | 21.03 |
| ATOM | 1743 | CG | TYR | 1103 | 100.594 | 25.458 | 129.486 | 1.00 | 21.58 |
| ATOM | 1744 | CD1 | TYR | 1103 | 101.568 | 24.605 | 128.961 | 1.00 | 22.58 |
| ATOM | 1745 | CE1 | TYR | 1103 | 101.460 | 24.083 | 127.672 | 1.00 | 22.23 |
| ATOM | 1746 | CD2 | TYR | 1103 | 99.501 | 25.775 | 128.683 | 1.00 | 20.55 |
| ATOM | 1747 | CE2 | TYR | 1103 | 99.383 | 25.257 | 127.390 | 1.00 | 22.04 |
| ATOM | 1748 | CZ | TYR | 1103 | 100.364 | 24.415 | 126.887 | 1.00 | 22.33 |
| ATOM | 1749 | OH | TYR | 1103 | 100.263 | 23.922 | 125.596 | 1.00 | 21.39 |
| ATOM | 1750 | C | TYR | 1103 | 100.627 | 25.424 | 133.326 | 1.00 | 21.79 |
| ATOM | 1751 | O | TYR | 1103 | 99.947 | 26.096 | 134.076 | 1.00 | 23.68 |
| ATOM | 1752 | N | ASN | 1104 | 101.819 | 24.971 | 133.669 | 1.00 | 22.54 |
| ATOM | 1753 | CA | ASN | 1104 | 102.387 | 25.299 | 134.970 | 1.00 | 23.11 |
| ATOM | 1754 | CB | ASN | 1104 | 102.982 | 24.061 | 135.641 | 1.00 | 21.78 |

TABLE 6-continued

FGF2/FGFR1/Heparin Ternary Complex

| ATOM | 1755 | CG | ASN | 1104 | 101.953 | 23.244 | 136.358 | 1.00 | 19.51 |
|---|---|---|---|---|---|---|---|---|---|
| ATOM | 1756 | OD1 | ASN | 1104 | 100.761 | 23.516 | 136.271 | 1.00 | 18.29 |
| ATOM | 1757 | ND2 | ASN | 1104 | 102.408 | 22.228 | 137.075 | 1.00 | 18.41 |
| ATOM | 1758 | C | ASN | 1104 | 103.484 | 26.325 | 134.815 | 1.00 | 24.80 |
| ATOM | 1759 | O | ASN | 1104 | 104.102 | 26.442 | 133.757 | 1.00 | 25.15 |
| ATOM | 1760 | N | THR | 1105 | 103.729 | 27.067 | 135.883 | 1.00 | 25.84 |
| ATOM | 1761 | CA | THR | 1105 | 104.776 | 28.060 | 135.863 | 1.00 | 26.64 |
| ATOM | 1762 | CB | THR | 1105 | 104.186 | 29.483 | 135.731 | 1.00 | 25.73 |
| ATOM | 1763 | OG1 | THR | 1105 | 103.226 | 29.720 | 136.765 | 1.00 | 27.01 |
| ATOM | 1764 | CG2 | THR | 1105 | 103.513 | 29.634 | 134.389 | 1.00 | 25.56 |
| ATOM | 1765 | C | THR | 1105 | 105.588 | 27.909 | 137.141 | 1.00 | 27.82 |
| ATOM | 1766 | O | THR | 1105 | 105.038 | 27.824 | 138.242 | 1.00 | 27.80 |
| ATOM | 1767 | N | TYR | 1106 | 106.902 | 27.849 | 136.981 | 1.00 | 28.80 |
| ATOM | 1768 | CA | TYR | 1106 | 107.792 | 27.697 | 138.118 | 1.00 | 30.47 |
| ATOM | 1769 | CB | TYR | 1106 | 108.760 | 26.553 | 137.832 | 1.00 | 29.61 |
| ATOM | 1770 | CG | TYR | 1106 | 108.023 | 25.253 | 137.768 | 1.00 | 29.12 |
| ATOM | 1771 | CD1 | TYR | 1106 | 107.828 | 24.493 | 138.914 | 1.00 | 30.78 |
| ATOM | 1772 | CE1 | TYR | 1106 | 107.020 | 23.362 | 138.903 | 1.00 | 30.90 |
| ATOM | 1773 | CD2 | TYR | 1106 | 107.397 | 24.846 | 136.597 | 1.00 | 29.58 |
| ATOM | 1774 | CE2 | TYR | 1106 | 106.583 | 23.720 | 136.572 | 1.00 | 30.55 |
| ATOM | 1775 | CZ | TYR | 1106 | 106.398 | 22.984 | 137.734 | 1.00 | 31.06 |
| ATOM | 1776 | OH | TYR | 1106 | 105.583 | 21.881 | 137.740 | 1.00 | 31.17 |
| ATOM | 1777 | C | TYR | 1106 | 108.525 | 29.000 | 138.393 | 1.00 | 32.52 |
| ATOM | 1778 | O | TYR | 1106 | 109.573 | 29.273 | 137.806 | 1.00 | 33.70 |
| ATOM | 1779 | N | ARG | 1107 | 107.954 | 29.805 | 139.286 | 1.00 | 33.59 |
| ATOM | 1780 | CA | ARG | 1107 | 108.519 | 31.098 | 139.637 | 1.00 | 33.71 |
| ATOM | 1781 | CB | ARG | 1107 | 107.395 | 32.094 | 139.922 | 1.00 | 34.16 |
| ATOM | 1782 | CG | ARG | 1107 | 107.888 | 33.456 | 140.363 | 1.00 | 35.95 |
| ATOM | 1783 | CD | ARG | 1107 | 106.743 | 34.421 | 140.627 | 1.00 | 37.06 |
| ATOM | 1784 | NE | ARG | 1107 | 105.738 | 33.845 | 141.517 | 1.00 | 39.01 |
| ATOM | 1785 | CZ | ARG | 1107 | 104.896 | 34.553 | 142.264 | 1.00 | 38.49 |
| ATOM | 1786 | NH1 | ARG | 1107 | 104.929 | 35.878 | 142.238 | 1.00 | 38.07 |
| ATOM | 1787 | NH2 | ARG | 1107 | 104.028 | 33.930 | 143.048 | 1.00 | 38.62 |
| ATOM | 1788 | C | ARG | 1107 | 109.439 | 30.998 | 140.835 | 1.00 | 34.38 |
| ATOM | 1789 | O | ARG | 1107 | 109.050 | 30.486 | 141.882 | 1.00 | 34.01 |
| ATOM | 1790 | N | SER | 1108 | 110.662 | 31.498 | 140.678 | 1.00 | 35.71 |
| ATOM | 1791 | CA | SER | 1108 | 111.642 | 31.450 | 141.759 | 1.00 | 38.01 |
| ATOM | 1792 | CB | SER | 1108 | 112.977 | 32.060 | 141.337 | 1.00 | 39.41 |
| ATOM | 1793 | OG | SER | 1108 | 113.881 | 32.099 | 142.438 | 1.00 | 40.69 |
| ATOM | 1794 | C | SER | 1108 | 111.161 | 32.180 | 142.991 | 1.00 | 38.82 |
| ATOM | 1795 | O | SER | 1108 | 110.839 | 33.369 | 142.932 | 1.00 | 38.18 |
| ATOM | 1796 | N | ARG | 1109 | 111.129 | 31.460 | 144.110 | 1.00 | 39.76 |
| ATOM | 1797 | CA | ARG | 1109 | 110.689 | 32.041 | 145.370 | 1.00 | 40.06 |
| ATOM | 1798 | CB | ARG | 1109 | 110.539 | 30.951 | 146.430 | 1.00 | 39.42 |
| ATOM | 1799 | CG | ARG | 1109 | 109.916 | 31.444 | 147.706 | 1.00 | 39.10 |
| ATOM | 1800 | CD | ARG | 1109 | 109.331 | 30.300 | 148.500 | 1.00 | 38.91 |
| ATOM | 1801 | NE | ARG | 1109 | 110.356 | 29.444 | 149.079 | 1.00 | 39.39 |
| ATOM | 1802 | CZ | ARG | 1109 | 110.552 | 29.301 | 150.385 | 1.00 | 40.16 |
| ATOM | 1803 | NH1 | ARG | 1109 | 109.788 | 29.966 | 151.251 | 1.00 | 40.03 |
| ATOM | 1804 | NH2 | ARG | 1109 | 111.505 | 28.486 | 150.824 | 1.00 | 40.40 |
| ATOM | 1805 | C | ARG | 1109 | 111.671 | 33.108 | 145.852 | 1.00 | 40.49 |
| ATOM | 1806 | O | ARG | 1109 | 111.284 | 34.035 | 146.570 | 1.00 | 39.63 |
| ATOM | 1807 | N | LYS | 1110 | 112.934 | 32.970 | 145.445 | 1.00 | 41.21 |
| ATOM | 1808 | CA | LYS | 1110 | 113.987 | 33.914 | 145.813 | 1.00 | 41.55 |
| ATOM | 1809 | CB | LYS | 1110 | 115.351 | 33.274 | 145.566 | 1.00 | 42.81 |
| ATOM | 1810 | CG | LYS | 1110 | 116.498 | 33.927 | 146.296 | 1.00 | 44.18 |
| ATOM | 1811 | CD | LYS | 1110 | 116.463 | 33.554 | 147.765 | 1.00 | 45.85 |
| ATOM | 1812 | CE | LYS | 1110 | 117.705 | 34.044 | 148.494 | 1.00 | 45.51 |
| ATOM | 1813 | NZ | LYS | 1110 | 117.731 | 33.606 | 149.913 | 1.00 | 44.54 |
| ATOM | 1814 | C | LYS | 1110 | 113.847 | 35.177 | 144.955 | 1.00 | 41.30 |
| ATOM | 1815 | O | LYS | 1110 | 113.522 | 36.250 | 145.450 | 1.00 | 41.19 |
| ATOM | 1816 | N | TYR | 1111 | 114.080 | 35.047 | 143.659 | 1.00 | 40.34 |
| ATOM | 1817 | CA | TYR | 1111 | 113.967 | 36.195 | 142.793 | 1.00 | 40.72 |
| ATOM | 1818 | CB | TYR | 1111 | 115.054 | 36.105 | 141.731 | 1.00 | 42.65 |
| ATOM | 1819 | CG | TYR | 1111 | 116.376 | 35.699 | 142.349 | 1.00 | 44.83 |
| ATOM | 1820 | CD1 | TYR | 1111 | 116.894 | 36.390 | 143.441 | 1.00 | 46.11 |
| ATOM | 1821 | CE1 | TYR | 1111 | 118.072 | 35.980 | 144.066 | 1.00 | 46.16 |
| ATOM | 1822 | CD2 | TYR | 1111 | 117.078 | 34.586 | 141.890 | 1.00 | 45.77 |
| ATOM | 1823 | CE2 | TYR | 1111 | 118.254 | 34.172 | 142.507 | 1.00 | 45.94 |
| ATOM | 1824 | CZ | TYR | 1111 | 118.741 | 34.872 | 143.595 | 1.00 | 46.79 |
| ATOM | 1825 | OH | TYR | 1111 | 119.891 | 34.454 | 144.223 | 1.00 | 48.18 |
| ATOM | 1826 | C | TYR | 1111 | 112.556 | 36.205 | 142.222 | 1.00 | 40.96 |
| ATOM | 1827 | O | TYR | 1111 | 112.338 | 36.113 | 141.009 | 1.00 | 40.93 |
| ATOM | 1828 | N | THR | 1112 | 111.611 | 36.345 | 143.150 | 1.00 | 40.69 |
| ATOM | 1829 | CA | THR | 1112 | 110.160 | 36.346 | 142.909 | 1.00 | 41.96 |
| ATOM | 1830 | CB | THR | 1112 | 109.387 | 37.022 | 144.083 | 1.00 | 42.40 |
| ATOM | 1831 | OC1 | THR | 1112 | 109.881 | 38.349 | 144.294 | 1.00 | 43.03 |

TABLE 6-continued

FGF2/FGFR1/Heparin Ternary Complex

| ATOM | 1832 | CG2 | THR | 1112 | 109.525 | 36.206 | 145.359 | 1.00 | 43.31 |
|---|---|---|---|---|---|---|---|---|---|
| ATOM | 1833 | C | THR | 1112 | 109.516 | 36.878 | 141.630 | 1.00 | 41.46 |
| ATOM | 1834 | O | THR | 1112 | 108.302 | 36.748 | 141.461 | 1.00 | 41.50 |
| ATOM | 1835 | N | SER | 1113 | 110.279 | 37.476 | 140.729 | 1.00 | 41.45 |
| ATOM | 1836 | CA | SER | 1113 | 109.652 | 37.967 | 139.510 | 1.00 | 41.57 |
| ATOM | 1837 | CB | SER | 1113 | 109.912 | 39.459 | 139.332 | 1.00 | 40.56 |
| ATOM | 1838 | OC | SER | 1113 | 109.240 | 40.186 | 140.339 | 1.00 | 40.01 |
| ATOM | 1839 | C | SER | 1113 | 110.107 | 37.216 | 138.278 | 1.00 | 42.04 |
| ATOM | 1840 | O | SER | 1113 | 109.700 | 37.546 | 137.170 | 1.00 | 42.45 |
| ATOM | 1841 | N | TRP | 1114 | 110.943 | 36.199 | 138.472 | 1.00 | 42.64 |
| ATOM | 1842 | CA | TRP | 1114 | 111.442 | 35.415 | 137.348 | 1.00 | 42.72 |
| ATOM | 1843 | CB | TRP | 1114 | 112.966 | 35.412 | 137.327 | 1.00 | 44.69 |
| ATOM | 1844 | CG | TRP | 1114 | 113.565 | 36.761 | 137.407 | 1.00 | 46.18 |
| ATOM | 1845 | CD2 | TRP | 1114 | 114.924 | 37.068 | 137.724 | 1.00 | 46.92 |
| ATOM | 1846 | CE2 | TRP | 1114 | 115.052 | 38.471 | 137.691 | 1.00 | 46.89 |
| ATOM | 1847 | CE3 | TRP | 1114 | 116.050 | 36.291 | 138.033 | 1.00 | 46.48 |
| ATOM | 1848 | CD1 | TRP | 1114 | 112.939 | 37.952 | 137.195 | 1.00 | 45.40 |
| ATOM | 1849 | NE1 | TRP | 1114 | 113.824 | 38.985 | 137.365 | 1.00 | 46.95 |
| ATOM | 1850 | CZ2 | TRP | 1114 | 116.256 | 39.117 | 137.959 | 1.00 | 46.46 |
| ATOM | 1851 | CZ3 | TRP | 1114 | 117.245 | 36.929 | 138.298 | 1.00 | 46.25 |
| ATOM | 1852 | CH2 | TRP | 1114 | 117.339 | 38.329 | 138.260 | 1.00 | 47.38 |
| ATOM | 1853 | C | TRP | 1114 | 110.958 | 33.976 | 137.355 | 1.00 | 41.32 |
| ATOM | 1854 | O | TRP | 1114 | 110.705 | 33.391 | 138.407 | 1.00 | 41.19 |
| ATOM | 1855 | N | TYR | 1115 | 110.848 | 33.402 | 136.166 | 1.00 | 40.12 |
| ATOM | 1856 | CA | TYR | 1115 | 110.392 | 32.033 | 136.042 | 1.00 | 39.14 |
| ATOM | 1857 | CB | TYR | 1115 | 109.154 | 31.942 | 135.155 | 1.00 | 40.95 |
| ATOM | 1858 | CG | TYR | 1115 | 107.946 | 32.713 | 135.625 | 1.00 | 42.57 |
| ATOM | 1859 | CD1 | TYR | 1115 | 107.879 | 34.097 | 135.489 | 1.00 | 43.25 |
| ATOM | 1860 | CE1 | TYR | 1115 | 106.737 | 34.801 | 135.860 | 1.00 | 43.70 |
| ATOM | 1861 | CD2 | TYR | 1115 | 106.844 | 32.052 | 136.152 | 1.00 | 42.47 |
| ATOM | 1862 | CE2 | TYR | 1115 | 105.705 | 32.741 | 136.525 | 1.00 | 43.45 |
| ATOM | 1863 | CZ | TYR | 1115 | 105.651 | 34.114 | 136.377 | 1.00 | 43.67 |
| ATOM | 1864 | OH | TYR | 1115 | 104.507 | 34.794 | 136.741 | 1.00 | 43.60 |
| ATOM | 1865 | C | TYR | 1115 | 111.439 | 31.139 | 135.427 | 1.00 | 37.49 |
| ATOM | 1866 | O | TYR | 1115 | 112.450 | 31.602 | 134.892 | 1.00 | 37.76 |
| ATOM | 1867 | N | VAL | 1116 | 111.183 | 29.841 | 135.514 | 1.00 | 35.40 |
| ATOM | 1868 | CA | VAL | 1116 | 112.061 | 28.861 | 134.909 | 1.00 | 33.52 |
| ATOM | 1869 | CB | VAL | 1116 | 111.905 | 27.491 | 135.565 | 1.00 | 31.20 |
| ATOM | 1870 | CG1 | VAL | 1116 | 112.733 | 26.472 | 134.837 | 1.00 | 30.76 |
| ATOM | 1871 | CG2 | VAL | 1116 | 112.331 | 27.572 | 137.002 | 1.00 | 31.44 |
| ATOM | 1872 | C | VAL | 1116 | 111.499 | 28.831 | 133.497 | 1.00 | 33.90 |
| ATOM | 1873 | O | VAL | 1116 | 110.276 | 28.797 | 133.309 | 1.00 | 33.24 |
| ATOM | 1874 | N | ALA | 1117 | 112.373 | 28.877 | 132.500 | 1.00 | 33.87 |
| ATOM | 1875 | CA | ALA | 1117 | 111.889 | 28.885 | 131.135 | 1.00 | 33.71 |
| ATOM | 1876 | CB | ALA | 1117 | 111.443 | 30.292 | 130.763 | 1.00 | 34.03 |
| ATOM | 1877 | C | ALA | 1117 | 112.892 | 28.388 | 130.124 | 1.00 | 33.59 |
| ATOM | 1878 | O | ALA | 1117 | 114.093 | 28.397 | 130.359 | 1.00 | 32.47 |
| ATOM | 1879 | N | LEU | 1118 | 112.375 | 27.954 | 128.984 | 1.00 | 34.46 |
| ATOM | 1880 | CA | LEU | 1118 | 113.218 | 27.471 | 127.912 | 1.00 | 36.34 |
| ATOM | 1881 | CB | LEU | 1118 | 112.948 | 25.988 | 127.631 | 1.00 | 35.80 |
| ATOM | 1882 | CG | LEU | 1118 | 113.447 | 24.981 | 128.665 | 1.00 | 35.65 |
| ATOM | 1883 | CD1 | LEU | 1118 | 113.236 | 23.573 | 128.137 | 1.00 | 35.34 |
| ATOM | 1884 | CD2 | LEU | 1118 | 114.919 | 25.224 | 128.955 | 1.00 | 35.14 |
| ATOM | 1885 | C | LEU | 1118 | 112.944 | 28.279 | 126.657 | 1.00 | 37.87 |
| ATOM | 1886 | O | LEU | 1118 | 111.819 | 28.718 | 126.418 | 1.00 | 37.12 |
| ATOM | 1887 | N | LYS | 1119 | 113.989 | 28.483 | 125.868 | 1.00 | 40.57 |
| ATOM | 1888 | CA | LYS | 1119 | 113.874 | 29.216 | 124.621 | 1.00 | 43.52 |
| ATOM | 1889 | CB | LYS | 1119 | 115.246 | 29.756 | 124.202 | 1.00 | 46.49 |
| ATOM | 1890 | CG | LYS | 1119 | 115.889 | 30.729 | 125.193 | 1.00 | 49.41 |
| ATOM | 1891 | CD | LYS | 1119 | 117.235 | 31.252 | 124.667 | 1.00 | 51.97 |
| ATOM | 1892 | CE | LYS | 1119 | 118.247 | 30.117 | 124.423 | 1.00 | 54.07 |
| ATOM | 1893 | NZ | LYS | 1119 | 119.659 | 30.590 | 124.192 | 1.00 | 53.57 |
| ATOM | 1894 | C | LYS | 1119 | 113.370 | 28.238 | 123.571 | 1.00 | 43.83 |
| ATOM | 1895 | O | LYS | 1119 | 113.392 | 27.030 | 123.789 | 1.00 | 43.14 |
| ATOM | 1896 | N | ARG | 1120 | 112.922 | 28.752 | 122.433 | 1.00 | 45.00 |
| ATOM | 1897 | CA | ARG | 1120 | 112.433 | 27.891 | 121.354 | 1.00 | 46.36 |
| ATOM | 1898 | CB | ARG | 1120 | 111.674 | 28.734 | 120.323 | 1.00 | 47.22 |
| ATOM | 1899 | CG | ARG | 1120 | 112.434 | 29.992 | 119.949 | 1.00 | 47.48 |
| ATOM | 1900 | CD | ARG | 1120 | 111.698 | 30.906 | 118.988 | 1.00 | 47.23 |
| ATOM | 1901 | NE | ARG | 1120 | 112.375 | 32.199 | 118.949 | 1.00 | 47.79 |
| ATOM | 1902 | CZ | ARG | 1120 | 112.119 | 33.166 | 118.079 | 1.00 | 48.69 |
| ATOM | 1903 | NH1 | ARG | 1120 | 111.192 | 33.001 | 117.146 | 1.00 | 50.68 |
| ATOM | 1904 | NH2 | ARG | 1120 | 112.786 | 34.307 | 118.151 | 1.00 | 49.30 |
| ATOM | 1905 | C | ARG | 1120 | 113.626 | 27.224 | 120.678 | 1.00 | 46.59 |
| ATOM | 1906 | O | ARG | 1120 | 113.477 | 26.494 | 119.700 | 1.00 | 47.90 |
| ATOM | 1907 | N | THR | 1121 | 114.808 | 27.481 | 121.220 | 1.00 | 45.62 |
| ATOM | 1908 | CA | THR | 1121 | 116.043 | 26.946 | 120.685 | 1.00 | 45.18 |

TABLE 6-continued

FGF2/FGFR1/Heparin Ternary Complex

| ATOM | 1909 | CB | THR | 1121 | 117.096 | 28.037 | 120.658 | 1.00 | 47.00 |
|---|---|---|---|---|---|---|---|---|---|
| ATOM | 1910 | OG1 | THR | 1121 | 117.243 | 28.581 | 121.978 | 1.00 | 47.87 |
| ATOM | 1911 | OG2 | THR | 1121 | 116.675 | 29.144 | 119.709 | 1.00 | 48.44 |
| ATOM | 1912 | C | THR | 1121 | 116.588 | 25.785 | 121.505 | 1.00 | 44.47 |
| ATOM | 1913 | O | THR | 1121 | 117.621 | 25.216 | 121.167 | 1.00 | 43.67 |
| ATOM | 1914 | N | GLY | 1122 | 115.914 | 25.448 | 122.597 | 1.00 | 44.23 |
| ATOM | 1915 | CA | GLY | 1122 | 116.378 | 24.345 | 123.420 | 1.00 | 44.06 |
| ATOM | 1916 | C | GLY | 1122 | 117.257 | 24.718 | 124.603 | 1.00 | 44.26 |
| ATOM | 1917 | O | GLY | 1122 | 117.724 | 23.845 | 125.336 | 1.00 | 43.92 |
| ATOM | 1918 | N | GLN | 1123 | 117.496 | 26.009 | 124.792 | 1.00 | 44.58 |
| ATOM | 1919 | CA | GLN | 1123 | 118.314 | 26.462 | 125.903 | 1.00 | 45.08 |
| ATOM | 1920 | CB | GLN | 1123 | 119.447 | 27.352 | 125.391 | 1.00 | 46.52 |
| ATOM | 1921 | CG | GLN | 1123 | 120.503 | 26.603 | 124.608 | 1.00 | 48.98 |
| ATOM | 1922 | CD | GLN | 1123 | 121.063 | 25.421 | 125.393 | 1.00 | 52.53 |
| ATOM | 1923 | OE1 | GLN | 1123 | 121.477 | 25.561 | 126.547 | 1.00 | 55.31 |
| ATOM | 1924 | NE2 | GLN | 1123 | 121.075 | 24.250 | 124.768 | 1.00 | 53.43 |
| ATOM | 1925 | C | GLN | 1123 | 117.406 | 27.237 | 126.828 | 1.00 | 44.24 |
| ATOM | 1926 | O | GLN | 1123 | 116.265 | 27.733 | 126.393 | 1.00 | 43.79 |
| ATOM | 1927 | N | TYR | 1124 | 117.781 | 27.351 | 128.095 | 1.00 | 43.32 |
| ATOM | 1928 | CA | TYR | 1124 | 116.926 | 28.078 | 129.014 | 1.00 | 43.63 |
| ATOM | 1929 | CB | TYR | 1124 | 117.378 | 27.845 | 130.444 | 1.00 | 43.93 |
| ATOM | 1930 | CG | TYR | 1124 | 118.702 | 28.462 | 130.800 | 1.00 | 45.08 |
| ATOM | 1931 | CD1 | TYR | 1124 | 118.810 | 29.834 | 131.055 | 1.00 | 45.15 |
| ATOM | 1932 | CE1 | TYR | 1124 | 120.015 | 30.398 | 131.480 | 1.00 | 45.60 |
| ATOM | 1933 | CD2 | TYR | 1124 | 119.839 | 27.664 | 130.965 | 1.00 | 45.30 |
| ATOM | 1934 | CE2 | TYR | 1124 | 121.051 | 28.217 | 131.387 | 1.00 | 45.76 |
| ATOM | 1935 | CZ | TYR | 1124 | 121.129 | 29.584 | 131.647 | 1.00 | 45.95 |
| ATOM | 1936 | OH | TYR | 1124 | 122.313 | 30.125 | 132.091 | 1.00 | 46.50 |
| ATOM | 1937 | C | TYR | 1124 | 116.924 | 29.561 | 128.694 | 1.00 | 44.09 |
| ATOM | 1938 | O | TYR | 1124 | 117.623 | 30.007 | 127.791 | 1.00 | 43.93 |
| ATOM | 1939 | N | LYS | 1125 | 116.120 | 30.318 | 129.431 | 1.00 | 45.08 |
| ATOM | 1940 | CA | LYS | 1125 | 116.021 | 31.759 | 129.237 | 1.00 | 45.69 |
| ATOM | 1941 | CB | LYS | 1125 | 114.638 | 32.138 | 128.757 | 1.00 | 47.45 |
| ATOM | 1942 | CG | LYS | 1125 | 114.513 | 33.591 | 128.391 | 1.00 | 51.87 |
| ATOM | 1943 | CD | LYS | 1125 | 113.087 | 33.908 | 127.989 | 1.00 | 55.02 |
| ATOM | 1944 | CE | LYS | 1125 | 112.509 | 32.801 | 127.120 | 1.00 | 56.51 |
| ATOM | 1945 | NZ | LYS | 1125 | 113.491 | 32.290 | 126.111 | 1.00 | 57.79 |
| ATOM | 1946 | C | LYS | 1125 | 116.270 | 32.451 | 130.558 | 1.00 | 45.66 |
| ATOM | 1947 | O | LYS | 1125 | 115.652 | 32.105 | 131.568 | 1.00 | 46.25 |
| ATOM | 1948 | N | LEU | 1126 | 117.166 | 33.434 | 130.556 | 1.00 | 45.63 |
| ATOM | 1949 | CA | LEU | 1126 | 117.483 | 34.154 | 131.779 | 1.00 | 44.89 |
| ATOM | 1950 | CB | LEU | 1126 | 118.397 | 35.337 | 131.470 | 1.00 | 45.08 |
| ATOM | 1951 | CG | LEU | 1126 | 119.805 | 34.879 | 131.076 | 1.00 | 45.49 |
| ATOM | 1952 | CD1 | LEU | 1126 | 120.710 | 36.090 | 130.900 | 1.00 | 44.77 |
| ATOM | 1953 | CD2 | LEU | 1126 | 120.363 | 33.944 | 132.155 | 1.00 | 44.32 |
| ATOM | 1954 | C | LEU | 1126 | 116.223 | 34.622 | 132.492 | 1.00 | 44.51 |
| ATOM | 1955 | O | LEU | 1126 | 115.379 | 35.292 | 131.899 | 1.00 | 43.78 |
| ATOM | 1956 | N | GLY | 1127 | 116.092 | 34.246 | 133.762 | 1.00 | 44.39 |
| ATOM | 1957 | CA | GLY | 1127 | 114.928 | 34.643 | 134.529 | 1.00 | 44.48 |
| ATOM | 1958 | C | GLY | 1127 | 114.696 | 36.122 | 134.340 | 1.00 | 45.13 |
| ATOM | 1959 | O | GLY | 1127 | 113.572 | 36.572 | 134.144 | 1.00 | 45.43 |
| ATOM | 1960 | N | SER | 1128 | 115.783 | 36.878 | 134.394 | 1.00 | 46.06 |
| ATOM | 1961 | CA | SER | 1128 | 115.741 | 38.321 | 134.212 | 1.00 | 47.14 |
| ATOM | 1962 | CB | SER | 1128 | 117.170 | 38.865 | 134.190 | 1.00 | 48.37 |
| ATOM | 1963 | OG | SER | 1128 | 117.981 | 38.083 | 133.323 | 1.00 | 50.04 |
| ATOM | 1964 | C | SER | 1128 | 115.036 | 38.702 | 132.913 | 1.00 | 47.38 |
| ATOM | 1965 | O | SER | 1128 | 114.670 | 39.864 | 132.717 | 1.00 | 48.31 |
| ATOM | 1966 | N | LYS | 1129 | 114.862 | 37.723 | 132.027 | 1.00 | 47.45 |
| ATOM | 1967 | CA | LYS | 1129 | 114.213 | 37.934 | 130.729 | 1.00 | 46.81 |
| ATOM | 1968 | CB | LYS | 1129 | 115.068 | 37.362 | 129.584 | 1.00 | 47.07 |
| ATOM | 1969 | CG | LYS | 1129 | 115.843 | 38.379 | 128.751 | 1.00 | 47.89 |
| ATOM | 1970 | CD | LYS | 1129 | 115.787 | 38.062 | 127.237 | 1.00 | 48.45 |
| ATOM | 1971 | CE | LYS | 1129 | 116.364 | 36.686 | 126.873 | 1.00 | 48.23 |
| ATOM | 1972 | NZ | LYS | 1129 | 116.321 | 36.413 | 125.406 | 1.00 | 47.29 |
| ATOM | 1973 | C | LYS | 1129 | 112.842 | 37.271 | 130.660 | 1.00 | 46.09 |
| ATOM | 1974 | O | LYS | 1129 | 112.156 | 37.379 | 129.644 | 1.00 | 46.51 |
| ATOM | 1975 | N | THR | 1130 | 112.450 | 36.576 | 131.725 | 1.00 | 44.67 |
| ATOM | 1976 | CA | THR | 1130 | 111.161 | 35.881 | 131.754 | 1.00 | 43.50 |
| ATOM | 1977 | CB | THR | 1130 | 111.166 | 34.743 | 132.768 | 1.00 | 44.14 |
| ATOM | 1978 | OG1 | THR | 1130 | 111.272 | 35.291 | 134.087 | 1.00 | 45.49 |
| ATOM | 1979 | CG2 | THR | 1130 | 112.344 | 33.816 | 132.514 | 1.00 | 44.12 |
| ATOM | 1980 | C | THR | 1130 | 110.022 | 36.814 | 132.117 | 1.00 | 41.64 |
| ATOM | 1981 | O | THR | 1130 | 110.242 | 37.845 | 132.730 | 1.00 | 41.80 |
| ATOM | 1982 | N | GLY | 1131 | 108.804 | 36.444 | 131.740 | 1.00 | 40.73 |
| ATOM | 1983 | CA | GLY | 1131 | 107.657 | 37.285 | 132.032 | 1.00 | 40.05 |
| ATOM | 1984 | C | GLY | 1131 | 106.308 | 36.611 | 131.838 | 1.00 | 40.05 |
| ATOM | 1985 | O | GLY | 1131 | 106.158 | 35.741 | 130.979 | 1.00 | 39.10 |

TABLE 6-continued

FGF2/FGFR1/Heparin Ternary Complex

| ATOM | 1986 | N | PRO | 1132 | 105.293 | 37.029 | 132.611 | 1.00 | 40.35 |
|---|---|---|---|---|---|---|---|---|---|
| ATOM | 1987 | CD | PRO | 1132 | 105.371 | 38.307 | 133.333 | 1.00 | 40.07 |
| ATOM | 1988 | CA | PRO | 1132 | 103.908 | 36.533 | 132.618 | 1.00 | 40.62 |
| ATOM | 1989 | CB | PRO | 1132 | 103.148 | 37.621 | 133.373 | 1.00 | 39.90 |
| ATOM | 1990 | CG | PRO | 1132 | 103.978 | 38.841 | 133.150 | 1.00 | 40.34 |
| ATOM | 1991 | C | PRO | 1132 | 103.263 | 36.203 | 131.275 | 1.00 | 40.73 |
| ATOM | 1992 | O | PRO | 1132 | 102.640 | 35.151 | 131.129 | 1.00 | 41.94 |
| ATOM | 1993 | N | GLY | 1133 | 103.400 | 37.086 | 130.295 | 1.00 | 40.65 |
| ATOM | 1994 | CA | GLY | 1133 | 102.800 | 36.813 | 129.001 | 1.00 | 40.72 |
| ATOM | 1995 | C | GLY | 1133 | 103.587 | 35.877 | 128.091 | 1.00 | 40.28 |
| ATOM | 1996 | O | GLY | 1133 | 103.111 | 35.536 | 127.007 | 1.00 | 40.90 |
| ATOM | 1997 | N | GLN | 1134 | 104.771 | 35.443 | 128.523 | 1.00 | 39.26 |
| ATOM | 1998 | CA | GLN | 1134 | 105.617 | 34.568 | 127.708 | 1.00 | 38.73 |
| ATOM | 1999 | CB | GLN | 1134 | 107.073 | 34.670 | 128.167 | 1.00 | 39.96 |
| ATOM | 2000 | CG | GLN | 1134 | 107.705 | 36.024 | 127.933 | 1.00 | 41.43 |
| ATOM | 2001 | CD | GLN | 1134 | 109.218 | 35.975 | 128.005 | 1.00 | 42.47 |
| ATOM | 2002 | OE1 | GLN | 1134 | 109.871 | 35.256 | 127.237 | 1.00 | 43.63 |
| ATOM | 2003 | NE2 | GLN | 1134 | 109.787 | 36.743 | 128.924 | 1.00 | 42.75 |
| ATOM | 2004 | C | GLN | 1134 | 105.239 | 33.090 | 127.630 | 1.00 | 38.46 |
| ATOM | 2005 | O | GLN | 1134 | 104.686 | 32.513 | 128.576 | 1.00 | 38.92 |
| ATOM | 2006 | N | LYS | 1135 | 105.570 | 32.491 | 126.487 | 1.00 | 37.04 |
| ATOM | 2007 | CA | LYS | 1135 | 105.315 | 31.086 | 126.197 | 1.00 | 35.96 |
| ATOM | 2008 | CB | LYS | 1135 | 105.212 | 30.899 | 124.679 | 1.00 | 36.41 |
| ATOM | 2009 | CG | LYS | 1135 | 105.119 | 29.460 | 124.192 | 1.00 | 38.29 |
| ATOM | 2010 | CD | LYS | 1135 | 105.087 | 29.400 | 122.659 | 1.00 | 39.86 |
| ATOM | 2011 | CE | LYS | 1135 | 105.142 | 27.959 | 122.134 | 1.00 | 39.82 |
| ATOM | 2012 | NZ | LYS | 1135 | 105.459 | 27.863 | 120.671 | 1.00 | 39.42 |
| ATOM | 2013 | C | LYS | 1135 | 106.443 | 30.226 | 126.761 | 1.00 | 35.48 |
| ATOM | 2014 | O | LYS | 1135 | 106.263 | 29.034 | 126.997 | 1.00 | 35.40 |
| ATOM | 2015 | N | ALA | 1136 | 107.602 | 30.834 | 126.992 | 1.00 | 34.91 |
| ATOM | 2016 | CA | ALA | 1136 | 108.746 | 30.091 | 127.518 | 1.00 | 34.69 |
| ATOM | 2017 | CB | ALA | 1136 | 110.020 | 30.921 | 127.415 | 1.00 | 34.51 |
| ATOM | 2018 | C | ALA | 1136 | 108.558 | 29.619 | 128.953 | 1.00 | 33.97 |
| ATOM | 2019 | O | ALA | 1136 | 109.147 | 28.619 | 129.357 | 1.00 | 33.77 |
| ATOM | 2020 | N | ILE | 1137 | 107.733 | 30.334 | 129.710 | 1.00 | 32.70 |
| ATOM | 2021 | CA | ILE | 1137 | 107.476 | 30.010 | 131.113 | 1.00 | 32.21 |
| ATOM | 2022 | CB | ILE | 1137 | 106.915 | 31.254 | 131.857 | 1.00 | 31.38 |
| ATOM | 2023 | CG2 | ILE | 1137 | 107.975 | 32.348 | 131.928 | 1.00 | 30.84 |
| ATOM | 2024 | CG1 | ILE | 1137 | 105.645 | 31.745 | 131.146 | 1.00 | 30.94 |
| ATOM | 2025 | CD1 | ILE | 1137 | 104.820 | 32.734 | 131.927 | 1.00 | 29.44 |
| ATOM | 2026 | C | ILE | 1137 | 106.491 | 28.857 | 131.361 | 1.00 | 31.36 |
| ATOM | 2027 | O | ILE | 1137 | 106.534 | 28.202 | 132.403 | 1.00 | 32.48 |
| ATOM | 2028 | N | LEU | 1138 | 105.609 | 28.616 | 130.404 | 1.00 | 29.32 |
| ATOM | 2029 | CA | LEU | 1138 | 104.588 | 27.597 | 130.554 | 1.00 | 28.65 |
| ATOM | 2030 | CB | LEU | 1138 | 103.480 | 27.870 | 129.540 | 1.00 | 29.90 |
| ATOM | 2031 | CG | LEU | 1138 | 103.086 | 29.350 | 129.460 | 1.00 | 29.89 |
| ATOM | 2032 | CD1 | LEU | 1138 | 102.268 | 29.600 | 128.209 | 1.00 | 28.56 |
| ATOM | 2033 | CD2 | LEU | 1138 | 102.333 | 29.759 | 130.730 | 1.00 | 29.29 |
| ATOM | 2034 | C | LEU | 1138 | 105.090 | 26.172 | 130.414 | 1.00 | 28.55 |
| ATOM | 2035 | O | LEU | 1138 | 105.711 | 25.822 | 129.413 | 1.00 | 30.20 |
| ATOM | 2036 | N | PHE | 1139 | 104.822 | 25.344 | 131.420 | 1.00 | 27.45 |
| ATOM | 2037 | CA | PHE | 1139 | 105.247 | 23.948 | 131.368 | 1.00 | 26.67 |
| ATOM | 2038 | CB | PHE | 1139 | 106.353 | 23.650 | 132.377 | 1.00 | 27.49 |
| ATOM | 2039 | CG | PHE | 1139 | 107.670 | 24.280 | 132.044 | 1.00 | 27.20 |
| ATOM | 2040 | CD1 | PHE | 1139 | 107.893 | 25.630 | 132.299 | 1.00 | 25.89 |
| ATOM | 2041 | CD2 | PHE | 1139 | 108.690 | 23.518 | 131.483 | 1.00 | 27.89 |
| ATOM | 2042 | CE1 | PHE | 1139 | 109.101 | 26.212 | 132.011 | 1.00 | 26.60 |
| ATOM | 2043 | CE2 | PHE | 1139 | 109.913 | 24.088 | 131.184 | 1.00 | 28.43 |
| ATOM | 2044 | CZ | PHE | 1139 | 110.123 | 25.443 | 131.450 | 1.00 | 28.31 |
| ATOM | 2045 | C | PHE | 1139 | 104.094 | 23.003 | 131.624 | 1.00 | 25.43 |
| ATOM | 2046 | O | PHE | 1139 | 103.171 | 23.315 | 132.368 | 1.00 | 24.30 |
| ATOM | 2047 | N | LEU | 1140 | 104.166 | 21.832 | 131.009 | 1.00 | 24.47 |
| ATOM | 2048 | CA | LEU | 1140 | 103.123 | 20.840 | 131.156 | 1.00 | 23.19 |
| ATOM | 2049 | CB | LEU | 1140 | 102.554 | 20.497 | 129.783 | 1.00 | 22.43 |
| ATOM | 2050 | CG | LEU | 1140 | 101.042 | 20.378 | 129.638 | 1.00 | 22.70 |
| ATOM | 2051 | CD1 | LEU | 1140 | 100.347 | 21.532 | 130.323 | 1.00 | 22.43 |
| ATOM | 2052 | CD2 | LEU | 1140 | 100.702 | 20.368 | 128.155 | 1.00 | 23.99 |
| ATOM | 2053 | C | LEU | 1140 | 103.708 | 19.609 | 131.810 | 1.00 | 23.00 |
| ATOM | 2054 | O | LEU | 1140 | 104.572 | 18.943 | 131.252 | 1.00 | 24.30 |
| ATOM | 2055 | N | PRO | 1141 | 103.263 | 19.302 | 133.027 | 1.00 | 22.81 |
| ATOM | 2056 | CD | PRO | 1141 | 102.349 | 20.065 | 133.894 | 1.00 | 22.88 |
| ATOM | 2057 | CA | PRO | 1141 | 103.777 | 18.126 | 133.721 | 1.00 | 22.66 |
| ATOM | 2058 | CB | PRO | 1141 | 103.290 | 18.344 | 135.151 | 1.00 | 22.42 |
| ATOM | 2059 | CG | PRO | 1141 | 102.003 | 19.050 | 134.960 | 1.00 | 22.65 |
| ATOM | 2060 | C | PRO | 1141 | 103.237 | 16.840 | 133.103 | 1.00 | 23.04 |
| ATOM | 2061 | O | PRO | 1141 | 102.044 | 16.719 | 132.832 | 1.00 | 21.39 |
| ATOM | 2062 | N | MET | 1142 | 104.125 | 15.881 | 132.896 | 1.00 | 24.58 |

TABLE 6-continued

FGF2/FGFR1/Heparin Ternary Complex

| ATOM | 2063 | CA | MET | 1142 | 103.757 | 14.606 | 132.310 | 1.00 | 26.08 |
|---|---|---|---|---|---|---|---|---|---|
| ATOM | 2064 | CB | MET | 1142 | 104.282 | 14.537 | 130.889 | 1.00 | 24.74 |
| ATOM | 2065 | CG | MET | 1142 | 103.748 | 15.661 | 130.039 | 1.00 | 23.66 |
| ATOM | 2066 | SD | MET | 1142 | 104.337 | 15.545 | 128.375 | 1.00 | 25.16 |
| ATOM | 2067 | CE | MET | 1142 | 103.295 | 14.240 | 127.721 | 1.00 | 24.74 |
| ATOM | 2068 | C | MET | 1142 | 104.311 | 13.457 | 133.129 | 1.00 | 27.87 |
| ATOM | 2069 | O | MET | 1142 | 105.429 | 13.518 | 133.635 | 1.00 | 28.66 |
| ATOM | 2070 | N | SER | 1143 | 103.520 | 12.401 | 133.246 | 1.00 | 30.37 |
| ATOM | 2071 | CA | SER | 1143 | 103.892 | 11.233 | 134.025 | 1.00 | 31.39 |
| ATOM | 2072 | CB | SER | 1143 | 102.731 | 10.252 | 134.044 | 1.00 | 32.34 |
| ATOM | 2073 | OG | SER | 1143 | 102.373 | 9.911 | 132.717 | 1.00 | 32.97 |
| ATOM | 2074 | C | SER | 1143 | 105.138 | 10.521 | 133.522 | 1.00 | 32.02 |
| ATOM | 2075 | O | SER | 1143 | 105.568 | 10.697 | 132.379 | 1.00 | 30.87 |
| ATOM | 2076 | N | ALA | 1144 | 105.704 | 9.700 | 134.402 | 1.00 | 32.96 |
| ATOM | 2077 | CA | ALA | 1144 | 106.893 | 8.925 | 134.089 | 1.00 | 33.67 |
| ATOM | 2078 | CB | ALA | 1144 | 108.129 | 9.807 | 134.174 | 1.00 | 33.96 |
| ATOM | 2079 | C | ALA | 1144 | 107.007 | 7.748 | 135.057 | 1.00 | 34.12 |
| ATOM | 2080 | O | ALA | 1144 | 106.518 | 6.656 | 134.683 | 1.00 | 32.94 |
| ATOM | 2081 | CB | MET | 2149 | 101.053 | 53.171 | 93.062 | 1.00 | 57.58 |
| ATOM | 2082 | CG | MET | 2149 | 99.622 | 52.593 | 93.151 | 1.00 | 59.75 |
| ATOM | 2083 | SD | MET | 2149 | 98.295 | 53.481 | 92.279 | 1.00 | 60.90 |
| ATOM | 2084 | CE | MET | 2149 | 98.247 | 52.549 | 90.723 | 1.00 | 59.28 |
| ATOM | 2085 | C | MET | 2149 | 100.602 | 54.176 | 95.322 | 1.00 | 55.07 |
| ATOM | 2086 | O | MET | 2149 | 100.145 | 53.082 | 95.647 | 1.00 | 55.37 |
| ATOM | 2087 | N | MET | 2149 | 102.837 | 54.415 | 94.242 | 1.00 | 56.18 |
| ATOM | 2088 | CA | MET | 2149 | 101.360 | 54.347 | 94.000 | 1.00 | 56.33 |
| ATOM | 2089 | N | PRO | 2150 | 100.451 | 55.262 | 96.097 | 1.00 | 53.63 |
| ATOM | 2090 | CD | PRO | 2150 | 100.990 | 56.605 | 95.830 | 1.00 | 53.80 |
| ATOM | 2091 | CA | PRO | 2150 | 99.753 | 55.236 | 97.389 | 1.00 | 52.35 |
| ATOM | 2092 | CB | PRO | 2150 | 99.719 | 56.709 | 97.792 | 1.00 | 52.99 |
| ATOM | 2093 | CG | PRO | 2150 | 100.984 | 57.228 | 97.216 | 1.00 | 53.82 |
| ATOM | 2094 | C | PRO | 2150 | 98.359 | 54.618 | 97.391 | 1.00 | 50.70 |
| ATOM | 2095 | O | PRO | 2150 | 97.569 | 54.821 | 96.467 | 1.00 | 50.65 |
| ATOM | 2096 | N | VAL | 2151 | 98.073 | 53.870 | 98.453 | 1.00 | 49.03 |
| ATOM | 2097 | CA | VAL | 2151 | 96.785 | 53.209 | 98.643 | 1.00 | 47.15 |
| ATOM | 2098 | CB | VAL | 2151 | 96.776 | 51.794 | 98.067 | 1.00 | 47.39 |
| ATOM | 2099 | CG1 | VAL | 2151 | 95.359 | 51.234 | 98.121 | 1.00 | 47.16 |
| ATOM | 2100 | CG2 | VAL | 2151 | 97.330 | 51.800 | 96.653 | 1.00 | 48.15 |
| ATOM | 2101 | C | VAL | 2151 | 96.506 | 53.065 | 100.125 | 1.00 | 45.27 |
| ATOM | 2102 | O | VAL | 2151 | 97.367 | 52.602 | 100.875 | 1.00 | 44.84 |
| ATOM | 2103 | N | ALA | 2152 | 95.306 | 53.448 | 100.546 | 1.00 | 43.54 |
| ATOM | 2104 | CA | ALA | 2152 | 94.938 | 53.336 | 101.953 | 1.00 | 43.04 |
| ATOM | 2105 | CB | ALA | 2152 | 93.699 | 54.174 | 102.247 | 1.00 | 42.03 |
| ATOM | 2106 | C | ALA | 2152 | 94.684 | 51.872 | 102.315 | 1.00 | 42.13 |
| ATOM | 2107 | O | ALA | 2152 | 94.254 | 51.077 | 101.481 | 1.00 | 42.41 |
| ATOM | 2108 | N | PRO | 2153 | 94.960 | 51.490 | 103.564 | 1.00 | 41.04 |
| ATOM | 2109 | CD | PRO | 2153 | 95.360 | 52.284 | 104.734 | 1.00 | 41.11 |
| ATOM | 2110 | CA | PRO | 2153 | 94.726 | 50.099 | 103.936 | 1.00 | 40.71 |
| ATOM | 2111 | CB | PRO | 2153 | 95.118 | 50.066 | 105.408 | 1.00 | 40.77 |
| ATOM | 2112 | CG | PRO | 2153 | 94.820 | 51.449 | 105.862 | 1.00 | 41.38 |
| ATOM | 2113 | C | PRO | 2153 | 93.280 | 49.704 | 103.691 | 1.00 | 40.37 |
| ATOM | 2114 | O | PRO | 2153 | 92.366 | 50.478 | 103.947 | 1.00 | 40.64 |
| ATOM | 2115 | N | TYR | 2154 | 93.080 | 48.497 | 103.180 | 1.00 | 39.94 |
| ATOM | 2116 | CA | TYR | 2154 | 91.740 | 48.016 | 102.894 | 1.00 | 40.42 |
| ATOM | 2117 | CB | TYR | 2154 | 91.394 | 48.289 | 101.428 | 1.00 | 42.56 |
| ATOM | 2118 | CG | TYR | 2154 | 92.311 | 47.597 | 100.447 | 1.00 | 45.15 |
| ATOM | 2119 | CD1 | TYR | 2154 | 93.656 | 47.944 | 100.357 | 1.00 | 46.86 |
| ATOM | 2120 | CE1 | TYR | 2154 | 94.518 | 47.266 | 99.494 | 1.00 | 48.33 |
| ATOM | 2121 | CD2 | TYR | 2154 | 91.845 | 46.559 | 99.642 | 1.00 | 45.83 |
| ATOM | 2122 | CE2 | TYR | 2154 | 92.697 | 45.876 | 98.775 | 1.00 | 46.76 |
| ATOM | 2123 | CZ | TYR | 2154 | 94.030 | 46.230 | 98.711 | 1.00 | 47.85 |
| ATOM | 2124 | OH | TYR | 2154 | 94.884 | 45.524 | 97.898 | 1.00 | 49.09 |
| ATOM | 2125 | C | TYR | 2154 | 91.593 | 46.523 | 103.195 | 1.00 | 39.88 |
| ATOM | 2126 | O | TYR | 2154 | 92.564 | 45.766 | 103.153 | 1.00 | 38.80 |
| ATOM | 2127 | N | TRP | 2155 | 90.367 | 46.110 | 103.499 | 1.00 | 38.54 |
| ATOM | 2128 | CA | TRP | 2155 | 90.070 | 44.724 | 103.809 | 1.00 | 37.07 |
| ATOM | 2129 | CB | TRP | 2155 | 88.639 | 44.624 | 104.319 | 1.00 | 35.60 |
| ATOM | 2130 | CG | TRP | 2155 | 88.409 | 45.458 | 105.518 | 1.00 | 34.08 |
| ATOM | 2131 | CD2 | TRP | 2155 | 89.249 | 45.540 | 106.672 | 1.00 | 33.12 |
| ATOM | 2132 | CE2 | TRP | 2155 | 88.632 | 46.434 | 107.574 | 1.00 | 33.83 |
| ATOM | 2133 | CE3 | TRP | 2155 | 90.462 | 44.945 | 107.035 | 1.00 | 32.00 |
| ATOM | 2134 | CD1 | TRP | 2155 | 87.348 | 46.282 | 105.753 | 1.00 | 33.78 |
| ATOM | 2135 | NE1 | TRP | 2155 | 87.473 | 46.872 | 106.986 | 1.00 | 33.15 |
| ATOM | 2136 | CZ2 | TRP | 2155 | 89.191 | 46.745 | 108.823 | 1.00 | 33.85 |
| ATOM | 2137 | CZ3 | TRP | 2155 | 91.017 | 45.256 | 108.272 | 1.00 | 32.16 |
| ATOM | 2138 | CH2 | TRP | 2155 | 90.381 | 46.148 | 109.151 | 1.00 | 32.30 |
| ATOM | 2139 | C | TRP | 2155 | 90.219 | 43.879 | 102.557 | 1.00 | 37.57 |

TABLE 6-continued

FGF2/FGFR1/Heparin Ternary Complex

| ATOM | 2140 | O | TRP | 2155 | 89.580 | 44.161 | 101.544 | 1.00 | 37.17 |
|------|------|------|-----|------|--------|--------|---------|------|-------|
| ATOM | 2141 | N | THR | 2156 | 91.053 | 42.845 | 102.623 | 1.00 | 37.89 |
| ATOM | 2142 | CA | THR | 2156 | 91.263 | 41.963 | 101.479 | 1.00 | 38.70 |
| ATOM | 2143 | CB | THR | 2156 | 92.707 | 41.387 | 101.449 | 1.00 | 38.01 |
| ATOM | 2144 | OG1 | THR | 2156 | 92.982 | 40.682 | 102.665 | 1.00 | 36.69 |
| ATOM | 2145 | CG2 | THR | 2156 | 93.720 | 42.496 | 101.295 | 1.00 | 38.03 |
| ATOM | 2146 | C | THR | 2156 | 90.272 | 40.806 | 101.485 | 1.00 | 40.73 |
| ATOM | 2147 | O | THR | 2156 | 89.873 | 40.329 | 100.434 | 1.00 | 40.95 |
| ATOM | 2148 | N | SER | 2157 | 89.875 | 40.359 | 102.673 | 1.00 | 43.95 |
| ATOM | 2149 | CA | SER | 2157 | 88.920 | 39.254 | 102.812 | 1.00 | 47.06 |
| ATOM | 2150 | CB | SER | 2157 | 89.622 | 38.009 | 103.352 | 1.00 | 46.16 |
| ATOM | 2151 | OG | SER | 2157 | 90.642 | 37.586 | 102.471 | 1.00 | 46.00 |
| ATOM | 2152 | C | SER | 2157 | 87.819 | 39.678 | 103.774 | 1.00 | 49.00 |
| ATOM | 2153 | O | SER | 2157 | 87.689 | 39.143 | 104.869 | 1.00 | 49.66 |
| ATOM | 2154 | N | PRO | 2158 | 86.992 | 40.631 | 103.353 | 1.00 | 50.85 |
| ATOM | 2155 | CD | PRO | 2158 | 86.797 | 40.916 | 101.923 | 1.00 | 51.12 |
| ATOM | 2156 | CA | PRO | 2158 | 85.883 | 41.179 | 104.131 | 1.00 | 52.38 |
| ATOM | 2157 | CB | PRO | 2158 | 85.188 | 42.080 | 103.130 | 1.00 | 52.28 |
| ATOM | 2158 | CG | PRO | 2158 | 85.334 | 41.288 | 101.877 | 1.00 | 52.37 |
| ATOM | 2159 | C | PRO | 2158 | 84.922 | 40.154 | 104.692 | 1.00 | 53.86 |
| ATOM | 2160 | O | PRO | 2158 | 84.401 | 40.326 | 105.796 | 1.00 | 53.93 |
| ATOM | 2161 | N | GLU | 2159 | 84.682 | 39.095 | 103.921 | 1.00 | 55.27 |
| ATOM | 2162 | CA | GLU | 2159 | 83.731 | 38.062 | 104.322 | 1.00 | 56.66 |
| ATOM | 2163 | CB | GLU | 2159 | 83.480 | 37.080 | 103.172 | 1.00 | 58.65 |
| ATOM | 2164 | CG | GLU | 2159 | 82.250 | 36.186 | 103.394 | 1.00 | 62.88 |
| ATOM | 2165 | CD | GLU | 2159 | 81.955 | 35.237 | 102.220 | 1.00 | 65.39 |
| ATOM | 2166 | OE1 | GLU | 2159 | 81.698 | 35.732 | 101.095 | 1.00 | 65.81 |
| ATOM | 2167 | OE2 | GLU | 2159 | 81.977 | 33.995 | 102.422 | 1.00 | 66.67 |
| ATOM | 2168 | C | GLU | 2159 | 84.132 | 37.296 | 105.567 | 1.00 | 56.11 |
| ATOM | 2169 | O | GLU | 2159 | 83.274 | 36.950 | 106.384 | 1.00 | 56.78 |
| ATOM | 2170 | N | LYS | 2160 | 85.423 | 37.025 | 105.721 | 1.00 | 54.57 |
| ATOM | 2171 | CA | LYS | 2160 | 85.854 | 36.311 | 106.908 | 1.00 | 53.84 |
| ATOM | 2172 | CB | LYS | 2160 | 87.172 | 35.567 | 106.657 | 1.00 | 55.32 |
| ATOM | 2173 | CG | LYS | 2160 | 88.375 | 36.432 | 106.353 | 1.00 | 57.32 |
| ATOM | 2174 | CD | LYS | 2160 | 89.645 | 35.584 | 106.283 | 1.00 | 57.82 |
| ATOM | 2175 | CE | LYS | 2160 | 89.594 | 34.570 | 105.150 | 1.00 | 59.01 |
| ATOM | 2176 | NZ | LYS | 2160 | 90.778 | 33.672 | 105.173 | 1.00 | 62.14 |
| ATOM | 2177 | C | LYS | 2160 | 85.966 | 37.257 | 108.113 | 1.00 | 52.94 |
| ATOM | 2178 | O | LYS | 2160 | 86.763 | 37.041 | 109.029 | 1.00 | 52.74 |
| ATOM | 2179 | N | MET | 2161 | 85.144 | 38.304 | 108.104 | 1.00 | 51.47 |
| ATOM | 2180 | CA | MET | 2161 | 85.104 | 39.283 | 109.187 | 1.00 | 49.13 |
| ATOM | 2181 | CB | MET | 2161 | 85.700 | 40.610 | 108.736 | 1.00 | 49.15 |
| ATOM | 2182 | CG | MET | 2161 | 87.121 | 40.500 | 108.241 | 1.00 | 49.16 |
| ATOM | 2183 | SD | MET | 2161 | 87.834 | 42.120 | 107.942 | 1.00 | 49.46 |
| ATOM | 2184 | CE | MET | 2161 | 88.397 | 42.506 | 109.578 | 1.00 | 50.63 |
| ATOM | 2185 | C | MET | 2161 | 83.650 | 39.484 | 109.569 | 1.00 | 47.71 |
| ATOM | 2186 | O | MET | 2161 | 83.321 | 40.305 | 110.422 | 1.00 | 46.77 |
| ATOM | 2187 | N | GLU | 2162 | 82.789 | 38.707 | 108.928 | 1.00 | 46.49 |
| ATOM | 2188 | CA | GLU | 2162 | 81.362 | 38.763 | 109.154 | 1.00 | 46.30 |
| ATOM | 2189 | CB | GLU | 2162 | 80.680 | 37.832 | 108.164 | 1.00 | 48.00 |
| ATOM | 2190 | CG | GLU | 2162 | 79.214 | 38.119 | 107.992 | 1.00 | 51.96 |
| ATOM | 2191 | CD | GLU | 2162 | 78.966 | 39.454 | 107.321 | 1.00 | 54.10 |
| ATOM | 2192 | OE1 | GLU | 2162 | 79.457 | 40.479 | 107.846 | 1.00 | 55.94 |
| ATOM | 2193 | OE2 | GLU | 2162 | 78.284 | 39.475 | 106.268 | 1.00 | 56.14 |
| ATOM | 2194 | C | GLU | 2162 | 80.944 | 38.398 | 110.582 | 1.00 | 45.40 |
| ATOM | 2195 | O | GLU | 2162 | 80.121 | 39.081 | 111.190 | 1.00 | 45.60 |
| ATOM | 2196 | N | LYS | 2163 | 81.506 | 37.319 | 111.118 | 1.00 | 44.38 |
| ATOM | 2197 | CA | LYS | 2163 | 81.153 | 36.896 | 112.468 | 1.00 | 42.97 |
| ATOM | 2198 | CB | LYS | 2163 | 81.607 | 35.459 | 112.747 | 1.00 | 43.63 |
| ATOM | 2199 | CG | LYS | 2163 | 81.071 | 34.923 | 114.078 | 1.00 | 43.85 |
| ATOM | 2200 | CD | LYS | 2163 | 81.675 | 33.576 | 114.468 | 1.00 | 44.67 |
| ATOM | 2201 | CE | LYS | 2163 | 83.171 | 33.672 | 114.728 | 1.00 | 44.08 |
| ATOM | 2202 | NZ | LYS | 2163 | 83.546 | 34.722 | 115.741 | 1.00 | 45.08 |
| ATOM | 2203 | C | LYS | 2163 | 81.759 | 37.817 | 113.511 | 1.00 | 42.14 |
| ATOM | 2204 | O | LYS | 2163 | 82.889 | 37.607 | 113.956 | 1.00 | 41.65 |
| ATOM | 2205 | N | LYS | 2164 | 80.993 | 38.830 | 113.911 | 1.00 | 41.38 |
| ATOM | 2206 | CA | LYS | 2164 | 81.459 | 39.791 | 114.907 | 1.00 | 40.83 |
| ATOM | 2207 | CB | LYS | 2164 | 80.715 | 41.121 | 114.766 | 1.00 | 42.68 |
| ATOM | 2208 | CG | LYS | 2164 | 81.076 | 41.904 | 113.502 | 1.00 | 45.26 |
| ATOM | 2209 | CD | LYS | 2164 | 81.126 | 43.406 | 113.792 | 1.00 | 47.67 |
| ATOM | 2210 | CE | LYS | 2164 | 81.036 | 44.253 | 112.519 | 1.00 | 47.25 |
| ATOM | 2211 | NZ | LYS | 2164 | 79.682 | 44.252 | 111.886 | 1.00 | 48.33 |
| ATOM | 2212 | C | LYS | 2164 | 81.372 | 39.314 | 116.354 | 1.00 | 39.23 |
| ATOM | 2213 | O | LYS | 2164 | 82.065 | 39.846 | 117.222 | 1.00 | 39.43 |
| ATOM | 2214 | N | LEU | 2165 | 80.522 | 38.324 | 116.619 | 1.00 | 36.91 |
| ATOM | 2215 | CA | LEU | 2165 | 80.391 | 37.790 | 117.969 | 1.00 | 33.81 |
| ATOM | 2216 | CB | LEU | 2165 | 78.939 | 37.752 | 118.420 | 1.00 | 32.68 |

TABLE 6-continued

FGF2/FGFR1/Heparin Ternary Complex

| ATOM | 2217 | CG | LEU | 2165 | 78.777 | 36.988 | 119.740 | 1.00 | 30.79 |
|---|---|---|---|---|---|---|---|---|---|
| ATOM | 2218 | CD1 | LEU | 2165 | 79.495 | 37.744 | 120.834 | 1.00 | 29.86 |
| ATOM | 2219 | CD2 | LEU | 2165 | 77.310 | 36.829 | 120.098 | 1.00 | 29.83 |
| ATOM | 2220 | C | LEU | 2165 | 80.925 | 36.382 | 118.059 | 1.00 | 32.95 |
| ATOM | 2221 | O | LEU | 2165 | 80.433 | 35.485 | 117.381 | 1.00 | 31.95 |
| ATOM | 2222 | N | HIS | 2166 | 81.929 | 36.184 | 118.902 | 1.00 | 32.94 |
| ATOM | 2223 | CA | HIS | 2166 | 82.482 | 34.863 | 119.074 | 1.00 | 33.18 |
| ATOM | 2224 | CB | HIS | 2166 | 83.967 | 34.837 | 118.748 | 1.00 | 38.15 |
| ATOM | 2225 | CG | HIS | 2166 | 84.471 | 33.461 | 118.447 | 1.00 | 44.40 |
| ATOM | 2226 | CD2 | HIS | 2166 | 83.813 | 32.337 | 118.067 | 1.00 | 45.92 |
| ATOM | 2227 | ND1 | HIS | 2166 | 85.801 | 33.110 | 118.548 | 1.00 | 47.16 |
| ATOM | 2228 | CE1 | HIS | 2166 | 85.940 | 31.829 | 118.249 | 1.00 | 48.42 |
| ATOM | 2229 | NE2 | HIS | 2166 | 84.748 | 31.337 | 117.953 | 1.00 | 47.24 |
| ATOM | 2230 | C | HIS | 2166 | 82.249 | 34.367 | 120.487 | 1.00 | 30.67 |
| ATOM | 2231 | O | HIS | 2166 | 82.909 | 34.791 | 121.428 | 1.00 | 29.79 |
| ATOM | 2232 | N | ALA | 2167 | 81.281 | 33.469 | 120.625 | 1.00 | 29.14 |
| ATOM | 2233 | CA | ALA | 2167 | 80.946 | 32.898 | 121.914 | 1.00 | 27.52 |
| ATOM | 2234 | CB | ALA | 2167 | 79.423 | 32.832 | 122.095 | 1.00 | 26.36 |
| ATOM | 2235 | C | ALA | 2167 | 81.553 | 31.511 | 121.912 | 1.00 | 26.95 |
| ATOM | 2236 | O | ALA | 2167 | 81.368 | 30.742 | 120.965 | 1.00 | 26.26 |
| ATOM | 2237 | N | VAL | 2168 | 82.294 | 31.206 | 122.971 | 1.00 | 25.92 |
| ATOM | 2238 | CA | VAL | 2168 | 82.954 | 29.921 | 123.100 | 1.00 | 24.85 |
| ATOM | 2239 | CB | VAL | 2168 | 84.389 | 30.007 | 122.556 | 1.00 | 25.27 |
| ATOM | 2240 | CG1 | VAL | 2168 | 84.377 | 30.434 | 121.101 | 1.00 | 25.08 |
| ATOM | 2241 | CG2 | VAL | 2168 | 85.198 | 30.996 | 123.390 | 1.00 | 24.21 |
| ATOM | 2242 | C | VAL | 2168 | 83.058 | 29.492 | 124.559 | 1.00 | 24.37 |
| ATOM | 2243 | O | VAL | 2168 | 82.950 | 30.312 | 125.465 | 1.00 | 24.58 |
| ATOM | 2244 | N | PRO | 2169 | 83.241 | 28.186 | 124.805 | 1.00 | 23.79 |
| ATOM | 2245 | CD | PRO | 2169 | 83.022 | 27.050 | 123.895 | 1.00 | 22.95 |
| ATOM | 2246 | CA | PRO | 2169 | 83.371 | 27.732 | 126.193 | 1.00 | 23.24 |
| ATOM | 2247 | CB | PRO | 2169 | 83.049 | 26.241 | 126.097 | 1.00 | 21.71 |
| ATOM | 2248 | CG | PRO | 2169 | 83.503 | 25.889 | 124.721 | 1.00 | 22.73 |
| ATOM | 2249 | C | PRO | 2169 | 84.826 | 28.019 | 126.581 | 1.00 | 23.62 |
| ATOM | 2250 | O | PRO | 2169 | 85.687 | 28.147 | 125.709 | 1.00 | 22.49 |
| ATOM | 2251 | N | ALA | 2170 | 85.110 | 28.121 | 127.873 | 1.00 | 24.54 |
| ATOM | 2252 | CA | ALA | 2170 | 86.466 | 28.446 | 128.309 | 1.00 | 25.37 |
| ATOM | 2253 | CB | ALA | 2170 | 86.532 | 28.488 | 129.830 | 1.00 | 25.45 |
| ATOM | 2254 | C | ALA | 2170 | 87.523 | 27.504 | 127.781 | 1.00 | 25.81 |
| ATOM | 2255 | O | ALA | 2170 | 87.228 | 26.370 | 127.423 | 1.00 | 26.77 |
| ATOM | 2256 | N | ALA | 2171 | 88.756 | 28.001 | 127.749 | 1.00 | 26.06 |
| ATOM | 2257 | CA | ALA | 2171 | 89.933 | 27.266 | 127.302 | 1.00 | 26.68 |
| ATOM | 2258 | CB | ALA | 2171 | 89.954 | 25.877 | 127.885 | 1.00 | 26.19 |
| ATOM | 2259 | C | ALA | 2171 | 90.058 | 27.185 | 125.806 | 1.00 | 28.23 |
| ATOM | 2260 | O | ALA | 2171 | 91.168 | 27.056 | 125.275 | 1.00 | 29.90 |
| ATOM | 2261 | N | LYS | 2172 | 88.937 | 27.256 | 125.108 | 1.00 | 28.87 |
| ATOM | 2262 | CA | LYS | 2172 | 89.016 | 27.164 | 123.664 | 1.00 | 29.95 |
| ATOM | 2263 | CB | LYS | 2172 | 87.632 | 27.295 | 123.034 | 1.00 | 31.07 |
| ATOM | 2264 | CG | LYS | 2172 | 87.607 | 26.846 | 121.584 | 1.00 | 32.86 |
| ATOM | 2265 | CD | LYS | 2172 | 86.196 | 26.624 | 121.097 | 1.00 | 33.53 |
| ATOM | 2266 | CE | LYS | 2172 | 86.242 | 26.136 | 119.681 | 1.00 | 34.62 |
| ATOM | 2267 | NZ | LYS | 2172 | 87.076 | 27.064 | 118.858 | 1.00 | 37.40 |
| ATOM | 2268 | C | LYS | 2172 | 89.950 | 28.256 | 123.159 | 1.00 | 29.64 |
| ATOM | 2269 | O | LYS | 2172 | 90.022 | 29.327 | 123.749 | 1.00 | 29.37 |
| ATOM | 2270 | N | THR | 2173 | 90.693 | 27.960 | 122.096 | 1.00 | 29.36 |
| ATOM | 2271 | CA | THR | 2173 | 91.616 | 28.929 | 121.503 | 1.00 | 28.42 |
| ATOM | 2272 | CB | THR | 2173 | 92.679 | 28.248 | 120.603 | 1.00 | 28.14 |
| ATOM | 2273 | OG1 | THR | 2173 | 93.569 | 27.471 | 121.407 | 1.00 | 29.92 |
| ATOM | 2274 | CG2 | THR | 2173 | 93.474 | 29.277 | 119.831 | 1.00 | 26.11 |
| ATOM | 2275 | C | THR | 2173 | 90.814 | 29.856 | 120.610 | 1.00 | 28.51 |
| ATOM | 2276 | O | THR | 2173 | 89.989 | 29.402 | 119.815 | 1.00 | 27.97 |
| ATOM | 2277 | N | VAL | 2174 | 91.054 | 31.154 | 120.737 | 1.00 | 29.34 |
| ATOM | 2278 | CA | VAL | 2174 | 90.340 | 32.124 | 119.921 | 1.00 | 30.30 |
| ATOM | 2279 | CB | VAL | 2174 | 89.595 | 33.149 | 120.781 | 1.00 | 30.41 |
| ATOM | 2280 | CG1 | VAL | 2174 | 88.985 | 34.203 | 119.892 | 1.00 | 31.26 |
| ATOM | 2281 | CG2 | VAL | 2174 | 88.512 | 32.463 | 121.584 | 1.00 | 30.49 |
| ATOM | 2282 | C | VAL | 2174 | 91.312 | 32.875 | 119.037 | 1.00 | 30.86 |
| ATOM | 2283 | O | VAL | 2174 | 92.387 | 33.259 | 119.476 | 1.00 | 31.22 |
| ATOM | 2284 | N | LYS | 2175 | 90.911 | 33.086 | 117.792 | 1.00 | 31.57 |
| ATOM | 2285 | CA | LYS | 2175 | 91.727 | 33.785 | 116.816 | 1.00 | 33.31 |
| ATOM | 2286 | CB | LYS | 2175 | 92.308 | 32.771 | 115.823 | 1.00 | 35.27 |
| ATOM | 2287 | CG | LYS | 2175 | 92.892 | 33.378 | 114.550 | 1.00 | 38.22 |
| ATOM | 2288 | CD | LYS | 2175 | 93.420 | 32.294 | 113.610 | 1.00 | 41.78 |
| ATOM | 2289 | CE | LYS | 2175 | 94.239 | 32.888 | 112.452 | 1.00 | 44.24 |
| ATOM | 2290 | NZ | LYS | 2175 | 94.879 | 31.850 | 111.566 | 1.00 | 45.00 |
| ATOM | 2291 | C | LYS | 2175 | 90.878 | 34.807 | 116.061 | 1.00 | 34.00 |
| ATOM | 2292 | O | LYS | 2175 | 89.881 | 34.445 | 115.437 | 1.00 | 33.89 |
| ATOM | 2293 | N | PHE | 2176 | 91.272 | 36.078 | 116.128 | 1.00 | 34.33 |

TABLE 6-continued

FGF2/FGFR1/Heparin Ternary Complex

| ATOM | 2294 | CA | PHE | 2176 | 90.570 | 37.154 | 115.428 | 1.00 | 34.12 |
|---|---|---|---|---|---|---|---|---|---|
| ATOM | 2295 | CB | PHE | 2176 | 90.262 | 38.304 | 116.389 | 1.00 | 32.91 |
| ATOM | 2296 | CG | PHE | 2176 | 89.290 | 37.946 | 117.466 | 1.00 | 31.94 |
| ATOM | 2297 | CD1 | PHE | 2176 | 87.994 | 37.574 | 117.152 | 1.00 | 30.90 |
| ATOM | 2298 | CD2 | PHE | 2176 | 89.671 | 37.971 | 118.797 | 1.00 | 31.99 |
| ATOM | 2299 | CE1 | PHE | 2176 | 87.091 | 37.231 | 118.148 | 1.00 | 31.11 |
| ATOM | 2300 | CE2 | PHE | 2176 | 88.770 | 37.626 | 119.806 | 1.00 | 31.88 |
| ATOM | 2301 | CZ | PHE | 2176 | 87.479 | 37.255 | 119.478 | 1.00 | 30.39 |
| ATOM | 2302 | C | PHE | 2176 | 91.485 | 37.652 | 114.318 | 1.00 | 34.66 |
| ATOM | 2303 | O | PHE | 2176 | 92.662 | 37.941 | 114.570 | 1.00 | 34.60 |
| ATOM | 2304 | N | LYS | 2177 | 90.956 | 37.753 | 113.099 | 1.00 | 34.79 |
| ATOM | 2305 | CA | LYS | 2177 | 91.759 | 38.212 | 111.967 | 1.00 | 35.78 |
| ATOM | 2306 | CB | LYS | 2177 | 91.971 | 37.064 | 110.980 | 1.00 | 36.77 |
| ATOM | 2307 | CG | LYS | 2177 | 90.722 | 36.268 | 110.696 | 1.00 | 39.23 |
| ATOM | 2308 | CD | LYS | 2177 | 91.062 | 34.929 | 110.073 | 1.00 | 41.52 |
| ATOM | 2309 | CE | LYS | 2177 | 89.818 | 34.068 | 109.929 | 1.00 | 44.06 |
| ATOM | 2310 | NZ | LYS | 2177 | 90.138 | 32.776 | 109.261 | 1.00 | 45.50 |
| ATOM | 2311 | C | LYS | 2177 | 91.181 | 39.408 | 111.231 | 1.00 | 35.77 |
| ATOM | 2312 | O | LYS | 2177 | 89.969 | 39.596 | 111.179 | 1.00 | 35.34 |
| ATOM | 2313 | N | CYS | 2178 | 92.070 | 40.219 | 110.668 | 1.00 | 35.64 |
| ATOM | 2314 | CA | CYS | 2178 | 91.669 | 41.396 | 109.915 | 1.00 | 35.78 |
| ATOM | 2315 | C | CYS | 2178 | 92.463 | 41.503 | 108.623 | 1.00 | 37.33 |
| ATOM | 2316 | O | CYS | 2178 | 93.258 | 42.428 | 108.432 | 1.00 | 37.67 |
| ATOM | 2317 | CB | CYS | 2178 | 91.852 | 42.656 | 110.752 | 1.00 | 34.60 |
| ATOM | 2318 | SG | CYS | 2178 | 90.535 | 42.925 | 111.984 | 1.00 | 35.18 |
| ATOM | 2319 | N | PRO | 2179 | 92.247 | 40.548 | 107.711 | 1.00 | 38.50 |
| ATOM | 2320 | CD | PRO | 2179 | 91.225 | 39.495 | 107.822 | 1.00 | 39.46 |
| ATOM | 2321 | CA | PRO | 2179 | 92.911 | 40.480 | 106.410 | 1.00 | 39.04 |
| ATOM | 2322 | CB | PRO | 2179 | 92.131 | 39.394 | 105.680 | 1.00 | 39.14 |
| ATOM | 2323 | CG | PRO | 2179 | 91.673 | 38.511 | 106.779 | 1.00 | 39.46 |
| ATOM | 2324 | C | PRO | 2179 | 92.763 | 41.801 | 105.706 | 1.00 | 39.02 |
| ATOM | 2325 | O | PRO | 2179 | 91.650 | 42.181 | 105.358 | 1.00 | 39.25 |
| ATOM | 2326 | N | SER | 2180 | 93.878 | 42.491 | 105.498 | 1.00 | 39.35 |
| ATOM | 2327 | CA | SER | 2180 | 93.862 | 43.775 | 104.815 | 1.00 | 40.27 |
| ATOM | 2328 | CB | SER | 2180 | 93.639 | 44.898 | 105.826 | 1.00 | 38.75 |
| ATOM | 2329 | OG | SER | 2180 | 94.704 | 44.963 | 106.746 | 1.00 | 37.59 |
| ATOM | 2330 | C | SER | 2180 | 95.163 | 44.019 | 104.054 | 1.00 | 41.09 |
| ATOM | 2331 | O | SER | 2180 | 96.146 | 43.309 | 104.248 | 1.00 | 41.62 |
| ATOM | 2332 | N | SER | 2181 | 95.153 | 45.025 | 103.184 | 1.00 | 41.78 |
| ATOM | 2333 | CA | SER | 2181 | 96.323 | 45.391 | 102.390 | 1.00 | 42.47 |
| ATOM | 2334 | CB | SER | 2181 | 96.303 | 44.688 | 101.032 | 1.00 | 41.93 |
| ATOM | 2335 | OG | SER | 2181 | 96.561 | 43.307 | 101.165 | 1.00 | 43.05 |
| ATOM | 2336 | C | SER | 2181 | 96.353 | 46.891 | 102.153 | 1.00 | 43.03 |
| ATOM | 2337 | O | SER | 2181 | 95.466 | 47.622 | 102.589 | 1.00 | 43.52 |
| ATOM | 2338 | N | GLY | 2182 | 97.371 | 47.344 | 101.435 | 1.00 | 43.41 |
| ATOM | 2339 | CA | GLY | 2182 | 97.487 | 48.759 | 101.152 | 1.00 | 44.12 |
| ATOM | 2340 | C | GLY | 2182 | 98.941 | 49.155 | 101.091 | 1.00 | 44.00 |
| ATOM | 2341 | O | GLY | 2182 | 99.760 | 48.631 | 101.837 | 1.00 | 44.97 |
| ATOM | 2342 | N | THR | 2183 | 99.268 | 50.089 | 100.210 | 1.00 | 43.66 |
| ATOM | 2343 | CA | THR | 2183 | 100.646 | 50.514 | 100.058 | 1.00 | 42.77 |
| ATOM | 2344 | CB | THR | 2183 | 101.111 | 50.256 | 98.634 | 1.00 | 41.91 |
| ATOM | 2345 | OG1 | THR | 2183 | 100.517 | 51.224 | 97.769 | 1.00 | 41.95 |
| ATOM | 2346 | CG2 | THR | 2183 | 100.673 | 48.865 | 98.183 | 1.00 | 41.42 |
| ATOM | 2347 | C | THR | 2183 | 100.835 | 51.989 | 100.391 | 1.00 | 42.68 |
| ATOM | 2348 | O | THR | 2183 | 100.083 | 52.841 | 99.928 | 1.00 | 43.54 |
| ATOM | 2349 | N | PRO | 2184 | 101.841 | 52.305 | 101.217 | 1.00 | 41.92 |
| ATOM | 2350 | CD | PRO | 2184 | 102.188 | 53.676 | 101.616 | 1.00 | 41.42 |
| ATOM | 2351 | CA | PRO | 2184 | 102.767 | 51.343 | 101.820 | 1.00 | 41.86 |
| ATOM | 2352 | CB | PRO | 2184 | 103.800 | 52.240 | 102.494 | 1.00 | 41.71 |
| ATOM | 2353 | CG | PRO | 2184 | 103.000 | 53.442 | 102.863 | 1.00 | 41.80 |
| ATOM | 2354 | C | PRO | 2184 | 102.083 | 50.402 | 102.811 | 1.00 | 41.92 |
| ATOM | 2355 | O | PRO | 2184 | 101.066 | 50.753 | 103.414 | 1.00 | 42.43 |
| ATOM | 2356 | N | GLN | 2185 | 102.651 | 49.210 | 102.962 | 1.00 | 40.80 |
| ATOM | 2357 | CA | GLN | 2185 | 102.132 | 48.191 | 103.867 | 1.00 | 40.57 |
| ATOM | 2358 | CB | GLN | 2185 | 103.230 | 47.171 | 104.158 | 1.00 | 40.77 |
| ATOM | 2359 | CG | GLN | 2185 | 102.746 | 45.902 | 104.792 | 1.00 | 40.48 |
| ATOM | 2360 | CD | GLN | 2185 | 101.819 | 45.131 | 103.878 | 1.00 | 41.61 |
| ATOM | 2361 | OE1 | GLN | 2185 | 101.392 | 44.028 | 104.212 | 1.00 | 43.14 |
| ATOM | 2362 | NE2 | GLN | 2185 | 101.497 | 45.705 | 102.720 | 1.00 | 40.31 |
| ATOM | 2363 | C | GLN | 2185 | 101.643 | 48.784 | 105.187 | 1.00 | 40.32 |
| ATOM | 2364 | O | GLN | 2185 | 102.407 | 49.433 | 105.902 | 1.00 | 41.24 |
| ATOM | 2365 | N | PRO | 2186 | 100.360 | 48.569 | 105.529 | 1.00 | 39.44 |
| ATOM | 2366 | CD | PRO | 2186 | 99.262 | 48.067 | 104.684 | 1.00 | 39.20 |
| ATOM | 2367 | CA | PRO | 2186 | 99.851 | 49.121 | 106.790 | 1.00 | 38.75 |
| ATOM | 2368 | CB | PRO | 2186 | 98.334 | 49.118 | 106.586 | 1.00 | 38.97 |
| ATOM | 2369 | CG | PRO | 2186 | 98.123 | 47.966 | 105.662 | 1.00 | 39.83 |
| ATOM | 2370 | C | PRO | 2186 | 100.293 | 48.343 | 108.024 | 1.00 | 37.46 |

TABLE 6-continued

FGF2/FGFR1/Heparin Ternary Complex

| ATOM | 2371 | O | PRO | 2186 | 100.662 | 47.172 | 107.939 | 1.00 | 38.41 |
|------|------|------|------|------|---------|--------|---------|------|-------|
| ATOM | 2372 | N | THR | 2187 | 100.283 | 49.017 | 109.165 | 1.00 | 36.11 |
| ATOM | 2373 | CA | THR | 2187 | 100.667 | 48.407 | 110.432 | 1.00 | 35.86 |
| ATOM | 2374 | CB | THR | 2187 | 101.258 | 49.448 | 111.378 | 1.00 | 36.05 |
| ATOM | 2375 | OG1 | THR | 2187 | 100.284 | 50.475 | 111.622 | 1.00 | 35.43 |
| ATOM | 2376 | CG2 | THR | 2187 | 102.499 | 50.062 | 110.771 | 1.00 | 35.70 |
| ATOM | 2377 | C | THR | 2187 | 99.419 | 47.825 | 111.097 | 1.00 | 35.74 |
| ATOM | 2378 | O | THR | 2187 | 98.309 | 48.332 | 110.902 | 1.00 | 36.38 |
| ATOM | 2379 | N | LEU | 2188 | 99.606 | 46.779 | 111.898 | 1.00 | 34.42 |
| ATOM | 2380 | CA | LEU | 2188 | 98.490 | 46.120 | 112.574 | 1.00 | 33.53 |
| ATOM | 2381 | CB | LEU | 2188 | 98.435 | 44.643 | 112.171 | 1.00 | 32.39 |
| ATOM | 2382 | CG | LEU | 2188 | 97.143 | 43.839 | 112.361 | 1.00 | 32.55 |
| ATOM | 2383 | CD1 | LEU | 2188 | 97.476 | 42.351 | 112.346 | 1.00 | 31.88 |
| ATOM | 2384 | CD2 | LEU | 2188 | 96.459 | 44.208 | 113.655 | 1.00 | 32.73 |
| ATOM | 2385 | C | LEU | 2188 | 98.615 | 46.193 | 114.094 | 1.00 | 33.67 |
| ATOM | 2386 | O | LEU | 2188 | 99.650 | 45.836 | 114.656 | 1.00 | 34.52 |
| ATOM | 2387 | N | ARG | 2189 | 97.566 | 46.652 | 114.764 | 1.00 | 32.45 |
| ATOM | 2388 | CA | ARG | 2189 | 97.601 | 46.705 | 116.213 | 1.00 | 31.36 |
| ATOM | 2389 | CB | ARG | 2189 | 98.046 | 48.098 | 116.694 | 1.00 | 30.49 |
| ATOM | 2390 | CG | ARG | 2189 | 97.078 | 49.248 | 116.499 | 1.00 | 31.19 |
| ATOM | 2391 | CD | ARG | 2189 | 97.797 | 50.576 | 116.766 | 1.00 | 32.99 |
| ATOM | 2392 | NE | ARG | 2189 | 96.896 | 51.703 | 117.021 | 1.00 | 34.94 |
| ATOM | 2393 | CZ | ARG | 2189 | 96.462 | 52.050 | 118.232 | 1.00 | 36.42 |
| ATOM | 2394 | NH1 | ARG | 2189 | 96.857 | 51.349 | 119.289 | 1.00 | 37.29 |
| ATOM | 2395 | NH2 | ARG | 2189 | 95.639 | 53.090 | 118.397 | 1.00 | 35.50 |
| ATOM | 2396 | C | ARG | 2189 | 96.226 | 46.303 | 116.751 | 1.00 | 31.00 |
| ATOM | 2397 | O | ARG | 2189 | 95.225 | 46.406 | 116.037 | 1.00 | 31.19 |
| ATOM | 2398 | N | TRP | 2190 | 96.173 | 45.813 | 117.988 | 1.00 | 29.63 |
| ATOM | 2399 | CA | TRP | 2190 | 94.905 | 45.382 | 118.571 | 1.00 | 28.95 |
| ATOM | 2400 | CB | TRP | 2190 | 94.941 | 43.885 | 118.851 | 1.00 | 27.63 |
| ATOM | 2401 | CG | TRP | 2190 | 94.984 | 43.058 | 117.625 | 1.00 | 27.16 |
| ATOM | 2402 | CD2 | TRP | 2190 | 93.861 | 42.498 | 116.935 | 1.00 | 27.28 |
| ATOM | 2403 | CE2 | TRP | 2190 | 94.366 | 41.822 | 115.797 | 1.00 | 28.20 |
| ATOM | 2404 | CE3 | TRP | 2190 | 92.476 | 42.502 | 117.165 | 1.00 | 25.80 |
| ATOM | 2405 | CD1 | TRP | 2190 | 96.086 | 42.713 | 116.907 | 1.00 | 27.06 |
| ATOM | 2406 | NE1 | TRP | 2190 | 95.728 | 41.969 | 115.807 | 1.00 | 27.55 |
| ATOM | 2407 | CZ2 | TRP | 2190 | 93.531 | 41.151 | 114.883 | 1.00 | 28.99 |
| ATOM | 2408 | CZ3 | TRP | 2190 | 91.644 | 41.835 | 116.258 | 1.00 | 26.84 |
| ATOM | 2409 | CH2 | TRP | 2190 | 92.177 | 41.168 | 115.129 | 1.00 | 27.57 |
| ATOM | 2410 | C | TRP | 2190 | 94.509 | 46.108 | 119.841 | 1.00 | 29.55 |
| ATOM | 2411 | O | TRP | 2190 | 95.359 | 46.620 | 120.567 | 1.00 | 30.93 |
| ATOM | 2412 | N | LEU | 2191 | 93.210 | 46.131 | 120.116 | 1.00 | 29.19 |
| ATOM | 2413 | CA | LEU | 2191 | 92.697 | 46.803 | 121.304 | 1.00 | 30.59 |
| ATOM | 2414 | CB | LEU | 2191 | 92.063 | 48.138 | 120.935 | 1.00 | 29.16 |
| ATOM | 2415 | CG | LEU | 2191 | 92.931 | 49.249 | 120.379 | 1.00 | 27.44 |
| ATOM | 2416 | CD1 | LEU | 2191 | 92.052 | 50.472 | 120.222 | 1.00 | 25.74 |
| ATOM | 2417 | CD2 | LEU | 2191 | 94.104 | 49.521 | 121.308 | 1.00 | 27.11 |
| ATOM | 2418 | C | LEU | 2191 | 91.646 | 46.001 | 122.049 | 1.00 | 32.08 |
| ATOM | 2419 | O | LEU | 2191 | 90.678 | 45.521 | 121.453 | 1.00 | 31.85 |
| ATOM | 2420 | N | LYS | 2192 | 91.824 | 45.876 | 123.358 | 1.00 | 32.21 |
| ATOM | 2421 | CA | LYS | 2192 | 90.856 | 45.159 | 124.160 | 1.00 | 32.88 |
| ATOM | 2422 | CB | LYS | 2192 | 91.567 | 44.330 | 125.225 | 1.00 | 32.95 |
| ATOM | 2423 | CG | LYS | 2192 | 90.653 | 43.486 | 126.089 | 1.00 | 32.27 |
| ATOM | 2424 | CD | LYS | 2192 | 91.452 | 42.389 | 126.781 | 1.00 | 33.72 |
| ATOM | 2425 | CE | LYS | 2192 | 90.622 | 41.595 | 127.794 | 1.00 | 34.06 |
| ATOM | 2426 | NZ | LYS | 2192 | 91.298 | 40.309 | 128.159 | 1.00 | 34.85 |
| ATOM | 2427 | C | LYS | 2192 | 90.006 | 46.240 | 124.788 | 1.00 | 34.32 |
| ATOM | 2428 | O | LYS | 2192 | 90.506 | 47.043 | 125.564 | 1.00 | 35.63 |
| ATOM | 2429 | N | ASN | 2193 | 88.728 | 46.278 | 124.424 | 1.00 | 36.52 |
| ATOM | 2430 | CA | ASN | 2193 | 87.795 | 47.284 | 124.931 | 1.00 | 38.57 |
| ATOM | 2431 | CB | ASN | 2193 | 87.482 | 47.020 | 126.400 | 1.00 | 38.98 |
| ATOM | 2432 | CG | ASN | 2193 | 86.819 | 45.683 | 126.613 | 1.00 | 39.97 |
| ATOM | 2433 | OD1 | ASN | 2193 | 85.844 | 45.353 | 125.934 | 1.00 | 40.22 |
| ATOM | 2434 | ND2 | ASN | 2193 | 87.336 | 44.903 | 127.558 | 1.00 | 40.04 |
| ATOM | 2435 | C | ASN | 2193 | 88.326 | 48.707 | 124.765 | 1.00 | 39.79 |
| ATOM | 2436 | O | ASN | 2193 | 88.290 | 49.504 | 125.696 | 1.00 | 39.94 |
| ATOM | 2437 | N | GLY | 2194 | 88.823 | 49.019 | 123.573 | 1.00 | 40.67 |
| ATOM | 2438 | CA | GLY | 2194 | 89.351 | 50.349 | 123.325 | 1.00 | 40.52 |
| ATOM | 2439 | C | GLY | 2194 | 90.767 | 50.590 | 123.820 | 1.00 | 40.79 |
| ATOM | 2440 | O | GLY | 2194 | 91.576 | 51.183 | 123.117 | 1.00 | 41.69 |
| ATOM | 2441 | N | LYS | 2195 | 91.074 | 50.136 | 125.027 | 1.00 | 40.12 |
| ATOM | 2442 | CA | LYS | 2195 | 92.402 | 50.330 | 125.589 | 1.00 | 40.52 |
| ATOM | 2443 | CB | LYS | 2195 | 92.387 | 50.012 | 127.087 | 1.00 | 39.82 |
| ATOM | 2444 | C | LYS | 2195 | 93.464 | 49.483 | 124.889 | 1.00 | 41.22 |
| ATOM | 2445 | O | LYS | 2195 | 93.146 | 48.483 | 124.243 | 1.00 | 41.36 |
| ATOM | 2446 | N | GLU | 2196 | 94.725 | 49.893 | 125.024 | 1.00 | 41.29 |
| ATOM | 2447 | CA | GLU | 2196 | 95.851 | 49.189 | 124.422 | 1.00 | 41.22 |

TABLE 6-continued

| FGF2/FGFR1/Heparin Ternary Complex | | | | | | | | |
|---|---|---|---|---|---|---|---|---|
| ATOM | 2448 | CB | GLU | 2196 | 97.128 | 50.014 | 124.548 | 1.00 | 42.15 |
| ATOM | 2449 | CG | GLU | 2196 | 98.403 | 49.191 | 124.357 | 1.00 | 42.05 |
| ATOM | 2450 | CD | GLU | 2196 | 99.644 | 49.865 | 124.928 | 1.00 | 42.46 |
| ATOM | 2451 | OE1 | GLE | 2196 | 99.608 | 50.302 | 126.101 | 1.00 | 42.02 |
| ATOM | 2452 | OE2 | GLU | 2196 | 100.663 | 49.946 | 124.210 | 1.00 | 43.16 |
| ATOM | 2453 | C | GLU | 2196 | 96.098 | 47.838 | 125.069 | 1.00 | 41.45 |
| ATOM | 2454 | O | GLU | 2196 | 96.266 | 47.740 | 126.277 | 1.00 | 40.77 |
| ATOM | 2455 | N | PHE | 2197 | 96.157 | 46.808 | 124.237 | 1.00 | 41.80 |
| ATOM | 2456 | CA | PHE | 2197 | 96.378 | 45.433 | 124.664 | 1.00 | 42.48 |
| ATOM | 2457 | CB | PHE | 2197 | 95.756 | 44.540 | 123.578 | 1.00 | 41.27 |
| ATOM | 2458 | CG | PHE | 2197 | 95.269 | 43.195 | 124.054 | 1.00 | 39.86 |
| ATOM | 2459 | CD1 | PHE | 2197 | 94.888 | 42.230 | 123.128 | 1.00 | 38.62 |
| ATOM | 2460 | CD2 | PHE | 2197 | 95.197 | 42.881 | 125.400 | 1.00 | 40.20 |
| ATOM | 2461 | CE1 | PHE | 2197 | 94.449 | 40.974 | 123.528 | 1.00 | 38.94 |
| ATOM | 2462 | CE2 | PHE | 2197 | 94.756 | 41.618 | 125.812 | 1.00 | 39.99 |
| ATOM | 2463 | CZ | PHE | 2197 | 94.383 | 40.666 | 124.872 | 1.00 | 39.73 |
| ATOM | 2464 | C | PHE | 2197 | 97.901 | 45.207 | 124.766 | 1.00 | 43.80 |
| ATOM | 2465 | O | PHE | 2197 | 98.668 | 45.900 | 124.108 | 1.00 | 45.77 |
| ATOM | 2466 | N | LYS | 2198 | 98.337 | 44.253 | 125.586 | 1.00 | 44.13 |
| ATOM | 2467 | CA | LYS | 2198 | 99.768 | 43.928 | 125.739 | 1.00 | 44.71 |
| ATOM | 2468 | CB | LYS | 2198 | 100.454 | 44.829 | 126.777 | 1.00 | 45.08 |
| ATOM | 2469 | CG | LYS | 2198 | 100.915 | 46.175 | 126.239 | 1.00 | 46.46 |
| ATOM | 2470 | CD | LYS | 2198 | 101.578 | 47.027 | 127.319 | 1.00 | 48.52 |
| ATOM | 2471 | CE | LYS | 2198 | 101.944 | 48.421 | 126.776 | 1.00 | 49.18 |
| ATOM | 2472 | NZ | LYS | 2198 | 102.534 | 49.339 | 127.804 | 1.00 | 48.52 |
| ATOM | 2473 | C | LYS | 2198 | 99.898 | 42.477 | 126.183 | 1.00 | 44.72 |
| ATOM | 2474 | O | LYS | 2198 | 99.252 | 42.060 | 127.141 | 1.00 | 45.40 |
| ATOM | 2475 | N | PRO | 2199 | 100.739 | 41.686 | 125.497 | 1.00 | 43.97 |
| ATOM | 2476 | CD | PRO | 2199 | 101.524 | 42.007 | 124.298 | 1.00 | 43.28 |
| ATOM | 2477 | CA | PRO | 2199 | 100.918 | 40.276 | 125.850 | 1.00 | 43.87 |
| ATOM | 2478 | CB | PRO | 2199 | 102.173 | 39.901 | 125.084 | 1.00 | 42.82 |
| ATOM | 2479 | CG | PRO | 2199 | 101.948 | 40.624 | 123.817 | 1.00 | 42.83 |
| ATOM | 2480 | C | PRO | 2199 | 100.951 | 39.908 | 127.340 | 1.00 | 44.42 |
| ATOM | 2481 | O | PRO | 2199 | 100.379 | 38.888 | 127.728 | 1.00 | 45.33 |
| ATOM | 2482 | N | ASP | 2200 | 101.587 | 40.712 | 128.184 | 1.00 | 43.91 |
| ATOM | 2483 | CA | ASP | 2200 | 101.586 | 40.379 | 129.601 | 1.00 | 44.12 |
| ATOM | 2484 | CB | ASP | 2200 | 102.720 | 41.121 | 130.330 | 1.00 | 47.94 |
| ATOM | 2485 | CG | ASP | 2200 | 102.936 | 42.544 | 129.815 | 1.00 | 52.10 |
| ATOM | 2486 | OD1 | ASP | 2200 | 101.955 | 43.321 | 129.716 | 1.00 | 54.71 |
| ATOM | 2487 | OD2 | ASP | 2200 | 104.101 | 42.890 | 129.518 | 1.00 | 52.51 |
| ATOM | 2488 | C | ASP | 2200 | 100.217 | 40.657 | 130.268 | 1.00 | 42.28 |
| ATOM | 2489 | O | ASP | 2200 | 100.046 | 40.441 | 131.466 | 1.00 | 41.60 |
| ATOM | 2490 | N | HIS | 2201 | 99.243 | 41.113 | 129.484 | 1.00 | 39.83 |
| ATOM | 2491 | CA | HIS | 2201 | 97.902 | 41.408 | 129.994 | 1.00 | 38.18 |
| ATOM | 2492 | CB | HIS | 2201 | 97.095 | 42.252 | 129.000 | 1.00 | 36.78 |
| ATOM | 2493 | CG | HIS | 2201 | 97.474 | 43.699 | 128.956 | 1.00 | 35.18 |
| ATOM | 2494 | CD2 | HIS | 2201 | 97.140 | 44.675 | 128.078 | 1.00 | 33.45 |
| ATOM | 2495 | ND1 | HIS | 2201 | 98.255 | 44.300 | 129.920 | 1.00 | 33.71 |
| ATOM | 2496 | CE1 | HIS | 2201 | 98.386 | 45.584 | 129.636 | 1.00 | 33.15 |
| ATOM | 2497 | NE2 | HIS | 2201 | 97.719 | 45.837 | 128.524 | 1.00 | 33.26 |
| ATOM | 2498 | C | HIS | 2201 | 97.050 | 40.178 | 130.293 | 1.00 | 37.71 |
| ATOM | 2499 | O | HIS | 2201 | 95.958 | 40.307 | 130.842 | 1.00 | 37.87 |
| ATOM | 2500 | N | ARG | 2202 | 97.510 | 38.998 | 129.895 | 1.00 | 36.98 |
| ATOM | 2501 | CA | ARG | 2202 | 96.757 | 37.774 | 130.152 | 1.00 | 36.37 |
| ATOM | 2502 | CB | ARG | 2202 | 95.773 | 37.490 | 129.014 | 1.00 | 35.42 |
| ATOM | 2503 | CG | ARG | 2202 | 96.408 | 36.963 | 127.733 | 1.00 | 32.75 |
| ATOM | 2504 | CD | ARG | 2202 | 95.375 | 36.864 | 126.619 | 1.00 | 30.71 |
| ATOM | 2505 | NE | ARG | 2202 | 94.316 | 35.902 | 126.909 | 1.00 | 29.13 |
| ATOM | 2506 | CZ | ARG | 2202 | 94.454 | 34.584 | 126.808 | 1.00 | 30.20 |
| ATOM | 2507 | NH1 | ARG | 2202 | 95.608 | 34.058 | 126.424 | 1.00 | 31.83 |
| ATOM | 2508 | NH2 | ARG | 2202 | 93.435 | 33.784 | 127.070 | 1.00 | 30.13 |
| ATOM | 2509 | C | ARG | 2202 | 97.740 | 36.623 | 130.266 | 1.00 | 37.00 |
| ATOM | 2510 | O | ARG | 2202 | 98.799 | 36.652 | 129.640 | 1.00 | 35.95 |
| ATOM | 2511 | N | ILE | 2203 | 97.407 | 35.609 | 131.058 | 1.00 | 38.08 |
| ATOM | 2512 | CA | ILE | 2203 | 98.330 | 34.493 | 131.181 | 1.00 | 39.00 |
| ATOM | 2513 | CB | ILE | 2203 | 97.884 | 33.446 | 132.213 | 1.00 | 39.18 |
| ATOM | 2514 | CC2 | ILE | 2203 | 96.685 | 32.657 | 131.694 | 1.00 | 38.82 |
| ATOM | 2515 | CG1 | ILE | 2203 | 99.053 | 32.499 | 132.495 | 1.00 | 39.82 |
| ATOM | 2516 | CD1 | ILE | 2203 | 100.275 | 33.187 | 133.083 | 1.00 | 37.47 |
| ATOM | 2517 | C | ILE | 2203 | 98.508 | 33.817 | 129.830 | 1.00 | 39.98 |
| ATOM | 2518 | O | ILE | 2203 | 97.544 | 33.559 | 129.100 | 1.00 | 40.24 |
| ATOM | 2519 | N | GLY | 2204 | 99.759 | 33.538 | 129.499 | 1.00 | 40.59 |
| ATOM | 2520 | CA | GLY | 2204 | 100.051 | 32.927 | 128.219 | 1.00 | 41.35 |
| ATOM | 2521 | C | GLY | 2204 | 100.042 | 34.010 | 127.157 | 1.00 | 41.56 |
| ATOM | 2522 | O | GLY | 2204 | 100.469 | 33.789 | 126.025 | 1.00 | 41.20 |
| ATOM | 2523 | N | GLY | 2205 | 99.548 | 35.187 | 127.537 | 1.00 | 41.55 |
| ATOM | 2524 | CA | GLY | 2205 | 99.469 | 36.316 | 126.626 | 1.00 | 40.71 |

TABLE 6-continued

FGF2/FGFR1/Heparin Ternary Complex

| ATOM | 2525 | C | GLY | 2205 | 98.821 | 36.028 | 125.281 | 1.00 | 40.50 |
|---|---|---|---|---|---|---|---|---|---|
| ATOM | 2526 | O | GLY | 2205 | 98.122 | 35.027 | 125.113 | 1.00 | 39.66 |
| ATOM | 2527 | N | TYR | 2206 | 99.021 | 36.932 | 124.325 | 1.00 | 40.49 |
| ATOM | 2528 | CA | TYR | 2206 | 98.482 | 36.723 | 122.993 | 1.00 | 40.63 |
| ATOM | 2529 | CB | TYR | 2206 | 97.446 | 37.775 | 122.580 | 1.00 | 39.91 |
| ATOM | 2530 | CG | TYR | 2206 | 97.850 | 39.221 | 122.748 | 1.00 | 40.02 |
| ATOM | 2531 | CD1 | TYR | 2206 | 97.755 | 39.850 | 123.994 | 1.00 | 40.48 |
| ATOM | 2532 | CE1 | TYR | 2206 | 98.058 | 41.199 | 124.151 | 1.00 | 39.15 |
| ATOM | 2533 | CD2 | TYR | 2206 | 98.268 | 39.980 | 121.660 | 1.00 | 38.56 |
| ATOM | 2534 | CE2 | TYR | 2206 | 98.576 | 41.332 | 121.805 | 1.00 | 38.64 |
| ATOM | 2535 | CZ | TYR | 2206 | 98.468 | 41.940 | 123.056 | 1.00 | 39.43 |
| ATOM | 2536 | OH | TYR | 2206 | 98.762 | 43.285 | 123.211 | 1.00 | 38.19 |
| ATOM | 2537 | C | TYR | 2206 | 99.605 | 36.681 | 121.988 | 1.00 | 41.31 |
| ATOM | 2538 | O | TYR | 2206 | 100.753 | 37.004 | 122.298 | 1.00 | 41.16 |
| ATOM | 2539 | N | LYS | 2207 | 99.264 | 36.247 | 120.784 | 1.00 | 42.04 |
| ATOM | 2540 | CA | LYS | 2207 | 100.223 | 36.121 | 119.703 | 1.00 | 43.21 |
| ATOM | 2541 | CB | LYS | 2207 | 100.465 | 34.647 | 119.398 | 1.00 | 44.52 |
| ATOM | 2542 | CG | LYS | 2207 | 101.339 | 34.407 | 118.187 | 1.00 | 47.14 |
| ATOM | 2543 | CD | LYS | 2207 | 101.051 | 33.041 | 117.596 | 1.00 | 49.53 |
| ATOM | 2544 | CE | LYS | 2207 | 101.862 | 32.797 | 116.344 | 1.00 | 50.27 |
| ATOM | 2545 | NZ | LYS | 2207 | 101.553 | 31.473 | 115.742 | 1.00 | 51.00 |
| ATOM | 2546 | C | LYS | 2207 | 99.659 | 36.802 | 118.469 | 1.00 | 43.19 |
| ATOM | 2547 | O | LYS | 2207 | 98.533 | 36.518 | 118.057 | 1.00 | 43.68 |
| ATOM | 2548 | N | VAL | 2208 | 100.432 | 37.704 | 117.877 | 1.00 | 42.85 |
| ATOM | 2549 | CA | VAL | 2208 | 99.959 | 38.396 | 116.687 | 1.00 | 42.83 |
| ATOM | 2550 | CB | VAL | 2208 | 100.080 | 39.937 | 116.819 | 1.00 | 42.12 |
| ATOM | 2551 | CG1 | VAL | 2208 | 99.676 | 40.608 | 115.516 | 1.00 | 41.15 |
| ATOM | 2552 | CG2 | VAL | 2208 | 99.182 | 40.433 | 117.932 | 1.00 | 41.53 |
| ATOM | 2553 | C | VAL | 2208 | 100.722 | 37.946 | 115.455 | 1.00 | 42.80 |
| ATOM | 2554 | O | VAL | 2208 | 101.942 | 38.056 | 115.396 | 1.00 | 42.90 |
| ATOM | 2555 | N | ARG | 2209 | 99.987 | 37.422 | 114.481 | 1.00 | 43.49 |
| ATOM | 2556 | CA | ARG | 2209 | 100.565 | 36.953 | 113.222 | 1.00 | 43.88 |
| ATOM | 2557 | CB | ARG | 2209 | 100.000 | 35.584 | 112.835 | 1.00 | 44.05 |
| ATOM | 2558 | CG | ARG | 2209 | 100.652 | 34.440 | 113.565 | 1.00 | 45.90 |
| ATOM | 2559 | CD | ARG | 2209 | 102.020 | 34.172 | 112.999 | 1.00 | 48.17 |
| ATOM | 2560 | NE | ARG | 2209 | 102.967 | 33.768 | 114.030 | 1.00 | 51.06 |
| ATOM | 2561 | CZ | ARG | 2209 | 104.083 | 33.079 | 113.801 | 1.00 | 53.29 |
| ATOM | 2562 | NH1 | ARG | 2209 | 104.397 | 32.705 | 112.565 | 1.00 | 53.46 |
| ATOM | 2563 | NH2 | ARG | 2209 | 104.891 | 32.765 | 114.807 | 1.00 | 55.10 |
| ATOM | 2564 | C | ARG | 2209 | 100.263 | 37.945 | 112.112 | 1.00 | 44.04 |
| ATOM | 2565 | O | ARG | 2209 | 99.323 | 37.755 | 111.340 | 1.00 | 43.78 |
| ATOM | 2566 | N | TYR | 2210 | 101.061 | 39.008 | 112.035 | 1.00 | 43.71 |
| ATOM | 2567 | CA | TYR | 2210 | 100.850 | 40.019 | 111.011 | 1.00 | 42.27 |
| ATOM | 2568 | CB | TYR | 2210 | 101.966 | 41.056 | 110.993 | 1.00 | 43.20 |
| ATOM | 2569 | CG | TYR | 2210 | 102.161 | 41.743 | 112.316 | 1.00 | 45.09 |
| ATOM | 2570 | CD1 | TYR | 2210 | 102.831 | 41.103 | 113.358 | 1.00 | 46.50 |
| ATOM | 2571 | CE1 | TYR | 2210 | 102.994 | 41.723 | 114.604 | 1.00 | 47.53 |
| ATOM | 2572 | CD2 | TYR | 2210 | 101.655 | 43.023 | 112.543 | 1.00 | 45.57 |
| ATOM | 2573 | CE2 | TYR | 2210 | 101.811 | 43.655 | 113.786 | 1.00 | 46.60 |
| ATOM | 2574 | CZ | TYR | 2210 | 102.482 | 42.997 | 114.811 | 1.00 | 47.26 |
| ATOM | 2575 | OH | TYR | 2210 | 102.646 | 43.593 | 116.039 | 1.00 | 47.71 |
| ATOM | 2576 | C | TYR | 2210 | 100.799 | 39.321 | 109.685 | 1.00 | 40.96 |
| ATOM | 2577 | O | TYR | 2210 | 100.130 | 39.775 | 108.772 | 1.00 | 41.30 |
| ATOM | 2578 | N | ALA | 2211 | 101.502 | 38.203 | 109.588 | 1.00 | 40.54 |
| ATOM | 2579 | CA | ALA | 2211 | 101.521 | 37.428 | 108.357 | 1.00 | 40.16 |
| ATOM | 2580 | CB | ALA | 2211 | 102.254 | 36.112 | 108.595 | 1.00 | 40.83 |
| ATOM | 2581 | C | ALA | 2211 | 100.089 | 37.168 | 107.873 | 1.00 | 39.20 |
| ATOM | 2582 | O | ALA | 2211 | 99.832 | 37.054 | 106.678 | 1.00 | 37.66 |
| ATOM | 2583 | N | THR | 2212 | 99.158 | 37.073 | 108.814 | 1.00 | 39.40 |
| ATOM | 2584 | CA | THR | 2212 | 97.765 | 36.846 | 108.462 | 1.00 | 39.47 |
| ATOM | 2585 | CB | THR | 2212 | 97.312 | 35.401 | 108.767 | 1.00 | 40.20 |
| ATOM | 2586 | OG1 | THR | 2212 | 97.752 | 35.004 | 110.077 | 1.00 | 41.45 |
| ATOM | 2587 | CG2 | THR | 2212 | 97.872 | 34.462 | 107.722 | 1.00 | 40.38 |
| ATOM | 2588 | C | THR | 2212 | 96.834 | 37.837 | 109.148 | 1.00 | 38.95 |
| ATOM | 2589 | O | THR | 2212 | 95.623 | 37.620 | 109.218 | 1.00 | 38.42 |
| ATOM | 2590 | N | TRP | 2213 | 97.415 | 38.931 | 109.637 | 1.00 | 38.83 |
| ATOM | 2591 | CA | TRP | 2213 | 96.662 | 39.999 | 110.290 | 1.00 | 38.61 |
| ATOM | 2592 | CB | TRP | 2213 | 95.779 | 40.736 | 109.276 | 1.00 | 40.70 |
| ATOM | 2593 | CG | TRP | 2213 | 96.537 | 41.323 | 108.162 | 1.00 | 42.61 |
| ATOM | 2594 | CD2 | TRP | 2213 | 97.098 | 42.634 | 108.118 | 1.00 | 43.58 |
| ATOM | 2595 | CE2 | TRP | 2213 | 97.789 | 42.749 | 106.896 | 1.00 | 44.29 |
| ATOM | 2596 | CE3 | TRP | 2213 | 97.084 | 43.726 | 108.994 | 1.00 | 43.52 |
| ATOM | 2597 | CD1 | TRP | 2213 | 96.895 | 40.710 | 107.002 | 1.00 | 43.01 |
| ATOM | 2598 | NE1 | TRP | 2213 | 97.650 | 41.558 | 106.233 | 1.00 | 44.09 |
| ATOM | 2599 | CZ2 | TRP | 2213 | 98.461 | 43.916 | 106.526 | 1.00 | 44.49 |
| ATOM | 2600 | CZ3 | TRP | 2213 | 97.750 | 44.883 | 108.627 | 1.00 | 43.51 |
| ATOM | 2601 | CH2 | TRP | 2213 | 98.429 | 44.969 | 107.403 | 1.00 | 44.41 |

TABLE 6-continued

FGF2/FGFR1/Heparin Ternary Complex

| ATOM | 2602 | C | TRP | 2213 | 95.774 | 39.442 | 111.371 | 1.00 | 37.32 |
|---|---|---|---|---|---|---|---|---|---|
| ATOM | 2603 | O | TRP | 2213 | 94.617 | 39.846 | 111.507 | 1.00 | 37.76 |
| ATOM | 2604 | N | SER | 2214 | 96.308 | 38.512 | 112.143 | 1.00 | 35.32 |
| ATOM | 2605 | CA | SER | 2214 | 95.516 | 37.892 | 113.190 | 1.00 | 33.63 |
| ATOM | 2606 | CB | SER | 2214 | 95.370 | 36.392 | 112.924 | 1.00 | 33.71 |
| ATOM | 2607 | OG | SER | 2214 | 94.681 | 36.144 | 111.720 | 1.00 | 34.61 |
| ATOM | 2608 | C | SER | 2214 | 96.104 | 38.058 | 114.572 | 1.00 | 31.52 |
| ATOM | 2609 | O | SER | 2214 | 97.281 | 38.396 | 114.736 | 1.00 | 31.05 |
| ATOM | 2610 | N | ILE | 2215 | 95.259 | 37.810 | 115.565 | 1.00 | 28.95 |
| ATOM | 2611 | CA | ILE | 2215 | 95.664 | 37.854 | 116.960 | 1.00 | 26.54 |
| ATOM | 2612 | CB | ILE | 2215 | 94.951 | 38.965 | 117.733 | 1.00 | 23.98 |
| ATOM | 2613 | CG2 | ILE | 2215 | 93.471 | 38.938 | 117.434 | 1.00 | 22.03 |
| ATOM | 2614 | CG1 | ILE | 2215 | 95.239 | 38.798 | 119.220 | 1.00 | 22.66 |
| ATOM | 2615 | CD1 | ILE | 2215 | 94.372 | 39.645 | 120.105 | 1.00 | 23.72 |
| ATOM | 2616 | C | ILE | 2215 | 95.195 | 36.509 | 117.486 | 1.00 | 25.62 |
| ATOM | 2617 | O | ILE | 2215 | 94.132 | 36.024 | 117.090 | 1.00 | 26.30 |
| ATOM | 2618 | N | ILE | 2216 | 95.967 | 35.890 | 118.361 | 1.00 | 23.36 |
| ATOM | 2619 | CA | ILE | 2216 | 95.546 | 34.600 | 118.866 | 1.00 | 23.42 |
| ATOM | 2620 | CB | ILE | 2216 | 96.436 | 33.461 | 118.341 | 1.00 | 24.04 |
| ATOM | 2621 | CG2 | ILE | 2216 | 95.658 | 32.164 | 118.362 | 1.00 | 22.84 |
| ATOM | 2622 | CG1 | ILE | 2216 | 96.924 | 33.763 | 116.918 | 1.00 | 26.50 |
| ATOM | 2623 | CD1 | ILE | 2216 | 96.007 | 33.275 | 115.788 | 1.00 | 27.77 |
| ATOM | 2624 | C | ILE | 2216 | 95.571 | 34.522 | 120.380 | 1.00 | 24.32 |
| ATOM | 2625 | O | ILE | 2216 | 96.529 | 34.949 | 121.037 | 1.00 | 24.53 |
| ATOM | 2626 | N | MET | 2217 | 94.503 | 33.971 | 120.935 | 1.00 | 24.28 |
| ATOM | 2627 | CA | MET | 2217 | 94.415 | 33.803 | 122.360 | 1.00 | 24.21 |
| ATOM | 2628 | CB | MET | 2217 | 93.352 | 34.715 | 122.959 | 1.00 | 24.38 |
| ATOM | 2629 | CG | MET | 2217 | 93.798 | 36.155 | 123.093 | 1.00 | 22.92 |
| ATOM | 2630 | SD | MET | 2217 | 92.463 | 37.174 | 123.666 | 1.00 | 21.81 |
| ATOM | 2631 | CE | MET | 2217 | 91.382 | 37.054 | 122.235 | 1.00 | 20.91 |
| ATOM | 2632 | C | MET | 2217 | 94.109 | 32.354 | 122.639 | 1.00 | 24.86 |
| ATOM | 2633 | O | MET | 2217 | 93.064 | 31.820 | 122.250 | 1.00 | 24.66 |
| ATOM | 2634 | N | ASP | 2218 | 95.076 | 31.727 | 123.294 | 1.00 | 25.10 |
| ATOM | 2635 | CA | ASP | 2218 | 94.993 | 30.344 | 123.687 | 1.00 | 24.19 |
| ATOM | 2636 | CB | ASP | 2218 | 96.385 | 29.741 | 123.795 | 1.00 | 24.55 |
| ATOM | 2637 | CG | ASP | 2218 | 96.751 | 28.908 | 122.600 | 1.00 | 25.12 |
| ATOM | 2638 | OD1 | ASP | 2218 | 95.908 | 28.741 | 121.693 | 1.00 | 25.15 |
| ATOM | 2639 | OD2 | ASP | 2218 | 97.895 | 28.411 | 122.575 | 1.00 | 25.43 |
| ATOM | 2640 | C | ASP | 2218 | 94.309 | 30.273 | 125.041 | 1.00 | 25.23 |
| ATOM | 2641 | O | ASP | 2218 | 94.398 | 31.203 | 125.847 | 1.00 | 24.60 |
| ATOM | 2642 | N | SER | 2219 | 93.613 | 29.162 | 125.268 | 1.00 | 25.53 |
| ATOM | 2643 | CA | SER | 2219 | 92.913 | 28.901 | 126.520 | 1.00 | 24.58 |
| ATOM | 2644 | CB | SER | 2219 | 93.900 | 28.304 | 127.536 | 1.00 | 26.55 |
| ATOM | 2645 | OG | SER | 2219 | 93.242 | 27.559 | 128.559 | 1.00 | 30.52 |
| ATOM | 2646 | C | SER | 2219 | 92.258 | 30.145 | 127.104 | 1.00 | 22.73 |
| ATOM | 2647 | O | SER | 2219 | 92.674 | 30.645 | 128.140 | 1.00 | 21.07 |
| ATOM | 2648 | N | VAL | 2220 | 91.215 | 30.637 | 126.450 | 1.00 | 22.94 |
| ATOM | 2649 | CA | VAL | 2220 | 90.548 | 31.835 | 126.935 | 1.00 | 23.29 |
| ATOM | 2650 | CB | VAL | 2220 | 89.682 | 32.470 | 125.839 | 1.00 | 21.85 |
| ATOM | 2651 | CG1 | VAL | 2220 | 90.564 | 32.792 | 124.638 | 1.00 | 21.42 |
| ATOM | 2652 | CG2 | VAL | 2220 | 88.544 | 31.549 | 125.455 | 1.00 | 19.27 |
| ATOM | 2653 | C | VAL | 2220 | 89.713 | 31.601 | 128.184 | 1.00 | 24.09 |
| ATOM | 2654 | O | VAL | 2220 | 89.290 | 30.485 | 128.466 | 1.00 | 25.16 |
| ATOM | 2655 | N | VAL | 2221 | 89.496 | 32.664 | 128.946 | 1.00 | 24.97 |
| ATOM | 2656 | CA | VAL | 2221 | 88.712 | 32.585 | 130.177 | 1.00 | 25.49 |
| ATOM | 2657 | CB | VAL | 2221 | 89.608 | 32.400 | 131.424 | 1.00 | 24.80 |
| ATOM | 2658 | CG1 | VAL | 2221 | 90.294 | 31.048 | 131.374 | 1.00 | 24.92 |
| ATOM | 2659 | CG2 | VAL | 2221 | 90.626 | 33.526 | 131.511 | 1.00 | 25.00 |
| ATOM | 2660 | C | VAL | 2221 | 87.870 | 33.840 | 130.374 | 1.00 | 25.44 |
| ATOM | 2661 | O | VAL | 2221 | 88.061 | 34.837 | 129.687 | 1.00 | 25.70 |
| ATOM | 2662 | N | PRO | 2222 | 86.922 | 33.807 | 131.323 | 1.00 | 26.28 |
| ATOM | 2663 | CD | PRO | 2222 | 86.620 | 32.728 | 132.281 | 1.00 | 26.63 |
| ATOM | 2664 | CA | PRO | 2222 | 86.063 | 34.969 | 131.579 | 1.00 | 27.30 |
| ATOM | 2665 | CB | PRO | 2222 | 85.534 | 34.698 | 132.981 | 1.00 | 25.99 |
| ATOM | 2666 | CG | PRO | 2222 | 85.346 | 33.230 | 132.951 | 1.00 | 26.68 |
| ATOM | 2667 | C | PRO | 2222 | 86.760 | 36.321 | 131.489 | 1.00 | 27.54 |
| ATOM | 2668 | O | PRO | 2222 | 86.225 | 37.268 | 130.908 | 1.00 | 27.07 |
| ATOM | 2669 | N | SER | 2223 | 87.951 | 36.412 | 132.069 | 1.00 | 28.28 |
| ATOM | 2670 | CA | SER | 2223 | 88.699 | 37.667 | 132.053 | 1.00 | 29.16 |
| ATOM | 2671 | CB | SER | 2223 | 90.073 | 37.486 | 132.721 | 1.00 | 30.38 |
| ATOM | 2672 | OG | SER | 2223 | 91.045 | 36.980 | 131.812 | 1.00 | 31.85 |
| ATOM | 2673 | C | SER | 2223 | 88.894 | 38.215 | 130.638 | 1.00 | 28.77 |
| ATOM | 2674 | O | SER | 2223 | 89.073 | 39.417 | 130.447 | 1.00 | 29.12 |
| ATOM | 2675 | N | ASP | 2224 | 88.847 | 37.334 | 129.649 | 1.00 | 28.24 |
| ATOM | 2676 | CA | ASP | 2224 | 89.045 | 37.747 | 128.279 | 1.00 | 27.95 |
| ATOM | 2677 | CB | ASP | 2224 | 89.609 | 36.577 | 127.476 | 1.00 | 29.00 |
| ATOM | 2678 | CG | ASP | 2224 | 90.940 | 36.103 | 128.022 | 1.00 | 29.75 |

TABLE 6-continued

FGF2/FGFR1/Heparin Ternary Complex

| ATOM | 2679 | OD1 | ASP | 2224 | 91.806 | 36.968 | 128.293 | 1.00 | 30.18 |
|---|---|---|---|---|---|---|---|---|---|
| ATOM | 2680 | OD2 | ASP | 2224 | 91.119 | 34.876 | 128.183 | 1.00 | 29.10 |
| ATOM | 2681 | C | ASP | 2224 | 87.792 | 38.300 | 127.629 | 1.00 | 27.30 |
| ATOM | 2682 | O | ASP | 2224 | 87.866 | 38.939 | 126.585 | 1.00 | 27.89 |
| ATOM | 2683 | N | LYS | 2225 | 86.641 | 38.073 | 128.243 | 1.00 | 27.44 |
| ATOM | 2684 | CA | LYS | 2225 | 85.403 | 38.582 | 127.669 | 1.00 | 29.05 |
| ATOM | 2685 | CB | LYS | 2225 | 84.240 | 38.398 | 128.640 | 1.00 | 30.40 |
| ATOM | 2686 | CG | LYS | 2225 | 84.042 | 36.969 | 129.081 | 1.00 | 31.45 |
| ATOM | 2687 | CD | LYS | 2225 | 82.580 | 36.664 | 129.267 | 1.00 | 34.02 |
| ATOM | 2688 | CE | LYS | 2225 | 81.939 | 37.559 | 130.300 | 1.00 | 35.70 |
| ATOM | 2689 | NZ | LYS | 2225 | 80.492 | 37.226 | 130.416 | 1.00 | 38.06 |
| ATOM | 2690 | C | LYS | 2225 | 85.589 | 40.056 | 127.370 | 1.00 | 29.01 |
| ATOM | 2691 | O | LYS | 2225 | 86.169 | 40.779 | 128.178 | 1.00 | 29.46 |
| ATOM | 2692 | N | GLY | 2226 | 85.115 | 40.499 | 126.210 | 1.00 | 28.77 |
| ATOM | 2693 | CA | GLY | 2226 | 85.257 | 41.899 | 125.860 | 1.00 | 29.00 |
| ATOM | 2694 | C | GLY | 2226 | 85.247 | 42.191 | 124.372 | 1.00 | 29.03 |
| ATOM | 2695 | O | GLY | 2226 | 84.906 | 41.336 | 123.562 | 1.00 | 29.33 |
| ATOM | 2696 | N | ASN | 2227 | 85.605 | 43.421 | 124.016 | 1.00 | 29.41 |
| ATOM | 2697 | CA | ASN | 2227 | 85.654 | 43.832 | 122.623 | 1.00 | 29.45 |
| ATOM | 2698 | CB | ASN | 2227 | 85.078 | 45.229 | 122.453 | 1.00 | 30.02 |
| ATOM | 2699 | CG | ASN | 2227 | 83.646 | 45.307 | 122.876 | 1.00 | 31.29 |
| ATOM | 2700 | OD1 | ASN | 2227 | 82.765 | 44.769 | 122.207 | 1.00 | 32.09 |
| ATOM | 2701 | ND2 | ASN | 2227 | 83.397 | 45.967 | 124.006 | 1.00 | 31.20 |
| ATOM | 2702 | C | ASN | 2227 | 87.099 | 43.858 | 122.205 | 1.00 | 29.08 |
| ATOM | 2703 | O | ASN | 2227 | 87.959 | 44.302 | 122.955 | 1.00 | 30.38 |
| ATOM | 2704 | N | TYR | 2228 | 87.369 | 43.385 | 121.005 | 1.00 | 27.71 |
| ATOM | 2705 | CA | TYR | 2228 | 88.721 | 43.374 | 120.514 | 1.00 | 28.06 |
| ATOM | 2706 | CB | TYR | 2228 | 89.195 | 41.921 | 120.363 | 1.00 | 28.22 |
| ATOM | 2707 | CG | TYR | 2228 | 89.471 | 41.237 | 121.692 | 1.00 | 27.12 |
| ATOM | 2708 | CD1 | TYR | 2228 | 88.432 | 40.824 | 122.531 | 1.00 | 25.93 |
| ATOM | 2709 | CE1 | TYR | 2228 | 88.698 | 40.271 | 123.793 | 1.00 | 26.56 |
| ATOM | 2710 | CD2 | TYR | 2228 | 90.779 | 41.074 | 122.143 | 1.00 | 27.73 |
| ATOM | 2711 | CE2 | TYR | 2228 | 91.053 | 40.526 | 123.399 | 1.00 | 27.06 |
| ATOM | 2712 | CZ | TYR | 2228 | 90.016 | 40.129 | 124.215 | 1.00 | 26.74 |
| ATOM | 2713 | OH | TYR | 2228 | 90.326 | 39.598 | 125.442 | 1.00 | 27.37 |
| ATOM | 2714 | C | TYR | 2228 | 88.719 | 44.119 | 119.188 | 1.00 | 29.09 |
| ATOM | 2715 | O | TYR | 2228 | 87.966 | 43.769 | 118.278 | 1.00 | 29.31 |
| ATOM | 2716 | N | THR | 2229 | 89.544 | 45.159 | 119.087 | 1.00 | 29.61 |
| ATOM | 2717 | CA | THR | 2229 | 89.608 | 45.959 | 117.872 | 1.00 | 29.63 |
| ATOM | 2718 | CB | THR | 2229 | 89.333 | 47.437 | 118.158 | 1.00 | 28.68 |
| ATOM | 2719 | OG1 | THR | 2229 | 88.084 | 47.574 | 118.831 | 1.00 | 27.17 |
| ATOM | 2720 | CG2 | THR | 2229 | 89.300 | 48.223 | 116.858 | 1.00 | 28.49 |
| ATOM | 2721 | C | THR | 2229 | 90.952 | 45.913 | 117.175 | 1.00 | 30.97 |
| ATOM | 2722 | O | THR | 2229 | 92.004 | 46.149 | 117.784 | 1.00 | 30.73 |
| ATOM | 2723 | N | CYS | 2230 | 90.913 | 45.639 | 115.882 | 1.00 | 32.04 |
| ATOM | 2724 | CA | CYS | 2230 | 92.136 | 45.615 | 115.110 | 1.00 | 33.92 |
| ATOM | 2725 | C | CYS | 2230 | 92.179 | 46.950 | 114.387 | 1.00 | 34.62 |
| ATOM | 2726 | O | CYS | 2230 | 91.147 | 47.457 | 113.961 | 1.00 | 34.44 |
| ATOM | 2727 | CB | CYS | 2230 | 92.110 | 44.483 | 114.084 | 1.00 | 33.63 |
| ATOM | 2728 | SG | CYS | 2230 | 90.959 | 44.779 | 112.710 | 1.00 | 32.18 |
| ATOM | 2729 | N | ILE | 2231 | 93.372 | 47.518 | 114.261 | 1.00 | 35.98 |
| ATOM | 2730 | CA | ILE | 2231 | 93.545 | 48.786 | 113.577 | 1.00 | 36.56 |
| ATOM | 2731 | CB | ILE | 2231 | 93.892 | 49.900 | 114.556 | 1.00 | 35.25 |
| ATOM | 2732 | CG2 | ILE | 2231 | 94.255 | 51.160 | 113.805 | 1.00 | 36.52 |
| ATOM | 2733 | CG1 | ILE | 2231 | 92.699 | 50.170 | 115.457 | 1.00 | 35.13 |
| ATOM | 2734 | CD1 | ILE | 2231 | 92.949 | 51.257 | 116.448 | 1.00 | 35.38 |
| ATOM | 2735 | C | ILE | 2231 | 94.653 | 48.694 | 112.547 | 1.00 | 38.34 |
| ATOM | 2736 | O | ILE | 2231 | 95.840 | 48.685 | 112.891 | 1.00 | 38.80 |
| ATOM | 2737 | N | VAL | 2232 | 94.258 | 48.617 | 111.283 | 1.00 | 39.59 |
| ATOM | 2738 | CA | VAL | 2232 | 95.213 | 48.546 | 110.193 | 1.00 | 41.70 |
| ATOM | 2739 | CB | VAL | 2232 | 94.705 | 47.653 | 109.084 | 1.00 | 42.55 |
| ATOM | 2740 | CG1 | VAL | 2232 | 95.767 | 47.522 | 108.005 | 1.00 | 43.06 |
| ATOM | 2741 | CG2 | VAL | 2232 | 94.340 | 46.304 | 109.658 | 1.00 | 43.42 |
| ATOM | 2742 | C | VAL | 2232 | 95.353 | 49.958 | 109.667 | 1.00 | 42.90 |
| ATOM | 2743 | O | VAL | 2232 | 94.356 | 50.625 | 109.405 | 1.00 | 42.57 |
| ATOM | 2744 | N | GLU | 2233 | 96.589 | 50.408 | 109.488 | 1.00 | 44.86 |
| ATOM | 2745 | CA | GLU | 2233 | 96.802 | 51.775 | 109.050 | 1.00 | 46.62 |
| ATOM | 2746 | CB | GLU | 2233 | 96.569 | 52.671 | 110.253 | 1.00 | 48.43 |
| ATOM | 2747 | CG | GLU | 2233 | 97.511 | 52.278 | 111.386 | 1.00 | 52.28 |
| ATOM | 2748 | CD | GLU | 2233 | 97.188 | 52.948 | 112.701 | 1.00 | 54.75 |
| ATOM | 2749 | OE1 | GLU | 2233 | 96.683 | 54.092 | 112.668 | 1.00 | 56.35 |
| ATOM | 2750 | OE2 | GLU | 2233 | 97.457 | 52.338 | 113.764 | 1.00 | 55.00 |
| ATOM | 2751 | C | GLU | 2233 | 98.181 | 52.096 | 108.466 | 1.00 | 46.69 |
| ATOM | 2752 | O | GLU | 2233 | 99.210 | 51.595 | 108.924 | 1.00 | 45.42 |
| ATOM | 2753 | N | ASN | 2234 | 98.181 | 52.940 | 107.442 | 1.00 | 47.28 |
| ATOM | 2754 | CA | ASN | 2234 | 99.415 | 53.408 | 106.837 | 1.00 | 48.02 |
| ATOM | 2755 | CB | ASN | 2234 | 99.665 | 52.807 | 105.440 | 1.00 | 48.62 |

TABLE 6-continued

FGF2/FGFR1/Heparin Ternary Complex

| ATOM | 2756 | CG | ASN | 2234 | 98.596 | 53.170 | 104.434 | 1.00 | 49.97 |
|---|---|---|---|---|---|---|---|---|---|
| ATOM | 2757 | OD1 | ASN | 2234 | 97.922 | 54.196 | 104.563 | 1.00 | 50.42 |
| ATOM | 2758 | ND2 | ASN | 2234 | 98.448 | 52.336 | 103.404 | 1.00 | 50.09 |
| ATOM | 2759 | C | ASN | 2234 | 99.253 | 54.925 | 106.782 | 1.00 | 48.23 |
| ATOM | 2760 | O | ASN | 2234 | 98.372 | 55.473 | 107.439 | 1.00 | 47.22 |
| ATOM | 2761 | N | GLU | 2235 | 100.083 | 55.598 | 106.000 | 1.00 | 48.98 |
| ATOM | 2762 | CA | GLU | 2235 | 100.051 | 57.052 | 105.905 | 1.00 | 49.40 |
| ATOM | 2763 | CB | GLU | 2235 | 101.323 | 57.527 | 105.210 | 1.00 | 51.16 |
| ATOM | 2764 | CC | GLU | 2235 | 102.574 | 56.796 | 105.669 | 1.00 | 55.19 |
| ATOM | 2765 | CD | GLU | 2235 | 103.767 | 57.050 | 104.756 | 1.00 | 58.69 |
| ATOM | 2766 | OE1 | GLU | 2235 | 103.660 | 56.759 | 103.539 | 1.00 | 60.15 |
| ATOM | 2767 | OE2 | GLU | 2235 | 104.811 | 57.539 | 105.257 | 1.00 | 58.99 |
| ATOM | 2768 | C | GLU | 2235 | 98.845 | 57.662 | 105.191 | 1.00 | 48.61 |
| ATOM | 2769 | O | GLU | 2235 | 98.562 | 58.845 | 105.357 | 1.00 | 47.90 |
| ATOM | 2770 | N | TYR | 2236 | 98.128 | 56.869 | 104.408 | 1.00 | 48.32 |
| ATOM | 2771 | CA | TYR | 2236 | 96.997 | 57.413 | 103.662 | 1.00 | 48.33 |
| ATOM | 2772 | CB | TYR | 2236 | 97.152 | 57.090 | 102.178 | 1.00 | 50.15 |
| ATOM | 2773 | CG | TYR | 2236 | 98.554 | 57.340 | 101.694 | 1.00 | 53.62 |
| ATOM | 2774 | CD1 | TYR | 2236 | 99.607 | 56.542 | 102.137 | 1.00 | 55.10 |
| ATOM | 2775 | CE1 | TYR | 2236 | 100.917 | 56.815 | 101.784 | 1.00 | 57.18 |
| ATOM | 2776 | CD2 | TYR | 2236 | 98.850 | 58.420 | 100.868 | 1.00 | 55.01 |
| ATOM | 2777 | CE2 | TYR | 2236 | 100.167 | 58.704 | 100.504 | 1.00 | 57.17 |
| ATOM | 2778 | CZ | TYR | 2236 | 101.196 | 57.895 | 100.972 | 1.00 | 57.54 |
| ATOM | 2779 | OH | TYR | 2236 | 102.507 | 58.170 | 100.655 | 1.00 | 59.18 |
| ATOM | 2780 | C | TYR | 2236 | 95.638 | 56.958 | 104.141 | 1.00 | 47.36 |
| ATOM | 2781 | O | TYR | 2236 | 94.657 | 57.050 | 103.408 | 1.00 | 47.35 |
| ATOM | 2782 | N | GLY | 2237 | 95.573 | 56.476 | 105.375 | 1.00 | 46.08 |
| ATOM | 2783 | CA | GLY | 2237 | 94.302 | 56.026 | 105.903 | 1.00 | 43.02 |
| ATOM | 2784 | C | GLY | 2237 | 94.425 | 54.969 | 106.980 | 1.00 | 41.26 |
| ATOM | 2785 | O | GLY | 2237 | 95.512 | 54.455 | 107.270 | 1.00 | 40.98 |
| ATOM | 2786 | N | SER | 2238 | 93.286 | 54.654 | 107.585 | 1.00 | 38.81 |
| ATOM | 2787 | CA | SER | 2238 | 93.214 | 53.654 | 108.635 | 1.00 | 35.42 |
| ATOM | 2788 | CB | SER | 2238 | 93.350 | 54.294 | 110.007 | 1.00 | 34.17 |
| ATOM | 2789 | OG | SER | 2238 | 92.170 | 54.064 | 110.755 | 1.00 | 30.78 |
| ATOM | 2790 | C | SER | 2238 | 91.860 | 52.996 | 108.556 | 1.00 | 34.05 |
| ATOM | 2791 | O | SER | 2238 | 90.883 | 53.624 | 108.170 | 1.00 | 34.61 |
| ATOM | 2792 | N | ILE | 2239 | 91.813 | 51.728 | 108.926 | 1.00 | 32.36 |
| ATOM | 2793 | CA | ILE | 2239 | 90.580 | 50.968 | 108.929 | 1.00 | 30.84 |
| ATOM | 2794 | CB | ILE | 2239 | 90.540 | 49.998 | 107.745 | 1.00 | 30.29 |
| ATOM | 2795 | CG2 | ILE | 2239 | 90.206 | 50.742 | 106.481 | 1.00 | 30.27 |
| ATOM | 2796 | CG1 | ILE | 2239 | 91.891 | 49.299 | 107.611 | 1.00 | 29.92 |
| ATOM | 2797 | CD1 | ILE | 2239 | 92.028 | 48.517 | 106.356 | 1.00 | 30.31 |
| ATOM | 2798 | C | ILE | 2239 | 90.582 | 50.185 | 110.230 | 1.00 | 30.38 |
| ATOM | 2799 | O | ILE | 2239 | 91.627 | 50.039 | 110.872 | 1.00 | 30.66 |
| ATOM | 2800 | N | ASN | 2240 | 89.424 | 49.678 | 110.624 | 1.00 | 29.34 |
| ATOM | 2801 | CA | ASN | 2240 | 89.356 | 48.924 | 111.859 | 1.00 | 28.33 |
| ATOM | 2802 | CB | ASN | 2240 | 89.456 | 49.875 | 113.032 | 1.00 | 27.41 |
| ATOM | 2803 | CG | ASN | 2240 | 88.246 | 50.745 | 113.143 | 1.00 | 27.47 |
| ATOM | 2804 | OD1 | ASN | 2240 | 87.304 | 50.428 | 113.858 | 1.00 | 30.26 |
| ATOM | 2805 | ND2 | ASN | 2240 | 88.244 | 51.839 | 112.405 | 1.00 | 28.28 |
| ATOM | 2806 | C | ASN | 2240 | 88.062 | 48.142 | 111.972 | 1.00 | 28.33 |
| ATOM | 2807 | O | ASN | 2240 | 87.001 | 48.607 | 111.568 | 1.00 | 29.54 |
| ATOM | 2808 | N | HIS | 2241 | 88.165 | 46.943 | 112.524 | 1.00 | 27.96 |
| ATOM | 2809 | CA | HIS | 2241 | 87.010 | 46.106 | 112.727 | 1.00 | 26.95 |
| ATOM | 2810 | CB | HIS | 2241 | 87.081 | 44.867 | 111.848 | 1.00 | 27.14 |
| ATOM | 2811 | CG | HIS | 2241 | 85.795 | 44.109 | 111.785 | 1.00 | 25.98 |
| ATOM | 2812 | CD2 | HIS | 2241 | 85.365 | 43.023 | 112.468 | 1.00 | 26.60 |
| ATOM | 2813 | ND1 | HIS | 2241 | 84.757 | 44.482 | 110.962 | 1.00 | 25.66 |
| ATOM | 2814 | CE1 | HIS | 2241 | 83.743 | 43.656 | 111.138 | 1.00 | 27.38 |
| ATOM | 2815 | NE2 | HIS | 2241 | 84.085 | 42.761 | 112.047 | 1.00 | 28.32 |
| ATOM | 2816 | C | HIS | 2241 | 87.042 | 45.727 | 114.195 | 1.00 | 26.83 |
| ATOM | 2817 | O | HIS | 2241 | 88.097 | 45.791 | 114.840 | 1.00 | 27.26 |
| ATOM | 2818 | N | THR | 2242 | 85.895 | 45.334 | 114.726 | 1.00 | 26.44 |
| ATOM | 2819 | CA | THR | 2242 | 85.827 | 44.978 | 116.129 | 1.00 | 26.55 |
| ATOM | 2820 | CB | THR | 2242 | 85.252 | 46.153 | 116.937 | 1.00 | 24.58 |
| ATOM | 2821 | OG1 | THR | 2242 | 86.180 | 47.241 | 116.898 | 1.00 | 22.77 |
| ATOM | 2822 | CG2 | THR | 2242 | 84.995 | 45.756 | 118.375 | 1.00 | 22.55 |
| ATOM | 2823 | C | THR | 2242 | 85.004 | 43.728 | 116.374 | 1.00 | 27.83 |
| ATOM | 2824 | O | THR | 2242 | 83.844 | 43.650 | 115.970 | 1.00 | 29.08 |
| ATOM | 2825 | N | TYR | 2243 | 85.619 | 42.754 | 117.037 | 1.00 | 28.35 |
| ATOM | 2826 | CA | TYR | 2243 | 84.949 | 41.504 | 117.347 | 1.00 | 29.79 |
| ATOM | 2827 | CB | TYR | 2243 | 85.867 | 40.329 | 117.040 | 1.00 | 30.18 |
| ATOM | 2828 | CG | TYR | 2243 | 86.383 | 40.323 | 115.618 | 1.00 | 30.20 |
| ATOM | 2829 | CD1 | TYR | 2243 | 87.669 | 40.761 | 115.324 | 1.00 | 29.45 |
| ATOM | 2830 | CE1 | TYR | 2243 | 88.161 | 40.716 | 114.027 | 1.00 | 31.01 |
| ATOM | 2831 | CD2 | TYR | 2243 | 85.595 | 39.847 | 114.573 | 1.00 | 29.56 |
| ATOM | 2832 | CE2 | TYR | 2243 | 86.076 | 39.800 | 113.271 | 1.00 | 30.63 |

TABLE 6-continued

FGF2/FGFR1/Heparin Ternary Complex

| ATOM | 2833 | CZ | TYR | 2243 | 87.362 | 40.231 | 113.001 | 1.00 | 31.28 |
|---|---|---|---|---|---|---|---|---|---|
| ATOM | 2834 | OH | TYR | 2243 | 87.856 | 40.162 | 111.715 | 1.00 | 31.89 |
| ATOM | 2835 | C | TYR | 2243 | 84.552 | 41.478 | 118.810 | 1.00 | 30.90 |
| ATOM | 2836 | O | TYR | 2243 | 85.180 | 42.131 | 119.641 | 1.00 | 32.19 |
| ATOM | 2837 | N | GLN | 2244 | 83.507 | 40.725 | 119.127 | 1.00 | 31.55 |
| ATOM | 2838 | CA | GLN | 2244 | 83.040 | 40.629 | 120.501 | 1.00 | 32.33 |
| ATOM | 2839 | CB | GLN | 2244 | 81.541 | 40.895 | 120.579 | 1.00 | 34.66 |
| ATOM | 2840 | CG | GLN | 2244 | 81.114 | 42.118 | 119.818 | 1.00 | 41.95 |
| ATOM | 2841 | CD | GLN | 2244 | 79.612 | 42.191 | 119.631 | 1.00 | 46.48 |
| ATOM | 2842 | OE1 | GLN | 2244 | 78.980 | 41.210 | 119.228 | 1.00 | 50.88 |
| ATOM | 2843 | NE2 | GLN | 2244 | 79.029 | 43.360 | 119.911 | 1.00 | 47.45 |
| ATOM | 2844 | C | GLN | 2244 | 83.299 | 39.225 | 120.971 | 1.00 | 30.93 |
| ATOM | 2845 | O | CLN | 2244 | 82.847 | 38.281 | 120.342 | 1.00 | 32.32 |
| ATOM | 2846 | N | LEU | 2245 | 84.031 | 39.081 | 122.066 | 1.00 | 29.70 |
| ATOM | 2847 | CA | LEU | 2245 | 84.314 | 37.764 | 122.595 | 1.00 | 28.82 |
| ATOM | 2848 | CB | LEU | 2245 | 85.803 | 37.613 | 122.932 | 1.00 | 29.07 |
| ATOM | 2849 | CG | LEU | 2245 | 86.203 | 36.301 | 123.622 | 1.00 | 28.66 |
| ATOM | 2850 | CD1 | LEU | 2245 | 85.712 | 35.124 | 122.828 | 1.00 | 28.15 |
| ATOM | 2851 | CD2 | LEU | 2245 | 87.707 | 36.236 | 123.769 | 1.00 | 29.54 |
| ATOM | 2852 | C | LEU | 2245 | 83.495 | 37.542 | 123.839 | 1.00 | 27.92 |
| ATOM | 2853 | O | LEU | 2245 | 83.411 | 38.416 | 124.694 | 1.00 | 28.60 |
| ATOM | 2854 | N | ASP | 2246 | 82.872 | 36.376 | 123.923 | 1.00 | 27.25 |
| ATOM | 2855 | CA | ASP | 2246 | 82.086 | 36.015 | 125.086 | 1.00 | 27.26 |
| ATOM | 2856 | CB | ASP | 2246 | 80.593 | 36.149 | 124.805 | 1.00 | 28.12 |
| ATOM | 2857 | CG | ASP | 2246 | 79.757 | 36.109 | 126.076 | 1.00 | 30.44 |
| ATOM | 2858 | OD1 | ASP | 2246 | 78.511 | 36.132 | 125.976 | 1.00 | 33.16 |
| ATOM | 2859 | OD2 | ASP | 2246 | 80.343 | 36.061 | 127.180 | 1.00 | 29.88 |
| ATOM | 2860 | C | ASP | 2246 | 82.441 | 34.578 | 125.426 | 1.06 | 27.63 |
| ATOM | 2861 | O | ASP | 2246 | 82.342 | 33.682 | 124.585 | 1.00 | 27.86 |
| ATOM | 2862 | N | VAL | 2247 | 82.881 | 34.370 | 126.661 | 1.00 | 27.19 |
| ATOM | 2863 | CA | VAL | 2247 | 83.275 | 33.049 | 127.116 | 1.00 | 26.28 |
| ATOM | 2864 | CB | VAL | 2247 | 84.661 | 33.111 | 127.724 | 1.00 | 26.83 |
| ATOM | 2865 | CG1 | VAL | 2247 | 85.186 | 31.704 | 127.951 | 1.00 | 26.77 |
| ATOM | 2866 | CG2 | VAL | 2247 | 85.573 | 33.926 | 126.799 | 1.00 | 26.27 |
| ATOM | 2867 | C | VAL | 2247 | 82.270 | 32.478 | 128.117 | 1.00 | 25.49 |
| ATOM | 2868 | O | VAL | 2247 | 81.866 | 33.135 | 129.070 | 1.00 | 25.04 |
| ATOM | 2869 | N | VAL | 2248 | 81.861 | 31.241 | 127.883 | 1.00 | 25.33 |
| ATOM | 2870 | CA | VAL | 2248 | 80.875 | 30.577 | 128.728 | 1.00 | 24.03 |
| ATOM | 2871 | CB | VAL | 2248 | 79.725 | 29.997 | 127.854 | 1.00 | 22.77 |
| ATOM | 2872 | CG1 | VAL | 2248 | 78.704 | 29.305 | 128.707 | 1.00 | 21.53 |
| ATOM | 2873 | CG2 | VAL | 2248 | 79.080 | 31.093 | 127.056 | 1.00 | 21.73 |
| ATOM | 2874 | C | VAL | 2248 | 81.525 | 29.432 | 129.501 | 1.00 | 24.15 |
| ATOM | 2875 | O | VAL | 2248 | 82.047 | 28.504 | 128.891 | 1.00 | 24.08 |
| ATOM | 2876 | N | GLU | 2249 | 81.538 | 29.492 | 130.833 | 1.00 | 24.50 |
| ATOM | 2877 | CA | GLU | 2249 | 82.133 | 28.392 | 131.605 | 1.00 | 25.67 |
| ATOM | 2878 | CB | GLU | 2249 | 82.573 | 28.855 | 133.002 | 1.00 | 25.92 |
| ATOM | 2879 | CG | GLU | 2249 | 83.681 | 29.907 | 133.001 | 1.00 | 27.35 |
| ATOM | 2880 | CD | GLU | 2249 | 84.096 | 30.356 | 134.400 | 1.00 | 28.29 |
| ATOM | 2881 | OE1 | GLU | 2249 | 83.223 | 30.792 | 135.169 | 1.00 | 29.15 |
| ATOM | 2882 | OE2 | GLU | 2249 | 85.298 | 30.287 | 134.729 | 1.00 | 28.96 |
| ATOM | 2883 | C | GLU | 2249 | 81.089 | 27.287 | 131.731 | 1.00 | 25.94 |
| ATOM | 2884 | O | GLU | 2249 | 79.934 | 27.550 | 132.090 | 1.00 | 27.27 |
| ATOM | 2885 | N | ARG | 2250 | 81.488 | 26.055 | 131.434 | 1.00 | 24.48 |
| ATOM | 2886 | CA | ARG | 2250 | 80.564 | 24.931 | 131.494 | 1.00 | 24.34 |
| ATOM | 2887 | CB | ARG | 2250 | 80.731 | 24.071 | 130.239 | 1.00 | 22.86 |
| ATOM | 2888 | CG | ARG | 2250 | 80.671 | 24.831 | 128.918 | 1.00 | 21.47 |
| ATOM | 2889 | CD | ARG | 2250 | 79.364 | 25.574 | 128.775 | 1.00 | 20.47 |
| ATOM | 2890 | NE | ARG | 2250 | 78.209 | 24.684 | 128.907 | 1.00 | 18.58 |
| ATOM | 2891 | CZ | ARG | 2250 | 77.726 | 23.919 | 127.934 | 1.00 | 16.19 |
| ATOM | 2892 | NH1 | ARG | 2250 | 78.277 | 23.928 | 226.732 | 1.00 | 15.47 |
| ATOM | 2893 | NH2 | ARG | 2250 | 76.681 | 23.150 | 128.172 | 1.00 | 14.35 |
| ATOM | 2894 | C | ARG | 2250 | 80.734 | 24.048 | 132.737 | 1.00 | 25.57 |
| ATOM | 2895 | O | ARG | 2250 | 81.855 | 23.784 | 133.154 | 1.00 | 26.62 |
| ATOM | 2896 | N | SER | 2251 | 79.622 | 23.588 | 133.318 | 1.00 | 27.67 |
| ATOM | 2897 | CA | SER | 2251 | 79.648 | 22.705 | 134.498 | 1.00 | 29.59 |
| ATOM | 2898 | CB | SER | 2251 | 78.802 | 23.289 | 135.645 | 1.00 | 29.49 |
| ATOM | 2899 | OG | SER | 2251 | 79.417 | 24.407 | 136.271 | 1.00 | 29.28 |
| ATOM | 2900 | C | SER | 2251 | 79.094 | 21.322 | 134.138 | 1.00 | 30.92 |
| ATOM | 2901 | O | SER | 2251 | 77.887 | 21.103 | 134.227 | 1.00 | 30.80 |
| ATOM | 2902 | N | PRO | 2252 | 79.972 | 20.372 | 133.747 | 1.00 | 32.52 |
| ATOM | 2903 | CD | PRO | 2252 | 81.428 | 20.579 | 133.660 | 1.00 | 33.32 |
| ATOM | 2904 | CA | PRO | 2252 | 79.641 | 18.996 | 133.357 | 1.00 | 33.64 |
| ATOM | 2905 | CB | PRO | 2252 | 80.797 | 18.638 | 132.462 | 1.00 | 32.97 |
| ATOM | 2906 | CG | PRO | 2252 | 81.936 | 19.192 | 133.257 | 1.00 | 33.41 |
| ATOM | 2907 | C | PRO | 2252 | 79.557 | 18.052 | 134.554 | 1.00 | 35.26 |
| ATOM | 2908 | O | PRO | 2252 | 80.393 | 17.162 | 134.709 | 1.00 | 35.60 |
| ATOM | 2909 | N | HIS | 2253 | 78.547 | 18.245 | 135.390 | 1.00 | 36.75 |

TABLE 6-continued

FGF2/FGFR1/Heparin Ternary Complex

| ATOM | 2910 | CA  | HIS | 2253 | 78.380 | 17.423 | 136.577 | 1.00 | 39.62 |
|------|------|-----|-----|------|--------|--------|---------|------|-------|
| ATOM | 2911 | CB  | HIS | 2253 | 78.988 | 18.135 | 137.782 | 1.00 | 43.57 |
| ATOM | 2912 | CG  | HIS | 2253 | 80.472 | 18.278 | 137.709 | 1.00 | 48.09 |
| ATOM | 2913 | CD2 | HIS | 2253 | 81.447 | 17.888 | 138.563 | 1.00 | 49.70 |
| ATOM | 2914 | ND1 | HIS | 2253 | 81.110 | 18.861 | 136.636 | 1.00 | 50.53 |
| ATOM | 2915 | CE1 | HIS | 2253 | 82.416 | 18.821 | 136.831 | 1.00 | 52.26 |
| ATOM | 2916 | NE2 | HIS | 2253 | 82.647 | 18.236 | 137.994 | 1.00 | 51.65 |
| ATOM | 2917 | C   | HIS | 2253 | 76.918 | 17.175 | 136.860 | 1.00 | 38.87 |
| ATOM | 2918 | O   | HIS | 2253 | 76.053 | 17.848 | 136.305 | 1.00 | 39.07 |
| ATOM | 2919 | N   | ARG | 2254 | 76.634 | 16.213 | 137.731 | 1.00 | 37.62 |
| ATOM | 2920 | CA  | ARG | 2254 | 75.249 | 15.958 | 138.065 | 1.00 | 36.58 |
| ATOM | 2921 | CB  | ARG | 2254 | 75.111 | 14.724 | 138.963 | 1.00 | 37.86 |
| ATOM | 2922 | CG  | ARG | 2254 | 75.908 | 14.745 | 140.243 | 1.00 | 39.87 |
| ATOM | 2923 | CD  | ARG | 2254 | 75.703 | 13.437 | 141.000 | 1.00 | 41.72 |
| ATOM | 2924 | NE  | ARG | 2254 | 75.427 | 13.677 | 142.414 | 1.00 | 44.34 |
| ATOM | 2925 | CZ  | ARG | 2254 | 76.355 | 13.791 | 143.358 | 1.00 | 44.80 |
| ATOM | 2926 | NH1 | ARG | 2254 | 77.643 | 13.672 | 143.050 | 1.00 | 46.11 |
| ATOM | 2927 | NH2 | ARG | 2254 | 75.989 | 14.058 | 144.607 | 1.00 | 45.02 |
| ATOM | 2928 | C   | ARG | 2254 | 74.757 | 17.219 | 138.756 | 1.00 | 34.56 |
| ATOM | 2929 | O   | ARG | 2254 | 75.548 | 18.025 | 139.229 | 1.00 | 34.81 |
| ATOM | 2930 | N   | PRO | 2255 | 73.443 | 17.428 | 138.792 | 1.00 | 33.17 |
| ATOM | 2931 | CD  | PRO | 2255 | 72.344 | 16.608 | 138.261 | 1.00 | 32.67 |
| ATOM | 2932 | CA  | PRO | 2255 | 72.937 | 18.638 | 139.445 | 1.00 | 31.64 |
| ATOM | 2933 | CB  | PRO | 2255 | 71.422 | 18.512 | 139.288 | 1.00 | 31.80 |
| ATOM | 2934 | CG  | PRO | 2255 | 71.219 | 17.022 | 139.152 | 1.00 | 33.31 |
| ATOM | 2935 | C   | PRO | 2255 | 73.382 | 18.777 | 140.887 | 1.00 | 30.09 |
| ATOM | 2936 | O   | PRO | 2255 | 73.759 | 17.807 | 141.520 | 1.00 | 29.82 |
| ATOM | 2937 | N   | ILE | 2256 | 73.351 | 20.001 | 141.391 | 1.00 | 29.29 |
| ATOM | 2938 | CA  | ILE | 2256 | 73.742 | 20.275 | 142.763 | 1.00 | 29.70 |
| ATOM | 2939 | CB  | ILE | 2256 | 74.964 | 21.191 | 142.795 | 1.00 | 30.13 |
| ATOM | 2940 | CG2 | ILE | 2256 | 75.252 | 21.633 | 144.218 | 1.00 | 30.25 |
| ATOM | 2941 | CG1 | ILE | 2256 | 76.149 | 20.472 | 142.163 | 1.00 | 29.49 |
| ATOM | 2942 | CD1 | ILE | 2256 | 77.398 | 21.292 | 142.128 | 1.00 | 32.07 |
| ATOM | 2943 | C   | ILE | 2256 | 72.593 | 20.953 | 143.511 | 1.00 | 30.42 |
| ATOM | 2944 | O   | ILE | 2256 | 72.040 | 21.950 | 143.036 | 1.00 | 30.59 |
| ATOM | 2945 | N   | LEU | 2257 | 72.234 | 20.414 | 144.677 | 1.00 | 29.49 |
| ATOM | 2946 | CA  | LEU | 2257 | 71.140 | 20.986 | 145.453 | 1.00 | 29.81 |
| ATOM | 2947 | CB  | LEU | 2257 | 70.230 | 19.888 | 146.023 | 1.00 | 30.16 |
| ATOM | 2948 | CG  | LEU | 2257 | 69.651 | 18.754 | 145.166 | 1.00 | 30.57 |
| ATOM | 2949 | CD1 | LEU | 2257 | 68.237 | 18.428 | 145.650 | 1.00 | 28.49 |
| ATOM | 2950 | CD2 | LEU | 2257 | 69.619 | 19.160 | 143.703 | 1.00 | 30.97 |
| ATOM | 2951 | C   | LEU | 2257 | 71.681 | 21.813 | 146.606 | 1.00 | 30.20 |
| ATOM | 2952 | O   | LEU | 2257 | 72.579 | 21.370 | 147.311 | 1.00 | 31.09 |
| ATOM | 2953 | N   | GLN | 2258 | 71.137 | 23.013 | 146.804 | 1.00 | 29.96 |
| ATOM | 2954 | CA  | GLN | 2258 | 71.585 | 23.869 | 147.902 | 1.00 | 28.96 |
| ATOM | 2955 | CB  | GLN | 2258 | 70.717 | 25.122 | 148.021 | 1.00 | 28.83 |
| ATOM | 2956 | C   | GLN | 2258 | 71.485 | 23.092 | 149.201 | 1.00 | 28.90 |
| ATOM | 2957 | O   | GLN | 2258 | 70.412 | 22.631 | 149.584 | 1.00 | 29.36 |
| ATOM | 2958 | N   | ALA | 2259 | 72.614 | 22.935 | 149.874 | 1.00 | 28.31 |
| ATOM | 2959 | CA  | ALA | 2259 | 72.637 | 22.232 | 151.141 | 1.00 | 26.85 |
| ATOM | 2960 | CB  | ALA | 2259 | 74.014 | 22.353 | 151.773 | 1.00 | 26.17 |
| ATOM | 2961 | C   | ALA | 2259 | 71.596 | 22.859 | 152.057 | 1.00 | 26.35 |
| ATOM | 2962 | O   | ALA | 2259 | 71.340 | 24.057 | 151.989 | 1.00 | 26.69 |
| ATOM | 2963 | N   | GLY | 2260 | 70.987 | 22.048 | 152.908 | 1.00 | 26.17 |
| ATOM | 2964 | CA  | GLY | 2260 | 70.010 | 22.580 | 153.831 | 1.00 | 26.69 |
| ATOM | 2965 | C   | GLY | 2260 | 68.583 | 22.528 | 153.332 | 1.00 | 27.47 |
| ATOM | 2966 | O   | GLY | 2260 | 67.647 | 22.592 | 154.135 | 1.00 | 27.56 |
| ATOM | 2967 | N   | LEU | 2261 | 68.405 | 22.433 | 152.017 | 1.00 | 27.03 |
| ATOM | 2968 | CA  | LEU | 2261 | 67.066 | 22.364 | 151.454 | 1.00 | 26.14 |
| ATOM | 2969 | CB  | LEU | 2261 | 66.824 | 23.561 | 150.548 | 1.00 | 23.68 |
| ATOM | 2970 | CG  | LEU | 2261 | 67.108 | 24.907 | 151.206 | 1.00 | 21.44 |
| ATOM | 2971 | CD1 | LEU | 2261 | 66.415 | 26.001 | 150.409 | 1.00 | 19.96 |
| ATOM | 2972 | CD2 | LEU | 2261 | 66.606 | 24.901 | 152.631 | 1.00 | 20.06 |
| ATOM | 2973 | C   | LEU | 2261 | 66.844 | 21.055 | 150.694 | 1.00 | 27.99 |
| ATOM | 2974 | O   | LEU | 2261 | 67.742 | 20.569 | 149.995 | 1.00 | 29.22 |
| ATOM | 2975 | N   | PRO | 2262 | 65.641 | 20.461 | 150.824 | 1.00 | 28.27 |
| ATOM | 2976 | CD  | PRO | 2262 | 65.334 | 19.148 | 150.228 | 1.00 | 27.52 |
| ATOM | 2977 | CA  | PRO | 2262 | 64.507 | 20.941 | 151.626 | 1.00 | 27.27 |
| ATOM | 2978 | CB  | PRO | 2262 | 63.380 | 19.991 | 151.232 | 1.00 | 26.90 |
| ATOM | 2979 | CG  | PRO | 2262 | 64.107 | 18.717 | 151.000 | 1.00 | 27.49 |
| ATOM | 2980 | C   | PRO | 2262 | 64.822 | 20.899 | 153.110 | 1.00 | 26.77 |
| ATOM | 2981 | O   | PRO | 2262 | 65.772 | 20.243 | 153.526 | 1.00 | 25.45 |
| ATOM | 2982 | N   | ALA | 2263 | 64.025 | 21.590 | 153.911 | 1.00 | 27.41 |
| ATOM | 2983 | CA  | ALA | 2263 | 64.293 | 21.629 | 155.342 | 1.00 | 28.52 |
| ATOM | 2984 | CB  | ALA | 2263 | 64.411 | 23.068 | 155.794 | 1.00 | 29.22 |
| ATOM | 2985 | C   | ALA | 2263 | 63.261 | 20.915 | 156.183 | 1.00 | 29.21 |
| ATOM | 2986 | O   | ALA | 2263 | 62.068 | 21.002 | 155.909 | 1.00 | 29.99 |

TABLE 6-continued

| | | | FGF2/FGFR1/Heparin Ternary Complex | | | | | |
|---|---|---|---|---|---|---|---|---|
| ATOM | 2987 | N | ASN | 2264 | 63.716 | 20.213 | 157.213 | 1.00 | 29.48 |
| ATOM | 2988 | CA | ASN | 2264 | 62.782 | 19.522 | 158.075 | 1.00 | 30.81 |
| ATOM | 2989 | CB | ASN | 2264 | 63.511 | 18.779 | 159.183 | 1.00 | 31.19 |
| ATOM | 2990 | CG | ASN | 2264 | 64.414 | 17.697 | 158.653 | 1.00 | 33.95 |
| ATOM | 2991 | OD1 | ASN | 2264 | 64.021 | 16.915 | 157.791 | 1.00 | 35.19 |
| ATOM | 2992 | ND2 | ASN | 2264 | 65.635 | 17.635 | 159.173 | 1.00 | 36.12 |
| ATOM | 2993 | C | ASN | 2264 | 61.870 | 20.562 | 158.688 | 1.00 | 32.46 |
| ATOM | 2994 | O | ASN | 2264 | 62.313 | 21.654 | 159.049 | 1.00 | 33.58 |
| ATOM | 2995 | N | LYS | 2265 | 60.589 | 20.242 | 158.788 | 1.00 | 33.38 |
| ATOM | 2996 | CA | LYS | 2265 | 59.651 | 21.169 | 159.387 | 1.00 | 34.69 |
| ATOM | 2997 | CB | LYS | 2265 | 58.895 | 21.962 | 158.325 | 1.00 | 33.92 |
| ATOM | 2998 | CG | LYS | 2265 | 59.765 | 22.767 | 157.408 | 1.00 | 35.31 |
| ATOM | 2999 | CD | LYS | 2265 | 58.923 | 23.796 | 156.699 | 1.00 | 38.59 |
| ATOM | 3000 | CE | LYS | 2265 | 59.563 | 24.252 | 155.406 | 1.00 | 40.99 |
| ATOM | 3001 | NZ | LYS | 2265 | 59.557 | 23.168 | 154.382 | 1.00 | 42.54 |
| ATOM | 3002 | C | LYS | 2265 | 58.660 | 20.408 | 160.241 | 1.00 | 36.45 |
| ATOM | 3003 | O | LYS | 2265 | 58.172 | 19.345 | 159.857 | 1.00 | 38.01 |
| ATOM | 3004 | N | THR | 2266 | 58.384 | 20.950 | 161.417 | 1.00 | 37.19 |
| ATOM | 3005 | CA | THR | 2266 | 57.421 | 20.365 | 162.331 | 1.00 | 37.14 |
| ATOM | 3006 | CB | THR | 2266 | 58.019 | 20.261 | 163.744 | 1.00 | 37.39 |
| ATOM | 3007 | OG1 | THR | 2266 | 59.134 | 19.361 | 163.715 | 1.00 | 37.04 |
| ATOM | 3008 | CG2 | THR | 2266 | 56.994 | 19.753 | 164.729 | 1.00 | 37.38 |
| ATOM | 3009 | C | THR | 2266 | 56.255 | 21.343 | 162.293 | 1.00 | 37.21 |
| ATOM | 3010 | O | THR | 2266 | 56.450 | 22.548 | 162.427 | 1.00 | 36.61 |
| ATOM | 3011 | N | VAL | 2267 | 55.048 | 20.840 | 162.069 | 1.00 | 38.23 |
| ATOM | 3012 | CA | VAL | 2267 | 53.889 | 21.723 | 161.988 | 1.00 | 39.46 |
| ATOM | 3013 | CB | VAL | 2267 | 53.548 | 22.067 | 160.534 | 1.00 | 39.17 |
| ATOM | 3014 | CG1 | VAL | 2267 | 54.768 | 22.625 | 159.824 | 1.00 | 39.01 |
| ATOM | 3015 | CG2 | VAL | 2267 | 53.027 | 20.829 | 159.831 | 1.00 | 39.27 |
| ATOM | 3016 | C | VAL | 2267 | 52.635 | 21.138 | 162.608 | 1.00 | 40.66 |
| ATOM | 3017 | O | VAL | 2267 | 52.543 | 19.932 | 162.848 | 1.00 | 42.01 |
| ATOM | 3018 | N | ALA | 2268 | 51.664 | 22.012 | 162.843 | 1.00 | 41.22 |
| ATOM | 3019 | CA | ALA | 2268 | 50.400 | 21.627 | 163.439 | 1.00 | 41.45 |
| ATOM | 3020 | CB | ALA | 2268 | 49.697 | 22.853 | 163.965 | 1.00 | 41.09 |
| ATOM | 3021 | C | ALA | 2268 | 49.512 | 20.910 | 162.435 | 1.00 | 41.95 |
| ATOM | 3022 | O | ALA | 2268 | 49.542 | 21.197 | 161.238 | 1.00 | 42.09 |
| ATOM | 3023 | N | LEU | 2269 | 48.730 | 19.962 | 162.927 | 1.00 | 42.41 |
| ATOM | 3024 | CA | LEU | 2269 | 47.826 | 19.221 | 162.069 | 1.00 | 43.71 |
| ATOM | 3025 | CB | LEU | 2269 | 46.992 | 18.259 | 162.922 | 1.00 | 44.16 |
| ATOM | 3026 | CG | LEU | 2269 | 45.907 | 17.412 | 162.257 | 1.00 | 44.43 |
| ATOM | 3027 | CD1 | LEU | 2269 | 45.865 | 16.040 | 162.909 | 1.00 | 44.37 |
| ATOM | 3028 | CD2 | LEU | 2269 | 44.559 | 18.122 | 162.361 | 1.00 | 44.90 |
| ATOM | 3029 | C | LEU | 2269 | 46.933 | 20.226 | 161.342 | 1.00 | 44.37 |
| ATOM | 3030 | O | LEU | 2269 | 46.468 | 21.193 | 161.940 | 1.00 | 44.68 |
| ATOM | 3031 | N | GLY | 2270 | 46.718 | 20.016 | 160.047 | 1.00 | 44.77 |
| ATOM | 3032 | CA | GLY | 2270 | 45.873 | 20.920 | 159.286 | 1.00 | 44.86 |
| ATOM | 3033 | C | GLY | 2270 | 46.569 | 22.151 | 158.725 | 1.00 | 45.21 |
| ATOM | 3034 | O | GLY | 2270 | 45.978 | 22.898 | 157.938 | 1.00 | 46.08 |
| ATOM | 3035 | N | SER | 2271 | 47.821 | 22.368 | 159.120 | 1.00 | 44.66 |
| ATOM | 3036 | CA | SER | 2271 | 48.599 | 23.514 | 158.643 | 1.00 | 44.47 |
| ATOM | 3037 | CB | SER | 2271 | 49.962 | 23.551 | 159.337 | 1.00 | 43.11 |
| ATOM | 3038 | OG | SER | 2271 | 49.839 | 23.441 | 160.737 | 1.00 | 43.71 |
| ATOM | 3039 | C | SER | 2271 | 48.870 | 23.488 | 157.134 | 1.00 | 44.57 |
| ATOM | 3040 | O | SER | 2271 | 48.425 | 22.592 | 156.406 | 1.00 | 45.14 |
| ATOM | 3041 | N | ASN | 2272 | 49.622 | 24.487 | 156.685 | 1.00 | 43.89 |
| ATOM | 3042 | CA | ASN | 2272 | 50.040 | 24.605 | 155.290 | 1.00 | 43.78 |
| ATOM | 3043 | CB | ASN | 2272 | 49.604 | 25.931 | 154.672 | 1.00 | 45.49 |
| ATOM | 3044 | CG | ASN | 2272 | 48.121 | 26.029 | 154.494 | 1.00 | 47.22 |
| ATOM | 3045 | OD1 | ASN | 2272 | 47.515 | 25.236 | 153.769 | 1.00 | 48.34 |
| ATOM | 3046 | ND2 | ASN | 2272 | 47.514 | 27.010 | 155.155 | 1.00 | 49.19 |
| ATOM | 3047 | C | ASN | 2272 | 51.553 | 24.603 | 155.341 | 1.00 | 42.43 |
| ATOM | 3048 | O | ASN | 2272 | 52.146 | 25.277 | 156.176 | 1.00 | 42.15 |
| ATOM | 3049 | N | VAL | 2273 | 52.185 | 23.858 | 154.451 | 1.00 | 41.35 |
| ATOM | 3050 | CA | VAL | 2273 | 53.636 | 23.811 | 154.445 | 1.00 | 40.09 |
| ATOM | 3051 | CB | VAL | 2273 | 54.156 | 22.581 | 155.213 | 1.00 | 39.83 |
| ATOM | 3052 | CG1 | VAL | 2273 | 53.383 | 21.362 | 154.797 | 1.00 | 40.44 |
| ATOM | 3053 | CG2 | VAL | 2273 | 55.640 | 22.369 | 154.931 | 1.00 | 39.62 |
| ATOM | 3054 | C | VAL | 2273 | 54.164 | 23.747 | 153.035 | 1.00 | 39.30 |
| ATOM | 3055 | O | VAL | 2273 | 53.531 | 23.169 | 152.156 | 1.00 | 39.51 |
| ATOM | 3056 | N | GLU | 2274 | 55.317 | 24.360 | 152.818 | 1.00 | 38.06 |
| ATOM | 3057 | CA | GLU | 2274 | 55.926 | 24.320 | 151.512 | 1.00 | 38.64 |
| ATOM | 3058 | CB | GLU | 2274 | 55.685 | 25.638 | 150.763 | 1.00 | 40.66 |
| ATOM | 3059 | CG | GLU | 2274 | 56.370 | 26.881 | 151.318 | 1.00 | 43.80 |
| ATOM | 3060 | CD | GLU | 2274 | 55.780 | 28.173 | 150.741 | 1.00 | 45.03 |
| ATOM | 3061 | OE1 | GLU | 2274 | 54.604 | 28.468 | 151.045 | 1.00 | 46.22 |
| ATOM | 3062 | OE2 | GLU | 2274 | 56.479 | 28.887 | 149.985 | 1.00 | 44.78 |
| ATOM | 3063 | C | GLU | 2274 | 57.410 | 23.997 | 151.637 | 1.00 | 37.72 |

TABLE 6-continued

FGF2/FGFR1/Heparin Ternary Complex

| ATOM | 3064 | O | GLU | 2274 | 58.132 | 24.605 | 152.428 | 1.00 | 38.00 |
|---|---|---|---|---|---|---|---|---|---|
| ATOM | 3065 | N | PHE | 2275 | 57.843 | 22.995 | 150.880 | 1.00 | 36.09 |
| ATOM | 3066 | CA | PHE | 2275 | 59.234 | 22.567 | 150.882 | 1.00 | 34.28 |
| ATOM | 3067 | CB | PHE | 2275 | 59.320 | 21.059 | 150.722 | 1.00 | 32.50 |
| ATOM | 3068 | CG | PHE | 2275 | 59.230 | 20.314 | 152.011 | 1.00 | 31.28 |
| ATOM | 3069 | CD1 | PHE | 2275 | 60.273 | 20.366 | 152.928 | 1.00 | 30.79 |
| ATOM | 3070 | CD2 | PHE | 2275 | 58.113 | 19.552 | 152.310 | 1.00 | 30.84 |
| ATOM | 3071 | CE1 | PHE | 2275 | 60.206 | 19.672 | 154.116 | 1.00 | 29.97 |
| ATOM | 3072 | CE2 | PHE | 2275 | 58.035 | 18.850 | 153.500 | 1.00 | 29.96 |
| ATOM | 3073 | CZ | PHE | 2275 | 59.084 | 18.910 | 154.405 | 1.00 | 30.45 |
| ATOM | 3074 | C | PHE | 2275 | 59.966 | 23.238 | 149.745 | 1.00 | 33.99 |
| ATOM | 3075 | O | PHE | 2275 | 59.389 | 23.511 | 148.701 | 1.00 | 33.87 |
| ATOM | 3076 | N | MET | 2276 | 61.246 | 23.497 | 149.933 | 1.00 | 33.77 |
| ATOM | 3077 | CA | MET | 2276 | 61.983 | 24.162 | 148.890 | 1.00 | 34.52 |
| ATOM | 3078 | CB | MET | 2276 | 62.365 | 25.544 | 149.387 | 1.00 | 37.58 |
| ATOM | 3079 | CG | MET | 2276 | 62.775 | 26.494 | 148.306 | 1.00 | 43.79 |
| ATOM | 3080 | SD | MET | 2276 | 62.744 | 28.176 | 148.933 | 1.00 | 52.43 |
| ATOM | 3081 | CE | MET | 2276 | 63.765 | 28.004 | 150.468 | 1.00 | 49.38 |
| ATOM | 3082 | C | MET | 2276 | 63.207 | 23.385 | 148.416 | 1.00 | 33.46 |
| ATOM | 3083 | O | MET | 2276 | 63.807 | 22.615 | 149.165 | 1.00 | 32.44 |
| ATOM | 3084 | N | CYS | 2277 | 63.563 | 23.586 | 147.152 | 1.00 | 32.65 |
| ATOM | 3085 | CA | CYS | 2277 | 64.700 | 22.898 | 146.572 | 1.00 | 32.07 |
| ATOM | 3086 | C | CYS | 2277 | 65.361 | 23.762 | 145.510 | 1.00 | 31.59 |
| ATOM | 3087 | O | CYS | 2277 | 64.772 | 24.050 | 144.473 | 1.00 | 32.69 |
| ATOM | 3088 | CB | CYS | 2277 | 64.234 | 21.579 | 145.967 | 1.00 | 31.67 |
| ATOM | 3089 | SG | CYS | 2277 | 65.563 | 20.403 | 145.571 | 1.00 | 33.74 |
| ATOM | 3090 | N | LYS | 2278 | 66.590 | 24.179 | 145.785 | 1.00 | 31.20 |
| ATOM | 3091 | CA | LYS | 2278 | 67.360 | 25.024 | 144.876 | 1.00 | 30.18 |
| ATOM | 3092 | CB | LYS | 2278 | 68.083 | 26.122 | 145.672 | 1.00 | 28.01 |
| ATOM | 3093 | C | LYS | 2278 | 68.371 | 24.164 | 144.119 | 1.00 | 29.96 |
| ATOM | 3094 | O | LYS | 2278 | 69.321 | 23.637 | 144.707 | 1.00 | 30.70 |
| ATOM | 3095 | N | VAL | 2279 | 68.170 | 24.033 | 142.811 | 1.00 | 28.81 |
| ATOM | 3096 | CA | VAL | 2279 | 69.036 | 23.201 | 141.979 | 1.00 | 27.68 |
| ATOM | 3097 | CB | VAL | 2279 | 68.186 | 22.212 | 141.121 | 1.00 | 25.96 |
| ATOM | 3098 | CG1 | VAL | 2279 | 69.068 | 21.351 | 140.274 | 1.00 | 24.56 |
| ATOM | 3099 | CG2 | VAL | 2279 | 67.352 | 21.345 | 142.010 | 1.00 | 26.30 |
| ATOM | 3100 | C | VAL | 2279 | 69.950 | 23.976 | 141.034 | 1.00 | 27.72 |
| ATOM | 3101 | O | VAL | 2279 | 69.568 | 25.006 | 140.479 | 1.00 | 27.19 |
| ATOM | 3102 | N | TYR | 2280 | 71.171 | 23.473 | 140.869 | 1.00 | 28.17 |
| ATOM | 3103 | CA | TYR | 2280 | 72.135 | 24.064 | 139.947 | 1.00 | 27.42 |
| ATOM | 3104 | CB | TYR | 2280 | 73.405 | 24.525 | 140.652 | 1.00 | 27.41 |
| ATOM | 3105 | CG | TYR | 2280 | 74.394 | 25.059 | 139.655 | 1.00 | 27.18 |
| ATOM | 3106 | CD1 | TYR | 2280 | 74.222 | 26.321 | 139.097 | 1.00 | 28.01 |
| ATOM | 3107 | CE1 | TYR | 2280 | 75.029 | 26.771 | 138.067 | 1.00 | 26.71 |
| ATOM | 3108 | CD2 | TYR | 2280 | 75.417 | 24.258 | 139.159 | 1.00 | 26.24 |
| ATOM | 3109 | CE2 | TYR | 2280 | 76.231 | 24.701 | 138.124 | 1.00 | 25.96 |
| ATOM | 3110 | CZ | TYR | 2280 | 76.023 | 25.959 | 137.582 | 1.00 | 26.31 |
| ATOM | 3111 | OH | TYR | 2280 | 76.780 | 26.400 | 136.529 | 1.00 | 28.45 |
| ATOM | 3112 | C | TYR | 2280 | 72.520 | 22.975 | 138.956 | 1.00 | 27.11 |
| ATOM | 3113 | O | TYR | 2280 | 72.691 | 21.820 | 139.341 | 1.00 | 28.12 |
| ATOM | 3114 | N | SER | 2281 | 72.674 | 23.337 | 137.689 | 1.00 | 25.08 |
| ATOM | 3115 | CA | SER | 2281 | 73.028 | 22.359 | 136.676 | 1.00 | 23.95 |
| ATOM | 3116 | CB | SER | 2281 | 71.908 | 21.324 | 136.533 | 1.00 | 24.09 |
| ATOM | 3117 | OG | SER | 2281 | 72.181 | 20.398 | 135.489 | 1.00 | 22.96 |
| ATOM | 3118 | C | SER | 2281 | 73.238 | 23.031 | 135.345 | 1.00 | 23.28 |
| ATOM | 3119 | O | SER | 2281 | 72.375 | 23.764 | 134.878 | 1.00 | 22.83 |
| ATOM | 3120 | N | ASP | 2282 | 74.380 | 22.784 | 134.715 | 1.00 | 23.54 |
| ATOM | 3121 | CA | ASP | 2282 | 74.604 | 23.389 | 133.422 | 1.00 | 22.96 |
| ATOM | 3122 | CB | ASP | 2282 | 76.019 | 23.128 | 132.924 | 1.00 | 24.67 |
| ATOM | 3123 | CG | ASP | 2282 | 76.314 | 23.850 | 131.637 | 1.00 | 27.89 |
| ATOM | 3124 | OG1 | ASP | 2282 | 77.502 | 23.973 | 131.293 | 1.00 | 29.40 |
| ATOM | 3125 | OD2 | ASP | 2282 | 75.358 | 24.291 | 130.960 | 1.00 | 30.16 |
| ATOM | 3126 | C | ASP | 2282 | 73.563 | 22.754 | 132.524 | 1.00 | 21.66 |
| ATOM | 3127 | O | ASP | 2282 | 72.618 | 23.409 | 132.125 | 1.00 | 21.72 |
| ATOM | 3128 | N | PRO | 2283 | 73.695 | 21.456 | 132.228 | 1.00 | 21.91 |
| ATOM | 3129 | CD | PRO | 2283 | 74.691 | 20.479 | 132.692 | 1.00 | 22.08 |
| ATOM | 3130 | CA | PRO | 2283 | 72.701 | 20.802 | 131.371 | 1.00 | 22.90 |
| ATOM | 3131 | CB | PRO | 2283 | 73.166 | 19.354 | 131.342 | 1.00 | 22.53 |
| ATOM | 3132 | CG | PRO | 2283 | 74.626 | 19.447 | 131.616 | 1.00 | 21.93 |
| ATOM | 3133 | C | PRO | 2283 | 71.323 | 20.916 | 132.019 | 1.00 | 23.26 |
| ATOM | 3134 | O | PRO | 2283 | 71.191 | 20.844 | 133.240 | 1.00 | 22.90 |
| ATOM | 3135 | N | GLN | 2284 | 70.298 | 21.077 | 131.203 | 1.00 | 23.49 |
| ATOM | 3136 | CA | GLN | 2284 | 68.946 | 21.192 | 131.714 | 1.00 | 24.43 |
| ATOM | 3137 | CB | GLN | 2284 | 67.964 | 21.127 | 130.542 | 1.00 | 25.05 |
| ATOM | 3138 | CG | GLN | 2284 | 66.814 | 22.065 | 130.681 | 1.00 | 25.12 |
| ATOM | 3139 | CD | GLN | 2284 | 67.292 | 23.440 | 131.000 | 1.00 | 25.68 |
| ATOM | 3140 | OE1 | GLN | 2284 | 67.992 | 24.077 | 130.202 | 1.00 | 27.13 |

TABLE 6-continued

FGF2/FGFR1/Heparin Ternary Complex

| ATOM | 3141 | NE2 | GLN | 2284 | 66.941 | 23.914 | 132.181 | 1.00 | 26.58 |
|---|---|---|---|---|---|---|---|---|---|
| ATOM | 3142 | C | GLN | 2284 | 68.646 | 20.052 | 132.695 | 1.00 | 24.85 |
| ATOM | 3143 | O | GLN | 2284 | 68.624 | 18.881 | 132.303 | 1.00 | 25.65 |
| ATOM | 3144 | N | PRO | 2285 | 68.417 | 20.373 | 133.978 | 1.00 | 24.45 |
| ATOM | 3145 | CD | PRO | 2285 | 68.537 | 21.685 | 134.637 | 1.00 | 24.26 |
| ATOM | 3146 | CA | PRO | 2285 | 68.119 | 19.336 | 134.969 | 1.00 | 24.12 |
| ATOM | 3147 | CB | PRO | 2285 | 68.541 | 19.980 | 136.271 | 1.00 | 23.75 |
| ATOM | 3148 | CG | PRO | 2285 | 68.097 | 21.378 | 136.070 | 1.00 | 22.99 |
| ATOM | 3149 | C | PRO | 2285 | 66.637 | 18.990 | 134.988 | 1.00 | 24.46 |
| ATOM | 3150 | O | PRO | 2285 | 65.787 | 19.759 | 134.533 | 1.00 | 25.13 |
| ATOM | 3151 | N | HIS | 2286 | 66.327 | 17.823 | 135.519 | 1.00 | 24.23 |
| ATOM | 3152 | CA | HIS | 2286 | 64.946 | 17.408 | 135.620 | 1.00 | 24.03 |
| ATOM | 3153 | CB | HIS | 2286 | 64.712 | 16.157 | 134.784 | 1.00 | 24.57 |
| ATOM | 3154 | CG | HIS | 2286 | 63.319 | 15.629 | 134.894 | 1.00 | 25.55 |
| ATOM | 3155 | CD2 | HIS | 2286 | 62.275 | 15.690 | 134.040 | 1.00 | 25.90 |
| ATOM | 3156 | ND1 | HIS | 2286 | 62.853 | 14.997 | 136.026 | 1.00 | 26.20 |
| ATOM | 3157 | CE1 | HIS | 2286 | 61.580 | 14.689 | 135.863 | 1.00 | 26.25 |
| ATOM | 3158 | NE2 | HIS | 2286 | 61.205 | 15.098 | 134.664 | 1.00 | 26.27 |
| ATOM | 3159 | C | HIS | 2286 | 64.615 | 17.158 | 137.090 | 1.00 | 23.84 |
| ATOM | 3160 | O | HIS | 2286 | 65.011 | 16.154 | 137.673 | 1.00 | 22.43 |
| ATOM | 3161 | N | ILE | 2287 | 63.896 | 18.097 | 137.689 | 1.00 | 24.72 |
| ATOM | 3162 | CA | ILE | 2287 | 63.541 | 18.003 | 139.095 | 1.00 | 25.15 |
| ATOM | 3163 | CB | ILE | 2287 | 63.338 | 19.400 | 139.682 | 1.00 | 24.12 |
| ATOM | 3164 | CG2 | ILE | 2287 | 63.106 | 19.311 | 141.166 | 1.00 | 26.07 |
| ATOM | 3165 | CG1 | ILE | 2287 | 64.572 | 20.248 | 139.411 | 1.00 | 22.78 |
| ATOM | 3166 | CD1 | ILE | 2287 | 64.445 | 21.660 | 139.880 | 1.00 | 23.38 |
| ATOM | 3167 | C | ILE | 2287 | 62.279 | 17.188 | 139.289 | 1.00 | 26.72 |
| ATOM | 3168 | O | ILE | 2287 | 61.423 | 17.134 | 138.404 | 1.00 | 28.94 |
| ATOM | 3169 | N | GLN | 2288 | 62.159 | 16.560 | 140.453 | 1.00 | 25.98 |
| ATOM | 3170 | CA | GLN | 2288 | 60.998 | 15.742 | 140.749 | 1.00 | 25.93 |
| ATOM | 3171 | CB | GLN | 2288 | 61.194 | 14.364 | 140.128 | 1.00 | 26.69 |
| ATOM | 3172 | CG | GLN | 2288 | 59.997 | 13.458 | 140.215 | 1.00 | 27.14 |
| ATOM | 3173 | CD | GLN | 2288 | 60.212 | 12.198 | 139.411 | 1.00 | 27.36 |
| ATOM | 3174 | OE1 | GLN | 2288 | 59.344 | 11.777 | 138.636 | 1.00 | 26.74 |
| ATOM | 3175 | NE2 | GLN | 2288 | 61.376 | 11.587 | 139.583 | 1.00 | 23.82 |
| ATOM | 3176 | C | GLN | 2288 | 60.834 | 15.627 | 142.252 | 1.00 | 25.36 |
| ATOM | 3177 | O | GLN | 2288 | 61.803 | 15.376 | 142.955 | 1.00 | 25.09 |
| ATOM | 3178 | N | TRP | 2289 | 59.615 | 15.820 | 142.750 | 1.00 | 25.01 |
| ATOM | 3179 | CA | TRP | 2289 | 59.378 | 15.724 | 144.188 | 1.00 | 24.43 |
| ATOM | 3180 | CB | TRP | 2289 | 58.474 | 16.848 | 144.687 | 1.00 | 25.01 |
| ATOM | 3181 | CG | TRP | 2289 | 59.160 | 18.185 | 144.825 | 1.00 | 26.96 |
| ATOM | 3182 | CD2 | TRP | 2289 | 59.838 | 18.695 | 145.983 | 1.00 | 26.71 |
| ATOM | 3183 | CE2 | TRP | 2289 | 60.271 | 20.005 | 145.673 | 1.00 | 27.05 |
| ATOM | 3184 | CE3 | TRP | 2289 | 60.118 | 18.173 | 147.251 | 1.00 | 28.37 |
| ATOM | 3185 | CD1 | TRP | 2289 | 59.218 | 19.174 | 143.888 | 1.00 | 28.38 |
| ATOM | 3186 | NE1 | TRP | 2289 | 59.880 | 20.273 | 144.389 | 1.00 | 27.75 |
| ATOM | 3187 | CZ2 | TRP | 2289 | 60.965 | 20.807 | 146.586 | 1.00 | 28.09 |
| ATOM | 3188 | CZ3 | TRP | 2289 | 60.815 | 18.975 | 148.169 | 1.00 | 29.60 |
| ATOM | 3189 | CH2 | TRP | 2289 | 61.228 | 20.278 | 147.828 | 1.00 | 29.72 |
| ATOM | 3190 | C | TRP | 2289 | 58.772 | 14.389 | 144.567 | 1.00 | 24.28 |
| ATOM | 3191 | O | TRP | 2289 | 57.858 | 13.915 | 143.921 | 1.00 | 25.11 |
| ATOM | 3192 | N | LEU | 2290 | 59.299 | 13.784 | 145.623 | 1.00 | 24.33 |
| ATOM | 3193 | CA | LEU | 2290 | 58.830 | 12.490 | 146.086 | 1.00 | 25.05 |
| ATOM | 3194 | CB | LEU | 2290 | 59.894 | 11.423 | 145.890 | 1.00 | 24.75 |
| ATOM | 3195 | CG | LEU | 2290 | 60.013 | 10.744 | 144.543 | 1.00 | 25.63 |
| ATOM | 3196 | CD1 | LEU | 2290 | 60.314 | 11.755 | 143.453 | 1.00 | 26.85 |
| ATOM | 3197 | CD2 | LEU | 2290 | 61.120 | 9.737 | 144.636 | 1.00 | 27.55 |
| ATOM | 3198 | C | LEU | 2290 | 58.455 | 12.456 | 147.543 | 1.00 | 26.65 |
| ATOM | 3199 | O | LEU | 2290 | 58.983 | 13.210 | 148.359 | 1.00 | 28.27 |
| ATOM | 3200 | N | LYS | 2291 | 57.549 | 11.544 | 147.867 | 1.00 | 26.88 |
| ATOM | 3201 | CA | LYS | 2291 | 57.109 | 11.338 | 149.234 | 1.00 | 27.14 |
| ATOM | 3202 | CB | LYS | 2291 | 55.609 | 11.607 | 149.350 | 1.00 | 26.47 |
| ATOM | 3203 | CG | LYS | 2291 | 54.919 | 11.054 | 150.589 | 1.00 | 25.04 |
| ATOM | 3204 | CD | LYS | 2291 | 55.424 | 11.645 | 151.865 | 1.00 | 24.51 |
| ATOM | 3205 | CE | LYS | 2291 | 54.493 | 11.304 | 153.015 | 1.00 | 24.39 |
| ATOM | 3206 | NZ | LYS | 2291 | 54.334 | 9.840 | 153.244 | 1.00 | 26.35 |
| ATOM | 3207 | C | LYS | 2291 | 57.430 | 9.874 | 149.469 | 1.00 | 28.21 |
| ATOM | 3208 | O | LYS | 2291 | 57.182 | 9.043 | 148.602 | 1.00 | 27.88 |
| ATOM | 3209 | N | HIS | 2292 | 58.018 | 9.570 | 150.620 | 1.00 | 29.84 |
| ATOM | 3210 | CA | HIS | 2292 | 58.390 | 8.204 | 150.954 | 1.00 | 31.43 |
| ATOM | 3211 | CB | HIS | 2292 | 59.652 | 8.193 | 151.792 | 1.00 | 31.88 |
| ATOM | 3212 | CG | HIS | 2292 | 60.871 | 8.573 | 151.027 | 1.00 | 34.89 |
| ATOM | 3213 | CD2 | HIS | 2292 | 61.500 | 9.764 | 150.883 | 1.00 | 36.36 |
| ATOM | 3214 | ND1 | HIS | 2292 | 61.561 | 7.677 | 150.240 | 1.00 | 35.92 |
| ATOM | 3215 | CE1 | HIS | 2292 | 62.563 | 8.299 | 149.644 | 1.00 | 35.84 |
| ATOM | 3216 | NE2 | HIS | 2292 | 62.548 | 9.566 | 150.016 | 1.00 | 36.34 |
| ATOM | 3217 | C | HIS | 2292 | 57.282 | 7.549 | 151.717 | 1.00 | 32.87 |

TABLE 6-continued

FGF2/FGFR1/Heparin Ternary Complex

| ATOM | 3218 | O | HIS | 2292 | 56.847 | 8.053 | 152.743 | 1.00 | 33.04 |
|------|------|------|-----|------|--------|--------|---------|------|-------|
| ATOM | 3219 | N | ILE | 2293 | 56.841 | 6.412 | 151.208 | 1.00 | 35.01 |
| ATOM | 3220 | CA | ILE | 2293 | 55.761 | 5.668 | 151.812 | 1.00 | 37.06 |
| ATOM | 3221 | CB | ILE | 2293 | 54.772 | 5.220 | 150.740 | 1.00 | 35.63 |
| ATOM | 3222 | CG2 | ILE | 2293 | 53.512 | 4.692 | 151.384 | 1.00 | 35.81 |
| ATOM | 3223 | CG1 | ILE | 2293 | 54.441 | 6.399 | 149.837 | 1.00 | 35.30 |
| ATOM | 3224 | CD1 | ILE | 2293 | 53.900 | 7.592 | 150.575 | 1.00 | 38.63 |
| ATOM | 3225 | C | ILE | 2293 | 56.243 | 4.438 | 152.565 | 1.00 | 39.27 |
| ATOM | 3226 | O | ILE | 2293 | 57.374 | 3.979 | 152.395 | 1.00 | 39.33 |
| ATOM | 3227 | N | GLU | 2294 | 55.362 | 3.926 | 153.413 | 1.00 | 41.94 |
| ATOM | 3228 | CA | GLU | 2294 | 55.619 | 2.731 | 154.192 | 1.00 | 45.71 |
| ATOM | 3229 | CB | GLU | 2294 | 55.745 | 3.080 | 155.680 | 1.00 | 44.67 |
| ATOM | 3230 | C | GLU | 2294 | 54.378 | 1.878 | 153.936 | 1.00 | 48.77 |
| ATOM | 3231 | O | GLU | 2294 | 53.269 | 2.292 | 154.270 | 1.00 | 49.30 |
| ATOM | 3232 | N | VAL | 2295 | 54.550 | 0.711 | 153.316 | 1.00 | 52.41 |
| ATOM | 3233 | CA | VAL | 2295 | 53.409 | −0.166 | 153.033 | 1.00 | 55.38 |
| ATOM | 3234 | CB | VAL | 2295 | 53.689 | −1.086 | 151.812 | 1.00 | 55.33 |
| ATOM | 3235 | CG1 | VAL | 2295 | 52.454 | −1.913 | 151.468 | 1.00 | 55.99 |
| ATOM | 3236 | CG2 | VAL | 2295 | 54.073 | −0.247 | 150.618 | 1.00 | 55.54 |
| ATOM | 3237 | C | VAL | 2295 | 53.081 | −1.003 | 154.276 | 1.00 | 57.06 |
| ATOM | 3238 | O | VAL | 2295 | 52.143 | −1.806 | 154.282 | 1.00 | 57.53 |
| ATOM | 3239 | N | ASN | 2296 | 53.871 | −0.774 | 155.324 | 1.00 | 58.69 |
| ATOM | 3240 | CA | ASN | 2296 | 53.754 | −1.401 | 156.643 | 1.00 | 59.89 |
| ATOM | 3241 | CB | ASN | 2296 | 54.078 | −2.893 | 156.586 | 1.00 | 60.71 |
| ATOM | 3242 | CG | ASN | 2296 | 53.175 | −3.645 | 155.646 | 1.00 | 63.08 |
| ATOM | 3243 | OD1 | ASN | 2296 | 51.976 | −3.787 | 155.901 | 1.00 | 63.11 |
| ATOM | 3244 | ND2 | ASN | 2296 | 53.736 | −4.117 | 154.534 | 1.00 | 64.26 |
| ATOM | 3245 | C | ASN | 2296 | 54.845 | −0.689 | 157.427 | 1.00 | 60.02 |
| ATOM | 3246 | O | ASN | 2296 | 55.143 | 0.477 | 157.164 | 1.00 | 59.99 |
| ATOM | 3247 | N | GLY | 2297 | 55.445 | −1.380 | 158.387 | 1.00 | 60.38 |
| ATOM | 3248 | CA | GLY | 2297 | 56.538 | −0.774 | 159.122 | 1.00 | 59.68 |
| ATOM | 3249 | C | GLY | 2297 | 57.721 | −0.845 | 158.168 | 1.00 | 59.19 |
| ATOM | 3250 | O | GLY | 2297 | 58.866 | −0.575 | 158.538 | 1.00 | 60.10 |
| ATOM | 3251 | N | SER | 2298 | 57.420 | −1.216 | 156.923 | 1.00 | 57.45 |
| ATOM | 3252 | CA | SER | 2298 | 58.413 | −1.360 | 155.868 | 1.00 | 55.47 |
| ATOM | 3253 | CB | SER | 2298 | 58.111 | −2.601 | 155.031 | 1.00 | 55.58 |
| ATOM | 3254 | OG | SER | 2298 | 56.830 | −2.494 | 154.431 | 1.00 | 56.51 |
| ATOM | 3255 | C | SER | 2298 | 58.413 | −0.149 | 154.960 | 1.00 | 54.17 |
| ATOM | 3256 | O | SER | 2298 | 57.396 | 0.183 | 154.351 | 1.00 | 53.71 |
| ATOM | 3257 | N | LYS | 2299 | 59.565 | 0.503 | 154.872 | 1.00 | 52.79 |
| ATOM | 3258 | CA | LYS | 2299 | 59.717 | 1.673 | 154.027 | 1.00 | 51.38 |
| ATOM | 3259 | CB | LYS | 2299 | 60.450 | 2.779 | 154.795 | 1.00 | 51.47 |
| ATOM | 3260 | CG | LYS | 2299 | 59.620 | 3.315 | 155.958 | 1.00 | 52.71 |
| ATOM | 3261 | CD | LYS | 2299 | 60.371 | 4.258 | 156.888 | 1.00 | 53.68 |
| ATOM | 3262 | CE | LYS | 2299 | 59.521 | 4.555 | 158.132 | 1.00 | 54.50 |
| ATOM | 3263 | NZ | LYS | 2299 | 60.194 | 5.439 | 159.126 | 1.00 | 53.51 |
| ATOM | 3264 | C | LYS | 2299 | 60.490 | 1.242 | 152.794 | 1.00 | 50.17 |
| ATOM | 3265 | O | LYS | 2299 | 60.744 | 2.034 | 151.885 | 1.00 | 49.68 |
| ATOM | 3266 | N | ILE | 2300 | 60.841 | −0.040 | 152.770 | 1.00 | 48.86 |
| ATOM | 3267 | CA | ILE | 2300 | 61.578 | −0.619 | 151.657 | 1.00 | 47.52 |
| ATOM | 3268 | CB | ILE | 2300 | 62.953 | −1.145 | 152.116 | 1.00 | 45.85 |
| ATOM | 3269 | CG2 | ILE | 2300 | 63.751 | −1.628 | 150.920 | 1.00 | 44.48 |
| ATOM | 3270 | CG1 | ILE | 2300 | 63.726 | −0.028 | 152.810 | 1.00 | 44.67 |
| ATOM | 3271 | CD1 | ILE | 2300 | 63.996 | 1.184 | 151.917 | 1.00 | 43.92 |
| ATOM | 3272 | C | ILE | 2300 | 60.790 | −1.763 | 151.030 | 1.00 | 47.39 |
| ATOM | 3273 | O | ILE | 2300 | 60.215 | −2.592 | 151.727 | 1.00 | 47.74 |
| ATOM | 3274 | N | GLY | 2301 | 60.767 | −1.793 | 149.704 | 1.00 | 47.56 |
| ATOM | 3275 | CA | GLY | 2301 | 60.055 | −2.838 | 148.995 | 1.00 | 47.21 |
| ATOM | 3276 | C | GLY | 2301 | 60.917 | −4.057 | 148.717 | 1.00 | 47.10 |
| ATOM | 3277 | O | GLY | 2301 | 62.140 | −4.031 | 148.908 | 1.00 | 46.68 |
| ATOM | 3278 | N | PRO | 2302 | 60.298 | −5.155 | 148.259 | 1.00 | 46.75 |
| ATOM | 3279 | CD | PRO | 2302 | 58.848 | −5.306 | 148.038 | 1.00 | 46.14 |
| ATOM | 3280 | CA | PRO | 2302 | 60.998 | −6.403 | 147.949 | 1.00 | 45.69 |
| ATOM | 3281 | CB | PRO | 2302 | 59.943 | −7.193 | 147.187 | 1.00 | 45.56 |
| ATOM | 3282 | CG | PRO | 2302 | 58.695 | −6.813 | 147.918 | 1.00 | 45.16 |
| ATOM | 3283 | C | PRO | 2302 | 62.285 | −6.211 | 147.155 | 1.00 | 44.61 |
| ATOM | 3284 | O | PRO | 2302 | 63.273 | −6.889 | 147.411 | 1.00 | 44.15 |
| ATOM | 3285 | N | ASP | 2303 | 62.270 | −5.285 | 146.200 | 1.00 | 44.35 |
| ATOM | 3286 | CA | ASP | 2303 | 63.447 | −5.014 | 145.377 | 1.00 | 43.97 |
| ATOM | 3287 | CB | ASP | 2303 | 63.034 | −4.353 | 144.058 | 1.00 | 44.64 |
| ATOM | 3288 | CG | ASP | 2303 | 62.144 | −3.146 | 144.259 | 1.00 | 45.77 |
| ATOM | 3289 | OD1 | ASP | 2303 | 61.861 | −2.450 | 143.262 | 1.00 | 46.62 |
| ATOM | 3290 | OD2 | ASP | 2303 | 61.719 | −2.893 | 145.407 | 1.00 | 46.99 |
| ATOM | 3291 | C | ASP | 2303 | 64.497 | −4.144 | 146.067 | 1.00 | 43.64 |
| ATOM | 3292 | O | ASP | 2303 | 65.417 | −3.656 | 145.426 | 1.00 | 43.58 |
| ATOM | 3293 | N | ASN | 2304 | 64.356 | −3.957 | 147.373 | 1.00 | 43.36 |
| ATOM | 3294 | CA | ASN | 2304 | 65.294 | −3.154 | 148.145 | 1.00 | 43.46 |

TABLE 6-continued

FGF2/FGFR1/Heparin Ternary Complex

| ATOM | 3295 | CB | ASN | 2304 | 66.703 | −3.767 | 148.086 | 1.00 | 43.04 |
|---|---|---|---|---|---|---|---|---|---|
| ATOM | 3296 | CG | ASN | 2304 | 67.536 | −3.457 | 149.334 | 1.00 | 42.69 |
| ATOM | 3297 | OD1 | ASN | 2304 | 67.156 | −3.807 | 150.454 | 1.00 | 43.07 |
| ATOM | 3298 | ND2 | ASN | 2304 | 68.674 | −2.801 | 149.142 | 1.00 | 42.29 |
| ATOM | 3299 | C | ASN | 2304 | 65.330 | −1.694 | 147.685 | 1.00 | 43.63 |
| ATOM | 3300 | O | ASN | 2304 | 66.373 | −1.032 | 147.732 | 1.00 | 44.41 |
| ATOM | 3301 | N | LEU | 2305 | 64.189 | −1.199 | 147.217 | 1.00 | 43.10 |
| ATOM | 3302 | CA | LEU | 2305 | 64.072 | 0.198 | 146.806 | 1.00 | 42.32 |
| ATOM | 3303 | CB | LEU | 2305 | 63.580 | 0.335 | 145.359 | 1.00 | 43.10 |
| ATOM | 3304 | CG | LEU | 2305 | 64.518 | 0.106 | 144.166 | 1.00 | 43.78 |
| ATOM | 3305 | CD1 | LEU | 2305 | 65.804 | 0.884 | 144.359 | 1.00 | 43.80 |
| ATOM | 3306 | CD2 | LEU | 2305 | 64.821 | −1.368 | 144.028 | 1.00 | 44.83 |
| ATOM | 3307 | C | LEU | 2305 | 63.028 | 0.773 | 147.748 | 1.00 | 41.36 |
| ATOM | 3308 | O | LEU | 2305 | 62.285 | 0.026 | 148.377 | 1.00 | 41.91 |
| ATOM | 3309 | N | PRO | 2306 | 62.959 | 2.102 | 147.866 | 1.00 | 39.92 |
| ATOM | 3310 | CD | PRO | 2306 | 63.946 | 3.081 | 147.384 | 1.00 | 39.37 |
| ATOM | 3311 | CA | PRO | 2306 | 61.980 | 2.739 | 148.754 | 1.00 | 38.59 |
| ATOM | 3312 | CB | PRO | 2306 | 62.674 | 4.038 | 149.126 | 1.00 | 38.32 |
| ATOM | 3313 | CG | PRO | 2306 | 63.337 | 4.402 | 147.837 | 1.00 | 38.73 |
| ATOM | 3314 | C | PRO | 2306 | 60.608 | 2.989 | 148.114 | 1.00 | 37.71 |
| ATOM | 3315 | O | PRO | 2306 | 60.527 | 3.486 | 146.987 | 1.00 | 37.51 |
| ATOM | 3316 | N | TYR | 2307 | 59.535 | 2.643 | 148.833 | 1.00 | 36.33 |
| ATOM | 3317 | CA | TYR | 2307 | 58.180 | 2.862 | 148.334 | 1.00 | 34.33 |
| ATOM | 3318 | CB | TYR | 2307 | 57.125 | 2.304 | 149.286 | 1.00 | 34.31 |
| ATOM | 3319 | CG | TYR | 2307 | 57.182 | 0.824 | 149.564 | 1.00 | 34.95 |
| ATOM | 3320 | CD1 | TYR | 2307 | 57.601 | 0.353 | 150.809 | 1.00 | 36.33 |
| ATOM | 3321 | CE1 | TYR | 2307 | 57.585 | −1.004 | 151.117 | 1.00 | 36.54 |
| ATOM | 3322 | CD2 | TYR | 2307 | 56.753 | −0.107 | 148.620 | 1.00 | 35.00 |
| ATOM | 3323 | CE2 | TYR | 2307 | 56.733 | −1.476 | 148.917 | 1.00 | 36.35 |
| ATOM | 3324 | CZ | TYR | 2307 | 57.150 | −1.914 | 150.172 | 1.00 | 36.96 |
| ATOM | 3325 | OH | TYR | 2307 | 57.129 | −3.255 | 150.495 | 1.00 | 36.36 |
| ATOM | 3326 | C | TYR | 2307 | 57.994 | 4.364 | 148.276 | 1.00 | 33.55 |
| ATOM | 3327 | O | TYR | 2307 | 58.064 | 5.036 | 149.292 | 1.00 | 33.97 |
| ATOM | 3328 | N | VAL | 2308 | 57.744 | 4.901 | 147.098 | 1.00 | 32.60 |
| ATOM | 3329 | CA | VAL | 2308 | 57.574 | 6.337 | 146.980 | 1.00 | 32.06 |
| ATOM | 3330 | CB | VAL | 2308 | 58.792 | 6.988 | 146.319 | 1.00 | 32.31 |
| ATOM | 3331 | CG1 | VAL | 2308 | 59.938 | 7.053 | 147.309 | 1.00 | 33.39 |
| ATOM | 3332 | CG2 | VAL | 2308 | 59.193 | 6.194 | 145.085 | 1.00 | 30.33 |
| ATOM | 3333 | C | VAL | 2308 | 56.356 | 6.749 | 146.194 | 1.00 | 31.70 |
| ATOM | 3334 | O | VAL | 2308 | 55.769 | 5.970 | 145.462 | 1.00 | 32.93 |
| ATOM | 3335 | N | GLN | 2309 | 55.992 | 8.007 | 146.348 | 1.00 | 31.09 |
| ATOM | 3336 | CA | GLN | 2309 | 54.852 | 8.561 | 145.656 | 1.00 | 30.56 |
| ATOM | 3337 | CB | GLN | 2309 | 53.779 | 8.899 | 146.680 | 1.00 | 31.43 |
| ATOM | 3338 | CG | GLN | 2309 | 52.448 | 9.284 | 146.111 | 1.00 | 34.85 |
| ATOM | 3339 | CD | GLN | 2309 | 51.490 | 9.728 | 147.202 | 1.00 | 37.78 |
| ATOM | 3340 | OE1 | GLN | 2309 | 51.412 | 9.112 | 148.273 | 1.00 | 39.39 |
| ATOM | 3341 | NE2 | GLN | 2309 | 50.751 | 10.799 | 146.936 | 1.00 | 39.29 |
| ATOM | 3342 | C | GLN | 2309 | 55.317 | 9.822 | 144.914 | 1.00 | 29.60 |
| ATOM | 3343 | O | GLN | 2309 | 55.737 | 10.805 | 145.530 | 1.00 | 30.26 |
| ATOM | 3344 | N | ILE | 2310 | 55.285 | 9.784 | 143.589 | 1.00 | 27.79 |
| ATOM | 3345 | CA | ILE | 2310 | 55.688 | 10.948 | 142.822 | 1.00 | 26.22 |
| ATOM | 3346 | CB | ILE | 2310 | 55.675 | 10.656 | 141.314 | 1.00 | 24.98 |
| ATOM | 3347 | CG2 | ILE | 2310 | 56.189 | 11.847 | 140.533 | 1.00 | 23.09 |
| ATOM | 3348 | CG1 | ILE | 2310 | 56.533 | 9.429 | 141.037 | 1.00 | 24.99 |
| ATOM | 3349 | CD1 | ILE | 2310 | 57.879 | 9.459 | 141.724 | 1.00 | 23.91 |
| ATOM | 3350 | C | ILE | 2310 | 54.658 | 12.016 | 143.133 | 1.00 | 26.61 |
| ATOM | 3351 | O | ILE | 2310 | 53.460 | 11.752 | 143.093 | 1.00 | 27.09 |
| ATOM | 3352 | N | LEU | 2311 | 55.117 | 13.218 | 143.458 | 1.00 | 26.14 |
| ATOM | 3353 | CA | LEU | 2311 | 54.202 | 14.301 | 143.785 | 1.00 | 25.19 |
| ATOM | 3354 | CB | LEU | 2311 | 54.504 | 14.839 | 145.183 | 1.00 | 24.23 |
| ATOM | 3355 | CG | LEU | 2311 | 54.577 | 13.816 | 146.316 | 1.00 | 23.86 |
| ATOM | 3356 | CD1 | LEU | 2311 | 55.022 | 14.515 | 147.555 | 1.00 | 25.05 |
| ATOM | 3357 | CD2 | LEU | 2311 | 53.242 | 13.158 | 146.551 | 1.00 | 22.35 |
| ATOM | 3358 | C | LEU | 2311 | 54.261 | 15.448 | 142.790 | 1.00 | 25.59 |
| ATOM | 3359 | O | LEU | 2311 | 53.276 | 16.156 | 142.600 | 1.00 | 26.28 |
| ATOM | 3360 | N | LYS | 2312 | 55.405 | 15.620 | 142.142 | 1.00 | 25.78 |
| ATOM | 3361 | CA | LYS | 2312 | 55.592 | 16.714 | 141.197 | 1.00 | 25.94 |
| ATOM | 3362 | CB | LYS | 2312 | 55.973 | 17.969 | 141.988 | 1.00 | 26.21 |
| ATOM | 3363 | CG | LYS | 2312 | 55.700 | 19.283 | 141.305 | 1.00 | 27.55 |
| ATOM | 3364 | CD | LYS | 2312 | 55.687 | 20.408 | 142.335 | 1.00 | 27.49 |
| ATOM | 3365 | CE | LYS | 2312 | 55.331 | 21.753 | 141.713 | 1.00 | 26.53 |
| ATOM | 3366 | NZ | LYS | 2312 | 55.102 | 22.769 | 142.780 | 1.00 | 26.35 |
| ATOM | 3367 | C | LYS | 2312 | 56.701 | 16.320 | 140.220 | 1.00 | 26.55 |
| ATOM | 3368 | O | LYS | 2312 | 57.722 | 15.756 | 140.625 | 1.00 | 27.08 |
| ATOM | 3369 | N | THR | 2313 | 56.509 | 16.610 | 138.937 | 1.00 | 26.65 |
| ATOM | 3370 | CA | THR | 2313 | 57.507 | 16.237 | 137.937 | 1.00 | 27.27 |
| ATOM | 3371 | CB | THR | 2313 | 57.049 | 15.020 | 137.142 | 1.00 | 25.47 |

TABLE 6-continued

FGF2/FGFR1/Heparin Ternary Complex

| ATOM | 3372 | OG1 | THR | 2313 | 55.968 | 14.397 | 137.834 | 1.00 | 26.44 |
|------|------|-----|-----|------|--------|--------|---------|------|-------|
| ATOM | 3373 | CG2 | THR | 2313 | 58.172 | 14.024 | 136.977 | 1.00 | 24.30 |
| ATOM | 3374 | C | THR | 2313 | 57.726 | 17.347 | 136.938 | 1.00 | 28.50 |
| ATOM | 3375 | O | THR | 2313 | 56.771 | 17.827 | 136.333 | 1.00 | 29.05 |
| ATOM | 3376 | N | ALA | 2314 | 58.981 | 17.737 | 136.744 | 1.00 | 29.23 |
| ATOM | 3377 | CA | ALA | 2314 | 59.301 | 18.800 | 135.806 | 1.00 | 30.80 |
| ATOM | 3378 | CB | ALA | 2314 | 60.802 | 19.052 | 135.807 | 1.00 | 31.98 |
| ATOM | 3379 | C | ALA | 2314 | 58.836 | 18.425 | 134.409 | 1.00 | 31.39 |
| ATOM | 3380 | O | ALA | 2314 | 58.810 | 17.249 | 134.051 | 1.00 | 32.01 |
| ATOM | 3381 | N | GLY | 2315 | 58.470 | 19.426 | 133.617 | 1.00 | 31.57 |
| ATOM | 3382 | CA | GLY | 2315 | 58.026 | 19.151 | 132.265 | 1.00 | 31.47 |
| ATOM | 3383 | C | GLY | 2315 | 57.150 | 20.257 | 131.726 | 1.00 | 32.10 |
| ATOM | 3384 | O | GLY | 2315 | 56.911 | 21.264 | 132.394 | 1.00 | 32.59 |
| ATOM | 3385 | N | VAL | 2316 | 56.656 | 20.065 | 130.514 | 1.00 | 32.49 |
| ATOM | 3386 | CA | VAL | 2316 | 55.811 | 21.055 | 129.881 | 1.00 | 33.21 |
| ATOM | 3387 | CB | VAL | 2316 | 55.371 | 20.559 | 128.509 | 1.00 | 32.94 |
| ATOM | 3388 | CG1 | VAL | 2316 | 54.382 | 21.522 | 127.913 | 1.00 | 36.27 |
| ATOM | 3389 | CG2 | VAL | 2316 | 56.581 | 20.426 | 127.602 | 1.00 | 31.90 |
| ATOM | 3390 | C | VAL | 2316 | 54.582 | 21.416 | 130.710 | 1.00 | 34.17 |
| ATOM | 3391 | O | VAL | 2316 | 54.135 | 22.554 | 130.704 | 1.00 | 34.38 |
| ATOM | 3392 | N | ASN | 2317 | 54.040 | 20.452 | 131.433 | 1.00 | 36.03 |
| ATOM | 3393 | CA | ASN | 2317 | 52.853 | 20.715 | 132.233 | 1.00 | 37.90 |
| ATOM | 3394 | CB | ASN | 2317 | 52.062 | 19.416 | 132.430 | 1.00 | 41.91 |
| ATOM | 3395 | CG | ASN | 2317 | 51.529 | 18.844 | 131.115 | 1.00 | 44.25 |
| ATOM | 3396 | OD1 | ASN | 2317 | 51.106 | 17.688 | 131.060 | 1.00 | 46.64 |
| ATOM | 3397 | ND2 | ASN | 2317 | 51.539 | 19.656 | 130.058 | 1.00 | 44.82 |
| ATOM | 3398 | C | ASN | 2317 | 53.196 | 21.336 | 133.578 | 1.00 | 37.48 |
| ATOM | 3399 | O | ASN | 2317 | 52.357 | 21.998 | 134.204 | 1.00 | 38.61 |
| ATOM | 3400 | N | THR | 2318 | 54.436 | 21.127 | 134.003 | 1.00 | 35.92 |
| ATOM | 3401 | CA | THR | 2318 | 54.920 | 21.636 | 135.268 | 1.00 | 34.27 |
| ATOM | 3402 | CB | THR | 2318 | 55.033 | 20.511 | 136.263 | 1.00 | 34.40 |
| ATOM | 3403 | OG1 | THR | 2318 | 53.888 | 19.665 | 136.140 | 1.00 | 34.31 |
| ATOM | 3404 | CG2 | THR | 2318 | 55.112 | 21.061 | 137.669 | 1.00 | 36.18 |
| ATOM | 3405 | C | THR | 2318 | 56.302 | 22.168 | 135.001 | 1.00 | 33.31 |
| ATOM | 3406 | O | THR | 2318 | 57.287 | 21.446 | 135.144 | 1.00 | 33.84 |
| ATOM | 3407 | N | THR | 2319 | 56.372 | 23.429 | 134.608 | 1.00 | 31.80 |
| ATOM | 3408 | CA | THR | 2319 | 57.637 | 24.061 | 134.288 | 1.00 | 30.00 |
| ATOM | 3409 | CB | THR | 2319 | 57.360 | 25.345 | 133.542 | 1.00 | 29.99 |
| ATOM | 3410 | OG1 | THR | 2319 | 56.618 | 25.018 | 132.363 | 1.00 | 26.20 |
| ATOM | 3411 | CG2 | THR | 2319 | 58.658 | 26.054 | 133.166 | 1.00 | 31.40 |
| ATOM | 3412 | C | THR | 2319 | 58.546 | 24.312 | 135.485 | 1.00 | 29.12 |
| ATOM | 3413 | O | THR | 2319 | 58.094 | 24.386 | 136.624 | 1.00 | 29.08 |
| ATOM | 3414 | N | ASP | 2320 | 59.836 | 24.441 | 135.212 | 1.00 | 28.31 |
| ATOM | 3415 | CA | ASP | 2320 | 60.807 | 24.655 | 136.260 | 1.00 | 28.93 |
| ATOM | 3416 | CB | ASP | 2320 | 62.215 | 24.767 | 135.625 | 1.00 | 25.80 |
| ATOM | 3417 | CG | ASP | 2320 | 62.652 | 23.462 | 134.890 | 1.00 | 24.47 |
| ATOM | 3418 | OD1 | ASP | 2320 | 62.224 | 22.354 | 135.281 | 1.00 | 22.80 |
| ATOM | 3419 | OD2 | ASP | 2320 | 63.447 | 23.527 | 133.925 | 1.00 | 22.27 |
| ATOM | 3420 | C | ASP | 2320 | 60.451 | 25.857 | 137.164 | 1.00 | 31.01 |
| ATOM | 3421 | O | ASP | 2320 | 60.950 | 25.977 | 138.281 | 1.00 | 32.39 |
| ATOM | 3422 | N | LYS | 2321 | 59.558 | 26.723 | 136.697 | 1.00 | 33.47 |
| ATOM | 3423 | CA | LYS | 2321 | 59.140 | 27.884 | 137.476 | 1.00 | 35.16 |
| ATOM | 3424 | CB | LYS | 2321 | 58.009 | 28.623 | 136.758 | 1.00 | 36.60 |
| ATOM | 3425 | CG | LYS | 2321 | 58.167 | 28.692 | 135.255 | 1.00 | 40.39 |
| ATOM | 3426 | CD | LYS | 2321 | 56.971 | 29.396 | 134.595 | 1.00 | 43.03 |
| ATOM | 3427 | CE | LYS | 2321 | 56.860 | 29.066 | 133.076 | 1.00 | 43.90 |
| ATOM | 3428 | NZ | LYS | 2321 | 58.066 | 29.382 | 132.239 | 1.00 | 40.93 |
| ATOM | 3429 | C | LYS | 2321 | 58.635 | 27.442 | 138.846 | 1.00 | 36.16 |
| ATOM | 3430 | O | LYS | 2321 | 59.090 | 27.923 | 139.882 | 1.00 | 37.35 |
| ATOM | 3431 | N | GLU | 2322 | 57.687 | 26.516 | 138.843 | 1.00 | 36.64 |
| ATOM | 3432 | CA | GLU | 2322 | 57.104 | 26.038 | 140.082 | 1.00 | 38.06 |
| ATOM | 3433 | CB | GLU | 2322 | 55.611 | 25.818 | 139.876 | 1.00 | 40.30 |
| ATOM | 3434 | CG | GLU | 2322 | 55.279 | 25.252 | 138.516 | 1.00 | 42.80 |
| ATOM | 3435 | CD | GLU | 2322 | 53.782 | 25.177 | 138.265 | 1.00 | 45.28 |
| ATOM | 3436 | OE1 | GLU | 2322 | 53.099 | 24.367 | 138.938 | 1.00 | 46.14 |
| ATOM | 3437 | OE2 | GLU | 2322 | 53.291 | 25.932 | 137.393 | 1.00 | 45.44 |
| ATOM | 3438 | C | GLU | 2322 | 57.727 | 24.785 | 140.674 | 1.00 | 37.57 |
| ATOM | 3439 | O | GLU | 2322 | 57.266 | 24.299 | 141.703 | 1.00 | 37.88 |
| ATOM | 3440 | N | MET | 2323 | 58.782 | 24.274 | 140.051 | 1.00 | 37.12 |
| ATOM | 3441 | CA | MET | 2323 | 59.422 | 23.054 | 140.533 | 1.00 | 36.36 |
| ATOM | 3442 | CB | MET | 2323 | 60.233 | 22.387 | 139.413 | 1.00 | 35.76 |
| ATOM | 3443 | CG | MET | 2323 | 59.388 | 21.689 | 138.343 | 1.00 | 34.71 |
| ATOM | 3444 | SD | MET | 2323 | 58.178 | 20.516 | 139.009 | 1.00 | 33.46 |
| ATOM | 3445 | CE | MET | 2323 | 59.263 | 19.280 | 139.761 | 1.00 | 34.08 |
| ATOM | 3446 | C | MET | 2323 | 60.308 | 23.200 | 141.755 | 1.00 | 36.28 |
| ATOM | 3447 | O | MET | 2323 | 60.597 | 22.213 | 142.426 | 1.00 | 35.30 |
| ATOM | 3448 | N | GLU | 2324 | 60.744 | 24.411 | 142.063 | 1.00 | 37.11 |

TABLE 6-continued

FGF2/FGFR1/Heparin Ternary Complex

| ATOM | 3449 | CA | GLU | 2324 | 61.601 | 24.563 | 143.227 | 1.00 | 38.55 |
|---|---|---|---|---|---|---|---|---|---|
| ATOM | 3450 | CB | GLU | 2324 | 62.547 | 25.750 | 143.028 | 1.00 | 40.58 |
| ATOM | 3451 | CG | GLU | 2324 | 63.556 | 25.485 | 141.907 | 1.00 | 42.57 |
| ATOM | 3452 | CD | GLU | 2324 | 64.704 | 26.486 | 141.850 | 1.00 | 43.05 |
| ATOM | 3453 | OE1 | GLU | 2324 | 64.438 | 27.689 | 141.632 | 1.00 | 44.25 |
| ATOM | 3454 | OE2 | GLU | 2324 | 65.873 | 26.063 | 142.014 | 1.00 | 41.59 |
| ATOM | 3455 | C | GLU | 2324 | 60.855 | 24.653 | 144.565 | 1.00 | 38.27 |
| ATOM | 3456 | O | GLU | 2324 | 61.471 | 24.819 | 145.616 | 1.00 | 37.49 |
| ATOM | 3457 | N | VAL | 2325 | 59.533 | 24.503 | 144.532 | 1.00 | 37.66 |
| ATOM | 3458 | CA | VAL | 2325 | 58.750 | 24.565 | 145.754 | 1.00 | 37.45 |
| ATOM | 3459 | CB | VAL | 2325 | 58.252 | 25.987 | 146.008 | 1.00 | 37.38 |
| ATOM | 3460 | CG1 | VAL | 2325 | 57.319 | 26.409 | 144.893 | 1.00 | 38.00 |
| ATOM | 3461 | CG2 | VAL | 2325 | 57.548 | 26.056 | 147.342 | 1.00 | 38.48 |
| ATOM | 3462 | C | VAL | 2325 | 57.550 | 23.620 | 145.747 | 1.00 | 37.40 |
| ATOM | 3463 | O | VAL | 2325 | 56.720 | 23.649 | 144.841 | 1.00 | 38.13 |
| ATOM | 3464 | N | LEU | 2326 | 57.469 | 22.788 | 146.781 | 1.00 | 37.18 |
| ATOM | 3465 | CA | LEU | 2326 | 56.392 | 21.815 | 146.936 | 1.00 | 36.35 |
| ATOM | 3466 | CB | LEU | 2326 | 56.961 | 20.471 | 147.396 | 1.00 | 34.79 |
| ATOM | 3467 | CG | LEU | 2326 | 55.955 | 19.339 | 147.516 | 1.00 | 33.40 |
| ATOM | 3468 | CD1 | LEU | 2326 | 55.279 | 19.158 | 146.182 | 1.00 | 33.58 |
| ATOM | 3469 | CD2 | LEU | 2326 | 56.657 | 18.064 | 147.931 | 1.00 | 31.96 |
| ATOM | 3470 | C | LEU | 2326 | 55.403 | 22.321 | 147.974 | 1.00 | 37.00 |
| ATOM | 3471 | O | LEU | 2326 | 55.769 | 22.553 | 149.125 | 1.00 | 36.12 |
| ATOM | 3472 | N | HIS | 2327 | 54.149 | 22.489 | 147.564 | 1.00 | 38.27 |
| ATOM | 3473 | CA | HIS | 2327 | 53.112 | 22.975 | 148.466 | 1.00 | 38.34 |
| ATOM | 3474 | CB | HIS | 2327 | 52.195 | 23.963 | 147.741 | 1.00 | 40.16 |
| ATOM | 3475 | CG | HIS | 2327 | 52.866 | 25.242 | 147.342 | 1.00 | 43.09 |
| ATOM | 3476 | CD2 | HIS | 2327 | 53.264 | 25.701 | 146.130 | 1.00 | 42.98 |
| ATOM | 3477 | ND1 | HIS | 2327 | 53.198 | 26.226 | 148.252 | 1.00 | 43.74 |
| ATOM | 3478 | CE1 | HIS | 2327 | 53.768 | 27.236 | 147.617 | 1.00 | 43.62 |
| ATOM | 3479 | NE2 | HIS | 2327 | 53.821 | 26.943 | 146.329 | 1.00 | 44.01 |
| ATOM | 3480 | C | HIS | 2327 | 52.269 | 21.835 | 149.018 | 1.00 | 38.16 |
| ATOM | 3481 | O | HIS | 2327 | 51.658 | 21.074 | 148.267 | 1.00 | 38.38 |
| ATOM | 3482 | N | LEU | 2328 | 52.244 | 21.720 | 150.340 | 1.00 | 37.91 |
| ATOM | 3483 | CA | LEU | 2328 | 51.461 | 20.696 | 151.012 | 1.00 | 37.84 |
| ATOM | 3484 | CB | LEU | 2328 | 52.318 | 19.939 | 152.034 | 1.00 | 36.72 |
| ATOM | 3485 | CG | LEU | 2328 | 53.402 | 18.969 | 151.535 | 1.00 | 36.31 |
| ATOM | 3486 | CD1 | LEU | 2328 | 54.295 | 18.550 | 152.683 | 1.00 | 35.20 |
| ATOM | 3487 | CD2 | LEU | 2328 | 52.757 | 17.751 | 150.909 | 1.00 | 36.53 |
| ATOM | 3488 | C | LEU | 2328 | 50.362 | 21.449 | 151.725 | 1.00 | 39.07 |
| ATOM | 3489 | O | LEU | 2328 | 50.593 | 22.023 | 152.789 | 1.00 | 39.32 |
| ATOM | 3490 | N | ARG | 2329 | 49.169 | 21.459 | 151.137 | 1.00 | 40.36 |
| ATOM | 3491 | CA | ARG | 2329 | 48.052 | 22.175 | 151.738 | 1.00 | 41.25 |
| ATOM | 3492 | CB | ARG | 2329 | 47.116 | 22.703 | 150.650 | 1.00 | 41.14 |
| ATOM | 3493 | C | ARG | 2329 | 47.273 | 21.355 | 152.769 | 1.00 | 42.07 |
| ATOM | 3494 | O | ARG | 2329 | 47.039 | 20.154 | 152.601 | 1.00 | 41.21 |
| ATOM | 3495 | N | ASN | 2330 | 46.897 | 22.039 | 153.847 | 1.00 | 43.83 |
| ATOM | 3496 | CA | ASN | 2330 | 46.151 | 21.463 | 154.962 | 1.00 | 45.93 |
| ATOM | 3497 | CB | ASN | 2330 | 44.652 | 21.498 | 154.676 | 1.00 | 49.05 |
| ATOM | 3498 | CG | ASN | 2330 | 43.834 | 21.086 | 155.877 | 1.00 | 52.00 |
| ATOM | 3499 | OD1 | ASN | 2330 | 43.787 | 19.907 | 156.235 | 1.00 | 53.82 |
| ATOM | 3500 | ND2 | ASN | 2330 | 43.201 | 22.063 | 156.527 | 1.00 | 53.24 |
| ATOM | 3501 | C | ASN | 2330 | 46.576 | 20.043 | 155.276 | 1.00 | 45.58 |
| ATOM | 3502 | O | ASN | 2330 | 45.868 | 19.085 | 154.973 | 1.00 | 45.29 |
| ATOM | 3503 | N | VAL | 2331 | 47.733 | 19.928 | 155.914 | 1.00 | 45.27 |
| ATOM | 3504 | CA | VAL | 2331 | 48.328 | 18.647 | 156.266 | 1.00 | 44.77 |
| ATOM | 3505 | CB | VAL | 2331 | 49.705 | 18.893 | 156.864 | 1.00 | 43.57 |
| ATOM | 3506 | CG1 | VAL | 2331 | 50.467 | 19.858 | 155.978 | 1.00 | 42.63 |
| ATOM | 3507 | CG2 | VAL | 2331 | 49.566 | 19.469 | 158.248 | 1.00 | 42.71 |
| ATOM | 3508 | C | VAL | 2331 | 47.520 | 17.772 | 157.218 | 1.00 | 44.99 |
| ATOM | 3509 | O | VAL | 2331 | 46.598 | 18.235 | 157.878 | 1.00 | 46.10 |
| ATOM | 3510 | N | SER | 2332 | 47.891 | 16.499 | 157.278 | 1.00 | 45.10 |
| ATOM | 3511 | CA | SER | 2332 | 47.237 | 15.517 | 158.131 | 1.00 | 45.49 |
| ATOM | 3512 | CB | SER | 2332 | 46.184 | 14.756 | 157.334 | 1.00 | 44.55 |
| ATOM | 3513 | OG | SER | 2332 | 46.716 | 14.303 | 156.100 | 1.00 | 42.28 |
| ATOM | 3514 | C | SER | 2332 | 48.304 | 14.555 | 158.612 | 1.00 | 46.64 |
| ATOM | 3515 | O | SER | 2332 | 49.397 | 14.523 | 158.056 | 1.00 | 47.33 |
| ATOM | 3516 | N | PHE | 2333 | 47.994 | 13.770 | 159.639 | 1.00 | 47.66 |
| ATOM | 3517 | CA | PHE | 2333 | 48.956 | 12.812 | 160.168 | 1.00 | 48.81 |
| ATOM | 3518 | CB | PHE | 2333 | 48.298 | 11.942 | 161.235 | 1.00 | 50.74 |
| ATOM | 3519 | CG | PHE | 2333 | 48.494 | 12.451 | 162.627 | 1.00 | 53.07 |
| ATOM | 3520 | CD1 | PHE | 2333 | 48.721 | 11.561 | 163.679 | 1.00 | 54.72 |
| ATOM | 3521 | CD2 | PHE | 2333 | 48.475 | 13.817 | 162.890 | 1.00 | 53.83 |
| ATOM | 3522 | CE1 | PHE | 2333 | 48.932 | 12.026 | 164.984 | 1.00 | 56.27 |
| ATOM | 3523 | CE2 | PHE | 2333 | 48.684 | 14.298 | 164.184 | 1.00 | 56.09 |
| ATOM | 3524 | CZ | PHE | 2333 | 48.914 | 13.397 | 165.238 | 1.00 | 56.78 |
| ATOM | 3525 | C | PHE | 2333 | 49.532 | 11.927 | 159.065 | 1.00 | 48.00 |

TABLE 6-continued

| | | | FGF2/FGFR1/Heparin Ternary Complex | | | | | |
|---|---|---|---|---|---|---|---|---|
| ATOM | 3526 | O | PHE | 2333 | 50.653 | 11.419 | 159.167 | 1.00 | 47.65 |
| ATOM | 3527 | N | GLU | 2334 | 48.749 | 11.756 | 158.009 | 1.00 | 47.38 |
| ATOM | 3528 | CA | GLU | 2334 | 49.150 | 10.937 | 156.882 | 1.00 | 46.61 |
| ATOM | 3529 | CB | GLU | 2334 | 47.984 | 10.764 | 155.897 | 1.00 | 48.93 |
| ATOM | 3530 | CG | GLU | 2334 | 46.775 | 9.973 | 156.415 | 1.00 | 53.50 |
| ATOM | 3531 | CD | GLU | 2334 | 45.860 | 10.760 | 157.379 | 1.00 | 57.12 |
| ATOM | 3532 | OE1 | GLU | 2334 | 46.224 | 10.929 | 158.572 | 1.00 | 58.37 |
| ATOM | 3533 | OE2 | GLU | 2334 | 44.768 | 11.208 | 156.941 | 1.00 | 57.75 |
| ATOM | 3534 | C | GLU | 2334 | 50.318 | 11.595 | 156.170 | 1.00 | 44.79 |
| ATOM | 3535 | O | GLU | 2334 | 51.326 | 10.955 | 155.895 | 1.00 | 44.39 |
| ATOM | 3536 | N | ASP | 2335 | 50.181 | 12.882 | 155.879 | 1.00 | 42.84 |
| ATOM | 3537 | CA | ASP | 2335 | 51.230 | 13.618 | 155.181 | 1.00 | 41.47 |
| ATOM | 3538 | CB | ASP | 2335 | 50.817 | 15.073 | 154.958 | 1.00 | 42.11 |
| ATOM | 3539 | CG | ASP | 2335 | 49.568 | 15.199 | 154.119 | 1.00 | 42.52 |
| ATOM | 3540 | OD1 | ASP | 2335 | 49.399 | 14.405 | 153.163 | 1.00 | 40.64 |
| ATOM | 3541 | OD2 | ASP | 2335 | 48.763 | 16.110 | 154.414 | 1.00 | 43.61 |
| ATOM | 3542 | C | ASP | 2335 | 52.559 | 13.594 | 155.920 | 1.00 | 39.66 |
| ATOM | 3543 | O | ASP | 2335 | 53.599 | 13.957 | 155.370 | 1.00 | 38.79 |
| ATOM | 3544 | N | ALA | 2336 | 52.523 | 13.178 | 157.176 | 1.00 | 37.90 |
| ATOM | 3545 | CA | ALA | 2336 | 53.732 | 13.110 | 157.972 | 1.00 | 35.84 |
| ATOM | 3546 | CB | ALA | 2336 | 53.402 | 12.565 | 159.357 | 1.00 | 35.87 |
| ATOM | 3547 | C | ALA | 2336 | 54.711 | 12.193 | 157.257 | 1.00 | 34.69 |
| ATOM | 3548 | O | ALA | 2336 | 54.307 | 11.198 | 156.646 | 1.00 | 34.69 |
| ATOM | 3549 | N | GLY | 2337 | 55.994 | 12.523 | 157.318 | 1.00 | 32.66 |
| ATOM | 3550 | CA | GLY | 2337 | 56.966 | 11.679 | 156.659 | 1.00 | 31.48 |
| ATOM | 3551 | C | GLY | 2337 | 58.111 | 12.389 | 155.972 | 1.00 | 30.67 |
| ATOM | 3552 | O | GLY | 2337 | 58.294 | 13.590 | 156.108 | 1.00 | 30.86 |
| ATOM | 3553 | N | GLU | 2338 | 58.879 | 11.624 | 155.211 | 1.00 | 29.73 |
| ATOM | 3554 | CA | GLU | 2338 | 60.037 | 12.137 | 154.515 | 1.00 | 29.01 |
| ATOM | 3555 | CB | GLU | 2338 | 61.181 | 11.145 | 154.647 | 1.00 | 29.00 |
| ATOM | 3556 | CG | GLU | 2338 | 62.364 | 11.401 | 153.752 | 1.00 | 29.50 |
| ATOM | 3557 | CD | GLU | 2338 | 63.415 | 10.343 | 153.957 | 1.00 | 30.76 |
| ATOM | 3558 | OE1 | GLU | 2338 | 63.021 | 9.169 | 154.106 | 1.00 | 31.01 |
| ATOM | 3559 | OE2 | GLU | 2338 | 64.622 | 10.668 | 153.974 | 1.00 | 31.61 |
| ATOM | 3560 | C | GLU | 2338 | 59.799 | 12.436 | 153.052 | 1.00 | 28.96 |
| ATOM | 3561 | O | GLU | 2338 | 59.389 | 11.573 | 152.284 | 1.00 | 30.22 |
| ATOM | 3562 | N | TYR | 2339 | 60.071 | 13.672 | 152.668 | 1.00 | 27.97 |
| ATOM | 3563 | CA | TYR | 2339 | 59.906 | 14.075 | 151.291 | 1.00 | 27.40 |
| ATOM | 3564 | CB | TYR | 2339 | 59.145 | 15.395 | 151.216 | 1.00 | 27.47 |
| ATOM | 3565 | CG | TYR | 2339 | 57.696 | 15.266 | 151.646 | 1.00 | 28.45 |
| ATOM | 3566 | CD1 | TYR | 2339 | 57.359 | 14.954 | 152.970 | 1.00 | 27.51 |
| ATOM | 3567 | CE1 | TYR | 2339 | 56.035 | 14.821 | 153.361 | 1.00 | 26.85 |
| ATOM | 3568 | CD2 | TYR | 2339 | 56.658 | 15.441 | 150.724 | 1.00 | 27.65 |
| ATOM | 3569 | CE2 | TYR | 2339 | 55.338 | 15.310 | 151.106 | 1.00 | 26.77 |
| ATOM | 3570 | CZ | TYR | 2339 | 55.031 | 15.001 | 152.422 | 1.00 | 27.88 |
| ATOM | 3571 | OH | TYR | 2339 | 53.710 | 14.862 | 152.783 | 1.00 | 30.57 |
| ATOM | 3572 | C | TYR | 2339 | 61.286 | 14.200 | 150.670 | 1.00 | 27.30 |
| ATOM | 3573 | O | TYR | 2339 | 62.271 | 14.467 | 151.360 | 1.00 | 27.32 |
| ATOM | 3574 | N | THR | 2340 | 61.354 | 14.004 | 149.360 | 1.00 | 26.14 |
| ATOM | 3575 | CA | THR | 2340 | 62.623 | 14.057 | 148.677 | 1.00 | 25.92 |
| ATOM | 3576 | CB | THR | 2340 | 63.077 | 12.645 | 148.289 | 1.00 | 25.98 |
| ATOM | 3577 | OG1 | THR | 2340 | 63.349 | 11.894 | 149.477 | 1.00 | 26.37 |
| ATOM | 3578 | CG2 | THR | 2340 | 64.316 | 12.700 | 147.426 | 1.00 | 24.86 |
| ATOM | 3579 | C | THR | 2340 | 62.582 | 14.891 | 147.424 | 1.00 | 26.30 |
| ATOM | 3580 | O | THR | 2340 | 61.628 | 14.830 | 146.662 | 1.00 | 26.81 |
| ATOM | 3581 | N | CYS | 2341 | 63.627 | 15.679 | 147.224 | 1.00 | 26.04 |
| ATOM | 3582 | CA | CYS | 2341 | 63.723 | 16.482 | 146.035 | 1.00 | 26.62 |
| ATOM | 3583 | C | CYS | 2341 | 64.785 | 15.782 | 145.252 | 1.00 | 27.07 |
| ATOM | 3584 | O | CYS | 2341 | 65.926 | 15.682 | 145.698 | 1.00 | 28.08 |
| ATOM | 3585 | CB | CYS | 2341 | 64.186 | 17.890 | 146.341 | 1.00 | 28.45 |
| ATOM | 3586 | SG | CYS | 2341 | 64.529 | 18.842 | 144.834 | 1.00 | 26.76 |
| ATOM | 3587 | N | LEU | 2342 | 64.394 | 15.280 | 144.092 | 1.00 | 27.03 |
| ATOM | 3588 | CA | LEU | 2342 | 65.290 | 14.552 | 143.221 | 1.00 | 26.61 |
| ATOM | 3589 | CB | LEU | 2342 | 64.696 | 13.172 | 142.917 | 1.00 | 25.47 |
| ATOM | 3590 | CG | LEU | 2342 | 65.260 | 12.404 | 141.723 | 1.00 | 26.27 |
| ATOM | 3591 | CD1 | LEU | 2342 | 66.785 | 12.333 | 141.808 | 1.00 | 26.88 |
| ATOM | 3592 | CD2 | LEU | 2342 | 64.648 | 11.020 | 141.685 | 1.00 | 25.17 |
| ATOM | 3593 | C | LEU | 2342 | 65.473 | 15.330 | 141.940 | 1.00 | 27.03 |
| ATOM | 3594 | O | LEU | 2342 | 64.501 | 15.725 | 141.301 | 1.00 | 29.20 |
| ATOM | 3595 | N | ALA | 2343 | 66.722 | 15.561 | 141.565 | 1.00 | 25.87 |
| ATOM | 3596 | CA | ALA | 2343 | 67.009 | 16.282 | 140.339 | 1.00 | 24.38 |
| ATOM | 3597 | CB | ALA | 2343 | 67.383 | 17.698 | 140.648 | 1.00 | 25.43 |
| ATOM | 3598 | C | ALA | 2343 | 68.159 | 15.582 | 139.658 | 1.00 | 23.96 |
| ATOM | 3599 | O | ALA | 2343 | 69.145 | 15.229 | 140.300 | 1.00 | 22.49 |
| ATOM | 3600 | N | GLY | 2344 | 68.031 | 15.365 | 138.357 | 1.00 | 23.92 |
| ATOM | 3601 | CA | GLY | 2344 | 69.092 | 14.693 | 137.644 | 1.00 | 24.37 |
| ATOM | 3602 | C | GLY | 2344 | 69.197 | 15.126 | 136.206 | 1.00 | 25.75 |

TABLE 6-continued

FGF2/FGFR1/Heparin Ternary Complex

| ATOM | 3603 | O | GLY | 2344 | 68.211 | 15.535 | 135.602 | 1.00 | 27.54 |
|---|---|---|---|---|---|---|---|---|---|
| ATOM | 3604 | N | ASN | 2345 | 70.405 | 15.068 | 135.666 | 1.00 | 26.24 |
| ATOM | 3605 | CA | ASN | 2345 | 70.623 | 15.412 | 134.277 | 1.00 | 26.80 |
| ATOM | 3606 | CB | ASN | 2345 | 71.532 | 16.641 | 134.132 | 1.00 | 26.94 |
| ATOM | 3607 | CG | ASN | 2345 | 72.889 | 16.461 | 134.784 | 1.00 | 26.87 |
| ATOM | 3608 | OD1 | ASN | 2345 | 73.504 | 15.402 | 134.694 | 1.00 | 27.94 |
| ATOM | 3609 | ND2 | ASN | 2345 | 73.375 | 17.514 | 135.427 | 1.00 | 26.75 |
| ATOM | 3610 | C | ASN | 2345 | 71.259 | 14.193 | 133.632 | 1.00 | 27.51 |
| ATOM | 3611 | O | ASN | 2345 | 71.281 | 13.116 | 134.225 | 1.00 | 25.72 |
| ATOM | 3612 | N | SER | 2346 | 71.779 | 14.363 | 132.425 | 1.00 | 28.32 |
| ATOM | 3613 | CA | SER | 2346 | 72.400 | 13.261 | 131.709 | 1.00 | 29.50 |
| ATOM | 3614 | CB | SER | 2346 | 72.668 | 13.698 | 130.268 | 1.00 | 30.89 |
| ATOM | 3615 | OG | SER | 2346 | 73.341 | 12.687 | 129.542 | 1.00 | 31.93 |
| ATOM | 3616 | C | SER | 2346 | 73.700 | 12.742 | 132.324 | 1.00 | 28.96 |
| ATOM | 3617 | O | SER | 2346 | 74.239 | 11.736 | 131.880 | 1.00 | 30.38 |
| ATOM | 3618 | N | ILE | 2347 | 74.206 | 13.418 | 133.343 | 1.00 | 28.17 |
| ATOM | 3619 | CA | ILE | 2347 | 75.463 | 13.012 | 133.948 | 1.00 | 28.00 |
| ATOM | 3620 | CB | ILE | 2347 | 76.346 | 14.236 | 134.206 | 1.00 | 26.86 |
| ATOM | 3621 | CG2 | ILE | 2347 | 77.646 | 13.823 | 134.859 | 1.00 | 25.01 |
| ATOM | 3622 | CG1 | ILE | 2347 | 76.607 | 14.955 | 132.886 | 1.00 | 27.00 |
| ATOM | 3623 | CD1 | ILE | 2347 | 77.300 | 16.281 | 133.041 | 1.00 | 26.83 |
| ATOM | 3624 | C | ILE | 2347 | 75.292 | 12.257 | 135.247 | 1.00 | 29.80 |
| ATOM | 3625 | O | ILE | 2347 | 76.087 | 11.374 | 135.568 | 1.00 | 30.99 |
| ATOM | 3626 | N | GLY | 2348 | 74.266 | 12.605 | 136.010 | 1.00 | 30.31 |
| ATOM | 3627 | CA | GLY | 2348 | 74.052 | 11.918 | 137.267 | 1.00 | 31.07 |
| ATOM | 3628 | C | GLY | 2348 | 72.780 | 12.343 | 137.966 | 1.00 | 31.25 |
| ATOM | 3629 | O | GLY | 2348 | 72.037 | 13.181 | 137.449 | 1.00 | 32.24 |
| ATOM | 3630 | N | LEU | 2349 | 72.530 | 11.763 | 139.139 | 1.00 | 29.67 |
| ATOM | 3631 | CA | LEU | 2349 | 71.345 | 12.083 | 139.918 | 1.00 | 28.44 |
| ATOM | 3632 | CB | LEU | 2349 | 70.467 | 10.851 | 140.109 | 1.00 | 29.09 |
| ATOM | 3633 | CG | LEU | 2349 | 69.628 | 10.359 | 138.930 | 1.00 | 31.74 |
| ATOM | 3634 | CD1 | LEU | 2349 | 68.586 | 11.417 | 138.581 | 1.00 | 31.84 |
| ATOM | 3635 | CD2 | LEU | 2349 | 70.528 | 10.034 | 137.729 | 1.00 | 32.28 |
| ATOM | 3636 | C | LEU | 2349 | 71.721 | 12.613 | 141.286 | 1.00 | 27.83 |
| ATOM | 3637 | O | LEU | 2349 | 72.689 | 12.154 | 141.890 | 1.00 | 27.97 |
| ATOM | 3638 | N | SER | 2350 | 70.946 | 13.583 | 141.766 | 1.00 | 26.94 |
| ATOM | 3639 | CA | SER | 2350 | 71.151 | 14.188 | 143.076 | 1.00 | 24.05 |
| ATOM | 3640 | CB | SER | 2350 | 71.825 | 15.551 | 142.958 | 1.00 | 22.64 |
| ATOM | 3641 | OG | SER | 2350 | 73.228 | 15.423 | 142.889 | 1.00 | 21.98 |
| ATOM | 3642 | C | SER | 2350 | 69.803 | 14.362 | 143.730 | 1.00 | 24.25 |
| ATOM | 3643 | O | SER | 2350 | 68.796 | 14.580 | 143.055 | 1.00 | 24.27 |
| ATOM | 3644 | N | HIS | 2351 | 69.784 | 14.268 | 145.051 | 1.00 | 24.81 |
| ATOM | 3645 | CA | HIS | 2351 | 68.545 | 14.413 | 145.791 | 1.00 | 25.48 |
| ATOM | 3646 | CB | HIS | 2351 | 67.769 | 13.106 | 145.770 | 1.00 | 26.54 |
| ATOM | 3647 | CG | HIS | 2351 | 68.520 | 11.963 | 146.377 | 1.00 | 28.96 |
| ATOM | 3648 | CD2 | HIS | 2351 | 68.539 | 11.479 | 147.642 | 1.00 | 30.01 |
| ATOM | 3649 | ND1 | HIS | 2351 | 69.435 | 11.213 | 145.667 | 1.00 | 29.42 |
| ATOM | 3650 | CE1 | HIS | 2351 | 69.983 | 10.316 | 146.466 | 1.00 | 30.00 |
| ATOM | 3651 | NE2 | HIS | 2351 | 69.458 | 10.457 | 147.670 | 1.00 | 31.92 |
| ATOM | 3652 | C | HIS | 2351 | 68.808 | 14.777 | 147.235 | 1.00 | 25.95 |
| ATOM | 3653 | O | HIS | 2351 | 69.811 | 14.378 | 147.809 | 1.00 | 26.85 |
| ATOM | 3654 | N | HIS | 2352 | 67.890 | 15.539 | 147.816 | 1.00 | 26.51 |
| ATOM | 3655 | CA | HIS | 2352 | 67.967 | 15.941 | 149.215 | 1.00 | 26.09 |
| ATOM | 3656 | CB | HIS | 2352 | 68.141 | 17.444 | 149.350 | 1.00 | 26.91 |
| ATOM | 3657 | CG | HIS | 2352 | 69.542 | 17.904 | 149.164 | 1.00 | 27.75 |
| ATOM | 3658 | CD2 | HIS | 2352 | 70.689 | 17.210 | 148.980 | 1.00 | 28.62 |
| ATOM | 3659 | ND1 | HIS | 2352 | 69.894 | 19.235 | 149.191 | 1.00 | 27.71 |
| ATOM | 3660 | CE1 | HIS | 2352 | 71.200 | 19.341 | 149.036 | 1.00 | 29.91 |
| ATOM | 3661 | NE2 | HIS | 2352 | 71.707 | 18.126 | 148.905 | 1.00 | 29.86 |
| ATOM | 3662 | C | HIS | 2352 | 66.632 | 15.582 | 149.812 | 1.00 | 26.59 |
| ATOM | 3663 | O | HIS | 2352 | 65.600 | 15.862 | 149.216 | 1.00 | 27.59 |
| ATOM | 3664 | N | SER | 2353 | 66.638 | 14.959 | 150.978 | 1.00 | 26.84 |
| ATOM | 3665 | CA | SER | 2353 | 65.383 | 14.603 | 151.615 | 1.00 | 27.71 |
| ATOM | 3666 | CB | SER | 2353 | 65.453 | 13.186 | 152.165 | 1.00 | 27.98 |
| ATOM | 3667 | OG | SER | 2353 | 65.621 | 12.260 | 151.105 | 1.00 | 29.93 |
| ATOM | 3668 | C | SER | 2353 | 65.100 | 15.588 | 152.730 | 1.00 | 28.03 |
| ATOM | 3669 | O | SER | 2353 | 65.860 | 16.533 | 152.930 | 1.00 | 29.62 |
| ATOM | 3670 | N | ALA | 2354 | 63.999 | 15.381 | 153.440 | 1.00 | 27.45 |
| ATOM | 3671 | CA | ALA | 2354 | 63.613 | 16.252 | 154.548 | 1.00 | 27.88 |
| ATOM | 3672 | CB | ALA | 2354 | 63.217 | 17.614 | 154.052 | 1.00 | 28.75 |
| ATOM | 3673 | C | ALA | 2354 | 62.438 | 15.600 | 155.226 | 1.00 | 28.41 |
| ATOM | 3674 | O | ALA | 2354 | 61.669 | 14.895 | 154.586 | 1.00 | 29.30 |
| ATOM | 3675 | N | TRP | 2355 | 62.292 | 15.837 | 156.519 | 1.00 | 28.44 |
| ATOM | 3676 | CA | TRP | 2355 | 61.210 | 15.231 | 157.248 | 1.00 | 28.71 |
| ATOM | 3677 | CB | TRP | 2355 | 61.763 | 14.530 | 158.468 | 1.00 | 31.13 |
| ATOM | 3678 | CG | TRP | 2355 | 61.507 | 13.072 | 158.407 | 1.00 | 37.37 |
| ATOM | 3679 | CD2 | TRP | 2355 | 62.409 | 12.078 | 157.920 | 1.00 | 38.88 |

TABLE 6-continued

FGF2/FGFR1/Heparin Ternary Complex

| ATOM | 3680 | CE2 | TRP | 2355 | 61.718 | 10.838 | 157.941 | 1.00 | 39.14 |
|---|---|---|---|---|---|---|---|---|---|
| ATOM | 3681 | CE3 | TRP | 2355 | 63.735 | 12.113 | 157.463 | 1.00 | 39.77 |
| ATOM | 3682 | CD1 | TRP | 2355 | 60.331 | 12.415 | 158.706 | 1.00 | 38.18 |
| ATOM | 3683 | NE1 | TRP | 2355 | 60.455 | 11.074 | 158.425 | 1.00 | 38.62 |
| ATOM | 3684 | CZ2 | TRP | 2355 | 62.311 | 9.646 | 157.519 | 1.00 | 39.98 |
| ATOM | 3685 | CZ3 | TRP | 2355 | 64.324 | 10.932 | 157.044 | 1.00 | 40.99 |
| ATOM | 3686 | CH2 | TRP | 2355 | 63.610 | 9.710 | 157.074 | 1.00 | 40.93 |
| ATOM | 3687 | C | TRP | 2355 | 60.099 | 16.170 | 157.663 | 1.00 | 28.81 |
| ATOM | 3688 | O | TRP | 2355 | 60.348 | 17.281 | 158.121 | 1.00 | 29.84 |
| ATOM | 3689 | N | LEU | 2356 | 58.862 | 15.727 | 157.484 | 1.00 | 28.47 |
| ATOM | 3690 | CA | LEU | 2356 | 57.719 | 16.526 | 157.889 | 1.00 | 27.92 |
| ATOM | 3691 | CB | LEU | 2356 | 56.648 | 16.570 | 156.805 | 1.00 | 26.20 |
| ATOM | 3692 | CG | LEU | 2356 | 55.726 | 17.794 | 156.877 | 1.00 | 26.11 |
| ATOM | 3693 | CD1 | LEU | 2356 | 54.319 | 17.376 | 156.538 | 1.00 | 26.99 |
| ATOM | 3694 | CD2 | LEU | 2356 | 55.747 | 18.427 | 158.253 | 1.00 | 25.04 |
| ATOM | 3695 | C | LEU | 2356 | 57.134 | 15.882 | 159.151 | 1.00 | 28.92 |
| ATOM | 3696 | O | LEU | 2356 | 56.722 | 14.716 | 159.143 | 1.00 | 28.83 |
| ATOM | 3697 | N | THR | 2357 | 57.135 | 16.648 | 160.238 | 1.00 | 29.45 |
| ATOM | 3698 | CA | THR | 2357 | 56.602 | 16.201 | 161.522 | 1.00 | 30.00 |
| ATOM | 3699 | CB | THR | 2357 | 57.582 | 16.504 | 162.694 | 1.00 | 28.55 |
| ATOM | 3700 | OG1 | THR | 2357 | 58.603 | 15.505 | 162.745 | 1.00 | 29.02 |
| ATOM | 3701 | CG2 | THR | 2357 | 56.849 | 16.510 | 164.016 | 1.00 | 26.69 |
| ATOM | 3702 | C | THR | 2357 | 55.288 | 16.939 | 161.783 | 1.00 | 32.06 |
| ATOM | 3703 | O | THR | 2357 | 55.259 | 18.175 | 161.827 | 1.00 | 32.27 |
| ATOM | 3704 | N | VAL | 2358 | 54.206 | 16.181 | 161.956 | 1.00 | 33.20 |
| ATOM | 3705 | CA | VAL | 2358 | 52.898 | 16.772 | 162.211 | 1.00 | 34.64 |
| ATOM | 3706 | CB | VAL | 2358 | 51.846 | 16.259 | 161.211 | 1.00 | 35.47 |
| ATOM | 3707 | CG1 | VAL | 2358 | 50.480 | 16.796 | 161.586 | 1.00 | 35.84 |
| ATOM | 3708 | CG2 | VAL | 2358 | 52.209 | 16.696 | 159.797 | 1.00 | 36.10 |
| ATOM | 3709 | C | VAL | 2358 | 52.400 | 16.476 | 163.621 | 1.00 | 35.63 |
| ATOM | 3710 | O | VAL | 2358 | 52.435 | 15.330 | 164.071 | 1.00 | 36.05 |
| ATOM | 3711 | N | LEU | 2359 | 51.924 | 17.511 | 164.311 | 1.00 | 35.87 |
| ATOM | 3712 | CA | LEU | 2359 | 51.424 | 17.340 | 165.668 | 1.00 | 35.60 |
| ATOM | 3713 | CB | LEU | 2359 | 52.380 | 18.055 | 166.616 | 1.00 | 33.76 |
| ATOM | 3714 | CG | LEU | 2359 | 53.810 | 17.511 | 166.468 | 1.00 | 33.43 |
| ATOM | 3715 | CD1 | LEU | 2359 | 54.807 | 18.419 | 167.188 | 1.00 | 30.83 |
| ATOM | 3716 | CD2 | LEU | 2359 | 53.874 | 16.071 | 167.002 | 1.00 | 31.95 |
| ATOM | 3717 | C | LEU | 2359 | 49.973 | 17.824 | 165.846 | 1.00 | 36.53 |
| ATOM | 3718 | O | LEU | 2359 | 49.261 | 17.260 | 166.716 | 1.00 | 36.43 |
| ATOM | 3719 | CB | MET | 3149 | 110.903 | 20.490 | 84.760 | 1.00 | 57.84 |
| ATOM | 3720 | CG | MET | 3149 | 112.225 | 20.282 | 85.488 | 1.00 | 60.66 |
| ATOM | 3721 | SD | MET | 3149 | 113.293 | 19.105 | 84.603 | 1.00 | 64.12 |
| ATOM | 3722 | CE | MET | 3149 | 114.208 | 20.229 | 83.476 | 1.00 | 62.64 |
| ATOM | 3723 | C | MET | 3149 | 109.773 | 18.509 | 85.792 | 1.00 | 53.78 |
| ATOM | 3724 | O | MET | 3149 | 109.675 | 19.157 | 86.834 | 1.00 | 53.83 |
| ATOM | 3725 | N | MET | 3149 | 108.962 | 19.445 | 83.629 | 1.00 | 55.00 |
| ATOM | 3726 | CA | MET | 3149 | 110.163 | 19.183 | 84.475 | 1.00 | 55.34 |
| ATOM | 3727 | N | PRO | 3150 | 109.571 | 17.185 | 85.762 | 1.00 | 52.17 |
| ATOM | 3728 | CD | PRO | 3150 | 109.866 | 16.279 | 84.640 | 1.00 | 51.98 |
| ATOM | 3729 | CA | PRO | 3150 | 109.183 | 16.418 | 86.948 | 1.00 | 50.85 |
| ATOM | 3730 | CB | PRO | 3150 | 109.140 | 14.979 | 86.435 | 1.00 | 49.99 |
| ATOM | 3731 | CG | PRO | 3150 | 110.150 | 14.975 | 85.356 | 1.00 | 51.28 |
| ATOM | 3732 | C | PRO | 3150 | 110.063 | 16.578 | 88.182 | 1.00 | 49.83 |
| ATOM | 3733 | O | PRO | 3150 | 111.288 | 16.687 | 88.089 | 1.00 | 49.14 |
| ATOM | 3734 | N | VAL | 3151 | 109.402 | 16.602 | 89.338 | 1.00 | 48.76 |
| ATOM | 3735 | CA | VAL | 3151 | 110.056 | 16.731 | 90.636 | 1.00 | 46.73 |
| ATOM | 3736 | CB | VAL | 3151 | 110.317 | 18.214 | 90.995 | 1.00 | 45.76 |
| ATOM | 3737 | CG1 | VAL | 3151 | 110.372 | 18.396 | 92.488 | 1.00 | 45.78 |
| ATOM | 3738 | CG2 | VAL | 3151 | 111.642 | 18.648 | 90.406 | 1.00 | 46.31 |
| ATOM | 3739 | C | VAL | 3151 | 109.196 | 16.074 | 91.711 | 1.00 | 45.95 |
| ATOM | 3740 | O | VAL | 3151 | 107.983 | 16.300 | 91.789 | 1.00 | 45.41 |
| ATOM | 3741 | N | ALA | 3152 | 109.834 | 15.242 | 92.527 | 1.00 | 44.98 |
| ATOM | 3742 | CA | ALA | 3152 | 109.135 | 14.542 | 93.594 | 1.00 | 43.99 |
| ATOM | 3743 | CB | ALA | 3152 | 109.994 | 13.404 | 94.122 | 1.00 | 44.25 |
| ATOM | 3744 | C | ALA | 3152 | 108.786 | 15.504 | 94.720 | 1.00 | 42.90 |
| ATOM | 3745 | O | ALA | 3152 | 109.503 | 16.471 | 94.981 | 1.00 | 43.11 |
| ATOM | 3746 | N | PRO | 3153 | 107.675 | 15.245 | 95.411 | 1.00 | 41.61 |
| ATOM | 3747 | CD | PRO | 3153 | 106.876 | 14.008 | 95.417 | 1.00 | 40.38 |
| ATOM | 3748 | CA | PRO | 3153 | 107.284 | 16.132 | 96.504 | 1.00 | 40.65 |
| ATOM | 3749 | CB | PRO | 3153 | 106.062 | 15.433 | 97.082 | 1.00 | 41.36 |
| ATOM | 3750 | CG | PRO | 3153 | 106.355 | 13.984 | 96.820 | 1.00 | 41.00 |
| ATOM | 3751 | C | PRO | 3153 | 108.407 | 16.268 | 97.517 | 1.00 | 40.38 |
| ATOM | 3752 | O | PRO | 3153 | 109.068 | 15.285 | 97.849 | 1.00 | 40.88 |
| ATOM | 3753 | N | TYR | 3154 | 108.633 | 17.479 | 98.004 | 1.00 | 39.09 |
| ATOM | 3754 | CA | TYR | 3154 | 109.682 | 17.689 | 98.991 | 1.00 | 37.91 |
| ATOM | 3755 | CB | TYR | 3154 | 110.971 | 18.119 | 98.296 | 1.00 | 37.75 |
| ATOM | 3756 | CG | TYR | 3154 | 110.841 | 19.437 | 97.570 | 1.00 | 40.09 |

TABLE 6-continued

FGF2/FGFR1/Heparin Ternary Complex

| ATOM | 3757 | CD1 | TYR | 3154 | 110.157 | 19.522 | 96.356 | 1.00 | 40.03 |
|---|---|---|---|---|---|---|---|---|---|
| ATOM | 3758 | CE1 | TYR | 3154 | 109.999 | 20.751 | 95.704 | 1.00 | 39.70 |
| ATOM | 3759 | CD2 | TYR | 3154 | 111.368 | 20.617 | 98.117 | 1.00 | 39.82 |
| ATOM | 3760 | CE2 | TYR | 3154 | 111.214 | 21.846 | 97.472 | 1.00 | 38.84 |
| ATOM | 3761 | CZ | TYR | 3154 | 110.528 | 21.905 | 96.270 | 1.00 | 39.55 |
| ATOM | 3762 | OH | TYR | 3154 | 110.356 | 23.113 | 95.634 | 1.00 | 39.77 |
| ATOM | 3763 | C | TYR | 3154 | 109.274 | 18.739 | 100.026 | 1.00 | 36.94 |
| ATOM | 3764 | O | TYR | 3154 | 108.474 | 19.622 | 99.743 | 1.00 | 37.50 |
| ATOM | 3765 | N | TRP | 3155 | 109.822 | 18.631 | 101.230 | 1.00 | 35.27 |
| ATOM | 3766 | CA | TRP | 3155 | 109.518 | 19.574 | 102.299 | 1.00 | 33.87 |
| ATOM | 3767 | CB | TRP | 3155 | 110.107 | 19.093 | 103.621 | 1.00 | 32.01 |
| ATOM | 3768 | CG | TRP | 3155 | 109.573 | 17.786 | 104.143 | 1.00 | 28.02 |
| ATOM | 3769 | CD2 | TRP | 3155 | 108.220 | 17.322 | 104.097 | 1.00 | 26.45 |
| ATOM | 3770 | CE2 | TRP | 3155 | 108.185 | 16.066 | 104.746 | 1.00 | 25.14 |
| ATOM | 3771 | CE3 | TRP | 3155 | 107.035 | 17.841 | 103.569 | 1.00 | 26.33 |
| ATOM | 3772 | CD1 | TRP | 3155 | 110.281 | 16.824 | 104.802 | 1.00 | 27.15 |
| ATOM | 3773 | NE1 | TRP | 3155 | 109.455 | 15.787 | 105.167 | 1.00 | 25.80 |
| ATOM | 3774 | CZ2 | TRP | 3155 | 107.017 | 15.328 | 104.885 | 1.00 | 24.17 |
| ATOM | 3775 | CZ3 | TRP | 3155 | 105.871 | 17.101 | 103.708 | 1.00 | 26.53 |
| ATOM | 3776 | CH2 | TRP | 3155 | 105.874 | 15.856 | 104.361 | 1.00 | 24.65 |
| ATOM | 3777 | C | TRP | 3155 | 110.111 | 20.938 | 101.969 | 1.00 | 35.28 |
| ATOM | 3778 | O | TRP | 3155 | 111.311 | 21.051 | 101.712 | 1.00 | 35.18 |
| ATOM | 3779 | N | THR | 3156 | 109.273 | 21.972 | 101.983 | 1.00 | 36.76 |
| ATOM | 3780 | CA | THR | 3156 | 109.728 | 23.325 | 101.678 | 1.00 | 37.57 |
| ATOM | 3781 | CB | THR | 3156 | 108.621 | 24.143 | 101.025 | 1.00 | 35.80 |
| ATOM | 3782 | OG1 | THR | 3156 | 107.605 | 24.430 | 101.990 | 1.00 | 36.19 |
| ATOM | 3783 | CG2 | THR | 3156 | 108.010 | 23.373 | 99.889 | 1.00 | 34.67 |
| ATOM | 3784 | C | THR | 3156 | 110.198 | 24.056 | 102.929 | 1.00 | 39.50 |
| ATOM | 3785 | O | THR | 3156 | 111.095 | 24.893 | 102.861 | 1.00 | 39.18 |
| ATOM | 3786 | N | SER | 3157 | 109.588 | 23.737 | 104.066 | 1.00 | 42.72 |
| ATOM | 3787 | CA | SER | 3157 | 109.954 | 24.356 | 105.342 | 1.00 | 46.50 |
| ATOM | 3788 | CB | SER | 3157 | 108.848 | 25.302 | 105.822 | 1.00 | 46.20 |
| ATOM | 3789 | OG | SER | 3157 | 108.611 | 26.330 | 104.878 | 1.00 | 46.67 |
| ATOM | 3790 | C | SER | 3157 | 110.165 | 23.250 | 106.368 | 1.00 | 48.51 |
| ATOM | 3791 | O | SER | 3157 | 109.391 | 23.103 | 107.317 | 1.00 | 49.78 |
| ATOM | 3792 | N | PRO | 3158 | 111.232 | 22.462 | 106.194 | 1.00 | 49.73 |
| ATOM | 3793 | CD | PRO | 3158 | 112.328 | 22.734 | 105.255 | 1.00 | 50.01 |
| ATOM | 3794 | CA | PRO | 3158 | 111.586 | 21.347 | 107.072 | 1.00 | 51.06 |
| ATOM | 3795 | CB | PRO | 3158 | 112.908 | 20.870 | 106.490 | 1.00 | 51.19 |
| ATOM | 3796 | CG | PRO | 3158 | 113.496 | 22.119 | 105.971 | 1.00 | 50.83 |
| ATOM | 3797 | C | PRO | 3158 | 111.698 | 21.681 | 108.549 | 1.00 | 51.91 |
| ATOM | 3798 | O | PRO | 3158 | 111.358 | 20.861 | 109.402 | 1.00 | 51.46 |
| ATOM | 3799 | N | GLU | 3159 | 112.170 | 22.885 | 108.847 | 1.00 | 52.94 |
| ATOM | 3800 | CA | GLU | 3159 | 112.345 | 23.302 | 110.231 | 1.00 | 54.81 |
| ATOM | 3801 | CB | GLU | 3159 | 113.107 | 24.623 | 110.296 | 1.00 | 56.84 |
| ATOM | 3802 | CG | GLU | 3159 | 114.546 | 24.464 | 109.871 | 1.00 | 59.34 |
| ATOM | 3803 | CD | GLU | 3159 | 115.006 | 23.015 | 109.980 | 1.00 | 60.57 |
| ATOM | 3804 | OE1 | GLU | 3159 | 114.875 | 22.424 | 111.085 | 1.00 | 60.07 |
| ATOM | 3805 | OE2 | GLU | 3159 | 115.487 | 22.476 | 108.954 | 1.00 | 61.42 |
| ATOM | 3806 | C | GLU | 3159 | 111.070 | 23.415 | 111.032 | 1.00 | 54.75 |
| ATOM | 3807 | O | GLU | 3159 | 111.051 | 23.108 | 112.224 | 1.00 | 55.32 |
| ATOM | 3808 | N | LYS | 3160 | 110.007 | 23.861 | 110.380 | 1.00 | 53.40 |
| ATOM | 3809 | CA | LYS | 3160 | 108.726 | 24.004 | 111.039 | 1.00 | 51.90 |
| ATOM | 3810 | CB | LYS | 3160 | 107.859 | 24.954 | 110.216 | 1.00 | 52.24 |
| ATOM | 3811 | CG | LYS | 3160 | 108.533 | 26.301 | 109.981 | 1.00 | 52.84 |
| ATOM | 3812 | CD | LYS | 3160 | 107.643 | 27.268 | 109.218 | 1.00 | 53.85 |
| ATOM | 3813 | CE | LYS | 3160 | 108.256 | 28.667 | 109.190 | 1.00 | 55.22 |
| ATOM | 3814 | NZ | LYS | 3160 | 107.372 | 29.643 | 108.476 | 1.00 | 57.31 |
| ATOM | 3815 | C | LYS | 3160 | 108.054 | 22.637 | 111.184 | 1.00 | 51.08 |
| ATOM | 3816 | O | LYS | 3160 | 106.834 | 22.543 | 111.304 | 1.00 | 50.56 |
| ATOM | 3817 | N | MET | 3161 | 108.867 | 21.583 | 111.177 | 1.00 | 49.65 |
| ATOM | 3818 | CA | MET | 3161 | 108.380 | 20.211 | 111.295 | 1.00 | 47.64 |
| ATOM | 3819 | CB | MET | 3161 | 108.561 | 19.473 | 109.966 | 1.00 | 47.44 |
| ATOM | 3820 | CG | MET | 3161 | 107.940 | 20.187 | 108.776 | 1.00 | 46.79 |
| ATOM | 3821 | SD | MET | 3161 | 107.895 | 19.168 | 107.309 | 1.00 | 45.53 |
| ATOM | 3822 | CE | MET | 3161 | 106.487 | 18.124 | 107.661 | 1.00 | 44.33 |
| ATOM | 3823 | C | MET | 3161 | 109.174 | 19.499 | 112.376 | 1.00 | 47.02 |
| ATOM | 3824 | O | MET | 3161 | 108.979 | 18.314 | 112.631 | 1.00 | 45.87 |
| ATOM | 3825 | N | GLU | 3162 | 110.072 | 20.245 | 113.006 | 1.00 | 46.47 |
| ATOM | 3826 | CA | GLU | 3162 | 110.934 | 19.719 | 114.059 | 1.00 | 45.43 |
| ATOM | 3827 | CB | GLU | 3162 | 111.932 | 20.793 | 114.506 | 1.00 | 47.92 |
| ATOM | 3828 | CG | GLU | 3162 | 113.089 | 21.027 | 113.534 | 1.00 | 50.70 |
| ATOM | 3829 | CD | GLU | 3162 | 114.183 | 19.977 | 113.665 | 1.00 | 52.22 |
| ATOM | 3830 | OE1 | GLU | 3162 | 113.858 | 18.766 | 113.670 | 1.00 | 51.98 |
| ATOM | 3831 | OE2 | GLU | 3162 | 115.370 | 20.369 | 113.763 | 1.00 | 54.08 |
| ATOM | 3832 | C | GLU | 3162 | 110.187 | 19.207 | 115.274 | 1.00 | 43.38 |
| ATOM | 3833 | O | GLU | 3162 | 110.501 | 18.146 | 115.793 | 1.00 | 42.60 |

TABLE 6-continued

FGF2/FGFR1/Heparin Ternary Complex

| ATOM | 3834 | N | LYS | 3163 | 109.206 | 19.973 | 115.724 | 1.00 | 41.71 |
|---|---|---|---|---|---|---|---|---|---|
| ATOM | 3835 | CA | LYS | 3163 | 108.408 | 19.637 | 116.897 | 1.00 | 40.08 |
| ATOM | 3836 | CB | LYS | 3163 | 107.611 | 20.888 | 117.282 | 1.00 | 40.36 |
| ATOM | 3837 | CG | LYS | 3163 | 106.778 | 20.829 | 118.542 | 1.00 | 38.95 |
| ATOM | 3838 | CD | LYS | 3163 | 106.402 | 22.238 | 118.954 | 1.00 | 36.52 |
| ATOM | 3839 | CE | LYS | 3163 | 105.293 | 22.223 | 119.970 | 1.00 | 37.21 |
| ATOM | 3840 | NZ | LYS | 3163 | 104.029 | 21.737 | 119.350 | 1.00 | 36.99 |
| ATOM | 3841 | C | LYS | 3163 | 107.480 | 18.461 | 116.608 | 1.00 | 39.82 |
| ATOM | 3842 | O | LYS | 3163 | 106.334 | 18.656 | 116.212 | 1.00 | 39.27 |
| ATOM | 3843 | N | LYS | 3164 | 107.970 | 17.243 | 116.819 | 1.00 | 39.56 |
| ATOM | 3844 | CA | LYS | 3164 | 107.175 | 16.054 | 116.535 | 1.00 | 39.20 |
| ATOM | 3845 | CB | LYS | 3164 | 108.094 | 14.855 | 116.266 | 1.00 | 39.52 |
| ATOM | 3846 | CG | LYS | 3164 | 109.030 | 15.028 | 115.064 | 1.00 | 40.34 |
| ATOM | 3847 | CD | LYS | 3164 | 109.768 | 13.723 | 114.719 | 1.00 | 42.08 |
| ATOM | 3848 | CE | LYS | 3164 | 110.723 | 13.882 | 113.519 | 1.00 | 44.01 |
| ATOM | 3849 | NZ | LYS | 3164 | 111.437 | 12.625 | 113.081 | 1.00 | 42.94 |
| ATOM | 3850 | C | LYS | 3164 | 106.162 | 15.699 | 117.617 | 1.00 | 38.41 |
| ATOM | 3851 | O | LYS | 3164 | 105.194 | 14.986 | 117.349 | 1.00 | 39.65 |
| ATOM | 3852 | N | LEU | 3165 | 106.374 | 16.187 | 118.833 | 1.00 | 35.73 |
| ATOM | 3853 | CA | LEU | 3165 | 105.442 | 15.901 | 119.913 | 1.00 | 33.17 |
| ATOM | 3854 | CB | LEU | 3165 | 106.164 | 15.301 | 121.110 | 1.00 | 30.21 |
| ATOM | 3855 | CG | LEU | 3165 | 105.251 | 15.064 | 122.311 | 1.00 | 26.93 |
| ATOM | 3856 | CD1 | LEU | 3165 | 104.238 | 13.986 | 121.980 | 1.00 | 26.38 |
| ATOM | 3857 | CD2 | LEU | 3165 | 106.081 | 14.681 | 123.506 | 1.00 | 24.15 |
| ATOM | 3858 | C | LEU | 3165 | 104.716 | 17.162 | 120.357 | 1.00 | 33.21 |
| ATOM | 3859 | O | LEU | 3165 | 105.333 | 18.125 | 120.798 | 1.00 | 31.84 |
| ATOM | 3860 | N | HIS | 3166 | 103.395 | 17.143 | 120.242 | 1.00 | 33.42 |
| ATOM | 3861 | CA | HIS | 3166 | 102.572 | 18.279 | 120.635 | 1.00 | 33.38 |
| ATOM | 3862 | CB | HIS | 3166 | 101.581 | 18.665 | 119.528 | 1.00 | 34.28 |
| ATOM | 3863 | CG | HIS | 3166 | 102.181 | 19.418 | 118.383 | 1.00 | 35.41 |
| ATOM | 3864 | CD2 | HIS | 3166 | 101.790 | 20.562 | 117.774 | 1.00 | 36.20 |
| ATOM | 3865 | ND1 | HIS | 3166 | 103.268 | 18.959 | 117.672 | 1.00 | 37.05 |
| ATOM | 3866 | CE1 | HIS | 3166 | 103.518 | 19.785 | 116.671 | 1.00 | 36.57 |
| ATOM | 3867 | NE2 | HIS | 3166 | 102.634 | 20.766 | 116.710 | 1.00 | 36.72 |
| ATOM | 3868 | C | HIS | 3166 | 101.745 | 17.918 | 121.855 | 1.00 | 32.56 |
| ATOM | 3869 | O | HIS | 3166 | 100.723 | 17.237 | 121.727 | 1.00 | 33.30 |
| ATOM | 3870 | N | ALA | 3167 | 102.172 | 18.372 | 123.027 | 1.00 | 30.59 |
| ATOM | 3871 | CA | ALA | 3167 | 101.430 | 18.112 | 124.253 | 1.00 | 29.28 |
| ATOM | 3872 | CB | ALA | 3167 | 102.377 | 17.761 | 125.374 | 1.00 | 29.41 |
| ATOM | 3873 | C | ALA | 3167 | 100.688 | 19.397 | 124.576 | 1.00 | 28.81 |
| ATOM | 3874 | O | ALA | 3167 | 101.289 | 20.473 | 124.624 | 1.00 | 28.26 |
| ATOM | 3875 | N | VAL | 3168 | 99.381 | 19.290 | 124.778 | 1.00 | 27.99 |
| ATOM | 3876 | CA | VAL | 3168 | 98.572 | 20.465 | 125.084 | 1.00 | 26.35 |
| ATOM | 3877 | CB | VAL | 3168 | 97.977 | 21.081 | 123.792 | 1.00 | 25.05 |
| ATOM | 3878 | CG1 | VAL | 3168 | 99.034 | 21.179 | 122.739 | 1.00 | 24.87 |
| ATOM | 3879 | CG2 | VAL | 3168 | 96.831 | 20.241 | 123.286 | 1.00 | 25.52 |
| ATOM | 3880 | C | VAL | 3168 | 97.420 | 20.113 | 126.023 | 1.00 | 25.97 |
| ATOM | 3881 | O | VAL | 3168 | 97.073 | 18.939 | 126.177 | 1.00 | 25.00 |
| ATOM | 3882 | N | PRO | 3169 | 96.637 | 21.125 | 126.693 | 1.00 | 25.48 |
| ATOM | 3883 | CD | PRO | 3169 | 97.374 | 22.466 | 126.974 | 1.00 | 24.61 |
| ATOM | 3884 | CA | PRO | 3169 | 95.720 | 20.819 | 127.594 | 1.00 | 24.17 |
| ATOM | 3885 | CB | PRO | 3169 | 95.670 | 22.028 | 128.532 | 1.00 | 24.08 |
| ATOM | 3886 | CG | PRO | 3169 | 97.053 | 22.605 | 128.449 | 1.00 | 24.31 |
| ATOM | 3887 | C | PRO | 3169 | 94.506 | 20.736 | 126.687 | 1.00 | 23.77 |
| ATOM | 3888 | O | PRO | 3169 | 94.515 | 21.295 | 125.584 | 1.00 | 23.57 |
| ATOM | 3889 | N | ALA | 3170 | 93.466 | 20.050 | 127.135 | 1.00 | 24.25 |
| ATOM | 3890 | CA | ALA | 3170 | 92.279 | 19.888 | 126.308 | 1.00 | 24.77 |
| ATOM | 3891 | CS | ALA | 3170 | 91.234 | 19.093 | 127.059 | 1.00 | 22.87 |
| ATOM | 3892 | C | ALA | 3170 | 91.687 | 21.206 | 125.817 | 1.00 | 25.55 |
| ATOM | 3893 | O | ALA | 3170 | 91.932 | 22.274 | 126.378 | 1.00 | 25.43 |
| ATOM | 3894 | N | ALA | 3171 | 90.915 | 21.110 | 124.743 | 1.00 | 27.40 |
| ATOM | 3895 | CA | ALA | 3171 | 90.244 | 22.256 | 124.153 | 1.00 | 29.23 |
| ATOM | 3896 | CB | ALA | 3171 | 89.640 | 23.129 | 125.239 | 1.00 | 28.46 |
| ATOM | 3897 | C | ALA | 3171 | 91.158 | 23.090 | 123.283 | 1.00 | 30.83 |
| ATOM | 3898 | O | ALA | 3171 | 90.697 | 23.708 | 122.313 | 1.00 | 33.12 |
| ATOM | 3899 | N | LYS | 3172 | 92.446 | 23.125 | 123.618 | 1.00 | 30.69 |
| ATOM | 3900 | CA | LYS | 3172 | 93.372 | 23.919 | 122.821 | 1.00 | 30.07 |
| ATOM | 3901 | CB | LYS | 3172 | 94.804 | 23.723 | 123.305 | 1.00 | 30.73 |
| ATOM | 3902 | CG | LYS | 3172 | 95.795 | 24.767 | 122.777 | 1.00 | 33.07 |
| ATOM | 3903 | CD | LYS | 3172 | 96.484 | 24.317 | 121.491 | 1.00 | 35.20 |
| ATOM | 3904 | CE | LYS | 3172 | 97.620 | 25.260 | 121.058 | 1.00 | 36.63 |
| ATOM | 3905 | NZ | LYS | 3172 | 97.159 | 26.611 | 120.587 | 1.00 | 38.22 |
| ATOM | 3906 | C | LYS | 3172 | 93.247 | 23.485 | 121.371 | 1.00 | 29.82 |
| ATOM | 3907 | O | LYS | 3172 | 93.014 | 22.311 | 121.090 | 1.00 | 30.27 |
| ATOM | 3908 | N | THR | 3173 | 93.363 | 24.432 | 120.450 | 1.00 | 28.89 |
| ATOM | 3909 | CA | THR | 3173 | 93.275 | 24.093 | 119.042 | 1.00 | 28.50 |
| ATOM | 3910 | CB | THR | 3173 | 92.761 | 25.281 | 118.242 | 1.00 | 29.15 |

TABLE 6-continued

FGF2/FGFR1/Heparin Ternary Complex

| ATOM | 3911 | OG1 | THR | 3173 | 91.377 | 25.480 | 118.570 | 1.00 | 30.98 |
|------|------|-----|-----|------|--------|--------|---------|------|-------|
| ATOM | 3912 | CG2 | THR | 3173 | 92.929 | 25.047 | 116.744 | 1.00 | 26.93 |
| ATOM | 3913 | C | THR | 3173 | 94.645 | 23.650 | 118.559 | 1.00 | 27.27 |
| ATOM | 3914 | O | THR | 3173 | 95.664 | 24.264 | 118.877 | 1.00 | 27.15 |
| ATOM | 3915 | N | VAL | 3174 | 94.679 | 22.556 | 117.815 | 1.00 | 25.48 |
| ATOM | 3916 | CA | VAL | 3174 | 95.951 | 22.068 | 117.340 | 1.00 | 25.53 |
| ATOM | 3917 | CB | VAL | 3174 | 96.244 | 20.665 | 117.882 | 1.00 | 23.48 |
| ATOM | 3918 | CG1 | VAL | 3174 | 97.396 | 20.050 | 117.136 | 1.00 | 23.44 |
| ATOM | 3919 | CG2 | VAL | 3174 | 96.586 | 20.752 | 119.343 | 1.00 | 21.93 |
| ATOM | 3920 | C | VAL | 3174 | 95.999 | 22.069 | 115.835 | 1.00 | 27.17 |
| ATOM | 3921 | O | VAL | 3174 | 95.004 | 21.782 | 115.176 | 1.00 | 28.23 |
| ATOM | 3922 | N | LYS | 3175 | 97.162 | 22.423 | 115.229 | 1.00 | 28.65 |
| ATOM | 3923 | CA | LYS | 3175 | 97.365 | 22.466 | 113.865 | 1.00 | 30.59 |
| ATOM | 3924 | CB | LYS | 3175 | 97.332 | 23.917 | 113.365 | 1.00 | 32.06 |
| ATOM | 3925 | CG | LYS | 3175 | 97.451 | 24.062 | 111.838 | 1.00 | 33.55 |
| ATOM | 3926 | CD | LYS | 3175 | 97.142 | 25.485 | 111.358 | 1.00 | 33.90 |
| ATOM | 3927 | CE | LYS | 3175 | 98.385 | 26.315 | 111.081 | 1.00 | 35.82 |
| ATOM | 3928 | NZ | LYS | 3175 | 99.220 | 26.546 | 112.288 | 1.00 | 38.45 |
| ATOM | 3929 | C | LYS | 3175 | 98.697 | 21.825 | 113.505 | 1.00 | 31.31 |
| ATOM | 3930 | O | LYS | 3175 | 99.745 | 22.214 | 114.029 | 1.00 | 31.44 |
| ATOM | 3931 | N | PHE | 3176 | 98.647 | 20.826 | 112.626 | 1.00 | 32.28 |
| ATOM | 3932 | CA | PHE | 3176 | 99.858 | 20.140 | 112.152 | 1.00 | 33.01 |
| ATOM | 3933 | CB | PHE | 3176 | 99.736 | 18.613 | 112.242 | 1.00 | 30.80 |
| ATOM | 3934 | CG | PHE | 3176 | 99.591 | 18.092 | 113.637 | 1.00 | 30.50 |
| ATOM | 3935 | CD1 | PHE | 3176 | 100.476 | 18.480 | 114.638 | 1.00 | 30.97 |
| ATOM | 3936 | CD2 | PHE | 3176 | 98.565 | 17.211 | 113.958 | 1.00 | 30.24 |
| ATOM | 3937 | CE1 | PHE | 3176 | 100.337 | 18.001 | 115.944 | 1.00 | 29.88 |
| ATOM | 3938 | CE2 | PHE | 3176 | 98.423 | 16.728 | 115.260 | 1.00 | 30.76 |
| ATOM | 3939 | CZ | PHE | 3176 | 99.312 | 17.127 | 116.254 | 1.00 | 29.37 |
| ATOM | 3940 | C | PHE | 3176 | 100.043 | 20.515 | 110.692 | 1.00 | 33.92 |
| ATOM | 3941 | O | PHE | 3176 | 99.088 | 20.452 | 109.911 | 1.00 | 33.90 |
| ATOM | 3942 | N | LYS | 3177 | 101.261 | 20.912 | 110.323 | 1.00 | 35.49 |
| ATOM | 3943 | CA | LYS | 3177 | 101.538 | 21.292 | 108.935 | 1.00 | 36.35 |
| ATOM | 3944 | CB | LYS | 3177 | 101.779 | 22.802 | 108.824 | 1.00 | 38.05 |
| ATOM | 3945 | CG | LYS | 3177 | 102.870 | 23.348 | 109.711 | 1.00 | 42.43 |
| ATOM | 3946 | CD | LYS | 3177 | 102.944 | 24.865 | 109.583 | 1.00 | 46.97 |
| ATOM | 3947 | CE | LYS | 3177 | 103.939 | 25.463 | 110.586 | 1.00 | 50.46 |
| ATOM | 3948 | NZ | LYS | 3177 | 104.026 | 26.962 | 110.524 | 1.00 | 52.89 |
| ATOM | 3949 | C | LYS | 3177 | 102.695 | 20.536 | 108.293 | 1.00 | 35.62 |
| ATOM | 3950 | O | LYS | 3177 | 103.642 | 20.119 | 108.961 | 1.00 | 35.64 |
| ATOM | 3951 | N | CYS | 3178 | 102.596 | 20.357 | 106.982 | 1.00 | 34.67 |
| ATOM | 3952 | CA | CYS | 3178 | 103.612 | 19.659 | 106.222 | 1.00 | 34.74 |
| ATOM | 3953 | C | CYS | 3178 | 103.955 | 20.424 | 104.958 | 1.00 | 35.58 |
| ATOM | 3954 | O | CYS | 3178 | 103.741 | 19.937 | 103.853 | 1.00 | 35.54 |
| ATOM | 3955 | CB | CYS | 3178 | 103.117 | 18.261 | 105.884 | 1.00 | 33.60 |
| ATOM | 3956 | SG | CYS | 3178 | 103.038 | 17.226 | 107.372 | 1.00 | 35.88 |
| ATOM | 3957 | N | PRO | 3179 | 104.498 | 21.644 | 105.109 | 1.00 | 36.84 |
| ATOM | 3958 | CD | PRO | 3179 | 104.979 | 22.257 | 106.356 | 1.00 | 38.05 |
| ATOM | 3959 | CA | PRO | 3179 | 104.871 | 22.475 | 103.970 | 1.00 | 37.36 |
| ATOM | 3960 | CB | PRO | 3179 | 105.558 | 23.672 | 104.625 | 1.00 | 37.13 |
| ATOM | 3961 | CG | PRO | 3179 | 106.122 | 23.106 | 105.856 | 1.00 | 37.15 |
| ATOM | 3962 | C | PRO | 3179 | 105.779 | 21.711 | 103.033 | 1.00 | 38.78 |
| ATOM | 3963 | O | PRO | 3179 | 106.888 | 21.316 | 103.404 | 1.00 | 39.64 |
| ATOM | 3964 | N | SER | 3180 | 105.283 | 21.504 | 101.818 | 1.00 | 39.40 |
| ATOM | 3965 | CA | SER | 3180 | 106.013 | 20.772 | 100.795 | 1.00 | 40.28 |
| ATOM | 3966 | CB | SER | 3180 | 105.687 | 19.287 | 100.892 | 1.00 | 40.13 |
| ATOM | 3967 | OG | SER | 3180 | 104.294 | 19.079 | 100.743 | 1.00 | 41.29 |
| ATOM | 3968 | C | SER | 3180 | 105.653 | 21.265 | 99.402 | 1.00 | 40.83 |
| ATOM | 3969 | O | SER | 3180 | 104.695 | 22.014 | 99.224 | 1.00 | 41.33 |
| ATOM | 3970 | N | SER | 3181 | 106.432 | 20.838 | 98.415 | 1.00 | 41.29 |
| ATOM | 3971 | CA | SER | 3181 | 106.196 | 21.216 | 97.032 | 1.00 | 41.67 |
| ATOM | 3972 | CB | SER | 3181 | 106.933 | 22.501 | 96.684 | 1.00 | 41.34 |
| ATOM | 3973 | OG | SER | 3181 | 106.679 | 22.841 | 95.336 | 1.00 | 42.45 |
| ATOM | 3974 | C | SER | 3181 | 106.667 | 20.114 | 96.108 | 1.00 | 42.58 |
| ATOM | 3975 | O | SER | 3181 | 107.169 | 19.078 | 96.557 | 1.00 | 42.52 |
| ATOM | 3976 | N | GLY | 3182 | 106.515 | 20.347 | 94.809 | 1.00 | 43.39 |
| ATOM | 3977 | CA | GLY | 3182 | 106.926 | 19.358 | 93.832 | 1.00 | 44.36 |
| ATOM | 3978 | C | GLY | 3182 | 106.023 | 19.414 | 92.624 | 1.00 | 44.64 |
| ATOM | 3979 | O | GLY | 3182 | 104.828 | 19.686 | 92.744 | 1.00 | 45.60 |
| ATOM | 3980 | N | THR | 3183 | 106.584 | 19.145 | 91.455 | 1.00 | 44.26 |
| ATOM | 3981 | CA | THR | 3183 | 105.809 | 19.199 | 90.226 | 1.00 | 43.39 |
| ATOM | 3982 | CB | THR | 3183 | 106.416 | 20.225 | 89.257 | 1.00 | 44.07 |
| ATOM | 3983 | OG1 | THR | 3183 | 107.601 | 19.679 | 88.664 | 1.00 | 43.89 |
| ATOM | 3984 | CG2 | THR | 3183 | 106.784 | 21.510 | 90.009 | 1.00 | 44.02 |
| ATOM | 3985 | C | THR | 3183 | 105.739 | 17.848 | 89.528 | 1.00 | 41.94 |
| ATOM | 3986 | O | THR | 3183 | 106.749 | 17.182 | 89.337 | 1.00 | 41.73 |
| ATOM | 3987 | N | PRO | 3184 | 104.533 | 17.419 | 89.154 | 1.00 | 40.89 |

TABLE 6-continued

FGF2/FGFR1/Heparin Ternary Complex

| ATOM | 3988 | CD | PRO | 3184 | 104.324 | 16.173 | 88.403 | 1.00 | 40.85 |
|---|---|---|---|---|---|---|---|---|---|
| ATOM | 3989 | CA | PRO | 3184 | 103.263 | 18.126 | 89.357 | 1.00 | 41.35 |
| ATOM | 3990 | CB | PRO | 3184 | 102.264 | 17.255 | 88.596 | 1.00 | 41.51 |
| ATOM | 3991 | CG | PRO | 3184 | 102.877 | 15.878 | 88.685 | 1.00 | 41.48 |
| ATOM | 3992 | C | PRO | 3184 | 102.899 | 18.273 | 90.842 | 1.00 | 41.37 |
| ATOM | 3993 | O | PRO | 3184 | 103.304 | 17.443 | 91.662 | 1.00 | 41.55 |
| ATOM | 3994 | N | GLN | 3185 | 102.136 | 19.317 | 91.178 | 1.00 | 40.22 |
| ATOM | 3995 | CA | GLN | 3185 | 101.741 | 19.555 | 92.565 | 1.00 | 38.60 |
| ATOM | 3996 | CB | GLN | 3185 | 100.632 | 20.603 | 92.686 | 1.00 | 38.52 |
| ATOM | 3997 | CG | GLN | 3185 | 101.130 | 22.019 | 92.551 | 1.00 | 38.62 |
| ATOM | 3998 | CD | GLN | 3185 | 102.396 | 22.266 | 93.350 | 1.00 | 39.26 |
| ATOM | 3999 | OE1 | GLN | 3185 | 102.349 | 22.553 | 94.555 | 1.00 | 38.93 |
| ATOM | 4000 | NE2 | GLN | 3185 | 103.544 | 22.143 | 92.682 | 1.00 | 37.47 |
| ATOM | 4001 | C | GLN | 3185 | 101.286 | 18.292 | 93.255 | 1.00 | 38.04 |
| ATOM | 4002 | O | GLN | 3185 | 100.398 | 17.582 | 92.773 | 1.00 | 38.76 |
| ATOM | 4003 | N | PRO | 3186 | 101.891 | 17.996 | 94.411 | 1.00 | 36.43 |
| ATOM | 4004 | CD | PRO | 3186 | 103.019 | 18.718 | 95.029 | 1.00 | 34.31 |
| ATOM | 4005 | CA | PRO | 3186 | 101.549 | 16.803 | 95.180 | 1.00 | 35.01 |
| ATOM | 4006 | CB | PRO | 3186 | 102.727 | 16.680 | 96.129 | 1.00 | 34.21 |
| ATOM | 4007 | CG | PRO | 3186 | 103.077 | 18.112 | 96.384 | 1.00 | 33.80 |
| ATOM | 4008 | C | PRO | 3186 | 100.225 | 16.928 | 95.914 | 1.00 | 34.50 |
| ATOM | 4009 | O | PRO | 3186 | 99.776 | 18.023 | 96.214 | 1.00 | 34.54 |
| ATOM | 4010 | N | THR | 3187 | 99.602 | 15.797 | 96.198 | 1.00 | 34.48 |
| ATOM | 4011 | CA | THR | 3187 | 98.344 | 15.791 | 96.914 | 1.00 | 33.96 |
| ATOM | 4012 | CB | THR | 3187 | 97.476 | 14.650 | 96.460 | 1.00 | 34.40 |
| ATOM | 4013 | OG1 | THR | 3187 | 98.076 | 13.415 | 96.867 | 1.00 | 37.04 |
| ATOM | 4014 | CG2 | THR | 3187 | 97.355 | 14.661 | 94.958 | 1.00 | 32.72 |
| ATOM | 4015 | C | THR | 3187 | 98.669 | 15.609 | 98.386 | 1.00 | 34.06 |
| ATOM | 4016 | O | THR | 3187 | 99.694 | 15.025 | 98.733 | 1.00 | 34.86 |
| ATOM | 4017 | N | LEU | 3188 | 97.784 | 16.094 | 99.247 | 1.00 | 33.45 |
| ATOM | 4018 | CA | LEU | 3188 | 97.989 | 16.025 | 100.689 | 1.00 | 32.42 |
| ATOM | 4019 | CB | LEU | 3188 | 98.058 | 17.459 | 101.222 | 1.00 | 32.45 |
| ATOM | 4020 | CG | LEU | 3188 | 98.424 | 17.833 | 102.657 | 1.00 | 32.62 |
| ATOM | 4021 | CD1 | LEU | 3188 | 97.176 | 17.927 | 103.496 | 1.00 | 33.45 |
| ATOM | 4022 | CD2 | LEU | 3188 | 99.412 | 16.837 | 103.214 | 1.00 | 32.98 |
| ATOM | 4023 | C | LEU | 3188 | 96.888 | 15.241 | 101.394 | 1.00 | 32.45 |
| ATOM | 4024 | O | LEU | 3188 | 95.703 | 15.500 | 101.184 | 1.00 | 33.51 |
| ATOM | 4025 | N | ARG | 3189 | 97.273 | 14.276 | 102.222 | 1.00 | 31.58 |
| ATOM | 4026 | CA | ARG | 3189 | 96.292 | 13.482 | 102.960 | 1.00 | 31.46 |
| ATOM | 4027 | CB | ARG | 3189 | 96.034 | 12.171 | 102.244 | 1.00 | 32.71 |
| ATOM | 4028 | CG | ARG | 3189 | 97.254 | 11.655 | 101.536 | 1.00 | 35.33 |
| ATOM | 4029 | CD | ARG | 3189 | 96.964 | 10.360 | 100.823 | 1.00 | 36.64 |
| ATOM | 4030 | NE | ARG | 3189 | 97.343 | 9.221 | 101.640 | 1.00 | 39.14 |
| ATOM | 4031 | CZ | ARG | 3189 | 97.196 | 7.967 | 101.251 | 1.00 | 40.05 |
| ATOM | 4032 | NH1 | ARG | 3189 | 96.667 | 7.724 | 100.062 | 1.00 | 41.48 |
| ATOM | 4033 | NH2 | ARG | 3189 | 97.598 | 6.968 | 102.029 | 1.00 | 40.09 |
| ATOM | 4034 | C | ARG | 3189 | 96.806 | 13.215 | 104.357 | 1.00 | 30.48 |
| ATOM | 4035 | O | ARG | 3189 | 98.015 | 13.216 | 104.570 | 1.00 | 31.15 |
| ATOM | 4036 | N | TRP | 3190 | 95.900 | 12.993 | 105.309 | 1.00 | 28.92 |
| ATOM | 4037 | CA | TRP | 3190 | 96.312 | 12.744 | 106.689 | 1.00 | 27.43 |
| ATOM | 4038 | CB | TRP | 3190 | 95.807 | 13.861 | 107.601 | 1.00 | 25.06 |
| ATOM | 4039 | CG | TRP | 3190 | 96.413 | 15.186 | 107.297 | 1.00 | 24.52 |
| ATOM | 4040 | CD2 | TRP | 3190 | 97.573 | 15.751 | 107.913 | 1.00 | 23.12 |
| ATOM | 4041 | CE2 | TRP | 3190 | 97.811 | 17.001 | 107.290 | 1.00 | 22.92 |
| ATOM | 4042 | CE3 | TRP | 3190 | 98.439 | 15.323 | 108.926 | 1.00 | 21.94 |
| ATOM | 4043 | CD1 | TRP | 3190 | 96.000 | 16.091 | 106.349 | 1.00 | 25.01 |
| ATOM | 4044 | NE1 | TRP | 3190 | 96.838 | 17.185 | 106.343 | 1.00 | 23.24 |
| ATOM | 4045 | CZ2 | TRP | 3190 | 98.876 | 17.823 | 107.650 | 1.00 | 22.66 |
| ATOM | 4046 | CZ3 | TRP | 3190 | 99.498 | 16.142 | 109.287 | 1.00 | 21.32 |
| ATOM | 4047 | CH2 | TRP | 3190 | 99.708 | 17.379 | 108.650 | 1.00 | 22.50 |
| ATOM | 4048 | C | TRP | 3190 | 95.872 | 11.405 | 107.253 | 1.00 | 27.66 |
| ATOM | 4049 | O | TRP | 3190 | 94.887 | 10.824 | 106.810 | 1.00 | 27.65 |
| ATOM | 4050 | N | LEU | 3191 | 96.610 | 10.926 | 108.249 | 1.00 | 28.41 |
| ATOM | 4051 | CA | LEU | 3191 | 96.307 | 9.650 | 108.888 | 1.00 | 28.83 |
| ATOM | 4052 | CB | LEU | 3191 | 97.260 | 8.566 | 108.390 | 1.00 | 27.63 |
| ATOM | 4053 | CG | LEU | 3191 | 97.094 | 8.114 | 106.946 | 1.00 | 26.93 |
| ATOM | 4054 | CD1 | LEU | 3191 | 98.157 | 7.108 | 106.615 | 1.00 | 24.92 |
| ATOM | 4055 | CD2 | LEU | 3191 | 95.720 | 7.514 | 106.758 | 1.00 | 28.55 |
| ATOM | 4056 | C | LEU | 3191 | 96.399 | 9.696 | 110.400 | 1.00 | 30.38 |
| ATOM | 4057 | O | LEU | 3191 | 97.392 | 10.169 | 110.964 | 1.00 | 31.46 |
| ATOM | 4058 | N | LYS | 3192 | 95.366 | 9.191 | 111.059 | 1.00 | 30.65 |
| ATOM | 4059 | CA | LYS | 3192 | 95.365 | 9.153 | 112.511 | 1.00 | 31.26 |
| ATOM | 4060 | CB | LYS | 3192 | 93.968 | 9.452 | 113.048 | 1.00 | 30.21 |
| ATOM | 4061 | CG | LYS | 3192 | 93.849 | 9.483 | 114.559 | 1.00 | 28.59 |
| ATOM | 4062 | CD | LYS | 3192 | 92.490 | 10.045 | 114.934 | 1.00 | 28.49 |
| ATOM | 4063 | CE | LYS | 3192 | 92.225 | 10.011 | 116.429 | 1.00 | 27.72 |
| ATOM | 4064 | NZ | LYS | 3192 | 91.766 | 8.673 | 116.913 | 1.00 | 27.67 |

TABLE 6-continued

FGF2/FGFR1/Heparin Ternary Complex

| ATOM | 4065 | C | LYS | 3192 | 95.770 | 7.738 | 112.841 | 1.00 | 32.77 |
|---|---|---|---|---|---|---|---|---|---|
| ATOM | 4066 | O | LYS | 3192 | 95.060 | 6.803 | 112.493 | 1.00 | 32.79 |
| ATOM | 4067 | N | ASN | 3193 | 96.922 | 7.586 | 113.489 | 1.00 | 34.65 |
| ATOM | 4068 | CA | ASN | 3193 | 97.442 | 6.271 | 113.865 | 1.00 | 35.77 |
| ATOM | 4069 | CB | ASN | 3193 | 96.586 | 5.615 | 114.951 | 1.00 | 34.84 |
| ATOM | 4070 | CG | ASN | 3193 | 96.362 | 6.510 | 116.142 | 1.00 | 36.02 |
| ATOM | 4071 | OD1 | ASN | 3193 | 97.310 | 7.003 | 116.754 | 1.00 | 37.08 |
| ATOM | 4072 | ND2 | ASN | 3193 | 95.097 | 6.726 | 116.485 | 1.00 | 35.16 |
| ATOM | 4073 | C | ASN | 3193 | 97.470 | 5.338 | 112.672 | 1.00 | 36.81 |
| ATOM | 4074 | O | ASN | 3193 | 97.022 | 4.201 | 112.770 | 1.00 | 37.65 |
| ATOM | 4075 | N | GLY | 3194 | 97.976 | 5.818 | 111.543 | 1.00 | 37.81 |
| ATOM | 4076 | CA | GLY | 3194 | 98.052 | 4.980 | 110.358 | 1.00 | 39.40 |
| ATOM | 4077 | C | GLY | 3194 | 96.770 | 4.835 | 109.562 | 1.00 | 39.98 |
| ATOM | 4078 | O | GLY | 3194 | 96.783 | 4.871 | 108.339 | 1.00 | 39.69 |
| ATOM | 4079 | N | LYS | 3195 | 95.653 | 4.667 | 110.251 | 1.00 | 42.10 |
| ATOM | 4080 | CA | LYS | 3195 | 94.371 | 4.514 | 109.575 | 1.00 | 43.61 |
| ATOM | 4081 | CS | LYS | 3195 | 93.322 | 4.012 | 110.576 | 1.00 | 45.37 |
| ATOM | 4082 | CG | LYS | 3195 | 93.783 | 2.809 | 111.409 | 1.00 | 47.51 |
| ATOM | 4083 | CD | LYS | 3195 | 94.260 | 1.672 | 110.507 | 1.00 | 50.03 |
| ATOM | 4084 | CE | LYS | 3195 | 94.801 | 0.473 | 111.294 | 1.00 | 51.90 |
| ATOM | 4085 | NZ | LYS | 3195 | 93.749 | −0.297 | 112.031 | 1.00 | 52.89 |
| ATOM | 4086 | C | LYS | 3195 | 93.912 | 5.826 | 108.925 | 1.00 | 43.68 |
| ATOM | 4087 | O | LYS | 3195 | 94.371 | 6.912 | 109.291 | 1.00 | 44.03 |
| ATOM | 4088 | N | GLU | 3196 | 93.005 | 5.718 | 107.961 | 1.00 | 43.97 |
| ATOM | 4089 | CA | GLU | 3196 | 92.503 | 6.891 | 107.265 | 1.00 | 45.11 |
| ATOM | 4090 | CB | GLU | 3196 | 91.764 | 6.472 | 106.001 | 1.00 | 47.79 |
| ATOM | 4091 | CG | GLU | 3196 | 92.191 | 7.266 | 104.776 | 1.00 | 51.56 |
| ATOM | 4092 | CD | GLU | 3196 | 91.085 | 7.376 | 103.743 | 1.00 | 54.33 |
| ATOM | 4093 | OE1 | GLU | 3196 | 91.305 | 8.031 | 102.701 | 1.00 | 55.06 |
| ATOM | 4094 | OE2 | GLU | 3196 | 89.993 | 6.811 | 103.984 | 1.00 | 54.21 |
| ATOM | 4095 | C | GLU | 3196 | 91.586 | 7.743 | 108.132 | 1.00 | 44.77 |
| ATOM | 4096 | O | GLU | 3196 | 90.632 | 7.246 | 108.718 | 1.00 | 43.69 |
| ATOM | 4097 | N | PHE | 3197 | 91.883 | 9.036 | 108.207 | 1.00 | 46.09 |
| ATOM | 4098 | CA | PHE | 3197 | 91.087 | 9.969 | 109.007 | 1.00 | 46.85 |
| ATOM | 4099 | CB | PHE | 3197 | 91.911 | 11.198 | 109.409 | 1.00 | 49.07 |
| ATOM | 4100 | CG | PHE | 3197 | 91.574 | 12.424 | 108.602 | 1.00 | 54.99 |
| ATOM | 4101 | CD1 | PHE | 3197 | 90.857 | 13.473 | 109.171 | 1.00 | 57.46 |
| ATOM | 4102 | CD2 | PHE | 3197 | 91.855 | 12.473 | 107.226 | 1.00 | 56.59 |
| ATOM | 4103 | CE1 | PHE | 3197 | 90.414 | 14.557 | 108.386 | 1.00 | 59.23 |
| ATOM | 4104 | CE2 | PHE | 3197 | 91.416 | 13.549 | 106.427 | 1.00 | 57.43 |
| ATOM | 4105 | CZ | PHE | 3197 | 90.692 | 14.590 | 107.009 | 1.00 | 58.59 |
| ATOM | 4106 | C | PHE | 3197 | 89.920 | 10.447 | 108.148 | 1.00 | 46.85 |
| ATOM | 4107 | O | PHE | 3197 | 89.960 | 10.359 | 106.923 | 1.00 | 47.12 |
| ATOM | 4108 | N | LYS | 3198 | 88.889 | 10.973 | 108.793 | 1.00 | 46.00 |
| ATOM | 4109 | CA | LYS | 3198 | 87.732 | 11.508 | 108.080 | 1.00 | 45.84 |
| ATOM | 4110 | CB | LYS | 3198 | 86.786 | 10.374 | 107.661 | 1.00 | 44.01 |
| ATOM | 4111 | C | LYS | 3198 | 87.025 | 12.527 | 108.993 | 1.00 | 45.86 |
| ATOM | 4112 | O | LYS | 3198 | 86.769 | 12.252 | 110.164 | 1.00 | 46.51 |
| ATOM | 4113 | N | PRO | 3199 | 86.697 | 13.716 | 108.461 | 1.00 | 45.11 |
| ATOM | 4114 | CD | PRO | 3199 | 86.516 | 13.932 | 107.014 | 1.00 | 44.01 |
| ATOM | 4115 | CA | PRO | 3199 | 86.026 | 14.783 | 109.214 | 1.00 | 44.59 |
| ATOM | 4116 | CB | PRO | 3199 | 85.430 | 15.657 | 108.110 | 1.00 | 43.96 |
| ATOM | 4117 | CG | PRO | 3199 | 85.235 | 14.702 | 106.979 | 1.00 | 42.96 |
| ATOM | 4118 | C | PRO | 3199 | 84.980 | 14.341 | 110.237 | 1.00 | 44.16 |
| ATOM | 4119 | O | PRO | 3199 | 84.950 | 14.847 | 111.347 | 1.00 | 44.80 |
| ATOM | 4120 | N | ASP | 3200 | 84.116 | 13.404 | 109.870 | 1.00 | 43.90 |
| ATOM | 4121 | CA | ASP | 3200 | 83.100 | 12.933 | 110.805 | 1.00 | 44.02 |
| ATOM | 4122 | CB | ASP | 3200 | 82.073 | 12.043 | 110.097 | 1.00 | 45.82 |
| ATOM | 4123 | CG | ASP | 3200 | 81.157 | 12.813 | 109.189 | 1.00 | 47.10 |
| ATOM | 4124 | OD1 | ASP | 3200 | 81.586 | 13.149 | 108.064 | 1.00 | 48.67 |
| ATOM | 4125 | OD2 | ASP | 3200 | 80.010 | 13.084 | 109.606 | 1.00 | 46.58 |
| ATOM | 4126 | C | ASP | 3200 | 83.685 | 12.109 | 111.950 | 1.00 | 43.57 |
| ATOM | 4127 | O | ASP | 3200 | 82.956 | 11.695 | 112.848 | 1.00 | 43.75 |
| ATOM | 4128 | N | HIS | 3201 | 84.988 | 11.856 | 111.928 | 1.00 | 42.90 |
| ATOM | 4129 | CA | HIS | 3201 | 85.577 | 11.024 | 112.966 | 1.00 | 42.12 |
| ATOM | 4130 | CB | HIS | 3201 | 86.819 | 10.322 | 112.412 | 1.00 | 45.05 |
| ATOM | 4131 | CG | HIS | 3201 | 86.513 | 9.409 | 111.258 | 1.00 | 48.69 |
| ATOM | 4132 | CD2 | HIS | 3201 | 87.276 | 8.503 | 110.601 | 1.00 | 49.14 |
| ATOM | 4133 | ND1 | HIS | 3201 | 85.280 | 9.393 | 110.633 | 1.00 | 49.54 |
| ATOM | 4134 | CE1 | HIS | 3201 | 85.298 | 8.519 | 109.643 | 1.00 | 49.00 |
| ATOM | 4135 | NE2 | HIS | 3201 | 86.497 | 7.966 | 109.600 | 1.00 | 49.34 |
| ATOM | 4136 | C | HIS | 3201 | 85.839 | 11.693 | 114.306 | 1.00 | 40.12 |
| ATOM | 4137 | O | HIS | 3201 | 86.315 | 11.051 | 115.234 | 1.00 | 39.87 |
| ATOM | 4138 | N | ARG | 3202 | 85.511 | 12.975 | 114.419 | 1.00 | 38.19 |
| ATOM | 4139 | CA | ARG | 3202 | 85.666 | 13.680 | 115.690 | 1.00 | 37.19 |
| ATOM | 4140 | CB | ARG | 3202 | 87.094 | 14.212 | 115.858 | 1.00 | 33.66 |
| ATOM | 4141 | CG | ARG | 3202 | 87.423 | 15.447 | 115.033 | 1.00 | 30.85 |

TABLE 6-continued

FGF2/FGFR1/Heparin Ternary Complex

| ATOM | 4142 | CD | ARG | 3202 | 88.874 | 15.897 | 115.215 | 1.00 | 28.38 |
|---|---|---|---|---|---|---|---|---|---|
| ATOM | 4143 | NE | ARG | 3202 | 89.213 | 16.267 | 116.595 | 1.00 | 26.89 |
| ATOM | 4144 | CZ | ARG | 3202 | 89.081 | 17.486 | 117.116 | 1.00 | 24.63 |
| ATOM | 4145 | NH1 | ARG | 3202 | 88.614 | 18.490 | 116.378 | 1.00 | 22.77 |
| ATOM | 4146 | NH2 | ARG | 3202 | 89.426 | 17.701 | 118.379 | 1.00 | 22.19 |
| ATOM | 4147 | C | ARG | 3202 | 84.665 | 14.826 | 115.713 | 1.00 | 38.70 |
| ATOM | 4148 | O | ARG | 3202 | 84.313 | 15.352 | 114.656 | 1.00 | 39.97 |
| ATOM | 4149 | N | ILE | 3203 | 84.187 | 15.197 | 116.899 | 1.00 | 38.96 |
| ATOM | 4150 | CA | ILE | 3203 | 83.228 | 16.302 | 117.020 | 1.00 | 40.54 |
| ATOM | 4151 | CB | ILE | 3203 | 82.888 | 16.619 | 118.497 | 1.00 | 40.79 |
| ATOM | 4152 | CG2 | ILE | 3203 | 81.583 | 15.975 | 118.896 | 1.00 | 41.16 |
| ATOM | 4153 | CG1 | ILE | 3203 | 84.046 | 16.187 | 119.394 | 1.00 | 41.69 |
| ATOM | 4154 | CD1 | ILE | 3203 | 83.854 | 16.577 | 120.829 | 1.00 | 42.35 |
| ATOM | 4155 | C | ILE | 3203 | 83.850 | 17.560 | 116.437 | 1.00 | 41.00 |
| ATOM | 4156 | O | ILE | 3203 | 84.987 | 17.889 | 116.769 | 1.00 | 40.32 |
| ATOM | 4157 | N | GLY | 3204 | 83.106 | 18.265 | 115.588 | 1.00 | 42.04 |
| ATOM | 4158 | CA | GLY | 3204 | 83.633 | 19.475 | 114.983 | 1.00 | 42.18 |
| ATOM | 4159 | C | GLY | 3204 | 84.576 | 19.121 | 113.856 | 1.00 | 42.43 |
| ATOM | 4160 | O | GLY | 3204 | 85.010 | 19.989 | 113.098 | 1.00 | 43.78 |
| ATOM | 4161 | N | GLY | 3205 | 84.899 | 17.837 | 113.759 | 1.00 | 41.56 |
| ATOM | 4162 | CA | GLY | 3205 | 85.784 | 17.365 | 112.714 | 1.00 | 42.05 |
| ATOM | 4163 | C | GLY | 3205 | 87.106 | 18.088 | 112.573 | 1.00 | 41.88 |
| ATOM | 4164 | O | GLY | 3205 | 87.525 | 18.832 | 113.458 | 1.00 | 41.59 |
| ATOM | 4165 | N | TYR | 3206 | 87.752 | 17.852 | 111.436 | 1.00 | 41.98 |
| ATOM | 4166 | CA | TYR | 3206 | 89.041 | 18.435 | 111.113 | 1.00 | 43.16 |
| ATOM | 4167 | CB | TYR | 3206 | 90.030 | 17.357 | 110.639 | 1.00 | 45.88 |
| ATOM | 4168 | CG | TYR | 3206 | 90.059 | 16.016 | 111.348 | 1.00 | 49.67 |
| ATOM | 4169 | CD1 | TYR | 3206 | 88.973 | 15.145 | 111.312 | 1.00 | 50.70 |
| ATOM | 4170 | CE1 | TYR | 3206 | 89.054 | 13.868 | 111.912 | 1.00 | 52.54 |
| ATOM | 4171 | CD2 | TYR | 3206 | 91.222 | 15.586 | 111.998 | 1.00 | 52.55 |
| ATOM | 4172 | CE2 | TYR | 3206 | 91.313 | 14.326 | 112.593 | 1.00 | 52.68 |
| ATOM | 4173 | CZ | TYR | 3206 | 90.233 | 13.473 | 112.549 | 1.00 | 52.36 |
| ATOM | 4174 | OH | TYR | 3206 | 90.349 | 12.237 | 113.142 | 1.00 | 51.75 |
| ATOM | 4175 | C | TYR | 3206 | 88.875 | 19.378 | 109.924 | 1.00 | 43.10 |
| ATOM | 4176 | O | TYR | 3206 | 87.904 | 19.281 | 109.176 | 1.00 | 42.27 |
| ATOM | 4177 | N | LYS | 3207 | 89.863 | 20.247 | 109.726 | 1.00 | 42.87 |
| ATOM | 4178 | CA | LYS | 3207 | 89.871 | 21.175 | 108.608 | 1.00 | 43.44 |
| ATOM | 4179 | CB | LYS | 3207 | 89.669 | 22.612 | 109.091 | 1.00 | 44.45 |
| ATOM | 4180 | CG | LYS | 3207 | 88.451 | 22.815 | 109.968 | 1.00 | 46.86 |
| ATOM | 4181 | CD | LYS | 3207 | 87.585 | 23.959 | 109.464 | 1.00 | 48.99 |
| ATOM | 4182 | CE | LYS | 3207 | 88.323 | 25.281 | 109.476 | 1.00 | 50.26 |
| ATOM | 4183 | NZ | LYS | 3207 | 87.603 | 26.258 | 108.623 | 1.00 | 53.62 |
| ATOM | 4184 | C | LYS | 3207 | 91.241 | 21.062 | 107.956 | 1.00 | 43.63 |
| ATOM | 4185 | O | LYS | 3207 | 92.262 | 21.210 | 108.637 | 1.00 | 43.12 |
| ATOM | 4186 | N | VAL | 3208 | 91.274 | 20.800 | 106.651 | 1.00 | 43.43 |
| ATOM | 4187 | CA | VAL | 3208 | 92.550 | 20.696 | 105.959 | 1.00 | 43.96 |
| ATOM | 4188 | CB | VAL | 3208 | 92.649 | 19.384 | 105.160 | 1.00 | 44.46 |
| ATOM | 4189 | CG1 | VAL | 3208 | 94.059 | 19.208 | 104.641 | 1.00 | 44.59 |
| ATOM | 4190 | CG2 | VAL | 3208 | 92.273 | 18.204 | 106.038 | 1.00 | 44.71 |
| ATOM | 4191 | C | VAL | 3208 | 92.764 | 21.880 | 105.021 | 1.00 | 43.87 |
| ATOM | 4192 | O | VAL | 3208 | 91.978 | 22.107 | 104.108 | 1.00 | 43.48 |
| ATOM | 4193 | N | ARG | 3209 | 93.832 | 22.632 | 105.269 | 1.00 | 43.97 |
| ATOM | 4194 | CA | ARG | 3209 | 94.175 | 23.800 | 104.471 | 1.00 | 44.14 |
| ATOM | 4195 | CB | ARG | 3209 | 94.563 | 24.969 | 105.385 | 1.00 | 43.74 |
| ATOM | 4196 | C | ARG | 3209 | 95.335 | 23.471 | 103.542 | 1.00 | 44.62 |
| ATOM | 4197 | O | ARG | 3209 | 96.492 | 23.792 | 103.841 | 1.00 | 45.16 |
| ATOM | 4198 | N | TYR | 3210 | 95.018 | 22.823 | 102.422 | 1.00 | 42.65 |
| ATOM | 4199 | CA | TYR | 3210 | 96.024 | 22.457 | 101.445 | 1.00 | 40.69 |
| ATOM | 4200 | CB | TYR | 3210 | 95.337 | 21.964 | 100.180 | 1.00 | 39.58 |
| ATOM | 4201 | CG | TYR | 3210 | 94.363 | 20.838 | 100.449 | 1.00 | 39.88 |
| ATOM | 4202 | CD1 | TYR | 3210 | 93.015 | 21.095 | 100.655 | 1.00 | 39.52 |
| ATOM | 4203 | CE1 | TYR | 3210 | 92.121 | 20.067 | 100.947 | 1.00 | 39.34 |
| ATOM | 4204 | CD2 | TYR | 3210 | 94.801 | 19.511 | 100.541 | 1.00 | 39.83 |
| ATOM | 4205 | CE2 | TYR | 3210 | 93.914 | 18.475 | 100.837 | 1.00 | 40.07 |
| ATOM | 4206 | CZ | TYR | 3210 | 92.571 | 18.761 | 101.041 | 1.00 | 39.67 |
| ATOM | 4207 | OH | TYR | 3210 | 91.681 | 17.750 | 101.361 | 1.00 | 38.31 |
| ATOM | 4208 | C | TYR | 3210 | 96.868 | 23.679 | 101.154 | 1.00 | 39.91 |
| ATOM | 4209 | O | TYR | 3210 | 98.069 | 23.585 | 100.928 | 1.00 | 40.83 |
| ATOM | 4210 | N | ALA | 3211 | 96.225 | 24.835 | 101.184 | 1.00 | 38.73 |
| ATOM | 4211 | CA | ALA | 3211 | 96.901 | 26.092 | 100.926 | 1.00 | 38.16 |
| ATOM | 4212 | CB | ALA | 3211 | 95.958 | 27.240 | 101.235 | 1.00 | 38.71 |
| ATOM | 4213 | C | ALA | 3211 | 98.174 | 26.220 | 101.762 | 1.00 | 37.62 |
| ATOM | 4214 | O | ALA | 3211 | 99.137 | 26.870 | 101.363 | 1.00 | 37.03 |
| ATOM | 4215 | N | THR | 3212 | 98.172 | 25.580 | 102.921 | 1.00 | 36.93 |
| ATOM | 4216 | CA | THR | 3212 | 99.300 | 25.634 | 103.836 | 1.00 | 36.17 |
| ATOM | 4217 | CB | THR | 3212 | 98.900 | 26.426 | 105.078 | 1.00 | 35.91 |
| ATOM | 4218 | OG1 | THR | 3212 | 97.654 | 25.919 | 105.570 | 1.00 | 36.61 |

TABLE 6-continued

FGF2/FGFR1/Heparin Ternary Complex

| ATOM | 4219 | CG2 | THR | 3212 | 98.711 | 27.889 | 104.734 | 1.00 | 35.63 |
|---|---|---|---|---|---|---|---|---|---|
| ATOM | 4220 | C | THR | 3212 | 99.749 | 24.238 | 104.260 | 1.00 | 35.52 |
| ATOM | 4221 | O | THR | 3212 | 100.523 | 24.085 | 105.211 | 1.00 | 33.54 |
| ATOM | 4222 | N | TRP | 3213 | 99.242 | 23.231 | 103.549 | 1.00 | 34.65 |
| ATOM | 4223 | CA | TRP | 3213 | 99.565 | 21.837 | 103.819 | 1.00 | 34.22 |
| ATOM | 4224 | CB | TRP | 3213 | 101.012 | 21.547 | 103.413 | 1.00 | 34.03 |
| ATOM | 4225 | CG | TRP | 3213 | 101.313 | 21.954 | 101.999 | 1.00 | 33.35 |
| ATOM | 4226 | CD2 | TRP | 3213 | 101.134 | 21.155 | 100.824 | 1.00 | 33.01 |
| ATOM | 4227 | CE2 | TRP | 3213 | 101.442 | 21.969 | 99.716 | 1.00 | 32.31 |
| ATOM | 4228 | CE3 | TRP | 3213 | 100.740 | 19.830 | 100.601 | 1.00 | 33.41 |
| ATOM | 4229 | CD1 | TRP | 3213 | 101.719 | 23.185 | 101.564 | 1.00 | 31.79 |
| ATOM | 4230 | NE1 | TRP | 3213 | 101.795 | 23.203 | 100.196 | 1.00 | 31.39 |
| ATOM | 4231 | CZ2 | TRP | 3213 | 101.365 | 21.500 | 98.401 | 1.00 | 32.41 |
| ATOM | 4232 | CZ3 | TRP | 3213 | 100.664 | 19.366 | 99.298 | 1.00 | 32.89 |
| ATOM | 4233 | CH2 | TRP | 3213 | 100.976 | 20.199 | 98.214 | 1.00 | 32.99 |
| ATOM | 4234 | C | TRP | 3213 | 99.371 | 21.523 | 105.287 | 1.00 | 33.48 |
| ATOM | 4235 | O | TRP | 3213 | 100.189 | 20.846 | 105.896 | 1.00 | 33.88 |
| ATOM | 4236 | N | SER | 3214 | 98.284 | 22.016 | 105.860 | 1.00 | 32.56 |
| ATOM | 4237 | CA | SER | 3214 | 98.038 | 21.768 | 107.265 | 1.00 | 30.87 |
| ATOM | 4238 | CB | SER | 3214 | 98.190 | 23.064 | 108.065 | 1.00 | 30.97 |
| ATOM | 4239 | OG | SER | 3214 | 97.317 | 24.070 | 107.580 | 1.00 | 32.89 |
| ATOM | 4240 | C | SER | 3214 | 96.687 | 21.137 | 107.550 | 1.00 | 29.28 |
| ATOM | 4241 | O | SER | 3214 | 95.795 | 21.093 | 106.694 | 1.00 | 28.57 |
| ATOM | 4242 | N | ILE | 3215 | 96.569 | 20.616 | 108.763 | 1.00 | 26.55 |
| ATOM | 4243 | CA | ILE | 3215 | 95.341 | 20.007 | 109.216 | 1.00 | 24.71 |
| ATOM | 4244 | CB | ILE | 3215 | 95.506 | 18.501 | 109.433 | 1.00 | 22.40 |
| ATOM | 4245 | CG2 | ILE | 3215 | 96.431 | 18.229 | 110.581 | 1.00 | 22.23 |
| ATOM | 4246 | CG1 | ILE | 3215 | 94.152 | 17.890 | 109.736 | 1.00 | 22.18 |
| ATOM | 4247 | CD1 | ILE | 3215 | 94.208 | 16.425 | 109.972 | 1.00 | 23.12 |
| ATOM | 4248 | C | ILE | 3215 | 95.044 | 20.712 | 110.532 | 1.00 | 24.92 |
| ATOM | 4249 | O | ILE | 3215 | 95.966 | 21.045 | 111.288 | 1.00 | 25.19 |
| ATOM | 4250 | N | ILE | 3216 | 93.773 | 20.974 | 110.810 | 1.00 | 24.01 |
| ATOM | 4251 | CA | ILE | 3216 | 93.463 | 21.666 | 112.048 | 1.00 | 22.52 |
| ATOM | 4252 | CB | ILE | 3216 | 93.060 | 23.111 | 111.775 | 1.00 | 20.84 |
| ATOM | 4253 | CG2 | ILE | 3216 | 92.815 | 23.824 | 113.079 | 1.00 | 19.15 |
| ATOM | 4254 | CG1 | ILE | 3216 | 94.178 | 23.797 | 110.988 | 1.00 | 19.92 |
| ATOM | 4255 | CD1 | ILE | 3216 | 93.906 | 25.215 | 110.623 | 1.00 | 19.51 |
| ATOM | 4256 | C | ILE | 3216 | 92.399 | 20.999 | 112.897 | 1.00 | 22.87 |
| ATOM | 4257 | O | ILE | 3216 | 91.357 | 20.555 | 112.401 | 1.00 | 22.78 |
| ATOM | 4258 | N | MET | 3217 | 92.690 | 20.914 | 114.189 | 1.00 | 22.18 |
| ATOM | 4259 | CA | MET | 3217 | 91.779 | 20.321 | 115.139 | 1.00 | 21.68 |
| ATOM | 4260 | CB | MET | 3217 | 92.347 | 19.053 | 115.763 | 1.00 | 19.39 |
| ATOM | 4261 | CG | MET | 3217 | 92.456 | 17.917 | 114.775 | 1.00 | 18.56 |
| ATOM | 4262 | SD | MET | 3217 | 92.952 | 16.333 | 115.467 | 1.00 | 17.16 |
| ATOM | 4263 | CE | MET | 3217 | 94.691 | 16.580 | 115.746 | 1.00 | 16.06 |
| ATOM | 4264 | C | MET | 3217 | 91.493 | 21.327 | 116.216 | 1.00 | 23.31 |
| ATOM | 4265 | O | MET | 3217 | 92.362 | 21.729 | 116.995 | 1.00 | 22.47 |
| ATOM | 4266 | N | ASP | 3218 | 90.230 | 21.714 | 116.217 | 1.00 | 24.72 |
| ATOM | 4267 | CA | ASP | 3218 | 89.633 | 22.670 | 117.114 | 1.00 | 25.55 |
| ATOM | 4268 | CB | ASP | 3218 | 88.403 | 23.180 | 116.368 | 1.00 | 26.32 |
| ATOM | 4269 | CG | ASP | 3218 | 87.752 | 24.337 | 117.024 | 1.00 | 27.13 |
| ATOM | 4270 | OD1 | ASP | 3218 | 86.517 | 24.401 | 116.912 | 1.00 | 28.80 |
| ATOM | 4271 | OD2 | ASP | 3218 | 88.452 | 25.179 | 117.622 | 1.00 | 28.71 |
| ATOM | 4272 | C | ASP | 3218 | 89.251 | 21.923 | 118.407 | 1.00 | 25.13 |
| ATOM | 4273 | O | ASP | 3218 | 88.839 | 20.764 | 118.349 | 1.00 | 24.83 |
| ATOM | 4274 | N | SER | 3219 | 89.384 | 22.591 | 119.553 | 1.00 | 24.85 |
| ATOM | 4275 | CA | SER | 3219 | 89.059 | 22.012 | 120.858 | 1.00 | 25.80 |
| ATOM | 4276 | CB | SER | 3219 | 87.601 | 22.321 | 121.227 | 1.00 | 26.52 |
| ATOM | 4277 | OG | SER | 3219 | 87.342 | 22.022 | 122.598 | 1.00 | 27.15 |
| ATOM | 4278 | C | SER | 3219 | 89.340 | 20.498 | 120.943 | 1.00 | 25.85 |
| ATOM | 4279 | O | SER | 3219 | 88.430 | 19.659 | 120.911 | 1.00 | 25.51 |
| ATOM | 4280 | N | VAL | 3220 | 90.623 | 20.169 | 121.062 | 1.00 | 24.81 |
| ATOM | 4281 | CA | VAL | 3220 | 91.075 | 18.787 | 121.136 | 1.00 | 23.17 |
| ATOM | 4282 | CB | VAL | 3220 | 92.610 | 18.705 | 120.943 | 1.00 | 21.31 |
| ATOM | 4283 | CG1 | VAL | 3220 | 93.004 | 19.434 | 119.676 | 1.00 | 18.39 |
| ATOM | 4284 | CG2 | VAL | 3220 | 93.330 | 19.297 | 122.137 | 1.00 | 21.38 |
| ATOM | 4285 | C | VAL | 3220 | 90.696 | 18.149 | 122.457 | 1.00 | 23.53 |
| ATOM | 4286 | O | VAL | 3220 | 90.519 | 18.835 | 123.452 | 1.00 | 23.23 |
| ATOM | 4287 | N | VAL | 3221 | 90.597 | 16.827 | 122.458 | 1.00 | 24.67 |
| ATOM | 4288 | CA | VAL | 3221 | 90.203 | 16.079 | 123.644 | 1.00 | 25.29 |
| ATOM | 4289 | CB | VAL | 3221 | 88.685 | 15.861 | 123.588 | 1.00 | 25.96 |
| ATOM | 4290 | CG1 | VAL | 3221 | 87.963 | 17.203 | 123.771 | 1.00 | 24.07 |
| ATOM | 4291 | CG2 | VAL | 3221 | 88.304 | 15.265 | 122.217 | 1.00 | 22.59 |
| ATOM | 4292 | C | VAL | 3221 | 90.939 | 14.737 | 123.694 | 1.00 | 26.24 |
| ATOM | 4293 | O | VAL | 3221 | 91.462 | 14.268 | 122.687 | 1.00 | 27.55 |
| ATOM | 4294 | N | PRO | 3222 | 90.977 | 14.092 | 124.861 | 1.00 | 25.89 |
| ATOM | 4295 | CD | PRO | 3222 | 90.340 | 14.464 | 126.133 | 1.00 | 25.13 |

TABLE 6-continued

FGF2/FGFR1/Heparin Ternary Complex

| ATOM | 4296 | CA | PRO | 3222 | 91.676 | 12.805 | 124.972 | 1.00 | 25.81 |
|---|---|---|---|---|---|---|---|---|---|
| ATOM | 4297 | CB | PRO | 3222 | 91.119 | 12.239 | 126.270 | 1.00 | 25.90 |
| ATOM | 4298 | CG | PRO | 3222 | 91.008 | 13.496 | 127.112 | 1.00 | 26.13 |
| ATOM | 4299 | C | PRO | 3222 | 91.513 | 11.872 | 123.774 | 1.00 | 25.76 |
| ATOM | 4300 | O | PRO | 3222 | 92.471 | 11.243 | 123.343 | 1.00 | 25.53 |
| ATOM | 4301 | N | SER | 3223 | 90.305 | 11.806 | 123.230 | 1.00 | 26.32 |
| ATOM | 4302 | CA | SER | 3223 | 90.028 | 10.950 | 122.085 | 1.00 | 27.65 |
| ATOM | 4303 | CB | SER | 3223 | 88.599 | 11.185 | 121.592 | 1.00 | 29.55 |
| ATOM | 4304 | OG | SER | 3223 | 88.603 | 11.913 | 120.360 | 1.00 | 34.94 |
| ATOM | 4305 | C | SER | 3223 | 90.983 | 11.226 | 120.923 | 1.00 | 27.77 |
| ATOM | 4306 | O | SER | 3223 | 91.247 | 10.348 | 120.099 | 1.00 | 28.27 |
| ATOM | 4307 | N | ASP | 3224 | 91.484 | 12.454 | 120.849 | 1.00 | 27.50 |
| ATOM | 4308 | CA | ASP | 3224 | 92.381 | 12.851 | 119.769 | 1.00 | 26.47 |
| ATOM | 4309 | CB | ASP | 3224 | 92.377 | 14.368 | 119.588 | 1.00 | 26.22 |
| ATOM | 4310 | CG | ASP | 3224 | 91.016 | 14.911 | 119.194 | 1.00 | 26.25 |
| ATOM | 4311 | OD1 | ASP | 3224 | 90.558 | 14.634 | 118.071 | 1.00 | 26.37 |
| ATOM | 4312 | OD2 | ASP | 3224 | 90.407 | 15.620 | 120.018 | 1.00 | 26.47 |
| ATOM | 4313 | C | ASP | 3224 | 93.813 | 12.401 | 119.964 | 1.00 | 26.68 |
| ATOM | 4314 | O | ASP | 3224 | 94.589 | 12.406 | 119.016 | 1.00 | 27.42 |
| ATOM | 4315 | N | LYS | 3225 | 94.182 | 12.033 | 121.186 | 1.00 | 27.01 |
| ATOM | 4316 | CA | LYS | 3225 | 95.539 | 11.566 | 121.436 | 1.00 | 26.78 |
| ATOM | 4317 | CB | LYS | 3225 | 95.645 | 10.893 | 122.798 | 1.00 | 27.79 |
| ATOM | 4318 | CG | LYS | 3225 | 95.778 | 11.806 | 123.993 | 1.00 | 28.57 |
| ATOM | 4319 | CD | LYS | 3225 | 96.060 | 10.984 | 125.240 | 1.00 | 28.90 |
| ATOM | 4320 | CE | LYS | 3225 | 96.143 | 11.863 | 126.464 | 1.00 | 31.24 |
| ATOM | 4321 | NZ | LYS | 3225 | 96.642 | 11.133 | 127.674 | 1.00 | 32.68 |
| ATOM | 4322 | C | LYS | 3225 | 95.892 | 10.536 | 120.378 | 1.00 | 27.67 |
| ATOM | 4323 | O | LYS | 3225 | 95.082 | 9.663 | 120.063 | 1.00 | 28.05 |
| ATOM | 4324 | N | GLY | 3226 | 97.093 | 10.632 | 119.828 | 1.00 | 28.00 |
| ATOM | 4325 | CA | GLY | 3226 | 97.505 | 9.671 | 118.821 | 1.00 | 29.59 |
| ATOM | 4326 | C | GLY | 3226 | 98.593 | 10.173 | 117.889 | 1.00 | 30.53 |
| ATOM | 4327 | O | GLY | 3226 | 99.216 | 11.211 | 118.132 | 1.00 | 32.30 |
| ATOM | 4328 | N | ASN | 3227 | 98.845 | 9.423 | 116.824 | 1.00 | 29.28 |
| ATOM | 4329 | CA | ASN | 3227 | 99.840 | 9.827 | 115.853 | 1.00 | 28.54 |
| ATOM | 4330 | CB | ASN | 3227 | 100.713 | 8.647 | 115.436 | 1.00 | 29.62 |
| ATOM | 4331 | CG | ASN | 3227 | 101.767 | 8.299 | 116.459 | 1.00 | 30.02 |
| ATOM | 4332 | OD1 | ASN | 3227 | 102.592 | 9.133 | 116.832 | 1.00 | 30.16 |
| ATOM | 4333 | ND2 | ASN | 3227 | 101.757 | 7.050 | 116.906 | 1.00 | 28.97 |
| ATOM | 4334 | C | ASN | 3227 | 99.088 | 10.336 | 114.641 | 1.00 | 28.93 |
| ATOM | 4335 | O | ASN | 3227 | 98.057 | 9.779 | 114.251 | 1.00 | 29.62 |
| ATOM | 4336 | N | TYR | 3228 | 99.597 | 11.403 | 114.048 | 1.00 | 28.13 |
| ATOM | 4337 | CA | TYR | 3228 | 98.977 | 11.958 | 112.858 | 1.00 | 27.28 |
| ATOM | 4338 | CB | TYR | 3228 | 98.413 | 13.353 | 113.136 | 1.00 | 24.03 |
| ATOM | 4339 | CG | TYR | 3228 | 97.233 | 13.292 | 114.060 | 1.00 | 21.44 |
| ATOM | 4340 | CD1 | TYR | 3228 | 97.404 | 13.225 | 115.437 | 1.00 | 20.30 |
| ATOM | 4341 | CE1 | TYR | 3228 | 96.325 | 13.042 | 116.284 | 1.00 | 19.53 |
| ATOM | 4342 | CD2 | TYR | 3228 | 95.947 | 13.184 | 113.556 | 1.00 | 19.11 |
| ATOM | 4343 | CE2 | TYR | 3228 | 94.867 | 12.999 | 114.389 | 1.00 | 18.07 |
| ATOM | 4344 | CZ | TYR | 3228 | 95.057 | 12.927 | 115.750 | 1.00 | 18.86 |
| ATOM | 4345 | OH | TYR | 3228 | 93.972 | 12.708 | 116.575 | 1.00 | 20.59 |
| ATOM | 4346 | C | TYR | 3228 | 100.026 | 12.007 | 111.775 | 1.00 | 28.52 |
| ATOM | 4347 | O | TYR | 3228 | 101.091 | 12.584 | 111.964 | 1.00 | 29.79 |
| ATOM | 4348 | N | THR | 3229 | 99.734 | 11.382 | 110.642 | 1.00 | 29.19 |
| ATOM | 4349 | CA | THR | 3229 | 100.679 | 11.366 | 109.540 | 1.00 | 29.34 |
| ATOM | 4350 | CB | THR | 3229 | 101.048 | 9.949 | 109.133 | 1.00 | 28.43 |
| ATOM | 4351 | OG1 | THR | 3229 | 101.531 | 9.232 | 110.270 | 1.00 | 28.14 |
| ATOM | 4352 | CG2 | THR | 3229 | 102.119 | 9.988 | 108.069 | 1.00 | 27.79 |
| ATOM | 4353 | C | THR | 3229 | 100.174 | 12.056 | 108.288 | 1.00 | 31.13 |
| ATOM | 4354 | O | THR | 3229 | 99.069 | 11.778 | 107.808 | 1.00 | 30.37 |
| ATOM | 4355 | N | CYS | 3230 | 100.993 | 12.956 | 107.755 | 1.00 | 32.69 |
| ATOM | 4356 | CA | CYS | 3230 | 100.633 | 13.645 | 106.531 | 1.00 | 33.78 |
| ATOM | 4357 | C | CYS | 3230 | 101.391 | 12.932 | 105.433 | 1.00 | 34.55 |
| ATOM | 4358 | O | CYS | 3230 | 102.527 | 12.503 | 105.629 | 1.00 | 34.62 |
| ATOM | 4359 | CB | CYS | 3230 | 101.049 | 15.105 | 106.567 | 1.00 | 34.39 |
| ATOM | 4360 | SG | CYS | 3230 | 102.843 | 15.340 | 106.660 | 1.00 | 36.87 |
| ATOM | 4361 | N | ILE | 3231 | 100.751 | 12.806 | 104.282 | 1.00 | 35.44 |
| ATOM | 4362 | CA | ILE | 3231 | 101.336 | 12.126 | 103.144 | 1.00 | 36.41 |
| ATOM | 4363 | CB | ILE | 3231 | 100.585 | 10.814 | 102.870 | 1.00 | 35.62 |
| ATOM | 4364 | CG2 | ILE | 3231 | 101.145 | 10.131 | 101.638 | 1.00 | 35.26 |
| ATOM | 4365 | CG1 | ILE | 3231 | 100.687 | 9.904 | 104.086 | 1.00 | 34.89 |
| ATOM | 4366 | CD1 | ILE | 3231 | 99.936 | 8.621 | 103.927 | 1.00 | 35.47 |
| ATOM | 4367 | C | ILE | 3231 | 101.246 | 12.997 | 101.906 | 1.00 | 38.07 |
| ATOM | 4368 | O | ILE | 3231 | 100.176 | 13.125 | 101.303 | 1.00 | 39.42 |
| ATOM | 4369 | N | VAL | 3232 | 102.364 | 13.600 | 101.526 | 1.00 | 38.92 |
| ATOM | 4370 | CA | VAL | 3232 | 102.391 | 14.441 | 100.342 | 1.00 | 40.39 |
| ATOM | 4371 | CB | VAL | 3232 | 103.264 | 15.669 | 100.578 | 1.00 | 39.85 |
| ATOM | 4372 | CG1 | VAL | 3232 | 103.271 | 16.546 | 99.351 | 1.00 | 39.62 |

TABLE 6-continued

FGF2/FGFR1/Heparin Ternary Complex

| ATOM | 4373 | CG2 | VAL | 3232 | 102.736 | 16.437 | 101.775 | 1.00 | 39.18 |
|---|---|---|---|---|---|---|---|---|---|
| ATOM | 4374 | C | VAL | 3232 | 102.957 | 13.582 | 99.221 | 1.00 | 42.03 |
| ATOM | 4375 | O | VAL | 3232 | 104.005 | 12.959 | 99.384 | 1.00 | 42.84 |
| ATOM | 4376 | N | GLU | 3233 | 102.267 | 13.548 | 98.084 | 1.00 | 43.41 |
| ATOM | 4377 | CA | GLU | 3233 | 102.698 | 12.700 | 96.977 | 1.00 | 44.19 |
| ATOM | 4378 | CB | GLU | 3233 | 102.249 | 11.268 | 97.253 | 1.00 | 44.16 |
| ATOM | 4379 | CG | GLU | 3233 | 100.801 | 11.210 | 97.745 | 1.00 | 46.42 |
| ATOM | 4380 | CD | GLU | 3233 | 100.302 | 9.798 | 98.011 | 1.00 | 47.74 |
| ATOM | 4381 | OE1 | GLU | 3233 | 99.245 | 9.660 | 98.677 | 1.00 | 46.48 |
| ATOM | 4382 | OE2 | GLU | 3233 | 100.960 | 8.833 | 97.551 | 1.00 | 48.12 |
| ATOM | 4383 | C | GLU | 3233 | 102.201 | 13.080 | 95.589 | 1.00 | 44.58 |
| ATOM | 4384 | O | GLU | 3233 | 101.077 | 13.537 | 95.418 | 1.00 | 43.85 |
| ATOM | 4385 | N | ASN | 3234 | 103.066 | 12.876 | 94.602 | 1.00 | 45.20 |
| ATOM | 4386 | CA | ASN | 3234 | 102.734 | 13.111 | 93.210 | 1.00 | 45.75 |
| ATOM | 4387 | CB | ASN | 3234 | 103.476 | 14.334 | 92.615 | 1.00 | 45.13 |
| ATOM | 4388 | CG | ASN | 3234 | 104.982 | 14.134 | 92.491 | 1.00 | 44.18 |
| ATOM | 4389 | OD1 | ASN | 3234 | 105.467 | 13.020 | 92.346 | 1.00 | 43.62 |
| ATOM | 4390 | ND2 | ASN | 3234 | 105.723 | 15.233 | 92.520 | 1.00 | 43.12 |
| ATOM | 4391 | C | ASN | 3234 | 103.152 | 11.825 | 92.514 | 1.00 | 46.39 |
| ATOM | 4392 | O | ASN | 3234 | 103.416 | 10.828 | 93.173 | 1.00 | 46.09 |
| ATOM | 4393 | N | GLU | 3235 | 103.235 | 11.852 | 91.194 | 1.00 | 47.69 |
| ATOM | 4394 | CA | GLU | 3235 | 103.592 | 10.669 | 90.425 | 1.00 | 48.68 |
| ATOM | 4395 | CB | GLU | 3235 | 103.195 | 10.907 | 88.975 | 1.00 | 50.55 |
| ATOM | 4396 | CG | GLU | 3235 | 103.360 | 9.735 | 88.053 | 1.00 | 53.73 |
| ATOM | 4397 | CD | GLU | 3235 | 102.929 | 10.088 | 86.647 | 1.00 | 56.51 |
| ATOM | 4398 | OE1 | GLU | 3235 | 103.437 | 11.103 | 86.115 | 1.00 | 56.67 |
| ATOM | 4399 | OE2 | GLU | 3235 | 102.083 | 9.360 | 86.078 | 1.00 | 59.10 |
| ATOM | 4400 | C | GLU | 3235 | 105.059 | 10.242 | 90.499 | 1.00 | 48.11 |
| ATOM | 4401 | O | GLU | 3235 | 105.398 | 9.114 | 90.157 | 1.00 | 48.22 |
| ATOM | 4402 | N | TYR | 3236 | 105.925 | 11.127 | 90.972 | 1.00 | 47.64 |
| ATOM | 4403 | CA | TYR | 3236 | 107.352 | 10.835 | 91.034 | 1.00 | 46.82 |
| ATOM | 4404 | CB | TYR | 3236 | 108.112 | 11.980 | 90.359 | 1.00 | 47.99 |
| ATOM | 4405 | CG | TYR | 3236 | 107.695 | 12.162 | 88.924 | 1.00 | 49.09 |
| ATOM | 4406 | CD1 | TYR | 3236 | 106.387 | 12.517 | 88.596 | 1.00 | 50.10 |
| ATOM | 4407 | CE1 | TYR | 3236 | 105.964 | 12.578 | 87.272 | 1.00 | 50.72 |
| ATOM | 4408 | CD2 | TYR | 3236 | 108.575 | 11.886 | 87.889 | 1.00 | 49.80 |
| ATOM | 4409 | CE2 | TYR | 3236 | 108.163 | 11.946 | 86.563 | 1.00 | 50.77 |
| ATOM | 4410 | CZ | TYR | 3236 | 106.859 | 12.289 | 86.264 | 1.00 | 50.58 |
| ATOM | 4411 | OH | TYR | 3236 | 106.454 | 12.313 | 84.957 | 1.00 | 50.48 |
| ATOM | 4412 | C | TYR | 3236 | 107.898 | 10.610 | 92.429 | 1.00 | 45.57 |
| ATOM | 4413 | O | TYR | 3236 | 109.104 | 10.652 | 92.645 | 1.00 | 45.09 |
| ATOM | 4414 | N | GLY | 3237 | 107.011 | 10.372 | 93.381 | 1.00 | 44.21 |
| ATOM | 4415 | CA | GLY | 3237 | 107.468 | 10.159 | 94.736 | 1.00 | 41.97 |
| ATOM | 4416 | C | GLY | 3237 | 106.448 | 10.529 | 95.786 | 1.00 | 39.88 |
| ATOM | 4417 | O | GLY | 3237 | 105.378 | 11.048 | 95.482 | 1.00 | 40.72 |
| ATOM | 4418 | N | SER | 3238 | 106.795 | 10.249 | 97.033 | 1.00 | 37.18 |
| ATOM | 4419 | CA | SER | 3238 | 105.938 | 10.530 | 98.161 | 1.00 | 34.84 |
| ATOM | 4420 | CB | SER | 3238 | 105.051 | 9.329 | 98.446 | 1.00 | 33.70 |
| ATOM | 4421 | OG | SER | 3238 | 105.132 | 8.981 | 99.816 | 1.00 | 33.08 |
| ATOM | 4422 | C | SER | 3238 | 106.806 | 10.788 | 99.374 | 1.00 | 34.34 |
| ATOM | 4423 | O | SER | 3238 | 107.893 | 10.241 | 99.484 | 1.00 | 35.66 |
| ATOM | 4424 | N | ILE | 3239 | 106.347 | 11.653 | 100.266 | 1.00 | 33.12 |
| ATOM | 4425 | CA | ILE | 3239 | 107.062 | 11.907 | 101.511 | 1.00 | 31.89 |
| ATOM | 4426 | CB | ILE | 3239 | 107.867 | 13.215 | 101.533 | 1.00 | 32.23 |
| ATOM | 4427 | CG2 | ILE | 3239 | 109.033 | 13.115 | 100.564 | 1.00 | 33.32 |
| ATOM | 4428 | CG1 | ILE | 3239 | 106.967 | 14.400 | 101.227 | 1.00 | 32.64 |
| ATOM | 4429 | CD1 | ILE | 3239 | 107.746 | 15.668 | 100.981 | 1.00 | 33.49 |
| ATOM | 4430 | C | ILE | 3239 | 106.011 | 11.957 | 102.592 | 1.00 | 31.51 |
| ATOM | 4431 | O | ILE | 3239 | 104.804 | 12.047 | 102.308 | 1.00 | 32.20 |
| ATOM | 4432 | N | ASN | 3240 | 106.458 | 11.877 | 103.835 | 1.00 | 29.70 |
| ATOM | 4433 | CA | ASN | 3240 | 105.513 | 11.876 | 104.938 | 1.00 | 28.30 |
| ATOM | 4434 | CB | ASN | 3240 | 104.794 | 10.520 | 105.012 | 1.00 | 26.31 |
| ATOM | 4435 | CG | ASN | 3240 | 105.655 | 9.440 | 105.630 | 1.00 | 25.18 |
| ATOM | 4436 | OD1 | ASN | 3240 | 105.819 | 9.384 | 106.844 | 1.00 | 25.49 |
| ATOM | 4437 | ND2 | ASN | 3240 | 106.221 | 8.584 | 104.794 | 1.00 | 24.73 |
| ATOM | 4438 | C | ASN | 3240 | 106.195 | 12.164 | 106.258 | 1.00 | 27.90 |
| ATOM | 4439 | O | ASN | 3240 | 107.323 | 11.739 | 106.502 | 1.00 | 27.83 |
| ATOM | 4440 | N | HIS | 3241 | 105.487 | 12.895 | 107.104 | 1.00 | 27.06 |
| ATOM | 4441 | CA | HIS | 3241 | 105.978 | 13.261 | 108.414 | 1.00 | 26.58 |
| ATOM | 4442 | CB | HIS | 3241 | 106.143 | 14.775 | 108.498 | 1.00 | 26.17 |
| ATOM | 4443 | CG | HIS | 3241 | 106.970 | 15.226 | 109.656 | 1.00 | 25.26 |
| ATOM | 4444 | CD2 | HIS | 3241 | 106.617 | 15.707 | 110.870 | 1.00 | 25.19 |
| ATOM | 4445 | ND1 | HIS | 3241 | 108.345 | 15.183 | 109.646 | 1.00 | 24.49 |
| ATOM | 4446 | CE1 | HIS | 3241 | 108.805 | 15.621 | 110.802 | 1.00 | 25.12 |
| ATOM | 4447 | NE2 | HIS | 3241 | 107.777 | 15.946 | 111.563 | 1.00 | 25.55 |
| ATOM | 4448 | C | HIS | 3241 | 104.900 | 12.811 | 109.387 | 1.00 | 26.77 |
| ATOM | 4449 | O | HIS | 3241 | 103.739 | 12.667 | 109.007 | 1.00 | 27.47 |

TABLE 6-continued

FGF2/FGFR1/Heparin Ternary Complex

| ATOM | 4450 | N   | THR | 3242 | 105.275 | 12.597 | 110.638 | 1.00 | 26.59 |
|------|------|-----|-----|------|---------|--------|---------|------|-------|
| ATOM | 4451 | CA  | THR | 3242 | 104.317 | 12.156 | 111.631 | 1.00 | 26.19 |
| ATOM | 4452 | CB  | THR | 3242 | 104.465 | 10.661 | 111.915 | 1.00 | 26.59 |
| ATOM | 4453 | OG1 | THR | 3242 | 103.849 | 9.915  | 110.858 | 1.00 | 27.70 |
| ATOM | 4454 | CG2 | THR | 3242 | 103.828 | 10.297 | 113.245 | 1.00 | 26.65 |
| ATOM | 4455 | C   | THR | 3242 | 104.471 | 12.894 | 112.934 | 1.00 | 26.79 |
| ATOM | 4456 | O   | THR | 3242 | 105.542 | 12.906 | 113.518 | 1.00 | 26.77 |
| ATOM | 4457 | N   | TYR | 3243 | 103.382 | 13.502 | 113.390 | 1.00 | 28.48 |
| ATOM | 4458 | CA  | TYR | 3243 | 103.370 | 14.243 | 114.645 | 1.00 | 29.17 |
| ATOM | 4459 | CB  | TYR | 3243 | 102.625 | 15.570 | 114.486 | 1.00 | 29.29 |
| ATOM | 4460 | CG  | TYR | 3243 | 103.268 | 16.528 | 113.519 | 1.00 | 28.26 |
| ATOM | 4461 | CD1 | TYR | 3243 | 102.774 | 16.678 | 112.241 | 1.00 | 27.48 |
| ATOM | 4462 | CE1 | TYR | 3243 | 103.364 | 17.556 | 111.345 | 1.00 | 29.98 |
| ATOM | 4463 | CD2 | TYR | 3243 | 104.379 | 17.282 | 113.890 | 1.00 | 28.49 |
| ATOM | 4464 | CE2 | TYR | 3243 | 104.981 | 18.162 | 113.003 | 1.00 | 28.64 |
| ATOM | 4465 | CZ  | TYR | 3243 | 104.470 | 18.299 | 111.728 | 1.00 | 29.37 |
| ATOM | 4466 | OH  | TYR | 3243 | 105.049 | 19.176 | 110.834 | 1.00 | 29.75 |
| ATOM | 4467 | C   | TYR | 3243 | 102.673 | 13.424 | 115.709 | 1.00 | 29.58 |
| ATOM | 4468 | O   | TYR | 3243 | 101.807 | 12.604 | 115.410 | 1.00 | 30.21 |
| ATOM | 4469 | N   | GLN | 3244 | 103.048 | 13.648 | 116.956 | 1.00 | 30.31 |
| ATOM | 4470 | CA  | GLN | 3244 | 102.431 | 12.918 | 118.035 | 1.00 | 30.89 |
| ATOM | 4471 | CB  | GLN | 3244 | 103.487 | 12.215 | 118.875 | 1.00 | 32.36 |
| ATOM | 4472 | CG  | GLN | 3244 | 103.029 | 10.858 | 119.367 | 1.00 | 33.61 |
| ATOM | 4473 | CD  | GLN | 3244 | 103.674 | 10.485 | 120.676 | 1.00 | 33.52 |
| ATOM | 4474 | OE1 | GLN | 3244 | 104.901 | 10.500 | 120.800 | 1.00 | 34.41 |
| ATOM | 4475 | NE2 | GLN | 3244 | 102.850 | 10.154 | 121.669 | 1.00 | 31.76 |
| ATOM | 4476 | C   | GLN | 3244 | 101.660 | 13.901 | 118.886 | 1.00 | 31.02 |
| ATOM | 4477 | O   | GLN | 3244 | 102.225 | 14.875 | 119.389 | 1.00 | 31.24 |
| ATOM | 4478 | N   | LEU | 3245 | 100.365 | 13.652 | 119.038 | 1.00 | 30.44 |
| ATOM | 4479 | CA  | LEU | 3245 | 99.528  | 14.521 | 119.844 | 1.00 | 29.31 |
| ATOM | 4480 | CB  | LEU | 3245 | 98.191  | 14.800 | 119.156 | 1.00 | 28.75 |
| ATOM | 4481 | CG  | LEU | 3245 | 97.199  | 15.558 | 120.052 | 1.00 | 28.69 |
| ATOM | 4482 | CD1 | LEU | 3245 | 97.836  | 16.833 | 120.593 | 1.00 | 27.11 |
| ATOM | 4483 | CD2 | LEU | 3245 | 95.946  | 15.873 | 119.270 | 1.00 | 27.94 |
| ATOM | 4484 | C   | LEU | 3245 | 99.252  | 13.878 | 121.177 | 1.00 | 28.63 |
| ATOM | 4485 | O   | LEU | 3245 | 98.953  | 12.694 | 121.248 | 1.00 | 29.05 |
| ATOM | 4486 | N   | ASP | 3246 | 99.368  | 14.672 | 122.231 | 1.00 | 27.91 |
| ATOM | 4487 | CA  | ASP | 3246 | 99.095  | 14.214 | 123.582 | 1.00 | 27.90 |
| ATOM | 4488 | CB  | ASP | 3246 | 100.391 | 13.965 | 124.350 | 1.00 | 27.24 |
| ATOM | 4489 | CG  | ASP | 3246 | 100.150 | 13.276 | 125.677 | 1.00 | 27.72 |
| ATOM | 4490 | OD1 | ASP | 3246 | 101.128 | 12.946 | 126.379 | 1.00 | 29.17 |
| ATOM | 4491 | OD2 | ASP | 3246 | 98.973  | 13.059 | 126.022 | 1.00 | 27.39 |
| ATOM | 4492 | C   | ASP | 3246 | 98.292  | 15.321 | 124.266 | 1.00 | 28.92 |
| ATOM | 4493 | O   | ASP | 3246 | 98.747  | 16.472 | 124.359 | 1.00 | 29.31 |
| ATOM | 4494 | N   | VAL | 3247 | 97.092  | 14.965 | 124.726 | 1.00 | 28.06 |
| ATOM | 4495 | CA  | VAL | 3247 | 96.182  | 15.895 | 125.388 | 1.00 | 26.11 |
| ATOM | 4496 | CB  | VAL | 3247 | 94.729  | 15.709 | 124.860 | 1.00 | 25.73 |
| ATOM | 4497 | CG1 | VAL | 3247 | 93.838  | 16.839 | 125.351 | 1.00 | 26.58 |
| ATOM | 4498 | CG2 | VAL | 3247 | 94.722  | 15.652 | 123.348 | 1.00 | 23.43 |
| ATOM | 4499 | C   | VAL | 3247 | 96.189  | 15.650 | 126.890 | 1.00 | 25.57 |
| ATOM | 4500 | O   | VAL | 3247 | 95.985  | 14.534 | 127.335 | 1.00 | 25.19 |
| ATOM | 4501 | N   | VAL | 3248 | 96.404  | 16.711 | 127.660 | 1.00 | 25.99 |
| ATOM | 4502 | CA  | VAL | 3248 | 96.467  | 16.636 | 129.115 | 1.00 | 25.90 |
| ATOM | 4503 | CB  | VAL | 3248 | 97.739  | 17.334 | 129.639 | 1.00 | 24.68 |
| ATOM | 4504 | OG1 | VAL | 3248 | 97.791  | 17.250 | 131.150 | 1.00 | 25.57 |
| ATOM | 4505 | CG2 | VAL | 3248 | 98.969  | 16.702 | 129.039 | 1.00 | 23.95 |
| ATOM | 4506 | C   | VAL | 3248 | 95.294  | 17.289 | 129.820 | 1.00 | 26.80 |
| ATOM | 4507 | O   | VAL | 3248 | 95.012  | 18.460 | 129.598 | 1.00 | 28.79 |
| ATOM | 4508 | N   | GLU | 3249 | 94.643  | 16.533 | 130.692 | 1.00 | 27.86 |
| ATOM | 4509 | CA  | GLU | 3249 | 93.543  | 17.062 | 131.475 | 1.00 | 30.65 |
| ATOM | 4510 | CB  | GLU | 3249 | 92.473  | 15.989 | 131.695 | 1.00 | 33.93 |
| ATOM | 4511 | CG  | GLU | 3249 | 91.804  | 15.484 | 130.420 | 1.00 | 39.01 |
| ATOM | 4512 | CD  | GLU | 3249 | 91.336  | 14.032 | 130.540 | 1.00 | 42.24 |
| ATOM | 4513 | OE1 | GLU | 3249 | 92.203  | 13.129 | 130.667 | 1.00 | 43.35 |
| ATOM | 4514 | OE2 | GLU | 3249 | 90.105  | 13.791 | 130.508 | 1.00 | 44.63 |
| ATOM | 4515 | C   | GLU | 3249 | 94.221  | 17.414 | 132.797 | 1.00 | 30.24 |
| ATOM | 4516 | O   | GLU | 3249 | 95.051  | 16.654 | 133.283 | 1.00 | 29.98 |
| ATOM | 4517 | N   | ARG | 3250 | 93.895  | 18.569 | 133.366 | 1.00 | 30.25 |
| ATOM | 4518 | CA  | ARG | 3250 | 94.505  | 18.987 | 134.623 | 1.00 | 30.41 |
| ATOM | 4519 | CB  | ARG | 3250 | 95.033  | 20.424 | 134.528 | 1.00 | 30.07 |
| ATOM | 4520 | CG  | ARG | 3250 | 96.019  | 20.709 | 133.402 | 1.00 | 28.85 |
| ATOM | 4521 | CD  | ARG | 3250 | 97.304  | 19.922 | 133.576 | 1.00 | 27.97 |
| ATOM | 4522 | NE  | ARG | 3250 | 97.881  | 20.115 | 134.902 | 1.00 | 26.90 |
| ATOM | 4523 | CZ  | ARG | 3250 | 98.860  | 20.967 | 135.188 | 1.00 | 26.21 |
| ATOM | 4524 | NH1 | ARG | 3250 | 99.398  | 21.726 | 134.243 | 1.00 | 23.51 |
| ATOM | 4525 | NH2 | ARG | 3250 | 99.300  | 21.053 | 136.433 | 1.00 | 27.00 |
| ATOM | 4526 | C   | ARG | 3250 | 93.475  | 18.928 | 135.728 | 1.00 | 31.02 |

TABLE 6-continued

| | | | FGF2/FGFR1/Heparin Ternary Complex | | | | | |
|---|---|---|---|---|---|---|---|---|
| ATOM | 4527 | O | ARG | 3250 | 92.307 | 19.200 | 135.501 | 1.00 | 31.46 |
| ATOM | 4528 | N | SER | 3251 | 93.908 | 18.567 | 136.924 | 1.00 | 31.93 |
| ATOM | 4529 | CA | SER | 3251 | 93.002 | 18.509 | 138.050 | 1.00 | 34.02 |
| ATOM | 4530 | CS | SER | 3251 | 93.086 | 17.158 | 138.745 | 1.00 | 35.31 |
| ATOM | 4531 | OG | SER | 3251 | 92.196 | 16.241 | 138.138 | 1.00 | 39.58 |
| ATOM | 4532 | C | SER | 3251 | 93.349 | 19.622 | 139.019 | 1.00 | 34.88 |
| ATOM | 4533 | O | SER | 3251 | 94.106 | 19.430 | 139.975 | 1.00 | 35.54 |
| ATOM | 4534 | N | PRO | 3252 | 92.794 | 20.812 | 138.777 | 1.00 | 35.37 |
| ATOM | 4535 | CD | PRO | 3252 | 91.905 | 21.123 | 137.643 | 1.00 | 35.49 |
| ATOM | 4536 | CA | PRO | 3252 | 93.003 | 22.009 | 139.586 | 1.00 | 36.36 |
| ATOM | 4537 | CB | PRO | 3252 | 92.649 | 23.124 | 138.621 | 1.00 | 35.28 |
| ATOM | 4538 | CG | PRO | 3252 | 91.459 | 22.545 | 137.954 | 1.00 | 35.69 |
| ATOM | 4539 | C | PRO | 3252 | 92.121 | 22.034 | 140.829 | 1.00 | 37.74 |
| ATOM | 4540 | O | PRO | 3252 | 91.161 | 22.802 | 140.908 | 1.00 | 37.38 |
| ATOM | 4541 | N | HIS | 3253 | 92.447 | 21.194 | 141.799 | 1.00 | 39.53 |
| ATOM | 4542 | CA | HIS | 3253 | 91.678 | 21.159 | 143.029 | 1.00 | 41.88 |
| ATOM | 4543 | CB | HIS | 3253 | 90.529 | 20.134 | 142.918 | 1.00 | 46.74 |
| ATOM | 4544 | CG | HIS | 3253 | 90.943 | 18.791 | 142.384 | 1.00 | 52.59 |
| ATOM | 4545 | CD2 | HIS | 3253 | 90.540 | 18.108 | 141.283 | 1.00 | 54.92 |
| ATOM | 4546 | ND1 | HIS | 3253 | 91.857 | 17.975 | 143.024 | 1.00 | 55.10 |
| ATOM | 4547 | CE1 | HIS | 3253 | 91.995 | 16.850 | 142.343 | 1.00 | 55.48 |
| ATOM | 4548 | NE2 | HIS | 3253 | 91.206 | 16.904 | 141.283 | 1.00 | 55.66 |
| ATOM | 4549 | C | HIS | 3253 | 92.577 | 20.854 | 144.221 | 1.00 | 40.56 |
| ATOM | 4550 | O | HIS | 3253 | 93.738 | 20.478 | 144.051 | 1.00 | 39.99 |
| ATOM | 4551 | N | ARG | 3254 | 92.052 | 21.054 | 145.426 | 1.00 | 39.06 |
| ATOM | 4552 | CA | ARG | 3254 | 92.819 | 20.761 | 146.629 | 1.00 | 36.99 |
| ATOM | 4553 | CB | ARG | 3254 | 92.008 | 21.110 | 147.887 | 1.00 | 37.56 |
| ATOM | 4554 | CG | ARG | 3254 | 90.502 | 20.865 | 147.776 | 1.00 | 39.95 |
| ATOM | 4555 | CD | ARG | 3254 | 89.743 | 21.410 | 149.003 | 1.00 | 43.17 |
| ATOM | 4556 | NE | ARG | 3254 | 88.289 | 21.496 | 148.798 | 1.00 | 46.65 |
| ATOM | 4557 | CZ | ARG | 3254 | 87.679 | 22.342 | 147.959 | 1.00 | 48.09 |
| ATOM | 4558 | NH1 | ARG | 3254 | 88.384 | 23.198 | 147.228 | 1.00 | 48.53 |
| ATOM | 4559 | NH2 | ARG | 3254 | 86.356 | 22.327 | 147.831 | 1.00 | 48.59 |
| ATOM | 4560 | C | ARG | 3254 | 93.129 | 19.275 | 146.584 | 1.00 | 34.92 |
| ATOM | 4561 | O | ARG | 3254 | 92.444 | 18.516 | 145.909 | 1.00 | 34.69 |
| ATOM | 4562 | N | PRO | 3255 | 94.179 | 18.837 | 147.284 | 1.00 | 33.60 |
| ATOM | 4563 | CD | PRO | 3255 | 95.155 | 19.619 | 148.060 | 1.00 | 33.94 |
| ATOM | 4564 | CA | PRO | 3255 | 94.530 | 17.413 | 147.285 | 1.00 | 32.24 |
| ATOM | 4565 | CB | PRO | 3255 | 95.702 | 17.353 | 148.253 | 1.00 | 32.62 |
| ATOM | 4566 | CG | PRO | 3255 | 96.346 | 18.701 | 148.074 | 1.00 | 33.33 |
| ATOM | 4567 | C | PRO | 3255 | 93.369 | 16.527 | 147.735 | 1.00 | 30.77 |
| ATOM | 4568 | O | PRO | 3255 | 92.468 | 16.979 | 148.431 | 1.00 | 31.17 |
| ATOM | 4569 | N | ILE | 3256 | 93.396 | 15.263 | 147.338 | 1.00 | 29.48 |
| ATOM | 4570 | CA | ILE | 3256 | 92.341 | 14.332 | 147.703 | 1.00 | 28.59 |
| ATOM | 4571 | CB | ILE | 3256 | 91.587 | 13.839 | 146.449 | 1.00 | 27.91 |
| ATOM | 4572 | CG2 | ILE | 3256 | 90.507 | 12.845 | 146.834 | 1.00 | 29.43 |
| ATOM | 4573 | CG1 | ILE | 3256 | 90.941 | 15.022 | 145.736 | 1.00 | 25.98 |
| ATOM | 4574 | CD1 | ILE | 3256 | 90.229 | 14.643 | 144.477 | 1.00 | 26.04 |
| ATOM | 4575 | C | ILE | 3256 | 92.965 | 13.151 | 148.425 | 1.00 | 29.03 |
| ATOM | 4576 | O | ILE | 3256 | 93.915 | 12.548 | 147.926 | 1.00 | 29.94 |
| ATOM | 4577 | N | LEU | 3257 | 92.434 | 12.826 | 149.602 | 1.00 | 28.80 |
| ATOM | 4578 | CA | LEU | 3257 | 92.962 | 11.721 | 150.399 | 1.00 | 28.38 |
| ATOM | 4579 | CB | LEE | 3257 | 93.061 | 12.139 | 151.869 | 1.00 | 26.67 |
| ATOM | 4580 | CG | LEU | 3257 | 93.601 | 13.547 | 152.154 | 1.00 | 24.49 |
| ATOM | 4581 | CD1 | LEU | 3257 | 93.584 | 13.840 | 153.644 | 1.00 | 22.81 |
| ATOM | 4582 | CD2 | LEU | 3257 | 94.997 | 13.659 | 151.613 | 1.00 | 23.52 |
| ATOM | 4583 | C | LEU | 3257 | 92.072 | 10.495 | 150.274 | 1.00 | 28.27 |
| ATOM | 4584 | O | LEU | 3257 | 90.857 | 10.598 | 150.393 | 1.00 | 28.75 |
| ATOM | 4585 | N | GLN | 3258 | 92.680 | 9.337 | 150.025 | 1.00 | 28.85 |
| ATOM | 4586 | CA | GLN | 3258 | 91.933 | 8.089 | 149.891 | 1.00 | 28.72 |
| ATOM | 4587 | CB | GLN | 3258 | 92.896 | 6.903 | 149.780 | 1.00 | 27.32 |
| ATOM | 4588 | C | GLN | 3258 | 91.040 | 7.925 | 151.114 | 1.00 | 28.84 |
| ATOM | 4589 | O | GLN | 3258 | 91.528 | 7.882 | 152.251 | 1.00 | 29.72 |
| ATOM | 4590 | N | ALA | 3259 | 89.732 | 7.862 | 150.888 | 1.00 | 27.60 |
| ATOM | 4591 | CA | ALA | 3259 | 88.805 | 7.704 | 151.992 | 1.00 | 26.97 |
| ATOM | 4592 | CB | ALA | 3259 | 87.404 | 7.573 | 151.469 | 1.00 | 26.90 |
| ATOM | 4593 | C | ALA | 3259 | 89.204 | 6.461 | 152.777 | 1.00 | 27.13 |
| ATOM | 4594 | O | ALA | 3259 | 89.718 | 5.500 | 152.208 | 1.00 | 27.15 |
| ATOM | 4595 | N | GLY | 3260 | 88.991 | 6.492 | 154.086 | 1.00 | 26.91 |
| ATOM | 4596 | CA | GLY | 3260 | 89.335 | 5.347 | 154.900 | 1.00 | 26.38 |
| ATOM | 4597 | C | GLY | 3260 | 90.718 | 5.420 | 155.508 | 1.00 | 26.52 |
| ATOM | 4598 | O | GLY | 3260 | 90.988 | 4.767 | 156.519 | 1.00 | 26.75 |
| ATOM | 4599 | N | LEU | 3261 | 91.598 | 6.210 | 154.903 | 1.00 | 26.39 |
| ATOM | 4600 | CA | LEU | 3261 | 92.958 | 6.359 | 155.417 | 1.00 | 27.04 |
| ATOM | 4601 | CB | LEU | 3261 | 93.962 | 6.022 | 154.333 | 1.00 | 26.16 |
| ATOM | 4602 | CG | LEU | 3261 | 93.859 | 4.620 | 153.767 | 1.00 | 24.65 |
| ATOM | 4603 | CD1 | LEU | 3261 | 94.803 | 4.487 | 152.597 | 1.00 | 25.97 |

TABLE 6-continued

FGF2/FGFR1/Heparin Ternary Complex

| ATOM | 4604 | CD2 | LEU | 3261 | 94.196 | 3.623 | 154.848 | 1.00 | 23.96 |
|---|---|---|---|---|---|---|---|---|---|
| ATOM | 4605 | C | LEU | 3261 | 93.231 | 7.781 | 155.887 | 1.00 | 27.98 |
| ATOM | 4606 | O | LEU | 3261 | 92.841 | 8.743 | 155.221 | 1.00 | 28.15 |
| ATOM | 4607 | N | PRO | 3262 | 93.915 | 7.935 | 157.034 | 1.00 | 27.82 |
| ATOM | 4608 | CD | PRO | 3262 | 94.199 | 9.267 | 157.596 | 1.00 | 27.04 |
| ATOM | 4609 | CA | PRO | 3262 | 94.443 | 6.879 | 157.905 | 1.00 | 27.29 |
| ATOM | 4610 | CB | PRO | 3262 | 95.255 | 7.657 | 158.928 | 1.00 | 26.57 |
| ATOM | 4611 | CG | PRO | 3262 | 94.507 | 8.949 | 159.031 | 1.00 | 25.59 |
| ATOM | 4612 | C | PRO | 3262 | 93.320 | 6.090 | 158.549 | 1.00 | 27.40 |
| ATOM | 4613 | O | PRO | 3262 | 92.171 | 6.527 | 158.540 | 1.00 | 27.33 |
| ATOM | 4614 | N | ALA | 3263 | 93.649 | 4.940 | 159.122 | 1.00 | 27.92 |
| ATOM | 4615 | CA | ALA | 3263 | 92.624 | 4.108 | 159.748 | 1.00 | 28.71 |
| ATOM | 4616 | CB | ALA | 3263 | 92.638 | 2.730 | 159.125 | 1.00 | 28.45 |
| ATOM | 4617 | C | ALA | 3263 | 92.749 | 3.976 | 161.254 | 1.00 | 28.80 |
| ATOM | 4618 | O | ALA | 3263 | 93.841 | 3.831 | 161.779 | 1.00 | 29.46 |
| ATOM | 4619 | N | ASN | 3264 | 91.622 | 4.019 | 161.949 | 1.00 | 28.97 |
| ATOM | 4620 | CA | ASN | 3264 | 91.645 | 3.864 | 163.389 | 1.00 | 28.99 |
| ATOM | 4621 | CB | ASN | 3264 | 90.234 | 3.840 | 163.954 | 1.00 | 27.63 |
| ATOM | 4622 | CG | ASN | 3264 | 89.562 | 5.166 | 163.857 | 1.00 | 28.47 |
| ATOM | 4623 | OD1 | ASN | 3264 | 90.224 | 6.183 | 163.687 | 1.00 | 29.69 |
| ATOM | 4624 | ND2 | ASN | 3264 | 88.241 | 5.181 | 163.982 | 1.00 | 29.95 |
| ATOM | 4625 | C | ASN | 3264 | 92.303 | 2.537 | 163.689 | 1.00 | 30.40 |
| ATOM | 4626 | O | ASN | 3264 | 92.068 | 1.559 | 162.991 | 1.00 | 31.27 |
| ATOM | 4627 | N | LYS | 3265 | 93.131 | 2.497 | 164.722 | 1.00 | 32.26 |
| ATOM | 4628 | CA | LYS | 3265 | 93.784 | 1.259 | 165.096 | 1.00 | 34.23 |
| ATOM | 4629 | CB | LYS | 3265 | 95.195 | 1.197 | 164.512 | 1.00 | 33.73 |
| ATOM | 4630 | CG | LYS | 3265 | 95.200 | 1.353 | 163.001 | 1.00 | 36.20 |
| ATOM | 4631 | CD | LYS | 3265 | 96.425 | 0.751 | 162.324 | 1.00 | 35.68 |
| ATOM | 4632 | CE | LYS | 3265 | 96.349 | 0.942 | 160.802 | 1.00 | 36.29 |
| ATOM | 4633 | NZ | LYS | 3265 | 96.399 | 2.381 | 160.343 | 1.00 | 36.19 |
| ATOM | 4634 | C | LYS | 3265 | 93.861 | 1.143 | 166.598 | 1.00 | 36.25 |
| ATOM | 4635 | O | LYS | 3265 | 94.239 | 2.095 | 167.283 | 1.00 | 37.73 |
| ATOM | 4636 | N | THR | 3266 | 93.475 | −0.020 | 167.113 | 1.00 | 37.24 |
| ATOM | 4637 | CA | THR | 3266 | 93.553 | −0.280 | 168.546 | 1.00 | 36.86 |
| ATOM | 4638 | CB | THR | 3266 | 92.287 | −0.948 | 169.090 | 1.00 | 37.14 |
| ATOM | 4639 | OG1 | THR | 3266 | 91.211 | 0.001 | 169.119 | 1.00 | 38.13 |
| ATOM | 4640 | CG2 | THR | 3266 | 92.541 | −1.480 | 170.486 | 1.00 | 37.17 |
| ATOM | 4641 | C | THR | 3266 | 94.699 | −1.257 | 168.690 | 1.00 | 36.59 |
| ATOM | 4642 | O | THR | 3266 | 94.750 | −2.266 | 167.992 | 1.00 | 35.31 |
| ATOM | 4643 | N | VAL | 3267 | 95.637 | −0.950 | 169.570 | 1.00 | 37.49 |
| ATOM | 4644 | CA | VAL | 3267 | 96.765 | −1.839 | 169.756 | 1.00 | 38.41 |
| ATOM | 4645 | CB | VAL | 3267 | 97.956 | −1.443 | 168.889 | 1.00 | 37.78 |
| ATOM | 4646 | CG1 | VAL | 3267 | 97.582 | −1.534 | 167.427 | 1.00 | 36.85 |
| ATOM | 4647 | CG2 | VAL | 3267 | 98.424 | −0.056 | 169.269 | 1.00 | 38.27 |
| ATOM | 4648 | C | VAL | 3267 | 97.251 | −1.931 | 171.184 | 1.00 | 39.74 |
| ATOM | 4649 | O | VAL | 3267 | 96.917 | −1.103 | 172.037 | 1.00 | 39.65 |
| ATOM | 4650 | N | ALA | 3268 | 98.062 | −2.958 | 171.415 | 1.00 | 41.45 |
| ATOM | 4651 | CA | ALA | 3268 | 98.634 | −3.248 | 172.719 | 1.00 | 42.65 |
| ATOM | 4652 | CB | ALA | 3268 | 99.206 | −4.659 | 172.717 | 1.00 | 42.62 |
| ATOM | 4653 | C | ALA | 3268 | 99.716 | −2.248 | 173.102 | 1.00 | 42.98 |
| ATOM | 4654 | O | ALA | 3268 | 100.460 | −1.753 | 172.254 | 1.00 | 42.72 |
| ATOM | 4655 | N | LEU | 3269 | 99.793 | −1.949 | 174.390 | 1.00 | 43.80 |
| ATOM | 4656 | CA | LEU | 3269 | 100.799 | −1.025 | 174.878 | 1.00 | 44.03 |
| ATOM | 4657 | CB | LEU | 3269 | 100.722 | −0.936 | 176.402 | 1.00 | 43.53 |
| ATOM | 4658 | CG | LEU | 3269 | 101.513 | 0.180 | 177.076 | 1.00 | 43.63 |
| ATOM | 4659 | CD1 | LEU | 3269 | 101.185 | 0.198 | 178.554 | 1.00 | 42.55 |
| ATOM | 4660 | CD2 | LEU | 3269 | 102.997 | −0.026 | 176.847 | 1.00 | 43.57 |
| ATOM | 4661 | C | LEU | 3269 | 102.157 | −1.562 | 174.443 | 1.00 | 44.04 |
| ATOM | 4662 | O | LEU | 3269 | 102.408 | −2.767 | 174.518 | 1.00 | 44.70 |
| ATOM | 4663 | N | GLY | 3270 | 103.019 | −0.670 | 173.967 | 1.00 | 44.06 |
| ATOM | 4664 | CA | GLY | 3270 | 104.345 | −1.072 | 173.533 | 1.00 | 44.11 |
| ATOM | 4665 | C | GLY | 3270 | 104.444 | −1.611 | 172.120 | 1.00 | 43.68 |
| ATOM | 4666 | O | GLY | 3270 | 105.537 | −1.870 | 171.631 | 1.00 | 44.34 |
| ATOM | 4667 | N | SER | 3271 | 103.313 | −1.782 | 171.452 | 1.00 | 43.40 |
| ATOM | 4668 | CA | SER | 3271 | 103.331 | −2.300 | 170.095 | 1.00 | 43.72 |
| ATOM | 4669 | CB | SER | 3271 | 101.916 | −2.647 | 169.654 | 1.00 | 44.49 |
| ATOM | 4670 | OG | SER | 3271 | 101.400 | −3.715 | 170.425 | 1.00 | 47.59 |
| ATOM | 4671 | C | SER | 3271 | 103.937 | −1.324 | 169.100 | 1.00 | 43.31 |
| ATOM | 4672 | O | SER | 3271 | 104.451 | −0.272 | 169.472 | 1.00 | 43.23 |
| ATOM | 4673 | N | ASN | 3272 | 103.893 | −1.702 | 167.828 | 1.00 | 42.89 |
| ATOM | 4674 | CA | ASN | 3272 | 104.381 | −0.853 | 166.754 | 1.00 | 42.44 |
| ATOM | 4675 | CB | ASN | 3272 | 105.553 | −1.500 | 166.020 | 1.00 | 42.30 |
| ATOM | 4676 | CG | ASN | 3272 | 106.897 | −1.031 | 166.560 | 1.00 | 43.38 |
| ATOM | 4677 | OD1 | ASN | 3272 | 107.047 | −0.801 | 167.760 | 1.00 | 44.26 |
| ATOM | 4678 | ND2 | ASN | 3272 | 107.882 | −0.895 | 165.678 | 1.00 | 42.85 |
| ATOM | 4679 | C | ASN | 3272 | 103.207 | −0.638 | 165.826 | 1.00 | 41.87 |
| ATOM | 4680 | O | ASN | 3272 | 102.445 | −1.562 | 165.533 | 1.00 | 42.45 |

TABLE 6-continued

FGF2/FGFR1/Heparin Ternary Complex

| ATOM | 4681 | N | VAL | 3273 | 103.031 | 0.594 | 165.386 | 1.00 | 40.66 |
|---|---|---|---|---|---|---|---|---|---|
| ATOM | 4682 | CA | VAL | 3273 | 101.922 | 0.876 | 164.506 | 1.00 | 40.23 |
| ATOM | 4683 | CB | VAL | 3273 | 100.717 | 1.369 | 165.329 | 1.00 | 40.17 |
| ATOM | 4684 | CG1 | VAL | 3273 | 101.096 | 2.625 | 166.103 | 1.00 | 40.95 |
| ATOM | 4685 | CG2 | VAL | 3273 | 99.523 | 1.601 | 164.420 | 1.00 | 40.27 |
| ATOM | 4686 | C | VAL | 3273 | 102.312 | 1.882 | 163.427 | 1.00 | 39.67 |
| ATOM | 4687 | O | VAL | 3273 | 103.176 | 2.743 | 163.638 | 1.00 | 38.85 |
| ATOM | 4688 | N | GLU | 3274 | 101.697 | 1.740 | 162.258 | 1.00 | 38.75 |
| ATOM | 4689 | CA | GLU | 3274 | 101.973 | 2.635 | 161.153 | 1.00 | 39.69 |
| ATOM | 4690 | CB | GLU | 3274 | 102.820 | 1.930 | 160.090 | 1.00 | 41.41 |
| ATOM | 4691 | CG | GLU | 3274 | 102.174 | 0.682 | 159.520 | 1.00 | 45.93 |
| ATOM | 4692 | CD | GLU | 3274 | 102.775 | 0.252 | 158.193 | 1.00 | 47.99 |
| ATOM | 4693 | OE1 | GLU | 3274 | 103.969 | −0.130 | 158.166 | 1.00 | 49.33 |
| ATOM | 4694 | OE2 | GLU | 3274 | 102.046 | 0.303 | 157.174 | 1.00 | 48.79 |
| ATOM | 4695 | C | GLU | 3274 | 100.658 | 3.111 | 160.540 | 1.00 | 39.16 |
| ATOM | 4696 | O | GLU | 3274 | 99.771 | 2.307 | 160.239 | 1.00 | 39.37 |
| ATOM | 4697 | N | PHE | 3275 | 100.533 | 4.426 | 160.377 | 1.00 | 37.34 |
| ATOM | 4698 | CA | PHE | 3275 | 99.343 | 5.025 | 159.794 | 1.00 | 35.65 |
| ATOM | 4699 | CB | PHE | 3275 | 98.988 | 6.312 | 160.531 | 1.00 | 35.93 |
| ATOM | 4700 | CG | PHE | 3275 | 98.371 | 6.086 | 161.888 | 1.00 | 36.46 |
| ATOM | 4701 | CD1 | PHE | 3275 | 97.000 | 5.865 | 162.018 | 1.00 | 36.34 |
| ATOM | 4702 | CD2 | PHE | 3275 | 99.158 | 6.108 | 163.039 | 1.00 | 36.18 |
| ATOM | 4703 | CE1 | PHE | 3275 | 96.425 | 5.677 | 163.266 | 1.00 | 35.66 |
| ATOM | 4704 | CE2 | PHE | 3275 | 98.593 | 5.920 | 164.288 | 1.00 | 35.26 |
| ATOM | 4705 | CZ | PHE | 3275 | 97.223 | 5.706 | 164.403 | 1.00 | 36.25 |
| ATOM | 4706 | C | PHE | 3275 | 99.623 | 5.325 | 158.340 | 1.00 | 34.81 |
| ATOM | 4707 | O | PHE | 3275 | 100.748 | 5.633 | 157.980 | 1.00 | 35.61 |
| ATOM | 4708 | N | MET | 3276 | 98.605 | 5.232 | 157.497 | 1.00 | 33.75 |
| ATOM | 4709 | CA | MET | 3276 | 98.805 | 5.490 | 156.087 | 1.00 | 32.92 |
| ATOM | 4710 | CB | MET | 3276 | 98.557 | 4.243 | 155.262 | 1.00 | 34.99 |
| ATOM | 4711 | CG | MET | 3276 | 99.786 | 3.391 | 155.060 | 1.00 | 38.18 |
| ATOM | 4712 | SD | MET | 3276 | 99.571 | 2.378 | 153.591 | 1.00 | 42.05 |
| ATOM | 4713 | CE | MET | 3276 | 99.885 | 3.632 | 152.264 | 1.00 | 41.35 |
| ATOM | 4714 | C | MET | 3276 | 97.958 | 6.602 | 155.543 | 1.00 | 31.97 |
| ATOM | 4715 | O | MET | 3276 | 96.865 | 6.874 | 156.026 | 1.00 | 31.01 |
| ATOM | 4716 | N | CYS | 3277 | 98.475 | 7.231 | 154.500 | 1.00 | 32.15 |
| ATOM | 4717 | CA | CYS | 3277 | 97.797 | 8.345 | 153.874 | 1.00 | 32.48 |
| ATOM | 4718 | C | CYS | 3277 | 98.093 | 8.406 | 152.389 | 1.00 | 32.61 |
| ATOM | 4719 | O | CYS | 3277 | 99.217 | 8.710 | 152.001 | 1.00 | 33.63 |
| ATOM | 4720 | CB | CYS | 3277 | 98.268 | 9.629 | 154.515 | 1.00 | 31.50 |
| ATOM | 4721 | SG | CYS | 3277 | 97.213 | 11.028 | 154.104 | 1.00 | 32.81 |
| ATOM | 4722 | N | LYS | 3278 | 97.086 | 8.124 | 151.566 | 1.00 | 32.56 |
| ATOM | 4723 | CA | LYS | 3278 | 97.234 | 8.140 | 150.113 | 1.00 | 32.30 |
| ATOM | 4724 | CB | LYS | 3278 | 96.478 | 6.953 | 149.507 | 1.00 | 34.17 |
| ATOM | 4725 | CG | LYS | 3278 | 97.321 | 6.022 | 148.640 | 1.00 | 37.65 |
| ATOM | 4726 | CD | LYS | 3278 | 96.442 | 5.147 | 147.720 | 1.00 | 40.56 |
| ATOM | 4727 | CE | LYS | 3278 | 95.583 | 5.998 | 146.746 | 1.00 | 41.33 |
| ATOM | 4728 | NZ | LYS | 3278 | 94.680 | 5.218 | 145.833 | 1.00 | 38.90 |
| ATOM | 4729 | C | LYS | 3278 | 96.684 | 9.462 | 149.554 | 1.00 | 31.44 |
| ATOM | 4730 | O | LYS | 3278 | 95.478 | 9.710 | 149.599 | 1.00 | 31.95 |
| ATOM | 4731 | N | VAL | 3279 | 97.565 | 10.307 | 149.024 | 1.00 | 29.86 |
| ATOM | 4732 | CA | VAL | 3279 | 97.158 | 11.607 | 148.489 | 1.00 | 27.85 |
| ATOM | 4733 | CB | VAL | 3279 | 98.071 | 12.734 | 148.985 | 1.00 | 26.96 |
| ATOM | 4734 | CG1 | VAL | 3279 | 97.568 | 14.064 | 148.475 | 1.00 | 25.70 |
| ATOM | 4735 | CG2 | VAL | 3279 | 98.140 | 12.728 | 150.483 | 1.00 | 28.06 |
| ATOM | 4736 | C | VAL | 3279 | 97.188 | 11.716 | 146.980 | 1.00 | 27.93 |
| ATOM | 4737 | O | VAL | 3279 | 98.060 | 11.149 | 146.327 | 1.00 | 28.90 |
| ATOM | 4738 | N | TYR | 3280 | 96.227 | 12.453 | 146.431 | 1.00 | 27.27 |
| ATOM | 4739 | CA | TYR | 3280 | 96.186 | 12.703 | 144.998 | 1.00 | 26.48 |
| ATOM | 4740 | CB | TYR | 3280 | 94.926 | 12.163 | 144.340 | 1.00 | 26.34 |
| ATOM | 4741 | CG | TYR | 3280 | 94.883 | 12.547 | 142.877 | 1.00 | 26.58 |
| ATOM | 4742 | CD1 | TYR | 3280 | 95.678 | 11.883 | 141.945 | 1.00 | 26.09 |
| ATOM | 4743 | CE1 | TYR | 3280 | 95.758 | 12.303 | 140.626 | 1.00 | 25.75 |
| ATOM | 4744 | CD2 | TYR | 3280 | 94.146 | 13.649 | 142.445 | 1.00 | 26.17 |
| ATOM | 4745 | CE2 | TYR | 3280 | 94.215 | 14.084 | 141.126 | 1.00 | 27.68 |
| ATOM | 4746 | CZ | TYR | 3280 | 95.033 | 13.408 | 140.218 | 1.00 | 28.39 |
| ATOM | 4747 | OH | TYR | 3280 | 95.172 | 13.866 | 138.917 | 1.00 | 29.19 |
| ATOM | 4748 | C | TYR | 3280 | 96.195 | 14.212 | 144.820 | 1.00 | 26.25 |
| ATOM | 4749 | O | TYR | 3280 | 95.560 | 14.930 | 145.585 | 1.00 | 26.63 |
| ATOM | 4750 | N | SER | 3281 | 96.911 | 14.697 | 143.816 | 1.00 | 25.82 |
| ATOM | 4751 | CA | SER | 3281 | 96.964 | 16.130 | 143.570 | 1.00 | 25.99 |
| ATOM | 4752 | CB | SER | 3281 | 97.601 | 16.859 | 144.764 | 1.00 | 27.74 |
| ATOM | 4753 | OG | SER | 3281 | 97.606 | 18.270 | 144.578 | 1.00 | 29.73 |
| ATOM | 4754 | C | SER | 3281 | 97.757 | 16.405 | 142.317 | 1.00 | 24.60 |
| ATOM | 4755 | O | SER | 3281 | 98.848 | 15.882 | 142.143 | 1.00 | 24.71 |
| ATOM | 4756 | N | ASP | 3282 | 97.194 | 17.217 | 141.431 | 1.00 | 24.73 |
| ATOM | 4757 | CA | ASP | 3282 | 97.891 | 17.549 | 140.206 | 1.00 | 24.05 |

TABLE 6-continued

FGF2/FGFR1/Heparin Ternary Complex

| ATOM | 4758 | CB | ASP | 3282 | 96.981 | 18.367 | 139.285 | 1.00 | 24.90 |
|---|---|---|---|---|---|---|---|---|---|
| ATOM | 4759 | CG | ASP | 3282 | 97.553 | 18.525 | 137.897 | 1.00 | 26.63 |
| ATOM | 4760 | OD1 | ASP | 3282 | 96.849 | 19.040 | 136.992 | 1.00 | 26.29 |
| ATOM | 4761 | OD2 | ASP | 3282 | 98.719 | 18.127 | 137.717 | 1.00 | 28.43 |
| ATOM | 4762 | C | ASP | 3282 | 99.096 | 18.357 | 140.673 | 1.00 | 23.14 |
| ATOM | 4763 | O | ASP | 3282 | 100.230 | 17.872 | 140.629 | 1.00 | 23.70 |
| ATOM | 4764 | N | PRO | 3283 | 98.867 | 19.584 | 141.173 | 1.00 | 21.96 |
| ATOM | 4765 | CD | PRO | 3283 | 97.607 | 20.287 | 141.441 | 1.00 | 21.41 |
| ATOM | 4766 | CA | PRO | 3283 | 99.988 | 20.391 | 141.634 | 1.00 | 21.24 |
| ATOM | 4767 | CB | PRO | 3283 | 99.316 | 21.668 | 142.111 | 1.00 | 20.49 |
| ATOM | 4768 | CG | PRO | 3283 | 98.043 | 21.698 | 141.376 | 1.00 | 19.84 |
| ATOM | 4769 | C | PRO | 3283 | 100.673 | 19.652 | 142.775 | 1.00 | 22.00 |
| ATOM | 4770 | O | PRO | 3283 | 100.019 | 18.974 | 143.569 | 1.00 | 22.58 |
| ATOM | 4771 | N | GLN | 3284 | 101.985 | 19.787 | 142.862 | 1.00 | 21.77 |
| ATOM | 4772 | CA | GLN | 3284 | 102.731 | 19.100 | 143.894 | 1.00 | 22.25 |
| ATOM | 4773 | CB | GLN | 3284 | 104.193 | 19.519 | 143.817 | 1.00 | 22.11 |
| ATOM | 4774 | CG | GLN | 3284 | 105.167 | 18.363 | 143.885 | 1.00 | 21.39 |
| ATOM | 4775 | CD | GLN | 3284 | 104.727 | 17.168 | 143.070 | 1.00 | 20.44 |
| ATOM | 4776 | OE1 | GLN | 3284 | 104.308 | 17.294 | 141.927 | 1.00 | 21.08 |
| ATOM | 4777 | NE2 | GLN | 3284 | 104.839 | 15.993 | 143.659 | 1.00 | 22.03 |
| ATOM | 4778 | C | GLN | 3284 | 102.138 | 19.397 | 145.259 | 1.00 | 23.07 |
| ATOM | 4779 | O | GLN | 3284 | 102.113 | 20.541 | 145.696 | 1.00 | 25.06 |
| ATOM | 4780 | N | PRO | 3285 | 101.625 | 18.365 | 145.943 | 1.00 | 23.82 |
| ATOM | 4781 | CD | PRO | 3285 | 101.402 | 16.995 | 145.447 | 1.00 | 23.47 |
| ATOM | 4782 | CA | PRO | 3285 | 101.022 | 18.529 | 147.266 | 1.00 | 24.63 |
| ATOM | 4783 | CB | PRO | 3285 | 100.077 | 17.342 | 147.355 | 1.00 | 23.30 |
| ATOM | 4784 | CG | PRO | 3285 | 100.879 | 16.277 | 146.685 | 1.00 | 23.16 |
| ATOM | 4785 | C | PRO | 3285 | 102.052 | 18.501 | 148.379 | 1.00 | 25.09 |
| ATOM | 4786 | O | PRO | 3285 | 103.148 | 17.968 | 148.206 | 1.00 | 25.46 |
| ATOM | 4787 | N | HIS | 3286 | 101.700 | 19.080 | 149.518 | 1.00 | 25.38 |
| ATOM | 4788 | CA | HIS | 3286 | 102.610 | 19.062 | 150.635 | 1.00 | 25.96 |
| ATOM | 4789 | CB | HIS | 3286 | 103.016 | 20.461 | 151.040 | 1.00 | 26.69 |
| ATOM | 4790 | CG | HIS | 3286 | 104.002 | 20.468 | 152.154 | 1.00 | 27.68 |
| ATOM | 4791 | CD2 | HIS | 3286 | 105.002 | 19.608 | 152.454 | 1.00 | 28.17 |
| ATOM | 4792 | ND1 | HIS | 3286 | 104.003 | 21.419 | 153.148 | 1.00 | 29.66 |
| ATOM | 4793 | CE1 | HIS | 3286 | 104.960 | 21.141 | 154.016 | 1.00 | 30.81 |
| ATOM | 4794 | NE2 | HIS | 3286 | 105.581 | 20.045 | 153.617 | 1.00 | 29.40 |
| ATOM | 4795 | C | HIS | 3286 | 101.947 | 18.357 | 151.810 | 1.00 | 26.58 |
| ATOM | 4796 | O | HIS | 3286 | 101.061 | 18.905 | 152.472 | 1.00 | 26.84 |
| ATOM | 4797 | N | ILE | 3287 | 102.384 | 17.128 | 152.055 | 1.00 | 26.39 |
| ATOM | 4798 | CA | ILE | 3287 | 101.846 | 16.312 | 153.131 | 1.00 | 26.11 |
| ATOM | 4799 | CB | ILE | 3287 | 102.083 | 14.831 | 152.853 | 1.00 | 24.99 |
| ATOM | 4800 | CG2 | ILE | 3287 | 101.725 | 13.997 | 154.069 | 1.00 | 22.95 |
| ATOM | 4801 | CG1 | ILE | 3287 | 101.288 | 14.420 | 151.626 | 1.00 | 23.31 |
| ATOM | 4802 | CD1 | ILE | 3287 | 101.531 | 13.009 | 151.238 | 1.00 | 25.95 |
| ATOM | 4803 | C | ILE | 3287 | 102.483 | 16.630 | 154.464 | 1.00 | 26.79 |
| ATOM | 4804 | O | ILE | 3287 | 103.640 | 17.022 | 154.533 | 1.00 | 28.01 |
| ATOM | 4805 | N | GLN | 3288 | 101.728 | 16.429 | 155.532 | 1.00 | 26.95 |
| ATOM | 4806 | CA | GLN | 3288 | 102.231 | 16.695 | 156.868 | 1.00 | 27.08 |
| ATOM | 4807 | CB | GLN | 3288 | 102.097 | 18.183 | 157.182 | 1.00 | 26.69 |
| ATOM | 4808 | CG | GLN | 3288 | 102.317 | 18.539 | 158.635 | 1.00 | 27.45 |
| ATOM | 4809 | CD | GLN | 3288 | 102.359 | 20.033 | 158.867 | 1.00 | 27.88 |
| ATOM | 4810 | OE1 | GLN | 3288 | 103.433 | 20.619 | 159.023 | 1.00 | 29.46 |
| ATOM | 4811 | NE2 | GLN | 3288 | 101.190 | 20.663 | 158.880 | 1.00 | 26.56 |
| ATOM | 4812 | C | GLN | 3288 | 101.445 | 15.870 | 157.871 | 1.00 | 27.00 |
| ATOM | 4813 | O | GLN | 3288 | 100.217 | 15.850 | 157.821 | 1.00 | 26.94 |
| ATOM | 4814 | N | TRP | 3289 | 102.156 | 15.192 | 158.772 | 1.00 | 25.98 |
| ATOM | 4815 | CA | TRP | 3289 | 101.527 | 14.360 | 159.784 | 1.00 | 25.52 |
| ATOM | 4816 | CB | TRP | 3289 | 102.339 | 13.077 | 159.985 | 1.00 | 24.71 |
| ATOM | 4817 | CG | TRP | 3289 | 102.001 | 12.024 | 158.990 | 1.00 | 23.67 |
| ATOM | 4818 | CD2 | TRP | 3289 | 100.833 | 11.188 | 159.005 | 1.00 | 23.20 |
| ATOM | 4819 | CE2 | TRP | 3289 | 100.883 | 10.379 | 157.843 | 1.00 | 23.28 |
| ATOM | 4820 | CE3 | TRP | 3289 | 99.748 | 11.039 | 159.886 | 1.00 | 21.68 |
| ATOM | 4821 | CD1 | TRP | 3289 | 102.692 | 11.702 | 157.857 | 1.00 | 22.61 |
| ATOM | 4822 | NE1 | TRP | 3289 | 102.026 | 10.715 | 157.157 | 1.00 | 22.39 |
| ATOM | 4823 | CZ2 | TRP | 3289 | 99.890 | 9.435 | 157.539 | 1.00 | 22.38 |
| ATOM | 4824 | CZ3 | TRP | 3289 | 98.760 | 10.100 | 159.588 | 1.00 | 20.53 |
| ATOM | 4825 | CH2 | TRP | 3289 | 98.840 | 9.311 | 158.425 | 1.00 | 21.32 |
| ATOM | 4826 | C | TRP | 3289 | 101.388 | 15.099 | 161.099 | 1.00 | 25.71 |
| ATOM | 4827 | O | TRP | 3289 | 102.340 | 15.701 | 161.562 | 1.00 | 26.33 |
| ATOM | 4828 | N | LEU | 3290 | 100.202 | 15.036 | 161.698 | 1.00 | 26.63 |
| ATOM | 4829 | CA | LEU | 3290 | 99.917 | 15.711 | 162.964 | 1.00 | 27.02 |
| ATOM | 4830 | CB | LEU | 3290 | 98.867 | 16.788 | 162.753 | 1.00 | 26.33 |
| ATOM | 4831 | CG | LEU | 3290 | 99.341 | 18.190 | 162.414 | 1.00 | 27.76 |
| ATOM | 4832 | CD1 | LEU | 3290 | 100.458 | 18.139 | 161.383 | 1.00 | 27.91 |
| ATOM | 4833 | CD2 | LEU | 3290 | 98.144 | 19.000 | 161.925 | 1.00 | 28.54 |
| ATOM | 4834 | C | LEU | 3290 | 99.392 | 14.804 | 164.050 | 1.00 | 27.20 |

TABLE 6-continued

FGF2/FGFR1/Heparin Ternary Complex

| ATOM | 4835 | O | LEU | 3290 | 98.741 | 13.814 | 163.769 | 1.00 | 27.70 |
|---|---|---|---|---|---|---|---|---|---|
| ATOM | 4836 | N | LYS | 3291 | 99.665 | 15.174 | 165.296 | 1.00 | 28.78 |
| ATOM | 4837 | CA | LYS | 3291 | 99.177 | 14.445 | 166.459 | 1.00 | 29.05 |
| ATOM | 4838 | CB | LYS | 3291 | 100.329 | 13.897 | 167.291 | 1.00 | 29.73 |
| ATOM | 4839 | CG | LYS | 3291 | 99.984 | 12.618 | 168.038 | 1.00 | 31.72 |
| ATOM | 4840 | CD | LYS | 3291 | 98.679 | 12.748 | 168.800 | 1.00 | 33.36 |
| ATOM | 4841 | CE | LYS | 3291 | 98.430 | 11.538 | 169.679 | 1.00 | 34.04 |
| ATOM | 4842 | NZ | LYS | 3291 | 99.427 | 11.440 | 170.784 | 1.00 | 35.47 |
| ATOM | 4843 | C | LYS | 3291 | 98.439 | 15.516 | 167.238 | 1.00 | 29.09 |
| ATOM | 4844 | O | LYS | 3291 | 98.938 | 16.622 | 167.388 | 1.00 | 28.60 |
| ATOM | 4845 | N | HIS | 3292 | 97.239 | 15.208 | 167.703 | 1.00 | 30.58 |
| ATOM | 4846 | CA | HIS | 3292 | 96.445 | 16.185 | 168.444 | 1.00 | 31.34 |
| ATOM | 4847 | CB | HIS | 3292 | 94.970 | 16.004 | 168.131 | 1.00 | 31.40 |
| ATOM | 4848 | CG | HIS | 3292 | 94.605 | 16.387 | 166.738 | 1.00 | 32.93 |
| ATOM | 4849 | CD2 | HIS | 3292 | 95.140 | 17.299 | 165.895 | 1.00 | 35.18 |
| ATOM | 4850 | ND1 | HIS | 3292 | 93.543 | 15.824 | 166.068 | 1.00 | 34.66 |
| ATOM | 4851 | CE1 | HIS | 3292 | 93.437 | 16.372 | 164.870 | 1.00 | 36.22 |
| ATOM | 4852 | NE2 | HIS | 3292 | 94.395 | 17.271 | 164.740 | 1.00 | 35.90 |
| ATOM | 4853 | C | HIS | 3292 | 96.659 | 16.037 | 169.929 | 1.00 | 31.79 |
| ATOM | 4854 | O | HIS | 3292 | 96.496 | 14.943 | 170.458 | 1.00 | 32.99 |
| ATOM | 4855 | N | VAL | 3308 | 98.305 | 20.855 | 168.555 | 1.00 | 33.31 |
| ATOM | 4856 | CA | VAL | 3308 | 98.883 | 19.814 | 167.709 | 1.00 | 33.62 |
| ATOM | 4857 | CB | VAL | 3308 | 98.555 | 20.032 | 166.217 | 1.00 | 35.09 |
| ATOM | 4858 | CG1 | VAL | 3308 | 97.059 | 19.930 | 165.979 | 1.00 | 36.03 |
| ATOM | 4859 | CG2 | VAL | 3308 | 99.094 | 21.385 | 165.765 | 1.00 | 35.70 |
| ATOM | 4860 | C | VAL | 3308 | 100.397 | 19.718 | 167.794 | 1.00 | 32.33 |
| ATOM | 4861 | O | VAL | 3308 | 101.075 | 20.661 | 168.186 | 1.00 | 32.08 |
| ATOM | 4862 | N | GLN | 3309 | 100.910 | 18.560 | 167.397 | 1.00 | 31.42 |
| ATOM | 4863 | CA | GLN | 3309 | 102.336 | 18.288 | 167.392 | 1.00 | 30.75 |
| ATOM | 4864 | CB | GLN | 3309 | 102.675 | 17.191 | 168.410 | 1.00 | 31.95 |
| ATOM | 4865 | CG | GLN | 3309 | 104.007 | 16.468 | 168.141 | 1.00 | 34.88 |
| ATOM | 4866 | CD | GLN | 3309 | 104.304 | 15.344 | 169.141 | 1.00 | 35.19 |
| ATOM | 4867 | OE1 | GLN | 3309 | 103.392 | 14.756 | 169.711 | 1.00 | 36.34 |
| ATOM | 4868 | NE2 | GLN | 3309 | 105.583 | 15.035 | 169.336 | 1.00 | 35.52 |
| ATOM | 4869 | C | GLN | 3309 | 102.723 | 17.832 | 165.995 | 1.00 | 29.59 |
| ATOM | 4870 | O | GLN | 3309 | 102.300 | 16.772 | 165.539 | 1.00 | 28.60 |
| ATOM | 4871 | N | ILE | 3310 | 103.513 | 18.637 | 165.300 | 1.00 | 28.64 |
| ATOM | 4872 | CA | ILE | 3310 | 103.928 | 18.245 | 163.966 | 1.00 | 28.25 |
| ATOM | 4873 | CB | ILE | 3310 | 104.687 | 19.375 | 163.290 | 1.00 | 27.05 |
| ATOM | 4874 | CG2 | ILE | 3310 | 104.924 | 19.036 | 161.827 | 1.00 | 27.29 |
| ATOM | 4875 | CG1 | ILE | 3310 | 103.867 | 20.659 | 163.402 | 1.00 | 25.95 |
| ATOM | 4876 | CD1 | ILE | 3310 | 102.474 | 20.535 | 162.842 | 1.00 | 25.28 |
| ATOM | 4877 | C | ILE | 3310 | 104.817 | 17.023 | 164.137 | 1.00 | 28.35 |
| ATOM | 4878 | O | ILE | 3310 | 105.716 | 17.029 | 164.966 | 1.00 | 30.56 |
| ATOM | 4879 | N | LEU | 3311 | 104.559 | 15.969 | 163.376 | 1.00 | 26.83 |
| ATOM | 4880 | CA | LEU | 3311 | 105.338 | 14.757 | 163.507 | 1.00 | 26.51 |
| ATOM | 4881 | CB | LEU | 3311 | 104.407 | 13.586 | 163.794 | 1.00 | 27.78 |
| ATOM | 4882 | CG | LEU | 3311 | 103.551 | 13.603 | 165.062 | 1.00 | 29.96 |
| ATOM | 4883 | CD1 | LEU | 3311 | 102.534 | 12.465 | 165.022 | 1.00 | 29.35 |
| ATOM | 4884 | CD2 | LEU | 3311 | 104.444 | 13.467 | 166.271 | 1.00 | 29.85 |
| ATOM | 4885 | C | LEU | 3311 | 106.167 | 14.432 | 162.274 | 1.00 | 26.85 |
| ATOM | 4886 | O | LEU | 3311 | 107.209 | 13.770 | 162.373 | 1.00 | 27.47 |
| ATOM | 4887 | N | LYS | 3312 | 105.710 | 14.900 | 161.118 | 1.00 | 25.90 |
| ATOM | 4888 | CA | LYS | 3312 | 106.378 | 14.616 | 159.854 | 1.00 | 25.76 |
| ATOM | 4889 | CB | LYS | 3312 | 105.872 | 13.280 | 159.324 | 1.00 | 25.36 |
| ATOM | 4890 | CG | LYS | 3312 | 106.915 | 12.282 | 158.892 | 1.00 | 25.89 |
| ATOM | 4891 | CD | LYS | 3312 | 106.235 | 10.938 | 158.654 | 1.00 | 27.58 |
| ATOM | 4892 | CE | LYS | 3312 | 107.197 | 9.869 | 158.178 | 1.00 | 28.64 |
| ATOM | 4893 | NZ | LYS | 3312 | 107.855 | 10.257 | 156.901 | 1.00 | 32.12 |
| ATOM | 4894 | C | LYS | 3312 | 106.002 | 15.698 | 158.860 | 1.00 | 27.10 |
| ATOM | 4895 | O | LYS | 3312 | 104.842 | 16.084 | 158.787 | 1.00 | 27.89 |
| ATOM | 4896 | N | THR | 3313 | 106.962 | 16.197 | 158.092 | 1.00 | 28.16 |
| ATOM | 4897 | CA | THR | 3313 | 106.626 | 17.209 | 157.111 | 1.00 | 28.36 |
| ATOM | 4898 | CB | THR | 3313 | 106.904 | 18.605 | 157.619 | 1.00 | 28.41 |
| ATOM | 4899 | OG1 | THR | 3313 | 106.321 | 18.776 | 158.922 | 1.00 | 26.38 |
| ATOM | 4900 | CG2 | THR | 3313 | 106.297 | 19.613 | 156.654 | 1.00 | 27.90 |
| ATOM | 4901 | C | THR | 3313 | 107.371 | 16.994 | 155.812 | 1.00 | 29.78 |
| ATOM | 4902 | O | THR | 3313 | 108.585 | 16.786 | 155.802 | 1.00 | 30.51 |
| ATOM | 4903 | N | ALA | 3314 | 106.631 | 17.030 | 154.709 | 1.00 | 30.89 |
| ATOM | 4904 | CA | ALA | 3314 | 107.217 | 16.813 | 153.395 | 1.00 | 31.26 |
| ATOM | 4905 | CB | ALA | 3314 | 106.135 | 16.832 | 152.330 | 1.00 | 30.42 |
| ATOM | 4906 | C | ALA | 3314 | 108.282 | 17.858 | 153.095 | 1.00 | 32.51 |
| ATOM | 4907 | O | ALA | 3314 | 108.206 | 19.003 | 153.561 | 1.00 | 33.18 |
| ATOM | 4908 | N | GLY | 3315 | 109.287 | 17.452 | 152.326 | 1.00 | 32.40 |
| ATOM | 4909 | CA | GLY | 3315 | 110.354 | 18.368 | 151.989 | 1.00 | 33.03 |
| ATOM | 4910 | C | GLY | 3315 | 111.629 | 17.655 | 151.605 | 1.00 | 33.19 |
| ATOM | 4911 | O | GLY | 3315 | 111.676 | 16.430 | 151.559 | 1.00 | 33.31 |

TABLE 6-continued

FGF2/FGFR1/Heparin Ternary Complex

| ATOM | 4912 | N | VAL | 3316 | 112.674 | 18.422 | 151.334 | 1.00 | 33.28 |
|---|---|---|---|---|---|---|---|---|---|
| ATOM | 4913 | CA | VAL | 3316 | 113.940 | 17.835 | 150.939 | 1.00 | 33.88 |
| ATOM | 4914 | CB | VAL | 3316 | 115.005 | 18.914 | 150.733 | 1.00 | 34.21 |
| ATOM | 4915 | CG1 | VAL | 3316 | 116.285 | 18.277 | 150.230 | 1.00 | 34.24 |
| ATOM | 4916 | CG2 | VAL | 3316 | 114.501 | 19.962 | 149.751 | 1.00 | 36.08 |
| ATOM | 4917 | C | VAL | 3316 | 114.468 | 16.826 | 151.954 | 1.00 | 33.92 |
| ATOM | 4918 | O | VAL | 3316 | 115.084 | 15.832 | 151.589 | 1.00 | 34.86 |
| ATOM | 4919 | N | ASN | 3317 | 114.227 | 17.083 | 153.231 | 1.00 | 34.25 |
| ATOM | 4920 | CA | ASN | 3317 | 114.692 | 16.199 | 154.301 | 1.00 | 35.21 |
| ATOM | 4921 | CB | ASN | 3317 | 114.673 | 16.942 | 155.633 | 1.00 | 35.24 |
| ATOM | 4922 | CG | ASN | 3317 | 116.009 | 17.517 | 155.997 | 1.00 | 35.15 |
| ATOM | 4923 | OD1 | ASN | 3317 | 116.098 | 18.352 | 156.890 | 1.00 | 36.57 |
| ATOM | 4924 | ND2 | ASN | 3317 | 117.063 | 17.066 | 155.325 | 1.00 | 34.76 |
| ATOM | 4925 | C | ASN | 3317 | 113.836 | 14.951 | 154.452 | 1.00 | 35.25 |
| ATOM | 4926 | O | ASN | 3317 | 114.295 | 13.913 | 154.928 | 1.00 | 34.93 |
| ATOM | 4927 | N | THR | 3318 | 112.574 | 15.085 | 154.074 | 1.00 | 35.45 |
| ATOM | 4928 | CA | THR | 3318 | 111.613 | 14.004 | 154.154 | 1.00 | 34.57 |
| ATOM | 4929 | CB | THR | 3318 | 110.697 | 14.188 | 155.359 | 1.00 | 34.63 |
| ATOM | 4930 | OG1 | THR | 3318 | 111.387 | 13.740 | 156.524 | 1.00 | 35.24 |
| ATOM | 4931 | CG2 | THR | 3318 | 109.425 | 13.398 | 155.205 | 1.00 | 35.62 |
| ATOM | 4932 | C | THR | 3318 | 110.810 | 14.030 | 152.875 | 1.00 | 34.43 |
| ATOM | 4933 | O | THR | 3318 | 109.789 | 14.717 | 152.772 | 1.00 | 35.33 |
| ATOM | 4934 | N | THR | 3319 | 111.299 | 13.280 | 151.894 | 1.00 | 33.51 |
| ATOM | 4935 | CA | THR | 3319 | 110.676 | 13.198 | 150.575 | 1.00 | 33.00 |
| ATOM | 4936 | CB | THR | 3319 | 111.553 | 12.422 | 149.605 | 1.00 | 33.68 |
| ATOM | 4937 | OG1 | THR | 3319 | 111.709 | 11.081 | 150.088 | 1.00 | 35.48 |
| ATOM | 4938 | CG2 | THR | 3319 | 112.907 | 13.074 | 149.491 | 1.00 | 34.63 |
| ATOM | 4939 | C | THR | 3319 | 109.333 | 12.501 | 150.580 | 1.00 | 31.26 |
| ATOM | 4940 | O | THR | 3319 | 109.050 | 11.693 | 151.458 | 1.00 | 29.93 |
| ATOM | 4941 | N | ASP | 3320 | 108.523 | 12.795 | 149.568 | 1.00 | 30.50 |
| ATOM | 4942 | CA | ASP | 3320 | 107.210 | 12.182 | 149.461 | 1.00 | 30.55 |
| ATOM | 4943 | CB | ASP | 3320 | 106.503 | 12.584 | 148.161 | 1.00 | 28.17 |
| ATOM | 4944 | CG | ASP | 3320 | 106.042 | 14.019 | 148.167 | 1.00 | 27.85 |
| ATOM | 4945 | OD1 | ASP | 3320 | 105.597 | 14.487 | 149.231 | 1.00 | 27.23 |
| ATOM | 4946 | OD2 | ASP | 3320 | 106.105 | 14.684 | 147.106 | 1.00 | 28.78 |
| ATOM | 4947 | C | ASP | 3320 | 107.286 | 10.658 | 149.533 | 1.00 | 31.92 |
| ATOM | 4948 | O | ASP | 3320 | 106.290 | 10.004 | 149.809 | 1.00 | 32.69 |
| ATOM | 4949 | N | LYS | 3321 | 108.461 | 10.086 | 149.292 | 1.00 | 33.95 |
| ATOM | 4950 | CA | LYS | 3321 | 108.610 | 8.629 | 149.339 | 1.00 | 36.05 |
| ATOM | 4951 | CB | LYS | 3321 | 110.082 | 8.207 | 149.235 | 1.00 | 37.48 |
| ATOM | 4952 | CG | LYS | 3321 | 110.875 | 8.827 | 148.104 | 1.00 | 40.58 |
| ATOM | 4953 | CD | LYS | 3321 | 112.334 | 8.364 | 148.143 | 1.00 | 41.71 |
| ATOM | 4954 | CE | LYS | 3321 | 113.216 | 9.147 | 147.143 | 1.00 | 43.81 |
| ATOM | 4955 | NZ | LYS | 3321 | 113.474 | 10.569 | 147.540 | 1.00 | 42.72 |
| ATOM | 4956 | C | LYS | 3321 | 108.081 | 8.089 | 150.662 | 1.00 | 36.80 |
| ATOM | 4957 | O | LYS | 3321 | 107.245 | 7.192 | 150.697 | 1.00 | 37.06 |
| ATOM | 4958 | N | GLU | 3322 | 108.587 | 8.655 | 151.749 | 1.00 | 37.48 |
| ATOM | 4959 | CA | GLU | 3322 | 108.230 | 8.231 | 153.090 | 1.00 | 37.30 |
| ATOM | 4960 | CB | GLU | 3322 | 109.474 | 8.348 | 153.979 | 1.00 | 37.73 |
| ATOM | 4961 | CG | GLU | 3322 | 110.240 | 9.669 | 153.828 | 1.00 | 38.94 |
| ATOM | 4962 | CD | GLU | 3322 | 111.531 | 9.733 | 154.670 | 1.00 | 40.03 |
| ATOM | 4963 | OE1 | GLU | 3322 | 111.461 | 9.579 | 155.907 | 1.00 | 40.38 |
| ATOM | 4964 | OE2 | GLU | 3322 | 112.619 | 9.949 | 154.096 | 1.00 | 38.38 |
| ATOM | 4965 | C | GLU | 3322 | 107.068 | 8.973 | 153.736 | 1.00 | 37.08 |
| ATOM | 4966 | O | GLU | 3322 | 106.689 | 8.669 | 154.866 | 1.00 | 37.38 |
| ATOM | 4967 | N | MET | 3323 | 106.482 | 9.927 | 153.028 | 1.00 | 36.89 |
| ATOM | 4968 | CA | MET | 3323 | 105.398 | 10.701 | 153.617 | 1.00 | 36.85 |
| ATOM | 4969 | CB | MET | 3323 | 105.262 | 12.050 | 152.916 | 1.00 | 36.10 |
| ATOM | 4970 | CG | MET | 3323 | 106.301 | 13.046 | 153.360 | 1.00 | 35.17 |
| ATOM | 4971 | SD | MET | 3323 | 106.375 | 13.079 | 155.146 | 1.00 | 34.67 |
| ATOM | 4972 | CE | MET | 3323 | 105.124 | 14.366 | 155.511 | 1.00 | 36.26 |
| ATOM | 4973 | C | MET | 3323 | 104.040 | 10.043 | 153.681 | 1.00 | 37.22 |
| ATOM | 4974 | O | MET | 3323 | 103.179 | 10.478 | 154.436 | 1.00 | 36.96 |
| ATOM | 4975 | N | GLU | 3324 | 103.832 | 8.995 | 152.904 | 1.00 | 38.41 |
| ATOM | 4976 | CA | GLU | 3324 | 102.534 | 8.345 | 152.925 | 1.00 | 39.48 |
| ATOM | 4977 | CB | GLU | 3324 | 102.279 | 7.610 | 151.601 | 1.00 | 41.21 |
| ATOM | 4978 | CG | GLU | 3324 | 101.872 | 8.557 | 150.470 | 1.00 | 44.98 |
| ATOM | 4979 | CD | GLU | 3324 | 101.655 | 7.860 | 149.133 | 1.00 | 47.50 |
| ATOM | 4980 | OE1 | GLU | 3324 | 102.561 | 7.112 | 148.693 | 1.00 | 49.13 |
| ATOM | 4981 | OE2 | GLU | 3324 | 100.583 | 8.073 | 148.517 | 1.00 | 47.27 |
| ATOM | 4982 | C | GLU | 3324 | 102.348 | 7.400 | 154.102 | 1.00 | 38.42 |
| ATOM | 4983 | O | GLU | 3324 | 101.277 | 6.819 | 154.264 | 1.00 | 38.84 |
| ATOM | 4984 | N | VAL | 3325 | 103.373 | 7.254 | 154.934 | 1.00 | 36.79 |
| ATOM | 4985 | CA | VAL | 3325 | 103.251 | 6.369 | 156.082 | 1.00 | 36.97 |
| ATOM | 4986 | CB | VAL | 3325 | 103.781 | 4.964 | 155.751 | 1.00 | 37.10 |
| ATOM | 4987 | CG1 | VAL | 3325 | 105.287 | 5.005 | 155.589 | 1.00 | 38.60 |
| ATOM | 4988 | CG2 | VAL | 3325 | 103.362 | 3.978 | 156.839 | 1.00 | 37.47 |

TABLE 6-continued

FGF2/FGFR1/Heparin Ternary Complex

| ATOM | 4989 | C | VAL | 3325 | 103.949 | 6.887 | 157.343 | 1.00 | 36.67 |
|------|------|------|-----|------|---------|--------|---------|------|-------|
| ATOM | 4990 | O | VAL | 3325 | 105.134 | 7.228 | 157.326 | 1.00 | 36.97 |
| ATOM | 4991 | N | LEU | 3326 | 103.187 | 6.947 | 158.434 | 1.00 | 36.14 |
| ATOM | 4992 | CA | LEU | 3326 | 103.676 | 7.414 | 159.726 | 1.00 | 35.61 |
| ATOM | 4993 | CB | LEU | 3326 | 102.621 | 8.285 | 160.401 | 1.00 | 34.11 |
| ATOM | 4994 | CG | LEU | 3326 | 102.948 | 8.760 | 161.820 | 1.00 | 32.88 |
| ATOM | 4995 | CD1 | LEU | 3326 | 103.965 | 9.873 | 161.749 | 1.00 | 32.34 |
| ATOM | 4996 | CD2 | LEU | 3326 | 101.691 | 9.260 | 162.514 | 1.00 | 32.32 |
| ATOM | 4997 | C | LEU | 3326 | 103.973 | 6.229 | 160.626 | 1.00 | 36.01 |
| ATOM | 4998 | O | LEU | 3326 | 103.082 | 5.450 | 160.938 | 1.00 | 35.57 |
| ATOM | 4999 | N | HIS | 3327 | 105.219 | 6.100 | 161.055 | 1.00 | 37.25 |
| ATOM | 5000 | CA | HIS | 3327 | 105.589 | 4.988 | 161.917 | 1.00 | 38.62 |
| ATOM | 5001 | CB | HIS | 3327 | 106.946 | 4.418 | 161.499 | 1.00 | 38.38 |
| ATOM | 5002 | CG | HIS | 3327 | 106.946 | 3.801 | 160.137 | 1.00 | 38.81 |
| ATOM | 5003 | CD2 | HIS | 3327 | 107.578 | 4.160 | 158.995 | 1.00 | 39.55 |
| ATOM | 5004 | ND1 | HIS | 3327 | 106.192 | 2.691 | 159.827 | 1.00 | 39.56 |
| ATOM | 5005 | CE1 | HIS | 3327 | 106.358 | 2.392 | 158.550 | 1.00 | 40.57 |
| ATOM | 5006 | NE2 | HIS | 3327 | 107.193 | 3.269 | 158.022 | 1.00 | 40.54 |
| ATOM | 5007 | C | HIS | 3327 | 105.637 | 5.393 | 163.380 | 1.00 | 39.22 |
| ATOM | 5008 | O | HIS | 3327 | 106.352 | 6.323 | 163.759 | 1.00 | 40.18 |
| ATOM | 5009 | N | LEU | 3328 | 104.860 | 4.700 | 164.200 | 1.00 | 39.00 |
| ATOM | 5010 | CA | LEU | 3328 | 104.844 | 4.969 | 165.628 | 1.00 | 39.52 |
| ATOM | 5011 | CB | LEU | 3328 | 103.411 | 5.206 | 166.109 | 1.00 | 37.32 |
| ATOM | 5012 | CG | LEU | 3328 | 102.827 | 6.503 | 165.553 | 1.00 | 34.16 |
| ATOM | 5013 | CD1 | LEU | 3328 | 101.395 | 6.658 | 165.989 | 1.00 | 33.49 |
| ATOM | 5014 | CD2 | LEU | 3328 | 103.662 | 7.666 | 166.027 | 1.00 | 31.86 |
| ATOM | 5015 | C | LEU | 3328 | 105.455 | 3.743 | 166.289 | 1.00 | 40.92 |
| ATOM | 5016 | O | LEU | 3328 | 104.804 | 2.701 | 166.411 | 1.00 | 42.42 |
| ATOM | 5017 | N | ARG | 3329 | 106.716 | 3.872 | 166.691 | 1.00 | 41.43 |
| ATOM | 5018 | CA | ARG | 3329 | 107.458 | 2.779 | 167.309 | 1.00 | 42.24 |
| ATOM | 5019 | CB | ARG | 3329 | 108.961 | 2.978 | 167.055 | 1.00 | 41.52 |
| ATOM | 5020 | C | ARG | 3329 | 107.198 | 2.632 | 168.808 | 1.00 | 43.06 |
| ATOM | 5021 | O | ARG | 3329 | 107.152 | 3.619 | 169.548 | 1.00 | 42.13 |
| ATOM | 5022 | N | ASN | 3330 | 107.041 | 1.381 | 169.237 | 1.00 | 44.91 |
| ATOM | 5023 | CA | ASN | 3330 | 106.779 | 1.021 | 170.631 | 1.00 | 46.49 |
| ATOM | 5024 | CB | ASN | 3330 | 108.098 | 0.789 | 171.368 | 1.00 | 49.25 |
| ATOM | 5025 | CG | ASN | 3330 | 107.918 | −0.062 | 172.612 | 1.00 | 52.46 |
| ATOM | 5026 | OD1 | ASN | 3330 | 107.584 | 0.447 | 173.687 | 1.00 | 54.72 |
| ATOM | 5027 | ND2 | ASN | 3330 | 108.115 | −1.371 | 172.466 | 1.00 | 52.46 |
| ATOM | 5028 | C | ASN | 3330 | 105.925 | 2.052 | 171.360 | 1.00 | 45.35 |
| ATOM | 5029 | O | ASN | 3330 | 106.423 | 2.855 | 172.149 | 1.00 | 44.07 |
| ATOM | 5030 | N | VAL | 3331 | 104.623 | 1.997 | 171.092 | 1.00 | 45.27 |
| ATOM | 5031 | CA | VAL | 3331 | 103.669 | 2.940 | 171.665 | 1.00 | 45.66 |
| ATOM | 5032 | CB | VAL | 3331 | 102.279 | 2.808 | 171.012 | 1.00 | 45.12 |
| ATOM | 5033 | CG1 | VAL | 3331 | 102.402 | 3.009 | 169.527 | 1.00 | 45.99 |
| ATOM | 5034 | CG2 | VAL | 3331 | 101.676 | 1.456 | 171.311 | 1.00 | 45.51 |
| ATOM | 5035 | C | VAL | 3331 | 103.493 | 2.883 | 173.168 | 1.00 | 45.52 |
| ATOM | 5036 | O | VAL | 3331 | 103.907 | 1.936 | 173.822 | 1.00 | 45.96 |
| ATOM | 5037 | N | SER | 3332 | 102.865 | 3.925 | 173.696 | 1.00 | 46.11 |
| ATOM | 5038 | CA | SER | 3332 | 102.604 | 4.070 | 175.124 | 1.00 | 46.31 |
| ATOM | 5039 | CB | SER | 3332 | 103.630 | 4.995 | 175.762 | 1.00 | 45.69 |
| ATOM | 5040 | OG | SER | 3332 | 103.286 | 6.351 | 175.497 | 1.00 | 42.92 |
| ATOM | 5041 | C | SER | 3332 | 101.246 | 4.739 | 175.266 | 1.00 | 47.42 |
| ATOM | 5042 | O | SER | 3332 | 100.731 | 5.312 | 174.308 | 1.00 | 48.20 |
| ATOM | 5043 | N | PHE | 3333 | 100.677 | 4.698 | 176.465 | 1.00 | 48.10 |
| ATOM | 5044 | CA | PHE | 3333 | 99.379 | 5.326 | 176.700 | 1.00 | 49.03 |
| ATOM | 5045 | CB | PHE | 3333 | 98.985 | 5.212 | 178.184 | 1.00 | 50.19 |
| ATOM | 5046 | CG | PHE | 3333 | 98.614 | 3.811 | 178.610 | 1.00 | 52.17 |
| ATOM | 5047 | CD1 | PHE | 3333 | 98.798 | 3.397 | 179.918 | 1.00 | 51.95 |
| ATOM | 5048 | CD2 | PHE | 3333 | 98.076 | 2.906 | 177.699 | 1.00 | 54.66 |
| ATOM | 5049 | CE1 | PHE | 3333 | 98.454 | 2.099 | 180.317 | 1.00 | 52.46 |
| ATOM | 5050 | CE2 | PHE | 3333 | 97.729 | 1.607 | 178.088 | 1.00 | 54.62 |
| ATOM | 5051 | CZ | PHE | 3333 | 97.920 | 1.207 | 179.396 | 1.00 | 53.30 |
| ATOM | 5052 | C | PHE | 3333 | 99.395 | 6.793 | 176.263 | 1.00 | 48.80 |
| ATOM | 5053 | O | PHE | 3333 | 98.353 | 7.371 | 175.942 | 1.00 | 48.37 |
| ATOM | 5054 | N | GLU | 3334 | 100.588 | 7.381 | 176.242 | 1.00 | 48.33 |
| ATOM | 5055 | CA | GLU | 3334 | 100.756 | 8.770 | 175.847 | 1.00 | 47.86 |
| ATOM | 5056 | CB | GLU | 3334 | 102.200 | 9.195 | 176.125 | 1.00 | 50.65 |
| ATOM | 5057 | CG | GLU | 3334 | 102.766 | 8.660 | 177.449 | 1.00 | 54.59 |
| ATOM | 5058 | CD | GLU | 3334 | 104.295 | 8.797 | 177.548 | 1.00 | 57.36 |
| ATOM | 5059 | OE1 | GLU | 3334 | 104.886 | 8.330 | 178.558 | 1.00 | 57.26 |
| ATOM | 5060 | OE2 | GLU | 3334 | 104.906 | 9.372 | 176.611 | 1.00 | 58.15 |
| ATOM | 5061 | C | GLU | 3334 | 100.441 | 8.910 | 174.355 | 1.00 | 45.94 |
| ATOM | 5062 | O | GLU | 3334 | 99.681 | 9.790 | 173.946 | 1.00 | 44.87 |
| ATOM | 5063 | N | ASP | 3335 | 101.024 | 8.025 | 173.550 | 1.00 | 43.47 |
| ATOM | 5064 | CA | ASP | 3335 | 100.826 | 8.047 | 172.104 | 1.00 | 41.39 |
| ATOM | 5065 | CB | ASP | 3335 | 101.644 | 6.929 | 171.432 | 1.00 | 41.09 |

TABLE 6-continued

FGF2/FGFR1/Heparin Ternary Complex

| ATOM | 5066 | CG | ASP | 3335 | 103.109 | 6.931 | 171.845 | 1.00 | 39.73 |
|---|---|---|---|---|---|---|---|---|---|
| ATOM | 5067 | OD1 | ASP | 3335 | 103.734 | 8.012 | 171.866 | 1.00 | 39.97 |
| ATOM | 5068 | OD2 | ASP | 3335 | 103.641 | 5.842 | 172.134 | 1.00 | 38.03 |
| ATOM | 5069 | C | ASP | 3335 | 99.355 | 7.893 | 171.723 | 1.00 | 39.49 |
| ATOM | 5070 | O | ASP | 3335 | 98.972 | 8.129 | 170.583 | 1.00 | 38.45 |
| ATOM | 5071 | N | ALA | 3336 | 98.533 | 7.478 | 172.678 | 1.00 | 38.06 |
| ATOM | 5072 | CA | ALA | 3336 | 97.111 | 7.307 | 172.414 | 1.00 | 36.62 |
| ATOM | 5073 | CB | ALA | 3336 | 96.393 | 6.846 | 173.665 | 1.00 | 37.25 |
| ATOM | 5074 | C | ALA | 3336 | 96.545 | 8.638 | 171.957 | 1.00 | 35.50 |
| ATOM | 5075 | O | ALA | 3336 | 96.944 | 9.695 | 172.448 | 1.00 | 35.26 |
| ATOM | 5076 | N | GLY | 3337 | 95.616 | 8.594 | 171.012 | 1.00 | 34.12 |
| ATOM | 5077 | CA | GLY | 3337 | 95.039 | 9.831 | 170.535 | 1.00 | 31.90 |
| ATOM | 5078 | C | GLY | 3337 | 94.719 | 9.874 | 169.058 | 1.00 | 31.35 |
| ATOM | 5079 | O | GLY | 3337 | 94.781 | 8.870 | 168.342 | 1.00 | 30.70 |
| ATOM | 5080 | N | GLU | 3338 | 94.384 | 11.076 | 168.606 | 1.00 | 30.67 |
| ATOM | 5081 | CA | GLU | 3338 | 94.009 | 11.311 | 167.224 | 1.00 | 29.11 |
| ATOM | 5082 | CB | GLU | 3338 | 92.804 | 12.243 | 167.203 | 1.00 | 28.40 |
| ATOM | 5083 | CG | GLU | 3338 | 92.428 | 12.753 | 165.846 | 1.00 | 28.42 |
| ATOM | 5084 | CD | GLU | 3338 | 91.158 | 13.562 | 165.895 | 1.00 | 28.49 |
| ATOM | 5085 | OE1 | GLU | 3338 | 90.975 | 14.325 | 166.874 | 1.00 | 26.39 |
| ATOM | 5086 | OE2 | GLU | 3338 | 90.349 | 13.437 | 164.953 | 1.00 | 28.88 |
| ATOM | 5087 | C | GLU | 3338 | 95.130 | 11.881 | 166.371 | 1.00 | 28.24 |
| ATOM | 5088 | O | GLU | 3338 | 95.684 | 12.923 | 166.680 | 1.00 | 27.97 |
| ATOM | 5089 | N | TYR | 3339 | 95.453 | 11.179 | 165.293 | 1.00 | 28.00 |
| ATOM | 5090 | CA | TYR | 3339 | 96.491 | 11.604 | 164.375 | 1.00 | 28.21 |
| ATOM | 5091 | CB | TYR | 3339 | 97.395 | 10.427 | 164.030 | 1.00 | 29.45 |
| ATOM | 5092 | CG | TYR | 3339 | 98.151 | 9.935 | 165.223 | 1.00 | 32.54 |
| ATOM | 5093 | CD1 | TYR | 3339 | 97.493 | 9.304 | 166.272 | 1.00 | 34.64 |
| ATOM | 5094 | CE1 | TYR | 3339 | 98.176 | 8.901 | 167.409 | 1.00 | 36.15 |
| ATOM | 5095 | CD2 | TYR | 3339 | 99.520 | 10.149 | 165.340 | 1.00 | 33.64 |
| ATOM | 5096 | CE2 | TYR | 3339 | 100.215 | 9.751 | 166.475 | 1.00 | 34.99 |
| ATOM | 5097 | CZ | TYR | 3339 | 99.536 | 9.129 | 167.504 | 1.00 | 36.68 |
| ATOM | 5098 | OH | TYR | 3339 | 100.217 | 8.743 | 168.634 | 1.00 | 39.85 |
| ATOM | 5099 | C | TYR | 3339 | 95.824 | 12.138 | 163.126 | 1.00 | 27.68 |
| ATOM | 5100 | O | TYR | 3339 | 94.730 | 11.716 | 162.776 | 1.00 | 28.83 |
| ATOM | 5101 | N | THR | 3340 | 96.479 | 13.066 | 162.446 | 1.00 | 26.46 |
| ATOM | 5102 | CA | THR | 3340 | 95.895 | 13.640 | 161.258 | 1.00 | 25.69 |
| ATOM | 5103 | CB | THR | 3340 | 95.373 | 15.047 | 161.511 | 1.00 | 25.05 |
| ATOM | 5104 | OG1 | THR | 3340 | 94.384 | 15.008 | 162.537 | 1.00 | 23.21 |
| ATOM | 5105 | CG2 | THR | 3340 | 94.771 | 15.615 | 160.256 | 1.00 | 24.64 |
| ATOM | 5106 | C | THR | 3340 | 96.878 | 13.740 | 160.129 | 1.00 | 27.33 |
| ATOM | 5107 | O | THR | 3340 | 98.035 | 14.118 | 160.327 | 1.00 | 27.05 |
| ATOM | 5108 | N | CYS | 3341 | 96.402 | 13.391 | 158.938 | 1.00 | 28.01 |
| ATOM | 5109 | CA | CYS | 3341 | 97.213 | 13.495 | 157.747 | 1.00 | 29.00 |
| ATOM | 5110 | C | CYS | 3341 | 96.683 | 14.734 | 157.063 | 1.00 | 29.47 |
| ATOM | 5111 | O | CYS | 3341 | 95.522 | 14.788 | 156.668 | 1.00 | 29.93 |
| ATOM | 5112 | CB | CYS | 3341 | 97.029 | 12.310 | 156.825 | 1.00 | 29.94 |
| ATOM | 5113 | SG | CYS | 3341 | 97.954 | 12.509 | 155.263 | 1.00 | 32.69 |
| ATOM | 5114 | N | LEU | 3342 | 97.540 | 15.736 | 156.949 | 1.00 | 29.61 |
| ATOM | 5115 | CA | LEU | 3342 | 97.171 | 16.987 | 156.334 | 1.00 | 29.36 |
| ATOM | 5116 | CB | LEU | 3342 | 97.447 | 18.122 | 157.313 | 1.00 | 30.40 |
| ATOM | 5117 | CG | LEU | 3342 | 97.185 | 19.556 | 156.860 | 1.00 | 31.71 |
| ATOM | 5118 | CD1 | LEU | 3342 | 95.734 | 19.717 | 156.409 | 1.00 | 31.75 |
| ATOM | 5119 | CD2 | LEU | 3342 | 97.506 | 20.494 | 158.013 | 1.00 | 31.14 |
| ATOM | 5120 | C | LEU | 3342 | 97.995 | 17.155 | 155.069 | 1.00 | 29.77 |
| ATOM | 5121 | O | LEU | 3342 | 99.220 | 17.015 | 155.089 | 1.00 | 31.00 |
| ATOM | 5122 | N | ALA | 3343 | 97.318 | 17.438 | 153.962 | 1.00 | 28.45 |
| ATOM | 5123 | CA | ALA | 3343 | 97.994 | 17.631 | 152.695 | 1.00 | 26.45 |
| ATOM | 5124 | CB | ALA | 3343 | 97.905 | 16.384 | 151.861 | 1.00 | 26.67 |
| ATOM | 5125 | C | ALA | 3343 | 97.320 | 18.778 | 151.989 | 1.00 | 25.63 |
| ATOM | 5126 | O | ALA | 3343 | 96.096 | 18.852 | 151.932 | 1.00 | 24.67 |
| ATOM | 5127 | N | GLY | 3344 | 98.123 | 19.685 | 151.457 | 1.00 | 25.58 |
| ATOM | 5128 | CA | GLY | 3344 | 97.550 | 20.819 | 150.770 | 1.00 | 25.13 |
| ATOM | 5129 | C | GLY | 3344 | 98.438 | 21.340 | 149.673 | 1.00 | 24.86 |
| ATOM | 5130 | O | GLY | 3344 | 99.656 | 21.156 | 149.702 | 1.00 | 24.14 |
| ATOM | 5131 | N | ASN | 3345 | 97.813 | 21.973 | 148.689 | 1.00 | 24.80 |
| ATOM | 5132 | CA | ASN | 3345 | 98.540 | 22.558 | 147.581 | 1.00 | 25.78 |
| ATOM | 5133 | CB | ASN | 3345 | 98.186 | 21.853 | 146.288 | 1.00 | 25.40 |
| ATOM | 5134 | CG | ASN | 3345 | 96.724 | 21.900 | 146.007 | 1.00 | 25.53 |
| ATOM | 5135 | OD1 | ASN | 3345 | 95.961 | 22.501 | 146.764 | 1.00 | 24.29 |
| ATOM | 5136 | ND2 | ASN | 3345 | 96.311 | 21.273 | 144.915 | 1.00 | 25.08 |
| ATOM | 5137 | C | ASN | 3345 | 98.123 | 24.018 | 147.516 | 1.00 | 26.26 |
| ATOM | 5138 | O | ASN | 3345 | 97.480 | 24.526 | 148.431 | 1.00 | 25.61 |
| ATOM | 5139 | N | SER | 3346 | 98.468 | 24.700 | 146.438 | 1.00 | 27.10 |
| ATOM | 5140 | CA | SER | 3346 | 98.112 | 26.104 | 146.355 | 1.00 | 28.73 |
| ATOM | 5141 | CB | SER | 3346 | 98.920 | 26.789 | 145.262 | 1.00 | 29.91 |
| ATOM | 5142 | OG | SER | 3346 | 98.798 | 26.073 | 144.047 | 1.00 | 34.21 |

TABLE 6-continued

FGF2/FGFR1/Heparin Ternary Complex

| ATOM | 5143 | C | SER | 3346 | 96.634 | 26.374 | 146.144 | 1.00 | 28.92 |
|---|---|---|---|---|---|---|---|---|---|
| ATOM | 5144 | O | SER | 3346 | 96.221 | 27.524 | 146.108 | 1.00 | 30.67 |
| ATOM | 5145 | N | ILE | 3347 | 95.820 | 25.338 | 146.008 | 1.00 | 28.26 |
| ATOM | 5146 | CA | ILE | 3347 | 94.402 | 25.582 | 145.805 | 1.00 | 27.39 |
| ATOM | 5147 | CB | ILE | 3347 | 93.842 | 24.701 | 144.673 | 1.00 | 25.86 |
| ATOM | 5148 | CG2 | ILE | 3347 | 92.337 | 24.856 | 144.580 | 1.00 | 24.00 |
| ATOM | 5149 | CG1 | ILE | 3347 | 94.491 | 25.100 | 143.349 | 1.00 | 25.68 |
| ATOM | 5150 | CD1 | ILE | 3347 | 93.974 | 24.348 | 142.146 | 1.00 | 24.70 |
| ATOM | 5151 | C | ILE | 3347 | 93.583 | 25.375 | 147.073 | 1.00 | 29.34 |
| ATOM | 5152 | O | ILE | 3347 | 92.573 | 26.045 | 147.284 | 1.00 | 29.91 |
| ATOM | 5153 | N | GLY | 3348 | 94.012 | 24.460 | 147.932 | 1.00 | 30.15 |
| ATOM | 5154 | CA | GLY | 3348 | 93.256 | 24.221 | 149.144 | 1.00 | 31.26 |
| ATOM | 5155 | C | GLY | 3348 | 93.947 | 23.250 | 150.065 | 1.00 | 31.82 |
| ATOM | 5156 | O | GLY | 3348 | 95.044 | 22.780 | 149.769 | 1.00 | 32.85 |
| ATOM | 5157 | N | LEU | 3349 | 93.294 | 22.936 | 151.176 | 1.00 | 31.34 |
| ATOM | 5158 | CA | LEU | 3349 | 93.857 | 22.030 | 152.157 | 1.00 | 30.48 |
| ATOM | 5159 | CB | LEU | 3349 | 94.101 | 22.814 | 153.439 | 1.00 | 32.95 |
| ATOM | 5160 | CG | LEU | 3349 | 95.251 | 22.419 | 154.356 | 1.00 | 35.10 |
| ATOM | 5161 | CD1 | LEU | 3349 | 96.569 | 22.425 | 153.588 | 1.00 | 35.73 |
| ATOM | 5162 | CD2 | LEU | 3349 | 95.297 | 23.412 | 155.516 | 1.00 | 35.50 |
| ATOM | 5163 | C | LEU | 3349 | 92.901 | 20.866 | 152.410 | 1.00 | 29.83 |
| ATOM | 5164 | O | LEU | 3349 | 91.682 | 21.048 | 152.406 | 1.00 | 30.17 |
| ATOM | 5165 | N | SER | 3350 | 93.462 | 19.675 | 152.609 | 1.00 | 27.99 |
| ATOM | 5166 | CA | SER | 3350 | 92.688 | 18.467 | 152.878 | 1.00 | 26.00 |
| ATOM | 5167 | CB | SER | 3350 | 92.587 | 17.596 | 151.638 | 1.00 | 25.80 |
| ATOM | 5168 | OG | SER | 3350 | 91.556 | 18.049 | 150.790 | 1.00 | 28.58 |
| ATOM | 5169 | C | SER | 3350 | 93.366 | 17.676 | 153.969 | 1.00 | 25.61 |
| ATOM | 5170 | O | SER | 3350 | 94.587 | 17.670 | 154.074 | 1.00 | 25.80 |
| ATOM | 5171 | N | HIS | 3351 | 92.571 | 16.993 | 154.777 | 1.00 | 24.88 |
| ATOM | 5172 | CA | HIS | 3351 | 93.124 | 16.212 | 155.859 | 1.00 | 24.27 |
| ATOM | 5173 | CB | HIS | 3351 | 93.435 | 17.121 | 157.047 | 1.00 | 25.69 |
| ATOM | 5174 | CG | HIS | 3351 | 92.221 | 17.760 | 157.656 | 1.00 | 25.82 |
| ATOM | 5175 | CD2 | HIS | 3351 | 91.564 | 17.505 | 158.812 | 1.00 | 26.04 |
| ATOM | 5176 | ND1 | HIS | 3351 | 91.534 | 18.785 | 157.045 | 1.00 | 25.47 |
| ATOM | 5177 | CE1 | HIS | 3351 | 90.507 | 19.135 | 157.799 | 1.00 | 24.76 |
| ATOM | 5178 | NE2 | HIS | 3351 | 90.502 | 18.375 | 158.876 | 1.00 | 24.62 |
| ATOM | 5179 | C | HIS | 3351 | 92.164 | 15.132 | 156.309 | 1.00 | 24.04 |
| ATOM | 5180 | O | HIS | 3351 | 90.954 | 15.313 | 156.260 | 1.00 | 23.23 |
| ATOM | 5181 | N | HIS | 3352 | 92.727 | 14.013 | 156.753 | 1.00 | 24.01 |
| ATOM | 5182 | CA | HIS | 3352 | 91.959 | 12.888 | 157.263 | 1.00 | 24.04 |
| ATOM | 5183 | CB | HIS | 3352 | 92.094 | 11.665 | 156.356 | 1.00 | 23.34 |
| ATOM | 5184 | CG | HIS | 3352 | 91.255 | 11.731 | 155.116 | 1.00 | 22.87 |
| ATOM | 5185 | CD2 | HIS | 3352 | 90.379 | 12.666 | 154.680 | 1.00 | 21.30 |
| ATOM | 5186 | ND1 | HIS | 3352 | 91.272 | 10.743 | 154.153 | 1.00 | 22.70 |
| ATOM | 5187 | CE1 | HIS | 3352 | 90.442 | 11.068 | 153.180 | 1.00 | 22.46 |
| ATOM | 5188 | NE2 | HIS | 3352 | 89.889 | 12.230 | 153.475 | 1.00 | 21.35 |
| ATOM | 5189 | C | HIS | 3352 | 92.551 | 12.567 | 158.612 | 1.00 | 24.61 |
| ATOM | 5190 | O | HIS | 3352 | 93.764 | 12.509 | 158.754 | 1.00 | 25.71 |
| ATOM | 5191 | N | SER | 3353 | 91.699 | 12.363 | 159.603 | 1.00 | 24.94 |
| ATOM | 5192 | CA | SER | 3353 | 92.174 | 12.052 | 160.933 | 1.00 | 25.88 |
| ATOM | 5193 | CB | SER | 3353 | 91.383 | 12.863 | 161.940 | 1.00 | 26.18 |
| ATOM | 5194 | OG | SER | 3353 | 91.482 | 14.231 | 161.586 | 1.00 | 26.96 |
| ATOM | 5195 | C | SER | 3353 | 92.005 | 10.572 | 161.185 | 1.00 | 26.54 |
| ATOM | 5196 | O | SER | 3353 | 91.513 | 9.857 | 160.313 | 1.00 | 29.28 |
| ATOM | 5197 | N | ALA | 3354 | 92.413 | 10.110 | 162.365 | 1.00 | 25.50 |
| ATOM | 5198 | CA | ALA | 3354 | 92.304 | 8.703 | 162.722 | 1.00 | 25.00 |
| ATOM | 5199 | CB | ALA | 3354 | 93.287 | 7.873 | 161.912 | 1.00 | 24.32 |
| ATOM | 5200 | C | ALA | 3354 | 92.628 | 8.592 | 164.184 | 1.00 | 25.54 |
| ATOM | 5201 | O | ALA | 3354 | 93.415 | 9.376 | 164.695 | 1.00 | 27.31 |
| ATOM | 5202 | N | TRP | 3355 | 92.044 | 7.616 | 164.863 | 1.00 | 25.44 |
| ATOM | 5203 | CA | TRP | 3355 | 92.302 | 7.469 | 166.281 | 1.00 | 26.04 |
| ATOM | 5204 | CB | TRP | 3355 | 90.979 | 7.384 | 167.031 | 1.00 | 25.50 |
| ATOM | 5205 | CG | TRP | 3355 | 90.743 | 8.569 | 167.909 | 1.00 | 26.64 |
| ATOM | 5206 | CD2 | TRP | 3355 | 89.937 | 9.706 | 167.605 | 1.00 | 26.69 |
| ATOM | 5207 | CE2 | TRP | 3355 | 90.021 | 10.590 | 168.717 | 1.00 | 27.16 |
| ATOM | 5208 | CE3 | TRP | 3355 | 89.151 | 10.066 | 166.507 | 1.00 | 27.07 |
| ATOM | 5209 | CD1 | TRP | 3355 | 91.273 | 8.797 | 169.151 | 1.00 | 27.17 |
| ATOM | 5210 | NE1 | TRP | 3355 | 90.843 | 10.010 | 169.643 | 1.00 | 27.30 |
| ATOM | 5211 | CZ2 | TRP | 3355 | 89.347 | 11.807 | 168.761 | 1.00 | 27.41 |
| ATOM | 5212 | CZ3 | TRP | 3355 | 88.475 | 11.281 | 166.546 | 1.00 | 29.89 |
| ATOM | 5213 | CH2 | TRP | 3355 | 88.578 | 12.141 | 167.675 | 1.00 | 30.13 |
| ATOM | 5214 | C | TRP | 3355 | 93.175 | 6.288 | 166.648 | 1.00 | 26.74 |
| ATOM | 5215 | O | TRP | 3355 | 93.033 | 5.203 | 166.097 | 1.00 | 27.96 |
| ATOM | 5216 | N | LEU | 3356 | 94.095 | 6.507 | 167.579 | 1.00 | 26.34 |
| ATOM | 5217 | CA | LEU | 3356 | 94.955 | 5.433 | 168.038 | 1.00 | 25.59 |
| ATOM | 5218 | CB | LEU | 3356 | 96.416 | 5.883 | 168.041 | 1.00 | 25.10 |
| ATOM | 5219 | CG | LEU | 3356 | 97.565 | 4.878 | 168.208 | 1.00 | 23.47 |

TABLE 6-continued

FGF2/FGFR1/Heparin Ternary Complex

| ATOM | 5220 | CD1 | LEU | 3356 | 98.387 | 5.260 | 169.408 | 1.00 | 23.10 |
|---|---|---|---|---|---|---|---|---|---|
| ATOM | 5221 | CD2 | LEU | 3356 | 97.040 | 3.474 | 168.342 | 1.00 | 23.28 |
| ATOM | 5222 | C | LEU | 3356 | 94.506 | 5.083 | 169.453 | 1.00 | 25.98 |
| ATOM | 5223 | O | LEU | 3356 | 94.533 | 5.925 | 170.347 | 1.00 | 25.12 |
| ATOM | 5224 | N | THR | 3357 | 94.069 | 3.841 | 169.636 | 1.00 | 27.25 |
| ATOM | 5225 | CA | THR | 3357 | 93.613 | 3.362 | 170.931 | 1.00 | 28.50 |
| ATOM | 5226 | CB | THR | 3357 | 92.274 | 2.665 | 170.800 | 1.00 | 27.20 |
| ATOM | 5227 | OG1 | THR | 3357 | 91.388 | 3.484 | 170.028 | 1.00 | 27.39 |
| ATOM | 5228 | CG2 | THR | 3357 | 91.686 | 2.413 | 172.166 | 1.00 | 25.04 |
| ATOM | 5229 | C | THR | 3357 | 94.636 | 2.369 | 171.464 | 1.00 | 30.57 |
| ATOM | 5230 | O | THR | 3357 | 94.927 | 1.367 | 170.812 | 1.00 | 31.40 |
| ATOM | 5231 | N | VAL | 3358 | 95.174 | 2.648 | 172.646 | 1.00 | 32.08 |
| ATOM | 5232 | CA | VAL | 3358 | 96.180 | 1.787 | 173.250 | 1.00 | 34.35 |
| ATOM | 5233 | CB | VAL | 3358 | 97.431 | 2.612 | 173.561 | 1.00 | 35.58 |
| ATOM | 5234 | CG1 | VAL | 3358 | 98.575 | 1.695 | 173.966 | 1.00 | 37.54 |
| ATOM | 5235 | CG2 | VAL | 3358 | 97.799 | 3.448 | 172.342 | 1.00 | 35.52 |
| ATOM | 5236 | C | VAL | 3358 | 95.689 | 1.089 | 174.530 | 1.00 | 34.72 |
| ATOM | 5237 | O | VAL | 3358 | 95.143 | 1.737 | 175.424 | 1.00 | 34.13 |
| ATOM | 5238 | N | LEU | 3359 | 95.900 | −0.227 | 174.614 | 1.00 | 34.83 |
| ATOM | 5239 | CA | LEU | 3359 | 95.464 | −1.017 | 175.768 | 1.00 | 34.41 |
| ATOM | 5240 | CB | LEU | 3359 | 94.495 | −2.102 | 175.305 | 1.00 | 33.37 |
| ATOM | 5241 | CG | LEU | 3359 | 93.526 | −1.718 | 174.191 | 1.00 | 32.23 |
| ATOM | 5242 | CD1 | LEU | 3359 | 92.604 | −2.876 | 173.883 | 1.00 | 30.21 |
| ATOM | 5243 | CD2 | LEU | 3359 | 92.730 | −0.509 | 174.614 | 1.00 | 33.35 |
| ATOM | 5244 | C | LEU | 3359 | 96.638 | −1.678 | 176.507 | 1.00 | 35.37 |
| ATOM | 5245 | O | LEU | 3359 | 96.510 | −1.972 | 177.729 | 1.00 | 35.11 |
| ATOM | 5246 | C1 | UAP | 301 | 89.711 | 29.378 | 112.680 | 1.00 | 66.40 |
| ATOM | 5247 | C2 | UAP | 301 | 90.274 | 28.285 | 113.574 | 1.00 | 65.84 |
| ATOM | 5248 | C3 | UAP | 301 | 91.103 | 27.178 | 112.923 | 1.00 | 64.73 |
| ATOM | 5249 | C4 | UAP | 301 | 91.933 | 27.611 | 111.696 | 1.00 | 65.90 |
| ATOM | 5250 | C5 | UAP | 301 | 91.697 | 29.046 | 111.263 | 1.00 | 66.11 |
| ATOM | 5251 | C6 | UAP | 301 | 92.706 | 29.570 | 110.253 | 1.00 | 66.51 |
| ATOM | 5252 | O2 | UAP | 301 | 91.058 | 28.863 | 114.568 | 1.00 | 67.12 |
| ATOM | 5253 | O3 | UAP | 301 | 90.224 | 26.188 | 112.541 | 1.00 | 63.41 |
| ATOM | 5254 | O5 | UAP | 301 | 90.720 | 29.905 | 111.807 | 1.00 | 66.68 |
| ATOM | 5255 | O61 | UAP | 301 | 93.591 | 28.817 | 109.808 | 1.00 | 66.33 |
| ATOM | 5256 | O62 | UAP | 301 | 92.603 | 30.772 | 109.940 | 1.00 | 67.20 |
| ATOM | 5257 | S | UAP | 301 | 90.405 | 28.619 | 116.174 | 1.00 | 68.07 |
| ATOM | 5258 | O1S | UAP | 301 | 91.196 | 29.370 | 117.070 | 1.00 | 68.75 |
| ATOM | 5259 | O2S | UAP | 301 | 90.491 | 27.233 | 116.500 | 1.00 | 69.12 |
| ATOM | 5260 | O3S | UAP | 301 | 89.046 | 29.095 | 116.161 | 1.00 | 68.06 |
| ATOM | 5261 | C1 | SGN | 302 | 85.562 | 29.966 | 109.305 | 1.00 | 62.50 |
| ATOM | 5262 | C2 | SGN | 302 | 86.994 | 30.437 | 109.045 | 1.00 | 64.17 |
| ATOM | 5263 | C3 | SGN | 302 | 88.007 | 29.612 | 109.794 | 1.00 | 64.64 |
| ATOM | 5264 | C4 | SGN | 302 | 87.691 | 29.587 | 111.293 | 1.00 | 64.51 |
| ATOM | 5265 | C5 | SGN | 302 | 86.301 | 28.963 | 111.428 | 1.00 | 64.20 |
| ATOM | 5266 | C6 | SGN | 302 | 85.816 | 28.793 | 112.869 | 1.00 | 65.88 |
| ATOM | 5267 | N | SGN | 302 | 87.263 | 30.060 | 107.685 | 1.00 | 65.96 |
| ATOM | 5268 | O1 | SGN | 302 | 85.341 | 28.763 | 108.606 | 1.00 | 60.28 |
| ATOM | 5269 | O3 | SGN | 302 | 89.279 | 30.155 | 109.516 | 1.00 | 65.38 |
| ATOM | 5270 | O4 | SGN | 302 | 88.643 | 28.775 | 111.959 | 1.00 | 65.65 |
| ATOM | 5271 | O5 | SGN | 302 | 85.353 | 29.807 | 110.723 | 1.00 | 62.62 |
| ATOM | 5272 | O6 | SGN | 302 | 86.626 | 29.514 | 113.779 | 1.00 | 67.31 |
| ATOM | 5273 | S1 | SGN | 302 | 87.587 | 31.308 | 106.514 | 1.00 | 68.31 |
| ATOM | 5274 | O1S | SGN | 302 | 88.294 | 30.730 | 105.396 | 1.00 | 67.08 |
| ATOM | 5275 | O2S | SGN | 302 | 88.391 | 32.298 | 107.167 | 1.00 | 67.69 |
| ATOM | 5276 | O3S | SGN | 302 | 86.329 | 31.882 | 106.091 | 1.00 | 66.97 |
| ATOM | 5277 | S2 | SGN | 302 | 85.909 | 30.962 | 114.464 | 1.00 | 69.09 |
| ATOM | 5278 | O4S | SGN | 302 | 86.882 | 31.639 | 115.271 | 1.00 | 68.92 |
| ATOM | 5279 | O5S | SGN | 302 | 84.773 | 30.572 | 115.252 | 1.00 | 69.02 |
| ATOM | 5280 | O65 | SGN | 302 | 85.463 | 31.801 | 113.377 | 1.00 | 69.15 |
| ATOM | 5281 | C1 | IDU | 303 | 84.509 | 25.797 | 106.897 | 1.00 | 55.63 |
| ATOM | 5282 | C2 | IDU | 303 | 84.659 | 27.144 | 106.163 | 1.00 | 57.90 |
| ATOM | 5283 | C3 | IDU | 303 | 83.864 | 28.339 | 106.732 | 1.00 | 58.91 |
| ATOM | 5284 | C4 | IDU | 303 | 84.000 | 28.441 | 108.262 | 1.00 | 59.03 |
| ATOM | 5285 | C5 | IDU | 303 | 83.766 | 27.063 | 108.825 | 1.00 | 58.04 |
| ATOM | 5286 | C6 | IDU | 303 | 83.412 | 27.066 | 110.293 | 1.00 | 59.02 |
| ATOM | 5287 | O2 | IDU | 303 | 85.993 | 27.486 | 106.028 | 1.00 | 61.09 |
| ATOM | 5288 | O3 | IDU | 303 | 82.534 | 28.219 | 106.368 | 1.00 | 58.89 |
| ATOM | 5289 | O5 | IDU | 303 | 84.507 | 25.992 | 108.310 | 1.00 | 56.83 |
| ATOM | 5290 | O61 | IDU | 303 | 82.304 | 27.518 | 110.648 | 1.00 | 60.56 |
| ATOM | 5291 | O62 | IDU | 303 | 84.204 | 26.466 | 111.054 | 1.00 | 58.07 |
| ATOM | 5292 | S | IDU | 303 | 86.568 | 27.438 | 104.373 | 1.00 | 64.62 |
| ATOM | 5293 | O1S | IDU | 303 | 87.498 | 26.359 | 104.282 | 1.00 | 64.85 |
| ATOM | 5294 | O2S | IDU | 303 | 87.221 | 28.679 | 104.077 | 1.00 | 64.30 |
| ATOM | 5295 | O3S | IDU | 303 | 85.426 | 27.210 | 103.521 | 1.00 | 65.20 |
| ATOM | 5296 | C1 | SGN | 304 | 81.524 | 21.415 | 106.321 | 1.00 | 48.29 |

TABLE 6-continued

FGF2/FGFR1/Heparin Ternary Complex

| ATOM | 5297 | C2  | SGN | 304 | 81.423 | 22.246 | 107.606 | 1.00 | 47.44 |
| ATOM | 5298 | C3  | SGN | 304 | 81.681 | 23.714 | 107.324 | 1.00 | 47.98 |
| ATOM | 5299 | C4  | SGN | 304 | 83.079 | 23.842 | 106.723 | 1.00 | 48.95 |
| ATOM | 5300 | C5  | SGN | 304 | 83.103 | 23.041 | 105.431 | 1.00 | 48.77 |
| ATOM | 5301 | C6  | SGN | 304 | 84.454 | 23.117 | 104.741 | 1.00 | 49.71 |
| ATOM | 5302 | N   | SGN | 304 | 80.070 | 22.142 | 108.071 | 1.00 | 45.66 |
| ATOM | 5303 | O1  | SGN | 304 | 80.479 | 21.788 | 105.427 | 1.00 | 49.32 |
| ATOM | 5304 | O3  | SGN | 304 | 81.599 | 24.434 | 108.533 | 1.00 | 47.11 |
| ATOM | 5305 | O4  | SGN | 304 | 83.322 | 25.205 | 106.432 | 1.00 | 51.46 |
| ATOM | 5306 | O5  | SGN | 304 | 82.816 | 21.657 | 105.741 | 1.00 | 48.30 |
| ATOM | 5307 | O6  | SGN | 304 | 85.185 | 21.924 | 104.984 | 1.00 | 50.11 |
| ATOM | 5308 | S1  | SGN | 304 | 79.664 | 20.705 | 108.987 | 1.00 | 44.63 |
| ATOM | 5309 | O1S | SGN | 304 | 79.613 | 19.567 | 108.119 | 1.00 | 45.33 |
| ATOM | 5310 | O2S | SGN | 304 | 78.396 | 20.914 | 109.582 | 1.00 | 46.11 |
| ATOM | 5311 | O3S | SGN | 304 | 80.650 | 20.507 | 110.002 | 1.00 | 45.41 |
| ATOM | 5312 | S2  | SGN | 304 | 86.826 | 22.096 | 105.597 | 1.00 | 50.54 |
| ATOM | 5313 | O4S | SGN | 304 | 86.839 | 21.724 | 106.976 | 1.00 | 51.41 |
| ATOM | 5314 | O5S | SGN | 304 | 87.269 | 23.462 | 105.450 | 1.00 | 50.31 |
| ATOM | 5315 | O6S | SGN | 304 | 87.672 | 21.234 | 104.812 | 1.00 | 50.79 |
| ATOM | 5316 | C1  | IDU | 305 | 78.695 | 22.818 | 102.676 | 1.00 | 58.45 |
| ATOM | 5317 | C2  | IDU | 305 | 77.977 | 22.187 | 103.924 | 1.00 | 55.41 |
| ATOM | 5318 | C3  | IDU | 305 | 78.507 | 20.821 | 104.375 | 1.00 | 52.78 |
| ATOM | 5319 | C4  | IDU | 305 | 80.037 | 20.825 | 104.454 | 1.00 | 51.52 |
| ATOM | 5320 | C5  | IDU | 305 | 80.549 | 21.288 | 103.101 | 1.00 | 52.02 |
| ATOM | 5321 | C6  | IDU | 305 | 81.993 | 20.963 | 102.837 | 1.00 | 51.75 |
| ATOM | 5322 | O2  | IDU | 305 | 78.106 | 23.074 | 105.015 | 1.00 | 55.80 |
| ATOM | 5323 | O3  | IDU | 305 | 78.061 | 19.864 | 103.503 | 1.00 | 54.66 |
| ATOM | 5324 | O5  | IDU | 305 | 80.056 | 22.449 | 102.505 | 1.00 | 54.74 |
| ATOM | 5325 | O61 | IDU | 305 | 82.416 | 19.815 | 103.042 | 1.00 | 52.45 |
| ATOM | 5326 | O62 | IDU | 305 | 82.704 | 21.926 | 102.502 | 1.00 | 51.18 |
| ATOM | 5327 | S   | IDU | 305 | 76.837 | 23.003 | 106.213 | 1.00 | 53.85 |
| ATOM | 5328 | O1S | IDU | 305 | 77.342 | 22.266 | 107.302 | 1.00 | 52.70 |
| ATOM | 5329 | O2S | IDU | 305 | 75.691 | 22.363 | 105.650 | 1.00 | 53.75 |
| ATOM | 5330 | O3S | IDU | 305 | 76.559 | 24.346 | 106.605 | 1.00 | 53.55 |
| ATOM | 5331 | C1  | SGN | 306 | 75.154 | 21.393 | 98.778  | 1.00 | 78.80 |
| ATOM | 5332 | C2  | SGN | 306 | 74.770 | 21.467 | 100.267 | 1.00 | 79.74 |
| ATOM | 5333 | C3  | SGN | 306 | 75.639 | 22.506 | 100.972 | 1.00 | 76.61 |
| ATOM | 5334 | C4  | SGN | 306 | 77.112 | 22.075 | 100.839 | 1.00 | 72.68 |
| ATOM | 5335 | C5  | SGN | 306 | 77.424 | 22.049 | 99.326  | 1.00 | 74.98 |
| ATOM | 5336 | C6  | SGN | 306 | 78.861 | 21.644 | 99.022  | 1.00 | 76.09 |
| ATOM | 5337 | N   | SGN | 306 | 73.403 | 21.965 | 100.351 | 1.00 | 82.98 |
| ATOM | 5338 | O1  | SGN | 306 | 74.371 | 20.399 | 98.144  | 1.00 | 81.41 |
| ATOM | 5339 | O3  | SGN | 306 | 75.270 | 22.557 | 102.339 | 1.00 | 77.49 |
| ATOM | 5340 | O4  | SGN | 306 | 77.915 | 23.069 | 101.487 | 1.00 | 65.99 |
| ATOM | 5341 | O5  | SGN | 306 | 76.557 | 21.082 | 98.708  | 1.00 | 76.02 |
| ATOM | 5342 | O6  | SGN | 306 | 78.873 | 20.683 | 97.944  | 1.00 | 78.66 |
| ATOM | 5343 | S1  | SGN | 306 | 72.288 | 21.244 | 101.549 | 1.00 | 86.61 |
| ATOM | 5344 | O1S | SGN | 306 | 72.520 | 19.819 | 101.628 | 1.00 | 86.13 |
| ATOM | 5345 | O2S | SGN | 306 | 70.954 | 21.508 | 101.095 | 1.00 | 85.70 |
| ATOM | 5346 | O3S | SGN | 306 | 72.482 | 21.855 | 102.841 | 1.00 | 85.42 |
| ATOM | 5347 | S2  | SGN | 306 | 78.623 | 21.211 | 96.238  | 1.00 | 80.07 |
| ATOM | 5348 | O4S | SGN | 306 | 77.928 | 20.181 | 95.265  | 1.00 | 78.72 |
| ATOM | 5349 | O5S | SGN | 306 | 79.908 | 21.419 | 95.639  | 1.00 | 80.77 |
| ATOM | 5350 | O6S | SGN | 306 | 77.876 | 22.453 | 96.196  | 1.00 | 79.95 |
| ATOM | 5351 | C1  | IDU | 307 | 72.715 | 17.940 | 96.060  | 1.00 | 88.33 |
| ATOM | 5352 | C2  | IDU | 307 | 72.875 | 19.430 | 95.641  | 1.00 | 86.54 |
| ATOM | 5353 | C3  | IDU | 307 | 74.326 | 19.967 | 95.727  | 1.00 | 86.02 |
| ATOM | 5354 | C4  | IDU | 307 | 74.981 | 19.647 | 97.082  | 1.00 | 84.48 |
| ATOM | 5355 | C5  | IDU | 307 | 74.745 | 18.190 | 97.392  | 1.00 | 83.71 |
| ATOM | 5356 | C6  | IDU | 307 | 75.601 | 17.687 | 98.529  | 1.00 | 83.21 |
| ATOM | 5357 | O2  | IDU | 307 | 72.493 | 19.517 | 94.285  | 1.00 | 87.26 |
| ATOM | 5358 | O3  | IDU | 307 | 74.328 | 21.338 | 95.507  | 1.00 | 85.33 |
| ATOM | 5359 | O5  | IDU | 307 | 73.457 | 17.651 | 97.250  | 1.00 | 86.50 |
| ATOM | 5360 | O61 | IDU | 307 | 76.299 | 16.692 | 98.323  | 1.00 | 81.29 |
| ATOM | 5361 | O62 | IDU | 307 | 75.326 | 18.118 | 99.672  | 1.00 | 82.32 |
| ATOM | 5362 | S   | IDU | 307 | 71.672 | 20.988 | 93.788  | 1.00 | 88.72 |
| ATOM | 5363 | O1S | IDU | 307 | 72.664 | 21.855 | 93.236  | 1.00 | 88.23 |
| ATOM | 5364 | O2S | IDU | 307 | 71.032 | 21.589 | 94.928  | 1.00 | 88.48 |
| ATOM | 5365 | O3S | IDU | 307 | 70.717 | 20.595 | 92.783  | 1.00 | 88.33 |
| ATOM | 5366 | C1  | SGN | 308 | 69.092 | 13.994 | 96.200  | 1.00 | 94.38 |
| ATOM | 5367 | C2  | SGN | 308 | 70.317 | 14.199 | 97.107  | 1.00 | 95.70 |
| ATOM | 5368 | C3  | SGN | 308 | 70.606 | 15.663 | 97.398  | 1.00 | 93.91 |
| ATOM | 5369 | C4  | SGN | 308 | 70.981 | 16.226 | 96.030  | 1.00 | 92.64 |
| ATOM | 5370 | C5  | SGM | 308 | 69.768 | 16.104 | 95.072  | 1.00 | 94.34 |
| ATOM | 5371 | C6  | SGN | 308 | 70.155 | 16.638 | 93.684  | 1.00 | 95.74 |
| ATOM | 5372 | N   | SGN | 308 | 70.243 | 13.442 | 98.339  | 1.00 | 99.23 |
| ATOM | 5373 | O1  | SGN | 308 | 67.922 | 14.465 | 96.870  | 1.00 | 93.44 |

TABLE 6-continued

FGF2/FGFR1/Heparin Ternary Complex

| ATOM | 5374 | O3 | SGN | 308 | 71.728 | 15.764 | 98.252 | 1.00 | 92.74 |
|---|---|---|---|---|---|---|---|---|---|
| ATOM | 5375 | O4 | SGN | 308 | 71.327 | 17.609 | 96.157 | 1.00 | 90.67 |
| ATOM | 5376 | O5 | SGN | 308 | 69.339 | 14.705 | 94.949 | 1.00 | 94.10 |
| ATOM | 5377 | O6 | SGN | 308 | 71.085 | 15.714 | 93.059 | 1.00 | 97.55 |
| ATOM | 5378 | S1 | SGN | 308 | 71.661 | 12.414 | 98.738 | 1.00 | 101.81 |
| ATOM | 5379 | O1S | SGN | 308 | 71.720 | 11.295 | 97.822 | 1.00 | 101.81 |
| ATOM | 5380 | O2S | SGN | 308 | 71.485 | 11.950 | 100.088 | 1.00 | 101.81 |
| ATOM | 5381 | O3S | SGN | 308 | 72.886 | 13.189 | 98.639 | 1.00 | 101.81 |
| ATOM | 5382 | S2 | SGN | 308 | 72.736 | 16.256 | 92.593 | 1.00 | 98.46 |
| ATOM | 5383 | O4S | SGN | 308 | 72.700 | 17.607 | 92.120 | 1.00 | 97.88 |
| ATOM | 5384 | O5S | SGN | 308 | 73.216 | 15.397 | 91.547 | 1.00 | 97.59 |
| ATOM | 5385 | O6S | SGN | 308 | 73.612 | 16.123 | 93.731 | 1.00 | 96.16 |
| ATOM | 5386 | C1 | UAP | 1301 | 99.984 | 28.369 | 114.585 | 1.00 | 63.64 |
| ATOM | 5387 | C2 | UAP | 1301 | 98.784 | 28.735 | 115.438 | 1.00 | 63.25 |
| ATOM | 5388 | C3 | UAP | 1301 | 98.294 | 30.192 | 115.433 | 1.00 | 64.22 |
| ATOM | 5389 | C4 | UAP | 1301 | 98.524 | 30.968 | 114.107 | 1.00 | 64.45 |
| ATOM | 5390 | C5 | UAP | 1301 | 99.311 | 30.177 | 113.059 | 1.00 | 64.79 |
| ATOM | 5391 | C6 | UAP | 1301 | 99.312 | 30.805 | 111.668 | 1.00 | 65.66 |
| ATOM | 5392 | O2 | UAP | 1301 | 97.709 | 27.939 | 115.078 | 1.00 | 61.67 |
| ATOM | 5393 | O3 | UAP | 1301 | 98.934 | 30.847 | 116.486 | 1.00 | 63.94 |
| ATOM | 5394 | O5 | UAP | 1301 | 99.907 | 28.911 | 113.266 | 1.00 | 63.51 |
| ATOM | 5395 | O61 | UAP | 1301 | 98.751 | 31.902 | 111.474 | 1.00 | 65.52 |
| ATOM | 5396 | O62 | UAP | 1301 | 99.869 | 30.146 | 110.766 | 1.00 | 66.61 |
| ATOM | 5397 | S | UAP | 1301 | 96.989 | 27.084 | 116.416 | 1.00 | 59.96 |
| ATOM | 5398 | O1S | UAP | 1301 | 95.599 | 27.032 | 116.168 | 1.00 | 59.72 |
| ATOM | 5399 | O2S | UAP | 1301 | 97.243 | 27.788 | 117.649 | 1.00 | 60.99 |
| ATOM | 5400 | O3S | UAP | 1301 | 97.572 | 25.776 | 116.405 | 1.00 | 59.85 |
| ATOM | 5401 | C1 | SGN | 1302 | 105.076 | 27.945 | 115.940 | 1.00 | 66.27 |
| ATOM | 5402 | C2 | SGN | 1302 | 104.590 | 28.121 | 114.499 | 1.00 | 65.68 |
| ATOM | 5403 | C3 | SGN | 1302 | 103.305 | 28.937 | 114.471 | 1.00 | 64.98 |
| ATOM | 5404 | C4 | SGN | 1302 | 102.273 | 28.162 | 115.267 | 1.00 | 64.94 |
| ATOM | 5405 | C5 | SGN | 1302 | 102.753 | 28.002 | 116.704 | 1.00 | 65.77 |
| ATOM | 5406 | C6 | SGN | 1302 | 101.712 | 27.239 | 117.521 | 1.00 | 66.32 |
| ATOM | 5407 | N | SGN | 1302 | 105.593 | 28.906 | 113.815 | 1.00 | 66.15 |
| ATOM | 5408 | O1 | SGN | 1302 | 105.374 | 29.247 | 116.443 | 1.00 | 67.50 |
| ATOM | 5409 | O3 | SGN | 1302 | 102.858 | 29.086 | 113.138 | 1.00 | 64.85 |
| ATOM | 5410 | O4 | SGN | 1302 | 101.080 | 28.882 | 115.277 | 1.00 | 64.61 |
| ATOM | 5411 | O5 | SGN | 1302 | 104.021 | 27.294 | 116.694 | 1.00 | 65.72 |
| ATOM | 5412 | O6 | SGN | 1302 | 102.251 | 26.030 | 118.025 | 1.00 | 67.95 |
| ATOM | 5413 | S1 | SGN | 1302 | 106.415 | 28.196 | 112.415 | 1.00 | 66.53 |
| ATOM | 5414 | O1S | SGN | 1302 | 105.883 | 28.790 | 111.214 | 1.00 | 65.81 |
| ATOM | 5415 | O2S | SGN | 1302 | 106.164 | 26.789 | 112.436 | 1.00 | 65.66 |
| ATOM | 5416 | O3S | SGN | 1302 | 107.837 | 28.429 | 112.508 | 1.00 | 65.29 |
| ATOM | 5417 | S2 | SGN | 1302 | 101.822 | 25.610 | 119.680 | 1.00 | 69.68 |
| ATOM | 5418 | O4S | SGN | 1302 | 102.732 | 26.252 | 120.587 | 1.00 | 70.12 |
| ATOM | 5419 | O5S | SGN | 1302 | 101.904 | 24.179 | 119.820 | 1.00 | 68.94 |
| ATOM | 5420 | O6S | SGN | 1302 | 100.465 | 26.036 | 119.920 | 1.00 | 69.87 |
| ATOM | 5421 | C1 | IDU | 1303 | 107.412 | 32.109 | 117.309 | 1.00 | 70.24 |
| ATOM | 5422 | C2 | IDU | 1303 | 107.919 | 30.853 | 116.576 | 1.00 | 70.77 |
| ATOM | 5423 | C3 | IDU | 1303 | 107.641 | 29.512 | 117.278 | 1.00 | 69.95 |
| ATOM | 5424 | C4 | IDU | 1303 | 106.154 | 29.370 | 117.637 | 1.00 | 69.26 |
| ATOM | 5425 | C5 | IDU | 1303 | 105.701 | 30.661 | 118.318 | 1.00 | 69.74 |
| ATOM | 5426 | C6 | IDU | 1303 | 104.297 | 30.559 | 118.843 | 1.00 | 70.20 |
| ATOM | 5427 | O2 | IDU | 1303 | 107.390 | 30.815 | 115.289 | 1.00 | 73.31 |
| ATOM | 5428 | O3 | IDU | 1303 | 108.438 | 29.393 | 118.402 | 1.00 | 70.32 |
| ATOM | 5429 | O5 | IDU | 1303 | 106.078 | 31.915 | 117.781 | 1.00 | 69.63 |
| ATOM | 5430 | O61 | IDU | 1303 | 104.088 | 29.945 | 119.899 | 1.00 | 70.68 |
| ATOM | 5431 | O62 | IDU | 1303 | 103.458 | 31.288 | 118.281 | 1.00 | 70.21 |
| ATOM | 5432 | S | IDU | 1303 | 108.350 | 31.678 | 114.099 | 1.00 | 75.41 |
| ATOM | 5433 | O1S | IDU | 1303 | 108.386 | 33.051 | 114.484 | 1.00 | 75.11 |
| ATOM | 5434 | O2S | IDU | 1303 | 107.730 | 31.538 | 112.814 | 1.00 | 75.13 |
| ATOM | 5435 | O3S | IDU | 1303 | 109.661 | 31.083 | 114.128 | 1.00 | 74.40 |
| ATOM | 5436 | C1 | SGN | 1304 | 108.865 | 35.363 | 121.338 | 1.00 | 73.27 |
| ATOM | 5437 | C2 | SGN | 1304 | 108.137 | 34.041 | 121.685 | 1.00 | 71.39 |
| ATOM | 5438 | C3 | SGN | 1304 | 108.445 | 32.956 | 120.649 | 1.00 | 71.09 |
| ATOM | 5439 | C4 | SGN | 1304 | 108.034 | 33.464 | 119.263 | 1.00 | 71.78 |
| ATOM | 5440 | C5 | SGN | 1304 | 108.843 | 34.746 | 118.973 | 1.00 | 73.44 |
| ATOM | 5441 | C6 | SGN | 1304 | 108.516 | 35.340 | 117.611 | 1.00 | 75.39 |
| ATOM | 5442 | N | 5GM | 1304 | 108.696 | 33.559 | 122.927 | 1.00 | 68.96 |
| ATOM | 5443 | O1 | SGN | 1304 | 110.283 | 35.211 | 121.488 | 1.00 | 75.58 |
| ATOM | 5444 | O3 | SGN | 1304 | 107.738 | 31.776 | 120.988 | 1.00 | 69.69 |
| ATOM | 5445 | O4 | SGN | 1304 | 108.348 | 32.447 | 118.309 | 1.00 | 70.53 |
| ATOM | 5446 | O5 | SGN | 1304 | 108.520 | 35.735 | 119.988 | 1.00 | 73.79 |
| ATOM | 5447 | O6 | SGN | 1304 | 107.318 | 36.107 | 117.720 | 1.00 | 77.19 |
| ATOM | 5448 | S1 | SGN | 1304 | 108.114 | 34.231 | 124.446 | 1.00 | 66.75 |
| ATOM | 5449 | O1S | SGN | 1304 | 108.335 | 35.645 | 124.481 | 1.00 | 67.47 |
| ATOM | 5450 | O2S | SGN | 1304 | 108.833 | 33.590 | 125.494 | 1.00 | 66.13 |

TABLE 6-continued

FGF2/FGFR1/Heparin Ternary Complex

| ATOM | 5451 | O3S | SGN | 1304 | 106.720 | 33.957 | 124.574 | 1.00 | 67.93 |
|---|---|---|---|---|---|---|---|---|---|
| ATOM | 5452 | S2 | SGN | 1304 | 106.061 | 35.870 | 116.506 | 1.00 | 78.60 |
| ATOM | 5453 | O4S | SGN | 1304 | 105.417 | 37.125 | 116.243 | 1.00 | 79.30 |
| ATOM | 5454 | O5S | SGN | 1304 | 105.107 | 34.932 | 117.038 | 1.00 | 78.89 |
| ATOM | 5455 | O6S | SGN | 1304 | 106.671 | 35.336 | 115.310 | 1.00 | 78.63 |
| ATOM | 5456 | C1 | IDU | 1305 | 114.018 | 35.900 | 122.301 | 1.00 | 83.03 |
| ATOM | 5457 | C2 | IDU | 1305 | 113.051 | 35.540 | 123.454 | 1.00 | 80.20 |
| ATOM | 5458 | C3 | IDU | 1305 | 111.573 | 35.996 | 123.419 | 1.00 | 78.83 |
| ATOM | 5459 | C4 | IDU | 1305 | 110.999 | 36.329 | 122.025 | 1.00 | 77.88 |
| ATOM | 5460 | C5 | IDU | 1305 | 112.092 | 36.738 | 121.040 | 1.00 | 79.17 |
| ATOM | 5461 | C6 | IDU | 1305 | 111.548 | 37.212 | 119.687 | 1.00 | 79.44 |
| ATOM | 5462 | O2 | IDU | 1305 | 113.215 | 34.215 | 123.956 | 1.00 | 77.79 |
| ATOM | 5463 | O3 | IDU | 1305 | 111.404 | 37.056 | 124.273 | 1.00 | 78.31 |
| ATOM | 5464 | O5 | IDU | 1305 | 113.352 | 36.113 | 121.058 | 1.00 | 80.89 |
| ATOM | 5465 | O61 | IDU | 1305 | 110.438 | 37.771 | 119.627 | 1.00 | 79.07 |
| ATOM | 5466 | O62 | IDU | 1305 | 112.215 | 36.905 | 118.679 | 1.00 | 78.65 |
| ATOM | 5467 | S | IDU | 1305 | 112.571 | 32.870 | 123.007 | 1.00 | 75.82 |
| ATOM | 5468 | O1S | IDU | 1305 | 112.705 | 33.181 | 121.627 | 1.00 | 76.64 |
| ATOM | 5469 | O2S | IDU | 1305 | 111.205 | 32.675 | 123.345 | 1.00 | 76.15 |
| ATOM | 5470 | O3S | IDU | 1305 | 113.350 | 31.733 | 123.340 | 1.00 | 73.63 |
| ATOM | 5471 | C1 | SGN | 1306 | 118.222 | 36.383 | 120.003 | 1.00 | 98.21 |
| ATOM | 5472 | C2 | SGN | 1306 | 118.143 | 35.478 | 121.253 | 1.00 | 98.39 |
| ATOM | 5473 | C3 | SGN | 1306 | 116.756 | 35.509 | 121.875 | 1.00 | 97.23 |
| ATOM | 5474 | C4 | SGN | 1306 | 116.298 | 36.952 | 122.158 | 1.00 | 94.94 |
| ATOM | 5475 | C5 | SGN | 1306 | 116.362 | 37.752 | 120.844 | 1.00 | 96.28 |
| ATOM | 5476 | C6 | SGN | 1306 | 115.932 | 39.207 | 121.039 | 1.00 | 97.55 |
| ATOM | 5477 | N | SGN | 1306 | 118.381 | 34.086 | 120.796 | 1.00 | 99.10 |
| ATOM | 5478 | O1 | SGN | 1306 | 117.465 | 35.806 | 118.949 | 1.00 | 99.21 |
| ATOM | 5479 | O3 | SGN | 1306 | 116.745 | 34.697 | 123.043 | 1.00 | 99.21 |
| ATOM | 5480 | O4 | SGN | 1306 | 114.946 | 36.939 | 122.709 | 1.00 | 89.42 |
| ATOM | 5481 | O5 | SGN | 1306 | 117.728 | 37.702 | 120.348 | 1.00 | 97.38 |
| ATOM | 5482 | O6 | SGN | 1306 | 117.053 | 40.079 | 120.827 | 1.00 | 98.80 |
| ATOM | 5483 | S1 | SGN | 1306 | 117.056 | 32.951 | 120.302 | 1.00 | 99.45 |
| ATOM | 5484 | O1S | SGN | 1306 | 115.892 | 33.658 | 119.812 | 1.00 | 99.12 |
| ATOM | 5485 | O2S | SGN | 1306 | 116.723 | 32.178 | 121.456 | 1.00 | 99.28 |
| ATOM | 5486 | O3S | SGN | 1306 | 117.543 | 32.068 | 119.277 | 1.00 | 99.02 |
| ATOM | 5487 | S2 | SGN | 1306 | 117.386 | 40.657 | 119.172 | 1.00 | 99.96 |
| ATOM | 5488 | O4S | SGN | 1306 | 118.013 | 41.944 | 119.241 | 1.00 | 99.55 |
| ATOM | 5489 | O5S | SGN | 1306 | 116.148 | 40.755 | 118.444 | 1.00 | 99.37 |
| ATOM | 5490 | O6S | SGN | 1306 | 118.244 | 39.703 | 118.514 | 1.00 | 100.23 |

We claim:

1. A crystal comprising the purified polypeptide of SEQ ID NO: 1 co-crystallized with the FGF-1 of SEQ ID NO: 17 having tetragonal space group symmetry P1 and the unit cell dimensions of a=62.55 Å, b=64.06 Å, c=64.14 Å, α=93.40°, β=111.17°, and γ97.18°.

* * * * *